United States Patent
Chen et al.

(10) Patent No.: US 8,658,646 B2
(45) Date of Patent: *Feb. 25, 2014

(54) PYRROLOPYRAZINE KINASE INHIBITORS

(75) Inventors: Shaoqing Chen, Bridgewater, NJ (US);
Javier de Vicente Fidalgo, Foster City, CA (US); Matthew Michael Hamilton, Hackettstown, NJ (US); Johannes Cornelius Hermann, Jersey City, NJ (US); Joshua Kennedy-Smith, New York, NY (US); Hongju Li, Edison, NJ (US); Allen John Lovey, North Caldwell, NJ (US); Matthew C. Lucas, Verona, NJ (US); Kin-Chun Thomas Luk, North Caldwell, NJ (US); Stephen M. Lynch, Westfield, NJ (US); Counde O'yang, Beijing (CN); Fernando Padilla, Verona, NJ (US); Ryan Craig Schoenfeld, Basking Ridge, NJ (US); Achyutharao Sidduri, Livingston, NJ (US); Michael Soth, Glen Rock, NJ (US); Ce Wang, Beijing (CN); Peter Michael Wovkulich, Nutley, NJ (US); Xiaohu Zhang, Jiangsu (CN)

(73) Assignee: Hoffmann-LaRoche Inc., Nutley, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 13/600,863

(22) Filed: Aug. 31, 2012

(65) Prior Publication Data
US 2013/0059834 A1   Mar. 7, 2013

(30) Foreign Application Priority Data
Sep. 1, 2011 (WO) ................ PCT/CN2011/001489

(51) Int. Cl.
*A61K 31/495* (2006.01)

(52) U.S. Cl.
USPC .......... 514/249; 544/117; 544/350; 546/118; 546/139; 546/152; 546/199; 546/276.7; 548/235; 548/360.1; 548/361.1; 548/518; 548/950; 549/356; 549/429

(58) Field of Classification Search
USPC .......... 514/249; 544/117, 350; 546/118, 139, 546/152, 199, 276.7; 548/235, 360.1, 548/361.1, 518, 950; 549/356, 429
See application file for complete search history.

(56) References Cited

U.S. PATENT DOCUMENTS

| | | | |
|---|---|---|---|
| 7,902,197 B2 | 3/2011 | Elworthy et al. |
| 7,932,254 B2 | 4/2011 | DuBois et al. |
| 7,939,531 B2 | 5/2011 | Bamberg et al. |
| 8,008,298 B2 | 8/2011 | Bamberg et al. |
| 8,119,636 B2 | 2/2012 | Du Bois et al. |
| 2011/0230414 A1 | 9/2011 | Hendricks et al. |
| 2011/0230462 A1 | 9/2011 | Hendricks et al. |
| 2011/0288067 A1 | 11/2011 | Hendricks et al. |
| 2011/0288097 A1 | 11/2011 | Hendricks et al. |

OTHER PUBLICATIONS (International Search Report for PCT/EP2012/066567 Dec. 3, 2012).
Leonard et al., "JAKS and STATS: biological implications" Annual Rev. Immunol 16:293-322 ( 1998).
Turner et al., "Perinatal lethality and blocked b-cell development in mice lacking the tyrosine kinase Syk:" Nature 378:298-302 ( 1995).
Cheng et al., "Syk tyrosine kinase required for mouse viability and B-cell developement" Nature 378:303-306 ( 1995).

*Primary Examiner* — Douglas M Willis

(57) ABSTRACT

The present invention relates to the use of novel pyrrolopyrazine derivatives of Formula I,

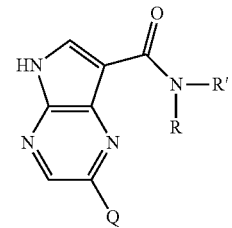

wherein the variables are defined as described herein, which inhibit JAK and SYK and are useful for the treatment of auto-immune and inflammatory diseases.

17 Claims, No Drawings

PYRROLOPYRAZINE KINASE INHIBITORS

CROSS-REFERENCE TO RELATED APPLICATIONS

This application is entitled to the benefit of U.S. provisional patent application Ser. No. PCT/CN2011/001489 filed on Sep. 1, 2011, the disclosure of which is incorporated herein by reference.

FIELD OF THE INVENTION

The present invention relates to the use of novel pyrrolopyrazine derivatives which are JAK and SYK inhibitors and selectively inhibit JAK3 and are useful for the treatment of autoimmune and inflammatory diseases. This application is related to U.S. application Ser. Nos. 13/110,062, filed May 18, 2011, 13/110,053, filed May 18, 2011, 13/040,310, filed March 4, 13/039,433, filed Mar. 3, 2011, 12/378,837, filed on Feb. 20, 2009, 12/378,869, filed on Feb. 20, 2009, 12/378,971, filed on Feb. 20, 2009, 12/378,977, filed on Feb. 20, 2009, and 12/378,978, filed on Feb. 20, 2009, the disclosures of which are incorporated herein by reference.

The JAKs (JAnus Kinases) are a family of cytoplasmic protein tyrosine kinases including JAK1, JAK2, JAK3 and TYK2. Each of the JAKs is preferentially associated with the intracytoplasmic portion of discrete cytokine receptors (*Annu. Rev. Immunol.* 16 (1998), pp. 293-322).

JAK/STAT signaling has been implicated in the mediation of many abnormal immune responses such as allergies, asthma, autoimmune diseases such as transplant (allograft) rejection, rheumatoid arthritis, amyotrophic lateral sclerosis and multiple sclerosis, as well as in solid and hematologic malignancies such as leukemia and lymphomas.

Animal studies have suggested that JAK3 not only plays a critical role in B and T lymphocyte maturation, but that JAK3 is constitutively required to maintain T cell function. Modulation of immune activity through this novel mechanism can prove useful in the treatment of T cell proliferative disorders such as transplant rejection and autoimmune diseases.

JAK3 inhibitors are useful therapy as immunosuppressive agents for organ transplants, xeno transplantation, lupus, multiple sclerosis, rheumatoid arthritis, psoriasis, Type I diabetes and complications from diabetes, cancer, asthma, atopic dermatitis, autoimmune thyroid disorders, ulcerative colitis, Crohn's disease, Alzheimer's disease, Leukemia and other indications where immunosuppression would be desirable.

SYK (Spleen Tyrosine Kinase) is a non-receptor tyrosine kinase that is essential for B-cell activation through BCR signaling. SYK become activated upon binding to phosphoryated BCR and thus initiates the early signaling events following BCR activation. Mice deficient in SYK exhibit an early block in B-cell development (Cheng et al. Nature 378: 303, 1995; Turner et al. Nature 378:298, 1995). Therefore inhibition of SYK enzymatic activity in cells is proposed as a treatment for autoimmune disease through its effects on autoantibody production.

SYK is implicated in allergic disorders including asthma (reviewed in Wong et al. Expert Opin Investig Drugs 13:743, 2004). Therefore, small molecule inhibitors of SYK will be useful for treatment of allergy-induced inflammatory diseases including asthma.

In view of the numerous conditions that are contemplated to benefit by treatment involving modulation of the JAK and/or SYK pathways it is immediately apparent that new compounds that modulate JAK and/or SYK pathways and methods of using these compounds should provide substantial therapeutic benefits to a wide variety of patients. Provided herein are novel pyrrolopyrazine derivatives for use in the treatment of conditions in which targeting of the JAK and/or SYK pathways or inhibition of JAK or SYK kinases, particularly JAK3, and are therapeutically useful for the treatment of auto-immune and inflammatory diseases.

SUMMARY OF THE INVENTION

The novel pyrrolopyrazine derivatives provided herein selectively inhibit JAK3 and/or SYK pathways and are useful for the treatment of auto-immune and inflammatory diseases. For example, the compounds of the invention may inhibit JAK3 and SYK. Furthermore, the compounds of the invention may inhibit JAK3 and JAK2, wherein preferred compounds are selective for JAK3 of the JAK kinases, and are useful novel pyrrolopyrazine derivatives for the treatment of auto-immune and inflammatory diseases. Similarly, the compounds of the invention may inhibit JAK3 and JAK1, wherein preferred compounds are selective for JAK3 of the JAK kinases, and are useful novel pyrrolopyrazine derivatives for the treatment of auto-immune and inflammatory diseases. In particular, the bicyclic heteroaryl sidechain off the pyrrolopyrazine core of the compound of Formula I, denoted by variable Q, renders these molecules unexpectedly increasingly selective for JAK3 of the JAK kinases, and/or SYK. In combination with the amido linked sidechains (—C(=O)NRR') off of the pyrrolopyrazine core, which renders the compounds of Formula I unexpectedly potent over pyrrolopyrazine compounds with sidechains other than amido sidechains at the same position on the pyrrolopyrazine core, the compounds of formula I are both unexpectedly potent and selective for JAK3 of the JAK kinases, and/or SYK.

The application provides a compound of Formula I

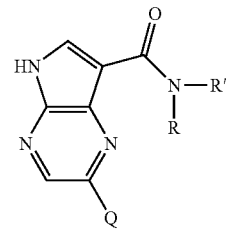

wherein:
R is H;
R' is lower alkoxy or

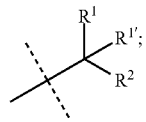

or R and R' together form heterocycloalkyl, optionally substituted with —CN;
$R^1$ is H or $R^{1a}$;
$R^{1a}$ is lower alkyl, cycloalkyl, lower alkoxyl, hydroxy lower alkyl, or lower haloalkyl;
$R^{1'}$ is H or lower alkyl;
or $R^{1a}$ and $R^{1'}$ together form heterocycloalkyl, cycloalkyl, indan-1-yl, phenyl, or heteroaryl, optionally substituted with one or more $R^{1''}$;

each $R^{1''}$ is independently hydroxy, amino, oxo, lower alkyl, —C(=O)NH$_2$, —CN, lower haloalkyl, benzyl, cyano lower alkyl, or —NHC(=O)OC(CH$_3$)$_3$;

$R^2$ is H, hydroxy, —CN, —C(=O)NH$_2$, —C(=O)OH, —C(=O)OC(CH$_3$)$_3$, $R^{2a}$, or $R^{2b}$;

$R^{2a}$ is lower alkyl, phenyl, phenyl lower alkyl, cycloalkyl, heteroaryl, heterocycloalkyl, heterocycloalkyl lower alkyl, heteroaryl lower alkyl, phenyl lower alkoxy, lower alkoxy, optionally substituted with one or more $R^{2a'}$;

each $R^{2a'}$ is independently hydroxy, —CN, amino, lower alkyl sulfonylamino, lower alkoxy, halo, lower alkyl, cyano lower alkyl, lower haloalkyl, lower alkyl sulfonyl, oxo, halo lower alkoxy, cycloalkyl, —C(=O)OCH$_3$;

$R^{2b}$ is —C(O)R$^3$ or —CH$_2$C(=O)R$^3$;

$R^3$ is heterocycloalkyl, optionally substituted with one or more $R^{3'}$;

each $R^{3'}$ is independently —CN, halo, lower alkyl, or lower alkyl sulfonyl;

Q is a 5,6-bicyclic heteroaryl ring system, 6,6-bicyclic heteroaryl ring system, 5,5-bicyclic heteroaryl ring system, 6,5-bicyclic heteroaryl ring system, or 5,7-bicyclic heteroaryl ring system, optionally substituted with one or more $Q^a$ or $Q^b$;

each $Q^a$ is independently halo, —CN, hydroxy, or —(CH$_2$)—C(=O)$Q^{a'}$;

each $Q^{a'}$ is independently hydroxy, amino, or heterocycloalkyl, wherein heterocycloalkyl is optionally substituted by one or more $Q^{a''}$;

each $Q^{a''}$ is independently lower alkyl or lower haloalkyl;

n is 1, 2, or 3;

each $Q^b$ is independently lower alkyl, cycloalkyl, lower alkoxy, phenoxy, lower alkyl sulfonyl, heterocycloalkyl, heterocycloalkyl lower alkyl, or heteroaryl lower alkyl, optionally substituted with one or more $Q^{b'}$; and each $Q^{b'}$ is independently hydroxy, halo, —CN, amino, heterocycloalkyl, lower alkyl, benzyl, or lower alkyl sulfonyl;

or a pharmaceutically acceptable salt thereof.

DETAILED DESCRIPTION OF THE INVENTION

Definitions

The phrase "a" or "an" entity as used herein refers to one or more of that entity; for example, a compound refers to one or more compounds or at least one compound. As such, the terms "a" (or "an"), "one or more", and "at least one" can be used interchangeably herein.

As used in this specification, whether in a transitional phrase or in the body of the claim, the terms "comprise(s)" and "comprising" are to be interpreted as having an open-ended meaning That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or".

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable (e.g., X, X', or Q) occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or "------" drawn through a bond each refer to the point of attachment of a functional group or other chemical moiety to the rest of the molecule of which it is a part. Thus, for example:

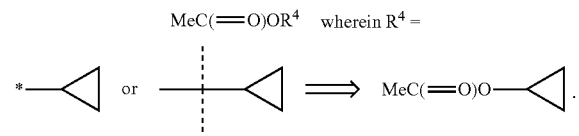

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The phrase "come together to form a bicyclic ring system" as used herein means join to form a bicyclic ring system, wherein each ring may be made up of either 4-7 carbon atoms or 4-7 carbon and heteroatoms, and may be saturated or unsaturated.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

The definitions described herein may be appended to form chemically-relevant combinations, such as "heteroalkylaryl," "haloalkylheteroaryl," "arylalkylheterocyclyl," "alkylcarbonyl," "alkoxyalkyl," "cycloalkylalkyl" and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (het)aryl refers to either an aryl or a heteroaryl group.

Compounds of formula I may exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH-Δ-C(—OH)=CH—), amide/imidic acid (—C(=O)—NH-Δ-C(—OH)=N—) and amidine (—C(=NR)—NH-Δ-C(—NHR)=N—) tautomers. The latter two are particularly common in heteroaryl and heterocyclic rings and the present invention encompasses all tautomeric forms of the compounds.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, 10$^{th}$ Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

The term "acyl" as used herein denotes a group of formula —C(=O)R wherein R is hydrogen or lower alkyl as defined herein. The term or "alkylcarbonyl" as used herein denotes a group of formula C(=O)R wherein R is alkyl as defined herein. The term $C_{1-6}$ acyl refers to a group —C(=O)R contain 6 carbon atoms. The term "arylcarbonyl" as used herein means a group of formula C(=O)R wherein R is an aryl group; the term "benzoyl" as used herein an "arylcarbonyl" group wherein R is phenyl.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl, and are optionally fully or partially deuterated.

When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" denotes the radical R'R"—, wherein R' is a phenyl radical, and R" is an alkylene radical as defined herein with the understanding that the attachment point of the phenylalkyl moiety will be on the alkylene radical. Examples of arylalkyl radicals include, but are not limited to, benzyl, phenylethyl, 3-phenylpropyl. The terms "arylalkyl", "aryl alkyl", or "aralkyl" are interpreted similarly except R' is an aryl radical. The terms "heteroaryl alkyl" or "heteroarylalkyl" are interpreted similarly except R' is optionally an aryl or a heteroaryl radical.

The term "haloalkyl" as used herein denotes a unbranched or branched chain alkyl group as defined above wherein 1, 2, 3 or more hydrogen atoms are substituted by a halogen. The term "lower haloalkyl" denotes a straight or branched chain hydrocarbon residue containing 1 to 6 carbon atoms, wherein 1, 2, 3 or more hydrogen atoms are substituted by a halogen. Examples are 1-fluoromethyl, 1-chloromethyl, 1-bromomethyl, 1-iodomethyl, difluoromethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-dichloroethyl, 3-bromopropyl or 2,2,2-trifluoroethyl.

The term "alkylene" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe- or —CH$_2$CH (i-Pr)CH$_2$—), unless otherwise indicated. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined, and are optionally fully or partially deuterated.

The term "hydroxyalkyl" as used herein denotes an alkyl radical as herein defined wherein one to three hydrogen atoms on different carbon atoms is/are replaced by hydroxyl groups.

The term "cycloalkyl" as used herein refers to a saturated carbocyclic ring containing 3 to 8 carbon atoms, i.e. cyclopropyl, cyclobutyl, cyclopentyl, cyclohexyl, cycloheptyl or cyclooctyl. "$C_{3-7}$ cycloalkyl" as used herein refers to an cycloalkyl composed of 3 to 7 carbons in the carbocyclic ring.

The term "cycloalkenyl" refers to a partially unsaturated carbocyclic containing 5 to 7 carbon atoms unless otherwise specified and having a carbon-carbon double bond within the ring. For example, $C_{5-6}$ cycloalkenyl refers to a cycloalkenyl group having from 5 to 6 member atoms. In certain embodiments cycloalkenyl groups have one carbon-carbon double bond within the ring. In other embodiments, cycloalkenyl groups have more than one carbon-carbon double bond within the ring. However, cycloalkenyl rings are not aromatic. Cycloalkenyl groups may be optionally substituted with one or more substituent. Examples of cycloalkenyl include, but are not limited to, cyclopentenyl and cyclohexenyl.

The term "halogen" or "halo" as used herein means fluorine, chlorine, bromine, or iodine. The term "amino" as used herein encompasses —NR$_2$, wherein each R group is independently H or lower alky, wherein lower alkyl is as defined herein. Examples of amino groups include dimethylamino, methylamino and NH$_2$.

As used herein, the term "aryl" means a monocyclic or bicyclic (also referred to as "biaryl"), substituted or unsubstituted carbocyclic aromatic group. Examples of aryl groups are phenyl, naphthyl and the like.

The term "heteroaryl" as used herein means a monocyclic, bicyclic, or tricyclic radical of 5 to 18 ring atoms having at least one aromatic ring containing four to eight atoms per ring, incorporating one or more N, O, or S heteroatoms, the remaining ring atoms being carbon, with the understanding that the attachment point of the heteroaryl radical will be on an aromatic ring. As well known to those skilled in the art, heteroaryl rings have less aromatic character than their all-carbon counter parts. Thus, for the purposes of the invention, a heteroaryl group need only have some degree of aromatic character. Examples of heteroaryl moieties include monocyclic aromatic heterocycles having 5 to 6 ring atoms and 1 to 3 heteroatoms include, but is not limited to, pyridinyl, pyrimidinyl, pyrazinyl, pyrrolyl, pyrazolyl, imidazolyl, indolyl oxazol, isoxazole, thiazole, isothiazole, triazoline, triazolyl, thiophenyl, furanyl, thiadiazole and oxadiaxoline which can optionally be substituted with one or more, preferably one or two substituents selected from hydroxy, cyano, alkyl, alkoxy, thio, lower haloalkoxy, alkylthio, halo, haloalkyl, alkylsulfinyl, alkylsulfonyl, halogen, amino, alkylamino, dialkylamino, aminoalkyl, alkylaminoalkyl, and dialkylaminoalkyl, nitro, alkoxycarbonyl and carbamoyl, alkylcarbamoyl, dialkylcarbamoyl, arylcarbamoyl, alkylcarbonylamino and arylcarbonylamino. Examples of bicyclic moieties include, but are not limited to, quinolinyl, indazolyl, isoquinolinyl, benzofuryl, benzothiophenyl, benzoxazole, benzisoxazole, benzothiazole, pyrrolopyridinyl, pyrrolopyrazinyl and benzisothiazole.

The term "5,6-bicyclic heteroaryl ring system" as used herein denotes a partially saturated or unsaturated 5,6-bicyclic ring system containing at least one N, O, or S heteroatom, the remaining ring atoms being carbon, with the understanding that the attachment point of the heteroaryl ring system will be on the 5-membered ring. Examples include, but are not limited to: 1H-indazol-3-yl, 4,5,6,7-tetrahydro-1H-indazol-3-yl, 1H-indol-3-yl, 5,6,7,8-Tetrahydro-imidazo[1,5-a]pyridin-1-yl, imidazo[1,5-a]pyridin-1-yl, indazol-1-yl, 1H-pyrazolo[3,4-b]pyridin-3-yl, 1H-pyrazolo[4,3-b]pyridin-3-yl, imidazo[1,2-a]pyridin-3-yl, 2-oxy-4,5,6,7-tetrahydro-1H-indazol-3-yl and benzoimidazol-1-yl, each of which may be optionally substituted.

The term "6,6-bicyclic heteroaryl ring system" as used herein denotes a partially saturated or unsaturated 6,6-bicyclic ring system containing at least one N, O, or S heteroatom, the remaining ring atoms being carbon, with the understanding that the attachment point of the heteroaryl ring system will be on a 6-membered ring containing at least one N, O, or S heteroatom. Examples include, but are not limited to: isoquinolin-1-yl and isoquinolin-8-yl, each of which may be optionally substituted.

The term "5,5-bicyclic heteroaryl ring system" as used herein denotes a partially saturated or unsaturated bicyclic ring system containing at least one N, O, or S heteroatom, the remaining ring atoms being carbon, with the understanding that the attachment point of the heteroaryl ring system will be on a 5-membered ring containing at least one N, O, or S heteroatom. Examples include, but are not limited to: 1H-thieno[3,2-c]pyrazol-3-yl, 1,4,5,6-tetrahydro-cyclopentapyrazol-3-yl, and 5,6-dihydro-4H-cyclopentapyrazol-1-yl, each of which may be optionally substituted.

The term "5,7-bicyclic heteroaryl ring system" as used herein denotes a partially saturated or unsaturated bicyclic ring system containing at least one N, O, or S heteroatom, the remaining ring atoms being carbon, with the understanding that the attachment point of the heteroaryl ring system will be on a 5-membered ring containing at least one N, O, or S heteroatom. Examples include, but are not limited to: 1,4,5,6,7,8-hexahydro-cycloheptapyrazol-3-yl, each of which may be optionally substituted.

The term "6,5-bicyclic heteroaryl ring system" as used herein denotes a partially saturated or unsaturated 6,5-bicyclic ring system containing at least one N, O, or S heteroatom, the remaining ring atoms being carbon, with the understanding that the attachment point of the heteroaryl ring system will be on the 6-membered ring, which optionally contains one or more N, O, or S heteroatoms. Examples include, but are not limited to: 1H-indol-7-yl, 1H-pyrrolo[2,3-c]pyridin-7-yl, 1H-indazol-4-yl, and 1H-indazol-7-yl, each of which may be optionally substituted.

The term "heterocycloalkyl", "heterocyclyl" or "heterocycle" as used herein denotes a monovalent saturated cyclic radical, consisting of one or more rings, preferably one to two rings or three rings, of three to eight atoms per ring, incorporating one or more ring carbon atoms and one or more ring heteroatoms (chosen from N, O or $S(=O)_{0-2}$), wherein the point of attachment can be through either a carbon atom or a heteroatom, and which can optionally be independently substituted with one or more, preferably one or two or three substituents selected from hydroxy, oxo, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, unless otherwise indicated. Examples of heterocyclic radicals include, but are not limited to, azetidinyl, pyrrolidinyl, hexahydroazepinyl, oxetanyl, tetrahydrofuranyl, tetrahydrothiophenyl, oxazolidinyl, thiazolidinyl, isoxazolidinyl, pyrrolidinyl, morpholinyl, piperazinyl, piperidinyl, isoindolinyl, dihydroisoquinolinyle, tetrahydropyranyl, tetrahydrocarbolinyl, imidazolinyl, thiomorpholinyl, quinuclidinyl and imidazolinyl.

The phrase "organ rejection" includes acute allograft or xenograft rejection and chronic allograft or xenograft rejection in the setting of vascularized and/or non-vascularized (e.g. bone marrow, pancreatic islet cells) transplants.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Inhibitors of JAK3 and/or SYK

The application provides a compound of Formula I
A compound of Formula I

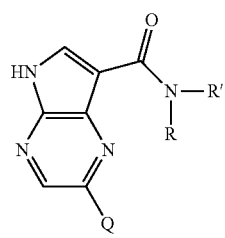

wherein:
R is H;
R' is lower alkoxy or

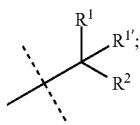

or R and R' together form heterocycloalkyl, optionally substituted with —CN;
$R^1$ is H or $R^{1a}$;
$R^{1a}$ is lower alkyl, cycloalkyl, lower alkoxyl, hydroxy lower alkyl, or lower haloalkyl;
$R^{1'}$ is H or lower alkyl;
or $R^{1a}$ and $R^{1'}$ together form heterocycloalkyl, cycloalkyl, indan-1-yl, phenyl, or heteroaryl, optionally substituted with one or more $R^{1''}$;
each $R^{1''}$ is independently hydroxy, amino, oxo, lower alkyl, —C(=O)NH$_2$, —CN, lower haloalkyl, benzyl, cyano lower alkyl, or —NHC(=O)OC(CH$_3$)$_3$;
$R^2$ is H, hydroxy, —CN, —C(=O)NH$_2$, —C(=O)OH, —C(=O)OC(CH$_3$)$_3$, $R^{2a}$, or $R^{2b}$;
$R^{2a}$ is lower alkyl, phenyl, phenyl lower alkyl, cycloalkyl, heteroaryl, heterocycloalkyl, heterocycloalkyl lower alkyl, heteroaryl lower alkyl, phenyl lower alkoxy, lower alkoxy, optionally substituted with one or more $R^{2a'}$;
each $R^{2a'}$ is independently hydroxy, —CN, amino, lower alkyl sulfonylamino, lower alkoxy, halo, lower alkyl, cyano lower alkyl, lower haloalkyl, lower alkyl sulfonyl, oxo, halo lower alkoxy, cycloalkyl, —C(=O)OCH$_3$;
$R^{2b}$ is C(O)$R^3$ or —CH$_2$C(=O)$R^3$;
$R^3$ is heterocycloalkyl, optionally substituted with one or more $R^{3'}$;
each $R^{3'}$ is independently —CN, halo, lower alkyl, or lower alkyl sulfonyl;
Q is a 5,6-bicyclic heteroaryl ring system, 6,6-bicyclic heteroaryl ring system, 5,5-bicyclic heteroaryl ring system, 6,5-bicyclic heteroaryl ring system, or 5,7-bicyclic heteroaryl ring system, optionally substituted with one or more $Q^a$ or $Q^b$;

each $Q^a$ is independently halo, —CN, hydroxy, or —(CH$_2$)—C(=O)$Q^{a'}$;
each $Q^{a'}$ is independently hydroxy, amino, or heterocycloalkyl, wherein heterocycloalkyl is optionally substituted by one or more $Q^{a''}$;
each $Q^{a''}$ is independently lower alkyl or lower haloalkyl;
n is 1, 2, or 3;
each $Q^b$ is independently lower alkyl, cycloalkyl, lower alkoxy, phenoxy, lower alkyl sulfonyl, heterocycloalkyl, heterocycloalkyl lower alkyl, or heteroaryl lower alkyl, optionally substituted with one or more $Q^{b'}$; and
each $Q^{b'}$ is independently hydroxy, halo, —CN, amino, heterocycloalkyl, lower alkyl, benzyl, or lower alkyl sulfonyl;
or a pharmaceutically acceptable salt thereof.

The application provides the compound of Formula I, wherein R is H.

The application provides the compound of Formula I, wherein R' is

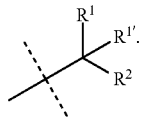

The application provides the compound of Formula I, wherein R is H and R' is

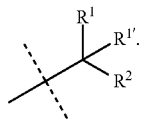

The application provides the compound of Formula I, wherein $R^{1'}$ is H or lower alkyl.

The application provides the compound of Formula I, wherein $R^{1'}$ is H or lower alkyl R is H, and R' is

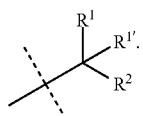

The application provides the compound of Formula I, wherein $R^1$ is lower alkyl.

The application provides the compound of Formula I, wherein $R^1$ is lower alkyl, $R^{1'}$ is H or lower alkyl, R is H, and R' is

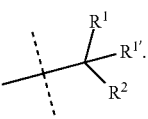

The application provides the compound of Formula I, wherein both $R^1$ and $R^{1'}$ are H.

The application provides the compound of Formula I, wherein R is H, R' is

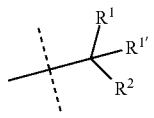

and both $R^1$ and $R^{1'}$ are H.

The application provides the compound of Formula I, wherein $R^2$ is —C(=O)$R^3$.

The application provides the compound of Formula I, wherein $R^2$ is —C(=O)$R^3$, $R^1$ is lower alkyl, $R^{1'}$ is H or lower alkyl, R is H, and R' is

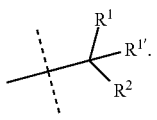

The application provides the compound of Formula I, wherein $R^2$ is lower alkyl, optionally substituted with one or more $R^{2a'}$.

The application provides the compound of Formula I, wherein $R^2$ is lower alkyl, optionally substituted with one or more $R^{2a'}$, $R^1$ is lower alkyl, $R^{1'}$ is H or lower alkyl, R is H, and R' is

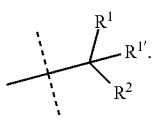

The application provides the compound of Formula I, wherein Q is a 5,6-bicyclic heteroaryl ring system, optionally substituted with one or more $Q^a$ or $Q^b$.

The application provides the compound of Formula I, wherein Q is a 5,6-bicyclic heteroaryl ring system, optionally substituted with one or more $Q^a$ or $Q^b$, $R^2$ is lower alkyl, optionally substituted with one or more $R^{2a'}$, $R^1$ is lower alkyl, $R^{1'}$ is H or lower alkyl, R is H, and R' is

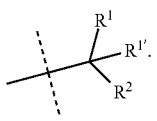

The application provides the compound of Formula I, wherein Q is indazol-3-yl, optionally substituted with one or more $Q^a$ or $Q^b$.

The application provides the compound of Formula I, wherein $Q^a$ is halo or lower alkyl.

The application provides the compound of Formula I, wherein Q is indazol-3-yl, optionally substituted with one or more $Q^a$ or $Q^b$, and $Q^a$ is halo or lower alkyl.

The application provides the compound of Formula I, wherein $Q^b$ is lower alkyl.

The application provides the compound of Formula I, wherein Q is indazol-3-yl, optionally substituted with one or more $Q^a$ or $Q^b$, and $Q^a$ is halo or lower alkyl, and $Q^b$ is lower alkyl.

The application provides the compound of Formula I, wherein $R^{1a}$ and $R^{1'}$ together form heterocycloalkyl or cycloalkyl, optionally substituted with one or more $R^{1''}$.

The application provides the compound of Formula I, wherein $R^{1a}$ and $R^{1'}$ together form heterocycloalkyl or cycloalkyl, optionally substituted with one or more $R^{1''}$, Q is indazol-3-yl, optionally substituted with one or more $Q^a$ or $Q^b$, and $Q^a$ is halo or lower alkyl, and $Q^b$ is lower alkyl.

The application provides the compound of Formula I, wherein $R^{1''}$ is amino or —CN.

The application provides the compound of Formula I, wherein $R^{1''}$ is amino or —CN, $R^{1a}$ and $R^{1'}$ together form heterocycloalkyl or cycloalkyl, optionally substituted with one or more $R^{1''}$, Q is indazol-3-yl, optionally substituted with one or more $Q^a$ or $Q^b$, and $Q^a$ is halo or lower alkyl, and $Q^b$ is lower alkyl.

The application provides the compound of Formula I, wherein $R^2$ is lower alkyl.

The application provides the compound of Formula I, wherein $R^2$ is lower alkyl, $R^{1''}$ is amino or —CN, $R^{1a}$ and $R^{1'}$ together form heterocycloalkyl or cycloalkyl, optionally substituted with one or more $R^{1''}$, Q is indazol-3-yl, optionally substituted with one or more $Q^a$ or $Q^b$, and $Q^a$ is halo or lower alkyl, and $Q^b$ is lower alkyl.

The application provides a compound selected from the compounds listed in Table I.

The application provides a method for treating an inflammatory or autoimmune condition comprising administering to a patient in need thereof a therapeutically effective amount of the compound of Formula I.

The application provides the above method, further comprising administering an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, or an agent for treating immunodeficiency disorders.

The application provides a method for treating rheumatoid arthritis comprising administering to a patient in need thereof a therapeutically effective amount of the compound of Formula I.

The application provides a method for treating asthma comprising administering to a patient in need thereof a therapeutically effective amount of the compound of Formula I.

The application provides a method for treating an inflammatory condition comprising administering to a patient in need thereof a therapeutically effective amount of the compound of Formula I.

The application provides a method for inhibiting T-cell proliferative disorder comprising administering to a patient in need thereof a therapeutically effective amount of the compound of Formula I.

The application provides a method for inhibiting T-cell proliferative disorder comprising administering to a patient in need thereof a therapeutically effective amount of the compound of Formula I The application provides the above method, wherein the proliferative disorder is cancer.

The application provides a method for treating a B-cell proliferative disorder comprising administering to a patient in need thereof a therapeutically effective amount of the compound of Formula I.

The application provides a method for treating an immune disorder including lupus, multiple sclerosis, rheumatoid arthritis, psoriasis, Type I diabetes, complications from organ transplants, xeno transplantation, diabetes, cancer, asthma, atopic dermatitis, autoimmune thyroid disorders, ulcerative colitis, Crohn's disease, Alzheimer's disease, and Leukemia, comprising administering to a patient in need thereof a therapeutically effective amount of the compound of Formula I.

The application provides a method for preventing or treating all forms of organ rejection, including acute allograft or xenograft rejection and chronic allograft or xenograft rejection, of vascularized or non-vascularized transplants, comprising administering to a patient in need thereof the compound of Formula I.

The application provides a method for inhibiting JAK3 activity comprising administering the compound of Formula I, wherein the compound exhibits an $IC_{50}$ of 50 micromolar or less in an in vitro biochemical assay of JAK3 activity.

The application provides the above method, wherein the compound exhibits an $IC_{50}$ of 100 nanomolar or less in an in vitro biochemical assay of JAK3 activity.

The application provides the above method, wherein the compound exhibits an $IC_{50}$ of 10 nanomolar or less in an in vitro biochemical assay of JAK3 activity.

A method for inhibiting SYK activity comprising administering the compound of Formula I, wherein the compound exhibits an $IC_{50}$ of 50 micromolar or less in an in vitro biochemical assay of SYK activity.

The application provides the above method, wherein the compound exhibits an $IC_{50}$ of 100 nanomolar or less in an in vitro biochemical assay of SYK activity.

The application provides the above method, wherein the compound exhibits an $IC_{50}$ of 10 nanomolar or less in an in vitro biochemical assay of SYK activity.

The application provides a method for treating an inflammatory condition comprising co-administering to a patient in need thereof a therapeutically effective amount of an anti-inflammatory compound in combination with the compound of Formula I.

The application provides a method for treating an immune disorder comprising co-administering to a patient in need thereof a therapeutically effective amount of an immunosuppressant compound in combination with the compound of Formula I.

The application provides a pharmaceutical composition comprising the compound of Formula I, admixed with at least one pharmaceutically acceptable carrier, excipient or diluent.

The application provides the above composition, further comprising an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, and an agent for treating immunodeficiency disorders.

The application provides a process for preparing the compound of Formula I.

The application provides the use of the compound of Formula I in the manufacture of a medicament for the treatment of an inflammatory disorder.

The application provides the use of the compound of Formula I in the manufacture of a medicament for the treatment of an autoimmune disorder.

The application provides the use of the compound of any one of claims 1-15 in the preparation of a medicament for the treatment of arthritis or asthma.

The application provides the invention as hereinbefore described.

Compounds

Examples of representative compounds encompassed by the present invention and within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

In general, the nomenclature used in this application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE I depicts exemplified compounds according to Formula I.

TABLE I

| COMPOUND | STRUCTURE | SYSTEMATIC NAME |
|---|---|---|
| I-1 | 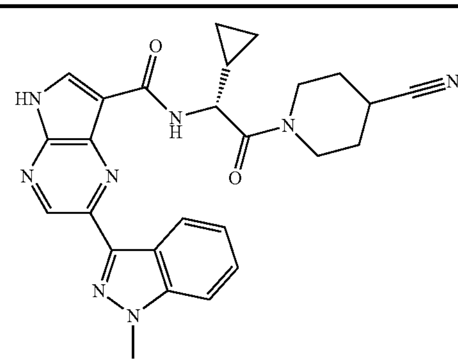 | 2-(1-Methyl-1H-indazol-3-yl-5H-pyrrolo[2,3-b]pyrazine-7-carboxylic acid [(R)-2-(4-cyano-piperidin-1-yl)-1-cyclopropyl-2-oxo-ethyl]-amide |

TABLE I-continued

| COMPOUND | STRUCTURE | SYSTEMATIC NAME |
|---|---|---|
| I-2 | 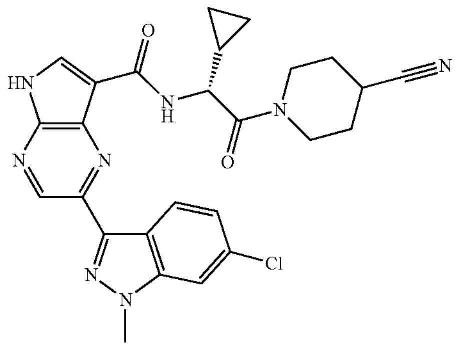 [SMILES: Cn1nc(-c2cnc3[nH]cc(C(=O)N[C@@H](C(=O)N4CCC(C#N)CC4)C4CC4)c3n2)c2ccc(Cl)cc21] | 2-(6-Chloro-1-methyl-1H-indazol-3-yl)-5H-pyrrolo[2,3-b]pyrazine-7-carboxylic acid [(R)-2-(4-cyano-piperidin-1-yl)-1-cyclopropyl-2-oxo-ethyl]-amide |
| I-3 | 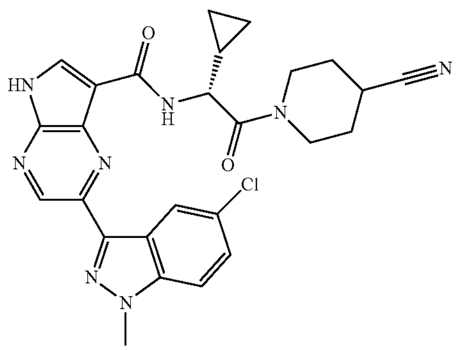 [SMILES: Cn1nc(-c2cnc3[nH]cc(C(=O)N[C@@H](C(=O)N4CCC(C#N)CC4)C4CC4)c3n2)c2cc(Cl)ccc21] | 2-(5-Chloro-1-methyl-1H-indazol-3-yl)-5H-pyrrolo[2,3-b]pyrazine-7-carboxylic acid [(R)-2-(4-cyano-piperidin-1-yl)-1-cyclopropyl-2-oxo-ethyl]-amide |
| I-4 | 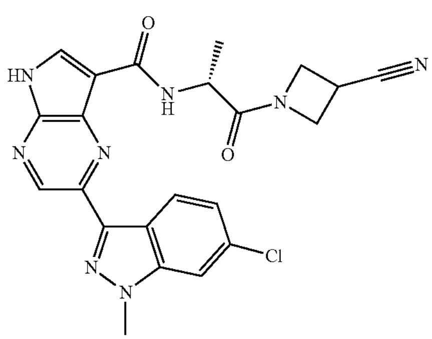 [SMILES: C[C@@H](NC(=O)c1c[nH]c2ncc(-c3nn(C)c4cc(Cl)ccc34)nc12)C(=O)N1CC(C#N)C1] | 2-(6-Chloro-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide |
| I-5 | 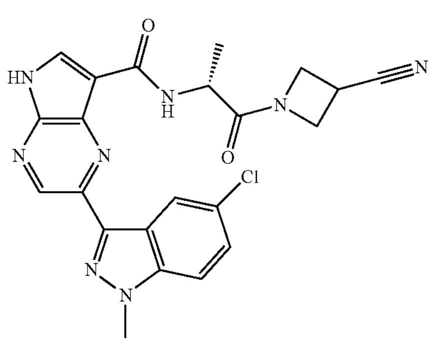 [SMILES: C[C@@H](NC(=O)c1c[nH]c2ncc(-c3nn(C)c4ccc(Cl)cc34)nc12)C(=O)N1CC(C#N)C1] | 2-(5-Chloro-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide |

TABLE I-continued

| COMPOUND | STRUCTURE | SYSTEMATIC NAME |
| --- | --- | --- |
| I-6 | 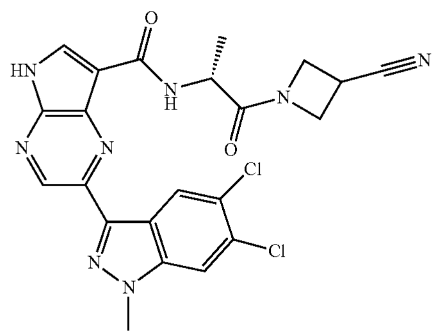 | 2-(5,6-Dichloro-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide |
| I-7 | 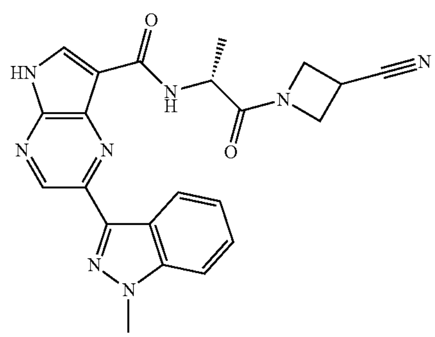 [SMILES: C[C@@H](NC(=O)c1c[nH]c2ncc(-c3nn(C)c4ccccc34)nc12)C(=O)N1CC(C#N)C1] | 2-(1-Methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide |
| I-8 | 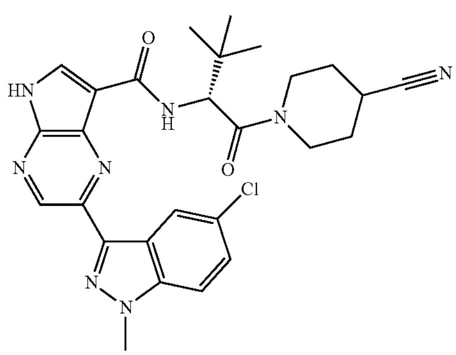 [SMILES: Cn1nc(-c2cnc3[nH]cc(C(=O)N[C@@H](C(=O)N4CCC(C#N)CC4)C(C)(C)C)c3n2)c2cc(Cl)ccc21] | 2-(5-Chloro-1-methyl-1H-indazol-3-yl)-5H-pyrrolo[2,3-b]pyrazine-7-carboxylic acid [(R)-1-(4-cyano-piperidine-1-carbonyl)-2,2-dimethyl-propyl]-amide |
| I-9 | 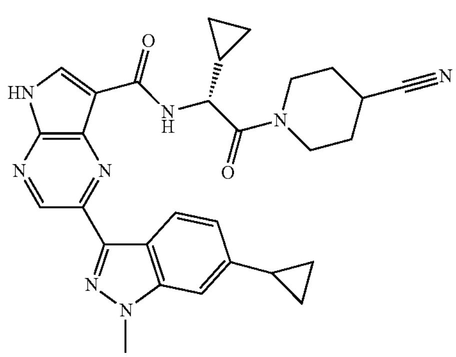 [SMILES: Cn1nc(-c2cnc3[nH]cc(C(=O)N[C@@H](C(=O)N4CCC(C#N)CC4)C4CC4)c3n2)c2ccc(C3CC3)cc21] | 2-(6-Cyclopropyl-1-methyl-1H-indazol-3-yl)-5H-pyrrolo[2,3-b]pyrazine-7-carboxylic acid [(R)-2-(4-cyano-piperidin-1-yl)-1-cyclopropyl-2-oxo-ethyl]-amide |

TABLE I-continued

| COMPOUND | STRUCTURE | SYSTEMATIC NAME |
|---|---|---|
| I-10 | 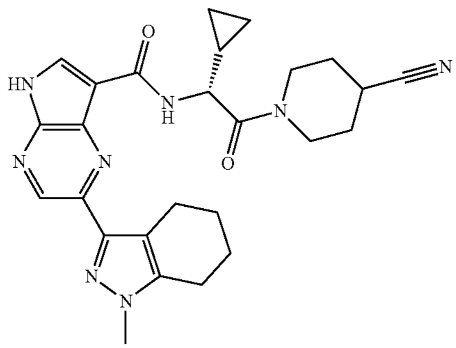 [SMILES: Cn1nc(-c2cnc3[nH]cc(C(=O)N[C@@H](C(=O)N4CCC(C#N)CC4)C4CC4)c3n2)c2c1CCCC2] | 2-(1-Methyl-4,5,6,7-tetrahydro-1H-indazol-3-yl)-5H-pyrrolo[2,3-b]pyrazine-7-carboxylic acid [(R)-2-(4-cyano-piperidin-1-yl)-1-cyclopropyl-2-oxo-ethyl]-amide |
| I-11 | 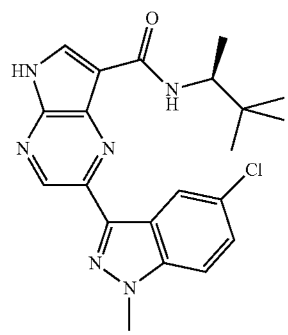 [SMILES: C[C@H](NC(=O)c1c[nH]c2ncc(-c3nn(C)c4ccc(Cl)cc34)nc12)C(C)(C)C] | 2-(5-Chloro-1-methyl-1H-indazol-3-yl)-5H-pyrrolo[2,3-b]pyrazine-7-carboxylic acid ((S)-1,2,2-trimethyl-propyl)-amide |
| I-12 | 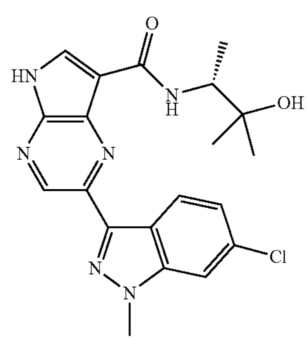 [SMILES: C[C@@H](NC(=O)c1c[nH]c2ncc(-c3nn(C)c4cc(Cl)ccc34)nc12)C(C)(C)O] | 2-(6-Chloro-1-methyl-1H-indazol-3-yl)-5H-pyrrolo[2,3-b]pyrazine-7-carboxylic acid ((R)-2-hydroxy-1,2-dimethyl-propyl)-amide |
| I-13 | 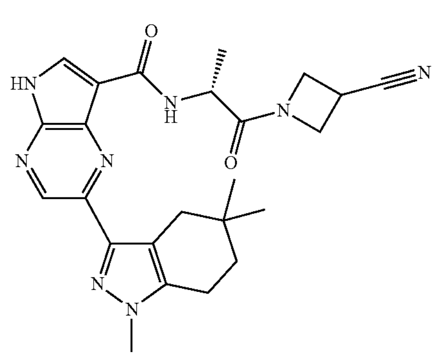 [SMILES: C[C@@H](NC(=O)c1c[nH]c2ncc(-c3nn(C)c4c3CC(C)(C)CC4)nc12)C(=O)N1CC(C#N)C1] | 2-(1,5,5-Trimethyl-4,5,6,7-tetrahydro-1H-indazol-3-yl)-5H-pyrrolo[2,3-b]pyrazine-7-carboxylic acid [(R-2-(3-cyano-azetidin-1-yl)-1-methyl-2-oxo-ethyl]-amide |

TABLE I-continued

| COMPOUND | STRUCTURE | SYSTEMATIC NAME |
|---|---|---|
| I-14 | 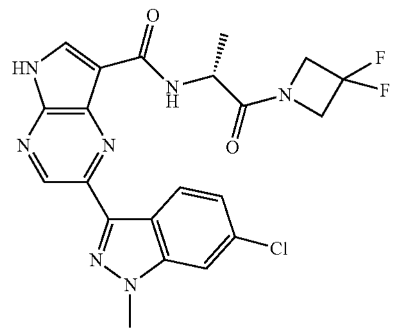 [SMILES: C[C@@H](NC(=O)c1c[nH]c2ncc(-c3nn(C)c4cc(Cl)ccc34)nc12)C(=O)N1CC(F)(F)C1] | 2-(6-Chloro-1-methyl-1H-indazol-3-yl)-5H-pyrrolo[2,3-b]pyrazine-7-carboxylic acid [(R)-2-(3,3-difluoro-azetidin-1-yl)-1-methyl-2-oxo-ethyl]-amide |
| I-15 | 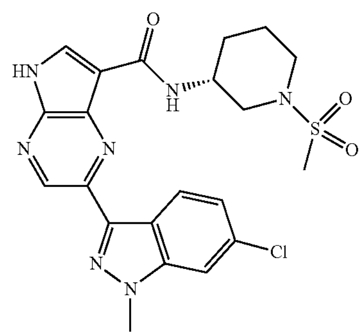 [SMILES: Cn1nc(-c2cnc3[nH]cc(C(=O)N[C@@H]4CCCN(S(C)(=O)=O)C4)c3n2)c2ccc(Cl)cc21] | 2-(6-Chloro-1-methyl-1H-indazol-3-yl)-5H-pyrrolo[2,3-b]pyrazine-7-carboxylic acid ((R)-1-methanesulfonyl-piperidin-3-yl)-amide |
| I-16 | 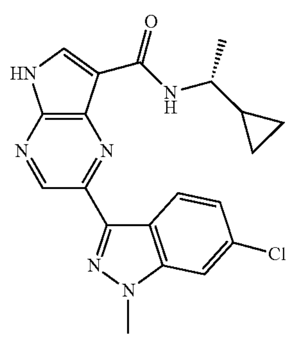 [SMILES: C[C@@H](NC(=O)c1c[nH]c2ncc(-c3nn(C)c4cc(Cl)ccc34)nc12)C1CC1] | 2-(6-Chloro-1-methyl-1H-indazol-3-yl)-5H-pyrrolo[2,3-b]pyrazine-7-carboxylic acid ((R)-1-cyclopropyl-ethyl)-amide |
| I-17 | 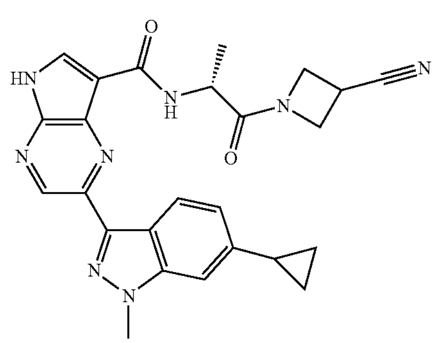 [SMILES: C[C@@H](NC(=O)c1c[nH]c2ncc(-c3nn(C)c4cc(C5CC5)ccc34)nc12)C(=O)N1CC(C#N)C1] | 2-(6-Cyclopropyl-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide |

TABLE I-continued

| COMPOUND | STRUCTURE | SYSTEMATIC NAME |
|---|---|---|
| I-18 | 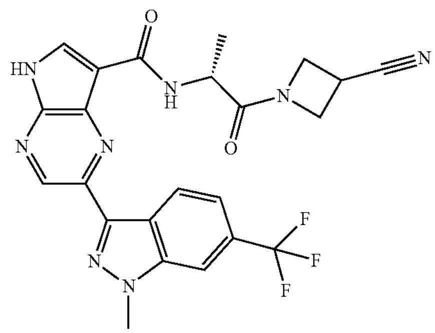 [SMILES: C[C@@H](NC(=O)c1c[nH]c2ncc(-c3nn(C)c4cc(C(F)(F)F)ccc34)nc12)C(=O)N1CC(C#N)C1] | 2-(1-Methyl-6-trifluoromethyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide |
| I-19 | 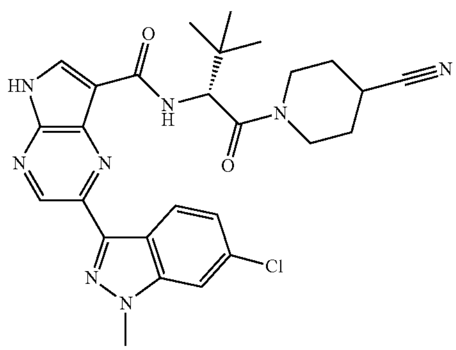 [SMILES: Cn1nc(-c2cnc3[nH]cc(C(=O)N[C@@H](C(=O)N4CCC(C#N)CC4)C(C)(C)C)c3n2)c2ccc(Cl)cc21] | 2-(6-Chloro-1-methyl-1H-indazol-3-yl)-5H-pyrrolo[2,3-b]pyrazine-7-carboxylic acid [(R)-1-(4-cyano-piperidine-1-carbonyl)-2,2-dimethyl-propyl]-amide |
| I-20 | 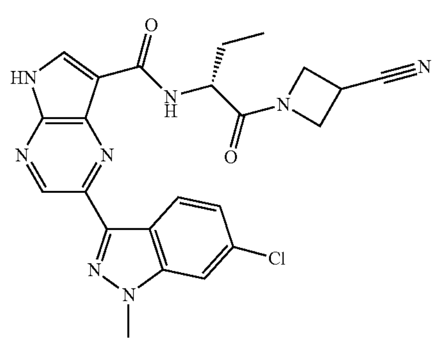 [SMILES: CC[C@@H](NC(=O)c1c[nH]c2ncc(-c3nn(C)c4cc(Cl)ccc34)nc12)C(=O)N1CC(C#N)C1] | 2-(6-Chloro-1-methyl-1H-indazol-3-yl)-5H-pyrrolo[2,3-b]pyrazine-7-carboxylic acid [(R)-1-(3-cyano-azetidine-1-carbonyl)-propyl]-amide |
| I-21 | 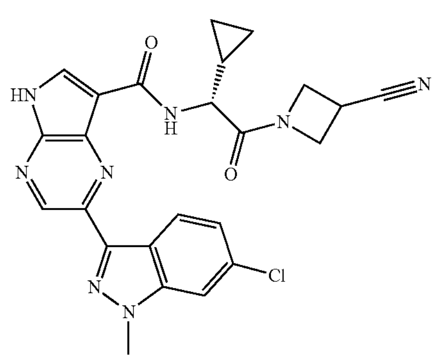 [SMILES: Cn1nc(-c2cnc3[nH]cc(C(=O)N[C@@H](C(=O)N4CC(C#N)C4)C4CC4)c3n2)c2ccc(Cl)cc21] | 2-(6-Chloro-1-methyl-1H-indazol-3-yl)-5H-pyrrolo[2,3-b]pyrazine-7-carboxylic acid [(R)-2-(3-cyano-azetidin-1-yl)-1-cyclopropyl-2-oxo-ethyl]-amide |

TABLE I-continued

| COMPOUND | STRUCTURE | SYSTEMATIC NAME |
|---|---|---|
| I-22 | 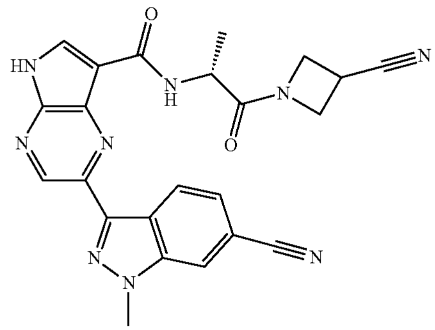 [SMILES: C[C@@H](NC(=O)c1c[nH]c2ncc(-c3nn(C)c4cc(C#N)ccc34)nc12)C(=O)N1CC(C#N)C1] | 2-(6-Cyano-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide |
| I-23 | 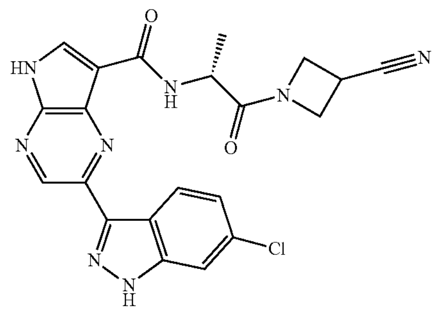 [SMILES: C[C@@H](NC(=O)c1c[nH]c2ncc(-c3n[nH]c4cc(Cl)ccc34)nc12)C(=O)N1CC(C#N)C1] | 2-(6-Chloro-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide |
| I-24 | 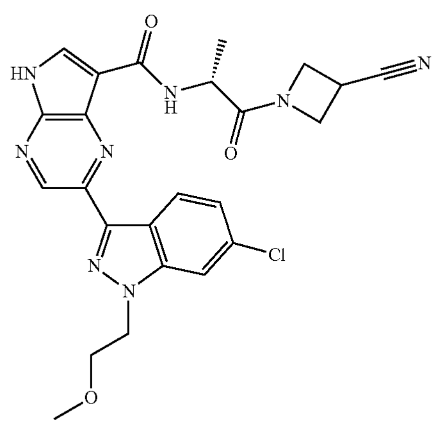 [SMILES: COCCn1nc(-c2cnc3[nH]cc(C(=O)N[C@H](C)C(=O)N4CC(C#N)C4)c3n2)c2ccc(Cl)cc21] | 2-[6-Chloro-1-(2-methoxy-ethyl)-1H-indazol-3-yl]-5H-pyrrolo[2,3-b]pyrazine-7-carboxylic acid [(R)-2-(3-cyano-azetidin-1-yl)-1-methyl-2-oxo-ethyl]-amide |
| I-25 | 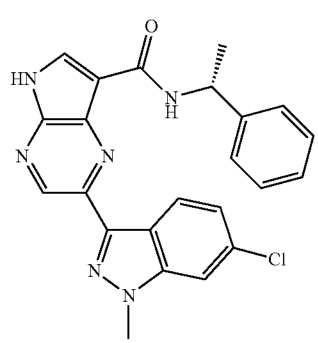 [SMILES: C[C@@H](NC(=O)c1c[nH]c2ncc(-c3nn(C)c4cc(Cl)ccc34)nc12)c1ccccc1] | 2-(6-Chloro-1-methyl-1H-indazol-3-yl)-5H-pyrrolo[2,3-b]pyrazine-7-carboxylic acid ((R)-1-phenyl-ethyl)-amide |

TABLE I-continued

| COMPOUND | STRUCTURE | SYSTEMATIC NAME |
|---|---|---|
| I-26 | 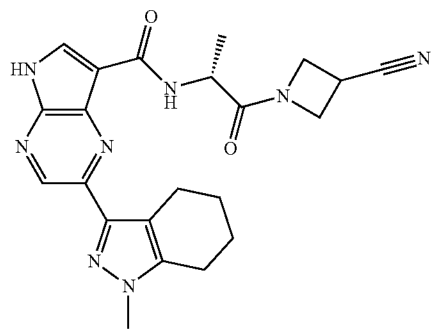 [SMILES: C[C@@H](NC(=O)c1c[nH]c2ncc(-c3nn(C)c4c3CCCC4)nc12)C(=O)N1CC(C#N)C1] | 2-(1-Methyl-4,5,6,7-tetrahydro-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide |
| I-27 | 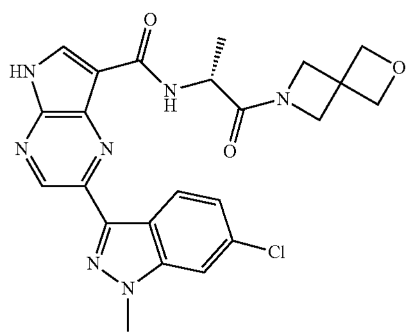 [SMILES: C[C@@H](NC(=O)c1c[nH]c2ncc(-c3nn(C)c4cc(Cl)ccc34)nc12)C(=O)N1CC2(COC2)C1] | 2-(6-Chloro-1-methyl-1H-indazol-3-yl)-5H-pyrrolo[2,3-b]pyrazine-7-carboxylic acid [(R)-1-methyl-2-(2-oxa-6-aza-spiro[3.3]hept-6-yl)-2-oxo-ethyl]-amide |
| I-28 | 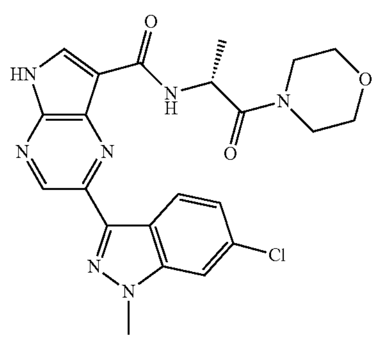 [SMILES: C[C@@H](NC(=O)c1c[nH]c2ncc(-c3nn(C)c4cc(Cl)ccc34)nc12)C(=O)N1CCOCC1] | 2-(6-Chloro-1-methyl-1H-indazol-3-yl)-5H-pyrrolo[2,3-b]pyrazine-7-carboxylic acid ((R)-1-methyl-2-morpholin-4-yl-2-oxo-ethyl)-amide |
| I-29 | 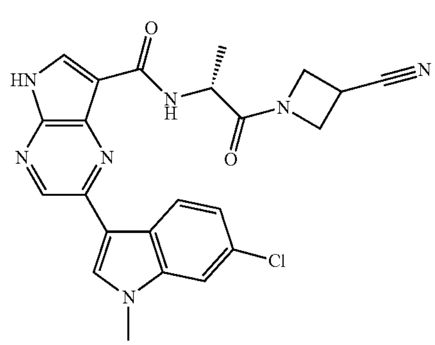 [SMILES: C[C@@H](NC(=O)c1c[nH]c2ncc(-c3cn(C)c4cc(Cl)ccc34)nc12)C(=O)N1CC(C#N)C1] | 2-(6-Chloro-1-methyl-1H-indol-3-yl)-5H-pyrrolo[2,3-b]pyrazine-7-carboxylic acid [(R)-2-(3-cyano-azetidin-1-yl)-1-methyl-2-oxo-ethyl]-amide |

TABLE I-continued

| COMPOUND | STRUCTURE | SYSTEMATIC NAME |
|---|---|---|
| I-30 | 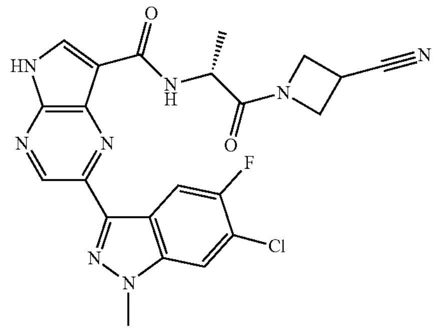 [SMILES: C[C@@H](NC(=O)c1c[nH]c2ncc(-c3nn(C)c4cc(Cl)c(F)cc34)nc12)C(=O)N1CC(C#N)C1] | 2-(6-Chloro-5-fluoro-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide |
| I-31 | 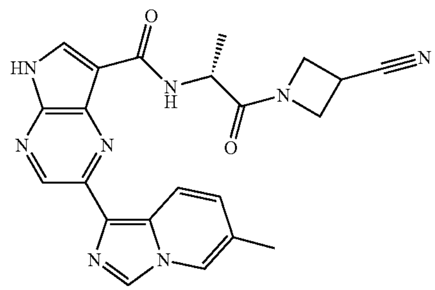 | 2-(6-Methyl-imidazo[1,5-a]pyridin-1-yl)-5H-pyrrolo[2,3-b]pyrazine-7-carboxylic acid [(R)-2-(3-cyano-azetidin-1-yl)-1-methyl-2-oxo-ethyl]-amide |
| I-32 | 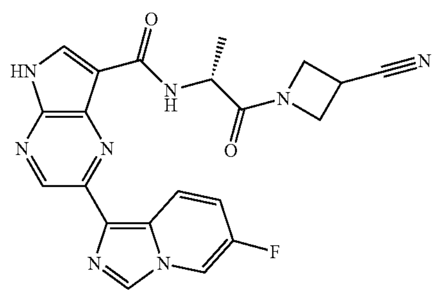 [SMILES: C[C@@H](NC(=O)c1c[nH]c2ncc(-c3ncn4cc(F)ccc34)nc12)C(=O)N1CC(C#N)C1] | 2-(6-Fluoro-imidazo[1,5-a]pyridin-1-yl)-5H-pyrrolo[2,3-b]pyrazine-7-carboxylic acid [(R)-2-(3-cyano-azetidin-1-yl)-1-methyl-2-oxo-ethyl)-amide |
| I-33 | 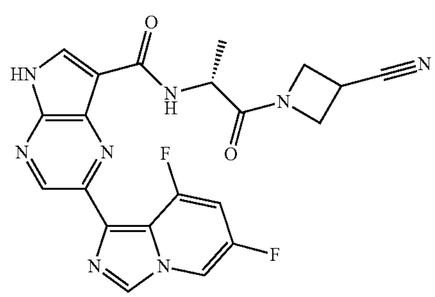 [SMILES: C[C@@H](NC(=O)c1c[nH]c2ncc(-c3ncn4cc(F)cc(F)c34)nc12)C(=O)N1CC(C#N)C1] | 2-(6,8-Difluoro-imidazo[1,5-a]pyridin-1-yl)-5H-pyrrolo[2,3-b]pyrazine-7-carboxylic acid [(R)-2-(3-cyano-azetidin-1-yl)-1-methyl-2-oxo-ethyl]-amide |
| I-34 | 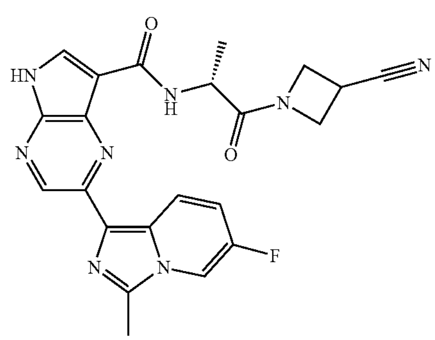 [SMILES: Cc1nc(-c2cnc3[nH]cc(C(=O)N[C@H](C)C(=O)N4CC(C#N)C4)c3n2)c2ccc(F)cn12] | 2-(6-Fluoro-3-methyl-imidazo[1,5-a]pyridin-1-yl)-5H-pyrrolo[2,3-b]pyrazine-7-carboxylic acid [(R)-2-(3-cyano-azetidin-1-yl)-1-methyl-2-oxo-ethyl]-amide |

TABLE I-continued

| COMPOUND | STRUCTURE | SYSTEMATIC NAME |
| --- | --- | --- |
| I-35 | 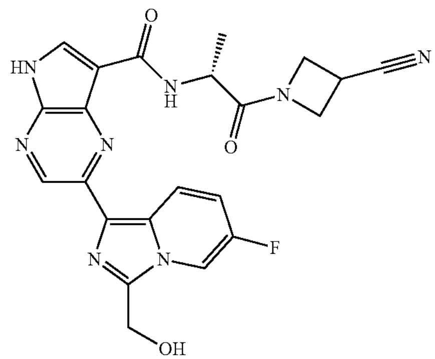 [SMILES: C[C@@H](NC(=O)c1c[nH]c2ncc(-c3nc(CO)n4cc(F)ccc34)nc12)C(=O)N1CC(C#N)C1] | 2-(6-Fluoro-3-hydroxymethyl-imidazo[1,5-a]pyridin-1-yl)-5H-pyrrolo[2,3-b]pyradine-7-carboxylic acid [(R)-2-(3-cyano-azetidin-1-yl)-1-methyl-2-oxo-ethyl]-amide |
| I-36 | 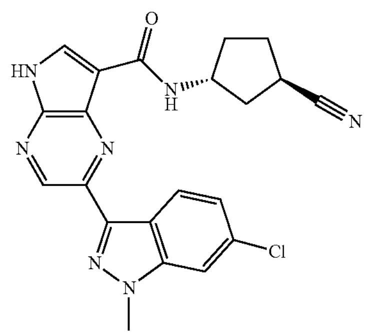 [SMILES: Cn1nc(-c2cnc3[nH]cc(C(=O)N[C@@H]4CC[C@@H](C#N)C4)c3n2)c2ccc(Cl)cc21] | 2-(6-Chloro-1-methyl-1H-indazol-3-yl)-5H-pyrrolo[2,3-b]pyrazine-7-carboxylic acid ((1R,3R)-3-cyano-cyclopentyl)-amide |
| I-37 | 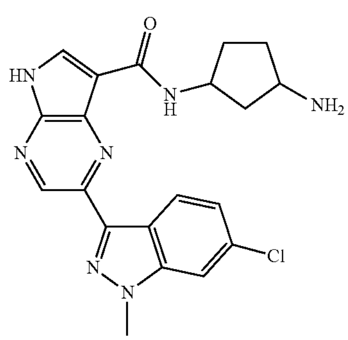 [SMILES: Cn1nc(-c2cnc3[nH]cc(C(=O)NC4CCC(N)C4)c3n2)c2ccc(Cl)cc21] | 2-(6-Chloro-1-methyl-1H-indazol-3-yl)-5H-pyrrolo[2,3-b]pyrazine-7-carboxylic acid (3-amino-cyclopentyl)-amide |
| I-38 | 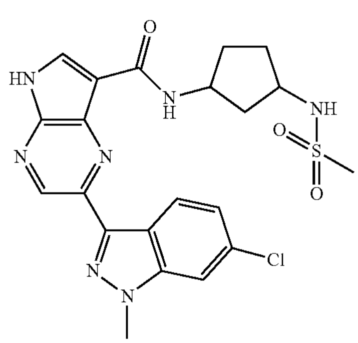 [SMILES: Cn1nc(-c2cnc3[nH]cc(C(=O)NC4CCC(NS(C)(=O)=O)C4)c3n2)c2ccc(Cl)cc21] | 2-(6-Chloro-1-methyl-1H-indazol-3-yl)-5H-pyrrolo[2,3-b]pyrazine-7-carboxylic acid (3-methanesulfonylamino-cyclopentyl)-amide |

TABLE I-continued

| COMPOUND | STRUCTURE | SYSTEMATIC NAME |
| --- | --- | --- |
| I-39 | 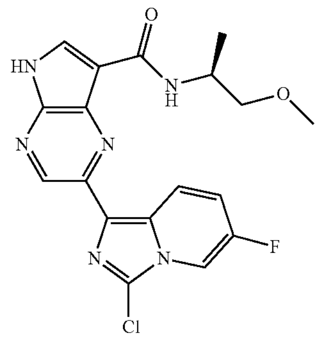 [SMILES: COC[C@H](C)NC(=O)c1c[nH]c2ncc(-c3nc(Cl)n4cc(F)ccc34)nc12] | 2-(3-Chloro-6-fluoro-imidazo[1,5-a]pyridin-1-yl)-5H-pyrrolo[2,3-b]pyrazine-7-carboxylic acid ((S)-2-methoxy-1-methyl-ethyl)-amide |
| I-40 | 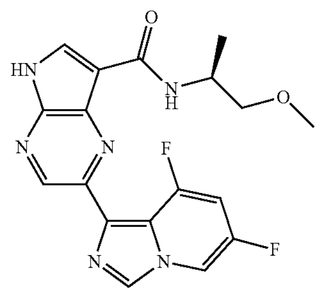 [SMILES: COC[C@H](C)NC(=O)c1c[nH]c2ncc(-c3ncn4cc(F)cc(F)c34)nc12] | 2-(6,8-Difluoro-imidazo[1,5-a]pyridin-1-yl)-5H-pyrrolo[2,3-b]pyradine-7-carboxylic acid ((S)-2-methoxy-1-methyl-ethyl)-amide |
| I-41 | 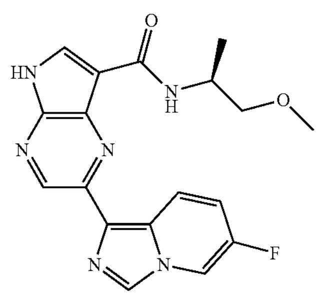 [SMILES: COC[C@H](C)NC(=O)c1c[nH]c2ncc(-c3ncn4cc(F)ccc34)nc12] | 2-(6-Fluoro-imidazo[1,5-a]pyridin-1-yl)-5H-pyrrolo[2,3-b]pyrazine-7-carboxylic acid ((S)-2-methoxy-1-methyl-ethyl)-amide |
| I-42 | 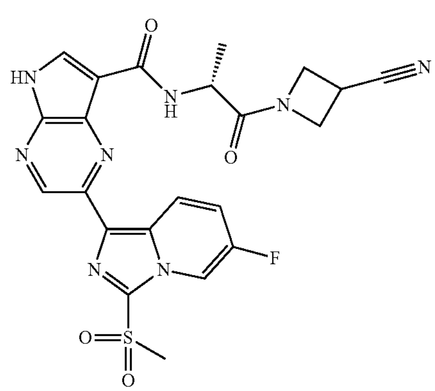 [SMILES: C[C@@H](NC(=O)c1c[nH]c2ncc(-c3nc(S(C)(=O)=O)n4cc(F)ccc34)nc12)C(=O)N1CC(C#N)C1] | 2-(6-Fluoro-3-methanesulfonyl-imidazo[1,5-a]pyridin-1-yl)-5H-pyrrolo[2,3-b]pyrazine-7-carboxylic acid [(R)-2-(3-cyano-azetidin-1-yl)-1-methyl-2-oxo-ethyl]-amide |

TABLE I-continued

| COMPOUND | STRUCTURE | SYSTEMATIC NAME |
| --- | --- | --- |
| I-43 | 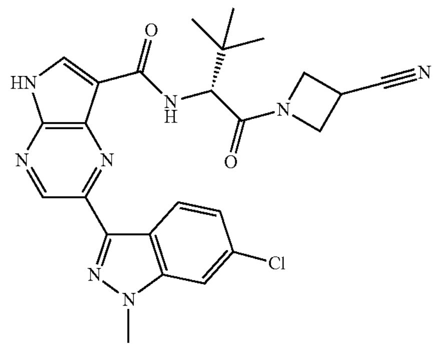 [SMILES: Cn1nc(-c2cnc3[nH]cc(C(=O)N[C@@H](C(=O)N4CC(C#N)C4)C(C)(C)C)c3n2)c2ccc(Cl)cc21] | 2-(6-Chloro-1-methyl-1H-indazol-3-yl)-5H-pyrrolo[2,3-b]pyrazine-7-carboxylic acid [(R)-1-(3-cyano-azetidine-1-carbonyl)-2,2-dimethyl-propyl]-amide |
| I-44 | 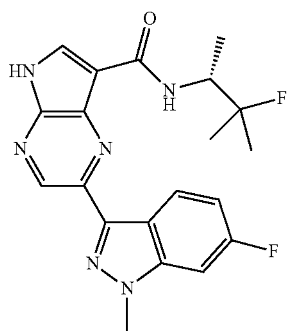 [SMILES: C[C@@H](NC(=O)c1c[nH]c2ncc(-c3nn(C)c4cc(F)ccc34)nc12)C(C)(C)F] | 2-(6-Fluoro-1-methyl-1H-indazol-3-yl)-5H-pyrrolo[2,3-b]pyrazine-7-carboxylic acid ((R)-2-fluoro-1,2-dimethyl-propyl)-amide |
| I-45 | 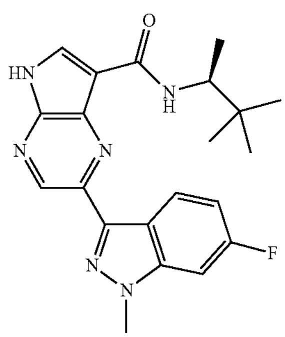 [SMILES: C[C@H](NC(=O)c1c[nH]c2ncc(-c3nn(C)c4cc(F)ccc34)nc12)C(C)(C)C] | 2-(6-Fluoro-1-methyl-1H-indazol-3-yl)-5H-pyrrolo[2,3-b]pyrazine-7-carboxylic acid ((S)-1,2,2-trimethyl-propyl)-amide |
| I-46 | 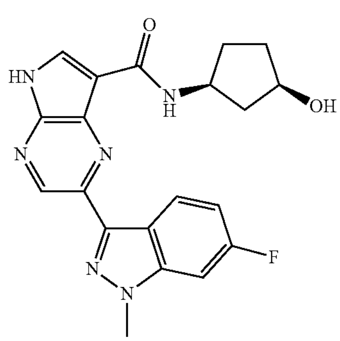 [SMILES: Cn1nc(-c2cnc3[nH]cc(C(=O)N[C@H]4CC[C@@H](O)C4)c3n2)c2ccc(F)cc21] | 2-(6-Fluoro-1-methyl-1H-indazol-3-yl)-5H-pyrrolo[2,3-b]pyrazine-7-carboxylic acid (cis-3-hydroxy-cyclopentyl)-amide |

TABLE I-continued

| COMPOUND | STRUCTURE | SYSTEMATIC NAME |
| --- | --- | --- |
| I-47 | 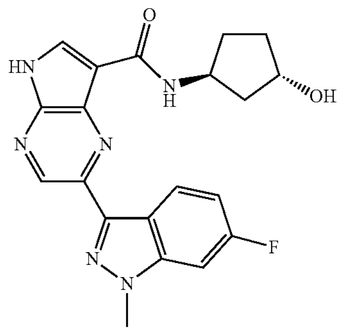 [SMILES: Cn1nc(-c2cnc3[nH]cc(C(=O)N[C@H]4CC[C@H](O)C4)c3n2)c2ccc(F)cc21] | 2-(6-Fluoro-1-methyl-1H-indazol-3-yl)-5H-pyrrolo[2,3-b]pyrazine-7-carboxylic acid (trans-3-hydroxy-cyclopentyl)-amide |
| I-48 | 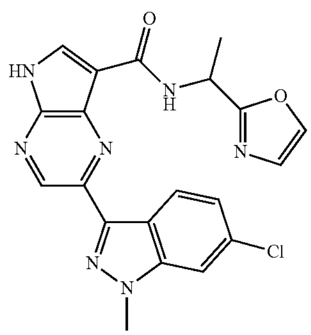 | 2-(6-Chloro-1-methyl-1H-indazol-3-yl)-5H-pyrrolo[2,3-b]pyrazine-7-carboxylic acid (1-oxazol-2-yl-ethyl)-amide |
| I-49 | 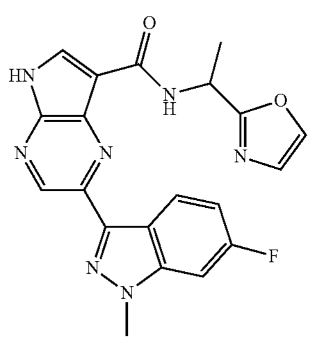 | 2-(6-Fluoro-1-methyl-1H-indazol-3-yl)-5H-pyrrolo[2,3-b]pyrazine-7-carboxylic acid (1-oxazol-2-yl-ethyl)-amide |
| I-50 | 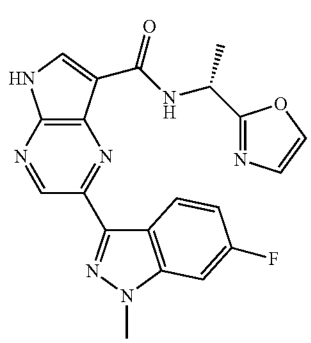 [SMILES: CC(NC(=O)c1c[nH]c2ncc(-c3nn(C)c4cc(Cl)ccc34)nc12)c1ncco1] | 2-(6-Fluoro-1-methyl-1H-indazol-3-yl)-5H-pyrrolo[2,3-b]pyrazine-7-carboxylic acid ((R)-1-oxazol-2-yl-ethyl)-amide |

TABLE I-continued

| COMPOUND | STRUCTURE | SYSTEMATIC NAME |
| --- | --- | --- |
| I-51 | 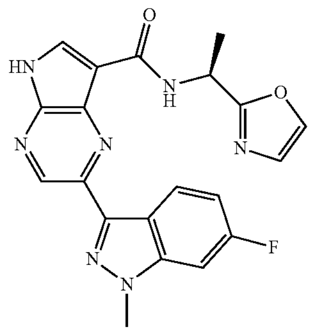 [SMILES: C[C@H](NC(=O)c1c[nH]c2ncc(-c3nn(C)c4cc(F)ccc34)nc12)c1ncco1] | 2-(6-Fluoro-1-methyl-1H-indazol-3-yl)-5H-pyrrolo[2,3-b]pyrazine-7-carboxylic acid ((S)-1-oxazol-2-yl-ethyl)-amide |
| I-52 | 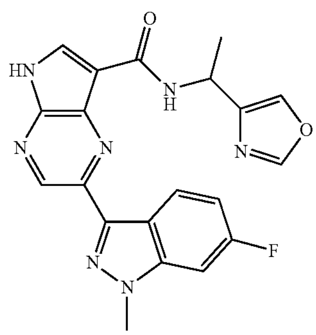 [SMILES: CC(NC(=O)c1c[nH]c2ncc(-c3nn(C)c4cc(F)ccc34)nc12)c1cocn1] | 2-(6-Fluoro-1-methyl-1H-indazol-3-yl)-5H-pyrrolo[2,3-b]pyrazine-7-carboxylic acid (1-oxazol-4-yl-ethyl)-amide |
| I-53 | 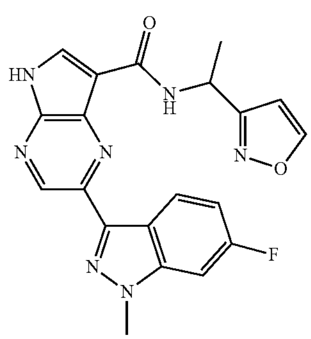 [SMILES: CC(NC(=O)c1c[nH]c2ncc(-c3nn(C)c4cc(F)ccc34)nc12)c1ccon1] | 2-(6-Fluoro-1-methyl-1H-indazol-3-yl)-5H-pyrrolo[2,3-b]pyrazine-7-carboxylic acid (1-isoxazol-3-yl-ethyl)-amide |
| I-54 | 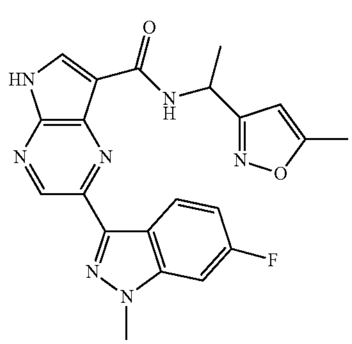 [SMILES: Cc1cc(C(C)NC(=O)c2c[nH]c3ncc(-c4nn(C)c5cc(F)ccc45)nc23)no1] | 2-(6-Fluoro-1-methyl-1H-indazol-3-yl)-5H-pyrrolo[2,3-b]pyrazine-7-carboxylic acid [1-(5-methyl-isoxazol-3-yl)-ethyl]-amide |

TABLE I-continued

| COMPOUND | STRUCTURE | SYSTEMATIC NAME |
| --- | --- | --- |
| I-55 | 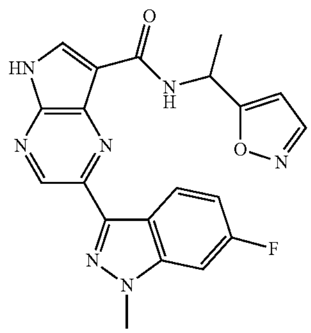 [SMILES: CC(NC(=O)c1c[nH]c2ncc(-c3nn(C)c4cc(F)ccc34)nc12)c1ccno1] | 2-(6-Fluoro-1-methyl-1H-indazol-3-yl)-5H-pyrrolo[2,3-b]pyrazine-7-carboxylic acid (1-isoxazol-5-yl-ethyl)-amide |
| I-56 | 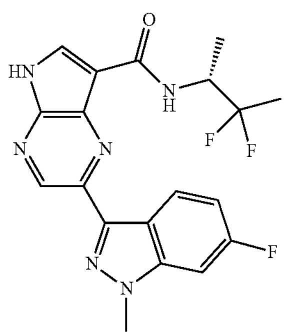 [SMILES: C[C@@H](NC(=O)c1c[nH]c2ncc(-c3nn(C)c4cc(F)ccc34)nc12)C(C)(F)F] | 2-(6-Fluoro-1-methyl-1H-indazol-3-yl)-5H-pyrrolo[2,3-b]pyrazine-7-carboxylic acid ((R)-2,2-difluoro-1-methyl-propyl)-amide |
| I-57 | 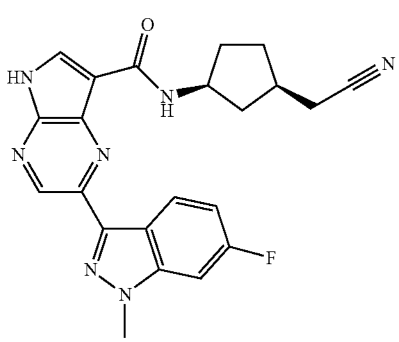 [SMILES: Cn1nc(-c2cnc3[nH]cc(C(=O)N[C@H]4CC[C@@H](CC#N)C4)c3n2)c2ccc(F)cc21] | 2-(6-Fluoro-1-methyl-1H-indazol-3-yl)-5H-pyrrolo[2,3-b]pyrazine-7-carboxylic acid (cis-3-cyanomethyl-cyclopentyl)-amide |
| I-58 | 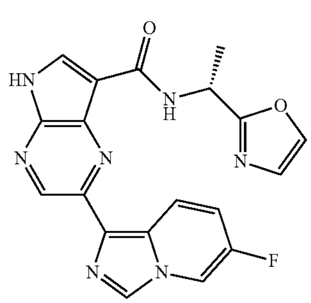 [SMILES: C[C@@H](NC(=O)c1c[nH]c2ncc(-c3ncn4cc(F)ccc34)nc12)c1ncco1] | 2-(6-Fluoro-imidazo[1,5-a]pyridin-1-yl)-5H-pyrrolo[2,3-b]pyrazine-7-carboxylic acid ((R)-1-oxazol-2-yl-ethyl)-amide |

TABLE I-continued

| COMPOUND | STRUCTURE | SYSTEMATIC NAME |
| --- | --- | --- |
| I-59 | 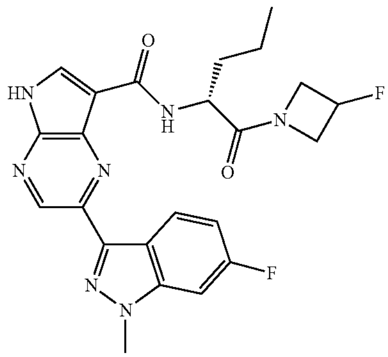 [SMILES: CCC[C@@H](NC(=O)c1c[nH]c2ncc(-c3nn(C)c4cc(F)ccc34)nc12)C(=O)N1CC(F)C1] | 2-(6-Fluoro-1-methyl-1H-indazol-3-yl)-5H-pyrrolo[2,3-b]pyrazine-7-carboxylic acid [(R)-1-(3-fluoro-azetidine-1-carbonyl)-butyl]-amide |
| I-60 | 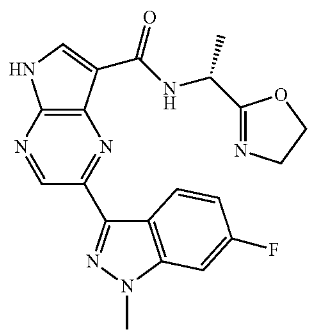 [SMILES: C[C@@H](NC(=O)c1c[nH]c2ncc(-c3nn(C)c4cc(F)ccc34)nc12)C1=NCCO1] | 2-(6-Fluoro-1-methyl-1H-indazol-3-yl)-5H-pyrrolo[2,3-b]pyrazine-7-carboxylic acid [(R)-1-(4,5-dihydro-oxazol-2-yl)-ethyl]-amide |
| I-61 | 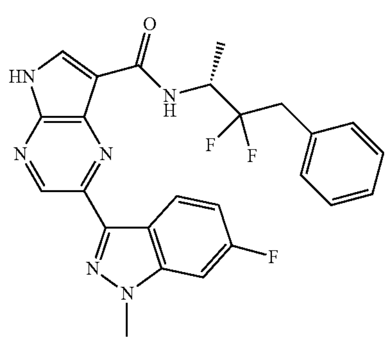 [SMILES: C[C@@H](NC(=O)c1c[nH]c2ncc(-c3nn(C)c4cc(F)ccc34)nc12)C(F)(F)Cc1ccccc1] | 2-(6-Fluoro-1-methyl-1H-indazol-3-yl)-5H-pyrrolo[2,3-b]pyrazine-7-carboxylic acid ((R)-2,2-difluoro-1-methyl-3-phenyl-propyl)-amide |
| I-62 | 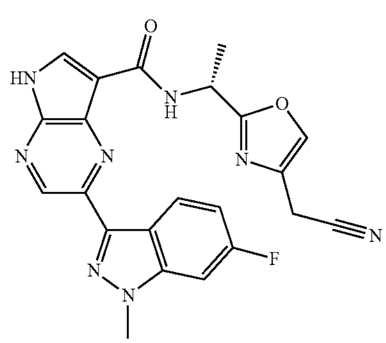 [SMILES: C[C@@H](NC(=O)c1c[nH]c2ncc(-c3nn(C)c4cc(F)ccc34)nc12)c1nc(CC#N)co1] | 2-(6-Fluoro-1-methyl-1H-indazol-3-yl)-5H-pyrrolo[2,3-b]pyrazine-7-carboxylic acid [(R)-1-(4-cyanomethyl-oxazol-2-yl)-ethyl]-amide |

TABLE I-continued

| COMPOUND | STRUCTURE | SYSTEMATIC NAME |
| --- | --- | --- |
| I-63 | 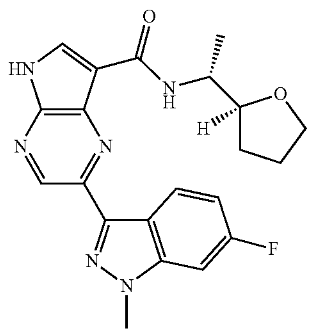 [SMILES: C[C@@H](NC(=O)c1c[nH]c2ncc(-c3nn(C)c4cc(F)ccc34)nc12)[C@@H]1CCCO1] | 2-(6-Fluoro-1-methyl-1H-indazol-3-yl)-5H-pyrrolo[2,3-b]pyrazine-7-carboxylic acid [(R)-(S)-1-(tetrahydro-furan-2-yl)-ethyl]-amide |
| I-64 | 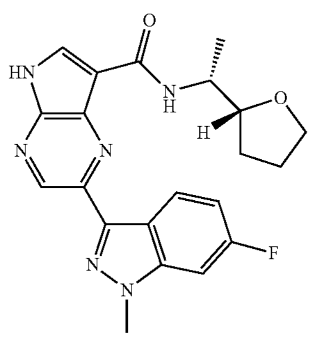 [SMILES: C[C@@H](NC(=O)c1c[nH]c2ncc(-c3nn(C)c4cc(F)ccc34)nc12)[C@H]1CCCO1] | 2-(6-Fluoro-1-methyl-1H-indazol-3-yl)-5H-pyrrolo[2,3-b]pyrazine-7-carboxylic acid [(R)-(R)-1-(tetrahydro-furan-2-yl)-ethyl]-amide |
| I-65 | 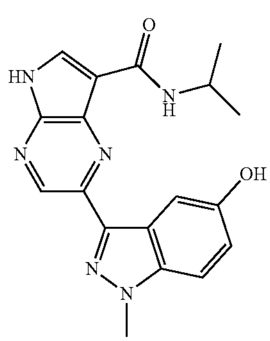 [SMILES: CC(C)NC(=O)c1c[nH]c2ncc(-c3nn(C)c4ccc(O)cc34)nc12] | 2-(5-Hydroxy-1-methyl-1H-indazol-3-yl)-5H-pyrrolo[2,3-b]pyrazine-7-carboxylic acid isopropylamide |
| I-66 | 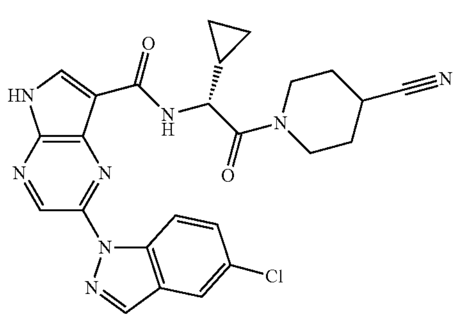 [SMILES: N#CC1CCN(C(=O)[C@H](NC(=O)c2c[nH]c3ncc(-n4ncc5cc(Cl)ccc54)nc23)C2CC2)CC1] | 2-(5-Chloro-indazol-1-yl)-5H-pyrrolo[2,3-b]pyrazine-7-carboxylic acid [(R)-2-(4-cyano-piperidin-1-yl)-1-cyclopropyl-2-oxo-ethyl]-amide |

TABLE I-continued

| COMPOUND | STRUCTURE | SYSTEMATIC NAME |
|---|---|---|
| I-67 | 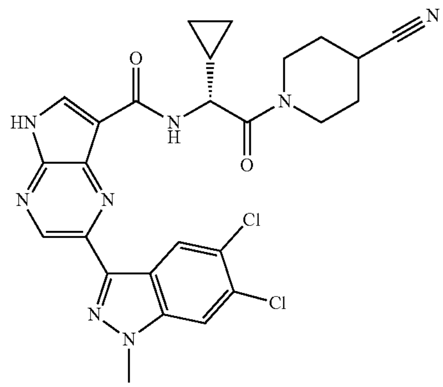 [SMILES: Cn1nc(-c2cnc3[nH]cc(C(=O)N[C@@H](C(=O)N4CCC(C#N)CC4)C4CC4)c3n2)c2cc(Cl)c(Cl)cc21] | 2-(5,6-Dichloro-1-methyl-1H-indazol-3-yl)-5H-pyrrolo[2,3-b]pyrazine-7-carboxylic acid [(R)-2-(4-cyano-piperidin-1-yl)-1-cyclopropyl-2-oxo-ethyl]-amide |
| I-68 | 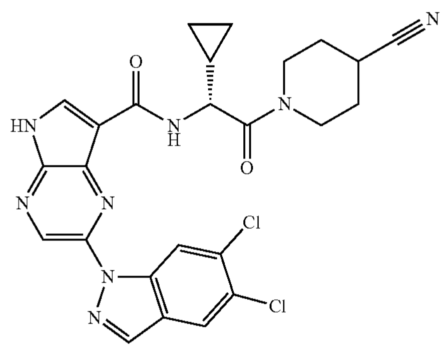 [SMILES: N#CC1CCN(C(=O)[C@H](NC(=O)c2c[nH]c3ncc(-n4ncc5cc(Cl)c(Cl)cc54)nc23)C2CC2)CC1] | 2-(5,6-Dichloro-indazol-1-yl)-5H-pyrrolo[2,3-b]pyrazine-7-carboxylic acid [(R)-2-(4-cyano-piperidin-1-yl)-1-cyclopropyl-2-oxo-ethyl]-amide |
| I-69 | 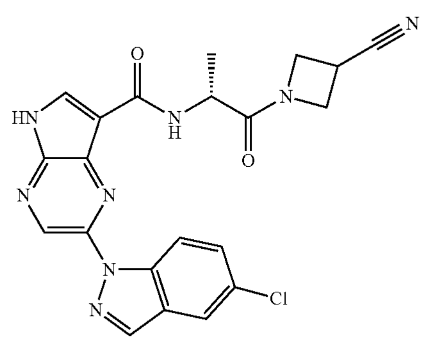 [SMILES: C[C@@H](NC(=O)c1c[nH]c2ncc(-n3ncc4cc(Cl)ccc43)nc12)C(=O)N1CC(C#N)C1] | 2-(5-Chloro-indazol-1-yl)-5H-pyrrolo[2,3-b]pyrazine-7-carboxylic acid [(R)-2-(3-cyano-azetidin-1-yl)-1-methyl-2-oxo-ethyl]-amide |
| I-70 | 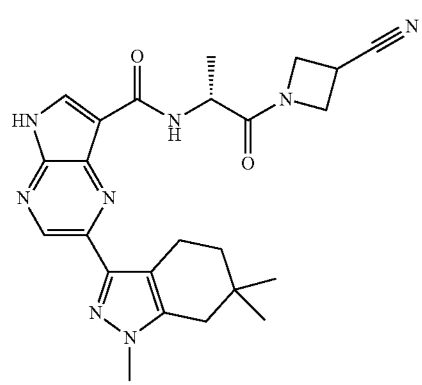 [SMILES: C[C@@H](NC(=O)c1c[nH]c2ncc(-c3nn(C)c4c3CCC(C)(C)C4)nc12)C(=O)N1CC(C#N)C1] | 2-(1,6,6-Trimethyl-4,5,6,7-tetrahydro-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide |

TABLE I-continued

| COMPOUND | STRUCTURE | SYSTEMATIC NAME |
| --- | --- | --- |
| I-71 | 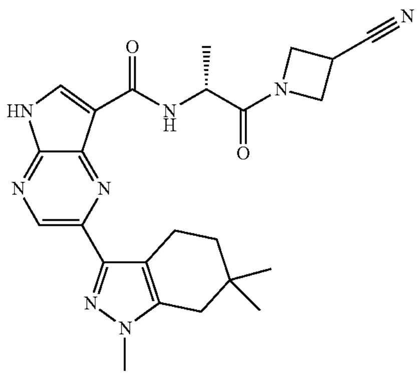 [SMILES: C[C@@H](NC(=O)c1c[nH]c2ncc(-c3nn(C)c4c3CCC(C)(C)C4)nc12)C(=O)N1CC(C#N)C1] | 2-(6-Chloro-1-methyl-1H-indazol-3-yl)-5H-pyrrolo[2,3-b]pyrazine-7-carboxylic acid [1-(1-methanesulfonyl-azetidin-3-yl)-ethyl]-amide |
| I-72 | 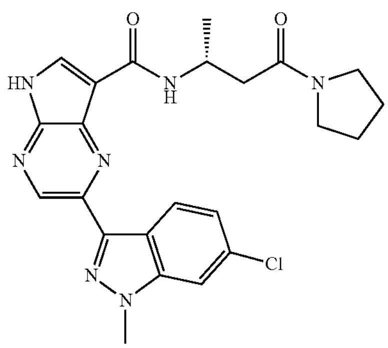 [SMILES: C[C@H](CC(=O)N1CCCC1)NC(=O)c1c[nH]c2ncc(-c3nn(C)c4cc(Cl)ccc34)nc12] | 2-(6-Chloro-1-methyl-1H-indazol-3-yl)-5H-pyrrolo[2,3-b]pyrazine-7-carboxylic acid ((R)-1-methyl-3-oxo-3-pyrrolidin-1-yl-propyl)-amide |
| I-73 | 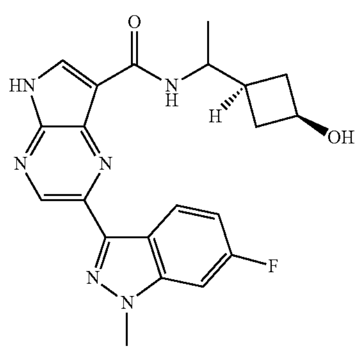 [SMILES: CC(NC(=O)c1c[nH]c2ncc(-c3nn(C)c4cc(F)ccc34)nc12)[C@H]1C[C@@H](O)C1] | 2-(6-Fluoro-1-methyl-1H-indazol-3-yl)-5H-pyrrolo[2,3-b]pyrazine-7-carboxylic acid [1-(cis-3-hydroxy-cyclobutyl)-ethyl]-amide |
| I-74 | 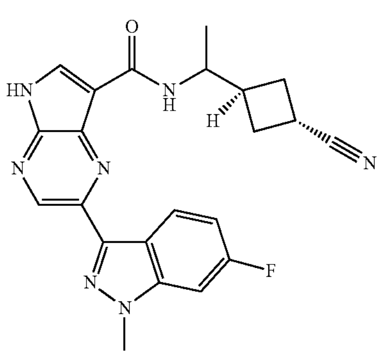 [SMILES: CC(NC(=O)c1c[nH]c2ncc(-c3nn(C)c4cc(F)ccc34)nc12)[C@H]1C[C@H](C#N)C1] | 2-(6-Fluoro-1-methyl-1H-indazol-3-yl)-5H-pyrrolo[2,3-b]pyrazine-7-carboxylic acid [1-(trans-3-cyano-cyclobutyl)-ethyl]-amide |

TABLE I-continued

| COMPOUND | STRUCTURE | SYSTEMATIC NAME |
| --- | --- | --- |
| I-75 | 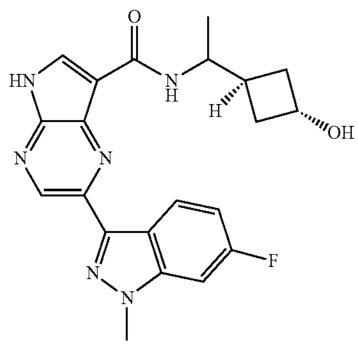 [SMILES: CC(NC(=O)c1c[nH]c2ncc(-c3nn(C)c4cc(F)ccc34)nc12)[C@H]1C[C@H](O)C1] | 2-(6-Fluoro-1-methyl-1H-indazol-3-yl)-5H-pyrrolo[2,3-b]pyrazine-7-carboxylic acid [1-(trans-3-hydroxy-cyclobutyl)-ethyl]-amide |
| I-76 | 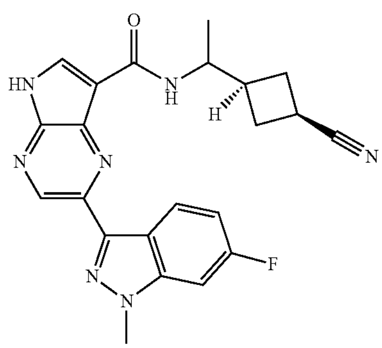 [SMILES: CC(NC(=O)c1c[nH]c2ncc(-c3nn(C)c4cc(F)ccc34)nc12)[C@H]1C[C@@H](C#N)C1] | 2-(6-Fluoro-1-methyl-1H-indazol-3-yl)-5H-pyrrolo[2,3-b]pyrazine-7-carboxylic acid [1-(cis-3-cyano-cyclobutyl)-ethyl]-amide |
| I-77 | 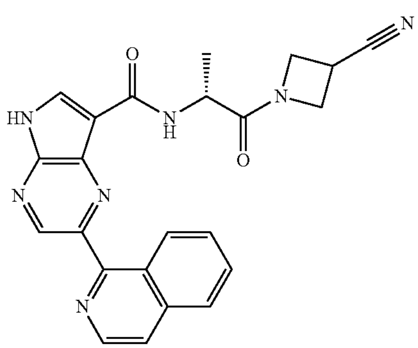 [SMILES: C[C@@H](NC(=O)c1c[nH]c2ncc(-c3nccc4ccccc34)nc12)C(=O)N1CC(C#N)C1] | 2-Isoquinolin-1-yl-5H-pyrrolo[2,3-b]pyrazine-7-carboxylic acid [(R)-2-(3-cyano-azetidin-1-yl)-1-methyl-2-oxo-ethyl]-amide |
| I-78 | 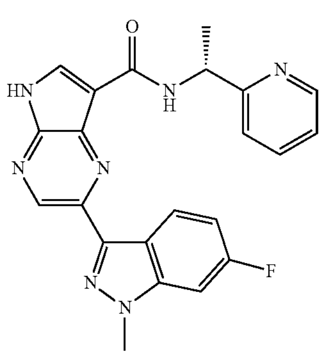 [SMILES: C[C@@H](NC(=O)c1c[nH]c2ncc(-c3nn(C)c4cc(F)ccc34)nc12)c1ccccn1] | 2-(6-Fluoro-1-methyl-1H-indazol-3-yl)-5H-pyrrolo[2,3-b]pyrazine-7-carboxylic acid ((R)-1-pyridin-2-yl-ethyl)-amide |

TABLE I-continued

| COMPOUND | STRUCTURE | SYSTEMATIC NAME |
|---|---|---|
| I-79 | 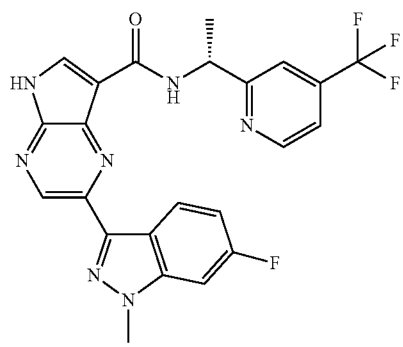 [SMILES: C[C@@H](NC(=O)c1c[nH]c2ncc(-c3nn(C)c4cc(F)ccc34)nc12)c1cc(C(F)(F)F)ccn1] | 2-(6-Fluoro-1-methyl-1H-indazol-3-yl)-5H-pyrrolo[2,3-b]pyrazine-7-carboxylic acid [(R)-1-(4-trifluoromethyl-pyridin-2-yl)-ethyl]-amide |
| I-80 | 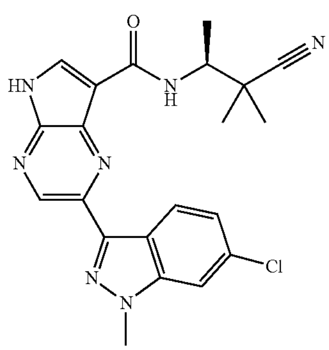 [SMILES: C[C@H](NC(=O)c1c[nH]c2ncc(-c3nn(C)c4cc(Cl)ccc34)nc12)C(C)(C)C#N] | 2-(6-Chloro-1-methyl-1H-indazol-3-yl)-5H-pyrrolo[2,3-b]pyrazine-7-carboxylic acid ((S)-2-cyano-1,2,2-trimethyl-ethyl)-amide |
| I-81 | 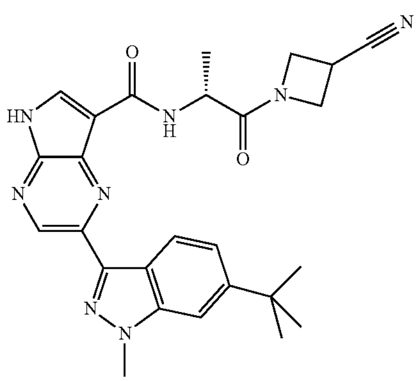 [SMILES: C[C@@H](NC(=O)c1c[nH]c2ncc(-c3nn(C)c4cc(C(C)(C)C)ccc34)nc12)C(=O)N1CC(C#N)C1] | 2-(6-tert-Butyl-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide |
| I-82 | 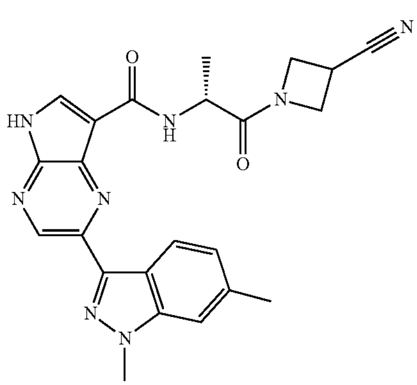 | 2-(1,6-Dimethyl-1H-indazol-3-yl)-5H-pyrrolo[2,3-b]pyrazine-7-carboxylic acid [(R)-2-(3-cyano-azetidin-1-yl)-1-methyl-2-oxo-ethyl-amide |

TABLE I-continued

| COMPOUND | STRUCTURE | SYSTEMATIC NAME |
| --- | --- | --- |
| I-83 | 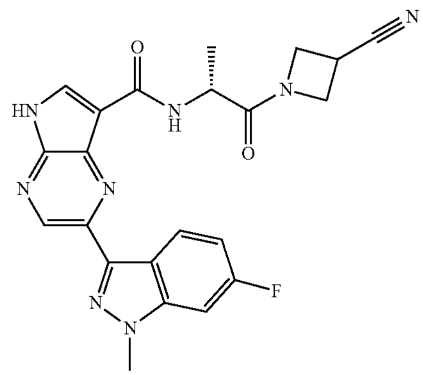 [SMILES: C[C@@H](NC(=O)c1c[nH]c2ncc(-c3nn(C)c4cc(F)ccc34)nc12)C(=O)N1CC(C#N)C1] | 2-(6-Fluoro-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide |
| I-84 | 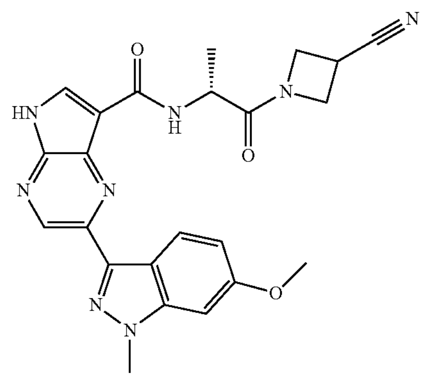 [SMILES: COc1ccc2c(-c3cnc4[nH]cc(C(=O)N[C@H](C)C(=O)N5CC(C#N)C5)c4n3)nn(C)c2c1] | 2-(6-Methoxy-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide |
| I-85 | 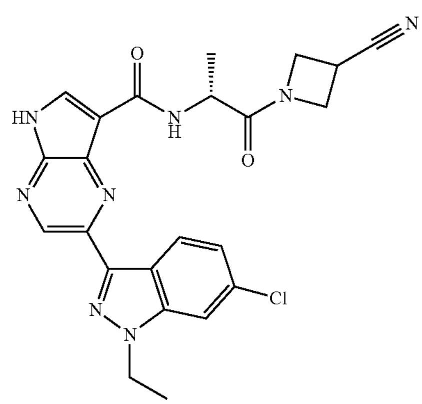 [SMILES: CCn1nc(-c2cnc3[nH]cc(C(=O)N[C@H](C)C(=O)N4CC(C#N)C4)c3n2)c2ccc(Cl)cc21] | 2-(6-Chloro-1-ethyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide |
| I-86 | 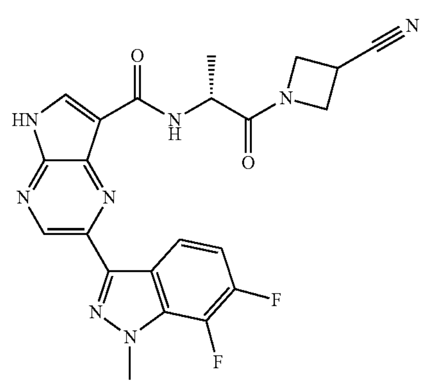 [SMILES: C[C@@H](NC(=O)c1c[nH]c2ncc(-c3nn(C)c4c(F)c(F)ccc34)nc12)C(=O)N1CC(C#N)C1] | 2-(6,7-Difluoro-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide |

TABLE I-continued

| COMPOUND | STRUCTURE | SYSTEMATIC NAME |
|---|---|---|
| I-87 | 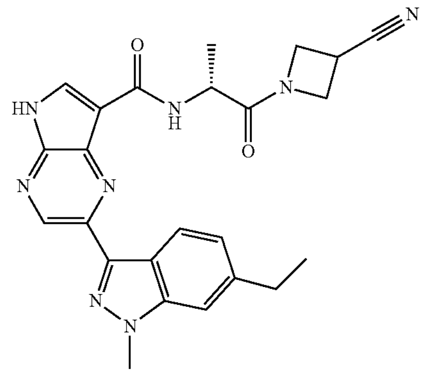 [SMILES: CCc1ccc2c(-c3cnc4[nH]cc(C(=O)N[C@H](C)C(=O)N5CC(C#N)C5)c4n3)nn(C)c2c1] | 2-(6-Ethyl-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide |
| I-88 | 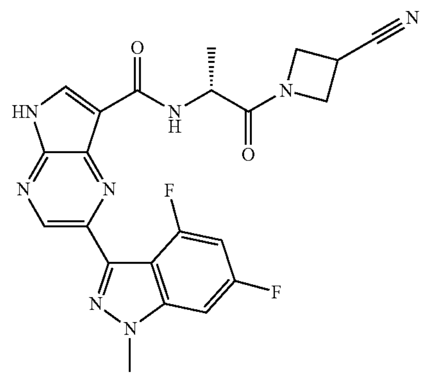 [SMILES: C[C@@H](NC(=O)c1c[nH]c2ncc(-c3nn(C)c4cc(F)cc(F)c34)nc12)C(=O)N1CC(C#N)C1] | 2-(4,6-Difluoro-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide |
| I-89 | 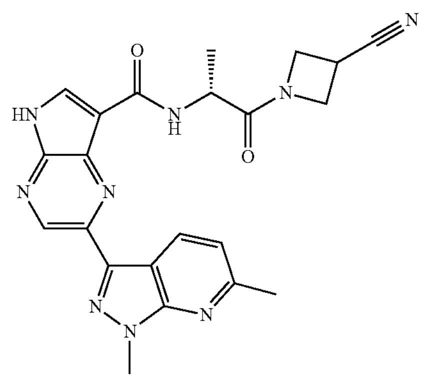 [SMILES: Cc1ccc2c(-c3cnc4[nH]cc(C(=O)N[C@H](C)C(=O)N5CC(C#N)C5)c4n3)nn(C)c2n1] | 2-(1,6-Dimethyl-1H-pyrazolo[3,4-b]pyridin-3-yl)-5H-pyrrolo[2,3-b]pyrazine-7-carboxylic acid [(R)-2-(3-cyano-azetidin-1-yl)-1-methyl-2-oxo-ethyl]-amide |
| I-90 | 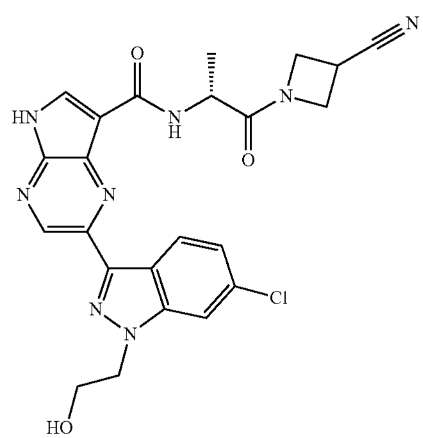 [SMILES: C[C@@H](NC(=O)c1c[nH]c2ncc(-c3nn(CCO)c4cc(Cl)ccc34)nc12)C(=O)N1CC(C#N)C1] | 2-[6-Chloro-1-(2-hydroxy-ethyl)-1H-indazol-3-yl]-5H-pyrrolo[2,3-b]pyrazine-7-carboxylic acid [(R)-2-(3-cyano-azetidin-1-yl)-1-methyl-2-oxo-ethyl]-amide |

TABLE I-continued

| COMPOUND | STRUCTURE | SYSTEMATIC NAME |
|---|---|---|
| I-91 | 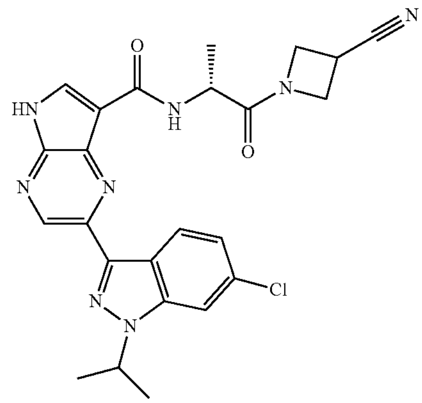 [SMILES: CC(C)n1nc(-c2cnc3[nH]cc(C(=O)N[C@H](C)C(=O)N4CC(C#N)C4)c3n2)c2ccc(Cl)cc21] | 2-(6-Chloro-1-isopropyl-1H-indazol-3-yl)-5H-pyrrolo[2,3-b]pyrazine-7-carboxylic acid [(R)-2-(3-cyano-azetidin-1-yl)-1-methyl-2-oxo-ethyl)-amide |
| I-92 | 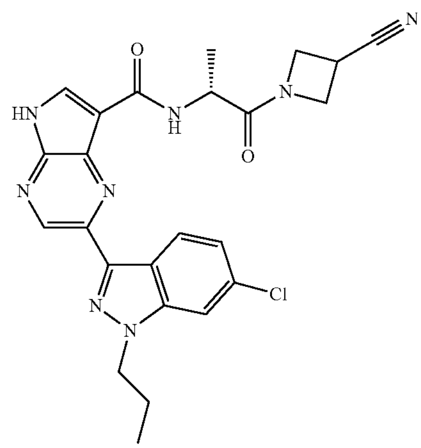 [SMILES: CCCn1nc(-c2cnc3[nH]cc(C(=O)N[C@H](C)C(=O)N4CC(C#N)C4)c3n2)c2ccc(Cl)cc21] | 2-(6-Chloro-1-propyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide |
| I-93 | 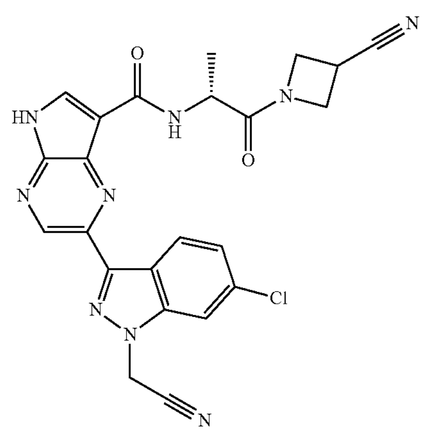 [SMILES: C[C@@H](NC(=O)c1c[nH]c2ncc(-c3nn(CC#N)c4cc(Cl)ccc34)nc12)C(=O)N1CC(C#N)C1] | 2-(6-Chloro-1-cyanomethyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide |

TABLE I-continued

| COMPOUND | STRUCTURE | SYSTEMATIC NAME |
| --- | --- | --- |
| I-94 | 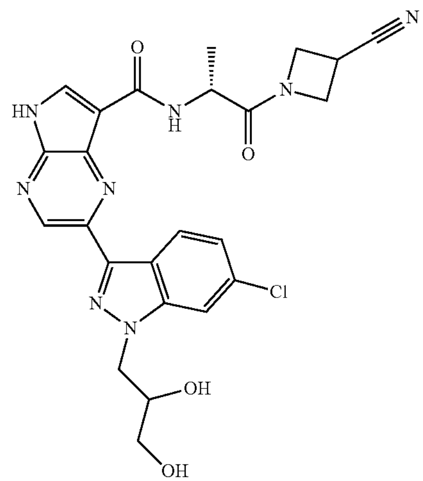 [SMILES: C[C@@H](NC(=O)c1c[nH]c2ncc(-c3nn(CC(O)CO)c4cc(Cl)ccc34)nc12)C(=O)N1CC(C#N)C1] | 2-[6-Chloro-1-(2,3-dihydroxy-propyl)-1H-indazol-3-yl]-5H-pyrrolo[2,3-b]pyrazine-7-carboxylic acid [(R)-2-(3-cyano-azetidin-1-yl)-1-methyl-2-oxo-ethyl)-amide |
| I-95 | 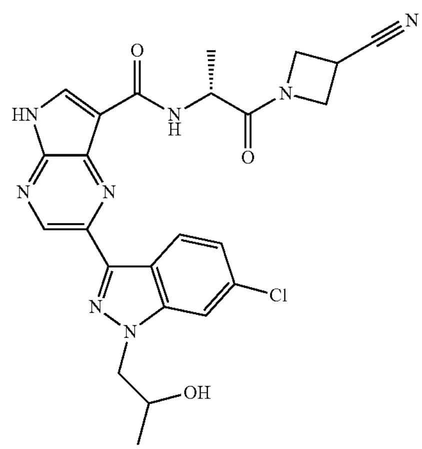 [SMILES: CC(O)Cn1nc(-c2cnc3[nH]cc(C(=O)N[C@H](C)C(=O)N4CC(C#N)C4)c3n2)c2ccc(Cl)cc21] | 2-[6-Chloro-1-(2-hydroxy-propyl)-1H-indazol-3-yl]-5H-pyrrolo[2,3-b]pyrazine-7-carboxylic acid [(R)-2-(3-cyano-azetidin-1-yl)-1-methyl-2-oxo-ethyl]-amide |
| I-96 | 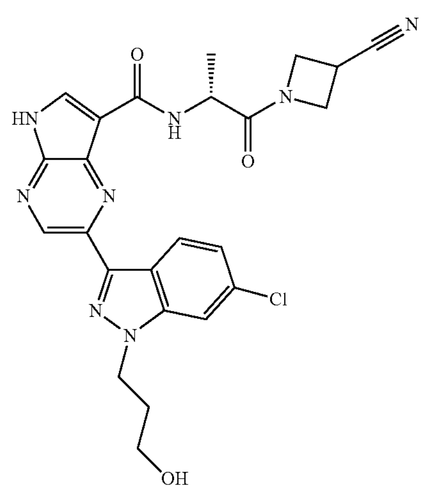 [SMILES: C[C@@H](NC(=O)c1c[nH]c2ncc(-c3nn(CCCO)c4cc(Cl)ccc34)nc12)C(=O)N1CC(C#N)C1] | 2-[6-Chloro-1-(3-hydroxy-propyl)-1H-indazol-3-yl]-5H-pyrrolo[2,3-b]pyrazine-7-carboxylic acid [(R)-2-(3-cyano-azetidin-1-yl)-1-methyl-2-oxo-ethyl]-amide |

TABLE I-continued

| COMPOUND | STRUCTURE | SYSTEMATIC NAME |
|---|---|---|
| I-97 | 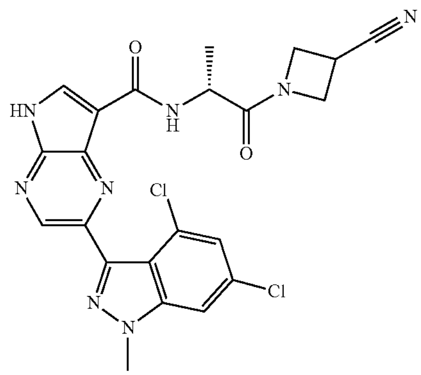 [SMILES: C[C@@H](NC(=O)c1c[nH]c2ncc(-c3nn(C)c4cc(Cl)cc(Cl)c34)nc12)C(=O)N1CC(C#N)C1] | 2-(4,6-Dichloro-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide |
| I-98 | 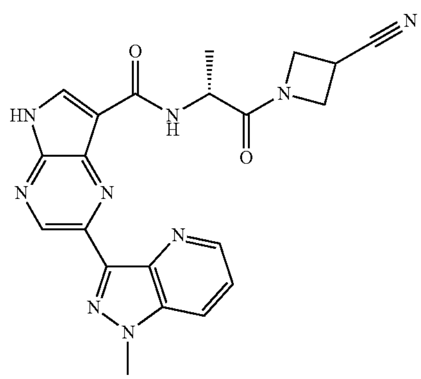 [SMILES: C[C@@H](NC(=O)c1c[nH]c2ncc(-c3nn(C)c4cccnc34)nc12)C(=O)N1CC(C#N)C1] | 2-(1-Methyl-1H-pyrazolo[4,3-b]pyridin-3-yl)-5H-pyrrolo[2,3-b]pyrazine-7-carboxylic acid [(R)-2-(3-cyano-azetidin-1-yl)-1-methyl-2-oxo-ethyl]-amide |
| I-99 | 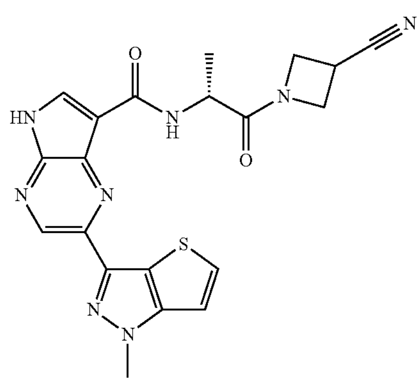 [SMILES: C[C@@H](NC(=O)c1c[nH]c2ncc(-c3nn(C)c4ccsc34)nc12)C(=O)N1CC(C#N)C1] | 2-(1-Methyl-1H-thieno[3,2-c]pyrazol-3-yl)-5H-pyrrolo[2,3-b]pyrazine-7-carboxylic acid [(R)-2-(3-cyano-azetidin-1-yl)-1-methyl-2-oxo-ethyl]-amide |
| I-100 | 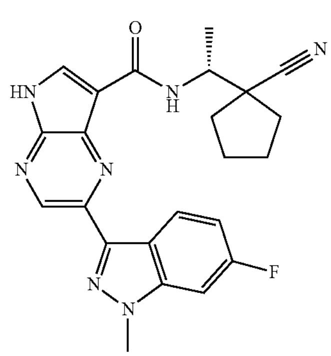 [SMILES: C[C@@H](NC(=O)c1c[nH]c2ncc(-c3nn(C)c4cc(F)ccc34)nc12)C1(C#N)CCCC1] | 2-(6-Fluoro-1-methyl-1H-indazol-3-yl)-5H-pyrrolo[2,3-b]pyrazine-7-carboxylic acid [(R)-1-(1-cyano-cyclopentyl)-ethyl]-amide |

TABLE I-continued

| COMPOUND | STRUCTURE | SYSTEMATIC NAME |
|---|---|---|
| I-101 | 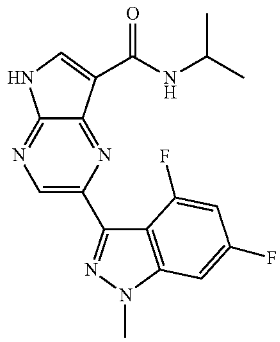 [SMILES: CC(C)NC(=O)c1c[nH]c2ncc(-c3nn(C)c4cc(F)cc(F)c34)nc12] | 2-(4,6-Difluoro-1-methyl-1H-indazol-3-yl)-5H-pyrrolo[2,3-b]pyrazine-7-carboxylic acid isopropylamide |
| I-102 | 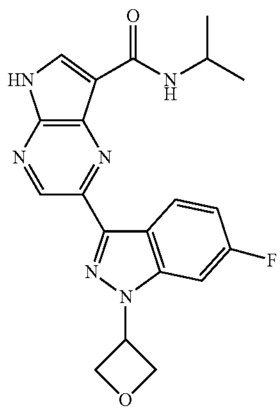 [SMILES: CC(C)NC(=O)c1c[nH]c2ncc(-c3nn(C4COC4)c4cc(F)ccc34)nc12] | 2-(6-Fluoro-1-oxetan-3-yl-1H-indazol-3-yl)-5H-pyrrolo[2,3-b]pyrazine-7-carboxylic acid isopropylamide |
| I-103 | 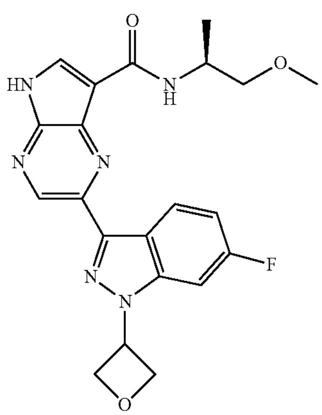 [SMILES: COC[C@H](C)NC(=O)c1c[nH]c2ncc(-c3nn(C4COC4)c4cc(F)ccc34)nc12] | 2-(6-Fluoro-1-oxetan-3-yl-1H-indazol-3-yl)-5H-pyrrolo[2,3-b]pyrazine-7-carboxylic acid ((S)-2-methoxy-1-methyl-ethyl)-amide |
| I-104 | 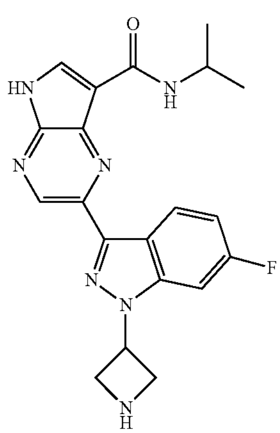 [SMILES: CC(C)NC(=O)c1c[nH]c2ncc(-c3nn(C4CNC4)c4cc(F)ccc34)nc12] | 2-(1-Azetidin-3-yl-6-fluoro-1H-indazol-3-yl)-5H-pyrrolo[2,3-b]pyrazine-7-carboxylic acid isopropylamide |

TABLE I-continued

| COMPOUND | STRUCTURE | SYSTEMATIC NAME |
|---|---|---|
| I-105 | 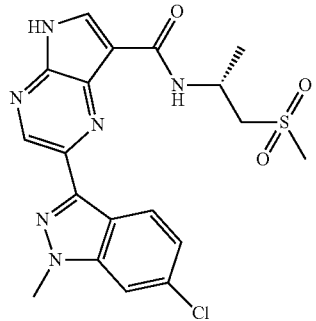 [SMILES: C[C@H](CS(C)(=O)=O)NC(=O)c1c[nH]c2ncc(-c3nn(C)c4cc(Cl)ccc34)nc12] | 2-(6-Chloro-1-methyl-1H-indazol-3-yl)-5H-pyrrolo[2,3-b]pyrazine-7-carboxylic acid ((R)-2-methanesulfonyl-1-methyl-ethyl)-amide |
| I-106 | 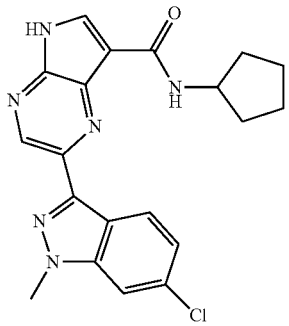 [SMILES: Cn1nc(-c2cnc3[nH]cc(C(=O)NC4CCCC4)c3n2)c2ccc(Cl)cc21] | 2-(6-Chloro-1-methyl-1H-indazol-3-yl)-5H-pyrrolo[2,3-b]pyrazine-7-carboxylic acid cyclopentylamide |
| I-107 | 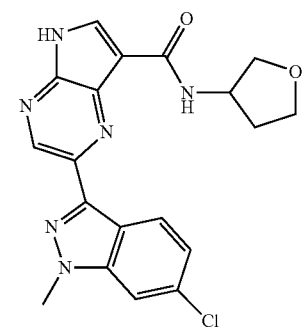 [SMILES: Cn1nc(-c2cnc3[nH]cc(C(=O)NC4CCOC4)c3n2)c2ccc(Cl)cc21] | 2-(6-Chloro-1-methyl-1H-indazol-3-yl)-5H-pyrrolo[2,3-b]pyrazine-7-carboxylic acid (tetrahydro-furan-3-yl)-amide |
| I-108 | 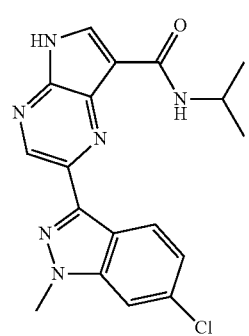 [SMILES: CC(C)NC(=O)c1c[nH]c2ncc(-c3nn(C)c4cc(Cl)ccc34)nc12] | 2-(6-Chloro-1-methyl-1H-indazol-3-yl)-5H-pyrrolo[2,3-b]pyrazine-7-carboxylic acid isopropylamide |

TABLE I-continued

| COMPOUND | STRUCTURE | SYSTEMATIC NAME |
|---|---|---|
| I-109 | 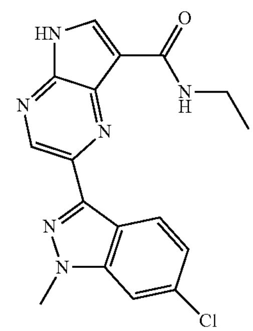 [SMILES: CCNC(=O)c1c[nH]c2ncc(-c3nn(C)c4cc(Cl)ccc34)nc12] | 2-(6-Chloro-1-methyl-1H-indazol-3-yl)-5H-pyrrolo[2,3-b]pyrazine-7-carboxylic acid ethylamide |
| I-110 | 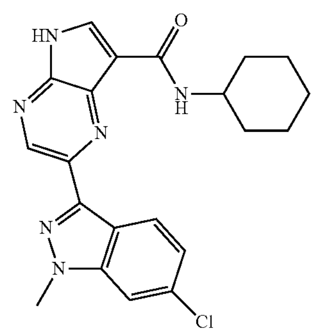 [SMILES: Cn1nc(-c2cnc3[nH]cc(C(=O)NC4CCCCC4)c3n2)c2ccc(Cl)cc21] | 2-(6-Chloro-1-methyl-1H-indazol-3-yl)-5H-pyrrolo[2,3-b]pyrazine-7-carboxylic acid cyclohexylamide |
| I-111 | 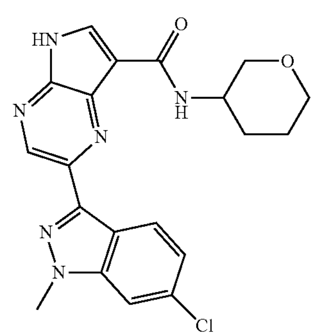 | 2-(6-Chloro-1-methyl-1H-indazol-3-yl)-5H-pyrrolo[2,3-b]pyrazine-7-carboxylic acid (tetrahydro-pyran-3-yl)-amide |
| I-112 | 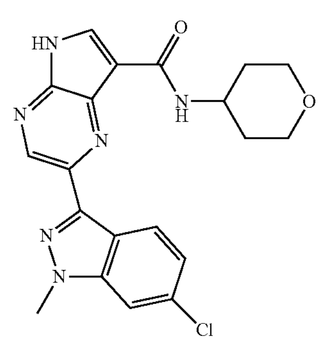 [SMILES: Cn1nc(-c2cnc3[nH]cc(C(=O)NC4CCOCC4)c3n2)c2ccc(Cl)cc21] | 2-(6-Chloro-1-methyl-1H-indazol-3-yl)-5H-pyrrolo[2,3-b]pyrazine-7-carboxylic acid (tetrahydro-pyran-4-yl)-amide |

TABLE I-continued

| COMPOUND | STRUCTURE | SYSTEMATIC NAME |
|---|---|---|
| I-113 | 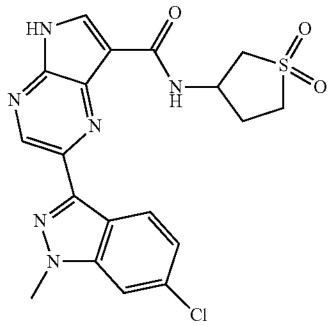 [SMILES: Cn1nc(-c2cnc3[nH]cc(C(=O)NC4CCS(=O)(=O)C4)c3n2)c2ccc(Cl)cc21] | 2-(6-Chloro-1-methyl-1H-indazol-3-yl)-5H-pyrrolo[2,3-b]pyrazine-7-carboxylic acid (1,1-dioxo-tetrahydro-1λ6-thiophen-3-yl)-amide |
| I-114 | 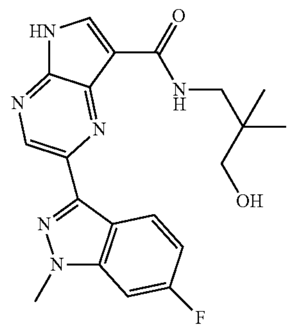 [SMILES: Cn1nc(-c2cnc3[nH]cc(C(=O)NCC(C)(C)CO)c3n2)c2ccc(F)cc21] | 2-(6-Fluoro-1-methyl-1H-indazol-3-yl)-5H-pyrrolo[2,3-b]pyrazine-7-carboxylic acid (3-hydroxy-2,2-dimethyl-propyl)-amide |
| I-115 | 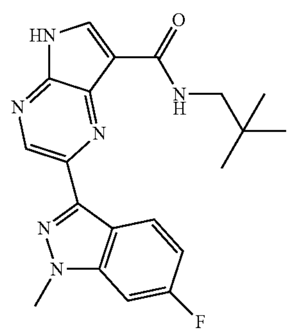 [SMILES: Cn1nc(-c2cnc3[nH]cc(C(=O)NCC(C)(C)C)c3n2)c2ccc(F)cc21] | 2-(6-Fluoro-1-methyl-1H-indazol-3-yl)-5H-pyrrolo[2,3-b]pyrazine-7-carboxylic acid (2,2-dimethyl-propyl)-amide |
| I-116 | 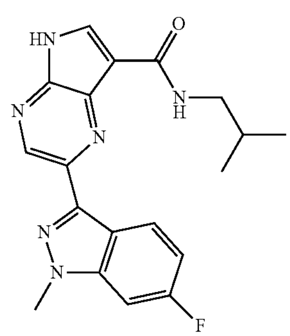 [SMILES: CC(C)CNC(=O)c1c[nH]c2ncc(-c3nn(C)c4cc(F)ccc34)nc12] | 2-(6-Fluoro-1-methyl-1H-indazol-3-yl)-5H-pyrrolo[2,3-b]pyrazine-7-carboxylic acid isobutyl-amide |

TABLE I-continued

| COMPOUND | STRUCTURE | SYSTEMATIC NAME |
|---|---|---|
| I-117 | 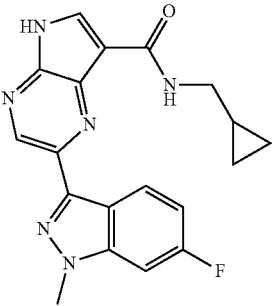 [SMILES: Cn1nc(-c2cnc3[nH]cc(C(=O)NCC4CC4)c3n2)c2ccc(F)cc21] | 2-(6-Fluoro-1-methyl-1H-indazol-3-yl)-5H-pyrrolo[2,3-b]pyrazine-7-carboxylic acid cyclopropylmethyl-amide |
| I-118 | 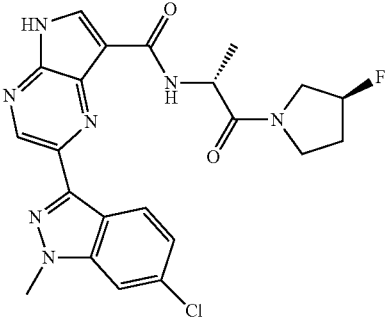 [SMILES: C[C@@H](NC(=O)c1c[nH]c2ncc(-c3nn(C)c4cc(Cl)ccc34)nc12)C(=O)N1CC[C@H](F)C1] | 2-(6-Chloro-1-methyl-1H-indazol-3-yl)-5H-pyrrolo[2,3-b]pyrazine-7-carboxylic acid [(R)-2-((S)-3-fluoro-pyrrolidin-1-yl)-1-methyl-2-oxo-ethyl]-amide |
| I-119 | 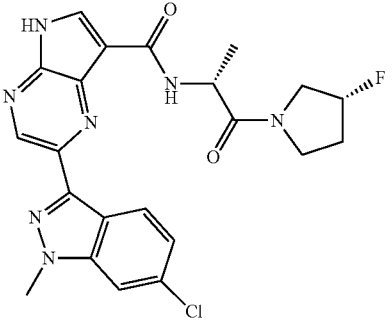 [SMILES: C[C@@H](NC(=O)c1c[nH]c2ncc(-c3nn(C)c4cc(Cl)ccc34)nc12)C(=O)N1CC[C@@H](F)C1] | 2-(6-Chloro-1-methyl-1H-indazol-3-yl)-5H-pyrrolo[2,3-b]pyrazine-7-carboxylic acid [(R)-2-((R)-3-fluoro-pyrrolidin-1-yl)-methyl-2-oxo-ethyl]-amide |
| I-120 | 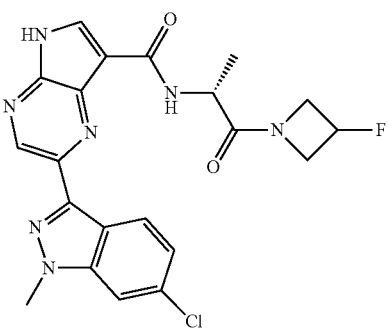 [SMILES: C[C@@H](NC(=O)c1c[nH]c2ncc(-c3nn(C)c4cc(Cl)ccc34)nc12)C(=O)N1CC(F)C1] | 2-(6-Chloro-1-methyl-1H-indazol-3-yl)-5H-pyrrolo[2,3-b]pyrazine-7-carboxylic acid [(R)-2-(3-fluoro-azetidin-1-yl)-1-methyl-2-oxo-ethyl)-amide |

TABLE I-continued

| COMPOUND | STRUCTURE | SYSTEMATIC NAME |
|---|---|---|
| I-121 | 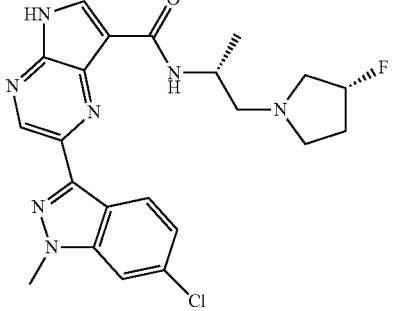 | 2-(6-Chloro-1-methyl-1H-indazol-3-yl)-5H-pyrrolo[2,3-b]pyrazine-7-carboxylic acid [(R)-2-((R)-3-fluoro-pyrrolidin-1-yl)-1-methyl-ethyl]-amide |
| I-122 | 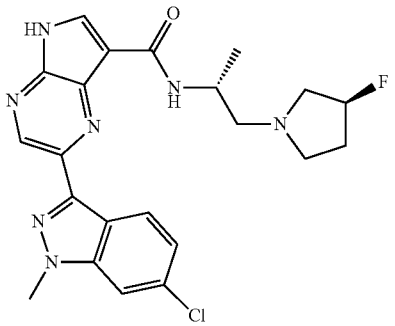 [SMILES: C[C@H](CN1CC[C@H](F)C1)NC(=O)c1c[nH]c2ncc(-c3nn(C)c4cc(Cl)ccc34)nc12] | 2-(6-Chloro-1-methyl-1H-indazol-3-yl)-5H-pyrrolo[2,3-b]pyrazine-7-carboxylic acid [(R)-2-((S)-3-fluoro-pyrrolidin-1-yl)-1-methyl-ethyl]-amide |
| I-123 | 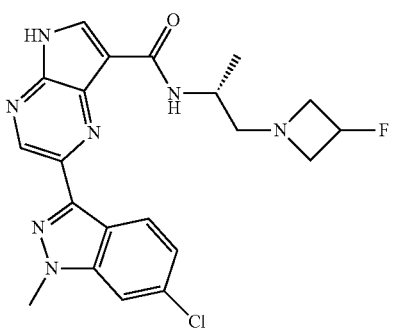 [SMILES: C[C@H](CN1CC(F)C1)NC(=O)c1c[nH]c2ncc(-c3nn(C)c4cc(Cl)ccc34)nc12] | 2-(6-Chloro-1-methyl-1H-indazol-3-yl)-5H-pyrrolo[2,3-b]pyrazine-7-carboxylic acid [(R)-2-(3-fluoro-azetidin-1-yl)-1-methyl-ethyl]-amide |
| I-124 | 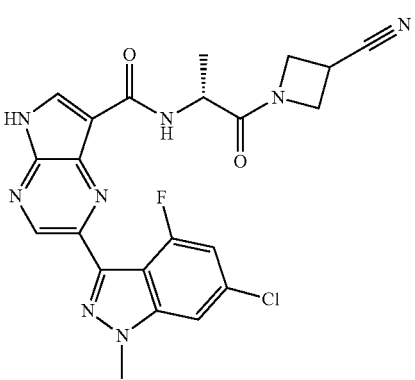 [SMILES: C[C@@H](NC(=O)c1c[nH]c2ncc(-c3nn(C)c4cc(Cl)cc(F)c34)nc12)C(=O)N1CC(C#N)C1] | 2-(6-Chloro-4-fluoro-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide |

TABLE I-continued

| COMPOUND | STRUCTURE | SYSTEMATIC NAME |
|---|---|---|
| I-125 | 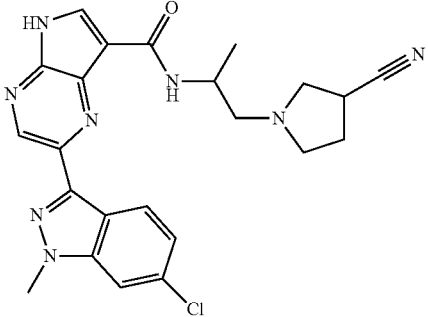 [SMILES: CC(CN1CCC(C#N)C1)NC(=O)c1c[nH]c2ncc(-c3nn(C)c4cc(Cl)ccc34)nc12] | 2-(6-Chloro-1-methyl-1H-indazol-3-yl)-5H-pyrrolo[2,3-b]pyrazine-7-carboxylic acid [2-(3-cyano-pyrrolidin-1-yl)-1-methyl-ethyl]-amide |
| I-126 | 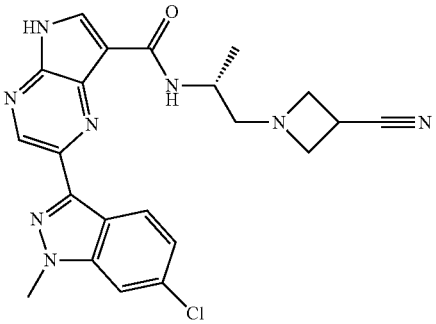 [SMILES: C[C@H](CN1CC(C#N)C1)NC(=O)c1c[nH]c2ncc(-c3nn(C)c4cc(Cl)ccc34)nc12] | 2-(6-Chloro-1-methyl-1H-indazol-3-yl)-5H-pyrrolo[2,3-b]pyrazine-7-carboxylic acid [(R)-2-(3-cyano-azetidin-1-yl)-1-methyl-ethyl]-amide |
| I-127 | 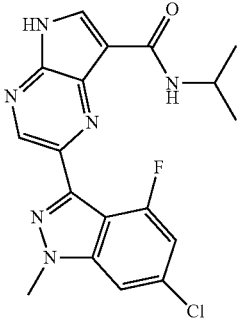 [SMILES: CC(C)NC(=O)c1c[nH]c2ncc(-c3nn(C)c4cc(Cl)cc(F)c34)nc12] | 2-(6-Chloro-4-fluoro-1-methyl-1H-indazol-3-yl)-5H-pyrrolo[2,3-b]pyrazine-7-carboxylic acid isopropylamide |
| I-128 | 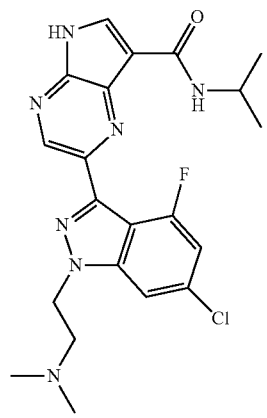 [SMILES: CC(C)NC(=O)c1c[nH]c2ncc(-c3nn(CCN(C)C)c4cc(Cl)cc(F)c34)nc12] | 2-[6-Chloro-1-(2-dimethylamino-ethyl)-4-fluoro-1H-indazol-3-yl]-5H-pyrrolo[2,3-b]pyrazine-7-carboxylic acid isopropylamide |

TABLE I-continued

| COMPOUND | STRUCTURE | SYSTEMATIC NAME |
| --- | --- | --- |
| I-129 | 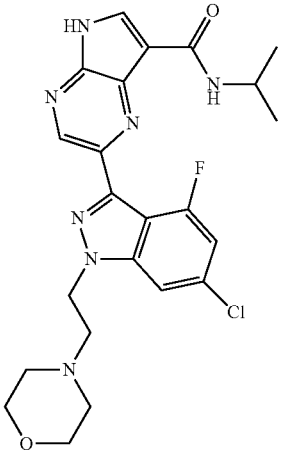 [SMILES: CC(C)NC(=O)c1c[nH]c2ncc(-c3nn(CCN4CCOCC4)c4cc(Cl)cc(F)c34)nc12] | 2-[6-Chloro-4-fluoro-1-(2-morpholin-4-yl-ethyl)-1H-indazol-3-yl]-5H-pyrrolo[2,3-b]pyrazine-7-carboxylic acid isopropylamide |
| I-130 | 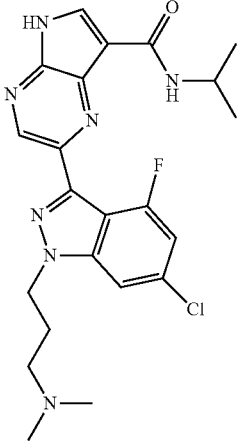 [SMILES: CC(C)NC(=O)c1c[nH]c2ncc(-c3nn(CCCN(C)C)c4cc(Cl)cc(F)c34)nc12] | 2-[6-Chloro-1-(3-dimethylamino-propyl)-4-fluoro-1H-indazol-3-yl]-5H-pyrrolo[2,3-b]pyrazine-7-carboxylic acid isopropylamide |
| I-131 | 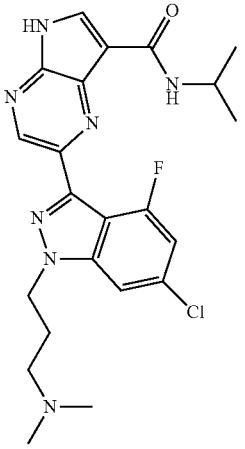 [SMILES: CC(C)NC(=O)c1c[nH]c2ncc(-c3nn(CCCN(C)C)c4cc(Cl)cc(F)c34)nc12] | 2-[6-Chloro-1-(3-dimethylamino-propyl)-4-fluoro-1H-indazol-3-yl]-5H-pyrrolo[2,3-b]pyrazine-7-carboxylic acid isopropylamide |

| COMPOUND | STRUCTURE | SYSTEMATIC NAME |
|---|---|---|
| I-132 | 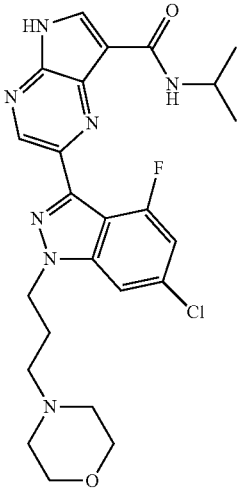 [SMILES: CC(C)NC(=O)c1c[nH]c2ncc(-c3nn(CCCN4CCOCC4)c4cc(Cl)cc(F)c34)nc12] | 2-[6-Chloro-4-fluoro-1-(3-morpholin-4-yl-propyl)-1H-indazol-3-yl]-5H-pyrrolo[2,3-b]pyrazine-7-carboxylic acid isopropylamide |
| I-133 | 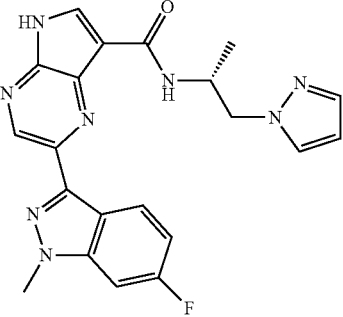 [SMILES: C[C@H](Cn1cccn1)NC(=O)c1c[nH]c2ncc(-c3nn(C)c4cc(F)ccc34)nc12] | 2-(6-Fluoro-1-methyl-1H-indazol-3-yl)-5H-pyrrolo[2,3-b]pyrazine-7-carboxylic acid ((R)-1-methyl-2-pyrazol-1-yl-ethyl)-amide |
| I-134 | 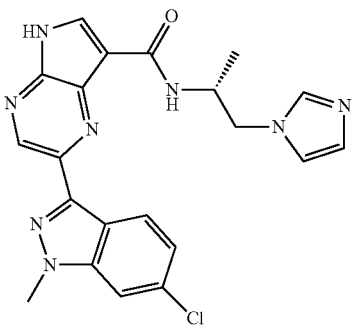 [SMILES: C[C@H](Cn1ccnc1)NC(=O)c1c[nH]c2ncc(-c3nn(C)c4cc(Cl)ccc34)nc12] | 2-(6-Chloro-1-methyl-1H-indazol-3-yl)-5H-pyrrolo[2,3-b]pyrazine-7-carboxylic acid ((R)-2-imidazol-1-yl-1-methyl-ethyl)-amide |
| I-135 | 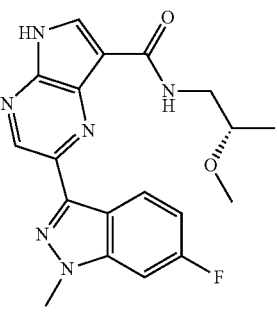 [SMILES: CO[C@@H](C)CNC(=O)c1c[nH]c2ncc(-c3nn(C)c4cc(F)ccc34)nc12] | 2-(6-Fluoro-1-methyl-1H-indazol-3-yl)-5H-pyrrolo[2,3-b]pyrazine-7-carboxylic acid ((S)-2-methoxy-propyl)-amide |

TABLE I-continued

| COMPOUND | STRUCTURE | SYSTEMATIC NAME |
|---|---|---|
| I-136 | 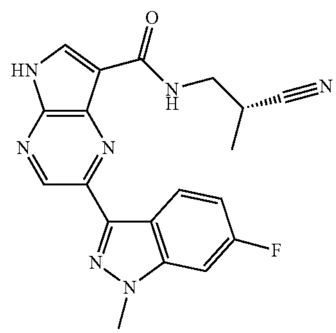 [SMILES: C[C@@H](C#N)CNC(=O)c1c[nH]c2ncc(-c3nn(C)c4cc(F)ccc34)nc12] | 2-(6-Fluoro-1-methyl-1H-indazol-3-yl)-5H-pyrrolo[2,3-b]pyrazine-7-carboxylic acid ((R)-2-cyano-2-methyl-ethyl)-amide |
| I-137 | 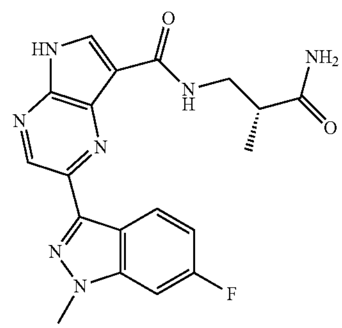 [SMILES: C[C@H](CNC(=O)c1c[nH]c2ncc(-c3nn(C)c4cc(F)ccc34)nc12)C(N)=O] | 2-(6-Fluoro-1-methyl-1H-indazol-3-yl)-5H-pyrrolo[2,3-b]pyrazine-7-carboxylic acid ((R)-2-carbamoyl-propyl)-amide |
| I-138 | 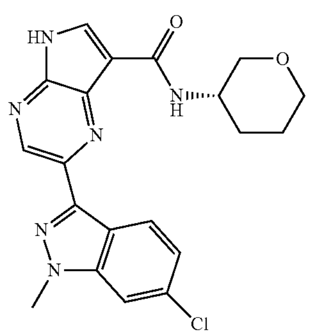 [SMILES: Cn1nc(-c2cnc3[nH]cc(C(=O)N[C@H]4CCCOC4)c3n2)c2ccc(Cl)cc21] | 2-(6-Chloro-1-methyl-1H-indazol-3-yl)-5H-pyrrolo[2,3-b]pyrazine-7-carboxylic acid (S)-tetrahydro-pyran-3-ylamide |
| I-139 | 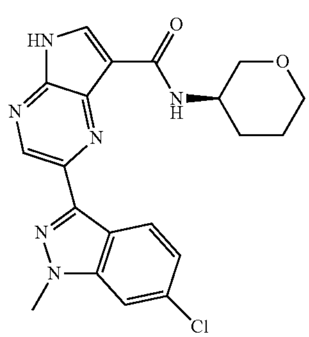 | 2-(6-Chloro-1-methyl-1H-indazol-3-yl)-5H-pyrrolo[2,3-b]pyrazine-7-carboxylic acid (R)-tetrahydro-pyran-3-ylamide |

TABLE I-continued

| COMPOUND | STRUCTURE | SYSTEMATIC NAME |
|---|---|---|
| I-140 | 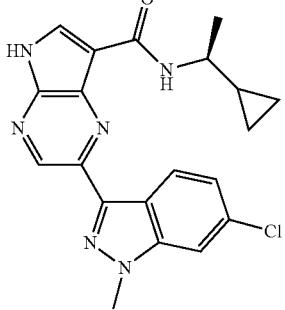 | 2-(6-Chloro-1-methyl-1H-indazol-3-yl)-5H-pyrrolo[2,3-b]pyrazine-7-carboxylic acid ((S)-1-cyclopropyl-ethyl)-amide |
| I-141 | 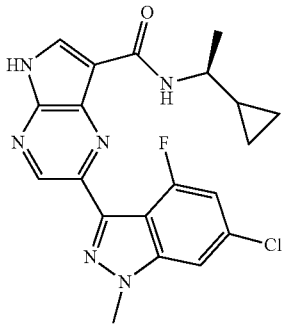 [SMILES: C[C@H](NC(=O)c1c[nH]c2ncc(-c3nn(C)c4cc(Cl)cc(F)c34)nc12)C1CC1] | 2-(6-Chloro-4-fluoro-1-methyl-1H-indazol-3-yl)-5H-pyrrolo[2,3-b]pyrazine-7-carboxylic acid ((S)-1-cyclopropyl-ethyl)-amide |
| I-142 | 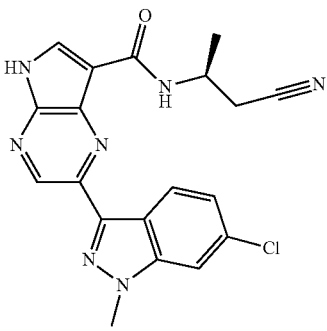 [SMILES: C[C@@H](CC#N)NC(=O)c1c[nH]c2ncc(-c3nn(C)c4cc(Cl)ccc34)nc12] | 2-(6-Chloro-1-methyl-1H-indazol-3-yl)-5H-pyrrolo[2,3-b]pyrazine-7-carboxylic acid ((S)-2-cyano-1-methyl-ethyl)-amide |
| I-143 | 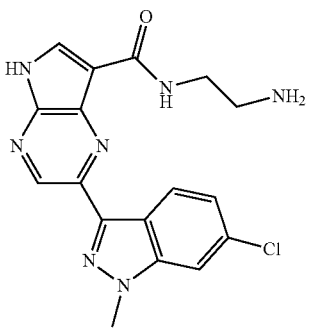 [SMILES: Cn1nc(-c2cnc3[nH]cc(C(=O)NCCN)c3n2)c2ccc(Cl)cc21] | 2-(6-Chloro-1-methyl-1H-indazol-3-yl)-5H-pyrrolo[2,3-b]pyrazine-7-carboxylic acid (2-amino-ethyl)-amide |

TABLE I-continued

| COMPOUND | STRUCTURE | SYSTEMATIC NAME |
| --- | --- | --- |
| I-144 | 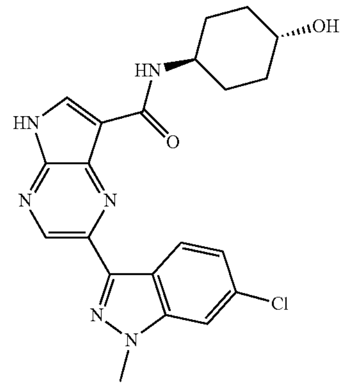 [SMILES: Cn1nc(-c2cnc3[nH]cc(C(=O)N[C@H]4CC[C@H](O)CC4)c3n2)c2ccc(Cl)cc21] | 2-(6-Chloro-1-methyl-1H-indazol-3-yl)-5H-pyrrolo[2,3-b]pyrazine-7-carboxylic acid (trans-4-hydroxy-cyclohexyl)-amide |
| I-145 | 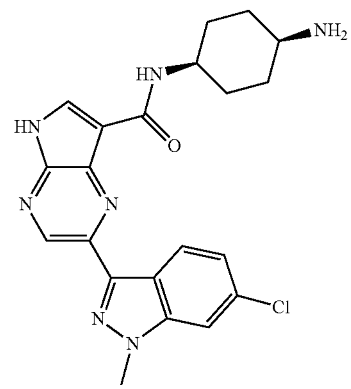 [SMILES: Cn1nc(-c2cnc3[nH]cc(C(=O)N[C@H]4CC[C@@H](N)CC4)c3n2)c2ccc(Cl)cc21] | 2-(6-Chloro-1-methyl-1H-indazol-3-yl)-5H-pyrrolo[2,3-b]pyrazine-7-carboxylic acid (cis-4-amino-cyclohexyl)-amide |
| I-146 | 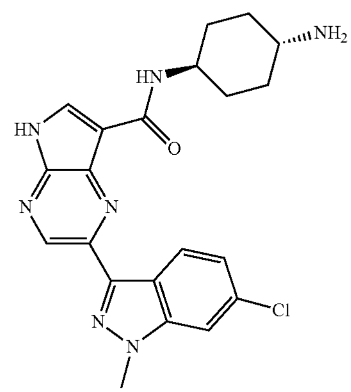 [SMILES: Cn1nc(-c2cnc3[nH]cc(C(=O)N[C@H]4CC[C@H](N)CC4)c3n2)c2ccc(Cl)cc21] | 2-(6-Chloro-1-methyl-1H-indazol-3-yl)-5H-pyrrolo[2,3-b]pyrazine-7-carboxylic acid (trans-4-amino-cyclohexyl)-amide |
| I-147 | 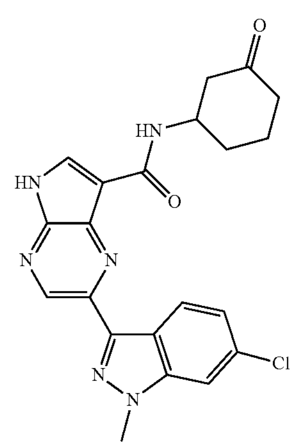 [SMILES: Cn1nc(-c2cnc3[nH]cc(C(=O)NC4CCCC(=O)C4)c3n2)c2ccc(Cl)cc21] | 2-(6-Chloro-1-methyl-1H-indazol-3-yl)-5H-pyrrolo[2,3-b]pyrazine-7-carboxylic acid (3-oxo-cyclohexyl)-amide |

TABLE I-continued

| COMPOUND | STRUCTURE | SYSTEMATIC NAME |
|---|---|---|
| I-148 | 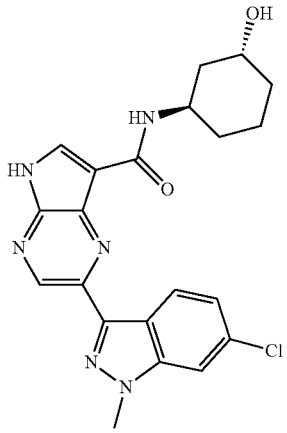 [SMILES: Cn1nc(-c2cnc3[nH]cc(C(=O)N[C@@H]4CCC[C@@H](O)C4)c3n2)c2ccc(Cl)cc21] | 2-(6-Chloro-1-methyl-1H-indazol-3-yl)-5H-pyrrolo[2,3-b]pyrazine-7-carboxylic acid (trans-3-hydroxy-cyclohexyl)-amide |
| I-149 | 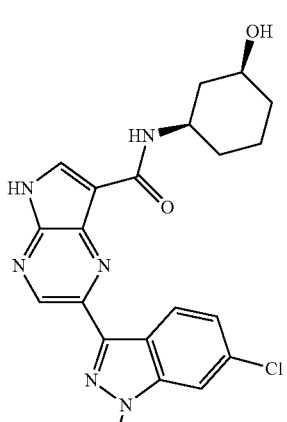 | 2-(6-Chloro-1-methyl-1H-indazol-3-yl)-5H-pyrrolo[2,3-b]pyrazine-7-carboxylic acid (cis-3-hydroxy-cyclohexyl)-amide |
| I-150 | 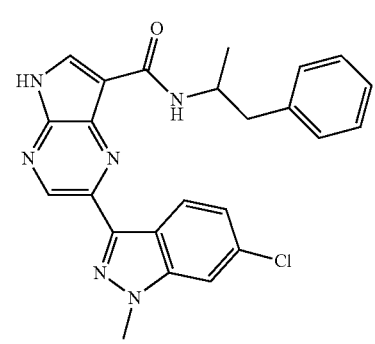 [SMILES: CC(Cc1ccccc1)NC(=O)c1c[nH]c2ncc(-c3nn(C)c4cc(Cl)ccc34)nc12] | 2-(6-Chloro-1-methyl-1H-indazol-3-yl)-5H-pyrrolo[2,3-b]pyrazine-7-carboxylic acid (1-methyl-2-phenyl-ethyl)-amide |
| I-151 | 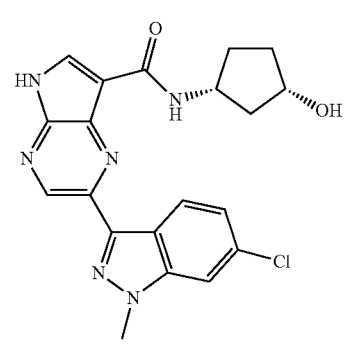 [SMILES: Cn1nc(-c2cnc3[nH]cc(C(=O)N[C@@H]4CC[C@H](O)C4)c3n2)c2ccc(Cl)cc21] | 2-(6-Chloro-1-methyl-1H-indazol-3-yl)-5H-pyrrolo[2,3-b]pyrazine-7-carboxylic acid ((1R,3S)-3-hydroxy-cyclopentyl)-amide |

TABLE I-continued

| COMPOUND | STRUCTURE | SYSTEMATIC NAME |
|---|---|---|
| I-152 | 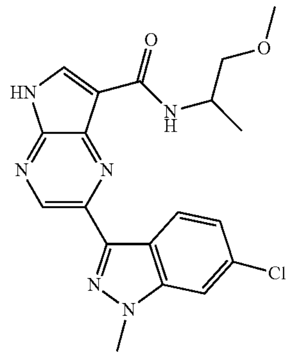 | 2-(6-Chloro-1-methyl-1H-indazol-3-yl)-5H-pyrrolo[2,3-b]pyrazine-7-carboxylic acid (2-methoxy-1-methyl-ethyl)-amide |
| I-153 | 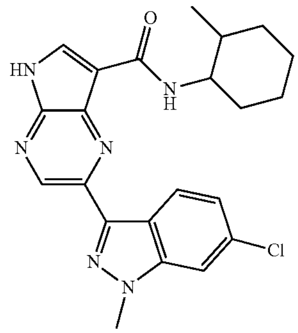 [SMILES: CC1CCCCC1NC(=O)c1c[nH]c2ncc(-c3nn(C)c4cc(Cl)ccc34)nc12] | 2-(6-Chloro-1-methyl-1H-indazol-3-yl)-5H-pyrrolo[2,3-b]pyrazine-7-carboxylic acid (2-methyl-cyclohexyl)-amide |
| I-154 | 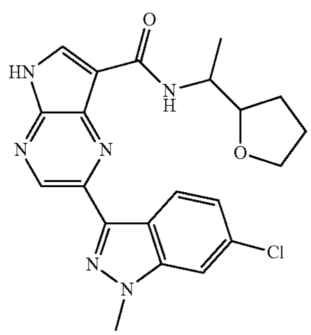 [SMILES: CC(NC(=O)c1c[nH]c2ncc(-c3nn(C)c4cc(Cl)ccc34)nc12)C1CCCO1] | 2-(6-Chloro-1-methyl-1H-indazol-3-yl)-5H-pyrrolo[2,3-b]pyrazine-7-carboxylic acid [1-(tetrahydro-furan-2-yl)-ethyl]-amide |
| I-155 | 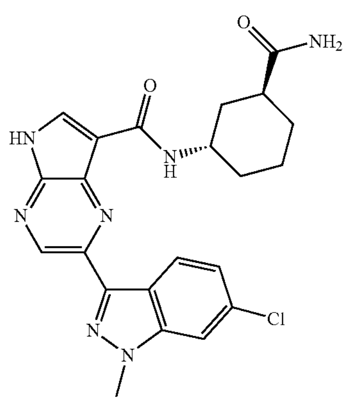 [SMILES: Cn1nc(-c2cnc3[nH]cc(C(=O)N[C@H]4CCC[C@H](C(N)=O)C4)c3n2)c2ccc(Cl)cc21] | 2-(6-Chloro-1-methyl-1H-indazol-3-yl)-5H-pyrrolo[2,3-b]pyrazine-7-carboxylic acid (trans-3-carbamoyl-cyclohexyl)-amide |

TABLE I-continued

| COMPOUND | STRUCTURE | SYSTEMATIC NAME |
| --- | --- | --- |
| I-156 | 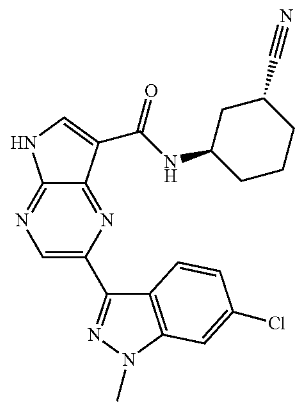 [SMILES: Cn1nc(-c2cnc3[nH]cc(C(=O)N[C@@H]4CCC[C@@H](C#N)C4)c3n2)c2ccc(Cl)cc21] | 2-(6-Chloro-1-methyl-1H-indazol-3-yl)-5H-pyrrolo[2,3-b]pyrazine-7-carboxylic acid (trans-3-cyano-cyclohexyl)-amide |
| I-157 | 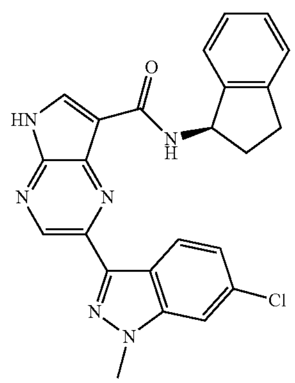 [SMILES: Cn1nc(-c2cnc3[nH]cc(C(=O)N[C@@H]4CCc5ccccc54)c3n2)c2ccc(Cl)cc21] | 2-(6-Chloro-1-methyl-1H-indazol-3-yl)-5H-pyrrolo[2,3-b]pyrazine-7-carboxylic acid (R)-indan-1-ylamide |
| I-158 | 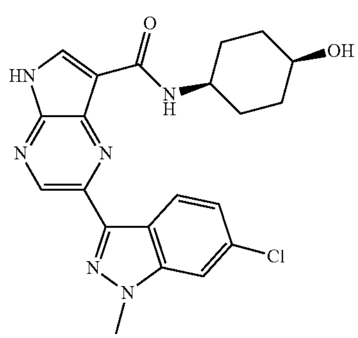 [SMILES: Cn1nc(-c2cnc3[nH]cc(C(=O)N[C@H]4CC[C@@H](O)CC4)c3n2)c2ccc(Cl)cc21] | 2-(6-Chloro-1-methyl-1H-indazol-3-yl)-5H-pyrrolo[2,3-b]pyrazine-7-carboxylic acid (cis-4-hydroxy-cyclohexyl)-amide |
| I-159 | 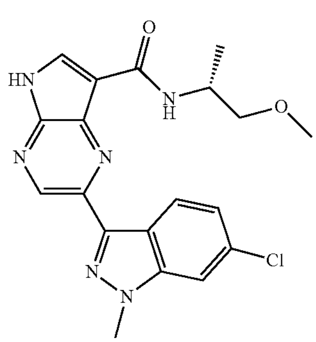 [SMILES: COC[C@@H](C)NC(=O)c1c[nH]c2ncc(-c3nn(C)c4cc(Cl)ccc34)nc12] | 2-(6-Chloro-1-methyl-1H-indazol-3-yl)-5H-pyrrolo[2,3-b]pyrazine-7-carboxylic acid ((R)-2-methoxy-1-methyl-ethyl)-amide |

TABLE I-continued

| COMPOUND | STRUCTURE | SYSTEMATIC NAME |
|---|---|---|
| I-160 | 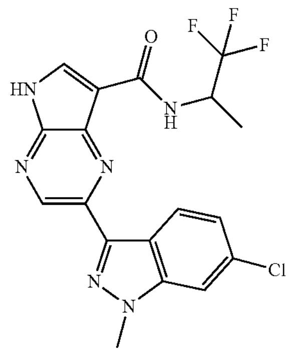 [SMILES: CC(NC(=O)c1c[nH]c2ncc(-c3nn(C)c4cc(Cl)ccc34)nc12)C(F)(F)F] | 2-(6-Chloro-1-methyl-1H-indazol-3-yl)-5H-pyrrolo[2,3-b]pyrazine-7-carboxylic acid (2,2,2-trifluoro-1-methyl-ethyl)-amide |
| I-161 | 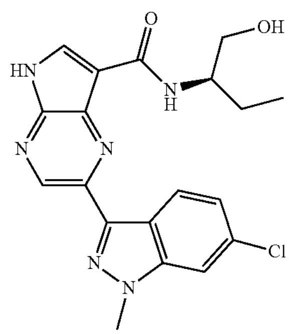 [SMILES: CC[C@H](CO)NC(=O)c1c[nH]c2ncc(-c3nn(C)c4cc(Cl)ccc34)nc12] | 2-(6-Chloro-1-methyl-1H-indazol-3-yl)-5H-pyrrolo[2,3-b]pyrazine-7-carboxylic acid ((R)-1-hydroxymethyl-propyl)-amide |
| I-162 | 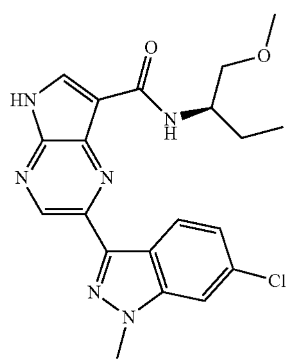 [SMILES: CC[C@H](COC)NC(=O)c1c[nH]c2ncc(-c3nn(C)c4cc(Cl)ccc34)nc12] | 2-(6-Chloro-1-methyl-1H-indazol-3-yl)-5H-pyrrolo[2,3-b]pyrazine-7-carboxylic acid ((R)-1-methoxymethyl-propyl)-amide |
| I-163 | 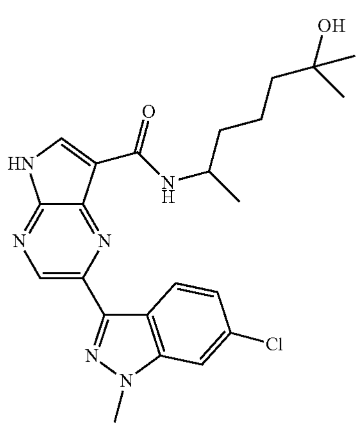 [SMILES: CC(CCCC(C)(C)O)NC(=O)c1c[nH]c2ncc(-c3nn(C)c4cc(Cl)ccc34)nc12] | 2-(6-Chloro-1-methyl-1H-indazol-3-yl)-5H-pyrrolo[2,3-b]pyrazine-7-carboxylic acid (5-hydroxy-1,5-dimethyl-hexyl)-amide |

TABLE I-continued

| COMPOUND | STRUCTURE | SYSTEMATIC NAME |
|---|---|---|
| I-164 | 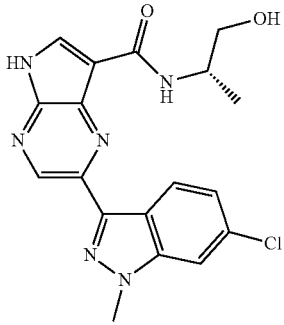 [SMILES: C[C@@H](CO)NC(=O)c1c[nH]c2ncc(-c3nn(C)c4cc(Cl)ccc34)nc12] | 2-(6-Chloro-1-methyl-1H-indazol-3-yl)-5H-pyrrolo[2,3-b]pyrazine-7-carboxylic acid ((S)-2-hydroxy-1-methyl-ethyl)-amide |
| I-165 | 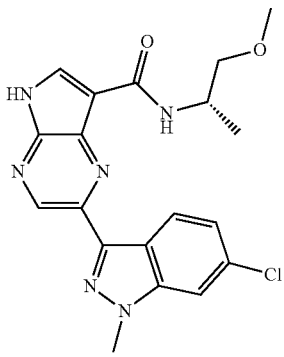 [SMILES: COC[C@H](C)NC(=O)c1c[nH]c2ncc(-c3nn(C)c4cc(Cl)ccc34)nc12] | 2-(6-Chloro-1-methyl-1H-indazol-3-yl)-5H-pyrrolo[2,3-b]pyrazine-7-carboxylic acid ((S)-2-methoxy-1-methyl-ethyl)-amide |
| I-166 | 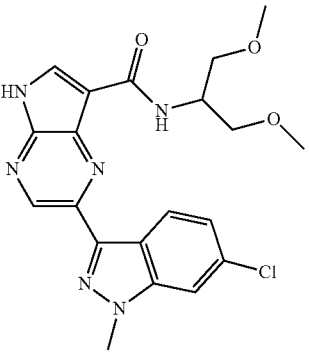 [SMILES: COCC(COC)NC(=O)c1c[nH]c2ncc(-c3nn(C)c4cc(Cl)ccc34)nc12] | 2-(6-Chloro-1-methyl-1H-indazol-3-yl)-5H-pyrrolo[2,3-b]pyrazine-7-carboxylic acid (2-methoxy-1-methoxymethyl-ethyl)-amide |
| I-167 | 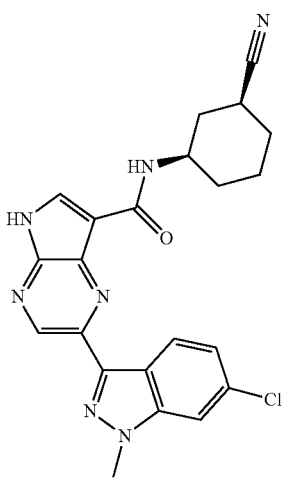 [SMILES: Cn1nc(-c2cnc3[nH]cc(C(=O)N[C@@H]4CCC[C@H](C#N)C4)c3n2)c2ccc(Cl)cc21] | 2-(6-Chloro-1-methyl-1H-indazol-3-yl)-5H-pyrrolo[2,3-b]pyrazine-7-carboxylic acid (cis-3-cyano-cyclohexyl)-amide |

TABLE I-continued
| COMPOUND | STRUCTURE | SYSTEMATIC NAME |
|---|---|---|
| I-168 | 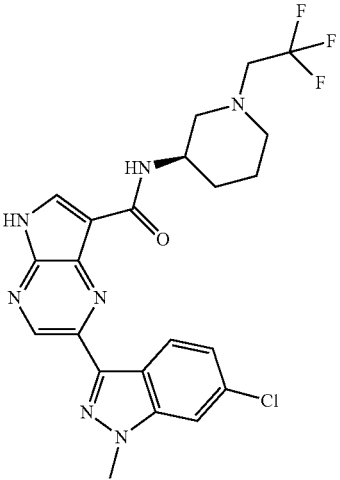 [SMILES: Cn1nc(-c2cnc3[nH]cc(C(=O)N[C@@H]4CCCN(CC(F)(F)F)C4)c3n2)c2ccc(Cl)cc21] | 2-(6-Chloro-1-methyl-1H-indazol-3-yl)-5H-pyrrolo[2,3-b]pyrazine-7-carboxylic acid [(R)-1-(2,2,2-trifluoro-ethyl)-piperidin-3-yl]-amide |
| I-169 | 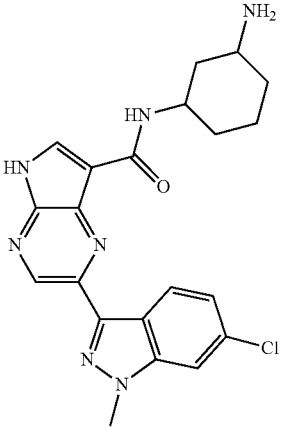 [SMILES: Cn1nc(-c2cnc3[nH]cc(C(=O)NC4CCCC(N)C4)c3n2)c2ccc(Cl)cc21] | 2-(6-Chloro-1-methyl-1H-indazol-3-yl)-5H-pyrrolo[2,3-b]pyrazine-7-carboxylic acid (3-amino-cyclohexyl)-amide |
| I-170 | 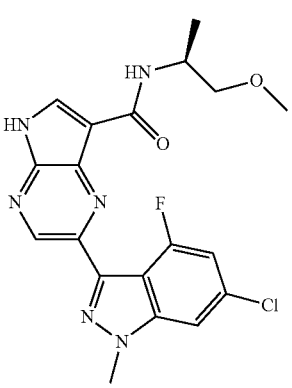 [SMILES: COC[C@H](C)NC(=O)c1c[nH]c2ncc(-c3nn(C)c4cc(Cl)cc(F)c34)nc12] | 2-(6-Chloro-4-fluoro-1-methyl-1H-indazol-3-yl)-5H-pyrrolo[2,3-b]pyrazine-7-carboxylic acid ((S)-2-methoxy-1-methyl-ethyl)-amide |

| COMPOUND | STRUCTURE | SYSTEMATIC NAME |
|---|---|---|
| I-171 | 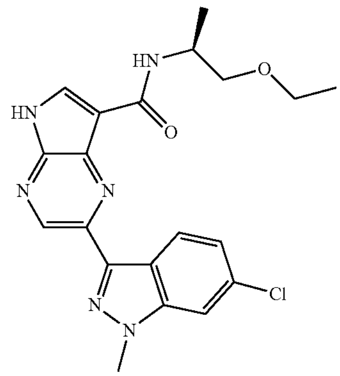 [SMILES: CCOC[C@H](C)NC(=O)c1c[nH]c2ncc(-c3nn(C)c4cc(Cl)ccc34)nc12] | 2-(6-Chloro-1-methyl-1H-indazol-3-yl)-5H-pyrrolo[2,3-b]pyrazine-7-carboxylic acid ((S)-2-ethoxy-1-methyl-ethyl)-amide |
| I-172 | 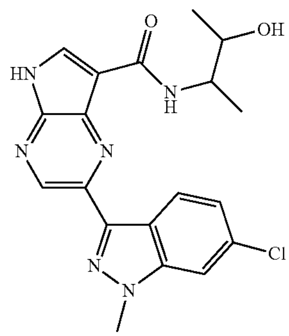 [SMILES: CC(O)C(C)NC(=O)c1c[nH]c2ncc(-c3nn(C)c4cc(Cl)ccc34)nc12] | 2-(6-Chloro-1-methyl-1H-indazol-3-yl)-5H-pyrrolo[2,3-b]pyrazine-7-carboxylic acid (2-hydroxy-1-methyl-propyl)-amide |
| I-173 | 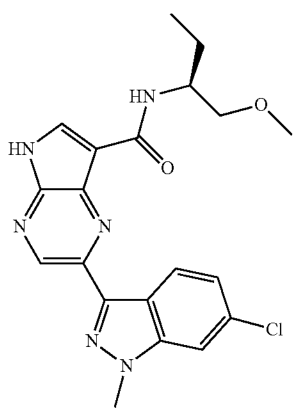 [SMILES: CC[C@@H](COC)NC(=O)c1c[nH]c2ncc(-c3nn(C)c4cc(Cl)ccc34)nc12] | 2-(6-Chloro-1-methyl-1H-indazol-3-yl)-5H-pyrrolo[2,3-b]pyrazine-7-carboxylic acid ((S)-1-methoxymethyl-propyl)-amide |
| I-174 | 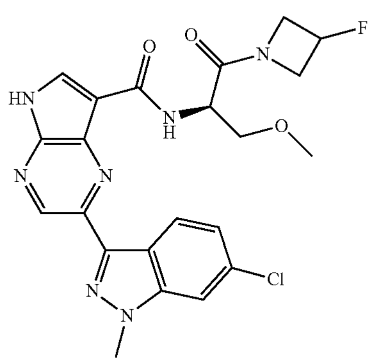 [SMILES: COC[C@@H](NC(=O)c1c[nH]c2ncc(-c3nn(C)c4cc(Cl)ccc34)nc12)C(=O)N1CC(F)C1] | 2-(6-Chloro-1-methyl-1H-indazol-3-yl)-5H-pyrrolo[2,3-b]pyrazine-7-carboxylic acid [(R)-2-(3-fluoro-azetidin-1-yl)-1-methoxymethyl-2-oxo-ethyl]-amide |

TABLE I-continued

| COMPOUND | STRUCTURE | SYSTEMATIC NAME |
| --- | --- | --- |
| I-175 | 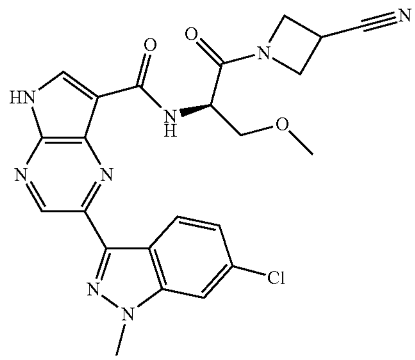 [SMILES: COC[C@@H](NC(=O)c1c[nH]c2ncc(-c3nn(C)c4cc(Cl)ccc34)nc12)C(=O)N1CC(C#N)C1] | 2-(6-Chloro-1-methyl-1H-indazol-3-yl)-5H-pyrrolo[2,3-b]pyrazine-7-carboxylic acid [(R)-2-(3-cyano-azetidin-1-yl)-1-methoxymethyl-2-oxo-ethyl]-amide |
| I-176 | 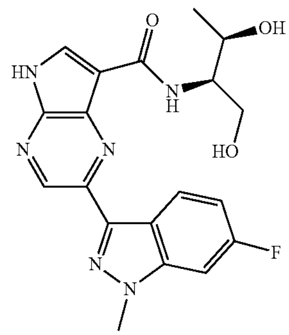 [SMILES: C[C@@H](O)[C@@H](CO)NC(=O)c1c[nH]c2ncc(-c3nn(C)c4cc(F)ccc34)nc12] | 2-(6-Fluoro-1-methyl-1H-indazol-3-yl)-5H-pyrrolo[2,3-b]pyrazine-7-carboxylic acid ((1R,2R)-2-hydroxy-1-hydroxymethyl-propyl)-amide |
| I-177 | 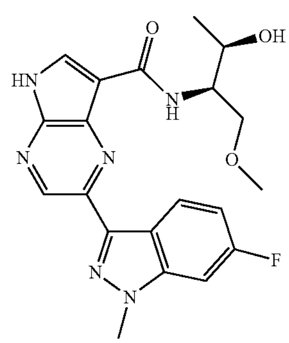 [SMILES: COC[C@@H](NC(=O)c1c[nH]c2ncc(-c3nn(C)c4cc(F)ccc34)nc12)[C@@H](C)O] | 2-(6-Fluoro-1-methyl-1H-indazol-3-yl)-5H-pyrrolo[2,3-b]pyrazine-7-carboxylic acid ((1R,2R)-2-hydroxy-1-methoxymethyl-propyl)-amide |
| I-178 | 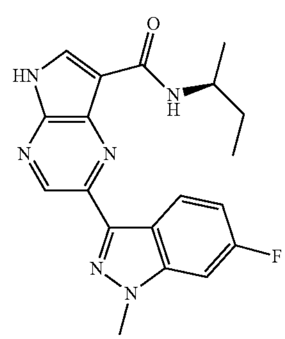 [SMILES: CC[C@H](C)NC(=O)c1c[nH]c2ncc(-c3nn(C)c4cc(F)ccc34)nc12] | 2-(6-Fluoro-1-methyl-1H-indazol-3-yl)-5H-pyrrolo[2,3-b]pyrazine-7-carboxylic acid ((S)-sec-butyl)-amide |

TABLE I-continued

| COMPOUND | STRUCTURE | SYSTEMATIC NAME |
|---|---|---|
| I-179 | 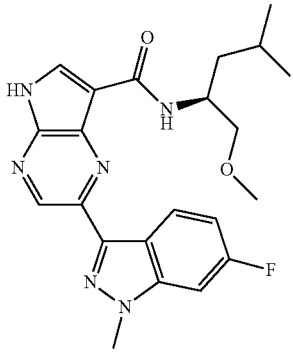 [SMILES: COC[C@H](CC(C)C)NC(=O)c1c[nH]c2ncc(-c3nn(C)c4cc(F)ccc34)nc12] | 2-(6-Fluoro-1-methyl-1H-indazol-3-yl)-5H-pyrrolo[2,3-b]pyrazine-7-carboxylic acid ((S)-1-methoxymethyl-3-methyl-butyl)-amide |
| I-180 | 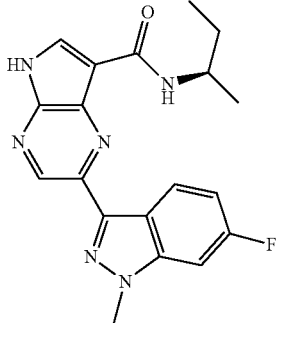 [SMILES: CC[C@@H](C)NC(=O)c1c[nH]c2ncc(-c3nn(C)c4cc(F)ccc34)nc12] | 2-(6-Fluoro-1-methyl-1H-indazol-3-yl)-5H-pyrrolo[2,3-b]pyrazine-7-carboxylic acid ((R)-sec-butyl)-amide |
| I-181 | 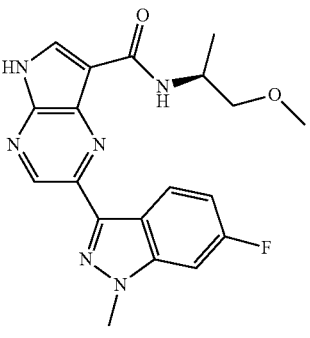 [SMILES: COC[C@H](C)NC(=O)c1c[nH]c2ncc(-c3nn(C)c4cc(F)ccc34)nc12] | 2-(6-Fluoro-1-methyl-1H-indazol-3-yl)-5H-pyrrolo[2,3-b]pyrazine-7-carboxylic acid ((S)-2-methoxy-1-methyl-ethyl)-amide |
| I-182 | 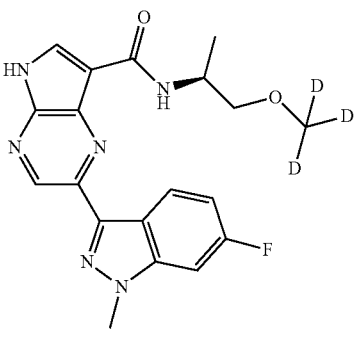 [SMILES: [2H]C([2H])([2H])OC[C@H](C)NC(=O)c1c[nH]c2ncc(-c3nn(C)c4cc(F)ccc34)nc12] | 2-(6-Fluoro-1-methyl-1H-indazol-3-yl)-5H-pyrrolo[2,3-b]pyrazine-7-carboxylic acid ((S)-1-methyl-2-trideuteromethoxy-ethyl)-amide |

TABLE I-continued

| COMPOUND | STRUCTURE | SYSTEMATIC NAME |
|---|---|---|
| I-183 | 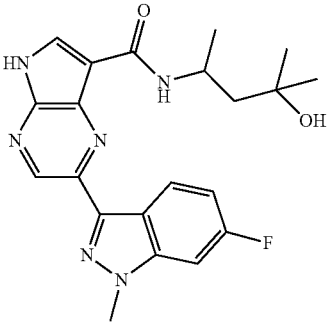 [SMILES: CC(CC(C)(C)O)NC(=O)c1c[nH]c2ncc(-c3nn(C)c4cc(F)ccc34)nc12] | 2-(6-Fluoro-1-methyl-1H-indazol-3-yl)-5H-pyrrolo[2,3-b]pyrazine-7-carboxylic acid (3-hydroxy-1,3-dimethyl-butyl)-amide |
| I-184 | 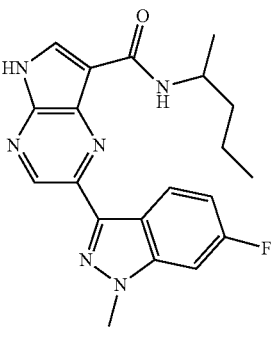 [SMILES: CCCC(C)NC(=O)c1c[nH]c2ncc(-c3nn(C)c4cc(F)ccc34)nc12] | 2-(6-Fluoro-1-methyl-1H-indazol-3-yl)-5H-pyrrolo[2,3-b]pyrazine-7-carboxylic acid (1-methyl-butyl)-amide |
| I-185 | 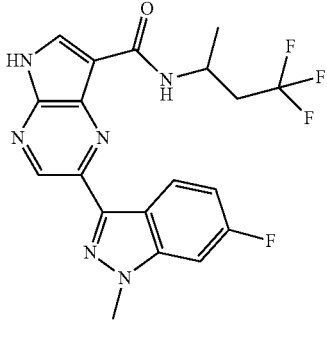 [SMILES: CC(CC(F)(F)F)NC(=O)c1c[nH]c2ncc(-c3nn(C)c4cc(F)ccc34)nc12] | 2-(6-Fluoro-1-methyl-1H-indazol-3-yl)-5H-pyrrolo[2,3-b]pyrazine-7-carboxylic acid (3,3,3-trifluoro-1-methyl-propyl)-amide |
| I-186 | 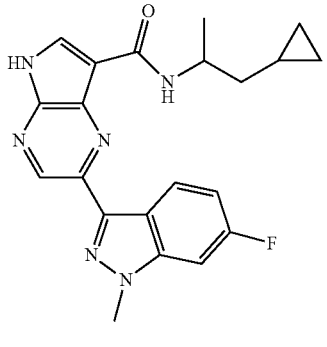 [SMILES: CC(CC1CC1)NC(=O)c1c[nH]c2ncc(-c3nn(C)c4cc(F)ccc34)nc12] | 2-(6-Fluoro-1-methyl-1H-indazol-3-yl)-5H-pyrrolo[2,3-b]pyrazine-7-carboxylic acid (2-cyclopropyl-1-methyl-ethyl)-amide |

TABLE I-continued

| COMPOUND | STRUCTURE | SYSTEMATIC NAME |
| --- | --- | --- |
| I-187 | 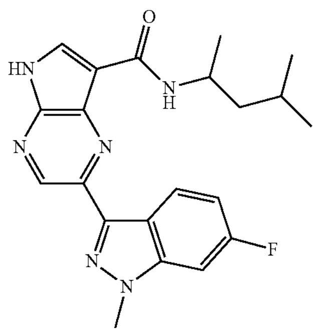 [SMILES: CC(C)CC(C)NC(=O)c1c[nH]c2ncc(-c3nn(C)c4cc(F)ccc34)nc12] | 2-(6-Fluoro-1-methyl-1H-indazol-3-yl)-5H-pyrrolo[2,3-b]pyrazine-7-carboxylic acid (1,3-dimethyl-butyl)-amide |
| I-188 | 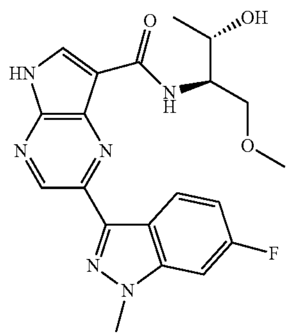 [SMILES: COC[C@@H](NC(=O)c1c[nH]c2ncc(-c3nn(C)c4cc(F)ccc34)nc12)[C@H](C)O] | 2-(6-Fluoro-1-methyl-1H-indazol-3-yl)-5H-pyrrolo[2,3-b]pyrazine-7-carboxylic acid ((1R,2S)-2-hydroxy-1-methoxymethyl-propyl)-amide |
| I-189 | 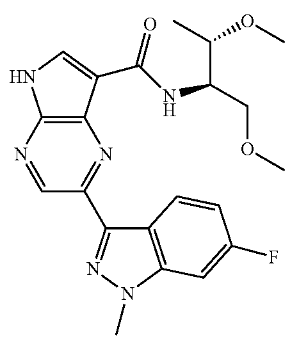 [SMILES: COC[C@@H](NC(=O)c1c[nH]c2ncc(-c3nn(C)c4cc(F)ccc34)nc12)[C@H](C)OC] | 2-(6-Fluoro-1-methyl-1H-indazol-3-yl)-5H-pyrrolo[2,3-b]pyrazine-7-carboxylic acid ((1R,2S)-2-methoxy-1-methoxymethyl-propyl)-amide |
| I-190 | 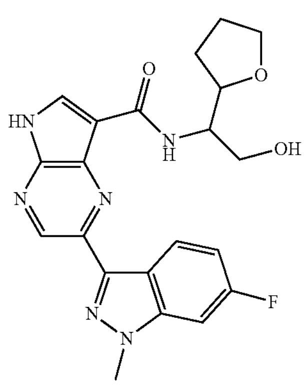 [SMILES: Cn1nc(-c2cnc3[nH]cc(C(=O)NC(CO)C4CCCO4)c3n2)c2ccc(F)cc21] | 2-(6-Fluoro-1-methyl-1H-indazol-3-yl)-5H-pyrrolo[2,3-b]pyrazine-7-carboxylic acid [2-hydroxy-1-(tetrahydro-furan-2-yl)-ethyl]-amide |

TABLE I-continued

| COMPOUND | STRUCTURE | SYSTEMATIC NAME |
| --- | --- | --- |
| I-191 | 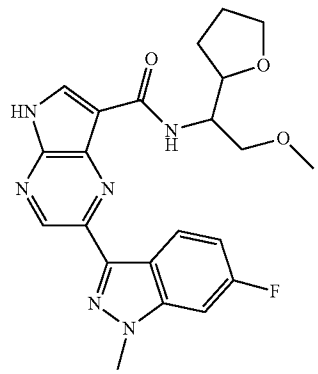 [SMILES: COCC(NC(=O)c1c[nH]c2ncc(-c3nn(C)c4cc(F)ccc34)nc12)C1CCCO1] | 2-(6-Fluoro-1-methyl-1H-indazol-3-yl)-5H-pyrrolo[2,3-b]pyrazine-7-carboxylic acid [2-methoxy-1-(tetrahydro-furan-2-yl)-ethyl]-amide |
| I-192 | 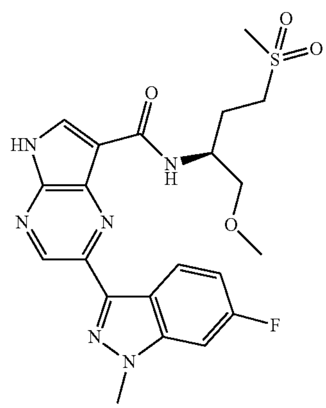 [SMILES: COC[C@H](CCS(C)(=O)=O)NC(=O)c1c[nH]c2ncc(-c3nn(C)c4cc(F)ccc34)nc12] | 2-(6-Fluoro-1-methyl-1H-indazol-3-yl)-5H-pyrrolo[2,3-b]pyrazine-7-carboxylic acid ((S)-3-methanesulfonyl-1-methoxymethyl-propyl)-amide |
| I-193 | 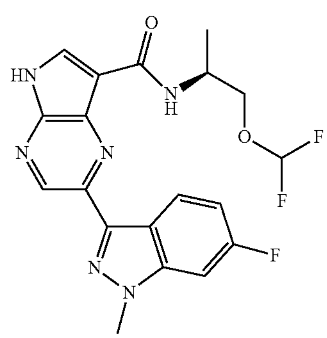 [SMILES: C[C@@H](COC(F)F)NC(=O)c1c[nH]c2ncc(-c3nn(C)c4cc(F)ccc34)nc12] | 2-(6-Fluoro-1-methyl-1H-indazol-3-yl)-5H-pyrrolo[2,3-b]pyrazine-7-carboxylic acid ((S)-2-difluoromethoxy-1-methyl-ethyl)-amide |
| I-194 | 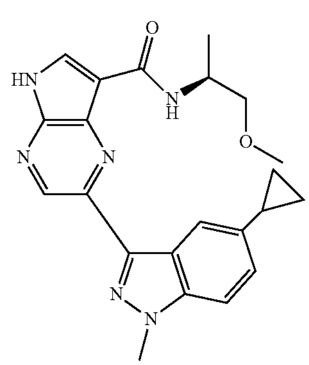 [SMILES: COC[C@H](C)NC(=O)c1c[nH]c2ncc(-c3nn(C)c4ccc(C5CC5)cc34)nc12] | 2-(5-Cyclopropyl-1-methyl-1H-indazol-3-yl)-5H-pyrrolo[2,3-b]pyrazine-7-carboxylic acid ((S)-2-methoxy-1-methyl-ethyl)-amide |

TABLE I-continued

| COMPOUND | STRUCTURE | SYSTEMATIC NAME |
|---|---|---|
| I-195 | 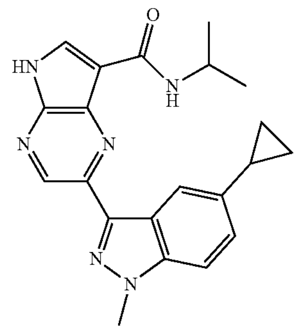 [SMILES: CC(C)NC(=O)c1c[nH]c2ncc(-c3nn(C)c4ccc(C5CC5)cc34)nc12] | 2-(5-Cyclopropyl-1-methyl-1H-indazol-3-yl)-5H-pyrrolo[2,3-b]pyrazine-7-carboxylic acid isopropylamide |
| I-196 | 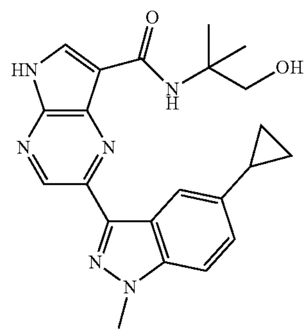 [SMILES: Cn1nc(-c2cnc3[nH]cc(C(=O)NC(C)(C)CO)c3n2)c2cc(C3CC3)ccc21] | 2-(5-Cyclopropyl-1-methyl-1H-indazol-3-yl)-5H-pyrrolo[2,3-b]pyrazine-7-carboxylic acid (2-hydroxy-1,1-dimethyl-ethyl)-amide |
| I-197 | 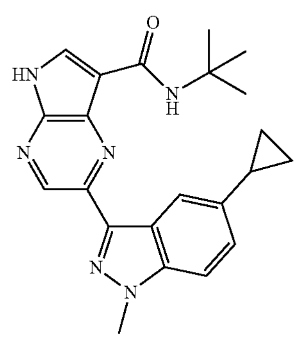 [SMILES: Cn1nc(-c2cnc3[nH]cc(C(=O)NC(C)(C)C)c3n2)c2cc(C3CC3)ccc21] | 2-(5-Cyclopropyl-1-methyl-1H-indazol-3-yl)-5H-pyrrolo[2,3-b]pyrazine-7-carboxylic acid tert-butylamide |
| I-198 | 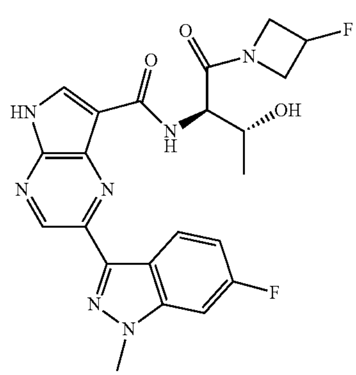 [SMILES: C[C@@H](O)[C@@H](NC(=O)c1c[nH]c2ncc(-c3nn(C)c4cc(F)ccc34)nc12)C(=O)N1CC(F)C1] | 2-(6-Fluoro-1-methyl-1H-indazol-3-yl)-5H-pyrrolo[2,3-b]pyrazine-7-carboxylic acid [(1R,2R)-1-(3-fluoro-azetidine-1-carbonyl)-2-hydroxy-propyl]-amide |

TABLE I-continued

| COMPOUND | STRUCTURE | SYSTEMATIC NAME |
| --- | --- | --- |
| I-199 | 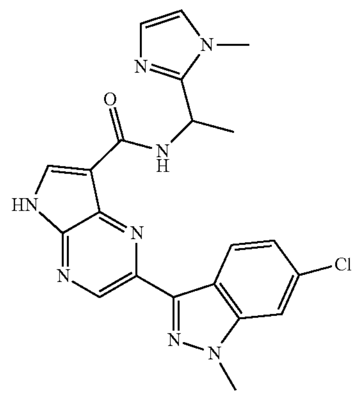 [SMILES: CC(NC(=O)c1c[nH]c2ncc(-c3nn(C)c4cc(Cl)ccc34)nc12)c1nccn1C] | 2-(6-Chloro-1-methyl-1H-indazol-3-yl)-5H-pyrrolo[2,3-b]pyrazine-7-carboxylic acid [1-(1-methyl-1H-imidazol-2-yl)-ethyl]-amide |
| I-200 | 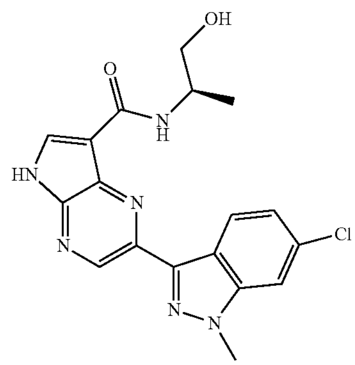 [SMILES: C[C@H](CO)NC(=O)c1c[nH]c2ncc(-c3nn(C)c4cc(Cl)ccc34)nc12] | 2-(6-Chloro-1-methyl-1H-indazol-3-yl)-5H-pyrrolo[2,3-b]pyrazine-7-carboxylic acid ((R)-2-hydroxy-1-methyl-ethyl)-amide |
| I-201 | 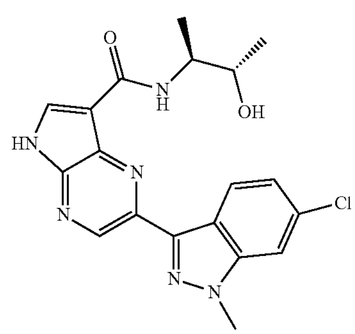 [SMILES: C[C@H](O)[C@H](C)NC(=O)c1c[nH]c2ncc(-c3nn(C)c4cc(Cl)ccc34)nc12] | 2-(6-Chloro-1-methyl-1H-indazol-3-yl)-5H-pyrrolo[2,3-b]pyrazine-7-carboxylic acid (trans-2-hydroxy-1-methyl-propyl)-amide |
| I-202 | 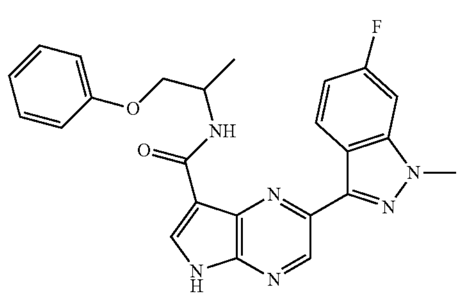 [SMILES: CC(COc1ccccc1)NC(=O)c1c[nH]c2ncc(-c3nn(C)c4cc(F)ccc34)nc12] | 2-(6-Fluoro-1-methyl-1H-indazol-3-yl)-5H-pyrrolo[2,3-b]pyrazine-7-carboxylic acid (1-methyl-2-phenoxy-ethyl)-amide |

TABLE I-continued

| COMPOUND | STRUCTURE | SYSTEMATIC NAME |
|---|---|---|
| I-203 | 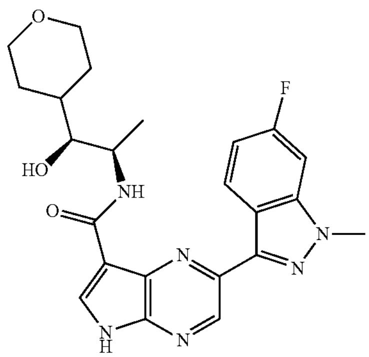 [SMILES: C[C@@H](NC(=O)c1c[nH]c2ncc(-c3nn(C)c4cc(F)ccc34)nc12)[C@@H](O)C1CCOCC1] | 2-(6-Fluoro-1-methyl-1H-indazol-3-yl)-5H-pyrrolo[2,3-b]pyrazine-7-carboxylic acid [cis-2-hydroxy-1-methyl-2-(tetrahydro-pyran-4-yl)-ethyl]-amide |
| I-204 | 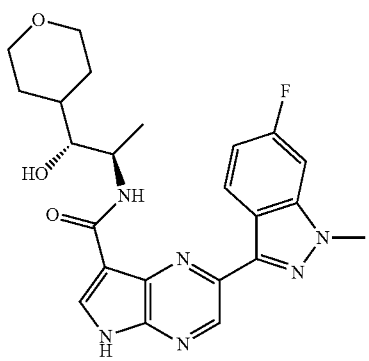 [SMILES: C[C@@H](NC(=O)c1c[nH]c2ncc(-c3nn(C)c4cc(F)ccc34)nc12)[C@H](O)C1CCOCC1] | 2-(6-Fluoro-1-methyl-1H-indazol-3-yl)-5H-pyrrolo[2,3-b]pyrazine-7-carboxylic acid [trans-2-hydroxy-1-methyl-2-(tetrahydro-pyran-4-yl)-ethyl]-amide |
| I-205 | 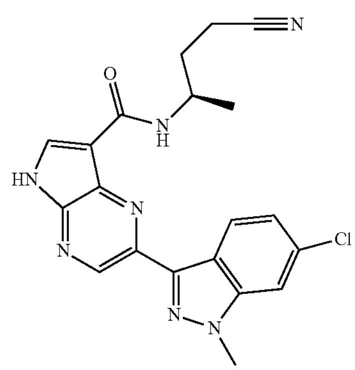 [SMILES: C[C@H](CCC#N)NC(=O)c1c[nH]c2ncc(-c3nn(C)c4cc(Cl)ccc34)nc12] | 2-(6-Chloro-1-methyl-1H-indazol-3-yl)-5H-pyrrolo[2,3-b]pyrazine-7-carboxylic acid ((R)-3-cyano-1-methyl-propyl)-amide |
| I-206 | 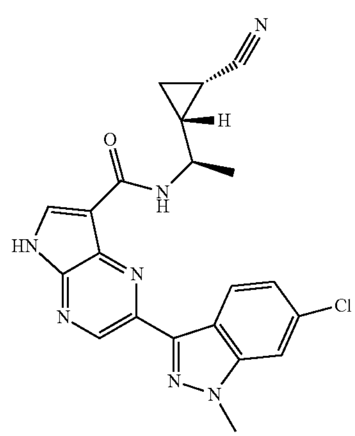 [SMILES: C[C@@H](NC(=O)c1c[nH]c2ncc(-c3nn(C)c4cc(Cl)ccc34)nc12)[C@@H]1C[C@@H]1C#N] | 2-(6-Chloro-1-methyl-1H-indazol-3-yl)-5H-pyrrolo[2,3-b]pyrazine-7-carboxylic acid [(R)-1-((1R,2S)-2-cyano-cyclopropyl)-ethyl]-amide |

TABLE I-continued

| COMPOUND | STRUCTURE | SYSTEMATIC NAME |
| --- | --- | --- |
| I-207 | 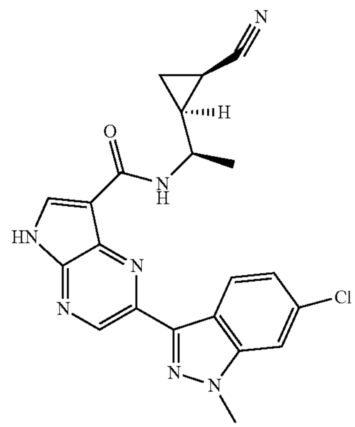 [SMILES: C[C@@H](NC(=O)c1c[nH]c2ncc(-c3nn(C)c4cc(Cl)ccc34)nc12)[C@H]1C[C@H]1C#N] | 2-(6-Chloro-1-methyl-1H-indazol-3-yl)-5H-pyrrolo[2,3-b]pyrazine-7-carboxylic acid [(R)-1-((1S,2R)-2-cyano-cyclopropyl)-ethyl]-amide |
| I-208 | 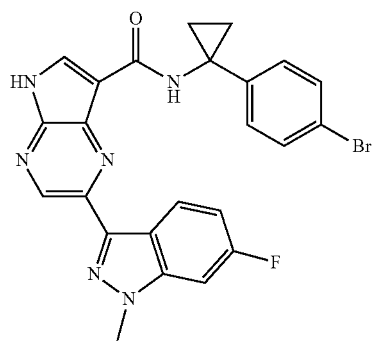 [SMILES: Cn1nc(-c2cnc3[nH]cc(C(=O)NC4(c5ccc(Br)cc5)CC4)c3n2)c2ccc(F)cc21] | 2-(6-Fluoro-1-methyl-1H-indazol-3-yl)-5H-pyrrolo[2,3-b]pyrazine-7-carboxylic acid [1-(4-bromo-phenyl)-cyclopropyl]-amide |
| I-209 | 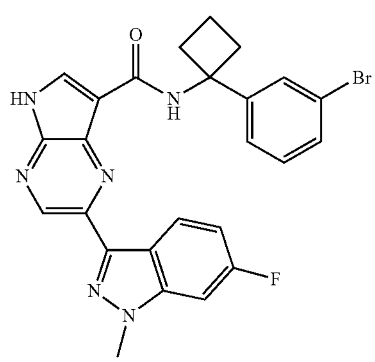 [SMILES: Cn1nc(-c2cnc3[nH]cc(C(=O)NC4(c5cccc(Br)c5)CCC4)c3n2)c2ccc(F)cc21] | 2-(6-Fluoro-1-methyl-1H-indazol-3-yl)-5H-pyrrolo[2,3-b]pyrazine-7-carboxylic acid [1-(3-bromo-phenyl)-cyclobutyl]-amide |
| I-210 | 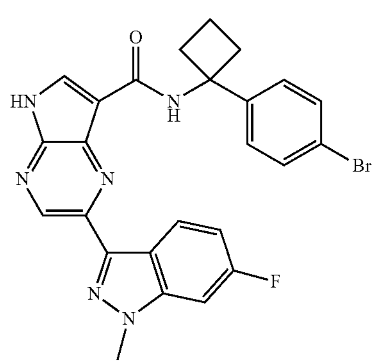 [SMILES: Cn1nc(-c2cnc3[nH]cc(C(=O)NC4(c5ccc(Br)cc5)CCC4)c3n2)c2ccc(F)cc21] | 2-(6-Fluoro-1-methyl-1H-indazol-3-yl)-5H-pyrrolo[2,3-b]pyrazine-7-carboxylic acid [1-(4-bromo-phenyl)-cyclobutyl]-amide |

TABLE I-continued

| COMPOUND | STRUCTURE | SYSTEMATIC NAME |
|---|---|---|
| I-211 | 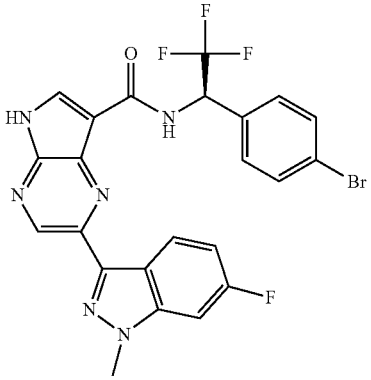 [SMILES: Cn1nc(-c2cnc3[nH]cc(C(=O)N[C@H](c4ccc(Br)cc4)C(F)(F)F)c3n2)c2ccc(F)cc21] | 2-(6-Fluoro-1-methyl-1H-indazol-3-yl)-5H-pyrrolo[2,3-b]pyrazine-7-carboxylic acid [(R)-1-(4-bromo-phenyl)-2,2,2-trifluoro-ethyl)-amide |
| I-212 | 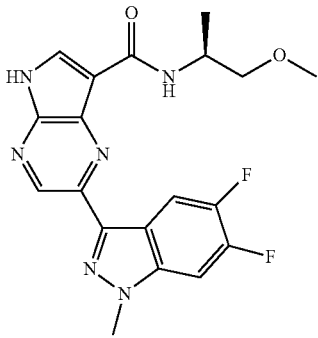 [SMILES: COC[C@H](C)NC(=O)c1c[nH]c2ncc(-c3nn(C)c4cc(F)c(F)cc34)nc12] | 2-(5,6-Difluoro-1-methyl-1H-indazol-3-yl)-5H-pyrrolo[2,3-b]pyrazine-7-carboxylic acid ((S)-2-methoxy-1-methyl-ethyl)-amide |
| I-213 | 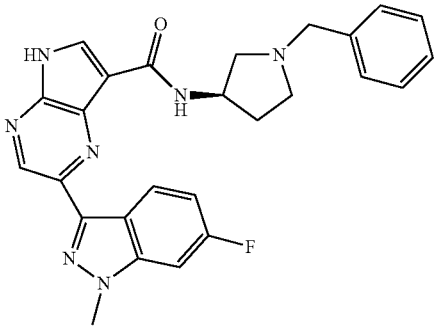 [SMILES: Cn1nc(-c2cnc3[nH]cc(C(=O)N[C@@H]4CCN(Cc5ccccc5)C4)c3n2)c2ccc(F)cc21] | 2-(6-Fluoro-1-methyl-1H-indazol-3-yl)-5H-pyrrolo[2,3-b]pyrazine-7-carboxylic acid ((R)-1-benzyl-pyrrolidin-3-yl)-amide |
| I-214 | 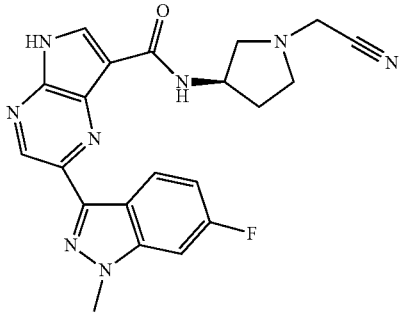 [SMILES: Cn1nc(-c2cnc3[nH]cc(C(=O)N[C@@H]4CCN(CC#N)C4)c3n2)c2ccc(F)cc21] | 2-(6-Fluoro-1-methyl-1H-indazol-3-yl)-5H-pyrrolo[2,3-b]pyrazine-7-carboxylic acid ((R)-1-cyanomethyl-pyrrolidin-3-yl)-amide |

TABLE I-continued

| COMPOUND | STRUCTURE | SYSTEMATIC NAME |
|---|---|---|
| I-215 | 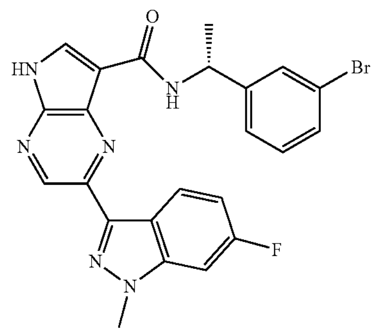 [SMILES: C[C@@H](NC(=O)c1c[nH]c2ncc(-c3nn(C)c4cc(F)ccc34)nc12)c1cccc(Br)c1] | 2-(6-Fluoro-1-methyl-1H-indazol-3-yl)-5H-pyrrolo[2,3-b]pyrazine-7-carboxylic acid [(R)-1-(3-bromo-phenyl)-ethyl]-amide |
| I-216 | 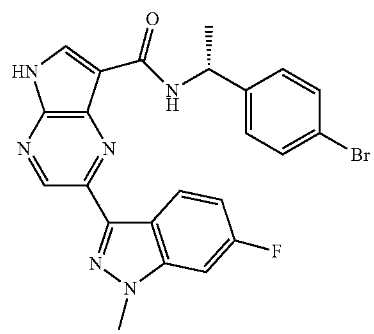 [SMILES: C[C@@H](NC(=O)c1c[nH]c2ncc(-c3nn(C)c4cc(F)ccc34)nc12)c1ccc(Br)cc1] | 2-(6-Fluoro-1-methyl-1H-indazol-3-yl)-5H-pyrrolo[2,3-b]pyrazine-7-carboxylic acid [(R)-1-(4-bromo-phenyl)-ethyl]-amide |
| I-217 | 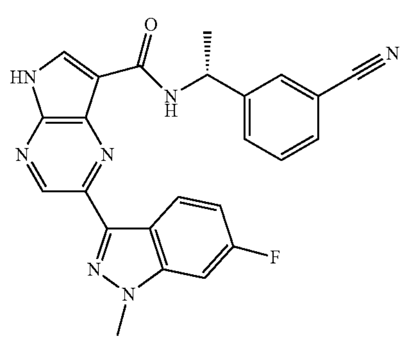 [SMILES: C[C@@H](NC(=O)c1c[nH]c2ncc(-c3nn(C)c4cc(F)ccc34)nc12)c1cccc(C#N)c1] | 2-(6-Fluoro-1-methyl-1H-indazol-3-yl)-5H-pyrrolo[2,3-b]pyrazine-7-carboxylic acid [(R)-1-(3-cyano-phenyl)-ethyl]-amide |
| I-218 | 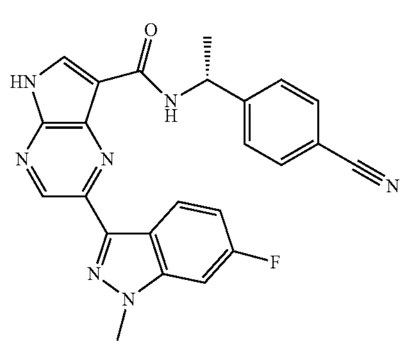 [SMILES: C[C@@H](NC(=O)c1c[nH]c2ncc(-c3nn(C)c4cc(F)ccc34)nc12)c1ccc(C#N)cc1] | 2-(6-Fluoro-1-methyl-1H-indazol-3-yl)-5H-pyrrolo[2,3-b]pyrazine-7-carboxylic acid [(R)-1-(4-cyano-phenyl)-ethyl]-amide |

TABLE I-continued

| COMPOUND | STRUCTURE | SYSTEMATIC NAME |
| --- | --- | --- |
| I-219 | 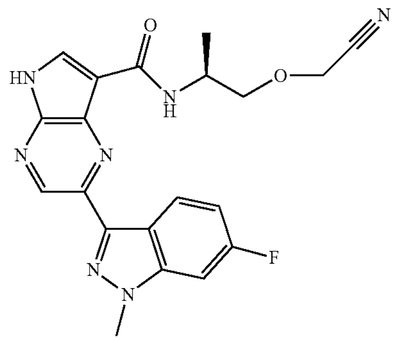 [SMILES: C[C@@H](COCC#N)NC(=O)c1c[nH]c2ncc(-c3nn(C)c4cc(F)ccc34)nc12] | 2-(6-Fluoro-1-methyl-1H-indazol-3-yl)-5H-pyrrolo[2,3-b]pyrazine-7-carboxylic acid ((S)-2-cyanomethoxy-1-methyl-ethyl)-amide |
| I-220 | 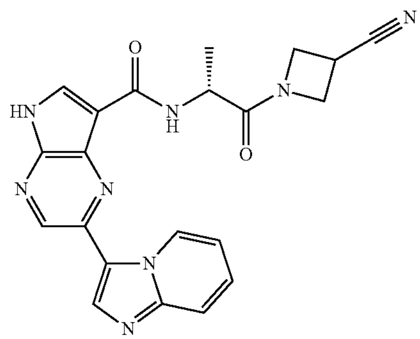 [SMILES: C[C@@H](NC(=O)c1c[nH]c2ncc(-c3cnc4ccccn34)nc12)C(=O)N1CC(C#N)C1] | 2-Imidazo[1,2-a]pyridin-3-yl-5H-pyrrolo[2,3-b]pyrazine-7-carboxylic acid [(R)-2-(3-cyano-azetidin-1-yl)-1-methyl-2-oxo-ethyl]-amide |
| I-221 | 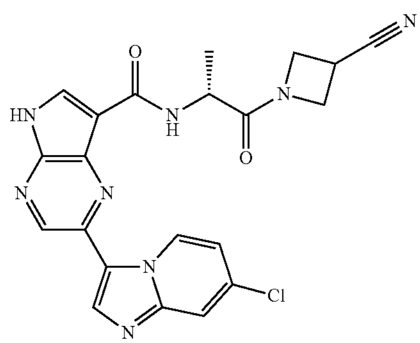 [SMILES: C[C@@H](NC(=O)c1c[nH]c2ncc(-c3cnc4cc(Cl)ccn34)nc12)C(=O)N1CC(C#N)C1] | 2-(7-Chloro-imidazo[1,2-a]pyridin-3-yl)-5H-pyrrolo[2,3-b]pyrazine-7-carboxylic acid [(R)-2-(3-cyano-azetidin-1-yl)-1-methyl-2-oxo-ethyl]-amide |
| I-222 | 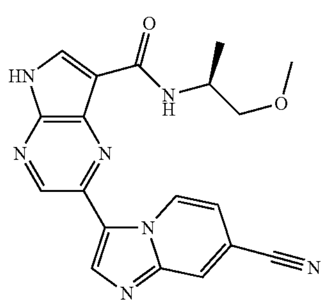 [SMILES: COC[C@H](C)NC(=O)c1c[nH]c2ncc(-c3cnc4cc(C#N)ccn34)nc12] | 2-(7-Cyano-imidazo[1,2-a]pyridin-3-yl)-5H-pyrrolo[2,3-b]pyrazine-7-carboxylic acid ((S)-2-methoxy-1-methyl-ethyl)-amide |
| I-223 | 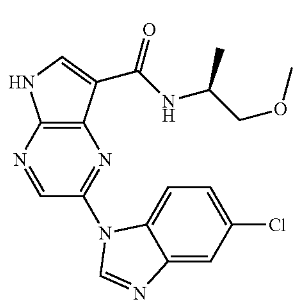 [SMILES: COC[C@H](C)NC(=O)c1c[nH]c2ncc(-n3cnc4cc(Cl)ccc43)nc12] | 2-(5-Chloro-benzoimidazol-1-yl)-5H-pyrrolo[2,3-b]pyrazine-7-carboxylic acid ((S)-2-methoxy-1-methyl-ethyl)-amide |

TABLE I-continued

| COMPOUND | STRUCTURE | SYSTEMATIC NAME |
|---|---|---|
| I-224 | 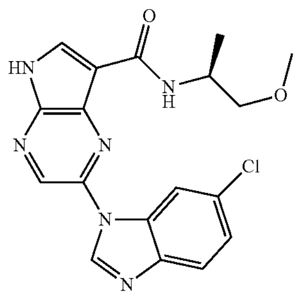 [SMILES: COC[C@H](C)NC(=O)c1c[nH]c2ncc(-n3cnc4ccc(Cl)cc43)nc12] | 2-(6-Chloro-benzoimidazol-1-yl)-5H-pyrrolo[2,3-b]pyrazine-7-carboxylic acid ((S)-2-methoxy-1-methyl-ethyl)-amide |
| I-225 | 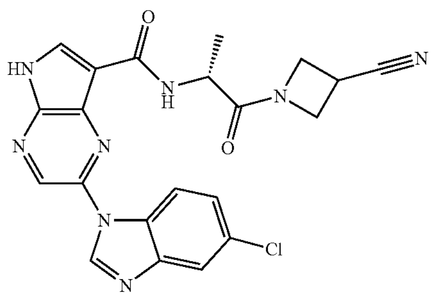 [SMILES: C[C@@H](NC(=O)c1c[nH]c2ncc(-n3cnc4cc(Cl)ccc43)nc12)C(=O)N1CC(C#N)C1] | 2-(5-Chloro-benzoimidazol-1-yl)-5H-pyrrolo[2,3-b]pyrazine-7-carboxylic acid [(R)-2-(3-cyano-azetidin-1-yl)-1-methyl-2-oxo-ethyl]-amide |
| I-226 | 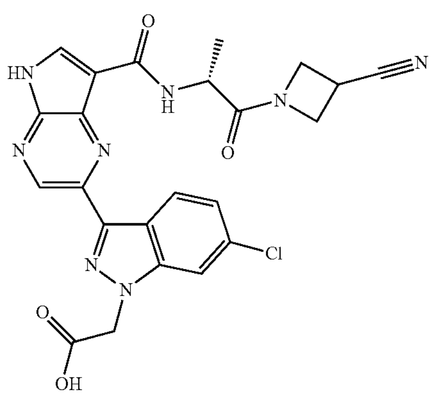 [SMILES: C[C@@H](NC(=O)c1c[nH]c2ncc(-c3nn(CC(=O)O)c4cc(Cl)ccc34)nc12)C(=O)N1CC(C#N)C1] | (6-Chloro-3-{7-[(R)-2-(3-cyano-azetidin-1-yl)-1-methyl-2-oxo-ethylcarbamoyl]-5H-pyrrolo[2,3-b]pyrazin-2-yl}-indazol-1-yl)-acetic acid |
| I-227 | 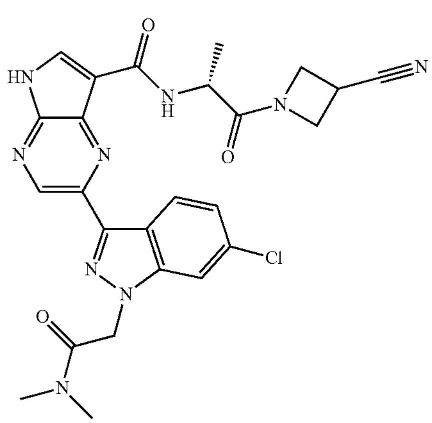 [SMILES: C[C@@H](NC(=O)c1c[nH]c2ncc(-c3nn(CC(=O)N(C)C)c4cc(Cl)ccc34)nc12)C(=O)N1CC(C#N)C1] | 2-(6-Chloro-1-dimethylcarbamoylmethyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide |

TABLE I-continued

| COMPOUND | STRUCTURE | SYSTEMATIC NAME |
| --- | --- | --- |
| I-228 | 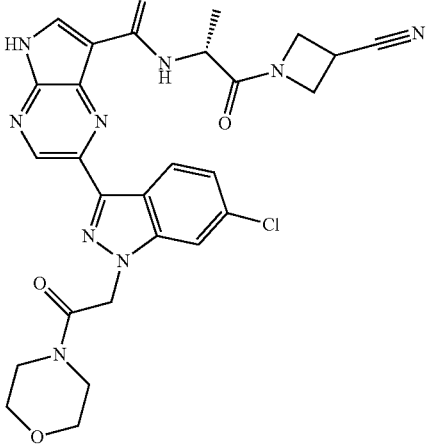 | 2-[6-Chloro-1-(2-morpholin-4-yl-2-oxo-ethyl)-1H-indazol-3-yl]-5H-pyrrolo[2,3-b]pyrazine-7-carboxylic acid [(R)-2-(3-cyano-azetidin-1-yl)-1-methyl-2-oxo-ethyl]-amide |
| I-229 | 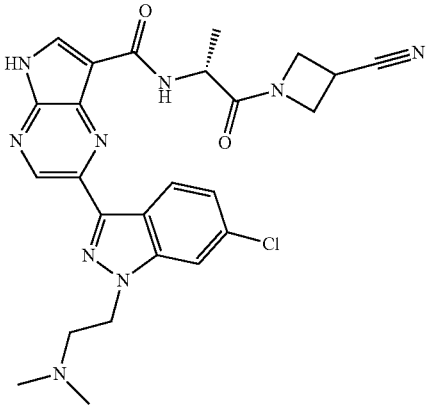 [SMILES: C[C@@H](NC(=O)c1c[nH]c2ncc(-c3nn(CCN(C)C)c4cc(Cl)ccc34)nc12)C(=O)N1CC(C#N)C1] | 2-[6-Chloro-1-(2-dimethylamino-ethyl)-1H-indazol-3-yl]-5H-pyrrolo[2,3-b]pyrazine-7-carboxylic acid [(R)-2-(3-cyano-azetidin-1-yl)-1-methyl-2-oxo-ethyl]-amide |
| I-230 | 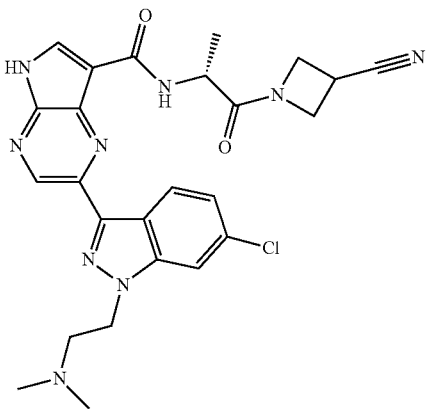 [SMILES: C[C@@H](NC(=O)c1c[nH]c2ncc(-c3nn(CCN(C)C)c4cc(Cl)ccc34)nc12)C(=O)N1CC(C#N)C1] | 2-[6-Chloro-1-(2-dimethylamino-ethyl)-1H-indazol-3-yl]-5H-pyrrolo[2,3-b]pyrazine-7-carboxylic acid [(R)-2-(3-cyano-azetidin-1-yl)-1-methyl-2-oxo-ethyl]-amide |

TABLE I-continued

| COMPOUND | STRUCTURE | SYSTEMATIC NAME |
| --- | --- | --- |
| I-231 | 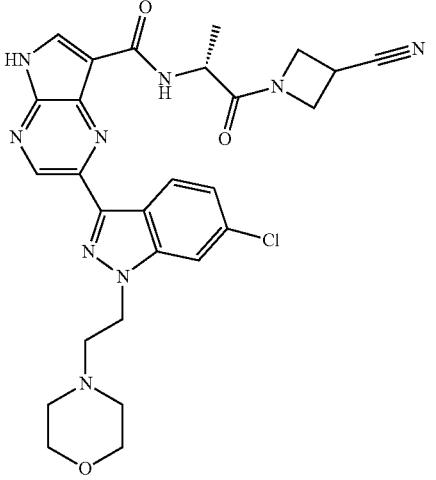 [SMILES: C[C@@H](NC(=O)c1c[nH]c2ncc(-c3nn(CCN4CCOCC4)c4cc(Cl)ccc34)nc12)C(=O)N1CC(C#N)C1] | 2-[6-Chloro-1-(2-morpholin-4-yl-ethyl)-1H-indazol-3-yl]-5H-pyrrolo[2,3-b]pyrazine-7-carboxylic acid [(R)-2-(3-cyano-azetidin-1-yl)-1-methyl-2-oxo-ethyl]-amide |
| I-232 | 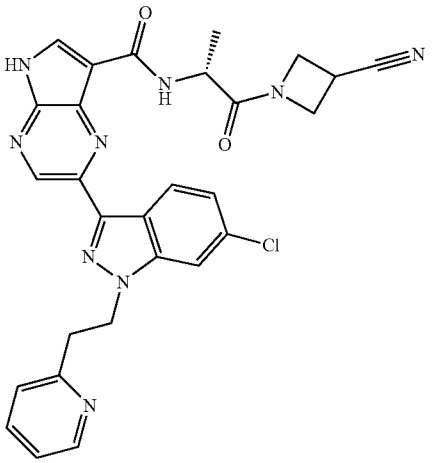 [SMILES: C[C@@H](NC(=O)c1c[nH]c2ncc(-c3nn(CCc4ccccn4)c4cc(Cl)ccc34)nc12)C(=O)N1CC(C#N)C1] | 2-[6-Chloro-1-(2-pyridin-2-yl-ethyl)-1H-indazol-3-yl]-5H-pyrrolo[2,3-b]pyrazine-7-carboxylic acid [(R)-2-(3-cyano-azetidin-1-yl)-1-methyl-2-oxo-ethyl]-amide |
| I-233 | 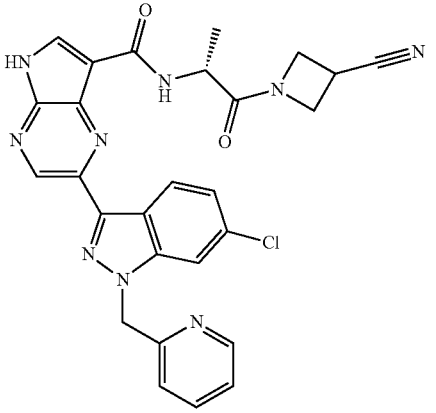 [SMILES: C[C@@H](NC(=O)c1c[nH]c2ncc(-c3nn(Cc4ccccn4)c4cc(Cl)ccc34)nc12)C(=O)N1CC(C#N)C1] | 2-(6-Chloro-1-pyridin-2-ylmethyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide |

TABLE I-continued

| COMPOUND | STRUCTURE | SYSTEMATIC NAME |
| --- | --- | --- |
| I-234 | 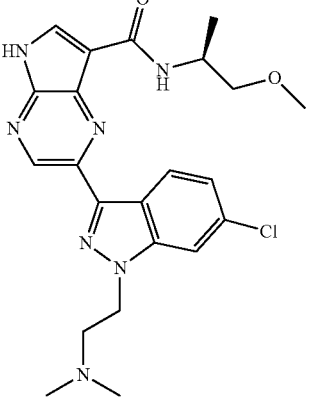 | 2-[6-Chloro-1-(2-dimethylamino-ethyl)-1H-indazol-3-yl]-5H-pyrrolo[2,3-b]pyrazine-7-carboxylic acid ((S)-2-methoxy-1-methyl-ethyl)-amide |
| I-235 | 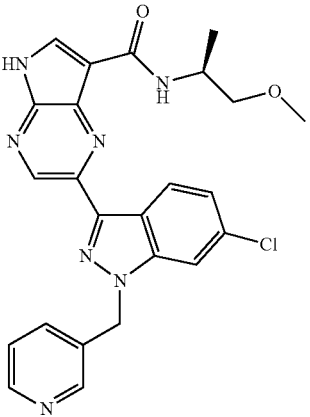 [SMILES: COC[C@H](C)NC(=O)c1c[nH]c2ncc(-c3nn(Cc4cccnc4)c4cc(Cl)ccc34)nc12] | 2-(6-Chloro-1-pyridin-3-ylmethyl-1H-indazol-3-yl)-5H-pyrrolo[2,3-b]pyrazine-7-carboxylic acid ((S)-2-methoxy-1-methyl-ethyl)-amide |
| I-236 | 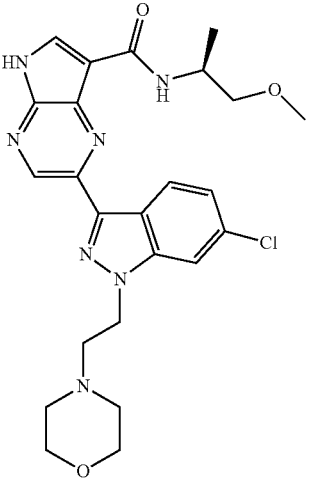 [SMILES: COC[C@H](C)NC(=O)c1c[nH]c2ncc(-c3nn(CCN4CCOCC4)c4cc(Cl)ccc34)nc12] | 2-[6-Chloro-1-(2-morpholin-4-yl-ethyl)-1H-indazol-3-yl]-5H-pyrrolo[2,3-b]pyrazine-7-carboxylic acid ((S)-2-methoxy-1-methyl-ethyl)-amide |

TABLE I-continued

| COMPOUND | STRUCTURE | SYSTEMATIC NAME |
| --- | --- | --- |
| I-237 | 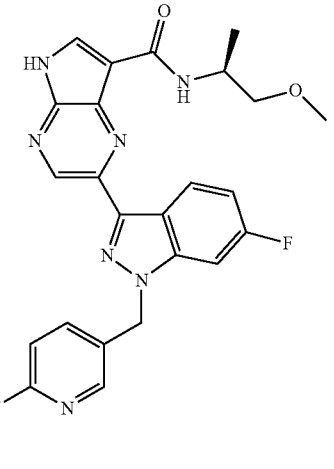 | 2-[6-Fluoro-1-(6-morpholin-4-yl-pyridin-3-ylmethyl)-1H-indazol-3-yl]-5H-pyrrolo[2,3-b]pyrazine-7-carboxylic acid ((S)-2-methoxy-1-methyl-ethyl)-amide |
| I-238 | 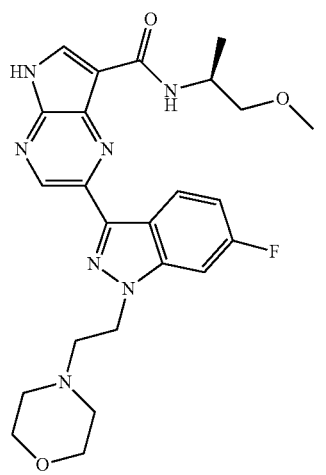 [SMILES: COC[C@H](C)NC(=O)c1c[nH]c2ncc(-c3nn(CCN4CCOCC4)c4cc(F)ccc34)nc12] | 2-[6-Fluoro-1-(2-morpholin-4-yl-ethyl)-1H-indazol-3-yl]-5H-pyrrolo[2,3-b]pyrazine-7-carboxylic acid ((S)-2-methoxy-1-methyl-ethyl)-amide |
| I-239 | 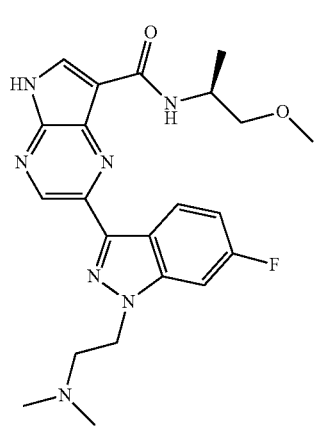 [SMILES: COC[C@H](C)NC(=O)c1c[nH]c2ncc(-c3nn(CCN(C)C)c4cc(F)ccc34)nc12] | 2-[1-(2-Dimethylamino-ethyl)-6-fluoro-1H-indazol-3-yl]-5H-pyrrolo[2,3-b]pyrazine-7-carboxylic acid ((S)-2-methoxy-1-methyl-ethyl)-amide |

TABLE I-continued

| COMPOUND | STRUCTURE | SYSTEMATIC NAME |
| --- | --- | --- |
| I-240 | 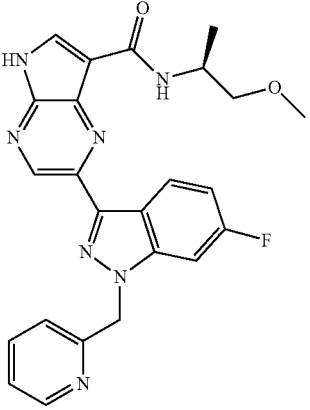 [SMILES: COC[C@H](C)NC(=O)c1c[nH]c2ncc(-c3nn(Cc4ccccn4)c4cc(F)ccc34)nc12] | 2-(6-Fluoro-1-pyridin-2-ylmethyl-1H-indazol-3-yl)-5H-pyrrolo[2,3-b]pyrazine-7-carboxylic acid ((S)-2-methoxy-1-methyl-ethyl)-amide |
| I-241 | 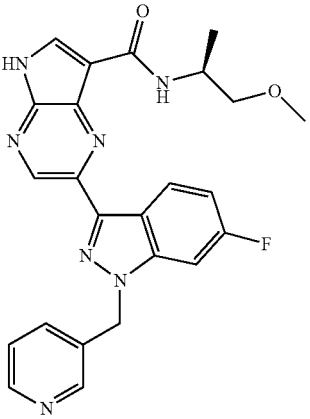 [SMILES: COC[C@H](C)NC(=O)c1c[nH]c2ncc(-c3nn(Cc4cccnc4)c4cc(F)ccc34)nc12] | 2-(6-Fluoro-1-pyridin-3-ylmethyl-1H-indazol-3-yl)-5H-pyrrolo[2,3-b]pyrazine-7-carboxylic acid ((S)-2-methoxy-1-methyl-ethyl)-amide |
| I-242 | 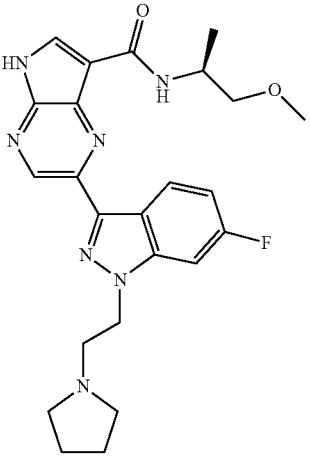 [SMILES: COC[C@H](C)NC(=O)c1c[nH]c2ncc(-c3nn(CCN4CCCC4)c4cc(F)ccc34)nc12] | 2-[6-Fluoro-1-(2-pyrrolidin-1-yl-ethyl)-1H-indazol-3-yl]-5H-pyrrolo[2,3-b]pyrazine-7-carboxylic acid ((S)-2-methoxy-1-methyl-ethyl)-amide |

TABLE I-continued

| COMPOUND | STRUCTURE | SYSTEMATIC NAME |
|---|---|---|
| I-243 | 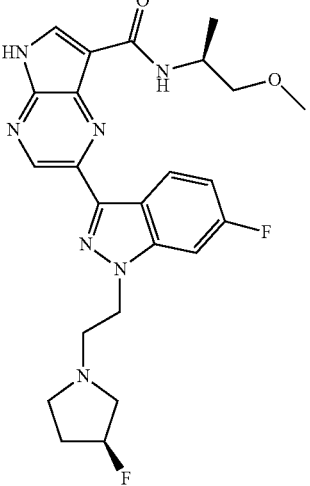 | 2-{6-Fluoro-1-[2-((S)-3-fluoro-pyrrolidin-1-yl)-ethyl]-1H-indazol-3-yl}-5H-pyrrolo[2,3-b]pyrazine-7-carboxylic acid ((S)-2-methoxy-1-methyl-ethyl)-amide |
| I-244 | 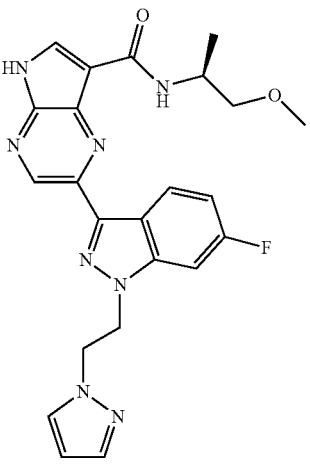 [SMILES: COC[C@H](C)NC(=O)c1c[nH]c2ncc(-c3nn(CCn4cccn4)c4cc(F)ccc34)nc12] | 2-[6-Fluoro-1-(2-pyrazol-1-yl-ethyl)-1H-indazol-3-yl]-5H-pyrrolo[2,3-b]pyrazine-7-carboxylic acid ((S)-2-methoxy-1-methyl-ethyl)-amide |
| I-245 | 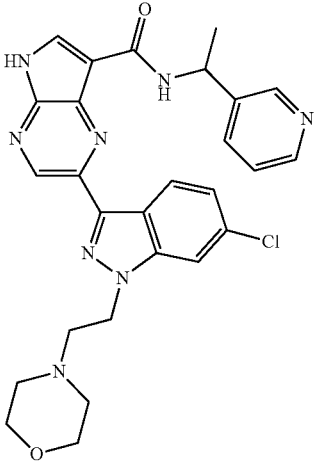 [SMILES: CC(NC(=O)c1c[nH]c2ncc(-c3nn(CCN4CCOCC4)c4cc(Cl)ccc34)nc12)c1cccnc1] | 2-[6-Chloro-1-(2-morpholin-4-yl-ethyl)-1H-indazol-3-yl]-5H-pyrrolo[2,3-b]pyrazine-7-carboxylic acid (1-pyridin-3-yl-ethyl)-amide |

TABLE I-continued
| COMPOUND | STRUCTURE | SYSTEMATIC NAME |
|---|---|---|
| I-246 | 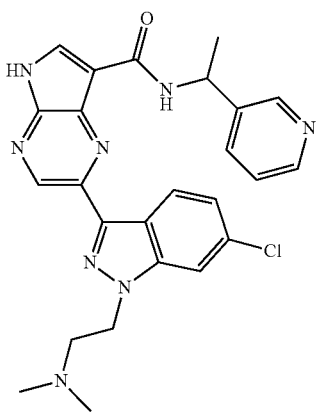 [SMILES: CC(NC(=O)c1c[nH]c2ncc(-c3nn(CCN(C)C)c4cc(Cl)ccc34)nc12)c1cccnc1] | 2-[6-Chloro-1-(2-dimethylamino-ethyl)-1H-indazol-3-yl]-5H-pyrrolo[2,3-b]pyrazine-7-carboxylic acid (1-pyridin-3-yl-ethyl)-amide |
| I-247 | 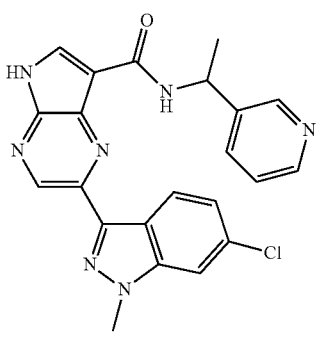 [SMILES: CC(NC(=O)c1c[nH]c2ncc(-c3nn(C)c4cc(Cl)ccc34)nc12)c1cccnc1] | 2-(6-Chloro-1-methyl-1H-indazol-3-yl)-5H-pyrrolo[2,3-b]pyrazine-7-carboxylic acid (1-pyridin-3-yl-ethyl)-amide |
| I-248 | 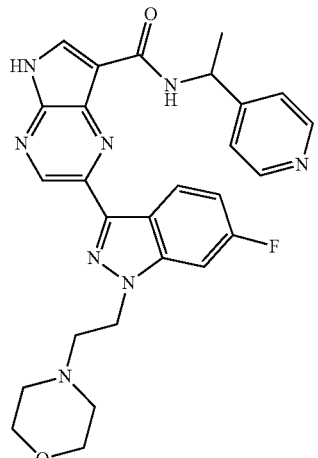 | 2-[6-Fluoro-1-(2-morpholin-4-yl-ethyl)-1H-indazol-3-yl]-5H-pyrrolo[2,3-b]pyrazine-7-carboxylic acid (1-pyridin-4-yl-ethyl)-amide |

TABLE I-continued

| COMPOUND | STRUCTURE | SYSTEMATIC NAME |
|---|---|---|
| I-249 | 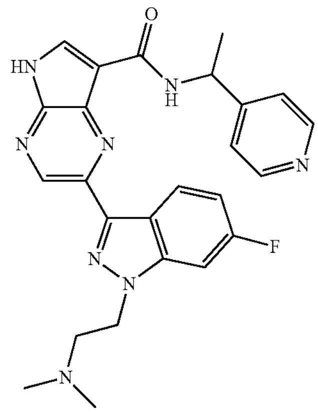 [SMILES: CC(NC(=O)c1c[nH]c2ncc(-c3nn(CCN(C)C)c4cc(F)ccc34)nc12)c1ccncc1] | 2-[1-(2-Dimethylamino-ethyl)-6-fluoro-1H-indazol-3-yl]-5H-pyrrolo[2,3-b]pyrazine-7-carboxylic acid (1-pyridin-4-yl-ethyl)-amide |
| I-250 | 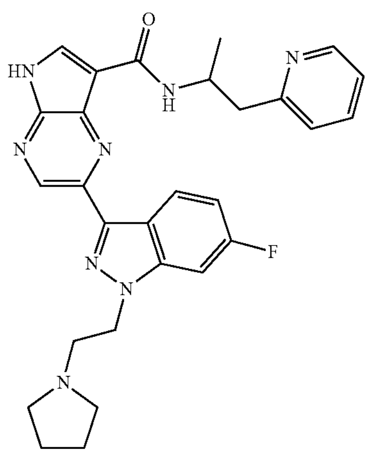 [SMILES: CC(Cc1ccccn1)NC(=O)c1c[nH]c2ncc(-c3nn(CCN4CCCC4)c4cc(F)ccc34)nc12] | 2-[6-Fluoro-1-(2-pyrrolidin-1-yl-ethyl)-1H-indazol-3-yl]-5H-pyrrolo[2,3-b]pyrazine-7-carboxylic acid (1-methyl-2-pyridin-2-yl-ethyl)-amide |
| I-251 | 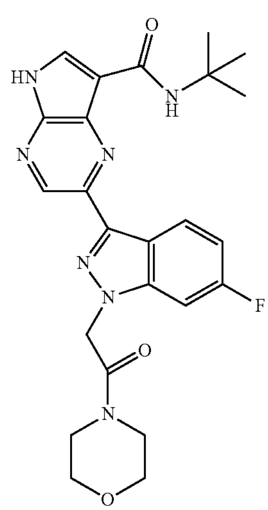 [SMILES: CC(C)(C)NC(=O)c1c[nH]c2ncc(-c3nn(CC(=O)N4CCOCC4)c4cc(F)ccc34)nc12] | 2-[6-Fluoro-1-(2-morpholin-4-yl-2-oxo-ethyl)-1H-indazol-3-yl]-5H-pyrrolo[2,3-b]pyrazine-7-carboxylic acid tert-butylamide |

TABLE I-continued

| COMPOUND | STRUCTURE | SYSTEMATIC NAME |
|---|---|---|
| I-252 | 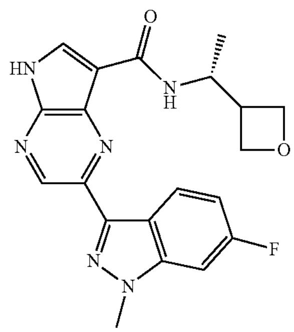 [SMILES: C[C@@H](NC(=O)c1c[nH]c2ncc(-c3nn(C)c4cc(F)ccc34)nc12)C1COC1] | 2-(6-Fluoro-1-methyl-1H-indazol-3-yl)-5H-pyrrolo[2,3-b]pyrazine-7-carboxylic acid ((R)-1-oxetan-3-yl-ethyl)-amide |
| I-253 | 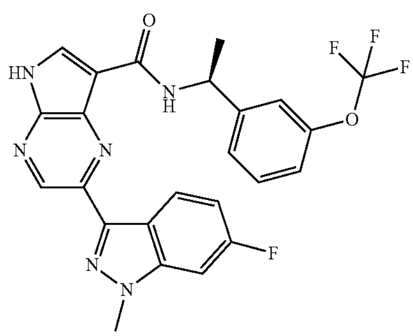 [SMILES: C[C@H](NC(=O)c1c[nH]c2ncc(-c3nn(C)c4cc(F)ccc34)nc12)c1cccc(OC(F)(F)F)c1] | 2-(6-Fluoro-1-methyl-1H-indazol-3-yl)-5H-pyrrolo[2,3-b]pyrazine-7-carboxylic acid [(S)-1-(3-trifluoromethoxy-phenyl)-ethyl]-amide |
| I-254 | 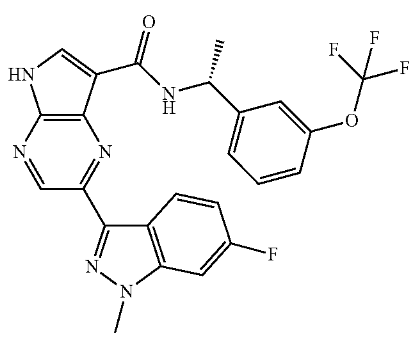 [SMILES: C[C@@H](NC(=O)c1c[nH]c2ncc(-c3nn(C)c4cc(F)ccc34)nc12)c1cccc(OC(F)(F)F)c1] | 2-(6-Fluoro-1-methyl-1H-indazol-3-yl)-5H-pyrrolo[2,3-b]pyrazine-7-carboxylic acid [(R)-1-(3-trifluoromethoxy-phenyl)-ethyl]-amide |
| I-255 | 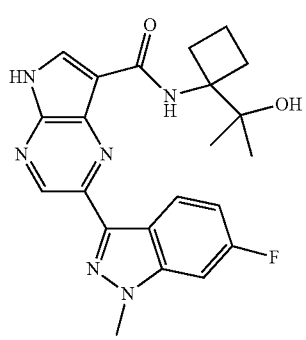 [SMILES: Cn1nc(-c2cnc3[nH]cc(C(=O)NC4(C(C)(C)O)CCC4)c3n2)c2ccc(F)cc21] | 2-(6-Fluoro-1-methyl-1H-indazol-3-yl)-5H-pyrrolo[2,3-b]pyrazine-7-carboxylic acid [1-(1-hydroxy-1-methyl-ethyl)-cyclobutyl]-amide |

| COMPOUND | STRUCTURE | SYSTEMATIC NAME |
|---|---|---|
| I-256 | 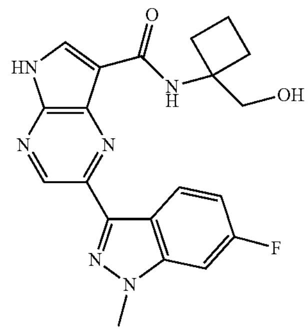 [SMILES: Cn1nc(-c2cnc3[nH]cc(C(=O)NC4(CO)CCC4)c3n2)c2ccc(F)cc21] | 2-(6-Fluoro-1-methyl-1H-indazol-3-yl)-5H-pyrrolo[2,3-b]pyrazine-7-carboxylic acid (1-hydroxymethyl-cyclobutyl)-amide |
| I-257 | 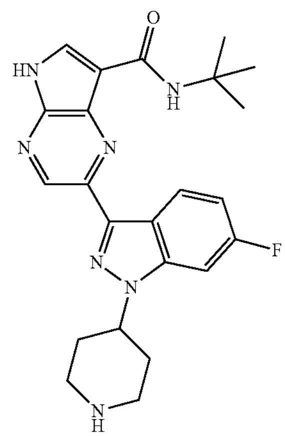 [SMILES: CC(C)(C)NC(=O)c1c[nH]c2ncc(-c3nn(C4CCNCC4)c4cc(F)ccc34)nc12] | 2-(6-Fluoro-1-piperidin-4-yl-1H-indazol-3-yl)-5H-pyrrolo[2,3-b]pyrazine-7-carboxylic acid tert-butylamide |
| I-258 | 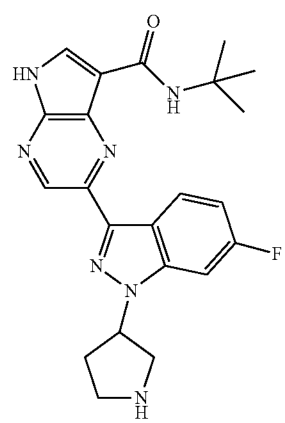 [SMILES: CC(C)(C)NC(=O)c1c[nH]c2ncc(-c3nn(C4CCNC4)c4cc(F)ccc34)nc12] | 2-(6-Fluoro-1-pyrrolidin-3-yl-1H-indazol-3-yl)-5H-pyrrolo[2,3-b]pyrazine-7-carboxylic acid tert-butylamide |
| I-259 | 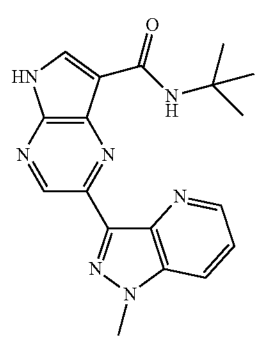 [SMILES: Cn1nc(-c2cnc3[nH]cc(C(=O)NC(C)(C)C)c3n2)c2ncccc21] | 2-(1-Methyl-1H-pyrazolo[4,3-b]pyridin-3-yl)-5H-pyrrolo[2,3-b]pyrazine-7-carboxylic acid tert-butylamide |

TABLE I-continued
| COMPOUND | STRUCTURE | SYSTEMATIC NAME |
|---|---|---|
| I-260 | 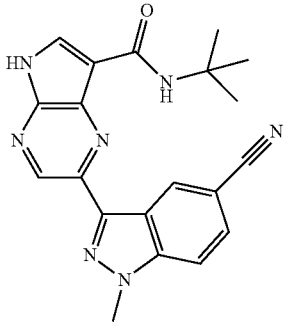 [SMILES: Cn1nc(-c2cnc3[nH]cc(C(=O)NC(C)(C)C)c3n2)c2cc(C#N)ccc21] | 2-(5-Cyano-1-methyl-1H-indazol-3-yl)-5H-pyrrolo[2,3-b]pyrazine-7-carboxylic acid tert-butylamide |
| I-261 | 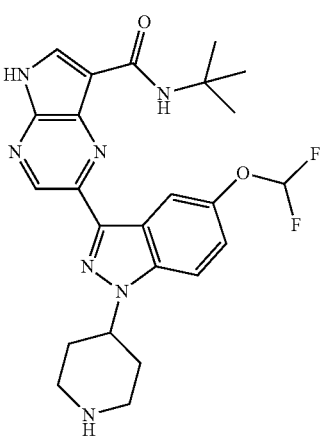 [SMILES: CC(C)(C)NC(=O)c1c[nH]c2ncc(-c3nn(C4CCNCC4)c4ccc(OC(F)F)cc34)nc12] | 2-(5-Difluoromethoxy-1-piperidin-4-yl-1H-indazol-3-yl)-5H-pyrrolo[2,3-b]pyrazine-7-carboxylic acid tert-butylamide |
| I-262 | 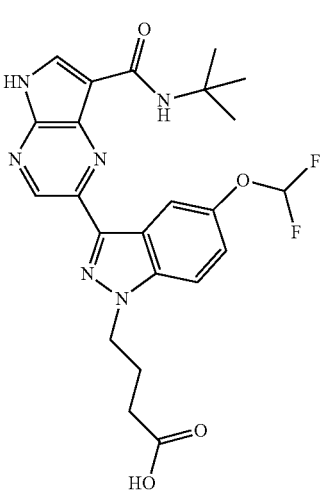 [SMILES: CC(C)(C)NC(=O)c1c[nH]c2ncc(-c3nn(CCCC(=O)O)c4ccc(OC(F)F)cc34)nc12] | 4-[3-(7-tert-Butylcarbamoyl-5H-pyrrolo[2,3-b]pyrazin-2-yl)-5-difluoromethoxy-indazol-1-yl]-butyric acid |

TABLE I-continued

| COMPOUND | STRUCTURE | SYSTEMATIC NAME |
|---|---|---|
| I-263 | 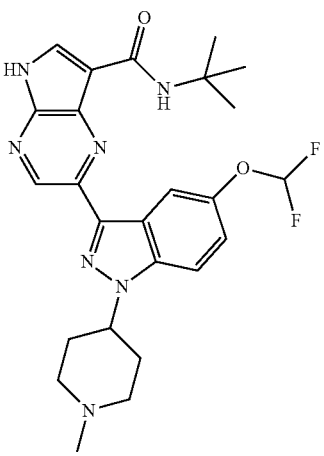 [SMILES: CN1CCC(n2nc(-c3cnc4[nH]cc(C(=O)NC(C)(C)C)c4n3)c3cc(OC(F)F)ccc32)CC1] | 2-[5-Difluoromethoxy-1-(1-methyl-piperidin-4-yl)-1H-indazol-3-yl]-5H-pyrrolo[2,3-b]pyrazine-7-carboxylic acid tert-butylamide |
| I-264 | 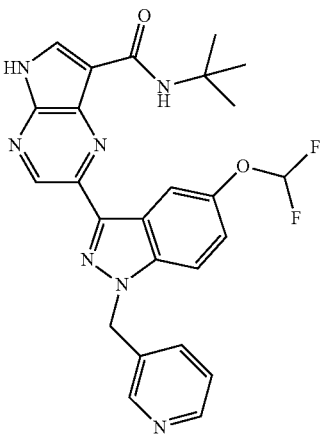 [SMILES: CC(C)(C)NC(=O)c1c[nH]c2ncc(-c3nn(Cc4cccnc4)c4ccc(OC(F)F)cc34)nc12] | 2-(5-Difluoromethoxy-1-pyridin-3-ylmethyl-1H-indazol-3-yl)-5H-pyrrolo[2,3-b]pyrazine-7-carboxylic acid tert-butylamide |
| I-265 | 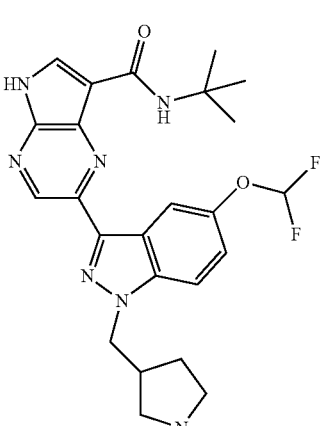 | 2-(5-Difluoromethoxy-1-pyrrolidin-3-ylmethyl-1H-indazol-3-yl)-5H-pyrrolo[2,3-b]pyrazine-7-carboxylic acid tert-butylamide |

TABLE I-continued

| COMPOUND | STRUCTURE | SYSTEMATIC NAME |
|---|---|---|
| I-266 | 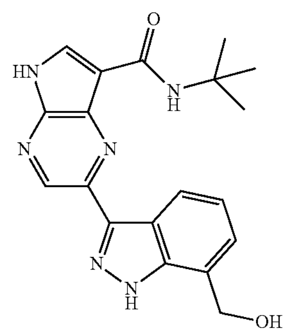 [SMILES: CC(C)(C)NC(=O)c1c[nH]c2ncc(-c3n[nH]c4c(CO)cccc34)nc12] | 2-(7-Hydroxymethyl-1H-indazol-3-yl)-5H-pyrrolo[2,3-b]pyrazine-7-carboxylic acid tert-butylamide |
| I-267 | 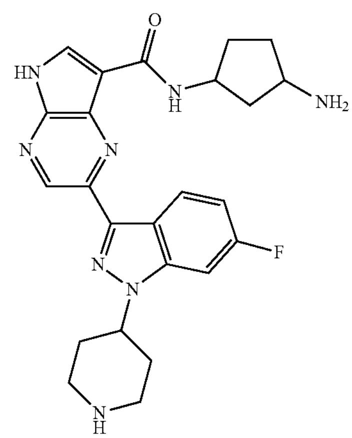 [SMILES: NC1CCC(NC(=O)c2c[nH]c3ncc(-c4nn(C5CCNCC5)c5cc(F)ccc45)nc23)C1] | 2-(6-Fluoro-1-piperidin-4-yl-1H-indazol-3-yl)-5H-pyrrolo[2,3-b]pyrazine-7-carboxylic acid (3-amino-cyclopentyl)-amide |
| I-268 | 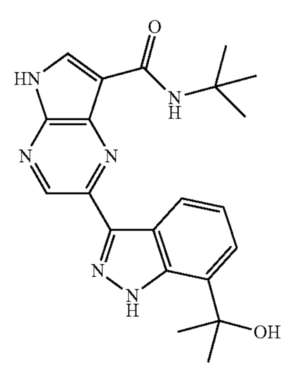 [SMILES: CC(C)(C)NC(=O)c1c[nH]c2ncc(-c3n[nH]c4c(C(C)(C)O)cccc34)nc12] | 2-[7-(1-Hydroxy-1-methyl-ethyl)-1H-indazol-3-yl]-5H-pyrrolo[2,3-b]pyrazine-7-carboxylic acid tert-butylamide |
| I-269 | 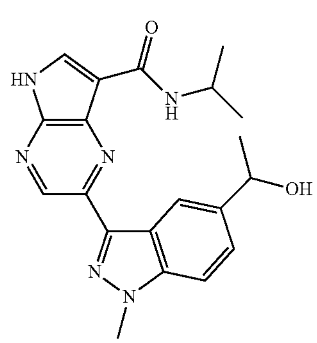 [SMILES: CC(C)NC(=O)c1c[nH]c2ncc(-c3nn(C)c4ccc(C(C)O)cc34)nc12] | 2-[5-(1-Hydroxy-ethyl)-1-methyl-1H-indazol-3-yl]-5H-pyrrolo[2,3-b]pyrazine-7-carboxylic acid isopropylamide |

TABLE I-continued

| COMPOUND | STRUCTURE | SYSTEMATIC NAME |
| --- | --- | --- |
| I-270 | 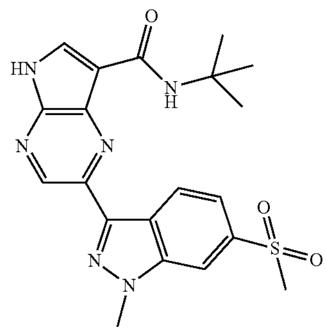 [SMILES: Cn1nc(-c2cnc3[nH]cc(C(=O)NC(C)(C)C)c3n2)c2ccc(S(C)(=O)=O)cc21] | 2-(6-Methanesulfonyl-1-methyl-1H-indazol-3-yl)-5H-pyrrolo[2,3-b]pyrazine-7-carboxylic acid tert-butylamide |
| I-271 | 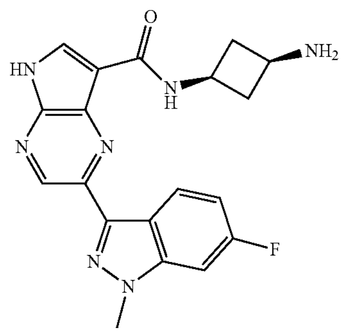 [SMILES: Cn1nc(-c2cnc3[nH]cc(C(=O)N[C@H]4C[C@@H](N)C4)c3n2)c2ccc(F)cc21] | 2-(6-Fluoro-1-methyl-1H-indazol-3-yl)-5H-pyrrolo[2,3-b]pyrazine-7-carboxylic acid (cis-3-amino-cyclobutyl)-amide |
| I-272 | 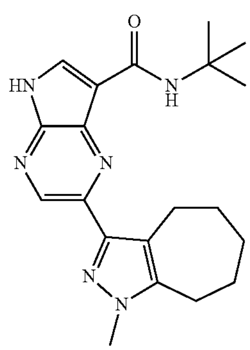 [SMILES: Cn1nc(-c2cnc3[nH]cc(C(=O)NC(C)(C)C)c3n2)c2c1CCCCC2] | 2-(1-Methyl-1,4,5,6,7,8-hexahydro-cycloheptapyrazol-3-yl)-5H-pyrrolo[2,3-b]pyrazine-7-carboxylic acid tert-butylamide |
| I-273 | 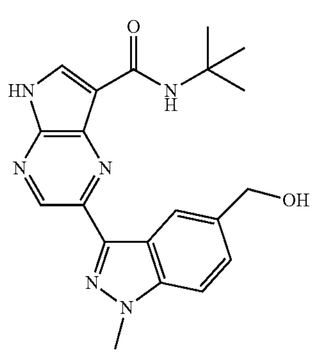 [SMILES: Cn1nc(-c2cnc3[nH]cc(C(=O)NC(C)(C)C)c3n2)c2cc(CO)ccc21] | 2-(5-Hydroxymethyl-1-methyl-1H-indazol-3-yl)-5H-pyrrolo[2,3-b]pyrazine-7-carboxylic acid tert-butylamide |

TABLE I-continued

| COMPOUND | STRUCTURE | SYSTEMATIC NAME |
| --- | --- | --- |
| I-274 | 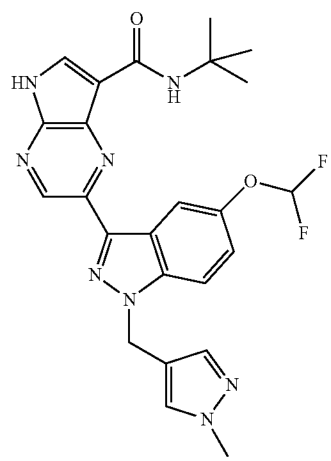 [SMILES: Cn1cc(Cn2nc(-c3cnc4[nH]cc(C(=O)NC(C)(C)C)c4n3)c3cc(OC(F)F)ccc32)cn1] | 2-[5-Difluoromethoxy-1-(1-methyl-1H-pyrazol-4-ylmethyl)-1H-indazol-3-yl]-5H-pyrrolo[2,3-b]pyrazine-7-carboxylic acid tert-butylamide |
| I-275 | 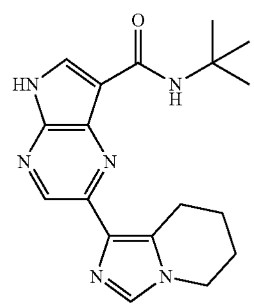 [SMILES: CC(C)(C)NC(=O)c1c[nH]c2ncc(-c3ncn4c3CCCC4)nc12] | 2-(5,6,7,8-Tetrahydro-imidazo[1,5-a]pyridin-1-yl)-5H-pyrrolo[2,3-b]pyrazine-7-carboxylic acid tert-butylamide |
| I-276 | 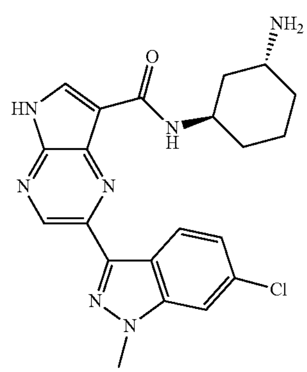 [SMILES: Cn1nc(-c2cnc3[nH]cc(C(=O)N[C@@H]4CCC[C@@H](N)C4)c3n2)c2ccc(Cl)cc21] | 2-(6-Chloro-1-methyl-1H-indazol-3-yl)-5H-pyrrolo[2,3-b]pyrazine-7-carboxylic acid (trans-3-amino-cyclohexyl)-amide |
| I-277 | 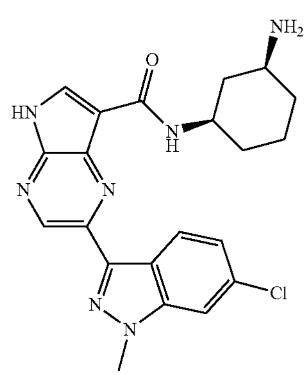 [SMILES: Cn1nc(-c2cnc3[nH]cc(C(=O)N[C@@H]4CCC[C@H](N)C4)c3n2)c2ccc(Cl)cc21] | 2-(6-Chloro-1-methyl-1H-indazol-3-yl)-5H-pyrrolo[2,3-b]pyrazine-7-carboxylic acid (cis-3-amino-cyclohexyl)-amide |

TABLE I-continued

| COMPOUND | STRUCTURE | SYSTEMATIC NAME |
|---|---|---|
| I-278 | 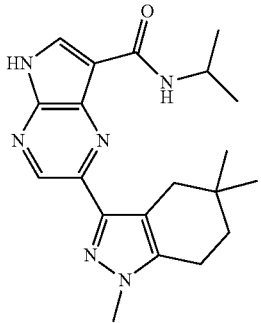 [SMILES: CC(C)NC(=O)c1c[nH]c2ncc(-c3nn(C)c4c3CC(C)(C)CC4)nc12] | 2-(1,5,5-Trimethyl-4,5,6,7-tetrahydro-1H-indazol-3-yl)-5H-pyrrolo[2,3-b]pyrazine-7-carboxylic acid isopropylamide |
| I-279 | 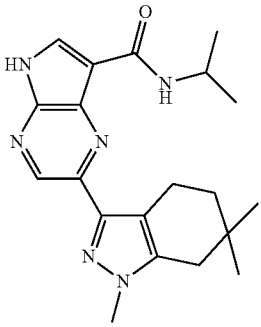 [SMILES: CC(C)NC(=O)c1c[nH]c2ncc(-c3nn(C)c4c3CCC(C)(C)C4)nc12] | 2-(1,6,6-Trimethyl-4,5,6,7-tetrahydro-1H-indazol-3-yl)-5H-pyrrolo[2,3-b]pyrazine-7-carboxylic acid isopropylamide |
| I-280 | 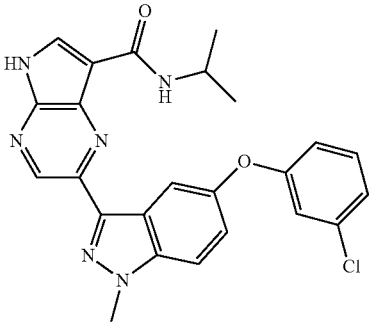 [SMILES: CC(C)NC(=O)c1c[nH]c2ncc(-c3nn(C)c4ccc(Oc5cccc(Cl)c5)cc34)nc12] | 2-[5-(3-Chloro-phenoxy)-1-methyl-1H-indazol-3-yl]-5H-pyrrolo[2,3-b]pyrazine-7-carboxylic acid isopropylamide |
| I-281 | 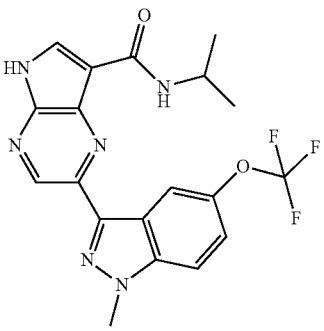 [SMILES: CC(C)NC(=O)c1c[nH]c2ncc(-c3nn(C)c4ccc(OC(F)(F)F)cc34)nc12] | 2-(1-Methyl-5-trifluoromethoxy-1H-indazol-3-yl)-5H-pyrrolo[2,3-b]pyrazine-7-carboxylic acid isopropylamide |

TABLE I-continued

| COMPOUND | STRUCTURE | SYSTEMATIC NAME |
|---|---|---|
| I-282 | 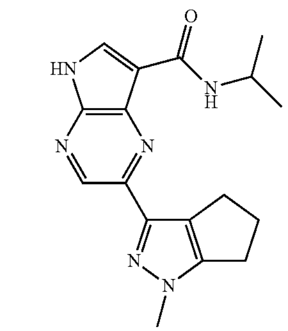 [SMILES: CC(C)NC(=O)c1c[nH]c2ncc(-c3nn(C)c4c3CCC4)nc12] | 2-(1-Methyl-1,4,5,6-tetrahydro-cyclopentapyrazol-3-yl)-5H-pyrrolo[2,3-b]pyrazine-7-carboxylic acid isopropylamide |
| I-283 | 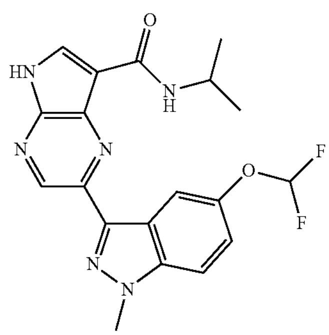 [SMILES: CC(C)NC(=O)c1c[nH]c2ncc(-c3nn(C)c4ccc(OC(F)F)cc34)nc12] | 2-(5-Difluoromethoxy-1-methyl-1H-indazol-3-yl)-5H-pyrrolo[2,3-b]pyrazine-7-carboxylic acid isopropylamide |
| I-284 | 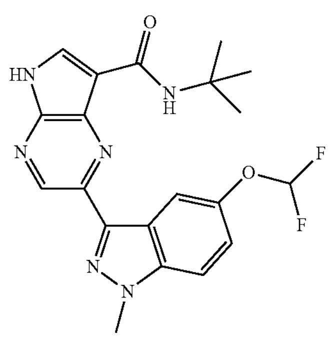 [SMILES: Cn1nc(-c2cnc3[nH]cc(C(=O)NC(C)(C)C)c3n2)c2cc(OC(F)F)ccc21] | 2-(5-Difluoromethoxy-1-methyl-1H-indazol-3-yl)-5H-pyrrolo[2,3-b]pyrazine-7-carboxylic acid tert-butylamide |
| I-285 | 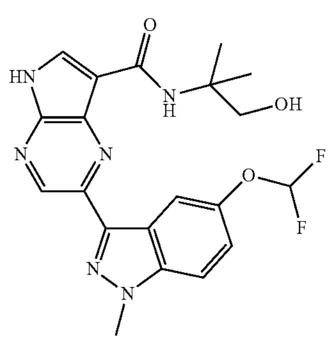 [SMILES: Cn1nc(-c2cnc3[nH]cc(C(=O)NC(C)(C)CO)c3n2)c2cc(OC(F)F)ccc21] | 2-(5-Difluoromethoxy-1-methyl-1H-indazol-3-yl)-5H-pyrrolo[2,3-b]pyrazine-7-carboxylic acid (2-hydroxy-1,1-dimethyl-ethyl)-amide |

TABLE I-continued

| COMPOUND | STRUCTURE | SYSTEMATIC NAME |
|---|---|---|
| I-286 | 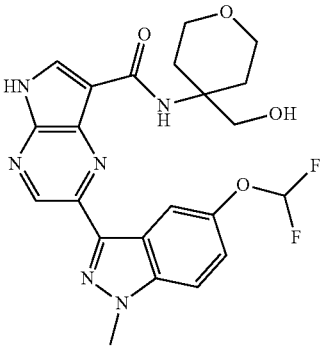 [SMILES: Cn1nc(-c2cnc3[nH]cc(C(=O)NC4(CO)CCOCC4)c3n2)c2cc(OC(F)F)ccc21] | 2-(5-Difluoromethoxy-1-methyl-1H-indazol-3-yl)-5H-pyrrolo[2,3-b]pyrazine-7-carboxylic acid (4-hydroxymethyl-tetrahydro-pyran-4-yl)-amide |
| I-287 | 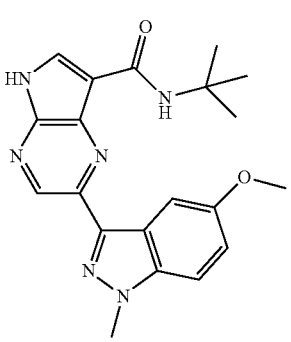 [SMILES: COc1ccc2c(c1)c(-c1cnc3[nH]cc(C(=O)NC(C)(C)C)c3n1)nn2C] | 2-(5-Methoxy-1-methyl-1H-indazol-3-yl)-5H-pyrrolo[2,3-b]pyrazine-7-carboxylic acid tert-butylamide |
| I-288 | 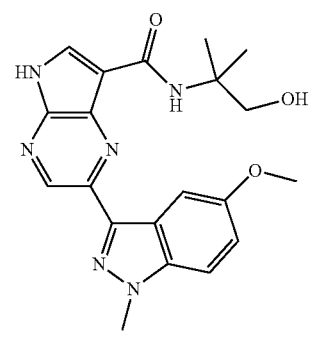 [SMILES: COc1ccc2c(c1)c(-c1cnc3[nH]cc(C(=O)NC(C)(C)CO)c3n1)nn2C] | 2-(5-Methoxy-1-methyl-1H-indazol-3-yl)-5H-pyrrolo[2,3-b]pyrazine-7-carboxylic acid (2-hydroxy-1,1-dimethyl-ethyl)-amide |
| I-289 | 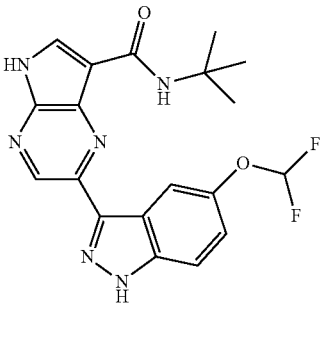 [SMILES: CC(C)(C)NC(=O)c1c[nH]c2ncc(-c3n[nH]c4ccc(OC(F)F)cc34)nc12] | 2-(5-Difluoromethoxy-1H-indazol-3-yl)-5H-pyrrolo[2,3-b]pyrazine-7-carboxylic acid tert-butylamide |

TABLE I-continued
| COMPOUND | STRUCTURE | SYSTEMATIC NAME |
| --- | --- | --- |
| I-290 | 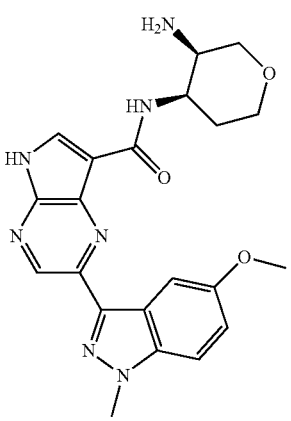 | 2-(5-Methoxy-1-methyl-1H-indazol-3-yl)-5H-pyrrolo[2,3-b]pyrazine-7-carboxylic acid ((3R,4R)-3-amino-tetrahydro-pyran-4-yl)-amide |
| I-291 | 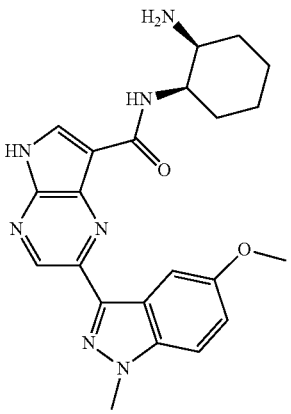 [SMILES: COc1ccc2c(c1)c(-c1cnc3[nH]cc(C(=O)N[C@@H]4CCOC[C@@H]4N)c3n1)nn2C] | 2-(5-Methoxy-1-methyl-1H-indazol-3-yl)-5H-pyrrolo[2,3-b]pyrazine-7-carboxylic acid ((1R,2S)-2-amino-cyclohexyl)-amide |
| I-292 | 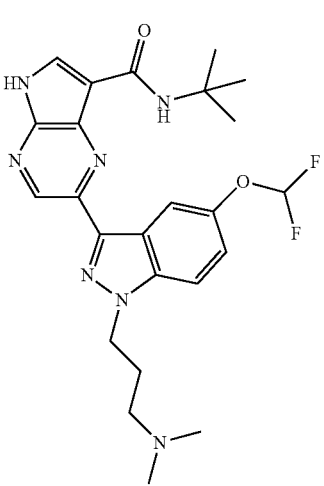 [SMILES: CN(C)CCCn1nc(-c2cnc3[nH]cc(C(=O)NC(C)(C)C)c3n2)c2cc(OC(F)F)ccc21] | 2-[5-Difluoromethoxy-1-(3-dimethylamino-propyl)-1H-indazol-3-yl]-5H-pyrrolo[2,3-b]pyrazine-7-carboxylic acid tert-butylamide |

TABLE I-continued

| COMPOUND | STRUCTURE | SYSTEMATIC NAME |
| --- | --- | --- |
| I-293 | 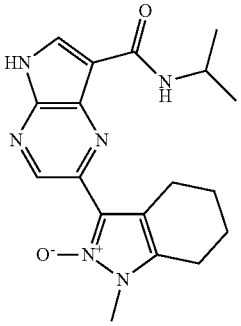 [SMILES: CC(C)NC(=O)c1c[nH]c2ncc(-c3c4c(n(C)[n+]3[O-])CCCC4)nc12] | 2-(1-Methyl-2-oxy-4,5,6,7-tetrahydro-1H-indazol-3-yl)-5H-pyrrolo[2,3-b]pyrazine-7-carboxylic acid isopropylamide |
| I-294 | 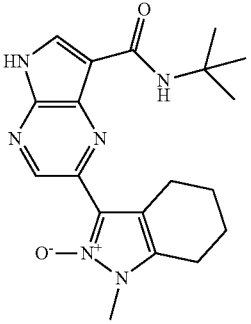 | 2-(1-Methyl-2-oxy-4,5,6,7-tetrahydro-1H-indazol-3-yl)-5H-pyrrolo[2,3-b]pyrazine-7-carboxylic acid tert-butylamide |
| I-295 | 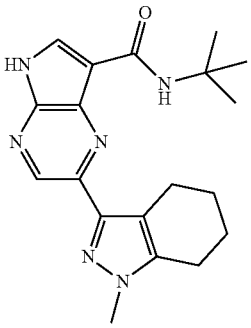 [SMILES: Cn1c2c(c(-c3cnc4[nH]cc(C(=O)NC(C)(C)C)c4n3)[n+]1[O-])CCCC2] | 2-(1-Methyl-4,5,6,7-tetrahydro-1H-indazol-3-yl)-5H-pyrrolo[2,3-b]pyrazine-7-carboxylic acid tert-butylamide |
| I-296 | 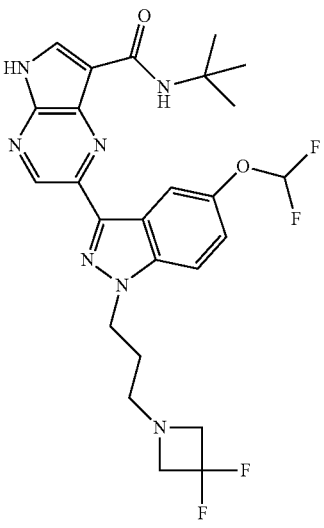 [SMILES: CC(C)(C)NC(=O)c1c[nH]c2ncc(-c3nn(CCCN4CC(F)(F)C4)c4ccc(OC(F)F)cc34)nc12] | 2-{1-[3-(3,3-Difluoro-azetidin-1-yl)-propyl]-5-difluoromethoxy-1H-indazol-3-yl}-5H-pyrrolo[2,3-b]pyrazine-7-carboxylic acid tert-butylamide |

TABLE I-continued

| COMPOUND | STRUCTURE | SYSTEMATIC NAME |
|---|---|---|
| I-297 | 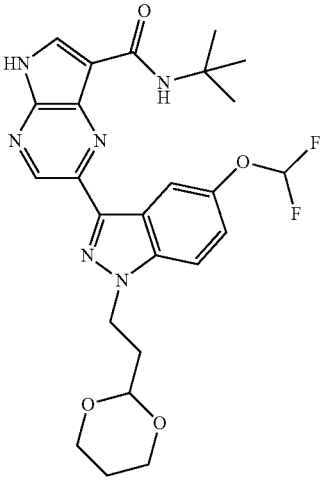 [SMILES: CC(C)(C)NC(=O)c1c[nH]c2ncc(-c3nn(CCC4OCCCO4)c4ccc(OC(F)F)cc34)nc12] | 2-[5-Difluoromethoxy-1-(2-[1,3]dioxan-2-yl-ethyl)-1H-indazol-3-yl]-5H-pyrrolo[2,3-b]pyrazine-7-carboxylic acid tert-butylamide |
| I-298 | 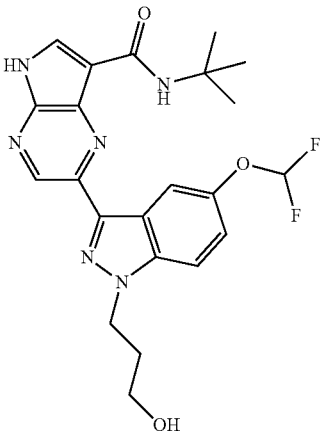 [SMILES: CC(C)(C)NC(=O)c1c[nH]c2ncc(-c3nn(CCCO)c4ccc(OC(F)F)cc34)nc12] | 2-[5-Difluoromethoxy-1-(3-hydroxy-propyl)-1H-indazol-3-yl]-5H-pyrrolo[2,3-b]pyrazine-7-carboxylic acid tert-butylamide |
| I-299 | 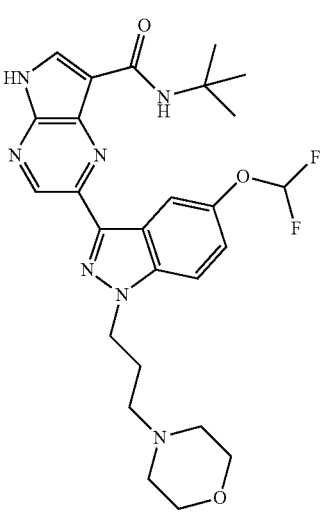 [SMILES: CC(C)(C)NC(=O)c1c[nH]c2ncc(-c3nn(CCCN4CCOCC4)c4ccc(OC(F)F)cc34)nc12] | 2-[5-Difluoromethoxy-1-(3-morpholin-4-yl-propyl)-1H-indazol-3-yl]-5H-pyrrolo[2,3-b]pyrazine-7-carboxylic acid tert-butylamide |

| COMPOUND | STRUCTURE | SYSTEMATIC NAME |
|---|---|---|
| I-300 | 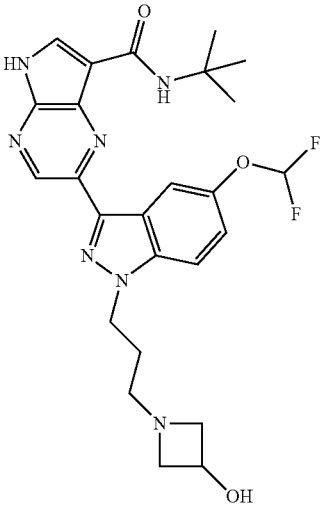 [SMILES: CC(C)(C)NC(=O)c1c[nH]c2ncc(-c3nn(CCCN4CC(O)C4)c4ccc(OC(F)F)cc34)nc12] | 2-{5-Difluoromethoxy-1-[3-(3-hydroxy-azetidin-1-yl)-propyl]-1H-indazol-3-yl}-5H-pyrrolo[2,3-b]pyrazine-7-carboxylic acid tert-butylamide |
| I-301 | 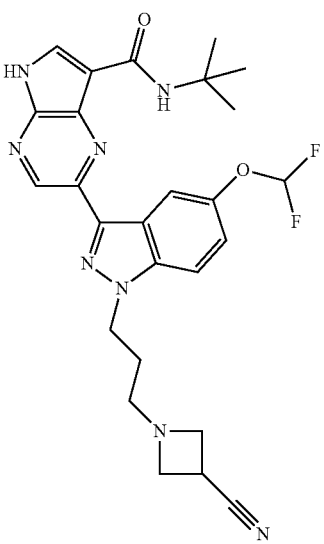 [SMILES: CC(C)(C)NC(=O)c1c[nH]c2ncc(-c3nn(CCCN4CC(C#N)C4)c4ccc(OC(F)F)cc34)nc12] | 2-{1-[3-(3-Cyano-azetidin-1-yl)-propyl]-5-difluoromethoxy-1H-indazol-3-yl}-5H-pyrrolo[2,3-b]pyrazine-7-carboxylic acid tert-butylamide |
| I-302 | 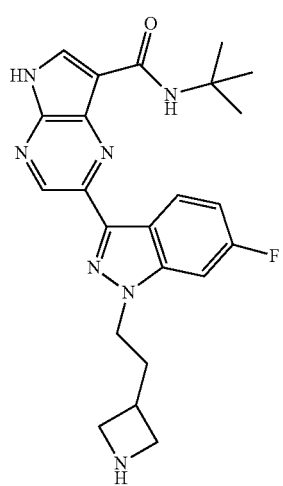 [SMILES: CC(C)(C)NC(=O)c1c[nH]c2ncc(-c3nn(CCC4CNC4)c4cc(F)ccc34)nc12] | 2-[1-(2-Azetidin-3-yl-ethyl)-6-fluoro-1H-indazol-3-yl]-5H-pyrrolo[2,3-b]pyrazine-7-carboxylic acid tert-butylamide |

TABLE I-continued

| COMPOUND | STRUCTURE | SYSTEMATIC NAME |
|---|---|---|
| I-303 | 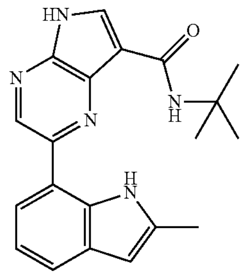 [SMILES: Cc1cc2cccc(-c3cnc4[nH]cc(C(=O)NC(C)(C)C)c4n3)c2[nH]1] | 2-(2-Methyl-1H-indol-7-yl)-5H-pyrrolo[2,3-b]pyrazine-7-carboxylic acid tert-butylamide |
| I-304 | 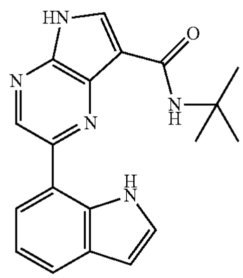 [SMILES: CC(C)(C)NC(=O)c1c[nH]c2ncc(-c3cccc4cc[nH]c34)nc12] | 2-(1H-Indol-7-yl)-5H-pyrrolo[2,3-b]pyrazine-7-carboxylic acid tert-butylamide |
| I-305 | 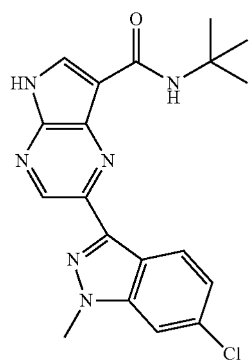 [SMILES: Cn1nc(-c2cnc3[nH]cc(C(=O)NC(C)(C)C)c3n2)c2ccc(Cl)cc21] | 2-(6-Chloro-1-methyl-1H-indazol-3-yl)-5H-pyrrolo[2,3-b]pyrazine-7-carboxylic acid tert-butylamide |
| I-306 | 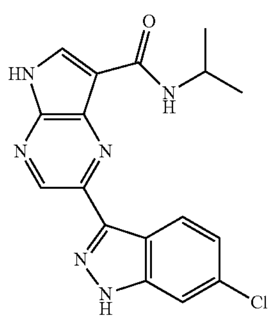 [SMILES: CC(C)NC(=O)c1c[nH]c2ncc(-c3n[nH]c4cc(Cl)ccc34)nc12] | 2-(6-Chloro-1H-indazol-3-yl)-5H-pyrrolo[2,3-b]pyrazine-7-carboxylic acid isopropylamide |
| I-307 | 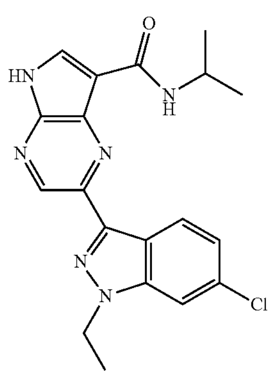 [SMILES: CCn1nc(-c2cnc3[nH]cc(C(=O)NC(C)C)c3n2)c2ccc(Cl)cc21] | 2-(6-Chloro-1-ethyl-1H-indazol-3-yl)-5H-pyrrolo[2,3-b]pyrazine-7-carboxylic acid isopropylamide |

TABLE I-continued
| COMPOUND | STRUCTURE | SYSTEMATIC NAME |
|---|---|---|
| I-308 | 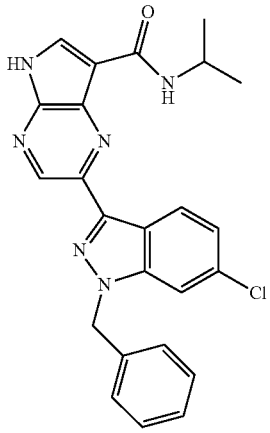 [SMILES: CC(C)NC(=O)c1c[nH]c2ncc(-c3nn(Cc4ccccc4)c4cc(Cl)ccc34)nc12] | 2-(1-Benzyl-6-chloro-1H-indazol-3-yl)-5H-pyrrolo[2,3-b]pyrazine-7-carboxylic acid isopropylamide |
| I-309 | 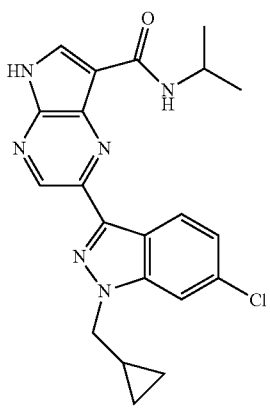 [SMILES: CC(C)NC(=O)c1c[nH]c2ncc(-c3nn(CC4CC4)c4cc(Cl)ccc34)nc12] | 2-(6-Chloro-1-cyclopropylmethyl-1H-indazol-3-yl)-5H-pyrrolo[2,3-b]pyrazine-7-carboxylic acid isopropylamide |
| I-310 | 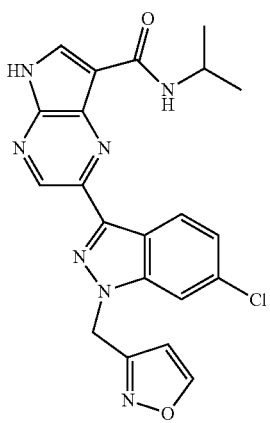 [SMILES: CC(C)NC(=O)c1c[nH]c2ncc(-c3nn(Cc4ccon4)c4cc(Cl)ccc34)nc12] | 2-(6-Chloro-1-isoxazol-3-ylmethyl-1H-indazol-3-yl)-5H-pyrrolo[2,3-b]pyrazine-7-carboxylic acid isopropylamide |

TABLE I-continued
| COMPOUND | STRUCTURE | SYSTEMATIC NAME |
|---|---|---|
| I-311 | 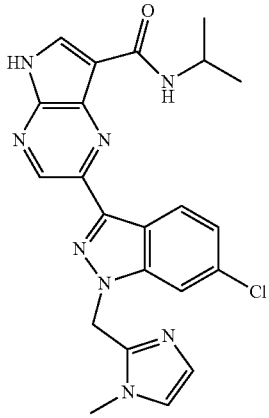 [SMILES: CC(C)NC(=O)c1c[nH]c2ncc(-c3nn(Cc4nccn4C)c4cc(Cl)ccc34)nc12] | 2-[6-Chloro-1-(1-methyl-1H-imidazol-2-ylmethyl)-1H-indazol-3-yl]-5H-pyrrolo[2,3-b]pyrazine-7-carboxylic acid isopropylamide |
| I-312 | 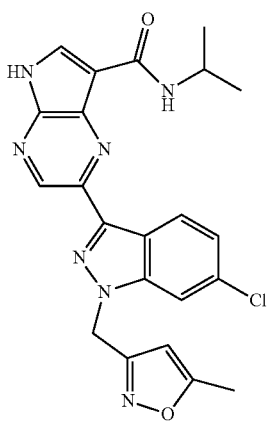 [SMILES: Cc1cc(Cn2nc(-c3cnc4[nH]cc(C(=O)NC(C)C)c4n3)c3ccc(Cl)cc32)no1] | 2-[6-Chloro-1-(5-methyl-isoxazol-3-ylmethyl)-1H-indazol-3-yl]-5H-pyrrolo[2,3-b]pyrazine-7-carboxylic acid isopropylamide |
| I-313 | 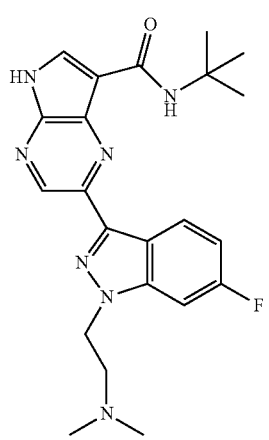 [SMILES: CN(C)CCn1nc(-c2cnc3[nH]cc(C(=O)NC(C)(C)C)c3n2)c2ccc(F)cc21] | 2-[1-(2-Dimethylamino-ethyl)-6-fluoro-1H-indazol-3-yl]-5H-pyrrolo[2,3-b]pyrazine-7-carboxylic acid tert-butylamide |

TABLE I-continued

| COMPOUND | STRUCTURE | SYSTEMATIC NAME |
|---|---|---|
| I-314 | 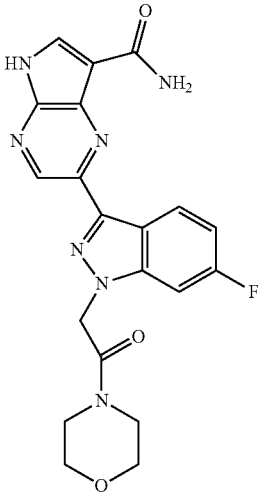 [SMILES: NC(=O)c1c[nH]c2ncc(-c3nn(CC(=O)N4CCOCC4)c4cc(F)ccc34)nc12] | 2-[6-Fluoro-1-(2-morpholin-4-yl-2-oxo-ethyl)-1H-indazol-3-yl]-5H-pyrrolo[2,3-b]pyrazine-7-carboxylic acid amide |
| I-315 | 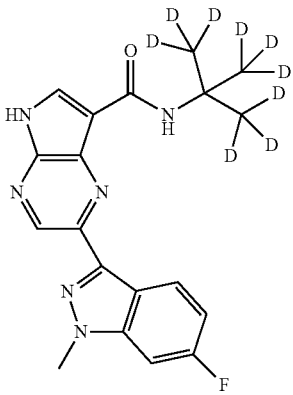 [SMILES: [2H]C([2H])([2H])C(NC(=O)c1c[nH]c2ncc(-c3nn(C)c4cc(F)ccc34)nc12)(C([2H])([2H])[2H])C([2H])([2H])[2H]] | 2-(6-Fluoro-1-methyl-1H-indazol-3-yl)-5H-pyrrolo[2,3-b]pyrazine-7-carboxylic acid -$d_9$-tert-butylamide |
| I-316 | 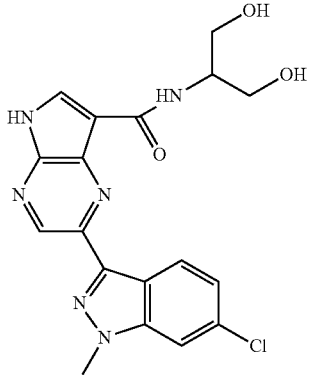 [SMILES: Cn1nc(-c2cnc3[nH]cc(C(=O)NC(CO)CO)c3n2)c2ccc(Cl)cc21] | 2-(6-Chloro-1-methyl-1H-indazol-3-yl)-5H-pyrrolo[2,3-b]pyrazine-7-carboxylic acid (2-hydroxy-1-hydroxymethyl-ethyl)-amide |
| I-317 | 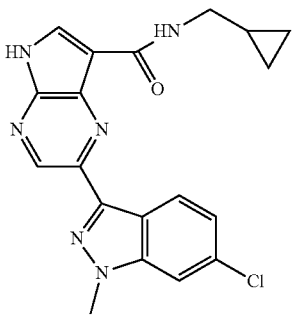 [SMILES: Cn1nc(-c2cnc3[nH]cc(C(=O)NCC4CC4)c3n2)c2ccc(Cl)cc21] | 2-(6-Chloro-1-methyl-1H-indazol-3-yl)-5H-pyrrolo[2,3-b]pyrazine-7-carboxylic acid cyclopropylmethyl-amide |

TABLE I-continued

| COMPOUND | STRUCTURE | SYSTEMATIC NAME |
|---|---|---|
| I-318 | 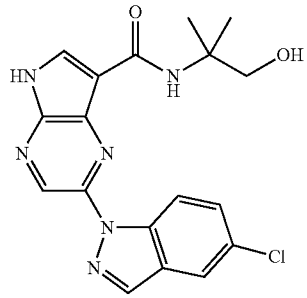 [SMILES: CC(C)(CO)NC(=O)c1c[nH]c2ncc(-n3ncc4cc(Cl)ccc43)nc12] | 2-(5-Chloro-indazol-1-yl)-5H-pyrrolo[2,3-b]pyrazine-7-carboxylic acid (2-hydroxy-1,1-dimethyl-ethyl)-amide |
| I-319 | 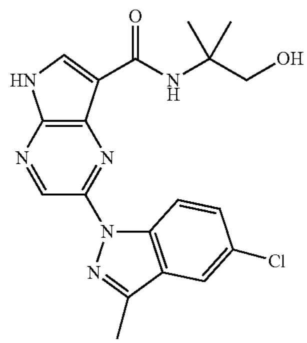 [SMILES: Cc1nn(-c2cnc3[nH]cc(C(=O)NC(C)(C)CO)c3n2)c2ccc(Cl)cc12] | 2-(5-Chloro-3-methyl-indazol-1-yl)-5H-pyrrolo[2,3-b]pyrazine-7 carboxylic acid (2-hydroxy-1,1-dimethyl-ethyl)-amide |
| I-320 | 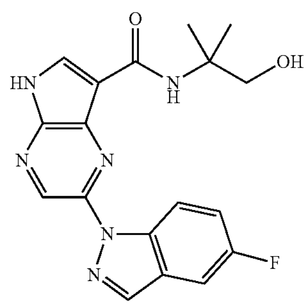 [SMILES: CC(C)(CO)NC(=O)c1c[nH]c2ncc(-n3ncc4cc(F)ccc43)nc12] | 2-(5-Fluoro-indazol-1-yl)-5H-pyrrolo[2,3-b]pyrazine-7-carboxylic acid (2-hydroxy-1,1-dimethyl-ethyl)-amide |
| I-321 | 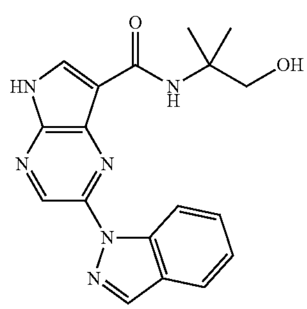 [SMILES: CC(C)(CO)NC(=O)c1c[nH]c2ncc(-n3ncc4ccccc43)nc12] | 2-Indazol-1-yl-5H-pyrrolo[2,3-b]pyrazine-7-carboxylic acid (2-hydroxy-1,1-dimethyl-ethyl)-amide |
| I-322 | 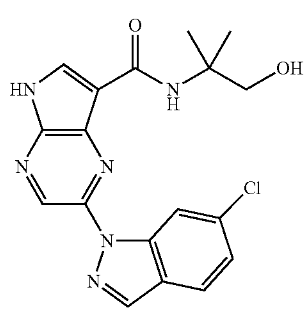 [SMILES: CC(C)(CO)NC(=O)c1c[nH]c2ncc(-n3ncc4ccc(Cl)cc43)nc12] | 2-(6-Chloro-indazol-1-yl)-5H-pyrrolo[2,3-b]pyrazine-7-carboxylic acid (2-hydroxy-1,1-dimethyl-ethyl)-amide |

TABLE I-continued

| COMPOUND | STRUCTURE | SYSTEMATIC NAME |
| --- | --- | --- |
| I-323 | 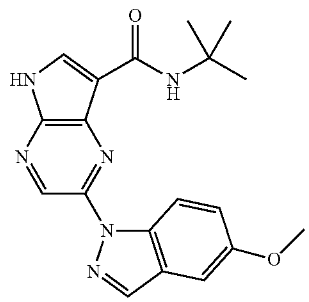 [SMILES: COc1ccc2c(cnn2-c2cnc3[nH]cc(C(=O)NC(C)(C)C)c3n2)c1] | 2-(5-Methoxy-indazol-1-yl)-5H-pyrrolo[2,3-b]pyrazine-7-carboxylic acid tert-butylamide |
| I-324 | 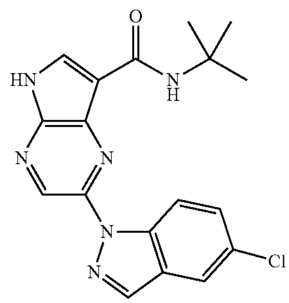 [SMILES: CC(C)(C)NC(=O)c1c[nH]c2ncc(-n3ncc4cc(Cl)ccc43)nc12] | 2-(5-Chloro-indazol-1-yl)-5H-pyrrolo[2,3-b]pyrazine-7-carboxylic acid tert-butylamide |
| I-325 | 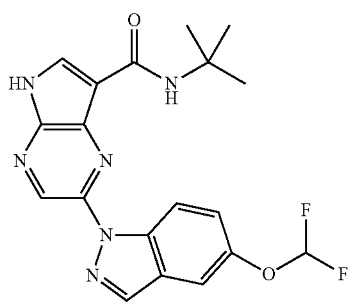 [SMILES: CC(C)(C)NC(=O)c1c[nH]c2ncc(-n3ncc4cc(OC(F)F)ccc43)nc12] | 2-(5-Difluoromethoxy-indazol-1-yl)-5H-pyrrolo[2,3-b]pyrazine-7-carboxylic acid tert-butylamide |
| I-326 | 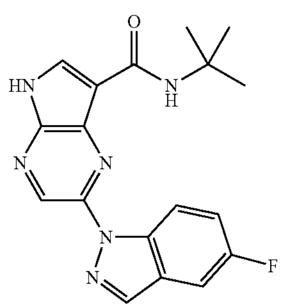 [SMILES: CC(C)(C)NC(=O)c1c[nH]c2ncc(-n3ncc4cc(F)ccc43)nc12] | 2-(5-Fluoro-indazol-1-yl)-5H-pyrrolo[2,3-b]pyrazine-7-carboxylic acid tert-butylamide |
| I-327 | 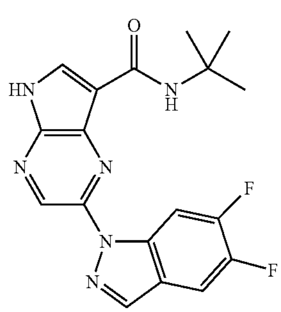 [SMILES: CC(C)(C)NC(=O)c1c[nH]c2ncc(-n3ncc4cc(F)c(F)cc43)nc12] | 2-(5,6-Difluoro-indazol-1-yl)-5H-pyrrolo[2,3-b]pyrazine-7-carboxylic acid tert-butylamide |

| COMPOUND | STRUCTURE | SYSTEMATIC NAME |
| --- | --- | --- |
| I-328 | 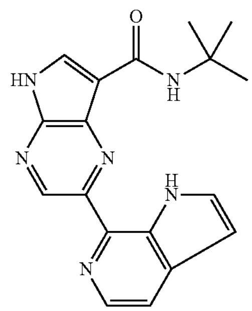 [SMILES: CC(C)(C)NC(=O)c1c[nH]c2ncc(-c3nccc4cc[nH]c34)nc12] | 2-(1H-Pyrrolo[2,3-c]pyridin-7-yl)-5H-pyrrolo[2,3-b]pyrazine-7 carboxylic acid tert-butylamide |
| I-329 | 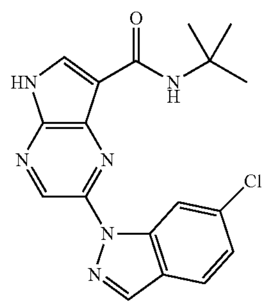 [SMILES: CC(C)(C)NC(=O)c1c[nH]c2ncc(-n3ncc4ccc(Cl)cc43)nc12] | 2-(6-Chloro-indazol-1-yl)-5H-pyrrolo[2,3-b]pyrazine-7-carboxylic acid tert-butylamide |
| I-330 | 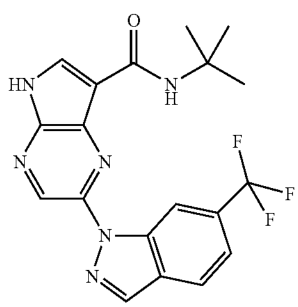 [SMILES: CC(C)(C)NC(=O)c1c[nH]c2ncc(-n3ncc4ccc(C(F)(F)F)cc43)nc12] | 2-(6-Trifluoromethyl-indazol-1-yl)-5H-pyrrolo[2,3-b]pyrazine-7-carboxylic acid tert-butylamide |
| I-331 | 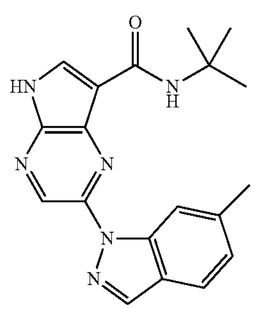 [SMILES: Cc1ccc2cnn(-c3cnc4[nH]cc(C(=O)NC(C)(C)C)c4n3)c2c1] | 2-(6-Methyl-indazol-1-yl)-5H-pyrrolo[2,3-b]pyrazine-7-carboxylic acid tert-butylamide |
| I-332 | 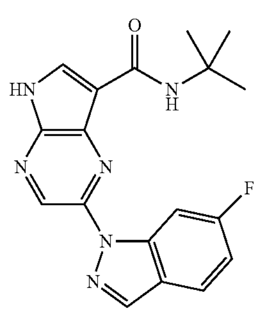 [SMILES: CC(C)(C)NC(=O)c1c[nH]c2ncc(-n3ncc4ccc(F)cc43)nc12] | 2-(6-Fluoro-indazol-1-yl)-5H-pyrrolo[2,3-b]pyrazine-7-carboxylic acid tert-butylamide |

TABLE I-continued

| COMPOUND | STRUCTURE | SYSTEMATIC NAME |
| --- | --- | --- |
| I-333 | 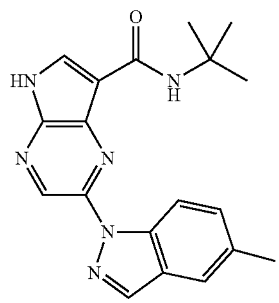 [SMILES: Cc1ccc2c(cnn2-c2cnc3[nH]cc(C(=O)NC(C)(C)C)c3n2)c1] | 2-(5-Methyl-indazol-1-yl)-5H-pyrrolo[2,3-b]pyrazine-7-carboxylic acid tert-butylamide |
| I-334 | 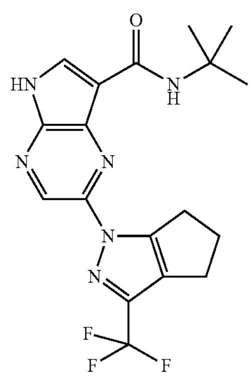 [SMILES: CC(C)(C)NC(=O)c1c[nH]c2ncc(-n3nc(C(F)(F)F)c4c3CCC4)nc12] | 2-(3-Trifluoromethyl-5,6-dihydro-4H-cyclopentapyrazol-1-yl)-5H-pyrrolo[2,3-b]pyrazine-7-carboxylic acid tert-butylamide |
| I-335 | 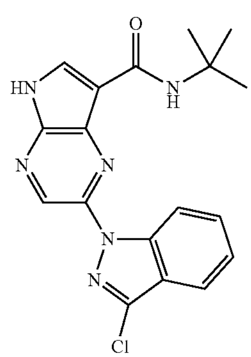 [SMILES: CC(C)(C)NC(=O)c1c[nH]c2ncc(-n3nc(Cl)c4ccccc43)nc12] | 2-(3-Chloro-indazol-1-yl)-5H-pyrrolo[2,3-b]pyrazine-7-carboxylic acid tert-butylamide |
| I-336 | 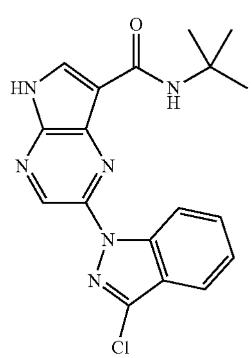 [SMILES: CC(C)(C)NC(=O)c1c[nH]c2ncc(-n3nc(Cl)c4ccccc43)nc12] | 2-(5-Methyl-pyrazolo[3,4-b]pyridin-1-yl)-5H-pyrrolo[2,3-b]pyrazine-7-carboxylic acid tert-butylamide |

TABLE I-continued

| COMPOUND | STRUCTURE | SYSTEMATIC NAME |
|---|---|---|
| I-337 | 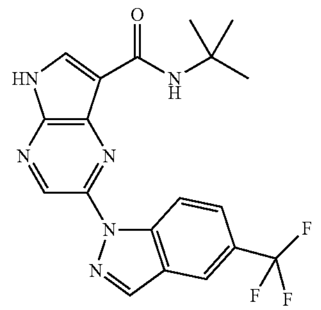 [SMILES: CC(C)(C)NC(=O)c1c[nH]c2ncc(-n3ncc4cc(C(F)(F)F)ccc43)nc12] | 2-(5-Trifluoromethyl-indazol-1-yl)-5H-pyrrolo[2,3-b]pyrazine-7-carboxylic acid tert-butylamide |
| I-338 | 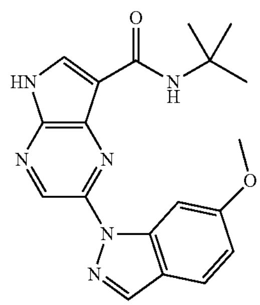 | 2-(6-Methoxy-indazol-1-yl)-5H-pyrrolo[2,3-b]pyrazine-7-carboxylic acid tert-butylamide |
| I-339 | 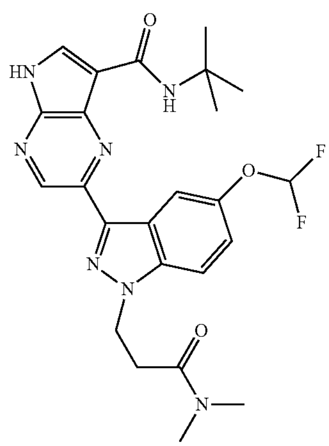 [SMILES: CN(C)C(=O)CCn1nc(-c2cnc3[nH]cc(C(=O)NC(C)(C)C)c3n2)c2cc(OC(F)F)ccc21] | 2-[5-Difluoromethoxy-1-(2-dimethylcarbamoyl-ethyl)-1H-indazol-3-yl]-5H-pyrrolo[2,3-b]pyrazine-7-carboxylic acid tert-butylamide |
| I-340 | 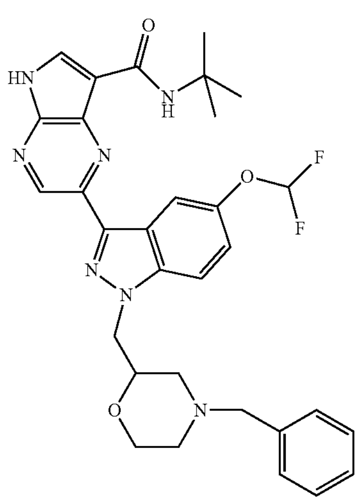 [SMILES: CC(C)(C)NC(=O)c1c[nH]c2ncc(-c3nn(CC4CN(Cc5ccccc5)CCO4)c4ccc(OC(F)F)cc34)nc12] | 2-[1-(4-Benzyl-morpholin-2-ylmethyl)-5-difluoromethoxy-1H-indazol-3-yl]-5H-pyrrolo[2,3-b]pyrazine-7-carboxylic acid tert-butylamide |

TABLE I-continued

| COMPOUND | STRUCTURE | SYSTEMATIC NAME |
|---|---|---|
| I-341 | 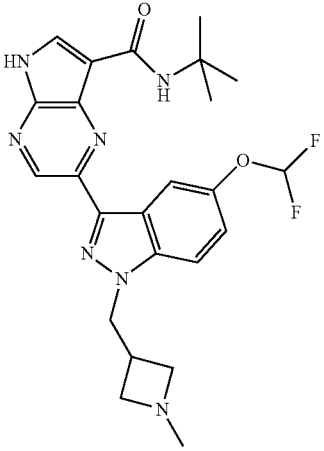 [SMILES: CN1CC(Cn2nc(-c3cnc4[nH]cc(C(=O)NC(C)(C)C)c4n3)c3cc(OC(F)F)ccc32)C1] | 2-[5-Difluoromethoxy-1-(1-methyl-azetidin-3-ylmethyl)-1H-indazol-3-yl]-5H-pyrrolo[2,3-b]pyrazine-7-carboxylic acid tert-butylamide |
| I-342 | 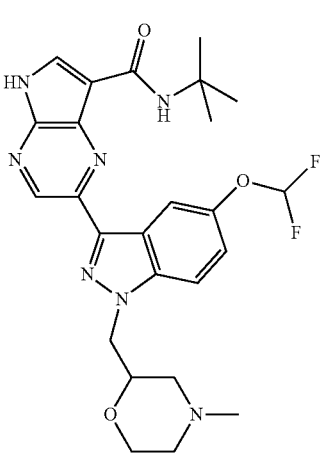 [SMILES: CN1CCOC(Cn2nc(-c3cnc4[nH]cc(C(=O)NC(C)(C)C)c4n3)c3cc(OC(F)F)ccc32)C1] | 2-[5-Difluoromethoxy-1-(4-methyl-morpholin-2-ylmethyl)-1H-indazol-3-yl]-5H-pyrrolo[2,3-b]pyrazine-7-carboxylic acid tert-butylamide |
| I-343 | 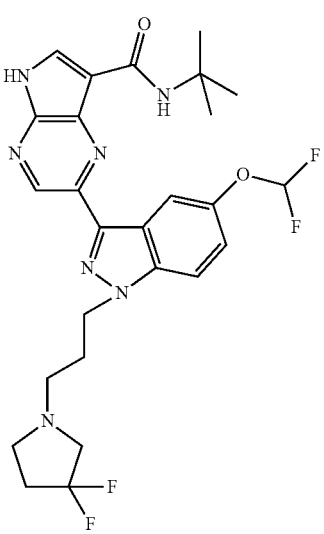 [SMILES: CC(C)(C)NC(=O)c1c[nH]c2ncc(-c3nn(CCCN4CCC(F)(F)C4)c4ccc(OC(F)F)cc34)nc12] | 2-{5-Difluoromethoxy-1-[3-(3,3-difluoro-pyrrolidin-1-yl)-propyl]-1H-indazol-3-yl}-5H-pyrrolo[2,3-b]pyrazine-7-carboxylic acid tert-butylamide |

TABLE I-continued

| COMPOUND | STRUCTURE | SYSTEMATIC NAME |
|---|---|---|
| I-344 | 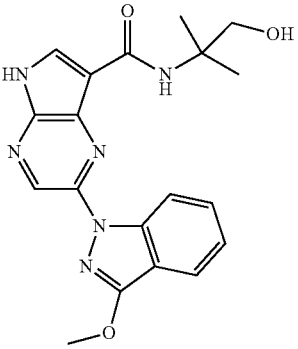 [SMILES: COc1nn(-c2cnc3[nH]cc(C(=O)NC(C)(C)CO)c3n2)c2ccccc12] | 2-(3-Methoxy-indazol-1-yl)-5H-pyrrolo[2,3-b]pyrazine-7-carboxylic acid (2-hydroxy-1,1-dimethyl-ethyl)-amide |
| I-345 | 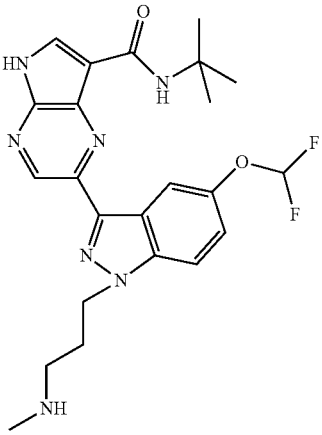 [SMILES: CNCCCn1nc(-c2cnc3[nH]cc(C(=O)NC(C)(C)C)c3n2)c2cc(OC(F)F)ccc21] | 2-[5-Difluoromethoxy-1-(3-methylamino-propyl)-1H-indazol-3-yl]-5H-pyrrolo[2,3-b]pyrazine-7-carboxylic acid tert-butylamide |
| I-346 | 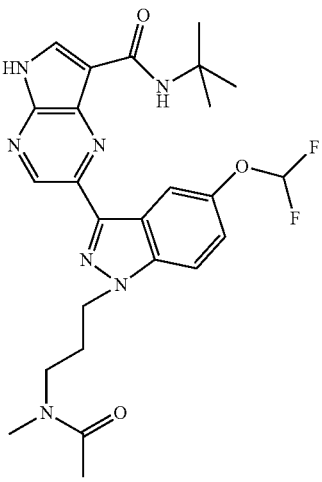 [SMILES: CC(=O)N(C)CCCn1nc(-c2cnc3[nH]cc(C(=O)NC(C)(C)C)c3n2)c2cc(OC(F)F)ccc21] | 2-{1-[3-(Acetyl-methyl-amino)-propyl]-5-difluoromethoxy-1H-indazol-3-yl}-5H-pyrrolo[2,3-b]pyrazine-7-carboxylic acid tert-butylamide |

TABLE I-continued

| COMPOUND | STRUCTURE | SYSTEMATIC NAME |
|---|---|---|
| I-347 | 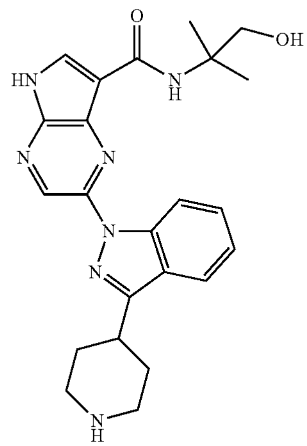 [SMILES: CC(C)(CO)NC(=O)c1c[nH]c2ncc(-n3nc(C4CCNCC4)c4ccccc43)nc12] | 2-(3-Piperidin-4-yl-indazol-1-yl)-5H-pyrrolo[2,3-b]pyrazine-7-carboxylic acid (2-hydroxy-1,1-dimethyl-ethyl)-amide |
| I-348 | 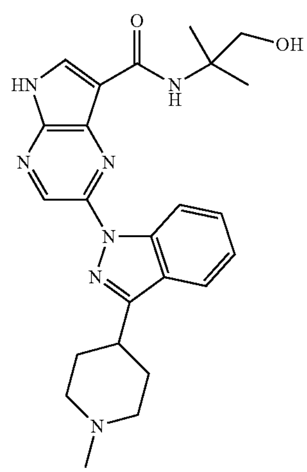 [SMILES: CN1CCC(c2nn(-c3cnc4[nH]cc(C(=O)NC(C)(C)CO)c4n3)c3ccccc23)CC1] | 2-[3-(1-Methyl-piperidin-4-yl)-indazol-1-yl]-5H-pyrrolo[2,3-b]pyrazine-7-carboxylic acid (2-hydroxy-1,1-dimethyl-ethyl)-amide |
| I-349 | 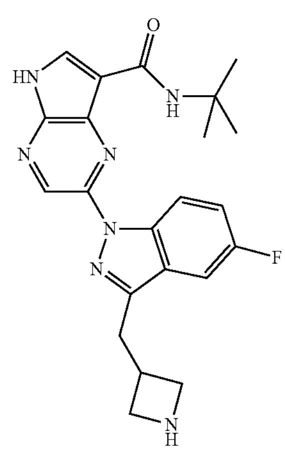 [SMILES: CC(C)(C)NC(=O)c1c[nH]c2ncc(-n3nc(CC4CNC4)c4cc(F)ccc43)nc12] | 2-(1-Azetidin-3-ylmethyl-6-fluoro-1H-indazol-3-yl)-5H-pyrrolo[2,3-b]pyrazine-7-carboxylic acid tert-butylamide |

| COMPOUND | STRUCTURE | SYSTEMATIC NAME |
|---|---|---|
| I-350 | 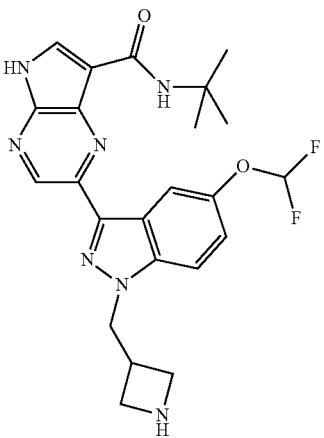 [SMILES: CC(C)(C)NC(=O)c1c[nH]c2ncc(-c3nn(CC4CNC4)c4ccc(OC(F)F)cc34)nc12] | 2-(1-Azetidin-3-ylmethyl-5-difluoromethoxy-1H-indazol-3-yl)-5H-pyrrolo[2,3-b]pyrazine-7-carboxylic acid tert-butylamide |
| I-351 | 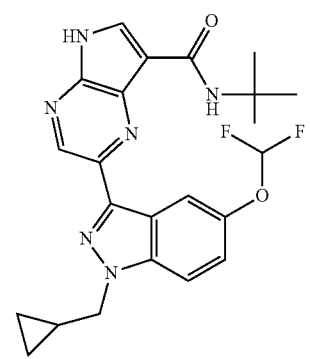 [SMILES: CC(C)(C)NC(=O)c1c[nH]c2ncc(-c3nn(CC4CC4)c4ccc(OC(F)F)cc34)nc12] | 2-(1-Cyclopropylmethyl-5-difluoromethoxy-1H-indazol-3-yl)-5H-pyrrolo[2,3-b]pyrazine-7-carboxylic acid tert-butylamide |
| I-352 | 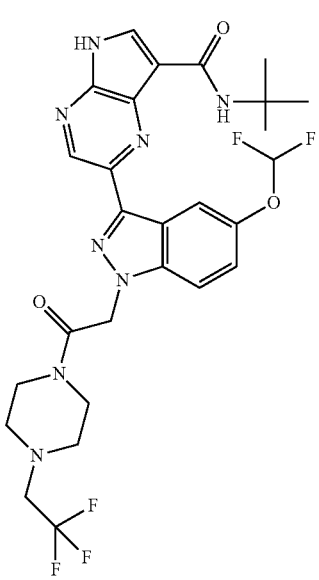 [SMILES: CC(C)(C)NC(=O)c1c[nH]c2ncc(-c3nn(CC(=O)N4CCN(CC(F)(F)F)CC4)c4ccc(OC(F)F)cc34)nc12] | 2-(5-Difluoromethoxy-1-{2-oxo-2-[4-(2,2,2-trifluoro-ethyl)-piperazin-1-yl]-ethyl}-1H-indazol-3-yl)-5H-pyrrolo[2,3-b]pyrazine-7-carboxylic acid tert-butylamide |

TABLE I-continued

| COMPOUND | STRUCTURE | SYSTEMATIC NAME |
|---|---|---|
| I-353 | 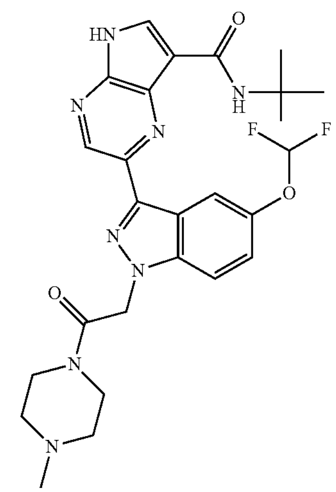 [SMILES: CN1CCN(C(=O)Cn2nc(-c3cnc4[nH]cc(C(=O)NC(C)(C)C)c4n3)c3cc(OC(F)F)ccc32)CC1] | 2-{5-Difluoromethoxy-1-[2-(4-methyl-piperazin-1-yl)-2-oxo-ethyl]-1H-indazol-3-yl}-5H-pyrrolo[2,3-b]pyrazine-7-carboxylic acid tert-butylamide |
| I-354 | 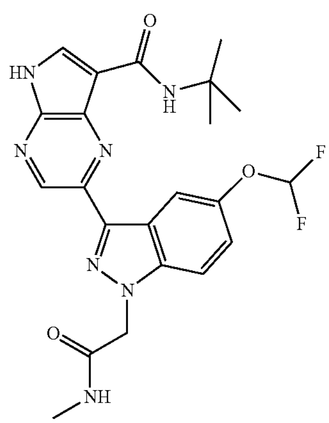 [SMILES: CNC(=O)Cn1nc(-c2cnc3[nH]cc(C(=O)NC(C)(C)C)c3n2)c2cc(OC(F)F)ccc21] | 2-(5-Difluoromethoxy-1-methylcarbamoylmethyl-1H-indazol-3-yl)-5H-pyrrolo[2,3-b]pyrazine-7-carboxylic acid tert-butylamide |
| I-355 | 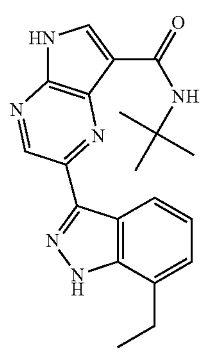 [SMILES: CCc1cccc2c(-c3cnc4[nH]cc(C(=O)NC(C)(C)C)c4n3)n[nH]c12] | 2-(7-Ethyl-1H-indazol-3-yl)-5H-pyrrolo[2,3-b]pyrazine-7-carboxylic acid tert-butylamide |
| I-356 | 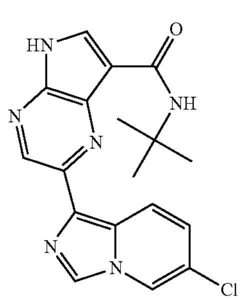 [SMILES: CC(C)(C)NC(=O)c1c[nH]c2ncc(-c3ncn4cc(Cl)ccc34)nc12] | 2-(6-Chloro-imidazo[1,5-a]pyridin-1-yl)-5H-pyrrolo[2,3-b]pyrazine-7-carboxylic acid tert-butylamide |

TABLE I-continued

| COMPOUND | STRUCTURE | SYSTEMATIC NAME |
|---|---|---|
| I-357 | 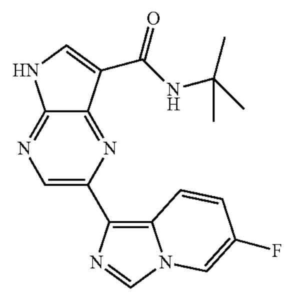 [SMILES: CC(C)(C)NC(=O)c1c[nH]c2ncc(-c3ncn4cc(F)ccc34)nc12] | 2-(6-Fluoro-imidazo[1,5-a]pyridin-1-yl)-5H-pyrrolo[2,3-b]pyrazine-7-carboxylic acid tert-butylamide |
| I-358 | 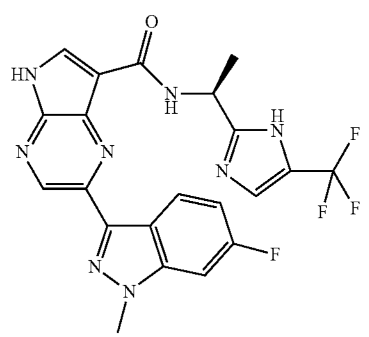 [SMILES: C[C@H](NC(=O)c1c[nH]c2ncc(-c3nn(C)c4cc(F)ccc34)nc12)c1ncc(C(F)(F)F)[nH]1] | 2-(6-Fluoro-1-methyl-1H-indazol-3-yl)-5H-pyrrolo[2,3-b]pyrazine-7-carboxylic acid [(S)-1-(5-trifluoromethyl-1H-imidazol-2-yl)-ethyl]-amide |
| I-359 | 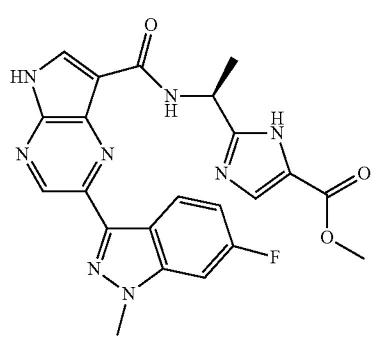 [SMILES: COC(=O)c1cnc([C@H](C)NC(=O)c2c[nH]c3ncc(-c4nn(C)c5cc(F)ccc45)nc23)[nH]1] | 2-((S)-1-{[2-(6-Fluoro-1-methyl-1H-indazol-3-yl)-5H-pyrrolo[2,3-b]pyrazine-7-carbonyl]-amino}-ethyl)-3H-imidazole-4-carboxylic acid methyl ester |
| I-360 | 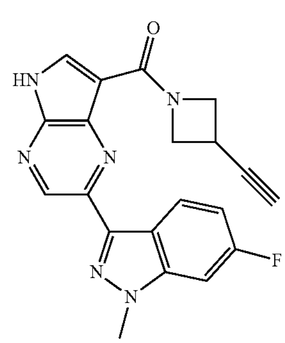 [SMILES: C#CC1CN(C(=O)c2c[nH]c3ncc(-c4nn(C)c5cc(F)ccc45)nc23)C1] | (3-Ethynyl-azetidin-1-yl)-[2-(6-fluoro-1-methyl-1H-indazol-3-yl)-5H-pyrrolo[2,3-b]pyrazin-7-yl]-methanone |

TABLE I-continued

| COMPOUND | STRUCTURE | SYSTEMATIC NAME |
| --- | --- | --- |
| I-361 | 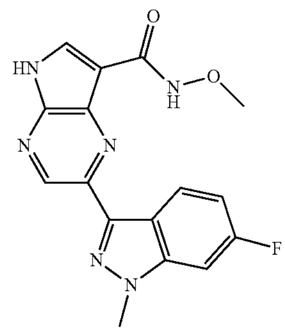 [SMILES: CONC(=O)c1c[nH]c2ncc(-c3nn(C)c4cc(F)ccc34)nc12] | 2-(6-Fluoro-1-methyl-1H-indazol-3-yl)-5H-pyrrolo[2,3-b]pyrazine-7-carboxylic acid methoxy-amide |
| I-362 | 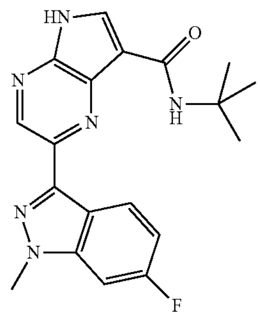 [SMILES: Cn1nc(-c2cnc3[nH]cc(C(=O)NC(C)(C)C)c3n2)c2ccc(F)cc21] | 2-(6-Fluoro-1-methyl-1H-indazol-3-yl)-5H-pyrrolo[2,3-b]pyrazine-7-carboxylic acid tert-butylamide |
| I-363 | 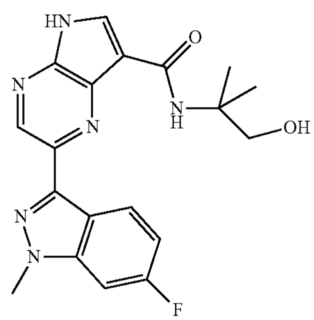 [SMILES: Cn1nc(-c2cnc3[nH]cc(C(=O)NC(C)(C)CO)c3n2)c2ccc(F)cc21] | 2-(6-Fluoro-1-methyl-1H-indazol-3-yl)-5H-pyrrolo[2,3-b]pyrazine-7-carboxylic acid (2-hydroxy-1,1-dimethyl-ethyl)-amide |
| I-364 | 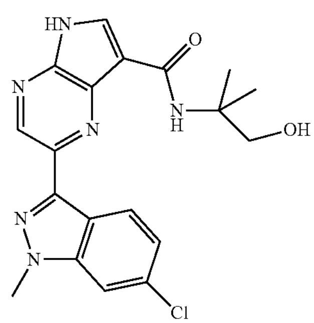 [SMILES: Cn1nc(-c2cnc3[nH]cc(C(=O)NC(C)(C)CO)c3n2)c2ccc(Cl)cc21] | 2-(6-Chloro-1-methyl-1H-indazol-3-yl)-5H-pyrrolo[2,3-b]pyrazine-7-carboxylic acid (2-hydroxy-1,1-dimethyl-ethyl)-amide |
| I-365 | 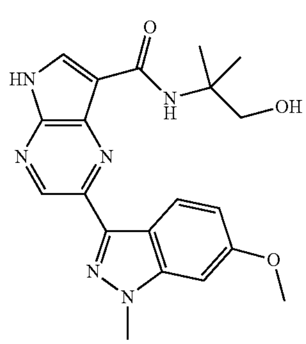 [SMILES: COc1ccc2c(-c3cnc4[nH]cc(C(=O)NC(C)(C)CO)c4n3)nn(C)c2c1] | 2-(6-Methoxy-1-methyl-1H-indazol-3-yl)-5H-pyrrolo[2,3-b]pyrazine-7-carboxylic acid (2-hydroxy-1,1-dimethyl-ethyl)-amide |

TABLE I-continued

| COMPOUND | STRUCTURE | SYSTEMATIC NAME |
| --- | --- | --- |
| I-366 | 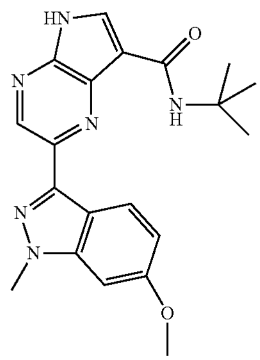 [SMILES: COc1ccc2c(-c3cnc4[nH]cc(C(=O)NC(C)(C)C)c4n3)nn(C)c2c1] | 2-(6-Methoxy-1-methyl-1H-indazol-3-yl)-5H-pyrrolo[2,3-b]pyrazine-7-carboxylic acid tert-butylamide |
| I-367 | 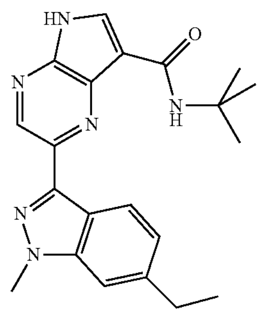 [SMILES: CCc1ccc2c(-c3cnc4[nH]cc(C(=O)NC(C)(C)C)c4n3)nn(C)c2c1] | 2-(6-Ethyl-1-methyl-1H-indazol-3-yl)-5H-pyrrolo[2,3-b]pyrazine-7-carboxylic acid tert-butylamide |
| I-368 | 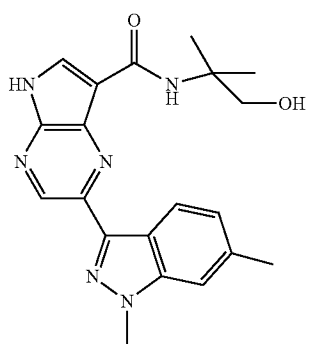 [SMILES: Cc1ccc2c(-c3cnc4[nH]cc(C(=O)NC(C)(C)CO)c4n3)nn(C)c2c1] | 2-(1,6-Dimethyl-1H-indazol-3-yl)-5H-pyrrolo[2,3-b]pyrazine-7-carboxylic acid (2-hydroxy-1,1-dimethyl-ethyl)-amide |
| I-369 | 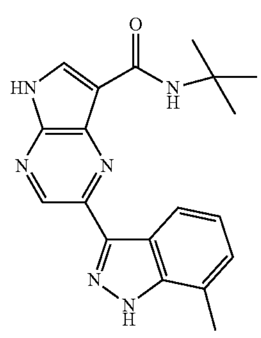 [SMILES: Cc1cccc2c(-c3cnc4[nH]cc(C(=O)NC(C)(C)C)c4n3)n[nH]c12] | 2-(7-Methyl-1H-indazol-3-yl)-5H-pyrrolo[2,3-b]pyrazine-7-carboxylic acid tert-butylamide |

TABLE I-continued

| COMPOUND | STRUCTURE | SYSTEMATIC NAME |
|---|---|---|
| I-370 | 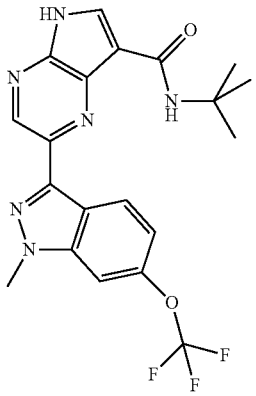 [SMILES: Cn1nc(-c2cnc3[nH]cc(C(=O)NC(C)(C)C)c3n2)c2ccc(OC(F)(F)F)cc21] | 2-(1-Methyl-6-trifluoromethoxy-1H-indazol-3-yl)-5H-pyrrolo[2,3-b]pyrazine-7-carboxylic acid tert-butylamide |
| I-371 | 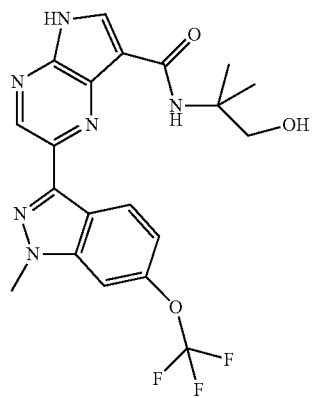 [SMILES: Cn1nc(-c2cnc3[nH]cc(C(=O)NC(C)(C)CO)c3n2)c2ccc(OC(F)(F)F)cc21] | 2-(1-Methyl-6-trifluoromethoxy-1H-indazol-3-yl)-5H-pyrrolo[2,3-b]pyrazine-7-carboxylic acid (2-hydroxy-1,1-dimethyl-ethyl)-amide |
| I-372 | 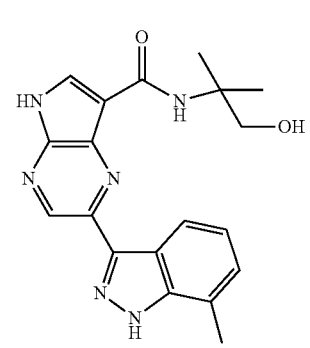 [SMILES: Cc1cccc2c(-c3cnc4[nH]cc(C(=O)NC(C)(C)CO)c4n3)n[nH]c12] | 2-(7-Methyl-1H-indazol-3-yl)-5H-pyrrolo[2,3-b]pyrazine-7-carboxylic acid (2-hydroxy-1,1-dimethyl-ethyl)-amide |
| I-373 | 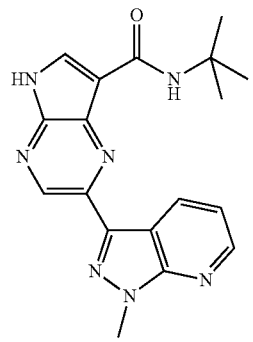 [SMILES: Cn1nc(-c2cnc3[nH]cc(C(=O)NC(C)(C)C)c3n2)c2cccnc21] | 2-(1-Methyl-1H-pyrazolo[3,4-b]pyridin-3-yl)-5H-pyrrolo[2,3-b]pyrazine-7-carboxylic acid tert-butylamide |

TABLE I-continued

| COMPOUND | STRUCTURE | SYSTEMATIC NAME |
| --- | --- | --- |
| I-374 | 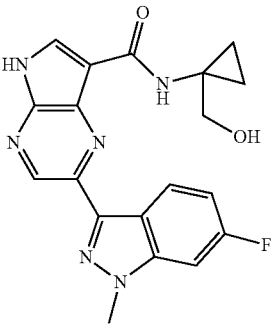 [SMILES: Cn1nc(-c2cnc3[nH]cc(C(=O)NC4(CO)CC4)c3n2)c2ccc(F)cc21] | 2-(6-Fluoro-1-methyl-1H-indazol-3-yl)-5H-pyrrolo[2,3-b]pyrazine-7-carboxylic acid (1-hydroxymethyl-cyclopropyl)-amide |
| I-375 | 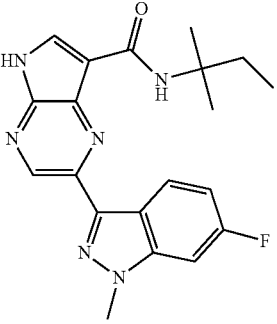 [SMILES: CCC(C)(C)NC(=O)c1c[nH]c2ncc(-c3nn(C)c4cc(F)ccc34)nc12] | 2-(6-Fluoro-1-methyl-1H-indazol-3-yl)-5H-pyrrolo[2,3-b]pyrazine-7-carboxylic acid (1,1-dimethyl-propyl)-amide |
| I-376 | 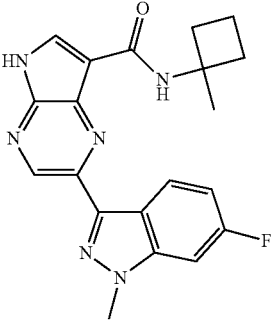 [SMILES: Cn1nc(-c2cnc3[nH]cc(C(=O)NC4(C)CCC4)c3n2)c2ccc(F)cc21] | 2-(6-Fluoro-1-methyl-1H-indazol-3-yl)-5H-pyrrolo[2,3-b]pyrazine-7-carboxylic acid (1-methyl-cyclobutyl)-amide |
| I-377 | 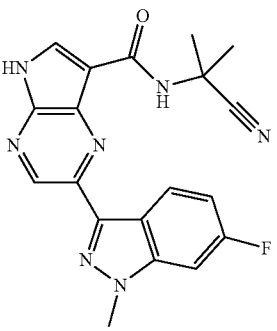 [SMILES: Cn1nc(-c2cnc3[nH]cc(C(=O)NC(C)(C)C#N)c3n2)c2ccc(F)cc21] | 2-(6-Fluoro-1-methyl-1H-indazol-3-yl)-5H-pyrrolo[2,3-b]pyrazine-7-carboxylic acid (cyano-dimethyl-methyl)-amide |

TABLE I-continued

| COMPOUND | STRUCTURE | SYSTEMATIC NAME |
|---|---|---|
| I-378 | 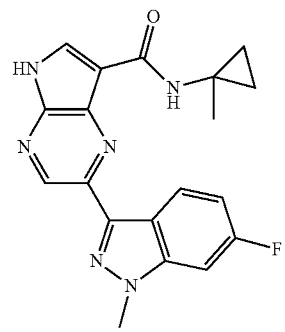 [SMILES: Cn1nc(-c2cnc3[nH]cc(C(=O)NC4(C)CC4)c3n2)c2ccc(F)cc21] | 2-(6-Fluoro-1-methyl-1H-indazol-3-yl)-5H-pyrrolo[2,3-b]pyrazine-7-carboxylic acid (1-methyl-cyclopropyl)-amide |
| I-379 | 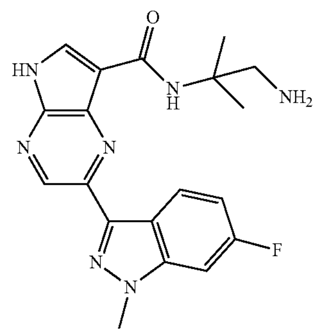 [SMILES: Cn1nc(-c2cnc3[nH]cc(C(=O)NC(C)(C)CN)c3n2)c2ccc(F)cc21] | 2-(6-Fluoro-1-methyl-1H-indazol-3-yl)-5H-pyrrolo[2,3-b]pyrazine-7-carboxylic acid (2-amino-1,1-dimethyl-ethyl)-amide |
| I-380 | 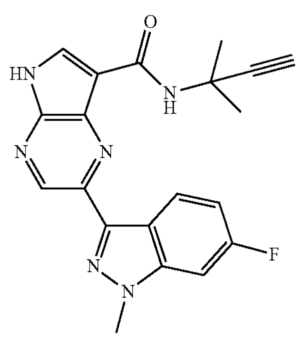 [SMILES: C#CC(C)(C)NC(=O)c1c[nH]c2ncc(-c3nn(C)c4cc(F)ccc34)nc12] | 2-(6-Fluoro-1-methyl-1H-indazol-3-yl)-5H-pyrrolo[2,3-b]pyrazine-7-carboxylic acid (1,1-dimethyl-prop-2-ynyl)-amide |
| I-381 | 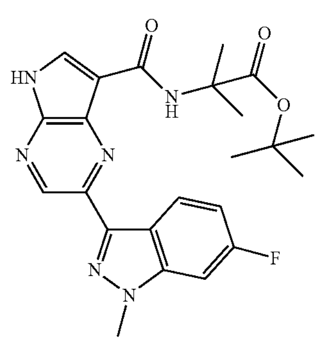 [SMILES: Cn1nc(-c2cnc3[nH]cc(C(=O)NC(C)(C)C(=O)OC(C)(C)C)c3n2)c2ccc(F)cc21] | 2-{[2-(6-Fluoro-1-methyl-1H-indazol-3-yl)-5H-pyrrolo[2,3-b]pyrazine-7-carbonyl]-amino}-2-methyl-propionic acid tert-butyl ester |

TABLE I-continued

| COMPOUND | STRUCTURE | SYSTEMATIC NAME |
|---|---|---|
| I-382 | 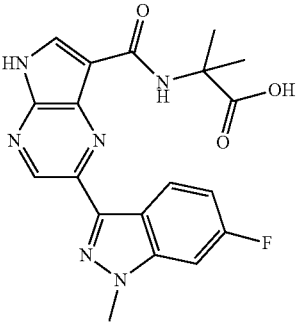 [SMILES: Cn1nc(-c2cnc3[nH]cc(C(=O)NC(C)(C)C(=O)O)c3n2)c2ccc(F)cc21] | 2-{[2-(6-Fluoro-1-methyl-1H-indazol-3-yl)-5H-pyrrolo[2,3-b]pyrazine-7-carbonyl]-amino}-2-methyl-propionic acid |
| I-383 | 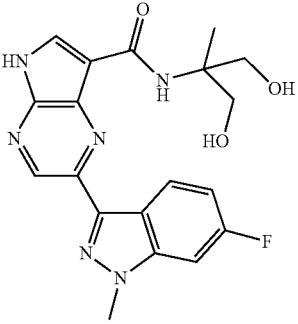 [SMILES: Cn1nc(-c2cnc3[nH]cc(C(=O)NC(C)(CO)CO)c3n2)c2ccc(F)cc21] | 2-(6-Fluoro-1-methyl-1H-indazol-3-yl)-5H-pyrrolo[2,3-b]pyrazine-7-carboxylic acid (2-hydroxy-1-hydroxymethyl-1-methyl-ethyl)-amide |
| I-384 | 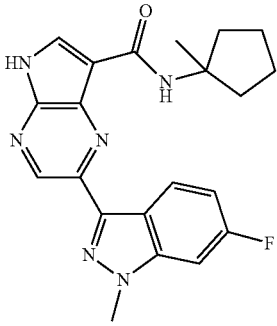 [SMILES: Cn1nc(-c2cnc3[nH]cc(C(=O)NC4(C)CCCC4)c3n2)c2ccc(F)cc21] | 2-(6-Fluoro-1-methyl-1H-indazol-3-yl)-5H-pyrrolo[2,3-b]pyrazine-7-carboxylic acid (1-methyl-cyclopentyl)-amide |
| I-385 | 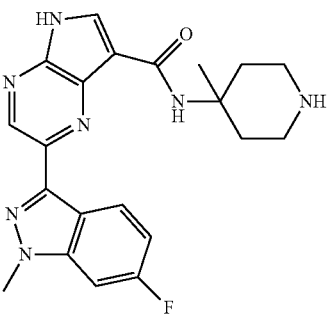 [SMILES: Cn1nc(-c2cnc3[nH]cc(C(=O)NC4(C)CCNCC4)c3n2)c2ccc(F)cc21] | 2-(6-Fluoro-1-methyl-1H-indazol-3-yl)-5H-pyrrolo[2,3-b]pyrazine-7-carboxylic acid (4-methyl-piperidin-4-yl)-amide |

TABLE I-continued

| COMPOUND | STRUCTURE | SYSTEMATIC NAME |
|---|---|---|
| I-386 | 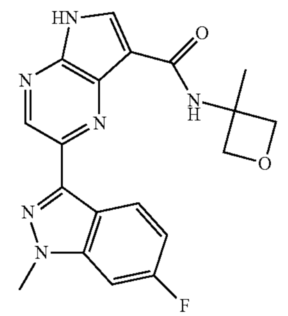 [SMILES: Cn1nc(-c2cnc3[nH]cc(C(=O)NC4(C)COC4)c3n2)c2ccc(F)cc21] | 2-(6-Fluoro-1-methyl-1H-indazol-3-yl)-5H-pyrrolo[2,3-b]pyrazine-7-carboxylic acid (3-methyl-oxetan-3-yl)-amide |
| I-387 | 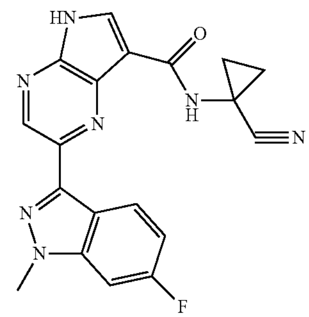 [SMILES: Cn1nc(-c2cnc3[nH]cc(C(=O)NC4(C#N)CC4)c3n2)c2ccc(F)cc21] | 2-(6-Fluoro-1-methyl-1H-indazol-3-yl)-5H-pyrrolo[2,3-b]pyrazine-7-carboxylic acid (1-cyano-cyclopropyl)-amide |
| I-388 | 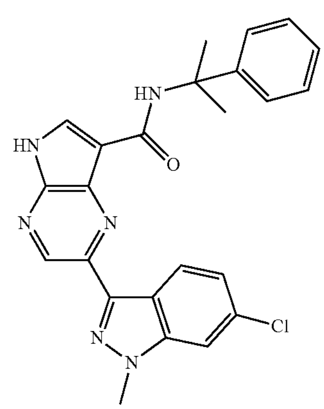 [SMILES: Cn1nc(-c2cnc3[nH]cc(C(=O)NC(C)(C)c4ccccc4)c3n2)c2ccc(Cl)cc21] | 2-(6-Chloro-1-methyl-1H-indazol-3-yl)-5H-pyrrolo[2,3-b]pyrazine-7-carboxylic acid (1-methyl-1-phenyl-ethyl)-amide |
| I-389 | 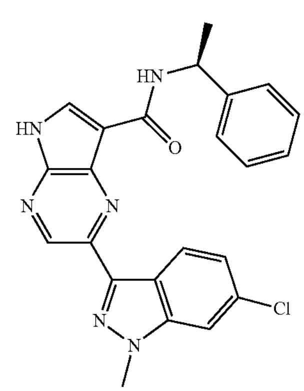 [SMILES: C[C@H](NC(=O)c1c[nH]c2ncc(-c3nn(C)c4cc(Cl)ccc34)nc12)c1ccccc1] | 2-(6-Chloro-1-methyl-1H-indazol-3-yl)-5H-pyrrolo[2,3-b]pyrazine-7 carboxylic acid ((S)-1-phenyl-ethyl)-amide |

TABLE I-continued

| COMPOUND | STRUCTURE | SYSTEMATIC NAME |
|---|---|---|
| I-390 | 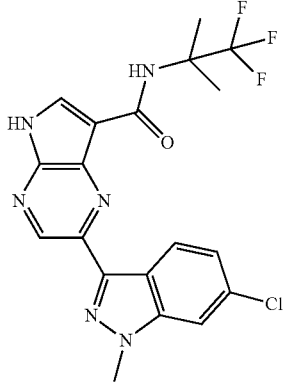 [SMILES: Cn1nc(-c2cnc3[nH]cc(C(=O)NC(C)(C)C(F)(F)F)c3n2)c2ccc(Cl)cc21] | 2-(6-Chloro-1-methyl-1H-indazol-3-yl)-5H-pyrrolo[2,3-b]pyrazine-7-carboxylic acid (2,2,2-trifluoro-1,1-dimethyl-ethyl)-amide |
| I-391 | 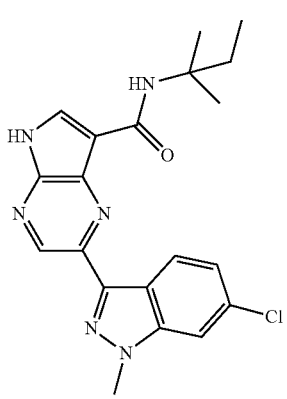 [SMILES: CCC(C)(C)NC(=O)c1c[nH]c2ncc(-c3nn(C)c4cc(Cl)ccc34)nc12] | 2-(6-Chloro-1-methyl-1H-indazol-3-yl)-5H-pyrrolo[2,3-b]pyrazine-7-carboxylic acid (1,1-dimethyl-propyl)-amide |
| I-392 | 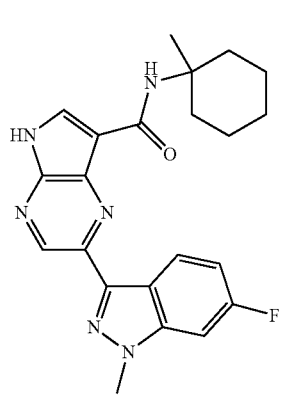 [SMILES: Cn1nc(-c2cnc3[nH]cc(C(=O)NC4(C)CCCCC4)c3n2)c2ccc(F)cc21] | 2-(6-Fluoro-1-methyl-1H-indazol-3-yl)-5H-pyrrolo[2,3-b]pyrazine-7-carboxylic acid (1-methyl-cyclohexyl)-amide |
| I-393 | 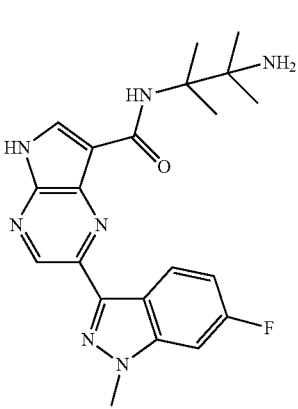 [SMILES: Cn1nc(-c2cnc3[nH]cc(C(=O)NC(C)(C)C(C)(C)N)c3n2)c2ccc(F)cc21] | 2-(6-Fluoro-1-methyl-1H-indazol-3-yl]-5H-pyrrolo[2,3-b]pyrazine-7-carboxylic acid (2-amino-1,1,2-trimethyl-propyl)-amide |

| COMPOUND | STRUCTURE | SYSTEMATIC NAME |
|---|---|---|
| I-394 | 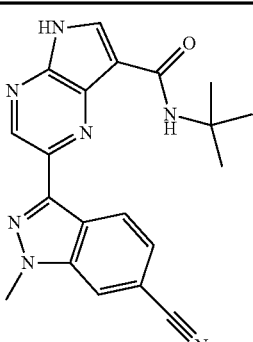 | 2-(6-Cyano-1-methyl-1H-indazol-3-yl)-5H-pyrrolo[2,3-b]pyrazine-7-carboxylic acid tert-butylamide |
| I-395 | 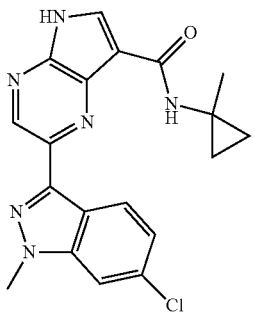 [SMILES: Cn1nc(-c2cnc3[nH]cc(C(=O)NC4(C)CC4)c3n2)c2ccc(Cl)cc21] | 2-(6-Chloro-1-methyl-1H-indazol-3-yl)-5H-pyrrolo[2,3-b]pyrazine-7-carboxylic acid (1-methyl-cyclopropyl)-amide |
| I-396 | 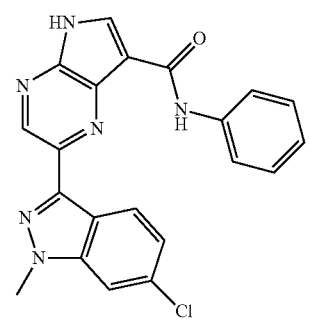 [SMILES: Cn1nc(-c2cnc3[nH]cc(C(=O)Nc4ccccc4)c3n2)c2ccc(Cl)cc21] | 2-(6-Chloro-1-methyl-1H-indazol-3-yl)-5H-pyrrolo[2,3-b]pyrazine-7-carboxylic acid phenylamide |
| I-397 | 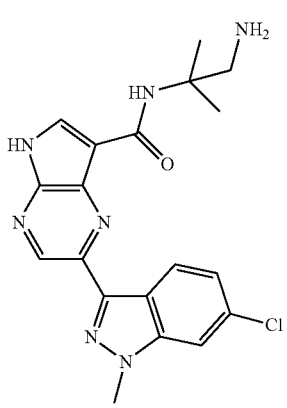 [SMILES: Cn1nc(-c2cnc3[nH]cc(C(=O)NC(C)(C)CN)c3n2)c2ccc(Cl)cc21] | 2-(6-Chloro-1-methyl-1H-indazol-3-yl)-5H-pyrrolo[2,3-b]pyrazine-7-carboxylic acid (2-amino-1,1-dimethyl-ethyl)-amide |

TABLE I-continued

| COMPOUND | STRUCTURE | SYSTEMATIC NAME |
|---|---|---|
| I-398 | 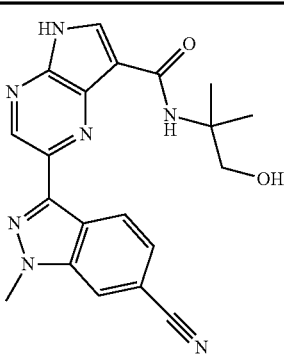 | 2-(6-Cyano-1-methyl-1H-indazol-3-yl)-5H-pyrrolo[2,3-b]pyrazine-7-carboxylic acid (2-hydroxy-1,1-dimethyl-ethyl)-amide |
| I-399 | 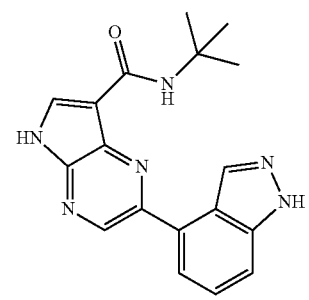 [SMILES: CC(C)(C)NC(=O)c1c[nH]c2ncc(-c3cccc4[nH]ncc34)nc12] | 2-(1H-Indazol-4-yl)-5H-pyrrolo[2,3-b]pyrazine-7-carboxylic acid tert-butylamide |
| I-400 | 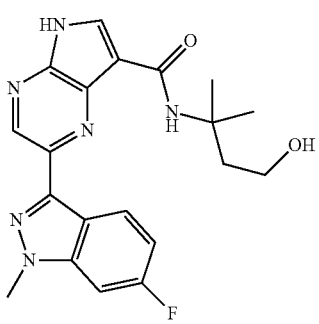 [SMILES: Cn1nc(-c2cnc3[nH]cc(C(=O)NC(C)(C)CCO)c3n2)c2ccc(F)cc21] | 2-(6-Fluoro-1-methyl-1H-indazol-3-yl)-5H-pyrrolo[2,3-b]pyrazine-7-carboxylic acid (3-hydroxy-1,1-dimethyl-propyl)-amide |
| I-401 | 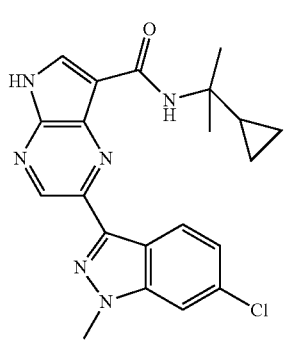 [SMILES: Cn1nc(-c2cnc3[nH]cc(C(=O)NC(C)(C)C4CC4)c3n2)c2ccc(Cl)cc21] | 2-(6-Chloro-1-methyl-1H-indazol-3-yl)-5H-pyrrolo[2,3-b]pyrazine-7-carboxylic acid (1-cyclopropyl-1-methyl-ethyl)-amide |

TABLE I-continued

| COMPOUND | STRUCTURE | SYSTEMATIC NAME |
|---|---|---|
| I-402 | 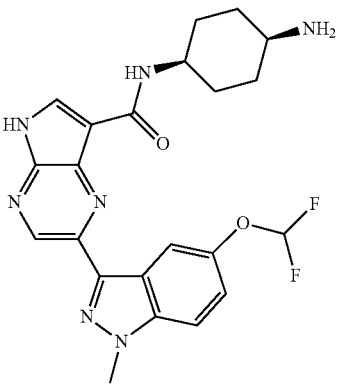 [SMILES: Cn1nc(-c2cnc3[nH]cc(C(=O)N[C@H]4CC[C@@H](N)CC4)c3n2)c2cc(OC(F)F)ccc21] | 2-(5-Difluoromethoxy-1-methyl-1H-indazol-3-yl)-5H-pyrrolo[2,3-b]pyrazine-7-carboxylic acid (cis-4-amino-cyclohexyl)-amide |
| I-403 | 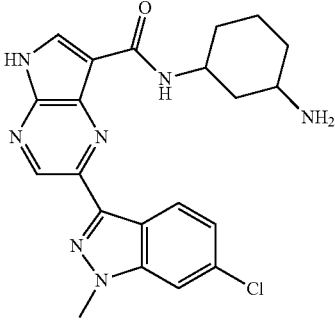 [SMILES: Cn1nc(-c2cnc3[nH]cc(C(=O)NC4CCCC(N)C4)c3n2)c2ccc(Cl)cc21] | 2-(6-Chloro-1-methyl-1H-indazol-3-yl)-5H-pyrrolo[2,3-b]pyrazine-7-carboxylic acid (3-amino-cyclohexyl)-amide |
| I-404 | 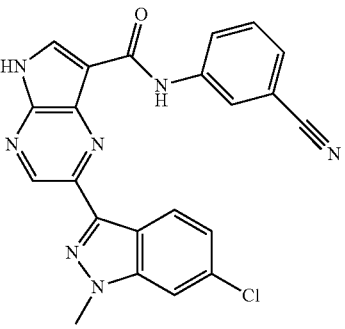 [SMILES: Cn1nc(-c2cnc3[nH]cc(C(=O)Nc4cccc(C#N)c4)c3n2)c2ccc(Cl)cc21] | 2-(6-Chloro-1-methyl-1H-indazol-3-yl)-5H-pyrrolo[2,3-b]pyrazine-7-carboxylic acid (3-cyano-phenyl)-amide |
| I-405 | 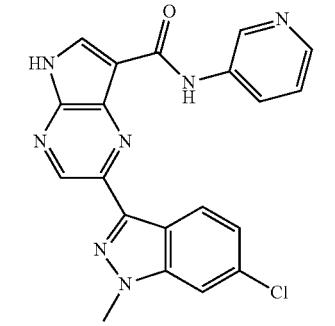 [SMILES: Cn1nc(-c2cnc3[nH]cc(C(=O)Nc4cccnc4)c3n2)c2ccc(Cl)cc21] | 2-(6-Chloro-1-methyl-1H-indazol-3-yl)-5H-pyrrolo[2,3-b]pyrazine-7-carboxylic acid pyridin-3-ylamide |

TABLE I-continued

| COMPOUND | STRUCTURE | SYSTEMATIC NAME |
|---|---|---|
| I-406 | 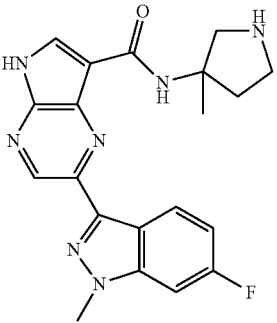 [SMILES: Cn1nc(-c2cnc3[nH]cc(C(=O)NC4(C)CCNC4)c3n2)c2ccc(F)cc21] | 2-(6-Fluoro-1-methyl-1H-indazol-3-yl)-5H-pyrrolo[2,3-b]pyrazine-7-carboxylic acid (3-methyl-pyrrolidin-3-yl)-amide |
| I-407 | 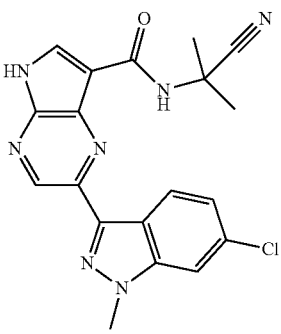 [SMILES: Cn1nc(-c2cnc3[nH]cc(C(=O)NC(C)(C)C#N)c3n2)c2ccc(Cl)cc21] | 2-(6-Chloro-1-methyl-1H-indazol-3-yl)-5H-pyrrolo[2,3-b]pyrazine-7-carboxylic acid (cyano-dimethyl-methyl)-amide |
| I-408 | 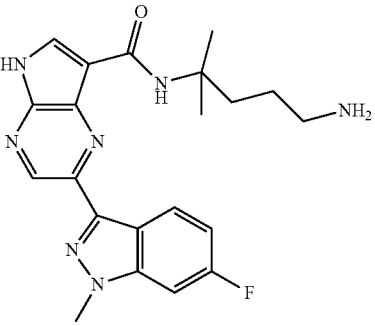 [SMILES: Cn1nc(-c2cnc3[nH]cc(C(=O)NC(C)(C)CCCN)c3n2)c2ccc(F)cc21] | 2-(6-Fluoro-1-methyl-1H-indazol-3-yl)-5H-pyrrolo[2,3-b]pyrazine-7-carboxylic acid (4-amino-1,1-dimethyl-butyl)-amide |
| I-409 | 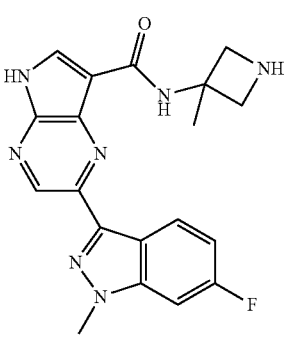 [SMILES: Cn1nc(-c2cnc3[nH]cc(C(=O)NC4(C)CNC4)c3n2)c2ccc(F)cc21] | 2-(6-Fluoro-1-methyl-1H-indazol-3-yl)-5H-pyrrolo[2,3-b]pyrazine-7-carboxylic acid (3-methyl-azetidin-3-yl)-amide |

TABLE I-continued

| COMPOUND | STRUCTURE | SYSTEMATIC NAME |
|---|---|---|
| I-410 | 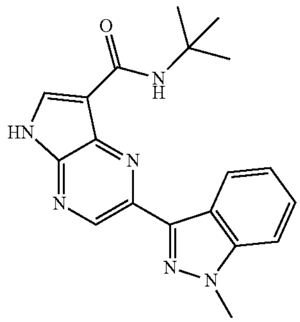 [SMILES: Cn1nc(-c2cnc3[nH]cc(C(=O)NC(C)(C)C)c3n2)c2ccccc21] | 2-(1-Methyl-1H-indazol-3-yl)-5H-pyrrolo[2,3-b]pyrazine-7-carboxylic acid tert-butylamide |
| I-411 | 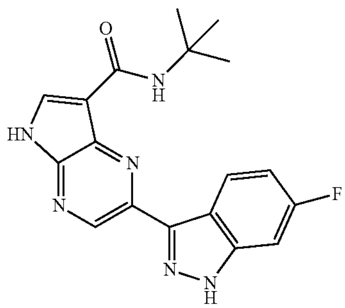 [SMILES: CC(C)(C)NC(=O)c1c[nH]c2ncc(-c3n[nH]c4cc(F)ccc34)nc12] | 2-(6-Fluoro-1H-indazol-3-yl)-5H-pyrrolo[2,3-b]pyrazine-7-carboxylic acid tert-butylamide |
| I-412 | 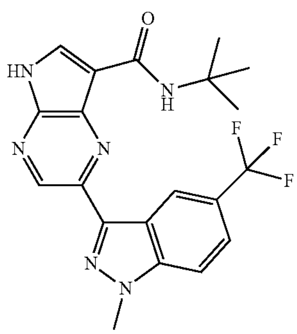 [SMILES: Cn1nc(-c2cnc3[nH]cc(C(=O)NC(C)(C)C)c3n2)c2cc(C(F)(F)F)ccc21] | 2-(1-Methyl-5-trifluoromethyl-1H-indazol-3-yl)-5H-pyrrolo[2,3-b]pyrazine-7-carboxylic acid tert-butylamide |
| I-413 | 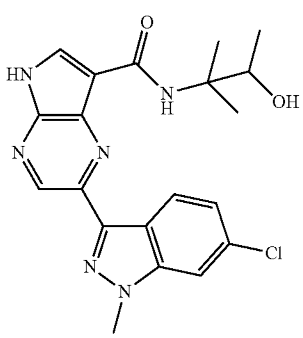 [SMILES: CC(O)C(C)(C)NC(=O)c1c[nH]c2ncc(-c3nn(C)c4cc(Cl)ccc34)nc12] | 2-(6-Chloro-1-methyl-1H-indazol-3-yl)-5H-pyrrolo[2,3-b]pyrazine-7-carboxylic acid (2-hydroxy-1,1-dimethyl-propyl)-amide |
| I-414 | 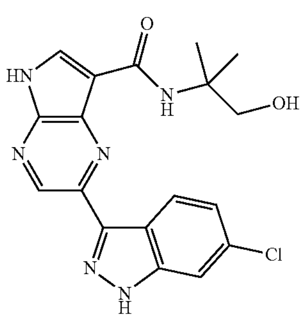 [SMILES: CC(C)(CO)NC(=O)c1c[nH]c2ncc(-c3n[nH]c4cc(Cl)ccc34)nc12] | 2-(6-Chloro-1H-indazol-3-yl)-5H-pyrrolo[2,3-b]pyrazine-7-carboxylic acid (2-hydroxy-1,1-dimethyl-ethyl)-amide |

TABLE I-continued

| COMPOUND | STRUCTURE | SYSTEMATIC NAME |
|---|---|---|
| I-415 | 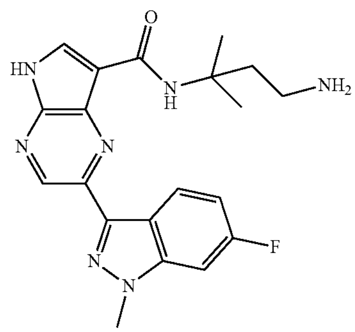 [SMILES: Cn1nc(-c2cnc3[nH]cc(C(=O)NC(C)(C)CCN)c3n2)c2ccc(F)cc21] | 2-(6-Fluoro-1-methyl-1H-indazol-3-yl)-5H-pyrrolo[2,3-b]pyrazine-7-carboxylic acid (3-amino-1,1-dimethyl-propyl)-amide |
| I-416 | 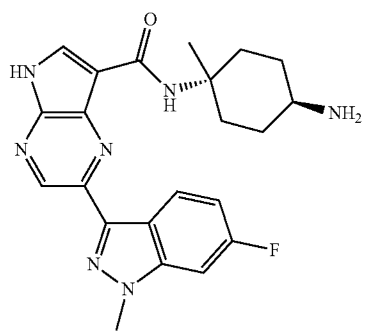 [SMILES: Cn1nc(-c2cnc3[nH]cc(C(=O)N[C@]4(C)CC[C@@H](N)CC4)c3n2)c2ccc(F)cc21] | 2-(6-Fluoro-1-methyl-1H-indazol-3-yl)-5H-pyrrolo[2,3-b]pyrazine-7-carboxylic acid (trans-4-amino-1-methyl-cyclohexyl)-amide |
| I-417 | 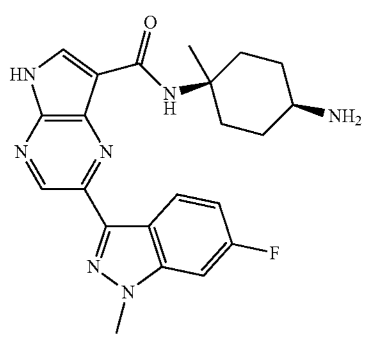 [SMILES: Cn1nc(-c2cnc3[nH]cc(C(=O)N[C@]4(C)CC[C@H](N)CC4)c3n2)c2ccc(F)cc21] | 2-(6-Fluoro-1-methyl-1H-indazol-3-yl)-5H-pyrrolo[2,3-b]pyrazine-7-carboxylic acid (cis-4-amino-1-methyl-cyclohexyl)-amide |
| I-418 | 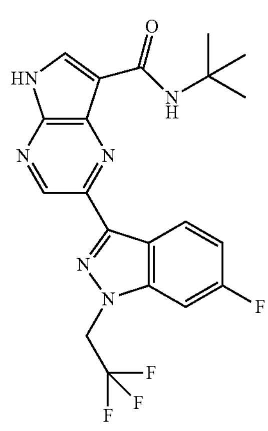 [SMILES: CC(C)(C)NC(=O)c1c[nH]c2ncc(-c3nn(CC(F)(F)F)c4cc(F)ccc34)nc12] | 2-[6-Fluoro-1-(2,2,2-trifluoro-ethyl)-1H-indazol-3-yl]-5H-pyrrolo[2,3-b]pyrazine-7-carboxylic acid tert-butylamide |

TABLE I-continued

| COMPOUND | STRUCTURE | SYSTEMATIC NAME |
|---|---|---|
| I-419 | 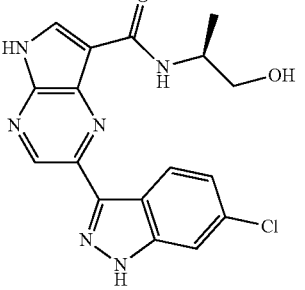 | 2-(6-Chloro-1H-indazol-3-yl)-5H-pyrrolo[2,3-b]pyrazine-7-carboxylic acid ((S)-2-hydroxy-1-methyl-ethyl)-amide |
| I-420 | 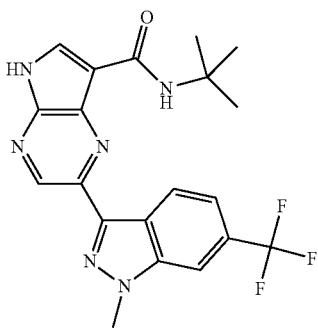 [SMILES: Cn1nc(-c2cnc3[nH]cc(C(=O)NC(C)(C)C)c3n2)c2ccc(C(F)(F)F)cc21] | 2-(1-Methyl-6-trifluoromethyl-1H-indazol-3-yl)-5H-pyrrolo[2,3-b]pyrazine-7 carboxylic acid tert-butylamide |
| I-421 | 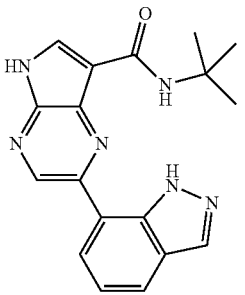 [SMILES: CC(C)(C)NC(=O)c1c[nH]c2ncc(-c3cccc4cn[nH]c34)nc12] | 2-(1H-Indazol-7-yl)-5H-pyrrolo[2,3-b]pyrazine-7-carboxylic acid tert-butylamide |
| I-422 | 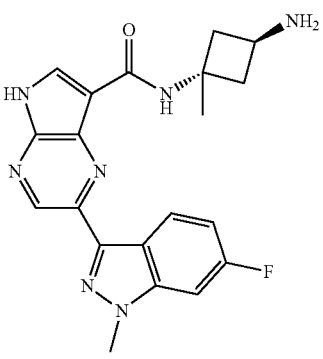 [SMILES: Cn1nc(-c2cnc3[nH]cc(C(=O)N[C@]4(C)C[C@@H](N)C4)c3n2)c2ccc(F)cc21] | 2-(6-Fluoro-1-methyl-1H-indazol-3-yl)-5H-pyrrolo[2,3-b]pyrazine-7-carboxylic acid (trans-3-amino-1-methyl-cyclobutyl)-amide |

TABLE I-continued

| COMPOUND | STRUCTURE | SYSTEMATIC NAME |
|---|---|---|
| I-423 | 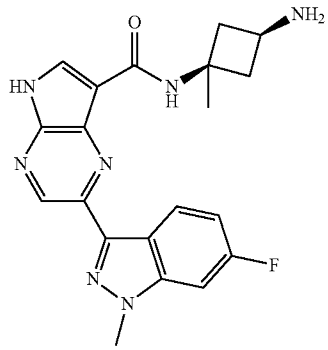 [SMILES: Cn1nc(-c2cnc3[nH]cc(C(=O)N[C@]4(C)C[C@H](N)C4)c3n2)c2ccc(F)cc21] | 2-(6-Fluoro-1-methyl-1H-indazol-3-yl)-5H-pyrrolo[2,3-b]pyrazine-7-carboxylic acid (cis-3-amino-1-methyl-cyclobutyl)-amide |
| I-424 | 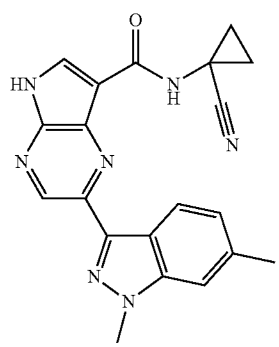 [SMILES: Cc1ccc2c(-c3cnc4[nH]cc(C(=O)NC5(C#N)CC5)c4n3)nn(C)c2c1] | 2-(1,6-Dimethyl-1H-indazol-3-yl)-5H-pyrrolo[2,3-b]pyrazine-7-carboxylic acid (1-cyano-cyclopropyl)-amide |
| I-425 | 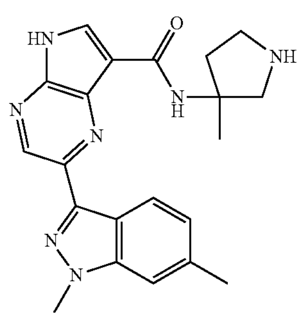 [SMILES: Cc1ccc2c(-c3cnc4[nH]cc(C(=O)NC5(C)CCNC5)c4n3)nn(C)c2c1] | 2-(1,6-Dimethyl-1H-indazol-3-yl)-5H-pyrrolo[2,3-b]pyrazine-7-carboxylic acid (3-methyl-pyrrolidin-3-yl)-amide |
| I-426 | 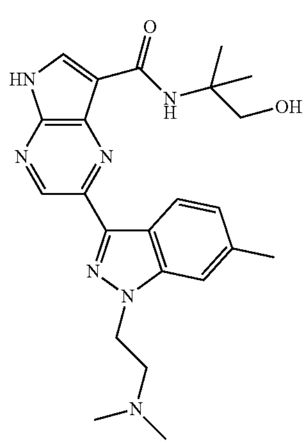 [SMILES: Cc1ccc2c(-c3cnc4[nH]cc(C(=O)NC(C)(C)CO)c4n3)nn(CCN(C)C)c2c1] | 2-[1-(2-Dimethylamino-ethyl)-6-methyl-1H-indazol-3-yl]-5H-pyrrolo[2,3-b]pyrazine-7-carboxylic acid (2-hydroxy-1,1-dimethyl-ethyl)-amide |

TABLE I-continued

| COMPOUND | STRUCTURE | SYSTEMATIC NAME |
|---|---|---|
| I-427 | 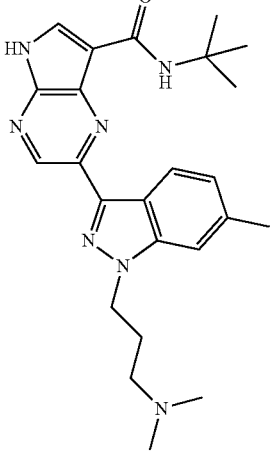 | 2-[1-(3-Dimethylamino-propyl)-6-methyl-1H-indazol-3-yl]-5H-pyrrolo[2,3-b]pyrazine-7-carboxylic acid tert-butylamide |
| I-428 | 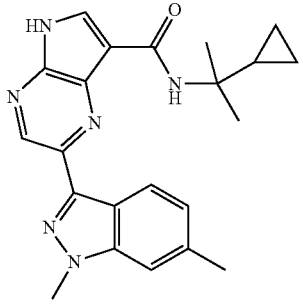 [SMILES: Cc1ccc2c(-c3cnc4[nH]cc(C(=O)NC(C)(C)C5CC5)c4n3)nn(C)c2c1] | 2-(1,6-Dimethyl-1H-indazol-3-yl)-5H-pyrrolo[2,3-b]pyrazine-7-carboxylic acid (1-cyclopropyl-1-methyl-ethyl)-amide |
| I-429 | 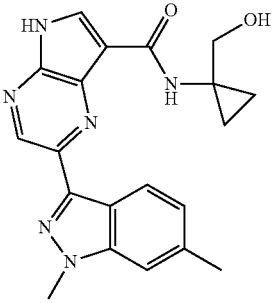 [SMILES: Cc1ccc2c(-c3cnc4[nH]cc(C(=O)NC5(CO)CC5)c4n3)nn(C)c2c1] | 2-(1,6-Dimethyl-1H-indazol-3-yl)-5H-pyrrolo[2,3-b]pyrazine-7-carboxylic acid (1-hydroxymethyl-cyclopropyl)-amide |
| I-430 | 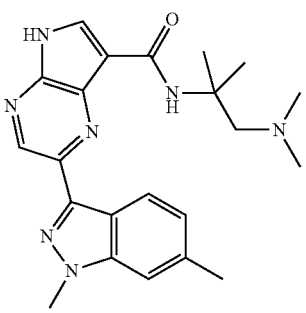 [SMILES: Cc1ccc2c(-c3cnc4[nH]cc(C(=O)NC(C)(C)CN(C)C)c4n3)nn(C)c2c1] | 2-(1,6-Dimethyl-1H-indazol-3-yl)-5H-pyrrolo[2,3-b]pyrazine-7-carboxylic acid (2-dimethylamino-1,1-dimethyl-ethyl)-amide |

TABLE I-continued

| COMPOUND | STRUCTURE | SYSTEMATIC NAME |
| --- | --- | --- |
| I-431 | 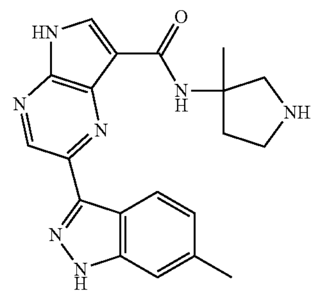 [SMILES: Cc1ccc2c(-c3cnc4[nH]cc(C(=O)NC5(C)CCNC5)c4n3)n[nH]c2c1] | 2-(6-Methyl-1H-indazol-3-yl)-5H-pyrrolo[2,3-b]pyrazine-7-carboxylic acid (3-methyl-pyrrolidin-3-yl)-amide |
| I-432 | 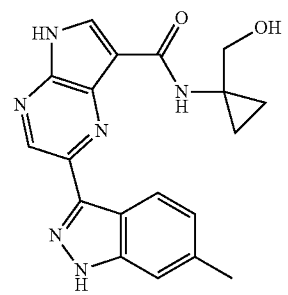 [SMILES: Cc1ccc2c(-c3cnc4[nH]cc(C(=O)NC5(CO)CC5)c4n3)n[nH]c2c1] | 2-(6-Methyl-1H-indazol-3-yl)-5H-pyrrolo[2,3-b]pyrazine-7-carboxylic acid (1-hydroxymethyl-cyclopropyl)-amide |
| I-433 | 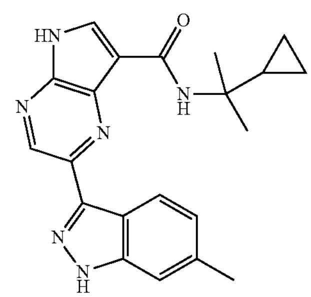 [SMILES: Cc1ccc2c(-c3cnc4[nH]cc(C(=O)NC(C)(C)C5CC5)c4n3)n[nH]c2c1] | 2-(6-Methyl-1H-indazol-3-yl)-5H-pyrrolo[2,3-b]pyrazine-7-carboxylic acid (1-cyclopropyl-1-methyl-ethyl)-amide |
| I-434 | 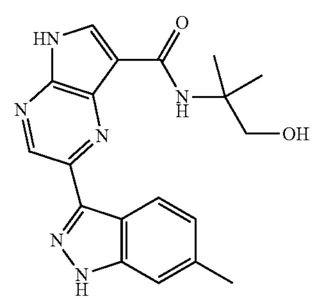 [SMILES: Cc1ccc2c(-c3cnc4[nH]cc(C(=O)NC(C)(C)CO)c4n3)n[nH]c2c1] | 2-(6-Methyl-1H-indazol-3-yl)-5H-pyrrolo[2,3-b]pyrazine-7-carboxylic acid (2-hydroxy-1,1-dimethyl-ethyl)-amide |
| I-435 | 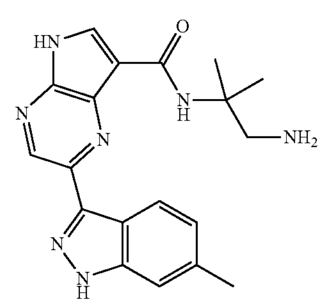 [SMILES: Cc1ccc2c(-c3cnc4[nH]cc(C(=O)NC(C)(C)CN)c4n3)n[nH]c2c1] | 2-(6-Methyl-1H-indazol-3-yl)-5H-pyrrolo[2,3-b]pyrazine-7-carboxylic acid (2-amino-1,1-dimethyl-ethyl)-amide |

TABLE I-continued

| COMPOUND | STRUCTURE | SYSTEMATIC NAME |
|---|---|---|
| I-436 | 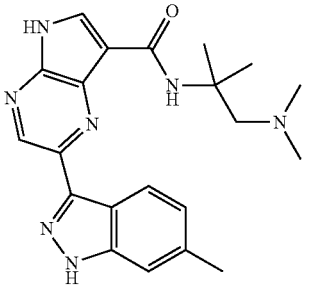 [SMILES: Cc1ccc2c(-c3cnc4[nH]cc(C(=O)NC(C)(C)CN(C)C)c4n3)n[nH]c2c1] | 2-(6-Methyl-1H-indazol-3-yl)-5H-pyrrolo[2,3-b]pyrazine-7-carboxylic acid (2-dimethylamino-1,1-dimethyl-ethyl)-amide |
| I-437 | 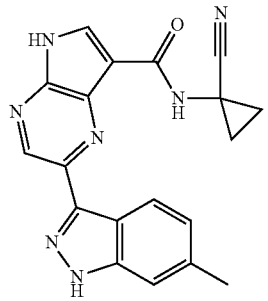 [SMILES: Cc1ccc2c(-c3cnc4[nH]cc(C(=O)NC5(C#N)CC5)c4n3)n[nH]c2c1] | 2-(6-Methyl-1H-indazol-3-yl)-5H-pyrrolo[2,3-b]pyrazine-7-carboxylic acid (1-cyano-cyclopropyl)-amide |
| I-438 | 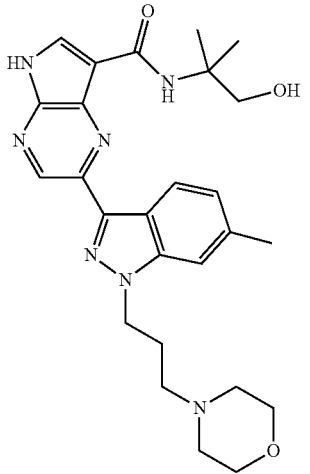 [SMILES: Cc1ccc2c(-c3cnc4[nH]cc(C(=O)NC(C)(C)CO)c4n3)nn(CCCN3CCOCC3)c2c1] | 2-[6-Methyl-1-(3-morpholin-4-yl-propyl)-1H-indazol-3-yl]-5H-pyrrolo[2,3-b]pyrazine-7-carboxylic acid (2-hydroxy-1,1-dimethyl-ethyl)-amide |
| I-439 | 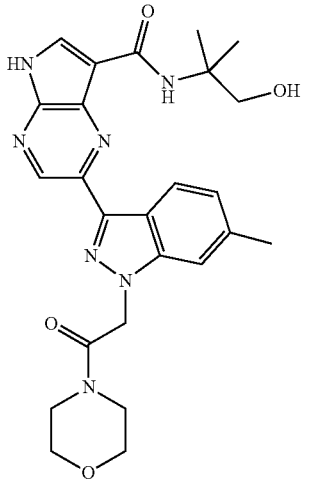 [SMILES: Cc1ccc2c(-c3cnc4[nH]cc(C(=O)NC(C)(C)CO)c4n3)nn(CC(=O)N3CCOCC3)c2c1] | 2-[6-Methyl-1-(2-morpholin-4-yl-2-oxo-ethyl)-1H-indazol-3-yl]-5H-pyrrolo[2,3-b]pyrazine-7-carboxylic acid (2-hydroxy-1,1-dimethyl-ethyl)-amide |

US 8,658,646 B2

TABLE I-continued

| COMPOUND | STRUCTURE | SYSTEMATIC NAME |
|---|---|---|
| I-440 | 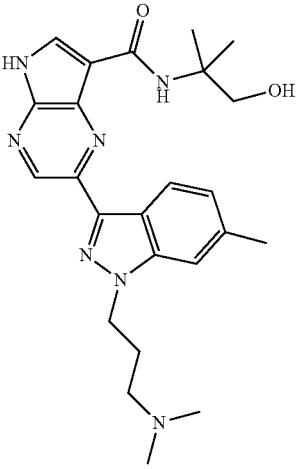 [SMILES: Cc1ccc2c(-c3cnc4[nH]cc(C(=O)NC(C)(C)CO)c4n3)nn(CCCN(C)C)c2c1] | 2-[1-(3-Dimethylamino-propyl)-6-methyl-1H-indazol-3-yl]-5H-pyrrolo[2,3-b]pyrazine-7-carboxylic acid (2-hydroxy-1,1-dimethyl-ethyl)-amide |
| I-441 | 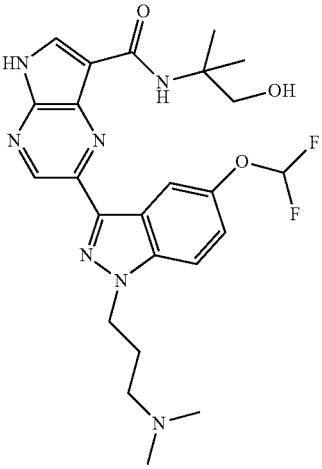 [SMILES: CN(C)CCCn1nc(-c2cnc3[nH]cc(C(=O)NC(C)(C)CO)c3n2)c2cc(OC(F)F)ccc21] | 2-[5-Difluoromethoxy-1-(3-dimethylamino-propyl)-1H-indazol-3-yl]-5H-pyrrolo[2,3-b]pyrazine-7-carboxylic acid (2-hydroxy-1,1-dimethyl-ethyl)-amide |
| I-442 | 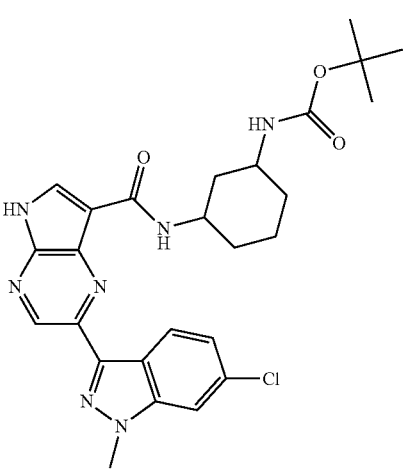 [SMILES: Cn1nc(-c2cnc3[nH]cc(C(=O)NC4CCCC(NC(=O)OC(C)(C)C)C4)c3n2)c2ccc(Cl)cc21] | (3-{[2-(6-Chloro-1-methyl-1H-indazol-3-yl)-5H-pyrrolo[2,3-b]pyrazine-7-carbonyl]-amino}-cyclohexyl)-carbamic acid tert-butyl ester |

TABLE I-continued

| COMPOUND | STRUCTURE | SYSTEMATIC NAME |
| --- | --- | --- |
| I-443 | 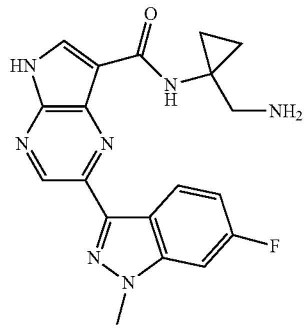 [SMILES: Cn1nc(-c2cnc3[nH]cc(C(=O)NC4(CN)CC4)c3n2)c2ccc(F)cc21] | 2-(6-Fluoro-1-methyl-1H-indazol-3-yl)-5H-pyrrolo[2,3-b]pyrazine-7-carboxylic acid (1-aminomethyl-cyclopropyl)-amide |
| I-444 | 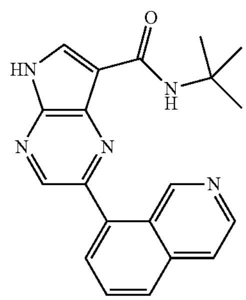 [SMILES: CC(C)(C)NC(=O)c1c[nH]c2ncc(-c3cccc4ccncc34)nc12] | 2-Isoquinolin-8-yl-5H-pyrrolo[2,3-b]pyrazine-7-carboxylic acid tert-butylamide |
| I-445 | 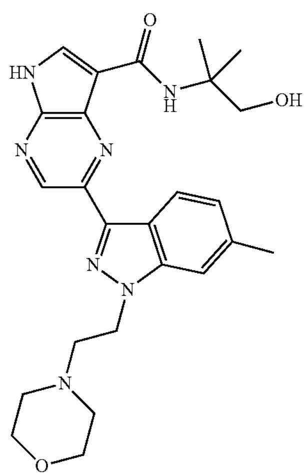 [SMILES: Cc1ccc2c(-c3cnc4[nH]cc(C(=O)NC(C)(C)CO)c4n3)nn(CCN3CCOCC3)c2c1] | 2-[6-Methyl-1-(2-morpholin-4-yl-ethyl)-1H-indazol-3-yl]-5H-pyrrolo[2,3-b]pyrazine-7-carboxylic acid (2-hydroxy-1,1-dimethyl-ethyl)-amide |
| I-446 | 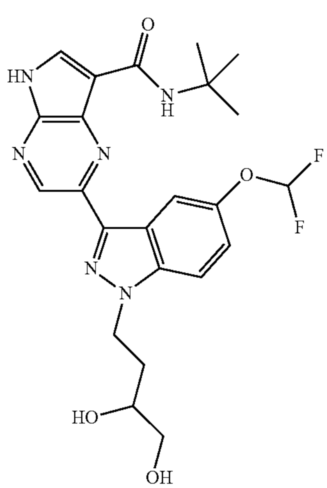 [SMILES: CC(C)(C)NC(=O)c1c[nH]c2ncc(-c3nn(CCC(O)CO)c4ccc(OC(F)F)cc34)nc12] | 2-[5-Difluoromethoxy-1-(3,4-dihydroxy-butyl)-1H-indazol-3-yl]-5H-pyrrolo[2,3-b]pyrazine-7-carboxylic acid tert-butylamide |

TABLE I-continued

| COMPOUND | STRUCTURE | SYSTEMATIC NAME |
|---|---|---|
| I-447 | 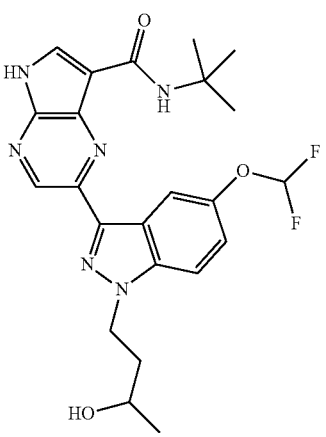 [SMILES: CC(O)CCn1nc(-c2cnc3[nH]cc(C(=O)NC(C)(C)C)c3n2)c2cc(OC(F)F)ccc21] | 2-[5-Difluoromethoxy-1-(3-hydroxy-butyl)-1H-indazol-3-yl]-5H-pyrrolo[2,3-b]pyrazine-7-carboxylic acid tert-butylamide |
| I-448 | 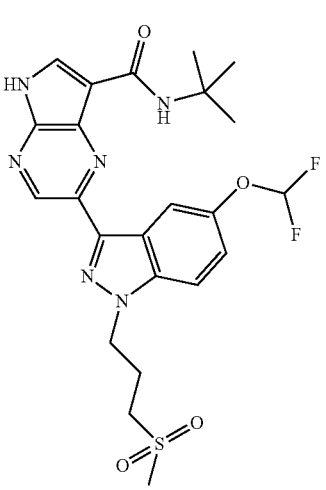 [SMILES: CC(C)(C)NC(=O)c1c[nH]c2ncc(-c3nn(CCCS(C)(=O)=O)c4ccc(OC(F)F)cc34)nc12] | 2-[5-Difluoromethoxy-1-(3-methanesulfonyl-propyl)-1H-indazol-3-yl]-5H-pyrrolo[2,3-b]pyrazine-7-carboxylic acid tert-butylamide |
| I-449 | 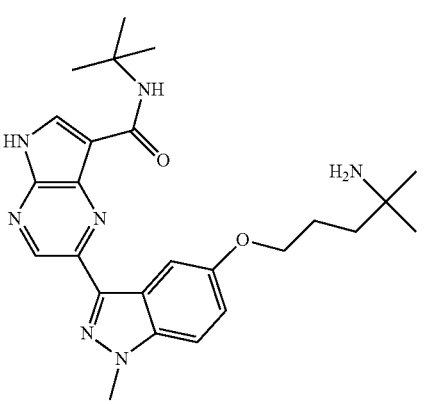 [SMILES: Cn1nc(-c2cnc3[nH]cc(C(=O)NC(C)(C)C)c3n2)c2cc(OCCCC(C)(C)N)ccc21] | 2-[5-(4-Amino-4-methyl-pentyloxy)-1-methyl-1H-indazol-3-yl]-5H-pyrrolo[2,3-b]pyrazine-7-carboxylic acid tert-butylamide |

TABLE I-continued
| COMPOUND | STRUCTURE | SYSTEMATIC NAME |
| --- | --- | --- |
| I-450 | 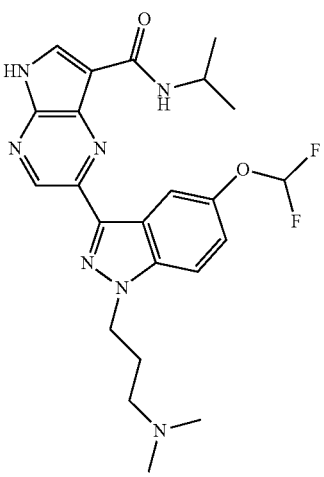 [SMILES: CC(C)NC(=O)c1c[nH]c2ncc(-c3nn(CCCN(C)C)c4ccc(OC(F)F)cc34)nc12] | 2-[5-Difluoromethoxy-1-(3-dimethylamino-propyl)-1H-indazol-3-yl]-5H-pyrrolo[2,3-b]pyrazine-7-carboxylic acid isopropylamide |
| I-451 | 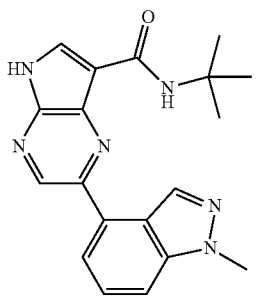 [SMILES: Cn1ncc2c(-c3cnc4[nH]cc(C(=O)NC(C)(C)C)c4n3)cccc21] | 2-(1-Methyl-1H-indazol-4-yl)-5H-pyrrolo[2,3-b]pyrazine-7-carboxylic acid tert-butylamide |
| I-452 | 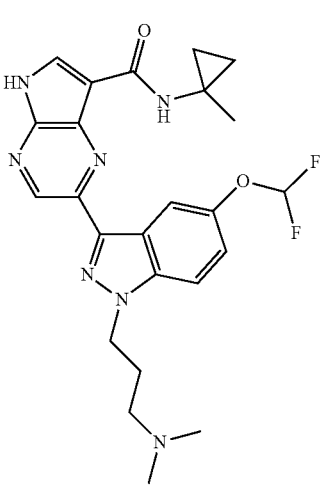 [SMILES: CN(C)CCCn1nc(-c2cnc3[nH]cc(C(=O)NC4(C)CC4)c3n2)c2cc(OC(F)F)ccc21] | 2-[5-Difluoromethoxy-1-(3-dimethylamino-propyl)-1H-indazol-3-yl]-5H-pyrrolo[2,3-b]pyrazine-7-carboxylic acid (1-methyl-cyclopropyl)-amide |

TABLE I-continued
| COMPOUND | STRUCTURE | SYSTEMATIC NAME |
|---|---|---|
| I-453 | 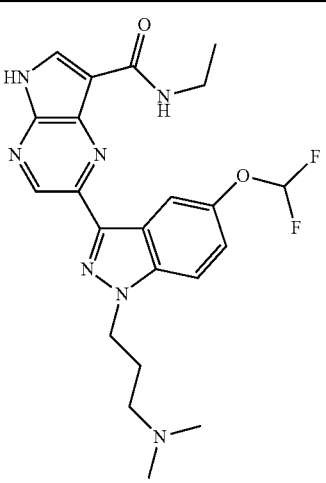 | 2-[5-Difluoromethoxy-1-(3-dimethylamino-propyl)-1H-indazol-3-yl]-5H-pyrrolo[2,3-b]pyrazine-7-carboxylic acid ethylamide |
| I-454 | 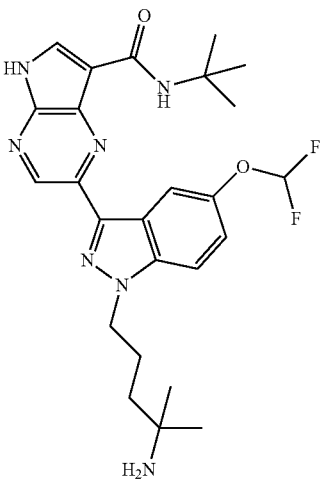 [SMILES: CC(C)(N)CCCn1nc(-c2cnc3[nH]cc(C(=O)NC(C)(C)C)c3n2)c2cc(OC(F)F)ccc21] | 2-[1-(4-Amino-4-methyl-pentyl)-5-difluoromethoxy-1H-indazol-3-yl]-5H-pyrrolo[2,3-b]pyrazine-7-carboxylic acid tert-butylamide |
| I-455 | 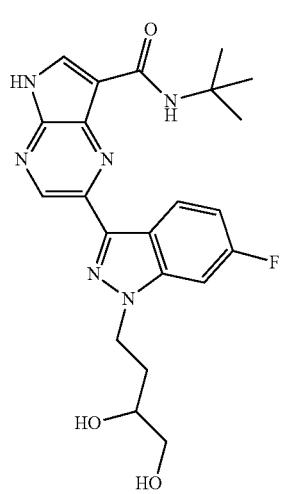 [SMILES: CC(C)(C)NC(=O)c1c[nH]c2ncc(-c3nn(CCC(O)CO)c4cc(F)ccc34)nc12] | 2-[1-(3,4-Dihydroxy-butyl)-6-fluoro-1H-indazol-3-yl]-5H-pyrrolo[2,3-b]pyrazine-7-carboxylic acid tert-butylamide |

TABLE I-continued

| COMPOUND | STRUCTURE | SYSTEMATIC NAME |
| --- | --- | --- |
| I-456 | 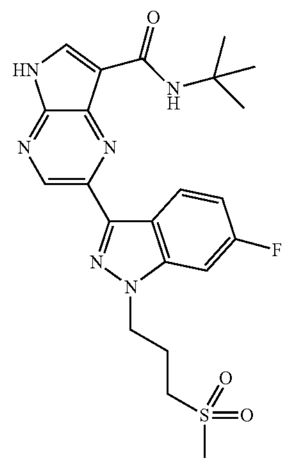 [SMILES: CC(C)(C)NC(=O)c1c[nH]c2ncc(-c3nn(CCCS(C)(=O)=O)c4cc(F)ccc34)nc12] | 2-[6-Fluoro-1-(3-methanesulfonyl-propyl)-1H-indazol-3-yl]-5H-pyrrolo[2,3-b]pyrazine-7-carboxylic acid tert-butylamide |
| I-457 | 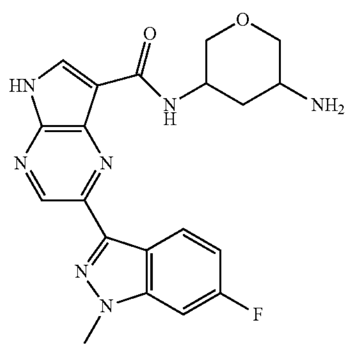 [SMILES: Cn1nc(-c2cnc3[nH]cc(C(=O)NC4COCC(N)C4)c3n2)c2ccc(F)cc21] | 2-(6-Fluoro-1-methyl-1H-indazol-3-yl)-5H-pyrrolo[2,3-b]pyrazine-7-carboxylic acid (5-amino-tetrahydro-pyran-3-yl)-amide |
| I-458 | 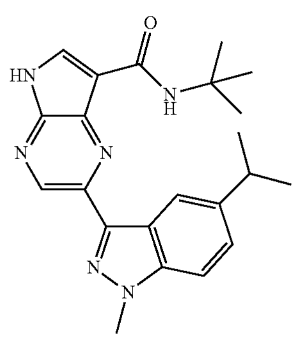 [SMILES: CC(C)c1ccc2c(c1)c(-c1cnc3[nH]cc(C(=O)NC(C)(C)C)c3n1)nn2C] | 2-(5-Isopropyl-1-methyl-1H-indazol-3-yl)-5H-pyrrolo[2,3-b]pyrazine-7-carboxylic acid tert-butylamide |
| I-459 | 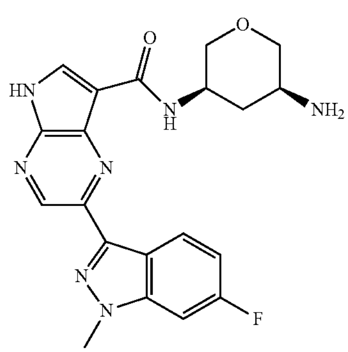 [SMILES: Cn1nc(-c2cnc3[nH]cc(C(=O)N[C@H]4COC[C@@H](N)C4)c3n2)c2ccc(F)cc21] | 2-(6-Fluoro-1-methyl-1H-indazol-3-yl)-5H-pyrrolo[2,3-b]pyrazine-7-carboxylic acid ((cis)-5-amino-tetrahydro-pyran-3-yl)-amide |

TABLE I-continued

| COMPOUND | STRUCTURE | SYSTEMATIC NAME |
|---|---|---|
| I-460 | 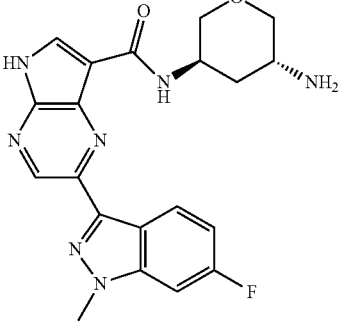 | 2-(6-Fluoro-1-methyl-1H-indazol-3-yl)-5H-pyrrolo[2,3-b]pyrazine-7-carboxylic acid ((trans)-5-amino-tetrahydro-pyran-3-yl)-amide |
| I-461 | 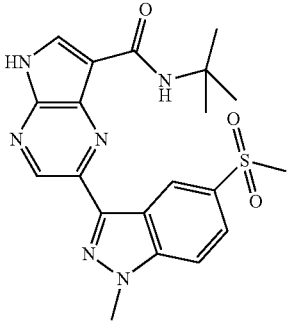 [SMILES: Cn1nc(-c2cnc3[nH]cc(C(=O)NC(C)(C)C)c3n2)c2cc(S(C)(=O)=O)ccc21] | 2-(5-Methanesulfonyl-1-methyl-1H-indazol-3-yl)-5H-pyrrolo[2,3-b]pyrazine-7-carboxylic acid tert-butylamide |
| I-462 | 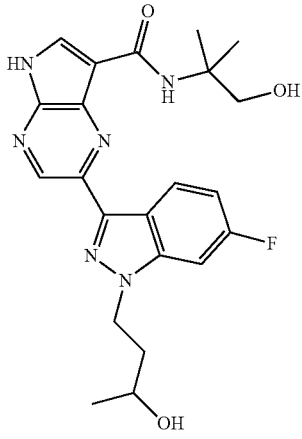 [SMILES: CC(O)CCn1nc(-c2cnc3[nH]cc(C(=O)NC(C)(C)CO)c3n2)c2ccc(F)cc21] | 2-[6-Fluoro-1-(3-hydroxy-butyl)-1H-indazol-3-yl]-5H-pyrrolo[2,3-b]pyrazine-7-carboxylic acid (2-hydroxy-1,1-dimethyl-ethyl)-amide |
| I-463 | 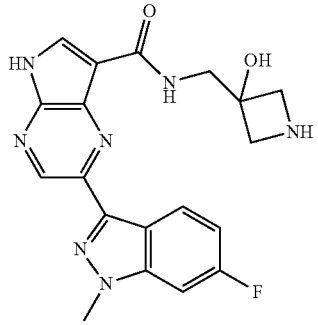 [SMILES: Cn1nc(-c2cnc3[nH]cc(C(=O)NCC4(O)CNC4)c3n2)c2ccc(F)cc21] | 2-(6-Fluoro-1-methyl-1H-indazol-3-yl)-5H-pyrrolo[2,3-b]pyrazine-7-carboxylic acid (3-hydroxy-azetidin-3-ylmethyl)-amide |

| COMPOUND | STRUCTURE | SYSTEMATIC NAME |
|---|---|---|
| I-464 | 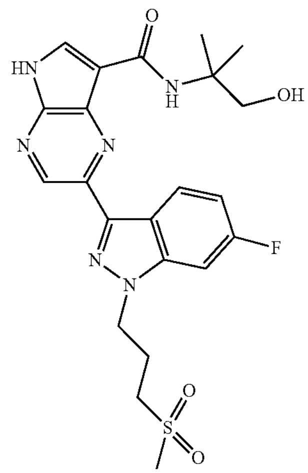 [SMILES: CC(C)(CO)NC(=O)c1c[nH]c2ncc(-c3nn(CCCS(C)(=O)=O)c4cc(F)ccc34)nc12] | 2-(6-Fluoro-1-(3-(methylsulfonyl)propyl)-1H-indazol-3-yl)-N-(1-hydroxy-2-methylpropan-2-yl)-5H-pyrrolo[3,2-b]pyrazine-7-carboxamide |
| I-465 | 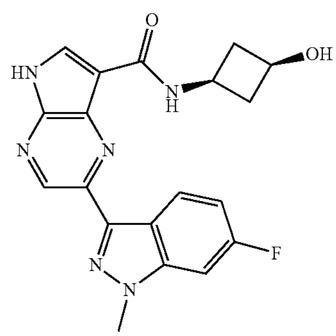 [SMILES: Cn1nc(-c2cnc3[nH]cc(C(=O)N[C@H]4C[C@@H](O)C4)c3n2)c2ccc(F)cc21] | 2-(6-Fluoro-1-methyl-1H-indazol-3-yl)-5H-pyrrolo[2,3-b]pyrazine-7-carboxylic acid (cis-3-hydroxy-cyclobutyl)-amide |
| I-466 | 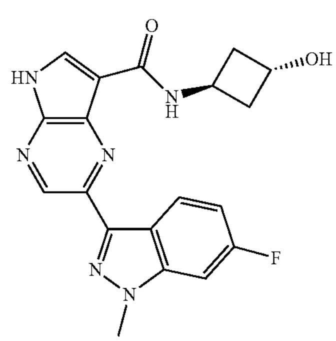 [SMILES: Cn1nc(-c2cnc3[nH]cc(C(=O)N[C@H]4C[C@H](O)C4)c3n2)c2ccc(F)cc21] | 2-(6-Fluoro-1-methyl-1H-indazol-3-yl)-5H-pyrrolo[2,3-b]pyrazine-7-carboxylic acid (trans-3-hydroxy-cyclobutyl)-amide |

Synthesis
General Schemes
Scheme 1.
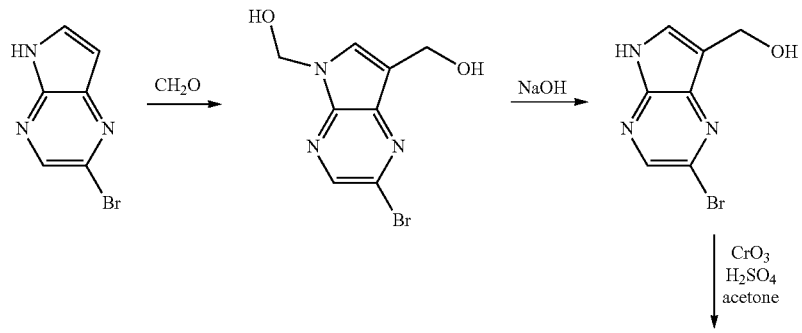
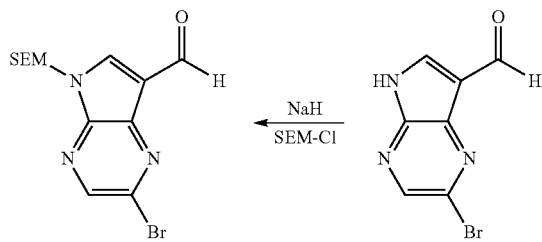
Scheme 2.
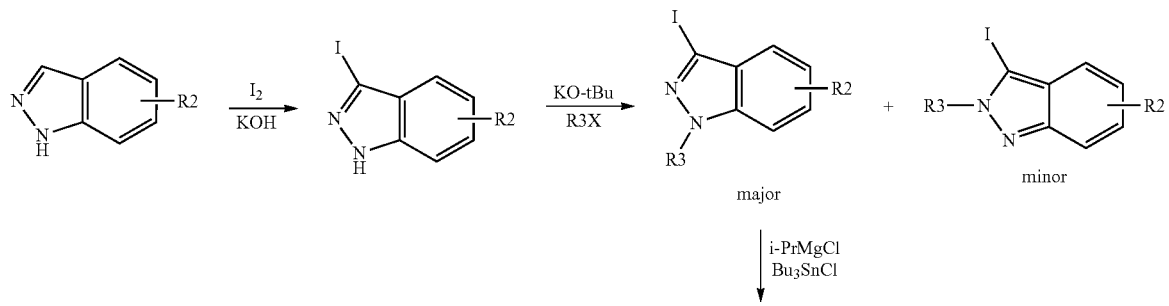
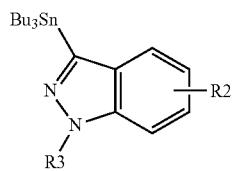

Scheme 3.
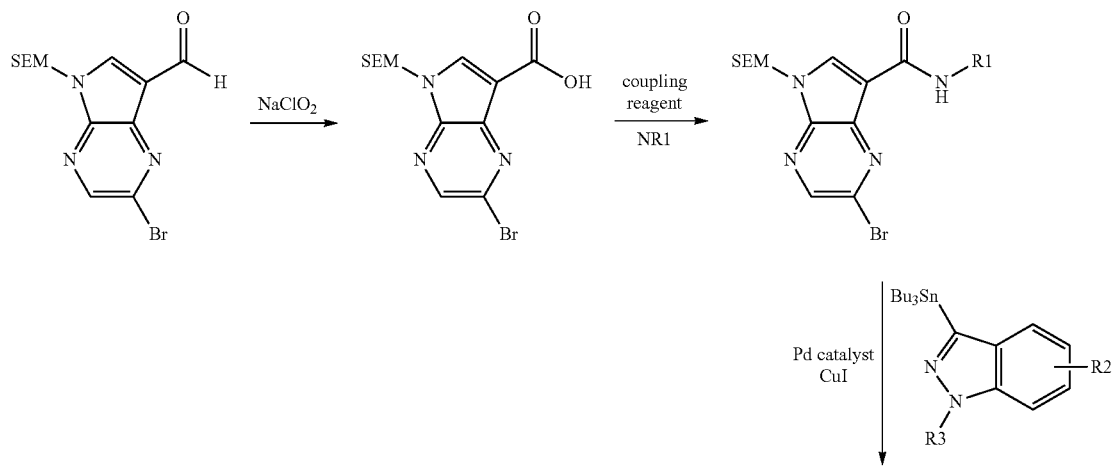
Scheme 4.
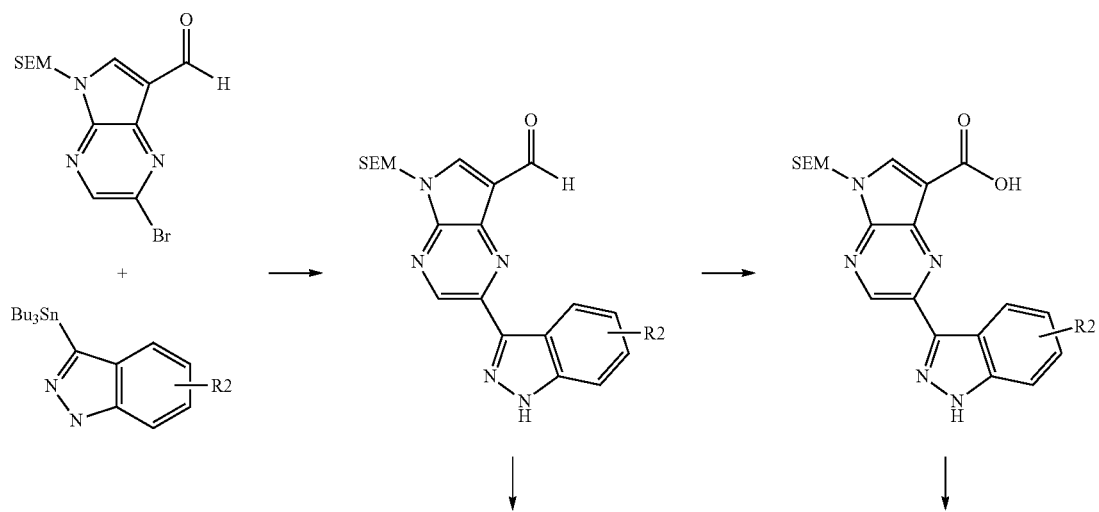

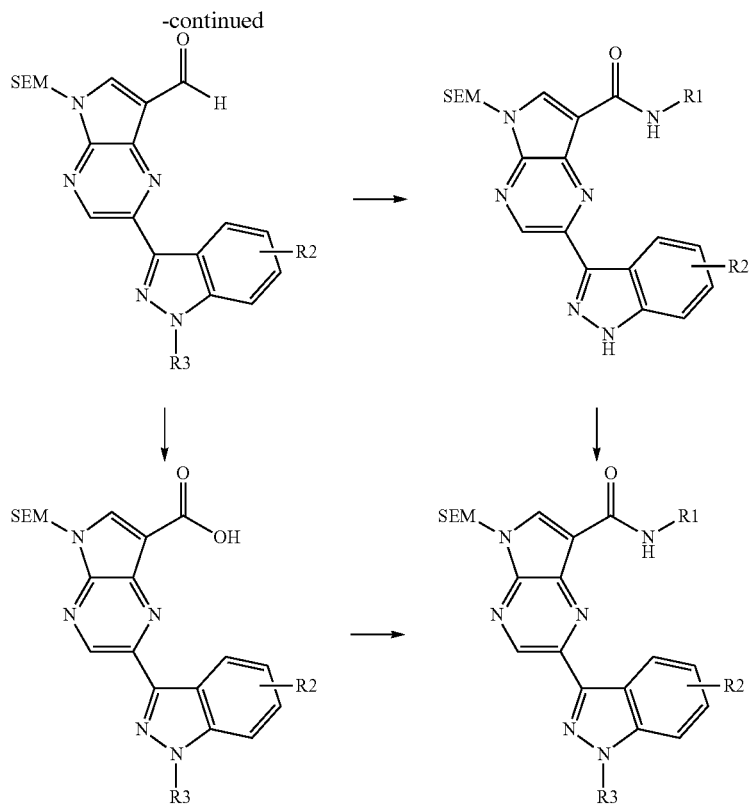

Procedure 1

2-Bromo-5-(2-trimethylsilanyl-ethoxymethyl)-5H-pyrrolo[2,3-b]pyrazine-7-carbaldehyde

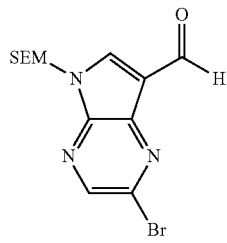 [SMILES: C[Si](C)(C)CCOCn1cc(C=O)c2nc(Br)cnc21]

Method A

Step 1

(2-Bromo-7-hydroxymethyl-pyrrolo[2,3-b]pyrazin-5-yl)-methanol

To a partial suspension of 2-bromo-5H-pyrrolo[2,3-b]pyrazine (5.0 g, 25.2 mmol) in 1,4-dioxane (100 mL) was added 2.0 M aqueous NaOH (25 mL, 50.0 mmol) and 37% aqueous formaldehyde (19 mL, 252 mmol). The dark homogenous reaction mixture was stirred at room temperature overnight. The organics were evaporated under reduced pressure. The aqueous layer was neutralized with 1.0 M HCl and extracted with EtOAc (2×). The combined organics were concentrated to afford 2.6 g of an orange solid. Upon standing, a thick brown precipitate formed in the aqueous layer. The precipitate was collected by filtration and dried. The brown solid was extracted with hot 10% MeOH/EtOAc (3×200 mL). The extracts were combined and evaporated to provide an additional 3.05 g of orange solid. Overall yield was 5.65 g (87%) of (2-bromo-7-hydroxymethyl-pyrrolo[2,3-b]pyrazin-5-yl)-methanol. $^1$H NMR (DMSO-$d_6$, 400 MHz): δ (ppm) 8.43 (s, 1H), 7.96 (s, 1H), 6.71 (t, J=7.3 Hz, 1H), 5.59 (d, J=7.6 Hz, 2H), 5.10 (t, J=5.3 Hz, 1H), 4.66 (d, J=5.6 Hz, 2H).

Step 2

(2-Bromo-5H-pyrrolo[2,3-b]pyrazin-7-yl)-methanol

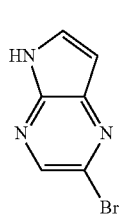

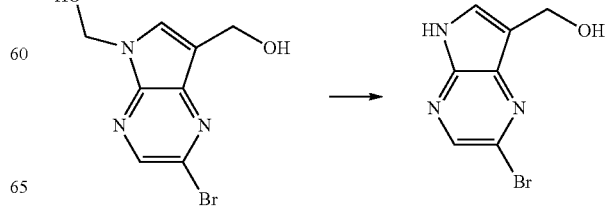

To a suspension of (2-bromo-7-hydroxymethyl-pyrrolo[2,3-b]pyrazin-5-yl)-methanol (5.65 g, 21.9 mmol) in THF (150 mL) was added a solution of 2.0 M aqueous NaOH (33 mL, 66 mmol). The homogeneous reaction mixture was stirred overnight then the organics were removed under reduced pressure. The aqueous residue was brought to pH 4 with 1.0 M aqueous HCl. The resulting precipitate was collected via filtration and rinsed with $H_2O$ to afford 3.68 g of a yellow solid. The filtrate was extracted with EtOAc (2×) and the organics were concentrated under reduced pressure to provide an additional 0.92 g of yellow solid. Overall yield was 4.60 g (92%) of (2-bromo-5H-pyrrolo[2,3-b]pyrazin-7-yl)-methanol. $^1$H NMR (DMSO-$d_6$, 300 MHz): δ (ppm) 12.19 (br. s., 1H), 8.33 (s, 1H), 7.85 (s, 1H), 4.96 (t, J=5.3 Hz, 1H), 4.62 (d, J=4.9 Hz, 2H).

Step 3

2-Bromo-5-(2-trimethylsilanyl-ethoxymethyl)-5H-pyrrolo[2,3-b]pyrazine-7-carbaldehyde

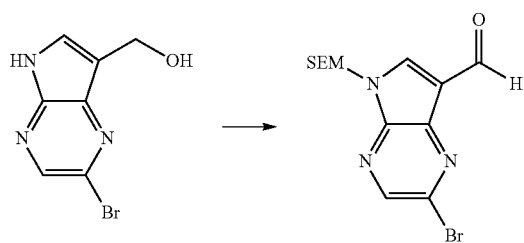 [SMILES: OCc1c[nH]c2ncc(Br)nc12 ; C[Si](C)(C)CCOCn1cc(C=O)c2nc(Br)cnc21]

A stock solution of Jones reagent (2.67 M) was prepared by carefully adding concentrated $H_2SO_4$ (2.3 mL) to $CrO_3$ (2.67 g) then diluting to 10 mL with $H_2O$. To a partial suspension of (2-bromo-5H-pyrrolo[2,3-b]pyrazin-7-yl)-methanol (4.6 g, 20.1 mmol) in acetone (300 mL) was slowly added Jones reagent (9 mL, 24.0 mmol). During the addition the starting material gradually dissolved and a thick green precipitate was formed. The reaction mixture was stirred for 15 min then quenched with i-PrOH (2 mL) and filtered over Celite, rinsing with acetone. The filtrate was concentrated to provide 4.76 g of 2-bromo-5H-pyrrolo[2,3-b]pyrazine-7-carbaldehyde as a yellow-orange solid that was used without further purification. To a solution of this solid in DMF (50 mL) at 0° C. was added NaH (60% in mineral oil, 1.2 g, 30.1 mmol). The reaction mixture was stirred at room temperature for 30 min then cooled back to 0° C. and 2-(trimethylsilyl)ethoxymethyl chloride (4.3 mL, 24.1 mmol) was slowly added. The reaction mixture was warmed to room temperature and stirred for 1 h then quenched with $H_2O$ and extracted with EtOAc (3×). The combined organics were washed with $H_2O$ (3×) and brine then dried over $MgSO_4$ and concentrated. The residue was purified by $SiO_2$ chromatography (20% to 30% EtOAc/hexanes) to isolate 3.82 g (53%) of 2-bromo-5-(2-trimethylsilanylethoxymethyl)-5H-pyrrolo[2,3-b]pyrazine-7-carbaldehyde as a yellow solid. $^1$H NMR (CDCl$_3$, 300 MHz): δ (ppm) 10.37 (s, 1H), 8.50 (s, 1H), 8.33 (s, 1H), 5.73 (s, 2H), 3.53-3.70 (m, 2H), 0.90-1.05 (m, 2H), 0.00 (s, 9H).

Method B

Step 1

2-Bromo-5-(2-trimethylsilanyl-ethoxymethyl)-5H-pyrrolo[2,3-b]pyrazine

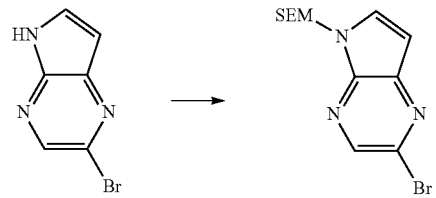 [SMILES: Brc1cnc2[nH]ccc2n1 ; C[Si](C)(C)CCOCn1ccc2nc(Br)cnc21]

In a dry round-bottomed flask, 2-bromo-5H-pyrrolo[2,3-b]pyrazine (5.0 g, 25.2 mmol) was dissolved in DMF (50 mL). The reaction mixture was cooled to 0° C. and sodium hydride (60% dispersion in mineral oil, 1.22 g, 30.6 mmol). The reaction mixture was warmed to room temperature and stirred for 15 min then cooled back to 0° C. and SEM-Cl (5.4 mL, 30.4 mmol) was slowly added. After the addition was complete, the ice bath was removed and the reaction mixture was stirred at room temperature for 1.5 h. The reaction mixture was quenched with 50 mL water and extracted with 150 mL diethyl ether (2×). The combined organic layers were washed twice with 30 mL water and once with 30 mL brine then dried over sodium sulfate, filtered and concentrated. The residue was absorbed on ~20 g $SiO_2$ and chromatographed over 200 g $SiO_2$ with EtOAc/Hexanes (gradient: 0-15% EtOAc). All fractions containing product were combined and concentrated to afford 6.61 g (80%) of 2-bromo-5-(2-trimethylsilanylethoxymethyl)-5H-pyrrolo[2,3-b]pyrazine as a pale yellow oil which gradually solidified. $^1$H NMR (CDCl$_3$, 300 MHz): δ (ppm) 8.38 (s, 1H), 7.70 (d, J=3.8 Hz, 1H), 6.76 (d, J=3.8 Hz, 1H), 5.68 (s, 2H), 3.50-3.65 (m, 2H), 0.88-1.03 (m, 2H), 0.00 (s, 9H).

Step 2

2-Bromo-5-(2-trimethylsilanyl-ethoxymethyl)-5H-pyrrolo[2,3-b]pyrazine-7-carbaldehyde

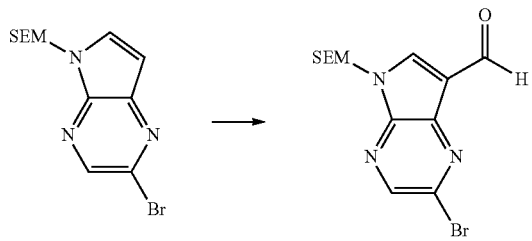 [SMILES: C[Si](C)(C)CCOCn1ccc2nc(Br)cnc21 ; C[Si](C)(C)CCOCn1cc(C=O)c2nc(Br)cnc21]

In a round-bottomed flask, 2-bromo-5-(2-trimethylsilanylethoxymethyl)-5H-pyrrolo[2,3-b]pyrazine (6.58 g, 20.0 mmol) was dissolved in chloroform (pentene stabilized, 120 mL) and chloromethylenedimethyliminium chloride (10.3 g, 80.2 mmol) was added. The reaction mixture was stirred at reflux for 8 h as a steady stream of nitrogen gas was bubbled through the reaction mixture. The dark brown solution was cooled to room temperature and stirred overnight. The reaction mixture was carefully quenched with ~100 mL saturated NaHCO₃-solution (caution: exothermic) and then extracted twice with 200 mL diethyl ether. The organic layers were combined, dried over sodium sulfate, filtered and concentrated. The residue was absorbed on ~20 g SiO₂ and chromatographed over 200 g SiO₂ with EtOAc/Hexanes (gradient: 0-25% EtOAc). All fractions containing product were combined and concentrated to afford 5.92 g (83%) of an approx 3:1 mixture of 2-bromo-5-(2-trimethylsilanylethoxymethyl)-5H-pyrrolo[2,3-b]pyrazine-7-carbaldehyde and 2-chloro-5-(2-trimethylsilanyl-ethoxymethyl)-5H-pyrrolo[2,3-b]pyrazine-7-carbaldehyde as a yellow solid. Bromide: ¹H NMR (CDCl₃, 300 MHz): δ (ppm) 10.37 (s, 1H), 8.50 (s, 1H), 8.33 (s, 1H), 5.73 (s, 2H), 3.56-3.67 (m, 2H), 0.91-1.02 (m, 2H), 0.00 (s, 9H); Chloride: ¹H NMR (CDCl₃, 300 MHz): δ (ppm) 10.36 (s, 1H), 8.41 (s, 1H), 8.35 (s, 1H), 5.74 (s, 2H), 3.56-3.67 (m, 2H), 0.91-1.02 (m, 2H), 0.00 (s, 9H).

Procedure 2

2-Bromo-5-(2-trimethylsilanylethoxymethyl)-5H-pyrrolo[2,3-b]pyrazine-7-carboxylic acid

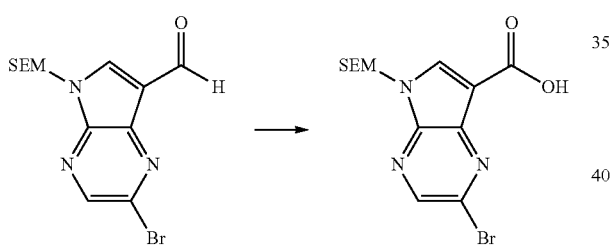

In a flask 2-bromo-5-(2-trimethylsilanylethoxymethyl)-5H-pyrrolo[2,3-b]pyrazine-7-carbaldehyde (3.11 g, 8.74 mmol) was dissolved in dioxane (120 mL) and H₂O (30 mL) and the mixture cooled at 0° C. Sufamic acid (5.09 g, 52.4 mmol) was added, followed by a solution of sodium chlorite (1.28 g, 11.4 mmol) and potassium dihydrogen phosphate (14.3 g, 104.9 mmol) in H₂O (75 mL) via an addition funnel over 15 min. The mixture was allowed to warm to room temperature over 2 h. The resulting yellow solid was filtered off, washed with H₂O and hexane and dried. The filtrate was then extracted with EtOAc, and the combined organics washed with brine, dried over MgSO₄ and concentrated to give additional product. In total 3.71 g of 2-bromo-5-(2-trimethylsilanylethoxymethyl)-5H-pyrrolo[2,3-b]pyrazine-7-carboxylic acid was obtained as a yellow solid. ¹H NMR (CDCl₃, 400 MHz): δ (ppm) 8.52 (s, 1H), 8.42 (s, 1H), 5.73 (s, 2H), 3.56-3.65 (m, 2H), 0.90-1.02 (m, 2H), 0.00 (s, 9H).

Procedure 3

2-Bromo-5H-pyrrolo[2,3-b]pyrazine-7-carboxylic acid methyl ester

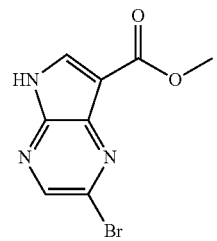

Step 1

2-Bromo-5H-pyrrolo[2,3-b]pyrazine-7-carboxylic acid

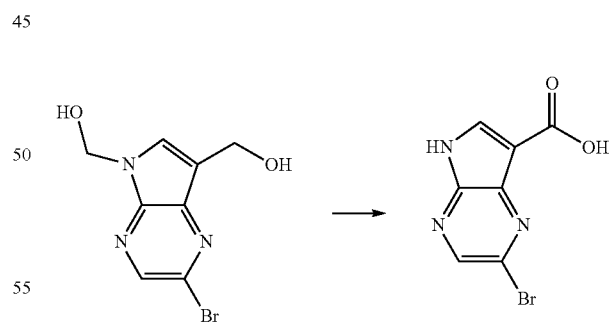

To a stirred solution of (2-bromo-7-hydroxymethyl-pyrrolo[2,3-b]pyrazin-5-yl)-methanol (0.525 g, 2.03 mmol) in 200 mL of acetone at 40° C. was added a solution of CrO₃ (0.832 g, 8.32 mmol) and H₂SO₄ (1.32 g, 13.4 mmol) in water (3 ml). Then the reaction was stirred at 40° C. for 16 hours then filtered through Celite. The filtrate was evaporated at 40° C. under reduced pressure to give 2-bromo-5H-pyrrolo[2,3-b]pyrazine-7-carboxylic acid (0.527 g) as an off-white solid.

LCMS: $(M+H)^+=264$; $^1H$ NMR (300 MHz, DMSO-$d_6$): δ 13.04 (s, 1H), 8.53 (s, 1H), 8.45 (s, 1H), 5.63 (s, 1H).

Step 2

2-Bromo-5H-pyrrolo[2,3-b]pyrazine-7-carboxylic acid methyl ester

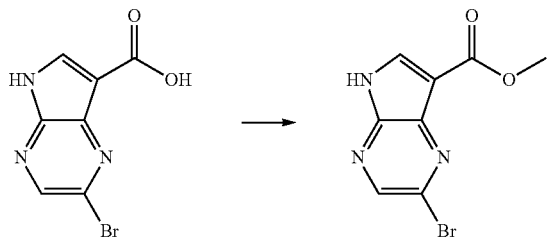

To a stirred solution of 2-bromo-5H-pyrrolo[2,3-b]pyrazine-7-carboxylic acid (0.527 g, 2.18 mmol) in 50 ml, of methanol was added $H_2SO_4$ (1.5 mL) slowly at room temperature. The reaction mixture was stirred at reflux for 16 h. The solvent was evaporated at 40° C. under reduced pressure then the residue was suspended in 5 mL of water and treated with solid $NaHCO_3$ until pH=7. The solution was extracted with ethyl acetate (90 mL), then the organics were washed with water (20 mL), brine (20 mL) and dried over anhydrous sodium sulfate. The drying agent was removed by filtration and the solvent was evaporated at 40° C. under reduced pressure to give a crude product, which was purified by column chromatography (silica gel, 200-300 mesh, eluting with a mixture of petroleum ether and ethyl acetate (1:1, v/v) to give 2-bromo-5H-pyrrolo[2,3-b]pyrazine-7-carboxylic acid methyl ester (0.24 g, 43%) as a white solid.

LCMS: $(M+H)^+=278$; $^1H$ NMR (300 MHz, DMSO-$d_6$): δ 8.62 (s, 1H), 8.48 (s, 1H), 3.91 (s, 3H).

Pharmaceutical Compositions and Administration

The compounds of the present invention may be formulated in a wide variety of oral administration dosage forms and carriers. Oral administration can be in the form of tablets, coated tablets, dragées, hard and soft gelatin capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi- solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to a skin-adhesive solid support. The compound of interest can also be combined with a penetration enhancer, e.g., Azone (1-dodecylazacycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and excipients are described in Remington: The Science and Practice of Pharmacy 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Indications and Method of Treatment

The application provides a method for treating an inflammatory or autoimmune condition comprising administering to a patient in need thereof a therapeutically effective amount of the compound of Formula I.

The application provides the above method, further comprising administering an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, or an agent for treating immunodeficiency disorders.

The application provides a method for treating rheumatoid arthritis comprising administering to a patient in need thereof a therapeutically effective amount of the compound of Formula I.

The application provides a method for treating asthma comprising administering to a patient in need thereof a therapeutically effective amount of the compound of Formula I.

The application provides a method for treating an inflammatory condition comprising administering to a patient in need thereof a therapeutically effective amount of the compound of Formula I.

The application provides a method for inhibiting T-cell proliferative disorder comprising administering to a patient in need thereof a therapeutically effective amount of the compound of Formula I.

The application provides a method for inhibiting T-cell proliferative disorder comprising administering to a patient in need thereof a therapeutically effective amount of the compound of Formula I The application provides the above method, wherein the proliferative disorder is cancer.

The application provides a method for treating a B-cell proliferative disorder comprising administering to a patient in need thereof a therapeutically effective amount of the compound of Formula I.

The application provides a method for treating an immune disorder including lupus, multiple sclerosis, rheumatoid arthritis, psoriasis, Type I diabetes, complications from organ transplants, xeno transplantation, diabetes, cancer, asthma, atopic dermatitis, autoimmune thyroid disorders, ulcerative colitis, Crohn's disease, Alzheimer's disease, and Leukemia, comprising administering to a patient in need thereof a therapeutically effective amount of the compound of Formula I.

The application provides a method for preventing or treating all forms of organ rejection, including acute allograft or xenograft rejection and chronic allograft or xenograft rejection, of vascularized or non-vascularized transplants, comprising administering to a patient in need thereof the compound of Formula I.

The application provides a method for inhibiting JAK3 activity comprising administering the compound of Formula I, wherein the compound exhibits an $IC_{50}$ of 50 micromolar or less in an in vitro biochemical assay of JAK3 activity.

The application provides the above method, wherein the compound exhibits an $IC_{50}$ of 100 nanomolar or less in an in vitro biochemical assay of JAK3 activity.

The application provides the above method, wherein the compound exhibits an $IC_{50}$ of 10 nanomolar or less in an in vitro biochemical assay of JAK3 activity.

A method for inhibiting SYK activity comprising administering the compound of Formula I, wherein the compound exhibits an $IC_{50}$ of 50 micromolar or less in an in vitro biochemical assay of SYK activity.

The application provides the above method, wherein the compound exhibits an $IC_{50}$ of 100 nanomolar or less in an in vitro biochemical assay of SYK activity.

The application provides the above method, wherein the compound exhibits an $IC_{50}$ of 10 nanomolar or less in an in vitro biochemical assay of SYK activity.

The application provides a method for treating an inflammatory condition comprising co-administering to a patient in need thereof a therapeutically effective amount of an anti-inflammatory compound in combination with the compound of Formula I.

The application provides a method for treating an immune disorder comprising co-administering to a patient in need thereof a therapeutically effective amount of an immunosuppressant compound in combination with the compound of Formula I.

EXAMPLES

The following examples illustrate the preparation and biological evaluation of compounds within the scope of the invention. In general, the nomenclature used in this section is based on AUTONOM™ v.4.0, as noted above, or, alternatively, based on ChemDraw. These examples and preparations which follow are provided to enable those skilled in the art to more clearly understand and to practice the present invention. They should not be considered as limiting the scope of the invention, but merely as being illustrative and representative thereof.

ABBREVIATIONS

Commonly used abbreviations include: acetyl (Ac), azo-bis-isobutyrylnitrile (AIBN), atmospheres (Atm), 9-borabicyclo[3.3.1]nonane (9-BBN or BBN), tert-butoxycarbonyl (Boc), di-tert-butyl pyrocarbonate or boc anhydride ($BOC_2O$), benzyl (Bn), butyl (Bu), Chemical Abstracts Registration Number (CASRN), benzyloxycarbonyl (CBZ or Z), carbonyl diimidazole (CDI), 1,4-diazabicyclo[2.2.2]octane (DABCO), diethylaminosulfur trifluoride (DAST), dibenzylideneacetone (dba), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), 1,1'-bis-(diphenylphosphino)ethane (dppe), 1,1'-bis-(diphenylphosphino)ferrocene (dppf), 1-(3-dimethylaminopropyl)-3-ethylcarbodiimide hydrochloride (EDCI), ethyl (Et), ethyl acetate (EtOAc), ethanol (EtOH), 2-ethoxy-2H-quinoline-1-carboxylic acid ethyl ester (EEDQ), diethyl ether ($Et_2O$), O-(7-azabenzotriazole-1-yl)-N,N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), lithium hexamethyl disilazane (LiHMDS), methanol (MeOH), melting point (mp or MP), $MeSO_2$— (mesyl or Ms), methyl (Me), acetonitrile (MeCN), m-chloroperbenzoic acid (MCPBA), mass spectrum (ms or MS), methyl t-butyl ether (MTBE), N-bromosuccinimide (NBS), N-carboxyanhydride (NCA), N-chlorosuccinimide (NCS), N-methylmorpholine (NMM), N-methylpyrrolidone (NMP), pyridinium chlorochromate (PCC), pyridinium dichromate (PDC), phenyl (Ph), propyl (Pr), iso-propyl (i-Pr), pounds per square inch (psi), pyridine (pyr), room temperature (rt or RT), 2-(trimethylsilyl) ethoxymethyl chloride (SEMC1), tert-butyldimethylsilyl or t-BuMe$_2$Si (TBDMS), triethylamine (TEA or Et$_3$N), 2,2,6,6-tetramethylpiperidine 1-oxyl (TEMPO), triflate or $CF_3SO_2$— (Tf), trifluoroacetic acid (TFA), 1,1'-bis-2,2,6,6-tetramethyl-heptane-2,6-dione (TMHD), O-benzotriazol-1-yl-N,N,N',

PREPARATIVE EXAMPLES

Example 1

2-(1-Methyl-1H-indazol-3-yl)-5H-pyrrolo[2,3-b]pyrazine-7-carboxylic acid [(R)-2-(4-cyano-piperidin-1-yl)-1-cyclopropyl-2-oxo-ethyl]-amide

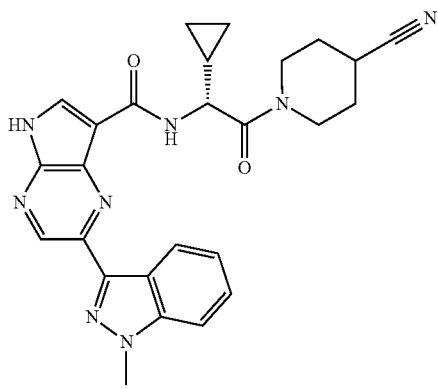 [SMILES: Cn1nc(-c2cnc3[nH]cc(C(=O)N[C@@H](C(=O)N4CCC(C#N)CC4)C4CC4)c3n2)c2ccccc21]

Step 1

3-Iodo-1H-indazole

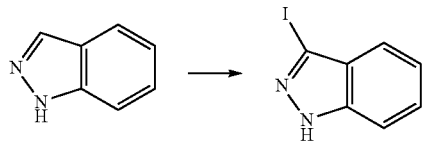 [SMILES: c1ccc2[nH]ncc2c1 ; Ic1n[nH]c2ccccc12]

In a 50 mL round-bottomed flask, indazole (0.80 g, 6.8 mmol) was dissolved in DMF (14 mL). Iodine (3.4 g, 13.5 mmol) was added followed by potassium hydroxide (1.47 g, 26.2 mmol). The dark reaction mixture was stirred at room temperature for 1.25 h then was quenched with 10% aq NaHSO$_3$ and extracted with diethyl ether (2×). The combined organic layers were washed with water and brine then dried over sodium sulfate, filtered and concentrated to give 1.65 g (95%) of 3-iodo-1H-indazole as a light yellow solid. $^1$H NMR (CDCl$_3$, 300 MHz): δ (ppm) 10.56 (br. s, 1H), 7.47-7.57 (m, 3H), 7.23-7.30 (m, 1H).

Step 2

3-Iodo-1-methyl-1H-indazole

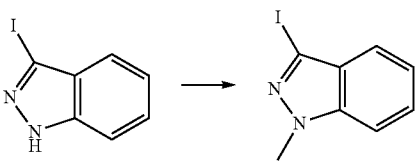

In a 50 ml round-bottomed flask, 3-iodo-1H-indazole (1.0 g, 3.9 mmol) was dissolved in THF (12 ml) and the solution was cooled to 0° C. Potassium tert-butoxide (612 mg, 5.45 mmol) was added and the reaction mixture was stirred at 0° C. for 1.25 h. Methyl iodide (0.29 ml, 4.64 mmol) was added dropwise then the ice bath was removed and the reaction mixture was stirred at room temperature for 2 h. The reaction mixture was quenched with water and extracted with EtOAc (2×). The combined organic layers were washed with water and brine then dried over sodium sulfate, filtered and concentrated. The residue was purified by chromatography over silica gel with EtOAc/Hexanes (gradient 0-10% EtOAc) to afford 863 mg (86%) of 3-iodo-1-methyl-1H-indazole as a yellow oil. $^1$H NMR (CDCl$_3$, 300 MHz): δ (ppm) 7.42-7.53 (m, 2H), 7.33-7.40 (m, 1H), 7.22 (ddd, J=8.0, 6.9, 0.9 Hz, 1H), 4.11 (s, 3H).

Step 3

1-Methyl-3-tributylstannanyl-1H-indazole

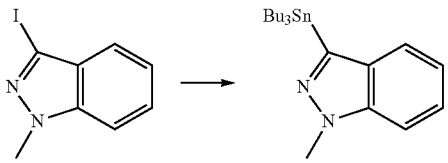

3-Iodo-1-methyl-1H-indazole (0.15 g, 0.58 mmol) was dissolved in THF (3 ml) and the solution was cooled to −16° C. using a NaCl/ice bath. Isopropylmagnesium chloride (2.0M in THF, 0.32 ml, 0.64 mmol) was added dropwise and the reaction mixture was stirred at −16° C. for 15 min. Tributylchlorostannane (0.18 ml, 0.66 mmol) was slowly added and the reaction mixture was allowed to warm to room temperature over 1.5 h. The reaction mixture was quenched with saturated NH$_4$Cl solution and extracted with EtOAc (2×). The combined organic layers were washed with water and brine then dried over sodium sulfate, filtered and concentrated. The residue was purified by chromatography over silica gel with EtOAc/Hexanes (0.5% triethylamine, gradient 0-5% EtOAc) to give 224 mg (92%) of 1-methyl-3-tributylstannanyl-1H-indazole as a colorless oil. $^1$H NMR (CDCl$_3$, 300 MHz): δ

(ppm) 7.70 (d, J=8.3 Hz, 1H), 7.32-7.45 (m, 2H), 7.11 (ddd, J=8.0, 6.3, 1.5 Hz, 1H), 1.52-1.69 (m, 6H), 1.19-1.44 (m, 12H), 0.83-0.95 (m, 9H).

Step 4

[(R)-2-(4-Cyanopiperidin-1-yl)-1-cyclopropyl-2-oxo-ethyl]-carbamic acid tert-butyl ester

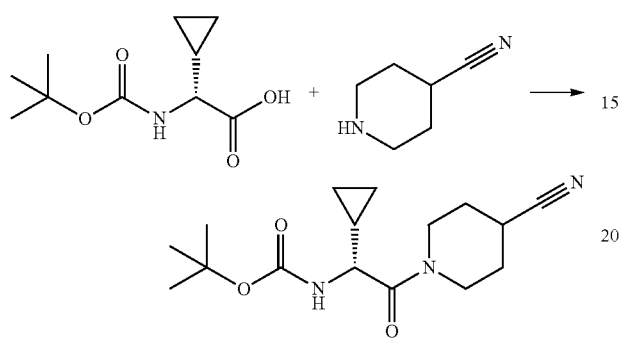

In a round-bottomed flask, Boc-D-cyclopropylglycine (1.80 g, 8.36 mmol) and piperidine-4-carbonitrile (1.2 g, 10.9 mmol) were dissolved in DMF (30 ml). HATU (3.5 g, 9.2 mmol) and N,N-diisopropylethylamine (2.3 ml, 13.2 mmol) were added and the yellow solution was stirred at room temperature overnight. The reaction mixture was quenched with water and extracted with diethyl ether (2×). The combined organic layers were washed twice with water and once with brine then dried over sodium sulfate, filtered and concentrated to afford 2.72 g (95%) of [(R)-2-(4-cyanopiperidin-1-yl)-1-cyclopropyl-2-oxo-ethyl]-carbamic acid tert-butyl ester as a light yellow oil which was used without further purification.

Step 5

1-((R)-2-Amino-2-cyclopropyl-acetyl)-piperidine-4-carbonitrile trifluoroacetate

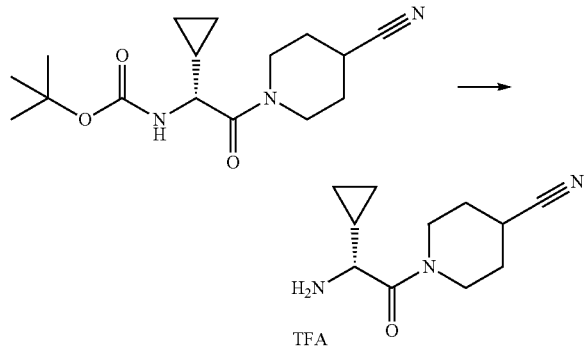

In a round-bottomed flask, [(R)-2-(4-cyanopiperidin-1-yl)-1-cyclopropyl-2-oxo-ethyl]-carbamic acid tert-butyl ester (2.71 g, 7.93 mmol) was dissolved in dichloromethane (50 ml). The solution was cooled to 0° C. and trifluoroacetic acid (18 ml, 234 mmol) was slowly added. After the addition was complete, the ice bath was removed and the reaction mixture was stirred at room temperature for 2 h. The reaction mixture was concentrated to provide 1-((R)-2-amino-2-cyclopropyl-acetyl)-piperidine-4-carbonitrile trifluoroacetate as a yellow oil which was used without further purification.

Step 6

2-Bromo-5-(2-trimethylsilanyl-ethoxymethyl)-5H-pyrrolo[2,3-b]pyrazine-7-carboxylic acid [(R)-2-(4-cyano-piperidin-1-yl)-1-cyclopropyl-2-oxo-ethyl]-amide

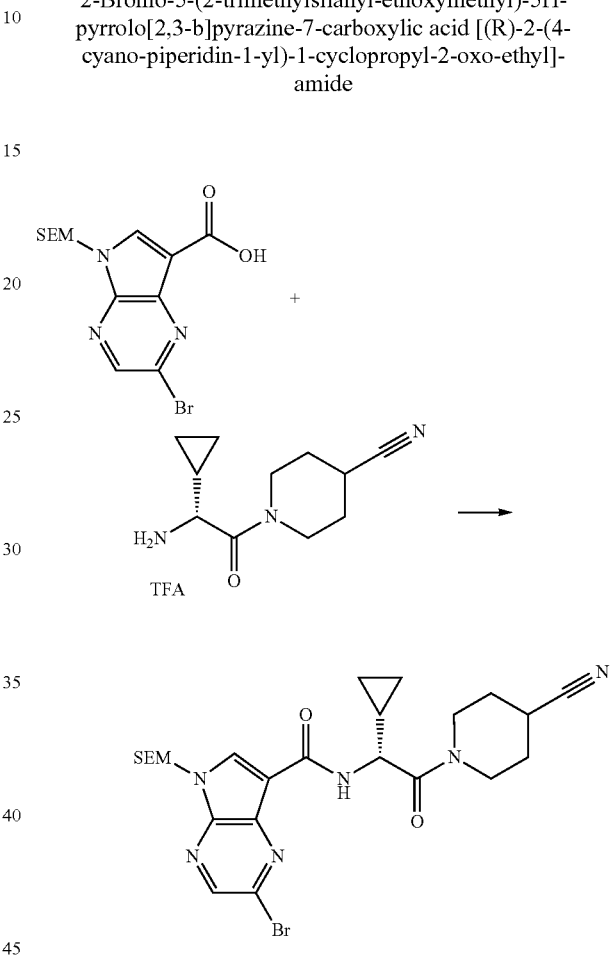

In a round-bottomed flask, 1-((R)-2-amino-2-cyclopropyl-acetyl)-piperidine-4-carbonitrile trifluoroacetate (5.19 g, 7.27 mmol) was dissolved in DMF (25 ml) and N,N-diisopropylethylamine (8.5 ml, 48.7 mmol) was added. Then 2-bromo-5-((2-(trimethylsilyl)ethoxy)methyl)-5H-pyrrolo[2,3-b]pyrazine-7-carboxylic acid (2.20 g, 5.91 mmol) (approx 2:1 Br:Cl) and HATU (2.47 g, 6.5 mmol) were added and the reaction mixture was stirred at room temperature overnight. The reaction was quenched with water and extracted with diethyl ether (2×). The combined organic layers were washed twice with water and once with brine then dried over sodium sulfate, filtered and concentrated. The residue was purified by chromatography over silica gel with EtOAc/Hexanes (gradient 0-80% EtOAc) to afford 3.0 g of an off-white foam. SFC chromatography (Chiralpak IA-H 2×25 column, 40% MeOH) afforded 1.71 g (52%) of 2-bromo-5-(2-trimethylsilanyl-ethoxymethyl)-5H-pyrrolo[2,3-b]pyrazine-7-carboxylic acid [(R)-2-(4-cyano-piperidin-1-yl)-1-cyclopropyl-2-oxo-ethyl]-amide as a white foam and 779 mg (26%) 2-chloro-5-(2-trimethylsilanyl-ethoxymethyl)-5H-pyrrolo

[2,3-b]pyrazine-7-carboxylic acid [(R)-2-(4-cyano-piperidin-1-yl)-1-cyclopropyl-2-oxo-ethyl]-amide as an off-white foam.

Step 7

2-(1-Methyl-1H-indazol-3-yl)-5-(2-trimethylsilanyl-ethoxymethyl)-5H-pyrrolo[2,3-b]pyrazine-7-carboxylic acid [(R)-2-(4-cyano-piperidin-1-yl)-1-cyclopropyl-2-oxo-ethyl]-amide

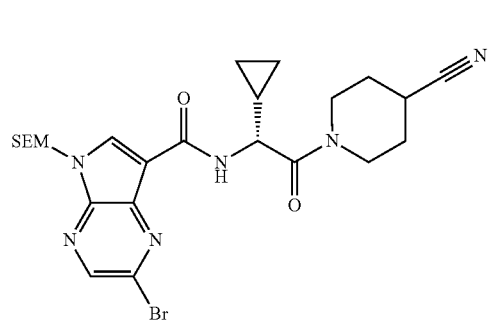

In a dry round-bottomed flask 2-bromo-5-(2-trimethylsilanyl-ethoxymethyl)-5H-pyrrolo[2,3-b]pyrazine-7-carboxylic acid [(R)-2-(4-cyano-piperidin-1-yl)-1-cyclopropyl-2-oxo-ethyl]-amide (0.12 g, 0.21 mmol) and 1-methyl-3-tributylstannanyl-1H-indazole (117 mg, 0.28 mmol) were dissolved in DMF (2 ml). The reaction mixture was evacuated and backfilled with Argon then tetrakis(triphenylphosphine)palladium(0) (13 mg, 0.011 mmol) and copper(I) iodide (9 mg, 0.047 mmol) were added. The reaction mixture was stirred at 80° C. for 1.5 h then cooled to room temperature, quenched with water and extracted with diethyl ether (2×). The combined organic layers were washed twice with water and brine then dried over sodium sulfate, filtered and concentrated. The residue was purified by chromatography over silica gel with MeOH/CH$_2$Cl$_2$ (0.5% NH$_4$OH) (gradient 0-3% MeOH) to afford 161 mg of 2-(1-methyl-1H-indazol-3-yl)-5-(2-trimethylsilanyl-ethoxymethyl)-5H-pyrrolo[2,3-b]pyrazine-7-carboxylic acid [(R)-2-(4-cyano-piperidin-1-yl)-1-cyclopropyl-2-oxo-ethyl]-amide as a yellow oil.

Step 8

2-(1-Methyl-1H-indazol-3-yl)-5H-pyrrolo[2,3-b]pyrazine-7-carboxylic acid [(R)-2-(4-cyano-piperidin-1-yl)-1-cyclopropyl-2-oxo-ethyl]-amide

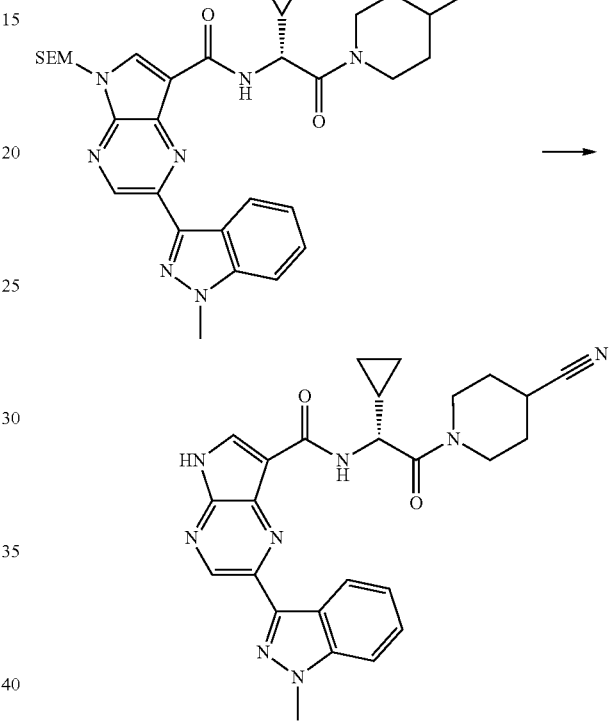

In a round-bottomed flask, 2-(1-methyl-1H-indazol-3-yl)-5-(2-trimethylsilanylethoxymethyl)-5H-pyrrolo[2,3-b]pyrazine-7-carboxylic acid [(R)-2-(4-cyano-piperidin-1-yl)-1-cyclopropyl-2-oxo-ethyl]-amide (0.158 g, 0.193 mmol) was dissolved in dichloromethane (1 ml) and trifluoroacetic acid (0.6 ml, 7.8 mmol) was added. The reaction mixture was stirred at room temperature for 2 h then concentrated. The residue was redissolved in dichloromethane (1 ml) and ethylenediamine (0.8 ml, 11.7 mmol) was added. The solution was stirred at room temperature for 1 h then quenched with water and extracted with EtOAc (2×). The combined organic layers were washed with water and brine then dried over sodium sulfate, filtered and concentrated. The residue was purified by chromatography over silica gel with MeOH/CH$_2$Cl$_2$ (0.5% NH$_4$OH) (gradient 0-4% MeOH) followed by trituration with ethyl acetate to afford 31 mg (32%) of 2-(1-methyl-1H-indazol-3-yl)-5H-pyrrolo[2,3-b]pyrazine-7-carboxylic acid [(R)-2-(4-cyano-piperidin-1-yl)-1-cyclopropyl-2-oxo-ethyl]-amide as a light yellow powder. MS: (M+H)$^+$= 483; $^1$H NMR (DMSO-d$_6$, 300 MHz): δ (ppm) 12.89 (br. s., 1H), 9.17 (s, 1H), 8.79 (d, J=7.9 Hz, 1H), 8.65 (d, J=8.3 Hz, 1H), 8.45 (d, J=9.4 Hz, 1H), 7.75 (d, J=8.3 Hz, 1H), 7.50 (t, J=7.6 Hz, 1H), 7.13-7.33 (m, 1H), 4.88 (t, J=7.9 Hz, 1H), 4.19

(s, 3H), 3.68-4.05 (m, 2H), 3.34-3.66 (m, 2H), 3.14 (br. s., 1H), 1.47-2.07 (m, 4H), 1.34 (br. s., 1H), 0.37-0.65 (m, 4H).

Example 2

2-(6-Chloro-1-methyl-1H-indazol-3-yl)-5H-pyrrolo[2,3-b]pyrazine-7-carboxylic acid [(R)-2-(4-cyano-piperidin-1-yl)-1-cyclopropyl-2-oxo-ethyl]-amide

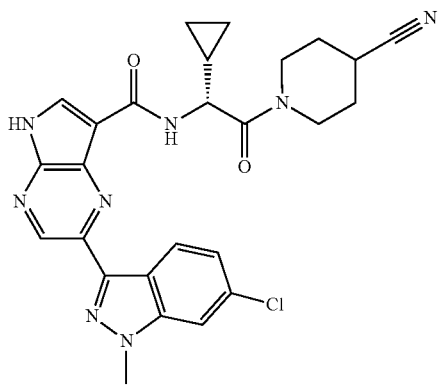 [SMILES: Cn1nc(-c2cnc3[nH]cc(C(=O)N[C@@H](C(=O)N4CCC(C#N)CC4)C4CC4)c3n2)c2ccc(Cl)cc21]

Prepared according to the procedure outlined in Example 1, substituting 6-chloro-1H-indazole for indazole in step 1. MS: (M+H)$^+$=517; $^1$H NMR (DMSO-d$_6$, 300 MHz): δ (ppm) 12.93 (s, 1H), 9.15 (s, 1H), 8.83 (dd, J=8.5, 2.8 Hz, 1H), 8.59 (d, J=8.3 Hz, 1H), 8.46 (d, J=7.9 Hz, 1H), 7.97 (d, J=1.5 Hz, 1H), 7.23 (t, J=7.0 Hz, 1H), 4.86-4.99 (m, 1H), 4.17 (s, 3H), 3.67-4.04 (m, 2H), 3.06-3.67 (m, 3H), 1.49-2.08 (m, 4H), 1.31 (br. s., 1H), 0.28-0.61 (m, 4H).

Example 3

2-(5-Chloro-1-methyl-1H-indazol-3-yl)-5H-pyrrolo[2,3-b]pyrazine-7-carboxylic acid [(R)-2-(4-cyano-piperidin-1-yl)-1-cyclopropyl-2-oxo-ethyl]-amide

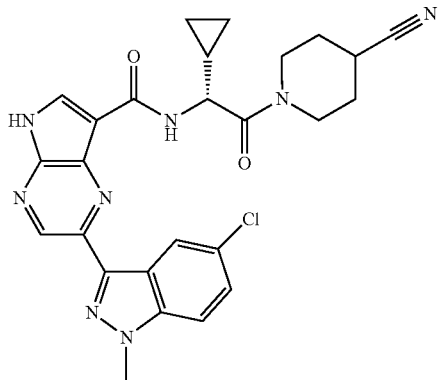 [SMILES: Cn1nc(-c2cnc3[nH]cc(C(=O)N[C@@H](C(=O)N4CCC(C#N)CC4)C4CC4)c3n2)c2cc(Cl)ccc21]

Prepared according to the procedure outlined in Example 1, substituting 5-chloro-1H-indazole for indazole in step 1. MS: (M+H)$^+$=517; $^1$H NMR (DMSO-d$_6$, 300 MHz): δ (ppm) 12.91 (s, 1H), 9.16 (s, 1H), 8.70 (br. s., 2H), 8.46 (d, J=9.4 Hz, 1H), 7.83 (d, J=8.9 Hz, 1H), 7.51 (dd, J=8.9, 1.5 Hz, 1H), 4.88 (t, J=7.7 Hz, 1H), 4.20 (s, 3H), 3.07-3.98 (m, 5H), 1.33-2.12 (m, 5H), 0.38-0.65 (m, 4H).

Example 4

2-(6-Chloro-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide

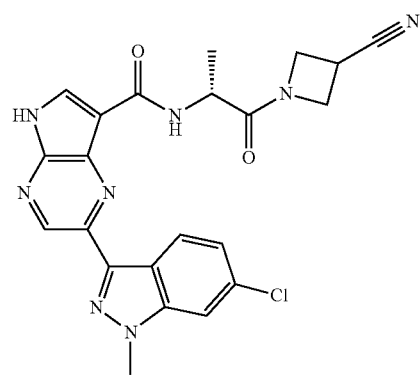 [SMILES: C[C@@H](NC(=O)c1c[nH]c2ncc(-c3nn(C)c4cc(Cl)ccc34)nc12)C(=O)N1CC(C#N)C1]

Step 1

6-Chloro-3-iodo-1H-indazole

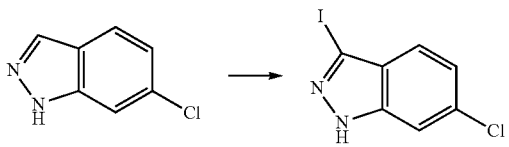 [SMILES: Clc1ccc2cn[nH]c2c1 ; Clc1ccc2c(I)n[nH]c2c1]

In a round-bottomed flask, 6-chloro-1H-indazole (90 mg, 0.59 mmol) was dissolved in DMF (1.4 mL). Iodine (300 mg, 1.18 mmol) was added followed by potassium hydroxide (128 mg, 2.28 mmol). The dark reaction mixture was stirred at room temperature for 3 h then was quenched with 10% aq NaHSO$_3$ and extracted with diethyl ether (2×). The combined organic layers were washed with water and brine then dried over sodium sulfate, filtered and concentrated to give 169 mg (98%) of 6-chloro-3-iodo-1H-indazole as an orange solid.

Step 2

6-Chloro-3-iodo-1-methyl-1H-indazole

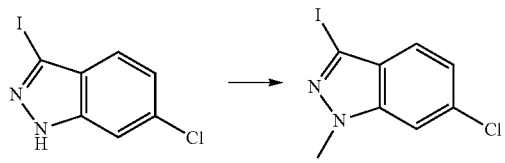

In a round-bottomed flask, 6-chloro-3-iodo-1H-indazole (167 mg, 0.57 mmol) was dissolved in THF (2 ml) and the solution was cooled to 0° C. Potassium tert-butoxide (90 mg, 0.80 mmol) was added and the reaction mixture was stirred at 0° C. for 1.25 h. Methyl iodide (0.045 ml, 0.72 mmol) was added dropwise then the ice bath was removed and the reaction mixture was stirred at room temperature for 2 h. The reaction mixture was quenched with water and extracted with EtOAc (2×). The combined organic layers were washed with water and brine then dried over sodium sulfate, filtered and concentrated. The residue was purified by chromatography over silica gel with EtOAc/Hexanes (gradient 0-5% EtOAc) to afford 110 mg (63%) of 6-chloro-3-iodo-1-methyl-1H-indazole as a yellow solid.

Step 3

6-Chloro-1-methyl-3-tributylstannanyl-1H-indazole

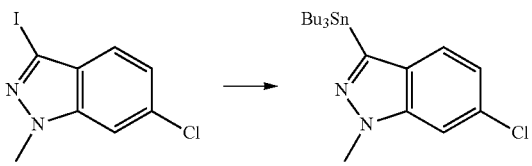

6-Chloro-3-iodo-1-methyl-1H-indazole (108 mg, 0.35 mmol) was dissolved in THF (2 ml) and the solution was cooled to −16° C. using a NaCl/ice bath. Isopropylmagnesium chloride (2.0M in THF, 0.20 ml, 0.40 mmol) was added dropwise and the reaction mixture was stirred at −16° C. for 15 min. Tributylchlorostannane (0.11 ml, 0.40 mmol) was slowly added and the reaction mixture was allowed to warm to room temperature over 1.5 h. The reaction mixture was quenched with saturated NH$_4$Cl solution and extracted with EtOAc (2×). The combined organic layers were washed with water and brine then dried over sodium sulfate, filtered and concentrated to afford 6-chloro-1-methyl-3-tributylstannanyl-1H-indazole as a brown oil which was used without further purification.

Step 4

[(R)-2-(3-Cyanoazetidin-1-yl)-1-methyl-2-oxo-ethyl]-carbamic acid tert-butyl ester

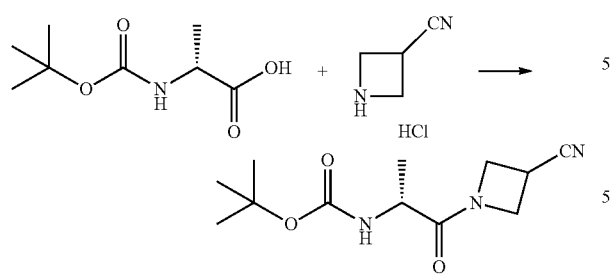

In a round-bottomed flask were combined Boc-D-alanine (500 mg, 2.64 mmol), azetidine-3-carbonitrile hydrochloride (376 mg, 3.17 mmol), HOBT (445 mg, 2.91 mmol) and HATU (1.11 g, 2.91 mmol). Then added DMF (5 mL) followed by N,N-diisopropylethylamine (1.38 mL, 7.93 mmol). The yellow reaction mixture was stirred at room temperature for 3 h then quenched with water and extracted with EtOAc (3×). The combined organics were washed with water (3×) dried over MgSO$_4$ and concentrated. The residue was purified by SiO$_2$ chromatography (50% to 100% EtOAc/hexanes) to afford 493 mg (74%) of [(R)-2-(3-cyanoazetidin-1-yl)-1-methyl-2-oxo-ethyl]-carbamic acid tert-butyl ester as a white solid.

Step 5

1-((R)-2-Amino-propionyl)-azetidine-3-carbonitrile trifluoroacetate

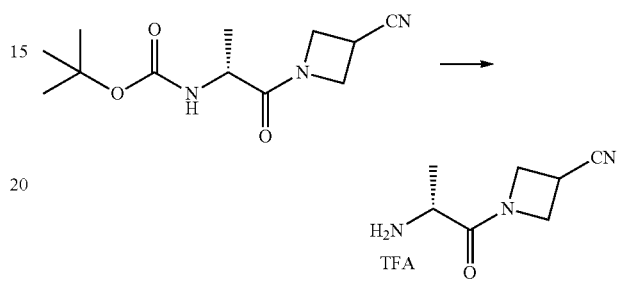

To a solution of [(R)-2-(3-cyanoazetidin-1-yl)-1-methyl-2-oxo-ethyl]-carbamic acid tert-butyl ester (860 mg, 3.4 mmol) in CH$_2$Cl$_2$ (20 mL) was added trifluoroacetic acid (4.0 mL). The reaction mixture was stirred at room temperature for 2 h then concentrated to afford 1-((R)-2-amino-propionyl)-azetidine-3-carbonitrile trifluoroacetate as a pale yellow oil which was used without further purification.

Step 6

2-Bromo-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide

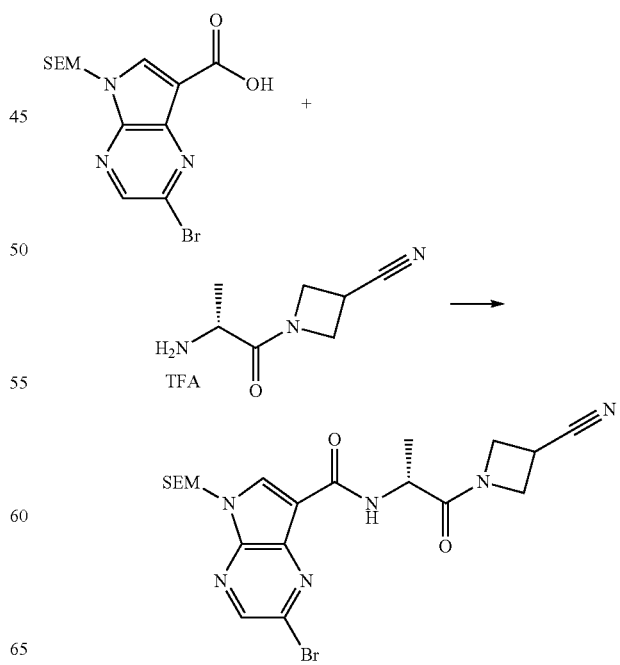

In a round-bottomed flask were combined 2-bromo-5-((2-(trimethylsilyl)ethoxy)methyl)-5H-pyrrolo[2,3-b]pyrazine-7-carboxylic acid (1.05 g, 2.82 mmol) (approx 3:1 Br:Cl), 1-((R)-2-amino-propionyl)-azetidine-3-carbonitrile trifluoroacetate (900 mg, 3.37 mmol), and HATU (1.18 g, 3.1 mmol). Then added DMF (10 mL) followed by N,N-diisopropylethylamine (1.48 mL, 8.46 mmol). The yellow reaction mixture was stirred at room temperature overnight then quenched with water and extracted with EtOAc (3×). The combined organics were washed with water (3×), dried over MgSO$_4$ and concentrated. The residue was purified by SiO$_2$ chromatography (30% to 100% EtOAc/hexanes) to afford 1.19 g (83%) of 2-bromo-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide as a white foamy solid (approx 3:1 mixture of Br and Cl compounds).

Step 7

2-(6-Chloro-1-methyl-1H-indazol-3-yl)-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide

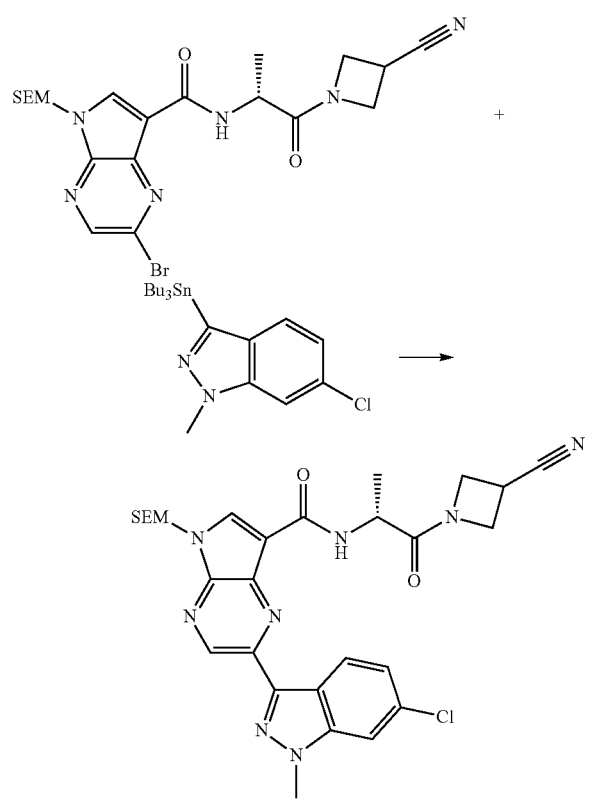

In a round-bottomed flask, 2-bromo-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide (0.135 g, 0.27 mmol) and 6-chloro-1-methyl-3-tributylstannyl-1H-indazole (crude from step 3, 342 mg, 0.38 mmol) were dissolved in DMF (2.4 ml). The flask was evacuated and backfilled with argon then tetrakis(triphenylphosphine)palladium(0) (16 mg, 0.014 mmol) and copper(I) iodide (11 mg, 0.058 mmol) were added. The reaction mixture was stirred at 90° C. in an oil bath for 3 h. The reaction mixture was cooled to room temperature, quenched with water and extracted with diethyl ether (2×). The combined organic layers were washed twice with water and once with brine then dried over sodium sulfate, filtered and concentrated. The residue was absorbed on silica gel and purified by chromatography with MeOH/CH$_2$Cl$_2$/0.5% NH$_4$OH (gradient 0-2.5% MeOH) to afford 157 mg (90%) of 2-(6-chloro-1-methyl-1H-indazol-3-yl)-5-(2-trimethylsilanylethoxymethyl)-5H-pyrrolo[2,3-b]pyrazine-7-carboxylic acid [(R)-2-(3-cyano-azetidin-1-yl)-1-methyl-2-oxo-ethyl]-amide as a light yellow solid.

Step 8

2-(6-Chloro-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide

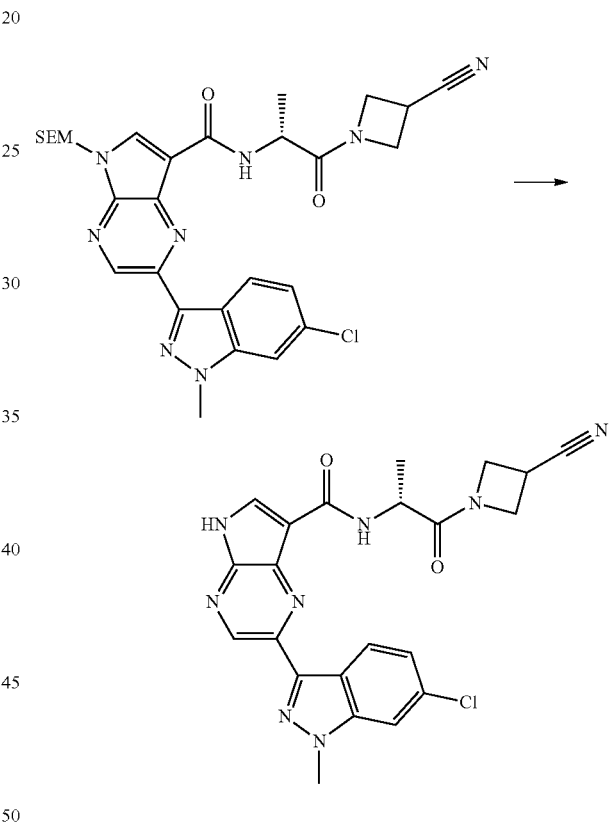

In a round-bottomed flask, 2-(6-chloro-1-methyl-1H-indazol-3-yl)-5-(2-trimethylsilanylethoxymethyl)-5H-pyrrolo[2,3-b]pyrazine-7-carboxylic acid [(R)-2-(3-cyano-azetidin-1-yl)-1-methyl-2-oxo-ethyl]-amide (154 mg, 0.23 mmol) was dissolved in dichloromethane (1.2 ml) and trifluoroacetic acid (0.72 ml, 9.35 mmol) was added. The orange reaction mixture was stirred at room temperature for 2 h then concentrated. The residue was redissolved in dichloromethane (1.2 ml) and ethylenediamine (1.0 ml, 14.8 mmol) was added. The solution was stirred at room temperature for 1.5 h then quenched with water and diluted with ethyl acetate. The resultant suspension was filtered, washing with water (hot), ethyl acetate and dichloromethane then dried under high vacuum to afford 37 mg (33%) of 2-(6-chloro-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide as a white powder. MS: (M+H)$^+$=463; $^1$H NMR (DMSO-d$_6$, 300 MHz): δ

(ppm) 12.70 (br. s., 1H), 9.15 (s, 1H), 8.73 (d, J=8.7 Hz, 1H), 8.47 (t, J=7.4 Hz, 2H), 7.98 (s, 1H), 7.27 (d, J=8.7 Hz, 1H), 4.47-4.84 (m, 3H), 4.18 (s, 3H), 4.02-4.32 (m, 2H), 3.86 (br. s., 1H), 1.42 (d, J=4.5 Hz, 3H).

8.47 (t, J=8.3 Hz, 2H), 8.24 (s, 1H), 4.47-4.79 (m, 3H), 4.18 (s, 3H), 3.97-4.27 (m, 2H), 3.77-3.93 (m, 1H), 1.48 (t, J=6.4 Hz, 3H).

Example 5

2-(5-Chloro-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide

Example 7

2-(1-Methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide

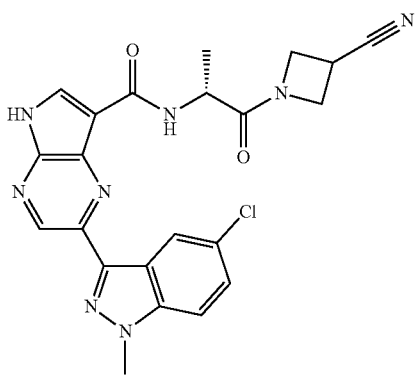 [SMILES: C[C@@H](NC(=O)c1c[nH]c2ncc(-c3nn(C)c4ccc(Cl)cc34)nc12)C(=O)N1CC(C#N)C1]

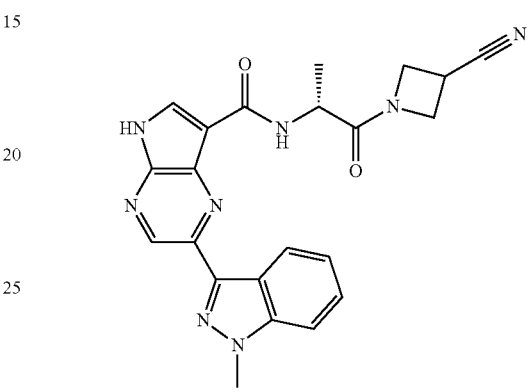

Prepared according to the procedure outlined in Example 4, substituting 5-chloro-1H-indazole for 6-chloro-1H-indazole in step 1. MS: (M+H)$^+$=463; $^1$H NMR (DMSO-d$_6$, 300 MHz): δ (ppm) 11.73 (br. s., 1H), 9.13 (s, 1H), 8.36-8.59 (m, 3H), 7.83 (d, J=9.1 Hz, 1H), 7.52 (d, J=8.7 Hz, 1H), 4.45-4.77 (m, 3H), 4.20 (s, 3H), 3.95-4.34 (m, 2H), 3.74-3.92 (m, 1H), 1.50 (t, J=6.0 Hz, 3H).

Prepared according to the procedure outlined in Example 5, substituting indazole for 6-chloro-1H-indazole in step 1. MS: (M+H)$^+$=429; $^1$H NMR (DMSO-d$_6$, 300 MHz): δ (ppm) 12.80 (br. s., 1H), 9.16 (s, 1H), 8.69 (d, J=7.9 Hz, 1H), 8.51 (d, J=7.9 Hz, 1H), 8.47 (d, J=8.7 Hz, 1H), 7.76 (d, J=8.7 Hz, 1H), 7.52 (t, J=7.6 Hz, 1H), 7.23-7.38 (m, 1H), 4.49-4.80 (m, 3H), 4.14-4.28 (m, 1H), 4.14-4.28 (m, 1H), 4.21 (s, 3H), 4.03-4.13 (m, 1H), 3.75-3.95 (m, 1H), 1.43 (dd, J=6.6, 4.3 Hz, 3H).

Example 6

2-(5,6-Dichloro-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide

Example 8

2-(5-Chloro-1-methyl-1H-indazol-3-yl)-5H-pyrrolo[2,3-b]pyrazine-7-carboxylic acid [(R)-1-(4-cyano-piperidine-1-carbonyl)-2,2-dimethyl-propyl]-amide

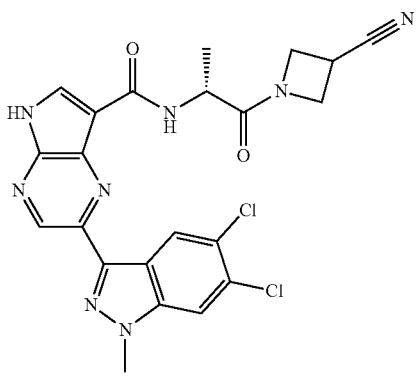

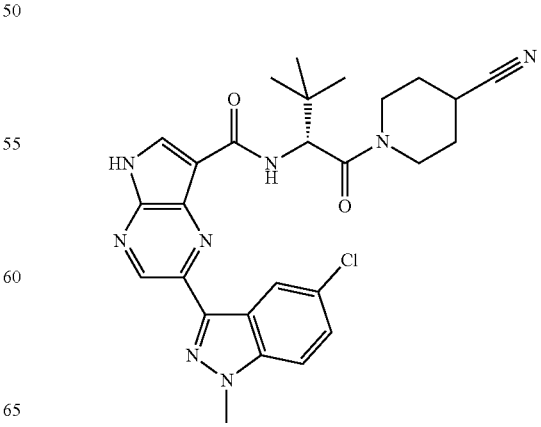

Prepared according to the procedure outlined in Example 5, substituting 5,6-dichloro-1H-indazole for 6-chloro-1H-indazole in step 1. MS: (M+H)$^+$=497; $^1$H NMR (DMSO-d$_6$, 300 MHz): δ (ppm) 12.82 (br. s., 1H), 9.11 (s, 1H), 8.71 (s, 1H), Step 1

[(R)-1-(4-Cyano-piperidine-1-carbonyl)-2,2-dimethyl-propyl]-carbamic acid tert-butyl ester

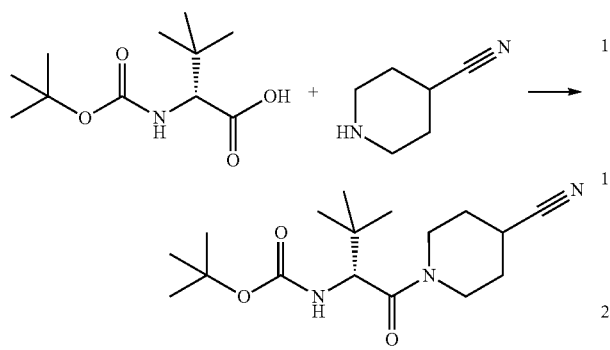

A round-bottomed flask was charged with Boc-D-tert-leucine (2.5 g, 10.8 mmol), HOBT (4.2 g, 24.9 mmol), EDC (4.77 g, 24.9 mmol) and piperidine-4-carbonitrile (2.98 g, 27.0 mmol). Then added DMF (50 mL) followed by N,N-diisopropylethylamine (10.7 ml, 61.6 mmol). The yellow reaction mixture was stirred at room temperature overnight then quenched with 10% citric acid and extracted with EtOAc (2×). The combined organic layers were washed twice with 10% citric acid, twice with sat'd LiCl and once with brine then dried over MgSO₄, filtered and concentrated to give 3.4 g (97%) of [(R)-1-(4-cyano-piperidine-1-carbonyl)-2,2-dimethyl-propyl]-carbamic acid tert-butyl ester as a beige foamy solid.

Step 2

1-((R)-2-Amino-3,3-dimethyl-butyryl)-piperidine-4-carbonitrile trifluoroacetate

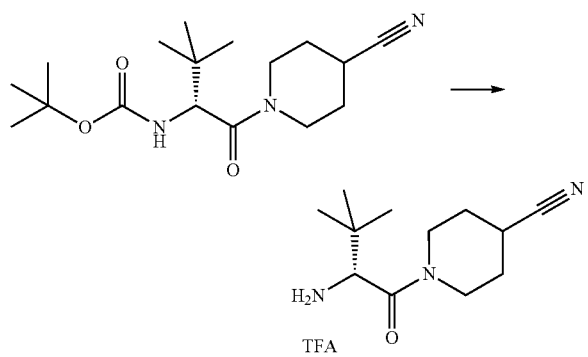

To a solution of [(R)-1-(4-cyano-piperidine-1-carbonyl)-2,2-dimethyl-propyl]-carbamic acid tert-butyl ester (3.4 g, 10.5 mmol) in CH₂Cl₂ (60 mL) was added trifluoroacetic acid (20 mL). The reaction mixture was stirred at room temperature overnight then concentrated to afford 1-((R)-2-amino-3,3-dimethyl-butyryl)-piperidine-4-carbonitrile trifluoroacetate as a light brown oil which was used without further purification.

Step 3

2-Bromo-5-(2-trimethylsilanyl-ethoxymethyl)-5H-pyrrolo[2,3-b]pyrazine-7-carboxylic acid [(R)-1-(4-cyano-piperidine-1-carbonyl)-2,2-dimethyl-propyl]-amide

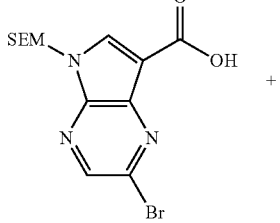

+

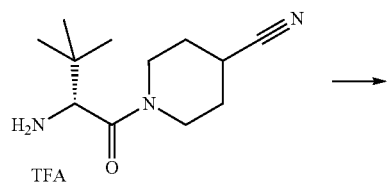

In a flask were combined 2-bromo-5-(2-trimethylsilanylethoxymethyl)-5H-pyrrolo[2,3-b]pyrazine-7-carboxylic acid (1.6 g, 4.3 mmol), 1-((R)-2-amino-3,3-dimethyl-butyryl)-piperidine-4-carbonitrile trifluoroacetate (crude from step 2), EDC (1.89 g, 9.9 mmol) and HOBt (1.67 g, 9.9 mmol). DMF (40 mL) was added followed by i-Pr₂NEt (5.2 mL, 30.1 mmol). The reaction mixture was stirred at room temperature for overnight and then concentrated. The residue was taken up in EtOAc and 10% citric acid and the organic layer washed with 10% citric acid, sat. NaHCO₃, sat LiCl and brine, dried over MgSO₄, and concentrated. The residue was purified by silica gel chromatography (40%-100% EtOAc/hexanes) to give 1.46 g (59%) of 2-bromo-5-(2-trimethylsilanyl-ethoxymethyl)-5H-pyrrolo[2,3-b]pyrazine-7-carboxylic acid [(R)-1-(4-cyano-piperidine-1-carbonyl)-2,2-dimethyl-propyl]-amide as a beige foamy solid.

Step 4

2-(5-Chloro-1-methyl-1H-indazol-3-yl)-5-(2-trimethylsilanyl-ethoxymethyl)-5H-pyrrolo[2,3-b]pyrazine-7-carboxylic acid [(R)-1-(4-cyano-piperidine-1-carbonyl)-2,2-dimethyl-propyl]-amide

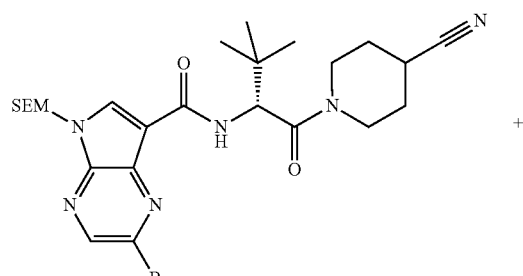

In a round-bottomed flask 2-bromo-5-(2-trimethylsilanyl-ethoxymethyl)-5H-pyrrolo[2,3-b]pyrazine-7-carboxylic acid [(R)-1-(4-cyano-piperidine-1-carbonyl)-2,2-dimethyl-propyl]-amide (150 mg, 0.26 mmol) and 5-chloro-1-methyl-3-tributylstannanyl-1H-indazole (372 mg, 0.45 mmol) were dissolved in DMF (2.4 ml). The flask was evacuated and backfilled with argon then tetrakis(triphenylphosphine)palladium(0) (15 mg, 0.013 mmol) and copper(I) iodide (10 mg, 0.053 mmol) were added. The reaction mixture was stirred at 90° C. in an oil bath for 3.5 h then cooled to room temperature, quenched with water and extracted with diethyl ether (2×). The combined organic layers were washed twice with water and once with brine then dried over sodium sulfate, filtered and concentrated. The residue was purified by chromatography over silica gel with MeOH/CH$_2$Cl$_2$/0.5% NH$_4$OH (gradient 0-2% MeOH) to isolate 137 mg (80%) of 2-(5-chloro-1-methyl-1H-indazol-3-yl)-5-(2-trimethylsilanyl-ethoxymethyl)-5H-pyrrolo[2,3-b]pyrazine-7-carboxylic acid [(R)-1-(4-cyano-piperidine-1-carbonyl)-2,2-dimethyl-propyl]-amide as a yellow oil.

Step 5

2-(5-Chloro-1-methyl-1H-indazol-3-yl)-5H-pyrrolo[2,3-b]pyrazine-7-carboxylic acid [(R)-1-(4-cyano-piperidine-1-carbonyl)-2,2-dimethyl-propyl]-amide

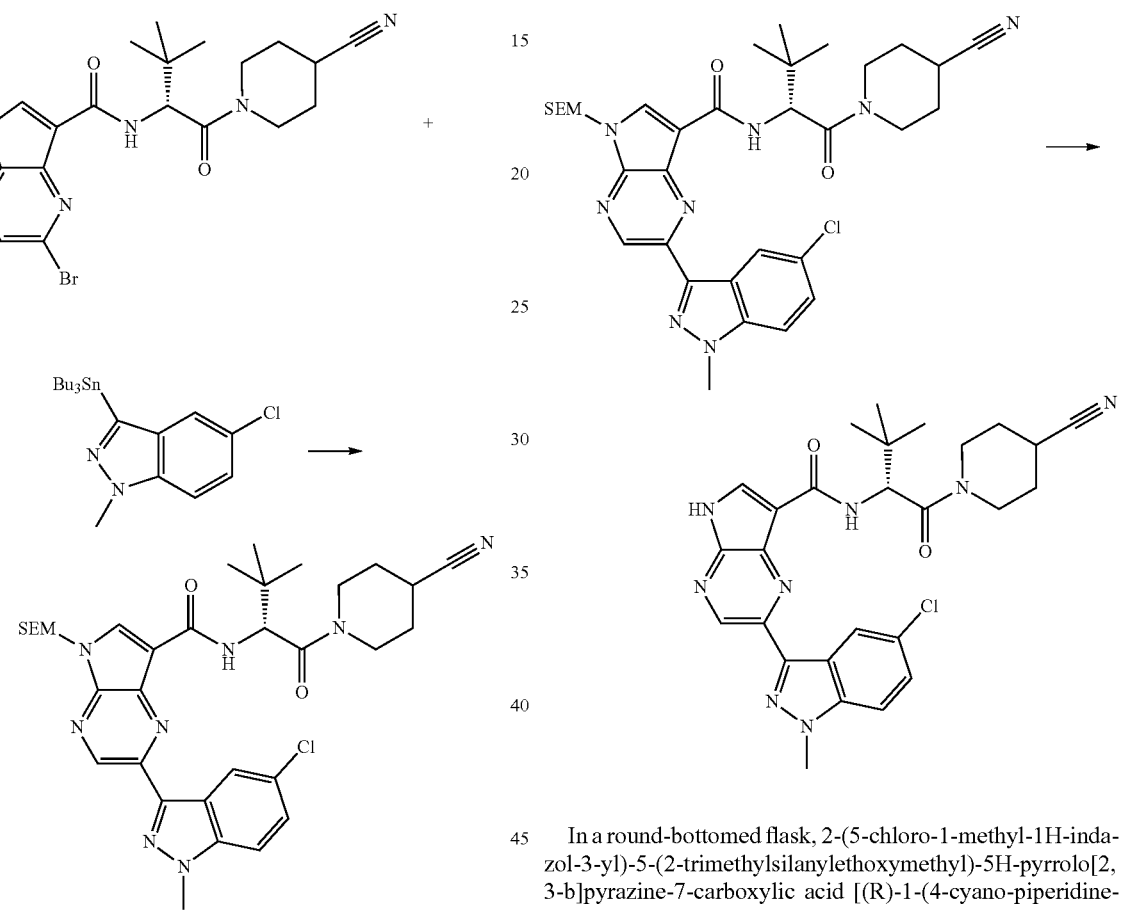

In a round-bottomed flask, 2-(5-chloro-1-methyl-1H-indazol-3-yl)-5-(2-trimethylsilanylethoxymethyl)-5H-pyrrolo[2,3-b]pyrazine-7-carboxylic acid [(R)-1-(4-cyano-piperidine-1-carbonyl)-2,2-dimethyl-propyl]-amide (0.158 g, 0.193 mmol) was dissolved in dichloromethane (1 ml) and trifluoroacetic acid (0.6 ml, 7.8 mmol) was added. The reaction mixture was stirred at room temperature for 2 h then concentrated. The residue was redissolved in dichloromethane (1 ml) and ethylenediamine (0.8 ml, 11.7 mmol) was added. The solution was stirred at room temperature for 1 h then quenched with water and extracted with EtOAc (2×). The combined organic layers were washed with water and brine then dried over sodium sulfate, filtered and concentrated. The residue was purified by chromatography over silica gel with EtOAc/hexanes (gradient 0-100% EtOAc) to afford 26 mg (24%) of 2-(5-chloro-1-methyl-1H-indazol-3-yl)-5H-pyrrolo[2,3-b]pyrazine-7-carboxylic acid [(R)-1-(4-cyano-piperidine-1-carbonyl)-2,2-dimethyl-propyl]-amide as an off-white solid. MS: (M+H)$^+$=533; $^1$H NMR (DMSO-d$_6$, 300 MHz): δ (ppm) 12.92 (br. s., 1H), 9.09 (s, 1H), 8.73 (d, J=6.8 Hz, 1H), 8.61 (t, J=8.1 Hz, 1H), 8.46 (d, J=9.1 Hz, 1H), 7.80 (d, J=9.1 Hz, 1H), 7.50 (d, J=9.1 Hz, 1H), 5.20 (d, J=9.4 Hz, 1H), 4.19 (s, 3H), 3.97-4.12 (m, 1H), 3.35-3.91 (m, 2H), 3.01-3.23 (m, 2H), 1.39-2.07 (m, 4H), 1.04 (d, J=6.4 Hz, 9H).

Example 9

2-(6-Cyclopropyl-1-methyl-1H-indazol-3-yl)-5H-pyrrolo[2,3-b]pyrazine-7-carboxylic acid [(R)-2-(4-cyano-piperidin-1-yl)-1-cyclopropyl-2-oxo-ethyl]-amide

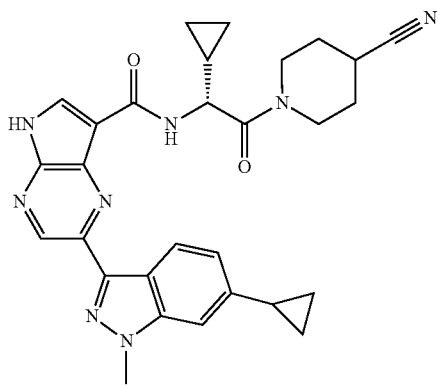 [SMILES: Cn1nc(-c2cnc3[nH]cc(C(=O)N[C@@H](C(=O)N4CCC(C#N)CC4)C4CC4)c3n2)c2ccc(C3CC3)cc21]

Step 1

6-Bromo-1-(2-trimethylsilanyl-ethoxymethyl)-1H-indazole

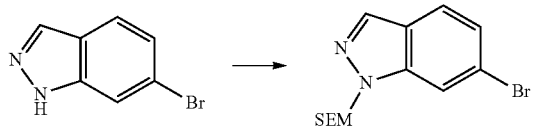 [SMILES: Brc1ccc2cn[nH]c2c1 ; C[Si](C)(C)CCOCn1ncc2ccc(Br)cc21]

In a round-bottomed flask 6-bromo-1H-indazole (0.70 g, 3.55 mmol) was dissolved in DMF (7.5 ml). The reaction mixture was cooled to 0° C. and sodium hydride (60% dispersion in mineral oil, 172 mg, 4.3 mmol) was added). The reaction mixture was warmed to room temperature and stirred for 30 min then cooled back to 0° C. and SEM-Cl (0.76 ml, 4.28 mmol) was slowly added. After the addition was complete, the ice bath was removed and the reaction mixture was warmed to room temperature. After 1.5 h the reaction was quenched with water and extracted with diethyl ether (2×). The combined organic layers were washed twice with water and once with brine then dried over sodium sulfate, filtered and concentrated. The residue was chromatographed over silica gel with EtOAc/Hexanes (gradient 0-10% EtOAc) to give 802 mg (69%) of 6-bromo-1-(2-trimethylsilanyl-ethoxymethyl)-1H-indazole as a light yellow oil.

Step 2

6-Cyclopropyl-1-(2-trimethylsilanyl-ethoxymethyl)-1H-indazole


A round-bottomed flask was charged with 6-bromo-1-(2-trimethylsilanyl-ethoxymethyl)-1H-indazole (0.80 g, 2.44 mmol), cyclopropylboronic acid (377 mg, 4.39 mmol), palladium(II) acetate (28 mg, 0.125 mmol), potassium phosphate tribasic (1.04 g, 4.88 mmol), toluene (9 ml) and water (0.9 ml). The reaction mixture was stirred at 100° C. in an oil bath overnight then cooled to room temperature, quenched with water and extracted with EtOAc (2×). The combined organic layers were washed with water and brine then dried over sodium sulfate, filtered and concentrated. The residue was chromatographed over silica gel with EtOAc/Hexanes (gradient 0-5% EtOAc) to afford 670 mg (90%) of 6-cyclopropyl-1-(2-trimethylsilanyl-ethoxymethyl)-1H-indazole as a light yellow oil.

Step 3

6-Cyclopropyl-1H-indazole

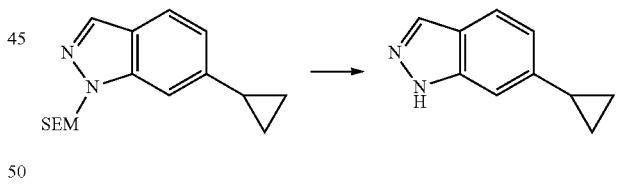

In a round-bottomed flask, 6-cyclopropyl-1-(2-trimethylsilanyl-ethoxymethyl)-1H-indazole (668 mg, 2.2 mmol) was dissolved in dichloromethane (12 ml) and trifluoroacetic acid (6.5 ml, 84.4 mmol) was added. The yellow reaction mixture was stirred at room temperature for 2.25 h then concentrated. The residue was redissolved in dichloromethane (12 ml) and ethylenediamine (9.0 ml, 133 mmol) was added. The solution was stirred at room temperature for 1 h then quenched with water and extracted with EtOAc (2×). The combined organic layers were washed with water and brine then dried over sodium sulfate, filtered and concentrated. The residue was chromatographed over silica gel with EtOAc/Hexanes (gradient 0-25% EtOAc) to provide 317 mg (91%) of 6-cyclopropyl-1H-indazole as a light yellow solid. $^1$H NMR (CDCl$_3$, 300 MHz): δ (ppm) 7.99-8.08 (m, 1H), 7.59-7.70 (m, 1H), 7.16-7.25 (m, 1H), 6.88-7.01 (m, 1H), 1.94-2.14 (m, 1H), 0.96-1.11 (m, 2H), 0.71-0.84 (m, 2H).

Step 4

2-(6-Cyclopropyl-1-methyl-1H-indazol-3-yl)-5H-pyrrolo[2,3-b]pyrazine-7-carboxylic acid [(R)-2-(4-cyano-piperidin-1-yl)-1-cyclopropyl-2-oxo-ethyl]-amide

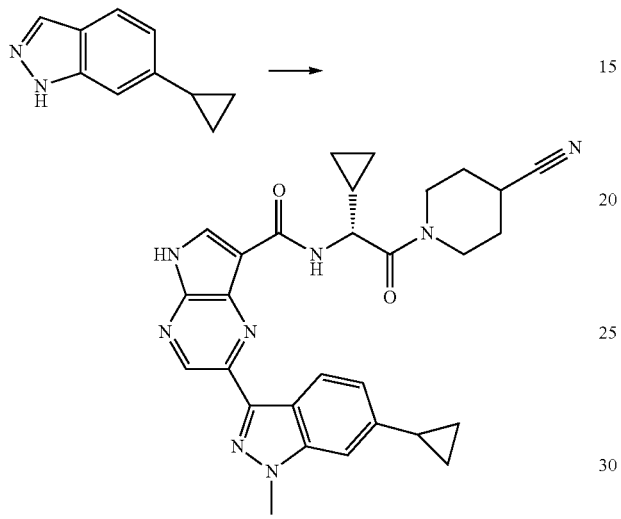

Prepared according to the procedure outlined in Example 1, substituting 6-cyclopropyl-1H-indazole for indazole in step 1. MS: (M+H)$^+$=523; $^1$H NMR (DMSO-d$_6$, 300 MHz): δ (ppm) 12.88 (br. s., 1H), 9.15 (s, 1H), 8.63 (t, J=8.7 Hz, 2H), 8.44 (d, J=9.4 Hz, 1H), 7.37 (s, 1H), 7.04 (br. s., 1H), 4.74-4.95 (m, 1H), 4.14 (s, 3H), 3.35-4.06 (m, 4H), 3.17 (br. s., 1H), 2.13 (br. s., 1H), 1.51-2.05 (m, 4H), 1.35 (br. s., 1H), 1.04 (d, J=6.8 Hz, 2H), 0.83 (d, J=3.4 Hz, 2H), 0.34-0.65 (m, 4H).

Example 10

2-(1-Methyl-4,5,6,7-tetrahydro-1H-indazol-3-yl)-5H-pyrrolo[2,3-b]pyrazine-7-carboxylic acid [(R)-2-(4-cyano-piperidin-1-yl)-1-cyclopropyl-2-oxo-ethyl]-amide

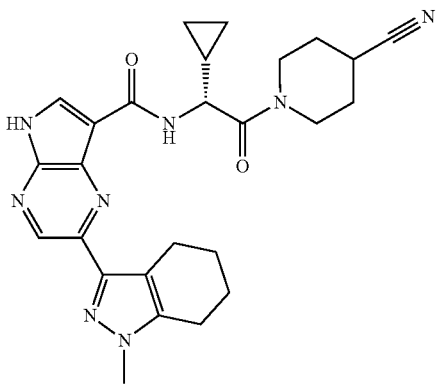 [SMILES: Cn1nc(-c2cnc3[nH]cc(C(=O)N[C@@H](C(=O)N4CCC(C#N)CC4)C4CC4)c3n2)c2c1CCCC2]

Prepared according to the procedure outlined in Example 1, substituting 4,5,6,7-tetrahydro-1H-indazole for indazole in step 1. MS: (M+H)$^+$=487; $^1$H NMR (DMSO-d$_6$, 400 MHz): δ (ppm) 12.76 (s, 1H), 8.93 (s, 1H), 8.58 (d, J=8.1 Hz, 1H), 8.36 (d, J=15.2 Hz, 1H), 4.66 (t, J=8.1 Hz, 1H), 3.78 (s, 3H), 3.34-4.04 (m, 4H), 2.84-3.18 (m, 3H), 2.60-2.70 (m, 2H), 1.44-1.97 (m, 8H), 1.17-1.31 (m, 1H), 0.29-0.66 (m, 4H).

Example 11

2-(5-Chloro-1-methyl-1H-indazol-3-yl)-5H-pyrrolo[2,3-b]pyrazine-7-carboxylic acid ((S)-1,2,2-trimethyl-propyl)-amide

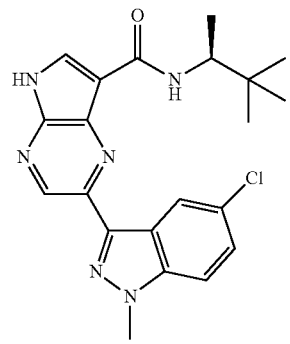 [SMILES: C[C@H](NC(=O)c1c[nH]c2ncc(-c3nn(C)c4ccc(Cl)cc34)nc12)C(C)(C)C]

Step 1

2-Bromo-5-(2-trimethylsilanyl-ethoxymethyl)-5H-pyrrolo[2,3-b]pyrazine-7-carboxylic acid ((S)-1,2,2-trimethyl-propyl)-amide

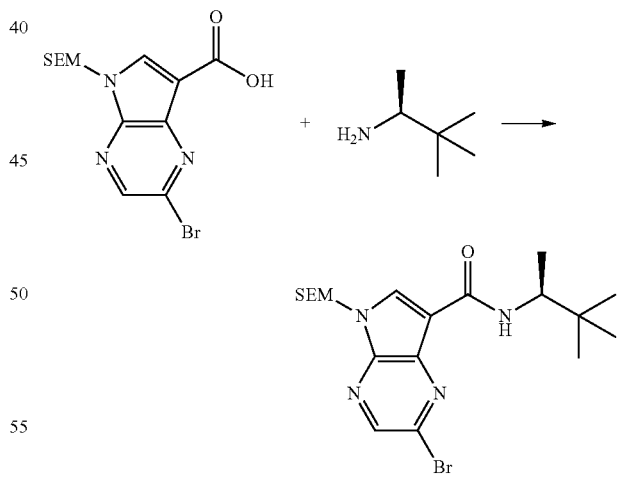

A round-bottomed flask was charged with 2-bromo-5-(2-trimethylsilanylethoxymethyl)-5H-pyrrolo[2,3-b]pyrazine-7-carboxylic acid (150 mg, 0.40 mmol), HOBT (68 mg, 0.44 mmol) and EDC (85 mg, 0.44 mmol). DMF (1.8 ml) was added followed by (S)-3,3-dimethylbutan-2-amine (0.10 ml, 0.73 mmol) and N,N-diisopropylethylamine (0.11 ml, 0.63 mmol). The reaction mixture was stirred at room temperature overnight then quenched with water and extracted with diethyl ether (2×). The combined organic layers were washed twice with water and once with brine then combined, dried over sodium sulfate, filtered and concentrated. The residue was chromatographed over silica gel with EtOAc/hexanes (gradient 0-20% EtOAc) to afford 97 mg (50%) of 2-bromo-5-(2-trimethylsilanyl-ethoxymethyl)-5H-pyrrolo[2,3-b]pyrazine-7-carboxylic acid ((S)-1,2,2-trimethyl-propyl)-amide as a light brown oil.

Step 2

2-(5-Chloro-1-methyl-1H-indazol-3-yl)-5-(2-trimethylsilanyl-ethoxymethyl)-5H-pyrrolo[2,3-b]pyrazine-7-carboxylic acid ((S)-1,2,2-trimethyl-propyl)-amide

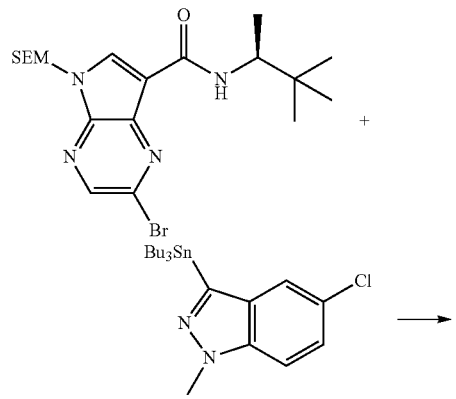

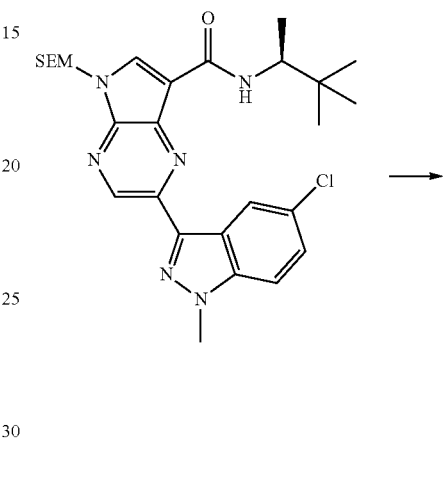

In a round-bottomed flask, 2-bromo-5-(2-trimethylsilanyl-ethoxymethyl)-5H-pyrrolo[2,3-b]pyrazine-7-carboxylic acid ((S)-1,2,2-trimethyl-propyl)-amide (94 mg, 0.21 mmol) and 5-chloro-1-methyl-3-tributylstannyl-1H-indazole (367 mg, 0.40 mmol) were dissolved in DMF (1.9 ml). The flask was evacuated and backfilled with argon then tetrakis(triphenylphosphine)palladium(0) (12 mg, 0.010 mmol) and copper(I) iodide (8 mg, 0.042 mmol) were added. The reaction mixture was stirred at 90° C. in an oil bath for 3.5 h then cooled to room temperature, quenched with water and extracted with diethyl ether (2×). The combined organic layers were washed twice with water and once with brine then dried over sodium sulfate, filtered and concentrated. The residue was chromatographed over silica gel with EtOAc/hexanes (gradient 0-40% EtOAc) to afford 92 mg (82%) of 2-(5-chloro-1-methyl-1H-indazol-3-yl)-5-(2-trimethylsilanyl-ethoxymethyl)-5H-pyrrolo[2,3-b]pyrazine-7-carboxylic acid ((S)-1,2,2-trimethyl-propyl)-amide as an off-white solid.

Step 3

2-(5-Chloro-1-methyl-1H-indazol-3-yl)-5H-pyrrolo[2,3-b]pyrazine-7-carboxylic acid ((S)-1,2,2-trimethyl-propyl)-amide

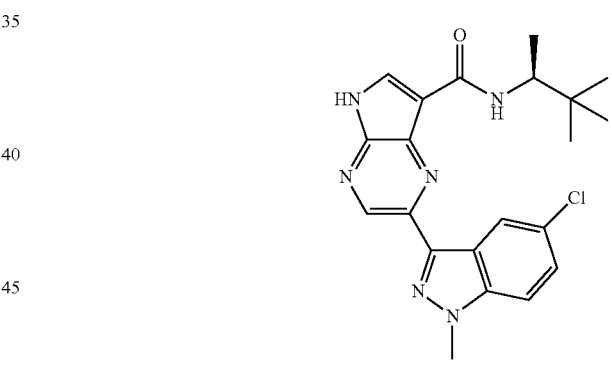

In a round-bottomed flask, 2-(5-chloro-1-methyl-1H-indazol-3-yl)-5-(2-trimethylsilanylethoxymethyl)-5H-pyrrolo[2,3-b]pyrazine-7-carboxylic acid ((S)-1,2,2-trimethyl-propyl)-amide (90 mg, 0.17 mmol) was dissolved in dichloromethane (0.8 ml) and trifluoroacetic acid (0.5 ml, 6.6 mmol) was added. The reaction mixture was stirred at room temperature for 2 h then concentrated. The residue was redissolved in dichloromethane (0.8 ml) and ethylenediamine (0.7 ml, 9.9 mmol) was added. The solution was stirred at room temperature for 1.5 h then quenched with water and diluted with ethyl acetate. The resultant suspension was filtered, rinsed with hot water and ethyl acetate then dried under high vacuum to provide 60 mg (83%) of 2-(5-chloro-1-methyl-1H-indazol-3-yl)-5H-pyrrolo[2,3-b]pyrazine-7-carboxylic acid ((S)-1,2,2-trimethyl-propyl)-amide as a light yellow powder. MS: $(M+H)^+ = 411$; $^1$H NMR (DMSO-$d_6$, 300 MHz): δ (ppm) 12.43 (br. s., 1H), 9.08 (s, 1H), 8.45 (s, 1H), 8.33 (s, 1H), 8.00

(d, J=10.2 Hz, 1H), 7.85 (d, J=8.9 Hz, 1H), 7.55 (dd, J=8.9, 1.5 Hz, 1H), 4.20 (s, 3H), 4.06-4.28 (m, 1H), 1.33 (d, J=6.8 Hz, 3H), 0.92 (s, 9H).

Example 12

2-(6-Chloro-1-methyl-1H-indazol-3-yl)-5H-pyrrolo[2,3-b]pyrazine-7-carboxylic acid ((R)-2-hydroxy-1,2-dimethyl-propyl)-amide

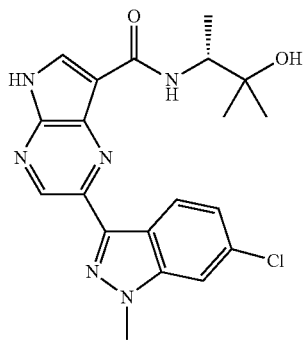 [SMILES: C[C@@H](NC(=O)c1c[nH]c2ncc(-c3nn(C)c4cc(Cl)ccc34)nc12)C(C)(C)O]

Step 1

((R)-2-Hydroxy-1,2-dimethyl-propyl)-carbamic acid tert-butyl ester

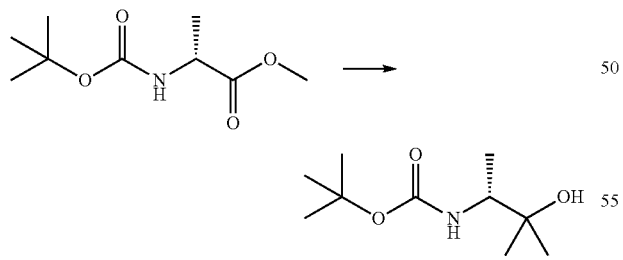

To a solution of Boc-D-alanine methyl ester (5.00 g, 24.6 mmol) in THF (100 mL) at 0° C. was slowly added methyl magnesium bromide (3.0 M in Et₂O, 28.7 mL, 86.1 mmol). The resultant white slurry was stirred at 0° C. for 1 h then at room temperature for 2 h. The reaction mixture was quenched with saturated aqueous NH₄Cl, diluted with H₂O and extracted with EtOAc. The combined organics were washed with brine, dried over MgSO₄ and concentrated to give 4.93 g (99%) ((R)-2-hydroxy-1,2-dimethyl-propyl)-carbamic acid tert-butyl ester as a colorless viscous oil.

Step 2

(R)-3-Amino-2-methyl-butan-2-ol hydrochloride

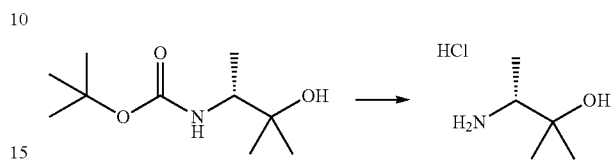

((R)-2-Hydroxy-1,2-dimethyl-propyl)-carbamic acid tert-butyl ester (4.93 g, 24.2 mmol) was dissolved in 1.0 M HCl (150 mL) and stirred at 50° C. for 4 h. Concentration gave 4.01 g of (R)-3-amino-2-methyl-butan-2-ol hydrochloride as a pale brown solid which was used without further purification.

Step 3

2-Bromo-5-(2-trimethylsilanyl-ethoxymethyl)-5H-pyrrolo[2,3-b]pyrazine-7-carboxylic acid ((R)-2-hydroxy-1,2-dimethyl-propyl)-amide

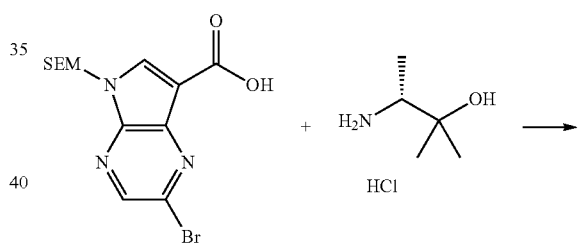

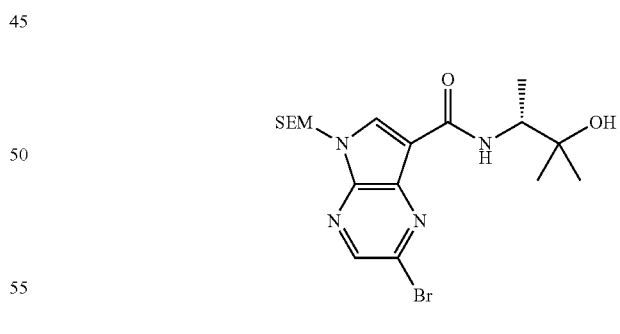

In a flask were combined 2-bromo-5-(2-trimethylsilanylethoxymethyl)-5H-pyrrolo[2,3-b]pyrazine-7-carboxylic acid (3.25 g, 8.74 mmol), (R)-3-amino-2-methyl-butan-2-ol hydrochloride (3.05 g, 21.9 mmol), EDC (3.85 g, 20.1 mmol) and HOBt (2.72 g, 20.1 mmol). Then added DMF (50 mL) followed by i-Pr₂NEt (4.87 mL, 28.0 mmol). The mixture was stirred at room temperature overnight then concentrated under reduced pressure. The residue purified by SiO₂ chromatography (20-100% EtOAc/hexane) to afford 2.40 g (60%) of 2-bromo-5-(2-trimethylsilanyl-ethoxymethyl)-5H-pyrrolo[2,3-b]pyrazine-7-carboxylic acid ((R)-2-hydroxy-1,2-dimethyl-propyl)-amide as a yellow solid.

Step 4

2-(6-Chloro-1-methyl-1H-indazol-3-yl)-5-(2-trimethylsilanyl-ethoxymethyl)-5H-pyrrolo[2,3-b]pyrazine-7-carboxylic acid ((R)-2-hydroxy-1,2-dimethyl-propyl)-amide

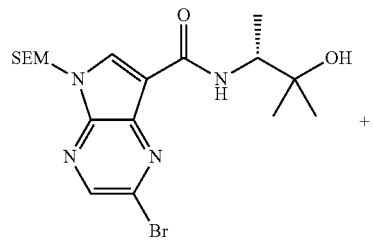

+

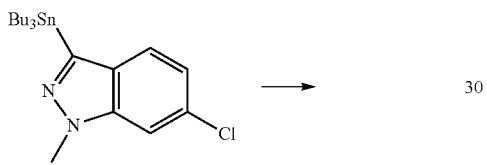

→

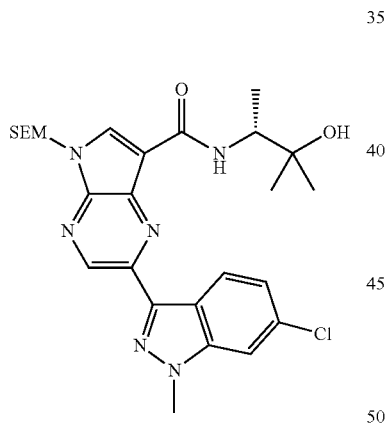

In a round-bottomed flask, 2-bromo-5-(2-trimethylsilanyl-ethoxymethyl)-5H-pyrrolo[2,3-b]pyrazine-7-carboxylic acid ((R)-2-hydroxy-1,2-dimethyl-propyl)-amide (120 mg, 0.26 mmol) and 6-chloro-1-methyl-3-tributylstannyl-1H-indazole (319 mg, 0.42 mmol) were dissolved in DMF (2.5 ml). The flask was evacuated and backfilled with argon then tetrakis(triphenylphosphine)palladium(0) (16 mg, 0.014 mmol) and copper(I) iodide (10 mg, 0.053 mmol) were added. The reaction mixture was stirred at 90° C. in an oil bath overnight then cooled to room temperature, quenched with water and extracted with diethyl ether (2×). The combined organic layers were washed twice with water and once with brine then dried over sodium sulfate, filtered and concentrated. The residue was chromatographed over silica gel with MeOH/CH$_2$Cl$_2$/0.5% NH$_4$OH (gradient 0-2% MeOH) to afford 122 mg (86%) of 2-(6-chloro-1-methyl-1H-indazol-3-yl)-5-(2-trimethylsilanyl-ethoxymethyl)-5H-pyrrolo[2,3-b]pyrazine-7-carboxylic acid ((R)-2-hydroxy-1,2-dimethyl-propyl)-amide as an off-white solid.

Step 5

2-(6-Chloro-1-methyl-1H-indazol-3-yl)-5H-pyrrolo[2,3-b]pyrazine-7-carboxylic acid ((R)-2-hydroxy-1,2-dimethyl-propyl)-amide

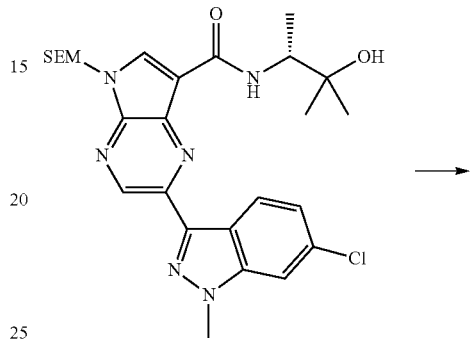

→

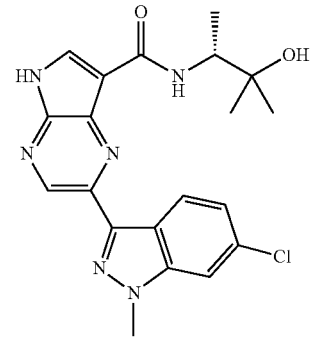

In a round-bottomed flask, 2-(6-chloro-1-methyl-1H-indazol-3-yl)-5-(2-trimethylsilanylethoxymethyl)-5H-pyrrolo[2,3-b]pyrazine-7-carboxylic acid ((R)-2-hydroxy-1,2-dimethyl-propyl)-amide (121 mg, 0.22 mmol) was dissolved in dichloromethane (1 ml) and trifluoroacetic acid (0.7 ml, 9.0 mmol) was added. The reaction mixture was stirred at room temperature for 2.5 h then concentrated. The residue was redissolved in dichloromethane (1 ml) and ethylenediamine (0.9 ml, 13.3 mmol) was added. The solution was stirred at room temperature for 1 h then quenched with water and diluted with ethyl acetate. The resultant suspension was filtered, rinsed with hot water and ethyl acetate then dried under high vacuum to provide 53 mg (58%) of 2-(6-chloro-1-methyl-1H-indazol-3-yl)-5H-pyrrolo[2,3-b]pyrazine-7-carboxylic acid ((R)-2-hydroxy-1,2-dimethyl-propyl)-amide as an off-white powder. MS: (M+H)$^+$=413; $^1$H NMR (DMSO-d$_6$, 300 MHz): δ (ppm) 12.83 (br. s., 1H), 9.14 (s, 1H), 8.75 (d, J=8.7 Hz, 1H), 8.42 (s, 1H), 8.16 (d, J=9.4 Hz, 1H), 7.95 (d, J=1.1 Hz, 1H), 7.36 (dd, J=8.7, 1.1 Hz, 1H), 4.78 (s, 1H), 4.17 (s, 3H), 4.03-4.16 (m, 1H), 1.22-1.28 (m, 6H), 1.16 (s, 3H).

Example 13

2-(1,5,5-Trimethyl-4,5,6,7-tetrahydro-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide

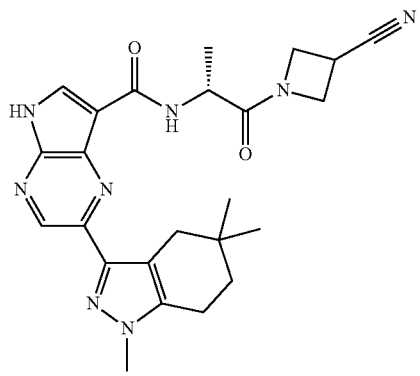 [SMILES: C[C@@H](NC(=O)c1c[nH]c2ncc(-c3nn(C)c4c3CC(C)(C)CC4)nc12)C(=O)N1CC(C#N)C1]

Step 1

2-[1-Hydroxy-meth-(Z)-ylidene]-4,4-dimethyl-cyclohexanone

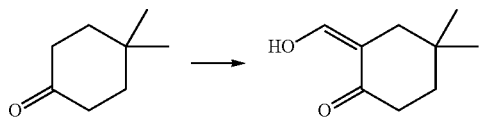

A dry round-bottomed flask was charged with sodium hydride (60% dispersion in mineral oil, 475 mg, 11.9 mmol) and diethyl ether (24 ml). The reaction was cooled to 0° C. and ethanol (0.06 ml, 1.03 mmol) was added dropwise. The suspension was stirred for at 0° C. for 20 min then a solution of 4,4-dimethylcyclohexanone (1.50 g, 11.9 mmol) and ethyl formate (1.45 ml, 17.8 mmol) in diethyl ether (3 ml) was added dropwise over 15 min. The yellow solution was stirred at 0° C. for 3 h then slowly allowed to warm to room temperature overnight. Ethanol (0.24 ml) was added and the mixture was stirred at room temperature for 1 h then quenched with water and extracted with diethyl ether. The aqueous layer was acidified with 6M HCl until pH=2 then extracted with diethyl ether (2×). The combined organic layers were washed with brine then dried over sodium sulfate, filtered and concentrated to give 1.30 g (71%) of 2-[1-hydroxy-meth-(Z)-ylidene]-4,4-dimethyl-cyclohexanone as a pale brown oil which was used without further purification.

$^1$H NMR (CDCl$_3$, 300 MHz): δ (ppm) 14.40 (br. s., 1H), 8.58 (s, 1H), 2.39 (t, J=6.8 Hz, 2H), 2.13 (s, 2H), 1.48 (t, J=6.8 Hz, 2H), 1.00 (s, 6H).

Step 2

5,5-Dimethyl-4,5,6,7-tetrahydro-1H-indazole

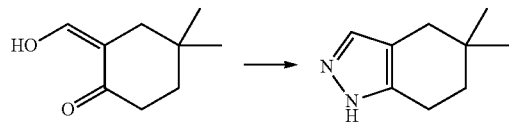

In a 100 ml round-bottomed flask, 2-[1-hydroxy-meth-(Z)-ylidene]-4,4-dimethyl-cyclohexanone (1.30 g, 8.43 mmol) was dissolved in methanol (8.5 ml). Hydrazine (0.27 ml, 8.43 mmol) was added very slowly which resulted in an exothermic reaction. The reaction mixture was stirred at room temperature for 50 min then concentrated. The residue was triturated with petroleum ether to afford 1.05 g (83%) of 5,5-dimethyl-4,5,6,7-tetrahydro-1H-indazole as a light brown solid. $^1$H NMR (CDCl$_3$, 300 MHz): δ (ppm) 7.28 (s, 1H), 2.67 (t, J=6.6 Hz, 2H), 2.32 (s, 2H), 1.60 (t, J=6.6 Hz, 2H), 0.99 (s, 6H).

Step 3

3-Iodo-5,5-dimethyl-4,5,6,7-tetrahydro-1H-indazole

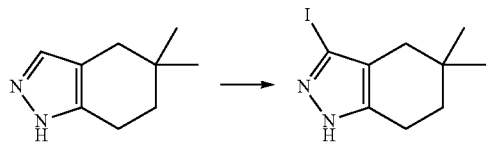

In a round-bottomed flask, 5,5-dimethyl-4,5,6,7-tetrahydro-1H-indazole (0.50 g, 3.33 mmol) was dissolved in DMF (7 mL). Iodine (1.69 g, 6.66 mmol) was added followed by potassium hydroxide (723 mg, 12.9 mmol). The dark reaction mixture was stirred at room temperature for 1.25 h. Additional iodine (1.69 g, 6.66 mmol) and potassium hydroxide (723 mg, 12.9 mmol) were added and the dark brown reaction mixture was stirred at room temperature for 1.5 h. The reaction was quenched with 10% aqueous NaHSO$_3$ solution and extracted with diethyl ether (2×). The combined organic layers were washed twice with water and once with brine then dried over sodium sulfate, filtered and concentrated. The residue was absorbed on silica gel and chromatographed with EtOAc/Hexanes (gradient 0-20% EtOAc) to give 645 mg (70%) of 3-iodo-5,5-dimethyl-4,5,6,7-tetrahydro-1H-indazole as a white solid. $^1$H NMR (CDCl$_3$, 300 MHz): δ (ppm) 2.66 (t, J=6.6 Hz, 2H), 2.14 (s, 2H), 1.59 (t, J=6.4 Hz, 2H), 1.01 (s, 6H).

Step 4

3-Iodo-1,5,5-trimethyl-4,5,6,7-tetrahydro-1H-indazole

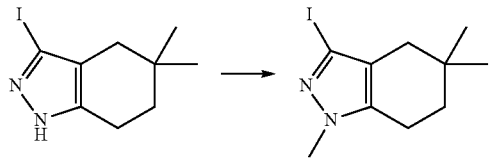

In a round-bottomed flask, 3-iodo-5,5-dimethyl-4,5,6,7-tetrahydro-1H-indazole (642 mg, 2.33 mmol) was dissolved in THF (8.5 ml). The solution was cooled to 0° C. and potassium tert-butoxide (365 mg, 3.26 mmol) was added. The reaction mixture was stirred at 0° C. for 40 min then methyl iodide (0.18 ml, 2.88 mmol) was added dropwise. The reaction mixture was warmed to room temperature and stirred for 1.5 h then quenched with water and extracted with EtOAc (2×). The combined organic layers were washed with water and brine then dried over sodium sulfate, filtered and concentrated. The residue was chromatographed over silica gel with EtOAc/Hexanes (gradient 0-15% EtOAc) to provide 497 mg (74%) of 3-iodo-1,5,5-trimethyl-4,5,6,7-tetrahydro-1H-indazole as a white solid. $^1$H NMR (CDCl$_3$, 300 MHz): δ (ppm) 3.76 (s, 3H), 2.53 (t, J=6.4 Hz, 2H), 2.11 (s, 2H), 1.58 (t, J=6.6 Hz, 2H), 0.99 (s, 6H).

Step 5

1,5,5-Trimethyl-3-tributylstannanyl-4,5,6,7-tetrahydro-1H-indazole

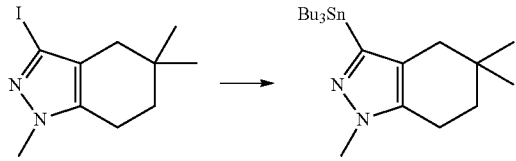

In a round-bottomed flask, 3-iodo-1,5,5-trimethyl-4,5,6,7-tetrahydro-1H-indazole (140 mg, 0.48 mmol) was dissolved in THF (3 ml). The colorless solution was cooled to −16° C. (NaCl/ice bath) and isopropylmagnesium chloride (2.0M in THF, 0.27 ml, 0.54 mmol) was added dropwise. The reaction mixture was stirred at −16° C. for 20 min then tributylchlorostannane (0.15 ml, 0.55 mmol) was slowly added. The reaction mixture was allowed to warm to room temperature over 1.5 h then quenched with saturated NH$_4$Cl, diluted with water and extracted with EtOAc (2×). The combined organic layers were washed with water and brine then dried over sodium sulfate, filtered and concentrated to afford 1,5,5-trimethyl-3-tributylstannanyl-4,5,6,7-tetrahydro-1H-indazole as a colorless oil which was used without further purification.

Step 6

5-(2-Trimethylsilanyl-ethoxymethyl)-2-(1,5,5-trimethyl-4,5,6,7-tetrahydro-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide

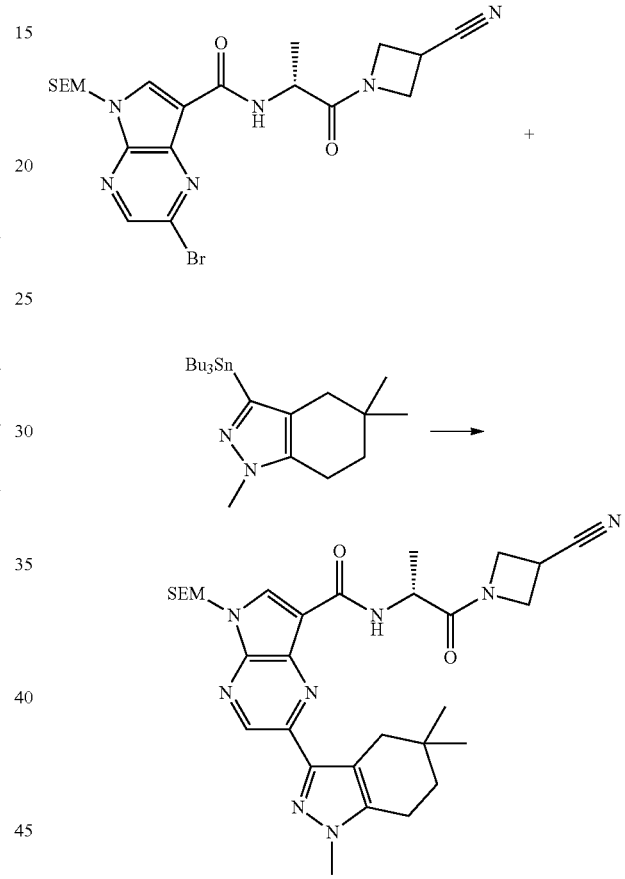

In a round-bottomed flask, 2-bromo-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide (130 mg, 0.26 mmol) and 1,5,5-trimethyl-3-(tributylstannyl)-4,5,6,7-tetrahydro-1H-indazole (375 mg, 0.41 mmol) were dissolved in DMF (2.4 ml). The flask was evacuated and backfilled with argon then tetrakis(triphenylphosphine)palladium(0) (15 mg, 0.013 mmol) and copper(I) iodide (10 mg, 0.053 mmol) were added. The reaction mixture was stirred at 90° C. in an oil bath for 2.5 h then cooled to room temperature, quenched with water and extracted with diethyl ether (2×). The combined organic layers were washed twice with water and once with brine then dried over sodium sulfate, filtered and concentrated. The residue was chromatographed over silica gel with MeOH/CH$_2$Cl$_2$/0.5% NH$_4$OH (gradient 0-5% MeOH) to afford 113 mg (75%) of 5-(2-trimethylsilanyl-ethoxymethyl)-2-(1,5,5-trimethyl-4,5,6,7-tetrahydro-1H-indazol-3-yl)-5H-pyrrolo[2,3-b]pyrazine-7- carboxylic acid [(R)-2-(3-cyano-azetidin-1-yl)-1-methyl-2-oxo-ethyl]-amide as a light yellow foam.

Step 7

2-(1,5,5-Trimethyl-4,5,6,7-tetrahydro-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide

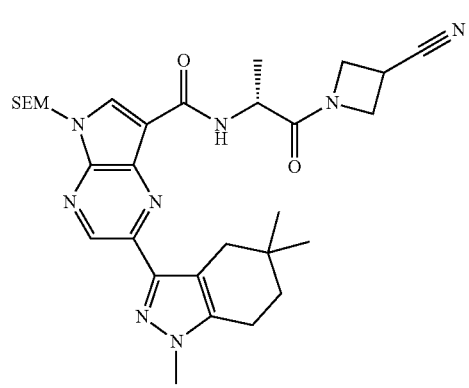

In a round-bottomed flask, 5-(2-trimethylsilanyl-ethoxymethyl)-2-(1,5,5-trimethyl-4,5,6,7-tetrahydro-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide (112 mg, 0.19 mmol) was dissolved in dichloromethane (0.9 ml) and trifluoroacetic acid (0.6 ml, 7.5 mmol) was added. The yellow solution was stirred at room temperature for 2.5 h then concentrated. The residue was redissolved in dichloromethane (0.9 ml) and ethylenediamine (0.8 ml, 11.4 mmol) was added. The reaction mixture was stirred at room temperature for 1 h then quenched with water and diluted with ethyl acetate. The resulting suspension was filtered, washed with hot water and ethyl acetate and dried under high vacuum to provide 47 mg (51%) of 2-(1,5,5-Trimethyl-4,5,6,7-tetrahydro-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide as a white powder. MS: (M+H)$^+$=461; $^1$H NMR (DMSO-d$_6$, 300 MHz): δ (ppm) 12.61 (br. s., 1H), 8.94 (s, 1H), 8.27-8.41 (m, 2H), 4.43-4.80 (m, 3H), 3.94-4.24 (m, 2H), 3.80 (s, 3H), 3.72-3.91 (m, 1H), 2.89 (d, J=15.9 Hz, 1H), 2.59-2.71 (m, 3H), 1.59 (t, J=6.2 Hz, 2H), 1.40 (dd, J=6.8, 3.0 Hz, 3H), 1.00 (s, 6H).

Example 14

2-(6-Chloro-1-methyl-1H-indazol-3-yl)-5H-pyrrolo[2,3-b]pyrazine-7-carboxylic acid [(R)-2-(3,3-difluoro-azetidin-1-yl)-1-methyl-2-oxo-ethyl]-amide

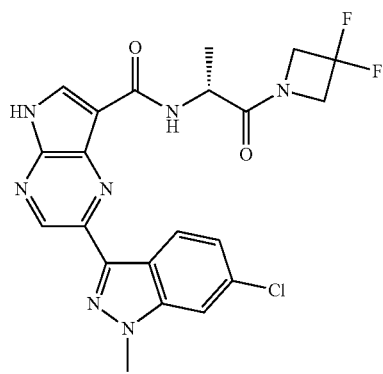 [SMILES: C[C@@H](NC(=O)c1c[nH]c2ncc(-c3nn(C)c4cc(Cl)ccc34)nc12)C(=O)N1CC(F)(F)C1]

Step 1

2-(6-Chloro-1-methyl-1H-indazol-3-yl)-5-(2-trimethylsilanyl-ethoxymethyl)-5H-pyrrolo[2,3-b]pyrazine-7-carbaldehyde

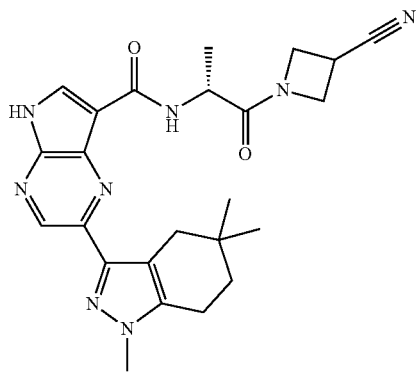

In a round-bottomed flask, 2-bromo-5-(2-trimethylsilanyl-ethoxymethyl)-5H-pyrrolo[2,3-b]pyrazine-7-carbaldehyde (400 mg, 1.12 mmol) and 6-chloro-1-methyl-3-tributylstannyl-1H-indazole (1.11 g, 1.7 mmol) were dissolved in DMF (10 mL). The flask was evacuated and backfilled with argon then tetrakis(triphenylphosphine)palladium(0) (65 mg, 0.056 mmol) and copper(I) iodide (43 mg, 0.23 mmol) were added. The reaction mixture was stirred at 80° C. in an oil bath overnight then cooled to room temperature, quenched with water and extracted with diethyl ether (2×). The combined organic layers were washed twice with water and once with brine then dried over sodium sulfate, filtered and concentrated. The residue was absorbed on silica gel and chromatographed with EtOAc/hexanes (gradient 0-30% EtOAc) to provide 416 mg (84%) of 2-(6-chloro-1-methyl-1H-indazol-3-yl)-5-(2-trimethylsilanyl-ethoxymethyl)-5H-pyrrolo[2,3-b]pyrazine-7-carbaldehyde as a yellow solid.

Step 2

2-(6-Chloro-1-methyl-1H-indazol-3-yl)-5-(2-trimethylsilanyl-ethoxymethyl)-5H-pyrrolo[2,3-b]pyrazine-7-carboxylic acid

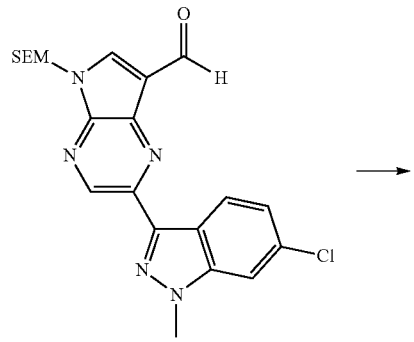

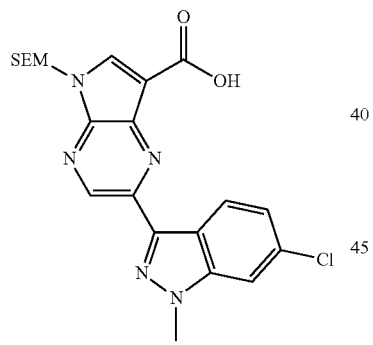

In a round-bottomed flask, 2-(6-chloro-1-methyl-1H-indazol-3-yl)-5-(2-trimethylsilanylethoxymethyl)-5H-pyrrolo[2,3-b]pyrazine-7-carbaldehyde (412 mg, 0.93 mmol) was suspended in 1,4-dioxane (15 ml) and water (3 ml). The suspension was cooled to 0° C. and sulfamic acid (543 mg, 5.59 mmol) was added. Then, a solution of sodium chlorite (80%, 137 mg, 1.21 mmol) and potassium dihydrogen phosphate (1.52 g, 11.2 mmol) in water (9 ml) was added via dropping funnel over ~20 min. After the addition was complete, the ice bath was removed and the reaction mixture was stirred at room temperature for 3 h. THF (15 ml) was added and the reaction mixture was stirred at room temperature for an additional 3 h. The reaction mixture was diluted with water and extracted with EtOAc (2×). The combined organic layers were washed with water and brine then dried over sodium sulfate, filtered and concentrated. The residue was triturated with ethyl acetate/hexanes to afford 358 mg (84%) of 2-(6-chloro-1-methyl-1H-indazol-3-yl)-5-(2-trimethylsilanyl-ethoxymethyl)-5H-pyrrolo[2,3-b]pyrazine-7-carboxylic acid as a light yellow powder.

Step 3

[(R)-2-(3,3-Difluoro-azetidin-1-yl)-1-methyl-2-oxo-ethyl]-carbamic acid tert-butyl ester

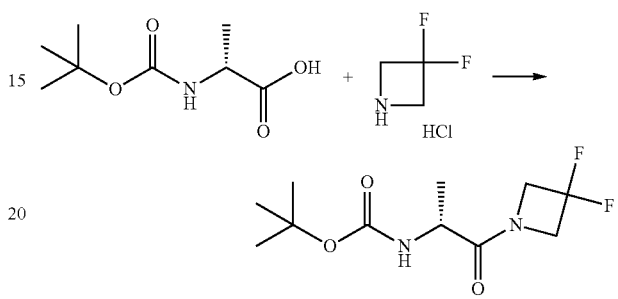

A round-bottomed flask was charged with Boc-D-alanine (400 mg, 2.11 mmol), 3,3-difluoroazetidine hydrochloride (383 mg, 2.96 mmol), HOBT (356 mg, 2.33 mmol) and EDC (446 mg, 2.33 mmol). DMF (9 ml) was added followed by N,N-diisopropylethylamine (1.0 ml, 5.73 mmol). The reaction mixture was stirred at room temperature for 48 h then quenched with water and extracted with diethyl ether (2×). The combined organic layers were washed twice with water and once with brine then dried over sodium sulfate, filtered and concentrated to give 509 mg (91%) of [(R)-2-(3,3-difluoro-azetidin-1-yl)-1-methyl-2-oxo-ethyl]-carbamic acid tert-butyl ester as a light yellow solid. $^1$H NMR (CDCl$_3$, 300 MHz): δ (ppm) 5.14 (d, J=7.2 Hz, 1H), 4.59-4.80 (m, 1H), 4.17-4.55 (m, 4H), 1.45 (s, 9H), 1.32 (d, J=7.2 Hz, 3H).

Step 4

(R)-2-Amino-1-(3,3-difluoro-azetidin-1-yl)-propan-1-one

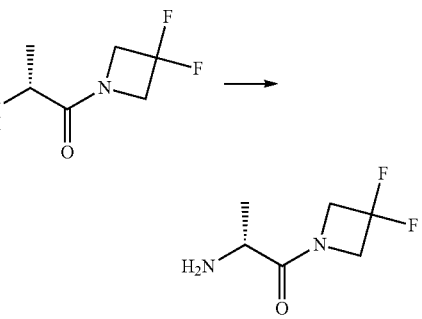

A 5 ml microwave vial was charged with [(R)-2-(3,3-difluoro-azetidin-1-yl)-1-methyl-2-oxo-ethyl]-carbamic acid tert-butyl ester (170 mg, 0.64 mmol) and 2,2,2-trifluoroethanol (2.4 ml, 32.9 mmol). The vial was flushed with argon, sealed and heated at 150° C. under microwave irradiation for 3 h. The reaction mixture was concentrated to afford 102 mg (97%) of (R)-2-amino-1-(3,3-difluoro-azetidin-1-yl)-propan-1-one as a brown oil which was used without further purification.

Step 5

2-(6-Chloro-1-methyl-1H-indazol-3-yl)-5-(2-trimethylsilanyl-ethoxymethyl)-5H-pyrrolo[2,3-b]pyrazine-7-carboxylic acid [(R)-2-(3,3-difluoro-azetidin-1-yl)-1-methyl-2-oxo-ethyl]-amide

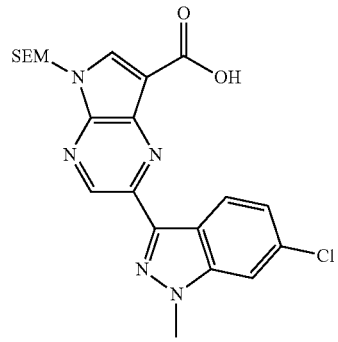

+

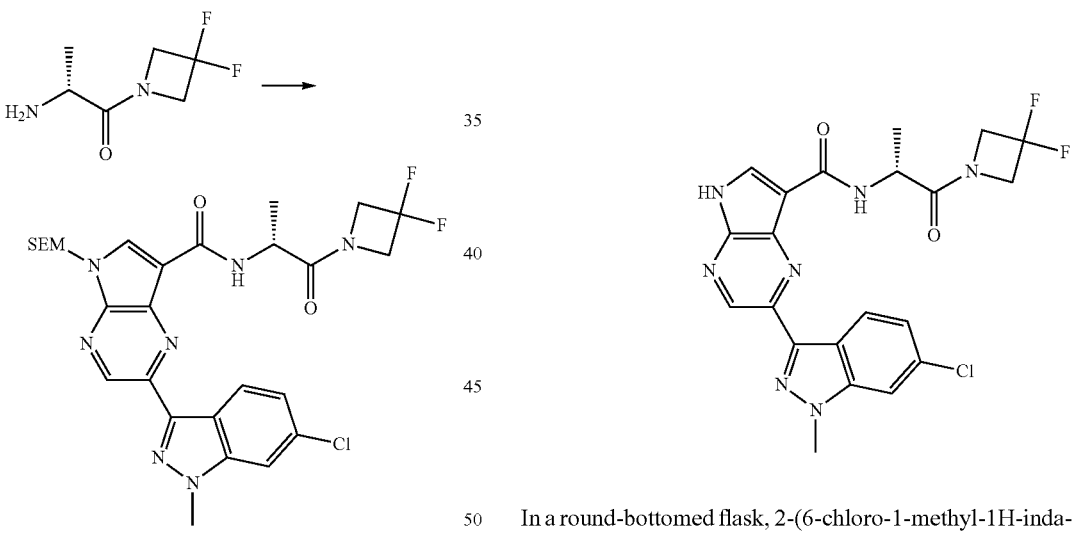

A round-bottomed flask was charged with 2-(6-chloro-1-methyl-1H-indazol-3-yl)-5-(2-trimethylsilanyl-ethoxymethyl)-5H-pyrrolo[2,3-b]pyrazine-7-carboxylic acid (110 mg, 0.24 mmol), (R)-2-amino-1-(3,3-difluoro-azetidin-1-yl)-propan-1-one (98 mg, 0.60 mmol), HOBT (41 mg, 0.27 mmol) and EDC (51 mg, 0.27 mmol). DMF (1.1 ml) was added followed by N,N-diisopropylethylamine (0.10 ml, 0.57 mmol). The reaction mixture was stirred at room temperature for 48 h then quenched with water and extracted with diethyl ether (2×). The combined organic layers were washed twice with water and once with brine then dried over sodium sulfate, filtered and concentrated. The residue was chromatographed over silica gel with EtOAc/Hexanes (gradient 0-50% EtOAc) to afford 89 mg (61%) of 2-(6-chloro-1-methyl-1H-indazol-3-yl)-5-(2-trimethylsilanyl-ethoxymethyl)-5H-pyrrolo[2,3-b]pyrazine-7-carboxylic acid [(R)-2-(3,3-difluoro-azetidin-1-yl)-1-methyl-2-oxo-ethyl]-amide as a light yellow solid.

Step 6

2-(6-Chloro-1-methyl-1H-indazol-3-yl)-5H-pyrrolo[2,3-b]pyrazine-7-carboxylic acid [(R)-2-(3,3-difluoro-azetidin-1-yl)-1-methyl-2-oxo-ethyl]-amide

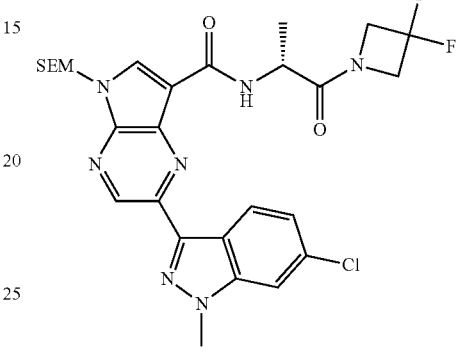

In a round-bottomed flask, 2-(6-chloro-1-methyl-1H-indazol-3-yl)-5-(2-trimethylsilanylethoxymethyl)-5H-pyrrolo[2,3-b]pyrazine-7-carboxylic acid [(R)-2-(3,3-difluoro-azetidin-1-yl)-1-methyl-2-oxo-ethyl]-amide (88 mg, 0.146 mmol) was dissolved in dichloromethane (0.7 ml) and trifluoroacetic acid (0.45 ml, 5.84 mmol) was added. The reaction mixture was stirred at room temperature for 2.5 h then concentrated. The residue was dissolved in dichloromethane (0.7 ml) and ethylenediamine (0.6 ml, 8.74 mmol) was added. The solution was stirred at room temperature for 1 h then quenched with water and diluted with ethyl acetate. The resultant suspension was filtered, washed with hot water and ethyl acetate and dried under high vacuum to provide 45 mg (62%) of 2-(6-chloro-1-methyl-1H-indazol-3-yl)-5H-pyrrolo[2,3-b] pyrazine-7-carboxylic acid [(R)-2-(3,3-difluoro-azetidin-1-yl)-1-methyl-2-oxo-ethyl]-amide as a light yellow powder. MS: (M+H)$^+$=474; $^1$H NMR (DMSO-d$_6$, 300 MHz): δ (ppm) 10.55-11.71 (b. s, 1H), 9.13 (s, 1H), 8.71 (d, J=8.7 Hz, 1H), 8.40-8.54 (m, 2H), 7.97 (d, J=1.5 Hz, 1H), 7.26 (dd, J=8.7, 1.5 Hz, 1H), 4.67-4.99 (m, 3H), 4.38 (t, J=12.7 Hz, 2H), 4.17 (s, 3H), 1.44 (d, J=6.8 Hz, 3H).

Example 15

2-(6-Chloro-1-methyl-1H-indazol-3-yl)-5H-pyrrolo[2,3-b]pyrazine-7-carboxylic acid ((R)-1-methanesulfonyl-piperidin-3-yl)-amide

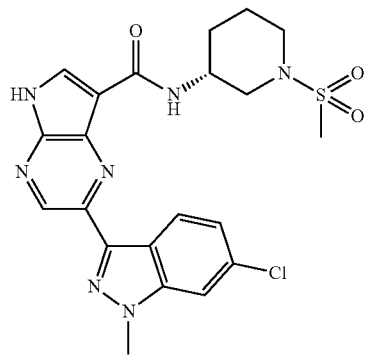 [SMILES: Cn1nc(-c2cnc3[nH]cc(C(=O)N[C@@H]4CCCN(S(C)(=O)=O)C4)c3n2)c2ccc(Cl)cc21]

Step 1

(R)-3-{[2-(6-Chloro-1-methyl-1H-indazol-3-yl)-5-(2-trimethylsilanyl-ethoxymethyl)-5H-pyrrolo[2,3-b]pyrazine-7-carbonyl]-amino}-piperidine-1-carboxylic acid tert-butyl ester

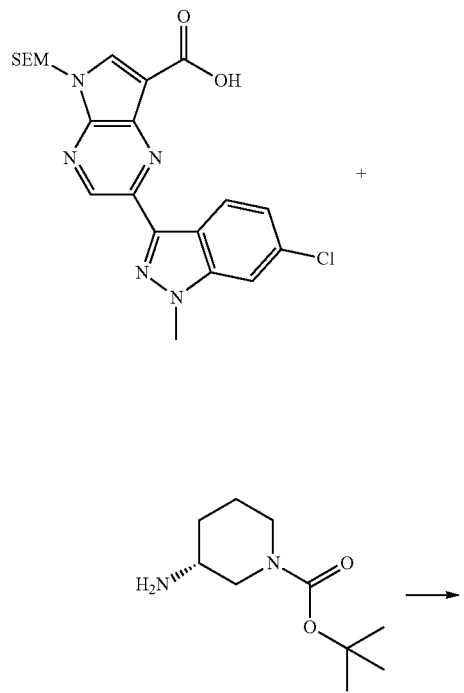

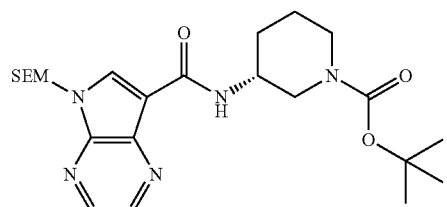

A round-bottomed flask was charged with 2-(6-chloro-1-methyl-1H-indazol-3-yl)-5-(2-trimethylsilanyl-ethoxymethyl)-5H-pyrrolo[2,3-b]pyrazine-7-carboxylic acid (120 mg, 0.26 mmol), (R)-tert-butyl 3-aminopiperidine-1-carboxylate (80 mg, 0.40 mmol), HOBT (45 mg, 0.29 mmol) and EDC (56 mg, 0.29 mmol). DMF (1.2 ml) was added followed by N,N-diisopropylethylamine (0.10 ml, 0.57 mmol). The reaction mixture was stirred at room temperature for 48 h then quenched with water and extracted with diethyl ether (2×). The combined organic layers were washed twice with water and once with brine then dried over sodium sulfate, filtered and concentrated. The residue was chromatographed over silica gel with EtOAc/hexanes (gradient 0-50% EtOAc) to provide 139 mg (83%) of (R)-3-{[2-(6-chloro-1-methyl-1H-indazol-3-yl)-5-(2-trimethylsilanyl-ethoxymethyl)-5H-pyrrolo[2,3-b]pyrazine-7-carbonyl]-amino}-piperidine-1-carboxylic acid tert-butyl ester as a light yellow solid.

Step 2

2-(6-Chloro-1-methyl-1H-indazol-3-yl)-5-(2-trimethylsilanyl-ethoxymethyl)-5H-pyrrolo[2,3-b]pyrazine-7-carboxylic acid (R)-piperidin-3-ylamide

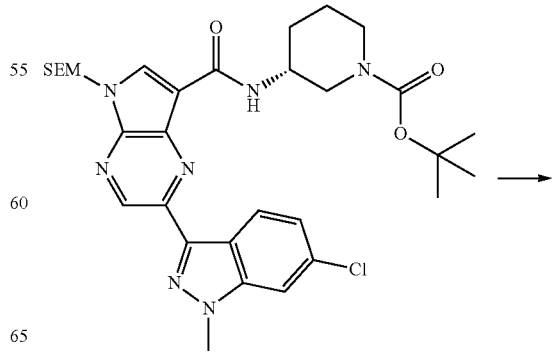

313
-continued

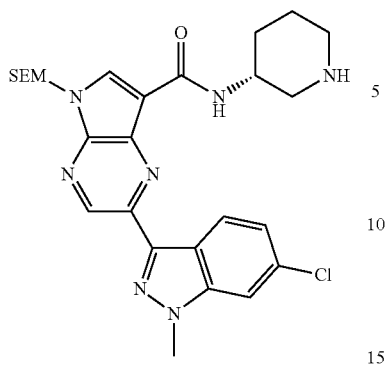

In a round-bottomed flask, (R)-3-{[2-(6-chloro-1-methyl-1H-indazol-3-yl)-5-(2-trimethylsilanyl-ethoxymethyl)-5H-pyrrolo[2,3-b]pyrazine-7-carbonyl]-amino}-piperidine-1-carboxylic acid tert-butyl ester (138 mg, 0.22 mmol) was suspended in methanol (2 ml). The reaction was cooled to 0° C. and acetyl chloride (0.30 ml, 4.22 mmol) was added dropwise over 10 min. The resultant bright yellow suspension was stirred at room temperature for 50 min. THF (1 ml) and methanol (1 ml) were added and stirred was continued for 1 h at room temperature then the solvent was evaporated at room temperature. The residue was suspended in dichloromethane and washed with saturated $Na_2CO_3$-solution. The aqueous layer was extracted with dichloromethane. The organic layers were combined, dried over sodium sulfate, filtered and concentrated to afford 105 mg (90%) of 2-(6-chloro-1-methyl-1H-indazol-3-yl)-5-(2-trimethylsilanyl-ethoxymethyl)-5H-pyrrolo[2,3-b]pyrazine-7-carboxylic acid (R)-piperidin-3-ylamide as a light yellow solid.

Step 3

2-(6-Chloro-1-methyl-1H-indazol-3-yl)-5-(2-trimethylsilanyl-ethoxymethyl)-5H-pyrrolo[2,3-b]pyrazine-7-carboxylic acid ((R)-1-methanesulfonyl-piperidin-3-yl)-amide

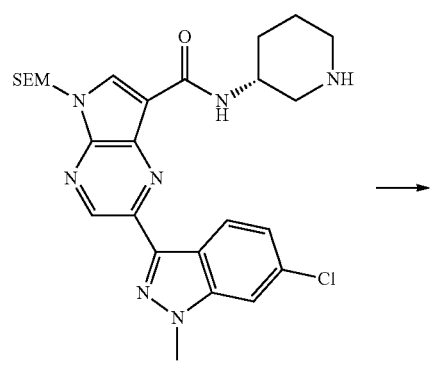

314
-continued

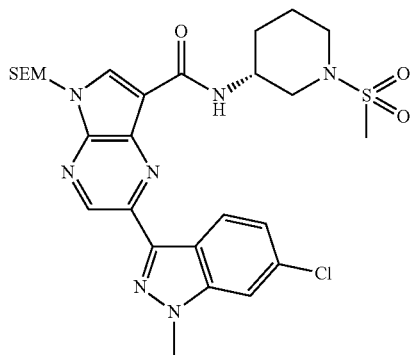

To a solution of 2-(6-chloro-1-methyl-1H-indazol-3-yl)-5-(2-trimethylsilanylethoxymethyl)-5H-pyrrolo[2,3-b]pyrazine-7-carboxylic acid (R)-piperidin-3-ylamide (104 mg, 0.19 mmol) in dichloromethane (1.5 ml) at 0° C. was added triethylamine (0.04 ml, 0.29 mmol) followed by methanesulfonyl chloride (0.02 ml, 0.26 mmol). The reaction mixture was stirred at room temperature overnight then quenched with water and extracted with dichloromethane (2×). The organic layers were combined, dried over sodium sulfate, filtered and concentrated. The residue was chromatographed over silica gel with $MeOH/CH_2Cl_2/0.5\%$ $NH_4OH$ (gradient 0-4% MeOH) then triturated with ethyl acetate to afford 106 mg (89%) of 2-(6-chloro-1-methyl-1H-indazol-3-yl)-5-(2-trimethylsilanyl-ethoxymethyl)-5H-pyrrolo[2,3-b]pyrazine-7-carboxylic acid ((R)-1-methanesulfonyl-piperidin-3-yl)-amide as a light yellow solid.

Step 4

2-(6-Chloro-1-methyl-1H-indazol-3-yl)-5H-pyrrolo[2,3-b]pyrazine-7-carboxylic acid ((R)-1-methanesulfonyl-piperidin-3-yl)-amide

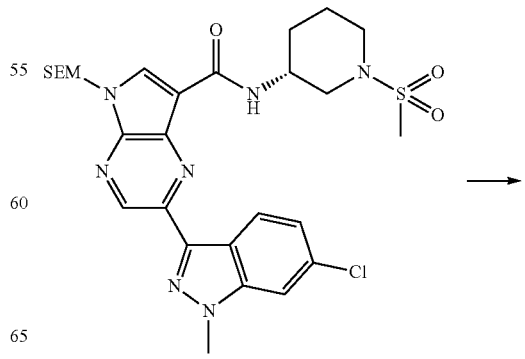

-continued

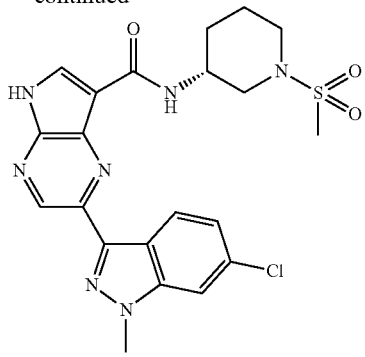

In a round-bottomed flask, 2-(6-chloro-1-methyl-1H-indazol-3-yl)-5-(2-trimethylsilanylethoxymethyl)-5H-pyrrolo[2,3-b]pyrazine-7-carboxylic acid ((R)-1-methanesulfonyl-piperidin-3-yl)-amide (103 mg, 0.167 mmol) was dissolved in dichloromethane (0.8 ml) and trifluoroacetic acid (0.5 ml, 6.6 mmol) was added. The reaction mixture was stirred at room temperature for 2.5 h then concentrated. The residue was dissolved in dichloromethane (0.8 ml) and ethylenediamine (0.67 ml, 9.92 mmol) was added. The resultant light yellow suspension was stirred at room temperature for 45 min then quenched with water and diluted with ethyl acetate. The suspension was filtered, washed with hot water and ethyl acetate and dried under high vacuum to provide 54 mg (63%) of 2-(6-chloro-1-methyl-1H-indazol-3-yl)-5H-pyrrolo[2,3-b]pyrazine-7-carboxylic acid ((R)-1-methanesulfonyl-piperidin-3-yl)-amide as a light yellow powder. MS: (M+H)$^+$=488; $^1$H NMR (DMSO-d$_6$, 300 MHz): δ (ppm) 9.06 (s, 1H), 8.47 (s, 1H), 8.41 (d, J=8.7 Hz, 1H), 8.13 (d, J=7.6 Hz, 1H), 8.00 (s, 1H), 7.36 (d, J=8.7 Hz, 1H), 4.17 (s, 3H), 4.06-4.15 (m, 1H), 3.66-3.75 (m, 1H), 3.34-3.41 (m, 1H), 2.89-2.99 (m, 1H), 2.86 (s, 3H), 2.80 (d, J=10.6 Hz, 1H), 2.11 (br. s., 1H), 1.87 (br. s., 1H), 1.51-1.74 (m, 2H)

Example 16

2-(6-Chloro-1-methyl-1H-indazol-3-yl)-5H-pyrrolo[2,3-b]pyrazine-7-carboxylic acid ((R)-1-cyclopropyl-ethyl)-amide

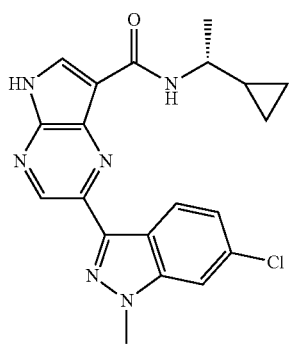 [SMILES: C[C@@H](NC(=O)c1c[nH]c2ncc(-c3nn(C)c4cc(Cl)ccc34)nc12)C1CC1]

Prepared according to the procedure outlined in Example 14, Steps 5-6, substituting (R)-1-cyclopropylethylamine for (R)-2-amino-1-(3,3-difluoro-azetidin-1-yl)-propan-1-one in Step 5.

MS: (M+H)$^+$=395; $^1$H NMR (DMSO-d$_6$,300 MHz): δ (ppm) 10.64 (br. s, 1H), 9.10 (s, 1H), 8.48 (d, J=8.7 Hz, 1H), 8.42 (s, 1H), 8.16 (d, J=8.4 Hz, 1H), 8.01 (s, 1H), 7.28 (dd, J=8.4, 0.9 Hz, 1H), 4.18 (s, 4H), 3.52-3.74 (m, 1H), 1.35 (d, J=6.8 Hz, 3H), 0.95-1.14 (m, 1H), 0.24-0.64 (m, 4H).

Example 17

2-(6-Cyclopropyl-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide

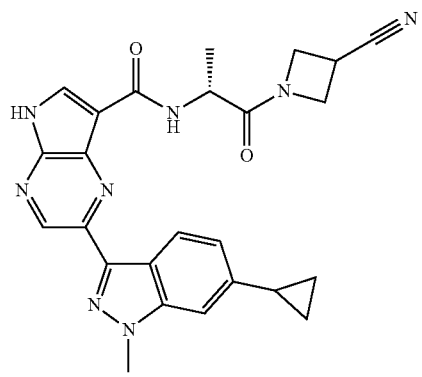 [SMILES: C[C@@H](NC(=O)c1c[nH]c2ncc(-c3nn(C)c4cc(C5CC5)ccc34)nc12)C(=O)N1CC(C#N)C1]

Prepared according to the procedure outlined in Example 4, substituting 6-cyclopropyl-1H-indazole for 6-chloro-1H-indazole in step 1. MS: (M+H)$^+$=469; $^1$H NMR (DMSO-d$_6$, 300 MHz): δ (ppm) 12.88 (br. s., 1H), 9.14 (s, 1H), 8.42-8.59 (m, 3H), 7.40 (s, 1H), 7.06 (dd, J=7.9, 3.8 Hz, 1H), 4.48-4.81 (m, 3H), 4.14 (s, 3H), 4.01-4.29 (m, 2H), 3.77-3.92 (m, 1H), 2.06-2.21 (m, 1H), 1.44 (dd, J=6.2, 4.3 Hz, 3H), 0.95-1.10 (m, 2H), 0.77-0.88 (m, 2H).

Example 18

2-(1-Methyl-6-trifluoromethyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide

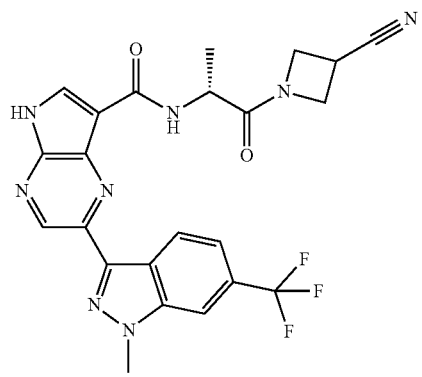 [SMILES: C[C@@H](NC(=O)c1c[nH]c2ncc(-c3nn(C)c4cc(C(F)(F)F)ccc34)nc12)C(=O)N1CC(C#N)C1]

Prepared according to the procedure outlined in Example 4, substituting 6-trifluoromethyl-1H-indazole for 6-chloro-1H-indazole in step 1. MS: (M+H)$^+$=497; $^1$H NMR (DMSO-d$_6$, 300 MHz): δ (ppm) 12.93 (br. s., 1H), 9.16 (s, 1H), 8.93 (d, J=8.3 Hz, 1H), 8.48 (t, J=7.6 Hz, 2H), 8.29 (s, 1H), 7.50 (dd, J=8.1, 4.0 Hz, 1H), 4.49-4.85 (m, 3H), 4.28 (s, 3H), 4.17-4.40 (m, 1H), 4.03-4.17 (m, 1H), 3.78-3.96 (m, 1H), 1.36-1.48 (m, 3H).

Example 19

2-(6-Chloro-1-methyl-1H-indazol-3-yl)-5H-pyrrolo[2,3-b]pyrazine-7-carboxylic acid [(R)-1-(4-cyano-piperidine-1-carbonyl)-2,2-dimethyl-propyl]-amide

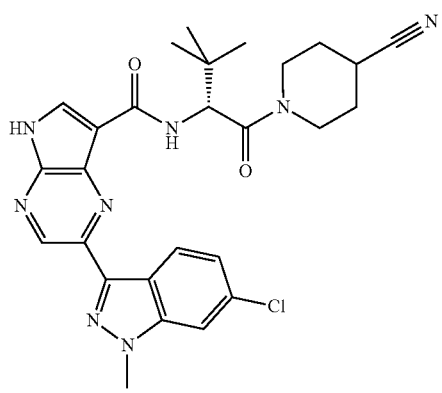 [SMILES: Cn1nc(-c2cnc3[nH]cc(C(=O)N[C@@H](C(=O)N4CCC(C#N)CC4)C(C)(C)C)c3n2)c2ccc(Cl)cc21]

Prepared according to the procedure outlined in Example 14, Steps 5-6, substituting 1-((R)-2-amino-3,3-dimethyl-butyryl)-piperidine-4-carbonitrile trifluoroacetate for (R)-2-amino-1-(3,3-difluoro-azetidin-1-yl)-propan-1-one in Step 5. MS: (M+H)$^+$=533; $^1$H NMR (DMSO-d$_6$, 300 MHz): δ (ppm) 12.94 (br. s., 1H), 9.16 (s, 1H), 9.02 (dd, J=8.5, 6.2 Hz, 1H), 8.60 (dd, J=9.6, 5.5 Hz, 1H), 8.47 (d, J=5.7 Hz, 1H), 7.95 (s, 1H), 7.12-7.28 (m, 1H), 5.30 (d, J=9.8 Hz, 1H), 4.17 (s, 3H), 3.40-4.10 (m, 4H), 3.05-3.26 (m, 1H), 1.44-2.10 (m, 4H), 1.02 (d, J=6.0 Hz, 9H).

Example 20

2-(6-Chloro-1-methyl-1H-indazol-3-yl)-5H-pyrrolo[2,3-b]pyrazine-7-carboxylic acid [(R)-1-(3-cyano-azetidine-1-carbonyl)-propyl]-amide

Step 1

[(R)-1-(3-Cyano-azetidine-1-carbonyl)-propyl]-carbamic acid tert-butyl ester

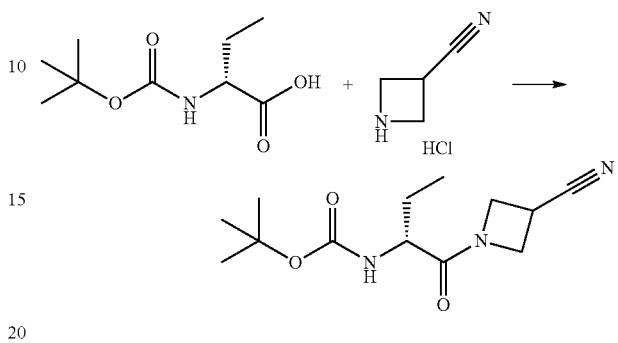

In a round-bottomed flask Boc-D-2-aminobutyric acid (400 mg, 1.97 mmol) and azetidine-3-carbonitrile hydrochloride (373 mg, 3.15 mmol) were dissolved in DMF (9 ml). N,N-Diisopropylethylamine (1.0 ml, 5.73 mmol) was added followed by HATU (823 mg, 2.16 mmol). The reaction mixture was stirred at room temperature for 48 h then quenched with water and extracted with diethyl ether (2×). The combined organic layers were washed twice with water and once with brine then dried over sodium sulfate, filtered and concentrated to provide 410 mg (70%) of [(R)-1-(3-cyano-azetidine-1-carbonyl)-propyl]-carbamic acid tert-butyl ester as an off-white solid.

Step 2

1-((R)-2-Amino-butyryl)-azetidine-3-carbonitrile trifluoroacetate

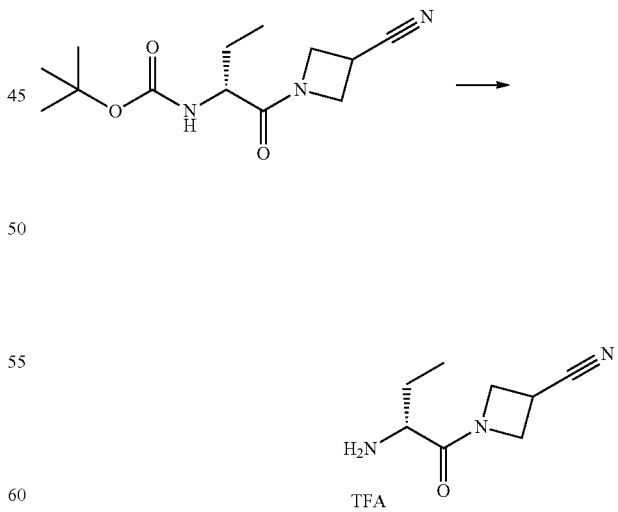

To a solution of [(R)-1-(3-cyano-azetidine-1-carbonyl)-propyl]-carbamic acid tert-butyl ester (200 mg, 0.67 mmol) in dichloromethane (4 ml) was added trifluoroacetic acid (1.8 ml, 23.4 mmol). The reaction mixture was stirred at room temperature for 2 h then concentrated to afford 1-((R)-2- amino-butyryl)-azetidine-3-carbonitrile trifluoroacetate as a light yellow oil which was used without further purification.

Step 3

2-(6-Chloro-1-methyl-1H-indazol-3-yl)-5H-pyrrolo[2,3-b]pyrazine-7-carboxylic acid [(R)-1-(3-cyano-azetidine-1-carbonyl)-propyl]-amide

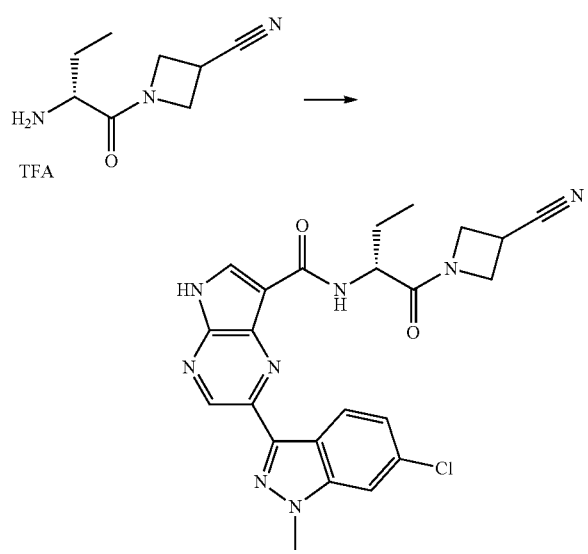

Prepared according to the procedure outlined in Example 14, Steps 5-6, substituting 1-((R)-2-amino-butyryl)-azetidine-3-carbonitrile trifluoroacetate for (R)-2-amino-1-(3,3-difluoro-azetidin-1-yl)-propan-1-one in Step 5. MS: (M+H)+= 477; $^1$H NMR (DMSO-d$_6$, 300 MHz): δ (ppm) 12.73 (s, 1H), 9.15 (s, 1H), 8.73 (d, J=8.7 Hz, 1H), 8.40-8.55 (m, 2H), 7.99 (s, 1H), 7.24 (d, J=8.3 Hz, 1H), 4.48-4.79 (m, 3H), 4.18 (s, 3H), 3.99-4.33 (m, 2H), 3.75-3.96 (m, 1H), 1.62-1.97 (m, 2H), 0.83-1.02 (m, 3H).

Example 21

2-(6-Chloro-1-methyl-1H-indazol-3-yl)-5H-pyrrolo[2,3-b]pyrazine-7-carboxylic acid [(R)-2-(3-cyano-azetidin-1-yl)-1-cyclopropyl-2-oxo-ethyl]-amide

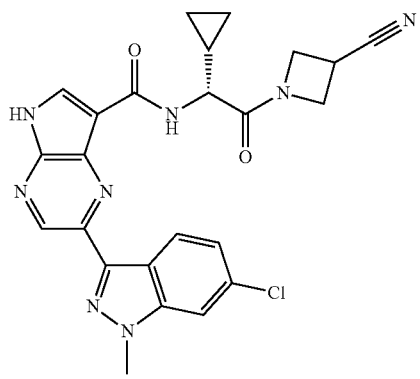 [SMILES: Cn1nc(-c2cnc3[nH]cc(C(=O)N[C@@H](C(=O)N4CC(C#N)C4)C4CC4)c3n2)c2ccc(Cl)cc21]

Step 1

[(R)-2-(3-Cyano-azetidin-1-yl)-1-cyclopropyl-2-oxo-ethyl]-carbamic acid tert-butyl ester

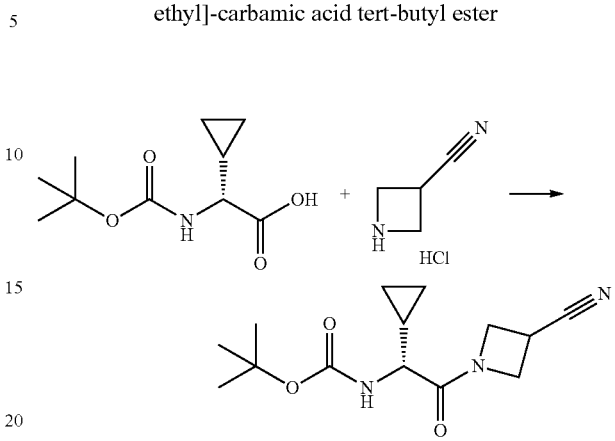

In a round-bottomed flask Boc-D-cyclopropylglycine (500 mg, 2.32 mmol) and azetidine-3-carbonitrile hydrochloride (441 mg, 3.72 mmol) were dissolved in DMF (10 ml). N,N-Diisopropylethylamine (1.2 ml, 6.87 mmol) was added followed by HATU (972 mg, 2.56 mmol). The reaction mixture was stirred at room temperature overnight then quenched with water and extracted with diethyl ether (2×). The combined organic layers were washed twice with water and once with brine then dried over sodium sulfate, filtered and concentrated. The residue was triturated with petroleum ether to afford 384 mg (59%) of [(R)-2-(3-cyano-azetidin-1-yl)-1-cyclopropyl-2-oxo-ethyl]-carbamic acid tert-butyl ester as an off-white solid.

Step 2

1-((R)-2-Amino-2-cyclopropyl-acetyl)-azetidine-3-carbonitrile trifluoroacetate

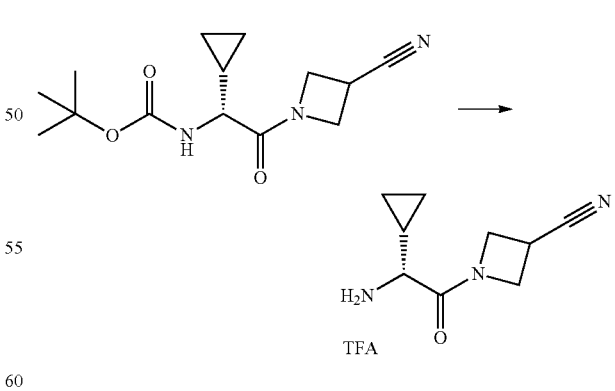

To a solution of [(R)-2-(3-cyano-azetidin-1-yl)-1-cyclopropyl-2-oxo-ethyl]-carbamic acid tert-butyl ester (190 mg, 0.69 mmol) in dichloromethane (4 ml) was added trifluoroacetic acid (1.8 ml, 23.4 mmol). The reaction mixture was stirred at room temperature for 2.5 h then concentrated to afford 1-((R)-2-amino-2-cyclopropyl-acetyl)-azetidine-3- carbonitrile trifluoroacetate as a light yellow oil which was used without further purification.

Step 3

2-(6-Chloro-1-methyl-1H-indazol-3-yl)-5H-pyrrolo[2,3-b]pyrazine-7-carboxylic acid [(R)-2-(3-cyano-azetidin-1-yl)-1-cyclopropyl-2-oxo-ethyl]-amide

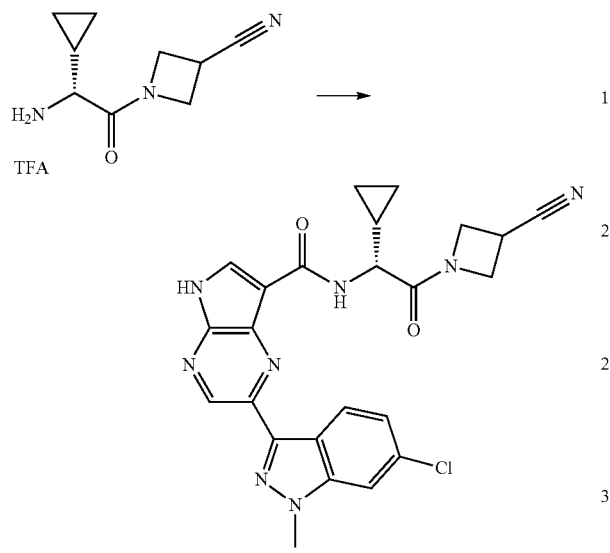

Prepared according to the procedure outlined in Example 14, Steps 5-6, substituting 1-((R)-2-amino-2-cyclopropyl-acetyl)-azetidine-3-carbonitrile trifluoroacetate for (R)-2-amino-1-(3,3-difluoro-azetidin-1-yl)-propan-1-one in Step 5. MS: (M+H)$^+$=489; $^1$H NMR (DMSO-d$_6$, 400 MHz): δ (ppm) 12.92 (br. s., 1H), 9.15 (s, 1H), 8.72 (dd, J=8.6, 3.5 Hz, 1H), 8.43-8.56 (m, 2H), 7.98 (s, 1H), 7.24 (t, J=7.1 Hz, 1H), 4.44-4.76 (m, 2H), 4.17 (s, 3H), 4.01-4.36 (m, 3H), 3.81-3.93 (m, 1H), 1.24-1.38 (m, 1H), 0.36-0.65 (m, 4H).

Example 22

2-(6-Cyano-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide

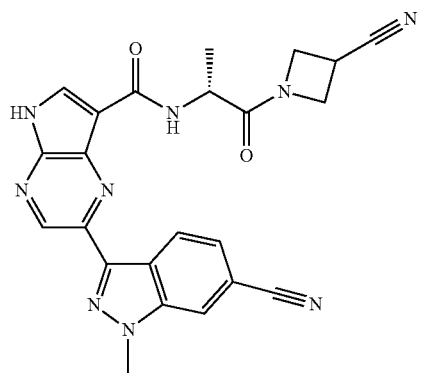 [SMILES: C[C@@H](NC(=O)c1c[nH]c2ncc(-c3nn(C)c4cc(C#N)ccc34)nc12)C(=O)N1CC(C#N)C1]

Prepared according to the procedure outlined in Example 4, substituting 6-cyano-1H-indazole for 6-chloro-1H-indazole in step 1. MS: (M+H)$^+$=454; $^1$H NMR (DMSO-d$_6$, 400 MHz): δ (ppm) 12.93 (br. s., 1H), 9.15 (s, 1H), 8.89 (d, J=8.1 Hz, 1H), 8.39-8.55 (m, 3H), 7.49-7.59 (m, 1H), 4.50-4.83 (m, 3H), 4.25 (s, 3H), 4.20-4.28 (m, 1H), 4.07-4.18 (m, 1H), 3.79-3.93 (m, 1H), 1.41 (t, J=6.8 Hz, 3H).

Example 23

2-(6-Chloro-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide

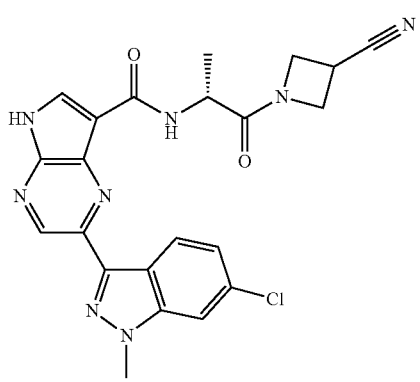 [SMILES: C[C@@H](NC(=O)c1c[nH]c2ncc(-c3nn(C)c4cc(Cl)ccc34)nc12)C(=O)N1CC(C#N)C1]

Step 1

6-Chloro-3-tributylstannanyl-1H-indazole

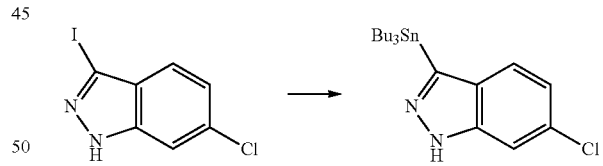

In a round-bottomed flask, 6-chloro-3-iodo-1H-indazole (250 mg, 0.85 mmol) was dissolved in THF (5 ml) and sodium hydride (60% dispersion in mineral oil, 41 mg, 1.03 mmol) was added. The reaction mixture was stirred at room temperature for 10 min then cooled to −16° C. (NaCl/ice bath) and isopropylmagnesium chloride (2.0 M in THF, 0.52 ml, 1.04 mmol) was added dropwise. The reaction mixture was stirred at −16° C. for 30 min then additional isopropylmagnesium chloride (2.0 M in THF (0.14 ml, 0.28 mmol) was added. The reaction mixture was stirred at −16° C. for 10 min then tributylchlorostannane (0.28 ml, 1.03 mmol) was slowly added. The reaction mixture was allowed to warm to room temperature over 2.5 h then quenched with saturated NH$_4$Cl-solution and extracted with EtOAc (2×). The combined organic layers were washed with water and brine then dried over sodium sulfate, filtered, concentrated to give 6-chloro-3-tributylstannanyl-1H-indazole as a yellow oil which was used without further purification.

Step 2

2-(6-Chloro-1H-indazol-3-yl)-5-(2-trimethylsilanylethoxymethyl)-5H-pyrrolo[2,3-b]pyrazine-7-carboxylic acid [(R)-2-(3-cyano-azetidin-1-yl)-1-methyl-2-oxo-ethyl]-amide

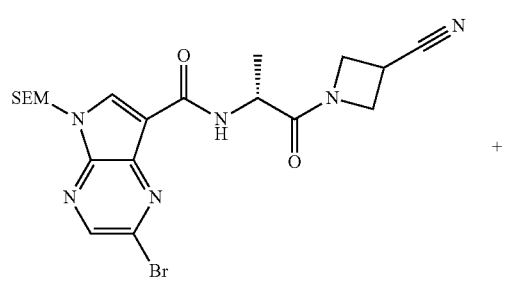

+

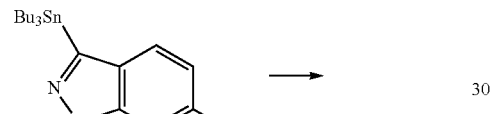

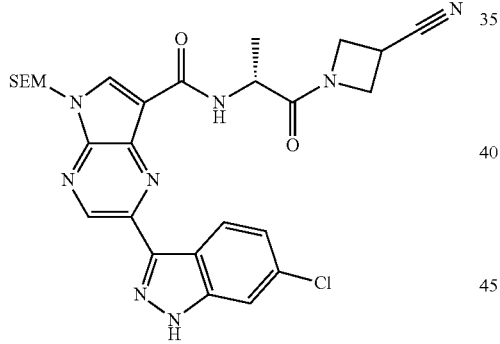

In a round-bottomed flask, 2-bromo-5-(2-trimethylsilanylethoxymethyl)-5H-pyrrolo[2,3-b]pyrazine-7-carboxylic acid [(R)-2-(3-cyano-azetidin-1-yl)-1-methyl-2-oxo-ethyl]-amide (190 mg, 0.37 mmol) and 6-chloro-3-tributylstannyl-1H-indazole (crude form step 1, 619 mg, 0.70 mmol) were dissolved in DMF (3.4 ml). The flask was evacuated and backfilled with argon then tetrakis(triphenylphosphine)palladium(0) (22 mg, 0.019 mmol) and copper(I) iodide (15 mg, 0.079 mmol) were added. The reaction mixture was stirred at 90° C. in an oil bath for 3 h then cooled to room temperature, quenched with water and extracted with diethyl ether (2×). The combined organic layers were washed twice with water and once with brine then concentrated. The residue was absorbed on silica gel and chromatographed with MeOH/CH$_2$Cl$_2$/0.5% NH$_4$OH (gradient 0-3% MeOH) then triturated with diethyl ether/ethyl acetate to afford 159 mg (73%) of 2-(6-chloro-1H-indazol-3-yl)-5-(2-trimethylsilanylethoxymethyl)-5H-pyrrolo[2,3-b]pyrazine-7-carboxylic acid [(R)-2-(3-cyano-azetidin-1-yl)-1-methyl-2-oxo-ethyl]-amide as a light brown powder.

Step 3

2-(6-Chloro-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide

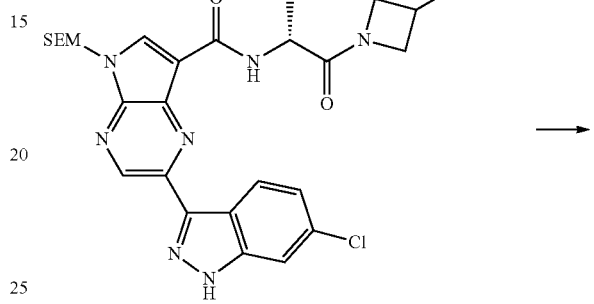

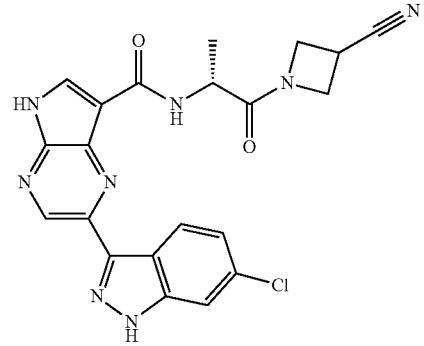

In a round-bottomed flask, 2-(6-chloro-1H-indazol-3-yl)-5-(2-trimethylsilanylethoxymethyl)-5H-pyrrolo[2,3-b]pyrazine-7-carboxylic acid [(R)-2-(3-cyano-azetidin-1-yl)-1-methyl-2-oxo-ethyl]-amide (65 mg, 0.112 mmol) was dissolved in dichloromethane (0.6 ml) and trifluoroacetic acid (0.35 ml, 4.5 mmol) was added. The reaction mixture was stirred at room temperature for 2 h then concentrated. The residue was redissolved in dichloromethane (0.6 ml) and ethylenediamine (0.46 ml, 6.8 mmol) was added. The solution was stirred at room temperature for 1 h then quenched with water and diluted with ethyl acetate. The resultant suspension was filtered, washed with hot water and ethyl acetate and dried under high vacuum to provide 30 mg (59%) of 2-(6-chloro-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide as a light yellow powder. MS: (M+H)$^+$=449.

$^1$H NMR (DMSO-d$_6$, 400 MHz): δ (ppm) 13.35-13.88 (m, 1H), 12.77 (s, 1H), 9.20 (s, 1H), 8.73 (dd, J=8.7, 2.9 Hz, 1H), 8.48 (d, J=8.0 Hz, 2H), 7.74 (d, J=1.5 Hz, 1H), 7.22-7.28 (m, 1H), 4.71-4.78 (m, 1H), 4.64-4.70 (m, 1H), 4.60 (d, J=7.8 Hz, 1H), 4.51-4.57 (m, 1H), 4.23 (td, J=9.5, 3.4 Hz, 1H), 4.06-4.15 (m, 1H), 3.80-3.93 (m, 1H), 1.41 (t, J=6.5 Hz, 3H).

Example 24

2-[6-Chloro-1-(2-methoxy-ethyl)-1H-indazol-3-yl]-5H-pyrrolo[2,3-b]pyrazine-7-carboxylic acid [(R)-2-(3-cyano-azetidin-1-yl)-1-methyl-2-oxo-ethyl]-amide

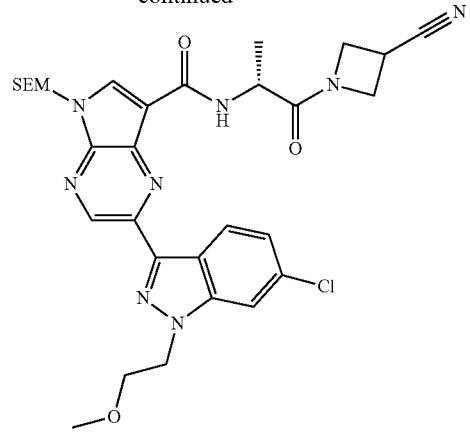

In a round-bottomed flask, 2-(6-chloro-1H-indazol-3-yl)-5-(2-trimethylsilanylethoxymethyl)-5H-pyrrolo[2,3-b]pyrazine-7-carboxylic acid [(R)-2-(3-cyano-azetidin-1-yl)-1-methyl-2-oxo-ethyl]-amide (90 mg, 0.155 mmol) was dissolved in DMF (1 ml). The reaction mixture was cooled to 0° C. and sodium hydride (60% dispersion in mineral oil, 8 mg, 0.20 mmol) was added. The reaction mixture was stirred at 0° C. for 30 min then 1-bromo-2-methoxyethane (22 µl, 0.23 mmol) was added. The reaction mixture was stirred at 0° C. for 3 h and then at room temperature overnight. The reaction mixture was quenched with water and extracted with diethyl ether (2×). The combined organic layers were washed twice with water and once with brine then dried over sodium sulfate, filtered and concentrated. The residue was chromatographed over silica gel with MeOH/CH$_2$Cl$_2$/0.5% NH$_4$OH (gradient 0-3% MeOH) to afford 51 mg (52%) of 2-[6-chloro-1-(2-methoxy-ethyl)-1H-indazol-3-yl]-5-(2-trimethylsilanylethoxymethyl)-5H-pyrrolo[2,3-b]pyrazine-7-carboxylic acid [(R)-2-(3-cyano-azetidin-1-yl)-1-methyl-2-oxo-ethyl]-amide as a yellow foam.

Step 2

2-[6-Chloro-1-(2-methoxy-ethyl)-1H-indazol-3-yl]-5H-pyrrolo[2,3-b]pyrazine-7-carboxylic acid [(R)-2-(3-cyano-azetidin-1-yl)-1-methyl-2-oxo-ethyl]-amide

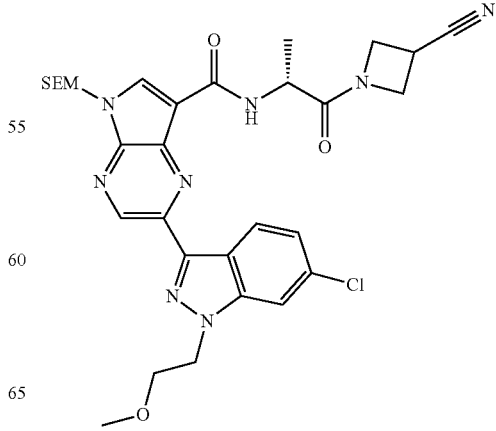

Step 1

2-[6-Chloro-1-(2-methoxy-ethyl)-1H-indazol-3-yl]-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide

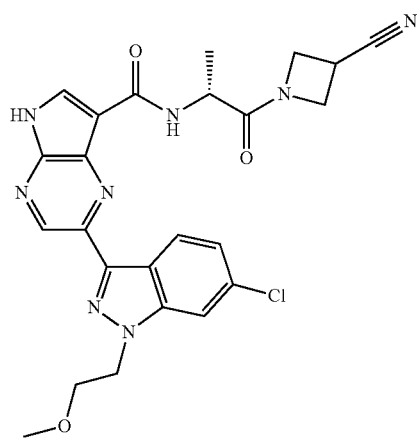 [SMILES: COCCn1nc(-c2cnc3[nH]cc(C(=O)N[C@H](C)C(=O)N4CC(C#N)C4)c3n2)c2ccc(Cl)cc21]

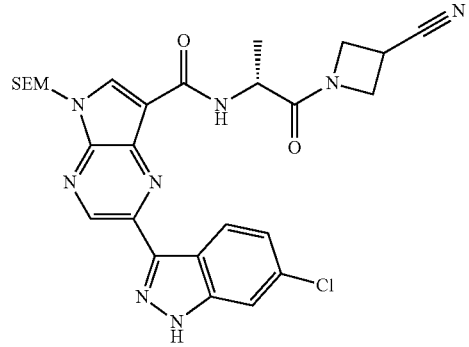

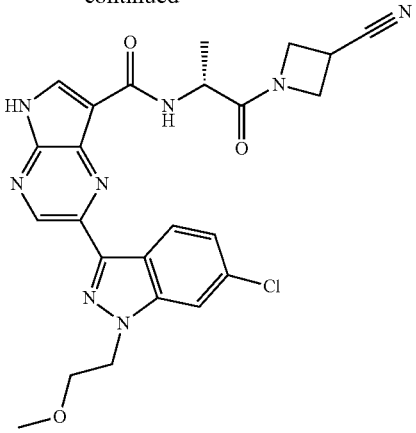

In a round-bottomed flask, 2-[6-chloro-1-(2-methoxy-ethyl)-1H-indazol-3-yl]-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide (50 mg, 0.079 mmol) was dissolved in dichloromethane (0.5 ml) and trifluoroacetic acid (0.25 ml, 3.24 mmol) was added. The reaction mixture was stirred at room temperature for 2 h then concentrated. The residue was dissolved in dichloromethane (0.5 ml) and ethylenediamine (0.32 ml, 4.74 mmol) was added. The reaction was stirred at room temperature for 1.5 h then quenched with water and diluted with ethyl acetate. The resultant suspension was filtered, washed with hot water and ethyl acetate and dried under high vacuum to provide 19 mg (48%) of 2-[6-chloro-1-(2-methoxy-ethyl)-1H-indazol-3-yl]-5H-pyrrolo[2,3-b]pyrazine-7-carboxylic acid [(R)-2-(3-cyano-azetidin-1-yl)-1-methyl-2-oxo-ethyl]-amide as a light yellow powder. MS: (M+H)$^+$=507; $^1$H NMR (DMSO-d$_6$, 400 MHz): δ (ppm) 12.88 (br. s., 1H), 9.16 (s, 1H), 8.72 (dd, J=8.6, 3.0 Hz, 1H), 8.49 (dd, J=8.6, 4.8 Hz, 2H), 8.00 (s, 1H), 7.23-7.30 (m, 1H), 4.52-4.79 (m, 5H), 4.19-4.28 (m, 1H), 4.08-4.16 (m, 1H), 3.85 (t, J=5.3 Hz, 3H), 3.24 (s, 3H), 1.41 (t, J=6.6 Hz, 3H).

Example 25

2-(6-Chloro-1-methyl-1H-indazol-3-yl)-5H-pyrrolo[2,3-b]pyrazine-7-carboxylic acid ((R)-1-phenyl-ethyl)-amide

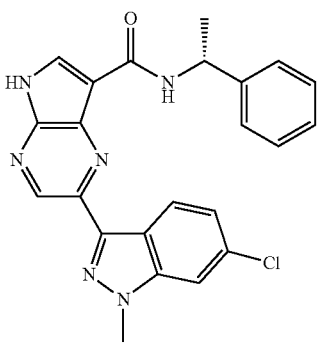 [SMILES: C[C@@H](NC(=O)c1c[nH]c2ncc(-c3nn(C)c4cc(Cl)ccc34)nc12)c1ccccc1]

Prepared according to the procedure outlined in Example 14, Steps 5-6, substituting (R)-1-phenylethylamine for (R)-2-amino-1-(3,3-difluoro-azetidin-1-yl)-propan-1-one in Step 5. MS: (M+H)$^+$=431; $^1$H NMR (DMSO-d$_6$,300 MHz): δ (ppm) 12.73 (br. s., 1H), 9.11 (s, 1H), 8.42-8.53 (m, 2H), 8.28 (d, J=8.7 Hz, 1H), 7.99 (d, J=1.1 Hz, 1H), 7.46 (d, J=7.6 Hz, 2H), 7.34 (t, J=7.4 Hz, 2H), 7.17-7.29 (m, 1H), 7.08 (dd, J=8.7, 1.5 Hz, 1H), 5.34 (quin, J=7.2 Hz, 1H), 4.17 (s, 3H), 1.64 (d, J=7.2 Hz, 3H).

Example 26

2-(1-Methyl-4,5,6,7-tetrahydro-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide

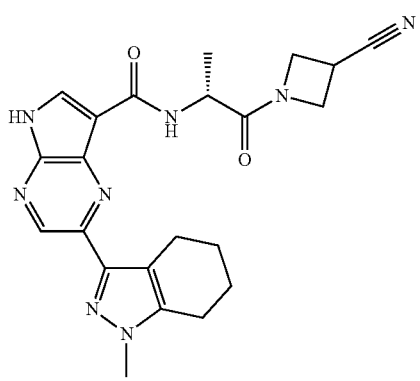 [SMILES: C[C@@H](NC(=O)c1c[nH]c2ncc(-c3nn(C)c4c3CCCC4)nc12)C(=O)N1CC(C#N)C1]

Prepared according to the procedure outlined in Example 4, substituting 4,5,6,7-tetrahydro-1H-indazole for 6-chloro-1H-indazole in step 1. MS: (M+H)$^+$=433; $^1$H NMR (DMSO-d$_6$, 300 MHz): δ (ppm) 12.64 (br. s., 1H), 8.93 (s, 1H), 8.36 (d, J=9.8 Hz, 2H), 4.57-4.73 (m, 2H), 4.43-4.57 (m, 1H), 4.08-4.20 (m, 1H), 3.95-4.06 (m, 1H), 3.79-3.89 (m, 1H), 3.77 (s, 3H), 2.93-3.07 (m, 1H), 2.86 (d, J=18.5 Hz, 1H), 2.58-2.68 (m, 2H), 1.76 (dd, J=13.6, 6.0 Hz, 4H), 1.33 (dd, J=6.8, 3.8 Hz, 3H).

Example 27

2-(6-Chloro-1-methyl-1H-indazol-3-yl)-5H-pyrrolo[2,3-b]pyrazine-7-carboxylic acid [(R)-1-methyl-2-(2-oxa-6-aza-spiro[3.3]hept-6-yl)-2-oxo-ethyl]-amide

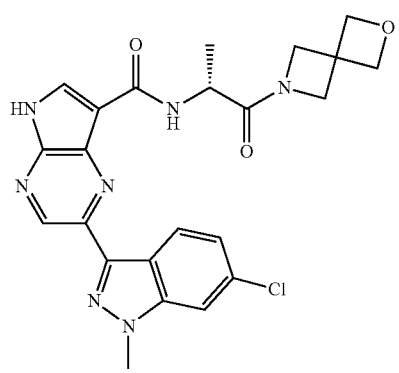 [SMILES: C[C@@H](NC(=O)c1c[nH]c2ncc(-c3nn(C)c4cc(Cl)ccc34)nc12)C(=O)N1CC2(COC2)C1]

Prepared according to the procedure outlined in Example 14, Steps 3-6, substituting 2-oxa-6-aza-spiro[3.3]heptane oxalate for 3,3-difluoroazetidine hydrochloride in Step 3. MS: (M+H)⁺=480; ¹H NMR (DMSO-d₆,300 MHz): δ (ppm) 12.83 (br. s., 1H), 9.14 (s, 1H), 8.78 (d, J=8.7 Hz, 1H), 8.40-8.49 (m, 2H), 7.96 (d, J=1.5 Hz, 1H), 7.24 (dd, J=8.7, 1.5 Hz, 1H), 4.59-4.82 (m, 5H), 4.40-4.56 (m, 2H), 4.16 (s, 3H), 4.11 (s, 2H), 1.37 (d, J=6.8 Hz, 3H).

Example 28

2-(6-Chloro-1-methyl-1H-indazol-3-yl)-5H-pyrrolo[2,3-b]pyrazine-7-carboxylic acid ((R)-1-methyl-2-morpholin-4-yl-2-oxo-ethyl)-amide

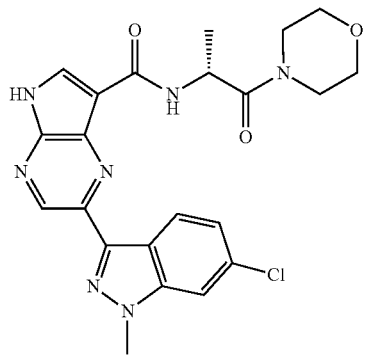 [SMILES: C[C@@H](NC(=O)c1c[nH]c2ncc(-c3nn(C)c4cc(Cl)ccc34)nc12)C(=O)N1CCOCC1]

Prepared according to the procedure outlined in Example 14, Steps 3-6, substituting morpholine for 3,3-difluoroazetidine hydrochloride in Step 3. MS: (M+H)⁺=468; ¹H NMR (DMSO-d₆,300 MHz): δ (ppm) 12.47 (br. s, 1H), 9.16 (s, 1H), 8.88 (d, J=8.7 Hz, 1H), 8.62 (d, J=8.3 Hz, 1H), 8.47 (s, 1H), 7.97 (d, J=1.5 Hz, 1H), 7.26 (dd, J=8.7, 1.5 Hz, 1H), 5.23 (quin, J=7.1 Hz, 1H), 4.18 (s, 3H), 3.47-3.73 (m, 8H), 1.42 (d, J=6.8 Hz, 3H).

Example 29

2-(6-Chloro-1-methyl-1H-indol-3-yl)-5H-pyrrolo[2,3-b]pyrazine-7-carboxylic acid [(R)-2-(3-cyano-azetidin-1-yl)-1-methyl-2-oxo-ethyl]-amide

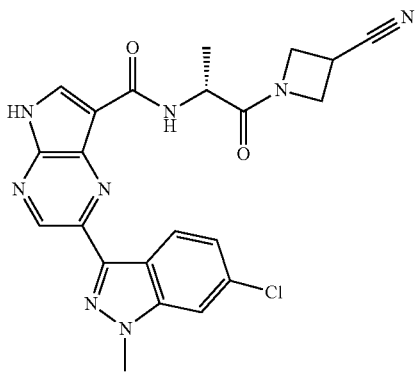 [SMILES: C[C@@H](NC(=O)c1c[nH]c2ncc(-c3nn(C)c4cc(Cl)ccc34)nc12)C(=O)N1CC(C#N)C1]

Step 1

2-(6-Chloro-1H-indol-3-yl)-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide

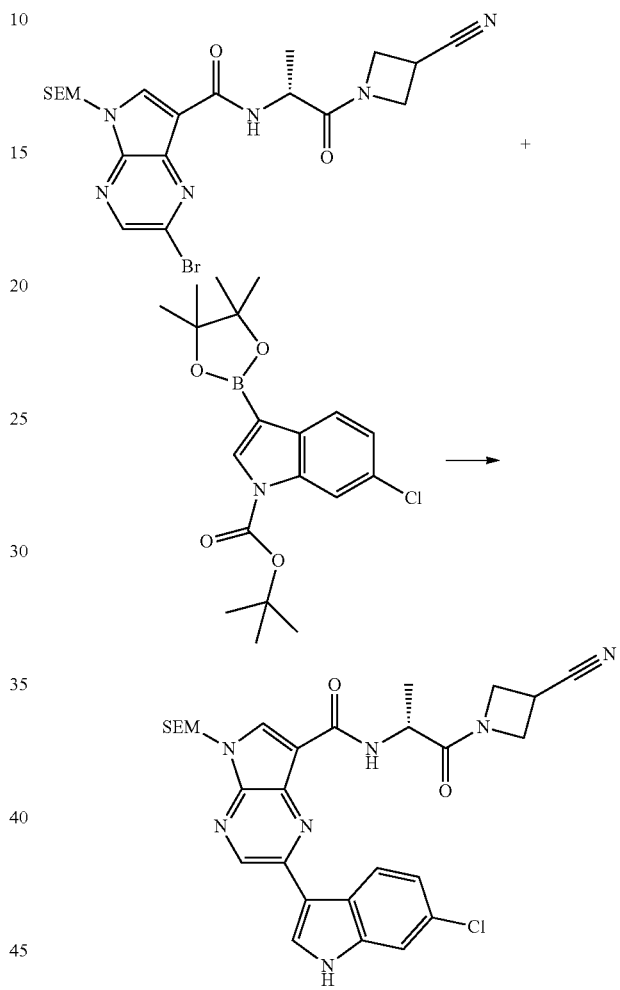

A vial was charged with 2-bromo-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide (158 mg, 0.31 mmol), tert-butyl 6-chloro-3-(4,4,5,5-tetramethyl-1,3,2-dioxaborolan-2-yl)-1H-indole-1-carboxylate (176 mg, 0.47 mmol) and tetrakis(triphenylphosphine)palladium(0) (18.0 mg, 0.016 mmol). The vial was evacuated and backfilled with argon then 1,2-dimethoxyethane (1.8 ml) and aqueous 2 M sodium carbonate (0.47 ml, 0.940 mmol) were added. The vial was sealed and the reaction was stirred at 90° C. in an oil bath overnight. The reaction mixture was cooled to room temperature, quenched with water and extracted with EtOAc (2×). The combined organic layers were washed with water and brine then dried over sodium sulfate, filtered and concentrated. The residue was chromatographed over silica gel with MeOH/CH₂Cl₂/0.5% NH₄OH (gradient 0-3% MeOH) to isolate 93 mg (52%) 2-(6-chloro-1H-indol-3-yl)-5-(2-trimethylsilanyl-ethoxymethyl)-5H-pyrrolo[2,3-b]pyrazine-7-carboxylic acid [(R)-2-(3-cyanoazetidin-1-yl)-1-methyl-2-oxo-ethyl]-amide as a light green foam. A minor amount of impure 6-chloro-3-[7-[(R)-2-(3-cyano-azetidin-1-yl)-1-methyl-2-oxo-ethylcarbamoyl]-5-(2-trimethylsilanyl-ethoxymethyl)-5H-pyrrolo[2,3-b]pyrazin-2-yl]-indole-1-carboxylic acid tert-butyl ester was also insolated as a light brown solid.

Step 2

2-(6-Chloro-1-methyl-1H-indol-3-yl)-5-(2-trimethyl-silanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide

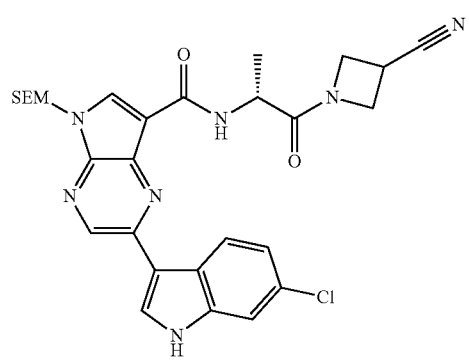

In a round-bottomed flask, 2-(6-chloro-1H-indol-3-yl)-5-(2-trimethylsilanylethoxymethyl)-5H-pyrrolo[2,3-b]pyrazine-7-carboxylic acid [(R)-2-(3-cyano-azetidin-1-yl)-1-methyl-2-oxo-ethyl]-amide (90 mg, 0.156 mmol) was dissolved in DMF (1 ml). The reaction mixture was cooled to 0° C. and sodium hydride (60% dispersion in mineral oil, 8 mg, 0.20 mmol) was added. The reaction mixture was stirred at 0° C. for 30 min then methyl iodide (10 μl, 0.16 mmol) was added. The reaction mixture was stirred at 0° C. for 1.5 h then quenched with water and extracted with diethyl ether (2×). The combined organic layers were washed twice with water and once with brine then dried over sodium sulfate, filtered and concentrated. The residue was chromatographed over silica gel with MeOH/CH$_2$Cl$_2$/0.5% NH$_4$OH (gradient 0-2% MeOH) to afford 56 mg (61%) of 2-(6-chloro-1-methyl-1H-indol-3-yl)-5-(2-trimethylsilanylethoxymethyl)-5H-pyrrolo[2,3-b]pyrazine-7-carboxylic acid [(R)-2-(3-cyano-azetidin-1-yl)-1-methyl-2-oxo-ethyl]-amide as a yellow foam.

Step 3

2-(6-Chloro-1-methyl-1H-indol-3-yl)-5H-pyrrolo[2,3-b]pyrazine-7-carboxylic acid [(R)-2-(3-cyano-azetidin-1-yl)-1-methyl-2-oxo-ethyl]-amide

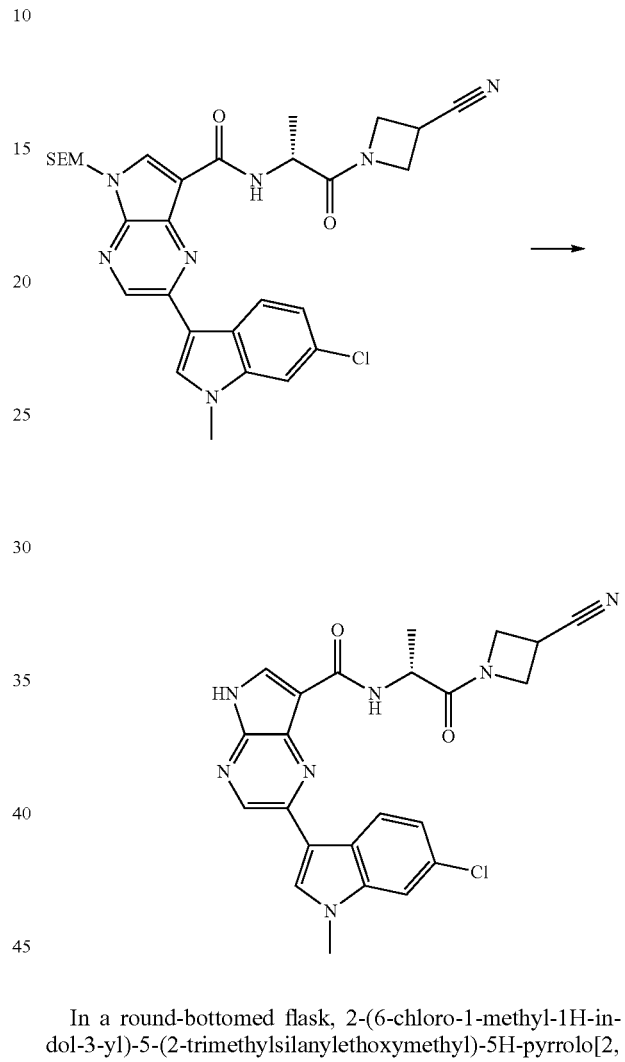

In a round-bottomed flask, 2-(6-chloro-1-methyl-1H-indol-3-yl)-5-(2-trimethylsilanylethoxymethyl)-5H-pyrrolo[2,3-b]pyrazine-7-carboxylic acid [(R)-2-(3-cyano-azetidin-1-yl)-1-methyl-2-oxo-ethyl]-amide (54 mg, 0.091 mmol) was dissolved in dichloromethane (0.5 ml) and trifluoroacetic acid (0.28 ml, 3.63 mmol) was added. The dark red solution was stirred at room temperature for 2 h then concentrated. The residue was redissolved in dichloromethane (0.5 ml) and ethylenediamine (0.37 ml, 5.48 mmol) was added. The reaction mixture was stirred at room temperature for 1 h then quenched with water and diluted with ethyl acetate. The resulting suspension was filtered, washed with hot water and ethyl acetate and dried under high vacuum to provide 28 mg (63%) of 2-(6-chloro-1-methyl-1H-indol-3-yl)-5H-pyrrolo[2,3-b]pyrazine-7-carboxylic acid [(R)-2-(3-cyano-azetidin-1-yl)-1-methyl-2-oxo-ethyl]-amide as a yellow powder.

MS: (M+H)$^+$=462; $^1$H NMR (DMSO-d$_6$, 300 MHz): δ (ppm) 12.62 (br. s., 1H), 8.88 (s, 1H), 8.61 (d, J=7.6 Hz, 1H), 8.55 (d, J=8.7 Hz, 1H), 8.27-8.39 (m, 2H), 7.70 (d, J=1.5 Hz, 1H), 7.17 (dd, J=8.5, 2.5 Hz, 1H), 4.46-4.77 (m, 3H), 4.14-

4.27 (m, 1H), 4.01-4.12 (m, 1H), 3.88 (s, 3H), 3.83 (br. s., 1H), 1.40 (dd, J=6.8, 4.2 Hz, 3H).

Example 30

2-(6-Chloro-5-fluoro-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide

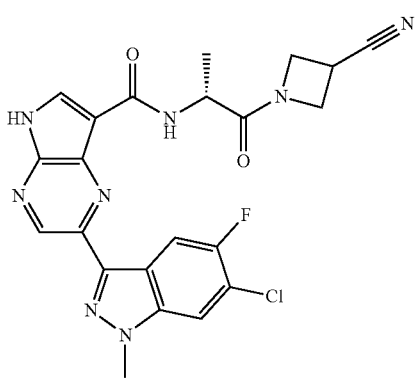 [SMILES: C[C@@H](NC(=O)c1c[nH]c2ncc(-c3nn(C)c4cc(Cl)c(F)cc34)nc12)C(=O)N1CC(C#N)C1]

Prepared according to the procedure outlined in Example 4, substituting 6-chloro-5-fluoro-1H-indazole for 6-chloro-1H-indazole in step 1. MS: (M+H)$^+$=481; $^1$H NMR (DMSO-d$_6$, 300 MHz): δ (ppm) 12.87 (br. s., 1H), 9.13 (s, 1H), 8.49 (d, J=7.9 Hz, 2H), 8.44 (d, J=7.6 Hz, 1H), 8.21 (d, J=6.0 Hz, 1H), 4.48-4.77 (m, 3H), 4.20 (s, 3H), 4.13-4.28 (m, 1H), 4.07 (dt, J=9.7, 5.1 Hz, 1H), 3.79-3.93 (m, 1H), 1.45 (t, J=6.2 Hz, 3H).

Example 31

2-(6-Methyl-imidazo[1,5-a]pyridin-1-yl)-5H-pyrrolo[2,3-b]pyrazine-7-carboxylic acid [(R)-2-(3-cyano-azetidin-1-yl)-1-methyl-2-oxo-ethyl]-amide

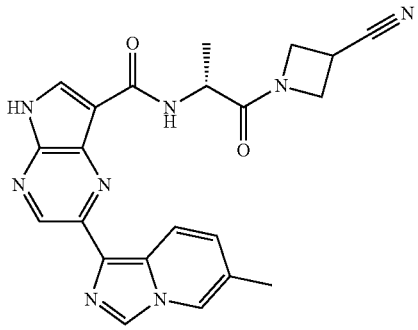 [SMILES: Cc1ccc2c(-c3cnc4[nH]cc(C(=O)N[C@H](C)C(=O)N5CC(C#N)C5)c4n3)ncn2c1]

Step 1

(5-Methyl-pyridin-2-yl)-methylamine

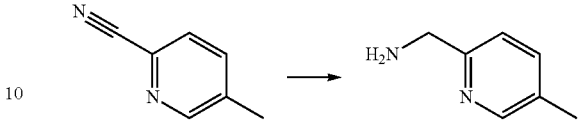

In a dry round-bottomed flask 5-methyl-pyridine-2-carbonitrile (1.0 g, 8.46 mmol) was dissolved in THF (45 ml). The solution was cooled to 0° C. and lithium aluminum hydride (1.0 M in THF, 25 ml, 25.0 mmol) was added dropwise over 20 min. The reaction mixture was stirred at 0° C. for 30 min then sodium sulfate decahydrate was carefully added. When gas evolution had ceased, the ice bath was removed, sodium sulfate was added and the mixture was stirred vigorously for 30 min at room temperature. The suspension was filtered over Celite and rinsed with ethyl acetate, dichloromethane, and methanol. The filtrate was concentrated to afford (5-methyl-pyridin-2-yl)-methylamine as a brown solid which was used without further purification.

Step 2

N-(5-Methyl-pyridin-2-ylmethyl)-formamide

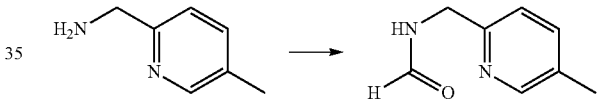

In a round-bottomed flask, (5-methyl-pyridin-2-yl)-methylamine (crude from step 1) was dissolved in 88% formic acid (6.0 ml, 156 mmol). The dark brown solution was stirred at reflux in an oil bath overnight. The reaction mixture was cooled to 0° C. and adjusted carefully to pH=8 by addition of 25% aqueous ammonium hydroxide. The mixture was diluted with water and the aqueous layer was extracted with dichloromethane (3×). The organic layers were combined, dried over sodium sulfate, filtered and concentrated to give N-(5-methyl-pyridin-2-ylmethyl)-formamide as a dark brown oil and used without further purification.

Step 3

6-Methyl-imidazo[1,5-a]pyridine

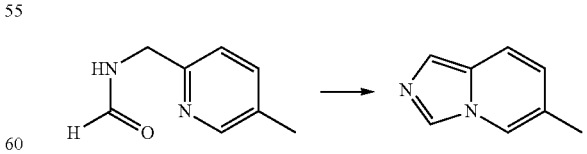

In a round-bottomed flask, N-(5-methyl-pyridin-2-ylmethyl)-formamide (crude from step 2) was dissolved in toluene (30 ml) and phosphorus oxychloride (1.2 ml, 12.9 mmol) was added. The reaction mixture was stirred at 100° C. in an oil bath overnight then cooled to 0° C. and carefully quenched with ice. Aqueous 25% ammonium hydroxide was added until pH=~9. The mixture was diluted with water and extracted with dichloromethane (2×). The organic layers were combined, dried over sodium sulfate, filtered and concentrated. The residue was absorbed on silica gel and chromatographed with EtOAc/hexanes (gradient 0-80% EtOAc) to give 386 mg (41%, 3 steps) of 6-methyl-imidazo[1,5-a]pyridine as a light brown solid. $^1$H NMR (CDCl$_3$, 300 MHz): δ (ppm) 8.09 (s, 1H), 7.74 (s, 1H), 7.32-7.43 (m, 2H), 6.60 (dd, J=9.4, 1.1 Hz, 1H), 2.25 (d, J=1.1 Hz, 3H).

Step 4

1-Iodo-6-methyl-imidazo[1,5-a]pyridine

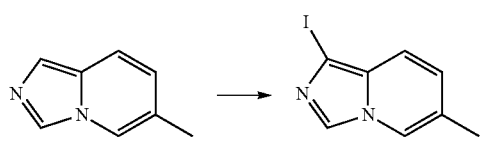

In a round-bottomed flask, sodium bicarbonate (215 mg, 2.56 mmol) was suspended in water (0.6 ml) and ethanol (1.2 ml). 6-methyl-imidazo[1,5-a]pyridine (90 mg, 0.68 mmol) was added followed by iodine (242 mg, 0.95 mmol). The dark brown suspension was stirred at room temperature overnight then quenched with 10% Na$_2$S$_2$O$_3$-solution and extracted with EtOAc (2×). The organic layers were washed with water and brine then dried over sodium sulfate, filtered and concentrated. The residue was chromatographed over silica gel with EtOAc/hexanes (gradient 0-30% EtOAc) to provide 99 mg (56%) of 1-iodo-6-methyl-imidazo[1,5-a]pyridine as a light brown solid. $^1$H NMR (CDCl$_3$, 300 MHz): δ (ppm) 8.11 (s, 1H), 7.73 (s, 1H), 7.24 (d, J=9.4 Hz, 1H), 6.67 (d, J=9.1 Hz, 1H), 2.27 (s, 3H).

Step 5

6-Methyl-1-tributylstannanyl-imidazo[1,5-a]pyridine

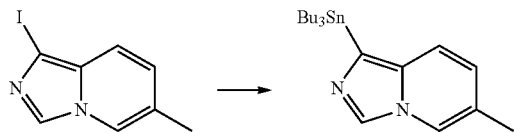

In a round-bottomed flask, 1-iodo-6-methyl-imidazo[1,5-a]pyridine (97 mg, 0.38 mmol) was dissolved in THF (3 ml). The solution was cooled to −16° C. (NaCl/ice bath) and isopropylmagnesium chloride (2.0M solution in THF, 0.23 ml, 0.46 mmol) was added dropwise. The reaction mixture was stirred at −16° C. for 20 min then tributylchlorostannane (0.12 ml, 0.44 mmol) was slowly added. The reaction mixture was allowed to warm to room temperature and stirred for 2 h then quenched with saturated aqueous NH$_4$Cl and extracted with EtOAc (2×). The combined organic layers were washed with water and brine then dried over sodium sulfate, filtered and concentrated to provide 6-methyl-1-tributylstannanyl-imidazo[1,5-a]pyridine as a brown oil which was used without further purification.

Step 6

2-(6-Methyl-imidazo[1,5-a]pyridin-1-yl)-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide

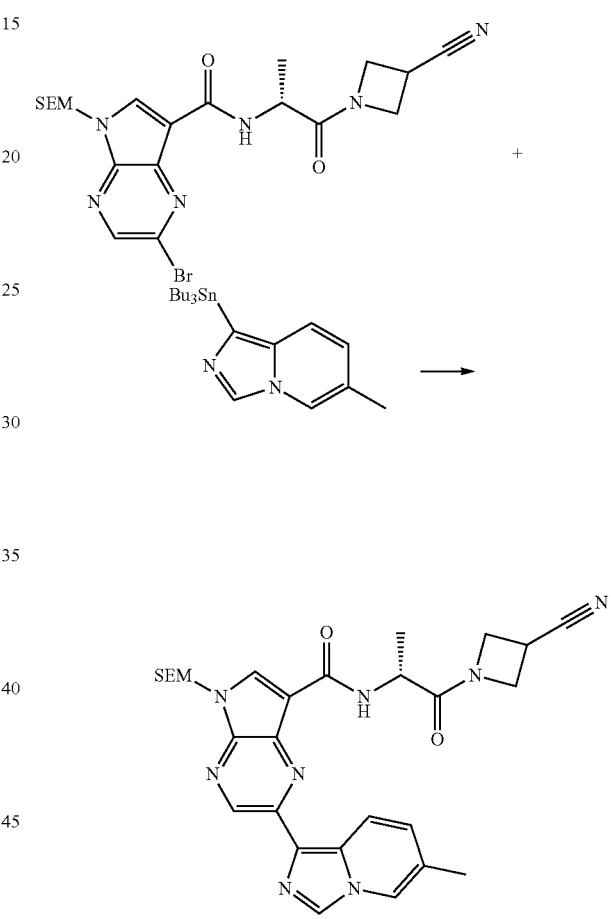

In a round-bottomed flask, 2-bromo-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide (100 mg, 0.20 mmol) and 6-methyl-1-tributylstannanyl-imidazo[1,5-a]pyridine (crude from step 5, 307 mg, 0.36 mmol) were dissolved in DMF (1.8 ml). The flask was evacuated and backfilled with argon then tetrakis(triphenylphosphine)palladium (0) (12 mg, 0.010 mmol) and copper (I) iodide (8 mg, 0.042 mmol) were added. The reaction mixture was stirred at 90° C. in an oil bath overnight then cooled to room temperature, quenched with water and extracted with diethyl ether (2×). The combined organic layers were washed twice with water and once with brine then dried over sodium sulfate, filtered and concentrated. The residue was absorbed on silica gel and chromatographed with MeOH/CH$_2$Cl$_2$/0.5% NH$_4$OH (gradient 0-3% MeOH) to afford 98 mg (89%) of 2-(6-methyl-imidazo[1,5-a]pyridin-1-yl)-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide as a yellow oil.

Step 7

2-(6-Methyl-imidazo[1,5-a]pyridin-1-yl)-5H-pyrrolo[2,3-b]pyrazine-7-carboxylic acid [(R)-2-(3-cyano-azetidin-1-yl)-1-methyl-2-oxo-ethyl]-amide

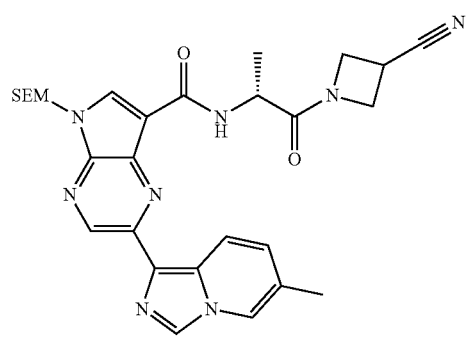

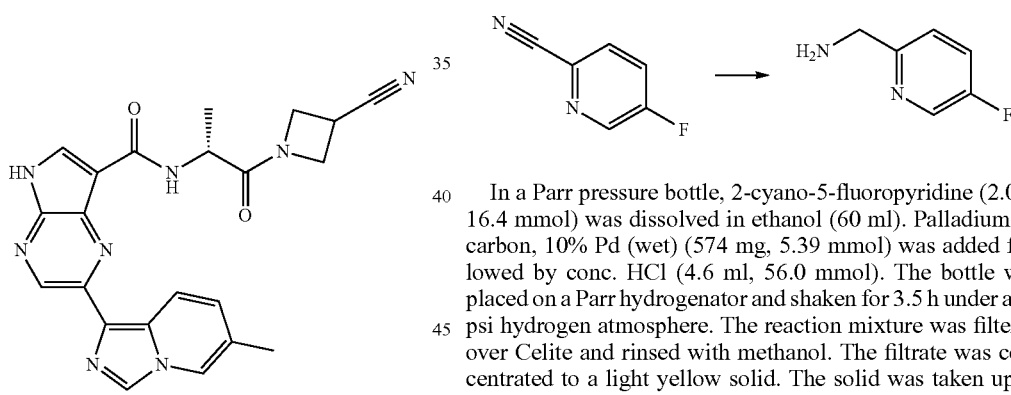

In a round-bottomed flask, 2-(6-methyl-imidazo[1,5-a]pyridin-1-yl)-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide (92 mg, 0.165 mmol) was dissolved in dichloromethane (0.8 ml) and trifluoroacetic acid (0.5 ml, 6.6 mmol) was added. The reaction mixture was stirred at room temperature for 2 h then concentrated. The residue was dissolved in dichloromethane (0.8 ml) and ethylenediamine (0.67 ml, 9.9 mmol) was added. The reaction was stirred at room temperature for 1 h then quenched with water and diluted with ethyl acetate. The resulting suspension was filtered, washed with hot water and ethyl acetate and dried under high vacuum to provide 48 mg (65%) of 2-(6-methyl-imidazo[1,5-a]pyridin-1-yl)-5H-pyrrolo[2,3-b]pyrazine-7-carboxylic acid [(R)-2-(3-cyano-azetidin-1-yl)-1-methyl-2-oxo-ethyl]-amide as a yellow powder. MS: (M+H)⁺= 429; ¹H NMR (DMSO-d₆, 300 MHz): δ (ppm) 12.40 (br. s, 1H), 9.11 (s, 1H), 8.39-8.61 (m, 3H), 8.34 (d, J=7.2 Hz, 1H), 8.28 (s, 1H), 6.79-7.05 (m, 1H), 4.41-4.86 (m, 3H), 4.15-4.33 (m, 1H), 3.99-4.15 (m, 1H), 3.71-3.94 (m, 1H), 2.26 (s, 3H), 1.40 (d, J=4.9 Hz, 3H).

Example 32

2-(6-Fluoro-imidazo[1,5-a]pyridin-1-yl)-5H-pyrrolo[2,3-b]pyrazine-7-carboxylic acid [(R)-2-(3-cyano-azetidin-1-yl)-1-methyl-2-oxo-ethyl]-amide

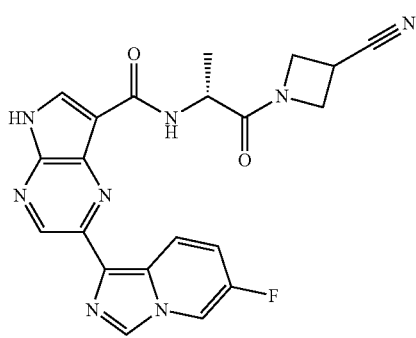 [SMILES: C[C@@H](NC(=O)c1c[nH]c2ncc(-c3ncn4cc(F)ccc34)nc12)C(=O)N1CC(C#N)C1]

Step 1

(5-Fluoro-pyridin-2-yl)-methylamine

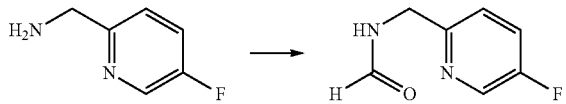 [SMILES: NCc1ccc(F)cn1 ; O=CNCc1ccc(F)cn1]

In a Parr pressure bottle, 2-cyano-5-fluoropyridine (2.0 g, 16.4 mmol) was dissolved in ethanol (60 ml). Palladium on carbon, 10% Pd (wet) (574 mg, 5.39 mmol) was added followed by conc. HCl (4.6 ml, 56.0 mmol). The bottle was placed on a Parr hydrogenator and shaken for 3.5 h under a 45 psi hydrogen atmosphere. The reaction mixture was filtered over Celite and rinsed with methanol. The filtrate was concentrated to a light yellow solid. The solid was taken up in dichloromethane, cooled to 0° C., and basified with saturated aqueous NaHCO₃. The aqueous layer was extracted with dichloromethane (3×) and the combined organics were dried over sodium sulfate, filtered and concentrated to give 558 mg (27%) of (5-fluoro-pyridin-2-yl)-methylamine as a yellow oil which was used without further purification.

Step 2

N-(5-Fluoro-pyridin-2-ylmethyl)-formamide

In a round-bottomed flask, (5-fluoro-pyridin-2-yl)methylamine (557 mg, 4.42 mmol) was dissolved in 88% formic acid (3.6 ml, 82.6 mmol). The brown solution was stirred at reflux in an oil bath overnight. The reaction mixture was cooled to 0° C. and adjusted carefully to pH=9 by addition of 25% aqueous ammonium hydroxide. The mixture was diluted with water and the aqueous layer was extracted with dichloromethane (3×). The organic layers were combined, dried over sodium sulfate, filtered and concentrated to give 614 mg (90%) of N-(5-fluoro-pyridin-2-ylmethyl)-formamide as a brown oil which was used without further purification.

Step 3

6-Fluoro-imidazo[1,5-a]pyridine

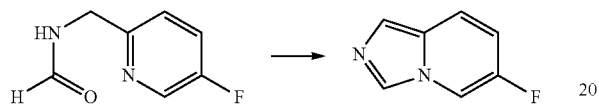

In a round-bottomed flask, N-(5-fluoro-pyridin-2-ylmethyl)-formamide (612 mg, 3.97 mmol) was dissolved in toluene (16 ml) and phosphorus oxychloride (0.68 ml, 7.3 mmol) was added. The reaction mixture was stirred at 100° C. in an oil bath for 4 h then cooled to 0° C. and carefully quenched with ice. Aqueous 25% ammonium hydroxide was added until pH=~9. The mixture was diluted with water and extracted with dichloromethane (3×). The organic layers were combined, dried over sodium sulfate, filtered and concentrated to give 517 mg (96%) of 6-fluoro-imidazo[1,5-a]pyridine as a light brown oil. $^1$H NMR (CDCl$_3$, 300 MHz): δ (ppm) 8.16 (s, 1H), 7.84-7.94 (m, 1H), 7.50 (s, 1H), 7.46 (dd, J=9.8, 5.3 Hz, 1H), 6.69 (ddd, J=9.8, 7.7, 2.1 Hz, 1H).

Step 4

2-(6-Fluoro-imidazo[1,5-a]pyridin-1-yl)-5H-pyrrolo[2,3-b]pyrazine-7-carboxylic acid [(R)-2-(3-cyano-azetidin-1-yl)-1-methyl-2-oxo-ethyl]-amide

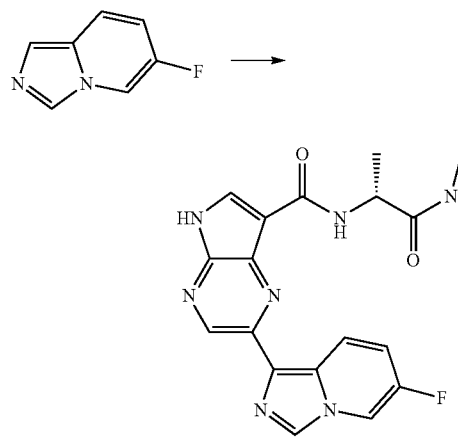

Prepared according to the procedure outlined in Example 31, Steps 4-7, substituting 6-fluoro-imidazo[1,5-a]pyridine for 6-methyl-imidazo[1,5-a]pyridine in Step 4. MS: (M+H)$^+$ =433; $^1$H NMR (DMSO-d$_6$, 300 MHz): δ (ppm) 12.76 (br. s., 1H), 9.14 (s, 1H), 8.62-8.80 (m, 2H), 8.53 (s, 1H), 8.31-8.47 (m, 2H), 7.00-7.15 (m, 1H), 4.44-4.83 (m, 3H), 4.25 (q, J=9.2 Hz, 1H), 4.05-4.18 (m, 1H), 3.77-3.94 (m, 1H), 1.40 (t, J=5.7 Hz, 3H).

Example 33

2-(6,8-Difluoro-imidazo[1,5-a]pyridin-1-yl)-5H-pyrrolo[2,3-b]pyrazine-7-carboxylic acid [(R)-2-(3-cyano-azetidin-1-yl)-1-methyl-2-oxo-ethyl]-amide

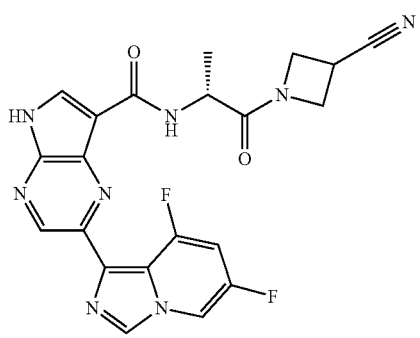 [SMILES: C[C@@H](NC(=O)c1c[nH]c2ncc(-c3ncn4cc(F)cc(F)c34)nc12)C(=O)N1CC(C#N)C1]

Step 1

(3,5-Difluoro-pyridin-2-yl)-methylamine

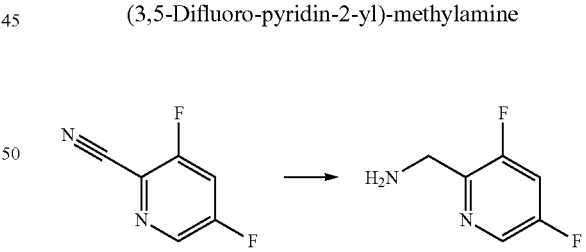

In a Parr pressure bottle, 2-cyano-3,5-difluoropyridine (1.0 g, 7.14 mmol) was dissolved in ethanol (30 ml). Palladium on carbon, 10% Pd (wet) (250 mg, 2.35 mmol) was added followed by conc. HCl (2.0 ml, 24.4 mmol). The bottle was placed on a Parr hydrogenator and shaken for 3.5 h under a 45 psi hydrogen atmosphere. The reaction mixture was filtered over Celite and rinsed with methanol. The filtrate was concentrated to a light yellow solid. The solid was taken up in dichloromethane, cooled to 0° C., and basified with saturated aqueous NaHCO$_3$. The aqueous layer was extracted with dichloromethane (3×) and the combined organics were dried over sodium sulfate, filtered and concentrated to give 662 mg (64%) of (3,5-difluoro-pyridin-2-yl)-methylamine as a light yellow oil which was used without further purification.

Step 2

N-(3,5-Difluoro-pyridin-2-ylmethyl)-formamide

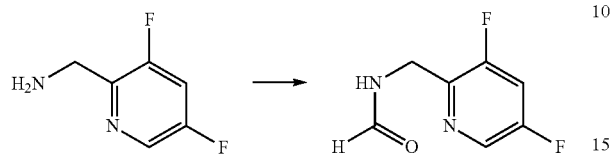

In a round-bottomed flask, (3,5-difluoro-pyridin-2-yl)methylamine (660 mg, 4.58 mmol) was dissolved in 88% formic acid (3.6 ml, 82.6 mmol). The brown solution was stirred at reflux in an oil bath overnight. The reaction mixture was cooled to 0° C. and adjusted carefully to pH=8 by addition of 25% aqueous ammonium hydroxide. The mixture was diluted with water and the aqueous layer was extracted with dichloromethane (3×). The organic layers were combined, dried over sodium sulfate, filtered and concentrated. NMR showed an approximate 50% ratio of starting material to product. This mixture was resubjected to identical reaction conditions. After workup, isolated 657 mg of a brown oil which was determined by NMR to be an approximate 3:1 ratio of N-(3,5-difluoro-pyridin-2-ylmethyl)-formamide to starting material. This product was used without further purification.

Step 3

6,8-Difluoro-imidazo[1,5-a]pyridine

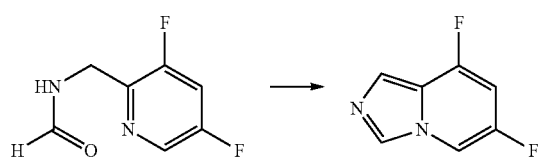 [SMILES: O=CNCc1ncc(F)cc1F ; Fc1cc(F)c2cncn2c1]

In a round-bottomed flask, N-(3,5-difluoro-pyridin-2-ylmethyl)-formamide (crude from Step 2) was dissolved in toluene (14 ml) and phosphorus oxychloride (0.65 ml, 7.0 mmol) was added. The reaction mixture was stirred at 100° C. in an oil bath for 3.5 h then cooled to 0° C. and carefully quenched with ice. Aqueous 25% ammonium hydroxide was added until pH=~9. The mixture was diluted with water and extracted with dichloromethane (3×). The organic layers were combined, dried over sodium sulfate, filtered and concentrated. The residue was absorbed on silica gel and chromatographed with EtOAc/hexanes (gradient 0-60% EtOAc) to give 319 mg (45%, 2 steps) of 6,8-difluoro-imidazo[1,5-a]pyridine as a yellow solid. $^1$H NMR (CDCl$_3$, 300 MHz): δ (ppm) 8.36 (d, J=3.0 Hz, 1H), 7.84 (d, J=3.4 Hz, 1H), 7.65 (s, 1H), 6.39-6.57 (m, 1H).

Step 4

2-(6,8-Difluoro-imidazo[1,5-a]pyridin-1-yl)-5H-pyrrolo[2,3-b]pyrazine-7-carboxylic acid [(R)-2-(3-cyano-azetidin-1-yl)-1-methyl-2-oxo-ethyl]-amide

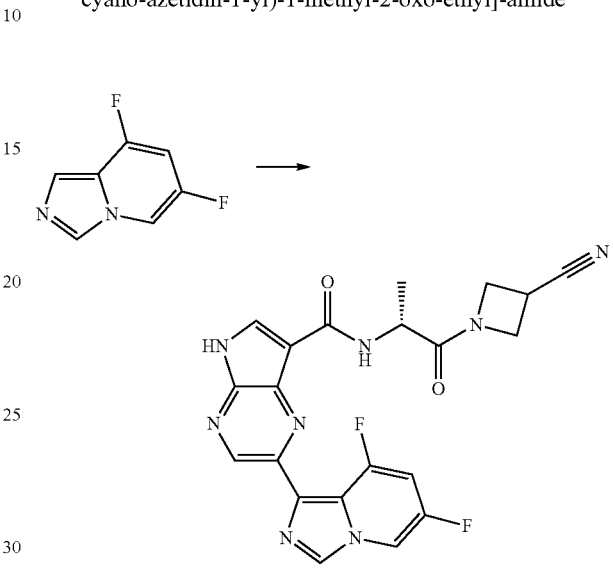

Prepared according to the procedure outlined in Example 31, Steps 4-7, substituting 6,8-difluoro-imidazo[1,5-a]pyridine for 6-methyl-imidazo[1,5-a]pyridine in Step 4. MS: (M+H)$^+$=451; $^1$H NMR (DMSO-d$_6$, 300 MHz): δ (ppm) 12.39 (br. s., 1H), 9.03 (s, 1H), 8.70 (d, J=2.3 Hz, 1H), 8.63 (dd, J=4.2, 1.5 Hz, 1H), 8.54 (d, J=7.2 Hz, 1H), 8.41 (d, J=11.0 Hz, 1H), 7.21 (t, J=10.2 Hz, 1H), 4.40-4.74 (m, 3H), 4.08-4.24 (m, 1H), 3.95-4.07 (m, 1H), 3.74-3.90 (m, 1H), 1.31-1.44 (m, 3H).

Example 34

2-(6-Fluoro-3-methyl-imidazo[1,5-a]pyridin-1-yl)-5H-pyrrolo[2,3-b]pyrazine-7-carboxylic acid [(R)-2-(3-cyano-azetidin-1-yl)-1-methyl-2-oxo-ethyl]-amide

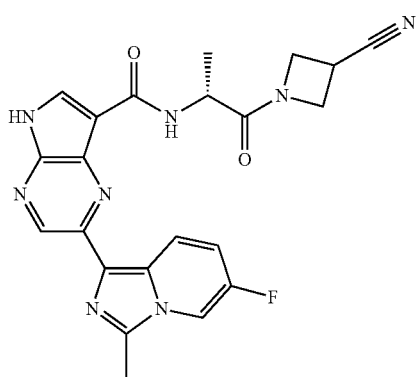 [SMILES: Cc1nc(-c2cnc3[nH]cc(C(=O)N[C@H](C)C(=O)N4CC(C#N)C4)c3n2)c2ccc(F)cn12]

Step 1

(5-Fluoro-pyridin-2-yl)-methylamine dihydrochloride

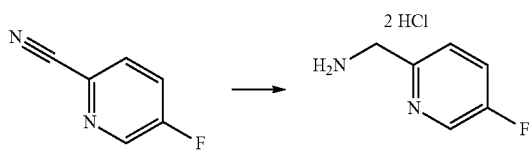 [SMILES: N#Cc1ccc(F)cn1 ; NCc1ccc(F)cn1]

In a Parr pressure bottle, 2-cyano-5-fluoropyridine (1.0 g, 8.2 mmol) was dissolved in ethanol (30 ml). Palladium on carbon, 10% Pd (wet) (290 mg, 2.73 mmol) was added followed by conc. HCl (2.3 ml, 28.0 mmol). The bottle was placed on a Parr hydrogenator and shaken for 4 h under a 45 psi hydrogen atmosphere. The reaction mixture was filtered over Celite and rinsed with methanol. The filtrate was concentrated to give 1.61 g (99%) of (5-fluoro-pyridin-2-yl)-methylamine dihydrochloride as a light yellow solid which was used without further purification.

Step 2

N-(5-Fluoro-pyridin-2-ylmethyl)-acetamide

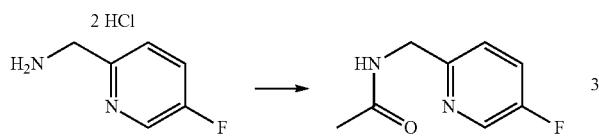

In a round-bottomed flask, (5-fluoropyridin-2-yl)methylamine dihydrochloride (800 mg, 4.0 mmol) was suspended in THF (15 ml). The suspension was cooled to 0° C. and triethylamine (1.75 ml, 12.6 mmol) was added followed by dropwise addition of acetyl chloride (0.30 ml, 4.22 mmol). After the addition was complete, the ice bath was removed and the reaction mixture was stirred at room temperature for 2 h. The reaction was quenched with water and extracted with EtOAc (2×). The combined organic layers were washed with water and brine then dried over sodium sulfate, filtered and concentrated to give 654 mg (97%) of N-(5-fluoro-pyridin-2-ylmethyl)-acetamide as a light brown oil which was used without further purification.

Step 3

6-Fluoro-3-methyl-imidazo[1,5-a]pyridine

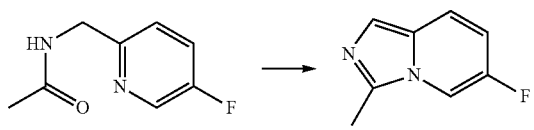

In a round-bottomed flask, N-(5-fluoro-pyridin-2-ylmethyl)-acetamide (653 mg, 3.88 mmol) was dissolved in toluene (19 ml) and phosphorus oxychloride (0.66 ml, 7.1 mmol) was added. The reaction mixture was stirred at 100° C. in an oil bath overnight then cooled to 0° C. and carefully quenched with ice. Aqueous 25% ammonium hydroxide was added until pH=~9. The mixture was diluted with water and extracted with dichloromethane (3×). The organic layers were combined, dried over sodium sulfate, filtered and concentrated. The residue was chromatographed over silica gel with EtOAc/hexanes (gradient 0-70% EtOAc) to give 255 mg (44%) of 6-fluoro-3-methyl-imidazo[1,5-a]pyridine as a yellow solid. $^1$H NMR (CDCl$_3$, 300 MHz): δ (ppm) 7.61 (d, J=5.3 Hz, 1H), 7.38-7.50 (m, 2H), 6.67 (ddd, J=9.7, 7.6, 1.9 Hz, 1H), 2.66 (s, 3H).

Step 4

2-(6-Fluoro-3-methyl-imidazo[1,5-a]pyridin-1-yl)-5H-pyrrolo[2,3-b]pyrazine-7-carboxylic acid [(R)-2-(3-cyano-azetidin-1-yl)-1-methyl-2-oxo-ethyl]-amide

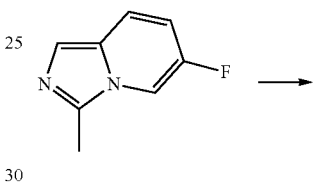

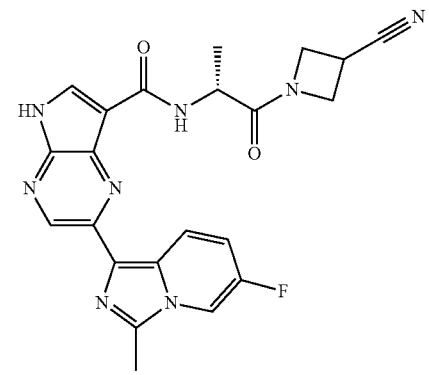

Prepared according to the procedure outlined in Example 31, Steps 4-7, substituting 6-fluoro-3-methyl-imidazo[1,5-a]pyridine for 6-methyl-imidazo[1,5-a]pyridine in Step 4. MS: (M+H)$^+$=447; $^1$H NMR (DMSO-d$_6$, 300 MHz): δ (ppm) 12.53 (br. s., 1H), 9.09 (s, 1H), 8.61-8.76 (m, 1H), 8.28-8.54

(m, 3H), 7.01 (br. s., 1H), 4.45-4.81 (m, 3H), 4.19-4.32 (m, 1H), 4.14 (br. s., 1H), 3.87 (br. s., 1H), 2.67 (s, 3H), 1.39 (br. s., 3H).

Example 35

2-(6-Fluoro-3-hydroxymethyl-imidazo[1,5-a]pyridin-1-yl)-5H-pyrrolo[2,3-b]pyrazine-7-carboxylic acid [(R)-2-(3-cyano-azetidin-1-yl)-1-methyl-2-oxo-ethyl]-amide

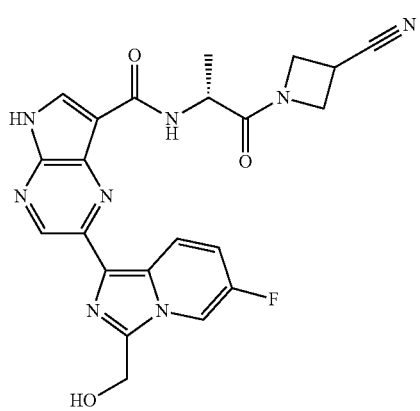 [SMILES: C[C@@H](NC(=O)c1c[nH]c2ncc(-c3nc(CO)n4cc(F)ccc34)nc12)C(=O)N1CC(C#N)C1]

Step 1

N-(5-Fluoro-pyridin-2-ylmethyl)-oxalamic acid methyl ester

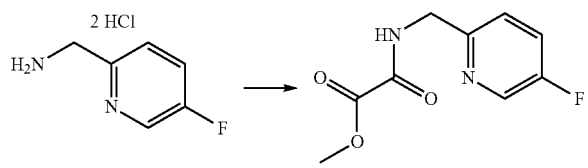

In a round-bottomed flask, (5-fluoropyridin-2-yl)methylamine dihydrochloride (800 mg, 4.0 mmol) was suspended in THF (15 ml). The suspension was cooled to 0° C. and triethylamine (1.75 ml, 12.6 mmol) was added followed by dropwise addition of methyl oxalyl chloride (0.40 ml, 4.18 mmol). After the addition was complete, the ice bath was removed and the reaction mixture was stirred at room temperature for 2.5 h. The reaction was quenched with water and extracted with EtOAc (2×). The combined organic layers were washed with water and brine then dried over sodium sulfate, filtered and concentrated to give N-(5-fluoro-pyridin-2-ylmethyl)-oxalamic acid methyl ester as a light brown oil which was used without further purification.

Step 2

6-Fluoro-imidazo[1,5-a]pyridine-3-carboxylic acid methyl ester

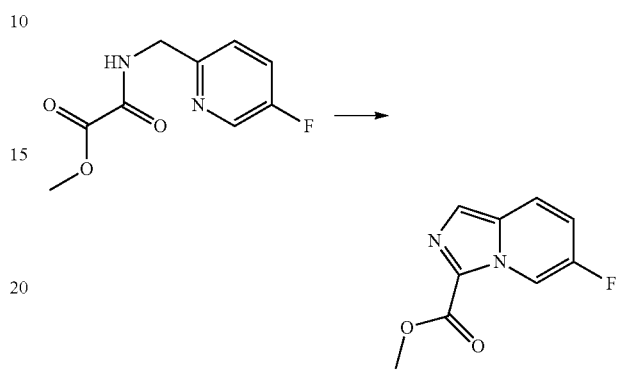

In a round-bottomed flask, N-(5-fluoro-pyridin-2-ylmethyl)-oxalamic acid methyl ester (crude from Step 1) was dissolved in toluene (8 ml) and phosphorus oxychloride (1.5 ml, 16.1 mmol) was added. The reaction mixture was stirred at 105° C. in an oil bath overnight then cooled to 0° C. and carefully quenched with ice. Aqueous 25% ammonium hydroxide was added until pH=~9. The mixture was diluted with water and extracted with dichloromethane (3×). The organic layers were combined, dried over sodium sulfate, filtered and concentrated. The residue was absorbed on silica gel and chromatographed with EtOAc/hexanes (gradient 0-50% EtOAc) to give 230 mg (31%, 2 steps) of 6-fluoro-imidazo[1,5-a]pyridine-3-carboxylic acid methyl ester as a light brown solid. $^1$H NMR (CDCl$_3$, 300 MHz): δ (ppm) 9.33 (dd, J=5.1, 1.3 Hz, 1H), 7.75 (s, 1H), 7.69 (dd, J=9.8, 5.3 Hz, 1H), 7.09 (ddd, J=9.7, 7.5, 2.1 Hz, 1H), 4.06 (s, 3H).

Step 3

(6-Fluoro-imidazo[1,5-a]pyridin-3-yl)-methanol

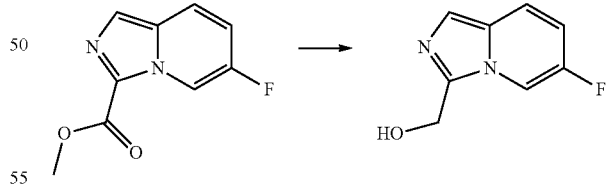

In a round-bottomed flask, 6-fluoro-imidazo[1,5-a]pyridine-3-carboxylic acid methyl ester (223 mg, 1.15 mmol) was dissolved in THF (7 ml). The solution was cooled to 0° C. and lithium aluminum hydride (1.0 M in THF, 1.4 ml, 1.4 mmol) was added dropwise. The reaction mixture was stirred at 0° C. for 1.5 h then sodium sulfate decahydrate was carefully added. When gas evolution had ceased, the ice bath was removed, sodium sulfate was added and the mixture was stirred vigorously for 30 min at room temperature. The suspension was filtered over Celite and rinsed with ethyl acetate and methanol. The filtrate was concentrated to give 225 mg of (6-fluoro-imidazo[1,5-a]pyridin-3-yl)-methanol as a brown solid which was used without further purification.

Step 4

(6-Fluoro-1-iodo-imidazo[1,5-a]pyridin-3-yl)-methanol

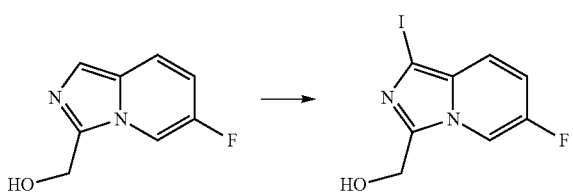 [SMILES: OCc1ncc2ccc(F)cn12 ; OCc1nc(I)c2ccc(F)cn12]

In a round-bottomed flask, (6-fluoro-imidazo[1,5-a]pyridin-3-yl)-methanol (225 mg, 1.15 mmol) was dissolved in ethanol (2 ml) and water (1 ml). Sodium bicarbonate (341 mg, 4.06 mmol) was added followed by iodine (383 mg, 1.51 mmol). The dark brown suspension was stirred at room temperature for 3 h then quenched with 10% $Na_2S_2O_3$-solution and extracted with EtOAc (2×). The organic layers were washed with water and brine then dried over sodium sulfate, filtered and concentrated. The residue was absorbed on silica gel and chromatographed with EtOAc/hexanes (gradient 0-40% EtOAc) to provide 157 mg (50%, 2 steps) of (6-fluoro-1-iodo-imidazo[1,5-a]pyridin-3-yl)-methanol as a light yellow solid.

Step 5

(6-Fluoro-1-tributylstannanyl-imidazo[1,5-a]pyridin-3-yl)-methanol

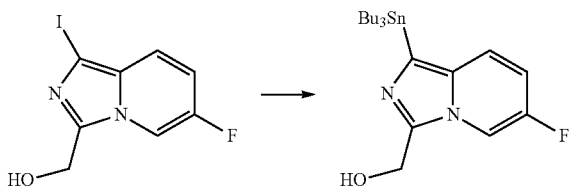

In a round-bottomed flask, (6-fluoro-1-iodo-imidazo[1,5-a]pyridin-3-yl)-methanol (156 mg, 0.53 mmol) was dissolved in THF (4 ml). Sodium hydride (60% dispersion in mineral oil, 26 mg, 0.65 mmol) was added and the reaction mixture was stirred at room temperature for 10 min. The reaction mixture was cooled to −16° C. (NaCl/ice bath) and isopropylmagnesium chloride (2.0 M in THF, 0.32 ml, 0.64 mmol) was added dropwise. The reaction was stirred at −16° C. for 25 min then tributylchlorostannane (0.17 ml, 0.63 mmol) was slowly added. The reaction mixture was allowed to warm to room temperature and stirred for 1.5 h then quenched with saturated aqueous $NH_4Cl$ and extracted with EtOAc (2×). The combined organic layers were washed with water and brine then dried over sodium sulfate, filtered and concentrated to afford (6-Fluoro-1-tributylstannanyl-imidazo[1,5-a]pyridin-3-yl)-methanol as a brown semisolid which was used without further purification.

Step 6

2-(6-Fluoro-3-hydroxymethyl-imidazo[1,5-a]pyridin-1-yl)-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide

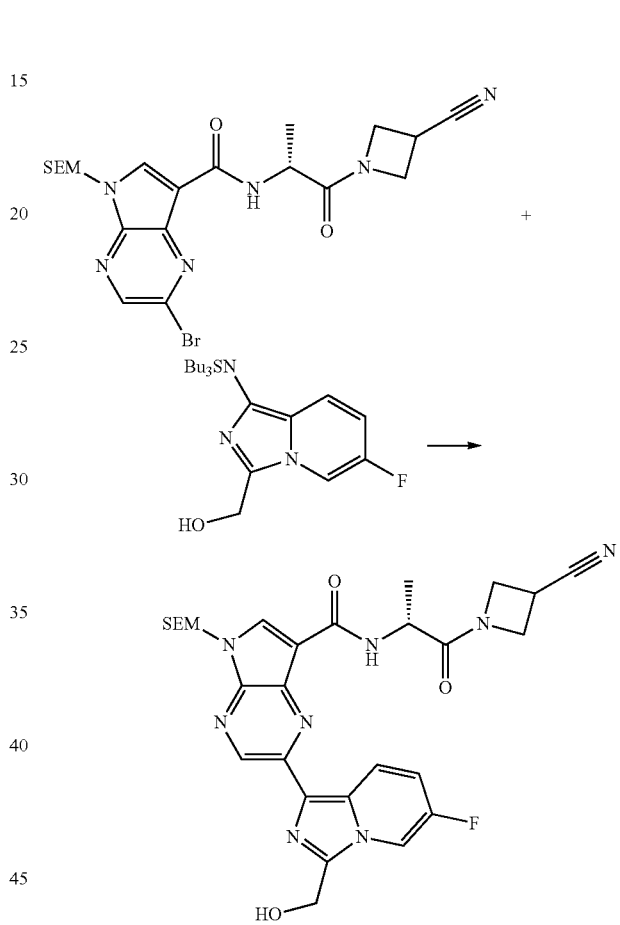

In a round-bottomed flask, 2-bromo-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide (100 mg, 0.20 mmol) and (6-Fluoro-1-tributylstannanyl-imidazo[1,5-a]pyridin-3-yl)-methanol (crude from Step 5) were dissolved in DMF (2 ml The flask was evacuated and backfilled with argon then tetrakis(triphenylphosphine)palladium (0) (12 mg, 0.010 mmol) and copper (I) iodide (8 mg, 0.042 mmol) were added. The reaction mixture was stirred at 90° C. in an oil bath for 3 h then cooled to room temperature, quenched with water and extracted with dichloromethane (2×). The combined organic layers were washed twice with water and once with brine then dried over sodium sulfate, filtered and concentrated. The residue was absorbed on silica gel and chromatographed with MeOH/$CH_2Cl_2$/0.5% $NH_4OH$ (gradient 0-3% MeOH) to afford 83 mg (71%) of 2-(6-fluoro-3-hydroxymethyl-imidazo[1,5-a]pyridin-1-yl)-5-(2-trimethylsilanylethoxymethyl)-5H-pyrrolo[2,3-b]pyrazine-7-carboxylic acid [(R)-2-(3-cyano-azetidin-1-yl)-1-methyl-2-oxo-ethyl]-amide as a light brown solid.

Step 7

2-(6-Fluoro-3-hydroxymethyl-imidazo[1,5-a]pyridin-1-yl)-5H-pyrrolo[2,3-b]pyrazine-7-carboxylic acid [(R)-2-(3-cyano-azetidin-1-yl)-1-methyl-2-oxo-ethyl]-amide

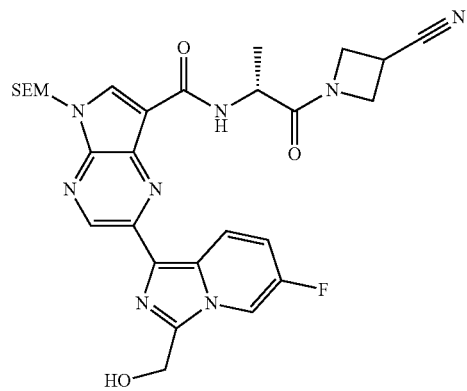

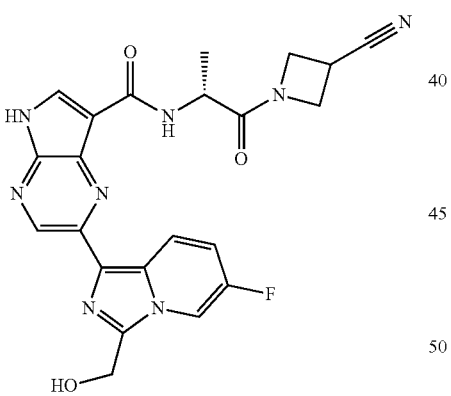

In a round-bottomed flask, 2-(6-fluoro-3-hydroxymethyl-imidazo[1,5-a]pyridin-1-yl)-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide (82 mg, 0.138 mmol) was dissolved in dichloromethane (0.7 ml) and trifluoroacetic acid (0.43 ml, 5.6 mmol) was added. The reaction was stirred at room temperature for 2 h then concentrated. The residue was dissolved in dichloromethane (0.7 ml) and ethylenediamine (0.56 ml, 8.3 mmol) was added. The reaction mixture was stirred at room temperature for 1 h then quenched with water and diluted with dichloromethane. The resulting precipitate was filtered, washing with water and dichloromethane then dried under high vacuum to provide 46 mg (68%) of 2-(6-fluoro-3-hydroxymethyl-imidazo[1,5-a] pyridin-1-yl)-5H-pyrrolo[2,3-b]pyrazine-7-carboxylic acid [(R)-2-(3-cyano-azetidin-1-yl)-1-methyl-2-oxo-ethyl]-amide as a yellow powder. MS: (M+H)$^+$=463; $^1$H NMR (DMSO-d$_6$, 300 MHz): δ (ppm) 12.30 (br. s, 1H), 9.12 (s, 1H), 8.79 (dd, J=9.6, 3.2 Hz, 1H), 8.55 (d, J=4.9 Hz, 1H), 8.44 (d, J=7.9 Hz, 1H), 8.40 (d, J=5.7 Hz, 1H), 7.07-7.17 (m, 1H), 5.61 (t, J=5.7 Hz, 1H), 4.94 (d, J=5.3 Hz, 2H), 4.50-4.81 (m, 3H), 4.20-4.32 (m, 1H), 4.14 (dt, J=10.3, 5.2 Hz, 1H), 3.81-3.93 (m, 1H), 1.40 (t, J=6.0 Hz, 3H).

Example 36

2-(6-Chloro-1-methyl-1H-indazol-3-yl)-5H-pyrrolo[2,3-b]pyrazine-7-carboxylic acid ((1R,3R)-3-cyano-cyclopentyl)-amide

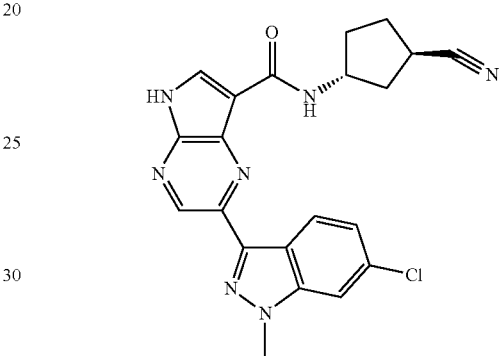

Step 1

((1R,3R)-3-Carbamoyl-cyclopentyl)-carbamic acid tert-butyl ester

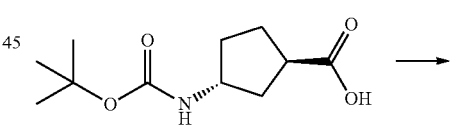

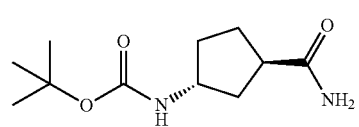

In a round-bottomed flask, (1R,3R)—N-Boc-1-aminocyclopentane-3-carboxylic acid (300 mg, 1.31 mmol) and ammonium chloride (210 mg, 3.93 mmol) were suspended in DMF (6 ml). HATU (547 mg, 1.44 mmol) and N,N-diisopropylethylamine (0.80 ml, 4.58 mmol) were added and the yellow suspension was stirred at room temperature for 72 h. The reaction mixture was quenched with water and extracted with diethyl ether (2×). The combined organic layers were washed twice with water and once with brine then dried over sodium sulfate, filtered and concentrated to afford 97 mg (33%) of ((1R,3R)-3-carbamoyl-cyclopentyl)-carbamic acid tert-butyl ester as a white solid.

Step 2

((1R,3R)-3-Cyano-cyclopentyl)-carbamic acid tert-butyl ester

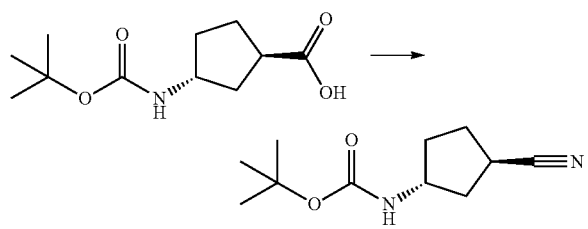

In a round-bottomed flask, ((1R,3R)-3-carbamoyl-cyclopentyl)-carbamic acid tert-butyl ester (96 mg, 0.42 mmol) was suspended in THF (2.5 ml). The reaction mixture was cooled to 0° C. and triethylamine (0.28 ml, 2.01 mmol) followed by trifluoroacetic anhydride (0.095 ml, 0.67 mmol) were added. The homogeneous reaction mixture was stirred at 0° C. for 1.5 h then quenched with water and extracted with dichloromethane (2×). The combined organic layers were dried over sodium sulfate, filtered and concentrated to afford ((1R,3R)-3-cyanocyclopentyl)-carbamic acid tert-butyl ester as an off-white waxy solid which contained some triethylamine trifluoroacetate as a major impurity. This material was used without further purification.

Step 3

(1R,3R)-3-Amino-cyclopentanecarbonitrile trifluoroacetate

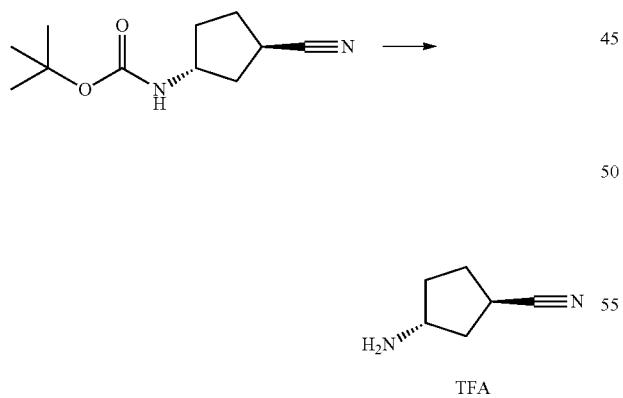

In a round-bottomed flask, ((1R,3R)-3-cyano-cyclopentyl)-carbamic acid tert-butyl ester (crude from Step 2) was dissolved in dichloromethane (2.5 ml). The solution was cooled to 0° C. and trifluoroacetic acid (1.1 ml, 14.3 mmol) was slowly added. After the addition was complete, the ice bath was removed and the reaction mixture was stirred at room temperature for 2 h then concentrated to give (1R,3R)-3-amino-cyclopentanecarbonitrile trifluoroacetate as a light brown oil which was used without further purification.

Step 4

2-(6-Chloro-1-methyl-1H-indazol-3-yl)-5H-pyrrolo [2,3-b]pyrazine-7-carboxylic acid ((1R,3R)-3-cyano-cyclopentyl)-amide

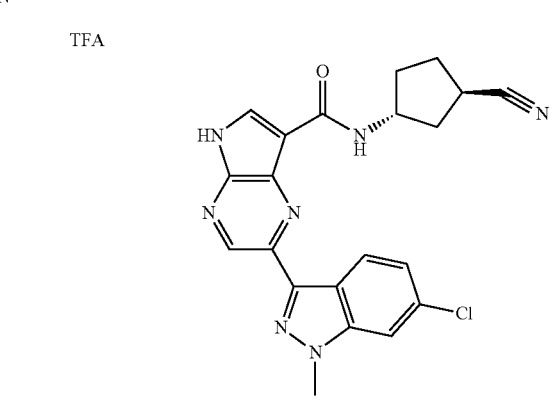

Prepared according to the procedure outlined in Example 14, Steps 5-6, substituting (1R,3R)-3-amino-cyclopentanecarbonitrile trifluoroacetate for (R)-2-amino-1-(3,3-difluoro-azetidin-1-yl)-propan-1-one in Step 5. MS: (M+H)⁺= 420; ¹H NMR (DMSO-d₆, 300 MHz): δ (ppm) 12.48 (br. s, 1H), 9.08 (s, 1H), 8.44 (s, 1H), 8.42 (d, J=8.7 Hz, 1H), 8.13 (d, J=6.8 Hz, 1H), 8.00 (s, 1H), 7.35 (dd, J=8.7, 1.5 Hz, 1H), 4.44-4.58 (m, 1H), 4.17 (s, 3H), 3.22-3.29 (m, 1H), 2.19-2.39 (m, 3H), 1.99-2.12 (m, 1H), 1.81-1.97 (m, 1H), 1.62-1.76 (m, 1H).

Example 37

2-(6-Chloro-1-methyl-1H-indazol-3-yl)-5H-pyrrolo [2,3-b]pyrazine-7-carboxylic acid (3-aminocyclopentyl)-amide

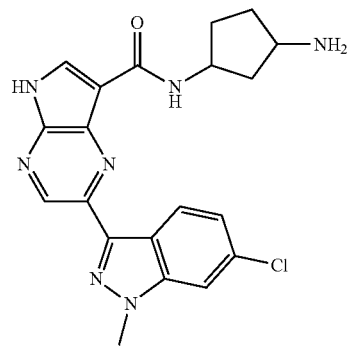 [SMILES: Cn1nc(-c2cnc3[nH]cc(C(=O)NC4CCC(N)C4)c3n2)c2ccc(Cl)cc21]

Step 1

(3-{[2-(6-Chloro-1-methyl-1H-indazol-3-yl)-5-(2-trimethylsilanyl-ethoxymethyl)-5H-pyrrolo[2,3-b]pyrazine-7-carbonyl]-amino}-cyclopentyl)-carbamic acid tert-butyl ester

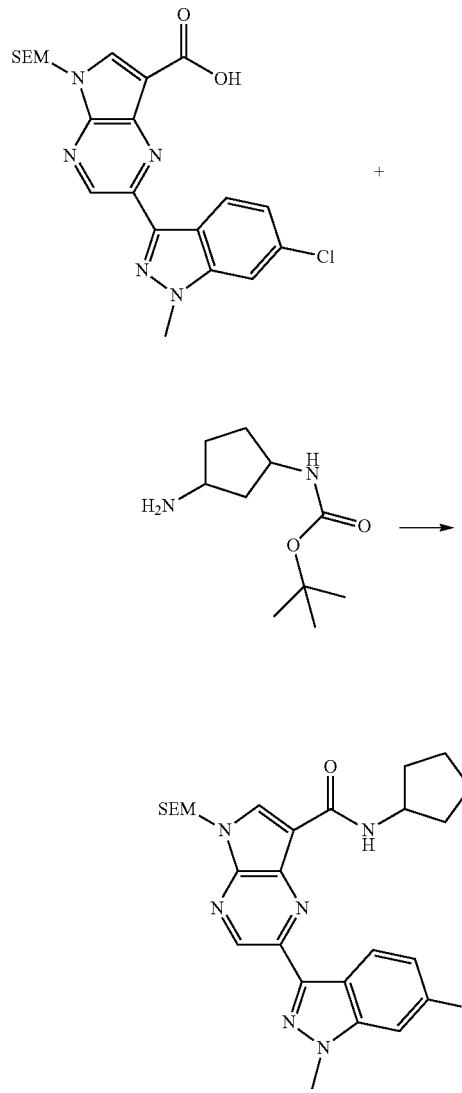

A round-bottomed flask was charged with 2-(6-chloro-1-methyl-1H-indazol-3-yl)-5-(2-trimethylsilanyl-ethoxymethyl)-5H-pyrrolo[2,3-b]pyrazine-7-carboxylic acid (300 mg, 0.66 mmol) and (3-aminocyclopentyl)-carbamic acid tert-butylester hydrochloride (233 mg, 0.98 mmol). DMF (3 ml) was added followed by HATU (274 mg, 0.72 mmol) and N,N-diisopropylethylamine (0.30 ml, 1.72 mmol). The reaction mixture was stirred at room temperature for 30 min. Additional DMF (2 ml) was added and the light yellow suspension was stirred at room temperature overnight. Water was added and the resulting suspension was filtered, washed with water and petroleum ether and dried under high vacuum to afford 413 mg (99%) of (3-{[2-(6-chloro-1-methyl-1H-indazol-3-yl)-5-(2-trimethylsilanyl-ethoxymethyl)-5H-pyrrolo[2,3-b]pyrazine-7-carbonyl]-amino}-cyclopentyl)-carbamic acid tert-butyl ester as an off-white powder. The isolated product was determined to be a single diastereomer of unknown relative stereochemistry by NMR analysis.

Step 2

2-(6-Chloro-1-methyl-1H-indazol-1-yl)-5H-pyrrolo[2,3-b]pyrazine-7-carboxylic acid (3-aminocyclopentyl)-amide

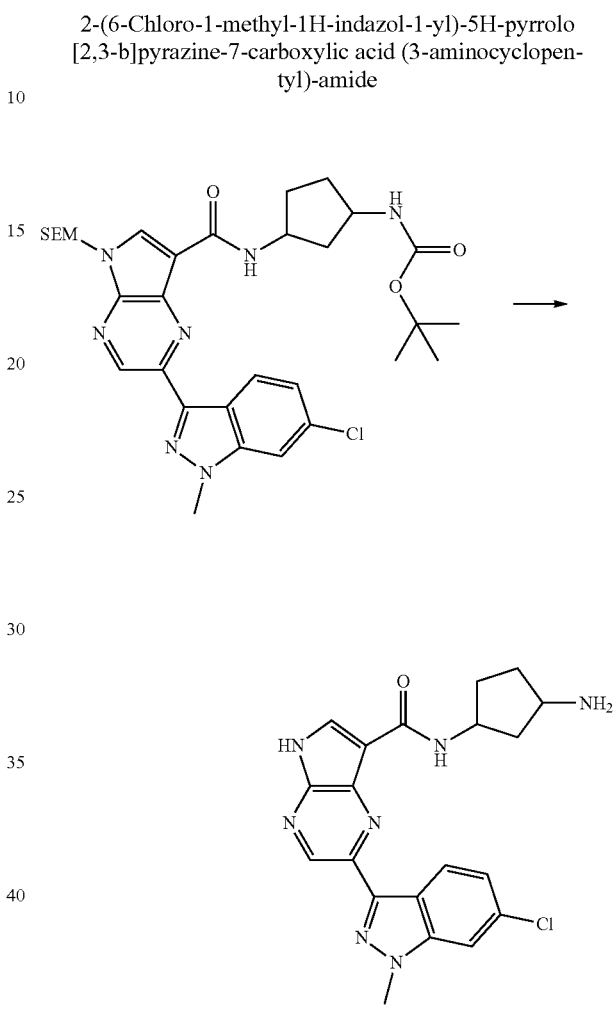

In a round-bottomed flask, (3-{[2-(6-chloro-1-methyl-1H-indazol-3-yl)-5-(2-trimethylsilanyl-ethoxymethyl)-5H-pyrrolo[2,3-b]pyrazine-7-carbonyl]-amino}-cyclopentyl)-carbamic acid tert-butyl ester (80 mg, 0.125 mmol) was dissolved in dichloromethane (0.7 ml) and trifluoroacetic acid (0.4 ml, 5.0 mmol) was added. The reaction mixture was stirred at room temperature for 3.5 h then concentrated. The residue was dissolved in dichloromethane (0.7 ml) and ethylenediamine (0.5 ml, 7.5 mmol) was added. The solution was stirred at room temperature for 2 h then quenched with water and diluted with ethyl acetate. The resultant suspension was filtered, washed with hot water and ethyl acetate and dried under high vacuum to provide 40 mg (74%) of 2-(6-chloro-1-methyl-1H-indazol-3-yl)-5H-pyrrolo[2,3-b]pyrazine-7-carboxylic acid (3-amino-cyclopentyl)-amide as an off-white powder. MS: $(M+H)^+$=410; $^1$H NMR (DMSO-$d_6$, 300 MHz): δ (ppm) 9.07 (s, 1H), 8.55 (d, J=8.7 Hz, 1H), 8.40 (s, 1H), 8.24 (d, J=7.6 Hz, 1H), 7.99 (s, 1H), 7.40 (d, J=9.1 Hz, 1H), 5.54 (br. s, 2H), 4.34-4.45 (m, 1H), 4.17 (s, 3H), 3.36-3.44 (m, 1H), 2.25-2.37 (m, 1H), 2.03-2.16 (m, 1H), 1.71-1.88 (m, 2H), 1.51-1.62 (m, 1H), 1.32-1.43 (m, 1H). The

355 isolated product was determined to be a single diastereomer of unknown relative stereochemistry by NMR analysis.

Example 38

2-(6-Chloro-1-methyl-1H-indazol-3-yl)-5H-pyrrolo[2,3-b]pyrazine-7-carboxylic acid (3-methanesulfonylamino-cyclopentyl)-amide

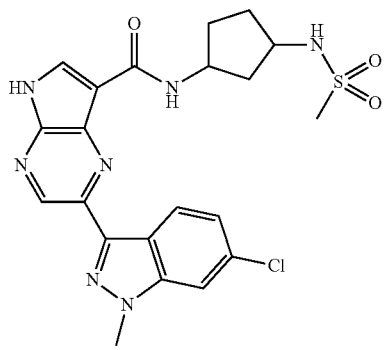 [SMILES: Cn1nc(-c2cnc3[nH]cc(C(=O)NC4CCC(NS(C)(=O)=O)C4)c3n2)c2ccc(Cl)cc21]

Step 1

2-(6-Chloro-1-methyl-1H-indazol-3-yl)-5-(2-trimethylsilanyl-ethoxymethyl)-5H-pyrrolo[2,3-b]pyrazine-7-carboxylic acid (3-amino-cyclopentyl)-amide hydrochloride

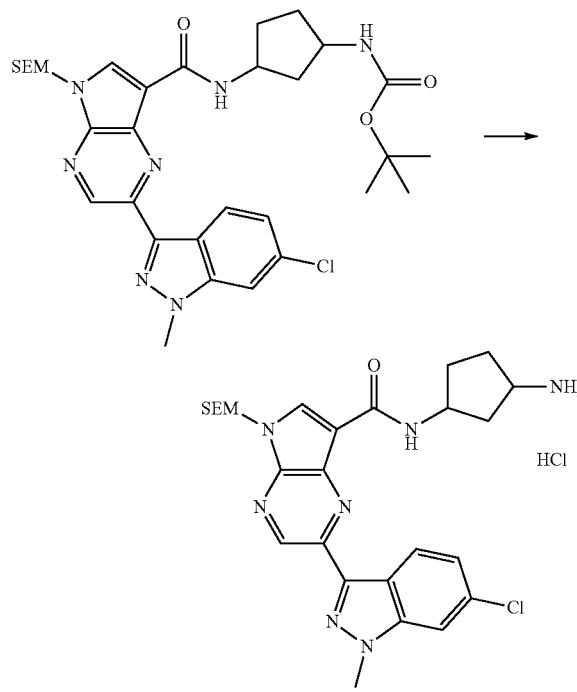

In a round-bottomed flask, (3-{[2-(6-chloro-1-methyl-1H-indazol-3-yl)-5-(2-trimethylsilanyl-ethoxymethyl)-5H-pyrrolo[2,3-b]pyrazine-7-carbonyl]-amino}-cyclopentyl)-carbamic acid tert-butyl ester (150 mg, 0.23 mmol) was suspended in methanol (2 ml). The reaction mixture was cooled to 0° C. and acetyl chloride (0.33 ml, 4.64 mmol) was added dropwise. The ice bath was removed and the reaction mixture was stirred at room temperature for 1.5 h. The solvent was evaporated at room temperature and the residue was dried under high vacuum to afford 147 mg (98%) of 2-(6-chloro-1-methyl-1H-indazol-3-yl)-5-(2-trimethylsilanylethoxymethyl)-5H-pyrrolo[2,3-b]pyrazine-7-carboxylic acid (3-amino-cyclopentyl)-amide hydrochloride as a light yellow solid.

Step 2

2-(6-Chloro-1-methyl-1H-indazol-3-yl)-5-(2-trimethylsilanyl-ethoxymethyl)-5H-pyrrolo[2,3-b]pyrazine-7-carboxylic acid (3-methanesulfonylamino-cyclopentyl)-amide

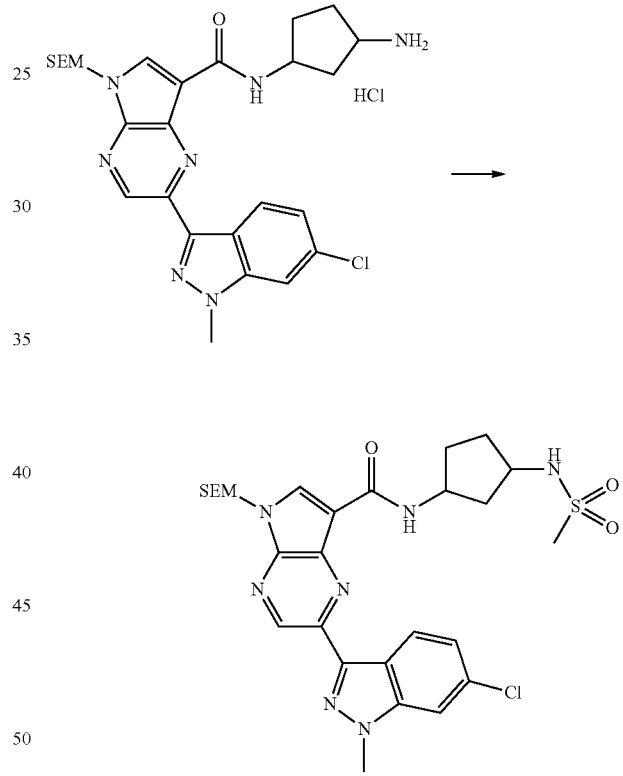

In a round-bottomed flask, 2-(6-chloro-1-methyl-1H-indazol-3-yl)-5-(2-trimethylsilanylethoxymethyl)-5H-pyrrolo[2,3-b]pyrazine-7-carboxylic acid (3-amino-cyclopentyl)-amide hydrochloride (145 mg, 0.23 mmol) was suspended in dichloromethane (2.5 ml). The suspension was cooled to 0° C. and triethylamine (0.10 ml, 0.72 mmol) was added followed by methanesulfonyl chloride (0.02 ml, 0.26 mmol). The reaction mixture was stirred at room temperature overnight then quenched with water and extracted with dichloromethane (2×). The combined organic layers were dried over sodium sulfate, filtered and concentrated. The residue was chromatographed over silica gel with MeOH/CH$_2$Cl$_2$/0.5% NH$_4$OH (gradient 0-5% MeOH) to afford 111 mg (79%) of 2-(6-chloro-1-methyl-1H-indazol-3-yl)-5-(2-trimethylsilanylethoxymethyl)-5H-pyrrolo[2,3-b]pyrazine-7-carboxylic acid (3-methanesulfonylamino-cyclopentyl)-amide as a light yellow solid.

Step 3

2-(6-Chloro-1-methyl-1H-indazol-3-yl)-5H-pyrrolo[2,3-b]pyrazine-7-carboxylic acid (3-methanesulfonylamino-cyclopentyl)-amide

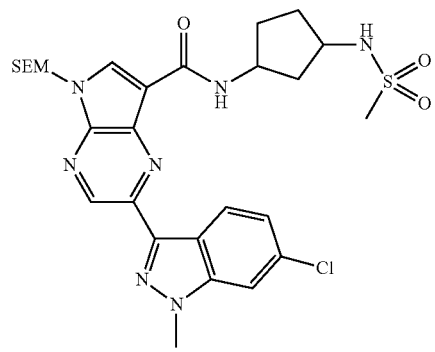

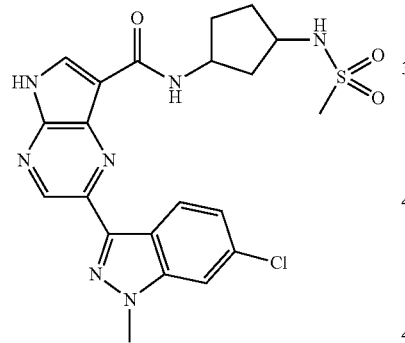

In a round-bottomed flask, 2-(6-chloro-1-methyl-1H-indazol-3-yl)-5-(2-trimethylsilanylethoxymethyl)-5H-pyrrolo[2,3-b]pyrazine-7-carboxylic acid (3-methanesulfonylamino-cyclopentyl)-amide (109 mg, 0.176 mmol) was dissolved in dichloromethane (0.9 ml) and trifluoroacetic acid (0.54 ml, 7.0 mmol) was added. The orange solution was stirred at room temperature for 2 h then concentrated. The residue was dissolved in dichloromethane (0.9 ml) and ethylenediamine (0.7 ml, 10.5 mmol) was added. The yellow solution was stirred at room temperature for 1.5 h then quenched with water and diluted with ethyl acetate. The resultant suspension was filtered, washed with hot water and ethyl acetate and dried under high vacuum to provide 76 mg (88%) of 2-(6-chloro-1-methyl-1H-indazol-3-yl)-5H-pyrrolo[2,3-b]pyrazine-7-carboxylic acid (3-methanesulfonylamino-cyclopentyl)-amide as an off-white powder. MS: (M+H)$^+$=488; $^1$H NMR (DMSO-d$_6$, 300 MHz): δ (ppm) 12.30 (br. s, 1H), 9.11 (s, 1H), 8.42-8.52 (m, 2H), 8.17 (d, J=7.2 Hz, 1H), 8.02 (s, 1H), 7.41 (dd, J=8.7, 1.5 Hz, 1H), 7.31 (d, J=7.2 Hz, 1H), 4.27-4.40 (m, 1H), 4.18 (s, 3H), 3.67-3.82 (m, 1H), 2.92 (s, 3H), 2.53-2.63 (m, 1H), 1.97-2.20 (m, 2H), 1.65-1.81 (m, 2H), 1.55 (dt, J=12.3, 9.0 Hz, 1H).

Example 39

2-(3-Chloro-6-fluoro-imidazo[1,5-a]pyridin-1-yl)-5H-pyrrolo[2,3-b]pyrazine-7-carboxylic acid ((S)-2-methoxy-1-methyl-ethyl)-amide

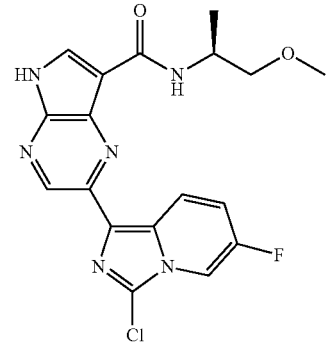 [SMILES: COC[C@H](C)NC(=O)c1c[nH]c2ncc(-c3nc(Cl)n4cc(F)ccc34)nc12]

Step 1

2-(6-Fluoro-imidazo[1,5-a]pyridin-1-yl)-5-(2-trimethylsilanyl-ethoxymethyl)-5H-pyrrolo[2,3-b]pyrazine-7-carbaldehyde

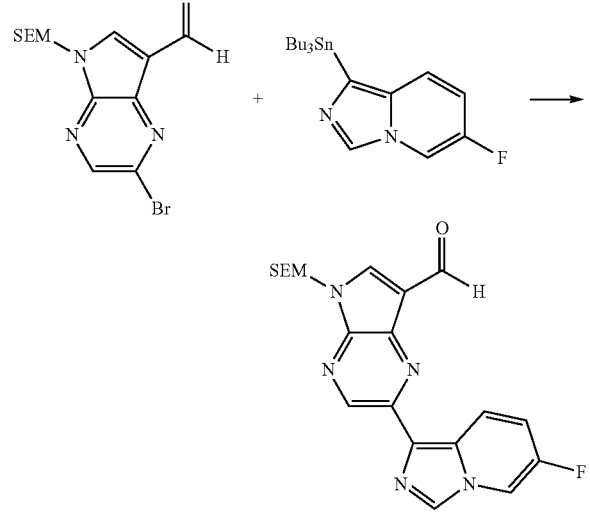

In a round-bottomed flask, 6-fluoro-1-tributylstannyl-imidazo[1,5-a]pyridine (577 mg, 0.81 mmol) and 2-bromo-5-(2-trimethylsilanyl-ethoxymethyl)-5H-pyrrolo[2,3-b]pyrazine-7-carbaldehyde (210 mg, 0.59 mmol) were dissolved in DMF (5 ml). The flask was evacuated and backfilled with argon then tetrakis(triphenylphosphine)palladium (0) (33 mg, 0.029 mmol) and copper (I) iodide (22 mg, 0.12 mmol) were added. The reaction mixture was stirred at 80° C. in an oil bath for 4 h then cooled to room temperature. Water was added and the resulting suspension was filtered. The filter cake was washed with water and petroleum ether then dried under high vacuum to afford 256 mg (95%) of 2-(6-fluoro-imidazo[1,5-a]pyridin-1-yl)-5-(2-trimethylsilanyl-ethoxymethyl)-5H-pyrrolo[2,3-b]pyrazine-7-carbaldehyde as a yellow powder.

Step 2

2-(3-Chloro-6-fluoro-imidazo[1,5-a]pyridin-1-yl)-5-(2-trimethylsilanyl-ethoxymethyl)-5H-pyrrolo[2,3-b]pyrazine-7-carboxylic acid

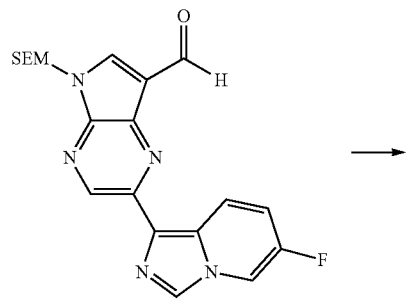

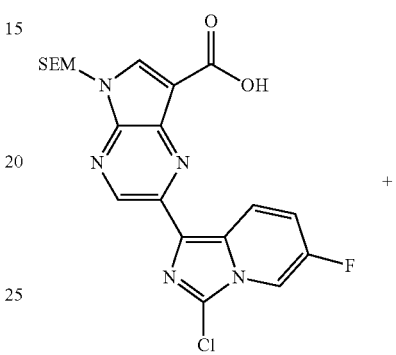

In a round-bottomed flask, 2-(6-fluoro-imidazo[1,5-a]pyridin-1-yl)-5-(2-trimethylsilanylethoxymethyl)-5H-pyrrolo[2,3-b]pyrazine-7-carbaldehyde (254 mg, 0.55 mmol) was suspended in THF (10 ml) and water (2 ml). The suspension was cooled to 0° C. and sulfamic acid (324 mg, 3.33 mmol) was added. Then, a solution of sodium chlorite (80%, 88 mg, 0.78 mmol) and potassium dihydrogen phosphate (907 mg, 6.67 mmol) in water (6 ml) was added dropwise over 10 min. After the addition was complete, the ice bath was removed and the reaction mixture was stirred at room temperature for 4 h. The reaction mixture was diluted with water and extracted with EtOAc (2×). The combined organic layers were washed with water and brine then dried over sodium sulfate, filtered and concentrated. The residue was triturated with hexanes to afford 184 mg of 2-(3-chloro-6-fluoro-imidazo[1,5-a]pyridin-1-yl)-5-(2-trimethylsilanylethoxymethyl)-5H-pyrrolo[2,3-b]pyrazine-7-carboxylic acid as a light green powder which was used without further purification.

Step 3

2-(3-Chloro-6-fluoro-imidazo[1,5-a]pyridin-1-yl)-5-(2-trimethylsilanyl-ethoxymethyl)-5H-pyrrolo[2,3-b]pyrazine-7-carboxylic acid ((S)-2-methoxy-1-methyl-ethyl)-amide

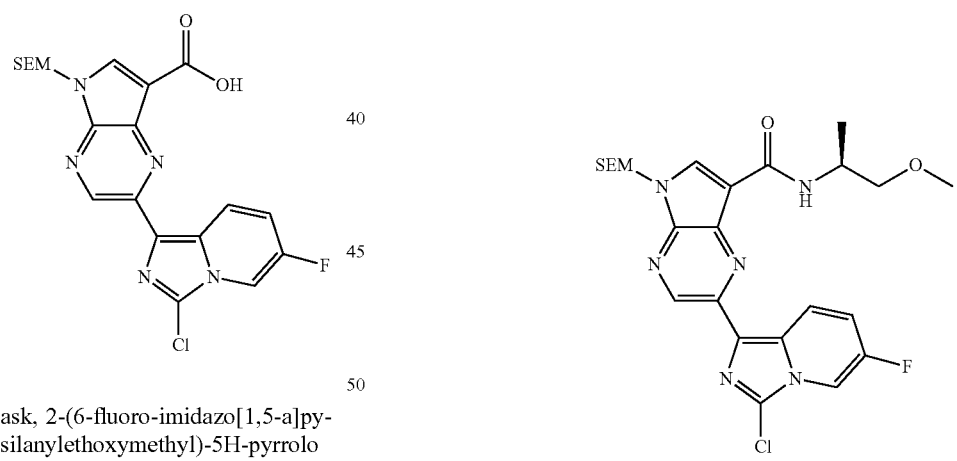

A round-bottomed flask was charged with 2-(3-chloro-6-fluoro-imidazo[1,5-a]pyridin-1-yl)-5-(2-trimethylsilanyl-ethoxymethyl)-5H-pyrrolo[2,3-b]pyrazine-7-carboxylic acid (90 mg, 0.16 mmol) and (S)-1-methoxypropan-2-amine hydrochloride (40 mg, 0.32 mmol). DMF (1 ml) was added followed by N,N-diisopropylethylamine (0.1 ml, 0.57 mmol) and HATU (71 mg, 0.19 mmol). The reaction mixture was stirred at room temperature overnight then water was added. The resulting suspension was filtered, washing with water and petroleum ether. The brown powder was chromatographed over silica gel with MeOH/CH$_2$Cl$_2$/0.5% NH$_4$OH (gradient 0-2% MeOH) to afford 37 mg (44%) of 2-(3-chloro-6-fluoro-imidazo[1,5-a]pyridin-1-yl)-5-(2-trimethylsilanylethoxymethyl)-5H-pyrrolo[2,3-b]pyrazine-7-carboxylic acid ((S)-2-methoxy-1-methyl-ethyl)-amide as a yellow solid.

Step 4

2-(3-Chloro-6-fluoro-imidazo[1,5-a]pyridin-1-yl)-5H-pyrrolo[2,3-b]pyrazine-7-carboxylic acid ((S)-2-methoxy-1-methyl-ethyl)-amide

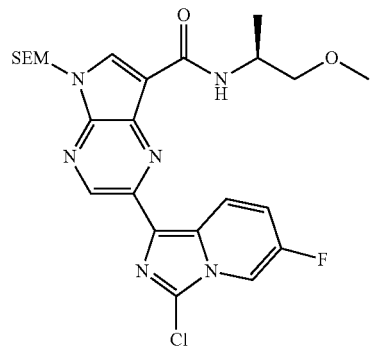

→

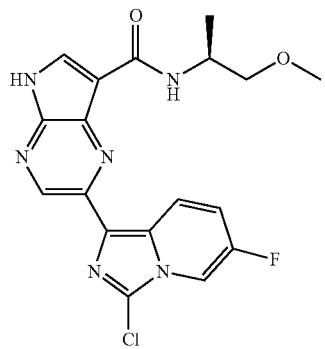

In a round-bottomed flask, 2-(3-chloro-6-fluoro-imidazo[1,5-a]pyridin-1-yl)-5-(2-trimethylsilanyl-ethoxymethyl)-5H-pyrrolo[2,3-b]pyrazine-7-carboxylic acid ((S)-2-methoxy-1-methyl-ethyl)-amide (36 mg, 0.068 mmol) was dissolved in dichloromethane (0.4 ml) and trifluoroacetic acid (0.22 ml, 2.86 mmol) was added. The reaction was stirred at room temperature for 2 h then concentrated. The residue was dissolved in dichloromethane (0.4 ml) and ethylenediamine (0.3 ml, 4.3 mmol) was added. The reaction mixture was stirred at room temperature for 1 h then quenched with water and diluted with ethyl acetate. The resulting suspension was filtered, washed with hot water and ethyl acetate and dried under high vacuum to provide 21 mg (77%) of 2-(3-chloro-6-fluoro-imidazo[1,5-a]pyridin-1-yl)-5H-pyrrolo[2,3-b]pyrazine-7-carboxylic acid ((S)-2-methoxy-1-methyl-ethyl)-amide as a yellow powder. MS: (M+H)$^+$=403; $^1$H NMR (DMSO-d$_6$, 300 MHz): δ (ppm) 12.01 (br. s, 1H), 9.03 (s, 1H), 8.58 (d, J=3.8 Hz, 1H), 8.49 (dd, J=10.0, 5.5 Hz, 1H), 8.40 (s, 1H), 8.10 (d, J=8.3 Hz, 1H), 7.18-7.29 (m, 1H), 4.39 (d, J=7.9 Hz, 1H), 3.50 (qd, J=9.9, 4.3 Hz, 2H), 3.30 (s, 3H), 1.31 (d, J=6.8 Hz, 3H).

Example 40

2-(6,8-Difluoro-imidazo[1,5-a]pyridin-1-yl)-5H-pyrrolo[2,3-b]pyrazine-7-carboxylic acid ((S)-2-methoxy-1-methyl-ethyl)-amide

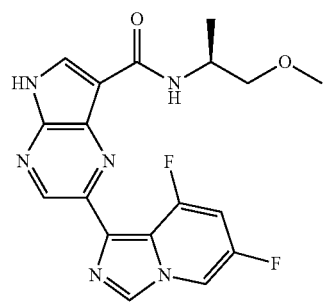 [SMILES: COC[C@H](C)NC(=O)c1c[nH]c2ncc(-c3ncn4cc(F)cc(F)c34)nc12]

Step 1

2-Bromo-5-(2-trimethylsilanyl-ethoxymethyl)-5H-pyrrolo[2,3-b]pyrazine-7-carboxylic acid ((S)-2-methoxy-1-methyl-ethyl)-amide

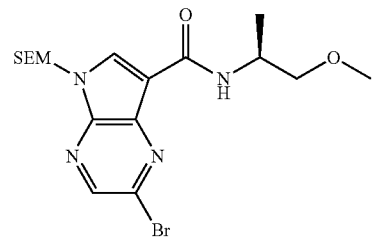

In a round-bottomed flask were combined 2-bromo-5-((2-(trimethylsilyl)ethoxy)methyl)-5H-pyrrolo[2,3-b]pyrazine-7-carboxylic acid (120 mg, 0.32 mmol) and (S)-1-methoxypropan-2-amine hydrochloride (61 mg, 0.49 mmol). DMF (1.5 mL) was added followed by N,N-diisopropylethylamine (0.15 mL, 0.86 mmol) and HATU (135 mg, 0.36 mmol). The yellow reaction mixture was stirred at room temperature overnight then water was added. The resulting suspension was filtered and the filter cake was washed with water and petroleum ether then dried under high vacuum to provide 129 mg (90%) of 2-bromo-5-(2-trimethylsilanyl-ethoxymethyl)-5H- pyrrolo[2,3-b]pyrazine-7-carboxylic acid ((S)-2-methoxy-1-methyl-ethyl)-amide as an off-white powder.

Step 2

2-(6,8-Difluoro-imidazo[1,5-a]pyridin-1-yl)-5-(2-trimethylsilanyl-ethoxymethyl)-5H-pyrrolo[2,3-b]pyrazine-7-carboxylic acid ((S)-2-methoxy-1-methyl-ethyl)-amide

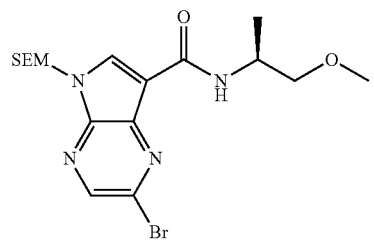

+

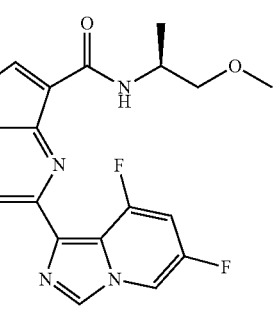

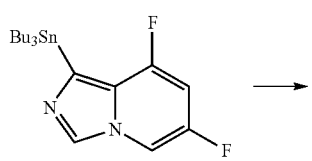

In a round-bottomed flask, 2-bromo-5-(2-trimethylsilanyl-ethoxymethyl)-5H-pyrrolo[2,3-b]pyrazine-7-carboxylic acid ((S)-2-methoxy-1-methyl-ethyl)-amide (125 mg, 0.28 mmol) and 6,8-difluoro-1-tributylstannyl-imidazo[1,5-a]pyridine (458 mg, 0.62 mmol) were dissolved in DMF (2.5 ml). The flask was evacuated and backfilled with argon then tetrakis(triphenylphosphine)palladium (0) (17 mg, 0.015 mmol) and copper (I) iodide (11 mg, 0.058 mmol) were added. The reaction mixture was stirred at 90° C. in an oil bath for 1.5 h then cooled to room temperature, quenched with water and extracted with diethyl ether (2×). The combined organic layers were washed twice with water and once with brine then dried over sodium sulfate, filtered and concentrated. The residue was chromatographed twice over silica gel with MeOH/CH$_2$Cl$_2$/0.5% NH$_4$OH (gradient 0-3% MeOH) to afford 136 mg (89%) of 2-(6,8-difluoro-imidazo[1,5-a]pyridin-1-yl)-5-(2-trimethylsilanyl-ethoxymethyl)-5H-pyrrolo[2,3-b]pyrazine-7-carboxylic acid ((S)-2-methoxy-1-methyl-ethyl)-amide as a yellow solid.

Step 3

2-(6,8-Difluoro-imidazo[1,5-a]pyridin-1-yl)-5H-pyrrolo[2,3-b]pyrazine-7-carboxylic acid ((S)-2-methoxy-1-methyl-ethyl)-amide

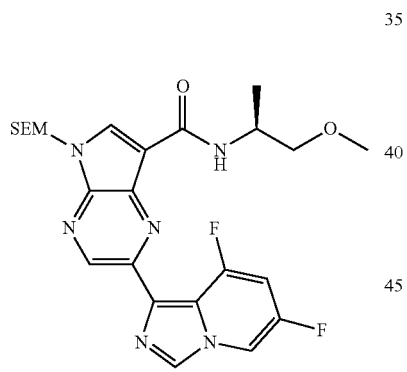

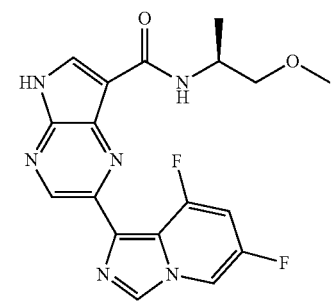

In a round-bottomed flask, 2-(6,8-difluoro-imidazo[1,5-a]pyridin-1-yl)-5-(2-trimethylsilanyl-ethoxymethyl)-5H-pyrrolo[2,3-b]pyrazine-7-carboxylic acid ((S)-2-methoxy-1-methyl-ethyl)-amide (134 mg, 0.25 mmol) was dissolved in dichloromethane (1.2 ml) and trifluoroacetic acid (0.75 ml, 9.8 mmol) was added. The reaction mixture was stirred at room temperature for 2 h then concentrated. The residue was dissolved in dichloromethane (1.2 ml) and ethylenediamine (1.0 ml, 14.8 mmol) was added. The yellow solution was stirred at room temperature for 1 h then quenched with water and diluted with ethyl acetate. The resulting suspension was filtered, washed with hot water and ethyl acetate and dried under high vacuum to provide 74 mg (78%) of 2-(6,8-difluoro-imidazo[1,5-a]pyridin-1-yl)-5H-pyrrolo[2,3-b]pyrazine-7-carboxylic acid ((S)-2-methoxy-1-methyl-ethyl)-amide as a yellow powder. MS: (M+H)$^+$=387; $^1$H NMR (DMSO-d$_6$, 300 MHz): δ (ppm) 12.14 (br. s., 1H), 9.03 (s, 1H), 8.70 (d, J=1.9 Hz, 1H), 8.63 (dd, J=4.2, 1.9 Hz, 1H), 8.37 (s, 1H), 8.29 (d, J=8.3 Hz, 1H), 7.24-7.36 (m, 1H), 4.32 (dt, J=13.2, 6.6 Hz, 1H), 3.42-3.51 (m, 1H), 3.35-3.41 (m, 1H), 3.25 (s, 3H), 1.24 (d, J=6.8 Hz, 3H).

Example 41

2-(6-Fluoro-imidazo[1,5-a]pyridin-1-yl)-5H-pyrrolo[2,3-b]pyrazine-7-carboxylic acid ((S)-2-methoxy-1-methyl-ethyl)-amide

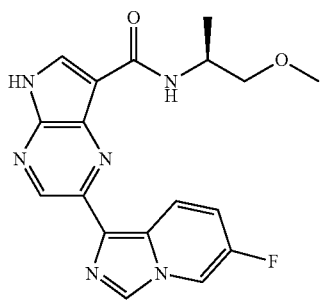 [SMILES: COC[C@H](C)NC(=O)c1c[nH]c2ncc(-c3ncn4cc(F)ccc34)nc12]

Prepared according to the procedure outlined in Example 40, Steps 2-3, substituting 6-fluoro-1-tributylstannyl-imidazo[1,5-a]pyridine for 6,8-difluoro-1-tributylstannyl-imidazo[1,5-a]pyridine in Step 2. MS: (M+H)+=369; $^1$H NMR (DMSO-d$_6$, 300 MHz): δ (ppm) 12.15 (br. s., 1H), 9.11 (s, 1H), 8.68-8.75 (m, 1H), 8.54 (s, 1H), 8.44 (dd, J=9.8, 5.7 Hz, 1H), 8.35 (s, 1H), 8.16 (d, J=8.7 Hz, 1H), 7.08-7.18 (m, 1H), 4.39 (d, J=7.2 Hz, 1H), 3.49 (qd, J=9.8, 4.5 Hz, 2H), 3.30 (s, 3H), 1.31 (d, J=6.8 Hz, 3H).

Example 42

2-(6-Fluoro-3-methanesulfonyl-imidazo[1,5-a]pyridin-1-yl)-5H-pyrrolo[2,3-b]pyrazine-7-carboxylic acid [(R)-2-(3-cyano-azetidin-1-yl)-1-methyl-2-oxo-ethyl]-amide

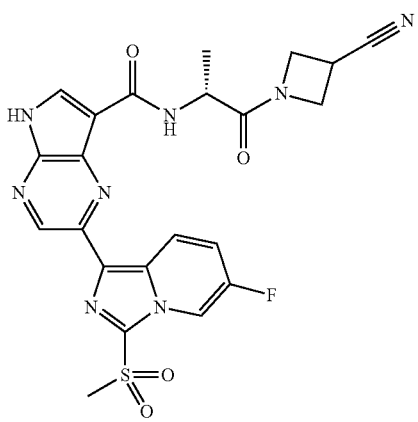 [SMILES: C[C@@H](NC(=O)c1c[nH]c2ncc(-c3nc(S(C)(=O)=O)n4cc(F)ccc34)nc12)C(=O)N1CC(C#N)C1]

Step 1

6-Fluoro-2H-imidazo[1,5-a]pyridine-3-thione

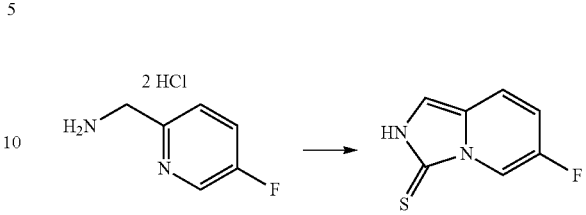

In a round-bottomed flask, (5-fluoropyridin-2-yl)methylamine dihydrochloride (600 mg, 3.0 mmol) was suspended in methanol (16 ml). Triethylamine (1.4 ml, 10.0 mmol) was added followed by carbon disulfide (1.4 ml, 23.2 mmol). The reaction mixture was stirred at reflux (oil bath temperature=75° C.) overnight then cooled to room temperature and then concentrated. The residue was partitioned between dichloromethane and water. The aqueous layer was extracted with dichloromethane then the organic layers were combined, dried over sodium sulfate, filtered and concentrated. The residue was absorbed on silica gel and chromatographed with EtOAc/hexanes (gradient 0-60% EtOAc) to afford 169 mg (33%) of 6-fluoro-2H-imidazo[1,5-a]pyridine-3-thione as an orange solid. $^1$H NMR (DMSO-d$_6$, 300 MHz): δ (ppm) 13.47 (br. s., 1H), 8.04 (dd, J=4.9, 1.1 Hz, 1H), 7.43-7.56 (m, 2H), 6.88 (ddd, J=10.0, 7.9, 2.1 Hz, 1H).

Step 2

6-Fluoro-3-methylsulfanyl-imidazo[1,5-a]pyridine

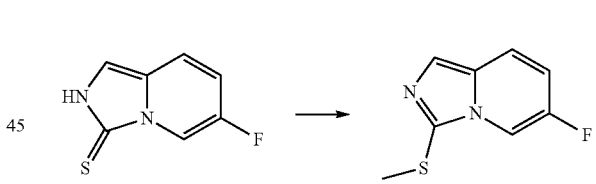

In a round-bottomed flask, 6-fluoro-2H-imidazo[1,5-a]pyridine-3-thione (158 mg, 0.94 mmol) was suspended in methanol (1 ml) and sodium methoxide (0.5 M in MeOH, 2.0 ml, 1.0 mmol) was added dropwise. The reaction was stirred at room temperature for 10 min then methyl iodide (0.07 ml, 1.12 mmol) was added dropwise. The reaction mixture was stirred at room temperature for 2 h then concentrated. The residue was partitioned between dichloromethane and water. The aqueous layer was extracted with dichloromethane then the organic layers were combined, dried over sodium sulfate, filtered and concentrated to afford 179 mg of 6-fluoro-3-methylsulfanyl-imidazo[1,5-a]pyridine as a brown oil which was used without further purification. $^1$H NMR (CDCl$_3$, 400

MHz): δ (ppm) 7.98-8.05 (m, 1H), 7.58 (s, 1H), 7.45 (dd, J=9.3, 4.8 Hz, 1H), 6.73 (ddd, J=9.6, 7.6, 2.0 Hz, 1H), 2.56 (s, 3H).

Step 3

6-Fluoro-1-iodo-3-methylsulfanyl-imidazo[1,5-a]pyridine

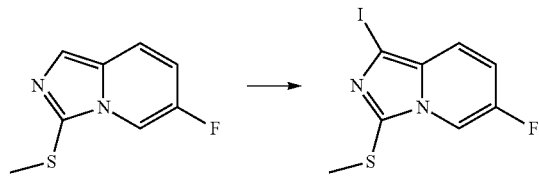

In a round-bottomed flask, 6-fluoro-3-methylsulfanyl-imidazo[1,5-a]pyridine (178 mg, 0.88 mmol) was dissolved in ethanol (1.6 ml). Water (0.8 ml), sodium bicarbonate (278 mg, 3.31 mmol) and iodine (312 mg, 1.23 mmol) were added. The dark brown suspension was stirred at room temperature overnight then quenched with 10% aqueous $Na_2S_2O_3$ and extracted with EtOAc (2×). The combined organic layers were washed with 10% aqueous $Na_2S_2O_3$, water, and brine then dried over sodium sulfate, filtered and concentrated. The residue was absorbed on silica gel and chromatographed with EtOAc/hexanes (gradient 0-10% EtOAc) to afford 110 mg (41%) of 6-fluoro-1-iodo-3-methylsulfanyl-imidazo[1,5-a]pyridine as a brown solid.

Step 4

6-Fluoro-3-methylsulfanyl-1-tributylstannanyl-imidazo[1,5-a]pyridine

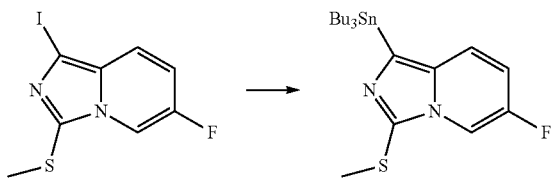

In a round-bottomed flask, 6-fluoro-1-iodo-3-methylsulfanyl-imidazo[1,5-a]pyridine (109 mg, 0.35 mmol) was dissolved in THF (3 ml). The light brown solution was cooled to −16° C. (NaCl/ice bath) and isopropylmagnesium chloride (2.0 M in THF, 0.21 ml, 0.42 mmol) was added dropwise. The reaction mixture was stirred at −16° C. for 20 min then tributylchlorostannane (0.11 ml, 0.40 mmol) was slowly added. The reaction mixture was allowed to warm to room temperature and stirred for 2 h then quenched with saturated aqueous $NH_4Cl$ and extracted with ethyl acetate (2×). The combined organic layers were washed with water and brine then dried over sodium sulfate, filtered and concentrated to give 6-fluoro-3-methylsulfanyl-1-tributylstannanyl-imidazo[1,5-a]pyridine as a brown oil which was used without further purification.

Step 5

2-(6-Fluoro-3-methylsulfanyl-imidazo[1,5-a]pyridin-1-yl)-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide

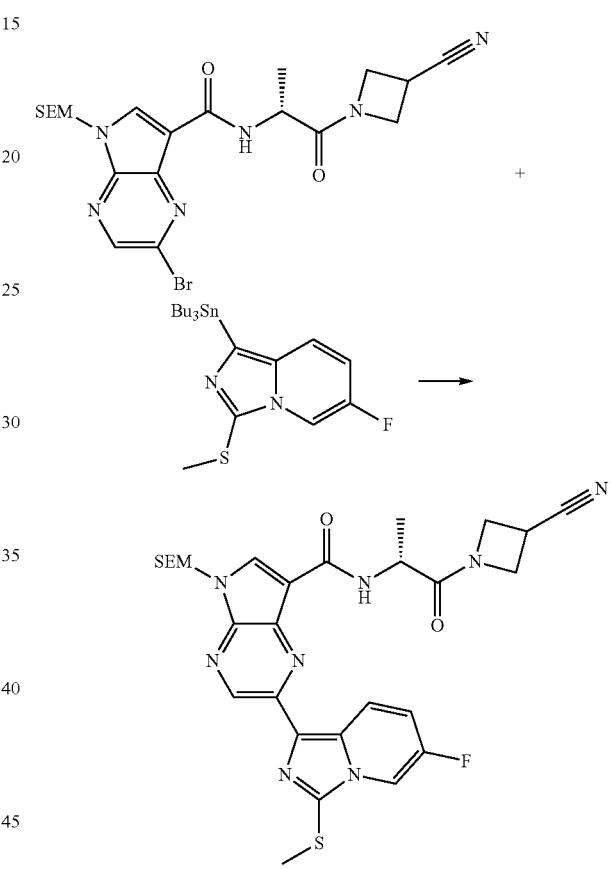

In a round-bottomed flask, 2-bromo-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide (100 mg, 0.20 mmol) and 6-fluoro-3-methylsulfanyl-1-tributylstannanyl-imidazo[1,5-a]pyridine (crude from Step 4) were dissolved in DMF (2 ml). The flask was evacuated and backfilled with argon then tetrakis(triphenylphosphine)palladium (0) (12 mg, 0.010 mmol) and copper (I) iodide (8 mg, 0.042 mmol) were added. The reaction mixture was stirred at 80° C. in an oil bath overnight then cooled to room temperature, quenched with water and extracted with diethyl ether (2×). The combined organic layers were washed twice with water and once with brine then dried over sodium sulfate, filtered and concentrated. The residue was chromatographed over silica gel with $MeOH/CH_2Cl_2/0.5\%$ $NH_4OH$ (gradient 0-2.5% MeOH) to afford 109 mg (82%) of 2-(6-fluoro-3-methylsulfanyl-imidazo[1,5-a]pyridin-1-yl)-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide as a brown oil.

Step 6

2-(6-Fluoro-3-methanesulfonyl-imidazo[1,5-a]pyridin-1-yl)-5-(2-trimethylsilanylethoxymethyl)-5H-pyrrolo[2,3-b]pyrazine-7-carboxylic acid [(R)-2-(3-cyano-azetidin-1-yl)-1-methyl-2-oxo-ethyl]-amide

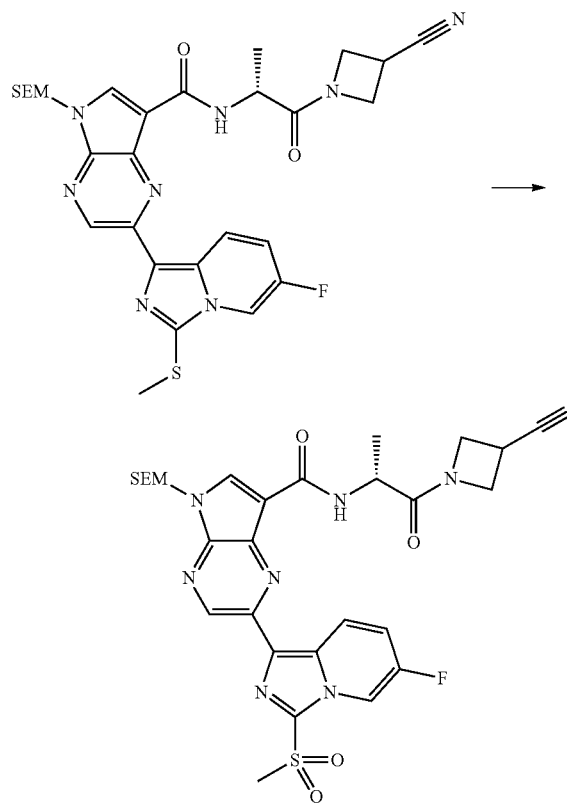

In a round-bottomed flask, 2-(6-fluoro-3-methylsulfanyl-imidazo[1,5-a]pyridin-1-yl)-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide (105 mg, 0.155 mmol) was dissolved in dichloromethane (4 ml). The solution was cooled to 0° C. and m-CPBA (75%, 79 mg, 0.343 mmol) was added. The ice bath was removed and the reaction mixture was stirred at room temperature overnight. Additional m-CPBA (75%, 36 mg, 0.155 mmol) was added and the reaction mixture was stirred at room temperature for 30 min. A solution of 10% aqueous $Na_2S_2O_3$ (3 ml) was added and the biphasic mixture was stirred at room temperature for 1 h. The reaction mixture was diluted with water and extracted with dichloromethane. The organic layer was washed with saturated aqueous $NaHCO_3$. The aqueous layer was extracted dichloromethane (2×). The combined organic layers were dried over sodium sulfate, filtered and concentrated. The residue was chromatographed over silica gel with MeOH/$CH_2Cl_2$/0.5% $NH_4OH$ (gradient 0-2.5% MeOH) to afford 25 mg (25%) of 2-(6-fluoro-3-methanesulfonyl-imidazo[1,5-a]pyridin-1-yl)-5-(2-trimethylsilanyl-ethoxym-ethyl)-5H-pyrrolo[2,3-b]pyrazine-7-carboxylic acid [(R)-2-(3-cyano-azetidin-1-yl)-1-methyl-2-oxo-ethyl]-amide as a light brown oil.

Step 7

2-(6-Fluoro-3-methanesulfonyl-imidazo[1,5-a]pyridin-1-yl)-5H-pyrrolo[2,3-b]pyrazine-7-carboxylic acid [(R)-2-(3-cyano-azetidin-1-yl)-1-methyl-2-oxo-ethyl]-amide

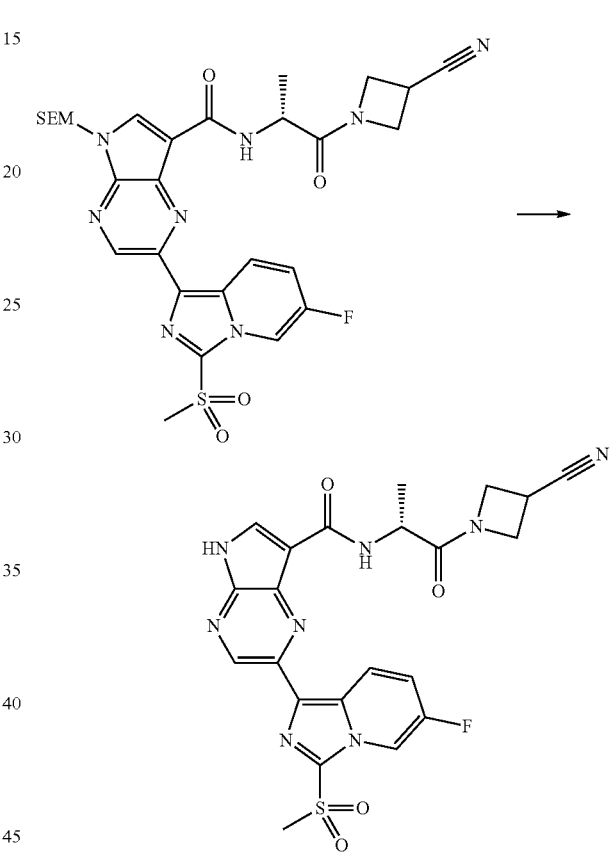

In a round-bottomed flask, 2-(6-fluoro-3-methanesulfonyl-imidazo[1,5-a]pyridin-1-yl)-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide (0.024 g, 37.5 μmol, Eq: 1.00) was dissolved in dichloromethane (0.3 ml) and trifluoroacetic acid (0.12 ml, 1.6 mmol) was added. The reaction mixture was stirred at room temperature for 2.5 h then concentrated. The residue was redissolved in dichloromethane/methanol/ammonium hydroxide (60:10:1) (3.5 ml). The solution was stirred at room temperature overnight then concentrated. The residue was absorbed on silica gel and chromatographed with MeOH/$CH_2Cl_2$/0.5% $NH_4OH$ (gradient 0-7% MeOH) to afford 6 mg (30%) of 2-(6-fluoro-3-methanesulfonyl-imidazo[1,5-a]pyridin-1-yl)-5H-pyrrolo[2,3-b]pyrazine-7-carboxylic acid [(R)-2-(3-cyano-azetidin-1-yl)-1-methyl-2-oxo-ethyl]-amide as a yellow solid. MS: $(M+H)^+$=511; $^1H$ NMR (DMSO-$d_6$, 300 MHz): δ (ppm) 12.92 (br. s., 1H), 9.17 (s, 1H), 9.01-9.10 (m, 1H), 8.95 (d, J=3.0 Hz, 1H), 8.47-8.53 (m, 1H), 8.42 (d, J=7.6 Hz, 1H), 7.43-7.53 (m, 1H), 4.51-4.80 (m, 3H), 4.27 (q, J=9.6 Hz, 1H), 4.11-4.21 (m, 1H), 3.81-3.94 (m, 1H), 3.57 (s, 3H), 1.40 (t, J=6.4 Hz, 3H).

Example 43

2-(6-Chloro-1-methyl-1H-indazol-3-yl)-5H-pyrrolo[2,3-b]pyrazine-7-carboxylic acid [(R)-1-(3-cyano-azetidine-1-carbonyl)-2,2-dimethyl-propyl]-amide

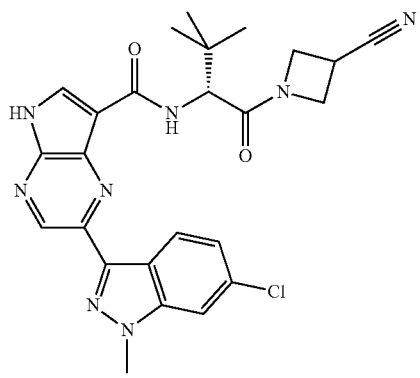 [SMILES: Cn1nc(-c2cnc3[nH]cc(C(=O)N[C@@H](C(=O)N4CC(C#N)C4)C(C)(C)C)c3n2)c2ccc(Cl)cc21]

Step 1

[(R)-1-(3-Cyano-azetidine-1-carbonyl)-2,2-dimethyl-propyl]-carbamic acid tert-butyl ester

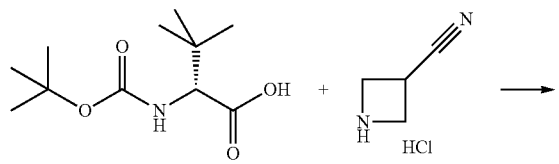

A round-bottomed flask was charged with Boc-D-tert-leucine (300 mg, 1.3 mmol) and azetidine-3-carbonitrile hydrochloride (231 mg, 1.95 mmol). DMF (6 ml) was added followed by N,N-diisopropylethylamine (0.68 ml, 3.9 mmol) and HATU (543 mg, 1.43 mmol). The light yellow solution was stirred at room temperature for 48 h then quenched with water and extracted with diethyl ether (2×). The combined organic layers were washed twice with water and once with brine then dried over sodium sulfate, filtered and concentrated to afford 458 mg of [(R)-1-(3-cyano-azetidine-1-carbonyl)-2,2-dimethyl-propyl]-carbamic acid tert-butyl ester as a light yellow oil.

Step 2

1-((R)-2-Amino-3,3-dimethyl-butyryl)-azetidine-3-carbonitrile trifluoroacetate

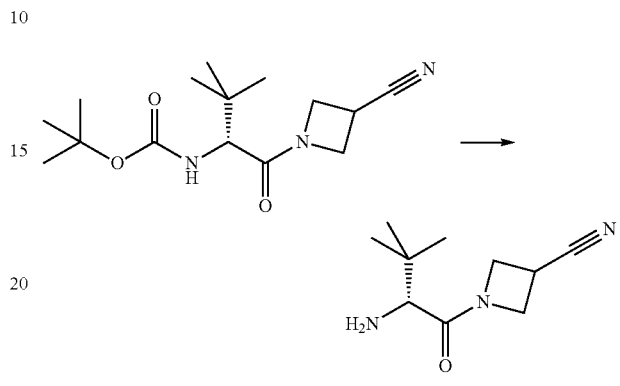

To a solution [(R)-1-(3-cyano-azetidine-1-carbonyl)-2,2-dimethyl-propyl]-carbamic acid tert-butyl ester (180 mg, 0.49 mmol) in dichloromethane (3 ml) at 0° C. was added trifluoroacetic acid (1.2 ml, 15.6 mmol). The reaction mixture was stirred at room temperature for 2 h then concentrated to afford 1-((R)-2-amino-3,3-dimethyl-butyryl)-azetidine-3-carbonitrile trifluoroacetate as a light yellow oil which was used without further purification.

Step 3

2-(6-Chloro-1-methyl-1H-indazol-3-yl)-5H-pyrrolo[2,3-b]pyrazine-7-carboxylic acid [(R)-1-(3-cyano-azetidine-1-carbonyl)-2,2-dimethyl-propyl]-amide

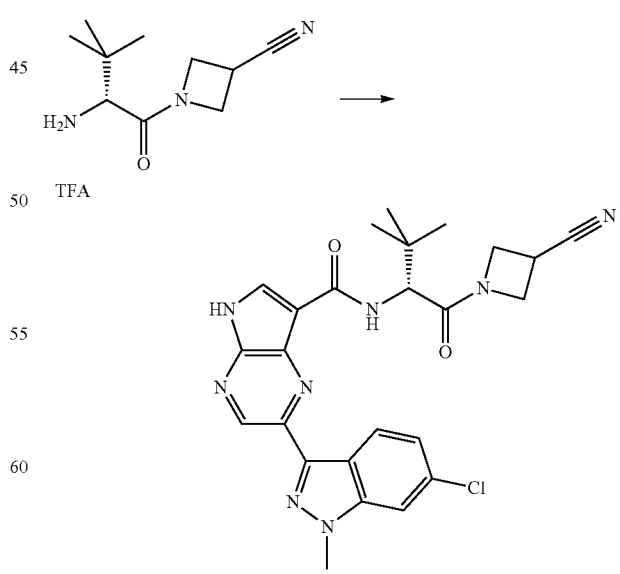

Prepared according to the procedure outlined in Example 14, Steps 5-6, substituting 1-((R)-2-amino-3,3-dimethyl-butyryl)-azetidine-3-carbonitrile trifluoroacetate for (R)-2-amino-1-(3,3-difluoro-azetidin-1-yl)-propan-1-one in Step 5. MS: (M+H)⁺=505; ¹H NMR (DMSO-d₆, 300 MHz): δ (ppm) 12.92 (br. s., 1H), 9.15 (s, 1H), 8.90 (dd, J=8.5, 5.9 Hz, 1H), 8.54 (d, J=9.8 Hz, 1H), 8.49 (d, J=7.6 Hz, 1H), 7.94 (s, 1H), 7.21 (d, J=8.7 Hz, 1H), 4.57-4.70 (m, 2H), 4.52 (m, 1H), 4.17 (s, 3H), 4.07-4.31 (m, 2H), 3.76-3.95 (m, 1H), 1.01 (d, J=4.2 Hz, 9H).

Example 44

2-(6-Fluoro-1-methyl-1H-indazol-3-yl)-5H-pyrrolo[2,3-b]pyrazine-7-carboxylic acid ((R)-2-fluoro-1,2-dimethyl-propyl)-amide

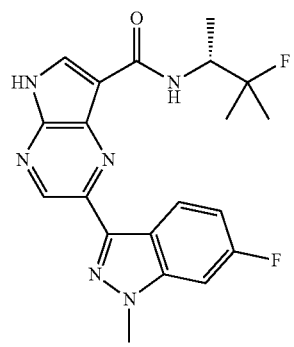 [SMILES: C[C@@H](NC(=O)c1c[nH]c2ncc(-c3nn(C)c4cc(F)ccc34)nc12)C(C)(C)F]

Step 1

((R)-2-Hydroxy-1,2-dimethyl-propyl)-carbamic acid tert-butyl ester

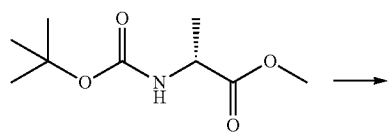

To a solution of Boc-D-alanine methyl ester (5.00 g, 24.6 mmol) in THF (100 mL) at 0° C. was slowly added methyl magnesium bromide (3.0 M in Et₂O, 28.7 mL, 86.1 mmol). The resultant white slurry was stirred at 0° C. for 1 h then at room temperature for 2 h. The reaction mixture was quenched with saturated aqueous NH₄Cl, diluted with H₂O and extracted with EtOAc. The combined organics were washed with brine, dried over MgSO₄ and concentrated to give 4.93 g (99%) ((R)-2-hydroxy-1,2-dimethyl-propyl)-carbamic acid tert-butyl ester as a colorless viscous oil.

Step 2

((R)-2-Fluoro-1,2-dimethyl-propyl)-carbamic acid tert-butyl ester

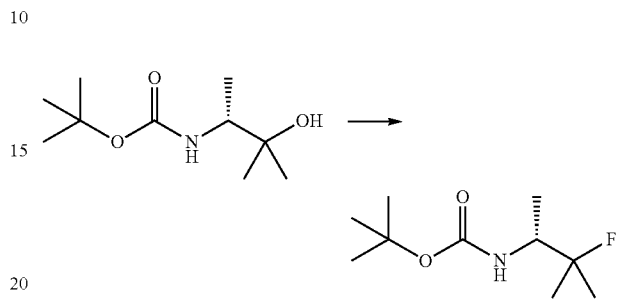

In a dry round-bottomed flask, ((R)-2-hydroxy-1,2-dimethyl-propyl)-carbamic acid tert-butyl ester (534 mg, 2.36 mmol) was dissolved in dichloromethane (22 ml). The solution was cooled to −76° C. and DAST (0.34 ml, 2.57 mmol) was added dropwise. The reaction mixture was stirred at −76° C. for 1.5 h then quenched with saturated aqueous NaHCO₃ (5 mL), warmed to room temperature and extracted with dichloromethane (2×). The organic layers were combined, dried over sodium sulfate, filtered and concentrated to afford 534 mg of ((R)-2-fluoro-1,2-dimethyl-propyl)-carbamic acid tert-butyl ester as a yellow oil which was used without further purification.

Step 3

(R)-2-Fluoro-1,2-dimethyl-propylamine hydrochloride

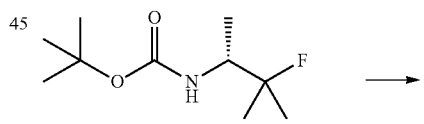

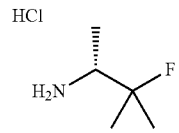

((R)-2-Fluoro-1,2-dimethyl-propyl)-carbamic acid tert-butyl ester (140 mg, 0.61 mmol) was dissolved in 1.0 M HCl solution in MeOH (10 mL). The reaction mixture was stirred at room temperature overnight then concentrated to provide

Step 4

2-(6-Fluoro-1-methyl-1H-indazol-3-yl)-5-(2-trimethylsilanyl-ethoxymethyl)-5H-pyrrolo[2,3-b]pyrazine-7-carboxylic acid ((R)-2-fluoro-1,2-dimethyl-propyl)-amide

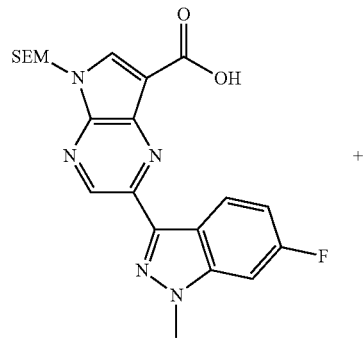

+

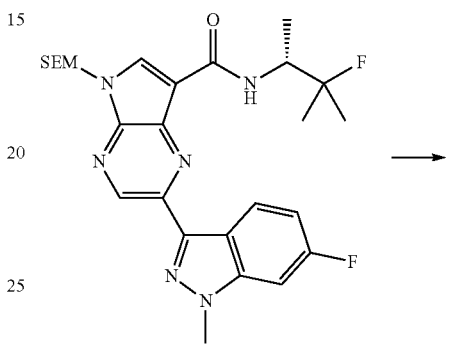

A 10 ml round-bottomed flask was charged with 2-(6-fluoro-1-methyl-1H-indazol-3-yl)-5-(2-trimethylsilanyl-ethoxymethyl)-5H-pyrrolo[2,3-b]pyrazine-7-carboxylic acid (120 mg, 0.27 mmol) and (R)-2-fluoro-1,2-dimethyl-propylamine hydrochloride (crude from Step 3, 155 mg, 0.55 mmol). DMF (1.2 ml) was added followed by N,N-diisopropylethylamine (0.20 ml, 1.15 mmol) and HATU (114 mg, 0.30 mmol). The reaction mixture was stirred at room temperature for 5 h. Water was added and the resultant suspension was filtered. The filter cake was washed with water and petroleum ether then dried under high vacuum to afford 95 mg (66%) of 2-(6-fluoro-1-methyl-1H-indazol-3-yl)-5-(2-trimethylsilanyl-ethoxymethyl)-5H-pyrrolo[2,3-b]pyrazine-7-carboxylic acid ((R)-2-fluoro-1,2-dimethyl-propyl)-amide as a light brown powder.

Step 5

2-(6-Fluoro-1-methyl-1H-indazol-3-yl)-5H-pyrrolo[2,3-b]pyrazine-7-carboxylic acid ((R)-2-fluoro-1,2-dimethyl-propyl)-amide

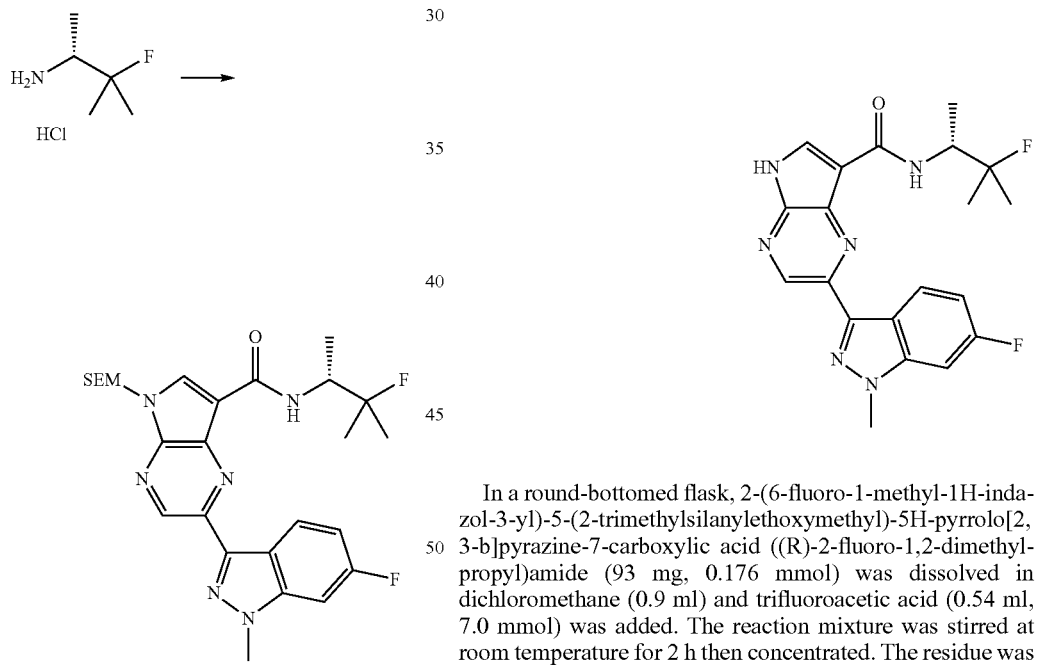

In a round-bottomed flask, 2-(6-fluoro-1-methyl-1H-indazol-3-yl)-5-(2-trimethylsilanylethoxymethyl)-5H-pyrrolo[2,3-b]pyrazine-7-carboxylic acid ((R)-2-fluoro-1,2-dimethyl-propyl)amide (93 mg, 0.176 mmol) was dissolved in dichloromethane (0.9 ml) and trifluoroacetic acid (0.54 ml, 7.0 mmol) was added. The reaction mixture was stirred at room temperature for 2 h then concentrated. The residue was dissolved in dichloromethane (0.9 ml) and ethylenediamine (0.7 ml, 10.5 mmol) was added. The yellow solution was stirred at room temperature for 1 h then quenched with water and extracted with dichloromethane (2×). The organic layers were combined, dried over sodium sulfate, filtered and concentrated. The residue was absorbed on silica gel and chromatographed with MeOH/CH$_2$Cl$_2$/0.5% NH$_4$OH (gradient 0-6% MeOH) then triturated with ethyl acetate to afford 34 mg (46%) of 2-(6-fluoro-1-methyl-1H-indazol-3-yl)-5H-pyrrolo[2,3-b]pyrazine-7-carboxylic acid ((R)-2-fluoro-1,2-dimethyl-propyl)-amide as a light yellow powder. MS: (M+H)$^+$=399; $^1$H NMR (DMSO-d$_6$, 300 MHz): δ (ppm) 12.90 (br. s., 1H), 9.12 (s, 1H), 8.45-8.54 (m, 2H), 8.25 (d, J=9.8 Hz, 1H), 7.68 (dd, J=9.8, 2.3 Hz, 1H), 7.09 (td, J=9.1, 2.3 Hz, 1H), 4.30-4.48 (m, 1H), 4.15 (s, 3H), 1.29-1.52 (m, 9H).

Example 45

2-(6-Fluoro-1-methyl-1H-indazol-3-yl)-5H-pyrrolo[2,3-b]pyrazine-7-carboxylic acid ((S)-1,2,2-trimethyl-propyl)-amide

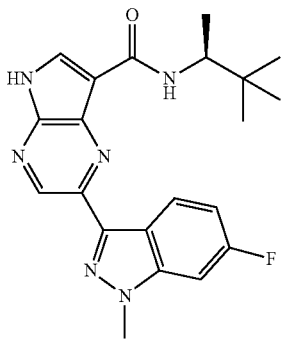 [SMILES: C[C@H](NC(=O)c1c[nH]c2ncc(-c3nn(C)c4cc(F)ccc34)nc12)C(C)(C)C]

Step 1

2-(6-Fluoro-1-methyl-1H-indazol-3-yl)-5-(2-trimethylsilanyl-ethoxymethyl)-5H-pyrrolo[2,3-b]pyrazine-7-carboxylic acid ((S)-1,2,2-trimethyl-propyl)-amide

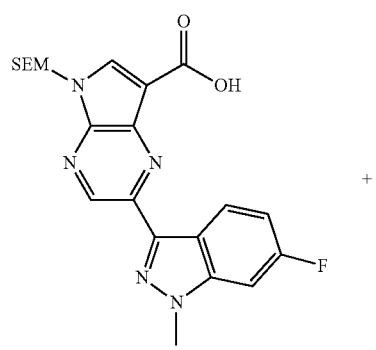

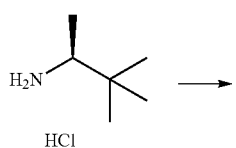

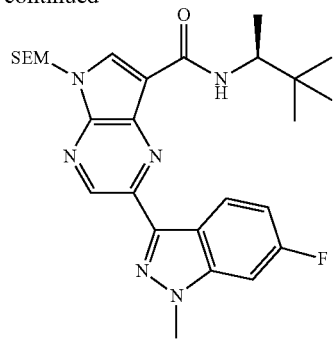

In a round-bottomed flask 2-(6-fluoro-1-methyl-1H-indazol-3-yl)-5-(2-trimethylsilanylethoxymethyl)-5H-pyrrolo[2,3-b]pyrazine-7-carboxylic acid (120 mg, 0.27 mmol) was dissolved in DMF (1.2 ml). (S)-3,3-Dimethylbutan-2-amine (0.25 ml, 1.84 mmol) was added followed by HATU (114 mg, 0.30 mmol) and the yellow solution was stirred at room temperature overnight. Water was added and the resulting suspension was filtered. The filter cake was washed with water and petroleum ether then dried under high vacuum to afford 104 mg (73%) of 2-(6-fluoro-1-methyl-1H-indazol-3-yl)-5-(2-trimethylsilanyl-ethoxymethyl)-5H-pyrrolo[2,3-b]pyrazine-7-carboxylic acid ((S)-1,2,2-trimethyl-propyl)-amide as a light yellow powder.

Step 2

2-(6-Fluoro-1-methyl-1H-indazol-3-yl)-5H-pyrrolo[2,3-b]pyrazine-7-carboxylic acid ((S)-1,2,2-trimethyl-propyl)-amide

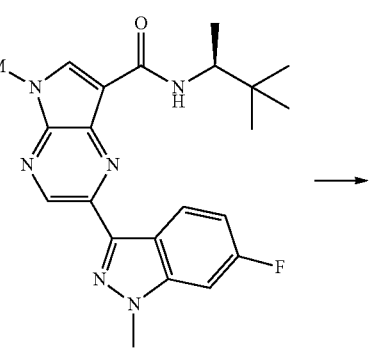

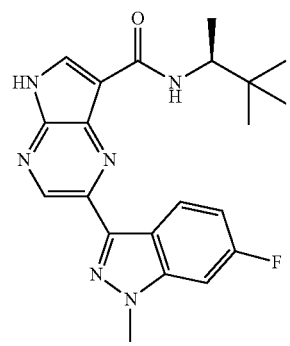

In a round-bottomed flask, 2-(6-fluoro-1-methyl-1H-indazol-3-yl)-5-(2-trimethylsilanylethoxymethyl)-5H-pyrrolo[2,3-b]pyrazine-7-carboxylic acid ((S)-1,2,2-trimethyl-propyl)- amide (102 mg, 0.194 mmol) was dissolved in dichloromethane (0.9 ml) and trifluoroacetic acid (0.6 ml, 7.8 mmol) was added. The reaction mixture was stirred at room temperature for 2 h then concentrated. The residue was dissolved in dichloromethane (0.9 ml) and ethylenediamine (0.8 ml, 11.7 mmol) was added. The yellow solution was stirred at room temperature for 1 h then quenched with water and diluted with ethyl acetate. The suspension was filtered, washed with hot water and ethyl acetate and dried under high vacuum to provide 52 mg (64%) of 2-(6-fluoro-1-methyl-1H-indazol-3-yl)-5H-pyrrolo[2,3-b]pyrazine-7-carboxylic acid ((S)-1,2,2-trimethyl-propyl)-amide as a light yellow powder. MS: (M+H)$^+$=395; $^1$H NMR (DMSO-d$_6$, 300 MHz): δ (ppm) 12.38 (br. s., 1H), 9.08 (s, 1H), 8.44 (s, 1H), 8.40 (dd, J=9.1, 5.3 Hz, 1H), 8.03 (d, J=9.8 Hz, 1H), 7.69 (dd, J=9.8, 1.9 Hz, 1H), 7.20 (td, J=9.1, 2.3 Hz, 1H), 4.15 (s, 3H), 4.09-4.19 (m, 1H), 1.26 (d, J=6.8 Hz, 3H), 0.93 (s, 9H).

Example 46

2-(6-Fluoro-1-methyl-1H-indazol-3-yl)-5H-pyrrolo[2,3-b]pyrazine-7-carboxylic acid (cis-3-hydroxy-cyclopentyl)-amide

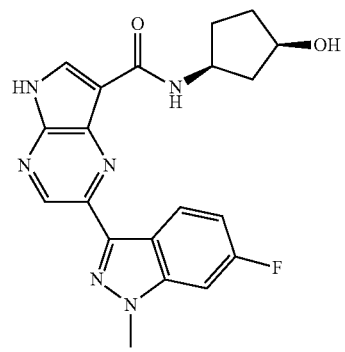 [SMILES: Cn1nc(-c2cnc3[nH]cc(C(=O)N[C@H]4CC[C@@H](O)C4)c3n2)c2ccc(F)cc21]

Step 1

(cis-3-Hydroxy-cyclopentyl)-carbamic acid tert-butyl ester and (trans-3-Hydroxy-cyclopentyl)-carbamic acid tert-butyl ester

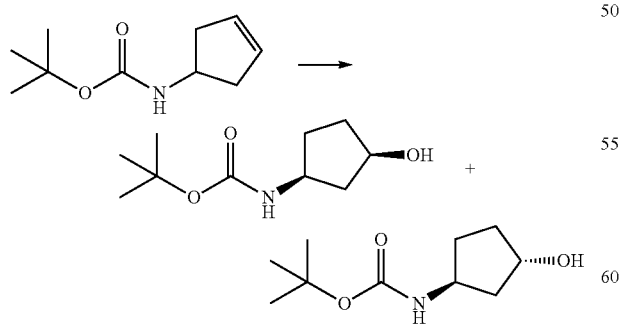

In a dry round-bottomed flask, N-1-Boc-amino-3-cyclopentene (1.0 g, 5.46 mmol) was dissolved in THF (7 ml). The solution was cooled to 0° C. and borane tetrahydrofuran complex (1.0M in THF, 6.0 ml, 6.0 mmol) was added dropwise. The reaction was stirred at 0° C. for 1 h then warmed to room temperature overnight. The mixture was cooled back to 0° C. and water (2 ml) was added. Then 10% aqueous sodium hydroxide (8 ml, 20.0 mmol) was added dropwise followed by dropwise addition of hydrogen peroxide (30% solution in water, 5.0 ml, 49 mmol). After the addition was complete, the ice bath was removed and the reaction mixture was stirred at room temperature for 5 h. The reaction mixture was extracted with ethyl acetate (2×). The combined organic layers were washed with brine then dried over sodium sulfate, filtered and concentrated. The residue was chromatographed over silica gel with EtOAc/hexanes (gradient 0-60% EtOAc) to afford 330 mg (30%) of (cis-3-hydroxy-cyclopentyl)-carbamic acid tert-butyl ester as a colorless oil. $^1$H NMR (CDCl$_3$, 300 MHz): δ (ppm) 5.12 (br. s., 1H), 4.39 (m, 1H), 4.03 (br. s., 1H), 1.95-2.17 (m, 2H), 1.78 (d, J=2.6 Hz, 3H), 1.64 (d, J=12.5 Hz, 1H), 1.44 (s, 9H). Also isolated 99 mg (9%) of (trans-3-hydroxy-cyclopentyl)-carbamic acid tert-butyl ester as a white solid. $^1$H NMR (CDCl$_3$, 300 MHz): δ (ppm) 4.35-4.51 (m, 2H), 4.15 (br. s, 1H), 2.15-2.30 (m, 1H), 1.98-2.10 (m, 2H), 1.45 (s, 9H), 1.34-1.72 (m, 3H).

Step 2 cis-3-Amino-cyclopentanol trifluoroacetate

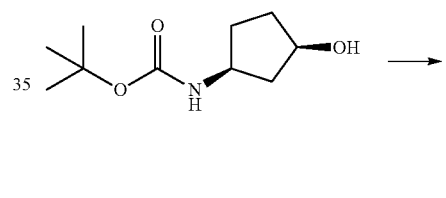

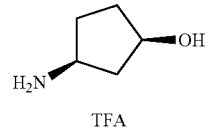

In a round-bottomed flask, (cis-3-hydroxy-cyclopentyl)-carbamic acid tert-butyl ester (320 mg, 1.59 mmol) was dissolved in dichloromethane (10 ml) and trifluoroacetic acid (3.6 ml, 46.7 mmol) was slowly added. The reaction mixture was stirred at room temperature for 2 h then concentrated to afford cis-3-amino-cyclopentanol trifluoroacetate as a light yellow oil which was used without further purification.

Step 3

2-(6-Fluoro-1-methyl-1H-indazol-3-yl)-5-(2-trimethylsilanyl-ethoxymethyl)-5H-pyrrolo[2,3-b]pyrazine-7-carboxylic acid (cis-3-hydroxy-cyclopentyl)-amide

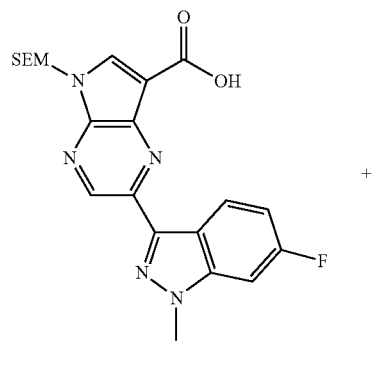

+

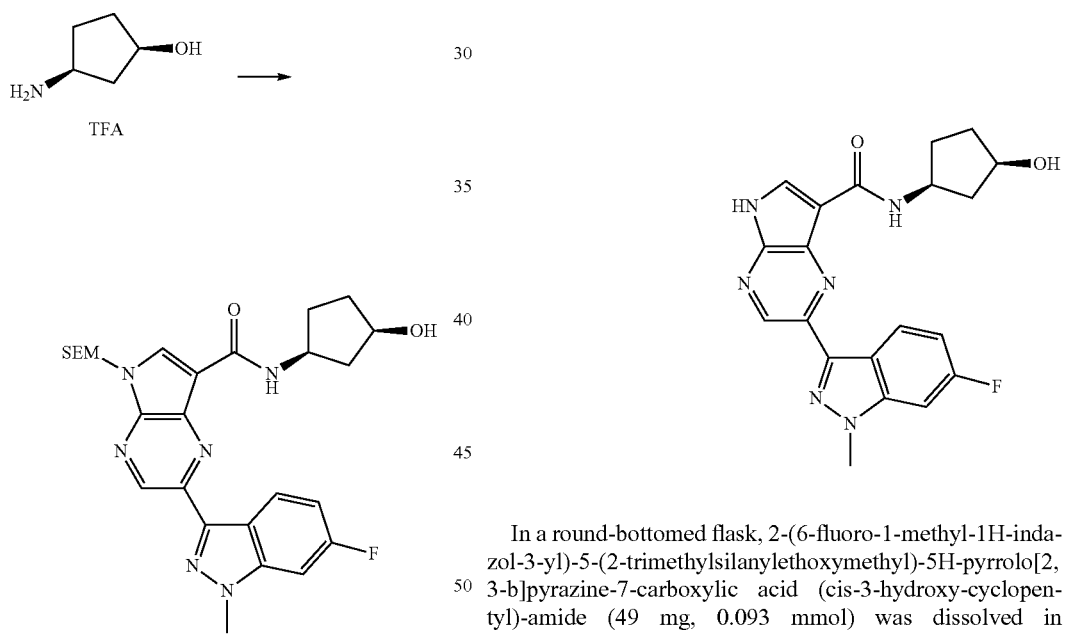

In a round-bottomed flask, cis-3-amino-cyclopentanol trifluoroacetate (crude from Step 2) was dissolved in DMF (1.2 ml) and N,N-diisopropylethylamine (0.40 ml, 2.3 mmol) was added. Then 2-(6-fluoro-1-methyl-1H-indazol-3-yl)-5-(2-trimethylsilanyl-ethoxymethyl)-5H-pyrrolo[2,3-b]pyrazine-7-carboxylic acid (120 mg, 0.27 mmol) and HATU (114 mg, 0.30 mmol) were added. The reaction mixture was stirred at room temperature overnight then quenched with water and extracted with diethyl ether (2×). The combined organic layers were washed twice with water and once with brine then concentrated. The residue was absorbed on silica gel and chromatographed with MeOH/CH$_2$Cl$_2$/0.5% NH$_4$OH (gradient 0-4% MeOH) to afford 50 mg (35%) of 2-(6-fluoro-1-methyl-1H-indazol-3-yl)-5-(2-trimethylsilanyl-ethoxymethyl)-5H-pyrrolo[2,3-b]pyrazine-7-carboxylic acid (cis-3-hydroxy-cyclopentyl)-amide as a light yellow solid.

Step 4

2-(6-Fluoro-1-methyl-1H-indazol-3-yl)-5H-pyrrolo[2,3-b]pyrazine-7-carboxylic acid (cis-3-hydroxy-cyclopentyl)-amide

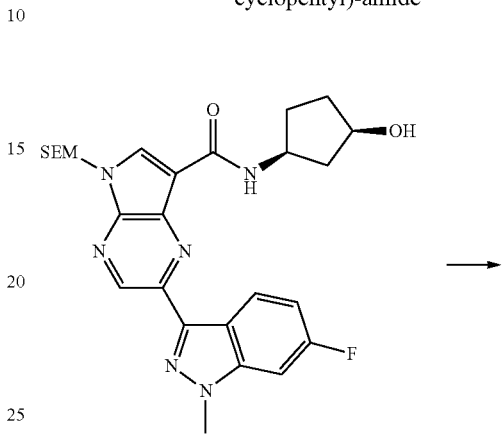

In a round-bottomed flask, 2-(6-fluoro-1-methyl-1H-indazol-3-yl)-5-(2-trimethylsilanylethoxymethyl)-5H-pyrrolo[2,3-b]pyrazine-7-carboxylic acid (cis-3-hydroxy-cyclopentyl)-amide (49 mg, 0.093 mmol) was dissolved in dichloromethane (0.5 ml) and trifluoroacetic acid (0.3 ml, 3.8 mmol) was added. The orange reaction mixture was stirred at room temperature for 2 h then concentrated. The residue was dissolved in dichloromethane (0.5 ml) and ethylenediamine (0.4 ml, 5.7 mmol) was added. The light yellow solution was stirred at room temperature for 1 h then quenched with water and diluted with ethyl acetate. The resulting precipitate was filtered, washed with hot water and ethyl acetate and dried under high vacuum to provide 29 mg (75%) of 2-(6-fluoro-1-methyl-1H-indazol-3-yl)-5H-pyrrolo[2,3-b]pyrazine-7-carboxylic acid (cis-3-hydroxy-cyclopentyl)-amide as an off-white powder. MS: (M+H)$^+$=395; $^1$H NMR (DMSO-d$_6$, 300 MHz): δ (ppm) 12.42 (br. s., 1H), 9.11 (s, 1H), 8.59 (dd, J=9.1, 5.3 Hz, 1H), 8.42 (s, 1H), 8.20 (d, J=8.3 Hz, 1H), 7.68 (dd, J=9.6, 2.1 Hz, 1H), 7.24 (td, J=9.2, 2.1 Hz, 1H), 4.78 (br.

s., 1H), 4.36-4.52 (m, 1H), 4.22 (br. s., 1H), 4.15 (s, 3H), 2.30 (ddd, J=13.7, 8.2, 5.7 Hz, 1H), 2.04-2.19 (m, 1H), 1.67-1.86 (m, 3H), 1.49-1.63 (m, 1H).

Example 47

2-(6-Fluoro-1-methyl-1H-indazol-3-yl)-5H-pyrrolo[2,3-b]pyrazine-7-carboxylic acid (trans-3-hydroxycyclopentyl)-amide

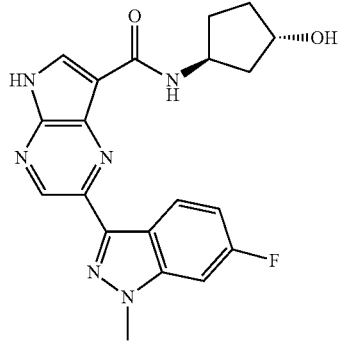 [SMILES: Cn1nc(-c2cnc3[nH]cc(C(=O)N[C@H]4CC[C@H](O)C4)c3n2)c2ccc(F)cc21]

Prepared according to the procedure outlined in Example 46, but substituting (trans-3-hydroxy-cyclopentyl)-carbamic acid tert-butyl ester for (cis-3-hydroxy-cyclopentyl)-carbamic acid tert-butyl ester in Step 2. MS: (M+H)$^+$=395. $^1$H NMR (DMSO-d$_6$, 300 MHz): δ (ppm) 12.26 (br. s., 1H), 9.06 (s, 1H), 8.36-8.47 (m, 2H), 8.09 (d, J=7.6 Hz, 1H), 7.69 (d, J=9.8 Hz, 1H), 7.06-7.22 (m, 1H), 4.49-4.71 (m, 2H), 4.30 (br. s., 1H), 4.13 (s, 3H), 2.17-2.32 (m, 1H), 1.92-2.10 (m, 2H), 1.65-1.77 (m, 1H), 1.43-1.62 (m, 2H).

Example 48

2-(6-Chloro-1-methyl-1H-indazol-3-yl)-5H-pyrrolo[2,3-b]pyrazine-7-carboxylic acid (1-oxazol-2-yl-ethyl)-amide

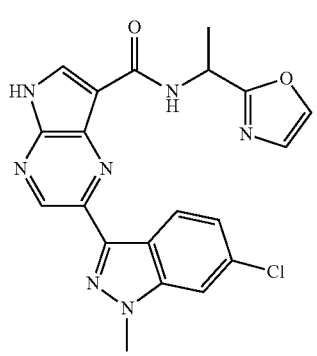 [SMILES: CC(NC(=O)c1c[nH]c2ncc(-c3nn(C)c4cc(Cl)ccc34)nc12)c1ncco1]

Step 1

2-Methyl-propane-2-sulfinic acid 1-oxazol-2-yl-meth-(E)-ylideneamide

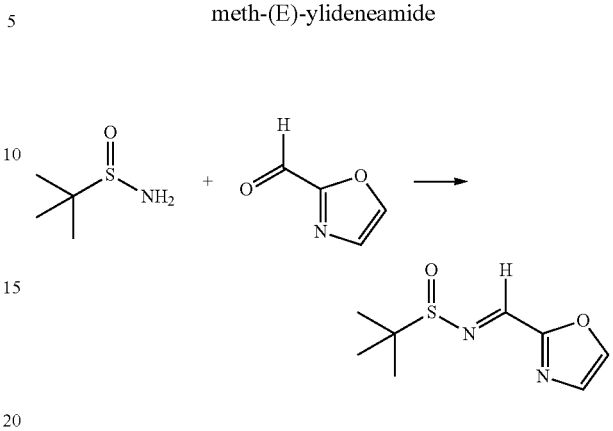

In a round-bottomed flask, oxazole-2-carbaldehyde (300 mg, 3.09 mmol) was dissolved in THF (7 ml) and 2-methyl-propane-2-sulfinamide (450 mg, 3.71 mmol) and titanium (IV) ethoxide (1.3 ml, 6.18 mmol) were added. The reaction mixture was stirred at room temperature overnight then slowly quenched by dropwise addition of brine (2 ml) which resulted in the formation of a thick yellow precipitate. The reaction mixture was diluted with ethyl acetate and stirred vigorously at room temperature for 10 min. The suspension was filtered over Celite and rinsed with ethyl acetate. The filtrate was concentrated and the residue was chromatographed over silica gel with EtOAc/hexanes (gradient 0-30% EtOAc) to afford 419 mg (68%) of 2-methyl-propane-2-sulfinic acid 1-oxazol-2-yl-meth-(E)-ylideneamide as a light yellow solid.

Step 2

2-Methyl-propane-2-sulfinic acid (1-oxazol-2-yl-ethyl)-amide

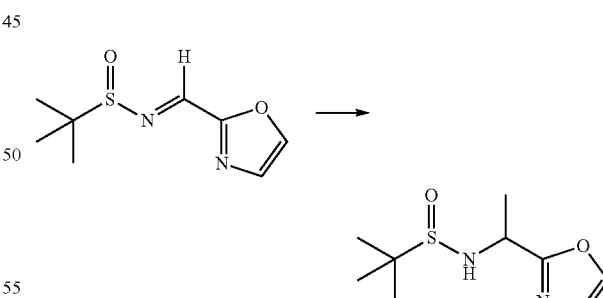

In a round-bottomed flask, 2-methyl-propane-2-sulfinic acid 1-oxazol-2-yl-meth-(E)-ylideneamide (414 mg, 2.07 mmol) was dissolved in dichloromethane (7 ml). The reaction mixture was cooled to 0° C. and methylmagnesium bromide (3.0 M in diethyl ether, 0.76 ml, 2.28 mmol) was added dropwise. The reaction mixture was stirred at 0° C. for 1 h then quenched with saturated aqueous NH$_4$Cl and extracted with ethyl acetate (2×). The combined organic layers were washed with water and brine then dried over sodium sulfate, filtered and concentrated to afford 453 mg (96%) of 2-methyl-propane-2-sulfinic acid (1-oxazol-2-yl-ethyl)-amide as a yellow oil.

Step 3

1-Oxazol-2-yl-ethylamine dihydrochloride

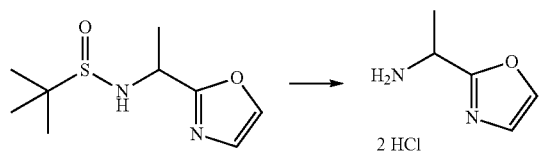

In a round-bottomed flask, 2-methyl-propane-2-sulfinic acid (1-oxazol-2-yl-ethyl)-amide (449 mg, 1.97 mmol) was dissolved in methanol (3.5 ml) and hydrogen chloride (4.0 M in 1,4-dioxane, 1.0 ml, 4.0 mmol) was added dropwise. The reaction mixture was stirred at room temperature for 15 min then concentrated to give 417 mg of 1-oxazol-2-yl-ethylamine dihydrochloride as an orange waxy solid which was used without further purification.

Step 4

2-(6-Chloro-1-methyl-1H-indazol-3-yl)-5-(2-trimethylsilanyl-ethoxymethyl)-5H-pyrrolo[2,3-b]pyrazine-7-carboxylic acid (1-oxazol-2-yl-ethyl)-amide

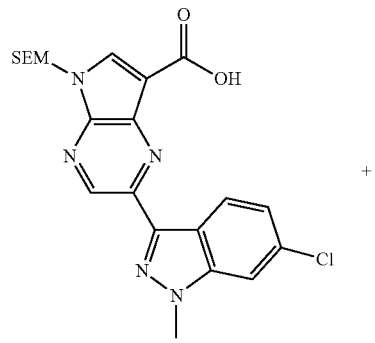

+

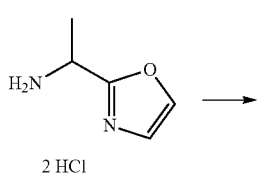

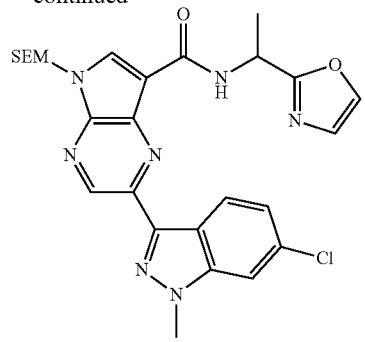

A round-bottomed flask was charged with 2-(6-chloro-1-methyl-1H-indazol-3-yl)-5-(2-trimethylsilanyl-ethoxymethyl)-5H-pyrrolo[2,3-b]pyrazine-7-carboxylic acid (100 mg, 0.22 mmol) and 1-oxazol-2-yl-ethylamine dihydrochloride (91 mg, 0.39 mmol). DMF (1 ml) was added followed by N,N-diisopropylethylamine (0.25 ml, 1.43 mmol) and HATU (92 mg, 0.24 mmol). The light yellow solution was stirred at room temperature for 48 h. Water was added and the resulting suspension was filtered. The solid was washed with water and petroleum ether then dried under high vacuum to afford 108 mg (90%) of 2-(6-chloro-1-methyl-1H-indazol-3-yl)-5-(2-trimethylsilanyl-ethoxymethyl)-5H-pyrrolo[2,3-b]pyrazine-7-carboxylic acid (1-oxazol-2-yl-ethyl)-amide as an off-white powder.

Step 5

2-(6-Chloro-1-methyl-1H-indazol-3-yl)-5H-pyrrolo[2,3-b]pyrazine-7-carboxylic acid (1-oxazol-2-yl-ethyl)-amide

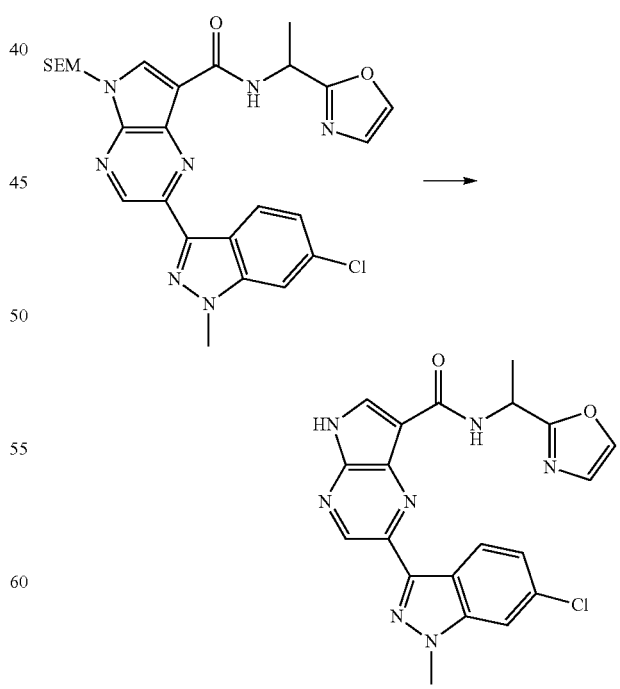

In a round-bottomed flask, 2-(6-chloro-1-methyl-1H-indazol-3-yl)-5-(2-trimethylsilanylethoxymethyl)-5H-pyrrolo[2, 3-b]pyrazine-7-carboxylic acid (1-oxazol-2-yl-ethyl)-amide (106 mg, 0.192 mmol) was dissolved in dichloromethane (0.9 ml) and trifluoroacetic acid (0.6 ml, 7.7 mmol) was added. The reaction mixture was stirred at room temperature for 2 h then concentrated. The residue was dissolved in dichloromethane (0.9 ml) and ethylenediamine (0.8 ml, 11.7 mmol) was added. The yellow solution was stirred at room temperature for 1 h then quenched with water and diluted with ethyl acetate. The resulting suspension was filtered, washed with hot water and ethyl acetate and dried under high vacuum to provide 66 mg (82%) of 2-(6-chloro-1-methyl-1H-indazol-3-yl)-5H-pyrrolo[2,3-b]pyrazine-7-carboxylic acid (1-oxazol-2-yl-ethyl)-amide as an off-white powder. MS: (M+H)$^+$=422; $^1$H NMR (DMSO-d$_6$, 300 MHz): δ (ppm) 12.91 (br. s., 1H), 9.13 (s, 1H), 8.66 (d, J=8.3 Hz, 1H), 8.51 (s, 1H), 8.46 (d, J=8.3 Hz, 1H), 8.11 (s, 1H), 8.00 (s, 1H), 7.23 (s, 1H), 7.15-7.21 (m, 1H), 5.47-5.61 (m, 1H), 4.18 (s, 3H), 1.66 (d, J=7.2 Hz, 3H).

Example 49

2-(6-Fluoro-1-methyl-1H-indazol-3-yl)-5H-pyrrolo[2,3-b]pyrazine-7-carboxylic acid (1-oxazol-2-yl-ethyl)-amide

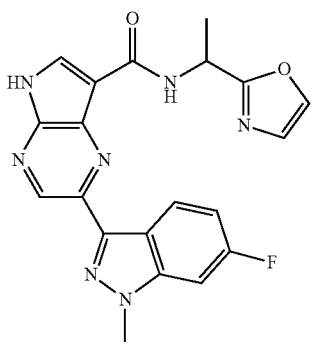

Step 1

2-(6-Fluoro-1-methyl-1H-indazol-3-yl)-5-(2-trimethylsilanyl-ethoxymethyl)-5H-pyrrolo[2,3-b]pyrazine-7-carboxylic acid (1-oxazol-2-yl-ethyl)-amide

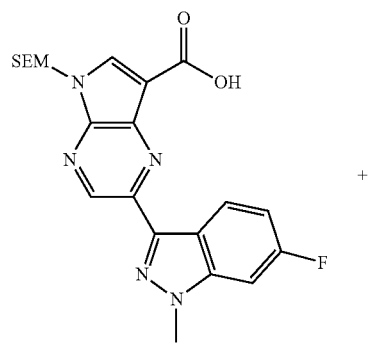

+

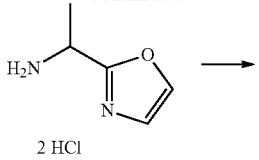

2 HCl

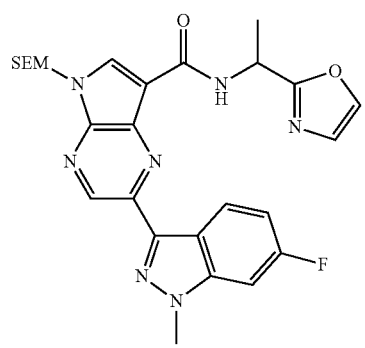

A round-bottomed flask was charged with 2-(6-fluoro-1-methyl-1H-indazol-3-yl)-5-(2-trimethylsilanyl-ethoxymethyl)-5H-pyrrolo[2,3-b]pyrazine-7-carboxylic acid (210 mg, 0.48 mmol) and 1-oxazol-2-yl-ethylamine dihydrochloride (198 mg, 0.86 mmol). DMF (2.2 ml) was added followed by N,N-diisopropylethylamine (0.55 ml, 3.15 mmol) and HATU (199 mg, 0.52 mmol). The light yellow solution was stirred at room temperature overnight. Water was added and the resulting suspension was filtered. The solid was washed with water and petroleum ether then dried under high vacuum to afford 248 mg (97%) of 2-(6-fluoro-1-methyl-1H-indazol-3-yl)-5-(2-trimethylsilanyl-ethoxymethyl)-5H-pyrrolo[2,3-b]pyrazine-7-carboxylic acid (1-oxazol-2-yl-ethyl)-amide as a light yellow powder.

Step 2

2-(6-Fluoro-1-methyl-1H-indazol-3-yl)-5H-pyrrolo[2,3-b]pyrazine-7-carboxylic acid (1-oxazol-2-yl-ethyl)-amide

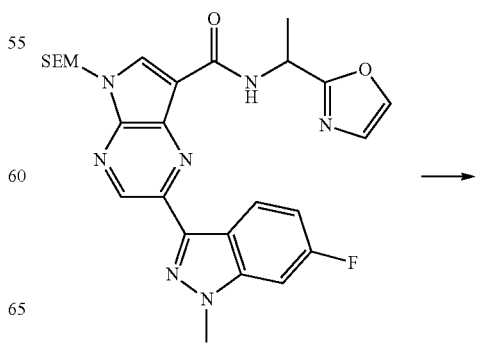

389
-continued

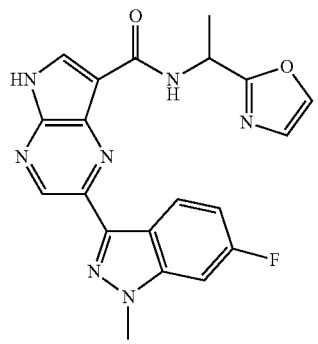

In a round-bottomed flask, 2-(6-fluoro-1-methyl-1H-indazol-3-yl)-5-(2-trimethylsilanylethoxymethyl)-5H-pyrrolo[2,3-b]pyrazine-7-carboxylic acid (1-oxazol-2-yl-ethyl)-amide (64 mg, 0.12 mmol) was dissolved in dichloromethane (0.6 ml) and trifluoroacetic acid (0.4 ml, 5.0 mmol) was added. The reaction mixture was stirred at room temperature for 2.5 h then concentrated. The residue was dissolved in dichloromethane (0.6 ml) and ethylenediamine (0.5 ml, 7.3 mmol) was added. The yellow solution was stirred at room temperature for 1 h then quenched with water and diluted with ethyl acetate. The resulting suspension was filtered, washed with hot water and ethyl acetate and dried under high vacuum to provide 33 mg (65%) of 2-(6-fluoro-1-methyl-1H-indazol-3-yl)-5H-pyrrolo[2,3-b]pyrazine-7-carboxylic acid (1-oxazol-2-yl-ethyl)-amide as a light yellow powder. MS: (M+H)$^+$= 406; $^1$H NMR (DMSO-d$_6$, 300 MHz): δ (ppm) 12.93 (br. s., 1H), 9.13 (s, 1H), 8.66 (d, J=8.7 Hz, 1H), 8.51 (s, 1H), 8.47 (dd, J=8.9, 5.5 Hz, 1H), 8.11 (s, 1H), 7.69 (dd, J=9.8, 2.3 Hz, 1H), 7.25 (s, 1H), 7.07 (td, J=9.2, 2.1 Hz, 1H), 5.48-5.61 (m, 1H), 4.15 (s, 3H), 1.67 (d, J=7.2 Hz, 3H).

Example 50

2-(6-Fluoro-1-methyl-1H-indazol-3-yl)-5H-pyrrolo[2,3-b]pyrazine-7-carboxylic acid ((R)-1-oxazol-2-yl-ethyl)-amide

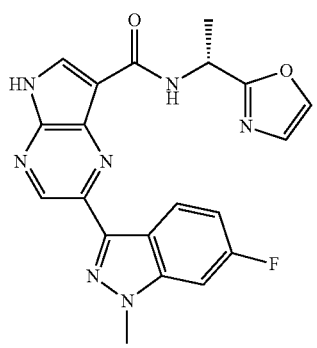

390

Step 1

2-(6-Fluoro-1-methyl-1H-indazol-3-yl)-5-(2-trimethylsilanyl-ethoxymethyl)-5H-pyrrolo[2,3-b]pyrazine-7-carboxylic acid ((R)-1-oxazol-2-yl-ethyl)-amide and 2-(6-Fluoro-1-methyl-1H-indazol-3-yl)-5-(2-trimethylsilanyl-ethoxymethyl)-5H-pyrrolo[2,3-b]pyrazine-7-carboxylic acid ((S)-1-oxazol-2-yl-ethyl)-amide

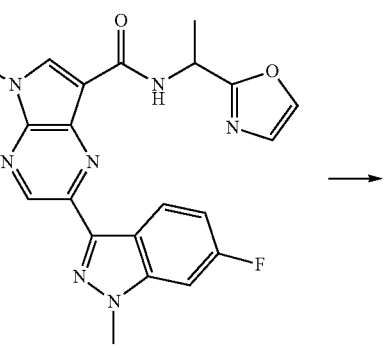

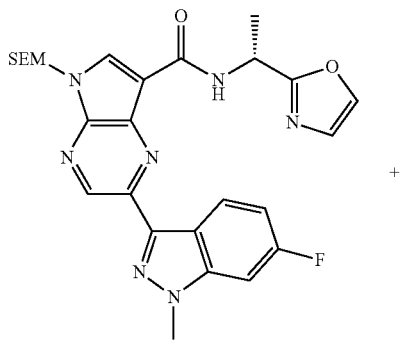

+

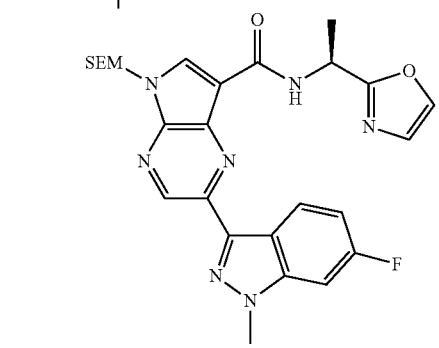

A racemic sample of 2-(6-fluoro-1-methyl-1H-indazol-3-yl)-5-(2-trimethylsilanylethoxymethyl)-5H-pyrrolo[2,3-b]pyrazine-7-carboxylic acid (1-oxazol-2-yl-ethyl)-amide (182 mg, 0.34 mmol) was subjected to chiral SFC chromatography. Separation of the enantiomers was achieved with a WHELK-O1 R,R column using 30% EtOH/CO$_2$ as the eluent. Obtained 76 mg (42%) of 2-(6-fluoro-1-methyl-1H-indazol-3-yl)-5-(2-trimethylsilanyl-ethoxymethyl)-5H-pyrrolo[2,3-b]pyrazine-7-carboxylic acid ((R)-1-oxazol-2-yl-ethyl)-amide as a light yellow solid and 72 mg (40%) of 2-(6-Fluoro-1-methyl-1H-indazol-3-yl)-5-(2-trimethylsilanyl-ethoxymethyl)-5H-pyrrolo[2,3-b]pyrazine-7-carboxylic acid ((S)-1-oxazol-2-yl-ethyl)-amide as a light yellow solid.

Step 2

2-(6-Fluoro-1-methyl-1H-indazol-3-yl)-5H-pyrrolo[2,3-b]pyrazine-7-carboxylic acid ((R)-1-oxazol-2-yl-ethyl)-amide

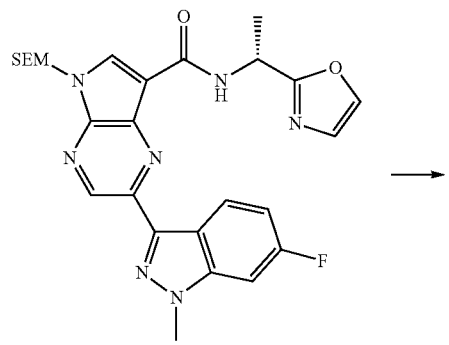

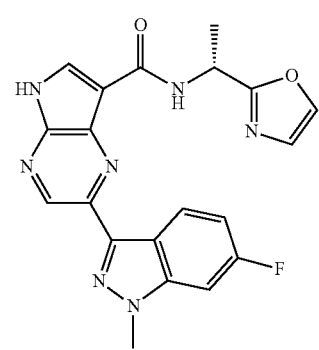

In a round-bottomed flask, 2-(6-fluoro-1-methyl-1H-indazol-3-yl)-5-(2-trimethylsilanylethoxymethyl)-5H-pyrrolo[2,3-b]pyrazine-7-carboxylic acid ((R)-1-oxazol-2-yl-ethyl)-amide (75 mg, 0.14 mmol) was dissolved in dichloromethane (0.7 ml) and trifluoroacetic acid (0.45 ml, 5.6 mmol) was added. The reaction mixture was stirred at room temperature for 2.5 h then concentrated. The residue was dissolved in dichloromethane (0.7 ml) and ethylenediamine (0.6 ml, 8.4 mmol) was added. The yellow solution was stirred at room temperature for 1 h then quenched with water and diluted with ethyl acetate. The resulting suspension was filtered, washed with hot water and ethyl acetate and dried under high vacuum to provide 23 mg (39%) of 2-(6-fluoro-1-methyl-1H-indazol-3-yl)-5H-pyrrolo[2,3-b]pyrazine-7-carboxylic acid ((R)-1-oxazol-2-yl-ethyl)-amide as a light yellow powder. MS: (M+H)$^+$=406; $^1$H NMR (DMSO-d$_6$, 300 MHz): δ (ppm) 12.95 (br. s., 1H), 9.13 (s, 1H), 8.66 (d, J=8.7 Hz, 1H), 8.51 (s, 1H), 8.47 (dd, J=9.1, 5.3 Hz, 1H), 8.11 (s, 1H), 7.69 (dd, J=9.6, 2.1 Hz, 1H), 7.24 (s, 1H), 7.02-7.11 (m, 1H), 5.48-5.60 (m, 1H), 4.15 (s, 3H), 1.66 (d, J=7.2 Hz, 3H).

Example 51

2-(6-Fluoro-1-methyl-1H-indazol-3-yl)-5H-pyrrolo[2,3-b]pyrazine-7-carboxylic acid ((S)-1-oxazol-2-yl-ethyl)-amide

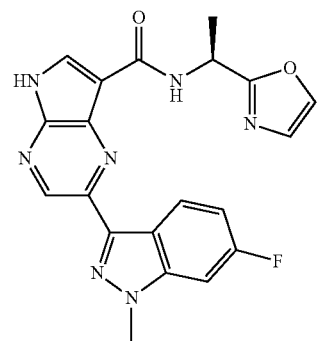 [SMILES: C[C@H](NC(=O)c1c[nH]c2ncc(-c3nn(C)c4cc(F)ccc34)nc12)c1ncco1]

Prepared according to Example 50, substituting 2-(6-fluoro-1-methyl-1H-indazol-3-yl)-5-(2-trimethylsilanyl-ethoxymethyl)-5H-pyrrolo[2,3-b]pyrazine-7-carboxylic acid ((S)-1-oxazol-2-yl-ethyl)-amide for 2-(6-fluoro-1-methyl-1H-indazol-3-yl)-5-(2-trimethylsilanyl-ethoxymethyl)-5H-pyrrolo[2,3-b]pyrazine-7-carboxylic acid ((R)-1-oxazol-2-yl-ethyl)-amide in Step 2. MS: (M+H)$^+$=406; $^1$H NMR (DMSO-d$_6$, 300 MHz): δ (ppm) 12.93 (br. s., 1H), 9.12 (s, 1H), 8.64 (d, J=8.7 Hz, 1H), 8.50 (s, 1H), 8.46 (dd, J=9.1, 5.3 Hz, 1H), 8.10 (s, 1H), 7.68 (dd, J=9.8, 2.3 Hz, 1H), 7.23 (s, 1H), 7.05 (td, J=9.1, 2.3 Hz, 1H), 5.53 (quin, J=7.5 Hz, 1H), 4.14 (s, 3H), 1.65 (d, J=7.2 Hz, 3H).

Example 52

2-(6-Fluoro-1-methyl-1H-indazol-3-yl)-5H-pyrrolo[2,3-b]pyrazine-7-carboxylic acid (1-oxazol-4-yl-ethyl)-amide

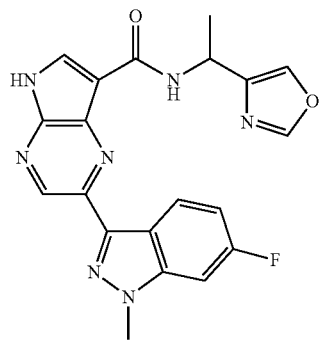 [SMILES: CC(NC(=O)c1c[nH]c2ncc(-c3nn(C)c4cc(F)ccc34)nc12)c1cocn1]

Step 1

2-Methyl-propane-2-sulfinic acid 1-oxazol-4-yl-meth-(E)-ylideneamide

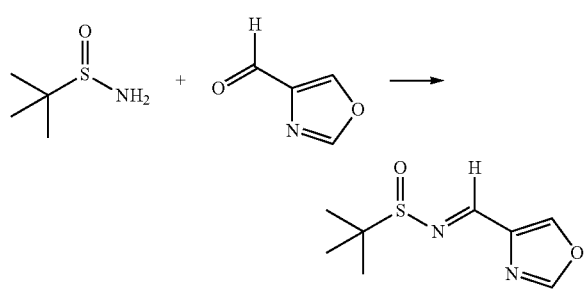

In a round-bottomed flask, oxazole-4-carbaldehyde (300 mg, 3.09 mmol) was dissolved in THF (7 ml) and 2-methyl-propane-2-sulfinamide (450 mg, 3.71 mmol) and titanium (IV) ethoxide (1.3 ml, 6.18 mmol) were added. The reaction mixture was stirred at room temperature overnight then slowly quenched by dropwise addition of brine (2 ml) which resulted in the formation of a thick light yellow precipitate. The reaction mixture was diluted with ethyl acetate and stirred vigorously at room temperature for 30 min. The suspension was filtered over Celite and rinsed with ethyl acetate. The filtrate was concentrated and the residue was chromatographed over silica gel with EtOAc/hexanes (gradient 0-40% EtOAc) to afford 552 mg (89%) of 2-methyl-propane-2-sulfinic acid 1-oxazol-4-yl-meth-(E)-ylideneamide as a white solid.

Step 2

2-Methyl-propane-2-sulfinic acid (1-oxazol-4-yl-ethyl)-amide

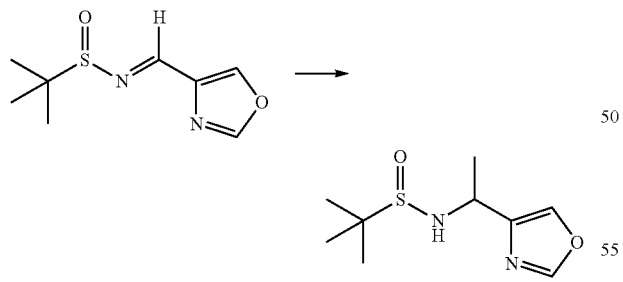

In a round-bottomed flask, 2-methyl-propane-2-sulfinic acid 1-oxazol-4-yl-meth-(E)-ylideneamide (548 mg, 2.74 mmol) was dissolved in dichloromethane (9 ml). The reaction mixture was cooled to 0° C. and methylmagnesium bromide (3.0 M in diethyl ether, 1.0 ml, 3.0 mmol) was added dropwise. The reaction mixture was stirred at 0° C. for 1 h then quenched with saturated aqueous NH₄Cl and extracted with ethyl acetate (2×). The combined organic layers were washed with water and brine then dried over sodium sulfate, filtered and concentrated to afford 588 mg of 2-methyl-propane-2-sulfinic acid (1-oxazol-4-yl-ethyl)-amide as a light yellow oil.

Step 3

1-Oxazol-4-yl-ethylamine dihydrochloride

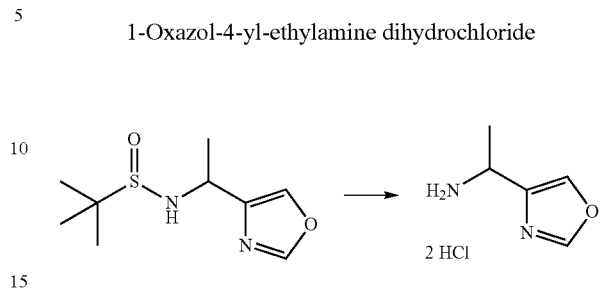

In a round-bottomed flask, 2-methyl-propane-2-sulfinic acid (1-oxazol-4-yl-ethyl)-amide (585 mg, 2.57 mmol) was dissolved in methanol (4.5 ml) and hydrogen chloride (4.0 M in 1,4-dioxane, 1.3 ml, 5.2 mmol) was added dropwise. The reaction mixture was stirred at room temperature for 15 min then concentrated to give 1-oxazol-4-yl-ethylamine dihydrochloride as a viscous orange oil which was used without further purification.

Step 4

2-(6-Fluoro-1-methyl-1H-indazol-3-yl)-5-(2-trimethylsilanyl-ethoxymethyl)-5H-pyrrolo[2,3-b]pyrazine-7-carboxylic acid (1-oxazol-4-yl-ethyl)-amide

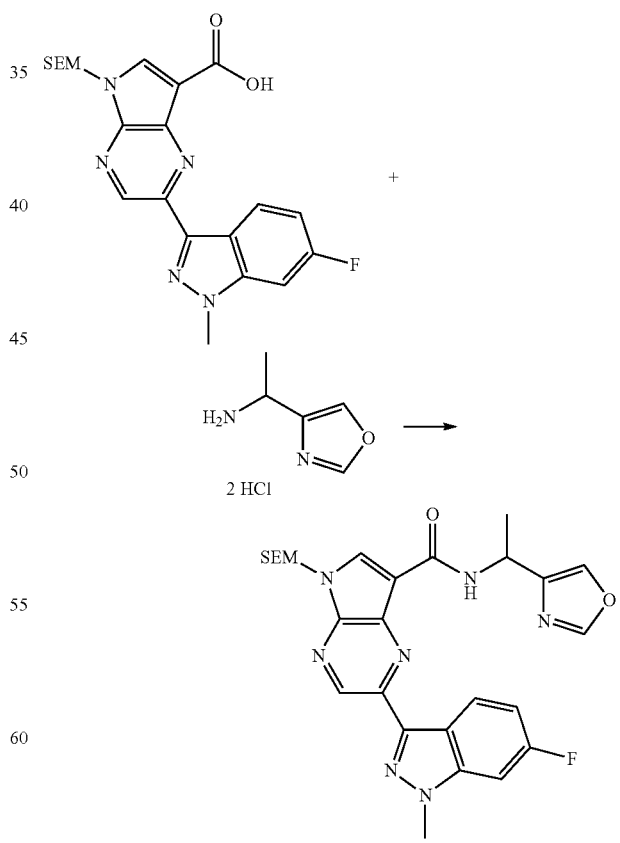

A round-bottomed flask was charged with 2-(6-fluoro-1-methyl-1H-indazol-3-yl)-5-(2-trimethylsilanyl-ethoxymethyl)-5H-pyrrolo[2,3-b]pyrazine-7-carboxylic acid (100 mg, 0.23 mmol) and 1-oxazol-2-yl-ethylamine dihydrochloride (crude from Step 3, 90 mg, 0.41 mmol). DMF (1.1 ml) was added followed by N,N-diisopropylethylamine (0.26 ml, 1.49 mmol) and HATU (95 mg, 0.25 mmol). The light yellow solution was stirred at room temperature for 48 h. Water was added and the resulting suspension was filtered. The solid was washed with water and petroleum ether then dried under high vacuum to afford 113 mg (93%) of 2-(6-fluoro-1-methyl-1H-indazol-3-yl)-5-(2-trimethylsilanyl-ethoxymethyl)-5H-pyrrolo[2,3-b]pyrazine-7-carboxylic acid (1-oxazol-4-yl-ethyl)-amide as an off-white powder.

Step 5

2-(6-Fluoro-1-methyl-1H-indazol-3-yl)-5H-pyrrolo[2,3-b]pyrazine-7-carboxylic acid (1-oxazol-4-yl-ethyl)-amide

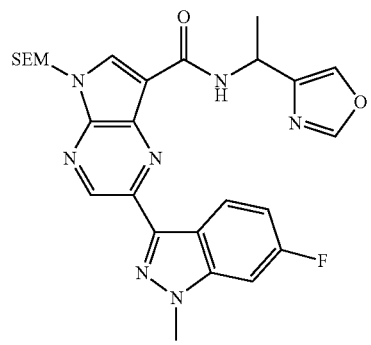

In a round-bottomed flask, 2-(6-fluoro-1-methyl-1H-indazol-3-yl)-5-(2-trimethylsilanylethoxymethyl)-5H-pyrrolo[2,3-b]pyrazine-7-carboxylic acid (1-oxazol-4-yl-ethyl)-amide (110 mg, 0.205 mmol) was dissolved in dichloromethane (1 ml) and trifluoroacetic acid (0.63 ml, 8.2 mmol) was added. The reaction mixture was stirred at room temperature for 2 h then concentrated. The residue was dissolved in dichloromethane (1 ml) and ethylenediamine (0.83 ml, 12.3 mmol) was added. The yellow solution was stirred at room temperature for 1 h then quenched with water and diluted with ethyl acetate. The resulting suspension was filtered, washed with hot water and ethyl acetate and dried under high vacuum to provide 58 mg (70%) of 2-(6-fluoro-1-methyl-1H-indazol-3-yl)-5H-pyrrolo[2,3-b]pyrazine-7-carboxylic acid (1-oxazol-4-yl-ethyl)-amide as a light yellow powder. MS: (M+H)$^+$= 406; $^1$H NMR (DMSO-d$_6$, 300 MHz): δ (ppm) 12.83 (br. s., 1H), 9.12 (s, 1H), 8.42-8.51 (m, 2H), 8.32-8.42 (m, 2H), 8.20 (s, 1H), 7.68 (dd, J=9.8, 1.9 Hz, 1H), 7.04 (td, J=9.3, 1.9 Hz, 1H), 5.28-5.46 (m, 1H), 4.14 (s, 3H), 1.58 (d, J=6.8 Hz, 3H).

Example 53

2-(6-Fluoro-1-methyl-1H-indazol-3-yl)-5H-pyrrolo[2,3-b]pyrazine-7-carboxylic acid (1-isoxazol-3-yl-ethyl)-amide

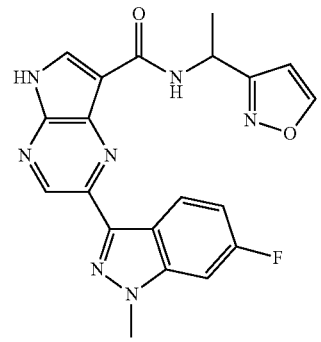

Step 1

2-Methyl-propane-2-sulfinic acid 1-isoxazol-3-yl-meth-(E)-ylideneamide

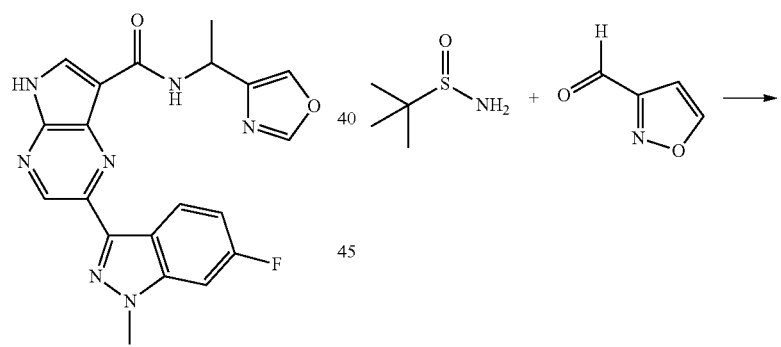

In a round-bottomed flask, isoxazole-3-carbaldehyde (300 mg, 3.09 mmol) was dissolved in THF (7 ml) and 2-methyl-propane-2-sulfinamide (450 mg, 3.71 mmol) and titanium (IV) ethoxide (1.3 ml, 6.18 mmol) were added. The reaction mixture was stirred at room temperature overnight then slowly quenched by dropwise addition of brine (2 ml) which resulted in the formation of a thick yellow precipitate. The reaction mixture was diluted with ethyl acetate and stirred vigorously at room temperature for 10 min. The suspension was filtered over Celite and rinsed with ethyl acetate. The filtrate was concentrated and the residue was chromatographed over silica gel with EtOAc/hexanes (gradient 0-20%

EtOAc) to afford 585 mg (95%) of 2-methyl-propane-2-sulfinic acid 1-isoxazol-3-yl-meth-(E)-ylideneamide as a colorless oil.

Step 2

2-Methyl-propane-2-sulfinic acid (1-isoxazol-3-yl-ethyl)-amide

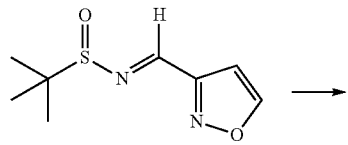

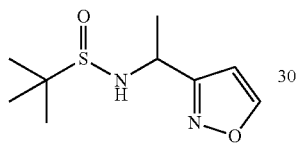

In a round-bottomed flask, 2-methyl-propane-2-sulfinic acid 1-isoxazol-3-yl-meth-(E)-ylideneamide (584 mg, 2.92 mmol) was dissolved in dichloromethane (10 ml). The reaction mixture was cooled to 0° C. and methylmagnesium bromide (3.0 M in diethyl ether, 1.1 ml, 3.3 mmol) was added dropwise. The reaction mixture was stirred at 0° C. for 2 h then quenched with saturated aqueous NH$_4$Cl and extracted with ethyl acetate (2x). The combined organic layers were washed with water and brine then dried over sodium sulfate, filtered and concentrated to afford 655 mg of 2-methyl-propane-2-sulfinic acid (1-isoxazol-3-yl-ethyl)-amide as a colorless oil.

Step 3

1-Isoxazol-3-yl-ethylamine hydrochloride

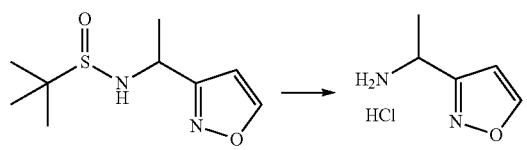

In a round-bottomed flask, 2-methyl-propane-2-sulfinic acid (1-isoxazol-3-yl-ethyl)-amide (652 mg, 2.71 mmol) was dissolved in methanol (5 ml) and hydrogen chloride (4.0 M in 1,4-dioxane, 1.4 ml, 5.6 mmol) was added dropwise. The reaction mixture was stirred at room temperature for 15 min then concentrated to give 1-isoxazol-3-yl-ethylamine hydrochloride as an off-white solid which was used without further purification.

Step 4

2-(6-Fluoro-1-methyl-1H-indazol-3-yl)-5-(2-trimethylsilanyl-ethoxymethyl)-5H-pyrrolo[2,3-b]pyrazine-7-carboxylic acid (1-isoxazol-3-yl-ethyl)-amide

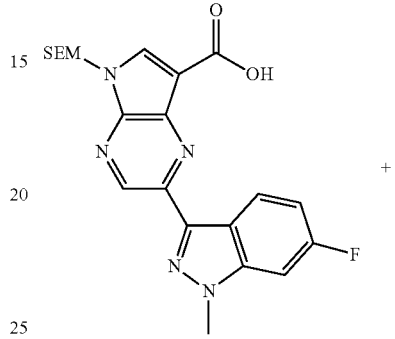

+

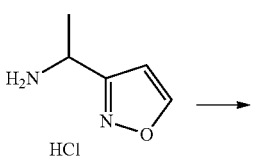

A round-bottomed flask was charged with 2-(6-fluoro-1-methyl-1H-indazol-3-yl)-5-(2-trimethylsilanyl-ethoxymethyl)-5H-pyrrolo[2,3-b]pyrazine-7-carboxylic acid (100 mg, 0.23 mmol) and 1-isoxazol-3-yl-ethylamine hydrochloride (crude from Step 3, 81 mg, 0.41 mmol). DMF (1.1 ml) was added followed by N,N-diisopropylethylamine (0.26 ml, 1.49 mmol) and HATU (95 mg, 0.25 mmol). The yellow solution was stirred at room temperature for 48 h. Water was added and the resulting suspension was filtered. The solid was washed with water and petroleum ether then dried under high vacuum to afford 115 mg (95%) of 2-(6-fluoro-1-methyl-1H-indazol-3-yl)-5-(2-trimethylsilanyl-ethoxymethyl)-5H-pyrrolo[2,3-b]pyrazine-7-carboxylic acid (1-isoxazol-3-yl-ethyl)-amide as an off-white powder.

Step 5

2-(6-Fluoro-1-methyl-1H-indazol-3-yl)-5H-pyrrolo[2,3-b]pyrazine-7-carboxylic acid (1-isoxazol-3-yl-ethyl)-amide

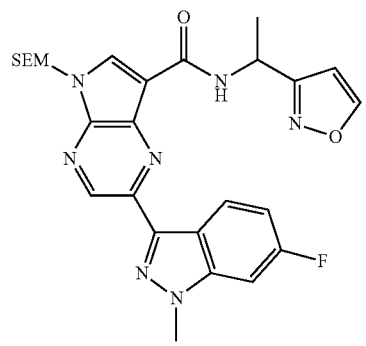

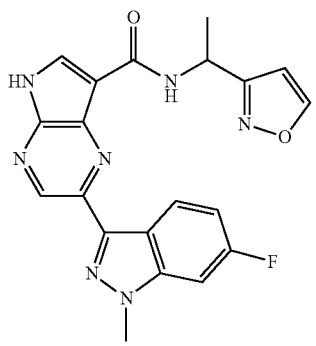 [SMILES: CC(NC(=O)c1c[nH]c2ncc(-c3nn(C)c4cc(F)ccc34)nc12)c1ccon1]

In a round-bottomed flask, 2-(6-fluoro-1-methyl-1H-indazol-3-yl)-5-(2-trimethylsilanylethoxymethyl)-5H-pyrrolo[2,3-b]pyrazine-7-carboxylic acid (1-isoxazol-3-yl-ethyl)-amide (113 mg, 0.211 mmol) was dissolved in dichloromethane (1.1 ml) and trifluoroacetic acid (0.65 ml, 8.4 mmol) was added. The reaction mixture was stirred at room temperature for 2 h then concentrated. The residue was dissolved in dichloromethane (1.1 ml) and ethylenediamine (0.86 ml, 12.7 mmol) was added. The yellow solution was stirred at room temperature for 1 h then quenched with water and diluted with ethyl acetate. The resulting suspension was filtered, washed with hot water and ethyl acetate and dried under high vacuum to provide 46 mg (54%) of 2-(6-fluoro-1-methyl-1H-indazol-3-yl)-5H-pyrrolo[2,3-b]pyrazine-7-carboxylic acid (1-isoxazol-3-yl-ethyl)-amide as a light yellow powder. MS: (M+H)$^+$=406; $^1$H NMR (DMSO-d$_6$, 300 MHz): δ (ppm) 12.89 (br. s., 1H), 9.12 (s, 1H), 8.91 (d, J=1.5 Hz, 1H), 8.58 (d, J=8.7 Hz, 1H), 8.50 (s, 1H), 8.44 (dd, J=8.9, 5.5 Hz, 1H), 7.68 (dd, J=9.6, 2.1 Hz, 1H), 7.02 (td, J=9.1, 1.9 Hz, 1H), 6.68 (d, J=1.5 Hz, 1H), 5.53 (quin, J=7.2 Hz, 1H), 4.15 (s, 3H), 1.65 (d, J=6.8 Hz, 3H).

Example 54

2-(6-Fluoro-1-methyl-1H-indazol-3-yl)-5H-pyrrolo[2,3-b]pyrazine-7-carboxylic acid [1-(5-methyl-isoxazol-3-yl)-ethyl]-amide

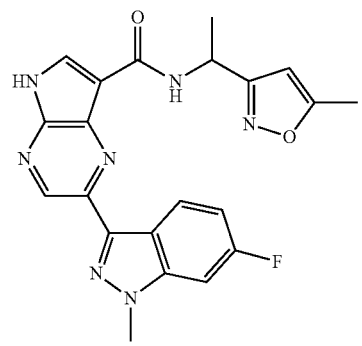 [SMILES: Cc1cc(C(C)NC(=O)c2c[nH]c3ncc(-c4nn(C)c5cc(F)ccc45)nc23)no1]

Prepared according to the procedure outlined in Example 53, substituting 5-methylisoxazole-3-carbaldehyde for isoxazole-3-carbaldehyde in Step 1. MS: (M+H)$^+$=420.

$^1$H NMR (DMSO-d$_6$, 300 MHz): δ (ppm) 12.86 (br. s., 1H), 9.12 (s, 1H), 8.55 (d, J=8.3 Hz, 1H), 8.50 (s, 1H), 8.45 (dd, J=8.9, 5.5 Hz, 1H), 7.68 (dd, J=9.8, 2.3 Hz, 1H), 7.04 (td, J=9.2, 2.1 Hz, 1H), 6.31 (s, 1H), 5.38-5.50 (m, 1H), 4.15 (s, 3H), 2.37 (s, 3H), 1.62 (d, J=7.2 Hz, 3H).

Example 55

2-(6-Fluoro-1-methyl-1H-indazol-3-yl)-5H-pyrrolo[2,3-b]pyrazine-7-carboxylic acid (1-isoxazol-5-yl-ethyl)-amide

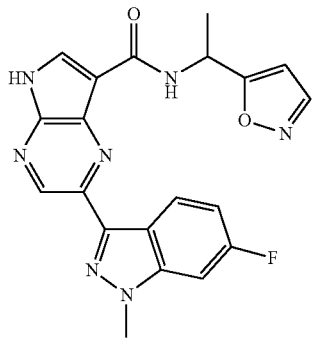 [SMILES: CC(NC(=O)c1c[nH]c2ncc(-c3nn(C)c4cc(F)ccc34)nc12)c1ccno1]

Step 1

Isoxazol-5-yl-methanol

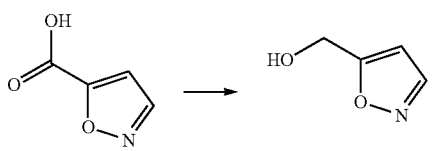 [SMILES: O=C(O)c1ccno1 ; OCc1ccno1]

In a round-bottomed flask, isoxazole-5-carboxylic acid (1.0 g, 8.84 mmol) was dissolved in THF (35 ml). The solution was cooled to 0° C. and triethylamine (1.4 ml, 10.0 mmol) was added followed by ethyl chloroformate (0.94 ml, 9.8 mmol). A thick precipitate was formed upon the addition of the latter. The suspension was stirred at 0° C. for 15 min then a solution of sodium borohydride (1.00 g, 26.5 mmol) in water (14 ml) was added portionwise via pipet. Vigorous gas evolution was observed. The reaction mixture was stirred at 0° C. for 1 h then diluted with water and saturated aqueous NH$_4$Cl and extracted with dichloromethane (3×). The organic layers were combined, dried over sodium sulfate, filtered and concentrated. The residue was chromatographed over silica gel with EtOAc/hexanes (gradient 0-50% EtOAc) to afford 513 mg (59%) of isoxazol-5-yl-methanol as a colorless oil. $^1$H NMR (CDCl$_3$, 300 MHz): δ (ppm) 8.23 (d, J=1.9 Hz, 1H), 6.26-6.30 (m, 1H), 4.82 (s, 2H), 2.13 (br. s., 1H).

Step 2

Isoxazole-5-carbaldehyde

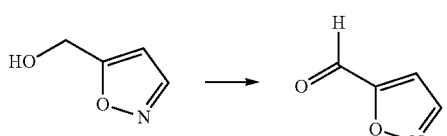

In a round-bottomed flask, isoxazol-5-yl-methanol (511 mg, 5.16 mmol) was dissolved in dichloromethane (30 ml). Dess-Martin periodinane (2.3 g, 5.41 mmol) was added and the reaction mixture was stirred at room temperature for 1.5 h. The reaction was quenched with 50 ml of a 1:1 solution of 10% aqueous Na$_2$S$_2$O$_3$ and saturated aqueous NaHCO$_3$ and then extracted with dichloromethane (2×). The organic layers were washed with saturated aqueous NaHCO$_3$, water and brine. The aqueous layers were back extracted with dichloromethane. The organic layers were combined, dried over sodium sulfate, filtered and concentrated. The residue was chromatographed over silica gel with EtOAc/hexanes (gradient 0-40% EtOAc) to afford 226 mg (45%) of isoxazole-5-carbaldehyde as a colorless oil. $^1$H NMR (CDCl$_3$, 300 MHz): δ (ppm) 10.05 (s, 1H), 8.44 (d, J=1.9 Hz, 1H), 7.02 (d, J=1.9 Hz, 1H).

Step 3

2-(6-Fluoro-1-methyl-1H-indazol-3-yl)-5H-pyrrolo[2,3-b]pyrazine-7-carboxylic acid (1-isoxazol-5-yl-ethyl)-amide

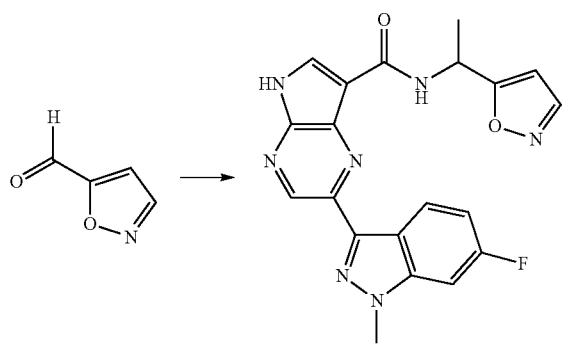 [SMILES: O=Cc1ccno1 ; CC(NC(=O)c1c[nH]c2ncc(-c3nn(C)c4cc(F)ccc34)nc12)c1ccno1]

Prepared according to the procedure outlined in Example 53, substituting isoxazole-5-carbaldehyde for isoxazole-3-carbaldehyde in Step 1. MS: (M+H)$^+$=406.

$^1$H NMR (DMSO-d$_6$, 300 MHz): δ (ppm) 12.94 (br. s., 1H), 9.12 (s, 1H), 8.49-8.62 (m, 3H), 8.34 (dd, J=8.9, 5.5 Hz, 1H), 7.69 (dd, J=9.8, 1.9 Hz, 1H), 7.12 (td, J=9.2, 2.1 Hz, 1H), 6.56 (d, J=1.9 Hz, 1H), 5.62 (quin, J=7.5 Hz, 1H), 4.15 (s, 3H), 1.67 (d, J=7.2 Hz, 3H).

Example 56

2-(6-Fluoro-1-methyl-1H-indazol-3-yl)-5H-pyrrolo[2,3-b]pyrazine-7-carboxylic acid ((R)-2,2-difluoro-1-methyl-propyl)-amide

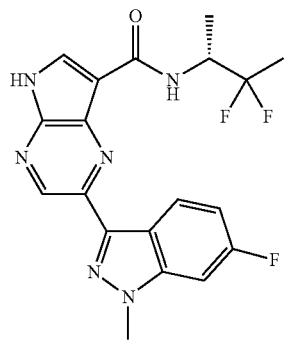 [SMILES: C[C@@H](NC(=O)c1c[nH]c2ncc(-c3nn(C)c4cc(F)ccc34)nc12)C(C)(F)F]

Step 1

[(R)-1-(Methoxy-methyl-carbamoyl)-ethyl]-carbamic acid tert-butyl ester

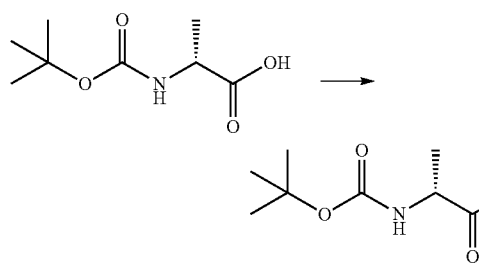

A round-bottomed flask was charged with Boc-D-alanine (1.0 g, 5.29 mmol) and N,O-dimethylhydroxylamine hydrochloride (670 mg, 6.87 mmol). DMF (12 ml) was added followed by N,N-diisopropylethylamine (2.4 ml, 13.7 mmol) and HATU (2.21 g, 5.81 mmol). The yellow suspension was stirred at room temperature for 48 h. The reaction mixture was quenched with water and petroleum ether was added. The resulting suspension was filtered, washed with water and petroleum ether and dried under high vacuum to afford 1.05 g (85%) of [(R)-1-(methoxymethyl-carbamoyl)-ethyl]-carbamic acid tert-butyl ester as a white powder.

Step 2

((R)-1-Methyl-2-oxo-propyl)-carbamic acid tert-butyl ester

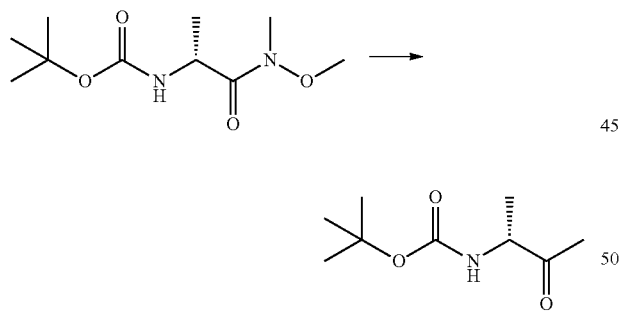

In a round-bottomed flask, [(R)-1-(methoxy-methyl-carbamoyl)-ethyl]-carbamic acid tert-butyl ester (3.00 g, 12.9 mmol) was dissolved in THF (100 ml). The solution was cooled to −16° C. (NaCl/ice bath) and methylmagnesium bromide (3.0 M in diethyl ether, 12.0 ml, 36.0 mmol) was added dropwise over 20 min. After the addition, the reaction mixture was allowed to warm slowly to room temperature overnight. The reaction mixture was cooled to 0° C., quenched with saturated aqueous NH$_4$Cl and extracted with EtOAc (2×). The combined organic layers were washed with water and brine then dried over sodium sulfate, filtered and concentrated. The residue was chromatographed over silica gel with EtOAc/hexanes (gradient 0-20% EtOAc) to afford 2.21 g (91%) of ((R)-1-methyl-2-oxo-propyl)-carbamic acid tert-butyl ester as a white solid.

Step 3

((R)-2,2-Difluoro-1-methyl-propyl)-carbamic acid tert-butyl ester

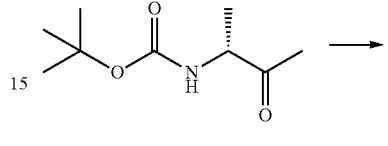

In a round-bottomed flask, ((R)-1-methyl-2-oxo-propyl)-carbamic acid tert-butyl ester (300 mg, 1.6 mmol) was dissolved in dichloromethane (15 ml). DAST (0.64 ml, 4.84 mmol) was added dropwise at room temperature and the reaction mixture was stirred at room temperature overnight then at reflux for 7 h. The reaction was cooled to room temperature, quenched with 15 ml of saturated aqueous NaHCO$_3$ and then extracted with dichloromethane (2×). The organic layers were combined, dried over sodium sulfate, filtered and concentrated. The residue was chromatographed over silica gel with EtOAc/hexanes (gradient 0-5% EtOAc) to afford 152 mg (45%) of ((R)-2,2-difluoro-1-methyl-propyl)-carbamic acid tert-butyl ester as a light yellow solid. $^1$H NMR (CDCl$_3$, 300 MHz): δ (ppm) 4.59 (br. s., 1H), 3.90-4.08 (m, 1H), 1.62 (t, J=18.9 Hz, 3H), 1.46 (s, 9H), 1.23 (d, J=6.8 Hz, 3H).

Step 4

(R)-2,2-Difluoro-1-methyl-propylamine trifluoroacetate

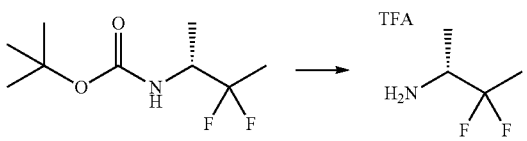

In a round-bottomed flask, ((R)-2,2-difluoro-1-methyl-propyl)-carbamic acid tert-butyl ester (148 mg, 0.71 mmol) was dissolved in dichloromethane (3 ml) and trifluoroacetic acid (1.6 ml, 20.8 mmol) was slowly added. The reaction mixture was stirred at room temperature for 1.5 h then concentrated to give (R)-2,2-difluoro-1-methyl-propylamine trifluoroacetate as a light brown oil which was used without further purification.

Step 5

2-(6-Fluoro-1-methyl-1H-indazol-3-yl)-5-(2-trimethylsilanyl-ethoxymethyl)-5H-pyrrolo[2,3-b]pyrazine-7-carboxylic acid ((R)-2,2-difluoro-1-methyl-propyl)-amide

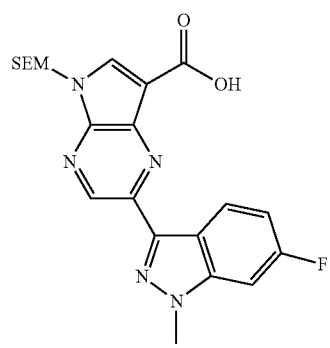

+

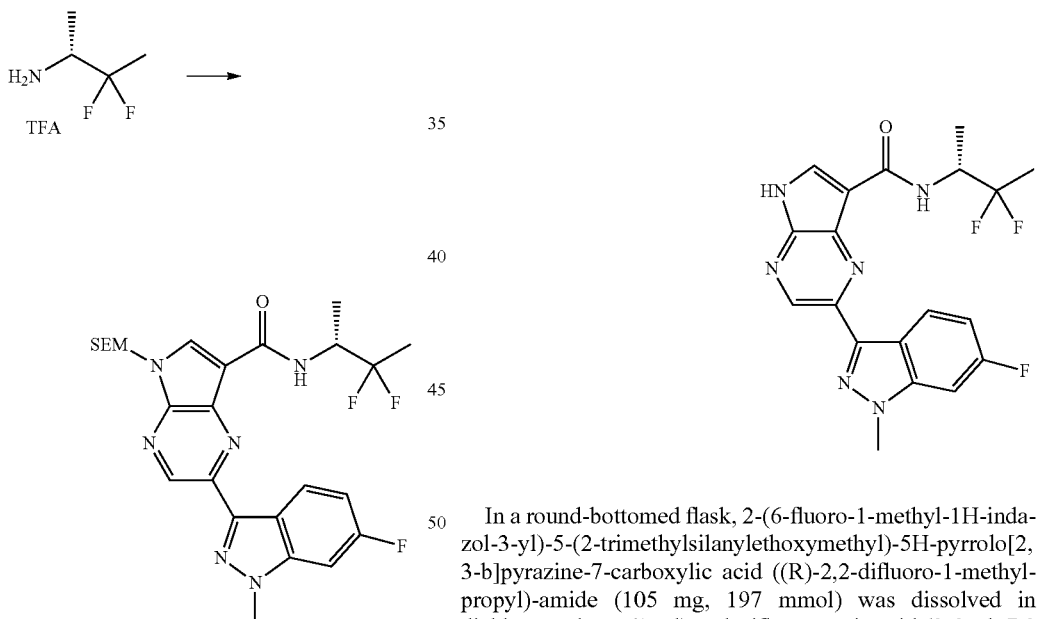

In a round-bottomed flask, (R)-2,2-difluoro-1-methyl-propylamine trifluoroacetate (crude from Step 4) was dissolved in DMF (1.2 ml) and N,N-diisopropylethylamine (0.5 ml, 2.86 mmol) was added. Then 2-(6-fluoro-1-methyl-1H-indazol-3-yl)-5-(2-trimethylsilanyl-ethoxymethyl)-5H-pyrrolo[2,3-b]pyrazine-7-carboxylic acid (110 mg, 0.25 mmol) was added followed by HATU (104 mg, 0.27 mmol). The yellow solution was stirred at room temperature overnight. Water was added and the suspension was filtered. The filter cake was washed with water and petroleum ether then dried under high vacuum to afford 108 mg (81%) of 2-(6-fluoro-1-methyl-1H-indazol-3-yl)-5-(2-trimethylsilanyl-ethoxymethyl)-5H-pyrrolo[2,3-b]pyrazine-7-carboxylic acid ((R)-2,2-difluoro-1-methyl-propyl)-amide as an off-white powder.

Step 6

2-(6-Fluoro-1-methyl-1H-indazol-3-yl)-5H-pyrrolo[2,3-b]pyrazine-7-carboxylic acid ((R)-2,2-difluoro-1-methyl-propyl)-amide

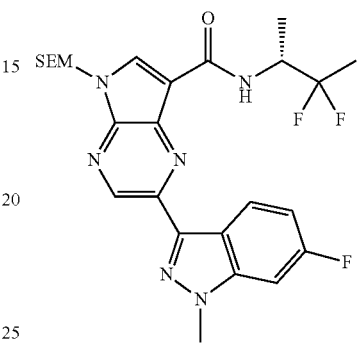

In a round-bottomed flask, 2-(6-fluoro-1-methyl-1H-indazol-3-yl)-5-(2-trimethylsilanylethoxymethyl)-5H-pyrrolo[2,3-b]pyrazine-7-carboxylic acid ((R)-2,2-difluoro-1-methyl-propyl)-amide (105 mg, 197 mmol) was dissolved in dichloromethane (1 ml) and trifluoroacetic acid (0.6 ml, 7.9 mmol) was added. The reaction mixture was stirred at room temperature for 2 h then concentrated. The residue was dissolved in dichloromethane (1 ml) and ethylenediamine (0.8 ml, 11.8 mmol) was added. The reaction was stirred at room temperature for 1 h then quenched with water and diluted with ethyl acetate. The resulting suspension was filtered, washed with hot water and ethyl acetate and dried under high vacuum to provide 48 mg (61%) of 2-(6-fluoro-1-methyl-1H-indazol-3-yl)-5H-pyrrolo[2,3-b]pyrazine-7-carboxylic acid ((R)-2,2-difluoro-1-methyl-propyl)-amide as an off-white powder. MS: (M+H)$^+$=403; $^1$H NMR (DMSO-d$_6$, 300 MHz): δ (ppm) 12.85 (br. s., 1H), 9.12 (s, 1H), 8.51 (s, 1H), 8.45 (dd, J=8.9, 5.5 Hz, 1H), 8.32 (d, J=9.8 Hz, 1H), 7.69 (dd, J=9.8, 2.3 Hz, 1H), 7.10 (td, J=9.1, 1.9 Hz, 1H), 4.56-4.80 (m, 1H), 4.15 (s, 3H), 1.72 (t, J=19.3 Hz, 3H), 1.37 (d, J=6.8 Hz, 3H).

Example 57

2-(6-Fluoro-1-methyl-1H-indazol-3-yl)-5H-pyrrolo[2,3-b]pyrazine-7-carboxylic acid (cis-3-cyanomethyl-cyclopentyl)-amide

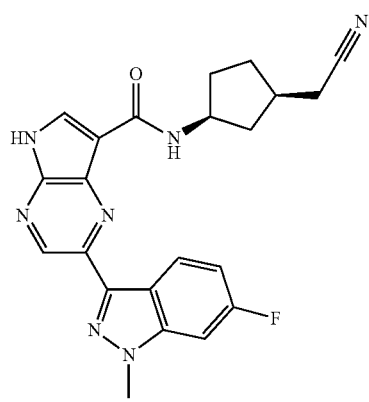 [SMILES: Cn1nc(-c2cnc3[nH]cc(C(=O)N[C@H]4CC[C@@H](CC#N)C4)c3n2)c2ccc(F)cc21]

Step 1

3-Oxo-2-aza-bicyclo[2.2.1]hept-5-ene-2-carboxylic acid tert-butyl ester

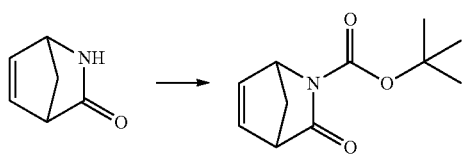

In a round-bottomed flask, 2-azabicyclo[2.2.1]hept-5-en-3-one (1.0 g, 9.16 mmol) was suspended in THF (10 ml) and triethylamine (1.9 ml, 13.6 mmol) di-tert-butyl dicarbonate (2.4 g, 11.0 mmol) and 4-dimethylaminopyridine (112 mg, 0.92 mmol were added. The reaction mixture was stirred at room temperature overnight then quenched with water and extracted with ethyl acetate (2×). The combined organic layers were washed with water and brine then dried over sodium sulfate, filtered and concentrated. The residue was chromatographed over silica gel with EtOAc/hexanes (gradient 0-30% EtOAc) to afford 1.79 g (93%) of 3-oxo-2-aza-bicyclo[2.2.1]hept-5-ene-2-carboxylic acid tert-butyl ester as a light yellow solid.

Step 2

3-Oxo-2-aza-bicyclo[2.2.1]heptane-2-carboxylic acid tert-butyl ester

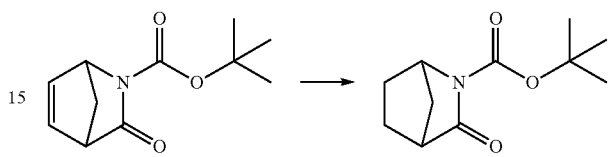

In a Parr pressure bottle, 3-oxo-2-aza-bicyclo[2.2.1]hept-5-ene-2-carboxylic acid tert-butyl ester (1.77 g, 8.46 mmol) was dissolved in methanol (12 ml) and 10% palladium on carbon (wet, 170 mg, 0.16 mmol) was carefully added. The bottle was placed on a Parr hydrogenator and shaken under 40 psi hydrogen pressure for 2 h. The reaction mixture was filtered over Celite and rinsed with methanol/ethyl acetate. The filtrate was concentrated to give 1.88 g of 3-oxo-2-aza-bicyclo[2.2.1]heptane-2-carboxylic acid tert-butyl ester as a light grey oil which was used without further purification.

Step 3

(cis-3-Hydroxymethyl-cyclopentyl)-carbamic acid tert-butyl ester

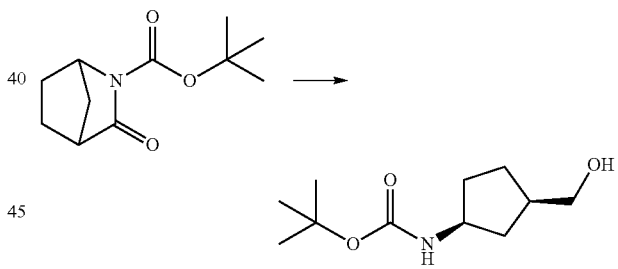

In a round-bottomed flask, 3-oxo-2-aza-bicyclo[2.2.1]heptane-2-carboxylic acid tert-butyl ester (crude from Step 2, 1.87 g) was dissolved in THF (20 ml) and water (2 ml). The reaction mixture was cooled to 0° C. and sodium borohydride (301 mg, 7.97 mmol) was added. The reaction was stirred at 0° C. for 30 min then a second portion of sodium borohydride (301 mg, 7.97 mmol) was added. The reaction mixture was stirred at 0° C. for 7.5 h then a third portion of sodium borohydride (602 mg, 15.94 mmol) was added. The reaction mixture was stirred at room temperature overnight then a fourth portion of sodium borohydride (602 mg, 15.94 mmol) was added. The reaction mixture was stirred at room temperature overnight then cooled to 0° C. and carefully quenched with 1M HCl. When gas evolution had ceased (pH=~6) the mixture was extracted with dichloromethane (3×). The organic layers were combined, dried over sodium sulfate, filtered and concentrated. The residue was chromatographed over silica gel with EtOAc/hexanes (gradient 0-60% EtOAc)

to afford 1.73 g (95%, 2 steps) of (cis-3-hydroxymethyl-cyclopentyl)-carbamic acid tert-butyl ester as an off-white solid.

Step 4

Methanesulfonic acid (cis)-3-tert-butoxycarbonylamino-cyclopentylmethyl ester

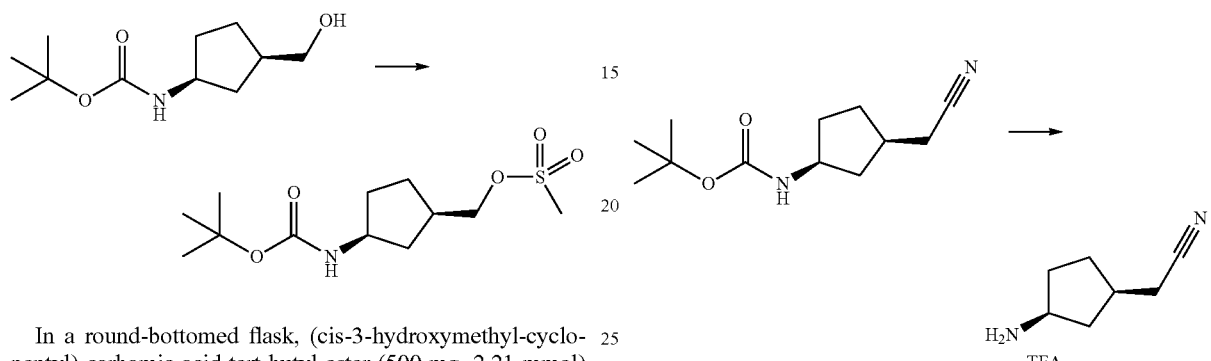

In a round-bottomed flask, (cis-3-hydroxymethyl-cyclopentyl)-carbamic acid tert-butyl ester (500 mg, 2.21 mmol) was dissolved in dichloromethane (5 ml). The solution was cooled to 0° C. and triethylamine (0.40 ml, 2.87 mmol) was added followed by methanesulfonyl chloride (0.20 ml, 2.57 mmol). The reaction mixture was stirred at 0° C. for 45 min then quenched with water and extracted with dichloromethane (2×). The organic layers were combined, dried over sodium sulfate, filtered and concentrated to give 780 mg of methanesulfonic acid (cis)-3-tert-butoxycarbonylamino-cyclopentylmethyl ester as a pale yellow oil which was used without further purification.

Step 5

(cis-3-Cyanomethyl-cyclopentyl)-carbamic acid tert-butyl ester

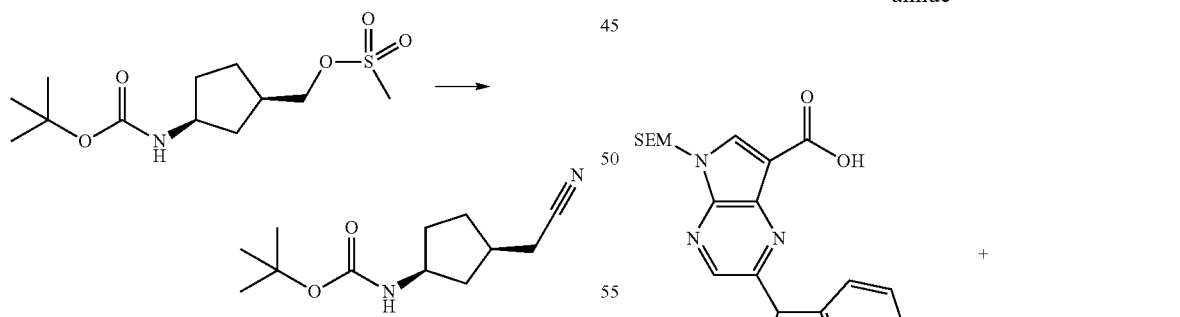

In a round-bottomed flask, methanesulfonic acid (cis)-3-tert-butoxycarbonylamino-cyclopentylmethyl ester (crude from Step 4, 779 mg) was dissolved in DMF (5 ml). Potassium cyanide (277 mg, 4.25 mmol) was added and the reaction mixture was stirred at 80° C. overnight. Sodium cyanide (104 mg, 2.12 mmol) was added and the reaction mixture was stirred at 80° C. for 48 h. The reaction was cooled to room temperature, quenched with water and extracted with diethyl ether (2×). The combined organic layers were washed twice with water and once with brine then dried over sodium sulfate, filtered and concentrated. The residue was chromatographed over silica gel with EtOAc/hexanes (gradient 0-30% EtOAc) to afford 190 mg (38%, 2 steps) of (cis-3-cyanomethyl-cyclopentyl)-carbamic acid tert-butyl ester as a light yellow oil.

Step 6

(cis-3-Amino-cyclopentyl)-acetonitrile trifluoroacetate

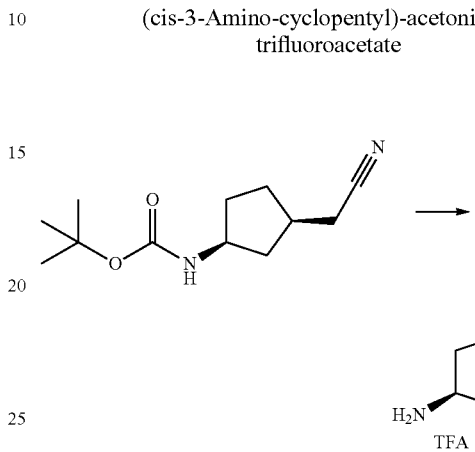

In a round-bottomed flask, (cis-3-cyanomethyl-cyclopentyl)-carbamic acid tert-butyl ester (188 mg, 0.84 mmol) was dissolved in dichloromethane (5 ml) and trifluoroacetic acid (2.0 ml, 26.0 mmol) was slowly added. The reaction mixture was stirred at room temperature for 2 h then concentrated to afford (cis-3-amino-cyclopentyl)-acetonitrile trifluoroacetate as a yellow oil which was used without further purification.

Step 7

2-(6-Fluoro-1-methyl-1H-indazol-3-yl)-5-(2-trimethylsilanyl-ethoxymethyl)-5H-pyrrolo[2,3-b]pyrazine-7-carboxylic acid (cis-3-cyanomethyl-cyclopentyl)-amide

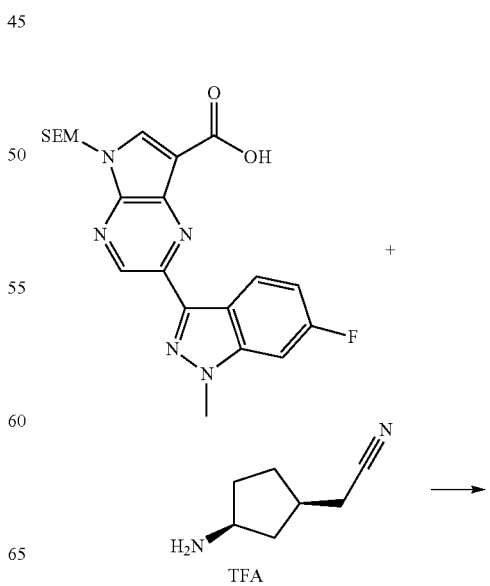

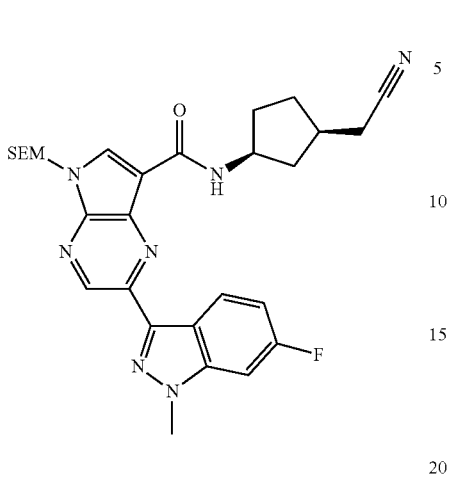

In a round-bottomed flask, (cis-3-amino-cyclopentyl)-acetonitrile trifluoroacetate (crude from Step 6) was dissolved in DMF (1.3 ml) and N,N-diisopropylethylamine (0.65 ml, 3.72 mmol) was added. Then, 2-(6-fluoro-1-methyl-1H-indazol-3-yl)-5-(2-trimethylsilanylethoxymethyl)-5H-pyrrolo[2,3-b]pyrazine-7-carboxylic acid (110 mg, 0.25 mmol) and HATU (104 mg, 0.27 mmol) were added. The yellow solution was stirred at room temperature for 48 h. Water and petroleum ether were added and the resulting suspension was filtered. The filter cake was washed with water and petroleum ether then dried under high vacuum to afford 128 mg (94%) of 2-(6-fluoro-1-methyl-1H-indazol-3-yl)-5-(2-trimethylsilanyl-ethoxymethyl)-5H-pyrrolo[2,3-b]pyrazine-7-carboxylic acid (cis-3-cyanomethyl-cyclopentyl)-amide as an off-white powder.

Step 8

2-(6-Fluoro-1-methyl-1H-indazol-3-yl)-5H-pyrrolo[2,3-b]pyrazine-7-carboxylic acid (cis-3-cyanomethyl-cyclopentyl)-amide

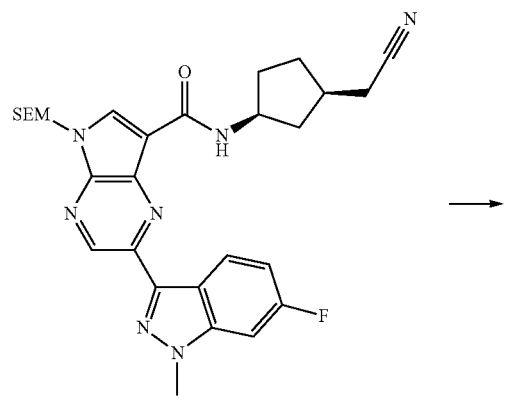

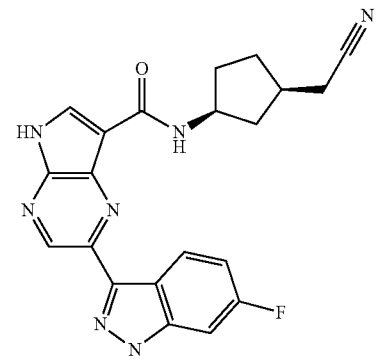

In a round-bottomed flask, 2-(6-fluoro-1-methyl-1H-indazol-3-yl)-5-(2-trimethylsilanylethoxymethyl)-5H-pyrrolo[2,3-b]pyrazine-7-carboxylic acid (cis-3-cyanomethyl-cyclopentyl)-amide (126 mg, 0.23 mmol) was dissolved in dichloromethane (1.2 ml) and trifluoroacetic acid (0.7 ml, 9.2 mmol) was added. The reaction mixture was stirred at room temperature for 2 h then concentrated. The residue was dissolved in dichloromethane (1.2 ml) and ethylenediamine (0.93 ml, 13.8 mmol) was added. The yellow solution was stirred at room temperature for 1.25 h then quenched with water and diluted with ethyl acetate. The resultant suspension was filtered, washed with hot water and ethyl acetate and dried under high vacuum to provide 75 mg (74%) of 2-(6-fluoro-1-methyl-1H-indazol-3-yl)-5H-pyrrolo[2,3-b]pyrazine-7-carboxylic acid (cis-3-cyanomethyl-cyclopentyl)-amide as a light yellow powder. MS: (M+H)$^{+}$=418; $^{1}$H NMR (DMSO-d$_6$, 300 MHz): δ (ppm) 12.61 (br. s., 1H), 9.09 (s, 1H), 8.40-8.49 (m, 2H), 8.18 (d, J=7.2 Hz, 1H), 7.69 (dd, J=9.8, 2.3 Hz, 1H), 7.24 (td, J=9.2, 2.1 Hz, 1H), 4.29-4.45 (m, 1H), 4.15 (s, 3H), 2.66 (d, J=6.4 Hz, 2H), 2.34-2.43 (m, 1H), 2.23-2.34 (m, 1H), 2.11-2.23 (m, 1H), 1.85-2.00 (m, 1H), 1.46-1.74 (m, 2H), 1.28-1.41 (m, 1H).

Example 58

2-(6-Fluoro-imidazo[1,5-a]pyridin-1-yl)-5H-pyrrolo[2,3-b]pyrazine-7-carboxylic acid ((R)-1-oxazol-2-yl-ethyl)-amide

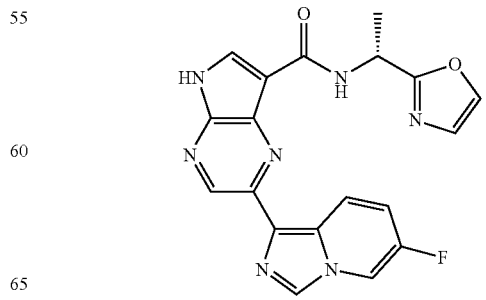

Step 1

2-Bromo-5-(2-trimethylsilanyl-ethoxymethyl)-5H-pyrrolo[2,3-b]pyrazine-7-carboxylic acid (1-oxazol-2-yl-ethyl)-amide

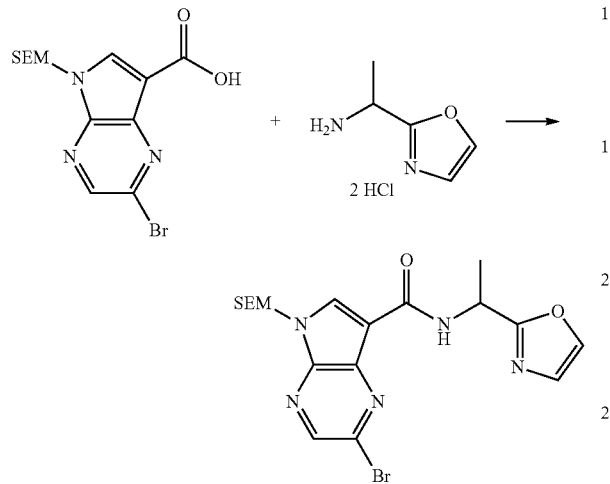

A round-bottomed flask was charged with 2-bromo-5-((2-(trimethylsilyl)ethoxy)methyl)-5H-pyrrolo[2,3-b]pyrazine-7-carboxylic acid (300 mg, 0.81 mmol) and 1-oxazol-2-yl-ethylamine dihydrochloride (244 mg, 1.0 mmol). DMF (4 ml) was added followed by N,N-diisopropylethylamine (0.9 ml, 5.15 mmol) and HATU (337 mg, 0.89 mmol). The reaction mixture was stirred at room temperature overnight then quenched with water and diluted with petroleum ether. The resulting suspension was filtered. The filter cake was washed with water and petroleum ether then dried under high vacuum to afford 268 mg (71%) of 2-bromo-5-(2-trimethylsilanyl-ethoxymethyl)-5H-pyrrolo[2,3-b]pyrazine-7-carboxylic acid (1-oxazol-2-yl-ethyl)-amide as an off-white powder.

Step 2

2-Bromo-5-(2-trimethylsilanyl-ethoxymethyl)-5H-pyrrolo[2,3-b]pyrazine-7-carboxylic acid ((R)-1-oxazol-2-yl-ethyl)-amide and 2-Bromo-5-(2-trimethylsilanyl-ethoxymethyl)-5H-pyrrolo[2,3-b]pyrazine-7-carboxylic acid ((S)-1-oxazol-2-yl-ethyl)-amide

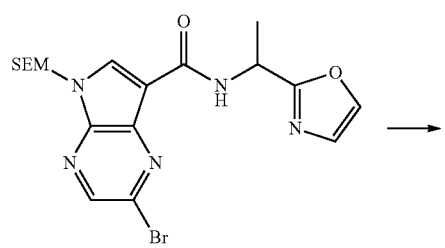

→

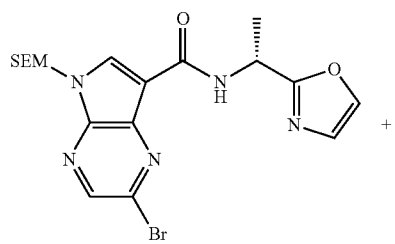

+

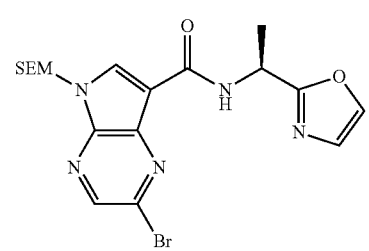

A racemic sample of 2-bromo-5-(2-trimethylsilanyl-ethoxymethyl)-5H-pyrrolo[2,3-b]pyrazine-7-carboxylic acid (1-oxazol-2-yl-ethyl)-amide (268 mg) was subjected to SFC chromatography. Separation of the enantiomers was achieved with a DAICEL OD 3×25 column using 20% MeOH/CO$_2$ as the eluent. Obtained 152 mg (57%) of 2-bromo-5-(2-trimethylsilanylethoxymethyl)-5H-pyrrolo[2,3-b]pyrazine-7-carboxylic acid ((R)-1-oxazol-2-yl-ethyl)-amide as an off-white powder and 85 mg (32%) of 2-bromo-5-(2-trimethylsilanyl-ethoxymethyl)-5H-pyrrolo[2,3-b]pyrazine-7-carboxylic acid ((S)-1-oxazol-2-yl-ethyl)-amide as an off-white powder.

Step 3

2-(6-Fluoro-imidazo[1,5-a]pyridin-1-yl)-5-(2-trimethylsilanyl-ethoxymethyl)-5H-pyrrolo[2,3-b]pyrazine-7-carboxylic acid ((R)-1-oxazol-2-yl-ethyl)-amide

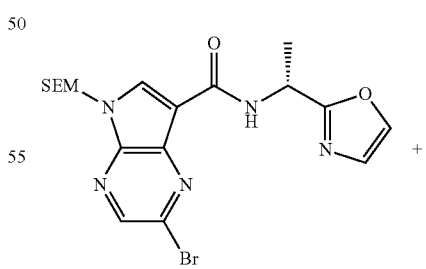

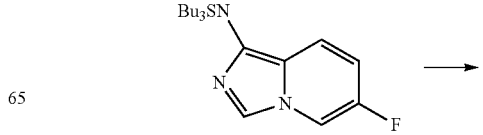

→

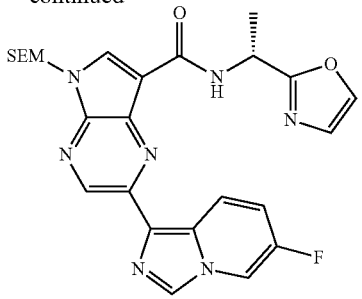

In a round-bottomed flask, 2-bromo-5-(2-trimethylsilanyl-ethoxymethyl)-5H-pyrrolo[2,3-b]pyrazine-7-carboxylic acid ((R)-1-oxazol-2-yl-ethyl)-amide (148 mg, 0.32 mmol) and 6-Fluoro-1-tributylstannyl-imidazo[1,5-a]pyridine (380 mg, 0.45 mmol) were dissolved in DMF (3 ml). The flask was evacuated and backfilled with argon then tetrakis(triphenylphosphine)palladium (0) (19 mg, 0.016 mmol) and copper (I) iodide (13 mg, 0.068 mmol) were added. The reaction mixture was stirred at 80° C. in an oil bath overnight then cooled to room temperature, quenched with water and extracted with diethyl ether (2×). The combined organic layers were washed twice with water and once with brine then dried over sodium sulfate, filtered and concentrated. The residue was chromatographed over silica sel with MeOH/CH$_2$Cl$_2$/0.5% NH$_4$OH (gradient 0-2% MeOH) to afford 109 mg (66%) of 2-(6-fluoro-imidazo[1,5-a]pyridin-1-yl)-5-(2-trimethylsilanyl-ethoxymethyl)-5H-pyrrolo[2,3-b]pyrazine-7-carboxylic acid ((R)-1-oxazol-2-yl-ethyl)-amide as a yellow solid.

Step 4

2-(6-Fluoro-imidazo[1,5-a]pyridin-1-yl)-5H-pyrrolo[2,3-b]pyrazine-7-carboxylic acid ((R)-1-oxazol-2-yl-ethyl)-amide

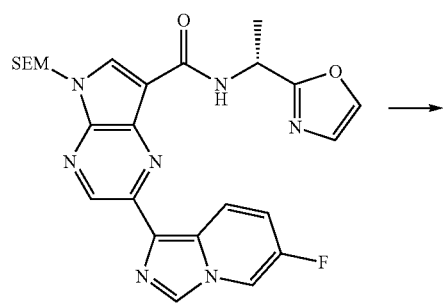

[2,3-b]pyrazine-7-carboxylic acid ((R)-1-oxazol-2-yl-ethyl)-amide (107 mg, 0.205 mmol) was dissolved in dichloromethane (1.1 ml) and trifluoroacetic acid (0.64 ml, 8.3 mmol) was added. The reaction mixture was stirred at room temperature for 2 h then concentrated. The residue was dissolved in dichloromethane (1.1 ml) and ethylenediamine (0.84 ml, 12.4 mmol) was added. The yellow reaction mixture was stirred at room temperature for 1 h then quenched with water and diluted with ethyl acetate. The resultant suspension was filtered, washed with hot water and ethyl acetate and dried under high vacuum to provide 76 mg (90%) of 2-(6-fluoro-imidazo[1,5-a]pyridin-1-yl)-5H-pyrrolo[2,3-b]pyrazine-7-carboxylic acid ((R)-1-oxazol-2-yl-ethyl)-amide as a yellow powder. MS: (M+Na)$^+$=414; $^1$H NMR (DMSO-d$_6$, 300 MHz): δ (ppm) 12.76 (br. s., 1H), 9.12 (s, 1H), 8.70 (dd, J=4.7, 2.1 Hz, 1H), 8.60 (d, J=8.7 Hz, 1H), 8.54 (s, 1H), 8.36-8.46 (m, 2H), 8.11 (s, 1H), 7.25 (s, 1H), 7.04 (ddd, J=9.9, 7.8, 1.9 Hz, 1H), 5.45-5.60 (m, 1H), 1.65 (d, J=6.8 Hz, 3H).

Example 59

2-(6-Fluoro-1-methyl-1H-indazol-3-yl)-5H-pyrrolo[2,3-b]pyrazine-7-carboxylic acid [(R)-1-(3-fluoro-azetidine-1-carbonyl)-butyl]-amide

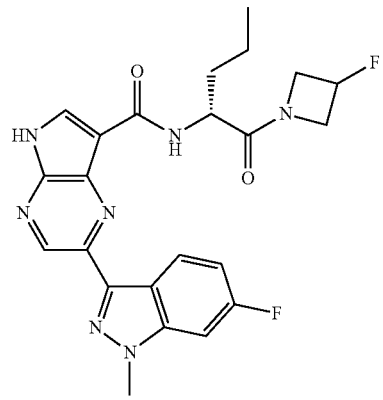

Step 1

[(R)-1-(3-Fluoro-azetidine-1-carbonyl)-butyl]-carbamic acid tert-butyl ester

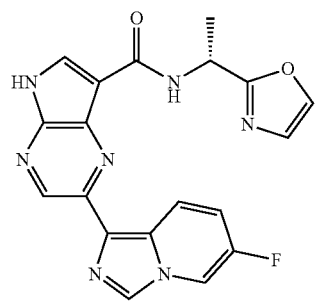 [SMILES: C[C@@H](NC(=O)c1c[nH]c2ncc(-c3ncn4cc(F)ccc34)nc12)c1ncco1]

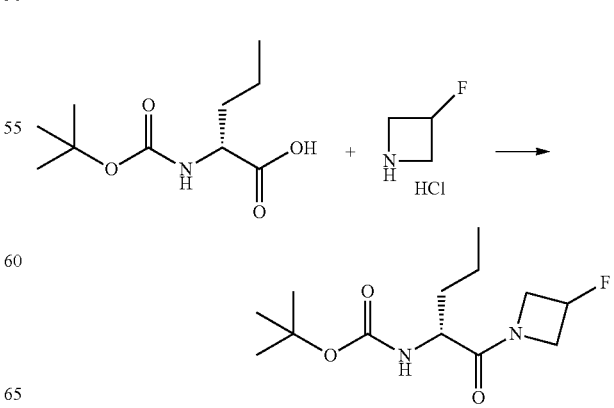

417

A round-bottomed flask was charged with Boc-D-norvaline (300 mg, 1.38 mmol) and 3-fluoroazetidine hydrochloride (216 mg, 1.93 mmol). DMF (6 ml) was added followed by N,N-diisopropylethylamine (0.65 ml, 3.72 mmol) and HATU (578 mg, 1.52 mmol). The yellow reaction mixture was stirred at room temperature for 48 h the quenched with water and extracted with diethyl ether (2×). The combined organic layers were washed twice with water and once with brine then dried over sodium sulfate, filtered and concentrated to give 417 mg of [(R)-1-(3-fluoro-azetidine-1-carbonyl)-butyl]-carbamic acid tert-butyl ester as a light yellow solid.

Step 2

(R)-2-Amino-1-(3-fluoro-azetidin-1-yl)-pentan-1-one trifluoroacetate

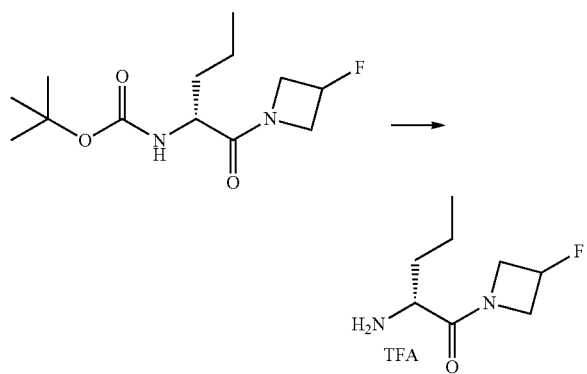

In a round-bottomed flask, [(R)-1-(3-fluoro-azetidine-1-carbonyl)-butyl]-carbamic acid tert-butyl ester (200 mg, 0.66 mmol) was dissolved in dichloromethane (4 ml) and trifluoroacetic acid (1.6 ml, 20.8 mmol) was slowly added. The reaction mixture was stirred at room temperature for 2 h then concentrated to provide (R)-2-amino-1-(3-fluoro-azetidin-1-yl)-pentan-1-one trifluoroacetate as a pale brown oil which was used without further purification.

Step 3

2-(6-Fluoro-1-methyl-1H-indazol-3-yl)-5-(2-trimethylsilanyl-ethoxymethyl)-5H-pyrrolo[2,3-b]pyrazine-7-carboxylic acid [(R)-1-(3-fluoro-azetidine-1-carbonyl)-butyl]-amide

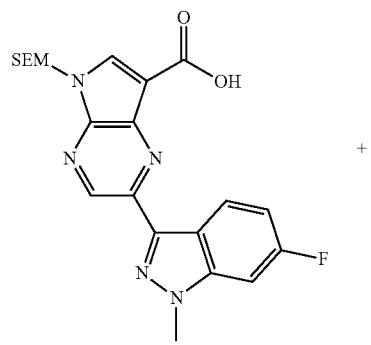

+

418

-continued

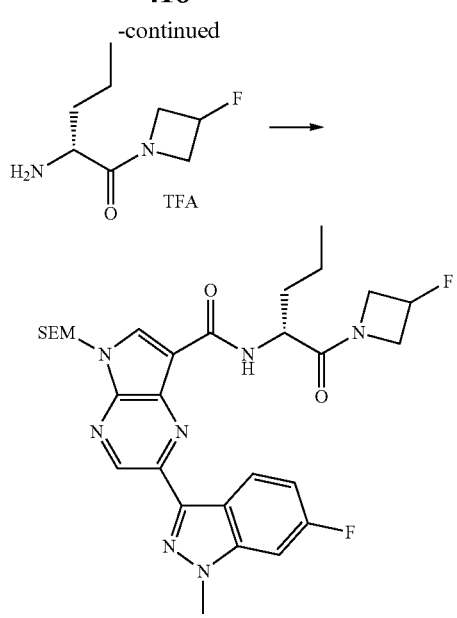

In a round-bottomed flask, (R)-2-amino-1-(3-fluoro-azetidin-1-yl)-pentan-1-one trifluoroacetate (crude from Step 2) was dissolved in DMF (1.5 ml) and N,N-diisopropylethylamine (0.60 ml, 3.44 mmol) was added. Then 2-(6-fluoro-1-methyl-1H-indazol-3-yl)-5-(2-trimethylsilanyl-ethoxymethyl)-5H-pyrrolo[2,3-b]pyrazine-7-carboxylic acid (110 mg, 0.25 mmol) and HATU (104 mg, 0.27 mmol) were added. The yellow reaction mixture was stirred at room temperature overnight then quenched with water and diluted with petroleum ether. The resulting suspension was filtered. The filter cake was washed with water and petroleum ether then dried under high vacuum to afford 128 mg (86%) of 2-(6-fluoro-1-methyl-1H-indazol-3-yl)-5-(2-trimethylsilanyl-ethoxymethyl)-5H-pyrrolo[2,3-b]pyrazine-7-carboxylic acid [(R)-1-(3-fluoro-azetidine-1-carbonyl)-butyl]-amide as an off-white powder.

Step 4

2-(6-Fluoro-1-methyl-1H-indazol-3-yl)-5H-pyrrolo[2,3-b]pyrazine-7-carboxylic acid [(R)-1-(3-fluoro-azetidine-1-carbonyl)-butyl]-amide

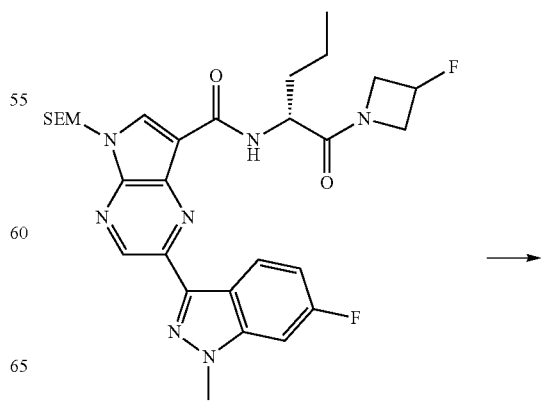

419
-continued

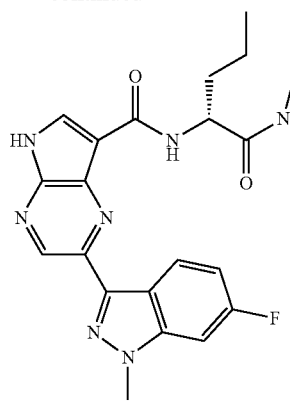

In a round-bottomed flask, 2-(6-fluoro-1-methyl-1H-indazol-3-yl)-5-(2-trimethylsilanylethoxymethyl)-5H-pyrrolo[2,3-b]pyrazine-7-carboxylic acid [(R)-1-(3-fluoro-azetidine-1-carbonyl)-butyl]-amide (126 mg, 0.21 mmol) was dissolved in dichloromethane (1.1 ml) and trifluoroacetic acid (0.65 ml, 8.4 mmol) was added. The reaction mixture was stirred at room temperature for 2.5 h then concentrated. The residue was dissolved in dichloromethane (1.1 ml) and ethylenediamine (0.85 ml, 12.7 mmol) was added. The reaction was stirred at room temperature for 1 h then quenched with water and diluted with ethyl acetate. The resulting suspension was filtered, washed with hot water and ethyl acetate and dried under high vacuum to provide 49 mg (50%) of 2-(6-fluoro-1-methyl-1H-indazol-3-yl)-5H-pyrrolo[2,3-b]pyrazine-7-carboxylic acid [(R)-1-(3-fluoro-azetidine-1-carbonyl)-butyl]-amide as an off-white powder. MS: (M+H)$^+$=468; $^1$H NMR (DMSO-d$_6$, 300 MHz): δ (ppm) 12.84 (br. s, 1H), 9.15 (s, 1H), 8.74 (dt, J=9.3, 4.6 Hz, 1H), 8.41-8.52 (m, 2H), 7.68 (d, J=7.9 Hz, 1H), 7.02-7.17 (m, 1H), 5.29-5.61 (m, 1H), 4.18-4.84 (m, 4H), 4.16 (s, 3H), 3.87-4.09 (m, 1H), 1.62-1.91 (m, 2H), 1.41 (d, J=7.2 Hz, 2H), 0.82-0.97 (m, 3H).

Example 60

2-(6-Fluoro-1-methyl-1H-indazol-3-yl)-5H-pyrrolo[2,3-b]pyrazine-7-carboxylic acid [(R)-1-(4,5-dihydro-oxazol-2-yl)-ethyl]-amide

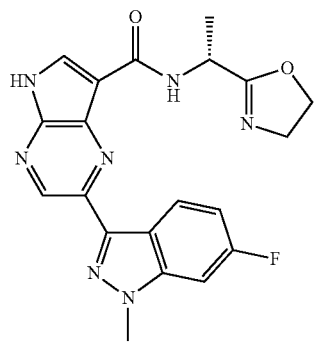 [SMILES: C[C@@H](NC(=O)c1c[nH]c2ncc(-c3nn(C)c4cc(F)ccc34)nc12)C1=NCCO1]

420
Step 1

[(R)-1-(2-Hydroxy-ethylcarbamoyl)-ethyl]-carbamic acid tert-butyl ester

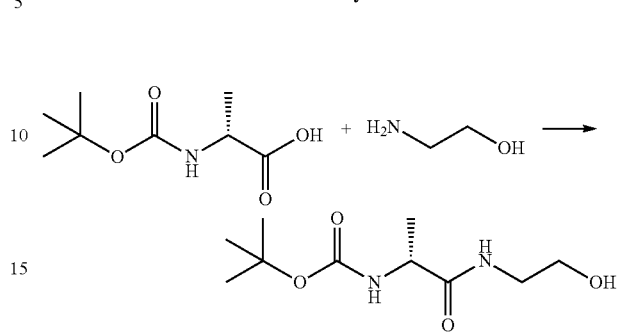

In a round-bottomed flask, Boc-D-alanine (1.0 g, 5.29 mmol) was dissolved in THF (40 ml) and 1,1'-carbonyldiimidazole (1.03 g, 6.34 mmol) was added. The reaction mixture was stirred at 60° C. for 45 min then cooled to room temperature and ethanolamine (3.2 ml, 52.9 mmol) was added. The reaction mixture was stirred at room temperature overnight then quenched with 1 M aqueous HCl (15 ml) and extracted with dichloromethane. The organic layer was washed with 1 M aqueous HCl, water and brine. The aqueous layers were back-extracted with dichloromethane (2×). The organic layers were combined, dried over sodium sulfate, filtered and concentrated to afford 1.11 g (90%) of [(R)-1-(2-hydroxy-ethylcarbamoyl)-ethyl]-carbamic acid tert-butyl ester as a colorless oil.

Step 2

(R)-2-Amino-N-(2-hydroxy-ethyl)-propionamide trifluoroacetate

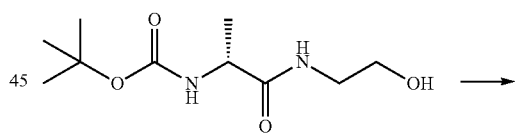

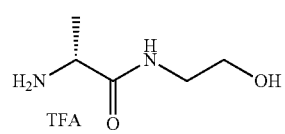

In a round-bottomed flask, [(R)-1-(2-hydroxy-ethylcarbamoyl)-ethyl]-carbamic acid tert-butyl ester (180 mg, 0.78 mmol) was dissolved in dichloromethane (5 ml) and trifluoroacetic acid (1.8 ml, 23.4 mmol) was slowly added. The pale yellow reaction mixture was stirred at room temperature for 2 h then concentrated to afford (R)-2-amino-N-(2-hydroxyethyl)-propionamide trifluoroacetate as a light yellow oil which was used without further purification.

Step 3

2-(6-Fluoro-1-methyl-1H-indazol-3-yl)-5-(2-trimethylsilanyl-ethoxymethyl)-5H-pyrrolo[2,3-b]pyrazine-7-carboxylic acid [(R)-1-(2-hydroxy-ethylcarbamoyl)-ethyl]-amide

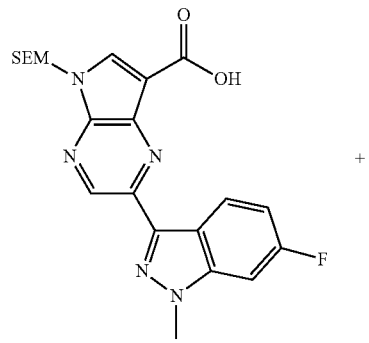

+

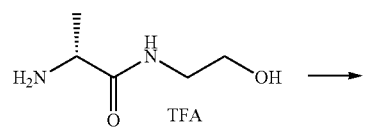

→

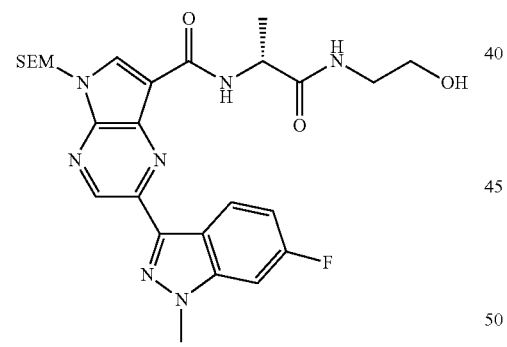

In a round-bottomed flask, (R)-2-amino-N-(2-hydroxyethyl)-propionamide trifluoroacetate (crude from Step 2) was dissolved in DMF (2 ml) and N,N-diisopropylethylamine (0.70 ml, 4.0 mmol) was added. Then 2-(6-fluoro-1-methyl-1H-indazol-3-yl)-5-(2-trimethylsilanyl-ethoxymethyl)-5H-pyrrolo[2,3-b]pyrazine-7-carboxylic acid (170 mg, 0.39 mmol) was added followed by HATU (161 mg, 0.42 mmol). The yellow reaction mixture was stirred at room temperature overnight then quenched with water and diluted with petroleum ether. The resulting suspension was filtered. The filter cake was washed with water and petroleum ether then dried under high vacuum. The residue was chromatographed over silica gel with EtOAc/hexanes (gradient 0-100% EtOAc) and MeOH/EtOAc (gradient 0-10% MeOH) to give 127 mg (59%) of 2-(6-fluoro-1-methyl-1H-indazol-3-yl)-5-(2-trimethylsilanylethoxymethyl)-5H-pyrrolo[2,3-b]pyrazine-7-carboxylic acid [(R)-1-(2-hydroxy-ethylcarbamoyl)-ethyl]-amide as an off-white solid.

Step 4

2-(6-Fluoro-1-methyl-1H-indazol-3-yl)-5-(2-trimethylsilanyl-ethoxymethyl)-5H-pyrrolo[2,3-b]pyrazine-7-carboxylic acid [(R)-1-(4,5-dihydro-oxazol-2-yl)-ethyl]-amide

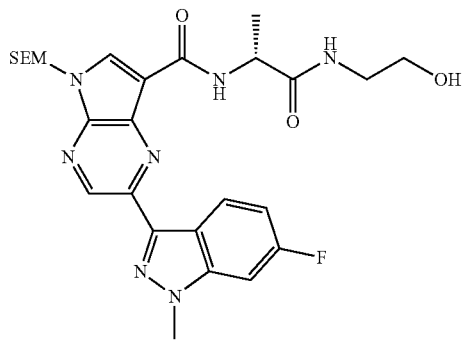

→

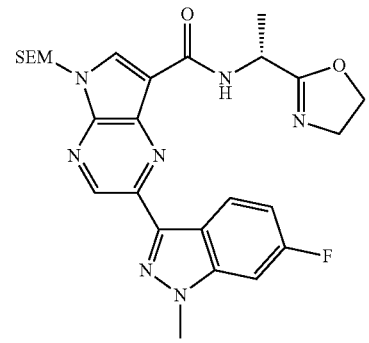

In a round-bottomed flask, 2-(6-fluoro-1-methyl-1H-indazol-3-yl)-5-(2-trimethylsilanylethoxymethyl)-5H-pyrrolo[2,3-b]pyrazine-7-carboxylic acid [(R)-1-(2-hydroxy-ethylcarbamoyl)-ethyl]-amide (126 mg, 0.23 mmol) was dissolved in dichloromethane (2.2 ml). The solution was cooled to −76° C. and DAST (45 µl, 0.34 mmol) was added. The pale yellow reaction mixture was stirred at −76° C. for 6 h then anhydrous potassium carbonate (64 mg, 0.46 mmol) was added in one portion. The reaction mixture was allowed to warm to room temperature, quenched with saturated aqueous NaHCO₃ and extracted with dichloromethane (3×). The organic layers were combined, dried over sodium sulfate, filtered and concentrated. The residue was chromatographed over silica gel with EtOAc/hexanes (gradient 0-90% EtOAc) to afford 86 mg (71%) of 2-(6-fluoro-1-methyl-1H-indazol-3-yl)-5-(2- trimethylsilanyl-ethoxymethyl)-5H-pyrrolo[2,3-b]pyrazine-7-carboxylic acid [(R)-1-(4,5-dihydro-oxazol-2-yl)-ethyl]-amide as a light yellow solid.

Step 5

2-(6-Fluoro-1-methyl-1H-indazol-3-yl)-5H-pyrrolo[2,3-b]pyrazine-7-carboxylic acid [(R)-1-(4,5-dihydro-oxazol-2-yl)-ethyl]-amide

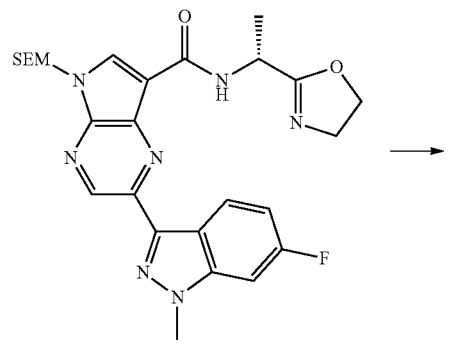

In a small vial, 2-(6-fluoro-1-methyl-1H-indazol-3-yl)-5-(2-trimethylsilanylethoxymethyl)-5H-pyrrolo[2,3-b]pyrazine-7-carboxylic acid [(R)-1-(4,5-dihydro-oxazol-2-yl)-ethyl]-amide (85 mg, 0.16 mmol) was dissolved in tetrabutylammonium fluoride (1.0 M in THF, 1.6 ml, 1.6 mmol). The yellow reaction mixture was stirred at 60° C. overnight then cooled to room temperature, quenched with water and extracted with EtOAc (2×). The combined organic layers were washed with water and brine then dried over sodium sulfate, filtered and concentrated. The residue was chromatographed over silica gel with MeOH/CH$_2$Cl$_2$/0.5% NH$_4$OH (gradient 0-5% MeOH) to afford 27 mg (40%) of 2-(6-fluoro-1-methyl-1H-indazol-3-yl)-5H-pyrrolo[2,3-b]pyrazine-7-carboxylic acid [(R)-1-(4,5-dihydro-oxazol-2-yl)-ethyl]-amide as an off-white solid. MS: (M+Na)$^+$=430; $^1$H NMR (DMSO-d$_6$, 300 MHz): δ (ppm) 12.93 (br. s., 1H), 9.14 (s, 1H), 8.69 (dd, J=9.1, 5.3 Hz, 1H), 8.57 (d, J=8.3 Hz, 1H), 8.49 (s, 1H), 7.69 (dd, J=9.8, 1.9 Hz, 1H), 7.14 (td, J=9.1, 2.3 Hz, 1H), 4.97 (quin, J=7.5 Hz, 1H), 4.27-4.39 (m, 2H), 4.16 (s, 3H), 3.79 (td, J=9.3, 4.3 Hz, 2H), 1.50 (d, J=7.2 Hz, 3H).

Example 61

2-(6-Fluoro-1-methyl-1H-indazol-3-yl)-5H-pyrrolo[2,3-b]pyrazine-7-carboxylic acid ((R)-2,2-difluoro-1-methyl-3-phenyl-propyl)-amide

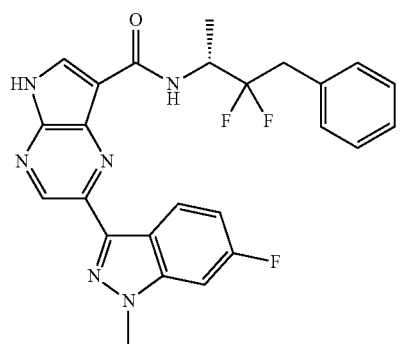 [SMILES: C[C@@H](NC(=O)c1c[nH]c2ncc(-c3nn(C)c4cc(F)ccc34)nc12)C(F)(F)Cc1ccccc1]

Step 1

((R)-1-Methyl-2-oxo-3-phenyl-propyl)-carbamic acid tert-butyl ester

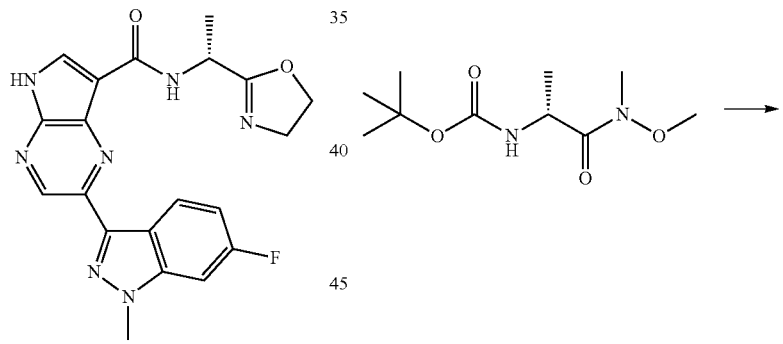

In a round-bottomed flask, [(R)-1-(methoxy-methyl-carbamoyl)-ethyl]-carbamic acid tert-butyl ester (300 mg, 1.29 mmol) was dissolved in THF (8 ml). The solution was cooled to −16° C. (NaCl/ice bath) and benzylmagnesium chloride (1.0 M in diethyl ether, 3.8 ml, 3.8 mmol) was added dropwise. After the addition, the reaction mixture was allowed to warm slowly to room temperature and stirred for 5.5 h. The reaction mixture was quenched with saturated aqueous NH$_4$Cl and extracted with EtOAc (2×). The combined organic layers were washed with water and brine then dried over sodium sulfate, filtered and concentrated. The residue was chromatographed over silica gel with EtOAc/hexanes

425

(gradient 0-20% EtOAc) to afford 353 mg (99%) of ((R)-1-methyl-2-oxo-3-phenyl-propyl)-carbamic acid tert-butyl ester as a colorless oil.

Step 2

((R)-2,2-Difluoro-1-methyl-3-phenyl-propyl)-carbamic acid tert-butyl ester

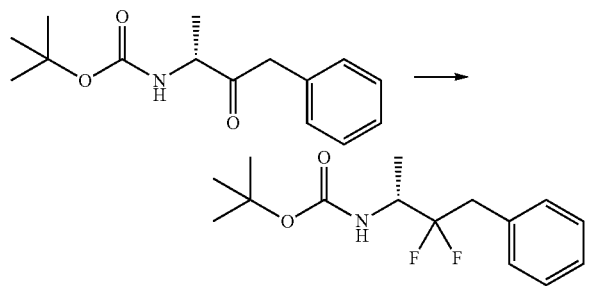

In a dry round-bottomed flask, ((R)-1-methyl-2-oxo-3-phenyl-propyl)-carbamic acid tert-butyl ester (171 mg, 0.65 mmol) was dissolved in dichloromethane (0.3 ml). DAST (0.26 ml, 1.97 mmol) was added dropwise at room temperature and the reaction mixture was stirred at room temperature overnight. The reaction mixture was diluted with dichloromethane and slowly quenched with 5 ml of saturated aqueous NaHCO$_3$. The aqueous layer was extracted with dichloromethane (2×). The organic layers were combined, dried over sodium sulfate, filtered and concentrated. The residue was chromatographed over silica gel with EtOAc/hexanes (gradient 0-5% EtOAc) to afford 95 mg (51%) of ((R)-2,2-difluoro-1-methyl-3-phenyl-propyl)-carbamic acid tert-butyl ester as a light yellow solid. $^1$H NMR (CDCl$_3$, 300 MHz): δ (ppm) 7.23-7.39 (m, 5H), 4.57-4.72 (m, 1H), 3.93-4.14 (m, 1H), 3.12-3.28 (m, 2H), 1.47 (s, 9H), 1.24 (dd, J=6.8, 1.1 Hz, 3H).

Step 3

(R)-2,2-Difluoro-1-methyl-3-phenyl-propylamine trifluoroacetate

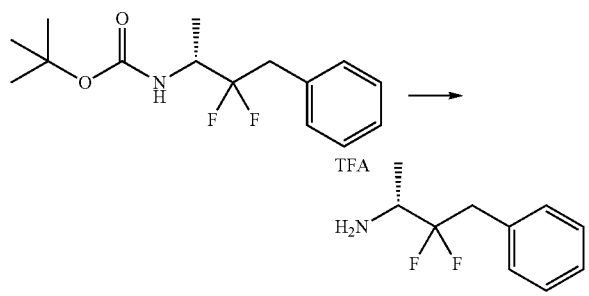

In a round-bottomed flask, ((R)-2,2-difluoro-1-methyl-3-phenyl-propyl)-carbamic acid tert-butyl ester (92 mg, 0.32 mmol) was dissolved in dichloromethane (2 ml) and trifluoroacetic acid (0.75 ml, 9.73 mmol) was slowly added. The reaction was stirred at room temperature for 2 h then concentrated to give (R)-2,2-difluoro-1-methyl-3-phenyl-propylamine trifluoroacetate as a light brown oil which was used without further purification Step 4

2-(6-Fluoro-1-methyl-1H-indazol-3-yl)-5-(2-trimethylsilanyl-ethoxymethyl)-5H-pyrrolo[2,3-b]pyrazine-7-carboxylic acid ((R)-2,2-difluoro-1-methyl-3-phenyl-propyl)-amide

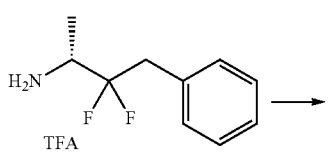

+

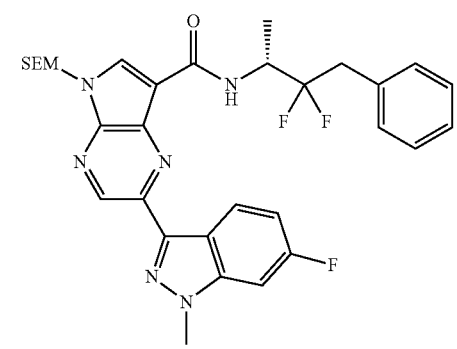

In a round-bottomed flask, (R)-2,2-difluoro-1-methyl-3-phenyl-propylamine trifluoroacetate (crude from Step 3) was dissolved in DMF (1.1 ml) and N,N-diisopropylethylamine (0.25 ml, 1.43 mmol) was added. Then 2-(6-fluoro-1-methyl-1H-indazol-3-yl)-5-(2-trimethylsilanyl-ethoxymethyl)-5H-pyrrolo[2,3-b]pyrazine-7-carboxylic acid (100 mg, 23 mmol) was added followed by HATU (95 mg, 0.25 mmol). The yellow reaction was stirred at room temperature overnight then quenched with water and extracted with diethyl ether (2×). The combined organic layers were washed twice with water and once with brine then dried over sodium sulfate, filtered and concentrated. The residue was triturated with petroleum ether to afford 136 mg (94%) of 2-(6-fluoro-1-methyl-1H-indazol-3-yl)-5-(2-trimethylsilanyl ethoxymethyl)-5H-pyrrolo[2,3-b]pyrazine-7-carboxylic acid ((R)-2,2-difluoro-1-methyl-3-phenyl-propyl)-amide as an off-white powder.

Step 5

2-(6-Fluoro-1-methyl-1H-indazol-3-yl)-5H-pyrrolo[2,3-b]pyrazine-7-carboxylic acid ((R)-2,2-difluoro-1-methyl-3-phenyl-propyl)-amide

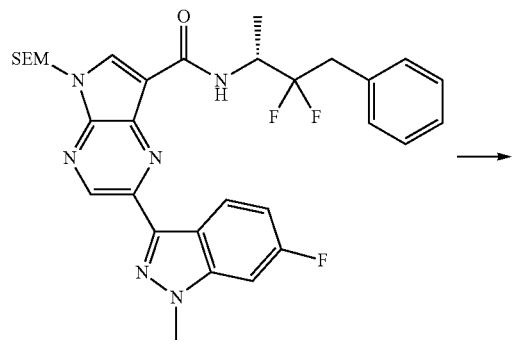

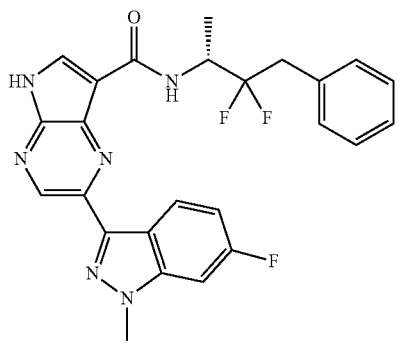

In a round-bottomed flask, 2-(6-fluoro-1-methyl-1H-indazol-3-yl)-5-(2-trimethylsilanylethoxymethyl)-5H-pyrrolo[2,3-b]pyrazine-7-carboxylic acid ((R)-2,2-difluoro-1-methyl-3-phenyl-propyl)-amide (133 mg, 0.21 mmol was dissolved in dichloromethane (1.1 ml) and trifluoroacetic acid (0.64 ml, 8.3 mmol) was added. The reaction mixture was stirred at room temperature for 2 h then concentrated. The residue was dissolved in dichloromethane (1.1 ml) and ethylenediamine (0.84 ml, 12.4 mmol) was added. The yellow solution was stirred at room temperature for 1 h then quenched with water and extracted with EtOAc (2×). The combined organic layers were washed with water and brine then dried over sodium sulfate, filtered and concentrated. The residue was triturated with 5% EtOAc/diethyl ether to afford 73 mg (70%) of 2-(6-fluoro-1-methyl-1H-indazol-3-yl)-5H-pyrrolo[2,3-b]pyrazine-7-carboxylic acid ((R)-2,2-difluoro-1-methyl-3-phenyl-propyl)-amide as a light yellow powder. MS: (M+Na)$^+$=501; $^1$H NMR (DMSO-d$_6$, 400 MHz): δ (ppm) 12.94 (br. s., 1H), 9.12 (s, 1H), 8.52 (s, 1H), 8.47 (dd, J=8.9, 5.4 Hz, 1H), 8.36 (d, J=9.8 Hz, 1H), 7.68 (dd, J=9.8, 2.0 Hz, 1H), 7.23-7.35 (m, 5H), 7.02 (td, J=9.0, 2.3 Hz, 1H), 4.60-4.78 (m, 1H), 4.15 (s, 3H), 3.33-3.45 (m, 2H), 1.41 (d, J=7.0 Hz, 3H).

Example 62

2-(6-Fluoro-1-methyl-1H-indazol-3-yl)-5H-pyrrolo[2,3-b]pyrazine-7-carboxylic acid [(R)-1-(4-cyanomethyl-oxazol-2-yl)-ethyl]-amide

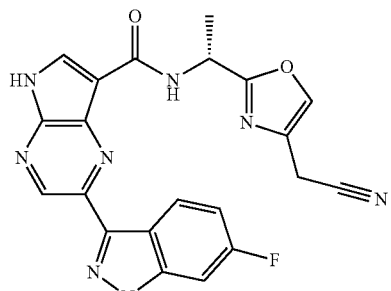

Step 1

2-((R)-2-tert-Butoxycarbonylamino-propionylamino)-3-hydroxy-propionic acid methyl ester

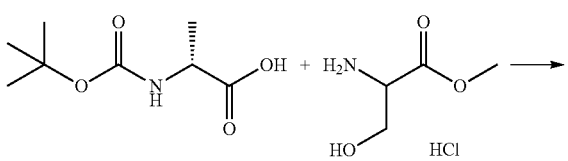

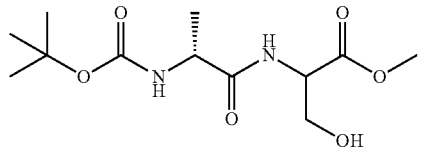

A round-bottomed flask was charged with Boc-D-alanine (600 mg, 3.17 mmol) and DL-serine methyl ester hydrochloride (691 mg, 4.44 mmol). DMF (12 ml) was added followed by N,N-diisopropylethylamine (1.5 ml, 8.6 mmol) and HATU (1.33 g, 3.49 mmol). The yellow reaction mixture was stirred at room temperature for 48 h then quenched with water and extracted with diethyl ether (2×). The combined organic layers were washed twice with water and once with brine then dried over sodium sulfate, filtered and concentrated to afford 422 mg (41%) of 2-((R)-2-tert-butoxycarbonylamino-propionylamino)-3-hydroxy-propionic acid methyl ester as a colorless oil.

Step 2

2-((R)-1-tert-Butoxycarbonylamino-ethyl)-4,5-dihydro-oxazole-4-carboxylic acid methyl ester

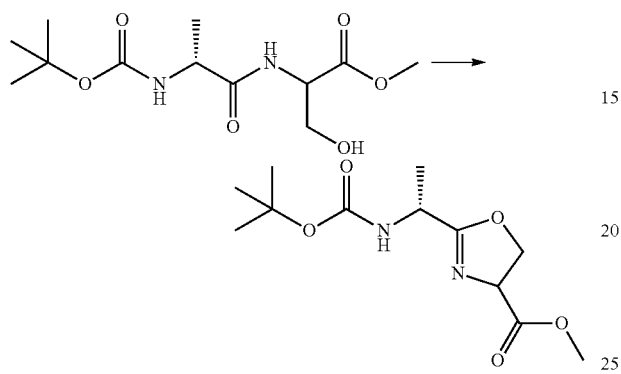

In a round-bottomed flask, 2-((R)-2-tert-butoxycarbonylamino-propionylamino)-3-hydroxy-propionic acid methyl ester (419 mg, 1.3 mmol) was dissolved in dichloromethane (11 ml). The solution was cooled to −76° C. and DAST (0.20 ml, 1.51 mmol) was added dropwise. The light yellow solution was stirred at −76° C. for 2 h then anhydrous potassium carbonate (269 mg, 1.95 mmol) was added in one portion. The reaction mixture was allowed to warm to room temperature, quenched with 10 ml of saturated aqueous NaHCO$_3$ and extracted with dichloromethane (3×). The organic layers were combined, dried over sodium sulfate, filtered and concentrated to afford 339 mg (91%) of 2-((R)-1-tert-butoxycarbonylamino-ethyl)-4,5-dihydro-oxazole-4-carboxylic acid methyl ester as a brown oil.

Step 3

2-((R)-1-tert-Butoxycarbonylamino-ethyl)-oxazole-4-carboxylic acid methyl ester

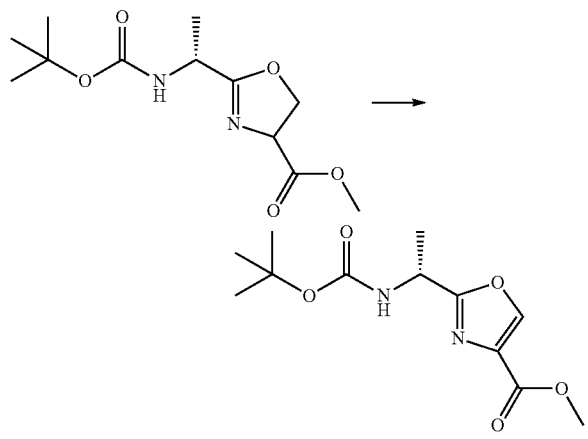

In a round-bottomed flask, 2-((R)-1-tert-butoxycarbonylamino-ethyl)-4,5-dihydro-oxazole-4-carboxylic acid methyl ester (337 mg, 1.18 mmol) was dissolved in dichloromethane (11 ml). The solution was cooled to −16° C. (NaCl/ice bath) and DBU (0.35 ml, 2.32 mmol) was added. After 5 min, bromotrichloromethane (0.13 ml, 1.33 mmol) was added and the reaction mixture was allowed slowly to warm to room temperature and stirred for 4 days. The reaction was quenched with 0.1 M aqueous HCl and extracted with EtOAc (2×). The combined organic layers were washed with water and brine then dried over sodium sulfate, filtered and concentrated. The residue was chromatographed over silica gel with EtOAc/hexanes (gradient 0-30% EtOAc) to afford 152 mg (48%) of 2-((R)-1-tert-butoxycarbonylamino-ethyl)-oxazole-4-carboxylic acid methyl ester as an off-white solid.

Step 4

[(R)-1-(4-Hydroxymethyl-oxazol-2-yl)-ethyl]-carbamic acid tert-butyl ester

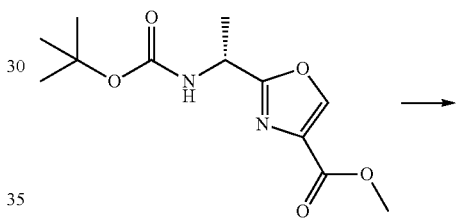

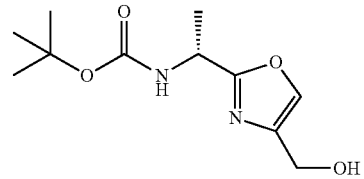

In a round-bottomed flask, 2-((R)-1-tert-butoxycarbonylamino-ethyl)-oxazole-4-carboxylic acid methyl ester (151 mg, 0.56 mmol) was dissolved in THF (4 ml). The pale yellow solution was cooled to 0° C. and lithium aluminum hydride (1.0 M in THF, 0.60 ml, 0.60 mmol) was added dropwise. The reaction mixture was stirred at 0° C. for 1.5 h then sodium sulfate decahydrate was carefully added. When gas evolution had ceased, the ice bath was removed, sodium sulfate was added and the mixture was stirred vigorously for 30 min at room temperature. The suspension was filtered over Celite and rinsed with ethyl acetate/methanol. The filtrate was concentrated to give 140 mg (93%) of [(R)-1-(4-hydroxymethyloxazol-2-yl)-ethyl]-carbamic acid tert-butyl ester as yellow oil which was used without further purification.

Step 5

[2-((R)-1-Amino-ethyl)-oxazol-4-yl]-methanol trifluoroacetate

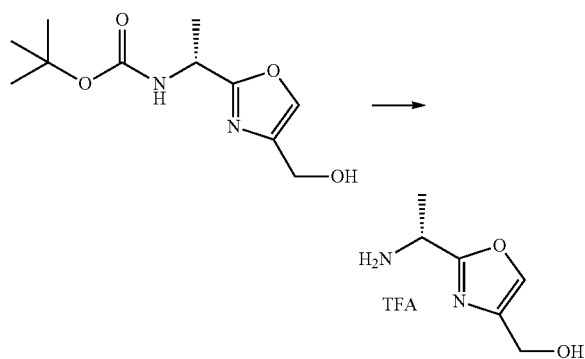

In a round-bottomed flask, [(R)-1-(4-hydroxymethyl-oxazol-2-yl)-ethyl]-carbamic acid tert-butyl ester (137 mg, 0.51 mmol) was dissolved in dichloromethane (3 ml) and trifluoroacetic acid (1.2 ml, 15.6 mmol) was slowly added. The reaction was stirred at room temperature for 1.5 h then concentrated to afford [2-((R)-1-amino-ethyl)-oxazol-4-yl]-methanol trifluoroacetate as a brown oil which was used without further purification.

Step 6

2-(6-Fluoro-1-methyl-1H-indazol-3-yl)-5-(2-trimethylsilanyl-ethoxymethyl)-5H-pyrrolo[2,3-b]pyrazine-7-carboxylic acid [(R)-1-(4-hydroxymethyl-oxazol-2-yl)-ethyl]-amide

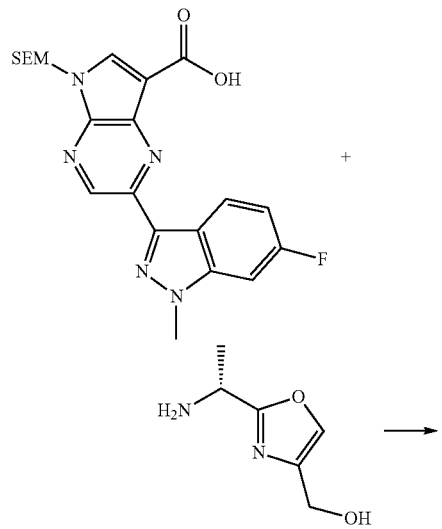

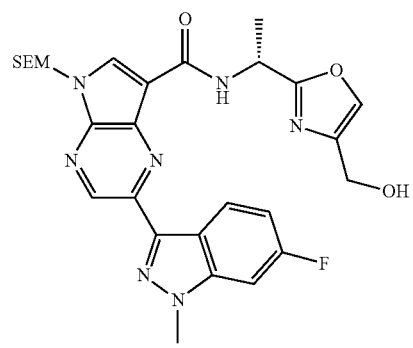

In a round-bottomed flask, [2-((R)-1-amino-ethyl)-oxazol-4-yl]-methanol trifluoroacetate (crude from Step 5) was dissolved in DMF (1.5 ml) and N,N-diisopropylethylamine (0.70 ml, 4.0 mmol) was added. Then 2-(6-fluoro-1-methyl-1H-indazol-3-yl)-5-(2-trimethylsilanylethoxymethyl)-5H-pyrrolo[2,3-b]pyrazine-7-carboxylic acid (140 mg, 0.32 mmol was added followed by HATU (133 mg, 0.35 mmol). The reaction was stirred at room temperature overnight then quenched with water and extracted with diethyl ether (2×). The combined organic layers were washed twice with water and once with brine then dried over sodium sulfate, filtered and concentrated. The residue was chromatographed over silica gel with EtOAc/hexanes (gradient 0-100% EtOAc) to afford 118 mg (66%) of 2-(6-fluoro-1-methyl-1H-indazol-3-yl)-5-(2-trimethylsilanyl-ethoxymethyl)-5H-pyrrolo[2,3-b]pyrazine-7-carboxylic acid [(R)-1-(4-hydroxymethyl-oxazol-2-yl)-ethyl]-amide as a light brown foam.

Step 7

Methanesulfonic acid 2-((R)-1-{[2-(6-fluoro-1-methyl-1H-indazol-3-yl)-5-(2-trimethylsilanylethoxymethyl)-5H-pyrrolo[2,3-b]pyrazine-7-carbonyl]-amino}-ethyl)-oxazol-4-ylmethyl ester

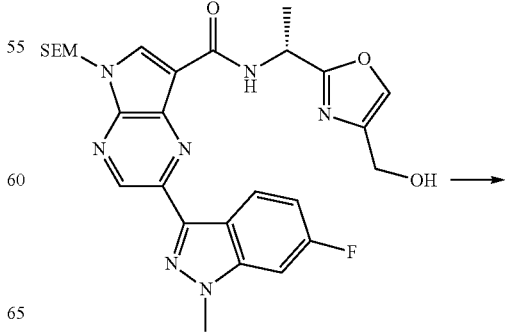

433
-continued

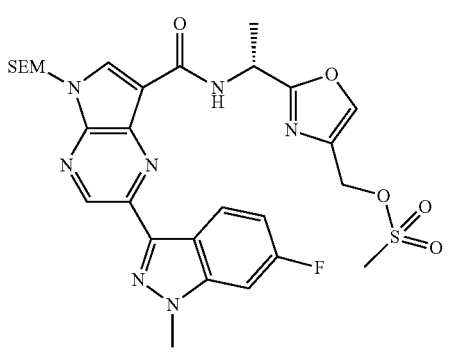

In a round-bottomed flask, 2-(6-fluoro-1-methyl-1H-indazol-3-yl)-5-(2-trimethylsilanylethoxymethyl)-5H-pyrrolo[2,3-b]pyrazine-7-carboxylic acid [(R)-1-(4-hydroxymethyl-oxazol-2-yl)-ethyl]-amide (115 mg, 0.20 mmol) was dissolved in dichloromethane (1 ml). The solution was cooled to 0° C. and triethylamine (0.04 ml, 0.29 mmol) and methanesulfonyl chloride (19 µl, 0.24 mmol) were added. The reaction mixture was stirred at 0° C. for 2 h then quenched with water and extracted with dichloromethane (2×). The organic layers were combined, dried over sodium sulfate, filtered and concentrated to afford 147 mg of methanesulfonic acid 2-((R)-1-{[2-(6-fluoro-1-methyl-1H-indazol-3-yl)-5-(2-trimethylsilanyl-ethoxymethyl)-5H-pyrrolo[2,3-b]pyrazine-7-carbonyl]-amino}-ethyl)-oxazol-4-ylmethyl ester as a yellow foam which was used without further purification.

Step 8

2-(6-Fluoro-1-methyl-1H-indazol-3-yl)-5-(2-trimethylsilanyl-ethoxymethyl)-5H-pyrrolo[2,3-b]pyrazine-7-carboxylic acid [(R)-1-(4-cyanomethyl-oxazol-2-yl)-ethyl]-amide

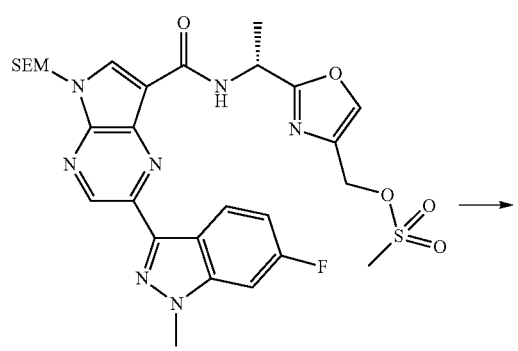

434
-continued

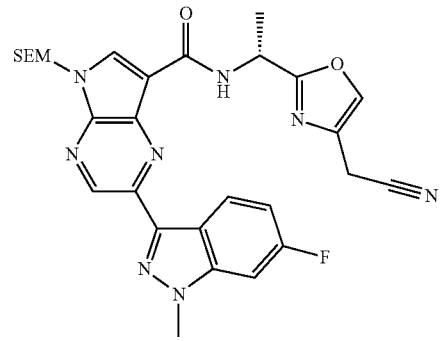

In a round-bottomed flask, methanesulfonic acid 2-((R)-1-{[2-(6-fluoro-1-methyl-1H-indazol-3-yl)-5-(2-trimethylsilanyl-ethoxymethyl)-5H-pyrrolo[2,3-b]pyrazine-7-carbonyl]-amino}-ethyl)-oxazol-4-ylmethyl ester (146 mg, 0.18 mmol) was dissolved in DMF (0.5 ml). Sodium cyanide (27 mg, 0.55 mmol) was added and the reaction mixture was stirred at 80° C. overnight. The reaction was cooled to room temperature, quenched with water and extracted with diethyl ether (2×). The combined organic layers were washed twice with water and once with brine then dried over sodium sulfate, filtered and concentrated. The residue was chromatographed over silica gel with EtOAc/hexanes (gradient 0-60% EtOAc) to isolate 37 mg (36%) of 2-(6-fluoro-1-methyl-1H-indazol-3-yl)-5-(2-trimethylsilanyl-ethoxymethyl)-5H-pyrrolo[2,3-b]pyrazine-7-carboxylic acid [(R)-1-(4-cyanomethyl-oxazol-2-yl)-ethyl]-amide as a yellow solid.

Step 9

2-(6-Fluoro-1-methyl-1H-indazol-3-yl)-5H-pyrrolo[2,3-b]pyrazine-7-carboxylic acid [(R)-1-(4-cyanomethyl-oxazol-2-yl)-ethyl]-amide

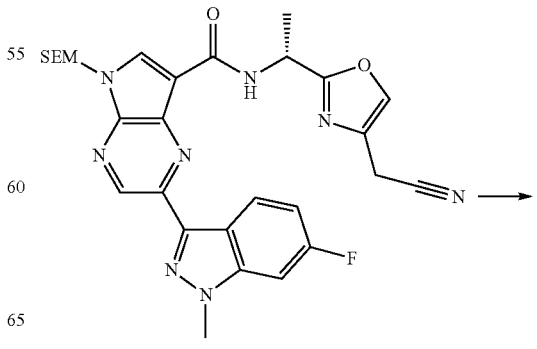

In a round-bottomed flask, 2-(6-fluoro-1-methyl-1H-indazol-3-yl)-5-(2-trimethylsilanylethoxymethyl)-5H-pyrrolo[2,3-b]pyrazine-7-carboxylic acid [(R)-1-(4-cyanomethyl-oxazol-2-yl)-ethyl]-amide (36 mg, 0.063 mmol) was dissolved in dichloromethane (0.4 ml) and trifluoroacetic acid (0.20 ml, 2.6 mmol) was added. The reaction mixture was stirred at room temperature for 2 h then concentrated. The residue was dissolved in dichloromethane (0.4 ml) and ethylenediamine (0.26 ml, 3.8 mmol) was added. The yellow solution was stirred at room temperature for 1 h then quenched with water and diluted with ethyl acetate. The resultant suspension was filtered, washed with hot water and ethyl acetate and dried under high vacuum to provide 18 mg (65%) of 2-(6-fluoro-1-methyl-1H-indazol-3-yl)-5H-pyrrolo[2,3-b]pyrazine-7-carboxylic acid [(R)-1-(4-cyanomethyl-oxazol-2-yl)-ethyl]-amide as an off-white powder. MS: (M+Na)$^+$=467; $^1$H NMR (DMSO-d$_6$, 400 MHz): δ (ppm) 12.93 (br. s., 1H), 9.12 (s, 1H), 8.66 (d, J=8.3 Hz, 1H), 8.50 (s, 1H), 8.46 (dd, J=8.9, 5.4 Hz, 1H), 8.06 (t, J=1.0 Hz, 1H), 7.69 (dd, J=9.7, 2.1 Hz, 1H), 7.12 (td, J=9.0, 2.3 Hz, 1H), 5.44-5.56 (m, 1H), 4.15 (s, 3H), 3.92 (d, J=1.3 Hz, 2H), 1.68 (d, J=7.0 Hz, 3H).

Example 63

2-(6-Fluoro-1-methyl-1H-indazol-3-yl)-5H-pyrrolo[2,3-b]pyrazine-7-carboxylic acid [(R)—(S)-1-(tetrahydro-furan-2-yl)-ethyl]-amide

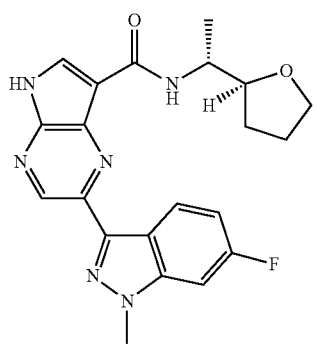 [SMILES: C[C@@H](NC(=O)c1c[nH]c2ncc(-c3nn(C)c4cc(F)ccc34)nc12)[C@@H]1CCCO1]

Step 1

(S)-2-Methyl-propane-2-sulfinic acid 1-furan-2-yl-meth-(E)-ylideneamide

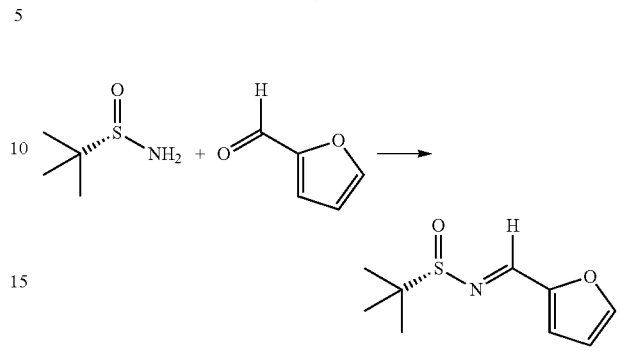

In a round-bottomed flask, furan-2-carbaldehyde (800 mg, 8.33 mmol) was dissolved in THF (20 ml) and (S)-2-methyl-propane-2-sulfinamide (1.21 g, 10.0 mmol) and titanium(IV) ethoxide (3.5 ml, 16.7 mmol) were added. The reaction mixture was stirred at room temperature for 5 h then slowly quenched by dropwise addition of brine (5 ml) which resulted in the formation of a thick precipitate. The reaction mixture was diluted with ethyl acetate and stirred vigorously at room temperature for 15 min. The suspension was filtered over Celite and rinsed with ethyl acetate. The filtrate was concentrated and the residue was chromatographed over silica gel with EtOAc/hexanes (gradient 0-25% EtOAc) to give 1.48 g (89%) of (S)-2-methyl-propane-2-sulfinic acid 1-furan-2-yl-meth-(E)-ylideneamide as a light yellow oil.

Step 2

(S)-2-Methyl-propane-2-sulfinic acid ((R)-1-furan-2-yl-ethyl)-amide

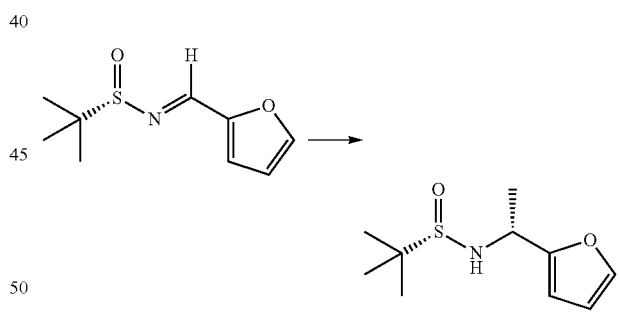

In a round-bottomed flask, (S)-2-methyl-propane-2-sulfinic acid 1-furan-2-yl-meth-(E)-ylideneamide (500 mg, 2.51 mmol) was dissolved in dichloromethane (10 ml). The solution was cooled to −76° C. and methylmagnesium bromide (3.0 M in diethyl ether, 1.0 ml, 3.00 mmol) was added dropwise. The reaction mixture was stirred at −76° C. for 1.5 h and then allowed to warm to room temperature over 1.5 h. The reaction mixture was recooled to −76° C. and a second portion of methylmagnesium bromide (3.0 M in diethyl ether, 1.0 ml, 3.00 mmol) was added dropwise. The reaction mixture was stirred at −76° C. for 1 h and then allowed to warm to room temperature over 3 h. The reaction mixture was recooled to −76° C. and a third portion of methylmagnesium bromide (3.0 M in diethyl ether, 0.5 ml, 1.5 mmol) was added dropwise. The reaction mixture was allowed to warm slowly to room temperature overnight then quenched with saturated aqueous NH$_4$Cl and extracted with ethyl acetate (2×). The combined organic layers were washed with water and brine then dried over sodium sulfate, filtered and concentrated to give 515 mg (91%) of a yellow solid. NMR analysis indicated a 9:1 mixture (80% de) of diastereomers with the major diastereomer assigned as (S)-2-methyl-propane-2-sulfinic acid ((R)-1-furan-2-yl-ethyl)-amide based on literature correlation.

Step 3

(R)-1-Furan-2-yl-ethylamine hydrochloride

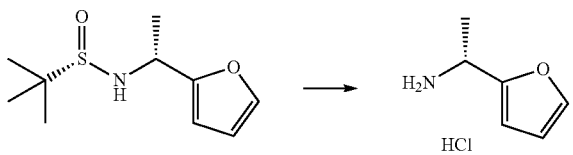

In a round-bottomed flask, (S)-2-methyl-propane-2-sulfinic acid ((R)-1-furan-2-yl-ethyl)-amide (514 mg, 2.27 mmol) was dissolved in methanol 4 ml) and hydrogen chloride (4.0 M in 1,4-dioxane, 1.2 ml, 4.8 mmol) was added dropwise. The reaction mixture was stirred at room temperature for 15 min then concentrated to give 416 mg of (R)-1-furan-2-yl-ethylamine hydrochloride as a dark brown waxy solid which was used without further purification.

Step 4

2-(6-Fluoro-1-methyl-1H-indazol-3-yl)-5-(2-trimethylsilanyl-ethoxymethyl)-5H-pyrrolo[2,3-b]pyrazine-7-carboxylic acid ((R)-1-furan-2-yl-ethyl)-amide

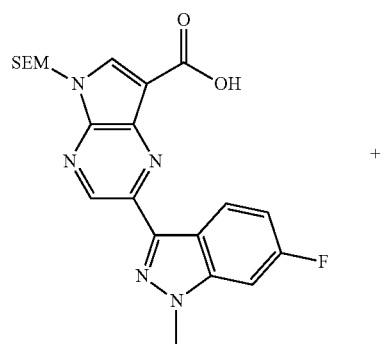

+

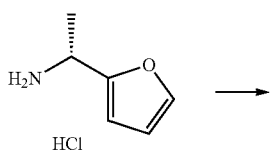

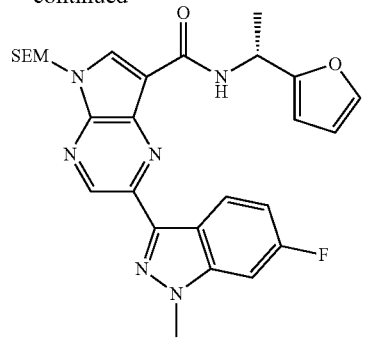

A round-bottomed flask was charged with 2-(6-fluoro-1-methyl-1H-indazol-3-yl)-5-(2-trimethylsilanyl-ethoxymethyl)-5H-pyrrolo[2,3-b]pyrazine-7-carboxylic acid (300 mg, 0.68 mmol) and (R)-1-furan-2-yl-ethylamine hydrochloride (416 mg, 1.55 mmol). DMF (3.5 ml) was added followed by N,N-diisopropylethylamine (0.85 ml, 4.87 mmol) and HATU (284 mg, 0.75 mmol). The reaction was stirred at room temperature overnight then water and petroleum ether were added. The resulting suspension was filtered. The filter cake was washed with water and petroleum ether then dried under high vacuum to afford 338 mg (88%) of 2-(6-fluoro-1-methyl-1H-indazol-3-yl)-5-(2-trimethylsilanyl-ethoxymethyl)-5H-pyrrolo[2,3-b]pyrazine-7-carboxylic acid ((R)-1-furan-2-yl-ethyl)-amide as a light brown powder.

Step 5

2-(6-Fluoro-1-methyl-1H-indazol-3-yl)-5-(2-trimethylsilanyl-ethoxymethyl)-5H-pyrrolo[2,3-b]pyrazine-7-carboxylic acid [(R)-1-(tetrahydro-furan-2-yl)-ethyl]-amide

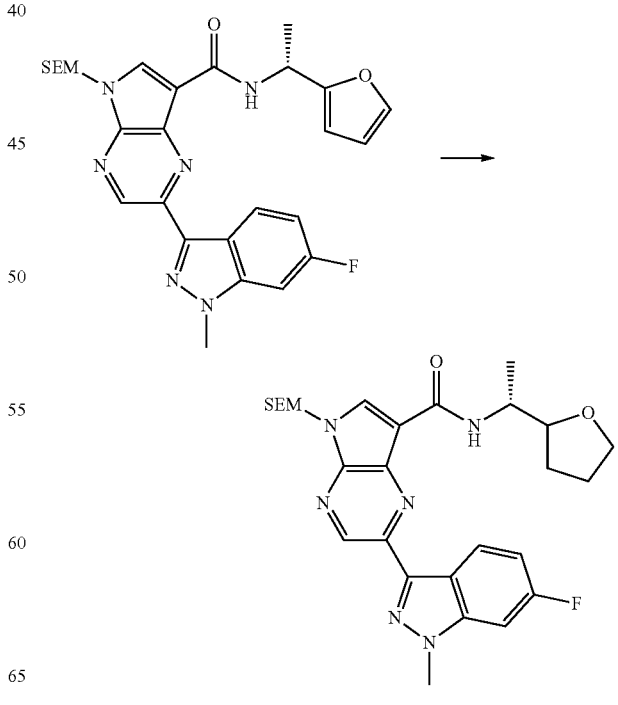

In a round-bottomed flask, 2-(6-fluoro-1-methyl-1H-indazol-3-yl)-5-(2-trimethylsilanylethoxymethyl)-5H-pyrrolo[2,3-b]pyrazine-7-carboxylic acid ((R)-1-furan-2-yl-ethyl)-amide (370 mg, 0.66 mmol) was dissolved in methanol (6 ml) and ethyl acetate (2 ml). The flask was flushed with argon then 20% palladium hydroxide on carbon (50% water, 100 mg, 0.71 mmol) was added. The reaction mixture was stirred under hydrogen atmosphere (balloon) at room temperature for 48 h then filtered over Celite and rinsed with dichloromethane/ethyl acetate. The filtrate was concentrated and the residue was chromatographed over silica gel with MeOH/CH$_2$Cl$_2$/0.5% NH$_4$OH (gradient 0-2.5% MeOH) to afford 300 mg (86%) of 2-(6-fluoro-1-methyl-1H-indazol-3-yl)-5-(2-trimethylsilanyl-ethoxymethyl)-5H-pyrrolo[2,3-b]pyrazine-7-carboxylic acid [(R)-1-(tetrahydro-furan-2-yl)-ethyl]-amide as a light yellow solid.

Step 6

2-(6-Fluoro-1-methyl-1H-indazol-3-yl)-5-(2-trimethylsilanyl-ethoxymethyl)-5H-pyrrolo[2,3-b]pyrazine-7-carboxylic acid [(R)—(S)-1-(tetrahydro-furan-2-yl)-ethyl]-amide and 2-(6-Fluoro-1-methyl-1H-indazol-3-yl)-5-(2-trimethylsilanyl-ethoxymethyl)-5H-pyrrolo[2,3-b]pyrazine-7-carboxylic acid [(R)—(R)-1-(tetrahydro-furan-2-yl)-ethyl]-amide

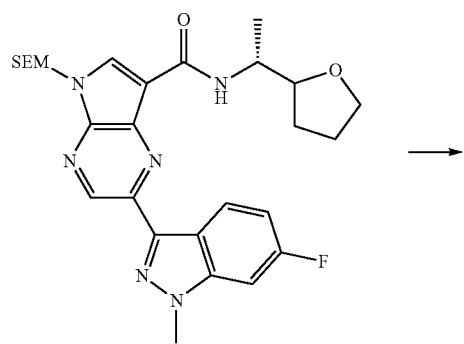

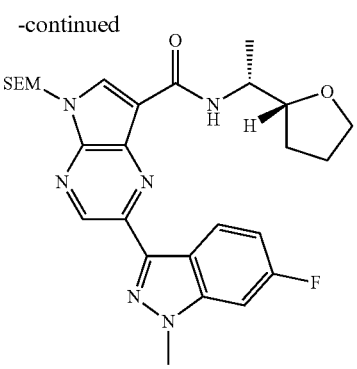

A sample of 2-(6-fluoro-1-methyl-1H-indazol-3-yl)-5-(2-trimethylsilanyl-ethoxymethyl)-5H-pyrrolo[2,3-b]pyrazine-7-carboxylic acid [(R)-1-(tetrahydro-furan-2-yl)-ethyl]-amide (300 mg, 0.56 mmol) was subjected to chiral SFC chromatography. Separation of the diastereomers was achieved with WHELK-O1 R,R 3×25 column using 45% MeOH/CO$_2$ (with 0.2% triethylamine added) as the eluent. Obtained 163 mg (54%) of 2-(6-fluoro-1-methyl-1H-indazol-3-yl)-5-(2-trimethylsilanylethoxymethyl)-5H-pyrrolo[2,3-b]pyrazine-7-carboxylic acid [(R)—(S)-1-(tetrahydro-furan-2-yl)-ethyl]-amide as an off-white solid and 38 mg (13%) 2-(6-fluoro-1-methyl-1H-indazol-3-yl)-5-(2-trimethylsilanyl-ethoxymethyl)-5H-pyrrolo[2,3-b]pyrazine-7-carboxylic acid [(R)—(R)-1-(tetrahydro-furan-2-yl)-ethyl]-amide as an off white powder.

Step 7

2-(6-Fluoro-1-methyl-1H-indazol-3-yl)-5H-pyrrolo[2,3-b]pyrazine-7-carboxylic acid [(R)—(S)-1-(tetrahydro-furan-2-yl)-ethyl]-amide

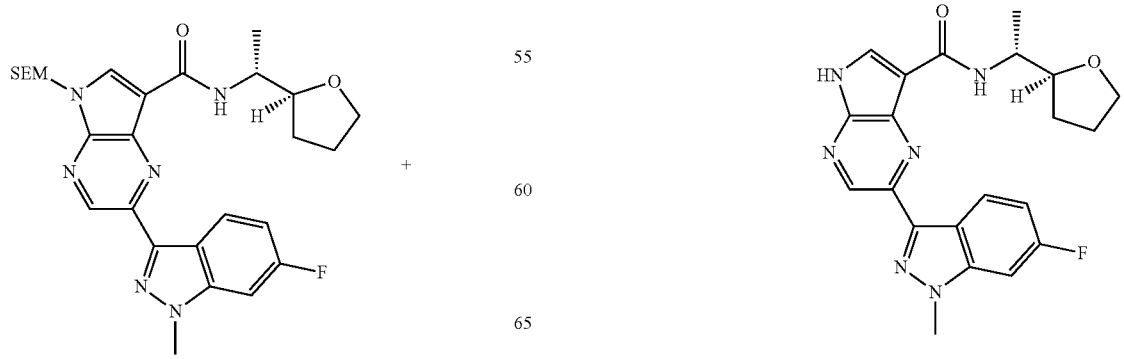

In a round-bottomed flask, 2-(6-fluoro-1-methyl-1H-indazol-3-yl)-5-(2-trimethylsilanylethoxymethyl)-5H-pyrrolo[2,3-b]pyrazine-7-carboxylic acid [(R)—(S)-1-(tetrahydro-furan-2-yl)-ethyl]-amide (152 mg, 0.28 mmol) was dissolved in dichloromethane (1.4 ml) and trifluoroacetic acid (0.87 ml, 11.3 mmol) was added. The reaction mixture was stirred at room temperature for 2 h then concentrated. The residue was dissolved in dichloromethane (1.4 ml) and ethylenediamine (1.2 ml, 17.8 mmol) was added. The yellow solution was stirred at room temperature for 1 h then quenched with water and diluted with ethyl acetate. The resulting suspension was filtered, washed with hot water and ethyl acetate and dried under high vacuum to provide 46 mg (40%) of 2-(6-fluoro-1-methyl-1H-indazol-3-yl)-5H-pyrrolo[2,3-b]pyrazine-7-carboxylic acid [(R)—(S)-1-(tetrahydro-furan-2-yl)-ethyl]-amide as an off-white powder. MS: (M+Na)$^+$=431; $^1$H NMR (DMSO-d$_6$, 300 MHz): δ (ppm) 12.09 (br. s., 1H), 9.13 (s, 1H), 8.64 (dd, J=8.7, 5.3 Hz, 1H), 8.44 (s, 1H), 8.22 (d, J=9.4 Hz, 1H), 7.67 (d, J=8.3 Hz, 1H), 7.10 (t, J=8.1 Hz, 1H), 4.32 (br. s., 1H), 4.15 (s, 3H), 3.96 (d, J=3.0 Hz, 1H), 3.52-3.68 (m, 2H), 1.86-2.00 (m, 1H), 1.52-1.84 (m, 3H), 1.33 (d, J=6.8 Hz, 3H).

Example 64

2-(6-Fluoro-1-methyl-1H-indazol-3-yl)-5H-pyrrolo[2,3-b]pyrazine-7-carboxylic acid [(R)—(R)-1-(tetrahydro-furan-2-yl)-ethyl]-amide

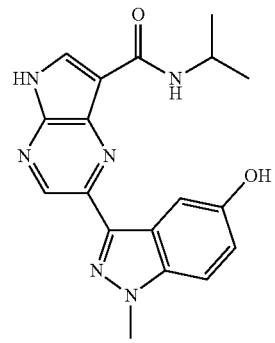 [SMILES: CC(C)NC(=O)c1c[nH]c2ncc(-c3nn(C)c4ccc(O)cc34)nc12]

Prepared according to Example 63, Step 7, substituting 2-(6-fluoro-1-methyl-1H-indazol-3-yl)-5-(2-trimethylsilanyl-ethoxymethyl)-5H-pyrrolo[2,3-b]pyrazine-7-carboxylic acid [(R)—(R)-1-(tetrahydro-furan-2-yl)-ethyl]-amide for 2-(6-fluoro-1-methyl-1H-indazol-3-yl)-5-(2-trimethylsilanyl-ethoxymethyl)-5H-pyrrolo[2,3-b]pyrazine-7-carboxylic acid [(R)—(S)-1-(tetrahydro-furan-2-yl)-ethyl]-amide. MS: (M+Na)$^+$=431; $^1$H NMR (DMSO-d$_6$, 300 MHz): δ (ppm) 9.12 (s, 1H), 8.56 (dd, J=8.7, 5.3 Hz, 1H), 8.44 (s, 1H), 8.24 (d, J=9.1 Hz, 1H), 7.69 (dd, J=9.8, 2.3 Hz, 1H), 7.14 (td, J=9.1, 2.3 Hz, 1H), 4.26 (dd, J=13.4, 7.0 Hz, 1H), 4.15 (s, 3H), 3.79-4.00 (m, 2H), 3.69 (q, J=7.3 Hz, 1H), 1.65-2.02 (m, 4H), 1.26 (d, J=6.4 Hz, 3H).

Example 65

2-(5-Hydroxy-1-methyl-1H-indazol-3-yl)-5H-pyrrolo[2,3-b]pyrazine-7-carboxylic acid isopropylamide

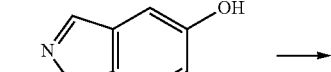

Step 1

5-(tert-Butyl-dimethyl-silanyloxy)-1H-indazole

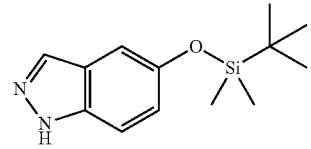

In a round-bottomed flask, 5-hydroxy-1H-indazole (700 mg, 5.22 mmol) was dissolved in DMF (15 ml) and TBDMS-Cl (865 mg, 5.74 mmol) and imidazole (426 mg, 6.26 mmol) were added. The reaction mixture was stirred at room temperature overnight then quenched with water and extracted with diethyl ether (2×). The combined organic layers were washed twice with water and once with brine then dried over sodium sulfate, filtered and concentrated. The residue was chromatographed over silica gel with EtOAc/hexanes (gradient 0-30% EtOAc) to afford 1.21 g (93%) of 5-(tert-butyl-dimethyl-silanyloxy)-1H-indazole as an off-white solid.

Step 2

5-(tert-Butyl-dimethyl-silanyloxy)-3-iodo-1H-indazole

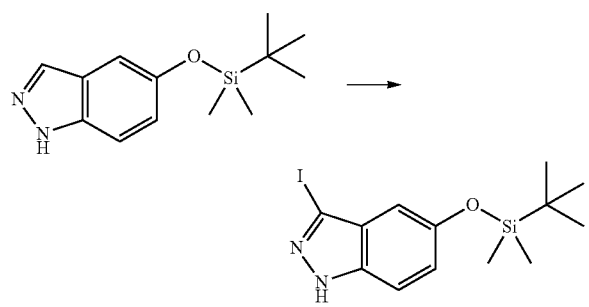

In a round-bottomed flask, 5-(tert-butyl-dimethyl-silanyloxy)-1H-indazole (1.20 g, 4.83 mmol) was dissolved in DMF (12 ml). Iodine (2.45 g, 9.66 mmol) was added followed by potassium carbonate (2.58 g, 18.7 mmol). The dark suspension was stirred at room temperature for 3 h then quenched with 10% aqueous $NaHSO_3$ and extracted with diethyl ether (2×). The combined organic layers were washed with 10% aqueous $NaHSO_3$, three times with water and once with brine then dried over sodium sulfate, filtered and concentrated to afford 1.65 g (91%) of 5-(tert-butyl-dimethyl-silanyloxy)-3-iodo-1H-indazole as a dark brown foam.

Step 3

5-(tert-Butyl-dimethyl-silanyloxy)-3-iodo-1-methyl-1H-indazole

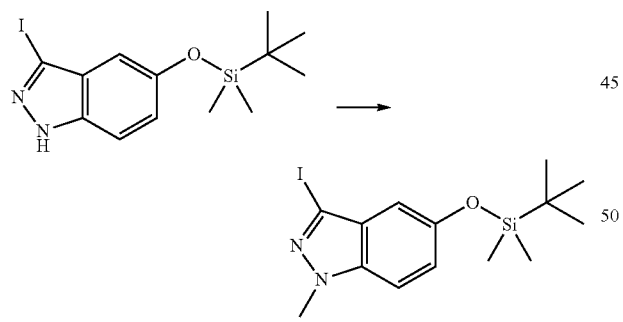

In a round-bottomed flask, 5-(tert-butyl-dimethyl-silanyloxy)-3-iodo-1H-indazole (1.65 g, 4.41 mmol) was dissolved in THF (16 ml). The solution was cooled to 0° C. and potassium tert-butoxide (697 mg, 6.22 mmol) was added. The reaction mixture was stirred at 0° C. for 30 min then methyl iodide (0.38 ml, 6.08 mmol) was added dropwise. After the addition was complete, the ice bath was removed and the reaction mixture was stirred at room temperature for 4.5 h. The reaction was quenched with water and extracted with EtOAc (2×). The combined organic layers were washed with water and brine then dried over sodium sulfate, filtered and concentrated. The residue was chromatographed over silica gel with EtOAc/hexanes (gradient 0-10% EtOAc) to give 770 mg (45%) of 5-(tert-butyl-dimethyl-silanyloxy)-3-iodo-1-methyl-1H-indazole as a light yellow solid.

Step 4

5-(tert-Butyl-dimethyl-silanyloxy)-1-methyl-3-tributylstannanyl-1H-indazole

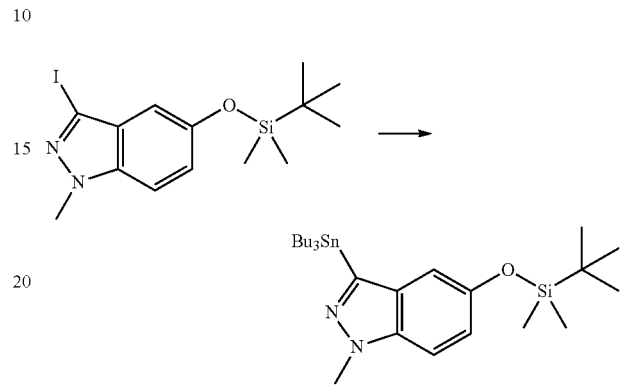

In a round-bottomed flask, 5-(tert-butyl-dimethyl-silanyloxy)-3-iodo-1-methyl-1H-indazole (140 mg, 0.36 mmol) was dissolved in THF (2 ml). The solution was cooled to −16° C. (NaCl/ice bath) and isopropylmagnesium chloride (2.0 M in THF, 0.22 ml, 0.44 mmol) was added dropwise. The reaction mixture was stirred at −16° C. for 20 min then tributylchlorostannane (0.11 ml, 0.41 mmol) was slowly added. The reaction mixture was allowed to warm to room temperature over 1.5 h then quenched with saturated aqueous $NH_4Cl$ and extracted with EtOAc (2×). The combined organic layers were washed with water and brine then dried over sodium sulfate, filtered and concentrated to provide 5-(tert-butyl-dimethyl-silanyloxy)-1-methyl-3-tributylstannanyl-1H-indazole as a light yellow oil which was used without further purification.

Step 5

2-[5-(tert-Butyl-dimethyl-silanyloxy)-1-methyl-1H-indazol-3-yl]-5-(2-trimethylsilanylethoxymethyl)-5H-pyrrolo[2,3-b]pyrazine-7-carboxylic acid isopropylamide

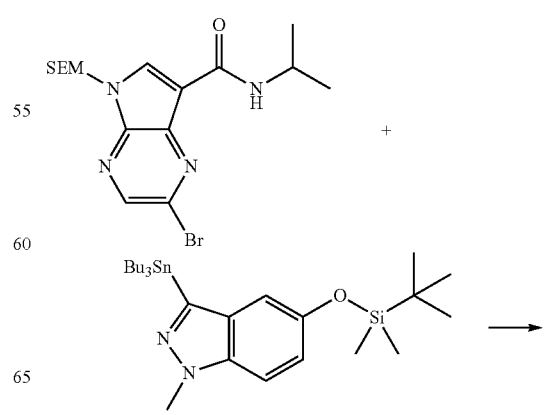

445
-continued

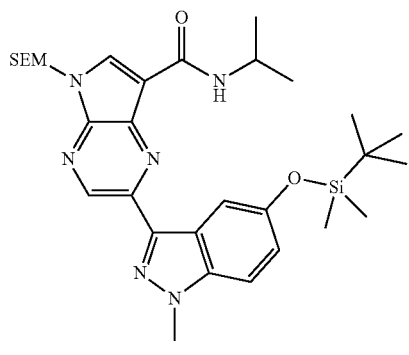

446
-continued

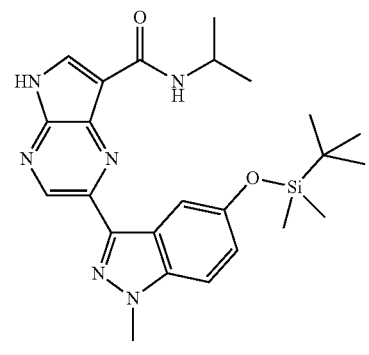

In a round-bottomed flask, 2-bromo-5-(2-trimethylsilanyl-ethoxymethyl)-5H-pyrrolo[2,3-b]pyrazine-7-carboxylic acid isopropylamide (100 mg, 0.24 mmol) and 5-(tert-butyl-dimethyl-silanyloxy)-1-methyl-3-tributylstannanyl-1H-indazole (crude from Step 4) were dissolved in DMF (2 ml). The flask was evacuated and backfilled with argon then tetrakis(triphenylphosphine)palladium (0) (14 mg, 0.012 mmol) and copper (I) iodide (10 mg, 0.053 mmol) were added. The reaction mixture was stirred at 80° C. for 2 h then cooled to room temperature, quenched with water and extracted with diethyl ether (2×). The combined organic layers were washed twice with water and once with brine then dried over sodium sulfate, filtered and concentrated. The residue was chromatographed over silica gel with EtOAc/hexanes (gradient 0-30% EtOAc) to afford 104 mg (72%) of 2-[5-(tert-butyl-dimethyl-silanyloxy)-1-methyl-1H-indazol-3-yl]-5-(2-trimethylsilanyl-ethoxymethyl)-5H-pyrrolo[2,3-b]pyrazine-7-carboxylic acid isopropylamide as a light yellow solid.

In a round-bottomed flask, 2-[5-(tert-butyl-dimethyl-silanyloxy)-1-methyl-1H-indazol-3-yl]-5-(2-trimethylsilanyl-ethoxymethyl)-5H-pyrrolo[2,3-b]pyrazine-7-carboxylic acid isopropylamide (100 mg, 0.168 mmol) was dissolved in dichloromethane (0.8 ml) and trifluoroacetic acid (0.52 ml, 6.75 mmol) was added. The reaction mixture was stirred at room temperature for 2 h then concentrated. The residue was dissolved in dichloromethane (0.8 ml) and ethylenediamine (0.68 ml, 10.1 mmol) was added. The yellow solution was stirred at room temperature for 1 h then quenched with water and extracted with EtOAc (2×). The combined organic layers were washed with water and brine then dried over sodium sulfate, filtered and concentrated. The residue was triturated with ethyl acetate to afford 55 mg (70%) of 2-[5-(tert-butyl-dimethyl-silanyloxy)-1-methyl-1H-indazol-3-yl]-5H-pyrrolo[2,3-b]pyrazine-7-carboxylic acid isopropylamide as a yellow powder.

Step 6

2-[5-(tert-Butyl-dimethyl-silanyloxy)-1-methyl-1H-indazol-3-yl]-5H-pyrrolo[2,3-b]pyrazine-7-carboxylic acid isopropylamide Step 7

2-(5-Hydroxy-1-methyl-1H-indazol-3-yl)-5H-pyrrolo[2,3-b]pyrazine-7-carboxylic acid isopropylamide

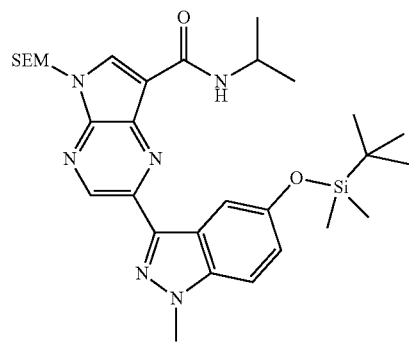

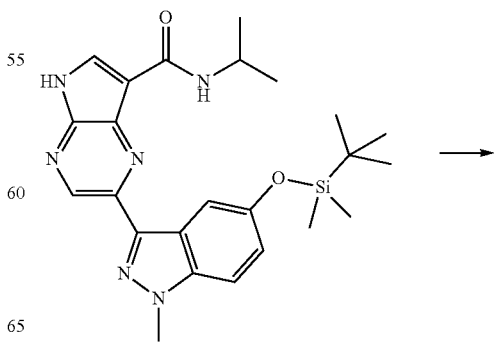

-continued

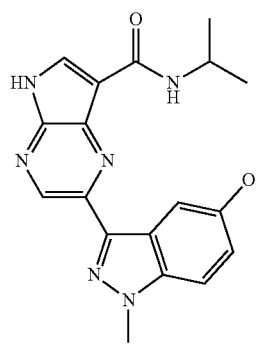

In a round-bottomed, 2-[5-(tert-butyl-dimethyl-silanyloxy)-1-methyl-1H-indazol-3-yl]-5H-pyrrolo[2,3-b]pyrazine-7-carboxylic acid isopropylamide (50 mg, 0.108 mmol) was suspended in THF (1.2 ml) and tetrabutylammonium fluoride (1.0 M in THF, 0.11 ml, 110 mmol) was added. The reaction mixture was stirred at room temperature for 1 h then quenched with water and diluted with ethyl acetate. The resulting suspension was filtered and the solid was washed with hot water and ethyl acetate then dried under high vacuum to provide 33 mg (83%) of 2-(5-hydroxy-1-methyl-1H-indazol-3-yl)-5H-pyrrolo[2,3-b]pyrazine-7-carboxylic acid isopropylamide as a yellow powder. MS: (M+Na)$^+$=373; $^1$H NMR (DMSO-d$_6$, 300 MHz): δ (ppm) 12.77 (br. s., 1H), 9.25 (s, 1H), 9.06 (s, 1H), 8.38 (s, 1H), 8.16 (d, J=7.6 Hz, 1H), 7.73 (d, J=1.9 Hz, 1H), 7.60 (d, J=9.1 Hz, 1H), 7.10 (dd, J=9.1, 2.3 Hz, 1H), 4.23 (dq, J=13.6, 6.7 Hz, 1H), 4.13 (s, 3H), 1.35 (d, J=6.8 Hz, 6H).

Example 66

2-(5-Chloro-indazol-1-yl)-5H-pyrrolo[2,3-b]pyrazine-7-carboxylic acid [(R)-2-(4-cyano-piperidin-1-yl)-1-cyclopropyl-2-oxo-ethyl]-amide

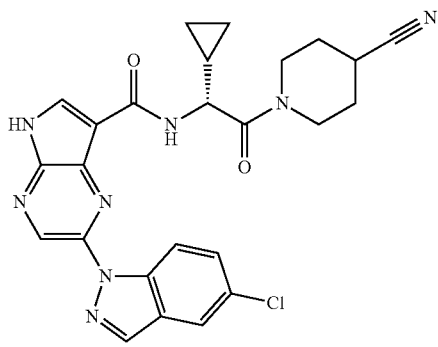 [SMILES: N#CC1CCN(C(=O)[C@H](NC(=O)c2c[nH]c3ncc(-n4ncc5cc(Cl)ccc54)nc23)C2CC2)CC1]

Step 1

2-(5-Chloro-indazol-1-yl)-5-(2-trimethylsilanyl-ethoxymethyl)-5H-pyrrolo[2,3-b]pyrazine-7-carboxylic acid [(R)-2-(4-cyano-piperidin-1-yl)-1-cyclopropyl-2-oxo-ethyl]-amide

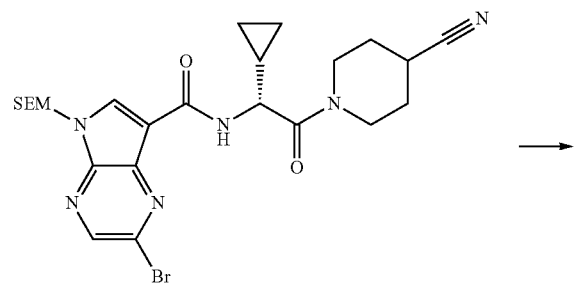

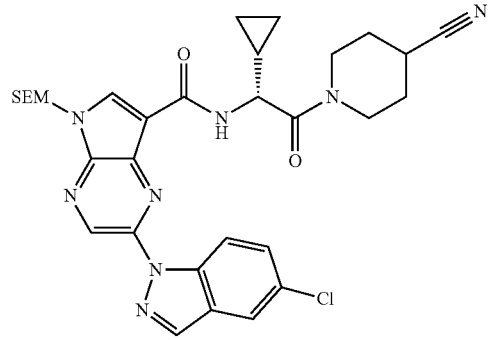

A 5 ml microwave vial was charged with 2-bromo-5-(2-trimethylsilanyl-ethoxymethyl)-5H-pyrrolo[2,3-b]pyrazine-7-carboxylic acid [(R)-2-(4-cyano-piperidin-1-yl)-1-cyclopropyl-2-oxo-ethyl]-amide (252 mg, 0.45 mmol), sodium iodide (112 mg, 0.75 mmol) and copper(I) iodide (8 mg, 0.04 mmol). The vial was evacuated, backfilled with argon then toluene (0.4 ml) and trans-N,N'-dimethylcyclohexane-1,2-diamine (0.015 ml, 0.095 mmol) were added via syringe. The vial was sealed and the reaction mixture was stirred at 110° C. in an oil bath for 22 h. The reaction was cooled to room temperature and 5-chloro-1H-indazole (57 mg, 0.37 mmol) and potassium phosphate tribasic (167 mg, 0.79 mmol) were added. The vial was again evacuated, backfilled with argon, sealed and stirred at 110° C. in an oil bath for 19 h. The reaction was cooled to room temperature, filtered through Celite and washed with ethyl acetate. The filtrate was concentrated and the residue was purified by chromatography over silica gel with MeOH/CH$_2$Cl$_2$ (0.5% NH$_4$OH) (gradient 0-2.5% MeOH) to give 53 mg (22%) of 2-(5-chloro-indazol-1-yl)-5-(2-trimethylsilanyl-ethoxymethyl)-5H-pyrrolo[2,3-b]pyrazine-7-carboxylic acid [(R)-2-(4-cyano-piperidin-1-yl)-1-cyclopropyl-2-oxo-ethyl]-amide as a yellow oil and 76 mg (33%) of 2-iodo-5-(2-trimethylsilanyl-ethoxymethyl)-

5H-pyrrolo[2,3-b]pyrazine-7-carboxylic acid [(R)-2-(4-cyano-piperidin-1-yl)-1-cyclopropyl-2-oxo-ethyl]-amide as a light brown solid.

Step 2

2-(5-Chloro-indazol-1-yl)-5H-pyrrolo[2,3-b]pyrazine-7-carboxylic acid [(R)-2-(4-cyano-piperidin-1-yl)-1-cyclopropyl-2-oxo-ethyl]-amide

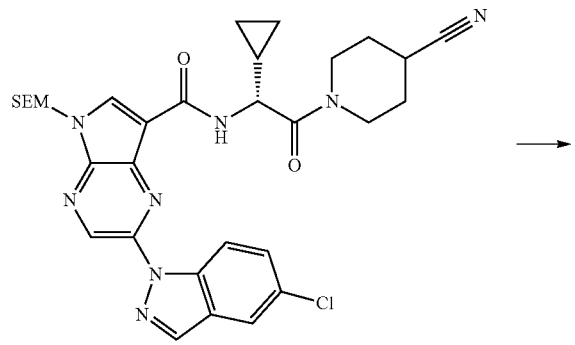

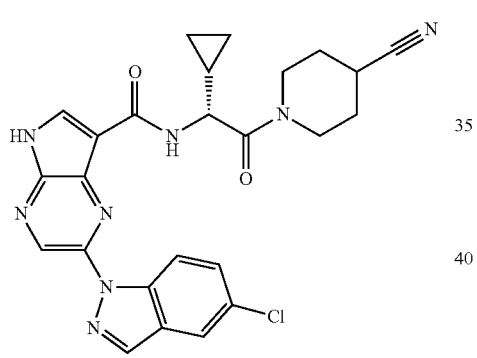

In a round-bottomed flask, 2-(5-chloro-indazol-1-yl)-5-(2-trimethylsilanylethoxymethyl)-5H-pyrrolo[2,3-b]pyrazine-7-carboxylic acid [(R)-2-(4-cyano-piperidin-1-yl)-1-cyclopropyl-2-oxo-ethyl]-amide (51 mg, 0.08 mmol) was dissolved in dichloromethane (0.5 ml) and trifluoroacetic acid (0.25 ml, 3.24 mmol) was added. The yellow reaction mixture was stirred at room temperature for 2.5 h then concentrated. The residue was dissolved in dichloromethane (0.5 ml) and ethylenediamine (0.33 ml, 4.89 mmol) was added. The reaction was stirred at room temperature for 1.5 h then quenched with water and extracted with EtOAc (2×30 ml). The combined organic layers were washed with water and brine then dried over sodium sulfate, filtered and concentrated. The residue was purified by chromatography over silica gel with EtOAc/hexanes (gradient 0-100% EtOAc) followed by trituration with EtOAc/hexanes (1:1) to provide 22 mg (52%) of 2-(5-chloro-indazol-1-yl)-5H-pyrrolo[2,3-b]pyrazine-7-carboxylic acid [(R)-2-(4-cyano-piperidin-1-yl)-1-cyclopropyl-2-oxo-ethyl]-amide as a yellow solid. MS: (M+H)$^+$=503; $^1$H NMR (DMSO-d$_6$, 300 MHz): δ (ppm) 13.01 (br. s., 1H), 9.10 (s, 1H), 8.94 (dd, J=8.9, 5.1 Hz, 1H), 8.54 (d, J=0.8 Hz, 1H), 8.51 (d, J=6.8 Hz, 1H), 8.29 (d, J=8.3 Hz, 1H), 8.07 (d, J=1.9 Hz, 1H), 7.56 (t, J=6.6 Hz, 1H), 4.92-5.02 (m, 1H), 3.70-4.06 (m, 2H), 3.09-3.68 (m, 3H), 1.50-2.08 (m, 4H), 1.20-1.39 (m, 1H), 0.31-0.61 (m, 4H).

Example 67

2-(5,6-Dichloro-1-methyl-1H-indazol-3-yl)-5H-pyrrolo[2,3-b]pyrazine-7-carboxylic acid [(R)-2-(4-cyano-piperidin-1-yl)-1-cyclopropyl-2-oxo-ethyl]-amide

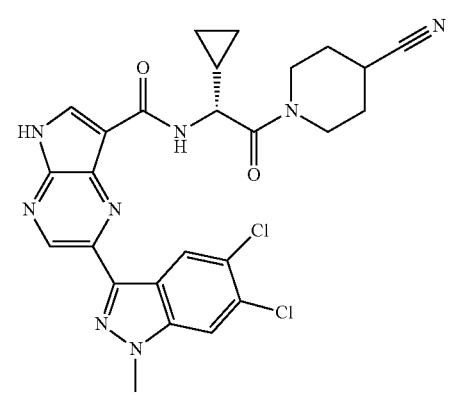 [SMILES: Cn1nc(-c2cnc3[nH]cc(C(=O)N[C@@H](C(=O)N4CCC(C#N)CC4)C4CC4)c3n2)c2cc(Cl)c(Cl)cc21]

Step 1

4,5-Dichloro-2-methylaniline

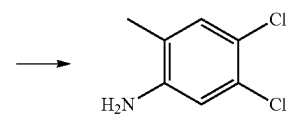

To a partial suspension of 1,2-dichloro-4-methyl-5-nitrobenzene (2.0 g, 9.71 mmol) in MeOH (25 ml), water (25 ml), and THF (10 ml) was added NH$_4$Cl (5.19 g, 97.1 mmol) followed by iron powder (2.71 g, 48.5 mmol). The heterogeneous reaction mixture was heated at 100° C. for 3 h then cooled to room temperature and filtered over a Buchner funnel, rinsing with MeOH. The filtrate was diluted with water and saturated aqueous NaHCO$_3$ then extracted with CH$_2$Cl$_2$ (3×). The combined organics were dried over MgSO$_4$ and concentrated to afford 1.69 g (99%) of 4,5-dichloro-2-methylaniline as a white solid. $^1$H NMR (CDCl$_3$, 300 MHz): δ (ppm) 7.10 (s, 1H), 6.75 (s, 1H), 3.74 (br. s., 2H), 2.12 (s, 3H).

Step 2

5,6-Dichloro-1H-indazole

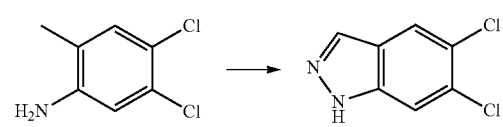

To a solution of 4,5-dichloro-2-methylaniline (1.69 g, 9.6 mmol) in CHCl₃ (25 ml) at 0° C. was slowly added acetic anhydride (2.09 ml, 22.1 mmol). The reaction mixture was warmed to room temperature and stirred for 1 h. A thick white precipitate had gradually formed. Potassium acetate (283 mg, 2.88 mmol) was added followed by slow addition of isoamyl nitrite (2.78 ml, 20.6 mmol). The reaction mixture was heated at reflux overnight. The homogeneous deep orange reaction mixture was cooled to room temperature and concentrated. Water (10 mL) was added and the mixture was reconcentrated to an orange solid. This solid was suspended in conc. HCl (15 mL) and heated at 60° C. for 2 h then cooled to 0° C. and neutralized with 50% NaOH. Extracted with EtOAc, dried over MgSO₄ and concentrated to an orange solid. This solid was dissolved in THF/MeOH (1:1, 25 mL) and 10% NaOH (3 mL) was added. The deep maroon reaction mixture was stirred at room temperature for 5 min then neutralized with 1.0 M HCl and diluted with water. The mixture was extracted with EtOAc (2×) then dried over MgSO₄ and concentrated. The residue was absorbed onto silica gel and purified by chromatography with 30% to 50% EtOAc/hexanes to afford 1.50 g (84%) of 5,6-dichloro-1H-indazole as a light orange solid. $^1$H NMR (CDCl₃, 300 MHz): δ (ppm) 8.04 (s, 1H), 7.89 (s, 1H), 7.68 (s, 1H).

Step 3

5,6-Dichloro-3-iodo-1H-indazole

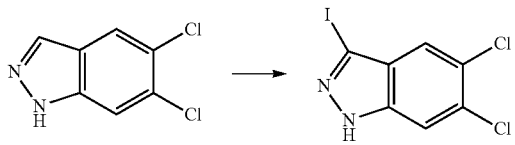 [SMILES: Clc1cc2cn[nH]c2cc1Cl ; Clc1cc2[nH]nc(I)c2cc1Cl]

To a solution of 5,6-dichloro-1H-indazole (0.50 g, 2.67 mmol) in DMF (8 ml) at room temperature was added powdered potassium hydroxide (450 mg, 8.02 mmol) and iodine (1.02 g, 4.01 mmol). The maroon reaction mixture was stirred at room temperature for 45 min then quenched with 10% aqueous Na₂S₂O₃ and diluted with water. The mixture was extracted with EtOAc (2×). The combined organics were washed with water (3×), dried over MgSO₄ and concentrated to afford 827 mg (99%) of 5,6-dichloro-3-iodo-1H-indazole as a pale yellow solid. $^1$H NMR (DMSO-d₆, 400 MHz): δ (ppm) 13.79 (s, 1H), 7.94 (s, 1H), 7.72 (s, 1H).

Step 4

5,6-Dichloro-3-iodo-1-methyl-1H-indazole

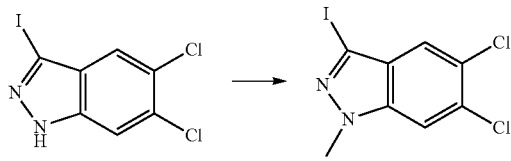

To a solution of 5,6-dichloro-3-iodo-1H-indazole (820 mg, 2.62 mmol) in THF (8 ml) at 0° C. was added KOt-Bu (412 mg, 3.67 mmol). The reaction mixture was stirred at 0° C. for 30 min then added iodomethane (0.23 ml, 3.67 mmol). Stirred at 0° C. for 30 min then warmed to room temperature and stirred for 1.5 hr. The reaction was quenched with water and extracted with EtOAc (2×). The combined organics were dried over MgSO₄ and concentrated. The crude residue was absorbed on silica gel and purified by chromatography with 20% to 30% EtOAc/hexanes to afford 585 mg (68%) of 5,6-dichloro-3-iodo-1-methyl-1H-indazole as a light yellow solid. $^1$H NMR (CDCl₃, 400 MHz): δ (ppm) 7.61 (s, 1H), 7.56 (s, 1H), 4.09 (s, 3H). The minor 5,6-dichloro-3-iodo-2-methyl-1H-indazole regioisomer was also observed but not isolated.

Step 5

5,6-Dichloro-1-methyl-3-tributylstannanyl-1H-indazole

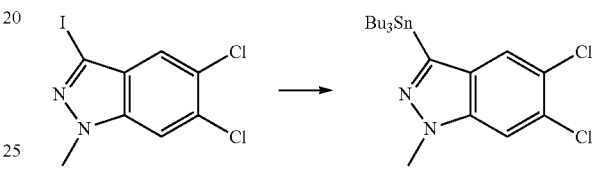

To a solution of 5,6-dichloro-3-iodo-1-methyl-1H-indazole (150 mg, 0.44 mmol) in THF (3 mL) at −10° C. (ice/acetone) was slowly added isopropylmagnesium chloride (2.0 M in THF, 0.26 mL, 0.52 mmol). The bright yellow heterogeneous reaction mixture was stirred at −10° C. for 15 min then tributylchlorostannane (0.14 mL, 0.52 mmol) was added dropwise. Stirring was continued at −10° C. for 30 min then at room temperature for 1 h. The reaction mixture was quenched with water and extracted with EtOAc (2×). The combined organics were dried over MgSO₄ and concentrated to afford 5,6-dichloro-1-methyl-3-tributylstannanyl-1H-indazole as a pale yellow oil which was used in the next step without further purification.

Step 6

2-(5,6-Dichloro-1-methyl-1H-indazol-3-yl)-5-(2-trimethylsilanyl-ethoxymethyl)-5H-pyrrolo[2,3-b]pyrazine-7-carboxylic acid [(R)-2-(4-cyano-piperidin-1-yl)-1-cyclopropyl-2-oxo-ethyl]-amide

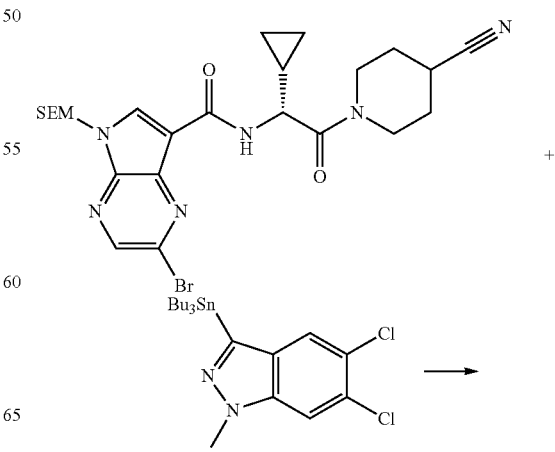

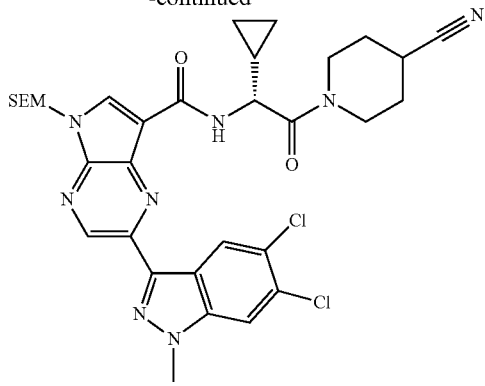
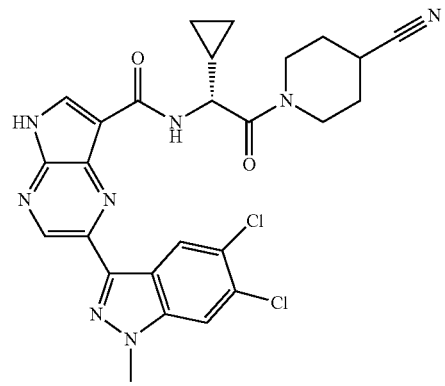

To a solution of 5,6-dichloro-1-methyl-3-tributylstannyl-1H-indazole (crude from Step 5, 218 mg, 0.44 mmol) and 2-bromo-5-(2-trimethylsilanyl-ethoxymethyl)-5H-pyrrolo[2,3-b]pyrazine-7-carboxylic acid [(R)-2-(4-cyano-piperidin-1-yl)-1-cyclopropyl-2-oxo-ethyl]-amide (125 mg, 0.22 mmol) in DMF (2 mL) were added Pd(PPh$_3$)$_4$ (12.9 mg, 0.011 mmol) and copper(I) iodide (8 mg, 0.044 mmol). The yellow reaction mixture was heated at 90° C. for 1.5 h then cooled to room temperature, quenched with water and extracted with EtOAc (2×). The combined organics were washed with water (3×) and brine then dried over MgSO$_4$ and concentrated. The crude residue was purified by silica gel chromatography with 50% to 100% EtOAc/hexanes to isolate 130 mg (86%) of 2-(5,6-dichloro-1-methyl-1H-indazol-3-yl)-5-(2-trimethyl-silanylethoxymethyl)-5H-pyrrolo[2,3-b]pyrazine-7-carboxylic acid [(R)-2-(4-cyano-piperidin-1-yl)-1-cyclopropyl-2-oxo-ethyl]-amide as a pale yellow foamy solid.

Step 7

2-(5,6-Dichloro-1-methyl-1H-indazol-3-yl)-5H-pyrrolo[2,3-b]pyrazine-7-carboxylic acid [(R)-2-(4-cyano-piperidin-1-yl)-1-cyclopropyl-2-oxo-ethyl]-amide To a solution of 2-(5,6-dichloro-1-methyl-1H-indazol-3-yl)-5-(2-trimethylsilanylethoxymethyl)-5H-pyrrolo[2,3-b]pyrazine-7-carboxylic acid [(R)-2-(4-cyano-piperidin-1-yl)-1-cyclopropyl-2-oxo-ethyl]-amide (130 mg, 0.19 mmol) in CH$_2$Cl$_2$ (4 mL) was added TFA (2.0 mL, 26.0 mmol). The reaction mixture was stirred at room temperature for 3 h then concentrated. The residue was redissolved in CH$_2$Cl$_2$ (4 mL) and ethylenediamine (0.4 mL, 5.92 mmol) was added. The reaction mixture was stirred at room temperature for 0.5 h then quenched with water and extracted with CH$_2$Cl$_2$ (3×). The combined organics were concentrated. The residue was purified by silica gel chromatography with 0% to 4% MeOH/CH$_2$Cl$_2$ (0.5% NH$_4$OH) followed by trituration with Et$_2$O to afford a white solid. This solid was further purified by recrystallization from MeOH/EtOAc to afford 22 mg of 2-(5,6-dichloro-1-methyl-1H-indazol-3-yl)-5H-pyrrolo[2,3-b]pyrazine-7-carboxylic acid [(R)-2-(4-cyano-piperidin-1-yl)-1-cyclopropyl-2-oxo-ethyl]-amide as a white solid. MS: (M+Na)$^+$=573; $^1$H NMR (DMSO-d$_6$, 300 MHz): δ (ppm) 12.92 (br. s., 1H), 9.14 (s, 1H), 8.88 (s, 1H), 8.69 (d, J=8.7 Hz, 1H), 8.46 (d, J=8.7 Hz, 1H), 8.24 (s, 1H), 4.93 (t, J=7.4 Hz, 1H), 4.18 (s, 3H), 3.45-3.94 (m, 3H), 3.15 (d, J=4.9 Hz, 2H), 1.35-1.91 (m, 5H), 0.51 (br. s., 4H).

Example 68

2-(5,6-Dichloroindazolz-1-yl)-5H-pyrrolo[2,3-b]pyrazine-7-carboxylic acid [(R)-2-(4-cyano-piperidin-1-yl)-1-cyclopropyl-2-oxo-ethyl]-amide

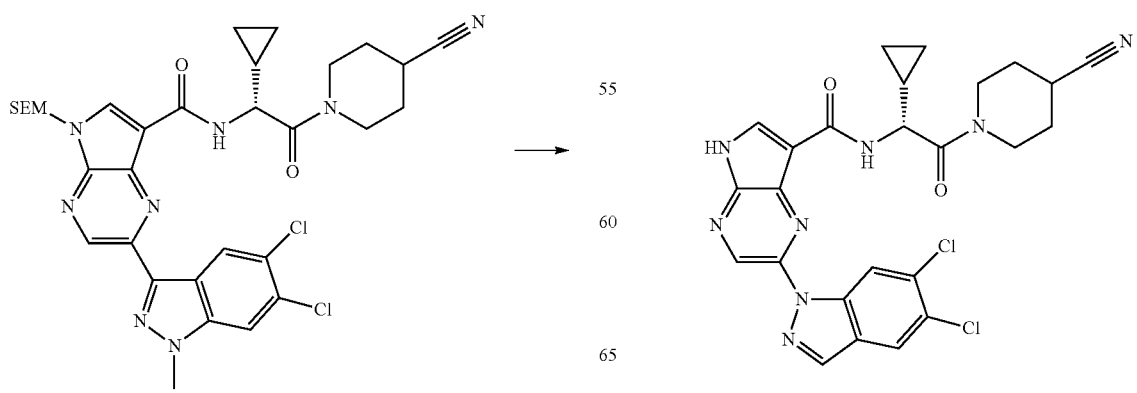

Step 1

2-Iodo-5-(2-trimethylsilanyl-ethoxymethyl)-5H-pyrrolo[2,3-b]pyrazine-7-carboxylic acid [(R)-2-(4-cyano-piperidin-1-yl)-1-cyclopropyl-2-oxo-ethyl]-amide

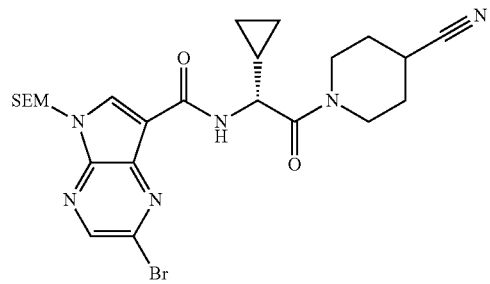

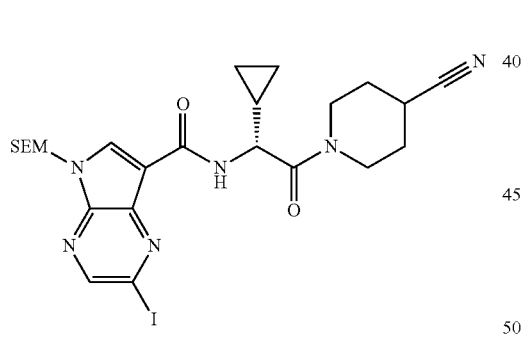

In a 5 mL microwave vial were placed copper(I) iodide (5 mg, 0.027 mmol), sodium iodide (120 mg, 0.80 mmol), 2-bromo-5-(2-trimethylsilanyl-ethoxymethyl)-5H-pyrrolo[2,3-b]pyrazine-7-carboxylic acid [(R)-2-(4-cyano-piperidin-1-yl)-1-cyclopropyl-2-oxo-ethyl]-amide (150 mg, 0.27 mmol), 1,4-dioxane (1 mL) and trans-N,N'-dimethylcyclohexane-1,2-diamine (8 mg, 0.054 mmol). The vial was purged with a stream of nitrogen then sealed and heated in an oil bath at 110° C. for 20 h. The reaction mixture was cooled to room temperature and quenched with sat'd aqueous NH₄OH (3 mL) then diluted with water and extracted with CH₂Cl₂. The organics were dried over MgSO₄ and concentrated. The residue was purified by silica gel chromatography with 50% to 80% EtOAc/hexanes to isolate 130 mg (80%) of 2-iodo-5-(2-trimethylsilanyl-ethoxymethyl)-5H-pyrrolo[2,3-b]pyrazine-7-carboxylic acid [(R)-2-(4-cyano-piperidin-1-yl)-1-cyclopropyl-2-oxo-ethyl]-amide as an orange foamy solid.

Step 2

2-(5,6-Dichloro-indazol-1-yl)-5-(2-trimethylsilanyl-ethoxymethyl)-5H-pyrrolo[2,3-b]pyrazine-7-carboxylic acid [(R)-2-(4-cyano-piperidin-1-yl)-1-cyclopropyl-2-oxo-ethyl]-amide

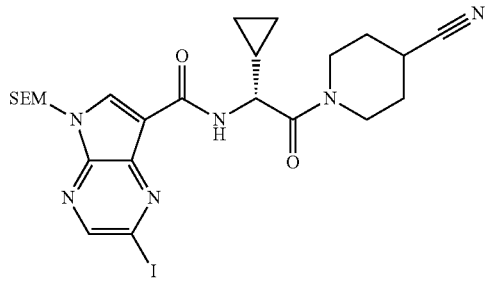

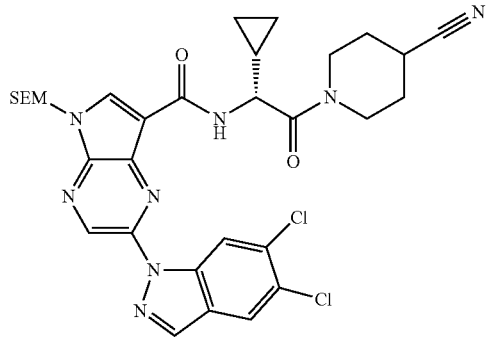

In a 5 mL microwave vial were placed copper(I) iodide (6 mg, 0.033 mmol), K₃PO₄ (146 mg, 0.69 mmol), 5,6-dichloro-1H-indazole (74 mg, 0.39 mmol), 2-iodo-5-(2-trimethylsilanylethoxymethyl)-5H-pyrrolo[2,3-b]pyrazine-7-carboxylic acid [(R)-2-(4-cyano-piperidin-1-yl)-1-cyclopropyl-2-oxo-ethyl]-amide (200 mg, 0.33 mmol), toluene (1.2 mL), and trans-N,N'-dimethylcyclohexane-1,2-diamine (9 mg, 0.066 mmol). The vial was purged with a stream of nitrogen then sealed and heated in an oil bath at 110° C. for 48 h. The reaction mixture was cooled to room temperature and diluted with EtOAc then filtered over a Buchner funnel, rinsing with EtOAc. The filtrate was concentrated and the resultant residue was purified by silica gel chromatography with 0% to 2% MeOH/CH₂Cl₂ (0.5% NH₄OH) to afford 215 mg (98%) of 2-(5,6-dichloro-indazol-1-yl)-5-(2-trimethylsilanyl-ethoxymethyl)-5H-pyrrolo[2,3-b]pyrazine-7-carboxylic acid [(R)-2-(4-cyano-piperidin-1-yl)-1-cyclopropyl-2-oxo-ethyl]-amide as a light yellow foam.

Step 3

2-(5,6-Dichloro-indazol-1-yl)-5H-pyrrolo[2,3-b]pyrazine-7-carboxylic acid [(R)-2-(4-cyano-piperidin-1-yl)-1-cyclopropyl-2-oxo-ethyl]-amide

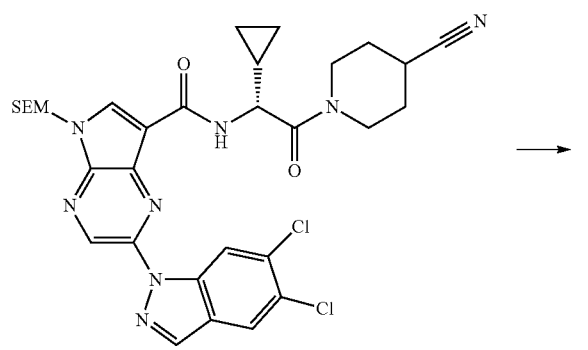

To a solution of 2-(5,6-dichloro-indazol-1-yl)-5-(2-trimethylsilanyl-ethoxymethyl)-5H-pyrrolo[2,3-b]pyrazine-7-carboxylic acid [(R)-2-(4-cyano-piperidin-1-yl)-1-cyclopropyl-2-oxo-ethyl]-amide (220 mg, 0.33 mmol) in CH$_2$Cl$_2$ (4 mL) was added TFA (2.0 mL, 26.0 mmol). The yellow reaction mixture was stirred at room temperature for 3 h then concentrated. The residue was redissolved in CH$_2$Cl$_2$ (4 mL) and ethylenediamine (0.4 mL, 5.92 mmol) was added. The reaction mixture was stirred at room temperature for 0.5 h then quenched with water and extracted with CH$_2$Cl$_2$ (3×). The combined organics were concentrated and the residue was purified by silica gel chromatography with 0% to 5% MeOH/CH$_2$Cl$_2$ (0.5% NH$_4$OH) then triturated with Et$_2$O to afford 95 mg (54%) of 2-(5,6-dichloro-indazol-1-yl)-5H-pyrrolo[2,3-b]pyrazine-7-carboxylic acid [(R)-2-(4-cyano-piperidin-1-yl)-1-cyclopropyl-2-oxo-ethyl]-amide as a light yellow solid. MS: (M+Na)$^+$=559; $^1$H NMR (DMSO-d$_6$, 300 MHz): δ (ppm) 12.91 (br. s., 1H), 8.91 (s, 1H), 8.79 (s, 1H), 8.44 (s, 1H), 8.41 (d, J=7.9 Hz, 1H), 8.29 (d, J=7.9 Hz, 1H), 8.18 (s, 1H), 4.77 (t, J=7.6 Hz, 1H), 3.59-3.86 (m, 2H), 3.32-3.46 (m, 1H), 2.95-3.05 (m, 2H), 1.45-1.92 (m, 4H), 1.24 (br. s., 1H), 0.32-0.48 (m, 4H).

Example 69

2-(5-Chloroindazol-1-yl)-5H-pyrrolo[2,3-b]pyrazine-7-carboxylic acid [(R)-2-(3-cyano-azetidin-1-yl)-1-methyl-2-oxo-ethyl]-amide

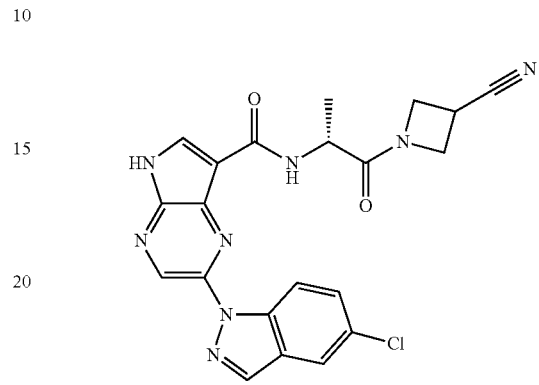

Step 1

2-Iodo-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide

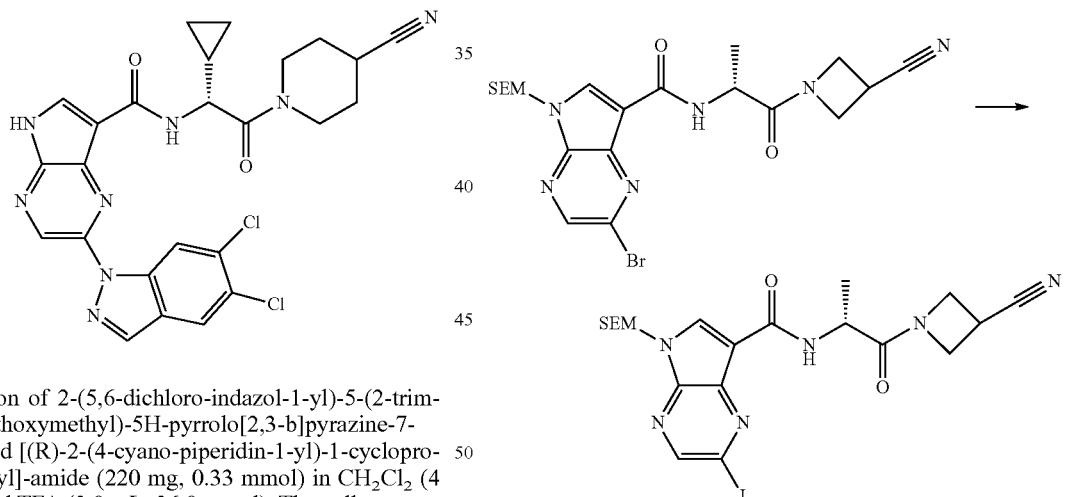

In a 5 mL microwave vial were placed copper(I) iodide (6 mg, 0.03 mmol), sodium iodide (133 mg, 0.89 mmol), 2-bromo-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide (150 mg, 0.30 mmol), 1,4-dioxane (1 mL) and trans-N,N'-dimethylcyclohexane-1,2-diamine (9 mg, 0.06 mmol). The vial was purged with a stream of nitrogen then sealed and heated in an oil bath at 110° C. for 48 h. The reaction mixture was cooled to room temperature and quenched with sat'd aqueous NH$_4$OH (3 mL) then diluted with water and extracted with CH$_2$Cl$_2$. The organics were dried over MgSO$_4$ and concentrated to afford 2-iodo-5-(2-trimethylsilanyl-ethoxymethyl)-5H-pyrrolo[2,3-b]pyrazine-7-carboxylic acid [(R)-2-(3-cyano-azetidin-1- yl)-1-methyl-2-oxo-ethyl]-amide as a maroon oil which was used without further purification.

Step 2

2-(5-Chloro-indazol-1-yl)-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide

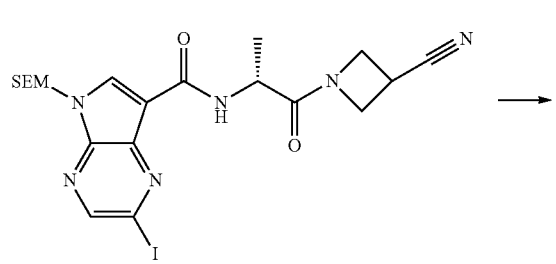

In a 5 mL microwave vial were placed copper(I) iodide (6 mg, 0.033 mmol), K₃PO₄ (132 mg, 0.62 mmol), 5-chloro-1H-indazole (54 mg, 0.36 mmol), 2-iodo-5-(2-trimethylsilanylethoxymethyl)-5H-pyrrolo[2,3-b]pyrazine-7-carboxylic acid [(R)-2-(3-cyano-azetidin-1-yl)-1-methyl-2-oxo-ethyl]-amide (164 mg, 0.30 mmol), toluene (1.2 mL), and trans-N,N'-dimethylcyclohexane-1,2-diamine (9 mg, 0.066 mmol). The vial was purged with a stream of nitrogen then sealed and heated in an oil bath at 110° C. for 24 h. The reaction mixture was cooled to room temperature and diluted with EtOAc then filtered over a Buchner funnel, rinsing with EtOAc. The filtrate was concentrated and the resultant residue was purified by silica gel chromatography with 50% to 80% EtOAc/hexanes to afford 100 mg (58%) of 2-(5-chloro-indazol-1-yl)-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide as a light yellow foam.

Step 3

2-(5-Chloroindazol-1-yl)-5H-pyrrolo[2,3-b]pyrazine-7-carboxylic acid [(R)-2-(3-cyano-azetidin-1-yl)-1-methyl-2-oxo-ethyl]-amide To a solution of 2-(5-chloro-indazol-1-yl)-5-(2-trimethyl-silanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide (100 mg, 0.17 mmol) in CH₂Cl₂ (4 mL) was added TFA (2.0 mL, 26.0 mmol). The yellow reaction mixture was stirred at room temperature for 3 h then concentrated. The residue was redissolved in CH₂Cl₂ (4 mL) and ethylenediamine (0.4 mL, 5.92 mmol) was added. The reaction mixture was stirred at room temperature for 0.5 h then quenched with water and extracted with CH₂Cl₂ (3×). The combined organics were concentrated and the residue was triturated with EtOAc to afford 45 mg (58%) of 2-(5-chloroindazol-1-yl)-5H-pyrrolo[2,3-b]pyrazine-7-carboxylic acid [(R)-2-(3-cyano-azetidin-1-yl)-1-methyl-2-oxo-ethyl]-amide as a light yellow solid. MS: (M+Na)⁺=471; ¹H NMR (DMSO-d₆, 300 MHz): δ (ppm) 12.88 (s, 1H), 8.95 (s, 1H), 8.72 (dd, J=9.1, 4.5 Hz, 1H), 8.36-8.43 (m, 2H), 7.99-8.07 (m, 1H), 7.94 (d, J=1.9 Hz, 1H), 7.41-7.52 (m, 1H), 4.36-4.66 (m, 3H), 4.06-4.18 (m, 1H), 3.94-4.04 (m, 1H), 3.66-3.81 (m, 1H), 1.26 (t, J=6.0 Hz, 3H).

Example 70

2-(1,6,6-Trimethyl-4,5,6,7-tetrahydro-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide

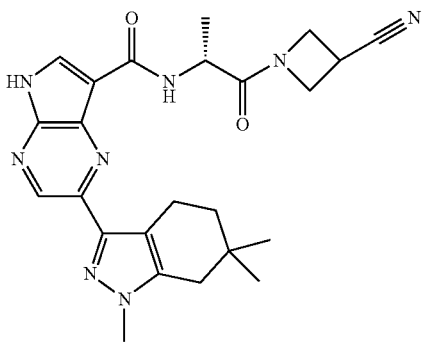 [SMILES: C[C@@H](NC(=O)c1c[nH]c2ncc(-c3nn(C)c4c3CCC(C)(C)C4)nc12)C(=O)N1CC(C#N)C1]

Step 1

2-[1-Hydroxy-meth-(Z)-ylidene]-5,5-dimethyl-cyclohexanone

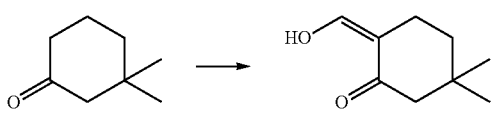

To a suspension of sodium hydride (60% dispersion in mineral oil, 475 mg, 11.9 mmol) in diethyl ether (25 mL) at 0° C. was added ethanol (0.06 ml, 1.03 mmol) dropwise. The grey suspension was stirred at 0° C. for 20 min. A solution of 3,3-dimethylcyclohexanone (1.50 g, 11.9 mmol) and ethyl formate (1.45 ml, 17.8 mmol) in diethyl ether (3 mL) was added dropwise over 10 min. The yellow heterogeneous reaction mixture was stirred at 0° C. for 1 h then warmed to room temperature and stirred for 2 h. Ethanol (1 mL) was added and the mixture was stirred at room temperature for 1 h then quenched with water (25 mL). The layers were separated and the aqueous phase was washed with diethyl ether. The aqueous layer was acidified with 1M HCl until pH=2 and then extracted with diethyl ether (2×). The combined organic layers were dried over MgSO$_4$ and concentrated to afford 1.64 g (90%) of 2-[1-hydroxy-meth-(Z)-ylidene]-5,5-dimethyl-cyclohexanone as a light yellow oil. $^1$H NMR (CDCl$_3$, 400 MHz): δ (ppm) 14.38 (br. s., 1H), 8.79 (s, 1H), 2.34-2.47 (m, 2H), 2.16 (s, 2H), 1.42-1.53 (m, 2H), 1.00 (s, 6H).

Step 2

6,6-Dimethyl-4,5,6,7-tetrahydro-1H-indazole

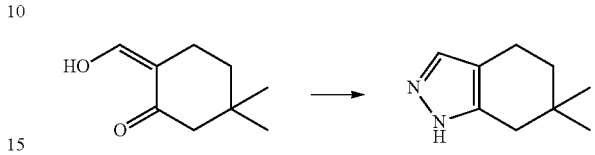

To a solution of 2-[1-hydroxy-meth-(Z)-ylidene]-5,5-dimethyl-cyclohexanone (1.64 g, 10.6 mmol) in MeOH (10 mL) was added hydrazine (0.33 mL, 10.6 mmol) dropwise. The exothermic reaction was controlled by intermitant use of an ice bath. The yellow reaction mixture was stirred at room temperature for 30 min then concentrated. The residue was dissolved in CH$_2$Cl$_2$ and washed with water. The organic layer was dried over MgSO$_4$ and concentrated to afford 1.53 g (96%) of 6,6-dimethyl-4,5,6,7-tetrahydro-1H-indazole as a yellow solid. $^1$H NMR (CDCl$_3$, 300 MHz): δ (ppm) 7.32 (s, 1H), 2.55 (t, J=6.4 Hz, 2H), 2.44 (s, 2H), 1.53 (t, J=6.4 Hz, 2H), 1.01 (s, 6H).

Step 3

3-Iodo-6,6-dimethyl-4,5,6,7-tetrahydro-1H-indazole

To a solution of 6,6-dimethyl-4,5,6,7-tetrahydro-1H-indazole (0.50 g, 3.33 mmol) in DMF (8 mL) at room temperature was added powdered potassium hydroxide (560 mg, 10.0 mmol) and iodine (1.69 g, 6.66 mmol). The maroon reaction mixture was stirred at room temperature for 45 min then quenched with 10% aqueous Na$_2$S$_2$O$_3$, diluted with water and extracted with EtOAc (2×). The combined organics were washed with water (3×), dried over MgSO$_4$ and concentrated to afford 920 mg (99%) of 3-iodo-6,6-dimethyl-4,5,6,7-tetrahydro-1H-indazole as a light yellow waxy solid. $^1$H NMR (CDCl₃, 300 MHz): δ (ppm) 2.44 (s, 2H), 2.35 (t, J=6.4 Hz, 2H), 1.55 (t, J=6.4 Hz, 2H), 1.01 (s, 6H).

Step 4

3-Iodo-1,6,6-trimethyl-4,5,6,7-tetrahydro-1H-indazole and 3-Iodo-2,6,6-trimethyl-4,5,6,7-tetrahydro-2H-indazole

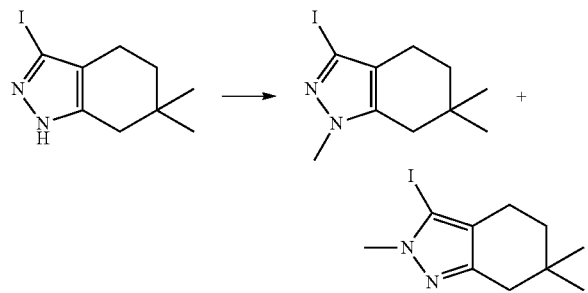

To a solution of 3-iodo-6,6-dimethyl-4,5,6,7-tetrahydro-1H-indazole (919 mg, 3.33 mmol) in THF (8 mL) at 0° C. was added KOt-Bu (523 mg, 4.66 mmol). The reaction mixture was stirred at 0° C. for 30 min then iodomethane (0.29 mL, 4.66 mmol) was added. The reaction mixture was stirred at 0° C. for 30 min then warmed to room temperature and stirred for 1.5 h. The reaction was quenched with water and extracted with EtOAc (2×). The combined organics were dried over MgSO₄ and concentrated. The residue was absorbed onto SiO₂ and purified by chromatography with 10% to 20% EtOAc/hexanes to afford 523 mg (54%) of 3-iodo-1,6,6-trimethyl-4,5,6,7-tetrahydro-1H-indazole as a colorless oil. ¹H NMR (CDCl₃, 300 MHz): δ (ppm) 3.72 (s, 3H), 2.33 (t, J=6.4 Hz, 2H), 2.29 (s, 2H), 1.51 (t, J=6.4 Hz, 2H), 1.02 (s, 6H). Also isolated 160 mg (17%) of 3-iodo-2,6,6-trimethyl-4,5,6,7-tetrahydro-2H-indazole as a white solid. ¹H NMR (CDCl₃, 300 MHz): δ (ppm) 3.87 (s, 3H), 2.41 (s, 2H), 2.36 (t, J=6.6 Hz, 2H), 1.54 (t, J=6.6 Hz, 2H), 1.00 (s, 6H).

Step 5

1,6,6-Trimethyl-3-tributylstannanyl-4,5,6,7-tetrahydro-1H-indazole

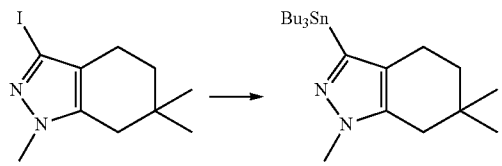

To a solution of 3-iodo-1,6,6-trimethyl-4,5,6,7-tetrahydro-1H-indazole (0.150 g, 0.49 mmol) in THF (3 mL) at 0° C. was slowly added isopropylmagnesium chloride (2.0 M in THF) (0.30 mL, 0.59 mmol). The reaction mixture was stirred at 0° C. for 20 min then tributylchlorostannane (0.16 mL, 0.59 mmol) was added dropwise. The reaction mixture was stirred at 0° C. for 30 min then warmed to room temperature and stirred for 1 h. The reaction was quenched with water and extracted with EtOAc (2×). The combined organics were dried over MgSO₄ and concentrated. The residue was purified by silica gel chromatography with 0% to 10% EtOAc/hexanes (0.5% Et₃N) to afford 116 mg (52%) of 1,6,6-trimethyl-3-tributylstannanyl-4,5,6,7-tetrahydro-1H-indazole as a colorless oil. ¹H NMR (CDCl₃, 300 MHz): δ (ppm) 3.74 (s, 3H), 2.49 (t, J=6.4 Hz, 2H), 2.30 (s, 2H), 1.45-1.61 (m, 8H), 1.25-1.41 (m, 6H), 1.04-1.13 (m, 6H), 1.01 (s, 6H), 0.89 (t, J=7.2 Hz, 9H).

Step 6

5-(2-Trimethylsilanyl-ethoxymethyl)-2-(1,6,6-trimethyl-4,5,6,7-tetrahydro-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide

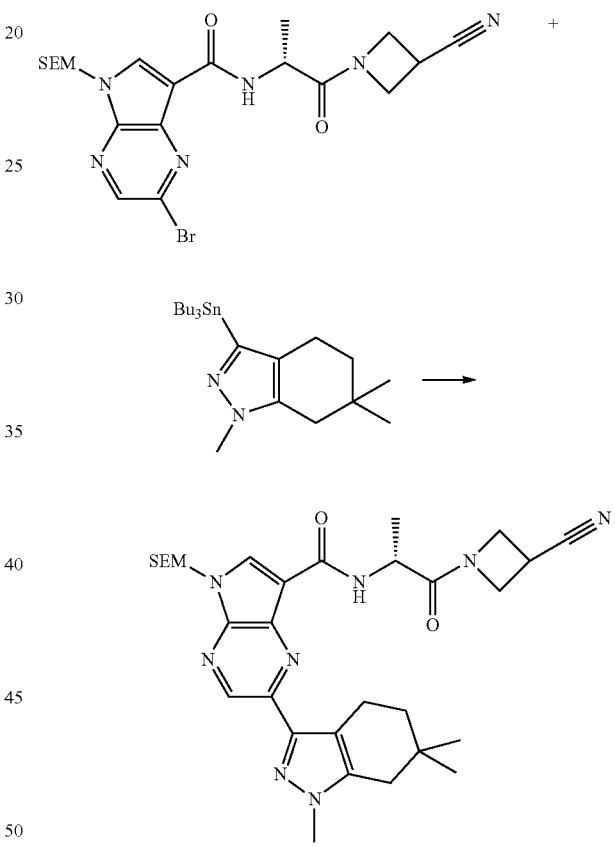

To a solution of 1,6,6-trimethyl-3-tributylstannyl-4,5,6,7-tetrahydro-1H-indazole (110 mg, 0.24 mmol) and 2-bromo-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide (95 mg, 0.19 mmol) in DMF (2 mL) were added Pd(PPh₃)₄ (11 mg, 0.01 mmol) and copper(I) iodide (7 mg, 0.037 mmol). The reaction mixture was heated at 90° C. for 2 h then cooled to room temperature and stirred overnight. The reaction was quenched with water and extracted with EtOAc (2×). The combined organics were washed with water (3×) and brine then dried over MgSO₄ and concentrated. The crude brown oil was purified by silica gel chromatography with 0% to 3% MeOH/CH₂Cl₂ to afford 43 mg (38%) of 5-(2-trimethylsilanyl-ethoxymethyl)-2-(1,6,6-trimethyl-4,5,6,7-tetrahydro-1H-indazol-3-yl)-5H-pyrrolo

[2,3-b]pyrazine-7-carboxylic acid [(R)-2-(3-cyano-azetidin-1-yl)-1-methyl-2-oxo-ethyl]-amide as a pale orange foam.

Step 7

2-(1,6,6-Trimethyl-4,5,6,7-tetrahydro-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide

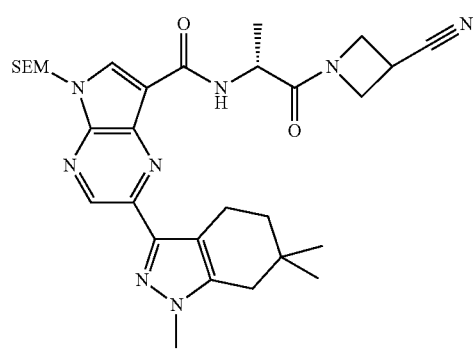

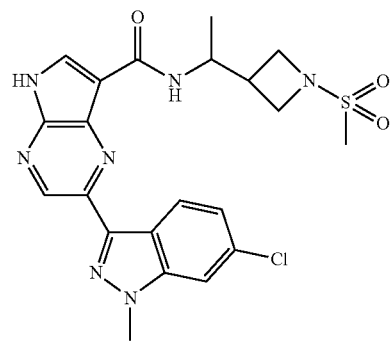 [SMILES: CC(NC(=O)c1c[nH]c2ncc(-c3nn(C)c4cc(Cl)ccc34)nc12)C1CN(S(C)(=O)=O)C1]

To a solution of 5-(2-trimethylsilanyl-ethoxymethyl)-2-(1,6,6-trimethyl-4,5,6,7-tetrahydro-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide (40 mg, 0.068 mmol) in CH$_2$Cl$_2$ (3 mL) was added TFA (1.5 mL, 19.5 mmol). The yellow reaction mixture was stirred at room temperature for 3 h then concentrated. The residue was redissolved in CH$_2$Cl$_2$ (3 mL) and ethylenediamine (0.3 mL, 4.44 mmol) was added. The reaction mixture was stirred at room temperature for 0.5 h then quenched with water and extracted with CH$_2$Cl$_2$ (3×). The combined organics were concentrated to a yellow oily solid. Trituration with EtOAc/Et$_2$O gave 17 mg (55%) of 2-(1,6,6-trimethyl-4,5,6,7-tetrahydro-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide as an off-white solid. MS (M+H)$^+$=461; $^1$H NMR (DMSO-d$_6$, 400 MHz): δ (ppm) 8.94 (d, J=2.0 Hz, 1H), 8.34-8.44 (m, 2H), 4.46-4.74 (m, 3H), 4.10-4.21 (m, 1H), 4.02 (dd, J=9.9, 6.4 Hz, 1H), 3.78-3.86 (m, 1H), 3.77 (s, 3H), 2.98-3.08 (m, 1H), 2.85-2.94 (m, 1H), 2.45 (s, 2H), 1.52 (t, J=6.4 Hz, 2H), 1.29-1.39 (m, 3H), 1.03 (s, 6H).

Example 71

2-(6-Chloro-1-methyl-1H-indazol-3-yl)-5H-pyrrolo[2,3-b]pyrazine-7-carboxylic acid [1-(1-methanesulfonyl-azetidin-3-yl)-ethyl]-amide

Step 1

3-{[(E)-2-Methyl-propane-2-sulfinylimino]-methyl}-azetidine-1-carboxylic acid tert-butyl ester

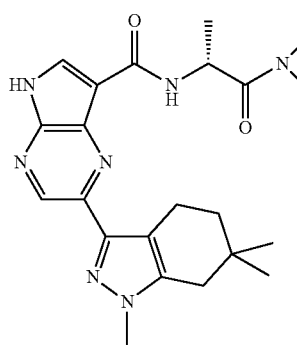

To a solution of 3-formyl-azetidine-1-carboxylic acid tert-butyl ester (1.0 g, 5.4 mmol) and 2-methylpropane-2-sulfinamide (654 mg, 5.4 mmol) in dry CH$_2$Cl$_2$ (10 mL) was added anhydrous CuSO$_4$ (1.9 g, 11.9 mmol). The heterogeneous reaction mixture was stirred at room temperature overnight then filtered over Celite, rinsing with CH$_2$Cl$_2$. The filtrate was concentrated and the resultant residue was absorbed onto SiO$_2$ and purified by column chromatography with 20% to 40% EtOAc/hexanes to provide 1.26 g (81%) of 3-{[(E)-2- methyl-propane-2-sulfinylimino]-methyl}-azetidine-1-carboxylic acid tert-butyl ester as a white solid.

¹H NMR (CDCl₃, 300 MHz): δ (ppm) 8.20 (d, J=4.5 Hz, 1H), 4.14-4.23 (m, 2H), 4.00-4.13 (m, 2H), 3.53-3.65 (m, 1H), 1.45 (s, 9H), 1.21 (s, 9H).

Step 2

3-[1-(2-Methyl-propane-2-sulfinylamino)-ethyl]-azetidine-1-carboxylic acid tert-butyl ester

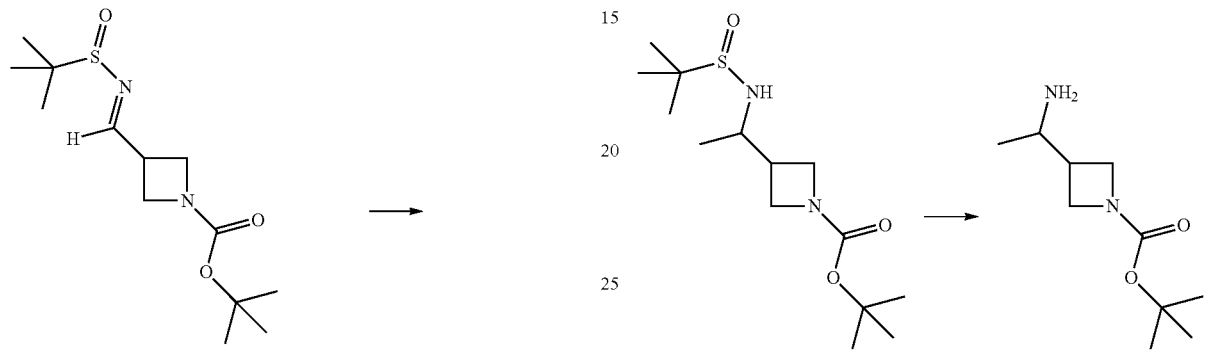

To a solution of 3-{[(E)-2-methyl-propane-2-sulfinylimino]-methyl}-azetidine-1-carboxylic acid tert-butyl ester (0.25 g, 0.87 mmol) in CH₂Cl₂ (4 mL) at 0° C. was added dropwise methylmagnesium bromide (3.0 M in Et₂O, 0.35 mL, 1.04 mmol). The reaction mixture was stirred at 0° C. for 1 h then quenched with saturated aqueous NH₄Cl, diluted with water and extracted with EtOAc (2×). The combined organics were dried over MgSO₄ and concentrated to afford 273 mg of 3-[1-(2-methyl-propane-2-sulfinylamino)-ethyl]-azetidine-1-carboxylic acid tert-butyl ester as an off-white foamy solid which was used without further purification.

Step 3

3-(1-Amino-ethyl)-azetidine-1-carboxylic acid tert-butyl ester

To a solution 3-[1-(2-methyl-propane-2-sulfinylamino)-ethyl]-azetidine-1-carboxylic acid tert-butyl ester (crude from step 2, 264 mg, 0.87 mmol) in MeOH at 0° C. was added 4.0 M HCl in dioxane (0.28 mL, 1.13 mmol) dropwise. The reaction mixture was stirred at 0° C. for 1 h then quenched with saturated aqueous NaHCO₃, diluted with water and extracted with CH₂Cl₂ (3×). The combined organics were dried over MgSO₄ and concentrated to afford 3-(1-aminoethyl)-azetidine-1-carboxylic acid tert-butyl ester as a thick colorless oil which was used without further purification.

Step 4

3-(1-{[2-(6-Chloro-1-methyl-1H-indazol-3-yl)-5-(2-trimethylsilanyl-ethoxymethyl)-5H-pyrrolo[2,3-b]pyrazine-7-carbonyl]-amino}-ethyl)-azetidine-1-carboxylic acid tert-butyl ester

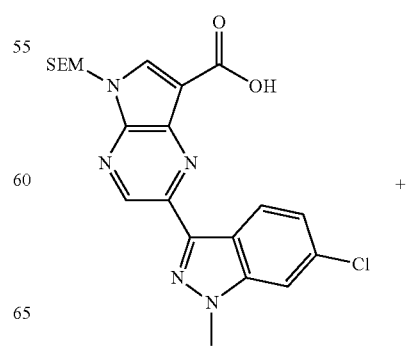

+

-continued

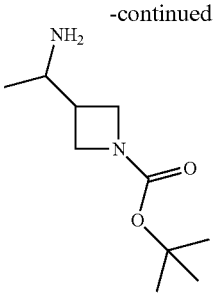

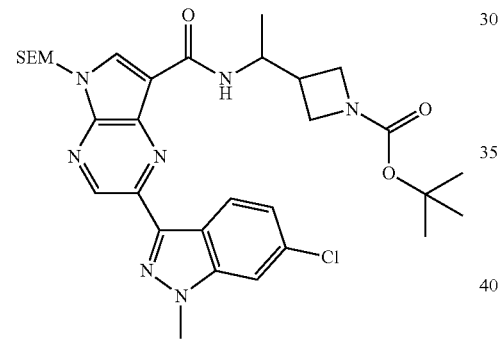

To a solution of 3-(1-amino-ethyl)-azetidine-1-carboxylic acid tert-butyl ester (crude from step 3, 63 mg, 0.31 mmol) in DMF (2 mL) were added N,N-diisopropylethylamine (69 μL, 0.39 mmol), 2-(6-chloro-1-methyl-1H-indazol-3-yl)-5-(2-trimethylsilanyl-ethoxymethyl)-5H-pyrrolo[2,3-b]pyrazine-7-carboxylic acid (120 mg, 0.26 mmol), and HATU (110 mg, 0.29 mmol). The yellow reaction mixture was stirred at room temperature overnight then quenched with water and extracted with EtOAc (3×). The combined organics were washed with water (3×) and brine then dried over MgSO$_4$ and concentrated. The residue was purified by silica gel chromatography with 30% to 60% EtOAc/hexanes to afford 158 mg (94%) of 3-(1-{[2-(6-chloro-1-methyl-1H-indazol-3-yl)-5-(2-trimethylsilanyl-ethoxymethyl)-5H-pyrrolo[2,3-b]pyrazine-7-carbonyl]-amino}-ethyl)-azetidine-1-carboxylic acid tert-butyl ester as a white foam. $^1$H NMR (CDCl$_3$, 300 MHz): δ (ppm) 9.23 (s, 1H), 8.36 (t, J=4.3 Hz, 2H), 8.18 (d, J=9.1 Hz, 1H), 7.52 (s, 1H), 7.24-7.29 (m, 1H), 5.73 (s, 2H), 4.57-4.68 (m, 1H), 4.18 (s, 3H), 3.87-4.08 (m, 3H), 3.79 (dd, J=8.7, 6.0 Hz, 1H), 3.55-3.65 (m, 2H), 2.73 (br. s., 1H), 1.39 (s, 9H), 1.36 (d, J=6.8 Hz, 6H), 0.89-1.01 (m, 2H), −0.03 (s, 9H).

Step 5

2-(6-Chloro-1-methyl-1H-indazol-3-yl)-5-(2-trimethylsilanyl-ethoxymethyl)-5H-pyrrolo[2,3-b]pyrazine-7-carboxylic acid (1-azetidin-3-yl-ethyl)-amide hydrochloride

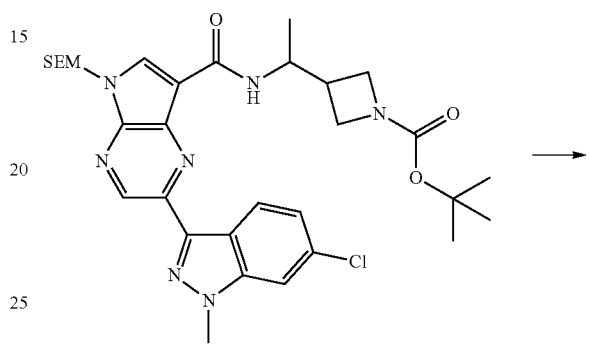

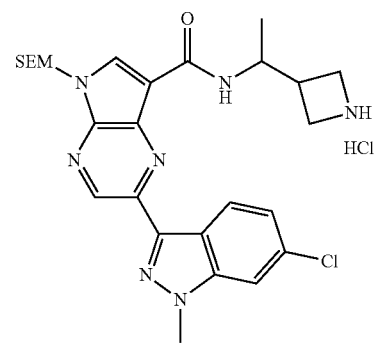

To a solution of 3-(1-{[2-(6-chloro-1-methyl-1H-indazol-3-yl)-5-(2-trimethylsilanylethoxymethyl)-5H-pyrrolo[2,3-b]pyrazine-7-carbonyl]-amino}-ethyl)-azetidine-1-carboxylic acid tert-butyl ester (150 mg, 0.23 mmol) in MeOH (4 mL) at 0° C. was added acetyl chloride (0.33 mL, 4.69 mmol) dropwise over 5 min. The reaction mixture was stirred at room temperature for 1 h as a thick precipitate gradually formed. The solvent was evaporated at room temperature and the residue was dried under high vacuum to isolate 145 mg of 2-(6-chloro-1-methyl-1H-indazol-3-yl)-5-(2-trimethylsilanyl-ethoxymethyl)-5H-pyrrolo[2,3-b]pyrazine-7-carboxylic acid (1-azetidin-3-yl-ethyl)-amide hydrochloride as a yellow solid.

Step 6

2-(6-Chloro-1-methyl-1H-indazol-3-yl)-5-(2-trimethylsilanyl-ethoxymethyl)-5H-pyrrolo[2,3-b]pyrazine-7-carboxylic acid [1-(1-methanesulfonyl-azetidin-3-yl)-ethyl]-amide

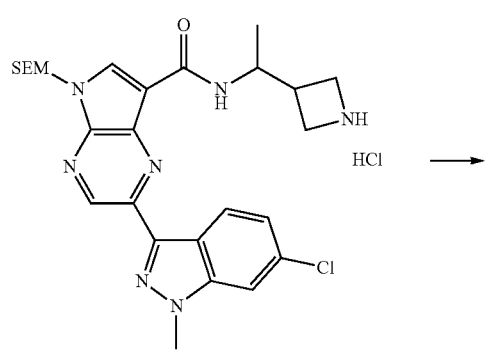

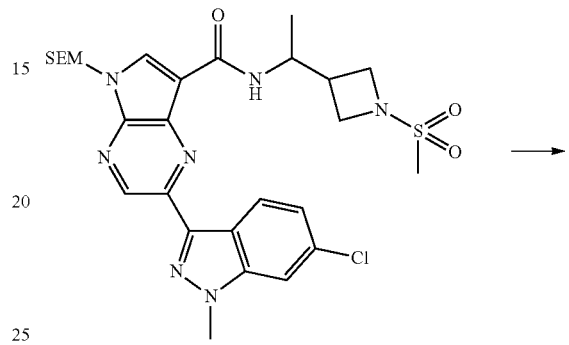

To a suspension of 2-(6-chloro-1-methyl-1H-indazol-3-yl)-5-(2-trimethylsilanylethoxymethyl)-5H-pyrrolo[2,3-b]pyrazine-7-carboxylic acid (1-azetidin-3-yl-ethyl)-amide hydrochloride (65 mg, 0.11 mmol) in $CH_2Cl_2$ (2 mL) at 0° C. was added triethylamine (47 µL, 0.33 mmol) followed by methanesulfonyl chloride (10 µL, 0.12 mmol). The reaction mixture was stirred at 0° C. for 30 min then at room temperature for 1 h. The reaction was quenched with water and extracted with $CH_2Cl_2$. The combined organics were dried over $MgSO_4$ and concentrated. The residue was purified by silica gel chromatography with 0% to 5% $MeOH/CH_2Cl_2$ (0.5% $NH_4OH$) to afford 35 mg (50%) of 2-(6-chloro-1-methyl-1H-indazol-3-yl)-5-(2-trimethylsilanyl-ethoxymethyl)-5H-pyrrolo[2,3-b]pyrazine-7-carboxylic acid [1-(1-methanesulfonyl-azetidin-3-yl)-ethyl]-amide as a pale yellow solid.

Step 7

2-(6-Chloro-1-methyl-1H-indazol-3-yl)-5H-pyrrolo[2,3-b]pyrazine-7-carboxylic acid [1-(1-methanesulfonyl-azetidin-3-yl)-ethyl]-amide

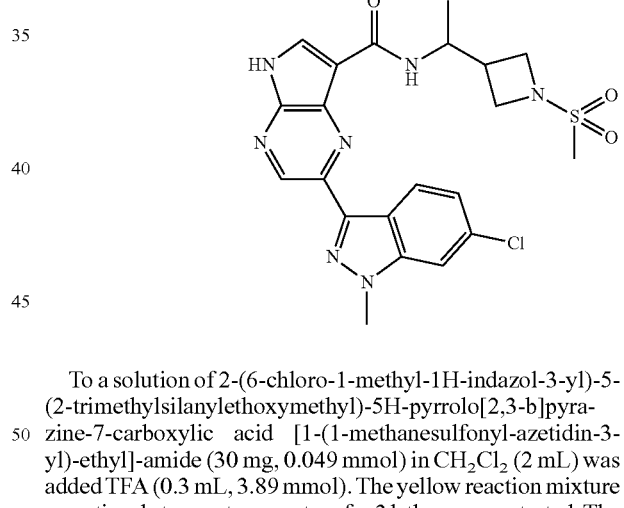

To a solution of 2-(6-chloro-1-methyl-1H-indazol-3-yl)-5-(2-trimethylsilanylethoxymethyl)-5H-pyrrolo[2,3-b]pyrazine-7-carboxylic acid [1-(1-methanesulfonyl-azetidin-3-yl)-ethyl]-amide (30 mg, 0.049 mmol) in $CH_2Cl_2$ (2 mL) was added TFA (0.3 mL, 3.89 mmol). The yellow reaction mixture was stirred at room temperature for 3 h then concentrated. The residue was redissolved in $CH_2Cl_2$ (2 mL) and ethylenediamine (0.3 mL, 4.49 mmol) was added. The reaction mixture was stirred at room temperature for 1 h then quenched with water and extracted with $MeOH/CH_2Cl_2$ (1:9). The organic layer was washed with water and the aqueous was back-extracted with $CH_2Cl_2$. The combined organics were concentrated and the residue was triturated with $MeOH/EtOAc/Et_2O$ to afford 15 mg (63%) of 2-(6-chloro-1-methyl-1H-indazol-3-yl)-5H-pyrrolo[2,3-b]pyrazine-7-carboxylic acid [1-(1-methanesulfonyl-azetidin-3-yl)-ethyl]-amide as a pale yellow solid. MS $(M+H)^+=488$; $^1H$ NMR (DMSO-$d_6$, 300 MHz): δ (ppm) 9.05 (br. s., 1H), 8.86 (s, 1H), 8.63 (s, 1H), 8.41 (d, J=8.7 Hz, 1H), 7.92 (s, 1H), 7.26 (d, J=8.7 Hz, 1H), 4.35-4.45 (m, 1H), 4.22-4.33 (m, 1H), 4.12 (s, 3H), 4.04-4.10

(m, 1H), 3.62-3.74 (m, 1H), 3.45-3.58 (m, 1H), 3.25 (s, 3H), 2.57-2.68 (m, 1H), 1.38 (d, J=6.8 Hz, 3H).

Example 72

2-(6-Chloro-1-methyl-1H-indazol-3-yl)-5H-pyrrolo[2,3-b]pyrazine-7-carboxylic acid ((R)-1-methyl-3-oxo-3-pyrrolidin-1-yl-propyl)-amide

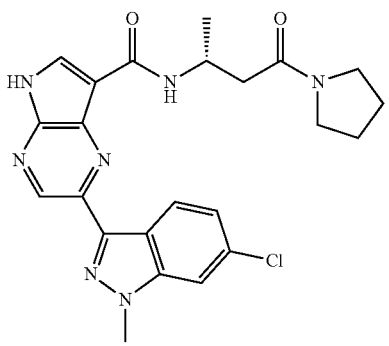 [SMILES: C[C@H](CC(=O)N1CCCC1)NC(=O)c1c[nH]c2ncc(-c3nn(C)c4cc(Cl)ccc34)nc12]

Step 1

((R)-1-Methyl-3-oxo-3-pyrrolidin-1-yl-propyl)-carbamic acid tert-butyl ester

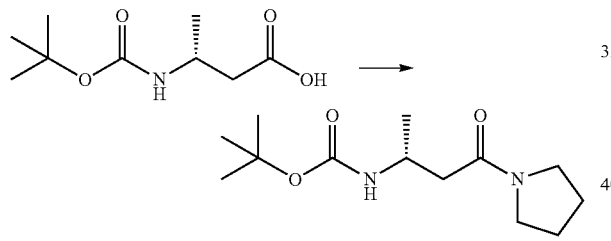

To a solution of (R)-3-tert-butoxycarbonylamino-butyric acid (150 mg, 0.74 mmol) and HATU (309 mg, 0.81 mmol) in DMF (2 mL) was added pyrrolidine (0.19 mL, 2.21 mmol). The resultant yellow reaction mixture was stirred at room temperature overnight then quenched with water and extracted with EtOAc (2×). The combined organics were washed with water (3×) and brine then dried over MgSO₄ and concentrated to afford ((R)-1-methyl-3-oxo-3-pyrrolidin-1-yl-propyl)-carbamic acid tert-butyl ester as a colorless oil which was used without further purification.

Step 2

(R)-3-Amino-1-pyrrolidin-1-yl-butan-1-one trifluoroacetate

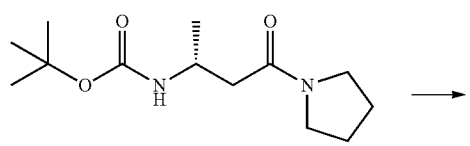

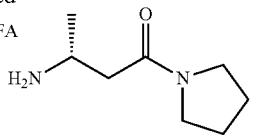

To a solution of ((R)-1-methyl-3-oxo-3-pyrrolidin-1-yl-propyl)-carbamic acid tert-butyl ester (crude from step 1, 189 mg, 0.74 mmol) in CH₂Cl₂ (5 mL) was added trifluoroacetic acid (2.0 mL, 27.0 mmol). The reaction mixture was stirred at room temperature for 2 h then concentrated to give (R)-3-amino-1-pyrrolidin-1-yl-butan-1-one trifluoroacetate as a pale yellow oil which was used without further purification.

Step 3

2-(6-Chloro-1-methyl-1H-indazol-3-yl)-5-(2-trimethylsilanyl-ethoxymethyl)-5H-pyrrolo[2,3-b]pyrazine-7-carboxylic acid ((R)-1-methyl-3-oxo-3-pyrrolidin-1-yl-propyl)-amide

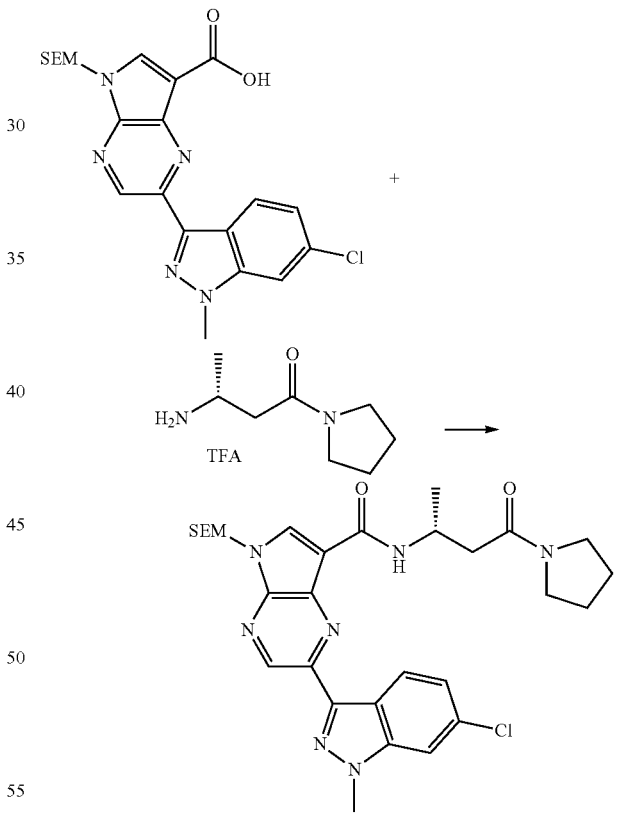

To a solution of (R)-3-amino-1-pyrrolidin-1-yl-butan-1-one trifluoroacetate (crude from step 2, 118 mg, 0.44 mmol) in DMF (2 mL) were added N,N-diisopropylethylamine (0.19 mL, 1.09 mmol), 2-(6-chloro-1-methyl-1H-indazol-3-yl)-5-(2-trimethylsilanyl-ethoxymethyl)-5H-pyrrolo[2,3-b]pyrazine-7-carboxylic acid (100 mg, 0.22 mmol), and HATU (91 mg, 0.24 mmol). The reaction mixture was stirred at room temperature overnight then quenched with water and extracted with EtOAc (3×). The combined organics were washed with water (3×) and brine then dried over MgSO₄ and concentrated. The residue was purified by silica gel chromatography with 50% to 100% EtOAc/hexanes to afford 125 mg (96%) of 2-(6-chloro-1-methyl-1H-indazol-3-yl)-5-(2-trimethylsilanyl-ethoxymethyl)-5H-pyrrolo[2,3-b]pyrazine-7-carboxylic acid ((R)-1-methyl-3-oxo-3-pyrrolidin-1-yl-propyl)-amide as a white solid.

Step 4

2-(6-Chloro-1-methyl-1H-indazol-3-yl)-5H-pyrrolo[2,3-b]pyrazine-7-carboxylic acid ((R)-1-methyl-3-oxo-3-pyrrolidin-1-yl-propyl)-amide

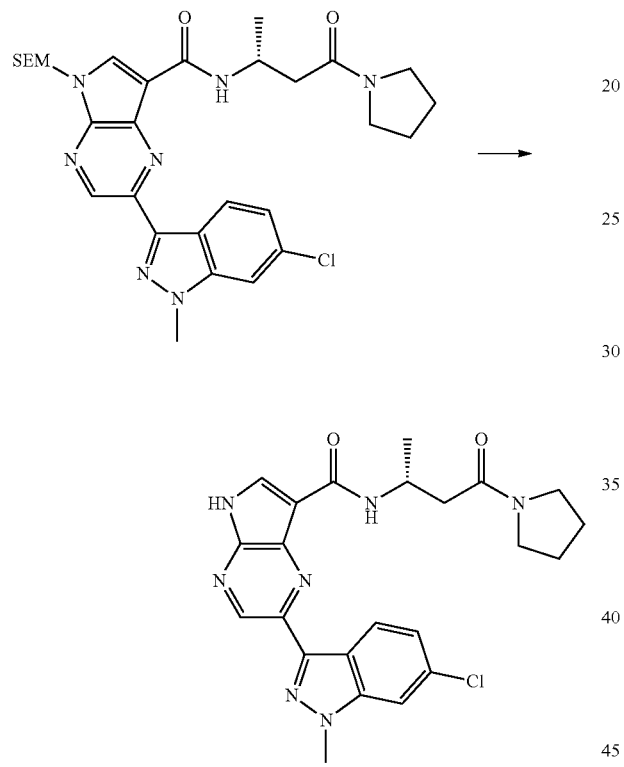

To a solution of 2-(6-chloro-1-methyl-1H-indazol-3-yl)-5-(2-trimethylsilanylethoxymethyl)-5H-pyrrolo[2,3-b]pyrazine-7-carboxylic acid ((R)-1-methyl-3-oxo-3-pyrrolidin-1-yl-propyl)-amide (125 mg, 0.21 mmol) in CH$_2$Cl$_2$ (2 mL) was added TFA (0.5 mL, 6.49 mmol). The yellow reaction mixture was stirred at room temperature for 3 h then concentrated. The residue was redissolved in CH$_2$Cl$_2$ (2 mL) and ethylenediamine (0.4 mL, 6.0 mmol) was added. The reaction mixture was stirred at room temperature for 1 h then quenched with water. The resultant precipitate was collected via filtration and washed with water and EtOAc. The solid was dissolved in 10% MeOH/CH$_2$Cl$_2$ and washed with water. The aqueous layer was back-extracted with CH$_2$Cl$_2$. The combined organics were dried over MgSO$_4$ and concentrated to afford 64 mg (66%) of 2-(6-Chloro-1-methyl-1H-indazol-3-yl)-5H-pyrrolo[2,3-b]pyrazine-7-carboxylic acid ((R)-1-methyl-3-oxo-3-pyrrolidin-1-yl-propyl)-amide as an off-white solid. MS: (M+H)$^+$=466; $^1$H NMR (DMSO-d$_6$, 300 MHz): δ (ppm) 9.07 (s, 1H), 8.57 (d, J=8.7 Hz, 1H), 8.41 (s, 1H), 8.26 (d, J=7.9 Hz, 1H), 7.97 (d, J=1.1 Hz, 1H), 7.28 (dd, J=8.7, 1.5 Hz, 1H), 4.36-4.54 (m, 1H), 4.16 (s, 3H), 3.40 (t, J=6.6 Hz, 2H), 3.10-3.25 (m, 2H), 2.52-2.76 (m, 2H), 1.61-1.90 (m, 4H), 1.38 (d, J=6.8 Hz, 3H).

Example 73

2-(6-Fluoro-1-methyl-1H-indazol-3-yl)-5H-pyrrolo[2,3-b]pyrazine-7-carboxylic acid [1-(cis-3-hydroxy-cyclobutyl)-ethyl]-amide

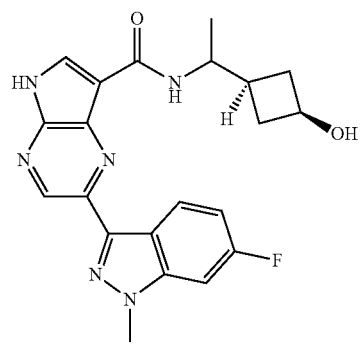 [SMILES: CC(NC(=O)c1c[nH]c2ncc(-c3nn(C)c4cc(F)ccc34)nc12)[C@H]1C[C@@H](O)C1]

Step 1 cis-3-Hydroxy-cyclobutanecarbonitrile

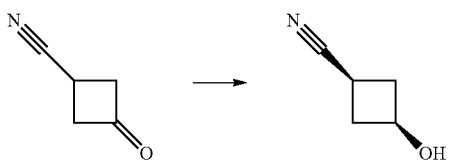 [SMILES: N#CC1CC(=O)C1 ; N#C[C@H]1C[C@@H](O)C1]

3-Oxocyclobutanecarbonitrile was prepared according to Elend, D.; Fengas, D.; Fray, J. M. *Synthetic Communications*, 2005, 35, 657. To a solution of 3-oxocyclobutanecarbonitrile (600 mg, 6.31 mmol) in MeOH (25 mL) at 0° C. was slowly added sodium borohydride (263 mg, 6.94 mmol). The reaction mixture was stirred at 0° C. for 1 h then quenched with water and brine and extracted with EtOAc (3×). The combined organics were dried over MgSO$_4$ and concentrated to afford 500 mg (82%) of cis-3-hydroxy-cyclobutanecarbonitrile as a colorless oil. $^1$H NMR (CDCl$_3$, 300 MHz): δ (ppm)

4.26 (quin, J=7.5 Hz, 1H), 2.70-2.82 (m, 2H), 2.50-2.66 (m, 1H), 2.26-2.41 (m, 2H), 2.09 (br. s., 1H).

Step 2 cis-3-(tert-Butyldimethylsilanyloxy)-cyclobutanecarbonitrile

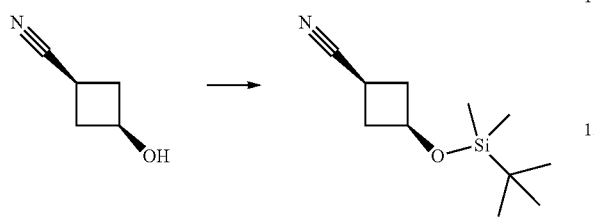

To a solution of cis-3-hydroxy-cyclobutanecarbonitrile (500 mg, 5.15 mmol in DMF (3 mL) at room temperature was added imidazole (876 mg, 12.9 mmol) followed by TBDMS-Cl (854 mg, 5.66 mmol). The reaction mixture was stirred at room temperature overnight then quenched with water and extracted with EtOAc (2×). The combined organics were washed with water (3×), dried over $MgSO_4$ and concentrated. The residue was purified by silica gel chromatography with 0% to 10% EtOAc/hexanes to afford 890 mg (82%) of cis-3-(tert-butyldimethylsilanyloxy)-cyclobutanecarbonitrile as a colorless oil. $^1H$ NMR ($CDCl_3$, 400 MHz): δ (ppm) 4.10-4.19 (m, 1H), 2.57-2.67 (m, 2H), 2.43-2.54 (m, 1H), 2.22-2.34 (m, 2H), 0.84 (s, 9H), 0.00 (s, 6H).

Step 3 cis-3-(tert-Butyldimethylsilanyloxy)-cyclobutanecarbaldehyde

To a solution of cis-3-(tert-butyldimethylsilyloxy)cyclobutanecarbonitrile (0.89 g, 4.21 mmol in $CH_2Cl_2$ (25 mL) at −70° C. was slowly added DIBAL-H (1.05 mL, 5.89 mmol). The reaction mixture was stirred for 2.5 h as the temperature gradually rose to 0° C. The cloudy reaction mixture was quenched with MeOH (1 mL) then diluted with $CH_2Cl_2$ (20 mL) and saturated aqueous Na+ K+ tartrate (25 mL) was added. The biphasic mixture was stirred vigorously at room temperature for 1 h. The layers were separated and the aqueous phase was extracted with $CH_2Cl_2$ (2×). The combined organics were dried over $MgSO_4$ and concentrated to give cis-3-(tert-butyldimethylsilanyloxy)-cyclobutanecarbaldehyde as a colorless oil which was used without further purification.

Step 4

2-Methyl-propane-2-sulfinic acid 1-[cis-3-(tert-butyldimethylsilanyloxy)-cyclobutyl]-meth-(E)-ylideneamide

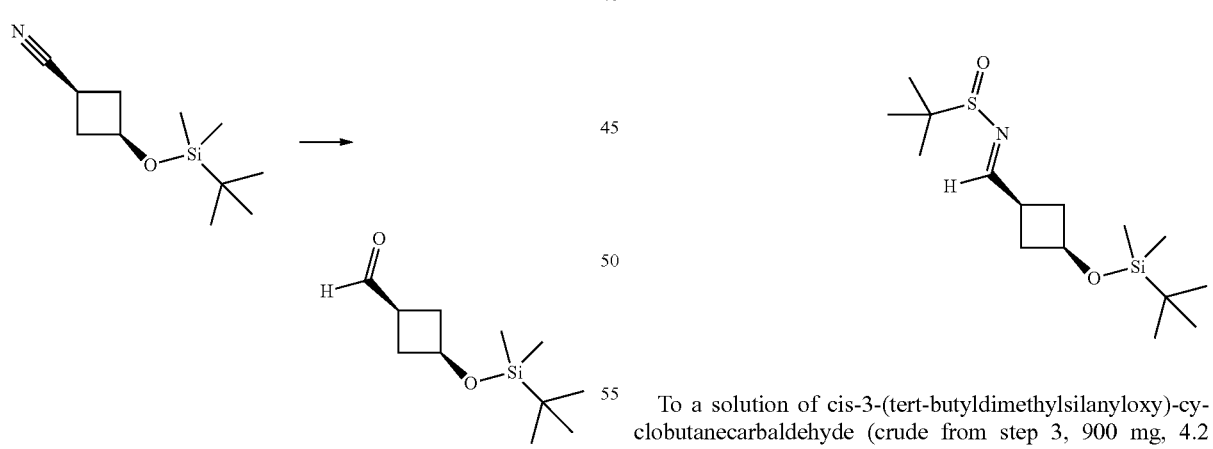

To a solution of cis-3-(tert-butyldimethylsilanyloxy)-cyclobutanecarbaldehyde (crude from step 3, 900 mg, 4.2 mmol) and 2-methylpropane-2-sulfinamide (509 mg, 4.2 mmol) in dry $CH_2Cl_2$ (10 mL) was added anhydrous $CuSO_4$ (1.47 g, 9.24 mmol). The heterogeneous reaction mixture was stirred at room temperature overnight then filtered over Celite, rinsing with $CH_2Cl_2$. The filtrate was absorbed onto $SiO_2$ and purified via chromatography with 0% to 20% EtOAc/hexanes to isolate 642 mg (48%) of 2-methyl-propane-2-sulfinic acid 1-[cis-3-(tert-butyldimethylsilanyloxy)-cyclobutyl]-meth-(E)-ylideneamide as a colorless oil. $^1H$ NMR ($CDCl_3$, 300 MHz): δ (ppm) 8.04 (d, J=5.3 Hz, 1H), 4.25 (quin, J=7.4 Hz, 1H), 2.73-2.88 (m, 1H), 2.46-2.59 (m, 2H), 2.06-2.18 (m, 2H), 1.19 (s, 9H), 0.89 (s, 9H), 0.05 (s, 6H).

(m, 2H), 1.59-1.76 (m, 3H), 1.20 (s, 9H), 1.18 (d, J=6.0 Hz, 3H), 0.88 (s, 9H), 0.03 (s, 6H).

Step 5

2-Methyl-propane-2-sulfinic acid {1-[cis-3-(tert-butyl-dimethyl-silanyloxy)-cyclobutyl]-ethyl}-amide Step 6 cis-3-(1-Aminoethyl)-cyclobutanol hydrochloride

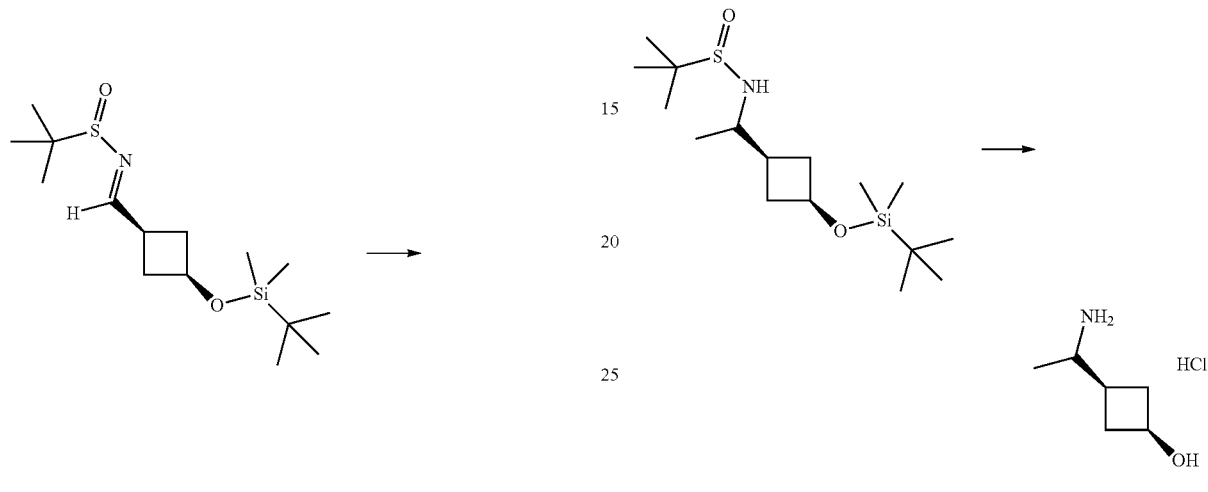

To a solution of 2-methyl-propane-2-sulfinic acid {1-[cis-3-(tert-butyl-dimethyl-silanyloxy)-cyclobutyl]-ethyl}-amide (200 mg, 0.60 mmol) in MeOH (3 mL) was added hydrogen chloride (4.0M in 1,4-dioxane, 0.30 mL, 1.2 mmol). The reaction mixture was stirred at room temperature for 20 min then concentrated to afford cis-3-(1-aminoethyl)-cyclobutanol hydrochloride as an off-white semisolid which was used without further purification. $^1$H NMR (METHANOL-$d_4$, 300 MHz): δ (ppm) 4.09 (quind, J=7.5, 3.8 Hz, 1H), 3.17 (dt, J=6.0, 3.0 Hz, 1H), 2.36-2.56 (m, 2H), 1.78-1.96 (m, 1H), 1.59-1.77 (m, 2H), 1.22 (dd, J=6.8, 3.8 Hz, 3H).

Step 7

2-(6-Fluoro-1-methyl-1H-indazol-3-yl)-5-(2-trimethylsilanyl-ethoxymethyl)-5H-pyrrolo[2,3-b]pyrazine-7-carboxylic acid [1-(cis-3-hydroxy-cyclobutyl)-ethyl]-amide To a solution of 2-methyl-propane-2-sulfinic acid 1-[cis-3-(tert-butyldimethylsilanyloxy)-cyclobutyl]-meth-(E)-ylideneamide (640 mg, 2.02 mmol) in CH$_2$Cl$_2$ (10 mL) at 0° C. was slowly added methylmagnesium bromide (3.0 M in Et$_2$O, 1.14 mL, 3.43 mmol). The reaction mixture was stirred at 0° C. for 1 h then quenched with saturated aqueous NH$_4$Cl, diluted with water and extracted with EtOAc (3×). The combined organics were dried over MgSO$_4$ and concentrated to provide 685 mg of 2-methyl-propane-2-sulfinic acid {1-[cis-3-(tert-butyl-dimethyl-silanyloxy)-cyclobutyl]-ethyl}-amide as an off-white waxy solid which was used without further purification. $^1$H NMR (CDCl$_3$, 300 MHz): δ (ppm) 4.05-4.18 (m, 1H), 3.16-3.31 (m, 1H), 2.85 (d, J=7.2 Hz, 1H), 2.21-2.44

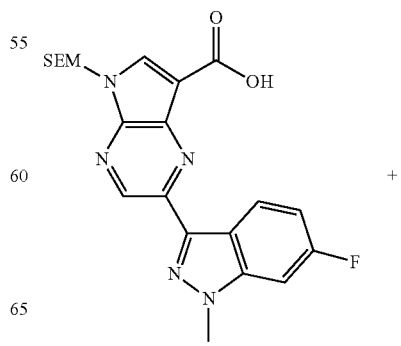

481

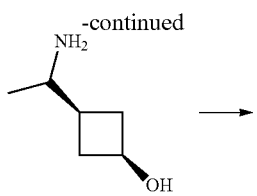


To a solution of cis-3-(1-aminoethyl)-cyclobutanol hydrochloride (crude from step 6, 91 mg, 0.60 mmol) in DMF (2 mL) were added N,N-diisopropylethylamine (0.24 mL, 1.36 mmol), 2-(6-fluoro-1-methyl-1H-indazol-3-yl)-5-(2-trimethylsilanyl-ethoxymethyl)-5H-pyrrolo[2,3-b]pyrazine-7-carboxylic acid (120 mg, 0.27 mmol), and HATU (114 mg, 0.30 mmol). The yellow reaction mixture was stirred at room temperature overnight then quenched with water and extracted with EtOAc (3×). The combined organics were washed with water (3×) and brine then dried over MgSO$_4$ and concentrated to a pale yellow solid. Trituration with EtOAc/Et$_2$O gave 108 mg (74%) of 2-(6-fluoro-1-methyl-1H-indazol-3-yl)-5-(2-trimethylsilanyl-ethoxymethyl)-5H-pyrrolo[2,3-b]pyrazine-7-carboxylic acid [1-(cis-3-hydroxycyclobutyl)-ethyl]-amide as a white solid.

Step 8

2-(6-Fluoro-1-methyl-1H-indazol-3-yl)-5H-pyrrolo[2,3-b]pyrazine-7-carboxylic acid [1-(cis-3-hydroxycyclobutyl)-ethyl]-amide

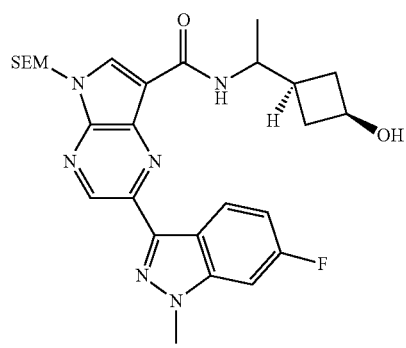

482

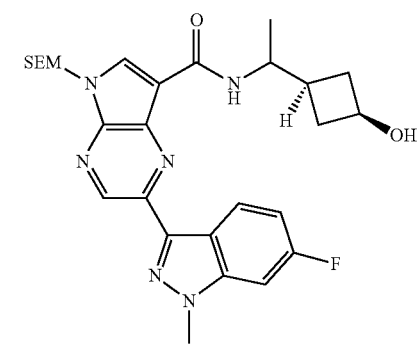

To a solution of 2-(6-fluoro-1-methyl-1H-indazol-3-yl)-5-(2-trimethylsilanylethoxymethyl)-5H-pyrrolo[2,3-b]pyrazine-7-carboxylic acid [1-(cis-3-hydroxy-cyclobutyl)-ethyl]-amide (60 mg, 0.11 mmol) in CH$_2$Cl$_2$ (2 mL) was added TFA (1 mL, 13.0 mmol). The bright yellow-orange reaction mixture was stirred at room temperature for 3 h then concentrated. The residue was redissolved in CH$_2$Cl$_2$ (2 mL) and ethylene diamine (0.4 mL, 6.0 mmol) was added. The reaction mixture was stirred at room temperature for 1 h then quenched with water and diluted with CH$_2$Cl$_2$. A very fine precipitate formed which was collected via filtration. This solid was taken up in MeOH/CH$_2$Cl$_2$ (200 mL) and filtered again, rinsing with MeOH/CH$_2$Cl$_2$. The filtrate was concentrated and triturated with EtOAc/MeOH to afford 28 mg (62%) of 2-(6-fluoro-1-methyl-1H-indazol-3-yl)-5H-pyrrolo[2,3-b]pyrazine-7-carboxylic acid [1-(cis-3-hydroxy-cyclobutyl)-ethyl]-amide as a light yellow solid. MS: (M+H)$^+$= 409; $^1$H NMR (DMSO-d$_6$, 300 MHz): δ (ppm) 9.08 (s, 1H), 8.37-8.48 (m, 2H), 7.96 (d, J=8.7 Hz, 1H), 7.70 (dd, J=9.8, 1.9 Hz, 1H), 7.18 (td, J=9.1, 2.3 Hz, 1H), 4.92 (br. s., 1H), 4.14 (s, 3H), 4.04-4.13 (m, 1H), 3.87 (br. s., 1H), 2.14-2.34 (m, 2H), 1.78-1.93 (m, 1H), 1.58 (quin, J=9.8 Hz, 2H), 1.19 (d, J=6.8 Hz, 3H).

Example 74

2-(6-Fluoro-1-methyl-1H-indazol-3-yl)-5H-pyrrolo[2,3-b]pyrazine-7-carboxylic acid [1-(trans-3-cyano-cyclobutyl)-ethyl]-amide

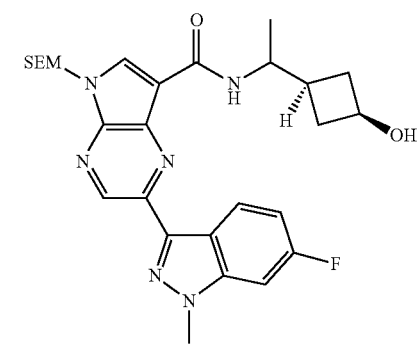

Step 1

Methanesulfonic acid cis-3-(1-{[2-(6-fluoro-1-methyl-1H-indazol-3-yl)-5-(2-trimethylsilanylethoxymethyl)-5H-pyrrolo[2,3-b]pyrazine-7-carbonyl]-amino}-ethyl)-cyclobutyl ester

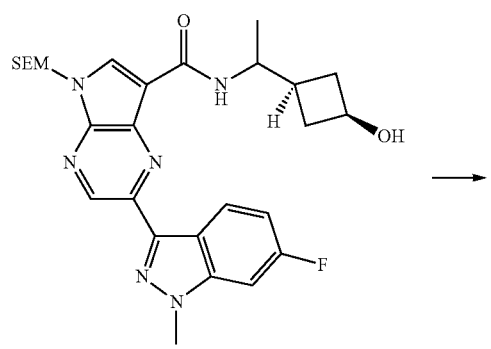

Step 2

2-(6-Fluoro-1-methyl-1H-indazol-3-yl)-5-(2-trimethylsilanyl-ethoxymethyl)-5H-pyrrolo[2,3-b]pyrazine-7-carboxylic acid [1-(trans-3-cyano-cyclobutyl)-ethyl]-amide

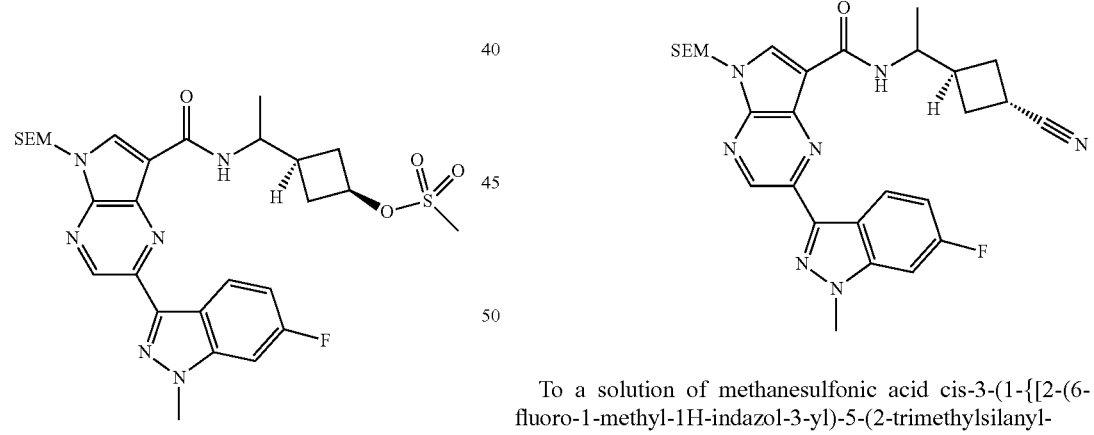

To a partial suspension of 2-(6-fluoro-1-methyl-1H-indazol-3-yl)-5-(2-trimethylsilanylethoxymethyl)-5H-pyrrolo[2,3-b]pyrazine-7-carboxylic acid [1-(cis-3-hydroxy-cyclobutyl)-ethyl]-amide (100 mg, 0.19 mmol) in CH$_2$Cl$_2$ (3 mL) at 0° C. was added triethylamine (39 μL, 0.28 mmol) followed by methanesulfonyl chloride (16 μL, 0.21 mmol). The reaction mixture was stirred at 0° C. for 1 h then quenched with water and extracted with CH$_2$Cl$_2$. The organics were dried over MgSO$_4$ and concentrated to give methanesulfonic acid cis-3-(1-{[2-(6-fluoro-1-methyl-1H-indazol-3-yl)-5-(2-trimethylsilanyl-ethoxymethyl)-5H-pyrrolo[2,3-b]pyrazine-7-carbonyl]-amino}-ethyl)-cyclobutyl ester as an off-white foam which was used without further purification.

To a solution of methanesulfonic acid cis-3-(1-{[2-(6-fluoro-1-methyl-1H-indazol-3-yl)-5-(2-trimethylsilanyl-ethoxymethyl)-5H-pyrrolo[2,3-b]pyrazine-7-carbonyl]-amino}-ethyl)-cyclobutyl ester (crude from step 1, 114 mg, 0.19 mmol) in DMSO (1.5 mL) at room temperature was added potassium cyanide (48 mg, 0.74 mmol). The reaction mixture was heated at 60° C. for 2.5 h. 18-Crown-6 (10 mg, 0.04 mmol) was added and heated was continued at 80° C. for 2 h then at 100° C. overnight. The reaction was cooled to room temperature, quenched with water, and extracted with EtOAc (3×). The combined organics were washed with water (3×) and brine then dried over MgSO$_4$ and concentrated. The residue was purified via chromatography with 30% to 50% EtOAc/hexanes to isolate 46 mg (45%) of 2-(6-fluoro-1-methyl-1H-indazol-3-yl)-5-(2-trimethylsilanyl-ethoxymethyl)-

5H-pyrrolo[2,3-b]pyrazine-7-carboxylic acid [1-(trans-3-cyano-cyclobutyl)-ethyl]-amide as a yellow foam.

Step 3

2-(6-Fluoro-1-methyl-1H-indazol-3-yl)-5H-pyrrolo[2,3-b]pyrazine-7-carboxylic acid [1-(trans-3-cyano-cyclobutyl)-ethyl]-amide

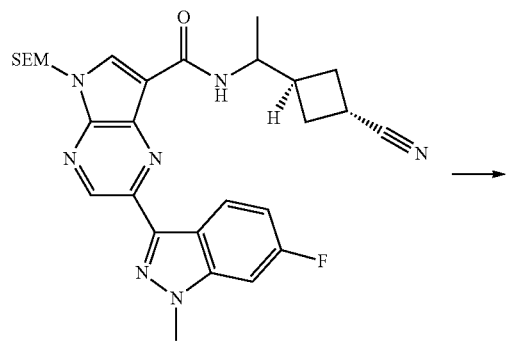

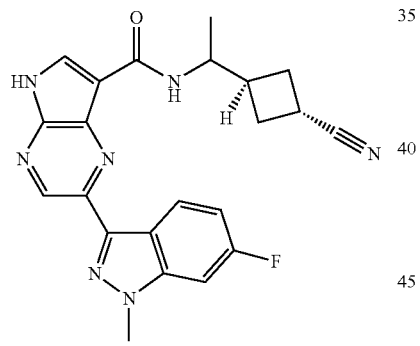

To a solution of 2-(6-fluoro-1-methyl-1H-indazol-3-yl)-5-(2-trimethylsilanylethoxymethyl)-5H-pyrrolo[2,3-b]pyrazine-7-carboxylic acid [1-(trans-3-cyano-cyclobutyl)-ethyl]-amide (44 mg, 0.08 mmol) in CH$_2$Cl$_2$ (2 mL) was added TFA (1 mL, 13.0 mmol). The bright yellow-orange reaction mixture was stirred at room temperature for 3 h then concentrated. The residue was redissolved in CH$_2$Cl$_2$ (2 mL) and ethylene diamine (0.4 mL, 6.0 mmol) was added. The reaction mixture was stirred at room temperature for 1 h then quenched with water and extracted with 5% MeOH/CH$_2$Cl$_2$ (2×). The combined organics were concentrated and the residue was triturated with EtOAc to afford 19 mg (57%) of 2-(6-fluoro-1-methyl-1H-indazol-3-yl)-5H-pyrrolo[2,3-b]pyrazine-7-carboxylic acid [1-(trans-3-cyanocyclobutyl)-ethyl]-amide as a light yellow solid. MS: (M+H)$^+$=418; $^1$H NMR (DMSO-d$_6$, 300 MHz): δ (ppm) 9.08 (s, 1H), 8.43 (s, 1H), 8.40 (dd, J=8.9, 5.5 Hz, 1H), 7.96 (d, J=9.1 Hz, 1H), 7.70 (dd, J=9.8, 2.3 Hz, 1H), 7.29 (td, J=9.1, 1.9 Hz, 1H), 4.19-4.31 (m, 1H), 4.14 (s, 3H), 2.64-2.77 (m, 2H), 2.34-2.45 (m, 1H), 2.22-2.33 (m, 3H), 1.18 (d, J=6.4 Hz, 3H).

Example 75

2-(6-Fluoro-1-methyl-1H-indazol-3-yl)-5H-pyrrolo[2,3-b]pyrazine-7-carboxylic acid [1-(trans-3-hydroxy-cyclobutyl)-ethyl]-amide

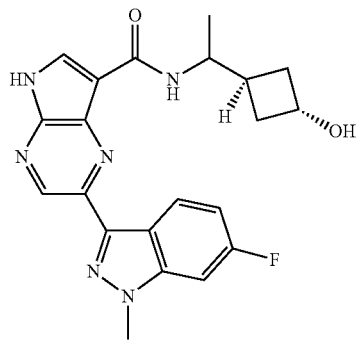 [SMILES: CC(NC(=O)c1c[nH]c2ncc(-c3nn(C)c4cc(F)ccc34)nc12)[C@H]1C[C@H](O)C1]

Step 1

4-Nitrobenzoic acid trans-3-(1-{[2-(6-fluoro-1-methyl-1H-indazol-3-yl)-5-(2-trimethylsilanylethoxymethyl)-5H-pyrrolo[2,3-b]pyrazine-7-carbonyl]-amino}-ethyl)-cyclobutyl ester

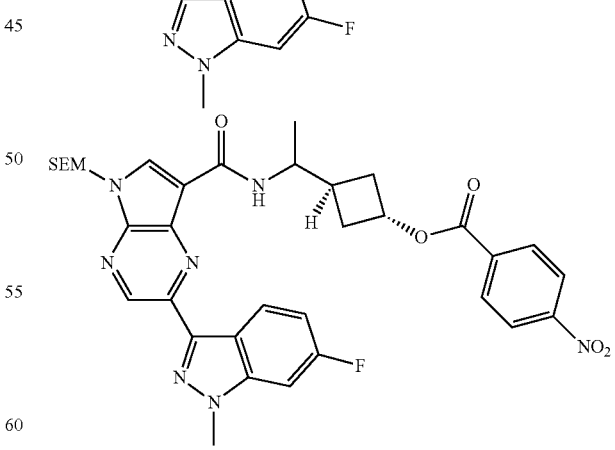

To a solution of 2-(6-fluoro-1-methyl-1H-indazol-3-yl)-5-(2-trimethylsilanylethoxymethyl)-5H-pyrrolo[2,3-b]pyrazine-7-carboxylic acid [1-(cis-3-hydroxy-cyclobutyl)-ethyl]-amide (200 mg, 0.37 mmol) in THF (4 mL) was added 4-nitrobenzoic acid (124 mg, 0.74 mmol) and triphenylphosphine (204 mg, 0.78 mmol). Then the reaction mixture was cooled to 0° C. and diethyl azodicarboxylate (123 µL, 0.78 mmol) was added dropwise. The reaction was stirred at room temperature overnight then diluted with CH$_2$Cl$_2$ (25 mL) and washed with 1.0 M aqueous NaOH. The aqueous phase was back-extracted with CH$_2$Cl$_2$ then the combined organics were dried over MgSO$_4$ and concentrated. The residue was absorbed onto SiO$_2$ and purified via chromatography with 20% to 80% EtOAc/hexanes to provide 250 mg (98%) of 4-nitrobenzoic acid trans-3-(1-{[2-(6-fluoro-1-methyl-1H-indazol-3-yl)-5-(2-trimethylsilanyl-ethoxymethyl)-5H-pyrrolo[2,3-b]pyrazine-7-carbonyl]-amino}-ethyl)-cyclobutyl ester as a white solid.

Step 2

2-(6-Fluoro-1-methyl-1H-indazol-3-yl)-5-(2-trimethylsilanyl-ethoxymethyl)-5H-pyrrolo[2,3-b]pyrazine-7-carboxylic acid [1-(trans-3-hydroxy-cyclobutyl)-ethyl]-amide

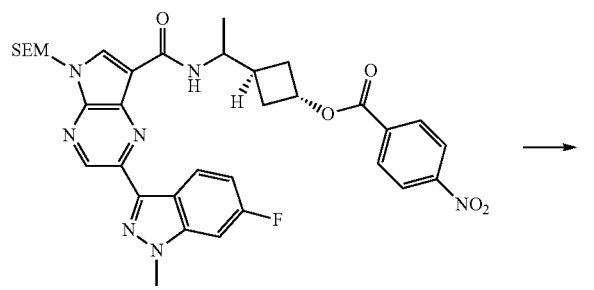

To a suspension of 4-nitrobenzoic acid trans-3-(1-{[2-(6-fluoro-1-methyl-1H-indazol-3-yl)-5-(2-trimethylsilanyl-ethoxymethyl)-5H-pyrrolo[2,3-b]pyrazine-7-carbonyl]-amino}-ethyl)-cyclobutyl ester (250 mg, 0.36 mmol) in THF (12 mL) was added 10% aqueous sodium hydroxide (0.44 mL, 1.09 mmol), water (1 mL), and MeOH (2 mL). The reaction mixture was stirred at room temperature for 30 min then diluted with water and extracted with CH$_2$Cl$_2$ (3×). The combined organics were dried over MgSO$_4$ and concentrated. The residue was purified by silica gel chromatography with 30% to 80% EtOAc/hexanes to afford 140 mg (72%) of 2-(6-fluoro-1-methyl-1H-indazol-3-yl)-5-(2-trimethylsilanyl-ethoxymethyl)-5H-pyrrolo[2,3-b]pyrazine-7-carboxylic acid [1-(trans-3-hydroxy-cyclobutyl)-ethyl]-amide as an off-white solid.

Step 3

2-(6-Fluoro-1-methyl-1H-indazol-3-yl)-5H-pyrrolo[2,3-b]pyrazine-7-carboxylic acid [1-(trans-3-hydroxy-cyclobutyl)-ethyl]-amide

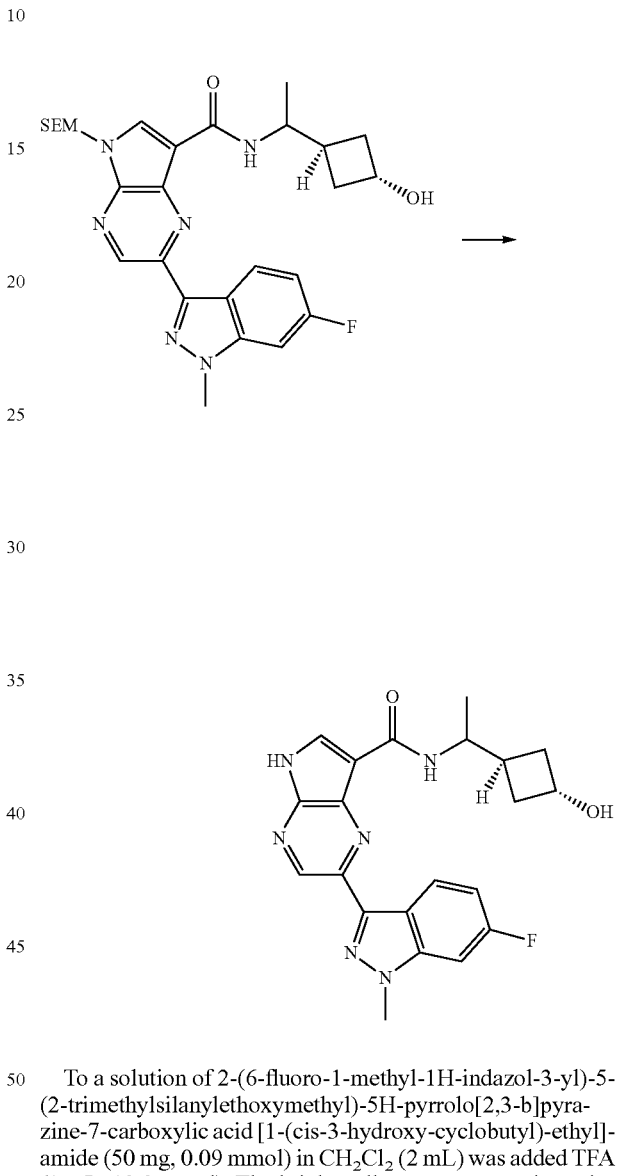

To a solution of 2-(6-fluoro-1-methyl-1H-indazol-3-yl)-5-(2-trimethylsilanylethoxymethyl)-5H-pyrrolo[2,3-b]pyrazine-7-carboxylic acid [1-(cis-3-hydroxy-cyclobutyl)-ethyl]-amide (50 mg, 0.09 mmol) in CH$_2$Cl$_2$ (2 mL) was added TFA (1 mL, 13.0 mmol). The bright yellow-orange reaction mixture was stirred at room temperature for 3 h then concentrated. The residue was redissolved in CH$_2$Cl$_2$ (2 mL) and ethylene diamine (0.4 mL, 6.0 mmol) was added. The reaction mixture was stirred at room temperature for 1 h then quenched with water and extracted with 5% MeOH/CH$_2$Cl$_2$ (2×). The combined organics were concentrated and triturated with EtOAc to afford 19 mg (50%) of 2-(6-fluoro-1-methyl-1H-indazol-3-yl)-5H-pyrrolo[2,3-b]pyrazine-7-carboxylic acid [1-(trans-3-hydroxy-cyclobutyl)-ethyl]-amide as a light yellow solid. MS: (M+H)$^+$=409; $^1$H NMR (DMSO-d$_6$, 300 MHz): δ (ppm) 9.09 (s, 1H), 8.42 (s, 1H), 8.39 (dd, J=8.7, 5.3 Hz, 1H), 7.94 (d, J=8.7 Hz, 1H), 7.71 (dd, J=9.6, 2.1 Hz, 1H), 7.26 (td, J=9.1, 1.9 Hz, 1H), 4.96 (br. s., 1H), 4.14 (s, 3H), 4.07-4.26 (m, 2H), 2.23-2.41 (m, 1H), 1.98-2.19 (m, 3H), 1.84-1.98 (m, 1H), 1.20 (d, J=6.4 Hz, 3H).

Example 76

2-(6-Fluoro-1-methyl-1H-indazol-3-yl)-5H-pyrrolo[2,3-b]pyrazine-7-carboxylic acid [1-(cis-3-cyanocyclobutyl)-ethyl]-amide

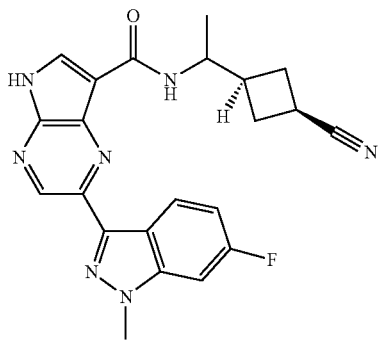 [SMILES: CC(NC(=O)c1c[nH]c2ncc(-c3nn(C)c4cc(F)ccc34)nc12)[C@H]1C[C@@H](C#N)C1]

Step 1

Methanesulfonic acid trans-3-(1-{[2-(6-fluoro-1-methyl-1H-indazol-3-yl)-5-(2-trimethylsilanylethoxymethyl)-5H-pyrrolo[2,3-b]pyrazine-7-carbonyl]-amino}-ethyl)-cyclobutyl ester

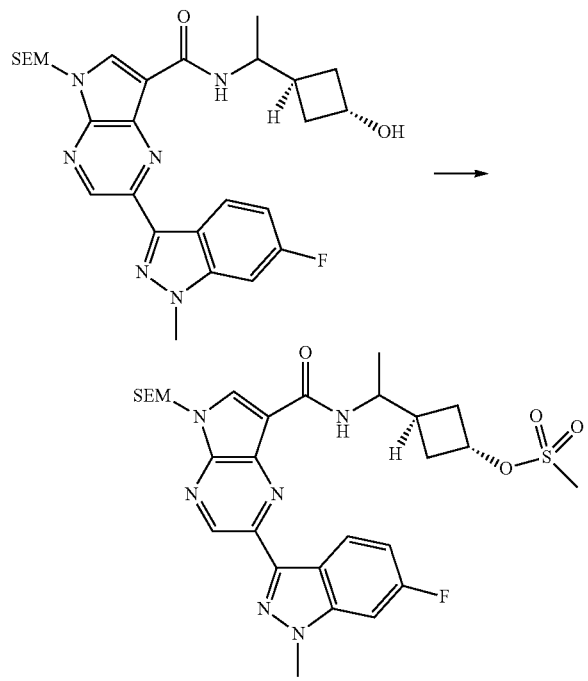

To a partial suspension of 2-(6-fluoro-1-methyl-1H-indazol-3-yl)-5-(2-trimethylsilanylethoxymethyl)-5H-pyrrolo[2,3-b]pyrazine-7-carboxylic acid [1-(trans-3-hydroxy-cyclobutyl)-ethyl]-amide (85 mg, 0.16 mmol) in CH$_2$Cl$_2$ (3 mL) at 0° C. was added triethylamine (33 μL, 0.24 mmol) followed by methanesulfonyl chloride (14 μL, 0.18 mmol). The reaction mixture was stirred at 0° C. for 1 h then quenched with water and extracted with CH$_2$Cl$_2$. The organics were dried over MgSO$_4$ and concentrated to give methanesulfonic acid trans-3-(1-{[2-(6-fluoro-1-methyl-1H-indazol-3-yl)-5-(2-trimethylsilanyl-ethoxymethyl)-5H-pyrrolo[2,3-b]pyrazine-7-carbonyl]-amino}-ethyl)-cyclobutyl ester as an off-white foam which was used without further purification.

Step 2

2-(6-Fluoro-1-methyl-1H-indazol-3-yl)-5-(2-trimethylsilanyl-ethoxymethyl)-5H-pyrrolo[2,3-b]pyrazine-7-carboxylic acid [1-(cis-3-cyano-cyclobutyl)-ethyl]-amide

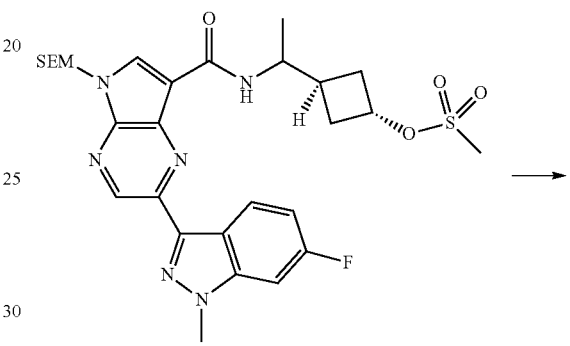

To a solution of methanesulfonic acid trans-3-(1-{[2-(6-fluoro-1-methyl-1H-indazol-3-yl)-5-(2-trimethylsilanyl-ethoxymethyl)-5H-pyrrolo[2,3-b]pyrazine-7-carbonyl]-amino}-ethyl)-cyclobutyl ester (crude from step 1, 97 mg, 0.16 mmol) in DMSO (1.5 mL) at room temperature was added potassium cyanide (41 mg, 0.63 mmol) and 18-crown-6 (8 mg, 0.03 mmol). The reaction mixture was heated at 100° C. overnight then cooled to room temperature, quenched with water, and extracted with EtOAc (3×). The combined organics were washed with water (3×) and brine then dried over MgSO$_4$ and concentrated. The residue was purified via chromatography with 20% to 50% EtOAc/hexanes to isolate 34 mg (40%) of 2-(6-fluoro-1-methyl-1H-indazol-3-yl)-5-(2-trimethylsilanyl-ethoxymethyl)-5H-pyrrolo[2,3-b]pyrazine-7-carboxylic acid [1-(cis-3-cyano-cyclobutyl)-ethyl]-amide as a yellow foam.

Step 3

2-(6-Fluoro-1-methyl-1H-indazol-3-yl)-5H-pyrrolo[2,3-b]pyrazine-7-carboxylic acid [1-(cis-3-cyanocyclobutyl)-ethyl]-amide

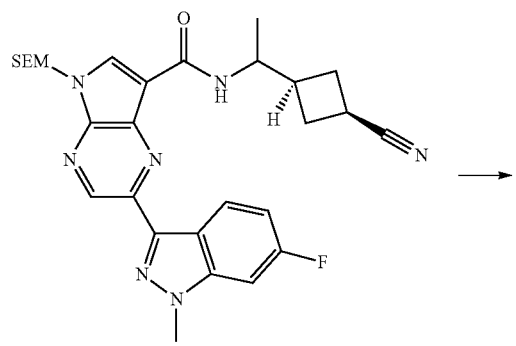

To a solution of 2-(6-fluoro-1-methyl-1H-indazol-3-yl)-5-(2-trimethylsilanylethoxymethyl)-5H-pyrrolo[2,3-b]pyrazine-7-carboxylic acid [1-(cis-3-cyano-cyclobutyl)-ethyl]-amide (34 mg, 0.06 mmol) in CH$_2$Cl$_2$ (2 mL) was added TFA (1 mL, 13.0 mmol). The bright yellow-orange reaction mixture was stirred at room temperature for 3 h then concentrated. The residue was redissolved in CH$_2$Cl$_2$ (2 mL) and ethylene diamine (0.4 mL, 6.0 mmol) was added. The reaction mixture was stirred at room temperature for 1 h then concentrated directly purified via silica gel chromatography with 50% to 100% EtOAc/hexanes to 5% MeOH/EtOAc to afford 15 mg (58%) of 2-(6-fluoro-1-methyl-1H-indazol-3-yl)-5H-pyrrolo[2,3-b]pyrazine-7-carboxylic acid [1-(cis-3-cyanocyclobutyl)-ethyl]-amide as a white solid. MS: (M+H)$^+$=418; $^1$H NMR (DMSO-d$_6$, 300 MHz): δ (ppm) 12.86 (br. s., 1H), 9.08 (s, 1H), 8.44 (s, 1H), 8.40 (dd, J=9.1, 5.3 Hz, 1H), 7.98 (d, J=8.7 Hz, 1H), 7.70 (dd, J=9.8, 1.9 Hz, 1H), 7.25 (td, J=9.0, 2.1 Hz, 1H), 4.17-4.28 (m, 1H), 4.14 (s, 3H), 3.20 (t, J=8.7 Hz, 1H), 2.30-2.46 (m, 3H), 2.04-2.20 (m, 2H), 1.18 (d, J=6.8 Hz, 3H).

Example 77

2-Isoquinolin-1-yl)-5H-pyrrolo[2,3-b]pyrazine-7-carboxylic acid [(R)-2-(3-cyano-azetidin-1-yl)-1-methyl-2-oxo-ethyl]-amide

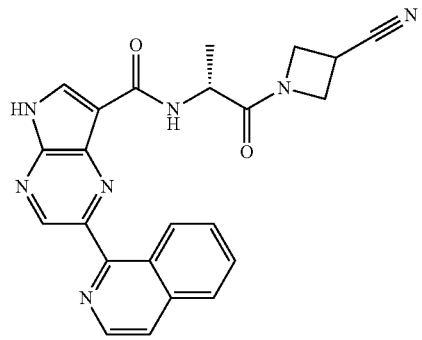 [SMILES: C[C@@H](NC(=O)c1c[nH]c2ncc(-c3nccc4ccccc34)nc12)C(=O)N1CC(C#N)C1]

Step 1

2-Isoquinolin-1-yl-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide

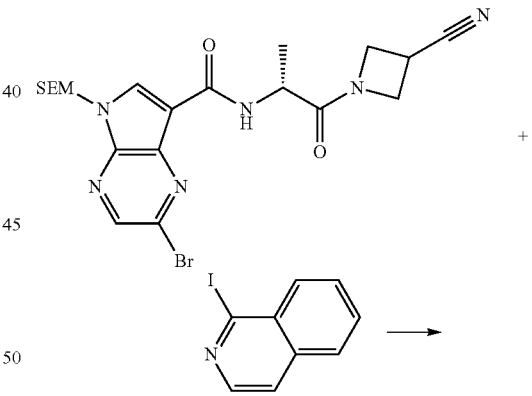

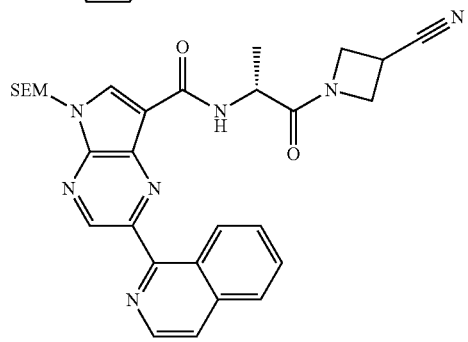

To a solution of hexamethylditin (90 mg, 0.28 mmol) and 2-bromo-5-(2-trimethylsilanylethoxymethyl)-5H-pyrrolo[2, 3-b]pyrazine-7-carboxylic acid [(R)-2-(3-cyano-azetidin-1-yl)-1-methyl-2-oxo-ethyl]-amide (100 mg, 0.20 mmol) in toluene (2 mL) was added Pd(Ph$_3$P)$_4$ (23 mg, 0.02 mmol). A stream of nitrogen gas was gently bubbled through the reaction mixture for 15 min then it was heated to 95° C. After 1.5 h 1-iodoisoquinoline (50 mg, 0.20 mmol) and Pd(Ph$_3$P)$_4$ (23 mg, 0.02 mmol) were added as solids in one portion. Heating was continued at 95° C. for 1.5 h and additional 1-iodoisoquinoline (25 mg, 0.10 mmol), DMF (0.5 mL) and copper (I) iodide (5 mg) were added. The reaction mixture was heated at 95° C. overnight. Additional 1-iodoquinoline (25 mg, 0.10 mmol) and Pd(Ph$_3$P)$_4$ (23 mg, 0.02 mmol) were added and heating was continued for 8 h. The reaction was cooled to room temperature, quenched with water, and extracted with EtOAc (3×). The combined organics were washed with water (3×) and brine, then dried over MgSO$_4$ and concentrated. The residue was purified by silica gel chromatography with 30% to 80% EtOAc/hexanes to afford 52 mg (48%) of 2-isoquinolin-1-yl-5-(2-trimethylsilanylethoxymethyl)-5H-pyrrolo[2,3-b]pyrazine-7-carboxylic acid [(R)-2-(3-cyano-azetidin-1-yl)-1-methyl-2-oxo-ethyl]-amide as a yellow foam.

Step 2

2-Isoquinolin-1-yl)-5H-pyrrolo[2,3-b]pyrazine-7-carboxylic acid [(R)-2-(3-cyano-azetidin-1-yl)-1-methyl-2-oxo-ethyl]-amide

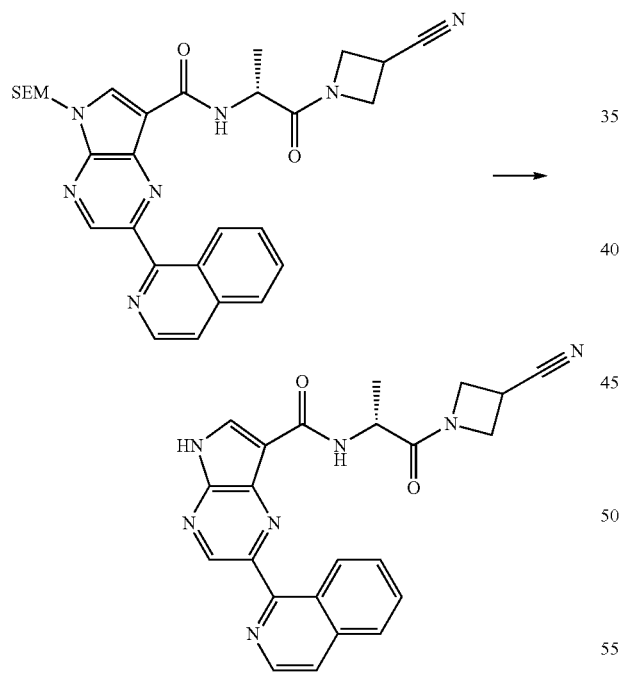

To a solution of 2-isoquinolin-1-yl-5-(2-trimethylsilanylethoxymethyl)-5H-pyrrolo[2,3-b]pyrazine-7-carboxylic acid [(R)-2-(3-cyano-azetidin-1-yl)-1-methyl-2-oxo-ethyl]-amide (52 mg, 0.094 mmol) in CH$_2$Cl$_2$ (2 mL) was added TFA (1 mL, 13.0 mmol). The reaction mixture was stirred at room temperature for 3 h then concentrated. The residue was redissolved in CH$_2$Cl$_2$ (2 mL) and ethylene diamine (0.4 mL, 6.0 mmol) was added. The reaction mixture was stirred for 1 h then quenched with water and extracted with CH$_2$Cl$_2$. The combined organics were concentrated and the residue was purified by silica gel chromatography with 0% to 5% MeOH/CH$_2$Cl$_2$ (0.5% NH$_4$OH) to afford 17 mg (43%) of 2-isoquinolin-1-yl)-5H-pyrrolo[2,3-b]pyrazine-7-carboxylic acid [(R)-2-(3-cyano-azetidin-1-yl)-1-methyl-2-oxo-ethyl]-amide as an off-white solid. MS (M+H)$^+$=426; mp=180-185° C.; $^1$H NMR (DMSO-d$_6$, 300 MHz): δ (ppm) 13.02 (br. s., 1H), 9.09 (s, 1H), 8.91 (d, J=8.7 Hz, 1H), 8.68 (d, J=5.7 Hz, 1H), 8.55 (d, J=9.1 Hz, 1H), 8.44 (d, J=7.6 Hz, 1H), 8.09 (d, J=7.9 Hz, 1H), 7.98 (d, J=5.7 Hz, 1H), 7.84 (t, J=7.6 Hz, 1H), 7.66-7.77 (m, 1H), 4.40-4.70 (m, 3H), 4.12 (q, J=9.7 Hz, 1H), 3.93-4.04 (m, 1H), 3.74-3.88 (m, 1H), 1.22 (t, J=6.6 Hz, 3H).

Example 78

2-(6-Fluoro-1-methyl-1H-indazol-3-yl)-5H-pyrrolo[2,3-b]pyrazine-7-carboxylic acid ((R)-1-pyridin-2-yl-ethyl)-amide hydrochloride

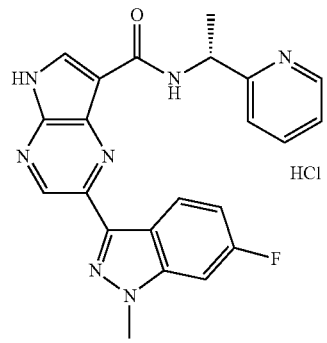 [SMILES: C[C@@H](NC(=O)c1c[nH]c2ncc(-c3nn(C)c4cc(F)ccc34)nc12)c1ccccn1 ; Cl]

Step 1

(R)-2-Methyl-propane-2-sulfinic acid ((R)-1-pyridin-2-yl-ethyl)-amide

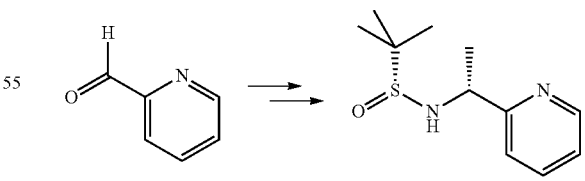

The title compound was prepared from pyridine-2-carboxaldehyde according to the procedure outlined by Kuduk, et. al. *Tetrahedron Lett.* 2004, 45, 6641. The product was obtained as a 10:1 mixture favoring the R$_S$R diastereomer as judged by NMR which is in agreement with the literature. $^1$H NMR (CDCl$_3$, 300 MHz): δ (ppm) 8.55 (d, J=4.9 Hz, 1H), 7.66 (td, J=7.6, 1.7 Hz, 1H), 7.29 (d, J=7.6 Hz, 1H), 7.18 (dd, J=7.6, 4.9 Hz, 1H), 4.83 (d, J=4.9 Hz, 1H), 4.53-4.66 (m, 1H), 1.51 (d, J=6.8 Hz, 3H), 1.26 (s, 9H).

Step 2

(R)-1-Pyridin-2-yl-ethylamine dihydrochloride

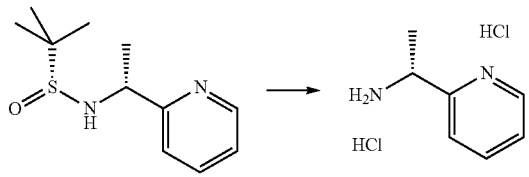

To a solution of (R)-2-methyl-propane-2-sulfinic acid ((R)-1-pyridin-2-yl-ethyl)-amide (1.10 g, 4.86 mmol) in MeOH (12 mL) was added 4.0 M hydrogen chloride in dioxane (3.04 mL, 12.1 mmol). The reaction mixture was stirred at room temperature for 30 min then concentrated and dried under high vacuum to afford 1.0 g of (R)-1-pyridin-2-yl-ethylamine dihydrochloride as a light yellow solid. $^1$H NMR (METHANOL-d$_4$, 300 MHz): δ (ppm) 8.80 (t, J=3.8 Hz, 1H), 8.32 (tdd, J=7.9, 4.5, 1.7 Hz, 1H), 7.88 (dd, J=7.9, 4.5 Hz, 1H), 7.72-7.83 (m, 1H), 4.78 (qd, J=6.9, 4.5 Hz, 1H), 1.73 (dd, J=6.9, 4.5 Hz, 3H). Assume 82% ee based on 10:1 dr of the starting material.

Step 3

2-(6-Fluoro-1-methyl-1H-indazol-3-yl)-5-(2-trimethylsilanyl-ethoxymethyl)-5H-pyrrolo[2,3-b]pyrazine-7-carboxylic acid ((R)-1-pyridin-2-yl-ethyl)-amide

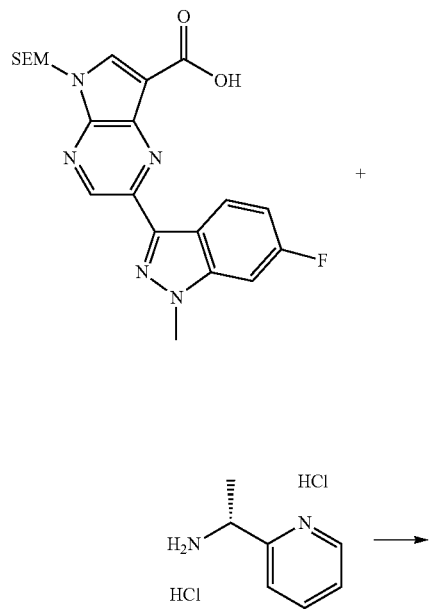

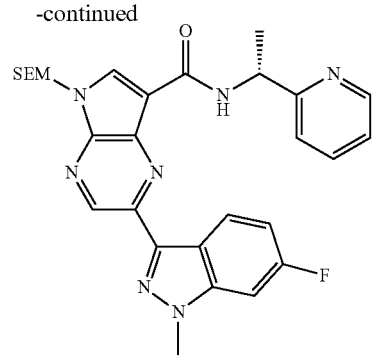

To a solution of (R)-1-pyridin-2-yl-ethylamine dihydrochloride (66 mg, 0.34 mmol) in DMF (2 mL) was added N,N-diisopropylethylamine (0.20 mL, 1.13 mmol), 2-(6-fluoro-1-methyl-1H-indazol-3-yl)-5-(2-trimethylsilanyl-ethoxymethyl)-5H-pyrrolo[2,3-b]pyrazine-7-carboxylic acid (100 mg, 0.23 mmol), and HATU (95 mg, 0.25 mmol). The yellow reaction mixture was stirred at room temperature overnight then quenched with water and extracted with EtOAc (3×). The combined organics were washed with water (3×) and brine then dried over MgSO$_4$ and concentrated. The residue was purified by silica gel chromatography with 50% to 100% EtOAc/hexanes to give 117 mg (95%) of 2-(6-fluoro-1-methyl-1H-indazol-3-yl)-5-(2-trimethylsilanyl-ethoxymethyl)-5H-pyrrolo[2,3-b]pyrazine-7-carboxylic acid ((R)-1-pyridin-2-yl-ethyl)-amide as a white solid.

Step 4

2-(6-Fluoro-1-methyl-1H-indazol-3-yl)-5H-pyrrolo[2,3-b]pyrazine-7-carboxylic acid ((R)-1-pyridin-2-yl-ethyl)-amide hydrochloride

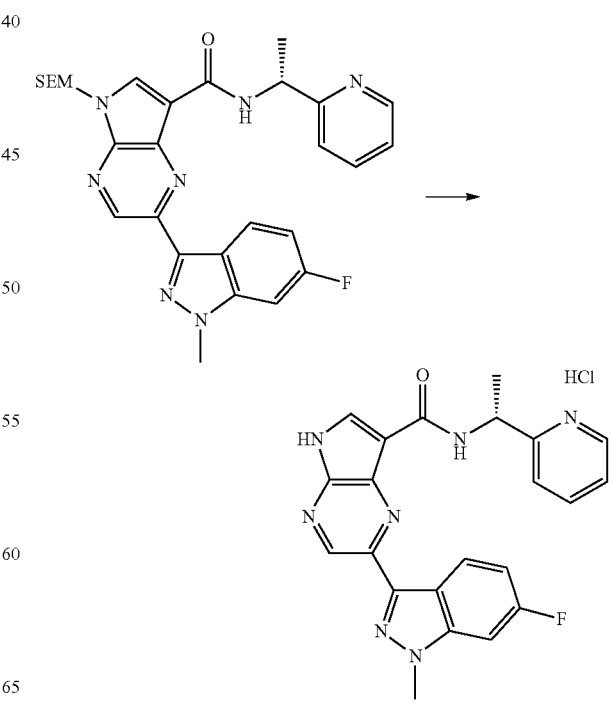

To a solution of 2-(6-fluoro-1-methyl-1H-indazol-3-yl)-5-(2-trimethylsilanylethoxymethyl)-5H-pyrrolo[2,3-b]pyrazine-7-carboxylic acid ((R)-1-pyridin-2-yl-ethyl)-amide (117 mg, 0.21 mmol) in CH$_2$Cl$_2$ (2 mL) was added TFA (1 mL, 13.0 mmol). The bright yellow-orange reaction mixture was stirred at room temperature for 3 h then concentrated. The residue was redissolved in CH$_2$Cl$_2$ (2 mL) and ethylene diamine (0.5 mL, 7.50 mmol) was added. The reaction mixture was stirred for 1 h then chromatographed directly with 50% to 100% EtOAc/hexanes to 5% MeOH/EtOAc. The white solid thus isolated was triturated with EtOAc then suspended in CH$_2$Cl$_2$ and MeOH (1:1, 6 mL). 1.0M HCl in MeOH (2 eq) was added which caused complete dissolution. The solution was concentrated and dried under high vacuum to afford 67 mg (69%) of 2-(6-fluoro-1-methyl-1H-indazol-3-yl)-5H-pyrrolo[2,3-b]pyrazine-7-carboxylic acid ((R)-1-pyridin-2-yl-ethyl)-amide hydrochloride as a light yellow solid. MS (M+H)$^+$=416; $^1$H NMR (DMSO-d$_6$, 300 MHz): δ (ppm) 12.93 (d, J=2.6 Hz, 1H), 9.13 (s, 1H), 8.83 (d, J=7.6 Hz, 1H), 8.73 (dd, J=8.9, 5.5 Hz, 1H), 8.59 (d, J=4.9 Hz, 1H), 8.44 (d, J=3.0 Hz, 1H), 8.07 (br. s., 1H), 7.76 (d, J=7.9 Hz, 1H), 7.68 (dd, J=9.6, 2.1 Hz, 1H), 7.53 (br. s., 1H), 7.05 (td, J=9.1, 1.9 Hz, 1H), 5.44 (quin, J=7.0 Hz, 1H), 4.15 (s, 3H), 1.67 (d, J=6.8 Hz, 3H).

Example 79

2-(6-Fluoro-1-methyl-1H-indazol-3-yl)-5H-pyrrolo[2,3-b]pyrazine-7-carboxylic acid [(R)-1-(4-trifluoromethyl-pyridin-2-yl)-ethyl]-amide

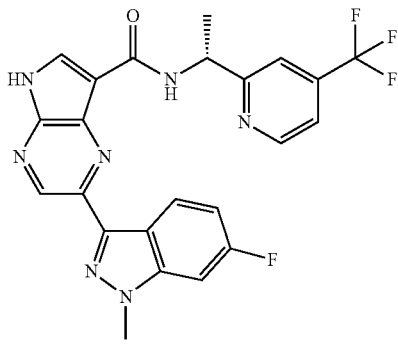 [SMILES: C[C@@H](NC(=O)c1c[nH]c2ncc(-c3nn(C)c4cc(F)ccc34)nc12)c1cc(C(F)(F)F)ccn1]

Step 1

(4-Trifluoromethyl-pyridin-2-yl)-methanol

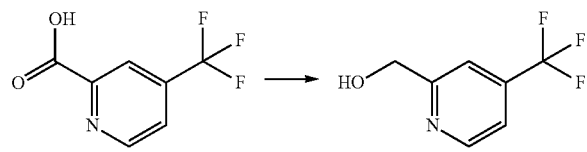 [SMILES: O=C(O)c1cc(C(F)(F)F)ccn1 ; OCc1cc(C(F)(F)F)ccn1]

To a solution of 4-trifluoromethyl-pyridine-2-carboxylic acid (500 mg, 2.62 mmol) in THF (20 mL) at 0° C. was added triethylamine (0.40 mL, 2.88 mmol) followed by ethyl chloroformate (0.28 mL, 2.88 mmol). A thick white precipitate formed. The reaction mixture was stirred at 0° C. for 15 min then a solution of sodium borohydride (297 mg, 7.85 mmol) in water (5 mL) was slowly added via pipet. Vigorous gas evolution was observed and all solids dissolved. The reaction was stirred at 0° C. for 10 min then warmed to room temperature and stirred for 1 h. The reaction was diluted with water and extracted with CH$_2$Cl$_2$ (3×). The combined organics were dried over MgSO$_4$ and concentrated. The residue was purified by chromatography with 20% to 50% EtOAc/hexanes to afford 296 mg (64%) of (4-trifluoromethyl-pyridin-2-yl)-methanol as a colorless oil that freezes just below room temperature. $^1$H NMR (CDCl$_3$, 300 MHz): δ (ppm) 8.76 (d, J=4.9 Hz, 1H), 7.55 (s, 1H), 7.45 (d, J=4.9 Hz, 1H), 4.87 (s, 2H).

Step 2

4-Trifluoromethyl-pyridine-2-carbaldehyde

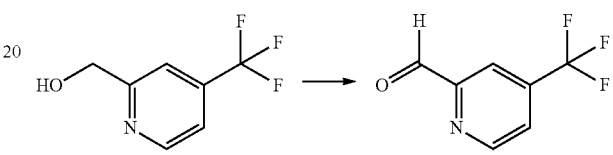

To a solution of (4-trifluoromethyl-pyridin-2-yl)-methanol (290 mg, 1.64 mmol) in CH$_2$Cl$_2$ (15 mL) at room temperature was added Dess-Martin periodinane (764 mg, 1.8 mmol). The reaction mixture was stirred at room temperature for 1 h then quenched with saturated aqueous NaHCO$_3$ (10 mL) and 10% aqueous Na$_2$S$_2$O$_3$ (10 mL). The biphasic mixture was diluted with CH$_2$Cl$_2$ and stirred vigorously for 10 min. The layers were separated and the aqueous layer was extracted with CH$_2$Cl$_2$. The combined organics were dried over MgSO$_4$ and concentrated to give 300 mg of 4-trifluoromethyl-pyridine-2-carbaldehyde as a pale yellow oil which was used without further purification. $^1$H NMR (CDCl$_3$, 300 MHz): δ (ppm) 10.15 (s, 1H), 9.00 (d, J=5.3 Hz, 1H), 8.19 (s, 1H), 7.77 (dd, J=5.3, 1.3 Hz, 1H).

Step 3

(R)-2-Methyl-propane-2-sulfinic acid 1-(4-trifluoromethyl-pyridin-2-yl)-meth-(E)-ylideneamide

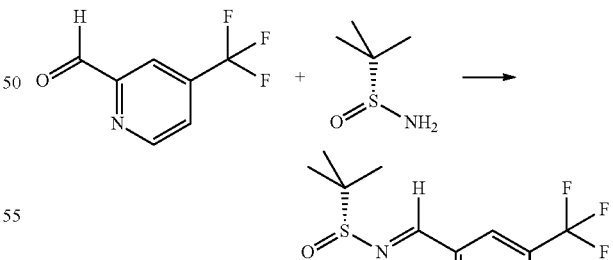

To a solution of 4-trifluoromethyl-pyridine-2-carbaldehyde (287 mg, 1.64 mmol) and (R)-2-methylpropane-2-sulfinamide (209 mg, 1.72 mmol) in CH$_2$Cl$_2$ (10 mL) was added anhydrous copper (II) sulfate (576 mg, 3.61 mmol). The reaction mixture was stirred at room temperature overnight then filtered over a Buchner funnel, rinsing with CH$_2$Cl$_2$. The filtrate was concentrated and the residue was absorbed on SiO₂ and purified by chromatography with 20% to 40% EtOAc/hexanes to give 340 mg (75%) of (R)-2-methyl-propane-2-sulfinic acid 1-(4-trifluoromethyl-pyridin-2-yl)-meth-(E)-ylideneamide as a pale yellow oil.

Step 4

(R)-2-Methyl-propane-2-sulfinic acid [(R)-1-(4-trifluoromethyl-pyridin-2-yl)-ethyl]-amide

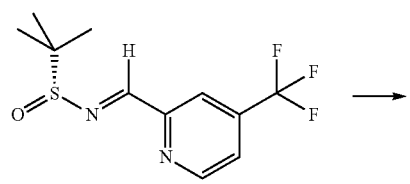

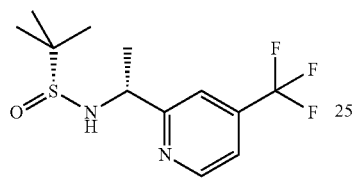

To a solution of (R)-2-methyl-propane-2-sulfinic acid 1-(4-trifluoromethyl-pyridin-2-yl)-meth-(E)-ylideneamide (0.34 g, 1.22 mmol) in THF (5 mL) at −78° C. was slowly added methylmagnesium bromide (3.0 M in Et₂O) (0.73 mL, 2.2 mmol). The reaction mixture was stirred at −78° C. for 30 min then quenched cold with saturated aqueous NH₄Cl. The mixture was warmed to room temperature, diluted with water, and extracted with EtOAc (2×). the combined organics were dried over MgSO₄ and concentrated. NMR analysis showed an approx 8:1 mixture of diastereomers. The residue was purified by chromatography with 50% to 100% EtOAc/hexanes to afford 225 mg (63%) of (R)-2-methyl-propane-2-sulfinic acid [(R)-1-(4-trifluoromethyl-pyridin-2-yl)-ethyl]-amide as a colorless oil. ¹H NMR (CDCl₃, 300 MHz): δ (ppm) 8.75 (d, J=5.3 Hz, 1H), 7.51 (s, 1H), 7.42 (d, J=5.3 Hz, 1H), 4.77 (d, J=4.9 Hz, 1H), 4.67 (quin, J=6.3 Hz, 1H), 1.55 (d, J=6.8 Hz, 3H), 1.27 (s, 9H). The single diastereomer obtained was assigned as R$_S$R based on literature precedent (Kuduk, et. al. *Tetrahedron Lett.* 2004, 45, 6641).

Step 5

(R)-1-(4-Trifluoromethyl-pyridin-2-yl)-ethylamine dihydrochloride

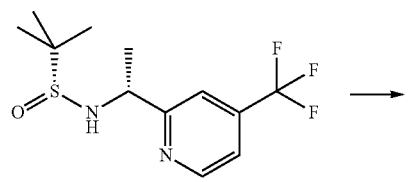

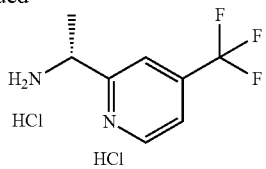

To a solution of (R)-2-methyl-propane-2-sulfinic acid [(R)-1-(4-trifluoromethyl-pyridin-2-yl)-ethyl]-amide (225 mg, 0.76 mmol) in MeOH (4 mL) was added 4.0 M hydrogen chloride in dioxane (0.48 mL, 1.9 mmol). The reaction mixture was stirred at room temperature for 30 min then concentrated and dried under high vacuum to afford 225 mg of (R)-1-(4-trifluoromethyl-pyridin-2-yl)-ethylamine dihydrochloride as a viscous colorless oil which was used without further purification.

Step 6

2-(6-Fluoro-1-methyl-1H-indazol-3-yl)-5-(2-trimethylsilanyl-ethoxymethyl)-5H-pyrrolo[2,3-b]pyrazine-7-carboxylic acid [(R)-1-(4-trifluoromethyl-pyridin-2-yl)-2-yl)-ethyl]-amide

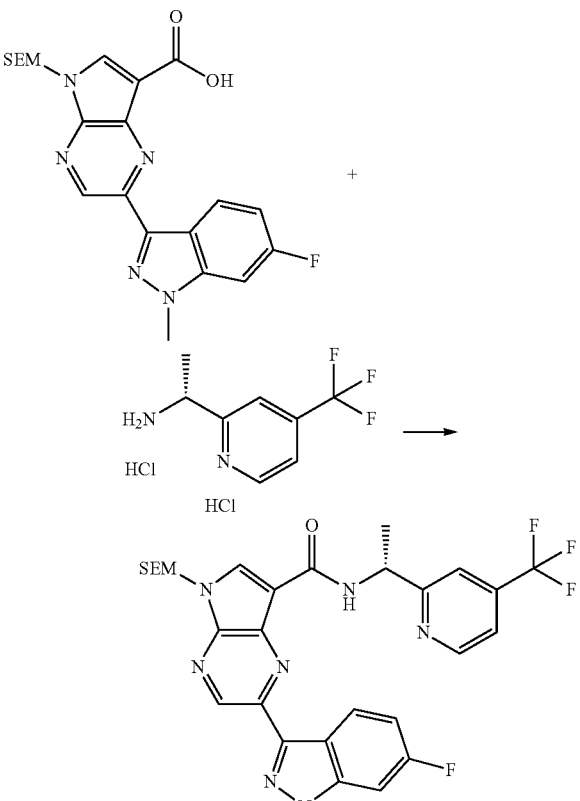

To a solution of (R)-1-(4-trifluoromethyl-pyridin-2-yl)-ethylamine dihydrochloride (89 mg, 0.34 mmol) in DMF (2 mL) was added N,N-diisopropylethylamine (0.20 mL, 1.13 mmol), 2-(6-fluoro-1-methyl-1H-indazol-3-yl)-5-(2-trimethylsilanyl-ethoxymethyl)-5H-pyrrolo[2,3-b]pyrazine-7-carboxylic acid (100 mg, 0.23 mmol), and HATU (95 mg, 0.25 mmol). The yellow reaction mixture was stirred at room temperature overnight then quenched with water and extracted with EtOAc (3×). The combined organics were washed with water (3×) and brine then dried over MgSO$_4$ and concentrated. The residue was purified by silica gel chromatography with 50% to 100% EtOAc/hexanes to give 122 mg (88%) of 2-(6-fluoro-1-methyl-1H-indazol-3-yl)-5-(2-trimethylsilanyl-ethoxymethyl)-5H-pyrrolo[2,3-b]pyrazine-7-carboxylic acid [(R)-1-(4-trifluoromethyl-pyridin-2-yl)-ethyl]-amide as a white solid.

Step 7

2-(6-Fluoro-1-methyl-1H-indazol-3-yl)-5H-pyrrolo[2,3-b]pyrazine-7-carboxylic acid [(R)-1-(4-trifluoromethyl-pyridin-2-yl)-ethyl]-amide

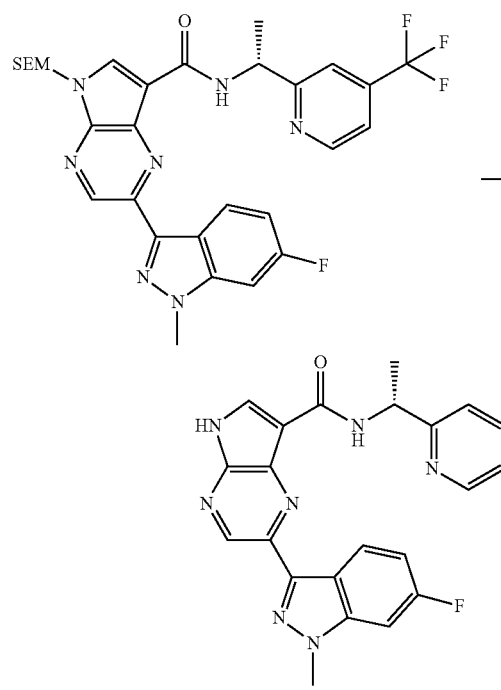

To a solution of 2-(6-fluoro-1-methyl-1H-indazol-3-yl)-5-(2-trimethylsilanylethoxymethyl)-5H-pyrrolo[2,3-b]pyrazine-7-carboxylic acid [(R)-1-(4-trifluoromethyl-pyridin-2-yl)-ethyl]-amide (122 mg, 0.20 mmol) in CH$_2$Cl$_2$ (3 mL) was added TFA (1 mL, 13.0 mmol). The bright yellow-orange reaction mixture was stirred at room temperature for 3 h then concentrated. The residue was redissolved in CH$_2$Cl$_2$ (3 mL) and ethylene diamine (0.5 mL, 7.50 mmol) was added. The reaction mixture was stirred for 1 h then quenched with water and extracted with 5% MeOH/CH$_2$Cl$_2$ (2×). The combined organics were concentrated and triturated with MeOH/CH$_2$Cl$_2$ to isolate 65 mg (68%) of 2-(6-Fluoro-1-methyl-1H-indazol-3-yl)-5H-pyrrolo[2,3-b]pyrazine-7-carboxylic acid [(R)-1-(4-trifluoromethyl-pyridin-2-yl)-ethyl]-amide as an off-white solid. MS: (M+Na)$^+$=506; $^1$H NMR (DMSO-d$_6$, 300 MHz): δ (ppm) 12.79 (br. s., 1H), 9.12 (s, 1H), 8.86 (d, J=7.9 Hz, 1H), 8.71-8.81 (m, 2H), 8.43 (s, 1H), 7.91 (s, 1H), 7.60-7.73 (m, 2H), 7.03 (td, J=9.2, 2.1 Hz, 1H), 5.55 (quin, J=7.3 Hz, 1H), 4.15 (s, 3H), 1.64 (d, J=6.8 Hz, 3H).

Example 80

2-(6-Chloro-1-methyl-1H-indazol-3-yl)-5H-pyrrolo[2,3-b]pyrazine-7-carboxylic acid ((S)-2-cyano-1,2,2-trimethyl-ethyl)-amide

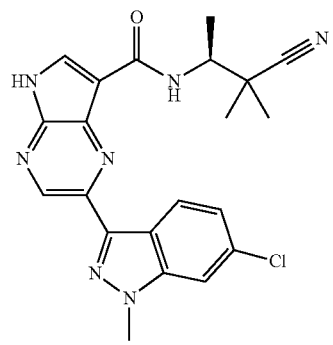 [SMILES: C[C@H](NC(=O)c1c[nH]c2ncc(-c3nn(C)c4cc(Cl)ccc34)nc12)C(C)(C)C#N]

Step 1

(R)-2-Methyl-propane-2-sulfinic acid (E)-ethylideneamide

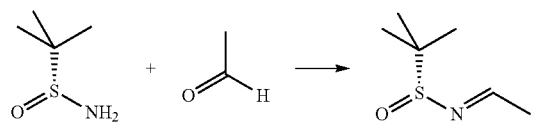

In a flask (R)-2-methyl-propane-2-sulfinic acid amide (4.00 g, 33.0 mmol) was dissolved in CH$_2$Cl$_2$ (14.0 mL). Acetaldehyde (16.7 mL, 297 mmol), MgSO$_4$ (11.9 g, 99.0 mmol) and pyridinium tosylate (415 mg, 1.65 mmol) were added. The reaction mixture was stirred overnight at room temperature, filtered and concentrated to give 5.21 g of (R)-2-methyl-propane-2-sulfinic acid (E)-ethylideneamide as a yellow oil which was used without further purification.

Step 2

(R)-2-Methyl-propane-2-sulfinic acid ((S)-2-cyano-1,2,2-trimethyl-ethyl)-amide

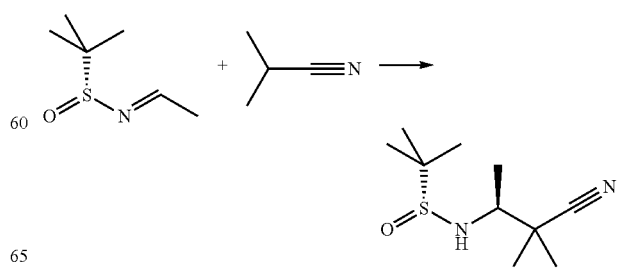

In a flask, isobutyronitrile (6.39 g, 92.4 mmol) was dissolved in diethyl ether (190 mL) and cooled at −78° C. NaHMDS (1.0 M in THF, 99.0 mL, 99.0 mmol) was added and the mixture stirred for 30 min at −78° C. A solution of (R)-2-methyl-propane-2-sulfinic acid (E)-ethylideneamide (crude from step 1, 5.21 g, 33.0 mmol) in THF (50.0 mL) was slowly added. The mixture was stirred at −78° C. for 2 h then allowed to warm to room temperature overnight. The reaction mixture was quenched with saturated aqueous ammonium chloride and extracted with EtOAc. The combined organics were washed with brine, dried over MgSO₄ and concentrated. The residue was purified by SiO₂ chromatography (20-100% EtOAc/hexane) to afford 2.93 g (41%) (R)-2-methyl-propane-2-sulfinic acid ((S)-2-cyano-1,2,2-trimethyl-ethyl)-amide as a light yellow oil. $^1$H NMR (CDCl₃, 300 MHz): δ (ppm) 3.28 (dq, J=8.7, 6.4 Hz, 1H), 3.08 (d, J=8.7 Hz, 1H), 1.45 (d, J=6.4 Hz, 3H), 1.39 (s, 3H), 1.34 (s, 3H), 1.26 (s, 9H).

Step 3

(S)-3-Amino-2,2-dimethyl-butyronitrile hydrochloride

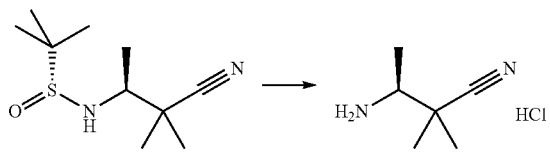

(R)-2-Methyl-propane-2-sulfinic acid (2-cyano-1,2,2-trimethyl-ethyl)-amide (2.93 g, 13.6 mmol) was dissolved in MeOH and HCl (4.0 M in 1,4-dioxane, 6.8 mL, 27.2 mmol) was added. The reaction mixture was stirred at room temperature for 1 h then concentrated to give 1.90 g (94%) of (S)-3-amino-2,2-dimethyl-butyronitrile hydrochloride as a white solid which was used without further purification.

Step 4

2-Bromo-5-(2-trimethylsilanyl-ethoxymethyl)-5H-pyrrolo[2,3-b]pyrazine-7-carboxylic acid ((S)-2-cyano-1,2,2-trimethyl-ethyl)-amide

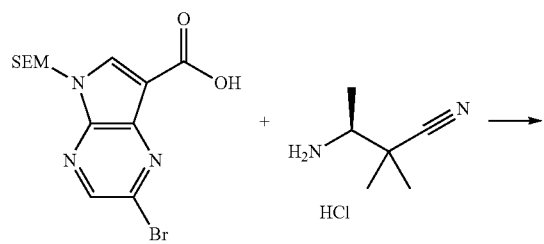

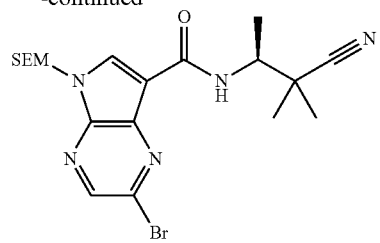

In a flask were combined 2-bromo-5-(2-trimethylsilanylethoxymethyl)-5H-pyrrolo[2,3-b]pyrazine-7-carboxylic acid (1.10 g, 2.95 mmol), (S)-3-amino-2,2-dimethyl-butyronitrile hydrochloride (439 mg, 2.95 mmol), EDC (1.3 g, 6.8 mmol) and HOBt (1.15 g, 6.8 mmol). DMF (27 mL) was added followed by i-Pr₂NEt (3.6 mL, 20.7 mmol). The reaction mixture was stirred at room temperature for 18 h and then quenched with water and extracted with EtOAc. The organics were washed with 10% citric acid, sat'd NaHCO₃, sat'd LiCl, and sat'd NaCl then dried over MgSO₄ and concentrated. The residue was purified by SiO₂ chromatography (50-100% EtOAc/hexane) to give 1.32 g (96%) of 2-bromo-5-(2-trimethylsilanyl-ethoxymethyl)-5H-pyrrolo[2,3-b]pyrazine-7-carboxylic acid ((S)-2-cyano-1,2,2-trimethyl-ethyl)-amide as an off-white powder.

Step 5

2-(6-Chloro-1-methyl-1H-indazol-3-yl)-5-(2-trimethylsilanyl-ethoxymethyl)-5H-pyrrolo[2,3-b]pyrazine-7-carboxylic acid ((S)-2-cyano-1,2,2-trimethyl-ethyl)-amide

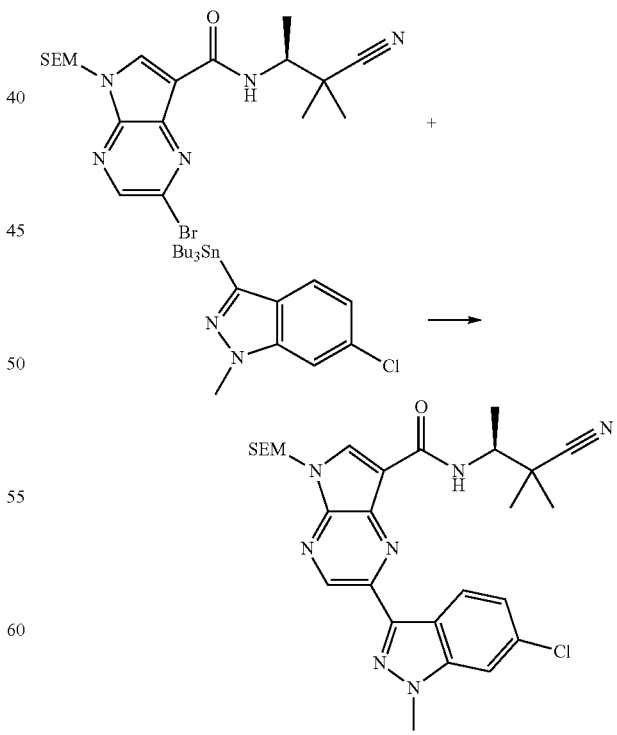

To a solution of 6-tert-butyl-1-methyl-3-tributylstannyl-1H-indazole (222 mg, 0.49 mmol) and 2-bromo-5-(2-trimethylsilanyl-ethoxymethyl)-5H-pyrrolo[2,3-b]pyrazine-7-carboxylic acid ((S)-2-cyano-1,2,2-trimethyl-ethyl)-amide (110 mg, 0.24 mmol) in DMF (1.5 mL) were added Pd(PPh₃)₄ (14 mg, 0.012 mmol) and copper(I) iodide (9 mg, 0.05 mmol). The yellow reaction mixture was purged with argon then heated at 80° C. for 2 h then cooled to room temperature, quenched with sat NH₄Cl and extracted with EtOAc (2×). The combined organics were washed with sat LiCl and brine then dried over MgSO₄ and concentrated. The crude residue was purified by silica gel chromatography with 20% to 50% EtOAc/heptane to isolate 120 mg (92%) of 2-(6-chloro-1-methyl-1H-indazol-3-yl)-5-(2-trimethylsilanyl-ethoxymethyl)-5H-pyrrolo[2,3-b]pyrazine-7-carboxylic acid ((S)-2-cyano-1,2,2-trimethyl-ethyl)-amide as a white powder.

Step 6

2-(6-Chloro-1-methyl-1H-indazol-3-yl)-5H-pyrrolo[2,3-b]pyrazine-7-carboxylic acid ((S)-2-cyano-1,2,2-trimethyl-ethyl)-amide

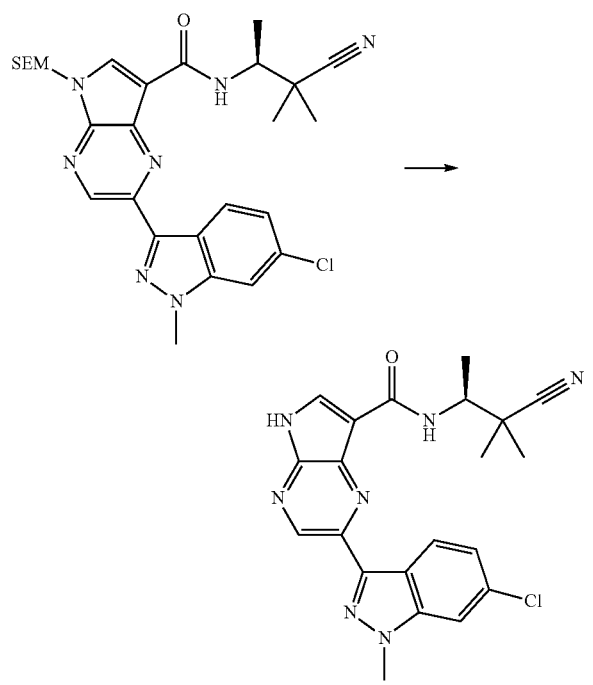

To a solution of 2-(6-chloro-1-methyl-1H-indazol-3-yl)-5-(2-trimethylsilanylethoxymethyl)-5H-pyrrolo[2,3-b]pyrazine-7-carboxylic acid ((S)-2-cyano-1,2,2-trimethyl-ethyl)-amide (120 mg, 0.22 mmol) in CH₂Cl₂ (2 mL) was added TFA (0.75 mL). The reaction mixture was stirred at room temperature for 2 h then concentrated. The residue was redissolved in 10:90:0.5 MeOH/CH₂Cl₂/NH₄OH (3 mL) and stirred at room temperature for 3 h then concentrated. The residue was taken up in 10% MeOH/CH₂Cl₂ and water was added. The resultant precipitate was collected via filtration then triturated with EtOAc to afford 77 mg (84%) of 2-(6-chloro-1-methyl-1H-indazol-3-yl)-5H-pyrrolo[2,3-b]pyrazine-7-carboxylic acid ((S)-2-cyano-1,2,2-trimethyl-ethyl)-amide as a light yellow powder. MS: (M+H)⁺=422; mp=322-328° C.; ¹H NMR (DMSO-d₆, 400 MHz): δ (ppm) 12.78 (s, 1H), 8.99 (s, 1H), 8.38 (s, 1H), 8.34 (d, J=9.1 Hz, 1H), 8.01 (d, J=9.6 Hz, 1H), 7.86 (d, J=1.5 Hz, 1H), 7.19 (dd, J=8.6, 1.5 Hz, 1H), 4.20-4.34 (m, 1H), 4.04 (s, 3H), 1.31 (d, J=6.6 Hz, 3H), 1.28 (s, 3H), 1.25 (s, 3H).

Example 81

2-(6-tert-Butyl-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide

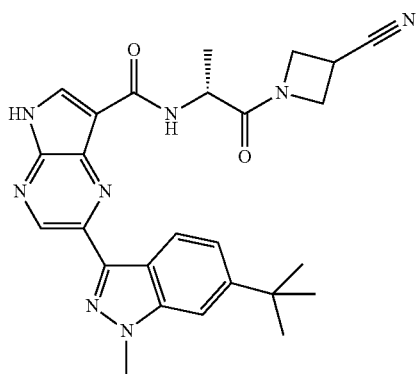 [SMILES: C[C@@H](NC(=O)c1c[nH]c2ncc(-c3nn(C)c4cc(C(C)(C)C)ccc34)nc12)C(=O)N1CC(C#N)C1]

Step 1

5-tert-Butyl-2-methylaniline

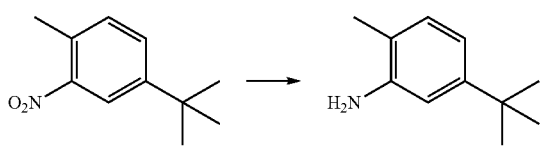

To a solution of 4-tert-butyl-1-methyl-2-nitrobenzene (3.58 g, 18.5 mmol) in MeOH (80 ml) was added 10% Pd on carbon (wet, 358 mg). The reaction mixture was stirred under an atmosphere of hydrogen (balloon) for 4 h then filtered over Celite, rinsing with EtOAc. The filtrate was concentrated to afford 2.48 g (82%) of 5-tert-butyl-2-methylaniline as a brown oil which was used without further purification.

Step 2

6-tert-Butyl-1H-indazole

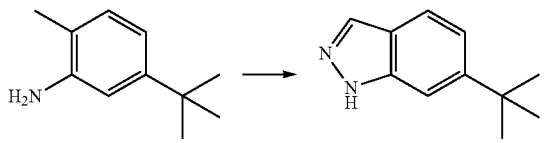

To a solution of 5-tert-butyl-2-methylaniline (2.48 g, 15.2 mmol) in CHCl₃ (40 ml) at 0° C. was slowly added acetic anhydride (3.3 ml, 34.9 mmol). The reaction mixture was warmed to room temperature and stirred for 1 h. Potassium acetate (446 mg, 4.55 mmol) was added followed by slow addition of isoamyl nitrite (4.4 ml, 32.6 mmol). The reaction mixture was heated at reflux overnight. The reaction mixture was cooled to room temperature and concentrated. The residue was dissolved in EtOAc and washed with water, sat'd NaHCO₃ and brine then dried over MgSO₄ and concentrated. The residue was dissolved in THF/MeOH (1:1, 40 mL) and 10% NaOH (4.5 mL) was added. The reaction mixture was stirred at room temperature for 10 min then neutralized with 1.0 M HCl, diluted with water and extracted with EtOAc (2×). The combined organics were washed with brine then dried over MgSO₄ and concentrated. The residue was purified by silica gel chromatography with 20% to 50% EtOAc/heptane to afford 1.02 g (39%) of 6-tert-butyl-1H-indazole as an off-white solid. ¹H NMR (CDCl₃, 300 MHz): δ (ppm) 8.03 (s, 1H), 7.70 (d, J=8.7 Hz, 1H), 7.48 (s, 1H), 7.29 (dd, J=8.7, 1.5 Hz, 1H), 1.40 (s, 9H).

Step 3

6-tert-Butyl-3-iodo-1H-indazole

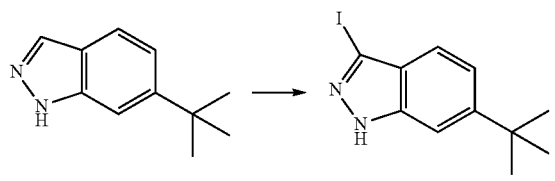

To a solution of 6-tert-butyl-1H-indazole (1.02 g, 5.84 mmol) in DMF (20 ml) at room temperature was added potassium hydroxide (983 mg, 17.5 mmol) and iodine (2.22 g, 8.76 mmol). The maroon reaction mixture was stirred at room temperature for 1 h then quenched with 10% aqueous Na₂S₂O₃ and diluted with water. The mixture was extracted with EtOAc (2×). The combined organics were washed with water, sat LiCl, and sat NaCl, then dried over MgSO₄ and concentrated to afford 1.92 g 6-tert-butyl-3-iodo-1H-indazole as a light brown solid.

Step 4

6-tert-Butyl-3-iodo-1-methyl-1H-indazole

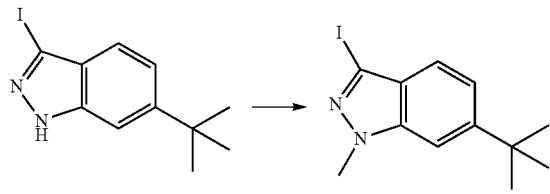

To a solution of 6-tert-butyl-3-iodo-1H-indazole (820 mg, 2.73 mmol) in THF (8 ml) at 0° C. was added KOt-Bu (429 mg, 3.82 mmol). The reaction mixture was stirred at 0° C. for 30 min then added iodomethane (0.24 ml, 3.82 mmol). Stirred at 0° C. for 30 min then warmed to room temperature and stirred for 1.5 h. The reaction was quenched with water and extracted with EtOAc (2×). The combined organics were washed with brine then dried over MgSO₄ and concentrated. The crude residue was purified by silica gel chromatography with 10% to 50% EtOAc/heptane to afford 592 mg (69%) of 6-tert-butyl-3-iodo-1-methyl-1H-indazole as a white solid. ¹H NMR (CDCl₃, 300 MHz): δ (ppm) 7.37-7.43 (m, 1H), 7.31 (d, J=9.8 Hz, 2H), 4.10 (s, 3H), 1.41 (s, 9H). The minor 6-tert-butyl-3-iodo-2-methyl-1H-indazole regioisomer was also observed but not isolated.

Step 5

6-tert-Butyl-1-methyl-3-tributylstannanyl-1H-indazole

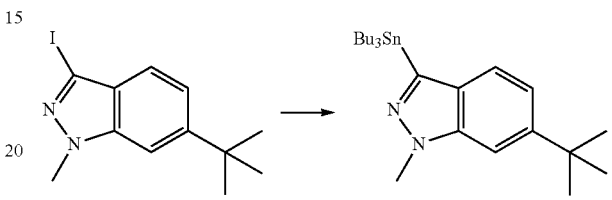

To a solution of 6-tert-butyl-3-iodo-1-methyl-1H-indazole (150 mg, 0.45 mmol) in THF (3 mL) at 0° C. was slowly added isopropylmagnesium chloride (2.0 M in THF, 0.27 mL, 0.54 mmol). The bright yellow heterogeneous reaction mixture was stirred at 0° C. for 1 h then tributylchlorostannane (0.15 mL, 0.54 mmol) was added dropwise. Stirring was continued at 0° C. for 20 min then at room temperature for 3 h. The reaction mixture was quenched with water and extracted with EtOAc (2×). The combined organics were washed with brine then dried over MgSO₄ and concentrated to afford 6-tert-butyl-1-methyl-3-tributylstannanyl-1H-indazole as a viscous yellow oil which was used in the next step without further purification.

Step 6

2-(6-tert-Butyl-1-methyl-1H-indazol-3-yl)-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide

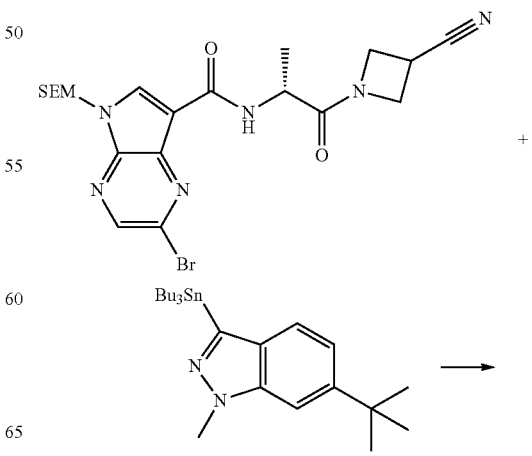

509
-continued

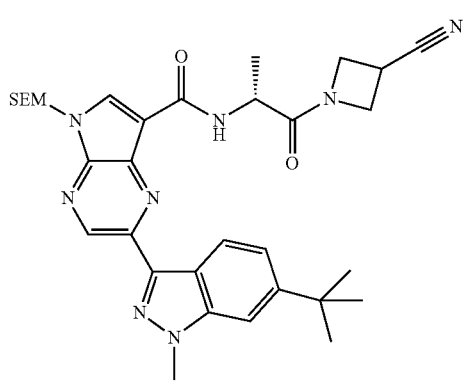

To a solution of 6-tert-butyl-1-methyl-3-tributylstannyl-1H-indazole (crude from Step 5, 217 mg, 0.45 mmol) and 2-bromo-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide (125 mg, 0.25 mmol) in DMF (1.5 mL) were added Pd(PPh$_3$)$_4$ (14 mg, 0.012 mmol) and copper(I) iodide (9 mg, 0.05 mmol). The yellow reaction mixture was purged with argon then heated at 80° C. for 1.5 h then cooled to room temperature, quenched with sat NH$_4$Cl and extracted with EtOAc (2×). The combined organics were washed with sat LiCl and brine then dried over MgSO$_4$ and concentrated. The crude residue was purified by silica gel chromatography with 50% to 100% EtOAc/heptane to isolate 129 mg (85%) of 2-(6-tert-butyl-1-methyl-1H-indazol-3-yl)-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide as a white solid.

Step 7

2-(6-tert-Butyl-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide

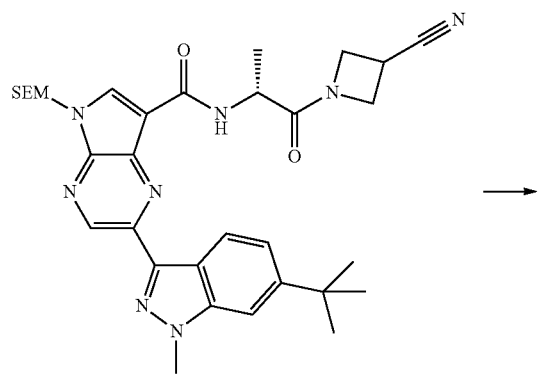

→

510
-continued

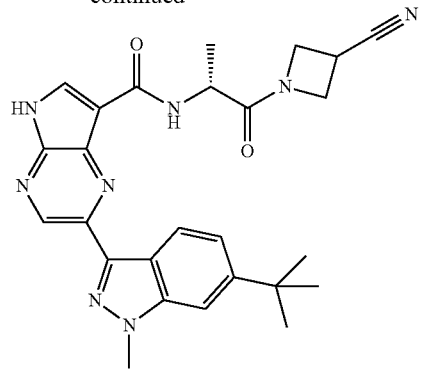

To a solution of 2-(6-tert-butyl-1-methyl-1H-indazol-3-yl)-5-(2-trimethylsilanylethoxymethyl)-5H-pyrrolo[2,3-b]pyrazine-7-carboxylic acid [(R)-2-(3-cyano-azetidin-1-yl)-1-methyl-2-oxo-ethyl]-amide (129 mg, 0.21 mmol) in CH$_2$Cl$_2$ (2 mL) was added TFA (0.75 mL). The reaction mixture was stirred at room temperature for 4 h then concentrated. The residue was redissolved in 10:90:0.5 MeOH/CH$_2$Cl$_2$/NH$_4$OH (3 mL) and stirred at room temperature for 3 h. The reaction mixture was concentrated and the residue was purified by silica gel chromatography with 0% to 5% MeOH/EtOAc to afford 74 mg (73%) of 2-(6-tert-butyl-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide as a light yellow powder. MS: (M+H)$^+$=485; mp=180-195° C.; $^1$H NMR (CDCl$_3$, 400 MHz): δ (ppm) 10.08-10.28 (m, 1H), 9.02-9.14 (m, 1H), 8.65 (d, J=7.1 Hz, 1H), 8.46 (d, J=8.6 Hz, 1H), 7.99-8.13 (m, 1H), 7.40-7.49 (m, 1H), 7.36 (s, 1H), 4.86-5.08 (m, 1H), 4.23-4.76 (m, 4H), 4.11 (s, 3H), 3.52-3.59 (m, 1H), 1.55-1.71 (m, 3H), 1.48 (s, 9H).

Example 82

2-(1,6-Dimethyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide

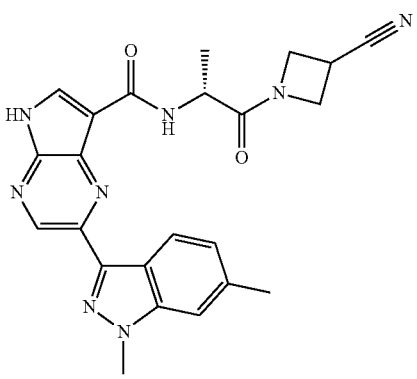 [SMILES: Cc1ccc2c(-c3cnc4[nH]cc(C(=O)N[C@H](C)C(=O)N5CC(C#N)C5)c4n3)nn(C)c2c1]

Prepared according to the procedure outlined in Example 81, Steps 3-7, substituting 6-methyl-1H-indazole for 6-tert-butyl-1H-indazole in Step 3. MS: (M+H)$^+$=443; mp=260-275° C.; $^1$H NMR (DMSO-d$_6$, 400 MHz): δ (ppm) 9.23 (s, 1H), 8.63 (d, J=8.1 Hz, 1H), 8.59 (d, J=8.1 Hz, 1H), 8.54 (d, J=11.6 Hz, 1H), 7.63 (s, 1H), 7.17-7.27 (m, 1H), 4.59-4.89

(m, 3H), 4.26-4.35 (m, 1H), 4.23 (s, 3H), 4.17 (dd, J=9.6, 6.1 Hz, 1H), 3.91-3.97 (m, 1H), 1.52 (t, J=6.3 Hz, 3H).

Example 83

2-(6-Fluoro-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide

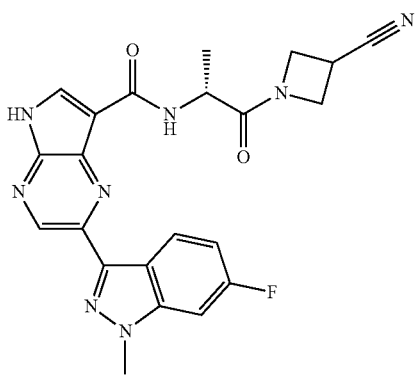 [SMILES: C[C@@H](NC(=O)c1c[nH]c2ncc(-c3nn(C)c4cc(F)ccc34)nc12)C(=O)N1CC(C#N)C1]

Prepared according to the procedure outlined in Example 81, Steps 3-7, substituting 6-fluoro-1H-indazole for 6-tert-butyl-1H-indazole in Step 3. MS: (M+H)$^+$=447; mp=270-277° C.; $^1$H NMR (DMSO-d$_6$, 400 MHz): δ (ppm) 12.91 (br. s., 1H), 9.15 (s, 1H), 8.71-8.80 (m, 1H), 8.42-8.52 (m, 2H), 7.68 (dd, J=9.9, 2.3 Hz, 1H), 7.13 (d, J=2.0 Hz, 1H), 4.50-4.80 (m, 3H), 4.19-4.29 (m, 1H), 4.16 (s, 3H), 4.11 (dd, J=9.9, 6.3 Hz, 1H), 3.82-3.93 (m, 1H), 1.42 (t, J=6.6 Hz, 3H).

Example 84

2-(6-Methoxy-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide

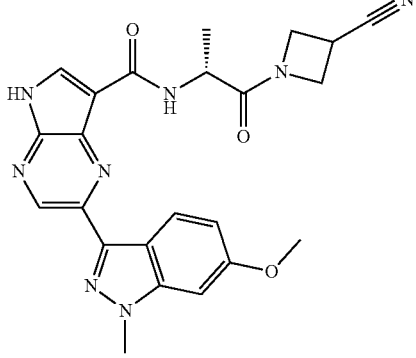

Prepared according to the procedure outlined in Example 81, Steps 3-7, substituting 6-methoxy-1H-indazole for 6-tert-butyl-1H-indazole in Step 3. MS: (M+Na)$^+$=481; mp=220-240° C.; $^1$H NMR (DMSO-d$_6$, 400 MHz): δ (ppm) 12.88 (br. s., 1H), 9.13 (s, 1H), 8.53 (d, J=9.1 Hz, 1H), 8.43-8.51 (m, 2H), 7.22 (d, J=2.0 Hz, 1H), 6.88 (dd, J=8.8, 2.8 Hz, 1H), 4.50-4.78 (m, 3H), 4.22 (td, J=9.5, 5.3 Hz, 1H), 4.14 (s, 3H), 4.05-4.12 (m, 1H), 3.91 (s, 3H), 3.81-3.90 (m, 1H), 1.42 (t, J=6.3 Hz, 3H).

Example 85

2-(6-Chloro-1-ethyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide

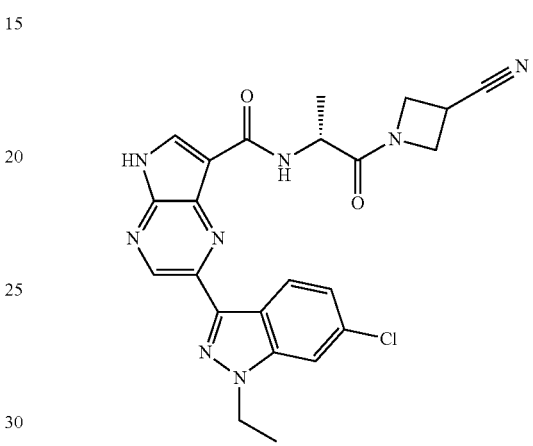

Step 1

6-Chloro-1-ethyl-3-iodo-1H-indazole

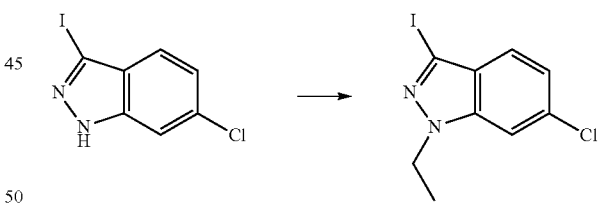

To a solution of 6-chloro-3-iodo-1H-indazole (913 mg, 3.28 mmol) in THF (12 ml) at 0° C. was added KOt-Bu (429 mg, 3.82 mmol). The reaction mixture was stirred at 0° C. for 30 min then added iodoethane (0.37 ml, 4.6 mmol). Stirred at 0° C. for 30 min then warmed to room temperature and stirred for 48 h. The reaction was quenched with water and extracted with EtOAc (2×). The combined organics were washed with brine then dried over MgSO$_4$ and concentrated. The crude residue was purified by silica gel chromatography with 10% to 50% EtOAc/heptane to afford 622 mg (62%) of 6-chloro-1-ethyl-3-iodo-1H-indazole as a white powder. $^1$H NMR (CDCl$_3$, 300 MHz): δ (ppm) 7.37-7.43 (m, 2H), 7.17 (dd, J=8.7, 1.1 Hz, 1H), 4.41 (q, J=7.2 Hz, 2H), 1.51 (t, J=7.2 Hz, 3H). Also isolated 174 mg (17%) of 6-chloro-2-ethyl-3-iodo-2H-indazole as a more polar, minor regioisomer. $^1$H NMR (CDCl$_3$, 300 MHz): δ (ppm) 7.66-7.70 (m, 1H), 7.35 (d, J=9.1 Hz, 1H), 7.04-7.12 (m, 1H), 4.56 (q, J=7.2 Hz, 2H), 1.58 (t, J=7.2 Hz, 3H).

Step 2

6-Chloro-1-ethyl-3-tributylstannanyl-1H-indazole

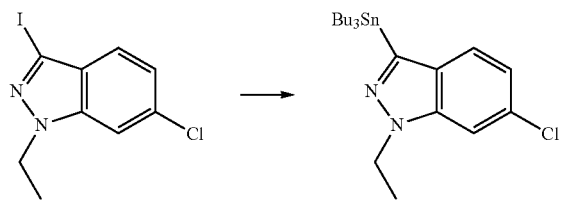

To a solution of 6-chloro-1-ethyl-3-iodo-1H-indazole (150 mg, 0.47 mmol) in THF (3 mL) at 0° C. was slowly added isopropylmagnesium chloride (2.0 M in THF, 0.28 mL, 0.56 mmol). The bright yellow heterogeneous reaction mixture was stirred at 0° C. for 20 min then tributylchlorostannane (0.15 mL, 0.56 mmol) was added dropwise. Stirring was continued at 0° C. for 20 min then at room temperature for 2 h. The reaction mixture was quenched with water and extracted with EtOAc (2×). The combined organics were washed with brine then dried over MgSO$_4$ and concentrated. The exact reaction was repeated once more on the same scale. The residues from the two runs were combined and purified by silica gel chromatography with 10% to 50% EtOAc/heptane (0.5% Et$_3$N) to provide 128 mg (29%) of 6-chloro-1-ethyl-3-tributylstannanyl-1H-indazole as a colorless oil.

Step 3

2-(6-Chloro-1-ethyl-1H-indazol-3-yl)-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide

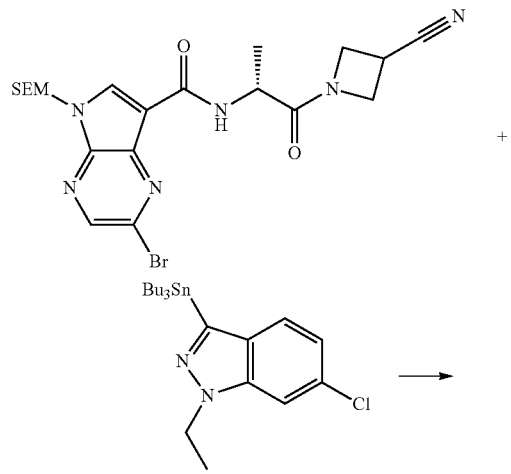

+

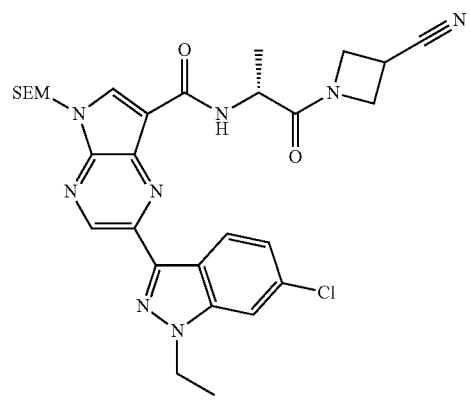

To a solution of 6-chloro-1-ethyl-3-tributylstannyl-1H-indazole (125 mg, 0.27 mmol) and 2-bromo-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide (125 mg, 0.25 mmol) in DMF (1.5 mL) were added Pd(PPh$_3$)$_4$ (14 mg, 0.012 mmol) and copper(I) iodide (9 mg, 0.05 mmol). The yellow reaction mixture was purged with argon then heated at 80° C. for 0.5 h then cooled to room temperature, quenched with sat NH$_4$Cl and extracted with EtOAc (2×). The combined organics were washed with sat LiCl and brine then dried over MgSO$_4$ and concentrated. The crude residue was purified by silica gel chromatography with 50% to 100% EtOAc/heptane to isolate 156 mg of 2-(6-chloro-1-ethyl-1H-indazol-3-yl)-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide as a viscous colorless oil.

Step 4

2-(6-Chloro-1-ethyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide

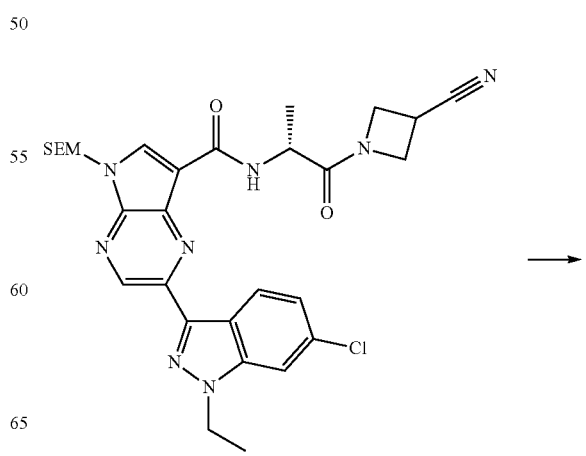

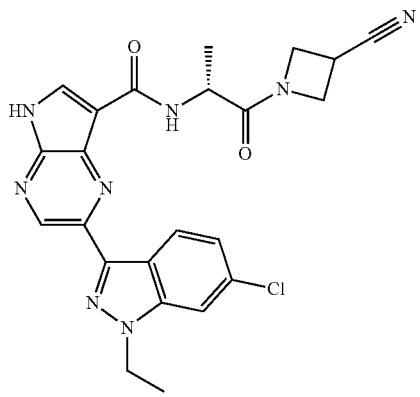 [SMILES: CCn1nc(-c2cnc3[nH]cc(C(=O)N[C@H](C)C(=O)N4CC(C#N)C4)c3n2)c2ccc(Cl)cc21]

To a solution of 2-(6-chloro-1-ethyl-1H-indazol-3-yl)-5-(2-trimethylsilanylethoxymethyl)-5H-pyrrolo[2,3-b]pyrazine-7-carboxylic acid [(R)-2-(3-cyano-azetidin-1-yl)-1-methyl-2-oxo-ethyl]-amide (150 mg, 0.25 mmol) in CH$_2$Cl$_2$ (2 mL) was added TFA (0.75 mL). The reaction mixture was stirred at room temperature for 5 h then concentrated. The residue was redissolved in 10:90:0.5 MeOH/CH$_2$Cl$_2$/NH$_4$OH (3 mL) and stirred at room temperature for 3 h. The reaction mixture was concentrated and the residue was purified by silica gel chromatography with 0% to 5% MeOH/EtOAc followed by trituration with MeOH to afford 88 mg (75%) of 2-(6-chloro-1-ethyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide as a white powder. MS: (M+Na)$^+$=499; mp=248-255° C.; $^1$H NMR (DMSO-d$_6$, 300 MHz): δ (ppm) 12.92 (br. s., 1H), 9.14 (s, 1H), 8.71 (d, J=8.7 Hz, 1H), 8.47 (dd, J=7.6, 3.4 Hz, 2H), 8.02 (s, 1H), 7.25 (d, J=8.7 Hz, 1H), 4.48-4.79 (m, 5H), 4.04-4.28 (m, 2H), 3.77-3.92 (m, 1H), 1.47 (t, J=7.2 Hz, 3H), 1.39 (dd, J=6.8, 4.5 Hz, 3H).

Example 86

2-(6,7-Difluoro-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide

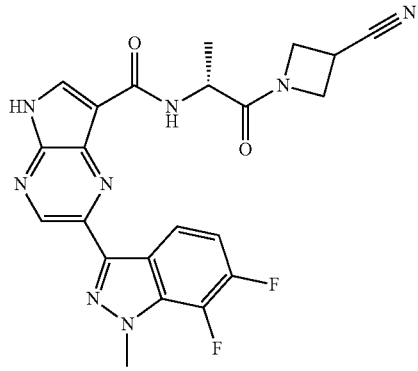 [SMILES: C[C@@H](NC(=O)c1c[nH]c2ncc(-c3nn(C)c4c(F)c(F)ccc34)nc12)C(=O)N1CC(C#N)C1]

Step 1

6,7-Difluoro-1H-indazole

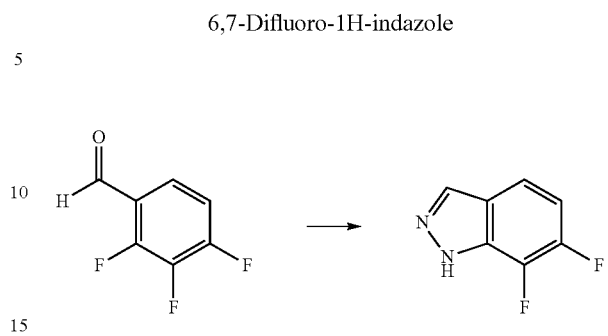

In a microwave vial 2,3,4-trifluorobenzaldehyde (1.5 g, 9.4 mmol) was dissolved in 1,4-dioxane (6 mL) and hydrazine (6 mL, 191 mmol) was added. The vial was sealed and heated under microwave irradiation at 150° C. for 30 min. The reaction was quenched with water and extracted with EtOAc. The organic layer was washed with brine then dried over MgSO$_4$ and concentrated. The residue was purified by silica gel chromatography with 20% to 50% EtOAc/heptane to provide 664 mg (46%) of 6,7-difluoro-1H-indazole as a light brown powder. $^1$H NMR (CDCl$_3$, 300 MHz): δ (ppm) 8.10 (d, J=3.4 Hz, 1H), 7.47 (dd, J=8.9, 4.0 Hz, 1H), 7.05 (ddd, J=10.6, 8.9, 6.6 Hz, 1H).

Step 2

2-(6,7-Difluoro-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide

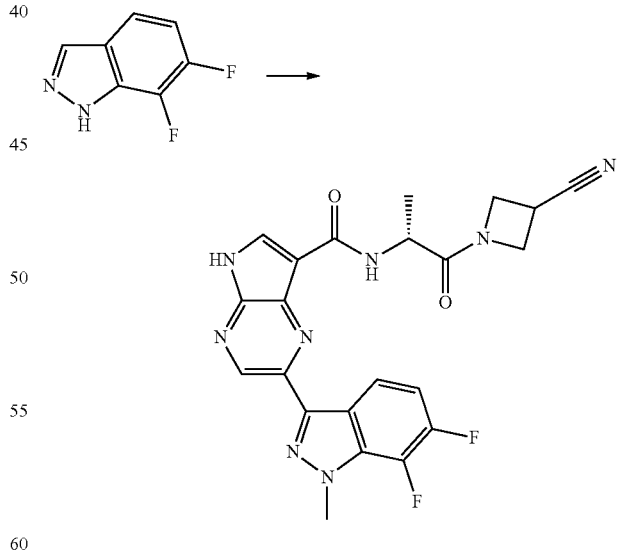

Prepared according to the procedure outlined in Example 81, Steps 3-7, substituting 6,7-difluoro-1H-indazole for 6-tert-butyl-1H-indazole in Step 3. MS: (M+Na)$^+$=487; mp=240-250° C.; $^1$H NMR (DMSO-d$_6$, 300 MHz): δ (ppm) 12.92 (s, 1H), 9.11 (s, 1H), 8.53 (dd, J=9.1, 4.2 Hz, 1H), 8.48 (d, J=6.8 Hz, 1H), 8.38 (d, J=7.6 Hz, 1H), 7.18-7.33 (m, 1H), 4.48-4.78 (m, 3H), 4.28 (s, 3H), 4.16-4.26 (m, 1H), 4.05-4.14 (m, 1H), 3.84 (dd, J=9.3, 5.1 Hz, 1H), 1.38 (t, J=5.9 Hz, 3H).

Example 87

2-(6-Ethyl-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide

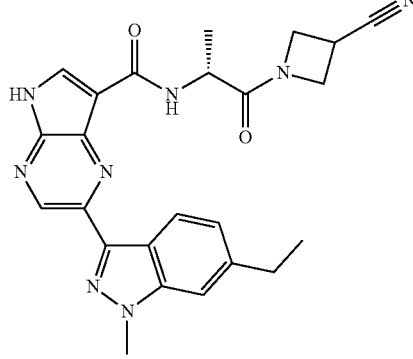

Step 1

6-Vinyl-1H-indazole

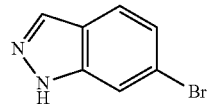 +  →

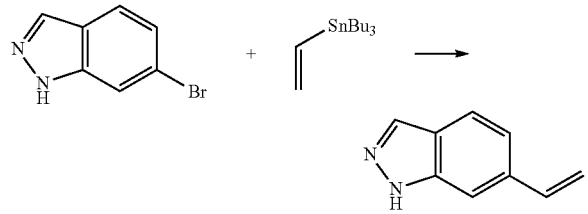

To a suspension of 6-bromo-1H-indazole (600 mg, 3.05 mmol) in toluene (18 ml) and 1,2-dimethoxyethane (6 ml) were added tributyl(vinyl)tin (1.33 ml, 4.57 mmol) and PdCl$_2$(PPh$_3$)$_2$ (214 mg, 0.31 mmol). The reaction was purged with argon then heated at reflux for 3 h. Additional tributyl(vinyl)tin (0.66 ml, 2.28 mmol) and PdCl$_2$(PPh$_3$)$_2$ (107 mg, 0.15 mmol) were added and heating was continued for 1 h. The same reaction was performed on an additional batch of 6-bromo-1H-indazole (200 mg, 1.02 mmol) and the two crude batches were combined. The reactions were diluted with ethyl acetate, washed with water and brine, dried over MgSO$_4$ and concentrated. The residue was purified by silica gel chromatography with 5% to 50% EtOAc/heptane to isolate 350 mg (60%) of 6-vinyl-1H-indazole as a yellow solid. $^1$H NMR (CDCl$_3$, 300 MHz): δ (ppm) 8.07 (s, 1H), 7.72 (d, J=8.3 Hz, 1H), 7.48 (s, 1H), 7.35 (d, J=8.3 Hz, 1H), 6.85 (dd, J=17.4, 11.0 Hz, 1H), 5.86 (d, J=17.4 Hz, 1H), 5.35 (d, J=11.0 Hz, 1H).

Step 2

6-Ethyl-1H-indazole

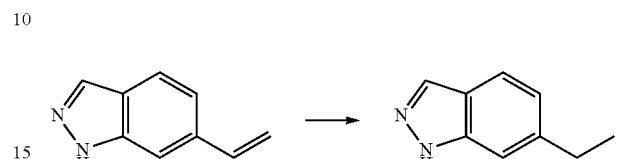

To a solution of 6-vinyl-1H-indazole (350 mg, 2.42 mmol) in MeOH (24 ml) was added 10% Pd on carbon (wet, 443 mg). The reaction mixture was stirred under an atmosphere of hydrogen (balloon) for 2.5 h then filtered over Celite, rinsing with EtOAc. The filtrate was concentrated to afford 305 mg (86%) of 6-ethyl-1H-indazole as a white semi-solid. $^1$H NMR (CDCl$_3$, 300 MHz): δ (ppm) 8.04 (s, 1H), 7.67 (d, J=8.3 Hz, 1H), 7.32 (s, 1H), 7.06 (d, J=8.3 Hz, 1H), 2.80 (q, J=7.6 Hz, 2H), 1.31 (t, J=7.6 Hz, 3H).

Step 3

2-(6-Ethyl-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide

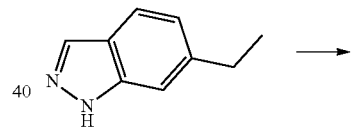 →

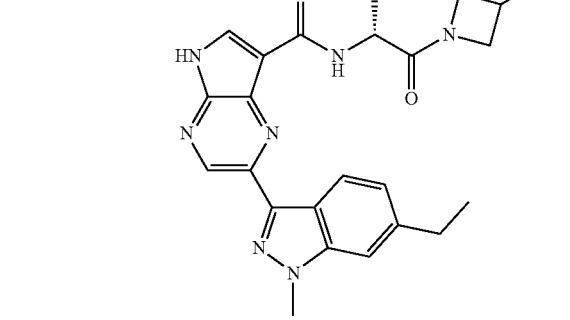

Prepared according to the procedure outlined in Example 81, Steps 3-7, substituting 6-ethyl-1H-indazole for 6-tert-butyl-1H-indazole in Step 3. MS: (M+Na)$^+$=479; mp=185-190° C.; $^1$H NMR (DMSO-d$_6$, 300 MHz): δ (ppm) 12.87 (br. s., 1H), 9.13 (s, 1H), 8.50-8.58 (m, 2H), 8.41-8.49 (m, 2H), 7.54 (s, 1H), 7.15 (dd, J=8.3, 3.0 Hz, 1H), 4.63-4.80 (m, 2H), 4.44-4.63 (m, 2H), 4.00-4.28 (m, 4H), 3.74-3.94 (m, 1H), 2.80 (q, J=7.6 Hz, 2H), 1.43 (dd, J=6.8, 4.2 Hz, 3H), 1.29 (t, J=7.6 Hz, 3H).

Example 88

2-(4,6-Difluoro-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide

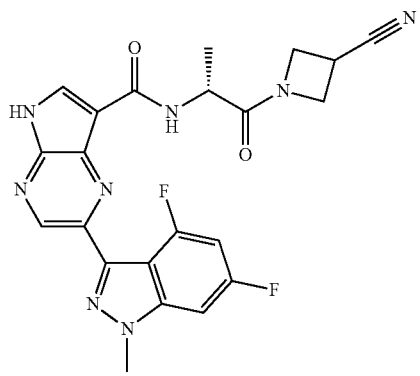 [SMILES: C[C@@H](NC(=O)c1c[nH]c2ncc(-c3nn(C)c4cc(F)cc(F)c34)nc12)C(=O)N1CC(C#N)C1]

Step 1

4,6-Difluoro-1H-indazole

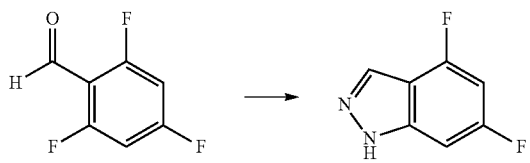 [SMILES: O=Cc1c(F)cc(F)cc1F ; Fc1cc(F)c2cn[nH]c2c1]

To a solution of 2,4,6-trifluorobenzaldehyde (0.80 g, 5.0 mmol) in 1,2-dimethoxyethane (10 mL) were added potassium carbonate (1.04 g, 7.5 mmol) and O-methylhydroxylamine hydrochloride (438 mg, 5.25 mmol). The reaction mixture was heated at 50° C. for 5 h then cooled to room temperature and filtered, rinsing with dichloromethane. The filtrate was concentrated. The residue was dissolved in 1,2-dimethoxyethane (10 mL) and hydrazine (0.17 mL, 5.5 mmol) was added. The reaction mixture was heated at 100° C. for 1.5 h. Additional hydrazine (0.17 mL, 5.5 mmol) was added and heating was continued for 30 min. The reaction was cooled to room temperature, poured into water, and extracted with ethyl acetate. The organic layer was washed with sat LiCl and brine then dried over $MgSO_4$ and concentrated. The residue was purified by silica gel chromatography with 20% to 50% EtOAc/heptane to provide 358 mg (47%) of 4,6-difluoro-1H-indazole as a light yellow solid. $^1H$ NMR (DMSO-$d_6$, 300 MHz): δ (ppm) 13.47 (br. s., 1H), 8.19 (s, 1H), 7.22 (d, J=9.1 Hz, 1H), 6.96 (td, J=10.0, 1.9 Hz, 1H).

Step 2

2-(4,6-Difluoro-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide

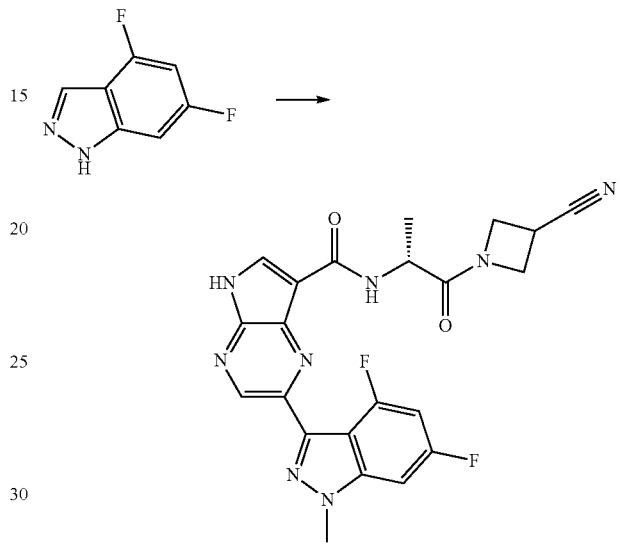

Prepared according to the procedure outlined in Example 81, Steps 3-7, substituting 4,6-difluoro-1H-indazole for 6-tert-butyl-1H-indazole in Step 3. MS: (M+Na)$^+$=487; mp=235-265° C.; $^1H$ NMR (DMSO-$d_6$, 300 MHz): δ (ppm) 12.94 (br. s., 1H), 8.99 (s, 1H), 8.54 (d, J=7.2 Hz, 1H), 8.47 (dd, J=10.8, 3.2 Hz, 1H), 7.55-7.63 (m, 1H), 7.09 (t, J=10.2 Hz, 1H), 4.40-4.68 (m, 3H), 4.15 (s, 3H), 4.08-4.17 (m, 1H), 3.93-4.03 (m, 1H), 3.73-3.86 (m, 1H), 1.35 (t, J=5.7 Hz, 3H).

Example 89

2-(1,6-Dimethyl-1H-pyrazolo[3,4-b]pyridin-3-yl)-5H-pyrrolo[2,3-b]pyrazine-7-carboxylic acid [(R)-2-(3-cyano-azetidin-1-yl)-1-methyl-2-oxo-ethyl]-amide

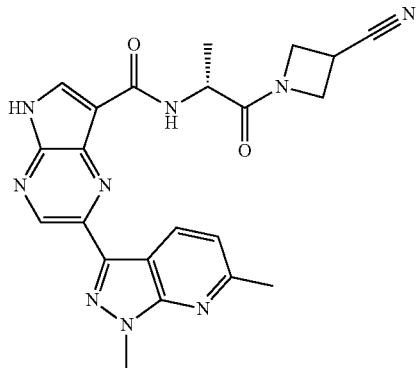 [SMILES: Cc1ccc2c(-c3cnc4[nH]cc(C(=O)N[C@H](C)C(=O)N5CC(C#N)C5)c4n3)nn(C)c2n1]

Step 1

2-Chloro-6-methylpyridine-3-carbaldehyde

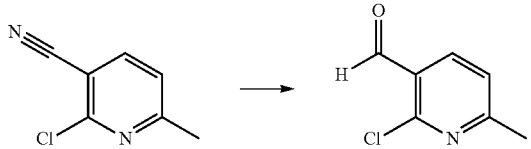

To a solution of 2-chloro-6-methylnicotinonitrile (2.0 g, 13.1 mmol) in dichloromethane (40 mL) at −78° C. was added DIBAL-H (2.92 mL, 16.4 mmol) dropwise. The reaction was stirred at −78° C. for 5 min then allowed to warm to room temperature and stirred for 6 h. The reaction was carefully quenched with 1N HCl (40 mL) and the mixture was heated at reflux for 30 min. After cooling the reaction was made basic with aqueous 10% NaOH and extracted with EtOAc (3×). The combined organics were washed with brine then dried over $MgSO_4$ and concentrated to afford 1.98 g (97%) of 2-chloro-6-methylpyridine-3-carbaldehyde as a light yellow solid.

Step 2

6-Methyl-1H-pyrazolo[3,4-b]pyridine

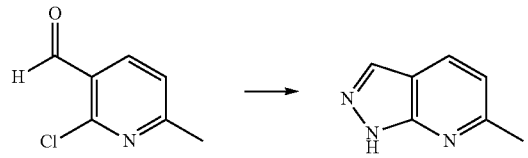

In a microwave vial 2-chloro-6-methylpyridine-3-carbaldehyde (1.98 g, 12.7 mmol) was dissolved in 1,4-dioxane (12 mL) and hydrazine (6.0 mL, 191 mmol) was added. The vial was sealed and heated under microwave irradiation at 150° C. for 1 h. The reaction was quenched with water and extracted with EtOAc. The organic layer was washed with brine then dried over $MgSO_4$ and concentrated. The residue was purified by silica gel chromatography with 50% to 100% EtOAc/heptane to provide 863 mg (41%) of 6-methyl-1H-pyrazolo[3,4-b]pyridine as a light yellow solid. $^1H$ NMR (CDCl$_3$, 300 MHz): δ (ppm) 8.06 (s, 1H), 8.03 (d, J=8.3 Hz, 1H), 7.07 (d, J=8.3 Hz, 1H), 2.79 (s, 3H).

Step 3

2-(1,6-Dimethyl-1H-pyrazolo[3,4-b]pyridin-3-yl)-5H-pyrrolo[2,3-b]pyrazine-7-carboxylic acid [(R)-2-(3-cyano-azetidin-1-yl)-1-methyl-2-oxo-ethyl]-amide

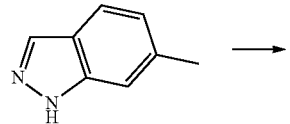

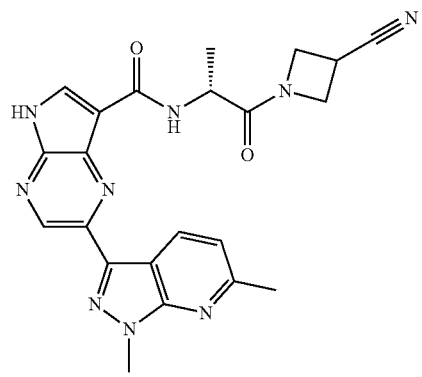

Prepared according to the procedure outlined in Example 81, Steps 3-7, substituting 6-methyl-1H-pyrazolo[3,4-b]pyridine for 6-tert-butyl-1H-indazole in Step 3. MS: (M+Na)$^+$= 466; mp=275-285° C.; $^1H$ NMR (DMSO-d$_6$, 300 MHz): δ (ppm) 12.92 (br. s., 1H), 9.14 (s, 1H), 8.98 (d, J=8.3 Hz, 1H), 8.47 (d, J=6.4 Hz, 2H), 7.22 (dd, J=8.3, 3.4 Hz, 1H), 4.46-4.80 (m, 3H), 4.17-4.30 (m, 1H), 4.13 (s, 3H), 4.07-4.15 (m, 1H), 3.77-3.93 (m, 1H), 2.66 (s, 3H), 1.31-1.48 (m, 3H).

Example 90

2-[6-Chloro-1-(2-hydroxy-ethyl)-1H-indazol-3-yl]-5H-pyrrolo[2,3-b]pyrazine-7-carboxylic acid [(R)-2-(3-cyano-azetidin-1-yl)-1-methyl-2-oxo-ethyl]-amide

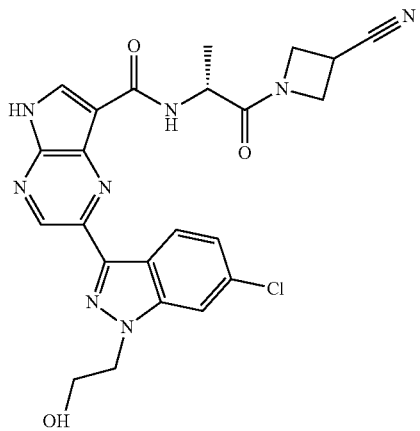 [SMILES: C[C@@H](NC(=O)c1c[nH]c2ncc(-c3nn(CCO)c4cc(Cl)ccc34)nc12)C(=O)N1CC(C#N)C1]

523

Step 1

2-{6-Chloro-1-[2-(tetrahydro-pyran-2-yloxy)-ethyl]-1H-indazol-3-yl}-5-(2-trimethylsilanylethoxymethyl)-5H-pyrrolo[2,3-b]pyrazine-7-carboxylic acid [(R)-2-(3-cyano-azetidin-1-yl)-1-methyl-2-oxo-ethyl]-amide

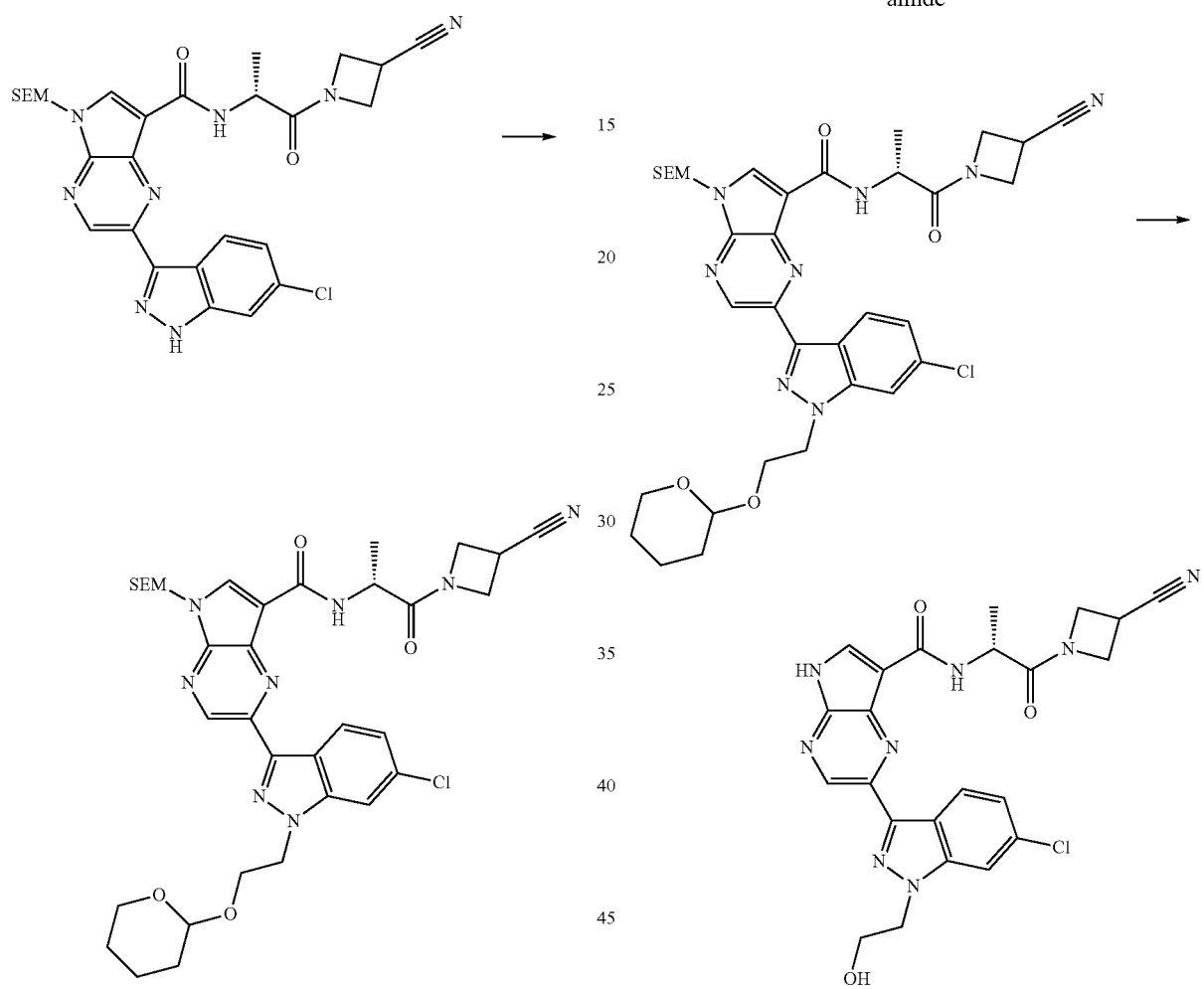

In a round-bottomed flask, 2-(6-chloro-1H-indazol-3-yl)-5-(2-trimethylsilanylethoxymethyl)-5H-pyrrolo[2,3-b]pyrazine-7-carboxylic acid [(R)-2-(3-cyano-azetidin-1-yl)-1-methyl-2-oxo-ethyl]-amide (see Example 23, 120 mg, 0.21 mmol) was dissolved in DMF (1.3 ml). The reaction mixture was cooled to 0° C. and sodium hydride (60% dispersion in mineral oil, 10 mg, 0.25 mmol) was added. The reaction mixture was stirred at 0° C. for 30 min then 2-(2-bromoethoxy)tetrahydro-2H-pyran (47 µl, 0.31 mmol) was added. The reaction mixture was stirred at 0° C. for 1 h and then at room temperature for 4 h. The reaction mixture was quenched with water and extracted with ethyl acetate (2×). The combined organic layers were washed with water, sat LiCl, and brine then dried over MgSO$_4$ and concentrated. The residue was chromatographed over silica gel with 50% to 100% EtOAc/heptane to afford 138 mg (94%) of 2-{6-chloro-1-[2-(tetrahydro-pyran-2-yloxy)-ethyl]-1H-indazol-3-yl}-5-(2-trimethylsilanylethoxymethyl)-5H-pyrrolo[2,3-b]pyrazine-

524

7-carboxylic acid [(R)-2-(3-cyano-azetidin-1-yl)-1-methyl-2-oxo-ethyl]-amide as a viscous yellow oil.

Step 2

2-[6-Chloro-1-(2-hydroxy-ethyl)-1H-indazol-3-yl]-5H-pyrrolo[2,3-b]pyrazine-7-carboxylic acid [(R)-2-(3-cyano-azetidin-1-yl)-1-methyl-2-oxo-ethyl]-amide To a solution of 2-{6-chloro-1-[2-(tetrahydro-pyran-2-yloxy)-ethyl]-1H-indazol-3-yl}-5-(2-trimethylsilanylethoxymethyl)-5H-pyrrolo[2,3-b]pyrazine-7-carboxylic acid [(R)-2-(3-cyano-azetidin-1-yl)-1-methyl-2-oxo-ethyl]-amide (138 mg, 0.20 mmol) in CH$_2$Cl$_2$ (2 mL) was added TFA (0.75 mL). The reaction mixture was stirred at room temperature for 6 h then concentrated. The residue was redissolved in 10:90:0.5 MeOH/CH$_2$Cl$_2$/NH$_4$OH (3 mL) and stirred at room temperature for 3 h. The reaction mixture was concentrated and the residue was purified by silica gel chromatography with 0% to 10% MeOH/CH$_2$Cl$_2$ to afford 63 mg (65%) of 2-[6-chloro-1-(2-hydroxy-ethyl)-1H-indazol-3-yl]-5H-pyrrolo[2,3-b]pyrazine-7-carboxylic acid [(R)-2-(3-cyano-azetidin-1-yl)-1-methyl-2-oxo-ethyl]-amide as a white solid. MS: (M+Na)$^+$=515; mp=225-250° C.; $^1$H NMR (DMSO-d$_6$, 300 MHz): δ (ppm) 12.92 (br. s., 1H), 9.14 (s, 1H), 8.69 (d, J=8.7 Hz, 1H), 8.47 (d, J=7.2 Hz, 2H), 7.95 (d, J=1.5 Hz, 1H), 7.24 (d, J=8.7 Hz, 1H), 4.92 (t, J=5.5 Hz, 1H), 4.49-4.78 (m, 5H), 4.17-4.27 (m, 1H), 4.05-4.15 (m, 1H), 3.83-3.93 (m, 3H), 1.39 (dd, J=6.6, 4.7 Hz, 3H).

Example 91

2-(6-Chloro-1-isopropyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide

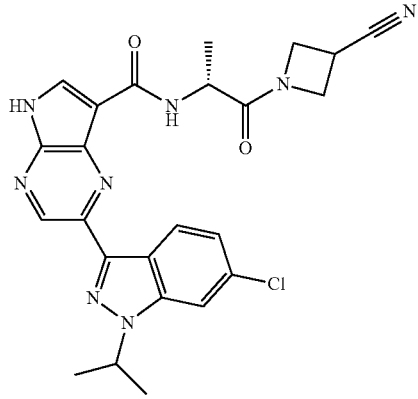 [SMILES: CC(C)n1nc(-c2cnc3[nH]cc(C(=O)N[C@H](C)C(=O)N4CC(C#N)C4)c3n2)c2ccc(Cl)cc21]

Prepared according to the procedure outlined in Example 90, substituting 2-bromopropane for 2-(2-bromoethoxy)tetrahydro-2H-pyran in Step 1. MS: (M+H)$^+$=491; mp=204-208° C.; $^1$H NMR (DMSO-d$_6$, 300 MHz): δ (ppm) 12.91 (br. s., 1H), 9.16 (s, 1H), 8.70 (d, J=8.3 Hz, 1H), 8.47 (dd, J=7.6, 2.6 Hz, 2H), 8.03 (d, J=1.1 Hz, 1H), 7.19-7.29 (m, 1H), 5.14 (quin, J=6.6 Hz, 1H), 4.46-4.79 (m, 3H), 4.15-4.27 (m, 1H), 4.03-4.14 (m, 1H), 3.78-3.92 (m, 1H), 1.56 (dd, J=6.6, 3.0 Hz, 6H), 1.39 (dd, J=6.6, 4.7 Hz, 3H).

Example 92

2-[6-Chloro-1-propyl-1H-indazol-3-yl]-5H-pyrrolo[2,3-b]pyrazine-7-carboxylic acid [(R)-2-(3-cyano-azetidin-1-yl)-1-methyl-2-oxo-ethyl]-amide

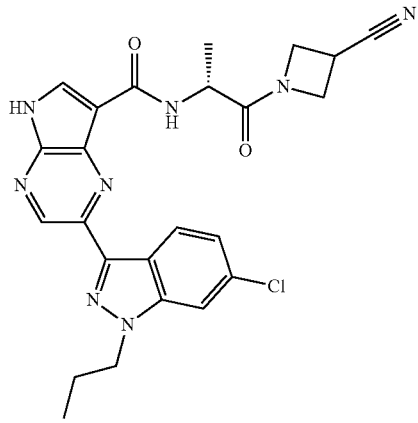 [SMILES: CCCn1nc(-c2cnc3[nH]cc(C(=O)N[C@H](C)C(=O)N4CC(C#N)C4)c3n2)c2ccc(Cl)cc21]

Step 1

2-(1-Allyl-6-chloro-1H-indazol-3-yl)-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide

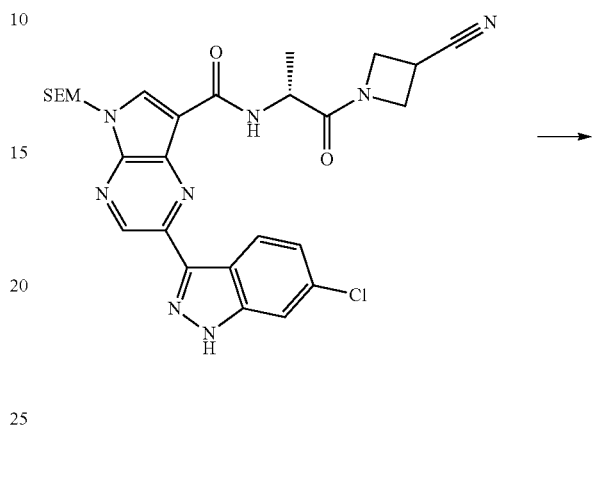

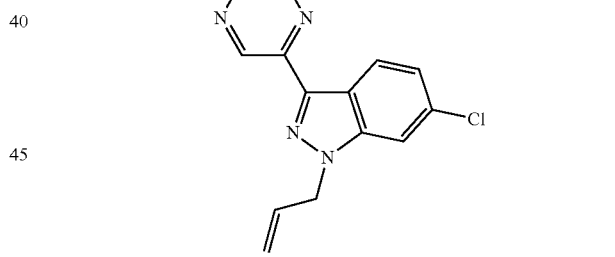

In a round-bottomed flask, 2-(6-chloro-1H-indazol-3-yl)-5-(2-trimethylsilanylethoxymethyl)-5H-pyrrolo[2,3-b]pyrazine-7-carboxylic acid [(R)-2-(3-cyano-azetidin-1-yl)-1-methyl-2-oxo-ethyl]-amide (see Example 23, 396 mg, 0.68 mmol) was dissolved in DMF (4.5 ml). The reaction mixture was cooled to 0° C. and sodium hydride (60% dispersion in mineral oil, 33 mg, 0.83 mmol) was added. The reaction mixture was stirred at 0° C. for 20 min then allyl bromide (65 µl, 0.75 mmol) was added. The reaction mixture was stirred at 0° C. for 20 min and then at room temperature for 1 h. The reaction mixture was quenched with water and extracted with ethyl acetate (2×). The combined organic layers were washed with water, sat LiCl, and brine then dried over MgSO$_4$ and concentrated. The residue was chromatographed over silica gel with 50% to 100% EtOAc/heptane to afford 388 mg (92%) of 2-(1-allyl-6-chloro-1H-indazol-3-yl)-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide as a light yellow foam.

Step 2

2-(6-Chloro-1-propyl-1H-indazol-3-yl)-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide b]pyrazine-7-carboxylic acid [(R)-2-(3-cyano-azetidin-1-yl)-1-methyl-2-oxo-ethyl]-amide as a viscous colorless oil.

Step 3

2-[6-Chloro-1-propyl-1H-indazol-3-yl]-5H-pyrrolo[2,3-b]pyrazine-7-carboxylic acid [(R)-2-(3-cyano-azetidin-1-yl)-1-methyl-2-oxo-ethyl]-amide

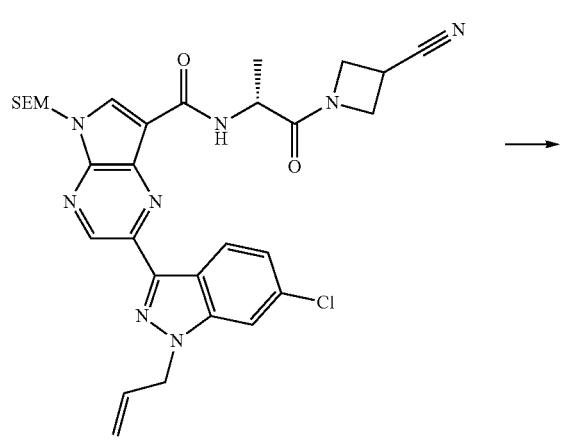

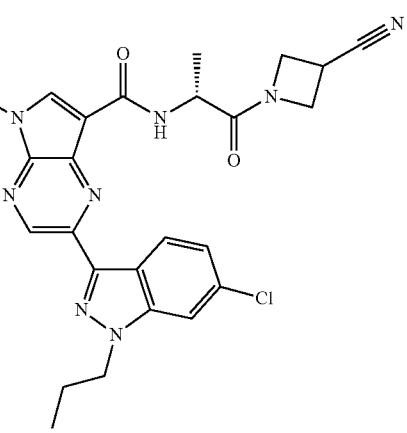

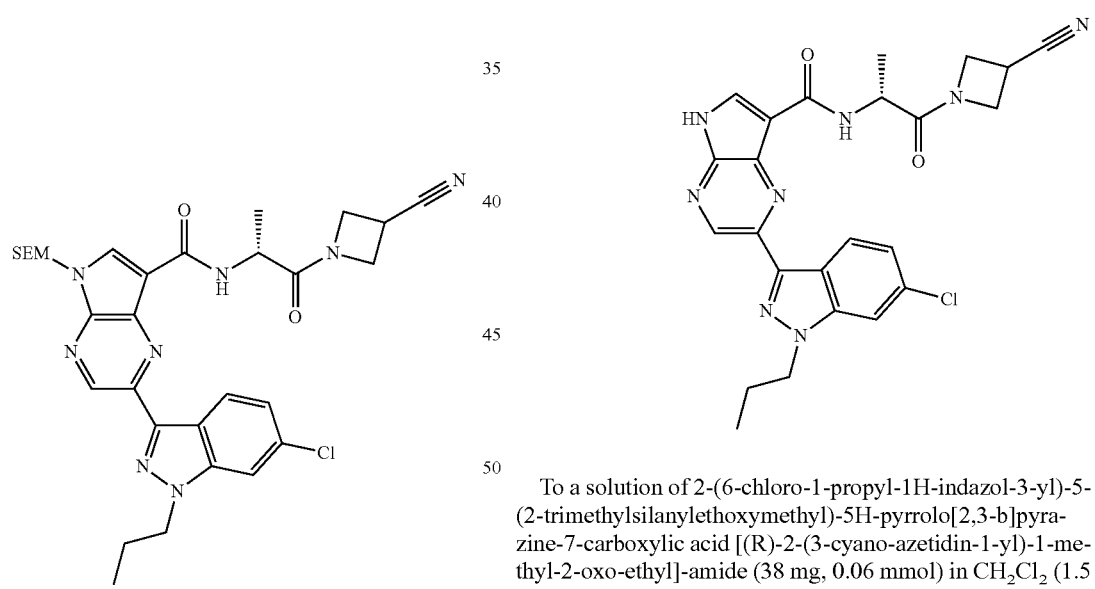

To a solution of 2-(1-allyl-6-chloro-1H-indazol-3-yl)-5-(2-trimethylsilanylethoxymethyl)-5H-pyrrolo[2,3-b]pyrazine-7-carboxylic acid [(R)-2-(3-cyano-azetidin-1-yl)-1-methyl-2-oxo-ethyl]-amide (50 mg, 0.08 mmol) in MeOH (6 ml) was added 10% Pd on carbon (wet, 17 mg). The reaction mixture was stirred under an atmosphere of hydrogen (balloon) for 1.5 h then filtered over Celite, rinsing with EtOAc. The filtrate was concentrated and the residue was purified by silica gel chromatography with 50% to 100% EtOAc/heptane to afford 38 mg (76%) of 2-(6-chloro-1-propyl-1H-indazol-3-yl)-5-(2-trimethylsilanyl-ethoxymethyl)-5H-pyrrolo[2,3-

To a solution of 2-(6-chloro-1-propyl-1H-indazol-3-yl)-5-(2-trimethylsilanylethoxymethyl)-5H-pyrrolo[2,3-b]pyrazine-7-carboxylic acid [(R)-2-(3-cyano-azetidin-1-yl)-1-methyl-2-oxo-ethyl]-amide (38 mg, 0.06 mmol) in $CH_2Cl_2$ (1.5 mL) was added TFA (0.5 mL). The reaction mixture was stirred at room temperature for 3 h then concentrated. The residue was redissolved in 10:90:0.5 MeOH/$CH_2Cl_2$/NH$_4$OH (3 mL) and stirred at room temperature for 3 h. The reaction mixture was concentrated and the residue was purified by silica gel chromatography with 0% to 10% MeOH/$CH_2Cl_2$ to afford 10 mg (32%) of 2-[6-chloro-1-propyl-1H-indazol-3-yl]-5H-pyrrolo[2,3-b]pyrazine-7-carboxylic acid [(R)-2-(3-cyano-azetidin-1-yl)-1-methyl-2-oxo-ethyl]-amide as a white solid. MS: (M+Na)$^+$=513; mp=219-221° C.; $^1$H NMR (DMSO-d$_6$, 300 MHz): δ (ppm) 12.93 (s, 1H), 9.13 (s, 1H), 8.71 (d, J=9.1 Hz, 1H), 8.46 (dd, J=7.6, 2.6 Hz, 2H), 8.03 (s, 1H), 7.25 (d, J=9.1 Hz, 1H), 4.43-4.78 (m, 5H), 4.16-4.27 (m, 1H), 4.05-4.13 (m, 1H), 3.78-3.91 (m, 1H), 1.86-1.96 (m, 2H), 1.39 (dd, J=6.6, 4.3 Hz, 3H), 0.89 (t, J=7.4 Hz, 3H).

Example 93

2-(6-Chloro-1-cyanomethyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide

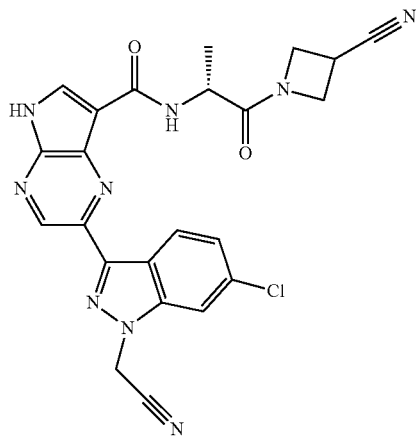 [SMILES: C[C@@H](NC(=O)c1c[nH]c2ncc(-c3nn(CC#N)c4cc(Cl)ccc34)nc12)C(=O)N1CC(C#N)C1]

Prepared according to the procedure outlined in Example 90, substituting 2-iodoacetonitrile for 2-(2-bromoethoxy)tetrahydro-2H-pyran in Step 1. MS: (M+Na)$^+$=510; $^1$H NMR (DMSO-d$_6$, 300 MHz): δ (ppm) 13.00 (br. s., 1H), 9.14 (s, 1H), 8.79 (dd, J=8.7, 2.3 Hz, 1H), 8.52 (d, J=6.4 Hz, 1H), 8.42 (d, J=7.9 Hz, 1H), 8.15 (s, 1H), 7.36 (d, J=9.1 Hz, 1H), 5.94 (s, 2H), 4.48-4.78 (m, 3H), 4.17-4.28 (m, 1H), 4.06-4.15 (m, 1H), 3.80-3.89 (m, 1H), 1.33-1.44 (m, 3H).

Example 94

2-[6-Chloro-1-(2,3-dihydroxy-propyl)-1H-indazol-3-yl]-5H-pyrrolo[2,3-b]pyrazine-7-carboxylic acid [(R)-2-(3-cyano-azetidin-1-yl)-1-methyl-2-oxo-ethyl]-amide

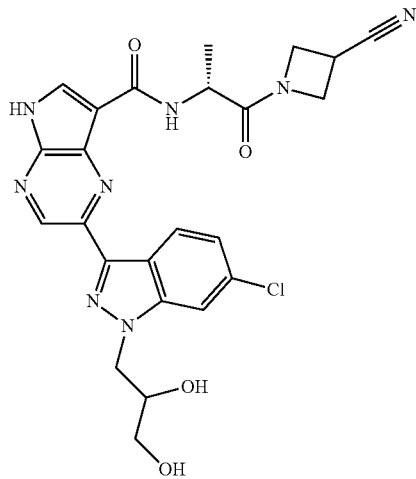 [SMILES: C[C@@H](NC(=O)c1c[nH]c2ncc(-c3nn(CC(O)CO)c4cc(Cl)ccc34)nc12)C(=O)N1CC(C#N)C1]

Step 1

Methanesulfonic acid 2,2-dimethyl-[1,3]dioxolan-4-ylmethyl ester

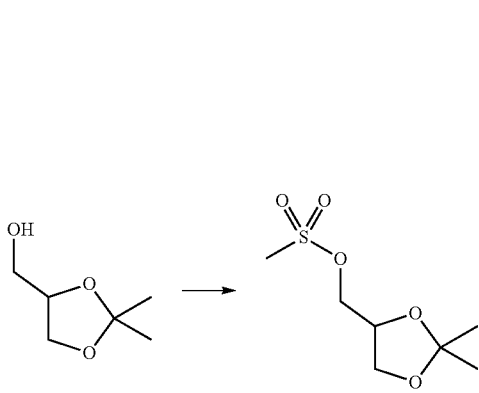

To a solution of (2,2-dimethyl-[1,3]dioxolan-4-yl)-methanol (1.25 g, 9.46 mmol) and triethylamine (9.2 ml, 66.2 mmol) in dichloromethane (60 ml) at 0° C. was slowly added methanesulfonyl chloride (2.2 ml, 28.4 mmol). The reaction mixture was stirred at 0° C. for 2 h then quenched with water and the aqueous layer was extracted with dichloromethane. The combined organics were washed with 10% citric acid, sat NaHCO$_3$, and brine then dried over MgSO$_4$ and concentrated to afford methanesulfonic acid 2,2-dimethyl-[1,3]dioxolan-4-ylmethyl ester as a light brown oil which was used without further purification.

Step 2

2-[6-Chloro-1-(2,2-dimethyl-[1,3]dioxolan-4-ylmethyl)-1H-indazol-3-yl]-5-(2-trimethylsilanylethoxymethyl)-5H-pyrrolo[2,3-b]pyrazine-7-carboxylic acid [(R)-2-(3-cyano-azetidin-1-yl)-1-methyl-2-oxo-ethyl]-amide

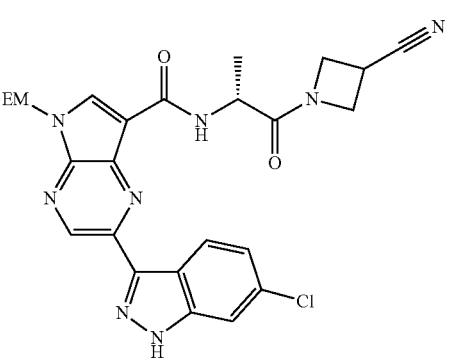

531

-continued

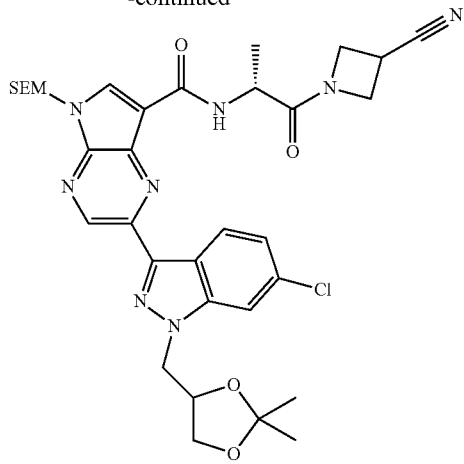

In a round-bottomed flask, 2-(6-chloro-1H-indazol-3-yl)-5-(2-trimethylsilanylethoxymethyl)-5H-pyrrolo[2,3-b]pyrazine-7-carboxylic acid [(R)-2-(3-cyano-azetidin-1-yl)-1-methyl-2-oxo-ethyl]-amide (see Example 23, 120 mg, 0.21 mmol) was dissolved in DMF (1.3 ml). The reaction mixture was cooled to 0° C. and sodium hydride (60% dispersion in mineral oil, 12 mg, 0.31 mmol) was added. The reaction mixture was stirred at 0° C. for 30 min then a solution of methanesulfonic acid 2,2-dimethyl-[1,3]dioxolan-4-ylmethyl ester (131 mg, 0.62 mmol) in DMF (0.5 ml) was added. The reaction mixture was stirred at 0° C. for 1 h and then at room temperature for 48 h. The reaction mixture was quenched with water and extracted with ethyl acetate (2×). The combined organic layers were washed with water, sat LiCl, and brine then dried over $MgSO_4$ and concentrated to give 2-[6-chloro-1-(2,2-dimethyl-[1,3]dioxolan-4-ylmethyl)-1H-indazol-3-yl]-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide as a light brown viscous oil which was used without further purification.

Step 3

2-[6-Chloro-1-(2,3-dihydroxy-propyl)-1H-indazol-3-yl]-5H-pyrrolo[2,3-b]pyrazine-7-carboxylic acid [(R)-2-(3-cyano-azetidin-1-yl)-1-methyl-2-oxo-ethyl]-amide

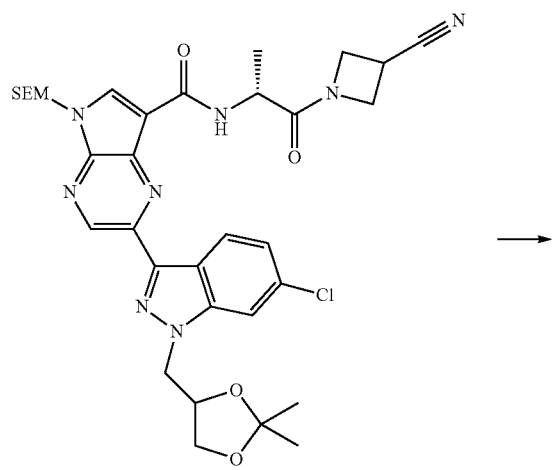

532

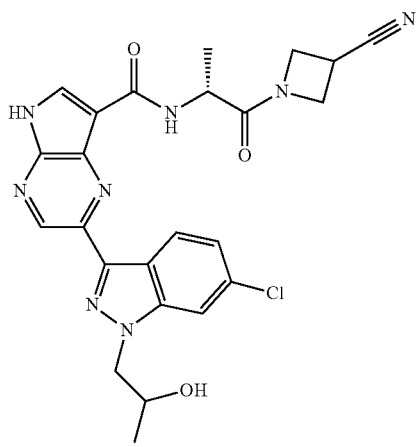 [SMILES: CC(O)Cn1nc(-c2cnc3[nH]cc(C(=O)N[C@H](C)C(=O)N4CC(C#N)C4)c3n2)c2ccc(Cl)cc21]

To a solution of 2-[6-chloro-1-(2,2-dimethyl-[1,3]dioxolan-4-ylmethyl)-1H-indazol-3-yl]-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide (crude from Step 2) in $CH_2Cl_2$ (3 mL) was added TFA (1 mL). The reaction mixture was stirred at room temperature for 48 h then concentrated. The residue was redissolved in 10:90:0.5 $MeOH/CH_2Cl_2/NH_4OH$ (3 mL) and stirred at room temperature for 3 h. The reaction mixture was concentrated and the residue was purified by silica gel chromatography with 0% to 10% $MeOH/CH_2Cl_2$ to afford 22 mg (20%, 2 steps) of 2-[6-Chloro-1-(2,3-dihydroxy-propyl)-1H-indazol-3-yl]-5H-pyrrolo[2,3-b]pyrazine-7-carboxylic acid [(R)-2-(3-cyano-azetidin-1-yl)-1-methyl-2-oxo-ethyl]-amide as a white solid. MS: $(M+Na)^+$=545; mp=165-180° C.; $^1H$ NMR (DMSO-$d_6$, 300 MHz): δ (ppm) 9.14 (s, 1H), 8.69 (d, J=8.7 Hz, 1H), 8.47 (d, J=7.6 Hz, 2H), 7.91 (s, 1H), 7.23 (d, J=6.8 Hz, 1H), 5.15 (d, J=5.3 Hz, 1H), 5.03 (dd, J=5.3, 3.0 Hz, 1H), 4.84 (t, J=5.5 Hz, 1H), 4.35-4.80 (m, 5H), 4.18-4.26 (m, 1H), 3.93-4.15 (m, 2H), 3.79-3.90 (m, 1H), 3.34-3.49 (m, 2H), 1.33-1.45 (m, 3H).

Example 95

2-[6-Chloro-1-(2-hydrox-ypropyl)-1H-indazol-3-yl]-5H-pyrrolo[2,3-b]pyrazine-7-carboxylic acid [(R)-2-(3-cyano-azetidin-1-yl)-1-methyl-2-oxo-ethyl]-amide

Step 1

2-(2-Bromo-1-methyl-ethoxy)-tetrahydro-2H-pyran

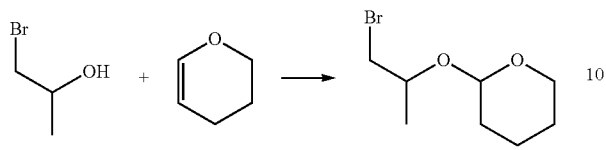

To a solution of 1-bromopropan-2-ol (1.25 g, 9.0 mmol) and 3,4-dihydro-2H-pyran (2.04 ml, 22.5 mmol) in dichloromethane (50 ml) at 0° C. was added p-toluenesulfonic acid monohydrate (85 mg, 0.45 mmol). The reaction mixture was stirred at 0° C. for 15 min then warmed to room temperature and stirred for 2 h. The reaction was diluted with EtOAc and washed with water, sat NaHCO₃, and brine then dried over MgSO₄ and concentrated to afford 2-(2-bromo-1-methyl-ethoxy)-tetrahydro-2H-pyran as a light brown oil which was used without further purification.

Step 2

2-[6-Chloro-1-(2-hydroxy-propyl)-1H-indazol-3-yl]-5H-pyrrolo[2,3-b]pyrazine-7-carboxylic acid [(R)-2-(3-cyano-azetidin-1-yl)-1-methyl-2-oxo-ethyl]-amide

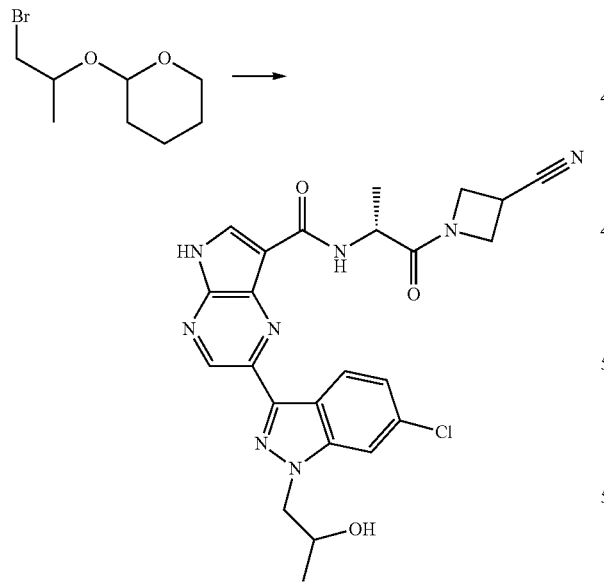

Prepared according to the procedure outlined in Example 90, substituting 2-(2-bromo-1-methyl-ethoxy)-tetrahydro-2H-pyran for 2-(2-bromoethoxy)tetrahydro-2H-pyran in Step 1. MS: (M+Na)⁺=529; mp=160-165° C.; ¹H NMR (DMSO-d₆, 300 MHz): δ (ppm) 12.91 (br. s., 1H), 9.13 (s, 1H), 8.69 (d, J=8.7 Hz, 1H), 8.47 (d, J=7.6 Hz, 2H), 7.95 (s, 1H), 7.17-7.27 (m, 1H), 4.93 (dd, J=5.1, 2.8 Hz, 1H), 4.49-4.78 (m, 3H), 4.42 (d, J=6.0 Hz, 2H), 4.06-4.27 (m, 3H), 3.80-3.87 (m, 1H), 1.39 (dd, J=6.6, 4.7 Hz, 3H), 1.11-1.21 (m, 3H).

Example 96

2-[6-Chloro-1-(3-hydroxy-propyl)-1H-indazol-3-yl]-5H-pyrrolo[2,3-b]pyrazine-7-carboxylic acid [(R)-2-(3-cyano-azetidin-1-yl)-1-methyl-2-oxo-ethyl]-amide

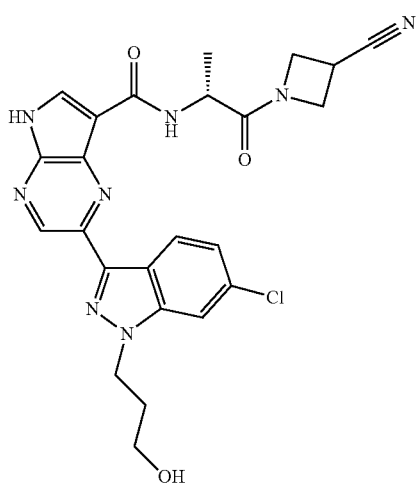

Step 1

2-(3-Bromopropoxy)-tetrahydro-2H-pyran

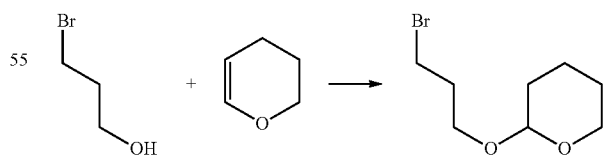

To a solution of 3-bromopropan-1-ol (1.25 g, 9.0 mmol) and 3,4-dihydro-2H-pyran (2.04 ml, 22.5 mmol) in dichloromethane (50 ml) at 0° C. was added p-toluenesulfonic acid monohydrate (85 mg, 0.45 mmol). The reaction mixture was stirred at 0° C. for 15 min then warmed to room temperature and stirred for 2 h. The reaction was diluted with EtOAc and washed with water, sat NaHCO₃, and brine then dried over MgSO$_4$ and concentrated to afford 2-(3-bromopropoxy)-tetrahydro-2H-pyran as a light brown oil which was used without further purification.

Step 2

2-[6-Chloro-1-(3-hydroxy-propyl)-1H-indazol-3-yl]-5H-pyrrolo[2,3-b]pyrazine-7-carboxylic acid [(R)-2-(3-cyano-azetidin-1-yl)-1-methyl-2-oxo-ethyl]-amide

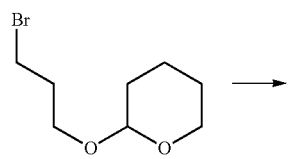

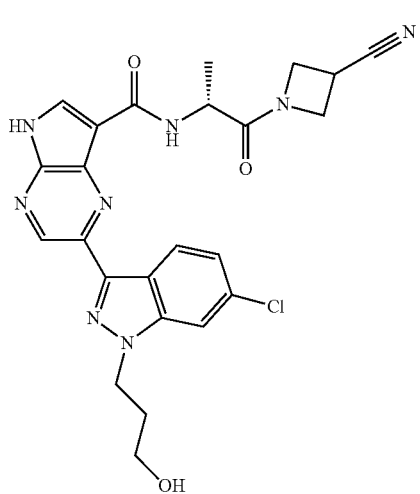 [SMILES: C[C@@H](NC(=O)c1c[nH]c2ncc(-c3nn(CCCO)c4cc(Cl)ccc34)nc12)C(=O)N1CC(C#N)C1]

Prepared according to the procedure outlined in Example 90, substituting 2-(3-bromopropoxy)-tetrahydro-2H-pyran for 2-(2-bromoethoxy)tetrahydro-2H-pyran in Step 1. MS: (M+Na)$^+$=529; mp=240-250° C.; $^1$H NMR (DMSO-d$_6$, 300 MHz): δ (ppm) 12.92 (br. s., 1H), 9.14 (s, 1H), 8.71 (d, J=9.1 Hz, 1H), 8.47 (dd, J=7.4, 4.0 Hz, 2H), 7.96 (d, J=1.5 Hz, 1H), 7.20-7.30 (m, 1H), 4.49-4.79 (m, 6H), 4.17-4.28 (m, 1H), 4.04-4.14 (m, 1H), 3.78-3.89 (m, 1H), 3.44 (q, J=5.9 Hz, 2H), 2.05 (t, J=6.6 Hz, 2H), 1.39 (dd, J=6.8, 4.5 Hz, 3H).

Example 97

2-(4,6-Dichloro-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide

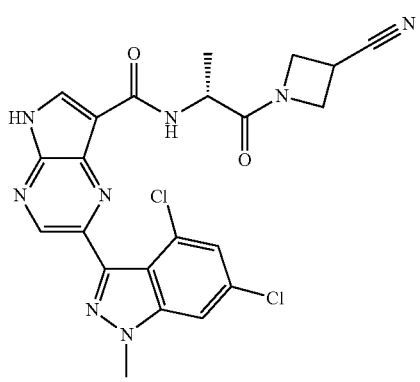

Step 1

2,4,6-Trichlorobenzaldehyde

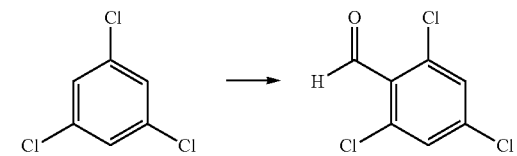 [SMILES: Clc1cc(Cl)cc(Cl)c1 ; O=Cc1c(Cl)cc(Cl)cc1Cl]

2,4,6-Trichlorobenzaldehyde was prepared according to the procedure outlined in *Synthesis* 2008, 279. To a solution of 1,3,5-trichlorobenzene (10.0 g, 55.1 mmol) in THF (200 ml) at −78° C. was slowly added n-BuLi (1.6 M in hexanes, 34.4 ml, 55.1 mmol) over 20 min. The reaction mixture was stirred at −78° C. for 30 min then DMF (7.5 ml, 96.4 mmol) was added dropwise. The reaction was stirred at −78° C. for an additional 1.5 h then quenched with 3 N HCl (200 ml) and warmed to room temperature. The mixture was extracted with EtOAc. The organic layer was washed with sat NaHCO$_3$ and brine then dried over MgSO$_4$ and concentrated to afford 10.7 g (93%) of 2,4,6-trichlorobenzaldehyde as a white solid.

Step 2

4,6-Dichloro-1H-indazole

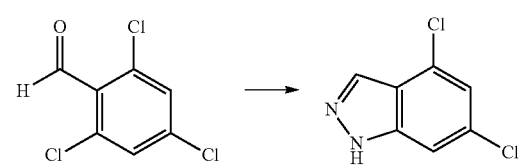 [SMILES: O=Cc1c(Cl)cc(Cl)cc1Cl ; Clc1cc(Cl)c2cn[nH]c2c1]

In a microwave vial 2,4,6-trichlorobenzaldehyde (4.0 g, 19.1 mmol) was dissolved in 1,4-dioxane (8 mL) and hydrazine (7.2 mL, 229 mmol) was added. The vial was sealed and heated under microwave irradiation at 160° C. for 30 min. The reaction was quenched with water and extracted with EtOAc. The organic layer was washed with brine then dried over MgSO$_4$ and concentrated. The residue was purified by silica gel chromatography with 50% to 100% EtOAc/heptane to provide 1.38 g (38%) of 4,6-dichloro-1H-indazole as a white solid. $^1$H NMR (CDCl$_3$, 300 MHz): δ (ppm) 8.14 (s, 1H), 7.44 (s, 1H), 7.20 (d, J=1.5 Hz, 15H).

Step 3

2-(4,6-Dichloro-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide

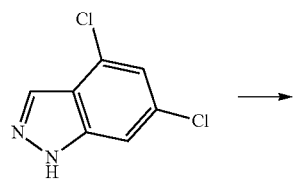

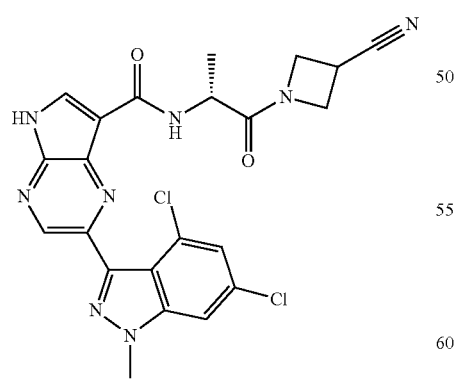

Prepared according to the procedure outlined in Example 81, Steps 3-7, substituting 4,6-dichloro-1H-indazole for 6-tert-butyl-1H-indazole in Step 3. MS: (M+Na)$^+$=519; mp=196-200° C.; $^1$H NMR (DMSO-d$_6$, 300 MHz): δ (ppm) 8.75 (s, 1H), 8.45-8.56 (m, 2H), 8.03 (s, 1H), 7.42 (s, 1H), 4.38-4.66 (m, 3H), 4.17 (s, 3H), 3.91-4.14 (m, 2H), 3.73-3.86 (m, 1H), 1.23-1.32 (m, 3H).

Example 98

2-(1-Methyl-1H-pyrazolo[4,3-b]pyridin-3-yl)-5H-pyrrolo[2,3-b]pyrazine-7-carboxylic acid [(R)-2-(3-cyano-azetidin-1-yl)-1-methyl-2-oxo-ethyl]-amide

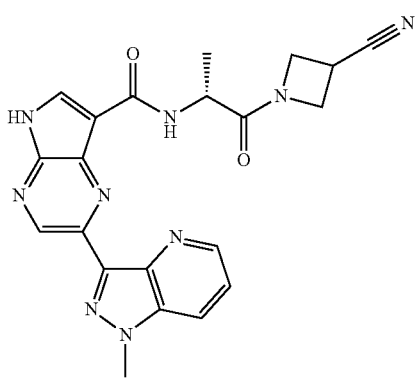 [SMILES: C[C@@H](NC(=O)c1c[nH]c2ncc(-c3nn(C)c4cccnc34)nc12)C(=O)N1CC(C#N)C1]

Step 1

1-Pyrazolo[4,3-b]pyridin-1-yl-ethanone

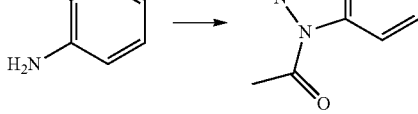

To a solution of 3-amino-2-methylpyridine (1.0 g, 9.25 mmol) in CHCl$_3$ (24 ml) at 0° C. was slowly added acetic anhydride (2.0 ml, 21.3 mmol). The reaction mixture was warmed to room temperature and stirred for 1 h. Potassium acetate (272 mg, 2.77 mmol) was added followed by slow addition of isoamyl nitrite (2.7 ml, 19.9 mmol). The reaction mixture was heated at reflux overnight. The reaction mixture was cooled to room temperature and concentrated. The residue was dissolved in EtOAc and washed with water, sat'd NaHCO$_3$ and brine then dried over MgSO$_4$ and concentrated. The residue was purified by silica gel chromatography with 20% to 100% EtOAc/heptane to give 973 mg (65%) of 1-pyrazolo[4,3-b]pyridin-1-yl-ethanone as a light yellow solid.

Step 2

1H-Pyrazolo[4,3-b]pyridine

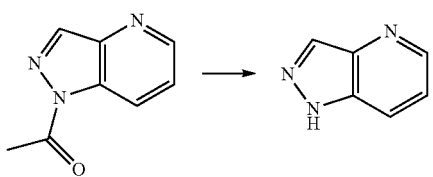

Pyrazolo[4,3-b]pyridin-1-yl-ethanone (973 mg, 6.04 mmol) was dissolved in THF/MeOH (1:1, 16 mL) and 10% NaOH (1.8 mL) was added. The reaction mixture was stirred at room temperature for 30 min then neutralized with 1.0 M HCl, diluted with water and extracted with EtOAc (2×). The combined organics were washed with brine then dried over MgSO$_4$ and concentrated to afford 687 mg (96%) of 1H-pyrazolo[4,3-b]pyridine as a light yellow solid. $^1$H NMR (DMSO-d$_6$, 300 MHz): δ (ppm) 13.29 (br. s., 1H), 8.50 (d, J=4.5 Hz, 1H), 8.27 (s, 1H), 8.00 (d, J=8.7 Hz, 1H), 7.34 (dd, J=8.7, 4.5 Hz, 1H).

Step 3

2-(1-Methyl-1H-pyrazolo[4,3-b]pyridin-3-yl)-5H-pyrrolo[2,3-b]pyrazine-7-carboxylic acid [(R)-2-(3-cyano-azetidin-1-yl)-1-methyl-2-oxo-ethyl]-amide

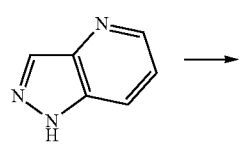

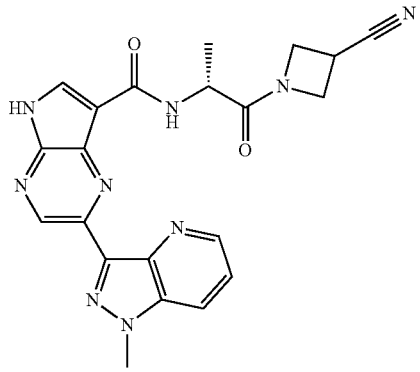

Prepared according to the procedure outlined in Example 81, Steps 3-7, substituting 1H-pyrazolo[4,3-b]pyridine for 6-tert-butyl-1H-indazole in Step 3. MS: (M+H)$^+$=430; mp=194-198° C.; $^1$H NMR (DMSO-d$_6$, 300 MHz): δ (ppm) 12.86 (br. s., 1H), 9.32 (s, 1H), 9.05 (t, J=7.9 Hz, 1H), 8.68 (d, J=4.2 Hz, 1H), 8.44 (d, J=12.1 Hz, 1H), 8.27 (d, J=8.3 Hz, 1H), 7.52 (dd, J=8.7, 4.2 Hz, 1H), 4.40-4.79 (m, 3H), 4.21 (s, 3H), 3.98-4.05 (m, 2H), 3.74-3.84 (m, 1H), 1.49 (d, J=6.8 Hz, 3H).

Example 99

2-(1-Methyl-1H-thieno[3,2-c]pyrazol-3-yl)-5H-pyrrolo[2,3-b]pyrazine-7-carboxylic acid [(R)-2-(3-cyano-azetidin-1-yl)-1-methyl-2-oxo-ethyl]-amide

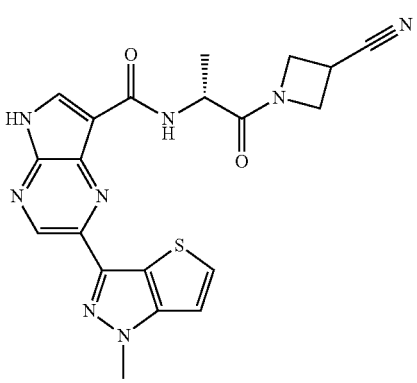 [SMILES: C[C@@H](NC(=O)c1c[nH]c2ncc(-c3nn(C)c4ccsc34)nc12)C(=O)N1CC(C#N)C1]

Step 1

N-Benzhydrylidene-N'-[1-(3-bromo-thiophen-2-yl)-meth-(E)-ylidene]-hydrazine

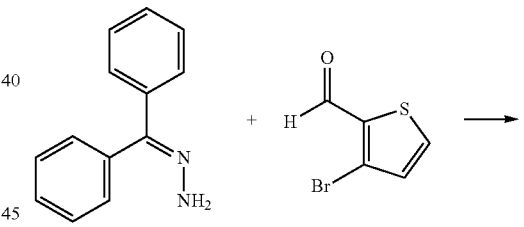

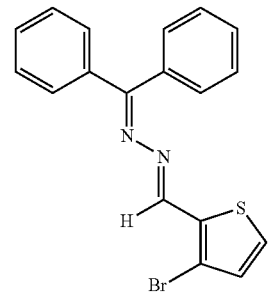

To a solution of 3-bromothiophene-2-carbaldehyde (5.57 g, 29.2 mmol) in EtOH (90 mL) was added (diphenylmethylene)hydrazine (6.3 g, 32.1 mmol). The reaction mixture was heated at 65° C. for 4 h then concentrated. The residue was purified by silica gel chromatography with 10% to 20%

EtOAc/heptane to afford 11 g of N-benzhydrylidene-N'-[1-(3-bromo-thiophen-2-yl)-meth-(E)-ylidene]-hydrazine as a viscous yellow oil.

Step 2

N-Benzhydrylidene-N'-[2-(benzhydrylidene-hydrazonomethyl)-thiophen-3-yl]-hydrazine

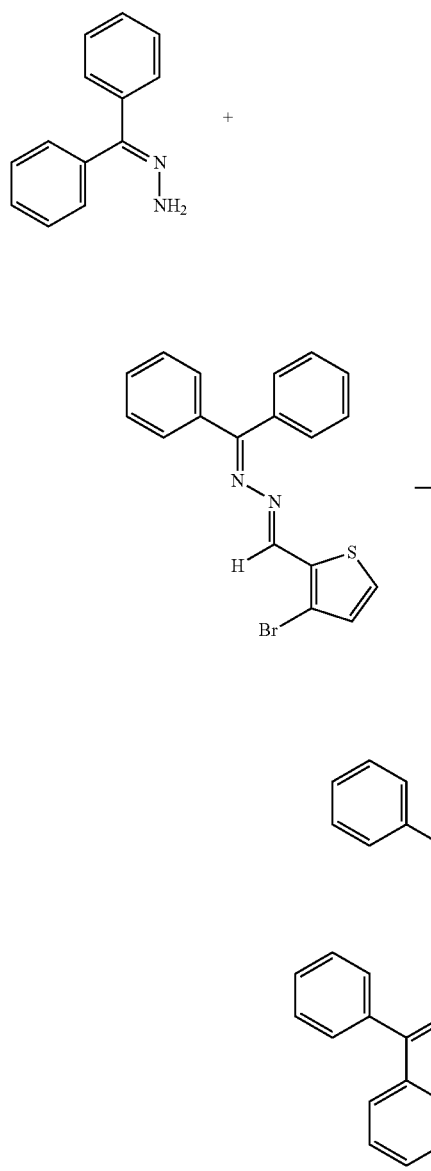

To a solution of N-benzhydrylidene-N'-[1-(3-bromo-thiophen-2-yl)-meth-(E)-ylidene]-hydrazine (10.8 g, 29.2 mmol) in toluene (200 mL) was added (diphenylmethylene)hydrazine (6.9 g, 35.1 mmol), cesium carbonate (16.2 g, 49.7 mmol), Pd(OAc)$_2$ (1.31 g, 5.85 mol), and 1,1'-bis(diphenylphosphino)ferrocene (2.43 g, 4.4 mmol). The reaction mixture was heated at 100° C. for 8.5 h then cooled to room temperature, diluted with EtOAc and filtered over Celite, rinsing with EtOAc. The filtrate was concentrated and the residue was purified by silica gel chromatography with 10% to 20% EtOAc/heptane to give 12.8 g of N-benzhydrylidene-N'-[2-(benzhydrylidene-hydrazonomethyl)-thiophen-3-yl]-hydrazine as a viscous brown oil.

Step 3

1H-Thieno[3,2-c]pyrazole

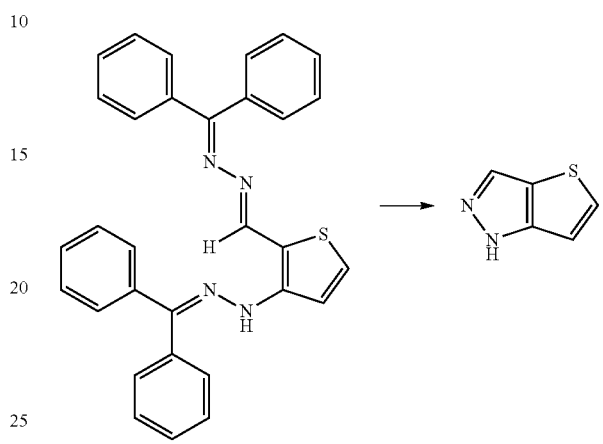

To a solution of N-benzhydrylidene-N'-[2-(benzhydrylidene-hydrazonomethyl)-thiophen-3-yl]-hydrazine (12.8 g, 26.4 mmol) in EtOH (300 mL) was added conc. HCl (150 mL). the deep red reaction mixture was stirred at 85° C. for 1 h then cooled to room temperature, diluted with water and neutralized with Na$_2$CO$_3$. The mixture was extracted with EtOAc. The organic layer was washed with brine then dried over MgSO$_4$ and concentrated. The residue was purified by silica gel chromatography with 20% to 100% EtOAc/heptane to afford 2.0 g (60%) of 1H-thieno[3,2-c]pyrazole as a brown solid. The NMR appears to display a mixture of 1H and 2H tautomers: major $^1$H NMR (DMSO-d$_6$, 300 MHz): δ (ppm) 13.00 (br. s., 1H), 7.74 (s, 1H), 7.60 (d, J=5.3 Hz, 1H), 7.09 (d, J=5.3 Hz, 1H); minor $^1$H NMR (DMSO-d$_6$, 300 MHz): δ (ppm) 13.32 (s, 1H), 8.02 (s, 1H), 7.56 (d, J=4.9 Hz, 1H), 7.13 (d, J=4.9 Hz, 1H).

Step 4

3-Iodo-1H-thieno[3,2-c]pyrazole

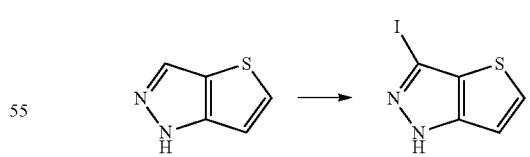

To a solution of 1H-thieno[3,2-c]pyrazole (1.0 g, 8.05 mmol) in DMF (65 ml) at room temperature was added potassium hydroxide (1.36 g, 24.2 mmol) and iodine (3.07 g, 12.1 mmol). The maroon reaction mixture was stirred at room temperature for 3 h then quenched with 10% aqueous Na$_2$S$_2$O$_3$ and diluted with water. The mixture was extracted with EtOAc (2×). The combined organics were washed with water, sat LiCl, and sat NaCl, then dried over MgSO$_4$ and concentrated to afford 2.0 g (99%) of 3-iodo-1H-thieno[3,2- c]pyrazole as a light brown solid. ¹H NMR (DMSO-d₆, 300 MHz): δ (ppm) 13.38 (br. s., 1H), 7.68 (d, J=5.3 Hz, 1H), 7.21 (d, J=5.3 Hz, 1H).

Step 5

3-Iodo-1-methyl-1H-thieno[3,2-c]pyrazole

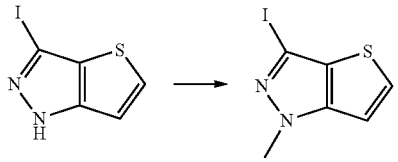

To a solution of 3-iodo-1H-thieno[3,2-c]pyrazole (500 mg, 2.0 mmol) in THF (7 ml) at 0° C. was added KOt-Bu (314 mg, 2.8 mmol). The reaction mixture was stirred at 0° C. for 30 min then added iodomethane (0.17 ml, 2.8 mmol). Stirred at 0° C. for 30 min then warmed to room temperature and stirred for 1.5 h. The reaction was quenched with water and extracted with EtOAc (2×). The combined organics were washed with brine then dried over MgSO₄ and concentrated. The crude residue was purified by silica gel chromatography with 20% to 50% EtOAc/heptane to afford 292 mg (55%) of 3-iodo-1-methyl-1H-thieno[3,2-c]pyrazole as a light brown viscous oil. ¹H NMR (CDCl₃, 300 MHz): δ (ppm) 7.41 (d, J=5.3 Hz, 1H), 6.97 (d, J=5.3 Hz, 1H), 4.05 (s, 3H). Also isolated 141 mg (27%) of 3-iodo-2-methyl-2H-thieno[3,2-c]pyrazole as an off-white solid. ¹H NMR (CDCl₃, 300 MHz): δ (ppm) 7.36 (d, J=5.3 Hz, 1H), 7.16 (d, J=5.3 Hz, 1H), 4.13 (s, 3H).

Step 6

1-Methyl-3-tributylstannanyl-1H-thieno[3,2-c]pyrazole

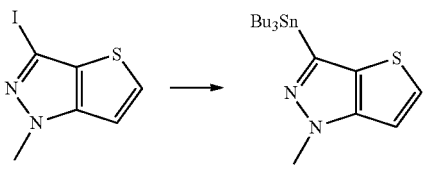

To a solution of 3-iodo-1-methyl-1H-thieno[3,2-c]pyrazole (290 mg, 1.10 mmol) in THF (6 mL) at −15° C. was slowly added isopropylmagnesium chloride (2.0 M in THF, 0.66 mL, 1.32 mmol). The bright yellow heterogeneous reaction mixture was stirred at −15° C. for 20 min then tributylchlorostannane (0.36 mL, 1.32 mmol) was added dropwise. Stirring was continued at −15° C. for 20 min then at room temperature for 2 h. The reaction mixture was quenched with water and extracted with EtOAc (2×). The combined organics were washed with brine then dried over MgSO₄ and concentrated. The residue was purified by silica gel chromatography with 10% to 20% EtOAc/heptane (0.5% Et₃N) gave 298 mg (63%) of 1-methyl-3-tributylstannanyl-1H-thieno[3,2-c]pyrazole as a pale yellow oil. ¹H NMR (CDCl₃, 300 MHz): δ (ppm) 7.36 (d, J=5.3 Hz, 1H), 6.90 (d, J=5.3 Hz, 1H), 4.06 (s, 3H), 1.54-1.67 (m, 6H), 1.36 (dq, J=14.7, 7.3 Hz, 6H), 1.13-1.22 (m, 6H), 0.90 (t, J=7.3 Hz, 9H).

Step 7

2-(1-Methyl-1H-thieno[3,2-c]pyrazol-3-yl)-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide

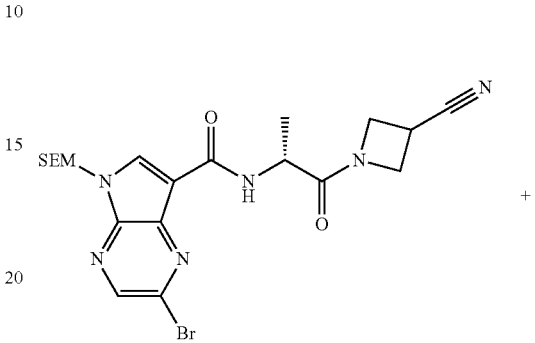

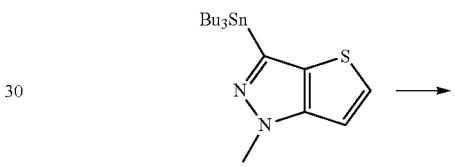

To a solution of 1-methyl-3-tributylstannanyl-1H-thieno[3,2-c]pyrazole (111 mg, 0.26 mmol) and 2-bromo-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide (120 mg, 0.24 mmol) in DMF (1.2 mL) were added Pd(PPh₃)₄ (14 mg, 0.012 mmol) and copper(I) iodide (9 mg, 0.05 mmol). The yellow reaction mixture was purged with argon then heated at 80° C. for 1.5 h then cooled to room temperature, quenched with sat NH₄Cl and extracted with EtOAc (2×). The combined organics were washed with sat LiCl and brine then dried over MgSO₄ and concentrated. The crude residue was purified by silica gel chromatography with 50% to 100% EtOAc/heptane to provide 131 mg (98%) of 2-(1-methyl-1H-thieno[3,2-c]pyrazol-3-yl)-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide as an off-white solid.

Step 8

2-(1-Methyl-1H-thieno[3,2-c]pyrazol-3-yl)-5H-pyrrolo[2,3-b]pyrazine-7-carboxylic acid [(R)-2-(3-cyano-azetidin-1-yl)-1-methyl-2-oxo-ethyl]-amide

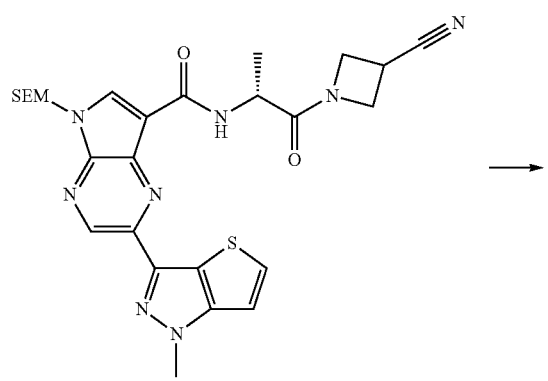

To a solution of 2-(1-methyl-1H-thieno[3,2-c]pyrazol-3-yl)-5-(2-trimethylsilanylethoxymethyl)-5H-pyrrolo[2,3-b]pyrazine-7-carboxylic acid [(R)-2-(3-cyano-azetidin-1-yl)-1-methyl-2-oxo-ethyl]-amide (131 mg, 0.23 mmol) in CH$_2$Cl$_2$ (2 mL) was added TFA (0.75 mL). The reaction mixture was stirred at room temperature for 5 h then concentrated. The residue was redissolved in 10:90:0.5 MeOH/CH$_2$Cl$_2$/NH$_4$OH (3 mL) and stirred at room temperature for 3 h. The reaction mixture was concentrated and the residue was purified by silica gel chromatography with 0% to 10% MeOH/CH$_2$Cl$_2$ to afford 83 mg (83%) of 2-(1-methyl-1H-thieno[3,2-c]pyrazol-3-yl)-5H-pyrrolo[2,3-b]pyrazine-7-carboxylic acid [(R)-2-(3-cyano-azetidin-1-yl)-1-methyl-2-oxo-ethyl]-amide as a white solid. MS (M+Na)$^+$=457; mp=310-320° C.; $^1$H NMR (DMSO-d$_6$, 300 MHz): δ (ppm) 12.93 (br. s., 1H), 9.07 (s, 1H), 8.46 (d, J=11.0 Hz, 1H), 8.19 (d, J=7.9 Hz, 1H), 7.82 (d, J=5.3 Hz, 1H), 7.32 (d, J=5.3 Hz, 1H), 4.42-4.77 (m, 3H), 4.13-4.21 (m, 1H), 4.12 (s, 3H), 3.97-4.08 (m, 1H), 3.76-3.89 (m, 1H), 1.51 (dd, J=6.8, 2.6 Hz, 3H).

Example 100

2-(6-Fluoro-1-methyl-1H-indazol-3-yl)-5H-pyrrolo[2,3-b]pyrazine-7-carboxylic acid [(R)-1-(1-cyano-cyclopentyl)-ethyl]-amide

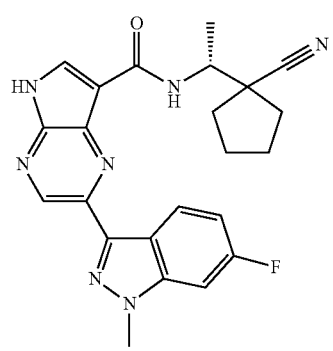 [SMILES: C[C@@H](NC(=O)c1c[nH]c2ncc(-c3nn(C)c4cc(F)ccc34)nc12)C1(C#N)CCCC1]

Step 1

(S)-2-Methyl-propane-2-sulfinic acid (E)-ethylideneamide

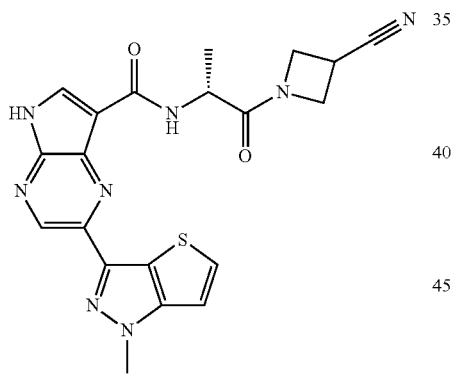

In a flask (S)-2-methyl-propane-2-sulfinic acid amide (1.50 g, 12.4 mmol) was dissolved in CH$_2$Cl$_2$ (6 mL). Acetaldehyde (6.25 mL, 111 mmol), MgSO$_4$ (4.47 g, 37.1 mmol) and pyridinium tosylate (156 mg, 0.62 mmol) were added. The reaction mixture was stirred overnight at room temperature, filtered and concentrated to give (S)-2-methyl-propane-2-sulfinic acid (E)-ethylideneamide as a pale red oil which was used without further purification.

Step 2

(S)-2-Methyl-propane-2-sulfinic acid [(R)-1-(1-cyano-cyclopentyl)-ethyl]-amide

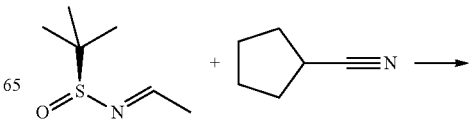

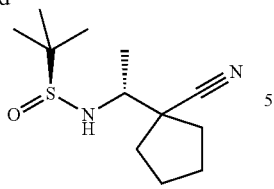

In a flask, cyclopentanecarbonitrile (3.53 g, 37.1 mmol) was dissolved in THF (40 mL) and cooled at −78° C. LiHMDS (1.0 M in THF, 41 mL, 41 mmol) was added and the mixture stirred for 30 min at −78° C. A solution of (S)-2-methyl-propane-2-sulfinic acid (E)-ethylideneamide (crude from step 1, 1.82 g, 12.4 mmol) in THF (10 mL) was slowly added. The mixture was stirred at −78° C. for 2 h then allowed to warm to room temperature overnight. The reaction mixture was quenched with saturated aqueous ammonium chloride and extracted with EtOAc. The combined organics were washed with brine, dried over MgSO$_4$ and concentrated. The residue was purified by SiO$_2$ chromatography (50-100% EtOAc/heptane) to afford 1.96 g (65%) of (S)-2-methyl-propane-2-sulfinic acid [(R)-1-(1-cyano-cyclopentyl)-ethyl]-amide as a white solid.

Step 3

1-((R)-1-Amino-ethyl)-cyclopentanecarbonitrile hydrochloride

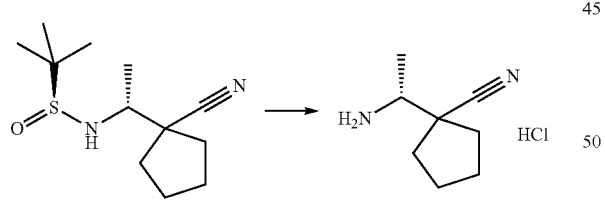

(S)-2-Methyl-propane-2-sulfinic acid [(R)-1-(1-cyano-cyclopentyl)-ethyl]-amide (1.96 g, 8.07 mmol) was dissolved in MeOH (16 mL) and HCl (4.0 M in 1,4-dioxane, 4.0 mL, 16.0 mmol) was added. The reaction mixture was stirred at room temperature for 30 min then concentrated to give 1-((R)-1-amino-ethyl)-cyclopentanecarbonitrile hydrochloride as an off-white solid which was used without further purification.

Step 4

2-(6-Fluoro-1-methyl-1H-indazol-3-yl)-5-(2-trimethylsilanyl-ethoxymethyl)-5H-pyrrolo[2,3-b]pyrazine-7-carboxylic acid [(R)-1-(1-cyano-cyclopentyl)-ethyl]-amide

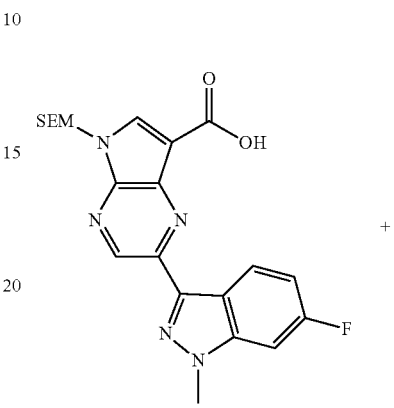

+

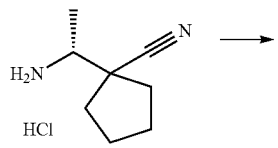

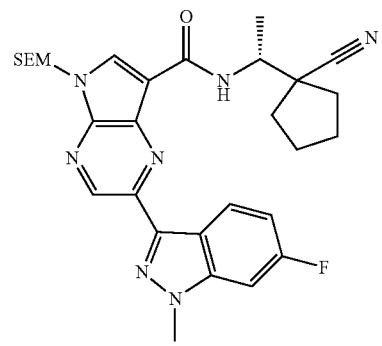

In a flask were combined 2-(6-fluoro-1-methyl-1H-indazol-3-yl)-5-(2-trimethylsilanylethoxymethyl)-5H-pyrrolo[2,3-b]pyrazine-7-carboxylic acid (120 mg, 0.27 mmol), 1-((R)-1-amino-ethyl)-cyclopentanecarbonitrile hydrochloride (48 mg, 0.27 mmol), EDC (120 mg, 0.63 mmol) and HOBt (106 g, 0.63 mmol). DMF (3 mL) was added followed by i-Pr$_2$NEt (0.28 mL, 1.63 mmol). The reaction mixture was stirred at room temperature for 3 h then quenched with water and extracted with EtOAc. The organics were washed with 10% citric acid, sat'd NaHCO$_3$, sat'd LiCl, and sat'd NaCl then dried over MgSO$_4$ and concentrated. The residue was purified by SiO$_2$ chromatography (20-100% EtOAc/heptane) to give 140 mg (92%) of 2-(6-fluoro-1-methyl-1H-indazol-3-yl)-5-

(2-trimethylsilanyl-ethoxymethyl)-5H-pyrrolo[2,3-b]pyrazine-7-carboxylic acid [(R)-1-(1-cyano-cyclopentyl)-ethyl]-amide as a white solid.

Step 5

2-(6-Fluoro-1-methyl-1H-indazol-3-yl)-5H-pyrrolo[2,3-b]pyrazine-7-carboxylic acid [(R)-1-(1-cyano-cyclopentyl)-ethyl]-amide

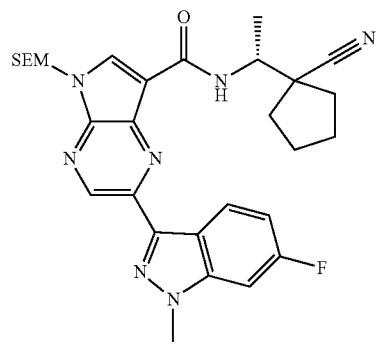

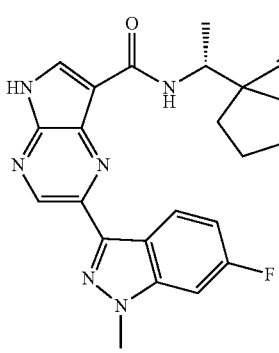

To a solution of 2-(6-fluoro-1-methyl-1H-indazol-3-yl)-5-(2-trimethylsilanylethoxymethyl)-5H-pyrrolo[2,3-b]pyrazine-7-carboxylic acid [(R)-1-(1-cyano-cyclopentyl)-ethyl]-amide (140 mg, 0.25 mmol) in CH$_2$Cl$_2$ (2 mL) was added TFA (0.75 mL). The reaction mixture was stirred at room temperature for 4 h then concentrated. The residue was redissolved in 10:90:0.5 MeOH/CH$_2$Cl$_2$/NH$_4$OH (3 mL) and stirred at room temperature for 3 h then concentrated. The residue was purified by silica gel chromatography with 0% to 5% MeOH/EtOAc to afford 92 mg (86%) of 2-(6-fluoro-1-methyl-1H-indazol-3-yl)-5H-pyrrolo[2,3-b]pyrazine-7-carboxylic acid [(R)-1-(1-cyano-cyclopentyl)-ethyl]-amide as a light yellow powder. MS (M+Na)$^+$=454; mp=300-315° C.; $^1$H NMR (DMSO-d$_6$, 300 MHz): δ (ppm) 12.96 (br. s., 1H), 9.11 (s, 1H), 8.51-8.56 (m, 1H), 8.50 (s, 1H), 8.19 (d, J=9.1 Hz, 1H), 7.67 (dd, J=9.8, 1.9 Hz, 1H), 7.15 (td, J=9.1, 2.3 Hz, 1H), 4.34-4.50 (m, 1H), 4.14 (s, 3H), 1.92-2.14 (m, 3H), 1.63-1.90 (m, 5H), 1.46 (d, J=6.8 Hz, 3H).

Example 101

2-(4,6-Difluoro-1-methyl-1H-indazol-3-yl)-5H-pyrrolo[2,3-b]pyrazine-7-carboxylic acid isopropylamide

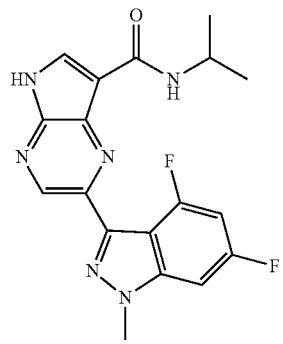 [SMILES: CC(C)NC(=O)c1c[nH]c2ncc(-c3nn(C)c4cc(F)cc(F)c34)nc12]

Step 1

4,6-Difluoro-3-iodo-1H-indazole

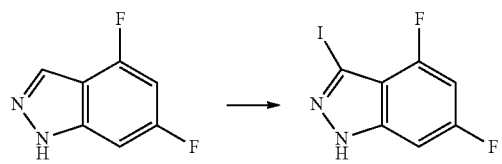 [SMILES: Fc1cc(F)c2cn[nH]c2c1 ; Fc1cc(F)c2c(I)n[nH]c2c1]

To a solution of 4,6-difluoro-1H-indazole (1.16 g, 7.53 mmol) in DMF (60 ml) at room temperature was added potassium hydroxide (1.27 g, 22.6 mmol) and iodine (2.87 g, 11.3 mmol). The maroon reaction mixture was stirred at room temperature for 2 h then quenched with 10% aqueous Na$_2$S$_2$O$_3$ and diluted with water. The mixture was extracted with EtOAc (2×). The combined organics were washed with water, sat LiCl, and sat NaCl, then dried over MgSO$_4$ and concentrated to afford 2.18 g of 4,6-difluoro-3-iodo-1H-indazole as a light brown solid.

Step 2

4,6-Difluoro-3-tributylstannanyl-1H-indazole

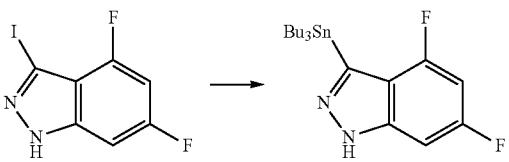

To a solution of 4,6-difluoro-3-iodo-1H-indazole (2.11 g, 7.53 mmol) in THF (45 mL) at 0° C. was slowly added sodium hydride (60% in mineral oil, 362 mg, 9.04 mmol). The reaction mixture was stirred at room temperature for 10 min then cooled to −10° C. and isopropylmagnesium chloride (2.0 M in THF, 4.52 mL, 9.04 mmol) was added. The reaction mixture was stirred at −10° C. for 30 min then tributylchlorostannane (2.66 mL, 9.8 mmol) was added dropwise. Stirring was continued at −10° C. for 20 min then at room temperature for 3 h. The reaction mixture was quenched with saturated aqueous NH₄Cl then diluted with water and extracted with EtOAc (2×). The combined organics were washed with brine then dried over MgSO₄ and concentrated. The residue was purified by silica gel chromatography with 10% to 20% EtOAc/heptane (0.5% Et₃N) to afford 1.94 g (58%) of 4,6-difluoro-3-tributylstannanyl-1H-indazole as a pale yellow viscous oil. ¹H NMR (CDCl₃, 300 MHz): δ (ppm) 7.03 (dd, J=8.9, 2.1 Hz, 1H), 6.60 (td, J=9.8, 2.1 Hz, 1H), 1.51-1.64 (m, 6H), 1.29-1.42 (m, 6H), 1.20-1.29 (m, 6H), 0.88 (t, J=7.4 Hz, 9H).

Step 3

2-(4,6-Difluoro-1H-indazol-3-yl)-5-(2-trimethylsilanyl-ethoxymethyl)-5H-pyrrolo[2,3-b]pyrazine-7-carbaldehyde

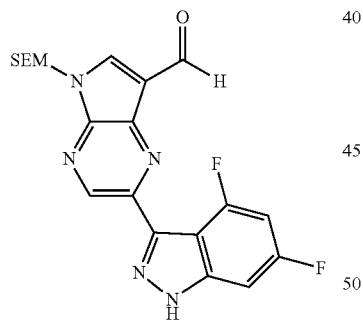

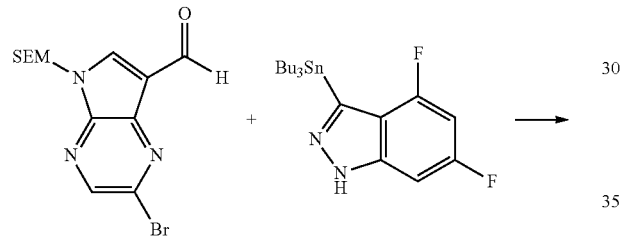

In a round-bottomed flask, 2-bromo-5-(2-trimethylsilanyl-ethoxymethyl)-5H-pyrrolo[2,3-b]pyrazine-7-carbaldehyde (1.56 g, 4.38 mmol) and 4,6-difluoro-3-tributylstannanyl-1H-indazole (1.94 g, 4.38 mmol) were dissolved in DMF (40 mL) and tetrakis(triphenylphosphine)palladium(0) (253 mg, 0.22 mmol) and copper(I) iodide (167 mg, 0.88 mmol) were added. The reaction mixture was purged with argon, stirred at room temperature for 4 h, then heated at 80° C. for 1 h. The reaction was cooled to room temperature, quenched with sat NH₄Cl and extracted with EtOAc (2×). The combined organics were washed with sat LiCl and brine then dried over MgSO₄ and concentrated. The crude residue was purified by silica gel chromatography with 50% to 100% EtOAc/heptane to provide 1.89 g of 2-(4,6-difluoro-1H-indazol-3-yl)-5-(2-trimethylsilanyl-ethoxymethyl)-5H-pyrrolo[2,3-b]pyrazine-7-carbaldehyde as a brown solid.

Step 4

2-(4,6-Difluoro-1-methyl-1H-indazol-3-yl)-5-(2-trimethylsilanyl-ethoxymethyl)-5H-pyrrolo[2,3-b]pyrazine-7-carbaldehyde

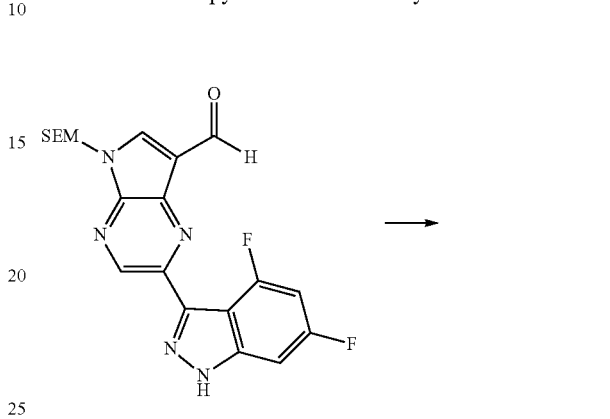

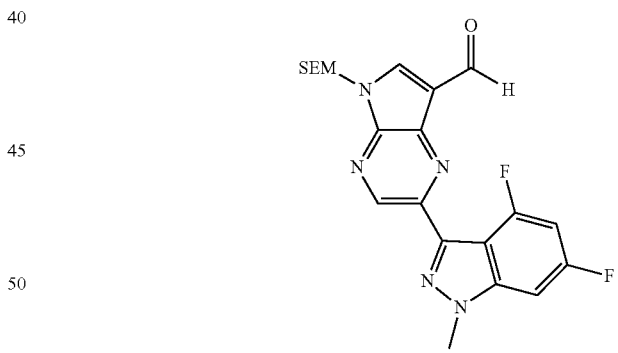

To a solution of 2-(4,6-difluoro-1H-indazol-3-yl)-5-(2-trimethylsilanyl-ethoxymethyl)-5H-pyrrolo[2,3-b]pyrazine-7-carbaldehyde (890 mg, 2.1 mmol) in DMF (9 ml) at 0° C. was added sodium hydride (60% in mineral oil, 279 mg, 2.49 mmol). The reaction mixture was stirred at 0° C. for 10 min then iodomethane (0.18 ml, 2.9 mmol) was slowly added. The mixture was stirred at 0° C. for 30 min then at room temperature for 30 min. The reaction was quenched with sat'd NH₄Cl, diluted with water and extracted with EtOAc (2×). The combined organics were washed with sat LiCl and brine then dried over MgSO₄ and concentrated. The crude residue was purified by silica gel chromatography with 20% to 100% EtOAc/heptane to provide 226 mg (22%) of 2-(4,6-difluoro- 1-methyl-1H-indazol-3-yl)-5-(2-trimethylsilanyl-ethoxymethyl)-5H-pyrrolo[2,3-b]pyrazine-7-carbaldehyde as a yellow solid.

Step 5

2-(4,6-Difluoro-1-methyl-1H-indazol-3-yl)-5-(2-trimethylsilanyl-ethoxymethyl)-5H-pyrrolo[2,3-b]pyrazine-7-carboxylic acid

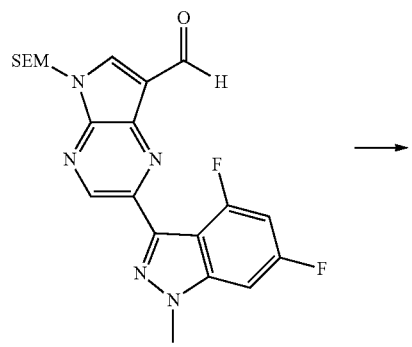

difluoro-1-methyl-1H-indazol-3-yl)-5-(2-trimethylsilanyl-ethoxymethyl)-5H-pyrrolo[2,3-b]pyrazine-7-carboxylic acid as a light yellow powder.

Step 6

2-(4,6-Difluoro-1-methyl-1H-indazol-3-yl)-5-(2-trimethylsilanyl-ethoxymethyl)-5H-pyrrolo[2,3-b]pyrazine-7-carboxylic acid isopropylamide

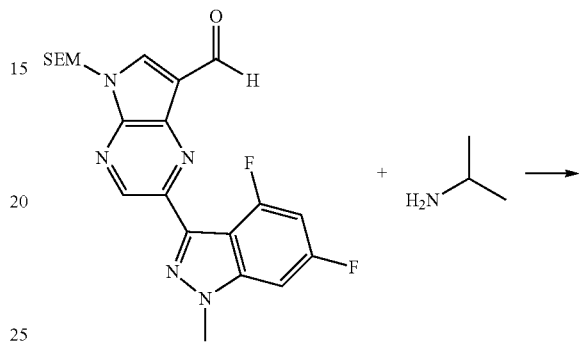

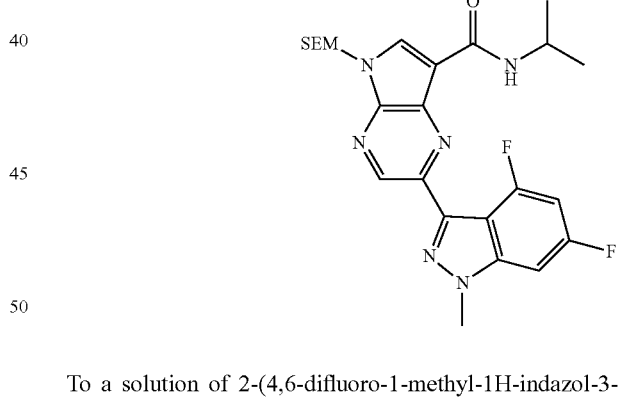

To a solution of 2-(4,6-difluoro-1-methyl-1H-indazol-3-yl)-5-(2-trimethylsilanylethoxymethyl)-5H-pyrrolo[2,3-b]pyrazine-7-carbaldehyde (226 mg, 0.51 mmol) in 1,4-dioxane (15 ml) and water (3 ml) at 0° C. was added sulfamic acid (297 mg, 3.06 mmol). Then a solution of sodium chlorite (80%, 75 mg, 0.66 mmol) and potassium dihydrogen phosphate (834 mg, 6.13 mmol) in water (12 ml) was added via dropping funnel over ~15 min. After the addition was complete, the ice bath was removed and the reaction mixture was stirred at room temperature for 3 h. The reaction mixture was diluted with water and extracted with EtOAc (3×). The combined organic layers were washed with brine then dried over MgSO$_4$ and concentrated to afford 230 mg (98%) of 2-(4,6-

To a solution of 2-(4,6-difluoro-1-methyl-1H-indazol-3-yl)-5-(2-trimethylsilanylethoxymethyl)-5H-pyrrolo[2,3-b]pyrazine-7-carboxylic acid (75 mg, 0.16 mmol), HOBt (63 mg, 0.38 mmol) and EDC (72 mg, 0.38 mmol) in DMF was added isopropylamine (84 ul, 0.98 mmol). The reaction mixture was stirred at room temperature for 1.5 h then additional HOBt, EDC, and isopropylamine were added. The reaction mixture was stirred at room temperature overnight then diisopropylethylamine (170 ul, 0.98 mmol) was added. The reaction was stirred for 1 h then quenched with water and extracted with EtOAc (2×). The combined organic layers were washed with 10% citric acid, sat NaHCO$_3$, sat LiCl, and brine then dried over MgSO$_4$ and concentrated. The residue was chromatographed over silica gel with 20% to 100% EtOAc/heptane to afford 30 mg (37%) of 2-(4,6-difluoro-1- methyl-1H-indazol-3-yl)-5-(2-trimethylsilanyl-ethoxymethyl)-5H-pyrrolo[2,3-b]pyrazine-7-carboxylic acid isopropylamide as a white solid.

Step 7

2-(4,6-Difluoro-1-methyl-1H-indazol-3-yl)-5H-pyrrolo[2,3-b]pyrazine-7-carboxylic acid isopropylamide

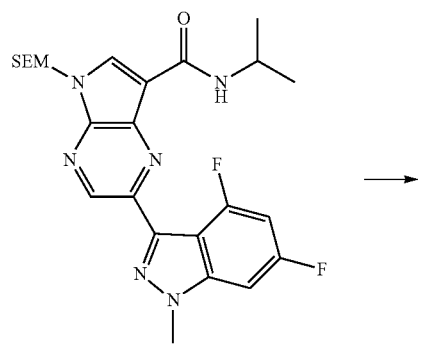

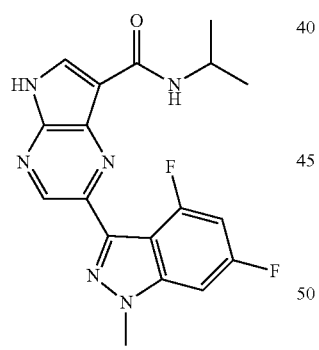

To a solution of 2-(4,6-difluoro-1-methyl-1H-indazol-3-yl)-5-(2-trimethylsilanylethoxymethyl)-5H-pyrrolo[2,3-b]pyrazine-7-carboxylic acid isopropylamide (30 mg, 0.06 mmol) in CH$_2$Cl$_2$ (1.5 mL) was added TFA (0.5 mL). The reaction mixture was stirred at room temperature for 4 h then concentrated. The residue was redissolved in 10:90:0.5 MeOH/CH$_2$Cl$_2$/NH$_4$OH (3 mL) and stirred at room temperature for 3 h then concentrated. The residue was purified by silica gel chromatography with 0% to 5% MeOH/EtOAc to afford 18 mg (82%) of 2-(4,6-difluoro-1-methyl-1H-indazol-3-yl)-5H-pyrrolo[2,3-b]pyrazine-7-carboxylic acid isopropylamide as a light yellow powder. MS (M+Na)$^+$=393; $^1$H NMR (DMSO-d$_6$, 300 MHz): δ (ppm) 12.83 (s, 1H), 8.99 (s, 1H), 8.40 (s, 1H), 8.27 (d, J=7.9 Hz, 1H), 7.59 (dd, J=9.1, 1.9 Hz, 1H), 7.12-7.23 (m, 1H), 4.16-4.27 (m, 1H), 4.14 (s, 3H), 1.22 (d, J=6.4 Hz, 6H).

Example 102

2-(6-Fluoro-1-oxetan-3-yl-1H-indazol-3-yl)-5H-pyrrolo[2,3-b]pyrazine-7-carboxylic acid isopropylamide

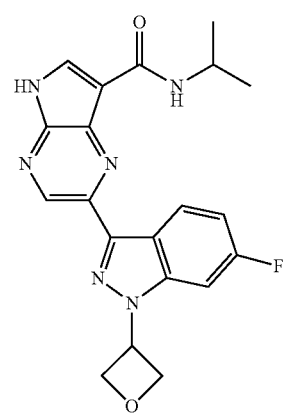 [SMILES: CC(C)NC(=O)c1c[nH]c2ncc(-c3nn(C4COC4)c4cc(F)ccc34)nc12]

Step 1

6-Fluoro-3-iodo-1H-indazole

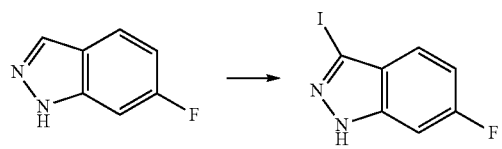 [SMILES: Fc1ccc2cn[nH]c2c1 ; Fc1ccc2c(I)n[nH]c2c1]

To a solution of 6-fluoro-1H-indazole (5.50 g, 40.4 mmol) in DMF (150 ml) at room temperature was added potassium hydroxide (6.8 g, 121 mmol) and iodine (15.4 g, 60.6 mmol). The maroon reaction mixture was stirred at room temperature for 8 h then quenched with 10% aqueous Na$_2$S$_2$O$_3$ and diluted with water. The mixture was extracted with EtOAc (2×). The combined organics were washed with water, sat LiCl, and sat NaCl, then dried over MgSO$_4$ and concentrated to afford 8.6 g (81%) of 6-fluoro-3-iodo-1H-indazole as a light yellow solid. $^1$H NMR (CDCl$_3$, 300 MHz): δ (ppm) 7.48 (dd, J=8.9, 5.1 Hz, 1H), 7.20 (dd, J=8.9, 2.1 Hz, 1H), 7.02 (td, J=9.1, 2.1 Hz, 1H)

Step 2

6-Fluoro-3-tributylstannanyl-1H-indazole

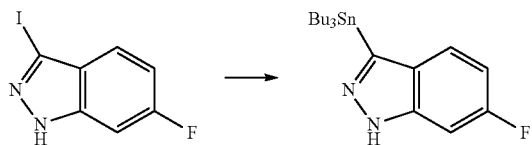

To a solution of 6-fluoro-3-iodo-1H-indazole (8.6 g, 32.8 mmol) in THF (200 mL) at 0° C. was slowly added portionwise sodium hydride (60% in mineral oil, 1.58 g, 39.4 mmol). The reaction mixture was stirred at room temperature for 10 min then cooled to −10° C. and isopropylmagnesium chloride (2.0 M in THF, 19.7 mL, 39.4 mmol) was added. The reaction mixture was stirred at −10° C. for 30 min then additional isopropylmagnesium chloride (2.0 M in THF, 8.2 mL, 16.4 mmol) was added. The reaction mixture was stirred at −10° C. for 30 min then tributylchlorostannane (11.6 mL, 42.7 mmol) was slowly added. Stirring was continued at −10° C. for 20 min then at room temperature for 3 h. The reaction mixture was quenched with saturated aqueous NH$_4$Cl then diluted with water and extracted with EtOAc (2×). The combined organics were washed with brine then dried over MgSO$_4$ and concentrated. The residue was purified by silica gel chromatography with 10% to 20% EtOAc/heptane (0.5% Et$_3$N) to afford 6.53 g (47%) of 6-fluoro-3-tributylstannanyl-1H-indazole as a light brown viscous oil. $^1$H NMR (CDCl$_3$, 300 MHz): δ (ppm) 7.65 (dd, J=8.7, 5.3 Hz, 1H), 7.20 (dd, J=9.3, 2.1 Hz, 1H), 6.92 (td, J=9.0, 2.1 Hz, 1H), 1.53-1.67 (m, 6H), 1.28-1.43 (m, 6H), 1.20-1.28 (m, 6H), 0.89 (t, J=7.4 Hz, 9H).

Step 3

2-(6-Fluoro-1H-indazol-3-yl)-5-(2-trimethylsilanyl-ethoxymethyl)-5H-pyrrolo[2,3-b]pyrazine-7-carbaldehyde

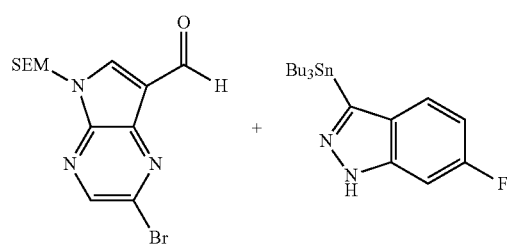

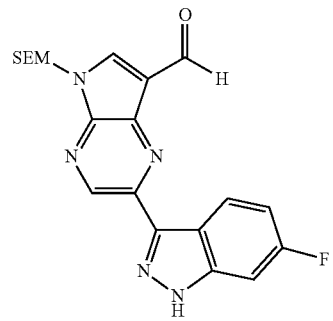

In a round-bottomed flask, 2-bromo-5-(2-trimethylsilanyl-ethoxymethyl)-5H-pyrrolo[2,3-b]pyrazine-7-carbaldehyde (5.47 g, 15.4 mmol) and 6-fluoro-3-tributylstannanyl-1H-indazole (6.53 g, 15.4 mmol) were dissolved in DMF (140 mL) and tetrakis(triphenylphosphine)palladium(0) (888 mg, 0.76 mmol) and copper(I) iodide (585 mg, 3.07 mmol) were added. The reaction mixture was purged with argon then heated at 80° C. for 1 h. The reaction was cooled to room temperature, quenched with sat NH$_4$Cl and extracted with EtOAc (2×). The combined organics were washed with sat LiCl and brine then dried over MgSO$_4$ and concentrated. The crude residue was recrystallized from EtOAc to afford 3.74 g of a white solid. The mother liquor was purified by silica gel chromatography with 50% to 100% EtOAc/heptane to provide an additional 1.75 g white solid. Overall yield was 5.49 g (87%) of 2-(6-fluoro-1H-indazol-3-yl)-5-(2-trimethylsilanyl-ethoxymethyl)-5H-pyrrolo[2,3-b]pyrazine-7-carbaldehyde. $^1$H NMR (CDCl$_3$, 300 MHz): δ (ppm) 10.49 (s, 1H), 9.34 (s, 1H), 8.83 (dd, J=9.1, 5.3 Hz, 1H), 8.32 (s, 1H), 7.08-7.25 (m, 2H), 5.77 (s, 2H), 3.55-3.71 (m, 2H), 0.87-1.03 (m, 2H), −0.03 (s, 9H).

Step 4

2-(6-Fluoro-1-oxetan-3-yl-1H-indazol-3-yl)-5-(2-trimethylsilanyl-ethoxymethyl)-5H-pyrrolo[2,3-b]pyrazine-7-carbaldehyde

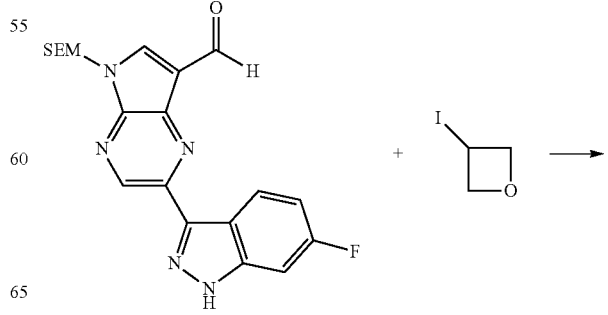

559
-continued

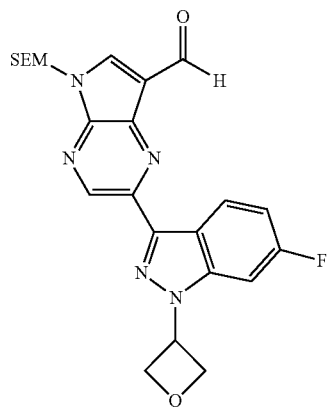

In a microwave vial 2-(6-fluoro-1H-indazol-3-yl)-5-(2-tri-methylsilanyl-ethoxymethyl)-5H-pyrrolo[2,3-b]pyrazine-7-carbaldehyde (300 mg, 0.73 mmol) was dissolved in DMF (5 ml) and cesium carbonate (714 mg, 2.19 mmol) and 3-iodooxetane (200 mg, 1.08 mmol) were added. The vial was sealed and heated at 100° C. under microwave irradiation for 2 h. The reaction was cooled, quenched with water and extracted with EtOAc (2×). The combined organics were washed with sat LiCl and brine then dried over MgSO$_4$ and concentrated. The crude residue was purified by silica gel chromatography with 20% to 100% EtOAc/heptane to provide 295 mg (86%) of 2-(6-fluoro-1-oxetan-3-yl-1H-indazol-3-yl)-5-(2-trimethylsilanyl-ethoxymethyl)-5H-pyrrolo[2,3-b]pyrazine-7-carbaldehyde as a white solid. $^1$H NMR (CDCl$_3$, 300 MHz): δ (ppm) 10.48 (s, 1H), 9.40 (s, 1H), 8.86 (dd, J=9.1, 5.3 Hz, 1H), 8.31 (s, 1H), 7.11-7.25 (m, 2H), 5.72-5.86 (m, 3H), 5.41 (t, J=6.6 Hz, 2H), 5.20 (t, J=7.4 Hz, 2H), 3.56-3.70 (m, 2H), 0.85-1.06 (m, 2H), −0.02 (s, 9H).

560
-continued

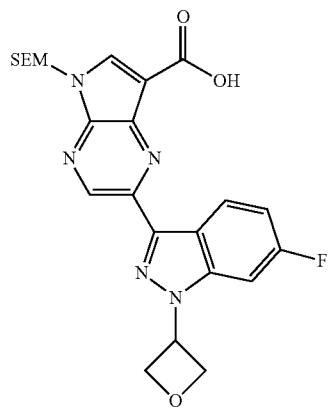

To a solution of 2-(6-fluoro-1-oxetan-3-yl-1H-indazol-3-yl)-5-(2-trimethylsilanylethoxymethyl)-5H-pyrrolo[2,3-b]pyrazine-7-carbaldehyde (293 mg, 0.63 mmol) in 1,4-dioxane (20 ml) and water (4 ml) at 0° C. was added sulfamic acid (365 mg, 3.76 mmol). Then a solution of sodium chlorite (80%, 92 mg, 0.82 mmol) and potassium dihydrogen phosphate (1.02 g, 7.52 mmol) in water (16 ml) was added over ~15 min. After the addition was complete, the ice bath was removed and the reaction mixture was stirred at room temperature for 30 min. THF (20 ml) was added and stirred was continued for 2 h. The reaction mixture was diluted with water and extracted with EtOAc (3×). The combined organic layers were washed with brine then dried over MgSO$_4$ and concentrated to afford 340 mg of 2-(6-fluoro-1-oxetan-3-yl-1H-indazol-3-yl)-5-(2-trimethylsilanyl-ethoxymethyl)-5H-pyrrolo[2,3-b]pyrazine-7-carboxylic acid as an off-white powder.

Step 5

2-(6-Fluoro-1-oxetan-3-yl-1H-indazol-3-yl)-5-(2-trimethylsilanyl-ethoxymethyl)-5H-pyrrolo[2,3-b]pyrazine-7-carboxylic acid

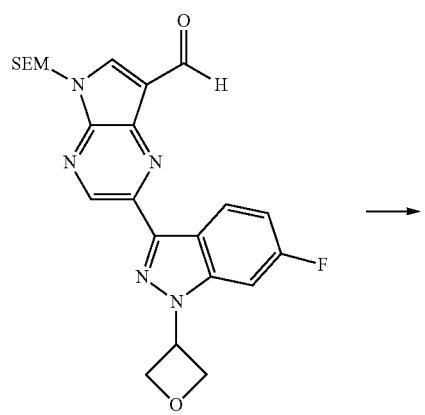

Step 6

2-(6-Fluoro-1-oxetan-3-yl-1H-indazol-3-yl)-5-(2-trimethylsilanyl-ethoxymethyl)-5H-pyrrolo[2,3-b]pyrazine-7-carboxylic acid isopropylamide

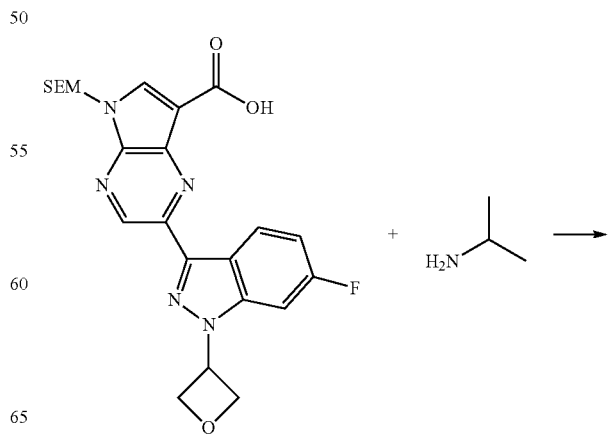

-continued

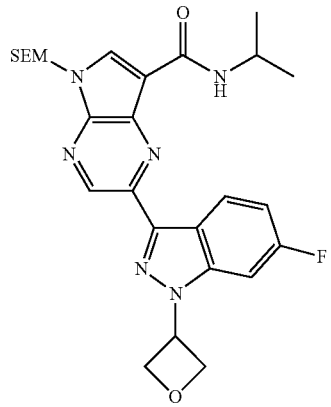

To a solution of 2-(4,6-difluoro-1-methyl-1H-indazol-3-yl)-5-(2-trimethylsilanylethoxymethyl)-5H-pyrrolo[2,3-b]pyrazine-7-carboxylic acid (115 mg, 0.23 mmol), HOBt (92 mg, 0.55 mmol) and EDC (105 mg, 0.55 mmol) in DMF (3 ml) was added isopropylamine (41 ul, 0.48 mmol) and N,N-diisopropylethylamine (0.17 ml, 0.95 mmol). The reaction mixture was stirred at room temperature overnight then quenched with water and extracted with EtOAc (2×). The combined organic layers were washed with 10% citric acid, sat NaHCO$_3$, sat LiCl, and brine then dried over MgSO$_4$ and concentrated. The residue was chromatographed over silica gel with 20% to 100% EtOAc/heptane to afford 98 mg (78%) of 2-(6-fluoro-1-oxetan-3-yl-1H-indazol-3-yl)-5-(2-trimethylsilanyl-ethoxymethyl)-5H-pyrrolo[2,3-b]pyrazine-7-carboxylic acid isopropylamide as a white solid.

Step 7

2-(6-Fluoro-1-oxetan-3-yl-1H-indazol-3-yl)-5H-pyrrolo[2,3-b]pyrazine-7-carboxylic acid isopropylamide

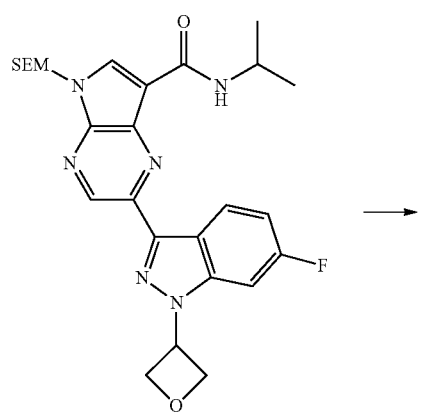

-continued

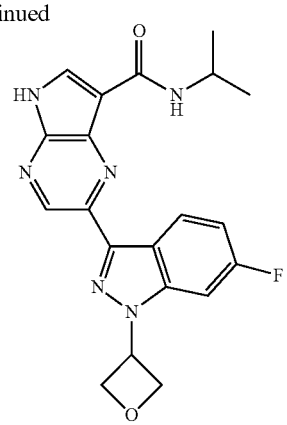

To a solution of 2-(6-fluoro-1-oxetan-3-yl-1H-indazol-3-yl)-5-(2-trimethylsilanylethoxymethyl)-5H-pyrrolo[2,3-b]pyrazine-7-carboxylic acid isopropylamide (98 mg, 0.18 mmol) in CH$_2$Cl$_2$ (1.5 mL) was added TFA (0.5 mL). The reaction mixture was stirred at room temperature for 3 h then concentrated. The residue was redissolved in 10:90:0.5 MeOH/CH$_2$Cl$_2$/NH$_4$OH (3 mL) and stirred at room temperature for 3 h then concentrated. The residue was portioned between water and 10% MeOH/CH$_2$Cl$_2$. The aqueous layer was extracted with 10% MeOH/CH$_2$Cl$_2$ (3×). The combined organics were concentrated and the residue was purified by silica gel chromatography with 0% to 5% MeOH/CH$_2$Cl$_2$ (0.5% NH$_4$OH) to afford 30 mg (41%) of 2-(6-fluoro-1-oxetan-3-yl-1H-indazol-3-yl)-5H-pyrrolo[2,3-b]pyrazine-7-carboxylic acid isopropylamide as a white solid. MS (M+Na)$^+$=417; $^1$H NMR (DMSO-d$_6$, 300 MHz): δ (ppm) 12.87 (br. s., 1H), 9.20 (s, 1H), 8.45-8.51 (m, 1H), 8.44 (s, 1H), 8.04 (d, J=7.6 Hz, 1H), 7.73 (dd, J=9.8, 1.9 Hz, 1H), 7.22 (td, J=9.1, 1.9 Hz, 1H), 6.13 (quin, J=7.0 Hz, 1H), 5.11-5.20 (m, 2H), 4.99-5.10 (m, 2H), 4.21 (dq, J=13.5, 6.4 Hz, 1H), 1.30 (d, J=6.4 Hz, 6H).

Example 103

2-(6-Fluoro-1-oxetan-3-yl-1H-indazol-3-yl)-5H-pyrrolo[2,3-b]pyrazine-7-carboxylic acid ((S)-2-methoxy-1-methyl-ethyl)-amide

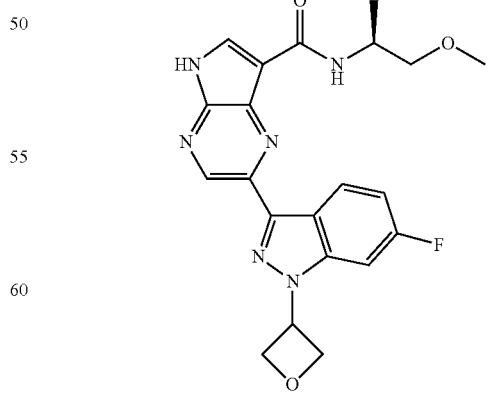

Prepared according to the procedure outlined in Example 102, Steps 6-7, substituting (S)-1-methoxypropan-2-amine hydrochloride for isopropylamine in Step 6. MS: (M+Na)$^+$= 447; $^1$H NMR (DMSO-d$_6$, 400 MHz): δ (ppm) 12.87 (br. s., 1H), 9.25 (s, 1H), 8.56 (dd, J=9.0, 5.2 Hz, 1H), 8.47 (s, 1H), 8.21 (d, J=8.3 Hz, 1H), 7.74 (dd, J=9.7, 2.1 Hz, 1H), 7.20 (td, J=9.0, 2.1 Hz, 1H), 6.09-6.22 (m, 1H), 5.18 (q, J=6.1 Hz, 2H), 5.03-5.11 (m, 2H), 4.34-4.44 (m, 1H), 3.40-3.57 (m, 2H), 3.31 (s, 3H), 1.32 (d, J=6.8 Hz, 3H).

Example 104

2-(1-Azetidin-3-yl-6-fluoro-1H-indazol-3-yl)-5H-pyrrolo[2,3-b]pyrazine-7-carboxylic acid isopropylamide

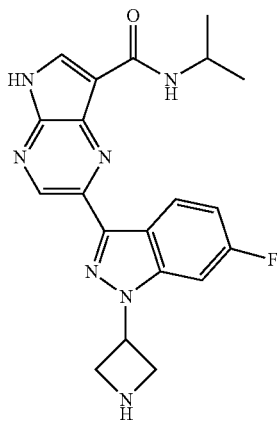 [SMILES: CC(C)NC(=O)c1c[nH]c2ncc(-c3nn(C4CNC4)c4cc(F)ccc34)nc12]

Step 1

2-[1-(1-Benzhydryl-azetidin-3-yl)-6-fluoro-1H-indazol-3-yl]-5-(2-trimethylsilanylethoxymethyl)-5H-pyrrolo[2,3-b]pyrazine-7-carbaldehyde

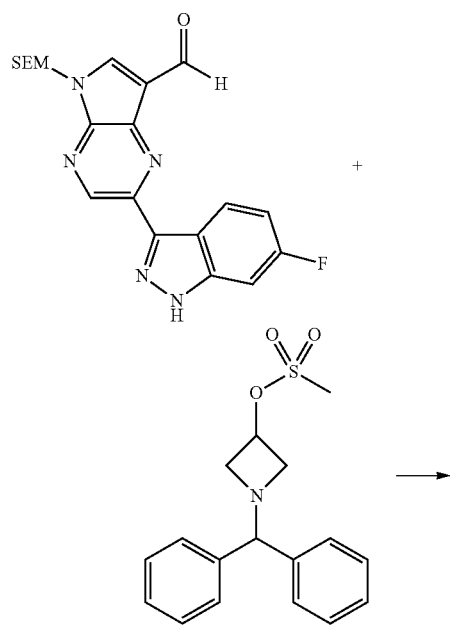

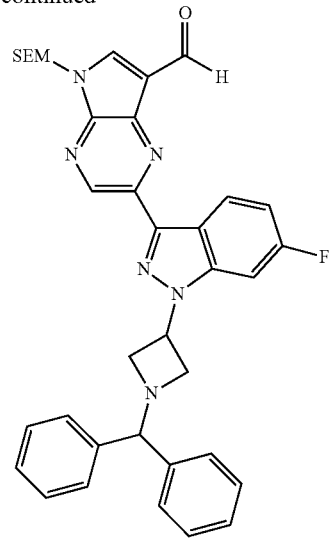

In a microwave vial 2-(6-fluoro-1H-indazol-3-yl)-5-(2-trimethylsilanyl-ethoxymethyl)-5H-pyrrolo[2,3-b]pyrazine-7-carbaldehyde (300 mg, 0.73 mmol) was dissolved in DMF (6 ml) and cesium carbonate (713 mg, 2.19 mmol) and methanesulfonic acid 1-benzhydryl-azetidin-3-yl ester (347 mg, 1.09 mmol) were added. The vial was sealed and heated in a microwave reactor at 100° C. 3 h. The reaction was cooled, quenched with water and extracted with EtOAc (2×). The combined organics were washed with water and brine then dried over MgSO$_4$ and concentrated. The crude residue was purified by silica gel chromatography with 20% to 30% EtOAc/hexanes to provide 176 mg (38%) of 2-[1-(1-benzhydryl-azetidin-3-yl)-6-fluoro-1H-indazol-3-yl]-5-(2-trimethylsilanyl-ethoxymethyl)-5H-pyrrolo[2,3-b]pyrazine-7-carbaldehyde as an orange foam.

Step 2

2-[1-(1-Benzhydryl-azetidin-3-yl)-6-fluoro-1H-indazol-3-yl]-5-(2-trimethylsilanylethoxymethyl)-5H-pyrrolo[2,3-b]pyrazine-7-carboxylic acid

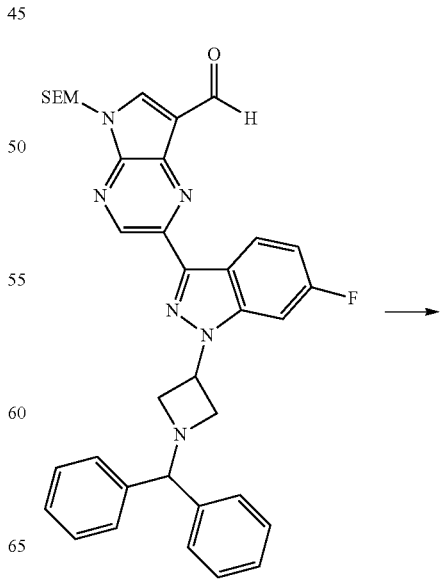

565

-continued

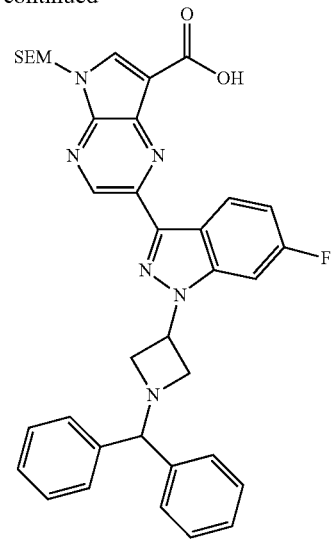

To a solution of 2-[1-(1-benzhydryl-azetidin-3-yl)-6-fluoro-1H-indazol-3-yl]-5-(2-trimethylsilanyl-ethoxymethyl)-5H-pyrrolo[2,3-b]pyrazine-7-carbaldehyde (170 mg, 0.27 mmol) in 1,4-dioxane (10 mL) and water (2 mL) at 0° C. was added sulfamic acid (157 mg, 1.61 mmol). Then added a solution of NaClO$_2$ (43 mg, 0.37 mmol) and KH$_2$PO$_4$ (439 mg, 3.22 mmol) in water (4 mL) dropwise over 5 min. The ice bath was removed and the yellow cloudy reaction mixture was stirred at room temperature overnight. The mixture was diluted with water and extracted with EtOAc (2×). The combined organic layers were dried over MgSO$_4$ and concentrated. The residue was triturated with petroleum ether to isolate 45 mg (26%) of 2-[1-(1-benzhydryl-azetidin-3-yl)-6-fluoro-1H-indazol-3-yl]-5-(2-trimethylsilanyl-ethoxymethyl)-5H-pyrrolo[2,3-b]pyrazine-7-carboxylic acid as a light yellow solid.

Step 3

2-[1-(1-Benzhydryl-azetidin-3-yl)-6-fluoro-1H-indazol-3-yl]-5-(2-trimethylsilanylethoxymethyl)-5H-pyrrolo[2,3-b]pyrazine-7-carboxylic acid isopropylamide

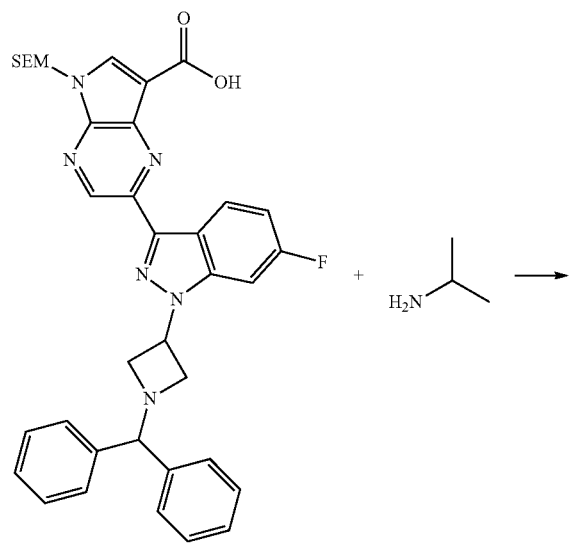

566

-continued

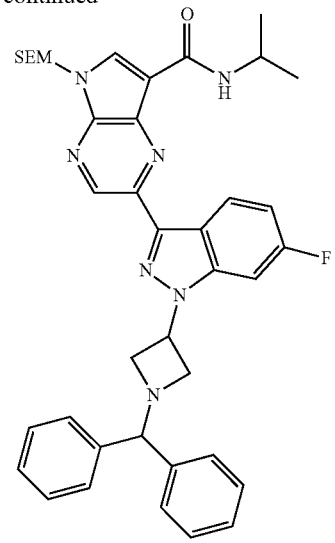

To a solution of 2-[1-(1-benzhydryl-azetidin-3-yl)-6-fluoro-1H-indazol-3-yl]-5-(2-trimethylsilanyl-ethoxymethyl)-5H-pyrrolo[2,3-b]pyrazine-7-carboxylic acid (130 mg, 0.20 mmol) in DMF (2 mL) were added HATU (84 mg, 0.22 mmol) and isopropylamine (86 μL, 1.00 mmol). The reaction mixture was stirred at room temperature overnight then quenched with water and extracted with EtOAc (2×). The combined organics were washed with water (3×) and brine then dried over MgSO$_4$ and concentrated. The residue was purified by silica gel chromatography with 50% EtOAc/hexanes to isolate 74 mg (54%) of 2-[1-(1-benzhydryl-azetidin-3-yl)-6-fluoro-1H-indazol-3-yl]-5-(2-trimethylsilanyl-ethoxymethyl)-5H-pyrrolo[2,3-b]pyrazine-7-carboxylic acid isopropylamide as an off-white foamy solid.

Step 4

2-(1-Azetidin-3-yl-6-fluoro-1H-indazol-3-yl)-5-(2-trimethylsilanyl-ethoxymethyl)-5H-pyrrolo[2,3-b]pyrazine-7-carboxylic acid isopropylamide

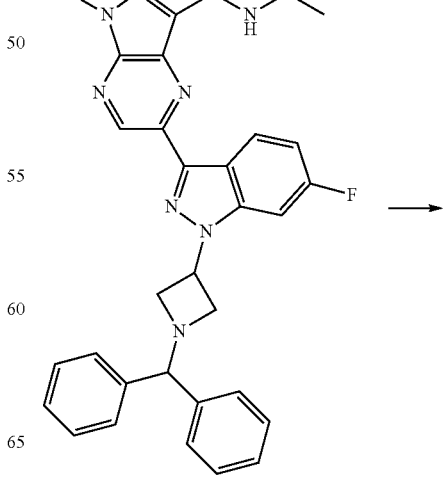

567
-continued

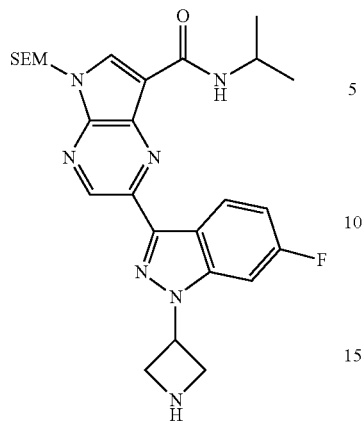

In a round-bottomed flask ammonium formate (135 mg, 2.15 mmol) was dissolved in MeOH (1.5 mL). This solution was added to a solution of 2-[1-(1-benzhydryl-azetidin-3-yl)-6-fluoro-1H-indazol-3-yl]-5-(2-trimethylsilanyl-ethoxymethyl)-5H-pyrrolo[2,3-b]pyrazine-7-carboxylic acid isopropylamide (74 mg, 0.107 mmol) in THF (1.5 mL) which caused a white precipitate to form. This slurry was transferred via pipet to a pressure tube containing 10% palladium on carbon (wet, 23 mg) in MeOH (1 mL). The tube was sealed and heated at 50° C. for 4 h then cooled to room temperature overnight. The mixture was filtered over Celite, rinsing with CH$_2$Cl$_2$. The filtrate was concentrated and the residue was absorbed onto SiO$_2$ and chromatographed with 0% to 10% MeOH/CH$_2$Cl$_2$ (0.5% NH$_4$OH) to afford 38 mg (68%) of 2-(1-azetidin-3-yl-6-fluoro-1H-indazol-3-yl)-5-(2-trimethylsilanyl-ethoxymethyl)-5H-pyrrolo[2,3-b]pyrazine-7-carboxylic acid isopropylamide as a pale yellow foamy solid.

Step 5

2-(1-Azetidin-3-yl-6-fluoro-1H-indazol-3-yl)-5H-pyrrolo[2,3-b]pyrazine-7-carboxylic acid isopropylamide

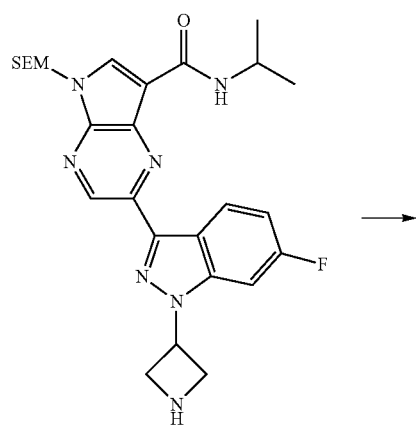

568
-continued

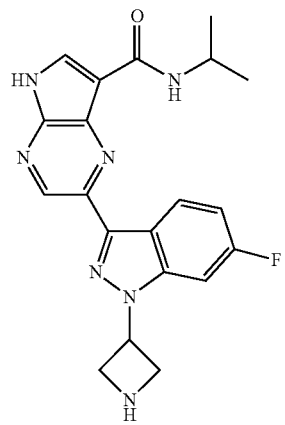

To a solution of 2-(1-azetidin-3-yl-6-fluoro-1H-indazol-3-yl)-5-(2-trimethylsilanylethoxymethyl)-5H-pyrrolo[2,3-b]pyrazine-7-carboxylic acid isopropylamide (36 mg, 0.69 mmol) in CH$_2$Cl$_2$ (1 mL) was added TFA (0.5 mL, 6.5 mmol). The reaction mixture was stirred at room temperature for 3 h then concentrated. The residue was redissolved in CH$_2$Cl$_2$ (1 mL) and ethylene diamine (0.2 mL, 3.00 mmol) was added. The reaction mixture was stirred at room temperature for 1 h then quenched with water and extracted with 5% MeOH/CH$_2$Cl$_2$ (3×). The combined organic layers were dried over MgSO$_4$ and concentrated. The residue was triturated with EtOAc to afford 17 mg (63%) of 2-(1-azetidin-3-yl-6-fluoro-1H-indazol-3-yl)-5H-pyrrolo[2,3-b]pyrazine-7-carboxylic acid isopropylamide as a pale yellow powder. MS: (M+H)$^+$= 394; $^1$H NMR (DMSO-d$_6$, 300 MHz): δ (ppm) 9.14 (s, 1H), 8.40-8.50 (m, 2H), 8.04 (d, J=7.6 Hz, 1H), 7.78-7.86 (m, 1H), 7.13-7.24 (m, 1H), 5.65-5.76 (m, 1H), 4.12-4.28 (m, 3H), 3.86 (t, J=7.9 Hz, 2H), 1.30 (d, J=6.4 Hz, 3H).

Example 105

2-(6-Chloro-1-methyl-1H-indazol-3-yl)-5H-pyrrolo[2,3-b]pyrazine-7-carboxylic acid ((R)-2-methanesulfonyl-1-methyl-ethyl)-amide

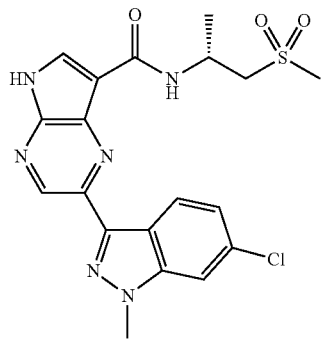 [SMILES: C[C@H](CS(C)(=O)=O)NC(=O)c1c[nH]c2ncc(-c3nn(C)c4cc(Cl)ccc34)nc12]

Step 1

2-(6-Chloro-1-methyl-1H-indazol-3-yl)-5-(2-trimethylsilanyl-ethoxymethyl)-5H-pyrrolo[2,3-b]pyrazine-7-carboxylic acid ((R)-2-methanesulfonyl-1-methyl-ethyl)-amide

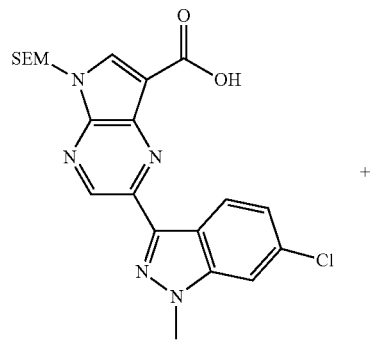

+

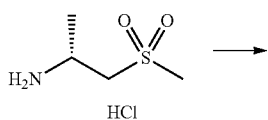

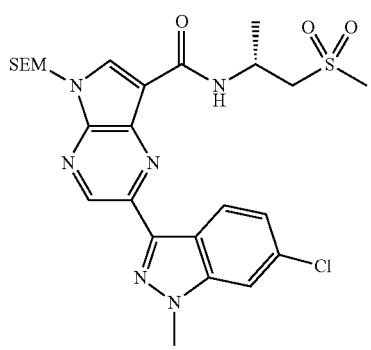

2-(6-Chloro-1-methyl-1H-indazol-3-yl)-5-(2-trimethylsilanyl-ethoxymethyl)-5H-pyrrolo[2,3-b]pyrazine-7-carboxylic acid (80 mg, 0.175 mmol), O-benzotriazol-1-yl-N,N,N',N'-tetramethyluronium tetrafluoroborate (84 mg, 0.26 mmol) and N,N-diisopropylethylamine (0.076 ml, 0.44 mmol) were dissolved in acetonitrile (1.75 ml). (R)-1-(Methylsulfonyl) propan-2-amine hydrochloride (36 mg, 0.21 mmol) was added and the mixture was stirred at room temperature for 3 h. Water and ethyl acetate were added, the layers were separated and the aqueous layer was extracted twice more with ethyl acetate. The combined organic layers were washed with sodium chloride solution, dried over sodium sulfate and concentrated. The residue was purified by silica gel chromatography (ethyl acetate/hexanes) to give 65 mg (64%) of 2-(6-chloro-1-methyl-1H-indazol-3-yl)-5-(2-trimethylsilanyl-ethoxymethyl)-5H-pyrrolo[2,3-b]pyrazine-7-carboxylic acid ((R)-2-methanesulfonyl-1-methyl-ethyl)-amide. (M+H)$^+$=578.

Step 2

2-(6-Chloro-1-methyl-1H-indazol-3-yl)-5H-pyrrolo[2,3-b]pyrazine-7-carboxylic acid ((R)-2-methanesulfonyl-1-methyl-ethyl)-amide 2-(6-Chloro-1-methyl-1H-indazol-3-yl)-5-(2-trimethylsilanyl-ethoxymethyl)-5H-pyrrolo[2,3-b]pyrazine-7-carboxylic acid ((R)-2-methanesulfonyl-1-methyl-ethyl)-amide (65 mg, 0.113 mmol) was dissolved in dichloromethane (0.8 ml) and then stirred in an ice bath. Trifluoroacetic acid (0.4 ml) was slowly added and the ice bath was removed. The reaction was stirred at room temperature for 3 h then cooled in ice bath. Sodium bicarbonate solution was added and the mixture was extracted three times with ethyl acetate. The combined organic layers were washed with sodium chloride solution and dried over sodium sulfate. After evaporation, the residue was dissolved in absolute ethanol (7 ml) and sodium acetate (185 mg, 2.25 mmol) was added. The mixture was stirred for 20 h at 60° C. The reaction was cooled, and water and ethyl acetate were added. The aqueous layer was extracted twice more with ethyl acetate. The combined organic layers were washed with sodium chloride solution, dried over sodium sulfate and evaporated to a residue. After purification by silica gel chromatography (methanol/dichloromethane), 18.6 mg (37%) of 2-(6-chloro-1-methyl-1H-indazol-3-yl)-5H-pyrrolo[2,3-b]pyrazine-7-carboxylic acid ((R)-2-methanesulfonyl-1-methyl-ethyl)-amide was obtained. MS: (M+H)$^+$=447; mp=287-290° C. $^1$H NMR (300 MHz, DMSO-d$_6$) δ ppm 12.91 (s, 1H) 9.10 (s, 1H) 8.54 (d, J=8.7 Hz, 1H) 8.47 (s, 1H) 8.26 (d, J=7.9 Hz, 1H) 7.97-8.02 (m, 1H) 7.35 (dd, J=8.7, 1.5

Hz, 1H) 4.60-4.72 (m, 1H) 4.18 (s, 3H) 3.45-3.63 (m, 2H) 3.06 (s, 3H) 1.52 (d, J=6.8 Hz, 3H).

Example 106

2-(6-Chloro-1-methyl-1H-indazol-3-yl)-5H-pyrrolo[2,3-b]pyrazine-7-carboxylic acid cyclopentylamide

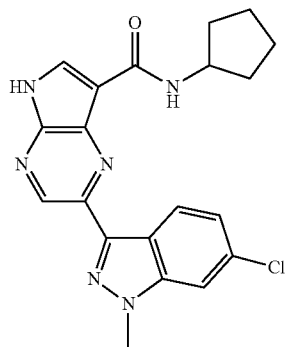 [SMILES: Cn1nc(-c2cnc3[nH]cc(C(=O)NC4CCCC4)c3n2)c2ccc(Cl)cc21]

Prepared according to the procedure outlined in Example 105, substituting cyclopentylamine for (R)-1-(methylsulfonyl)propan-2-amine hydrochloride in Step 1. MS: (M+H)$^+$=395; mp=341-343° C. $^1$H NMR (300 MHz, DMSO-d$_6$) δ ppm 12.81-12.89 (m, 1H) 9.07 (s, 1H) 8.42 (d, J=3.0 Hz, 1H) 8.39 (d, J=8.7 Hz, 1H) 8.05-8.13 (m, 1H) 8.00 (d, J=1.5 Hz, 1H) 7.24 (dd, J=8.7, 1.5 Hz, 1H) 4.30-4.43 (m, 1H) 4.16 (s, 3H) 2.00-2.15 (m, 2H) 1.50-1.83 (m, 6H).

Example 107

2-(6-Chloro-1-methyl-1H-indazol-3-yl)-5H-pyrrolo[2,3-b]pyrazine-7-carboxylic acid (tetrahydrofuran-3-yl)-amide

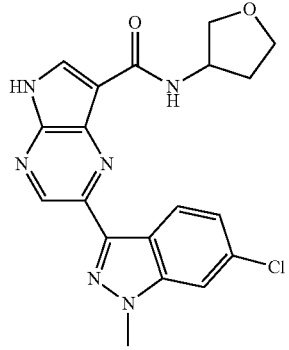 [SMILES: Cn1nc(-c2cnc3[nH]cc(C(=O)NC4CCOC4)c3n2)c2ccc(Cl)cc21]

Prepared according to the procedure outlined in Example 105, substituting tetrahydrofuran-3-ylamine hydrochloride for (R)-1-(methylsulfonyl)propan-2-amine hydrochloride in Step 1. MS: (M+Na)$^+$=419; mp=345-347° C. $^1$H NMR (300 MHz, DMSO-d$_6$) δ ppm 12.89 (br. s., 1H) 9.10 (s, 1H) 8.44 (d, J=8.7 Hz, 1H) 8.46 (d, J=3.4 Hz, 1H) 8.29 (d, J=7.6 Hz, 1H) 7.99 (s, 1H) 7.27 (dd, J=8.7, 1.5 Hz, 1H) 4.62-4.74 (m, 1H) 4.16 (s, 3H) 3.74-4.00 (m, 4H) 2.27-2.41 (m, 1H) 1.88-2.01 (m, 1H).

Example 108

2-(6-Chloro-1-methyl-1H-indazol-3-yl)-5H-pyrrolo[2,3-b]pyrazine-7-carboxylic acid isopropylamide

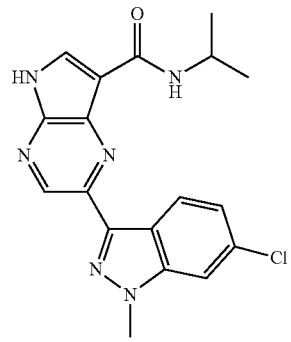 [SMILES: CC(C)NC(=O)c1c[nH]c2ncc(-c3nn(C)c4cc(Cl)ccc34)nc12]

Step 1

2-(6-Chloro-1-methyl-1H-indazol-3-yl)-5-(2-trimethylsilanyl-ethoxymethyl)-5H-pyrrolo[2,3-b]pyrazine-7-carboxylic acid isopropylamide

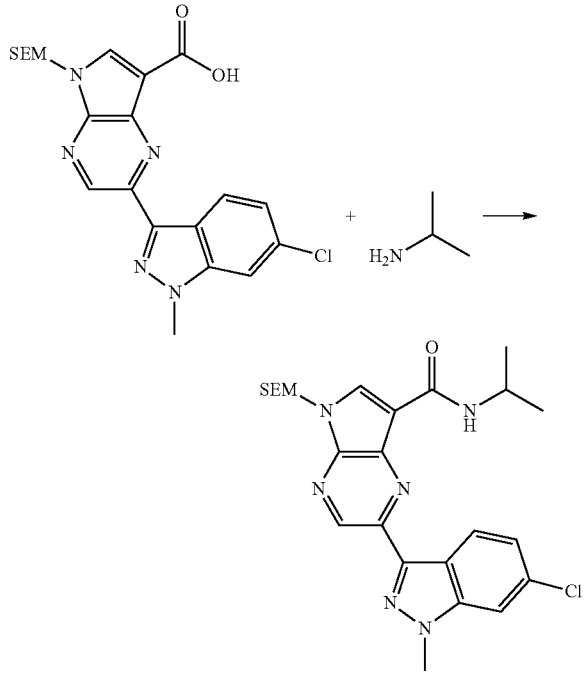

2-(6-Chloro-1-methyl-1H-indazol-3-yl)-5-(2-trimethylsilanyl-ethoxymethyl)-5H-pyrrolo[2,3-b]pyrazine-7-carboxylic acid (80 mg, 0.175 mmol), O-benzotriazol-1-yl-N,N,N',N'-tetramethyluronium tetrafluoroborate (84 mg, 0.26 mmol) and N,N-diisopropylethylamine (0.076 ml, 0.44 mmol) were dissolved in acetonitrile (1.75 ml). Isopropylamine (0.018 ml, 0.21 mmol) was added and the mixture was stirred at room temperature overnight. Water and ethyl acetate were added, the layers were separated and the aqueous layer was extracted twice more with ethyl acetate. The combined organic layers were washed with sodium chloride solution, dried over sodium sulfate and concentrated. The residue was purified by silica gel chromatography (ethyl acetate/hexanes) to give 45 mg (52%) of 2-(6-chloro-1-methyl-1H-indazol-3-yl)-5-(2-trimethylsilanyl-ethoxymethyl)-5H-pyrrolo[2,3-b]pyrazine-7-carboxylic acid isopropylamide. (M+H)$^+$=500.

Step 2

2-(6-Chloro-1-methyl-1H-indazol-3-yl)-5H-pyrrolo[2,3-b]pyrazine-7-carboxylic acid isopropylamide

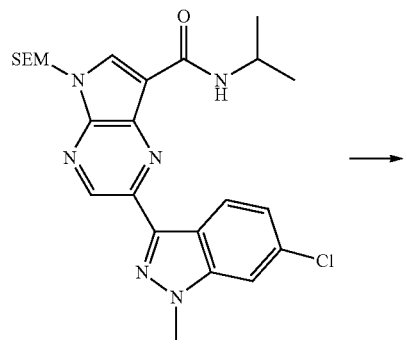

2-(6-Chloro-1-methyl-1H-indazol-3-yl)-5-(2-trimethylsilanyl-ethoxymethyl)-5H-pyrrolo[2,3-b]pyrazine-7-carboxylic acid isopropylamide (45 mg, 0.09 mmol) was dissolved in dichloromethane (0.9 ml) and cooled in ice bath. Trifluoroacetic acid (0.3 ml) was added slowly and the reaction was stirred at room temperature for 3.5 h. The reaction was evaporated and the residue was dissolved in dichloromethane (2 ml). Ethylenediamine (0.36 ml, 5.4 mmol) was added and the mixture was stirred at room temperature for 18 h. Water and then ethyl acetate were added to the mixture. The resulting precipitate was filtered off, rinsed with water and dried under high vacuum to give 21 mg (81%) of 2-(6-chloro-1-methyl-1H-indazol-3-yl)-5H-pyrrolo[2,3-b]pyrazine-7-carboxylic acid isopropylamide. (M+Na)$^+$=391; mp=356-362° C. $^1$H NMR (400 MHz, DMSO-d$_6$) δ ppm 12.79-12.90 (m, 1H) 9.09 (s, 1H) 8.44 (d, J=9.1 Hz, 1H) 8.42 (s, 1H) 8.02 (d, J=7.6 Hz, 1H) 8.00 (d, J=1.5 Hz, 1H) 7.30 (dd, J=8.8, 1.8 Hz, 1H) 4.19-4.27 (m, 1H) 4.17 (s, 3H) 1.32 (d, J=6.6 Hz, 6H).

Example 109

2-(6-Chloro-1-methyl-1H-indazol-3-yl)-5H-pyrrolo[2,3-b]pyrazine-7-carboxylic acid ethylamide

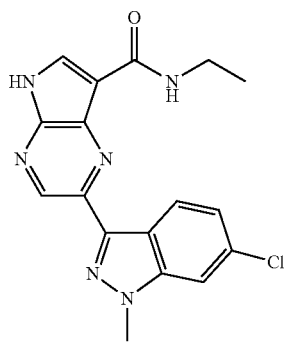 [SMILES: CCNC(=O)c1c[nH]c2ncc(-c3nn(C)c4cc(Cl)ccc34)nc12]

Prepared according to the procedure outlined in Example 108, substituting ethylamine for isopropylamine in Step 1. MS: (M+Na)$^+$=377; mp=373-377° C. $^1$H NMR (300 MHz, DMSO-d$_6$) δ: 12.79-12.88 (m, 1H), 9.09 (s, 1H), 8.42 (s, 1H), 8.43 (d, J=8.6 Hz, 1H), 8.07-8.14 (m, 1H), 7.99 (d, J=1.5 Hz, 1H), 7.32 (dd, J=8.6, 1.5 Hz, 1H), 4.17 (s, 3H), 3.44-3.54 (m, 2H), 1.31 (t, J=7.3 Hz, 3H).

Example 110

2-(6-Chloro-1-methyl-1H-indazol-3-yl)-5H-pyrrolo[2,3-b]pyrazine-7-carboxylic acid cyclohexylamide

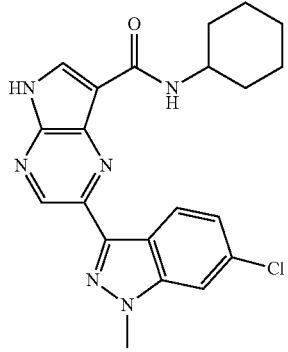 [SMILES: Cn1nc(-c2cnc3[nH]cc(C(=O)NC4CCCCC4)c3n2)c2ccc(Cl)cc21]

Prepared according to the procedure outlined in Example 108, substituting cyclohexylamine for isopropylamine in Step 1. MS: (M+H)$^+$=409; mp=321-323° C. $^1$H NMR (300 MHz, DMSO-d$_6$) δ: 12.81-12.89 (m, 1H), 9.08 (s, 1H), 8.41 (d, J=8.3 Hz, 1H), 8.43 (s, 1H), 8.06 (d, J=7.9 Hz, 1H), 8.00 (d, J=1.5 Hz, 1H), 7.27 (dd, J=8.7, 1.5 Hz, 1H), 4.17 (s, 3H), 3.84-3.98 (m, 1H), 1.99-2.09 (m, 2H), 1.74-1.84 (m, 2H), 1.59-1.70 (m, 1H), 1.20-1.49 (m, 5H).

Example 111

2-(6-Chloro-1-methyl-1H-indazol-3-yl)-5H-pyrrolo[2,3-b]pyrazine-7-carboxylic acid (tetrahydro-pyran-3-yl)-amide

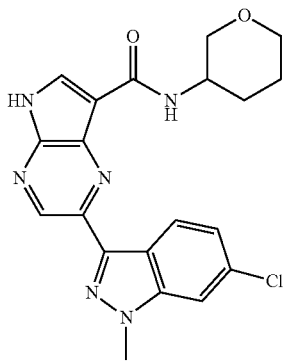 [SMILES: Cn1nc(-c2cnc3[nH]cc(C(=O)NC4CCCOC4)c3n2)c2ccc(Cl)cc21]

Prepared according to the procedure outlined in Example 108, substituting tetrahydro-2H-pyran-3-ylamine hydrochloride for isopropylamine in Step 1. MS: (M+Na)$^+$=433; mp=339-342° C. $^1$H NMR (300 MHz, DMSO-d$_6$) δ: 12.91-13.01 (m, 1H), 9.11 (s, 1H), 8.52 (d, J=8.3 Hz, 1H), 8.45 (d, J=3.0 Hz, 1H), 8.19 (d, J=7.9 Hz, 1H), 7.97-8.01 (m, 1H), 7.26 (dd, J=8.7, 1.5 Hz, 1H), 4.17 (s, 3H), 4.04-4.22 (m, 1H), 3.85-3.95 (m, 1H), 3.56-3.72 (m, 2H), 3.47-3.56 (m, 1H), 1.68-1.85 (m, 2H), 1.49-1.65 (m, 2H).

Example 112

2-(6-Chloro-1-methyl-1H-indazol-3-yl)-5H-pyrrolo[2,3-b]pyrazine-7-carboxylic acid (tetrahydro-pyran-4-yl)-amide

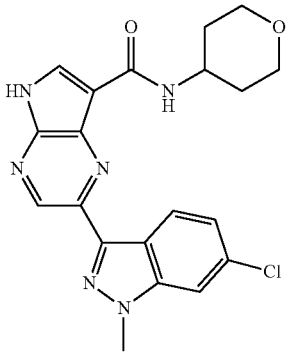 [SMILES: Cn1nc(-c2cnc3[nH]cc(C(=O)NC4CCOCC4)c3n2)c2ccc(Cl)cc21]

Prepared according to the procedure outlined in Example 108, substituting tetrahydro-2H-pyran-4-ylamine hydrochloride for isopropylamine in Step 1. MS: (M+Na)$^+$=433; mp=355-358° C. $^1$H NMR (300 MHz, DMSO-d$_6$) δ: 12.85-12.93 (m, 1H), 9.09 (s, 1H), 8.43 (d, J=8.3 Hz, 1H), 8.46 (s, 1H), 8.11 (d, J=7.6 Hz, 1H), 8.01 (s, 1H), 7.26-7.33 (m, 1H), 4.07-4.23 (m, 4H), 3.90-4.00 (m, 2H), 3.42-3.55 (m, 2H), 1.97-2.08 (m, 2H), 1.51-1.68 (m, 2H).

Example 113

2-(6-Chloro-1-methyl-1H-indazol-3-yl)-5H-pyrrolo[2,3-b]pyrazine-7-carboxylic acid (1,1-dioxotetrahydro-thiophen-3-yl)-amide

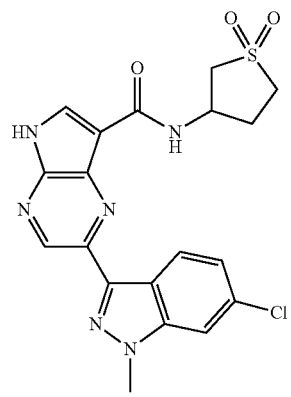 [SMILES: Cn1nc(-c2cnc3[nH]cc(C(=O)NC4CCS(=O)(=O)C4)c3n2)c2ccc(Cl)cc21]

Prepared according to the procedure outlined in Example 108, substituting 1,1-dioxotetrahydro-thiophen-3-ylamine (prepared as in WO2008033562 A2) for isopropylamine in Step 1.

MS: (M+Na)$^+$=467; mp=383-385° C. $^1$H NMR (300 MHz, DMSO-d$_6$) δ: 9.11 (s, 1H), 8.50 (d, J=9.8 Hz, 1H), 8.49 (s, 1H), 8.36 (d, J=7.2 Hz, 1H), 7.97-8.02 (m, 1H), 7.34-7.41 (m, 1H), 4.77-4.93 (m, 1H), 4.17 (s, 3H), 3.59-3.70 (m, 1H), 3.40-3.51 (m, 2H), 3.11-3.23 (m, 1H), 2.61-2.75 (m, 1H), 2.20-2.37 (m, 1H).

Example 114

2-(6-Fluoro-1-methyl-1H-indazol-3-yl)-5H-pyrrolo[2,3-b]pyrazine-7-carboxylic acid (3-hydroxy-2,2-dimethyl-propyl)-amide

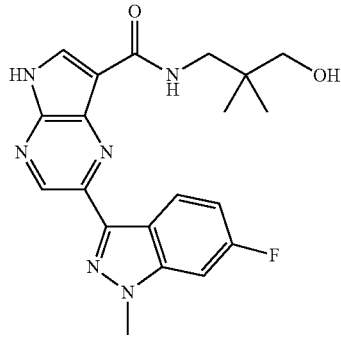

577

Step 1

2-(6-Fluoro-1-methyl-1H-indazol-3-yl)-5-(2-trimethylsilanyl-ethoxymethyl)-5H-pyrrolo[2,3-b]pyrazine-7-carboxylic acid (3-hydroxy-2,2-dimethyl-propyl)-amide

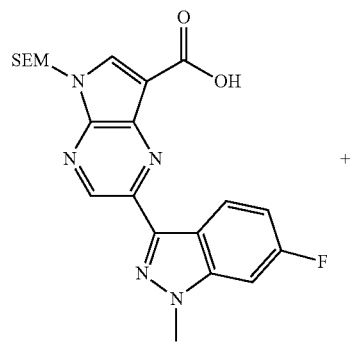

+

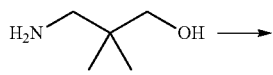

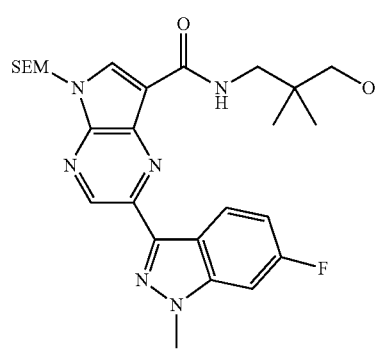

2-(6-Fluoro-1-methyl-1H-indazol-3-yl)-5-(2-trimethylsilanyl-ethoxymethyl)-5H-pyrrolo[2,3-b]pyrazine-7-carboxylic acid (80 mg, 0.18 mmol), O-benzotriazol-1-yl-N,N,N',N'-tetramethyluronium tetrafluoroborate (87 mg, 0.27 mmol) and N,N-diisopropylethylamine (0.16 ml, 0.91 mmol) were dissolved in acetonitrile (1.8 ml). 3-Amino-2,2-dimethylpropan-1-ol (22 mg, 0.22 mmol) was added and the mixture was stirred at room temperature overnight. Water and ethyl acetate were added, the layers were separated and the aqueous layer was extracted twice more with ethyl acetate. The combined organic layers were washed with sodium chloride solution, dried over sodium sulfate and concentrated. The residue was purified by silica gel chromatography (ethyl acetate/hexanes) to give 85 mg (89%) of 2-(6-fluoro-1-methyl-1H-indazol-3-

578 yl)-5-(2-trimethylsilanyl-ethoxymethyl)-5H-pyrrolo[2,3-b]pyrazine-7-carboxylic acid (3-hydroxy-2,2-dimethyl-propyl)-amide. (M+Na)$^+$=549.

Step 2

2-(6-Fluoro-1-methyl-1H-indazol-3-yl)-5H-pyrrolo[2,3-b]pyrazine-7-carboxylic acid (3-hydroxy-2,2-dimethyl-propyl)-amide

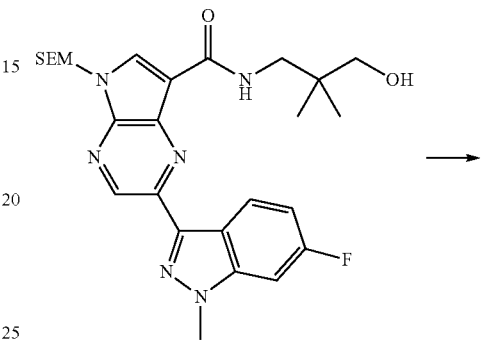

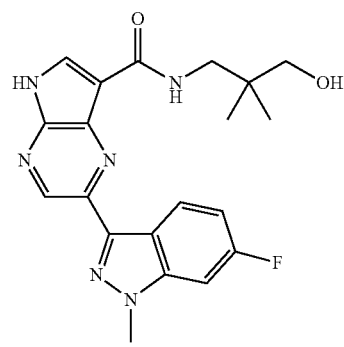 [SMILES: Cn1nc(-c2cnc3[nH]cc(C(=O)NCC(C)(C)CO)c3n2)c2ccc(F)cc21]

2-(6-Fluoro-1-methyl-1H-indazol-3-yl)-5-(2-trimethylsilanyl-ethoxymethyl)-5H-pyrrolo[2,3-b]pyrazine-7-carboxylic acid (3-hydroxy-2,2-dimethyl-propyl)-amide (82 mg, 0.156 mmol) was suspended in dichloromethane (1.1 ml) and cooled in ice bath. Trifluoroacetic acid (0.5 ml) was added slowly and the reaction was stirred at room temperature for 3.5 h. The reaction was evaporated and the residue was dissolved in dichloromethane (1.6 ml). Ethylenediamine (0.63 ml, 9.3 mmol) was added and the mixture was stirred at room temperature for 18 h. Water and then ethyl acetate were added to the mixture, the layers were separated and the aqueous layer was extracted twice more with ethyl acetate. The combined organic layers were washed with sodium chloride solution, dried over sodium sulfate and concentrated. The residue was purified by silica gel chromatography (methanol/dichloromethane) to give 39 mg (63%) of 2-(6-fluoro-1-methyl-1H-indazol-3-yl)-5H-pyrrolo[2,3-b]pyrazine-7-carboxylic acid (3-hydroxy-2,2-dimethyl-propyl)-amide as an off-white solid. (M+Na)$^+$=419; mp=291-293° C. $^1$H NMR (300 MHz, DMSO-d$_6$) δ: 9.10 (s, 1H), 8.45 (s, 1H), 8.41-8.49 (m, 1H), 8.19-8.27 (m, 1H), 7.67 (dd, J=9.8, 2.3 Hz, 1H), 7.14-7.23 (m, 1H), 4.63-4.72 (m, 1H), 4.14 (s, 3H), 3.37-3.43 (m, 2H), 3.16-3.24 (m, 2H), 0.90 (s, 6H).

Example 115

2-(6-Fluoro-1-methyl-1H-indazol-3-yl)-5H-pyrrolo[2,3-b]pyrazine-7-carboxylic acid (2,2-dimethylpropyl)-amide

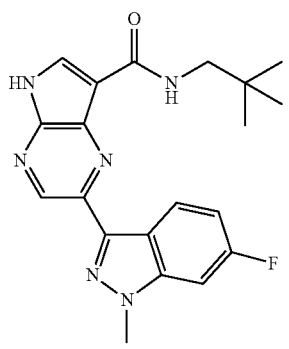 [SMILES: Cn1nc(-c2cnc3[nH]cc(C(=O)NCC(C)(C)C)c3n2)c2ccc(F)cc21]

Prepared according to the procedure outlined in Example 114, substituting 2,2-dimethylpropylamine for 3-amino-2,2-dimethylpropan-1-ol in Step 1. MS: (M+Na)$^+$=403; mp=294-295° C. $^1$H NMR (300 MHz, DMSO-d$_6$) δ: 12.81-12.93 (m, 1H), 9.09 (s, 1H), 8.44 (s, 1H), 8.41 (dd, J=8.9, 5.5 Hz, 1H), 8.21-8.29 (m, 1H), 7.67 (dd, J=9.8, 2.3 Hz, 1H), 7.12-7.22 (m, 1H), 4.14 (s, 3H), 3.33-3.38 (m, 2H), 0.95 (s, 9H).

Example 116

2-(6-Fluoro-1-methyl-1H-indazol-3-yl)-5H-pyrrolo[2,3-b]pyrazine-7-carboxylic acid isobutylamide

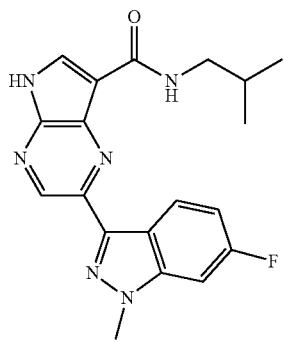 [SMILES: CC(C)CNC(=O)c1c[nH]c2ncc(-c3nn(C)c4cc(F)ccc34)nc12]

Prepared according to the procedure outlined in Example 114, substituting isobutylamine for 3-amino-2,2-dimethylpropan-1-ol in Step 1. MS: (M+H)$^+$=367; mp=285-287° C. $^1$H NMR (300 MHz, DMSO-d$_6$) δ: 12.79-12.89 (m, 1H), 9.09 (s, 1H), 8.42 (dd, J=9.1, 5.3 Hz, 1H), 8.43 (s, 1H), 8.18-8.28 (m, 1H), 7.68 (dd, J=9.6, 2.1 Hz, 1H), 7.13-7.23 (m, 1H), 4.14 (s, 3H), 3.34-3.37 (m, 2H), 1.91 (s, 1H), 0.98 (d, J=6.8 Hz, 6H).

Example 117

2-(6-Fluoro-1-methyl-1H-indazol-3-yl)-5H-pyrrolo[2,3-b]pyrazine-7-carboxylic acid cyclopropylmethyl-amide

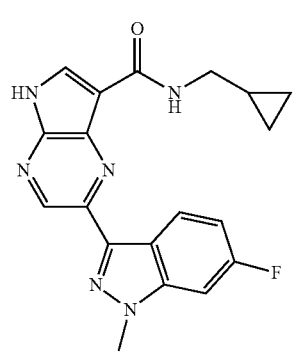 [SMILES: Cn1nc(-c2cnc3[nH]cc(C(=O)NCC4CC4)c3n2)c2ccc(F)cc21]

Prepared according to the procedure outlined in Example 114, substituting cyclopropylmethylamine for 3-amino-2,2-dimethylpropan-1-ol in Step 1. MS: (M+Na)$^+$=387; mp=319-322° C. $^1$H NMR (300 MHz, DMSO-d$_6$) δ: 12.80-12.88 (m, 1H), 9.09-9.12 (m, 1H), 8.48 (dd, J=8.9, 5.5 Hz, 1H), 8.43 (s, 1H), 8.17-8.25 (m, 1H), 7.68 (dd, J=9.8, 2.3 Hz, 1H), 7.13-7.23 (m, 1H), 4.15 (s, 3H), 3.34-3.39 (m, 2H), 1.08-1.22 (m, 1H), 0.52-0.60 (m, 2H), 0.29-0.36 (m, 2H).

Example 118

2-(6-Chloro-1-methyl-1H-indazol-3-yl)-5H-pyrrolo[2,3-b]pyrazine-7-carboxylic acid [(R)-2-((S)-3-fluoro-pyrrolidin-1-yl)-1-methyl-2-oxo-ethyl]-amide

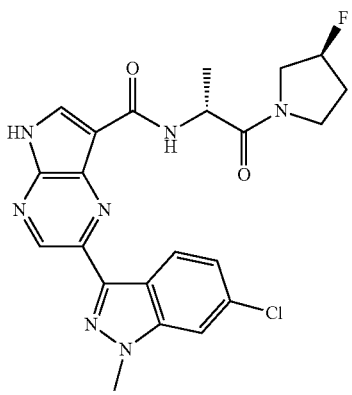

Step 1

[(R)-2-((S)-3-Fluoro-pyrrolidin-1-yl)-1-methyl-2-oxo-ethyl]-carbamic acid tert-butyl ester

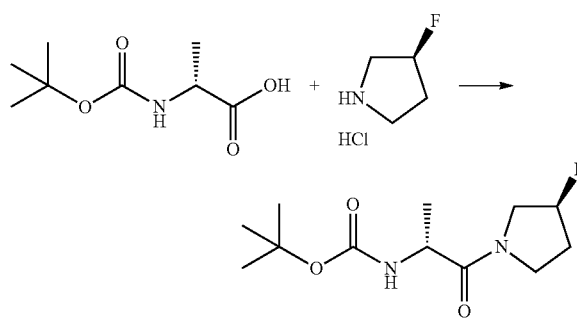

(R)-2-tert-Butoxycarbonylamino-propionic acid (1.0 g, 5.3 mmol), 1-(3-(dimethylamino)-propyl)-3-ethylcarbodiimide (2.33 g, 12.2 mmol) and hydroxybenzotriazole (1.64 g, 12.2 mmol) were dissolved in DMF (50 ml). (S)-3-Fluoropyrrolidine hydrochloride (1.66 g, 13.2 mmol) and N,N-diisopropylethylamine (2.95 ml, 16.9 mmol) were added and the mixture was stirred at room temperature for 16 h. Ethyl acetate was added and the solution was washed with 10% citric acid solution three times. The organic layer was washed with sodium bicarbonate solution which was then back-extracted with ethyl acetate four times. The combined organic layers were then washed further with lithium chloride solution, sodium chloride solution, and dried over magnesium sulfate. Concentration of the solution gave 1.3 g (94%) of [(R)-2-((S)-3-fluoro-pyrrolidin-1-yl)-1-methyl-2-oxo-ethyl]-carbamic acid tert-butyl ester.

Step 2

(R)-2-Amino-1-((S)-3-fluoro-pyrrolidin-1-yl)-propan-1-one trifluoroacetate

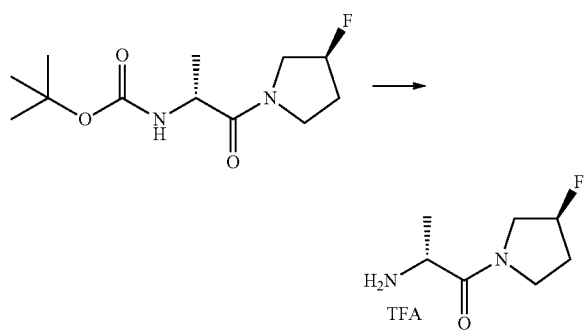

[(R)-2-((S)-3-Fluoro-pyrrolidin-1-yl)-1-methyl-2-oxo-ethyl]-carbamic acid tert-butyl ester (43 mg, 0.127 mmol) was dissolved in dichloromethane (1.6 ml) and cooled in an ice bath. Trifluoroacetic acid (0.8 ml) was slowly added and the reaction was stirred at room temperature for 3 h then evaporated and dried under high vacuum to afford (R)-2-amino-1-((S)-3-fluoro-pyrrolidin-1-yl)-propan-1-one trifluoroacetate which was used without further purification.

Step 3

2-(6-Chloro-1-methyl-1H-indazol-3-yl)-5-(2-trimethylsilanyl-ethoxymethyl)-5H-pyrrolo[2,3-b]pyrazine-7-carboxylic acid [(R)-2-((S)-3-fluoro-pyrrolidin-1-yl)-1-methyl-2-oxo-ethyl]-amide

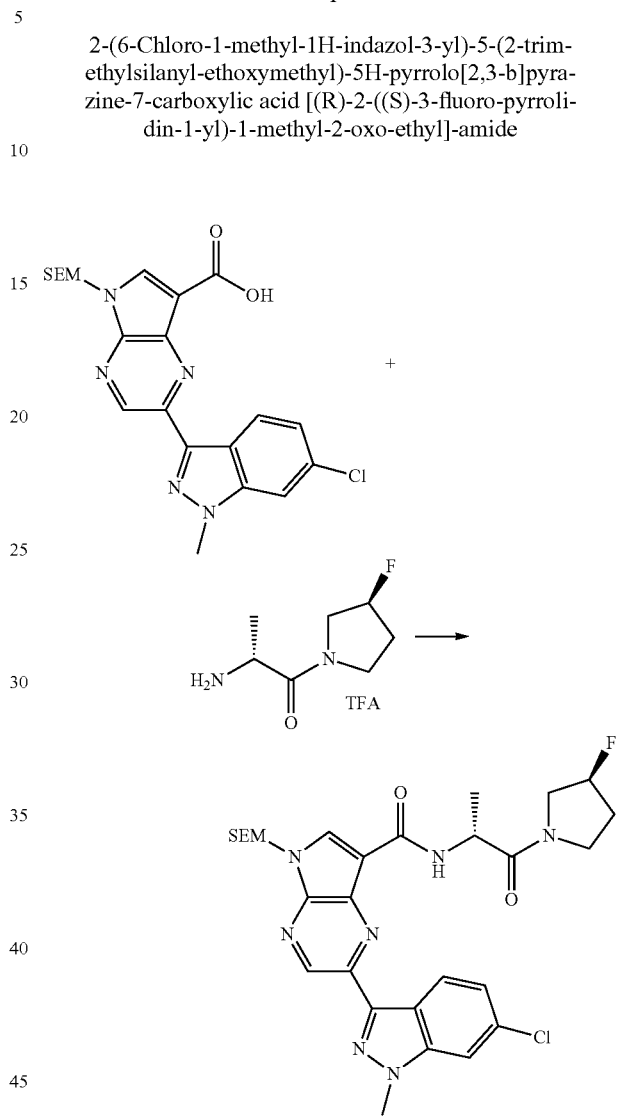

(R)-2-Amino-1-((S)-3-fluoro-pyrrolidin-1-yl)-propan-1-one trifluoroacetate (crude from Step 2) was dissolved in acetonitrile (4 ml) to which was then added 2-(6-chloro-1-methyl-1H-indazol-3-yl)-5-(2-trimethylsilanyl-ethoxymethyl)-5H-pyrrolo[2,3-b]pyrazine-7-carboxylic acid (60 mg, 0.13 mmol), O-benzotriazol-1-yl-N,N,N',N'-tetramethyluronium tetrafluoroborate (63 mg, 0.197 mmol) and N,N-diisopropylethylamine (0.092 ml, 0.52 mmol). The reaction was stirred at room temperature for 18 h and then water and ethyl acetate were added. The layers were separated and the aqueous layer was extracted once more with ethyl acetate. The combined organic layers were washed with sodium chloride solution and dried over sodium sulfate. After evaporation, the residue was purified by silica gel chromatography (ethyl acetate/hexanes) to afford 55 mg (70%) of 2-(6-chloro-1-methyl-1H-indazol-3-yl)-5-(2-trimethylsilanylethoxymethyl)-5H-pyrrolo[2,3-b]pyrazine-7-carboxylic acid [(R)-2-((S)-3-fluoro-pyrrolidin-1-yl)-1-methyl-2-oxo-ethyl]-amide. $^{1}$H NMR (300 MHz, CDCl$_3$) δ: 9.29 (s, 1H), 8.88-8.93 (m, 1H), 8.85 (d, J=8.1 Hz, 1H), 8.32 (s, 1H), 7.43-7.46 (m, 1H), 7.35-7.39 (m, 1H), 5.70-5.74 (m, 2H), 5.21-5.26 (m, 1H), 4.15 (s, 3H), 3.61-4.00 (m, 5H), 3.54-3.61 (m, 2H), 2.06-2.46 (m, 2H), 1.59 (d, J=6.6 Hz, 3H), 0.90-0.97 (m, 2H), −0.05 (s, 9H).

Step 4

2-(6-Chloro-1-methyl-1H-indazol-3-yl)-5H-pyrrolo[2,3-b]pyrazine-7-carboxylic acid [(R)-2-((S)-3-fluoro-pyrrolidin-1-yl)-1-methyl-2-oxo-ethyl]-amide

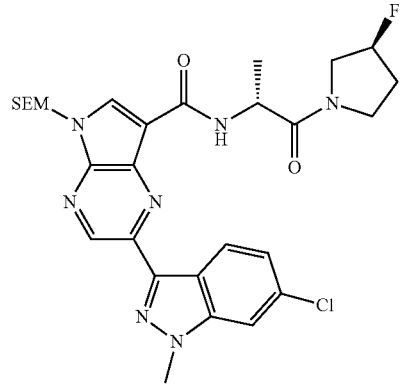

→

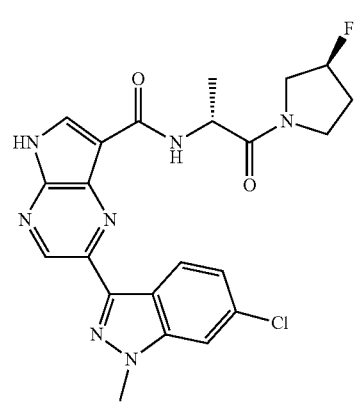 [SMILES: C[C@@H](NC(=O)c1c[nH]c2ncc(-c3nn(C)c4cc(Cl)ccc34)nc12)C(=O)N1CC[C@H](F)C1]

2-(6-Chloro-1-methyl-1H-indazol-3-yl)-5-(2-trimethylsilanyl-ethoxymethyl)-5H-pyrrolo[2,3-b]pyrazine-7-carboxylic acid [(R)-2-((S)-3-fluoro-pyrrolidin-1-yl)-1-methyl-2-oxo-ethyl]-amide (54 mg, 0.09 mmol) was dissolved in dichloromethane (0.9 ml) and cooled in ice bath. Trifluoroacetic acid (0.45 ml) was slowly added and the reaction was stirred at room temperature for 2.5 h. The reaction was evaporated and the residue was suspended in dichloromethane (0.9 ml). Ethylenediamine (0.36 ml, 5.4 mmol) was added and the mixture was stirred for 18 h. Water and then ethyl acetate were added to the mixture. The resulting precipitate was filtered off, rinsed with water and dried under high vacuum to give 24 mg (58%) of 2-(6-chloro-1-methyl-1H-indazol-3-yl)-5H-pyrrolo[2,3-b]pyrazine-7-carboxylic acid [(R)-2-((S)-3-fluoro-pyrrolidin-1-yl)-1-methyl-2-oxo-ethyl]-amide. MS: (M+H)+=470; mp=269-271° C. $^1$H NMR (300 MHz, DMSO-d$_6$) δ: 9.16 (s, 1H), 8.81-8.91 (m, 1H), 8.53-8.62 (m, 1H), 8.47 (d, J=2.0 Hz, 1H), 7.97 (s, 1H), 7.25-7.33 (m, 1H), 5.27-5.52 (m, 1H), 4.95-5.11 (m, 1H), 4.18 (s, 3H), 3.96-4.12 (m, 1H), 3.73-3.92 (m, 1H), 3.61-3.72 (m, 1H), 2.08-2.35 (m, 1H), 1.38-1.48 (m, 3H).

Example 119

2-(6-Chloro-1-methyl-1H-indazol-3-yl)-5H-pyrrolo[2,3-b]pyrazine-7-carboxylic acid [(R)-2-((R)-3-fluoro-pyrrolidin-1-yl)-1-methyl-2-oxo-ethyl]-amide

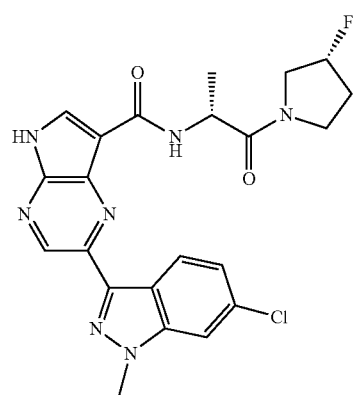

Prepared according to the procedure outlined in Example 118, substituting (R)-3-fluoropyrrolidine hydrochloride for (S)-3-fluoropyrrolidine hydrochloride in Step 1. MS: (M+H)+= 470; mp=272-274° C. $^1$H NMR (300 MHz, DMSO-d$_6$) δ: 12.85-12.95 (m, 1H), 9.15 (s, 1H), 8.80-8.87 (m, 1H), 8.55 (d, J=8.6 Hz, 1H), 8.46 (d, J=2.5 Hz, 1H), 7.97 (d, J=1.5 Hz, 1H), 7.24-7.32 (m, 1H), 5.26-5.53 (m, 1H), 4.92-5.09 (m, 1H), 4.18 (s, 3H), 3.67-3.95 (m, 2H), 3.36-3.62 (m, 2H), 2.09-2.34 (m, 2H), 1.40-1.47 (m, 3H).

Example 120

2-(6-Chloro-1-methyl-1H-indazol-3-yl)-5H-pyrrolo[2,3-b]pyrazine-7-carboxylic acid [(R)-2-(3-fluoro-azetidin-1-yl)-1-methyl-2-oxo-ethyl]-amide

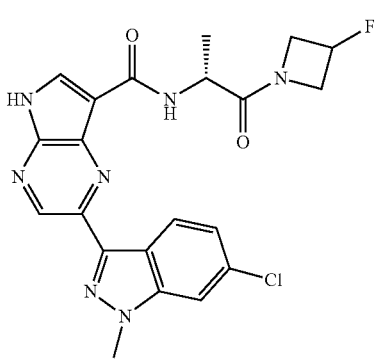 [SMILES: C[C@@H](NC(=O)c1c[nH]c2ncc(-c3nn(C)c4cc(Cl)ccc34)nc12)C(=O)N1CC(F)C1]

Prepared according to the procedure outlined in Example 118, substituting 3-fluoro-azetidine hydrochloride for (S)-3-fluoropyrrolidine hydrochloride in Step 1. MS: (M+H)+=456; mp=257-260° C. $^1$H NMR (300 MHz, DMSO-d$_6$) δ: 9.14 (s, 1H), 8.70-8.81 (m, 1H), 8.48 (br. s., 1H), 8.42-8.53 (m, 1H), 7.97 (s, 1H), 7.22-7.31 (m, 1H), 5.30-5.59 (m, 1H), 4.20-4.85 (m, 4H), 4.17 (s, 3H), 3.90-4.10 (m, 1H), 1.36-1.48 (m, 3H).

Example 121

2-(6-Chloro-1-methyl-1H-indazol-3-yl)-5H-pyrrolo[2,3-b]pyrazine-7-carboxylic acid [(R)-2-((R)-3-fluoro-pyrrolidin-1-yl)-1-methyl-ethyl]-amide

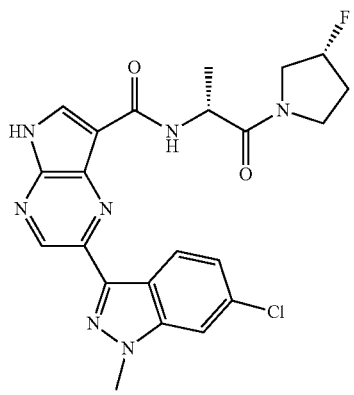 [SMILES: C[C@@H](NC(=O)c1c[nH]c2ncc(-c3nn(C)c4cc(Cl)ccc34)nc12)C(=O)N1CC[C@@H](F)C1]

Step 1

[(R)-2-((R)-3-Fluoro-pyrrolidin-1-yl)-1-methyl-2-oxo-ethyl]-carbamic acid tert-butyl ester

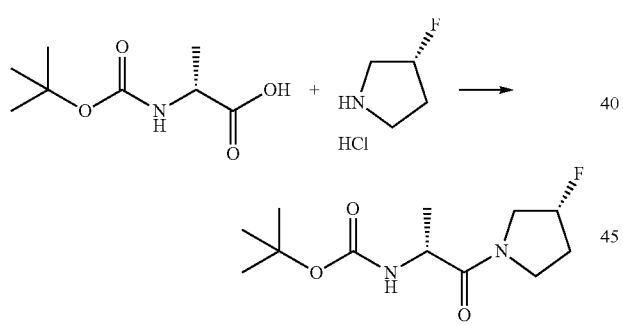

Step 1

(R)-2-tert-Butoxycarbonylamino-propionic acid (1.0 g, 5.3 mmol), 1-(3-(dimethylamino)-propyl)-3-ethylcarbodiimide (2.33 g, 12.2 mmol) and hydroxybenzotriazole (1.64 g, 12.2 mmol) were dissolved in DMF (50 ml). (R)-3-Fluoro-pyrrolidine hydrochloride (1.66 g, 13.2 mmol) and N,N-diisopropylethylamine (2.95 ml, 16.9 mmol) were added and the mixture was stirred at room temperature for 16 h. Ethyl acetate was added and the solution was washed with 10% citric acid solution three times. The organic layer was washed with sodium bicarbonate solution which was then back-extracted with ethyl acetate four times. The combined organic layers were then washed further with lithium chloride solution, sodium chloride solution, and dried over magnesium sulfate. Concentration of the solution gave 1.3 g (94%) of [(R)-2-((R)-3-fluoro-pyrrolidin-1-yl)-1-methyl-2-oxo-ethyl]-carbamic acid tert-butyl ester.

Step 2

[(R)-2-((R)-3-Fluoro-pyrrolidin-1-yl)-1-methyl-ethyl]-carbamic acid tert-butyl ester

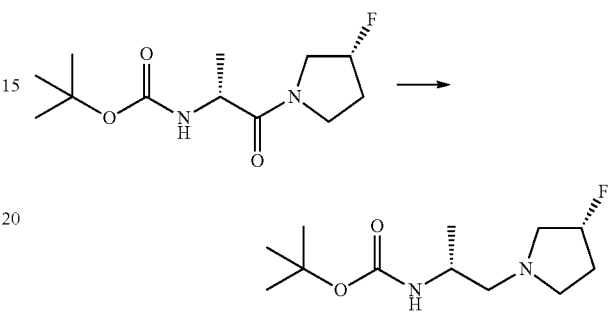

[(R)-2-((R)-3-fluoro-pyrrolidin-1-yl)-1-methyl-2-oxo-ethyl]-carbamic acid tert-butyl ester (50 mg, 0.19 mmol) was dissolved in diethyl ether (0.8 ml) and stirred in an ice/water bath. Lithium aluminum hydride (1.0 M in diethyl ether, 0.38 ml, 0.38 mmol) was added dropwise. The reaction was stirred at 0° C. and monitored by TLC. When the reaction was judged to be complete, water (15 ul), then 10% sodium hydroxide solution (23 ul), and then water (45 ul) were added. The reaction mixture was warmed to room temperature then filtered. The filtrate was evaporated to give 47 mg (99%) of [(R)-2-(R)-3-fluoro-pyrrolidin-1-yl)-1-methyl-ethyl]-carbamic acid tert-butyl ester.

Step 3

(R)-2-(R)-3-Fluoro-pyrrolidin-1-yl)-1-methyl-ethylamine bistrifluoroacetate

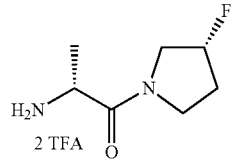

[(R)-2-((R)-3-Fluoro-pyrrolidin-1-yl)-1-methyl-ethyl]-carbamic acid tert-butyl ester (48 mg, 0.185 mmol) was dissolved in dichlormethane (1.2 ml) and cooled in an ice bath. Trifluoroacetic acid (0.74 ml) was slowly added and the reaction was stirred at room temperature for 2 h then evaporated to afford (R)-2-((R)-3-fluoro-pyrrolidin-1-yl)-1-methyl-ethylamine bistrifluoroacetate which was used without further purification.

Step 4

2-(6-Chloro-1-methyl-1H-indazol-3-yl)-5-(2-trimethylsilanyl-ethoxymethyl)-5H-pyrrolo[2,3-b]pyrazine-7-carboxylic acid [(R)-2-((R)-3-fluoro-pyrrolidin-1-yl)-1-methyl-ethyl]-amide

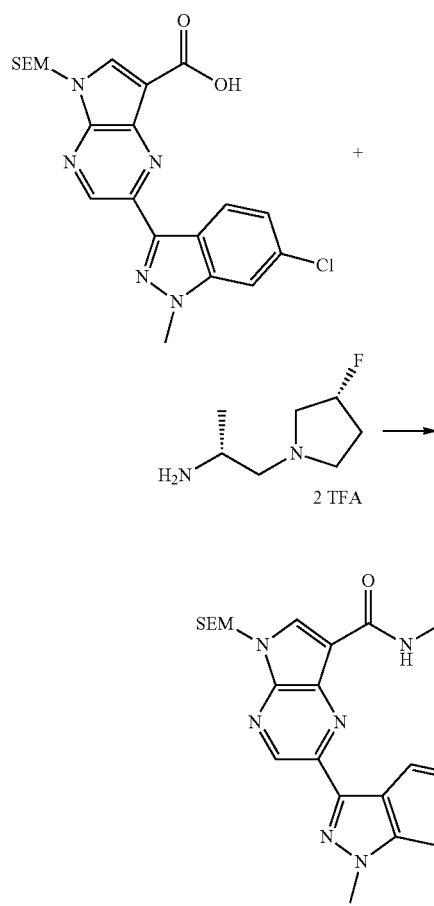

(R)-2-((R)-3-Fluoro-pyrrolidin-1-yl)-1-methyl-ethylamine bistrifluoroacetate (crude from Step 3) was dissolved in acetonitrile (4 ml) to which was then added 2-(6-chloro-1-methyl-1H-indazol-3-yl)-5-(2-trimethylsilanyl-ethoxymethyl)-5H-pyrrolo[2,3-b]pyrazine-7-carboxylic acid (65 mg, 0.14 mmol), O-benzotriazol-1-yl-N,N,N',N'-tetramethyluronium tetrafluoroborate (68 mg, 0.21 mmol) and N,N-diisopropylethylamine (0.12 ml, 0.71 mmol). The reaction was stirred at room temperature for 18 h and then water and ethyl acetate were added. The layers were separated and the aqueous layer was extracted once more with ethyl acetate. The combined organic layers were washed with sodium chloride solution and dried over sodium sulfate. After evaporation, the residue was purified by silica gel chromatography (methanol/dichloromethane) to afford 65 mg (78%) of 2-(6-chloro-1-methyl-1H-indazol-3-yl)-5-(2-trimethylsilanylethoxymethyl)-5H-pyrrolo[2,3-b]pyrazine-7-carboxylic acid [(R)-2-(R)-3-fluoro-pyrrolidin-1-yl)-1-methyl-ethyl]-amide. $(M+H)^+=586$.

Step 5

2-(6-Chloro-1-methyl-1H-indazol-3-yl)-5H-pyrrolo[2,3-b]pyrazine-7-carboxylic acid [(R)-2-((R)-3-fluoro-pyrrolidin-1-yl)-1-methyl-ethyl]-amide

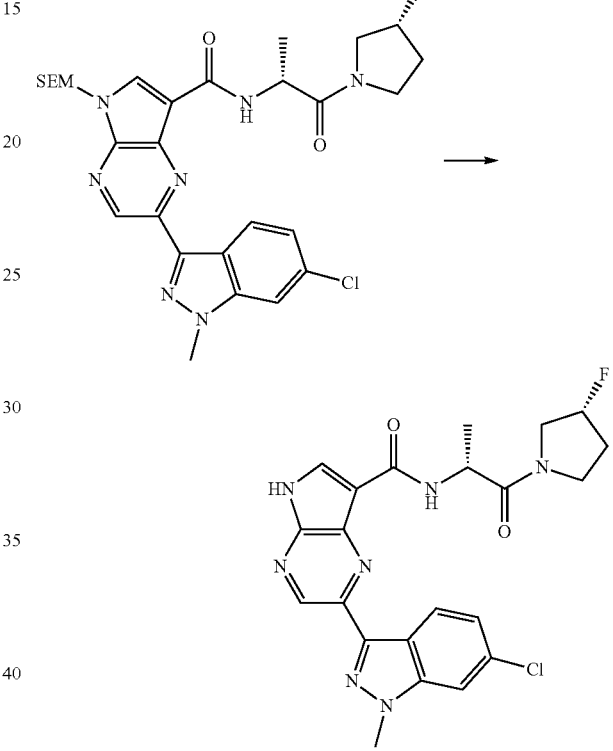

2-(6-Chloro-1-methyl-1H-indazol-3-yl)-5-(2-trimethylsilanyl-ethoxymethyl)-5H-pyrrolo[2,3-b]pyrazine-7-carboxylic acid [(R)-2-((R)-3-fluoro-pyrrolidin-1-yl)-1-methyl-ethyl]-amide (65 mg, 0.11 mmol) was dissolved in dichloromethane (0.7 ml) and cooled in ice bath. Trifluoroacetic acid (0.4 ml) was slowly added and the reaction was stirred at room temperature for 3 h. The reaction was evaporated and the residue was suspended in dichloromethane (1.1 ml). Ethylenediamine (0.45 ml, 6.65 mmol) was added and the mixture was stirred for 18 h. Water and then ethyl acetate were added to the mixture. The layers were separated and the aqueous layer was extracted twice more with ethyl acetate. The combined organic layers were washed with sodium chloride solution and dried over sodium sulfate. After evaporation, the residue was purified by silica gel chromatography (methanol/dichloromethane) to afford 33 mg (65%) of 2-(6-chloro-1-methyl-1H-indazol-3-yl)-5H-pyrrolo[2,3-b]pyrazine-7-carboxylic acid [(R)-2-((R)-3-fluoro-pyrrolidin-1-yl)-1-methyl-ethyl]-amide. MS $(M+H)^+=456$; mp=233-234° C. $^1$H NMR (300 MHz, DMSO-$d_6$) δ: 12.81-12.93 (m, 1H), 9.10 (s, 1H), 8.44 (s, 1H), 8.38-8.46 (m, 1H), 8.07 (d, J=8.3 Hz, 1H), 7.99-8.03 (m, 1H), 7.28-7.36 (m, 1H), 4.97-5.24 (m, 1H), 4.20-4.33 (m, 1H), 4.17 (s, 3H), 2.54-2.90 (m, 1H), 2.54-2.90 (m, 4H), 2.32-2.44 (m, 1H), 1.66-2.13 (m, 2H), 1.32 (d, J=6.4 Hz, 3H).

Example 122

2-(6-Chloro-1-methyl-1H-indazol-3-yl)-5H-pyrrolo[2,3-b]pyrazine-7-carboxylic acid [(R)-2-((S)-3-fluoro-pyrrolidin-1-yl)-1-methyl-ethyl]-amide

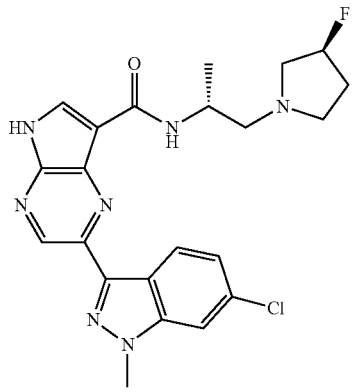 [SMILES: C[C@H](CN1CC[C@H](F)C1)NC(=O)c1c[nH]c2ncc(-c3nn(C)c4cc(Cl)ccc34)nc12]

Prepared according to the procedure outlined in Example 121, substituting (S)-3-fluoropyrrolidine hydrochloride for (R)-3-fluoropyrrolidine hydrochloride in Step 1. MS: (M+H)$^+$=456; mp=251-253° C. $^1$H NMR (300 MHz, DMSO-d$_6$) δ: 12.81-12.94 (m, 1H), 9.09 (s, 1H), 8.43 (s, 1H), 8.43 (d, J=8.7 Hz, 1H), 8.04-8.11 (m, 1H), 8.01 (d, J=1.1 Hz, 1H), 7.32 (dd, J=8.7, 1.5 Hz, 1H), 4.96-5.23 (m, 1H), 4.20-4.34 (m, 1H), 4.17 (s, 3H), 2.58-2.93 (m, 5H), 2.37-2.47 (m, 1H), 1.65-2.12 (m, 2H), 1.33 (d, J=6.4 Hz, 3H).

Example 123

2-(6-Chloro-1-methyl-1H-indazol-3-yl)-5H-pyrrolo[2,3-b]pyrazine-7-carboxylic acid [(R)-2-(3-fluoro-azetidin-1-yl)-1-methyl-ethyl]-amide

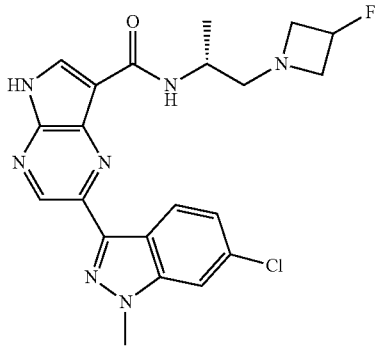 [SMILES: C[C@H](CN1CC(F)C1)NC(=O)c1c[nH]c2ncc(-c3nn(C)c4cc(Cl)ccc34)nc12]

Prepared according to the procedure outlined in Example 121, substituting 3-fluoro-azetidine hydrochloride for (R)-3-fluoropyrrolidine hydrochloride in Step 1. MS: (M+H)$^+$=442; mp=182-185° C. $^1$H NMR (300 MHz, DMSO-d$_6$) δ: 12.76-12.96 (m, 1H), 9.11 (s, 1H), 8.44 (s, 1H), 8.38-8.49 (m, 1H), 8.05 (d, J=8.3 Hz, 1H), 8.02 (d, J=1.5 Hz, 1H), 7.29-7.35 (m, 1H), 4.88-5.18 (m, 1H), 4.18 (s, 3H), 4.08-4.22 (m, 1H), 3.48-3.73 (m, 2H), 3.04-3.29 (m, 2H), 2.62-2.85 (m, 2H), 1.29 (d, J=6.8 Hz, 3H).

Example 124

2-(6-Chloro-4-fluoro-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide

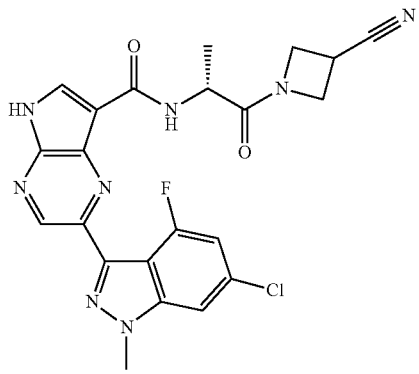 [SMILES: C[C@@H](NC(=O)c1c[nH]c2ncc(-c3nn(C)c4cc(Cl)cc(F)c34)nc12)C(=O)N1CC(C#N)C1]

Step 1

6-Chloro-4-fluoro-1H-indazole

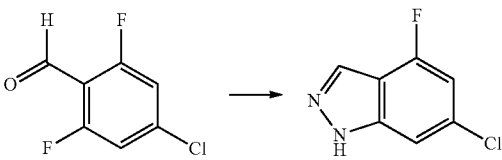 [SMILES: O=Cc1c(F)cc(Cl)cc1F ; Fc1cc(Cl)cc2[nH]ncc12]

4-Chloro-2,6-difluoro-benzaldehyde (15 g, 85 mmol) was dissolved in 1,2-dimethoxyethane 170 ml). O-Methyl-hydroxylamine hydrochloride (7.1 g, 85 mmol) and potassium carbonate (12.9 g, 93.5 mmol) were then added and the mixture was stirred at 35° C. for 24 h. The reaction was filtered, rinsed with dichloromethane, evaporated and redissolved in DMF (170 ml). Hydrazine (2.9 ml 93.5 mmol) was added and the reaction was stirred at 100° C. for 1 h. After cooling, water and ethyl acetate were added. The layers were separated and the aqueous layer was extracted twice more with ethyl acetate. The combined organic layers were washed with water and sodium chloride solution then dried over sodium sulfate. The solvent was evaporated to leave a solid which was purified by silica gel chromatography (diethyl ether/hexanes) to give 7 g (49%) of 6-chloro-4-fluoro-1H-indazole. (M+H)+= 171.

Step 2

6-Chloro-4-fluoro-3-iodo-1H-indazole

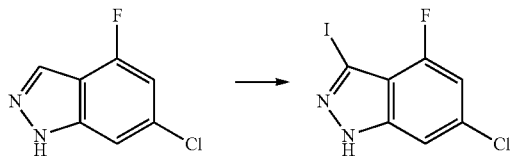 [SMILES: Fc1cc(Cl)cc2[nH]ncc12 ; Fc1cc(Cl)cc2[nH]nc(I)c12]

6-Chloro-4-fluoro-1H-indazole (7.6 g, 44.6 mmol) was dissolved in DMF (110 ml). Iodine (22.6 g, 89.1 mmol) was added followed by potassium hydroxide (9.5 g, 169 mmol). The reaction was stirred at room temperature for 1.5 h. Water, 1 M sodium thiosulfate solution and diethyl ether were added. The layers were separated and the aqueous layer was extracted once more with ether. The organic layers were washed with water and sodium chloride solution, and then dried over sodium sulfate. Evaporation of the solvent gave 11.16 g (85%) of 6-chloro-4-fluoro-3-iodo-1H-indazole as a light brown solid (M−H)−=295.

Step 3

6-Chloro-4-fluoro-3-tributylstannanyl-1H-indazole

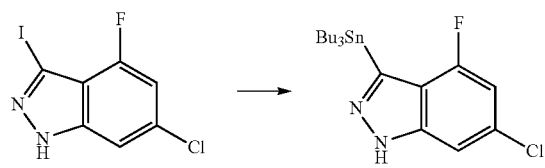

6-Chloro-4-fluoro-3-iodo-1H-indazole (10.1 g, 34.1 mmol) was dissolved in THF (170 ml). The reaction flask was stirred in a water bath and sodium hydride (60% dispersion, 1.64 g, 40.9 mmol) was added. The mixture was stirred for 15 min then cooled in an ice/salt bath to −15° C. Isopropylmagnesium chloride (2.0 M in THF, 20.6 ml, 41.2 mmol) was added dropwise. After 40 min, tributyltin chloride (11.6 ml, 42.6 mmol) was slowly added and the reaction was allowed to warm to room temperature. After an additional 2 h stirring, ammonium chloride solution and ethyl acetate were added. The layers were separated and the aqueous layer was extracted once more with ethyl acetate. The combined organic layers were washed with sodium chloride solution and dried over sodium sulfate. Evaporation of the solvent provided 6-chloro-4-fluoro-3-tributylstannanyl-1H-indazole as an oil which was used directly in the next step.

Step 4

2-(6-Chloro-4-fluoro-1H-indazol-3-yl)-5-(2-trimethylsilanyl-ethoxymethyl)-5H-pyrrolo[2,3-b]pyrazine-7-carbaldehyde

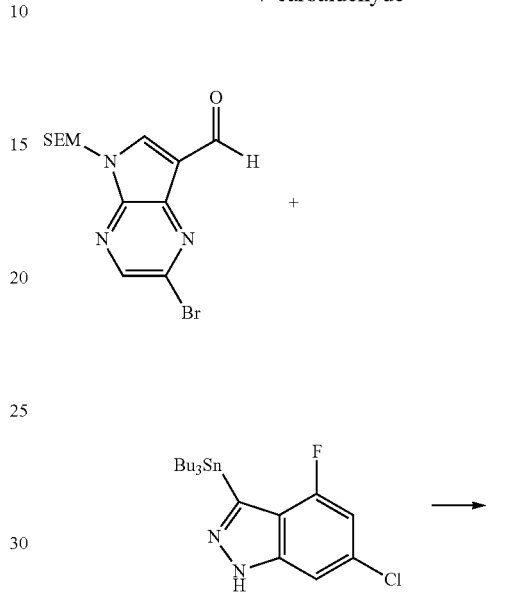

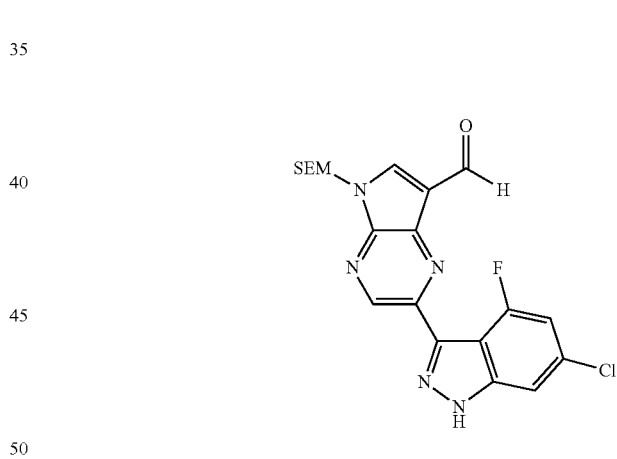

2-Bromo-5-(2-trimethylsilanyl-ethoxymethyl)-5H-pyrrolo[2,3-b]pyrazine-7-carbaldehyde (7.6 g, 18.6 mmol) and 6-chloro-4-fluoro-3-tributylstannanyl-1H-indazole (crude from Step 3) were dissolved in DMF (180 ml) and purged with Ar gas. Tetrakis(triphenylphosphine)palladium (1.07 g, 0.93 mmol) and then copper iodide (707 mg, 3.71 mmol) were added and the flask was stoppered and stirred in a 90° C. oil bath for 20 h. The reaction was cooled and water, ethyl acetate and sodium bicarbonate solution were added. The layers were separated, and the aqueous layer was extracted twice more with ethyl acetate. The combined organic layers were washed with water and sodium chloride solution, then dried over sodium sulfate. After evaporation, the residue was purified by silica gel chromatography (methanol/dichloromethane) followed by trituration with diethyl ether/hexanes to give 3.9 g (47%) of 2-(6-chloro-4-fluoro-1H-indazol- 3-yl)-5-(2-trimethylsilanyl-ethoxymethyl)-5H-pyrrolo[2,3-b]pyrazine-7-carbaldehyde. (M+H)⁺=446.

Step 5

2-(6-Chloro-4-fluoro-1-methyl-1H-indazol-3-yl)-5-(2-trimethylsilanyl-ethoxymethyl)-5H-pyrrolo[2,3-b]pyrazine-7-carbaldehyde

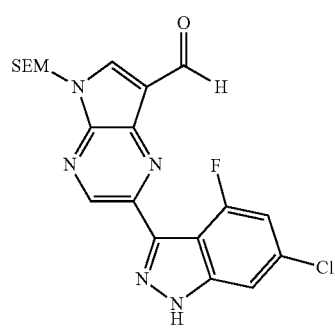

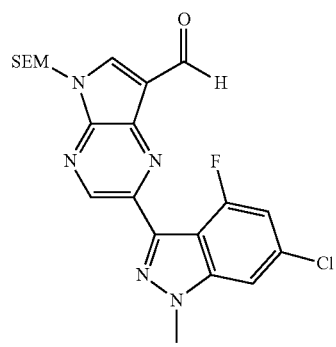

2-(6-Chloro-4-fluoro-1H-indazol-3-yl)-5-(2-trimethylsilanyl-ethoxymethyl)-5H-pyrrolo[2,3-b]pyrazine-7-carbaldehyde (0.5 g, 1.12 mmol) was dissolved in DMF (5.6 ml) and cooled in an ice bath. Sodium hydride (60% dispersion, 67 mg, 1.68 mmol) was carefully added. The mixture was stirred for 10 min then iodomethane (84 ul, 1.35 mmol) was added and the reaction was warmed to room temperature and stirred for 18 h. Water and ethyl acetate were added to the reaction. The layers were separated and the aqueous layer was extracted twice more with ethyl acetate. The combined organic layers were washed water and sodium chloride solution and dried over sodium sulfate. After evaporation the remaining residue was purified by silica gel chromatography (ethyl acetate/dichloromethane) to give 257 mg (50%) of 2-(6-chloro-4-fluoro-1-methyl-1H-indazol-3-yl)-5-(2-trimethylsilanyl-ethoxymethyl)-5H-pyrrolo[2,3-b]pyrazine-7-carbaldehyde. (M+H)⁺=460.

Step 6

2-(6-Chloro-4-fluoro-1-methyl-1H-indazol-3-yl)-5-(2-trimethylsilanyl-ethoxymethyl)-5H-pyrrolo[2,3-b]pyrazine-7-carboxylic acid

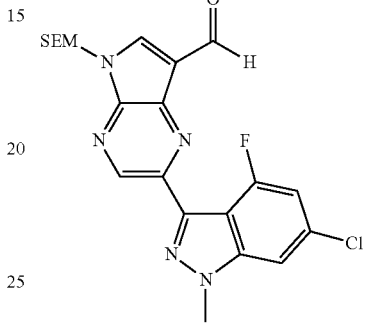

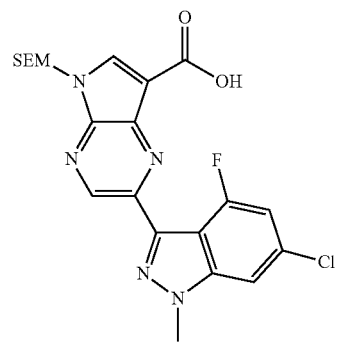

2-(6-Chloro-4-fluoro-1-methyl-1H-indazol-3-yl)-5-(2-trimethylsilanyl-ethoxymethyl)-5H-pyrrolo[2,3-b]pyrazine-7-carbaldehyde (255 mg, 0.55 mmol) was dissolved in THF (8.3 ml) and water (2.8 ml). Sulfamic acid (517 mg, 5.3 mmol) was added. The reaction flask was cooled in an ice/water bath and a solution of sodium chlorite (104 mg, 1.15 mmol) and potassium phosphate monobasic (1.45 g, 10.6 mmol) in water (8 ml) was slowly added. After 1 h the reaction mixture was poured into ethyl acetate and water. The layers were separated and the aqueous layer was extracted once more with ethyl acetate. The combined organic layers were washed with water and sodium chloride solution, and dried over sodium sulfate. Evaporation of the solvent gave 270 mg of 2-(6-chloro-4-fluoro-1-methyl-1H-indazol-3-yl)-5-(2-trimethylsilanylethoxymethyl)-5H-pyrrolo[2,3-b]pyrazine-7-carboxylic acid as a light yellow solid. (M+H)⁺=476.

Step 7

1-((R)-2-Amino-propionyl)-azetidine-3-carbonitrile trifluoroacetate

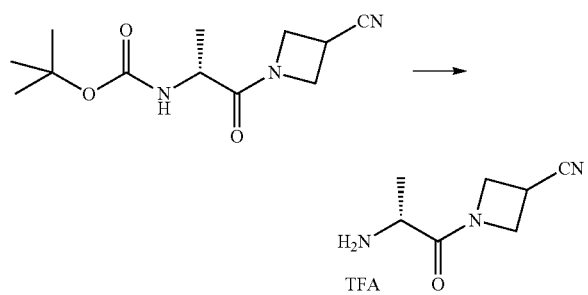

[(R)-2-(3-cyanoazetidin-1-yl)-1-methyl-2-oxo-ethyl]-carbamic acid tert-butyl ester (47 mg, 0.185 mmol) was dissolved in dichloromethane (1 ml) and cooled in an ice bath. Trifluoroacetic acid (0.5 ml) was slowly added and the reaction was stirred at room temperature for 2 h then evaporated and dried under high vacuum to afford 1-((R)-2-amino-propionyl)-azetidine-3-carbonitrile trifluoroacetate which was used without further purification.

Step 8

2-(6-Chloro-4-fluoro-1-methyl-1H-indazol-3-yl)-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide

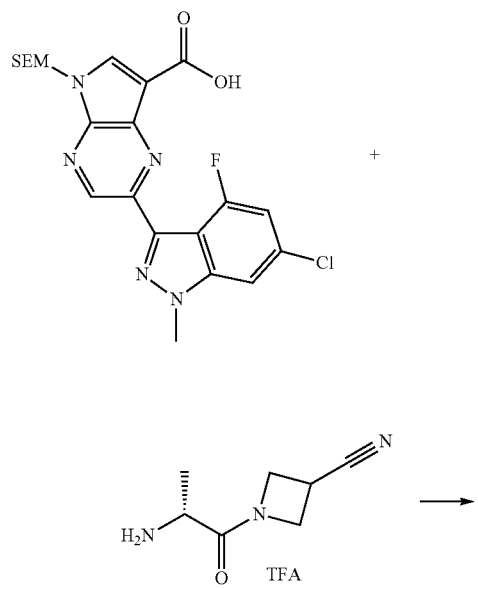

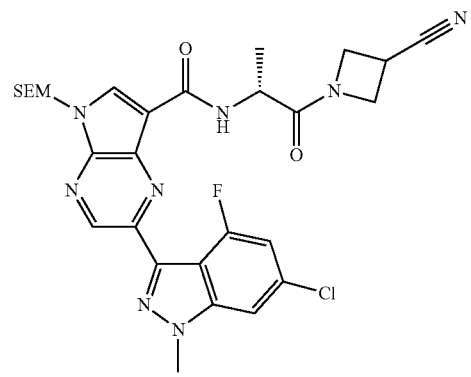

1-((R)-2-Amino-propionyl)-azetidine-3-carbonitrile trifluoroacetate (crude from Step 7) was dissolved in acetonitrile (2 ml) to which was then added 2-(6-chloro-4-fluoro-1-methyl-1H-indazol-3-yl)-5-(2-trimethylsilanyl-ethoxymethyl)-5H-pyrrolo[2,3-b]pyrazine-7-carboxylic acid (80 mg, 0.168 mmol), O-benzotriazol-1-yl-N,N,N',N'-tetramethyluronium tetrafluoroborate (81 mg, 0.252 mmol) and N,N-diisopropylethylamine (0.15 ml, 0.84 mmol). The reaction was stirred at room temperature for 18 h and then water and ethyl acetate were added. The layers were separated and the aqueous layer was extracted once more with ethyl acetate. The combined organic layers were washed with sodium chloride solution and dried over sodium sulfate. After evaporation, the residue was purified by silica gel chromatography (methanol/dichloromethane) to afford 84 mg (82%) of 2-(6-chloro-4-fluoro-1-methyl-1H-indazol-3-yl)-5-(2-trimethylsilanylethoxymethyl)-5H-pyrrolo[2,3-b]pyrazine-7-carboxylic acid [(R)-2-(3-cyano-azetidin-1-yl)-1-methyl-2-oxo-ethyl]-amide. (M+Na)⁺=633.

Step 9

2-(6-Chloro-4-fluoro-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide

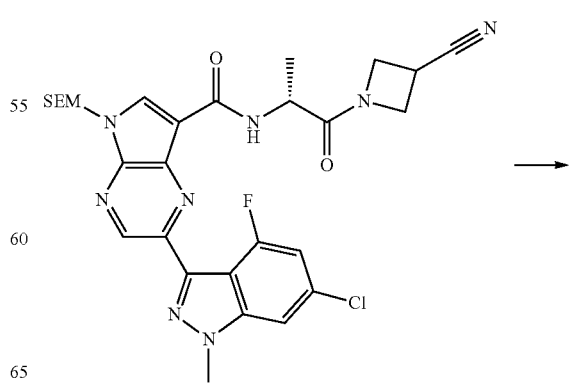

597
-continued

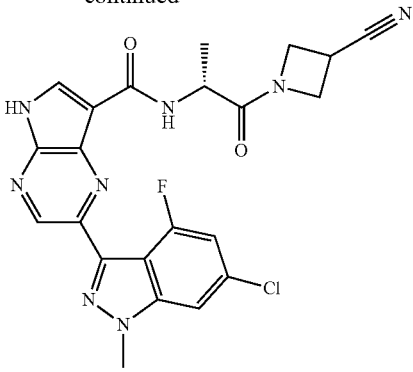

2-(6-Chloro-4-fluoro-1-methyl-1H-indazol-3-yl)-5-(2-tri-methylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide (84 mg, 0.137 mmol) was suspended in dichloromethane (2 ml) and cooled in an ice bath. Trifluoroacetic acid (0.9 ml) was slowly added and the reaction was stirred at room temperature for 3 h then evaporated. The residue was dissolved in dichloromethane (1.4 ml) and ethylenediamine (0.55 ml, 8.25 mmol) was added. The reaction was stirred for 8 h. Water was added giving a cloudy mixture, which was extracted with ethyl acetate eight times. The combined organic layers were washed with sodium chloride solution and dried over sodium sulfate. Drying agent was filtered off and rinsed with 10% methanol/dichloromethane, and evaporated to a residue. This was combined with solid which had appeared in the aqueous layer. The combined material was purified by silica gel chromatography (methanol/dichloromethane) to give 32 mg (48%) of 2-(6-chloro-4-fluoro-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide. (M+H)$^+$=481; mp=267-268° C. $^1$H NMR (300 MHz, DMSO-d$_6$) δ: 9.00 (s, 1H), 8.54 (d, J=7.2 Hz, 1H), 8.49 (d, J=10.6 Hz, 1H), 7.86-7.90 (m, 1H), 7.18 (d, J=10.2 Hz, 1H), 4.42-4.69 (m, 3H), 4.18 (s, 3H), 4.07-4.17 (m, 1H), 3.95-4.05 (m, 1H), 3.76-3.87 (m, 1H), 1.32-1.41 (m, 3H).

Example 125

2-(6-Chloro-1-methyl-1H-indazol-3-yl)-5H-pyrrolo[2,3-b]pyrazine-7-carboxylic acid [2-(3-cyano-pyrrolidin-1-yl)-1-methyl-ethyl]-amide

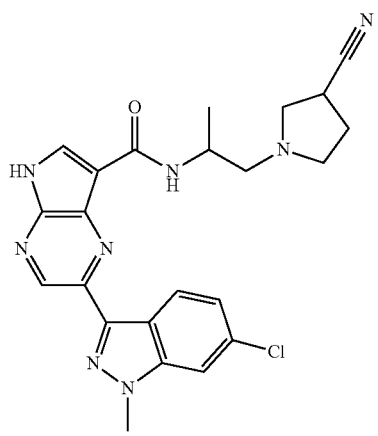 [SMILES: CC(CN1CCC(C#N)C1)NC(=O)c1c[nH]c2ncc(-c3nn(C)c4cc(Cl)ccc34)nc12]

598

Step 1

[2-(6-Chloro-1-methyl-1H-indazol-3-yl)-5-(2-trimethylsilanyl-ethoxymethyl)-5H-pyrrolo[2,3-b]pyrazin-7-yl]-(2-methyl-aziridin-1-yl)-methanone

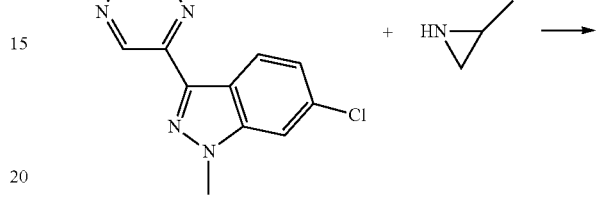

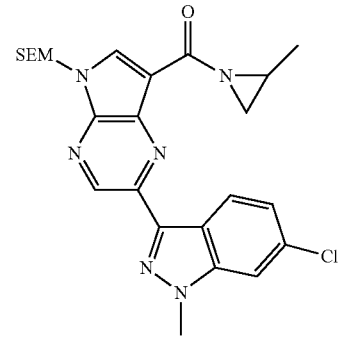

2-(6-Chloro-1-methyl-1H-indazol-3-yl)-5-((2-(trimethylsilyl)ethoxy)methyl)-5H-pyrrolo[3,2-b]pyrazine-7-carboxylic acid (100 mg, 0.218 mmol) was suspended in dichloromethane (2.2 ml). 4-Dimethylaminopyridine (5.3 mg, 0.044 mmol), N,N-diisopropylethylamine (76 ul, 0.44 mmol) and then 1-(3-(dimethylamino)-propyl)-3-ethylcarbodiimide (84 mg, 0.44 mmol) were added. The solution was stirred for 5 min then cooled in an ice bath. 2-Methylaziridine (23 ul, 0.33 mmol) was added and the reaction was warmed to room temperature. Stirring was continued until judged to be complete by TLC then water, dilute HCl and ethyl acetate were added. The aqueous layer was extracted once more with ethyl acetate and the combined organic layers were washed with sodium bicarbonate solution and dried over sodium sulfate. After evaporation the residue was purified by silica gel chromatography (ethyl acetate/hexanes) to give 70 mg (64%) of [2-(6-chloro-1-methyl-1H-indazol-3-yl)-5-(2-trimethylsilanyl-ethoxymethyl)-5H-pyrrolo[2,3-b]pyrazin-7-yl]-(2-methyl-aziridin-1-yl)-methanone. $^1$H NMR (300 MHz, CDCl$_3$) δ ppm 9.23 (s, 1H) 8.76 (d, J=8.7 Hz, 1H) 8.33 (s, 1H) 7.44 (s, 1H) 7.24 (d, J=8.7 Hz, 1H) 5.73 (s, 2H) 4.14 (s, 3H) 3.56-3.65

(m, 6H) 2.80-2.91 (m, 1H) 2.59 (d, J=6.0 Hz, 1H) 2.33 (d, J=3.8 Hz, 1H) 1.41 (d, J=5.3 Hz, 3H) 0.89-0.99 (m, 2H)-0.05 (s, 9H).

Step 2

2-(6-Chloro-1-methyl-1H-indazol-3-yl)-5-(2-trimethylsilanyl-ethoxymethyl)-5H-pyrrolo[2,3-b]pyrazine-7-carboxylic acid [2-(3-cyano-pyrrolidin-1-yl)-1-methyl-ethyl]-amide

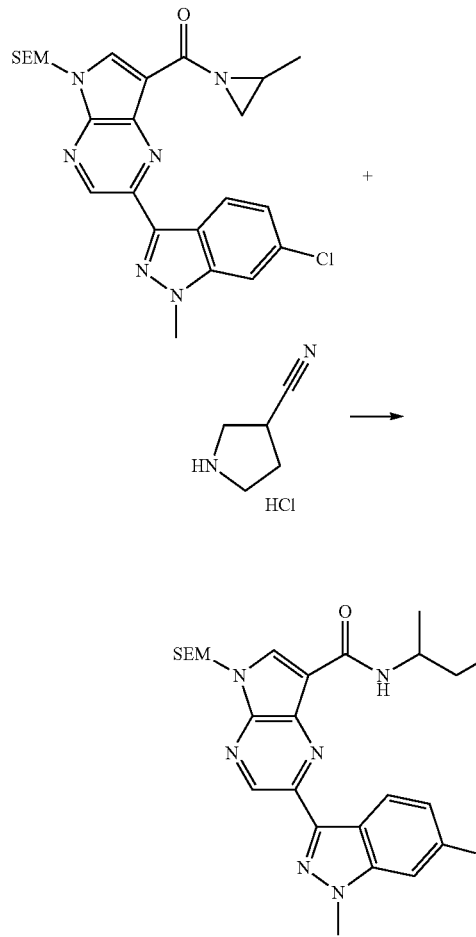

[2-(6-Chloro-1-methyl-1H-indazol-3-yl)-5-(2-trimethylsilanyl-ethoxymethyl)-5H-pyrrolo[2,3-b]pyrazin-7-yl]-(2-methyl-aziridin-1-yl)-methanone (70 mg, 0.14 mmol) was dissolved in 1:1 THF: acetonitrile (1.5 ml). 3-Cyanopyrrolidine hydrochloride (28 mg, 0.21 mmol) and N,N-diisopropylethylamine (37 ul, 0.21 mmol) were added and the reaction was heated in a microwave reactor at 120° C. for 2 h. An additional 0.5 eq of 3-cyanopyrrolidine hydrochloride and N,N-diisopropylethylamine were added and the heating was repeated twice more. Water and ethyl acetate were then added to the cooled solution. The aqueous layer was extracted twice more with ethyl acetate and the combined organics were washed with sodium chloride solution and dried over sodium sulfate. After evaporation of solvent the crude residue was purified by silica gel chromatography (ethyl acetate/dichloromethane) to give 21 mg (25%) of 2-(6-chloro-1-methyl-1H-indazol-3-yl)-5-(2-trimethylsilanyl-ethoxymethyl)-5H-pyrrolo[2,3-b]pyrazine-7-carboxylic acid [2-(3-cyano-pyrrolidin-1-yl)-1-methyl-ethyl]-amide. (M+H)$^+$=593.

Step 3

2-(6-Chloro-1-methyl-1H-indazol-3-yl)-5H-pyrrolo[2,3-b]pyrazine-7-carboxylic acid [2-(3-cyano-pyrrolidin-1-yl)-1-methyl-ethyl]-amide 2-(6-Chloro-1-methyl-1H-indazol-3-yl)-5-(2-trimethylsilanyl-ethoxymethyl)-5H-pyrrolo[2,3-b]pyrazine-7-carboxylic acid [2-(3-cyano-pyrrolidin-1-yl)-1-methyl-ethyl]-amide (37 mg, 0.062 mmol) was dissolved in dichloromethane (0.8 ml) and cooled in ice bath. Trifluoroacetic acid (0.4 ml) was slowly added and the reaction was stirred at room temperature for 2 h. The reaction was evaporated and the residue was dissolved in dichloromethane (1.2 ml). Ethylenediamine (0.25 ml, 3.7 mmol) was added and the mixture was stirred for 18 h. Water and then ethyl acetate were added to the mixture. The layers were separated and the aqueous layer was extracted twice more with ethyl acetate. The combined organic layers were washed with sodium chloride solution and dried over sodium sulfate. After evaporation, the residue was purified by silica gel chromatography (methanol/dichloromethane) to afford 15 mg (52%) of 2-(6-chloro-1-methyl-1H-indazol-3-yl)-5H-pyrrolo[2,3-b]pyrazine-7-carboxylic acid [2-(3-cyano-pyrrolidin-1-yl)-1-methyl-ethyl]-amide. MS: (M+H)$^+$=463; mp=206-209° C. $^1$H NMR (300 MHz, DMSO-d$_6$) δ: 12.83-12.94 (m, 1H), 9.10 (s, 1H), 8.38-8.51 (m, 2H), 8.04-8.13 (m, 1H), 7.99-8.04 (m, 1H), 7.30-7.39 (m, 1H), 4.20-4.36 (m, 1H), 4.18 (s, 3H), 3.07-3.22 (m, 1H), 2.53-2.88 (m, 5H), 1.99-2.15 (m, 1H), 1.74-1.92 (m, 1H), 1.33 (d, J=6.4 Hz, 3H).

Example 126

2-(6-Chloro-1-methyl-1H-indazol-3-yl)-5H-pyrrolo[2,3-b]pyrazine-7-carboxylic acid [(R)-2-(3-cyano-azetidin-1-yl)-1-methyl-ethyl]-amide

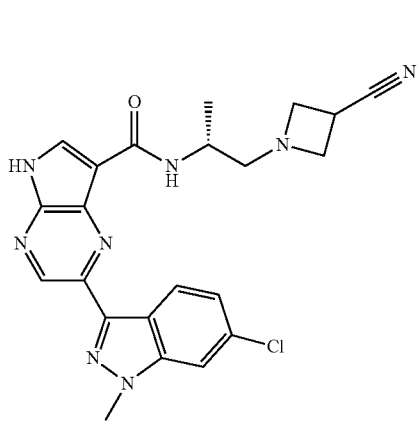

Step 1

(R)-2-methyl-1-(4-nitro-benzenesulfonyl)-aziridine

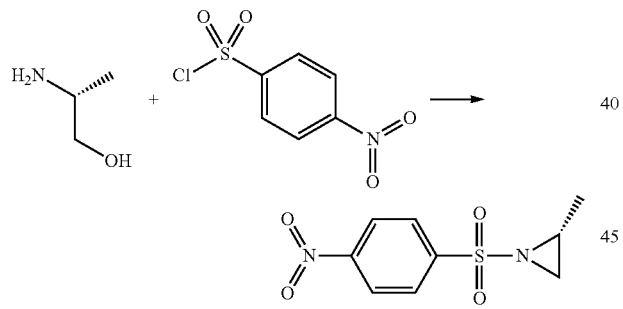

4-Nitrobenzene-1-sulfonyl chloride (6.9 g, 31 mmol) was dissolved in acetonitrile (8 ml) and stirred in an ice bath. A solution of (R)-2-aminopropan-1-ol (1 g, 13.3 mmol) in pyridine (5 ml) was added slowly and the reaction was stirred for 2 h. Ethyl acetate (25 ml) and water (10 ml) were added and the reaction was stirred for 10 min. The layers were separated and the organic layer was washed with 1M citric acid solution twice and with water once. The organic layer was cooled to 10° C. and 7 ml of water was added followed by dropwise addition of N,N-diisopropylethylamine (3.7 ml, 21.3 mmol). After stirring for 1 h the layers were separated and the aqueous layer was extracted with ethyl acetate. The combined organics were washed twice with 1M citric acid solution and twice with water. Isopropanol (70 ml) was then added and the solvents were evaporated slowly leaving mostly isopropanol. (R)-2-Methyl-1-(4-nitro-benzenesulfonyl)-aziridine 2.2 g (69%) was obtained after crystallization from isopropanol. $^1$H NMR (300 MHz, CDCl$_3$) δ: 8.40 (d, J=9.1 Hz, 2H), 8.16 (d, J=9.1 Hz, 2H), 2.92-3.04 (m, 1H), 2.74 (d, J=7.2 Hz, 1H), 2.13 (d, J=4.5 Hz, 1H), 1.30 (d, J=5.7 Hz, 3H).

Step 2

N—[(R)-2-(3-Cyano-azetidin-1-yl)-1-methyl-ethyl]-4-nitro-benzenesulfonamide

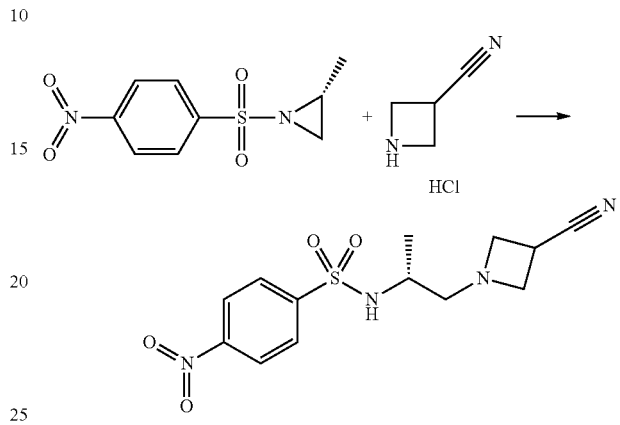

(R)-2-Methyl-1-(4-nitro-benzenesulfonyl)-aziridine (0.2 g, 0.83 mmol) was dissolved in THF (1 ml). 3-Cyanoazetidinine hydrochloride (117 mg, 0.99 mmol) and N,N-diisopropylethylamine (0.2 ml, 1.16 mmol) were added and the reaction was stirred for 64 h. Water and ethyl acetate were then added. The aqueous layer was extracted twice more with ethyl acetate, the combined organics were washed with sodium chloride solution and dried over sodium sulfate. After evaporation the residue was purified by silica gel chromatography (ethyl acetate/hexanes) to give 133 mg (49%) of N—[(R)-2-(3-cyano-azetidin-1-yl)-1-methyl-ethyl]-4-nitro-benzenesulfonamide. (M+H)$^+$=325.

Step 3

N—[(R)-2-(3-Cyano-azetidin-1-yl)-1-methyl-ethyl]-4-nitro-benzenesulfonamide

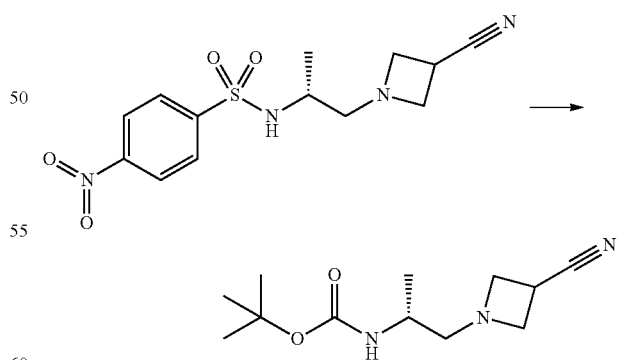

N—[(R)-2-(3-Cyano-azetidin-1-yl)-1-methyl-ethyl]-4-nitro-benzenesulfonamide (133 mg, 0.41 mmol) was dissolved in DMF (2 ml). Di-tert-butyldicarbonate (98 mg, 0.45 mmol) and 4-dimethylaminopyridine (55 mg, 0.45 mmol) were added and the reaction was stirred for 6 h. Thiophenol (63 ul, 0.615 mmol) and potassium carbonate (170 mg, 1.23 mmol)

were then added and the reaction was allowed to stand for 16 h at 0° C. Water, sodium hydroxide solution and ethyl acetate were then added. The aqueous layer was extracted once more with ethyl acetate and the combined organic layers were washed with sodium chloride solution and dried over sodium sulfate. After evaporation, the residue was purified by silica gel chromatography (ethyl acetate/hexanes) to give 75 mg (76%) of [(R)-2-(3-cyano-azetidin-1-yl)-1-methyl-ethyl]-carbamic acid tert-butyl ester. (M+H)$^+$=240.

Step 4

1-((R)-2-Amino-propyl)-azetidine-3-carbonitrile bistrifluoroacetate

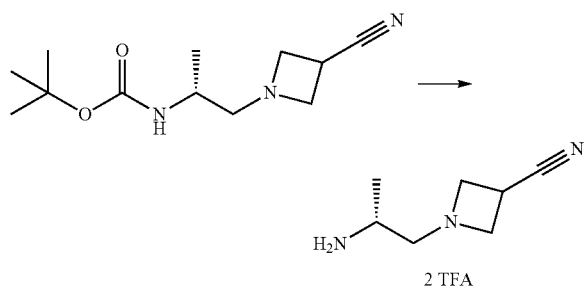

[(R)-2-(3-cyano-azetidin-1-yl)-1-methyl-ethyl]-carbamic acid tert-butyl ester (35 mg, 0.146 mmol) was dissolved in dichloromethane (1 ml) and cooled in an ice bath. Trifluoroacetic acid (0.45 ml) was slowly added and the reaction was stirred at room temperature for 2 h then evaporated and dried under high vacuum to afford 1-((R)-2-amino-propyl)-azetidine-3-carbonitrile bistrifluoroacetate which was used without further purification.

Step 5

2-(6-Chloro-1-methyl-1H-indazol-3-yl)-5-(2-trimethylsilanyl-ethoxymethyl)-5H-pyrrolo[2,3-b]pyrazine-7-carboxylic acid [(R)-2-(3-cyano-azetidin-1-yl)-1-methyl-ethyl]-amide

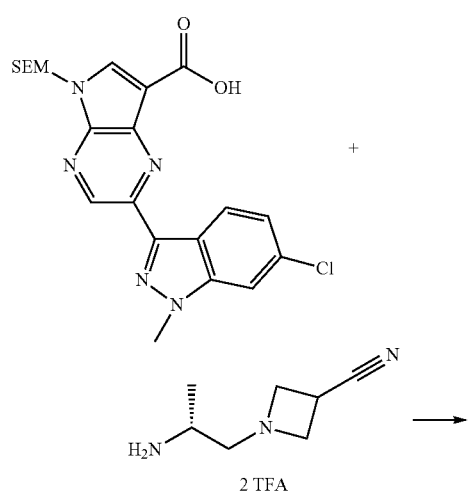

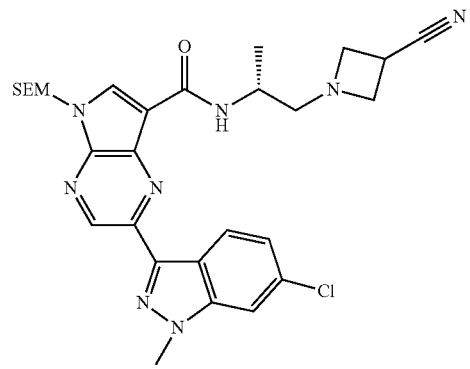

1-((R)-2-Amino-propyl)-azetidine-3-carbonitrile bistrifluoroacetate (crude from Step 4) was dissolved in acetonitrile (1.5 ml) to which was then added 2-(6-chloro-1-methyl-1H-indazol-3-yl)-5-(2-trimethylsilanyl-ethoxymethyl)-5H-pyrrolo[2,3-b]pyrazine-7-carboxylic acid (60 mg, 0.132 mmol), O-benzotriazol-1-yl-N,N,N',N'-tetramethyluronium tetrafluoroborate (70 mg, 0.22 mmol) and N,N-diisopropylethylamine (0.13 ml, 0.73 mmol). The reaction was stirred at room temperature for 18 h and then water and ethyl acetate were added. The layers were separated and the aqueous layer was extracted once more with ethyl acetate. The combined organic layers were washed with sodium chloride solution and dried over sodium sulfate. After evaporation, the residue was purified by silica gel chromatography (methanol/dichloromethane) to afford 58 mg (64%) of 2-(6-chloro-1-methyl-1H-indazol-3-yl)-5-(2-trimethylsilanyl-ethoxymethyl)-5H-pyrrolo[2,3-b]pyrazine-7-carboxylic acid [(R)-2-(3-cyano-azetidin-1-yl)-1-methyl-ethyl]-amide. (M+H)$^+$=579.

Step 6

2-(6-Chloro-1-methyl-1H-indazol-3-yl)-5H-pyrrolo[2,3-b]pyrazine-7-carboxylic acid [(R)-2-(3-cyano-azetidin-1-yl)-1-methyl-ethyl]-amide

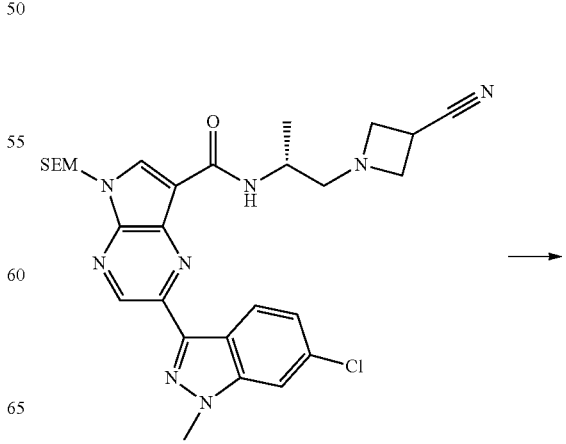

605
-continued

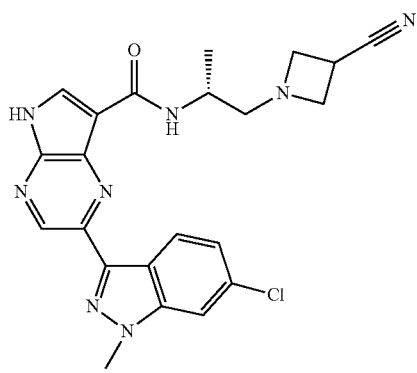 [SMILES: C[C@H](CN1CC(C#N)C1)NC(=O)c1c[nH]c2ncc(-c3nn(C)c4cc(Cl)ccc34)nc12]

2-(6-Chloro-1-methyl-1H-indazol-3-yl)-5-(2-trimethylsilanyl-ethoxymethyl)-5H-pyrrolo[2,3-b]pyrazine-7-carboxylic acid [(R)-2-(3-cyano-azetidin-1-yl)-1-methyl-ethyl]-amide (58 mg, 0.10 mmol) was dissolved in dichloromethane (1.4 ml) and cooled in ice bath. Trifluoroacetic acid (0.6 ml) was slowly added and the reaction was stirred at room temperature for 5 h. The reaction was evaporated and the residue was dissolved in dichloromethane (1 ml). Ethylenediamine (0.40 ml, 6.0 mmol) was added and the mixture was stirred for 18 h. Water and then ethyl acetate were added to the mixture. The layers were separated and the aqueous layer was extracted twice more with ethyl acetate. The combined organic layers were washed with sodium chloride solution and dried over sodium sulfate. After evaporation, the residue was purified by silica gel chromatography (methanol/dichloromethane) to afford 29 mg (64%) of 2-(6-chloro-1-methyl-1H-indazol-3-yl)-5H-pyrrolo[2,3-b]pyrazine-7-carboxylic acid [(R)-2-(3-cyano-azetidin-1-yl)-1-methyl-ethyl]-amide. MS: (M+H)$^+$=449; mp=235-238° C. $^1$H NMR (300 MHz, DMSO-d$_6$) δ: 9.10 (s, 1H), 8.44 (d, J=8.7 Hz, 1H), 8.43 (s, 1H), 8.01 (d, J=1.5 Hz, 1H), 8.02 (d, J=8.3 Hz, 1H), 7.34 (dd, J=8.7, 1.5 Hz, 1H), 4.18 (s, 3H), 4.04-4.16 (m, 1H), 3.36-3.53 (m, 4H), 3.28 (d, J=7.9 Hz, 1H), 2.60-2.68 (m, 2H), 1.28 (d, J=6.8 Hz, 3H).

Example 127

2-(6-Chloro-4-fluoro-1-methyl-1H-indazol-3-yl)-5H-pyrrolo[2,3-b]pyrazine-7-carboxylic acid isopropylamide

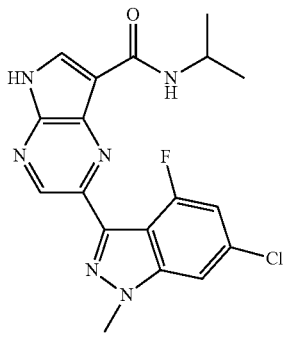 [SMILES: CC(C)NC(=O)c1c[nH]c2ncc(-c3nn(C)c4cc(Cl)cc(F)c34)nc12]

Step 1

2-(6-Chloro-4-fluoro-1-methyl-1H-indazol-3-yl)-5-(2-trimethylsilanyl-ethoxymethyl)-5H-pyrrolo[2,3-b]pyrazine-7-carboxylic acid isopropylamide

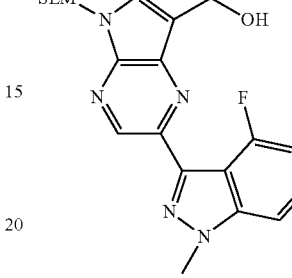

+ 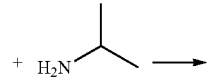 →

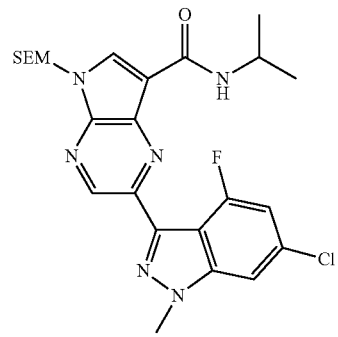

2-(6-Chloro-4-fluoro-1-methyl-1H-indazol-3-yl)-5-(2-trimethylsilanyl-ethoxymethyl)-5H-pyrrolo[2,3-b]pyrazine-7-carboxylic acid (59 mg, 0.124 mmol), O-benzotriazol-1-yl-N,N,N',N'-tetramethyluronium tetrafluoroborate (60 mg, 0.186 mmol), N,N-diisopropylethylamine (0.11 ml, 0.62 mmol) and isopropylamine (11 ul, 0.124 mmol) were added together in acetonitrile (1.3 ml). The reaction was stirred at room temperature for 18 h then water and ethyl acetate were added. The layers were separated and the aqueous layer was extracted twice more with ethyl acetate. The combined organic layers were washed with sodium chloride solution and dried over sodium sulfate. After evaporation, the residue was purified by silica gel chromatography (ethyl acetate/hexanes) to give 46 mg (72%) of 2-(6-chloro-4-fluoro-1-methyl-1H-indazol-3-yl)-5-(2-trimethylsilanyl-ethoxymethyl)-5H-pyrrolo[2,3-b]pyrazine-7-carboxylic acid isopropylamide. (M+H)⁺=517.

Step 2

2-(6-Chloro-4-fluoro-1-methyl-1H-indazol-3-yl)-5H-pyrrolo[2,3-b]pyrazine-7-carboxylic acid isopropylamide

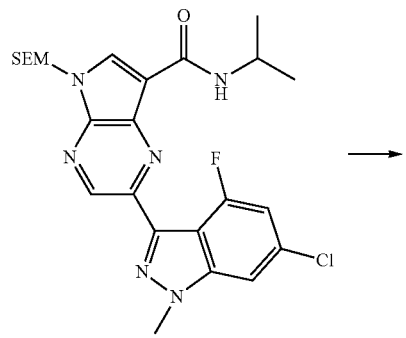

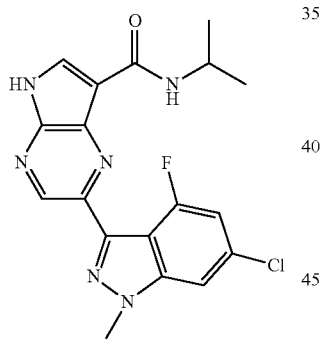

2-(6-Chloro-4-fluoro-1-methyl-1H-indazol-3-yl)-5-(2-trimethylsilanyl-ethoxymethyl)-5H-pyrrolo[2,3-b]pyrazine-7-carboxylic acid isopropylamide (46 mg, 0.09 mmol) was dissolved in dichloromethane (1.2 ml) and cooled in ice bath. Trifluoroacetic acid (0.6 ml) was slowly added and the reaction was stirred at room temperature for 2 h. The reaction was evaporated and the residue was dissolved in dichloromethane (1 ml). Ethylenediamine (0.36 ml, 5.3 mmol) was added and the mixture was stirred for 18 h. Water and then ethyl acetate were added to the mixture. The resulting precipitate was filtered off, rinsed with water diethyl ether and ethyl acetate and set aside. The organic filtrate was separated, washed with sodium chloride solution and dried over sodium sulfate. After evaporation, the residue was combined with the precipitate collected above. The solids were dried under high vacuum to afford 34 mg (98%) of 2-(6-chloro-4-fluoro-1-methyl-1H-indazol-3-yl)-5H-pyrrolo[2,3-b]pyrazine-7-carboxylic acid isopropylamide. MS: (M+H)⁺=387; mp=347-349° C. ¹H NMR (300 MHz, DMSO-d₆) δ: 9.01 (s, 1H), 8.42 (s, 1H), 8.22-8.33 (m, 1H), 7.88 (s, 1H), 7.20-7.32 (m, 1H), 4.13-4.30 (m, 1H), 4.18 (s, 3H), 1.24 (d, J=6.4 Hz, 6H).

Example 128

2-[6-Chloro-1-(2-dimethylamino-ethyl)-4-fluoro-1H-indazol-3-yl]-5H-pyrrolo[2,3-b]pyrazine-7-carboxylic acid isopropylamide hydrochloride

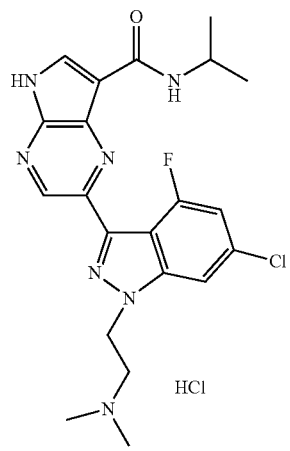 [SMILES: CC(C)NC(=O)c1c[nH]c2ncc(-c3nn(CCN(C)C)c4cc(Cl)cc(F)c34)nc12 ; Cl]

Step 1

2-[6-Chloro-1-(2-dimethylamino-ethyl)-4-fluoro-1H-indazol-3-yl]-5-(2-trimethylsilanylethoxymethyl)-5H-pyrrolo[2,3-b]pyrazine-7-carbaldehyde

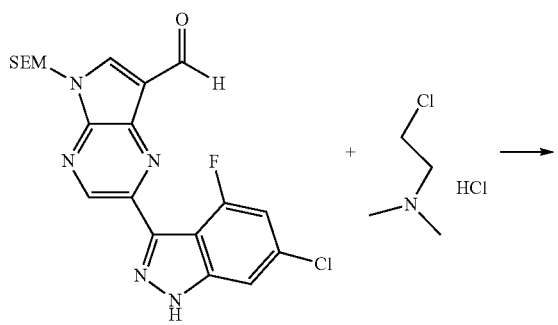

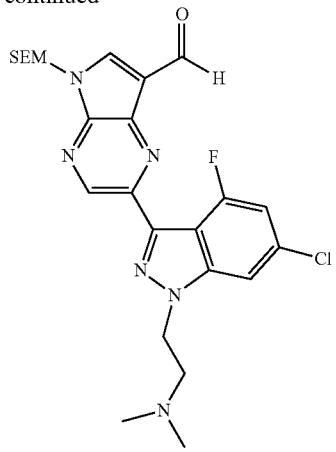

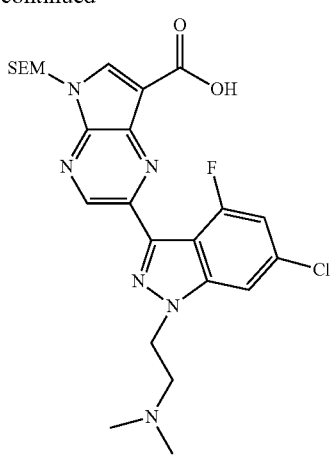

2-(6-Chloro-4-fluoro-1H-indazol-3-yl)-5-(2-trimethylsilanyl-ethoxymethyl)-5H-pyrrolo[2,3-b]pyrazine-7-carbaldehyde (100 mg, 0.22 mmol) was dissolved in DMF (0.5 ml) and cooled in an ice bath. Sodium hydride (60% dispersion, 22 mg, 0.56 mmol) was carefully added. The mixture was stirred for 10 min then dimethylaminoethyl chloride hydrochloride (36 mg, 0.25 mmol) and potassium iodide (4 mg, 0.022 mmol) were added and the reaction was warmed to room temperature then stirred at 50° C. overnight. After cooling to room temperature, water and ethyl acetate were added to the reaction. The layers were separated and the aqueous layer was extracted twice more with ethyl acetate. The combined organic layers were washed water and sodium chloride solution and dried over sodium sulfate. After evaporation, the residue was purified by silica gel chromatography (methanol/dichloromethane) to give 46 mg (40%) of 2-[6-chloro-1-(2-dimethylamino-ethyl)-4-fluoro-1H-indazol-3-yl]-5-(2-trimethylsilanylethoxymethyl)-5H-pyrrolo[2,3-b]pyrazine-7-carbaldehyde. $(M+H)^+$=517.

2-[6-Chloro-1-(2-dimethylamino-ethyl)-4-fluoro-1H-indazol-3-yl]-5-(2-trimethylsilanylethoxymethyl)-5H-pyrrolo[2,3-b]pyrazine-7-carbaldehyde (46 mg, 0.09 mmol) was dissolved in THF (1.3 ml) and water (0.4 ml) and sulfamic acid (83 mg, 0.85 mmol) was added. A solution of sodium chlorite (17 mg, 0.185 mmol) and potassium phosphate monobasic (232 mg, 1.7 mmol) in water (1.4 ml) was slowly added. After 1 h the reaction mixture was poured into ethyl acetate and water. The pH was adjusted to 6, the layers were separated and the aqueous layer was extracted five times with ethyl acetate. The combined organic layers were dried over sodium sulfate and concentrated to give 53 mg of 2-[6-chloro-1-(2-dimethylamino-ethyl)-4-fluoro-1H-indazol-3-yl]-5-(2-trimethylsilanyl-ethoxymethyl)-5H-pyrrolo[2,3-b]pyrazine-7-carboxylic acid.

Step 2

2-[6-Chloro-1-(2-dimethylamino-ethyl)-4-fluoro-1H-indazol-3-yl]-5-(2-trimethylsilanylethoxymethyl)-5H-pyrrolo[2,3-b]pyrazine-7-carboxylic acid Step 3

2-[6-Chloro-1-(2-dimethylamino-ethyl)-4-fluoro-1H-indazol-3-yl]-5-(2-trimethylsilanylethoxymethyl)-5H-pyrrolo[2,3-b]pyrazine-7-carboxylic acid isopropylamide

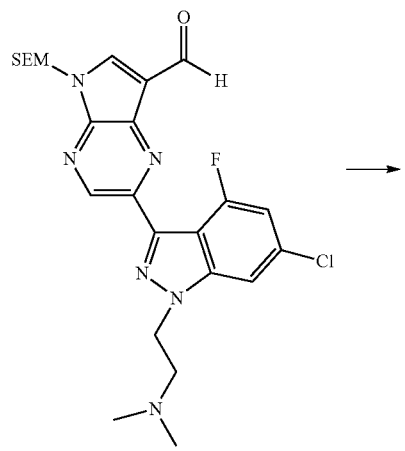

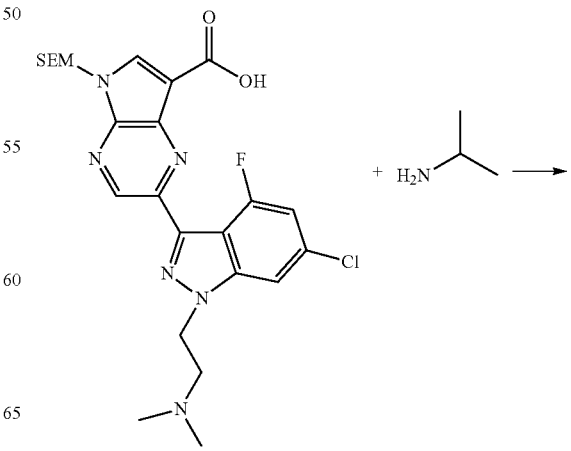

611
-continued

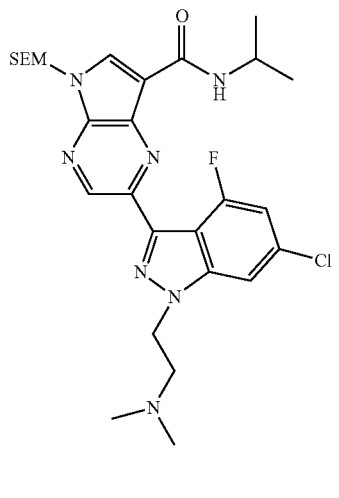

2-[6-Chloro-1-(2-dimethylamino-ethyl)-4-fluoro-1H-indazol-3-yl]-5-(2-trimethylsilanylethoxymethyl)-5H-pyrrolo[2,3-b]pyrazine-7-carboxylic acid (50 mg, 0.094 mmol), O-benzotriazol-1-yl-N,N,N',N'-tetramethyluronium tetrafluoroborate (45 mg, 0.14 mmol), N,N-diisopropylethylamine (0.08 ml, 0.47 mmol) and isopropylamine (10 ul, 0.11 mmol) were added together in acetonitrile (1 ml). The reaction was stirred at room temperature for 18 h then water and ethyl acetate were added. The layers were separated and the aqueous layer was extracted twice more with ethyl acetate. The combined organic layers were washed with sodium chloride solution and dried over sodium sulfate. After evaporation, the residue was purified by silica gel chromatography (methanol/dichloromethane) to give 35 mg (65%) of 2-[6-chloro-1-(2-dimethylamino-ethyl)-4-fluoro-1H-indazol-3-yl]-5-(2-trimethylsilanyl-ethoxymethyl)-5H-pyrrolo[2,3-b]pyrazine-7-carboxylic acid isopropylamide.

Step 4

2-[6-Chloro-1-(2-dimethylamino-ethyl)-4-fluoro-1H-indazol-3-yl]-5H-pyrrolo[2,3-b]pyrazine-7-carboxylic acid isopropylamide hydrochloride

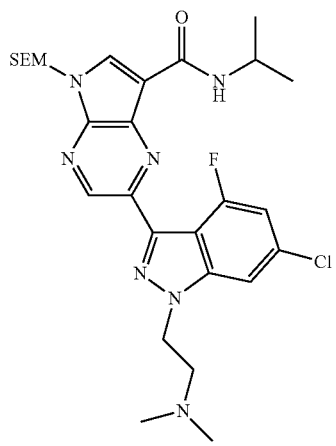

612
-continued

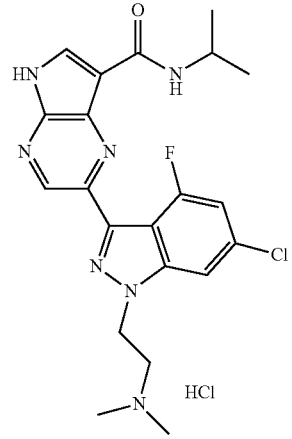

2-[6-Chloro-1-(2-dimethylamino-ethyl)-4-fluoro-1H-indazol-3-yl]-5-(2-trimethylsilanylethoxymethyl)-5H-pyrrolo[2,3-b]pyrazine-7-carboxylic acid isopropylamide (35 mg, 0.06 mmol) was dissolved in dichloromethane (1.6 ml) and cooled in ice bath. Trifluoroacetic acid (0.8 ml) was slowly added and the reaction was stirred at room temperature for 2 h. The reaction was evaporated and the residue was dissolved in dichloromethane (1 ml). Ethylenediamine (0.25 ml, 3.7 mmol) was added and the mixture was stirred for 18 h. Water and then ethyl acetate were added to the mixture. The layers were separated and the aqueous layer was extracted three times with ethyl acetate. The combined organic layers were washed with sodium chloride solution, dried over sodium sulfate and evaporated. The residue was purified by silica gel chromatography (methanol/dichloromethane). The product thus isolated was dissolved in methanol/dichloromethane and treated with 4 eq of 4 M HCl in 1,4-dioxane. Evaporation of the solvent provided a solid which was dried under high vacuum to afford 18 mg (62%) of 2-[6-chloro-1-(2-dimethylamino-ethyl)-4-fluoro-1H-indazol-3-yl]-5H-pyrrolo[2,3-b]pyrazine-7-carboxylic acid isopropylamide hydrochloride. MS: (M+H)$^+$=444; mp=281-283° C. $^1$H NMR (300 MHz, DMSO-d$_6$) δ: 10.17-10.33 (m, 1H), 9.08 (s, 1H), 8.44 (d, J=3.0 Hz, 1H), 8.26 (d, J=7.9 Hz, 1H), 8.03-8.08 (m, 1H), 7.34 (d, J=10.6 Hz, 1H), 4.94-5.05 (m, 2H), 4.14-4.30 (m, 1H), 3.66-3.77 (m, 2H), 2.89 (d, J=4.5 Hz, 6H), 1.24 (d, J=6.8 Hz, 6H).

Example 129

2-[6-Chloro-4-fluoro-1-(2-morpholin-4-yl-ethyl)-1H-indazol-3-yl]-5H-pyrrolo[2,3-b]pyrazine-7-carboxylic acid isopropylamide hydrochloride

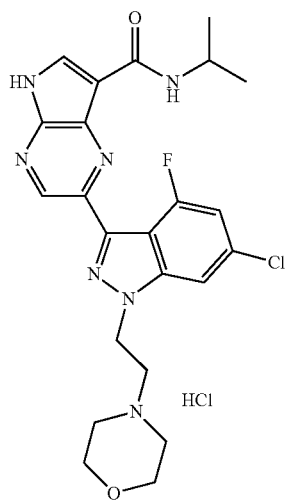 [SMILES: CC(C)NC(=O)c1c[nH]c2ncc(-c3nn(CCN4CCOCC4)c4cc(Cl)cc(F)c34)nc12 ; Cl]

Step 1

2-(6-Chloro-4-fluoro-1H-indazol-3-yl)-5-(2-trimethylsilanyl-ethoxymethyl)-5H-pyrrolo[2,3-b]pyrazine-7-carboxylic acid

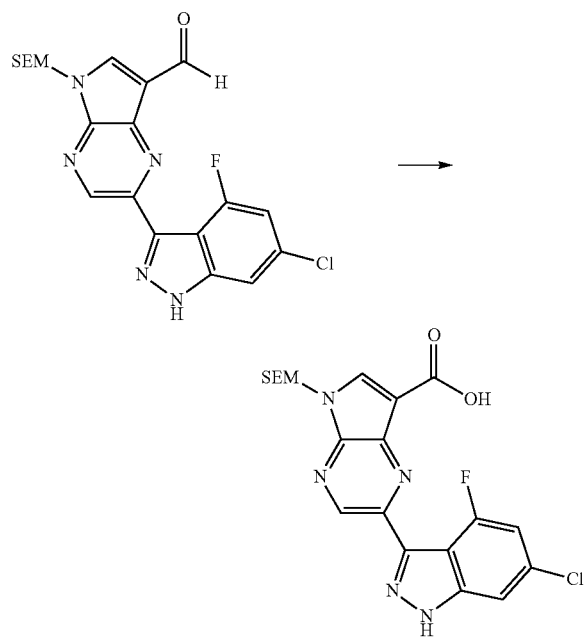

2-(6-Chloro-4-fluoro-1H-indazol-3-yl)-5-(2-trimethylsilanyl-ethoxymethyl)-5H-pyrrolo[2,3-b]pyrazine-7-carbaldehyde (139 mg, 0.31 mmol) was dissolved in THF (4.7 ml) and water (1.6 ml) and sulfamic acid (291 mg, 3.0 mmol) was added. A solution of sodium chlorite (17 mg, 0.185 mmol) and potassium phosphate monobasic (232 mg, 1.7 mmol) in water (1.4 ml) was slowly added. After 1 h the reaction mixture was poured into ethyl acetate and water. The layers were separated and the aqueous layer was extracted once more with ethyl acetate. The combined organic layers were dried over sodium sulfate and concentrated to give 136 mg of 2-(6-chloro-4-fluoro-1H-indazol-3-yl)-5-(2-trimethylsilanyl-ethoxymethyl)-5H-pyrrolo[2,3-b]pyrazine-7-carboxylic acid.

Step 2

2-(6-Chloro-4-fluoro-1H-indazol-3-yl)-5-(2-trimethylsilanyl-ethoxymethyl)-5H-pyrrolo[2,3-b]pyrazine-7-carboxylic acid isopropylamide

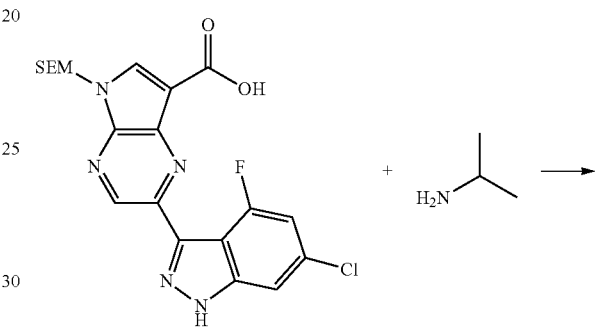

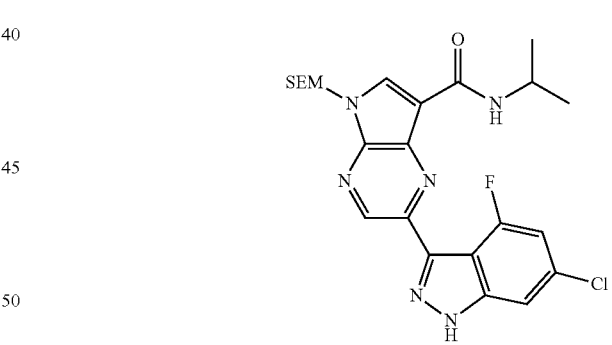

2-(6-Chloro-4-fluoro-1H-indazol-3-yl)-5-(2-trimethylsilanyl-ethoxymethyl)-5H-pyrrolo[2,3-b]pyrazine-7-carboxylic acid (140 mg, 0.30 mmol), O-benzotriazol-1-yl-N,N,N',N'-tetramethyluronium tetrafluoroborate (146 mg, 0.46 mmol), N,N-diisopropylethylamine (0.27 ml, 1.52 mmol) and isopropylamine (31 ul, 0.36 mmol) were added together in acetonitrile (1 ml). The reaction was stirred at room temperature for 18 h then water and ethyl acetate were added. The layers were separated and the aqueous layer was extracted twice more with ethyl acetate. The combined organic layers were washed with sodium chloride solution and dried over sodium sulfate. After evaporation, the residue was purified by silica gel chromatography (methanol/dichloromethane) to give 77 mg (51%) of 2-(6-chloro-4-fluoro-1H-indazol-3-yl)-

5-(2-trimethylsilanyl-ethoxymethyl)-5H-pyrrolo[2,3-b]pyrazine-7-carboxylic acid isopropylamide.

Step 3

2-[6-Chloro-4-fluoro-1-(2-morpholin-4-yl-ethyl)-1H-indazol-3-yl]-5-(2-trimethylsilanylethoxymethyl)-5H-pyrrolo[2,3-b]pyrazine-7-carboxylic acid isopropylamide

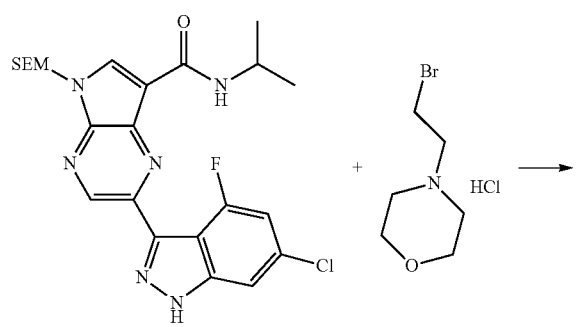

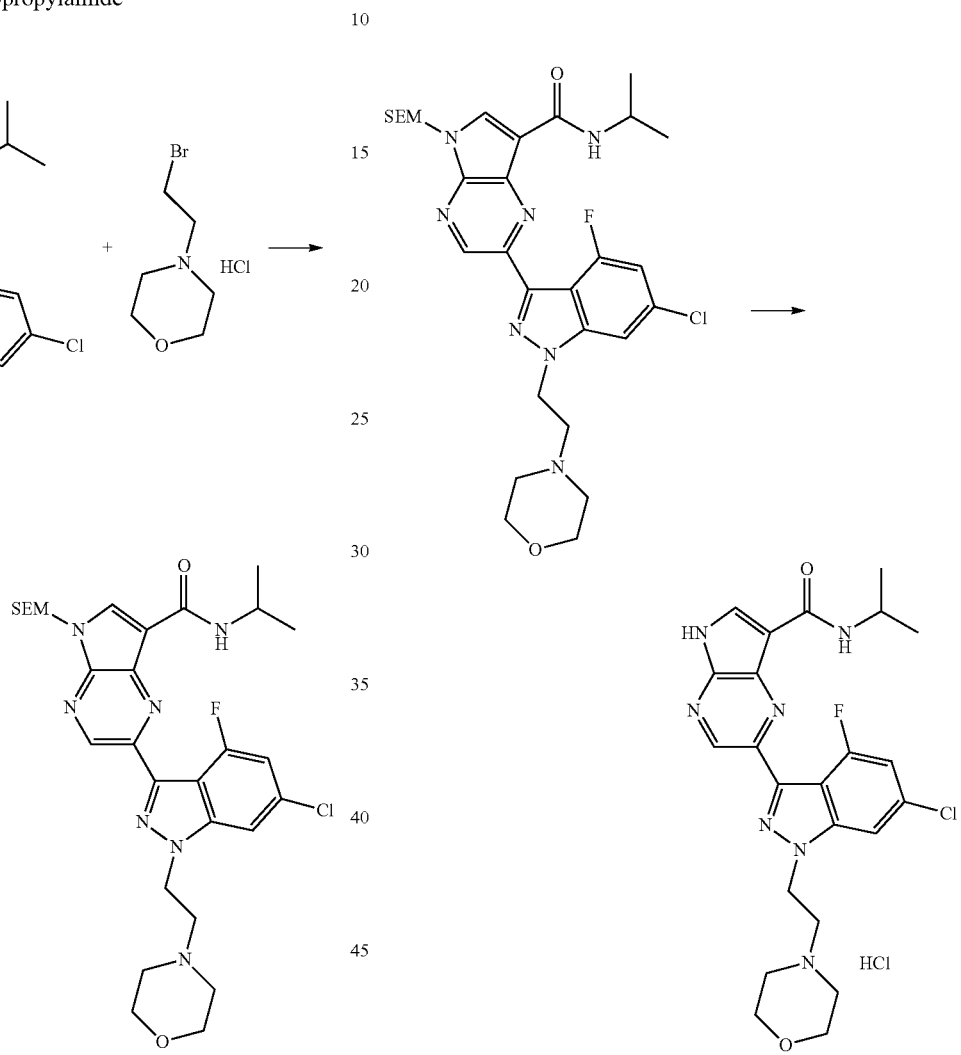

2-(6-Chloro-4-fluoro-1H-indazol-3-yl)-5-(2-trimethylsilanyl-ethoxymethyl)-5H-pyrrolo[2,3-b]pyrazine-7-carboxylic acid isopropylamide (77 mg, 0.15 mmol) was dissolved in DMF (2.5 ml) and cooled in an ice bath. Sodium hydride (60% dispersion, 8 mg, 0.20 mmol) was carefully added. The mixture was stirred for 15 min then additional sodium hydride (60% dispersion, 10 mg, 0.25 mmol) and 4-(2-bromoethyl)morpholine hydrochloride (42 mg, 0.18 mmol) were added. The reaction was warmed to room temperature and stirred overnight. Water, sodium bicarbonate solution and ethyl acetate were added to the reaction. The layers were separated and the aqueous layer was extracted three times with ethyl acetate. The combined organic layers were washed water and sodium chloride solution and dried over sodium sulfate. After evaporation, the residue was purified by silica gel chromatography (methanol/dichloromethane) to give 66 mg (70%) of 2-[6-chloro-4-fluoro-1-(2-morpholin-4-yl-ethyl)-1H-indazol-3-yl]-5-(2-trimethylsilanyl-ethoxymethyl)-5H-pyrrolo[2,3-b]pyrazine-7-carboxylic acid isopropylamide.

Step 4

2-[6-Chloro-4-fluoro-1-(2-morpholin-4-yl-ethyl)-1H-indazol-3-yl]-5H-pyrrolo[2,3-b]pyrazine-7-carboxylic acid isopropylamide hydrochloride 2-[6-Chloro-4-fluoro-1-(2-morpholin-4-yl-ethyl)-1H-indazol-3-yl]-5-(2-trimethylsilanylethoxymethyl)-5H-pyrrolo[2,3-b]pyrazine-7-carboxylic acid isopropylamide (66 mg, 0.107 mmol) was dissolved in dichloromethane (1.4 ml) and cooled in ice bath. Trifluoroacetic acid (0.7 ml) was slowly added and the reaction was stirred at room temperature for 2 h. The reaction was evaporated and the residue was dissolved in dichloromethane (1 ml). Ethylenediamine (0.43 ml, 6.4 mmol) was added and the mixture was stirred for 18 h. Water and then ethyl acetate were added to the mixture. The layers were separated and the aqueous layer was extracted three times with ethyl acetate. The combined organic layers were washed with sodium chloride solution, dried over sodium sulfate and evaporated. The residue was purified by silica gel chromatography (methanol/dichloromethane). The product thus isolated was dissolved in methanol/dichloromethane and treated with 2 eq of 4 M HCl in 1,4-dioxane. Evaporation of the solvent provided a solid which was dried under high vacuum to afford 40 mg (72%) of 2-[6-chloro-4-fluoro-1-(2-morpholin-4-yl-ethyl)-1H-indazol-3-yl]-5H-pyrrolo[2,3-b]pyrazine-7-carboxylic acid isopropylamide hydrochloride. MS: (M+H)$^+$=486; mp=190-195° C. $^1$H NMR (300 MHz, DMSO-d$_6$) δ: 12.86-12.98 (m, 1H), 10.92-11.17 (m, 1H), 9.06 (s, 1H), 8.45 (d, J=3.0 Hz, 1H), 8.26 (d, J=7.9 Hz, 1H), 8.05 (s, 1H), 7.35 (d, J=10.6 Hz, 1H), 5.05 (br. s., 2H), 4.14-4.30 (m, 1H), 3.93-4.09 (m, 2H), 3.68-3.85 (m, 4H), 3.54-3.64 (m, 2H), 3.11-3.30 (m, 2H), 1.24 (d, J=6.4 Hz, 6H).

Example 130

2-[6-Chloro-1-(3-dimethylamino-propyl)-4-fluoro-1H-indazol-3-yl]-5H-pyrrolo[2,3-b]pyrazine-7-carboxylic acid isopropylamide

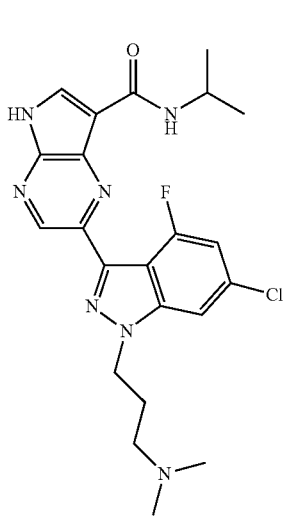 [SMILES: CC(C)NC(=O)c1c[nH]c2ncc(-c3nn(CCCN(C)C)c4cc(Cl)cc(F)c34)nc12]

Prepared according to the procedure outlined in Example 128, substituting dimethylaminopropyl chloride hydrochloride for dimethylaminoethyl chloride hydrochloride in Step 1. The salt of the final product was not formed in Step 4. MS: (M+H)$^+$=458; mp=249-255° C. $^1$H NMR (300 MHz, DMSO-d$_6$) δ: 9.04 (s, 1H), 8.43 (s, 1H), 8.27 (d, J=7.9 Hz, 1H), 7.93 (s, 1H), 7.28 (d, J=10.6 Hz, 1H), 4.59 (s, 2H), 4.18-4.30 (m, 1H), 2.56-2.66 (m, 2H), 2.39 (br. s., 6H), 2.12-2.16 (m, 2H), 1.24 (d, J=6.8 Hz, 6H).

Example 131

2-[6-Chloro-1-(3-dimethylamino-propyl)-4-fluoro-1H-indazol-3-yl]-5H-pyrrolo[2,3-b]pyrazine-7-carboxylic acid isopropylamide hydrochloride

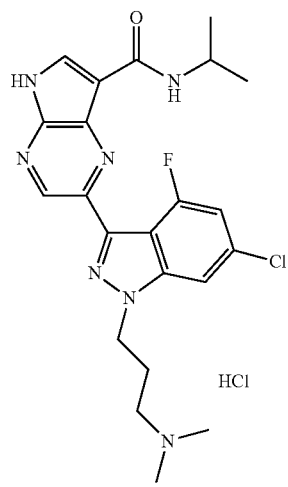 [SMILES: CC(C)NC(=O)c1c[nH]c2ncc(-c3nn(CCCN(C)C)c4cc(Cl)cc(F)c34)nc12 ; Cl]

Prepared according to the procedure outlined in Example 128, substituting dimethylaminopropyl chloride hydrochloride for dimethylaminoethyl chloride hydrochloride in Step 1. MS: (M+H)$^+$=458; mp=304-305° C. $^1$H NMR (300 MHz, DMSO-d$_6$) δ: 12.84-12.93 (m, 1H), 10.12-10.30 (m, 1H), 9.05 (s, 1H), 8.44 (d, J=3.0 Hz, 1H), 8.22-8.31 (m, 1H), 7.96-8.02 (m, 1H), 7.30 (d, J=9.8 Hz, 1H), 4.59-4.71 (m, 2H), 4.13-4.31 (m, 1H), 3.09-3.23 (m, 2H), 2.75 (d, J=4.9 Hz, 6H), 2.24-2.41 (m, 2H), 1.24 (d, J=6.8 Hz, 6H).

Example 132

2-[6-Chloro-4-fluoro-1-(3-morpholin-4-yl-propyl)-1H-indazol-3-yl]-5H-pyrrolo[2,3-b]pyrazine-7-carboxylic acid isopropylamide hydrochloride

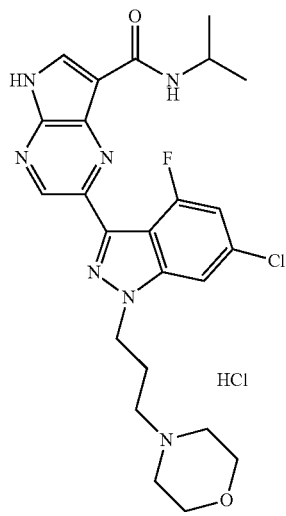 [SMILES: CC(C)NC(=O)c1c[nH]c2ncc(-c3nn(CCCN4CCOCC4)c4cc(Cl)cc(F)c34)nc12 ; Cl]

Prepared according to the procedure outlined in Example 128, substituting 4-(3-chloropropyl)morpholine for dimethylaminoethyl chloride hydrochloride in Step 1. MS: (M+H)$^+$ =500; mp=282-285° C. $^1$H NMR (300 MHz, DMSO-d$_6$) δ: 12.86-12.92 (m, 1H), 10.72-10.88 (m, 1H), 9.06 (s, 1H), 8.43 (d, J=3.0 Hz, 1H), 8.27 (d, J=7.9 Hz, 1H), 7.96-8.01 (m, 1H), 7.30 (d, J=10.6 Hz, 1H), 4.61-4.72 (m, 2H), 4.13-4.30 (m, 1H), 3.88-3.99 (m, 2H), 3.68-3.83 (m, 2H), 3.41-3.46 (m, 2H), 3.15-3.27 (m, 2H), 2.96-3.13 (m, 2H), 2.31-2.45 (m, 2H), 1.24 (d, J=6.8 Hz, 6H).

Example 133

2-(6-Fluoro-1-methyl-1H-indazol-3-yl)-5H-pyrrolo[2,3-b]pyrazine-7-carboxylic acid ((R)-1-methyl-2-pyrazol-1-yl-ethyl)-amide

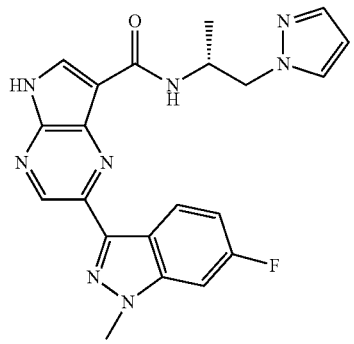 [SMILES: C[C@H](Cn1cccn1)NC(=O)c1c[nH]c2ncc(-c3nn(C)c4cc(F)ccc34)nc12]

Step 1

((R)-2-Hydroxy-1-methyl-ethyl)-carbamic acid tert-butyl ester

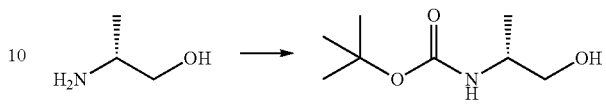

R-(−)-2-Aminopropan-1-ol (2.0 g, 26.6 mmol) was dissolved in dichloromethane (133 ml) and di-tert-butyldicarbonate (11.6 g, 53.3 mmol) was added in portions. The reaction was stirred at room temperature for 16 h. Water was added and the aqueous layer was extracted once with dichloromethane. The combined organic layers were washed with sodium chloride solution and dried over sodium sulfate. After evaporation, the residue was purified by silica gel chromatography (methanol/dichloromethane) to give 4.0 g (85%) of ((R)-2-hydroxy-1-methyl-ethyl)-carbamic acid tert-butyl ester. (M+Na)$^+$=198.

Step 2

Methanesulfonic acid (R)-2-tert-butoxycarbonylamino-propyl ester

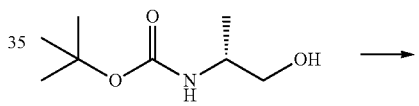

((R)-2-Hydroxy-1-methyl-ethyl)-carbamic acid tert-butyl ester (0.5 g, 2.85 mmol) was dissolved in dichloromethane (14 ml) and stirred in an ice bath. N,N-diisopropylethylamine (0.75 ml, 4.28 mmol) and then methanesulfonyl chloride (0.27 ml, 3.4 mmol) were slowly added and the reaction was warmed to room temperature over 16 h. Ammonium chloride solution was added to the reaction and it was extracted two times with ethyl acetate. The combined organics were washed with sodium chloride solution and dried over sodium sulfate. Evaporation gave 0.73 g of methanesulfonic acid (R)-2-tert-butoxycarbonylamino-propyl ester as a waxy white solid. $^1$H NMR (CDCl$_3$) δ: 4.51-4.68 (m, 1H), 4.19-4.28 (m, 1H), 4.11-4.18 (m, 1H), 3.90-4.04 (m, 1H), 3.03 (s, 3H), 1.24 (d, J=6.8 Hz, 3H).

Step 3

((R)-1-Methyl-2-pyrazol-1-yl-ethyl)-carbamic acid tert-butyl ester

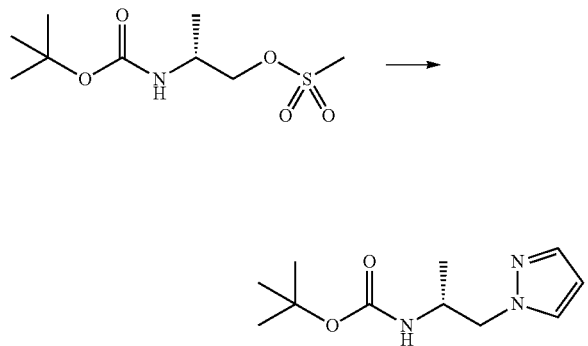

1H-Pyrazole (70 mg, 1.03 mmol) was dissolved in DMF (5 ml) and cooled in an ice bath. Sodium hydride (60% dispersion in mineral oil, 41 mg, 1.03 mmol) was added and the reaction was stirred for 15 min. Methanesulfonic acid (R)-2-tert-butoxycarbonylamino-propyl ester (200 mg, 0.79 mmol) was then added and the mixture was stirred at 50° C. for 16 h. The reaction was cooled to room temperature and water and ethyl acetate were added. The aqueous layer was extracted twice more with ethyl acetate and the combined organic layers were washed with sodium chloride solution and dried over sodium sulfate. After evaporation, the residue was purified by silica gel chromatography (methanol/dichloromethane) to give 129 mg (72%) of ((R)-1-methyl-2-pyrazol-1-yl-ethyl)-carbamic acid tert-butyl ester. (M+H)$^+$=226.

Step 4

(R)-1-Methyl-2-pyrazol-1-yl-ethylamine trifluoroacetate

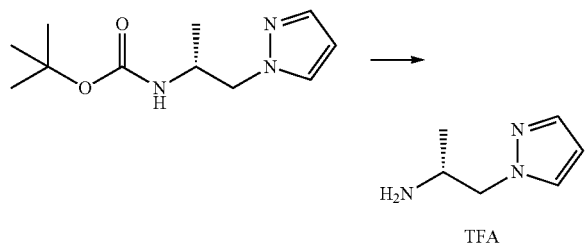

((R)-1-Methyl-2-pyrazol-1-yl-ethyl)-carbamic acid tert-butyl ester (49 mg, 0.22 mmol) was dissolved in dichloromethane (2.4 ml) and cooled in an ice bath. Trifluoroacetic acid (1.2 ml) was slowly added and the reaction was stirred at room temperature for 2 h then evaporated and dried under high vacuum to afford (R)-1-methyl-2-pyrazol-1-yl-ethylamine trifluoroacetate which was used without further purification.

Step 5

2-(6-Fluoro-1-methyl-1H-indazol-3-yl)-5-(2-trimethylsilanyl-ethoxymethyl)-5H-pyrrolo[2,3-b]pyrazine-7-carboxylic acid ((R)-1-methyl-2-pyrazol-1-yl-ethyl)-amide

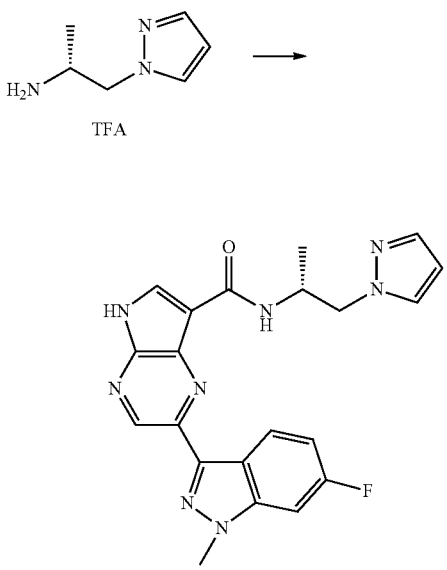

(R)-1-Methyl-2-pyrazol-1-yl-ethylamine trifluoroacetate (crude from Step 4) was dissolved in acetonitrile (1.8 ml) to which was then added 2-(6-fluoro-1-methyl-1H-indazol-3-yl)-5-(2-trimethylsilanyl-ethoxymethyl)-5H-pyrrolo[2,3-b]pyrazine-7-carboxylic acid (80 mg, 0.18 mmol), O-benzotriazol-1-yl-N,N,N',N'-tetramethyluronium tetrafluoroborate (87 mg, 0.27 mmol) and N,N-diisopropylethylamine (0.16 ml, 0.91 mmol). The reaction was stirred at room temperature for 18 h and then water and ethyl acetate were added. The layers were separated and the aqueous layer was extracted three times with ethyl acetate. The combined organic layers were washed with sodium chloride solution and dried over sodium sulfate. After evaporation, the residue was purified by silica gel chromatography (methanol/dichloromethane) to afford 89 mg (81%) of 2-(6-fluoro-1-methyl-1H-indazol-3- yl)-5-(2-trimethylsilanyl-ethoxymethyl)-5H-pyrrolo[2,3-b]pyrazine-7-carboxylic acid ((R)-1-methyl-2-pyrazol-1-yl-ethyl)-amide.

Step 6

2-(6-Fluoro-1-methyl-1H-indazol-3-yl)-5H-pyrrolo[2,3-b]pyrazine-7-carboxylic acid ((R)-1-methyl-2-pyrazol-1-yl-ethyl)-amide

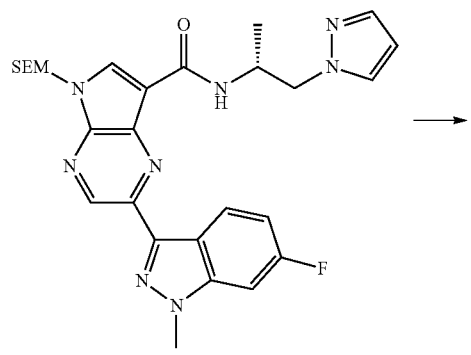

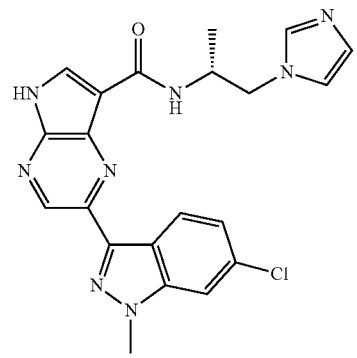 [SMILES: C[C@H](Cn1ccnc1)NC(=O)c1c[nH]c2ncc(-c3nn(C)c4cc(Cl)ccc34)nc12]

2-(6-Fluoro-1-methyl-1H-indazol-3-yl)-5-(2-trimethylsilanyl-ethoxymethyl)-5H-pyrrolo[2,3-b]pyrazine-7-carboxylic acid ((R)-1-methyl-2-pyrazol-1-yl-ethyl)-amide (86 mg, 0.16 mmol) was dissolved in dichloromethane (2.2 ml) and cooled in ice bath. Trifluoroacetic acid (1 ml) was slowly added and the reaction was stirred at room temperature for 2 h. The reaction was evaporated and the residue was dissolved in dichloromethane (1 ml). Ethylenediamine (0.63 ml, 9.4 mmol) was added and the mixture was stirred for 18 h. Water and then ethyl acetate were added to the mixture. The resulting precipitate was filtered off, rinsed with water and diethyl ether and dried under high vacuum to give 37 mg (57%) of 2-(6-fluoro-1-methyl-1H-indazol-3-yl)-5H-pyrrolo[2,3-b]pyrazine-7-carboxylic acid ((R)-1-methyl-2-pyrazol-1-yl-ethyl)-amide. MS: (M+Na)$^+$=441; mp=252-253° C. $^1$H NMR (300 MHz, DMSO-d$_6$) δ: 9.08 (s, 1H), 8.46 (s, 1H), 8.21-8.33 (m, 1H), 8.12 (d, J=7.9 Hz, 1H), 7.63-7.75 (m, 2H), 7.31-7.40 (m, 1H), 6.97-7.10 (m, 1H), 6.12-6.23 (m, 1H), 4.46-4.63 (m, 1H), 4.32-4.44 (m, 2H), 4.14 (s, 3H), 1.23 (d, J=6.4 Hz, 3H).

Example 134

2-(6-Chloro-1-methyl-1H-indazol-3-yl)-5H-pyrrolo[2,3-b]pyrazine-7-carboxylic acid ((R)-2-imidazol-1-yl-1-methyl-ethyl)-amide Prepared according to the procedure outlined in Example 133, substituting 1H-imidazole for 1H-pyrazole in Step 3 and substituting 2-(6-chloro-1-methyl-1H-indazol-3-yl)-5-((2-(trimethylsilyl)ethoxy)methyl)-5H-pyrrolo[3,2-b]pyrazine-7-carboxylic acid for 2-(6-fluoro-1-methyl-1H-indazol-3-yl)-5-(2-trimethylsilanyl-ethoxymethyl)-5H-pyrrolo[2,3-b]pyrazine-7-carboxylic acid in Step 5. MS: (M+H)$^+$=435; mp=276-279° C. $^1$H NMR (300 MHz, DMSO-d$_6$) δ: 12.76-13.03 (m, 1H), 9.08 (s, 1H), 8.47 (s, 1H), 8.01-8.14 (m, 2H), 7.98 (br. s., 1H), 7.62 (br. s., 1H), 7.18-7.27 (m, 1H), 7.15 (br. s., 1H), 6.82 (s, 1H), 4.36-4.50 (m, 1H), 4.16 (br. s., 3H), 4.09-4.36 (m, 2H), 1.26 (d, J=6.4 Hz, 3H).

Example 135

2-(6-Fluoro-1-methyl-1H-indazol-3-yl)-5H-pyrrolo[2,3-b]pyrazine-7-carboxylic acid ((S)-2-methoxy-propyl)-amide

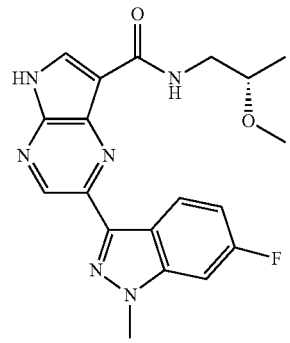

Step 1

((S)-2-Hydroxy-propyl)-carbamic acid tert-butyl ester

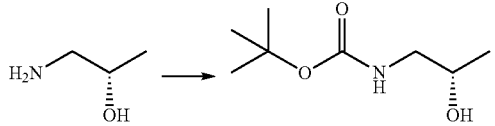

(S)-1-Aminopropan-2-ol (1.0 g, 13.3 mmol) was dissolved in dichloromethane (67 ml) and di-tert-butyldicarbonate (5.8 g, 26.6 mmol) was added in portions. The reaction was stirred at room temperature for 16 h. Ammonium chloride solution and water were added and the aqueous layer was extracted twice with ethyl acetate. The combined organic layers were washed with sodium chloride solution and dried over sodium sulfate. After evaporation, the residue was purified by silica gel chromatography (methanol/dichloromethane) to give 2.35 g (99%) of ((S)-2-hydroxy-propyl)-carbamic acid tert-butyl ester.

Step 2

((S)-2-Methoxy-propyl)-carbamic acid tert-butyl ester

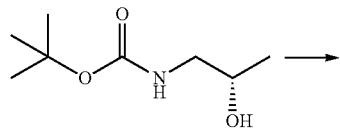

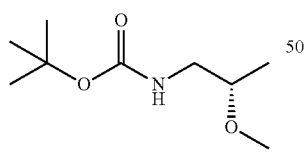

((S)-2-Hydroxy-propyl)-carbamic acid tert-butyl ester (0.25 g, 1.43 mmol) was dissolved in acetonitrile (14 ml) and iodomethane (1.78 ml, 28.5 mmol), and then silver oxide (0.53 g, 2.28 mmol; prepared as in *Org. Syn. Coll. Vol. VII*, p. 386) were added. The reaction flask was covered to protect from light and the reaction was heated at reflux for 24 h. Additional iodomethane (1.8 ml) and silver oxide (0.26 g) were added and heating was continued until the reaction was judged to be complete by standard reverse phase LC/MS. The reaction mixture was filtered through diatomaceous earth, rinsing with ethyl acetate. After evaporation the residue was purified by silica gel chromatography (ethyl acetate/hexanes) to give 85 mg (32%) of ((S)-2-methoxy-propyl)-carbamic acid tert-butyl ester. (M+Na)$^+$=212.

Step 3

2-(6-Fluoro-1-methyl-1H-indazol-3-yl)-5H-pyrrolo[2,3-b]pyrazine-7-carboxylic acid ((S)-2-methoxy-propyl)-amide

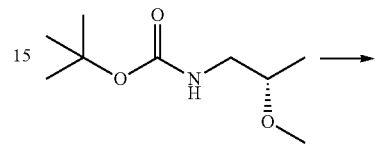

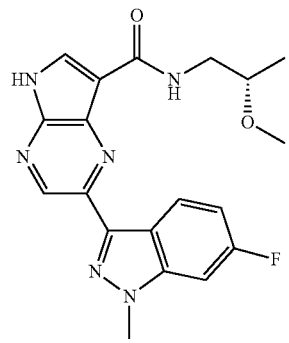 [SMILES: CO[C@@H](C)CNC(=O)c1c[nH]c2ncc(-c3nn(C)c4cc(F)ccc34)nc12]

Prepared according to the procedure outlined in Example 133, Steps 4-6, substituting ((S)-2-methoxy-propyl)-carbamic acid tert-butyl ester for ((R)-1-methyl-2-pyrazol-1-yl-ethyl)-carbamic acid tert-butyl ester in Step 4. MS: (M+H)$^+$= 383; mp=269-271° C. $^1$H NMR (300 MHz, DMSO-d$_6$) δ: 12.81-12.92 (m, 1H), 9.12 (s, 1H), 8.55 (dd, J=9.1, 5.3 Hz, 1H), 8.45 (s, 1H), 8.24-8.33 (m, 1H), 7.67 (dd, J=9.8, 2.3 Hz, 1H), 7.13 (ddd, J=9.1, 2.3 Hz, 1H), 4.15 (s, 3H), 3.65-3.75 (m, 1H), 3.40-3.60 (m, 2H), 3.26 (s, 3H), 1.17 (d, J=6.0 Hz, 3H).

Example 136

2-(6-Fluoro-1-methyl-1H-indazol-3-yl)-5H-pyrrolo[2,3-b]pyrazine-7-carboxylic acid ((R)-2-cyano-2-methyl-ethyl)-amide

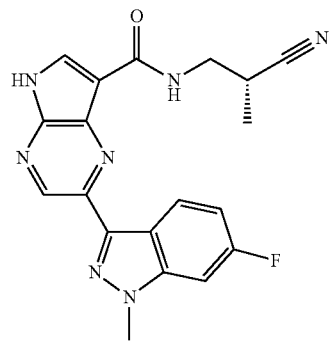 [SMILES: C[C@@H](C#N)CNC(=O)c1c[nH]c2ncc(-c3nn(C)c4cc(F)ccc34)nc12]

Step 1

((R)-2-Carbamoyl-propyl)-carbamic acid tert-butyl ester

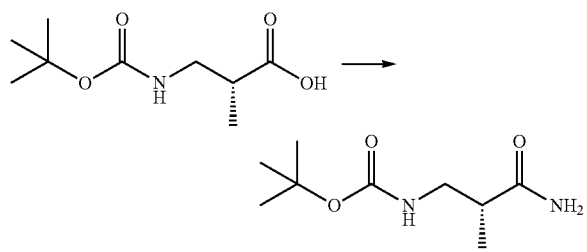

(R)-3-(tert-Butoxycarbonylamino)-2-methylpropanoic acid (465 mg, 2.3 mmol) was dissolved in dichloromethane (11 ml). 4-Dimethylaminopyridine (280 mg, 2.3 mmol) and 1-(3-dimethylaminopropyl)-3-ethylcarbodiimide (877 mg, 4.58 mmol) were added, followed by N-hydroxysuccinimide (290 mg, 2.52 mmol). After 4 h of stirring at room temperature, concentrated ammonium hydroxide (1.6 ml) was added slowly. The reaction mixture was stirred for an additional 20 min then aqueous HCl and ethyl acetate were added and the aqueous layer was extracted six times with ethyl acetate. The combined organic layers were washed with sodium bicarbonate solution and dried over sodium sulfate. After evaporation, the residue was purified by silica gel chromatography to give 335 mg (72%) of ((R)-2-carbamoyl-propyl)-carbamic acid tert-butyl ester. (M+Na)$^+$=225.

Step 2

((R)-2-Cyano-2-methyl-ethyl)-carbamic acid tert-butyl ester

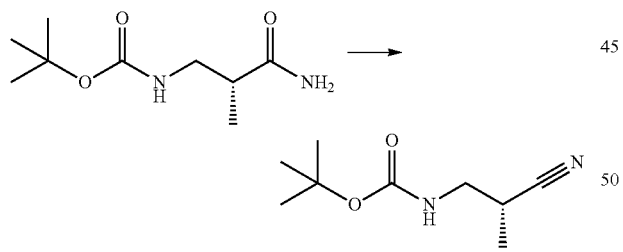

((R)-2-Carbamoyl-propyl)-carbamic acid tert-butyl ester (50 mg, 0.247 mmol) was dissolved in THF (1.4 ml). Pyridine (40 ul, 0.49 mmol) and then trifluoroacetic anhydride (42 ul, 0.30 mmol) were added dropwise. The reaction was stirred at room temperature for 1 h and then additional pyridine (40 ul, 0.49 mmol) and trifluoroacetic anhydride (42 ul, 0.30 mmol) were added. The reaction was stirred at room temperature for 16 h then water, sodium carbonate solution and ethyl acetate were added. The aqueous layer was extracted three times with ethyl acetate. The combined organic layers were washed with water and sodium chloride solution, and dried over sodium sulfate. After evaporation, the residue was purified by silica gel chromatography (methanol/dichloromethane) to give 40 mg (87%) of ((R)-2-cyano-2-methyl-ethyl)-carbamic acid tert-butyl ester. (M+Na)$^+$=207.

Step 3

(R)-3-Amino-2-methyl-propionitrile trifluoroacetate

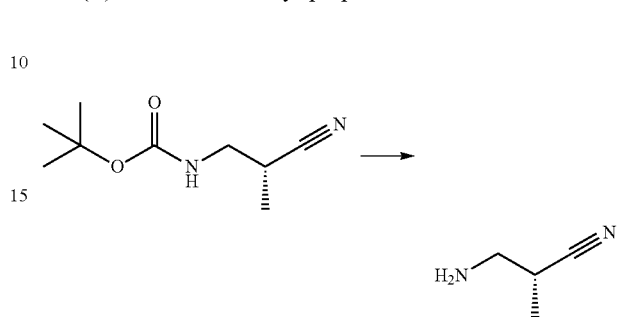

((R)-2-Cyano-2-methyl-ethyl)-carbamic acid tert-butyl ester (42 mg, 0.23 mmol) was dissolved in dichloromethane (1.2 ml) and cooled in an ice bath. Trifluoroacetic acid (0.7 ml) was slowly added and the reaction was stirred at room temperature for 3 h then evaporated and dried under high vacuum to afford (R)-3-amino-2-methyl-propionitrile trifluoroacetate which was used without further purification.

Step 4

2-(6-Fluoro-1-methyl-1H-indazol-3-yl)-5-(2-trimethylsilanyl-ethoxymethyl)-5H-pyrrolo[2,3-b]pyrazine-7-carboxylic acid ((R)-2-cyano-2-methyl-ethyl)-amide

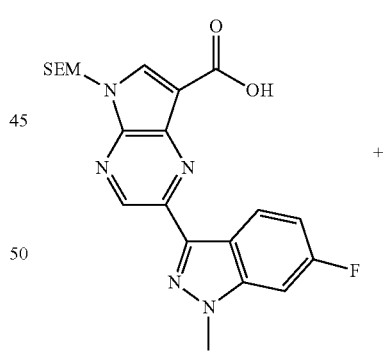

+

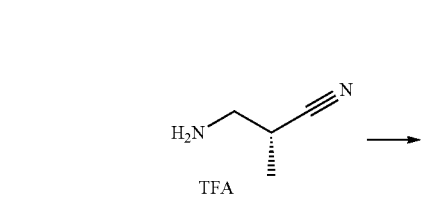

-continued

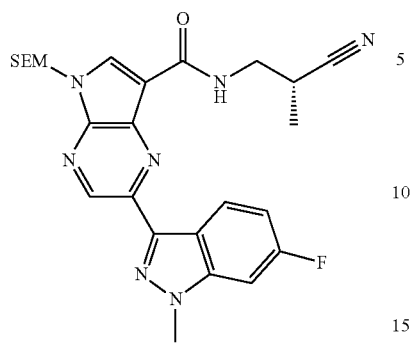

(R)-3-Amino-2-methyl-propionitrile trifluoroacetate (crude from Step 3) was dissolved in acetonitrile (2.8 ml) to which was then added 2-(6-fluoro-1-methyl-1H-indazol-3-yl)-5-(2-trimethylsilanyl-ethoxymethyl)-5H-pyrrolo[2,3-b]pyrazine-7-carboxylic acid (80 mg, 0.18 mmol), O-benzotriazol-1-yl-N,N,N',N'-tetramethyluronium tetrafluoroborate (70 mg, 0.22 mmol) and N,N-diisopropylethylamine (0.11 ml, 0.63 mmol). The reaction was stirred at room temperature for 18 h. Additional O-benzotriazol-1-yl-N,N,N',N'-tetramethyluronium tetrafluoroborate (50 mg, 0.16 mmol) and N,N-diisopropylethylamine (0.11 ml, 0.63 mmol) were added and stirring was continued for 24 h. Water and ethyl acetate were added. The layers were separated and the aqueous layer was extracted twice with ethyl acetate. The combined organic layers were washed with sodium chloride solution and dried over sodium sulfate. After evaporation, the residue was purified by silica gel chromatography (methanol/dichloromethane) to afford 33 mg (36%) of 2-(6-fluoro-1-methyl-1H-indazol-3-yl)-5-(2-trimethylsilanylethoxymethyl)-5H-pyrrolo[2,3-b]pyrazine-7-carboxylic acid ((R)-2-cyano-2-methyl-ethyl)-amide. (M+Na)$^+$=530.

Step 5

2-(6-Fluoro-1-methyl-1H-indazol-3-yl)-5H-pyrrolo[2,3-b]pyrazine-7-carboxylic acid ((R)-1-methyl-2-pyrazol-1-yl-ethyl)-amide

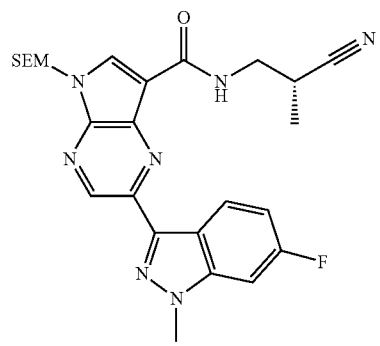

-continued

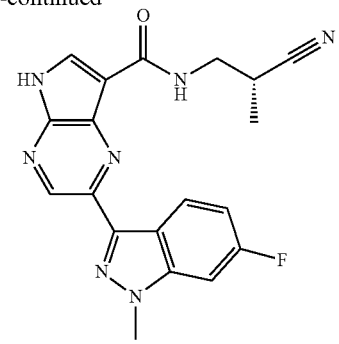

2-(6-Fluoro-1-methyl-1H-indazol-3-yl)-5-(2-trimethylsilanyl-ethoxymethyl)-5H-pyrrolo[2,3-b]pyrazine-7-carboxylic acid ((R)-2-cyano-2-methyl-ethyl)-amide (32 mg, 0.06 mmol) was dissolved in dichloromethane (1.6 ml) and cooled in ice bath. Trifluoroacetic acid (0.8 ml) was slowly added and the reaction was stirred at room temperature for 2.5 h. The reaction was evaporated and the residue was dissolved in dichloromethane (1 ml). Ethylenediamine (0.26 ml, 3.8 mmol) was added and the mixture was stirred for 18 h. Water and then ethyl acetate were added to the mixture. The layers were separated and the aqueous layer was extracted twice with ethyl acetate. The combined organic layers were washed with sodium chloride solution, dried over sodium sulfate and evaporated. The residue was purified by silica gel chromatography (methanol/dichloromethane) to give 5 mg (20%) of 2-(6-fluoro-1-methyl-1H-indazol-3-yl)-5H-pyrrolo[2,3-b]pyrazine-7-carboxylic acid ((R)-2-cyano-2-methyl-ethyl)-amide.

MS: (M+Na)$^+$=400. $^1$H NMR (300 MHz, DMSO-d$_6$) δ: 12.80-12.98 (m, 1H), 9.11 (s, 1H), 8.50 (s, 1H), 8.44-8.56 (m, 2H), 7.67 (dd, J=9.8, 2.3 Hz, 1H), 7.20 (ddd, J=9.3, 1.9 Hz, 1H), 4.15 (s, 3H), 3.64-3.76 (m, 2H), 3.18-3.27 (m, 1H), 1.34 (d, J=6.8 Hz, 3H).

Example 137

2-(6-Fluoro-1-methyl-1H-indazol-3-yl)-5H-pyrrolo[2,3-b]pyrazine-7-carboxylic acid ((R)-2-carbamoyl-propyl)-amide

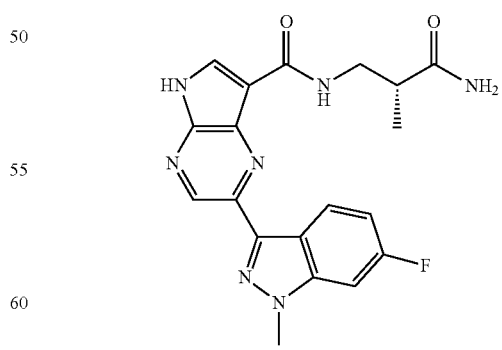

Isolated as an additional product (3 mg, 12%) from Example 136, Step 5. MS: (M+Na)$^+$=418. $^1$H NMR (300 MHz, DMSO-d$_6$) δ: 9.11 (s, 1H), 8.49-8.60 (m, 1H), 8.44 (s, 1H), 8.22-8.30 (m, 1H), 7.65 (dd, J=9.8, 2.3 Hz, 1H), 7.40 (s, 1H), 7.30 (ddd, J=9.3, 2.3 Hz, 1H), 6.84 (s, 1H), 4.15 (s, 3H), 3.39-3.67 (m, 2H), 2.62-2.74 (m, 1H), 1.13 (d, J=6.8 Hz, 3H).

Example 138

2-(6-Chloro-1-methyl-1H-indazol-3-yl)-5H-pyrrolo[2,3-b]pyrazine-7-carboxylic acid (S)—N-(tetrahydro-pyran-3-yl)-amide

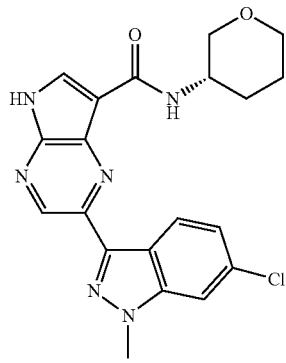 [SMILES: Cn1nc(-c2cnc3[nH]cc(C(=O)N[C@H]4CCCOC4)c3n2)c2ccc(Cl)cc21]

Step 1

(S)-2-tert-Butoxycarbonylamino-pentanedioic acid diethyl ester

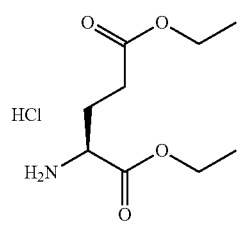

(S)-1,5-Diethoxy-1,5-dioxopentan-2-amine hydrochloride (1.0 g, 4.17 mmol) was dissolved in dichloromethane (10 ml) and cooled in an ice bath. Triethylamine (0.58 ml, 4.17 mmol) was added followed by di-tert-butyldicarbonate (1.09 g, 5.0 mmol) and the mixture was warmed to room temperature over 16 h. Water and ethyl acetate were added and the aqueous layer was extracted once more with ethyl acetate. The combined organic layers were washed with sodium chloride solution and dried over sodium sulfate. After evaporation, the residue was purified by silica gel chromatography (ethyl acetate/hexanes) to give 1.11 g (87%) of (S)-2-tert-butoxycarbonylamino-pentanedioic acid diethyl ester. $(M+Na)^+=326$.

Step 2

((S)-4-Hydroxy-1-hydroxymethyl-butyl)-carbamic acid tert-butyl ester

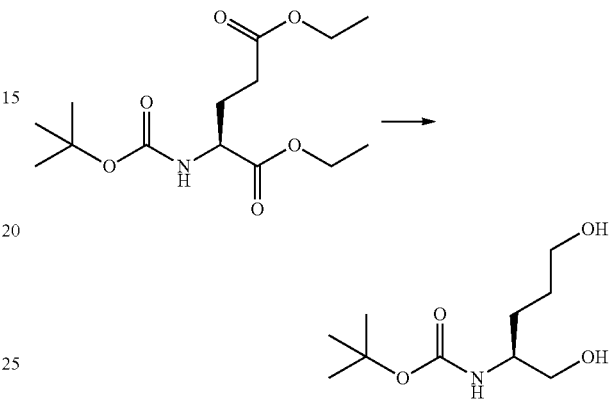

Lithium borohydride (2.0 M in THF, 4.12 ml, 8.24 mmol) was cooled in an ice bath and a solution of (S)-2-tert-butoxycarbonylamino-pentanedioic acid diethyl ester (0.5 g, 1.65 mmol) in THF (5.5 ml) was added dropwise. The reaction was warmed to room temperature and stirred 16 h. Methanol was added very slowly to the reaction mixture. After a delayed, vigorous gas evolution had subsided, water and ethyl acetate were added. The aqueous layer was extracted with ethyl acetate five times, and the combined organic layers were washed with sodium chloride solution and dried over sodium sulfate. After evaporation, the residue was purified by silica gel chromatography (methanol/dichloromethane) to give 0.3 g (83%) of ((S)-4-hydroxy-1-hydroxymethyl-butyl)-carbamic acid tert-butyl ester. $(M+Na)^+=242$.

Step 3

(S)-(Tetrahydro-pyran-3-yl)-carbamic acid tert-butyl ester

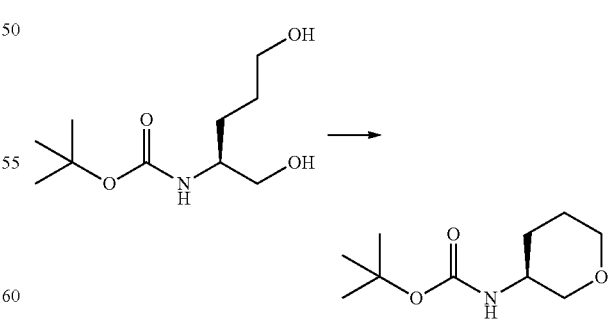

((S)-4-Hydroxy-1-hydroxymethyl-butyl)-carbamic acid tert-butyl ester (100 mg, 0.46 mmol) was dissolved in warm benzene (1.5 ml). Cyanomethylenetributylphosphorane (165 mg, 0.68 mmol) was added and the reaction vessel was sealed and stirred at 100° C. for 24 h. The reaction was cooled, evaporated and purified by silica gel chromatography (ethyl acetate/hexanes) to give 64 mg (69%) of (S)-(tetrahydro-pyran-3-yl)-carbamic acid tert-butyl ester. (M+Na)+=224.

Step 4

(S)-(Tetrahydro-pyran-3-yl)amine trifluoroacetate

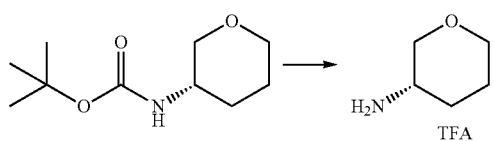

(S)-(Tetrahydro-pyran-3-yl)-carbamic acid tert-butyl ester (42 mg, 0.21 mmol) was dissolved in dichloromethane (2.2 ml) and cooled in an ice bath. Trifluoroacetic acid (1.2 ml) was slowly added and the reaction was stirred at room temperature for 3 h then evaporated and dried under high vacuum to afford (S)-(Tetrahydro-pyran-3-yl)amine trifluoroacetate which was used without further purification.

Step 5

2-(6-Chloro-1-methyl-1H-indazol-3-yl)-5-(2-trimethylsilanyl-ethoxymethyl)-5H-pyrrolo[2,3-b]pyrazine-7-carboxylic acid (S)—N-(tetrahydro-pyran-3-yl)-amide

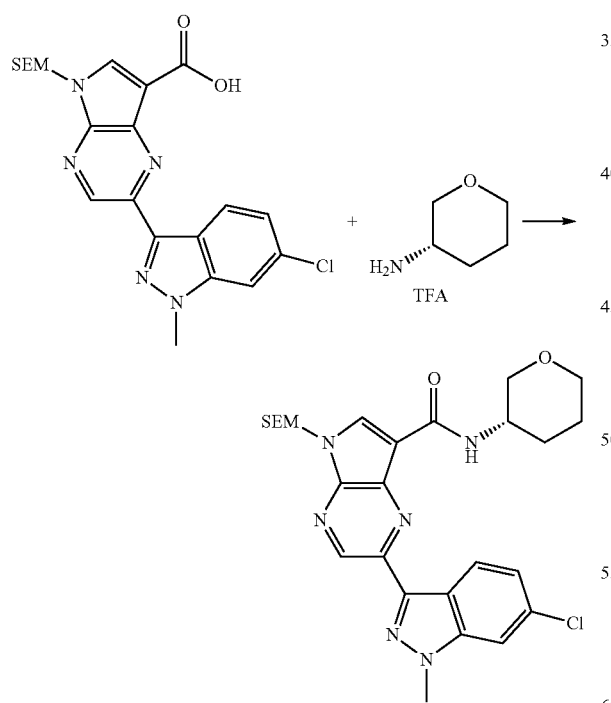

(S)-(Tetrahydro-pyran-3-yl)amine trifluoroacetate (crude from Step 4) was dissolved in acetonitrile (1.8 ml) to which was then added 2-(6-chloro-1-methyl-1H-indazol-3-yl)-5-(2-trimethylsilanyl-ethoxymethyl)-5H-pyrrolo[2,3-b]pyrazine-7-carboxylic acid (80 mg, 0.175 mmol), O-benzotriazol-1-yl-N,N,N',N'-tetramethyluronium tetrafluoroborate (84 mg, 0.26 mmol) and N,N-diisopropylethylamine (0.15 ml, 0.87 mmol). The reaction was stirred at room temperature for 18 h. Additional O-benzotriazol-1-yl-N,N,N',N'-tetramethyluronium tetrafluoroborate (50 mg, 0.16 mmol) and N,N-diisopropylethylamine (0.11 ml, 0.63 mmol) were added and stirring was continued for 24 h. Water and ethyl acetate were added. The layers were separated and the aqueous layer was extracted twice with ethyl acetate. The combined organic layers were washed with sodium chloride solution and dried over sodium sulfate. After evaporation, the residue was purified by silica gel chromatography (ethyl acetate/hexanes) to afford 55 mg (58%) of 2-(6-chloro-1-methyl-1H-indazol-3-yl)-5-(2-trimethylsilanylethoxymethyl)-5H-pyrrolo[2,3-b]pyrazine-7-carboxylic acid (S)—N-(tetrahydro-pyran-3-yl)-amide. (M+Na)+=563.

Step 6

2-(6-Chloro-1-methyl-1H-indazol-3-yl)-5H-pyrrolo[2,3-b]pyrazine-7-carboxylic acid (S)—N-(tetrahydro-pyran-3-yl)-amide

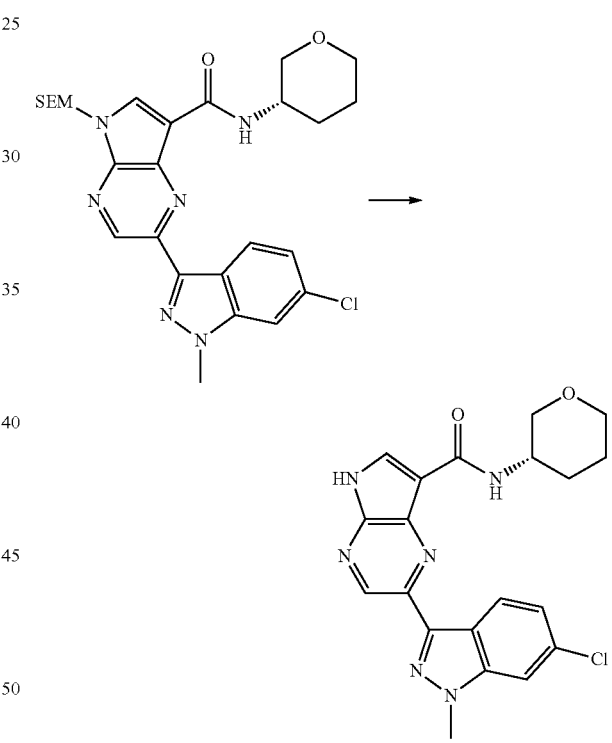

2-(6-Chloro-1-methyl-1H-indazol-3-yl)-5-(2-trimethylsilanyl-ethoxymethyl)-5H-pyrrolo[2,3-b]pyrazine-7-carboxylic acid (S)—N-(tetrahydro-pyran-3-yl)-amide (55 mg, 0.10 mmol) was dissolved in dichloromethane (1.2 ml) and cooled in ice bath. Trifluoroacetic acid (0.6 ml) was slowly added and the reaction was stirred at room temperature for 3 h. The reaction was evaporated and the residue was dissolved in dichloromethane (1 ml). Ethylenediamine (0.41 ml, 6.1 mmol) was added and the mixture was stirred for 18 h. Water and then ethyl acetate were added to the mixture. The layers were separated and the aqueous layer was extracted twice with ethyl acetate. The combined organic layers were washed with sodium chloride solution, dried over sodium sulfate and evaporated. The residue was purified by silica gel chromatography (methanol/dichloromethane) to give 30 mg (71%) of 2-(6-chloro-1-methyl-1H-indazol-3-yl)-5H-pyrrolo[2,3-b]pyrazine-7-carboxylic acid (S)—N-(tetrahydro-pyran-3-yl)-amide. MS: (M+H)$^+$=411; mp=320-323° C. $^1$H NMR (300 MHz, DMSO-d$_6$) δ: 9.10 (s, 1H), 8.50 (d, J=8.7 Hz, 1H), 8.44 (s, 1H), 8.16 (d, J=7.6 Hz, 1H), 7.96 (d, J=1.9 Hz, 1H), 7.24 (dd, J=8.5, 1.7 Hz, 1H), 4.16 (s, 3H), 4.04-4.14 (m, 1H), 3.86-3.94 (m, 1H), 3.62-3.73 (m, 2H), 3.46-3.55 (m, 1H), 1.93-2.08 (m, 1H), 1.69-1.89 (m, 2H), 1.50-1.68 (m, 1H).

Example 139

2-(6-Chloro-1-methyl-1H-indazol-3-yl)-5H-pyrrolo[2,3-b]pyrazine-7-carboxylic acid (R)—N-(tetrahydro-pyran-3-yl)-amide

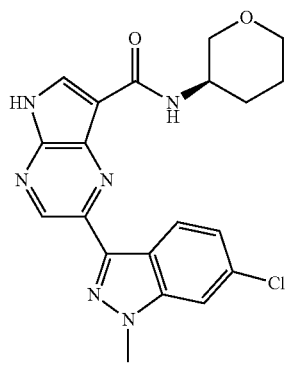 [SMILES: Cn1nc(-c2cnc3[nH]cc(C(=O)N[C@@H]4CCCOC4)c3n2)c2ccc(Cl)cc21]

Step 1

(R)-2-tert-Butoxycarbonylamino-pentanedioic acid dimethyl ester

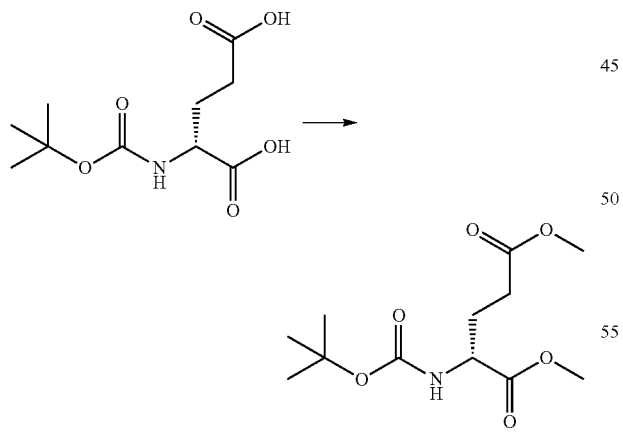

(R)-2-tert-Butyloxycarbonylamino)pentanedioic acid (1.0 g, 4.04 mmol) was dissolved in toluene (31.5 ml) and methanol (9 ml). The solution was stirred in an ice bath and TMS-diazomethane (2.0 M in diethyl ether, 16.2 ml, 32.4 mmol) was slowly added. The reaction was warmed to room temperature with stirring over 16 h. The reaction mixture was evaporated and purified by silica gel chromatography (ethyl acetate/hexanes) to give 0.95 g (85%) of (R)-2-tert-butoxycarbonylamino-pentanedioic acid dimethyl ester. (M+Na)$^+$=298.

Step 2

2-(6-Chloro-1-methyl-1H-indazol-3-yl)-5H-pyrrolo[2,3-b]pyrazine-7-carboxylic acid (R)—N-(tetrahydro-pyran-3-yl)-amide

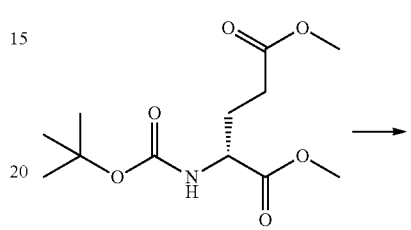

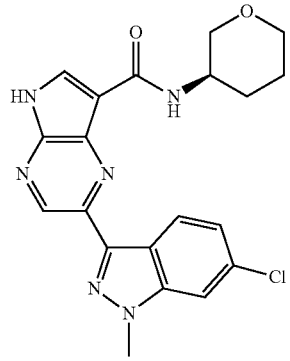

Prepared according to the procedure outlined in Example 138, Steps 2-6, substituting (R)-2-tert-butoxycarbonylamino-pentanedioic acid dimethyl ester for (S)-2-tert-butoxycarbonylamino-pentanedioic acid diethyl ester in Step 2. MS: (M+H)$^+$=411; mp=316-318° C. $^1$H NMR (300 MHz, DMSO-d$_6$) δ: 9.11 (s, 1H), 8.52 (d, J=8.7 Hz, 1H), 8.46 (s, 1H), 8.18 (d, J=7.9 Hz, 1H), 7.98 (d, J=1.5 Hz, 1H), 7.26 (dd, J=8.7, 1.5 Hz, 1H), 4.17 (s, 3H), 4.01-4.15 (m, 1H), 3.86-3.95

(m, 1H), 3.56-3.74 (m, 2H), 3.44-3.56 (m, 1H), 1.94-2.09 (m, 1H), 1.70-1.90 (m, 2H), 1.51-1.65 (m, 1H).

Example 140

2-(6-Chloro-1-methyl-1H-indazol-3-yl)-5H-pyrrolo[2,3-b]pyrazine-7-carboxylic acid ((S)-1-cyclopropyl-ethyl)-amide

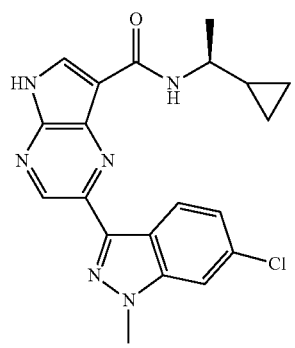 [SMILES: C[C@H](NC(=O)c1c[nH]c2ncc(-c3nn(C)c4cc(Cl)ccc34)nc12)C1CC1]

Step 1

2-(6-Chloro-1-methyl-1H-indazol-3-yl)-5-(2-trimethylsilanyl-ethoxymethyl)-5H-pyrrolo[2,3-b]pyrazine-7-carboxylic acid ((S)-1-cyclopropyl-ethyl)-amide

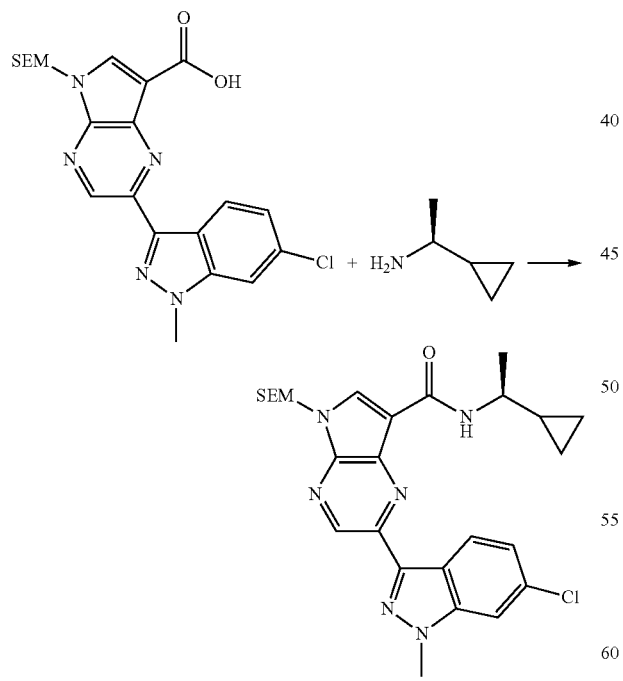

A solution of (S)-1-cyclopropylethanamine (32 mg, 0.373 mmol), 3 mL of dichloromethane, 2-(6-chloro-1-methyl-1H-indazol-3-yl)-5-(2-trimethylsilanyl-ethoxymethyl)-5H-pyrrolo[2,3-b]pyrazine-7-carboxylic acid (77 mg, 0.169 mmol), 4-dimethylaminopyridine (21 mg, 0.169 mmol) and N-(3-dimethylaminopropyl)-N'-ethylcarbodiimide hydrochloride (71 mg, 0.371 mmol) was stirred 18 h, then concentrated to an off-white solid. The solid was partitioned between 10 mL of ethyl acetate and 10 mL of a 10% citric acid solution. The organic layer was sequentially washed with 10 mL of water, 10 mL of a 10% NaOH solution, 10 mL of water, and 10 mL of a sat. aq. NaCl solution; dried over $Na_2SO_4$, filtered and concentrated to 70 mg (80%) of crude 2-(6-chloro-1-methyl-1H-indazol-3-yl)-5-(2-trimethylsilanyl-ethoxymethyl)-5H-pyrrolo[2,3-b]pyrazine-7-carboxylic acid ((S)-1-cyclopropyl-ethyl)-amide, which was used without further purification. MS: $(M+Na)^+$=547.

Step 2

2-(6-Chloro-1-methyl-1H-indazol-3-yl)-5H-pyrrolo[2,3-b]pyrazine-7-carboxylic acid ((S)-1-cyclopropyl-ethyl)-amide

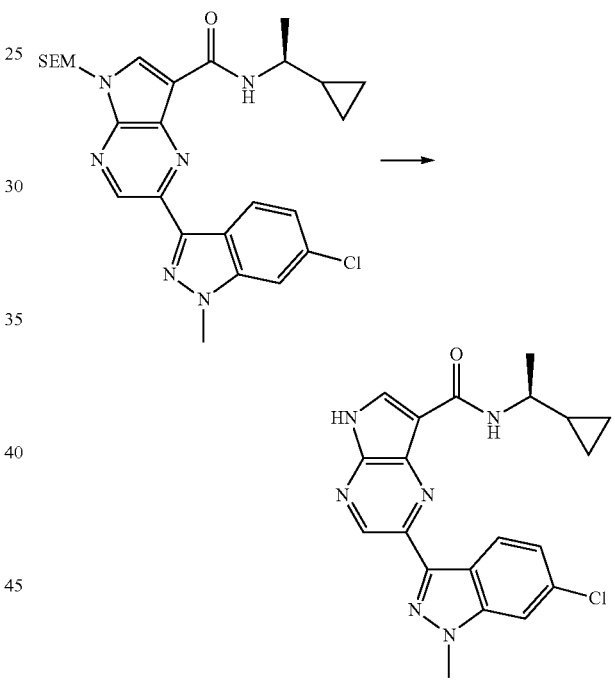

A solution of crude 2-(6-chloro-1-methyl-1H-indazol-3-yl)-5-(2-trimethylsilanylethoxymethyl)-5H-pyrrolo[2,3-b]pyrazine-7-carboxylic acid ((S)-1-cyclopropyl-ethyl)-amide (70 mg, 0.134 mmol), 2 mL of dichloromethane and 2 mL of trifluoroacetic acid was stirred 1 h, then concentrated to a yellow solid. The solid was dissolved in 2 mL of dichloromethane and 1 mL of ethylenediamine, and the yellow solution was stirred 30 min. Water (20 mL) was added. The resultant precipitate was isolated by Buchner filtration, rinsing well with water then dichloromethane, and dried by air then in vacuo to afford 33 mg (56%) of 2-(6-chloro-1-methyl-1H-indazol-3-yl)-5H-pyrrolo[2,3b]pyrazine-7-carboxylic acid ((S)-1-cyclopropyl-ethyl)-amide as a pale yellow solid. MS: $(M+Na)^+$=417; $^1$H NMR (300 MHz, DMSO-$d_6$) δ ppm 9.10 (s, 1 H), 8.46 (d, J=8.69 Hz, 1H), 8.42 (s, 1H), 8.14 (d, J=7.93 Hz, 1H), 8.00 (d, J=1.51 Hz, 1H), 7.27 (dd, J=8.50, 1.70 Hz, 1H), 4.17 (s, 3H), 3.55-3.70 (m, 1H), 1.34 (d, J=6.80

Hz, 3H), 1.00-1.16 (m, 1H), 0.56 (td, J=8.31, 3.40 Hz, 1H), 0.42-0.50 (m, 1H), 0.26-0.41 (m, 2H).

Example 141

2-(6-Chloro-4-fluoro-1-methyl-1H-indazol-3-yl)-5H-pyrrolo[2,3-b]pyrazine-7-carboxylic acid ((S)-1-cyclopropyl-ethyl)-amide

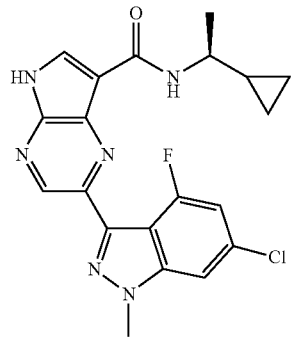 [SMILES: C[C@H](NC(=O)c1c[nH]c2ncc(-c3nn(C)c4cc(Cl)cc(F)c34)nc12)C1CC1]

Prepared according to the procedure outlined in Example 140, substituting 2-(6-chloro-4-fluoro-1-methyl-1H-indazol-3-yl)-5-(2-trimethylsilanyl-ethoxymethyl)-5H-pyrrolo[2,3-b]pyrazine-7-carboxylic acid for 2-(6-chloro-1-methyl-1H-indazol-3-yl)-5-(2-trimethylsilanylethoxymethyl)-5H-pyrrolo[2,3-b]pyrazine-7-carboxylic acid in Step 1. MS: (M−H)⁻=411; ¹H NMR (300 MHz, DMSO-d₆) δ ppm 12.84 (br. s., 1H), 9.01 (s, 1H), 8.41 (s, 1H), 8.37 (d, J=7.93 Hz, 1H), 7.87 (s, 1H), 7.26 (d, J=10.95 Hz, 1H), 4.17 (s, 3H), 3.57-3.70 (m, 1H), 1.21-1.32 (m, 3H), 0.94-1.08 (m, 1H), 0.18-0.52 (m, 4H).

Example 142

2-(6-Chloro-1-methyl-1H-indazol-3-yl)-5H-pyrrolo[2,3-b]pyrazine-7-carboxylic acid ((S)-2-cyano-1-methyl-ethyl)-amide

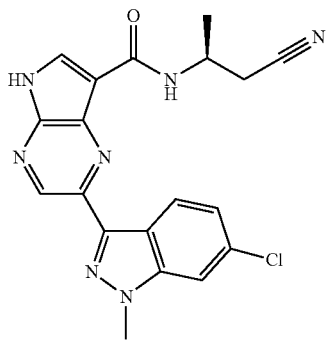 [SMILES: C[C@@H](CC#N)NC(=O)c1c[nH]c2ncc(-c3nn(C)c4cc(Cl)ccc34)nc12]

Prepared according to the procedure outlined in Example 140, substituting (S)-3-aminobutanenitrile for (S)-1-cyclopropylethanamine in Step 1. MS: (M−H)⁻=392; ¹H NMR (300 MHz, DMSO-d₆) δ ppm 12.92 (br. s., 1H), 9.09 (s, 1H), 8.47-8.54 (m, 2H), 8.21 (d, J=7.55 Hz, 1H), 7.99 (s, 1H), 7.27-7.34 (m, 1H), 4.33-4.45 (m, 1H), 4.17 (s, 3H), 2.96 (qd, J=16.62, 5.29 Hz, 2H), 1.44 (d, J=6.80 Hz, 3H).

Example 143

2-(6-Chloro-1-methyl-1H-indazol-3-yl)-5H-pyrrolo[2,3-b]pyrazine-7-carboxylic acid (2-aminoethyl)-amide trifluoroacetate

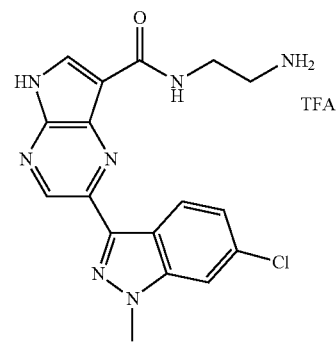 [SMILES: Cn1nc(-c2cnc3[nH]cc(C(=O)NCCN)c3n2)c2ccc(Cl)cc21]

Step 1

2-(6-Chloro-1-methyl-1H-indazol-3-yl)-5-(2-trimethylsilanyl-ethoxymethyl)-5H-pyrrolo[2,3-b]pyrazine-7-carboxylic acid (1H-imidazol-2-yl)-amide

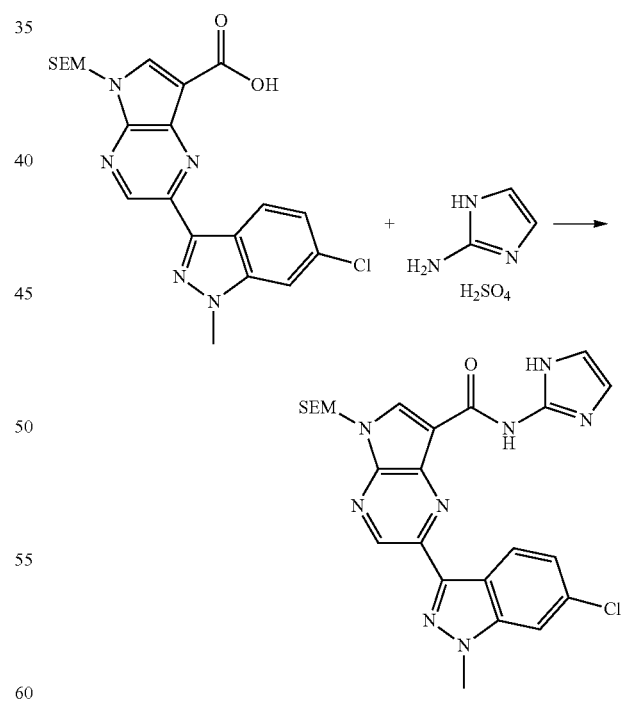

A solution of 2-(6-chloro-1-methyl-1H-indazol-3-yl)-5-(2-trimethylsilanylethoxymethyl)-5H-pyrrolo[2,3-b]pyrazine-7-carboxylic acid (205 mg, 0.447 mmol), 1 mL of N,N-dimethylformamide and O-(7-azabenzotriazole-1-yl)-N,N,N',N'-tetramethyluronium hexafluorophosphate (208 mg, 0.548 mmol) was stirred 10 min. To the solution was added freshly ground 2-aminoimidazole sulfate (62 mg, 0.468 mmol) and diisopropylethylamine (0.39 mL, 2.2 mmol). The flask was heated to 70° C. and the cloudy yellow solution was stirred 18.5 h, during which time a white precipitate formed. The mixture was allowed to cool, then treated with 20 mL of water. The precipitate was isolated by Buchner filtration, rinsing well with water and dried by air then in vacuo to afford 177 mg of impure 2-(6-chloro-1-methyl-1H-indazol-3-yl)-5-(2-trimethylsilanyl-ethoxymethyl)-5H-pyrrolo[2,3-b]pyrazine-7-carboxylic acid (1H-imidazol-2-yl)-amide as a pale yellow solid. MS: (M+H)$^+$=523.

Step 2

2-(6-Chloro-1-methyl-1H-indazol-3-yl)-5H-pyrrolo[2,3-b]pyrazine-7-carboxylic acid (2-aminoethyl)-amide trifluoroacetate

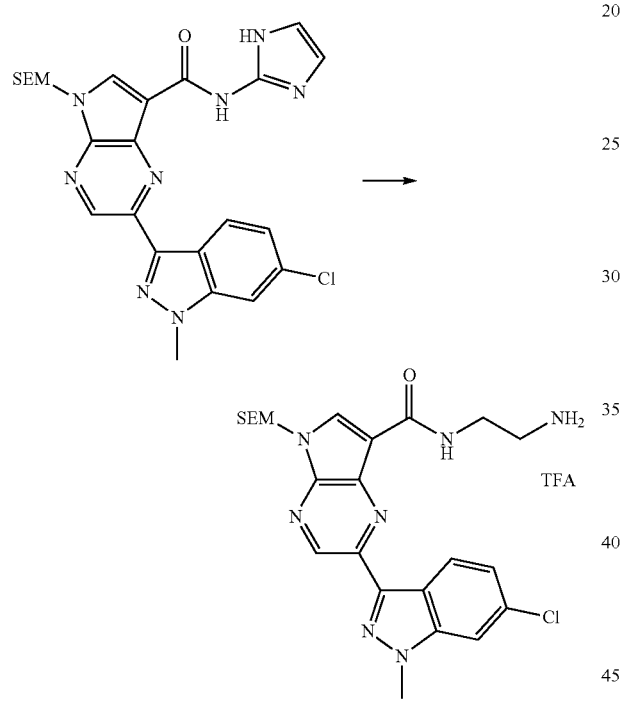

A solution of impure 2-(6-chloro-1-methyl-1H-indazol-3-yl)-5-(2-trimethylsilanylethoxymethyl)-5H-pyrrolo[2,3-b]pyrazine-7-carboxylic acid (1H-imidazol-2-yl)-amide from Step 1 (175 mg, 0.334 mmol) 2 mL of dichloromethane, and 2 mL of trifluoroacetic acid was stirred 1 h then concentrated to an orange oil. To the oil was added 5 mL of dichloromethane and 1 mL of ethylene diamine. The yellow suspension was stirred 30 min. Water (20 mL) was added, and precipitate was isolated by Buchner filtration, rinsing well with water and dichloromethane, and dried by air then in vacuo to afford 109 mg of tan solid. The solid was triturated in 15 mL of boiling methanol, the mixture was allowed to cool to room temperature, and solid was isolated by Buchner filtration, rinsing well with methanol and dried by air to afford 53 mg of a tan solid. The solid was treated with 2 mL of methanol and 1 mL of a 1.0 M HCl in methanol solution. Solid was precipitated with 10 mL of diethyl ether, isolated by Buchner filtration, and dried by air then in vacuo to afford 45 mg of orange solid. Final purification by reverse phase high performance liquid chromatography (C-18 2×10 cm column, eluting with (A) 0.05% TFA/Water (B) 0.05% TFA/Acetonitrile at 25 ml/mn in a linear gradient) afforded two products as trifluoroacetate salts: 7 mg (4%) of 2-(6-chloro-1-methyl-1H-indazol-3-yl)-5H-pyrrolo[2,3-b]pyrazine-7-carboxylic acid (1H-imidazol-2-yl)-amide trifluoroacetate as a pale yellow solid (second peak, MS: (M+H)$^+$=393; $^1$H NMR (300 MHz, DMSO-d$_6$) δ ppm 13.24 (br. s., 1H), 11.33 (br. s., 1H), 9.19 (s, 1H), 8.70-8.79 (m, 2H), 8.00 (s, 1H), 7.29 (d, J=8.69 Hz, 1H), 7.11 (br. s., 2H), 4.18 (s, 3H).) and 0.016 g (10%) of 2-(6-chloro-1-methyl-1H-indazol-3-yl)-5H-pyrrolo[2,3-b]pyrazine-7-carboxylic acid (2-amino-ethyl)-amide trifluoroacetate as a white solid (first peak, MS: (M+H)$^+$=370; $^1$H NMR (300 MHz, DMSO-d$_6$) δ ppm 12.92 (br. s., 1H), 9.10 (s, 1H), 8.44-8.51 (m, 2H), 8.33 (t, J=5.67 Hz, 1H), 8.00 (s, 1H), 7.85 (br. s., 3H), 7.38 (d, J=8.69 Hz, 1H), 4.17 (s, 3H), 3.70 (q, J=6.04 Hz, 2H), 3.02-3.16 (m, 2H).).

Example 144

2-(6-Chloro-1-methyl-1H-indazol-3-yl)-5H-pyrrolo[2,3-b]pyrazine-7-carboxylic acid (trans-4-hydroxy-cyclohexyl)-amide

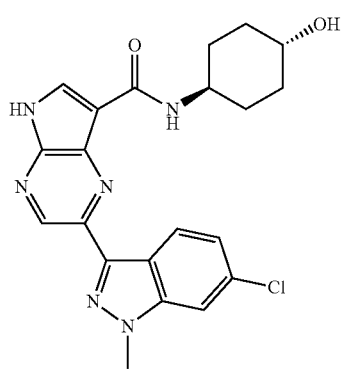 [SMILES: Cn1nc(-c2cnc3[nH]cc(C(=O)N[C@H]4CC[C@H](O)CC4)c3n2)c2ccc(Cl)cc21]

Step 1

2-(6-Chloro-1-methyl-1H-indazol-3-yl)-5-(2-trimethylsilanyl-ethoxymethyl)-5H-pyrrolo[2,3-b]pyrazine-7-carboxylic acid (trans-4-hydroxy-cyclohexyl) amide

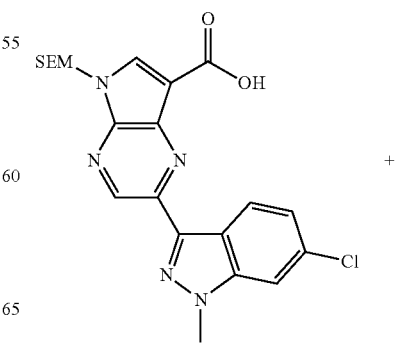

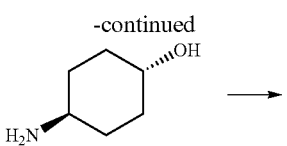

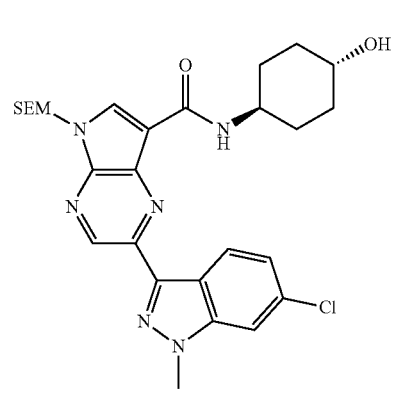

In a 100 mL round-bottomed flask, 2-(6-chloro-1-methyl-1H-indazol-3-yl)-5-(2-trimethylsilanyl-ethoxymethyl)-5H-pyrrolo[2,3-b]pyrazine-7-carboxylic acid (0.150 g, 0.295 mmol), EDC (61 mg, 0.32 mmol), DIEA (52 µl, 0.295 mmol) were combined with dichloromethane (3 ml) to give a yellow solution. Stirred for 30 min then trans-4-aminocyclohexanol (48 mg, 0.42 mmol) was added. The reaction mixture was stirred at room temperature for 24 h then diluted with dichloromethane and washed with water. The organic layer was dried over Na$_2$SO$_4$ and concentrated in vacuo. The crude material was purified by flash chromatography (silica gel, 0% to 5% MeOH in DCM) and recrystallized from ethyl acetate to afford 60 mg of 2-(6-chloro-1-methyl-1H-indazol-3-yl)-5-(2-trimethylsilanylethoxymethyl)-5H-pyrrolo[2,3-b]pyrazine-7-carboxylic acid (trans-4-hydroxy-cyclohexyl)amide as a white solid. MS: [M+H]$^+$=555.

Step 2

2-(6-Chloro-1-methyl-1H-indazol-3-yl)-5H-pyrrolo[2,3-b]pyrazine-7-carboxylic acid (trans-4-hydroxy-cyclohexyl)-amide

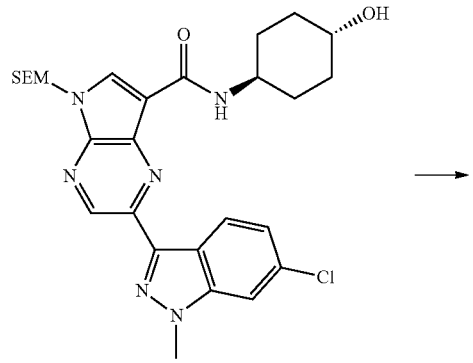

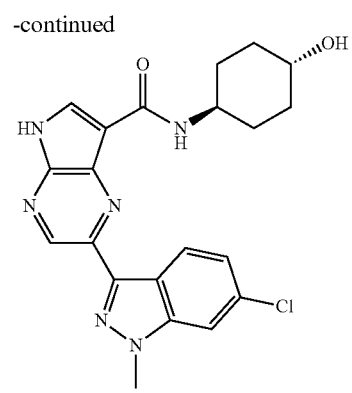

In a 25 mL round-bottomed flask, 2-(6-chloro-1-methyl-1H-indazol-3-yl)-5-(2-trimethylsilanyl-ethoxymethyl)-5H-pyrrolo[2,3-b]pyrazine-7-carboxylic acid (trans-4-hydroxy-cyclohexyl)amide (60 mg, 0.108 mmol) was dissolved in dichloromethane (3 mL). Trifluoroacetic acid (0.2 mL, 2.6 mmol) was added and the orange reaction mixture was stirred at room temperature for 15 h. Additional trifluoroacetic acid (0.7 mL) was added and the reaction stirred for an additional 5 h. The reaction mixture was then concentrated under reduced pressure. The resultant crude solid was dissolved in dichloromethane (3 mL) and ethylenediamine (0.20 mL, 2.96 mmol) was added. The light yellow reaction mixture was stirred at room temperature for 20 h. The reaction mixture was concentrated and the residue was precipitated with water. The suspension was stirred for 1 h and the crude solid collected by filtration. The crude solid was sequentially washed with water, dichloromethane, ethyl acetate, and hexanes to afford 28 mg (60%) of 2-(6-chloro-1-methyl-1H-indazol-3-yl)-5H-pyrrolo[2,3-b]pyrazine-7-carboxylic acid (trans-4-hydroxy-cyclohexyl)amide as a light yellow solid. MS: [M+H]$^+$=525; $^1$H NMR (300 MHz, DMSO-d$_6$) δ: 9.08 (s, 2H), 8.40 (s, 1H), 8.43 (d, J=1.0 Hz, 1H), 8.02 (d, J=1.0 Hz, 1H), 8.01 (s, 1H), 7.28 (dd, J=8.6, 2.0 Hz, 1H), 4.45-4.76 (m, 1H), 4.17 (s, 3H), 3.70-3.96 (m, 1H), 3.43-3.59 (m, 1H), 2.07 (d, J=11.1 Hz, 2H), 1.92 (d, J=10.6 Hz, 2H), 1.18-1.55 (m, 4H).

Example 145

2-(6-Chloro-1-methyl-1H-indazol-3-yl)-5H-pyrrolo[2,3-b]pyrazine-7-carboxylic acid (cis-4-amino-cyclohexyl)-amide

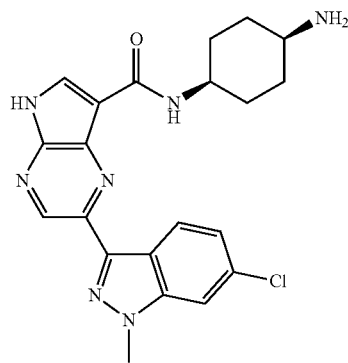 [SMILES: Cn1nc(-c2cnc3[nH]cc(C(=O)N[C@H]4CC[C@@H](N)CC4)c3n2)c2ccc(Cl)cc21]

Step 1

2-(6-Chloro-1-methyl-1H-indazol-3-yl)-5-(2-trimethylsilanyl-ethoxymethyl)-5H-pyrrolo[2,3-b]pyrazine-7-carboxylic acid (cis-4-amino-cyclohexyl) amide

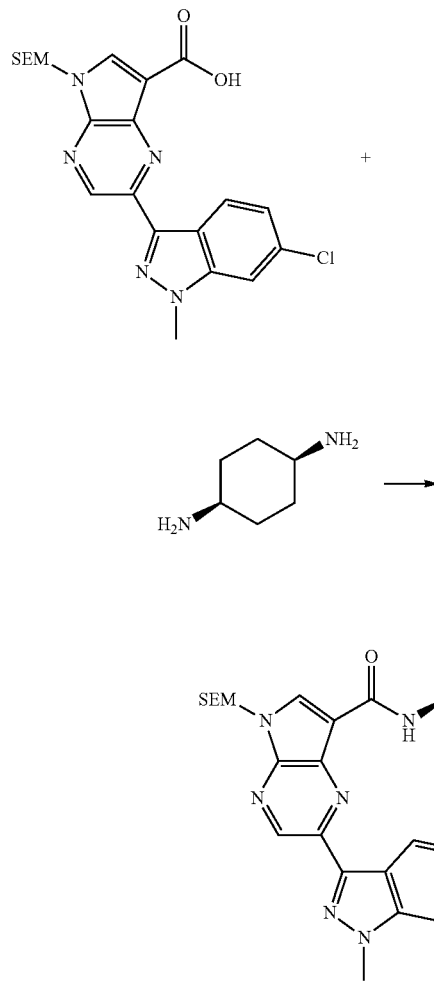

In a 20 mL scintillation vial, 2-(6-chloro-1-methyl-1H-indazol-3-yl)-5-(2-trimethylsilanyl-ethoxymethyl)-5H-pyrrolo[2,3-b]pyrazine-7-carboxylic acid (0.10 g, 0.22 mmol), 2-(1H-benzo[d][1,2,3]triazol-1-yl)-1,1,3,3-tetramethylisouronium hexafluorophosphate (91 mg, 0.24 mmol), 1H-benzo[d][1,2,3]triazol-1-ol (33 mg, 0.240 mmol), and N,N-diisopropylethylamine (38 µl, 0.22 mmol) were combined with DMF (4 ml) to give a light yellow solution. The reaction mixture was stirred at room temperature for 45 min. In a 20 mL round-bottomed flask, cis-cyclohexane-1,4-diamine (249 mg, 2.18 mmol) was dissolved in 0.4 mL DMF to give a colorless solution. The carboxylic acid reaction mixture was added dropwise to the amine solution. The reaction mixture was stirred at room temperature for 24 h. The reaction mixture was diluted with EtOAc (~50 mL) and washed with sat NaHCO$_3$ (3×25 mL) and H$_2$O (3×25 mL). The organic layer was dried over Na$_2$SO$_4$ and concentrated in vacuo. The crude material was purified by chromatography over SiO$_2$ with 0% to 10% MeOH in DCM with 0.1% NH$_4$OH to afford 86 mg of 2-(6-chloro-1-methyl-1H-indazol-3-yl)-5-(2-trimethylsilanylethoxymethyl)-5H-pyrrolo[2,3-b]pyrazine-7-carboxylic acid (cis-4-amino-cyclohexyl)amide as a white solid. MS: [M+H]$^+$=554.

Step 2

2-(6-Chloro-1-methyl-1H-indazol-3-yl)-5H-pyrrolo[2,3-b]pyrazine-7-carboxylic acid (cis-4-amino-cyclohexyl)-amide

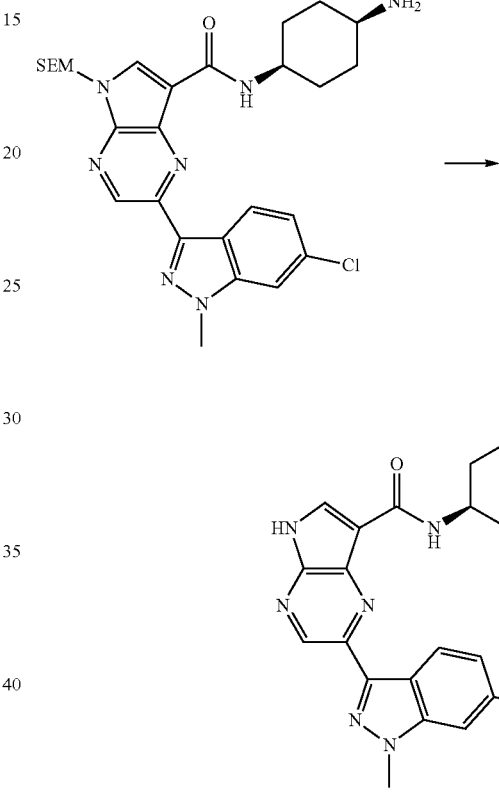

In a 25 mL round-bottomed flask, 2-(6-chloro-1-methyl-1H-indazol-3-yl)-5-(2-trimethylsilanyl-ethoxymethyl)-5H-pyrrolo[2,3-b]pyrazine-7-carboxylic acid (cis-4-aminocyclohexyl)amide (85 mg, 0.153 mmol) was dissolved in dichloromethane (8 mL). Trifluoroacetic acid (2.5 mL, 32.4 mmol) was added and the orange reaction mixture was stirred at room temperature for 3 h. The reaction mixture was then concentrated under reduced pressure. The resultant crude solid was dissolved in dichloromethane (8 mL) and ethylenediamine (1 mL, 14.8 mmol) was added. The reaction mixture was stirred at room temperature for 2 h. The reaction mixture was concentrated and the residue was precipitated with water. The suspension was stirred for 1 h and the crude solid collected by filtration. The crude solid was sequentially washed with water, dichloromethane, ethyl acetate, and hexanes to afford 61 mg (93%) of 2-(6-chloro-1-methyl-1H-indazol-3-yl)-5H-pyrrolo[2,3-b]pyrazine-7-carboxylic acid (cis-4-aminocyclohexyl)-amide as a light yellow solid. MS: [M+H]$^+$= 424; $^1$H NMR (300 MHz, DMSO-d$_6$) δ: 9.05 (d, J=1.0 Hz, 1H), 8.47 (d, J=9.1 Hz, 1H), 8.42 (d, J=1.0 Hz, 1H), 8.08 (d, J=7.1 Hz, 1H), 7.98 (s, 1H), 7.40 (d, J=9.1 Hz, 1H), 4.17 (d, J=1.0 Hz, 3H), 4.00 (br. s., 1H), 2.96 (br. s., 1H), 1.87-2.02 (m, 2H), 1.66-1.76 (m, 2H), 1.55-1.66 (m, 2H), 1.44-1.54 (m, 2H).

Example 146

2-(6-Chloro-1-methyl-1H-indazol-3-yl)-5H-pyrrolo[2,3-b]pyrazine-7-carboxylic acid (trans-4-aminocyclohexyl)-amide

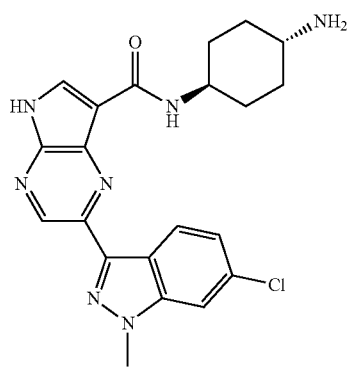 [SMILES: Cn1nc(-c2cnc3[nH]cc(C(=O)N[C@H]4CC[C@H](N)CC4)c3n2)c2ccc(Cl)cc21]

Prepared according to the procedure outlined in Example 2, substituting trans-cyclohexane-1,4-diamine for cis-cyclohexane-1,4,diamine in Step 1. The final compound was isolated as an off-white solid, 33 mg (68%); MS: [M+H]+=424; 1H NMR (300 MHz, DMSO-d6) δ: 9.04 (d, J=1.5 Hz, 1H), 8.44 (dd, J=8.6, 1.0 Hz, 1H), 8.41 (d, J=1.5 Hz, 1H), 8.03 (d, J=8.1 Hz, 1H), 8.00 (s, 1H), 7.26 (d, J=8.6 Hz, 1H), 4.17 (d, J=1.5 Hz, 3H), 3.83 (br. s., 1H), 2.64-2.76 (m, 1H), 2.08 (d, J=10.1 Hz, 2H), 1.88 (d, J=12.1 Hz, 2H), 1.33-1.43 (m, 2H), 1.18-1.30 (m, 2H).

Example 147

2-(6-Chloro-1-methyl-1H-indazol-3-yl)-5H-pyrrolo[2,3-b]pyrazine-7-carboxylic acid (3-oxo-cyclohexyl)-amide

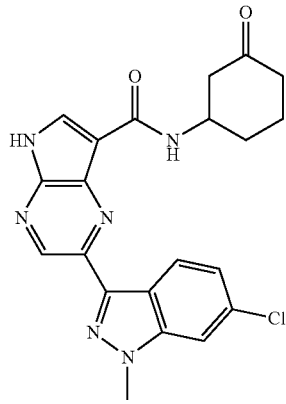

Step 1

2-(6-Chloro-1-methyl-1H-indazol-3-yl)-5-(2-trimethylsilanyl-ethoxymethyl)-5H-pyrrolo[2,3-b]pyrazine-7-carboxylic acid (3-hydroxy-cyclohexyl)amide

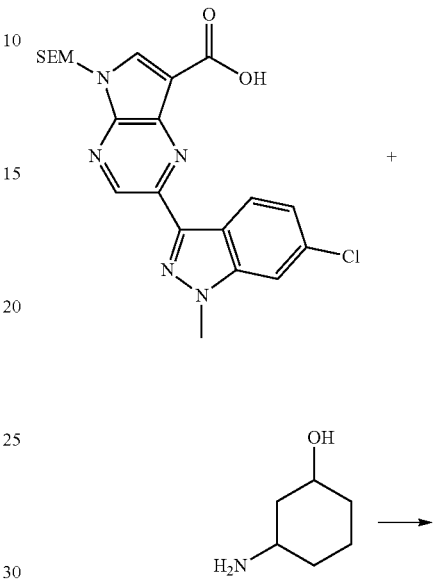

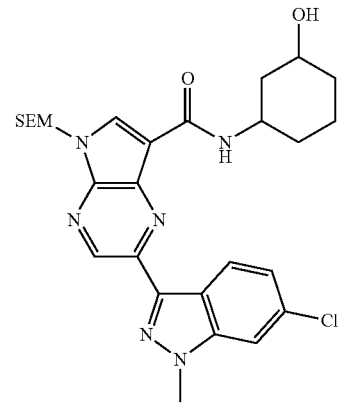

A 25 mL round-bottomed flask was charged with 2-(6-chloro-1-methyl-1H-indazol-3-yl)-5-(2-trimethylsilanyl-ethoxymethyl)-5H-pyrrolo[2,3-b]pyrazine-7-carboxylic acid (0.10 g, 0.22 mmol), 3-aminocyclohexanol (mixture of cis and trans) (45 mg, 0.39 mmol), HBTU (0.10 g, 0.26 mmol), and HOBT (0.03 g, 0.26 mmol). Then added DMF (1.0 mL) followed by N,N-diisopropylethylamine (0.07 ml, 0.26 mmol). The yellow reaction mixture was stirred at room temperature overnight then quenched with water and extracted with EtOAc (30 mL). The organic layer was washed once with saturated NaHCO3 and water. The combined aqueous layers were back extracted with EtOAc (25 mL). The combined organic layers was dried over sodium sulfate, filtered and concentrated. The residue was purified by chromatography over SiO2 with EtOAc/hexanes (gradient: 0-100% EtOAc) to afford 106 mg of 2-(6-chloro-1-methyl-1H-indazol-3-yl)-5-(2-trimethylsilanyl-ethoxymethyl)-5H-pyrrolo

[2,3-b]pyrazine-7-carboxylic acid (3-hydroxy-cyclohexyl) amide as an off-white foam. MS: [M+H]⁺=556.

Step 2

2-(6-Chloro-1-methyl-1H-indazol-3-yl)-5H-pyrrolo[2,3-b]pyrazine-7-carboxylic acid (3-hydroxy-cyclohexyl)-amide

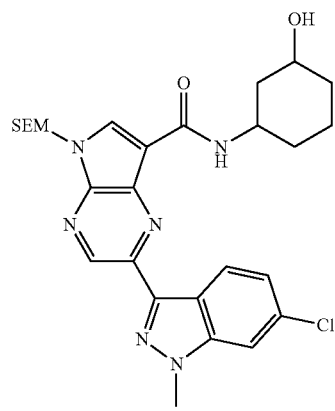

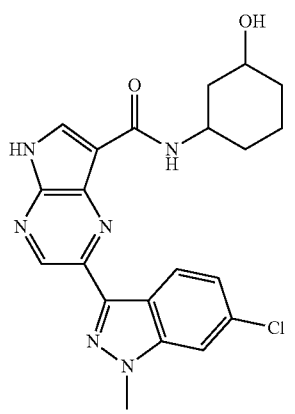

In a 25 mL round-bottomed flask, 2-(6-chloro-1-methyl-1H-indazol-3-yl)-5-(2-trimethylsilanyl-ethoxymethyl)-5H-pyrrolo[2,3-b]pyrazine-7-carboxylic acid (3-hydroxycyclohexyl)amide (106 mg, 0.19 mmol) was dissolved dichloromethane (3 mL). Trifluoroacetic acid (0.2 mL, 2.6 mmol) was added and the orange reaction mixture was stirred at room temperature for 15 h. Additional trifluoroacetic acid (0.7 mL) was added and the reaction stirred for an additional 5 h. The reaction mixture was then concentrated under reduced pressure. The resultant crude solid was dissolved in dichloromethane (3 mL) and ethylenediamine (0.20 mL, 2.96 mmol) was added. The light yellow reaction mixture was stirred at room temperature for 20 h. The reaction mixture was concentrated and the residue was precipitated with water. The suspension was stirred for 1 h and the crude solid collected by filtration. The crude solid was sequentially washed with water, dichloromethane, ethyl acetate, and hexanes to afford 74 mg (91%) of 2-(6-chloro-1-methyl-1H-indazol-3-yl)-5H-pyrrolo[2,3-b]pyrazine-7-carboxylic acid (3-hydroxy-cyclohexyl)-amide as a white solid and a 2:1 mixture of cis and trans isomers (unassigned). MS: [M+Na] 447.

Step 3

2-(6-Chloro-1-methyl-1H-indazol-3-yl)-5H-pyrrolo[2,3-b]pyrazine-7-carboxylic acid (3-oxo-cyclohexyl)-amide

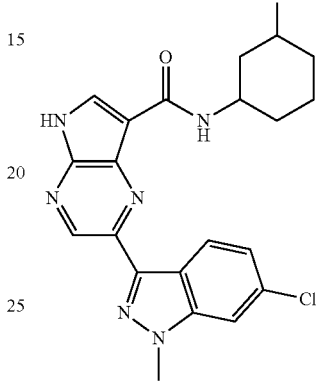

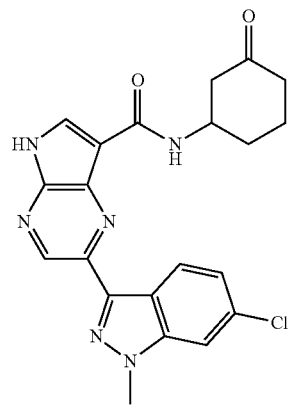 [SMILES: Cn1nc(-c2cnc3[nH]cc(C(=O)NC4CCCC(=O)C4)c3n2)c2ccc(Cl)cc21]

A 25 mL round-bottom flask was charged with 2-(6-chloro-1-methyl-1H-indazol-3-yl)-5H-pyrrolo[2,3-b]pyrazine-7-carboxylic acid (3-hydroxy-cyclohexyl) amide (22 mg, 0.052 mmol) and dichloromethane (5 mL). Dess-Martin periodinane (34.0 mg, 0.08 mmol) was added in one portion to the reaction mixture. The reaction mixture was placed under Ar and stirred for 2 h at room temperature. DMF (1.5 mL) was added and the reaction mixture was stirred for an additional 18 h. The reaction mixture was diluted to 100 mL with EtOAc and washed with sat NaHCO₃ (3×20 mL). The crude white precipitate was filtered and reserved. The organic layer was dried over Na₂SO₄ and concentrated in vacuo to give a crude solid. The combined crude solids were triturated with EtOAc (1×20 mL) then purified by chromatography over SiO₂ with MeOH/dichloromethane (gradient: 0%-5% MeOH) to afford 6 mg (27%) of 2-(6-chloro-1-methyl-1H-indazol-3-yl)-5H-pyrrolo[2,3-b]pyrazine-7-carboxylic acid (3-oxo-cyclohexyl)-amide as a white solid. MS: [M+H]⁺= 423, ¹H NMR (300 MHz, DMSO-d₆) δ: 12.89 (br. s., 1H), 9.09 (s, 1H), 8.47 (s, 1H), 8.42 (d, J=8.7 Hz, 1H), 8.16 (d, J=7.6 Hz, 1H), 8.01 (d, J=1.5 Hz, 1H), 7.39 (dd, J=8.7, 1.9 Hz, 1H), 4.23-4.41 (m, 1H), 4.18 (s, 3H), 2.69-2.78 (m, 1H), 2.58

(d, J=10.2 Hz, 1H), 2.42 (dd, J=11.1, 5.9 Hz, 1H), 2.17-2.34 (m, 2H), 1.96-2.08 (m, 1H), 1.80-1.93 (m, 1H), 1.65-1.80 (m, 1H).

Examples 148 and 149

2-(6-Chloro-1-methyl-1H-indazol-3-yl)-5H-pyrrolo[2,3-b]pyrazine-7-carboxylic acid (trans-3-hydroxy-cyclohexyl)-amide and 2-(6-Chloro-1-methyl-1H-indazol-3-yl)-5H-pyrrolo[2,3-b]pyrazine-7-carboxylic acid (cis-3-hydroxy-cyclohexyl)-amide

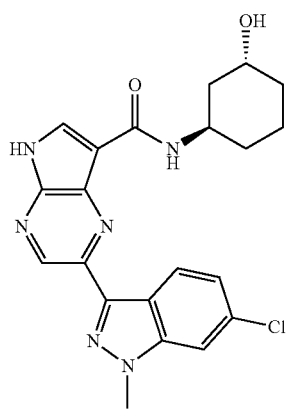

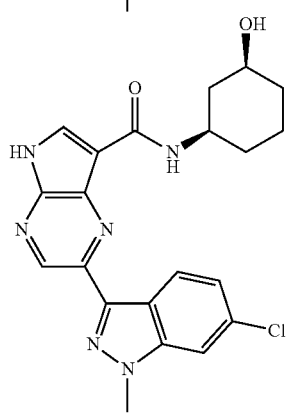

A sample of 2-(6-chloro-1-methyl-1H-indazol-3-yl)-5H-pyrrolo[2,3-b]pyrazine-7-carboxylic acid (3-hydroxy-cyclohexyl)-amide (Example 147, Step 2) was purified by chromatography over SiO$_2$ with MeOH/dichloromethane (gradient: 0%-10% MeOH with 0.1% NH$_4$OH) to afford 8 mg of 2-(6-chloro-1-methyl-1H-indazol-3-yl)-5H-pyrrolo[2,3-b]pyrazine-7-carboxylic acid (trans-3-hydroxy-cyclohexyl)-amide; $^1$H NMR (300 MHz, DMSO-d$_6$) δ: 12.85 (br s, 1H), 9.08 (s, 1H), 8.48 (d, J=8.7 Hz, 1H), 8.42 (s, 1H), 8.09 (d, J=7.9 Hz, 1H), 8.01 (d, J=1.1 Hz, 1H), 7.31 (dd, J=8.5, 1.3 Hz, 1H), 4.79 (br. s., 1H), 4.17 (s, 3H), 3.84-4.02 (m, 1H), 3.49-3.61 (m, 1H), 2.28 (app d, J=10.6 Hz, 1H), 2.03 (app d, J=12.8 Hz, 1H), 1.88 (app d, J=10.6 Hz, 1H), 1.77 (app d, J=13.2 Hz, 1H), 1.06-1.43 (m, 4H) and 3 mg of 2-(6-chloro-1-methyl-1H-indazol-3-yl)-5H-pyrrolo[2,3-b]pyrazine-7-carboxylic acid (cis-3-hydroxycyclohexyl)-amide; $^1$H NMR (300 MHz, DMSO-d$_6$) δ: 12.85 (br s, 1H), 9.10 (s, 1H), 8.46 (d, J=8.7 Hz, 1H), 8.40 (d, J=7.9 Hz, 1H), 8.02 (s, 1H), 8.01 (d, J=8.3 Hz, 1H), 7.30 (dd, J=9.1, 1.3 Hz, 1H), 4.57 (br d, J=3.8 Hz, 1H), 4.26-4.43 (m, 1H), 4.18 (s, 3H), 3.96-4.05 (m, 1H), 1.92 (app d, J=11.7 Hz, 1H), 1.77 (app d, J=13.2 Hz, 1H), 1.65 (app d, J=12.8 Hz, 1H), 1.49-1.58 (m, 1H), 1.10-1.43 (m, 4H).

Example 150

2-(6-Chloro-1-methyl-1H-indazol-3-yl)-5H-pyrrolo[2,3-b]pyrazine-7-carboxylic acid (1-methyl-2-phenyl-ethyl)-amide

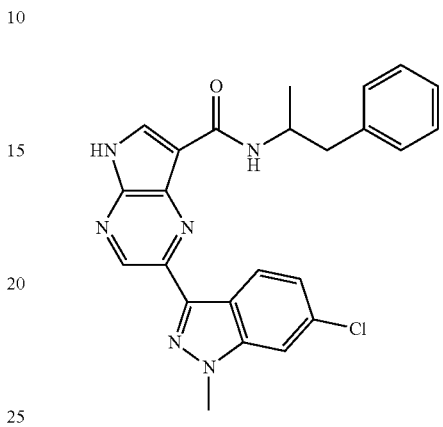

Prepared according to the procedure outlined in Example 145, substituting d,l-amphetamine sulfate for cis-cyclohexane-1,4,diamine in Step 1. The final compound was isolated as a light yellow solid, 31 mg (67%); MS: [M+Na]$^+$=467; $^1$H NMR (300 MHz, DMSO-d$_6$) δ ppm 12.83 (br. s., 1H) 9.09 (s, 1H) 8.44 (s, 1H) 8.16 (d, J=8.7 Hz, 1H) 8.09 (d, J=8.3 Hz, 1H) 7.99 (d, J=1.5 Hz, 1H) 7.04-7.31 (m, 6H) 4.41 (dt, J=13.8, 6.7 Hz, 1H) 4.17 (s, 3H) 2.84-3.05 (m, 2H) 1.27 (d, J=6.4 Hz, 3H).

Example 151

2-(6-Chloro-1-methyl-1H-indazol-3-yl)-5H-pyrrolo[2,3-b]pyrazine-7-carboxylic acid ((1R,3S)-3-hydroxy-cyclopentyl)-amide

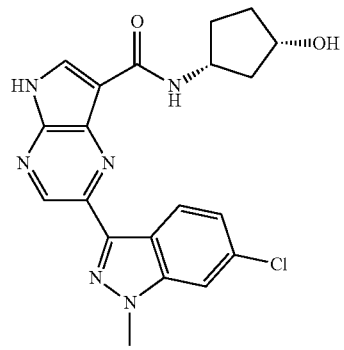 [SMILES: Cn1nc(-c2cnc3[nH]cc(C(=O)N[C@@H]4CC[C@H](O)C4)c3n2)c2ccc(Cl)cc21]

Prepared according to the procedure outlined in Example 145, substituting (1S,3R)-3-aminocyclopentanol for cis-cyclohexane-1,4,diamine in Step 1. The final compound was isolated as a light yellow solid, 26 mg (97%); MS: [M+Na]$^+$=432; $^1$H NMR (300 MHz, DMSO-d$_6$) δ: 12.61 (br. s., 1H), 9.12 (s, 1H), 8.57 (d, J=8.7 Hz, 1H), 8.42 (s, 1H), 8.19 (d, J=8.3 Hz, 1H), 7.99 (s, 1H), 7.37 (dd, J=8.5, 1.3 Hz, 3H), 4.80 (d, J=2.6 Hz, 1H), 4.44 (sxt, J=7.5 Hz, 1H), 4.20-4.26 (m, 1H), 4.17 (s, 3H), 2.30 (ddd, J=13.7, 8.2, 5.7 Hz, 1H), 2.07-2.18 (m, 1H), 1.69-1.86 (m, 3H), 1.51-1.62 (m, 1H).

Example 152

2-(6-Chloro-1-methyl-1H-indazol-3-yl)-5H-pyrrolo[2,3-b]pyrazine-7-carboxylic acid (2-methoxy-1-methyl-ethyl)-amide

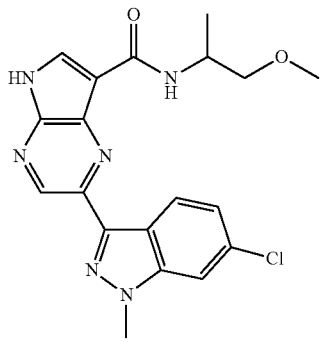 [SMILES: COCC(C)NC(=O)c1c[nH]c2ncc(-c3nn(C)c4cc(Cl)ccc34)nc12]

Prepared according to the procedure outlined in Example 145, substituting 1-methoxypropan-2-amine for cis-cyclohexane-1,4,diamine in Step 1. The final compound was isolated as a light yellow solid, 28 mg (69%); MS: [M+H]$^+$=399; $^1$H NMR (300 MHz, DMSO-d$_6$) δ: 9.11 (s, 1H), 8.53 (d, J=8.7 Hz, 1H), 8.44 (s, 1H), 8.20 (d, J=8.7 Hz, 1H), 8.01 (d, J=1.5 Hz, 1H), 7.28 (dd, J=8.7, 1.5 Hz, 1H), 4.30-4.47 (m, 1H), 4.18 (s, 3H), 3.50 (qd, J=9.6, 4.5 Hz, 2H), 3.27 (s, 3H), 1.31 (d, J=6.8 Hz, 3H).

Example 153

2-(6-Chloro-1-methyl-1H-indazol-3-yl)-5H-pyrrolo[2,3-b]pyrazine-7-carboxylic acid (2-methylcyclohexyl)-amide

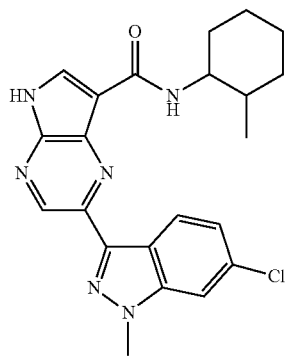 [SMILES: CC1CCCCC1NC(=O)c1c[nH]c2ncc(-c3nn(C)c4cc(Cl)ccc34)nc12]

Prepared according to the procedure outlined in Example 145, substituting 2-methylcyclohexylamine for cis-cyclohexane-1,4,diamine in Step 1. The final compound was isolated as a light yellow solid in a 2:3 mixture of diasteriomers, 39 mg (58%); MS: [M+H]$^+$=423; $^1$H NMR (300 MHz, DMSO-d$_6$) δ: 9.08 (s, 1H), 9.01 (s, 1H), 8.42 (s, 1H), 8.43 (d, J=8.7 Hz, 1H), 8.39 (s, 1H), 8.35 (d, J=8.7 Hz, 1H), 8.07 (s, 1H), 8.03 (d, J=8.7 Hz, 1H), 8.02 (d, J=8.9 Hz, 1H), 7.99 (s, 1H), 7.26 (d, J=8.3 Hz, 1H), 7.25 (d, J=8.3 Hz, 1H), 4.25 (br. s., 2H), 4.17 (s, 6H), 1.06-2.12 (m, 18H), 0.98 (d, J=6.4 Hz, 3H), 0.90 (d, J=6.8 Hz, 3H)).

Example 154

2-(6-Chloro-1-methyl-1H-indazol-3-yl)-5H-pyrrolo[2,3-b]pyrazine-7-carboxylic acid [1-(tetrahydrofuran-2-yl)-ethyl]-amide

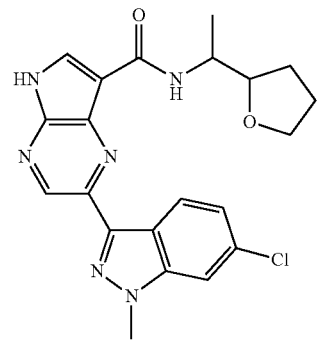

Prepared according to the procedure outlined in Example 145, substituting 1-(tetrahydrofuran-2-yl)ethylamine for cis-cyclohexane-1,4,diamine in Step 1. The final compound was isolated as an off-white solid and a mixture of isomers, 36 mg (71%) MS: [M+H]$^+$=425; $^1$H NMR (300 MHz, DMSO-d$_6$) δ: 12.81 (br. s., 2H), 9.15 (s, 1H), 9.12 (s, 1H), 8.64 (d, J=8.7 Hz, 1H), 8.54 (d, J=8.7 Hz, 1H), 8.45 (s, 2H), 8.23 (d, J=9.4 Hz, 2H), 8.00 (d, J=1.5 Hz, 2H), 7.27 (dd, J=8.7, 1.5 Hz, 1H), 7.25 (dd, J=8.7, 1.5 Hz, 1H), 4.18-4.41 (m, 2H), 4.18 (s, 6H), 3.91-4.02 (m, 1H), 3.85 (q, J=6.9 Hz, 1H), 3.65-3.75 (m, 1H), 3.53-3.66 (m, 1H), 3.36 (s, 2H), 1.52-2.05 (m, 8H), 1.34 (d, J=6.8 Hz, 3H), 1.26 (d, J=6.8 Hz, 3H).

Example 155

2-(6-Chloro-1-methyl-1H-indazol-3-yl)-5H-pyrrolo[2,3-b]pyrazine-7-carboxylic acid (trans-3-carbamoyl-cyclohexyl)-amide

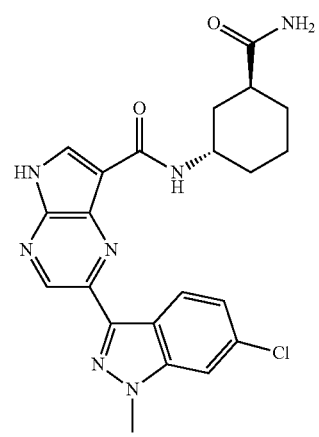 [SMILES: Cn1nc(-c2cnc3[nH]cc(C(=O)N[C@H]4CCC[C@H](C(N)=O)C4)c3n2)c2ccc(Cl)cc21]

Prepared according to the procedure outlined in Example 145, substituting trans-3-aminocyclohexanecarboxamide hydrochloride for cis-cyclohexane-1,4,diamine in Step 1. The final compound was isolated as an off-white solid, 4.5 mg (29%); MS: [M+Na]⁺=474; ¹H NMR (DMSO-d₆) δ: 12.85 (br. s., 1H), 9.05 (s, 1H), 8.46 (s, 1H), 8.41 (d, J=8.7 Hz, 1H), 8.12 (d, J=7.6 Hz, 1H), 8.00 (d, J=1.5 Hz, 1H), 7.27 (dd, J=8.7, 1.5 Hz, 1H), 7.16 (br. s., 1H), 6.69 (br. s., 1H), 4.27-4.39 (m, 1H), 4.18 (s, 3H), 2.39-2.52 (m, 1H), 1.43-1.95 (m, 8H).

Example 156

2-(6-Chloro-1-methyl-1H-indazol-3-yl)-5H-pyrrolo[2,3-b]pyrazine-7-carboxylic acid (trans-3-cyano-cyclohexyl)-amide

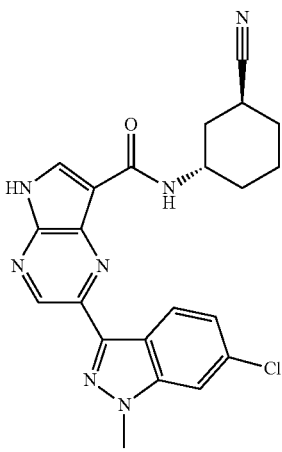 [SMILES: Cn1nc(-c2cnc3[nH]cc(C(=O)N[C@H]4CCC[C@H](C#N)C4)c3n2)c2ccc(Cl)cc21]

Step 1

2-(6-Chloro-1-methyl-1H-indazol-3-yl)-5-(2-trimethylsilanyl-ethoxymethyl)-5H-pyrrolo[2,3-b]pyrazine-7-carboxylic acid (trans-3-carbamoyl-cyclohexyl)-amide

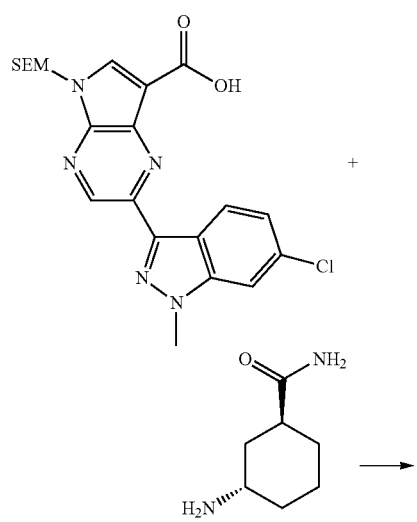

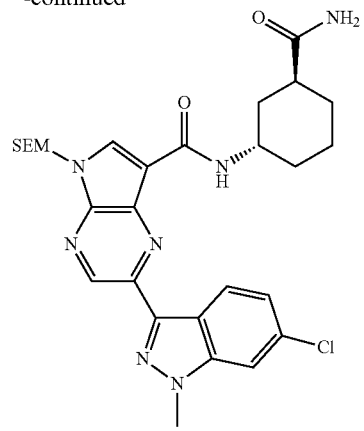

A 25 mL round-bottomed flask was charged with 2-(6-chloro-1-methyl-1H-indazol-3-yl)-5-(2-trimethylsilanyl-ethoxymethyl)-5H-pyrrolo[2,3-b]pyrazine-7-carboxylic acid (0.15 g, 0.33 mmol), trans-3-aminocyclohexanecarboxamide hydrochloride (88 mg, 0.49 mmol), HBTU (155 mg, 0.41 mmol), and HOBT (49 mg, 0.41 mmol). Then added DMF (1.0 mL) followed by N,N-diisopropylethylamine (0.17 mL, 0.97 mmol). The yellow reaction mixture was stirred at room temperature overnight then quenched with water and extracted with EtOAc (30 mL). The organic layer was washed once with saturated NaHCO₃ and water. The combined aqueous layers were back extracted with EtOAc (25 mL). The combined organic layers was dried over sodium sulfate, filtered and concentrated. The residue was purified by chromatography over SiO₂ with EtOAc/hexanes (gradient: 0-100% EtOAc) to afford 119 mg (62%) of 2-(6-chloro-1-methyl-1H-indazol-3-yl)-5-(2-trimethylsilanyl-ethoxymethyl)-5H-pyrrolo[2,3-b]pyrazine-7-carboxylic acid (trans-3-carbamoyl-cyclohexyl)-amide as a white solid. MS: [M+Na]⁺=604.

Step 2

2-(6-Chloro-1-methyl-1H-indazol-3-yl)-5-(2-trimethylsilanyl-ethoxymethyl)-5H-pyrrolo[2,3-b]pyrazine-7-carboxylic acid (trans-3-cyano-cyclohexyl)-amide

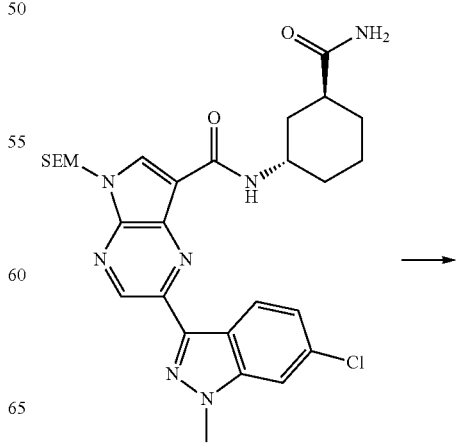

-continued

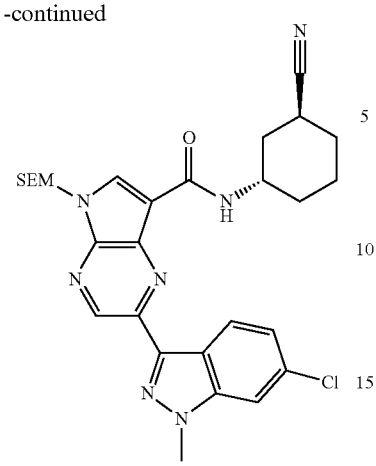

In a 25 mL pear-shaped flask, 2-(6-chloro-1-methyl-1H-indazol-3-yl)-5-(2-trimethylsilanyl-ethoxymethyl)-5H-pyrrolo[2,3-b]pyrazine-7-carboxylic acid (trans-3-carbamoyl-cyclohexyl)-amide (72 mg, 0.124 mmol) was combined with pyridine (412 μl) to give a off-white solution. The reaction mixture was cooled at 0° C. and trifluoroacetic anhydride (0.71 M in pyridine, 26 μl, 0.18 mmol) was added dropwise. The reaction mixture was allowed to stir at room temperature for 30 min and then concentrated. The residue was purified by chromatography over $SiO_2$ with EtOAc/hexanes (gradient: 0-50% EtOAc) to afford 27 mg (39%) of 2-(6-chloro-1-methyl-1H-indazol-3-yl)-5-(2-trimethylsilanyl-ethoxymethyl)-5H-pyrrolo[2,3-b]pyrazine-7-carboxylic acid (trans-3-cyano-cyclohexyl)-amide as a white solid. $^1$H NMR (300 MHz, DMSO-$d_6$) δ: 9.14 (s, 1H), 8.66 (s, 1H), 8.40 (d, J=8.7 Hz, 1H), 8.06 (d, J=7.9 Hz, 1H), 8.01 (d, J=1.0 Hz, 1H), 7.38 (dd, J=8.7, 1.0 Hz, 1H), 5.73 (s, 2H), 4.18 (s, 3H), 4.09-4.28 (m, 1H), 3.59 (t, J=7.9 Hz, 2H), 3.41-3.60 (br. s., 1H), 2.24 (app. d, J=12.5 Hz, 1H), 2.07 (app. d, J=12.1 Hz, 1H), 1.59-1.91 (m, 5H), 1.39-1.59 (m, 1H), 0.86 (t, J=7.9 Hz, 2H), −0.08 (s, 9H).

Step 3

2-(6-Chloro-1-methyl-1H-indazol-3-yl)-5H-pyrrolo[2,3-b]pyrazine-7-carboxylic acid (trans-3-cyano-cyclohexyl)-amide

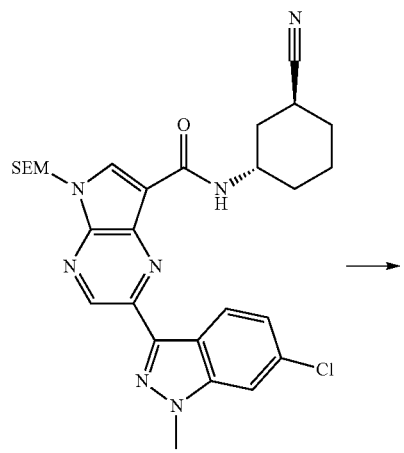

-continued

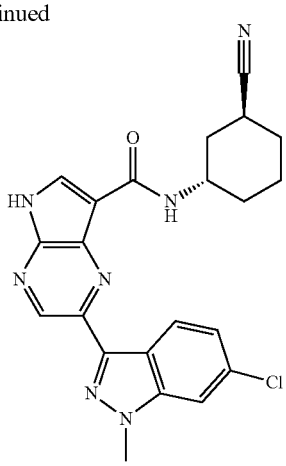

In a 25 mL round-bottomed flask, 2-(6-chloro-1-methyl-1H-indazol-3-yl)-5-(2-trimethylsilanyl-ethoxymethyl)-5H-pyrrolo[2,3-b]pyrazine-7-carboxylic acid (trans-3-cyanocyclohexyl)-amide (48 mg, 0.085 mmol) was dissolved in dichloromethane (3 mL). Trifluoroacetic acid (1.2 mL, 15.6 mmol) was added and the orange reaction mixture was stirred at room temperature for 2 h. The reaction mixture was then concentrated under reduced pressure. The resultant crude solid was dissolved in dichloromethane (3 mL) and ethylenediamine (0.50 mL, 7.4 mmol) was added. The light yellow reaction mixture was stirred at room temperature for 18 h. The reaction mixture was concentrated and the residue was precipitated with water. The suspension was stirred for 1 h and the crude solid collected by filtration. The crude solid was sequentially washed with water, ethyl acetate, and hexanes to afford 35 mg (95%) of 2-(6-chloro-1-methyl-1H-indazol-3-yl)-5H-pyrrolo[2,3-b]pyrazine-7-carboxylic acid (trans-3-cyanocyclohexyl)-amide as an off-white solid. MS: [M+Na]$^+$= 474; $^1$H NMR (DMSO-$d_6$) δ: 12.79 (br. s., 1H), 9.08 (s, 1H), 8.46 (s, 1H), 8.40 (d, J=8.7 Hz, 1H), 8.08 (d, J=7.9 Hz, 1H), 8.00 (d, J=0.8 Hz, 1H), 7.37 (dd, J=8.5, 1.1 Hz, 1H), 4.17 (s, 3H), 4.01-4.31 (m, 1H), 3.30-3.49 (m, 1H), 2.24 (d, J=13.2 Hz, 1H), 2.07 (d, J=12.1 Hz, 1H), 1.59-1.94 (m, 5H), 1.36-1.59 (m, 1H).

Example 157

2-(6-Chloro-1-methyl-1H-indazol-3-yl)-5H-pyrrolo[2,3-b]pyrazine-7-carboxylic acid (R)-indan-1-ylamide

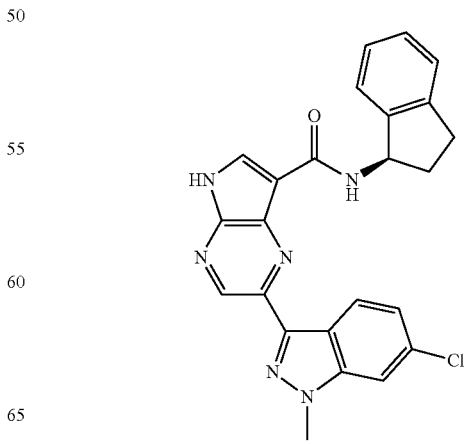

Prepared according to the procedure outlined in Example 145, substituting (R)-2,3-dihydro-1H-inden-1-amine for cis-cyclohexane-1,4,diamine in Step 1. The final compound was isolated as an off-white solid, 15 mg (21%); MS: [M+Na]$^+$= 475; $^1$H NMR (DMSO-d$_6$) δ: 12.91 (br. s., 1H), 9.09 (s, 1H), 8.52-8.55 (m, 1H), 8.50 (d, J=8.7 Hz, 1H), 7.91 (d, J=1.0 Hz, 1H), 7.83 (d, J=8.7 Hz, 1H), 7.41 (t, J=9.1 Hz, 1H), 7.32 (t, J=7.2 Hz, 2H), 7.22 (t, J=7.6 Hz, 1H), 6.51 (dd, J=8.7, 1.5 Hz, 1H), 5.73 (q, J=7.8 Hz, 1H), 4.14-4.20 (m, 1H), 4.12 (s, 3H), 3.01-3.16 (m, 1H), 2.86-3.01 (m, 1H), 2.59-2.77 (m, 1H), 1.79-2.02 (m, 1H).

Example 158

2-(6-Chloro-1-methyl-1H-indazol-3-yl)-5H-pyrrolo[2,3-b]pyrazine-7-carboxylic acid (cis-4-hydroxy-cyclohexyl)-amide

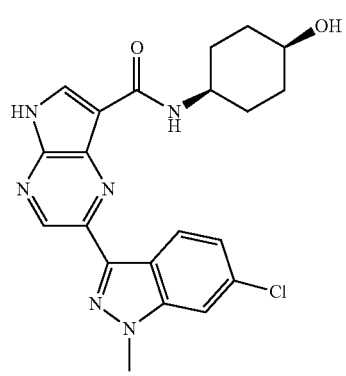 [SMILES: Cn1nc(-c2cnc3[nH]cc(C(=O)N[C@H]4CC[C@@H](O)CC4)c3n2)c2ccc(Cl)cc21]

Prepared according to the procedure outlined in Example 145, substituting cis-4-aminocyclohexanol hydrochloride for cis-cyclohexane-1,4,diamine in Step 1. The final compound was isolated as a light yellow solid, 47 mg (91%); MS: [M+Na]$^+$=447; $^1$H NMR (300 MHz, DMSO-d$_6$) δ: 12.35 (br. s., 1H), 9.11 (s, 1H), 8.47 (d, J=8.7 Hz, 1H), 8.43 (s, 1H), 8.14 (d, J=7.9 Hz, 1H), 8.00 (d, J=1.5 Hz, 1H), 7.42 (dd, J=8.7, 1.5 Hz, 1H), 4.58 (br. s., 1H), 4.18 (s, 3H), 3.88-4.09 (m, 1H), 3.81 (br. s., 1H), 1.53-1.93 (m, 8H).

Example 159

2-(6-Chloro-1-methyl-1H-indazol-3-yl)-5H-pyrrolo[2,3-b]pyrazine-7-carboxylic acid ((R)-2-methoxy-1-methyl-ethyl)-amide

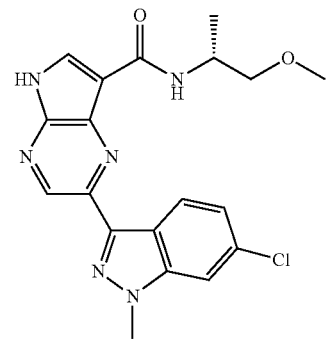 [SMILES: COC[C@@H](C)NC(=O)c1c[nH]c2ncc(-c3nn(C)c4cc(Cl)ccc34)nc12]

Step 1

2-(6-Chloro-1-methyl-1H-indazol-3-yl)-5-(2-trimethylsilanyl-ethoxymethyl)-5H-pyrrolo[2,3-b]pyrazine-7-carboxylic acid ((R)-2-hydroxy-1-methyl-ethyl)-amide

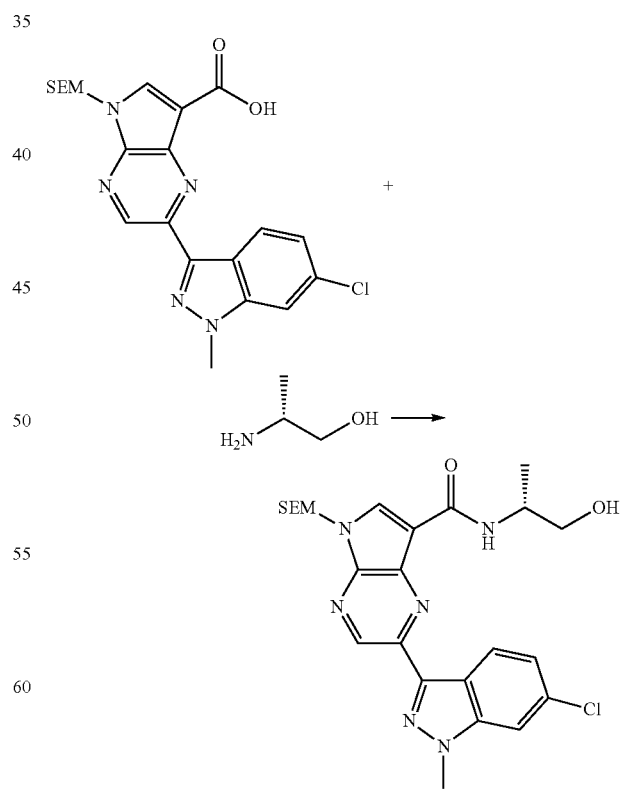

A 25 mL round-bottomed flask was charged with 2-(6-chloro-1-methyl-1H-indazol-3-yl)-5-(2-trimethylsilanylethoxymethyl)-5H-pyrrolo[2,3-b]pyrazine-7-carboxylic acid (0.15 g, 0.33 mmol), (R)-2-aminopropan-1-ol (49 mg, 0.66 mmol), HBTU (155 mg, 0.41 mmol), and HOBT (58 mg, 0.49 mmol). Then added DMF (1.1 mL) followed by N,N-diisopropylethylamine (0.17 mL, 0.97 mmol). The yellow reaction mixture was stirred at room temperature overnight then quenched with water and extracted with EtOAc (30 mL). The organic layer was washed once with saturated NaHCO$_3$ and water. The combined aqueous layers were back extracted with EtOAc (25 mL). The combined organic layers was dried over sodium sulfate, filtered and concentrated. The residue was purified by chromatography over SiO$_2$ with EtOAc/hexanes (gradient: 0-60% EtOAc) to afford 110 mg (65%) of 2-(6-chloro-1-methyl-1H-indazol-3-yl)-5-(2-trimethylsilanyl-ethoxymethyl)-5H-pyrrolo[2,3-b]pyrazine-7-carboxylic acid ((R)-2-hydroxy-1-methyl-ethyl)-amide as an off-white solid. MS: [M+H]$^+$=515.

Step 2

2-(6-Chloro-1-methyl-1H-indazol-3-yl)-5-(2-trimethylsilanyl-ethoxymethyl)-5H-pyrrolo[2,3-b]pyrazine-7-carboxylic acid ((R)-2-methoxy-1-methyl-ethyl)-amide

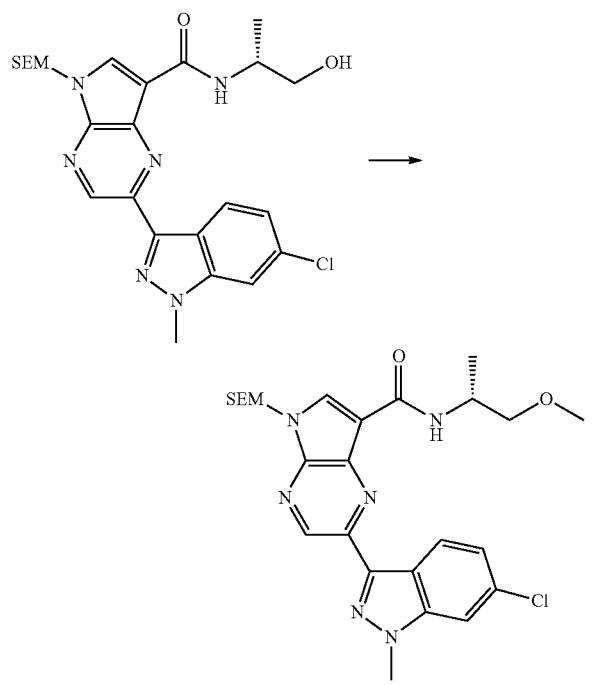

In a 25 mL round-bottomed flask, 2-(6-chloro-1-methyl-1H-indazol-3-yl)-5-(2-trimethylsilanyl-ethoxymethyl)-5H-pyrrolo[2,3-b]pyrazine-7-carboxylic acid ((R)-2-hydroxy-1-methyl-ethyl)-amide (70 mg, 0.136 mmol), silver oxide (51 mg, 0.22 mmol) and methyl iodide (100 µl, 1.6 mmol) were combined with MeCN to give a black suspension. The round bottom flask was wrapped in foil to exclude light. The system was placed in a sand bath and heated to 40° C. with stirring. The temperature was maintained for 2 days. Upon cooling, the reaction mixture was filtered through a pad a celite. The filtrate was concentrated. The crude material was purified by chromatography over SiO$_2$ with EtOAc/hexanes (gradient: 0%-40% EtOAc) to afford 32 mg (45%) of 2-(6-chloro-1-methyl-1H-indazol-3-yl)-5-(2-trimethylsilanylethoxymethyl)-5H-pyrrolo[2,3-b]pyrazine-7-carboxylic acid ((R)-2-methoxy-1-methyl-ethyl)-amide as an off-white solid. [M+Na]$^+$=551.

Step 3

2-(6-Chloro-1-methyl-1H-indazol-3-yl)-5H-pyrrolo[2,3-b]pyrazine-7-carboxylic acid ((R)-2-methoxy-1-methyl-ethyl)-amide

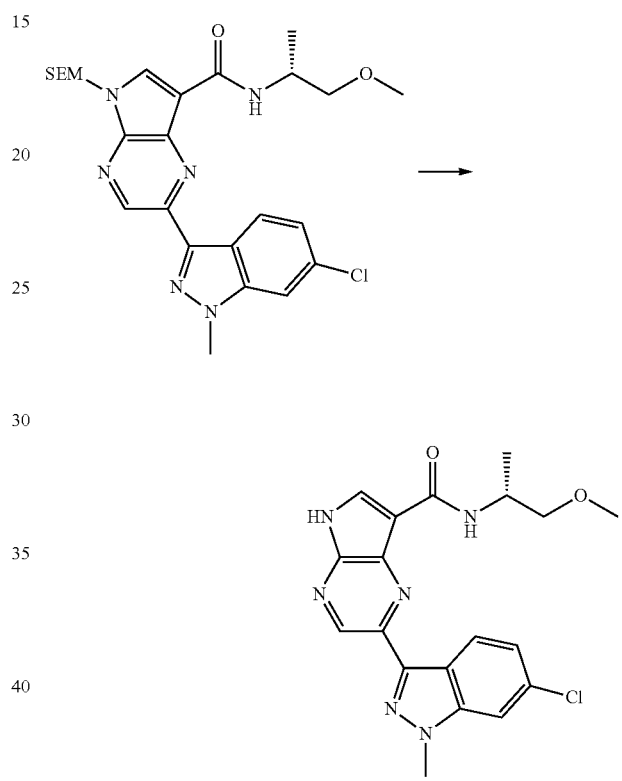

In a sealed 25 mL round-bottom flask, 2-(6-chloro-1-methyl-1H-indazol-3-yl)-5-(2-trimethylsilanyl-ethoxymethyl)-5H-pyrrolo[2,3-b]pyrazine-7-carboxylic acid ((R)-2-methoxy-1-methyl-ethyl)-amide (32 mg, 0.061 mmol) and TFA (0.9 ml, 11.7 mmol) were combined with dichloromethane (3 ml) to give an orange solution. The reaction mixture was stirred at room temperature until the consumption of starting material (2.5 h). The reaction mixture was then concentrated under reduced pressure. The resultant crude solid was dissolved in dichloromethane (3 mL) and ethylenediamine (300 µl, 4.44 mmol) was added. The reaction mixture was stirred at room temperature for 18 h. The reaction mixture was concentrated and the residue was precipitated with water. The suspension was stirred for 1 h and the crude solid collected by filtration. The crude solid was purified by trituration (1:1 dichloromethane/heptane) to afford 14 mg (59%) of 2-(6-chloro-1-methyl-1H-indazol-3-yl)-5H-pyrrolo[2,3-b]pyrazine-7-carboxylic acid ((R)-2-methoxy-1-methyl-ethyl)-amide as an off-white solid. MS: [M+H]$^+$=399; $^1$H NMR (300 MHz, DMSO-d$_6$) δ: 9.11 (s, 1H), 8.53 (d, J=8.6 Hz, 1H), 8.44 (s, 1H), 8.20 (d, J=8.6 Hz, 1H), 8.01 (d, J=1.5 Hz, 1H), 7.28 (dd, J=8.6, 2.0 Hz, 1H), 4.30-4.46 (m, 1H), 4.18 (s, 3H), 3.53 (dd, J=9.6, 5.1 Hz, 1H), 3.47 (dd, J=9.6, 4.5 Hz, 1H), 3.27 (s, 3H), 1.31 (d, J=6.6 Hz, 3H).

Example 160

2-(6-Chloro-1-methyl-1H-indazol-3-yl)-5H-pyrrolo[2,3-b]pyrazine-7-carboxylic acid (2,2,2-trifluoro-1-methyl-ethyl)-amide

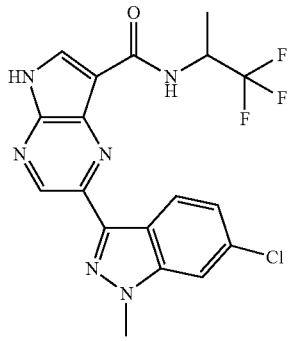 [SMILES: CC(NC(=O)c1c[nH]c2ncc(-c3nn(C)c4cc(Cl)ccc34)nc12)C(F)(F)F]

Prepared according to the procedure outlined in Example 145, substituting 1,1,1-trifluoropropan-2-amine for cis-cyclohexane-1,4,diamine in Step 1. The final compound was isolated as a light yellow solid, 25 mg (68%); MS: [M+H]$^+$= 423; $^1$H NMR (300 MHz, DMSO-d$_6$) δ: 12.76 (br. s., 1H), 9.13 (s, 1H), 8.57 (s, 1H), 8.42 (d, J=8.7 Hz, 1H), 8.43 (d, J=9.4 Hz, 1H), 8.02 (d, J=1.5 Hz, 1H), 7.26 (dd, J=8.7, 1.9 Hz, 1H), 4.96-5.15 (m, 1H), 4.18 (s, 3H), 1.49 (d, J=7.2 Hz, 3H).

Example 161

2-(6-Chloro-1-methyl-1H-indazol-3-yl)-5H-pyrrolo[2,3-b]pyrazine-7-carboxylic acid ((R)-1-hydroxymethyl-propyl)-amide

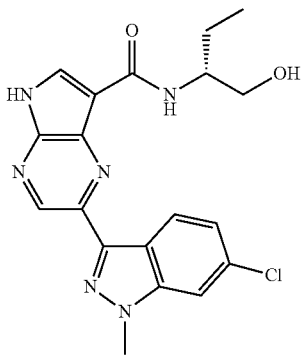 [SMILES: CC[C@H](CO)NC(=O)c1c[nH]c2ncc(-c3nn(C)c4cc(Cl)ccc34)nc12]

Step 1

2-(6-Chloro-1-methyl-1H-indazol-3-yl)-5-(2-trimethylsilanyl-ethoxymethyl)-5H-pyrrolo[2,3-b]pyrazine-7-carboxylic acid ((R)-1-hydroxymethyl-propyl)-amide A 25 mL round-bottomed flask was charged with 2-(6-chloro-1-methyl-1H-indazol-3-yl)-5-(2-trimethylsilanyl-ethoxymethyl)-5H-pyrrolo[2,3-b]pyrazine-7-carboxylic acid (0.10 g, 0.22 mmol), (R)-2-aminobutan-1-ol (65 mg, 0.73 mmol), HBTU (108 mg, 0.28 mmol), and HOBT (44 mg, 0.28 mmol). Then added DMF (1 mL) followed by N,N-diisopropylethylamine (0.11 mL, 0.66 mmol). The yellow reaction mixture was stirred at room temperature overnight then quenched with water and extracted with EtOAc (30 mL). The organic layer was washed once with saturated NaHCO$_3$ and water. The combined aqueous layers were back extracted with EtOAc (25 mL). The combined organic layers was dried over sodium sulfate, filtered and concentrated. The residue was purified by chromatography over SiO$_2$ with EtOAc/hexanes (gradient: 0-50% EtOAc) to afford 70 mg (61%) of 2-(6-chloro-1-methyl-1H-indazol-3-yl)-5-(2-trimethylsilanyl-ethoxymethyl)-5H-pyrrolo[2,3-b]pyrazine-7-carboxylic acid ((R)-1-hydroxymethyl-propyl)-amide as an off-white solid.

Step 2

2-(6-Chloro-1-methyl-1H-indazol-3-yl)-5H-pyrrolo [2,3-b]pyrazine-7-carboxylic acid ((R)-1-hydroxymethyl-propyl)-amide

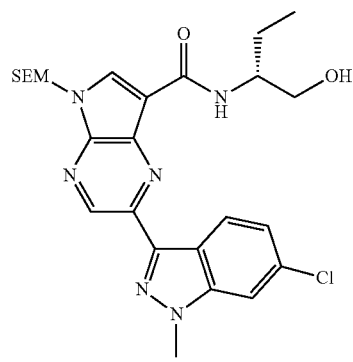

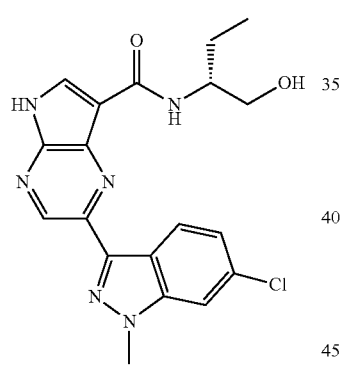

In a sealed 25 mL round-bottom flask, 2-(6-chloro-1-methyl-1H-indazol-3-yl)-5-(2-trimethylsilanyl-ethoxymethyl)-5H-pyrrolo[2,3-b]pyrazine-7-carboxylic acid ((R)-1-hydroxymethyl-propyl)-amide (34 mg, 0.064 mmol) and TFA (0.6 ml, 7.8 mmol) were combined with dichloromethane (2 ml) to give an orange solution. The reaction mixture was stirred at room temperature for 2.5 h. The reaction mixture was then concentrated under reduced pressure. The resultant crude solid was dissolved in dichloromethane (2 mL) and ethylenediamine (420 µl, 6.3 mmol) was added. The reaction mixture was stirred at room temperature for 18 h. The reaction mixture was concentrated and the residue was precipitated with water. The suspension was stirred for 1 h and the crude solid collected by filtration. The crude solid was purified by trituration (1:1 dichloromethane/heptane) to afford 8 mg (30%) of 2-(6-chloro-1-methyl-1H-indazol-3-yl)-5H-pyrrolo[2,3-b]pyrazine-7-carboxylic acid ((R)-1-hydroxymethyl-propyl)-amide as a yellow solid. MS: [M+H]$^+$=399; $^1$H NMR (DMSO-d$_6$) δ: 12.74 (br. s., 1H), 9.13 (s, 1H), 8.64 (d, J=8.7 Hz, 1H), 8.43 (s, 1H), 8.18 (d, J=9.1 Hz, 1H), 7.98 (d, J=1.1 Hz, 1H), 7.20-7.38 (m, 1H), 5.04 (t, J=5.1 Hz, 1H), 4.17 (s, 3H), 3.98-4.13 (m, 1H), 3.50-3.70 (m, 2H), 1.55-1.85 (m, 2H), 0.94 (t, J=7.4 Hz, 3H).

Example 162

2-(6-Chloro-1-methyl-1H-indazol-3-yl)-5H-pyrrolo [2,3-b]pyrazine-7-carboxylic acid ((R)-1-methoxymethyl-propyl)-amide

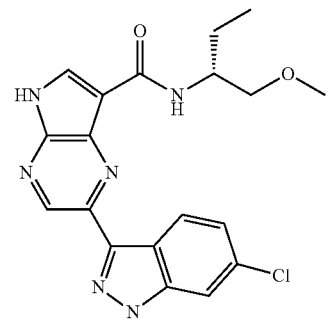

Step 1

2-(6-Chloro-1-methyl-1H-indazol-3-yl)-5-(2-trimethylsilanyl-ethoxymethyl)-5H-pyrrolo[2,3-b]pyrazine-7-carboxylic acid ((R)-1-methoxymethyl-propyl)-amide

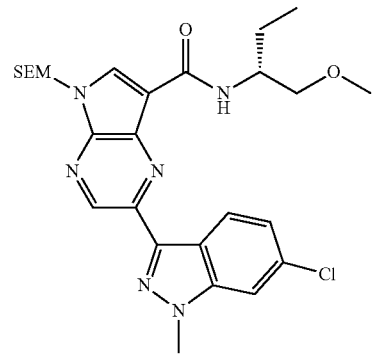

In a 25 mL reaction tube, NaH (60% in mineral oil, 20 mg, 0.50 mmol) was combined with DMF (0.2 ml) to give a grey suspension. The reaction was placed under argon and a solution of 2-(6-chloro-1-methyl-1H-indazol-3-yl)-5-(2-trimethylsilanyl-ethoxymethyl)-5H-pyrrolo[2,3-b]pyrazine-7-carboxylic acid ((R)-1-hydroxymethyl-propyl)-amide (161 mg, 0.30 mmol) in DMF (1 ml) was added. The reaction mixture was stirred at room temperature for 30 min then iodomethane (23 µl, 0.37 mmol) was added. The reaction was allowed to stir for 18 h then quenched with an aqueous solution of ammonium chloride (5 mL) and extracted with EtOAc (3×10 mL). The combined organic layers were washed with brine, dried over $Na_2SO_4$ and concentrated. The crude material was purified by chromatography over $SiO_2$ with EtOAc/hexanes (gradient: 0% to 40% EtOAc) to afford 25 mg (15%) of 2-(6-chloro-1-methyl-1H-indazol-3-yl)-5-(2-trimethylsilanyl-ethoxymethyl)-5H-pyrrolo[2,3b]pyrazine-7-carboxylic acid ((R)-1-methoxymethyl-propyl)-amide as an off-white solid. $^1$H NMR (DMSO-$d_6$) δ: 9.18 (s, 1H), 8.65 (s, 1H), 8.50 (d, J=8.7 Hz, 1H), 8.15 (d, J=9.4 Hz, 1H), 8.02 (d, J=1.5 Hz, 1H), 7.26 (dd, J=8.5, 1.7 Hz, 1H), 5.74 (s, 2H), 4.19 (s, 3H), 4.14-4.30 (m, 1H), 3.60 (t, J=7.9 Hz, 2H), 3.54-3.63 (m, 1H), 3.49 (dd, J=9.4, 4.2 Hz, 1H), 3.27 (s, 3H), 1.78 (dq, J=13.6, 6.9 Hz, 1H), 1.66 (dq, J=14.5, 7.0 Hz, 1H), 0.96 (t, J=7.4 Hz, 3H), 0.86 (t, J=7.9 Hz, 2H), −0.08 (s, 9H).

Step 2

2-(6-Chloro-1-methyl-1H-indazol-3-yl)-5H-pyrrolo[2,3-b]pyrazine-7-carboxylic acid ((R)-1-methoxymethyl-propyl)-amide

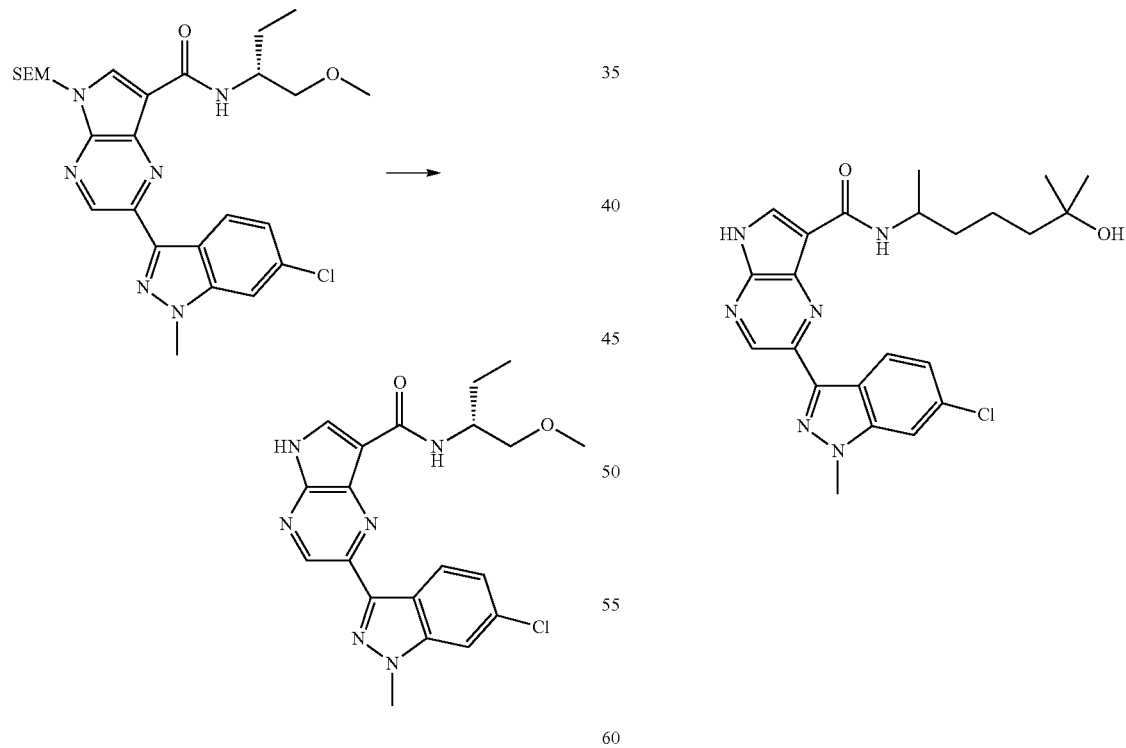

In a sealed 25 mL round-bottom flask, 2-(6-chloro-1-methyl-1H-indazol-3-yl)-5-(2-trimethylsilanyl-ethoxymethyl)-5H-pyrrolo[2,3-b]pyrazine-7-carboxylic acid ((R)-1-methoxymethyl-propyl)-amide (40 mg, 0.074 mmol) and TFA (0.9 ml, 11.7 mmol) were combined with dichloromethane (3 ml) to give an orange solution. The reaction mixture was stirred at room temperature for 2.5 h. The reaction mixture was then concentrated under reduced pressure. The resultant crude solid was dissolved in dichloromethane (3 mL) and ethylenediamine (500 µl, 7.4 mmol) was added. The reaction mixture was stirred at room temperature for 18 h. The reaction mixture was concentrated and the residue was precipitated with water. The suspension was stirred for 1 h and the crude solid collected by filtration. The crude solid was purified by trituration (11:1:1 hot heptane/dichloromethane/EtOAc) to afford 21 mg (69%) of 2-(6-chloro-1-methyl-1H-indazol-3-yl)-5H-pyrrolo[2,3-b]pyrazine-7-carboxylic acid ((R)-1-methoxymethyl-propyl)-amide as an off-white solid. MS: [M+H]$^+$=413; $^1$H NMR (DMSO-$d_6$) δ: 12.84 (br. s., 1H), 9.12 (s, 1H), 8.51 (d, J=8.7 Hz, 1H), 8.45 (s, 1H), 8.17 (d, J=9.1 Hz, 1H), 8.01 (d, J=1.5 Hz, 1H), 7.25 (dd, J=8.7, 1.5 Hz, 1H), 4.16-4.27 (m, 1H), 4.18 (s, 3H), 3.57 (dd, J=9.6, 4.3 Hz, 1H), 3.47 (dd, J=9.6, 4.3 Hz, 1H), 3.27 (s, 3H), 1.71-1.89 (m, 1H), 1.47-1.71 (m, 1H), 0.96 (t, J=7.4 Hz, 3H).

Example 163

2-(6-Chloro-1-methyl-1H-indazol-3-yl)-5H-pyrrolo[2,3-b]pyrazine-7-carboxylic acid (5-hydroxy-1,5-dimethyl-hexyl)-amide Prepared according to the procedure outlined in Example 145, substituting 6-amino-2-methylheptan-2-ol hydrochloride for cis-cyclohexane-1,4,diamine in Step 1. The final compound was isolated as a white solid, 23 mg (35%); [M+Na]$^+$=477; $^1$H NMR (DMSO-$d_6$) δ: 12.84 (br. s., 1H), 9.10 (s, 1H), 8.34-8.48 (m, 2H), 8.02 (t, J=4.2 Hz, 2H), 7.31

(dd, J=8.5, 1.3 Hz, 1H), 4.18 (s, 3H), 4.07-4.16 (m, 1H), 1.32-1.70 (m, 6H), 1.29 (d, J=6.8 Hz, 3H), 0.96 (d, J=2.3 Hz, 6H).

Example 164

2-(6-Chloro-1-methyl-1H-indazol-3-yl)-5H-pyrrolo[2,3-b]pyrazine-7-carboxylic acid ((S)-2-hydroxy-1-methyl-ethyl)-amide

Step 1

2-(6-Chloro-1-methyl-1H-indazol-3-yl)-5-(2-trimethylsilanyl-ethoxymethyl)-5H-pyrrolo[2,3-b]pyrazine-7-carboxylic acid ((S)-2-hydroxy-1-methyl-ethyl)-amide

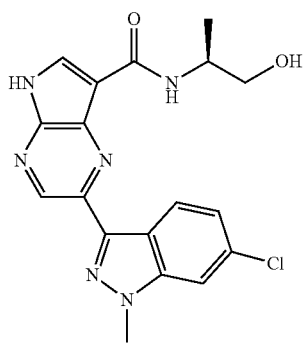 [SMILES: C[C@@H](CO)NC(=O)c1c[nH]c2ncc(-c3nn(C)c4cc(Cl)ccc34)nc12]

+

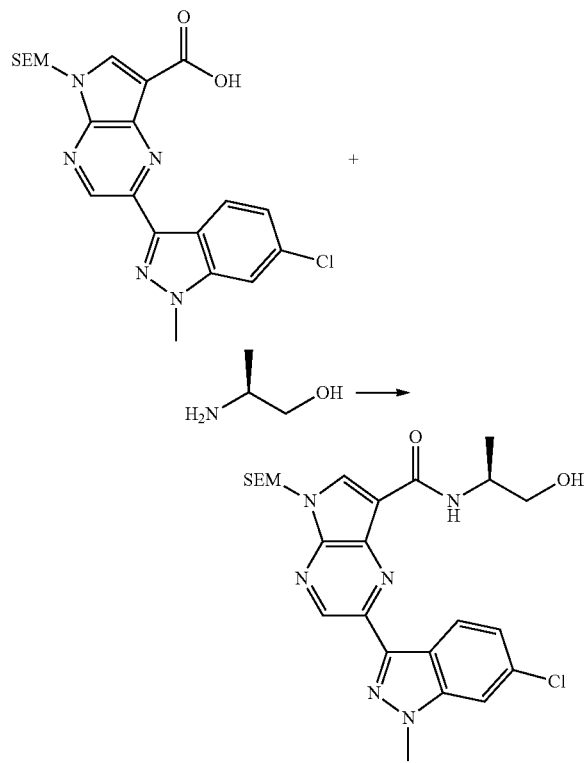

A 25 mL round-bottomed flask was charged with 2-(6-chloro-1-methyl-1H-indazol-3-yl)-5-(2-trimethylsilanyl-ethoxymethyl)-5H-pyrrolo[2,3-b]pyrazine-7-carboxylic acid (0.20 g, 0.44 mmol), (S)-2-aminopropan-1-ol (0.10 ml, 1.31 mmol), HBTU (331 mg, 0.87 mmol), and HOBT (134 mg, 0.87 mmol). Then added DMF (1 mL) followed by N,N-diisopropylethylamine (0.31 mL, 1.75 mmol). The yellow reaction mixture was stirred at room temperature overnight then quenched with water and extracted with EtOAc (30 mL). The organic layer was washed once with saturated NaHCO₃ and water. The combined aqueous layers were back extracted with EtOAc (25 mL). The combined organic layers was dried over sodium sulfate, filtered and concentrated. The residue was purified by chromatography over SiO₂ with EtOAc/hexanes (gradient: 0-100% EtOAc) to afford 149 mg (66%) of 2-(6-chloro-1-methyl-1H-indazol-3-yl)-5-(2-trimethylsilanyl-ethoxymethyl)-5H-pyrrolo[2,3-b]pyrazine-7-carboxylic acid ((S)-2-hydroxy-1-methyl-ethyl)-amide as a white solid.

Step 2

2-(6-Chloro-1-methyl-1H-indazol-3-yl)-5H-pyrrolo[2,3-b]pyrazine-7-carboxylic acid ((S)-2-hydroxy-1-methyl-ethyl)-amide

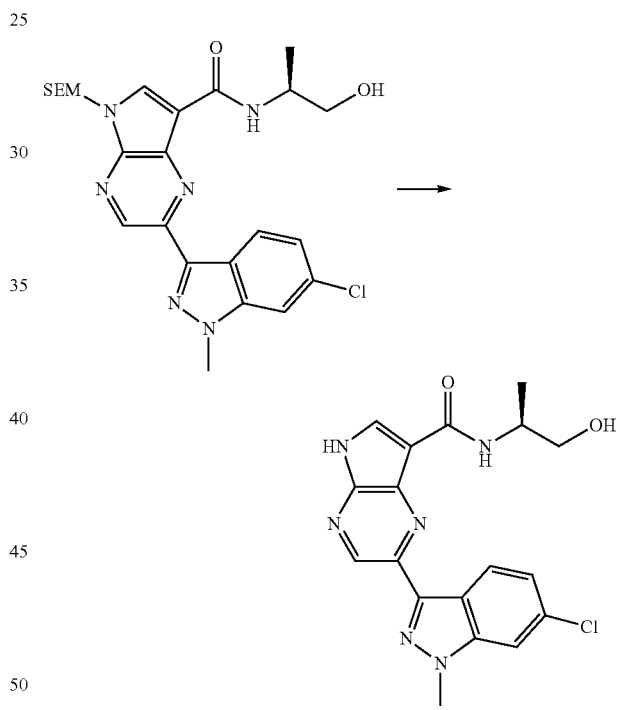

In a sealed 25 mL round-bottom flask, 2-(6-chloro-1-methyl-1H-indazol-3-yl)-5-(2-trimethylsilanyl-ethoxymethyl)-5H-pyrrolo[2,3-b]pyrazine-7-carboxylic acid ((S)-2-hydroxy-1-methyl-ethyl)-amide (41 mg, 0.080 mmol) and TFA (0.6 ml, 7.8 mmol) were combined with dichloromethane (2 ml) to give an orange solution. The reaction mixture was stirred at room temperature until the consumption of starting material (2.5 h). The reaction mixture was then concentrated under reduced pressure. The resultant crude solid was dissolved in dichloromethane (2 mL) and ethylenediamine (400 µl, 5.9 mmol) was added. The reaction mixture was stirred at room temperature for 18 h. The reaction mixture was concentrated and the residue was precipitated with water. The suspension was stirred for 1 h and the crude solid collected by filtration. The crude solid was purified by trituration (9:1 dichloromethane/MeOH) to afford 11 mg (36%) of 2-(6-chloro-1-methyl-1H-indazol-3-yl)-5H-pyrrolo[2,3-b]pyrazine-7-carboxylic acid ((S)-2-hydroxy-1-methyl-ethyl)-amide as an off-white solid. MS: [M+H]$^+$=385; $^1$H NMR (300 MHz, DMSO-d$_6$) δ: 12.84 (br. s., 1H), 9.13 (s, 1H), 8.66 (d, J=8.7 Hz, 1H), 8.43 (s, 1H), 8.21 (d, J=8.3 Hz, 1H), 7.91-8.04 (m, 1H), 7.32 (dd, J=8.7, 1.5 Hz, 1H), 5.09 (t, J=5.1 Hz, 1H), 4.18 (s, 3H), 4.08-4.33 (m, 1H), 3.58 (t, J=4.7 Hz, 2H), 1.28 (d, J=6.8 Hz, 3H).

Example 165

2-(6-Chloro-1-methyl-1H-indazol-3-yl)-5H-pyrrolo[2,3-b]pyrazine-7-carboxylic acid ((S)-2-methoxy-1-methyl-ethyl)-amide

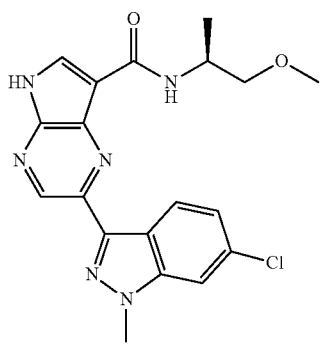

-continued

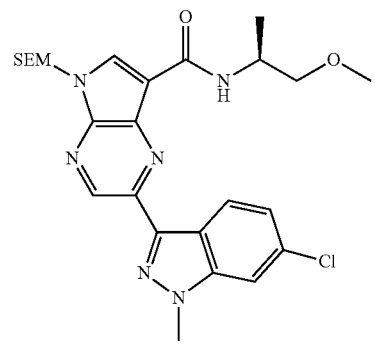

In a 10 mL round-bottomed flask, 2-(6-chloro-1-methyl-1H-indazol-3-yl)-5-(2-trimethylsilanyl-ethoxymethyl)-5H-pyrrolo[2,3-b]pyrazine-7-carboxylic acid ((S)-2-hydroxy-1-methyl-ethyl)-amide (44 mg, 0.085 mmol) was dissolved in THF (0.85 ml) to give a colorless solution. The reaction was cooled in an ice bath. Crushed KOH (64 mg, 1.14 mmol), catalytic 18-crown-6, and iodomethane (9 μl, 0.147 mmol) were added successively to the cooled solution. The reaction mixture was stirred at 0° C. for 1 h after which the ice bath was removed. The reaction mixture was stirred at room temperature for 2 h then diluted with dichloromethane (10 mL) and washed with aqueous ammonium chloride (10 mL), water (10 mL), and saturated sodium bicarbonate (10 mL). The organic layer was dried over Na$_2$SO$_4$ and concentrated. The crude material was purified by chromatography over SiO$_2$ with EtOAc/heptane (gradient: 0%-100% EtOAc) to afford 22 mg (49%) of 2-(6-chloro-1-methyl-1H-indazol-3-yl)-5-(2-trimethylsilanyl-ethoxymethyl)-5H-pyrrolo[2,3-b]pyrazine-7-carboxylic acid ((S)-2-methoxy-1-methyl-ethyl)-amide as a white solid. MS: [M+Na]$^+$=551.

Step 1

2-(6-Chloro-1-methyl-1H-indazol-3-yl)-5-(2-trimethylsilanyl-ethoxymethyl)-5H-pyrrolo[2,3-b]pyrazine-7-carboxylic acid ((S)-2-methoxy-1-methyl-ethyl)-amide Step 2

2-(6-Chloro-1-methyl-1H-indazol-3-yl)-5H-pyrrolo[2,3-b]pyrazine-7-carboxylic acid ((S)-2-methoxy-1-methyl-ethyl)-amide

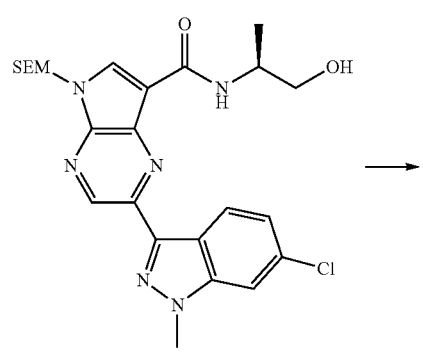

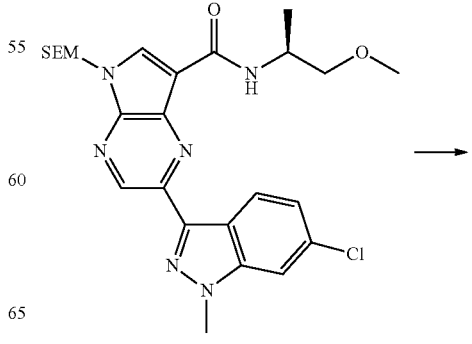

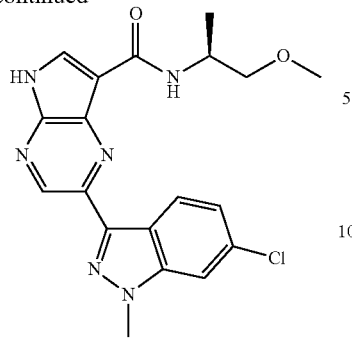

In a sealed 25 mL round-bottom flask, 2-(6-chloro-1-methyl-1H-indazol-3-yl)-5-(2-trimethylsilanyl-ethoxymethyl)-5H-pyrrolo[2,3-b]pyrazine-7-carboxylic acid ((S)-2-methoxy-1-methyl-ethyl)-amide (32 mg, 0.061 mmol) and TFA (1.2 ml, 15.6 mmol) were combined with dichloromethane (4 ml) to give an orange solution. The reaction mixture was stirred at room temperature until the consumption of starting material (2.5 h). The reaction mixture was then concentrated under reduced pressure. The resultant crude solid was dissolved in dichloromethane (2 mL) and ethylenediamine (300 µl, 4.5 mmol) was added. The reaction mixture was stirred at room temperature for 18 h. The reaction mixture was concentrated and the residue was precipitated with water. The suspension was stirred for 1 h and the crude solid collected by filtration. The crude solid was purified by trituration (9:1 dichloromethane/heptane) to afford 22 mg (93%) of 2-(6-chloro-1-methyl-1H-indazol-3-yl)-5H-pyrrolo[2,3-b]pyrazine-7-carboxylic acid ((S)-2-methoxy-1-methyl-ethyl)-amide as an off-white solid. MS: [M+H]$^+$=399; $^1$H NMR (DMSO-d$_6$) δ: 12.72 (br. s., 1H), 9.11 (s, 1H), 8.53 (d, J=8.7 Hz, 1H), 8.44 (s, 1H), 8.20 (d, J=8.7 Hz, 1H), 8.01 (d, J=1.9 Hz, 1H), 7.28 (dd, J=8.7, 1.9 Hz, 1H), 4.30-4.45 (m, 1H), 4.18 (s, 3H), 3.50 (qd, J=9.6, 4.7 Hz, 2H), 3.27 (s, 3H), 1.31 (d, J=6.8 Hz, 3H).

Example 166

2-(6-Chloro-1-methyl-1H-indazol-3-yl)-5H-pyrrolo[2,3-b]pyrazine-7-carboxylic acid (2-methoxy-1-methoxymethyl-ethyl)-amide

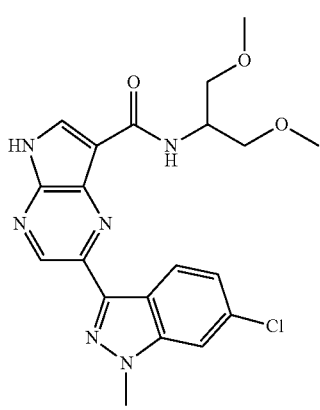 [SMILES: COCC(COC)NC(=O)c1c[nH]c2ncc(-c3nn(C)c4cc(Cl)ccc34)nc12]

Step 1

2-(6-Chloro-1-methyl-1H-indazol-3-yl)-5-(2-trimethylsilanyl-ethoxymethyl)-5H-pyrrolo[2,3-b]pyrazine-7-carboxylic acid (2-hydroxy-1-hydroxymethyl-ethyl)-amide

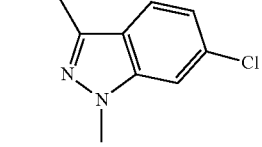

+

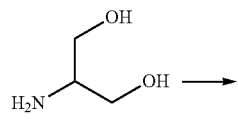

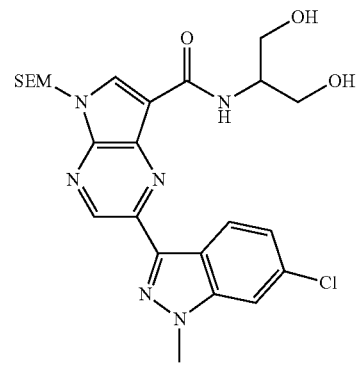

A 25 mL round-bottomed flask was charged with 2-(6-chloro-1-methyl-1H-indazol-3-yl)-5-(2-trimethylsilanyl-ethoxymethyl)-5H-pyrrolo[2,3-b]pyrazine-7-carboxylic acid (0.20 g, 0.44 mmol), 2-aminopropane-1,3-diol (119 mg, 1.31 mmol), HBTU (331 mg, 0.87 mmol), and HOBT (134 mg, 0.87 mmol). Then added DMF (1 mL) followed by N,N-diisopropylethylamine (0.31 mL, 1.75 mmol). The yellow reaction mixture was stirred at room temperature overnight then quenched with water and extracted with EtOAc (30 mL). The organic layer was washed once with saturated NaHCO$_3$ and water. The combined aqueous layers were back extracted with EtOAc (25 mL). The combined organic layers was dried over sodium sulfate, filtered and concentrated. The residue was purified by chromatography over SiO$_2$ with EtOAc/hexanes (gradient: 0-100% EtOAc) to afford 157 mg (68%) of 2-(6-chloro-1-methyl-1H-indazol-3-yl)-5-(2-trimethylsilanyl-ethoxymethyl)-5H-pyrrolo[2,3-b]pyrazine-7-carboxylic acid (2-hydroxy-1-hydroxymethyl-ethyl)-amide as a white solid. MS: [M+Na]+=552.

Step 2

2-(6-Chloro-1-methyl-1H-indazol-3-yl)-5-(2-trimethylsilanyl-ethoxymethyl)-5H-pyrrolo[2,3-b]pyrazine-7-carboxylic acid (2-methoxy-1-methoxymethyl-ethyl)-amide

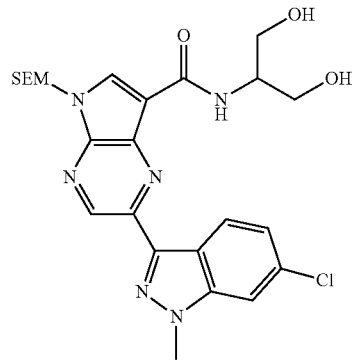

In a 10 mL round-bottomed flask, 2-(6-chloro-1-methyl-1H-indazol-3-yl)-5-(2-trimethylsilanyl-ethoxymethyl)-5H-pyrrolo[2,3-b]pyrazine-7-carboxylic acid (2-hydroxy-1-hydroxymethyl-ethyl)-amide (60 mg, 0.113 mmol) was dissolved in THF (2.5 ml). The reaction was cooled in an ice bath and crushed KOH (76 mg, 1.35 mmol), 18-crown-6 (15 mg, 0.057 mmol), and iodomethane (18 µl, 0.28 mmol) were added successively. The reaction mixture was stirred at 0° C. for 1 h after which the ice bath was removed. The reaction mixture was stirred at room temperature for 2 h then diluted with dichloromethane (10 mL) and washed with water (10 mL) and saturated sodium bicarbonate (10 mL). The organic layer was dried over Na$_2$SO$_4$ and concentrated. The crude material was purified by chromatography over SiO$_2$ with EtOAc/heptane (gradient: 0%-100% EtOAc) to afford 53 mg (84%) of 2-(6-chloro-1-methyl-1H-indazol-3-yl)-5-(2-trimethylsilanyl-ethoxymethyl)-5H-pyrrolo[2,3-b]pyrazine-7-carboxylic acid (2-methoxy-1-methoxymethyl-ethyl)-amide as a white solid. MS: [M+H]+=559.

Step 3

2-(6-Chloro-1-methyl-1H-indazol-3-yl)-5H-pyrrolo[2,3-b]pyrazine-7-carboxylic acid (2-methoxy-1-methoxymethyl-ethyl)-amide

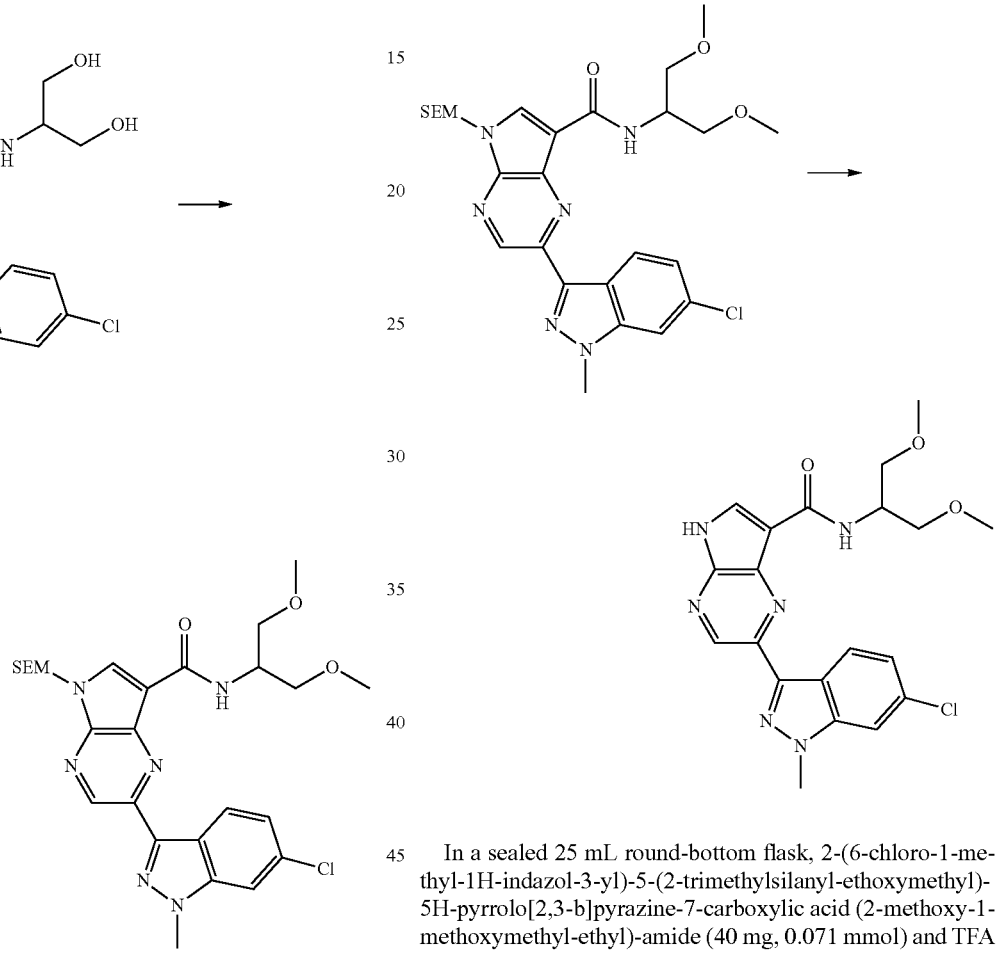

In a sealed 25 mL round-bottom flask, 2-(6-chloro-1-methyl-1H-indazol-3-yl)-5-(2-trimethylsilanyl-ethoxymethyl)-5H-pyrrolo[2,3-b]pyrazine-7-carboxylic acid (2-methoxy-1-methoxymethyl-ethyl)-amide (40 mg, 0.071 mmol) and TFA (0.6 ml, 7.8 mmol) were combined with dichloromethane (2 ml) to give an orange solution. The reaction mixture was stirred at room temperature until the consumption of starting material (2.5 h). The reaction mixture was then concentrated under reduced pressure. The resultant crude solid was dissolved in dichloromethane (2 mL) and ethylenediamine (400 µl, 5.9 mmol) was added. The reaction mixture was stirred at room temperature for 18 h. The reaction mixture was concentrated and the residue was precipitated with water. The suspension was stirred for 1 h and the crude solid collected by filtration. The crude solid was purified by trituration (hexanes/dichloromethane/EtOAc) to afford 19 mg (62%) of 2-(6-chloro-1-methyl-1H-indazol-3-yl)-5H-pyrrolo[2,3-b]pyrazine-7-carboxylic acid (2-methoxy-1-methoxymethyl-ethyl)-amide as an off-white solid. MS: [M+H]+=429; $^1$H NMR (300 MHz, DMSO-d$_6$) δ: 12.88 (br. s., 1H), 9.13 (s, 1H), 8.55 (d, J=8.7 Hz, 1H), 8.46 (s, 1H), 8.30 (d, J=9.1 Hz, 1H), 8.01 (s, 1H), 7.25 (dd, J=8.7, 1.1 Hz, 1H), 4.33-4.67 (m, 1H), 4.18 (s, 3H), 3.61 (dd, J=9.8, 5.3 Hz, 2H), 3.56 (dd, J=9.4, 5.3 Hz, 1H), 3.27 (s, 3H).

Example 167

2-(6-Chloro-1-methyl-1H-indazol-3-yl)-5H-pyrrolo[2,3-b]pyrazine-7-carboxylic acid (cis-3-cyano-cyclohexyl)-amide

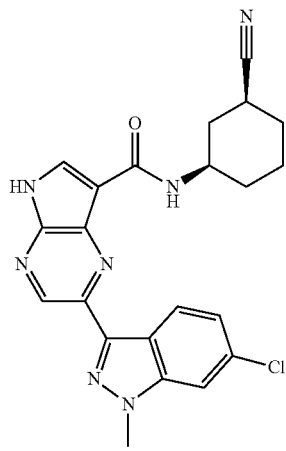 [SMILES: Cn1nc(-c2cnc3[nH]cc(C(=O)N[C@@H]4CCC[C@H](C#N)C4)c3n2)c2ccc(Cl)cc21]

Step 1

(cis-3-Carbamoyl-cyclohexyl)-carbamic acid tert-butyl ester

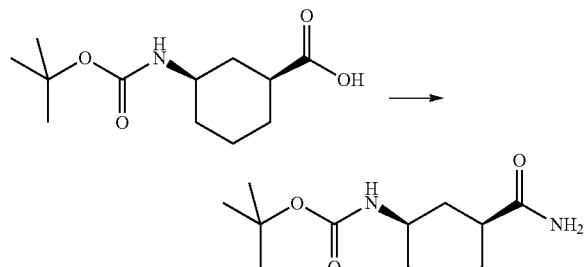

In a 100 mL round bottomed flask cis-3-(tertbutoxycarbonylamino)-cyclohexanecarboxylic acid (2.26 g, 9.29 mmol) was suspended in THF (15 mL). The suspension was cooled to −10° C. in an acetone-dry ice bath. To the cooled suspension was added slowly TEA (2.6 mL, 18.7 mmol) and subsequently ethyl chloroformate (1.03 mL, 10.7 mmol) so that the temperature is maintained. The cooling bath was removed upon addition and the reaction was stirred at room temperature for 3 h. The reaction mixture was cooled to −10° C. and NH₄OH (2.17 mL, 55.7 mmol) was added slowly. After stirring at room temperature for 18 h, the precipitate was collected by filtration. The precipitate was washed with water and dried in vacuo at 50° C. to afford 1.67 g (74%) of (cis-3-carbamoyl-cyclohexyl)-carbamic acid tert-butyl ester as a white solid. ¹H NMR (300 MHz, DMSO-d₆) δ: 7.19 (br. s., 1H), 6.76 (d, J=7.9 Hz, 1H), 6.65 (br. s., 1H), 3.04-3.30 (m, 1H), 1.98-2.21 (m, 1H), 1.50-1.84 (m, 4H), 1.37 (s, 9H), 0.90-1.29 (m, 4H)

Step 2 cis-(3-Cyano-cyclohexyl)-carbamic acid tert-butyl ester

In a 25 mL round bottomed flask (cis-3-carbamoyl-cyclohexyl)-carbamic acid tert-butyl ester (1.00 g, 4.13 mmol) was suspended in dichlormethane (7 mL). The suspension was cooled to −10° C. in an acetone-dry ice bath. To the cooled suspension was added slowly triethylamine (1.15 mL, 8.25 mmol) and subsequently TFAA (0.62 mL, 4.39 mmol) so that the temperature is maintained. The reaction mixture was stirred at that temperature for 3 h and then diluted with water and dichloromethane. The organic layer was washed with water, dried over Na₂SO₄ and concentrated in vacuo. The crude material was purified by flash chromatography (silica gel, 0% to 60% EtOAc in heptane) to afford 0.803 g (87%) of cis-(3-cyano-cyclohexyl)-carbamic acid tert-butyl ester as a white crystalline solid. ¹H NMR (300 MHz, DMSO-d₆) δ: 6.86 (d, J=7.9 Hz, 1H), 3.09-3.30 (m, 1H), 2.77 (tt, J=12.0, 3.3 Hz, 1H), 2.04 (d, J=12.1 Hz, 1H), 1.90 (d, J=9.1 Hz, 1H), 1.61-1.80 (m, 2H), 1.37 (s, 9H), 1.21-1.35 (m, 3H), 0.98-1.20 (m, 1H).

Step 3 cis-3-Amino-cyclohexanecarbonitrile trifluoroacetate

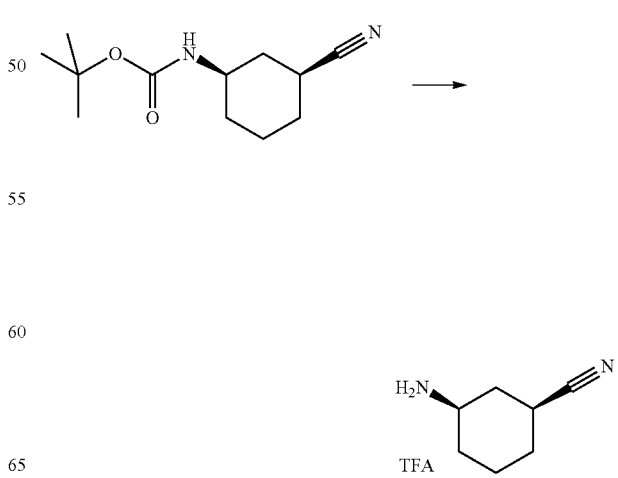

In a 25 mL round-bottomed flask, cis-(3-cyano-cyclohexyl)-carbamic acid tert-butyl ester (212 mg, 0.945 mmol) was combined with dichloromethane (3 ml) to give a colorless solution. Trifluoroacetic acid (0.9 mL, 11.7 mmol) was added to give a yellow solution which was stirred at room temperature for 1.5 h. The reaction mixture was then concentrated under reduced pressure. The residue was azeotroped with toluene to afford 321 mg of cis-3-aminocyclohexanecarbonitrile trifluoroacetate as a crude solid that was taken to the next step without purification. $^1$H NMR (300 MHz, DMSO-$d_6$) δ: 7.96 (br. s., 3H), 2.93-3.14 (m, 1H), 2.87 (tt, J=12.2, 3.5 Hz, 1H), 2.22 (d, J=12.1 Hz, 1H), 1.96 (d, J=10.2 Hz, 1H), 1.87 (d, J=11.3 Hz, 1H), 1.68-1.81 (m, 1H), 1.49 (q, J=12.1 Hz, 1H), 1.18-1.41 (m, 3H).

Step 4

2-(6-Chloro-1-methyl-1H-indazol-3-yl)-5H-pyrrolo[2,3-b]pyrazine-7-carboxylic acid (cis-3-cyano-cyclohexyl)-amide

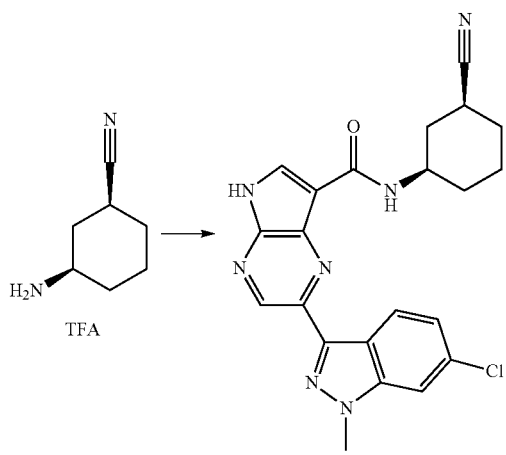 [SMILES: N#C[C@H]1CCC[C@@H](N)C1 ; Cn1nc(-c2cnc3[nH]cc(C(=O)N[C@@H]4CCC[C@H](C#N)C4)c3n2)c2ccc(Cl)cc21]

Prepared according to the procedure outlined in Example 2, substituting cis-3-aminocyclohexanecarbonitrile trifluoroacetate for cis-cyclohexane-1,4,diamine in Step 1. The final compound was isolated as an off-white solid, 37 mg (74%); MS: [M+H]$^+$=434; $^1$H NMR (DMSO-$d_6$) δ: 12.87 (br. s., 1H), 9.10 (s, 1H), 8.46 (s, 1H), 8.44 (d, J=8.7 Hz, 1H), 8.08 (d, J=7.6 Hz, 1H), 8.01 (d, J=1.5 Hz, 1H), 7.34 (dd, J=8.5, 1.7 Hz, 1H), 4.18 (s, 3H), 3.82-4.05 (m, 1H), 2.91-3.08 (m, 1H), 1.94-2.16 (m, 2H), 1.77-1.92 (m, J=7.2, 4.2 Hz, 1H), 1.29-1.73 (m, 5H).

Example 168

2-(6-Chloro-1-methyl-1H-indazol-3-yl)-5H-pyrrolo[2,3-b]pyrazine-7-carboxylic acid [(R)-1-(2,2,2-trifluoro-ethyl)-piperidin-3-yl]-amide hydrochloride

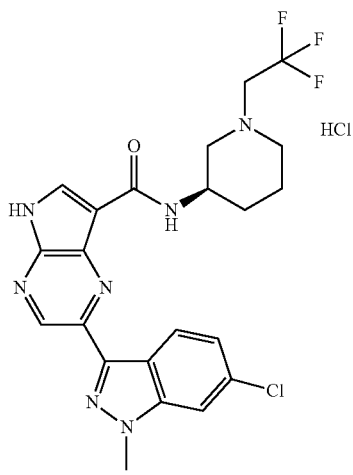 [SMILES: Cn1nc(-c2cnc3[nH]cc(C(=O)N[C@@H]4CCCN(CC(F)(F)F)C4)c3n2)c2ccc(Cl)cc21 ; Cl]

Step 1

[(R)-1-(2,2,2-Trifluoro-ethyl)-piperidin-3-yl]-carbamic acid tert-butyl ester

In a 25 mL round-bottomed flask, (R)-Piperidin-3-yl-carbamic acid tert-butyl ester (1.00 g, 4.99 mmol) and DIPEA (0.96 mL, 5.49 mmol) were combined with dichloromethane (20 ml). The reaction mixture was place under argon atmosphere and cooled in an ice bath. A solution of 1,1,1-trifluoro-2-(trifluoromethulsulfonyl)ethane (1.19 g, 5.49 mmol) was added dropwise. The reaction mixture was allow to warm to room temperature. After stirring for 18 h, the reaction mixture was diluted with dichlormethane and successively washed with water, saturated bicarbonate, and brine. The organic layer was dried over Na$_2$SO$_4$ and concentrated. The crude material was purified by flash chromatography (silica gel, 24 g, 0% to 70% EtOAc in heptane) to afford 1.20 g (85%) of [(R)-1-(2,2,2-trifluoro-ethyl)-piperidin-3-yl]-carbamic acid tert-butyl ester as a white crystalline solid. $^1$H NMR (300 MHz, CDCl$_3$) δ: 4.97 (br. s., 1H), 3.75 (br. s., 1H), 2.98 (q, J=9.4 Hz, 2H), 2.82 (app d, J=11.7 Hz, 1H), 2.64-2.76 (m, 1H), 2.46-2.64 (m, 2H), 1.66-1.81 (m, 1H), 1.60 (m., 3H), 1.45 (s, 9H).

Step 2

(R)-1-(2,2,2-trifluoroethyl)piperidin-3-amine dihydrochloride

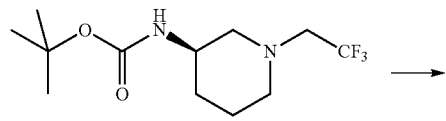

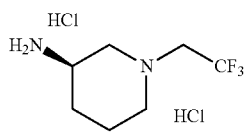

In a 250 mL round-bottomed flask, [(R)-1-(2,2,2-trifluoro-ethyl)-piperidin-3-yl]-carbamic acid tert-butyl ester (1.20 g, 4.25 mmol) was combined with MeOH (100 ml) to give a colorless suspension. The reaction mixture was place under a nitrogen atmosphere and cooled in an ice bath. Acetyl chloride (6.04 ml, 85.0 mmol) was added slowly. The reaction mixture was stirred at 5° C. for an additional 10 min then warmed to room temperature. After stirring at room temperature for 17 h, the reaction mixture was concentrated to dryness to afford 1.10 g (quantitative) of (R)-1-(2,2,2-trifluoroethyl)piperidin-3-amine dihydrochloride as a light yellow solid. $^1$H NMR (300 MHz, DMSO-d$_6$) δ: 8.27 (br. s., 3H), 3.39 (q, J=10.2 Hz, 2H), 3.15-3.27 (m, 1H), 3.10 (dd, J=11.3, 3.0 Hz, 1H), 2.83 (app d, J=11.7 Hz, 1H), 2.56 (d, J=10.2 Hz, 1H), 2.45 (d, J=9.8 Hz, 1H), 1.83-2.04 (m, 1H), 1.62-1.83 (m, 1H), 1.45-1.62 (m, 1H), 1.25-1.45 (m, 1H).

Step 3

2-(6-Chloro-1-methyl-1H-indazol-3-yl)-5H-pyrrolo[2,3-b]pyrazine-7-carboxylic acid [(R)-1-(2,2,2-trifluoro-ethyl)-piperidin-3-yl]-amide hydrochloride

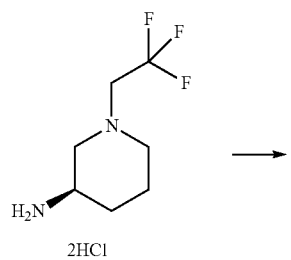

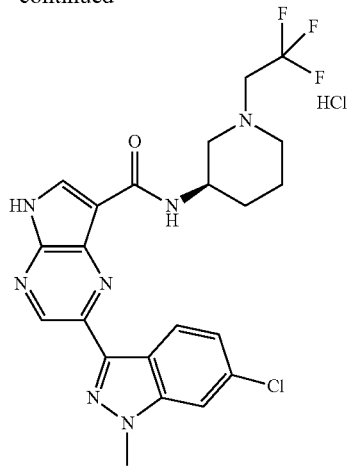

Prepared according to the procedure outlined in Example 2, substituting (R)-1-(2,2,2-trifluoroethyl)piperidin-3-amine dihydrochloride for cis-cyclohexane-1,4,diamine in Step 1. The final compound was treated with HCl (4.0 M in 1,4-dioxane) to isolate the salt as an orange solid, 32 mg (46%); MS: [M+H]$^+$=492; $^1$H NMR (300 MHz, DMSO-d$_6$) δ: 12.92 (d, J=2.6 Hz, 1H), 9.09 (s, 1H), 8.46 (d, J=3.0 Hz, 1H), 8.43 (d, J=8.7 Hz, 1H), 8.21 (br. s., 1H), 8.11 (d, J=8.3 Hz, 1H), 8.02 (s, 1H), 7.32 (dd, J=8.7, 1.1 Hz, 1H), 4.09-4.25 (m, 1H), 4.09-4.25 (m, 3H), 3.30-3.52 (m, 1H), 3.25 (br. d, J=9.8 Hz, 1H), 3.02-3.11 (m, 1H), 2.88-3.01 (m, 1H), 1.96-2.07 (m, 1H), 1.78-1.91 (m, 1H), 1.57-1.75 (m, 1H), 1.36-1.56 (m, 1H).

Example 169

2-(6-Chloro-1-methyl-1H-indazol-3-yl)-5H-pyrrolo[2,3-b]pyrazine-7-carboxylic acid (3-aminocyclohexyl)-amide hydrochloride

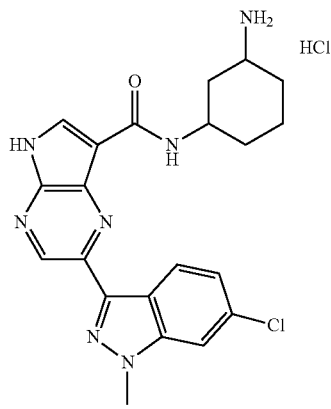 [SMILES: Cn1nc(-c2cnc3[nH]cc(C(=O)NC4CCCC(N)C4)c3n2)c2ccc(Cl)cc21 ; Cl]

Prepared according to the procedure outlined in Example 145, substituting cyclohexane-1,3-diamine for cis-cyclohexane-1,4,diamine in Step 1. The final compound was treated with HCl (4.0 M in 1,4-dioxane) to isolate the salt as a yellow solid (mixture of diastereomers), 34 mg (56%); MS: [M+H]$^+$= 424; $^1$H NMR (DMSO-d$_6$) δ: 12.92 (d, J=3.0 Hz, 1H), 9.12 (s, 1H), 8.48 (s, 1H), 8.42 (d, J=8.7 Hz, 1H), 8.11 (d, J=7.9 Hz, 1H), 8.03 (d, J=1.1 Hz, 1H), 7.46 (dd, J=8.7, 1.1 Hz, 1H), 4.18 (s, 3H), 3.96-4.12 (m, 1H), 3.19-3.30 (m, 1H), 1.18-2.14 (m, 8H).

Example 170

2-(6-Chloro-4-fluoro-1-methyl-1H-indazol-3-yl)-5H-pyrrolo[2,3-b]pyrazine-7-carboxylic acid ((S)-2-methoxy-1-methyl-ethyl)-amide

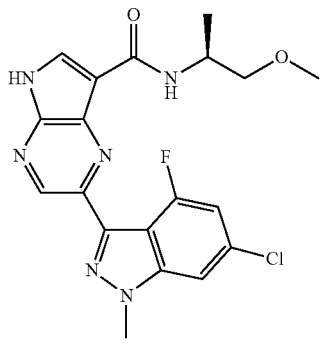 [SMILES: COC[C@H](C)NC(=O)c1c[nH]c2ncc(-c3nn(C)c4cc(Cl)cc(F)c34)nc12]

Step 1

2-(6-Chloro-4-fluoro-1H-indazol-3-yl)-5-(2-trimethylsilanyl-ethoxymethyl)-5H-pyrrolo[2,3-b]pyrazine-7-carboxylic acid ((S)-2-methoxy-1-methyl-ethyl)-amide

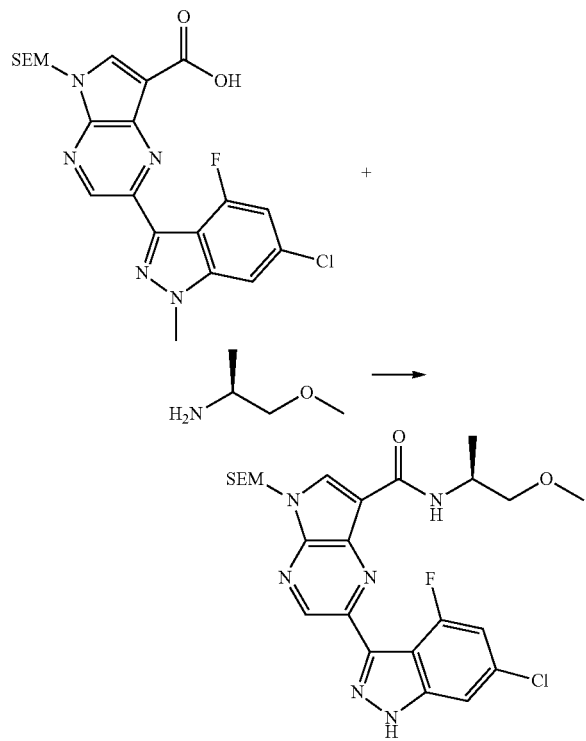

A 25 mL round-bottomed flask was charged with 2-(6-chloro-4-fluoro-1H-indazol-3-yl)-5-(2-trimethylsilanyl-ethoxymethyl)-5H-pyrrolo[2,3-b]pyrazine-7-carboxylic acid (0.39 g, 0.84 mmol), (S)-1-methoxypropan-2-amine hydrochloride (253 mg, 2.0 mmol), HBTU (457 mg, 1.27 mmol), and HOBT (125 mg, 0.93 mmol). Then added DMF (2 mL) followed by N,N-diisopropylethylamine (0.59 mL, 3.38 mmol). The yellow reaction mixture was stirred at room temperature overnight then quenched with water and extracted with EtOAc (30 mL). The organic layer was washed once with saturated NaHCO$_3$ and water. The combined aqueous layers were back extracted with EtOAc (25 mL). The combined organic layers was dried over sodium sulfate, filtered and concentrated. The residue was purified by chromatography over SiO$_2$ with EtOAc/heptane (gradient: 0-100% EtOAc) to afford 401 mg (89%) of 2-(6-chloro-4-fluoro-1H-indazol-3-yl)-5-(2-trimethylsilanyl-ethoxymethyl)-5H-pyrrolo[2,3-b]pyrazine-7-carboxylic acid ((S)-2-methoxy-1-methyl-ethyl)-amide as a light yellow solid. MS: [M+H]$^+$= 533.

Step 2

2-(6-Chloro-4-fluoro-1-methyl-1H-indazol-3-yl)-5-(2-trimethylsilanyl-ethoxymethyl)-5H-pyrrolo[2,3-b] pyrazine-7-carboxylic acid ((S)-2-methoxy-1-methyl-ethyl)-amide

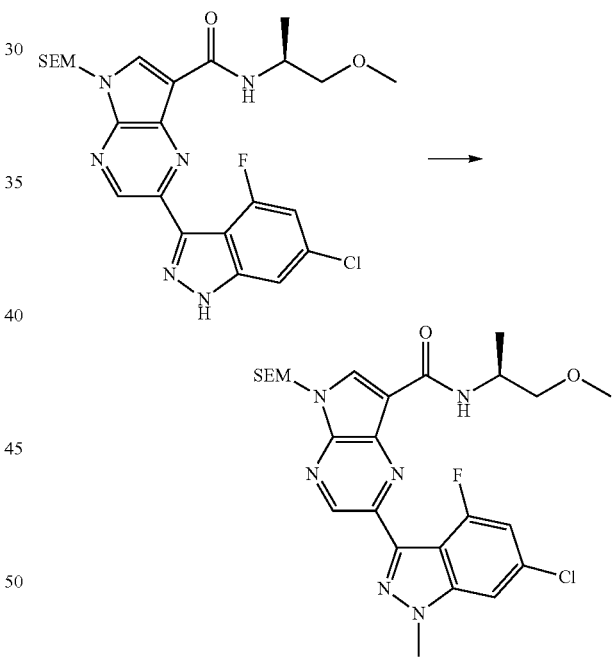

A 50 mL round-bottomed flask was charged with 2-(6-chloro-4-fluoro-1H-indazol-3-yl)-5-(2-trimethylsilanyl-ethoxymethyl)-5H-pyrrolo[2,3-b]pyrazine-7-carboxylic acid ((S)-2-methoxy-1-methyl-ethyl)-amide (120 mg, 0.225 mmol) and DMF (0.45 ml) to give a light yellow solution. The reaction mixture was placed under argon atmosphere and cooled in a 0° C. bath. NaH (60% in mineral oil, 23 mg, 0.575 mmol) was added. The reaction mixture was stirred at 0° C. for 10 min and at room temperature for 10 min then returned to the cooling bath and iodomethane (21 µl, 0.34 mmol) was added. The reaction was stirred at 0° C. for 10 min then the bath was removed and stirring continued at room temperature for an additional 18 h. The reaction was quenched with water and the precipitate collected by filtration. The crude material was purified by chromoatography over SiO$_2$ with EtOAc/heptane (gradient: 0-100% EtOAc) to afford 41 mg (33%) of 2-(6-chloro-4-fluoro-1-methyl-1H-indazol-3-yl)-5-(2-trimethylsilanylethoxymethyl)-5H-pyrrolo[2,3-b]pyrazine-7-carboxylic acid ((S)-2-methoxy-1-methyl-ethyl)-amide as an off-white solid. MS: [M+H]$^+$=547.

Step 3

2-(6-Chloro-4-fluoro-1-methyl-1H-indazol-3-yl)-5H-pyrrolo[2,3-b]pyrazine-7-carboxylic acid ((S)-2-methoxy-1-methyl-ethyl)-amide

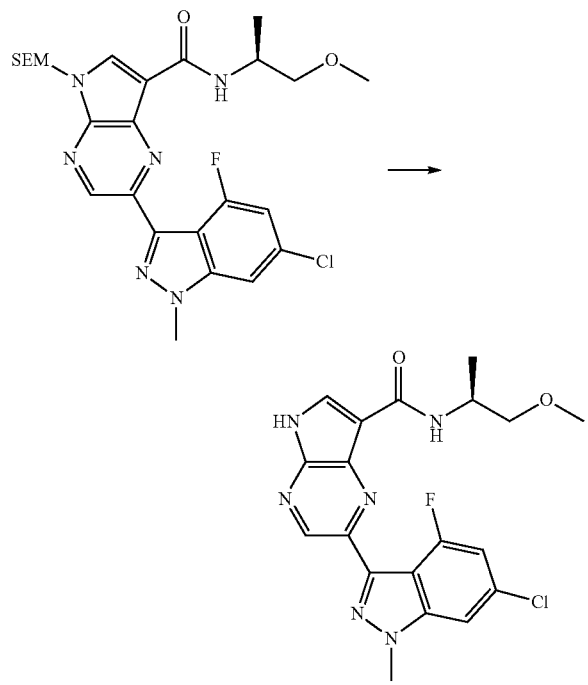 [SMILES: COC[C@H](C)NC(=O)c1cn(COCC[Si](C)(C)C)c2ncc(-c3n[nH]c4cc(Cl)cc(F)c34)nc12 ; COC[C@H](C)NC(=O)c1cn(COCC[Si](C)(C)C)c2ncc(-c3nn(C)c4cc(Cl)cc(F)c34)nc12]

In a 25 mL round-bottom flask, 2-(6-chloro-4-fluoro-1-methyl-1H-indazol-3-yl)-5-(2-trimethylsilanyl-ethoxymethyl)-5H-pyrrolo[2,3-b]pyrazine-7-carboxylic acid ((S)-2-methoxy-1-methyl-ethyl)-amide (40 mg, 0.073 mmol) and TFA (0.60 ml, 7.8 mmol) were combined with dichloromethane (2 ml) to give an orange solution. The reaction mixture was stirred at room temperature for 2.5 h then concentrated under reduced pressure. The resultant crude solid was dissolved in dichloromethane (2 mL) and ethylenediamine (0.40 ml, 5.9 mmol) was added. The reaction mixture was stirred at room temperature for 18 h then concentrated and the residue was precipitated with water. The suspension was stirred for 1 h and the crude solid collected by filtration. The crude solid was purified by trituration (dichloromethane/heptane) to afford 17 mg (55%) of 2-(6-chloro-4-fluoro-1-methyl-1H-indazol-3-yl)-5H-pyrrolo[2,3-b]pyrazine-7-carboxylic acid ((S)-2-methoxy-1-methyl-ethyl)-amide as an off-white solid. MS: [M+H]$^+$=417; $^1$H NMR (300 MHz, DMSO-d$_6$) δ: 12.68 (br. s., 1H), 9.00 (s, 1H), 8.44 (s, 1H), 8.32 (d, J=8.7 Hz, 1H), 7.89 (d, J=1.5 Hz, 1H), 7.27 (dd, J=10.6, 1.5 Hz, 1H), 4.31 (dt, J=13.5, 7.0 Hz, 1H), 4.19 (s, 3H), 3.45 (dd, J=9.3, 5.8 Hz, 3H), 3.36 (dd, J=9.8, 5.3 Hz, 1H), 3.20 (s, 3H), 1.22 (d, J=6.8 Hz, 3H).

Example 171

2-(6-Chloro-1-methyl-1H-indazol-3-yl)-5H-pyrrolo[2,3-b]pyrazine-7-carboxylic acid ((S)-2-ethoxy-1-methyl-ethyl)-amide

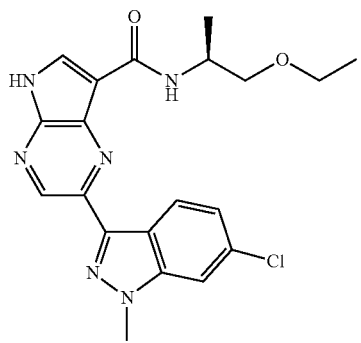 [SMILES: CCOC[C@H](C)NC(=O)c1c[nH]c2ncc(-c3nn(C)c4cc(Cl)ccc34)nc12]

Prepared according to the procedure outlined in Example 145, substituting (S)-1-ethoxypropan-2-amine hydrochloride for cis-cyclohexane-1,4,diamine in Step 1. The final compound was isolated as a white solid, 35 mg (68%); MS: [M+H]$^+$=413; $^1$H NMR (300 MHz, DMSO-d$_6$) δ: 12.49-13.15 (m, 1H), 9.11 (s, 1H), 8.41-8.48 (m, 1H), 8.41-8.56 (m, 2H), 8.21 (d, J=8.3 Hz, 1H), 8.00 (d, J=1.5 Hz, 1H), 7.28 (dd, J=8.7, 1.5 Hz, 1H), 4.27-4.45 (m, 1H), 4.18 (s, 3H), 3.56 (dd, J=9.4, 4.5 Hz, 1H), 3.48 (dd, J=9.2, 4.5 Hz, 1H), 3.45 (q, J=7.2 Hz, 2H), 1.33 (d, J=6.8 Hz, 3H), 0.97 (t, J=7.0 Hz, 3H).

Example 172

2-(6-Chloro-1-methyl-1H-indazol-3-yl)-5H-pyrrolo[2,3-b]pyrazine-7-carboxylic acid (2-hydroxy-1-methyl-propyl)-amide

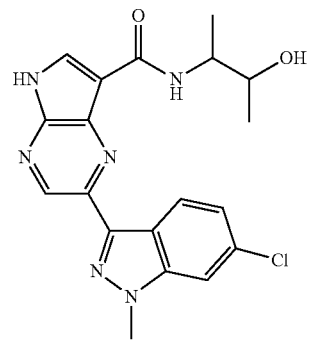 [SMILES: CC(O)C(C)NC(=O)c1c[nH]c2ncc(-c3nn(C)c4cc(Cl)ccc34)nc12]

Prepared according to the procedure outlined in Example 145, substituting 3-aminobutan-2-ol for cis-cyclohexane-1,4, diamine in Step 1. The final compound was isolated as an off-white solid (mixture of diastereomers), 22 mg (73%); [M+H]$^+$=399; $^1$H NMR (300 MHz, DMSO-d$_6$) δ: 12.76 (br. s., 1H), 9.15 (s, 1H), 8.78 (d, J=8.7 Hz, 1H), 8.42 (s, 1H), 8.12 (d, J=9.4 Hz, 1H), 7.96 (s, 1H), 7.33 (dd, J=8.7, 1.5 Hz, 1H), 5.18 (d, J=4.2 Hz, 1H), 4.17 (s, 3H), 4.12-4.22 (m, 1H), 3.77-3.89 (m, 1H), 1.27 (d, J=6.8 Hz, 3H), 1.11 (d, J=6.4 Hz, 3H).

Example 173

2-(6-Chloro-1-methyl-1H-indazol-3-yl)-5H-pyrrolo[2,3-b]pyrazine-7-carboxylic acid ((S)-1-methoxymethyl-propyl)-amide

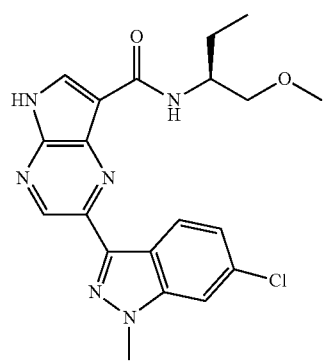 [SMILES: CC[C@@H](COC)NC(=O)c1c[nH]c2ncc(-c3nn(C)c4cc(Cl)ccc34)nc12]

Prepared according to the procedure outlined in Example 166, substituting (S)-2-aminobutan-1-ol for 2-aminopropane-1,3-diol in Step 1. The final compound was isolated as an off-white solid, 20 mg (70%); MS: [M+H]$^+$=413; $^1$H NMR (300 MHz, DMSO-d$_6$) δ: 12.85 (br. s., 1H), 9.12 (s, 1H), 8.50 (d, J=8.7 Hz, 1H), 8.44 (s, 1H), 8.17 (d, J=9.1 Hz, 1H), 8.00 (d, J=1.5 Hz, 1H), 7.25 (dd, J=8.7, 1.5 Hz, 1H), 4.15-4.20 (m, 3H), 4.10-4.32 (m, 1H), 3.57 (dd, J=9.5, 4.2 Hz, 1H), 3.47 (dd, J=9.7, 4.3 Hz, 1H), 3.27 (s, 3H), 1.50-1.92 (m, 2H), 0.96 (t, J=7.4 Hz, 3H).

Example 174

2-(6-Chloro-1-methyl-1H-indazol-3-yl)-5H-pyrrolo[2,3-b]pyrazine-7-carboxylic acid [(R)-2-(3-fluoro-azetidin-1-yl)-1-methoxymethyl-2-oxo-ethyl]-amide

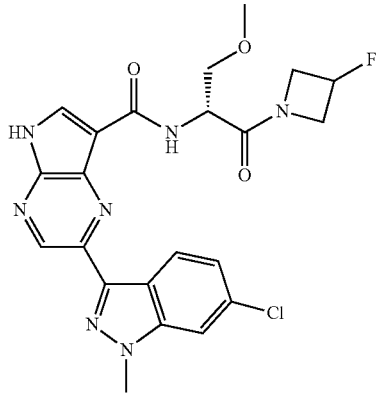 [SMILES: COC[C@@H](NC(=O)c1c[nH]c2ncc(-c3nn(C)c4cc(Cl)ccc34)nc12)C(=O)N1CC(F)C1]

Step 1

[(R)-2-(3-Fluoro-azetidin-1-yl)-1-methoxymethyl-2-oxo-ethyl]-carbamic acid tert-butyl ester

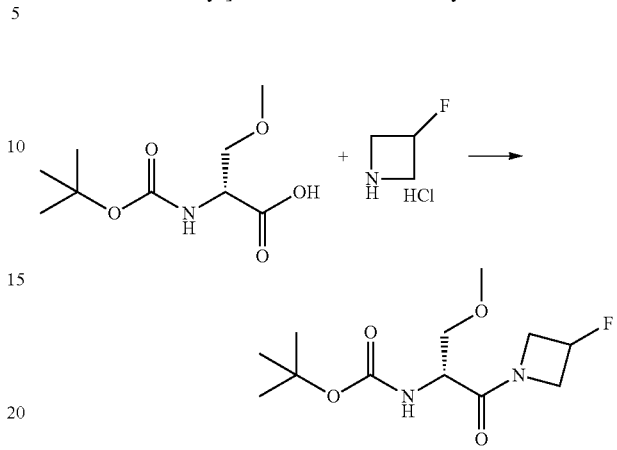

A 25 mL round-bottomed flask was charged with (R)-2-tert-butoxycarbonylamino-3-methoxy-propionic acid (0.40 g, 1.82 mmol), 3-fluoroazetidine hydrochloride (204 mg, 1.82 mmol), HBTU (989 mg, 2.74 mmol), and HOBt (375 mg, 2.74 mmol). Then added DMF (3.6 mL) followed by N,N-diisopropylethylamine (1.27 mL, 7.3 mmol). The reaction mixture was stirred at room temperature overnight then quenched with water and extracted with EtOAc (30 mL). The organic layer was washed once with saturated NaHCO$_3$ and water. The combined aqueous layers were back extracted with EtOAc (25 mL). The combined organic layers was dried over sodium sulfate, filtered and concentrated. The residue was purified by chromatography over SiO$_2$ with EtOAc/heptane (gradient: 0-50% EtOAc) to afford 267 mg (53%) of [(R)-2-(3-fluoro-azetidin-1-yl)-1-methoxymethyl-2-oxo-ethyl]-carbamic acid tert-butyl ester as a white solid.

Step 2

(R)-2-Amino-1-(3-fluoro-azetidin-1-yl)-3-methoxy-propan-1-one trifluoroacetate

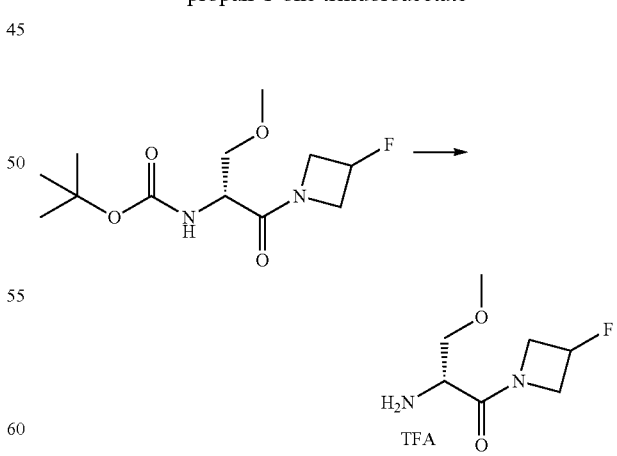

In a 25 mL round-bottomed flask, [(R)-2-(3-fluoro-azetidin-1-yl)-1-methoxymethyl-2-oxo-ethyl]-carbamic acid tert-butyl ester (265 mg, 0.96 mmol) was dissolved in dichloromethane (5 ml). The reaction was cooled to 0° C. and trifluoroacetic acid (1.5 ml, 19.5 mmol) was slowly added.

The reaction mixture was stirred at room temperature for 3 h then concentrated to provide (R)-2-amino-1-(3-fluoro-azetidin-1-yl)-3-methoxy-propan-1-one trifluoroacetate as a colorless viscous oil which was used without further purification.

Step 3

2-(6-Chloro-1-methyl-1H-indazol-3-yl)-5-(2-trimethylsilanyl-ethoxymethyl)-5H-pyrrolo[2,3-b]pyrazine-7-carboxylic acid [(R)-2-(3-fluoro-azetidin-1-yl)-1-methoxymethyl-2-oxo-ethyl]-amide

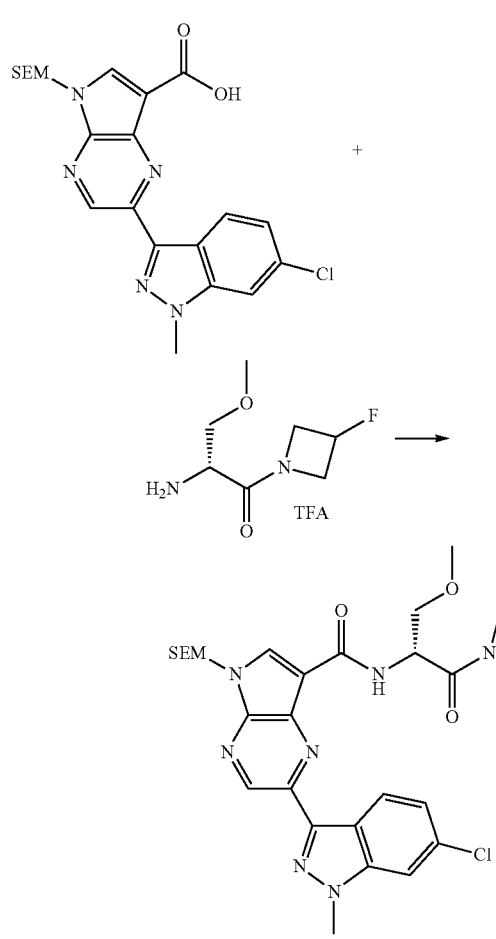

A 10 mL round-bottomed flask was charged with 2-(6-chloro-1-methyl-1H-indazol-3-yl)-5-(2-trimethylsilanyl-ethoxymethyl)-5H-pyrrolo[2,3-b]pyrazine-7-carboxylic acid (75 mg, 0.16 mmol), (R)-2-amino-1-(3-fluoro-azetidin-1-yl)-3-methoxy-propan-1-one trifluoroacetate (63 mg, 0.21 mmol), and HATU (63 mg, 0.21 mmol). Then added acetonitrile (1 mL) followed by N,N-diisopropylethylamine (0.55 mL, 3.15 mmol). The light yellow reaction mixture was stirred at room temperature overnight then quenched with water. The mixture was extracted with dichloromethane. The organic layers were combined, dried over $Na_2SO_4$, and concentrated. The residue was purified by chromatography over $SiO_2$ with EtOAc/heptanes (gradient: 5-90% EtOAc) to afford 47 mg (47%) of 2-(6-chloro-1-methyl-1H-indazol-3-yl)-5-(2-trimethylsilanylethoxymethyl)-5H-pyrrolo[2,3-b]pyrazine-7-carboxylic acid [(R)-2-(3-fluoro-azetidin-1-yl)-1-methoxymethyl-2-oxo-ethyl]-amide as an off-white solid. MS: [M+H]$^+$=616.

Step 4

2-(6-Chloro-1-methyl-1H-indazol-3-yl)-5H-pyrrolo[2,3-b]pyrazine-7-carboxylic acid [(R)-2-(3-fluoro-azetidin-1-yl)-1-methoxymethyl-2-oxo-ethyl]-amide

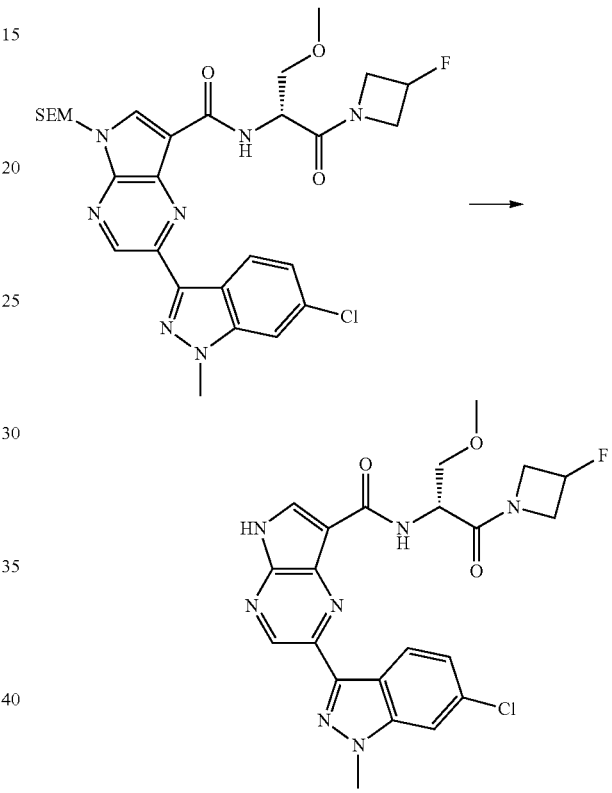

In a 25 mL round-bottom flask, 2-(6-chloro-1-methyl-1H-indazol-3-yl)-5-(2-trimethylsilanyl-ethoxymethyl)-5H-pyrrolo[2,3-b]pyrazine-7-carboxylic acid [(R)-2-(3-fluoro-azetidin-1-yl)-1-methoxymethyl-2-oxo-ethyl]-amide (47 mg, 0.076 mmol) and TFA (1.2 ml, 15.6 mmol) were combined with dichloromethane (4 ml) to give an orange solution. The reaction mixture was stirred at room temperature for 2.5 h then concentrated under reduced pressure. The resultant crude solid was dissolved in dichloromethane (4 mL) and ethylenediamine (0.36 ml, 5.3 mmol) was added. The reaction mixture was stirred at room temperature for 18 h then concentrated and the residue was precipitated with water. The suspension was stirred for 1 h and the crude solid collected by filtration. The crude solid was purified by trituration (dichloromethane/heptane) to afford 24 mg (64%) of 2-(6-chloro-1-methyl-1H-indazol-3-yl)-5H-pyrrolo[2,3-b]pyrazine-7-carboxylic acid [(R)-2-(3-fluoro-azetidin-1-yl)-1-methoxymethyl-2-oxo-ethyl]-amide as an off-white solid. MS: [M+H]$^+$=486; $^1$H NMR (300 MHz, DMSO-$d_6$) δ: 12.85 (br. s., 1H), 9.16 (s, 1H), 8.76 (dd, J=8.7, 5.3 Hz, 1H), 8.55 (d, J=8.3 Hz, 1H), 8.49 (s, 1H), 7.97 (d, J=1.5 Hz, 1H), 7.24 (d, J=9.1 Hz, 1H), 5.23-5.58 (m, 1H), 4.97 (dt, J=8.1, 5.8 Hz, 1H), 4.56-4.82 (m, 1H), 4.21-4.56 (m, 2H), 4.18 (s, 3H), 3.87-4.10 (m, 1H), 3.68 (qd, J=9.8, 5.7 Hz, 2H), 3.28 (app. d, J=3.4 Hz, 3H).

Example 175

2-(6-Chloro-1-methyl-1H-indazol-3-yl)-5H-pyrrolo[2,3-b]pyrazine-7-carboxylic acid [(R)-2-(3-cyano-azetidin-1-yl)-1-methoxymethyl-2-oxo-ethyl]-amide

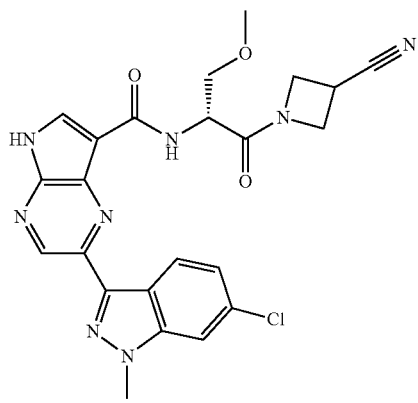

Step 1

[(R)-2-(3-Cyano-azetidin-1-yl)-1-methoxymethyl-2-oxo-ethyl]-carbamic acid tert-butyl ester

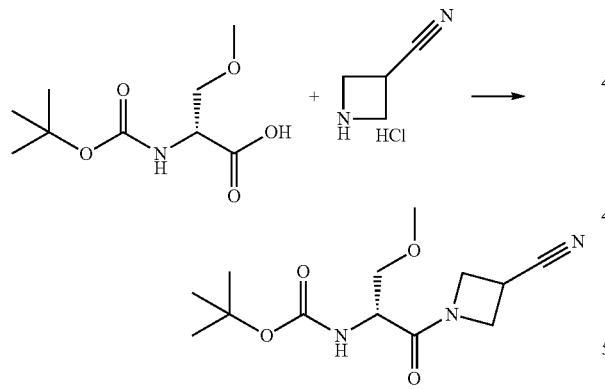

A 25 mL round-bottomed flask was charged with (R)-2-tert-butoxycarbonylamino-3-methoxy-propionic acid (0.475 g, 2.17 mmol), azetidine-3-carbonitrile hydrochloride (314 mg, 2.65 mmol) and HATU (832 mg, 2.19 mmol). Then added DMF (3.6 mL) followed by N,N-diisopropylethylamine (1.5 mL, 8.67 mmol). The reaction mixture was stirred at room temperature overnight then quenched with water and extracted with EtOAc (30 mL). The organic layer was washed once with saturated NaHCO₃ and water. The combined aqueous layers were back extracted with EtOAc (25 mL). The combined organic layers were dried over sodium sulfate, filtered and concentrated. The residue was purified by chromatography over SiO₂ with EtOAc/heptane (gradient: 0-100% EtOAc) to afford 288 mg (47%) of [(R)-2-(3-cyano-azetidin-1-yl)-1-methoxymethyl-2-oxo-ethyl]-carbamic acid tert-butyl ester as a viscous colorless oil.

Step 2

1-((R)-2-Amino-3-methoxy-propionyl)-azetidine-3-carbonitrile trifluoroacetate

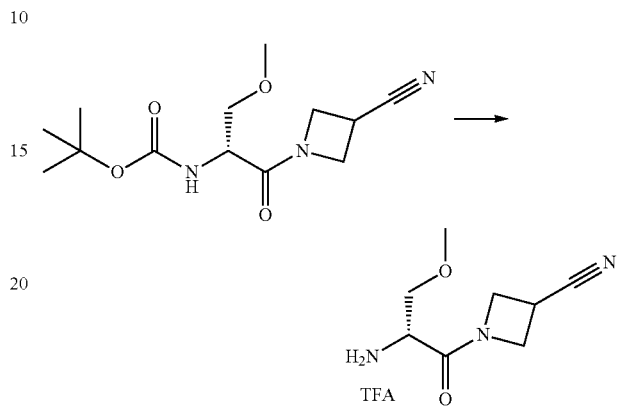

In a 25 mL round-bottomed flask, [(R)-2-(3-cyano-azetidin-1-yl)-1-methoxymethyl-2-oxo-ethyl]-carbamic acid tert-butyl ester (286 mg, 1.00 mmol) was dissolved in dichloromethane (4 ml). The reaction was cooled to 0° C. and trifluoroacetic acid (1.2 ml, 15.6 mmol) was slowly added. The reaction mixture was stirred at room temperature for 3 h then concentrated to provide 1-((R)-2-amino-3-methoxy-propionyl)-azetidine-3-carbonitrile trifluoroacetate as a colorless viscous oil which was used without further purification.

Step 3

2-(6-Chloro-1-methyl-1H-indazol-3-yl)-5-(2-trimethylsilanyl-ethoxymethyl)-5H-pyrrolo[2,3-b]pyrazine-7-carboxylic acid [(R)-2-(3-cyano-azetidin-1-yl)-1-methoxymethyl-2-oxo-ethyl]-amide

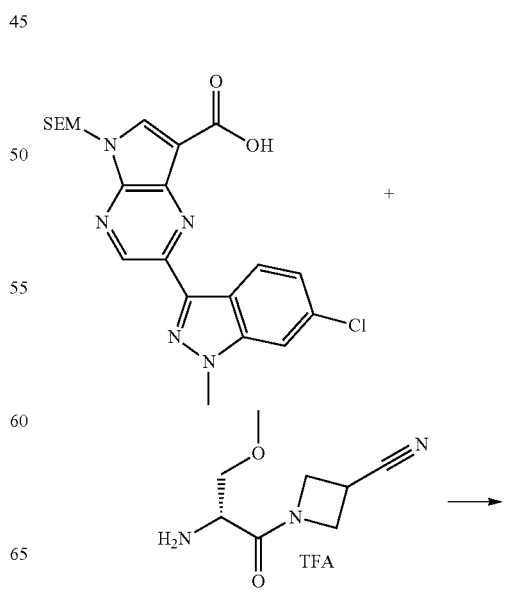

693
-continued

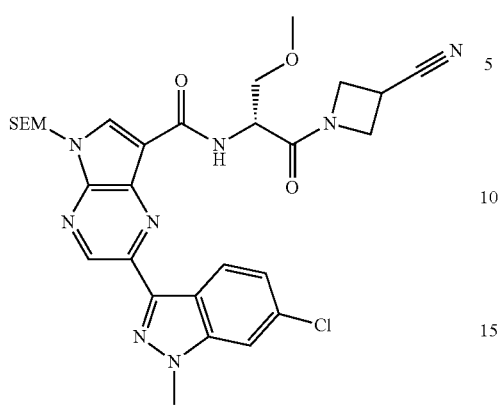

A 10 mL round-bottomed flask was charged with 2-(6-chloro-1-methyl-1H-indazol-3-yl)-5-(2-trimethylsilanyl-ethoxymethyl)-5H-pyrrolo[2,3-b]pyrazine-7-carboxylic acid (50 mg, 0.11 mmol), 1-((R)-2-amino-3-methoxy-propionyl)-azetidine-3-carbonitrile trifluoroacetate (42 mg, 0.14 mmol), and HATU (42 mg, 0.11 mmol). Then added acetonitrile (1 mL) followed by N,N-diisopropylethylamine (0.19 mL, 1.1 mmol). The light yellow reaction mixture was stirred at room temperature overnight then quenched with water. The mixture was extracted with dichloromethane. The organic layers were combined, dried over $Na_2SO_4$, and concentrated. The residue was purified by chromatography over $SiO_2$ with EtOAc/heptanes (gradient: 5-90% EtOAc) to afford 44 mg (63%) of 2-(6-chloro-1-methyl-1H-indazol-3-yl)-5-(2-trimethylsilanylethoxymethyl)-5H-pyrrolo[2,3-b]pyrazine-7-carboxylic acid [(R)-2-(3-cyano-azetidin-1-yl)-1-methoxymethyl-2-oxo-ethyl]-amide as an off-white solid. MS: $[M+H]^+=623$.

Step 4

2-(6-Chloro-1-methyl-1H-indazol-3-yl)-5H-pyrrolo[2,3-b]pyrazine-7-carboxylic acid [(R)-2-(3-cyano-azetidin-1-yl)-1-methoxymethyl-2-oxo-ethyl]-amide

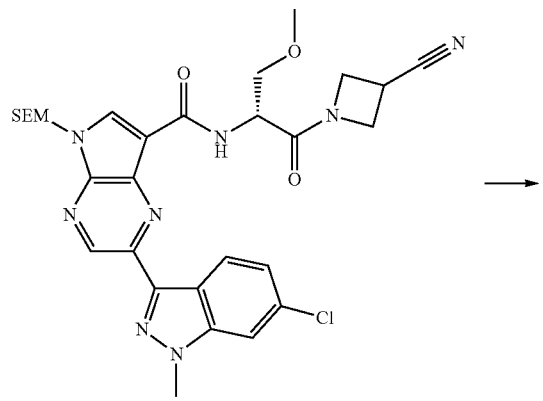

694
-continued

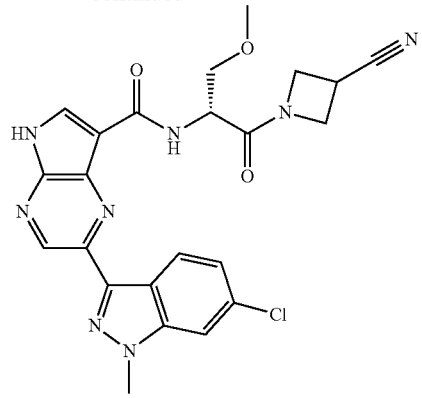 [SMILES: COC[C@@H](NC(=O)c1c[nH]c2ncc(-c3nn(C)c4cc(Cl)ccc34)nc12)C(=O)N1CC(C#N)C1]

In a 25 mL round-bottom flask, 2-(6-chloro-1-methyl-1H-indazol-3-yl)-5-(2-trimethylsilanyl-ethoxymethyl)-5H-pyrrolo[2,3-b]pyrazine-7-carboxylic acid [(R)-2-(3-cyano-azetidin-1-yl)-1-methoxymethyl-2-oxo-ethyl]-amide (44 mg, 0.071 mmol) and TFA (1.8 ml, 23.4 mmol) were combined with dichloromethane (6 ml) to give an orange solution. The reaction mixture was stirred at room temperature for 2.5 h then concentrated under reduced pressure. The resultant crude solid was dissolved in dichloromethane (4 mL) and ethylenediamine (0.30 ml, 4.4 mmol) was added. The reaction mixture was stirred at room temperature for 18 h then concentrated and the residue was precipitated with water. The suspension was stirred for 1 h and the crude solid collected by filtration. The crude solid was purified by trituration (hot dichloromethane/heptane) to afford 21 mg (59%) of 2-(6-chloro-1-methyl-1H-indazol-3-yl)-5H-pyrrolo[2,3-b]pyrazine-7-carboxylic acid [(R)-2-(3-cyano-azetidin-1-yl)-1-methoxymethyl-2-oxo-ethyl]-amide as a white solid. MS: $[M+H]^+=492$; $^1H$ NMR (300 MHz, DMSO-$d_6$) δ: 12.72 (br. s, 1H), 9.16 (s, 1H), 8.74 (d, J=8.7 Hz, 1H), 8.55 (d, J=8.3 Hz, 1H), 8.50 (d, J=4.9 Hz, 1H), 7.97 (d, J=1.5 Hz, 1H), 7.23 (d, J=8.7 Hz, 1H), 4.86-5.04 (m, 1H), 4.46-4.73 (m, 2H), 4.17-4.19 (m, 1H), 4.16-4.28 (m, 4H), 4.04-4.16 (m, 1H), 3.77-3.93 (m, 1H), 3.72 (dd, J=9.5, 4.9 Hz, 1H), 3.59-3.68 (m, 1H), 3.27 (app d, J=4.9 Hz, 3H).

Example 176

2-(6-Chloro-1-methyl-1H-indazol-3-yl)-5H-pyrrolo[2,3-b]pyrazine-7-carboxylic acid (2-hydroxy-1-methyl-propyl)-amide

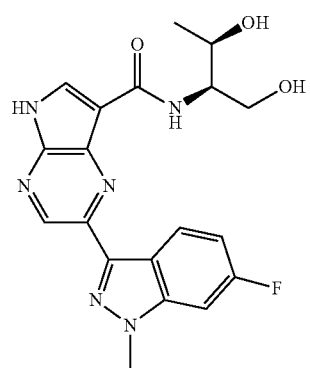 [SMILES: C[C@@H](O)[C@@H](CO)NC(=O)c1c[nH]c2ncc(-c3nn(C)c4cc(F)ccc34)nc12]

Step 1

2-(6-Fluoro-1-methyl-1H-indazol-3-yl)-5-(2-trimethylsilanyl-ethoxymethyl)-5H-pyrrolo[2,3-b]pyrazine-7-carboxylic acid ((1R,2R)-2-hydroxy-1-hydroxymethyl-propyl)-amide

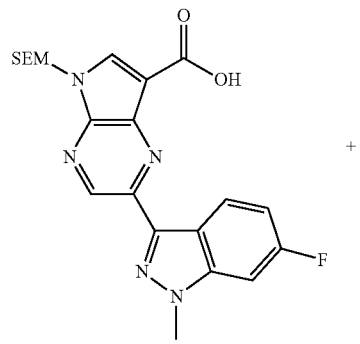

+

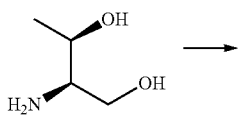

→

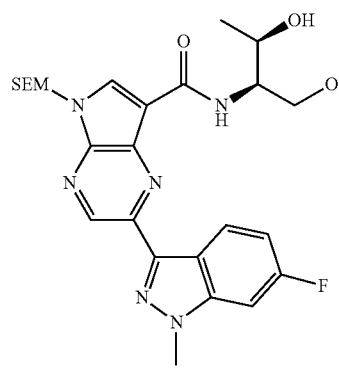

A 25 mL round-bottomed flask was charged with 2-(6-fluoro-1-methyl-1H-indazol-3-yl)-5-(2-trimethylsilanyl-ethoxymethyl)-5H-pyrrolo[2,3-b]pyrazine-7-carboxylic acid (100 mg, 0.226 mmol), (2R,3R)-2-aminobutane-1,3-diol (25 mg, 0.24 mmol), and HATU (90 mg, 0.24 mmol). Then added acetonitrile (2 mL) followed by N,N-diisopropylethylamine (0.10 mL, 0.57 mmol). The reaction mixture was stirred at room temperature overnight then quenched with water. The mixture was extracted with ethyl acetate (3×). The organic layers were combined, dried over Na$_2$SO$_4$, and concentrated. The residue was purified by trituration with 1:1 heptane/dichloromethane to afford 115 mg (96%) of 2-(6-fluoro-1-methyl-1H-indazol-3-yl)-5-(2-trimethylsilanyl-ethoxymethyl)-5H-pyrrolo[2,3-b]pyrazine-7-carboxylic acid ((1R,2R)-2-hydroxy-1-hydroxymethyl-propyl)-amide as a white solid. MS: [M+H]$^+$=529.

Step 2

2-(6-Fluoro-1-methyl-1H-indazol-3-yl)-5H-pyrrolo[2,3-b]pyrazine-7-carboxylic acid ((1R,2R)-2-hydroxy-1-hydroxymethyl-propyl)-amide

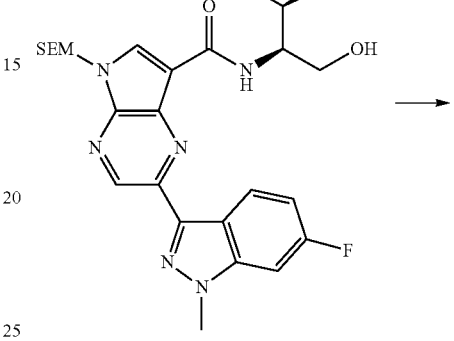

→

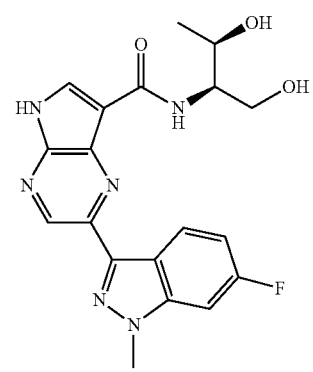

In a 10 mL round-bottom flask, 2-(6-fluoro-1-methyl-1H-indazol-3-yl)-5-(2-trimethylsilanyl-ethoxymethyl)-5H-pyrrolo[2,3-b]pyrazine-7-carboxylic acid ((1R,2R)-2-hydroxy-1-hydroxymethyl-propyl)-amide (30 mg, 0.057 mmol) and TFA (0.3 ml, 3.9 mmol) were combined with dichloromethane (1 ml) to give an orange solution. The reaction mixture was stirred at room temperature for 2.5 h then concentrated under reduced pressure. The resultant crude solid was dissolved in dichloromethane (1 mL) and ethylenediamine (0.10 ml, 1.5 mmol) was added. The reaction mixture was stirred at room temperature for 18 h then concentrated and the residue was precipitated with water. The suspension was stirred for 1 h and the crude solid collected by filtration. The crude solid was purified by trituration (hot dichloromethane/heptane) to afford 9 mg (40%) of 2-(6-fluoro-1-methyl-1H-indazol-3-yl)-5H-pyrrolo[2,3-b]pyrazine-7-carboxylic acid ((1R,2R)-2-hydroxy-1-hydroxymethyl-propyl)-amide as a light yellow solid. MS: [M+H]$^+$=399; $^1$H NMR (DMSO-d$_6$) δ: 12.61 (br. s., 1H), 9.16 (s, 1H), 8.83 (dd, J=8.9, 5.5 Hz, 1H), 8.44 (s, 1H), 8.15 (d, J=9.4 Hz, 1H), 7.64 (dd, J=9.8, 1.9 Hz, 1H), 7.15 (td, J=9.3, 1.9 Hz, 1H), 5.07 (d, J=4.2

Hz, 1H), 4.85 (t, J=4.9 Hz, 1H), 4.15 (s, 3H), 3.98-4.24 (m, 2H), 3.54-3.71 (m, 2H), 1.13 (d, J=6.0 Hz, 3H).

Example 177

2-(6-Fluoro-1-methyl-1H-indazol-3-yl)-5H-pyrrolo[2,3-b]pyrazine-7-carboxylic acid ((1R,2R)-2-hydroxy-1-methoxymethyl-propyl)-amide

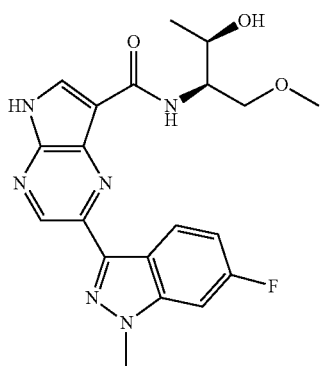 [SMILES: COC[C@@H](NC(=O)c1c[nH]c2ncc(-c3nn(C)c4cc(F)ccc34)nc12)[C@@H](C)O]

Step 1

2-(6-Fluoro-1-methyl-1H-indazol-3-yl)-5-(2-trimethylsilanyl-ethoxymethyl)-5H-pyrrolo[2,3-b]pyrazine-7-carboxylic acid ((1R,2R)-2-hydroxy-1-methoxymethyl-propyl)-amide

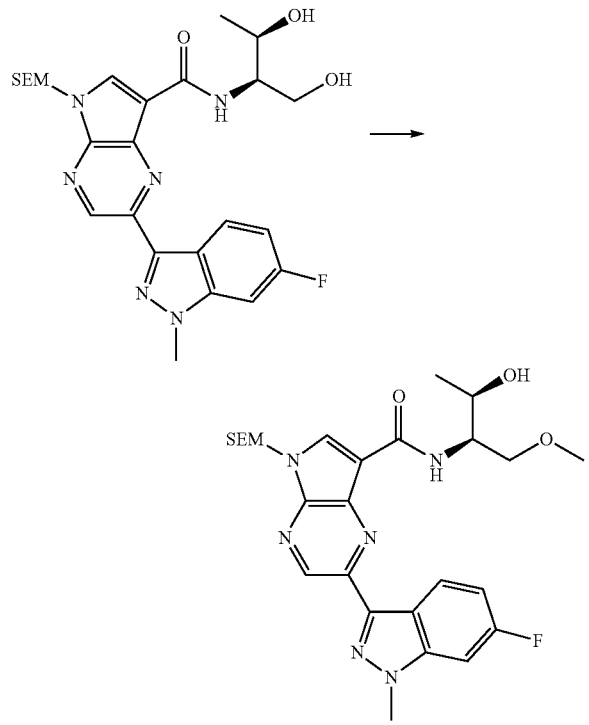

In a 10 mL round-bottomed flask, 2-(6-fluoro-1-methyl-1H-indazol-3-yl)-5-(2-trimethylsilanyl-ethoxymethyl)-5H-pyrrolo[2,3-b]pyrazine-7-carboxylic acid ((1R,2R)-2-hydroxy-1-hydroxymethyl-propyl)-amide (81 mg, 0.152 mmol) was dissolved in THF (1.5 ml) to give a colorless solution. The reaction was cooled in an ice bath and crushed KOH (86 mg, 1.52 mmol), 18-crown-6 (40 mg, 0.152 mmol), and iodomethane (10 µl, 0.152 mmol) were added successively. The reaction mixture was stirred at 0° C. for 1 h after which the ice bath was removed. The reaction mixture was stirred at room temperature for 2 h then diluted with dichloromethane (10 mL) and washed with aqueous ammonium chloride (10 mL), water (10 mL), and saturated sodium bicarbonate (10 mL). The organic layer was dried over Na$_2$SO$_4$ and concentrated. The crude material was purified by chromatography over SiO$_2$ with EtOAc/heptane (gradient: 0%-60% EtOAc) to afford 30 mg (36%) of 2-(6-fluoro-1-methyl-1H-indazol-3-yl)-5-(2-trimethylsilanyl-ethoxymethyl)-5H-pyrrolo[2,3-b]pyrazine-7-carboxylic acid ((1R,2R)-2-hydroxy-1-methoxymethyl-propyl)-amide as an off-white solid. $^1$H NMR (300 MHz, DMSO-d$_6$) δ: 9.22 (s, 1H), 8.78 (dd, J=8.9, 5.5 Hz, 1H), 8.66 (s, 1H), 8.14 (d, J=9.4 Hz, 1H), 7.67 (dd, J=9.8, 2.3 Hz, 1H), 7.17 (td, J=9.2, 2.1 Hz, 1H), 5.75 (s, 2H), 5.21 (d, J=4.2 Hz, 1H), 4.22-4.34 (m, 1H), 4.17 (s, 3H), 3.97-4.12 (m, 1H), 3.61 (app t, J=8.2 Hz, 3H), 3.52 (dd, J=9.8, 6.4 Hz, 1H), 3.28 (s, 3H), 1.14 (d, J=6.4 Hz, 3H), 0.87 (t, J=7.9 Hz, 2H), −0.07 (s, 9H).

Step 2

2-(6-Fluoro-1-methyl-1H-indazol-3-yl)-5H-pyrrolo[2,3-b]pyrazine-7-carboxylic acid ((1R,2R)-2-hydroxy-1-methoxymethyl-propyl)-amide

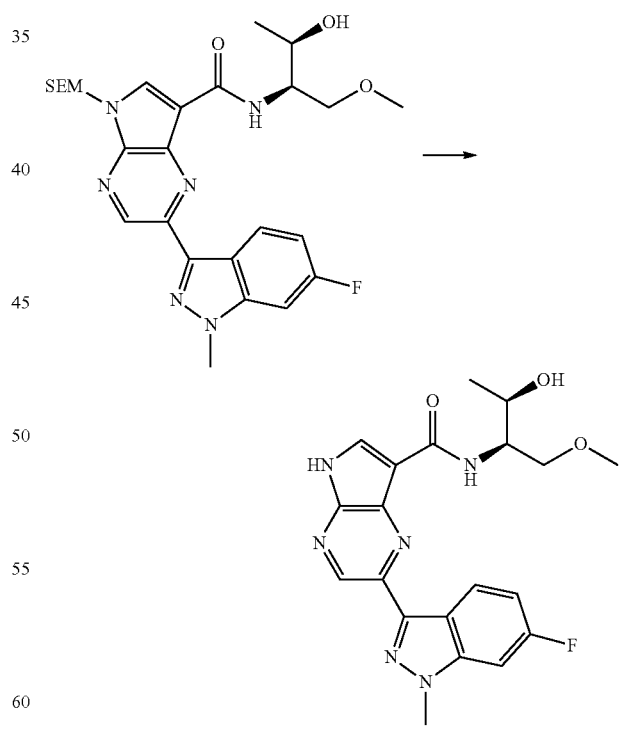

In a 10 mL round-bottom flask, 2-(6-fluoro-1-methyl-1H-indazol-3-yl)-5-(2-trimethylsilanyl-ethoxymethyl)-5H-pyrrolo[2,3-b]pyrazine-7-carboxylic acid ((1R,2R)-2-hydroxy-1-methoxymethyl-propyl)-amide (30 mg, 0.055 mmol) and TFA (0.3 ml, 3.9 mmol) were combined with dichloromethane (1 ml) to give an orange solution. The reaction mixture was stirred at room temperature for 2.5 h then concentrated under reduced pressure. The resultant crude solid was dissolved in dichloromethane (1 mL) and ethylenediamine (0.26 ml, 3.9 mmol) was added. The reaction mixture was stirred at room temperature for 18 h then concentrated and the residue was precipitated with water. The suspension was stirred for 1 h and the crude solid collected by filtration. The crude solid was purified by trituration (hot dichloromethane/heptane) to afford 11 mg (47%) of 2-(6-fluoro-1-methyl-1H-indazol-3-yl)-5H-pyrrolo[2,3-b]pyrazine-7-carboxylic acid ((1R,2R)-2-hydroxy-1-methoxymethyl-propyl)-amide as a light yellow solid. $^1$H NMR (300 MHz, DMSO-d$_6$) δ: 12.85 (br. s., 1H), 9.16 (s, 1H), 8.78 (dd, J=8.9, 5.5 Hz, 1H), 8.43 (s, 1H), 8.15 (d, J=9.4 Hz, 1H), 7.65 (dd, J=9.6, 2.1 Hz, 1H), 7.15 (td, J=9.2, 2.5 Hz, 1H), 5.17 (d, J=4.2 Hz, 1H), 4.20-4.33 (m, 1H), 4.15 (s, 3H), 3.98-4.09 (m, 1H), 3.59 (dd, J=9.8, 6.8 Hz, 1H), 3.50 (dd, J=9.4, 6.4 Hz, 1H), 3.27 (s, 3H), 1.13 (d, J=6.4 Hz, 3H).

Example 178

2-(6-Fluoro-1-methyl-1H-indazol-3-yl)-5H-pyrrolo[2,3-b]pyrazine-7-carboxylic acid ((S)-secbutyl)-amide

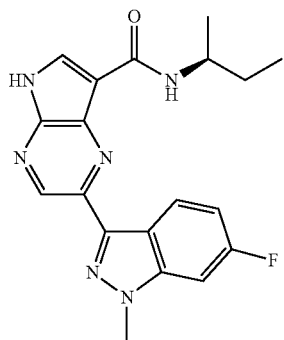

Step 1

2-(6-Fluoro-1-methyl-1H-indazol-3-yl)-5-(2-trimethylsilanyl-ethoxymethyl)-5H-pyrrolo[2,3-b]pyrazine-7-carboxylic acid ((S)-sec-butyl)-amide

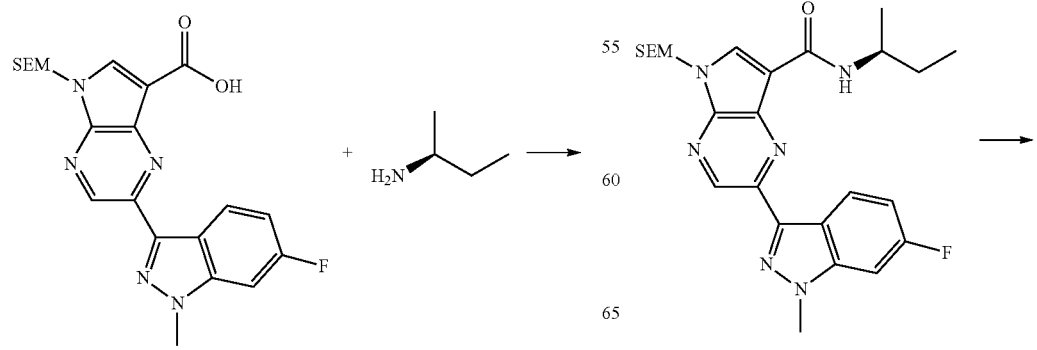

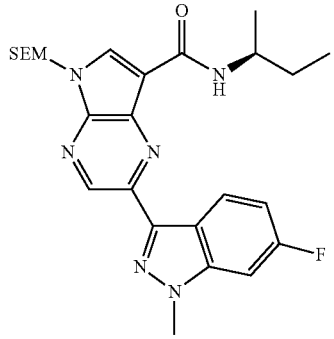

A 25 mL round-bottomed flask was charged with 2-(6-fluoro-1-methyl-1H-indazol-3-yl)-5-(2-trimethylsilanyl-ethoxymethyl)-5H-pyrrolo[2,3-b]pyrazine-7-carboxylic acid (50 mg, 0.11 mmol), (S)-butan-2-amine (9 mg, 0.12 mmol), and HATU (45 mg, 0.12 mmol). Then added acetonitrile (1 mL) followed by N,N-diisopropylethylamine (0.09 mL, 0.55 mmol). The reaction mixture was stirred at room temperature overnight then quenched with water. The mixture was extracted with ethyl acetate (3×). The organic layers were combined, dried over Na$_2$SO$_4$, and concentrated. The residue was purified by chromatography over SiO$_2$ with EtOAc/heptanes (gradient: 0-50% EtOAc) to afford 40 mg (71%) of 2-(6-fluoro-1-methyl-1H-indazol-3-yl)-5-(2-trimethylsilanyl-ethoxymethyl)-5H-pyrrolo[2,3-b]pyrazine-7-carboxylic acid ((S)-sec-butyl)-amide as a white solid. [M+Na]$^+$=519.

Step 2

2-(6-Fluoro-1-methyl-1H-indazol-3-yl)-5H-pyrrolo[2,3-b]pyrazine-7-carboxylic acid ((S)-secbutyl)-amide -continued

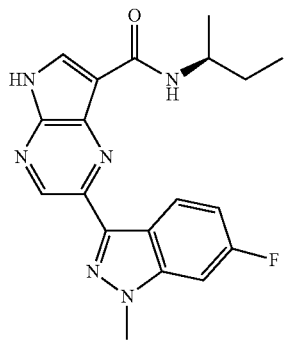 [SMILES: CC[C@H](C)NC(=O)c1c[nH]c2ncc(-c3nn(C)c4cc(F)ccc34)nc12]

In a 10 mL round-bottom flask, 2-(6-fluoro-1-methyl-1H-indazol-3-yl)-5-(2-trimethylsilanyl-ethoxymethyl)-5H-pyrrolo[2,3-b]pyrazine-7-carboxylic acid ((S)-sec-butyl)-amide (40 mg, 0.080 mmol) and TFA (0.9 ml, 11.7 mmol) were combined with dichloromethane (3 ml) to give an orange solution. The reaction mixture was stirred at room temperature for 2.5 h then concentrated under reduced pressure. The resultant crude solid was dissolved in dichloromethane (3 mL) and ethylenediamine (0.38 ml, 5.6 mmol) was added. The reaction mixture was stirred at room temperature for 18 h then concentrated and the residue was precipitated with water. The suspension was stirred for 1 h and the crude solid collected by filtration. The crude solid was purified by trituration (hot dichloromethane/heptane) to afford 19 mg (67%) of 2-(6-fluoro-1-methyl-1H-indazol-3-yl)-5H-pyrrolo[2,3-b]pyrazine-7-carboxylic acid ((S)-sec-butyl)-amide as an off-white solid. [M+H]$^+$=367; $^1$H NMR (300 MHz, DMSO-d$_6$) δ: 12.77 (br. s., 1H), 9.09 (s, 1H), 8.43 (s, 1H), 8.43 (dd, J=9.1, 5.5 Hz, 1H), 8.00 (d, J=8.7 Hz, 1H), 7.70 (dd, J=9.8, 1.9 Hz, 1H), 7.19 (td, J=9.1, 2.3 Hz, 1H), 4.15 (s, 3H), 4.03-4.14 (m, 1H), 1.57-1.73 (m, 2H), 1.28 (d, J=6.4 Hz, 3H).

Example 179

2-(6-Fluoro-1-methyl-1H-indazol-3-yl)-5H-pyrrolo[2,3-b]pyrazine-7-carboxylic acid ((S)-1-methoxymethyl-3-methyl-butyl)-amide

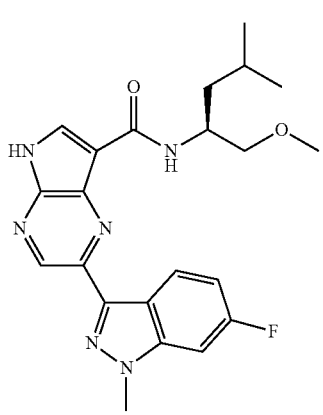 [SMILES: COC[C@H](CC(C)C)NC(=O)c1c[nH]c2ncc(-c3nn(C)c4cc(F)ccc34)nc12]

Step 1

2-(6-Fluoro-1-methyl-1H-indazol-3-yl)-5-(2-trimethylsilanyl-ethoxymethyl)-5H-pyrrolo[2,3-b]pyrazine-7-carboxylic acid ((S)-1-hydroxymethyl-3-methyl-butyl)-amide

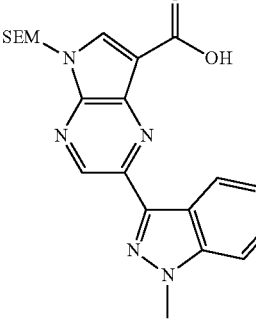

+

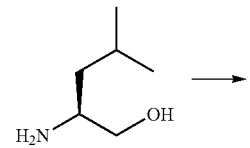

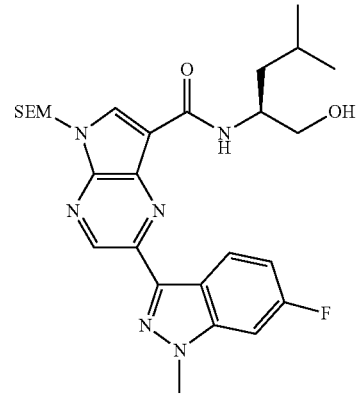

A 25 mL round-bottomed flask was charged with 2-(6-fluoro-1-methyl-1H-indazol-3-yl)-5-(2-trimethylsilanyl-ethoxymethyl)-5H-pyrrolo[2,3-b]pyrazine-7-carboxylic acid (100 mg, 0.226 mmol), (S)-2-amino-4-methylpentan-1-ol (28 mg, 0.24 mmol), and HATU (90 mg, 0.24 mmol). Then added acetonitrile (2 mL) followed by N,N-diisopropylethylamine (0.13 mL, 0.77 mmol). The reaction mixture was stirred at room temperature overnight then quenched with water. The mixture was extracted with ethyl acetate (3×). The organic layers were combined, dried over Na$_2$SO$_4$, and concentrated to afford 73 mg (59%) of 2-(6-fluoro-1-methyl-1H-indazol-3-yl)-5-(2-trimethylsilanyl-ethoxymethyl)-5H-pyrrolo[2,3-b]pyrazine-7-carboxylic acid ((S)-1-hydroxymethyl-3-methyl-butyl)-amide as a white solid. MS: [M+H]+=541.

Step 2

2-(6-Fluoro-1-methyl-1H-indazol-3-yl)-5-(2-trimethylsilanyl-ethoxymethyl)-5H-pyrrolo[2,3-b]pyrazine-7-carboxylic acid ((S)-1-methoxymethyl-3-methyl-butyl)-amide

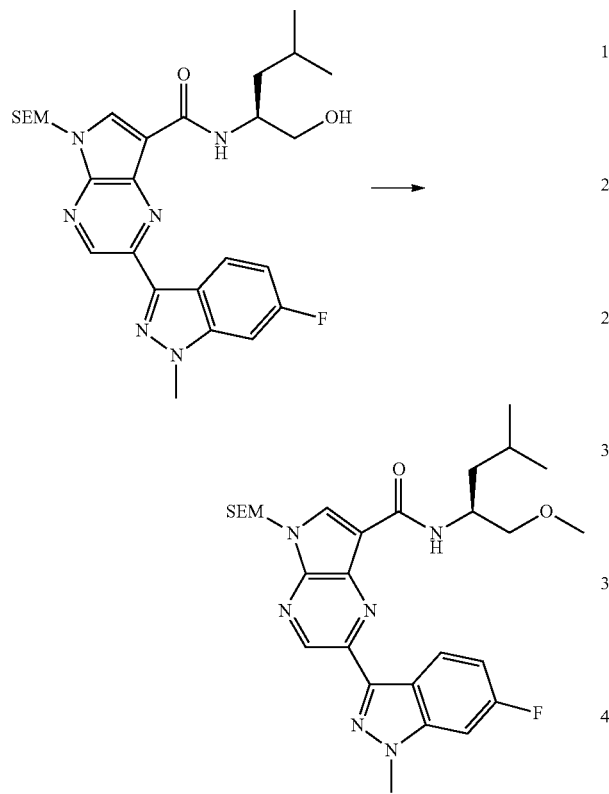

In a 10 mL round-bottomed flask, 2-(6-fluoro-1-methyl-1H-indazol-3-yl)-5-(2-trimethylsilanyl-ethoxymethyl)-5H-pyrrolo[2,3-b]pyrazine-7-carboxylic acid ((S)-1-hydroxymethyl-3-methyl-butyl)-amide (73 mg, 0.135 mmol) was dissolved in THF (1.4 ml) to give a colorless solution. The reaction was cooled in an ice bath and crushed KOH (76 mg, 1.35 mmol), 18-crown-6 (36 mg, 0.135 mmol), and iodomethane (9 µl, 0.135 mmol) were added successively. The reaction mixture was stirred at 0° C. for 1 h after which the ice bath was removed. The reaction mixture was stirred at room temperature for 2 h then diluted with dichloromethane (10 mL) and washed with aqueous ammonium chloride (10 mL), water (10 mL), and saturated sodium bicarbonate (10 mL). The organic layer was dried over $Na_2SO_4$ and concentrated. The crude material was purified by chromatography over $SiO_2$ with EtOAc/heptane (gradient: 0%-70% EtOAc) to afford 38 mg (50%) of 2-(6-fluoro-1-methyl-1H-indazol-3-yl)-5-(2-trimethylsilanyl-ethoxymethyl)-5H-pyrrolo[2,3-b]pyrazine-7-carboxylic acid ((S)-1-methoxymethyl-3-methyl-butyl)-amide as an off-white solid. 1H NMR (300 MHz, DMSO-$d_6$) δ: 9.18 (s, 1H), 8.64 (s, 1H), 8.52 (dd, J=9.1, 5.3 Hz, 1H), 8.15 (d, J=9.4 Hz, 1H), 7.72 (dd, J=9.6, 2.1 Hz, 1H), 7.13 (td, J=9.1, 1.9 Hz, 1H), 5.73 (s, 2H), 4.41 (td, J=9.0, 5.1 Hz, 1H), 4.17 (s, 3H), 3.60 (t, J=7.9 Hz, 2H), 3.44-3.55 (m, 2H), 3.27 (s, 3H), 1.48-1.72 (m, 3H), 0.91 (d, J=6.0 Hz, 3H), 0.86 (d, J=6.0 Hz, 3H), 0.85 (t, J=7.6 Hz, 2H), −0.08 (s, 9H).

Step 3

2-(6-Fluoro-1-methyl-1H-indazol-3-yl)-5H-pyrrolo[2,3-b]pyrazine-7-carboxylic acid ((S)-1-methoxymethyl-3-methyl-butyl)-amide

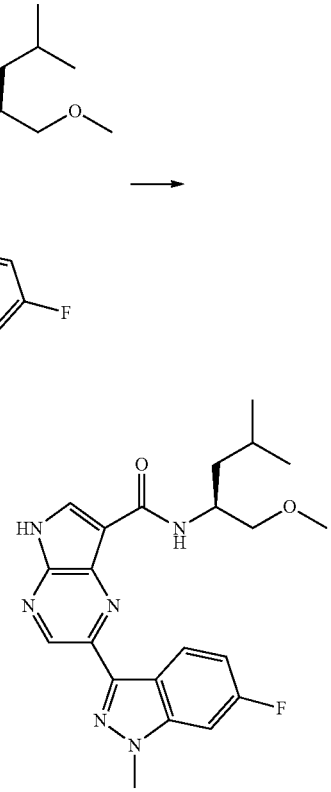

In a 10 mL round-bottom flask, 2-(6-fluoro-1-methyl-1H-indazol-3-yl)-5-(2-trimethylsilanyl-ethoxymethyl)-5H-pyrrolo[2,3-b]pyrazine-7-carboxylic acid ((S)-1-methoxymethyl-3-methyl-butyl)-amide (35 mg, 0.063 mmol) and TFA (0.6 ml, 7.8 mmol) were combined with dichloromethane (2 ml) to give an orange solution. The reaction mixture was stirred at room temperature for 2.5 h then concentrated under reduced pressure. The resultant crude solid was dissolved in dichloromethane (1 mL) and ethylenediamine (0.32 ml, 4.7 mmol) was added. The reaction mixture was stirred at room temperature for 18 h then concentrated and the residue was precipitated with water. The suspension was stirred for 1 h and the crude solid collected by filtration. The crude solid was purified by trituration (hot dichloromethane/heptane) to afford 16 mg (60%) of 2-(6-fluoro-1-methyl-1H-indazol-3-yl)-5H-pyrrolo[2,3-b]pyrazine-7-carboxylic acid ((S)-1-methoxymethyl-3-methyl-butyl)-amide as a white solid. MS: [M+H]+=425, 1H NMR (300 MHz, DMSO-$d_6$) δ: 12.87 (s, 1H), 9.13 (s, 1H), 8.53 (dd, J=8.7, 5.3 Hz, 1H), 8.44 (s, 1H), 8.17 (d, J=9.4 Hz, 1H), 7.71 (dd, J=9.8, 2.3 Hz, 1H), 7.11 (td, J=9.1, 2.3 Hz, 1H), 4.41 (td, J=9.1, 4.9 Hz, 1H), 4.16 (s, 3H), 3.52 (dd, J=9.4, 4.2 Hz, 1H), 3.46 (dd, J=9.4, 4.2 Hz, 1H), 3.27 (s, 3H), 1.48-1.75 (m, 3H), 0.91 (d, J=6.4 Hz, 3H), 0.86 (d, J=6.0 Hz, 3H).

Example 180

2-(6-Fluoro-1-methyl-1H-indazol-3-yl)-5H-pyrrolo[2,3-b]pyrazine-7-carboxylic acid ((R)-secbutyl)-amide

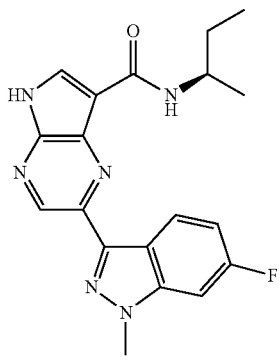 [SMILES: CC[C@@H](C)NC(=O)c1c[nH]c2ncc(-c3nn(C)c4cc(F)ccc34)nc12]

Prepared according to the procedure outlined in Example 178, substituting (R)-butan-2-amine for (S)-butan-2-amine in Step 1. The final compound was isolated as an off-white solid, 17 mg (82%); [M+H]$^+$=367; $^1$H NMR (300 MHz, DMSO-d$_6$) δ: 12.76 (br. s., 1H), 9.10 (s, 1H), 8.43 (s, 1H), 8.43 (dd, J=8.7, 5.4 Hz, 2H), 8.01 (d, J=8.7 Hz, 1H), 7.71 (dd, J=9.8, 2.3 Hz, 1H), 7.19 (td, J=9.1, 1.9 Hz, 1H), 4.15 (s, 3H), 4.02-4.14 (m, 1H), 1.56-1.75 (m, 2H), 1.28 (d, J=6.8 Hz, 3H), 0.96 (t, J=7.6 Hz, 3H).

Example 181

2-(6-Fluoro-1-methyl-1H-indazol-3-yl)-5H-pyrrolo[2,3-b]pyrazine-7-carboxylic acid ((S)-2-methoxy-1-methyl-ethyl)-amide

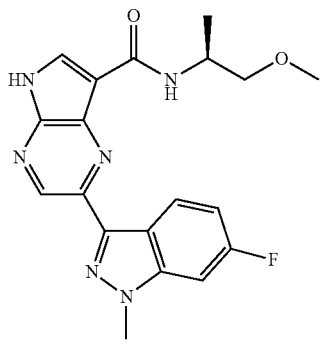 [SMILES: COC[C@H](C)NC(=O)c1c[nH]c2ncc(-c3nn(C)c4cc(F)ccc34)nc12]

Prepared according to the procedure outlined in Example 178, substituting (S)-1-methoxypropan-2-amine hydrochloride for (S)-butan-2-amine in Step 1. The final compound was isolated as an off-white solid, 27 mg (73%); MS: [M+Na]$^+$= 405; $^1$H NMR (300 MHz, DMSO-d$_6$) δ: 12.85 (br. s., 1H), 9.12 (s, 1H), 8.54 (dd, J=9.1, 5.3 Hz, 1H), 8.44 (s, 1H), 8.21 (d, J=8.3 Hz, 1H), 7.70 (dd, J=9.8, 2.3 Hz, 1H), 7.16 (td, J=9.1, 2.3 Hz, 1H), 4.30-4.47 (m, 1H), 4.15 (s, 3H), 3.50 (qd, J=9.3, 4.5 Hz, 2H), 3.28 (s, 3H), 1.31 (d, J=6.4 Hz, 3H).

Example 182

2-(6-Fluoro-1-methyl-1H-indazol-3-yl)-5H-pyrrolo[2,3-b]pyrazine-7-carboxylic acid ((S)-1-methyl-2-trideuteromethoxy-ethyl)-amide

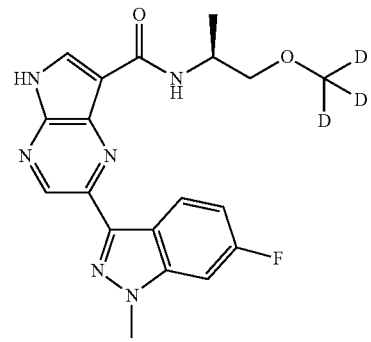 [SMILES: [2H]C([2H])([2H])OC[C@H](C)NC(=O)c1c[nH]c2ncc(-c3nn(C)c4cc(F)ccc34)nc12]

Step 1

2-(6-Fluoro-1-methyl-1H-indazol-3-yl)-5-(2-trimethylsilanyl-ethoxymethyl)-5H-pyrrolo[2,3-b]pyrazine-7-carboxylic acid ((S)-2-hydroxy-1-methyl-ethyl)-amide

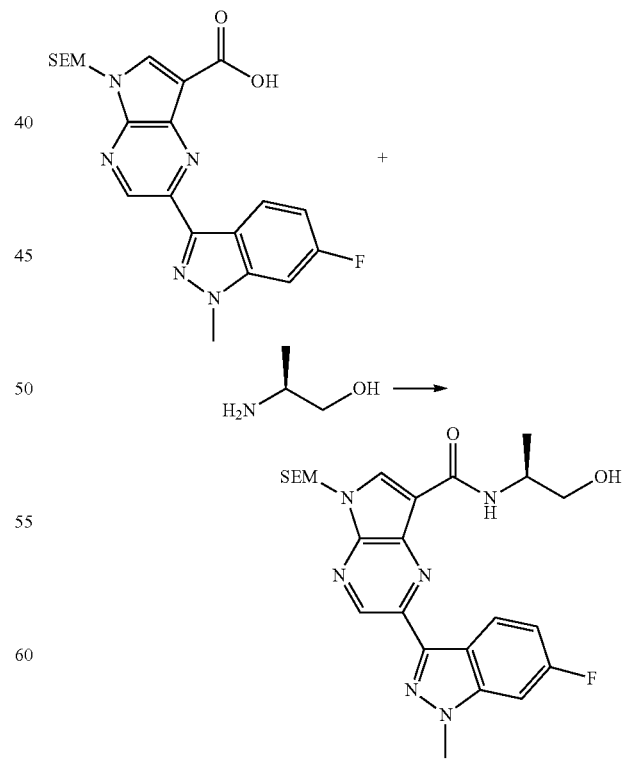

A 25 mL round-bottomed flask was charged with 2-(6-fluoro-1-methyl-1H-indazol-3-yl)-5-(2-trimethylsilanylethoxymethyl)-5H-pyrrolo[2,3-b]pyrazine-7-carboxylic acid (115 mg, 0.26 mmol), (S)-2-aminopropan-1-ol (0.21 ul, 0.27 mmol), and HATU (104 mg, 0.27 mmol). Then added acetonitrile (2 mL) followed by N,N-diisopropylethylamine (0.2 mL, 1.12 mmol). The yellow reaction mixture was stirred at room temperature overnight then quenched with water and extracted with EtOAc (3×). The organic layers were combined, dried over sodium sulfate, filtered and concentrated to provide 76 mg (57%) of 2-(6-fluoro-1-methyl-1H-indazol-3-yl)-5-(2-trimethylsilanyl-ethoxymethyl)-5H-pyrrolo[2,3-b]pyrazine-7-carboxylic acid ((S)-2-hydroxy-1-methyl-ethyl)-amide as a white solid.

Step 2

2-(6-Fluoro-1-methyl-1H-indazol-3-yl)-5-(2-trimethylsilanyl-ethoxymethyl)-5H-pyrrolo[2,3-b]pyrazine-7-carboxylic acid ((S)-1-methyl-2-trideuteromethoxy-ethyl)-amide

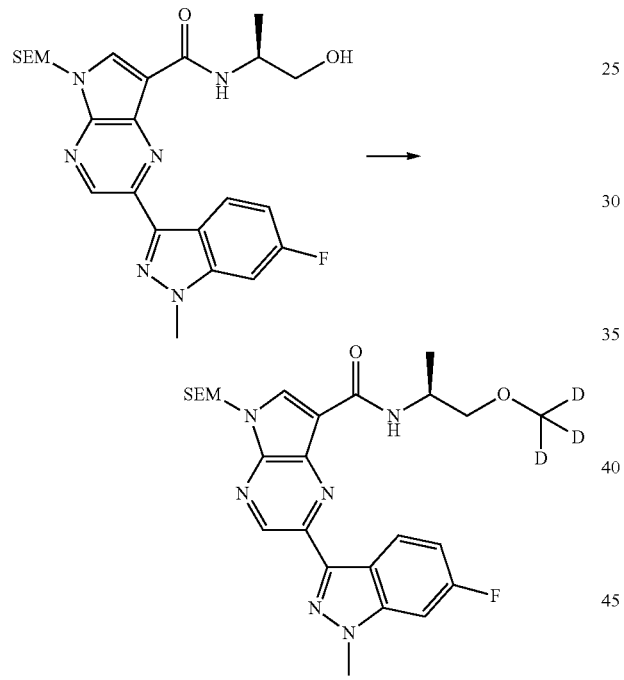

In a 10 mL round-bottomed flask, 2-(6-fluoro-1-methyl-1H-indazol-3-yl)-5-(2-trimethylsilanyl-ethoxymethyl)-5H-pyrrolo[2,3-b]pyrazine-7-carboxylic acid ((S)-2-hydroxy-1-methyl-ethyl)-amide (70 mg, 0.14 mmol) was dissolved in THF (1.4 ml) to give a colorless solution. The reaction was cooled in an ice bath and crushed KOH (91 mg, 1.62 mmol), 18-crown-6 (44 mg, 0.166 mmol), and iodotrideuteromethane (9 μl, 0.147 mmol) were added successively. The reaction mixture was stirred at 0° C. for 1 h after which the ice bath was removed. The reaction mixture was stirred at room temperature for 2 h then diluted with dichloromethane (10 mL) and washed with aqueous ammonium chloride (10 mL), water (10 mL), and saturated sodium bicarbonate (10 mL). The organic layer was dried over $Na_2SO_4$ and concentrated. The crude material was purified by chromatography over $SiO_2$ with EtOAc/heptane (gradient: 5%-60% EtOAc) to afford 38 mg (53%) of 2-(6-fluoro-1-methyl-1H-indazol-3-yl)-5-(2-trimethylsilanyl-ethoxymethyl)-5H-pyrrolo[2,3-b]pyrazine-7-carboxylic acid ((S)-1-methyl-2-trideuteromethoxy-ethyl)-amide as a white solid. MS: $[M+Na]^+=538$.

Step 3

2-(6-Fluoro-1-methyl-1H-indazol-3-yl)-5H-pyrrolo[2,3-b]pyrazine-7-carboxylic acid ((S)-1-methyl-2-trideuteromethoxy-ethyl)-amide

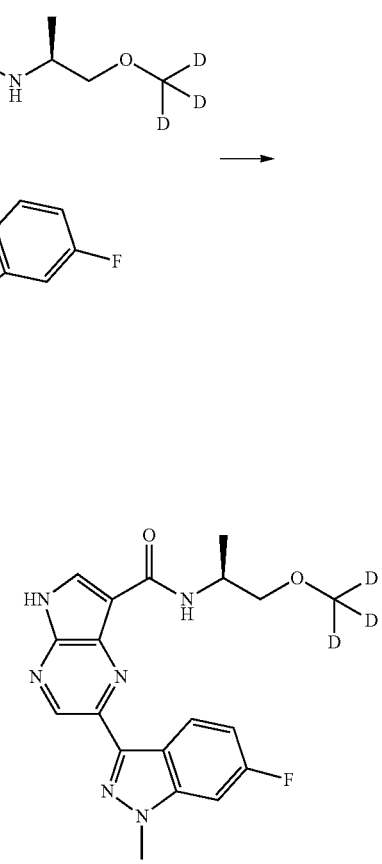

In a 10 mL round-bottom flask, 2-(6-fluoro-1-methyl-1H-indazol-3-yl)-5-(2-trimethylsilanyl-ethoxymethyl)-5H-pyrrolo[2,3-b]pyrazine-7-carboxylic acid ((S)-1-methyl-2-trideuteromethoxy-ethyl)-amide (38 mg, 0.074 mmol) and TFA (0.5 ml, 6.5 mmol) were combined with dichloromethane (1.5 ml) to give an orange solution. The reaction mixture was stirred at room temperature for 2.5 h then concentrated under reduced pressure. The resultant crude solid was dissolved in dichloromethane (1 mL) and ethylenediamine (0.10 ml, 1.5 mmol) was added. The reaction mixture was stirred at room temperature for 18 h then concentrated and the residue was precipitated with water. The suspension was stirred for 1 h and the crude solid collected by filtration. The crude solid was purified by trituration (dichloromethane/heptane) to afford 27 mg (96%) of 2-(6-fluoro-1-methyl-1H-indazol-3-yl)-5H-pyrrolo[2,3-b]pyrazine-7-carboxylic acid ((S)-1-methyl-2-trideuteromethoxy-ethyl)-amide as an off-white solid. MS: $[M+H]^+=386$; $^1$H NMR (300 MHz, DMSO-$d_6$) δ: 12.85 (br. s., 1H), 9.11 (s, 1H), 8.54 (dd, J=8.9, 5.5 Hz, 1H), 8.44 (s, 1H), 8.21 (d, J=8.3 Hz, 1H), 7.70 (dd, J=9.8, 2.3 Hz, 1H), 7.15 (td, J=9.1, 2.3 Hz, 1H), 4.25-4.45 (m, 1H), 4.15 (s, 3H), 3.49 (qd, J=9.3, 4.5 Hz, 2H), 1.31 (d, J=6.8 Hz, 3H).

Example 183

2-(6-Fluoro-1-methyl-1H-indazol-3-yl)-5H-pyrrolo[2,3-b]pyrazine-7-carboxylic acid (3-hydroxy-1,3-dimethyl-butyl)-amide

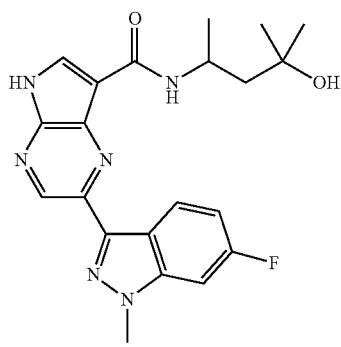 [SMILES: CC(CC(C)(C)O)NC(=O)c1c[nH]c2ncc(-c3nn(C)c4cc(F)ccc34)nc12]

Step 1

2-(6-Fluoro-1-methyl-1H-indazol-3-yl)-5-(2-trimethylsilanyl-ethoxymethyl)-5H-pyrrolo[2,3-b]pyrazine-7-carboxylic acid (3-hydroxy-1,3-dimethyl-butyl)-amide

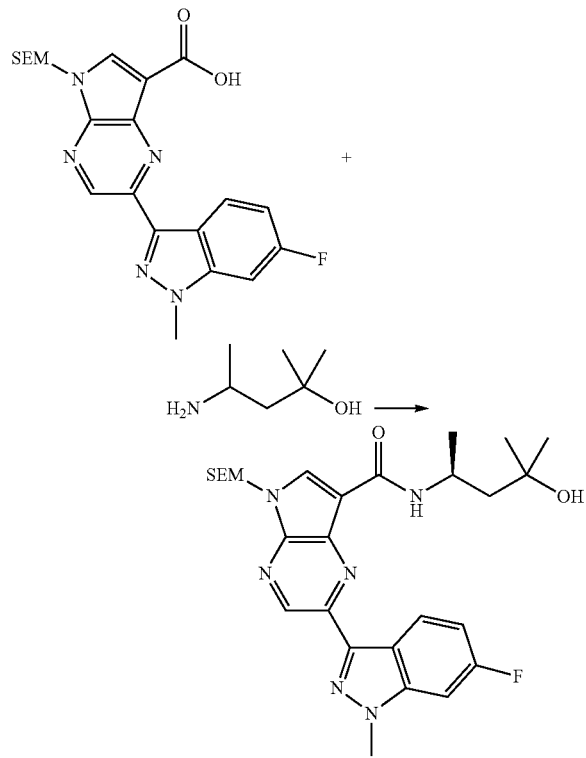

A 25 mL round-bottomed flask was charged with 2-(6-fluoro-1-methyl-1H-indazol-3-yl)-5-(2-trimethylsilanyl-ethoxymethyl)-5H-pyrrolo[2,3-b]pyrazine-7-carboxylic acid (98 mg, 0.22 mmol), 4-amino-2-methylpentan-2-ol [prepared according to US 2003/0171584 A1] (27 mg, 0.23 mmol), and HATU (89 mg, 0.23 mmol). Then added acetonitrile (2 mL) followed by N,N-diisopropylethylamine (0.2 mL, 1.12 mmol). The yellow reaction mixture was stirred at room temperature overnight then diluted with EtOAc and washed with water (3×). The organic layer was combined, dried over Na$_2$SO$_4$, and concentrated. The residue was purified by chromatography over SiO$_2$ with EtOAc/heptanes (gradient: 5-90% EtOAc) to afford 75 mg (63%) of 2-(6-fluoro-1-methyl-1H-indazol-3-yl)-5-(2-trimethylsilanyl-ethoxymethyl)-5H-pyrrolo[2,3-b]pyrazine-7-carboxylic acid (3-hydroxy-1,3-dimethyl-butyl)-amide as an off-white solid. MS: [M+H]$^+$=541.

Step 2

2-(6-Fluoro-1-methyl-1H-indazol-3-yl)-5H-pyrrolo[2,3-b]pyrazine-7-carboxylic acid (3-hydroxy-1,3-dimethyl-butyl)-amide

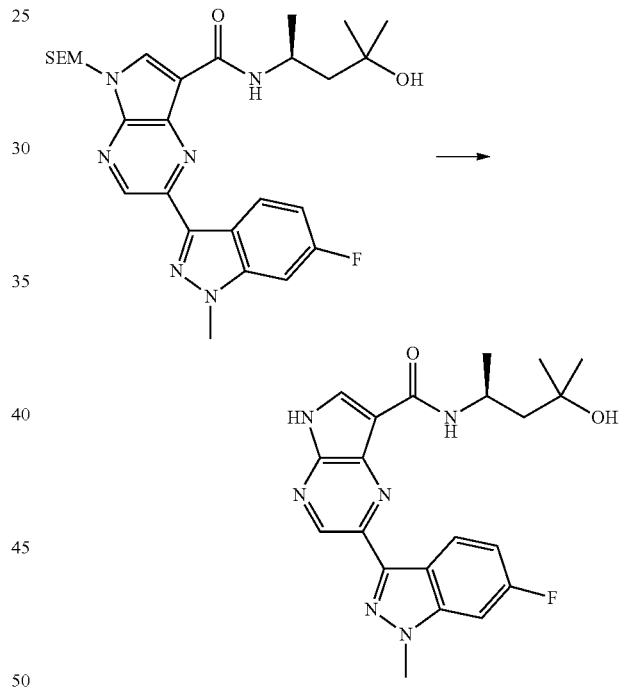

In a 125 mL round-bottomed flask, 2-(6-fluoro-1-methyl-1H-indazol-3-yl)-5-(2-trimethylsilanyl-ethoxymethyl)-5H-pyrrolo[2,3-b]pyrazine-7-carboxylic acid (3-hydroxy-1,3-dimethyl-butyl)-amide (25 mg, 0.046 mmol), cesium fluoride (70 mg, 0.46 mmol) and 18-crown-6 (12 mg, 0.046 mmol) were combined with acetonitrile to give an off-white suspension. The reaction was stirred at reflux for 72 h. A large excess of CsF and 18-crown-6 was added and the reaction was heated for an additional 24 h. The reaction mixture was diluted with ethyl acetate and washed with water. The organic layer was dried over Na$_2$SO$_4$ and concentrated. The crude material was suspended in water and collected by filtration then triturated with 1:2 dichloromethane/heptane to afford 4 mg (21%) of 2-(6-fluoro-1-methyl-1H-indazol-3-yl)-5H-pyrrolo[2,3-b]pyrazine-7-carboxylic acid (3-hydroxy-1,3-dimethyl-butyl)-amide as a yellow solid. MS: [M+Na]$^+$=433, $^1$H NMR (300

MHz, DMSO-$d_6$) δ: 12.83 (br. s., 1H), 9.10 (s, 1H), 8.57 (dd, J=8.9, 5.5 Hz, 1H), 8.41 (d, J=2.3 Hz, 1H), 8.15 (d, J=8.3 Hz, 1H), 7.71 (dd, J=9.8, 1.9 Hz, 1H), 7.20 (td, J=9.1, 2.3 Hz, 1H), 4.35 (s, 1H), 4.29-4.43 (m, 1H), 4.16 (s, 3H), 1.83 (dd, J=14.4, 7.9 Hz, 1H), 1.73 (dd, J=16.6, 4.9 Hz, 1H), 1.31 (d, J=6.4 Hz, 3H), 1.15 (s, 3H), 1.12 (s, 3H).

Example 184

2-(6-Fluoro-1-methyl-1H-indazol-3-yl)-5H-pyrrolo[2,3-b]pyrazine-7-carboxylic acid (1-methylbutyl)-amide

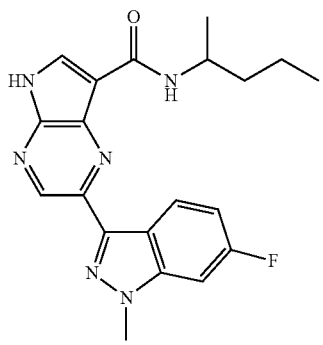 [SMILES: CCCC(C)NC(=O)c1c[nH]c2ncc(-c3nn(C)c4cc(F)ccc34)nc12]

Prepared according to the procedure outlined in Example 178, substituting 1-methylbutylamine for (S)-butan-2-amine in Step 1. The final compound was isolated as a light yellow solid, 25 mg (96%); MS: [M+H]⁺=403; ¹H NMR (300 MHz, DMSO-$d_6$) δ: 12.83 (br. s., 1H), 9.10 (s, 1H), 8.42 (s, 1H), 8.43 (dd, J=8.9, 5.3 Hz, 1H), 8.00 (d, J=8.7 Hz, 1H), 7.71 (dd, J=9.8, 1.9 Hz, 1H), 7.18 (td, J=9.1, 2.3 Hz, 1H), 4.15 (s, 3H), 4.18 (quin, J=6.8 Hz, 1H), 1.55-1.67 (m, 2H), 1.36-1.48 (m, 2H), 1.28 (d, J=6.4 Hz, 3H), 0.89 (t, J=7.4 Hz, 3H).

Example 185

2-(6-Fluoro-1-methyl-1H-indazol-3-yl)-5H-pyrrolo[2,3-b]pyrazine-7-carboxylic acid (3,3,3-trifluoro-1-methyl-propyl)-amide

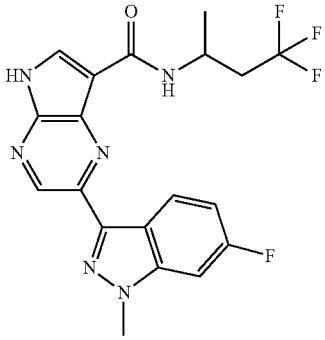 [SMILES: CC(CC(F)(F)F)NC(=O)c1c[nH]c2ncc(-c3nn(C)c4cc(F)ccc34)nc12]

Step 1

3,3,3-Trifluoro-1-methyl-propylamine hydrochloride

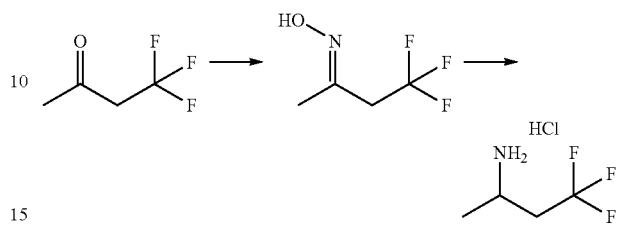

The amine salt was prepared according to the procedure outlined in Gassen, K.-R; Kirmse, W. *Chem. Ber.*, 1986, 119, 2233-2248.

Step 2

2-(6-Fluoro-1-methyl-1H-indazol-3-yl)-5H-pyrrolo[2,3-b]pyrazine-7-carboxylic acid (3,3,3-trifluoro-1-methyl-propyl)-amide

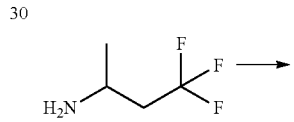

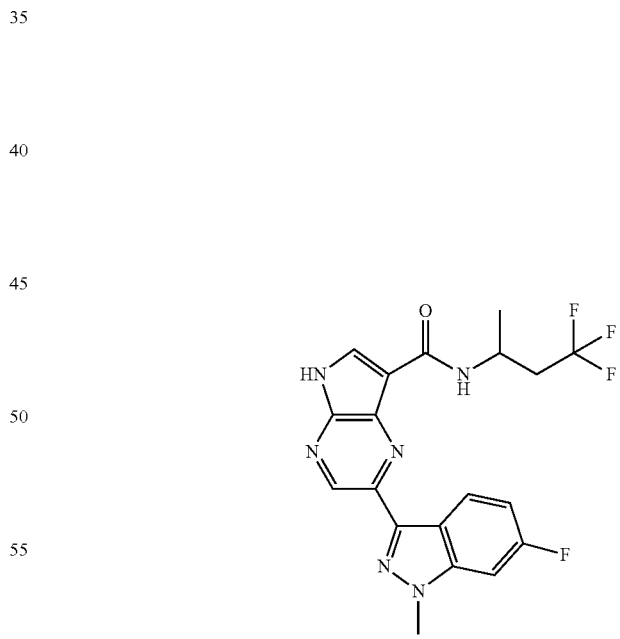

Prepared according to the procedure outlined in Example 178, substituting 3,3,3-trifluoro-1-methyl-propylamine hydrochloride for (S)-butan-2-amine in Step 1. The final compound was isolated as an off-white solid, 16 mg (38%); MS: [M+H]⁺=421; ¹H NMR (300 MHz, DMSO-$d_6$) δ: 12.83 (br. s., 1H), 9.10 (s, 1H), 8.45-8.46 (m, 1H), 8.48 (dd, J=9.0, 5.3 Hz, 1H), 8.17 (d, J=8.3 Hz, 1H), 7.70 (dd, J=9.8, 2.3 Hz, 1H), 7.18 (td, J=9.1, 2.3 Hz, 1H), 4.42-4.59 (m, 1H), 4.15 (s, 3H), 2.70-2.78 (m, 1H), 2.62-2.70 (m, 1H), 1.43 (d, J=6.8 Hz, 3H).

Example 186

2-(6-Fluoro-1-methyl-1H-indazol-3-yl)-5H-pyrrolo[2,3-b]pyrazine-7-carboxylic acid (2-cyclopropyl-1-methyl-ethyl)-amide

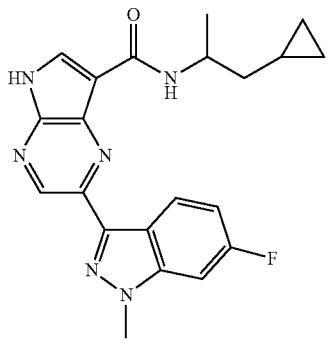 [SMILES: CC(CC1CC1)NC(=O)c1c[nH]c2ncc(-c3nn(C)c4cc(F)ccc34)nc12]

Step 1

2-Methyl-propane-2-sulfinic acid [2-cyclopropyl-1-methyl-eth-(E)-ylidene]-amide

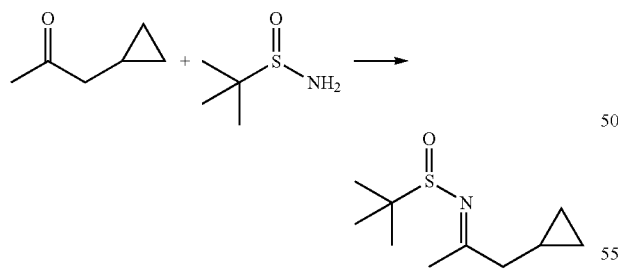

A 25 mL round bottomed flask was charged with Ti(OEt)₄ (technical grade, 0.37 mL, 1.4 mmol) and 1-cyclopropylpropan-2-one (79.0 mg, 0.81 mmol) in THF (1.45 mL), under an argon atmosphere. Then 2-methylpropane-2-sulfinamide (88.7 mg, 0.73 mmol) was added and the reaction mixture was heated to reflux overnight. After cooling to room temperature the reaction mixture was poured onto brine (1.7 mL), with rapid stirring. The resulting suspension was filtered through a pad of celite. The filtrate was concentrated under reduced pressure to afford crude 2-methyl-propane-2-sulfinic acid [2-cyclopropyl-1-methyl-eth-(E)-ylidene]-amide which was taken directly to the next step without purification.

Step 2

2-Methyl-propane-2-sulfinic acid (2-cyclopropyl-1-methyl-ethyl)-amide

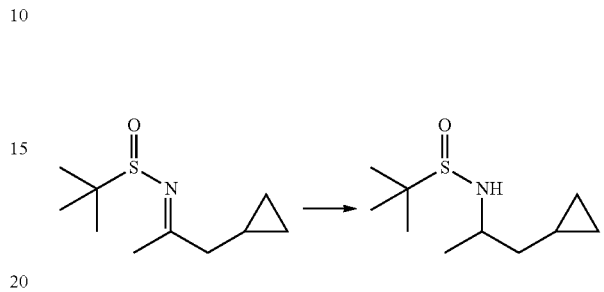

A 25 mL round-bottomed flask was charged with 2-methyl-propane-2-sulfinic acid [2-cyclopropyl-1-methyl-eth-(E)-ylidene]-amide (120 mg, 0.596 mmol) and dichloromethane (2 ml) under an argon atmosphere. The reaction mixture was cooled in a −78° C. bath. DIBAL-H (0.80 ml, 0.800 mmol) was added slowly dropwise. The reaction mixture was allowed to stir for 45 min after which the cooling bath was removed. The reaction mixture was stirred for 15 min at room temperature, after which the reaction mixture was returned to the cooling bath. The reaction was quenched with MeOH (0.08 mL, 1.98 mmol). The reaction mixture was diluted with dichloromethane (8 mL) and 1.0 M aqueous Na⁺K⁺ tartrate solution (5 mL). After stirring at room temperature overnight, the mixture was extracted with dichloromethane. The organic layer was concentrated to afford 50 mg of 2-methyl-propane-2-sulfinic acid (2-cyclopropyl-1-methyl-ethyl)-amide which was used in the next step directly without purification.

Step 3

2-Cyclopropyl-1-methyl-ethylamine hydrochloride

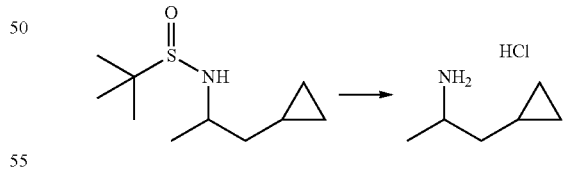

To a cooled (5° C.) 50 mL round-bottomed flask containing MeOH (10 mL) was slowly added acetyl chloride (0.10 mL, 1.41 mmol). The solution was allowed to stir for 30 min. The freshly prepared HCl in MeOH was transferred to a round-bottomed flask containing 2-methyl-propane-2-sulfinic acid (2-cyclopropyl-1-methyl-ethyl)-amide (50 mg, 0.25 mmol). After stirring for 30 min at room temperature, the reaction mixture was concentrated to afford the 2-cyclopropyl-1-methyl-ethylamine hydrochloride which was used without further purification.

MS: [M+H]⁺=100.

Step 4

2-(6-Fluoro-1-methyl-1H-indazol-3-yl)-5H-pyrrolo[2,3-b]pyrazine-7-carboxylic acid (2-cyclopropyl-1-methyl-ethyl)-amide

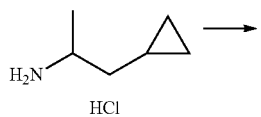

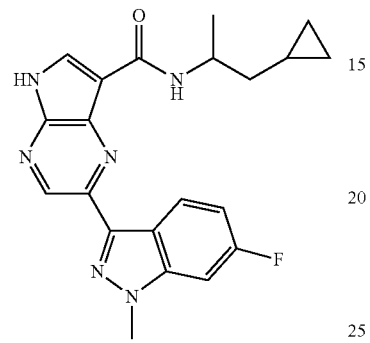

Prepared according to the procedure outlined in Example 178, substituting 2-cyclopropyl-1-methyl-ethylamine hydrochloride for (S)-butan-2-amine in Step 1. The final compound was isolated as light yellow needles, 9 mg (28%); MS: [M+H]$^+$=393; $^1$H NMR (300 MHz, DMSO-d$_6$) δ: 12.70 (br. s., 1H), 9.10 (s, 1H), 8.46 (dd, J=9.1, 5.3 Hz, 1H), 8.42 (s, 1H), 7.17 (td, J=9.1, 2.3 Hz, 1H), 4.17-4.31 (m, 1H), 4.15 (s, 3H), 1.63 (dt, J=13.7, 6.8 Hz, 1H), 1.47 (dt, J=13.7, 6.6 Hz, 1H), 1.35 (d, J=6.8 Hz, 3H), 0.72-0.93 (m, 1H), 0.32-0.43 (m, 2H), 0.08 (app. t, J=5.3 Hz, 2H).

Example 187

2-(6-Fluoro-1-methyl-1H-indazol-3-yl)-5H-pyrrolo[2,3-b]pyrazine-7-carboxylic acid (1,3-dimethyl-butyl)-amide

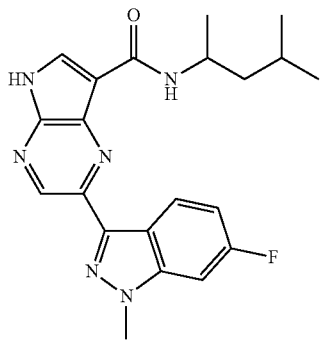 [SMILES: CC(C)CC(C)NC(=O)c1c[nH]c2ncc(-c3nn(C)c4cc(F)ccc34)nc12]

Prepared according to the procedure outlined in Example 178, substituting 1,3-dimethylbutylamine for (S)-butan-2-amine in Step 1. The final compound was isolated as light yellow needles, 24 mg (76%); MS: [M+Na]$^+$=417; $^1$H NMR (DMSO-d$_6$) δ: 12.83 (br. s., 1H), 9.09 (s, 1H), 8.42 (s, 1H), 8.41 (dd, J=8.9, 5.7 Hz, 1H), 7.98 (d, J=8.7 Hz, 1H), 7.70 (dd, J=9.8, 2.3 Hz, 1H), 7.16 (td, J=9.1, 2.3 Hz, 1H), 4.18-4.34 (m, 1H), 4.15 (s, 3H), 1.64-1.78 (m, 1H), 1.51-1.65 (m, 1H), 1.38-1.51 (m, 1H), 1.27 (d, J=6.4 Hz, 3H), 0.92 (d, J=6.4 Hz, 3H), 0.87 (d, J=6.4 Hz, 3H).

Example 188

2-(6-Fluoro-1-methyl-1H-indazol-3-yl)-5H-pyrrolo[2,3-b]pyrazine-7-carboxylic acid ((1R,2S)-2-hydroxy-1-methoxymethyl-propyl)-amide

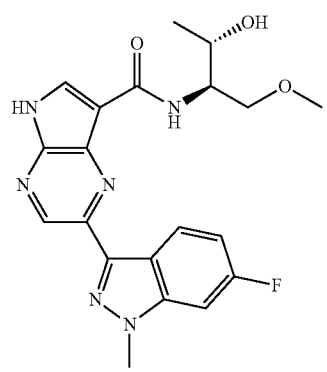

Step 1

2-(6-Fluoro-1-methyl-1H-indazol-3-yl)-5-(2-trimethylsilanyl-ethoxymethyl)-5H-pyrrolo[2,3-b]pyrazine-7-carboxylic acid ((1R,2S)-2-hydroxy-1-hydroxymethyl-propyl)-amide

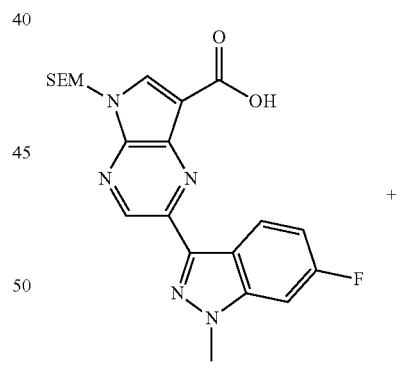

+

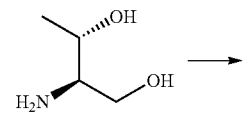

717
-continued

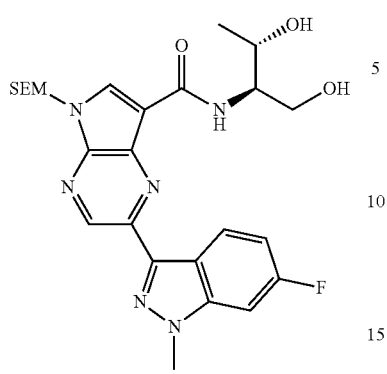

Step 2

2-(6-Fluoro-1-methyl-1H-indazol-3-yl)-5-(2-trimethylsilanyl-ethoxymethyl)-5H-pyrrolo[2,3-b]pyrazine-7-carboxylic acid ((1R,2S)-2-hydroxy-1-methoxymethyl-propyl)-amide and 2-(6-Fluoro-1-methyl-1H-indazol-3-yl)-5-(2-trimethylsilanyl-ethoxymethyl)-5H-pyrrolo[2,3-b]pyrazine-7-carboxylic acid ((1R,2S)-2-methoxy-1-methoxymethyl-propyl)-amide

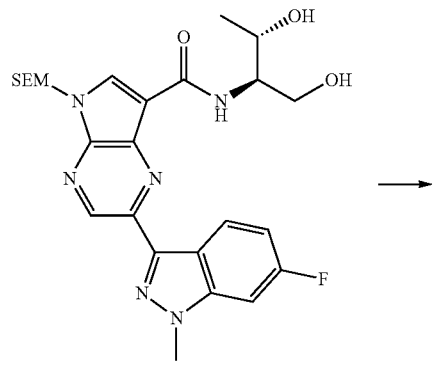 →

718
-continued

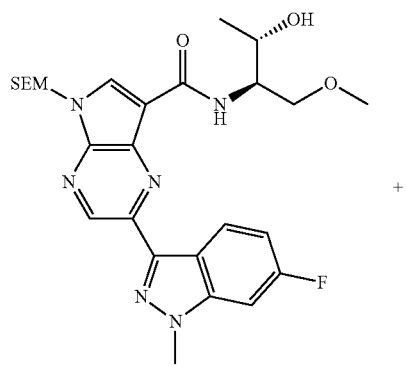

+

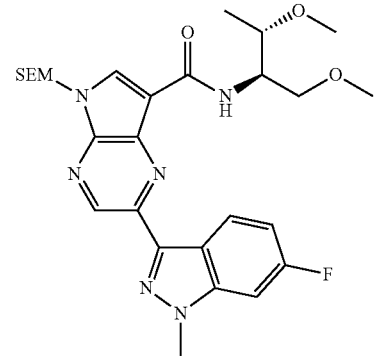

A 25 mL round-bottomed flask was charged with 2-(6-fluoro-1-methyl-1H-indazol-3-yl)-5-(2-trimethylsilanyl-ethoxymethyl)-5H-pyrrolo[2,3-b]pyrazine-7-carboxylic acid (102 mg, 0.23 mmol), (2R,3S)-2-aminobutane-1,3-diol (34 mg, 0.32 mmol), and HATU (97 mg, 0.25 mmol). Then added acetonitrile (6 mL) followed by N,N-diisopropylethylamine (0.25 mL, 1.43 mmol). The reaction mixture was stirred at room temperature overnight then quenched with water. The mixture was extracted with ethyl acetate (3×). The organic layers were combined, dried over $Na_2SO_4$, and concentrated. The residue was purified by chromatography over $SiO_2$ with EtOAc/heptanes (gradient: 5-100% EtOAc) to afford 100 mg (82%) of 2-(6-fluoro-1-methyl-1H-indazol-3-yl)-5-(2-trimethylsilanyl-ethoxymethyl)-5H-pyrrolo[2,3-b]pyrazine-7-carboxylic acid ((1R,2S)-2-hydroxy-1-hydroxymethyl-propyl)-amide as a white solid. MS: $[M+Na]^+$=551.

In a pressure tube, 2-(6-fluoro-1-methyl-1H-indazol-3-yl)-5-(2-trimethylsilanylethoxymethyl)-5H-pyrrolo[2,3-b]pyrazine-7-carboxylic acid ((1R,2S)-2-hydroxy-1-hydroxymethyl-propyl)-amide (93 mg, 0.176 mmol), silver oxide (83 mg, 0.36 mmol) and methyl iodide (200 µl, 3.2 mmol) were combined with acetonitrile to give a black suspension. The tube was wrapped in foil to exclude light. The system was placed in a sand bath and heated to 40° C. with stirring. The temperature was maintained for 21 h. Upon cooling, the reaction mixture was filtered through a pad a celite. The filtrate was concentrated. The crude material was purified by chromatography over $SiO_2$ with EtOAc/hexanes (gradient: 15%-90% EtOAc) to afford 45 mg (47%) of 2-(6-fluoro-1-methyl-1H-indazol-3-yl)-5-(2-trimethylsilanylethoxymethyl)-5H-pyrrolo[2,3-b]pyrazine-7-carboxylic acid ((1R,2S)-2-hydroxy-1-methoxymethyl-propyl)-amide as a light yellow solid ($[M+H]^+$=543) and 20 mg (20%) of 2-(6-fluoro-1-methyl-1H-indazol-3-yl)-5-(2-trimethylsilanyl-ethoxymethyl)-

5H-pyrrolo[2,3-b]pyrazine-7-carboxylic acid ((1R,2S)-2-methoxy-1-methoxymethyl-propyl)-amide as a white solid ([M+H]$^+$=557).

Step 3

2-(6-Fluoro-1-methyl-1H-indazol-3-yl)-5H-pyrrolo[2,3-b]pyrazine-7-carboxylic acid ((1R,2S)-2-hydroxy-1-methoxymethyl-propyl)-amide

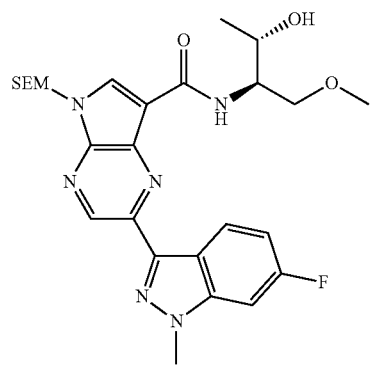

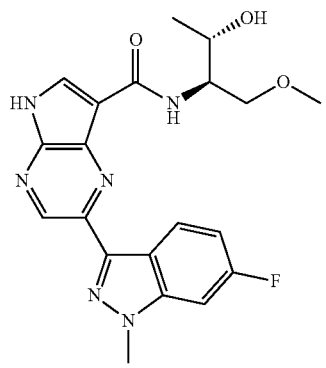 [SMILES: COC[C@@H](NC(=O)c1c[nH]c2ncc(-c3nn(C)c4cc(F)ccc34)nc12)[C@H](C)O]

In a 10 mL round-bottom flask, 2-(6-fluoro-1-methyl-1H-indazol-3-yl)-5-(2-trimethylsilanyl-ethoxymethyl)-5H-pyrrolo[2,3-b]pyrazine-7-carboxylic acid ((1R,2S)-2-hydroxy-1-methoxymethyl-propyl)-amide (44 mg, 0.081 mmol) and TFA (0.3 ml, 3.9 mmol) were combined with dichloromethane (1 ml) to give an orange solution. The reaction mixture was stirred at room temperature for 2.5 h then concentrated under reduced pressure. The resultant crude solid was dissolved in dichloromethane (1 mL) and ethylenediamine (0.15 ml, 2.2 mmol) was added. The reaction mixture was stirred at room temperature for 18 h then concentrated and the residue was precipitated with water. The suspension was stirred for 1 h and the crude solid collected by filtration. The crude solid was purified by trituration (hot dichloromethane/heptane) to afford 15 mg (46%) of 2-(6-fluoro-1-methyl-1H-indazol-3-yl)-5H-pyrrolo[2,3-b]pyrazine-7-carboxylic acid ((1R,2S)-2-hydroxy-1-methoxymethyl-propyl)-amide as an off-white solid. MS: [M+H]$^+$=413; $^1$H NMR (300 MHz, DMSO-d$_6$) δ: 12.83 (br. s., 1H), 8.62 (dd, J=8.8, 5.3 Hz, 1H), 8.44 (s, 1H), 8.30 (d, J=9.6 Hz, 1H), 7.68 (dd, J=9.6, 1.8 Hz, 1H), 7.13 (td, J=9.1, 2.0 Hz, 1H), 4.94 (d, J=5.6 Hz, 1H), 4.17-4.23 (m, 1H), 4.15 (s, 3H), 3.85-3.96 (m, 1H), 3.75 (dd, J=9.6, 5.6 Hz, 1H), 3.57 (dd, J=9.6, 3.5 Hz, 1H), 3.25 (s, 3H), 1.17 (d, J=6.1 Hz, 3H).

Example 189

2-(6-Fluoro-1-methyl-1H-indazol-3-yl)-5H-pyrrolo[2,3-b]pyrazine-7-carboxylic acid ((1R,2S)-2-hydroxy-1-methoxymethyl-propyl)-amide

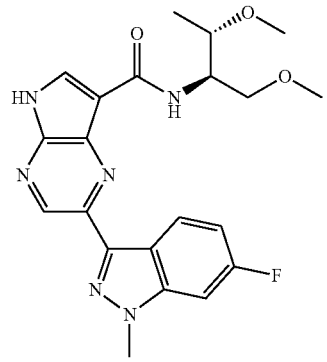 [SMILES: COC[C@@H](NC(=O)c1c[nH]c2ncc(-c3nn(C)c4cc(F)ccc34)nc12)[C@H](C)OC]

Prepared according to the procedure outlined in Example 188, Step 3, substituting 2-(6-fluoro-1-methyl-1H-indazol-3-yl)-5-(2-trimethylsilanyl-ethoxymethyl)-5H-pyrrolo[2,3-b]pyrazine-7-carboxylic acid ((1R,2S)-2-methoxy-1-methoxymethyl-propyl)-amide for 2-(6-fluoro-1-methyl-1H-indazol-3-yl)-5-(2-trimethylsilanyl-ethoxymethyl)-5H-pyrrolo[2,3-b]pyrazine-7-carboxylic acid ((1R,2S)-2-hydroxy-1-methoxymethyl-propyl)-amide. The final compound was isolated as a white solid, 11 mg (81%); MS: [M+H]$^+$=427; $^1$H NMR (DMSO-d$_6$) δ: 12.87 (br. s., 1H), 9.14 (s, 1H), 8.58 (dd, J=8.8, 5.3 Hz, 1H), 8.45 (s, 1H), 8.33 (d, J=9.6 Hz, 1H), 7.69 (dd, J=9.6, 2.0 Hz, 1H), 7.10 (td, J=9.0, 2.3 Hz, 1H), 4.38 (dq, J=9.7, 5.0 Hz, 1H), 4.16 (s, 3H), 3.69 (dd, J=10.1, 5.6 Hz, 1H), 3.56-3.60 (m, 1H), 3.56 (dd, J=10.1, 4.0 Hz, 1H), 3.28 (s, 3H), 3.25 (s, 3H), 1.17 (d, J=6.1 Hz, 3H).

Example 190

2-(6-Fluoro-1-methyl-1H-indazol-3-yl)-5H-pyrrolo[2,3-b]pyrazine-7-carboxylic acid [2-hydroxy-1-(tetrahydro-furan-2-yl)-ethyl]-amide

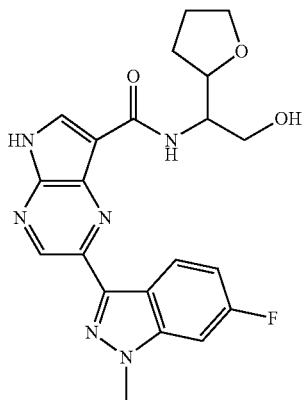 [SMILES: Cn1nc(-c2cnc3[nH]cc(C(=O)NC(CO)C4CCCO4)c3n2)c2ccc(F)cc21]

Prepared according to the procedure outlined in Example 178, substituting 2-amino-2-(tetrahydrofuran-2-yl)ethanol for (S)-butan-2-amine in Step 1. The final compound was isolated as an off-white solid (mixture of diastereomers), 10 mg (59%); MS: [M+H]$^+$=425; $^1$H NMR (300 MHz, DMSO-d$_6$) δ: 12.87 (br. s., 2H), 9.14 (s, 2H), 8.71 (dd, J=9.0, 5.5 Hz, 1H), 8.70 (dd, J=9.1, 5.2 Hz, 1H), 8.45 (s, 2H), 8.35 (t, J=9.1 Hz, 2H), 7.67 (dd, J=9.8, 1.9 Hz, 2H), 7.16 (tt, J=9.1, 2.1 Hz, 2H), 5.16 (t, J=4.2 Hz, 1H), 5.13 (t, J=4.9 Hz, 1H), 4.15 (s, 6H), 4.10-4.27 (m, 2H), 3.88 (t, J=7.9 Hz, 1H), 3.75 (t, J=8.3 Hz, 1H), 3.45-3.76 (m, 10H), 2.58-2.69 (m, 2H), 2.01-2.13 (m, 1H), 1.85-1.97 (m, 1H), 1.63-1.78 (m, 2H).

Example 191

2-(6-Fluoro-1-methyl-1H-indazol-3-yl)-5H-pyrrolo[2,3-b]pyrazine-7-carboxylic acid [2-methoxy-1-(tetrahydro-furan-2-yl)-ethyl]-amide

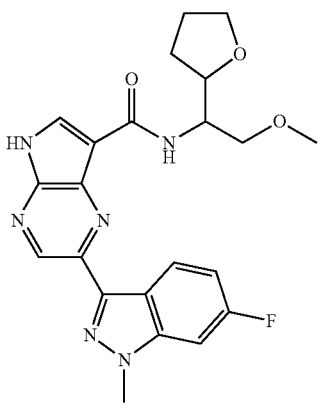 [SMILES: COCC(NC(=O)c1c[nH]c2ncc(-c3nn(C)c4cc(F)ccc34)nc12)C1CCCO1]

Prepared according to the procedure outlined in Example 179, substituting 2-amino-2-(tetrahydrofuran-2-yl)ethanol for (S)-2-amino-4-methylpentan-1-ol in Step 1. The final compound was isolated as an off-white solid (1:1 mixture of diastereomers), 12 mg (53%); MS: [M+Na]$^+$=461; $^1$H NMR (300 MHz, DMSO-d$_6$) δ: 12.88 (br. s., 2H), 9.13 (s, 2H), 8.56 (dd, J=9.1, 5.3 Hz, 2H), 8.46 (s, 2H), 8.33 (t, J=9.3 Hz, 2H), 7.70 (dd, J=9.8, 2.3 Hz, 2H), 7.15 (tt, J=9.0, 2.3 Hz, 2H), 4.26-4.41 (m, 2H), 4.16 (s, 6H), 3.86 (t, J=7.9 Hz, 1H), 3.76 (t, J=8.1 Hz, 1H), 3.43-3.74 (m, 10H), 3.27 (s, 3H), 3.26 (s, 3H), 2.56-2.67 (m, 2H), 1.99-2.11 (m, 1H), 1.86-1.98 (m, 1H), 1.64-1.82 (m, 2H).

Example 192

2-(6-Fluoro-1-methyl-1H-indazol-3-yl)-5H-pyrrolo[2,3-b]pyrazine-7-carboxylic acid ((S)-3-methanesulfonyl-1-methoxymethyl-propyl)-amide

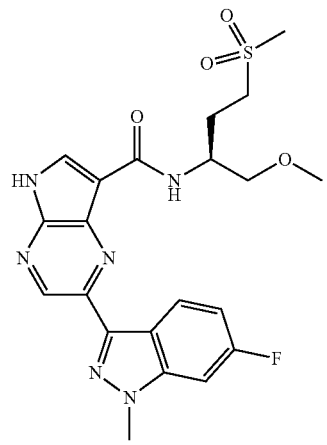 [SMILES: COC[C@H](CCS(C)(=O)=O)NC(=O)c1c[nH]c2ncc(-c3nn(C)c4cc(F)ccc34)nc12]

Step 1

2-(6-Fluoro-1-methyl-1H-indazol-3-yl)-5-(2-trimethylsilanyl-ethoxymethyl)-5H-pyrrolo[2,3-b]pyrazine-7-carboxylic acid ((S)-1-hydroxymethyl-3-methylsulfanyl-propyl)-amide

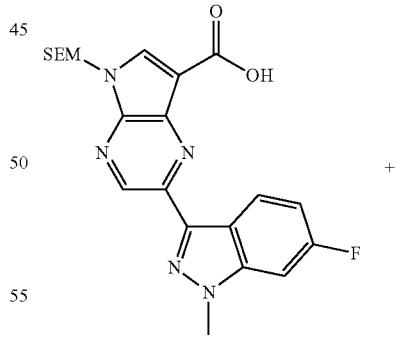

+

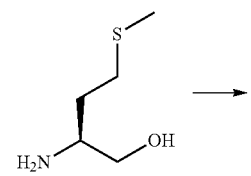

723
-continued

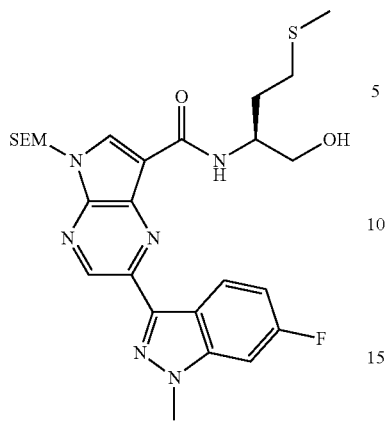

A 25 mL round-bottomed flask was charged with 2-(6-fluoro-1-methyl-1H-indazol-3-yl)-5-(2-trimethylsilanyl-ethoxymethyl)-5H-pyrrolo[2,3-b]pyrazine-7-carboxylic acid (100 mg, 0.23 mmol), (S)-2-amino-4-(methylthio)butan-1-ol (32 mg, 0.24 mmol), and HATU (90 mg, 0.24 mmol). Then added acetonitrile (4 mL) followed by N,N-diisopropylethylamine (0.19 mL, 1.1 mmol). The reaction mixture was stirred at room temperature overnight then quenched with water. The mixture was extracted with ethyl acetate (3×). The organic layers were combined, dried over $Na_2SO_4$, and concentrated. The residue was purified by chromatography over $SiO_2$ with EtOAc/heptanes (gradient: 5-50% EtOAc) to afford 105 mg (83%) of 2-(6-fluoro-1-methyl-1H-indazol-3-yl)-5-(2-trimethylsilanyl-ethoxymethyl)-5H-pyrrolo[2,3-b]pyrazine-7-carboxylic acid ((S)-1-hydroxymethyl-3-methylsulfanyl-propyl)-amide as an off-white foam. MS: $[M+H]^+$= 559.

Step 2

2-(6-Fluoro-1-methyl-1H-indazol-3-yl)-5-(2-trimethylsilanyl-ethoxymethyl)-5H-pyrrolo[2,3-b]pyrazine-7-carboxylic acid ((S)-1-hydroxymethyl-3-methanesulfonyl-propyl)-amide

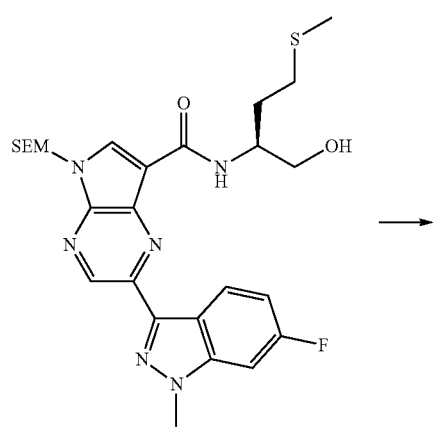

724
-continued

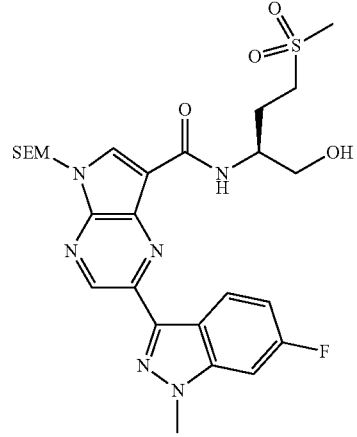

In a 25 mL round-bottomed flask, 2-(6-fluoro-1-methyl-1H-indazol-3-yl)-5-(2-trimethylsilanyl-ethoxymethyl)-5H-pyrrolo[2,3-b]pyrazine-7-carboxylic acid ((S)-1-hydroxymethyl-3-methylsulfanyl-propyl)-amide (105 mg, 0.188 mmol) was combined with dichloromethane (2 ml) to give a off-white solution. The solution was cooled to 5° C. with an ice bath. A solution of mCPBA (87 mg, 0.388 mmol) in dichloromethane (2 ml) was slowly added. The reaction mixture was allowed to stir at room temperature for 1 h, after which 20 drops of MeOH was added. The reaction mixture was allowed to stir at room temperature for 18 h then diluted with dichloromethane and washed with a saturated solution of sodium bicarbonate (2×15 mL). The organic layer was dried over $Na_2SO_4$ and concentrated to give 2-(6-fluoro-1-methyl-1H-indazol-3-yl)-5-(2-trimethylsilanyl-ethoxymethyl)-5H-pyrrolo[2,3-b]pyrazine-7-carboxylic acid ((S)-1-hydroxymethyl-3-methanesulfonyl-propyl)-amide which was used without further purification.

Step 3

2-(6-Fluoro-1-methyl-1H-indazol-3-yl)-5-(2-trimethylsilanyl-ethoxymethyl)-5H-pyrrolo[2,3-b]pyrazine-7-carboxylic acid ((S)-1-methoxymethyl-3-methanesulfonyl-propyl)-amide

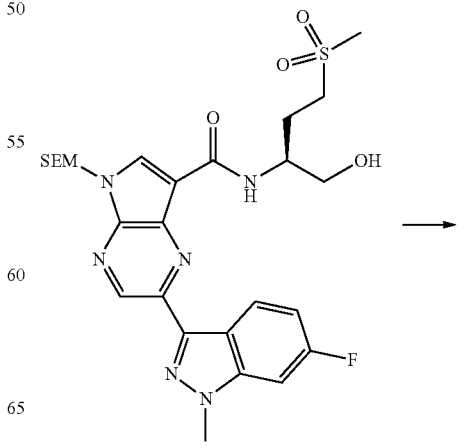

725
-continued

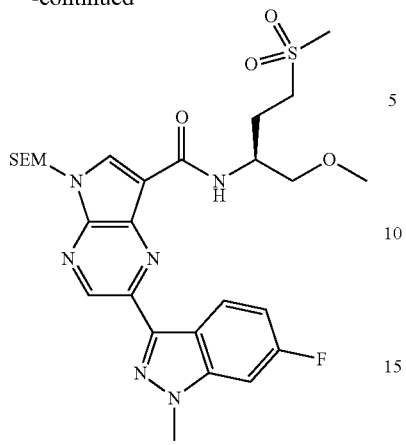

In a 10 mL round-bottomed flask, 2-(6-fluoro-1-methyl-1H-indazol-3-yl)-5-(2-trimethylsilanyl-ethoxymethyl)-5H-pyrrolo[2,3-b]pyrazine-7-carboxylic acid ((S)-1-hydroxymethyl-3-methanesulfonyl-propyl)-amide (102 mg, 0.173 mmol) was dissolved in THF (1.9 ml) to give a colorless solution. The reaction was cooled in an ice bath and crushed KOH (97 mg, 1.73 mmol), 18-crown-6 (46 mg, 0.173 mmol), and iodomethane (11 μl, 0.173 mmol) were added successively. The reaction mixture was stirred at 0° C. for 1 h after which the ice bath was removed. The reaction mixture was stirred at room temperature for 2 h then diluted with dichloromethane (10 mL) and washed with aqueous ammonium chloride (10 mL), water (10 mL), and saturated sodium bicarbonate (10 mL). The organic layer was dried over $Na_2SO_4$ and concentrated. The crude material was purified by chromatography over $SiO_2$ with EtOAc/heptane (gradient: 0%-60% EtOAc) to afford 30 mg (29%) of 2-(6-fluoro-1-methyl-1H-indazol-3-yl)-5-(2-trimethylsilanyl-ethoxymethyl)-5H-pyrrolo[2,3-b]pyrazine-7-carboxylic acid ((S)-1-methoxymethyl-3-methanesulfonyl-propyl)-amide as an off-white solid. MS: $[M+Na]^+=627$).

Step 4

2-(6-Fluoro-1-methyl-1H-indazol-3-yl)-5H-pyrrolo[2,3-b]pyrazine-7-carboxylic acid ((S)-3-methanesulfonyl-1-methoxymethyl-propyl)-amide

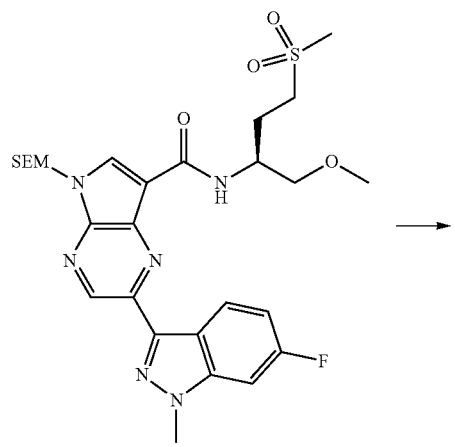

726
-continued

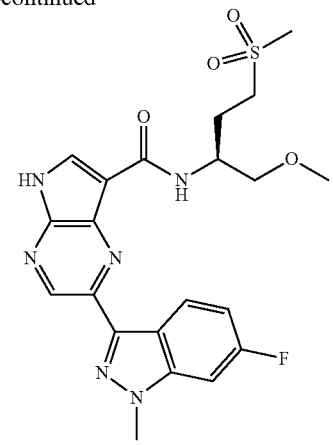

In a 10 mL round-bottom flask, 2-(6-fluoro-1-methyl-1H-indazol-3-yl)-5-(2-trimethylsilanyl-ethoxymethyl)-5H-pyrrolo[2,3-b]pyrazine-7-carboxylic acid ((S)-1-methoxymethyl-3-methanesulfonyl-propyl)-amide (35 mg, 0.058 mmol) and TFA (0.5 ml, 6.5 mmol) were combined with dichloromethane (1.5 ml) to give an orange solution. The reaction mixture was stirred at room temperature for 2.5 h then concentrated under reduced pressure. The resultant crude solid was dissolved in dichloromethane (1 mL) and ethylenediamine (0.19 ml, 2.8 mmol) was added. The reaction mixture was stirred at room temperature for 18 h then concentrated and the residue was precipitated with water. The suspension was stirred for 1 h and the crude solid collected by filtration. The crude solid was purified by trituration (dichloromethane/heptane) to afford 12 mg (44%) of 2-(6-fluoro-1-methyl-1H-indazol-3-yl)-5H-pyrrolo[2,3-b]pyrazine-7-carboxylic acid ((S)-3-methanesulfonyl-1-methoxymethyl-propyl)-amide as a light yellow solid. MS: $[M+Na]^+=497$; $^1H$ NMR (300 MHz, DMSO-$d_6$) δ: 12.87 (br. s., 1H), 9.12 (s, 1H), 8.54 (dd, J=8.7, 5.3 Hz, 1H), 8.47 (s, 1H), 8.28 (d, J=9.1 Hz, 1H), 7.69 (dd, J=9.8, 2.3 Hz, 1H), 7.19 (td, J=9.1, 2.3 Hz, 1H), 4.35-4.55 (m, 1H), 4.15 (s, 3H), 3.60 (dd, J=9.8, 4.2 Hz, 1H), 3.51 (dd, J=9.4, 4.2 Hz, 1H), 3.26 (s, 3H), 3.20-3.28 (m, 2H), 2.97 (s, 3H), 2.02-2.23 (m, 2H).

Example 193

2-(6-Fluoro-1-methyl-1H-indazol-3-yl)-5H-pyrrolo[2,3-b]pyrazine-7-carboxylic acid ((S)-2-difluoromethoxy-1-methyl-ethyl)-amide

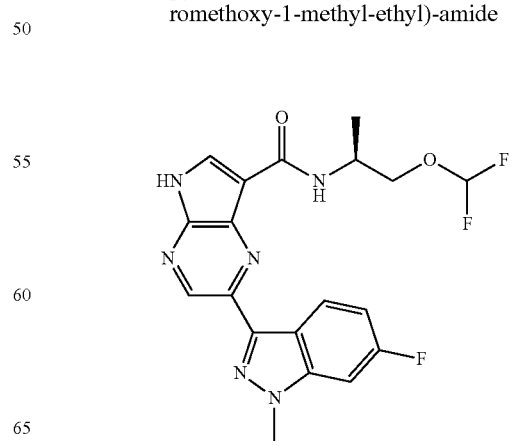

Step 1

2-(6-Fluoro-1-methyl-1H-indazol-3-yl)-5-(2-trimethylsilanyl-ethoxymethyl)-5H-pyrrolo[2,3-b]pyrazine-7-carboxylic acid ((S)-2-difluoromethoxy-1-methyl-ethyl)-amide

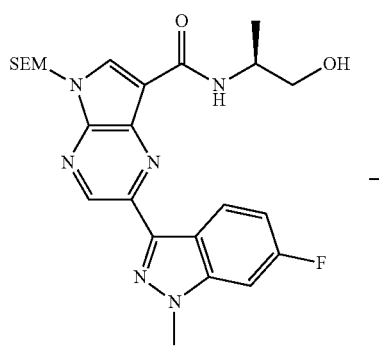

In a 25 mL pressure tube, 2-(6-fluoro-1-methyl-1H-indazol-3-yl)-5-(2-trimethylsilanylethoxymethyl)-5H-pyrrolo[2,3-b]pyrazine-7-carboxylic acid ((S)-2-hydroxy-1-methyl-ethyl)-amide (60 mg, 0.12 mmol) and copper(I) iodide (14 mg, 0.070 mmol) were combined with acetonitrile (3 mL) to give a light yellow suspension. The mixture was degassed and placed under argon. The reaction mixture was heated to 50° C. in a sand bath. 2,2-Difluoro-2-(fluorosulfonyl)acetic acid (12 µL, 0.112 mmol) was added dropwise slowly to give a light yellow solution. The reaction was stirred for an additional 5 min. The reaction was quenched with water and extracted with ethyl acetate. The combined organics were successively washed with water, saturated sodium bicarbonate, and brine then dried over Na$_2$SO$_4$ and concentrated. The crude material was purified by flash chromatography over silica gel (gradient: 0% to 50% EtOAc in hexanes) to afford 12 mg (18%) of 2-(6-fluoro-1-methyl-1H-indazol-3-yl)-5-(2-trimethylsilanyl-ethoxymethyl)-5H-pyrrolo[2,3-b]pyrazine-7-carboxylic acid ((S)-2-difluoromethoxy-1-methyl-ethyl)-amide as a white solid. MS: [M+H]$^+$=549.

Step 2

2-(6-Fluoro-1-methyl-1H-indazol-3-yl)-5H-pyrrolo[2,3-b]pyrazine-7-carboxylic acid ((S)-2-difluoromethoxy-1-methyl-ethyl)-amide In a 10 mL round-bottom flask, 2-(6-fluoro-1-methyl-1H-indazol-3-yl)-5-(2-trimethylsilanyl-ethoxymethyl)-5H-pyrrolo[2,3-b]pyrazine-7-carboxylic acid ((S)-2-difluoromethoxy-1-methyl-ethyl)-amide (10 mg, 0.018 mmol) and TFA (0.5 ml, 6.5 mmol) were combined with dichloromethane (1.5 ml) to give an orange solution. The reaction mixture was stirred at room temperature for 2.5 h then concentrated under reduced pressure. The resultant crude solid was dissolved in dichloromethane (1 mL) and ethylenediamine (30 ul, 0.46 mmol) was added. The reaction mixture was stirred at room temperature for 18 h then concentrated and the residue was precipitated with water. The suspension was stirred for 1 h and the crude solid collected by filtration. The crude solid was purified by trituration (dichloromethane) to afford 2 mg (32%) of 2-(6-fluoro-1-methyl-1H-indazol-3-yl)-5H-pyrrolo[2,3-b]pyrazine-7-carboxylic acid ((S)-2-difluoromethoxy-1-methyl-ethyl)-amide as an off-white solid. MS: [M+H]$^+$=419; $^1$H NMR (300 MHz, DMSO-d$_6$) δ: 12.86 (br. s., 1H), 9.11 (s, 1H), 8.47 (s, 1H), 8.49 (dd, J=9.1, 5.3 Hz, 1H), 8.19 (d, J=8.3 Hz, 1H), 7.70 (dd, J=9.8, 2.3 Hz, 1H), 7.15

(td, J=9.2, 2.1 Hz, 1H), 6.70 (t, J=75.2 Hz, 1H), 4.36-4.54 (m, 1H), 4.16 (s, 3H), 4.00 (d, J=4.5 Hz, 2H), 1.37 (d, J=6.8 Hz, 3H).

Example 194

2-(5-Cyclopropyl-1-methyl-1H-indazol-3-yl)-5H-pyrrolo[2,3-b]pyrazine-7-carboxylic acid ((S)-2-methoxy-1-methyl-ethyl)-amide

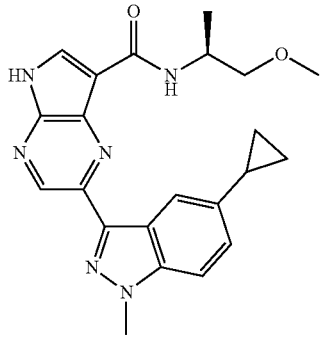 [SMILES: COC[C@H](C)NC(=O)c1c[nH]c2ncc(-c3nn(C)c4ccc(C5CC5)cc34)nc12]

Step 1

5-Cyclopropyl-1-(2-trimethylsilanyl-ethoxymethyl)-1H-indazole

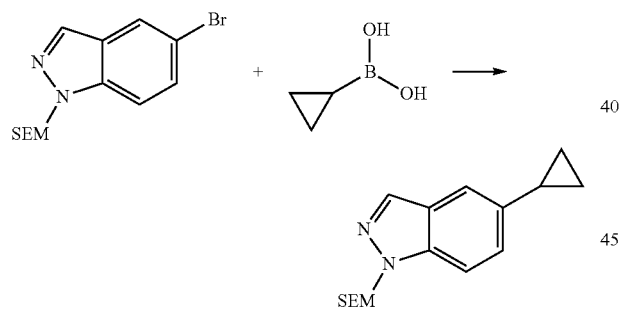

A 250 ml 2-neck round-bottomed flask was charged with 5-bromo-1-((2-(trimethylsilyl)ethoxy)methyl)-1H-indazole (2.5 g, 7.64 mmol), cyclopropylboronic acid (1.18 g, 13.7 mmol), palladium (II) acetate (85.7 mg, 0.38 mmol), tricyclohexylphosphine (214 mg, 0.764 mmol), potassium phosphate tribasic (3.24 g, 15.3 mmol), toluene (40 ml) and water (4 ml). The reaction mixture was stirred at 100° C. overnight. The reaction mixture was cooled to room temperature and then diluted with EtOAc (100 ml) and water (20 ml). The mixture was extracted with EtOAc (100 mL). The organic layers were washed with water (20 mL) and brine (20 mL). The organic layer was dried over sodium sulfate, filtered, and concentrated. The residue was absorbed onto SiO$_2$ and purified by chromatography over SiO$_2$ with EtOAc/CH$_2$Cl$_2$ (gradient: 0-10% EtOAc) to afford 1.7 g (77%) of 5-cyclopropyl-1-(2-trimethylsilanylethoxymethyl)-1H-indazole as a light yellow oil. $^1$H NMR (300 MHz, CDCl$_3$) δ: 7.93 (s, 1H), 7.48 (d, J=8.7 Hz, 1H), 7.44 (s, 1H), 7.19 (dd, J=8.5, 1.7 Hz, 1H), 3.53 (app t, J=8.3 Hz, 2H), 1.93-2.12 (m, 1H), 0.92-1.04 (m, 2H), 0.88 (app t, J=8.3 Hz, 2H), 0.64-0.78 (m, 2H), −0.07 (s, 9H).

Step 2

5-Cyclopropyl-1H-indazole

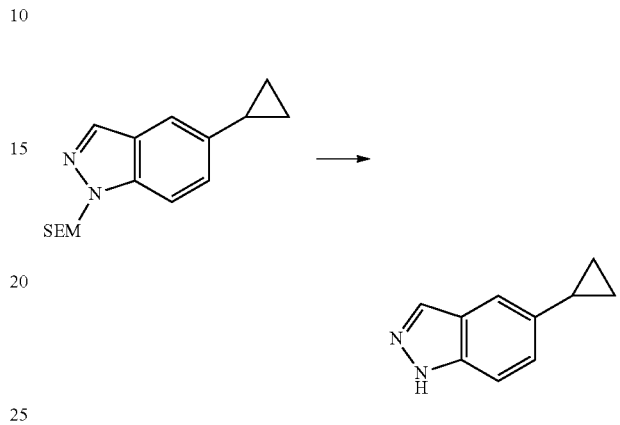

In a 1 L round-bottomed flask, 5-cyclopropyl-1-(2-trimethylsilanyl-ethoxymethyl)-1H-indazole (1.7 g, 5.89 mmol) was dissolved in a solution of dichloromethane (292 mL) and trifluoroacetic acid (194 mL). After stirring at room temperature overnight, the reaction mixture was concentrated under reduced pressure. The resultant crude solid was dissolved in dichloromethane and ethylenediamine (24.2 mL, 5.89 mmol) was added. After stirring at room temperature overnight, the reaction mixture was poured onto water (50 mL) and extracted with EtOAc (2×100 mL). The organic layers were dried over MgSO$_4$ and concentrated under reduced pressure to afford 1 g of 5-cyclopropyl-1H-indazole that was used without further purification.

MS: [M+H]$^+$=299

Step 3

5-Cyclopropyl-1-methyl-3-tributylstannanyl-1H-indazole

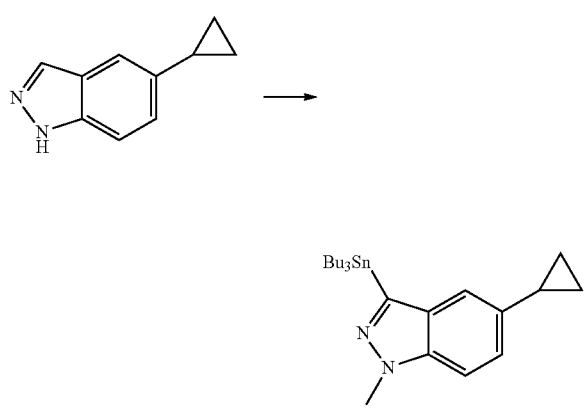

Prepared according to the procedure outlined in Example 1, Steps 1-3, substituting 5-cyclopropyl-1H-indazole for indazole in Step 1.

Step 4

2-(5-Cyclopropyl-1-methyl-1H-indazol-3-yl)-5-(2-trimethylsilanyl-ethoxymethyl)-5H-pyrrolo[2,3-b]pyrazine-7-carboxylic acid

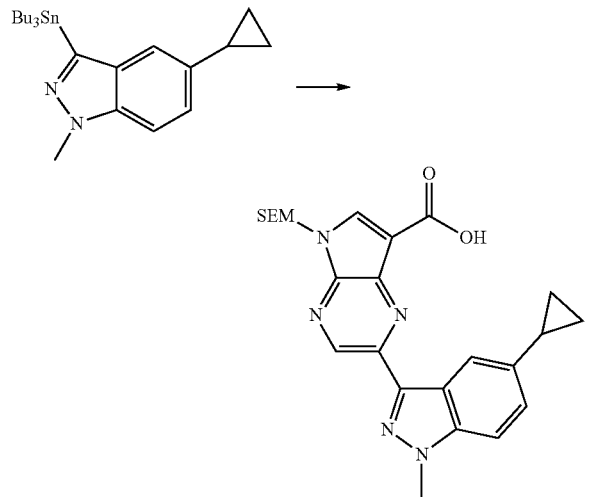

Prepared according to the procedure outlined in Example 14, Steps 1-2, substituting 5-cyclopropyl-1-methyl-3-tributylstannanyl-1H-indazole for 6-chloro-1-methyl-3-tributylstannanyl-1H-indazole in Step 1. $^1$H NMR (300 MHz, DMSO-$d_6$) δ: 9.10 (s, 1H), 8.69 (s, 1H), 8.62 (s, 1H), 7.61 (d, J=9.1 Hz, 1H), 7.34 (dd, J=8.7, 1.9 Hz, 1H), 5.72 (s, 2H), 4.14 (s, 3H), 3.60 (t, J=8.2 Hz, 2H), 2.01-2.15 (m, 1H), 0.94-1.03 (m, 2H), 0.85 (t, J=8.3 Hz, 2H), 0.78-0.85 (m, 2H), −0.09 (s, 9H).

Step 5

2-(5-Cyclopropyl-1-methyl-1H-indazol-3-yl)-5-(2-trimethylsilanyl-ethoxymethyl)-5H-pyrrolo[2,3-b]pyrazine-7-carboxylic acid ((S)-2-methoxy-1-methyl-ethyl)-amide

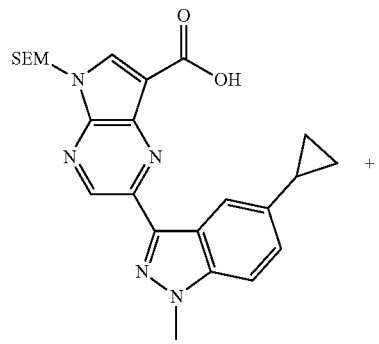

+

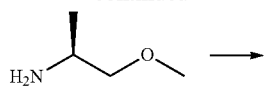

→

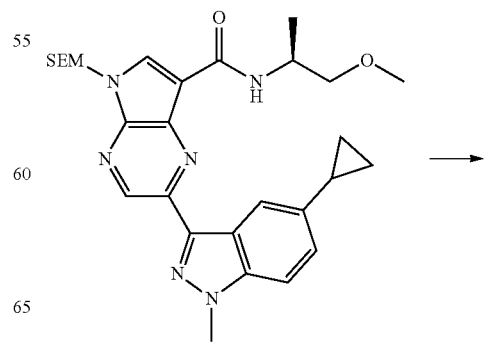

A 25 mL round-bottomed flask was charged with 2-(5-cyclopropyl-1-methyl-1H-indazol-3-yl)-5-(2-trimethylsilanyl-ethoxymethyl)-5H-pyrrolo[2,3-b]pyrazine-7-carboxylic acid (70 mg, 0.15 mmol), (S)-1-methoxypropan-2-amine hydrochloride (21 mg, 0.16 mmol), and HATU (63 mg, 0.16 mmol). Then added acetonitrile (2 mL) followed by N,N-diisopropylethylamine (0.08 mL, 0.45 mmol). The reaction mixture was stirred at room temperature overnight then quenched with water. The mixture was extracted with ethyl acetate (3×). The organic layers were combined, dried over Na$_2$SO$_4$, and concentrated. The crude material was purified by flash chromatography over silica gel (gradient: 15% to 100% EtOAc in heptane) to afford 34 mg (42%) of 2-(5-cyclopropyl-1-methyl-1H-indazol-3-yl)-5-(2-trimethylsilanyl-ethoxymethyl)-5H-pyrrolo[2,3-b]pyrazine-7-carboxylic acid ((S)-2-methoxy-1-methyl-ethyl)-amide as a white solid.

MS: [M+H]$^+$=535.

Step 6

2-(5-Cyclopropyl-1-methyl-1H-indazol-3-yl)-5H-pyrrolo[2,3-b]pyrazine-7-carboxylic acid ((S)-2-methoxy-1-methyl-ethyl)-amide -continued

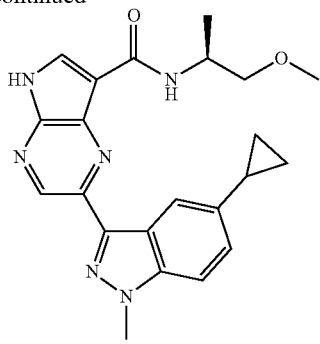

In a 10 mL round-bottom flask, 2-(5-cyclopropyl-1-methyl-1H-indazol-3-yl)-5-(2-trimethylsilanyl-ethoxymethyl)-5H-pyrrolo[2,3-b]pyrazine-7-carboxylic acid ((S)-2-methoxy-1-methyl-ethyl)-amide (34 mg, 0.065 mmol) and TFA (0.5 ml, 6.5 mmol) were combined with dichloromethane (1.5 ml) to give an orange solution. The reaction mixture was stirred at room temperature for 2.5 h then concentrated under reduced pressure. The resultant crude solid was dissolved in dichloromethane (1.5 mL) and ethylenediamine (0.11 ml, 1.6 mmol) was added. The reaction mixture was stirred at room temperature for 18 h then concentrated and the residue was precipitated with water. The suspension was stirred for 1 h and the crude solid collected by filtration. The crude solid was purified by trituration (dichloromethane/heptane) to afford 10 mg (38%) of 2-(5-cyclopropyl-1-methyl-1H-indazol-3-yl)-5H-pyrrolo[2,3-b]pyrazine-7-carboxylic acid ((S)-2-methoxy-1-methyl-ethyl)-amide as an off-white solid. MS: [M+H]$^+$=405; $^1$H NMR (300 MHz, DMSO-d$_6$) δ: 12.79 (br. s., 1H), 9.09 (s, 1H), 8.42 (s, 1H), 8.30 (s, 1H), 8.26 (d, J=8.3 Hz, 1H), 7.66 (d, J=8.7 Hz, 1H), 7.10 (dd, J=8.7, 1.5 Hz, 1H), 4.28-4.43 (m, 1H), 4.15 (s, 3H), 3.53 (dd, J=9.1, 4.5 Hz, 1H), 3.45 (dd, J=9.1, 4.9 Hz, 1H), 3.20 (s, 3H), 2.18-2.25 (m, 1H), 1.35 (d, J=6.8 Hz, 3H), 0.94-1.02 (m, 2H), 0.76 (td, J=5.3, 4.2 Hz, 2H).

Example 195

2-(5-Cyclopropyl-1-methyl-1H-indazol-3-yl)-5H-pyrrolo[2,3-b]pyrazine-7-carboxylic acid isopropylamide

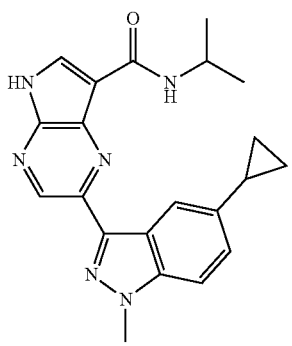 [SMILES: CC(C)NC(=O)c1c[nH]c2ncc(-c3nn(C)c4ccc(C5CC5)cc34)nc12]

Prepared according to the procedure outlined in Example 194, Steps 5-6, substituting isopropylamine for (S)-1-methoxypropan-2-amine hydrochloride in Step 5. The final compound was isolated as an off-white solid, 18 mg (62%); MS: [M+H]$^+$=375; $^1$H NMR (300 MHz, DMSO-d$_6$) δ: 12.72 (br. s., 1H), 9.06 (s, 1H), 8.41 (s, 1H), 8.26 (s, 1H), 8.13 (d, J=7.9 Hz, 1H), 7.67 (d, J=8.7 Hz, 1H), 7.15 (dd, J=8.7, 1.5 Hz, 1H), 4.24 (dq, J=13.9, 6.8 Hz, 1H), 4.15 (s, 3H), 2.12 (app. quin, J=4.9 Hz, 1H), 1.34 (s, 3H), 1.32 (s, 3H), 0.93-1.02 (m, 2H), 0.70-80 (m, 2H).

Example 196

2-(5-Cyclopropyl-1-methyl-1H-indazol-3-yl)-5H-pyrrolo[2,3-b]pyrazine-7-carboxylic acid (2-hydroxy-1,1-dimethyl-ethyl)-amide

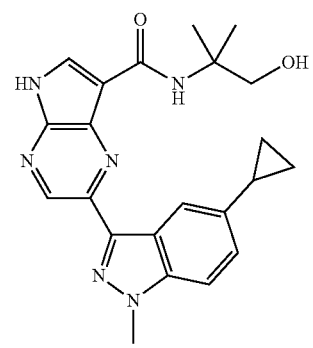 [SMILES: Cn1nc(-c2cnc3[nH]cc(C(=O)NC(C)(C)CO)c3n2)c2cc(C3CC3)ccc21]

Prepared according to the procedure outlined in Example 194, Steps 5-6, substituting 2-amino-2-methylpropan-1-ol for (S)-1-methoxypropan-2-amine hydrochloride in Step 5. The final compound was isolated as an off-white solid, 25 mg (55%); MS: [M+H]$^+$=405; $^1$H NMR (300 MHz, DMSO-d$_6$) δ: 12.70 (br. s., 1H), 9.03 (s, 1H), 8.37 (s, 1H), 8.29 (s, 1H), 8.02 (s, 1H), 7.64 (d, J=8.7 Hz, 1H), 7.11 (dd, J=8.7, 1.5 Hz, 1H), 5.00 (t, J=5.7 Hz, 1H), 4.14 (s, 3H), 3.65 (d, J=5.3 Hz, 2H), 2.18 (app. quin, J=4.9 Hz, 1H), 1.44 (s, 6H), 0.92-1.00 (m, 2H), 0.69-0.76 (m, 2H).

Example 197

2-(5-Cyclopropyl-1-methyl-1H-indazol-3-yl)-5H-pyrrolo[2,3-b]pyrazine-7-carboxylic acid tert-butylamide

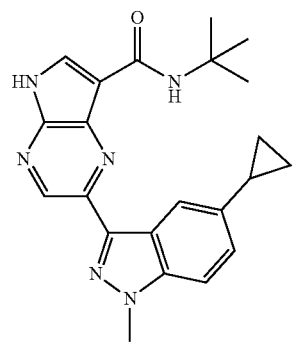 [SMILES: Cn1nc(-c2cnc3[nH]cc(C(=O)NC(C)(C)C)c3n2)c2cc(C3CC3)ccc21]

Prepared according to the procedure outlined in Example 194, Steps 5-6, substituting tert-butylamine for (S)-1-methoxypropan-2-amine hydrochloride in Step 5. The final compound was isolated as an off-white solid, 25 mg (79%); MS: [M+H]$^+$=389; $^1$H NMR (300 MHz, DMSO-d$_6$) δ: 12.17 (br.

s., 1H), 9.01 (s, 1H), 8.36 (s, 1H), 8.24 (s, 1H), 8.06 (s, 1H), 7.65 (d, J=8.7 Hz, 1H), 7.14 (dd, J=8.7, 1.5 Hz, 1H), 4.14 (s, 3H), 2.10 (s, 1H), 1.51 (s, 9H), 0.88-1.08 (m, 2H), 0.65-0.80 (m, 2H).

Example 198

2-(6-Fluoro-1-methyl-1H-indazol-3-yl)-5H-pyrrolo[2,3-b]pyrazine-7-carboxylic acid [(1R,2R)-1-(3-fluoro-azetidine-1-carbonyl)-2-hydroxy-propyl]-amide

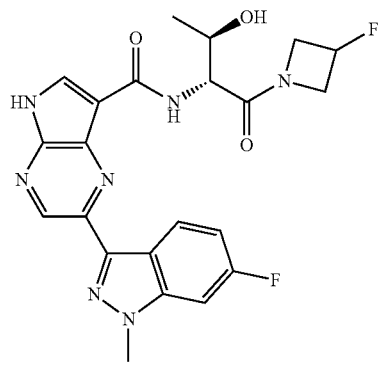 [SMILES: C[C@@H](O)[C@@H](NC(=O)c1c[nH]c2ncc(-c3nn(C)c4cc(F)ccc34)nc12)C(=O)N1CC(F)C1]

Step 1

[(1R,2R)-1-(3-Fluoro-azetidine-1-carbonyl)-2-hydroxy-propyl]-carbamic acid 9H-fluoren-9-ylmethyl ester

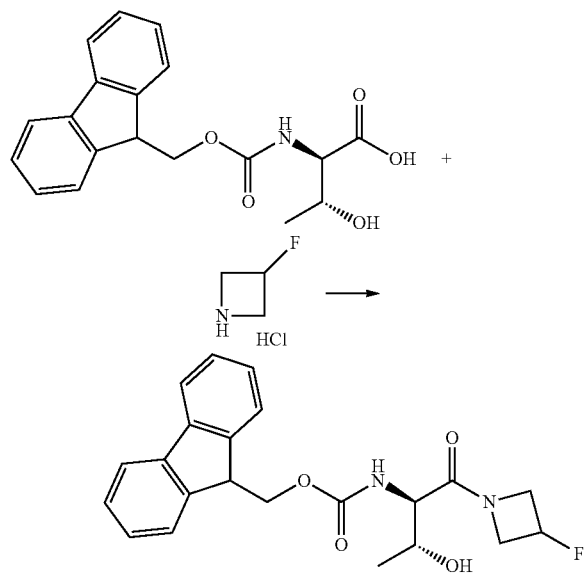

A 25 mL round-bottomed flask was charged with (2R,3R)-2-(((9H-fluoren-9-yl)methoxy)carbonylamino)-3-hydroxybutanoic acid (184 mg, 0.54 mmol), 3-fluoroazetidine hydrochloride (66 mg, 0.59 mmol), and HATU (242 mg, 0.64 mmol). Then added acetonitrile (1.1 mL) followed by N,N-diisopropylethylamine (0.20 mL, 1.1 mmol) and N-methyl-morpholine (0.05 mL, 0.45 mmol). The reaction mixture was stirred at room temperature overnight then concentrated. The crude solid was purified by chromatography over SiO$_2$ with EtOAc/heptane (gradient: 10-80% EtOAc) to afford 112 mg (52%) of [(1R,2R)-1-(3-fluoro-azetidine-1-carbonyl)-2-hydroxy-propyl]-carbamic acid 9H-fluoren-9-ylmethyl ester as a white solid. MS: [M+H]$^+$=399.

Step 2

(2R,3R)-2-Amino-1-(3-fluoro-azetidin-1-yl)-3-hydroxy-butan-1-one

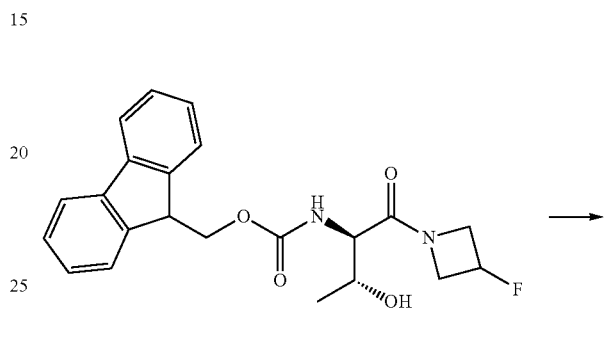

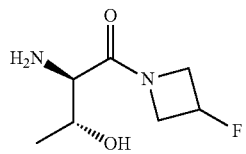

In a 25 ml, round-bottomed flask, [1R,2R)-1-(3-fluoro-azetidine-1-carbonyl)-2-hydroxy-propyl]-carbamic acid 9H-fluoren-9-ylmethyl ester (112 mg, 0.28 mmol) and diethylamine (0.29 ml, 2.81 mmol) were combined with acetonitrile (6 ml) to give a white suspension. The reaction was stirred at room temperature for 2.5 h and then concentrated to dryness to afford (2R,3R)-2-amino-1-(3-fluoro-azetidin-1-yl)-3-hydroxy-butan-1-one which was used without further purification.

Step 3

2-(6-Fluoro-1-methyl-1H-indazol-3-yl)-5H-pyrrolo[2,3-b]pyrazine-7-carboxylic acid [(1R,2R)-1-(3-fluoro-azetidine-1-carbonyl)-2-hydroxy-propyl]-amide

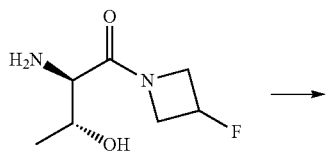

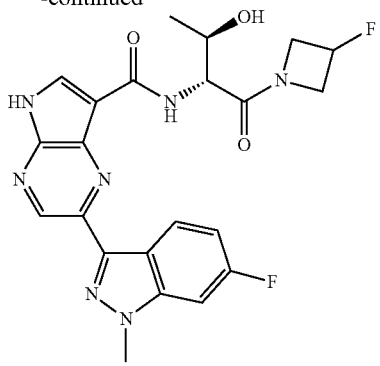

Prepared according to the procedure outlined in Example 178, substituting (2R,3R)-2-amino-1-(3-fluoro-azetidin-1-yl)-3-hydroxy-butan-1-one for (S)-butan-2-amine in Step 1. The final compound was isolated as a white solid, 31 mg (63%), MS: [M+H]+=470; ¹H NMR (300 MHz, DMSO-d₆) δ: 12.58 (br. s, 1H), 9.14 (s, 1H), 8.65-8.98 (m, 1H), 8.47 (s, 1H), 8.48 (d, J=13.2 Hz, 1H), 7.65 (dd, J=9.6, 2.1 Hz, 1H), 7.10 (tt, J=9.0, 2.5 Hz, 1H), 5.43 (d, J=56.3 Hz, 1H), 5.19 (br. s., 1H), 4.69-4.77 (m, 1H), 4.64 (t, J=8.3 Hz, 1H), 4.32-4.52 (m, 1H), 4.18-4.32 (m, 1H), 4.14 (s, 3H), 3.98 (br. s., 2H), 1.16 (d, J=6.0 Hz, 3H).

Example 199

2-(6-Chloro-1-methyl-1H-indazol-3-yl)-5H-pyrrolo[2,3-b]pyrazine-7-carboxylic acid [1-(1-methyl-1H-imidazol-2-yl)-ethyl]-amide

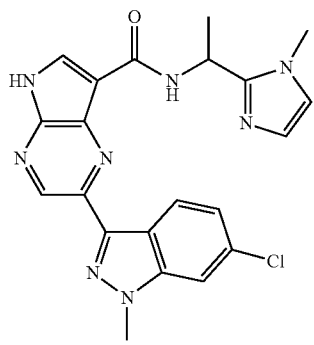 [SMILES: CC(NC(=O)c1c[nH]c2ncc(-c3nn(C)c4cc(Cl)ccc34)nc12)c1nccn1C]

Step 1

2-Methyl-propane-2-sulfinic acid 1-(1-methyl-1H-imidazol-2-yl)-meth-(E)-ylideneamide

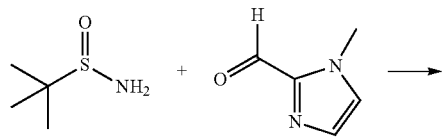

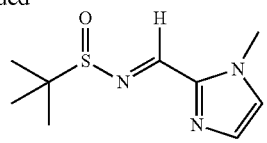

In a 25 mL vial, cupric sulfate (1.96 g, 12.3 mmol), 1-methyl-1H-imidazole-2-carbaldehyde (450 mg, 4.09 mmol) and 2-methylpropane-2-sulfinamide (594 mg, 4.9 mmol) were combined with dichloromethane (2 ml) to give a light blue suspension. The reaction mixture was stirred at 25° C. for 15 h then filtered through Celite. The reaction mixture was filtered again through silica gel eluting with ethyl acetate. The crude reaction mixture was concentrated in vacuo to provide 670 mg (76%) of 2-methyl-propane-2-sulfinic acid 1-(1-methyl-1H-imidazol-2-yl)-meth-(E)-ylideneamide as an oil. ¹H NMR (300 MHz, CDCl₃): δ 8.62 (s, 1H), 7.27 (bs, 1H), 7.08 (bs, 1H), 4.02 (s, 1H), 1.26 (s, 9H).

Step 2

2-Methyl-propane-2-sulfinic acid [1-(1-methyl-1H-imidazol-2-yl)-ethyl]-amide

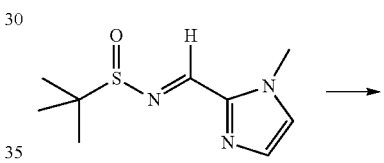

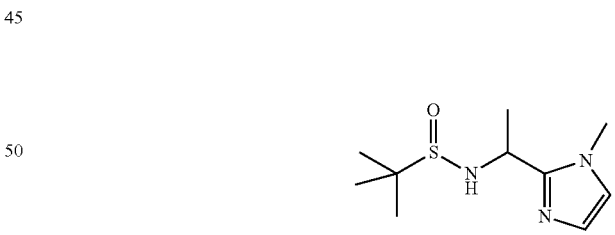

In a 250 mL round-bottomed flask, 2-methyl-propane-2-sulfinic acid 1-(1-methyl-1H-imidazol-2-yl)-meth-(E)-ylideneamide (670 mg, 3.14 mmol) was combined with THF to give a colorless solution. Methylmagnesium bromide in ether (3.0 M, 5.24 ml, 15.7 mmol) was added at 0° C. The reaction was stirred at 0° C. for 2 h. The reaction mixture was diluted with sat aq. NH₄Cl. The aqueous layer was back-extracted with dichloromethane (2×100 mL). The aqueous layer was back-extracted with EtOAc (1×125 mL). The crude reaction mixture was concentrated in vacuo to provide 700 mg (92%) of 2-methyl-propane-2-sulfinic acid [1-(1-methyl-1H-imidazol-2-yl)-ethyl]-amide as a single diastereomer. ¹H NMR (300 MHz, DMSO-d$_6$): δ 6.98 (bs, 1H), 6.82 (bs, 1H), 4.61 (q, 1H, J=6 Hz), 4.10 (bs, 1H), 1.61 (d, 1H, J=6 Hz), 1.29 (s, 9H).

Step 3

1-(1-Methyl-1H-imidazol-2-yl)-ethylamine dihydrochloride

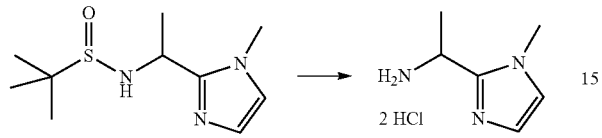

In a 250 mL round-bottomed flask, 2-methyl-propane-2-sulfinic acid [1-(1-methyl-1H-imidazol-2-yl)-ethyl]-amide (700 mg, 3.05 mmol) was combined with methanol at 0° C. to give a colorless solution. Hydrogen chloride (4.0 M in 1,4-dioxane, 10 ml, 40.0 mmol) was added. The reaction mixture was stirred at 0° C. for 2 h then concentrated in vacuo to provide 1-(1-methyl-1H-imidazol-2-yl)-ethylamine dihydrochloride. $^1$H NMR (300 MHz, DMSO-d$_6$): δ 9.28 (bs, 1H), 7.67 (bs, 2H), 4.92 (bs, 1H), 3.93 (bd, 1H), 1.67 (bd, 3H).

Step 4

2-(6-Chloro-1-methyl-1H-indazol-3-yl)-5-(2-trimethylsilanyl-ethoxymethyl)-5H-pyrrolo[2,3-b]pyrazine-7-carboxylic acid [1-(1-methyl-1H-imidazol-2-yl)-ethyl]-amide

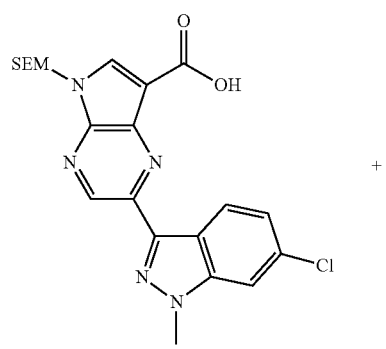

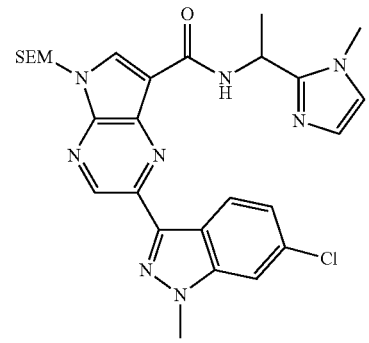

In a 20 mL scintillation vial, 2-(6-chloro-1-methyl-1H-indazol-3-yl)-5-(2-trimethylsilanyl-ethoxymethyl)-5H-pyrrolo[2,3-b]pyrazine-7-carboxylic acid (400 mg, 0.87 mmol), 1-(1-methyl-1H-imidazol-2-yl)-ethylamine dihydrochloride (219 mg, 1.75 mmol), HBTU (431 mg, 1.14 mmol), HOBt (153 mg, 1.14 mmol) and DIPEA (0.31 ml, 1.75 mmol) were combined with DMF (6 ml) to give a light yellow solution. After stirring at room temperature overnight, the reaction mixture was diluted with EtOAc (50 mL) and washed with sat NaHCO$_3$ (3×25 mL) and H$_2$O (3×25 mL). The organic layer was dried over Na$_2$SO$_4$ and concentrated in vacuo. The crude material was purified by flash chromatography (silica gel, 4 g, 0% to 10% MeOH in DCM with 0.1% NH$_4$OH) to provide 300 mg (61%) of 2-(6-chloro-1-methyl-1H-indazol-3-yl)-5-(2-trimethylsilanyl-ethoxymethyl)-5H-pyrrolo[2,3-b]pyrazine-7-carboxylic acid [1-(1-methyl-1H-imidazol-2-yl)-ethyl]-amide. MS: (M+H)$^+$=566.

Step 5

2-(6-Chloro-1-methyl-1H-indazol-3-yl)-5H-pyrrolo[2,3-b]pyrazine-7-carboxylic acid [1-(1-methyl-1H-imidazol-2-yl)-ethyl]-amide

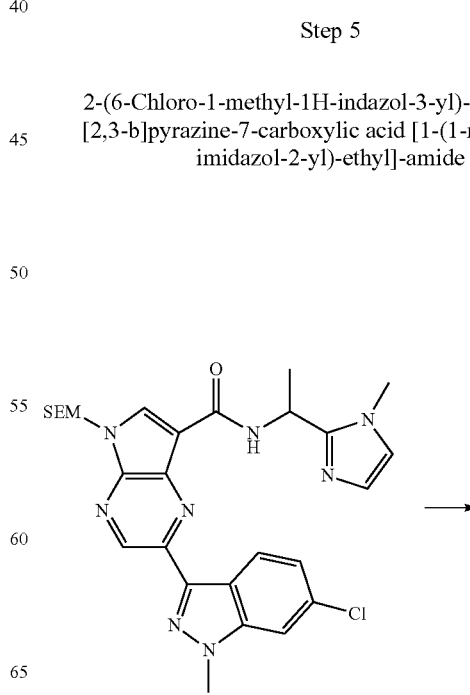

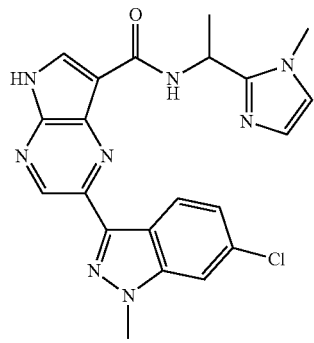

2-(6-Chloro-1-methyl-1H-indazol-3-yl)-5-(2-trimethylsilanyl-ethoxymethyl)-5H-pyrrolo[2,3-b]pyrazine-7-carboxylic acid [1-(1-methyl-1H-imidazol-2-yl)-ethyl]-amide (300 mg, 0.531 mol) was dissolved in a 4:6 solution of TFA:DCM (142 mL). After stirring at room temperature overnight, the volatiles were removed under reduced pressure. The crude material was then dissolved in dichloromethane and treated with ethylenediamine (319 mg, 5.31 mmol). After stirring at room temperature overnight, the precipitate was collected by filtration to afford 100 mg (43%) of 2-(6-chloro-1-methyl-1H-indazol-3-yl)-5H-pyrrolo[2,3-b]pyrazine-7-carboxylic acid [1-(1-methyl-1H-imidazol-2-yl)-ethyl]-amide as a yellow solid. MS: (M+H)$^+$=435; $^1$H NMR (300 MHz, DMSO-d$_6$) δ ppm 9.12 (s, 1H) 8.50-8.63 (m, 2H) 8.49-8.50 (m, 1H) 7.96 (d, J=1.51 Hz, 1H) 7.29 (dd, J=8.69, 1.51 Hz, 1H) 7.09 (s, 1H) 6.85 (s, 1H) 5.40-5.68 (m, 1H) 4.15 (s, 3H) 3.63-3.77 (m, 3H) 1.61 (d, J=6.80 Hz, 3H).

Example 200

2-(6-Chloro-1-methyl-1H-indazol-3-yl)-5H-pyrrolo[2,3-b]pyrazine-7-carboxylic acid ((R)-2-hydroxy-1-methyl-ethyl)-amide

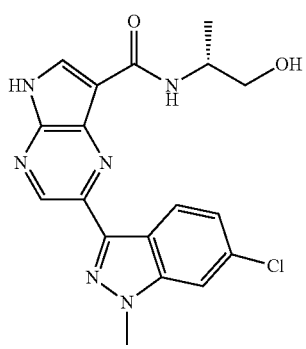 [SMILES: C[C@H](CO)NC(=O)c1c[nH]c2ncc(-c3nn(C)c4cc(Cl)ccc34)nc12]

Step 1

2-(6-Chloro-1-methyl-1H-indazol-3-yl)-5-(2-trimethylsilanyl-ethoxymethyl)-5H-pyrrolo[2,3-b]pyrazine-7-carboxylic acid ((R)-2-hydroxy-1-methyl-ethyl)-amide

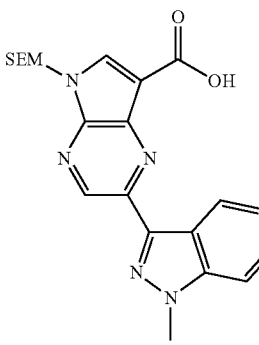

+

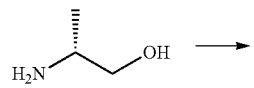

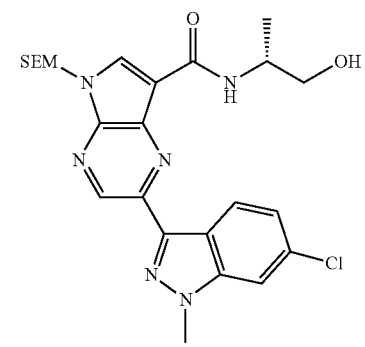

In a 20 mL scintillation vial, 2-(6-chloro-1-methyl-1H-indazol-3-yl)-5-(2-trimethylsilanyl-ethoxymethyl)-5H-pyrrolo[2,3-b]pyrazine-7-carboxylic acid (400 mg, 0.87 mmol), D-alaninol (131 mg, 1.75 mmol), HBTU (431 mg, 1.14 mmol), HOBt (153 mg, 1.14 mmol) and DIPEA (0.31 ml, 1.75 mmol) were combined with DMF (6 ml) to give a light yellow solution. After stirring at room temperature overnight, the reaction mixture was diluted with EtOAc (50 mL) and washed with sat NaHCO$_3$ (3×25 mL) and H$_2$O (3×25 mL). The organic layer were dried over Na$_2$SO$_4$ and concentrated in vacuo. The crude material was purified by flash chromatography (silica gel, 4 g, 0% to 10% MeOH in DCM with 0.1% NH$_4$OH) to provide 250 mg (56%) of 2-(6-chloro-1-methyl-1H-indazol-3-yl)-5-(2-trimethylsilanyl-ethoxymethyl)-5H-pyrrolo[2,3-b]pyrazine-7-carboxylic acid ((R)-2-hydroxy-1-methyl-ethyl)-amide as an off-white solid. MS: (M+H)⁺=516.

Step 2

2-(6-Chloro-1-methyl-1H-indazol-3-yl)-5H-pyrrolo[2,3-b]pyrazine-7-carboxylic acid ((R)-2-hydroxy-1-methyl-ethyl)-amide

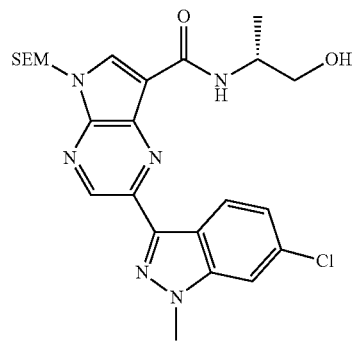

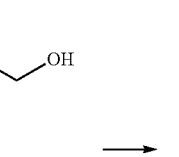

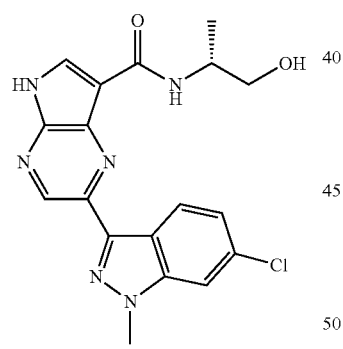

2-(6-Chloro-1-methyl-1H-indazol-3-yl)-5-(2-trimethylsilanyl-ethoxymethyl)-5H-pyrrolo[2,3-b]pyrazine-7-carboxylic acid ((R)-2-hydroxy-1-methyl-ethyl)-amide (35 mg, 0.068 mol) was dissolved in a 4:6 solution of TFA:DCM (10 mL). After stirring at room temperature overnight, the volatiles were removed under reduced pressure. The crude material was then dissolved in dichloromethane and treated with ethylenediamine (41 mg, 0.68 mmol). After stirring at room temperature overnight, the precipitate was collected by filtration to afford 15 mg (57%) of 2-(6-chloro-1-methyl-1H-indazol-3-yl)-5H-pyrrolo[2,3-b]pyrazine-7-carboxylic acid ((R)-2-hydroxy-1-methyl-ethyl)-amide as a yellow solid. MS: (M+H)⁺=385; ¹H NMR (300 MHz, DMSO-d₆) δ ppm 8.97 (d, J=2.64 Hz, 1H) 8.66 (d, J=8.69 Hz, 1H) 8.36 (s, 1H) 8.15 (d, J=7.93 Hz, 1H) 7.92 (s, 1H) 7.26 (d, J=8.31 Hz, 1H) 3.96-4.39 (m, 3H) 3.31-3.68 (m, 1H) 1.25 (d, J=6.80 Hz, 3H).

Example 201

2-(6-Chloro-1-methyl-1H-indazol-3-yl)-5H-pyrrolo[2,3-b]pyrazine-7-carboxylic acid (trans-2-hydroxy-1-methyl-propyl)-amide

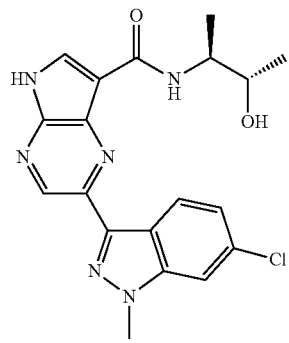 [SMILES: C[C@H](O)[C@H](C)NC(=O)c1c[nH]c2ncc(-c3nn(C)c4cc(Cl)ccc34)nc12]

Step 1 trans-3-Amino-butan-2-ol

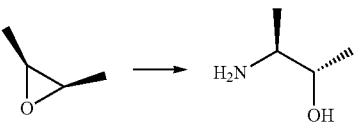

To a 20 mL microwave vial was added ammonia (7.87 g, 10 ml, 462 mmol), cis-2,3-dimethyloxirane (1.0 g, 13.9 mmol) and isopropyl alcohol (3 ml). The vial was capped and heated in the microwave at 160° C. for 1 h. The reaction was cooled to room temperature and the solvent evaporated to provide a 1.24 g of trans-3-amino-butan-2-ol as a colorless oil. ¹H NMR (300 MHz, d6-DMSO): δ 4.36 (bs, 1H), 3.19 (q, 1H, J=12 Hz), 2.48 (m, 1H), 1.39 (bs, 2H), 0.97 (m, 3H), 0.86 (m, 3H).

Step 2

2-(6-Chloro-1-methyl-1H-indazol-3-yl)-5-(2-trimethylsilanyl-ethoxymethyl)-5H-pyrrolo[2,3-b]pyrazine-7-carboxylic acid (trans-2-hydroxy-1-methyl-propyl)-amide

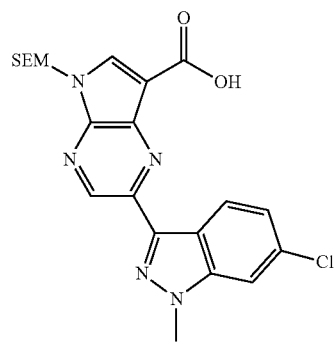

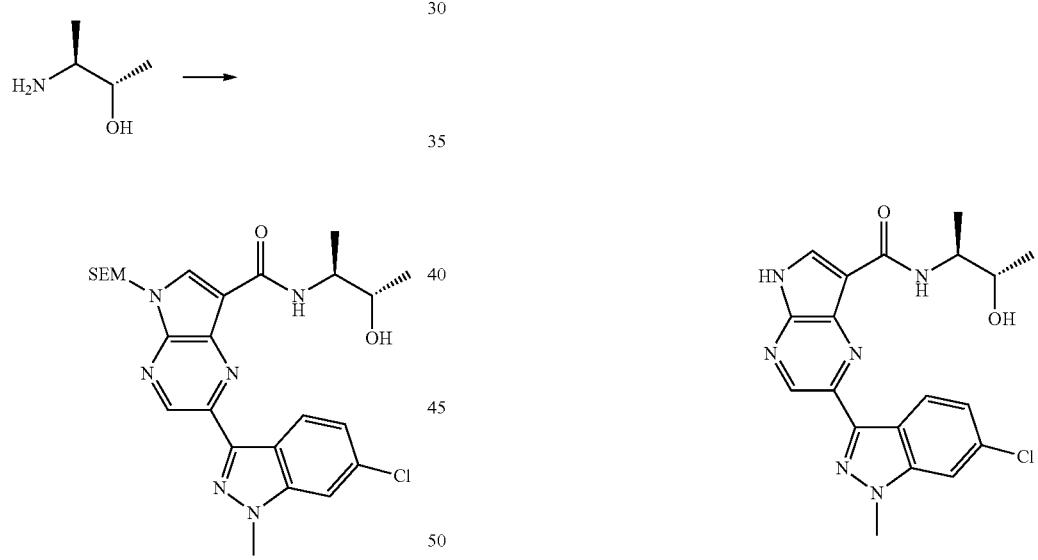

In a 20 mL scintillation vial, 2-(6-chloro-1-methyl-1H-indazol-3-yl)-5-(2-trimethylsilanyl-ethoxymethyl)-5H-pyrrolo[2,3-b]pyrazine-7-carboxylic acid (120 mg, 0.26 mmol), trans-3-aminobutan-2-ol (47 mg, 0.524 mmol), HBTU (129 mg, 0.341 mmol), HOBt (46 mg, 0.341 mmol) and DIPEA (169 mg, 1.31 mmol) were combined with DMF (1.8 ml) to give a light yellow solution. After stirring at room temperature overnight, the reaction mixture was diluted with EtOAc (50 mL) and washed with sat NaHCO$_3$ (3×25 mL) and H$_2$O (3×25 mL). The organic layer was dried over Na$_2$SO$_4$ and concentrated in vacuo. The crude material was purified by flash chromatography (silica gel, 4 g, 0% to 10% MeOH in DCM with 0.1% NH$_4$OH) to provide 127 mg (91%) of 2-(6-chloro-1-methyl-1H-indazol-3-yl)-5-(2-trimethylsilanylethoxymethyl)-5H-pyrrolo[2,3-b]pyrazine-7-carboxylic acid (trans-2-hydroxy-1-methyl-propyl)-amide as an off-white solid. MS: (M+H)$^+$=530.

Step 3

2-(6-Chloro-1-methyl-1H-indazol-3-yl)-5H-pyrrolo[2,3-b]pyrazine-7-carboxylic acid (trans-2-hydroxy-1-methyl-propyl)-amide 2-(6-Chloro-1-methyl-1H-indazol-3-yl)-5-(2-trimethylsilanyl-ethoxymethyl)-5H-pyrrolo[2,3-b]pyrazine-7-carboxylic acid (trans-2-hydroxy-1-methyl-propyl)-amide (120 mg, 0.227 mol) was dissolved in a 4:6 solution of TFA:DCM (34 mL). After stirring at room temperature overnight, the volatiles were removed under reduced pressure. The crude material was then dissolved in dichloromethane and treated with ethylenediamine (136 mg, 2.27 mmol). After stirring at room temperature overnight, water was added and the resulting precipitate was collected by filtration to afford 77 mg (85%) of 2-(6-chloro-1-methyl-1H-indazol-3-yl)-5H-pyrrolo[2,3-b]pyrazine-7-carboxylic acid (trans-2-hydroxy-1-methyl-propyl)-amide as a yellow solid. MS: (M+H)$^+$=399. $^1$H NMR (300 MHz, DMSO-d$_6$) δ ppm 12.65 (br. s., 1H) 9.13 (s, 1H) 8.76 (d, J=8.69 Hz, 1H) 8.40 (s, 1H) 8.10 (d, J=9.06 Hz, 1H)

7.94 (s, 5H) 7.32 (d, J=8.69 Hz, 1H) 5.16 (br. s., 1H) 4.01-4.30 (m, 4H) 3.81 (br. s., 1H) 1.26 (d, J=6.80 Hz, 3H) 1.09 (d, J=6.04 Hz, 3H).

Example 202

2-(6-Fluoro-1-methyl-1H-indazol-3-yl)-5H-pyrrolo[2,3-b]pyrazine-7-carboxylic acid (1-methyl-2-phenoxy-ethyl)-amide

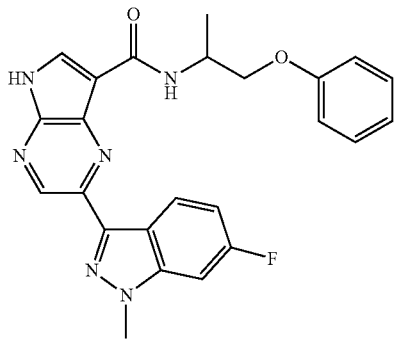 [SMILES: CC(COc1ccccc1)NC(=O)c1c[nH]c2ncc(-c3nn(C)c4cc(F)ccc34)nc12]

Step 1

2-(6-Fluoro-1-methyl-1H-indazol-3-yl)-5-(2-trimethylsilanyl-ethoxymethyl)-5H-pyrrolo[2,3-b]pyrazine-7-carboxylic acid (1-methyl-2-phenoxy-ethyl)-amide

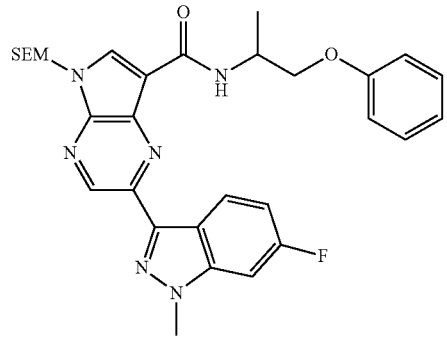

In a 100 mL round-bottomed flask, HBTU (78 mg, 0.21 mmol), Hunig's base (0.14 ml, 0.79 mmol) and 2-(6-fluoro-1-methyl-1H-indazol-3-yl)-5-(2-trimethylsilanyl-ethoxymethyl)-5H-pyrrolo[2,3-b]pyrazine-7-carboxylic acid (70 mg, 0.16 mmol) were combined with DMF (3 ml) to give a light yellow solution. 1-Phenoxypropan-2-amine (48 mg, 0.32 mmol) was added and the reaction mixture was stirred at 25° C. for 16 h. The reaction mixture was diluted with EtOAc. The reaction mixture was poured into 50 mL sat NaHCO₃ and extracted with EtOAc (2×50 mL). The organic layers were combined and washed with water (2×50 mL) then dried over MgSO₄ and concentrated in vacuo to provide 81 mg (89%) of 2-(6-fluoro-1-methyl-1H-indazol-3-yl)-5-(2-trimethylsilanyl-ethoxymethyl)-5H-pyrrolo[2,3-b]pyrazine-7-carboxylic acid (1-methyl-2-phenoxy-ethyl)-amide as a white solid. MS: (M+H)⁺=575.

Step 2

2-(6-Fluoro-1-methyl-1H-indazol-3-yl)-5H-pyrrolo[2,3-b]pyrazine-7-carboxylic acid (1-methyl-2-phenoxy-ethyl)-amide

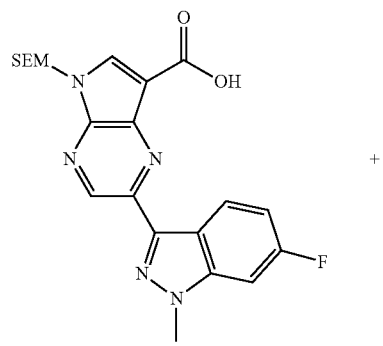

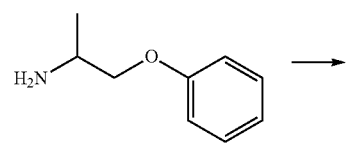

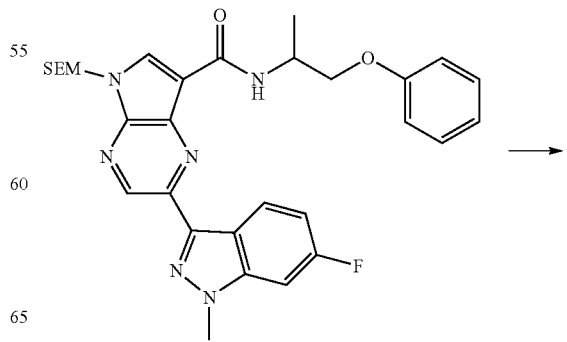

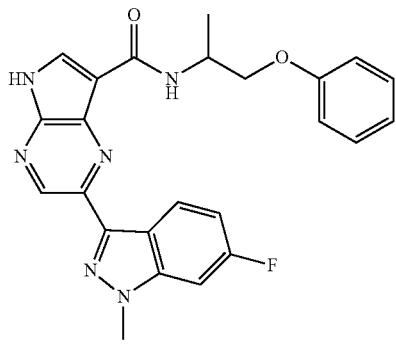

2-(6-Fluoro-1-methyl-1H-indazol-3-yl)-5-(2-trimethylsilanyl-ethoxymethyl)-5H-pyrrolo[2,3-b]pyrazine-7-carboxylic acid (1-methyl-2-phenoxy-ethyl)-amide (80 mg, 0.139 mol) was dissolved in a 4:6 solution of TFA:DCM (6.5 mL). After stirring at room temperature overnight, the volatiles were removed under reduced pressure. The crude material was then dissolved in dichloromethane and treated with ethylenediamine (837 mg, 13.9 mmol). After stirring at room temperature overnight, water was added and the resulting precipitate was collected by filtration to provide 35 mg (57%) of 2-(6-fluoro-1-methyl-1H-indazol-3-yl)-5H-pyrrolo[2,3-b]pyrazine-7-carboxylic acid (1-methyl-2-phenoxy-ethyl)-amide as a yellow solid.

MS: (M+H)$^+$=445; $^1$H NMR (300 MHz, DMSO-d$_6$) δ ppm 12.56 (s, 1H) 9.09 (s, 1H) 8.37-8.61 (m, 2H) 8.30 (d, J=7.93 Hz, 1H) 7.67 (d, J=7.93 Hz, 1H) 7.11-7.36 (m, 2H) 6.76-7.07 (m, 4H) 4.54 (br. s., 1H) 3.98-4.27 (m, 5H) 1.18-1.62 (m, 3H).

Example 203

2-(6-Fluoro-1-methyl-1H-indazol-3-yl)-5H-pyrrolo[2,3-b]pyrazine-7-carboxylic acid [2-hydroxy-1-methyl-2-(tetrahydro-pyran-4-yl)-ethyl]-amide (diastereomer A)

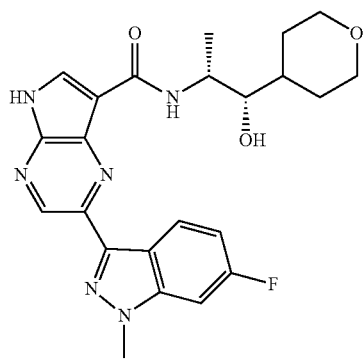 [SMILES: C[C@@H](NC(=O)c1c[nH]c2ncc(-c3nn(C)c4cc(F)ccc34)nc12)[C@@H](O)C1CCOCC1]

Step 1

2-Nitro-1-(tetrahydro-pyran-4-yl)-propan-1-ol

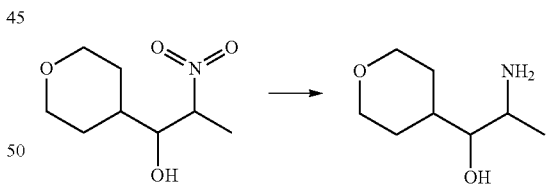

In a 100 mL round-bottomed flask, nitroethane (1.42 ml, 26.3 mmol) and tetrahydro-2H-pyran-4-carbaldehyde (1.0 g, 8.76 mmol) were combined with THF (5 ml) and tert-butanol to give a colorless solution. Potassium tert-butoxide (197 mg, 1.75 mmol,) was added at room temperature. After 30 min at room temperature, the reaction mixture was diluted with EtOAc and water. The organic phase was separated, dried, and evaporated to provide 1.3 g (79%) of crude 2-nitro-1-(tetrahydro-pyran-4-yl)-propan-1-ol as a colorless oil. $^1$H NMR (300 MHz, CDCl$_3$) δ ppm 4.74 (quin, J=6.61 Hz, 1H), 4.61 (qd, J=6.80, 3.02 Hz, 1H), 3.91-4.10 (m, 7H), 3.60 (t, J=5.48 Hz, 1H), 3.28-3.54 (m, 3H), 2.20-2.28 (m, 3H), 1.89-2.00 (m, 4H), 1.11-1.74 (m, 16H).

Step 2

2-Amino-1-(tetrahydro-pyran-4-yl)-propan-1-ol

2-Nitro-1-(tetrahydro-pyran-4-yl)-propan-1-ol (1.3 g, 6.87 mmol) was dissolved in ethanol (55 mL) and treated with palladium on carbon (0.2 g) under 1 atm of hydrogen. After stirring at room temperature overnight, the palladium was filtered off and the solvent reduced under reduced pressure to provide 1.0 g (91%) of 2-amino-1-(tetrahydro-pyran-4-yl)-propan-1-ol.

MS: (M+H)$^+$=160.

Step 3

2-(6-Fluoro-1-methyl-1H-indazol-3-yl)-5-(2-trimethylsilanyl-ethoxymethyl)-5H-pyrrolo[2,3-b]pyrazine-7-carboxylic acid [2-hydroxy-1-methyl-2-(tetrahydro-pyran-4-yl)-ethyl]-amide (diasteromer A and diasteromer B)

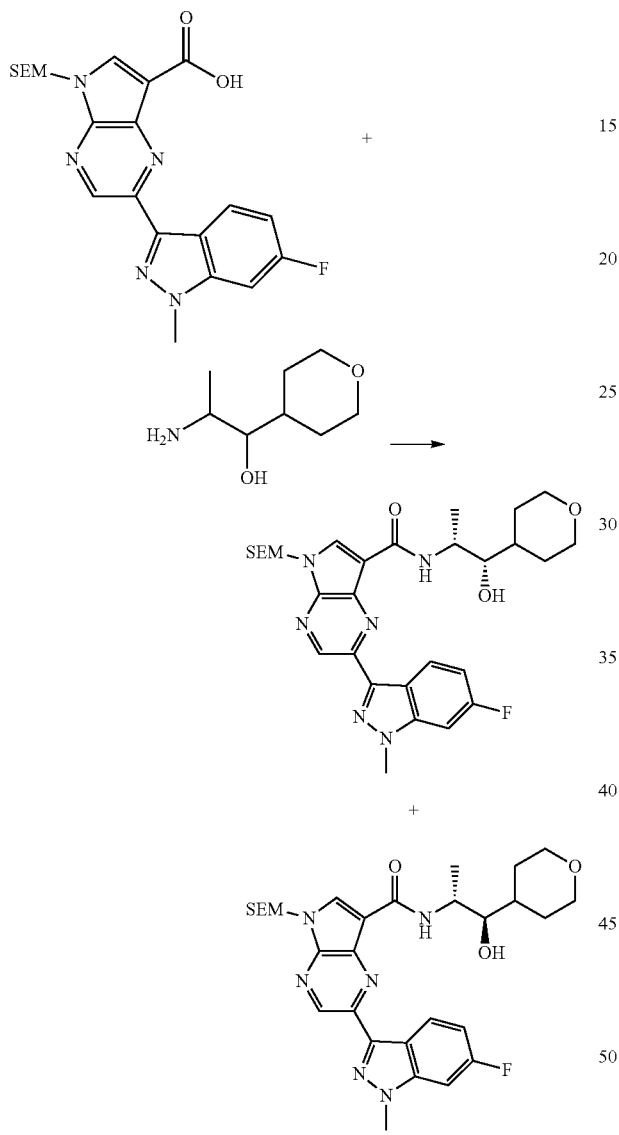

In a 100 mL round-bottomed flask, HBTU (112 mg, 0.29 mmol), Hunig's base (0.20 ml, 1.13 mmol) and 2-(6-fluoro-1-methyl-1H-indazol-3-yl)-5-(2-trimethylsilanyl-ethoxymethyl)-5H-pyrrolo[2,3-b]pyrazine-7-carboxylic acid (100 mg, 0.23 mmol) were combined with DMF (3.0 ml) to give a light yellow solution. 2-Amino-1-(tetrahydro-2H-pyran-4-yl)propan-1-ol (72 mg, 0.45 mmol) was added and the reaction mixture was stirred at 25° C. for 16 h. The reaction mixture was diluted with EtOAc. The reaction mixture was poured into 50 mL sat NaHCO₃ and extracted with EtOAc (2×50 mL). The organic layers were combined and washed with H₂O (2×50 mL) then dried over MgSO₄ and concentrated in vacuo to provide the crude material. The product was purified by flash chromatography (silica gel, 80 g, 20% to 50% EtOAc in hexanes) to provide 2-(6-fluoro-1-methyl-1H-indazol-3-yl)-5-(2-trimethylsilanyl-ethoxymethyl)-5H-pyrrolo[2,3-b]pyrazine-7-carboxylic acid [2-hydroxy-1-methyl-2-(tetrahydro-pyran-4-yl)-ethyl]-amide as two discreet diastereomers (arbitrarily assigned). Diastereomer A (30 mg, 22%) as a white powder: ¹H NMR (300 MHz, CDCl₃) δ ppm 9.20 (m, 1H), 8.68 (dd, J=8.69, 5.29 Hz, 1H), 8.41 (d, J=9.44 Hz, 1H), 8.27 (s, 1H) 6.96-7.13 (m, 2H) 5.70 (s, 2H) 4.54-4.67 (m, 1H) 4.06-4.20 (m, 4H) 3.87-4.04 (m, 2H) 3.56-3.65 (m, 2H) 3.42 (d, J=6.80 Hz, 1H) 3.21-3.39 (m, 2H), 2.53 (d, J=4.15 Hz, 1H) 1.85 (d, J=12.84 Hz, 2H) 1.76 (ddd, J=11.52, 7.93, 3.97 Hz, 1H), 1.33-1.56 (m, 5H), 0.75-1.04 (m, 2H), −0.05 (s, 9H). Diastereomer B (70 mg, 53%) as a white powder: ¹H NMR (300 MHz, CDCl₃) δ ppm 9.21 (s, 1H) 8.42-8.61 (m, 2H) 8.27 (s, 1H) 6.96-7.15 (m, 2H) 5.51-5.76 (m, 2H) 4.40-4.64 (m, 1H) 3.93-4.24 (m, 3H) 3.62-3.83 (m, 2H) 3.50-3.62 (m, 2H) 3.26-3.50 (m, 2H) 2.70 (d, J=5.29 Hz, 1H) 1.92-2.10 (m, 2H) 1.14-1.84 (m, 5H) 0.67-1.07 (m, 2H) −0.33-0.16 (m, 9H).

Step 4

2-(6-Fluoro-1-methyl-1H-indazol-3-yl)-5H-pyrrolo[2,3-b]pyrazine-7-carboxylic acid [2-hydroxy-1-methyl-2-(tetrahydro-pyran-4-yl)-ethyl]-amide (diastereomer A)

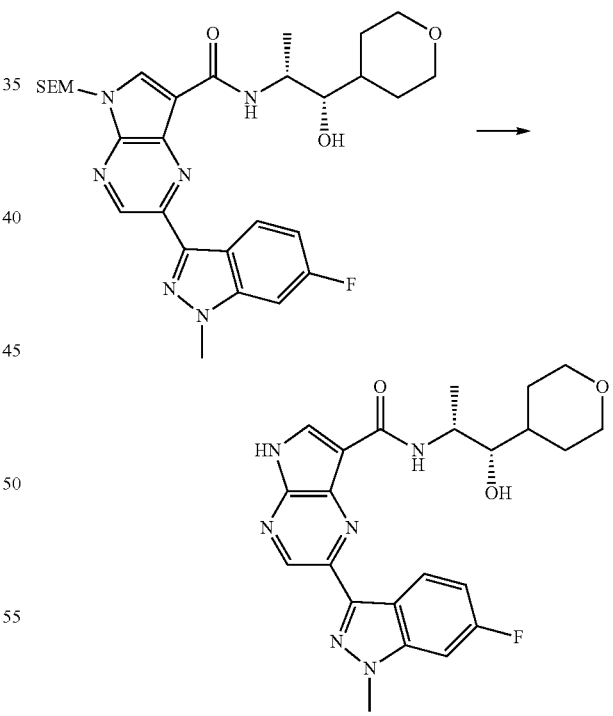

2-(6-Fluoro-1-methyl-1H-indazol-3-yl)-5-(2-trimethylsilanyl-ethoxymethyl)-5H-pyrrolo[2,3-b]pyrazine-7-carboxylic acid [2-hydroxy-1-methyl-2-(tetrahydro-pyran-4-yl)-ethyl]-amide, diastereomer A (26 mg, 0.034 mmol) was dissolved in a 4:6 solution of TFA:DCM (5.7 mL). After stirring at room temperature overnight, the volatiles were removed under reduced pressure. The crude material was then dissolved in dichloromethane and treated with ethylenediamine (206 mg, 3.43 mmol). After stirring at room temperature overnight, water was added and the resulting precipitate was collected by filtration to afford 13 mg (83%) of 2-(6-fluoro-1-methyl-1H-indazol-3-yl)-5H-pyrrolo[2,3-b]pyrazine-7-carboxylic acid [2-hydroxy-1-methyl-2-(tetrahydro-pyran-4-yl)-ethyl]-amide (diastereomer A) as an off-white solid. MS: (M+H)$^+$=453. $^1$H NMR (300 MHz, DMSO-d$_6$) δ ppm 12.79 (br. s., 1H) 9.15 (s, 1H) 8.85 (dd, J=8.88, 5.48 Hz, 1H) 8.40 (s, 1H) 8.13 (d, J=9.44 Hz, 1H) 7.56-7.78 (m, 1H) 7.11-7.37 (m, 1H) 5.49 (d, J=5.67 Hz, 1H) 4.34-4.53 (m, 1H) 4.13 (s, 3H) 3.80 (d, J=10.58 Hz, 2H) 3.18-3.28 (m, 1H) 3.11 (t, J=11.14 Hz, 2H) 1.66-1.89 (m, 2H) 1.42-1.66 (m, 1H) 1.10-1.36 (m, 5H).

Example 204

2-(6-Fluoro-1-methyl-1H-indazol-3-yl)-5H-pyrrolo[2,3-b]pyrazine-7-carboxylic acid [2-hydroxy-1-methyl-2-(tetrahydro-pyran-4-yl)-ethyl]-amide (diastereomer B)

2-(6-Fluoro-1-methyl-1H-indazol-3-yl)-5-(2-trimethylsilanyl-ethoxymethyl)-5H-pyrrolo[2,3-b]pyrazine-7-carboxylic acid [2-hydroxy-1-methyl-2-(tetrahydro-pyran-4-yl)-ethyl]-amide, diastereomer B (70 mg, 0.120 mmol) was dissolved in a 4:6 solution of TFA:DCM (5.7 mL). After stirring at room temperature overnight, the volatiles were removed under reduced pressure. The crude material was then dissolved in dichloromethane and treated with ethylenediamine (722 mg, 12 mmol). After stirring at room temperature overnight, water was added and the resulting precipitate was collected by filtration to provide 30 mg (55%) of 2-(6-fluoro-1-methyl-1H-indazol-3-yl)-5H-pyrrolo[2,3-b]pyrazine-7-carboxylic acid [2-hydroxy-1-methyl-2-(tetrahydro-pyran-4-yl)-ethyl]-amide (diastereomer B) as an off-white solid. MS: (M+H)$^+$=453. $^1$H NMR (300 MHz, DMSO-d$_6$) δ ppm 12.73 (br. s., 1H) 8.99-9.30 (m, 1H) 8.70 (dd, J=9.06, 5.29 Hz, 1H) 8.22-8.48 (m, 1H) 7.65 (dd, J=9.82, 1.89 Hz, 2H) 6.94-7.22 (m, 1H) 4.97 (d, J=6.80 Hz, 1H) 4.35 (m, 1H) 4.2 (s, 1H), 3.71 (m, 2H) 1.87 (d, J=13.60 Hz, 1H) 1.43-1.77 (m, 2H) 0.97-1.43 (m, 5H).

Example 205

2-(6-Chloro-1-methyl-1H-indazol-3-yl)-5H-pyrrolo[2,3-b]pyrazine-7-carboxylic acid ((R)-3-cyano-1-methyl-propyl)-amide

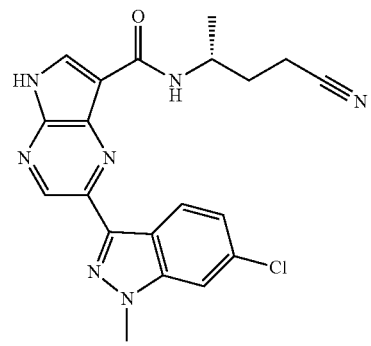 [SMILES: C[C@H](CCC#N)NC(=O)c1c[nH]c2ncc(-c3nn(C)c4cc(Cl)ccc34)nc12]

Step 1

((R)-3-Cyano-1-methyl-allyl)-carbamic acid tert-butyl ester

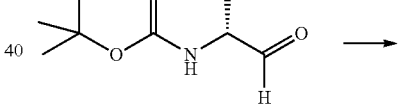

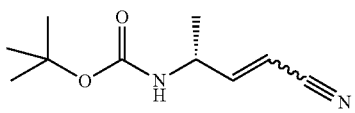

In a 20 mL scintillation vial, ((R)-1-methyl-2-oxo-ethyl)-carbamic acid tert-butyl ester (2.5 g, 14.4 mmol) and (triphenylphosphoranylidene)acetonitrile (6.52 g, 21.7 mmol) were mixed in dichloromethane (20 mL) and stirred at room temperature for 16 h. The solvent was evaporated to give the crude material, which was purified by column chromatography (silica gel, gradient n-hexanes ethyl acetate) to provide 1.8 g (63%) of ((R)-3-cyano-1-methyl-allyl)-carbamic acid tert-butyl ester in a 3:1 diastereoselectivity (E:Z) as a colorless oil. $^1$H NMR (300 MHz, CDCl$_3$) δ ppm 6.38-6.79 (m, 1H), 5.47 (dd, J=16.24, 1.89 Hz, 1H), 4.48 (bs, 1H), 4.47 (bs, 1H), 1.45 (s, 1H), 1.28 (d, J=7.18 Hz, 9H).

Step 2

((R)-3-Cyano-1-methyl-propyl)-carbamic acid tert-butyl ester

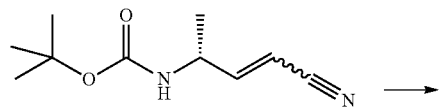

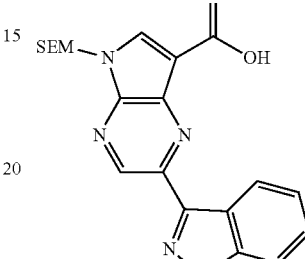

In a 250 mL round-bottomed flask, palladium on carbon (150 mg) and a mixture of 3:1 E:Z olefins ((R)-3-cyano-1-methyl-allyl)-carbamic acid tert-butyl ester (375 mg, 1.91 mmol) were combined with ethanol to give a black suspension. The reaction mixture was stirred at 25° C. for 16 h under a hydrogen balloon. The reaction mixture was filtered through celite. The crude reaction mixture was concentrated in vacuo to provide 250 mg (66%) of ((R)-3-cyano-1-methyl-propyl)-carbamic acid tert-butyl ester as a colorless oil which was used without further purification. $^1$H NMR (300 MHz, CDCl$_3$) δ ppm 4.30-4.65 (m, 1H), 3.52-3.81 (m, 1H), 2.28 (m, 1H), 2.72 (m, 1H), 1.58-1.97 (m, 1H), 1.04-1.24 (m, 3H).

Step 3

(R)-4-Aminopentanenitrile trifluoroacetate

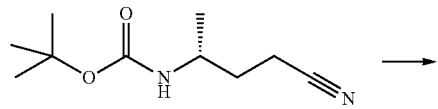

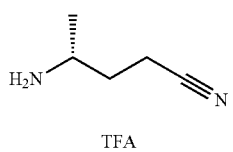

TFA

In a 100 mL round-bottomed flask, ((R)-3-cyano-1-methyl-propyl)-carbamic acid tert-butyl ester (158 mg, 0.80 mmol) was combined with TFA (2 ml) and dichloromethane (8 mL) to give a colorless solution. The reaction mixture was stirred at 25° C. for 15 h. The solvent was evaporated to provide 53 mg (68%) of (R)-4-aminopentanenitrile trifluoroacetate which was used in the next step without further purification.

Step 4

2-(6-Chloro-1-methyl-1H-indazol-3-yl)-5-(2-trimethylsilanyl-ethoxymethyl)-5H-pyrrolo[2,3-b]pyrazine-7-carboxylic acid ((R)-3-cyano-1-methyl-propyl)-amide

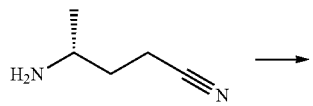

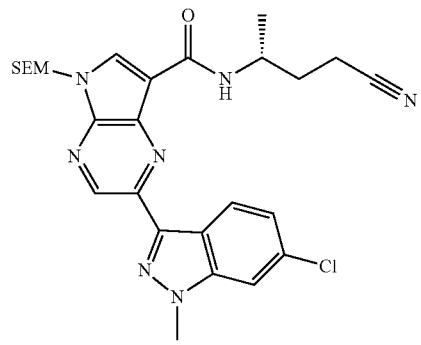

In a 20 mL scintillation vial, 2-(6-chloro-1-methyl-1H-indazol-3-yl)-5-(2-trimethylsilanyl-ethoxymethyl)-5H-pyrrolo[2,3-b]pyrazine-7-carboxylic acid (120 mg, 0.26 mmol), (R)-4-aminopentanenitrile trifluoroacetate (51 mg, 0.524 mmol), HBTU (129 mg, 0.341 mmol), HOBt (46 mg, 0.341 mmol) and DIPEA (169 mg, 1.31 mmol) were combined with DMF (1.8 ml) to give a light yellow solution. After stirring at room temperature overnight the reaction mixture was diluted with EtOAc (50 mL) and washed with sat NaHCO$_3$ (3×25 mL) and H$_2$O (3×25 mL). The organic layer was dried over Na$_2$SO$_4$ and concentrated in vacuo. The crude material was purified by flash chromatography (silica gel, 4 g, 0% to 10% MeOH in DCM with 0.1% NH$_4$OH) to provide 99 mg (70%) of 2-(6-chloro-1-methyl-1H-indazol-3-yl)-5-(2-trimethylsilanyl-ethoxymethyl)-5H-pyrrolo[2,3-b]pyrazine-7-carboxylic acid ((R)-3-cyano-1-methyl-propyl)-amide as an off-white solid. MS: (M+H)+=539.

Step 5

2-(6-Chloro-1-methyl-1H-indazol-3-yl)-5H-pyrrolo[2,3-b]pyrazine-7-carboxylic acid ((R)-3-cyano-1-methyl-propyl)-amide

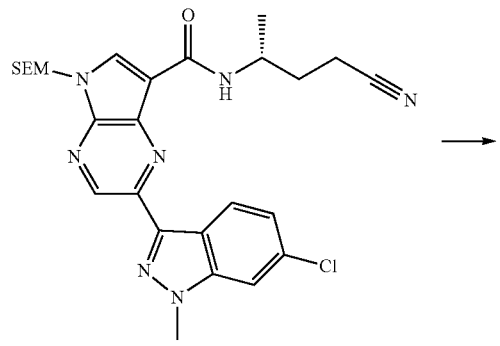

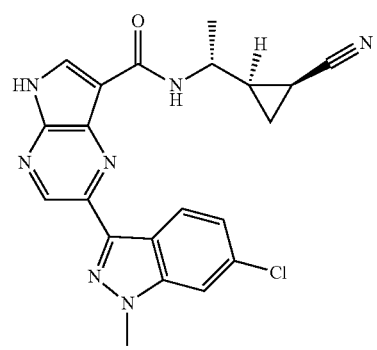 [SMILES: C[C@@H](NC(=O)c1c[nH]c2ncc(-c3nn(C)c4cc(Cl)ccc34)nc12)[C@@H]1C[C@@H]1C#N]

2-(6-Chloro-1-methyl-1H-indazol-3-yl)-5-(2-trimethylsilanyl-ethoxymethyl)-5H-pyrrolo[2,3-b]pyrazine-7-carboxylic acid ((R)-3-cyano-1-methyl-propyl)-amide (120 mg, 0.223 mmol) was dissolved in a 4:6 solution of TFA:DCM (57 mL). After stirring at room temperature overnight, the volatiles were removed under reduced pressure. The crude material was then dissolved in dichloromethane and treated with ethylenediamine (134 mg, 2.23 mmol). After stirring at room temperature overnight, water was added and the resulting precipitate was collected by filtration to provide 45 mg (49%) of 2-(6-chloro-1-methyl-1H-indazol-3-yl)-5H-pyrrolo[2,3-b]pyrazine-7-carboxylic acid ((R)-3-cyano-1-methyl-propyl)-amide as a yellow solid.

MS: (M+H)+=408. $^1$H NMR (300 MHz, DMSO-d$_6$) δ ppm 12.81 (br. s., 1H) 8.88-9.14 (m, 1H) 8.35-8.51 (m, 1H) 7.93-8.10 (m, 2H) 7.35 (dd, J=8.69, 1.89 Hz, 1H) 4.08-4.36 (m, 4H) 2.61 (t, J=7.36 Hz, 2H) 1.76-2.02 (m, 2H) 1.32 (d, J=6.80 Hz, 3H).

Example 206

2-(6-Chloro-1-methyl-1H-indazol-3-yl)-5H-pyrrolo[2,3-b]pyrazine-7-carboxylic acid [(R)-1-(2-cyano-cyclopropyl)-ethyl]-amide (diastereomer A)

Step 1

[(R)-1-(2-Cyano-cyclopropyl)-ethyl]-carbamic acid tert-butyl ester (diasteromer A and diasteromer B)

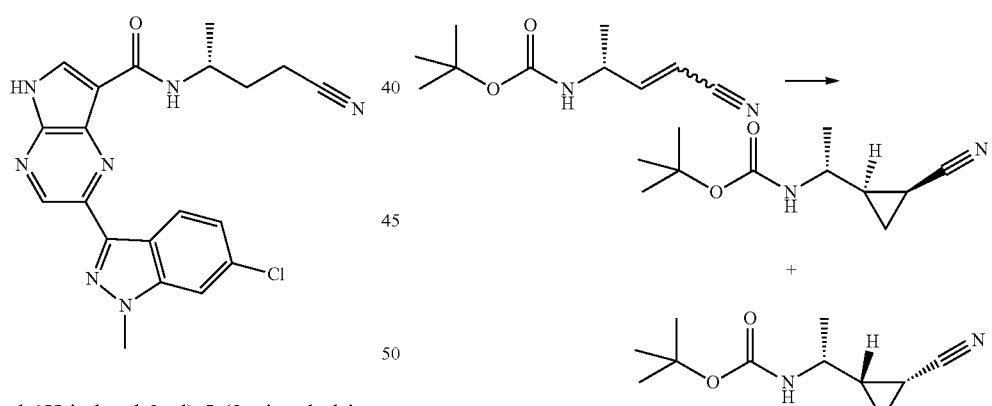

DMSO was added to trimethylsulfonium iodide (1.79 g, 8.15 mmol) and sodium hydride (60% in mineral oil, 326 mg, 8.15 mmol) at 0° C. Then a 3:1 E:Z mixture of ((R)-3-cyano-1-methyl-allyl)-carbamic acid tert-butyl ester (0.4 g, 2.04 mmol) in DMSO was added. The reaction mixture was left to warm up to room temperature overnight. The reaction was stirred at room temperature for 2 days then diluted with water and ethyl acetate. The organic layers were dried over MgSO$_4$ and concentrated in vacuo. The crude material was purified by flash chromatography (silica gel, 80 g, 20% to 50% EtOAc in hexanes) to provide [(R)-1-(2-cyanocyclopropyl)-ethyl]-carbamic acid tert-butyl ester as two discreet diastereomers (arbitrarily assigned). Diastereomer A (250 mg, 58%) as a colorless oil; MS: (M+H)⁺=211. Diastereomer B (130 mg, 30%) as a white powder; M+Na⁺=233.

Step 2

2-((R)-1-Amino-ethyl)-cyclopropanecarbonitrile trifluoroacetate (diastereomer A)

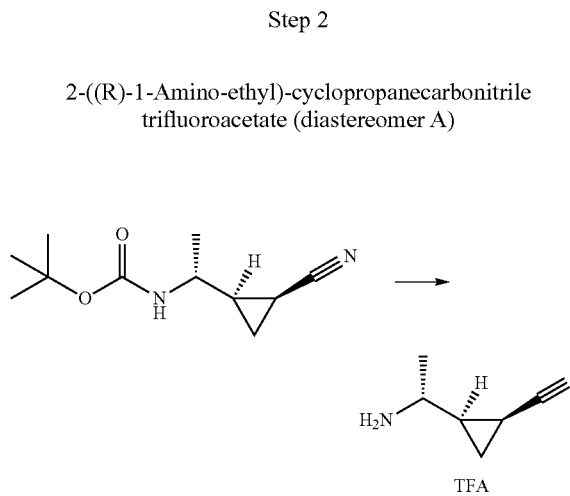

In a 100 mL round-bottomed flask, [(R)-1-(2-cyano-cyclopropyl)-ethyl]-carbamic acid tert-butyl ester, diastereomer A (250 mg, 1.19 mmol) was dissolved in TFA (2 ml) and dichloromethane (8 mL). The reaction mixture was stirred at 25° C. for 15 h and the volatiles were removed under reduced pressure to afford 2-((R)-1-amino-ethyl)-cyclopropanecarbonitrile trifluoroacetate (diastereomer A) which was used in the next step without further purification.

Step 3

2-(6-Chloro-1-methyl-1H-indazol-3-yl)-5-(2-trimethylsilanyl-ethoxymethyl)-5H-pyrrolo[2,3-b]pyrazine-7-carboxylic acid [(R)-1-(2-cyano-cyclopropyl)-ethyl]-amide (diastereomer A)

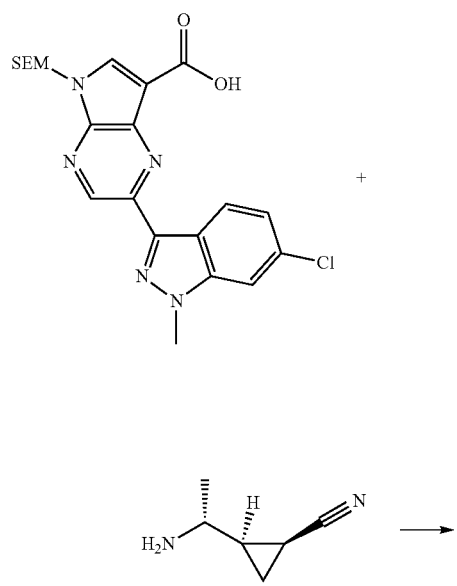

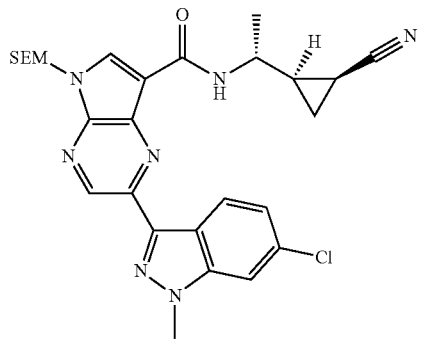

2-((R)-1-Amino-ethyl)-cyclopropanecarbonitrile trifluoroacetate, diastereomer A (crude from Step 2) was treated with 1-hydroxybenzotriazole (153 mg, 1.14 mmol), 2-(1H-benzo[d][1,2,3]triazol-1-yl)-1,1,3,3-tetramethylisouronium hexafluorophosphate(V) (662 mg, 1.75 mmol,), DIPEA (0.76 ml, 4.37 mmol), 2-(6-chloro-1-methyl-1H-indazol-3-yl)-5-(2-trimethylsilanyl-ethoxymethyl)-5H-pyrrolo[2,3-b]pyrazine-7-carboxylic acid (400 mg, 0.87 mmol) and DMF (6.0 ml) to give a light yellow solution. After stirring at room temperature overnight, the reaction mixture was diluted with ethyl acetate and water. The organic layers were dried over MgSO₄ and concentrated in vacuo. The crude material was purified by flash chromatography (silica gel, 40 g, EtOAc in heptane gradient) to provide 210 mg (44%) of 2-(6-chloro-1-methyl-1H-indazol-3-yl)-5-(2-trimethylsilanyl-ethoxymethyl)-5H-pyrrolo[2,3-b]pyrazine-7-carboxylic acid [(R)-1-(2-cyano-cyclopropyl)-ethyl]-amide (diastereomer A) as a colorless oil. MS: (M+H)⁺=551.

Step 4

2-(6-Chloro-1-methyl-1H-indazol-3-yl)-5H-pyrrolo[2,3-b]pyrazine-7-carboxylic acid [(R)-1-(2-cyano-cyclopropyl)-ethyl]-amide (diastereomer A)

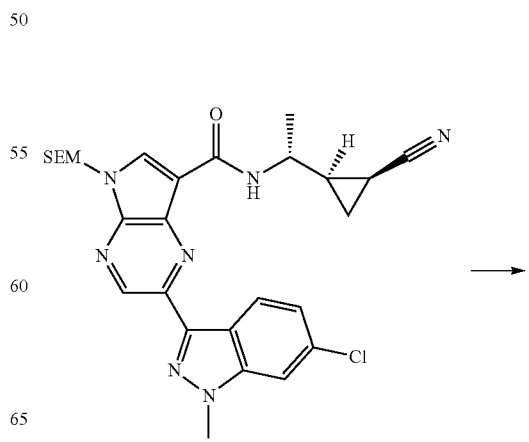

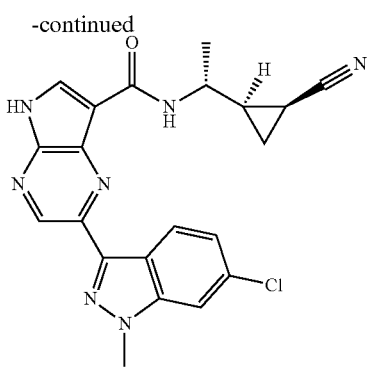

2-(6-Chloro-1-methyl-1H-indazol-3-yl)-5-(2-trimethylsilanyl-ethoxymethyl)-5H-pyrrolo[2,3-b]pyrazine-7-carboxylic acid [(R)-1-(2-cyano-cyclopropyl)-ethyl]-amide, diastereomer A (210 mg, 0.382 mmol) was dissolved in a 4:6 solution of TFA:DCM (57 mL). After stirring at room temperature overnight, the volatiles were removed under reduced pressure. The crude material was then dissolved in dichloromethane and treated with ethylenediamine (229 mg, 3.82 mmol). After stirring at room temperature overnight, water was added and the resulting precipitate was collected by filtration to give 140 mg (87%) of 2-(6-chloro-1-methyl-1H-indazol-3-yl)-5H-pyrrolo[2,3-b]pyrazine-7-carboxylic acid [(R)-1-(2-cyano-cyclopropyl)-ethyl]-amide (diastereomer A) as a light yellow solid. MS: (M+H)$^+$=420. $^1$H NMR (300 MHz, DMSO-$d_6$) δ ppm 9.70 (bs, 1H) 9.08 (s, 4H) 8.32-8.58 (m, 2H) 8.13 (dd, J=12.27, 8.12 Hz, 1H) 7.98 (s, 1H) 7.24-7.44 (m, 1H) 4.16 (s, 3H) 3.80 (d, J=5.29 Hz, 1H) 1.61-1.96 (m, 2H) 1.40 (m, 3H) 0.98-1.30 (m, 2H).

Example 207

2-(6-Chloro-1-methyl-1H-indazol-3-yl)-5H-pyrrolo[2,3-b]pyrazine-7-carboxylic acid [(R)-1-(2-cyano-cyclopropyl)-ethyl]-amide (diastereomer B)

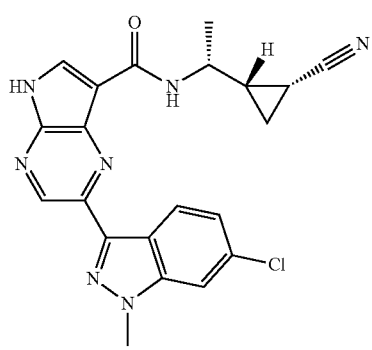 [SMILES: C[C@@H](NC(=O)c1c[nH]c2ncc(-c3nn(C)c4cc(Cl)ccc34)nc12)[C@H]1C[C@H]1C#N]

Prepared according to the procedure outlined in Example 206, Steps 2-4, substituting [(R)-1-(2-cyano-cyclopropyl)-ethyl]-carbamic acid tert-butyl ester, diastereomer B for [(R)-1-(2-cyano-cyclopropyl)-ethyl]-carbamic acid tert-butyl ester, diastereomer A in Step 2. the product was isolated as a light yellow solid. MS: (M+H)$^+$=420 (M+H)$^+$. $^1$H NMR (300 MHz, DMSO-$d_6$) δ ppm 9.10 (s, 1H) 8.40-8.52 (m, 2H) 8.32 (d, J=7.93 Hz, 1H) 7.99 (s, 1H) 7.35 (d, J=8.69 Hz, 1H) 4.06-4.22 (m, 3H) 3.80 (d, J=9.82 Hz, 1H) 1.92-2.10 (m, 1H) 1.56-1.73 (m, 1H) 1.49 (d, J=6.80 Hz, 3H) 0.94-1.35 (m, 2H).

Example 208

2-(6-Fluoro-1-methyl-1H-indazol-3-yl)-5H-pyrrolo[2,3-b]pyrazine-7-carboxylic acid [1-(4-bromo-phenyl)-cyclopropyl]-amide

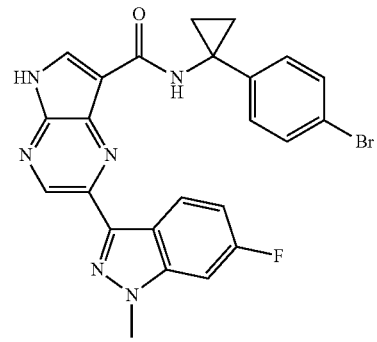

Step 1

2-(6-Fluoro-1-methyl-1H-indazol-3-yl)-5-(2-trimethylsilanyl-ethoxymethyl)-5H-pyrrolo[2,3-b]pyrazine-7-carboxylic acid [1-(4-bromo-phenyl)-cyclopropyl]-amide

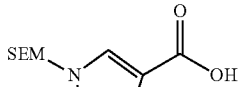

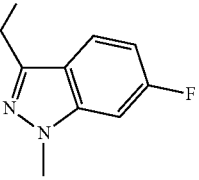

+

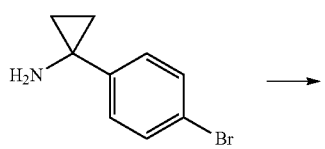

-continued

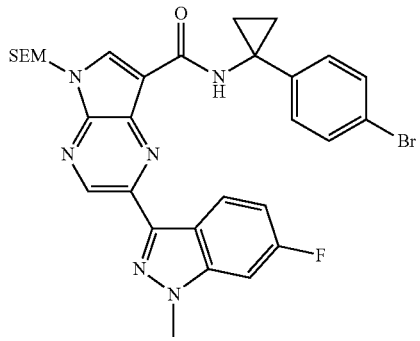

To a stirred suspension of 2-(6-fluoro-1-methyl-1H-indazol-3-yl)-5-(2-trimethylsilanylethoxymethyl)-5H-pyrrolo[2,3-b]pyrazine-7-carboxylic acid (150 mg, 0.34 mmol) in DMF (5 mL) were added HATU (258 mg, 0.68 mmol) and 1-(4-bromo-phenyl)-cyclopropanamine (108 mg, 0.51 mmol) followed by DIPEA (0.24 mL, 1.36 mmol) at room temperature under nitrogen atmosphere. The resulting light yellow solution was stirred for 15 h by which time TLC analysis (Hex: EA, 1:1, $R_f$=0.5) indicated the presence of a new spot. Then, the reaction mixture was diluted with water and the organic compound was extracted into EtOAc (3×25 mL). The combined extracts were washed with brine solution and then dried over anhydrous MgSO$_4$. Filtration of the drying agent and concentration of the filtrate gave the crude product which was purified using by ISCO column chromatography (40 g) eluting with EtOAc in hexanes (0-60%) in 10 minutes. The desired fractions were combined and the solvent was removed under vacuum to obtain 197 mg (91%) of 2-(6-fluoro-1-methyl-1H-indazol-3-yl)-5-(2-trimethylsilanylethoxymethyl)-5H-pyrrolo[2,3-b]pyrazine-7-carboxylic acid [1-(4-bromo-phenyl)-cyclopropyl]-amide as a off-white solid.

Step 2

2-(6-Fluoro-1-methyl-1H-indazol-3-yl)-5H-pyrrolo[2,3-b]pyrazine-7-carboxylic acid [1-(4-bromo-phenyl)-cyclopropyl]-amide

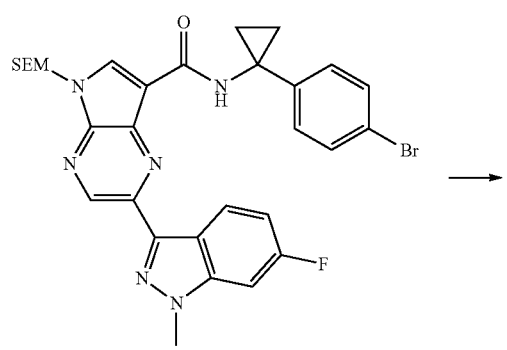

-continued

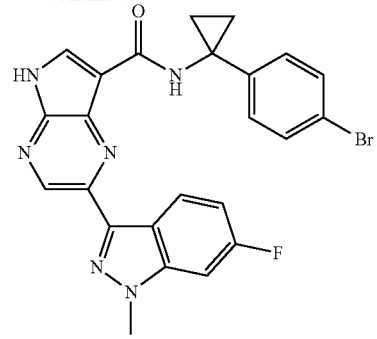 [SMILES: Cn1nc(-c2cnc3[nH]cc(C(=O)NC4(c5ccc(Br)cc5)CC4)c3n2)c2ccc(F)cc21]

To a stirred solution of 2-(6-fluoro-1-methyl-1H-indazol-3-yl)-5-(2-trimethylsilanylethoxymethyl)-5H-pyrrolo[2,3-b]pyrazine-7-carboxylic acid [1-(4-bromo-phenyl)-cyclopropyl]-amide (50 mg, 0.078 mmol) in THF (3 mL) was added a solution of TBAF (1.0 M in THF, 1.18 mL, 1.18 mmol) at room temperature. The resulting light brown solution was heated to 85° C. and stirred for 3 h at which time TLC analysis (EA, $R_f$=0.3) indicated the absence of starting material. Then, the reaction mixture was cooled to room temperature and 3 mL of acetone and 9 mL of saturated sodium bicarbonate solution were added and the resulting suspension was stirred for 1 h. The reaction suspension was diluted with water and the organic compound was extracted into EtOAc (3×25 mL) and the combined extracts were washed with brine solution and dried over MgSO$_4$. Filtration of the drying agent and removal of the solvent under vacuum gave the crude solid which was dissolved in acetonitrile with heating. The resulting greenish solution was stored in the refrigerator for 15 h and the solids were collected by filtration and washed with acetonitrile. After drying in air, 25 mg (63%) of 2-(6-fluoro-1-methyl-1H-indazol-3-yl)-5H-pyrrolo[2,3-b]pyrazine-7-carboxylic acid [1-(4-bromo-phenyl)-cyclopropyl]-amide was isolated as a off-white solid. LC-MS (M+H)$^+$=507; $^1$H NMR (300 MHz, DMSO-d$_6$) δ: 12.91 (s, 1H), 9.11 (s, 1H), 8.99 (s, 1H), 8.52 (s, 1H), 8.39-8.51 (m, 1H), 7.68 (dd, J=9.7, 1.9 Hz, 1H), 7.47 (d, J=8.5 Hz, 2H), 7.27 (d, J=8.5 Hz, 2H), 7.14 (td, J=9.0, 2.0 Hz, 1H), 4.14 (s, 3H), 1.44 (s, 4H).

Example 209

2-(6-Fluoro-1-methyl-1H-indazol-3-yl)-5H-pyrrolo[2,3-b]pyrazine-7-carboxylic acid [1-(3-bromo-phenyl)-cyclobutyl]-amide

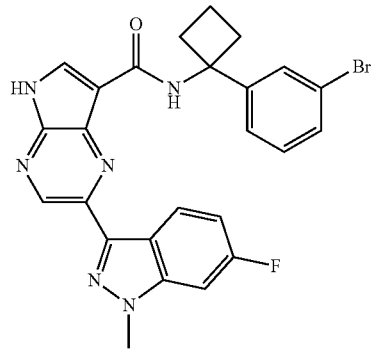 [SMILES: Cn1nc(-c2cnc3[nH]cc(C(=O)NC4(c5cccc(Br)c5)CCC4)c3n2)c2ccc(F)cc21]

Step 1

2-(6-Fluoro-1-methyl-1H-indazol-3-yl)-5-(2-trimethylsilanyl-ethoxymethyl)-5H-pyrrolo[2,3-b]pyrazine-7-carboxylic acid [1-(3-bromo-phenyl)-cyclobutyl]-amide

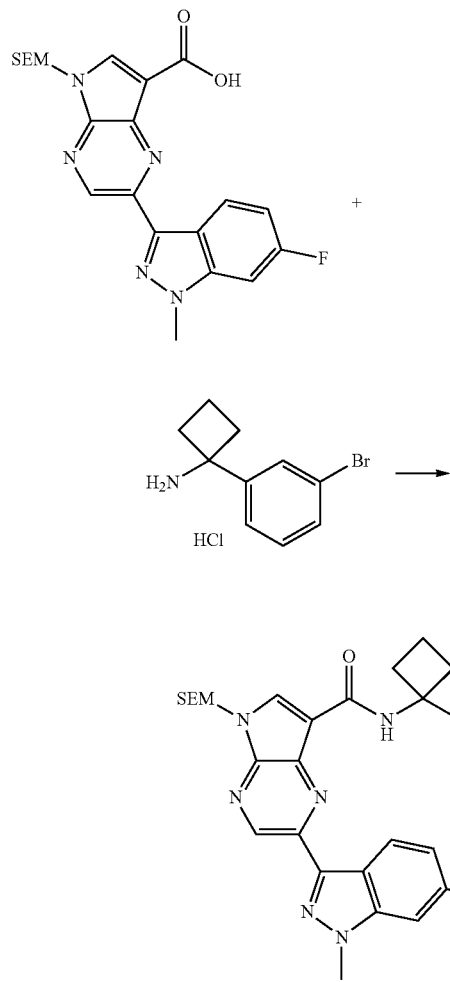

To a stirred suspension of 2-(6-fluoro-1-methyl-1H-indazol-3-yl)-5-(2-trimethylsilanylethoxymethyl)-5H-pyrrolo[2,3-b]pyrazine-7-carboxylic acid (200 mg, 0.45 mmol) in DMF (5 mL) were added HATU (344 mg, 0.91 mmol) and 1-(3-bromo-phenyl)-cyclobutanamine hydrochloride (178 mg, 0.68 mmol) followed by DIPEA (0.40 mL, 2.26 mmol) at room temperature under nitrogen atmosphere. The resulting light yellow solution was stirred for 15 h by which time TLC analysis (Hex:EA, 1:1, $R_f$=0.5) indicated the presence of a new spot. Then, the reaction mixture was diluted with water and the organic compound was extracted into EtOAc (3×25 mL). The combined extracts were washed with brine solution and then dried over anhydrous $MgSO_4$. Filtration of the drying agent and concentration of the filtrate gave the crude product which was purified using by ISCO column chromatography (40 g) eluting with EtOAc in hexanes (0-60%) in 10 minutes. The desired fractions were combined and the solvent was removed under vacuum to obtain 234 mg (80%) of 2-(6-fluoro-1-methyl-1H-indazol-3-yl)-5-(2-trimethylsilanyl-ethoxymethyl)-5H-pyrrolo[2,3-b]pyrazine-7-carboxylic acid [1-(3-bromophenyl)-cyclobutyl]-amide as a light brown solid.

Step 2

2-(6-Fluoro-1-methyl-1H-indazol-3-yl)-5H-pyrrolo[2,3-b]pyrazine-7-carboxylic acid [1-(3-bromo-phenyl)-cyclobutyl]-amide

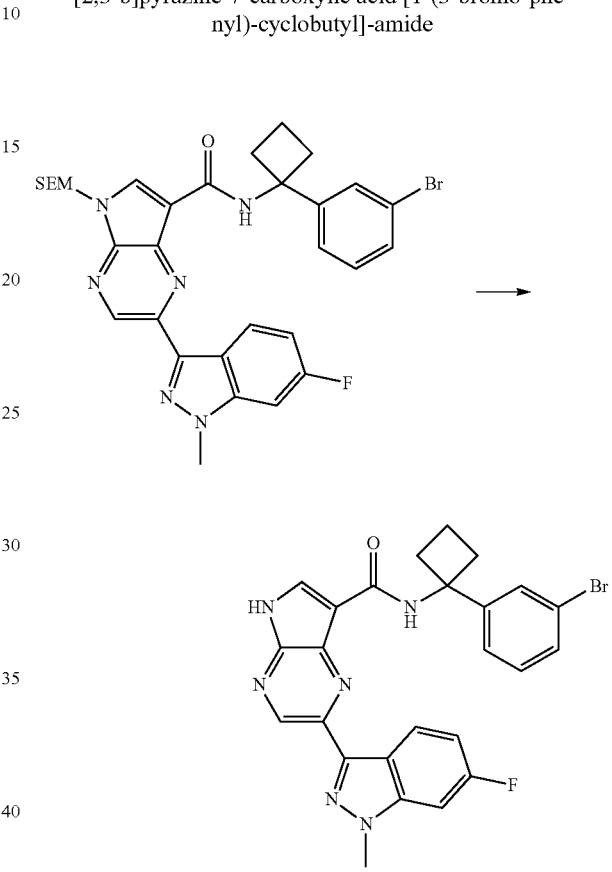

To a light brown solution of 2-(6-fluoro-1-methyl-1H-indazol-3-yl)-5-(2-trimethylsilanylethoxymethyl)-5H-pyrrolo[2,3-b]pyrazine-7-carboxylic acid [1-(3-bromo-phenyl)-cyclobutyl]-amide (50 mg, 0.077 mmol) in dichloromethane (3 mL) was added an excess of TFA (1.2 mL, 15.4 mmol) at room temperature under nitrogen atmosphere. The resulting light brown solution was stirred for 4 h at which time TLC analysis (EA, $R_f$=0.35) indicated the absence of starting material. Then, the solvent was removed under vacuum and the residue was azeotroped with toluene to obtain a light brown solid. Then, this solid was treated with an excess of triethylamine (1.07 mL, 7.7 mmol) in methanol (3 mL) at room temperature under nitrogen atmosphere. The resulting suspension was stirred for 15 h and then the solvent was removed under vacuum. The residue was triturated with acetonitrile and the solids were collected by filtration and washed with acetonitrile. After drying in air, 15 mg (38%) of the 2-(6-fluoro-1-methyl-1H-indazol-3-yl)-5H-pyrrolo[2,3-b]pyrazine-7-carboxylic acid [1-(3-bromo-phenyl)-cyclobutyl]-amide was isolated as a light yellow solid. LC-MS $(M+H)^+$=519; $^1H$ NMR (300 MHz, DMSO-$d_6$) δ: 12.80 (br. s., 1H), 9.10 (s, 1H), 8.77 (s, 1H), 8.55 (dd, J=8.8, 5.5 Hz, 1H), 8.36 (s, 1H), 7.64-7.80 (m, 2H), 7.57 (d, J=7.8 Hz, 1H), 7.41

(d, J=7.8 Hz, 1H), 7.23-7.35 (m, 1H), 7.15 (t, J=8.2 Hz, 1H), 4.15 (s, 3H), 2.56-2.81 (m, 4H), 2.19 (d, J=8.5 Hz, 1H), 1.96 (d, J=8.3 Hz, 1H).

Example 210

2-(6-Fluoro-1-methyl-1H-indazol-3-yl)-5H-pyrrolo[2,3-b]pyrazine-7-carboxylic acid [1-(4-bromo-phenyl)-cyclobutyl]-amide

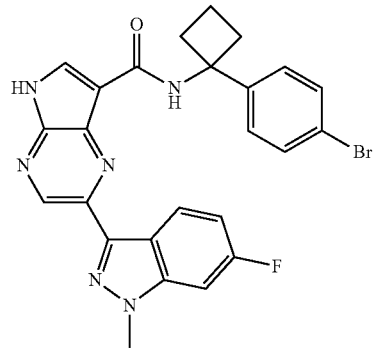 [SMILES: Cn1nc(-c2cnc3[nH]cc(C(=O)NC4(c5ccc(Br)cc5)CCC4)c3n2)c2ccc(F)cc21]

Prepared according to the procedure outlined in Example 209, substituting 1-(4-bromophenyl)-cyclobutanamine hydrochloride for 1-(3-bromo-phenyl)-cyclobutanamine hydrochloride in Step 1. LC-MS (M+H)⁺=519; ¹H NMR (300 MHz, DMSO-d₆) δ: 12.87 (br. s., 1H), 9.10 (s, 1H), 8.76 (s, 1H), 8.48 (dd, J=8.5, 5.3 Hz, 1H), 8.35 (s, 1H), 7.69 (d, J=9.3 Hz, 1H), 7.52 (s, 4H), 7.13 (t, J=8.5 Hz, 1H), 4.15 (s, 3H), 2.68 (t, J=7.4 Hz, 4H), 2.17 (d, J=7.8 Hz, 1H), 1.85-2.03 (m, 1H).

Example 211

2-(6-Fluoro-1-methyl-1H-indazol-3-yl)-5H-pyrrolo[2,3-b]pyrazine-7-carboxylic acid [(R)-1-(4-bromo-phenyl)-2,2,2-trifluoro-ethyl]-amide

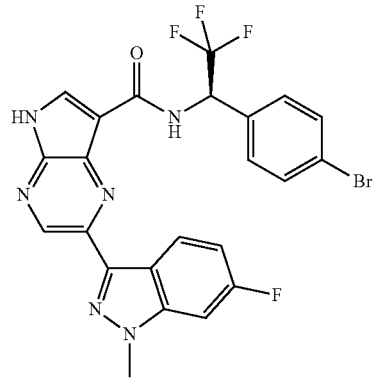 [SMILES: Cn1nc(-c2cnc3[nH]cc(C(=O)N[C@H](c4ccc(Br)cc4)C(F)(F)F)c3n2)c2ccc(F)cc21]

Prepared according to the procedure outlined in Example 209, substituting (R)-1-(4-bromo-phenyl)-2,2,2-trifluoroethanamine for 1-(3-bromo-phenyl)-cyclobutanamine hydrochloride in Step 1. LC-MS (M+H)⁺=547; ¹H NMR (300 MHz, DMSO-d₆) δ: 12.87 (br. s., 1H), 8.81-9.13 (m, 2H), 8.47 (s, 1H), 8.21-8.36 (m, 1H), 7.34-7.69 (m, 4H), 6.88 (t, J=8.4 Hz, 1H), 6.08-6.27 (m, 1H), 5.63 (s, 1H), 4.03 (s, 3H).

Example 212

2-(5,6-Difluoro-1-methyl-1H-indazol-3-yl)-5H-pyrrolo[2,3-b]pyrazine-7-carboxylic acid ((S)-2-methoxy-1-methyl-ethyl)-amide

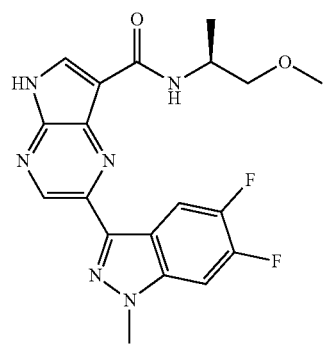 [SMILES: COC[C@H](C)NC(=O)c1c[nH]c2ncc(-c3nn(C)c4cc(F)c(F)cc34)nc12]

Step 1

3-Bromo-5,6-difluoro-1-methyl-1H-indazole

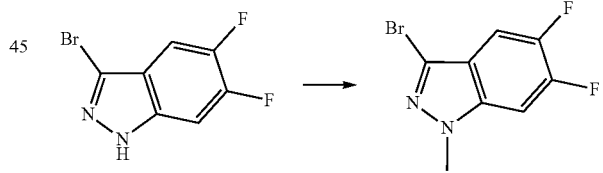

To a light brown suspension of 3-bromo-5,6-difluoro-1H-indazole (1.0 g, 4.29 mmol) and potassium carbonate (4.15 g, 30.0 mmol) in N-methylpyrrolidine (20 mL) was added iodomethane (0.81 mL, 12.9 mmol) at room temperature. The resulting dark brown solution was stirred for 15 h at room temperature under nitrogen atmosphere by which time the TLC (2:1, Hex:EA, Rf=0.6, major and 0.4, minor) indicated the presence of the desired compound. The reaction was diluted with water (~100 mL), the organic compound was extracted with ethyl acetate (3×50 mL) and the combined extracts were washed with brine solution. After drying over MgSO₄, the filtrate was concentrated to obtain the crude light brown solid which was purified by chromatography using an ISCO (80 g) column eluting with hexanes (1 min), 0-15% EA in hexanes (2 min), 15-40% EA in hexanes (15 min) to obtain 746 mg (70%) of 3-bromo-5,6-difluoro-1-methyl-1H-indazole as a white solid and 186 mg (18%) of 3-bromo-5,6-difluoro-2-methyl-2H-indazole as a light yellow solid.

Step 2

2-Bromo-5-(2-trimethylsilanyl-ethoxymethyl)-5H-pyrrolo[2,3-b]pyrazine-7-carboxylic acid ((S)-2-methoxy-1-methyl-ethyl)-amide

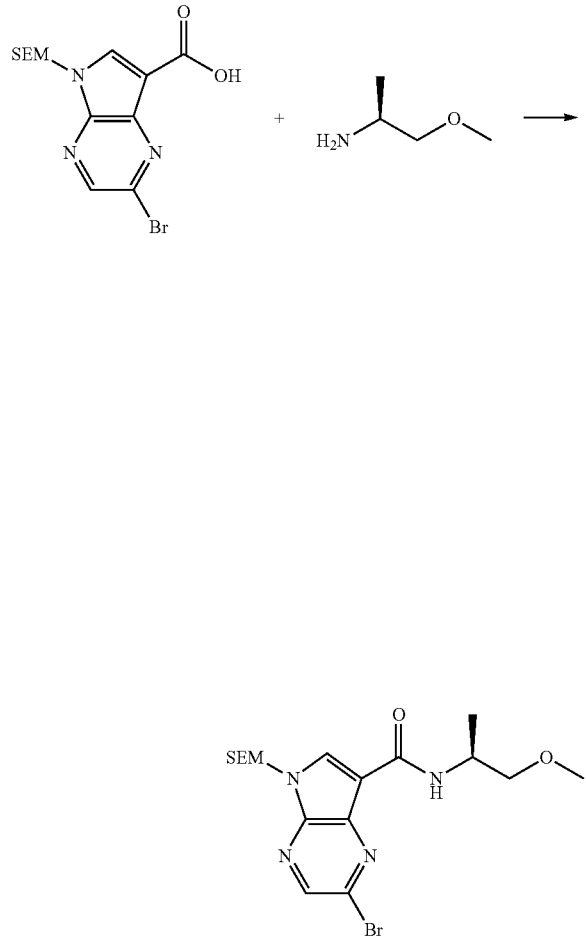

To a mixture of 2-bromo-5-(2-trimethylsilanyl-ethoxymethyl)-5H-pyrrolo[2,3-b]pyrazine-7-carboxylic acid (2.0 g, 5.37 mmol), (S)-1-methoxypropan-2-amine (718 mg, 8.06 mmol), and HATU (4.09 g, 10.7 mmol) were added DMF (20 mL) and DIPEA (3.75 mL, 21.5 mmol) at room temperature under nitrogen atmosphere. The resulting solution was stirred for 15 h at room temperature at which time LCMS analysis and TLC (1:1, Hex:EA, Rf=0.4) system indicated the presence of the desired compound. The reaction was diluted with water (~100 mL), the organic compound was extracted with ethyl acetate (3×50 mL) and the combined extracts were washed with brine solution. After drying over MgSO$_4$, the filtrate was concentrated to obtain the crude light brown solid (~4.1 g) which was purified by chromatography using an ISCO (120 g) column eluting with hexanes (1 min), 0-30% EA in hexanes (2 min), 30-60% EA in hexanes (15 min) to obtain 1.9 g (80%) of 2-bromo-5-(2-trimethylsilanyl-ethoxymethyl)-5H-pyrrolo[2,3-b]pyrazine-7-carboxylic acid ((S)-2-methoxy-1-methyl-ethyl)-amide as a white solid.

Step 3

2-(5,6-Difluoro-1-methyl-1H-indazol-3-yl)-5-(2-trimethylsilanyl-ethoxymethyl)-5H-pyrrolo[2,3-b]pyrazine-7-carboxylic acid ((S)-2-methoxy-1-methyl-ethyl)-amide

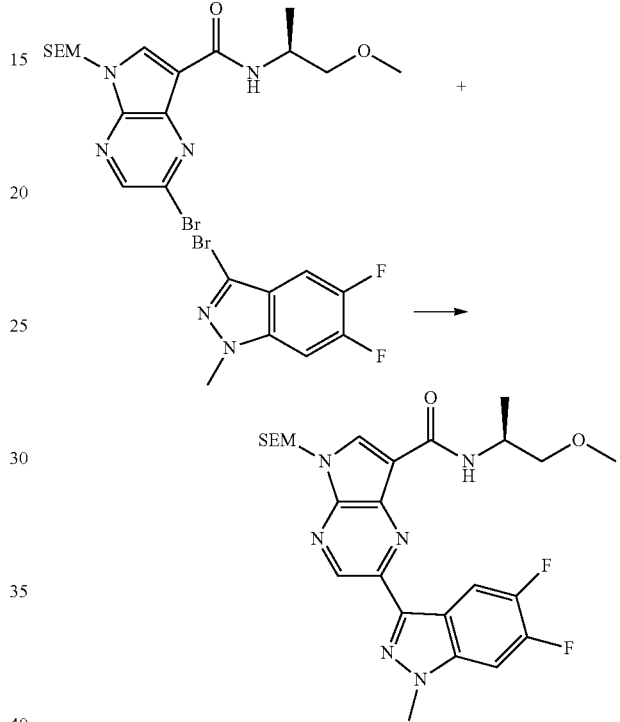

To a colorless solution of 3-bromo-5,6-difluoro-1-methyl-1H-indazole (247 mg, 1.00 mmol) in THF (3 mL, distilled) at −5° C. (ice/acetone) was added dropwise a solution of iso-propylmagnesium chloride (2.0 M in THF, 0.715 mL, 1.43 mmol) over 3-5 min. The resulting very light yellow solution was stirred for 2 h at 0° C. at which time TLC analysis (Hex:EA, 2:1, Rf=0.5 new spot, R$_f$=0.65, SM) of the hydrolyzed aliquot indicated the presence of a more polar spot, but starting material is also present. The clear light yellow solution was slowly allowed to warm to room temperature. During this period a yellow suspension formed which was stirred for another 3 h to complete the reaction. Then, a solution of zinc chloride (273 mg, 2.0 mmol) (anhydrous ZnCl$_2$ was heated with heat gun to melt under high vacuum and then cooled to room temperature before dissolving in THF) in THF (3 mL) was added to the yellow suspension at room temperature. The resulting light yellow suspension was stirred for 10 min.

In a separate, single neck 25 mL round-bottomed flask, bis-(dibenzylidineacetone)-palladium (29 mg, 0.050 mmol) and tri-ortho-tolylphosphine (61 mg, 0.20 mmol) were charged and the flask was purged with nitrogen gas. THF (1 mL) was added and the resulting light brown suspension was stirred for 5 min before the addition of a solution of 2-bromo-5-(2-trimethylsilanyl-ethoxymethyl)-5H-pyrrolo[2,3-b]pyrazine-7-carboxylic acid ((S)-2-methoxy-1-methyl-ethyl)- amide (111 mg, 0.25 mmol) in THF (2 mL) at room temperature under nitrogen atmosphere. Then, the above prepared yellow zinc suspension was added to this mixture. During the addition, it turned to a light brown solution which then heated to 60° C. and stirred for 15 h at which time, TLC analysis (Hex:EA, 1:1, $R_f$=0.5 and 0.55 for SM) of the hydrolyzed reaction mixture indicated the presence of a new spot. The reaction was cooled to room temperature and diluted with saturated ammonium chloride solution and EtOAc. The two layers were separated and the aqueous layer was extracted with EtOAc. The combined organic extracts were washed with brine solution and dried over anhydrous MgSO$_4$. Filtration of the drying agent and concentration of the filtrate gave the crude product which was purified by chromatography using an ISCO (40 g) column and eluting with hexanes (1 min), 0-25% EA in hexanes (2 min), 25-60% EA in hexanes (10 min), 60-100% EA in hexanes (2 min), and pure EA (5 min). The desired fractions were combined and the solvent was removed under vacuum to obtain 57 mg (43%) of 2-(5,6-difluoro-1-methyl-1H-indazol-3-yl)-5-(2-trimethylsilanyl-ethoxymethyl)-5H-pyrrolo[2,3-b]pyrazine-7-carboxylic acid ((S)-2-methoxy-1-methyl-ethyl)-amide as a light brown solid.

Step 4

2-(5,6-Difluoro-1-methyl-1H-indazol-3-yl)-5H-pyrrolo[2,3-b]pyrazine-7-carboxylic acid ((S)-2-methoxy-1-methyl-ethyl)-amide

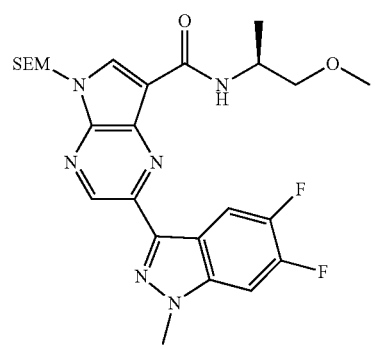

To a stirred solution of 2-(5,6-difluoro-1-methyl-1H-indazol-3-yl)-5-(2-trimethylsilanylethoxymethyl)-5H-pyrrolo[2,3-b]pyrazine-7-carboxylic acid ((S)-2-methoxy-1-methyl-ethyl)-amide (52 mg, 0.098 mmol) in THF (3 mL) was added a solution of TBAF (1.0 M in THF, 1.96 mL, 1.96 mmol) at room temperature. The resulting light brown solution was heated to 85° C. and stirred for 3 h at which time TLC analysis (EA, $R_f$=0.3) indicated the absence of starting material. Then, the reaction mixture was cooled to room temperature and 3 mL of acetone and 9 mL of saturated sodium bicarbonate solution were added and the resulting suspension was stirred for 2 h. The reaction suspension was diluted with water and the organic compound was extracted into EtOAc (3×) and the combined extracts were washed with water and brine solution then dried over MgSO$_4$. Filtration of the drying agent and removal of the solvent under vacuum gave the crude product which was dissolved in hot acetonitrile. EtOAc was added and the solution was stored in the refrigerator for 15 h. The resulting solid was collected by filtration, washed with acetonitrile, and air dried to afford 15 mg of off-white solid. The mother liquor was purified by chromatography using an ISCO (40 g) column eluting with dichloromethane (1 min), 0-100% (10% methanol in dichloromethane) in dichloromethane (5 min), and 10% methanol in dichloromethane (5 min) to obtain the an additional 10 mg of light yellow solid. Overall, 25 mg (64%) of 2-(5,6-difluoro-1-methyl-1H-indazol-3-yl)-5H-pyrrolo[2,3-b]pyrazine-7-carboxylic acid ((S)-2-methoxy-1-methyl-ethyl)-amide was isolated. LC-MS (M+H)$^+$=401; mp=295-297° C.; $^1$H NMR (300 MHz, DMSO-d$_6$) δ: 12.87 (br. s., 1H), 9.09 (s, 1H), 8.44 (s, 1H), 8.34 (dd, J=10.2, 7.9 Hz, 1H), 8.12 (d, J=8.5 Hz, 1H), 8.00 (dd, J=10.7, 6.7 Hz, 1H), 4.27-4.48 (m, 1H), 4.16 (s, 3H), 3.42-3.57 (m, 2H), 3.32 (br. s., 3H), 1.33 (d, J=6.8 Hz, 3H).

Example 213

2-(6-Fluoro-1-methyl-1H-indazol-3-yl)-5H-pyrrolo[2,3-b]pyrazine-7-carboxylic acid ((R)-1-benzyl-pyrrolidin-3-yl)-amide

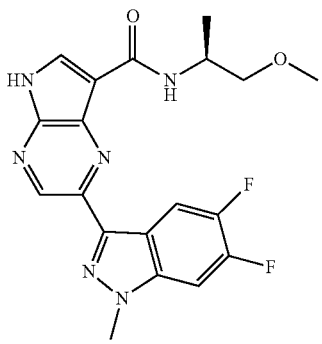

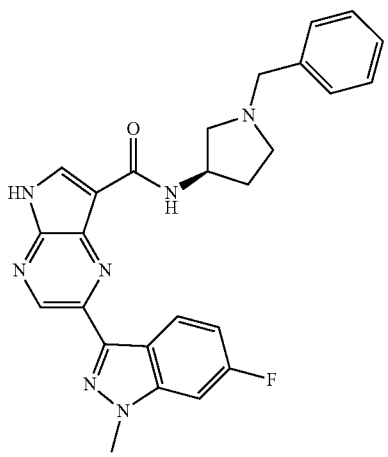 [SMILES: Cn1nc(-c2cnc3[nH]cc(C(=O)N[C@@H]4CCN(Cc5ccccc5)C4)c3n2)c2ccc(F)cc21]

Step 1

2-Bromo-5-(2-trimethylsilanyl-ethoxymethyl)-5H-pyrrolo[2,3-b]pyrazine-7-carboxylic acid ((R)-1-benzyl-pyrrolidin-3-yl)-amide

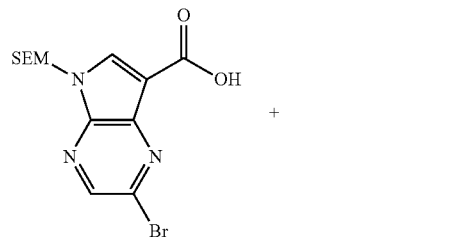

7-carboxylic acid ((R)-1-benzyl-pyrrolidin-3-yl)-amide as a clear viscous semisolid with a slight red/brown tint. LC-MS (M+H)$^+$=530.

Step 2

2-(6-Fluoro-1-methyl-1H-indazol-3-yl)-5-(2-trimethylsilanyl-ethoxymethyl)-5H-pyrrolo[2,3-b]pyrazine-7-carboxylic acid ((R)-1-benzyl-pyrrolidin-3-yl)-amide

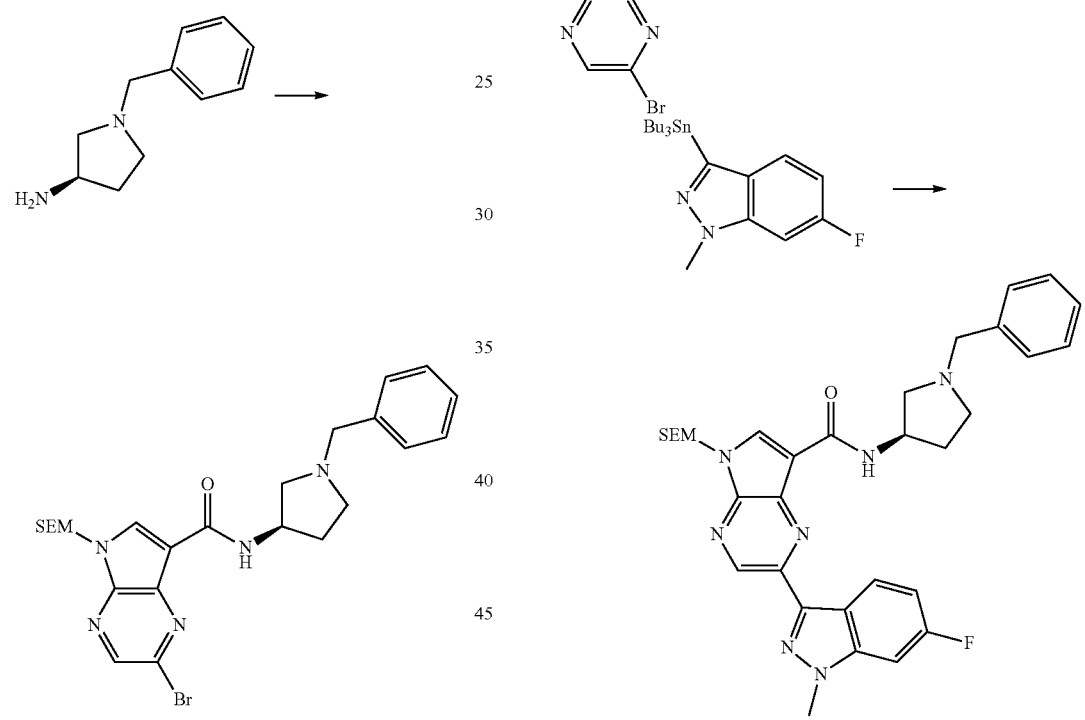

In a 100 mL round-bottomed flask, 2-bromo-5-(2-trimethylsilanyl-ethoxymethyl)-5H-pyrrolo[2,3-b]pyrazine-7-carboxylic acid (1.0 g, 2.69 mmol) was combined with dichloromethane (3 ml) to give a yellow solution. (R)-1-Benzylpyrrolidin-3-amine (710 mg, 4.03 mmol) and then DIEA (1.88 ml, 10.7 mmol) were added. To the clear solution was added HATU (2.04 g, 5.37 mmol) and to this mixture was added DMF (4 ml). The reaction was stirred under nitrogen overnight then concentrated and partioned between water (100 ml) and EtOAc (100 ml). The aqueous layer was washed with EtOAc (50 ml) then the combined organics were washed with brine, dried over MgSO$_4$, filtered and concentrated. The crude was dissolved in EtOAc, supported on silica gel, and purified by flash chromatography (120 g silicycle) with 0% to 100% EtOAc in hexanes. The appropriate fractions combined and concentrated to yield 1.38 g (97%) of 2-bromo-5-(2-trimethylsilanyl-ethoxymethyl)-5H-pyrrolo[2,3-b]pyrazine- In a 40 ml vial containing 2-bromo-5-(2-trimethylsilanyl-ethoxymethyl)-5H-pyrrolo[2,3-b]pyrazine-7-carboxylic acid ((R)-1-benzyl-pyrrolidin-3-yl)-amide (1.32 g, 2.49 mmol) was added a solution of 6-fluoro-1-methyl-3-tributylstannyl-1H-indazole (1.20 g, 2.73 mmol) in DMF (25 ml). The vial was backfilled with nitrogen and tetrakis(triphenylphosphine)palladium (0) (159 mg, 0.14 mmol) and copper (I) iodide (107 mg, 0.56 mmol) were added. Again the vial was backfilled with nitrogen, then sealed and the reaction mixture was stirred in a heating block at 80° C. for 4 h. The reaction mixture was cooled to room temperature diluted with EtOAc/hexanes (100/30 ml) and washed with water (100 ml). The aqueous layer was extracted with EtOAc/hexanes (100/30 ml). The combined organic layers were washed with brine then dried over MgSO$_4$, filtered, and concentrated. The crude was purified by flash chromatography (120 g Analogix) with 20% to 100% EtOAc in hexanes. The appropriate fractions were combined and concentrated to yield 1.02 g (62%) of 2-(6-fluoro-1-methyl-1H-indazol-3-yl)-5-(2-trimethylsilanyl-ethoxymethyl)-5H-pyrrolo[2,3-b]pyrazine-7-carboxylic acid ((R)-1-benzyl-pyrrolidin-3-yl)-amide as a light yellow solid. LC-MS (M+H)+=600.

Step 3

2-(6-Fluoro-1-methyl-1H-indazol-3-yl)-5H-pyrrolo[2,3-b]pyrazine-7-carboxylic acid ((R)-1-benzyl-pyrrolidin-3-yl)-amide

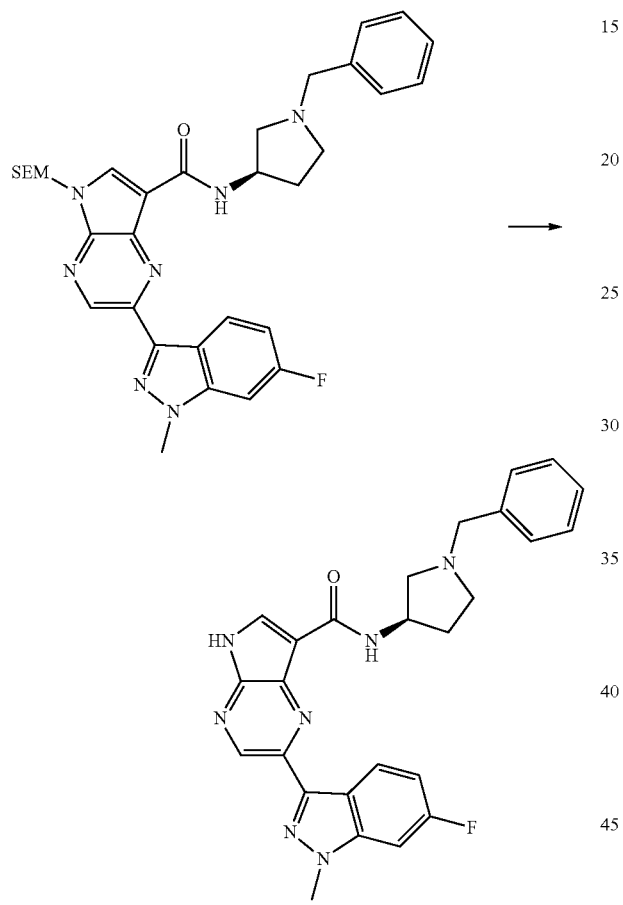

To a 20 ml vial containing 2-(6-fluoro-1-methyl-1H-indazol-3-yl)-5-(2-trimethylsilanylethoxymethyl)-5H-pyrrolo[2,3-b]pyrazine-7-carboxylic acid ((R)-1-benzyl-pyrrolidin-3-yl)-amide (51 mg, 0.085 mmol) dissolved in THF (1 ml) was added TBAF (1.0 M in THF, 1.0 ml, 1.0 mmol). The vial was backfilled with nitrogen then sealed and placed in heat block at 80° C. for 3 h. The reaction was cooled to room temperature, quenched with acetone (2 ml) and sat'd NaHCO₃ (20 ml). The mixture was stirred for 1 h then extracted with EtOAc and the organics washed with brine. The aqueous was again extracted with EtOAc and the organics washed with brine. The organics were combined, dried over MgSO₄, filtered and concentrated. The crude was dissolved in MeOH and EtOAc, supported on Celite, and purified by flash chromatography (4 g silicycle) with 0% to 10% MeOH in dichloromethane to 10% MeOH in EtOAc. The appropriate fractions were combined and concentrated. The solid was triturated with dichloromethane, Et₂O, and hexanes to isolate 11 mg (29%) of 2-(6-fluoro-1-methyl-1H-indazol-3-yl)-5H-pyrrolo[2,3-b]pyrazine-7-carboxylic acid ((R)-1-benzyl-pyrrolidin-3-yl)-amide as a white solid. LC-MS (M+H)+=470; ¹H NMR (300 MHz, DMSO-d₆) δ: 12.87 (br. s., 1H), 9.10 (s, 1H), 8.34-8.54 (m, 3H), 7.68 (dd, J=9.8, 1.8 Hz, 1H), 7.11-7.26 (m, 5H), 6.97 (td, J=9.1, 1.9 Hz, 1H), 4.60 (br. s., 1H), 4.16 (s, 3H), 3.61 (s, 2H), 2.82-2.97 (m, 1H), 2.58-2.75 (m, 2H), 2.29-2.44 (m, 2H), 1.75 (br. s., 1H).

Example 214

2-(6-Fluoro-1-methyl-1H-indazol-3-yl)-5H-pyrrolo[2,3-b]pyrazine-7-carboxylic acid ((R)-1-cyanomethyl-pyrrolidin-3-yl)-amide

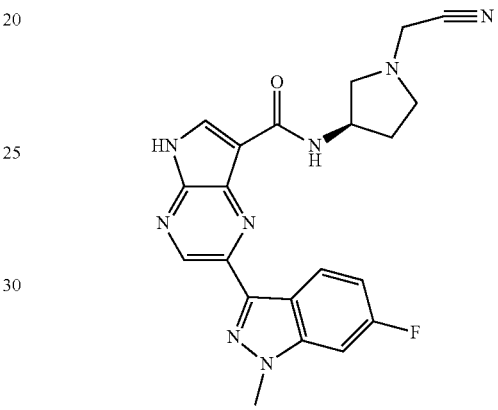

Step 1

2-(6-Fluoro-1-methyl-1H-indazol-3-yl)-5-(2-trimethylsilanyl-ethoxymethyl)-5H-pyrrolo[2,3-b]pyrazine-7-carboxylic acid (R)-pyrrolidin-3-ylamide

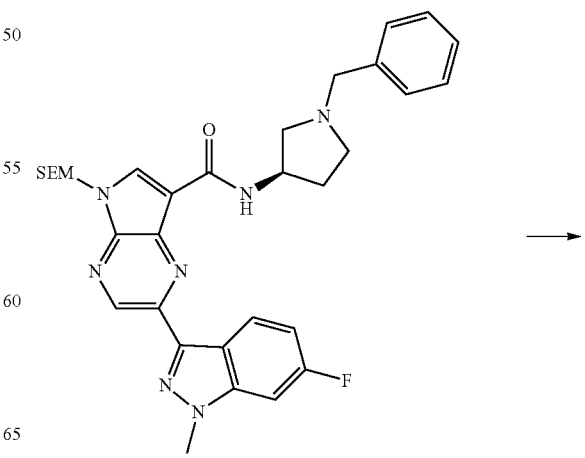

-continued

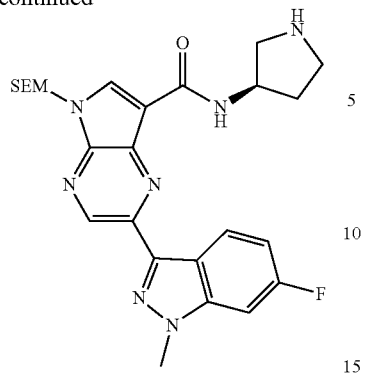

To a 100 ml round bottom flask containing 2-(6-fluoro-1-methyl-1H-indazol-3-yl)-5-(2-trimethylsilanyl-ethoxymethyl)-5H-pyrrolo[2,3-b]pyrazine-7-carboxylic acid ((R)-1-benzyl-pyrrolidin-3-yl)-amide (530 mg, 0.88 mmol) and proton sponge (132 mg, 0.62 mmol) was added 1,2 dichloroethane (20 ml). The clear solution was stirred under nitrogen and cooled in an ice bath for 10 min. To this was added 1-chloroethyl chloroformate (0.19 ml, 1.77 mmol). The reaction was stirred in the ice bath for 5 min, the bath removed and the reaction warmed to room temperature for 20 min. The reaction was placed in an oil bath and heated at 85° C. for 4 h then allowed to cool to room temperature overnight and concentrated. The residue was suspended in methanol (20 ml) and heated at reflux for 3 h then removed from the heat and allowed to cool to room temperature. Some product precipitated during cooling and was filtered off and washed with methanol. The remaining product was recovered from the mother liquor. The liquid was concentrated, suspended in ethyl acetate and washed with aqueous sodium bicarbonate. The aqueous solution with solids was extracted four times with dichloromethane. The organic layers were combined and washed with brine (100 ml), dried over magnesium sulfate, filtered, concentrated, and dried from a mixture of ethyl acetate and hexanes. The crude was suspended in boiling ethyl acetate (20 ml), cooled, filtered and washed with ethyl acetate and hexanes to afford 2-(6-fluoro-1-methyl-1H-indazol-3-yl)-5-(2-trimethylsilanyl-ethoxymethyl)-5H-pyrrolo[2,3-b]pyrazine-7-carboxylic acid (R)-pyrrolidin-3-ylamide as a white solid. This material was combined with the product that precipitated from the reaction and was used without further purification. LC-MS: (M+H)$^+$=510.

Step 2

2-(6-Fluoro-1-methyl-1H-indazol-3-yl)-5-(2-trimethylsilanyl-ethoxymethyl)-5H-pyrrolo[2,3-b]pyrazine-7-carboxylic acid ((R)-1-cyanomethyl-pyrrolidin-3-yl)-amide

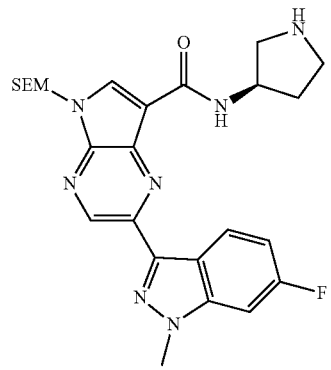

-continued

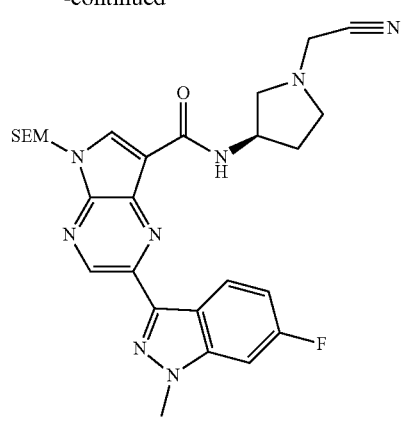

2-(6-Fluoro-1-methyl-1H-indazol-3-yl)-5-(2-trimethylsilanyl-ethoxymethyl)-5H-pyrrolo[2,3-b]pyrazine-7-carboxylic acid (R)-pyrrolidin-3-ylamide from Step 1 was dissolved in dichloromethane with the addition of triethylamine and bromo-acetonitrile. The reaction was concentrated and dried from mixtures of dichloromethane and hexanes. The crude was dissolved in a mixture dichloromethane, tetrahydrofuran, and methanol, supported on silica gel and purified by flash chromatography (4 g silicycle) with 0% to 10% MeOH in dichloromethane (0.5% Et$_3$N). The appropriate fractions were combined and concentrated. The solid obtained was triturated with Et$_2$O and hexanes. The solid was discarded and the mother liquor was concentrated to afford 220 mg (45%) of 2-(6-fluoro-1-methyl-1H-indazol-3-yl)-5-(2-trimethylsilanyl-ethoxymethyl)-5H-pyrrolo[2,3-b]pyrazine-7-carboxylic acid ((R)-1-cyanomethyl-pyrrolidin-3-yl)-amide as a white solid, 220 mg (45% yield). LC-MS (M+H)$^+$=549.

Step 3

2-(6-Fluoro-1-methyl-1H-indazol-3-yl)-5H-pyrrolo[2,3-b]pyrazine-7-carboxylic acid ((R)-1-cyanomethyl-pyrrolidin-3-yl)-amide

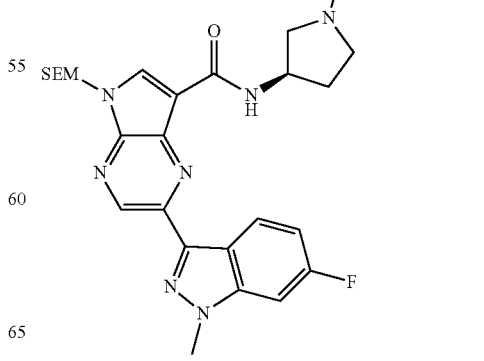

-continued

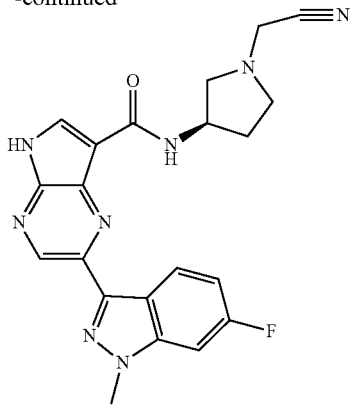

To a 100 ml round-bottomed flask containing 2-(6-fluoro-1-methyl-1H-indazol-3-yl)-5-(2-trimethylsilanyl-ethoxymethyl)-5H-pyrrolo[2,3-b]pyrazine-7-carboxylic acid ((R)-1-cyanomethyl-pyrrolidin-3-yl)-amide (216 mg, 0.394 mmol) suspended in THF (5 ml) was added TBAF (1.0 M in THF, 5.0 ml, 5.0 mmol). The vial was backfilled with nitrogen then sealed and heated in an oil bath at 85° C. for 2 h. The reaction was cooled to room temperature, quenched with acetone (5 ml) and sat'd NaHCO$_3$ (10 ml). The mixture was stirred for 1 h then diluted with water and extracted with EtOAc. Brine was added and the aqueous layer was extracted twice with EtOAc. The combined organics were washed with water and brine then dried over MgSO$_4$, filtered and concentrated. The crude solid was triturated with Et$_2$O, EtOAc, and hexanes to afford 54 mg (33%) of 2-(6-Fluoro-1-methyl-1H-indazol-3-yl)-5H-pyrrolo[2,3-b]pyrazine-7-carboxylic acid ((R)-1-cyanomethyl-pyrrolidin-3-yl)-amide as a white solid. LC-MS (M+H)$^+$=419; $^1$H NMR (300 MHz, DMSO-d$_6$) δ: 12.87 (br. s., 1H), 9.10 (s, 1H), 8.39-8.52 (m, 2H), 8.31 (d, J=7.8 Hz, 1H), 7.63-7.73 (m, 1H), 7.18-7.31 (m, 1H), 4.64 (br. s., 1H), 4.14 (s, 3H), 3.81-4.05 (m, 2H), 2.97 (td, J=8.6, 4.6 Hz, 1H), 2.86 (dd, J=9.2, 6.7 Hz, 1H), 2.72 (dd, J=9.3, 3.5 Hz, 1H), 2.52-2.62 (m, 1H), 2.36-2.45 (m, 1H), 1.70-1.85 (m, 1H).

Example 215

2-(6-Fluoro-1-methyl-1H-indazol-3-yl)-5H-pyrrolo[2,3-b]pyrazine-7-carboxylic acid [(R)-1-(3-bromo-phenyl)-ethyl]-amide

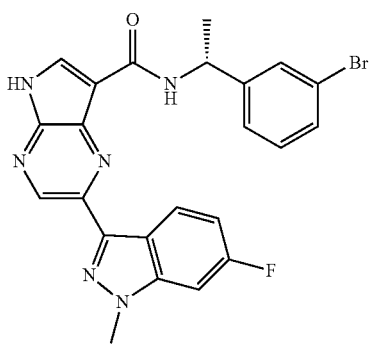 [SMILES: C[C@@H](NC(=O)c1c[nH]c2ncc(-c3nn(C)c4cc(F)ccc34)nc12)c1cccc(Br)c1]

Prepared according to the procedure outlined in Example 208, substituting (R)-1-(3-bromophenyl)ethanamine for 1-(4-bromo-phenyl)-cyclopropanamine in Step 1. LC-MS (M+H)$^+$=493/495; $^1$H NMR (300 MHz, DMSO-d$_6$) δ: 12.91 (br. s., 1H), 9.11 (s, 1H), 8.31-8.59 (m, 3H), 7.60-7.75 (m, 2H), 7.46 (t, J=6.5 Hz, 2H), 7.24-7.37 (m, 1H), 7.03 (td, J=9.0, 2.0 Hz, 1H), 5.30 (quin, J=7.0 Hz, 1H), 4.15 (s, 3H), 1.64 (d, J=7.0 Hz, 3H).

Example 216

2-(6-Fluoro-1-methyl-1H-indazol-3-yl)-5H-pyrrolo[2,3-b]pyrazine-7-carboxylic acid [(R)-1-(4-bromo-phenyl)-ethyl]-amide

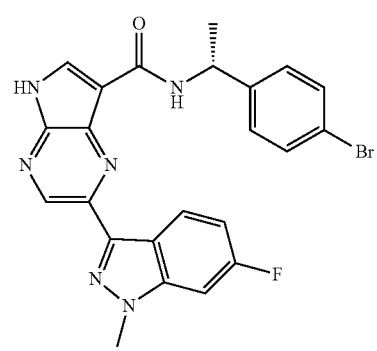 [SMILES: C[C@@H](NC(=O)c1c[nH]c2ncc(-c3nn(C)c4cc(F)ccc34)nc12)c1ccc(Br)cc1]

Prepared according to the procedure outlined in Example 208, substituting (R)-1-(4-bromophenyl)ethanamine for 1-(4-bromo-phenyl)-cyclopropanamine in Step 1. LC-MS (M+H)$^+$=493/495; $^1$H NMR (300 MHz, DMSO-d$_6$) δ: 12.90 (br. s., 1H), 9.10 (s, 1H), 8.41-8.54 (m, 2H), 8.28 (dd, J=8.9, 5.4 Hz, 1H), 7.68 (dd, J=9.8, 2.0 Hz, 1H), 7.53 (d, J=8.5 Hz, 2H), 7.42 (d, J=8.3 Hz, 2H), 6.98 (td, J=9.1, 2.1 Hz, 1H), 5.28 (quin, J=7.0 Hz, 1H), 4.14 (s, 3H), 1.62 (d, J=6.8 Hz, 3H).

Example 217

2-(6-Fluoro-1-methyl-1H-indazol-3-yl)-5H-pyrrolo[2,3-b]pyrazine-7-carboxylic acid [(R)-1-(3-cyano-phenyl)-ethyl]-amide

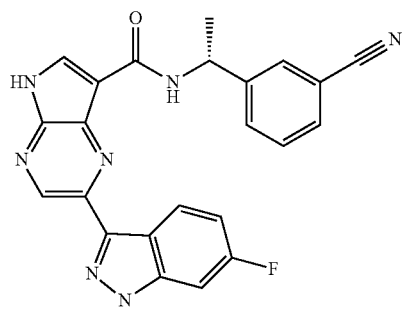

Prepared according to the procedure outlined in Example 208, substituting (R)-1-(3-cyanophenyl)ethanamine for 1-(4-bromo-phenyl)-cyclopropanamine in Step 1. LC-MS (M+H)$^+$=440; $^1$H NMR (300 MHz, DMSO-d$_6$) δ: 12.91 (br. s., 1H), 9.11 (s, 1H), 8.54 (d, J=7.3 Hz, 1H), 8.35-8.49 (m, 2H), 7.94 (s, 1H), 7.80 (d, J=7.8 Hz, 1H), 7.65-7.76 (m, 2H), 7.48-7.61 (m, 1H), 7.05 (t, J=8.0 Hz, 1H), 5.32 (t, J=6.9 Hz, 1H), 4.15 (s, 3H), 1.66 (d, J=7.0 Hz, 3H).

Example 218

2-(6-Fluoro-1-methyl-1H-indazol-3-yl)-5H-pyrrolo[2,3-b]pyrazine-7-carboxylic acid [(R)-1-(4-cyano-phenyl)-ethyl]-amide

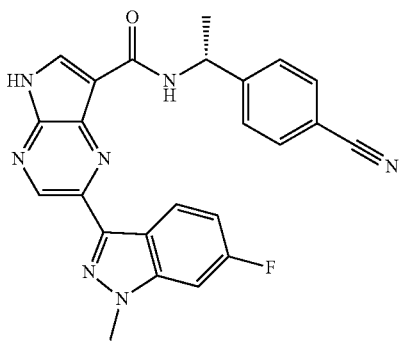 [SMILES: C[C@@H](NC(=O)c1c[nH]c2ncc(-c3nn(C)c4cc(F)ccc34)nc12)c1ccc(C#N)cc1]

Step 1

2-(6-Fluoro-1-methyl-1H-indazol-3-yl)-5-(2-trimethylsilanyl-ethoxymethyl)-5H-pyrrolo[2,3-b]pyrazine-7-carboxylic acid [(R)-1-(4-cyano-phenyl)-ethyl]-amide

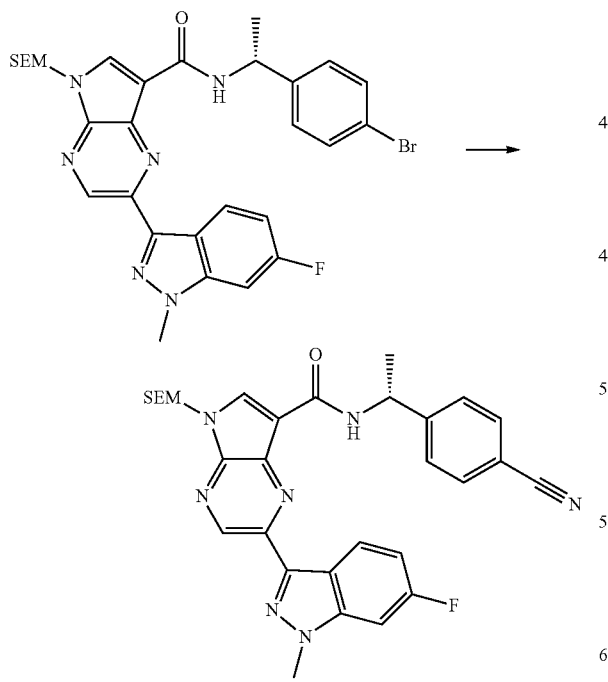

To a 20 ml microwave vial was added 2-(6-fluoro-1-methyl-1H-indazol-3-yl)-5-(2-trimethylsilanyl-ethoxymethyl)-5H-pyrrolo[2,3-b]pyrazine-7-carboxylic acid [(R)-1-(4-bromophenyl)-ethyl]-amide (62 mg, 0.10 mmol), copper (I) cyanide (18 mg, 0.20 mmol), and N-methyl-pyrrolidinone (6 ml) (HPLC grade, dried with 4A powdered molecular sieves). The resulting solution was purged with nitrogen then the vial sealed, and heated in an oil bath at 200° C. After 2.5 h the reaction was allowed to cool to room temperature over 17 h. The reaction was separated into two vials and each was independently subjected to heating in a microwave reactor at 200-230° C. for 2.5 h. The reactions were combined, diluted with water (50 ml), and extracted with ethyl acetate (50 ml) two times (5 ml of brine was added to clear phases). The organic layers were washed with brine (25 ml), combined, dried over magnesium sulfate, filtered, and further dried under a stream of nitrogen. The crude brown solid was purified by flash chromatography (4 g silicycle) with 0% to 60% EtOAc in hexanes. The appropriate fractions were combined and dried from a mixture dichloromethane and hexanes yielding 32 mg (56%) of 2-(6-fluoro-1-methyl-1H-indazol-3-yl)-5-(2-trimethylsilanyl-ethoxymethyl)-5H-pyrrolo[2,3-b]pyrazine-7-carboxylic acid [(R)-1-(4-cyano-phenyl)-ethyl]-amide as a light yellow solid.

Step 2

2-(6-Fluoro-1-methyl-1H-indazol-3-yl)-5H-pyrrolo[2,3-b]pyrazine-7-carboxylic acid [(R)-1-(4-cyano-phenyl)-ethyl]-amide

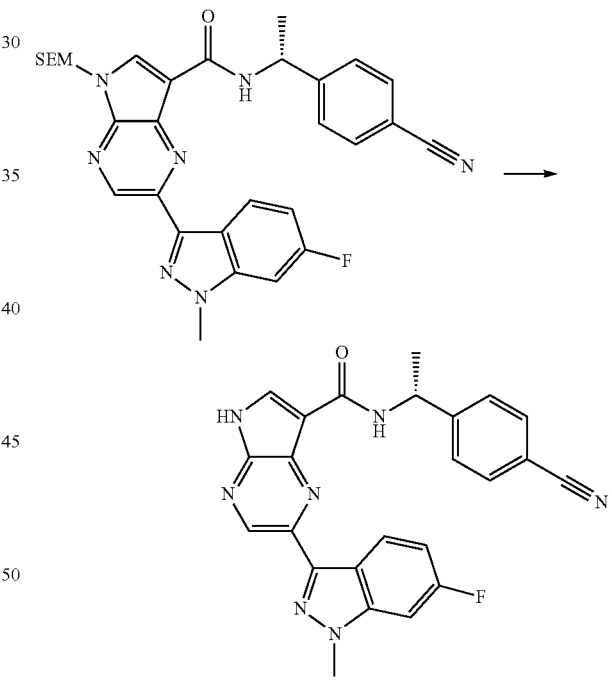

In a round-bottomed flask containing 2-(6-fluoro-1-methyl-1H-indazol-3-yl)-5-(2-trimethylsilanyl-ethoxymethyl)-5H-pyrrolo[2,3-b]pyrazine-7-carboxylic acid [(R)-1-(4-cyanophenyl)-ethyl]-amide (32 mg, 0.056 mmol) dissolved in THF (1 ml) was added TBAF (1.0 M in THF, 1.0 ml, 1.0 mmol). The flask was backfilled with nitrogen then sealed and placed in an oil bath at 85° C. for 2 h. The reaction was cooled to room temperature, quenched with acetone (2 ml) and sat'd NaHCO₃ (4 ml). The mixture was stirred for 1 h then diluted with water and extracted with EtOAc. Brine was added and the aqueous layer was extracted twice with EtOAc. The combined organics were washed with water and brine then dried over MgSO₄, filtered and concentrated. The crude solid was purified by flash chromatography (4 g silicycle) with 0% to 7.5% MeOH in dichloromethane. The appropriate fractions were combined and concentrated to afford 4 mg (19%) of 2-(6-fluoro-1-methyl-1H-indazol-3-yl)-5H-pyrrolo[2,3-b]pyrazine-7-carboxylic acid [(R)-1-(4-cyano-phenyl)-ethyl]-amide as a white solid. LC-MS (M+H)⁺=440; ¹H NMR (300 MHz, DMSO-d₆) δ: 12.97 (br. s., 1H), 9.17 (s, 1H), 8.33-8.69 (m, 3H), 7.85 (d, J=8.3 Hz, 2H), 7.64-7.78 (m, 3H), 7.08 (d, J=2.0 Hz, 1H), 5.39 (br. s., 1H), 4.20 (s, 3H), 1.70 (d, J=7.0 Hz, 3H).

Example 219

2-(6-Fluoro-1-methyl-1H-indazol-3-yl)-5H-pyrrolo[2,3-b]pyrazine-7-carboxylic acid ((S)-2-cyanomethoxy-1-methyl-ethyl)-amide

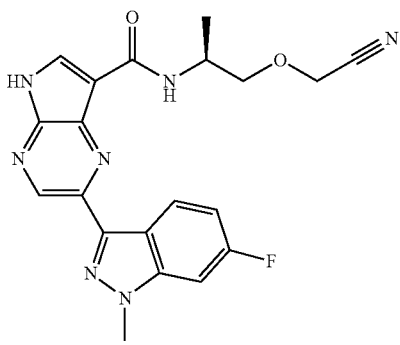

Step 1

2-(6-Fluoro-1-methyl-1H-indazol-3-yl)-5-(2-trimethylsilanyl-ethoxymethyl)-5H-pyrrolo[2,3-b]pyrazine-7-carboxylic acid ((S)-2-cyanomethoxy-1-methyl-ethyl)-amide

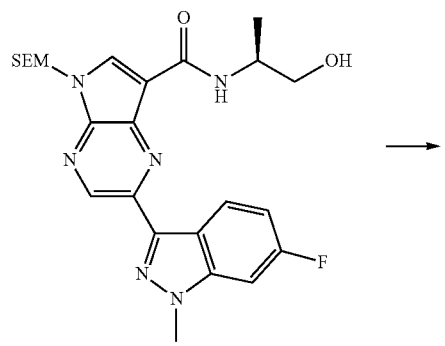

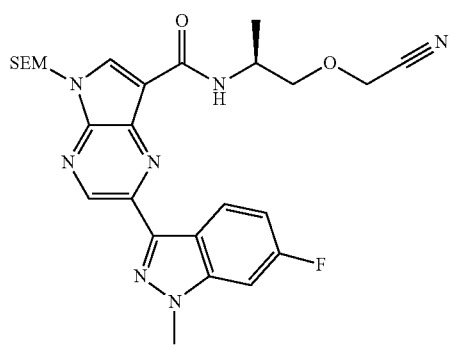

To a 100 ml three necked flask containing 2-(6-fluoro-1-methyl-1H-indazol-3-yl)-5-(2-trimethylsilanyl-ethoxymethyl)-5H-pyrrolo[2,3-b]pyrazine-7-carboxylic acid (S)-2-hydroxy-1-methyl-ethyl)-amide (176 mg, 0.35 mmol) was added THF (4 ml) under nitrogen and the mixture was cooled in an ice bath. To the mixture was added dropwise lithium bis(trimethylsilyl)amide (1.0 M in THF, 1.06 ml, 1.06 mmol) which resulted in a clear, red solution. After 30 min the reaction was removed from the ice bath and allowed to warm to room temperature over 1 h. 2-Bromoacetonitrile (0.10 ml, 1.44 mmol) was added dropwise which caused the reaction to become dark brown/green. After 3 h, additional 2-bromoacetonitrile (0.10 ml, 1.44 mmol) was added and the reaction was stirred at room temperature for 3 days. The reaction was diluted with water and extracted three times with ethyl acetate (brine was added to clear emulsion). The organic layers were washed with brine, combined, dried over magnesium sulfate, filtered, and concentrated to a brown semisolid. The crude material was purified by flash chromatography (12 g Analogix) with 0% to 75% ethyl acetate in. The appropriate fractions were combined and concentrated to afford 57 mg (30%) of 2-(6-fluoro-1-methyl-1H-indazol-3-yl)-5-(2-trimethylsilanyl-ethoxymethyl)-5H-pyrrolo[2,3-b]pyrazine-7-carboxylic acid ((S)-2-cyanomethoxy-1-methyl-ethyl)-amide as a yellow solid.

Step 2

2-(6-Fluoro-1-methyl-1H-indazol-3-yl)-5H-pyrrolo[2,3-b]pyrazine-7-carboxylic acid ((S)-2-cyanomethoxy-1-methyl-ethyl)-amide

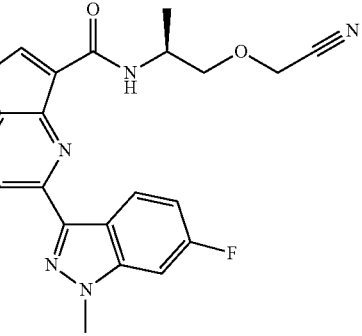

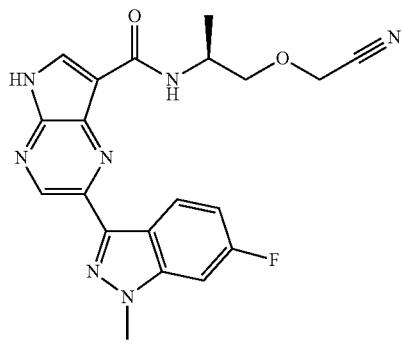 [SMILES: C[C@@H](COCC#N)NC(=O)c1c[nH]c2ncc(-c3nn(C)c4cc(F)ccc34)nc12]

In a round-bottomed flask containing 2-(6-fluoro-1-methyl-1H-indazol-3-yl)-5-(2-trimethylsilanyl-ethoxymethyl)-5H-pyrrolo[2,3-b]pyrazine-7-carboxylic acid ((S)-2-cyanomethoxy-1-methyl-ethyl)-amide (55 mg, 0.102 mmol) dissolved in THF (1 ml) was added TBAF (1.0 M in THF, 1.0 ml, 1.0 mmol). The flask was backfilled with nitrogen then sealed and placed in an oil bath at 85° C. for 2 h. The reaction was cooled to room temperature, quenched with acetone (2 ml) and sat'd NaHCO$_3$ (4 ml). The mixture was stirred for 1 h then diluted with water and extracted twice with EtOAc. The combined organics were washed with water and brine then dried over MgSO$_4$, filtered and concentrated. The crude solid was purified by flash chromatography (4 g silicycle) with 0% to 10% MeOH in dichloromethane. The appropriate fractions were combined and concentrated. The solid was triturated with Et$_2$O to afford 7 mg (16%) of 2-(6-fluoro-1-methyl-1H-indazol-3-yl)-5H-pyrrolo[2,3-b]pyrazine-7-carboxylic acid ((S)-2-cyanomethoxy-1-methyl-ethyl)-amide as a light brown solid. LC-MS (M+H)$^+$=408; $^1$H NMR (300 MHz, DMSO-d$_6$) δ: 12.95 (br. s., 1H), 9.17 (s, 1H), 8.47-8.62 (m, 2H), 8.26 (d, J=8.5 Hz, 1H), 7.76 (dd, J=9.8, 2.0 Hz, 1H), 7.25 (td, J=9.0, 2.3 Hz, 1H), 4.57 (s, 2H), 4.43-4.53 (m, 1H), 4.21 (s, 3H), 3.66-3.85 (m, 2H), 1.40 (d, J=6.8 Hz, 3H).

Example 220

2-Imidazo[1,2-a]pyridin-3-yl-5H-pyrrolo[2,3-b]pyrazine-7-carboxylic acid [(R)-2-(3-cyano-azetidin-1-yl)-1-methyl-2-oxo-ethyl]-amide

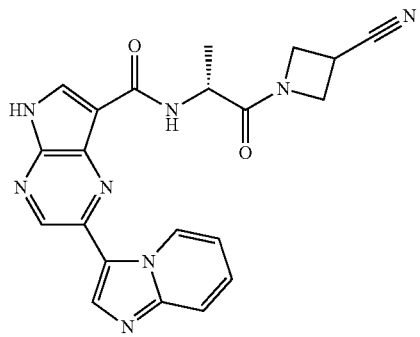

Step 1

3-Iodoimidazo[1,2-a]pyridine

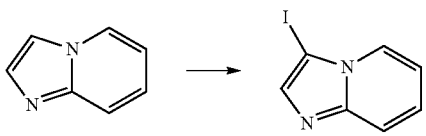 [SMILES: c1ccn2ccnc2c1 ; Ic1cnc2ccccn12]

In a 1 L three-necked flask, imidazo[1,2-a]pyridine (4.1 g, 34.7 mmol), in THF was treated with butyllithium (14.6 ml, 36.4 mmol) at −50° C. N-iodosuccinimide (8.59 g, 38.2 mmol) in 50 ml THF and added slowly and temp allowed to rise to 0° C. This was diluted with water and hexane. The organic layer was washed with 10% brine/water (2×), dried (MgSO$_4$) and evaporated to give a solid. The solid was dissolved in THF/DCM and purified by flash chromatography (80-100% ethyl acetate/hexane) to give the desired isomer 3-iodoimidazo[1,2-a]pyridine. $^1$H NMR (300 MHz, DMSO-d$_6$) δ: 8.32 (m, 1H) 7.72 (s, 1H) 7.62 (m, 1H) 7.34 (m, 1H) 7.06 (t, 1H).

Step 2

3-Tributylstannanyl-imidazo[1,2-a]pyridine

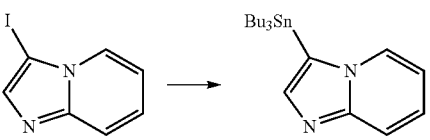

In a 100 mL three-necked flask, 3-iodoimidazo[1,2-a]pyridine (0.9 g, 3.69 mmol) was dissolved in 50 ml THF at −5° C. using an acetone/ice bath. Isopropylmagnesium chloride (1.3 M, 2.84 ml, 3.69 mmol) was added via a syringe and a light white suspension formed. After 0.5 h, tributylchlorostannane (1.15 g, 0.95 μl, 3.69 mmol) was added. This was stirred at 20° C. for 1.5 h. The reaction mixture was diluted with hexane (100 ml), quenched with a saturated solution of ammonium chloride and the organics were washed with 50% brine/water. The organic layer was dried over sodium sulfate, filtered and concentrated to give 3-tributylstannanyl-imidazo

[1,2-a]pyridine as an oil. $^1$H NMR (300 MHz, CDCl$_3$) δ 8.03 (d, 1H) 7.61 (d, 1H) 7.59 (s, 1H) 7.17 (m, 1H) 6.72 (m, 1H) 0.9-1.55 (m, 27).

Step 3

2-Imidazo[1,2-a]pyridin-3-yl-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide

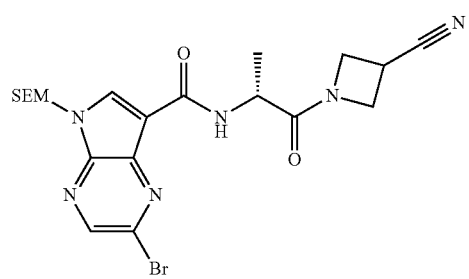

+

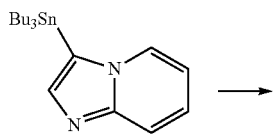

⟶

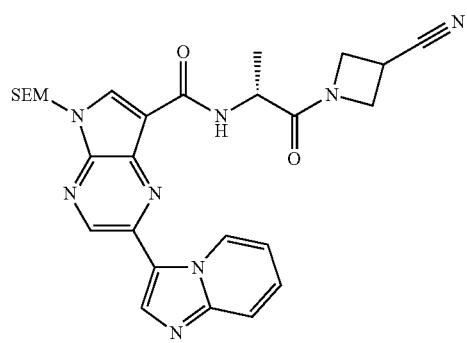

2-Bromo-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]amide (110 mg, 0.22 mmol) was combined with 3-tributylstannanyl-imidazo[1,2-a]pyridine (159 mg, 0.39 mmol) in DMF that had been sparged with nitrogen for 10 min. To this was added tetrakis(triphenylphosphine)palladium(0) (25 mg, 0.022 mmol) and the mixture heated to 70-80° C. for 3 h. All solvent was removed by high vacuum evaporation and the product purified by silica gel chromatography to give 2-imidazo[1,2-a]pyridin-3-yl-5-(2-trimethylsilanylethoxymethyl)-5H-pyrrolo[2,3-b]pyrazine-7-carboxylic acid [(R)-2-(3-cyano-azetidin-1-yl)-1-methyl-2-oxo-ethyl]-amide. LCMS: (M+H)$^+$=544.

Step 4

2-Imidazo[1,2-a]pyridin-3-yl-5H-pyrrolo[2,3-b]pyrazine-7-carboxylic acid [(R)-2-(3-cyano-azetidin-1-yl)-1-methyl-2-oxo-ethyl]-amide

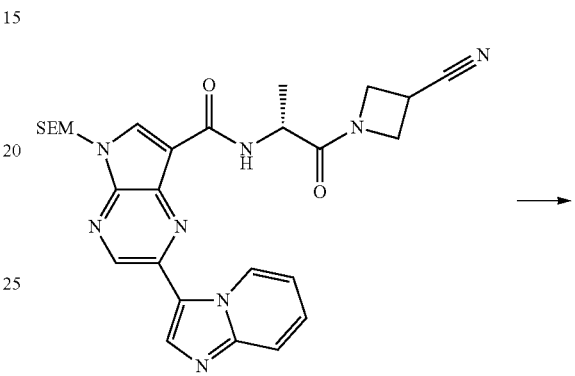

⟶

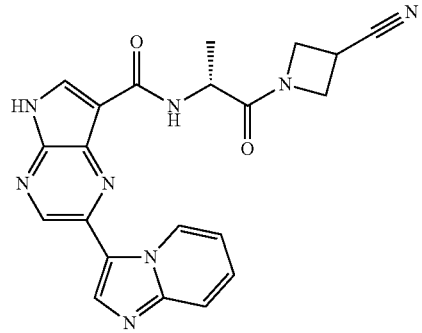

2-Imidazo[1,2-a]pyridin-3-yl-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide was deprotected using the described two step procedure (TFA followed by aqueous base) followed by chromatography to give 2-imidazo[1,2-a]pyridin-3-yl-5H-pyrrolo[2,3-b]pyrazine-7-carboxylic acid [(R)-2-(3-cyano-azetidin-1-yl)-1-methyl-2-oxo-ethyl]-amide. (ES+): 414. $^1$H NMR (300 MHz, DMSO-d$_6$) δ: 12.9 (m, 1H, 9.86 (m, 1H) 9.11 (s, 1H)

8.57 (s, 1H) 8.42 (d, 1H) 8.34 (d, 1H) 7.78 (d, 1H) 7.47 (t, 1H) 7.19 (m, 1H) 4.65 (m, 1H) 4.13 (m, 2H) 3.89 (m, 2H) 3.78 (m, 1H) 1.39 (d, 3H)

Example 221

2-(7-Chloro-imidazo[1,2-a]pyridin-3-yl)-5H-pyrrolo[2,3-b]pyrazine-7-carboxylic acid [(R)-2-(3-cyano-azetidin-1-yl)-1-methyl-2-oxo-ethyl]-amide

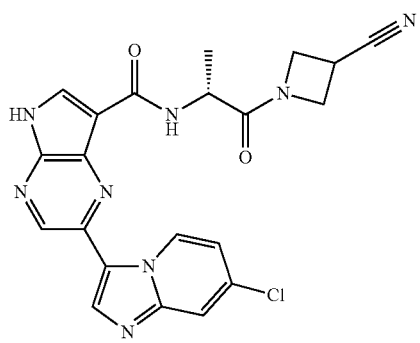 [SMILES: C[C@@H](NC(=O)c1c[nH]c2ncc(-c3cnc4cc(Cl)ccn34)nc12)C(=O)N1CC(C#N)C1]

Prepared according to the procedure outlined in Example 220, substituting 7-chloroimidazo[1,2-a]pyridine for imidazo[1,2-a]pyridine in Step 1. LCMS: (M+H)$^+$=448.

Example 222

2-(7-Cyano-imidazo[1,2-a]pyridin-3-yl)-5H-pyrrolo[2,3-b]pyrazine-7-carboxylic acid ((S)-2-methoxy-1-methyl-ethyl)-amide

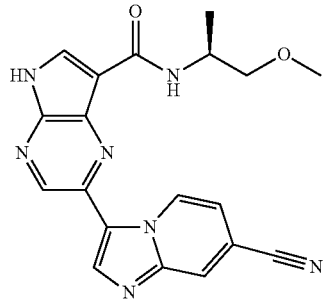 [SMILES: COC[C@H](C)NC(=O)c1c[nH]c2ncc(-c3cnc4cc(C#N)ccn34)nc12]

Step 1

3-Iodo-imidazo[1,2-a]pyridine-7-carbonitrile

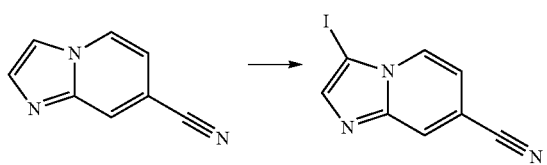 [SMILES: N#Cc1ccn2ccnc2c1 ; N#Cc1ccn2c(I)cnc2c1]

In a 50 mL round-bottomed flask, imidazo[1,2-a]pyridine-7-carbonitrile (1.1 g, 7.68 mmol) and N-iodosuccinimide (2.07 g, 9.22 mmol) were combined with DMF (50 ml) to give a colorless solution. The reaction mixture kept at 20° C. and stirred for 2 h. The reaction mixture was diluted with ethyl acetate (150 ml), THF (50 ml) and 300 ml of 5% sodium thiosulfate and well shaken. The aqueous layer was back-extracted with ethyl acetate (1×100 mL). The organic layers were combined, washed with water, brine, dried (MgSO$_4$) and evaporated. The crude material was purified by flash chromatography (silica gel, 60% to 80% ethyl acetate/hexanes) to give 3-iodo-imidazo[1,2-a]pyridine-7-carbonitrile. $^1$H NMR (300 MHz, DMSO-d$_6$) δ: 8.52 (d, 1H) 8.44 (d, 1H) 8.04 (d, 1H) 7.36 (dd, 1H).

Step 2

2-(7-Cyano-imidazo[1,2-a]pyridin-3-yl)-5-(2-trimethylsilanyl-ethoxymethyl)-5H-pyrrolo[2,3-b]pyrazine-7-carboxylic acid ((S)-2-methoxy-1-methyl-ethyl)-amide

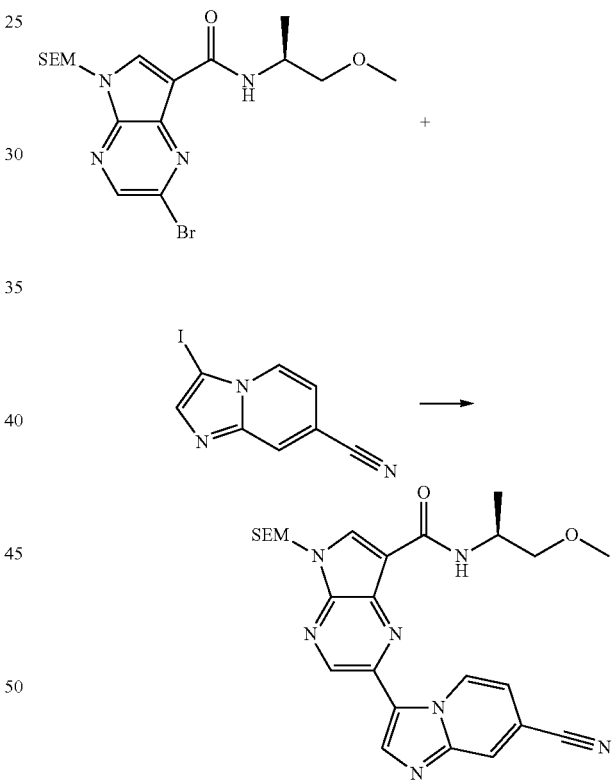

2-Bromo-5-(2-trimethylsilanyl-ethoxymethyl)-5H-pyrrolo[2,3-b]pyrazine-7-carboxylic acid ((S)-2-methoxy-1-methyl-ethyl)-amide (100 mg, 0.196 mmol) and hexamethylditin (72 mg, 0.22 mmol) were combined in a nitrogen sparged toluene (5 ml) solution. Tetrakis(triphenylphosphine)palladium(0) (19.5 mg, 0.17 mmol) was added and the solution heated to 95° C. for 2 h. The reaction was cooled and 3-iodo-imidazo[1,2-a]pyridine-7-carbonitrile (54 mg, 0.2 mmol) was added with additional tetrakis(triphenylphosphine)palladium(0) (20 mg, 0.02 mmol). The mixture was heated at 100° C. for 14 h, cooled and directly purified by silica gel chromatography to afford 2-(7-cyano-imidazo[1,2- a]pyridin-3-yl)-5-(2-trimethylsilanyl-ethoxymethyl)-5H-pyrrolo[2,3-b]pyrazine-7-carboxylic acid ((S)-2-methoxy-1-methyl-ethyl)-amide.

Step 3

2-(7-Cyano-imidazo[1,2-a]pyridin-3-yl)-5H-pyrrolo[2,3-b]pyrazine-7-carboxylic acid ((S)-2-methoxy-1-methyl-ethyl)-amide

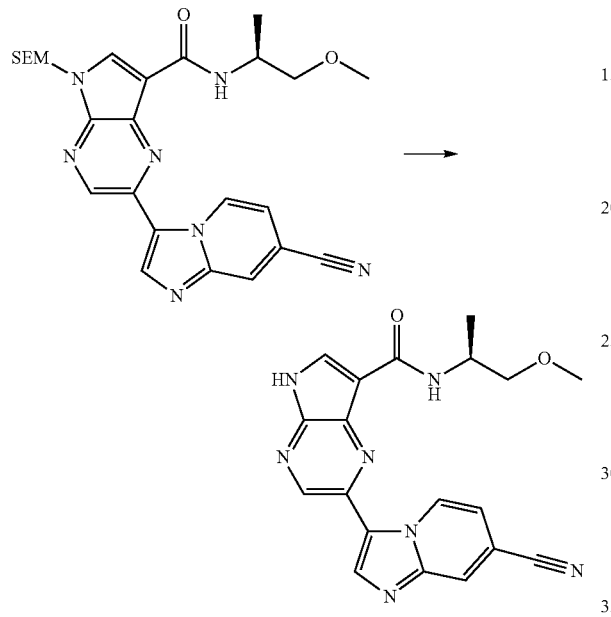

Standard deprotection using the described two step procedure (TFA followed by aqueous base) gave a solid which was purified by chromatography to give 2-(7-cyano-imidazo[1,2-a]pyridin-3-yl)-5H-pyrrolo[2,3-b]pyrazine-7-carboxylic acid ((S)-2-methoxy-1-methyl-ethyl)amide. LCMS: (M+H)$^+$ = 376. $^1$H NMR (300 MHz, DMSO-d$_6$) δ: 12.9 (m, 1H) 9.68 (m, 1H) 9.10 (s, 1H) 8.75 (s, 1H) 8.56 (m, 1H) 8.45 (s, 1H) 7.96 (d, 1H) 7.36 (m, 1H) 4.35 (m, 1H) 3.48-3.52 (m, 2H) 3.27 (s, 3H) 1.29 (d, 3H).

Example 223

2-(5-Chloro-benzoimidazol-1-yl)-5H-pyrrolo[2,3-b]pyrazine-7-carboxylic acid ((S)-2-methoxy-1-methyl-ethyl)-amide

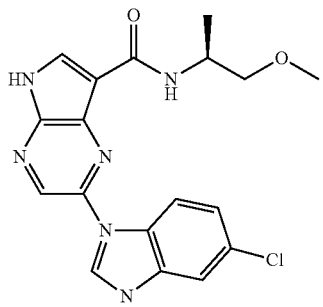

Step 1

2-(5-Chloro-benzoimidazol-1-yl)-5-(2-trimethylsilanyl-ethoxymethyl)-5H-pyrrolo[2,3-b]pyrazine and 2-(6-Chloro-benzoimidazol-1-yl)-5-(2-trimethylsilanyl-ethoxymethyl)-5H-pyrrolo[2,3-b]pyrazine

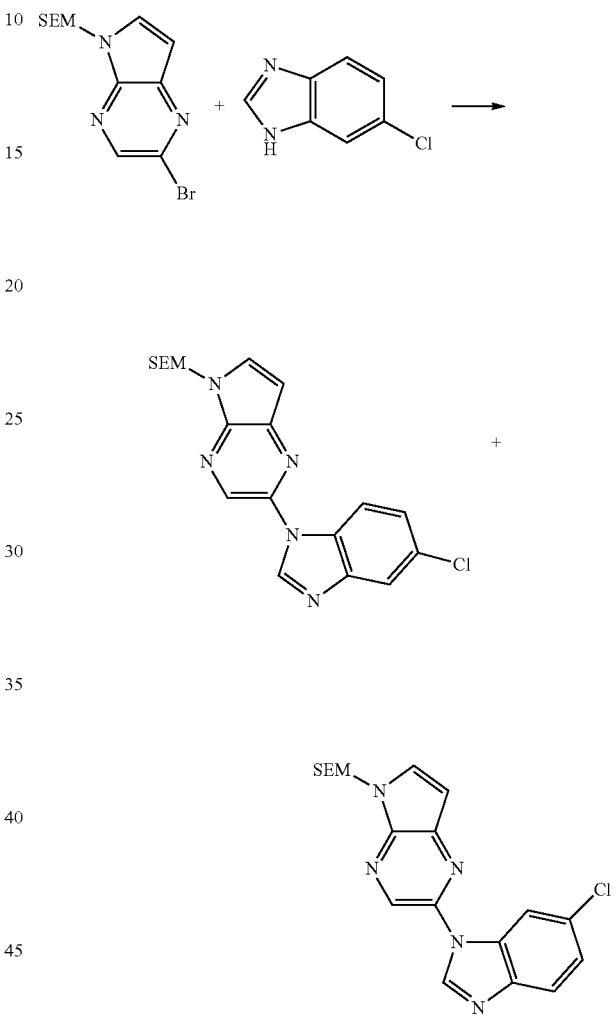

In a 75 mL three-necked flask, sodium hydride (60% dispersion, 134 mg, 3.35 mmol) and 6-chloro-1H-benzo[d]imidazole (511 mg, 3.35 mmol) were combined with NMP (15 ml) to give a light brown solution. 2-Bromo-5-(2-trimethylsilanyl-ethoxymethyl)-5H-pyrrolo[2,3-b]pyrazine (1.0 g, 3.05 mmol) was added. The reaction mixture was heated to 135° C. and stirred for 15 h. The reaction was cooled, poured into 50% water/brine and extracted into 50% ethyl acetate/hexane. The crude material was purified by flash chromatography (silica gel, 40% to 50% ethyl acetate in hexanes) to afford two regioisomers: 2-(5-chloro-benzoimidazol-1-yl)-5-(2-trimethylsilanyl-ethoxymethyl)-5H-pyrrolo[2,3-b]pyrazine; $^1$H NMR (300 MHz, DMSO-d$_6$) δ: 9.15 (s, 1H) 9.02 (s, 1H) 8.38 (m, 1H) 8.31 (m, 1H) 7.90 (d, 1H) 7.48 (m, 1H) 6.99 (d, 1H) 5.75 (s, 2H) 3.66 (t, 2H) 0.94 (t, 2H) 0.02 (s, 9H); and 2-(6-chloro-benzoimidazol-1-yl)-5-(2-trimethylsilanyl-ethoxymethyl)-5H-pyrrolo[2,3-b]pyrazine; $^1$H NMR (300 MHz, DMSO-d$_6$) δ: 9.16 (s, 1H) 9.02 (s, 1H) 8.36 (m, 1H)

8.34 (m, 1H) 7.96 (d, 1H) 7.48 (m, 1H) 6.94 (d, 1H) 5.75 (s, 2H) 3.66 (t, 2H) 0.94 (t, 2H) 0.02 (s, 9H).

Step 2

2-(5-Chloro-benzoimidazol-1-yl)-5-(2-trimethylsilanyl-ethoxymethyl)-5H-pyrrolo[2,3-b]pyrazine-7-carbaldehyde

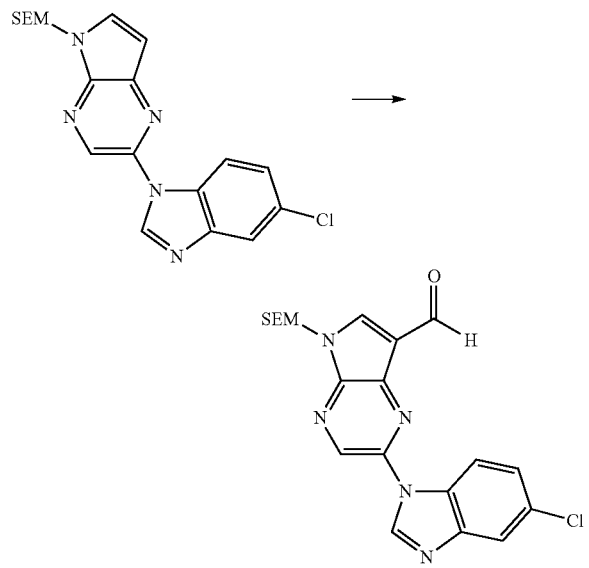

A solution of DMF at 5° C. was treated with phosphoryl trichloride (483 mg, 3.2 mmol) for 0.5 h. 2-(5-Chloro-benzoimidazol-1-yl)-5-(2-trimethylsilanyl-ethoxymethyl)-5H-pyrrolo[2,3-b]pyrazine (210 mg, 0.52 mmol) was added and the mixture was stirred at 65-70° C. for 7 h. The reaction was cooled and quenched with NaHCO$_3$ (aq) then extracted into ethyl acetate (2x). The organics were washed with water and brine then dried (MgSO$_4$). Purification was by flash chromatography gave 2-(5-chloro-benzoimidazol-1-yl)-5-(2-trimethylsilanylethoxymethyl)-5H-pyrrolo[2,3-b]pyrazine-7-carbaldehyde. LCMS: (M+H)$^+$=428.

Step 3

2-(5-Chloro-benzoimidazol-1-yl)-5-(2-trimethylsilanyl-ethoxymethyl)-5H-pyrrolo[2,3-b]pyrazine-7-carboxylic acid

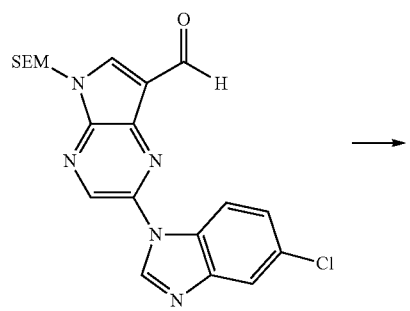

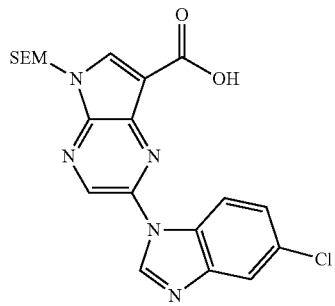

In a 50 mL round-bottomed flask, sulfamic acid (187 mg, 1.54 mmol) and 2-(5-chloro-benzoimidazol-1-yl)-5-(2-trimethylsilanyl-ethoxymethyl)-5H-pyrrolo[2,3-b]pyrazine-7-carbaldehyde (110 mg, 0.26 mmol) were combined with dioxane (6 ml) to give a off-white suspension. The reaction mixture was cooled to 5° C. and a solution of sodium chlorite (30.2 mg, 0.33 mmol) and potassium dihydrogen phosphate (35.0 mg, 0.26 mmol) in water (2 ml) was added dropwise via syringe over 5 min. The reaction warmed to room temperature and stirred for 1 h. The reaction was diluted with EtOAc (25 ml) and washed with 50% brine/water. The aqueous layer was back-extracted with EtOAc (15 mL). The organic layers were combined, washed with brine and dried (MgSO$_4$). Evaporation of the solvent gave 90 mg (79%) of 2-(5-chloro-benzoimidazol-1-yl)-5-(2-trimethylsilanyl-ethoxymethyl)-5H-pyrrolo[2,3-b]pyrazine-7-carboxylic acid as a solid. (M+H)$^+$= 444.

Step 4

2-(5-Chloro-2-benzoimidazol-1-yl)-5-(trimethylsilanyl-ethoxymethyl)-5H-pyrrolo[2,3-b]pyrazine-7-carboxylic acid ((S)-2-methoxy-1-methyl-ethyl)-amide

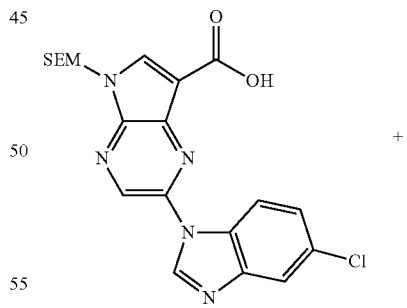

+

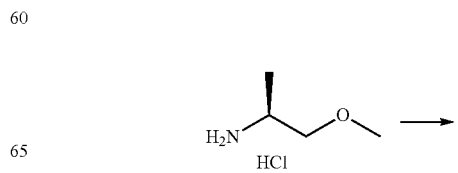

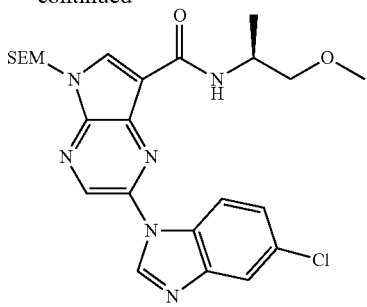

In a 5 mL pear-shaped flask, 2-(5-chloro-benzoimidazol-1-yl)-5-(2-trimethylsilanylethoxymethyl)-5H-pyrrolo[2,3-b]pyrazine-7-carboxylic acid (40 mg, 0.09 mmol, (S)-1-methoxypropan-2-amine hydrochloride (12.0 mg, 0.135 mmol) and HATU (51 mg, 0.135 mmol) were combined with DMF (3 ml) and N,N-diisopropylethylamine (0.22 ml, 1.26 mmol). The reaction was stirred at room temperature for 16 h then concentrated. The residue was diluted with water and extracted with EtOAc (2×). The organic layers were dried over MgSO₄ and concentrated to afford 2-(5-chloro-2-benzoimidazol-1-yl)-5-(trimethylsilanyl-ethoxymethyl)-5H-pyrrolo[2,3-b]pyrazine-7-carboxylic acid ((S)-2-methoxy-1-methyl-ethyl)-amide.

Step 5

2-(5-Chloro-benzoimidazol-1-yl)-5H-pyrrolo[2,3-b]pyrazine-7-carboxylic acid ((S)-2-methoxy-1-methyl-ethyl)-amide

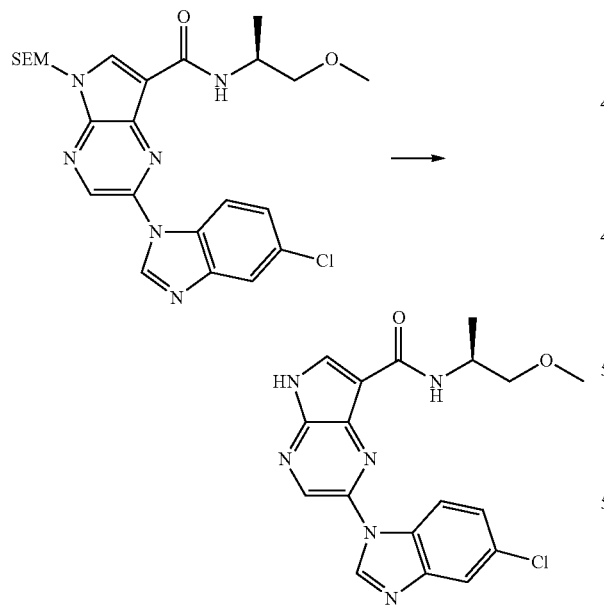

2-(5-Chloro-2-benzoimidazol-1-yl)-5-(trimethylsilanyl-ethoxymethyl)-5H-pyrrolo[2,3-b]pyrazine-7-carboxylic acid ((S)-2-methoxy-1-methyl-ethyl)-amide (40 mg, 0.078 mmol) was dissolved in dichloromethane (2 ml) at room temperature and 1.5 ml of TFA was added. The reaction was stirred for 4 h then all solvent was evaporated and the residue was dried under high vacuum. The crude material was dissolved in methanol and treated with 0.5 ml of triethylamine. The reaction mixture was stirred for 14 h. The solvent was evaporated and residue was suspended in 10% THF/EtOAc (20 ml), diluted with 50% ethyl acetate/hexanes (25 ml) and washed with water and brine, dried and evaporated. The residue was triturated with ether and filtered to give 22 mg (73%) of 2-(5-chloro-benzoimidazol-1-yl)-5H-pyrrolo[2,3-b]pyrazine-7-carboxylic acid ((S)-2-methoxy-1-methyl-ethyl)-amide as a white solid. MS: (M+H)⁺=385, ¹H NMR (300 MHz, DMSO-d₆) δ: 13.1 (s, 1H) 9.11 (s, 1H) 9.01 (s, 1H) 8.58 (m, 1H) 8.29 (d, 1H) 7.95-8.01 (m, 2H) 7.47 (d, 1H) 4.28 (m, 1H) 3.48 (m, 2H) 3.28 (s, 3H) 1.23 (d, 3H).

Example 224

2-(6-Chloro-benzoimidazol-1-yl)-5H-pyrrolo[2,3-b]pyrazine-7-carboxylic acid ((S)-2-methoxy-1-methyl-ethyl)-amide

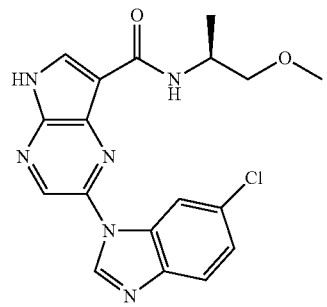 [SMILES: COC[C@H](C)NC(=O)c1c[nH]c2ncc(-n3cnc4ccc(Cl)cc43)nc12]

Prepared according to the procedure outlined in Example 223, Steps 2-5, substituting 2-(6-chloro-benzoimidazol-1-yl)-5-(2-trimethylsilanyl-ethoxymethyl)-5H-pyrrolo[2,3-b]pyrazine for 2-(5-chloro-benzoimidazol-1-yl)-5-(2-trimethylsilanyl-ethoxymethyl)-5H-pyrrolo[2,3-b]pyrazine in Step 2. MS: (M+H)⁺=385. ¹H NMR (300 MHz, DMSO-d₆) δ: 10.5 (s, 1H) 8.66 (s, 1H) 8.49 (s, 1H) 8.39 (m, 1H) 8.06 (d, 1H) 7.89 (m, 1H) 7.76 (d, 1H) 7.34 (d, 1H) 4.44 (m, 1H) 3.50 (m, 2H) 3.28 (s, 3H) 1.31 (d, 3H).

Example 225

2-(5-Chloro-benzoimidazol-1-yl)-5H-pyrrolo[2,3-b]pyrazine-7-carboxylic acid [(R)-2-(3-cyano-azetidin-1-yl)-1-methyl-2-oxo-ethyl]-amide

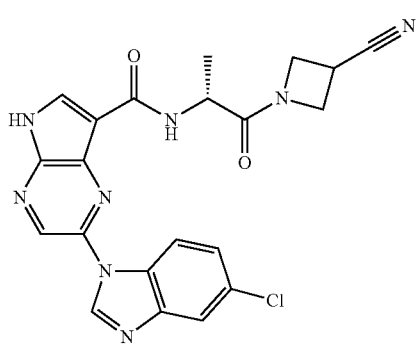 [SMILES: C[C@@H](NC(=O)c1c[nH]c2ncc(-n3cnc4cc(Cl)ccc43)nc12)C(=O)N1CC(C#N)C1]

Prepared according to the procedure outlined in Example 223, Steps 4-5, substituting 1-((R)-2-amino-propionyl)-azetidine-3-carbonitrile trifluoroacetate for (S)-1-methoxypropan-2-amine hydrochloride in Step 4. MS: (M+H)$^+$=449. $^1$H NMR (300 MHz, DMSO-d$_6$) δ: 13.1 (s, 1H) 9.16 (s, 1H) 9.03 (s, 1H) 8.59 (d, 1H) 8.42 (d, 1H) 7.29 (d, 1H) 7.91 (s, 1H) 7.42 (d, 1H) 4.48-4.71 (m, 3H) 4.20 (m, 1H) 4.09 (m, 1H) 3.83 (m, 1H) 1.33 (d, 3H).

Example 226

(6-Chloro-3-{7-[(R)-2-(3-cyano-azetidin-1-yl)-1-methyl-2-oxo-ethylcarbamoyl]-5H-pyrrolo[2,3-b]pyrazin-2-yl}-indazol-1-yl)-acetic acid

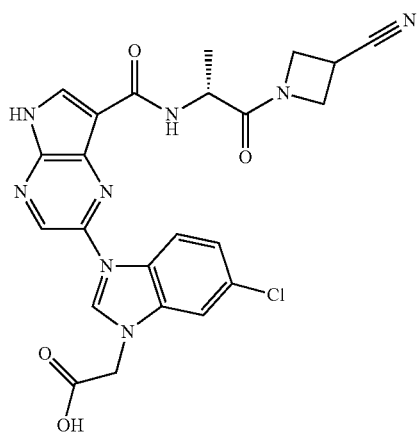

Step 1

{6-Chloro-3-[7-[(R)-2-(3-cyano-azetidin-1-yl)-1-methyl-2-oxo-ethylcarbamoyl]-5-(2-trimethylsilanyl-ethoxymethyl)-5H-pyrrolo[2,3-b]pyrazin-2-yl]-indazol-1-yl}-acetic acid tert-butyl ester

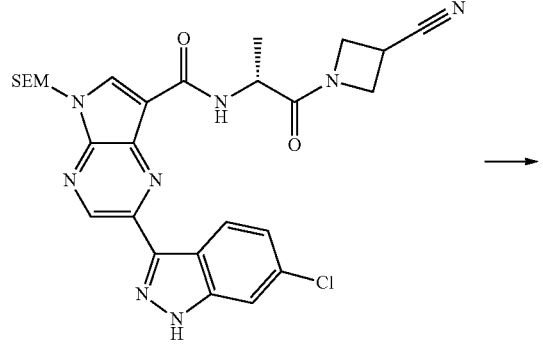

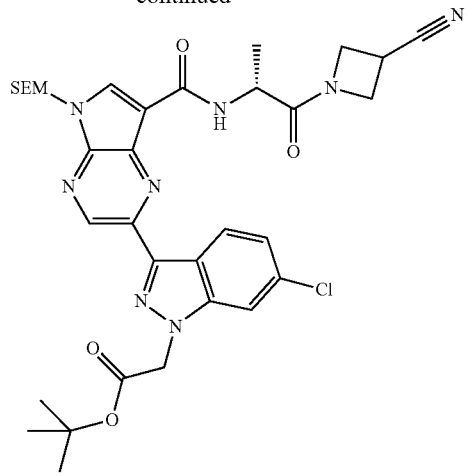

In a 20 mL pear-shaped flask, 2-(6-chloro-1H-indazol-3-yl)-5-(2-trimethylsilanylethoxymethyl)-5H-pyrrolo[2,3-b]pyrazine-7-carboxylic acid [(R)-2-(3-cyano-azetidin-1-yl)-1-methyl-2-oxo-ethyl]-amide (80 mg, 0.14 mmol) was combined with THF (3 ml) to give a light yellow solution. It was cooled to 0° C. and potassium tert-butoxide (19 mg, 0.17 mmol) was added. It was stirred at 0° C. for 30 min and tert-butyl 2-bromoacetate (22 μl, 0.14 mmol) was added dropwise and the reaction was stirred at 0° C. for 1 h. The reaction mixture was diluted with aqueous NH$_4$Cl and water, then extracted with Et$_2$O (2×30 ml). The combined organics were washed with water and brine then dried over MgSO$_4$ and concentrated. The crude residue was purified by SiO$_2$ chromatography (5% to 80% EtOAc/CH$_2$Cl$_2$) to isolate 35 mg (37%) {6-Chloro-3-[7-[(R)-2-(3-cyano-azetidin-1-yl)-1-methyl-2-oxo-ethylcarbamoyl]-5-(2-trimethylsilanyl-ethoxymethyl)-5H-pyrrolo[2,3-b]pyrazin-2-yl]-indazol-1-yl}-acetic acid tert-butyl ester as a foaming solid. MS: (M+H)$^+$=694.

Step 2

(6-Chloro-3-{7-[(R)-2-(3-cyano-azetidin-1-yl)-1-methyl-2-oxo-ethylcarbamoyl]-5H-pyrrolo[2,3-b]pyrazin-2-yl}-indazol-1-yl)-acetic acid

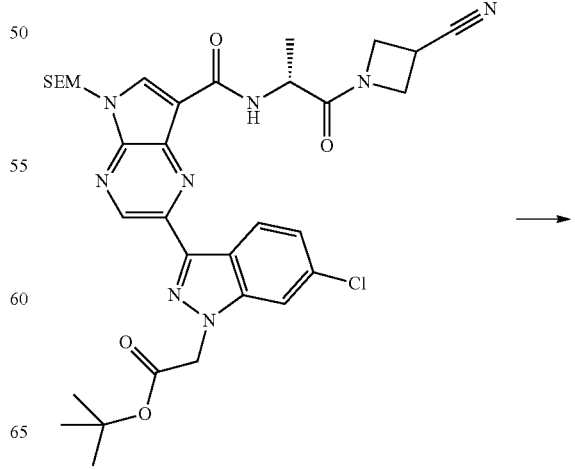

-continued

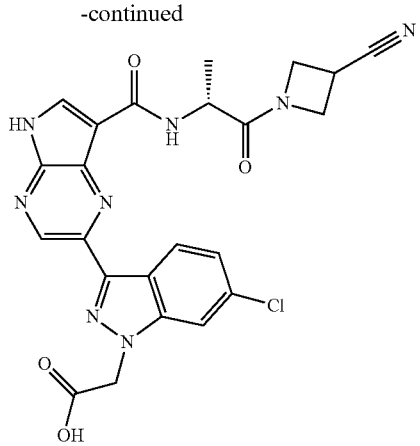

In a 5 mL pear-shaped flask, {6-chloro-3-[7-[(R)-2-(3-cyano-azetidin-1-yl)-1-methyl-2-oxo-ethylcarbamoyl]-5-(2-trimethylsilanyl-ethoxymethyl)-5H-pyrrolo[2,3-b]pyrazin-2-yl]-indazol-1-yl}-acetic acid tert-butyl ester (30 mg, 0.043 mmol) was combined with CH$_2$Cl$_2$ (1 ml) to give a light yellow solution. TFA (0.10 ml, 1.3 mmol) was added and the reaction was stirred at room temperature for 2 h. The crude reaction mixture was concentrated in vacuo and redissolved in CH$_2$Cl$_2$. Ethylenediamine (88 µl, 1.3 mmol) was added dropwise and the reaction was stirred at room temperature for 30 min. The crude reaction mixture was concentrated in vacuo. The residue was dissolved in water and it was lyophilized overnight. The yellow waxy solid was suspended in water and filtered, washing with water then dried on high vacuum to give 8 mg (32%) of (6-Chloro-3-{7-[(R)-2-(3-cyano-azetidin-1-yl)-1-methyl-2-oxo-ethylcarbamoyl]-5H-pyrrolo[2,3-b]pyrazin-2-yl}-indazol-1-yl)-acetic acid as a yellow solid. MS: (M+H)$^+$=507.

Example 227

2-(6-Chloro-1-dimethylcarbamoylmethyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide

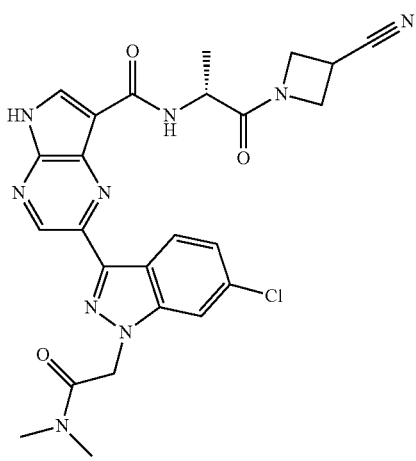 [SMILES: C[C@@H](NC(=O)c1c[nH]c2ncc(-c3nn(CC(=O)N(C)C)c4cc(Cl)ccc34)nc12)C(=O)N1CC(C#N)C1]

Prepared according to the procedure outlined in Example 226 substituting 2-chloro-N,N-dimethylacetamide for tert-butyl 2-bromoacetate in Step 1. MS: (M+H)$^+$=534; $^1$H NMR (DMSO-d$_6$) δ: 9.05-9.13 (m, 1H), 8.73 (dd, J=8.6, 4.3 Hz, 1H), 8.42-8.53 (m, 2H), 7.90 (s, 1H), 7.12-7.37 (m, 1H), 5.58 (s, 2H), 4.46-4.83 (m, 3H), 4.18-4.31 (m, 1H), 4.06-4.16 (m, 1H), 3.86 (d, J=5.9 Hz, 1H), 3.15 (s, 3H), 2.88 (s, 3H), 1.41 (t, J=6.2 Hz, 3H).

Example 228

2-[6-Chloro-1-(2-morpholin-4-yl-2-oxo-ethyl)-1H-indazol-3-yl]-5H-pyrrolo[2,3-b]pyrazine-7-carboxylic acid [(R)-2-(3-cyano-azetidin-1-yl)-1-methyl-2-oxo-ethyl]-amide

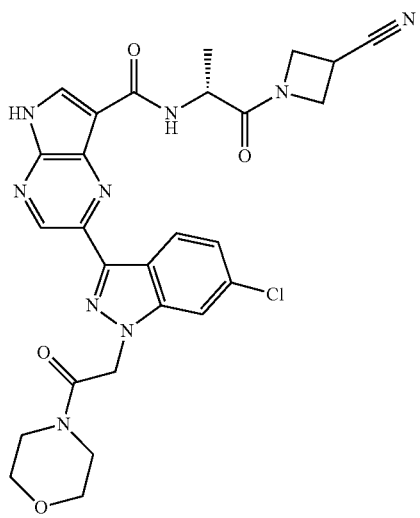 [SMILES: C[C@@H](NC(=O)c1c[nH]c2ncc(-c3nn(CC(=O)N4CCOCC4)c4cc(Cl)ccc34)nc12)C(=O)N1CC(C#N)C1]

Prepared according to the procedure outlined in Example 226 substituting 2-chloro-1-morpholinoethanone for tert-butyl 2-bromoacetate in Step 1. MS: (M+H)$^+$=577;

$^1$H NMR (DMSO-d$_6$) δ: 9.20 (s, 1H), 8.83 (dd, J=8.6, 3.9 Hz, 1H), 8.55-8.65 (m, 2H), 8.02 (s, 2H), 7.37 (d, J=7.0 Hz,

1H), 5.73 (s, 2H), 4.55-4.92 (m, 3H), 4.28-4.39 (m, 1H), 4.15-4.25 (m, 1H), 3.82 (br. s., 1H), 3.71 (br. s., 4H), 3.54 (d, J=4.3 Hz, 4H), 1.90 (s, 3H).

Example 229

2-[6-Chloro-1-(2-dimethylamino-ethyl)-1H-indazol-3-yl]-5H-pyrrolo[2,3-b]pyrazine-7-carboxylic acid [(R)-2-(3-cyano-azetidin-1-yl)-1-methyl-2-oxo-ethyl]-amide

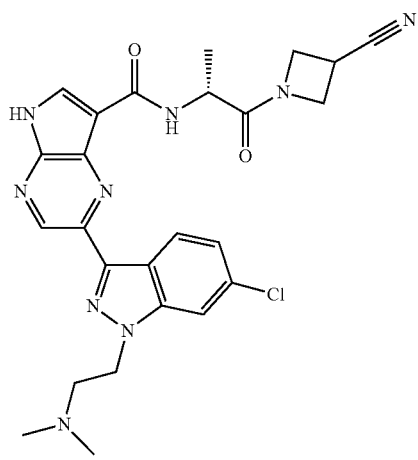 [SMILES: C[C@@H](NC(=O)c1c[nH]c2ncc(-c3nn(CCN(C)C)c4cc(Cl)ccc34)nc12)C(=O)N1CC(C#N)C1]

Step 1

2-[6-Chloro-1-(2-dimethylamino-ethyl)-1H-indazol-3-yl]-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide

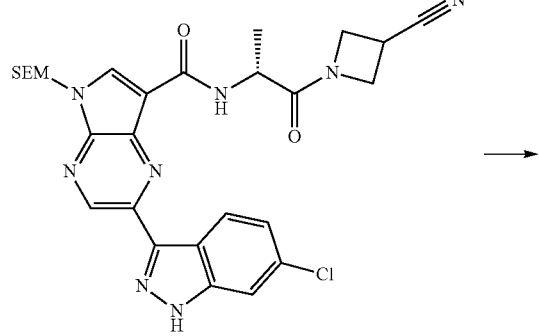

-continued

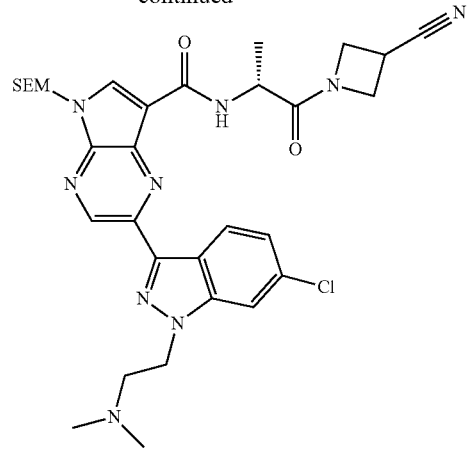

In a 10 mL pear-shaped flask, 2-(6-chloro-1H-indazol-3-yl)-5-(2-trimethylsilanylethoxymethyl)-5H-pyrrolo[2,3-b]pyrazine-7-carboxylic acid [(R)-2-(3-cyano-azetidin-1-yl)-1-methyl-2-oxo-ethyl]-amide (280 mg, 0.48 mmol) was combined with DMF (8 ml) at 0° C. to give a yellow solution. Sodium hydride (60% in mineral oil, 70 mg, 1.74 mmol) was added and the reaction was stirred at 0° C. for 10 min. Dimethylaminoethyl bromide hydrobromide (169 mg, 0.73 mmol) was added and the reaction was stirred at 0° C. for 30 min then allowed to warm up to room temperature and stirred for 2 h. The reaction was quenched with 5 ml of brine and 10 ml of water then extracted with EtOAc (2×). The combined organics were washed with water and brine then dried and purified by SiO$_2$ chromatography (0% to 10% MeOH/CH$_2$Cl$_2$ to isolate 135 mg (43%) of 2-[6-chloro-1-(2-dimethylamino-ethyl)-1H-indazol-3-yl]-5-(2-trimethylsilanylethoxymethyl)-5H-pyrrolo[2,3-b]pyrazine-7-carboxylic acid [(R)-2-(3-cyano-azetidin-1-yl)-1-methyl-2-oxo-ethyl]-amide as a foaming solid. MS: (M+H)$^+$=651.

Step 2

2-[6-Chloro-1-(2-dimethylamino-ethyl)-1H-indazol-3-yl]-5H-pyrrolo[2,3-b]pyrazine-7-carboxylic acid [(R)-2-(3-cyano-azetidin-1-yl)-1-methyl-2-oxo-ethyl]-amide

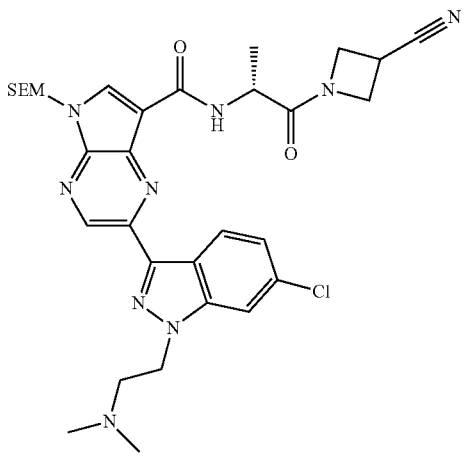

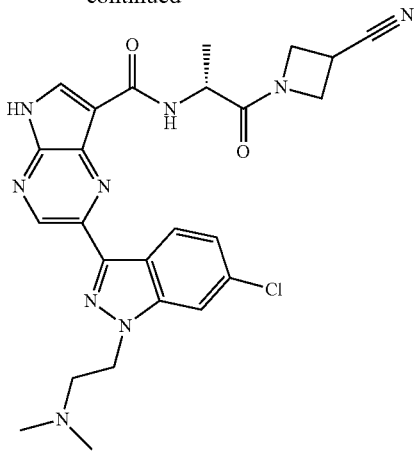

In a 10 mL pear-shaped flask, 2-[6-chloro-1-(2-dimethylamino-ethyl)-1H-indazol-3-yl]-5-(2-trimethylsilanyl-ethoxymethyl)-5H-pyrrolo[2,3-b]pyrazine-7-carboxylic acid [(R)-2-(3-cyano-azetidin-1-yl)-1-methyl-2-oxo-ethyl]-amide (130 mg, 0.20 mmol) was combined with $CH_2Cl_2$ (1 ml) to give a yellow solution. TFA (0.24 ml, 3.2 mmol) was added and the reaction was stirred at room temperature for 2 h. The crude reaction mixture was concentrated in vacuo and redissolved in $CH_2Cl_2$. Ethylenediamine (0.33 ml, 5.0 mmol) was added dropwise and the reaction was stirred at room temperature for 20 min. The crude reaction mixture was concentrated in vacuo. The residue was suspended in cold water and filtered, washing with water then dried on high vacuum to give 70 mg (64%) of 2-[6-chloro-1-(2-dimethylamino-ethyl)-1H-indazol-3-yl]-5H-pyrrolo[2,3-b]pyrazine-7-carboxylic acid [(R)-2-(3-cyano-azetidin-1-yl)-1-methyl-2-oxo-ethyl]-amide as a yellow solid. MS: (M+H)$^+$=520; $^1$H NMR (DMSO-d$_6$) δ: 9.14 (s, 1H), 8.70 (d, J=7.0 Hz, 1H), 8.36-8.63 (m, 2H), 8.03 (s, 1H), 7.25 (d, J=6.6 Hz, 1H), 4.48-4.82 (m, 5H), 4.16-4.34 (m, 1H), 4.01-4.15 (m, 1H), 3.86 (d, J=5.1 Hz, 1H), 3.33 (br. s., 1H), 2.80 (t, J=6.1 Hz, 2H), 2.20 (s, 6H), 1.40 (t, J=6.4 Hz, 3H).

Example 230

2-[6-Chloro-1-(2-dimethylamino-ethyl)-1H-indazol-3-yl]-5H-pyrrolo[2,3-b]pyrazine-7-carboxylic acid [(R)-2-(3-cyano-azetidin-1-yl)-1-methyl-2-oxo-ethyl]-amide hydrochloride

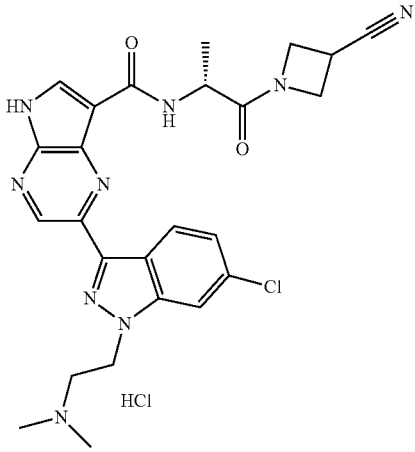 [SMILES: C[C@@H](NC(=O)c1c[nH]c2ncc(-c3nn(CCN(C)C)c4cc(Cl)ccc34)nc12)C(=O)N1CC(C#N)C1 ; Cl]

In a 10 mL pear-shaped flask, 2-[6-chloro-1-(2-dimethylamino-ethyl)-1H-indazol-3-yl]-5H-pyrrolo[2,3-b]pyrazine-7-carboxylic acid [(R)-2-(3-cyano-azetidin-1-yl)-1-methyl-2-oxo-ethyl]-amide hydrochloride (40 mg, 0.077 mmol) was combined with HCl (4N in dioxane) (0.2 mL, 0.80 mmol) to give a suspension. Water was added and it became a yellow pasty suspension. Et$_2$O was added, the mixture stirred and organic layer was decanted. This was repeated 5 times (5×8 ml). The yellow solid was filtered and washed with Et$_2$O and dried under high vacuum to give 35 mg (85%) of 2-[6-chloro-1-(2-dimethylamino-ethyl)-1H-indazol-3-yl]-5H-pyrrolo[2,3-b]pyrazine-7-carboxylic acid [(R)-2-(3-cyano-azetidin-1-yl)-1-methyl-2-oxo-ethyl]-amide hydrochloride as a yellow solid. MS: (M+H)$^+$=520; $^1$H NMR (DMSO-d$_6$) δ: 13.03 (br. s., 1H), 10.22 (br. s., 1H), 9.20 (s, 1H), 8.76 (d, J=8.6 Hz, 1H), 8.44-8.54 (m, 2H), 8.15 (s, 1H), 7.29-7.35 (m, 1H), 4.96-5.02 (m, 2H), 4.99 (t, J=6.1 Hz, 2H), 4.64-4.79 (m, 1H), 4.52-4.62 (m, 1H), 4.07-4.26 (m, 2H), 3.72 (d, J=5.9 Hz, 2H), 2.89 (d, J=4.7 Hz, 6H), 1.40 (t, J=6.8 Hz, 3H).

Example 231

2-[6-Chloro-1-(2-morpholin-4-yl-ethyl)-1H-indazol-3-yl]-5H-pyrrolo[2,3-b]pyrazine-7-carboxylic acid [(R)-2-(3-cyano-azetidin-1-yl)-1-methyl-2-oxo-ethyl]-amide

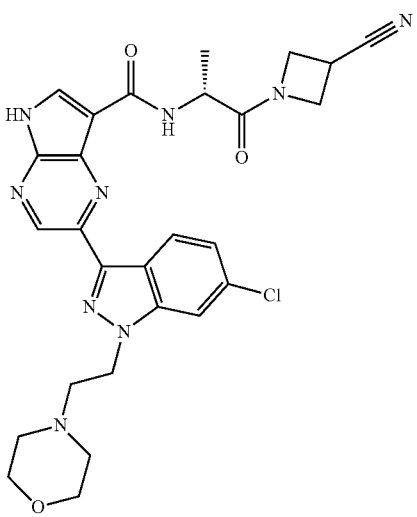 [SMILES: C[C@@H](NC(=O)c1c[nH]c2ncc(-c3nn(CCN4CCOCC4)c4cc(Cl)ccc34)nc12)C(=O)N1CC(C#N)C1]

Prepared according to the procedure outlined in Example 229, substituting 4-(2-bromoethyl)morpholine for dimethylaminoethyl bromide hydrobromide in Step 1. MS: (M+H)$^+$=563; $^1$H NMR (DMSO-d$_6$) δ: 9.15 (s, 1H), 8.70 (d, J=8.0 Hz, 1H), 8.42-8.50 (m, 2H), 8.05 (s, 1H), 7.25 (d, J=8.0 Hz, 1H), 4.45-4.80 (m., 5H), 4.20-4.28 (m, 1H), 4.05-4.12 (br. s., 1H), 3.80-3.90 (m, 1H), 3.45-3.52 (m., 4H), 3.26-3.32 (m, 4H), 2.80-2.88 (m., 2H), 1.40 (t, J=6.4 Hz, 3H).

Example 232

2-[6-Chloro-1-(2-pyridin-2-yl-ethyl)-1H-indazol-3-yl]-5H-pyrrolo[2,3-b]pyrazine-7-carboxylic acid [(R)-2-(3-cyano-azetidin-1-yl)-1-methyl-2-oxo-ethyl]-amide

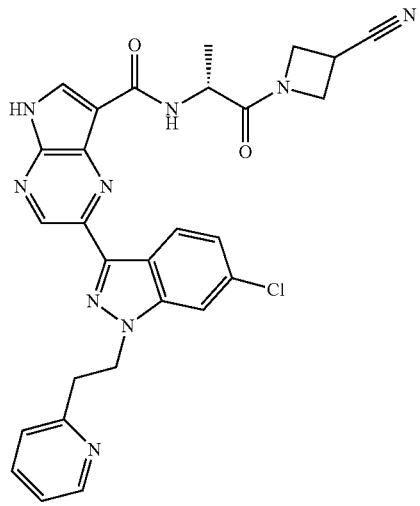 [SMILES: C[C@@H](NC(=O)c1c[nH]c2ncc(-c3nn(CCc4ccccn4)c4cc(Cl)ccc34)nc12)C(=O)N1CC(C#N)C1]

Prepared according to the procedure outlined in Example 229, substituting 2-(2-bromoethyl)pyridine hydrobromide for dimethylaminoethyl bromide hydrobromide in Step 1.
MS: (M+H)$^+$=555; $^1$H NMR (DMSO-d$_6$) δ: 9.11 (s, 1H), 8.68 (d, J=6.8 Hz, 1H), 8.41-8.54 (m, 3H), 7.81 (s, 1H), 7.64 (t, J=7.2 Hz, 1H), 7.16-7.31 (m, 3H), 4.92 (t, J=6.4 Hz, 2H), 4.49-4.81 (m, 3H), 4.23 (br. s., 1H), 4.10 (br. s., 1H), 3.86 (br. s., 1H), 3.39 (t, J=6.7 Hz, 2H), 1.33-1.47 (m, 3H).

Example 233

2-(6-Chloro-1-pyridin-2-ylmethyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide

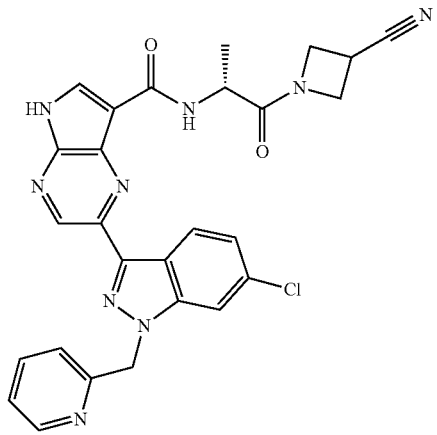 [SMILES: C[C@@H](NC(=O)c1c[nH]c2ncc(-c3nn(Cc4ccccn4)c4cc(Cl)ccc34)nc12)C(=O)N1CC(C#N)C1]

Prepared according to the procedure outlined in Example 229, substituting 2-(chloromethyl)pyridine hydrochloride for dimethylaminoethyl bromide hydrobromide in Step 1. MS: (M+H)$^+$=540; $^1$H NMR (DMSO-d$_6$) δ: 9.10 (s, 1H), 8.75 (d, J=7.0 Hz, 1H), 8.35-8.57 (m, 3H), 8.01 (s, 1H), 7.78 (t, J=7.4 Hz, 1H), 7.16-7.37 (m, 3H), 5.92 (s, 2H), 4.48-4.82 (m, 3H), 4.04-4.29 (m, 2H), 3.86 (br. s., 1H), 1.34-1.47 (m, 3H).

Example 234

2-[6-Chloro-1-(2-dimethylamino-ethyl)-1H-indazol-3-yl]-5H-pyrrolo[2,3-b]pyrazine-7-carboxylic acid ((S)-2-methoxy-1-methyl-ethyl)-amide

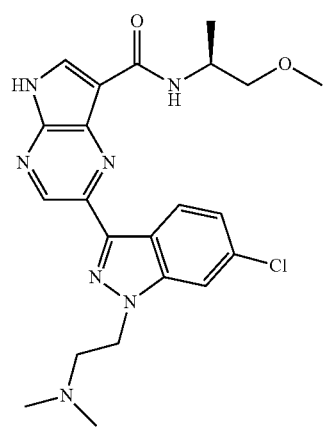

Step 1

2-(6-Chloro-1H-indazol-3-yl)-5-(2-trimethylsilanyl-ethoxymethyl)-5H-pyrrolo[2,3-b]pyrazine-7-carboxylic acid ((S)-2-methoxy-1-methyl-ethyl)-amide

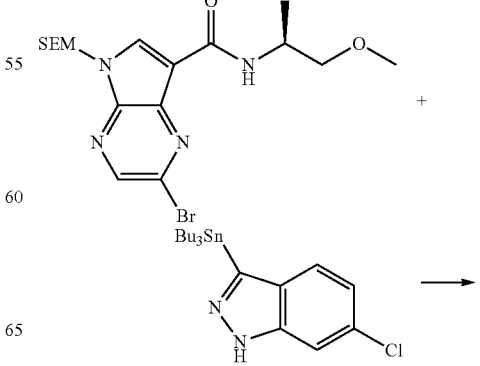

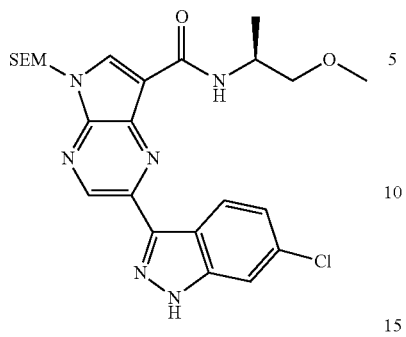

6-Chloro-3-tributylstannyl-1H-indazole (1.04 g, 2.35 mmol), copper(I) iodide (17 mg, 0.09 mmol,) and 2-bromo-5-(2-trimethylsilanyl-ethoxymethyl)-5H-pyrrolo[2,3-b]pyrazine-7-carboxylic acid ((S)-2-methoxy-1-methyl-ethyl)-amide (400 mg, 0.90 mmol) were combined with DMF (6 mL) to give a yellow solution. The mixture was degassed with bubbling nitrogen for 10 min, then tetrakis(triphenylphosphine)palladium (0) (52 mg, 0.045 mmol) was added and the reaction was stirred under nitrogen at 90° C. for 15 h. The reaction mixture was cooled, diluted with diethyl ether (60 mL) and washed with water and brine. The organic layer was dried over sodium sulfate, filtered and concentrated in vacuo. The crude material was purified by silica gel chromatography (0-10% methanol in dichloromethane with 0.5% ammonium hydroxide) to afford 300 mg (65%) of 2-(6-chloro-1H-indazol-3-yl)-5-(2-trimethylsilanyl-ethoxymethyl)-5H-pyrrolo[2,3-b]pyrazine-7-carboxylic acid ((S)-2-methoxy-1-methyl-ethyl)-amide as a foaming solid. MS: (M+H)$^+$=516.

Step 2

2-[6-Chloro-1-(2-dimethylamino-ethyl)-1H-indazol-3-yl]-5-(2-trimethylsilanyl-ethoxymethyl)-5H-pyrrolo[2,3-b]pyrazine-7-carboxylic acid ((S)-2-methoxy-1-methyl-ethyl)-amide

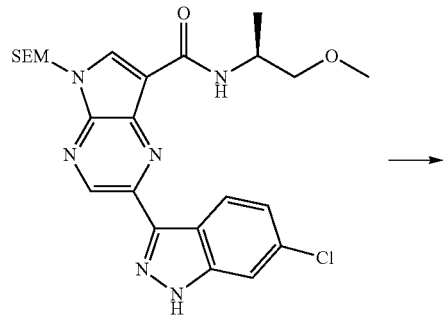

2-(6-Chloro-1H-indazol-3-yl)-5-(2-trimethylsilanyl-ethoxymethyl)-5H-pyrrolo[2,3-b]pyrazine-7-carboxylic acid ((S)-2-methoxy-1-methyl-ethyl)-amide (80 mg, 0.16 mmol) was combined with DMF (8 mL) at 0° C. to give a yellow solution. Sodium hydride (60% in mineral oil, 19 mg, 0.47 mmol) was added and the reaction was stirred at 0° C. for 10 min. Dimethylaminoethyl bromide hydrobromide (54 mg, 0.23 mmol) was added and the reaction was stirred at 0° C. for 30 min, then allowed to warm to room temperature and stirred for 2 h. The reaction mixture was quenched with 5 mL of brine and 10 mL of water, then extracted with ethyl acetate (2×30 mL). The combined organic layers were washed with water and brine, then dried and concentrated in vacuo. The crude material was purified by silica gel chromatography (0-10% methanol in dichloromethane) to afford 50 mg (55%) of 2-[6-chloro-1-(2-dimethylamino-ethyl)-1H-indazol-3-yl]-5-(2-trimethylsilanyl-ethoxymethyl)-5H-pyrrolo[2,3-b]pyrazine-7-carboxylic acid ((S)-2-methoxy-1-methyl-ethyl)-amide as a foaming solid. MS: (M+H)$^+$=587.

Step 3

2-[6-Chloro-1-(2-dimethylamino-ethyl)-1H-indazol-3-yl]-5H-pyrrolo[2,3-b]pyrazine-7-carboxylic acid ((S)-2-methoxy-1-methyl-ethyl)-amide

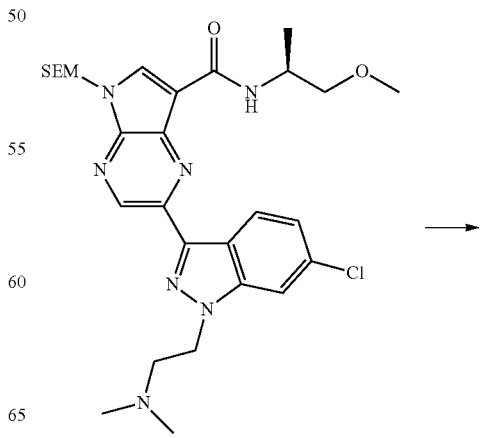

-continued

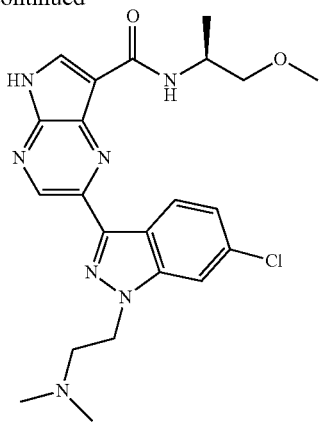

2-[6-Chloro-1-(2-dimethylamino-ethyl)-1H-indazol-3-yl]-5-(2-trimethylsilanylethoxymethyl)-5H-pyrrolo[2,3-b]pyrazine-7-carboxylic acid ((S)-2-methoxy-1-methyl-ethyl)amide (50 mg, 0.085 mmol) was combined with dichloromethane (1 mL) and trifluoroacetic acid (0.19 ml, 2.56 mmol) was added. After stirring for 2 h, the reaction mixture was concentrated in vacuo and the residue was dissolved in dichloromethane (1 mL). Ethylenediamine (0.17 ml, 2.56 mmol) was added. After stirring for 20 min, the reaction was concentrated in vacuo. The residue was triturated with water (2 mL). The precipitate was filtered, washed with water and dried to obtain 30 mg (73%) of 2-[6-chloro-1-(2-dimethylamino-ethyl)-1H-indazol-3-yl]-5H-pyrrolo[2,3-b]pyrazine-7-carboxylic acid ((S)-2-methoxy-1-methyl-ethyl)-amide as a yellow solid. MS: (M+H)$^+$=456; $^1$H NMR (DMSO-d$_6$) δ: 9.11 (s, 1H), 8.51 (d, J=8.5 Hz, 1H), 8.44 (s, 1H), 8.45 (s., 1H), 8.20 (d, J=8.0 Hz, 1H), 8.06 (s, 1H), 7.26 (d, J=8.3 Hz, 1H), 4.62 (br. s., 2H), 4.38 (br. s., 1H), 3.50 (dd, J=16.1, 4.0 Hz, 2H), 3.28 (s, 3H), 2.81 (br. s., 2H), 2.21 (s, 6H), 1.31 (d, J=6.5 Hz, 3H).

Example 235

2-(6-Chloro-1-pyridin-3-ylmethyl-1H-indazol-3-yl)-5H-pyrrolo[2,3-b]pyrazine-7-carboxylic acid ((S)-2-methoxy-1-methyl-ethyl)-amide

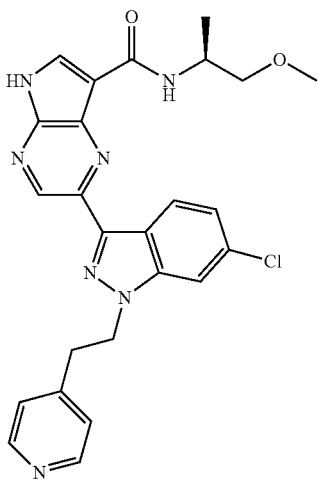 [SMILES: COC[C@H](C)NC(=O)c1c[nH]c2ncc(-c3nn(CCc4ccncc4)c4cc(Cl)ccc34)nc12]

Prepared according to the procedure outlined in Example 234, Steps 2-3, substituting 3-(chloromethyl)pyridine hydrochloride for dimethylaminoethyl bromide hydrobromide in Step 2.

MS: (M+H)$^+$=476; $^1$H NMR (DMSO-d$_6$) δ: 9.22 (s, 1H), 8.77 (br. s., 1H), 8.48-8.69 (m, 3H), 8.21-8.34 (m, 2H), 7.84 (d, J=7.3 Hz, 1H), 7.32-7.54 (m, 3H), 5.94 (br. s., 2H), 4.46 (br. s., 1H), 3.57 (dd, J=15.4, 3.9 Hz, 2H), 3.35 (s, 3H), 1.39 (d, J=6.3 Hz, 3H).

Example 236

2-[6-Chloro-1-(2-morpholin-4-yl-ethyl)-1H-indazol-3-yl]-5H-pyrrolo[2,3-b]pyrazine-7-carboxylic acid ((S)-2-methoxy-1-methyl-ethyl)-amide

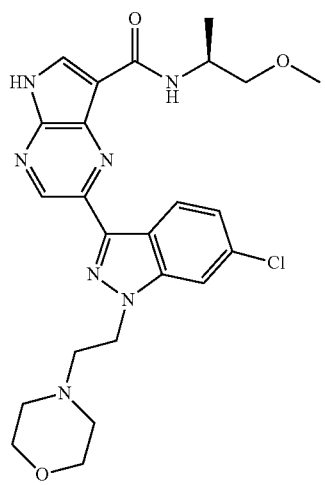 [SMILES: COC[C@H](C)NC(=O)c1c[nH]c2ncc(-c3nn(CCN4CCOCC4)c4cc(Cl)ccc34)nc12]

Prepared according to the procedure outlined in Example 234, Steps 2-3, substituting 4-(2-bromoethyl)morpholine hydrochloride for dimethylaminoethyl bromide hydrobromide in Step 2. MS: (M+H)$^+$=498; $^1$H NMR (DMSO-d$_6$) δ: 9.12 (s, 1H), 8.51 (d, J=8.5 Hz, 1H), 8.45 (s, 1H), 8.20 (d, J=8.0 Hz, 1H), 8.06 (br. s., 2H), 7.27 (d, J=8.0 Hz, 1H), 4.66

(br. s., 2H), 4.38 (br. s., 1H), 3.51 (br. s., 7H), 3.21-3.38 (m, 5H), 2.85 (br. s., 2H), 1.32 (d, J=6.3 Hz, 3H).

Example 237

2-[6-Fluoro-1-(6-morpholin-4-yl-pyridin-3-ylmethyl)-1H-indazol-3-yl]-5H-pyrrolo[2,3-b]pyrazine-7-carboxylic acid ((S)-2-methoxy-1-methyl-ethyl)-amide

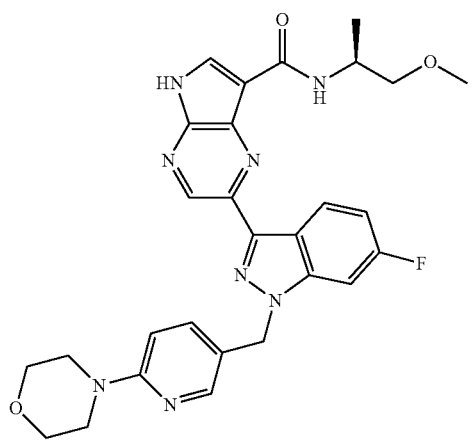 [SMILES: COC[C@H](C)NC(=O)c1c[nH]c2ncc(-c3nn(Cc4ccc(N5CCOCC5)nc4)c4cc(F)ccc34)nc12]

Step 1

2-(6-Fluoro-1H-indazol-3-yl)-5-(2-trimethylsilanyl-ethoxymethyl)-5H-pyrrolo[2,3-b]pyrazine-7-carboxylic acid ((S)-2-methoxy-1-methyl-ethyl)-amide

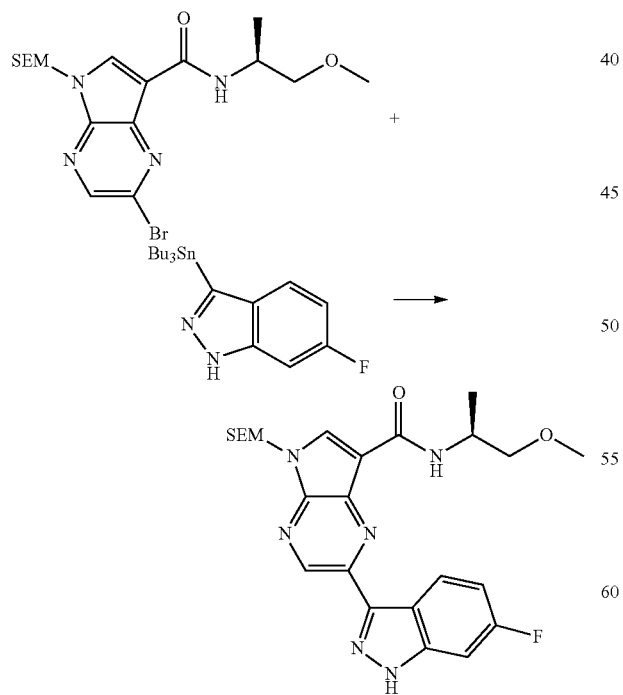

6-Fluoro-3-tributylstannyl-1H-indazole (1.10 g, 2.59 mmol), copper(I) iodide (24 mg, 0.13 mmol,) and 2-bromo-5-(2-trimethylsilanyl-ethoxymethyl)-5H-pyrrolo[2,3-b]pyrazine-7-carboxylic acid ((S)-2-methoxy-1-methyl-ethyl)-amide (560 mg, 1.26 mmol) were combined with DMF (6 mL) to give a yellow solution. The mixture was degassed with bubbling nitrogen for 10 min, then tetrakis(triphenylphosphine)palladium (0) (73 mg, 0.06 mmol) was added and the reaction was stirred under nitrogen at 80° C. for 2 h. The reaction mixture was cooled, diluted with diethyl ether (60 mL) and washed with water and brine. The organic layer was dried over sodium sulfate, filtered and concentrated in vacuo. The crude material was purified by silica gel chromatography (0-10% methanol in dichloromethane with 0.5% ammonium hydroxide) to obtain 580 mg (92%) of 2-(6-fluoro-1H-indazol-3-yl)-5-(2-trimethylsilanyl-ethoxymethyl)-5H-pyrrolo[2,3-b]pyrazine-7-carboxylic acid ((S)-2-methoxy-1-methyl-ethyl)-amide as an off-white solid. MS: $(M+H)^+=499$.

Step 2

2-[6-Fluoro-1-(6-morpholin-4-yl-pyridin-3-ylmethyl)-1H-indazol-3-yl]-5-(2-trimethylsilanylethoxymethyl)-5H-pyrrolo[2,3-b]pyrazine-7-carboxylic acid ((S)-2-methoxy-1-methyl-ethyl)amide

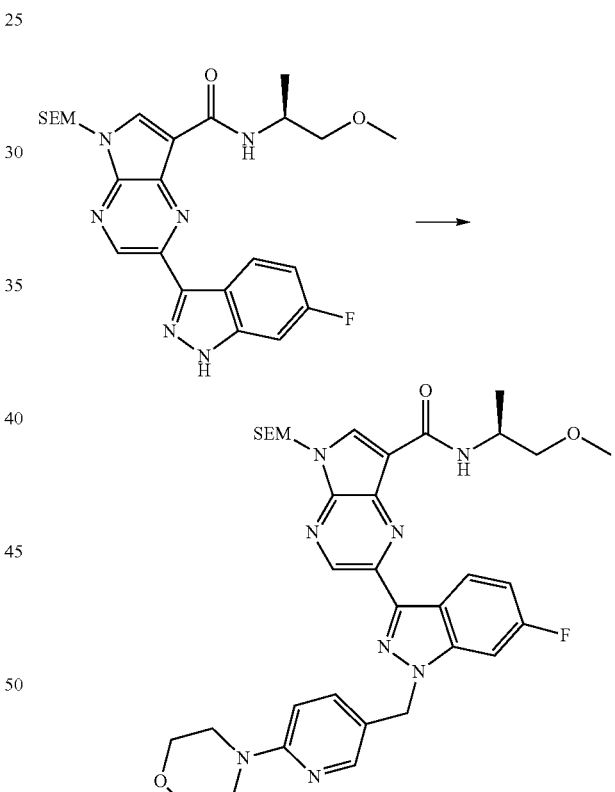

2-(6-Fluoro-1H-indazol-3-yl)-5-(2-trimethylsilanyl-ethoxymethyl)-5H-pyrrolo[2,3-b]pyrazine-7-carboxylic acid ((S)-2-methoxy-1-methyl-ethyl)-amide (80 mg, 0.16 mmol) was combined with DMF (8 mL) at 0° C. to give a yellow solution. Sodium hydride (60% in mineral oil, 19 mg, 0.48 mmol) was added and the reaction was stirred at 0° C. for 10 min. 4-(5-(Chloromethyl)pyridin-2-yl)morpholine hydrochloride (60 mg, 0.24 mmol) was added and the reaction mixture was stirred at 0° C. for 30 min then warmed to room temperature and stirred for 2 h. The reaction mixture was quenched with 5 mL of brine and 10 mL of water and extracted with ethyl acetate (2×30 mL). The combined organic layers were washed with water and brine then dried and concentrated in vacuo. The crude material was purified by silica gel chromatography (0-10% methanol in dichloromethane) to afford 58 mg (53%) of 2-[6-fluoro-1-(6-morpholin-4-yl-pyridin-3-ylmethyl)-1H-indazol-3-yl]-5-(2-trimethylsilanyl-ethoxymethyl)-5H-pyrrolo[2,3-b]pyrazine-7-carboxylic acid ((S)-2-methoxy-1-methyl-ethyl)-amide as a foaming solid. MS: (M+H)⁺=675.

Step 3

2-[6-Fluoro-1-(6-morpholin-4-yl-pyridin-3-ylmethyl)-1H-indazol-3-yl]-5H-pyrrolo[2,3-b]pyrazine-7-carboxylic acid ((S)-2-methoxy-1-methyl-ethyl)-amide

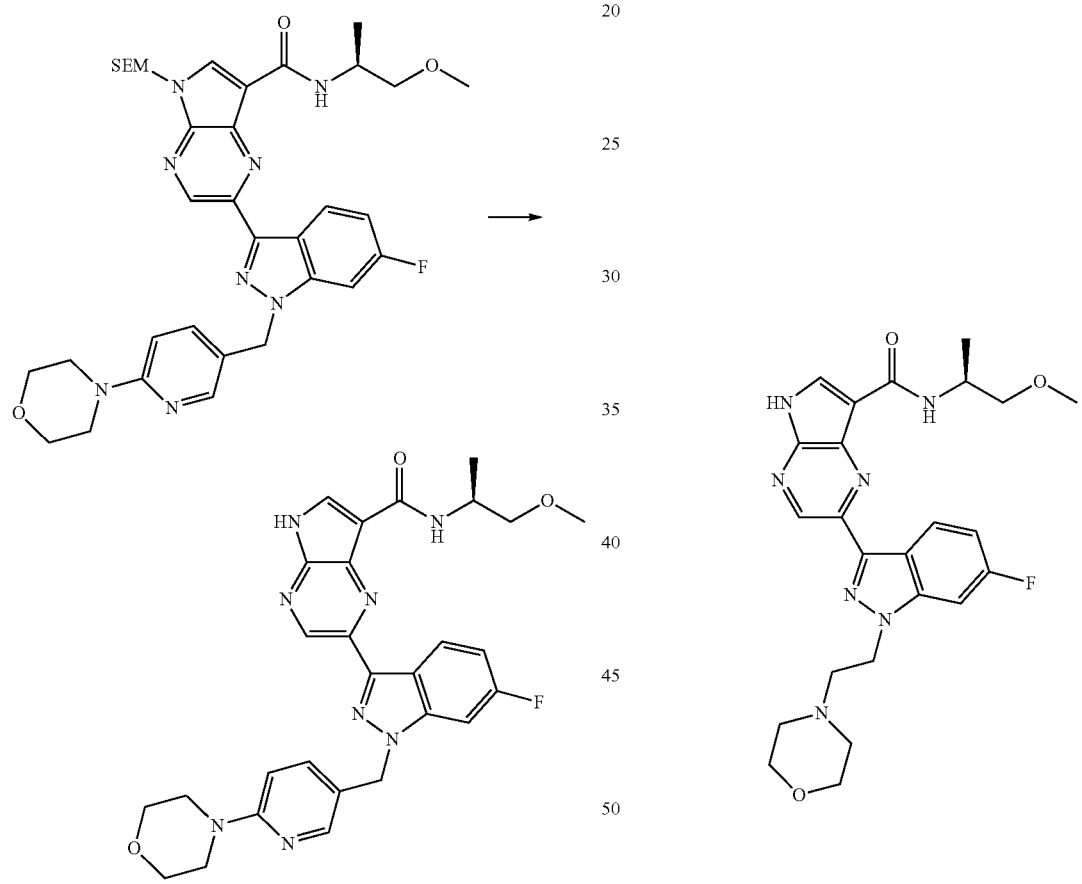

2-[6-Fluoro-1-(6-morpholin-4-yl-pyridin-3-ylmethyl)-1H-indazol-3-yl]-5-(2-trimethylsilanyl-ethoxymethyl)-5H-pyrrolo[2,3-b]pyrazine-7-carboxylic acid ((S)-2-methoxy-1-methyl-ethyl)-amide (50 mg, 0.074 mmol) was combined with dichloromethane (1 mL) and trifluoroacetic acid (0.17 ml, 2.22 mmol) was added. After stirring for 2 h, the reaction mixture was concentrated in vacuo. The residue was dissolved in dichloromethane (1 mL) and ethylenediamine (0.15 ml, 2.22 mmol) was added. After 20 min the reaction mixture was concentrated in vacuo and the residue was triturated with water (2 mL). The precipitate was filtered, washed with water and dried to afford 33 mg (77%) of 2-[6-fluoro-1-(6-morpholin-4-yl-pyridin-3-ylmethyl)-1H-indazol-3-yl]-5H-pyrrolo[2,3-b]pyrazine-7-carboxylic acid ((S)-2-methoxy-1-methyl-ethyl)-amide as a light yellow solid. MS: (M+H)⁺=545; ¹H NMR (DMSO-d₆) δ: 9.14 (s, 1H), 8.52-8.60 (m, 1H), 8.45 (s, 1H), 8.31 (br. s., 1H), 8.19 (d, J=8.3 Hz, 1H), 7.89 (d, J=9.5 Hz, 1H), 7.63 (d, J=8.3 Hz, 1H), 7.16 (t, J=9.0 Hz, 1H), 6.79 (d, J=8.3 Hz, 1H), 5.63 (br. s., 2H), 4.37 (br. s., 1H), 3.65 (br. s., 4H), 3.44-3.57 (m, 2H), 3.39 (br. s., 4H), 3.27 (s, 3H), 1.30 (d, J=6.3 Hz, 3H).

Example 238

2-[6-Fluoro-1-(2-morpholin-4-yl-ethyl)-1H-indazol-3-yl]-5H-pyrrolo[2,3-b]pyrazine-7-carboxylic acid ((S)-2-methoxy-1-methyl-ethyl)-amide Prepared according to the procedure outlined in Example 237, Steps 2-3, substituting 4-(2-bromoethyl)morpholine hydrochloride for 4-(5-(chloromethyl)pyridin-2-yl)morpholine hydrochloride in Step 2. MS: (M+H)⁺=482; ¹H NMR (DMSO-d₆) δ: 9.12 (s, 1H), 8.53 (dd, J=8.7, 5.4 Hz, 1H), 8.44 (s, 1H), 8.21 (d, J=8.5 Hz, 1H), 7.76 (d, J=9.8 Hz, 1H), 7.15

(t, J=8.2 Hz, 1H), 4.62 (t, J=6.3 Hz, 2H), 4.38 (br. s., 1H), 3.41-3.62 (m, 7H), 3.30 (d, J=18.3 Hz, 6H), 2.85 (t, J=6.3 Hz, 2H), 1.31 (d, J=6.8 Hz, 3H).

Example 239

2-[1-(2-Dimethylamino-ethyl)-6-fluoro-1H-indazol-3-yl]-5H-pyrrolo[2,3-b]pyrazine-7-carboxylic acid ((S)-2-methoxy-1-methyl-ethyl)-amide

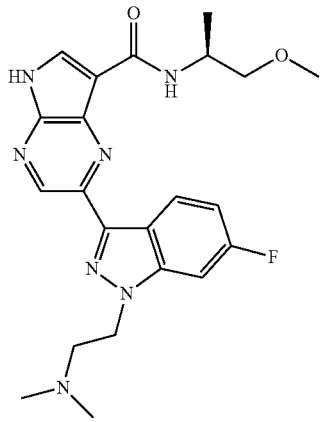 [SMILES: COC[C@H](C)NC(=O)c1c[nH]c2ncc(-c3nn(CCN(C)C)c4cc(F)ccc34)nc12]

Prepared according to the procedure outlined in Example 237, Steps 2-3, substituting dimethylaminoethyl bromide hydrobromide for 4-(5-(chloromethyl)pyridin-2-yl)morpholine hydrochloride in Step 2. MS: (M+H)$^+$=440; $^1$H NMR (DMSO-d$_6$) δ: 9.11 (s, 1H), 8.52 (dd, J=8.5, 5.3 Hz, 1H), 8.44 (s, 1H), 8.21 (d, J=8.3 Hz, 1H), 7.76 (d, J=9.3 Hz, 1H), 7.14 (t, J=8.4 Hz, 1H), 4.59 (t, J=6.0 Hz, 2H), 4.38 (br. s., 1H), 3.42-3.61 (m, 2H), 3.28 (s, 3H), 2.80 (t, J=6.1 Hz, 2H), 2.20 (s., 6H), 1.31 (d, J=6.5 Hz, 3H).

Example 240

2-(6-Fluoro-1-pyridin-2-ylmethyl-1H-indazol-3-yl)-5H-pyrrolo[2,3-b]pyrazine-7-carboxylic acid ((S)-2-methoxy-1-methyl-ethyl)-amide

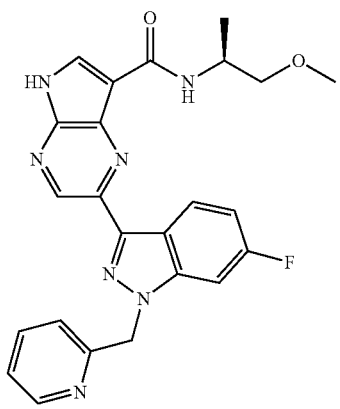 [SMILES: COC[C@H](C)NC(=O)c1c[nH]c2ncc(-c3nn(Cc4ccccn4)c4cc(F)ccc34)nc12]

Prepared according to the procedure outlined in Example 237, Steps 2-3, substituting 2-(chloromethyl)pyridine hydrochloride for 4-(5-(chloromethyl)pyridin-2-yl)morpholine hydrochloride in Step 2. MS: (M+H)$^+$=460; $^1$H NMR (DMSO-d$_6$) δ: 9.08 (s, 1H), 8.48-8.63 (m, 2H), 8.45 (s, 1H), 8.20 (d, J=8.5 Hz, 1H), 7.69-7.78 (m, 2H), 7.29-7.39 (m, 1H), 7.15-7.26 (m, 2H), 5.89 (s, 2H), 4.38 (br. s., 1H), 3.42-3.59 (m, 2H), 3.28 (s, 3H), 1.31 (d, J=6.8 Hz, 3H).

Example 241

2-(6-Fluoro-1-pyridin-3-ylmethyl-1H-indazol-3-yl)-5H-pyrrolo[2,3-b]pyrazine-7-carboxylic acid ((S)-2-methoxy-1-methyl-ethyl)-amide

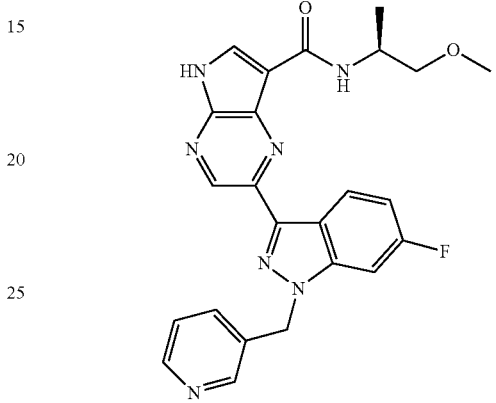

Prepared according to the procedure outlined in Example 237, Steps 2-3, substituting 3-(chloromethyl)pyridine hydrochloride for 4-(5-(chloromethyl)pyridin-2-yl)morpholine hydrochloride in Step 2. MS: (M+H)$^+$=460; $^1$H NMR (DMSO-d$_6$) δ: 9.13 (s, 1H), 8.69 (s, 1H), 8.40-8.61 (m, 3H), 8.18 (d, J=8.5 Hz, 1H), 7.88 (d, J=8.8 Hz, 1H), 7.77 (d, J=7.8 Hz, 1H), 7.32-7.45 (m, 1H), 7.18 (t, J=8.2 Hz, 1H), 5.82 (s, 2H), 4.37 (br. s., 1H), 3.49 (dd, J=14.1, 4.5 Hz, 2H), 3.27 (s, 3H), 1.30 (d, J=6.8 Hz, 3H).

Example 242

2-[6-Fluoro-1-(2-pyrrolidin-1-yl-ethyl)-1H-indazol-3-yl]-5H-pyrrolo[2,3-b]pyrazine-7-carboxylic acid ((S)-2-methoxy-1-methyl-ethyl)-amide

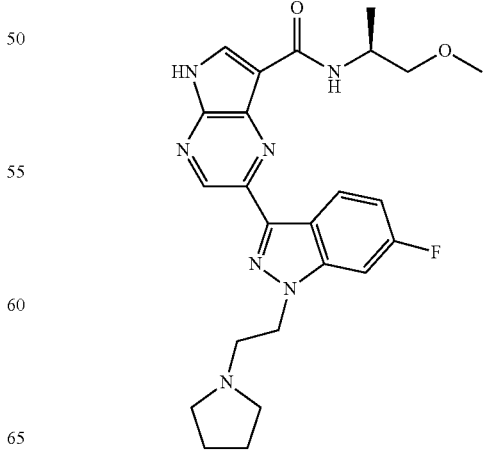

Prepared according to the procedure outlined in Example 237, Steps 2-3, substituting 1-(2-bromoethyl)pyrrolidine for 4-(5-(chloromethyl)pyridin-2-yl)morpholine hydrochloride in Step 2. MS: (M+H)$^+$=466; $^1$H NMR (DMSO-d$_6$) δ: 9.12 (s, 1H), 8.53 (br. s., 1H), 8.43 (s, 1H), 8.20 (d, J=8.0 Hz, 1H), 7.74 (d, J=9.5 Hz, 1H), 7.03-7.22 (m, 1H), 4.61 (br. s., 2H), 3.43-3.57 (m, 2H), 3.29 (m, 8H), 2.98 (br. s., 2H), 1.64 (br. s., 4H), 1.31 (d, J=6.5 Hz, 3H).

Example 243

2-{6-Fluoro-1-[2-((S)-3-fluoro-pyrrolidin-1-yl)-ethyl]-1H-indazol-3-yl}-5H-pyrrolo[2,3-b]pyrazine-7-carboxylic acid ((S)-2-methoxy-1-methyl-ethyl)-amide

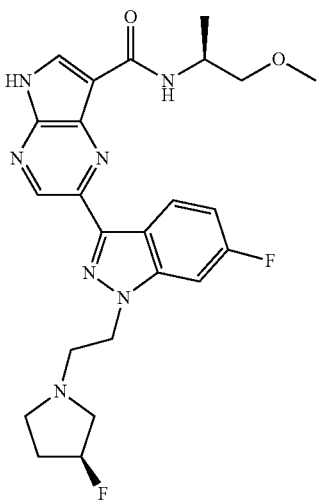 [SMILES: COC[C@H](C)NC(=O)c1c[nH]c2ncc(-c3nn(CCN4CC[C@H](F)C4)c4cc(F)ccc34)nc12]

Prepared according to the procedure outlined in Example 237, Steps 2-3, substituting (S)-1-(2-chloroethyl)-3-fluoropyrrolidine for 4-(5-(chloromethyl)pyridin-2-yl)morpholine hydrochloride in Step 2. MS: (M+H)$^+$=484; $^1$H NMR (DMSO-d$_6$) δ: 9.12 (s, 1H), 8.53 (dd, J=8.8, 5.3 Hz, 1H), 8.43 (s, 1H), 8.20 (d, J=8.3 Hz, 1H), 7.76 (d, J=9.0 Hz, 1H), 7.15 (t, J=8.7 Hz, 1H), 5.23 (br. s., 1H), 5.09 (br. s., 1H), 4.62 (t, J=6.3 Hz, 2H), 4.38 (br. s., 1H), 3.40-3.59 (m, 2H), 3.23-3.32 (s, 3H), 2.79-3.10 (m, 4H), 2.57-2.75 (m, 1H), 2.32-2.47 (m, 1H), 2.05 (m., 1H), 1.31 (d, J=6.8 Hz, 3H).

Example 244

2-[6-Fluoro-1-(2-pyrazol-1-yl-ethyl)-1H-indazol-3-yl]-5H-pyrrolo[2,3-b]pyrazine-7-carboxylic acid ((S)-2-methoxy-1-methyl-ethyl)-amide

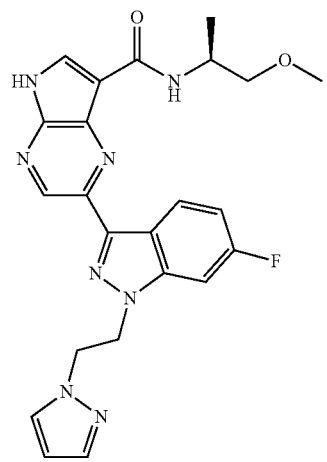 [SMILES: COC[C@H](C)NC(=O)c1c[nH]c2ncc(-c3nn(CCn4cccn4)c4cc(F)ccc34)nc12]

Prepared according to the procedure outlined in Example 237, Steps 2-3, substituting 1-(2-bromoethyl)-1H-pyrazole for 4-(5-(chloromethyl)pyridin-2-yl)morpholine hydrochloride in Step 2. MS: (M+H)$^+$=463; $^1$H NMR (DMSO-d$_6$) δ: 12.84 (br. s., 1H), 9.11 (s, 1H), 8.37-8.58 (m, 2H), 8.17 (d, J=8.3 Hz, 1H), 7.49 (d, J=2.0 Hz, 1H), 7.39 (s, 1H), 7.22-7.31 (m, 1H), 6.97-7.17 (m, 1H), 6.08 (s, 1H), 4.91 (t, J=5.5 Hz, 2H), 4.62-4.74 (m, 2H), 4.37 (br. s., 1H), 3.49 (dt, J=17.9, 4.7 Hz, 2H), 3.27 (s, 3H), 1.30 (d, J=6.8 Hz, 3H).

Example 245

2-[6-Chloro-1-(2-morpholin-4-yl-ethyl)-1H-indazol-3-yl]-5H-pyrrolo[2,3-b]pyrazine-7-carboxylic acid (1-pyridin-3-yl-ethyl)-amide

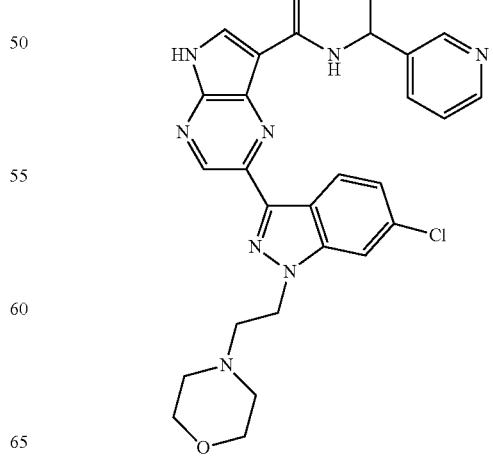

Step 1

2-Bromo-5-(2-trimethylsilanyl-ethoxymethyl)-5H-pyrrolo[2,3-b]pyrazine-7-carboxylic acid (1-pyridin-3-yl-ethyl)-amide

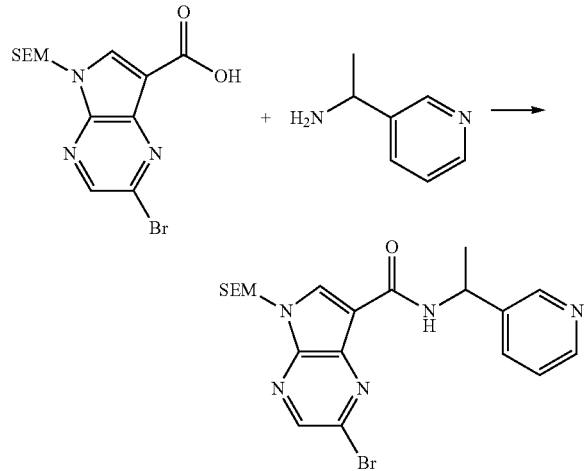

2-Bromo-5-((2-(trimethylsilyl)ethoxy)methyl)-5H-pyrrolo[2,3-b]pyrazine-7-carboxylic acid (300 mg, 0.81 mmol), 1-(pyridin-3-yl)ethanamine (148 mg, 1.21 mmol) and DIPEA (0.42 mL, 2.42 mmol) were combined with DMF (5 mL) to give a yellow solution. Then HATU (306 mg, 0.81 mmol) was added and the reaction mixture stirred at room temperature for 4 h. The reaction mixture was diluted with brine and extracted with ethyl acetate (2×30 mL). The combined organic layers were washed with water and brine then dried over MgSO$_4$, filtered and concentrated in vacuo to afford 350 mg (91%) of 2-bromo-5-(2-trimethylsilanyl-ethoxymethyl)-5H-pyrrolo[2,3-b]pyrazine-7-carboxylic acid (1-pyridin-3-yl-ethyl)-amide as a yellow oil. MS: (M+H)$^+$=477.

Step 2

2-(6-Chloro-1H-indazol-3-yl)-5-(2-trimethylsilanyl-ethoxymethyl)-5H-pyrrolo[2,3-b]pyrazine-7-carboxylic acid (1-pyridin-3-yl-ethyl)-amide

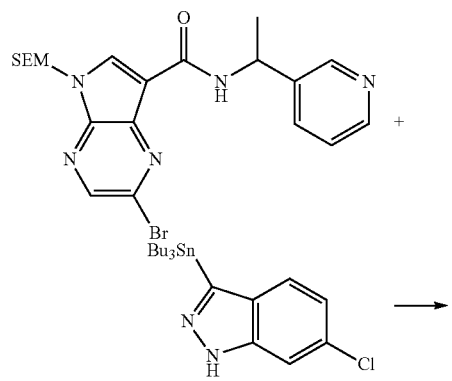

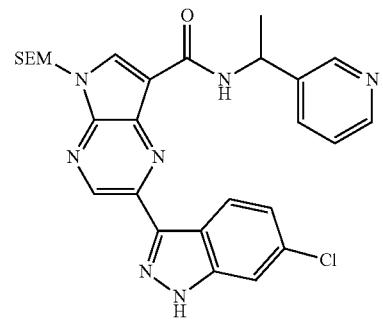

6-Chloro-3-tributylstannyl-1H-indazole (584 mg, 1.32 mmol), copper(I) iodide (14 mg, 0.074 mmol) and 2-bromo-5-(2-trimethylsilanyl-ethoxymethyl)-5H-pyrrolo[2,3-b]pyrazine-7-carboxylic acid (1-pyridin-3-yl-ethyl)-amide (350 mg, 0.74 mmol) were combined with DMF (6 mL) to give a yellow solution. The mixture was degassed with nitrogen for 10 min then tetrakis(triphenylphosphine)palladium (0) (42 mg, 0.037 mmol) was added and the reaction was stirred under nitrogen at 90° C. for 15 h. The reaction mixture was cooled, diluted with ether (60 mL) and washed with water and brine. The organic layer was dried over sodium sulfate, filtered and concentrated in vacuo. The residue was purified by silica gel chromatography (0-3% methanol in dichloromethane with 0.5% ammonium hydroxide) to afford 203 mg (48%) of 2-(6-chloro-1H-indazol-3-yl)-5-(2-trimethylsilanyl-ethoxymethyl)-5H-pyrrolo[2,3-b]pyrazine-7-carboxylic acid (1-pyridin-3-yl-ethyl)-amide as a foaming solid. MS: (M+H)$^+$=549.

Step 3

2-[6-Chloro-1-(2-morpholin-4-yl-ethyl)-1H-indazol-3-yl]-5-(2-trimethylsilanyl-ethoxymethyl)-5H-pyrrolo[2,3-b]pyrazine-7-carboxylic acid (1-pyridin-3-yl-ethyl)-amide

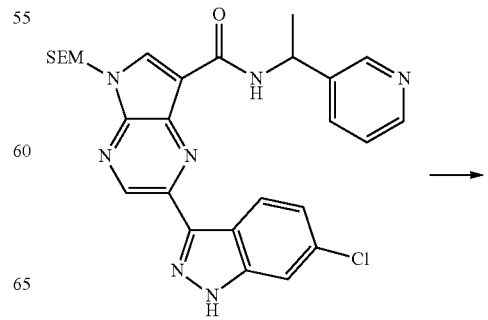

-continued

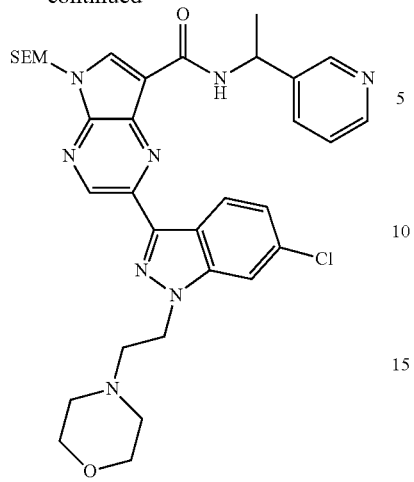

2-(6-Chloro-1H-indazol-3-yl)-5-(2-trimethylsilanyl-ethoxymethyl)-5H-pyrrolo[2,3-b]pyrazine-7-carboxylic acid (1-pyridin-3-yl-ethyl)-amide (100 mg, 0.18 mmol) was combined with DMF (2 mL) at 0° C. to give a yellow solution. Sodium hydride (60% in mineral oil, 22 mg, 0.55 mmol) was added and the reaction was stirred at 0° C. for 10 min. 4-(2-Bromoethyl)morpholine hydrocholoride (63 mg, 0.27 mmol) was added and the reaction was stirred at 0° C. for 30 min then warmed to room temperature and stirred for 2 h. The reaction mixture was quenched with 5 mL of brine and 10 mL of water and extracted with ethyl acetate (2×30 mL). The combined organic layers were washed with water and brine then dried with MgSO$_4$, filtered and concentrated in vacuo. The crude material was purified by silica gel chromatography (0-10% methanol in dichloromethane) to afford 40 mg (33%) of 2-[6-chloro-1-(2-morpholin-4-yl-ethyl)-1H-indazol-3-yl]-5-(2-trimethylsilanyl-ethoxymethyl)-5H-pyrrolo[2,3-b]pyrazine-7-carboxylic acid (1-pyridin-3-yl-ethyl)-amide as a foaming solid. MS: (M+H)$^+$=662.

Step 4

2-[6-Chloro-1-(2-morpholin-4-yl-ethyl)-1H-indazol-3-yl]-5H-pyrrolo[2,3-b]pyrazine-7-carboxylic acid (1-pyridin-3-yl-ethyl)-amide

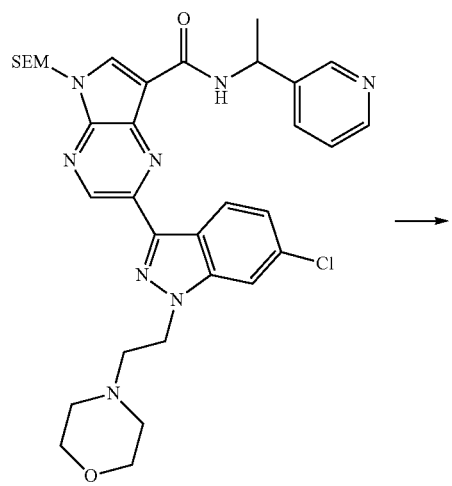

-continued

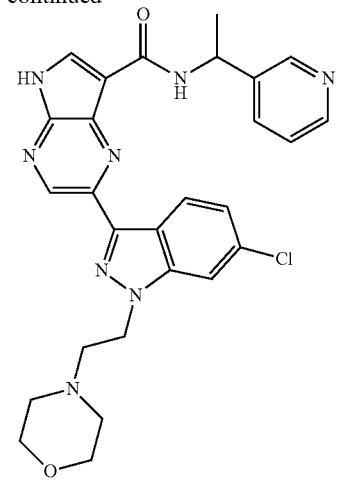

2-[6-Chloro-1-(2-morpholin-4-yl-ethyl)-1H-indazol-3-yl]-5-(2-trimethylsilanylethoxymethyl)-5H-pyrrolo[2,3-b]pyrazine-7-carboxylic acid (1-pyridin-3-yl-ethyl)-amide (50 mg, 0.076 mmol) was combined with dichloromethane (1 mL) and trifluoroacetic acid (0.17 ml, 2.27 mmol) was added. After stirring for 2 h, the reaction mixture was concentrated in vacuo. The residue was dissolved in dichloromethane (1 mL) and ethylenediamine (0.15 ml, 2.27 mmol) was added. The reaction mixture was stirred for 20 min then concentrated in vacuo and the residue was triturated with water (2 mL). The precipitate was filtered, washed with water and dried to afford 29 mg (68%) of 2-[6-chloro-1-(2-morpholin-4-yl-ethyl)-1H-indazol-3-yl]-5H-pyrrolo[2,3-b]pyrazine-7-carboxylic acid (1-pyridin-3-yl-ethyl)-amide as a yellow solid. MS: (M+H)$^+$= 531; $^1$H NMR (DMSO-d$_6$) δ: 9.11 (s, 1H), 8.71 (br. s., 1H), 8.43-8.58 (m, 3H), 8.29-8.38 (m, 1H), 8.05 (s, 1H), 7.86 (d, J=7.3 Hz, 1H), 7.36 (br. s., 1H), 7.15 (d, J=8.3 Hz, 1H), 5.35 (t, J=6.9 Hz, 1H), 4.65 (br. s., 2H), 3.50 (br. s., 4H), 3.33 (br. s., 4H), 2.84 (br. s., 2H), 1.68 (d, J=6.3 Hz, 3H).

Example 246

2-[6-Chloro-1-(2-dimethylamino-ethyl)-1H-indazol-3-yl]-5H-pyrrolo[2,3-b]pyrazine-7-carboxylic acid (1-pyridin-3-yl-ethyl)-amide

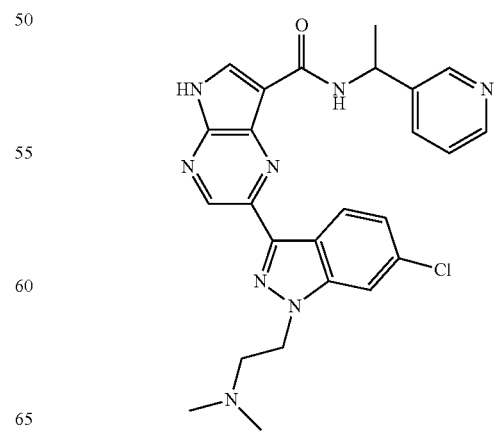

Prepared according to the procedure outlined in Example 245, Steps 3-4, substituting 2-bromo-N,N-dimethylethanamine hydrobromide for 4-(2-bromoethyl)morpholine hydrocholoride in Step 3. MS: (M+H)⁺=489; ¹H NMR (DMSO-d₆) δ: 9.11 (s, 1H), 8.71 (br. s., 1H), 8.43-8.55 (m, 3H), 8.31 (d, J=8.5 Hz, 1H), 8.04 (s, 1H), 7.85 (d, J=7.5 Hz, 1H), 7.33-7.39 (m, 1H), 7.15 (d, J=8.5 Hz, 1H), 5.34 (t, J=6.8 Hz, 1H), 4.61 (br. s., 2H), 2.72-2.84 (m, 2H), 2.20 (s, 6H), 1.68 (d, J=6.5 Hz, 3H).

Example 247

2-(6-Chloro-1-methyl-1H-indazol-3-yl)-5H-pyrrolo[2,3-b]pyrazine-7-carboxylic acid (1-pyridin-3-yl-ethyl)-amide

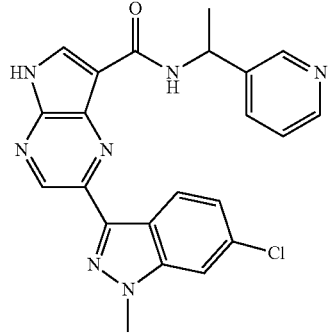 [SMILES: CC(NC(=O)c1c[nH]c2ncc(-c3nn(C)c4cc(Cl)ccc34)nc12)c1cccnc1]

Prepared according to the procedure outlined in Example 245, Steps 3-4, substituting iodomethane for 4-(2-bromoethyl)morpholine hydrocholoride in Step 3. MS: (M+H)⁺=431.

Example 248

2-[6-Fluoro-1-(2-morpholin-4-yl-ethyl)-1H-indazol-3-yl]-5H-pyrrolo[2,3-b]pyrazine-7-carboxylic acid (1-pyridin-4-yl-ethyl)-amide

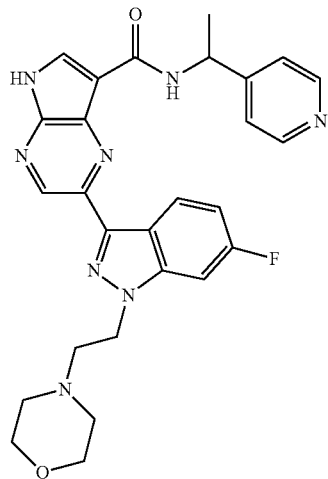 [SMILES: CC(NC(=O)c1c[nH]c2ncc(-c3nn(CCN4CCOCC4)c4cc(F)ccc34)nc12)c1ccncc1]

Step 1

2-Bromo-5-(2-trimethylsilanyl-ethoxymethyl)-5H-pyrrolo[2,3-b]pyrazine-7-carboxylic acid (1-pyridin-4-yl-ethyl)-amide

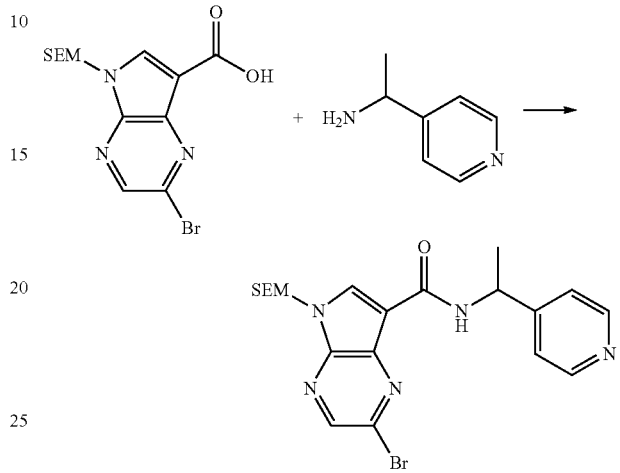

2-Bromo-5-((2-(trimethylsilyl)ethoxy)methyl)-5H-pyrrolo[2,3-b]pyrazine-7-carboxylic acid (320 mg, 0.86 mmol), 1-(pyridin-4-yl)ethanamine (105 mg, 0.86 mmol) and DIPEA (449 mg, 2.58 mmol) were combined with DMF (5 mL) to give a yellow solution. HATU (327 mg, 0.86 mmol) was added and the reaction mixture was stirred at room temperature for 2 h. The reaction mixture was diluted with brine and extracted with ethyl acetate (3×20 mL). The combined organic layers were washed with water and brine then dried with MgSO₄, filtered and concentrated in vacuo to afford 380 mg (93%) of 2-bromo-5-(2-trimethylsilanyl-ethoxymethyl)-5H-pyrrolo[2,3-b]pyrazine-7-carboxylic acid (1-pyridin-4-yl-ethyl)-amide as a red oil. MS: (M+H)⁺=477.

Step 2

2-(6-Fluoro-1H-indazol-3-yl)-5-(2-trimethylsilanyl-ethoxymethyl)-5H-pyrrolo[2,3-b]pyrazine-7-carboxylic acid (1-pyridin-4-yl-ethyl)-amide

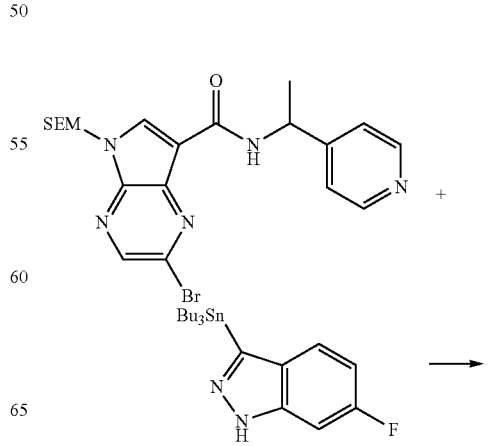

-continued

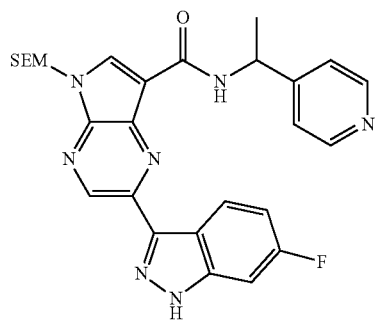

6-Fluoro-3-tributylstannyl-1H-indazole (0.48 g, 1.13 mmol), copper(I) iodide (16 mg, 0.084 mmol) and 2-bromo-5-(2-trimethylsilanyl-ethoxymethyl)-5H-pyrrolo[2,3-b]pyrazine-7-carboxylic acid (1-pyridin-4-yl-ethyl)-amide (400 mg, 0.84 mmol) were combined with DMF (6 mL) to give a yellow solution. The mixture was degassed for 10 min then tetrakis(triphenylphosphine)palladium (0) (45 mg, 0.039 mmol) was added. The reaction mixture was stirred under nitrogen at 90° C. for 15 h. The reaction mixture was cooled, diluted with ether (60 mL) and washed with water and brine. The organic layer was dried over anhydrous sodium sulfate, filtered and concentrated in vacuo. The residue was purified by silica gel chromatography (0-3% methanol in dichloromethane with 0.5% ammonium hydroxide) to afford 390 mg (87%) of 2-(6-fluoro-1H-indazol-3-yl)-5-(2-trimethylsilanyl-ethoxymethyl)-5H-pyrrolo[2,3-b]pyrazine-7-carboxylic acid (1-pyridin-4-yl-ethyl)-amide as a yellow solid. MS: (M+H)$^+$=532.

Step 3

2-[6-Fluoro-1-(2-morpholin-4-yl-ethyl)-1H-indazol-3-yl]-5-(2-trimethylsilanyl-ethoxymethyl)-5H-pyrrolo[2,3-b]pyrazine-7-carboxylic acid (1-pyridin-4-yl-ethyl)-amide

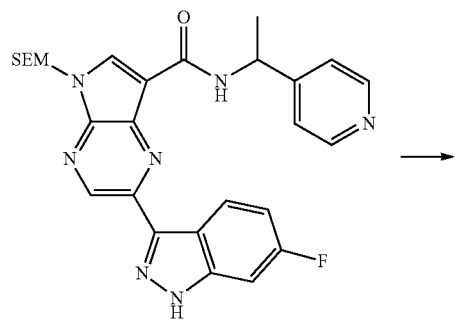

-continued

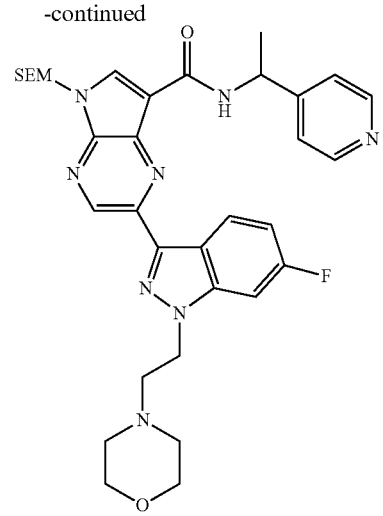

2-(6-Fluoro-1H-indazol-3-yl)-5-(2-trimethylsilanyl-ethoxymethyl)-5H-pyrrolo[2,3-b]pyrazine-7-carboxylic acid (1-pyridin-4-yl-ethyl)-amide (100 mg, 0.19 mmol) was combined with DMF (2 mL) at 0° C. to give a yellow solution. Sodium hydride (60% in mineral oil, 23 mg, 0.56 mmol) was added and the reaction was stirred at 0° C. for 10 min. 4-(2-Bromoethyl)morpholine hydrochloride (55 mg, 0.28 mmol) was added and the reaction was stirred at 0° C. for 30 min then warmed to room temperature. The reaction mixture was stirred for 2 h at room temperature then quenched with 5 mL of brine and 10 mL of water and extracted with ethyl acetate (2×30 mL). The combined organic layers were washed with water and brine then dried with MgSO$_4$, filtered and concentrated in vacuo. The crude material was purified by silica gel chromatography (0-10% methanol in dichloromethane) to give 70 mg (58%) of 2-[6-fluoro-1-(2-morpholin-4-yl-ethyl)-1H-indazol-3-yl]-5-(2-trimethylsilanyl-ethoxymethyl)-5H-pyrrolo[2,3-b]pyrazine-7-carboxylic acid (1-pyridin-4-yl-ethyl)-amide as a foaming solid. MS: (M+H)$^+$=645.

Step 4

2-[6-Fluoro-1-(2-morpholin-4-yl-ethyl)-1H-indazol-3-yl]-5H-pyrrolo[2,3-b]pyrazine-7-carboxylic acid (1-pyridin-4-yl-ethyl)-amide

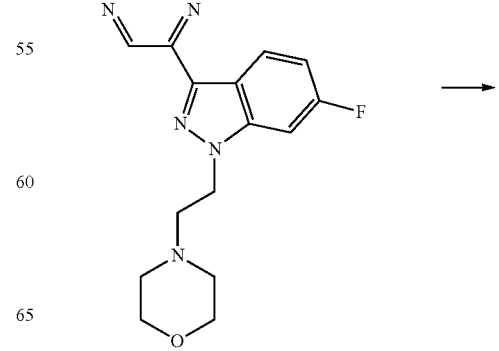

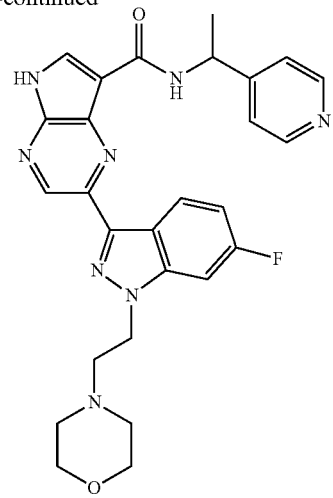

2-[6-Fluoro-1-(2-morpholin-4-yl-ethyl)-1H-indazol-3-yl]-5-(2-trimethylsilanylethoxymethyl)-5H-pyrrolo[2,3-b]pyrazine-7-carboxylic acid (1-pyridin-4-yl-ethyl)-amide (70 mg, 0.11 mmol) was combined with dichloromethane (1 mL) then trifluoroacetic acid (0.24 ml, 3.26 mmol) was added. After stirring for 2 h, the reaction mixture was concentrated in vacuo. The residue was dissolved in dichloromethane (1 mL) and ethylenediamine (0.22 ml, 3.26 mmol) was added. The reaction mixture was stirred for 20 min then concentrated in vacuo. The residue was diluted with water then extracted with CH$_2$Cl$_2$ (2×20 ml). The combined organic layers were dried with MgSO$_4$, filtered and concentrated in vacuo to afford 26 mg (44%) of 2-[6-fluoro-1-(2-morpholin-4-yl-ethyl)-1H-indazol-3-yl]-5H-pyrrolo[2,3-b]pyrazine-7-carboxylic acid (1-pyridin-4-yl-ethyl)-amide as a yellow solid. MS: (M+H)$^+$= 515; $^1$H NMR (DMSO-d$_6$) δ: 9.13 (s, 1H), 8.44-8.62 (m, 4H), 8.35 (dd, J=8.9, 5.4 Hz, 1H), 7.73 (dd, J=10.0, 2.0 Hz, 1H), 7.45 (d, J=6.0 Hz, 2H), 6.98 (d, J=2.0 Hz, 1H), 5.29 (t, J=7.2 Hz, 1H), 4.62 (t, J=6.4 Hz, 2H), 3.42-3.59 (m, 4H), 3.30 (m, 4H), 2.85 (t, J=6.4 Hz, 2H), 1.65 (d, J=7.0 Hz, 3H).

Example 249

2-[6-Fluoro-1-(2-dimethylamino-ethyl)-1H-indazol-3-yl]-5H-pyrrolo[2,3-b]pyrazine-7-carboxylic acid (1-pyridin-4-yl-ethyl)-amide

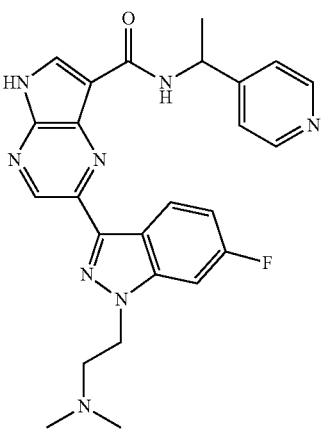 [SMILES: CC(NC(=O)c1c[nH]c2ncc(-c3nn(CCN(C)C)c4cc(F)ccc34)nc12)c1ccncc1]

Prepared according to the procedure outlined in Example 248, Steps 3-4, substituting 2-bromo-N,N-dimethylethanamine hydrobromide for 4-(2-bromoethyl)morpholine hydrocholoride in Step 3. MS: (M+H)$^+$=473; $^1$H NMR (DMSO-d$_6$) δ: 9.12 (s, 1H), 8.42-8.63 (m, 4H), 8.35 (dd, J=8.8, 5.3 Hz, 1H), 7.70-7.81 (m, 1H), 7.45 (d, J=5.8 Hz, 2H), 6.98 (d, J=1.8 Hz, 1H), 5.29 (t, J=7.2 Hz, 1H), 4.58 (t, J=6.4 Hz, 2H), 2.81 (t, J=6.4 Hz, 2H), 2.21 (s, 6H), 1.65 (d, J=7.0 Hz, 3H).

Example 250

2-[6-Fluoro-1-(2-pyrrolidin-1-yl-ethyl)-1H-indazol-3-yl]-5H-pyrrolo[2,3-b]pyrazine-7-carboxylic acid (1-methyl-2-pyridin-2-yl-ethyl)-amide

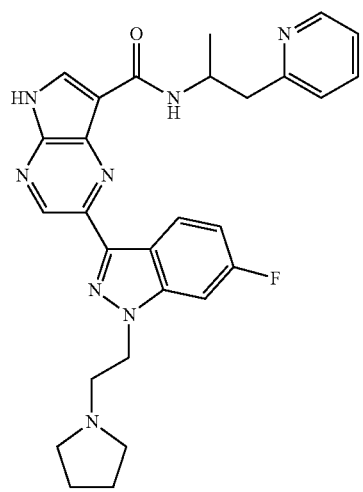 [SMILES: CC(Cc1ccccn1)NC(=O)c1c[nH]c2ncc(-c3nn(CCN4CCCC4)c4cc(F)ccc34)nc12]

Step 1

2-Bromo-5-(2-trimethylsilanyl-ethoxymethyl)-5H-pyrrolo[2,3-b]pyrazine-7-carboxylic acid (1-methyl-2-pyridin-2-yl-ethyl)-amide

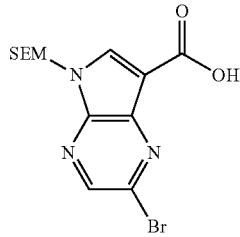

+

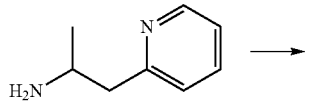

829
-continued

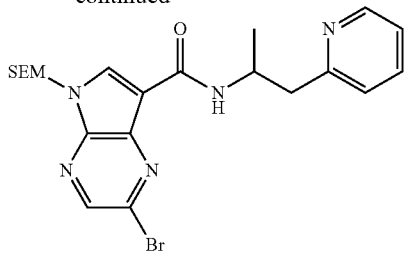

2-Bromo-5-((2-(trimethylsilyl)ethoxy)methyl)-5H-pyrrolo[2,3-b]pyrazine-7-carboxylic acid (300 mg, 0.81 mmol), 1-(pyridin-2-yl)propan-2-amine (165 mg, 1.21 mmol) and DIPEA (312 mg, 2.42 mmol) were combined with DMF (5 mL) to give a yellow solution. HATU (306 mg, 0.81 mmol) was added and the reaction was stirred at room temperature overnight. The reaction mixture was diluted with brine and extracted with ethyl acetate (2×30 mL). The combined organic layers were washed with water and brine then dried with MgSO₄, filtered and concentrated in vacuo. The residue was purified by silica gel chromatography (0-5% methanol in dichloromethane) to afford 360 mg (86%) of 2-bromo-5-(2-trimethylsilanyl-ethoxymethyl)-5H-pyrrolo[2,3-b]pyrazine-7-carboxylic acid (1-methyl-2-pyridin-2-yl-ethyl)-amide as a yellow oil. MS: (M+H)⁺=491.

Step 2

2-(6-Fluoro-1H-indazol-3-yl)-5-(2-trimethylsilanyl-ethoxymethyl)-5H-pyrrolo[2,3-b]pyrazine-7-carboxylic acid (1-methyl-2-pyridin-2-yl-ethyl)-amide

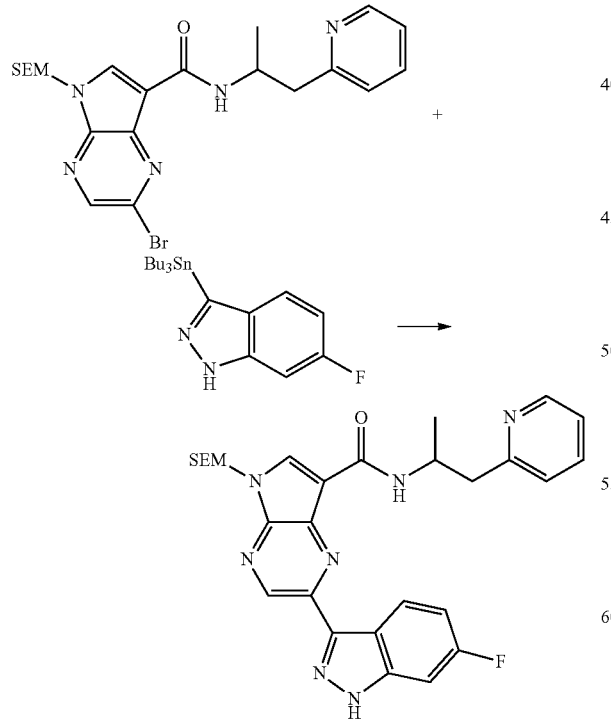

6-Fluoro-3-tributylstannyl-1H-indazole (0.20 g, 0.47 mmol), copper(I) iodide (12 mg, 0.06 mmol) and 2-bromo-

830

5-(2-trimethylsilanyl-ethoxymethyl)-5H-pyrrolo[2,3-b]pyrazine-7-carboxylic acid (1-methyl-2-pyridin-2-yl-ethyl)-amide (200 mg, 0.41 mmol) were combined with DMF (6 mL) to give a yellow solution. The mixture was degassed with nitrogen for 10 min then tetrakis(triphenylphosphine)palladium (0) (23 mg, 0.02 mmol) was added. The reaction was stirred at 90° C. under nitrogen for 15 h. The reaction mixture was cooled, diluted with ether (60 mL) and washed with water and brine. The organic layer was dried over anhydrous sodium sulfate, filtered and concentrated in vacuo. The residue was purified by silica gel chromatography (0-3% methanol in dichloromethane with 0.5% ammonium hydroxide) to give 136 mg (61%) of 2-(6-fluoro-1H-indazol-3-yl)-5-(2-trimethylsilanyl-ethoxymethyl)-5H-pyrrolo[2,3-b]pyrazine-7-carboxylic acid (1-methyl-2-pyridin-2-yl-ethyl)-amide as a foaming solid. MS: (M+H)⁺=546.

Step 3

2-[6-Fluoro-1-(2-pyrrolidin-1-yl-ethyl)-1H-indazol-3-yl]-5-(2-trimethylsilanyl-ethoxymethyl)-5H-pyrrolo[2,3-b]pyrazine-7-carboxylic acid (1-methyl-2-pyridin-2-yl-ethyl)-amide

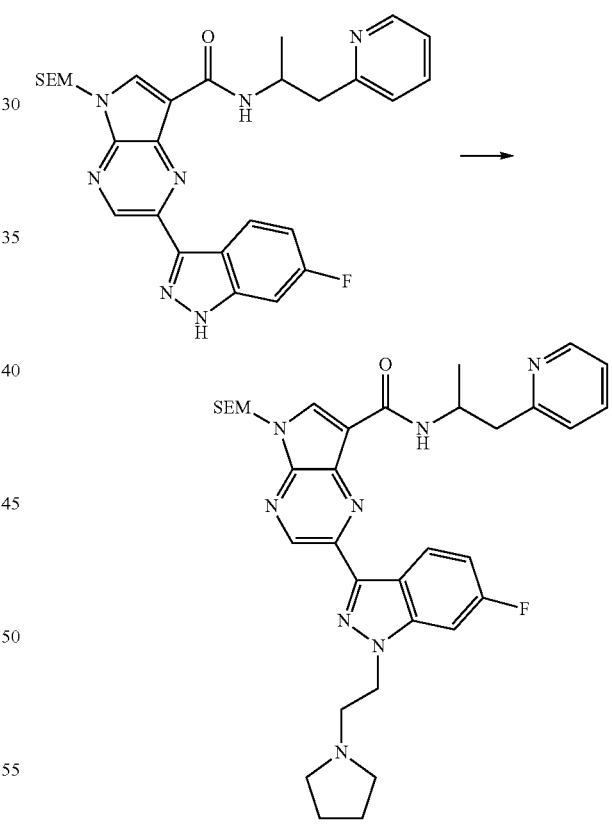

2-(6-Fluoro-1H-indazol-3-yl)-5-(2-trimethylsilanyl-ethoxymethyl)-5H-pyrrolo[2,3-b]pyrazine-7-carboxylic acid (1-methyl-2-pyridin-2-yl-ethyl)-amide (70 mg, 0.13 mmol) was combined with DMF (2 mL) at 0° C. to give a yellow solution. Sodium hydride (60% in mineral oil, 14 mg, 0.385 mmol) was added and the reaction was stirred at 0° C. for 10 min. 1-(2-Bromoethyl)pyrrolidine hydrochloride (41 mg, 0.19 mmol) was added and teh reaction was stirred at 0° C. for 30 min then warmed to room temperature. The reaction mixture was stirred for 2 h then quenched with 5 mL of brine and 10 mL of water and extracted with ethyl acetate (2×30 mL). The combined organic layers were washed with water and brine then dried with MgSO₄, filtered and concentrated in vacuo. The residue was purified by silica gel chromatography (0-10% methanol in dichloromethane) to afford 75 mg (91%) of 2-[6-fluoro-1-(2-pyrrolidin-1-yl-ethyl)-1H-indazol-3-yl]-5-(2-trimethylsilanyl-ethoxymethyl)-5H-pyrrolo[2,3-b]pyrazine-7-carboxylic acid (1-methyl-2-pyridin-2-yl-ethyl)-amide as a foaming solid. MS: (M+H)⁺=643.

Step 4

2-[6-Fluoro-1-(2-pyrrolidin-1-yl-ethyl)-1H-indazol-3-yl]-5H-pyrrolo[2,3-b]pyrazine-7-carboxylic acid (1-methyl-2-pyridin-2-yl-ethyl)-amide

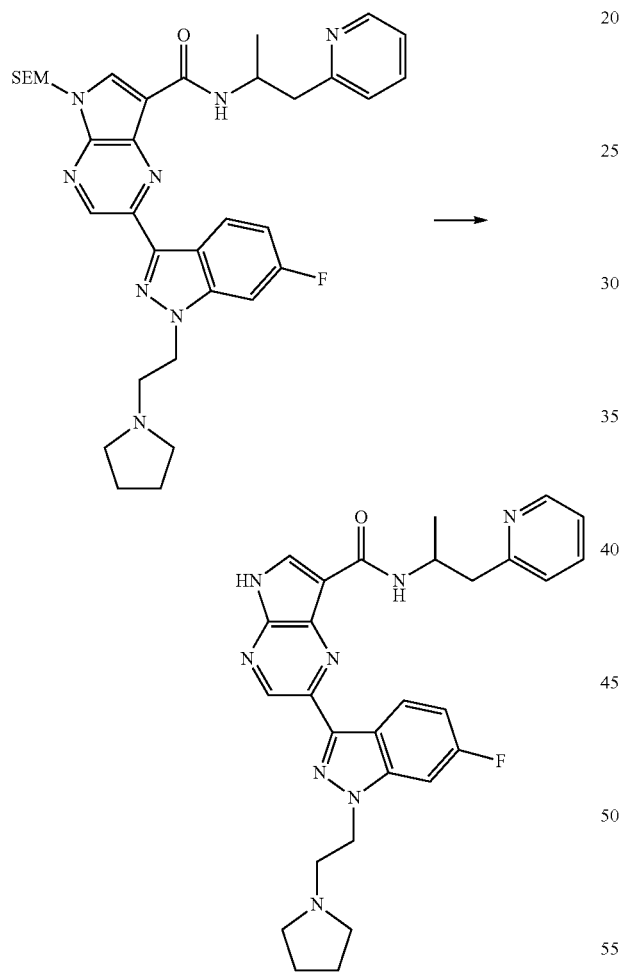

2-[6-Fluoro-1-(2-pyrrolidin-1-yl-ethyl)-1H-indazol-3-yl]-5-(2-trimethylsilanylethoxymethyl)-5H-pyrrolo[2,3-b]pyrazine-7-carboxylic acid (1-methyl-2-pyridin-2-yl-ethyl) amide (75 mg, 0.117 mmol) was combined with dichloromethane (1 mL) then trifluoroacetic acid (0.26 ml, 3.50 mmol) was added. After stirring for 2 h, the reaction mixture was concentrated in vacuo. The residue was dissolved in dichloromethane (1 mL) and ethylenediamine (0.23 ml, 3.50 mmol) was added and the reaction was stirred at room temperature for 20 min. The reaction mixture was concentrated in vacuo and the residue was triturated with water (2 mL). The precipitate was filtered, washed with water and dried to afford 26 mg (41%) of 2-[6-fluoro-1-(2-pyrrolidin-1-yl-ethyl)-1H-indazol-3-yl]-5H-pyrrolo[2,3-b]pyrazine-7-carboxylic acid (1-methyl-2-pyridin-2-yl-ethyl)-amide (26 mg, 41%) as a yellow solid. MS: (M+H)⁺=513; ¹H NMR (DMSO-d₆) δ: 9.07 (s, 1H), 8.32-8.44 (m, 2H), 8.22 (d, J=8.3 Hz, 1H), 7.73 (d, J=9.8 Hz, 1H), 7.50-7.66 (m, 2H), 7.27 (d, J=7.8 Hz, 1H), 7.03-7.16 (m, 2H), 4.53-4.67 (m, 4H), 4.46 (s, 1H), 3.02-3.25 (m, 2H), 2.98 (t, J=6.5 Hz, 3H), 1.64 (br. s., 5H), 1.29 (d, J=6.5 Hz, 3H).

Example 251

2-[6-Fluoro-1-(2-morpholin-4-yl-2-oxo-ethyl)-1H-indazol-3-yl]-5H-pyrrolo[2,3-b]pyrazine-7-carboxylic acid tert-butylamide

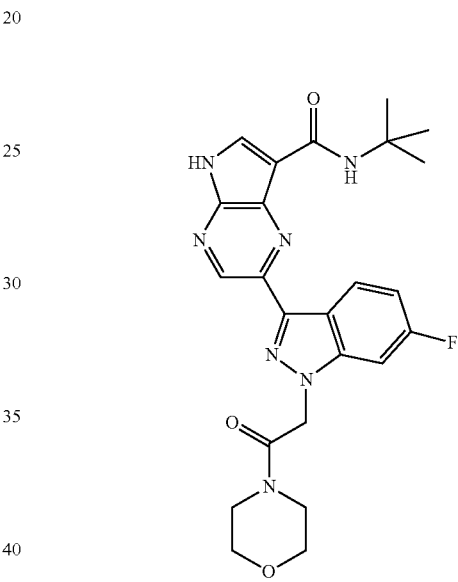

Step 1

2-[6-Fluoro-1-(2-morpholin-4-yl-2-oxo-ethyl)-1H-indazol-3-yl]-5-(2-trimethylsilanylethoxymethyl)-5H-pyrrolo[2,3-b]pyrazine-7-carbaldehyde

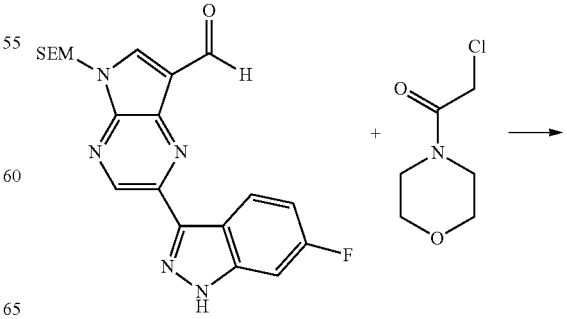

833

-continued

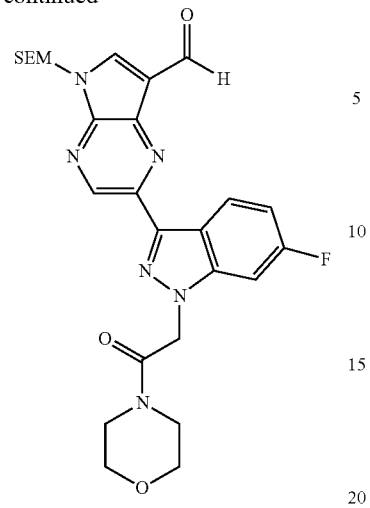

A 5 ml microwave vial was charged with 2-(6-fluoro-1H-indazol-3-yl)-5-(2-trimethylsilanyl-ethoxymethyl)-5H-pyrrolo[2,3-b]pyrazine-7-carbaldehyde (300 mg, 0.73 mmol), 4-(2-chloroacetyl)morpholine (0.19 ml, 1.46 mmol), cesium carbonate (713 mg, 2.19 mmol) and DMF (3.3 ml). The vial was flushed with argon, sealed and heated in a microwave reactor at 100° C. for 2 h. The reaction mixture was quenched with water and extracted with diethyl ether (2×). The organic layers were washed twice with water and once with brine then dried over sodium sulfate, filtered and concentrated. The residue was chromatographed over silica gel with EtOAc/hexanes (gradient 0-70% EtOAc) to afford 268 mg (68%) of 2-[6-fluoro-1-(2-morpholin-4-yl-2-oxo-ethyl)-1H-indazol-3-yl]-5-(2-trimethylsilanyl-ethoxymethyl)-5H-pyrrolo[2,3-b]pyrazine-7-carbaldehyde as a yellow powder.

Step 2

2-[6-Fluoro-1-(2-morpholin-4-yl-2-oxo-ethyl)-1H-indazol-3-yl]-5-(2-trimethylsilanylethoxymethyl)-5H-pyrrolo[2,3-b]pyrazine-7-carboxylic acid

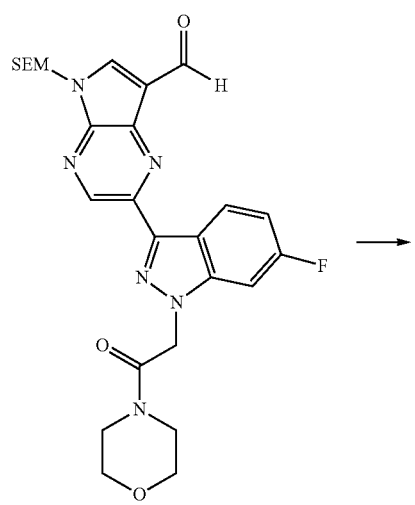

834

-continued

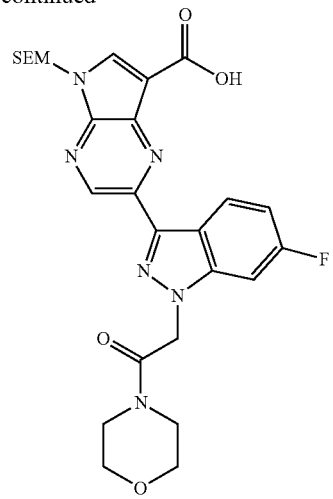

In a 50 ml round-bottomed flask, 2-[6-fluoro-1-(2-morpholin-4-yl-2-oxo-ethyl)-1H-indazol-3-yl]-5-(2-trimethylsilanyl-ethoxymethyl)-5H-pyrrolo[2,3-b]pyrazine-7-carbaldehyde (265 mg, 0.49 mmol) was dissolved in THF (10 ml) and water (2 ml). The yellow solution was cooled to 0° C. and sulfamic acid (287 mg, 2.95 mmol) was added. Then, a solution of sodium chlorite (80%, 76 mg, 0.67 mmol) and potassium dihydrogen phosphate (803 mg, 5.9 mmol) in water (6 ml) was added dropwise via pipette. After the addition was complete, the ice bath was removed and the reaction mixture was stirred at room temperature for 2 h. The reaction mixture was diluted with water and extracted with EtOAc (2×). The combined organic layers were washed with water and brine then dried over sodium sulfate, filtered and concentrated. The residue was triturated with hexanes/ethyl acetate to afford 259 mg (95%) of 2-[6-fluoro-1-(2-morpholin-4-yl-2-oxo-ethyl)-1H-indazol-3-yl]-5-(2-trimethylsilanyl-ethoxymethyl)-5H-pyrrolo[2,3-b]pyrazine-7-carboxylic acid as a light yellow powder.

Step 3

2-[6-Fluoro-1-(2-morpholin-4-yl-2-oxo-ethyl)-1H-indazol-3-yl]-5-(2-trimethylsilanyl-ethoxymethyl)-5H-pyrrolo[2,3-b]pyrazine-7-carboxylic acid tert-butylamide

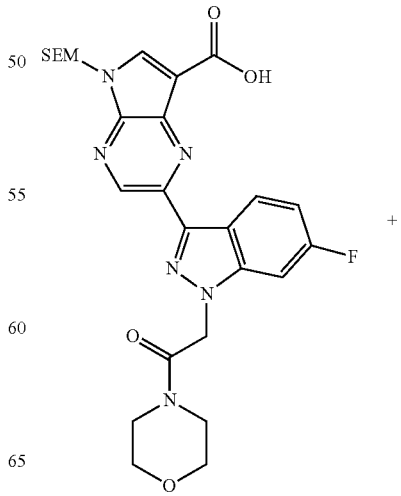

+

835
-continued

836
Step 4

2-[6-Fluoro-1-(2-morpholin-4-yl-2-oxo-ethyl)-1H-indazol-3-yl]-5H-pyrrolo[2,3-b]pyrazine-7-carboxylic acid tert-butylamide

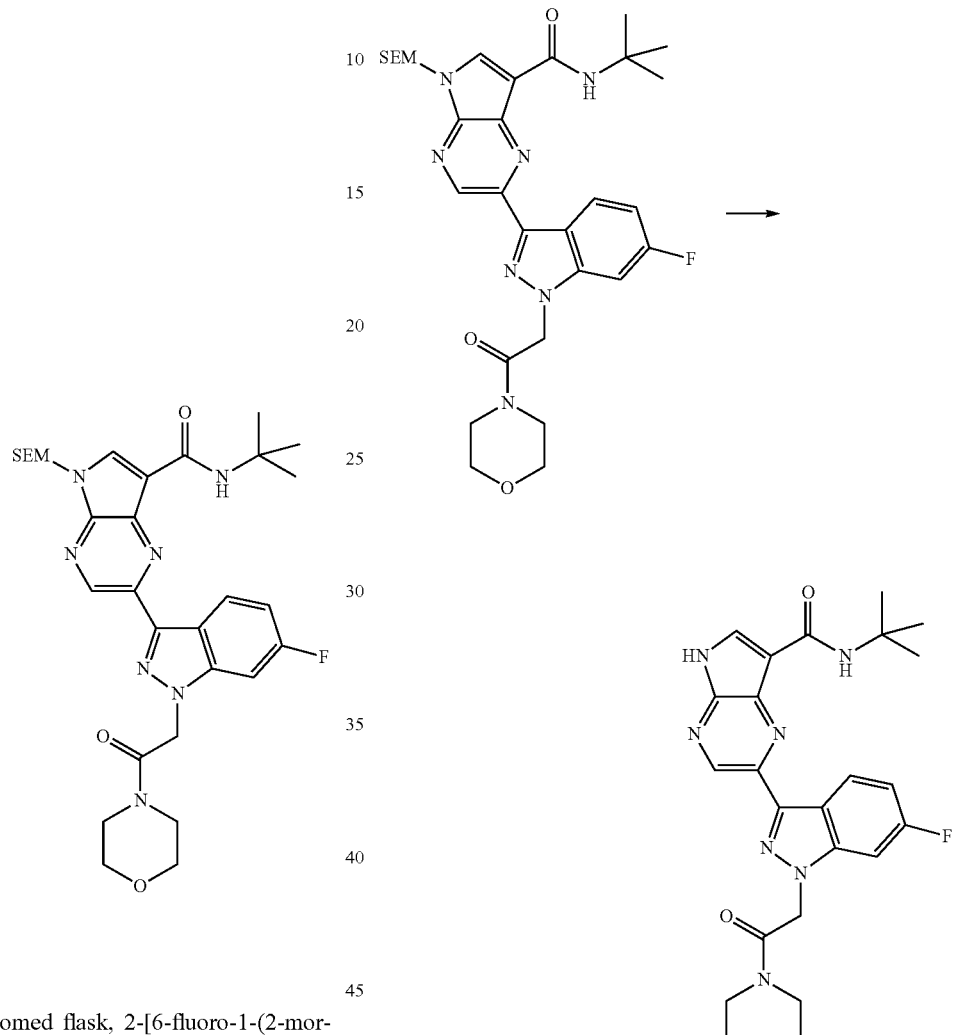

In a 15 ml round-bottomed flask, 2-[6-fluoro-1-(2-morpholin-4-yl-2-oxo-ethyl)-1H-indazol-3-yl]-5-(2-trimethylsilanyl-ethoxymethyl)-5H-pyrrolo[2,3-b]pyrazine-7-carboxylic acid (110 mg, 0.20 mmol) was suspended in THF (3 ml) and 1,1'-carbonyldiimidazole (39 mg, 0.24 mmol) was added. The light yellow suspension was stirred at 60° C. for 45 min during which time all solids dissolved. The reaction mixture was cooled to room temperature, tert-butylamine (0.20 ml, 1.9 mmol) was added, and the reaction was stirred at room temperature overnight. The reaction mixture was quenched with water and extracted with EtOAc (2×). The combined organic layers were washed with water and brine then dried over sodium sulfate, filtered and concentrated. The residue was chromatographed over silica gel with EtOAc/hexanes (gradient: 0-80% EtOAc) to afford 84 mg (70%) of 2-[6-fluoro-1-(2-morpholin-4-yl-2-oxo-ethyl)-1H-indazol-3-yl]-5-(2-trimethylsilanyl-ethoxymethyl)-5H-pyrrolo[2,3-b]pyrazine-7-carboxylic acid tert-butylamide as an off-white solid.

In a round-bottomed flask, 2-[6-fluoro-1-(2-morpholin-4-yl-2-oxo-ethyl)-1H-indazol-3-yl]-5-(2-trimethylsilanyl-ethoxymethyl)-5H-pyrrolo[2,3-b]pyrazine-7-carboxylic acid tert-butylamide (81 mg, 0.13 mmol) was dissolved in dichloromethane (0.7 ml) and trifluoroacetic acid (0.41 ml, 5.32 mmol) was added. The yellow reaction mixture was stirred at room temperature for 2 h then concentrated. The residue was dissolved in dichloromethane (0.7 ml) and ethylenediamine (0.54 ml, 8.00 mmol) was added. The reaction was stirred at room temperature for 1 h then quenched with water and diluted with ethyl acetate. The resulting suspension was filtered and washed with hot water and ethyl acetate and dried under high vacuum to provide 38 mg (60%) of 2-[6-fluoro-1-(2-morpholin-4-yl-2-oxo-ethyl)-1H-indazol-3-yl]-5H-pyrrolo[2,3-b]pyrazine-7-carboxylic acid tert-butylamide as an off-white powder. MS: (M+Na)$^+$=502; $^1$H NMR (DMSO-$d_6$, 400 MHz): δ (ppm) 12.81 (br. s., 1H), 9.04 (s, 1H), 8.49 (dd, J=8.8, 5.3 Hz, 1H), 8.40 (s, 1H), 7.95 (s, 1H), 7.62 (dd, J=10.0, 2.1 Hz, 1H), 7.16 (td, J=9.1, 2.3 Hz, 1H), 5.60 (s, 2H), 3.69-3.77 (m, 2H), 3.57-3.67 (m, 4H), 3.42-3.50 (m, 2H), 1.53 (s, 9H).

Example 252

2-(6-Fluoro-1-methyl-1H-indazol-3-yl)-5H-pyrrolo[2,3-b]pyrazine-7-carboxylic acid ((R)-1-oxetan-3-yl-ethyl)-amide

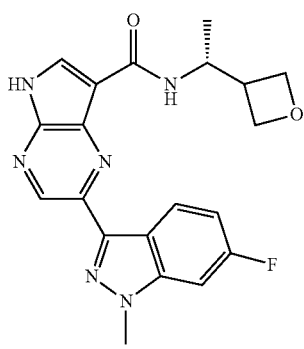 [SMILES: C[C@@H](NC(=O)c1c[nH]c2ncc(-c3nn(C)c4cc(F)ccc34)nc12)C1COC1]

Step 1

Oxetane-3-carbaldehyde

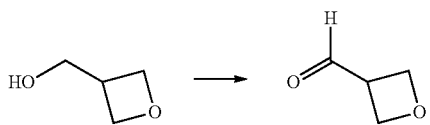 [SMILES: OCC1COC1 ; O=CC1COC1]

In a 50 ml round-bottomed flask, oxetan-3-ylmethanol (330 mg, 3.75 mmol) was dissolved in dichloromethane (16 ml). Pyridinium chlorochromate (888 mg, 4.12 mmol) was added and the reaction mixture was stirred at room temperature overnight. The dark brown suspension was filtered over Celite and rinsed with dichloromethane. The filtrate was concentrated at room temperature to afford oxetane-3-carbaldehyde as a dark brown oil which was used without further purification.

Step 2

(S)-2-Methyl-propane-2-sulfinic acid 1-oxetan-3-yl-meth-(E)-ylideneamide

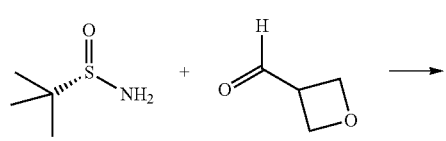

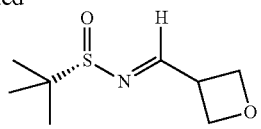

In a round-bottomed flask, oxetane-3-carbaldehyde (452 mg, 3.15 mmol) was dissolved in dichloromethane (18 ml) and (S)-2-methylpropane-2-sulfinamide (435 mg, 3.59 mmol) and anhydrous copper (II) sulfate (1.11 g, 6.93 mmol) were added. The reaction mixture was stirred at room temperature for 48 h then filtered through a glass microfiber filter, rinsing with dichloromethane. The filtrate was concentrated and the residue was chromatographed over silica gel with EtOAc/hexanes (gradient: 0-30% EtOAc) to afford 173 mg (29%) of (S)-2-methyl-propane-2-sulfinic acid 1-oxetan-3-yl-meth-(E)-ylideneamide as a colorless oil. $^1$H NMR (CDCl$_3$, 300 MHz): δ (ppm) 8.28 (d, J=4.9 Hz, 1H), 4.74-5.00 (m, 4H), 4.00-4.19 (m, 1H), 1.23 (s, 9H).

Step 3

(S)-2-Methyl-propane-2-sulfinic acid ((R)-1-oxetan-3-yl-ethyl)-amide

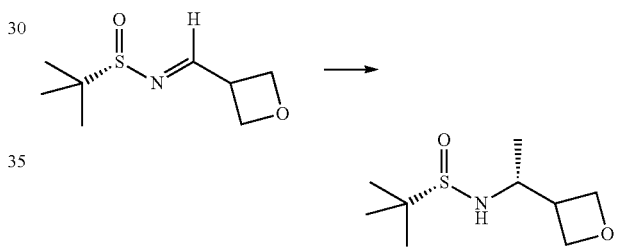

In a round-bottomed flask, (S)-2-methyl-propane-2-sulfinic acid 1-oxetan-3-yl-meth-(E)-ylideneamide (172 mg, 0.91 mmol) was dissolved in dichloromethane (3.6 ml). The colorless solution was cooled to −76° C. and methylmagnesium bromide (3.0 M in diethyl ether, 0.91 ml, 2.73 mmol) was added dropwise. The reaction mixture was stirred at −76° C. for 3 h and then allowed to warm slowly to room temperature overnight. The reaction was quenched with saturated NH$_4$Cl-solution then extracted with EtOAc (2×). The combined organic layers were washed with water and brine then dried over sodium sulfate, filtered and concentrated to provide 143 mg (77%) of (S)-2-methyl-propane-2-sulfinic acid ((R)-1-oxetan-3-yl-ethyl)-amide as a light yellow oil which was used without further purification.

Step 3

(R)-1-Oxetan-3-yl-ethylamine

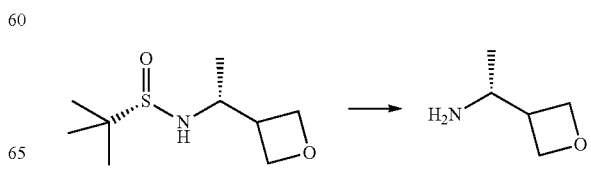

In a round-bottomed flask, (S)-2-methyl-propane-2-sulfinic acid ((R)-1-oxetan-3-yl-ethyl)-amide (142 mg, 0.69 mmol) was dissolved in methanol (3 ml). The pale yellow solution was cooled to 0° C. and hydrogen chloride (4.0 M in 1,4-dioxane, 0.24 ml, 0.96 mmol) was added dropwise. The reaction mixture was stirred at 0° C. for 1 h then quenched with saturated aqueous NaHCO$_3$ and extracted with dichloromethane (2×). The combined organic layers were dried over sodium sulfate, filtered and concentrated to give (R)-1-oxetan-3-yl-ethylamine as a light yellow oil which was used without further purification.

Step 4

2-(6-Fluoro-1-methyl-1H-indazol-3-yl)-5-(2-trimethylsilanyl-ethoxymethyl)-5H-pyrrolo[2,3-b]pyrazine-7-carboxylic acid ((R)-1-oxetan-3-yl-ethyl)-amide

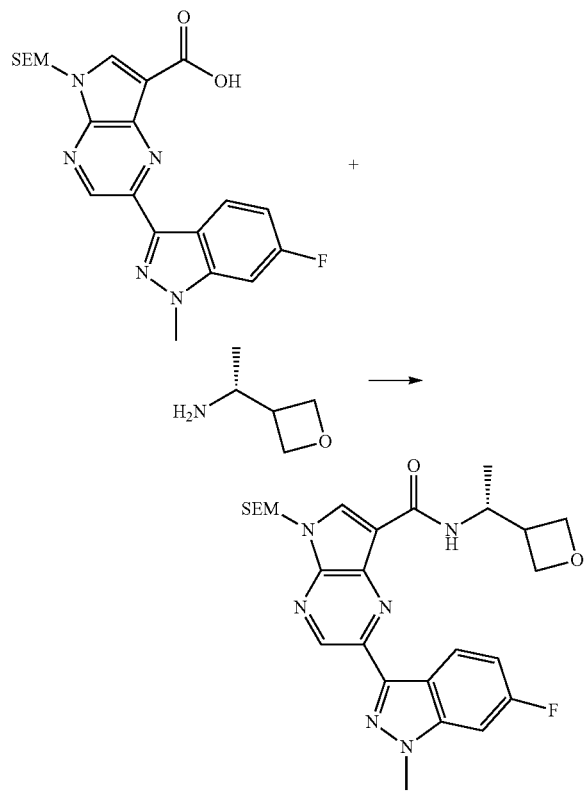

A round-bottomed flask was charged with 2-(6-fluoro-1-methyl-1H-indazol-3-yl)-5-(2-trimethylsilanyl-ethoxymethyl)-5H-pyrrolo[2,3-b]pyrazine-7-carboxylic acid (100 mg, 0.23 mmol) and (R)-1-oxetan-3-yl-ethylamine (120 mg, 0.59 mmol). DMF (1 ml) was added followed by N,N-diisopropylethylamine (0.16 ml, 0.92 mmol) and HATU (95 mg, 0.25 mmol). The yellow reaction mixture was stirred at room temperature overnight then quenched with water and extracted with diethyl ether (2×). The combined organic layers were washed twice with water and once with brine then dried over sodium sulfate, filtered and concentrated. The residue was chromatographed over silica gel with EtOAc/hexanes (gradient: 0-60% EtOAc) to afford 31 mg (26%) of 2-(6-fluoro-1-methyl-1H-indazol-3-yl)-5-(2-trimethylsilanyl-ethoxymethyl)-5H-pyrrolo[2,3-b]pyrazine-7-carboxylic acid ((R)-1-oxetan-3-yl-ethyl)-amide as an off-white solid.

Step 5

2-(6-Fluoro-1-methyl-1H-indazol-3-yl)-5H-pyrrolo[2,3-b]pyrazine-7-carboxylic acid ((R)-1-oxetan-3-yl-ethyl)-amide In a round-bottomed flask, 2-(6-fluoro-1-methyl-1H-indazol-3-yl)-5-(2-trimethylsilanylethoxymethyl)-5H-pyrrolo[2,3-b]pyrazine-7-carboxylic acid ((R)-1-oxetan-3-yl-ethyl)-amide (29 mg, 0.055 mmol) was dissolved in tetrabutylammonium fluoride (1.0 M in THF, 0.56 ml, 0.56 mmol). The light brown reaction mixture was stirred at 70° C. for 4 h then cooled to room temperature, quenched with water and extracted with EtOAc (2×). The combined organic layers were washed with water and brine then dried over sodium sulfate, filtered and concentrated. The residue was chromatographed over silica gel with MeOH/CH$_2$Cl$_2$ (0.5% NH$_4$OH) (gradient: 0-5% MeOH) to afford 14 mg (64%) of 2-(6-fluoro-1-methyl-1H-indazol-3-yl)-5H-pyrrolo[2,3-b]pyrazine-7-carboxylic acid ((R)-1-oxetan-3-yl-ethyl)-amide as a light yellow solid. Optical purity was determined to be 60% ee by chiral HPLC. MS: (M+Na)$^+$=417; $^1$H NMR (DMSO-d$_6$, 400 MHz): δ (ppm) 12.87 (br. s., 1H), 9.10 (s, 1H), 8.46 (s, 1H), 8.42 (dd, J=8.8, 5.3 Hz, 1H), 8.07 (d, J=8.6 Hz, 1H), 7.71 (dd, J=9.9, 1.8 Hz, 1H), 7.25 (td, J=9.1, 2.0 Hz, 1H), 4.69 (dd, J=7.6, 6.1 Hz, 1H), 4.53-4.65 (m, 2H), 4.50 (t, J=6.1 Hz, 1H), 4.42 (t, J=6.3 Hz, 1H), 4.16 (s, 3H), 3.10-3.23 (m, 1H), 1.24 (d, J=6.6 Hz, 3H).

Example 253

2-(6-Fluoro-1-methyl-1H-indazol-3-yl)-5H-pyrrolo[2,3-b]pyrazine-7-carboxylic acid [(S)-1-(3-trifluoromethoxy-phenyl)-ethyl]-amide

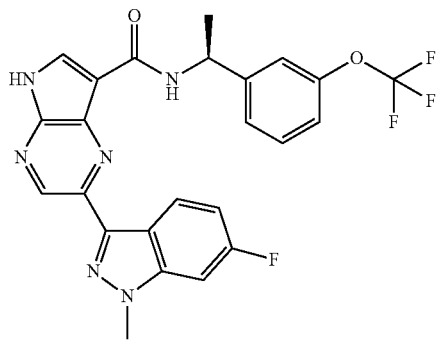 [SMILES: C[C@H](NC(=O)c1c[nH]c2ncc(-c3nn(C)c4cc(F)ccc34)nc12)c1cccc(OC(F)(F)F)c1]

Step 1

(S)-2-Methyl-propane-2-sulfinic acid 1-(3-trifluoromethoxy-phenyl)-meth-(E)-ylideneamide

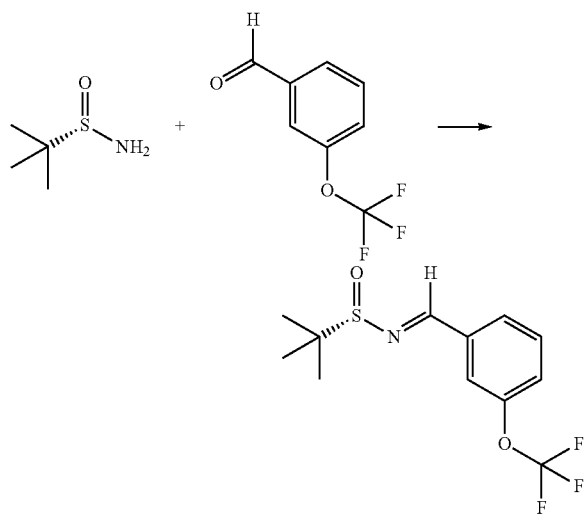

In a 50 ml round-bottomed flask, 3-(trifluoromethoxy)benzaldehyde (400 mg, 2.1 mmol) was dissolved in dichloromethane (12 ml) and (S)-2-methylpropane-2-sulfinamide (281 mg, 2.31 mmol) and anhydrous copper (II) sulfate (739 mg, 4.63 mmol) were added. The reaction mixture was stirred at room temperature overnight then filtered through a glass microfiber filter, rinsing with dichloromethane. The filtrate was concentrated and the residue was chromatographed over silica gel with EtOAc/hexanes (gradient 0-20% EtOAc) to afford 430 mg (70%) of (S)-2-methyl-propane-2-sulfinic acid 1-(3-trifluoromethoxy-phenyl)-meth-(E)-ylideneamide as a light yellow oil.

Step 2

(S)-2-Methyl-propane-2-sulfinic acid [(R)-1-(3-trifluoromethoxy-phenyl)-ethyl]-amide and (S)-2-Methyl-propane-2-sulfinic acid [(S)-1-(3-trifluoromethoxy-phenyl)-ethyl]-amide

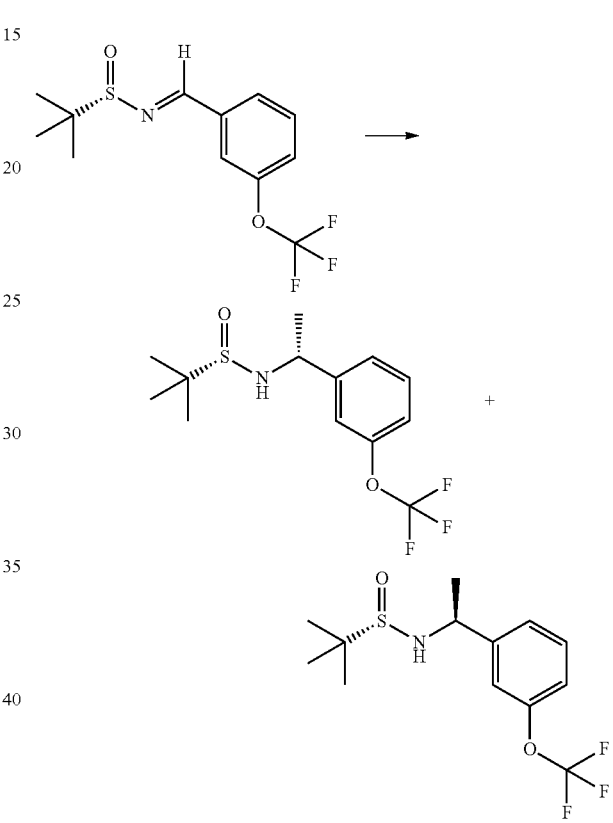

In a round-bottomed flask, (S)-2-methyl-propane-2-sulfinic acid 1-(3-trifluoromethoxyphenyl)-meth-(E)-ylideneamide (424 mg, 1.45 mmol) was dissolved in THF (2.9 ml). The light yellow solution was cooled to −76° C. and methylmagnesium bromide (3.0 M in diethyl ether, 0.86 ml, 2.58 mmol) was added dropwise. The reaction mixture was allowed to warm slowly to room temperature overnight then quenched with saturated aqueous $NH_4Cl$ and extracted with EtOAc (2×). The combined organic layers were washed with water and brine then dried over sodium sulfate, filtered and concentrated. The residue was chromatographed over silica gel with EtOAc/hexanes (gradient: 0-10% EtOAc) to give 225 mg (50%) of (S)-2-methyl-propane-2-sulfinic acid [(R)-1-(3-trifluoromethoxy-phenyl)-ethyl]-amide as a colorless oil. $^1$H NMR (CDCl$_3$, 400 MHz): δ (ppm) 7.33-7.41 (m, 1H), 7.24-7.28 (m, 1H), 7.22 (s, 1H), 7.13 (dd, J=8.1, 1.0 Hz, 1H), 4.62 (q, J=6.7 Hz, 1H), 1.55 (d, J=6.6 Hz, 3H), 1.22 (s, 9H). Also isolated 161 mg (36%) of (S)-2-methyl-propane-2-sulfinic acid [(S)-1-(3-trifluoromethoxy-phenyl)ethyl]-amide as a colorless oil. $^1$H NMR (CDCl$_3$, 400 MHz): δ

(ppm) 7.35-7.43 (m, 1H), 7.28-7.33 (m, 1H), 7.21 (s, 1H), 7.11-7.18 (m, 1H), 4.58 (qd, J=6.4, 2.9 Hz, 1H), 1.53 (d, J=6.6 Hz, 3H), 1.25 (s, 9H).

Step 3

(S)-1-(3-Trifluoromethoxy-phenyl)-ethylamine hydrochloride

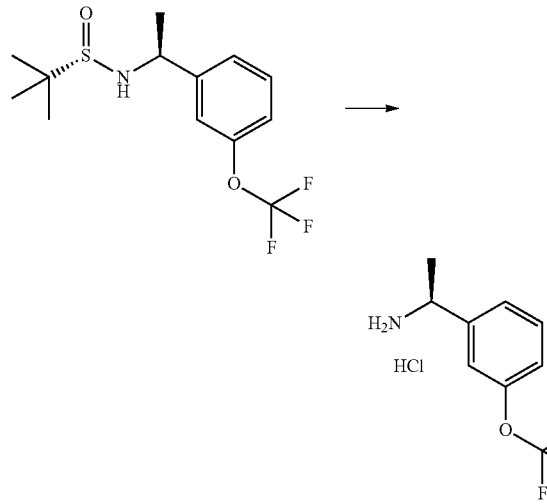

In a 25 ml round-bottomed flask, (S)-2-methyl-propane-2-sulfinic acid [(S)-1-(3-trifluoromethoxy-phenyl)-ethyl]-amide (157 mg, 0.51 mmol) was dissolved in methanol (1 ml) and hydrogen chloride (4.0 M in 1,4-dioxane, 0.26 ml, 1.04 mmol) was added dropwise. The reaction was stirred at room temperature for 20 min then concentrated to give (S)-1-(3-trifluoromethoxy-phenyl)-ethylamine hydrochloride as an off-white waxy solid which was used without further purification.

Step 4

2-(6-Fluoro-1-methyl-1H-indazol-3-yl)-5-(2-trimethylsilanyl-ethoxymethyl)-5H-pyrrolo[2,3-b]pyrazine-7-carboxylic acid [(S)-1-(3-trifluoromethoxy-phenyl)-ethyl]-amide

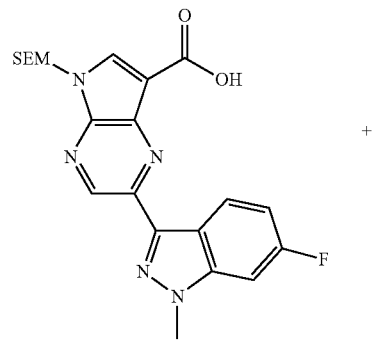

+

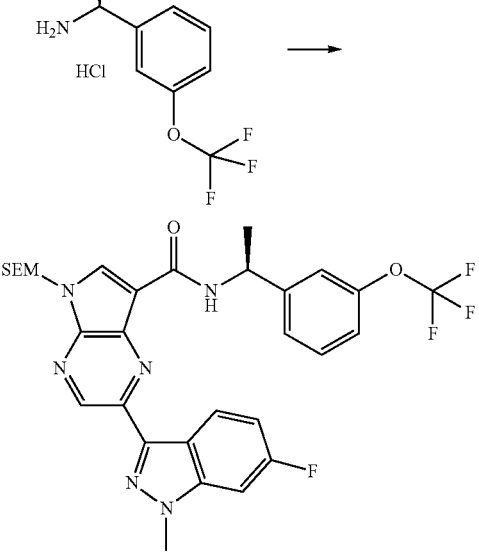

A 10 ml round-bottomed flask was charged with 2-(6-fluoro-1-methyl-1H-indazol-3-yl)-5-(2-trimethylsilanyl-ethoxymethyl)-5H-pyrrolo[2,3-b]pyrazine-7-carboxylic acid (100 mg, 0.23 mmol) and (S)-1-(3-trifluoromethoxy-phenyl)-ethylamine hydrochloride (155 mg, 0.45 mmol). DMF (1.1 ml) was added followed by N,N-diisopropylethylamine (0.28 ml, 1.6 mmol) and HATU (95 mg, 0.25 mmol). The yellow reaction mixture was stirred at room temperature overnight then water and petroleum ether were added. The resulting off-white precipitate was collected by filtration. The filter cake was washed with water and petroleum ether then dried under high vacuum to afford 126 mg (89%) of 2-(6-fluoro-1-methyl-1H-indazol-3-yl)-5-(2-trimethylsilanyl-ethoxymethyl)-5H-pyrrolo[2,3-b]pyrazine-7-carboxylic acid [(S)-1-(3-trifluoromethoxy-phenyl)-ethyl]-amide as an off-white powder.

Step 5

2-(6-Fluoro-1-methyl-1H-indazol-3-yl)-5H-pyrrolo[2,3-b]pyrazine-7-carboxylic acid [(S)-1-(3-trifluoromethoxy-phenyl)-ethyl]-amide

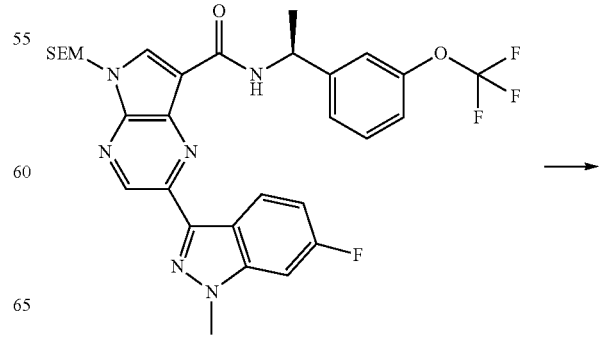

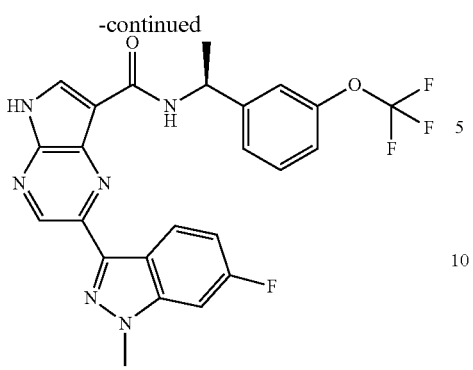

In a 10 ml round-bottomed flask, 2-(6-fluoro-1-methyl-1H-indazol-3-yl)-5-(2-trimethylsilanyl-ethoxymethyl)-5H-pyrrolo[2,3-b]pyrazine-7-carboxylic acid [(S)-1-(3-trifluoromethoxy-phenyl)-ethyl]-amide (123 mg, 0.196 mmol) was dissolved in dichloromethane (1 ml) and trifluoroacetic acid (0.6 ml, 7.9 mmol) was added. The light yellow reaction was stirred at room temperature for 2 h then concentrated. The residue was dissolved in dichloromethane (1 ml) and ethylenediamine (0.80 ml, 11.8 mmol) was added. The yellow reaction mixture was stirred at room temperature for 1 h then quenched with water and diluted with ethyl acetate. The resulting suspension was filtered and washed with hot water and ethyl acetate and the solid collected was dried under high vacuum to provide 56 mg (57%) of 2-(6-fluoro-1-methyl-1H-indazol-3-yl)-5H-pyrrolo[2,3-b]pyrazine-7-carboxylic acid [(S)-1-(3-trifluoromethoxy-phenyl)-ethyl]-amide as a light yellow powder. MS: $(M+Na)^+=521$; $^1H$ NMR (DMSO-$d_6$, 400 MHz): δ (ppm) 12.85 (br. s., 1H), 9.11 (s, 1H), 8.53 (d, J=7.8 Hz, 1H), 8.45 (s, 1H), 8.36 (dd, J=9.2, 5.2 Hz, 1H), 7.67 (dd, J=9.7, 1.9 Hz, 1H), 7.39-7.54 (m, 3H), 7.24 (d, J=7.1 Hz, 1H), 6.98 (td, J=9.0, 2.1 Hz, 1H), 5.27-5.43 (m, 1H), 4.14 (s, 3H), 1.65 (d, J=7.1 Hz, 3H).

Example 254

2-(6-Fluoro-1-methyl-1H-indazol-3-yl)-5H-pyrrolo[2,3-b]pyrazine-7-carboxylic acid [(R)-1-(3-trifluoromethoxy-phenyl)-ethyl]-amide

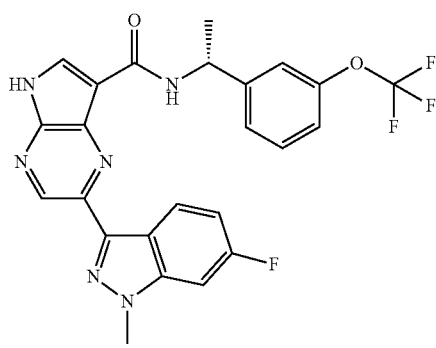 [SMILES: C[C@@H](NC(=O)c1c[nH]c2ncc(-c3nn(C)c4cc(F)ccc34)nc12)c1cccc(OC(F)(F)F)c1]

Prepared according to the procedure outlined in Example 253, Steps 3-5, substituting (S)-2-methyl-propane-2-sulfinic acid [(R)-1-(3-trifluoromethoxy-phenyl)-ethyl]-amide for (S)-2-methyl-propane-2-sulfinic acid [(S)-1-(3-trifluoromethoxy-phenyl)-ethyl]-amide in Step 3. MS: $(M+Na)^+=521$; $^1H$ NMR (DMSO-$d_6$, 400 MHz): δ (ppm) 12.85 (br. s, 1H), 9.11 (s, 1H), 8.54 (d, J=7.8 Hz, 1H), 8.45 (s, 1H), 8.37 (dd, J=8.6, 5.6 Hz, 1H), 7.67 (dd, J=9.9, 2.0 Hz, 1H), 7.39-7.54 (m, 3H), 7.24 (d, J=7.1 Hz, 1H), 6.98 (td, J=9.0, 2.1 Hz, 1H), 5.28-5.42 (m, 1H), 4.15 (s, 3H), 1.66 (d, J=7.1 Hz, 3H).

Example 255

2-(6-Fluoro-1-methyl-1H-indazol-3-yl)-5H-pyrrolo[2,3-b]pyrazine-7-carboxylic acid [1-(1-hydroxy-1-methyl-ethyl)-cyclobutyl]-amide

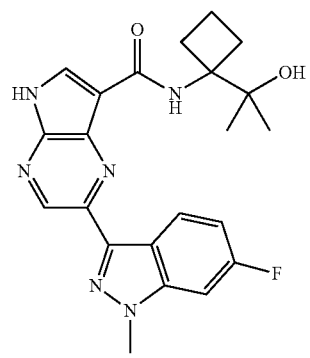 [SMILES: Cn1nc(-c2cnc3[nH]cc(C(=O)NC4(C(C)(C)O)CCC4)c3n2)c2ccc(F)cc21]

Step 1

1-tert-Butoxycarbonylamino-cyclobutanecarboxylic acid ethyl ester

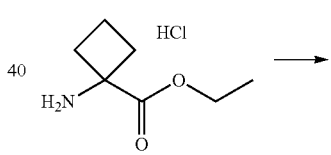

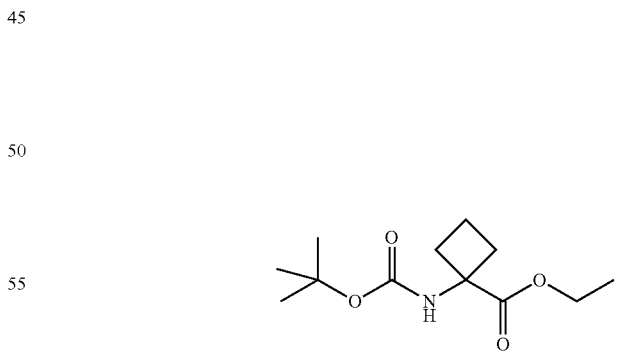

To a solution of ethyl 1-amino-1-cyclobutane-carboxylate hydrochloride (1.20 g, 6.67 mmol) in DMF (13 mL) was added di-tert-butyldicarbonate (1.61 g, 7.35 mmol). Triethylamine (1.12 mL, 8.04 mmol) was added dropwise and the reaction mixture was stirred at room temperature for 3.5 h then water and diethyl ether were added. The aqueous layer was extracted with diethyl ether. The combined organic layers were washed with 1.0 M HCl, water and brine then dried over Na$_2$SO$_4$ and concentrated to afford 1.58 g (97%) of 1-tert-butoxycarbonylamino-cyclobutanecarboxylic acid ethyl ester as an off-white solid.

Step 2

[1-(1-Hydroxy-1-methyl-ethyl)-cyclobutyl]-carbamic acid tert-butyl ester

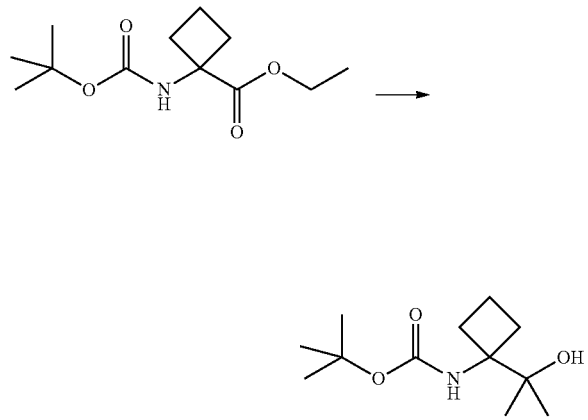

In a 100 mL 3-neck round-bottomed flask 1-tert-butoxycarbonylamino-cyclobutanecarboxylic acid ethyl ester (700 mg, 3.05 mmol) was dissolved in THF (22 mL). The solution was cooled to 0° C. and methylmagnesium bromide (3.0 M in Et$_2$O, 4.0 mL, 12.0 mmol) was added dropwise over 15 min. The reaction mixture was allowed to warm slowly to room temperature overnight. The reaction mixture was cooled to 0° C. and quenched with saturated aqueous NH$_4$Cl, then diluted with 1.0 M aqueous HCl and extracted with EtOAc (2×). The combined organics were washed with H$_2$O and brine then dried over Na$_2$SO$_4$ and concentrated. The residue was purified by chromatography over 24 g of SiO$_2$ using EtOAc/hexanes (gradient: 0-20% EtOAc) to provide 492 mg (70%) of [1-(1-hydroxy-1-methyl-ethyl)-cyclobutyl]-carbamic acid tert-butyl ester as a pale yellow oil.

Step 3

2-(1-Amino-cyclobutyl)-propan-2-ol trifluoroacetate

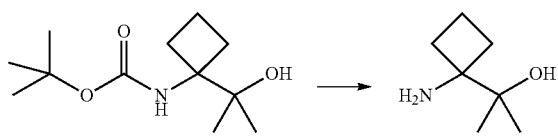

In a 25 ml round-bottomed flask, [1-(1-hydroxy-1-methyl-ethyl)-cyclobutyl]-carbamic acid tert-butyl ester (150 mg, 0.65 mmol) was dissolved in dichloromethane (3.8 ml) and trifluoroacetic acid (1.5 ml, 19.5 mmol) was slowly added. The pale yellow reaction mixture was stirred at room temperature for 2.5 h then concentrated to give 2-(1-amino-cyclobutyl)-propan-2-ol trifluoroacetate as a light brown oil which was used without further purification.

Step 4

2-(6-Fluoro-1-methyl-1H-indazol-3-yl)-5-(2-trimethylsilanyl-ethoxymethyl)-5H-pyrrolo[2,3-b]pyrazine-7-carboxylic acid [1-(1-hydroxy-1-methyl-ethyl)-cyclobutyl]-amide In a round-bottomed flask, 2-(1-amino-cyclobutyl)-propan-2-ol trifluoroacetate (214 mg, 0.62 mmol) was dissolved in DMF (1.2 ml) and N,N-diisopropylethylamine (0.44 ml, 2.52 mmol). Then 2-(6-fluoro-1-methyl-1H-indazol-3-yl)-5-(2-trimethylsilanyl-ethoxymethyl)-5H-pyrrolo[2,3-b]pyrazine-7-carboxylic acid (110 mg, 0.25 mmol) and HATU (104 mg, 0.27 mmol) were added. The yellow reaction mixture was stirred at room temperature overnight then water and petroleum ether were added. The resulting precipitate was collected by filtration. The filter cake was washed with water and petroleum ether then dried under high vacuum to afford 142 mg (98%) of 2-(6-fluoro-1-methyl-1H-indazol-3-yl)-5-(2-trimethylsilanyl-ethoxymethyl)-5H-pyrrolo[2,3-b]pyrazine- 7-carboxylic acid [1-(1-hydroxy-1-methyl-ethyl)-cyclobutyl]-amide as an off-white powder.

Step 5

2-(6-Fluoro-1-methyl-1H-indazol-3-yl)-5H-pyrrolo[2,3-b]pyrazine-7-carboxylic acid [1-(1-hydroxy-1-methyl-ethyl)-cyclobutyl]-amide

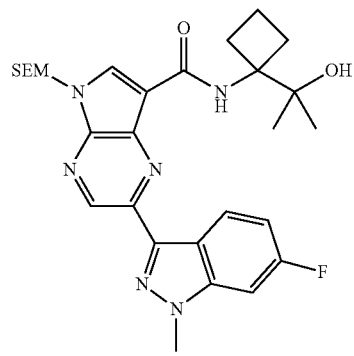
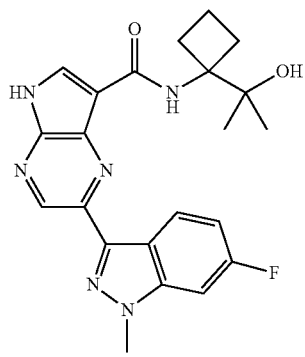

In a 10 ml round-bottomed flask, 2-(6-fluoro-1-methyl-1H-indazol-3-yl)-5-(2-trimethylsilanyl-ethoxymethyl)-5H-pyrrolo[2,3-b]pyrazine-7-carboxylic acid [1-(1-hydroxy-1-methyl-ethyl)-cyclobutyl]-amide (140 mg, 0.24 mmol) was dissolved in dichloromethane (1.2 ml) and trifluoroacetic acid (0.75 ml, 9.7 mmol) was added. The orange reaction mixture was stirred at room temperature for 3 h then concentrated. The residue was dissolved in dichloromethane (1.2 ml) and ethylenediamine (1.0 ml, 14.8 mmol) was added. The reaction was stirred at room temperature for 1 h then quenched with water and diluted with ethyl acetate. The resulting suspension was filtered and washed with hot water and ethyl acetate then dried under high vacuum to provide 67 mg (63%) of 2-(6-fluoro-1-methyl-1H-indazol-3-yl)-5H-pyrrolo[2,3-b]pyrazine-7-carboxylic acid [1-(1-hydroxy-1-methyl-ethyl)-cyclobutyl]-amide as a light yellow powder. MS: (M+Na)$^+$= 445; $^1$H NMR (DMSO-d$_6$, 300 MHz): δ (ppm) 9.11 (s, 1H), 8.53 (dd, J=8.9, 5.5 Hz, 1H), 8.41 (s, 1H), 8.31 (s, 1H), 7.68 (dd, J=9.8, 2.3 Hz, 1H), 7.08-7.23 (m, 1H), 4.99 (br. s., 1H), 4.15 (s, 3H), 2.38-2.62 (m, 4H), 1.84-2.02 (m, 1H), 1.66-1.83 (m, 1H), 1.23 (s, 6H).

Example 256

2-(6-Fluoro-1-methyl-1H-indazol-3-yl)-5H-pyrrolo[2,3-b]pyrazine-7-carboxylic acid (1-hydroxymethyl-cyclobutyl)-amide

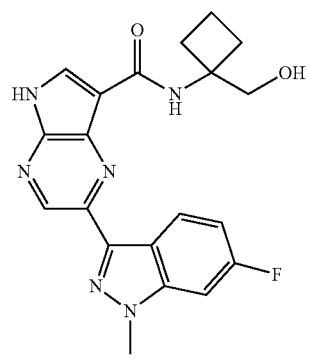 [SMILES: Cn1nc(-c2cnc3[nH]cc(C(=O)NC4(CO)CCC4)c3n2)c2ccc(F)cc21]

Step 1

(1-Hydroxymethyl-cyclobutyl)-carbamic acid tert-butyl ester

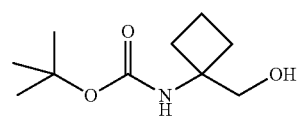

In a 15 ml round-bottomed flask, 1-tert-butoxycarbonylamino-cyclobutanecarboxylic acid ethyl ester (180 mg, 0.74 mmol) was dissolved in THF (4 ml). The colorless solution was cooled to 0° C. and lithium aluminum hydride (1.0 M in THF, 0.78 ml, 0.78 mmol) was added dropwise. The reaction mixture was stirred at 0° C. for 1.5 h then sodium sulfate decahydrate was carefully added. When gas evolution has ceased, the ice bath was removed, sodium sulfate was added and the mixture was stirred for 30 min at room temperature. The suspension was filtered over Celite and rinsed with ethyl acetate/methanol. The filtrate was concentrated to give (1-hydroxymethyl-cyclobutyl)-carbamic acid tert-butyl ester as an off-white waxy solid which was used without further purification.

Step 2

2-(6-Fluoro-1-methyl-1H-indazol-3-yl)-5H-pyrrolo[2,3-b]pyrazine-7-carboxylic acid (1-hydroxymethyl-cyclobutyl)-amide

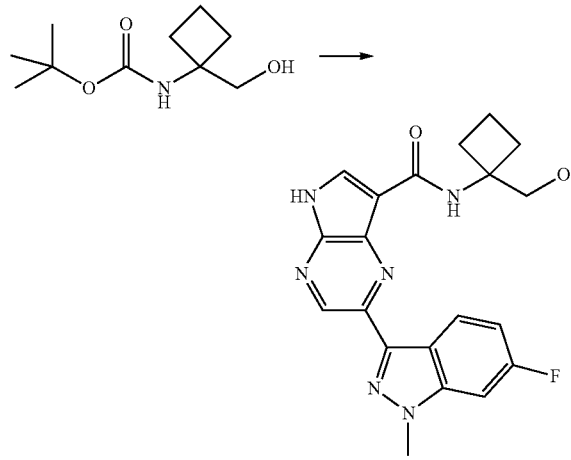

Prepared according to the procedure outlined in Example 255, Steps 3-5, substituting (1-hydroxymethyl-cyclobutyl)-carbamic acid tert-butyl ester for [1-(1-hydroxy-1-methyl-ethyl)cyclobutyl]-carbamic acid tert-butyl ester in Step 3. MS: (M+Na)$^+$=417. $^1$H NMR (DMSO-d$_6$, 400 MHz): δ (ppm) 9.09 (s, 1H), 8.56 (dd, J=9.0, 5.2 Hz, 1H), 8.37 (s, 1H), 8.31 (s, 1H), 7.66 (dd, J=9.9, 2.0 Hz, 1H), 7.14 (td, J=9.1, 2.3 Hz, 1H), 5.10 (br. s., 1H), 4.14 (s, 3H), 3.75 (s, 2H), 2.34-2.45 (m, 2H), 2.16-2.27 (m, 2H), 1.80-1.98 (m, 2H).

Example 257

2-(6-Fluoro-1-piperidin-4-yl-1H-indazol-3-yl)-5H-pyrrolo[2,3-b]pyrazine-7-carboxylic acid tert-butylamide

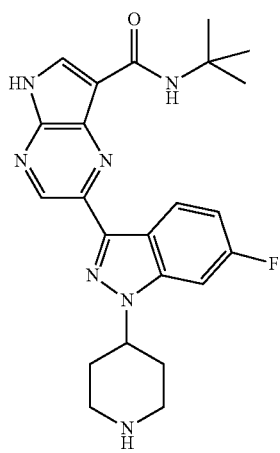 [SMILES: CC(C)(C)NC(=O)c1c[nH]c2ncc(-c3nn(C4CCNCC4)c4cc(F)ccc34)nc12]

Step 1

4-{6-Fluoro-3-[7-formyl-5-(2-trimethylsilanyl-ethoxymethyl)-5H-pyrrolo[2,3-b]pyrazin-2-yl]-indazol-1-yl}-piperidine-1-carboxylic acid tert-butyl ester

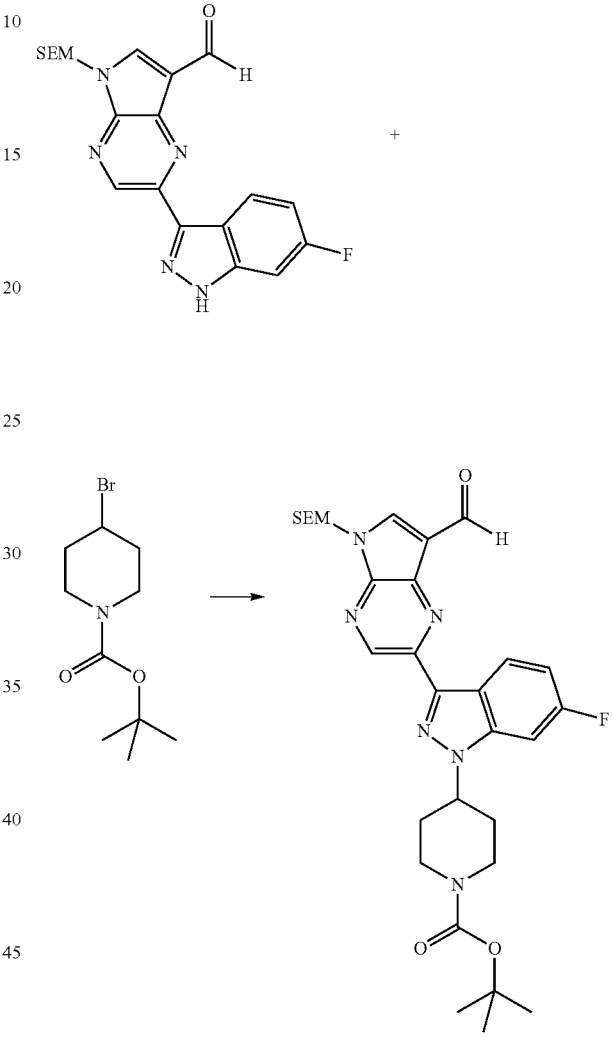

A microwave vial was charged with 2-(6-fluoro-1H-indazol-3-yl)-5-(2-trimethylsilanylethoxymethyl)-5H-pyrrolo[2,3-b]pyrazine-7-carbaldehyde (182 mg, 0.44 mmol), tert-butyl 4-bromopiperidine-1-carboxylate (234 mg, 0.89 mmol), cesium carbonate (432 mg, 1.33 mmol) and DMF (2 ml). The vial was flushed with argon, sealed, and heated in a microwave reactor at 100° C. for 2 h. The reaction was quenched with water and extracted with diethyl ether (2×). The combined organic layers were washed twice with water and once with brine then dried over sodium sulfate, filtered and concentrated. The residue was chromatographed over silica gel with EtOAc/hexanes (gradient: 0-30% EtOAc to give 108 mg (41%) of 4-{6-fluoro-3-[7-formyl-5-(2-trimethylsilanylethoxymethyl)-5H-pyrrolo[2,3-b]pyrazin-2-yl]-indazol-1-yl}-piperidine-1-carboxylic acid tert-butyl ester as a light brown solid.

Step 2

2-[1-(1-tert-Butoxycarbonyl-piperidin-4-yl)-6-fluoro-1H-indazol-3-yl]-5-(2-trimethylsilanylethoxymethyl)-5H-pyrrolo[2,3-b]pyrazine-7-carboxylic acid

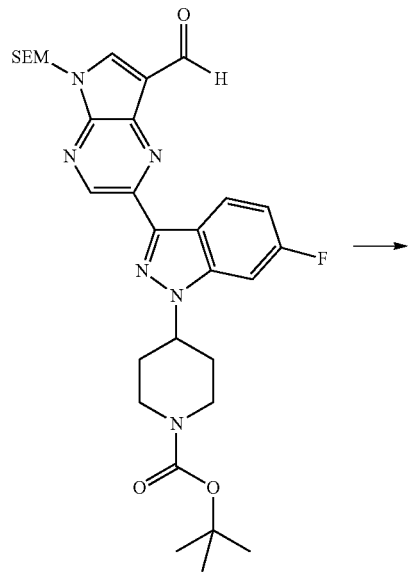

In a 50 ml round-bottomed flask, 4-{6-fluoro-3-[7-formyl-5-(2-trimethylsilanylethoxymethyl)-5H-pyrrolo[2,3-b]pyrazin-2-yl]-indazol-1-yl}-piperidine-1-carboxylic acid tert-butyl ester (190 mg, 0.32 mmol) was dissolved in THF (7 ml) and water (1.4 ml). The light yellow solution was cooled to 0° C. and sulfamic acid (186 mg, 1.92 mmol) was added. Then, a solution of sodium chlorite (80%, 50 mg, 0.44 mmol) and potassium dihydrogen phosphate (522 mg, 3.83 mmol) in water (4.2 ml) was added dropwise via pipette. After the addition was complete, the ice bath was removed and the reaction mixture was stirred at room temperature for 1.5 h. The reaction was diluted with water and extracted with EtOAc (2×). The combined organic layers were washed with water and brine then dried over sodium sulfate, filtered and concentrated. The residue was triturated with hexanes to afford 176 mg (90%) of 2-[1-(1-tertbutoxycarbonyl-piperidin-4-yl)-6-fluoro-1H-indazol-3-yl]-5-(2-trimethylsilanylethoxymethyl)-5H-pyrrolo[2,3-b]pyrazine-7-carboxylic acid as a light yellow powder.

Step 3

2-[1-(1-tert-Butoxycarbonyl-piperidin-4-yl)-6-fluoro-1H-indazol-3-yl]-5-(2-trimethylsilanylethoxymethyl)-5H-pyrrolo[2,3-b]pyrazine-7-carboxylic acid tert-butylamide

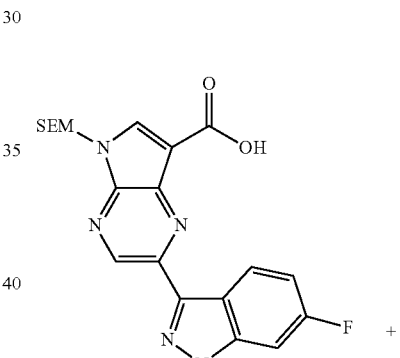

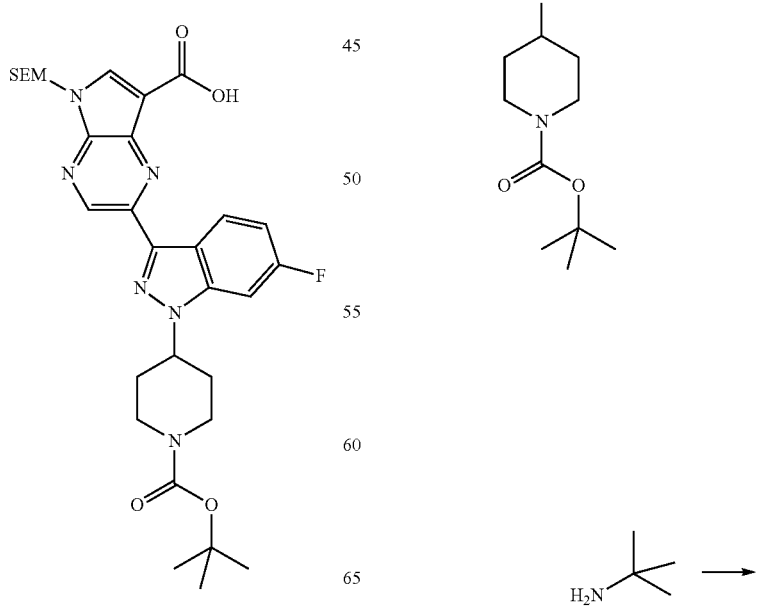

-continued

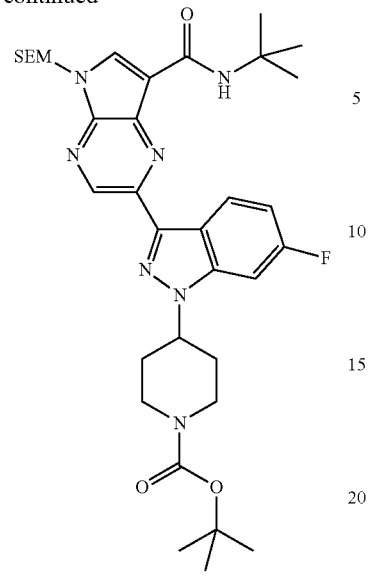

In a 10 ml round-bottomed flask, 2-[1-(1-tert-butoxycarbonyl-piperidin-4-yl)-6-fluoro-1H-indazol-3-yl]-5-(2-trimethylsilanyl-ethoxymethyl)-5H-pyrrolo[2,3-b]pyrazine-7-carboxylic acid (85 mg, 0.14 mmol) was dissolved in DMF (1.5 ml) and tert-butylamine (0.06 ml, 0.57 mmol) and HATU (59 mg, 0.155 mmol) were added. The light yellow suspension was stirred at room temperature overnight then water and petroleum ether were added. The resulting suspension was filtered. The filter cake was washed with water and petroleum ether then dried under high vacuum. The residue was chromatographed over 8 g silica gel with EtOAc/hexanes (gradient: 0-30% EtOAc) to afford 47 mg (51%) of 2-[1-(1-tert-butoxycarbonyl-piperidin-4-yl)-6-fluoro-1H-indazol-3-yl]-5-(2-trimethylsilanyl-ethoxymethyl)-5H-pyrrolo[2,3-b]pyrazine-7-carboxylic acid tert-butylamide as an off-white solid.

Step 4

2-(6-Fluoro-1-piperidin-4-yl-1H-indazol-3-yl)-5H-pyrrolo[2,3-b]pyrazine-7-carboxylic acid tert-butylamide

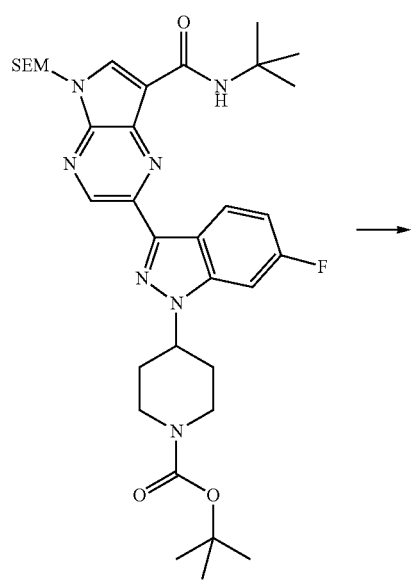

-continued

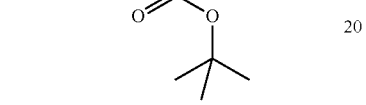

In a 10 ml round-bottomed flask, 2-[1-(1-tert-butoxycarbonyl-piperidin-4-yl)-6-fluoro-1H-indazol-3-yl]-5-(2-trimethylsilanyl-ethoxymethyl)-5H-pyrrolo[2,3-b]pyrazine-7-carboxylic acid tert-butylamide (46 mg, 0.069 mmol) was dissolved in dichloromethane (0.4 ml) and trifluoroacetic acid (0.22 ml, 2.86 mmol) was added. The reaction mixture was stirred at room temperature for 2 h then concentrated. The residue was suspended in dichloromethane (0.4 ml) and ethylenediamine (0.28 ml, 4.15 mmol) was added. The light yellow suspension was stirred at room temperature for 1 h then quenched with water and diluted with ethyl acetate. The suspension was filtered and washed with hot water and ethyl acetate then dried under high vacuum to provide 27 mg (85%) of 2-(6-fluoro-1-piperidin-4-yl-1H-indazol-3-yl)-5H-pyrrolo[2,3-b]pyrazine-7-carboxylic acid tert-butylamide as a light yellow powder. MS: (M+H)$^+$=436; $^1$H NMR (DMSO-d$_6$, 300 MHz): δ (ppm) 9.08 (s, 1H), 8.47 (dd, J=8.9, 5.5 Hz, 1H), 8.39 (s, 1H), 7.96 (s, 1H), 7.77-7.85 (m, 1H), 7.10-7.22 (m, 1H), 4.70-4.88 (m, 1H), 3.13 (d, J=12.1 Hz, 2H), 2.67-2.81 (m, 2H), 2.01-2.20 (m, 2H), 1.88-2.01 (m, 2H), 1.52 (s, 9H).

Example 258

2-(6-Fluoro-1-pyrrolidin-3-yl-1H-indazol-3-yl)-5H-pyrrolo[2,3-b]pyrazine-7-carboxylic acid tert-butylamide

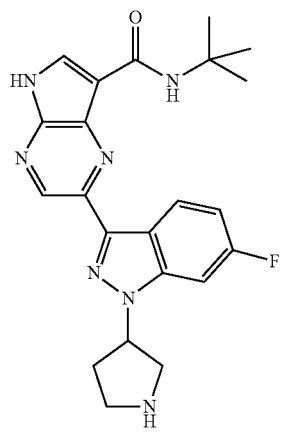 [SMILES: CC(C)(C)NC(=O)c1c[nH]c2ncc(-c3nn(C4CCNC4)c4cc(F)ccc34)nc12]

Step 1

3-Methanesulfonyloxy-pyrrolidine-1-carboxylic acid tert-butyl ester

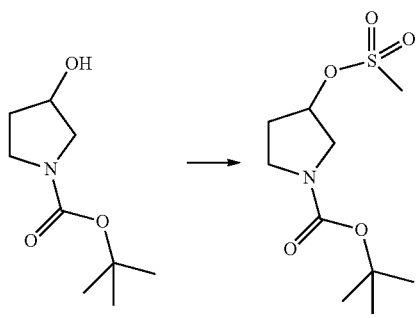 [SMILES: CC(C)(C)OC(=O)N1CCC(O)C1 ; CC(C)(C)OC(=O)N1CCC(OS(C)(=O)=O)C1]

In a 50 ml round-bottomed flask, 3-hydroxypyrrolidine-1-carboxylic acid tert-butyl ester (300 mg, 1.6 mmol) was dissolved in dichloromethane 912 ml). The colorless solution was cooled to 0° C. and triethylamine (0.34 ml, 2.44 mmol) and methanesulfonyl chloride (0.14 ml, 1.8 mmol) were added. The reaction mixture was stirred at 0° C. for 1.5 h then quenched with water and extracted with dichloromethane (2×). The organic layers were combined, dried over sodium sulfate, filtered and concentrated to give 3-methanesulfonyloxy-pyrrolidine-1-carboxylic acid tert-butyl ester as a yellow oil which was used without further purification.

Step 2

2-(6-Fluoro-1-pyrrolidin-3-yl-1H-indazol-3-yl)-5H-pyrrolo[2,3-b]pyrazine-7-carboxylic acid tert-butylamide

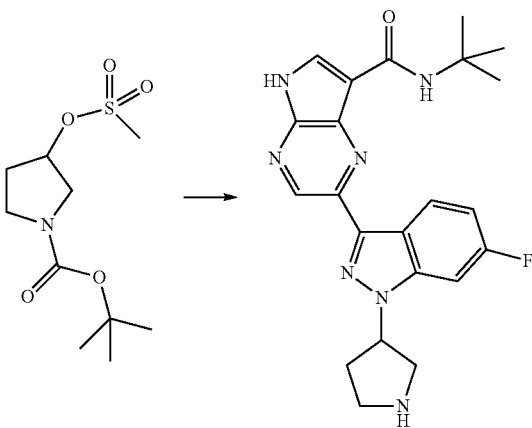 [SMILES: CC(C)(C)OC(=O)N1CCC(OS(C)(=O)=O)C1 ; CC(C)(C)NC(=O)c1c[nH]c2ncc(-c3nn(C4CCNC4)c4cc(F)ccc34)nc12]

Prepared according to the procedure outlined in Example 257, substituting 3-methanesulfonyloxy-pyrrolidine-1-carboxylic acid tert-butyl ester for tert-butyl 4-bromopiperidine-1-carboxylate in Step 1. MS: (M+H)$^+$=422. $^1$H NMR (DMSO-d$_6$, 300 MHz): δ (ppm) 9.11 (s, 1H), 8.46 (dd, J=8.9, 5.5 Hz, 1H), 8.37 (s, 1H), 7.94 (s, 1H), 7.78 (dd, J=10.2, 1.9 Hz, 1H), 7.15 (td, J=9.1, 1.9 Hz, 1H), 5.25-5.42 (m, 1H), 3.10-3.31 (m, 3H), 2.88-3.01 (m, 1H), 2.12-2.38 (m, 2H), 1.51 (s, 9H).

Example 259

2-(1-Methyl-1H-pyrazolo[4,3-b]pyridin-3-yl)-5H-pyrrolo[2,3-b]pyrazine-7-carboxylic acid tert-butylamide

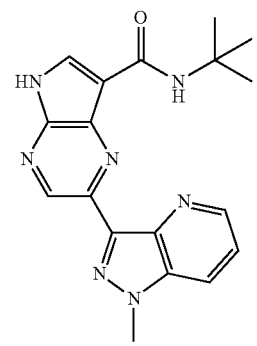 [SMILES: Cn1nc(-c2cnc3[nH]cc(C(=O)NC(C)(C)C)c3n2)c2ncccc21]

Step 1

2-Bromo-5-(2-trimethylsilanyl-ethoxymethyl)-5H-pyrrolo[2,3-b]pyrazine-7-carboxylic acid tert-butylamide

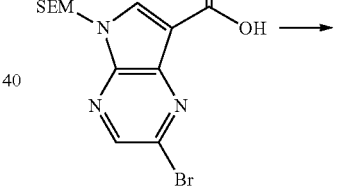

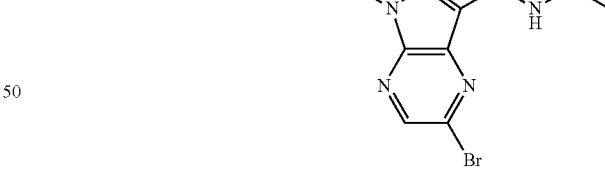

In a 100 ml round-bottomed flask, 2-bromo-5-(2-trimethylsilanyl-ethoxymethyl)-5H-pyrrolo[2,3-b]pyrazine-7-carboxylic acid (1.00 g, 2.69 mmol) was dissolved in DMF (6 ml). tert-Butylamine (1.7 ml, 16.2 mmol) was added followed by HATU (1.12 g, 2.95 mmol). The yellow suspension was stirred at room temperature for 72 h then quenched with water and extracted with a mixture of diethyl ether and EtOAc. The organic layers were washed twice with water and once with brine then combined, dried over sodium sulfate, filtered and concentrated. The residue was triturated with petroleum ether to afford 989 mg (86%) of 2-bromo-5-(2-trimethylsilanylethoxymethyl)-5H-pyrrolo[2,3-b]pyrazine-7-carboxylic acid tert-butylamide as an off-white powder. $^1$H NMR (CDCl₃, 300 MHz): δ (ppm) 8.40 (s, 1H), 8.31 (s, 1H), 7.86 (s, 1H), 5.65 (s, 2H), 3.46-3.58 (m, 2H), 1.54 (s, 9H), 0.84-0.98 (m, 2H), −0.04 (s, 9H).

Step 2

2-(1-Methyl-1H-pyrazolo[4,3-b]pyridin-3-yl)-5-(2-trimethylsilanyl-ethoxymethyl)-5H-pyrrolo[2,3-b]pyrazine-7-carboxylic acid tert-butylamide

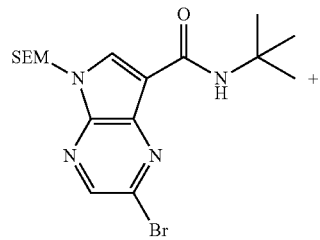

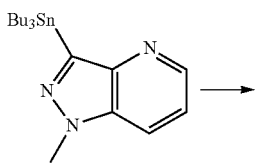

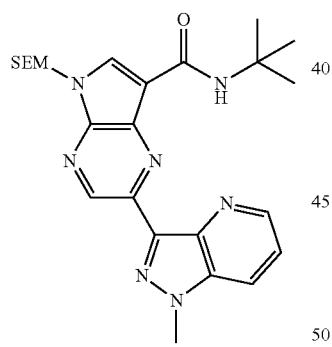

In a round-bottomed flask, 2-bromo-5-(2-trimethylsilanyl-ethoxymethyl)-5H-pyrrolo[2,3-b]pyrazine-7-carboxylic acid tert-butylamide (110 mg, 0.26 mmol) and 1-methyl-3-tributylstannyl-1H-pyrazolo[4,3-b]pyridine (see Example 98, 340 mg, 0.40 mmol) were dissolved in DMF (2.4 ml). The reaction mixture was evacuated and backfilled with argon then tetrakis(triphenylphosphine)palladium (0) (15 mg, 0.013 mmol) and copper (I) iodide (10 mg, 0.053 mmol) were added. The reaction mixture was stirred at 80° C. overnight then cooled to room temperature, quenched with water and extracted with diethyl ether (2×). The combined organic layers were washed twice with water and once with brine then dried over sodium sulfate, filtered and concentrated. The residue was chromatographed over 12 g silica gel with EtOAc/hexanes (gradient: 0-70% EtOAc) to afford 51 mg (41%) of 2-(1-methyl-1H-pyrazolo[4,3-b]pyridin-3-yl)-5-(2-trimethylsilanyl-ethoxymethyl)-5H-pyrrolo[2,3-b]pyrazine-7-carboxylic acid tert-butylamide as a light yellow solid.

Step 3

2-(1-Methyl-1H-pyrazolo[4,3-b]pyridin-3-yl)-5H-pyrrolo[2,3-b]pyrazine-7-carboxylic acid tert-butylamide

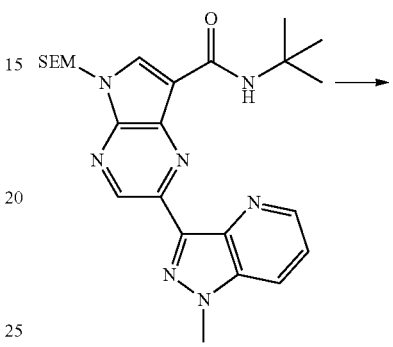

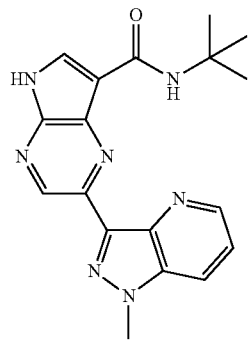

In a 10 ml round-bottomed flask, 2-(1-methyl-1H-pyrazolo[4,3-b]pyridin-3-yl)-5-(2-trimethylsilanyl-ethoxymethyl)-5H-pyrrolo[2,3-b]pyrazine-7-carboxylic acid tert-butylamide (49 mg, 0.102 mmol) was dissolved in dichloromethane (0.6 ml) and trifluoroacetic acid (0.32 ml, 4.15 mmol) was added. The yellow reaction mixture was stirred at room temperature for 2 h then concentrated. The residue was dissolved in dichloromethane (0.6 ml) and ethylenediamine (0.42 ml, 6.22 mmol) was added. The yellow solution was stirred at room temperature for 1 h then quenched with water and diluted with ethyl acetate. The resulting suspension was filtered and washed with hot water and ethyl acetate and the product dried under high vacuum to provide 23 mg (64%) of 2-(1-methyl-1H-pyrazolo[4,3-b]pyridin-3-yl)-5H-pyrrolo[2,3-b]pyrazine-7-carboxylic acid tert-butylamide as a light yellow powder. MS: (M+H)⁺=350; ¹H NMR (DMSO-d₆, 400 MHz): δ (ppm) 12.58 (br. s., 1H), 9.34 (s, 1H), 8.69 (s, 1H), 8.65 (dd, J=4.3, 1.3 Hz, 1H), 8.34 (s, 1H), 8.27 (dd, J=8.6, 1.3 Hz, 1H), 7.52 (dd, J=8.6, 4.3 Hz, 1H), 4.21 (s, 3H), 1.53 (s, 9H).

Example 260

2-(5-Cyano-1-methyl-1H-indazol-3-yl)-5H-pyrrolo[2,3-b]pyrazine-7-carboxylic acid tert-butylamide

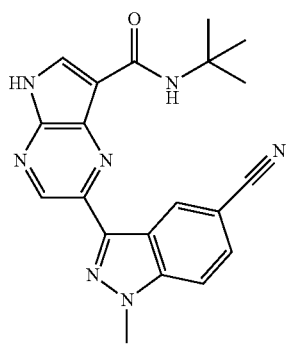 [SMILES: Cn1nc(-c2cnc3[nH]cc(C(=O)NC(C)(C)C)c3n2)c2cc(C#N)ccc21]

Step 1

3-Iodo-1H-indazole-5-carbonitrile

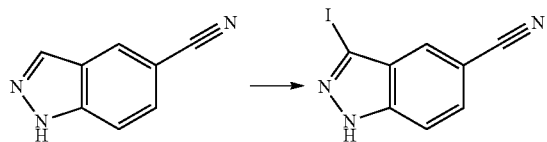 [SMILES: N#Cc1ccc2[nH]ncc2c1 ; N#Cc1ccc2[nH]nc(I)c2c1]

In a 25 ml round-bottomed flask, 1H-indazole-5-carbonitrile (400 mg, 2.79 mmol) was dissolved in DMF (7 ml). Potassium hydroxide (607 mg, 10.8 mmol) was added followed by iodine (1.42 g, 5.59 mmol). The dark brown suspension was stirred at room temperature for 3 h then was quenched with 10% aqueous NaHSO₃ and extracted with diethyl ether (2×). The combined organic layers were washed twice with water and once with brine then dried over sodium sulfate, filtered and concentrated to give 396 mg (53%) of 3-iodo-1H-indazole-5-carbonitrile as a light yellow powder.

Step 2

3-Iodo-1-methyl-1H-indazole-5-carbonitrile

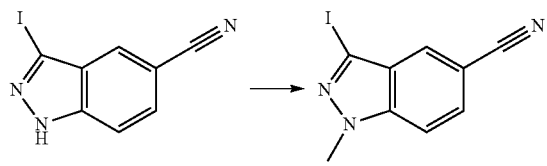

In a round-bottomed flask, 3-iodo-1H-indazole-5-carbonitrile (391 mg, 1.45 mmol) was dissolved in THF (5.3 ml). The light yellow solution was cooled to 0° C. and potassium tert-butoxide (230 mg, 2.05 mmol) was added. The reaction mixture was stirred at 0° C. for 30 min then iodomethane (0.12 ml, 1.92 mmol) was added dropwise. After the addition was complete, the ice bath was removed and the reaction mixture was stirred at room temperature for 1.5 h. The reaction was quenched with water and extracted with EtOAc (2×). The combined organic layers were washed with water and brine then dried over sodium sulfate, filtered and concentrated to give 384 mg (93%) of a light yellow solid. NMR analysis of the crude product showed an approximate 5:1 mixture of 3-iodo-1-methyl-1H-indazole-5-carbonitrile (major) and 3-iodo-2-methyl-2H-indazole-5-carbonitrile (minor). The mixture was used without further purification.

Step 3

1-Methyl-3-tributylstannanyl-1H-indazole-5-carbonitrile

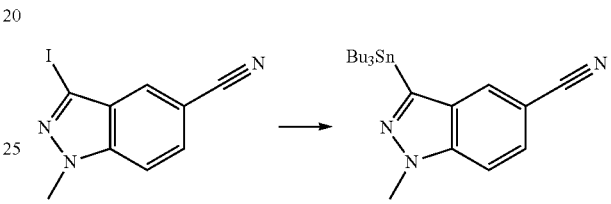

In a round-bottomed flask, 3-iodo-1-methyl-1H-indazole-5-carbonitrile (383 mg, 1.35 mmol) was partially dissolved in THF (10 ml). The light yellow suspension was cooled to −16° C. (NaCl/ice bath) and isopropylmagnesium chloride (2.0 M in THF, 0.82 ml, 1.64 mmol) was added dropwise. The reaction mixture was stirred at −16° C. for 30 min then tributylchlorostannane (0.43 ml, 1.59 mmol) was slowly added. The reaction mixture was allowed to warm to room temperature and stirred for 1.5 h then quenched with saturated aqueous NH₄Cl and extracted with EtOAc (2×). The combined organic layers were washed with water and brine then dried over sodium sulfate, filtered and concentrated to provide 1-methyl-3-tributylstannanyl-1H-indazole-5-carbonitrile as a brown oil which was used without further purification.

Step 4

2-(5-Cyano-1-methyl-1H-indazol-3-yl)-5-(2-trimethylsilanyl-ethoxymethyl)-5H-pyrrolo[2,3-b]pyrazine-7-carboxylic acid tert-butylamide

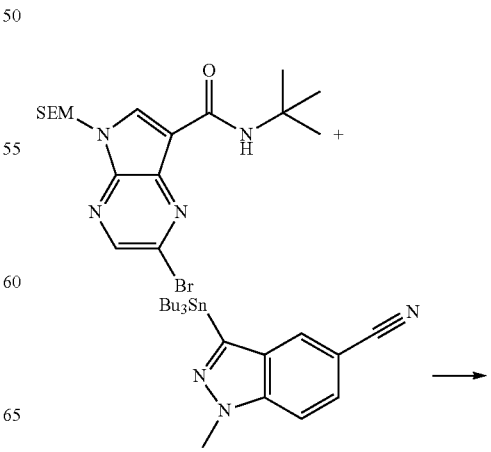

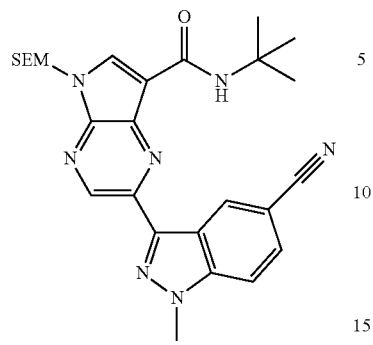

In a 50 ml round-bottomed flask, 2-bromo-5-(2-trimethyl-silanyl-ethoxymethyl)-5H-pyrrolo[2,3-b]pyrazine-7-carboxylic acid tert-butylamide (300 mg, 0.70 mmol) and 1-methyl-3-tributylstannyl-1H-indazole-5-carbonitrile (crude from Step 3, 847 mg, 1.14 mmol) were dissolved in DMF (6.6 ml). The reaction mixture was evacuated and backfilled with argon then tetrakis(triphenylphosphine)palladium (0) (41 mg, 0.036 mmol) and copper (I) iodide (27 mg, 0.14 mmol) were added. The reaction mixture was stirred at 80° C. overnight then cooled to room temperature and water and diethyl ether were added. The resulting brown precipitate was collected via filtration washing with water and diethyl ether. The brown powder was absorbed on silica gel and chromatographed with MeOH/CH$_2$Cl$_2$/0.5% NH$_4$OH (gradient: 0-2% MeOH) to afford 254 mg (72%) of 2-(5-cyano-1-methyl-1H-indazol-3-yl)-5-(2-trimethylsilanylethoxymethyl)-5H-pyrrolo[2,3-b]pyrazine-7-carboxylic acid tert-butylamide as a light yellow solid.

Step 5

2-(5-Cyano-1-methyl-1H-indazol-3-yl)-5H-pyrrolo[2,3-b]pyrazine-7-carboxylic acid tert-butylamide

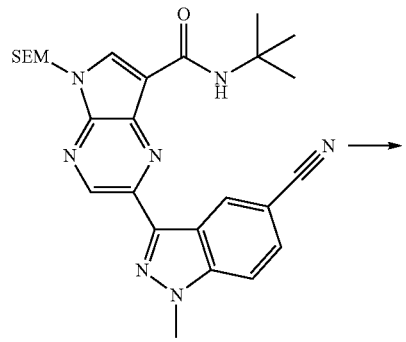

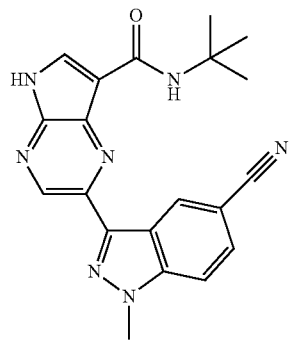

In a round-bottomed flask, 2-(5-cyano-1-methyl-1H-indazol-3-yl)-5-(2-trimethylsilanylethoxymethyl)-5H-pyrrolo[2,3-b]pyrazine-7-carboxylic acid tert-butylamide (80 mg, 0.16 mmol) was dissolved in dichloromethane (0.8 ml) and trifluoroacetic acid (0.5 ml, 6.4 mmol) was added. The reaction mixture was stirred at room temperature for 2 h then concentrated. The residue was suspended in dichloromethane (0.8 ml) and ethylenediamine (0.65 ml, 9.63 mmol) was added. The light yellow suspension was stirred at room temperature for 1 h then water and ethyl acetate were added. The suspension was filtered and washed with hot water and ethyl acetate. The product collected was dried under high vacuum to provide 43 mg (73%) of 2-(5-cyano-1-methyl-1H-indazol-3-yl)-5H-pyrrolo[2,3-b]pyrazine-7-carboxylic acid tert-butylamide as a yellow powder. MS: (M+Na)$^+$=396; $^1$H NMR (DMSO-d$_6$, 300 MHz): δ (ppm) 12.48 (br. s., 1H), 9.10 (s, 1H), 8.87 (s, 1H), 8.41 (s, 1H), 7.93-8.05 (m, 1H), 7.78-7.90 (m, 2H), 4.23 (s, 3H), 1.54 (s, 9H).

Example 261

2-(5-Difluoromethoxy-1-piperidin-4-yl-1H-indazol-3-yl)-5H-pyrrolo[2,3-b]pyrazine-7-carboxylic acid tert-butylamide

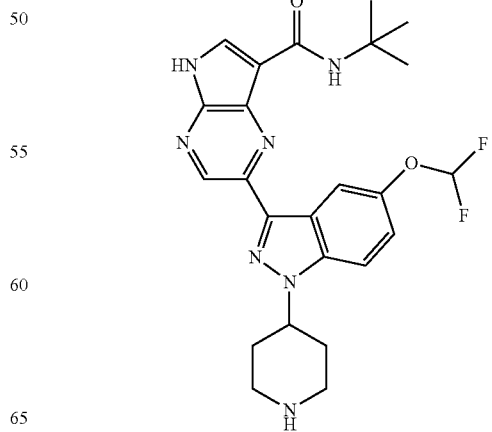

Step 1

5-Difluoromethoxy-3-tributylstannanyl-1H-indazole

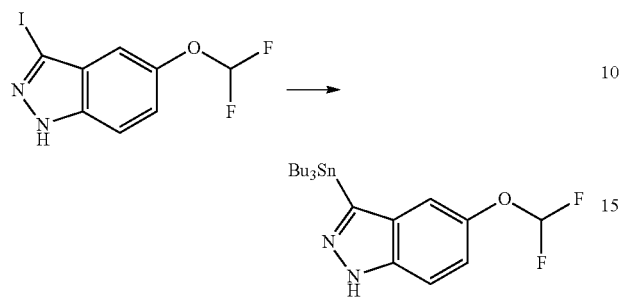

In a round-bottomed flask, 5-difluoromethoxy-3-iodo-1H-indazole (200 mg, 0.6 mmol) was dissolved in THF (3.6 ml) and sodium hydride (60% in mineral oil, 64 mg, 1.6 mmol) was added. The reaction mixture was stirred at room temperature for 10 min then cooled to −16° C. (NaCl/ice bath) and isopropylmagnesium chloride (2.0 M in THF, 0.46 ml, 0.920 mmol) was added dropwise. The reaction mixture was stirred at −16° C. for 30 min then tributylchlorostannane (0.22 ml, 0.81 mmol) was slowly added. The reaction mixture was allowed to warm to room temperature and stirred for 1 h then quenched with saturated NH$_4$Cl— solution and extracted with EtOAc (2×). The combined organic layers were washed with water and brine then dried over sodium sulfate, filtered and concentrated to give 5-difluoromethoxy-3-tributylstannanyl-1H-indazole as a yellow oil which was used without further purification.

Step 2

2-(5-Difluoromethoxy-1H-indazol-3-yl)-5-(2-trimethylsilanyl-ethoxymethyl)-5H-pyrrolo[2,3-b]pyrazine-7-carboxylic acid tert-butylamide

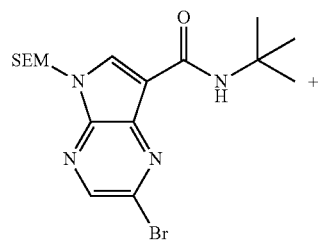

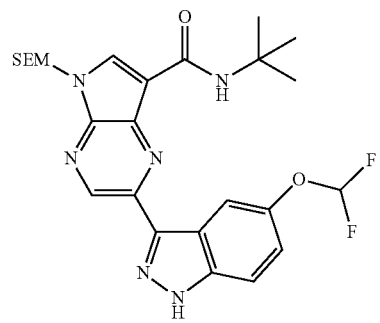

In a round-bottomed flask, 2-bromo-5-(2-trimethylsilanyl-ethoxymethyl)-5H-pyrrolo[2,3-b]pyrazine-7-carboxylic acid tert-butylamide (200 mg, 0.47 mmol) and 5-difluoromethoxy-3-tributylstannyl-1H-indazole (crude from Step 1, 509 mg, 0.59 mmol) were dissolved in DMF (3.2 ml). The reaction mixture was evacuated and backfilled with argon then tetrakis(triphenylphosphine)palladium (0) (27.0 mg, 0.023 mmol) and copper (I) iodide (18 mg, 0.095 mmol) were added. The reaction mixture was stirred at 90° C. for 2 h then cooled to room temperature, quenched with water and extracted with ethyl acetate/diethyl ether (2×). The combined organic layers were washed three times with water and once with brine then concentrated. The residue was absorbed on silica gel and chromatographed with EtOAc/dichloromethane (gradient: 0-30% EtOAc). The appropriate fractions were combined and concentrated and the residue was triturated with diethyl ether to afford 158 mg (64%) of 2-(5-difluoromethoxy-1H-indazol-3-yl)-5-(2-trimethylsilanyl-ethoxymethyl)-5H-pyrrolo[2,3-b]pyrazine-7-carboxylic acid tert-butylamide as an off-white powder.

Step 3

4-{3-[7-tert-Butylcarbamoyl-5-(2-trimethylsilanyl-ethoxymethyl)-5H-pyrrolo[2,3-b]pyrazin-2-yl]-5-difluoromethoxy-indazol-1-yl}-piperidine-1-carboxylic acid tert-butyl ester

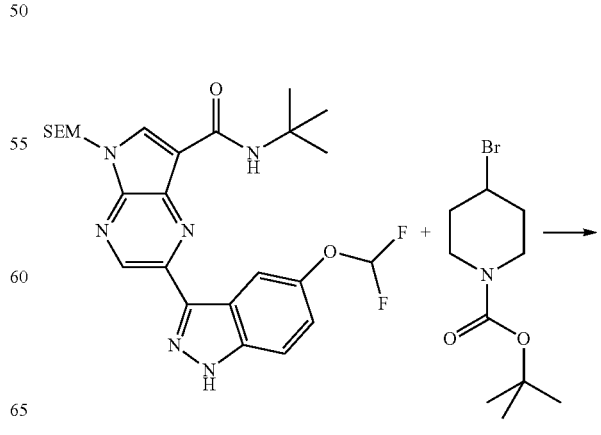

867
-continued

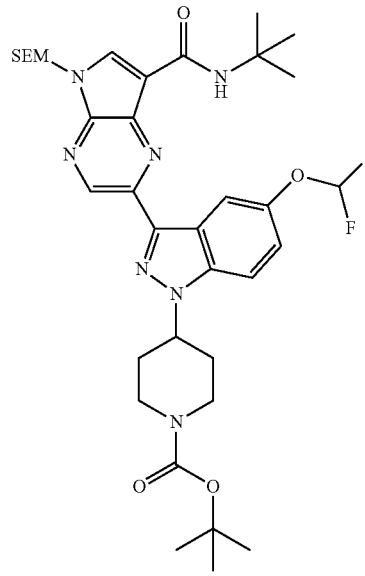

A pressure tube was charged with 2-(5-difluoromethoxy-1H-indazol-3-yl)-5-(2-trimethylsilanyl-ethoxymethyl)-5H-pyrrolo[2,3-b]pyrazine-7-carboxylic acid tert-butylamide (180 mg, 0.34 mmol), tert-butyl 4-bromopiperidine-1-carboxylate (179 mg, 0.68 mmol), cesium carbonate (332 mg, 1.02 mmol) and DMF (1.5 ml). The tube was flushed with argon, sealed and stirred at 100° C. in an oil bath overnight. The reaction was cooled to room temperature and additional tert-butyl 4-bromopiperidine-1-carboxylate (179 mg, 0.68 mmol) and cesium carbonate (332 mg, 1.02 mmol) were added. The tube was again flushed with argon, sealed and stirred at 100° C. in an oil bath for 6 h. The reaction mixture was cooled to room temperature, quenched with water and extracted with diethyl ether (2×). The combined organic layers were washed twice with water and once with brine then dried over sodium sulfate, filtered and concentrated. The residue was chromatographed over 25 g silica gel with EtOAc/hexanes (gradient: 0-30% EtOAc) to afford 197 mg (81%) of 4-{3-[7-tert-butylcarbamoyl-5-(2-trimethylsilanyl-ethoxymethyl)-5H-pyrrolo[2,3-b]pyrazin-2-yl]-5-difluoromethoxy-indazol-1-yl}-piperidine-1-carboxylic acid tert-butyl ester as an off-white solid.

868

Step 4

2-(5-Difluoromethoxy-1-piperidin-4-yl-1H-indazol-3-yl)-5H-pyrrolo[2,3-b]pyrazine-7-

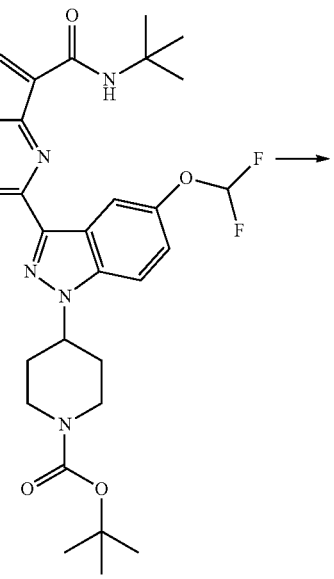

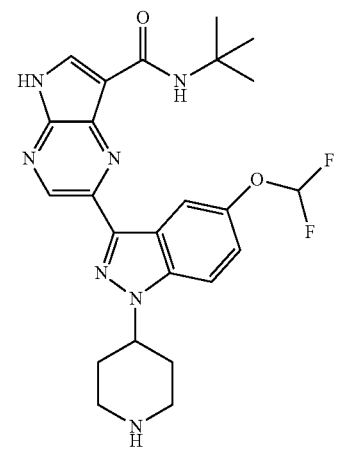 [SMILES: CC(C)(C)NC(=O)c1c[nH]c2ncc(-c3nn(C4CCNCC4)c4ccc(OC(F)F)cc34)nc12]

In a round-bottomed flask, 4-{3-[7-tert-butylcarbamoyl-5-(2-trimethylsilanylethoxymethyl)-5H-pyrrolo[2,3-b]pyrazin-2-yl]-5-difluoromethoxy-indazol-1-yl}-piperidine-1-carboxylic acid tert-butyl ester (65 mg, 0.091 mmol) was dissolved in dichloromethane (0.5 ml) and trifluoroacetic acid (0.28 ml, 3.63 mmol) was added. The reaction mixture was stirred at room temperature for 2 h then concentrated. The residue was dissolved in dichloromethane (0.5 ml) and ethylenediamine (0.37 ml, 5.48 mmol) was added. The reaction was stirred at room temperature for 1 h then water and ethyl acetate were added. The resulting suspension was filtered and washed with hot water and ethyl acetate. The product collected was dried under high vacuum to provide 37 mg (80%) of 2-(5-difluoromethoxy-1-piperidin-4-yl-1H-indazol-3-yl)-5H-pyrrolo[2,3-b]pyrazine-7-carboxylic acid tert-butylamide as an off-white powder. MS: (M+H)$^+$=484; $^1$H NMR (DMSO-d$_6$, 300 MHz): δ (ppm) 9.06 (s, 1H), 8.37 (s, 1H), 8.19 (d, J=2.3 Hz, 1H), 7.96 (d, J=9.1 Hz, 1H), 7.89 (s, 1H), 7.38 (dd, J=9.1, 2.3 Hz, 1H), 7.18 (t, J=74.8 Hz, 1H), 4.73-4.93 (m, 1H), 3.12 (d, J=12.8 Hz, 2H), 2.63-2.81 (m, 2H), 2.01-2.19 (m, 2H), 1.89-2.01 (m, 2H), 1.49 (s, 9H).

Example 262

4-[3-(7-tert-Butylcarbamoyl-5H-pyrrolo[2,3-b]pyrazin-2-yl)-5-difluoromethoxy-indazol-1-yl]-butyric acid

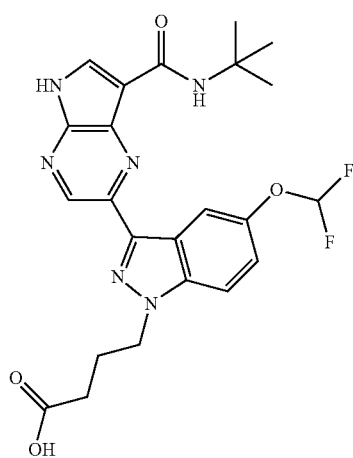 [SMILES: CC(C)(C)NC(=O)c1c[nH]c2ncc(-c3nn(CCCC(=O)O)c4ccc(OC(F)F)cc34)nc12]

Step 1

4-{3-[7-tert-Butylcarbamoyl-5-(2-trimethylsilanyl-ethoxymethyl)-5H-pyrrolo[2,3-b]pyrazin-2-yl]-5-difluoromethoxy-indazol-1-yl}-butyric acid methyl ester

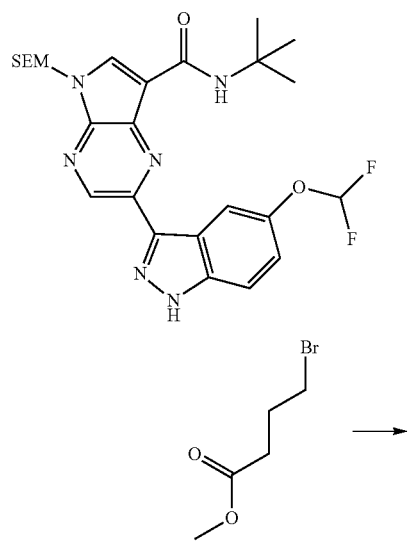

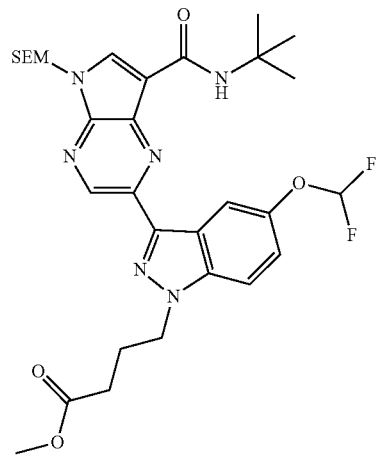

A microwave vial was charged with 2-(5-difluoromethoxy-1H-indazol-3-yl)-5-(2-trimethylsilanyl-ethoxymethyl)-5H-pyrrolo[2,3-b]pyrazine-7-carboxylic acid tert-butylamide (100 mg, 0.19 mmol), methyl 4-bromobutanoate (69 mg, 0.38 mmol), cesium carbonate (184 mg, 0.57 mmol) and DMF (0.85 ml). The vial was flushed with argon, sealed and heated in a microwave reactor at 100° C. for 2 h. The reaction was quenched with water and extracted with diethyl ether (2×). The combined organic layers were washed twice with water and once with brine then dried over sodium sulfate, filtered and concentrated. The residue was chromatographed over 12 g silica gel with EtOAc/hexanes (gradient: 0-30% EtOAc) to afford 99 mg (83%) of 4-{3-[7-tert-butylcarbamoyl-5-(2-trimethylsilanyl-ethoxymethyl)-5H-pyrrolo[2,3-b]pyrazin-2-yl]-5-difluoromethoxy-indazol-1-yl}-butyric acid methyl ester as a light yellow solid.

Step 2

4-{3-[7-tert-Butylcarbamoyl-5-(2-trimethylsilanyl-ethoxymethyl)-5H-pyrrolo[2,3-b]pyrazin-2-yl]-5-difluoromethoxy-indazol-1-yl}-butyric acid

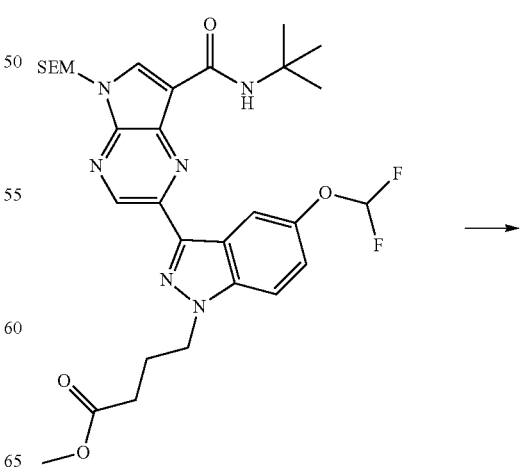

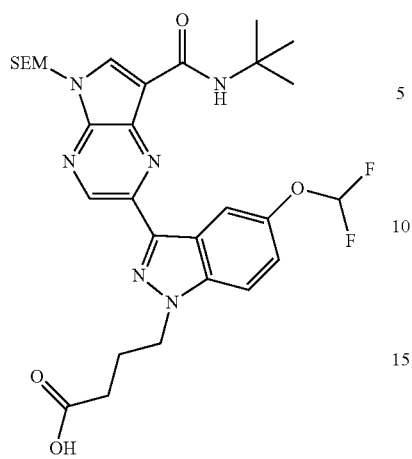

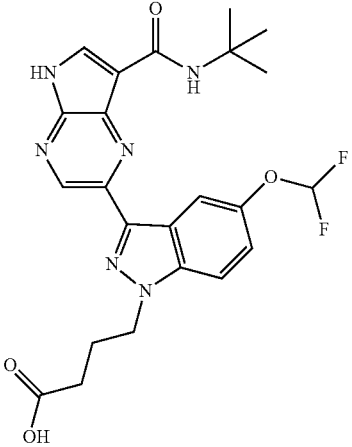

In a round-bottomed flask, 4-{3-[7-tert-butylcarbamoyl-5-(2-trimethylsilanylethoxymethyl)-5H-pyrrolo[2,3-b]pyrazin-2-yl]-5-difluoromethoxy-indazol-1-yl}-butyric acid methyl ester (98 mg, 0.155 mmol) was suspended in THF (1.1 ml), methanol (1.1 ml) and water (1.1 ml). Then, aqueous 1.0 M lithium hydroxide (0.80 ml, 0.80 mmol) was added. The light yellow suspension was stirred at 75° C. for 8 h then cooled to room temperature and stirred overnight. The reaction was diluted with water and acidified with 1 M HCl until pH=~2 then extracted with dichloromethane (3×). The organic layers were combined, dried over sodium sulfate, filtered and concentrated. The residue was triturated with diethyl ether to afford 81 mg (85%) of 4-{3-[7-tert-butylcarbamoyl-5-(2-trimethylsilanyl-ethoxymethyl)-5H-pyrrolo[2,3-b]pyrazin-2-yl]-5-difluoromethoxy-indazol-1-yl}-butyric acid as a brown powder.

Step 3

4-[3-(7-tert-Butylcarbamoyl-5H-pyrrolo[2,3-b]pyrazin-2-yl)-5-difluoromethoxy-indazol-1-yl]-butyric acid In a round-bottomed flask, 4-{3-[7-tert-butylcarbamoyl-5-(2-trimethylsilanylethoxymethyl)-5H-pyrrolo[2,3-b]pyrazin-2-yl]-5-difluoromethoxy-indazol-1-yl}-butyric acid (80 mg, 0.13 mmol) was dissolved in dichloromethane (0.7 ml) and trifluoroacetic acid (0.40 ml, 5.2 mmol) was added. The reaction mixture was stirred at room temperature for 2 h then concentrated. The residue was dissolved in dichloromethane (0.7 ml) and ethylenediamine (0.53 ml, 7.85 mmol) was added. The reaction was stirred at room temperature for 1 h then diluted with water and acidified with 1 M HCl then conc. HCl to pH=~4. The resulting suspension was filtered and washed with hot water and ethyl acetate and the product was dried under high vacuum to provide 27 mg (41%) of 4-[3-(7-tert-butylcarbamoyl-5H-pyrrolo[2,3-b]pyrazin-2-yl)-5-difluoromethoxy-indazol-1-yl]-butyric acid as a brown powder. MS: $(M+Na)^+$=509; $^1$H NMR (DMSO-$d_6$, 400 MHz): δ (ppm) 9.09 (s, 1H), 8.39 (s, 1H), 8.22 (d, J=2.0 Hz, 1H), 7.86-7.92 (m, 2H), 7.42 (dd, J=9.1, 2.3 Hz, 1H), 7.21 (t, J=74.3 Hz, 1H), 4.59 (t, J=6.8 Hz, 2H), 2.26-2.33 (m, 2H), 2.08-2.19 (m, 2H), 1.51 (s, 9H).

Example 263

2-[5-Difluoromethoxy-1-(1-methyl-piperidin-4-yl)-1H-indazol-3-yl]-5H-pyrrolo[2,3-b]pyrazine-7-carboxylic acid tert-butylamide

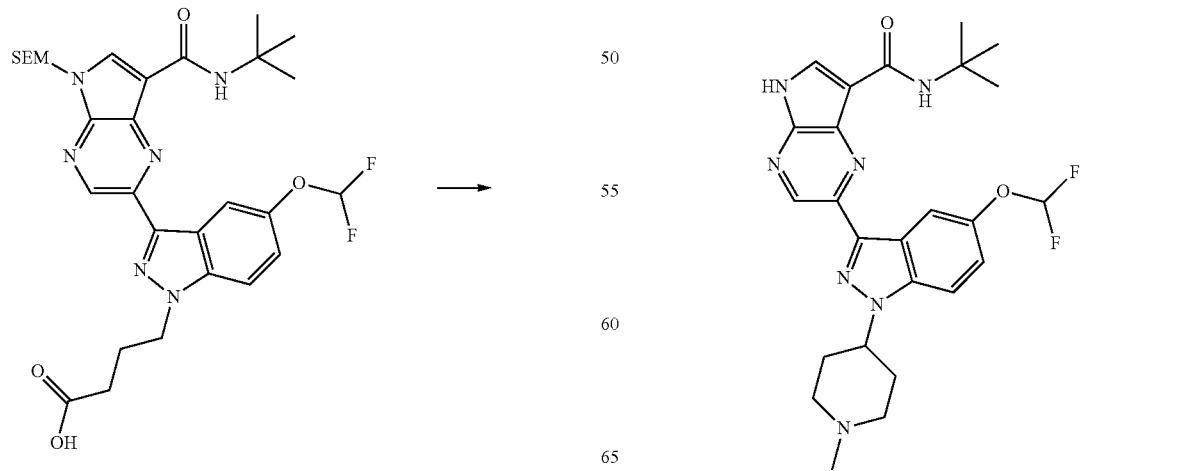

Step 1

2-(5-Difluoromethoxy-1-piperidin-4-yl-1H-indazol-3-yl)-5-(2-trimethylsilanyl-ethoxymethyl)-5H-pyrrolo[2,3-b]pyrazine-7-carboxylic acid tert-butylamide hydrochloride

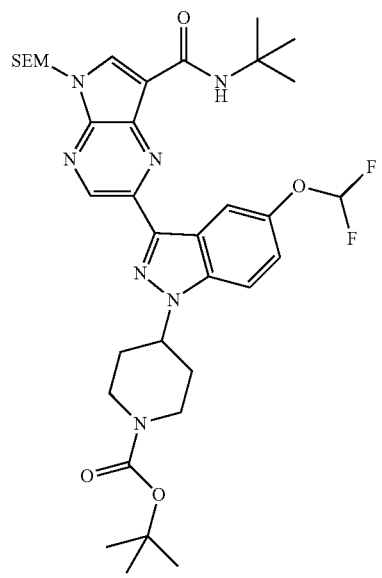

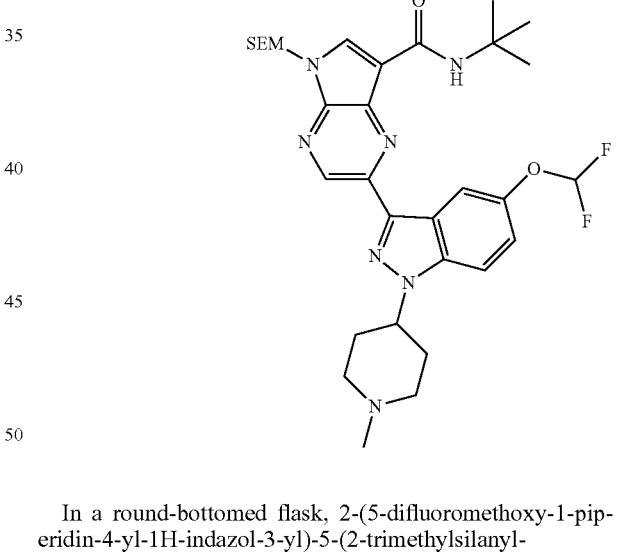

In a round-bottomed flask, 4-{3-[7-tert-butylcarbamoyl-5-(2-trimethylsilanylethoxymethyl)-5H-pyrrolo[2,3-b]pyrazin-2-yl]-5-difluoromethoxy-indazol-1-yl}-piperidine-1-carboxylic acid tert-butyl ester (102 mg, 0.143 mmol) was suspended in methanol (1.4 ml). The suspension was cooled to 0° C. and acetyl chloride (0.20 ml, 2.81 mmol) was added dropwise. After the addition was complete, the ice bath was removed and the reaction mixture was stirred at room temperature for 1.5 h. The solvent was evaporated at room temperature and the residue dried under high vacuum to afford 92 mg (99%) of 2-(5-difluoromethoxy-1-piperidin-4-yl-1H-indazol-3-yl)-5-(2-trimethylsilanyl-ethoxymethyl)-5H-pyrrolo[2,3-b]pyrazine-7-carboxylic acid tert-butylamide hydrochloride as a yellow solid which was used without further purification.

Step 2

2-[5-Difluoromethoxy-1-(1-methyl-piperidin-4-yl)-1H-indazol-3-yl]-5-(2-trimethylsilanylethoxymethyl)-5H-pyrrolo[2,3-b]pyrazine-7-carboxylic acid tert-butylamide

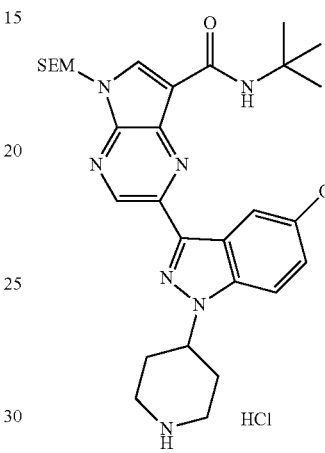

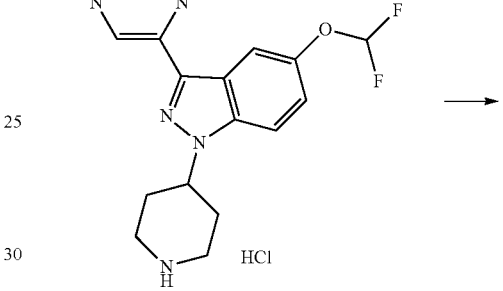

In a round-bottomed flask, 2-(5-difluoromethoxy-1-piperidin-4-yl-1H-indazol-3-yl)-5-(2-trimethylsilanyl-ethoxymethyl)-5H-pyrrolo[2,3-b]pyrazine-7-carboxylic acid tert-butylamide hydrochloride (91 mg, 0.14 mmol) was suspended in 1,2-dichloroethane (1.5 ml) and triethylamine (0.03 ml, 0.22 mmol) was added. The mixture was stirred room temperature for 10 min then formaldehyde (37% aqueous solution, 13 μl, 0.175 mmol) and sodium triacetoxyborohydride (119 mg, 0.56 mmol) were added. The yellow suspension was stirred at room temperature for 1.5 h then quenched with saturated aqueous NaHCO$_3$ and extracted with dichloromethane (3×). The organic layers were combined, dried over sodium sulfate, filtered and concentrated to afford 2-[5-difluoromethoxy-1-(1-methyl-piperidin-4-yl)-1H-indazol-3-yl]-5-(2-trimethylsilanyl-ethoxymethyl)-5H- pyrrolo[2,3-b]pyrazine-7-carboxylic acid tert-butylamide as a yellow foam which was used without further purification.

Step 3

2-[5-Difluoromethoxy-1-(1-methyl-piperidin-4-yl)-1H-indazol-3-yl]-5H-pyrrolo[2,3-b]pyrazine-7-carboxylic acid tert-butylamide

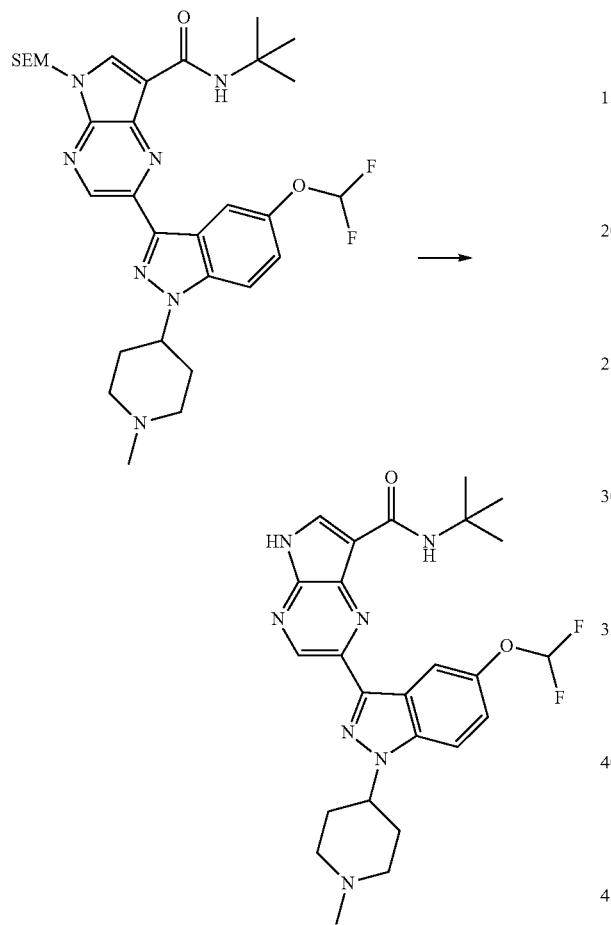

In a 10 ml round-bottomed flask, 2-[5-difluoromethoxy-1-(1-methyl-piperidin-4-yl)-1H-indazol-3-yl]-5-(2-trimethyl-silanyl-ethoxymethyl)-5H-pyrrolo[2,3-b]pyrazine-7-carboxylic acid tert-butylamide (crude from Step 2, 103 mg, 0.131 mmol) was dissolved in dichloromethane (0.7 ml) and trifluoroacetic acid (0.40 ml, 5.2 mmol) was added. The reaction mixture was stirred at room temperature for 2 h then concentrated. The residue was suspended in dichloromethane (0.7 ml) and ethylenediamine (0.53 ml, 7.85 mmol) was added. The light yellow suspension was stirred at room temperature for 1 h then water and ethyl acetate were added. The suspension was filtered and washed with hot water and ethyl acetate. The product collected was dried under high vacuum to provide 57 mg (83%) of 2-[5-difluoromethoxy-1-(1-methyl-piperidin-4-yl)-1H-indazol-3-yl]-5H-pyrrolo[2,3-b]pyrazine-7-carboxylic acid tert-butylamide as a light yellow powder. MS: (M+H)$^+$=498; $^1$H NMR (DMSO-d$_6$, 300 MHz): δ (ppm) 9.08 (s, 1H), 8.38 (s, 1H), 8.20 (s, 1H), 7.86-8.00 (m, 2H), 7.39 (d, J=8.3 Hz, 1H), 7.19 (t, J=74.4 Hz, 1H), 4.67-4.83 (m, 1H), 2.95 (d, J=7.9 Hz, 2H), 2.27 (s, 3H), 2.12-2.32 (m, 4H), 2.00 (d, J=10.2 Hz, 2H), 1.50 (s, 9H).

Example 264

2-(5-Difluoromethoxy-1-pyridin-3-ylmethyl-1H-indazol-3-yl)-5H-pyrrolo[2,3-b]pyrazine-7-carboxylic acid tert-butylamide

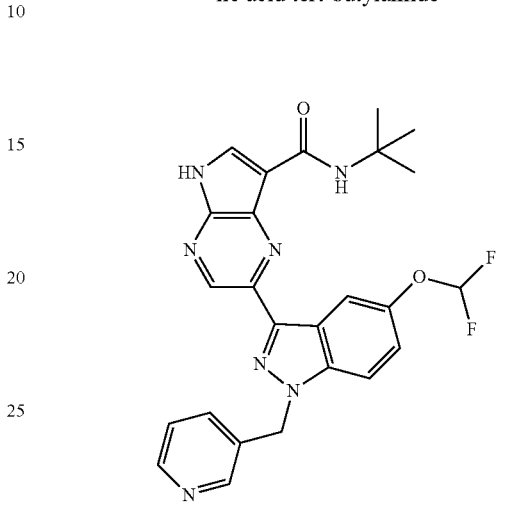

Step 1

2-(5-Difluoromethoxy-1-pyridin-3-ylmethyl-1H-indazol-3-yl)-5-(2-trimethylsilanylethoxymethyl)-5H-pyrrolo[2,3-b]pyrazine-7-carboxylic acid tert-butylamide

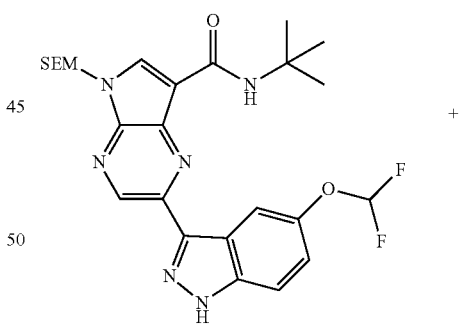 +

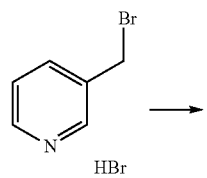

HBr

-continued

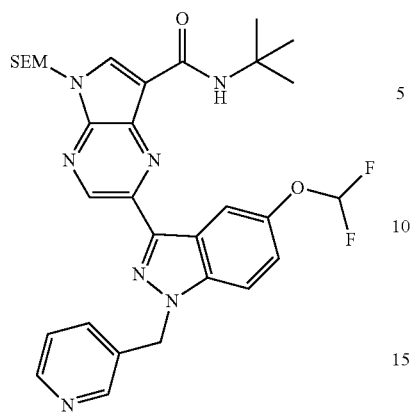

In a 25 ml round-bottomed flask, 2-(5-difluoromethoxy-1H-indazol-3-yl)-5-(2-trimethylsilanyl-ethoxymethyl)-5H-pyrrolo[2,3-b]pyrazine-7-carboxylic acid tert-butylamide (120 mg, 0.23 mmol) was dissolved in DMF (1.7 ml). The light yellow solution was cooled to 0° C. and sodium hydride (60% in mineral oil, 37 mg, 0.93 mmol) was added. The reaction was stirred at 0° C. for 15 min then 3-(bromomethyl)pyridine hydrobromide (91 mg, 0.36 mmol) was added. The reaction mixture was stirred at 0° C. for 1 h then quenched with water and diluted with petroleum ether. The suspension was filtered, washed with water and petroleum ether and the product collected was dried under high vacuum to afford 126 mg (90%) of 2-(5-difluoromethoxy-1-pyridin-3-ylmethyl-1H-indazol-3-yl)-5-(2-trimethylsilanyl-ethoxymethyl)-5H-pyrrolo[2,3-b]pyrazine-7-carboxylic acid tert-butylamide as a yellow powder.

Step 2

2-(5-Difluoromethoxy-1-pyridin-3-ylmethyl-1H-indazol-3-yl)-5H-pyrrolo[2,3-b]pyrazine-7-carboxylic acid tert-butylamide

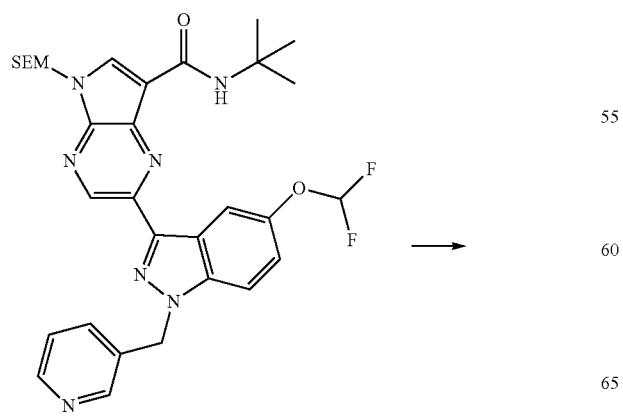

-continued

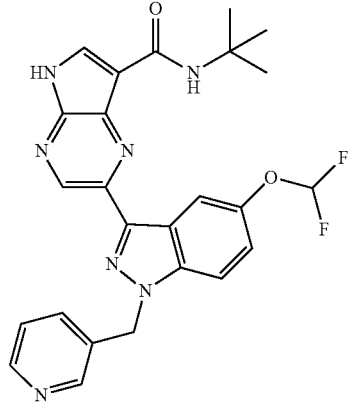 [SMILES: CC(C)(C)NC(=O)c1c[nH]c2ncc(-c3nn(Cc4cccnc4)c4ccc(OC(F)F)cc34)nc12]

In a round-bottomed flask, 2-(5-difluoromethoxy-1-pyridin-3-ylmethyl-1H-indazol-3-yl)-5-(2-trimethylsilanyl-ethoxymethyl)-5H-pyrrolo[2,3-b]pyrazine-7-carboxylic acid tert-butylamide (124 mg, 0.20 mmol) was dissolved in dichloromethane (1 ml) and trifluoroacetic acid (0.62 ml, 8.05 mmol) was added. The reaction mixture was stirred at room temperature for 2 h then concentrated. The residue was dissolved in dichloromethane (1 ml) and ethylenediamine (0.81 ml, 12.0 mmol) was added. The yellow solution was stirred at room temperature for 1 h then quenched with water and extracted with EtOAc (2×). The combined organic layers were washed with water and brine then dried over sodium sulfate, filtered and concentrated. The residue was triturated with a small amount of diethyl ether containing a few drops of ethyl acetate to afford 83 mg (80%) of 2-(5-difluoromethoxy-1-pyridin-3-ylmethyl-1H-indazol-3-yl)-5H-pyrrolo[2,3-b]pyrazine-7-carboxylic acid tert-butylamide as a light yellow powder. MS: (M+H)$^+$=492; $^1$H NMR (DMSO-d$_6$, 300 MHz): δ (ppm) 12.78 (br. s., 1H), 9.09 (s, 1H), 8.68 (d, J=1.9 Hz, 1H), 8.50 (dd, J=4.7, 1.3 Hz, 1H), 8.39 (s, 1H), 8.22 (d, J=2.3 Hz, 1H), 8.02 (d, J=9.4 Hz, 1H), 7.87 (s, 1H), 7.75 (d, J=7.9 Hz, 1H), 7.32-7.46 (m, 2H), 7.07 (t, J=74.0 Hz, 1H), 5.88 (s, 2H), 1.50 (s, 9H).

Example 265

2-(5-Difluoromethoxy-1-pyrrolidin-3-ylmethyl-1H-indazol-3-yl)-5H-pyrrolo[2,3-b]pyrazine-7-carboxylic acid tert-butylamide

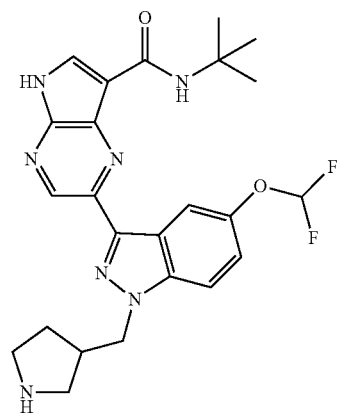 [SMILES: CC(C)(C)NC(=O)c1c[nH]c2ncc(-c3nn(CC4CCNC4)c4ccc(OC(F)F)cc34)nc12]

Step 1

3-Methanesulfonyloxymethyl-pyrrolidine-1-carboxylic acid tert-butyl ester

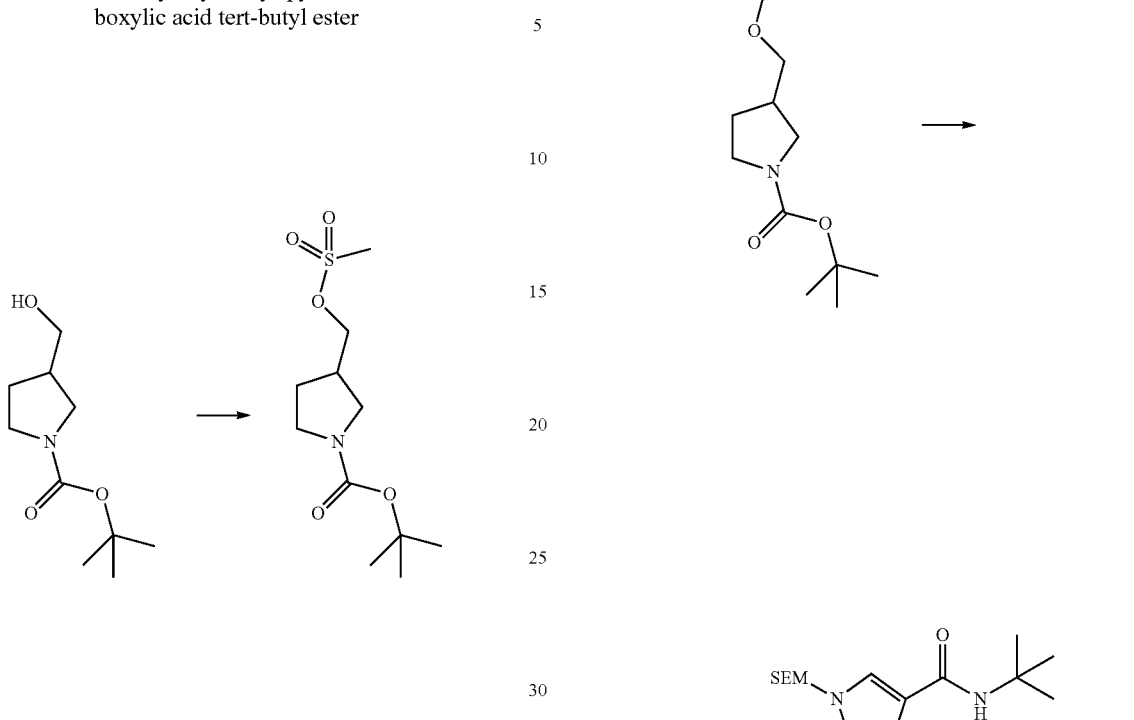

In a round-bottomed flask, 3-(hydroxymethyl)pyrrolidine-1-carboxylic acid tert-butyl ester (120 mg, 0.60 mmol) was dissolved in dichloromethane (4.4 ml). The colorless solution was cooled to 0° C. and triethylamine (0.13 ml, 0.93 mmol) methanesulfonyl chloride (0.05 ml, 0.64 mmol) were added. The reaction mixture was stirred at 0° C. for 3 h then quenched with water and extracted with dichloromethane (2×). The organic layers were combined, dried over sodium sulfate, filtered and concentrated to give 3-methanesulfonyloxymethyl-pyrrolidine-1-carboxylic acid tert-butyl ester as a light yellow oil which was used without further purification.

Step 2

3-{3-[7-tert-Butylcarbamoyl-5-(2-trimethylsilanylethoxymethyl)-5H-pyrrolo[2,3-b]pyrazin-2-yl]-5-difluoromethoxy-indazol-1-ylmethyl}-pyrrolidine-1-carboxylic acid tert-butyl ester

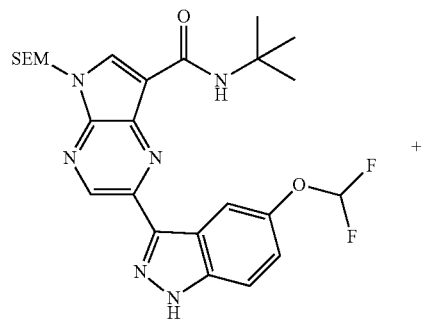

A round-bottomed flask was charged with 2-(5-difluoromethoxy-1H-indazol-3-yl)-5-(2-trimethylsilanylethoxymethyl)-5H-pyrrolo[2,3-b]pyrazine-7-carboxylic acid tert-butylamide (120 mg, 0.23 mmol), 3-methanesulfonyloxymethyl-pyrrolidine-1-carboxylic acid tert-butyl ester (crude from Step 1, 215 mg, 0.54 mmol), cesium carbonate (258 mg, 0.79 mmol) and DMF (1 ml). The reaction mixture was stirred at 110° C. for 1.5 h then cooled to room temperature, quenched with water and extracted with diethyl ether (2×). The combined organic layers were washed twice with water and once with brine then dried over sodium sulfate, filtered and concentrated. The residue was chromatographed over 12 g silica gel with EtOAc/hexanes (gradient: 0-40% EtOAc). The appropriate fractions were combined and concentrated and the residue was triturated with petroleum ether to afford 138 mg (86%) of 3-{3-[7-tert-butylcarbamoyl-5-(2-trimethylsilanyl-ethoxymethyl)-5H-pyrrolo[2,3-b]pyrazin- 2-yl]-5-difluoromethoxy-indazol-1-ylmethyl}-pyrrolidine-1-carboxylic acid tert-butyl ester as a light yellow powder.

Step 3

2-(5-Difluoromethoxy-1-pyrrolidin-3-ylmethyl-1H-indazol-3-yl)-5H-pyrrolo[2,3-b]pyrazine-7-carboxylic acid tert-butylamide

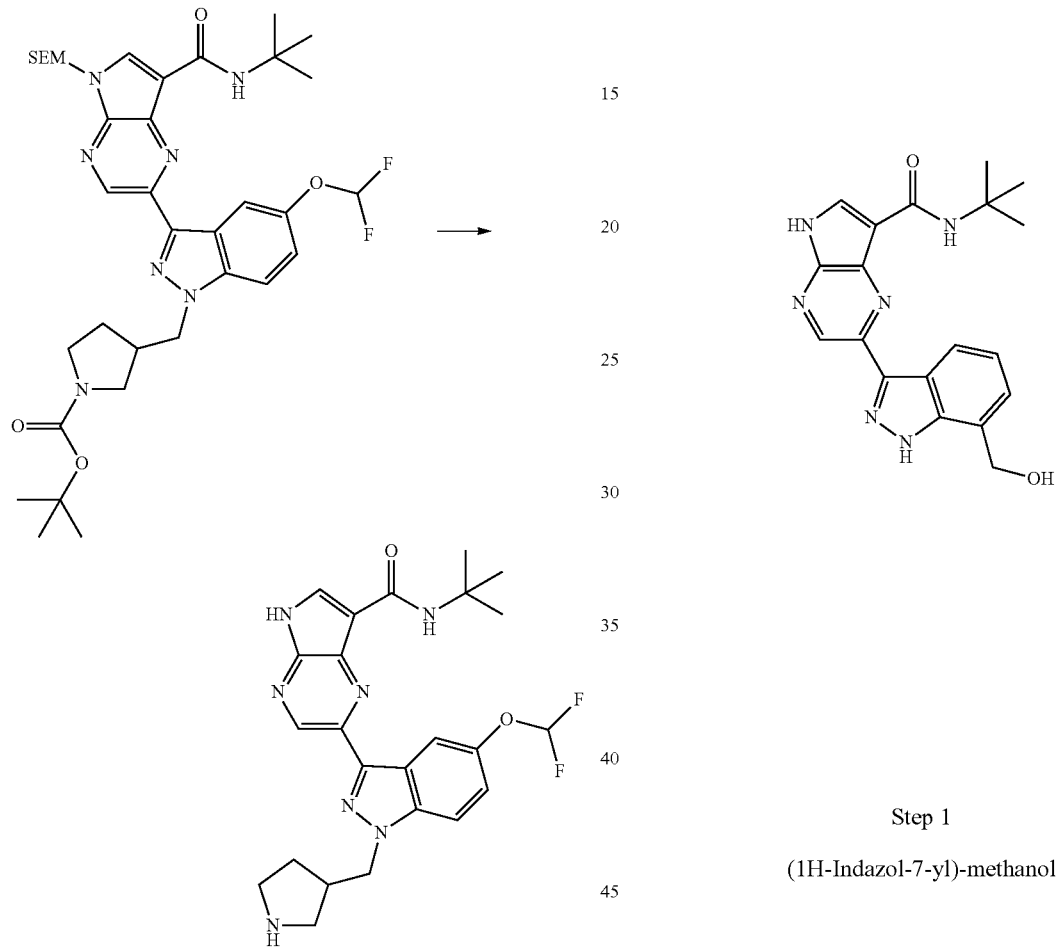

In a round-bottomed flask, 3-{3-[7-tert-butylcarbamoyl-5-(2-trimethylsilanylethoxymethyl)-5H-pyrrolo[2,3-b]pyrazin-2-yl]-5-difluoromethoxy-indazol-1-ylmethyl}-pyrrolidine-1-carboxylic acid tert-butyl ester (134 mg, 0.188 mmol) was dissolved in dichloromethane (1 ml) and trifluoroacetic acid (0.58 ml, 7.53 mmol) was added. The reaction mixture was stirred at room temperature for 2 h then concentrated. The residue was dissolved in dichloromethane (1 ml) and ethylenediamine (0.76 ml, 11.3 mmol) was added. The light yellow solution was stirred at room temperature for 45 min then water and ethyl acetate were added. The resulting suspension was filtered and washed with hot water and ethyl acetate then dried under high vacuum to provide 33 mg (35%) of 2-(5-difluoromethoxy-1-pyrrolidin-3-ylmethyl-1H-indazol-3-yl)-5H-pyrrolo[2,3-b]pyrazine-7-carboxylic acid tert-butylamide as a light yellow powder. MS: (M+H)$^+$=484; $^1$H NMR (DMSO-d$_6$, 300 MHz): δ (ppm) 9.06 (s, 1H), 8.38 (s, 1H), 8.21 (s, 1H), 7.94 (d, J=9.1 Hz, 1H), 7.88 (s, 1H), 7.40 (d, J=9.1 Hz, 1H), 7.20 (t, J=74.8 Hz, 1H), 4.50 (d, J=6.8 Hz, 2H), 2.58-2.97 (m, 6H), 1.69-1.84 (m, 1H), 1.51 (s, 9H).

Example 266

2-(7-Hydroxymethyl-1H-indazol-3-yl)-5H-pyrrolo[2,3-b]pyrazine-7-carboxylic acid tert-butylamide

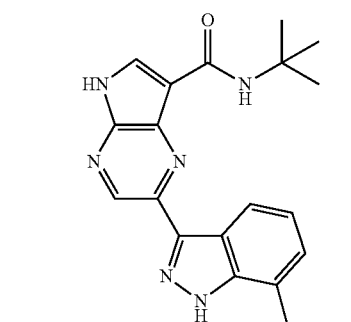

Step 1

(1H-Indazol-7-yl)-methanol

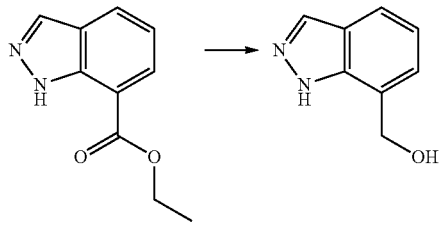

In a round-bottomed flask, ethyl 1H-indazole-7-carboxylate (600 mg, 3.15 mmol) was dissolved in THF (16 ml). The light yellow solution was cooled to 0° C. and lithium aluminum hydride (1.0 M in THF, 3.8 ml, 3.8 mmol) was added dropwise. The bright yellow reaction mixture was stirred at 0° C. for 1.25 h then sodium sulfate decahydrate was carefully added. When gas evolution had stopped, the ice bath was removed, sodium sulfate was added and the mixture was stirred for 30 min at room temperature. The suspension was filtered over Celite and rinsed with ethyl acetate/methanol.

The filtrate was concentrated to afford (1H-indazol-7-yl)-methanol as a light yellow solid which was used without further purification.

Step 2

(3-Iodo-1H-indazol-7-yl)-methanol

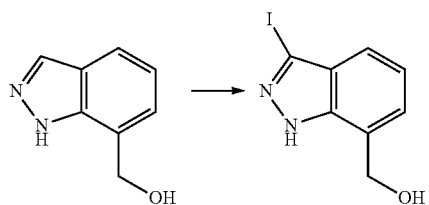 [SMILES: OCc1cccc2cn[nH]c12 ; OCc1cccc2c(I)n[nH]c12]

In a round-bottomed flask, (1H-indazol-7-yl)-methanol (572 mg, 3.09 mmol) was dissolved in DMF (8 ml) and potassium hydroxide (671 mg, 12.0 mmol) and iodine (1.57 g, 6.18 mmol) were added. The dark brown suspension was stirred at room temperature overnight then quenched with aqueous 10% $Na_2S_2O_3$ and extracted with diethyl ether (2×). The combined organic layers were washed twice with water and once with brine then dried over sodium sulfate, filtered and concentrated to give 433 mg (51%) of (3-iodo-1H-indazol-7-yl)-methanol as a light yellow solid.

Step 3

7-(tert-Butyl-dimethyl-silanyloxymethyl)-3-iodo-1H-indazole

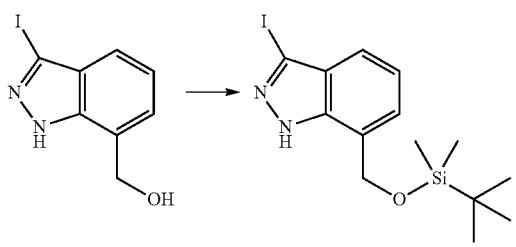 [SMILES: OCc1cccc2c(I)n[nH]c12 ; CC(C)(C)[Si](C)(C)OCc1cccc2c(I)n[nH]c12]

In a round-bottomed flask, (3-iodo-1H-indazol-7-yl)-methanol (317 mg, 1.16 mmol) was dissolved in DMF (3.6 ml) and imidazole (197 mg, 2.89 mmol) and tert-butyldimethylsilyl chloride (192 mg, 1.27 mmol) were added. The reaction mixture was stirred at room temperature for 72 h then quenched with water and extracted with diethyl ether (2×). The combined organic layers were washed twice with water and once with brine then dried over sodium sulfate, filtered and concentrated. The residue was chromatographed over 12 g silica gel with EtOAc/hexanes (gradient: 0-5% EtOAc) to give 357 mg (80%) of 7-(tert-butyl-dimethyl-silanyloxymethyl)-3-iodo-1H-indazole as an off-white solid. $^1$H NMR (CDCl$_3$, 300 MHz): δ (ppm) 10.76 (br. s., 1H), 7.42 (dd, J=6.8, 2.3 Hz, 1H), 7.15-7.20 (m, 2H), 5.09 (s, 2H), 0.95 (s, 9H), 0.13 (s, 6H).

Step 4

7-(tert-Butyl-dimethyl-silanyloxymethyl)-3-tributyl-stannanyl-1H-indazole

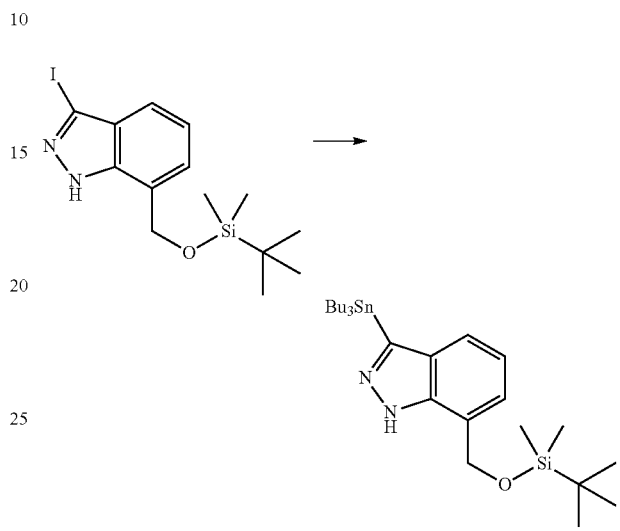

In a round-bottomed flask, 7-(tert-butyl-dimethyl-silanyloxymethyl)-3-iodo-1H-indazole (200 mg, 0.52 mmol) was dissolved in THF (2.8 ml) and sodium hydride (60% in mineral oil, 25 mg, 0.63 mmol) was added. The reaction mixture was stirred at room temperature for 10 min then cooled to −16° C. (NaCl/ice bath) and isopropylmagnesium chloride (2.0 M in THF, 0.36 ml, 0.72 mmol) was added dropwise. The reaction mixture was stirred at −16° C. for 30 min then tributylchlorostannane (0.16 ml, 0.59 mmol) was slowly added. The reaction mixture was allowed to warm to room temperature and stirred for 2.5 h then quenched with saturated aqueous NH$_4$Cl and extracted with EtOAc (2×). The organic layers were washed with water and brine then dried over sodium sulfate, filtered and concentrated to give 7-(tert-butyl-dimethyl-silanyloxymethyl)-3-tributylstannanyl-1H-indazole as a yellow oil which was used without further purification.

Step 5

2-[7-(tert-Butyl-dimethyl-silanyloxymethyl)-1H-indazol-3-yl]-5-(2-trimethylsilanylethoxymethyl)-5H-pyrrolo[2,3-b]pyrazine-7-carboxylic acid tert-butylamide

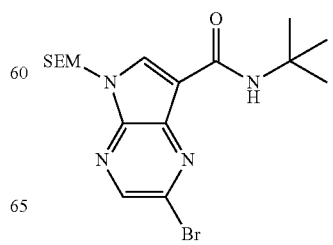

+

-continued

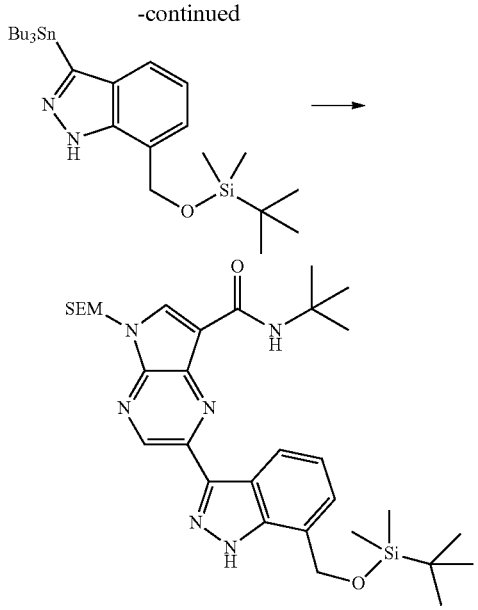

In a 25 ml round-bottomed flask, 2-bromo-5-(2-trimethyl-silanyl-ethoxymethyl)-5H-pyrrolo[2,3-b]pyrazine-7-carboxylic acid tert-butylamide (180 mg, 0.42 mmol) and 7-(tert-butyldimethyl-silanyloxymethyl)-3-tributylstannanyl-1H-indazole (crude from Step 4, 462 mg, 0.50 mmol) were dissolved in DMF (2.8 ml). The reaction mixture was evacuated and backfilled with argon and tetrakis(triphenylphosphine)palladium (0) (25 mg, 0.022 mmol) and copper (I) iodide (16 mg, 0.084 mmol) were added. The reaction mixture was stirred at 80° C. overnight then cooled to room temperature, quenched with water and extracted with diethyl ether (2×). The combined organic layers were washed twice with water and once with brine then concentrated. The residue was chromatographed over 25 g silica gel with EtOAc/hexanes (gradient: 0-30% EtOAc) to afford 86 mg (34%) of 2-[7-(tert-butyl-dimethyl-silanyloxymethyl)-1H-indazol-3-yl]-5-(2-trimethylsilanyl-ethoxymethyl)-5H-pyrrolo[2,3-b]pyrazine-7-carboxylic acid tert-butylamide as a light yellow solid.

Step 6

2-(7-Hydroxymethyl-1H-indazol-3-yl)-5H-pyrrolo[2,3-b]pyrazine-7-carboxylic acid tert-butylamide

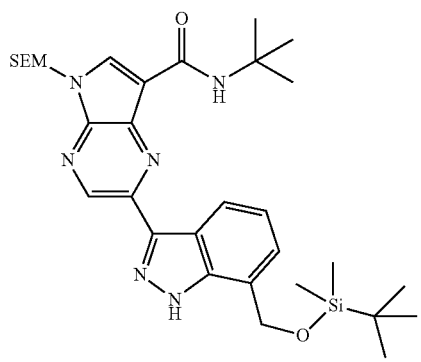

-continued

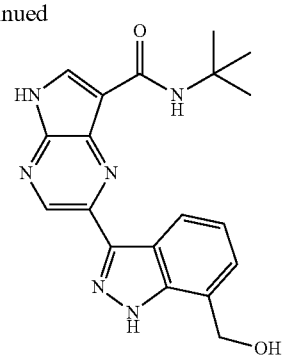

In a round-bottomed flask, 2-[7-(tert-butyl-dimethyl-silanyloxymethyl)-1H-indazol-3-yl]-5-(2-trimethylsilanyl-ethoxymethyl)-5H-pyrrolo[2,3-b]pyrazine-7-carboxylic acid tert-butylamide (85 mg, 0.14 mmol) was dissolved in THF (0.7 ml) and tetrabutylammonium fluoride (1.0 M in THF, 1.4 ml, 1.4 mmol) was added dropwise. The light brown solution was stirred at room temperature for 10 min then heated at 70° C. for 2.5 h. The reaction mixture was cooled to room temperature, quenched with water and extracted with EtOAc (2×). The combined organic layers were washed with water and brine then dried over sodium sulfate, filtered and concentrated. The residue was absorbed on silica gel and chromatographed with MeOH/CH$_2$Cl$_2$/0.5% NH$_4$OH (gradient: 0-10% MeOH). The appropriate fractions were combined and concentrated and the residue was triturated with ethyl acetate containing a few drops of methanol to afford 21 mg (41%) of 2-(7-hydroxymethyl-1H-indazol-3-yl)-5H-pyrrolo[2,3-b]pyrazine-7-carboxylic acid tert-butylamide as an off-white powder. MS: (M+Na)'=387; $^1$H NMR (DMSO-d$_6$, 400 MHz): δ (ppm) 13.49 (s, 1H), 12.77 (s, 1H), 9.15 (s, 1H), 8.39 (d, J=8.1 Hz, 1H), 8.36 (d, J=3.0 Hz, 1H), 8.01 (s, 1H), 7.38-7.46 (m, 1H), 7.16-7.25 (m, 1H), 5.37 (t, J=5.6 Hz, 1H), 4.88 (d, J=5.6 Hz, 2H), 1.53 (s, 9H).

Example 267

2-(6-Fluoro-1-piperidin-4-yl-1H-indazol-3-yl)-5H-pyrrolo[2,3-b]pyrazine-7-carboxylic acid (3-amino-cyclopentyl)-amide

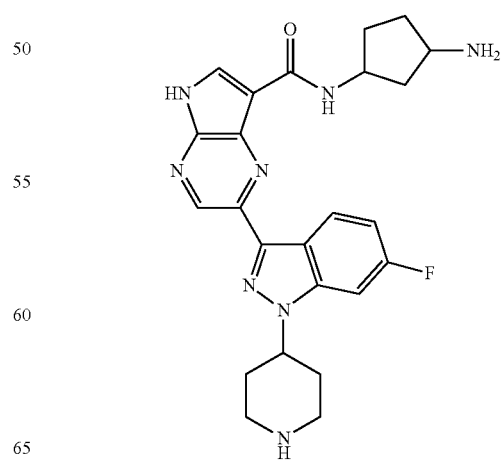

887

Step 1

4-{3-[7-(3-tert-Butoxycarbonylamino-cyclopentyl-carbamoyl)-5-(2-trimethylsilanylethoxymethyl)-5H-pyrrolo[2,3-b]pyrazin-2-yl]-6-fluoro-indazol-1-yl}-piperidine-1-carboxylic acid tert-butyl ester

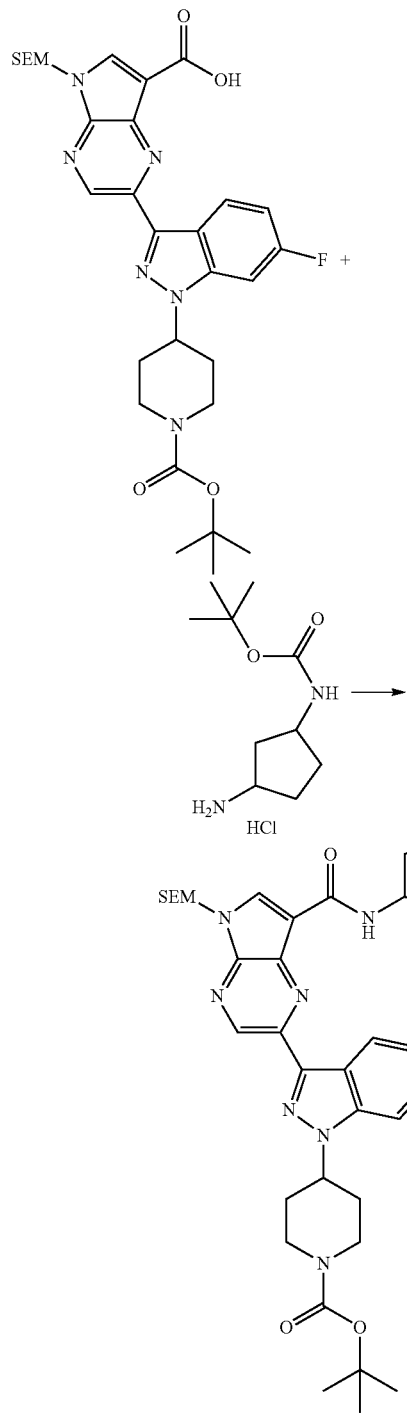

A 10 ml round-bottomed flask was charged with 2-[1-(1-tert-butoxycarbonyl-piperidin-4-yl)-6-fluoro-1H-indazol-3-yl]-5-(2-trimethylsilanyl-ethoxymethyl)-5H-pyrrolo[2,3-b]pyrazine-7-carboxylic acid (85 mg, 0.14 mmol) and (3-aminocyclopentyl)-carbamic acid tert-butyl ester hydrochloride (50 mg, 0.21 mmol). Then, DMF (1 ml) was added followed by N,N-diisopropylethylamine (0.07 ml, 0.40 mmol) and HATU (59 mg, 0.155 mmol). The reaction mixture was stirred at room temperature overnight then quenched with water and extracted with diethyl ether (2×). The combined organic layers were washed twice with water and once with brine then dried over sodium sulfate, filtered and concentrated. The residue was chromatographed over 12 g silica gel with EtOAc/hexanes (gradient: 0-50% EtOAc) to afford 121 mg (99%) of 4-{3-[7-(3-tert-butoxycarbonylamino-cyclopentylcarbamoyl)-5-(2-trimethylsilanyl-ethoxymethyl)-5H-pyrrolo[2,3-b]pyrazin-2-yl]-6-fluoro-indazol-1-yl}-piperidine-1-carboxylic acid tert-butyl ester as a light yellow oil. The isolated product was determined to be a single diastereomer of unknown relative stereochemistry by NMR analysis.

Step 2

2-(6-Fluoro-1-piperidin-4-yl-1H-indazol-3-yl)-5H-pyrrolo[2,3-b]pyrazine-7-carboxylic acid (3-amino-cyclopentyl)-amide

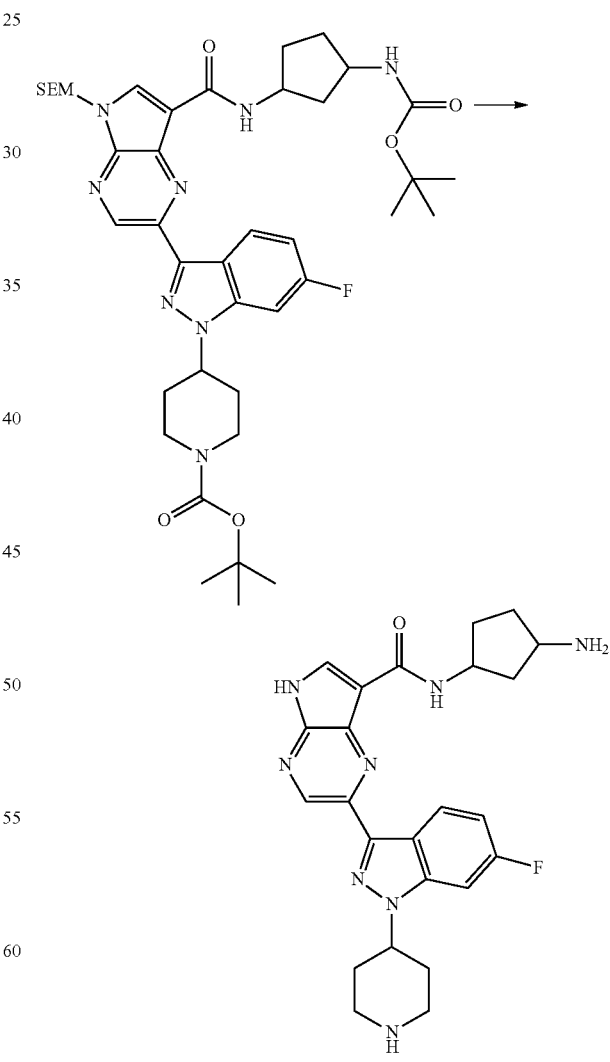

In a round-bottomed flask, 4-{3-[7-(3-tert-butoxycarbony-lamino-cyclopentylcarbamoyl)-5-(2-trimethylsilanylethoxymethyl)-5H-pyrrolo[2,3-b]pyrazin-2-yl]-6-fluoro-indazol-1-yl}-piperidine-1-carboxylic acid tert-butyl ester (113 mg, 0.13 mmol) was dissolved in dichloromethane (0.7 ml) and trifluoroacetic acid (0.40 ml, 5.2 mmol) was added. The reaction mixture was stirred at room temperature for 2 h then concentrated. The residue was dissolved in dichloromethane (0.7 ml) and ethylenediamine (0.52 ml, 7.7 mmol) was added. The light yellow reaction was stirred at room temperature for 1 h then water and ethyl acetate were added. The resulting suspension was filtered and washed with hot water and ethyl acetate then dried under high vacuum to provide 43 mg (73%) of 2-(6-fluoro-1-piperidin-4-yl-1H-indazol-3-yl)-5H-pyrrolo[2,3-b]pyrazine-7-carboxylic acid (3-amino-cyclopentyl)-amide as an off-white powder.

MS: (M+H)$^+$=463; $^1$H NMR (DMSO-d$_6$, 400 MHz): δ (ppm) 9.08 (s, 1H), 8.56 (dd, J=9.1, 5.6 Hz, 1H), 8.40 (s, 1H), 8.27 (d, J=7.8 Hz, 1H), 7.76-7.85 (m, 1H), 7.27 (t, J=9.0 Hz, 1H), 4.69-4.85 (m, 1H), 4.32-4.47 (m, 1H), 3.33-3.42 (m, 1H), 3.12 (d, J=12.6 Hz, 2H), 2.72 (t, J=11.2 Hz, 2H), 2.25-2.37 (m, 1H), 2.02-2.17 (m, 3H), 1.88-2.00 (m, 2H), 1.70-1.86 (m, 2H), 1.49-1.62 (m, 1H), 1.30-1.42 (m, 1H).

Example 268

2-[7-(1-Hydroxy-1-methyl-ethyl)-1H-indazol-3-yl]-5H-pyrrolo[2,3-b]pyrazine-7-carboxylic acid tert-butylamide

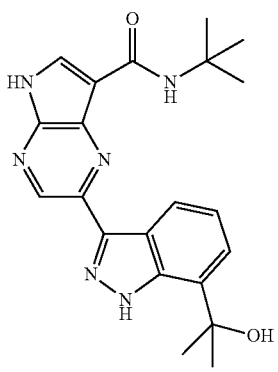 [SMILES: CC(C)(C)NC(=O)c1c[nH]c2ncc(-c3n[nH]c4c(C(C)(C)O)cccc34)nc12]

Step 1

2-(1H-Indazol-7-yl)-propan-2-ol

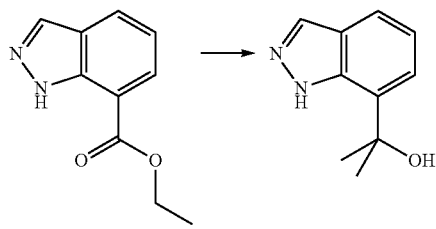

In a 50 ml round-bottomed flask, ethyl 1H-indazole-7-carboxylate (350 mg, 1.84 mmol) was dissolved in THF (10 ml). The yellow solution was cooled to 0° C. and methylmagnesium bromide (3.0 M in diethyl ether, 2.2 ml, 6.6 mmol) was added dropwise. The reaction mixture was stirred at 0° C. for 1.5 h then quenched with saturated aqueous NH$_4$Cl and extracted with EtOAc (2×). The combined organic layers were washed with water and brine then dried over sodium sulfate, filtered and concentrated. The residue was chromatographed over 12 g silica gel with EtOAc/hexanes (gradient: 0-50% EtOAc) to afford 225 mg (69%) of 2-(1H-indazol-7-yl)propan-2-ol as a yellow oil.

Step 2

2-(3-Iodo-1H-indazol-7-yl)-propan-2-ol

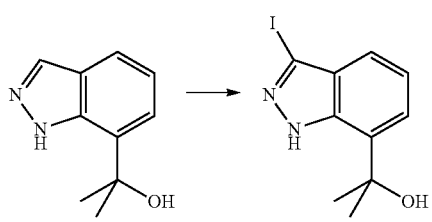

In a round-bottomed flask, 2-(1H-indazol-7-yl)-propan-2-ol (204 mg, 1.16 mmol) was dissolved in DMF (3 ml) and iodine (588 mg, 2.32 mmol) and potassium hydroxide (251 mg, 4.48 mmol) were added. The dark brown suspension was stirred at room temperature for 5 h then quenched with 10% aqueous NaHSO$_3$ and extracted with a mixture of diethyl ether and EtOAc (2×). The combined organic layers were washed twice with water and once with brine then dried over sodium sulfate, filtered and concentrated to afford 2-(3-iodo-1H-indazol-7-yl)-propan-2-ol as a light yellow oil which was used without further purification.

Step 3

3-Iodo-7-(1-methyl-1-trimethylsilanyloxy-ethyl)-1H-indazole

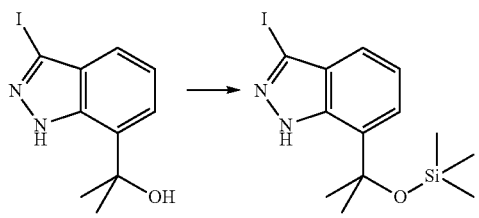 [SMILES: CC(C)(O)c1cccc2c(I)n[nH]c12 ; CC(C)(O[Si](C)(C)C)c1cccc2c(I)n[nH]c12]

In a round-bottomed flask, 2-(3-iodo-1H-indazol-7-yl)-propan-2-ol (crude from Step 2, 479 mg, 1.11 mmol) was dissolved in DMF (3.2 ml) and imidazole (189 mg, 2.77 mmol) and trimethylsilyl chloride (0.17 ml, 1.33 mmol) were added. The reaction mixture was stirred at room temperature overnight then quenched with water and extracted with diethyl ether (2×). The combined organic layers were washed twice with water and once with brine then dried over sodium sulfate, filtered and concentrated to give 383 mg (88%) of 3-iodo-7-(1-methyl-1-trimethylsilanyloxy-ethyl)-1H-indazole as a light yellow solid. $^1$H NMR (CDCl$_3$, 300 MHz): δ

(ppm) 10.86 (br. s., 1H), 7.40 (dd, J=6.8, 2.3 Hz, 1H), 7.12-7.21 (m, 2H), 1.73 (s, 6H), 0.11 (s, 9H).

Step 4

2-[7-(1-Hydroxy-1-methyl-ethyl)-1H-indazol-3-yl]-5H-pyrrolo[2,3-b]pyrazine-7-carboxylic acid tert-butylamide

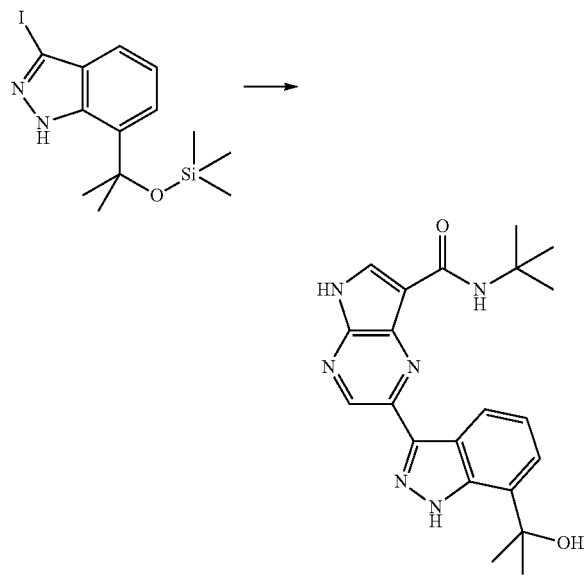

Prepared according to the procedure outlined in Example 266, Step 4-6, substituting 3-iodo-7-(1-methyl-1-trimethylsilanyloxy-ethyl)-1H-indazole for 7-(tert-butyl-dimethyl-silanyloxymethyl)-3-iodo-1H-indazole in Step 4. MS: (M+Na)$^+$= 415. $^1$H NMR (DMSO-d$_6$, 400 MHz): δ (ppm) 13.08 (s, 1H), 12.78 (br. s., 1H), 9.14 (s, 1H), 8.39 (d, J=7.8 Hz, 1H), 8.35 (s, 1H), 8.03 (s, 1H), 7.35 (d, J=6.3 Hz, 1H), 7.16 (t, J=7.7 Hz, 1H), 5.49 (s, 1H), 1.64 (s, 6H), 1.53 (s, 9H).

Example 269

2-[5-(1-Hydroxy-ethyl)-1-methyl-1H-indazol-3-yl]-5H-pyrrolo[2,3-b]pyrazine-7-carboxylic acid isopropylamide

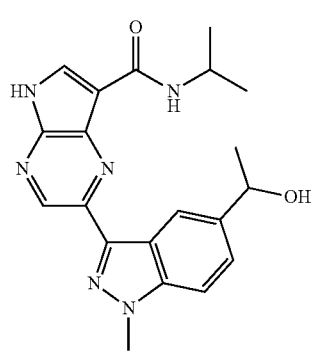 [SMILES: CC(C)NC(=O)c1c[nH]c2ncc(-c3nn(C)c4ccc(C(C)O)cc34)nc12]

Step 1

2-[5-(tert-Butyl-dimethyl-silanyloxymethyl)-1-methyl-1H-indazol-3-yl]-5-(2-trimethylsilanylethoxymethyl)-5H-pyrrolo[2,3-b]pyrazine-7-carboxylic acid isopropylamide

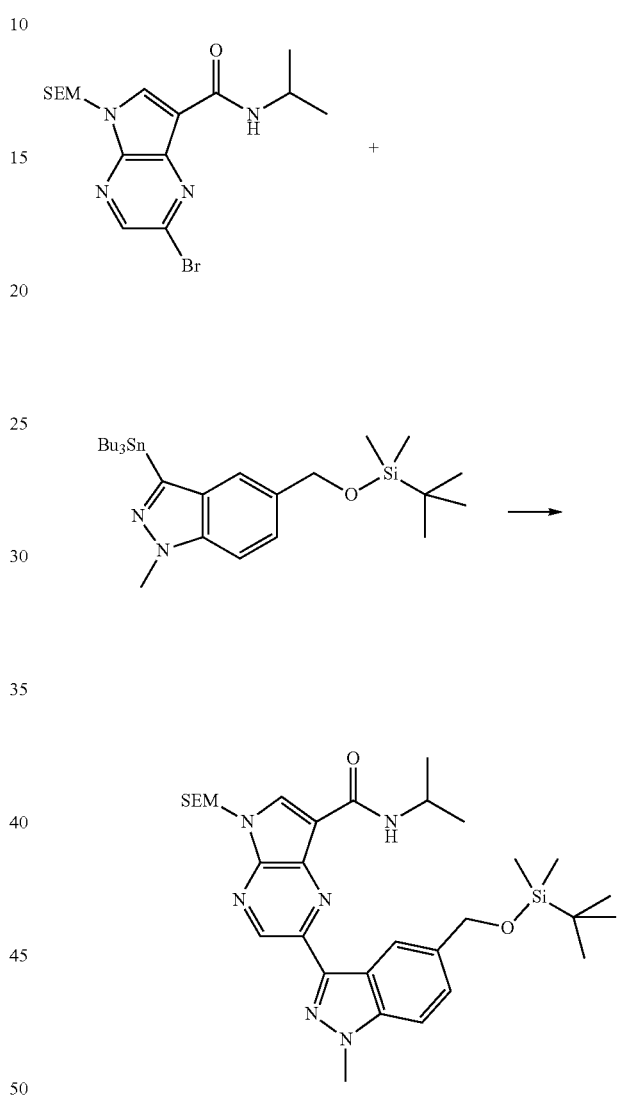

In a round-bottomed flask, 2-bromo-5-(2-trimethylsilanyl-ethoxymethyl)-5H-pyrrolo[2,3-b]pyrazine-7-carboxylic acid isopropylamide (300 mg, 0.73 mmol) and 5-(tert-butyl-dimethyl-silanyloxymethyl)-1-methyl-3-tributylstannanyl-1H-indazole (Example 273, 665 mg, 0.82 mmol) were dissolved in DMF (4.8 ml). The reaction mixture was evacuated and backfilled with argon then tetrakis(triphenylphosphine) palladium (0) (42 mg, 0.036 mmol) and copper (I) iodide (28 mg, 0.147 mmol) were added. The reaction mixture was stirred at 80° C. overnight then cooled to room temperature, quenched with water and diluted with petroleum ether. The resulting suspension was filtered and the solids washed with water, petroleum ether and a minimal amount of diethyl ether then dried under high vacuum to afford 426 mg (92%) of 2-[5-(tert-butyldimethyl-silanyloxymethyl)-1-methyl-1H- indazol-3-yl]-5-(2-trimethylsilanyl-ethoxymethyl)-5H-pyrrolo[2,3-b]pyrazine-7-carboxylic acid isopropylamide as a brown powder.

Step 2

2-(5-Hydroxymethyl-1-methyl-1H-indazol-3-yl)-5-(2-trimethylsilanyl-ethoxymethyl)-5H-pyrrolo[2,3-b]pyrazine-7-carboxylic acid isopropylamide

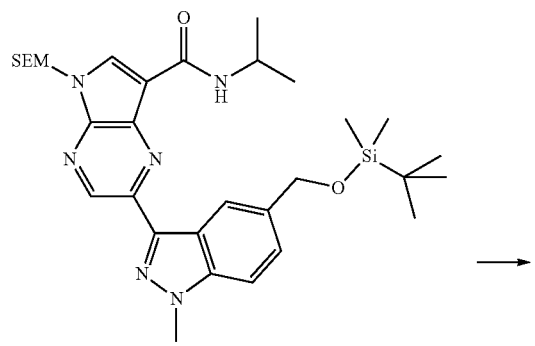

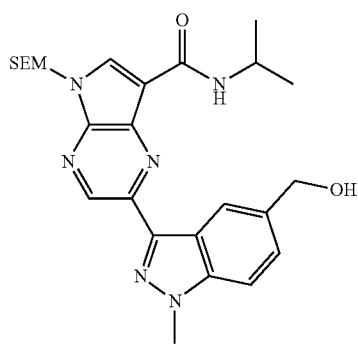

In a round-bottomed flask, 2-[5-(tert-butyl-dimethyl-silanyloxymethyl)-1-methyl-1H-indazol-3-yl]-5-(2-trimethylsilanyl-ethoxymethyl)-5H-pyrrolo[2,3-b]pyrazine-7-carboxylic acid isopropylamide (425 mg, 0.66 mmol) was dissolved in THF (6 ml). The light yellow solution was cooled to 0° C. and tetrabutylammonium fluoride (1.0 M in THF, 0.24 ml, 0.240 mmol) was added dropwise. The reaction mixture was allowed to warm slowly to room temperature over 2 h then quenched with water and extracted with EtOAc (2×). The combined organic layers were washed with water and brine then concentrated. The residue was triturated with diethyl ether to afford 2-(5-hydroxymethyl-1-methyl-1H-indazol-3-yl)-5-(2-trimethylsilanyl-ethoxymethyl)-5H-pyrrolo[2,3-b]pyrazine-7-carboxylic acid isopropylamide as a yellow powder which was used without further purification.

Step 3

2-(5-Formyl-1-methyl-1H-indazol-3-yl)-5-(2-trimethylsilanyl-ethoxymethyl)-5H-pyrrolo[2,3-b]pyrazine-7-carboxylic acid isopropylamide

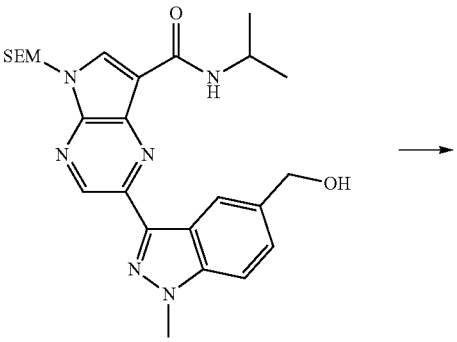

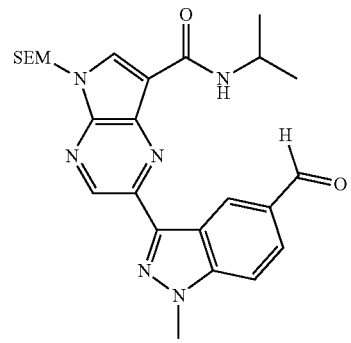

In a round-bottomed flask, 2-(5-hydroxymethyl-1-methyl-1H-indazol-3-yl)-5-(2-trimethylsilanyl-ethoxymethyl)-5H-pyrrolo[2,3-b]pyrazine-7-carboxylic acid isopropylamide (crude from Step 2, 476 mg, 0.625 mmol) was dissolved in dichloromethane (3.2 ml) and Dess-Martin periodinane (292 mg, 0.688 mmol) was added. The reaction mixture was stirred at room temperature for 1.5 h then quenched with 10 ml of a 1:1 mixture of 10% aqueous $Na_2S_2O_3$ and saturated aqueous $NaHCO_3$ and extracted with dichloromethane. The organic layer was washed with saturated aqueous $NaHCO_3$ then the aqueous layers were back-extracted with dichloromethane. The combined organic layers were dried over sodium sulfate, filtered and concentrated. The residue was absorbed on silica gel and chromatographed with EtOAc/Hexanes (gradient: 0-60% EtOAc) to afford 218 mg (71%) of 2-(5-formyl-1-methyl-1H-indazol-3-yl)-5-(2-trimethylsilanyl-ethoxymethyl)-5H-pyrrolo[2,3-b]pyrazine-7-carboxylic acid isopropylamide as a light yellow solid. $^1$H NMR (CDCl$_3$, 400 MHz): δ (ppm) 9.25 (s, 1H), 8.97 (dd, J=1.4, 0.9 Hz, 1H), 8.41 (s, 1H), 8.11 (d, J=8.6 Hz, 1H), 8.07 (dd, J=8.8, 1.5 Hz, 1H), 7.60 (d, J=8.8 Hz, 1H), 5.75 (s, 2H), 4.42-4.53 (m, 1H), 4.26 (s, 3H), 3.56-3.64 (m, 2H), 1.41 (d, J=6.6 Hz, 6H), 0.92-1.00 (m, 2H), −0.03 (s, 9H).

Step 4

2-[5-(1-Hydroxy-ethyl)-1-methyl-1H-indazol-3-yl]-5-(2-trimethylsilanyl-ethoxymethyl)-5H-pyrrolo[2,3-b]pyrazine-7-carboxylic acid isopropylamide

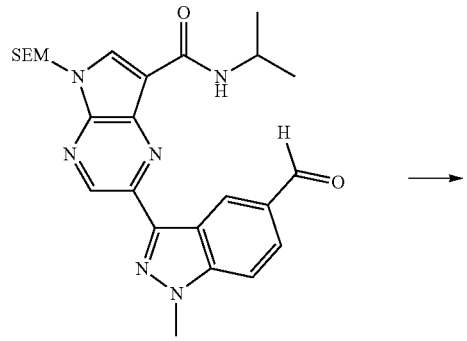

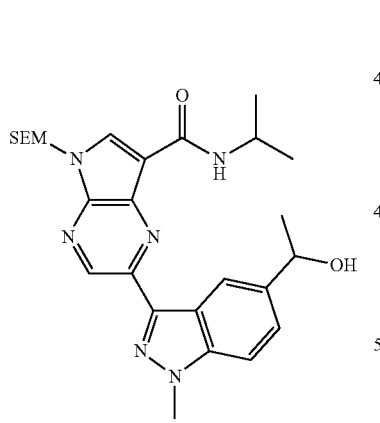

In a round-bottomed flask, 2-(5-formyl-1-methyl-1H-indazol-3-yl)-5-(2-trimethylsilanylethoxymethyl)-5H-pyrrolo[2,3-b]pyrazine-7-carboxylic acid isopropylamide (111 mg, 0.225 mmol) was suspended in THF (3 ml). The pale yellow suspension was cooled to 0° C. and methylmagnesium bromide (3.0 M in diethyl ether, 0.23 ml, 0.69 mmol) was added dropwise. The dark red suspension was stirred at 0° C. for 1 h then quenched with saturated aqueous NH$_4$Cl and extracted with dichloromethane (2×). The organic layers were combined, dried over sodium sulfate, filtered and concentrated. The residue was chromatographed over 12 g silica gel with EtOAc/hexanes (gradient: 0-80% EtOAc) to afford 42 mg (37%) of 2-[5-(1-hydroxy-ethyl)-1-methyl-1H-indazol-3-yl]-5-(2-trimethylsilanyl-ethoxymethyl)-5H-pyrrolo[2,3-b]pyrazine-7-carboxylic acid isopropylamide as a light yellow solid.

Step 5

2-[5-(1-Hydroxy-ethyl)-1-methyl-1H-indazol-3-yl]-5H-pyrrolo[2,3-b]pyrazine-7-carboxylic acid isopropylamide

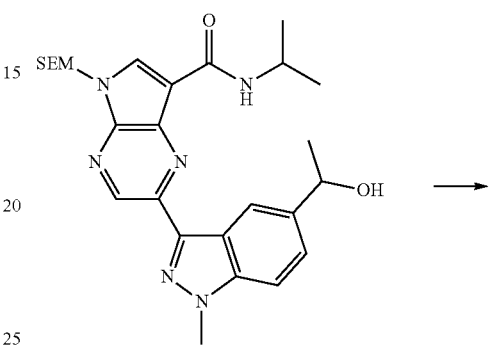

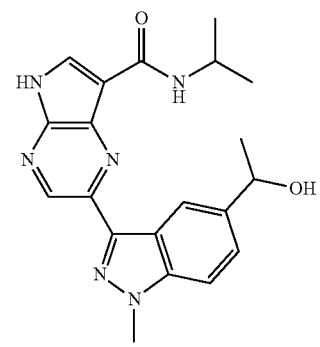

In a round-bottomed flask, 2-[5-(1-hydroxy-ethyl)-1-methyl-1H-indazol-3-yl]-5-(2-trimethylsilanyl-ethoxymethyl)-5H-pyrrolo[2,3-b]pyrazine-7-carboxylic acid isopropylamide (41 mg, 0.08 mmol) was dissolved in tetrabutylammonium fluoride (1.0 M in THF, 0.90 ml, 0.90 mmol). The reaction mixture was stirred at 60° C. overnight then cooled to room temperature, quenched with water and extracted with EtOAc (2×). The combined organic layers were washed with water and brine then concentrated. The residue was triturated with water, ethyl acetate and a few drops of methanol to afford 21 mg (65%) of 2-[5-(1-hydroxy-ethyl)-1-methyl-1H-indazol-3-yl]-5H-pyrrolo[2,3-b]pyrazine-7-carboxylic acid isopropylamide as a yellow powder. MS: (M+Na)$^+$=401; $^1$H NMR (DMSO-d$_6$, 300 MHz): δ (ppm) 12.82 (br. s., 1H), 9.09 (s, 1H), 8.41 (s, 1H), 8.30 (s, 1H), 8.04 (d, J=7.9 Hz, 1H), 7.73 (d, J=8.7 Hz, 1H), 7.55 (d, J=8.3 Hz, 1H), 5.27 (d, J=3.8 Hz, 1H), 4.87-5.00 (m, 1H), 4.19-4.32 (m, 1H), 4.17 (s, 3H), 1.41 (d, J=6.0 Hz, 3H), 1.33 (d, J=6.8 Hz, 6H).

Example 270

2-(6-Methanesulfonyl-1-methyl-1H-indazol-3-yl)-5H-pyrrolo[2,3-b]pyrazine-7-carboxylic acid tert-butylamide

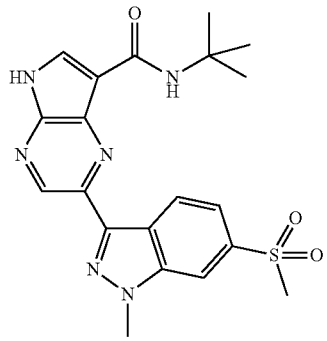 [SMILES: Cn1nc(-c2cnc3[nH]cc(C(=O)NC(C)(C)C)c3n2)c2ccc(S(C)(=O)=O)cc21]

Step 1

3-Iodo-6-methanesulfonyl-1H-indazole

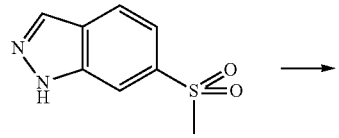

In a 25 ml round-bottomed flask, 6-methylsulfonyl-1H-indazole (250 mg, 1.27 mmol) was dissolved in DMF (3.2 ml) and potassium hydroxide (277 mg, 4.93 mmol) and iodine (647 mg, 2.55 mmol) were added. The dark brown suspension was stirred at room temperature for 4 h then quenched with aqueous 10% $Na_2S_2O_3$ and extracted with a mixture of diethyl ether and EtOAc (2×). The combined organic layers were washed twice with water and once with brine then dried over sodium sulfate, filtered and concentrated to give 165 mg of an orange oil. The combined aqueous layers were extracted twice with dichloromethane. The organic layers were combined, dried over sodium sulfate, filtered and concentrated. The residue was combined with the 165 mg orange oil from the first extraction and dried under high vacuum to afford 401 mg (98%) of 3-iodo-6-methanesulfonyl-1H-indazole as an orange solid.

Step 2

3-Iodo-6-methanesulfonyl-1-methyl-1H-indazole

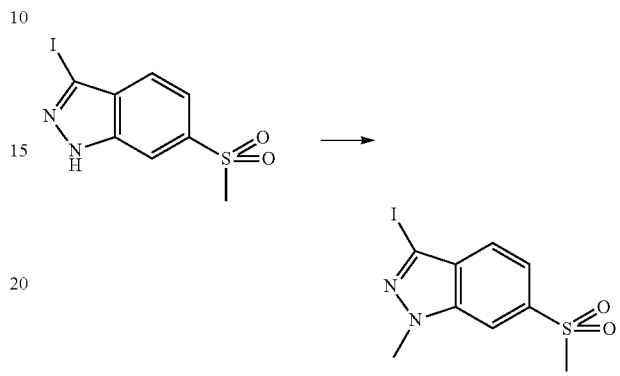

In a round-bottomed flask, 3-iodo-6-methylsulfonyl-1H-indazole (396 mg, 1.23 mmol) was dissolved in THF (4.4 ml). The orange solution was cooled to 0° C. and potassium tert-butoxide (200 mg, 1.78 mmol) was added. The reaction mixture was stirred at 0° C. for 30 min then iodomethane (0.11 ml, 1.76 mmol) was added dropwise. After the addition was complete, the ice bath was removed and the reaction mixture was stirred at room temperature for 4 h then quenched with water and extracted with EtOAc (2×). The combined organic layers were washed with water and brine then dried over sodium sulfate, filtered and concentrated. The residue was absorbed on silica gel and chromatographed with EtOAc/hexanes (gradient: 0-30% EtOAc) to give 251 mg (61%) of 3-iodo-6-methanesulfonyl-1-methyl-1H-indazole as an off-white solid. The minor regioisomer 3-iodo-6-methanesulfonyl-2-methyl-2H-indazole was also observed, but not isolated.

Step 3

6-Methanesulfonyl-1-methyl-3-tributylstannanyl-1H-indazole

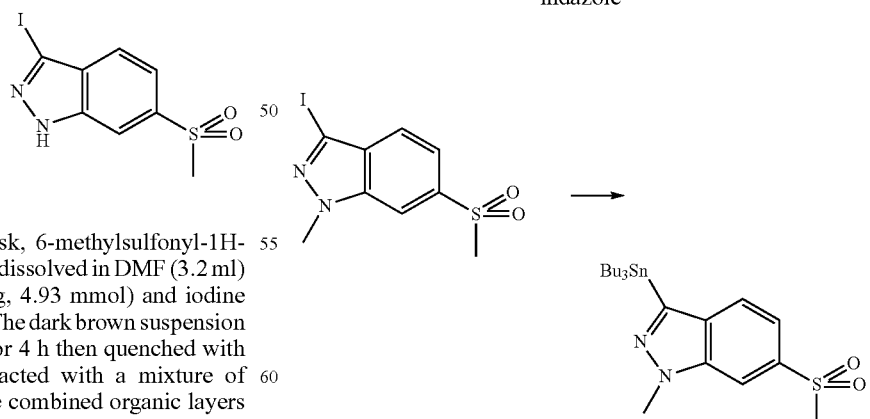

In a round-bottomed flask, 3-iodo-6-methanesulfonyl-1-methyl-1H-indazole (120 mg, 0.36 mmol) was dissolved in THF (2 ml). The colorless solution was cooled to −16° C. (NaCl/ice bath) and isopropylmagnesium chloride (2.0 M in THF, 0.25 ml, 0.50 mmol) was added dropwise. The reaction mixture was stirred at −16° C. for 1 h then tributylchlorostannane (0.12 ml, 0.44 mmol) was slowly added. The reaction mixture was allowed to warm to room temperature over 2.5 h then quenched with saturated NH$_4$Cl-solution and extracted with EtOAc (2×). The combined organic layers were washed with water and brine then dried over sodium sulfate, filtered and concentrated to afford 6-methanesulfonyl-1-methyl-3-tributylstannanyl-1H-indazole as a light yellow oil which was used without further purification.

Step 4

2-(6-Methanesulfonyl-1-methyl-1H-indazol-3-yl)-5-(2-trimethylsilanyl-ethoxymethyl)-5H-pyrrolo[2,3-b]pyrazine-7-carboxylic acid tert-butylamide nylethoxymethyl)-5H-pyrrolo[2,3-b]pyrazine-7-carboxylic acid tert-butylamide as a light brown solid.

Step 5

2-(6-Methanesulfonyl-1-methyl-1H-indazol-3-yl)-5H-pyrrolo[2,3-b]pyrazine-7-carboxylic acid tert-butylamide

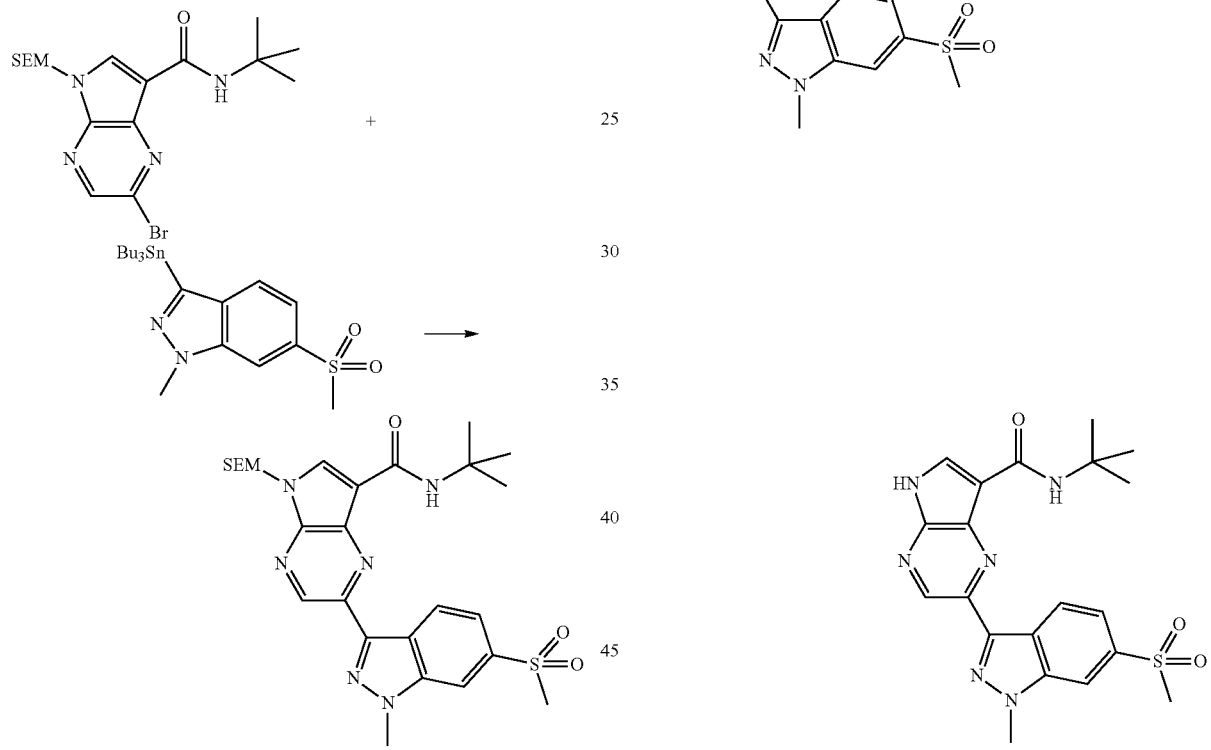

In a round-bottomed flask, 2-bromo-5-(2-trimethylsilanyl-ethoxymethyl)-5H-pyrrolo[2,3-b]pyrazine-7-carboxylic acid tert-butylamide (110 mg, 0.26 mmol) and 6-methanesulfonyl-1-methyl-3-tributylstannanyl-1H-indazole (crude from Step 3, 330 mg, 0.33 mmol) were dissolved in DMF (1.7 ml). The flask was evacuated and backfilled with argon and tetrakis(triphenylphosphine)palladium (0) (15 mg, 0.013 mmol) and copper (I) iodide (10 mg, 0.053 mmol) were added. The reaction mixture was stirred at 90° C. for 3 h then allowed to cool to room temperature overnight. The reaction was quenched with water and extracted with diethyl ether (2×) and EtOAc. The combined organic layers were washed twice with water and once with brine then dried over sodium sulfate, filtered and concentrated. The residue was chromatographed over 25 g silica gel with EtOAc/hexanes (gradient: 0-40% EtOAc) to afford 79 mg (55%) of 2-(6-methanesulfonyl-1-methyl-1H-indazol-3-yl)-5-(2-trimethylsila- In a round-bottomed flask, 2-(6-methanesulfonyl-1-methyl-1H-indazol-3-yl)-5-(2-trimethylsilanyl-ethoxymethyl)-5H-pyrrolo[2,3-b]pyrazine-7-carboxylic acid tert-butylamide (76 mg, 0.137 mmol) was dissolved in dichloromethane (0.7 ml) and trifluoroacetic acid (0.42 ml, 5.45 mmol) was added. The reaction mixture was stirred at room temperature for 2.5 h then concentrated. The residue was dissolved in dichloromethane (0.7 ml) and ethylenediamine (0.55 ml, 8.14 mmol) was added. The reaction was stirred at room temperature for 1 h then water and ethyl acetate were added. The resulting suspension was filtered and washed with hot water and ethyl acetate. The product collected was dried under high vacuum to provide 39 mg (67%) of 2-(6-methanesulfonyl-1-methyl-1H-indazol-3-yl)-5H-pyrrolo[2,3-b]pyrazine-7-carboxylic acid tert-butylamide as a light yellow powder. MS: (2M+Na)$^+$=875; $^1$H NMR (DMSO-d$_6$, 300 MHz): δ (ppm) 12.89 (br. s, 1H), 9.13 (s, 1H), 8.71 (d, J=8.3 Hz, 1H), 8.46 (s, 1H), 8.42 (s, 1H), 7.92 (s, 1H), 7.76 (d, J=8.7 Hz, 1H), 4.31 (s, 3H), 3.35 (s, 3H), 1.55 (s, 9H).

Example 271

2-(6-Fluoro-1-methyl-1H-indazol-3-yl)-5H-pyrrolo[2,3-b]pyrazine-7-carboxylic acid (cis-3-amino-cyclobutyl)-amide

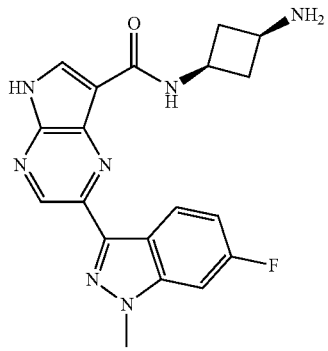 [SMILES: Cn1nc(-c2cnc3[nH]cc(C(=O)N[C@H]4C[C@@H](N)C4)c3n2)c2ccc(F)cc21]

Step 1

(cis-3-{[2-(6-Fluoro-1-methyl-1H-indazol-3-yl)-5-(2-trimethylsilanyl-ethoxymethyl)-5H-pyrrolo[2,3-b]pyrazine-7-carbonyl]-amino}-cyclobutyl)-carbamic acid tert-butyl ester

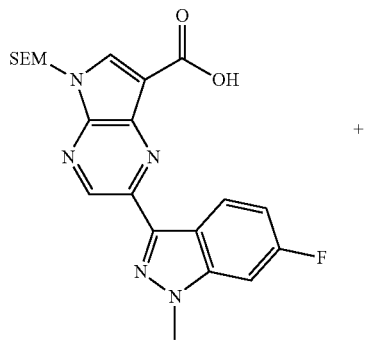

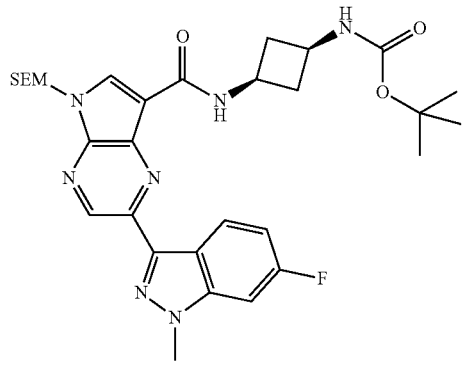

A round-bottomed flask was charged with 2-(6-fluoro-1-methyl-1H-indazol-3-yl)-5-(2-trimethylsilanyl-ethoxymethyl)-5H-pyrrolo[2,3-b]pyrazine-7-carboxylic acid (110 mg, 0.25 mmol) and cis-tert-butyl 3-aminocyclobutylcarbamate (65 mg, 0.35 mmol). Then DMF (1.2 ml) was added followed by N,N-diisopropylethylamine (0.12 ml, 0.69 mmol) and HATU (104 mg, 0.27 mmol). The yellow reaction mixture was stirred at room temperature overnight then water and petroleum ether were added. The suspension was filtered and the solids were washed with water and a little petroleum ether. The product collected was dried under high vacuum to afford 145 mg (95%) of (cis-3-{[2-(6-fluoro-1-methyl-1H-indazol-3-yl)-5-(2-trimethylsilanylethoxymethyl)-5H-pyrrolo[2,3-b]pyrazine-7-carbonyl]-amino}-cyclobutyl)-carbamic acid tert-butyl ester as an off-white powder.

Step 2

2-(6-Fluoro-1-methyl-1H-indazol-3-yl)-5H-pyrrolo[2,3-b]pyrazine-7-carboxylic acid (cis-3-amino-cyclobutyl)-amide

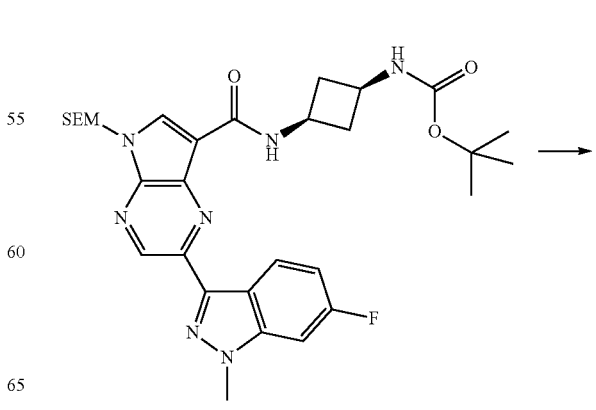

903
-continued

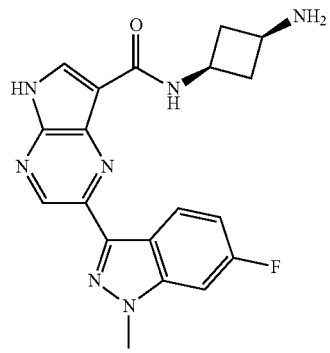

In a round-bottomed flask, (cis-3-{[2-(6-fluoro-1-methyl-1H-indazol-3-yl)-5-(2-trimethylsilanyl-ethoxymethyl)-5H-pyrrolo[2,3-b]pyrazine-7-carbonyl]-amino}-cyclobutyl)carbamic acid tert-butyl ester (144 mg, 0.236 mmol) was dissolved in dichloromethane (1.2 ml) and trifluoroacetic acid (0.73 ml, 9.48 mmol) was added. The reaction mixture was stirred at room temperature for 2 h then concentrated. The residue was suspended in dichloromethane (1.2 ml) and ethylenediamine (0.96 ml, 14.2 mmol) was added. The light yellow suspension was stirred at room temperature for 1 h then water and ethyl acetate were added. The suspension was filtered and washed with hot water and ethyl acetate. The product was dried under high vacuum to provide 86 mg (91%) of 2-(6-fluoro-1-methyl-1H-indazol-3-yl)-5H-pyrrolo[2,3-b]pyrazine-7-carboxylic acid (cis-3-amino-cyclobutyl)-amide as a light yellow powder. MS: (M+H)$^+$=380; $^1$H NMR (DMSO-d$_6$, 300 MHz): δ (ppm) 9.09 (s, 1H), 8.54 (dd, J=8.7, 5.3 Hz, 1H), 8.41 (s, 1H), 8.28 (d, J=7.6 Hz, 1H), 7.71 (dd, J=9.8, 1.9 Hz, 1H), 7.28 (td, J=9.1, 1.9 Hz, 1H), 5.54 (br. s., 2H), 4.15 (s, 3H), 4.04-4.18 (m, 1H), 3.07-3.22 (m, 1H), 2.65-2.80 (m, 2H), 1.66-1.80 (m, 2H).

Example 272

2-(1-Methyl-1,4,5,6,7,8-hexahydrocycloheptapyrazol-3-yl)-5H-pyrrolo[2,3-b]pyrazine-7-carboxylic acid tert-butylamide

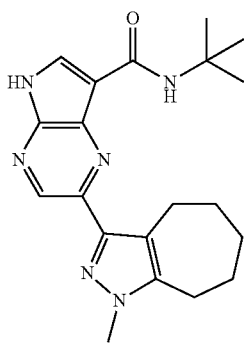 [SMILES: Cn1nc(-c2cnc3[nH]cc(C(=O)NC(C)(C)C)c3n2)c2c1CCCCC2]

904

Step 1

2-[1-Hydroxy-meth-(Z)-ylidene]-cycloheptanone

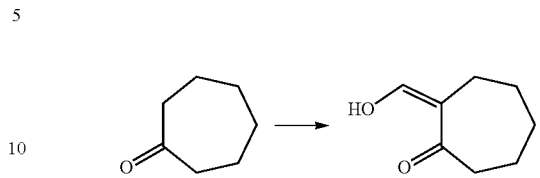

To a suspension of sodium hydride (60% dispersion in mineral oil, 535 mg, 13.4 mmol) in diethyl ether (25 mL) at 0° C. was added ethanol (0.06 ml, 1.03 mmol) dropwise. The grey suspension was stirred at 0° C. for 20 min. A solution of cycloheptanone (1.58 ml, 13.4 mmol) and ethyl formate (1.63 ml, 20.1 mmol) in diethyl ether (3 mL) was added dropwise over 10 min. The pale yellow heterogeneous reaction mixture was stirred at 0° C. for 1 h then warmed to room temperature for 4 h. The reaction was carefully quenched with ethanol (2 mL) then water (25 mL) was added. The layers were separated and the aqueous phase was washed with diethyl ether. The organic layers were set aside and later discarded. The aqueous layer was acidified with 1M HCl until pH=2 and then extracted with diethyl ether (2×). The combined organic layers were dried over MgSO$_4$ and concentrated to afford 1.41 g (75%) of 2-[1-hydroxy-meth-(Z)-ylidene]-cycloheptanone as a yellow oil. $^1$H NMR (CDCl$_3$, 400 MHz): δ (ppm) 14.69 (d, J=8.8 Hz, 1H), 7.66 (d, J=8.1 Hz, 1H), 2.52-2.61 (m, 2H), 2.23-2.32 (m, 2H), 1.67-1.82 (m, 4H), 1.58-1.67 (m, 2H).

Step 2

1,4,5,6,7,8-Hexahydrocycloheptapyrazole

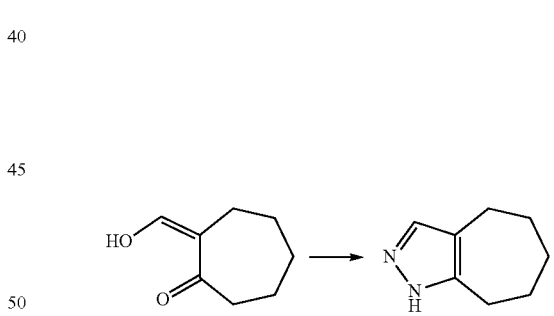

To a solution of 2-[1-hydroxy-meth-(Z)-ylidene]-cycloheptanone (1.35 g, 9.63 mmol) in MeOH (10 mL) at 0° C. was added hydrazine (0.30 mL, 9.63 mmol) dropwise. The yellow reaction mixture was stirred at room temperature for 30 min then concentrated. The residue was dissolved in CH$_2$Cl$_2$ and washed with water. The organic layer was dried over MgSO$_4$ and concentrated to provide 1.24 g (95%) of 1,4,5,6,7,8-hexahydrocycloheptapyrazole as a pale yellow solid. $^1$H NMR (CDCl₃, 400 MHz): δ (ppm) 7.28 (s, 1H), 2.75-2.82 (m, 2H), 2.54-2.62 (m, 2H), 1.80-1.91 (m, 2H), 1.60-1.75 (m, 4H).

Step 3

3-Iodo-1,4,5,6,7,8-hexahydrocycloheptapyrazole

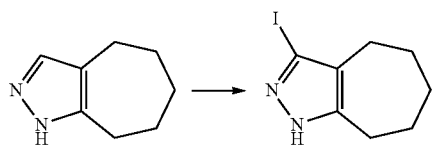 [SMILES: c1n[nH]c2c1CCCCC2 ; Ic1n[nH]c2c1CCCCC2]

To a solution of 1,4,5,6,7,8-hexahydrocycloheptapyrazole (500 mg, 3.67 mmol) in DMF (8 ml) at room temperature was added powdered potassium hydroxide (618 mg, 11.0 mmol) and iodine (1.86 g, 7.34 mmol). The maroon reaction mixture was stirred at room temperature for 1 h then quenched with aqueous 10% Na₂S₂O₃, diluted with water, and extracted with EtOAc (2×). The combined organics were washed with water (3×), dried over MgSO₄ and concentrated. The residue was purified by SiO₂ chromatography with 20% to 50% EtOAc/hexanes to afford 600 mg (62%) of 3-iodo-1,4,5,6,7,8-hexahydrocycloheptapyrazole as a white solid. ¹H NMR (CDCl₃, 400 MHz): δ (ppm) 2.75-2.84 (m, 2H), 2.46-2.55 (m, 2H), 1.80-1.91 (m, 2H), 1.63-1.77 (m, 4H).

Step 4

3-Iodo-1-methyl-1,4,5,6,7,8-hexahydrocycloheptapyrazole and 3-Iodo-2-methyl-2,4,5,6,7,8-hexahydrocycloheptapyrazole

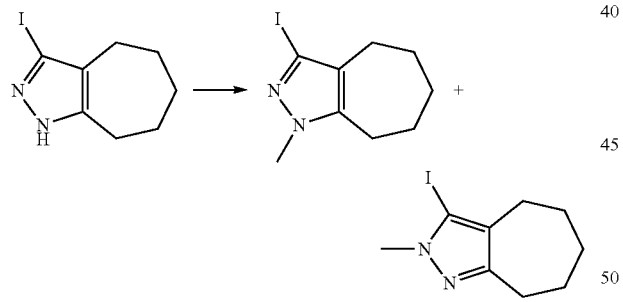

To a solution of 3-iodo-1,4,5,6,7,8-hexahydrocycloheptapyrazole (600 mg, 2.29 mmol) in THF (8 ml) at 0° C. was added KOt-Bu (360 mg, 3.2 mmol). The reaction mixture was stirred at 0° C. for 30 min then iodomethane (0.20 ml, 3.2 mmol) was added. Stirring was continued at 0° C. for 30 min then at room temperature for 2 h. The reaction was quenched with water and extracted with EtOAc (2×). The organics were dried over MgSO₄ and concentrated. The residue was absorbed on SiO₂ and chromatographed with 10% to 20% EtOAc/hexanes to afford 387 mg (61%) of 3-iodo-1-methyl-1,4,5,6,7,8-hexahydrocycloheptapyrazole as a colorless oil. ¹H NMR (CDCl₃, 300 MHz): δ (ppm) 3.77 (s, 3H), 2.65-2.76 (m, 2H), 2.43-2.54 (m, 2H), 1.77-1.88 (m, 2H), 1.59-1.76 (m, 4H). Also isolated 200 mg (32%) of the less polar 3-iodo-2-methyl-2,4,5,6,7,8-hexahydrocycloheptapyrazole as a white solid. ¹H NMR (CDCl₃, 300 MHz): δ (ppm) 3.84 (s, 3H), 2.70-2.79 (m, 2H), 2.42-2.51 (m, 2H), 1.77-1.88 (m, 2H), 1.57-1.73 (m, 4H).

Step 5

1-Methyl-3-tributylstannanyl-1,4,5,6,7,8-hexahydrocycloheptapyrazole

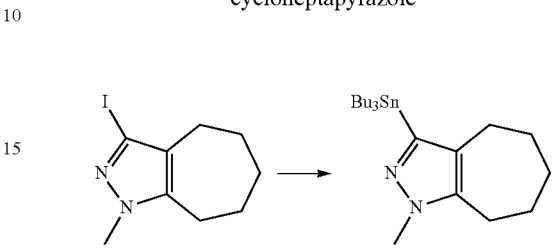

To a solution of 3-iodo-2-methyl-2,4,5,6,7,8-hexahydrocycloheptapyrazole (180 mg, 0.62 mmol) in THF (3 mL) at −10° C. (ice/acetone) was slowly added isopropylmagnesium chloride (2.0 M in THF, 0.37 mL, 0.74 mmol). The reaction mixture was stirred at −10° C. for 30 min then additional isopropylmagnesium chloride (2.0 M in THF, 0.10 mL, 0.20 mmol) was added. Stirring was continued at −10° C. for 20 min then tributylchlorostannane (0.20 mL, 0.74 mmol) was added dropwise. The reaction mixture was warmed to room temperature and stirred for 1 h then quenched with water and extracted with EtOAc (2×). The organics were dried over MgSO₄ and concentrated. The residue was purified by silica gel chromatography with 0% to 10% EtOAc/hexanes (0.5% Et₃N spike in hexanes) to afford 76 mg (28%) of 1-methyl-3-tributylstannanyl-1,4,5,6,7,8-hexahydrocycloheptapyrazole as a colorless oil. ¹H NMR (CDCl₃, 400 MHz): δ (ppm) 3.82 (s, 3H), 2.66-2.76 (m, 2H), 2.50-2.60 (m, 2H), 1.80-1.89 (m, 2H), 1.61-1.74 (m, 4H), 1.51-1.61 (m, 6H), 1.29-1.41 (m, 6H), 1.04-1.12 (m, 6H), 0.91 (t, J=7.3 Hz, 9H).

Step 6

2-(1-Methyl-1,4,5,6,7,8-hexahydrocycloheptapyrazol-3-yl)-5-(2-trimethylsilanyl-ethoxymethyl)-5H-pyrrolo[2,3-b]pyrazine-7-carboxylic acid tert-butylamide

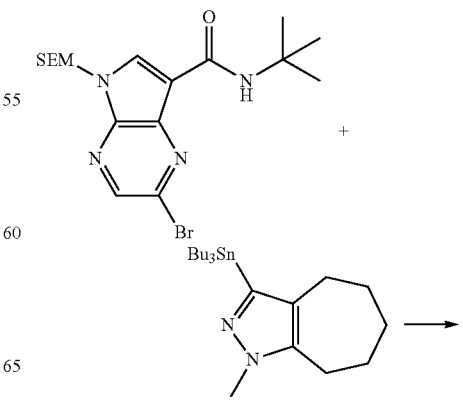

907

-continued

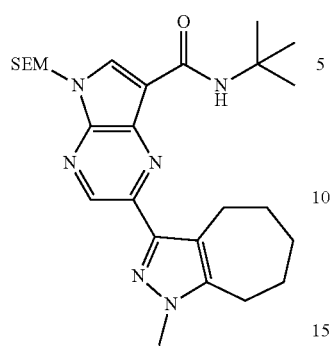

To a solution of 1-methyl-3-tributylstannyl-1,4,5,6,7,8-hexahydrocycloheptapyrazole (74 mg, 0.17 mmol) and 2-bromo-5-(2-trimethylsilanyl-ethoxymethyl)-5H-pyrrolo[2,3-b]pyrazine-7-carboxylic acid tert-butylamide (60 mg, 0.14 mmol) in DMF (2 mL) were added Pd(PPh$_3$)$_4$ (8 mg, 0.007 mmol) and copper(I) iodide (5 mg, 0.028 mmol). The reaction mixture was heated at 80° C. for 1.5 h then cooled to room temperature, quenched with water and extracted with EtOAc (2×). The combined organics were washed with water (3×) and brine then dried over MgSO$_4$ and concentrated. The residue was absorbed on SiO$_2$ and chromatographed with 20% to 50% EtOAc/hexanes to isolate 42 mg (60%) of 2-(1-methyl-1,4,5,6,7,8-hexahydrocycloheptapyrazol-3-yl)-5-(2-trimethylsilanyl-ethoxymethyl)-5H-pyrrolo[2,3-b]pyrazine-7-carboxylic acid tert-butylamide as a pale orange-yellow solid.

Step 7

2-(1-Methyl-1,4,5,6,7,8-hexahydrocycloheptapyrazol-3-yl)-5H-pyrrolo[2,3-b]pyrazine-7-carboxylic acid tert-butylamide

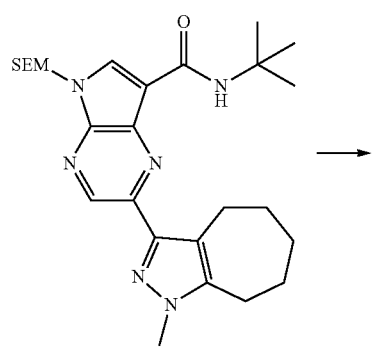

908

-continued

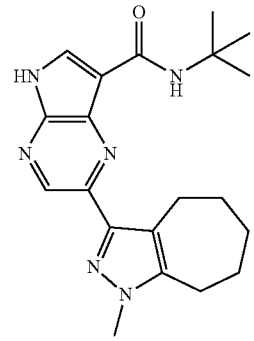

To a solution of 2-(1-methyl-1,4,5,6,7,8-hexahydrocycloheptapyrazol-3-yl)-5-(2-trimethylsilanyl-ethoxymethyl)-5H-pyrrolo[2,3-b]pyrazine-7-carboxylic acid tert-butylamide (40 mg, 0.08 mmol) in CH$_2$Cl$_2$ (2 mL) was added TFA (1.0 mL, 13.0 mmol). The yellow reaction mixture was stirred at room temperature for 3 h then concentrated. The residue was redissolved in CH$_2$Cl$_2$ (2 mL) and ethylenediamine (0.1 mL, 1.48 mmol) was added. The reaction mixture was stirred at room temperature for 0.5 h then concentrated and directly purified by silica gel chromatography with 0% to 3% MeOH/EtOAc to isolate 20 mg (68%) of 2-(1-methyl-1,4,5,6,7,8-hexahydrocycloheptapyrazol-3-yl)-5H-pyrrolo[2,3-b]pyrazine-7-carboxylic acid tert-butylamide as an off-white solid. MS: (M+Na)$^+$=389; $^1$H NMR (DMSO-d$_6$, 300 MHz): δ (ppm) 12.63 (br. s., 1H), 8.80 (s, 1H), 8.27 (s, 1H), 7.83 (s, 1H), 3.81 (s, 3H), 3.02-3.12 (m, 2H), 2.74-2.83 (m, 2H), 1.82 (br. s., 2H), 1.57-1.73 (m, 4H), 1.44 (s, 9H).

Example 273

2-(5-Hydroxymethyl-1-methyl-1H-indazol-3-yl)-5H-pyrrolo[2,3-b]pyrazine-7-carboxylic acid tert-butylamide

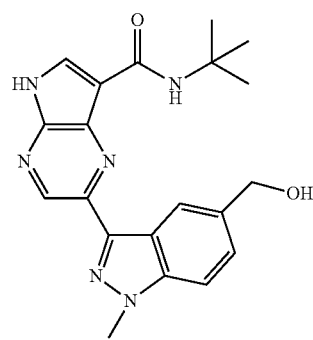 [SMILES: Cn1nc(-c2cnc3[nH]cc(C(=O)NC(C)(C)C)c3n2)c2cc(CO)ccc21]

Step 1

3-Iodo-1-methyl-1H-indazole-5-carboxylic acid methyl ester

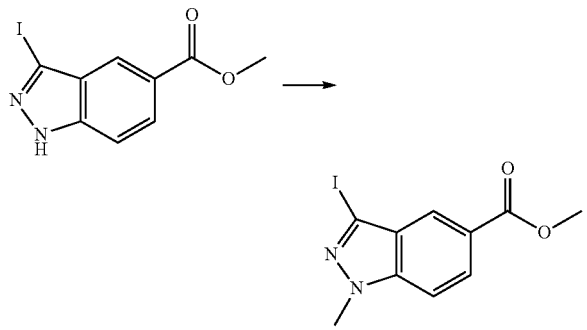

To a solution of 3-iodo-1H-indazole-5-carboxylic acid methyl ester (1.0 g, 3.31 mmol) in THF (12 mL) at 0° C. was added KOt-Bu (520 mg, 4.63 mmol). The reaction mixture was stirred at 0° C. for 30 min then added iodomethane (0.29 mL, 4.63 mmol). Stirred at 0° C. for 30 min then warmed to room temperature and stirred for 2 h. The reaction was quenched with water and extracted with EtOAc (2×) then with CH$_2$Cl$_2$ (2×). The combined organics were dried over MgSO$_4$ and concentrated to afford 950 mg of 3-iodo-1-methyl-1H-indazole-5-carboxylic acid methyl ester a pale yellow solid. NMR analysis revealed an 8:1 mixture of N1:N2 alkylated regioisomers. Major: $^1$H NMR (CDCl$_3$, 300 MHz): δ (ppm) 8.25 (s, 1H), 8.13 (dd, J=8.7, 1.5 Hz, 1H), 7.39 (d, J=8.7 Hz, 1H), 4.13 (s, 3H), 3.98 (s, 3H).

Step 2

(3-Iodo-1-methyl-1H-indazol-5-yl)-methanol

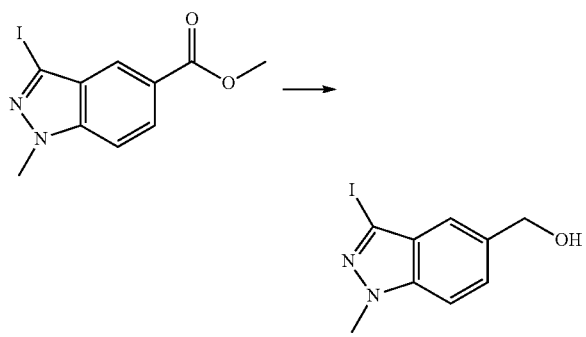

To a solution of 3-iodo-1-methyl-1H-indazole-5-carboxylic acid methyl ester (0.95 g, 3.01 mmol) in CH$_2$Cl$_2$ (30 mL) at 0° C. was slowly added DIBAL-H (1.18 mL, 6.61 mmol). The reaction mixture was stirred at 0° C. for 1.5 h. Carefully quenched with MeOH (1 mL) then diluted with CH$_2$Cl$_2$ (20 mL) and added saturated aqueous Na+K+ tartrate (30 mL). The biphasic mixture was stirred vigorously at room temp for 1 h. The layers were separated and the aqueous phase was extracted with CH$_2$Cl$_2$. The combined organics were washed with water then dried over MgSO$_4$ and concentrated to afford 810 mg of (3-iodo-1-methyl-1H-indazol-5-yl)methanol as a yellow waxy solid.

Step 3

5-(tert-Butyl-dimethylsilanyloxymethyl)-3-iodo-1-methyl-1H-indazole

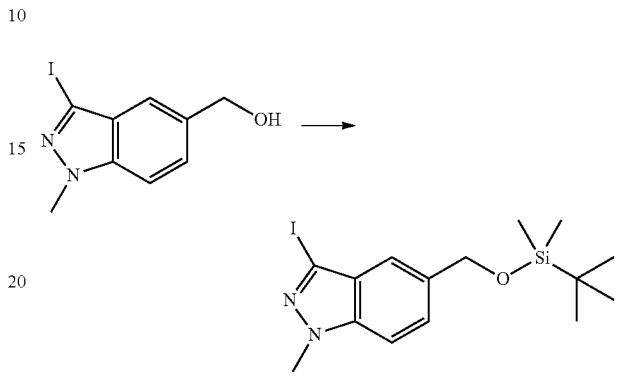

To a solution of (3-iodo-1-methyl-1H-indazol-5-yl)-methanol (810 mg, 2.81 mmol) in DMF (9 mL) was added imidazole (479 mg, 7.03 mmol) followed by tert-butyldimethylsilyl chloride (466 mg, 3.09 mmol). The reaction mixture was stirred at room temperature overnight then quenched with water and extracted with EtOAc (2×). The combined organics were washed with water (3×) then dried over MgSO$_4$ and concentrated. The residue was purified by silica gel chromatography with 10% EtOAc/hexanes to afford 732 mg (65%) of 5-(tert-butyldimethylsilanyloxymethyl)-3-iodo-1-methyl-1H-indazole as a pale yellow solid. $^1$H NMR (CDCl$_3$, 300 MHz): δ (ppm) 7.26-7.34 (m, 2H), 7.17-7.23 (m, 1H), 4.73 (s, 2H), 3.97 (s, 3H), 0.84 (s, 9H), 0.00 (s, 6H).

Step 4

5-(tert-Butyl-dimethyl-silanyloxymethyl)-1-methyl-3-tributylstannanyl-1H-indazole

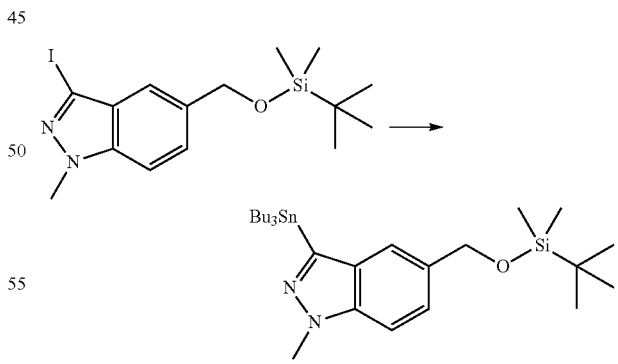

To a solution of 5-(tert-butyl-dimethylsilanyloxymethyl)-3-iodo-1-methyl-1H-indazole (201 mg, 0.50 mmol) in THF (3 mL) at −10° C. (ice/acetone) was added isopropylmagnesium chloride (2.0 M in THF) (0.30 mL, 0.60 mmol). The pale yellow reaction mixture was stirred at −10° C. for 20 min then tributylchlorostannane (0.16 mL, 0.60 mmol) was added. Stirring was continued at −10° C. for 30 min then at room temperature for 1 h. The reaction was quenched with water

911 and extracted with EtOAc (2×). The combined organics were dried over MgSO$_4$ and concentrated to give 5-(tert-butyl-dimethyl-silanyloxymethyl)-1-methyl-3-tributylstannanyl-1H-indazole as an almost colorless oil which was used without further purification.

Step 5

2-[5-(tert-Butyl-dimethyl-silanyloxymethyl)-1-methyl-1H-indazol-3-yl]-5-(2-trimethylsilanylethoxymethyl)-5H-pyrrolo[2,3-b]pyrazine-7-carboxylic acid tert-butylamide

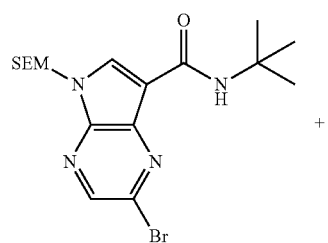

+

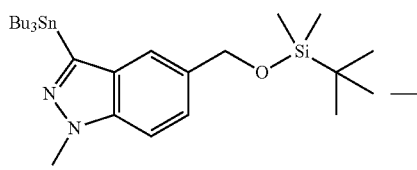

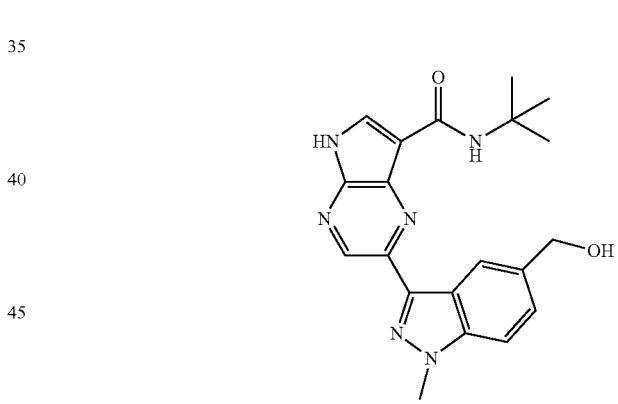

To a solution of 5-(tert-butyl-dimethyl-silanyloxymethyl)-1-methyl-3-tributylstannanyl-1H-indazole (265 mg, 0.47 mmol) and 2-bromo-5-(2-trimethylsilanyl-ethoxymethyl)-5H-pyrrolo[2,3-b]pyrazine-7-carboxylic acid tert-butylamide (100 mg, 0.23 mmol) in DMF (2 mL) were added Pd(PPh$_3$)$_4$ (14 mg, 0.012 mmol) and copper(I) iodide (9 mg, 0.047 mmol). The reaction mixture was heated at 90° C. for 1 h then cooled to room temperature, quenched with water and extracted with EtOAc (2×). The combined organics were washed with water (3×) and brine then dried over MgSO$_4$ and concentrated. The residue was absorbed on silica gel and chromatographed with 20% to 50% EtOAc/hexanes to isolate 106 mg (73%) of 2-[5-(tert-butyldimethyl-silanyloxymethyl)-1-methyl-1H-indazol-3-yl]-5-(2-trimethylsilanyl-

912 ethoxymethyl)-5H-pyrrolo[2,3-b]pyrazine-7-carboxylic acid tert-butylamide as a beige solid.

Step 6

2-(5-Hydroxymethyl-1-methyl-1H-indazol-3-yl)-5H-pyrrolo[2,3-b]pyrazine-7-carboxylic acid tert-butylamide

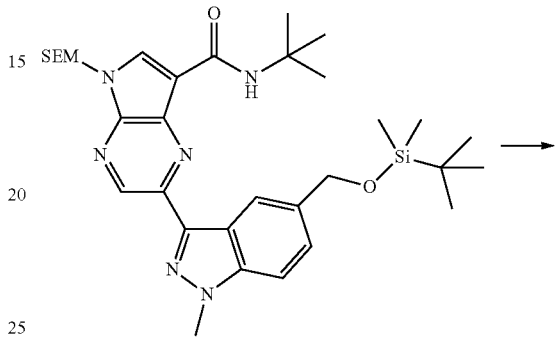

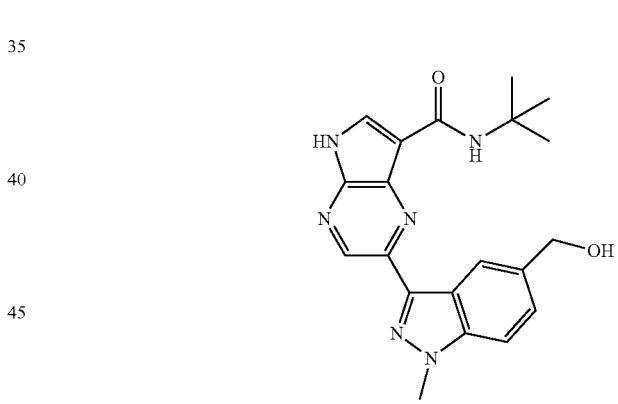

To a solution of 2-[5-(tert-butyl-dimethyl-silanyloxymethyl)-1-methyl-1H-indazol-3-yl]-5-(2-trimethylsilanyl-ethoxymethyl)-5H-pyrrolo[2,3-b]pyrazine-7-carboxylic acid tert-butylamide (106 mg, 0.17 mmol) in THF (2 mL) was added tetrabutylammonium fluoride (1.0 M in THF, 1.7 mL, 1.7 mmol). The reaction mixture was stirred at room temperature for 10 min then heated at reflux for 2 h. After cooling to room temperature, the reaction was quenched with water and extracted with EtOAc and then with 5% MeOH/CH$_2$Cl$_2$. The combined organic layers were dried over MgSO$_4$ and concentrated. The residue was triturated with EtOAc/MeOH and the solids collected via filtration to afford 30 mg (47%) of 2-(5-hydroxymethyl-1-methyl-1H-indazol-3-yl)-5H-pyrrolo[2,3-b]pyrazine-7-carboxylic acid tert-butylamide as a light yellow solid.

MS: (M+Na)$^+$=401; $^1$H NMR (DMSO-d$_6$, 300 MHz): δ (ppm) 12.76 (br. s., 1H), 9.04 (s, 1H), 8.35 (s, 1H), 8.31 (s, 1H), 8.00 (s, 1H), 7.71 (d, J=8.7 Hz, 1H), 7.48 (d, J=8.7 Hz, 1H), 5.20 (t, J=5.5 Hz, 1H), 4.64 (d, J=5.3 Hz, 2H), 4.16 (s, 3H), 1.49 (s, 9H).

Example 274

2-[5-Difluoromethoxy-1-(1-methyl-1H-pyrazol-4-ylmethyl)-1H-indazol-3-yl]-5H-pyrrolo[2,3-b]pyrazine-7-carboxylic acid tert-butylamide

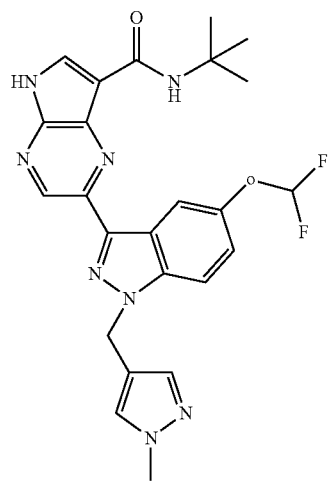

Step 1

(1-Methyl-1H-pyrazol-4-yl)-methanol

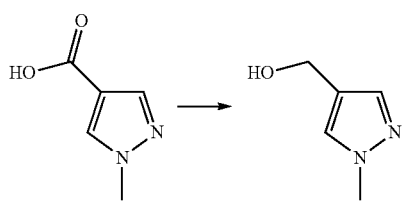

To a solution of 1-methyl-1H-pyrazole-4-carboxylic acid (0.50 g, 3.96 mmol) in THF (10 mL) at 0° C. was added triethylamine (61 mL, 4.36 mmol) followed by ethyl chloroformate (0.42 mL, 4.36 mmol). The thick slurry was stirred at 0° C. for 15 min then a solution of sodium borohydride (450 mg, 11.9 mmol) in water (4 mL) was carefully added portionwise via pipet. Vigorous gas evolution was observed. The reaction was stirred at 0° C. for 30 min then diluted with water and saturated aqueous NH$_4$Cl and extracted with EtOAc (3×). The combined organics were dried over MgSO$_4$ and concentrated. The residue was purified by silica gel chromatography with 30% to 80% EtOAc/hexanes to isolate 150 mg (34%) of (1-methyl-1H-pyrazol-4-yl)-methanol as a waxy white solid.

$^1$H NMR (CDCl$_3$, 300 MHz): δ (ppm) 7.69 (s, 1H), 7.49 (s, 1H), 4.59 (s, 2H), 3.99 (s, 3H).

Step 2

Methanesulfonic acid 1-methyl-1H-pyrazol-4-ylmethyl ester

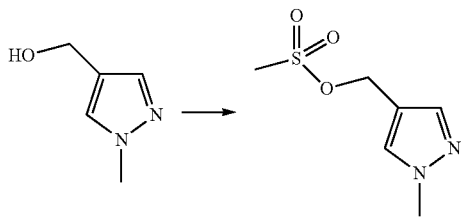

To a partial suspension of (1-methyl-1H-pyrazol-4-yl)methanol (75 mg, 0.67 mmol) in CH$_2$Cl$_2$ (4 mL) at 0° C. was added triethylamine (0.19 mL, 1.34 mmol) followed by methanesulfonyl chloride (57 μL, 0.74 mmol). The cloudy reaction mixture was stirred at 0° C. for 1 h then quenched with water and extracted with CH$_2$Cl$_2$. The organics were dried over MgSO$_4$ and concentrated to give 110 mg of methanesulfonic acid 1-methyl-1H-pyrazol-4-ylmethyl ester a colorless oil which was used without further purification.

Step 3

2-[5-Difluoromethoxy-1-(1-methyl-1H-pyrazol-4-ylmethyl)-1H-indazol-3-yl]-5-(2-trimethylsilanyl-ethoxymethyl)-5H-pyrrolo[2,3-b]pyrazine-7-carboxylic acid tert-butylamide

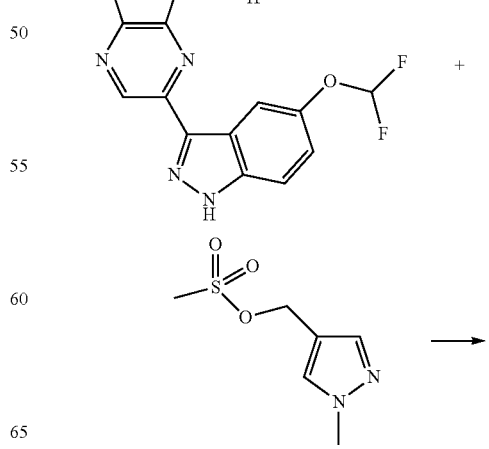

915
-continued

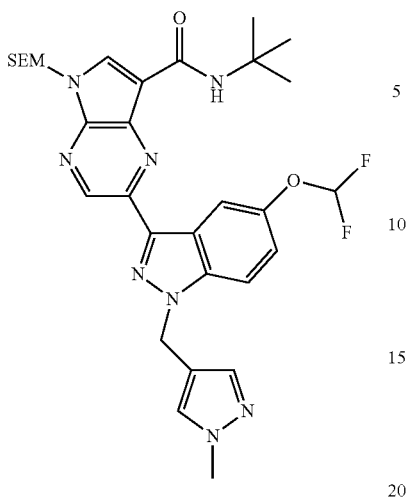

To a solution of methanesulfonic acid 1-methyl-1H-pyrazol-4-ylmethyl ester (108 mg, 0.57 mmol) in DMF (2 mL) were added 2-(5-difluoromethoxy-1H-indazol-3-yl)-5-(2-trimethylsilanyl-ethoxymethyl)-5H-pyrrolo[2,3-b]pyrazine-7-carboxylic acid tert-butylamide (100 mg, 0.19 mmol) and Cs$_2$CO$_3$ (184 mg, 0.57 mmol). The bright yellow reaction mixture was heated at 90° C. for 2 h then cooled to room temperature, quenched with water and extracted with EtOAc (2×). The combined organics were washed with water (3×) dried over MgSO$_4$ and concentrated. The residue was chromatographed with 50% to 100% EtOAc/hexanes to afford 60 mg (51%) of 2-[5-difluoromethoxy-1-(1-methyl-1H-pyrazol-4-ylmethyl)-1H-indazol-3-yl]-5-(2-trimethylsilanyl-ethoxymethyl)-5H-pyrrolo[2,3-b]pyrazine-7-carboxylic acid tert-butylamide as a light yellow solid.

Step 4

2-[5-Difluoromethoxy-1-(1-methyl-1H-pyrazol-4-ylmethyl)-1H-indazol-3-yl]-5H-pyrrolo[2,3-b]pyrazine-7-carboxylic acid tert-butylamide

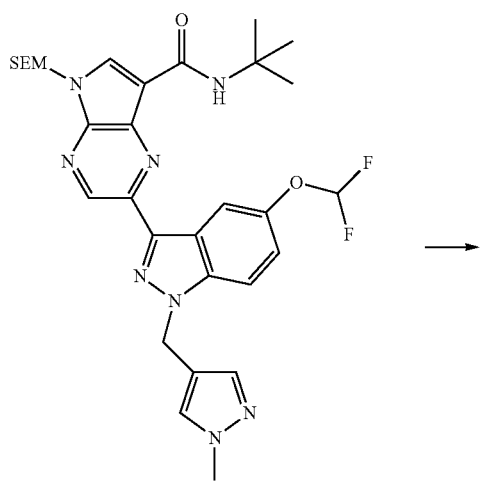

916
-continued

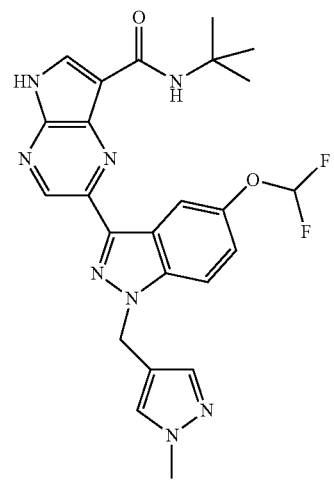

To a solution of 2-[5-difluoromethoxy-1-(1-methyl-1H-pyrazol-4-ylmethyl)-1H-indazol-3-yl]-5-(2-trimethylsilanyl-ethoxymethyl)-5H-pyrrolo[2,3-b]pyrazine-7-carboxylic acid tert-butylamide (56 mg, 0.09 mmol) in CH$_2$Cl$_2$ (2 mL) was added trifluoroacetic acid (0.5 mL, 6.5 mmol). The reaction mixture was stirred at room temperature for 3 h then concentrated. The residue was dissolved in CH$_2$Cl$_2$ (2 mL) and ethylenediamine (0.2 mL, 2.96 mmol) was added. The reaction mixture was stirred at room temperature for 30 min then quenched with water and extracted with 5% MeOH/CH$_2$Cl$_2$. The organics were dried over MgSO$_4$ and concentrated. The residue was triturated with EtOAc/Et$_2$O and the product was collected via filtration to afford 29 mg (65%) of 2-[5-difluoromethoxy-1-(1-methyl-1H-pyrazol-4-ylmethyl)-1H-indazol-3-yl]-5H-pyrrolo[2,3-b]pyrazine-7-carboxylic acid tert-butylamide as a light yellow solid. MS: (M+Na)$^+$=517; $^1$H NMR (DMSO-d$_6$, 300 MHz): δ (ppm) 12.62 (br. s., 1H), 8.97 (s, 1H), 8.26 (s, 1H), 8.06 (d, J=1.9 Hz, 1H), 7.85 (d, J=9.1 Hz, 1H), 7.74 (s, 1H), 7.65 (s, 1H), 7.38 (s, 1H), 7.27 (dd, J=9.1, 1.9 Hz, 1H), 7.06 (7, J=75 Hz, 1H), 5.51 (s, 2H), 3.19 (s, 6H), 1.36 (s, 9H).

Example 275

2-(5,6,7,8-Tetrahydro-imidazo[1,5-a]pyridin-1-yl)-5H-pyrrolo[2,3-b]pyrazine-7-carboxylic acid tert-butylamide

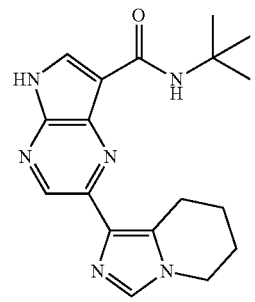 [SMILES: CC(C)(C)NC(=O)c1c[nH]c2ncc(-c3ncn4c3CCCC4)nc12]

Step 1

1-Iodo-imidazo[1,5-a]pyridine

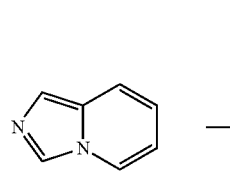 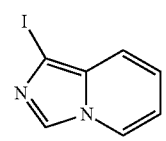

To a solution of imidazo[1,5-a]pyridine (0.50 g, 4.23 mmol) in EtOH (8 mL) and water (4 mL) was added sodium bicarbonate (1.07 g, 12.7 mmol) followed by iodine (1.61 g, 6.35 mmol). The dark maroon-brown heterogeneous reaction mixture was stirred at room temperature overnight then quenched with aqueous 10% $Na_2S_2O_3$, diluted with water and extracted with EtOAc (3×). The combined organics were washed with water, dried over $MgSO_4$ and concentrated. The residue was purified by silica gel chromatography with 20% to 50% EtOAc/hexanes to afford 649 mg (63%) of 1-iodo-imidazo[1,5-a]pyridine as a light brown solid (light sensitive). $^1H$ NMR ($CDCl_3$, 300 MHz): δ (ppm) 8.13 (s, 1H), 7.92 (d, J=6.8 Hz, 1H), 7.33 (d, J=9.4 Hz, 1H), 6.80 (dd, J=9.4, 6.8 Hz, 1H), 6.56-6.69 (m, 1H).

Step 2

1-Tributylstannanyl-imidazo[1,5-a]pyridine

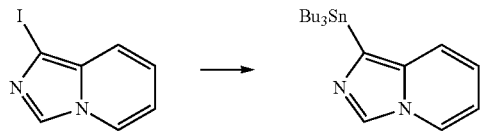

To a solution of 1-iodo-imidazo[1,5-a]pyridine (150 mg, 0.62 mmol) in THF (3 mL) at −10° C. (ice/acetone) was added isopropylmagnesium chloride (2.0 M in THF, 37 mL, 0.74 mmol). The reaction mixture was stirred at −10° C. for 20 min then tributylchlorostannane (0.20 mL, 0.74 mmol) was added. The reaction was stirred at −10° C. for 30 min then warmed to room temperature and stirred for 1 h. The reaction was quenched with water and extracted with EtOAc (2×). The combined organics were dried over $MgSO_4$ and concentrated to afford 1-tributylstannanyl-imidazo[1,5-a]pyridine as a yellow oil which was used without further purification.

Step 3

2-Imidazo[1,5-a]pyridin-1-yl-5-(2-trimethylsilanyl-ethoxymethyl)-5H-pyrrolo[2,3-b]pyrazine-7-carboxylic acid tert-butylamide

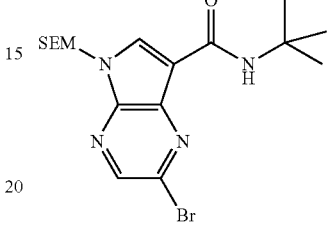

+

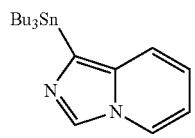 →

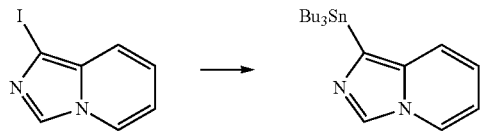

To a solution of 1-tributylstannyl-imidazo[1,5-a]pyridine (250 mg, 0.61 mmol) and 2-bromo-5-(2-trimethylsilanyl-ethoxymethyl)-5H-pyrrolo[2,3-b]pyrazine-7-carboxylic acid tert-butylamide (150 mg, 0.35 mmol) in DMF (2 mL) were added Pd(PPh$_3$)$_4$ (20 mg, 0.018 mmol) and copper(I) iodide (13 mg, 0.07 mmol). The reaction mixture was heated at 90° C. for 2 h then cooled to room temperature overnight. The reaction was quenched with water and extracted with EtOAc (3×). The combined organics were washed with water (3×) then dried over $MgSO_4$ and concentrated. The residue was chromatographed once with 0% to 3% MeOH/$CH_2Cl_2$ (0.5% $NH_4OH$) and then with 30% to 60% EtOAc/hexanes to afford 74 mg (45%) of 2-imidazo[1,5-a]pyridin-1-yl-5-(2-trimethylsilanyl-ethoxymethyl)-5H-pyrrolo[2,3-b]pyrazine-7-carboxylic acid tert-butylamide as a bright yellow solid. $^1H$ NMR ($CDCl_3$, 300 MHz): δ (ppm) 9.35 (s, 1H), 8.53 (d, J=9.4 Hz, 1H), 8.38 (s, 1H), 8.32 (s, 1H), 8.12 (d, J=7.2 Hz, 1H), 8.05 (s, 1H), 6.99 (dd, J=9.4, 6.6 Hz, 1H), 6.77-6.87 (m, 1H), 5.74 (s, 2H), 3.54-3.68 (m, 2H), 1.67 (s, 9H), 0.90-1.06 (m, 2H), 0.00 (s, 9H).

Step 4

2-(5,6,7,8-Tetrahydro-imidazo[1,5-a]pyridin-1-yl)-5H-pyrrolo[2,3-b]pyrazine-7-carboxylic acid tert-butylamide

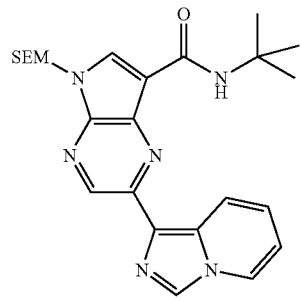

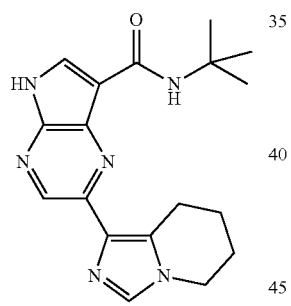

To a solution of 2-imidazo[1,5-a]pyridin-1-yl-5-(2-trimethylsilanyl-ethoxymethyl)-5H-pyrrolo[2,3-b]pyrazine-7-carboxylic acid tert-butylamide (70 mg, 0.15 mmol) in TFA (2 mL) was added platinum(IV) oxide (7 mg, 0.03 mmol). The reaction mixture was stirred under hydrogen (balloon) for 6 h then filtered over Celite, rinsing with $CH_2Cl_2$. The filtrate was concentrated. The residue was dissolved in $CH_2Cl_2$ (3 mL) and treated with ethylenediamine (0.4 mL). The reaction mixture was stirred for 1 h then quenched with water and extracted with $CH_2Cl_2$ (2×). The combined organics were dried over $MgSO_4$ and concentrated. The residue was purified by silica gel chromatography with 0% to 3% MeOH/$CH_2Cl_2$ (0.5% $NH_4OH$). The appropriate fractions were combined and concentrated to afford a yellow solid which was triturated with $Et_2O$ to obtain 13 mg (26%) of 2-(5,6,7,8-tetrahydro-imidazo[1,5-a]pyridin-1-yl)-5H-pyrrolo[2,3-b]pyrazine-7-carboxylic acid tert-butylamide as a pale yellow solid. MS: $(M+H)^+$=339; $^1H$ NMR (DMSO-$d_6$, 300 MHz): δ (ppm) 12.50 (br. s., 1H), 8.96 (s, 1H), 8.21 (s, 1H), 7.75 (s, 1H), 7.66 (s, 1H), 4.06 (t, J=5.9 Hz, 2H), 3.21 (t, J=6.2 Hz, 2H), 1.76-1.98 (m, 4H), 1.46 (s, 9H).

Example 276

2-(6-Chloro-1-methyl-1H-indazol-3-yl)-5H-pyrrolo[2,3-b]pyrazine-7-carboxylic acid (3-aminocyclohexyl)-amide (diastereomer A)

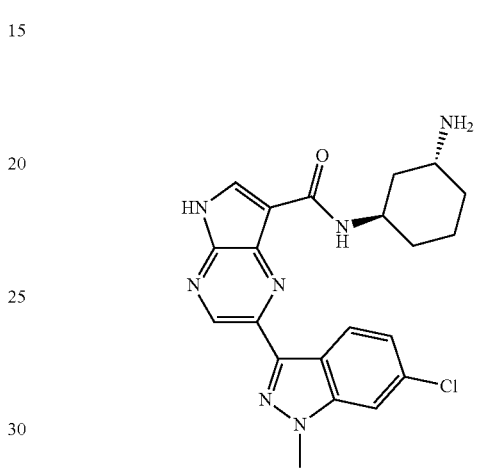

Step 1

(3-{[2-(6-Chloro-1-methyl-1H-indazol-3-yl)-5H-pyrrolo[2,3-b]pyrazine-7-carbonyl]-amino}-cyclohexyl)-carbamic acid tert-butyl ester (diastereomer A and diastereomer B)

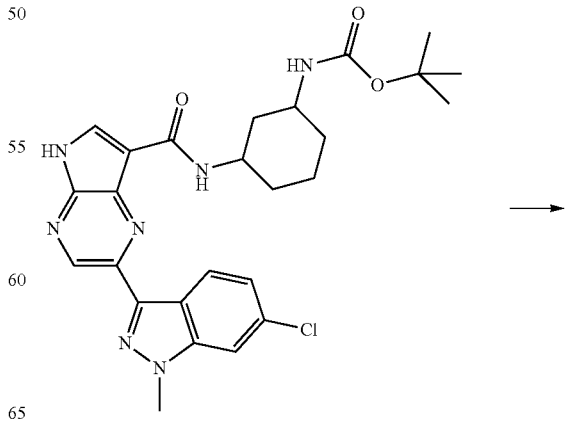

921
-continued

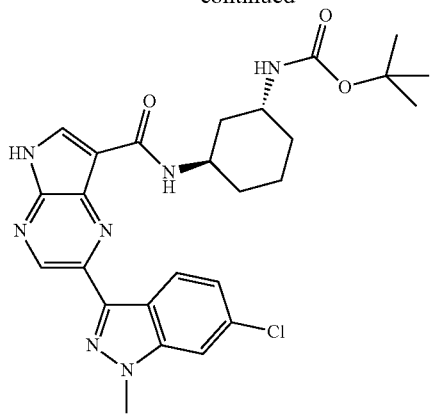

+

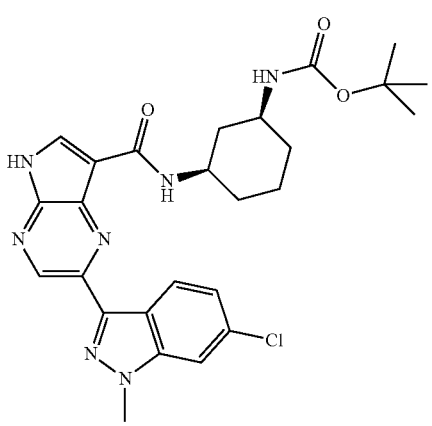

A racemic sample of (3-{[2-(6-chloro-1-methyl-1H-indazol-3-yl)-5H-pyrrolo[2,3-b]pyrazine-7-carbonyl]-amino}-cyclohexyl)-carbamic acid tert-butyl ester (see Example 442) was resolved into 2 fractions, each fraction consisting of two diastereoisomers, by using a Thar/Waters Multigram II SFC system by a Daicel AD column 3×25 cm eluted at 70 ml/min with 30% MeOH/CO$_2$ and 15 mg stacked injections at 220 nM with forced time windows collection. The diastereomeric pairs were arbitrarily assigned as trans (diastereomer A, 53 mg, light yellow solid, more polar) and cis (diastereomer B, 66 mg, off-white solid, less polar).

Step 2

2-(6-Chloro-1-methyl-1H-indazol-3-yl)-5H-pyrrolo[2,3-b]pyrazine-7-carboxylic acid (3-aminocyclohexyl)-amide (diastereomer A)

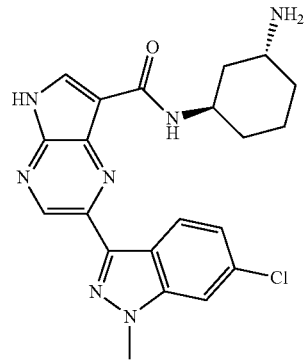 [SMILES: Cn1nc(-c2cnc3[nH]cc(C(=O)N[C@@H]4CCC[C@@H](N)C4)c3n2)c2ccc(Cl)cc21]

The more polar, diastereomer A of (3-{[2-(6-chloro-1-methyl-1H-indazol-3-yl)-5H-pyrrolo[2,3-b]pyrazine-7-carbonyl]-amino}-cyclohexyl)-carbamic acid tert-butyl ester (53 mg, 101 μmol) was dissolved in dichloromethane (5 mL) and treated with TFA (1.19 g, 803 μL, 10.4 mmol), the light yellow solution became a bright red-orange solution, stirring continued for 18 h at room temperature. Solvents were evaporated and the residue dissolved in dichloromethane/MeOH, adsorbed on silica gel and purified by chromatography (25 g column, 50 μm from Thomson, 0-10% MeOH containing 10% ammonium hydroxide in dichloromethane, 10 min gradient) to give an off white solid that was sonicated in MeOH and allowed to stand to promote complete solid formation. The solid was separated by decanting the mother liquor and dried under high vacuum to give 2-(6-chloro-1-methyl-1H-indazol-3-yl)-5H-pyrrolo[2,3-b]pyrazine-7-carboxylic acid (3-amino-cyclohexyl)-amide (diastereomer A) (27 mg, 63%) as an off-white solid. MS (M+H)$^+$=424; $^1$H NMR (DMSO-d$_6$) δ: 9.05 (s, 1H), 8.38-8.49 (m, 2H), 8.06 (d, J=7.9 Hz, 1H), 7.99 (s, 1H), 7.33 (d, J=10.2 Hz, 1H), 4.16 (s, 3H), 3.91 (d, J=4.2 Hz, 1H), 3.32 (br. s., 1H), 3.15 (s, 1H), 2.22 (d, J=11.0 Hz, 1H), 2.04 (d, J=11.7 Hz, 1H), 1.79 (br. s., 1H), 0.98-1.24 (m, 3H).

Example 277

2-(6-Chloro-1-methyl-1H-indazol-3-yl)-5H-pyrrolo[2,3-b]pyrazine-7-carboxylic acid (3-aminocyclohexyl)-amide (diastereomer B)

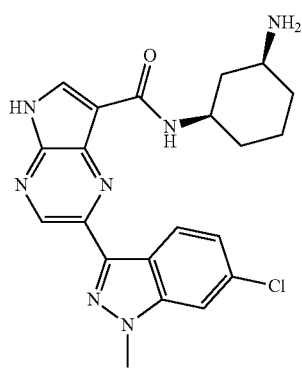 [SMILES: Cn1nc(-c2cnc3[nH]cc(C(=O)N[C@@H]4CCC[C@H](N)C4)c3n2)c2ccc(Cl)cc21]

The less polar, diastereomer B of (3-{[2-(6-chloro-1-methyl-1H-indazol-3-yl)-5H-pyrrolo[2,3-b]pyrazine-7-carbonyl]-amino}-cyclohexyl)-carbamic acid tert-butyl ester (66 mg, 126 µmol) isolated from Example 276 was dissolved in dichloromethane (5 mL) and treated with TFA (1.48 g, 1 mL, 13.0 mmol). After 18 h at room temperature the solvents were evaporated and the residue dissolved in dichloromethane/MeOH, adsorbed on silica gel and purified by chromatography (25 g column, 50 µm from Thomson, 0 to 5% MeOH containing 10% ammonium hydroxide) in dichloromethane, 20 min gradient) to give an off white residue that was dissolved in dichloromethane containing few drops of MeOH. Cyclohexane was added to promote solid formation. The precipitate was separated by decanting the mother liquor and dried under high vacuum to give 2-(6-chloro-1-methyl-1H-indazol-3-yl)-5H-pyrrolo[2,3-b]pyrazine-7-carboxylic acid (3-amino-cyclohexyl)-amide (diastereomer B) (18 mg, 33.7%) as a white solid. MS (M+H)$^+$=424; $^1$H NMR (DMSO-d$_6$) δ: 9.02 (s, 1H), 8.42 (s, 1H), 8.37 (d, J=8.7 Hz, 1H), 8.05 (d, J=7.9 Hz, 1H), 7.98 (s, 1H), 7.30 (d, J=10.2 Hz, 1H), 4.36 (br. s., 1H), 4.16 (s, 3H), 3.33 (br. s., 1H), 3.13 (br. s., 1H), 2.54 (br. s., 1H), 1.79 (br. s., 1H), 1.59-1.71 (m, 2H), 1.53 (d, J=9.4 Hz, 1H), 1.38 (s, 1H), 1.32 (s, 1H).

Example 278

N-Isopropyl-2-(1,5,5-trimethyl-4,5,6,7-tetrahydro-1H-indazol-3-yl)-5H-pyrrolo[2,3-b]pyrazine-7-carboxamide

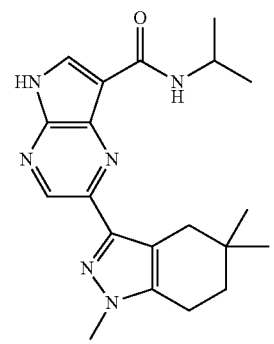 [SMILES: CC(C)NC(=O)c1c[nH]c2ncc(-c3nn(C)c4c3CC(C)(C)CC4)nc12]

Step 1

2-Bromo-N-isopropyl-5-((2-(trimethylsilyl)ethoxy)methyl)-5H-pyrrolo[2,3-b]pyrazine-7-carboxamide

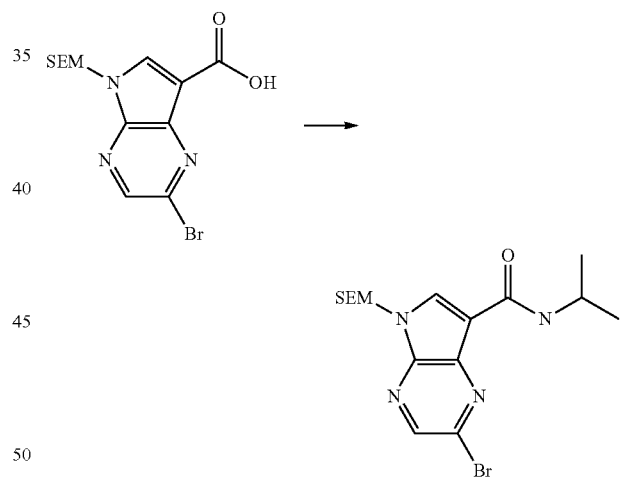

2-Bromo-5-((2-(trimethylsilyl)ethoxy)methyl)-5H-pyrrolo[2,3-b]pyrazine-7-carboxylic acid (1.12 g, 3.01 mmol) and HATU (1.37 g, 3.61 mmol) were combined with DMF (5.2 mL) then propan-2-amine (711 mg, 1.03 mL, 12.0 mmol) was added via syringe. The reaction mixture was stirred at 25° C. After 14 h, water (50 mL) was added and the mixture extracted with EtOAc (4×50 mL). The combined organics were washed with water (30 mL), saturated sodium chloride solution (3×20 mL) and dried with MgSO$_4$. Solvents were evaporated and the residue purified by chromatography (silica, 0 to 30% EtOAc in hexanes over 15 min) to yield 2-bromo-N-isopropyl-5-((2-(trimethylsilyl)ethoxy)methyl)-5H-pyrrolo[2,3-b]pyrazine-7-carboxamide (1.17 g, 2.83 mmol, 94%) as a white solid. MS (M+Na)$^+$=435; $^1$H NMR (CDCl$_3$) δ: 8.41 (s, 1H), 8.35 (s, 1H), 7.72 (d, J=4.9 Hz, 1H), 5.65 (s, 2H), 4.19-4.45 (m, 1H), 3.41-3.69 (m, 2H), 1.34 (d, J=6.8 Hz, 6H), 0.82-0.97 (m, 2H), −0.13-0.09 (m, 9H).

Step 2

N-Isopropyl-2-(1,5,5-trimethyl-4,5,6,7-tetrahydro-1H-indazol-3-yl)-5-((2-(trimethylsilyl)ethoxy)methyl)-5H-pyrrolo[2,3-b]pyrazine-7-carboxamide

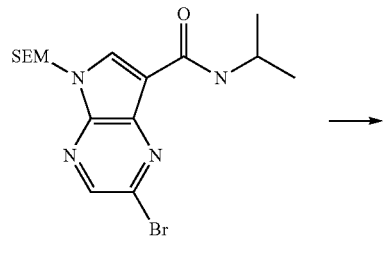

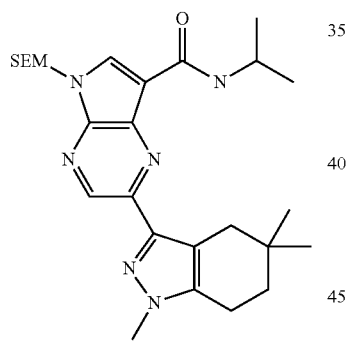

2-Bromo-N-isopropyl-5-((2-(trimethylsilyl)ethoxy)methyl)-5H-pyrrolo[2,3-b]pyrazine-7-carboxamide (124 mg, 301 μmol) and 1,5,5-trimethyl-3-(tributylstannyl)-4,5,6,7-tetrahydro-1H-indazole (see Example 13, 219 mg, 483 μmol.61) were dissolved in DMF (2.5 mL) under argon, tetrakis(triphenylphosphine)palladium (0) (17.4 mg, 15.0 μmol) and CuI (5.39 mg, 60.2 μmol, Eq: 0.20) were added and the mixture sonicated for 5 min with bubbling argon. The reaction mixture was stirred at 90° C. (oil bath temperature) for 2.5 h. The reaction mixture was concentrated under high vacuum and the residue was purified by chromatography (115 g column, 50 μm from Analogix, 0-70% EtOAc/hexanes, 30 min gradient) to give N-isopropyl-2-(1,5,5-trimethyl-4,5,6,7-tetrahydro-1H-indazol-3-yl)-5-((2-(trimethylsilyl)ethoxy)methyl)-5H-pyrrolo[2,3-b]pyrazine-7-carboxamide (113 mg, 227 μmol, 76%) as a light yellow solid. MS (M+Na)⁺= 497; ¹H NMR (CDCl₃) δ: 9.08 (s, 1H), 8.28 (s, 1H), 5.68 (s, 2H), 4.38-4.56 (m, 1H), 3.86 (s, 3H), 3.50-3.59 (m, 2H), 2.80 (s, 2H), 2.65 (t, J=6.4 Hz, 2H), 1.69 (t, J=6.6 Hz, 2H), 1.36 (d, J=6.8 Hz, 6H), 1.07 (s, 6H), 0.88-0.96 (m, 2H), −0.06 (s, 9H).

Step 3

N-isopropyl-2-(1,5,5-trimethyl-4,5,6,7-tetrahydro-1H-indazol-3-yl)-5H-pyrrolo[2,3-b]pyrazine-7-carboxamide

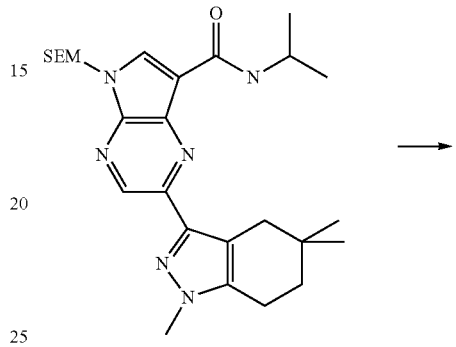

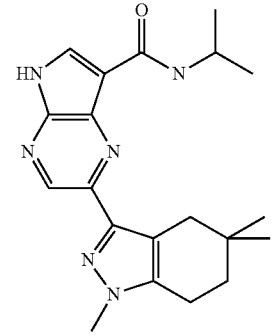

To a solution of N-isopropyl-2-(1,5,5-trimethyl-4,5,6,7-tetrahydro-1H-indazol-3-yl)-5-((2-(trimethylsilyl)ethoxy)methyl)-5H-pyrrolo[2,3-b]pyrazine-7-carboxamide (113 mg, 227 mmol) in dichloromethane (3 mL) was added TFA (1.48 g, 1 mL, 13.0 mmol). The reaction mixture was stirred at 25° C. for 15 h then concentrated. The residue was re-dissolved in 5 mL of a solution of dichloromethane/MeOH/ammonium hydroxide; 60:10:1 and stirred at 25° C. for 3 h, then evaporated to a yellow solid. The solid was dissolved in dichloromethane (containing a few drops of MeOH) and purified by chromatography (40 g, 50 μm particle size, Analogix, 0 to 5% MeOH containing 10% ammonium hydroxide in dichloromethane, 15 min). The pure product was re-dissolved in MeOH and allowed to stand for solid formation. The solid was separated by decanting the mother liquors and then dried to give N-isopropyl-2-(1,5,5-trimethyl-4,5,6,7-tetrahydro-1H-indazol-3-yl)-5H-pyrrolo[2,3-b]pyrazine-7-carboxamide (60 mg, 164 μmol, 72%) as a white needles. MS (M+H)⁺= 367; ¹H NMR (300 MHz, DMSO-d₆) δ ppm 12.47-12.74 (m, 1H), 8.91 (s, 1H), 8.31 (s, 1H), 7.92 (d, J=8.31 Hz, 1H), 4.07-4.48 (m, 1H), 3.78 (s, 3H), 2.72 (s, 2H), 2.64 (t, J=6.42 Hz, 2H), 1.60 (t, J=6.42 Hz, 2H), 1.26 (d, J=6.42 Hz, 6H), 1.01 (s, 6H).

Example 279

N-Isopropyl-2-(1,6,6-trimethyl-4,5,6,7-tetrahydro-1H-indazol-3-yl)-5H-pyrrolo[2,3-b]pyrazine-7-carboxamide

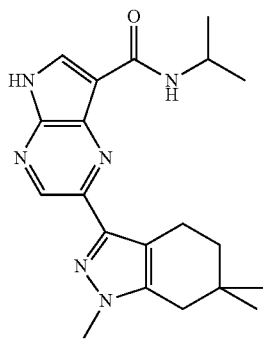 [SMILES: CC(C)NC(=O)c1c[nH]c2ncc(-c3nn(C)c4c3CCC(C)(C)C4)nc12]

Step 1

N-isopropyl-2-(1,6,6-trimethyl-4,5,6,7-tetrahydro-1H-indazol-3-yl)-5-((2-(trimethylsilyl)ethoxy)methyl)-5H-pyrrolo[2,3-b]pyrazine-7-carboxamide

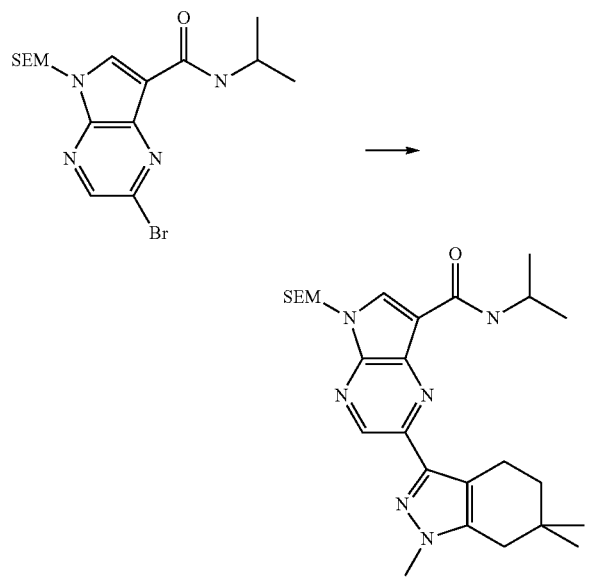

2-Bromo-N-isopropyl-5-((2-(trimethylsilyl)ethoxy)methyl)-5H-pyrrolo[2,3-b]pyrazine-7-carboxamide (107 mg, 259 µmol) and 1,6,6-trimethyl-3-(tributylstannyl)-4,5,6,7-tetrahydro-1H-indazole (see Example 70, 188 mg, 414 µmol.6) were dissolved in DMF (2.5 mL) under argon, tetrakis(triphenylphosphine)palladium (0) (15.0 mg, 12.9 µmol) and CuI (4.64 mg, 51.8 µmol, Eq: 0.20) were added and the mixture sonicated for 5 min with bubbling argon. The reaction mixture was stirred at 90° C. (oil bath temperature) for 2.5 h. The reaction mixture was concentrated under high vacuum and the residue was purified by chromatography (silica, 40 g column, 50 µm from Analogix, 0-50% EtOAc in hexanes over 15 min) to give N-isopropyl-2-(1,6,6-trimethyl-4,5,6,7-tetrahydro-1H-indazol-3-yl)-5-((2-(trimethylsilyl)ethoxy)methyl)-5H-pyrrolo[2,3-b]pyrazine-7-carboxamide (90 mg, 181 µmol, 70.0%) as a light yellow solid and of approximately 75% purity. MS (M+H)$^+$=497.1; $^1$H NMR (CDCl$_3$) δ: 9.10 (s, 1H), 8.26 (s, 1H), 8.18 (d, J=7.9 Hz, 1H), 5.68 (s, 2H), 4.34-4.60 (m, 1H), 3.82 (s, 3H), 3.48-3.61 (m, 2H), 3.03 (t, J=6.2 Hz, 2H), 2.41 (s, 2H), 1.61 (t, J=6.4 Hz, 2H), 1.33 (d, J=6.8 Hz, 6H), 1.09 (s, 6H), 0.83-0.97 (m, 2H), −0.06 (s, 9H). NMR and LCMS showed an impurity that was identified as the dimer of the tetrahydroindazole (MW 326.49) linked at the 3-position.

Step 5

N-Isopropyl-2-(1,6,6-trimethyl-4,5,6,7-tetrahydro-1H-indazol-3-yl)-5H-pyrrolo[2,3-b]pyrazine-7-carboxamide

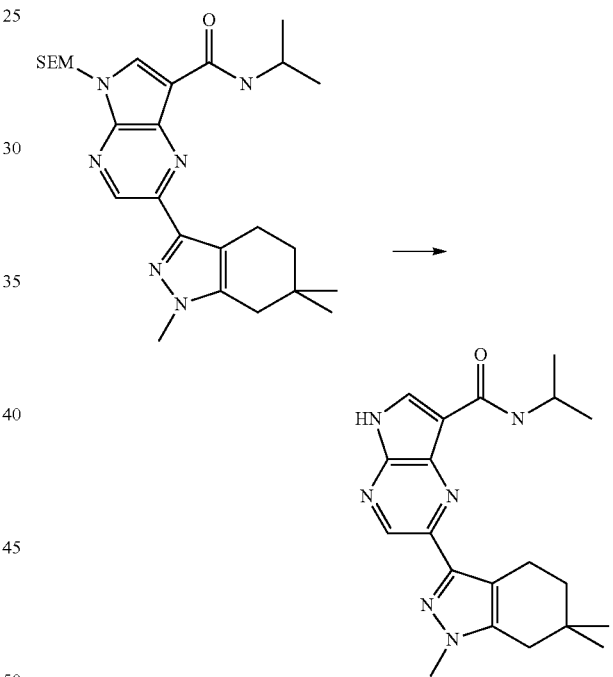

To a solution of N-isopropyl-2-(1,6,6-trimethyl-4,5,6,7-tetrahydro-1H-indazol-3-yl)-5-((2-(trimethylsilyl)ethoxy)methyl)-5H-pyrrolo[2,3-b]pyrazine-7-carboxamide (90 mg, 181 µmol) in dichloromethane (3 mL) was added TFA (1.48 g, 1.00 mL, 13.0 mmol). The reaction mixture was stirred at 25° C. for 18 h then concentrated. The residue was re-dissolved in 5 mL of a solution of dichloromethane/MeOH/ammonium hydroxide (60:10:1) and stirred at 25° C. for 3 h, then evaporated and purified by chromatography (40 g, 50 µm particle size, Analogix, 0 to 5% MeOH containing 10% ammonium hydroxide in dichloromethane, 15 min gradient). The pure product was suspended in dichloromethane and cyclohexane added to promote solid formation. The solid was separated by decanting the mother liquors and then dried to give N-isopropyl-2-(1,6,6-trimethyl-4,5,6,7-tetrahydro-1H-indazol-3-yl)-5H-pyrrolo[2,3-b]pyrazine-7-carboxamide (54 mg, 147 μmol, 81.3%) as a white solid. MS (M+H)⁺=367; ¹H NMR (300 MHz, DMSO-d₆) δ ppm 12.68 (m, 1H), 8.91 (s, 1H), 8.31 (s, 1H), 8.04 (d, J=8.31 Hz, 1H), 4.17-4.26 (m, 1H), 3.75 (s, 3H), 2.92 (t, J=6.42 Hz, 2H), 1.52 (t, J=6.42 Hz, 2H), 1.37 (s, 2H), 1.22 (d, J=6.42 Hz, 6H), 1.01 (s, 6H).

Example 280

N-Isopropyl-2-(1,6,6-trimethyl-4,5,6,7-tetrahydro-1H-indazol-3-yl)-5H-pyrrolo[2,3-b]pyrazine-7-carboxamide

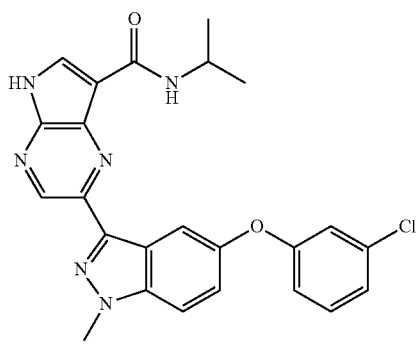 [SMILES: CC(C)NC(=O)c1c[nH]c2ncc(-c3nn(C)c4ccc(Oc5cccc(Cl)c5)cc34)nc12]

Step 1

4-(3-Chloro-phenoxy)-2-methyl-1-nitro-benzene

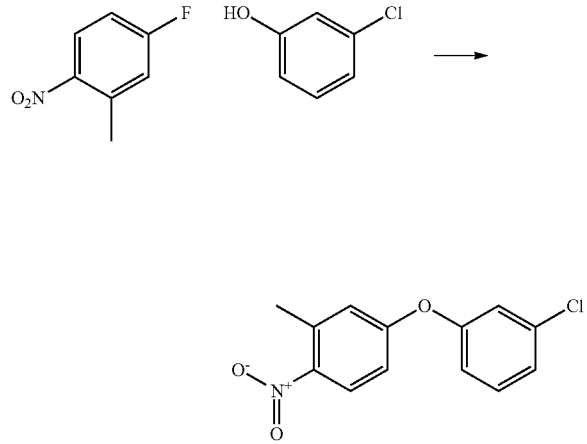

To a suspension of 3-chloro-phenol (1.65 g, 12.89 mmol) in DMF (10 mL), was added KOH (1.45 g, 25.78 mmol) and the mixture heated at 110° C. for 30 min. The mixture was cooled to 25° C. and 4-fluoro-2-methyl-1-nitro-benzene (0.5 g, 3.22 mmol) was added. This mixture was then heated to 130° C. for 12 h. The reaction mixture was treated with 10% NaOH solution and extracted with EtOAc (3×25 mL). The organic phase was washed with brine (3×5 mL), dried over sodium sulfate and concentrated. The residue was purified by column chromatography (silica, 0.5% EtOAc in hexanes) to afford 4-(3-chloro-phenoxy)-2-methyl-1-nitro-benzene (400 mg, 47%). MS (M+H)⁺=263; ¹H NMR (CDCl₃) δ: 8.05 (d, J=7.1 Hz, 1H), 7.33 (t, J=6.0 Hz, 1H), 7.20 (d, J=5.3 Hz, 1H), 7.06 (s, 1H), 7.03-6.85 (m, 3H), 2.59 (s, 3H).

Step 2

4-(3-Chloro-phenoxy)-2-methyl-phenylamine

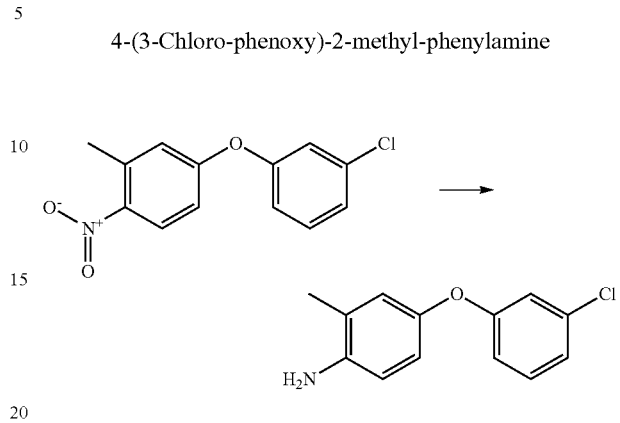

To a stirred solution of 4-(3-chloro-phenoxy)-2-methyl-1-nitro-benzene (0.56 g, 2.12 mmol) in ethanol and water, iron (594 mg, 10.6 mmol) and saturated ammonium chloride (569 mg, 10.6 mmol) were added. This reaction mixture was then heated to reflux for 12 h. This was then filtered through celite and then extracted with EtOAc (3×15 mL). The EtOAc layer was washed with brine, dried over sodium sulfate and concentrated. This was then purified by chromatography (11% EtOAc in hexanes) to afford 4-(3-chloro-phenoxy)-2-methyl-phenylamine (0.43 g, 87%). MS (M+H)⁺=234.1; ¹H NMR (CDCl₃) δ: 7.17 (t, J=6.0 Hz, 1H), 6.95 (d, J=2.8 Hz, 1H), 6.88-6.86 (m, 1H), 6.82-6.71 (m, 2H), 6.65 (d, J=6.27 Hz, 1H).

Step 3

5-(3-Chloro-phenoxy)-1H-indazole

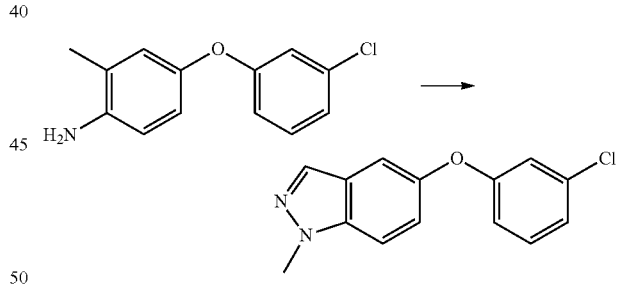

4-(3-Chloro-phenoxy)-2-methyl-phenylamine (0.87 g, 3.74 mmol) was dissolved in chloroform. Ac₂O (0.878 g, 8.61 mmol) was then added dropwise over 10 min at 0° C. and the mixture was stirred for 1 h at 25° C. Potassium acetate (110 mg, 1.12 mmol) and t-butyl nitrite (829 mg, 8.05 mmol) were added to the reaction mixture and the mixture was heated at 80° C. for 16 h. This was then concentrated, conc. HBr was added and the mixture was stirred for 16 h at 25° C. The pH of the mixture was adjusted to pH 7 using KOH solution and the resulting mixture was extracted with EtOAc (3×50 mL). The organic phase was washed with brine (3×10 mL), dried over sodium sulfate and concentrated. The residue was purified by column chromatography (11% EtOAc in hexanes) to afford 5-(3-chloro-phenoxy)-1H-indazole (152 mg, 17%). MS (M+H)⁺=245; ¹H NMR (CDCl₃) δ: 8.03 (s, 1H), 7.50 (d, J=8.7 Hz, 1H), 7.37 (br.s., 1H), 7.21 (d, J=6.18

Hz, 1H), 7.16 (dd, J=6.5, 1.1 Hz, 1H); 7.08 (d, J=5.8 Hz, 1H), 6.93 (br.s., 1H), 6.86 (d, J=6.0 Hz, 1H).

Step 4

5-(3-Chlorophenoxy)-3-iodo-1H-indazole

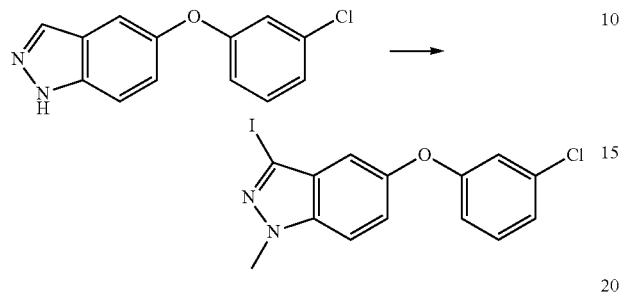

To a solution of 5-(3-chlorophenoxy)-1H-indazole (152 mg, 621 µmol) in DMF (2.36 mL) at 25° C. was added potassium hydroxide (105 mg, 1.86 mmol) and iodine (237 mg, 932 µmol). The reaction mixture was stirred at 25° C. for 75 min then quenched with 10% $Na_2S_2O_3$ and diluted with water. The mixture was extracted with EtOAc (3×), then the combined organics were washed with water and brine (2×), dried over $MgSO_4$ and concentrated to afford a pale yellow oil which was purified by chromatography (silica, 115 g, 50 µm from Analogix, 0 to 30% EtOAc in hexanes, 15 min) to give 5-(3-chlorophenoxy)-3-iodo-1H-indazole (194 mg, 524 µmol, 84%) as an off-white solid. MS (M+H)$^+$=370.8; $^1$H NMR (CDCl$_3$) δ: 7.73 (d, J=8.7 Hz, 1H), 7.28 (d, J=5.3 Hz, 1H), 7.22-7.25 (m, 1H), 7.17 (d, J=1.9 Hz, 1H), 7.08 (dt, J=7.9, 0.9 Hz, 1H), 6.98 (t, J=2.3 Hz, 1H), 6.89 (dd, J=8.3, 2.3 Hz, 1H).

Step 5

5-(3-Chlorophenoxy)-3-iodo-1-methyl-1H-indazole

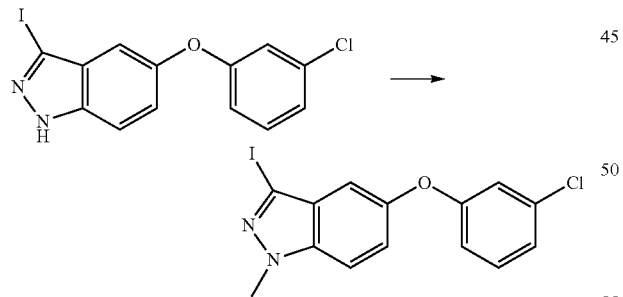

To a solution of 5-(3-chlorophenoxy)-3-iodo-1H-indazole (194 mg, 524 µmol) in THF (5 mL) at 0° C. was added KOtBu (82.2 mg, 733 µmol) and the mixture stirred at 0° C. for 30 min. MeI (104 mg, 45.8 µL, 733 µmol) was added. The reaction mixture was stirred at 0° C. for 30 min then warmed to 25° C. and stirred for 1.5 h. The reaction mixture was quenched with saturated ammonium chloride in water and extracted with dichloromethane. The combined organics were dried over $MgSO_4$ and concentrated to a clear oil, then purified by chromatography (40 g column, 50 µm from Analogix, 0-20% EtOAc in hexanes over 20 min) to afford the desired less polar 5-(3-chlorophenoxy)-3-iodo-1-methyl-1H-indazole (154 mg, 400 mmol, 77%) as a clear yellow oil. MS (M+H)$^+$=384.8; $^1$H NMR (CDCl$_3$) δ: 7.38 (d, J=9.1 Hz, 1H), 7.17-7.29 (m, 2H), 7.11 (d, J=2.3 Hz, 1H), 7.06 (dt, J=7.9, 0.9 Hz, 1H), 6.94 (t, J=2.3 Hz, 1H), 6.86 (dd, J=8.3, 2.3 Hz, 1H), 4.12 (s, 3H). The regioisomer, 5-(3-chlorophenoxy)-3-iodo-2-methyl-2H-indazole, (32 mg, 83.2 µmol, 16%) was also obtained as a clear yellow oil.

Step 6

5-(3-Chlorophenoxyl-1-methyl-3-(tributylstannyl)-1H-indazole

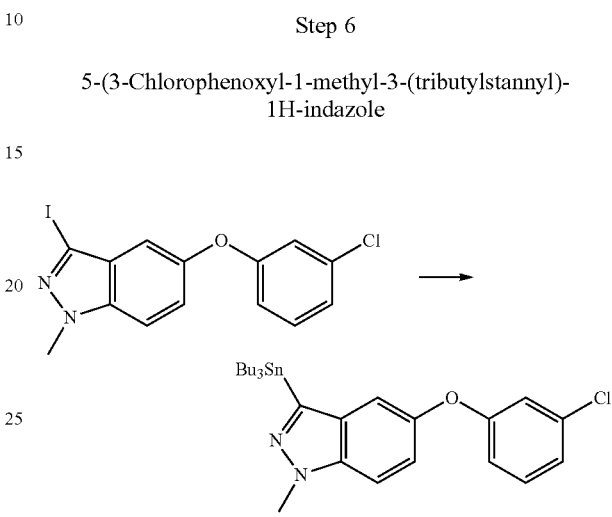

5-(3-Chlorophenoxy)-3-iodo-1-methyl-1H-indazole (0.154 g, 400 µmol) was dissolved in THF (3.00 mL). The colorless solution was cooled to −16° C. (NaCl/ice bath) then isopropylmagnesium chloride (2M in THF, 224 µL, 448 µmol) was added dropwise at −16° C. The reaction mixture was stirred at −16° C. for 20 min then tributylchlorostannane (150 mg, 125 µL, 460 µmol) was added slowly. The reaction mixture was warmed to 25° C. and stirred for 1.5 h. The reaction mixture was quenched with saturated ammonium chloride solution, extracted with dichloromethane, and the combined organics dried over $MgSO_4$ and concentrated to a yellow oil. The residue was dried under high vacuum to give 5-(3-chlorophenoxy)-1-methyl-3-(tributylstannyl)-1H-indazole. The mass of this material was greater than the theoretical yield of the desired product. The yield was assumed to be quantitative, and the material was used directly in the next step without further purification.

Step 7

2-(5-(3-Chlorophenoxy)-1-methyl-1H-indazol-3-yl)-N-isopropyl-5-((2-(trimethylsilyl)ethoxy)methyl)-5H-pyrrolo[2,3-b]pyrazine-7-carboxamide

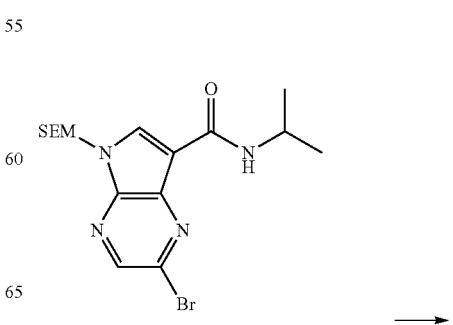

933
-continued

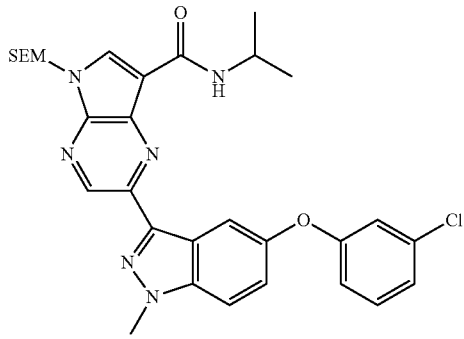

2-Bromo-N-isopropyl-5-((2-(trimethylsilyl)ethoxy)methyl)-5H-pyrrolo[2,3-b]pyrazine-7-carboxamide (103 mg, 250 µmol) and 5-(3-chlorophenoxy)-1-methyl-3-(tributylstannyl)-1H-indazole (219 mg, 400 µmol.6) were dissolved in DMF (2.5 mL) under argon, tetrakis(triphenylphosphine) palladium (0) (14.4 mg, 12.5 µmol) and CuI (9.52 mg, 50.0 µmol, Eq: 0.20) were added and the mixture sonicated for 5 min with bubbling argon. The reaction mixture was stirred at 90° C. (oil bath temperature) for 2.5 h. The reaction mixture was concentrated under high vacuum and the residue was purified by chromatography (40 g column, 50 µm from Analogix, 0-50% over 30 min) to give 2-(5-(3-chlorophenoxy)-1-methyl-1H-indazol-3-yl)-N-isopropyl-5-((2-(trimethylsilyl)ethoxy)methyl)-5H-pyrrolo[2,3-b]pyrazine-7-carboxamide (113 mg, 191 µmol, 77%) as a light yellow solid. $^1$H NMR (CDCl$_3$) δ: 9.27 (s, 1H), 8.32 (s, 1H), 8.28 (d, J=2.3 Hz, 1H), 8.05 (d, J=8.3 Hz, 1H), 7.52 (d, J=8.7 Hz, 1H), 7.17-7.28 (m, 2H), 6.97-7.06 (m, 1H), 6.79-6.90 (m, 2H), 5.71 (s, 2H), 4.28-4.46 (m, 1H), 4.23 (s, 3H), 3.51-3.66 (m, 2H), 1.22 (d, J=6.4 Hz, 6H), 0.85-1.03 (m, 2H), −0.04 (s, 9H).

Step 8

N-Isopropyl-2-(1,6,6-trimethyl-4,5,6,7-tetrahydro-1H-indazol-3-yl)-5H-pyrrolo[2,3-b]pyrazine-7-carboxamide

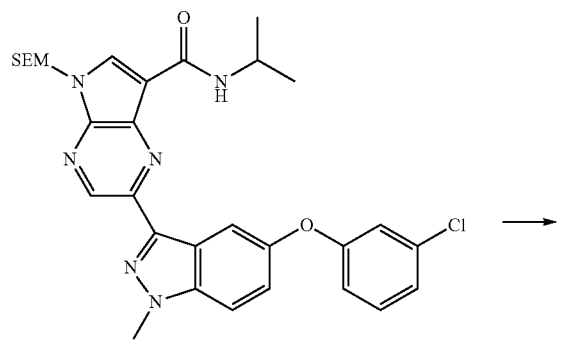

934
-continued

To a solution of N-isopropyl-2-(1,6,6-trimethyl-4,5,6,7-tetrahydro-1H-indazol-3-yl)-5-((2-(trimethylsilyl)ethoxy)methyl)-5H-pyrrolo[2,3-b]pyrazine-7-carboxamide (90 mg, 181 µmol) in dichloromethane (3 mL) was added TFA (1.48 g, 1.00 mL, 13.0 mmol). The reaction mixture was stirred at 25° C. overnight then concentrated. The residue was re-dissolved in 5 mL of a mixture of dichloromethane/MeOH/ammonium hydroxide (60:10:1) and stirred at 25° C. for 3 h, then evaporated to a yellow solid, dissolved in dichloromethane (containing a few drops of MeOH) and purified by chromatography (40 g, 50 µm particle size, Analogix, 0 to 5% MeOH containing 10% ammonium hydroxide in dichloromethane). The pure product was suspended in dichloromethane and cyclohexane added to promote solid formation. The solid was separated by decanting the mother liquors and then dried to give N-isopropyl-2-(1,6,6-trimethyl-4,5,6,7-tetrahydro-1H-indazol-3-yl)-5H-pyrrolo[2,3-b]pyrazine-7-carboxamide (54 mg, 147 µmol, 81%) as a white solid. MS (M+H)$^+$=461; $^1$H NMR (DMSO-d$_6$) δ: 9.11 (s, 1H), 8.37 (s, 1H), 8.17 (d, J=1.9 Hz, 1H), 7.90 (s, 1H), 7.87 (s, 1H), 7.27-7.38 (m, 2H), 7.06-7.15 (m, 1H), 6.91 (t, J=2.1 Hz, 1H), 6.80-6.89 (m, 1H), 4.20 (s, 3H), 4.11 (dq, J=13.9, 6.8 Hz, 1H), 1.06 (d, J=6.4 Hz, 6H).

Example 281

N-Isopropyl-2-(1-methyl-5-(trifluoromethoxy)-1H-indazol-3-yl)-5H-pyrrolo[2,3-b]pyrazine-7-carboxamide

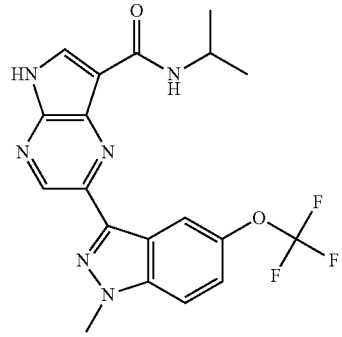 [SMILES: CC(C)NC(=O)c1c[nH]c2ncc(-c3nn(C)c4ccc(OC(F)(F)F)cc34)nc12]

Step 1

3-Iodo-5-(trifluoromethoxy)-1H-indazole

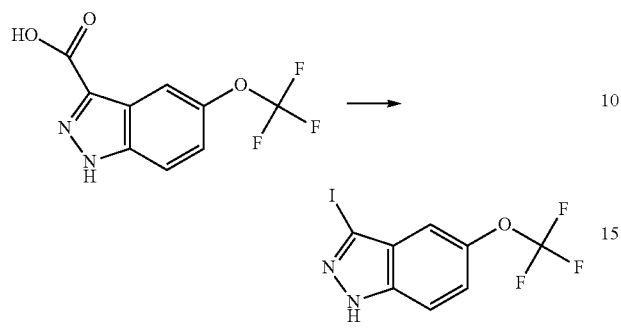

To a mixture of 5-(trifluoromethoxy)-1H-indazole-3-carboxylic acid (0.2 g, 813 µmol), and sodium bicarbonate (225 mg, 104 µL, 2.68 mmol) in dichloroethane (2 mL) and water (2.00 mL) were added in one portion sodium iodide (317 mg, 2.11 mmol) and iodine (268 mg, 1.06 mmol) and the mixture heated at 100° C. (oil bath temperature) with vigorous stirring for 45 minutes. After cooling to 25° C. the mixture was diluted with dichloromethane, then washed with 10% $Na_2S_2O_3$ and saturated $NaHCO_3$. The organics were dried ($MgSO_4$) and concentrated to an off-white solid which was dissolved in dichloromethane, cyclohexane added to promote solid formation, and allowed to stand. The solid was separated by filtration and dried to give 3-iodo-5-(trifluoromethoxy)-1H-indazole (178 mg, 543 µmol, 67%) as white needles. MS (M−H)⁻=326.8; $^1$H NMR (CDCl$_3$) δ: 7.51 (d, J=9.1 Hz, 1H), 7.40 (s, 1H), 7.32-7.38 (m, 1H).

Step 2

3-Iodo-1-methyl-5-(trifluoromethoxy)-1H-indazole

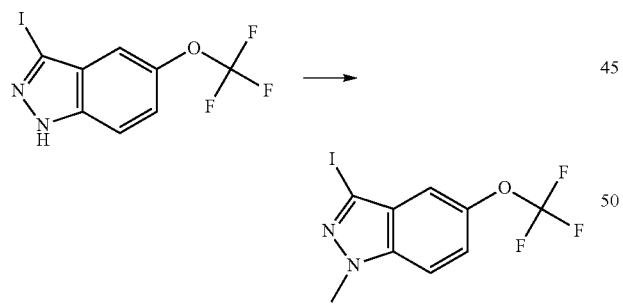

To a solution of 3-iodo-5-(trifluoromethoxy)-1H-indazole (178 mg, 543 µmol) in THF (5 mL) at 0° C. was added KOtBu (85.2 mg, 760 µmol) and the mixture stirred at 0° C. for 30 min then MeI (108 mg, 47.5 µL, 760 µmol) was added. The reaction mixture was stirred at 0° C. for 30 min then warmed to 25° C. and stirred for 1.5 h. The reaction mixture was quenched with saturated ammonium chloride in water and extracted with dichloromethane (3×30 mL). The combined organics were dried over $MgSO_4$ and concentrated to a clear oil. Purification by chromatography (40 g column, 50 µm from Analogix, 0-20% EtOAc in hexanes over 20 min) gave 3-iodo-1-methyl-5-(trifluoromethoxy)-1H-indazole (141 mg, 412 µmol, 76%) as a white solid. MS (M+H)⁺=342.8; $^1$H NMR (CDCl$_3$) δ: 7.36-7.43 (m, 1H), 7.23-7.36 (m, 2H), 4.12 (s, 3H); LCMS ESI+ TIC MS showed 100% purity, [M+H]⁺= 342.8. The regioisomer, 3-iodo-2-methyl-5-(trifluoromethoxy)-2H-indazole, (29 mg, 84.8 µmol, 16%) was also obtained as a waxy off-white solid.

Step 3

1-Methyl-3-(tributylstannyl)-5-(trifluoromethoxy)-1H-indazole

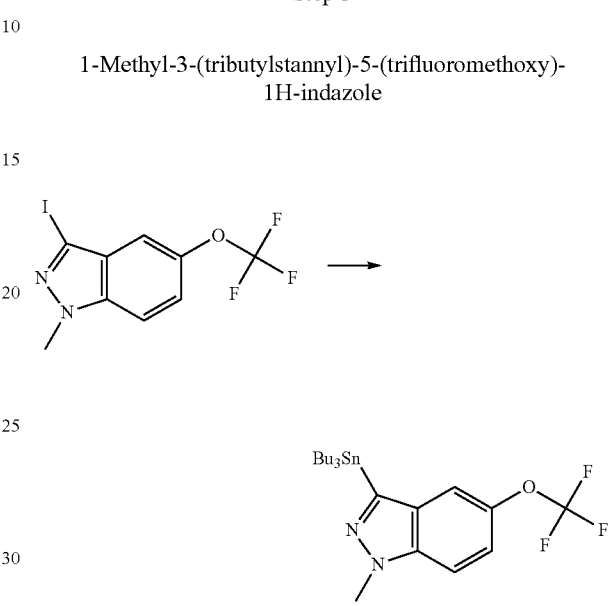

3-Iodo-1-methyl-5-(trifluoromethoxy)-1H-indazole (0.141 g, 412 µmol) was dissolved in THF (3.00 mL). The colorless solution was cooled to −16° C. (NaCl/ice bath), then isopropylmagnesium chloride 2M in THF (231 µL, 462 µmol) was added dropwise at −16° C. The reaction mixture was stirred at −16° C. for 20 min. Tributylchlorostannane (154 mg, 129 µL, 474 µmol) was added slowly. The reaction mixture was warmed to 25° C. and stirred for 1.5 h. The reaction mixture was quenched with saturated ammonium chloride solution, extracted with dichloromethane (3×30 mL), the organics dried over $MgSO_4$ and concentrated to a yellow oil. The residue was dried under high vacuum and taken into the next step without further purification.

Step 4

N-Isopropyl-2-(1-methyl-5-(trifluoromethoxy)-1H-indazol-3-yl)-5-((2-(trimethylsilyl)ethoxy)methyl)-5H-pyrrolo[2,3-b]pyrazine-7-carboxamide

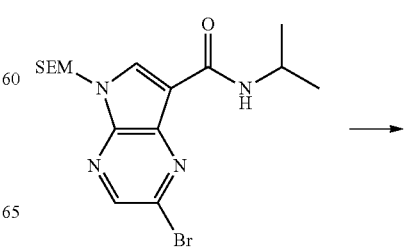

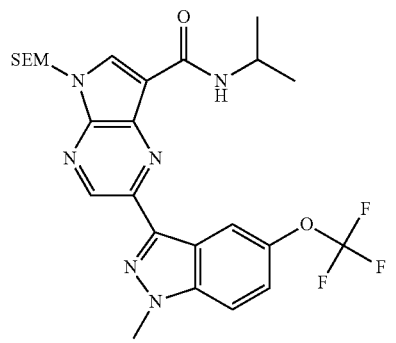

In a 25 mL round-bottomed flask, 2-bromo-N-isopropyl-5-((2-(trimethylsilyl)ethoxy)methyl)-5H-pyrrolo[2,3-b]pyrazine-7-carboxamide (107 mg, 258 μmol) and 1-methyl-3-(tributylstannyl)-5-(trifluoromethoxy)-1H-indazole (209 mg, 413 μmol) were dissolved in DMF (2.5 mL) under argon, tetrakis(triphenylphosphine)palladium (0) (14.9 mg, 12.9 μmol) and CuI (9.83 mg, 51.6 μmol, Eq: 0.20) were added and the mixture sonicated for 5 min with bubbling argon. The reaction mixture was stirred at 90° C. (oil bath temperature) for 2.5 h. The reaction mixture was concentrated under high vacuum and the residue was purified by chromatography (40 g column, 50 μm from Analogix, 0-50% EtOAc in hexanes over 30 min) to give N-isopropyl-2-(1-methyl-5-(trifluoromethoxy)-1H-indazol-3-yl)-5-((2-(trimethylsilyl)ethoxy)methyl)-5H-pyrrolo[2,3-b]pyrazine-7-carboxamide (113 mg, 206 μmol, 80%) as a light yellow solid. MS (M+H)$^+$= 549; $^1$H NMR (CDCl$_3$) δ: 9.23 (s, 1H), 8.35 (s, 2H), 8.01 (d, J=7.9 Hz, 1H), 7.44-7.53 (m, 1H), 7.34-7.43 (m, 1H), 5.70 (s, 2H), 4.38-4.56 (m, 1H), 4.19 (s, 3H), 3.52-3.64 (m, 2H), 1.42 (d, J=6.4 Hz, 6H), 0.84-1.00 (m, 2H), −0.05 (s, 9H).

To a slightly yellow clear solution of N-isopropyl-2-(1-methyl-5-(trifluoromethoxy)-1H-indazol-3-yl)-5-((2-(trimethylsilyl)ethoxy)methyl)-5H-pyrrolo[2,3-b]pyrazine-7-carboxamide (113 mg, 206 μmol) in dichloromethane (5 mL) was added TFA (1.48 g, 1.00 mL, 13.0 mmol), the reaction mixture was stirred overnight then concentrated. The residue was re-dissolved in 5 mL of a solution of dichloromethane/MeOH/ammonium hydroxide (60:10:1) and stirred at 25° C. for 3 h, then evaporated to a light yellow solid, dissolved in dichloromethane (containing a few drops of MeOH) and purified by chromatography (40 g column, 50 μm from Analogix, 0 to 5% MeOH containing 10% ammonium hydroxide)/dichloromethane). The pure product was suspended in dichloromethane and cyclohexane added to promote solid formation, then the solid was separated by filtration and dried to give N-isopropyl-2-(1-methyl-5-(trifluoromethoxy)-1H-indazol-3-yl)-5H-pyrrolo[2,3-b]pyrazine-7-carboxamide (78 mg, 186 μmol, 91%) as a white solid. MS (M+H)$^+$=419; $^1$H NMR (DMSO-d$_6$) δ: 12.86 (br. s., 1H), 9.12 (s, 1H), 8.42 (s, 1H), 8.34 (s, 1H), 7.88-7.97 (m, 2H), 7.56 (d, J=9.1 Hz, 1H), 4.14-4.36 (m, 4H), 1.30 (d, J=6.4 Hz, 6H).

Step 5

N-isopropyl-2-(1-methyl-5-(trifluoromethoxy)-1H-indazol-3-yl)-5H-pyrrolo[2,3-b]pyrazine-7-carboxamide Example 282

N-Isopropyl-2-(1-methyl-1,4,5,6-tetrahydrocyclopenta[c]pyrazol-3-yl)-5H-pyrrolo[2,3-b]pyrazine-7-carboxamide

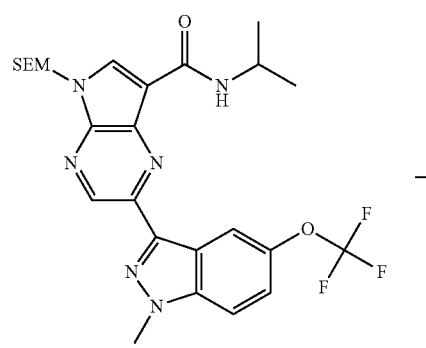

Step 1

3-Iodo-1,4,5,6-tetrahydrocyclopenta[c]pyrazole

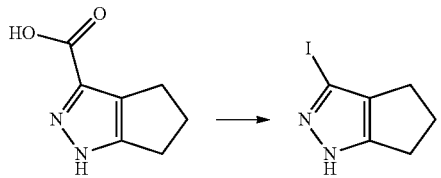 [SMILES: O=C(O)c1n[nH]c2c1CCC2 ; Ic1n[nH]c2c1CCC2]

To a mixture of 1,4,5,6-tetrahydrocyclopenta[c]pyrazole-3-carboxylic acid (0.5 g, 3.29 mmol), and sodium bicarbonate (911 mg, 422 μL, 10.8 mmol) in dichloroethane (5 mL) and water (5 mL) were added in one portion sodium iodide (1.28 g, 8.54 mmol) and iodine (1.08 g, 4.27 mmol) and the mixture heated at to 100° C. (oil bath temperature) with vigorous stirring for 24 h. After cooling to 25° C. the mixture was diluted with dichloromethane then washed with 10% $Na_2S_2O_3$ and saturated $NaHCO_3$. The organic phases were combined, dried ($MgSO_4$) and concentrated to a yellow solid which was dissolved in dichloromethane, cyclohexane added to promote solid formation and allowed to stand. The solid was separated by filtration and dried to give 3-iodo-1,4,5,6-tetrahydrocyclopenta[c]pyrazole (580 mg, 2.48 mmol, 75%) as needles. MS $(M+H)^+$=234.9; $^1$H NMR ($CDCl_3$) δ: 2.71-2.99 (m, 31H), 2.39-2.66 (m, 4H).

Step 2

3-Iodo-1-methyl-1,4,5,6-tetrahydrocyclopenta[c]pyrazole

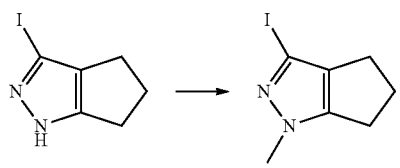

To a solution of 3-iodo-1,4,5,6-tetrahydrocyclopenta[c]pyrazole (305 mg, 1.3 mmol) in THF (8.51 mL) at 0° C. was added KOtBu 1M in THF (1.82 mL, 1.82 mmol) and the mixture stirred at 0° C. for 30 min where it became a pale yellow solution then added MeI (259 mg, 114 μL, 1.82 mmol). The reaction mixture was stirred at 0° C. for 30 min then warmed to 25° C. and stirred for 1.5 h. The reaction mixture was quenched with saturated ammonium chloride in water and extracted with dichloromethane (3×30 mL), organics dried over $MgSO_4$ and concentrated to a clear oil. Then dissolved in toluene and purified by chromatography (40 g column, 50 μm from Analogix, 0-20% EtOAc in hexanes over 20 min) to afford the more polar desired 3-iodo-1-methyl-1,4,5,6-tetrahydrocyclopenta[c]pyrazole (177 mg, 714 μmol, 55%) as a white solid. MS $(M+H)^+$=249; $^1$H NMR ($CDCl_3$) δ: 3.78 (s, 30H), 2.68-2.79 (m, 20H), 2.51-2.58 (m, 4H). The regisomeric product, 3-iodo-2-methyl-2,4,5,6-tetrahydrocyclopenta[c]pyrazole, (125 mg, 504 μmol, 39%) was also obtained as a white solid.

Step 3

1-Methyl-3-(tributylstannyl)-1,4,5,6-tetrahydrocyclopenta[c]pyrazole

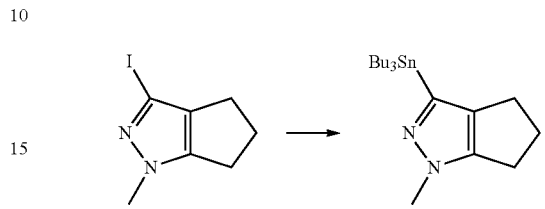

3-Iodo-1-methyl-1,4,5,6-tetrahydrocyclopenta[c]pyrazole (177 mg, 714 μmol) was dissolved in THF (3 mL). The colorless solution was cooled to −16° C. (NaCl/ice bath). isopropylmagnesium chloride 2 M in THF (400 μL, 799 μmol) was added dropwise at −16° C. The reaction mixture was stirred at −16° C. for 20 min. Then, tributylchlorostannane (267 mg, 223 μL, 821 μmol) was added slowly. The reaction mixture was warmed to 25° C. and stirred for 1.5 h. The reaction mixture was quenched with saturated ammonium chloride solution and then extracted with EtOAc (3×30 mL), the combined organics were washed with water (20 mL), brine (2×20 mL), dried over $MgSO_4$ and concentrated. The residue was dried under high vacuum yielding 1-methyl-3-(tributylstannyl)-1,4,5,6-tetrahydrocyclopenta[c]pyrazole which was taken into the next step without further treatment.

Step 4

N-Isopropyl-2-(1-methyl-1,4,5,6-tetrahydrocyclopenta[c]pyrazol-3-yl)-5-((2-(trimethylsilyl)ethoxy)methyl)-5H-pyrrolo[2,3-b]pyrazine-7-carboxamide

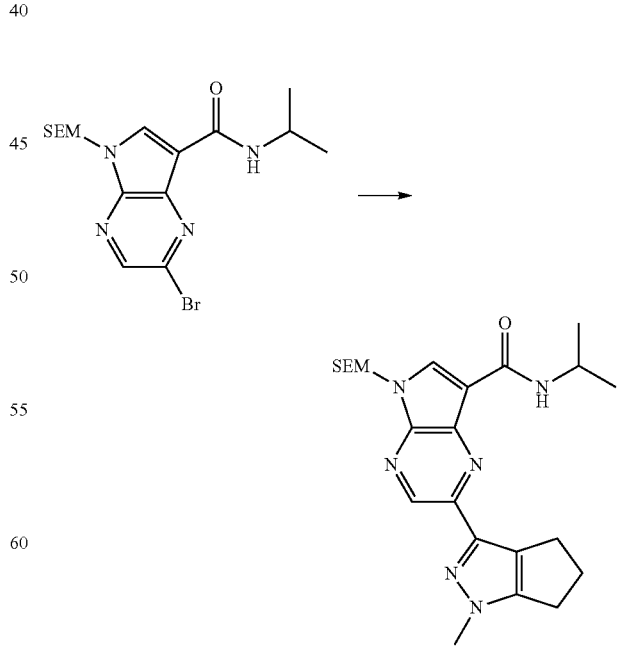

2-Bromo-N-isopropyl-5-((2-(trimethylsilyl)ethoxy)methyl)-5H-pyrrolo[2,3-b]pyrazine-7-carboxamide (184 mg, 446 µmol) and 1-methyl-3-(tributylstannyl)-1,4,5,6-tetrahydrocyclopenta[c]pyrazole (293 mg, 714 µmol) were dissolved in DMF (2.5 mL) under argon, tetrakis(triphenylphosphine)palladium (0) (25.8 mg, 22.3 µmol) and CuI (17.0 mg, 89.2 mmol) were added and the mixture sonicated for 5 min with bubbling argon. The reaction mixture was stirred at 90° C. (oil bath temperature) for 2.5 h. The reaction mixture was concentrated under high vacuum and the residue was purified by chromatography (40 g column, 50 µm from Analogix, 0-50% EtOAc in hexanes over 30 min) to give N-isopropyl-2-(1-methyl-1,4,5,6-tetrahydrocyclopenta[c]pyrazol-3-yl)-5-((2-(trimethylsilyl)ethoxy)methyl)-5H-pyrrolo[2,3-b]pyrazine-7-carboxamide (68 mg, 150 µmol, 34%) as a light yellow solid. MS (M+Na)$^+$=477; $^1$H NMR (CDCl$_3$) δ: 9.06 (s, 1H), 8.28 (s, 1H), 8.13 (d, J=8.3 Hz, 1H), 5.68 (s, 2H), 4.44 (dq, J=14.5, 6.6 Hz, 1H), 3.89 (s, 3H), 3.47-3.64 (m, 2H), 3.04 (t, J=7.0 Hz, 2H), 2.62-2.86 (m, 4H), 1.34 (d, J=6.8 Hz, 6H), 0.86-0.96 (m, 2H), −0.06 (s, 9H).

Step 5

N-Isopropyl-2-(1-methyl-1,4,5,6-tetrahydrocyclopenta[c]pyrazol-3-yl)-5H-pyrrolo[2,3-b]pyrazine-7-carboxamide

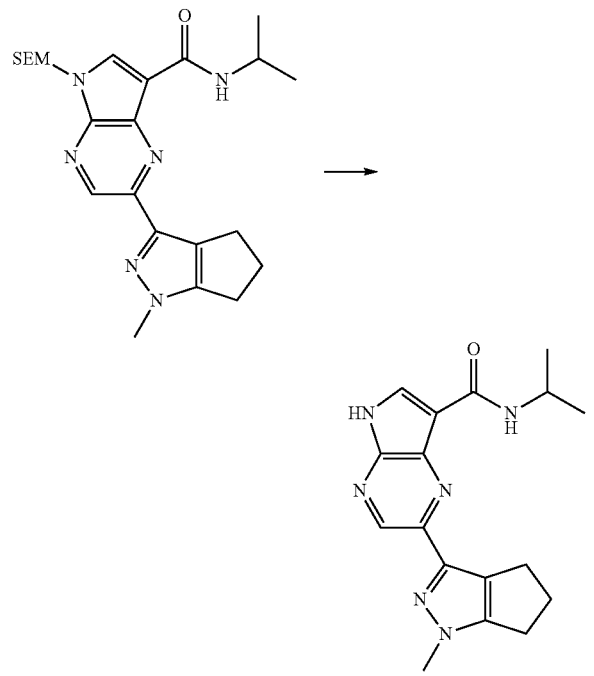

To a solution of N-isopropyl-2-(1-methyl-1,4,5,6-tetrahydrocyclopenta[c]pyrazol-3-yl)-5-((2-(trimethylsilyl)ethoxy)methyl)-5H-pyrrolo[2,3-b]pyrazine-7-carboxamide (68 mg, 150 µmol) in dichloromethane (5 mL) was added TFA (1.48 g, 1.00 mL, 13.0 mmol) and the reaction mixture stirred for 15 h then concentrated. The residue was re-dissolved in 5 mL of a solution of dichloromethane/MeOH/ammonium hydroxide (60:10:1) and stirred at 25° C. for 3 h, then evaporated and purified by chromatography (40 g column, 50 µm from Analogix, 0 to 5% MeOH containing 10% ammonium hydroxide in dichloromethane). The pure product was suspended in dichloromethane and cyclohexane added to promote solid formation, which was separated by decantation and dried under high vacuum to give N-isopropyl-2-(1-methyl-1,4,5,6-tetrahydrocyclopenta[c]pyrazol-3-yl)-5H-pyrrolo[2,3-b]pyrazine-7-carboxamide (45 mg, 139 mmol, 93%) as a white solid. MS (M+H)$^+$=325; $^1$H NMR (DMSO-d$_6$) δ: 12.68 (br. s., 1H), 8.87 (s, 1H), 8.31 (s, 1H), 8.00 (d, J=7.9 Hz, 1H), 4.02-4.46 (m, 1H), 3.79 (s, 3H), 2.92 (t, J=6.4 Hz, 2H), 2.73 (t, J=6.4 Hz, 2H), 2.60 (t, J=6.4 Hz, 2H), 1.24 (d, J=6.4 Hz, 6H).

Example 283

2-(5-(Difluoromethoxy)-1-methyl-1H-indazol-3-yl)-N-isopropyl-5H-pyrrolo[2,3-b]pyrazine-7-carboxamide

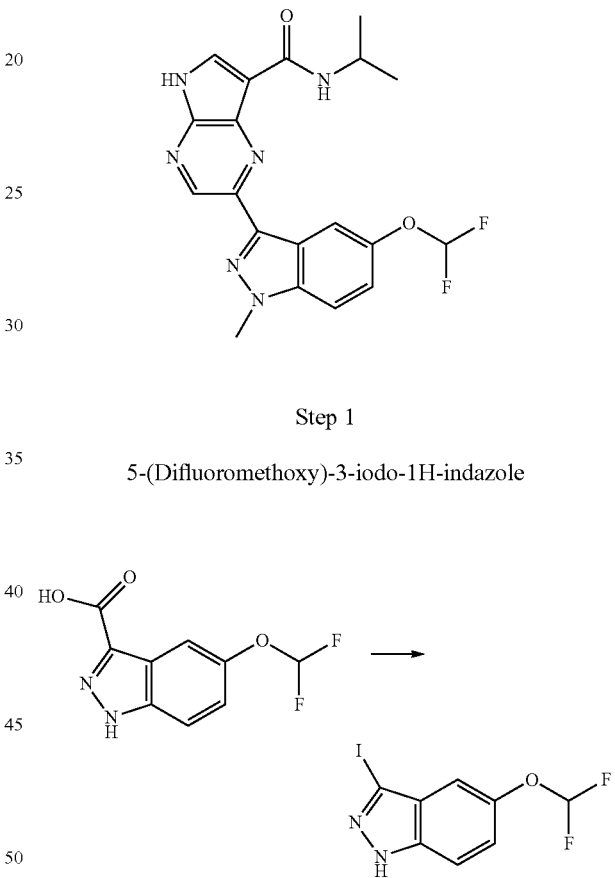

Step 1

5-(Difluoromethoxy)-3-iodo-1H-indazole

To a mixture of 5-(difluoromethoxy)-1H-indazole-3-carboxylic acid (1 g, 4.38 mmol), and sodium bicarbonate (1.22 g, 563 µL, 14.5 mmol) in dichloroethane (10.0 mL) and water (10.0 mL) were added in one portion sodium iodide (1.71 g, 11.4 mmol) and iodine (1.45 g, 5.7 mmol) and the mixture heated at to 100° C. (oil bath temperature) with vigorous stirring for 45 minutes. After cooling to 25° C. the mixture was diluted with dichloromethane then washed with 10% Na$_2$S$_2$O$_3$ and saturated NaHCO$_3$. The organic phases were combined, dried (MgSO$_4$) and concentrated to an off-white solid which was dissolved in dichloromethane, hexane added to promote solid formation and allowed to stand. The solid formed was separated by decanting the mother liquor and dried to give 5-(difluoromethoxy)-3-iodo-1H-indazole (1145 mg, 3.69 mmol, 84.3%) as a white fluffy solid. MS (M−H)$^−$ =308.9; $^1$H NMR (CDCl$_3$) δ: 7.52 (d, J=9.1 Hz, 1H), 7.28-7.36 (m, 1H), 6.57 (t, J=73.7 Hz, 1H).

Step 2

5-(Difluoromethoxy)-3-iodo-1-methyl-1H-indazole

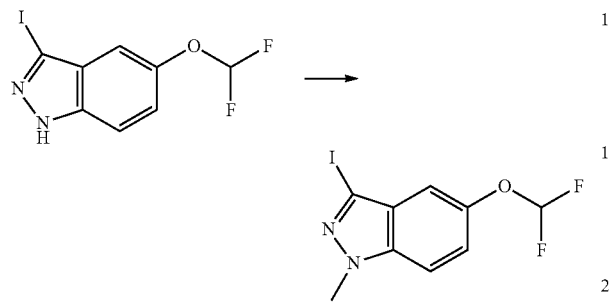

To a solution of 5-(difluoromethoxy)-3-iodo-1H-indazole (562 mg, 1.81 mmol) in THF (10.00 mL) at 0° C. was added KOtBu (1M in THF, 2.54 mL, 2.54 mmol) and the mixture stirred at 0° C. for 30 min then MeI (360 mg, 159 µL, 2.54 mmol) added. The reaction mixture was stirred at 0° C. for 30 min then warmed to 25° C. and stirred for 1.5 h. The reaction mixture was quenched with saturated ammonium chloride in water and extracted with dichloromethane (3×30 mL), organics dried over MgSO$_4$ and concentrated to a clear oil. Purification by chromatography (80 g column, 50 µm from Analogix, 0-20% EtOAc in hexanes over 20 min) gave 5-(difluoromethoxy)-3-iodo-1-methyl-1H-indazole (465 mg, 1.43 mmol, 79.2%) as a waxy off-white solid. MS (M+H)$^+$=324.9; $^1$H NMR (CDCl$_3$) δ: 7.32-7.40 (m, 1H), 7.24-7.30 (m, 1H), 7.21 (d, J=2.3 Hz, 1H), 6.55 (t, J=73.7 Hz, 1H), 4.10 (s, 3H). The regioisomeric product, 5-(difluoromethoxy)-3-iodo-2-methyl-2H-indazole, (108 mg, 333 µmol, 18%) was also obtained as a white solid.

Step 3

5-(Difluoromethoxy)-1-methyl-3-(tributylstannyl)-1H-indazole

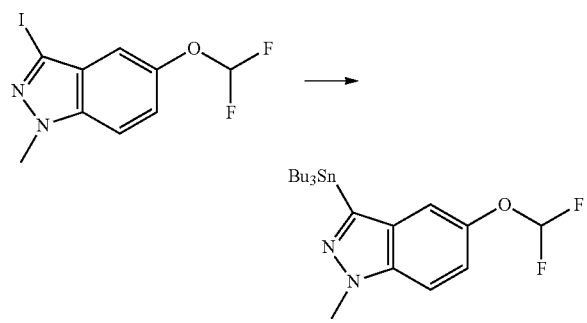

5-(Difluoromethoxy)-3-iodo-1-methyl-1H-indazole (0.265 g, 818 µmol) was dissolved in THF (3.00 mL). The colorless solution was cooled to −16° C. (NaCl/ice bath) then isopropylmagnesium chloride (2M in THF, 458 µL, 916 µmol) added dropwise at −16° C. The reaction mixture was stirred at −16° C. for 20 min then tributylchlorostannane (306 mg, 255 µL, 940 µmol) was added slowly. The reaction mixture was warmed to 25° C. and stirred for 1.5 h. The reaction mixture was quenched with saturated ammonium chloride solution, extracted with dichloromethane (3×30 mL), organics dried over MgSO$_4$ and concentrated to a yellow oil. The residue was dried under high vacuum and taken into next step without further purification.

Step 4

2-(5-(Difluoromethoxy)-1-methyl-1H-indazol-3-yl)-5-((2-(trimethylsilyl)ethoxy)methyl)-5H-pyrrolo[2,3-b]pyrazine-7-carbaldehyde

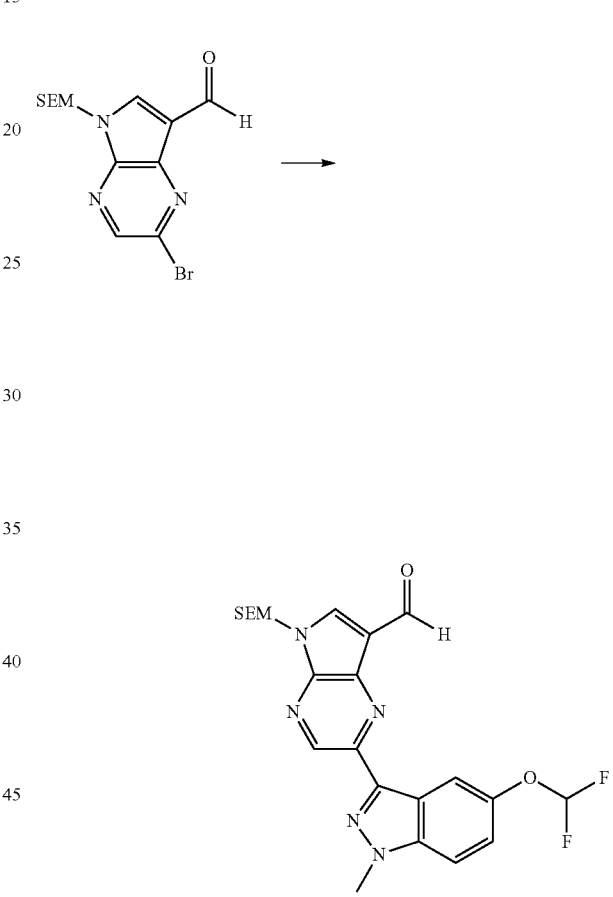

2-Bromo-5-((2-(trimethylsilyl)ethoxy)methyl)-5H-pyrrolo[2,3-b]pyrazine-7-carbaldehyde (224 mg, 629 µmol) and 5-(difluoromethoxy)-1-methyl-3-(tributylstannyl)-1H-indazole (398 mg, 818 µmol.30) were dissolved in DMF (3 mL) under argon, tetrakis(triphenylphosphine)palladium (0) (36.3 mg, 31.4 µmol) and CuI (24.0 mg, 126 µmol, Eq: 0.20) were added and the mixture sonicated for 5 min with bubbling argon. The reaction mixture was stirred at 90° C. (oil bath temperature) for 2.5 h. The reaction mixture was concentrated under high vacuum and the residue was purified by chromatography (80 g column, 50 µm from Analogix, 0-50% EtOAc in hexanes over 30 min) to give 2-(5-(difluoromethoxy)-1-methyl-1H-indazol-3-yl)-5-((2-(trimethylsilyl)ethoxy)methyl)-5H-pyrrolo[2,3-b]pyrazine-7-carbaldehyde (217 mg, 458 µmol, 72.9%) as a light brown solid. MS (M+H)$^+$=474; $^1$H NMR (CDCl$_3$) δ: 10.51 (br. s., 1H), 9.29 (s, 1H), 8.61 (s, 1H), 8.30 (s, 1H), 7.38-7.52 (m, 1H), 7.27-7.36 (m, 1H), 6.69

(t, J=74.8 Hz, 1H), 5.76 (s, 2H), 4.20 (s, 3H), 3.56-3.70 (m, 2H), 0.91-1.02 (m, 2H), −0.08-0.06 (m, 9H).

Step 5

2-(5-(Difluoromethoxy)-1-methyl-1H-indazol-3-yl)-5-((2-(trimethylsilyl)ethoxy)methyl)-5H-pyrrolo[2,3-b]pyrazine-7-carboxylic acid

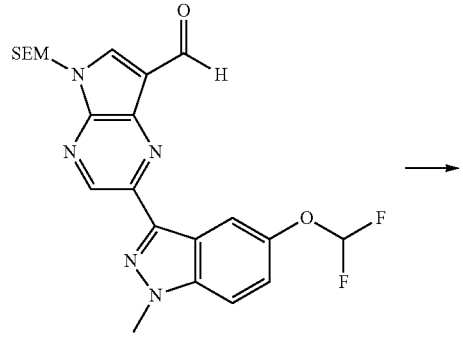

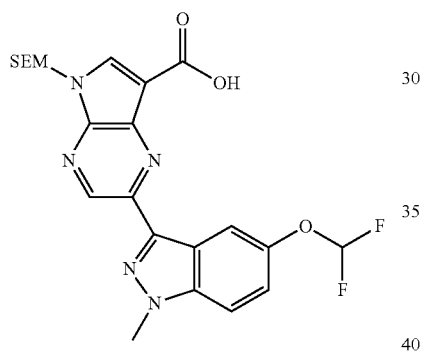

To a solution of 2-(5-(difluoromethoxy)-1-methyl-1H-indazol-3-yl)-5-((2-(trimethylsilyl)ethoxy)methyl)-5H-pyrrolo[2,3-b]pyrazine-7-carbaldehyde (217 mg, 458 µmol) in dioxane (6.5 mL) and water (2 mL) at 0° C. was added sulfamic acid (267 mg, 2.75 mmol), followed by drop-wise addition of a solution of sodium chlorite (67.3 mg, 596 µmol) and KH$_2$PO$_4$ (748 mg, 5.5 mmol) in water (4.5 mL) via dropping funnel over 15 min. The ice bath was removed and the light yellow suspension was stirred at 25° C. for 18 h. THF (6.5 mL) added to the yellow suspension and reaction continued at 25° C. for 2 h, then sulfamic acid (267 mg, 2.75 mmol) was added followed by dropwise addition of sodium chlorite (67.3 mg, 596 µmol) and KH$_2$PO$_4$ (748 mg, 5.5 mmol) in 5 mL of water. After 2 h the mixture was diluted with water (20 mL) and extracted with dichloromethane (3×30 mL). The combined organic layers were dried (MgSO$_4$) and evaporated. The light yellow solid residue was dissolved in dichloromethane/MeOH and dichloromethane evaporated to promote solid formation, the solid separated by filtration, rinsed with MeOH and hexanes then dried to give 2-(5-(difluoromethoxy)-1-methyl-1H-indazol-3-yl)-5-((2-(trimethylsilyl)ethoxy)methyl)-5H-pyrrolo[2,3-b]pyrazine-7-carboxylic acid (127 mg, 259 µmol, 57%) as a light yellow solid. MS (M+H)$^+$=490; $^1$H NMR (DMSO-d$_6$) δ: 12.57 (br. s., 1H), 9.12 (s, 1H), 8.69 (s, 1H), 8.65 (d, J=2.3 Hz, 1H), 7.80 (d, J=9.1 Hz, 1H), 7.35 (dd, J=8.9, 2.5 Hz, 1H), 7.20 (t, J=74.8 Hz, 1H), 5.71 (s, 2H), 4.18 (s, 3H), 3.58 (t, J=7.9 Hz, 2H), 0.84 (t, J=7.9 Hz, 2H), −0.21--0.01 (s, 9H).

Step 6

2-(5-(Difluoromethoxy)-1-methyl-1H-indazol-3-yl)-N-isopropyl-5-((2-(trimethylsilyl)ethoxy)methyl)-5H-pyrrolo[2,3-b]pyrazine-7-carboxamide

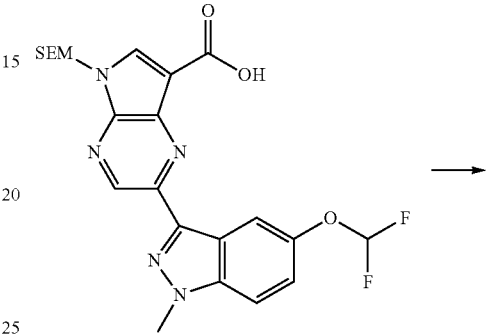

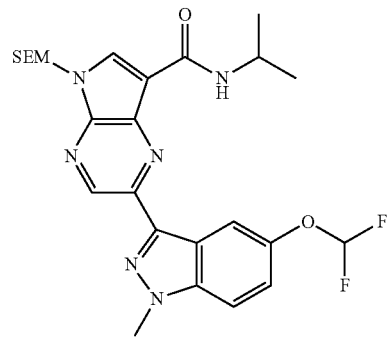

In a 16×100 mm screw cap test tube were added HATU (28.0 mg, 73.5 µmol.20) and propan-2-amine (14.5 mg, 21.0 µL, 245 µmol) then 2-(5-(difluoromethoxy)-1-methyl-1H-indazol-3-yl)-5-((2-(trimethylsilyl)ethoxy)methyl)-5H-pyrrolo[2,3-b]pyrazine-7-carboxylic acid (30 mg, 61.3 µmol) and DMF (2 mL). The reaction mixture was stirred at 25° C. for 15 h. Propan-2-amine (14.5 mg, 21.0 µL, 245 µmol) and HATU (28.0 mg, 73.5 µmol) were added. After 3 h the solvents were evaporated and the residue purified by chromatography (spherical silica 20-45 µm, 23 g, Versaflash Supelco, 0 to 50% EtOAc in hexanes over 30 min) to yield 2-(5-(difluoromethoxy)-1-methyl-1H-indazol-3-yl)-N-isopropyl-5-((2-(trimethylsilyl)ethoxy)methyl)-5H-pyrrolo[2,3-b]pyrazine-7-carboxamide (32.5 mg, 61.3 µmol, 100%) as a light yellow solid. MS (M+Na)$^+$=553.1; $^1$H NMR (CDCl$_3$) δ: 9.25 (s, 1H), 8.40 (s, 1H), 8.27 (d, J=2.3 Hz, 1H), 8.20 (d, J=7.6 Hz, 1H), 7.45-7.53 (m, 1H), 7.36 (dd, J=8.9, 2.1 Hz, 1H), 6.53 (t, J=74.0 Hz, 1H), 5.73 (s, 2H), 4.38-4.59 (m, 1H), 4.21 (s, 3H), 3.55-3.64 (m, 2H), 1.42 (d, J=6.4 Hz, 6H), 0.88-1.03 (m, 2H), −0.04 (s, 9H).

Step 7

2-(5-(Difluoromethoxy)-1-methyl-1H-indazol-3-yl)-N-isopropyl-5H-pyrrolo[2,3-b]pyrazine-7-carboxamide

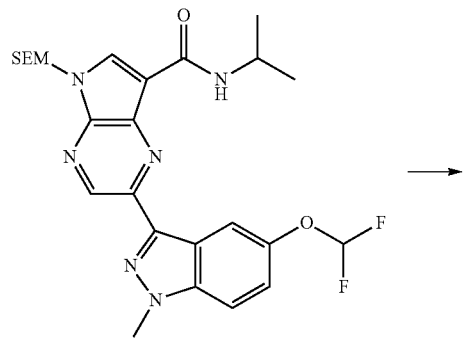

→

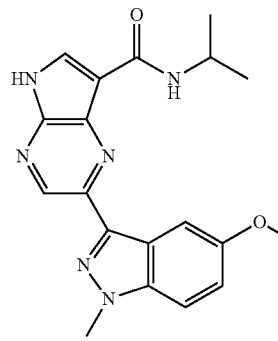

To a pale yellow solution of 2-(5-(difluoromethoxy)-1-methyl-1H-indazol-3-yl)-N-isopropyl-5-((2-(trimethylsilyl)ethoxy)methyl)-5H-pyrrolo[2,3-b]pyrazine-7-carboxamide (32.5 mg, 61.2 µmol) in dichloromethane (1.44 mL) was added TFA (426 mg, 288 µL, 3.73 mmol) and stirred at 25° C. for 15 h. The mixture was concentrated then re-dissolved in 5 mL of a solution of dichloromethane/MeOH/ammonium hydroxide (60:10:1) and stirred at 25° C. for 3 h, then evaporated to an off-white solid which was purified by chromatography (spherical silica 20-45 µm, 23 g, Versaflash Supelco, 0 to 5% MeOH containing 10% ammonium hydroxide in dichloromethane). The pure product was dissolved in dichloromethane/MeOH and dichloromethane evaporated to allow solid formation, then the solid was collected by filtration and dried to give 2-(5-(difluoromethoxy)-1-methyl-1H-indazol-3-yl)-N-isopropyl-5H-pyrrolo[2,3-b]pyrazine-7-carboxamide (23 mg, 57.4 µmol, 94%) as a light yellow solid. MS (M+H)⁺=401; ¹H NMR (DMSO-d₆) δ: 12.83 (br. s., 1H), 9.10 (s, 1H), 8.41 (s, 1H), 8.20 (d, J=2.3 Hz, 1H), 7.96 (d, J=7.9 Hz, 1H), 7.86 (d, J=9.4 Hz, 1H), 7.42 (dd, J=9.1, 1.9 Hz, 1H), 7.21 (t, J=74.4 Hz, 1H), 4.12-4.33 (m, 4H), 2.49 (s, 9H), 1.30 (d, J=6.4 Hz, 6H).

Example 284

2-(5-Difluoromethoxy-1-methyl-1H-indazol-3-yl)-5H-pyrrolo[2,3-b]pyrazine-7-carboxylic acid tert-butylamide

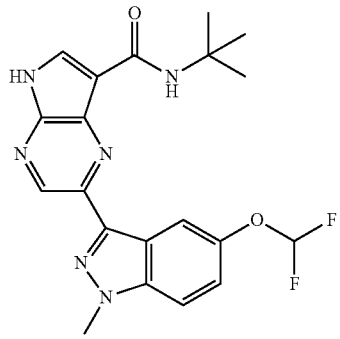 [SMILES: Cn1nc(-c2cnc3[nH]cc(C(=O)NC(C)(C)C)c3n2)c2cc(OC(F)F)ccc21]

Step 1

N-tert-Butyl-2-(5-(difluoromethoxy)-1-methyl-1H-indazol-3-yl)-5-((2-(trimethylsilyl)ethoxy)methyl)-5H-pyrrolo[2,3-b]pyrazine-7-carboxamide

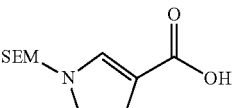

→

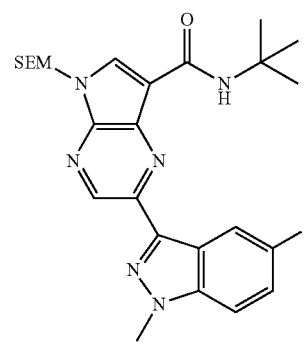

In a 16×100 mm screw cap test tube were added HATU (28.0 mg, 73.5 µmol.20) and 2-methylpropan-2-amine (17.9 mg, 245 µmol) then 2-(5-(difluoromethoxy)-1-methyl-1H-indazol-3-yl)-5-((2-(trimethylsilyl)ethoxy)methyl)-5H-pyrrolo[2,3-b]pyrazine-7-carboxylic acid (30 mg, 61.3 µmol)

dissolved in DMF (2.00 mL) was added to give a light yellow solution which immediately formed a white precipitated. The reaction mixture stirred at 25° C. overnight. TLC and LCMS showed incomplete reaction, added 2-methylpropan-2-amine (17.9 mg, 245 µmol) and HATU (28.0 mg, 73.5 µmol.20) then the reaction continued at 25° C. for 3 h. Solvents evaporated and residue purified by chromatography (spherical silica 20-45 µm, 23 g, Versaflash Supelco) eluting with 0 to 50% EtOAc in hexanes over 30 min to yield N-tert-butyl-2-(5-(difluoromethoxy)-1-methyl-1H-indazol-3-yl)-5-((2-(trimethylsilyl)ethoxy)methyl)-5H-pyrrolo[2,3-b]pyrazine-7-carboxamide (33.4 mg, 61.3 µmol, 100%) as an off-white solid. $^1$H NMR (CDCl$_3$) δ: 9.21 (s, 1H), 8.35 (s, 1H), 8.29 (d, J=2.3 Hz, 1H), 8.04 (s, 1H), 7.44-7.53 (m, 1H), 7.30-7.38 (m, 1H), 7.27 (s, 2H), 6.39 (t, J=74.0 Hz, 1H), 5.72 (s, 2H), 4.21 (s, 3H), 3.50-3.65 (m, 2H), 1.61 (s, 9H), 0.86-1.07 (m, 2H), −0.04 (s, 9H).

Step 2

2-(5-Difluoromethoxy)-1-methyl-1H-indazol-3-yl)-5H-pyrrolo[2,3-b]pyrazine-7-carboxylic acid tert-butylamide

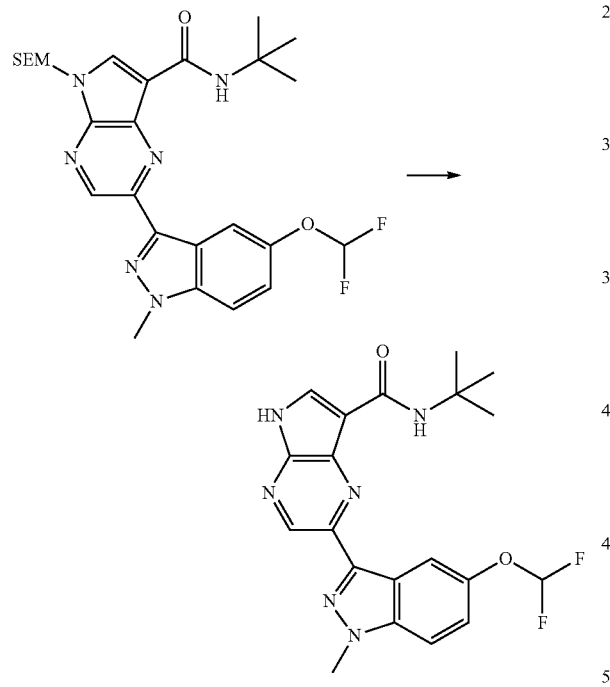

To a pale yellow solution of N-tert-butyl-2-(5-(difluoromethoxy)-1-methyl-1H-indazol-3-yl)-5-((2-(trimethylsilyl)ethoxy)methyl)-5H-pyrrolo[2,3-b]pyrazine-7-carboxamide (33.4 mg, 61.3 µmol) in dichloromethane (1.44 mL) was added TFA (426 mg, 288 µL, 3.74 mmol, 61 equiv.). The reaction mixture turned orange and was stirred at 25° C. overnight then concentrated. The residue was re-dissolved in 5 mL of a solution of (dichloromethane/MeOH/ammonium hydroxide; 60:10:1) and stirred at 25° C. for 3 h, then evaporated to a light yellow solid, dissolved in dichloromethane (containing a few drops of MeOH) and purified by chromatography (spherical silica 20-45 µm, 23 g, Versaflash Supelco) eluting with 0 to 5% over 15 min (MeOH containing 10% ammonium hydroxide)/dichloromethane. The pure product dissolved in dichloromethane/MeOH and dichloromethane evaporated to allow solid formation, the solid was separated by filtration and dried to give N-tert-butyl-2-(5-(difluoromethoxy)-1-methyl-1H-indazol-3-yl)-5H-pyrrolo[2,3-b]pyrazine-7-carboxamide (23 mg, 55.5 µmol, 90.5%) as an off-white solid. MS (M+H)$^+$=415; $^1$H NMR (DMSO-d$_6$) δ: 12.80 (br. s., 1H), 9.06 (s, 1H), 8.37 (s, 1H), 8.20 (d, J=1.9 Hz, 1H), 7.85 (d, J=8.7 Hz, 2H), 7.40 (dd, J=8.9, 2.1 Hz, 1H), 7.19 (t, J=74.4 Hz, 1H), 4.19 (s, 3H), 1.49 (s, 9H).

Example 285

2-(5-Difluoromethoxy-1-methyl-1H-indazol-3-yl)-5H-pyrrolo[2,3-b]pyrazine-7-carboxylic acid (2-hydroxy-1,1-dimethyl-ethyl)-amide

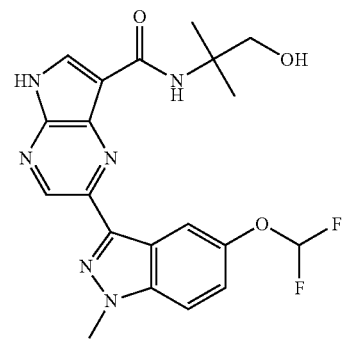 [SMILES: Cn1nc(-c2cnc3[nH]cc(C(=O)NC(C)(C)CO)c3n2)c2cc(OC(F)F)ccc21]

Step 1

2-(5-(Difluoromethoxy)-1-methyl-1H-indazol-3-yl)-N-(1-hydroxy-2-methylpropan-2-yl)-5-((2-(trimethylsilyl)ethoxy)methyl)-5H-pyrrolo[2,3-b]pyrazine-7-carboxamide

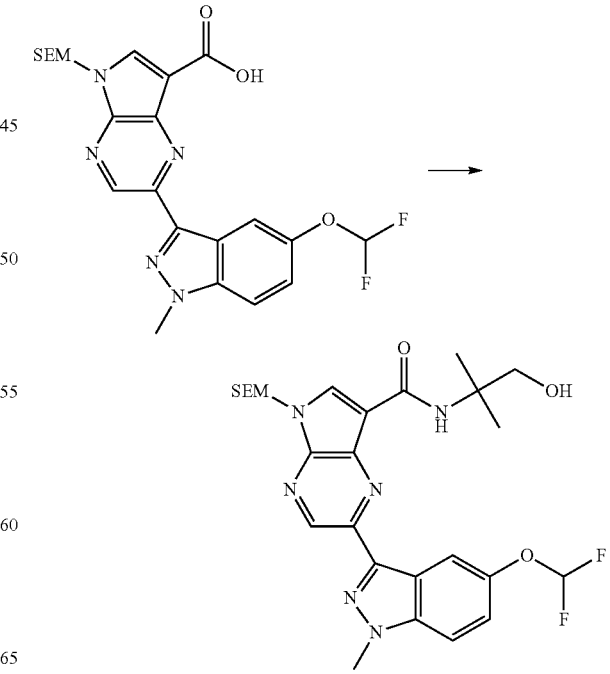

In a 16×100 mm screw cap test tube were added HATU (28.0 mg, 73.5 μmol.20) and 2-amino-2-methylpropan-1-ol (21.8 mg, 245 μmol) then 2-(5-(difluoromethoxy)-1-methyl-1H-indazol-3-yl)-5-((2-(trimethylsilyl)ethoxy)methyl)-5H-pyrrolo[2,3-b]pyrazine-7-carboxylic acid (30 mg, 61.3 μmol) dissolved in DMF (2.00 mL) was added to give a light yellow solution. The reaction mixture stirred at 25° C. overnight. TLC and LCMS showed incomplete reaction added 2-amino-2-methylpropan-1-ol (21.8 mg, 245 μmol) and HATU (28.0 mg, 73.5 μmol) and the reaction continued at 25° C. for 3 h. Solvents evaporated and residue purified by chromatography (spherical silica 20-45 μm, 23 g, Versaflash Supelco) eluting with 0 to 50% EtOAc in hexanes over 30 min to yield 2-(5-(difluoromethoxy)-1-methyl-1H-indazol-3-yl)-N-(1-hydroxy-2-methylpropan-2-yl)-5-((2-(trimethylsilyl)ethoxy)methyl)-5H-pyrrolo[2,3-b]pyrazine-7-carboxamide (34.4 mg, 61.3 μmol, 100%) as an off-white solid. $^1$H NMR (CDCl$_3$) δ: 9.22 (s, 1H), 8.35 (s, 1H), 8.31 (s, 1H), 8.24 (d, J=2.3 Hz, 1H), 7.43-7.52 (m, 1H), 7.34 (dd, J=8.9, 2.1 Hz, 1H), 6.53 (t, J=75.0 Hz, 1H), 5.72 (s, 2H), 4.21 (s, 3H), 3.79 (s, 2H), 3.53-3.64 (m, 2H), 1.55 (s, 6H), 0.85-1.07 (m, 2H), −0.03 (s, 9H).

Step 2

2-(5-Difluoromethoxy-1-methyl-1H-indazol-3-yl)-5H-pyrrolo[2,3-b]pyrazine-7-carboxylic acid (2-hydroxy-1,1-dimethyl-ethyl)-amide

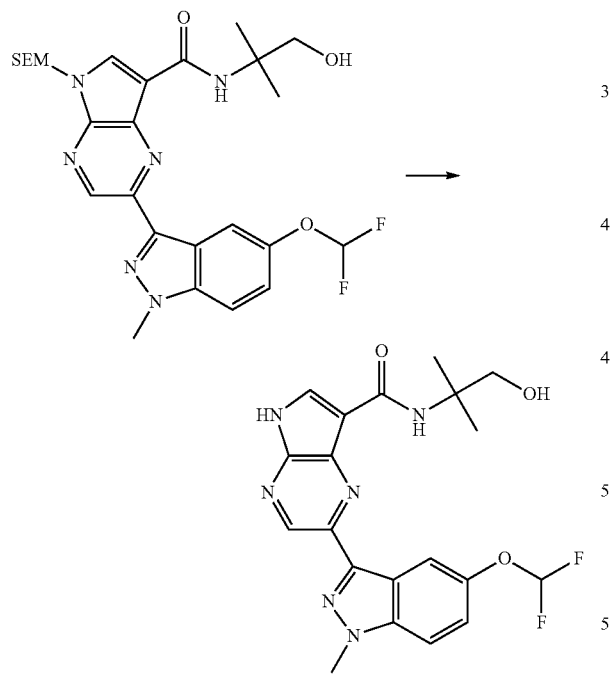

To a pale yellow solution of 2-(5-(difluoromethoxy)-1-methyl-1H-indazol-3-yl)-N-(1-hydroxy-2-methylpropan-2-yl)-5-((2-(trimethylsilyl)ethoxy)methyl)-5H-pyrrolo[2,3-b]pyrazine-7-carboxamide (34.4 mg, 61.4 μmol) in dichloromethane (1.44 mL) was added TFA (426 mg, 288 μL, 3.74 mmol, Eq: 60.9), the reaction mixture turned orange and was stirred at 25° C. overnight then concentrated. The residue was re-dissolved in 5 mL of a solution of (dichloromethane/MeOH/ammonium hydroxide; 60:10:1) and stirred at 25° C. for 3 h, then evaporated to a light yellow solid, dissolved in dichloromethane (containing a few drops of MeOH) and purified by chromatography (spherical silica 20-45 μm, 23 g, Versaflash Supelco) eluting with 0 to 5% over 15 min (MeOH containing 10% ammonium hydroxide)/dichloromethane to give a mixture of 2 compounds, no pure compound obtained. Mixture combined again and purified by preparative TLC (Silica GF 1000 μm, 20×40 cm (Gypsum Binder, Fluorescent Indicator)) to give the desired 2-(5-(difluoromethoxy)-1-methyl-1H-indazol-3-yl)-N-(1-hydroxy-2-methylpropan-2-yl)-5H-pyrrolo[2,3-b]pyrazine-7-carboxamide (20 mg, 46.5 μmol, 75.7%) as white needles. MS (M+H)$^+$=431; $^1$H NMR (DMSO-d$_6$) δ: 9.07 (s, 1H), 8.37 (s, 1H), 8.21 (d, J=1.9 Hz, 1H), 7.80-7.90 (m, 2H), 7.35-7.42 (m, 1H), 7.18 (t, J=74.4 Hz, 1H), 4.95 (t, J=5.7 Hz, 1H), 4.19 (s, 3H), 3.62 (d, J=5.7 Hz, 2H), 1.42 (s, 6H).

Example 286

2-(5-Difluoromethoxy-1-methyl-1H-indazol-3-yl)-5H-pyrrolo[2,3-b]pyrazine-7-carboxylic acid (4-hydroxymethyl-tetrahydro-pyran-4-yl)-amide

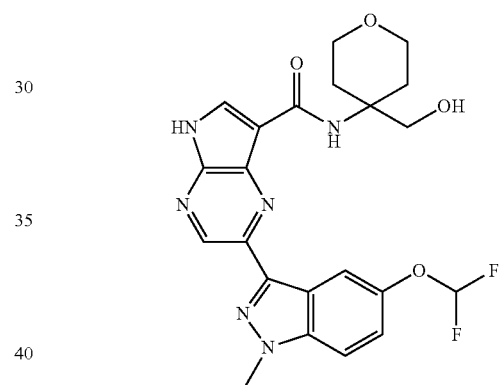

Step 1

2-(5-(Difluoromethoxy)-1-methyl-1H-indazol-3-yl)-N-(4-(hydroxymethyl)tetrahydro-2H-pyran-4-yl)-5-((2-(trimethylsilyl)ethoxy)methyl)-5H-pyrrolo[2,3-b]pyrazine-7-carboxamide

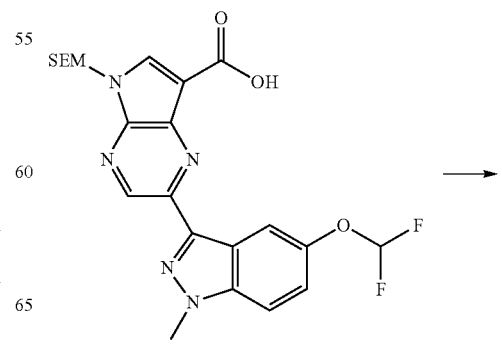

953
-continued

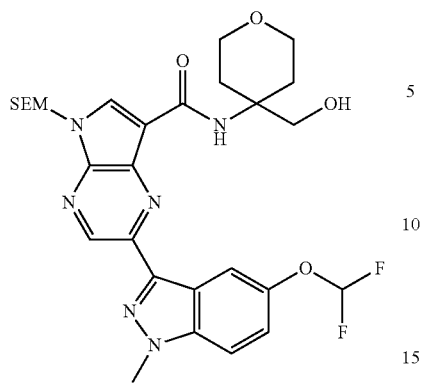

In a 16×100 mm screw cap test tube were added HATU (34.5 mg, 90.7 μmol.20), (4-aminotetrahydro-2H-pyran-4-yl)methanol (39.7 mg, 302 μmol) and 2-(5-(difluoromethoxy)-1-methyl-1H-indazol-3-yl)-5-((2-(trimethylsilyl)ethoxy)methyl)-5H-pyrrolo[2,3-b]pyrazine-7-carboxylic acid (37 mg, 75.6 μmol) then the mixture was dissolved in DMF (3 mL) to give a light yellow solution. The reaction mixture stirred at 25° C. overnight. Solvents evaporated and residue purified by chromatography (spherical silica 20-45 μm, 23 g, Versaflash Supelco) eluting with 0 to 5% over 30 min (MeOH containing 10% ammonium hydroxide)/dichloromethane to give 2-(5-(difluoromethoxy)-1-methyl-1H-indazol-3-yl)-N-(4-(hydroxymethyl)tetrahydro-2H-pyran-4-yl)-5-((2-(trimethylsilyl)ethoxy)methyl)-5H-pyrrolo[2,3-b]pyrazine-7-carboxamide (40 mg, 66.4 μmol, 87.8%) as a white solid. MS (M+H)$^+$=603; $^1$H NMR (CDCl$_3$) δ: 9.19 (s, 1H), 8.45 (s, 1H), 8.36 (s, 1H), 8.07 (d, J=2.3 Hz, 1H), 7.45-7.51 (m, 1H), 7.33 (dd, J=9.1, 2.3 Hz, 1H), 6.55 (t, J=76.0 Hz, 1H), 5.74 (s, 2H), 4.22 (s, 3H), 3.95 (s, 2H), 3.68-3.78 (m, 4H), 3.55-3.66 (m, 2H), 2.11-2.28 (m, 2H), 1.89-2.07 (m, 2H), 0.88-1.04 (m, 2H), −0.02 (s, 9H).

Step 2

2-(5-Difluoromethoxy-1-methyl-1H-indazol-3-yl)-5H-pyrrolo[2,3-b]pyrazine-7-carboxylic acid (4-hydroxymethyl-tetrahydro-pyran-4-yl)-amide

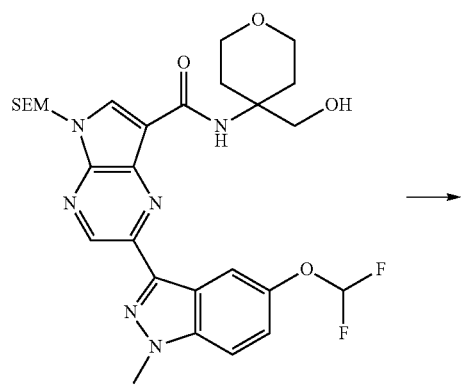

954
-continued

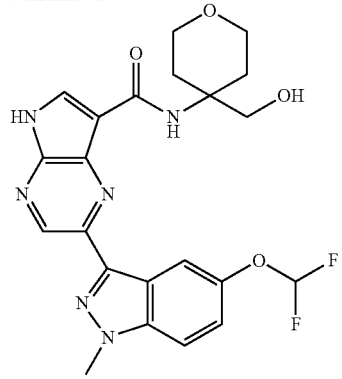 [SMILES: Cn1nc(-c2cnc3[nH]cc(C(=O)NC4(CO)CCOCC4)c3n2)c2cc(OC(F)F)ccc21]

To a solution of 2-(5-(difluoromethoxy)-1-methyl-1H-indazol-3-yl)-N-(4-(hydroxymethyl)tetrahydro-2H-pyran-4-yl)-5-((2-(trimethylsilyl)ethoxy)methyl)-5H-pyrrolo[2,3-b]pyrazine-7-carboxamide (40 mg, 66.4 μmol) in acetonitrile (6 mL) was added CsF (50.4 mg, 332 μmol, Eq: 5.00) and 18-crown-6 (17.5 mg, 66.4 μmol), the reaction mixture was heated to reflux for 72 h, then diluted with dichloromethane (20 mL), filtered over celite and concentrated. The residue was dissolved in dichloromethane and purified by chromatography (spherical silica 20-45 μm, 23 g, Versaflash Supelco) eluting with 0 to 5% over 15 min (MeOH containing 10% ammonium hydroxide)/dichloromethane. The pure product dissolved in dichloromethane/MeOH and cyclohexane added to allow solid formation, which was separated by filtration and dried to give 2-(5-(difluoromethoxy)-1-methyl-1H-indazol-3-yl)-N-(4-(hydroxymethyl)tetrahydro-2H-pyran-4-yl)-5H-pyrrolo[2,3-b]pyrazine-7-carboxamide (16 mg, 33.9 μmol, 51.0%) as an off-white solid. MS (M+H)$^+$= 473 (>90% purity); $^1$H NMR (DMSO-d$_6$) δ: 9.07 (s, 1H), 8.40 (s, 1H), 8.04 (d, J=1.9 Hz, 1H), 7.78-7.88 (m, 2H), 7.37-7.43 (m, 1H), 7.21 (t, J=74.4 Hz, 1H), 4.92 (t, J=5.7 Hz, 1H), 4.19 (s, 3H), 3.73 (d, J=5.7 Hz, 2H), 3.50-3.69 (m, 4H), 2.21 (d, J=13.6 Hz, 2H), 1.70-1.89 (m, 2H). Unreacted starting material (11 mg, 27%) was also recovered.

Example 287

2-(5-Methoxy-1-methyl-1H-indazol-3-yl)-5H-pyrrolo[2,3-b]pyrazine-7-carboxylic acid tert-butylamide

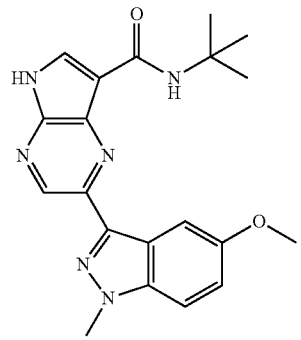 [SMILES: COc1ccc2c(c1)c(-c1cnc3[nH]cc(C(=O)NC(C)(C)C)c3n1)nn2C]

Step 1

3-Iodo-5-methoxy-1-methyl-1H-indazole

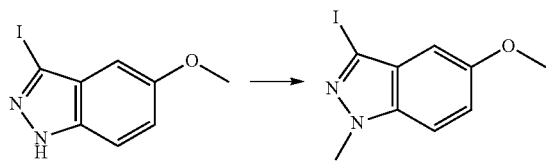

To a solution of 3-iodo-5-methoxy-1H-indazole (442 mg, 1.61 mmol) in THF (10.0 mL) at 0° C. was added KOtBu 1M in THF (2.26 mL, 2.26 mmol) and the mixture stirred at 0° C. for 30 min where it became a pale brown reddish solution then added MeI (320 mg, 141 μL, 2.26 mmol). The reaction mixture was stirred at 0° C. for 30 min then warmed to 25° C. and stirred for 1.5 h. The reaction mixture was quenched with saturated ammonium chloride in water and extracted with dichloromethane (3×30 mL), organics dried over MgSO$_4$ and concentrated to a clear oil. Then dissolved in toluene and purified by chromatography (80 g column, 50 μm from Analogix, 0-20% EtOAc in hexanes over 20 min to afford 3-iodo-5-methoxy-1-methyl-1H-indazole (355 mg, 1.23 mmol, 76.4%) as an off-white solid. MS (M+H)$^+$=288.9 (>90% purity); $^1$H NMR (CDCl$_3$) δ: 7.24 (d, J=9.1 Hz, 1H), 7.10 (dd, J=9.1, 2.6 Hz, 1H), 6.75 (d, J=2.6 Hz, 1H), 4.06 (s, 3H), 3.88 (s, 3H). The regioisomer 3-iodo-5-methoxy-2-methyl-2H-indazole (89 mg, 309 μmol, 19.2%) was also obtained as a white solid.

Step 2

5-Methoxy-1-methyl-3-(tributylstannyl)-1H-indazole

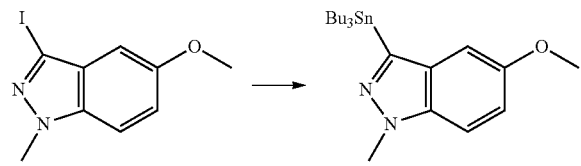

3-iodo-5-methoxy-1-methyl-1H-indazole (0.355 g, 1.23 mmol) was dissolved in THF (3.00 mL). The yellow solution was cooled to −16° C. (NaCl/ice bath), isopropylmagnesium chloride 2M in THF (690 μL, 1.38 mmol.12) was added dropwise at −16° C. The reaction mixture was stirred at −16° C. for 20 min where a solid precipitated. Then, tributylchlorostannane (461 mg, 384 μL, 1.42 mmol.15) was added slowly. The reaction mixture was warmed to 25° C. and stirred for 1.5 h. The reaction mixture was quenched with saturated ammonium chloride solution, extracted with dichloromethane (3×30 mL), organics dried over MgSO$_4$ and concentrated to a yellow oil. The residue was dried under high vacuum to give crude 5-methoxy-1-methyl-3-(tributylstannyl)-1H-indazole, which was used directly in the next step without further purification. The crude mass exceeded the expected amount so the yield was assumed to be quantitative.

Step 3

2-(5-Methoxy-1-methyl-1H-indazol-3-yl)-5-((2-(trimethylsilyl)ethoxy)methyl)-5H-pyrrolo[2,3-b]pyrazine-7-carbaldehyde

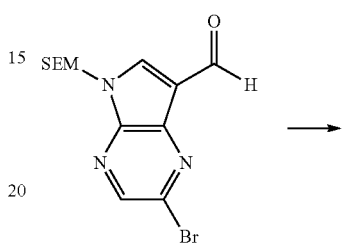

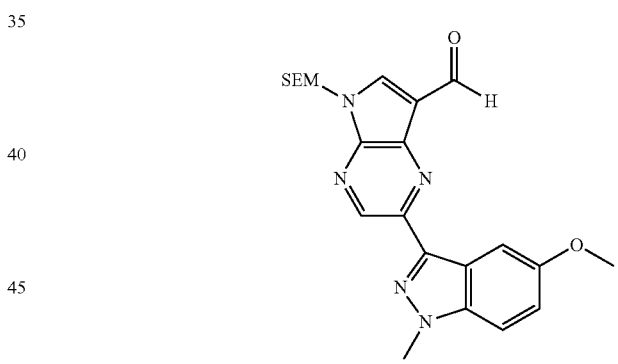

In a 25 mL round-bottomed flask, 2-bromo-5-((2-(trimethylsilyl)ethoxy)methyl)-5H-pyrrolo[2,3-b]pyrazine-7-carbaldehyde (439 mg, 1.23 mmol) and 5-methoxy-1-methyl-3-(tributylstannyl)-1H-indazole (556 mg, 1.23 mmol) were dissolved in DMF (3.00 mL) under argon, tetrakis(triphenylphosphine)palladium (0) (71.2 mg, 61.6 μmol) and CuI (46.9 mg, 246 μmol, Eq: 0.20) were added and the mixture sonicated for 5 min with bubbling argon. The reaction mixture was stirred at 90° C. (oil bath temperature) for 2.5 h. The reaction mixture was concentrated under high vacuum and the residue was purified by chromatography (80 g column, 50 μm from Analogix, 0-50% EtOAc in hexanes over 30 min) to give 2-(5-methoxy-1-methyl-1H-indazol-3-yl)-5-((2-(trimethylsilyl)ethoxy)methyl)-5H-pyrrolo[2,3-b]pyrazine-7-carbaldehyde (443 mg, 1.01 mmol, 82.2%) as a yellow solid. MS (M+H)$^+$=438 (>90% purity); $^1$H NMR (CDCl$_3$) δ: 10.50 (s, 1H), 9.34 (s, 1H), 8.37 (d, J=2.3 Hz, 1H), 8.30 (s, 1H), 7.39 (d, J=9.1 Hz, 1H), 7.19 (dd, J=9.1, 2.3 Hz, 1H), 5.80 (s, 2H), 4.21 (s, 3H), 4.07 (s, 3H), 3.59-3.73 (m, 2H), 0.91-1.06 (m, 2H), 0.00 (s, 8H).

Step 4

2-(5-Methoxy-1-methyl-1H-indazol-3-yl)-5-((2-(trimethylsilyl)ethoxy)methyl)-5H-pyrrolo[2,3-b]pyrazine-7-carboxylic acid

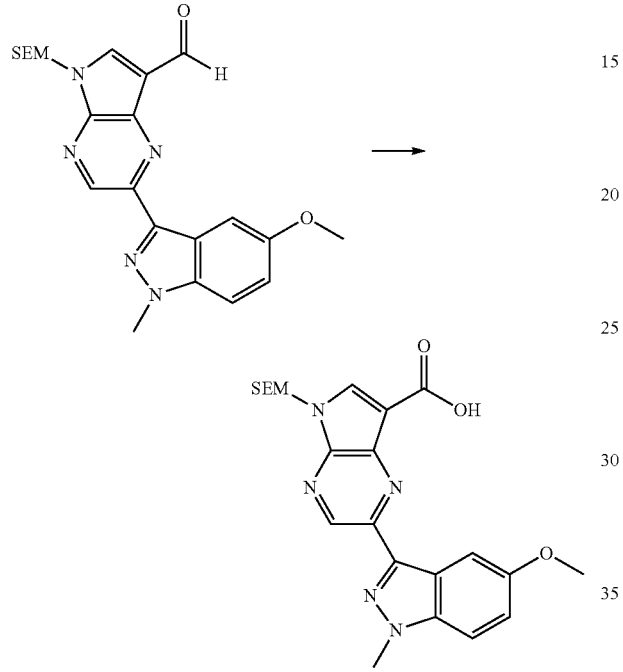

To a yellow suspension of 2-(5-methoxy-1-methyl-1H-indazol-3-yl)-5-((2-(trimethylsilyl)ethoxy)methyl)-5H-pyrrolo[2,3-b]pyrazine-7-carbaldehyde (443 mg, 1.01 mmol) in dioxane (14 mL) and water (4 mL) at 0° C. was added sulfamic acid (590 mg, 6.07 mmol, Eq: 6.00), followed by dropwise addition of a solution of sodium chlorite (149 mg, 1.32 mmol) and $KH_2PO_4$ (1.65 g, 12.1 mmol2.00) in water (4.5 mL) via dropping funnel over 15 min. The ice bath was removed and the light yellow suspension was stirred at 25° C. for 18 h. LCMS indicated reaction about 50% complete, THF (10 mL) added to the yellow suspension then addition at 25° C. of more reagents: sulfamic acid (590 mg, 6.07 mmol, Eq: 6.00) solid, followed by a dropwise addition of a solution of sodium chlorite (149 mg, 1.32 mmol) and $KH_2PO_4$ (1.65 g, 12.1 mmo12.00) in 10 mL of water and stirring continued at 25° C. for 4 h. Mixture diluted with water (50 mL) and extracted with dichloromethane (3×40 mL). The combined organic layers were dried ($MgSO_4$), added some charcoal heated to reflux, after cooling down to 25° C., filtered over a celite pad and evaporated. Light yellow solid residue was dissolved in dichloromethane/MeOH and dichloromethane evaporated to promote solid formation, solid separated by filtration, rinsed with MeOH and hexanes and dried to give 2-(5-methoxy-1-methyl-1H-indazol-3-yl)-5-((2-(trimethylsilyl)ethoxy)methyl)-5H-pyrrolo[2,3-b]pyrazine-7-carboxylic acid (238 mg, 525 μmol, 51.8%). MS (M+H)$^+$=454 (>90% purity); $^1$H NMR (CDCl$_3$) δ: 9.38 (s, 1H), 8.38 (s, 1H), 7.92 (d, J=2.6 Hz, 1H), 7.41 (d, J=9.1 Hz, 1H), 7.19 (dd, J=9.3, 2.5 Hz, 1H), 5.79 (s, 2H), 4.21 (s, 3H), 3.99 (s, 3H), 3.60-3.73 (m, 2H), 0.93-1.06 (m, 2H), 0.00 (s, 9H).

Step 5

N-tert-Butyl-2-(5-methoxy-1-methyl-1H-indazol-3-yl)-5-((2-(trimethylsilyl)ethoxy)methyl)-5H-pyrrolo[2,3-b]pyrazine-7-carboxamide

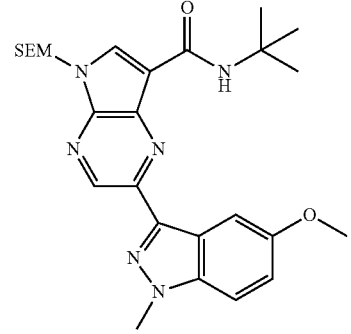

In a 16×100 mm screw cap test tube were added HATU (40.2 mg, 106 μmol.20) and 2-methylpropan-2-amine (25.8 mg, 353 μmol) then 2-(5-methoxy-1-methyl-1H-indazol-3-yl)-5-((2-(trimethylsilyl)ethoxy)methyl)-5H-pyrrolo[2,3-b]pyrazine-7-carboxylic acid (40 mg, 88.2 mmol) dissolved in DMF (2.00 mL) was added to give a light yellow solution which immediately formed a white precipitated. The reaction mixture stirred at 25° C. overnight, solvents evaporated and residue purified by chromatography (spherical silica 20-45 μm, 23 g, Versaflash Supelco) eluting with 0 to 50% EtOAc in hexanes over 30 min to yield N-tert-butyl-2-(5-methoxy-1-methyl-1H-indazol-3-yl)-5-((2-(trimethylsilyl)ethoxy)methyl)-5H-pyrrolo[2,3-b]pyrazine-7-carboxamide (40 mg, 78.6 μmol, 89.2%) as an off-white solid. MS (M+H)$^+$=509 (>90% purity); $^1$H NMR (CDCl$_3$) δ: 9.11 (s, 1H), 8.32 (s, 1H), 8.20 (s, 1H), 7.85 (d, J=2.3 Hz, 1H), 7.40 (d, J=9.1 Hz, 1H), 7.20 (dd, J=9.1, 2.3 Hz, 1H), 5.72 (s, 2H), 4.18 (s, 3H), 3.92 (s, 3H), 3.54-3.64 (m, 2H), 1.58 (s, 9H), 0.90-1.01 (m, 2H), −0.03 (s, 9H).

Step 6

2-(5-Methoxy-1-methyl-1H-indazol-3-yl)-5H-pyrrolo[2,3-b]pyrazine-7-carboxylic acid tert-butylamide

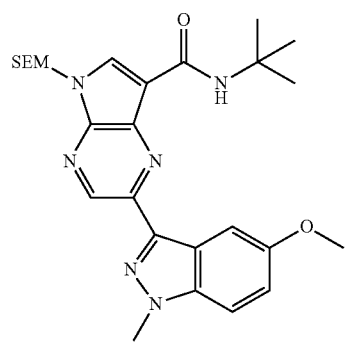

To a pale yellow solution of N-tert-butyl-2-(5-methoxy-1-methyl-1H-indazol-3-yl)-5-((2-(trimethylsilyl)ethoxy)methyl)-5H-pyrrolo[2,3-b]pyrazine-7-carboxamide (40 mg, 78.6 μmol) in dichloromethane (2 mL) was added TFA (2.96 g, 2000 μL, 26.0 mmol, Eq: 330), the reaction mixture turned bright orange and was stirred at 25° C. for 3 h, then concentrated. The residue was re-dissolved in 5 mL of a solution of (dichloromethane/MeOH/ammonium hydroxide; 60:10:1) and stirred at 25° C. overnight then evaporated to a light yellow solid, dissolved in dichloromethane (containing a few drops of MeOH) and purified by chromatography (spherical silica 20-45 μm, 23 g, Versaflash Supelco) eluting with 0 to 5% over 15 min (MeOH containing 10% ammonium hydroxide)/dichloromethane. The pure product dissolved in a small amount of dichloromethane/MeOH, added cyclohexane and some solvents evaporated to allow solid formation, which was separated by filtration and dried to give N-tert-butyl-2-(5-methoxy-1-methyl-1H-indazol-3-yl)-5H-pyrrolo[2,3-b]pyrazine-7-carboxamide (25 mg, 66.1 μmol, 84.0%) as an off-white solid. MS (M+H)$^+$=379 (>90% purity); $^1$H NMR (CDCl$_3$) δ: 9.11 (s, 1H), 8.31 (d, J=3.0 Hz, 1H), 8.22 (s, 1H), 7.86 (d, J=2.3 Hz, 1H), 7.41 (d, J=9.1 Hz, 1H), 7.26 (br. s., 2H), 7.17-7.23 (m, 1H), 4.18 (s, 3H), 3.92 (s, 3H), 1.59 (s, 9H).

Example 288

2-(5-Methoxy-1-methyl-1H-indazol-3-yl)-5H-pyrrolo[2,3-b]pyrazine-7-carboxylic acid (2-hydroxy-1,1-dimethyl-ethyl)-amide

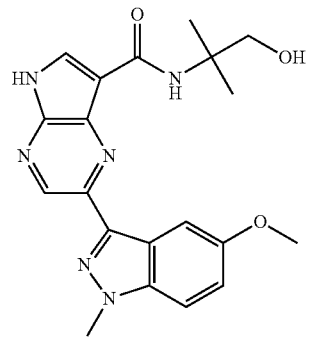 [SMILES: COc1ccc2c(c1)c(-c1cnc3[nH]cc(C(=O)NC(C)(C)CO)c3n1)nn2C]

Step 1

N-(1-Hydroxy-2-methylpropan-2-yl)-2-(5-methoxy-1-methyl-1H-indazol-3-yl)-5-((2-(trimethylsilyl)ethoxy)methyl)-5H-pyrrolo[2,3-b]pyrazine-7-carboxamide

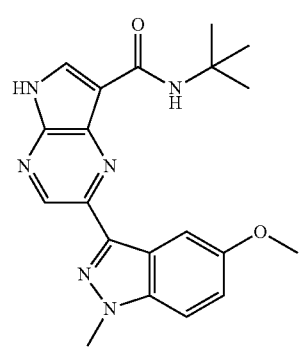

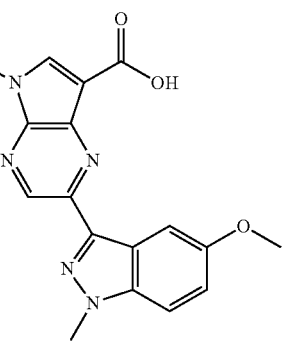

In a 16×100 mm screw cap test tube were added HATU (40.2 mg, 106 μmol.20) and 2-amino-2-methylpropan-1-ol (31.4 mg, 353 μmol) then 2-(5-methoxy-1-methyl-1H-indazol-3-yl)-5-((2-(trimethylsilyl)ethoxy)methyl)-5H-pyrrolo

[2,3-b]pyrazine-7-carboxylic acid (40 mg, 88.2 mmol) dissolved in DMF (2.00 mL) was added to give a light yellow solution. The reaction mixture stirred at 25° C. overnight, solvents evaporated and residue purified by chromatography (spherical silica 20-45 µm, 23 g, Versaflash Supelco) eluting with 0 to 50% EtOAc in hexanes over 25 min to yield N-(1-hydroxy-2-methylpropan-2-yl)-2-(5-methoxy-1-methyl-1H-indazol-3-yl)-5-((2-(trimethylsilyl)ethoxy)methyl)-5H-pyrrolo[2,3-b]pyrazine-7-carboxamide (46.3 mg, 88.2 µmol, 100%) as an off-white solid. MS (M+Na)$^+$=547 (>90% purity); $^1$H NMR (CDCl$_3$) δ: 9.14 (s, 1H), 8.49 (s, 1H), 8.32 (s, 1H), 7.85 (d, J=2.3 Hz, 1H), 7.41 (d, J=9.1 Hz, 1H), 7.20 (dd, J=9.3, 2.5 Hz, 1H), 5.72 (s, 2H), 4.18 (s, 3H), 3.92 (s, 3H), 3.78 (s, 2H), 3.54-3.65 (m, 2H), 1.53 (s, 6H), 0.91-1.01 (m, 2H), −0.03 (s, 9H).

Step 2

N-(1-Hydroxy-2-methylpropan-2-yl)-2-(5-methoxy-1-methyl-1H-indazol-3-yl)-5H-pyrrolo[2,3-b]pyrazine-7-carboxamide

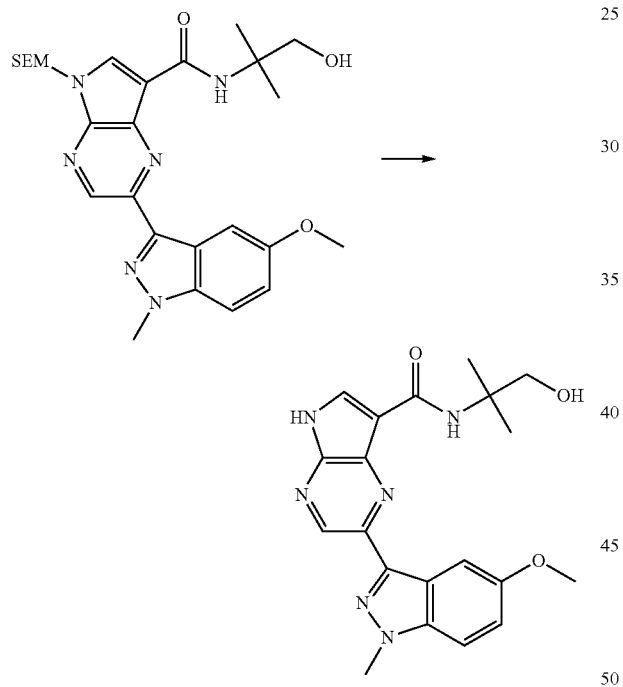

To a solution of N-(1-hydroxy-2-methylpropan-2-yl)-2-(5-methoxy-1-methyl-1H-indazol-3-yl)-5-((2-(trimethylsilyl)ethoxy)methyl)-5H-pyrrolo[2,3-b]pyrazine-7-carboxamide (46.3 mg, 88.2 µmol) in acetonitrile (5 mL) was added CsF (134 mg, 882 µmol) and 18-crown-6 (70.0 mg, 265 µmol), the reaction mixture was heated to reflux with stirring for 48 h, reaction diluted with dichloromethane (20 mL), filtered over celite and concentrated. The residue was dissolved in dichloromethane and purified by chromatography (spherical silica 20-45 µm, 23 g, Versaflash Supelco) eluting with 0 to 5% over 15 min (MeOH containing 10% ammonium hydroxide)/dichloromethane. The pure product dissolved in dichloromethane/MeOH and cyclohexane added to allow solid formation, which was separated by decantation and dried to give N-(1-hydroxy-2-methylpropan-2-yl)-2-(5-methoxy-1-methyl-1H-indazol-3-yl)-5H-pyrrolo[2,3-b]pyrazine-7-carboxamide (18 mg, 45.6 µmol, 51.7%) as a yellow solid. MS (M+H)$^+$=377; $^1$H NMR (DMSO-d$_6$) δ: 8.96 (s, 1H), 8.34 (s, 1H), 7.98 (br. s., 1H), 7.79 (br. s., 1H), 7.68 (d, J=9.1 Hz, 1H), 7.22 (d, J=8.3 Hz, 1H), 4.93 (br. s., 1H), 4.13 (s, 3H), 3.86 (s, 3H), 3.60 (d, J=4.9 Hz, 2H), 1.39 (s, 6H).

Example 289

2-(5-Difluoromethoxy-1H-indazol-3-yl)-5H-pyrrolo[2,3-b]pyrazine-7-carboxylic acid tert-butylamide

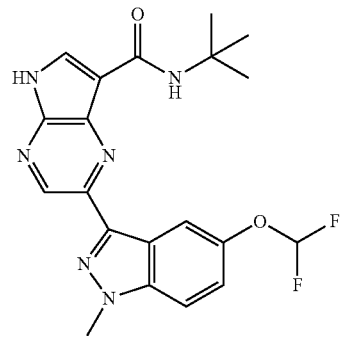 [SMILES: Cn1nc(-c2cnc3[nH]cc(C(=O)NC(C)(C)C)c3n2)c2cc(OC(F)F)ccc21]

Step 1

5-(Difluoromethoxy)-3-(tributylstannyl)-1H-indazole

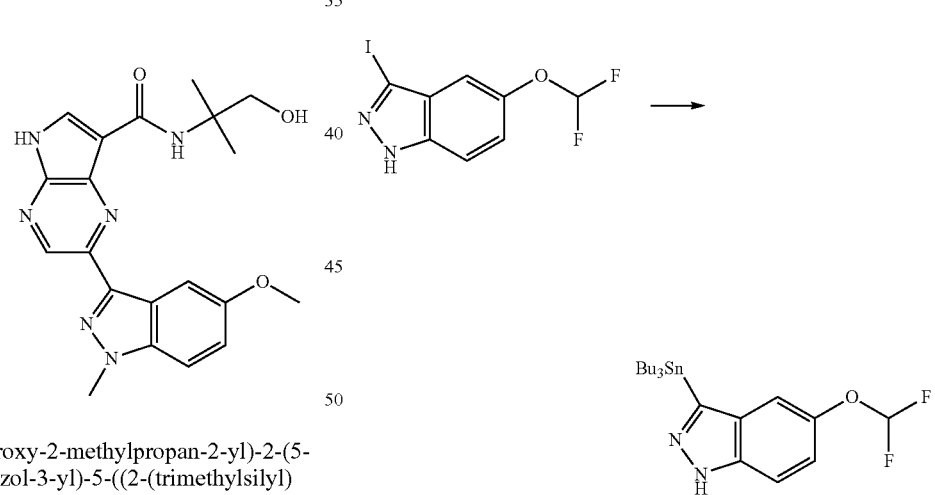

5-(Difluoromethoxy)-3-iodo-1H-indazole (0.175 g, 564 µmol) was dissolved in THF (3 mL). The colorless solution was cooled to −16° C. (NaCl/ice bath), isopropylmagnesium chloride 2M in THF (621 µL, 1.24 mmol.2) was added dropwise at −16° C. The reaction mixture was stirred at −16° C. for 20 min. Then, tributylchlorostannane (220 mg, 184 µL, 677 µmol.2) was added slowly. The reaction mixture was warmed to 25° C. and stirred for 1.5 h. The reaction mixture was quenched with saturated ammonium chloride solution, extracted with dichloromethane (3×30 mL), organics dried over MgSO$_4$ and concentrated to a yellow oil. The residue was dried under high vacuum and taken into next step without further purification yielding 5-(difluoromethoxy)-3-(tributylstannyl)-1H-indazole, crude mass exceeded yield, assumed quantitative.

Step 2

N-tert-Butyl-2-(5-(difluoromethoxy)-1H-indazol-3-yl)-5-((2-(trimethylsilyl)ethoxy)methyl)-5H-pyrrolo[2,3-b]pyrazine-7-carboxamide

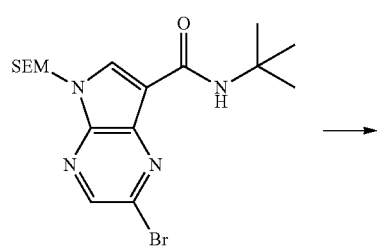

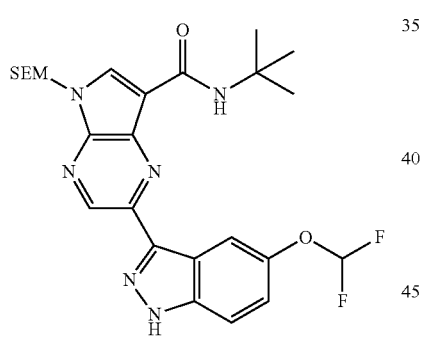

In a 25 mL round-bottomed flask, 2-bromo-N-tert-butyl-5-((2-(trimethylsilyl)ethoxy)methyl)-5H-pyrrolo[2,3-b]pyrazine-7-carboxamide (220 mg, 515 μmol) and 5-(difluoromethoxy)-3-(tributylstannyl)-1H-indazole (268 mg, 566 μmol.10) were dissolved in DMF (1.06 mL) under argon, tetrakis(triphenylphosphine)palladium (0) (29.7 mg, 25.7 μmol) and CuI (19.6 mg, 103 μmol, Eq: 0.20) were added and the mixture sonicated for 5 min with bubbling argon. The reaction mixture was stirred at 90° C. (oil bath temperature) for 2.5 h. The reaction mixture was concentrated under high vacuum and the residue was purified by chromatography (80 g column, 50 μm from Analogix, 0-50% EtOAc in hexanes over 30 min) to give N-tert-butyl-2-(5-(difluoromethoxy)-1H-indazol-3-yl)-5-((2-(trimethylsilyl)ethoxy)methyl)-5H-pyrrolo[2,3-b]pyrazine-7-carboxamide (159 mg, 300 μmol, 58.2%) as an off-white solid. MS (M+Na)$^+$=553 (>90% purity); $^1$H NMR (CDCl$_3$) δ: 10.74 (br. s., 1H), 9.29 (s, 1H), 8.42 (s, 1H), 8.36 (d, J=2.3 Hz, 1H), 8.09 (s, 1H), 7.64 (d, J=9.1 Hz, 1H), 7.40 (dd, J=8.9, 2.1 Hz, 1H), 6.57 (t, J=74.0 Hz, 1H), 5.76 (s, 2H), 3.56-3.70 (m, 2H), 1.67 (s, 9H), 0.92-1.04 (m, 2H), 0.00 (s, 9H).

Step 3

N-tert-Butyl-2-(5-(difluoromethoxy)-1H-indazol-3-yl)-5H-pyrrolo[2,3-b]pyrazine-7-carboxamide

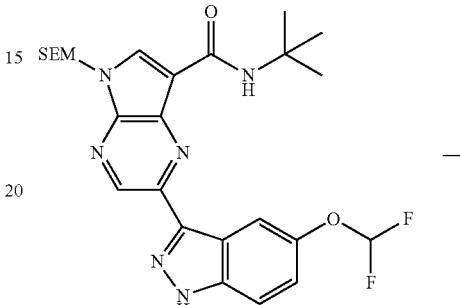

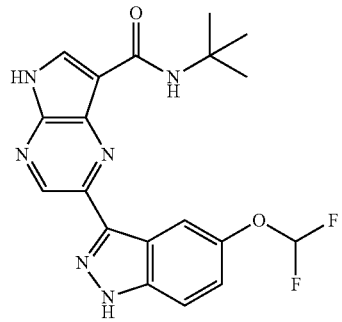

To a pale yellow solution of N-tert-butyl-2-(5-(difluoromethoxy)-1H-indazol-3-yl)-5-((2-(trimethylsilyl)ethoxy)methyl)-5H-pyrrolo[2,3-b]pyrazine-7-carboxamide (55 mg, 104 μmol) in dichloromethane (3 mL) was added TFA (1.48 g, 1000 μL, 13.0 mmol25), the reaction mixture turned orange and was stirred at 25° C. overnight then concentrated. The residue was re-dissolved in 5 mL of a solution of (dichloromethane/MeOH/ammonium hydroxide; 60:10:1) and stirred at 25° C. for 3 h, then evaporated to a light yellow solid, dissolved in dichloromethane (added few drops MeOH and heating) and purified by chromatography (spherical silica 20-45 μm, 23 g, Versaflash Supelco) eluting with 0 to 5% over 15 min (MeOH containing 10% ammonium hydroxide)/dichloromethane. The pure product suspended in dichloromethane and cyclohexane added to complete solid formation, solid was separated by decantation and dried under high vacuum to give N-tert-butyl-2-(5-(difluoromethoxy)-1H-indazol-3-yl)-5H-pyrrolo[2,3-b]pyrazine-7-carboxamide (26 mg, 64.9 μmol, 62.7%) as a white solid. MS (M+H)$^+$=401.1 (100% purity); $^1$H NMR (DMSO-d$_6$) δ: 9.12 (s, 1H), 8.36 (s, 1H), 8.21 (d, J=2.3 Hz, 1H), 7.88 (s, 1H), 7.72 (d, J=9.1 Hz, 1H), 7.35 (dd, J=9.1, 2.3 Hz, 1H), 7.17 (t, J=74.4 Hz, 1H), 1.50 (s, 9H).

Example 290

2-(5-Methoxy-1-methyl-1H-indazol-3-yl)-5H-pyrrolo[2,3-b]pyrazine-7-carboxylic acid ((3R,4R)-3-amino-tetrahydro-pyran-4-yl)-amide

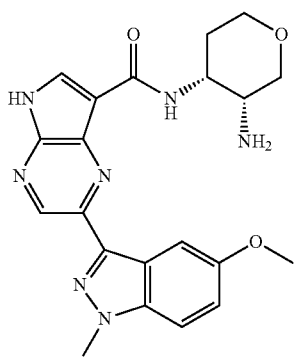

Step 1 tert-Butyl (3R,4R)-4-(2-(5-methoxy-1-methyl-1H-indazol-3-yl)-5-((2-(trimethylsilyl)ethoxy)methyl)-5H-pyrrolo[2,3-b]pyrazine-7-carboxamido)tetrahydro-2H-pyran-3-ylcarbamate

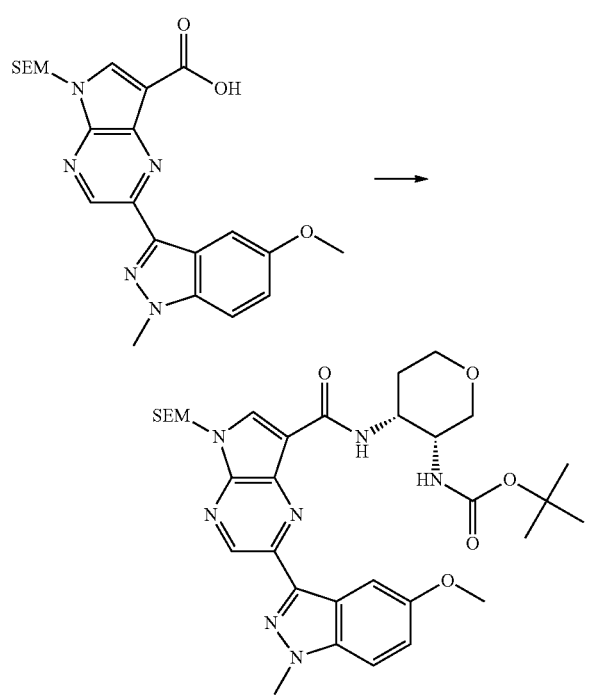

In a 16×100 mm screw cap test tube were added HATU (80.5 mg, 212 µmol.20) and tert-butyl (3R,4R)-4-aminotetrahydro-2H-pyran-3-ylcarbamate (prepared as described in WO2010/97248 A1, 2010; 38.1 mg, 176 µmol) then 2-(5-methoxy-1-methyl-1H-indazol-3-yl)-5-((2-(trimethylsilyl)ethoxy)methyl)-5H-pyrrolo[2,3-b]pyrazine-7-carboxylic acid (80 mg, 176 mmol) dissolved in DMF (2.00 mL) was added to give a light yellow solution which immediately formed a white precipitated. The reaction mixture stirred at 25° C. overnight, solvents evaporated and residue purified by chromatography (60 g column, 50 µm from Analogix, 0 to 5% over 15 min (MeOH containing 10% ammonium hydroxide)/dichloromethane to yield tert-butyl (3R,4R)-4-(2-(5-methoxy-1-methyl-1H-indazol-3-yl)-5-((2-(trimethylsilyl)ethoxy)methyl)-5H-pyrrolo[2,3-b]pyrazine-7-carboxamido)tetrahydro-2H-pyran-3-ylcarbamate (115 mg, 176 µmol, 100%) as a very light yellow solid. MS (M+Na)⁺=674 (>90% purity); ¹H NMR (CDCl₃) δ: 9.29 (s, 1H), 8.51 (d, J=9.1 Hz, 1H), 8.37 (s, 2H), 7.48 (d, J=9.1 Hz, 1H), 7.31 (dd, J=9.1, 3.0 Hz, 1H), 6.27 (d, J=10.2 Hz, 1H), 5.75 (s, 2H), 4.59-4.81 (m, 1H), 4.18-4.36 (m, 4H), 3.91-4.16 (m, 5H), 3.54-3.81 (m, 4H), 2.33 (qd, J=12.7, 4.9 Hz, 1H), 1.89 (d, J=13.2 Hz, 1H), 0.93-1.12 (m, 2H), 0.82 (s, 9H), 0.00 (s, 9H).

Step 2

N-((3R,4R)-3-Aminotetrahydro-2H-pyran-4-yl)-2-(5-methoxy-1-methyl-1H-indazol-3-yl)-5H-pyrrolo[2,3-b]pyrazine-7-carboxamide

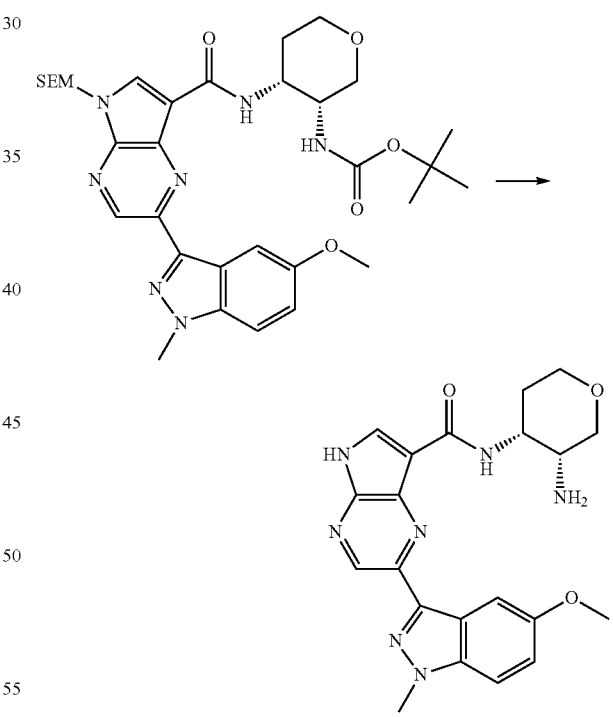

To a pale yellow solution of tert-butyl (3R,4R)-4-(2-(5-methoxy-1-methyl-1H-indazol-3-yl)-5-((2-(trimethylsilyl)ethoxy)methyl)-5H-pyrrolo[2,3-b]pyrazine-7-carboxamido)tetrahydro-2H-pyran-3-ylcarbamate (115 mg, 176 µmol) in dichloromethane (3.00 mL) was added TFA (1.48 g, 1.00 mL, 13.0 mmol, Eq: 73.6), the reaction mixture turned dark red and was stirred at 25° C. overnight then concentrated. The residue was re-dissolved in 5 mL of a solution of (dichloromethane/MeOH/ammonium hydroxide; 60:10:1) and stirred at 25° C. for 3 h, then evaporated to a light yellow solid, dissolved in dichloromethane (added few drops MeOH and heating) and purified by chromatography (60 g column, 50 μm from Analogix, 0 to 5% over 15 min (MeOH containing 10% ammonium hydroxide)/dichloromethane. The pure product dissolved in dichloromethane/MeOH and most dichloromethane evaporated for solid formation, solid was separated by decantation and dried under high vacuum to give N-((3R,4R)-3-aminotetrahydro-2H-pyran-4-yl)-2-(5-methoxy-1-methyl-1H-indazol-3-yl)-5H-pyrrolo[2,3-b]pyrazine-7-carboxamide (48 mg, 114 μmol, 64.6%) as an off-white solid. MS (M+H)$^+$=422 (100% purity); $^1$H NMR (DMSO-d$_6$) δ: 9.05 (s, 1H), 8.45 (d, J=8.3 Hz, 1H), 8.39 (s, 1H), 8.17 (d, J=2.6 Hz, 1H), 7.70 (d, J=9.1 Hz, 1H), 7.31 (dd, J=9.1, 2.3 Hz, 1H), 4.23 (td, J=7.6, 4.0 Hz, 1H), 4.14 (s, 3H), 4.08 (q, J=5.3 Hz, 1H), 3.87 (s, 3H), 3.84 (br. s., 1H), 3.52-3.72 (m, 2H), 3.38-3.51 (m, 1H), 3.15 (d, J=4.9 Hz, 2H), 2.88 (br. s., 1H), 1.85-2.07 (m, 1H), 1.70 (d, J=11.7 Hz, 1H).

Example 291

2-(5-Methoxy-1-methyl-1H-indazol-3-yl)-5H-pyrrolo[2,3-b]pyrazine-7-carboxylic acid ((1R,2S)-2-amino-cyclohexyl)-amide

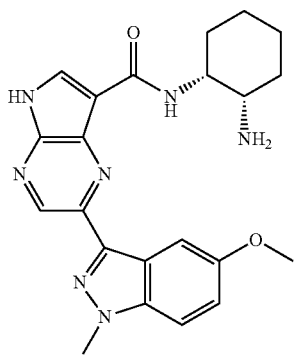 [SMILES: COc1ccc2c(c1)c(-c1cnc3[nH]cc(C(=O)N[C@@H]4CCCC[C@@H]4N)c3n1)nn2C]

Step 1

N-((1R,2S)-2-aminocyclohexyl)-2-(5-methoxy-1-methyl-1H-indazol-3-yl)-5-((2-(trimethylsilyl)ethoxy)methyl)-5H-pyrrolo[2,3-b]pyrazine-7-carboxamide

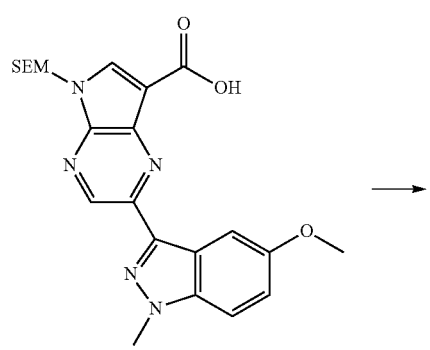

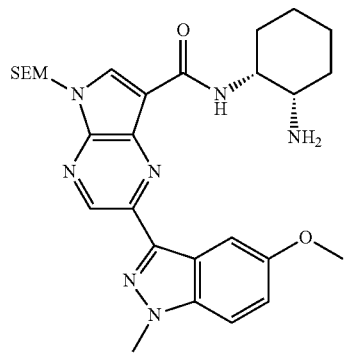

In a 16×100 mm screw cap test tube were added HATU (80.5 mg, 212 μmol.20) and (1R,2S)-cyclohexane-1,2-diamine (20.1 mg, 176 μmol) then 2-(5-methoxy-1-methyl-1H-indazol-3-yl)-5-((2-(trimethylsilyl)ethoxy)methyl)-5H-pyrrolo[2,3-b]pyrazine-7-carboxylic acid (80 mg, 176 μmol) dissolved in DMF (2.00 mL) was added to give a light yellow solution which immediately formed a white precipitated. The reaction mixture stirred at 25° C. overnight, solvents evaporated and residue purified by chromatography (60 g column, 50 μm from Analogix, 0 to 5% over 15 min (MeOH containing 10% ammonium hydroxide)/dichloromethane to give the desired N-((1R,2S)-2-aminocyclohexyl)-2-(5-methoxy-1-methyl-1H-indazol-3-yl)-5-((2-(trimethylsilyl)ethoxy)methyl)-5H-pyrrolo[2,3-b]pyrazine-7-carboxamide (21 mg, 38.2 μmol, 21.7%). MS (M+H)$^+$=550 (>90% purity); $^1$H NMR (CDCl$_3$) δ: 9.02 (s, 1H), 8.51 (s, 1H), 7.51 (s, 1H), 7.43 (d, J=9.1 Hz, 1H), 7.22 (dd, J=9.3, 2.1 Hz, 1H), 5.61-5.84 (m, 2H), 4.78 (br. s., 1H), 4.18 (s, 3H), 4.02 (t, J=3.2 Hz, 1H), 3.91 (s, 3H), 3.76 (br. s., 1H), 3.62-3.71 (m, 2H), 2.09 (br. s., 2H), 2.03 (s, 2H), 1.80-1.98 (m, 4H), 1.52-1.78 (m, 4H), 0.98 (dd, J=9.3, 7.4 Hz, 2H), 0.00 (s, 9H).

Step 2

2-(5-Methoxy-1-methyl-1H-indazol-3-yl)-5H-pyrrolo[2,3-b]pyrazine-7-carboxylic acid ((1R,2S)-2-amino-cyclohexyl)-amide

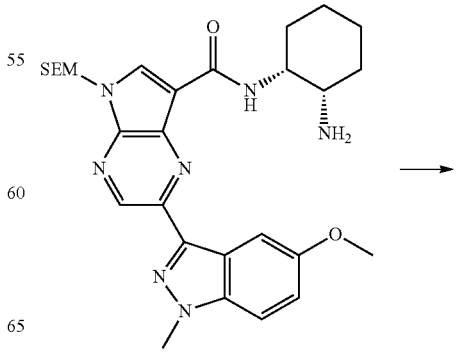

-continued

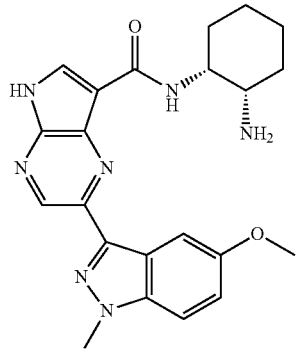

To a pale yellow solution of N-((1R,2S)-2-aminocyclohexyl)-2-(5-methoxy-1-methyl-1H-indazol-3-yl)-5-((2-(trimethylsilyl)ethoxy)methyl)-5H-pyrrolo[2,3-b]pyrazine-7-carboxamide (21 mg, 38.2 µmol) in dichloromethane (3.00 mL) was added TFA (1.48 g, 1.00 mL, 13.0 mmol, Eq: 340), the reaction mixture turned dark red and was stirred at 25° C. overnight then concentrated. The residue was re-dissolved in 5 mL of a solution of (dichloromethane/MeOH/ammonium hydroxide; 60:10:1) and stirred at 25° C. for 3 h, then evaporated to a light yellow solid, dissolved in dichloromethane (added few drops MeOH and heating) and purified by chromatography (spherical silica 20-45 µm, 23 g, Versaflash Supelco) eluting with 0 to 10% over 15 min (MeOH containing 10% ammonium hydroxide)/dichloromethane. The pure product dissolved in hot MeOH and allowed to stand overnight for solid formation. The solid was separated by decantation and dried under high vacuum to give N-((1R,2S)-2-aminocyclohexyl)-2-(5-methoxy-1-methyl-1H-indazol-3-yl)-5H-pyrrolo[2,3-b]pyrazine-7-carboxamide (9 mg, 21.5 µmol, 56.2%) as a white solid. MS (M+H)$^+$=420 (100% purity); $^1$H NMR (DMSO-d$_6$) δ: 9.02 (s, 1H), 8.34-8.45 (m, 2H), 8.07 (d, J=2.3 Hz, 1H), 7.69 (d, J=9.4 Hz, 1H), 7.29 (dd, J=9.3, 2.5 Hz, 1H), 4.14 (s, 3H), 4.01-4.10 (m, 1H), 3.88 (s, 3H), 3.05 (d, J=3.8 Hz, 1H), 1.50-1.82 (m, 6H), 1.40 (br. s., 2H).

Example 292

2-[5-Difluoromethoxy-1-(3-dimethylamino-propyl)-1H-indazol-3-yl]-5H-pyrrolo[2,3-b]pyrazine-7-carboxylic acid tert-butylamide

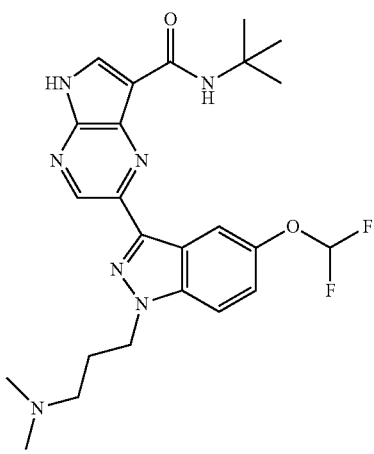 [SMILES: CN(C)CCCn1nc(-c2cnc3[nH]cc(C(=O)NC(C)(C)C)c3n2)c2cc(OC(F)F)ccc21]

Step 1

N-tert-butyl-2-(5-(difluoromethoxy)-1-(3-(dimethylamino)propyl)-1H-indazol-3-yl)-5-((2-(trimethylsilyl)ethoxy)methyl)-5H-pyrrolo[2,3-b]pyrazine-7-carboxamide

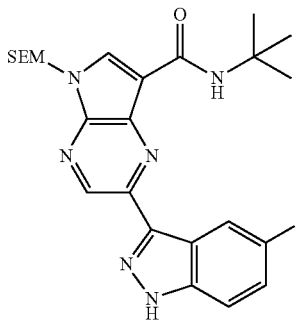

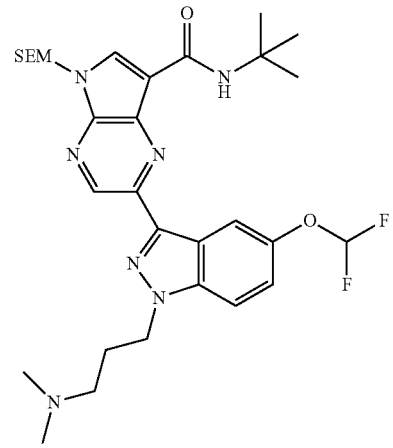

In a 2-(5 mL Biotage microwave vial were mixed N-tert-butyl-2-(5-(difluoromethoxy)-1H-indazol-3-yl)-5-((2-(trimethylsilyl)ethoxy)methyl)-5H-pyrrolo[2,3-b]pyrazine-7-carboxamide (109 mg, 205 µmol), 3-chloro-N,N-dimethylpropan-1-aminium chloride (97.4 mg, 616 µmol, Eq: 3.0) and Cs$_2$CO$_3$ (402 mg, 1.23 mmol, Eq: 6.00) in DMF (2 mL). The mixture was stirred ~10 min at 25° C. then heated to 100° C. in the Biotage microwave reactor for 30 min, diluted with 10 mL of dichloromethane and filtered through a celite pad, filtrate concentrated under high vacuum at 65° C. and residue dissolved in dichloromethane and purified by chromatography (spherical silica 20-45 µm, 23 g, Versaflash Supelco) eluting with 0 to 5% over 20 min (MeOH containing 10% ammonium hydroxide)/dichloromethane to give N-tert-butyl-2-(5-(difluoromethoxy)-1-(3-(dimethylamino)propyl)-1H-indazol-3-yl)-5-((2-(trimethylsilyl)ethoxy)methyl)-5H-pyrrolo[2,3-b]pyrazine-7-carboxamide (97 mg, 158 µmol, 76.7%) as a light brown solid. MS (M+H)$^+$=616 (>90% purity); $^1$H NMR (CDCl$_3$) δ: 9.24 (s, 1H), 8.36 (s, 1H), 8.32 (d, J=2.3 Hz, 1H), 8.06 (s, 1H), 7.60 (d, J=8.7 Hz, 1H), 7.35 (dd, J=9.1, 2.3 Hz, 1H), 6.55 (t, J=74.8 Hz, 1H), 5.75 (s, 2H), 4.60 (t, J=6.6 Hz, 2H), 3.53-3.74 (m, 2H), 2.33-2.42 (m, 2H), 2.29 (s, 6H), 2.14-2.27 (m, 2H), 1.65 (s, 9H), 0.90-1.07 (m, 2H), 0.00 (s, 9H).

Step 2

2-[5-Difluoromethoxy-1-(3-dimethylamino-propyl)-1H-indazol-3-yl]-5H-pyrrolo[2,3-b]pyrazine-7-carboxylic acid tert-butylamide

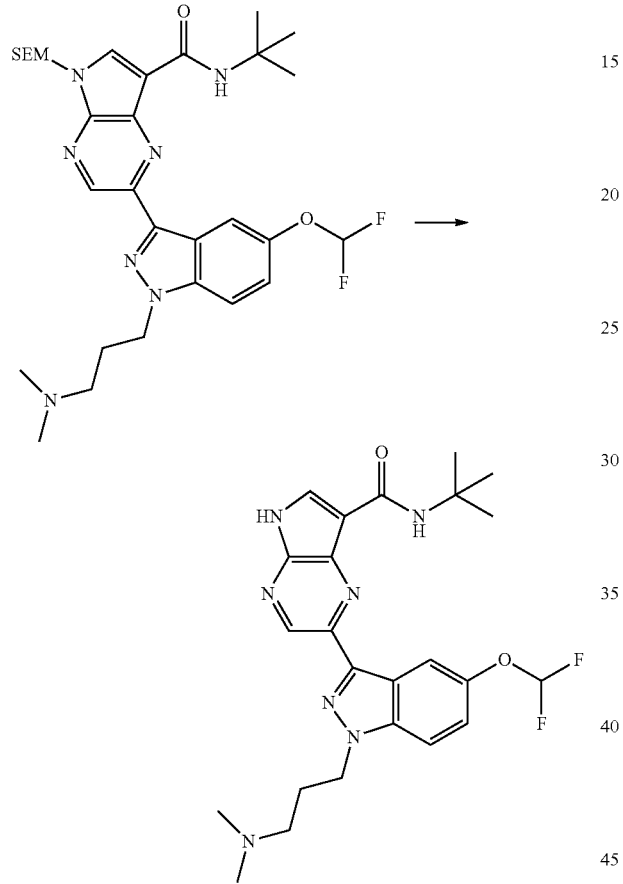

To a pale yellow solution of N-tert-butyl-2-(5-(difluoromethoxy)-1-(3-(dimethylamino)propyl)-1H-indazol-3-yl)-5-((2-(trimethylsilyl)ethoxy)methyl)-5H-pyrrolo[2,3-b]pyrazine-7-carboxamide (97 mg, 158 μmol) in dichloromethane (4 mL) was added TFA (1.48 g, 1 mL, 13.0 mmol, Eq: 82.4), the reaction mixture turned orange and was stirred at 25° C. for 2 h, mixture concentrated and the residue was re-dissolved in 5 mL of a solution of (dichloromethane/MeOH/ammonium hydroxide; 60:10:1) and stirred at 25° C. for 1 h, then evaporated to a yellow solid, which was dissolved in dichloromethane (with a couple of drops of MeOH) and purified by chromatography (40 g column, 20-40 μm spherical silica, HP Gold from Teledyne/Isco) eluting with 0 to 5% over 15 min (MeOH containing 10% ammonium hydroxide)/dichloromethane. The pure product dissolved in dichloromethane and cyclohexane added to allow solid formation, off-white solid was separated by decantation and dried under high vacuum to give N-tert-butyl-2-(5-(difluoromethoxy)-1-(3-(dimethylamino)propyl)-1H-indazol-3-yl)-5H-pyrrolo[2,3-b]pyrazine-7-carboxamide (62 mg, 128 μmol, 81.1%). MS (M+H)+=486 (100% purity); $^1$H NMR (DMSO-d$_6$) δ: 9.07 (s, 1H), 8.37 (s, 1H), 8.20 (s, 1H), 7.78-7.95 (m, 2H), 7.39 (d, J=8.7 Hz, 1H), 7.19 (s, 1H), 4.55 (t, J=6.2 Hz, 2H), 2.17-2.30 (m, 2H), 2.12 (s, 7H), 1.99-2.07 (m, 2H), 1.49 (s, 10H).

Example 293

2-(1-Methyl-2-oxy-4,5,6,7-tetrahydro-1H-indazol-3-yl)-5H-pyrrolo[2,3-b]pyrazine-7-carboxylic acid isopropylamide

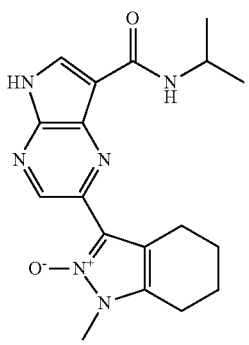 [SMILES: CC(C)NC(=O)c1c[nH]c2ncc(-c3c4c(n(C)[n+]3[O-])CCCC4)nc12]

Step 1

3-Iodo-4,5,6,7-tetrahydro-1H-indazole

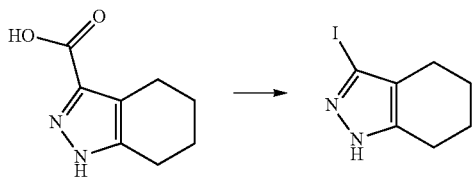 [SMILES: O=C(O)c1n[nH]c2c1CCCC2 ; Ic1n[nH]c2c1CCCC2]

To a mixture of 4,5,6,7-tetrahydro-1H-indazole-3-carboxylic acid (0.57 g, 3.43 mmol), and sodium bicarbonate (951 mg, 440 μL, 11.3 mmol) in dichloroethane (5 mL) and water (5 mL) were added in one portion sodium iodide (1.34 g, 8.92 mmol) and iodine (1.13 g, 4.46 mmol) and the mixture heated at to 100° C. (oil bath temperature) with vigorous stirring for 24 h. After cooling to 25° C. the mixture was diluted with dichloromethane, then washed with 10% Na$_2$S$_2$O$_3$ and saturated NaHCO$_3$. The organic phases were combined, dried (MgSO$_4$) and concentrated to an off-white solid which was purified by chromatography (115 g column, 50 μm from Analogix, 0 to 5% over 15 min (MeOH containing 10% ammonium hydroxide)/dichloromethane to give 3-iodo-4,5,6,7-tetrahydro-1H-indazole (674 mg, 2.72 mmol, 79.2%) as a white solid. MS (M+H)⁺=249 (>90% purity); ¹H NMR (CDCl₃) δ: 2.75 (t, J=5.7 Hz, 2H), 2.35 (t, J=5.7 Hz, 2H), 1.61-1.90 (m, 4H).

Step 2

3-Iodo-1-methyl-4,5,6,7-tetrahydro-1H-indazole

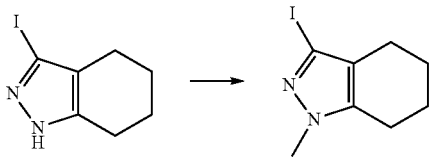

To a solution of 3-iodo-4,5,6,7-tetrahydro-1H-indazole (674 mg, 2.72 mmol) in THF (10 mL) at 0° C. was added KOtBu 1M in THF (3.8 mL, 3.8 mmol) and the mixture stirred at 0° C. for 30 min where it became a brown-reddish solution then added MeI (540 mg, 238 μL, 3.8 mmol). The reaction mixture was stirred at 0° C. for 30 min then warmed to 25° C. and stirred for 18 h. The reaction mixture was quenched with saturated ammonium chloride in water and extracted with dichloromethane (3×30 mL), organics dried over MgSO₄ and concentrated to an off-white solid. Then dissolved in toluene and purified by chromatography (115 g column, 50 μm from Analogix, 0-20% EtOAc in hexanes over 15 min to afford the more polar desired 3-iodo-1-methyl-4,5,6,7-tetrahydro-1H-indazole (570 mg, 2.17 mmol, 80.0%) as an off-white solid. MS (M+H)⁺=263 (100% purity); ¹H NMR (CDCl₃) δ: 3.72 (s, 3H), 2.42-2.72 (m, 2H), 2.30 (t, J=6.0 Hz, 2H), 1.56-1.93 (m, 4H). The regioisomer 3-iodo-2-methyl-4,5,6,7-tetrahydro-2H-indazole (182 mg, 694 μmol, 25.6%) as also obtained as a white solid.

Step 3

1-Methyl-3-(tributylstannyl)-4,5,6,7-tetrahydro-1H-indazole

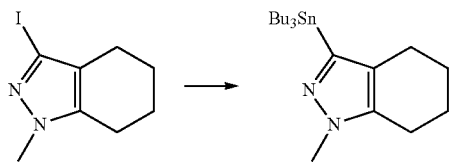

3-Iodo-1-methyl-4,5,6,7-tetrahydro-1H-indazole (300 mg, 1.14 mmol) was dissolved in THF (3.00 mL). The colorless solution was cooled to −16° C. (NaCl/ice bath). isopropylmagnesium chloride 2 M in THF (641 μL, 1.28 mmol.12) was added dropwise at −16° C. The reaction mixture was stirred at −16° C. for 20 min. Then, tributylchlorostannane (428 mg, 357 μL, 1.32 mmol. 15) was added slowly. The reaction mixture was warmed to 25° C. and stirred for 1.5 h. The reaction mixture was quenched with saturated ammonium chloride solution, extracted with dichloromethane (3×30 mL), organics dried over MgSO₄ and concentrated to a yellow oil. The residue was dried under high vacuum yielding 1-methyl-3-(tributylstannyl)-4,5,6,7-tetrahydro-1H-indazole assumed quantitative and taken into next step without further treatment.

Step 4

2-(1-Methyl-4,5,6,7-tetrahydro-1H-indazol-3-yl)-5-((2-(trimethylsilyl)ethoxy)methyl)-5H-pyrrolo[2,3-b]pyrazine-7-carbaldehyde

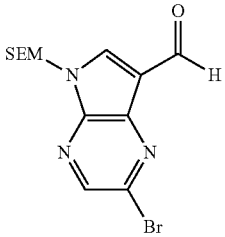

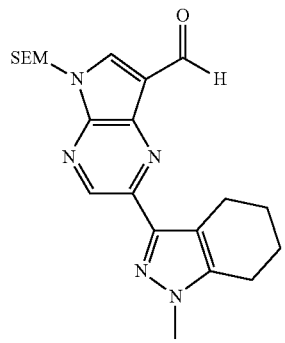

2-Bromo-5-((2-(trimethylsilyl)ethoxy)methyl)-5H-pyrrolo[2,3-b]pyrazine-7-carbaldehyde (406 mg, 1.14 mmol) and 1-methyl-3-(tributylstannyl)-4,5,6,7-tetrahydro-1H-indazole (485 mg, 1.14 mmol) were dissolved in DMF (3.00 mL) under argon, tetrakis(triphenylphosphine)palladium (0) (65.9 mg, 57.0 μmol) and CuI (43.4 mg, 228 μmol, Eq: 0.20) were added and the mixture sonicated for 5 min with bubbling argon. The reaction mixture was stirred at 90° C. (oil bath temperature) for 18 h. The reaction mixture was concentrated under high vacuum and the dark yellow solid residue was purified by chromatography (80 g column, 50 μm from SiliCycle) gradient 0-50% EtOAc in hexanes over 30 min) to give 2-(1-methyl-4,5,6,7-tetrahydro-1H-indazol-3-yl)-5-((2-(trimethylsilyl)ethoxy)methyl)-5H-pyrrolo[2,3-b]pyrazine-7-carbaldehyde (265 mg, 644 μmol, 56.5%) as a light yellow solid. MS (M+H)⁺=412; ¹H NMR (CDCl₃) δ: 10.50 (s, 1H), 9.07 (s, 1H), 8.29 (s, 1H), 5.77 (s, 2H), 3.89 (s, 3H), 3.57-3.72

(m, 2H), 3.05 (t, J=6.0 Hz, 2H), 2.69 (t, J=6.0 Hz, 2H), 1.80-2.02 (m, 4H), 0.92-1.09 (m, 2H), 0.00 (s, 9H).

Step 5

3-(7-Carboxy-5-((2-(trimethylsilyl)ethoxy)methyl)-5H-pyrrolo[2,3-b]pyrazin-2-yl)-1-methyl-4,5,6,7-tetrahydro-1H-indazole 2-oxide

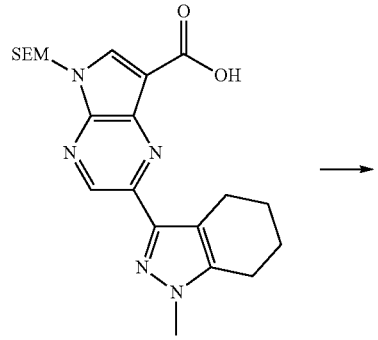

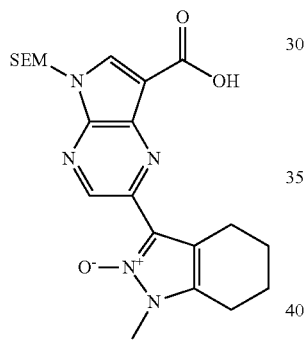

To a yellow-brown solution of 2-(1-methyl-4,5,6,7-tetrahydro-1H-indazol-3-yl)-5-((2-(trimethylsilyl)ethoxy)methyl)-5H-pyrrolo[2,3-b]pyrazine-7-carbaldehyde (265 mg, 644 μmol) in dioxane (14.0 mL) and water (4 mL) at 0° C. (became a suspension after cooling) was added sulfamic acid (375 mg, 3.86 mmol, Eq: 6.00), followed by drop-wise addition of a solution of sodium chlorite (94.6 mg, 837 μmol.30) and KH₂PO₄ (1.05 g, 7.73 mmol2.00) in water (4.5 mL) via dropping funnel over 15 min. The ice bath was removed and the light yellow suspension was stirred at 25° C. for 18 h. Mixture diluted with water (50 mL) and extracted with 5% MeOH in dichloromethane (3×40 mL). The combined organic layers were dried (MgSO₄) and evaporated. Light yellow solid residue was dissolved in dichloromethane and purified by chromatography (spherical silica 20-45 μm, 50 g, Versaflash Supelco) eluting with 0 to 5% MeOH in dichloromethane. Pure compound dissolved in dichloromethane, added some cyclohexane and dichloromethane evaporated to promote solid formation, solid separated by filtration, rinsed with hexanes and dried to give 3-(7-carboxy-5-((2-(trimethylsilyl)ethoxy)methyl)-5H-pyrrolo[2,3-b]pyrazin-2-yl)-1-methyl-4,5,6,7-tetrahydro-1H-indazole 2-oxide (147 mg, 331 μmol, 51.5%) as a white solid. MS (M+H)⁺=444 (100% purity); ¹H NMR (CDCl₃) δ: 9.19 (s, 1H), 8.45 (s, 1H), 5.76 (s, 2H), 3.58-3.71 (m, 2H), 3.50 (s, 3H), 2.39-2.55 (m, 2H), 2.24-2.38 (m, 2H), 1.99-2.22 (m, 4H), 0.91-1.07 (m, 2H), 0.00 (s, 9H).

Step 6

3-(7-(Isopropylcarbamoyl)-5-((2-(trimethylsilyl)ethoxy)methyl)-5H-pyrrolo[2,3-b]pyrazin-2-yl)-1-methyl-4,5,6,7-tetrahydro-1H-indazole 2-oxide

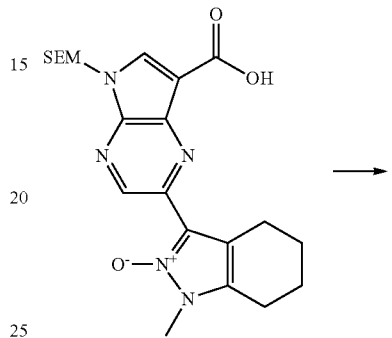

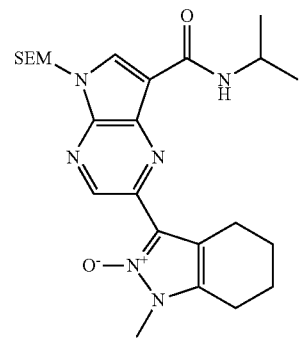

In a 16×100 mm screw cap test tube were added HATU (46.3 mg, 122 μmol.20) and propan-2-amine (24.0 mg, 406 μmol) then 3-(7-carboxy-5-((2-(trimethylsilyl)ethoxy)methyl)-5H-pyrrolo[2,3-b]pyrazin-2-yl)-1-methyl-4,5,6,7-tetrahydro-1H-indazole 2-oxide (45 mg, 101 μmol) dissolved in dichloromethane (2.50 mL) was added to give a light yellow solution which immediately formed a white precipitated. The reaction mixture stirred at 25° C. overnight, solvents evaporated and residue purified by chromatography (spherical silica 20-45 μm, 23 g, Versaflash Supelco) eluting with 0 to 50% EtOAc in hexanes over 30 min to yield 3-(7-(isopropylcarbamoyl)-5-((2-(trimethylsilyl)ethoxy)methyl)-5H-pyrrolo[2,3-b]pyrazin-2-yl)-1-methyl-4,5,6,7-tetrahydro-1H-indazole 2-oxide (45 mg, 92.8 μmol, 91.5%) as a clear foam. MS (M+H)⁺=485.1 (100% purity); ¹H NMR (CDCl₃) δ: 7.91 (s, 1H), 6.41 (d, J=8.1 Hz, 1H), 6.11 (s, 1H), 4.54 (s, 2H), 3.22-3.37 (m, 1H), 2.36-2.46 (m, 2H), 2.31 (s, 3H), 1.22-1.44

(m, 2H), 1.00-1.14 (m, 2H), 0.82-1.00 (m, 4H), 0.16 (d, J=6.6 Hz, 7H), −0.30-−0.12 (m, 2H), −1.19 (s, 9H).

Step 7

2-(1-Methyl-2-oxy-4,5,6,7-tetrahydro-1H-indazol-3-yl)-5H-pyrrolo[2,3-b]pyrazine-7-carboxylic acid isopropylamide

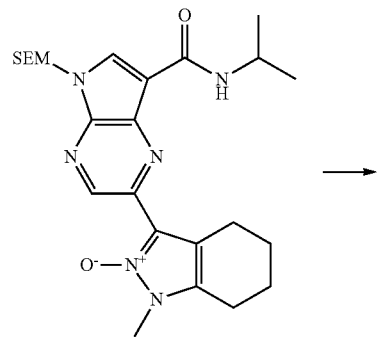

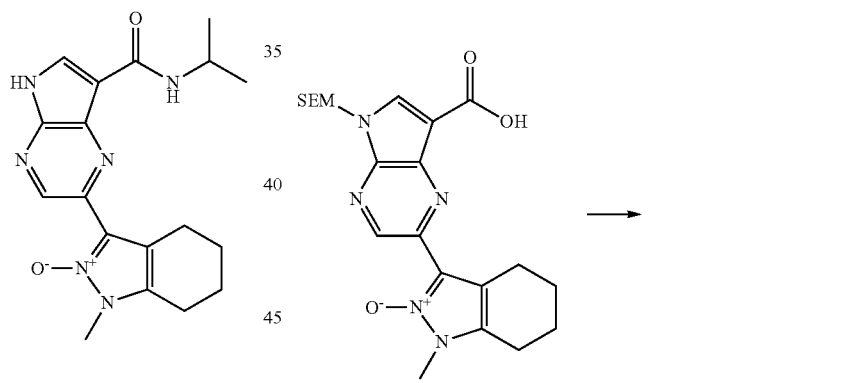

To a pale yellow solution of 3-(7-(isopropylcarbamoyl)-5-((2-(trimethylsilyl)ethoxy)methyl)-5H-pyrrolo[2,3-b]pyrazin-2-yl)-1-methyl-4,5,6,7-tetrahydro-1H-indazole 2-oxide (45 mg, 92.8 µmol) in dichloromethane (2.00 mL) was added TFA (1.48 g, 1.00 mL, 13.0 mmol40), the reaction mixture turned dark red and was stirred at 25° C. overnight then concentrated. The residue was re-dissolved in 5 mL of a solution of (dichloromethane/MeOH/ammonium hydroxide; 60:10:1) and stirred at 25° C. for 3 h, then evaporated to a light yellow solid, dissolved in dichloromethane (added few drops MeOH and heating) and purified by chromatography (spherical silica 20-45 µm, 23 g, Versaflash Supelco) eluting with 0 to 10% over 15 min (MeOH containing 10% ammonium hydroxide)/dichloromethane. Pure white solid product was sonicated with hexanes. The solid was separated by decantation and dried under high vacuum to give 3-(7-(isopropylcarbamoyl)-5H-pyrrolo[2,3-b]pyrazin-2-yl)-1-methyl-4,5,6,7-tetrahydro-1H-indazole 2-oxide (27 mg, 76.2 mmol, 82.1%) as a white solid. MS (M+H)⁺=377 (100% purity); $^1$H NMR (DMSO-d$_6$) δ: 12.93 (br. s., 1H), 8.93 (s, 1H), 8.45 (s, 1H), 7.45 (d, J=8.1 Hz, 1H), 4.13-4.33 (m, 1H), 3.35 (s, 3H), 2.37-2.46 (m, 2H), 1.83-2.18 (m, 6H), 1.22 (d, J=6.6 Hz, 6H).

Example 294

2-(1-Methyl-2-oxy-4,5,6,7-tetrahydro-1H-indazol-3-yl)-5H-pyrrolo[2,3-b]pyrazine-7-carboxylic acid tert-butylamide

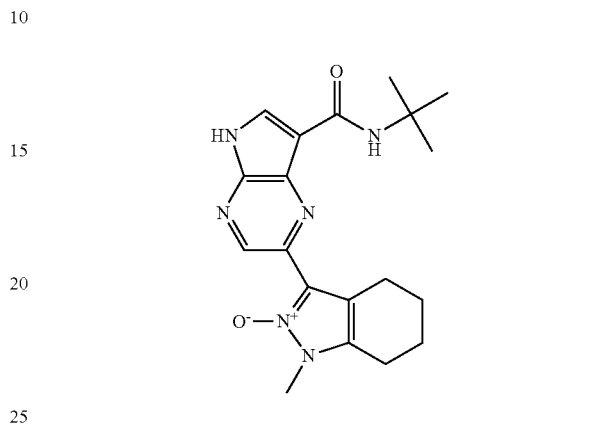

Step 1

3-(7-(tert-Butylcarbamoyl)-5-((2-(trimethylsilyl)ethoxy)methyl)-5H-pyrrolo[2,3-b]pyrazin-2-yl)-1-methyl-4,5,6,7-tetrahydro-1H-indazole 2-oxide In a 16×100 mm screw cap test tube were added HATU (46.3 mg, 122 µmol.20) and 2-methylpropan-2-amine (29.7 mg, 406 µmol) then 3-(7-carboxy-5-((2-(trimethylsilyl)ethoxy)methyl)-5H-pyrrolo[2,3-b]pyrazin-2-yl)-1-methyl-4,5,6,7-tetrahydro-1H-indazole 2-oxide (45 mg, 101 µmol) dissolved in DMF (2.00 mL) was added to give a light yellow solution which immediately formed a white precipitated. The reaction mixture stirred at 25° C. overnight, solvents evaporated and residue purified by chromatography (spherical silica 20-45 µm, 23 g, Versaflash Supelco) eluting with 0 to 50% EtOAc in hexanes over 30 min to yield 3-(7-(tert-butylcarbamoyl)-5-((2-(trimethylsilyl)ethoxy)methyl)-5H-pyrrolo[2,3-b]pyrazin-2-yl)-1-methyl-4,5,6,7-tetrahydro-1H-indazole 2-oxide (43 mg, 86.2 µmol, 85.0%) as a clear foam. MS (M+H)$^+$=499 (>90% purity); $^1$H NMR (CDCl$_3$) δ: 7.82 (s, 1H), 6.21 (s, 1H), 4.52 (s, 2H), 2.36-2.45 (m, 2H), 2.30 (s, 3H), 1.23-1.37 (m, 2H), 0.95-1.12 (m, 2H), 0.89 (dd, J=10.9, 5.6 Hz, 2H), 0.72-0.85 (m, 2H), 0.37 (s, 9H), −0.29--0.17 (m, 2H), −1.20 (s, 9H).

Step 2

2-(1-Methyl-2-oxy-4,5,6,7-tetrahydro-1H-indazol-3-yl)-5H-pyrrolo[2,3-b]pyrazine-7-carboxylic acid tert-butylamide

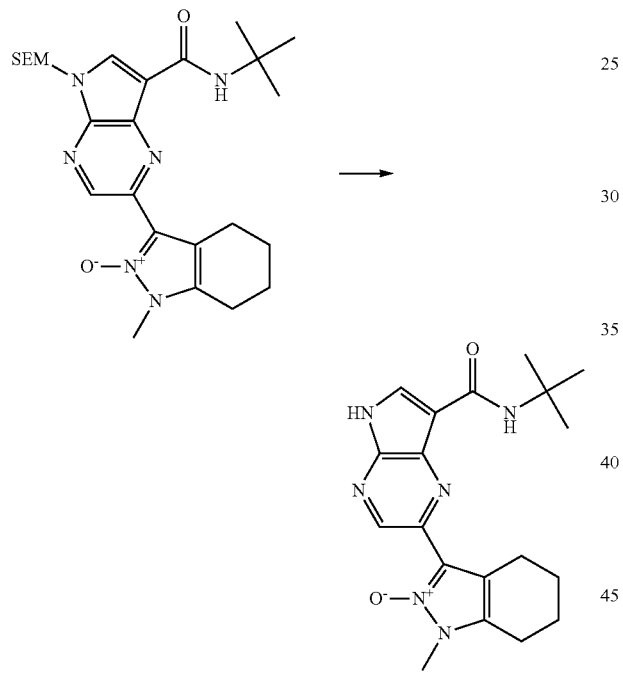

To a pale yellow solution of 3-(7-(tert-butylcarbamoyl)-5-((2-(trimethylsilyl)ethoxy)methyl)-5H-pyrrolo[2,3-b]pyrazin-2-yl)-1-methyl-4,5,6,7-tetrahydro-1H-indazole 2-oxide (43 mg, 86.2 µmol) in dichloromethane (2.00 mL) was added TFA (1.48 g, 1.00 mL, 13.0 mmol51), the reaction mixture turned dark red and was stirred at 25° C. overnight then concentrated. The residue was re-dissolved in 5 mL of a solution of (dichloromethane/MeOH/ammonium hydroxide; 60:10:1) and stirred at 25° C. for 3 h, then evaporated to a light yellow solid, dissolved in dichloromethane (added few drops MeOH and heating) and purified by chromatography (spherical silica 20-45 µm, 23 g, Versaflash Supelco) eluting with 0 to 10% over 15 min (MeOH containing 10% ammonium hydroxide)/dichloromethane. Pure white solid product was sonicated with hexanes. The solid was separated by decantation and dried under high vacuum to give 3-(7-(tert-butylcarbamoyl)-5H-pyrrolo[2,3-b]pyrazin-2-yl)-1-methyl-4,5,6,7-tetrahydro-1H-indazole 2-oxide (28 mg, 76.0 mmol, 88.1%) as a white solid. MS (M+H)$^+$=369.1 (100% purity); $^1$H NMR (DMSO-d$_6$) δ: 12.88 (br. s., 1H), 8.87 (s, 1H), 8.40 (s, 1H), 7.32 (s, 1H), 3.35 (s, 3H), 2.36-2.46 (m, 2H), 2.03 (br. s., 2H), 1.86-1.96 (m, 4H), 1.44 (s, 9H).

Example 295

2-(1-Methyl-4,5,6,7-tetrahydro-1H-indazol-3-yl)-5H-pyrrolo[2,3-b]pyrazine-7-carboxylic acid tert-butylamide

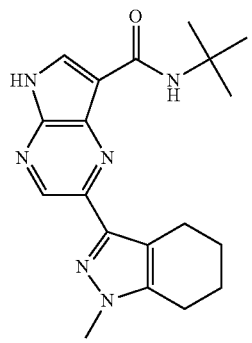 [SMILES: Cn1nc(-c2cnc3[nH]cc(C(=O)NC(C)(C)C)c3n2)c2c1CCCC2]

Step 1

1-Methyl-3-(tributylstannyl)-4,5,6,7-tetrahydro-1H-indazole

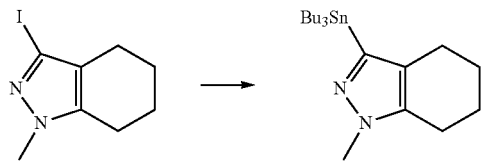

In a 25 mL round-bottomed flask, 3-iodo-1-methyl-4,5,6,7-tetrahydro-1H-indazole (62 mg, 237 µmol) was dissolved in THF (3 mL). The colorless solution was cooled to −16° C. (NaCl/ice bath) and isopropylmagnesium chloride 2 M in THF (132 µL, 265 µmol) was added dropwise at −16° C. The reaction mixture was stirred at −16° C. for 20 min. Then, tributylchlorostannane (88.6 mg, 73.8 µL, 272 µmol) was added slowly. The reaction mixture was warmed to 25° C. and stirred for 1.5 h. The reaction mixture was quenched with saturated ammonium chloride solution, extracted with dichloromethane (3×30 mL), organics dried over MgSO$_4$ and concentrated to an off-white waxy solid. The residue was dried under high vacuum yielding 1-methyl-3-(tributylstannyl)-4,5,6,7-tetrahydro-1H-indazole assumed quantitative and taken into next step without further treatment.

Step 2

N-tert-Butyl-2-(1-methyl-4,5,6,7-tetrahydro-1H-indazol-3-yl)-5-((2-(trimethylsilyl)ethoxy)methyl)-5H-pyrrolo[2,3-b]pyrazine-7-carboxamide

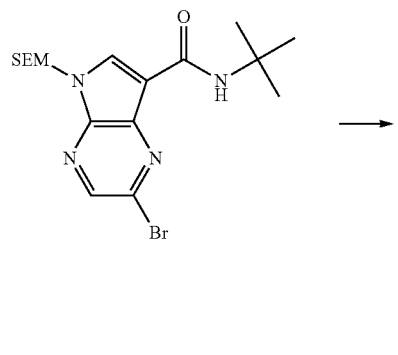

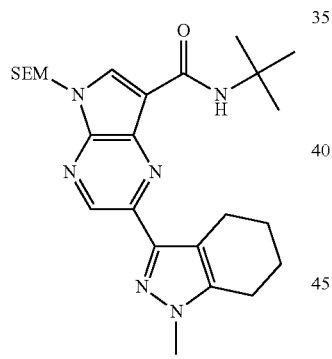

2-Bromo-N-tert-butyl-5-((2-(trimethylsilyl)ethoxy)methyl)-5H-pyrrolo[2,3-b]pyrazine-7-carboxamide (100 mg, 234 µmol) and 1-methyl-3-(tributylstannyl)-4,5,6,7-tetrahydro-1H-indazole (99.5 mg, 234 µmol) were dissolved in DMF (2.5 mL) under argon, tetrakis(triphenylphosphine)palladium (0) (13.5 mg, 11.7 µmol) and CuI (8.91 mg, 46.8 µmol, Eq: 0.20) were added and the mixture sonicated for 5 min with bubbling argon. The reaction mixture was stirred at 90° C. (oil bath temperature) for 2.5 h. The reaction mixture was concentrated under high vacuum and the residue was purified by chromatography (60 g column, 50 µm from Analogix, 0-50% EtOAc in hexanes over 30 min) to give N-tert-butyl-2-(1-methyl-4,5,6,7-tetrahydro-1H-indazol-3-yl)-5-((2-(trimethylsilyl)ethoxy)methyl)-5H-pyrrolo[2,3-b]pyrazine-7-carboxamide (25 mg, 51.8 µmol, 22.1%) as an off-white solid. MS (M+Na)$^+$=505; $^1$H NMR (CDCl$_3$) δ: 9.12 (s, 1H), 8.33 (s, 1H), 8.02 (s, 1H), 5.73 (s, 2H), 3.90 (s, 3H), 3.54-3.68 (m, 2H), 3.06 (t, J=6.0 Hz, 2H), 2.63-2.78 (m, 2H), 1.91-2.06 (m, 2H), 1.77-1.90 (m, 2H), 1.62 (s, 9H), 0.95-1.02 (m, 2H), 0.00 (s, 9H).

Step 3

2-(1-Methyl-4,5,6,7-tetrahydro-1H-indazol-3-yl)-5H-pyrrolo[2,3-b]pyrazine-7-carboxylic acid tert-butylamide

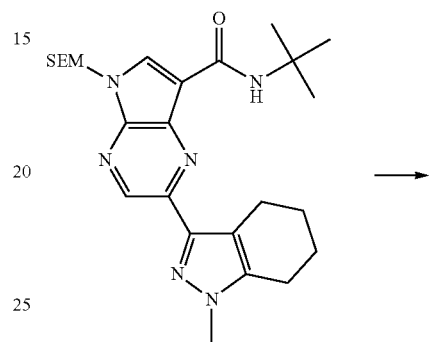

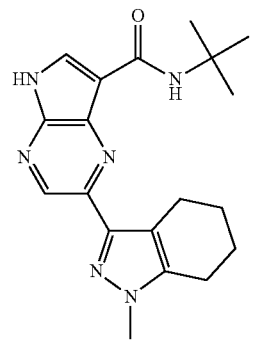

To a pale yellow solution of N-tert-butyl-2-(1-methyl-4,5,6,7-tetrahydro-1H-indazol-3-yl)-5-((2-(trimethylsilyl)ethoxy)methyl)-5H-pyrrolo[2,3-b]pyrazine-7-carboxamide (25 mg, 51.8 mmol) in dichloromethane (2.00 mL) was added TFA (2.96 g, 2.00 mL, 26.0 mmol, Eq: 501), the reaction mixture turned brown and was stirred at 25° C. for 18 h. The mixture was concentrated and the residue was re-dissolved in 5 mL of a solution of (dichloromethane/MeOH/ammonium hydroxide; 60:10:1) and stirred at 25° C. for 3 h, then evaporated to a light yellow solid, dissolved in dichloromethane (containing a few drops of MeOH) and purified by chromatography (spherical silica 20-45 µm, 23 g, Versaflash Supelco) eluting with 0 to 5% over 15 min (MeOH containing 10% ammonium hydroxide)/dichloromethane. Product isolated as an off-white solid which was sonicated with cyclohexane decanted and then sonicated again with MeOH, decanted and dried to give clean N-tert-butyl-2-(1-methyl-4,5,6,7-tetrahydro-1H-indazol-3-yl)-5H-pyrrolo[2,3-b]pyrazine-7-carboxamide (8 mg, 22.7 µmol, 43.8%). MS (M+H)$^+$= 353.1; $^1$H NMR (DMSO-d$_6$) δ: 8.91 (s, 1H), 8.26 (s, 1H), 7.74 (s, 1H), 3.76 (s, 3H), 2.91 (br. s., 2H), 2.64 (br. s., 2H), 1.65-1.84 (m, 4H), 1.45 (s, 9H); LCMS ESI⁺ TIC MS showed 100% purity, [M+H]⁺=353.1, [MNa]⁺=375.0.

Example 296

2-{1-[3-(3,3-Difluoro-azetidin-1-yl)-propyl]-5-difluoromethoxy-1H-indazol-3-yl}-5H-pyrrolo[2,3-b]pyrazine-7-carboxylic acid tert-butylamide

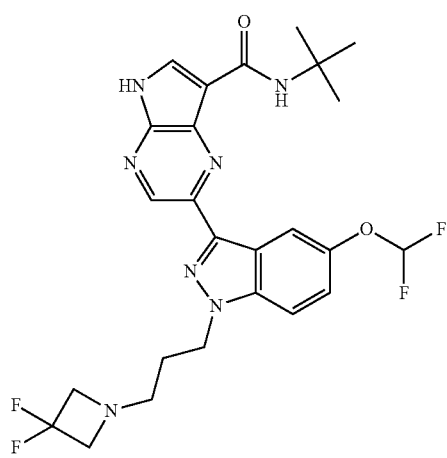 [SMILES: CC(C)(C)NC(=O)c1c[nH]c2ncc(-c3nn(CCCN4CC(F)(F)C4)c4ccc(OC(F)F)cc34)nc12]

Step 1

1-(2-(1,3-Dioxan-2-yl)ethyl)-5-(difluoromethoxy)-3-iodo-1H-indazole

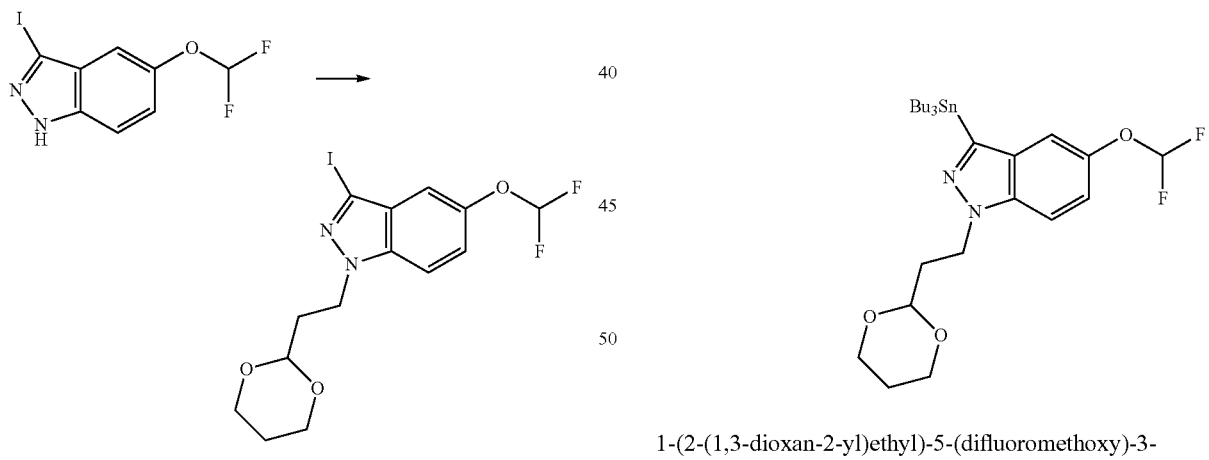

To a clear colorless solution of 5-(difluoromethoxy)-3-iodo-1H-indazole (250 mg, 806 µmol) in THF (5 mL) at 0° C. was added KOtBu 1M in THF (806 µL, 806 µmol) and the mixture stirred at 0° C. for 30 min to form a pale yellow suspension (mostly solution) then added 2-(2-bromoethyl)-1,3-dioxane (189 mg, 131 µL, 968 µmol.2). The reaction mixture was stirred at 0° C. for 30 min then warmed to 25° C. and stirred for 18 h and added more KOtBu 1M in THF (806 µL, 806 µmol) stirred for 10 min at 25° C. and added 2-(2-bromoethyl)-1,3-dioxane (189 mg, 131 µL, 968 µmol.2) and reaction heated to 50° C. for 18 h. The reaction mixture was quenched with saturated ammonium chloride in water and extracted with dichloromethane (3×30 mL), organics dried over MgSO₄ and concentrated to a clear oil. Then dissolved in toluene and purified by chromatography (80 g column, 50 µm from Analogix, 0-20% EtOAc in hexanes over 20 min to afford 1-(2-(1,3-dioxan-2-yl)ethyl)-5-(difluoromethoxy)-3-iodo-1H-indazole (242 mg, 571 µmol, 70.8%) as a clear dense oil. MS (M+H)⁺=424.8; ¹H NMR (CDCl₃) δ: 7.42 (d, J=8.7 Hz, 1H), 7.27 (s, 1H), 7.14-7.25 (m, 1H), 6.43 (t, J=73.7 Hz, 1H), 4.51 (t, J=6.8 Hz, 2H), 4.38 (t, J=5.1 Hz, 1H), 4.08 (dd, J=11.0, 4.9 Hz, 2H), 3.65 (td, J=12.3, 2.3 Hz, 2H), 2.16-2.26 (m, 2H), 1.96-2.15 (m, 1H), 1.32 (d, J=13.6 Hz, 1H). The regioisomer 2-(2-(1,3-dioxan-2-yl)ethyl)-5-(difluoromethoxy)-3-iodo-2H-indazole (a white waxy solid; 40.5 mg, 95.5 µmol, 12%) and unreacted starting material (31 mg, 12%) were also obtained.

Step 2

1-(2-(1,3-Dioxan-2-yl)ethyl)-5-(difluoromethoxy)-3-(tributylstannyl)-1H-indazole

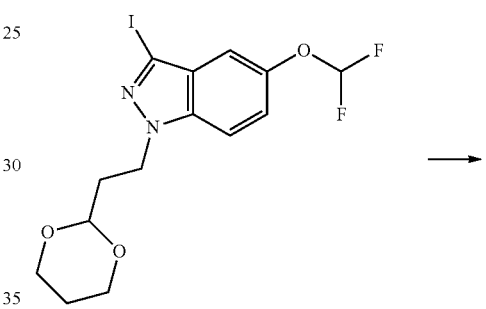

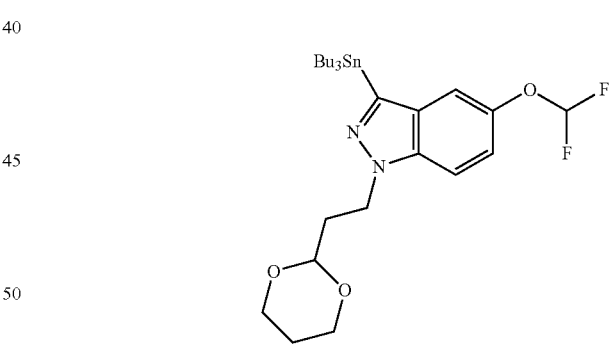

1-(2-(1,3-dioxan-2-yl)ethyl)-5-(difluoromethoxy)-3-iodo-1H-indazole (242 mg, 571 mmol) was dissolved in THF (3.00 mL). The colorless solution was cooled to −16° C. (NaCl/ice bath), isopropylmagnesium chloride 2M in THF (319 µL, 639 µmol) was added dropwise at −16° C. The reaction mixture was stirred at −16° C. for 20 min. Then, tributylchlorostannane (214 mg, 178 µL, 656 µmol) was added slowly. The reaction mixture was warmed to 25° C. and stirred for 1.5 h. The reaction mixture was quenched with saturated ammonium chloride solution, extracted with dichloromethane (3×30 mL), organics dried over MgSO₄ and concentrated to a yellow oil. The residue was dried under high vacuum and taken into next step without further purification yielding 1-(2-(1,3-dioxan-2-yl)ethyl)-5-(difluoromethoxy)-

3-(tributylstannyl)-1H-indazole, assumed quantitative and used into the next step without further purification.

Step 3

2-(1-(2-(1,3-Dioxan-2-yl)ethyl)-5-(difluoromethoxy)-1H-indazol-3-yl)-N-tert-butyl-5-((2-(trimethylsilyl)ethoxy)methyl)-5H-pyrrolo[2,3-b]pyrazine-7-carboxamide

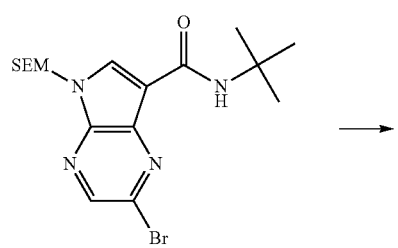

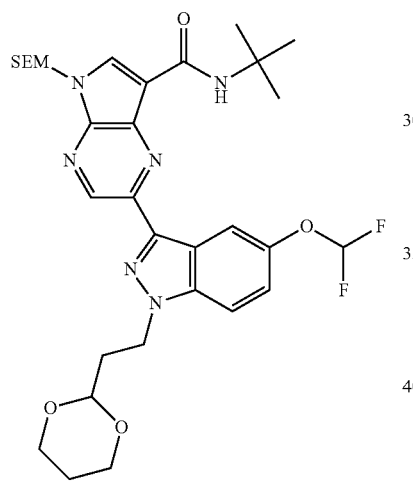

2-Bromo-N-tert-butyl-5-((2-(trimethylsilyl)ethoxy)methyl)-5H-pyrrolo[2,3-b]pyrazine-7-carboxamide (244 mg, 571 μmol) and 1-(2-(1,3-dioxan-2-yl)ethyl)-5-(difluoromethoxy)-3-(tributylstannyl)-1H-indazole (335 mg, 571 μmol) were dissolved in DMF (3.00 mL) under argon, tetrakis(triphenylphosphine)palladium (0) (33.0 mg, 28.6 μmol) and CuI (21.7 mg, 114 mmol, Eq: 0.20) were added and the mixture sonicated for 5 min with bubbling argon. The reaction mixture was stirred at 90° C. (oil bath temperature) for 4 h. The reaction mixture was concentrated under high vacuum and the residue (dark solid) was purified by chromatography (80 g column, 50 μm from Analogix, 0-50% EtOAc in hexanes over 30 min) to give 2-(1-(2-(1,3-dioxan-2-yl)ethyl)-5-(difluoromethoxy)-1H-indazol-3-yl)-N-tert-butyl-5-((2-(trimethylsilyl)ethoxy)methyl)-5H-pyrrolo[2,3-b]pyrazine-7-carboxamide (230 mg, 357 μmol, 62.5%) as an off-white solid. MS (M+Na)$^+$=667.1; $^1$H NMR (CDCl$_3$) δ: 9.25 (s, 1H), 8.37 (s, 1H), 8.32 (d, J=2.0 Hz, 1H), 8.06 (s, 1H), 7.56 (dd, J=9.1, 0.5 Hz, 1H), 7.35 (dd, J=9.1, 2.3 Hz, 1H), 6.55 (t, J=74.3 Hz, 1H), 5.75 (s, 2H), 4.65 (t, J=6.9 Hz, 2H), 4.55 (t, J=4.9 Hz, 1H), 4.12-4.21 (m, 2H), 3.74 (td, J=12.3, 2.5 Hz, 2H), 3.56-3.65 (m, 2H), 2.34 (td, J=6.8, 5.3 Hz, 2H), 2.05- 2.23 (m, 1H), 1.65 (s, 9H), 1.39 (dt, J=13.4, 1.3 Hz, 1H), 0.94-1.04 (m, 2H), −0.06-0.05 (m, 9H).

Step 4

N-tert-Butyl-2-(5-(difluoromethoxy)-1-(3-oxopropyl)-1H-indazol-3-yl)-5-((2-(trimethylsilyl)ethoxy)methyl)-5H-pyrrolo[2,3-b]pyrazine-7-carboxamide

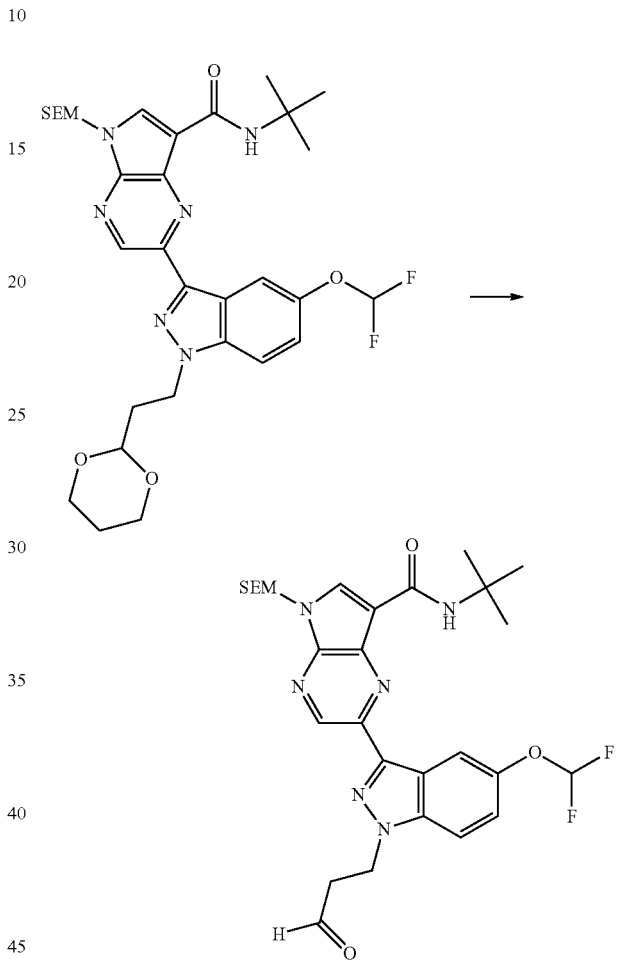

2-(1-(2-(1,3-Dioxan-2-yl)ethyl)-5-(difluoromethoxy)-1H-indazol-3-yl)-N-tert-butyl-5-((2-(trimethylsilyl)ethoxy)methyl)-5H-pyrrolo[2,3-b]pyrazine-7-carboxamide (130 mg, 202 μmol) was dissolved in THF (3 mL), and HCl 3N (672 μL, 2.02 mmol0.00) was added. After stirring the mixture at 25° C. overnight, TLC and LCMS showed about 10% conversion. Added 0.5 mL of concentrated HCl and reaction heated to 50° C. for 48 h more. A saturated aqueous sodium hydrogen carbonate solution was added to the reaction mixture, and the mixture was extracted with dichloromethane (5×30 mL). The obtained organic layer was dried over anhydrous magnesium sulfate. The solvent was evaporated, and the obtained residue was purified by silica gel chromatography (n-hexane-ethyl acetate 0 to 100% over 30 min to give N-tert-butyl-2-(5-(difluoromethoxy)-1-(3-oxopropyl)-1H-indazol-3-yl)-5-((2-(trimethylsilyl)ethoxy)methyl)-5H-pyrrolo[2,3-b]pyrazine-7-carboxamide (34 mg, 58.0 μmol, 28.7%). MS (M+H)$^+$=587; $^1$H NMR (CDCl$_3$) δ: 9.97 (s, 1H), 9.20 (s, 1H), 8.42 (s, 1H), 8.30 (d, J=2.3 Hz, 1H), 8.08 (s, 1H), 7.63 (d, J=9.1 Hz, 1H), 7.39 (dd, J=9.1, 2.3 Hz, 1H), 6.54 (t, J=74.4 Hz, 1H), 5.75 (s, 2H), 5.34 (s, 1H), 4.82 (t, J=6.2 Hz, 2H), 3.55-3.65 (m, 2H), 3.33 (t, J=6.4 Hz, 2H), 1.64 (s, 9H), 0.90-1.05 (m, 2H), 0.05-0.07 (m, 1H), 0.00 (s, 9H). Unreacted starting material (31 mg, 24%) as also obtained.

Step 5

N-tert-Butyl-2-(1-(3-(3,3-difluoroazetidin-1-yl)propyl)-5-(difluoromethoxy)-1H-indazol-3-yl)-5-((2-(trimethylsilyl)ethoxy)methyl)-5H-pyrrolo[2,3-b]pyrazine-7-carboxamide

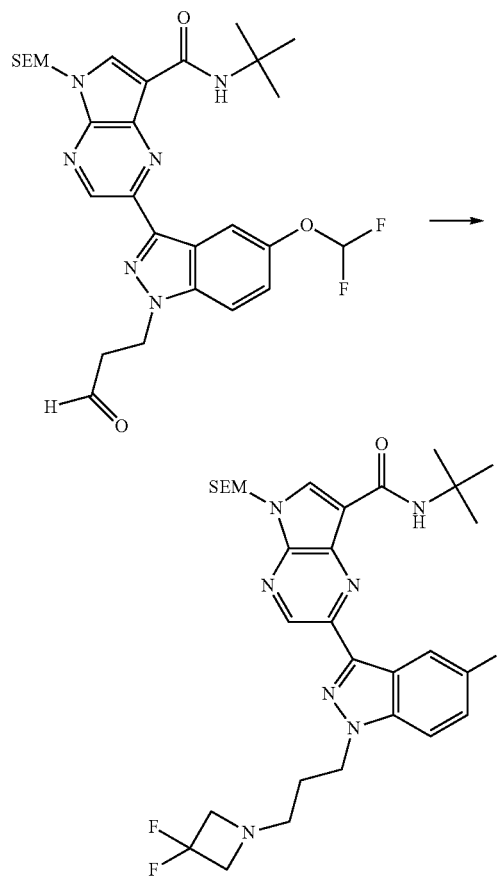

To a solution of N-tert-butyl-2-(5-(difluoromethoxy)-1-(3-oxopropyl)-1H-indazol-3-yl)-5-((2-(trimethylsilyl)ethoxy)methyl)-5H-pyrrolo[2,3-b]pyrazine-7-carboxamide (34 mg, 58.0 µmol) in dichloroethane (6 mL) was added 3,3-difluoroazetidine hydrochloride (9.76 mg, 75.3 µmol.30). The mixture was stirred at 25° C. for 15 min, then sodium triacetoxyborohydride (18.4 mg, 86.9 µmol0) was added and stirring was continued for 18 h. The reaction mixture was diluted with saturated NaHCO₃ solution and extracted with dichloromethane (5×20 mL). The organic layer was dried (MgSO₄) and concentrated in vacuo. The resultant residue was purified by chromatography (spherical silica 20-45 µm, 23 g, Versaflash Supelco) eluting with 0 to 5% over 20 min (MeOH containing 10% ammonium hydroxide)/dichloromethane to give N-tert-butyl-2-(1-(3-(3,3-difluoroazetidin-1-yl)propyl)-5-(difluoromethoxy)-1H-indazol-3-yl)-5-((2-(trimethylsilyl)ethoxy)methyl)-5H-pyrrolo[2,3-b]pyrazine-7-carboxamide (38 mg, 57.2 µmol, 98.8%) as an off-white solid. MS (M+Na)⁺=686; ¹H NMR (CDCl₃) δ: 9.22 (s, 1H), 8.36 (s, 1H), 8.32 (d, J=2.3 Hz, 1H), 8.05 (s, 1H), 7.59 (d, J=9.1 Hz, 1H), 7.36 (dd, J=9.1, 2.3 Hz, 1H), 6.55 (t, J=74.0 Hz, 1H), 5.75 (s, 2H), 4.61 (t, J=6.6 Hz, 2H), 3.53-3.72 (m, 6H), 2.64 (t, J=6.0 Hz, 2H), 2.14 (dq, J=6.8, 5.7 Hz, 2H), 1.64 (s, 9H), 0.91-1.08 (m, 2H), 0.00 (s, 9H).

Step 6

2-{1-[3-(3,3-Difluoro-azetidin-1-yl)-propyl]-5-difluoromethoxy-1H-indazol-3-yl}-5H-pyrrolo[2,3-b]pyrazine-7-carboxylic acid tert-butylamide

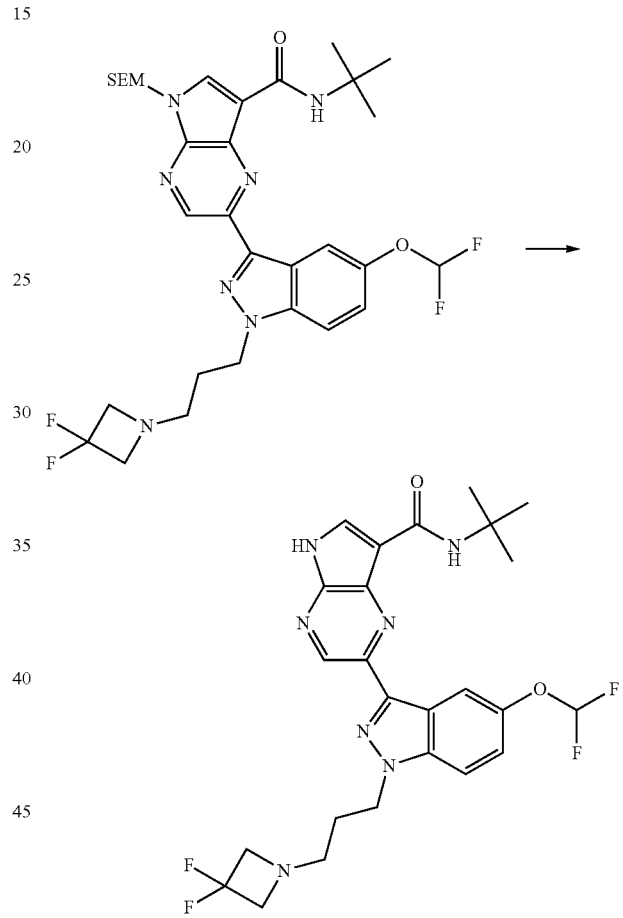

To a pale yellow solution of N-tert-butyl-2-(1-(3-(3,3-difluoroazetidin-1-yl)propyl)-5-(difluoromethoxy)-1H-indazol-3-yl)-5-((2-(trimethylsilyl)ethoxy)methyl)-5H-pyrrolo[2,3-b]pyrazine-7-carboxamide (38 mg, 57.2 µmol) in dichloromethane (4.00 mL) was added TFA (1.48 g, 1.00 mL, 13.0 mmol27), the reaction mixture turned orange and was stirred at 25° C. for 18 h, mixture concentrated and the residue was re-dissolved in 5 mL of a solution of (dichloromethane/MeOH/ammonium hydroxide; 60:10:1) and stirred at 25° C. for 1 h, then evaporated to a yellow solid, which was dissolved in dichloromethane and purified by chromatography (spherical silica 20-45 µm, 23 g, Versaflash Supelco) eluting with 0 to 5% over 20 min (MeOH containing 10% ammonium hydroxide)/dichloromethane. The pure product dissolved in dichloromethane and cyclohexane added to allow solid formation, off-white solid was separated by decantation and dried under high vacuum to give N-tert-butyl-2-(1-(3-(3,3- difluoroazetidin-1-yl)propyl)-5-(difluoromethoxy)-1H-indazol-3-yl)-5H-pyrrolo[2,3-b]pyrazine-7-carboxamide (29.5 mg, 55.3 μmol, 96.6%). MS (M+H)⁺=534; ¹H NMR (DMSO-d₆) δ: 9.07 (s, 1H), 8.37 (s, 1H), 8.19 (s, 1H), 7.81-7.96 (m, 2H), 7.40 (d, J=8.3 Hz, 1H), 7.19 (t, J=74.4 Hz, 1H), 4.56 (br. s., 2H), 3.56 (t, J=12.5 Hz, 4H), 2.54 (br. s., 2H), 1.95 (m, J=6.2 Hz, 2H), 1.49 (s, 9H).

Example 297

2-[5-Difluoromethoxy-1-(2-[1,3]dioxan-2-yl-ethyl)-1H-indazol-3-yl]-5H-pyrrolo[2,3-b]pyrazine-7-carboxylic acid tert-butylamide

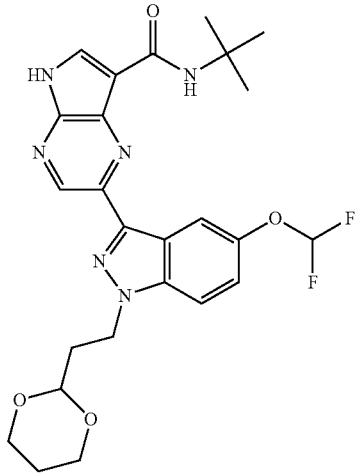 [SMILES: CC(C)(C)NC(=O)c1c[nH]c2ncc(-c3nn(CCC4OCCCO4)c4ccc(OC(F)F)cc34)nc12]

2-(1-(2-(1,3-dioxan-2-yl)ethyl)-5-(difluoromethoxy)-1H-indazol-3-yl)-N-tert-butyl-5-((2-(trimethylsilyl)ethoxy)methyl)-5H-pyrrolo[2,3-b]pyrazine-7-carboxamide (100 mg, 155 μmol) was dissolved in acetone (3 mL), and HCl 3N (1.2 g, 1 mL, 3.00 mmol9.3) was added. Heated to 50° C. with stirring and continued for 5 days. A saturated aqueous sodium hydrogen carbonate solution was added to the reaction mixture, and the mixture was extracted with dichloromethane (5×30 mL). The combined organic layers were dried over anhydrous magnesium sulfate. The solvent was evaporated, and the obtained residue was purified by silica gel chromatography (n-hexane-ethyl acetate 0 to 100% over 20 min) to give N-tert-butyl-2-(5-(difluoromethoxy)-1-(3-oxopropyl)-1H-indazol-3-yl)-5-((2-(trimethylsilyl)ethoxy)methyl)-5H-pyrrolo[2,3-b]pyrazine-7-carboxamide (27 mg, 46.0 μmol, 29.7%) and a small amount of the SEM group de-protection product 2-(1-(2-(1,3-dioxan-2-yl)ethyl)-5-(difluoromethoxy)-1H-indazol-3-yl)-N-tert-butyl-5H-pyrrolo[2,3-b]pyrazine-7-carboxamide (5 mg, 9.72 μmol, 6.27%) as light yellow needles. MS (M+H)⁺=515; ¹H NMR (DMSO-d₆) δ: 12.80 (br. s., 1H), 9.08 (s, 1H), 8.37 (s, 1H), 8.20 (d, J=2.3 Hz, 1H), 7.87 (s, 1H), 7.81 (d, J=9.1 Hz, 1H), 7.39 (dd, J=9.1, 2.3 Hz, 1H), 7.19 (t, J=74.4 Hz, 1H), 4.45-4.72 (m, 3H), 3.99 (dd, J=11.3, 4.5 Hz, 2H), 3.55-3.75 (m, 2H), 2.07-2.22 (m, 2H), 1.79-1.97 (m, 1H), 1.49 (s, 9H), 1.38 (s, 9H), 134 (m, 1H). Unreacted starting material (34 mg, 34%) was also obtained.

Example 298

2-[5-Difluoromethoxy-1-(3-hydroxy-propyl)-1H-indazol-3-yl]-5H-pyrrolo[2,3-b]pyrazine-7-carboxylic acid tert-butylamide

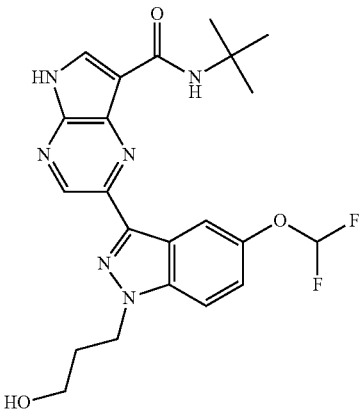 [SMILES: CC(C)(C)NC(=O)c1c[nH]c2ncc(-c3nn(CCCO)c4ccc(OC(F)F)cc34)nc12]

Step 1

N-tert-Butyl-2-(5-(difluoromethoxy)-1-(3-hydroxypropyl)-1H-indazol-3-yl)-5-((2-(trimethylsilyl)ethoxy)methyl)-5H-pyrrolo[2,3-b]pyrazine-7-carboxamide

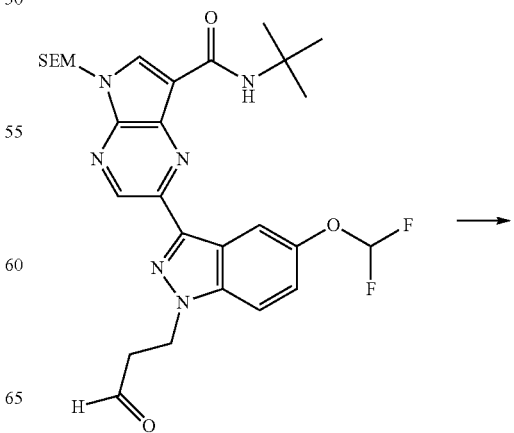

991

-continued

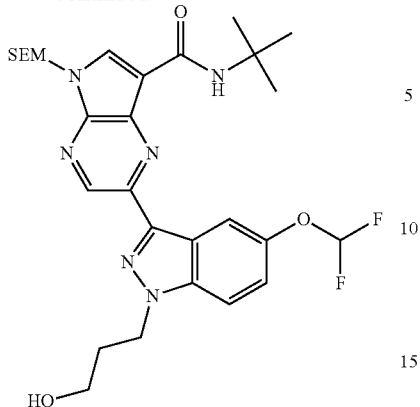

992

-continued

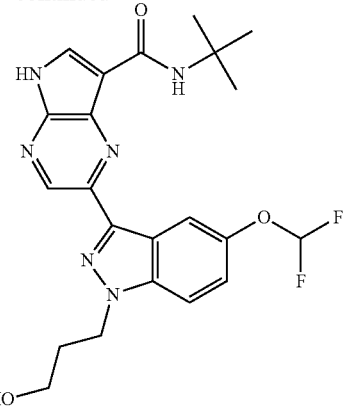

To a solution of N-tert-butyl-2-(5-(difluoromethoxy)-1-(3-oxopropyl)-1H-indazol-3-yl)-5-((2-(trimethylsilyl)ethoxy)methyl)-5H-pyrrolo[2,3-b]pyrazine-7-carboxamide (27 mg, 46.0 mmol) in dichloroethane (4.76 mL) was added azetidin-3-ol hydrochloride (6.55 mg, 59.8 µmol.30). The mixture was stirred at 25° C. for 15 min, then sodium triacetoxyborohydride (14.6 mg, 69.0 µmol0) was added and stirring was continued for 18 h. The reaction mixture was diluted with saturated NaHCO$_3$ solution and extracted with dichloromethane (5×20 mL). The organic layer was dried (MgSO$_4$) and concentrated in vacuo. The resultant residue was purified by chromatography (spherical silica 20-45 µm, 23 g, Versaflash Supelco) eluting with 0 to 5% over 20 min (MeOH containing 10% ammonium hydroxide)/dichloromethane to give traces of N-tert-butyl-2-(5-(difluoromethoxy)-1-(3-(3-hydroxyazetidin-1-yl)propyl)-1H-indazol-3-yl)-5-((2-(trimethylsilyl)ethoxy)methyl)-5H-pyrrolo[2,3-b]pyrazine-7-carboxamide and obtained mainly N-tert-butyl-2-(5-(difluoromethoxy)-1-(3-hydroxypropyl)-1H-indazol-3-yl)-5-((2-(trimethylsilyl)ethoxy)methyl)-5H-pyrrolo[2,3-b]pyrazine-7-carboxamide (17 mg, 28.9 µmol, 62.7%) as an off-white solid. MS (M+H)$^+$=589; $^1$H NMR (CDCl$_3$) δ: 9.21 (s, 1H), 8.37 (s, 1H), 8.32 (d, J=2.3 Hz, 1H), 8.06 (s, 1H), 7.59 (d, J=9.1 Hz, 1H), 7.37 (dd, J=8.9, 2.1 Hz, 1H), 6.55 (t, J=74.4 Hz, 1H), 5.75 (s, 2H), 4.70 (t, J=6.6 Hz, 2H), 3.74 (t, J=5.7 Hz, 2H), 3.55-3.67 (m, 2H), 2.29 (quin, J=6.0 Hz, 2H), 1.64 (s, 9H), 0.91-1.05 (m, 2H), 0.00 (s, 9H).

Step 2

2-[5-Difluoromethoxy-1-(3-hydroxy-propyl)-1H-indazol-3-yl]-5H-pyrrolo[2,3-b]pyrazine-7-carboxylic acid tert-butylamide

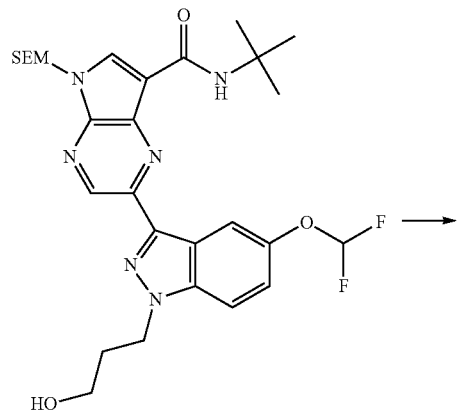

To a pale yellow solution of N-tert-butyl-2-(5-(difluoromethoxy)-1-(3-hydroxypropyl)-1H-indazol-3-yl)-5-((2-(trimethylsilyl)ethoxy)methyl)-5H-pyrrolo[2,3-b]pyrazine-7-carboxamide (17 mg, 28.9 µmol) in dichloromethane (4.00 mL) was added TFA (1480 mg, 1.0 mL, Eq 450), the reaction mixture turned orange and was stirred at 25° C. for 24 h, mixture concentrated and the residue was re-dissolved in 5 mL of a solution of (dichloromethane/MeOH/ammonium hydroxide; 60:10:1) and stirred at 25° C. for 1 h, then evaporated to an off-white solid, which was dissolved in dichloromethane and purified by chromatography (spherical silica 20-45 µm, 23 g, Versaflash Supelco) eluting with 0 to 5% over 20 min (MeOH containing 10% ammonium hydroxide)/dichloromethane. The pure product dissolved in dichloromethane and cyclohexane added to allow solid formation, light yellow solid was separated by filtration and dried under high vacuum to give N-tert-butyl-2-(5-(difluoromethoxy)-1-(3-hydroxypropyl)-1H-indazol-3-yl)-5H-pyrrolo[2,3-b]pyrazine-7-carboxamide (12 mg, 26.2 µmol, 90.6%). MS (M+H)$^+$=459; $^1$H NMR (DMSO-d$_6$) δ: 9.05 (s, 1H), 8.37 (s, 1H), 8.19 (s, 1H), 7.79-7.94 (m, 2H), 7.38 (d, J=8.7 Hz, 1H), 7.18 (t, J=74.4 Hz, 1H), 4.62-4.68 (m, 1H), 4.59 (t, J=6.8 Hz, 2H), 3.40-3.51 (m, 2H), 2.06 (t, J=6.2 Hz, 1H), 1.49 (s, 9H).

Example 299

2-[5-Difluoromethoxy-1-(3-morpholin-4-yl-propyl)-1H-indazol-3-yl]-5H-pyrrolo[2,3-b]pyrazine-7-carboxylic acid tert-butylamide

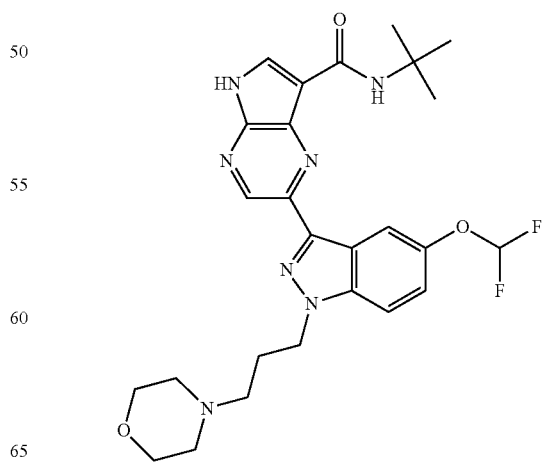

993

Step 1

N-tert-butyl-2-(5-(difluoromethoxy)-1-(3-morpholinopropyl)-1H-indazol-3-yl)-5-((2-(trimethylsilyl)ethoxy)methyl)-5H-pyrrolo[2,3-b]pyrazine-7-carboxamide

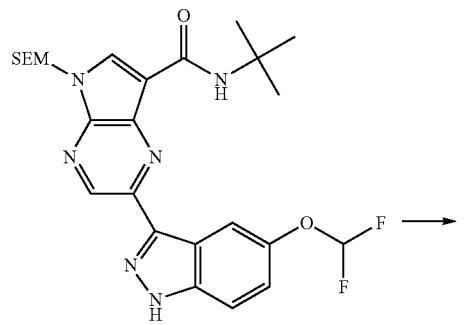

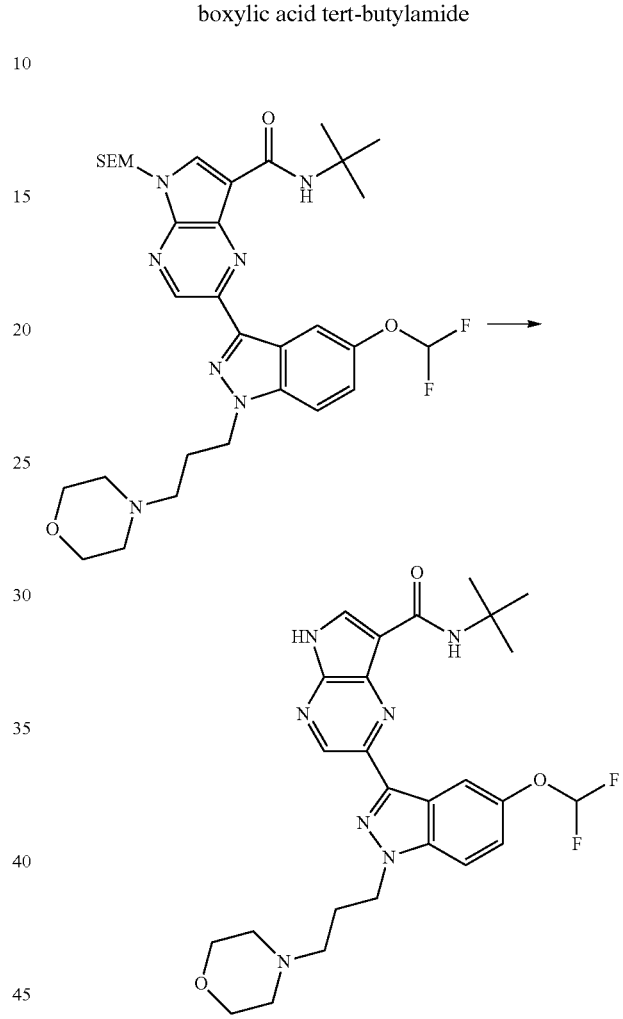

In a 2-(5 mL Biotage microwave vial were mixed N-tert-butyl-2-(5-(difluoromethoxy)-1H-indazol-3-yl)-5-((2-(trimethylsilyl)ethoxy)methyl)-5H-pyrrolo[2,3-b]pyrazine-7-carboxamide (60 mg, 113 µmol), 4-(3-chloropropyl)morpholine (55.5 mg, 339 µmol, Eq: 3.0) and Cs$_2$CO$_3$ (147 mg, 452 µmol) in DMF (2 mL). The mixture was stirred ~10 min at 25° C. then heated to 100° C. in the Biotage microwave reactor for 30 min. Then, diluted with 10 mL of dichloromethane and filtered through a celite pad, filtrate concentrated under high vacuum at 65° C. and residue dissolved in dichloromethane and purified by chromatography (spherical silica 20-45 µm, 23 g, Versaflash Supelco) eluting with 0 to 5% over 20 min (MeOH containing 10% ammonium hydroxide)/dichloromethane to give N-tert-butyl-2-(5-(difluoromethoxy)-1-(3-morpholinopropyl)-1H-indazol-3-yl)-5-((2-(trimethylsilyl)ethoxy)methyl)-5H-pyrrolo[2,3-b]pyrazine-7-carboxamide (62 mg, 94.2 µmol, 83.4%) as an off-white solid. MS (M+Na)$^+$=680; $^1$H NMR (CDCl$_3$) δ: 9.23 (s, 1H), 8.36 (s, 1H), 8.32 (d, J=2.3 Hz, 1H), 8.05 (s, 1H), 7.59 (d, J=9.1 Hz, 1H), 7.35 (dd, J=8.9, 2.1 Hz, 1H), 6.55 (t, J=74.4 Hz, 1H), 5.75 (s, 2H), 4.61 (t, J=6.4 Hz, 2H), 3.75 (br. s., 4H), 3.55-3.66 (m, 2H), 2.45 (br. s., 6H), 2.25 (br. s., 2H), 1.65 (s, 9H), 0.90-1.06 (m, 2H), 0.00 (s, 9H).

Step 2

2-[5-Difluoromethoxy-1-(3-morpholin-4-yl-propyl)-1H-indazol-3-yl]-5H-pyrrolo[2,3-b]pyrazine-7-carboxylic acid tert-butylamide To a pale yellow solution of N-tert-butyl-2-(5-(difluoromethoxy)-1-(3-morpholinopropyl)-1H-indazol-3-yl)-5-((2-(trimethylsilyl)ethoxy)methyl)-5H-pyrrolo[2,3-b]pyrazine-7-carboxamide (62 mg, 94.2 µmol) in dichloromethane (4.00 mL) was added TFA (1.48 g, 1.00 mL, 13.0 mmol38), the reaction mixture turned orange and was stirred at 25° C. for 18 h, mixture concentrated and the residue was re-dissolved in 5 mL of a solution of (dichloromethane/MeOH/ammonium hydroxide; 60:10:1) and stirred at 25° C. for 1 h, then evaporated to a yellow solid, which was dissolved in dichloromethane and purified by chromatography (spherical silica 20-45 µm, 23 g, Versaflash Supelco) eluting with 0 to 5% over 20 min (MeOH containing 10% ammonium hydroxide)/dichloromethane. The pure product dissolved in dichloromethane with few drops of MeOH and cyclohexane added to allow solid formation, light yellow flakes were separated by decantation and dried under high vacuum to give N-tert-butyl-2-(5-(difluoromethoxy)-1-(3-morpholinopropyl)-1H-indazol-3-yl)-5H-pyrrolo[2,3-b]pyrazine-7-carboxamide (45 mg, 85.3 µmol, 90.5%). MS (M+H)$^+$=528; $^1$H NMR (DMSO-d$_6$) δ: 12.80 (br. s., 1H), 9.06 (s, 1H), 8.37 (s, 1H), 8.19 (s, 1H), 7.77-7.98 (m, 2H), 7.38 (d, J=8.7 Hz, 1H), 7.18 (t, J=74.4 Hz, 1H), 4.57 (t, J=5.7 Hz, 2H), 3.49 (br. s., 4H), 2.26 (br. s., 6H), 2.00-2.15 (m, 2H), 1.49 (s, 9H).

Example 300

2-{5-Difluoromethoxy-1-[3-(3-hydroxy-azetidin-1-yl)-propyl]-1H-indazol-3-yl}-5H-pyrrolo[2,3-b]pyrazine-7-carboxylic acid tert-butylamide

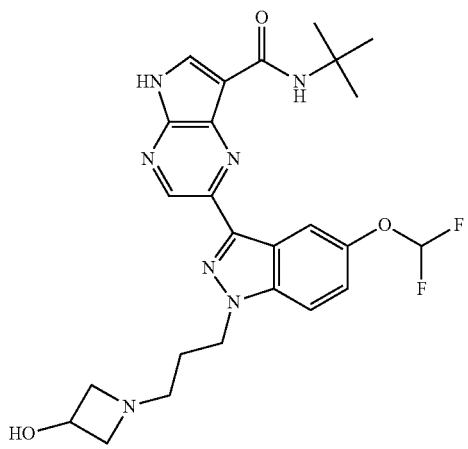 [SMILES: CC(C)(C)NC(=O)c1c[nH]c2ncc(-c3nn(CCCN4CC(O)C4)c4ccc(OC(F)F)cc34)nc12]

Step 1

1-(3-chloropropyl)azetidin-3-ol

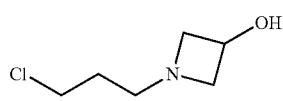

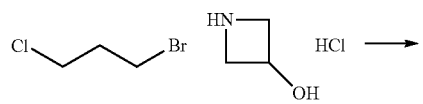

In a 25 mL round-bottomed flask were mixed with stirring azetidin-3-ol hydrochloride (available from Beta Pharma, 250 mg, 2.28 mmol) and 1-bromo-3-chloropropane (719 mg, 4.56 mmol.0) in acetonitrile (5 mL) to the suspension was added Cs$_2$CO$_3$ (1.86 g, 5.7 mmol.50). The mixture was stirred at 25° C. for 18 h, then diluted with 15 mL of EtOAc and filtered to remove solids. Filtrate was evaporated and residue purified by chromatography (40 g column, 50 μm from Analogix, 0 to 5% over 20 min (MeOH containing 10% ammonium hydroxide)/dichloromethane (developing TLC in an iodine chamber) to give 1-(3-chloropropyl)azetidin-3-ol (128 mg, 856 μmol, 37.5%) as a clear dense liquid. $^1$H NMR (CDCl$_3$) δ: 4.25-4.53 (m, 2H), 3.36-3.68 (m, 4H), 2.82-3.04 (m, 2H), 2.58 (t, J=7.2 Hz, 2H), 1.80 (quin, J=6.8 Hz, 2H).

Step 2

N-tert-butyl-2-(5-(difluoromethoxy)-1-(3-(3-hydroxyazetidin-1-yl)propyl)-1H-indazol-3-yl)-5-((2-(trimethylsilyl)ethoxy)methyl)-5H-pyrrolo[2,3-b]pyrazine-7-carboxamide

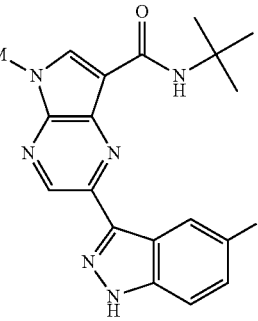

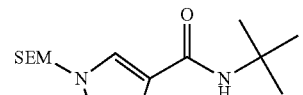

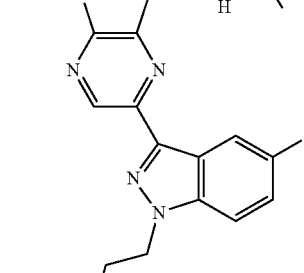

In a 2-5 mL Biotage microwave vial were mixed N-tert-butyl-2-(5-(difluoromethoxy)-1H-indazol-3-yl)-5-((2-(trimethylsilyl)ethoxy)methyl)-5H-pyrrolo[2,3-b]pyrazine-7-carboxamide (50 mg, 94.2 μmol), 1-(3-chloropropyl)azetidin-3-ol (42.3 mg, 283 μmol, Eq: 3.0) and Cs$_2$CO$_3$ (123 mg, 377 μmol) in DMF (2 mL). The mixture was stirred ~10 min at 25° C. then heated to 100° C. in the Biotage microwave reactor for 30 min. LCMS showed complete reaction, diluted with 10 mL of dichloromethane and filtered through a celite pad, filtrate concentrated under high vacuum at 65° C. and residue dissolved in dichloromethane and purified by chromatography (spherical silica 20-45 μm, 23 g, Versaflash Supelco) eluting with 0 to 5% over 20 min (MeOH containing 10% ammonium hydroxide)/dichloromethane to give N-tert-butyl-2-(5-(difluoromethoxy)-1-(3-(3-hydroxyazetidin-1-yl)propyl)-1H-indazol-3-yl)-5-((2-(trimethylsilyl)ethoxy)methyl)-5H-pyrrolo[2,3-b]pyrazine-7-carboxamide (40 mg, 62.1 μmol, 65.9%) as a light yellow semisolid. MS (M+H)$^+$=644; $^1$H NMR (CDCl$_3$) δ: 9.23 (s, 1H), 8.36 (s, 1H), 8.30 (d, J=2.3 Hz, 1H), 8.08 (s, 1H), 7.58 (d, J=9.1 Hz, 1H), 7.35 (dd, J=8.9, 2.1 Hz, 1H), 6.55 (t, J=74.8 Hz, 1H), 5.75 (s, 2H), 4.43-4.63 (m, 3H), 3.66-3.76 (m, 2H), 3.55-3.65 (m, 2H), 2.88-2.99 (m, 2H), 2.51-2.61 (m, 2H), 2.03-2.17 (m, 3H), 1.65 (s, 9H), 0.92-1.02 (m, 2H), 0.00 (s, 9H).

Step 3

2-{5-Difluoromethoxy-1-[3-(3-hydroxy-azetidin-1-yl)-propyl]-1H-indazol-3-yl}-5H-pyrrolo[2,3-b]pyrazine-7-carboxylic acid tert-butylamide

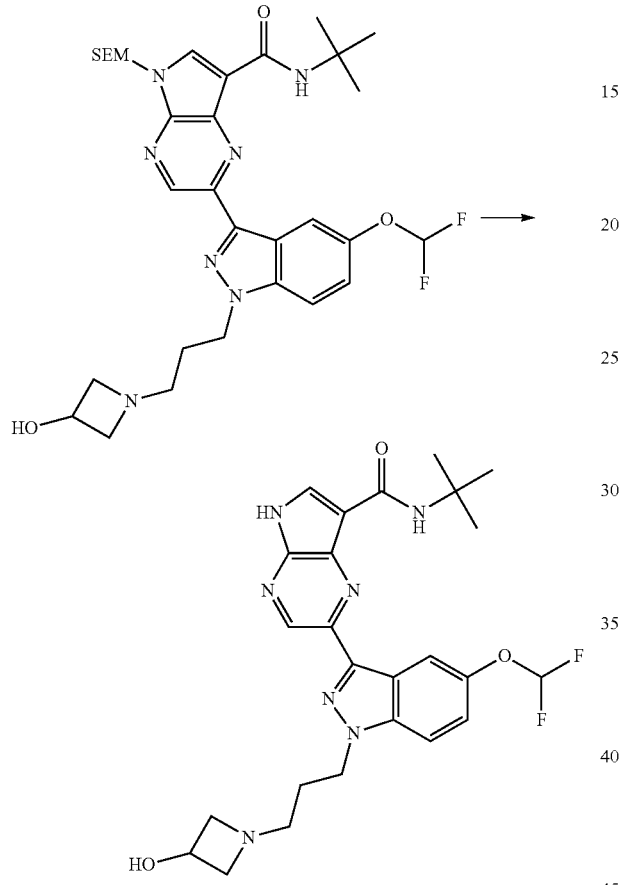

To a pale yellow solution of N-tert-butyl-2-(5-(difluoromethoxy)-1-(3-(3-hydroxyazetidin-1-yl)propyl)-1H-indazol-3-yl)-5-((2-(trimethylsilyl)ethoxy)methyl)-5H-pyrrolo[2,3-b]pyrazine-7-carboxamide (43 mg, 66.8 µmol) in dichloromethane (4.00 mL) was added TFA (740 mg, 0.5 mL, 6.49 mmol, Eq: 97.2), the reaction mixture turned orange and was stirred at 25° C. for 18 h, mixture concentrated and the residue was re-dissolved in 5 mL of a solution of (dichloromethane/MeOH/ammonium hydroxide; 60:10:1) and stirred at 25° C. for 1 h, then evaporated to a yellow foam, which was dissolved in dichloromethane (with few drops of MeOH) and purified by chromatography (spherical silica 20-45 µm, 23 g, Versaflash Supelco) eluting with 0 to 10% over 20 min (MeOH containing 10% ammonium hydroxide)/dichloromethane. The pure product dissolved in dichloromethane and cyclohexane added to allow solid formation, off-white solid was separated by decantation and dried under high vacuum to give N-tert-butyl-2-(5-(difluoromethoxy)-1-(3-(3-hydroxyazetidin-1-yl)propyl)-1H-indazol-3-yl)-5H-pyrrolo[2,3-b]pyrazine-7-carboxamide (21 mg, 40.9 µmol, 61.2%). MS (M+H)$^+$=514; $^1$H NMR (DMSO-d$_6$) δ: 9.06 (s, 1H), 8.37 (s, 1H), 8.19 (s, 1H), 7.81-7.91 (m, 2H), 7.39 (d, J=8.7 Hz, 1H), 7.19 (t, J=74.4 Hz, 1H), 5.23 (d, J=6.4 Hz, 1H), 4.53 (t, J=6.6 Hz, 2H), 4.07-4.25 (m, 1H), 3.50 (t, J=6.4 Hz, 2H), 2.62 (t, J=6.8 Hz, 2H), 2.35 (t, J=6.8 Hz, 2H), 1.78-2.01 (m, 2H), 1.49 (s, 9H).

Example 301

2-{1-[3-(3-Cyano-azetidin-1-yl)-propyl]-5-difluoromethoxy-1H-indazol-3-yl}-5H-pyrrolo[2,3-b]pyrazine-7-carboxylic acid tert-butylamide

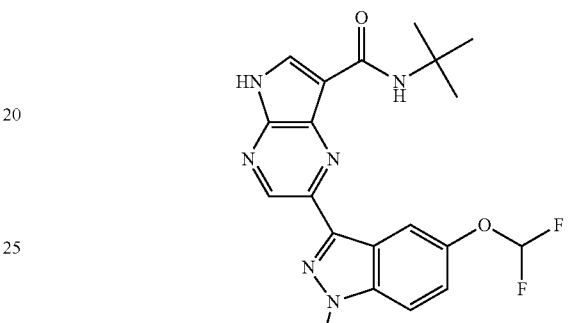

Step 1

1-(3-Chloropropyl)azetidine-3-carbonitrile

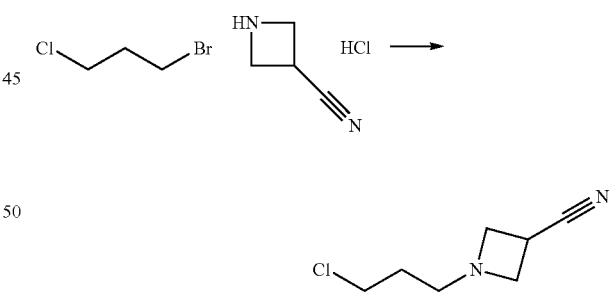

In a 25 mL round-bottomed flask were mixed with stirring azetidine-3-carbonitrile hydrochloride (available from ASW MedChem. Inc., 250 mg, 2.11 mmol) and 1-bromo-3-chloropropane (664 mg, 415 µL, 4.22 mmol.0) in acetonitrile (5 mL) to the suspension was added Cs$_2$CO$_3$ (2.06 g, 6.33 mmol). The mixture was stirred at 25° C. for 18 h, then diluted with 15 mL of EtOAc and filtered to remove solids. Filtrate was evaporated and residue purified by chromatography (40 g column, 50 µm from Analogix, 0 to 5% over 20 min (MeOH containing 10% ammonium hydroxide)/dichloromethane (developing TLC in an iodine chamber) to give 1-(3-chloropropyl)azetidine-3-carbonitrile (230 mg, 1.45 mmol, 68.8%)

as a clear dense liquid. $^1$H NMR (CDCl$_3$) δ: 3.46-3.59 (m, 4H), 3.20-3.31 (m, 3H), 2.55 (t, J=6.8 Hz, 2H), 1.75 (quin, J=6.6 Hz, 2H).

Step 2

N-tert-Butyl-2-(1-(3-(3-cyanoazetidin-1-yl)propyl)-5-(difluoromethoxy)-1H-indazol-3-yl)-5-((2-(trimethylsilyl)ethoxy)methyl)-5H-pyrrolo[2,3-b]pyrazine-7-carboxamide

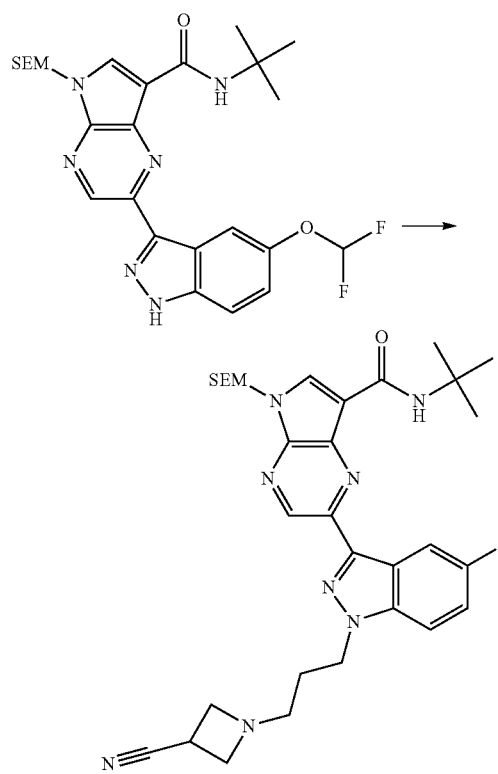

In a 2-5 mL Biotage microwave vial were mixed N-tert-butyl-2-(5-(difluoromethoxy)-1H-indazol-3-yl)-5-((2-(trimethylsilyl)ethoxy)methyl)-5H-pyrrolo[2,3-b]pyrazine-7-carboxamide (50 mg, 94.2 μmol), 1-(3-chloropropyl)azetidine-3-carbonitrile (44.8 mg, 283 μmol, Eq: 3.0) and Cs$_2$CO$_3$ (123 mg, 377 μmol) in DMF (2.00 mL). The mixture was stirred ~10 min at 25° C. then heated to 100° C. in the Biotage microwave reactor for 30 min. LCMS showed complete reaction, diluted with 10 mL of dichloromethane and filtered through a celite pad, filtrate concentrated under high vacuum at 65° C. and residue dissolved in dichloromethane and purified by chromatography (spherical silica 20-45 μm, 23 g, Versaflash Supelco) eluting with 0 to 5% over 20 min (MeOH containing 10% ammonium hydroxide)/dichloromethane to give N-tert-butyl-2-(1-(3-(3-cyanoazetidin-1-yl)propyl)-5-(difluoromethoxy)-1H-indazol-3-yl)-5-((2-(trimethylsilyl)ethoxy)methyl)-5H-pyrrolo[2,3-b]pyrazine-7-carboxamide (45 mg, 68.9 μmol, 73.2%) as a white solid. MS (M+H)$^+$= 53.1; $^1$H NMR (CDCl$_3$) δ: 9.22 (s, 1H), 8.36 (s, 1H), 8.31 (d, J=2.3 Hz, 1H), 8.04 (s, 1H), 7.58 (d, J=9.1 Hz, 1H), 7.36 (dd, J=8.9, 2.1 Hz, 1H), 6.56 (t, J=73.7 Hz, 1H), 5.75 (s, 2H), 4.57 (t, J=6.6 Hz, 2H), 3.24-3.40 (m, 3H), 2.50 (t, J=6.6 Hz, 2H), 2.08 (quin, J=6.5 Hz, 2H), 1.65 (s, 9H), 0.91-1.03 (m, 2H), 0.00 (s, 9H).

Step 3

2-{1-[3-(3-Cyano-azetidin-1-yl)-propyl]-5-difluoromethoxy-1H-indazol-3-yl}-5H-pyrrolo[2,3-b]pyrazine-7-carboxylic acid tert-butylamide

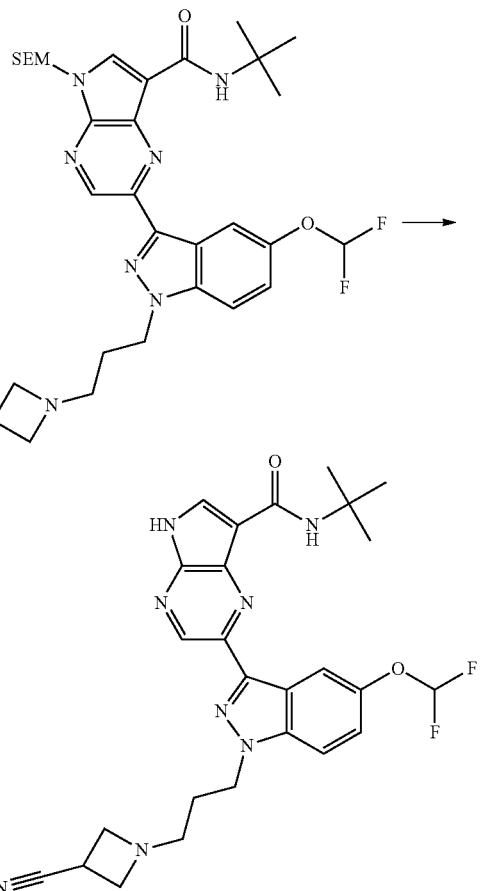

To a pale yellow solution of N-tert-butyl-2-(1-(3-(3-cyanoazetidin-1-yl)propyl)-5-(difluoromethoxy)-1H-indazol-3-yl)-5-((2-(trimethylsilyl)ethoxy)methyl)-5H-pyrrolo[2,3-b]pyrazine-7-carboxamide (45 mg, 68.9 μmol) in dichloromethane (4.00 mL) was added TFA (740 mg, 0.5 mL, 6.49 mmol, Eq: 94.1), the reaction mixture turned orange and was stirred at 25° C. for 18 h, mixture concentrated and the residue was re-dissolved in 5 mL of a solution of (dichloromethane/MeOH/ammonium hydroxide; 60:10:1) and stirred at 25° C. for 1 h, then evaporated to a yellow solid, which was dissolved in dichloromethane (added few drops of MeOH) and purified by chromatography (spherical silica 20-45 μm, 23 g, Versaflash Supelco) eluting with 0 to 5% over 20 min (MeOH containing 10% ammonium hydroxide)/dichloromethane. The pure product dissolved in dichloromethane and cyclohexane added to allow solid formation, light yellow flakes separated by decantation and dried under high vacuum to give N-tert-butyl-2-(1-(3-(3-cyanoazetidin-1-yl)propyl)-5-(difluoromethoxy)-1H-indazol-3-yl)-5H-pyrrolo[2,3-b]pyrazine-7-carboxamide (33 mg, 63.2 μmol, 91.6%). MS (M+H)⁺=523; ¹H NMR (DMSO-d₆) δ: 12.80 (br. s., 1H), 9.06 (s, 1H), 8.37 (s, 1H), 8.19 (d, J=2.3 Hz, 1H), 7.81-7.96 (m, 2H), 7.39 (dd, J=9.1, 2.3 Hz, 1H), 7.19 (t, J=74.4 Hz, 1H), 4.53 (t, J=6.6 Hz, 2H), 3.35-3.57 (m, 3H), 3.16-3.25 (m, 2H), 2.38 (t, J=6.8 Hz, 2H), 1.78-2.02 (m, 2H), 1.49 (s, 9H).

Example 302

2-[1-(2-Azetidin-3-yl-ethyl)-6-fluoro-1H-indazol-3-yl]-5H-pyrrolo[2,3-b]pyrazine-7-carboxylic acid tert-butylamide

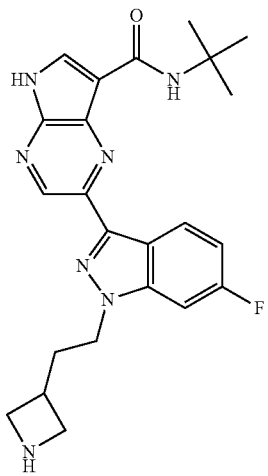 [SMILES: CC(C)(C)NC(=O)c1c[nH]c2ncc(-c3nn(CCC4CNC4)c4cc(F)ccc34)nc12]

Step 1 tert-Butyl 3-(2-hydroxyethyl)azetidine-1-carboxylate

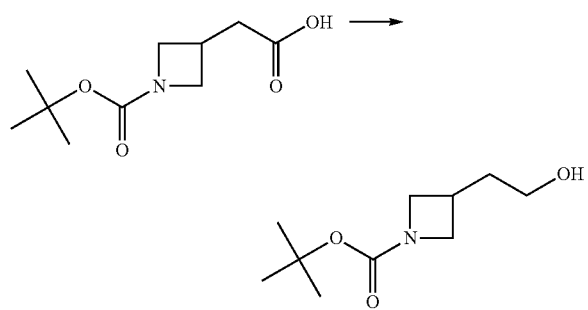

A solution of 2-(1-(tert-butoxycarbonyl)azetidin-3-yl)acetic acid (529 mg, 2.46 mmol) in THF (5.29 mL) was cooled to 0° C. and treated with a borane-methyl sulfide complex 2M in THF (2.46 mL, 4.92 mmol), then slowly warmed to rt. After stirring for 18 h, the reaction mixture was quenched by dropwise addition of 2 N NaOH (7 mL) then extracted with dichloromethane (4×30 mL). The organic layers were combined, dried (MgSO₄), and concentrated to give tert-butyl 3-(2-hydroxyethyl)azetidine-1-carboxylate (495 mg, 2.46 mmol, 100%) as a colorless oil. ¹H NMR (CDCl₃) δ: 3.96 (t, J=8.3 Hz, 2H), 3.47-3.64 (m, 4H), 2.50-2.67 (m, 1H), 1.73-1.86 (m, 2H), 1.37 (s, 9H).

Step 2 tert-Butyl 3-(2-iodoethyl)azetidine-1-carboxylate

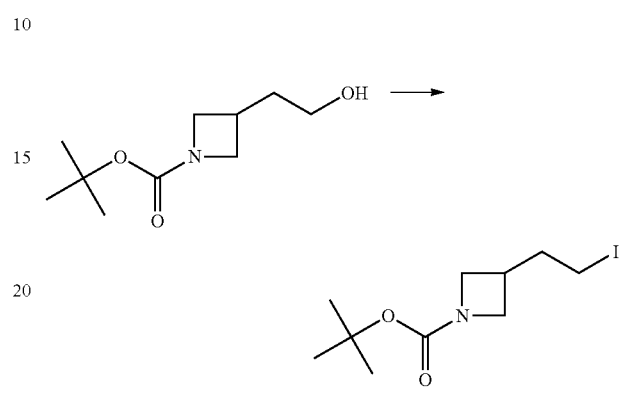

A stirred solution of tert-butyl 3-(2-hydroxyethyl)azetidine-1-carboxylate (254 mg, 1.26 mmol), Ph₃P (381 mg, 1.45 mmol.15), imidazole (129 mg, 1.89 mmol0) and acetonitrile (6.5 mL) at 0° C.; was treated with iodine (368 mg, 1.45 mmol.15). Mixture was allowed to reach 25° C. and stirring continued for 18 h. The reaction mixture was then diluted with water and extracted with hexanes (6×25 mL). The combined organics were dried (MgSO₄) and concentrated, then purified by chromatography (40 g column, 50 μm from Analogix, 0-30% EtOAc in hexanes over 15 min to give tert-butyl 3-(2-iodoethyl)azetidine-1-carboxylate (271 mg, 871 μmol, 69.0%) as a colorless oil. ¹H NMR (CDCl₃) δ: 4.03 (t, J=8.3 Hz, 2H), 3.56 (dd, J=8.7, 5.7 Hz, 2H), 3.10 (t, J=7.0 Hz, 2H), 2.63 (quint, J=7.8, 5.4 Hz, 1H), 2.13 (q, J=7.1 Hz, 2H), 1.42 (s, 9H).

Step 3 tert-Butyl 3-(2-(3-(7-(tert-butylcarbamoyl)-5-((2-(trimethylsilyl)ethoxy)methyl)-5H-pyrrolo[2,3-b]pyrazin-2-yl)-6-fluoro-1H-indazol-1-yl)ethyl)azetidine-1-carboxylate

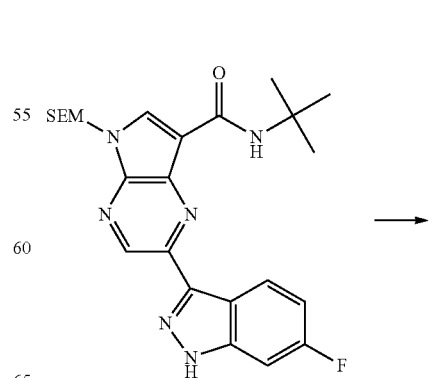

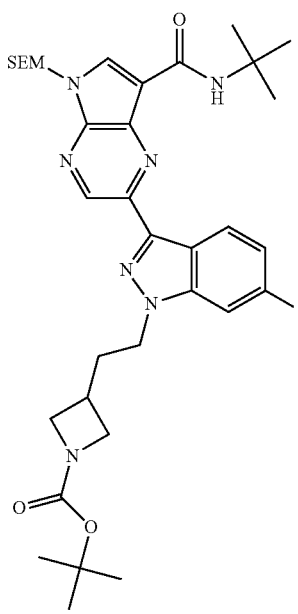

In a 2-5 mL Biotage microwave vial were mixed N-tert-butyl-2-(6-fluoro-1H-indazol-3-yl)-5-((2-(trimethylsilyl)ethoxy)methyl)-5H-pyrrolo[2,3-b]pyrazine-7-carboxamide (75 mg, 155 mmol), tert-butyl 3-(2-iodoethyl)azetidine-1-carboxylate (68 mg, 219 μmol.41) and $Cs_2CO_3$ (203 mg, 622 μmol) in DMF (2.00 mL). The mixture was stirred ~10 min at 25° C. then heated to 100° C. in the Biotage microwave reactor for 30 min, diluted with 10 mL of dichloromethane and filtered through a celite pad, filtrate concentrated under high vacuum at 65° C. and residue dissolved in dichloromethane and purified by chromatography (40 g column, 50 μm silica-gel from Analogix, 0 to 5% over 20 min (MeOH containing 10% ammonium hydroxide)/dichloromethane to give tert-butyl 3-(2-(3-(7-(tert-butylcarbamoyl)-5-((2-(trimethylsilyl)ethoxy)methyl)-5H-pyrrolo[2,3-b]pyrazin-2-yl)-6-fluoro-1H-indazol-1-yl)ethyl)azetidine-1-carboxylate (103 mg, 155 μmol, 99.5%) as a white solid. MS $(M+Na)^+$= 688; $^1H$ NMR $(CDCl_3)$ δ: 9.24 (s, 1H), 8.56 (dd, J=8.7, 5.3 Hz, 1H), 8.37 (s, 1H), 8.09 (s, 1H), 6.98-7.16 (m, 2H), 5.75 (s, 2H), 4.46 (t, J=6.4 Hz, 2H), 4.02 (t, J=8.3 Hz, 2H), 3.49-3.72 (m, 5H), 2.49-2.69 (m, 1H), 2.33 (q, J=6.8 Hz, 2H), 1.65 (s, 9H), 1.48 (s, 2H), 1.45 (s, 9H), 0.92-1.03 (m, 2H), 0.00 (s, 9H); LCMS ESI$^+$ TIC MS showed 100% purity, $[M+Na]^+$= 688.0.

Step 4

2-[1-(2-Azetidin-3-yl-ethyl)-6-fluoro-1H-indazol-3-yl]-5H-pyrrolo[2,3-b]pyrazine-7-carboxylic acid tert-butylamide

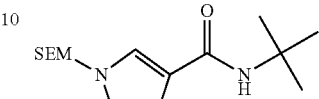

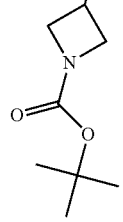

To a pale yellow solution of tert-butyl 3-(2-(3-(7-(tert-butylcarbamoyl)-5-((2-(trimethylsilyl)ethoxy)methyl)-5H-pyrrolo[2,3-b]pyrazin-2-yl)-6-fluoro-1H-indazol-1-yl)ethyl)azetidine-1-carboxylate (43 mg, 64.6 μmol) in dichloromethane (4.00 mL) was added TFA (740 mg, 500 μL, 6.49 mmol00), the reaction mixture turned orange and was stirred at 25° C. for 18 h. The reaction mixture was concentrated and the residue was re-dissolved in 5 mL of a solution of (dichloromethane/MeOH/ammonium hydroxide; 60:10:1) and stirred at 25° C. for 1 h, then evaporated to a yellow solid which was dissolved in dichloromethane (added few drops of MeOH) and purified by chromatography (spherical silica 20-45 μm, 23 g, Versaflash Supelco) eluting with 0 to 10% over 30 min (MeOH containing 10% ammonium hydroxide)/dichloromethane. The pure product dissolved in dichloromethane with few drops of MeOH and cyclohexane added to allow solid formation, off-white solid separated by decantation and dried under high vacuum to give 2-(1-(2-(azetidin-3-yl)ethyl)-6-fluoro-1H-indazol-3-yl)-N-tert-butyl-5H-pyrrolo[2,3-b]pyrazine-7-carboxamide (23 mg, 52.8 μmol, 81.8%). MS (M+H)+=436; ¹H NMR (DMSO-d₆) δ: 9.08 (s, 1H), 8.48 (dd, J=8.7, 5.3 Hz, 1H), 8.39 (s, 1H), 7.90 (s, 1H), 7.77 (dd, J=9.8, 1.9 Hz, 1H), 7.16 (td, J=9.1, 1.9 Hz, 1H), 4.49 (t, J=6.6 Hz, 2H), 3.68-3.85 (m, 2H), 3.44-3.56 (m, 2H), 2.75 (dt, J=15.2, 7.7 Hz, 1H), 2.20 (q, J=6.7 Hz, 2H), 1.51 (s, 9H).

Example 303

N-tert-Butyl-2-(2-Methyl-1H-indol-7-yl)-5H-pyrrolo[2,3-b]pyrazine-7-carboxamide

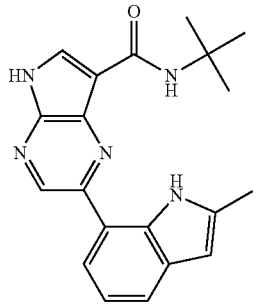 [SMILES: Cc1cc2cccc(-c3cnc4[nH]cc(C(=O)NC(C)(C)C)c4n3)c2[nH]1]

Step 1

2-Methyl-7-(4,4,5,5-tetramethyl-[1,3,2]dioxaborolan-2-yl)-1H indole

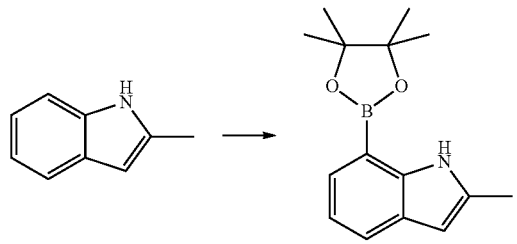

A mixture of 2-methyl-1H-indole (500 mg, 3.81 mmol), 4,4,4',4',5,5,5',5'-octamethyl-2,2'-bi(1,3,2-dioxaborolane) (726 mg, 2.86 mmol) and 4,4'-di-tert-butyl-2,2'-dipyridyl (40.9 mg, 152 μmol) was purged with nitrogen gas for 1 minute, then heptanes (5 mL) were added, the reaction was again purged with nitrogen gas for 1 min, then finally bis(1,5-cyclooctadiene)di-mu-methoxydiiridium(I) (50.5 mg, 76.2 μmol) was added, and the reaction heated to 50° C. After 18 h, the reaction was cooled to room temperature, diluted with ether, washed with water and brine, then dried (MgSO₄), filtered and concentrated in vacuo to give 2-methyl-7-(4,4,5, 5-tetramethyl-[1,3,2]dioxaborolan-2-yl)-1H indole (0.960 g) as a dark oil. This material was used directly in the next step without further purification.

Step 2

N-tert-Butyl-2-(2-Methyl-1H-indol-7-yl)-5-(2-trimethylsilanyl-ethoxymethyl)-5H-pyrrolo[2,3-b]pyrazine-7-carboxamide

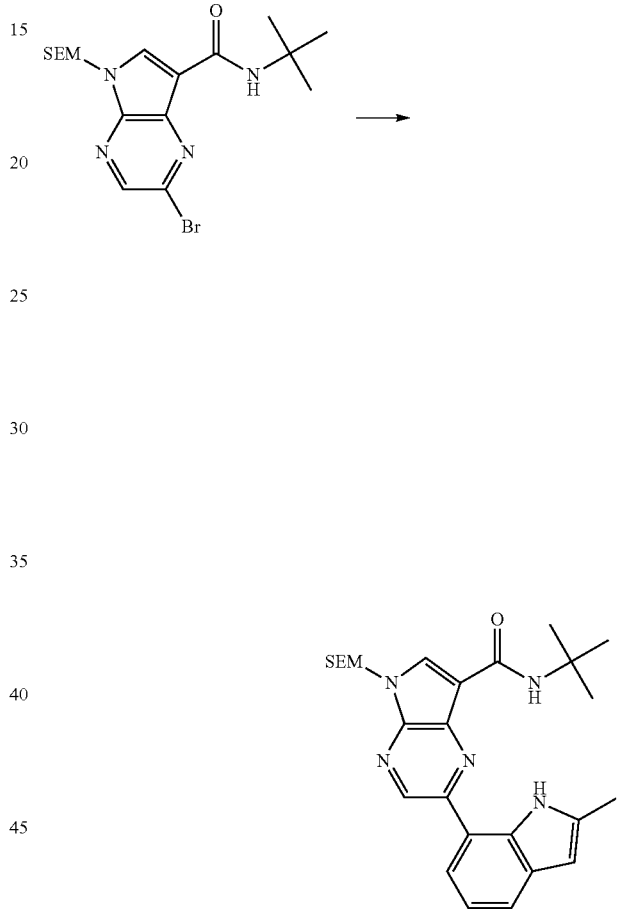

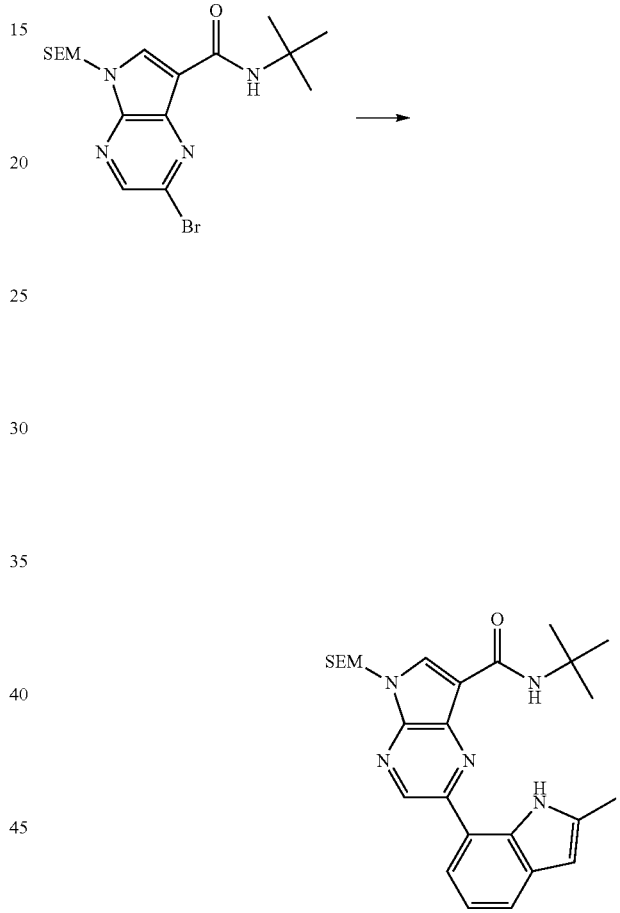

2-Bromo-N-tert-butyl-5-((2-(trimethylsilyl)ethoxy)methyl)-5H-pyrrolo[2,3-b]pyrazine-7-carboxamide (79 mg, 185 μmol), potassium carbonate (51.1 mg, 370 μmol) and 2-methyl-7-(4,4,5,5-tetramethyl-1,3,2-dioxaborolan-2-yl)-1H-indole (95.1 mg, 370 μmol) were dissolved in dioxane (5 mL) and water (0.5 mL), then the reaction was purged with nitrogen for 1 minute. Tetrakis(triphenylphosphine)palladium(0) (21.4 mg, 18.5 μmol) was then added, and the reaction was placed under a nitrogen atmosphere and the mixture heated at to 80° C. for 2 h. Methyl-7-(4,4,5,5-tetramethyl-1,3,2-dioxaborolan-2-yl)-1H-indole (45 mg), was added and the reaction was heated at 80° C. for an additional 2 h. The reaction mixture was cooled, diluted with ethyl acetate/ether (ca 3:1), washed water and brine, dried (MgSO₄), filtered and concentrated in vacuo. The crude residue was purified by chromatography (silica gel, 3-15% ethyl acetate in hexanes) to give N-tert-butyl-2-(2-methyl-1H-indol-7-yl)-5-(2-trimethylsilanyl-ethoxymethyl)-5H-pyrrolo[2,3-b]pyrazine-7-carboxamide (65 mg) as an oil. MS (M+H)⁺=478.3.

Step 3

N-tert-Butyl-2-(2-Methyl-1H-indol-7-yl)-5H-pyrrolo[2,3-b]pyrazine-7-carboxamide

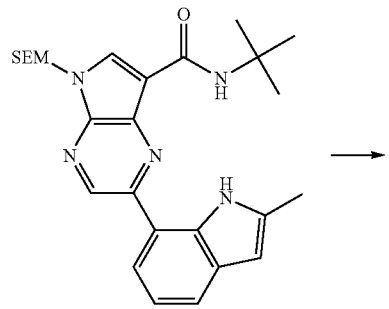

To a stirred solution of N-tert-butyl-2-(2-methyl-1H-indol-7-yl)-5-((2-(trimethylsilyl)ethoxy)methyl)-5H-pyrrolo[2,3-b]pyrazine-7-carboxamide (60 mg, 126 μmol) in DMF (4 mL) was added ethylenediamine (355 mg, 399 μL, 5.9 mmol) then tetrabutylammonium fluoride (389 μL, 389 μmol). The solution was heated to 60° C. with stirring under a nitrogen atmosphere for 20 h. The reaction mixture was cooled, diluted with ether, washed water and brine, then dried (MgSO₄), filtered, and concentrated in vacuo to give an oil which slowly crystallized. The crystals were triturated with water twice then dried under vacuum to give N-tert-butyl-2-(2-Methyl-1H-indol-7-yl)-5H-pyrrolo[2,3-b]pyrazine-7-carboxamide (29 mg) as a yellow solid. MS (M+H)⁺=348.1; ¹H NMR (CDCl₃) δ: 8.87 (s, 1H), 8.35 (d, J=3.0 Hz, 1H), 7.65 (d, J=7.8 Hz, 1H), 7.55-7.61 (m, 1H), 7.20-7.30 (m, 2H), 6.33-6.36 (m, 1H), 2.54 (s, 3H), 1.53 (s, 9H).

Example 304

N-tert-Butyl-2-(2-(1H-Indol-7-yl)-5H-pyrrolo[2,3-b]pyrazine-7-carboxamide

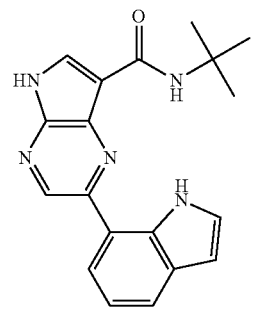 [SMILES: CC(C)(C)NC(=O)c1c[nH]c2ncc(-c3cccc4cc[nH]c34)nc12]

Step 1

N-tert-Butyl-2-(1H-Indol-7-yl)-5-(2-trimethylsilanyl-ethoxymethyl)-5H-pyrrolo[2,3-b]pyrazine-7-carboxamide

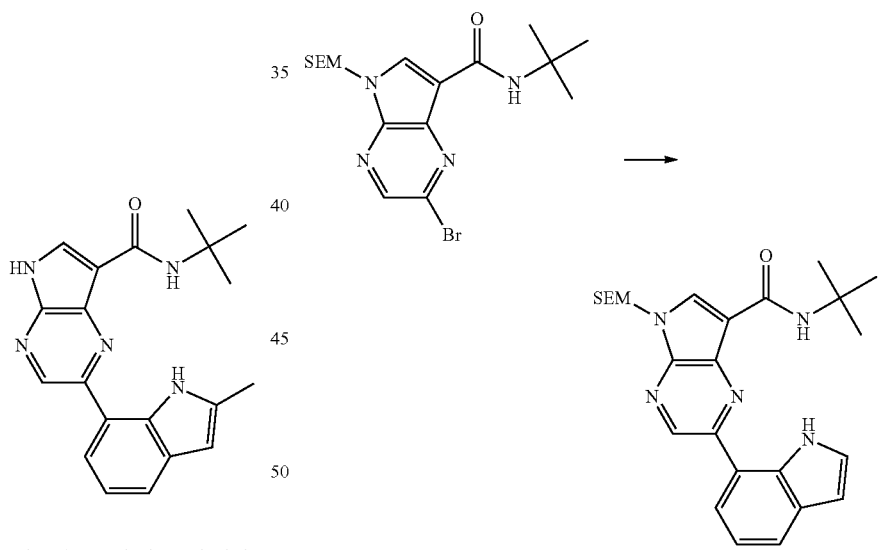

2-Bromo-N-tert-butyl-5-((2-(trimethylsilyl)ethoxy)methyl)-5H-pyrrolo[2,3-b]pyrazine-7-carboxamide (50 mg, 117 μmol), 7-(4,4,5,5-tetramethyl-1,3,2-dioxaborolan-2-yl)-1H-indole (37.0 mg, 152 μmol), potassium carbonate (16.2 mg, 117 μmol) were combined in a reaction tube with a teflon-threaded seal, dioxane (2.5 mL) and water (0.5 mL) were added, then the mixture degassed with nitrogen for 1 min. Tetrakis(triphenylphosphine)palladium(0) (13.5 mg, 11.7 μmol) was added, nitrogen was bubbled through for 1 minute, then the reaction was heated to 85° C. for 6 h, and then at 75° C. for an additional 15 h. The reaction mixture was cooled, concentrated in vacuo, and the residue purified by chromatography (silica, 1-15% ethyl acetate in hexanes) to give N-tert-butyl-2-(1H-indol-7-yl)-5-(2-trimethylsilanyl-ethoxymethyl)-5H-pyrrolo[2,3-b]pyrazine-7-carboxamide (54 mg) as an oil which slowly crystallized. MS (M+H)+= 464.2.

Step 2

N-tert-Butyl-2-(2-(1H-indol-7-yl)-5H-pyrrolo[2,3-b]pyrazine-7-carboxamide

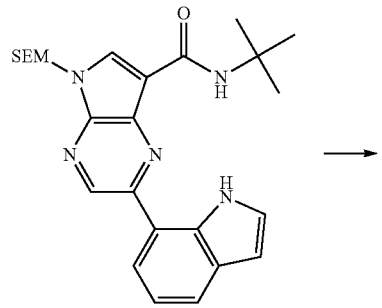

To a stirred solution of N-tert-butyl-2-(1H-indol-7-yl)-5-((2-(trimethylsilyl)ethoxy)methyl)-5H-pyrrolo[2,3-b]pyrazine-7-carboxamide (54 mg, 116 µmol) in DMF (3 mL) was added ethylenediamine (350 mg, 393 µL, 5.82 mmol) and the mixture heated at 60° C. After 72 h, the reaction mixture was cooled, diluted with water, and extracted into ethyl acetate. The organic phases were combined and washed with water and brine then dried (MgSO₄), filtered and concentrated in vacuo. The residue was triturated with ether, then water, diluted with dichloromethane, and finally the solvents removed in vacuo to give N-tert-butyl-2-(1H-indol-7-yl)-5H-pyrrolo[2,3-b]pyrazine-7-carboxamide (14 mg). MS (M+H)+=334.1; ¹H NMR (DMSO-d₆) δ: 12.83 (br. s., 1H), 11.46 (br. s., 1H), 9.01 (s, 1H), 8.49 (s, 1H), 8.24 (s, 1H), 7.81 (d, J=7.8 Hz, 1H), 7.73 (d, J=7.5 Hz, 1H), 7.52 (br. s., 1H), 7.30 (t, J=7.5 Hz, 1H), 6.69 (br. s., 1H), 1.55 (s, 9H).

Example 305

N-tert-Butyl-2-(6-chloro-1-methyl-1H-indazol-3-yl)-5H-pyrrolo[2,3-b]pyrazine-7-carboxamide

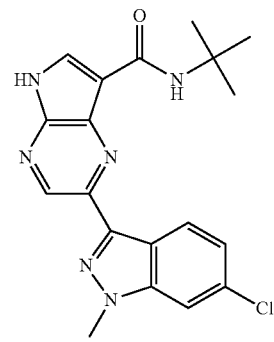 [SMILES: Cn1nc(-c2cnc3[nH]cc(C(=O)NC(C)(C)C)c3n2)c2ccc(Cl)cc21]

Step 1

N-tert-Butyl-2-(6-chloro-1-methyl-1H-indazol-3-yl)-5-((2-(trimethylsilyl)ethoxy)methyl)-5H-pyrrolo[2,3-b]pyrazine-7-carboxamide

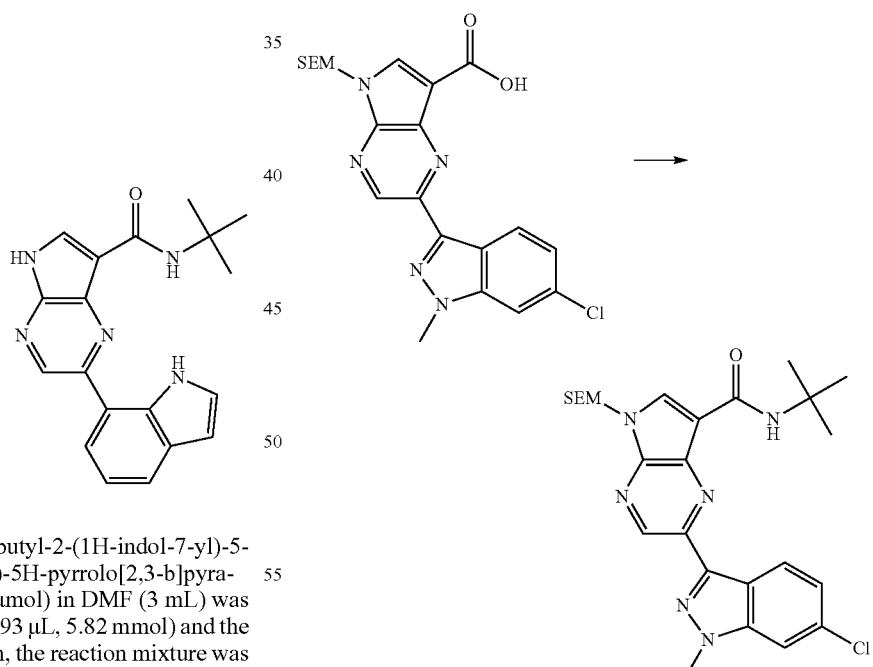

To a stirred suspension of 2-(6-chloro-1-methyl-1H-indazol-3-yl)-5-((2-(trimethylsilyl)ethoxy)methyl)-5H-pyrrolo[2,3-b]pyrazine-7-carboxylic acid (111 mg, 242 µmol) in DMF (4 mL) was added EDC (107 mg, 557 µmol), HOBT (107 mg, 557 µmol) and 2-methylpropan-2-amine (78.6 mg, 0.113 mL, 1.08 mmol) at 20° C. After 3 h the reaction mixture was diluted with ethyl acetate and washed with 10% citric acid solution. The organic layer was then washed with saturated sodium bicarbonate and brine then dried (sodium sulfate), filtered and concentrated in vacuo to give the crude N-tert-butyl-2-(6-chloro-1-methyl-1H-indazol-3-yl)-5-((2-(trimethylsilyl)ethoxy)methyl)-5H-pyrrolo[2,3-b]pyrazine-7-carboxamide (140 mg) as a light brown oil. This was used directly in the next step without further purification.

Step 2

N-tert-Butyl-2-(6-chloro-1-methyl-1H-indazol-3-yl)-5H-pyrrolo[2,3-b]pyrazine-7-carboxamide

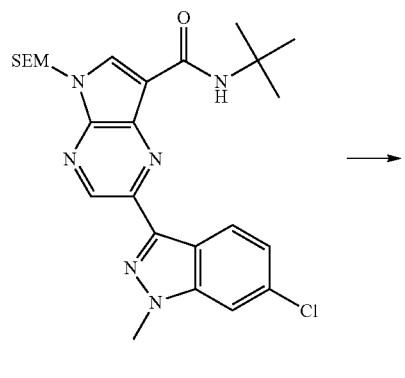

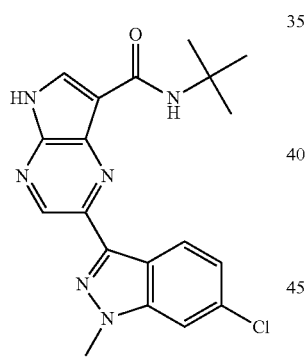

To a stirred solution of N-tert-butyl-2-(6-chloro-1-methyl-1H-indazol-3-yl)-5-((2-(trimethylsilyl)ethoxy)methyl)-5H-pyrrolo[2,3-b]pyrazine-7-carboxamide (140 mg, 273 μmol) in dichloromethane (5 mL) was added trifluoroacetic acid (3.11 g, 2.1 mL, 27.3 mmol) at 20° C. After 6 h, the mixture was concentrated in vacuo. The residue was diluted with dichloromethane and concentrated again. The residue was then suspended in dichloromethane (5 mL) and ethylenediamine (1.23 g, 1.38 mL, 20.5 mmol) added. The mixture was stirred for 15 h, then concentrated in vacuo. The residue was triturated with water and the solid obtained by filtration. Purification by chromatography (silica, 25 g pre-packed SiliCycle cartridge, 0-5% methanol in dichloromethane gradient increasing over 15 min) gave N-tert-butyl-2-(6-chloro-1-methyl-1H-indazol-3-yl)-5H-pyrrolo[2,3-b]pyrazine-7-carboxamide (63 mg, 165 μmol, 60%) as a pale yellow powder. MS (M+Na)$^+$=405; $^1$H NMR (CDCl$_3$) δ: 11.84 (br. s., 1H), 9.05 (s, 1H), 8.38 (d, J=8.7 Hz, 1H), 8.14 (d, J=3.4 Hz, 1H), 7.96 (s, 1H), 7.39 (d, J=1.5 Hz, 1H), 7.08 (dd, J=8.5, 1.7 Hz, 1H), 4.04 (s, 3H), 1.48 (s, 9H).

Example 306

2-(6-Chloro-1H-indazol-3-yl)-N-isopropyl-5H-pyrrolo[2,3-b]pyrazine-7-carboxamide

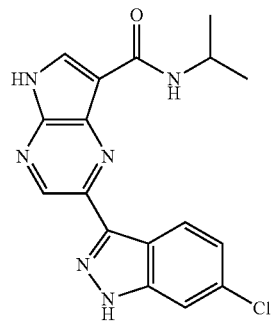 [SMILES: CC(C)NC(=O)c1c[nH]c2ncc(-c3n[nH]c4cc(Cl)ccc34)nc12]

Step 1

6-Chloro-3-tributylstannanyl-1H-indazole

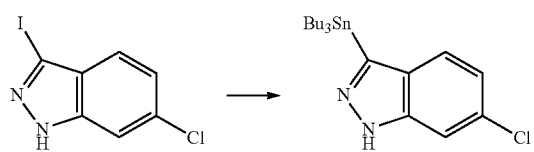

To a stirred solution of 6-chloro-3-iodo-1H-indazole (1.11 g, 4.0 mmol) in THF (25 mL) was added sodium hydride (192 mg, 4.8 mmol). After 15 min the mixture was cooled to −16° C. Isopropylmagnesium chloride (3.00 mL, 6.00 mmol) was added dropwise and the mixture stirred at −16° C. for 2 h. Tributyltin chloride (1.56 g, 1.3 mL, 4.8 mmol) was then added and the reaction mixture warmed to room temperature. After 15 h the mixture was diluted with water and ethyl acetate. The organic layer was washed with brine, dried (sodium sulfate) filtered and concentrated in vacuo. The crude brown oil was used directly in the next step without further purification.

Step 2

2-(6-Chloro-1H-indazol-3-yl)-N-isopropyl-5-((2-(trimethylsilyl)ethoxy)methyl)-5H-pyrrolo[2,3-b]pyrazine-7-carboxamide

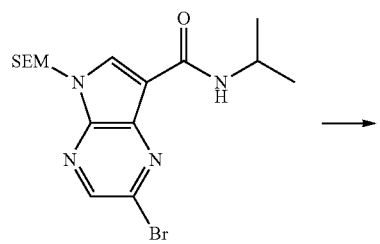

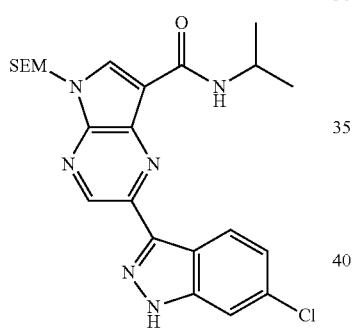

To a stirred solution of 2-bromo-N-isopropyl-5-((2-(trimethylsilyl)ethoxy)methyl)-5H-pyrrolo[2,3-b]pyrazine-7-carboxamide (289 mg, 700 μmol) and 6-chloro-3-(tributylstannyl)-1H-indazole (see Example 4, 2.01 g, 4.55 mmol) in DMF at 20° C. was added copper(I) iodide (25.1 mg, 280 μmol) and then the mixture degassed with bubbling Argon for 15 min. Tetrakis(triphenylphosphine)palladium(0) (80.9 mg, 70.0 μmol) was added then the reaction mixture was heated to 80° C. After 15 h the mixture was cooled and diluted with ethyl acetate and saturated aqueous saturated ammonium chloride solution. The organic layer was separated and washed with brine, then dried (sodium sulfate), filtered and concentrated in vacuo. The residue was purified by chromatography (silica, 40 g Analogix column, 20-50% ethyl acetate in hexanes, gradient over 15 min) to give 2-(6-chloro-1H-indazol-3-yl)-N-isopropyl-5-((2-(trimethylsilyl)ethoxy)methyl)-5H-pyrrolo[2,3-b]pyrazine-7-carboxamide (0.080 g) as a light brown oil. This was approximately 75% pure by $^1$H NMR with a single, major impurity tentatively assigned as 6,6'-dichloro-1H,1'H-[3,3']biindazolyl and was used directly in the next step without further purification. MS (M−H)$^−$=483; $^1$H NMR (CDCl$_3$) δ: 8.41 (s, 1H), 8.35 (s, 1H), 8.07 (br. s, 1H), 7.64-7.77 (m, 2H), 7.52 (s, 1H), 7.16 (d, J=8.7 Hz, 1H), 5.64 (s, 2H), 4.23-4.47 (m, 1H), 3.45-3.58 (m, 2H), 1.34 (d, J=6.4 Hz, 6H), 0.93 (s, 2H), −0.05 (s, 9H)

Step 3

2-(6-Chloro-1H-indazol-3-yl)-N-isopropyl-5H-pyrrolo[2,3-b]pyrazine-7-carboxamide

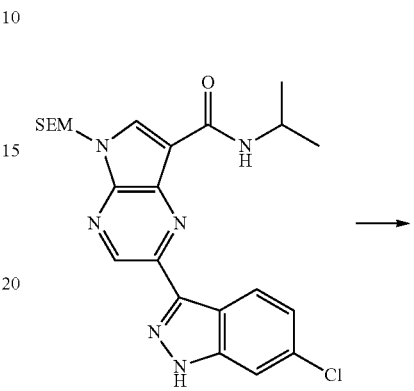

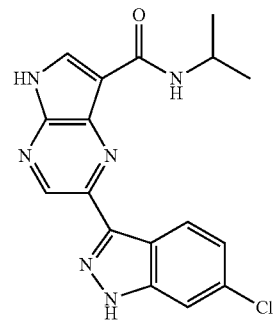

To a stirred solution of 2-(6-chloro-1H-indazol-3-yl)-N-isopropyl-5-((2-(trimethylsilyl)ethoxy)methyl)-5H-pyrrolo[2,3-b]pyrazine-7-carboxamide (0.080 g, 165 μmol) in dichloromethane (2 mL) was added trifluoroacetic acid (1.88 g, 1.27 mL, 16.5 mmol). The reaction mixture was stirred for 4 h, then was concentrated in vacuo. The residue was diluted with dichloromethane and concentrated in vacuo again, then was suspended in dichloromethane and ethylenediamine (743 mg, 0.835 mL, 12.4 mmol) added. After 15 h the mixture was concentrated, triturated with water and the solid obtained by filtration was dried and purified by chromatography (silica, SiliCycle 25 g cartridge, 0-5% methanol in dichloromethane, gradient over 15 min) to give 2-(6-chloro-1H-indazol-3-yl)-N-isopropyl-5H-pyrrolo[2,3-b]pyrazine-7-carboxamide (24 mg, 67.0 μmol, 41%) as a pale yellow powder. MS (M+Na)$^+$= 377; $^1$H NMR (DMSO-d$_6$) δ: 13.16 (br. s, 1H), 12.39 (br. s, 1H), 9.12 (s, 1H), 8.39 (d, J=8.7 Hz, 1H), 8.17 (d, J=2.6 Hz, 1H), 8.10 (d, J=7.9 Hz, 1H), 7.53 (s, 1H), 7.09 (dd, J=9.1, 1.0 Hz, 1H), 4.18-4.41 (m, 1H), 1.31 (d, J=6.4 Hz, 6H)

Example 307

2-(6-Chloro-1-ethyl-1H-indazol-3-yl)-N-isopropyl-5H-pyrrolo[2,3-b]pyrazine-7-carboxamide

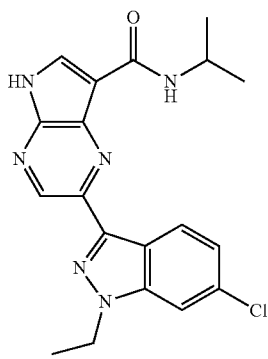 [SMILES: CCn1nc(-c2cnc3[nH]cc(C(=O)NC(C)C)c3n2)c2ccc(Cl)cc21]

Step 1

2-(6-Chloro-1-ethyl-1H-indazol-3-yl)-N-isopropyl-5-((2-(trimethylsilyl)ethoxy)methyl)-5H-pyrrolo[2,3-b]pyrazine-7-carboxamide

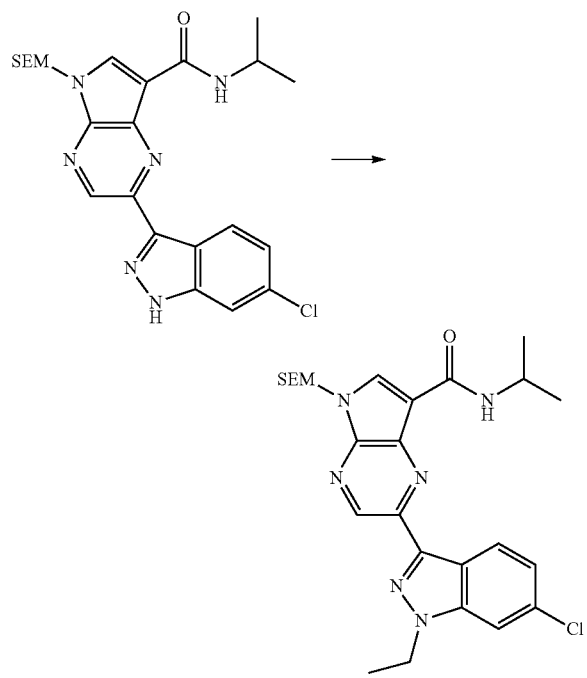

2-(6-Chloro-1H-indazol-3-yl)-N-isopropyl-5-((2-(trimethylsilyl)ethoxy)methyl)-5H-pyrrolo[2,3-b]pyrazine-7-carboxamide (120 mg, 247 μmol) was dissolved in DMF (1 mL) and cooled to 0° C. Sodium hydride (12.9 mg, 322 μmol) was added and the mixture was allowed to stir for 30 min at 0° C. Ethyl iodide (57.9 mg, 30.0 μL, 371 μmol) was added and the mixture was warmed to 20° C. After 15 h the mixture was diluted with water and extracted with ethyl acetate. The organic extracts were washed with brine, dried over anhydrous sodium sulfate and concentrated in vacuo. The residue was purified by chromatography (silica, 40 g Analogix prepacked column, 20-50% ethyl acetate in hexanes, 15 minute gradient) to give 2-(6-chloro-1-ethyl-1H-indazol-3-yl)-N-isopropyl-5-((2-(trimethylsilyl)ethoxy)methyl)-5H-pyrrolo[2,3-b]pyrazine-7-carboxamide (78 mg, 152 μmol, 61%) as a yellow powder. MS (M+Na)$^+$=535; $^1$H NMR (CDCl$_3$) δ: 9.26 (s, 1H), 8.44-8.49 (m, 1H), 8.39-8.42 (m, 1H), 8.20-8.28 (m, 1H), 7.47-7.56 (m, 1H), 7.23 (d, J=1.5 Hz, 1H), 5.67-5.77 (m, 2H), 4.43-4.59 (m, 1H), 4.13 (q, J=7.2 Hz, 1H), 3.52-3.67 (m, 1H), 1.57-1.65 (m, 4H), 1.42 (d, J=6.4 Hz, 4H), 0.88-1.01 (m, 2H)

Step 2

2-(6-Chloro-1-ethyl-1H-indazol-3-yl)-N-isopropyl-5H-pyrrolo[2,3-b]pyrazine-7-carboxamide

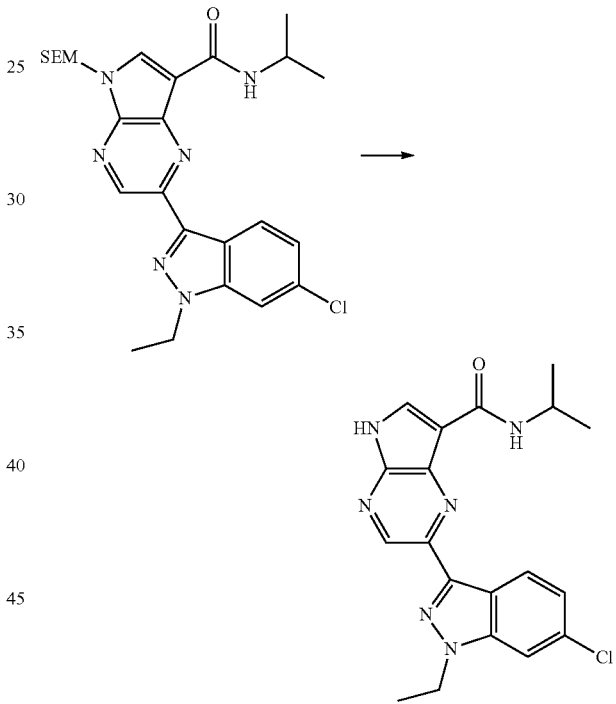

2-(6-Chloro-1-ethyl-1H-indazol-3-yl)-N-isopropyl-5-((2-(trimethylsilyl)ethoxy)methyl)-5H-pyrrolo[2,3-b]pyrazine-7-carboxamide (78 mg, 152 μmol) was dissolved in dichloromethane and to this was added trifluoroacetic acid (1.73 g, 1.17 mL, 15.2 mmol). The mixture was stirred for 4 h then concentrated en vacuo. The residue was diluted in dichloromethane and re-concentrated, and finally diluted again in dichloromethane and to this was added ethylenediamine (685 mg, 770 μL, 11.4 mmol). After 15 h the mixture was concentrated in vacuo, triturated with water and the collected solid was filtered and dried. The solid was purified by chromatography (Silica, SiliCycle 25 g cartridge, 0-5% methanol in dichloromethane, 15 min gradient) to give 2-(6-chloro-1-ethyl-1H-indazol-3-yl)-N-isopropyl-5H-pyrrolo[2,3-b]pyrazine-7-carboxamide (53 mg, 138 μmol, 91.1%) as a pale yellow powder. MS (M+H)$^+$=383; $^1$H NMR (CDCl$_3$) δ: 11.74 (br. s., 1H), 9.11-9.15 (m, 1H), 8.41 (d, J=8.7 Hz, 1H), 8.20 (d, J=3.0 Hz, 1H), 8.14 (d, J=7.9 Hz, 1H), 7.44 (s, 1H), 7.15 (dd, J=8.5, 1.3 Hz, 1H), 4.28-4.48 (m, 3H), 1.53 (t, J=7.2 Hz, 3H), 1.33 (d, J=6.4 Hz, 6H)

Example 308

2-(1-Benzyl-6-chloro-1H-indazol-3-yl)-N-isopropyl-5H-pyrrolo[2,3-b]pyrazine-7-carboxamide

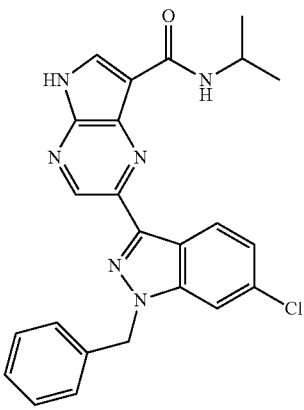 [SMILES: CC(C)NC(=O)c1c[nH]c2ncc(-c3nn(Cc4ccccc4)c4cc(Cl)ccc34)nc12]

Step 1

2-(1-Benzyl-6-chloro-1H-indazol-3-yl)-N-isopropyl-5-((2-(trimethylsilyl)ethoxy)methyl)-5H-pyrrolo[2,3-b]pyrazine-7-carboxamide

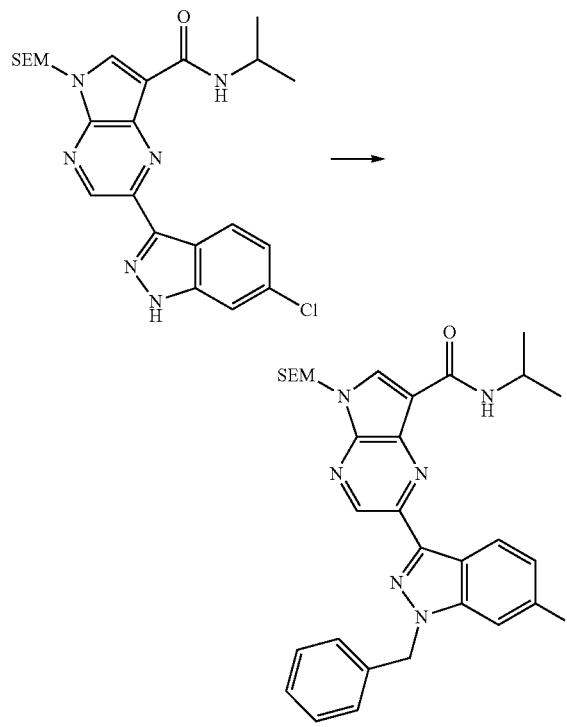

2-(6-Chloro-1H-indazol-3-yl)-N-isopropyl-5-((2-(trimethylsilyl)methyl)-5H-pyrrolo[2,3-b]pyrazine-7-carboxamide (120 mg, 247 µmol) was dissolved in DMF (1 mL) and cooled to 0° C. Sodium hydride (12.9 mg, 322 µmol) was added and the mixture was stirred for 30 min. Benzyl bromide (63.5 mg, 44.1 µL, 371 µmol) was added and the mixture was warmed to 20° C. After 15 h the mixture was diluted with water and extracted with ethyl acetate. The organic extracts were washed with brine, dried over anhydrous sodium sulfate and concentrated in vacuo. The residue was purified by chromatography (silica, 40 g Analogix column, 20-50% ethyl acetate in hexanes, 15 min gradient) to give 2-(1-benzyl-6-chloro-1H-indazol-3-yl)-N-isopropyl-5-((2-(trimethylsilyl)ethoxy)methyl)-5H-pyrrolo[2,3-b]pyrazine-7-carboxamide (87 mg, 151 µmol, 61.1%) as a pale yellow powder. $^1$H NMR (CDCl$_3$) δ: 9.29 (s, 1H), 8.48 (d, J=8.7 Hz, 1H), 8.38 (s, 1H), 8.20 (d, J=7.9 Hz, 1H), 7.43 (d, J=1.5 Hz, 1H), 7.20-7.39 (m, 6H), 5.73 (s, 2H), 5.68 (s, 2H), 4.38-4.55 (m, 1H), 3.52-3.64 (m, 2H), 1.42 (d, J=6.4 Hz, 6H), 0.86-1.00 (m, 2H), −0.03 (s, 9H).

Step 2

2-(1-Benzyl-6-chloro-1H-indazol-3-yl)-N-isopropyl-5H-pyrrolo[2,3-b]pyrazine-7-carboxamide

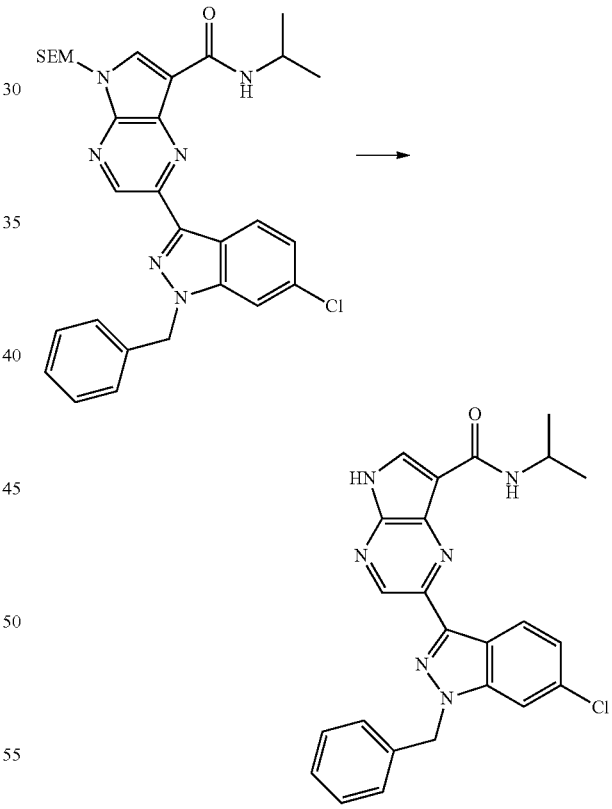

2-(1-Benzyl-6-chloro-1H-indazol-3-yl)-N-isopropyl-5-((2-(trimethylsilyl)ethoxy)methyl)-5H-pyrrolo[2,3-b]pyrazine-7-carboxamide (87 mg, 151 µmol) was dissolved in dichloromethane (25 mL) and to this was added trifluoroacetic acid (1.72 g, 1.17 mL, 15.1 mmol). The mixture was stirred for 4 h then concentrated in vacuo. The residue was diluted in dichloromethane and re-concentrated again, then suspended in dichloromethane and ethylenediamine (682 mg, 0.766 mL, 11.3 mmol) added. The mixture was stirred for 15 h then concentrated in vacuo. The residue was triturated with water and the solid collected by filtration and dried. The solid was adsorbed onto silica gel and purified by chromatography (silica, SiliCycle 25 g cartridge, 0-5% methanol in dichloromethane, 15 min gradient) to give 2-(1-benzyl-6-chloro-1H-indazol-3-yl)-N-isopropyl-5H-pyrrolo[2,3-b]pyrazine-7-carboxamide (78 mg, 175 μmol, quantitative) as a pale yellow powder. MS (M−H)⁻=443; ¹H NMR (DMSO-d₆) δ: 12.84 (br. s., 1H), 9.05-9.13 (m, 1H), 8.37-8.50 (m, 2H), 8.08 (d, J=1.1 Hz, 1H), 8.01 (d, J=7.6 Hz, 1H), 7.23-7.38 (m, 6H), 5.79 (s, 2H), 4.20 (dq, J=13.6, 6.7 Hz, 1H), 1.30 (d, J=6.4 Hz, 6H).

Example 309

2-(6-Chloro-1-(cyclopropylmethyl)-1H-indazol-3-yl)-N-isopropyl-5H-pyrrolo[2,3-b]pyrazine-7-carboxamide

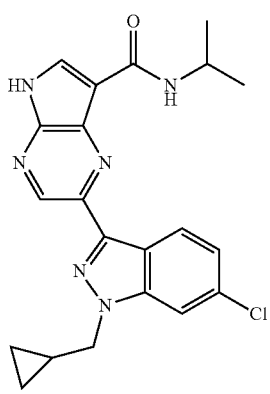

Step 1

2-(6-Chloro-1-(cyclopropylmethyl)-1H-indazol-3-yl)-N-isopropyl-5-((2-(trimethylsilyl)ethoxy)methyl)-5H-pyrrolo[2,3-b]pyrazine-7-carboxamide

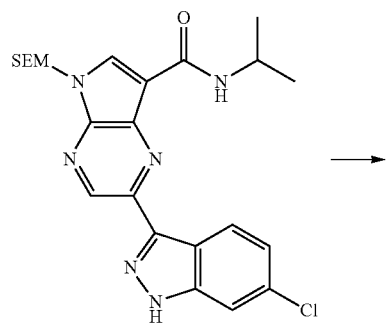

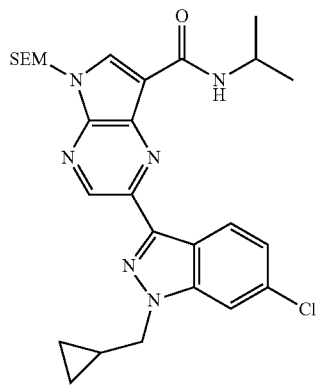

2-(6-Chloro-1H-indazol-3-yl)-N-isopropyl-5-((2-(trimethylsilyl)ethoxy)methyl)-5H-pyrrolo[2,3-b]pyrazine-7-carboxamide (120 mg, 247 μmol) was dissolved in DMF (1 mL) and cooled to 0° C. Sodium hydride (12.9 mg, 322 μmol) was added. After 30 min cyclopropylmethyl bromide (50.1 mg, 0.0360 mL, 371 μmol) was added and the mixture warmed to room temperature. After 15 h, the mixture was diluted with water and extracted with ethyl acetate. The organic extracts were washed with brine, dried over anhydrous sodium sulfate and concentrated in vacuo. The residue was purified by chromatography (silica, 40 g Analogix column, 20-50% ethyl acetate in hexanes, 15 min gradient) to give 2-(6-chloro-1-(cyclopropylmethyl)-1H-indazol-3-yl)-N-isopropyl-5-((2-(trimethylsilyl)ethoxy)methyl)-5H-pyrrolo[2,3-b]pyrazine-7-carboxamide (99 mg, 184 μmol, 74.2%) as a yellow powder. ¹H NMR (CDCl₃) δ: 9.27 (s, 1H), 8.43-8.50 (m, 2H), 8.31 (d, J=8.3 Hz, 1H), 7.54 (s, 1H), 7.23 (s, 1H), 5.73 (s, 2H), 4.40-4.56 (m, 1H), 4.35 (d, J=6.8 Hz, 2H), 3.54-3.64 (m, 2H), 1.42 (d, J=6.4 Hz, 7H), 0.89-1.00 (m, 2H), 0.62-0.71 (m, 2H), 0.51 (q, J=4.9 Hz, 2H), −0.07-−0.01 (m, 9H)

Step 2

2-(6-Chloro-1-(cyclopropylmethyl)-1H-indazol-3-yl)-N-isopropyl-5H-pyrrolo[2,3-b]pyrazine-7-carboxamide

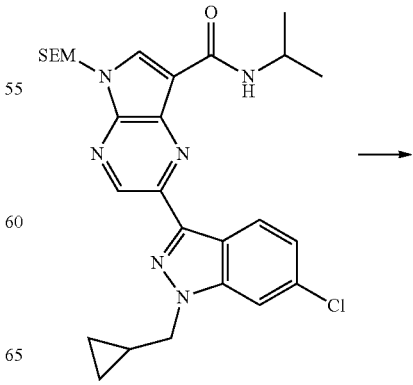

1021 -continued

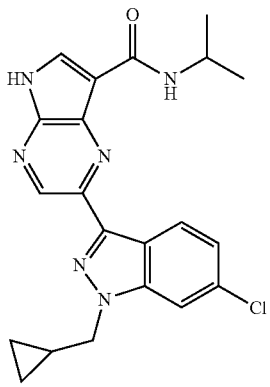 [SMILES: CC(C)NC(=O)c1c[nH]c2ncc(-c3nn(CC4CC4)c4cc(Cl)ccc34)nc12]

2-(6-Chloro-1-(cyclopropylmethyl)-1H-indazol-3-yl)-N-isopropyl-5-((2-(trimethylsilyl)ethoxy)methyl)-5H-pyrrolo[2,3-b]pyrazine-7-carboxamide (99 mg, 184 µmol) was dissolved in dichloromethane and to this was added trifluoroacetic acid (1.73 g, 1.17 mL, 15.2 mmol). After 72 h the mixture was concentrated in vacuo, the residue diluted in dichloromethane, and then and re-concentrated in vacuo. Purification by chromatography (silica, Analogix 40 g cartridge, 0-5% methanol in dichloromethane, gradient over 15 min) gave 2-(6-chloro-1-(cyclopropylmethyl)-1H-indazol-3-yl)-N-isopropyl-5H-pyrrolo[2,3-b]pyrazine-7-carboxamide (15 mg, 36.7 µmol, 20.0%) as an off-white powder. MS (M+Na)$^+$=431; $^1$H NMR (CDCl$_3$) δ: 9.67 (br. s., 1H), 9.19-9.31 (m, 1H), 8.46 (d, J=8.7 Hz, 1H), 8.38 (d, J=3.0 Hz, 1H), 8.25 (d, J=7.9 Hz, 1H), 7.53 (d, J=1.1 Hz, 1H), 7.21-7.26 (m, 1H), 4.41-4.55 (m, 1H), 4.34 (d, J=7.2 Hz, 2H), 1.43 (d, J=6.4 Hz, 6H), 1.04-1.21 (m, 1H), 0.62-0.71 (m, 2H), 0.51 (q, J=4.9 Hz, 2H).

Example 310

2-(6-Chloro-1-(isoxazol-3-ylmethyl)-1H-indazol-3-yl)-N-isopropyl-5H-pyrrolo[2,3-b]pyrazine-7-carboxamide

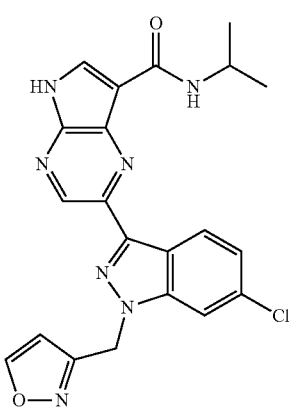 [SMILES: CC(C)NC(=O)c1c[nH]c2ncc(-c3nn(Cc4ccon4)c4cc(Cl)ccc34)nc12]

Step 1

2-(6-Chloro-1-(isoxazol-3-ylmethyl)-1H-indazol-3-yl)-N-isopropyl-5-((2-(trimethylsilyl)ethoxy)methyl)-5H-pyrrolo[2,3-b]pyrazine-7-carboxamide

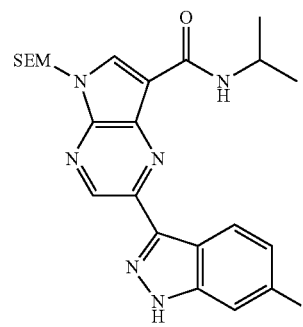

2-(6-Chloro-1H-indazol-3-yl)-N-isopropyl-5-((2-(trimethylsilyl)ethoxy)methyl)-5H-pyrrolo[2,3-b]pyrazine-7-carboxamide (80 mg, 165 µmol) was dissolved in DMF (1 mL) and cooled to 0° C. Sodium hydride (10.6 mg, 264 µmol) was added and the mixture was stirred for 30 min at 0° C. 3-(Bromomethyl)isoxazole (29.4 mg, 181 µmol) was added and the mixture warmed to room temperature. After 15 h, the mixture was diluted with water and extracted with ethyl acetate. The organic extracts were washed with brine, dried over anhydrous sodium sulfate and concentrated in vacuo. Purification by chromatography (silica, 24 g Analogix column, 20-50% ethyl acetate in hexanes, 15 min gradient) gave 2-(6-chloro-1-(isoxazol-3-ylmethyl)-1H-indazol-3-yl)-N-isopropyl-5-((2-(trimethylsilyl)ethoxy)methyl)-5H-pyrrolo[2,3-b]pyrazine-7-carboxamide (91 mg, 161 µmol, 97.5%) as a yellow powder. MS (M+Na)$^+$=588 (88% purity); $^1$H NMR (CDCl$_3$) δ: 9.27 (s, 1H), 8.47 (d, J=8.7 Hz, 1H), 8.34-8.43 (m, 2H), 8.16 (d, J=8.3 Hz, 1H), 8.03 (s, 1H), 7.57 (s, 1H), 6.33 (d, J=1.5 Hz, 1H), 5.77 (s, 2H), 5.73 (s, 2H), 4.38-4.56 (m, 1H), 3.53-3.65 (m, 2H), 1.35-1.46 (m, 6H), 0.89-1.01 (m, 2H), −0.07-0.02 (m, 9H)

Step 2

2-(6-Chloro-1-(isoxazol-3-ylmethyl)-1H-indazol-3-yl)-N-isopropyl-5H-pyrrolo[2,3-b]pyrazine-7-carboxamide

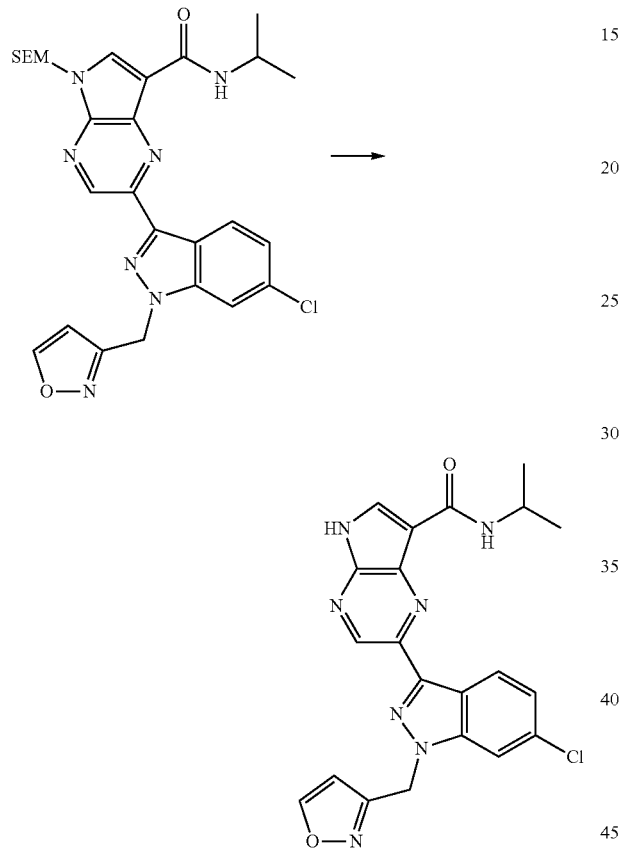

2-(6-Chloro-1-(isoxazol-3-ylmethyl)-1H-indazol-3-yl)-N-isopropyl-5-((2-(trimethylsilyl)ethoxy)methyl)-5H-pyrrolo[2,3-b]pyrazine-7-carboxamide was dissolved in dichloromethane and to this was added trifluoroacetic acid (1.79 g, 1.21 mL, 15.7 mmol). The mixture was stirred for 120 h. A precipitate had formed which was filtered off. The filtrates were concentrated in vacuo and combined with the solid to give intermediate 2-(6-chloro-1-(isoxazol-3-ylmethyl)-1H-indazol-3-yl)-5-(hydroxymethyl)-N-isopropyl-5H-pyrrolo[2,3-b]pyrazine-7-carboxamide (73 mg, 157 μmol). This was dissolved in 60:20:1 dichloromethane:methanol:ammonium hydroxide (10 mL), and the mixture was stirred for 2 h. The mixture was concentrated in vacuo, diluted with dichloromethane and reconcentrated to give 2-(6-chloro-1-(isoxazol-3-ylmethyl)-1H-indazol-3-yl)-N-isopropyl-5H-pyrrolo[2,3-b]pyrazine-7-carboxamide (67 mg, 154 μmol, 98.1%) as a white solid. MS (M+Na)$^+$=458; $^1$H NMR (CDCl$_3$) δ: 11.97 (br. s., 1H), 9.08 (s, 1H), 8.36 (d, J=8.3 Hz, 1H), 8.29 (d, J=1.5 Hz, 1H), 8.16 (d, J=3.0 Hz, 1H), 7.98-8.07 (m, 1H), 7.46 (s, 1H), 7.12 (dd, J=8.5, 1.3 Hz, 1H), 6.21 (d, J=1.5 Hz, 1H), 5.64 (s, 2H), 4.23-4.39 (m, 1H), 1.20-1.32 (m, 6H).

Example 311

2-(6-Chloro-1-((1-methyl-1H-imidazol-2-yl)methyl)-1H-indazol-3-yl)-N-isopropyl-5H-pyrrolo[2,3-b]pyrazine-7-carboxamide

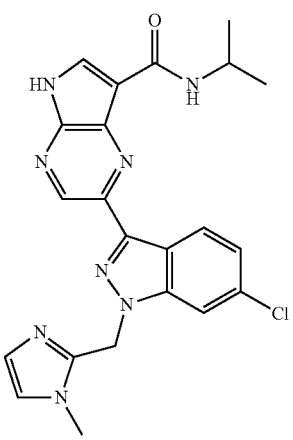 [SMILES: CC(C)NC(=O)c1c[nH]c2ncc(-c3nn(Cc4nccn4C)c4cc(Cl)ccc34)nc12]

Step 1

2-(6-Chloro-1-((1-methyl-1H-imidazol-2-yl)methyl)-1H-indazol-3-yl)-N-isopropyl-5-((2-(trimethylsilyl)ethoxy)methyl)-5H-pyrrolo[2,3-b]pyrazine-7-carboxamide

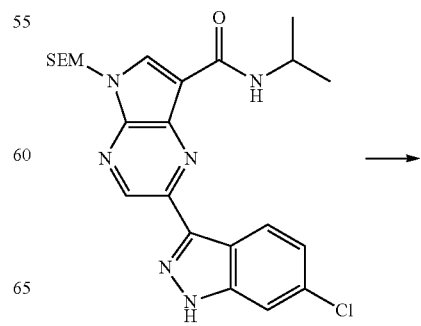

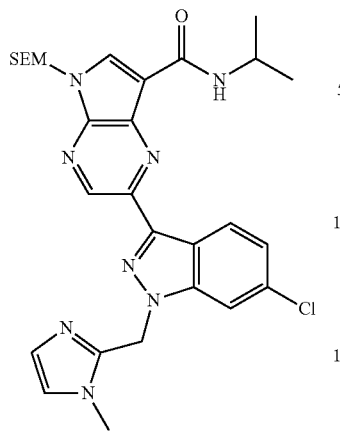

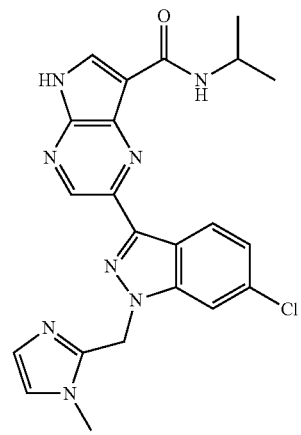

2-(6-Chloro-1H-indazol-3-yl)-N-isopropyl-5-((2-(trimethylsilyl)ethoxy)methyl)-5H-pyrrolo[2,3-b]pyrazine-7-carboxamide (80 mg, 165 µmol) was dissolved in DMF (1 mL) and cooled to 0° C. Sodium hydride (10.6 mg, 264 µmol) was added and the mixture was stirred for 30 min. 2-(Chloromethyl)-1-methyl-1H-imidazole (23.7 mg, 181 µmol) was added and the mixture warmed to room temperature. After 15 h the mixture was diluted with water and extracted with ethyl acetate. The organic extracts were washed with brine, dried over anhydrous sodium sulfate and concentrated in vacuo. The residue was purified by chromatography (silica, 24 g Analogix column, dichloromethane) to give 2-(6-chloro-1-((1-methyl-1H-imidazol-2-yl)methyl)-1H-indazol-3-yl)-N-isopropyl-5-((2-(trimethylsilyl)ethoxy)methyl)-5H-pyrrolo[2,3-b]pyrazine-7-carboxamide (106 mg) as a yellow solid. MS (M+H)$^+$=579.

Step 2

2-(6-Chloro-1-((1-methyl-1H-imidazol-2-yl)methyl)-1H-indazol-3-yl)-N-isopropyl-5H-pyrrolo[2,3-b]pyrazine-7-carboxamide

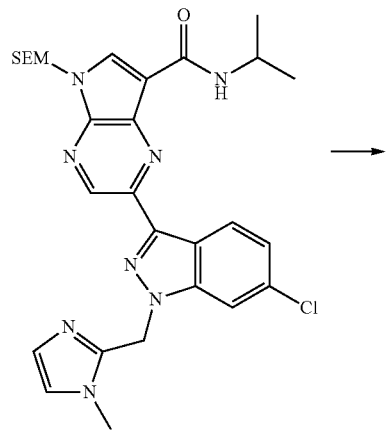

2-(6-Chloro-1-((1-methyl-1H-imidazol-2-yl)methyl)-1H-indazol-3-yl)-N-isopropyl-5-((2-(trimethylsilyl)ethoxy)methyl)-5H-pyrrolo[2,3-b]pyrazine-7-carboxamide (106 mg, 183 µmol) was dissolved in dichloroethane (10 mL). To this mixture was added trifluoroacetic acid (2.09 g, 1.41 mL, 18.3 mmol) and the mixture was heated to 80° C. After 15 h, the mixture was concentrated in vacuo. The residue was dissolved in 60:20:1 dichloromethane:methanol:ammonium hydroxide (10 mL). After 2 h the mixture was concentrated in vacuo, then purified by chromatography (silica, Analogix 40 g, 0-5% methanol in dichloromethane, over 15 min) to give 2-(6-chloro-1-((1-methyl-1H-imidazol-2-yl)methyl)-1H-indazol-3-yl)-N-isopropyl-5H-pyrrolo[2,3-b]pyrazine-7-carboxamide (87 mg, 194 µmol, 106%) as a yellow powder. MS (M+H)$^+$=449; $^1$H NMR (CDCl$_3$) δ: 11.90-12.06 (m, 1H), 8.97-9.07 (m, 1H), 8.27-8.35 (m, 1H), 8.11-8.17 (m, 1H), 7.95-8.05 (m, 1H), 7.72-7.82 (m, 1H), 7.05-7.13 (m, 1H), 6.94-7.03 (m, 1H), 6.81-6.92 (m, 1H), 5.69-5.83 (m, 2H), 4.17-4.38 (m, 1H), 3.72 (s, 3H), 1.24 (d, J=6.4 Hz, 6H).

Example 312

2-(6-Chloro-1-((5-methylisoxazol-3-yl)methyl)-1H-indazol-3-yl)-N-isopropyl-5H-pyrrolo[2,3-b]pyrazine-7-carboxamide

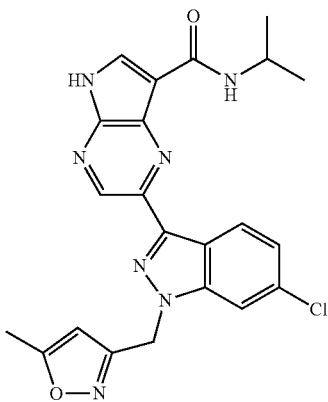 [SMILES: Cc1cc(Cn2nc(-c3cnc4[nH]cc(C(=O)NC(C)C)c4n3)c3ccc(Cl)cc32)no1]

Step 1

2-(6-Chloro-1-((5-methylisoxazol-3-yl)methyl)-1H-indazol-3-yl)-N-isopropyl-5-((2-(trimethylsilyl)ethoxy)methyl)-5H-pyrrolo[2,3-b]pyrazine-7-carboxamide

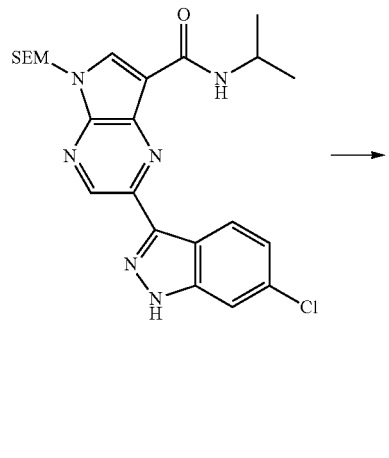

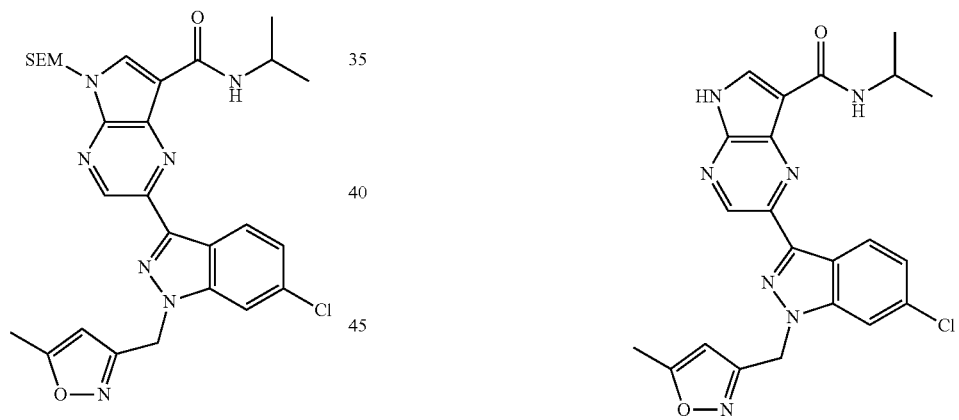

2-(6-Chloro-1H-indazol-3-yl)-N-isopropyl-5-((2-(trimethylsilyl)ethoxy)methyl)-5H-pyrrolo[2,3-b]pyrazine-7-carboxamide (80 mg, 165 μmol) was dissolved in DMF (1 mL) and cooled to 0° C. Sodium hydride (10.6 mg, 264 μmol) was added and the mixture was allowed to stir for 30 min. 3-(Bromomethyl)-5-methylisoxazole (31.9 mg, 181 μmol) was added and the mixture was warmed to room temperature. After 15 h, the mixture was diluted with water and extracted with ethyl acetate. The organic extracts were washed with brine, dried over anhydrous sodium sulfate and concentrated in vacuo. The residue was purified by chromatography (silica, 40 g Analogix column, 20%-50% ethyl acetate in hexanes 15 min) to give 2-(6-chloro-1-((5-methylisoxazol-3-yl)methyl)-1H-indazol-3-yl)-N-isopropyl-5-((2-(trimethylsilyl)ethoxy)methyl)-5H-pyrrolo[2,3-b]pyrazine-7-carboxamide (89 mg, 153 μmol, 93.0%) as a yellow powder. MS (M+Na)⁺=602; $^1$H NMR (CDCl$_3$) δ: 9.23-9.32 (m, 1H), 8.48 (s, 2H), 8.18-8.30 (m, 1H), 7.54-7.61 (m, 1H), 7.27 (m, 2H), 5.70-5.76 (m, 2H), 5.65-5.69 (m, 2H), 4.38-4.56 (m, 1H), 3.52-3.65 (m, 2H), 2.31-2.41 (m, 3H), 1.35-1.47 (m, 6H), 0.89-1.00 (m, 2H), −0.03 (s, 9H).

Step 2

2-(6-Chloro-1-((5-methylisoxazol-3-yl)methyl)-1H-indazol-3-yl)-N-isopropyl-5H-pyrrolo[2,3-b]pyrazine-7-carboxamide

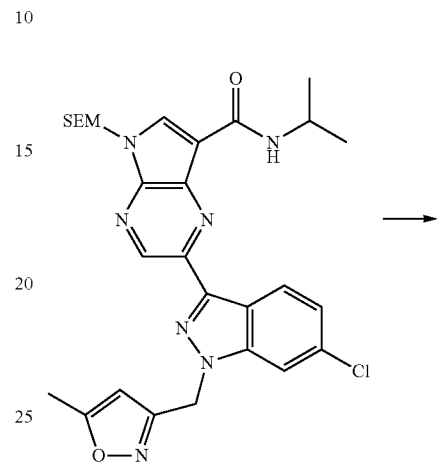

2-(6-Chloro-1-((5-methylisoxazol-3-yl)methyl)-1H-indazol-3-yl)-N-isopropyl-5-((2-(trimethylsilyl)ethoxy)methyl)-5H-pyrrolo[2,3-b]pyrazine-7-carboxamide (89 mg, 153 μmol) was dissolved in 1,2-dichloroethane (3 mL) and placed in a sealed tube. To this was added trifluoroacetic acid (1.75 g, 1.18 mL, 15.3 mmol). The tube was sealed and the mixture heated at to 80° C. After 15 h, the mixture was cooled and concentrated in vacuo. The residue was purified by chromatography (silica, 24 g Analogix column, 95:5 dichloromethane:methanol) then preparative TLC (95:5 dichloromethane/methanol) to give 2-(6-chloro-1-((5-methylisoxazol-3-yl)methyl)-1H-indazol-3-yl)-N-isopropyl-5H-pyrrolo[2,3-b]pyrazine-7-carboxamide (15 mg, 33.3 μmol, 22%). MS (M+Na)⁺=472; $^1$H NMR (CDCl$_3$) δ: 9.37 (s, 1H), 9.22-9.32 (m, 1H), 8.42-8.51 (m, 1H), 8.34-8.40 (m, 1H), 8.11-8.21 (m, 1H), 7.56-7.63 (m, 1H), 7.19-7.36 (m, 1H), 5.90-5.97 (m, 1H), 5.63-5.75 (m, 2H), 4.38-4.56 (m, 1H), 2.38 (s, 3H), 1.41 (d, J=6.4 Hz, 6H).

Example 313

N-tert-Butyl-2-(1-(2-(dimethylamino)ethyl)-6-fluoro-1H-indazol-3-yl)-5H-pyrrolo[2,3-b]pyrazine-7-carboxamide

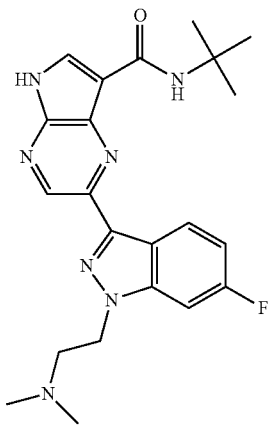 [SMILES: CN(C)CCn1nc(-c2cnc3[nH]cc(C(=O)NC(C)(C)C)c3n2)c2ccc(F)cc21]

N-tert-Butyl-2-(1-(2-(dimethylamino)ethyl)-6-fluoro-1H-indazol-3-yl)-5-((2-(trimethylsilyl)ethoxy)methyl)-5H-pyrrolo[2,3-b]pyrazine-7-carboxamide (0.085 g, 153 μmol) was placed in a sealed tube and dissolved in dichloromethane (2 mL). Trifluoroacetic acid (1.75 g, 1.18 mL, 15.3 mmol) was added and the tube sealed and the mixture heated at to 80° C. After 15 h the mixture was cooled and then concentrated in vacuo. The residue was crystallized from dichloromethane/methanol and cyclohexane to give N-tert-butyl-2-(1-(2-(dimethylamino)ethyl)-6-fluoro-1H-indazol-3-yl)-5H-pyrrolo[2,3-b]pyrazine-7-carboxamide (38 mg, 89.7 μmol, 58.5%) as a white powder. MS (M+H)$^+$=424; $^1$H NMR (CDCl$_3$) δ: 9.07 (s, 1H), 8.42-8.50 (m, 1H), 8.24 (s, 1H), 7.33-7.41 (m, 1H), 7.02 (s, 1H), 4.88 (s, 2H), 3.68-3.79 (m, 2H), 2.85 (s, 7H), 1.55 (s, 6H).

Example 314

2-(6-Fluoro-1-(2-morpholino-2-oxoethyl)-1H-indazol-3-yl)-5H-pyrrolo[2,3-b]pyrazine-7-carboxamide

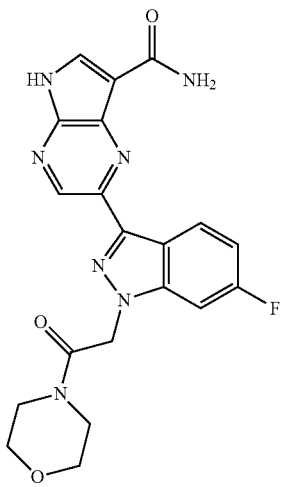 [SMILES: NC(=O)c1c[nH]c2ncc(-c3nn(CC(=O)N4CCOCC4)c4cc(F)ccc34)nc12]

N-tert-Butyl-2-(6-fluoro-1-(2-morpholino-2-oxoethyl)-1H-indazol-3-yl)-5-((2-(trimethylsilyl)ethoxy)methyl)-5H-pyrrolo[2,3-b]pyrazine-7-carboxamide (42 mg, 68.9 μmol) was placed in a sealed tube and dissolved in dichloromethane (2 mL). Trifluoroacetic acid (785 mg, 531 μL, 6.89 mmol) was added and the tube was sealed and the mixture heated at to 80° C. After 15 h the mixture was cooled and concentrated in vacuo. Recrystallization from dichloromethane/methanol and cyclohexane gave 2-(6-fluoro-1-(2-morpholino-2-oxoethyl)-1H-indazol-3-yl)-5H-pyrrolo[2,3-b]pyrazine-7-carboxamide (7 mg, 16.5 μmol, 24.0%) as a white powder. MS (M−H)$^-$=422; $^1$H NMR (DMSO-d$_6$) δ: 8.42 (s, 1H), 7.72 (dd, J=8.9, 5.1 Hz, 1H), 7.65 (s, 1H), 6.73 (d, J=9.4 Hz, 1H), 6.37-6.47 (m, 1H), 4.82 (s, 2H), 2.89-3.09 (m, 6H), 2.82 (d, J=4.9 Hz, 2H).

Example 315

2-(6-Fluoro-1-methyl-1H-indazol-3-yl)-5H-pyrrolo[2,3-b]pyrazine-7-carboxylic acid d9-tert-butylamide

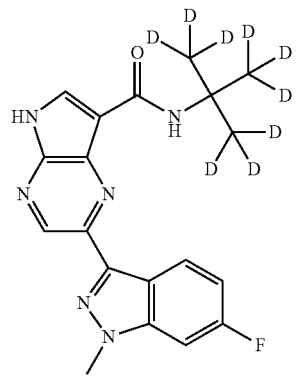

Step 1

2-(6-Fluoro-1-methyl-1H-indazol-3-yl)-5-(2-trimethylsilanyl-ethoxymethyl)-5H-pyrrolo[2,3-b]pyrazine-7-carboxylic acid d9-tert-butylamide

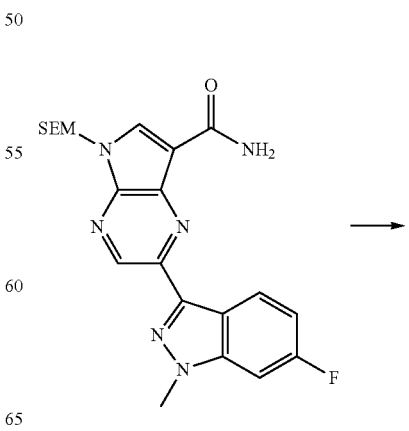

-continued

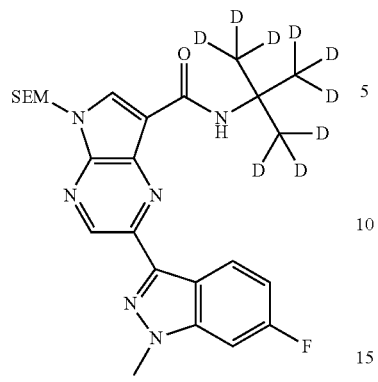

2-(6-Fluoro-1-methyl-1H-indazol-3-yl)-5-((2-(trimethylsilyl)ethoxy)methyl)-5H-pyrrolo[2,3-b]pyrazine-7-carboxylic acid (99 mg, 224 µmol), N1-((ethylimino)methylene)-N3,N3-dimethylpropane-1,3-diamine hydrochloride (98.9 mg, 516 µmol) and 1H-benzo[d][1,2,3]triazol-1-ol hydrate (98.7 mg, 516 µmol) were combined with DMF (4 mL) to give a colorless solution. tert-Butyl-d9-amine (73.7 mg, 897 µmol) was added. After 72 h the reaction mixture was poured into 10 mL citric acid solution (10%) and extracted with ethyl acetate (3×15 mL). The crude material was purified by chromatography (silica gel, 4 g, 25-70% ethyl acetate in hexanes) to give 2-(6-Fluoro-1-methyl-1H-indazol-3-yl)-5-(2-trimethylsilanylethoxymethyl)-5H-pyrrolo[2,3-b]pyrazine-7-carboxylic acid d9-tert-butylamide (80 mg, 127 mmol, 56.4%) contaminated with ~20% recovered starting material. This was used directly in the next step without further purification. MS (M+Na)$^+$=528; $^1$H NMR (CDCl$_3$) δ: 9.26 (s, 1H), 8.55 (dd, J=9.1, 4.9 Hz, 1H), 8.38 (s, 1H), 8.05-8.15 (m, 1H), 7.16 (dd, J=9.1, 2.3 Hz, 1H), 7.06 (dt, J=9.1, 2.3 Hz, 1H), 5.76 (s, 2H), 4.19 (s, 3H), 3.58-3.65 (m, 2H), 0.95-1.02 (m, 2H), −0.03-0.02 (m, 9H).

Step 2

2-(6-Fluoro-1-methyl-1H-indazol-3-yl)-5H-pyrrolo[2,3-b]pyrazine-7-carboxylic acid d9-tert-butylamide

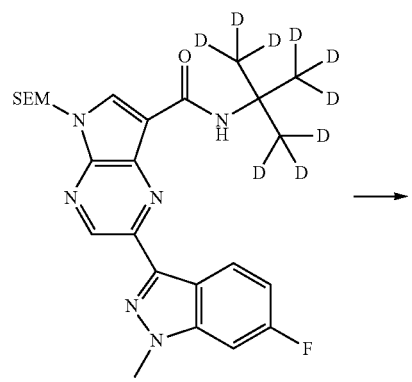

-continued

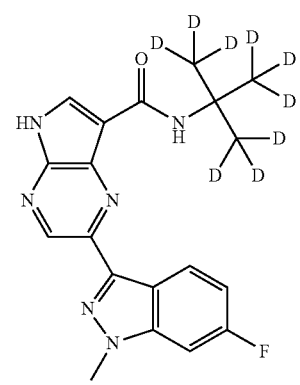 [SMILES: [2H]C([2H])([2H])C(NC(=O)c1c[nH]c2ncc(-c3nn(C)c4cc(F)ccc34)nc12)(C([2H])([2H])[2H])C([2H])([2H])[2H]]

2-(6-Fluoro-1-methyl-1H-indazol-3-yl)-5-(2-trimethylsilanyl-ethoxymethyl)-5H-pyrrolo[2,3-b]pyrazine-7-carboxylic acid d9-tert-butylamide (80 mg, 158 µmol) was dissolved in dichloromethane (2 mL). trifluoroacetic acid (1.35 g, 914 µL, 11.9 mmol) was added. After 15 h the mixture was concentrated in vacuo to a yellow solid. This was suspended in methanol:ammonium hydroxide (9:1, 10 mL), stirred for 15 min, then concentrated in vacuo and purified by chromatography (spherical silica gel, 11 g, 4-10% of a 1:9 mixture of ammonium hydroxide:methanol in dichloromethane) to give 2-(6-fluoro-1-methyl-1H-indazol-3-yl)-5H-pyrrolo[2,3-b]pyrazine-7-carboxylic acid d9-tert-butylamide (28 mg, 74.6 µmol, 47.1%) as a light yellow solid. MS (M+Na)$^+$=398; $^1$H NMR (DMSO-d$_6$) δ: 12.5 (br. S, 1H), 8.95 (s, 1H), 8.35 (dd, J=9.1, 5.3 Hz, 1H), 8.26 (s, 1H), 7.78 (s, 1H), 7.55 (dd, J=10.2, 2.3 Hz, 1H), 7.01 (dt, J=9.1, 2.6 Hz, 1H), 4.01 (s, 3H).

Example 316

2-(6-Chloro-1-methyl-1H-indazol-3-yl)-N-(1,3-dihydroxypropan-2-yl)-5H-pyrrolo[3,2-b]pyrazine-7-carboxamide

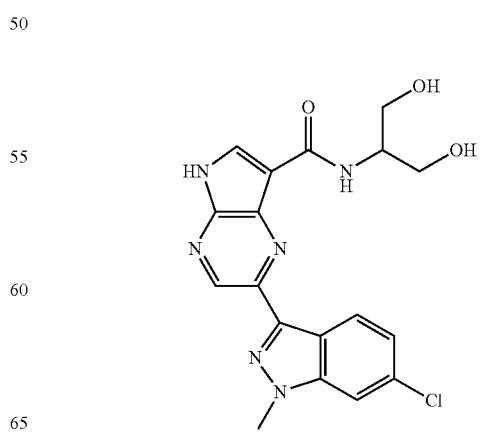

Step 1

2-(6-Chloro-1-methyl-1H-indazol-3-yl)-N-(1,3-dihydroxypropan-2-yl)-5-((2-(trimethylsilyl)ethoxy)methyl)-5H-pyrrolo[3,2-b]pyrazine-7-carboxamide

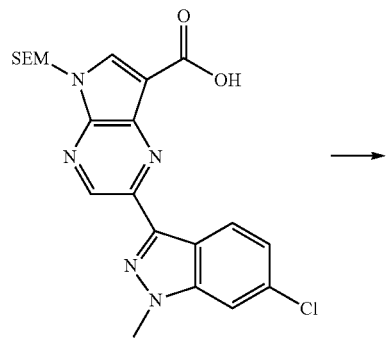

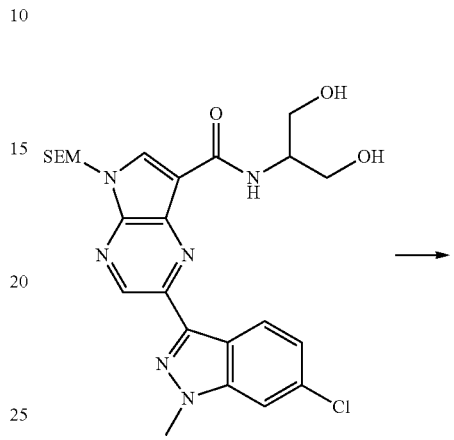

Step 2

2-(6-Chloro-1-methyl-1H-indazol-3-yl)-N-(1,3-dihydroxypropan-2-yl)-5H-pyrrolo[3,2-b]pyrazine-7-carboxamide

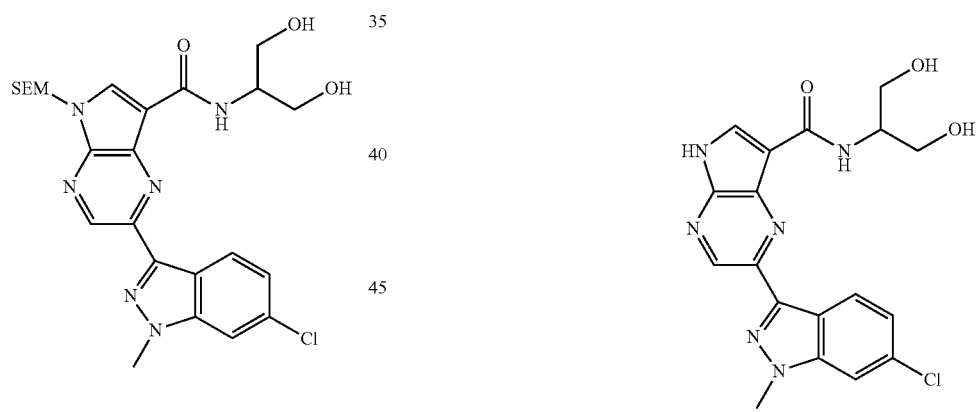

To a stirred mixture of 2-(6-chloro-1-methyl-1H-indazol-3-yl)-5-((2-(trimethylsilyl)ethoxy)methyl)-5H-pyrrolo[3,2-b]pyrazine-7-carboxylic acid (0.07 g, 0.15 mmol) and HATU (0.07 g, 0.18 mmol) in DMF (4.0 mL) was added N,N-diisopropyl-ethylamine (0.024 g, 0.032 mL, 0.18 mmol). The mixture was stirred at room temperature for 30 minutes then 2-aminopropane-1,3-diol (0.021 g, 0.23 mmol) was added. After 18 h the reaction mixture was diluted with ethyl acetate and water. The aqueous phase was extracted with EtOAc then the combined organic phase was washed with water and brine, dried (MgSO$_4$), filtered and concentrated. The residue was collected by filtration, washed with dichloromethane and dried in vacuum oven to give 2-(6-chloro-1-methyl-1H-indazol-3-yl)-N-(1,3-dihydroxypropan-2-yl)-5-((2-(trimethylsilyl)ethoxy)methyl)-5H-pyrrolo[3,2-b]pyrazine-7-carboxamide (0.035 g, 0.07 mmol, 43%) as a white solid. $^1$H NMR (CDCl$_3$) δ: 9.24 (s, 1H), 8.75 (d, J=7.3 Hz, 1H), 8.57 (d, J=8.5 Hz, 1H), 8.35 (s, 1H), 7.44 (s, 1H), 7.24 (s, 1H), 5.68 (s, 2H), 4.42 (br. s., 1H), 4.14 (s, 3H), 4.01-4.12 (m, 4H), 3.57 (t, J=8.0 Hz, 2H), 2.51 (br. s., 2H), 0.94 (t, J=7.9 Hz, 2H), −0.04 (s, 9H)

To a stirred solution of 2-(6-chloro-1-methyl-1H-indazol-3-yl)-N-(1,3-dihydroxypropan-2-yl)-5-((2-(trimethylsilyl)ethoxy)methyl)-5H-pyrrolo[3,2-b]pyrazine-7-carboxamide (0.035 g, 0.066 mmol) in dichloromethane (3 mL) was added TFA (0.38 g, 0.25 mL, 3.3 mmol) at 20° C. After 18 h, the mixture was concentrated in vacuo. The residue was diluted with dichloromethane and concentrated again. The residue was then suspended in dichloromethane (3 mL) and ethylenediamine (0.2 g, 0.22 mL, 3.3 mmol) added. The mixture was stirred for 3 h, then concentrated in vacuo. The residue was collected by filtration and purified by HPLC eluting with MeCN/water (20-95%) to give 2-(6-chloro-1-methyl-1H-indazol-3-yl)-N-(1,3-dihydroxypropan-2-yl)-5H-pyrrolo[3,2-b]pyrazine-7-carboxamide (0.009 g, 0.022 mmol, 34%) as a white powder. MS (M+H)$^+$=401; $^1$H NMR (DMSO-d$_6$) δ: 12.86 (br. s., 1H), 9.15 (s, 1H), 8.73 (d, J=8.5 Hz, 1H), 8.44 (s, 1H), 8.24 (d, J=8.8 Hz, 1H), 7.96 (s, 1H), 7.32 (d, J=8.8 Hz, 1H), 4.93-5.02 (m, 2H), 4.17 (s, 4H), 3.56-3.77 (m, 4H).

Example 317

2-(6-Chloro-1-methyl-1H-indazol-3-yl)-N-(cyclopropylmethyl)-5H-pyrrolo[3,2-b]pyrazine-7-carboxamide

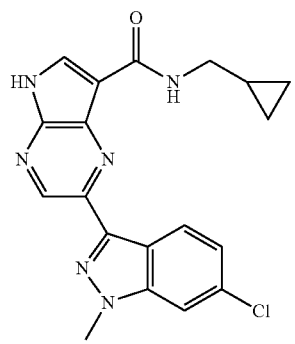 [SMILES: Cn1nc(-c2cnc3[nH]cc(C(=O)NCC4CC4)c3n2)c2ccc(Cl)cc21]

Step 1

2-(6-Chloro-1-methyl-1H-indazol-3-yl)-N-(cyclopropylmethyl)-5-((2-(trimethylsilyl)ethoxy)methyl)-5H-pyrrolo[3,2-b]pyrazine-7-carboxamide

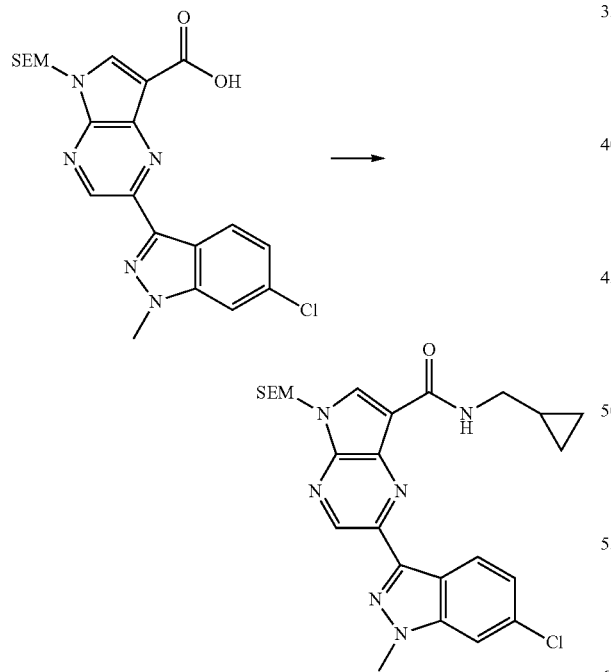

To a stirred mixture of 2-(6-chloro-1-methyl-1H-indazol-3-yl)-5-((2-(trimethylsilyl)ethoxy)methyl)-5H-pyrrolo[3,2-b]pyrazine-7-carboxylic acid (0.07 g, 0.15 mmol) and HATU (0.07 g, 0.18 mmol) in DMF (4.0 mL) was added N,N-diisopropyl-ethylamine (0.024 g, 0.032 mL, 0.18 mmol). After 30 min, cyclopropylmethanamine (0.016 g, 0.23 mmol) was added. After 18 h the reaction mixture was diluted with ethyl acetate and water. The aqueous phase was extracted with EtOAc then the combined organic phase was washed with water and brine, dried (MgSO$_4$). filtered and concentrated. The residue was purified by chromatography (silica, 24 g Analogix column, 30-100% EtOAc in hexanes, gradient over 40 min) to give 2-(6-chloro-1-methyl-1H-indazol-3-yl)-N-(cyclopropylmethyl)-5-((2-(trimethylsilyl)ethoxy)methyl)-5H-pyrrolo[3,2-b]pyrazine-7-carboxamide (0.049 g, 0.096 mmol, 63%) as a white solid. $^1$H NMR (CDCl$_3$) δ: 9.25 (s, 1H), 8.47 (d, J=8.8 Hz, 1H), 8.30-8.39 (m, 2H), 7.49 (s, 1H), 7.21 (d, J=8.8 Hz, 1H), 5.73 (s, 2H), 4.17 (s, 3H), 3.59 (t, J=8.2 Hz, 2H), 3.42-3.54 (m, 2H), 1.22 (dd, J=13.1, 6.5 Hz, 1H), 0.95 (t, J=8.0 Hz, 2H), 0.66 (d, J=7.5 Hz, 2H), 0.40 (d, J=4.3 Hz, 2H), −0.04 (s, 9H)

Step 2

2-(6-Chloro-1-methyl-1H-indazol-3-yl)-N-(cyclopropylmethyl)-5H-pyrrolo[3,2-b]pyrazine-7-carboxamide

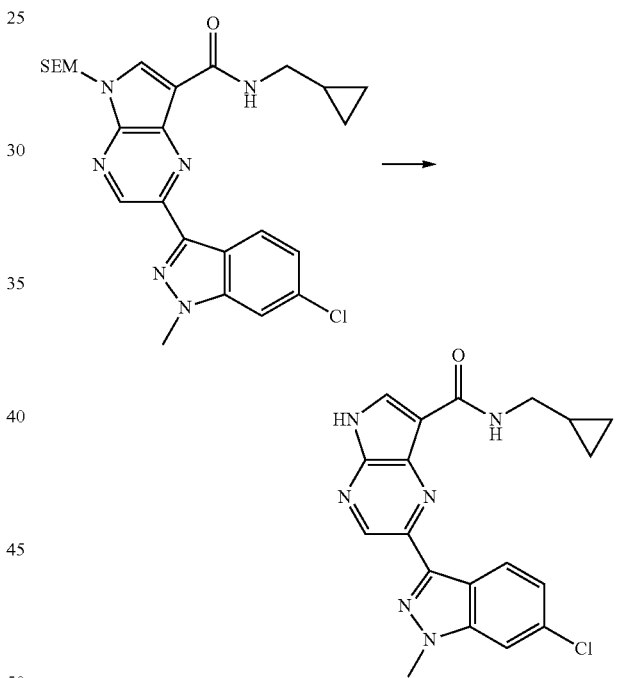

To a stirred solution of 2-(6-chloro-1-methyl-1H-indazol-3-yl)-N-(cyclopropylmethyl)-5-((2-(trimethylsilyl)ethoxy)methyl)-5H-pyrrolo[3,2-b]pyrazine-7-carboxamide (0.049 g, 0.096 mmol) in dichloromethane (5 mL) was added TFA (0.55 g, 0.36 mL, 4.78 mmol) at 20° C. After 18 h, the mixture was concentrated in vacuo. The residue was diluted with dichloromethane and concentrated again. The residue was then suspended in dichloromethane (5 mL) and ethylenediamine (0.29 g, 0.32 mL, 4.78 mmol) was added. The mixture was stirred for 18 h, then concentrated in vacuo. The residue was triturated with water and collected by filtration, washed with water and dried in a vacuum oven to give 2-(6-chloro-1-methyl-1H-indazol-3-yl)-N-(cyclopropylmethyl)-5H-pyrrolo[3,2-b]pyrazine-7-carboxamide (0.034 g, 0.089 mmol, 93%) as a yellow solid. MS (M+H)$^+$=381; $^1$H NMR (DMSO-d$_6$) δ: 9.10 (s, 1H), 8.47 (d, J=8.7 Hz, 2H), 8.44 (s, 1H), 8.21

(t, J=5.4 Hz, 1H), 8.00 (d, J=1.3 Hz, 2H), 7.31 (dd, J=8.6, 1.8 Hz, 2H), 4.18 (s, 3H), 3.33-3.40 (m, 2H), 1.04-1.28 (m, 1H), 0.48-0.65 (m, 2H), 0.27-0.41 (m, 2H).

Example 318

2-(5-Chloro-indazol-1-yl)-5H-pyrrolo[2,3-b]pyrazine-7-carboxylic acid (2-hydroxy-1,1-dimethyl-ethyl)-amide

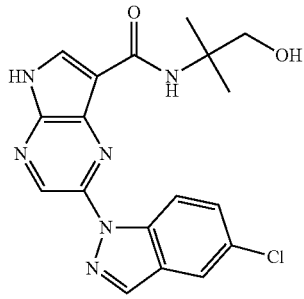 [SMILES: CC(C)(CO)NC(=O)c1c[nH]c2ncc(-n3ncc4cc(Cl)ccc43)nc12]

Step 1

2-(5-Chloro-1H-indazol-1-yl)-N-(1-hydroxy-2-methylpropan-2-yl)-5-((2-(trimethylsilyl)ethoxy)methyl)-5H-pyrrolo[2,3-b]pyrazine-7-carboxamide

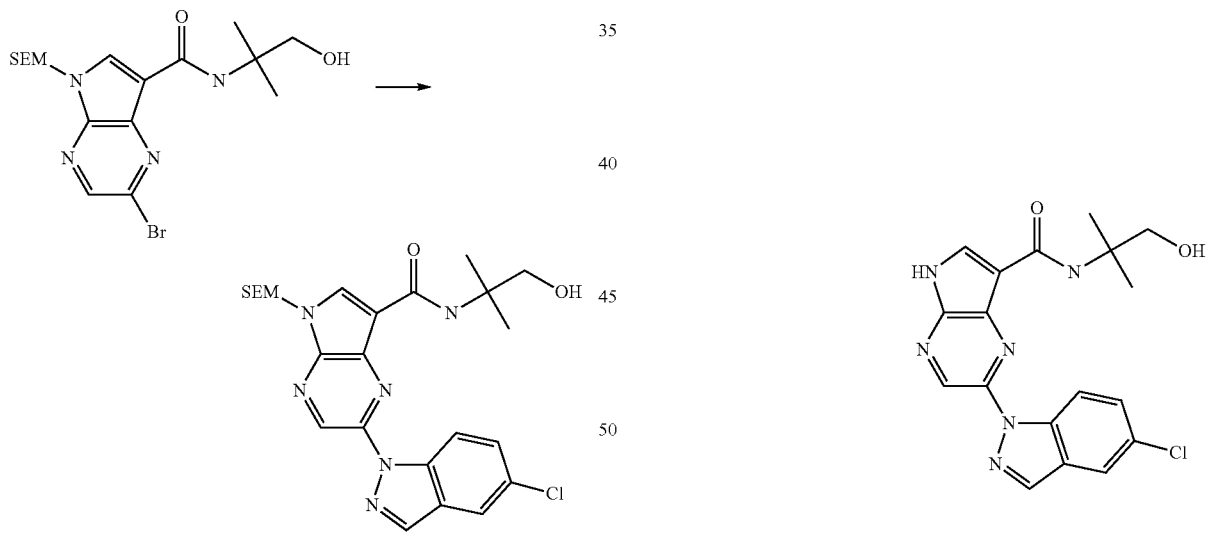

2-Bromo-N-(1-hydroxy-2-methylpropan-2-yl)-5-((2-(trimethylsilyl)ethoxy)methyl)-5H-pyrrolo[2,3-b]pyrazine-7-carboxamide (145 mg, 328 μmol) was dissolved in toluene (3 mL) and copper (I) iodide (3.29 mg, 36.7 μmol), sodium iodide (98.2 mg, 655 μmol) and trans-N,N'-dimethylcyclohexane-1,2-diamine (11.9 mg, 83.6 μmol) added. The mixture was degassed with bubbling nitrogen, then sealed and the mixture heated at to 110° C. After 15 h, 5-chloro-1H-indazole (50 mg, 328 μmol) and potassium phosphate tribasic (146 mg, 688 μmol) were added, the mixture degassed again, and the mixture sealed and the mixture heated at for an additional 24 h. The mixture was cooled, filtered the filtrates concentrated and purified by chromatography (silica, 24 g Analogix column, 0-40% ethyl Acetate in hexanes to give 2-(5-chloro-indazol-1-yl)-5-(2-trimethylsilanyl-ethoxymethyl)-5H-pyrrolo[2,3-b]pyrazine-7-carboxylic acid (2-hydroxy-1,1-dimethyl-ethyl)-amide (124 mg, 74%) as a solid. MS (M+H)$^+$ =515; $^1$H NMR (CDCl$_3$) d: 9.19 (s, 1H), 8.52 (d, J=8.9 Hz, 1H), 8.37 (s, 1H), 8.24 (s, 1H), 7.89 (s, 1H), 7.81-7.85 (m, 1H), 7.47 (dd, J=8.9, 1.9 Hz, 1H), 5.73 (s, 2H), 3.81 (s, 2H), 3.60 (dd, J=8.8, 7.6 Hz, 2H), 1.54 (s, 6H), 0.91-1.01 (m, 2H), −0.02 (s, 9H)

Step 2(7166-005)

2-(5-Chloro-indazol-1-yl)-5H-pyrrolo[2,3-b]pyrazine-7-carboxylic acid (2-hydroxy-1,1-dimethyl-ethyl)-amide

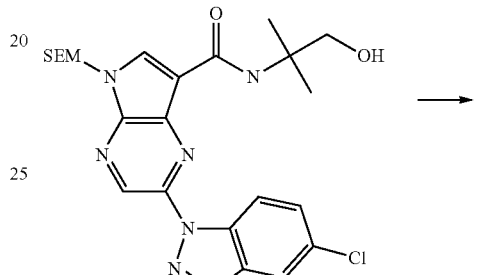

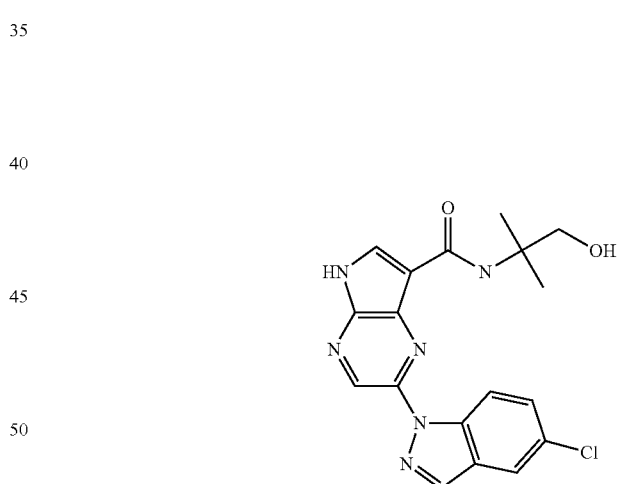

2-(5-Chloro-1H-indazol-1-yl)-N-(1-hydroxy-2-methylpropan-2-yl)-5-((2-(trimethylsilyl)ethoxy)methyl)-5H-pyrrolo[2,3-b]pyrazine-7-carboxamide (124 mg, 241 μmol) was dissolved in dichloromethane (3 mL) then trifluoroacetic acid (1 mL) added. After 15 h the mixture was concentrated in vacuo and Jan. 10, 1960 ammonium hydroxide/methanol/dichloromethane solution (25 mL) added. After 1 h the mixture was concentrated in vacuo and purified by chromatography (silica, 24 g Analogix column, 0-4% of methanol containing 10% ammonium hydroxide in dichloromethane) to give 2-(5-chloro-indazol-1-yl)-5H-pyrrolo[2,3-b]pyrazine-7-carboxylic acid (2-hydroxy-1,1-dimethyl-ethyl) amide (57.7 mg, 62%) as a solid. MS (M+H)$^+$=385; $^1$H NMR (DMSO-d$_6$) δ: 9.04 (s, 1H), 8.70 (d, J=9.0 Hz, 1H), 8.53 (s, 1H), 8.43 (s, 1H), 8.07 (d, J=1.5 Hz, 1H), 7.63 (s, 1H), 7.60 (d, J=2.1 Hz, 1H), 3.59 (d, J=5.7 Hz, 2H), 1.44 (s, 6H).

Example 319

2-(5-Chloro-3-methyl-indazol-1-yl)-5H-pyrrolo[2,3-b]pyrazine-7-carboxylic acid (2-hydroxy-1,1-dimethyl-ethyl)-amide

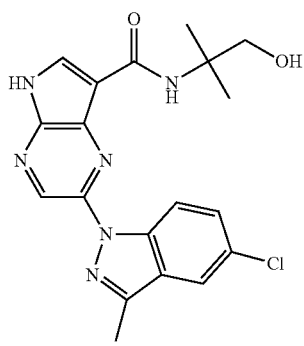 [SMILES: Cc1nn(-c2cnc3[nH]cc(C(=O)NC(C)(C)CO)c3n2)c2ccc(Cl)cc12]

Step 1

2-(5-Chloro-3-methyl-1H-indazol-1-yl)-N-(1-hydroxy-2-methylpropan-2-yl)-5-((2-(trimethylsilyl)ethoxy)methyl)-5H-pyrrolo[2,3-b]pyrazine-7-carboxamide

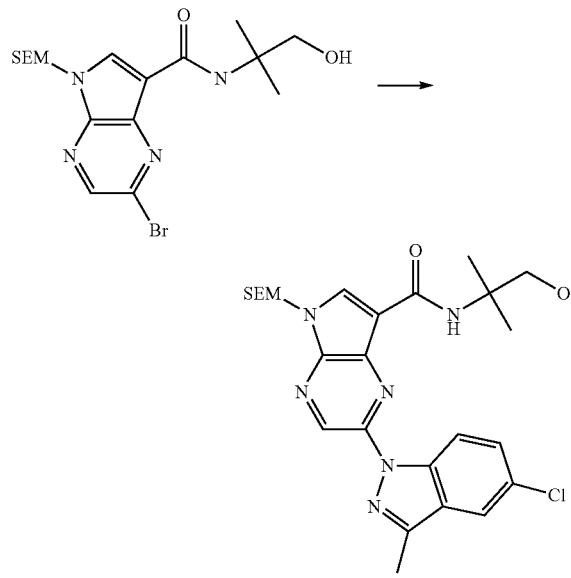

2-Bromo-N-(1-hydroxy-2-methylpropan-2-yl)-5-((2-(trimethylsilyl)ethoxy)methyl)-5H-pyrrolo[2,3-b]pyrazine-7-carboxamide (110 mg, 248 µmol) was dissolved in toluene (1.4 mL), and copper (I) iodide (2.49 mg, 27.8 µmol), sodium iodide (74.4 mg, 496 µmol) and trans-N,N'-dimethylcyclohexane-1,2-diamine (9.00 mg, 63.3 µmol) added. The mixture was sealed under nitrogen and the mixture heated at 110° C. After 15 h, 5-chloro-3-methyl-1H-indazole (41.3 mg, 248 µmol) and potassium phosphate tribasic (111 mg 521 µmol) were added, the mixture degassed under vacuum, backfilled with nitrogen, and the mixture heated at in sealed tube at 110° C. for 24 h. The mixture was cooled, filtered, and the cake washed with ethyl acetate. The combined filtrates were concentrated and purified by chromatography (silica, 24 g Analogix column, 0-40% ethyl acetate in hexanes) to give 2-(5-Chloro-3-methyl-1H-indazol-1-yl)-N-(1-hydroxy-2-methylpropan-2-yl)-5-((2-(trimethylsilyl)ethoxy)methyl)-5H-pyrrolo[2,3-b]pyrazine-7-carboxamide (80 mg, 61%). $^1$H NMR (CDCl$_3$) d: 9.15 (s, 1H), 8.47 (d, J=9.0 Hz, 1H), 8.34 (s, 1H), 7.91 (s, 1H), 7.75 (d, J=1.5 Hz, 1H), 7.45 (dd, J=8.9, 1.8 Hz, 1H), 5.72 (s, 2H), 3.81 (s, 2H), 3.53-3.65 (m, 2H), 2.68 (s, 3H), 1.54 (s, 6H), 0.89-1.01 (m, 2H), −0.03 (s, 9H).

Step 2

2-(5-Chloro-3-methyl-indazol-1-yl)-5H-pyrrolo[2,3-b]pyrazine-7-carboxylic acid (2hydroxy-1,1-dimethyl-ethyl)-amide

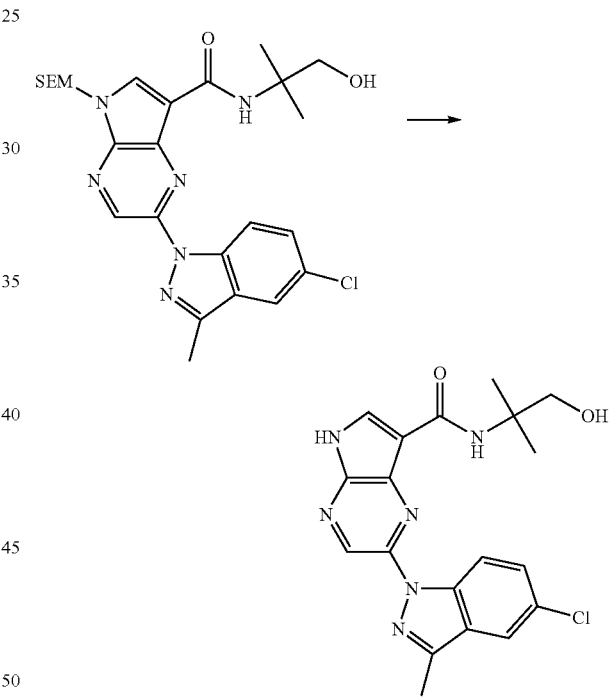

2-(5-Chloro-3-methyl-1H-indazol-1-yl)-N-(1-hydroxy-2-methylpropan-2-yl)-5-((2-(trimethylsilyl)ethoxy)methyl)-5H-pyrrolo[2,3-b]pyrazine-7-carboxamide (80 mg, 151 µmol) was dissolved in dichloromethane (2 mL) and trifluoroacetic acid (1 mL) added. After stirring for 15 h the mixture was concentrated in vacuo, a Jan. 10, 1960 mixture of ammonium hydroxide/methanol/dichloromethane (25 mL) added, and the mixture stirred for 1 h then concentrated in vacuo. Purification by chromatography (silica, 24 g Analogix column, 0-4% methanol containing 10% ammonium hydroxide in dichloromethane) gave 2-(5-chloro-3-methyl-indazol-1-yl)-5H-pyrrolo[2,3-b]pyrazine-7-carboxylic acid (2hydroxy-1,1-dimethyl-ethyl)-amide (46.8 mg 77%) as a solid. MS (M−H)$^−$=397; $^1$H NMR (DMSO-d$_6$) δ: 8.99 (s, 1H), 8.65 (d, J=9.0 Hz, 1H), 8.39 (d, J=2.6 Hz, 1H), 8.05 (d, J=1.5 Hz, 1H), 7.59-7.62 (m, 1H), 7.58 (d, J=2.1 Hz, 1H), 3.59 (d, J=5.7 Hz, 2H), 2.64 (s, 3H), 1.44 (s, 6H).

Example 320

2-(5-Fluoro-indazol-1-yl)-5H-pyrrolo[2,3-b]pyrazine-7-carboxylic acid (2-hydroxy-1,1-dimethyl-ethyl)-amide

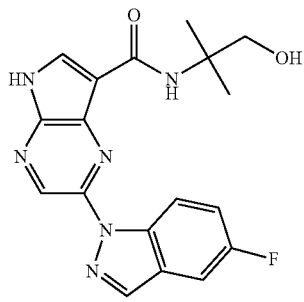

Step 1

2-(5-Fluoro-1H-indazol-1-yl)-N-(1-hydroxy-2-methylpropan-2-yl)-5-((2(trimethylsilyl)ethoxy)methyl)-5H-pyrrolo[2,3-b]pyrazine-7-carboxamide

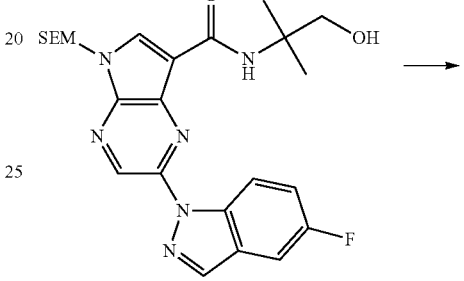

2-Bromo-N-(1-hydroxy-2-methylpropan-2-yl)-5-((2-(trimethylsilyl)ethoxy)methyl)-5H-pyrrolo[2,3-b]pyrazine-7-carboxamide (110 mg, 248 µmol) was dissolved in toluene (1.4 mL) and copper (I) iodide (2.49 mg, 27.8 µmol), sodium iodide (74.4 mg, 496 µmol) and trans-N,N'-dimethylcyclohexane-1,2-diamine (9.00 mg, 63.3 µmol) added. The mixture was sealed under nitrogen and the mixture heated at 110° C. for 15 h. 5-fluoro-1H-indazole (33.8 mg, 248 µmol) and potassium phosphate tribasic (111 mg 521 µmol) were added, the mixture degassed with nitrogen, and the mixture heated at in sealed tube at 110° C. for 15 h. The mixture was filtered, the cake washed with ethyl acetate, and the filtrate concentrated in vacuo. Purification by chromatography (silica, 24 g Analogix column, 0-40% ethyl acetate in hexanes) gave 2-(5-Fluoro-1H-indazol-1-yl)-N-(1-hydroxy-2-methylpropan-2-yl)-5((2(trimethylsilyl)ethoxy)methyl)-5H-pyrrolo[2,3-b]pyrazine-7-carboxamide (111 mg, 90%). $^1$H NMR (CDCl$_3$) δ: 9.19 (s, 1H), 8.55 (dd, J=9.1, 4.2 Hz, 1H), 8.37 (s, 1H), 8.26 (s, 1H), 7.92 (s, 1H), 7.49 (dd, J=8.1, 2.3 Hz, 1H), 7.28-7.33 (m, 1H), 5.73 (s, 2H), 3.81 (s, 2H), 3.53-3.66 (m, 2H), 1.54 (s, 6H), 0.91-1.01 (m, 2H), −0.02 (s, 9H).

Step 2

2-(5-Fluoro-indazol-1-yl)-5H-pyrrolo[2,3-b]pyrazine-7-carboxylic acid (2-hydroxy-1,1-dimethyl-ethyl)-amide

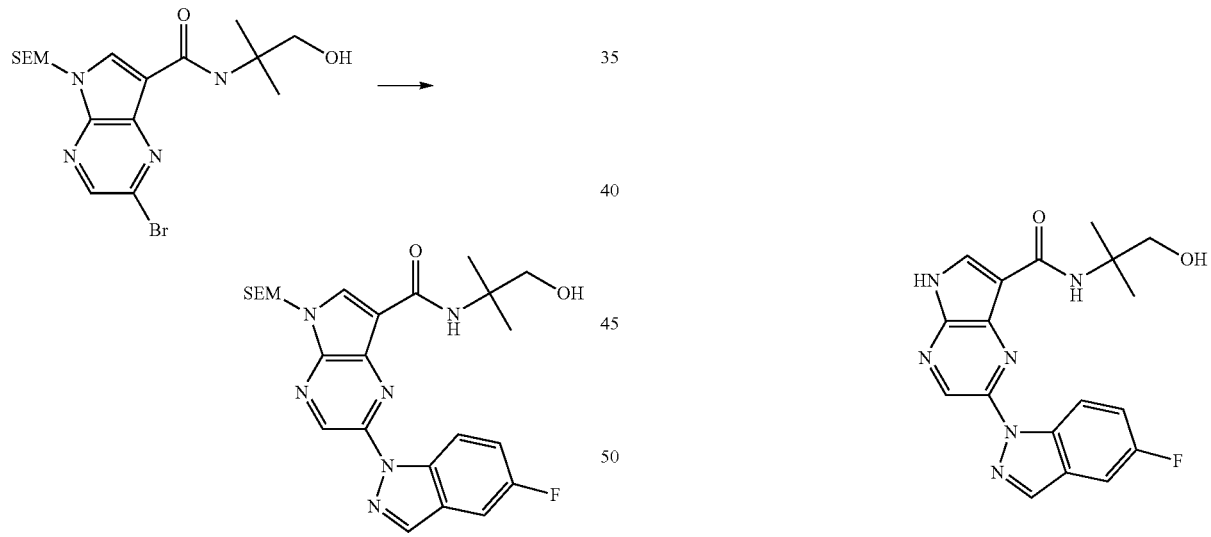

To a stirred solution of 2-(5-fluoro-1H-indazol-1-yl)-N-(1-hydroxy-2-methylpropan-2-yl)-5-((2-(trimethylsilyl)ethoxy)methyl)-5H-pyrrolo[2,3-b]pyrazine-7-carboxamide (50 mg, 100 mmol) in dichloromethane (2 mL) was added trifluoroacetic acid (1 mL). After 15 h, the mixture was concentrated in vacuo and a Jan. 10, 1960 mixture of ammonium hydroxide/methanol/dichloromethane (25 mL) added. After 1 h the mixture was concentrated in vacuo and purified by chromatography (silica, 24 g Analogix column, 0-4% methanol containing 10% ammonium hydroxide in dichloromethane) to give 2-(5-fluoro-indazol-1-yl)-5H-pyrrolo[2,3-b]pyrazine-7-carboxylic acid (2-hydroxy-1,1-dimethyl-ethyl)-amide (25 mg, 68%). MS (M−H)$^-$=367; $^1$H NMR (DMSO-d$_6$) δ: 9.04 (s, 1H), 8.70 (dd, J=9.3, 4.6 Hz, 1H), 8.52

(d, J=0.8 Hz, 1H), 8.41 (s, 1H), 7.76 (dd, J=8.9, 2.3 Hz, 1H), 7.63 (s, 1H), 7.49 (d, J=2.6 Hz, 1H), 3.57-3.62 (m, 2H), 1.44 (s, 6H).

Example 321

2-Indazol-1-yl)-5H-pyrrolo[2,3-b]pyrazine-7-carboxylic acid (2-hydroxy-1,1-dimethyl-ethyl)amide

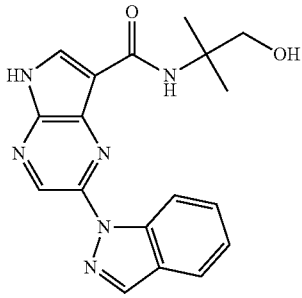 [SMILES: CC(C)(CO)NC(=O)c1c[nH]c2ncc(-n3ncc4ccccc43)nc12]

Step 1(7166-008)

N-(1-Hydroxy-2-methylpropan-2-yl)-2-(1H-indazol-1-yl)-5-((2-(trimethylsilyl)ethoxy)methyl)-5H-pyrrolo[2,3-b]pyrazine-7-carboxamide

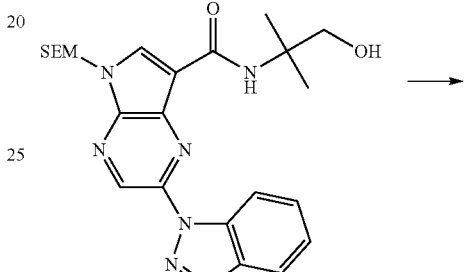

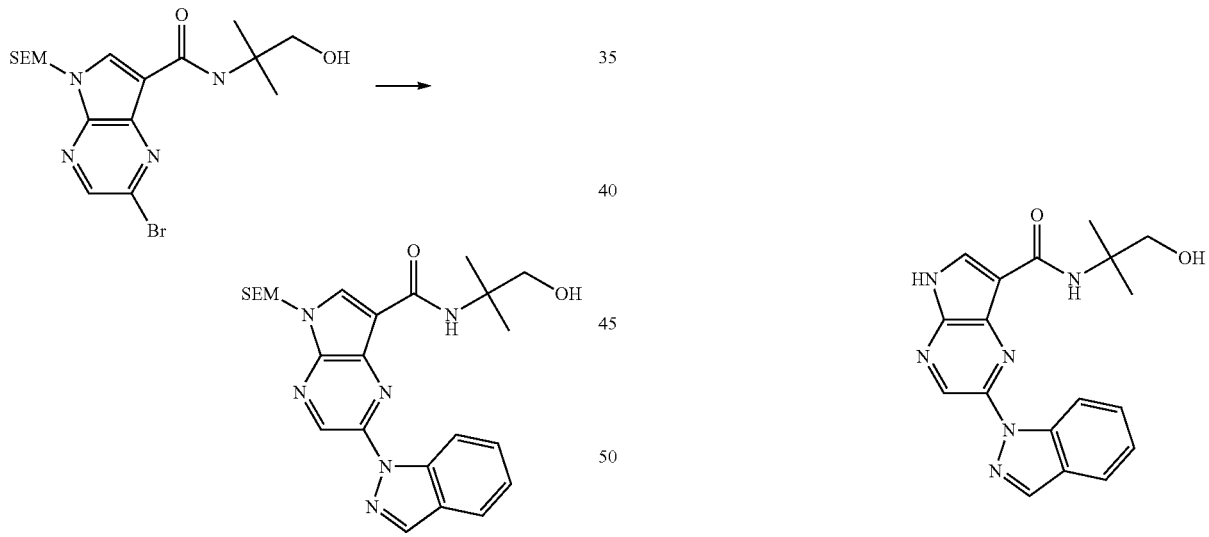

To a stirred solution of 2-bromo-N-(1-hydroxy-2-methyl-propan-2-yl)-5-((2-(trimethylsilyl)ethoxy)methyl)-5H-pyrrolo[2,3-b]pyrazine-7-carboxamide (140 mg, 316 μmol) in toluene (2 mL) was added copper (I) iodide (3.17 mg, 35.4 μmol), sodium iodide (94.7 mg, 631 mmol) and trans-N,N'-dimethylcyclohexane-1,2-diamine (11.5 mg, 80.5 μmol). The reaction mixture was sealed under nitrogen and the mixture heated at 110° C. for 15 h. To the mixture was added 1H-indazole (37.3 mg, 316 μmol) and potassium phosphate tribasic (141 mg, 663 μmol) then the reaction vessel was degassed, filled with nitrogen, and the mixture heated at in sealed tube at 110° C. for 15 h. The mixture was filtered, the cake washed with ethyl acetate, and the filtrate concentrated in vacuo Purification by chromatography (silica, 24 g Analogix column, 0-40% ethyl acetate in hexanes) gave N-(1-Hydroxy-2-methylpropan-2-yl)-2-(1H-indazol-1-yl)-5-((2-(trimethylsilyl)ethoxy)methyl)-5H-pyrrolo[2,3-b]pyrazine-7-carboxamide (112 mg, 74%). $^1$H NMR (CDCl$_3$) d: 9.21 (s, 1H), 8.58 (d, J=8.5 Hz, 1H), 8.35 (s, 1H), 8.30 (s, 1H), 8.01 (s, 1H), 7.87 (d, J=8.1 Hz, 1H), 7.53 (t, J=7.6 Hz, 1H), 7.31-7.41 (m, 1H), 5.73 (s, 2H), 3.81 (s, 2H), 3.55-3.66 (m, 2H), 1.55 (s, 6H), 0.89-1.04 (m, 2H), −0.02 (s, 9H).

Step 2

2-Indazol-1-yl)-5H-pyrrolo[2,3-b]pyrazine-7-carboxylic acid (2-hydroxy-1,1-dimethyl-ethyl)amide

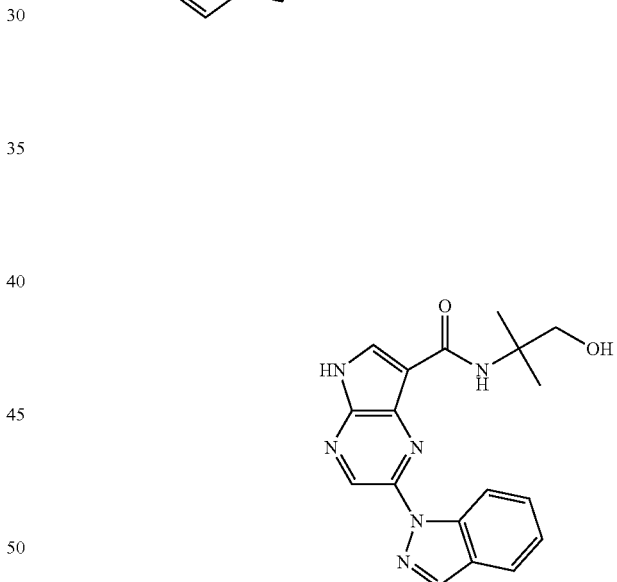

To a stirred solution of N-(1-hydroxy-2-methylpropan-2-yl)-2-(1H-indazol-1-yl-5-((2-(trimethylsilyl)ethoxy)methyl)-5H-pyrrolo[2,3-b]pyrazine-7-carboxamide (112 mg, 100 μmol) in dichloromethane (2 mL) was added trifluoroacetic acid (1 mL). After 15 h, the mixture was concentrated, 25 mL of a Jan. 10, 1960 mixture of ammonium hydroxide/methanol/dichloromethane added, and the mixture stirred for 1 h. The mixture was concentrated in vacuo then purified by chromatography (silica, 24 g Analogix column, 0-4% methanol containing 10% ammonium hydroxide in dichloromethane. 15 min gradient) to give 2-indazol-1-yl)-5H-pyrrolo[2,3-b]pyrazine-7-carboxylic acid (2-hydroxy-1,1-dimethyl-ethyl)-amide (51 mg, 63%). MS (M+H)$^+$=351; $^1$H NMR (DMSO-d$_6$) δ: 9.05 (s, 1H), 8.68 (d, J=8.1 Hz, 1H), 8.54 (s, 1H), 8.40 (s, 1H), 7.96 (d, J=7.9 Hz, 1H), 7.65 (s, 1H), 7.60 (t, J=7.8 Hz, 1H), 7.34-7.43 (m, 1H), 3.62 (d, J=5.5 Hz, 2H), 1.44 (s, 6H).

Example 322

2-(6-Chloro-indazol-1-yl)-5H-pyrrolo[2,3-b]pyrazine-7-carboxylic acid (2-hydroxy-1,1-dimethylethyl)-amide

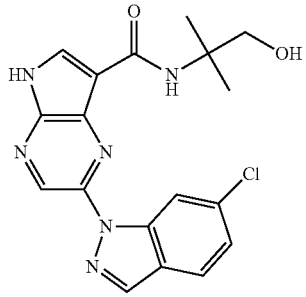 [SMILES: CC(C)(CO)NC(=O)c1c[nH]c2ncc(-n3ncc4ccc(Cl)cc43)nc12]

Step 1

2-(6-Chloro-1H-indazol-1-yl)-N-(1-hydroxy-2-methylpropan-2-yl)-5-((2-(trimethylsilyl)ethoxy)methyl)-5H-pyrrolo[2,3-b]pyrazine-7-carboxamide

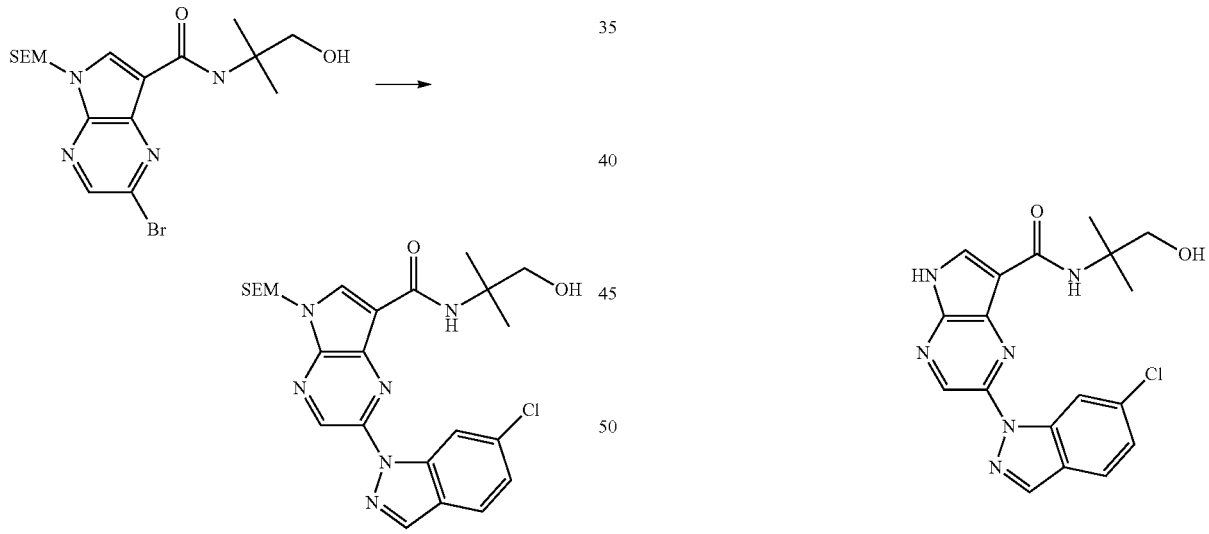

To a stirred solution of 2-bromo-N-(1-hydroxy-2-methylpropan-2-yl)-5-((2-(trimethylsilyl)ethoxy)methyl)-5H-pyrrolo[2,3-b]pyrazine-7-carboxamide (140 mg, 316 µmol) in toluene (2 mL) was added copper (I) iodide (3.17 mg, 35.4 µmol), sodium iodide (94.7 mg, 631 mmol) and trans-N,N'-dimethylcyclohexane-1,2-diamine (11.5 mg, 80.5 µmol). The reaction mixture was sealed under nitrogen and the mixture heated at 110° C. for 15 h. 6-Chloro-1H-indazole (48.2 mg, 316 µmol) and potassium phosphate tribasic (141 mg, 663 µmol) were added and the mixture degassed and filled with nitrogen, then heated in a sealed tube at 110° C. for 15 h. The mixture was filtered, the cake washed with ethyl acetate, and the filtrate concentrated in vacuo. Purification by chromatography (silica, 24 g Analogix column, 0-40% ethyl acetate in hexanes) gave 2-(6-chloro-1H-indazol-1-yl)-N-(1-hydroxy-2-methylpropan-2-yl)-5-(2-(trimethylsilyl)ethoxy)methyl)-5H-pyrrolo[2,3-b]pyrazine-7-carboxamide (124 mg, 76%). $^1$H NMR (CDCl$_3$) δ: 9.14 (s, 1H), 8.51-8.55 (m, 1H), 8.38 (s, 1H), 8.26 (d, J=1.0 Hz, 1H), 7.91 (s, 1H), 7.78 (dd, J=8.5, 0.5 Hz, 1H), 7.33 (dd, J=8.5, 1.8 Hz, 1H), 5.73 (s, 2H), 3.80 (s, 2H), 3.57-3.64 (m, 2H), 1.56 (s, 6H), 0.96 (dd, J=8.8, 7.8 Hz, 2H), −0.02 (s, 9H).

Step 2

2-(6-Chloro-indazol-1-yl)-5H-pyrrolo[2,3-b]pyrazine-7-carboxylic acid (2-hydroxy-1,1-dimethylethyl)-amide

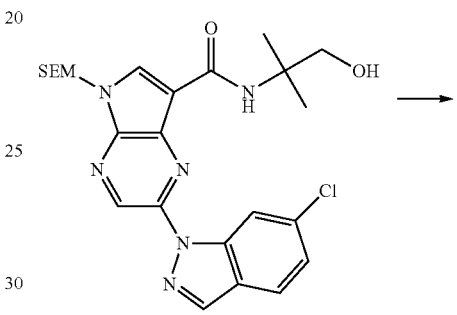

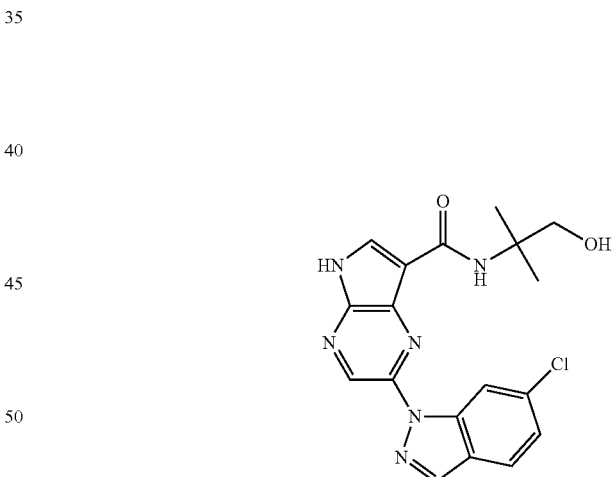

To a stirred solution of 2-(6-chloro-1H-indazol-1-yl)-N-(1-hydroxy-2-methylpropan-2-yl)-5-((2-(trimethylsilyl)ethoxy)methyl)-5H-pyrrolo[2,3-b]pyrazine-7-carboxamide (124 mg, 241 mmol) in dichloromethane (2 mL) was added trifluoroacetic acid (1 mL). After 15 h the mixture was concentrated and 25 mL of a Jan. 10, 1960 mixture of ammonium hydroxide/methanol/dichloromethane added. After 1 h the mixture was concentrated in vacuo. Purification by chromatography (silica, 24 g Analogix column, 0-4% of a methanol containing 10% ammonium hydroxide solution in dichloromethane) gave 2-(6-chloro-indazol-1-yl)-5H-pyrrolo[2,3-b]pyrazine-7-carboxylic acid (2-hydroxy-1,1-dimethylethyl)-amide (75 mg, 81%). MS (M+H)$^+$=385; $^1$H NMR (DMSO-d$_6$) δ: 8.97 (s, 1H), 8.56 (s, 2H), 8.44 (s, 1H), 7.99 (d, J=8.7 Hz, 1H), 7.64 (s, 1H), 7.36-7.48 (m, 1H), 3.62 (d, J=5.7 Hz, 2H), 1.43 (s, 6H).

Example 323

2-(5-Methoxy-indazol-1-yl)-5H-pyrrolo[2,3-b]pyrazine-7-carboxylic acid tert-butylamide

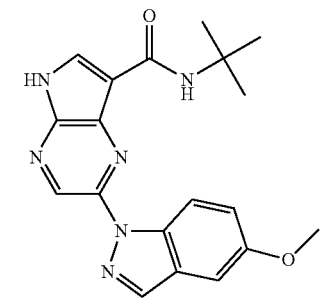 [SMILES: COc1ccc2c(cnn2-c2cnc3[nH]cc(C(=O)NC(C)(C)C)c3n2)c1]

Step 1

N-tert-Butyl-2-(5-methoxy-1H-indazol-1-yl)-5-((2-(trimethylsilyl)ethoxy)methyl)-5H-pyrrolo[2,3-b]pyrazine-7-carboxamide

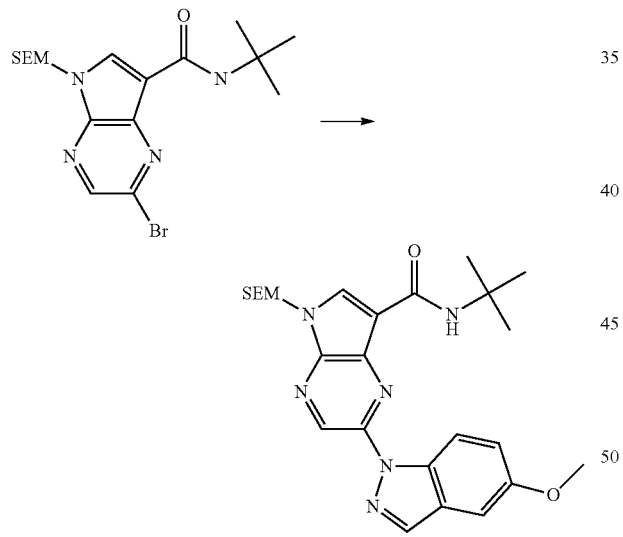

To a stirred solution of 2-bromo-N-tert-butyl-5-((2-(trimethylsilyl)ethoxy)methyl)-5H-pyrrolo[2,3-b]pyrazine-7-carboxamide (150 mg, 351 μmol) in toluene (1 mL) was added copper (I) iodide (3.52 mg, 39.3 μmol), sodium iodide (105 mg, 702 μmol) and trans-N,N'-dimethylcyclohexane-1,2-diamine (12.7 mg, 89.5 μmol). The reaction mixture was sealed under nitrogen and the mixture heated at 110° C. for 15 h. 5-Methoxy-1H-indazole (52.0 mg, 351 μmol) and potassium phosphate tribasic (156 mg, 737 μmol) were added and the mixture was degassed, filled with nitrogen, and the mixture heated at in sealed tube at 110° C. for 15 h. The mixture was filtered, the cake washed with ethyl acetate, and the filtrate concentrated in vacuo. Purification by chromatography (silica, 24 g Analogix column, 0-40% ethyl acetate in hexanes) gave N-tert-Butyl-2-(5-methoxy-1H-indazol-1-yl)-5-((2-(trimethylsilyl)ethoxy)methyl)-5H-pyrrolo[2,3-b]pyrazine-7-carboxamide (22 mg, 13%). $^1$H NMR (CDCl$_3$) δ: 9.18 (s, 1H), 8.52 (d, J=9.0 Hz, 1H), 8.34 (s, 1H), 8.20 (s, 1H), 7.75 (s, 1H), 7.10-7.22 (m, 2H), 5.71 (s, 2H), 3.93 (s, 3H), 3.53-3.64 (m, 2H), 1.61 (s, 9H), 0.89-1.00 (m, 2H), −0.03 (s, 9H).

Step 2

2-(5-Methoxy-indazol-1-yl)-5H-pyrrolo[2,3-b]pyrazine-7-carboxylic acid tert-butylamide

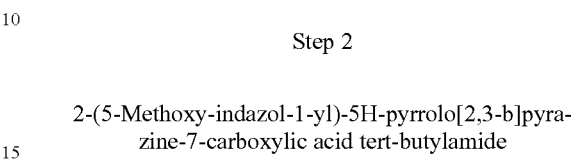

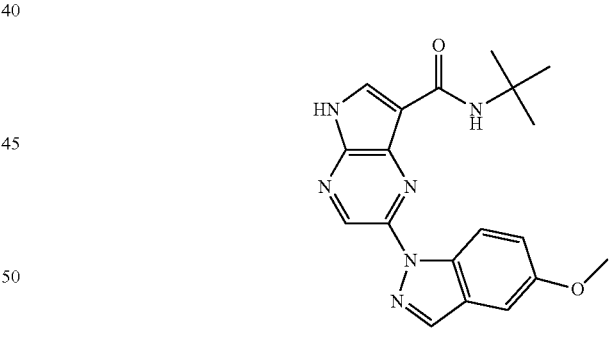

To a stirred solution of N-tert-butyl-2-(5-methoxy-1H-indazol-1-yl)-5-((2-(trimethylsilyl)ethoxy)methyl)-5H-pyrrolo[2,3-b]pyrazine-7-carboxamide (22 mg, 44.5 μmol) in dichloromethane (1 mL) was added trifluoroacetic acid (0.3 mL). After 15 h, the mixture was concentrated in vacuo and 25 mL of a Jan. 10, 1960 mixture of ammonium hydroxide/methanol/dichloromethane added. After 1 h the mixture was concentrated in vacuo. Purification by chromatography (silica, 24 g Analogix column, 0-5% of a methanol containing 10% ammonium hydroxide solution in dichloromethane) gave 2-(5-methoxy-indazol-1-yl)-5H-pyrrolo[2,3-b]pyrazine-7-carboxylic acid tert-butylamide (7.4 mg, 46%). MS (M+H)$^+$=365; $^1$H NMR (DMSO-d$_6$) d: 9.04 (s, 1H), 8.70 (dd, J=9.3, 4.6 Hz, 1H), 8.52 (d, J=0.8 Hz, 1H), 8.41 (s, 1H), 7.76 (dd, J=8.9, 2.3 Hz, 1H), 7.63 (s, 1H), 7.49 (d, J=2.6 Hz, 1H), 3.86 (s, 3H), 1.51 (s, 9H).

Example 324

2-(5-Chloro-indazol-1-yl)-5H-pyrrolo[2,3-b]pyrazine-7-carboxylic acid tert-butylamide

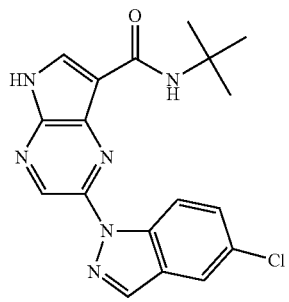 [SMILES: CC(C)(C)NC(=O)c1c[nH]c2ncc(-n3ncc4cc(Cl)ccc43)nc12]

Step 1

N-tert-Butyl-2-(5-chloro-1H-indazol-1-yl)-5-((2-(trimethylsilyl)ethoxy)methyl)-5H-pyrrolo[2,3-b]pyrazine-7-carboxamide

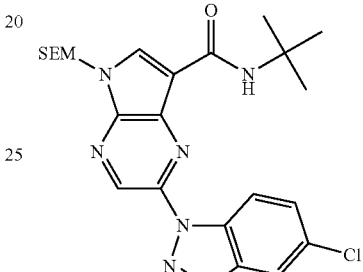

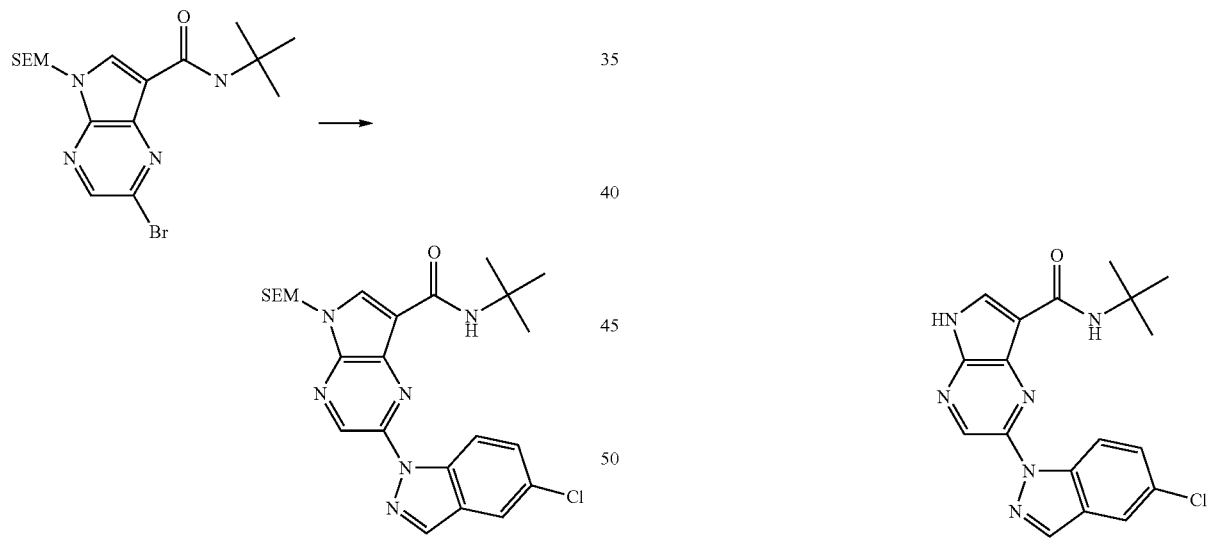

To a stirred solution of 2-bromo-N-tert-butyl-5-((2-(trimethylsilyl)ethoxy)methyl)-5H-pyrrolo[2,3-b]pyrazine-7-carboxamide (150 mg, 351 μmol) in toluene (1 mL) was added copper (I) iodide (3.52 mg, 39.3 μmol), sodium iodide (105 mg, 702 μmol) and trans-N,N'-dimethylcyclohexane-1,2-diamine (12.7 mg, 89.5 μmol). The reaction mixture was sealed under nitrogen and the mixture heated at 110° C. for 15 h then 5-chloro-1H-indazole (53.5 mg, 351 μmol) and potassium phosphate tribasic (156 mg, 737 μmol) were added. The mixture was degassed, filled with nitrogen, and the mixture heated at in sealed tube at 110° C. for 15 h. The mixture was filtered, the cake washed with ethyl acetate, and the filtrate concentrated in vacuo. Purification by chromatography (silica, 24 g Analogix column, 0-40% ethyl acetate in hexanes) gave N-tert-butyl-2-(5-chloro-1H-indazol-1-yl)-5-((2-(trimethylsilyl)ethoxy)methyl)-5H-pyrrolo[2,3-b]pyrazine-7-carboxamide (150 mg, 86%). $^1$H NMR (CDCl$_3$) δ: 9.17 (s, 1H), 8.56 (d, J=8.9 Hz, 1H), 8.37 (s, 1H), 8.24 (s, 1H), 7.83 (s, 1H), 7.68 (s, 1H), 7.46 (dd, J=8.9, 1.6 Hz, 1H), 5.72 (s, 2H), 3.51-3.65 (m, 2H), 1.61 (s, 9H), 0.87-1.03 (m, 2H), −0.03 (s, 9H).

Step 2

2-(5-Chloro-indazol-1-yl)-5H-pyrrolo[2,3-b]pyrazine-7-carboxylic acid tert-butylamide

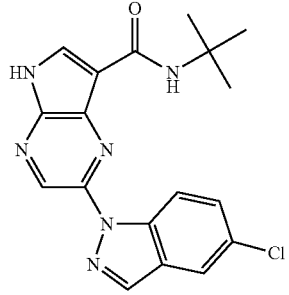

To a stirred solution of N-tert-butyl-2-(5-chloro-1H-indazol-1-yl)-5-((2-(trimethylsilyl)ethoxy)methyl)-5H-pyrrolo[2,3-b]pyrazine-7-carboxamide (144 mg, 289 μmol) in dichloromethane (3 mL) was added trifluoroacetic acid (1 mL). After 15 h then mixture was concentrated in vacuo then 25 mL Jan. 10, 1960 of a mixture of ammonium hydroxide/methanol/dichloromethane added. After 1 h the mixture was concentrated in vacuo. Purification by chromatography (silica, 24 g Analogix column, 0-5% of a solution of methanol containing 10% ammonium hydroxide in dichloromethane) gave 2-(5-chloro-indazol-1-yl)-5H-pyrrolo[2,3-b]pyrazine-7-carboxylic acid tert-butylamide (40.9 mg, 38%). MS (M+H)+=369; 1H NMR (DMSO-d6) δ: 9.02 (s, 1H), 8.60 (s, 1H), 8.57 (s, 1H), 8.53 (s, 1H), 8.43 (s, 1H), 8.09 (s, 1H), 7.61 (s, 1H), 1.50 (s, 9H).

Example 325

2-(5-Difluoromethoxy-indazol-1-yl)-5H-pyrrolo[2,3-b]pyrazine-7-carboxylic acid tert-butylamide

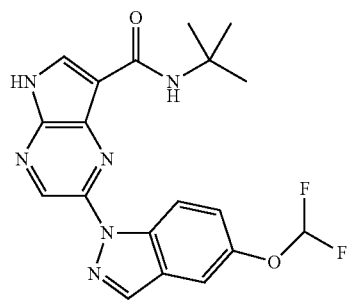 [SMILES: CC(C)(C)NC(=O)c1c[nH]c2ncc(-n3ncc4cc(OC(F)F)ccc43)nc12]

Step 1

N-tert-Butyl-2-(5-(difluoromethoxy)-1H-indazol-1-yl)-5-((2-(trimethylsilyl)ethoxy)methyl)-5H-pyrrolo[2,3-b]pyrazine-7-carboxamide

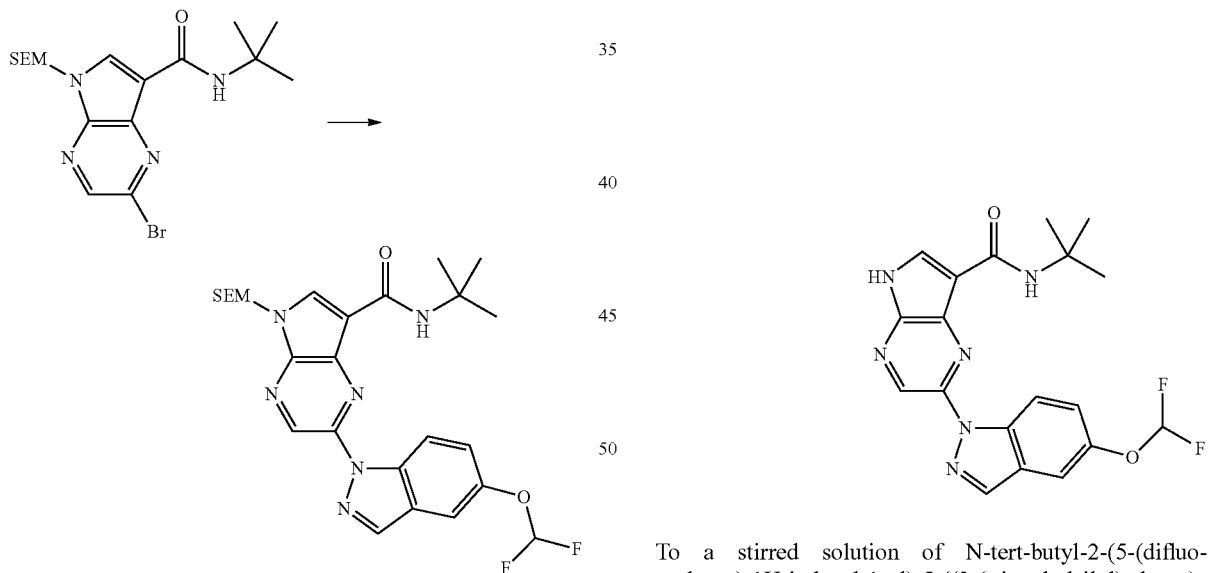

To a stirred solution of 2-bromo-N-tert-butyl-5-((2-(trimethylsilyl)ethoxy)methyl)-5H-pyrrolo[2,3-b]pyrazine-7-carboxamide (150 mg, 351 µmol) in toluene (1 mL) was added copper(I) iodide (3.52 mg, 39.3 µmol), sodium iodide (105 mg, 702 µmol) and trans-N,N'-dimethylcyclohexane-1,2-diamine (12.7 mg, 89.5 µmol). The reaction mixture was sealed under nitrogen and the mixture heated at 110° C. for 15 h. 5-(Difluoromethoxy)-1H-indazole (64.6 mg, 351 µmol) and potassium phosphate tribasic (156 mg, 737 µmol) were added then the mixture was degassed and the mixture heated at in sealed tube at 110° C. for 15 h. The mixture was filtered, the cake washed with ethyl acetate, and the filtrate concentrated in vacuo. Purification by chromatography (silica, 24 g Analogix column, 0-40% ethyl acetate in hexanes) gave N-tert-butyl-2-(5-(difluoromethoxy)-1H-indazol-1-yl)-5-((2-(trimethylsilyl)ethoxy)methyl)-5H-pyrrolo[2,3-b]pyrazine-7-carboxamide (130 mg, 70%). 1H NMR (CDCl3) δ: 9.18 (s, 1H), 8.61 (d, J=9.0 Hz, 1H), 8.36 (s, 1H), 8.27 (s, 1H), 7.69 (s, 1H), 7.59 (s, 1H), 7.32 (dd, J=9.0, 2.1 Hz, 1H), 6.27-6.89 (m, 1H), 5.72 (s, 2H), 3.53-3.66 (m, 2H), 1.61 (s, 9H), 0.87-1.07 (m, 2H), −0.03 (s, 9H).

Step 2

2-(5-Difluoromethoxy-indazol-1-yl)-5H-pyrrolo[2,3-b]pyrazine-7-carboxylic acid tert-butylamide

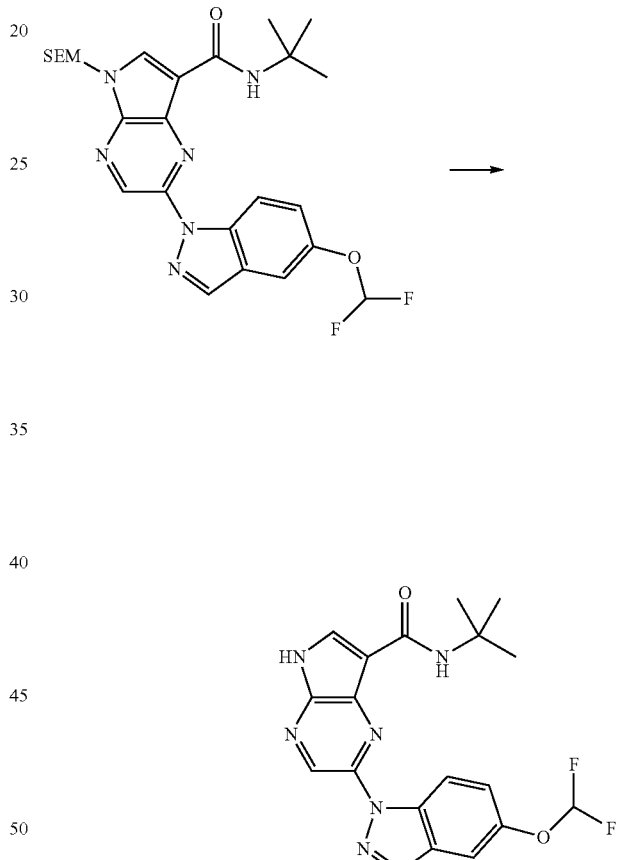

To a stirred solution of N-tert-butyl-2-(5-(difluoromethoxy)-1H-indazol-1-yl)-5-((2-(trimethylsilyl)ethoxy)methyl)-5H-pyrrolo[2,3-b]pyrazine-7-carboxamide (130 mg, 245 µmol) in dichloromethane (1 mL) was added trifluoroacetic acid (1 mL). After 15 h, then mixture was concentrated in vacuo and 25 mL of a Jan. 10, 1960 mixture of ammonium hydroxide/methanol/dichloromethane was added. After 1 h the mixture was concentrated in vacuo. Purification by chromatography (silica, 24 g Analogix column, 0-5% of a solution of methanol containing 10% ammonium hydroxide in dichloromethane) gave 245-difluoromethoxy-indazol-1-yl)-5H-pyrrolo[2,3-b]pyrazine-7-carboxylic acid tert-butylamide (55.3 mg, 56%). MS: (M+H)+=401; 1H NMR (DMSO-d6) δ: 9.09 (s, 1H), 8.57 (s, 1H), 8.51 (s, 1H), 7.78 (d, J=2.3 Hz, 2H), 7.43 (dd, J=9.0, 2.5 Hz, 2H), 7.31 (s, 1H), 1.51 (s, 9H).

Example 326

2-(5-Fluoro-indazol-1-yl)-5H-pyrrolo[2,3-b]pyrazine-7-carboxylic acid tert-butylamide

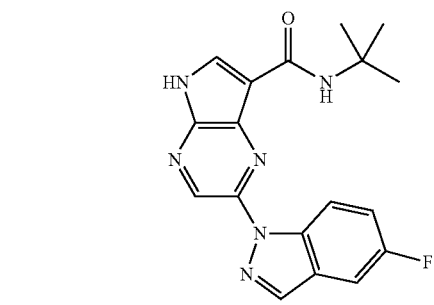 [SMILES: CC(C)(C)NC(=O)c1c[nH]c2ncc(-n3ncc4cc(F)ccc43)nc12]

Step 1

N-tert-Butyl-2-(5-fluoro-1H-indazol-1-yl)-5-((2-(trimethylsilyl)ethoxy)methyl)-5H-pyrrolo[2,3-b]pyrazine-7-carboxamide

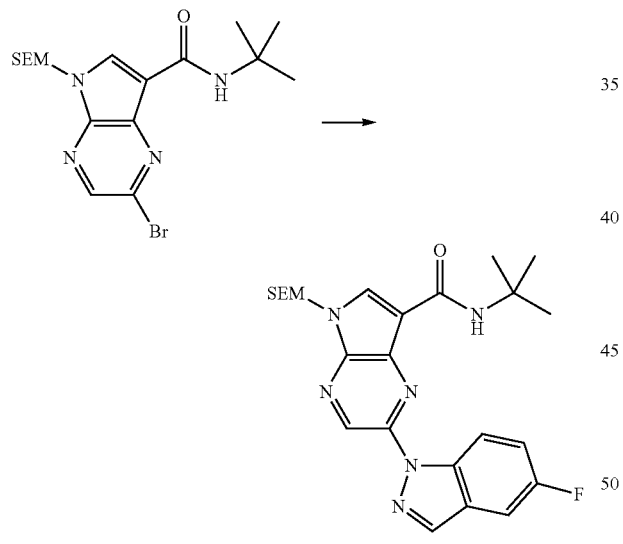

To a stirred solution of 2-bromo-N-tert-butyl-5-((2-(trimethylsilyl)ethoxy)methyl)-5H-pyrrolo[2,3-b]pyrazine-7-carboxamide (140 mg, 316 μmol) 5-fluoro-1H-indazole (43.0 mg, 316 mmol) in dioxane (2 mL) was added sodium tert-butoxide (66.8 mg, 695 μmol) and bis(tri-tert-butylphosphine)palladium(0) (16.1 mg, 31.6 μmol). The mixture was degassed then heated in sealed tube at 125° C. for 15 h. The mixture was cooled, filtered through celite, the cake washed with ethyl acetate, and the combined filtrates were concentrated in vacuo. Purification by chromatography (silica, 24 g Analogix column, 0-40% ethyl acetate in hexanes) gave N-tert-butyl-2-(5-fluoro-1H-indazol-1-yl)-5-((2-(trimethylsilyl)ethoxy)methyl)-5H-pyrrolo[2,3-b]pyrazine-7-carboxamide (120 mg, 76%). $^1$H NMR (CDCl$_3$) δ: 9.18 (s, 1H), 8.59

(dd, J=9.2, 4.4 Hz, 1H), 8.35 (s, 1H), 8.25 (d, J=0.8 Hz, 1H), 7.69 (s, 1H), 7.42-7.52 (m, 1H), 7.28 (d, J=2.5 Hz, 1H), 5.72 (s, 2H), 3.54-3.62 (m, 2H), 1.61 (s, 9H), 0.91-0.99 (m, 2H).

Step 2

2-(5-Fluoro-indazol-1-yl)-5H-pyrrolo[2,3-b]pyrazine-7-carboxylic acid tert-butylamide To a stirred solution of N-tert-butyl-2-(5-fluoro-1H-indazol-1-yl)-5-((2-(trimethylsilyl)ethoxy)methyl)-5H-pyrrolo[2,3-b]pyrazine-7-carboxamide (120 mg, 249 μmol) in dichloromethane (3 mL) was added trifluoroacetic acid (1 mL). After 15 h, the mixture was concentrated in vacuo then 25 mL Jan. 10, 1960 of a solution of ammonium hydroxide/methanol/dichloromethane was added. After 1 h the mixture was concentrated in vacuo then purified by chromatography (silica, 24 g Analogix column, 0-5% methanol containing 10% ammonium hydroxide in dichloromethane) to give 2-(5-fluoro-indazol-1-yl)-5H-pyrrolo[2,3-b]pyrazine-7-carboxylic acid tert-butylamide (24.4 mg, 28%). MS: (M+H)$^+$=353; $^1$H NMR (DMSO-d$_6$) δ: 9.02 (s, 1H), 8.56-8.61 (m, 2H), 8.53

(d, J=0.8 Hz, 2H), 8.42 (d, J=3.0 Hz, 1H), 7.78 (dd, J=8.8, 2.3 Hz, 1H), 7.62 (s, 1H), 7.49 (d, J=2.5 Hz, 1H), 1.50 (s, 9H).

Example 327

2-(5,6-Difluoro-indazol-1-yl)-5H-pyrrolo[2,3-b]pyrazine-7-carboxylic acid tert-butylamide

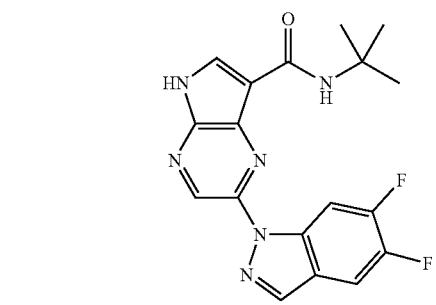 [SMILES: CC(C)(C)NC(=O)c1c[nH]c2ncc(-n3ncc4cc(F)c(F)cc43)nc12]

Step 1

N-tert-Butyl-2-(5,6-difluoro-1H-indazol-1-yl)-5-((2-(trimethylsilyl)ethoxy)methyl)-5H-pyrrolo[2,3-b]pyrazine-7-carboxamide

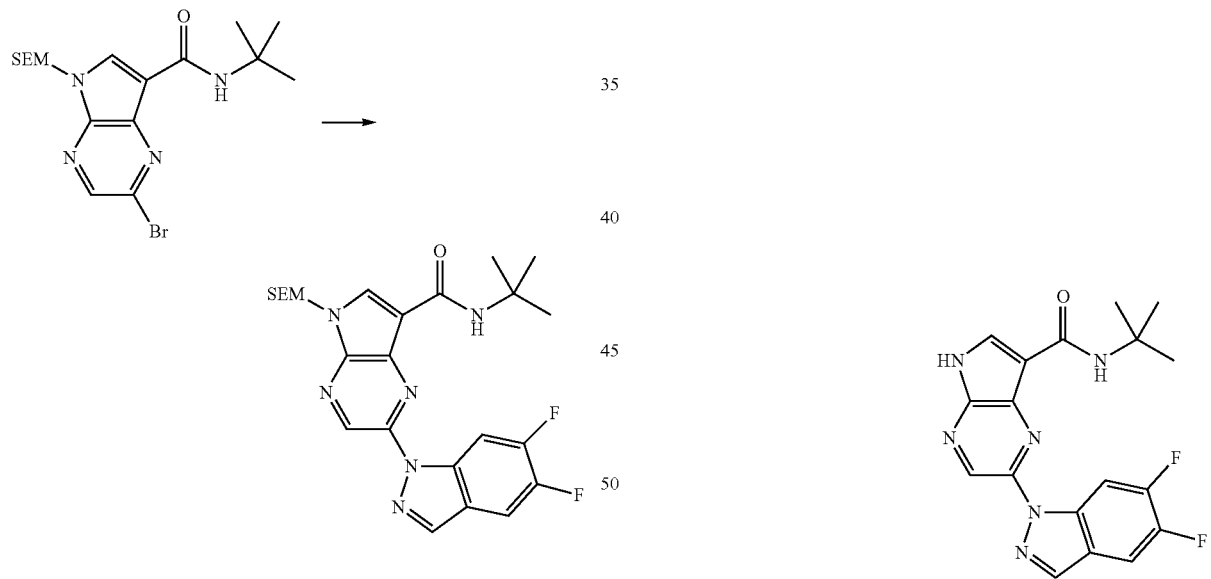

To a stirred solution of 2-bromo-N-tert-butyl-5-((2-(trimethylsilyl)ethoxy)methyl)-5H-pyrrolo[2,3-b]pyrazine-7-carboxamide (150 mg, 351 μmol) and 5,6-difluoro-1H-indazole (54.1 mg, 351 μmol) in dioxane (5.25 mL) was added sodium tert-butoxide (74.2 mg, 772 μmol) and bis(tri-tert-butylphosphine)palladium(0) (17.9 mg, 35.1 μmol). The mixture was degassed then heated in sealed tube at 125° C. for 15 h. The mixture was cooled, filtered through celite, the cake washed with ethyl acetate, and the combined filtrates were concentrated in vacuo. Purification by chromatography (silica, 24 g Analogix column, 0-40% ethyl acetate in hexanes) gave N-tert-butyl-2-(5,6-difluoro-1H-indazol-1-yl)-5-((2-(trimethylsilyl)ethoxy)methyl)-5H-pyrrolo[2,3-b]pyrazine-7-carboxamide (120 mg, 68%). $^1$H NMR (CDCl$_3$) δ: 9.17 (s, 1H), 8.50 (d, J=2.5 Hz, 1H), 8.44 (dd, J=10.0, 6.8 Hz, 1H), 8.37 (s, 1H), 8.30 (s, 1H), 8.24 (d, J=0.8 Hz, 1H), 5.72 (s, 2H), 3.55-3.61 (m, 2H), 1.61 (s, 9H), 0.93-0.96 (m, 2H), −0.03 (s, 9H).

Step 2

2-(5,6-Difluoro-indazol-1-yl)-5H-pyrrolo[2,3-b]pyrazine-7-carboxylic acid tert-butylamide To a stirred solution of N-tert-butyl-2-(5,6-difluoro-1H-indazol-1-yl)-5-((2-(trimethylsilyl)ethoxy)methyl)-5H-pyrrolo[2,3-b]pyrazine-7-carboxamide (120 mg, 240 μmol) in dichloromethane (3 mL) was added trifluoroacetic acid (1 mL). After 15 h, the mixture was concentrated in vacuo then 25 mL of a Jan. 10, 1960 mixture of ammonium hydroxide/methanol/dichloromethane added. After 1 h the mixture was concentrated in vacuo. Purification by chromatography (silica, 24 g Analogix column, 0 to 4% of a solution of methanol containing 10% ammonium hydroxide)/dichloromethane gave 2-(5,6-difluoro-indazol-1-yl)-5H-pyrrolo[2,3-b]pyrazine-7-carboxylic acid tert-butylamide (14.4 mg, 16%). MS:

(M+H)⁺=371; ¹H NMR (DMSO-d₆) δ: 9.02 (s, 1H), 8.53-8.60 (m, 2H), 8.44 (s, 1H), 8.06 (dd, J=10.0, 7.8 Hz, 1H), 7.56 (s, 1H), 1.50 (s, 9H).

Example 328

2-(1H-Pyrrolo[2,3-c]pyridin-7-yl)-5H-pyrrolo[2,3-b]pyrazine-7-carboxylic acid tert-butylamide

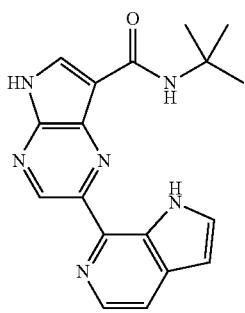 [SMILES: CC(C)(C)NC(=O)c1c[nH]c2ncc(-c3nccc4cc[nH]c34)nc12]

Step 1

7-Bromo-1-((2-(trimethylsilyl)ethoxy)methyl)-1H-pyrrolo[2,3-c]pyridine

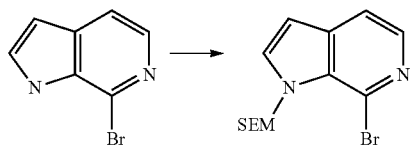 [SMILES: Brc1nccc2cc[nH]c12 ; C[Si](C)(C)CCOCn1ccc2ccnc(Br)c21]

To a stirred solution of 7-bromo-1H-pyrrolo[2,3-c]pyridine (0.2 g, 1.02 mmol) in DMF (5 mL), cooled to 0° C., was added sodium hydride (46.7 mg, 1.17 mmol). After 10 min the mixture was warmed to 25° C. After 20 min the mixture was recooled to 0° C. and (2-(chloromethoxy)ethyl)trimethylsilane (186 mg, 1.12 mmol) added drop-wise. After 5 min the mixture was warmed to 25° C. After 20 min the mixture was partitioned between ethyl acetate and water. The organic phase was washed with water then concentrated in vacuo. Purification by chromatography (silica, 12 g Analogix column, 0-8% ethyl acetate in hexanes) gave 7-bromo-1-((2-(trimethylsilyl)ethoxy)methyl)-1H-pyrrolo[2,3-c]pyridine (0.28 g, 84%) as a colorless oil.

MS: (M+H)⁺=327; ¹H NMR (CDCl₃) δ: 8.04 (dd, J=5.3, 4.3 Hz, 1H), 7.48 (dd, J=9.0, 5.3 Hz, 1H), 7.38 (dd, J=3.3, 2.0 Hz, 1H), 6.58 (dd, J=6.8, 3.3 Hz, 1H), 5.88 (d, J=16.8 Hz, 2H), 3.49-3.59 (m, 2H), 0.91 (td, J=8.2, 3.0 Hz, 2H), -0.07--0.03 (m, 9H).

Step 2

N-tert-Butyl-5-((2-(trimethylsilyl)ethoxy)methyl)-2-(1-((2-(trimethylsilyl)ethoxy)methyl)-1H-pyrrolo[2,3-c]pyridin-7-yl)-5H-pyrrolo[2,3-b]pyrazine-7-carboxamide

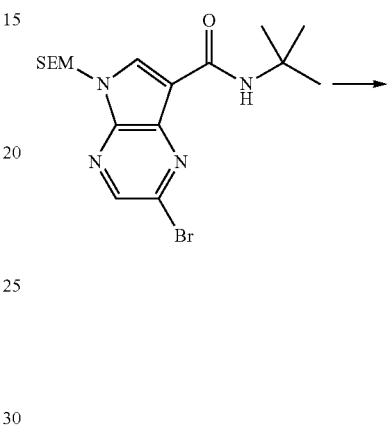

To a solution of 2-bromo-N-tert-butyl-5-((2-(trimethylsilyl)ethoxy)methyl)-5H-pyrrolo[2,3-b]pyrazine-7-carboxamide (0.2 g, 468 μmol) and hexamethylditin (215 mg, 655 mmol) in toluene (2.5 mL) was added Pd(Ph₃P)₄ (54 mg). After bubbling nitrogen through the reaction mixture for 15 min, it was heated to 95° C. After 1.5 h, 7-bromo-1-((2-(trimethylsilyl)ethoxy)methyl)-1H-pyrrolo[2,3-c]pyridine and Pd(Ph₃P)₄ (108 mg, 93.6 μmol) were added. After 72 h the reaction mixture was cooled, filtered through celite, and concentrated in vacuo. Purification by chromatography (silica, 24 g Analogix column, 0-40% ethyl acetate in hexanes) gave N-tert-butyl-5-((2-(trimethylsilyl)ethoxy)methyl)-2-(1-((2-(trimethylsilyl)ethoxy)methyl)-1H-pyrrolo[2,3-c]pyridin-7-yl)-5H-pyrrolo[2,3-b]pyrazine-7-carboxamide (0.13 g, 47%). ¹H NMR (CDCl₃) δ: 9.01 (s, 1H), 8.46 (d, J=5.3 Hz, 1H), 8.34 (s, 1H), 8.13 (s, 1H), 7.68 (d, J=5.3 Hz, 1H), 7.41 (d, J=3.0 Hz, 1H), 6.69 (d, J=3.3 Hz, 1H), 5.74 (s, 2H), 5.51 (s, 2H), 3.59 (dd, J=8.9, 7.7 Hz, 2H), 2.82-2.89 (m, 2H), 1.42 (s, 9H), 0.92-0.99 (m, 2H), 0.41-0.47 (m, 2H), −0.02 (s, 9H), −0.27 (s, 9H).

Step 3

2-(1H-Pyrrolo[2,3-c]pyridin-7-yl)-5H-pyrrolo[2,3-b]pyrazine-7-carboxylic acid tert-butylamide

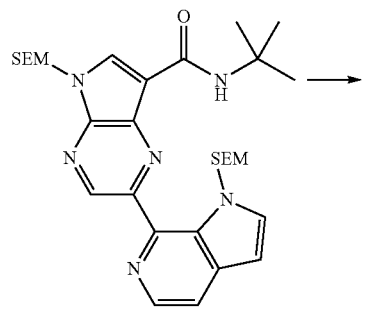

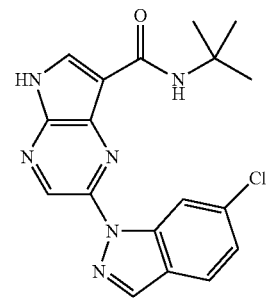 [SMILES: CC(C)(C)NC(=O)c1c[nH]c2ncc(-n3ncc4ccc(Cl)cc43)nc12]

To a stirred solution of N-tert-butyl-5-((2-(trimethylsilyl)ethoxy)methyl)-2-(1-((2-(trimethylsilyl)ethoxy)methyl)-1H-pyrrolo[2,3-c]pyridin-7-yl)-5H-pyrrolo[2,3-b]pyrazine-7-carboxamide (0.13 g, 219 µmol) in dichloromethane (2 mL) was added trifluoroacetic acid (1 mL). After 15 h, the mixture was concentrated in vacuo then 25 mL of a Jan. 10, 1960 mixture of ammonium hydroxide/methanol/dichloromethane added. After 1 h the mixture was concentrated in vacuo. Purification by chromatography (silica, 24 g Analogix column, 0 to 4% of a solution of methanol containing 10% ammonium hydroxide in dichloromethane) gave 2-(1H-pyrrolo[2,3-c]pyridin-7-yl)-5H-pyrrolo[2,3-b]pyrazine-7-carboxylic acid tert-butylamide (11 mg, 15%). MS: (M+H)$^+$= 335; $^1$H NMR (DMSO-d$_6$) δ: 9.25 (s, 1H), 8.43 (d, J=3.0 Hz, 1H), 8.28 (d, J=5.3 Hz, 1H), 7.96 (s, 1H), 7.65-7.69 (m, 2H), 6.65 (dd, J=2.9, 1.9 Hz, 1H), 1.46 (s, 8H).

Example 329

2-(6-Chloro-indazol-1-yl)-5H-pyrrolo[2,3-b]pyrazine-7-carboxylic acid tert-butylamide Step 1

N-tert-Butyl-2-(6-chloro-1H-indazol-1-yl)-5-((2-(trimethylsilyl)ethoxy)methyl)-5H-pyrrolo[2,3-b]pyrazine-7-carboxamide

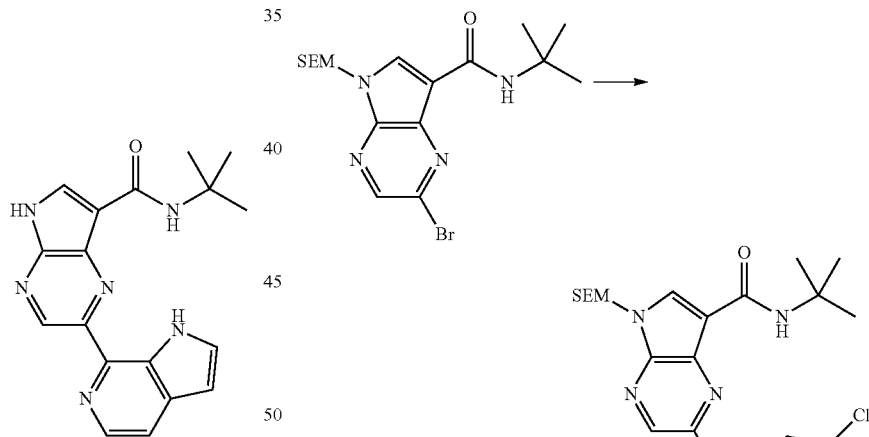

To a stirred solution of 2-bromo-N-tert-butyl-5-((2-(trimethylsilyl)ethoxy)methyl)-5H-pyrrolo[2,3-b]pyrazine-7-carboxamide (150 mg, 351 µmol) and 6-chloro-1H-indazole 64.3 mg, 421 µmoll) in dioxane (5.25 mL) was added sodium tert-butoxide (74.2 mg, 772 µmol) and bis(tri-tert-butylphosphine)palladium(0) (17.9 mg, 35.1 µmol). The mixture was degassed then heated in sealed tube at 125° C. for 15 h. The mixture was cooled, filtered through celite, the cake washed with ethyl acetate, and the combined filtrates were concentrated in vacuo. Purification by chromatography (silica, 24 g Analogix column, 0-40% ethyl acetate in hexanes) gave N-tert-butyl-2-(6-chloro-1H-indazol-1-yl)-5-((2-(trimethylsilyl)ethoxy)methyl)-5H-pyrrolo[2,3-b]pyrazine-7-carboxamide (120 mg, 69%).

Step 2

2-(6-Chloro-indazol-1-yl)-5H-pyrrolo[2,3-b]pyrazine-7-carboxylic acid tert-butylamide

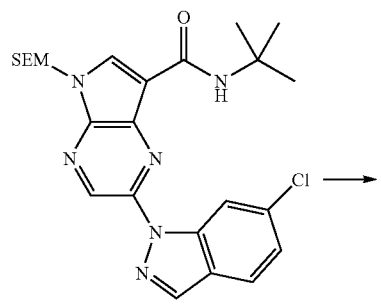

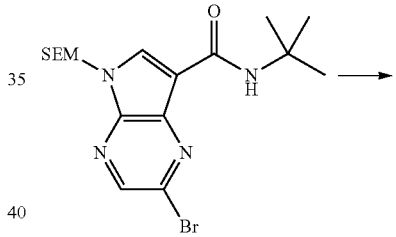

To a stirred solution of N-tert-butyl-2-(6-chloro-1H-indazol-1-yl)-5-((2-(trimethylsilyl)ethoxy)methyl)-5H-pyrrolo[2,3-b]pyrazine-7-carboxamide (120 mg, 240 µmol) in dichloromethane (3 mL) was added trifluoroacetic acid (1 mL). After 15 h, the mixture was concentrated in vacuo then 25 mL of a Jan. 10, 1960 mixture of ammonium hydroxide/methanol/dichloromethane added. After 1 h the mixture was concentrated in vacuo. Purification by chromatography (silica, 24 g Analogix column, 0 to 5% of a solution of methanol containing 10% ammonium hydroxide in dichloromethane) gave 2-(6-chloro-indazol-1-yl)-5H-pyrrolo[2,3-b]pyrazine-7-carboxylic acid tert-butylamide (50.4 mg, 57%). MS: (M+H)$^+$=369; $^1$H NMR (DMSO-d$_6$) δ: 8.97 (s, 1H), 8.57 (s, 2H), 8.43 (s, 1H), 8.00 (dd, J=8.5, 0.5 Hz, 1H), 7.61 (s, 1H), 7.41 (dd, J=8.5, 1.8 Hz, 1H), 1.50 (s, 9H).

Example 330

2-(6-Trifluoromethyl-indazol-1-yl)-5H-pyrrolo[2,3-b]pyrazine-7-carboxylic acid tert-butylamide

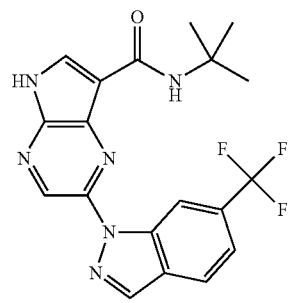 [SMILES: CC(C)(C)NC(=O)c1c[nH]c2ncc(-n3ncc4ccc(C(F)(F)F)cc43)nc12]

Step 1

N-tert-Butyl-2-(6-(trifluoromethyl)-1H-indazol-1-yl)-5-((2-(trimethylsilyl)ethoxy)methyl)-5H-pyrrolo[2,3-b]pyrazine-7-carboxamide

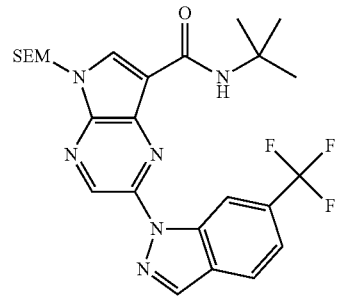

To a stirred solution of 2-bromo-N-tert-butyl-5-((2-(trimethylsilyl)ethoxy)methyl)-5H-pyrrolo[2,3-b]pyrazine-7-carboxamide (180 mg, 421 µmol) and 6-(trifluoromethyl)-1H-indazole (78.4 mg, 421 µmol) in dioxane (2 mL) was added sodium tert-butoxide (89.0 mg, 927 µmol) and bis(tri-tert-butylphosphine)palladium(0) (21.5 mg, 42.1 µmol). The mixture was degassed then heated in sealed tube at 125° C. for two days. The mixture was cooled, filtered through celite, the cake washed with ethyl acetate, and the combined filtrates were concentrated in vacuo. Purification by chromatography (silica, 24 g Analogix column, 0-40% ethyl acetate in hexanes) gave N-tert-Butyl-2-(6-(trifluoromethyl)-1H-indazol-1-yl)-5-((2-(trimethylsilyl)ethoxy)methyl)-5H-pyrrolo[2,3-b]pyrazine-7-carboxamide (110 mg, 49%). $^1$H NMR (CDCl₃) δ: 9.05 (s, 1H), 8.74 (d, J=0.5 Hz, 1H), 8.42 (s, 1H), 8.38 (d, J=1.0 Hz, 1H), 7.99 (d, J=8.5 Hz, 1H), 7.86 (s, 1H), 7.70 (s, 1H), 5.74 (s, 2H), 3.57-3.62 (m, 2H), 1.53 (s, 9H), 0.93-0.98 (m, 2H), −0.03 (s, 9H).

Step 2

2-(6-Trifluoromethyl-indazol-1-yl)-5H-pyrrolo[2,3-b]pyrazine-7-carboxylic acid tert-butylamide

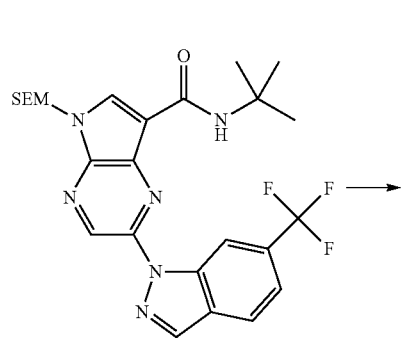

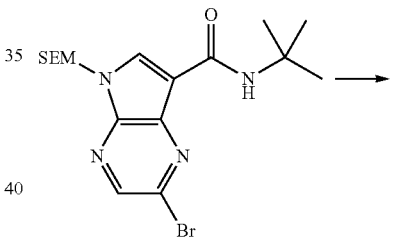

To a stirred solution of N-tert-butyl-2-(6-(trifluoromethyl)-1H-indazol-1-yl)-5-((2-(trimethylsilyl)ethoxy)methyl)-5H-pyrrolo[2,3-b]pyrazine-7-carboxamide (110 mg, 207 μmol) in dichloromethane (3 mL) was added trifluoroacetic acid (1 mL). After 15 h, the mixture was concentrated in vacuo then 25 mL of a Jan. 10, 1960 mixture of ammonium hydroxide/methanol/dichloromethane added. After 1 h the mixture was concentrated in vacuo. Purification by chromatography (silica, 24 g Analogix column, 0-4% over 15 min (methanol containing 10% ammonium hydroxide in dichloromethane) gave 2-(6-trifluoromethyl-indazol-1-yl)-5H-pyrrolo[2,3-b]pyrazine-7-carboxylic acid tert-butylamide (21.8 mg, 26%). MS (M+H)⁺=403; ¹H NMR (DMSO-d₆) δ: 8.93 (s, 1H), 8.78 (s, 1H), 8.71 (d, J=0.8 Hz, 1H), 8.46 (s, 1H), 8.23 (d, J=8.5 Hz, 1H), 7.68 (dd, J=8.5, 1.3 Hz, 1H), 7.62 (s, 1H), 1.41 (s, 9H).

Example 331

2-(6-Methyl-indazol-1-yl)-5H-pyrrolo[2,3-b]pyrazine-7-carboxylic acid tert-butylamide

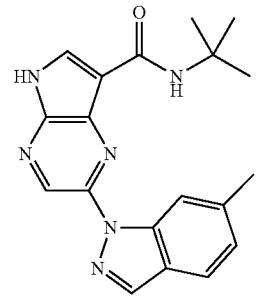 [SMILES: Cc1ccc2cnn(-c3cnc4[nH]cc(C(=O)NC(C)(C)C)c4n3)c2c1]

Step 1

N-tert-Butyl-2-(6-methyl-1H-indazol-1-yl)-5-((2-(trimethylsilyl)ethoxy)methyl)-5H-pyrrolo[2,3-b]pyrazine-7-carboxamide

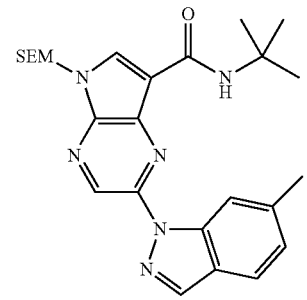

To a stirred solution of 2-bromo-N-tert-butyl-5-((2-(trimethylsilyl)ethoxy)methyl)-5H-pyrrolo[2,3-b]pyrazine-7-carboxamide (140 mg, 328 μmol), 6-methyl-1H-indazole (41.7 mg, 316 μmol) in dioxane (2 mL) was added sodium tert-butoxide (66.8 mg, 695 μmol) and bis(tri-tert-butylphosphine)palladium(0) (16.1 mg, 31.6 μmol). The mixture was degassed then heated in sealed tube at 125° C. for 15 h. The mixture was cooled, filtered through celite, the cake washed with ethyl acetate, and the combined filtrates were concentrated in vacuo. Purification by chromatography (silica, 24 g Analogix column, 0-40% ethyl acetate in hexanes) gave N-tert-butyl-2-(6-methyl-1H-indazol-1-yl)-5-((2-(trimethylsilyl)ethoxy)methyl)-5H-pyrrolo[2,3-b]pyrazine-7-carboxamide. ¹H NMR (CDCl₃) d: 9.08 (s, 1H), 8.35 (s, 1H), 8.30 (s, 1H), 8.23 (d, J=1.0 Hz, 1H), 8.03 (br. s., 1H), 7.85 (s, 1H), 7.29 (s, 1H), 5.72 (s, 2H), 3.55-3.61 (m, 2H), 2.50 (s, 3H), 1.59 (s, 9H), 0.77-1.01 (m, 2H), −0.03 (s, 9H).

Step 2

2-(6-Methyl-indazol-1-yl)-5H-pyrrolo[2,3-b]pyrazine-7-carboxylic acid tert-butylamide

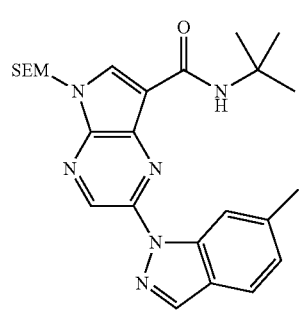

To a stirred solution of N-tert-butyl-2-(6-methyl-1H-indazol-1-yl)-5-((2-(trimethylsilyl)ethoxy)methyl)-5H-pyrrolo[2,3-b]pyrazine-7-carboxamide (100 mg, 209 µmol) in dichloromethane (3 mL) was added trifluoroacetic acid (1 mL). After 15 h, the mixture was concentrated in vacuo then 25 mL of a Jan. 10, 1960 mixture of ammonium hydroxide/methanol/dichloromethane added. After 1 h the mixture was concentrated in vacuo. Purification by chromatography (silica, 24 g Analogix column, 0-4% methanol containing 10% ammonium hydroxide in dichloromethane, 15 min gradient) gave 2-(6-methyl-indazol-1-yl)-5H-pyrrolo[2,3-b]pyrazine-7-carboxylic acid tert-butylamide (35 mg, 48%). MS (M+H)⁺=349; ¹H NMR (DMSO-d₆) δ: 8.95 (s, 1H), 8.45 (d, J=0.8 Hz, 1H), 8.41 (s, 1H), 8.29 (s, 1H), 7.84 (d, J=8.3 Hz, 1H), 7.71 (s, 1H), 7.21 (dd, J=8.3, 0.8 Hz, 1H), 2.53 (s, 3H), 1.49 (s, 9H).

Example 332

2-(6-Fluoro-indazol-1-yl)-5H-pyrrolo[2,3-b]pyrazine-7-carboxylic acid tert-butylamide

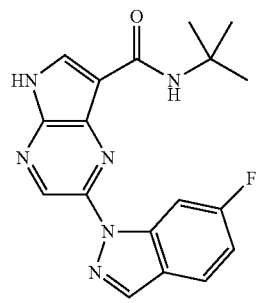

Step 1

N-tert-Butyl-2-(6-fluoro-1H-indazol-1-yl)-5-((2-(trimethylsilyl)ethoxy)methyl)-5H-pyrrolo[2,3-b]pyrazine-7-carboxamide

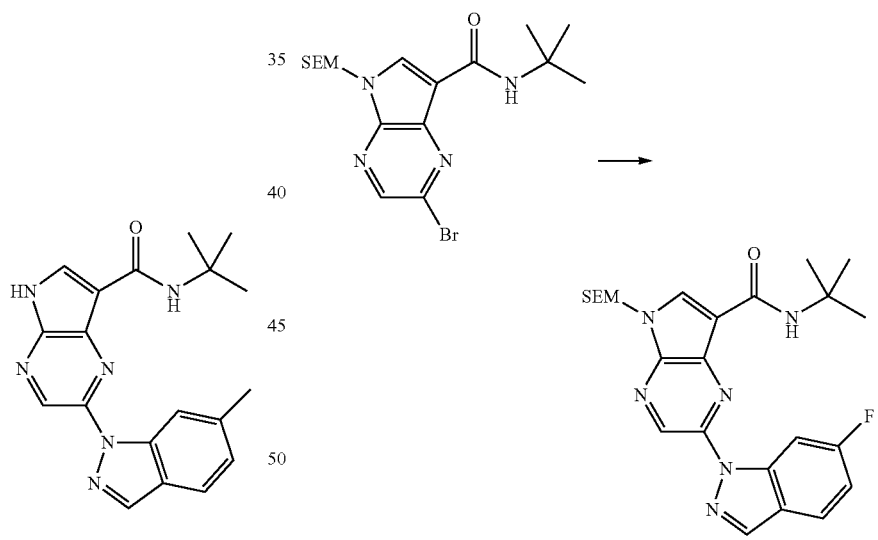

To a stirred solution of 2-bromo-N-tert-butyl-5-((2-(trimethylsilyl)ethoxy)methyl)-5H-pyrrolo[2,3-b]pyrazine-7-carboxamide (140 mg, 328 µmol), 6-fluoro-1H-indazole (43.0 mg, 316 mmol) in dioxane (2 mL) was added sodium tert-butoxide (66.8 mg, 695 µmol) and bis(tri-tert-butylphosphine)palladium(0) (16.1 mg, 31.6 µmol). The mixture was degassed then heated in sealed tube at 125° C. for two days. The mixture was cooled, filtered through celite, the cake washed with ethyl acetate, and the combined filtrates were concentrated in vacuo. Purification by chromatography (silica, 24 g Analogix column, 0-40% ethyl acetate in hexanes) gave N-tert-Butyl-2-(6-fluoro-1H-indazol-1-yl)-5-((2-(trimethylsilyl)methyl)-5H-pyrrolo[2,3-b]pyrazine- 7-carboxamide. ¹H NMR (CDCl₃) δ: 9.17 (s, 1H), 8.36 (s, 1H), 8.29 (dd, J=9.3, 2.3 Hz, 1H), 8.26 (d, J=1.0 Hz, 1H), 7.80 (dd, J=8.8, 5.0 Hz, 1H), 7.66 (s, 1H), 7.12 (td, J=8.9, 2.3 Hz, 1H), 5.72 (s, 2H), 3.54-3.63 (m, 2H), 1.62 (s, 9H), 0.90-1.00 (m, 2H), −0.03 (s, 9H).

Step 2

2-(6-Fluoro-indazol-1-yl)-5H-pyrrolo[2,3-b]pyrazine-7-carboxylic acid tert-butylamide

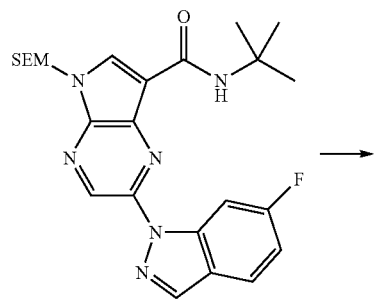

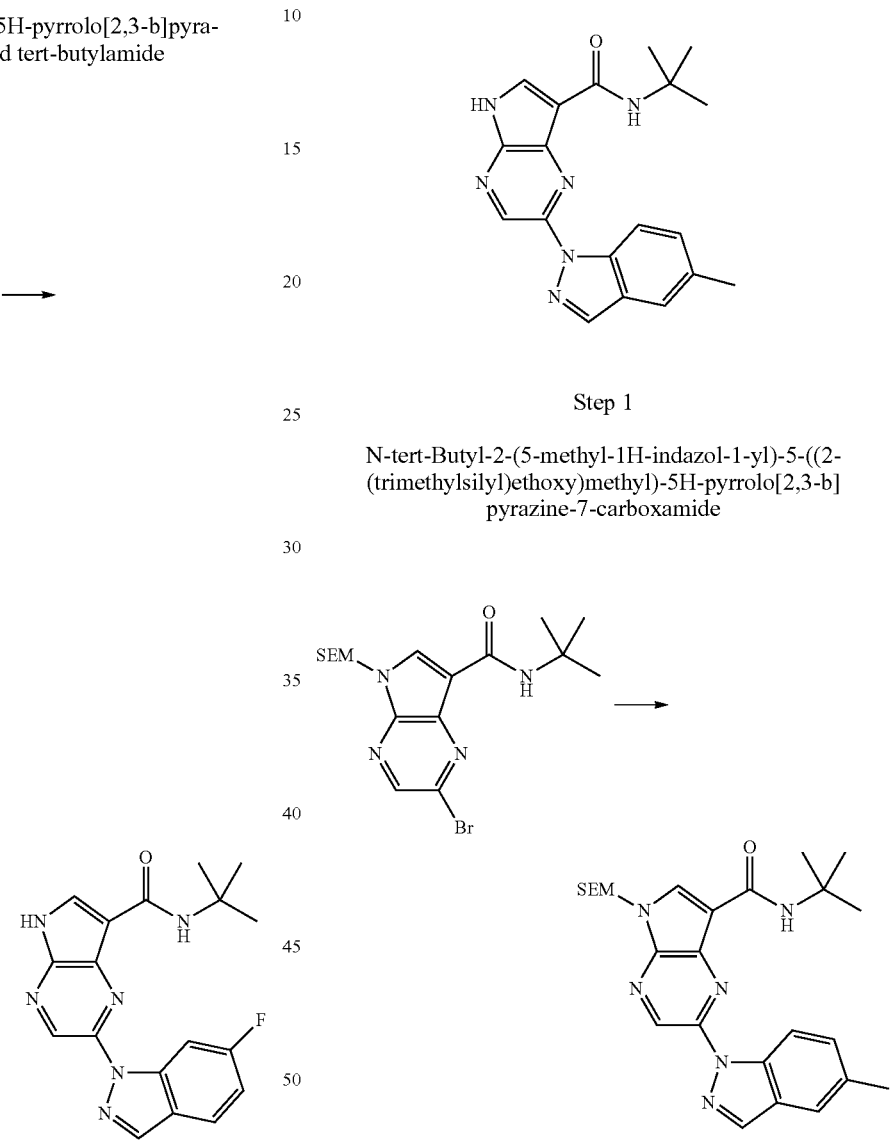

8.42 (s, 1H), 8.32 (dd, J=9.4, 2.1 Hz, 1H), 8.02 (dd, J=8.8, 5.3 Hz, 1H), 7.58 (s, 1H), 7.28 (d, J=2.3 Hz, 1H), 1.50 (s, 9H).

Example 333

2-(5-Methyl-indazol-1-yl)-5H-pyrrolo[2,3-b]pyrazine-7-carboxylic acid tert-butylamide

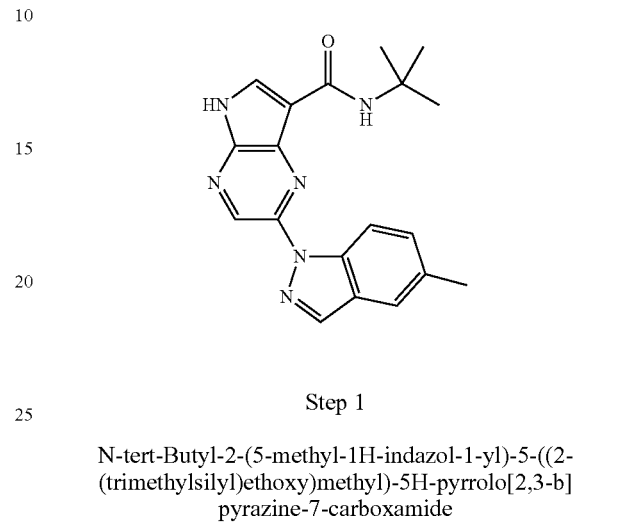

Step 1

N-tert-Butyl-2-(5-methyl-1H-indazol-1-yl)-5-((2-(trimethylsilyl)ethoxy)methyl)-5H-pyrrolo[2,3-b]pyrazine-7-carboxamide To a stirred solution of N-tert-butyl-2-(6-fluoro-1H-indazol-1-yl)-5-((2-(trimethylsilyl)ethoxy)methyl)-5H-pyrrolo[2,3-b]pyrazine-7-carboxamide (101 mg, 209 μmol) in dichloromethane (3 mL) was added trifluoroacetic acid (1 mL). After 15 h, the mixture was concentrated in vacuo then 25 mL of a Jan. 10, 1960 mixture of ammonium hydroxide/methanol/dichloromethane added. After 1 h the mixture was concentrated in vacuo. Purification by chromatography (silica, 24 g Analogix column, 0-4% methanol containing 10% ammonium hydroxide in dichloromethane) gave 2-(6-Fluoro-indazol-1-yl)-5H-pyrrolo[2,3-b]pyrazine-7-carboxylic acid tert-butylamide (31 mg, 42%). MS (M+H)⁺=351; ¹H NMR (DMSO-d₆) δ: 9.02 (s, 1H), 8.56 (d, J=1.0 Hz, 1H), To a stirred solution of 2-bromo-N-tert-butyl-5-((2-(trimethylsilyl)ethoxy)methyl)-5H-pyrrolo[2,3-b]pyrazine-7-carboxamide (140 mg, 328 μmol), 5-methyl-1H-indazole (41.7 mg, 316 μmol) in dioxane (2 mL) was added sodium tert-butoxide (66.8 mg, 695 μmol) and bis(tri-tert-butylphosphine)palladium(0) (16.1 mg, 31.6 μmol). The mixture was degassed then heated in sealed tube at 125° C. for two days. The mixture was cooled, filtered through celite, the cake washed with ethyl acetate, and the combined filtrates were concentrated in vacuo. Purification by chromatography (silica, 24 g Analogix column, 0-40% ethyl acetate in hexanes) gave N-tert-butyl-2-(5-methyl-1H-indazol-1-yl)-5-((2-(trimethylsilyl)ethoxy)methyl)-5H-pyrrolo[2,3-b]pyrazine-7-carboxamide. ¹H NMR (CDCl₃) δ: 9.18 (s, 1H), 8.50 (d, J=8.5 Hz, 1H), 8.34 (s, 1H), 8.20 (d, J=0.8 Hz, 1H), 7.95-8.07 (m, 1H), 7.78 (s, 1H), 7.24 (d, J=8.3 Hz, 1H), 5.71 (s, 2H), 3.55-3.60 (m, 2H), 2.53 (s, 3H), 1.63 (s, 9H), 0.92-0.98 (m, 2H), −0.04 (s, 9H).

Step 2

2-(5-Methyl-indazol-1-yl)-5H-pyrrolo[2,3-b]pyrazine-7-carboxylic acid tert-butylamide

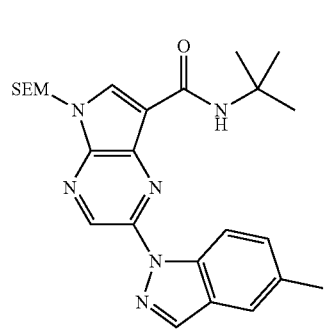
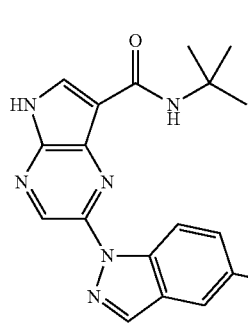

To a stirred solution of N-tert-butyl-2-(5-methyl-1H-indazol-1-yl)-5-((2-(trimethylsilyl)ethoxy)methyl)-5H-pyrrolo[2,3-b]pyrazine-7-carboxamide (0.1 g, 209 µmol) in dichloromethane (3 mL) was added trifluoroacetic acid (1 mL). After 15 h, the mixture was concentrated in vacuo then 25 mL of a Jan. 10, 1960 mixture of ammonium hydroxide/methanol/dichloromethane added. After 1 h the mixture was concentrated in vacuo. Purification by chromatography (silica, 24 g Analogix column, 0-4% methanol containing 10% ammonium hydroxide in dichloromethane) gave 2-(5-methyl-indazol-1-yl)-5H-pyrrolo[2,3-b]pyrazine-7-carboxylic acid tert-butylamide (19 mg, 26%). MS (M+H)⁺=349; ¹H NMR (DMSO-d₆) δ: 9.03 (s, 1H), 8.49 (d, J=8.5 Hz, 1H), 8.43-8.46 (m, 2H), 8.39 (d, J=3.0 Hz, 1H), 7.73 (s, 1H), 7.65 (s, 1H), 2.48 (br. s., 3H), 1.52 (s, 9H).

Example 334

2-(3-Trifluoromethyl-5,6-dihydro-4H-cyclopentapyrazol-1-yl)-5H-pyrrolo[2,3-b]pyrazine-7-carboxylic acid tert-butylamide

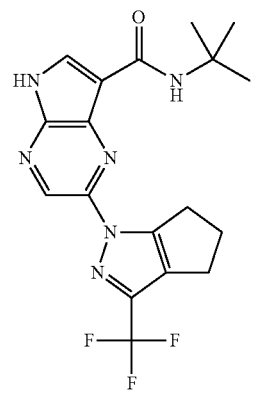 [SMILES: CC(C)(C)NC(=O)c1c[nH]c2ncc(-n3nc(C(F)(F)F)c4c3CCC4)nc12]

Step 1

N-tert-Butyl-2-(3-(trifluoromethyl)-5,6-dihydrocyclopenta[c]pyrazol-1(4H)-yl)-5-((2-(trimethylsilyl)ethoxy)methyl)-5H-pyrrolo[2,3-b]pyrazine-7-carboxamide

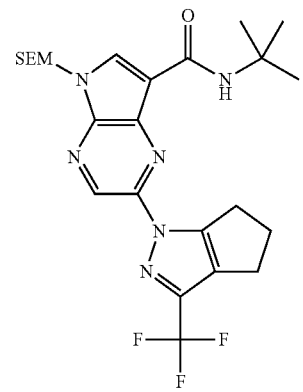

To a stirred solution of 2-bromo-N-tert-butyl-5-((2-(trimethylsilyl)ethoxy)methyl)-5H-pyrrolo[2,3-b]pyrazine-7-carboxamide (200 mg, 468 µmol), 3-(trifluoromethyl)-1,4,5,6-tetrahydrocyclopenta[c]pyrazole (82.4 mg, 468 µmol) in dioxane (5.15 mL) was added sodium tert-butoxide (98.9 mg, 1.03 mmol) and bis(tri-tert-butylphosphine)palladium(0) (23.9 mg, 46.8 mmol). The mixture was degassed then heated in sealed tube at 125° C. for two days. The mixture was cooled, filtered through celite, the cake washed with ethyl acetate, and the combined filtrates were concentrated in vacuo. Purification by chromatography (silica, 24 g Analogix column, 0-40% ethyl acetate in hexanes) gave N-tert-Butyl-2-(3-(trifluoromethyl)-5,6-dihydrocyclopenta[c]pyrazol-1(4H)—O-5-((2-(trimethylsilyl)ethoxy)methyl)-5H-pyrrolo[2,3-b]pyrazine-7-carboxamide. $^1$H NMR (CDCl$_3$) δ: 9.11 (s, 1H), 8.43 (s, 1H), 7.41 (s, 1H), 5.69 (d, J=8.0 Hz, 2H), 3.50-3.60 (m, 2H), 3.31 (t, J=7.3 Hz, 2H), 2.64 (d, J=1.0 Hz, 2H), 2.57 (d, J=1.5 Hz, 2H), 1.56 (d, J=5.3 Hz, 9H), 0.89-0.97 (m, 2H), −0.05 (d, J=5.0 Hz, 9H).

Step 2

2-(3-Trifluoromethyl-5,6-dihydro-4H-cyclopentapyrazol-1-yl)-5H-pyrrolo[2,3-b]pyrazine-7-carboxylic acid tert-butylamide

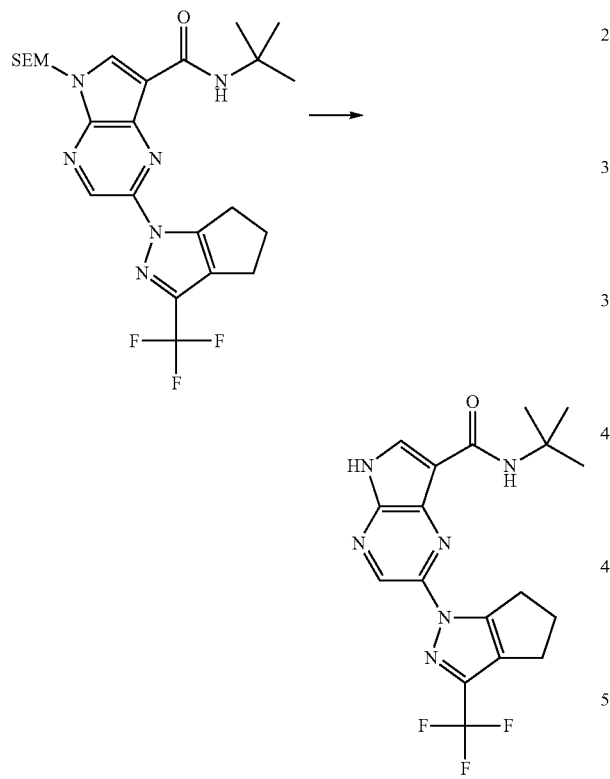

To a stirred solution of N-tert-butyl-2-(3-(trifluoromethyl)-5,6-dihydrocyclopenta[c]pyrazol-1(4H)—O-5-((2-(trimethylsilyl)ethoxy)methyl)-5H-pyrrolo[2,3-b]pyrazine-7-carboxamide (0.1 g, 209 μmol) in dichloromethane (3 mL) was added trifluoroacetic acid (1 mL). After 15 h, the mixture was concentrated in vacuo then 25 mL of a Jan. 10, 1960 mixture of ammonium hydroxide/methanol/dichloromethane added. After 1 h the mixture was concentrated in vacuo. Purification by chromatography (silica, 24 g Analogix column, 0-4% methanol containing 10% ammonium hydroxide in dichloromethane) gave 2-(3-trifluoromethyl-5,6-dihydro-4H-cyclopentapyrazol-1-yl)-5H-pyrrolo[2,3-b]pyrazine-7-carboxylic acid tert-butylamide (22 mg, 29%). MS (M+Na)$^+$= 415; $^1$H NMR (DMSO-d$_6$) δ: 8.92 (s, 1H), 8.47 (s, 1H), 7.33 (s, 1H), 3.25-3.31 (m, 2H), 2.72-2.82 (m, 2H), 2.60-2.70 (m, 2H), 1.47 (s, 9H).

Example 335

2-(3-Chloro-indazol-1-yl)-5H-pyrrolo[2,3-b]pyrazine-7-carboxylic acid tert-butylamide

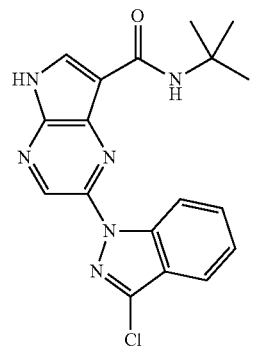 [SMILES: CC(C)(C)NC(=O)c1c[nH]c2ncc(-n3nc(Cl)c4ccccc43)nc12]

Step 1

N-tert-Butyl-2-(3-chloro-1H-indazol-1-yl)-5-((2-(trimethylsilyl)ethoxy)methyl)-5H-pyrrolo[2,3-b]pyrazine-7-carboxamide

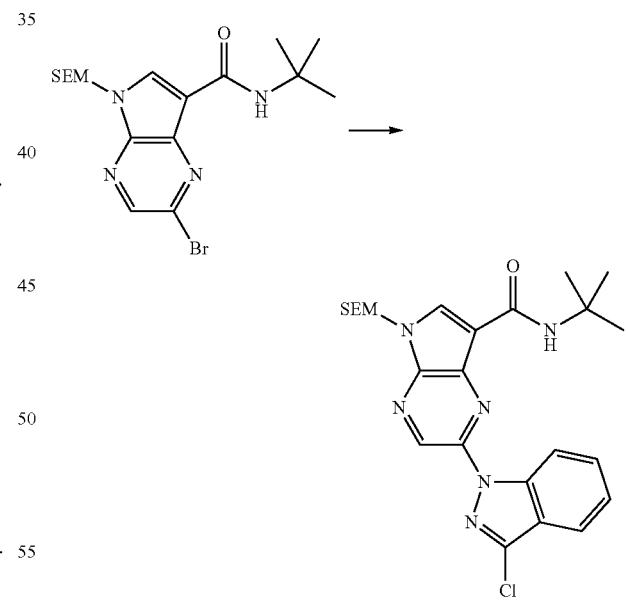

To a stirred solution of 2-bromo-N-tert-butyl-5-((2-(trimethylsilyl)ethoxy)methyl)-5H-pyrrolo[2,3-b]pyrazine-7-carboxamide (136 mg, 318 μmol), 3-chloro-1H-indazole (48.6 mg, 318 mmol) in dioxane (3.5 mL) was added sodium tert-butoxide (67.3 mg, 700 μmol) and bis(tri-tert-butylphosphine)palladium(0) (16.3 mg, 31.8 μmol). The mixture was degassed then heated in sealed tube at 125° C. for two days. The mixture was cooled, filtered through celite, the cake washed with ethyl acetate, and the combined filtrates were concentrated in vacuo. Purification by chromatography (silica, 24 g Analogix column, 0-40% ethyl acetate in hexanes) gave N-tert-butyl-2-(3-chloro-1H-indazol-1-yl)-5-((2-(trimethylsilyl)ethoxy)methyl)-5H-pyrrolo[2,3-b]pyrazine-7-carboxamide. $^1$H NMR (CDCl$_3$) δ: 9.12 (s, 1H), 8.61 (d, J=8.5 Hz, 1H), 8.36 (s, 1H), 7.82 (d, J=8.0 Hz, 1H), 7.70 (s, 1H), 7.58 (ddd, J=8.5, 7.2, 1.1 Hz, 1H), 7.42 (ddd, J=8.1, 7.1, 0.9 Hz, 1H), 5.72 (s, 2H), 3.55-3.62 (m, 2H), 1.61 (s, 9H), 0.95 (d, J=16.6 Hz, 2H), −0.03 (s, 9H).

Step 2

2-(3-Chloro-indazol-1-yl)-5H-pyrrolo[2,3-b]pyrazine-7-carboxylic acid tert-butylamide

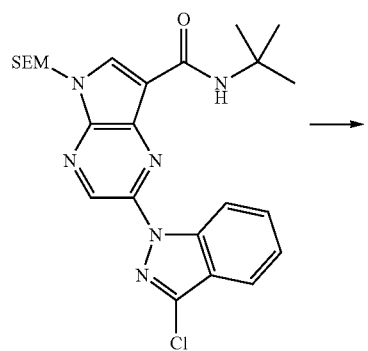

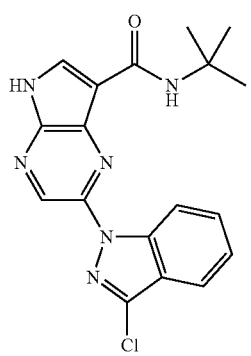

To a stirred solution of N-tert-butyl-2-(3-chloro-1H-indazol-1-yl)-5-((2-(trimethylsilyl)ethoxy)methyl)-5H-pyrrolo[2,3-b]pyrazine-7-carboxamide (0.1 g, 200 µmol) in dichloromethane (3 mL) was added trifluoroacetic acid (1 mL). After 15 h, the mixture was concentrated in vacuo then 25 mL of a Jan. 10, 1960 mixture of ammonium hydroxide/methanol/dichloromethane added. After 1 h the mixture was concentrated in vacuo. Purification by chromatography (silica, 24 g Analogix column, 0-4% methanol containing 10% ammonium hydroxide in dichloromethane) gave 2-(3-Chloro-indazol-1-yl)-5H-pyrrolo[2,3-b]pyrazine-7-carboxylic acid tert-butylamide (28 mg, 38%). MS (M−H)$^−$= 367; $^1$H NMR (DMSO-d$_6$) δ: 8.96 (s, 1H), 8.62 (d, J=8.8 Hz, 1H), 8.44 (s, 1H), 7.89 (d, J=8.0 Hz, 1H), 7.70 (ddd, J=8.4, 7.2, 1.0 Hz, 1H), 7.61 (s, 1H), 7.47-7.54 (m, 1H), 1.50 (s, 9H).

Example 336

2-(5-Methyl-pyrazolo[3,4-b]pyridin-1-yl)-5H-pyrrolo[2,3-b]pyrazine-7-carboxylic acid tert-butylamide

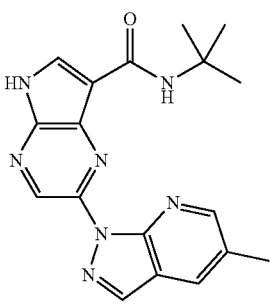

Step 1

N-tert-Butyl-2-(5-methyl-1H-pyrazolo[3,4-b]pyridin-1-yl)-5-((2-(trimethylsilyl)ethoxy)methyl)-5H-pyrrolo[2,3-b]pyrazine-7-carboxamide

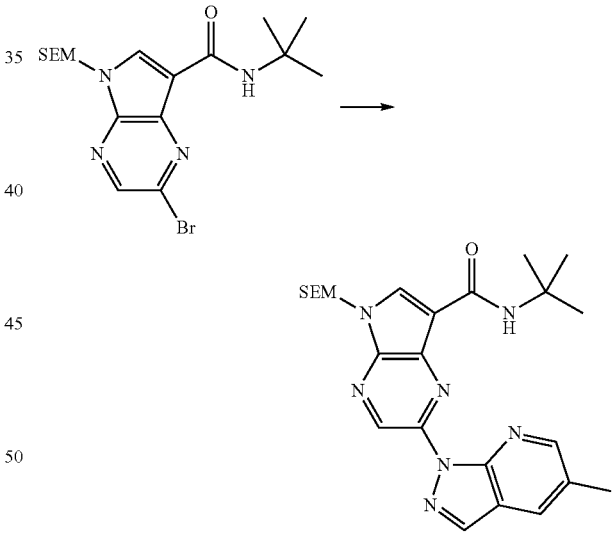

To a stirred solution of 2-bromo-N-tert-butyl-5-((2-(trimethylsilyl)ethoxy)methyl)-5H-pyrrolo[2,3-b]pyrazine-7-carboxamide (136 mg, 318 µmol), 5-methyl-1H-pyrazolo[3,4-b]pyridine (42.4 mg, 318 µmol) in dioxane (3.5 mL) was added sodium tert-butoxide (67.3 mg, 700 µmol) and bis(tri-tert-butylphosphine)palladium(0) (16.3 mg, 31.8 µmol). The mixture was degassed then heated in sealed tube at 125° C. for two days. The mixture was cooled, filtered through celite, the cake washed with ethyl acetate, and the combined filtrates were concentrated in vacuo. Purification by chromatography (silica, 24 g Analogix column, 0-30% ethyl acetate in hexanes) gave N-tert-butyl-2-(5-methyl-1H-pyrazolo[3,4-b]pyridin-1-yl)-5-((2-(trimethylsilyl)ethoxy)methyl)-5H-pyrrolo

[2,3-b]pyrazine-7-carboxamide. $^1$H NMR (CDCl$_3$) δ: 9.19 (s, 1H), 8.51 (d, J=1.8 Hz, 1H), 8.38 (s, 1H), 8.33 (s, 1H), 8.22 (s, 1H), 7.96 (dd, J=2.0, 1.0 Hz, 1H), 5.72 (s, 2H), 3.52-3.59 (m, 2H), 2.54 (s, 3H), 1.60 (s, 9H), 0.88-0.97 (m, 3H), −0.04 (s, 9H).

Step 2

2-(5-Methyl-pyrazolo[3,4-b]pyridin-1-yl)-5H-pyrrolo[2,3-b]pyrazine-7-carboxylic acid tert-butylamide

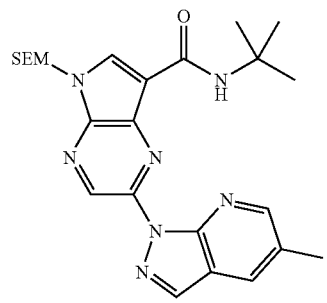

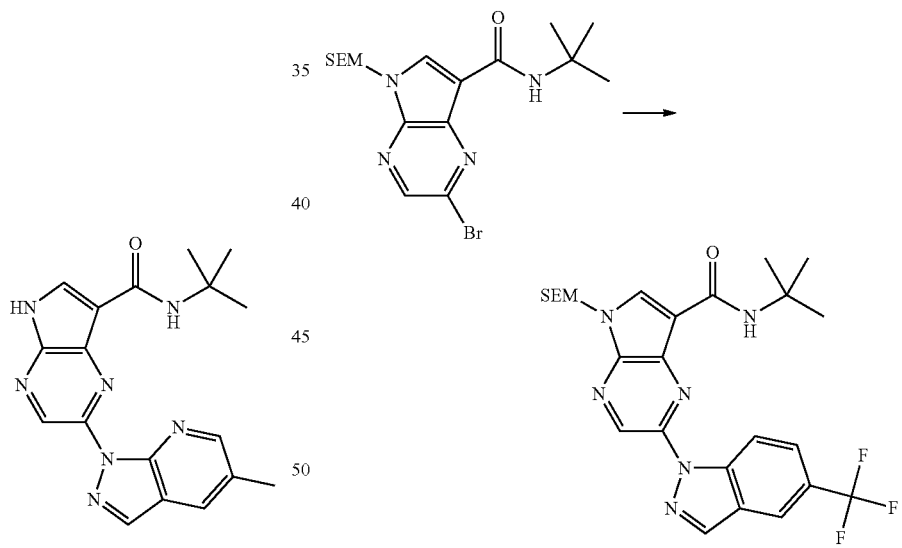

To a stirred solution of N-tert-butyl-2-(5-methyl-1H-pyrazolo[3,4-b]pyridin-1-yl)-5-((2-(trimethylsilyl)ethoxy)methyl)-5H-pyrrolo[2,3-b]pyrazine-7-carboxamide (0.1 g, 208 µmol) in dichloromethane (3 mL) was added trifluoroacetic acid (1 mL). After 15 h, the mixture was concentrated in vacuo then 25 mL of a Jan. 10, 1960 mixture of ammonium hydroxide/methanol/dichloromethane added. After 1 h the mixture was concentrated in vacuo. Purification by chromatography (silica, 24 g Analogix column, 0-4% methanol containing 10% ammonium hydroxide in dichloromethane) gave 2-(5-methyl-pyrazolo[3,4-b]pyridin-1-yl)-5H-pyrrolo[2,3-b]pyrazine-7-carboxylic acid tert-butylamide (10 mg, 14%). MS (M+H)$^+$=350; $^1$H NMR (DMSO-d$_6$) δ: 9.08 (s, 1H), 8.54 (d, J=1.8 Hz, 1H), 8.50 (s, 1H), 8.39 (s, 1H), 8.28 (s, 1H), 8.21 (dd, J=2.0, 0.8 Hz, 1H), 1.49 (s, 9H).

Example 337

2-(5-Trifluoromethyl-indazol-1-yl)-5H-pyrrolo[2,3-b]pyrazine-7-carboxylic acid tert-butylamide

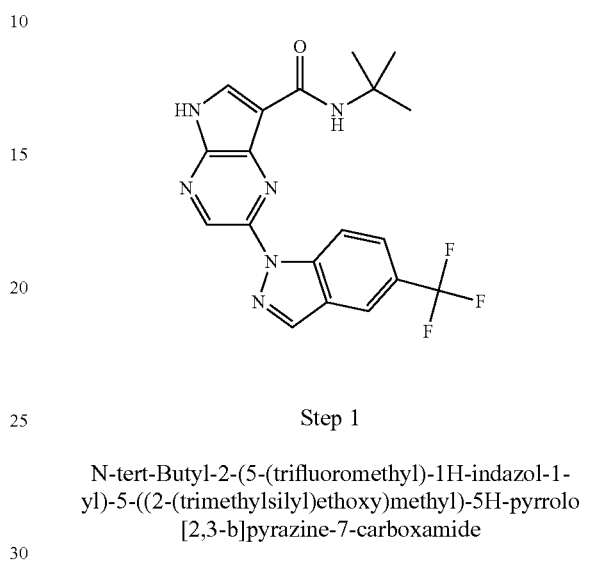

Step 1

N-tert-Butyl-2-(5-(trifluoromethyl)-1H-indazol-1-yl)-5-((2-(trimethylsilyl)ethoxy)methyl)-5H-pyrrolo[2,3-b]pyrazine-7-carboxamide To a stirred solution of 2-bromo-N-tert-butyl-5-((2-(trimethylsilyl)ethoxy)methyl)-5H-pyrrolo[2,3-b]pyrazine-7-carboxamide (200 mg, 468 µmol), 5-(trifluoromethyl)-1H-indazole (87.1 mg, 468 µmol) in dioxane (3.5 mL) was added sodium tert-butoxide (98.9 mg, 1.03 mmol) and bis(tri-tert-butylphosphine)palladium(0) (23.9 mg, 46.8 µmol). The mixture was degassed then heated in sealed tube at 125° C. for two days. The mixture was cooled, filtered through celite, the cake washed with ethyl acetate, and the combined filtrates were concentrated in vacuo. Purification by chromatography (silica, 24 g Analogix column, 0-30% ethyl acetate in hexanes) gave N-tert-butyl-2-(5-(trifluoromethyl)-1H-indazol-1-yl)-5-((2-(trimethylsilyl)ethoxy)methyl)-5H-pyrrolo[2,3- b]pyrazine-7-carboxamide (110 mg, 44%). $^1$H NMR (CDCl$_3$) δ: 9.20 (s, 1H), 8.69-8.74 (m, 2H), 8.42 (s, 2H), 8.39 (d, J=0.8 Hz, 1H), 8.33-8.36 (m, 1H), 8.18 (s, 2H), 7.70-7.74 (m, 1H), 5.73 (s, 2H), 3.59 (dd, J=8.9, 7.7 Hz, 2H), 1.63 (s, 9H), 0.92-0.98 (m, 2H), −0.04 (s, 9H).

Step 2

2-(5-Trifluoromethyl-indazol-1-yl)-5H-pyrrolo[2,3-b]pyrazine-7-carboxylic acid tert-butylamide

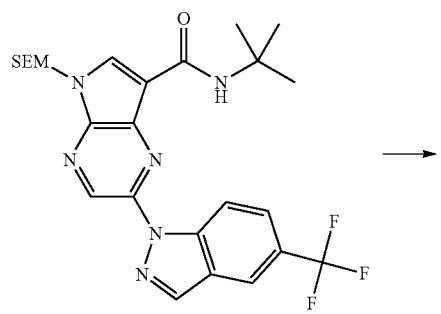

To a stirred solution of N-tert-butyl-2-(5-(trifluoromethyl)-1H-indazol-1-yl)-5-((2-(trimethylsilyl)ethoxy)methyl)-5H-pyrrolo[2,3-b]pyrazine-7-carboxamide (110 mg, 207 µmol) in dichloromethane (3 mL) was added trifluoroacetic acid (1 mL). After 15 h, the mixture was concentrated in vacuo, add 25 mL Jan. 10, 1960 mixture of ammonium hydroxide/methanol/dichloromethane, stir for 1 hour. concentrated in vacuo. Purification by chromatography (silica, 24 g Analogix column, 0-4% methanol containing 10% ammonium hydroxide in dichloromethane) gave 2-(5-trifluoromethyl-indazol-1-yl)-5H-pyrrolo[2,3-b]pyrazine-7-carboxylic acid tert-butylamide (6 mg, 7%). MS (M−H)$^-$=401; $^1$H NMR (DMSO-d$_6$) δ: 9.04 (s, 1H), 8.74 (d, J=9.0 Hz, 1H), 8.54 (d, J=2.8 Hz, 1H), 8.46 (s, 1H), 8.39 (d, J=2.5 Hz, 1H), 8.33 (s, 1H), 8.09 (s, 1H), 1.50 (s, 4H), 1.44 (s, 9H).

Example 338

2-(6-Methoxy-indazol-1-yl)-5H-pyrrolo[2,3-b]pyrazine-7-carboxylic acid tert-butylamide

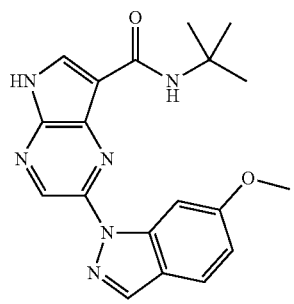 [SMILES: COc1ccc2cnn(-c3cnc4[nH]cc(C(=O)NC(C)(C)C)c4n3)c2c1]

Step 1

N-tert-Butyl-2-(6-methoxy-1H-indazol-1-yl)-5-((2-(trimethylsilyl)ethoxy)methyl)-5H-pyrrolo[2,3-b]pyrazine-7-carboxamide

To a stirred solution of 2-bromo-N-tert-butyl-5-((2-(trimethylsilyl)ethoxy)methyl)-5H-pyrrolo[2,3-b]pyrazine-7-carboxamide (200 mg, 468 µmol), 6-methoxy-1H-indazole (69.3 mg, 468 µmol) in dioxane (3.5 mL) was added sodium tert-butoxide (98.9 mg, 1.03 mmol) and bis(tri-tert-butylphosphine)palladium(0) (23.9 mg, 46.8 µmol). The mixture was degassed then heated in sealed tube at 125° C. for two days. The mixture was cooled, filtered through celite, the cake washed with ethyl acetate, and the combined filtrates were concentrated in vacuo. Purification by chromatography (silica, 24 g Analogix column, 0-30% ethyl acetate in hexanes) gave N-tert-butyl-2-(6-methoxy-1H-indazol-1-yl)-5-((2-(trimethylsilyl)ethoxy)methyl)-5H-pyrrolo[2,3-b]pyrazine-7-carboxamide (131 mg, 57%). $^1$H NMR (CDCl$_3$) δ:

9.06 (s, 1H), 8.33 (s, 1H), 8.18 (d, J=0.8 Hz, 1H), 7.95 (d, J=2.0 Hz, 1H), 7.80 (s, 1H), 7.73 (d, J=8.8 Hz, 1H), 7.01 (dd, J=8.8, 2.3 Hz, 1H), 5.71 (s, 2H), 3.94 (s, 3H), 3.53-3.63 (m, 2H), 1.57 (s, 9H), 0.91-0.98 (m, 2H), −0.03 (s, 9H).

Step 2

2-(6-Methoxy-indazol-1-yl)-5H-pyrrolo[2,3-b]pyrazine-7-carboxylic acid tert-butylamide

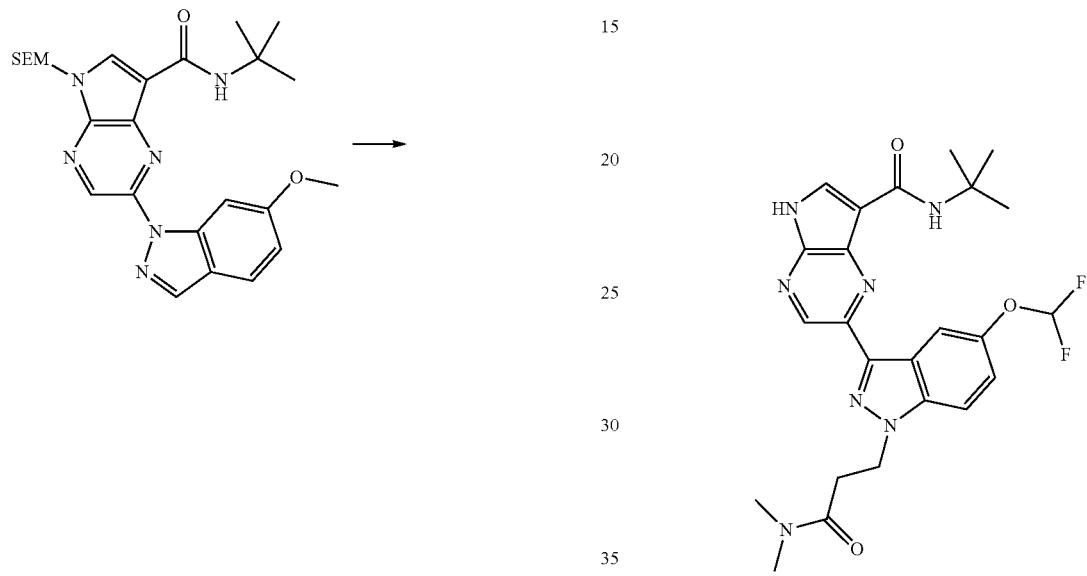

To a stirred solution of N-tert-butyl-2-(6-methoxy-1H-indazol-1-yl)-5-((2-(trimethylsilyl)ethoxy)methyl)-5H-pyrrolo[2,3-b]pyrazine-7-carboxamide (130 mg, 263 μmol) in dichloromethane (3 mL) was added trifluoroacetic acid (1 mL). After 15 h, the mixture was concentrated in vacuo, add 25 mL Jan. 10, 1960 mixture of ammonium hydroxide/methanol/dichloromethane, stir for 1 hour. concentrated in vacuo. Purification by chromatography (silica, 24 g Analogix column, 0-4% methanol containing 10% ammonium hydroxide in dichloromethane) gave 2-(6-methoxy-indazol-1-yl)-5H-pyrrolo[2,3-b]pyrazine-7-carboxylic acid tert-butylamide (63 mg, 66%). MS (M+H)$^+$=365; $^1$H NMR (DMSO-d$_6$) δ: 8.92 (s, 1H), 8.40 (d, J=5.1 Hz, 2H), 8.01 (s, 1H), 7.85 (d, J=8.9 Hz, 1H), 7.67 (s, 1H), 7.07 (dd, J=8.9, 2.0 Hz, 1H), 3.91 (s, 3H), 1.46 (s, 9H).

Example 339

2-[5-Difluoromethoxy-1-(2-dimethylcarbamoyl-ethyl)-1H-indazol-3-yl]-5H-pyrrolo[2,3-b]pyrazine-7-carboxylic acid tert-butylamide

Step 1

N-tert-Butyl-2-(5-(difluoromethoxy)-1-(3-(dimethylamino)-3-oxopropyl)-1H-indazol-3-yl)-5-((2-(trimethylsilyl)ethoxy)methyl)-5H-pyrrolo[2,3-b]pyrazine-7-carboxamide

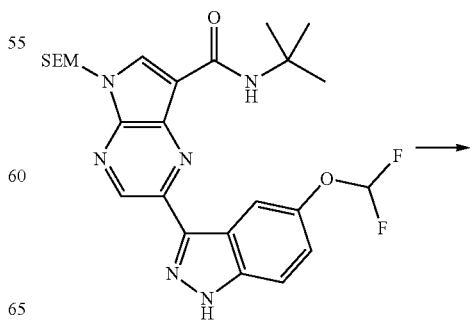

1081

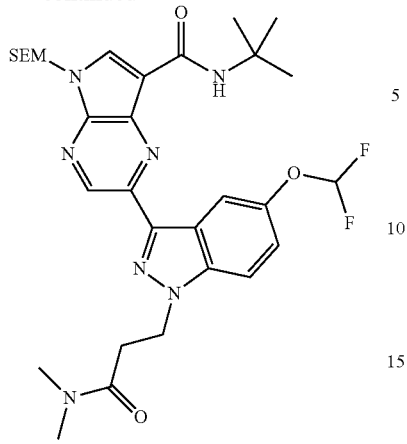

N-tert-Butyl-2-(5-(difluoromethoxy)-1H-indazol-3-yl)-5-((2-(trimethylsilyl)ethoxy)methyl)-5H-pyrrolo[2,3-b]pyrazine-7-carboxamide (100 mg, 188 μmol), 3-chloro-N,N-dimethylpropanamide (25.6 mg, 188 μmol) and cesium carbonate (184 mg, 565 mmol) in dimethylformamide (2 mL) were heated in a microwave at 150° C. for 30 min. The mixture was cooled, partitioned between ethyl acetate and water, washed with water 3 times, dried and concentrated in vacuo. Purification by chromatography (silica, 24 g Analogix column, 0-100% ethyl acetate in hexanes) gave N-tert-butyl-2-(5-(difluoromethoxy)-1-(3-(dimethylamino)-3-oxopropyl)-1H-indazol-3-yl)-5-((2-(trimethylsilyl)ethoxy)methyl)-5H-pyrrolo[2,3-b]pyrazine-7-carboxamide (70 mg, 59%) as an off-white solid. MS (M+H)$^+$=630; $^1$H NMR (CDCl$_3$) δ: 9.19 (s, 1H), 8.41 (s, 1H), 8.25 (d, J=1.9 Hz, 1H), 8.08 (s, 1H), 7.67 (d, J=8.7 Hz, 1H), 7.31-7.37 (m, 1H), 6.22-6.78 (m, 1H), 5.72 (s, 2H), 4.79-4.88 (m, 2H), 3.53-3.63 (m, 2H), 3.11 (t, J=6.7 Hz, 2H), 2.95 (d, J=9.2 Hz, 6H), 1.61 (s, 9H), 0.87-1.01 (m, 2H), −0.03 (s, 9H).

Step 2

2-[5-Difluoromethoxy-1-(2-dimethylcarbamoyl-ethyl)-1H-indazol-3-yl]-5H-pyrrolo[2,3-b]pyrazine-7-carboxylic acid tert-butylamide

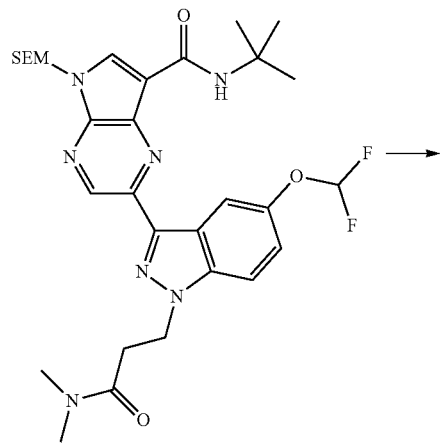

1082

To a stirred solution of N-tert-butyl-2-(5-(difluoromethoxy)-1-(3-(dimethylamino)-3-oxopropyl)-1H-indazol-3-yl)-5-((2-(trimethylsilyl)ethoxy)methyl)-5H-pyrrolo[2,3-b]pyrazine-7-carboxamide (70 mg, 111 μmol) in dichloromethane (4 mL) was added trifluoroacetic acid (1 mL). After 15 h, the mixture was concentrated in vacuo then 25 mL Jan. 10, 1960 mixture of ammonium hydroxide/methanol/dichloromethane added. After 1 h the mixture was concentrated in vacuo. Purification by chromatography (silica, 24 g Analogix column, 0-5% methanol containing 10% ammonium hydroxide in dichloromethane) gave 2-[5-difluoromethoxy-1-(2-dimethylcarbamoyl-ethyl)-1H-indazol-3-yl]-5H-pyrrolo[2,3-b]pyrazine-7-carboxylic acid tert-butylamide (50 mg, 90%). MS (M+H)$^+$=500; $^1$H NMR (CDCl$_3$) δ: 9.20 (s, 1H), 8.45 (d, J=3.0 Hz, 1H), 8.24 (d, J=2.0 Hz, 1H), 8.13 (s, 1H), 7.68 (d, J=9.3 Hz, 1H), 7.34 (dd, J=9.0, 2.3 Hz, 1H), 6.26-6.77 (m, 1H), 4.83 (t, J=6.7 Hz, 2H), 3.11 (t, J=6.7 Hz, 2H), 2.96 (d, J=14.1 Hz, 6H), 1.62 (s, 9H).

Example 340

2-[1-(4-Benzyl-morpholin-2-ylmethyl)-5-difluoromethoxy-1H-indazol-3-yl]-5H-pyrrolo[2,3-b]pyrazine-7-carboxylic acid tert-butylamide

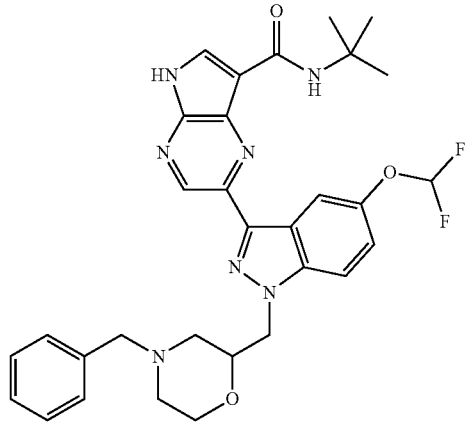 [SMILES: CC(C)(C)NC(=O)c1c[nH]c2ncc(-c3nn(CC4CN(Cc5ccccc5)CCO4)c4ccc(OC(F)F)cc34)nc12]

1083

Step 1

2-(1-((4-Benzylmorpholin-2-yl)methyl)-5-(difluoromethoxy)-1H-indazol-3-yl)-N-tert-butyl-5-((2-(trimethylsilyl)ethoxy)methyl)-5H-pyrrolo[2,3-b]pyrazine-7-carboxamide

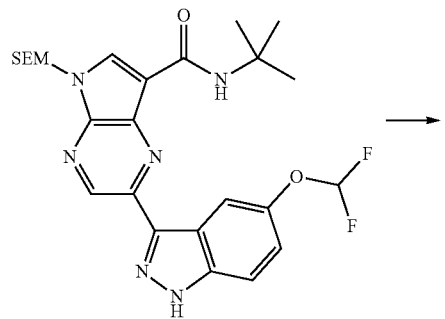

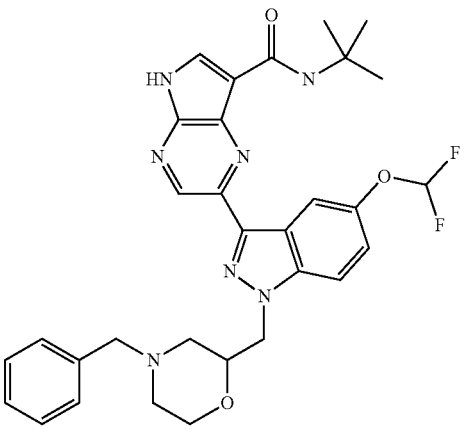

N-tert-Butyl-2-(5-(difluoromethoxy)-1H-indazol-3-yl)-5-((2-(trimethylsilyl)ethoxy)methyl)-5H-pyrrolo[2,3-b]pyrazine-7-carboxamide (100 mg, 188 μmol), 4-benzyl-2-(chloromethyl)morpholine (51.0 mg, 226 μmol) and cesium carbonate (184 mg, 565 mmol) in dimethylformamide (1.4 mL) were heated in a microwave at 100° C. for 45 min. The mixture was cooled, partitioned between ethyl acetate and water, and the organic phases combined and washed with water 3 times. The organic phase was dried and concentrated in vacuo. Purification by chromatography (silica, 24 g Analogix column, 0-40% ethyl acetate in hexanes) gave 2-(1-((4-benzylmorpholin-2-yl)methyl)-5-(difluoromethoxy)-

1084

1H-indazol-3-yl)-N-tert-butyl-5-((2-(trimethylsilyl)ethoxy)methyl)-5H-pyrrolo[2,3-b]pyrazine-7-carboxamide (67 mg, 49%).

Step 2

2-[1-(4-Benzyl-morpholin-2-ylmethyl)-5-difluoromethoxy-1H-indazol-3-yl]-5H-pyrrolo[2,3-b]pyrazine-7-carboxylic acid tert-butylamide

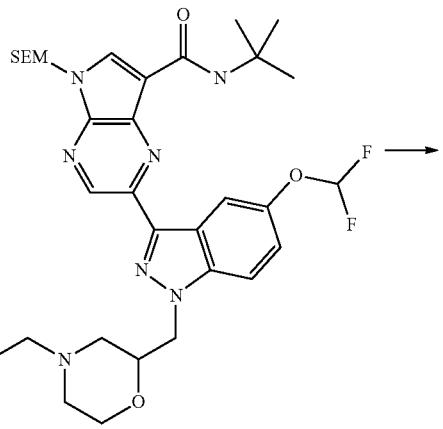

To a stirred solution of 2-(1-((4-benzylmorpholin-2-yl)methyl)-5-(difluoromethoxy)-1H-indazol-3-yl)-N-tert-butyl-5-((2-(trimethylsilyl)ethoxy)methyl)-5H-pyrrolo[2,3-b]pyrazine-7-carboxamide (40 mg, 55.6 μmol) in dichloromethane (10 mL) was added trifluoroacetic acid (1 mL). After 15 h, the mixture was concentrated in vacuo then 25 mL of a Jan. 10, 1960 mixture of ammonium hydroxide/methanol/dichloromethane added. After 1 h the mixture was concentrate. Purification by chromatography (silica, 24 g Analogix column, 0-5% methanol containing 10% ammonium hydroxide in dichloromethane) gave 2-[1-(4-benzyl-morpholin-2-ylmethyl)-5-difluoromethoxy-1H-indazol-3-yl]-5H-pyrrolo[2,3-b]pyrazine-7-carboxylic acid tert-butylamide (25 mg, 76%). MS (M+H)$^+$=590; $^1$H NMR (DMSO-d$_6$) δ: 9.04 (s, 1H), 8.39 (s, 1H), 8.18 (d, J=2.3 Hz, 1H), 7.88 (d, J=4.0 Hz, 1H), 7.36-7.41 (m, 1H), 7.29-7.33 (m, 5H), 7.22-7.27 (m, 1H), 6.98-7.21 (m, 1H), 4.54-4.68 (m, 2H), 3.96-4.03 (m, 1H), 3.74 (d, J=11.0 Hz, 1H), 3.49 (s, 2H), 3.40-3.48 (m, 1H), 2.86 (d, J=11.3 Hz, 1H), 2.58 (d, J=12.3 Hz, 1H), 1.87-2.11 (m, 2H), 1.50 (s, 9H).

Example 341

2-[5-Difluoromethoxy-1-(1-methyl-azetidin-3-ylmethyl)-1H-indazol-3-yl]-5H-pyrrolo[2,3-b]pyrazine-7-carboxylic acid tert-butylamide

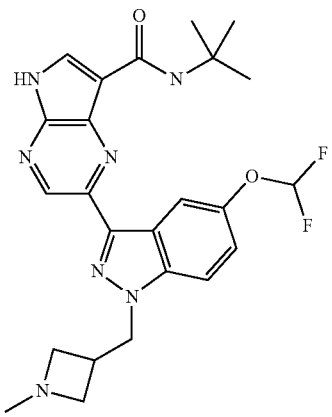 [SMILES: CN1CC(Cn2nc(-c3cnc4[nH]cc(C(=O)NC(C)(C)C)c4n3)c3cc(OC(F)F)ccc32)C1]

Step 1 tert-Butyl 3-((3-(7-(tert-butylcarbamoyl)-5-((2-(trimethylsilyl)ethoxy)methyl)-5H-pyrrolo[2,3-b]pyrazin-2-yl)-5-(difluoromethoxy)-1H-indazol-1-yl)methyl)azetidine-1-carboxylate

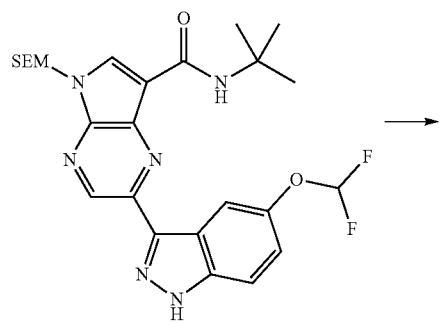

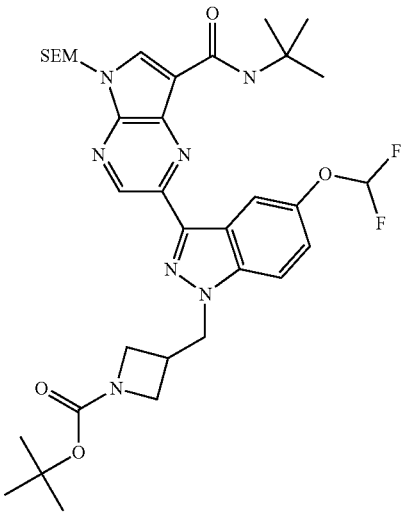

N-tert-Butyl-2-(5-(difluoromethoxy)-1H-indazol-3-yl)-5-((2-(trimethylsilyl)ethoxy)methyl)-5H-pyrrolo[2,3-b]pyrazine-7-carboxamide (100 mg, 188 µmol), tert-butyl 3-(iodomethyl)azetidine-1-carboxylate (56.0 mg, 188 µmol) and cesium carbonate (184 mg, 565 µmol) in dimethylformamide (2 mL) were heated in a microwave at 150° C. for 30 min. The mixture was cooled, partitioned between ethyl acetate and water, and the organic phase washed with water 3 times then dried and concentrated. Purification by chromatography (silica, 24 g Analogix column, 0-40% ethyl acetate in hexanes) gave tert-butyl 3-((3-(7-(tert-butylcarbamoyl)-5-((2-(trimethylsilyl)ethoxy)methyl)-5H-pyrrolo[2,3-b]pyrazin-2-yl)-5-(difluoromethoxy)-1H-indazol-1-yl)methyl)azetidine-1-carboxylate (108 mg, 82%). MS (M+H)$^+$=700; $^1$H NMR (CDCl$_3$) δ: 9.18 (s, 1H), 8.34 (s, 1H), 8.30 (d, J=2.1 Hz, 1H), 8.00 (s, 1H), 7.50 (d, J=9.0 Hz, 1H), 7.35 (dd, J=9.0, 2.1 Hz, 1H), 6.24-6.81 (m, 1H), 5.72 (s, 3H), 5.30 (s, 2H), 4.66 (d, J=7.5 Hz, 2H), 3.89 (dd, J=8.9, 5.2 Hz, 2H), 3.58 (dd, J=8.8, 7.6 Hz, 2H), 3.21-3.33 (m, 1H), 1.61 (s, 9H), 1.45 (s, 9H), 0.88-1.00 (m, 2H), −0.08--0.01 (m, 9H).

Step 2

2-(1-(Azetidin-3-ylmethyl)-5-(difluoromethoxy)-1H-indazol-3-yl)-N-tert-butyl-5-((2-(trimethylsilyl)ethoxy)methyl)-5H-pyrrolo[2,3-b]pyrazine-7-carboxamide

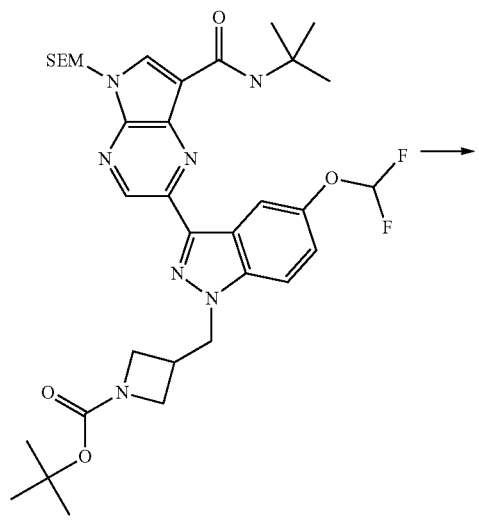

A stirred solution of tert-butyl 3-((3-(7-(tert-butylcarbamoyl)-5-((2-(trimethylsilyl)ethoxy)methyl)-5H-pyrrolo[2,3-b]pyrazin-2-yl)-5-(difluoromethoxy)-1H-indazol-1-yl)methyl)azetidine-1-carboxylate (180 mg, 257 µmol) in 2,2,2-trifluoroethanol (2 mL) was heated in a microwave at 150° C. for 6 h then cooled, concentrated and used in the next reaction without purification.

Step 3

N-tert-Butyl-2-(5-(difluoromethoxy)-1-((1-methylazetidin-3-yl)methyl)-1H-indazol-3-yl)-5-((2-(trimethylsilyl)ethoxy)methyl)-5H-pyrrolo[2,3-b]pyrazine-7-carboxamide

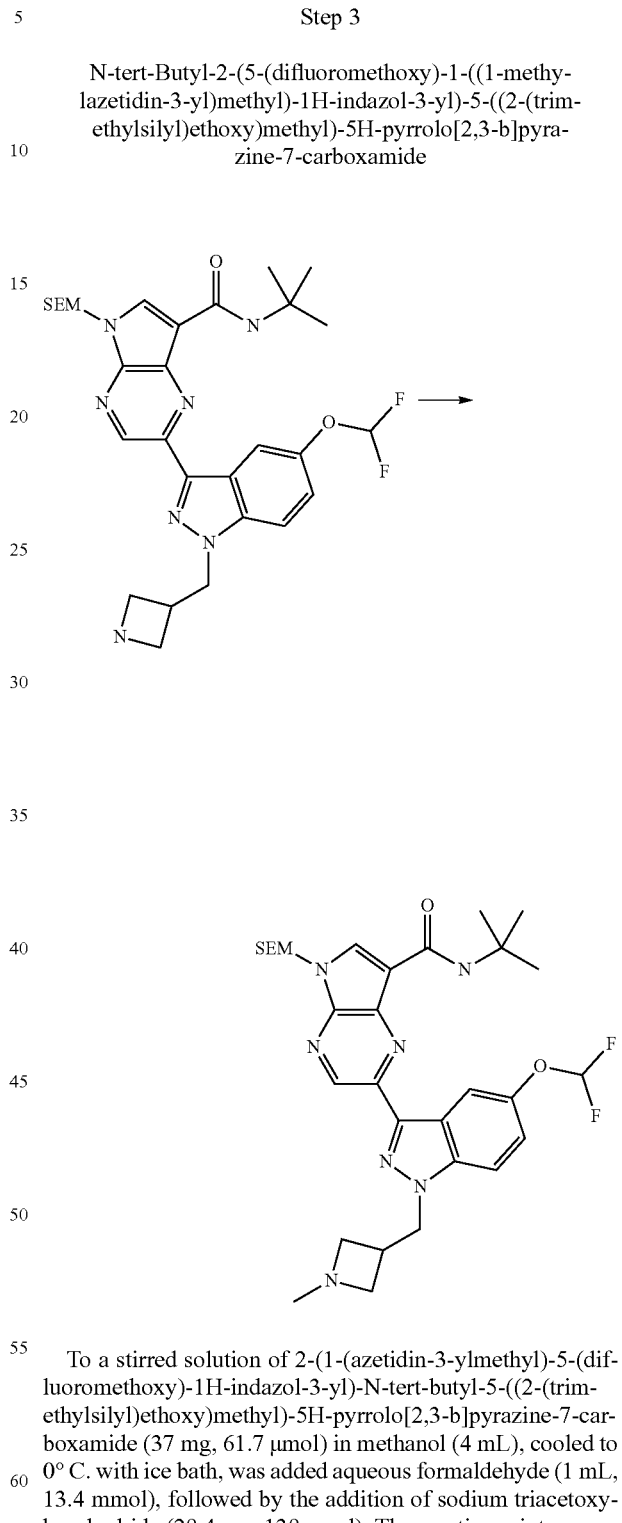

To a stirred solution of 2-(1-(azetidin-3-ylmethyl)-5-(difluoromethoxy)-1H-indazol-3-yl)-N-tert-butyl-5-((2-(trimethylsilyl)ethoxy)methyl)-5H-pyrrolo[2,3-b]pyrazine-7-carboxamide (37 mg, 61.7 µmol) in methanol (4 mL), cooled to 0° C. with ice bath, was added aqueous formaldehyde (1 mL, 13.4 mmol), followed by the addition of sodium triacetoxyborohydride (29.4 mg, 139 µmol). The reaction mixture was stirred at room temperature for 15 h then concentrated and purified by chromatography (silica, 4 g Analogix column, 0-10% methanol containing 10% ammonium hydroxide in dichloromethane) to give N-tert-butyl-2-(5-(difluoromethoxy)-1-((1-methylazetidin-3-yl)methyl)-1H-indazol- 3-yl)-5-((2-(trimethylsilyl)ethoxy)methyl)-5H-pyrrolo[2,3-b]pyrazine-7-carboxamide (33 mg, 87%). MS (M+H)⁺=614.

Step 4

2-[5-Difluoromethoxy-1-(1-methyl-azetidin-3-ylmethyl)-1H-indazol-3-yl]-5H-pyrrolo[2,3-b]pyrazine-7-carboxylic acid tert-butylamide

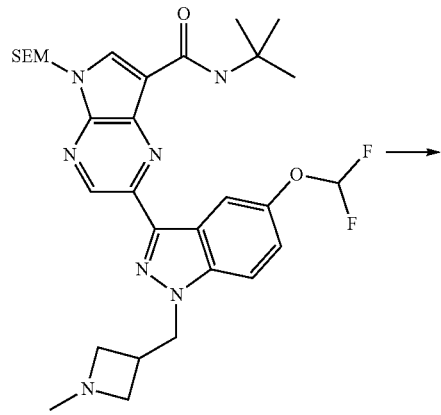

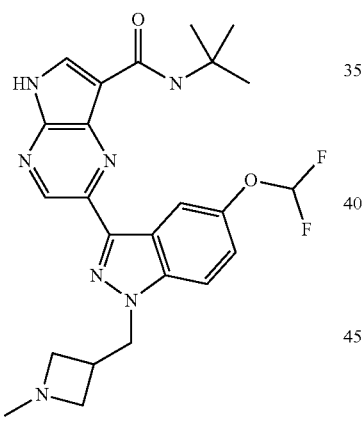

To a stirred solution of N-tert-butyl-2-(5-(difluoromethoxy)-1-((1-methylazetidin-3-yl)methyl)-1H-indazol-3-yl)-5-((2-(trimethylsilyl)ethoxy)methyl)-5H-pyrrolo[2,3-b]pyrazine-7-carboxamide (33 mg, 53.8 μmol) in dichloromethane (2 mL) was added trifluoroacetic acid (1 mL). After stirring at room temperature for 15 h the mixture was concentrated in vacuo then 25 mL of a Jan. 10, 1960 mixture of ammonium hydroxide/methanol/dichloromethane solution was added. After 1 h, the mixture was concentrated in vacuo. Purification by chromatography (silica, 24 g Analogix column, 0-4% methanol containing 10% ammonium hydroxide in dichloromethane) gave 2-[5-difluoromethoxy-1-(1-methyl-azetidin-3-ylmethyl)-1H-indazol-3-yl]-5H-pyrrolo[2,3-b]pyrazine-7-carboxylic acid tert-butylamide (18 mg, 69%). MS (M+H)⁺=484; ¹H NMR (DMSO-d₆) δ: 9.07 (s, 1H), 8.39 (s, 1H), 8.21 (d, J=2.3 Hz, 2H), 7.93 (d, J=9.0 Hz, 1H), 7.87 (s, 1H), 7.38-7.46 (m, 2H), 7.20 (s, 1H), 4.76 (d, J=7.3 Hz, 2H), 4.55 (s, 2H), 3.48 (t, J=8.0 Hz, 1H), 2.36 (s, 3H), 1.50 (s, 9H), 1.05 (t, J=7.3 Hz, 2H).

Example 342

2-[5-Difluoromethoxy-1-(4-methyl-morpholin-2-ylmethyl)-1H-indazol-3-yl]-5H-pyrrolo[2,3-b]pyrazine-7-carboxylic acid tert-butylamide

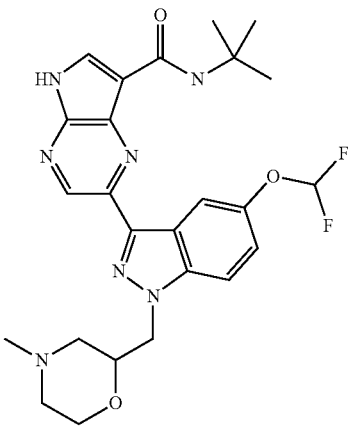 [SMILES: CN1CCOC(Cn2nc(-c3cnc4[nH]cc(C(=O)NC(C)(C)C)c4n3)c3cc(OC(F)F)ccc32)C1]

Step 1

N-tert-Butyl-2-(5-(difluoromethoxy)-1-(morpholin-2-ylmethyl)-1H-indazol-3-yl)-5-((2-(trimethylsilyl)ethoxy)methyl)-5H-pyrrolo[2,3-b]pyrazine-7-carboxamide

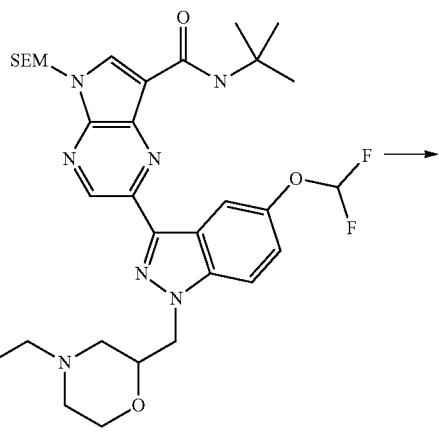

1091

-continued

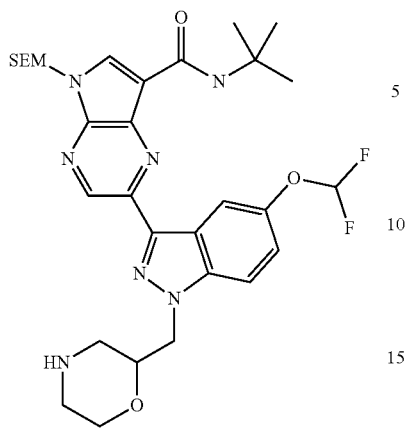

To a stirred solution of 2-(1-((4-benzylmorpholin-2-yl)methyl)-5-(difluoromethoxy)-1H-indazol-3-yl)-N-tert-butyl-5-((2-(trimethylsilyl)ethoxy)methyl)-5H-pyrrolo[2,3-b]pyrazine-7-carboxamide (see Example 340, 130 mg, 181 µmol) in ethyl acetate (2 mL) and methanol (1 mL) was added palladium on carbon (19.2 mg) and the mixture hydrogenated using a balloon filled with hydrogen gas. After stirring at room temperature for 15 h, the mixture was transferred to a Parr hydrogenator and shaken under 40 psi for 1 h. The mixture was filtered, concentrated in vacuo and then purified by chromatography (silica, 24 g Analogix column, 0-100% ethyl acetate in hexanes followed by 5% methanol in ethyl acetate) to give N-tert-butyl-2-(5-(difluoromethoxy)-1-(morpholin-2-ylmethyl)-1H-indazol-3-yl)-5-((2-(trimethylsilyl)ethoxy)methyl)-5H-pyrrolo[2,3-b]pyrazine-7-carboxamide (0.10 g 88%). MS (M+H)$^+$=630.

Step 2

N-tert-Butyl-2-(5-(difluoromethoxy)-1-((4-methylmorpholin-2-yl)methyl)-1H-indazol-3-yl)-5-((2-(trimethylsilyl)ethoxy)methyl)-5H-pyrrolo[2,3-b]pyrazine-7-carboxamide

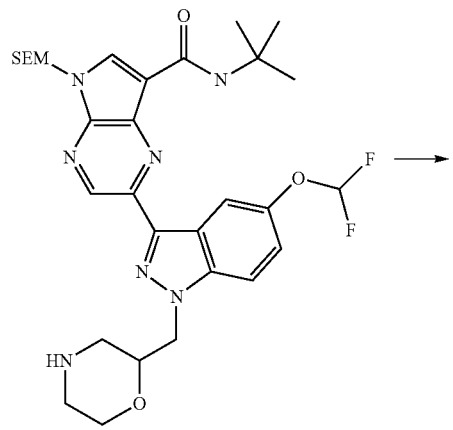

1092

-continued

To a stirred solution of N-tert-butyl-2-(5-(difluoromethoxy)-1-(morpholin-2-ylmethyl)-1H-indazol-3-yl)-5-((2-(trimethylsilyl)ethoxy)methyl)-5H-pyrrolo[2,3-b]pyrazine-7-carboxamide (100 mg, 159 µmol) in methanol (4 mL), cooled to 0° C. with ice bath, was added aqueous formaldehyde (1 mL, 13.4 mmol), followed by the addition of sodium triacetoxyborohydride (75.7 mg, 357 µmol). The reaction mixture was stirred at room temperature for 15 h then concentrated in vacuo. Purification by chromatography (silica, 4 g Analogix column, 0-10% methanol containing 10% ammonium hydroxide in dichloromethane) gave N-tert-butyl-2-(5-(difluoromethoxy)-1-(4-methylmorpholin-2-yl)methyl)-1H-indazol-3-yl)-5-((2-(trimethylsilyl)ethoxy)methyl)-5H-pyrrolo[2,3-b]pyrazine-7-carboxamide (63 mg, 62%). MS (M+H)$^+$=644.

Step 3

2-[5-Difluoromethoxy-1-(4-methyl-morpholin-2-ylmethyl)-1H-indazol-3-yl]-5H-pyrrolo[2,3-b]pyrazine-7-carboxylic acid tert-butylamide

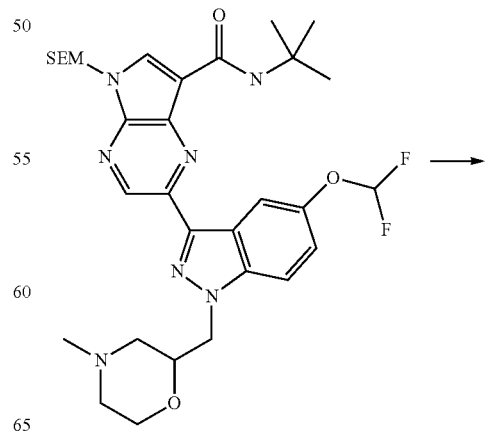

-continued

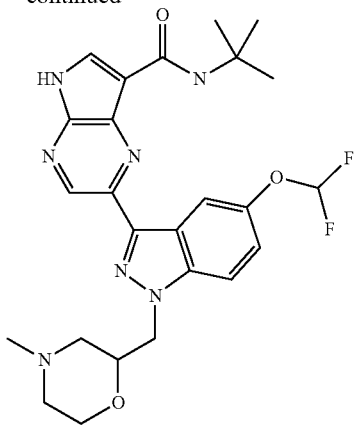

To a stirred solution of N-tert-butyl-2-(5-(difluoromethoxy)-1-((4-methylmorpholin-2-yl)methyl)-1H-indazol-3-yl)-5-((2-(trimethylsilyl)ethoxy)methyl)-5H-pyrrolo[2,3-b]pyrazine-7-carboxamide (63 mg, 97.9 μmol) in dichloromethane (2 mL) was added trifluoroacetic acid (1 mL). After stirring at room temperature for 15 h the mixture was concentrated in vacuo then 25 mL Jan. 10, 1960 mixture of ammonium hydroxide/methanol/dichloromethane was added. After 1 h the mixture was concentrated and purified by chromatography (silica, 24 g Analogix column, 0-4% methanol containing 10% ammonium hydroxide in dichloromethane) to give 2-[5-difluoromethoxy-1-(4-methyl-morpholin-2-ylmethyl)-1H-indazol-3-yl]-5H-pyrrolo[2,3-b]pyrazine-7-carboxylic acid tert-butylamide (22 mg, 43%). MS (M+H)$^+$=514; $^1$H NMR (DMSO-d$_6$) δ: 9.07 (s, 1H), 8.39 (s, 1H), 8.19 (d, J=2.3 Hz, 1H), 7.89 (s, 1H), 7.86 (s, 1H), 7.39 (dd, J=9.0, 2.3 Hz, 1H), 7.20 (s, 1H), 4.58-4.68 (m, 2H), 3.74 (d, J=11.9 Hz, 1H), 3.37-3.48 (m, 1H), 2.79 (d, J=11.3 Hz, 1H), 2.57 (br. s., 3H), 2.18 (s, 3H), 1.84-2.01 (m, 1H), 1.51 (s, 9H).

Example 343

2-{5-Difluoromethoxy-1-[3-(3,3-difluoro-pyrrolidin-1-yl)-propyl]-1H-indazol-3-yl}-5H-pyrrolo[2,3-b]pyrazine-7-carboxylic acid tert-butylamide

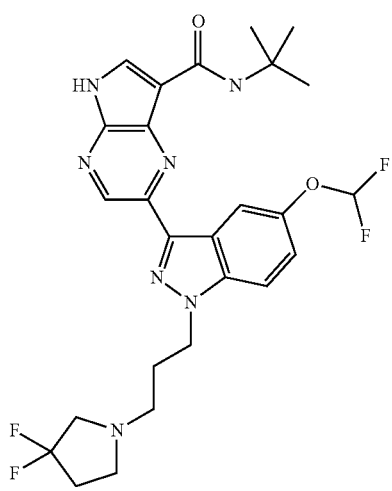 [SMILES: CC(C)(C)NC(=O)c1c[nH]c2ncc(-c3nn(CCCN4CCC(F)(F)C4)c4ccc(OC(F)F)cc34)nc12]

Step 1

N-tert-Butyl-2-(5-(difluoromethoxy)-1-(3-(3,3-difluoropyrrolidin-1-yl)propyl)-1H-indazol-3-yl)-5-((2-(trimethylsilyl)ethoxy)methyl)-5H-pyrrolo[2,3-b]pyrazine-7-carboxamide

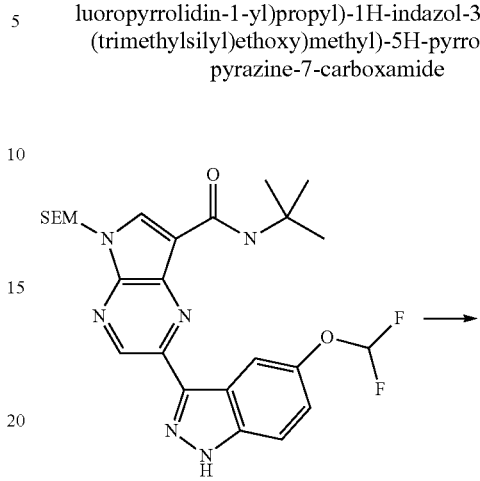

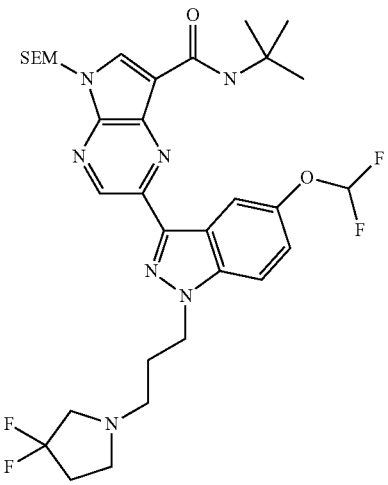

N-tert-Butyl-2-(5-(difluoromethoxy)-1H-indazol-3-yl)-5-((2-(trimethylsilyl)ethoxy)methyl)-5H-pyrrolo[2,3-b]pyrazine-7-carboxamide (100 mg, 188 μmol), 1-(3-chloropropyl)-3,3-difluoropyrrolidine (34.6 mg, 188 μmol) and cesium carbonate (184 mg, 565 μmol) in dimethylformamide (2 mL) were heated in a microwave at 100° C. for 30 min. The mixture was cooled and partitioned between ethyl acetate and water. The organic phase was washed with water 3 times then dried and concentrated in vacuo. Purification by chromatography (silica, 24 g Analogix column, 0-40% ethyl acetate in hexanes) gave N-tert-butyl-2-(5-(difluoromethoxy)-1-(3-(3,3-difluoropyrrolidin-1-yl)propyl)-1H-indazol-3-yl)-5-((2-

(trimethylsilyl)ethoxy)methyl)-5H-pyrrolo[2,3-b]pyrazine-7-carboxamide (91 mg, 72%). MS (M+H)+=678.

Step 2

2-{5-Difluoromethoxy-1-[3-(3,3-difluoro-pyrrolidin-1-yl)-propyl]-1H-indazol-3-yl}-5H-pyrrolo[2,3-b]pyrazine-7-carboxylic acid tert-butylamide

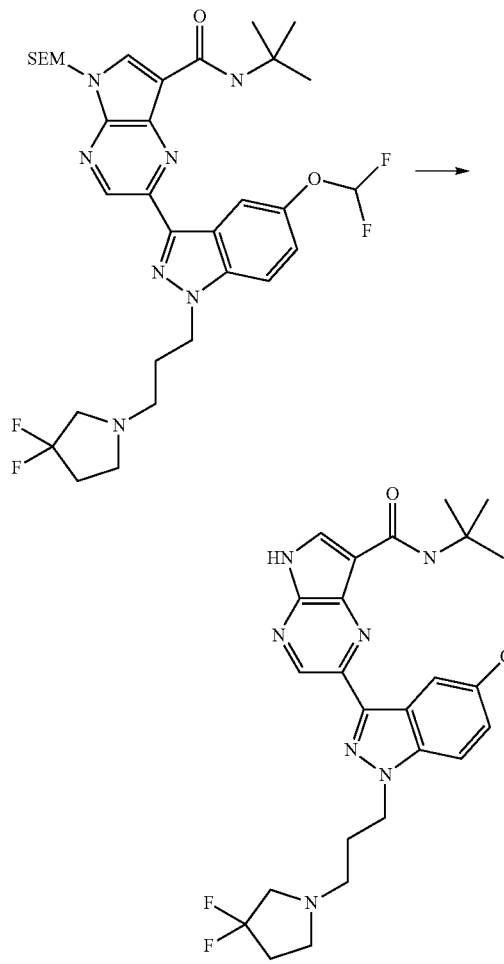

To a stirred solution of N-tert-butyl-2-(5-(difluoromethoxy)-1-(3-(3,3-difluoropyrrolidin-1-yl)propyl)-1H-indazol-3-yl)-5-((2-(trimethylsilyl)ethoxy)methyl)-5H-pyrrolo[2,3-b]pyrazine-7-carboxamide (91.4 mg, 135 µmol) in dichloromethane (2 mL) was added trifluoroacetic acid (1 mL). After 15 h the mixture was concentrated in vacuo. 25 mL of a Jan. 10, 1960 mixture of ammonium hydroxide/methanol/dichloromethane was added, and the reaction mixture stirred for 1 h then concentrated in vacuo. Purification by chromatography (silica, 24 g Analogix column, 0-4% methanol containing 10% ammonium hydroxide in dichloromethane) gave 2-{5-Difluoromethoxy-1-[3-(3,3-difluoro-pyrrolidin-1-yl)-propyl]-1H-indazol-3-yl}-5H-pyrrolo[2,3-b]pyrazine-7-carboxylic acid tert-butylamide (32 mg, 43%). MS (M+H)+=548; $^1$H NMR (DMSO-d$_6$) δ: 9.09 (s, 1H), 8.38 (s, 1H), 8.21 (d, J=2.3 Hz, 2H), 7.88 (s, 2H), 7.86 (s, 1H), 7.36-7.43 (m, 1H), 6.92-7.49 (m, 1H), 4.59 (t, J=6.8 Hz, 2H), 2.84 (t, J=13.6 Hz, 2H), 2.64 (t, J=7.0 Hz, 2H), 2.43 (t, J=6.7 Hz, 1H), 2.15-2.29 (m, 2H), 2.08 (t, J=7.0 Hz, 2H), 1.51 (s, 9H).

Example 344

2-(3-Methoxy-indazol-1-yl)-5H-pyrrolo[2,3-b]pyrazine-7-carboxylic acid (2-hydroxy-1,1-dimethyl-ethyl)-amide Step 1

N-(1-Hydroxy-2-methylpropan-2-yl)-2-(3-methoxy-1H-indazol-1-yl)-5-((2-(trimethylsilyl)ethoxy)methyl)-5H-pyrrolo[2,3-b]pyrazine-7-carboxamide To a stirred solution of 2-bromo-N-(1-hydroxy-2-methylpropan-2-yl)-5-((2-(trimethylsilyl)ethoxy)methyl)-5H-pyrrolo[2,3-b]pyrazine-7-carboxamide (150 mg, 338 µmol), 3-methoxy-1H-indazole (50.1 mg, 338 µmol) in dioxane (2 mL) was added sodium tert-butoxide (71.5 mg, 744 µmol) and bis(tri-tert-butylphosphine)palladium(0) (17.3 mg, 33.8 µmol). The mixture was degassed then heated in sealed tube at 125° C. for 15 h. The mixture was cooled, filtered through celite, and the filter cake washed with ethyl acetate. The combined filtrates were concentrated in vacuo and the crude residue purified by chromatography (silica, 24 g Analogix column, 0-40% ethyl acetate in hexanes) to give N-(1-hydroxy-2-methylpropan-2-yl)-2-(3-methoxy-1H-indazol-1-yl)-5-((2-(trimethylsilyl)ethoxy)methyl)-5H-pyrrolo[2,3-b]pyrazine-7-carboxamide (138 mg, 80%).

Step 2

2-(3-Methoxy-indazol-1-yl)-5H-pyrrolo[2,3-b]pyrazine-7-carboxylic acid (2-hydroxy-1,1-dimethyl-ethyl)-amide

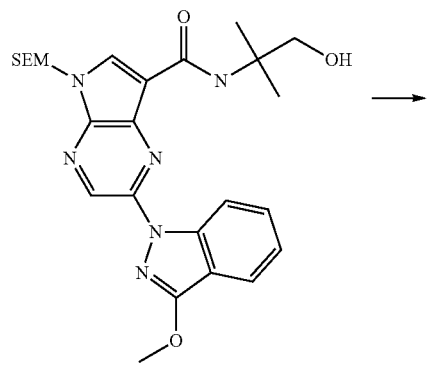

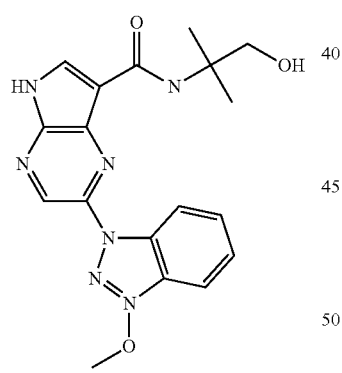

To a stirred solution of N-(1-hydroxy-2-methylpropan-2-yl)-2-(3-methoxy-1H-indazol-1-yl)-5-((2-(trimethylsilyl)ethoxy)methyl)-5H-pyrrolo[2,3-b]pyrazine-7-carboxamide (101 mg, 198 mmol) in dichloromethane (3 mL) was added trifluoroacetic acid (1 mL). After 15 h the mixture was concentrated in vacuo then 25 mL of a Jan. 10, 1960 mixture of ammonium hydroxide/methanol/dichloromethane solution was added. After 1 h, the mixture was concentrated in vacuo. Purification by chromatography (silica, 24 g Analogix column, 0-5% methanol containing 10% ammonium hydroxide in dichloromethane) gave 2-(3-methoxy-indazol-1-yl)-5H-pyrrolo[2,3-b]pyrazine-7-carboxylic acid (2-hydroxy-1,1-dimethyl-ethyl)amide (45 mg, 60%). MS (M+H)$^+$=381; $^1$H NMR (DMSO-d$_6$) δ: 8.94 (s, 1H), 8.62 (d, J=8.7 Hz, 1H), 8.33 (s, 1H), 7.79 (d, J=7.9 Hz, 1H), 7.61 (s, 2H), 7.28-7.38 (m, 1H), 4.19 (s, 3H), 3.62 (d, J=5.7 Hz, 2H), 1.45 (s, 6H).

Example 345

2-[5-Difluoromethoxy-1-(3-methylamino-propyl)-1H-indazol-3-yl]-5H-pyrrolo[2,3-b]pyrazine-7-carboxylic acid tert-butylamide

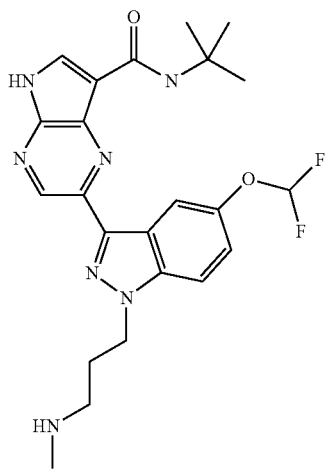 [SMILES: CNCCCn1nc(-c2cnc3[nH]cc(C(=O)NC(C)(C)C)c3n2)c2cc(OC(F)F)ccc21]

Step 1 tert-Butyl 3-(3-(7-(tert-butylcarbamoyl)-5-((2-(trimethylsilyl)ethoxy)methyl)-5H-pyrrolo[2,3-b]pyrazin-2-yl)-5-(difluoromethoxy)-1H-indazol-1-yl)propyl (methyl)carbamate

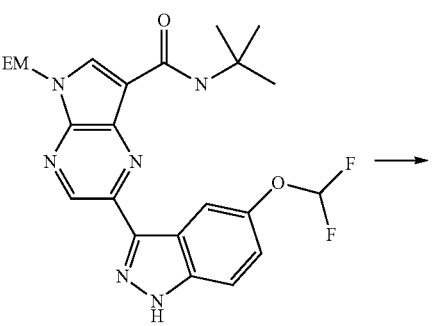

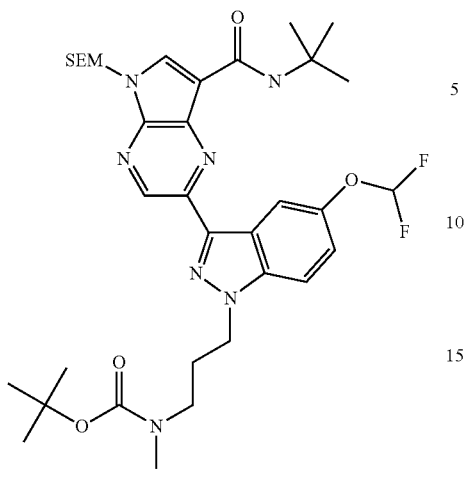

N-tert-Butyl-2-(5-(difluoromethoxy)-1H-indazol-3-yl)-5-((2-(trimethylsilyl)ethoxy)methyl)-5H-pyrrolo[2,3-b]pyrazine-7-carboxamide (280 mg, 528 μmol), tert-butyl 3-chloropropyl(methyl)carbamate (110 mg, 528 μmol) and cesium carbonate (516 mg, 1.58 mmol) in dimethylformamide (4 mL) were heated in a microwave at 100° C. for 30 min. The mixture was partitioned between ethyl acetate and water, then the organic phase washed with water 3 times, dried, filtered and concentrated. The crude residue was used in the next step without purification. MS (M+H)$^+$=702.

Step 2

2-[5-Difluoromethoxy-1-(3-methylamino-propyl)-1H-indazol-3-yl]-5H-pyrrolo[2,3-b]pyrazine-7-carboxylic acid tert-butylamide

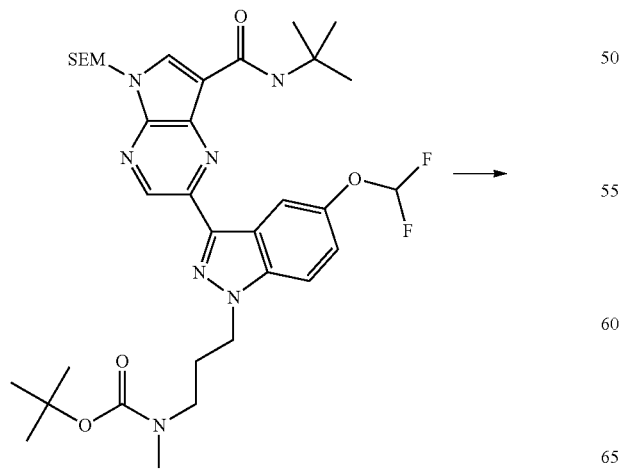

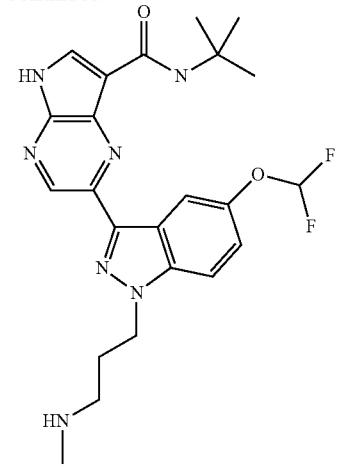

To a stirred solution of tert-butyl 3-(3-(7-(tert-butylcarbamoyl)-5-((2-(trimethylsilyl)ethoxy)methyl)-5H-pyrrolo[2,3-b]pyrazin-2-yl)-5-(difluoromethoxy)-1H-indazol-1-yl)propyl(methyl)carbamate (0.1 g, 142 μmol) in dichloromethane (3 mL) was added trifluoroacetic acid (1 mL). After 15 h the mixture was concentrated in vacuo. 25 mL of a Jan. 10, 1960 mixture of ammonium hydroxide/methanol/dichloromethane was added. After 1 h, the mixture was concentrated in vacuo. Purification by chromatography (silica, 24 g Analogix column, 0-5% methanol containing 10% ammonium hydroxide in dichloromethane) gave 2-[5-difluoromethoxy-1-(3-methylamino-propyl)-1H-indazol-3-yl]-5H-pyrrolo[2,3-b]pyrazine-7-carboxylic acid tert-butylamide (53 mg, 78%). MS (M+H)$^+$=472; $^1$H NMR (DMSO-d$_6$) δ: 9.30 (s, 1H), 8.61 (s, 1H), 8.43 (s, 1H), 8.08-8.14 (m, 2H), 7.59-7.68 (m, 1H), 7.12-7.71 (m, 1H), 4.82 (t, J=6.7 Hz, 4H), 3.54 (br. s., 3H), 2.27 (t, J=6.8 Hz, 2H), 1.73 (s, 9H).

Example 346

2-{1-[3-(Acetyl-methyl-amino)-propyl]-5-difluoromethoxy-1H-indazol-3-yl}-5H-pyrrolo[2,3-b]pyrazine-7-carboxylic acid tert-butylamide

1101

Step 1

N-tert-Butyl-2-(5-(difluoromethoxy)-1-(3-(N-methylacetamido)propyl)-1H-indazol-3-yl)-5-((2-(trimethylsilyl)ethoxy)methyl)-5H-pyrrolo[2,3-b]pyrazine-7-carboxamide

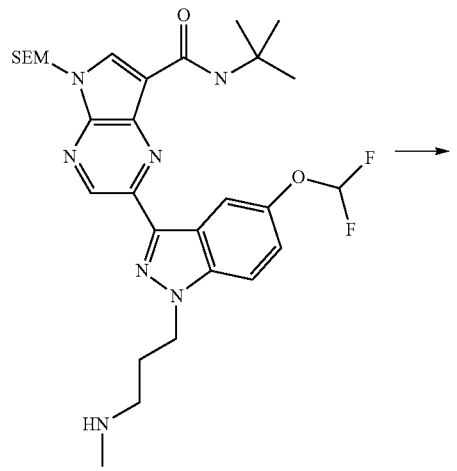

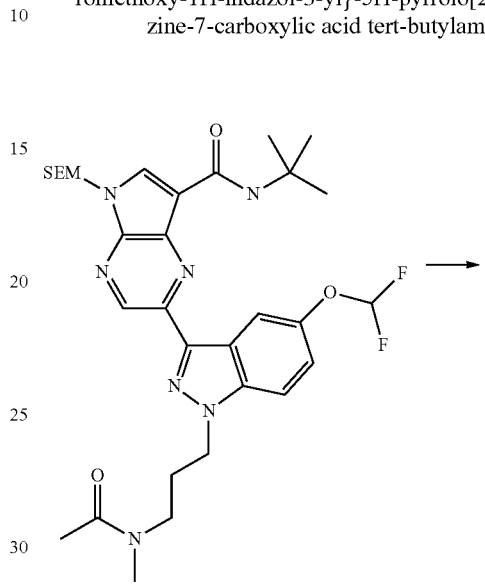

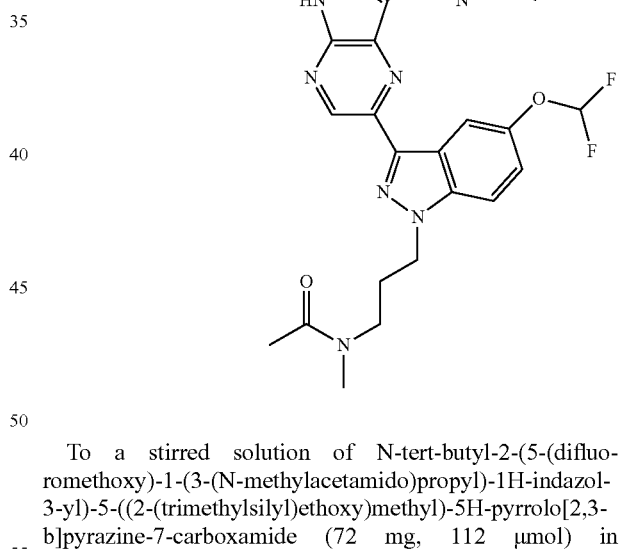

To a stirred solution of N-tert-butyl-2-(5-(difluoromethoxy)-1-(3-(methylamino)propyl)-1H-indazol-3-yl)-5-((2-(trimethylsilyl)ethoxy)methyl)-5H-pyrrolo[2,3-b]pyrazine-7-carboxamide (83 mg, 138 μmol) and cesium carbonate (135 mg, 414 μmol) in dimethylformamide (2 mL) was added acetyl chloride (10.8 mg, 138 μmol) and the mixture warmed to 90° C. After 2 h the mixture was cooled and concentrated in vacuo. Purification by chromatography (silica, 12 g Analogix column, 0-5% methanol containing 10% ammonium hydroxide in dichloromethane) gave N-tert-butyl-2-(5-(difluoromethoxy)-1-(3-(N-methylacetamido) propyl)-1H-indazol-3-yl)-5-((2-(trimethylsilyl)ethoxy)methyl)-5H-pyrrolo[2,3-b]pyrazine-7-carboxamide (72 mg, 81%). MS (M+H)$^+$=644.

Step 2

2-{1-[3-(Acetyl-methyl-amino)-propyl]-5-difluoromethoxy-1H-indazol-3-yl}-5H-pyrrolo[2,3-b]pyrazine-7-carboxylic acid tert-butylamide To a stirred solution of N-tert-butyl-2-(5-(difluoromethoxy)-1-(3-(N-methylacetamido)propyl)-1H-indazol-3-yl)-5-((2-(trimethylsilyl)ethoxy)methyl)-5H-pyrrolo[2,3-b]pyrazine-7-carboxamide (72 mg, 112 μmol) in dichloromethane (2 mL) was added trifluoroacetic acid (1 mL). After 15 h the mixture was concentrated in vacuo then 25 mL of a Jan. 10, 1960 mixture of ammonium hydroxide/methanol/dichloromethane was added. After 1 h the mixture was concentrated in vacuo. Purification by chromatography (silica, 24 g Analogix column, 0 to 5% methanol containing 10% ammonium hydroxide in dichloromethane) gave 2-{1-[3-(acetyl-methyl-amino)-propyl]-5-difluoromethoxy-1H-indazol-3-yl}-5H-pyrrolo[2,3-b]pyrazine-7-carboxylic acid tert-butylamide (32 mg, 56%). MS (M+H)$^+$=514; $^1$H NMR (DMSO-d$_6$) δ: 9.09 (s, 1H), 8.39 (s, 1H), 8.22 (br. s., 1H), 7.84-7.98 (m, 2H), 7.40 (d, J=9.8 Hz, 1H), 6.93-7.47 (m, 1H), 4.48-4.60 (m, 1H), 3.36-3.42 (m, 2H), 2.95 (s, 3H), 2.79 (s, 3H), 1.93 (d, J=7.5 Hz, 2H), 1.51 (s, 9H).

Example 347

2-(3-Piperidin-4-yl-indazol-1-yl)-5H-pyrrolo[2,3-b]pyrazine-7-carboxylic acid (2-hydroxy-1,1-dimethyl-ethyl)-amide

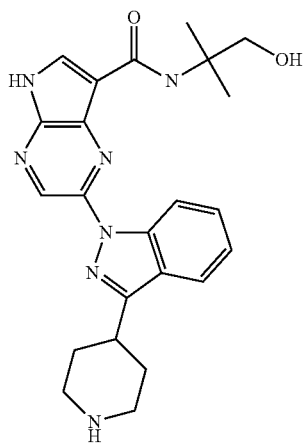 [SMILES: CC(C)(CO)NC(=O)c1c[nH]c2ncc(-n3nc(C4CCNCC4)c4ccccc43)nc12]

Step 1 tert-Butyl 4-(1-(7-(1-hydroxy-2-methylpropan-2-ylcarbamoyl)-5-((2-(trimethylsilyl)ethoxy)methyl)-5H-pyrrolo[2,3-b]pyrazin-2-yl)-1H-indazol-3-yl)piperidine-1-carboxylate

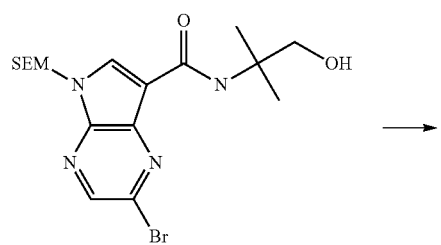

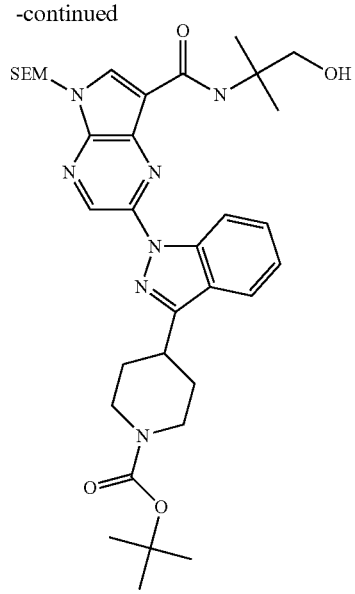

To a stirred solution of 2-bromo-N-(1-hydroxy-2-methylpropan-2-yl)-5-((2-(trimethylsilyl)ethoxy)methyl)-5H-pyrrolo[2,3-b]pyrazine-7-carboxamide (150 mg, 338 μmol), tert-butyl 4-(1H-indazol-3-yl)piperidine-1-carboxylate (102 mg, 338 μmol) in dioxane (2.5 mL) was added sodium tert-butoxide (71.5 mg, 744 μmol) and bis(tri-tert-butylphosphine)palladium(0) (17.3 mg, 33.8 μmol). The mixture was degassed then heated in sealed tube at 125° C. for 15 h. The mixture was cooled, filtered through celite, and the filter cake washed with ethyl acetate. The combined filtrates were concentrated in vacuo. Purification by chromatography (silica, 24 g Analogix column, 0-40% ethyl acetate in hexanes) gave tert-butyl 4-(1-(7-(1-hydroxy-2-methylpropan-2-ylcarbamoyl)-5-((2-(trimethylsilyl)ethoxy)methyl)-5H-pyrrolo[2,3-b]pyrazin-2-yl)-1H-indazol-3-yl)piperidine-1-carboxylate (198 mg, 88%).

Step 2

2-(3-Piperidin-4-yl-indazol-1-yl)-5H-pyrrolo[2,3-b]pyrazine-7-carboxylic acid (2-hydroxy-1,1-dimethyl-ethyl)-amide

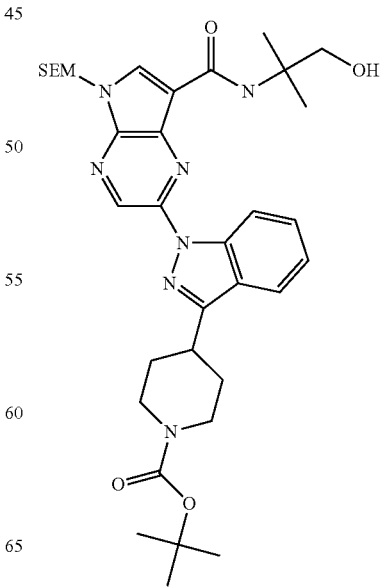

1105

-continued

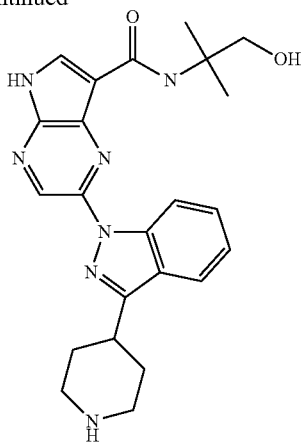

To a stirred solution of tert-butyl 4-(1-(7-(1-hydroxy-2-methylpropan-2-ylcarbamoyl)-5-((2-(trimethylsilyl)ethoxy)methyl)-5H-pyrrolo[2,3-b]pyrazin-2-yl)-1H-indazol-3-yl)piperidine-1-carboxylate (22 mg, 33.1 µmol) in dichloromethane (2 mL) was added trifluoroacetic acid (0.5 mL). After 15 h then mixture was concentrated in vacuo then 25 mL of a Jan. 10, 1960 mixture of ammonium hydroxide/methanol/dichloromethane added. After 1 h the mixture was concentrated in vacuo. Purification by chromatography (silica, 24 g Analogix column, 0-5% methanol containing 10% ammonium hydroxide in dichloromethane) gave 2-(3-piperidin-4-yl-indazol-1-yl)-5H-pyrrolo[2,3-b]pyrazine-7-carboxylic acid (2-hydroxy-1,1-dimethyl-ethyl)-amide (14 mg, 98%). MS (M+H)$^+$=434; $^1$H NMR (DMSO-d$_6$) δ: 8.98 (s, 1H), 8.63 (d, J=8.5 Hz, 1H), 8.37 (s, 1H), 8.01 (d, J=8.1 Hz, 1H), 7.65 (s, 1H), 7.57 (t, J=7.8 Hz, 1H), 7.30-7.41 (m, 1H), 3.61 (s, 4H), 3.20 (br. s., 3H), 2.80-2.93 (m, 2H), 1.88-2.12 (m, 2H), 1.43 (s, 6H).

Example 348

2-[3-(1-Methyl-piperidin-4-yl)-indazol-1-yl]-5H-pyrrolo[2,3-b]pyrazine-7-carboxylic acid (2-hydroxy-1,1-dimethyl-ethyl)-amide

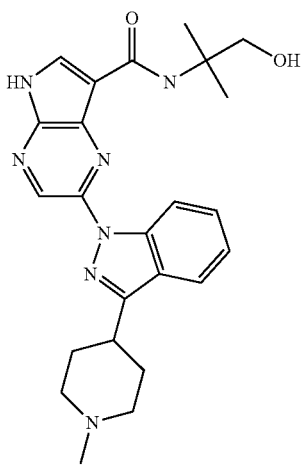 [SMILES: CN1CCC(c2nn(-c3cnc4[nH]cc(C(=O)NC(C)(C)CO)c4n3)c3ccccc23)CC1]

1106

Step 1

N-(1-hydroxy-2-methylpropan-2-yl)-2-(3-(piperidin-4-yl)-1H-indazol-1-yl)-5-((2-(trimethylsilyl)ethoxy)methyl)-5H-pyrrolo[2,3-b]pyrazine-7-carboxamide

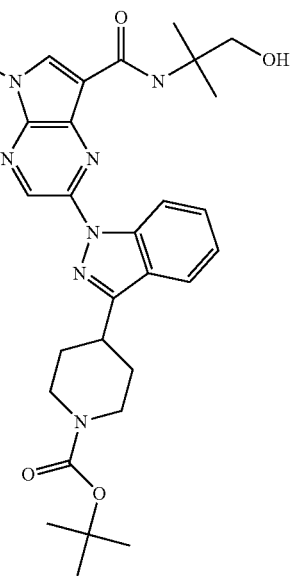

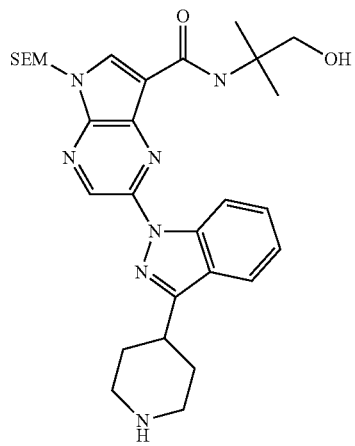

A stirred solution of tert-butyl 4-(1-(7-(1-hydroxy-2-methylpropan-2-ylcarbamoyl)-5-((2-(trimethylsilyl)ethoxy)methyl)-5H-pyrrolo[2,3-b]pyrazin-2-yl)-1H-indazol-3-yl)piperidine-1-carboxylate (120 mg, 181 µmol) in 2,2,2-

1107 trifluoroethanol (2 mL) was heated in a microwave at 150° C. for 4 h. The mixture was concentrated in vacuo and used in the next step without purification.

Step 2

N-(1-Hydroxy-2-methylpropan-2-yl)-2-(3-(1-methylpiperidin-4-yl)-1H-indazol-1-yl)-5-((2-(trimethylsilyl)ethoxy)methyl)-5H-pyrrolo[2,3-b]pyrazine-7-carboxamide


To a stirred solution of N-(1-hydroxy-2-methylpropan-2-yl)-2-(3-(piperidin-4-yl)-1H-indazol-1-yl)-5-((2-(trimethylsilyl)ethoxy)methyl)-5H-pyrrolo[2,3-b]pyrazine-7-carboxamide (100 mg, 177 μmol) in methanol (4 mL), cooled to 0° C. with an ice bath, was added 37% aqueous formaldehyde (1 mL, 13.4 mmol), followed by the addition of sodium triacetoxyborohydride (84.6 mg, 399 μmol). The reaction mixture was stirred at room temperature for 15 h then concentrated in vacuo. Purification by chromatography (silica, 4 g Analogix column, 0-6% methanol containing 10% ammonium hydroxide in dichloromethane) gave N-(1-hydroxy-2-methylpropan-2-yl)-2-(3-(1-methylpiperidin-4-yl)-1H-indazol-1-yl)-

1108

5-(2-(trimethylsilyl)ethoxy)methyl)-5H-pyrrolo[2,3-b]pyrazine-7-carboxamide (57 mg, 56%). MS (M+H)$^+$=578.

Step 3

2-[3-(1-Methyl-piperidin-4-yl)-indazol-1-yl]-5H-pyrrolo[2,3-b]pyrazine-7-carboxylic acid (2-hydroxy-1,1-dimethyl-ethyl)-amide To a stirred solution of N-(1-hydroxy-2-methylpropan-2-yl)-2-(3-(1-methylpiperidin-4-yl)-1H-indazol-1-yl)-5-((2-(trimethylsilyl)ethoxy)methyl)-5H-pyrrolo[2,3-b]pyrazine-7-carboxamide (57 m g, 98.7 μmol) in dichloromethane (3 mL) was added trifluoroacetic acid (1 mL). After 15 h the mixture was concentrated in vacuo then 25 mL of a Jan. 10, 1960 mixture of ammonium hydroxide/methanol/dichloromethane added. After 1 h the mixture was concentrated in vacuo. Purification by chromatography (silica, 24 g Analogix column, 0-6% methanol containing 10% ammonium hydroxide in dichloromethane) gave 2-[3-(1-methyl-piperidin-4-yl) indazol-1-yl]-5H-pyrrolo[2,3-b]pyrazine-7-carboxylic acid (2-hydroxy-1,1-dimethyl-ethyl)amide (10 mg, 23%). MS (M+H)$^+$=447; $^1$H NMR (DMSO-d$_6$) δ: 9.00 (s, 1H), 8.64 (d, J=8.5 Hz, 1H), 8.37 (s, 1H), 7.99 (d, J=7.9 Hz, 1H), 7.65 (s, 1H), 7.57 (t, J=7.3 Hz, 1H), 7.35 (t, J=7.5 Hz, 1H), 5.06 (t, J=5.7 Hz, 2H), 3.62 (d, J=5.7 Hz, 2H), 2.98 (d, J=11.5 Hz, 2H), 2.30 (s, 3H), 1.94-2.24 (m, 5H), 1.44 (s, 6H)

Example 349

2-(1-Azetidin-3-ylmethyl-6-fluoro-1H-indazol-3-yl)-5H-pyrrolo[2,3-b]pyrazine-7-carboxylic acid tert-butyl amide trifluoroacetate

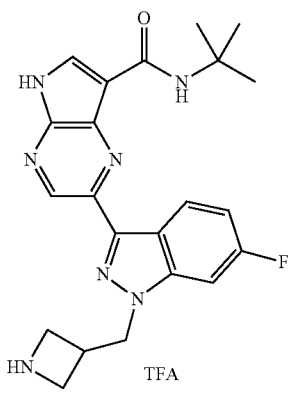 [SMILES: CC(C)(C)NC(=O)c1c[nH]c2ncc(-c3nn(CC4CNC4)c4cc(F)ccc34)nc12]

Step 1 tert-Butyl 3-((6-fluoro-3-(7-formyl-5-((2-(trimethylsilyl)ethoxy)methyl)-5H-pyrrolo[2,3-b]pyrazin-2-yl)-1H-indazol-1-yl)methyl)azetidine-1-carboxylate

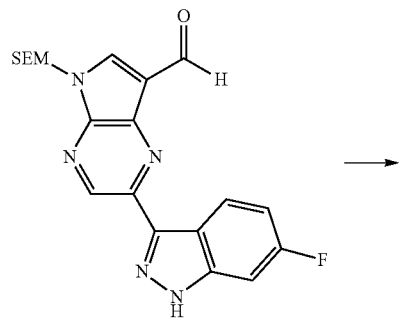

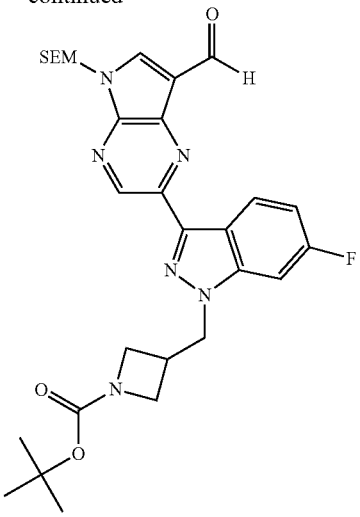

2-(6-Fluoro-1H-indazol-3-yl)-5-((2-(trimethylsilyl)ethoxy)methyl)-5H-pyrrolo[2,3-b]pyrazine-7-carbaldehyde (225 mg, 547 µmol), tert-butyl 3-(iodomethyl)azetidine-1-carboxylate (162 mg, 547 µmol) and cesium carbonate (534 mg, 1.64 mmol) in dimethylformamide (4 mL) were heated in a microwave at 150° C. for 30 min. The mixture was partitioned between ethyl acetate and water. Then the organic phase was washed with water 3 times, dried and concentrated in vacuo. Purification by chromatography (silica, 24 g Analogix column, 0-40% ethyl acetate in hexanes) gave tert-butyl 3-((6-fluoro-3-(7-formyl-5-((2-(trimethylsilyl)ethoxy)methyl)-5H-pyrrolo[2,3-b]pyrazin-2-yl)-1H-indazol-1-yl)methyl)azetidine-1-carboxylate (202 mg, 64%).

Step 2

2-(1-(((1-(tert-Butoxycarbonyl)azetidin-3-yl)methyl)-6-fluoro-1H-indazol-3-yl)-5-((2-(trimethylsilyl)ethoxy)methyl)-5H-pyrrolo[2,3-b]pyrazine-7-carboxylic acid

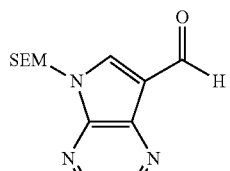

-continued

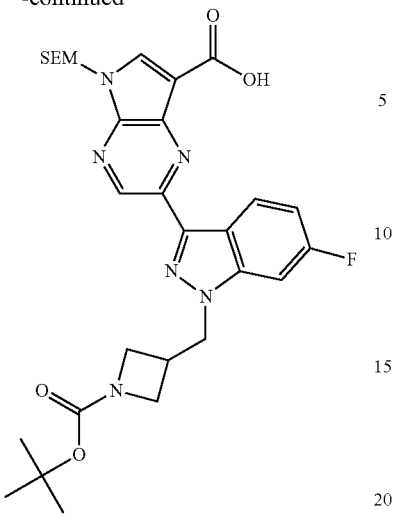

To a stirred solution of tert-butyl 3-((6-fluoro-3-(7-formyl-5-((2-(trimethylsilyl)ethoxy)methyl)-5H-pyrrolo[2,3-b]pyrazin-2-yl)-1H-indazol-1-yl)methyl)azetidine-1-carboxylate (160 mg, 276 μmol) and sulfamic acid (161 mg, 1.65 mmol) in dioxane (5 mL) and water (2 mL), cooled to 0° C., was added a solution of sodium chlorite (32.4 mg, 358 μmol) and potassium dihydrogen phosphate (450 mg, 3.31 mmol) in water (3 mL) dropwise. The mixture was warmed to room temperature. After 2.5 h, the mixture was partitioned between ethyl acetate and water and the organic phase separated and washed with water then dried and concentrated in vacuo. A quantitative yield was assumed and the crude residue used directly in the next step without further purification.

Step 3 tert-Butyl 3-((3-(7-(tert-butylcarbamoyl)-5-((2-(trimethylsilyl)ethoxy)methyl)-5H-pyrrolo[2,3-b]pyrazin-2-yl)-6-fluoro-1H-indazol-1-yl)methyl)azetidine-1-carboxylate

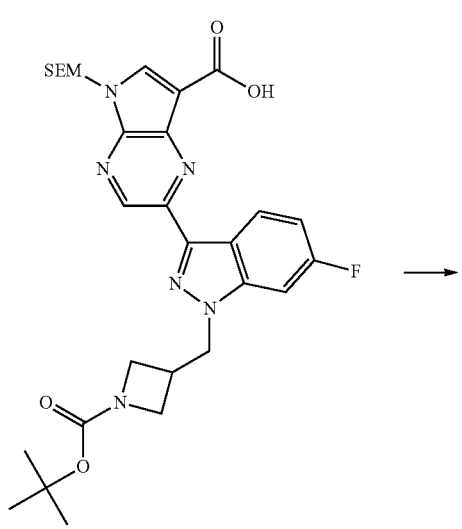

-continued

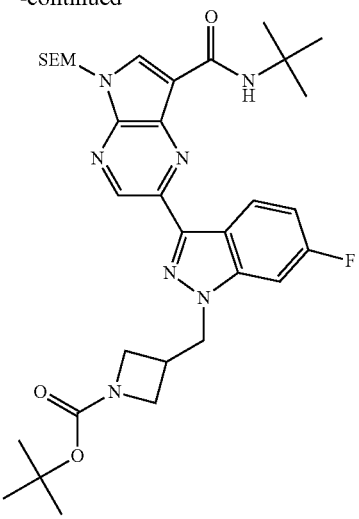

2-(1-((1-(tert-butoxycarbonyl)azetidin-3-yl)methyl)-6-fluoro-1H-indazol-3-yl)-5-((2-(trimethylsilyl)ethoxy)methyl)-5H-pyrrolo[2,3-b]pyrazine-7-carboxylic acid (150 mg, 251 μmol), 2-methylpropan-2-amine (18.4 mg, 251 μmol), HATU (105 mg, 277 μmol) and diisopropylamine (97.5 mg, 754 μmol) in dimethylformamide (12 mL) were stirred at room temperature for 15 h. The mixture was partitioned between ethyl acetate and water then the organic phase was washed with water then dried, filtered and concentrated in vacuo. Purification by chromatography (silica, 24 g Analogix column, 0-40% ethyl acetate in hexanes) gave tert-butyl 3-((3-(7-(tert-butylcarbamoyl)-5-((2-(trimethylsilyl)ethoxy)methyl)-5H-pyrrolo[2,3-b]pyrazin-2-yl)-6-fluoro-1H-indazol-1-yl)methyl)azetidine-1-carboxylate (150 mg, 91.5%).

Step 4

2-(1-Azetidin-3-ylmethyl-6-fluoro-1H-indazol-3-yl)-5H-pyrrolo[2,3-b]pyrazine-7-carboxylic acid tert-butyl amide trifluoroacetate

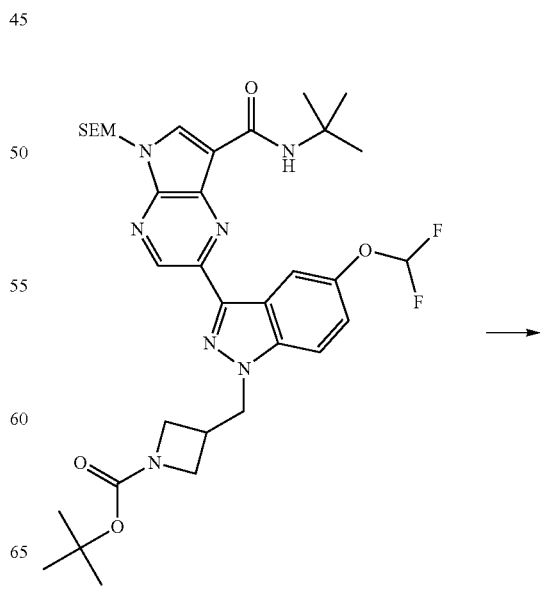

1113
-continued

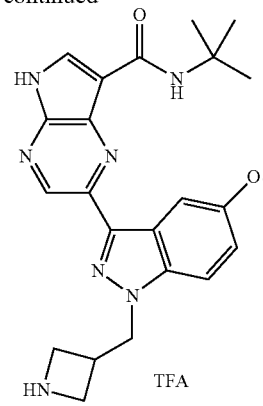
TFA

To a stirred solution of tert-butyl 3-((3-(7-(tert-butylcarbamoyl)-5-((2-(trimethylsilyl)ethoxy)methyl)-5H-pyrrolo[2,3-b]pyrazin-2-yl)-6-fluoro-1H-indazol-1-yl)methyl)azetidine-1-carboxylate (70 mg, 107 μmol) in dichloromethane (5 mL) was added trifluoroacetic acid (1 mL). After 15 h the mixture was concentrated in vacuo and the residue dissolved in 25 mL of a Jan. 10, 1960 mixture of ammonium hydroxide/methanol/dichloromethane. After 1 h the mixture was concentrated in vacuo. Purification by chromatography (silica, 24 g Analogix column, 0-6% methanol containing 10% ammonium hydroxide in dichloromethane) followed by SFC chromatography (eluent contained TFA) gave 2-(1-azetidin-3-ylmethyl-6-fluoro-1H-indazol-3-yl)-5H-pyrrolo[2,3-b]pyrazine-7-carboxylic acid tert-butyl amide trifluoroacetate (10 mg, 17%). MS (M+H)$^+$=422; $^1$H NMR (DMSO-d$_6$) δ: 9.09 (s, 1H), 8.49 (dd, J=8.9, 5.4 Hz, 1H), 8.40 (s, 1H), 7.92 (s, 1H), 7.77 (dd, J=9.8, 1.9 Hz, 1H), 7.20 (d, J=2.1 Hz, 1H), 4.77 (d, J=7.0 Hz, 2H), 3.87-4.18 (m, 4H), 1.52 (s, 9H), 1.24 (d, J=4.5 Hz, 1H).

Example 350

2-(1-Azetidin-3-ylmethyl-5-difluoromethoxy-1H-indazol-3-yl)-5H-pyrrolo[2,3-b]pyrazine-7-carboxylic acid tert-butylamide

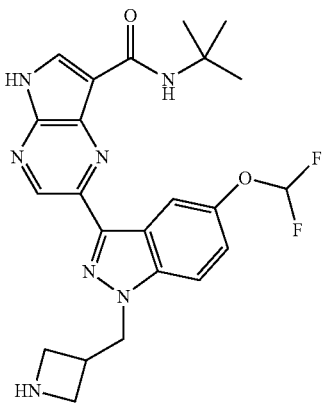 [SMILES: CC(C)(C)NC(=O)c1c[nH]c2ncc(-c3nn(CC4CNC4)c4ccc(OC(F)F)cc34)nc12]

1114
Step 1 tert-Butyl 3-((3-(7-(tert-butylcarbamoyl)-5-((2-(trimethylsilyl)ethoxy)methyl)-5H-pyrrolo[2,3-b]pyrazin-2-yl)-5-(difluoromethoxy)-1H-indazol-1-yl)methyl)azetidine-1-carboxylate

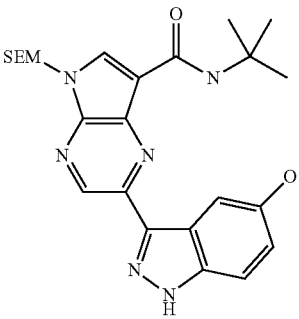

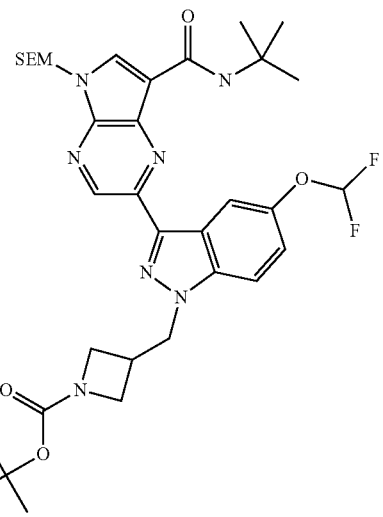

N-tert-Butyl-2-(5-(difluoromethoxy)-1H-indazol-3-yl)-5-((2-(trimethylsilyl)ethoxy)methyl)-5H-pyrrolo[2,3-b]pyrazine-7-carboxamide (152 mg, 286 μmol), tert-butyl 3-(iodomethyl)azetidine-1-carboxylate (85.1 mg, 286 μmol) and cesium carbonate (280 mg, 859 μmol) in dimethylformamide (3 mL) were heated in a microwave at 150° C. for 30 min. The mixture was partitioned between ethyl acetate and water, washed with water, dried and concentrated in vacuo. Purification by chromatography (silica, 24 g Analogix column, 0-40% ethyl acetate in hexanes) gave tert-butyl 3-((3-(7-(tert-butylcarbamoyl)-5-((2-(trimethylsilyl)ethoxy)methyl)-5H-pyrrolo[2,3-b]pyrazin-2-yl)-5-(difluoromethoxy)-1H-indazol-1-yl)methyl)azetidine-1-carboxylate that was used directly without purification. MS (M+H)+=702.

Step 2

2-(1-Azetidin-3-ylmethyl-5-difluoromethoxy-1H-indazol-3-yl)-5H-pyrrolo[2,3-b]pyrazine-7-carboxylic acid tert-butylamide

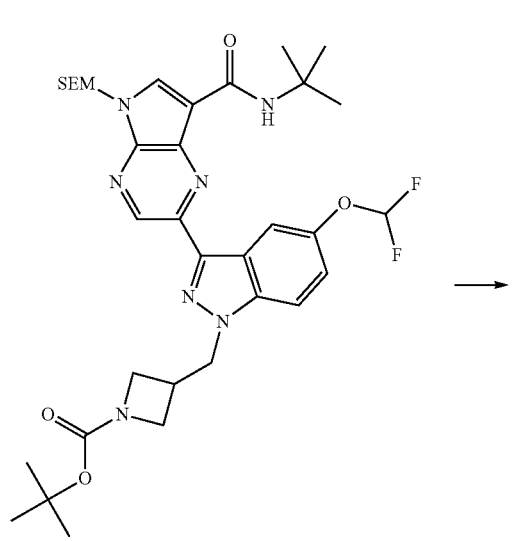

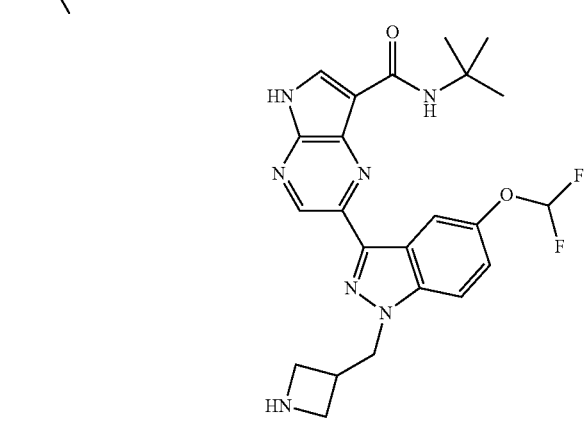

To a stirred solution of tert-butyl 3-((3-(7-(tert-butylcarbamoyl)-5-((2-(trimethylsilyl)ethoxy)methyl)-5H-pyrrolo[2,3-b]pyrazin-2-yl)-5-(difluoromethoxy)-1H-indazol-1-yl)methyl)azetidine-1-carboxylate (80 mg, 114 μmol) in dichloromethane (2 mL) was added trifluoroacetic acid (1 mL). After 15 h the mixture was concentrated in vacuo and the residue dissolved in 25 mL of a Jan. 10, 1960 mixture of ammonium hydroxide/methanol/dichloromethane. After 1 h, the mixture was concentrated in vacuo. Purification by chromatography (silica, 24 g Analogix column, 0-4% methanol containing 10% ammonium hydroxide in dichloromethane) gave 2-(1-azetidin-3-ylmethyl-5-difluoromethoxy-1H-indazol-3-yl)-5H-pyrrolo[2,3-b]pyrazine-7-carboxylic acid tert-butylamide (22 mg, 41%).

MS (M+H)+=470; 1H NMR (DMSO-d6, 300 MHz): δ=9.06 (d, J=4.0 Hz, 1H), 8.38 (d, J=7.7 Hz, 1H), 8.17-8.24 (m, 1H), 7.87 (s, 1H), 7.42 (d, J=9.4 Hz, 1H), 7.19 (d, J=4.1 Hz, 1H), 6.95 (d, J=4.1 Hz, 1H), 4.48-4.83 (m, 2H), 3.49-3.73 (m, 2H), 2.85-3.08 (m, 2H), 1.50 (d, J=3.8 Hz, 9H), 1.23 ppm (s, 1H)

Example 351

N-tert-Butyl-2-(1-(cyclopropylmethyl)-5-(difluoromethoxy)-1H-indazol-3-yl)-5H-pyrrolo[2,3-b]pyrazine-7-carboxamide

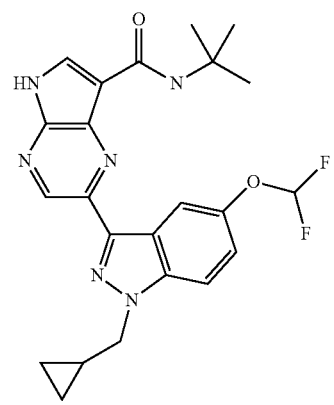 [SMILES: CC(C)(C)NC(=O)c1c[nH]c2ncc(-c3nn(CC4CC4)c4ccc(OC(F)F)cc34)nc12]

Step 1

N-tert-Butyl-2-(5-(difluoromethoxy)-1H-indazol-3-yl)-5-((2-(trimethylsilyl)ethoxy)methyl)-5H-pyrrolo[2,3-b]pyrazine-7-carboxamide

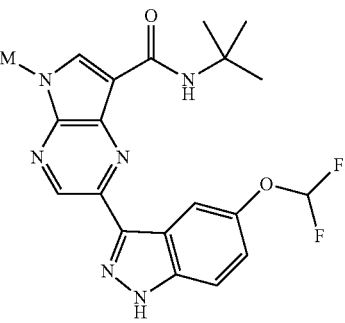

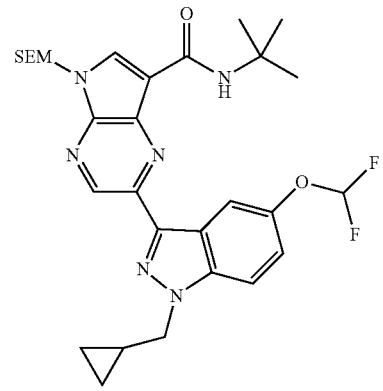

To a stirred solution of N-tert-butyl-2-(5-(difluoromethoxy)-1H-indazol-3-yl)-5-((2-(trimethylsilyl)ethoxy)methyl)-5H-pyrrolo[2,3-b]pyrazine-7-carboxamide (117.1 mg, 221 µmol) and (bromomethyl)cyclopropane (386 mg, 250 µL, 2.86 mmol) in DMF (60 mL) under Ar, cesium carbonate (750 mg, 2.3 mmol) was added in a single portion. The reaction mixture was stirred at 70° C. After 18 h, the reaction was cooled to 25° C. and quenched with water (200 mL). The mixture was extracted with ethyl acetate (3×75 mL) and the organics were washed with brine (100 mL). The organics were dried over sodium sulfate and concentrated to give N-tert-butyl-2-(1-(cyclopropylmethyl)-5-(difluoromethoxy)-1H-indazol-3-yl)-5-(2-(trimethylsilyl)ethoxy)methyl)-5H-pyrrolo[2,3-b]pyrazine-7-carboxamide (120 mg, 205 µmol, 86%). MS (M)'=585; $^1$H NMR (DMSO-d$_6$) δ: 9.14 (s, 1H), 8.59 (s, 1H), 8.20 (d, J=2.0 Hz, 1H), 7.93 (s, 1H), 7.87 (s, 1H), 7.41 (dd, J=2.0, 8.8 Hz, 1H), 7.21 (t, J=74.3 Hz, 1H), 5.86 (m, 1H), 5.07 (dd, J=1.5, 17.1 Hz, 1H), 4.98 (d, J=10.3 Hz, 1H), 4.64 (t, J=7.0 Hz, 2H), 3.58 (t, J=8.0 Hz, 2H), 2.70 (m, 2H), 1.51 (s, 9H), 0.86 (t, J=8.0 Hz, 2H), −0.08 (s, 9H).

Step 2

N-tert-Butyl-2-(1-(cyclopropylmethyl)-5-(difluoromethoxy)-1H-indazol-3-yl)-5H-pyrrolo[2,3-b]pyrazine-7-carboxamide

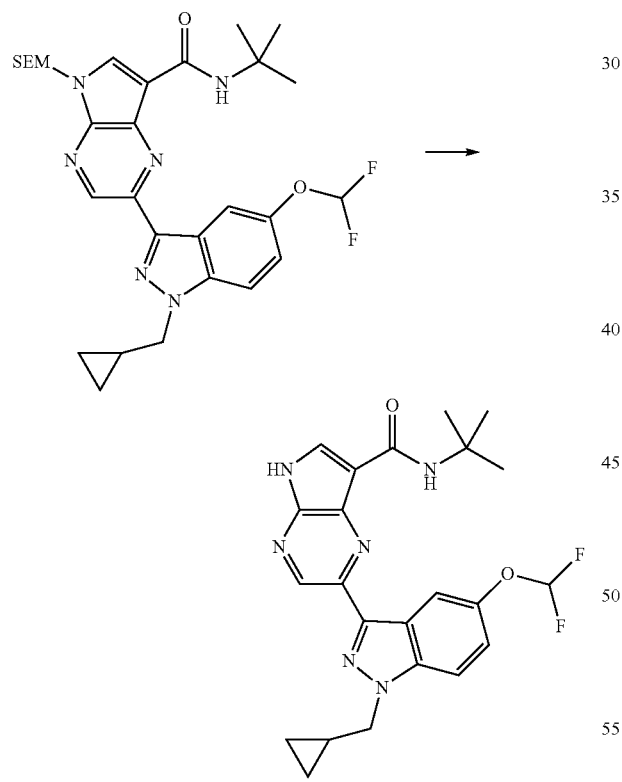

To a stirred solution of N-tert-butyl-2-(1-(cyclopropylmethyl)-5-(difluoromethoxy)-1H-indazol-3-yl)-5-((2-(trimethylsilyl)ethoxy)methyl)-5H-pyrrolo[2,3-b]pyrazine-7-carboxamide (140 mg, 239 µmol) in dichloromethane (10 mL) under Ar, trifluoroacetic acid (744 mg, 0.50 mL, 6.53 mmol) was added at 25° C. After 18 h, the reaction was concentrated in vacuo to give a light brown residue. The residue was dissolved in a mixture of dichloromethane/methanol/NH$_3$OH (3:2:0.25, 10.5 mL) and stirred at 25° C. After 2.5 h, the reaction was concentrated to give a yellow solid and dried in vacuo (200 mTorr, 25° C.). The solid was dissolved in ethanol (4.5 mL, 200 proof) and cooled to 4° C. After 18 h, the precipitated solid was isolated by filtration and dried in vacuo (200 mTorr, 40° C.) to give N-tert-butyl-2-(1-(cyclopropylmethyl)-5-(difluoromethoxy)-1H-indazol-3-yl)-5H-pyrrolo[2,3-b]pyrazine-7-carboxamide (72.8 mg, 160 µmol, 66.9%) as a yellow solid. MS (M)'=455; $^1$H NMR (DMSO-d$_6$) δ: 9.09 (s, 1H), 8.39 (s, 1H), 8.21 (d, J=2.3 Hz, 1H), 7.93 (d, J=9.0 Hz, 1H), 7.88 (s, 1H), 7.40 (dd, J=2.3, 9.0 Hz, 1H), 7.20 (t, J=74.3 Hz, 1H), 5.86 (m, 1H), 5.08 (dd, J=1.5, 17.3 Hz, 2H), 4.63 (t, J=7.0 Hz, 2H), 2.71 (m, 2H), 1.51 (s, 9H).

Example 352

N-tert-Butyl-2-(5-(difluoromethoxy)-1-(2-oxo-2-(4-(2,2,2-trifluoroethyl)piperazin-1-yl)ethyl)-1H-indazol-3-yl)-5H-pyrrolo[2,3-b]pyrazine-7-carboxamide

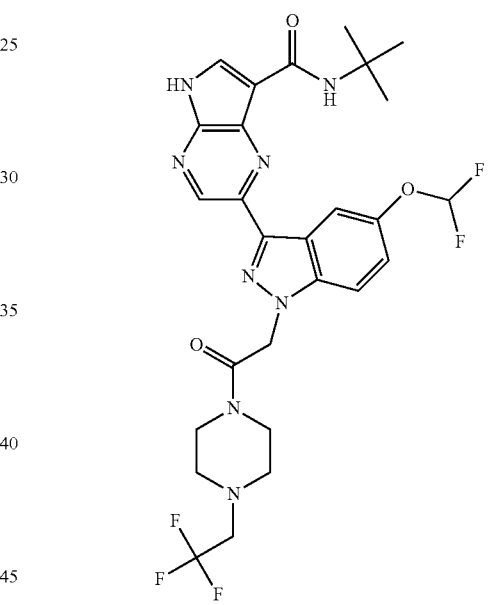

Step 1

2-Chloro-1-(4-(2,2,2-trifluoroethyl)piperazin-1-yl)ethanone

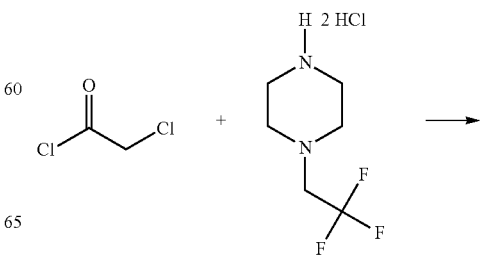

-continued

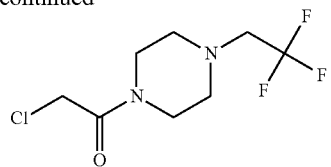

To as stirred solution of 1-(2,2,2-trifluoroethyl)piperazine dihydrochloride (181.6 mg, 753 µmol) and triethylamine (182 mg, 250 µL, 1.79 mmol) in dichloromethane (5 mL) cooled to 0° C., 2-chloroacetyl chloride (85.1 mg, 60.0 µL, 753 µmol) was added drop-wise over 2 min then stirred for 10 min. The reaction mixture was warmed to 25° C. over 3 h. The reaction mixture was partitioned between saturated sodium bicarbonate solution (25 mL) and dichloromethane (25 mL). The organic layer was separated, washed with water (25 mL) and brine (50 mL), dried over sodium sulfate, and concentrated to give 2-chloro-1-(4-(2,2,2-trifluoroethyl)piperazin-1-yl)ethanone (123.3 mg, 504 µmol, 67%) as an orange oil. $^1$H NMR (DMSO-$d_6$) δ: 4.73 (br. s, 2H), 3.45 (br. s, 4H), 3.23 (q, J=10.3 Hz, 2H), 2.61 (d, J=20.8 Hz, 4H).

Step 2

N-tert-Butyl-2-(5-(difluoromethoxy)-1-(2-oxo-2-(4-(2,2,2-trifluoroethyl)piperazin-1-yl)ethyl)-1H-indazol-3-yl)-5-((2-(trimethylsilyl)ethoxy)methyl)-5H-pyrrolo[2,3-b]pyrazine-7-carboxamide

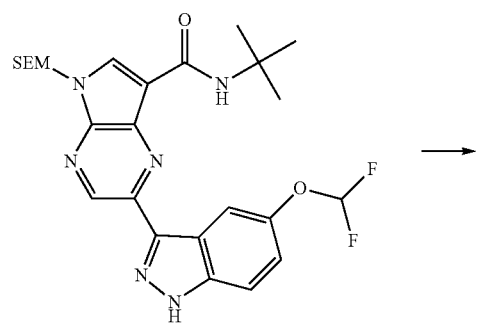

To a stirred solution of 2-chloro-1-(4-(2,2,2-trifluoroethyl)piperazin-1-yl)ethanone (115 mg, 471 µmol) in DMF (16 mL) under Ar, potassium carbonate (200 mg, 1.45 mmol) was added in a single portion at 25° C. After 1 h, a solution of N-tert-butyl-2-(5-(difluoromethoxy)-1H-indazol-3-yl)-5-((2-(trimethylsilyl)ethoxy)methyl)-5H-pyrrolo[2,3-b]pyrazine-7-carboxamide (50 mg, 94.2 µmol) in DMF (4.00 mL) was added in a single portion and the reaction was stirred at 60° C. After 18 h, the reaction was cooled to 25° C. and quenched with water (400 mL). The product was extracted with ethyl acetate (3×150 mL) and the organics were washed with brine (200 mL). The organics were dried over sodium sulfate and concentrated to give a yellow oil. The oil was dried in vacuo (300 mTorr, 25° C.) and purified by chromatography (silica, 12 g Analogix column, 5-80% ethyl acetate in hexanes, gradient over 1 h) to give N-tert-butyl-2-(5-(difluoromethoxy)-1-(2-oxo-2-(4-(2,2,2-trifluoroethyl)piperazin-1-yl)ethyl)-1H-indazol-3-yl)-5-((2-(trimethylsilyl)ethoxy)methyl)-5H-pyrrolo[2,3-b]pyrazine-7-carboxamide (69.0 mg, 93.3 mmol, 99%) as a yellow solid. MS (M)'=739; $^1$H NMR (DMSO-$d_6$) δ: 9.09 (s, 1H), 8.60 (s, 1H), 8.22 (d, J=2.0 Hz, 1H), 7.88 (s, 1H), 7.78 (d, J=9.3 Hz, 1H), 7.40 (dd, J=2.0, 8.8 Hz, 1H), 7.21 (t, J=74.3 Hz, 1H), 5.74 (s, 2H), 5.67 (s, 2H), 3.64 (br. s, 2H), 3.58 (t, J=8.0 Hz, 2H), 3.46 (d, J=4.5 Hz, 2H), 2.77 (br. s, 2H), 2.61 (d, J=18.8 Hz, 4H), 1.52 (s, 9H), 0.86 (t, J=8.0 Hz, 2H), −0.08 (s, 9H).

Step 3

N-tert-Butyl-2-(5-(difluoromethoxy)-1-(2-oxo-2-(4-(2,2,2-trifluoroethyl)piperazin-1-yl)ethyl)-1H-indazol-3-yl)-5H-pyrrolo[2,3-b]pyrazine-7-carboxamide

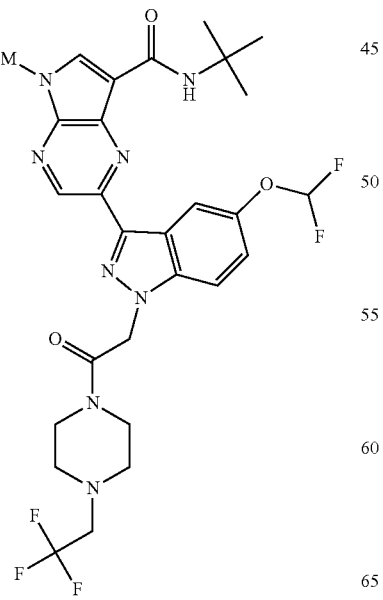

1121

-continued

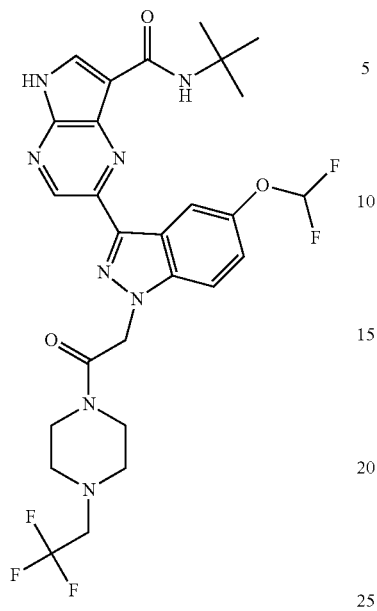

To a stirred solution of N-tert-butyl-2-(5-(difluoromethoxy)-1-(2-oxo-2-(4-(2,2,2-trifluoroethyl)piperazin-1-yl)ethyl)-1H-indazol-3-yl)-5-((2-(trimethylsilyl)ethoxy)methyl)-5H-pyrrolo[2,3-b]pyrazine-7-carboxamide (75.9 mg, 103 μmol) in dichloromethane (5 mL) under Ar, trifluoroacetic acid (744 mg, 0.50 mL, 6.52 mmol) was added at 25° C. After 96 h, the reaction was concentrated in vacuo and stirred in a mixture of dichloromethane/methanol/NH₃OH (3:2:0.25, 5.25 mL) at 25° C. After 2.5 h, the material was concentrated and dried in vacuo (200 mTorr, 25° C.) to give a yellow solid. The solid was purified by chromatography (silica, 12 g Analogix column, 10-100% ethyl acetate in hexanes, gradient over 1 h) to give a yellow oil. The oil was dissolved in ethanol (4.5 mL, 200 proof) and cooled to 4° C. The precipitated solid was isolated by filtration and dried in vacuo (100 mTorr, 40° C.) to give N-tert-butyl-2-(5-(difluoromethoxy)-1-(2-oxo-2-(4-(2,2,2-trifluoroethyl)piperazin-1-yl)ethyl)-1H-indazol-3-yl)-5H-pyrrolo[2,3-b]pyrazine-7-carboxamide (36.2 mg, 54.1 μmol, 53%) as a yellow solid. MS (M)'=609; ¹H NMR (DMSO-d₆) δ: 12.84 (d, J=3.0 Hz, 1H), 9.03 (s, 1H), 8.40 (d, J=3.0 Hz, 1H), 8.21 (d, J=2.3 Hz, 1H), 7.89 (s, 1H), 7.77 (d, J=9.0 Hz, 1H), 7.39 (dd, J=2.3, 9.0 Hz, 1H), 7.20 (t, J=74.5 Hz, 1H), 5.66 (s, 2H), 3.64 (br. s, 2H), 3.47 (br. s, 2H), 3.29 (q, J=10.3 Hz, 2H), 2.77 (br. s, 2H), 2.64 (br. s, 2H), 1.51 (s, 9H).

1122

Example 353

N-tert-Butyl-2-(5-(difluoromethoxy)-1-(2-(4-methylpiperazin-1-yl)-2-oxoethyl)-1H-indazol-3-yl)-5H-pyrrolo[2,3-b]pyrazine-7-carboxamide

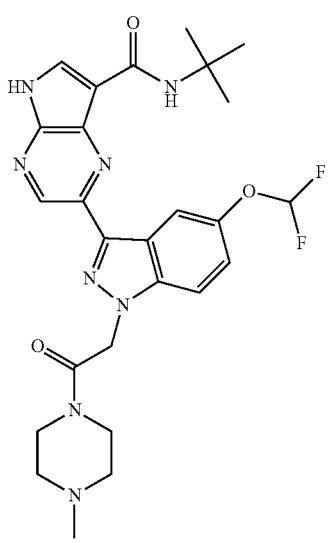 [SMILES: CN1CCN(C(=O)Cn2nc(-c3cnc4[nH]cc(C(=O)NC(C)(C)C)c4n3)c3cc(OC(F)F)ccc32)CC1]

Step 1

N-tert-Butyl-2-(5-(difluoromethoxy)-1-(2-(4-methylpiperazin-1-yl)-2-oxoethyl)-1H-indazol-3-yl)-5-((2-(trimethylsilyl)ethoxy)methyl)-5H-pyrrolo[2,3-b]pyrazine-7-carboxamide

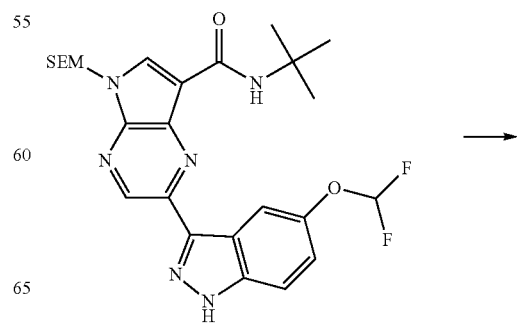

-continued

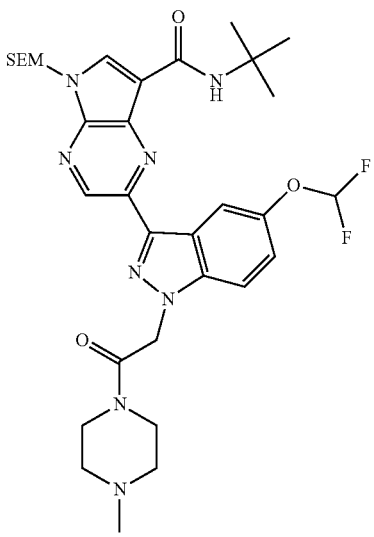

To a stirred solution of 2-chloro-1-(4-methylpiperazin-1-yl)ethanone (138.2 mg, 782 mmol) in DMF (32.0 mL) under Ar, potassium carbonate (328.5 mg, 2.38 mmol) was added at 25° C. After 1 h, N-tert-butyl-2-(5-(difluoromethoxy)-1H-indazol-3-yl)-5-((2-(trimethylsilyl)ethoxy)methyl)-5H-pyrrolo[2,3-b]pyrazine-7-carboxamide (80 mg, 151 µmol) in DMF (8.00 mL) was added and the reaction was stirred at 70° C. After 18 h, the reaction was cooled to 25° C. and quenched with water (350 mL). The product was extracted with ethyl acetate (2×250 mL). The organics were combined, dried over sodium sulfate, and the solvent removed to give a yellow oil. The solid was dried in vacuo (200 mTorr, 25° C.) to give a yellow solid. The solid was purified by chromatography (silica, 115 g Analogix column, 3-10% ethyl acetate in hexanes, gradient over 0.5 h) to give a yellow oil. The product was concentrated to a yellow oil and dried in vacuo to give N-tert-butyl-2-(5-(difluoromethoxy)-1-(2-(4-methylpiperazin-1-yl)-2-oxoethyl)-1H-indazol-3-yl)-5-((2-(trimethylsilyl)ethoxy)methyl)-5H-pyrrolo[2,3-b]pyrazine-7-carboxamide (41.7 mg, 62.2 µmol, 41.2%) as a yellow solid. MS (M)'=671; $^1$H NMR (DMSO-d$_6$) δ: 9.09 (s, 1H), 8.60 (s, 1H), 8.22 (d, J=2.3 Hz, 1H), 7.88 (s, 1H), 7.78 (d, J=9.0 Hz, 1H), 7.40 (dd, J=2.3, 8.8 Hz, 1H), 7.21 (t, J=74.4 Hz, 1H), 5.73 (s, 2H), 5.67 (s 2H), 3.61 (br. s, 2H), 3.58 (t, J=8.0 Hz, 2H), 3.45 (br. s, 2H), 2.45 (br. s, 2H), 2.32 (m, 2H), 2.33 (s, 3H), 1.52 (s, 9H), 0.86 (t, J=8.0 Hz, 2H), −0.08 (s, 9H).

Step 2

N-tert-Butyl-2-(5-(difluoromethoxy)-1-(2-(4-methylpiperazin-1-yl)-2-oxoethyl)-1H-indazol-3-yl)-5H-pyrrolo[2,3-b]pyrazine-7-carboxamide

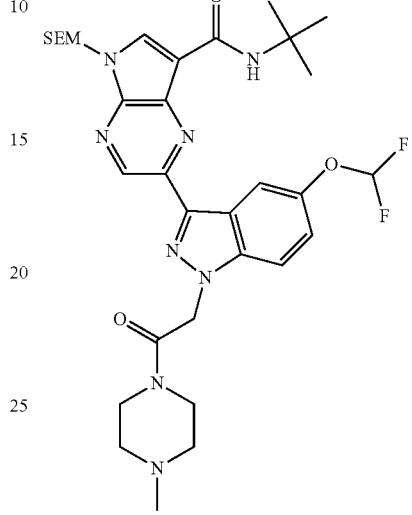

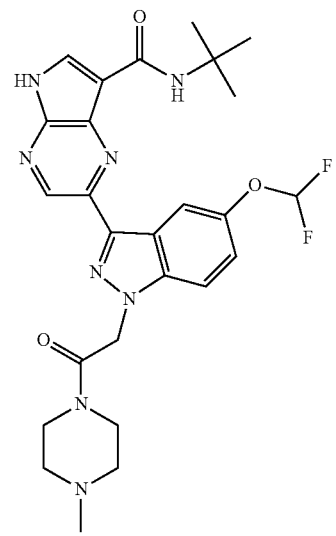

To a stirred solution of N-tert-butyl-2-(5-(difluoromethoxy)-1-(2-(4-methylpiperazin-1-yl)-2-oxoethyl)-1H-indazol-3-yl)-5-((2-(trimethylsilyl)ethoxy)methyl)-5H-pyrrolo[2,3-b]pyrazine-7-carboxamide (41.7 mg, 62.2 µmol) in dichloromethane (3 mL) under Ar trifluoroacetic acid (208 mg, 0.140 mL, 1.83 mmol) was added at 25° C. After 18 h, the reaction was concentrated in vacuo to give a yellow residue. The residue was dissolved in a mix of dichloromethane/methanol/NH$_3$OH (3:2:0.25, 5.25 mL) and stirred at 25° C. After 2.5 h, the material was concentrated and dried in vacuo (200 mTorr, 40° C.) to give N-tert-butyl-2-(5-(difluoromethoxy)-1-(2-(4-methylpiperazin-1-yl)-2-oxoethyl)-1H-indazol-3-yl)-5H-pyrrolo[2,3-b]pyrazine-7-carboxamide (22.4 mg, 41.4 mmol, 67%) as a yellow solid. MS (M)'=541; $^1$H NMR (DMSO-d$_6$) δ: 12.84 (d, J=2.8 Hz, 1H), 9.02 (s, 1H), 8.41 (d, J=3.0 Hz, 1H), 8.23 (d, J=2.3 Hz, 1H), 7.89 (s, 1H), 7.75 (d, J=9.3 Hz, 1H), 7.41 (dd, J=2.3, 9.0 Hz, 1H), 7.21 (t, J=74.5 Hz, 1H), 5.71 (br. s, 2H), 3.82 (br. s, 2H), 3.50 (br. s, 2H), 2.74 (br. s, 2H), 2.67 (br. s, 2H), 2.33 (s, 3H), 1.51 (s, 9H).

Example 354

N-tert-Butyl-2-(5-(difluoromethoxy)-1-(2-(methylamino)-2-oxoethyl)-1H-indazol-3-yl)-5H-pyrrolo[2,3-b]pyrazine-7-carboxamide

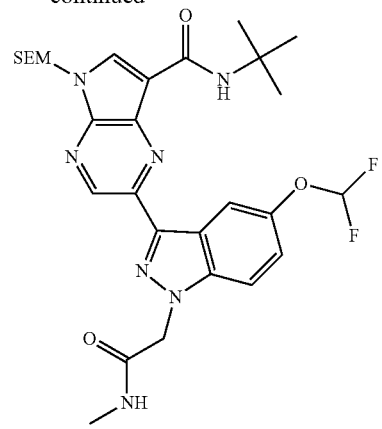

To a stirred solution of 2-chloro-N-methylacetamide (80 mg, 744 μmol) in DMF (28.0 mL) under Ar, potassium carbonate (280 mg, 2.03 mmol) was added at 25° C. After 1 h, N-tert-butyl-2-(5-(difluoromethoxy)-1H-indazol-3-yl)-5-((2-(trimethylsilyl)ethoxy)methyl)-5H-pyrrolo[2,3-b]pyrazine-7-carboxamide (70 mg, 132 μmol) in DMF (7.00 mL) was added and the reaction was stirred at 70° C. After 6 h, the reaction was cooled to 25° C. and quenched with water (350 mL). The product was extracted with ethyl acetate (2×250 mL). The organic layer was dried over sodium sulfate, filtered through Celite, and the solvent removed in vacuo to give a beige solid. The solid was triturated in hexanes (20 mL), filtered and dried in vacuo (200 mTorr, 25° C.) to give N-tert-butyl-2-(5-(difluoromethoxy)-1-(2-(methylamino)-2-oxoethyl)-1H-indazol-3-yl)-5-((2-(trimethylsilyl)ethoxy)methyl)-5H-pyrrolo[2,3-b]pyrazine-7-carboxamide (62.2 mg, 103 μmol, 78%) as a light brown solid. MS (M)'=602; $^1$H NMR (DMSO-$d_6$) δ: 9.10 (s, 1H), 8.60 (s, 1H), 8.22 (m, 2H), 7.88 (s, 1H), 7.82 (d, J=9.0 Hz, 1H), 7.41 (dd, J=2.3, 9.0 Hz, 1H), 7.21 (t, J=74.5 Hz, 1H), 5.73 (s, 2H), 5.27 (s 2H), 3.58 (t, J=8.0 Hz, 2H), 2.65 (d, J=4.5 Hz, 3H), 1.51 (s, 9H), 0.86 (t, J=7.8 Hz, 2H), −0.08 (s, 9H).

Step 1

N-tert-Butyl-2-(5-(difluoromethoxy)-1-(2-(methylamino)-2-oxoethyl)-1H-indazol-3-yl)-5-((2-(trimethylsilyl)ethoxy)methyl)-5H-pyrrolo[2,3-b]pyrazine-7-carboxamide

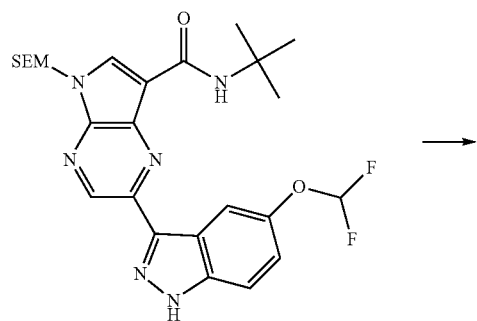

Step 2

N-tert-Butyl-2-(5-(difluoromethoxy)-1-(2-(methylamino)-2-oxoethyl)-1H-indazol-3-yl)-5H-pyrrolo[2,3-b]pyrazine-7-carboxamide

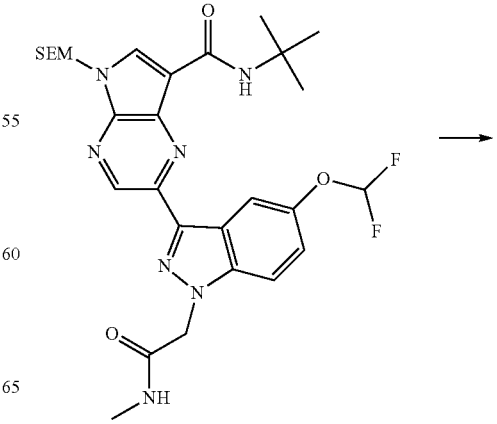

1127
-continued

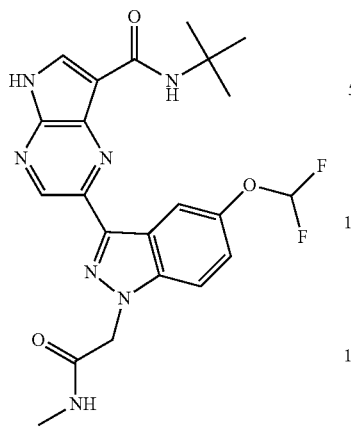

To a stirred solution of N-tert-butyl-2-(5-(difluoromethoxy)-1-(2-(methylamino)-2-oxoethyl)-1H-indazol-3-yl)-5-((2-(trimethylsilyl)ethoxy)methyl)-5H-pyrrolo[2,3-b]pyrazine-7-carboxamide (69.0 mg, 115 µmol) in dichloromethane (3.00 mL) under Ar, trifluoroacetic acid (372 mg, 0.25 mL, 3.26 mmol) was added at 25° C. After 18 h, the solvent was removed and the residue was dissolved in a mix of dichloromethane/methanol/NH₃OH (3:2:0.25, 5.25 mL) and stirred. After 2.5 h, the reaction was concentrated and dried in vacuo (200 mTorr, 25° C.). The solid residue was triturated with water (50 mL) and isolated by filtration. The solid was washed with water and hexanes and dried in vacuo (200 mTorr, 40° C.) to give N-tert-butyl-2-(5-(difluoromethoxy)-1-(2-(methylamino)-2-oxoethyl)-1H-indazol-3-yl)-5H-pyrrolo[2,3-b]pyrazine-7-carboxamide (45.6 mg, 91.9 µmol, 80%) as a light brown solid. MS (M)'=472; $^1$H NMR (DMSO-$d_6$) δ: 12.83 (br. s, 1H), 9.04 (s, 1H), 8.39 (d, J=2.8 Hz, 1H), 8.21 (m, 2H), 7.89 (s, 1H), 7.81 (d, J=9.0 Hz, 1H), 7.40 (dd, J=2.0, 9.0 Hz, 1H), 7.20 (t, J=74.3 Hz, 1H), 5.24 (s 2H), 2.65 (m, 3H), 1.51 (s, 9H).

Example 355

N-tert-Butyl-2-(7-ethyl-1H-indazol-3-yl)-5H-pyrrolo[3,2-b]pyrazine-7-carboxamide

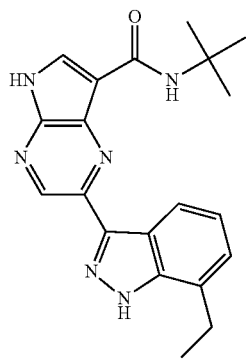 [SMILES: CCc1cccc2c(-c3cnc4[nH]cc(C(=O)NC(C)(C)C)c4n3)n[nH]c12]

Step 1

7-Ethyl-1H-indazole

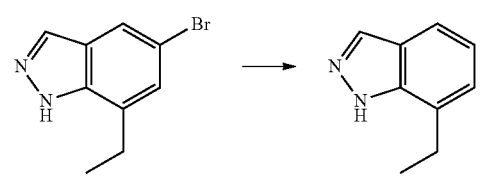

To a solution of 5-bromo-7-ethyl-1H-indazole (900 mg, 4.00 mmol) in ethanol (16.0 mL) flushed with nitrogen was added palladium on carbon (128 mg, 1.2 mmol) and the mixture stirred under H₂ at 1 atm. After 70 h the reaction was filtered over a pad of celite. The filtrate was collected and concentrated. The residue was dissolved in ethanol and 80 mg of palladium on carbon was added and stirred under H₂ at 1 atm. After 3 h another 80 mg of palladium on carbon was added and stirred under H₂ at 1 atm. After 16 h the reaction was filtered through a pad of celite. The filtrate was collected and concentrated. The yellow solid obtained was triturated with ether, filtered and dried under vacuum to give 7-ethyl-1H-indazole (771 mg, 5.27 mmol, 119%) as an off white solid. This was used directly without further purification. MS (M+H)⁺=146.8; $^1$H NMR (CDCl₃) δ: 8.54 (s, 1H), 7.78 (d, J=8.2 Hz, 1H), 7.59 (d, J=7.1 Hz, 1H), 7.43 (t, J=7.1 Hz, 1H), 3.25 (q, J=7.4 Hz, 2H), 1.48 (t, J=7.5 Hz, 3H).

Step 2

7-Ethyl-3-iodo-1H-indazole

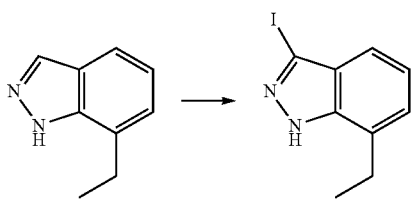

To a stirred solution of sodium bicarbonate (1.67 g, 19.8 mmol) in water (4.65 mL) and ethanol (9.3 mL) was added 7-ethyl-1H-indazole (771 mg, 5.27 mmol) followed by iodine (1.87 g, 7.38 mmol). After 16 h the reaction mixture was quenched with sodium thiosulfate, diluted with ethyl acetate and washed with water. The organic layer was collected and dried (MgSO₄). Purification by chromatography (silica, 5-25% ethyl acetate/hexanes) gave 7-ethyl-3-iodo-1H-indazole (690 mg, 2.54 mmol, 48%) as an off-white solid. MS (M+H)⁺=272.9; $^1$H NMR (CDCl₃) δ: 7.39 (d, J=8.1 Hz, 1H), 7.30 (d, J=7.1 Hz, 1H), 7.22 (t, J=7.1 Hz, 1H), 2.95 (q, J=7.5 Hz, 2H), 1.41 (t, J=7.5 Hz, 3H).

Step 3

N-tert-Butyl-2-(7-ethyl-1H-indazol-3-yl)-5-((2-(trimethylsilyl)ethoxy)methyl)-5H-pyrrolo[3,2-b]pyrazine-7-carboxamide

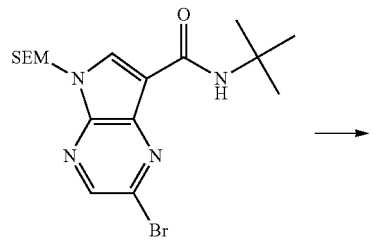

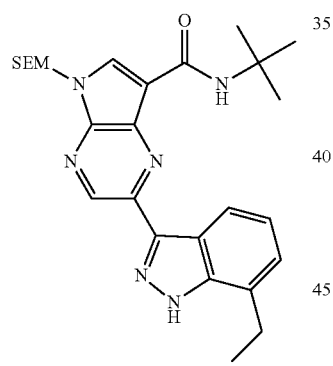

To a stirred solution of 2-bromo-N-tert-butyl-5-((2-(trimethylsilyl)ethoxy)methyl)-5H-pyrrolo[3,2-b]pyrazine-7-carboxamide (320 mg, 749 μmol) and 7-ethyl-3-iodo-1H-indazole (244 mg, 898 μmol) in DMF (2.5 mL) was added 1,1,1,2,2,2-hexabutyldistannane (651 mg, 412 μL, 1.12 mmol) under N$_2$. After 10 min tetrakis(triphenylphosphine)palladium (0) (43.3 mg, 37.4 mmol) was added and the reaction mixture heated to 115° C. After 16 h the reaction was cooled and concentrated. The residue was diluted with 10% methanol/dichloromethane and filtered through a pad of celite. Purification of the filtrate by chromatography (silica, 5-45% ethyl acetate/hexane) gave N-tert-butyl-2-(7-ethyl-1H-indazol-3-yl)-5-((2-(trimethylsilyl)ethoxy)methyl)-5H-pyrrolo[3,2-b]pyrazine-7-carboxamide (45 mg, 91.3 μmol, 12%) as an off-white solid. MS (M+H)$^+$=493.4; $^1$H NMR (CDCl$_3$) δ: 10.57 (s, 1H), 9.34 (s, 1H), 8.49 (d, J=7.5, 1H), 8.43 (s, 1H), 8.24 (s, 1H), 7.35 (d, J=7.1 Hz, 1H), 7.29 (t, J=7.1 Hz, 1H), 5.77 (s, 2H), 3.62 (t, J=8.3, 2H), 3.07 (q, J=7.5 Hz, 2H), 1.68 (s, 9H), 1.50 (t, J=7.5 Hz, 3H), 0.98 (t, J=8.3, 2H), 0.0 (s, 9H).

Step 4

N-tert-Butyl-2-(7-ethyl-1H-indazol-3-yl)-5H-pyrrolo[3,2-b]pyrazine-7-carboxamide

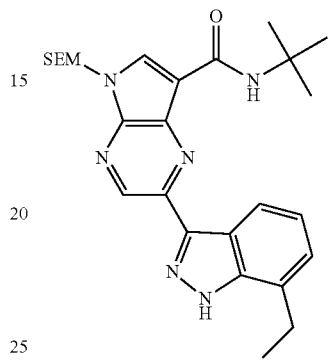

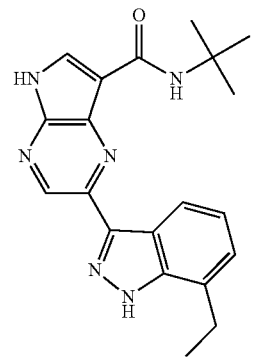

To a solution of N-tert-butyl-2-(7-ethyl-1H-indazol-3-yl)-5-((2(trimethylsilyl)ethoxy)methyl)-5H-pyrrolo[3,2-b]pyrazine-7-carboxamide (45 mg, 91.3 μmol) in dichloromethane (913 μL) was added trifluoroacetic acid (417 mg, 281 μL, 3.65 mmol) and stirred at room temperature. After 16 h the reaction mixture was concentrated. The residue was dissolved in dichloromethane (913 μL) and ethylenediamine (329 mg, 370 μL, 5.48 mmol) was added and stirred at room temperature. After 1 h the reaction was diluted with 10% methanol/dichloromethane. Purification by chromatography (silica, MeOH/DCM gradient) gave N-tert-butyl-2-(7-ethyl-1H-indazol-3-yl)-5H-pyrrolo[3,2-b]pyrazine-7-carboxamide (16 mg, 44.1 μmol, 48%) as a white solid. MS (M+H)$^+$=363.2; $^1$H NMR (CD$_3$OD) δ: 9.17 (s, 1H), 8.36 (d, J=7.5 Hz, 1H), 8.27 (s, 1H), 7.81 (s, 1H), 7.27 (d, J=7.5 Hz, 1H), 7.18 (t, J=7.5 Hz, 1H), 3.03 (q, J=7.7 Hz, 2H), 1.62 (s, 9H); 1.42 (t, J=7.7 Hz, 3H).

Example 356

N-tert-Butyl-2-(6-chloroimidazo[1,5-a]pyridin-1-yl)-5H-pyrrolo[3,2-b]pyrazine-7-carboxamide

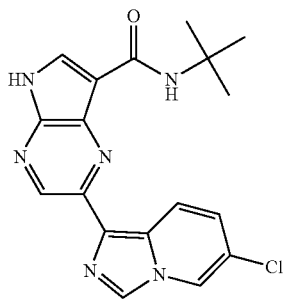 [SMILES: CC(C)(C)NC(=O)c1c[nH]c2ncc(-c3ncn4cc(Cl)ccc34)nc12]

Step 1

N-((5-Chloropyridin-2-yl)methyl)formamide

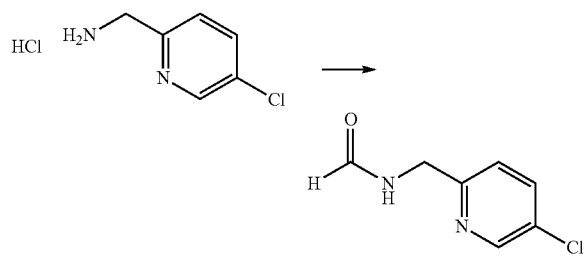

A solution of (5-chloropyridin-2-yl)methanamine hydrochloride (1.0 g, 5.31 mmol) in formic acid (5.09 g, 4.24 mL, 106 mmol) was refluxed at 110° C. After 20 h the reaction was cooled to 0° C. and 25% ammonium hydroxide in water was added until pH~9 was reached. The mixture was diluted with water and then extracted into dichloromethane (3×). The organic layers were combined and dried (MgSO$_4$), filtered and concentrated in vacuo. This was used directly in the next step without further purification. $^1$H NMR (CDCl$_3$) δ: 8.53 (s, 1H), 8.35 (s, 1H), 7.69 (m, 1H), 7.65 (m, 1H), 4.64 (d, J=5.3 Hz, 2H), 4.0 (s, 1H).

Step 2

6-Chloroimidazo[1,5-a]pyridine

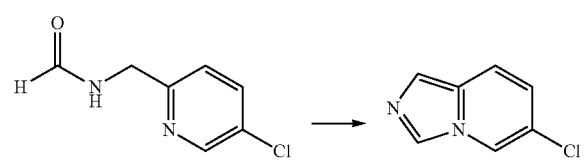

To a mixture of N-((5-chloropyridin-2-yl)methyl)formamide (740 mg, 4.34 mmol) in toluene (18.4 mL) was added phosphorus oxychloride (1.21 g, 736 µL, 7.89 mmol) and the mixture heated at to 100° C. After 16 h ice was added to the reaction mixture followed by the slow addition of 25% aqueous ammonium hydroxide until pH~9 was reached. The mixture was diluted with dichloromethane and extracted into dichloromethane (2×). The organic layers were washed with water and brine, dried (MgSO$_4$) and filtered. Purification of the filtrate by chromatography (silica, MeOH/DCM gradient) gave 6-chloroimidazo[1,5-a]pyridine (417 mg, 2.73 mmol, 63.0%) as a brown oil. MS (M+H)$^+$=152.8; $^1$H NMR (CDCl$_3$) δ: 8.10 (s, 1H), 8.01 (m, 1H), 7.47 (s, 1H), 7.43 (d, J=9.5 Hz, 1H), 6.69 (dd, J=9.5 Hz, 1.5 Hz, 1H).

Step 3

6-Chloro-1-iodoimidazo[1,5-a]pyridine

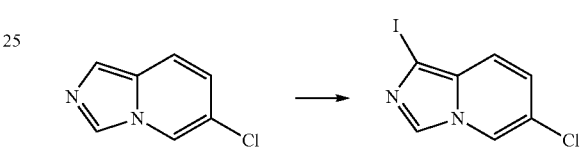

To a solution of 6-chloroimidazo[1,5-a]pyridine (417 mg, 2.73 mmol) in EtOH (5 mL) and water (2.4 mL) was added sodium bicarbonate (861 mg, 10.2 mmol) and iodine (832 mg, 3.28 mmol) and the mixture stirred at room temperature under N$_2$. After 16 h the reaction mixture was quenched with sodium thiosulfate, then extracted into ethyl acetate. The organic layer was washed with water and brine, dried (MgSO$_4$), filtered, and concentrated. Purification of the filtrate by chromatography (silica, 20-60% ethyl acetate/hexanes) gave 6-chloro-1-iodoimidazo[1,5-a]pyridine (271 mg, 973 µmol, 36%) as a brown solid. MS (M+H)$^+$=278.8; $^1$H NMR (CDCl$_3$) δ: 8.10 (s, 1H), 8.0 (m, 1H), 7.30 (d, J=9.5 Hz, 1H), 6.76 (9.5 m, 1H).

Step 4

N-tert-Butyl-2-(6-chloroimidazo[1,5-a]pyridin-1-yl)-5-((2-(trimethylsilyl)ethoxy)methyl)-5H-pyrrolo[3,2-b]pyrazine-7-carboxamide

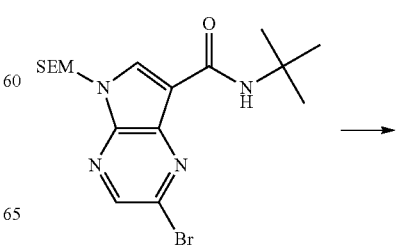

-continued

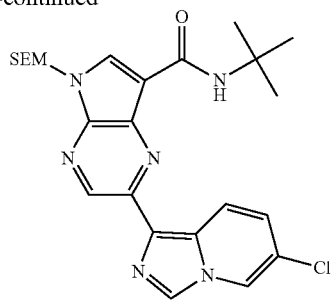

To a stirred solution of 6-chloro-1-iodoimidazo[1,5-a]pyridine (263 mg, 943 μmol) and 2-bromo-N-tert-butyl-5-((2-(trimethylsilyl)ethoxy)-5H-pyrrolo[3,2-b]pyrazine-7-carboxamide (300 mg, 726 μmol) in DMF (2 mL) was added 1,1,1,2,2,2-hexabutyldistannane (631 mg, 400 μL, 1.09 mmol) and tetrakis(triphenylphosphine)palladium(0) (41.9 mg, 36.3 μmol) under $N_2$. The temperature was increased to 120° C. After 16 h the reaction was cooled and concentrated. The residue was dissolved in dichloromethane and then purified by chromatography (silica, 30-70% ethyl acetate/hexane) to give N-tert-butyl-2-(6-chloroimidazo[1,5-a]pyridin-1-yl)-5-((2-(trimethylsilyl)ethoxy)methyl)-5H-pyrrolo[3,2-b]pyrazine-7-carboxamide (50 mg, 100 μmol, 13.8% yield) as a yellow oil. MS (M+H)+=499.3; $^1$H NMR (CDCl$_3$-d) δ: 9.31 (s, 1H), 8.48 (d, J=9.5 Hz, 1H), 8.33 (s, 1H), 8.23 (s, 1H), 8.13 (m, 1H), 7.99 (s, 1H), 6.9 (m, 1H), 5.74 (s, 2H), 3.61 (d, J=9.5 Hz, 2H), 1.67 (s, 9H); 0.98 (t, J=9.5 Hz, 2H), 0.0 (s, 9H).

Step 5

N-tert-Butyl-2-(6-chloroimidazo[1,5-a]pyridin-1-yl)-5H-pyrrolo[3,2-b]pyrazine-7-carboxamide

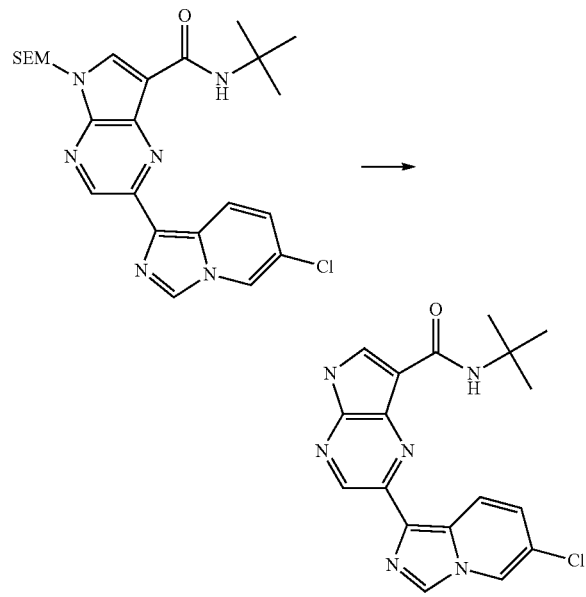

To a solution of N-tert-butyl-2-(6-chloroimidazo[1,5-a]pyridin-1-yl)-5-((2-(trimethylsilyl)ethoxy)methyl)-5H-pyrrolo[3,2-b]pyrazine-7-carboxamide (50 mg, 100 μmol) in dichloromethane (1.5 mL) was added trifluoroacetic acid (228 mg, 154 μL, 2.00 mmol) and the mixture stirred at room temperature. After 16 h the reaction mixture was concentrated, then the residue was redissolved in dichloromethane (2 mL), methanol (1 mL) and ammonium hydroxide (0.22 mL) and stirred at room temperature. After 2 h the reaction was concentrated in vacuo. The residue was purified by chromatography (silica, 30-100% of a 0.5:10:89.5 ammonium hydroxide:methanol:dichloromethane solution in dichloromethane). The collected material was concentrated, triturated with methanol and filtered to give N-tert-butyl-2-(6-chloroimidazo[1,5-a]pyridin-1-yl)-5H-pyrrolo[3,2-b]pyrazine-7-carboxamide (12 mg, 29.6 μmol, 30%) as a yellow solid. MS (M+H)+=369.1; $^1$H NMR (DMSO-d$_6$) δ: 12.69 (s, 1H), 9.08 (s, 1H), 8.79 (s, 1H), 8.53 (s, 1H), 8.34 (d, J=9.7 Hz, 1H), 8.30 (s, 1H), 7.84 (s, 1H), 7.05 (d, J=9.7 Hz, 1H); 1.52 (s, 9H).

Example 357

N-tert-Butyl-2-(6-fluoroimidazo[1,5-a]pyridin-1-yl)-5H-pyrrolo[2,3-b]pyrazine-7-carboxamide

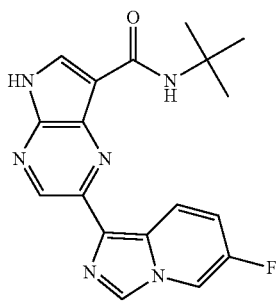 [SMILES: CC(C)(C)NC(=O)c1c[nH]c2ncc(-c3ncn4cc(F)ccc34)nc12]

Step 1

6-Fluoro-1-iodoimidazo[1,5-a]pyridine

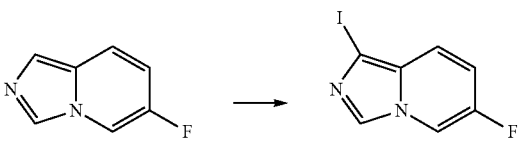 [SMILES: Fc1ccc2cncn2c1 ; Fc1ccc2c(I)ncn2c1]

To a solution of sodium bicarbonate (1.3 g, 15.4 mmol) in water (3.66 mL) was added 6-fluoroimidazo[1,5-a]pyridine (see Example 32, 560 mg, 4.11 mmol) in EtOH (7.31 mL) followed by iodine (1.46 g, 5.76 mmol) at room temperature. After 16 h another 800 mg of iodine was added. After a further 16 h the reaction mixture was quenched with sodium thiosulfate and diluted with ethyl acetate. The organic phase was washed with water and brine then dried (MgSO$_4$), filtered and concentrated in vacuo. Purification by chromatography (silica, ethyl acetate/hexane gradient). The product contained minor impurities and was used without further purification.

MS (M+H)⁺=262.9; ¹H NMR (CDCl₃) δ: 8.14 (s, 1H), 7.90 (m, 1H), 7.35 (m, 1H), 6.77 (m, 1H).

Step 2

6-Fluoro-1-(tributylstannyl)imidazo[1,5-a]pyridine

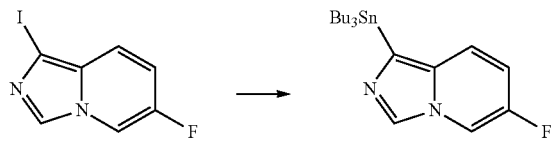

To a −16° C. solution of 6-fluoro-1-iodoimidazo[1,5-a]pyridine (158 mg, 603 µmol) in THF (4.64 mL) was added isopropylmagnesium chloride (368 µL, 736 µmol) dropwise. After 20 min tributylchlorostannane (232 mg, 193 µL, 712 µmol) was added dropwise at −16° C. and allowed to warm to room temperature. After 2 h the reaction was quenched with saturated ammonium chloride and diluted with ethyl acetate. The phases were separated and the organic phase washed with brine. The organic layer was collected, concentrated in vacuo, and used in the next step without further purification.

Step 3

N-tert-Butyl-2-(6-fluoroimidazo[1,5-a]pyridin-1-yl)-5-((2-(trimethylsilyl)ethoxy)methyl)-5H-pyrrolo[2,3-b]pyrazine-7-carboxamide

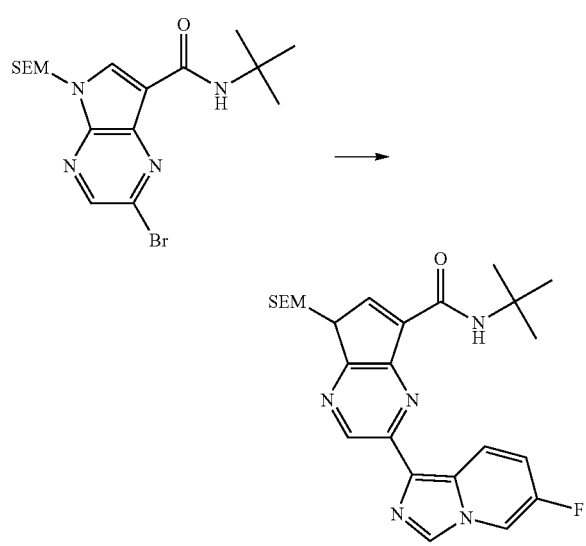

To a mixture of 2-bromo-N-tert-butyl-5-((2-(trimethylsilyl)ethoxy)methyl)-5H-pyrrolo[2,3-b]pyrazine-7-carboxamide (250 mg, 585 µmol), 6-fluoro-1-(tributylstannyl)imidazo[1,5-a]pyridine (400 mg, 564 µmol), tetrakis(triphenylphosphine)palladium (0) (33.8 mg, 29.2 µmol) and copper (I) iodide (22.3 mg, 117 µmol) was added DMF (5.85 mL) and the reaction mixture heated to 90° C. under N₂. After 16 h the reaction was diluted with ether, ethyl acetate and water. The organic phase was separated and washed with water (1×) and brine (2×) then dried (MgSO₄), filtered and concentrated in vacuo. Purification by chromatography (silica, 30-80% ethyl acetate/hexanes) gave N-tert-butyl-2-(6-fluoroimidazo[1,5-a]pyridin-1-yl)-5-((2-(trimethylsilyl)ethoxy)methyl)-5H-pyrrolo[2,3-b]pyrazine-7-carboxamide (88 mg, 182 µmol, 31.2%) as a yellow solid. MS (M+H)⁺=483.3; ¹H NMR (CDCl₃-d) δ: 9.34 (s, 1H), 8.54 (m, 1H), 8.34 (s, 2H), 8.04 (m, 1H), 7.98 (s, 1H), 6.9 (m, 1H), 5.74 (s, 2H), 3.61 (d, J=8.3 Hz, 2H), 1.66 (s, 9H); 0.98 (t, J=8.3 Hz, 2H), 0.0 (s, 9H).

Step 4

N-tert-Butyl-2-(6-fluoroimidazo[1,5-a]pyridin-1-yl)-5H-pyrrolo[2,3-b]pyrazine-7-carboxamide

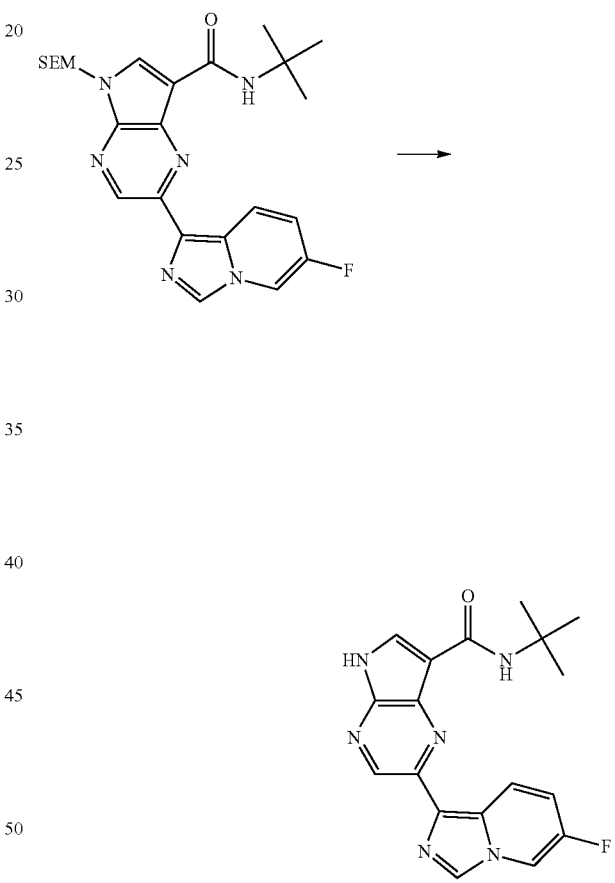

To a stirred solution of N-tert-butyl-2-(6-fluoroimidazo[1,5-a]pyridin-1-yl)-5-((2-(trimethylsilyl)ethoxy)methyl)-5H-pyrrolo[2,3-b]pyrazine-7-carboxamide (95 mg, 197 µmol) in dichloromethane (3 mL) was added trifluoroacetic acid (449 mg, 303 µL, 3.94 mmol) at room temperature. After 16 h the reaction was concentrated. The residue was dissolved in dichloromethane (3 mL), methanol (1.5 mL) and ammonium hydroxide (0.45 mL). After 1 h the reaction was concentrated. The residue was triturated with water and filtered. The solid was washed water and ether then dried under vacuum to give N-tert-butyl-2-(6-fluoroimidazo[1,5-a]pyridin-1-yl)-5H-pyrrolo[2,3-b]pyrazine-7-carboxamide (64 mg, 182 µmol, 92%) as a yellow solid. MS: (M+H)⁺=353; ¹H NMR (CD₃OD) δ: 9.10 (s, 1H), 8.48 (d, J=5.1 Hz, 1H), 8.45 (s, 1H), 8.42 (m, 1H), 8.25 (s, 1H), 7.03 (m, 1H), 1.62 (s, 9H).

Example 358

2-(6-Fluoro-1-methyl-1H-indazol-3-yl)-5H-pyrrolo[2,3-b]pyrazine-7-carboxylic acid [(S)-1-(5-trifluoromethyl-1H-imidazol-2-yl)-ethyl]-amide

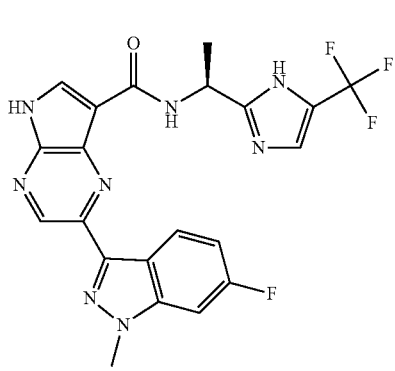 [SMILES: C[C@H](NC(=O)c1c[nH]c2ncc(-c3nn(C)c4cc(F)ccc34)nc12)c1ncc(C(F)(F)F)[nH]1]

Step 1

[(S)-1-(5-Trifluoromethyl-1H-imidazol-2-yl)-ethyl]-carbamic acid tert-butyl ester

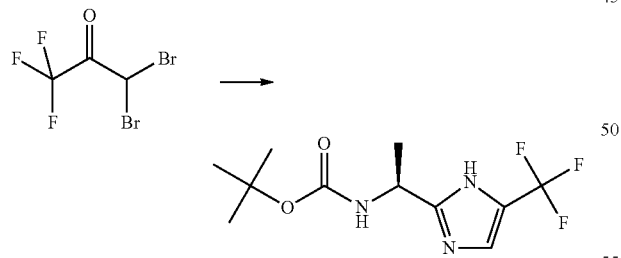

To a stirred solution of sodium acetate (1.44 g, 17.6 mmol) in water (4 mL) was added 3,3-dibromo-1,1,1-trifluoropropan-2-one (2.37 g, 8.8 mmol). The mixture was heated at 90° C. under nitrogen for 30 min. After the reaction mixture was cooled to 0° C., (R)-tert-butyl 1-oxopropan-2-ylcarbamate (1.39 g, 8 mmol) in methanol (20 mL) and ammonium hydroxide (6 mL) were added. After 3 h, the mixture was concentrated in vacuo, triturated with water and the solid obtained by filtration. The crude was purified by chromatography (silica, 40 g Analogix column, 0-50% ethyl acetate in hexanes, gradient over 30 min) to give [(S)-1-(5-trifluoromethyl-1H-imidazol-2-yl)-ethyl]-carbamic acid tert-butyl ester (510 mg, 23%) as a light yellow solid. LCMS, [M+H]=280.

Step 2

(S)-1-(5-Trifluoromethyl-1H-imidazol-2-yl)-ethylamine hydrochloride

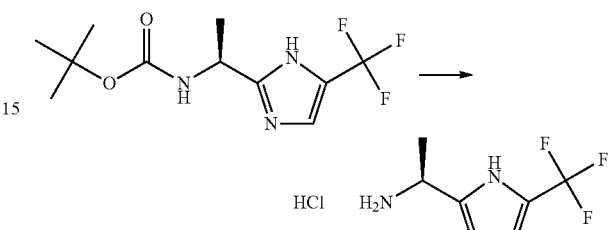

A solution of [(S)-1-(5-trifluoromethyl-1H-imidazol-2-yl)-ethyl]-carbamic acid tert-butyl ester (50 mg, 179 μmol) in 4M HCl in dioxane (2 mL) was stirred at room temperature for 15 h. The mixture was concentrated in vacuo then triturated with ether to give (S)-1-(5-trifluoromethyl-1H-imidazol-2-yl)-ethylamine hydrochloride (35 mg, quantitative) as a yellow oil. LCMS, [M+H]=180.

Step 3

2-(6-Fluoro-1-methyl-1H-indazol-3-yl)-5-((2-(trimethylsilyl)ethoxy)methyl)-5H-pyrrolo[2,3-b]pyrazine-7-carboxylic acid

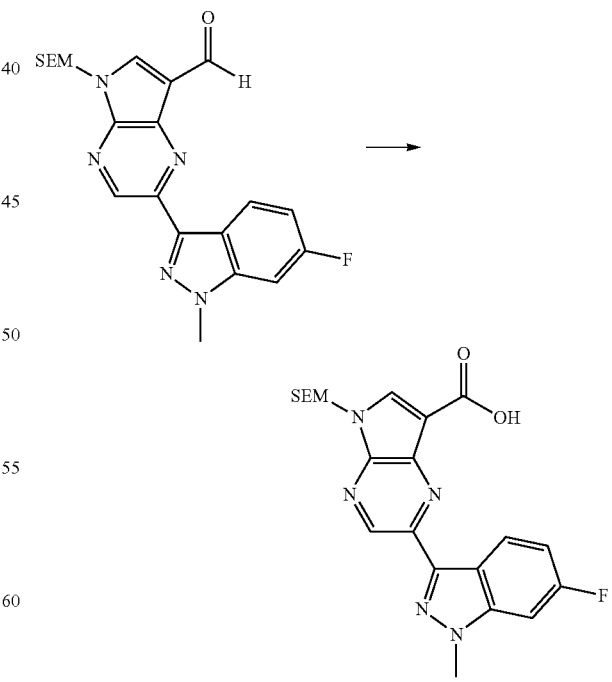

To a stirred suspension of 2-(6-fluoro-1-methyl-1H-indazol-3-yl)-5-((2-(trimethylsilyl)ethoxy)methyl)-5H-pyrrolo[2,3-b]pyrazine-7-carbaldehyde (500 mg, 1.18 mmol) and sulfamic acid (685 mg, 7.05 mmol) in dioxane (25 mL) and water (0.556 mL) in an ice bath was added a solution of sodium chlorite (146 mg, 1.61 mmol) and potassium dihydrogen phosphate (1.92 g, 14.1 mmol) in water (2.78 mL). The reaction mixture was stirred at room temperature for overnight. The reaction mixture was diluted with ethyl acetate and water. The organic layer was separated, washed with brine then dried (sodium sulfate), filtered and concentrated in vacuo. The crude residue was recrystallized from ethyl acetate and hexane to give 2-(6-fluoro-1-methyl-1H-indazol-3-yl)-5-((2-(trimethylsilyl)ethoxy)methyl)-5H-pyrrolo[2,3-b]pyrazine-7-carboxylic acid (467 mg, 89%) as a light yellow solid. This was used directly in the next step without further purification. LCMS, [M+H]=442.

Step 4

2-(6-Fluoro-1-methyl-1H-indazol-3-yl)-5-((2-(trimethylsilyl)ethoxy)methyl)-5H-pyrrolo[2,3-b]pyrazine-7-carboxylic acid [(S)-1-(5-trifluoromethyl-1H-imidazol-2-yl)-ethyl]-amide

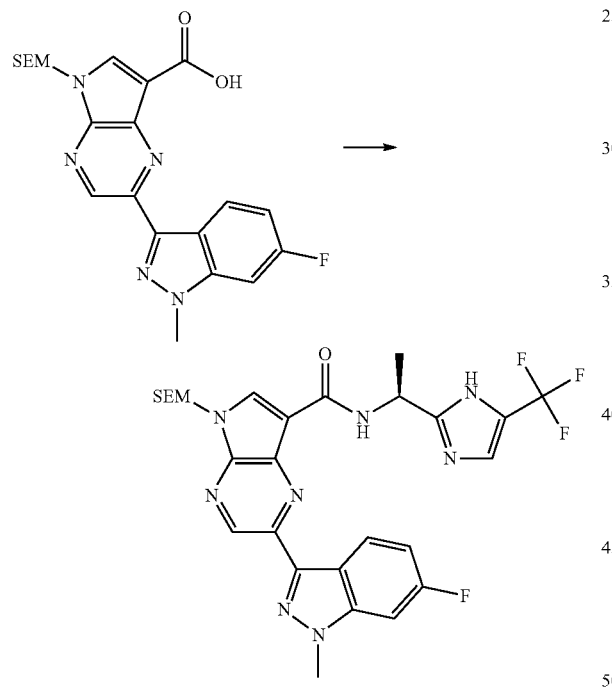

To a stirred solution of 2-(6-fluoro-1-methyl-1H-indazol-3-yl)-5-((2-(trimethylsilyl)ethoxy)methyl)-5H-pyrrolo[2,3-b]pyrazine-7-carboxylic acid (40 mg, 90.6 µmol), (S)-1-(5-(trifluoromethyl)-1H-imidazol-2-yl)ethanamine hydrochloride (32.5 mg, 151 µmol), diisopropylethylamine (63.3 µL, 362 µmol) in DMF (2 mL) was added o-(benzotriazol-1-yl)-N,N,N',N'-bis(tetramethylene)uronium hexafluorophosphate (43.0 mg, 99.7 µmol). After 15 hours the reaction mixture was diluted with dichloromethane and water. The organic layer was washed with saturated sodium carbonate and brine then dried (sodium sulfate), filtered and concentrated in vacuo. The residue was purified by chromatography (silica, 12 g Analogix column, 50-70% ethyl acetate in hexanes, gradient over 30 min) to give 2-(6-fluoro-1-methyl-1H-indazol-3-yl)-5-((2-(trimethylsilyl)ethoxy)methyl)-5H-pyrrolo[2,3-b]pyrazine-7-carboxylic acid [(S)-1-(5-trifluoromethyl-1H-imidazol-2-yl)-ethyl]-amide (34 mg, 62%) as a light yellow solid. LCMS, [M+H]=603.

Step 5

2-(6-Fluoro-1-methyl-1H-indazol-3-yl)-5H-pyrrolo[2,3-b]pyrazine-7-carboxylic acid [(S)-1-(5-trifluoromethyl-1H-imidazol-2-yl)-ethyl]-amide

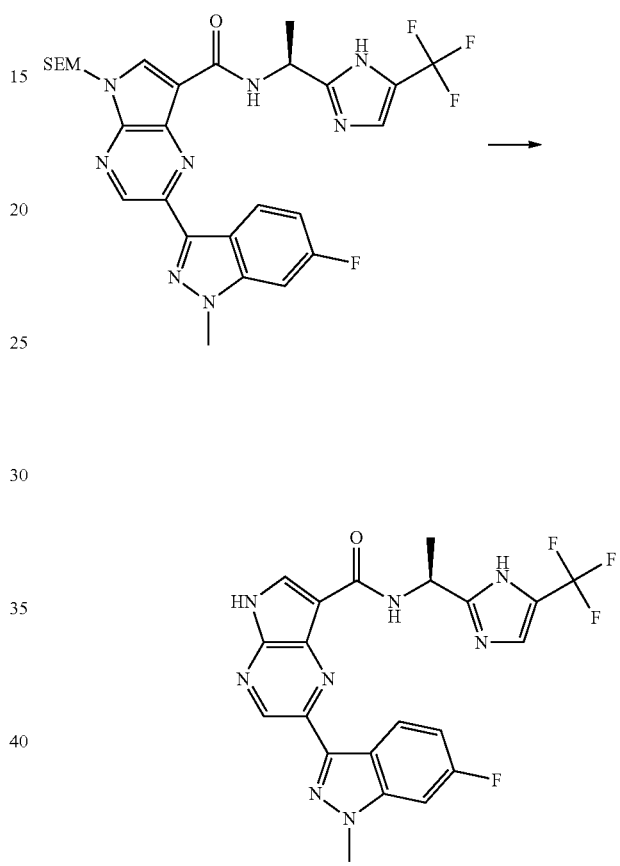

To a stirred solution of 2-(6-fluoro-1-methyl-1H-indazol-3-yl)-5-((2-(trimethylsilyl)ethoxy)methyl)-5H-pyrrolo[2,3-b]pyrazine-7-carboxylic acid [(S)-1-(5-trifluoromethyl-1H-imidazol-2-yl)-ethyl]-amide (34 mg, 56.4 µmol) in dichloromethane (0.5 mL) was added trifluoroacetic acid (174 µL, 2.26 mmol) at 20° C. After 3 h, the mixture was concentrated in vacuo. The residue was diluted with dichloromethane and concentrated again. The residue was then suspended in dichloromethane (1 mL) and ethylenediamine (229 µL, 3.39 mmol) added. The mixture was stirred for 1 h, then diluted with ethyl acetate and water. The organic layer was washed with brine, then dried (sodium sulfate), filtered and concentrated in vacuo. The residue was purified by chromatography (silica, 12 g Analogix column, 0-10% methanol in dichloromethane, gradient over 30 min) to give 2-(6-fluoro-1-methyl-1H-indazol-3-yl)-5H-pyrrolo[2,3-b]pyrazine-7-carboxylic acid [(S)-1-(5-trifluoromethyl-1H-imidazol-2-yl)ethyl]-amide (16 mg, 60%) as a light yellow solid. MS (M+H)$^+$=473; $^1$H NMR (DMSO-d$_6$) δ: 12.94 (d, J=3.0 Hz, 1H), 12.80 (br. s., 1H), 9.12 (s, 1H), 8.63 (d, J=8.5 Hz, 1H), 8.50 (d, J=3.3 Hz, 1H), 8.42-8.49 (m, 1H), 7.72 (s, 1H), 7.67 (dd, J=9.8, 2.0 Hz, 1H), 7.00 (td, J=9.2, 2.3 Hz, 1H), 5.32-5.59 (m, 1H), 4.14 (s, 3H), 1.64 (d, J=6.8 Hz, 3H).

Example 359

2-((S)-1-{[2-(6-Fluoro-1-methyl-1H-indazol-3-yl)-5H-pyrrolo[2,3-b]pyrazine-7-carboxyl]-amino}-ethyl)-3H-imidazol-4-carboxylic acid methyl ester

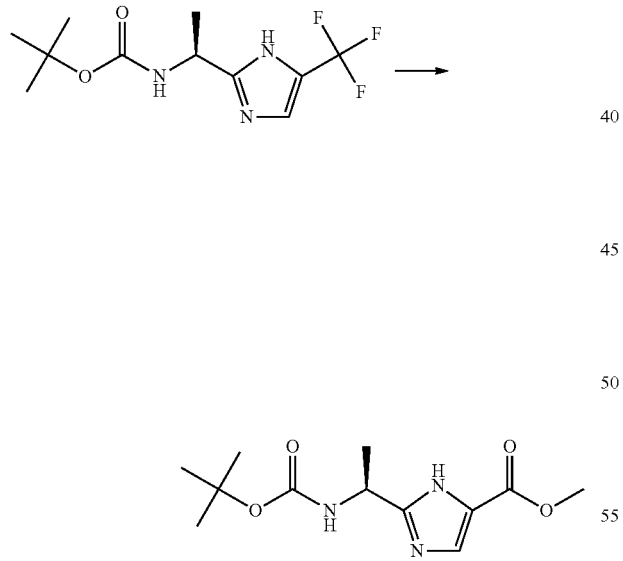

Step 1

2-((S)-1-tert-Butoxycarbonylamino-ethyl)-3H-imidazole-4-carboxylic acid methyl ester

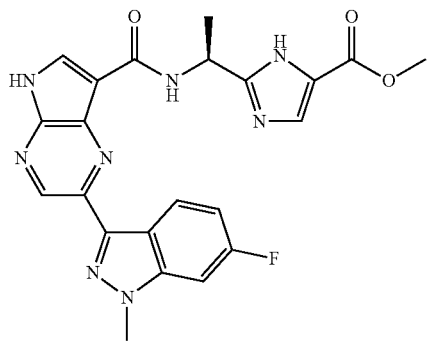 [SMILES: COC(=O)c1cnc([C@H](C)NC(=O)c2c[nH]c3ncc(-c4nn(C)c5cc(F)ccc45)nc23)[nH]1]

To a stirred solution of (S)-tert-butyl 1-(5-(trifluoromethyl)-1H-imidazol-2-yl)ethylcarbamate (200 mg, 716 μmol) in methanol (6 mL) was added sodium methoxide (77.4 mg, 1.43 mmol). The mixture was heated in microwave at 100° C. for 60 min. The mixture was concentrated in vacuo. The residue was dissolved in ethyl acetate, then washed saturated aqueous sodium carbonate, brine, then dried (sodium sulfate), filtered and concentrated in vacuo to give 2-((S)-1-tert-butoxycarbonylamino-ethyl)-3H-imidazole-4-carboxylic acid methyl ester (154 mg, 80%) as a yellow solid. This was used directly in the next step without further purification. LCMS, [M+H]=270.

Step 2

2-((S)-1-Amino-ethyl)-3H-imidazole-4-carboxylic acid methyl ester hydrochloride

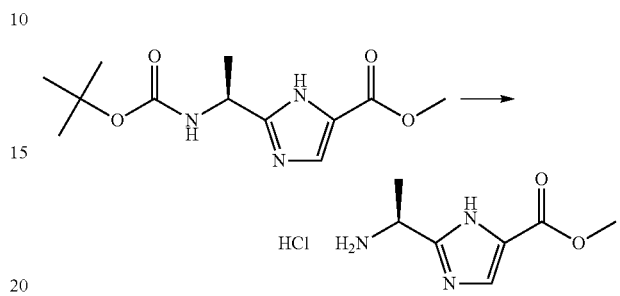

A solution of 2-((S)-1-tert-butoxycarbonylamino-ethyl)-3H-imidazole-4-carboxylic acid methyl ester hydrochloride (50 mg, 186 μmol) in 4M HCl in dioxane (2 mL) was stirred at room temperature for 15 h. The mixture was concentrated in vacuo, washed with ether to give 2-((S)-1-amino-ethyl)-3H-imidazole-4-carboxylic acid methyl ester hydrochloride (40 mg, quantitative) as a yellow oil, LCMS, [M+H]=170.

Step 3

2-((S)-1-{[2-(6-Fluoro-1-methyl-1H-indazol-3-yl)-5-(2-trimethylsilanyl-ethoxymethyl)-5H-pyrrolo[2,3-b]pyrazine-7-carboxyl]-amino}-ethyl)-3H-imidazol-4-carboxylic acid methyl ester

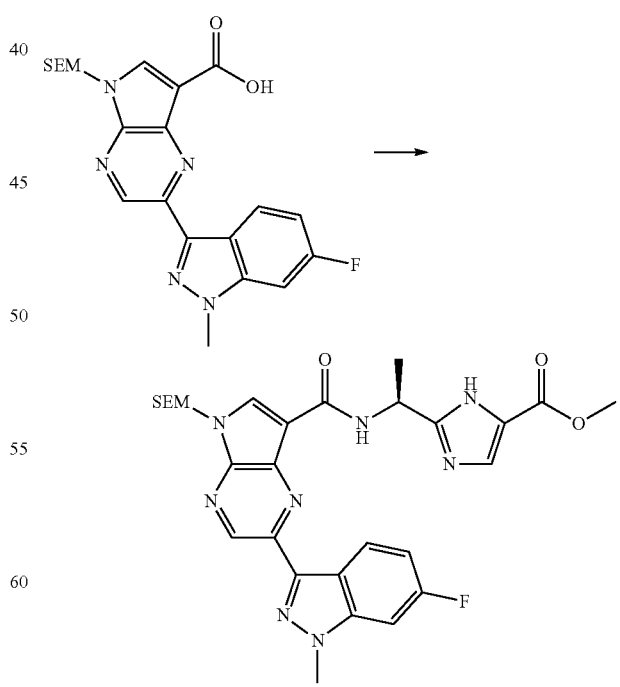

To a stirred solution of 2-(6-fluoro-1-methyl-1H-indazol-3-yl)-5-((2-(trimethylsilyl)ethoxy)methyl)-5H-pyrrolo[2,3- b]pyrazine-7-carboxylic acid (50 mg, 113 μmol), (S)-methyl 2-(1-aminoethyl)-1H-imidazole-5-carboxylate hydrochloride (38.3 mg, 186 μmol) and diisopropylethylamine (79.1 μL, 453 μmol) in DMF (2.5 mL) was added o-(benzotriazol-1-yl)-N,N,N',N'-bis(tetramethylene)uronium hexafluorophosphate (58.6 mg, 136 μmol). After 15 h, the reaction mixture was diluted with dichloromethane and water. The organic layer was washed with saturated sodium carbonate, and brine then dried (sodium sulfate), filtered and concentrated in vacuo. The residue was purified by chromatography (silica, 12 g Analogix column, 50-70% ethyl acetate in hexanes, gradient over 30 min) to give 2-((S)-1-{[2-(6-fluoro-1-methyl-1H-indazol-3-yl)-5-(2-trimethylsilanyl-ethoxymethyl)-5H-pyrrolo[2,3-b]pyrazine-7-carboxyl]-amino}-ethyl)-3H-imidazol-4-carboxylic acid methyl ester (35 mg, 52.1%) as a light yellow solid. LCMS, [M+H]=693.

Step 4

2-((S)-1-{[2-(6-Fluoro-1-methyl-1H-indazol-3-yl)-5H-pyrrolo[2,3-b]pyrazine-7-carboxyl]-amino}-ethyl)-3H-imidazol-4-carboxylic acid methyl ester

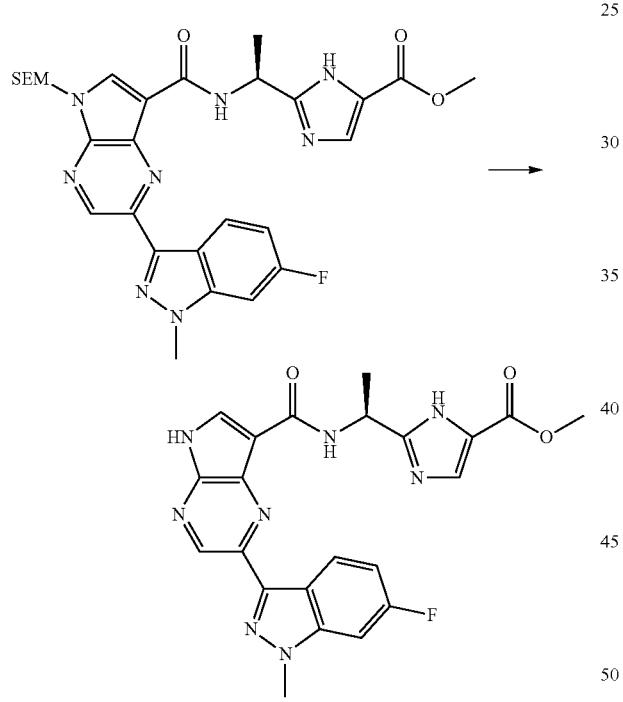

To a stirred solution of 2-((S)-1-{[2-(6-fluoro-1-methyl-1H-indazol-3-yl)-5-(2-trimethylsilanyl-ethoxymethyl)-5H-pyrrolo[2,3-b]pyrazine-7-carboxyl]-amino}-ethyl)-3H-imidazol-4-carboxylic acid methyl ester (32 mg, 54.0 μmol) in dichloromethane (0.5 mL) was added trifluoroacetic acid (249 μL, 3.24 mmol) at 20° C. After 15 h, the residue was diluted with dichloromethane and concentrated again. The residue was then suspended in dichloromethane (1 mL) and ethylenediamine (219 μL, 3.24 mmol) added. The mixture was stirred for 1 h, then diluted with ethyl acetate and water. The organic layer was washed with brine, then dried (sodium sulfate), filtered and concentrated in vacuo. The residue was purified by chromatography (silica, 12 g Analogix column, 0-3% methanol in dichloromethane, gradient over 30 min) to give 2-((S)-1-{[2-(6-fluoro-1-methyl-1H-indazol-3-yl)-5H-pyrrolo[2,3-b]pyrazine-7-carboxyl]-amino}-ethyl)-3H-imidazol-4-carboxylic acid methyl ester (18 mg, 72%) as a white solid. MS (M+H)$^+$=463; $^1$H NMR (DMSO-d$_6$) δ: 12.92 (br. s., 1H), 12.73 (br. s., 1H), 9.12 (s, 1H), 8.57 (d, J=8.5 Hz, 1H), 8.49 (s, 1H), 8.35 (dd, J=9.0, 5.3 Hz, 1H), 7.82 (d, J=2.0 Hz, 1H), 7.65 (dd, J=9.7, 2.1 Hz, 1H), 6.96-7.14 (m, 1H), 5.36-5.51 (m, 1H), 4.14 (s, 3H), 3.69 (s, 3H), 1.64 (d, J=7.0 Hz, 3H).

Example 360

(3-Ethynyl-azetindin-1-yl)-[2-(6-fluoro-1-methyl-1H-indazol-3-yl)-5H-pyrrolo[2,3-b]pyrazin-7-yl]-methanone

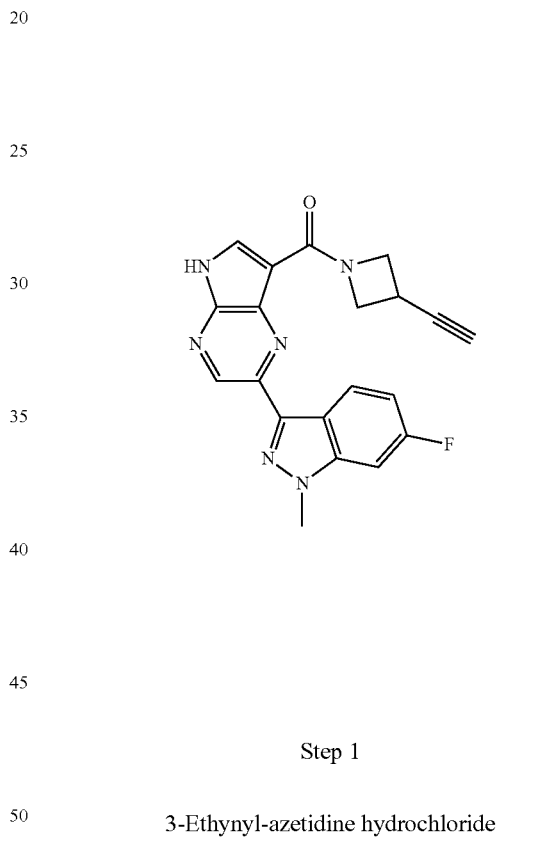

Step 1

3-Ethynyl-azetidine hydrochloride

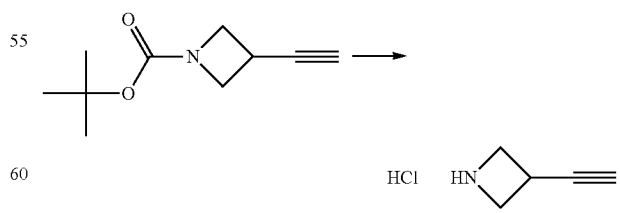

A solution of tert-butyl 3-ethynylazetidine-1-carboxylate (54 mg, 298 μmol) in 4M HCl in dioxane (2 mL) was stirred at room temperature for 15 h. The mixture was concentrated in vacuo. The residue was washed with ether, then dried in

1145 high vacuum to give 3-ethynyl-azetidine hydrochloride (36 mg, quantitative) as a white crystalline solid.

Step 2

(3-Ethynyl-azetindin-1-yl)-[2-(6-fluoro-1-methyl-1H-indazol-3-yl)-5-(2-trimethylsilanylethoxymethyl)-5H-pyrrolo[2,3-b]pyrazin-7-yl]-methanone

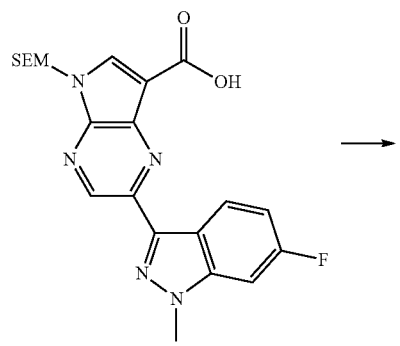

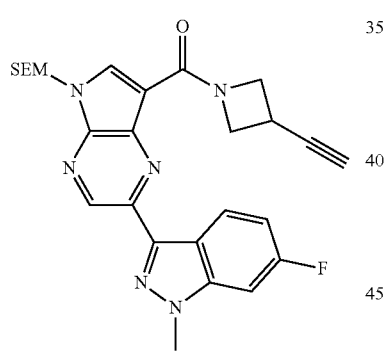

To a stirred solution of 2-(6-fluoro-1-methyl-1H-indazol-3-yl)-5-((2-(trimethylsilyl)ethoxy)methyl)-5H-pyrrolo[2,3-b]pyrazine-7-carboxylic acid (50 mg, 113 μmol), 3-ethynyl-azetidine hydrochloride (18.4 mg, 154 μmol), diisopropylethylamine (79.1 μL, 453 mmol) in DMF (2.5 mL) was added o-(benzotriazol-1-yl)-N,N,N',N'-bis(tetramethylene)uronium hexafluorophosphate (48.8 mg, 113 μmol). After 15 h, the reaction mixture was diluted with dichloromethane and water. The organic layer was washed with saturated sodium carbonate and brine then dried (sodium sulfate), filtered and concentrated in vacuo. The residue was purified by chromatography (silica, 12 g Analogix column, 40-70% ethyl acetate in hexanes, gradient over 30 min) to give (3-ethynyl-azetindin-1-yl)-[2-(6-fluoro-1-methyl-1H-indazol-3-yl)-5-(2-trimethylsilanyl-ethoxymethyl)-5H-pyrrolo[2,3-b]pyrazin-7-yl]-methanone (64 mg, 100%) as a yellow oil.

LCMS, [M+H]=505.

1146

Step 3

(3-Ethynyl-azetindin-1-yl)-[2-(6-fluoro-1-methyl-1H-indazol-3-yl)-5H-pyrrolo[2,3-b]pyrazin-7-yl]-methanone

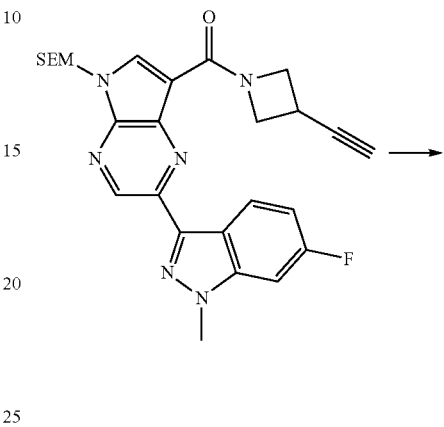

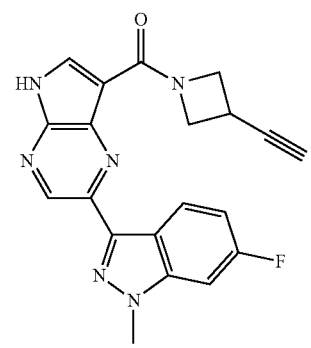 [SMILES: C#CC1CN(C(=O)c2c[nH]c3ncc(-c4nn(C)c5cc(F)ccc45)nc23)C1]

To a stirred solution of (3-ethynyl-azetindin-1-yl)-[2-(6-fluoro-1-methyl-1H-indazol-3-yl)-5-(2-trimethylsilanyl-ethoxymethyl)-5H-pyrrolo[2,3-b]pyrazin-7-yl]-methanone (61 mg, 121 mmol) in dichloromethane (0.5 mL) was added trifluoroacetic acid (373 μL, 4.84 mmol) at 20° C. After 3 h, the mixture was concentrated in vacuo. The residue was diluted with dichloromethane and concentrated again. The residue was then suspended in dichloromethane (1 mL) and ethylenediamine (490 μL, 7.24 mmol) added. The mixture was stirred for 1 h, then diluted with ethyl acetate and water. The organic layer was washed with brine, then dried (sodium sulfate), filtered and concentrated in vacuo. The residue was purified by chromatography (silica, 12 g Analogix column, 0-5% methanol in dichloromethane, gradient over 30 min) to give (3-ethynyl-azetindin-1-yl)-[2-(6-fluoro-1-methyl-1H-indazol-3-yl)-5H-pyrrolo[2,3-b]pyrazin-7-yl]-methanone (25 mg, 55%) as a light yellow solid. MS (M+H)$^+$=375; $^1$H NMR (DMSO-d$_6$) δ: 12.73 (br. s., 1H), 9.10 (s, 1H), 8.72 (dd, J=9.0, 5.5 Hz, 1H), 8.33 (s, 1H), 7.65 (dd, J=9.8, 2.0 Hz, 1H), 7.22 (td, J=9.1, 2.1 Hz, 1H), 4.53 (br. s., 4H), 4.14 (s, 3H), 3.47-3.58 (m, 1H), 3.38 (d, J=2.5 Hz, 3H).

Example 361

N-tert-Butyl-2-(6-chloro-1-methyl-1H-indazol-3-yl)-5H-pyrrolo[2,3-b]pyrazine-7-carboxamide

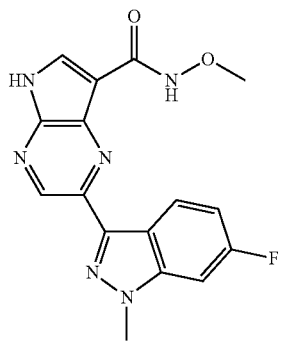 [SMILES: CONC(=O)c1c[nH]c2ncc(-c3nn(C)c4cc(F)ccc34)nc12]

Step 1

2-(6-Fluoro-1-methyl-1H-indazol-3-yl)-5-(2-trimethylsilanyl-ethoxymethyl)-5H-pyrrolo[2,3-b]pyrazine-7-carboxylic acid methoxy-amide

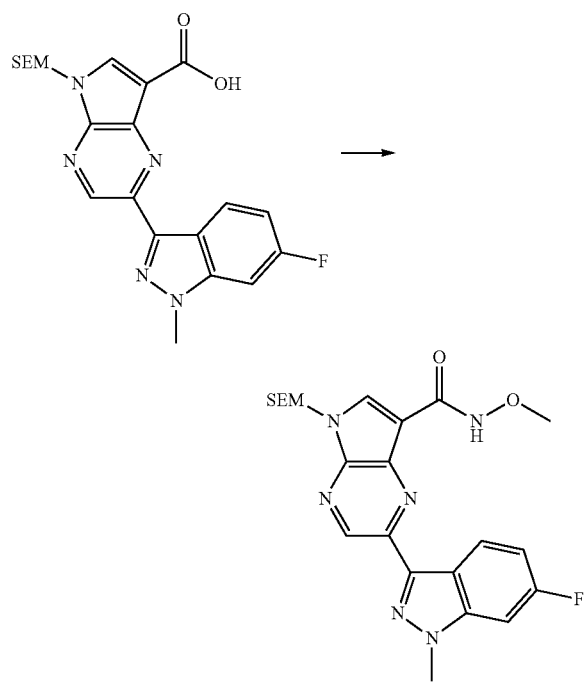

To a stirred suspension of 2-(6-fluoro-1-methyl-1H-indazol-3-yl)-5-((2-(trimethylsilyl)ethoxy)methyl)-5H-pyrrolo[2,3-b]pyrazine-7-carboxylic acid (50 mg, 113 µmol) and O-methylhydroxylamine hydrochloride (11.3 mg, 136 µmol) and diisopropylethylamine (79 µL, 453 µmol) in DMF (2 mL) was added o-(benzotriazol-1-yl)-N,N,N',N'-bis(tetramethylene)uronium hexafluorophosphate (58.6 mg, 136 µmol) at 20° C. for overnight. The reaction mixture was diluted with ethyl acetate and washed with 1 N HCl solution. The organic layer was then washed with saturated sodium bicarbonate and brine then dried (sodium sulfate), filtered and concentrated in vacuo to give the crude 2-(6-fluoro-1-methyl-1H-indazol-3-yl)-5-(2-trimethylsilanyl-ethoxymethyl)-5H-pyrrolo[2,3-b]pyrazine-7-carboxylic acid methoxy-amide (53 mg) as a white solid. This was used directly in the next step without further purification. MS (M+H)$^+$=471.

Step 2

2-(6-Fluoro-1-methyl-1H-indazol-3-yl)-5H-pyrrolo[2,3-b]pyrazine-7-carboxylic acid methoxy-amide

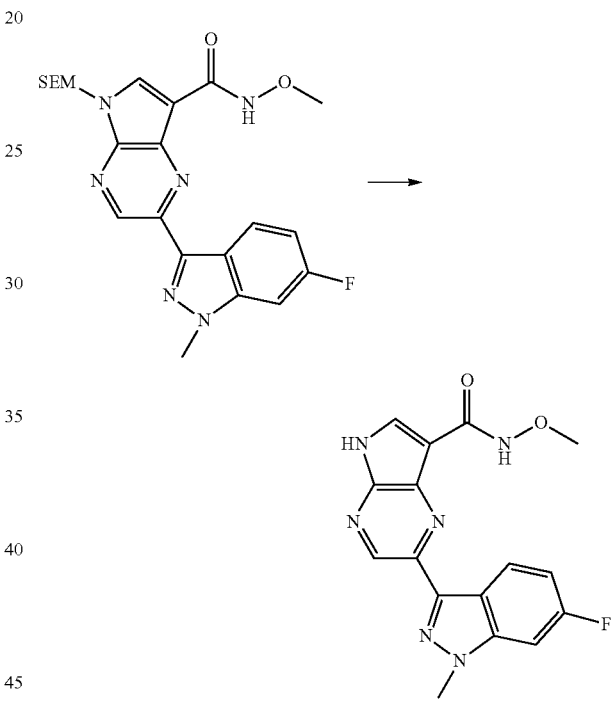

To a stirred solution of 2-(6-fluoro-1-methyl-1H-indazol-3-yl)-5-(2-trimethylsilanylethoxymethyl)-5H-pyrrolo[2,3-b]pyrazine-7-carboxylic acid methoxy-amide (53 mg, 113 µmol) in dichloromethane (2 mL) was added trifluoroacetic acid (0.4 mL, 5.19 mmol) at 20° C. After 2 h, the mixture was concentrated in vacuo. The residue was diluted with dichloromethane and concentrated again. The residue was then suspended in dichloromethane (2 mL) and ethylenediamine (0.4 mL, 5.92 mmol) added. The mixture was stirred for 1 h, then concentrated in vacuo. To the residue was added ethyl acetate and water. The organic layer was then washed with brine then dried (sodium sulfate), filtered and concentrated in vacuo. Purification by chromatography (silica, 25 g pre-packed SiliCycle cartridge, 40-80% EtOAc in hexane gradient increasing over 15 min) gave 2-(6-fluoro-1-methyl-1H-indazol-3-yl)-5H-pyrrolo[2,3-b]pyrazine-7-carboxylic acid methoxy-amide (45 mg, 0.39 µmol, 39%) as a light yellow powder. MS (M+H)$^+$=341; $^1$H NMR (DMSO-d$_6$) δ: 12.87 (br. s., 1H), 10.97 (s, 1H), 9.09 (s, 1H), 8.66 (dd, J=8.8, 5.3 Hz, 1H), 8.45 (s, 1H), 7.67 (d, J=9.8 Hz, 1H), 7.24 (t, J=9.3 Hz, 1H), 4.15 (s, 3H), 3.84 (s, 3H).

Example 362

2-(6-Fluoro-1-methyl-1H-indazol-3-yl)-5H-pyrrolo[2,3-b]pyrazine-7-carboxylic acid tert-butylamide

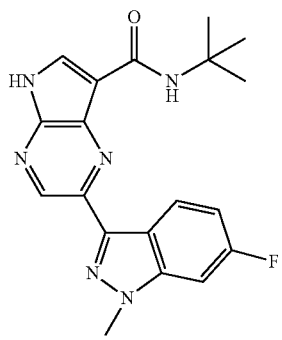 [SMILES: Cn1nc(-c2cnc3[nH]cc(C(=O)NC(C)(C)C)c3n2)c2ccc(F)cc21]

Step 1

2-(6-Fluoro-1-methyl-1H-indazol-3-yl)-5-((2-(trimethylsilyl)ethoxy)methyl)-5H-pyrrolo[2,3-b]pyrazine-7-carboxylic acid tert-butylamide

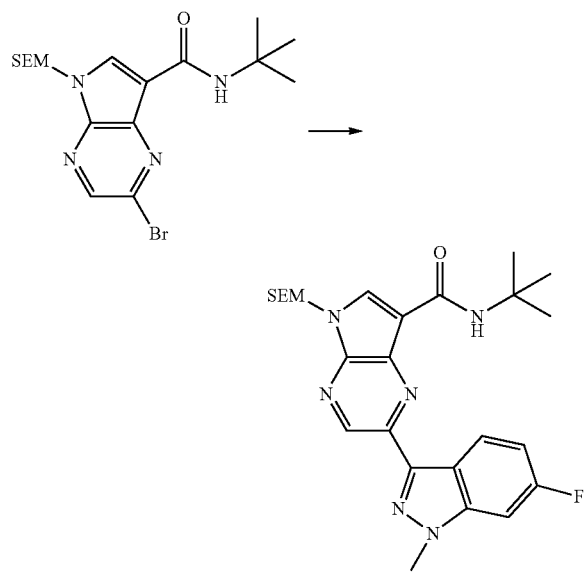

2-Bromo-N-tert-butyl-5-((2-(trimethylsilyl)ethoxy)methyl)-5H-pyrrolo[2,3-b]pyrazine-7-carboxamide (80 mg, 0.187 mmol) and 6-fluoro-1-methyl-3-(tributylstannyl)-1H-indazole (0.1 g, 0.228 mmol) were dissolved in DMF (3 mL). The reaction mixture was evacuated and filled with nitrogen. Copper(I) iodide (6.71 mg, 0.0749 mmol) and tetrakis(triphenylphosphine)palladium (0) (10.8 mg, 0.00936 mmol) were added. The reaction mixture was heated at 90° C. for 2 h. The mixture was cooled and partitioned between ethyl acetate and water, the organic phase washed with brine, then dried over magnesium sulfate. The crude compound was purified by chromatography using 25% ethyl acetate/hexanes to obtain 2-(6-fluoro-1-methyl-1H-indazol-3-yl)-5-((2-(trimethylsilyl)ethoxy)methyl)-5H-pyrrolo[2,3-b]pyrazine-7-carboxylic acid tert-butylamide (5 mg, 38%).

Step 2

2-(6-Fluoro-1-methyl-1H-indazol-3-yl)-5H-pyrrolo[2,3-b]pyrazine-7-carboxylic acid tert-butylamide

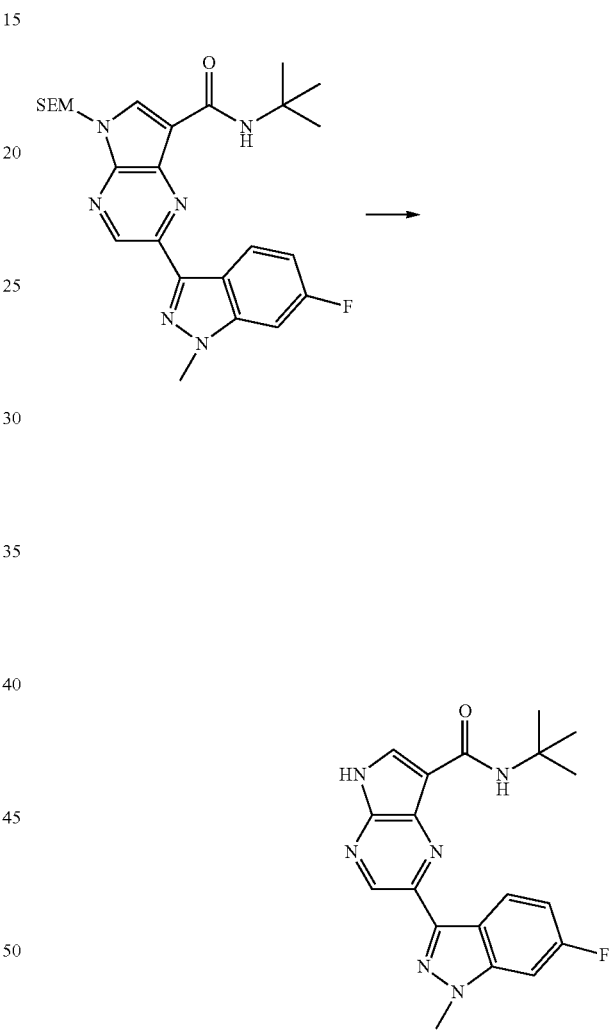

N-tert-Butyl-2-(6-fluoro-1-1H-indazol-3-yl)-5-((2-trimethylsilyl)ethoxy)methyl)-5H-pyrrolo[3,2-b]pyrazine-7-carboximide (35 mg, 0.0705 mmol) and trifluoroacetic acid (0.543 mL, 7.05 mmol) were dissolved in (3.0 mL). After 3 h the reaction mixture was concentrated to dryness and redissolved in dichloromethane. To this mixture was added ethylenediamine (0.476 mL, 7.05 mmol). After 1 h the mixture was concentrated and diluted with 2 mL water. The precipitate was filtered and dried to obtain 2-(6-fluoro-1-methyl-1H-indazol-3-yl)-5H-pyrrolo[2,3-b]pyrazine-7-carboxylic acid tert-butylamide (9 mg, 35%) as an off white solid. MS (M+H)$^+$=367; $^1$H NMR (DMSO-d$_6$) δ: 9.05 (s, 1H), 8.14-

8.62 (m, 2H), 7.92 (s, 1H), 7.69 (dd, J=9.7, 1.9 Hz, 1H), 6.84-7.32 (m, 1H), 4.15 (s, 3H), 1.52 (s, 6H).

Example 363

2-(6-Fluoro-1-methyl-1H-indazol-3-yl)-5H-pyrrolo[2,3-b]pyrazine-7-carboxylic acid (2-hydroxy-1,1-dimethyl-ethyl-amide

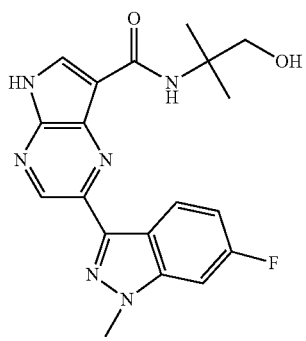 [SMILES: COc1ccc2c(-c3cnc4[nH]cc(C(=O)NC(C)(C)CO)c4n3)nn(C)c2c1]

Step 1

2-(6-Fluoro-1-methyl-indazol-3-yl)-5-(2-trimethyl-silanyl-ethoxymethyl)-5H-pyrrolo[2,3-b]pyrazine-7-carboxylic acid (2-hydroxy-1,1-dimethyl-ethyl)-amide

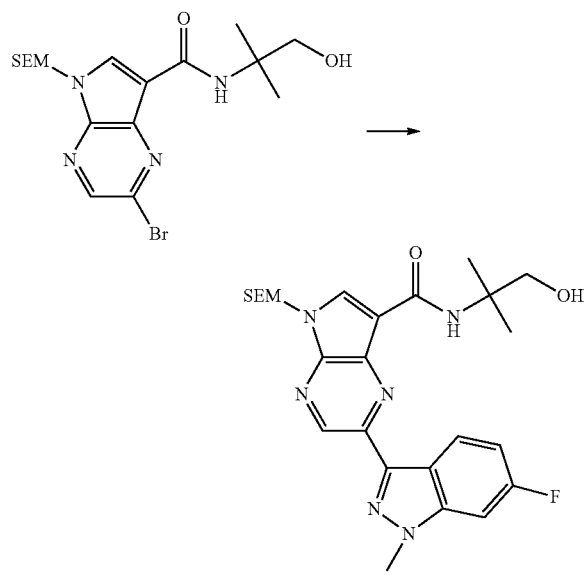

2-Bromo-N-(1-hydroxy-2-methylpropan-2-yl)-5-((2-trimethylsilyl)ethoxy)methyl-5H-pyrrolo-[2,3-]pyrazine-7-carboxamide (0.17 g, 0.383 mmol), 6-fluoro-1-methyl-3-(tributylstannyl)-1H-indazole (0.168 g, 0.383 mmol) and cooper(I) iodide (14.6 mg, 0.076 mmol) were combined in DMF (3.0 mL). The mixture was degassed and filled with nitrogen. Tetrakis(triphenylphosphine)palladium(0) (46 mg, 0.041 mmol) was added and the reaction mixture was heated at 90° C. for 2 h. The mixture was cooled and concentrated in vacuo then purified by chromatography (silica, 3:2 ethyl acetate:hexanes) to give 2-(6-fluoro-1-methyl-indazol-3-yl)-5-(2-trimethyl-silanyl-ethoxymethyl)-5H-pyrrolo[2,3-b]pyrazine-7-carboxylic acid (2-hydroxy-1,1-dimethyl-ethyl)-amide (80 mg, 40%).

Step 2

2-(6-Fluoro-1-methyl-1H-indazol-3-yl)-5H-pyrrolo[2,3-b]pyrazine-7-carboxylic acid (2-hydroxy-1,1-dimethyl-ethyl-amide

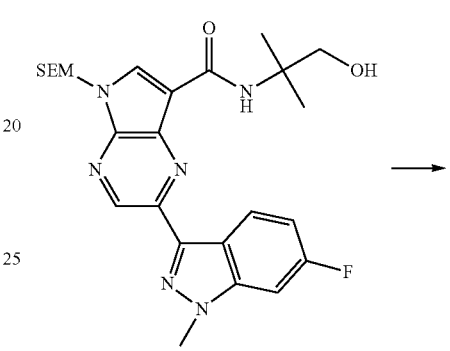

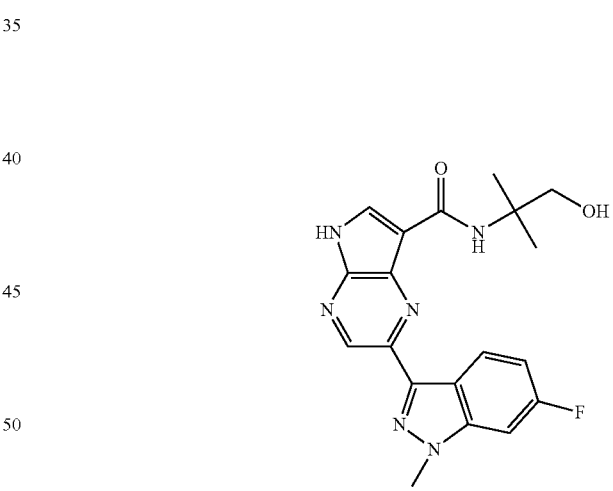

2-(6-Fluoro-1-methyl-1H-indazol-3-yl)-N-(1-hydroxy-2-methylpropan-2-yl)-5-((2-(trimethylsilyl)ethoxy)methyl)-5H-pyrrolo[2,3-b]pyrazine-7-carboxamide (0.08 g, 0.156 mmol), and trifluoroacetic acid (1 mL, 13.0 mmol) were stirred in dichloromethane for 15 h. The reaction mixture was concentrated in vacuo then ethylenediamine (1 mL, 14.8 mmol) in dichloromethane (5 mL) was added. After 1 h, the mixture was concentrated to dryness and water (1 mL) added. The solid precipitate was collected by filtration and dried to give 2-(6-fluoro-1-methyl-1H-indazol-3-yl)-5H-pyrrolo[2,3-b]pyrazine-7-carboxylic acid (2-hydroxy-1,1-dimethyl-ethyl-amide (24 mg, 36%). MS (M+H)$^+$=383; $^1$H NMR (DMSO-d$_6$) δ: 9.07 (s, 1H), 8.60 (dd, J=8.7, 5.5 Hz, 1H), 8.37

(s, 1H), 7.91 (s, 1H), 7.66 (d, J=9.8 Hz, 1H), 7.15 (t, J=8.3 Hz, 1H), 4.14 (s, 3H), 3.62 (s, 2H), 1.45 (s, 6H).

Example 364

2-(6-Chloro-1-methyl-1H-indazol-3-yl)-5H-pyrrolo[2,3-b]pyrazine-7-carboxylic acid (2-hydroxy-1,1-dimethyl-ethyl)-amide

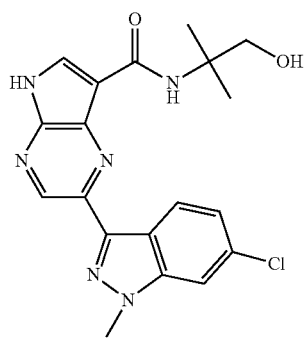

Step 1

2-(6-Chloro-1-methyl-1H-indazol-3-yl)-5-trimethyl-silanyl-ethoxymethyl)-5H-pyrrolo[2,3-b]pyrazine-7-carboxylic acid (2-hydroxy-1,1-dimethyl-ethyl)-amide

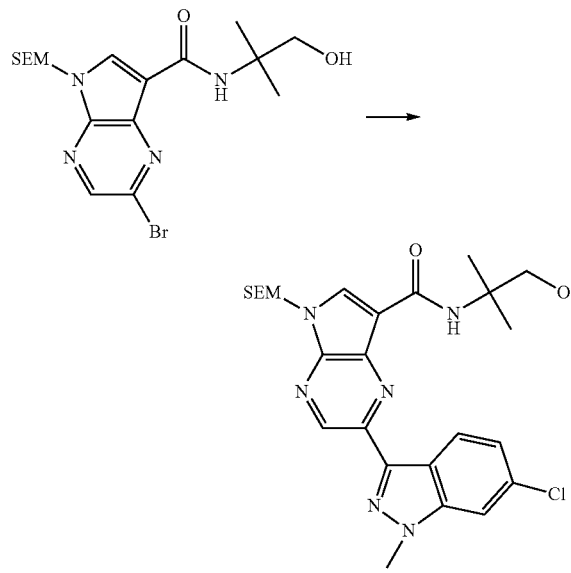

2-Bromo-N-tert-butyl-5-((2-(trimethylsilyl)ethoxy)methyl)-5H-pyrrolo[2,3-b]pyrazine-7-carboxamide (90 mg, 0.203 mmol) and 6-chloro-1-methyl-3-(tributylstannyl)-1H-indazole (0.148 g, 0.228 mmol) were dissolved in DMF (3 mL). The reaction mixture was evacuated and filled with nitrogen then copper(I) iodide (9 mg, 0.081 mmol) and tetrakis(triphenylphosphine)palladium (0) (46 mg, 0.046 mmol) were added. The reaction mixture was heated at 90° C. for 2 h then partitioned between ethyl acetate and water. The organic phase was washed with brine then dried over magnesium sulfate. The crude material was purified by chromatography using 25% ethyl acetate/hexane to obtain 2-(6-chloro-1-methyl-1H-indazol-3-yl)-5-trimethyl-silanyl-ethoxymethyl)-5H-pyrrolo[2,3-b]pyrazine-7-carboxylic acid (2-hydroxy-1,1-dimethyl-ethyl)-amide (40 mg, 37%).

Step 2

2-(6-Chloro-1-methyl-1H-indazol-3-yl)-5H-pyrrolo[2,3-b]pyrazine-7-carboxylic acid (2-hydroxy-1,1-dimethyl-ethyl)-amide

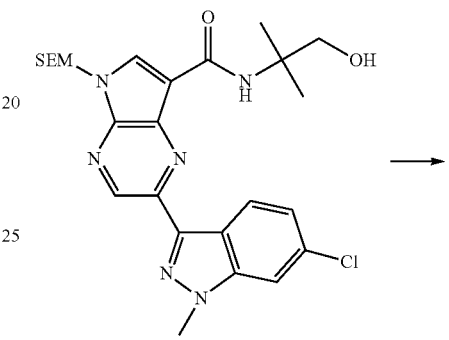

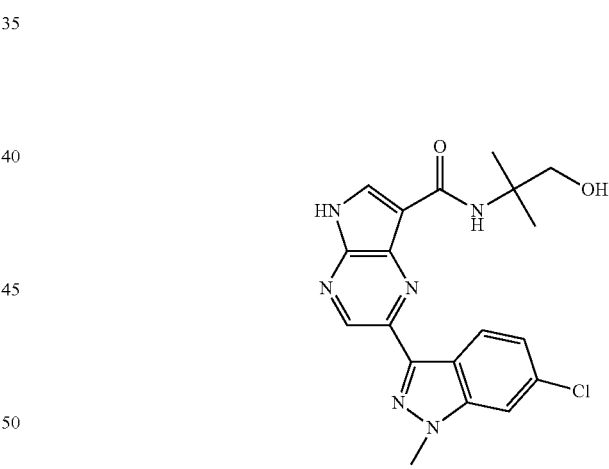

2-(6-Chloro-1-methyl-1H-indazol-3-yl)-N-(1-hydroxy-2-methylpropan-2-yl)-5-((2-(trimethylsilyl)ethoxy)methyl)-5H-pyrrolo[3,2-b]pyrazine-7-carboxamide (0.04 g, 0.076 mmol), trifluoroacetic acid (0.582 mL, 7.56 mmol) and dichloromethane (3.00 mL) were combined and stirred for 3 h. The reaction mixture was concentrated to dryness and diluted with dichloromethane (3 mL), then ethylenediamine (0.510 mL, 7.56 mmol) was added. After 1 h the mixture was concentrated to dryness and ice water (1 mL) added. The solid formed was collected by filtration then triturated with ethyl acetate to obtain 2-(6-chloro-1-methyl-1H-indazol-3-yl)-5H-pyrrolo[2,3-b]pyrazine-7-carboxylic acid (2-hydroxy-1,1-dimethyl-ethyl)-amide (5 mg, 16%). MS (M+H)$^+$=399; $^1$H NMR (DMSO-d$_6$) δ: 8.94-9.36 (m, 1H), 8.51-8.76 (m, 1H), 8.37 (s, 1H), 7.80-8.08 (m, 2H), 7.29 (t, J=8.8 Hz, 1H), 4.17 (d, J=5.8 Hz, 3H), 3.48-3.80 (m, 2H), 1.45 (d, J=3.3 Hz, 6H).

Example 365

2-(6-Methoxy-1-1H-indazole-3-yl-5H-pyrrolo[2,3-b]pyrazine-7-carboxylic (2-hydroxy-1,1-dimethyl-ethyl)-amide

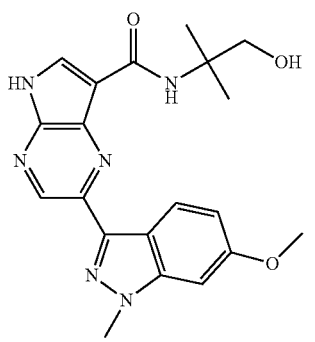

Prepared according to the procedure outlined in Example 364, substituting 6-methoxy-1-methyl-3-tributylstannanyl-1H-indazole for 6-chloro-1-methyl-3-tributylstannanyl-1H-indazole in Step 1. MS: (M+H)$^+$=395; $^1$H NMR (DMSO-d$_6$) δ: 9.04 (s, 1H), 8.20-8.65 (m, 2H), 7.93 (s, 1H), 7.20 (d, J=2.0 Hz, 1H), 6.88 (dd, J=8.9, 2.1 Hz, 1H), 4.12 (s, 3H), 3.90 (s, 3H), 3.63 (s, 2H), 1.44 (s, 6H).

Example 366

2-(6-Methoxy-1-methyl-1H-indazol-3-yl)-5H-pyrrolo[2,3-b]pyrazine-7-carboxylic acid tert-butylamide

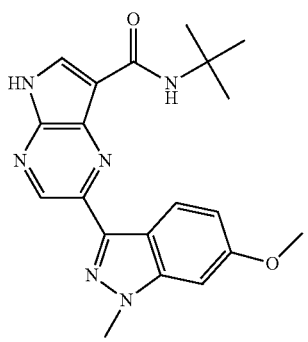 [SMILES: COc1ccc2c(-c3cnc4[nH]cc(C(=O)NC(C)(C)C)c4n3)nn(C)c2c1]

Prepared according to the procedure outlined in Example 362, substituting 6-methoxy-1-methyl-3-tributylstannanyl-1H-indazole for 6-fluoro-1-methyl-3-tributylstannanyl-1H-indazole in Step 1. MS: (M+H)$^+$=379; $^1$H NMR (DMSO-d$_6$)

δ: 9.05 (s, 1H), 8.15-8.58 (m, 2H), 7.95 (s, 1H), 7.22 (s, 1H), 6.86 (d, J=8.8 Hz, 1H), 4.13 (s, 3H), 3.90 (s, 3H), 1.52 (s, 9H).

Example 367

2-(6-Ethyl-1-methyl-1H-indazol-3-yl)-5H-pyrrolo[2,3-b]pyrazine-7-carboxylic acid tert-butylamide

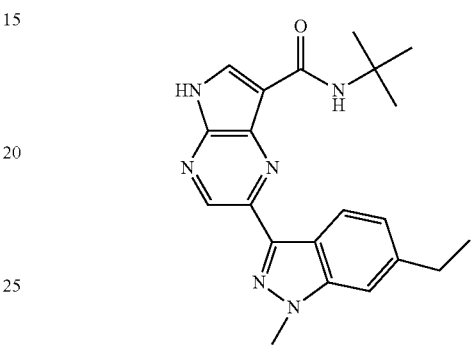

Step 1

2-(6-Ethyl-1-methyl-1H-indazol-3-yl)-5-((2-(trimethylsilyl)ethoxy)methyl)-5H-pyrrolo[2,3-b]pyrazine-7-carboxylic acid tert-butylamide

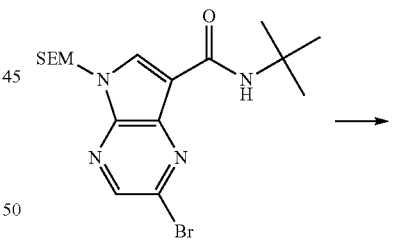

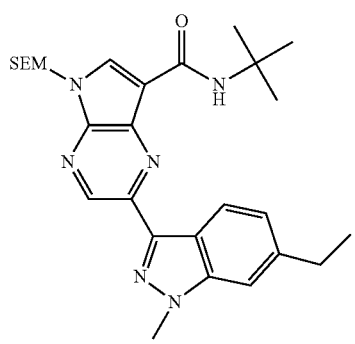

Prepared according to the procedure outlined in Example 162, Step 1, substituting 6-ethyl-1-methyl-3-tributylstannanyl-1H-indazole (see Example 87) for 6-fluoro-1-methyl-3-tributylstannanyl-1H-indazole.

Step 2

2-(6-Ethyl-1-methyl-1H-indazol-3-yl)-5H-pyrrolo[2,3-b]pyrazine-7-carboxylic acid tert-butylamide

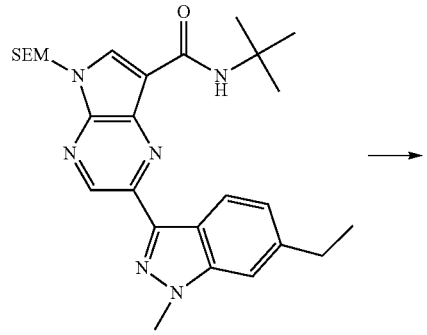

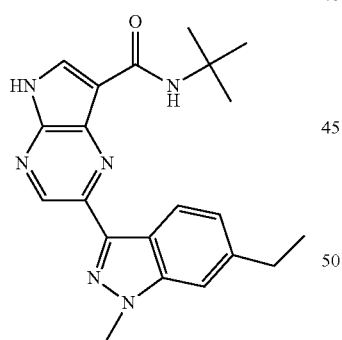

N-tert-Butyl-2-(6-ethyl-1-methyl-1H-indazol-3-yl)-5-((2-(trimethylsilyl)ethoxy)methyl)-5H-pyrrolo[3,2-b]pyrazine-7-carboxamide (0.03 g, 0.059 mmol), ethylenediamine (1 mL, 15.0 mmol) and TBAF (1 mL, 3.45 mmol) were combined with DMF (3.0 mL) and the reaction mixture warmed to 60° C. After 3 h, the mixture was concentrated to dryness and partitioned between ethyl acetate and water. The organic phase was concentrated in vacuo then purified by chromatography to give 2-(6-ethyl-1-methyl-1H-indazol-3-yl)-5H-pyrrolo[2,3-b]pyrazine-7-carboxylic acid tert-butylamide (5 mg, 22%). MS: (M+H)$^+$=377; $^1$H NMR (DMSO-d$_6$) δ: 12.79 (br. s., 1H), 8.96-9.28 (m, 1H), 8.19-8.49 (m, 2H), 7.97 (s, 1H), 7.57 (s, 1H), 6.98-7.25 (m, 1H), 4.16 (s, 3H), 2.81 (q, J=7.4 Hz, 2H), 1.41-1.66 (m, 9H), 1.21-1.35 (m, 3H).

Example 368

2-(1,6-Dimethyl-indazol-3-yl-5H-pyrrolo[2,3-b]pyrazine-7-carboxylic acid (2-hydroxy-1,1-dimethyl-ethyl)-amide

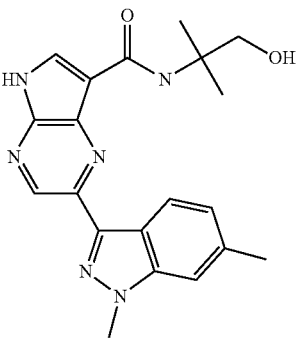 [SMILES: Cc1ccc2c(-c3cnc4[nH]cc(C(=O)NC(C)(C)CO)c4n3)nn(C)c2c1]

Prepared according to the procedure outlined in Example 364, substituting 6-methyl-1-methyl-3-tributylstannanyl-1H-indazole for 6-chloro-1-methyl-3-tributylstannanyl-1H-indazole in Step 1. MS: (M+H)$^+$=379; $^1$H NMR (DMSO-d$_6$) δ: 9.10 (s, 1H), 8.22-8.68 (m, 2H), 7.93 (s, 1H), 7.54 (s, 1H), 7.12 (d, J=7.5 Hz, 1H), 5.06 (t, J=5.9 Hz, 1H), 4.14 (s, 3H), 3.65 (d, J=5.5 Hz, 2H), 1.46 (s, 6H).

Example 369

2-(7-Methyl-1H-indazol-3-yl)-5H-pyrrolo[2,3-b]pyrazine-7-carboxylic acid tert-butylamide

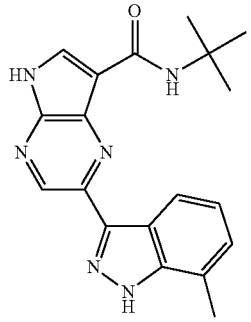 [SMILES: Cc1cccc2c(-c3cnc4[nH]cc(C(=O)NC(C)(C)C)c4n3)n[nH]c12]

Prepared according to the procedure outlined in Example 362, substituting 7-methyl-3-tributylstannanyl-1H-indazole for 6-fluoro-1-methyl-3-tributylstannanyl-1H-indazole in Step 1.

MS: (M+H)$^+$=349; $^1$H NMR (DMSO-d$_6$) δ: 9.09 (s, 1H), 8.34 (d, J=8.1 Hz, 2H), 8.00 (s, 1H), 6.96-7.37 (m, 2H), 2.58 (s, 3H), 1.35-1.58 (m, 9H).

Example 370

2-(1-Methyl-6-trifluoromethoxy-1H-indazol-3-yl)-5H-pyrrolo[2,3-b]pyrazine-7-carboxylic acid tert-butylamide

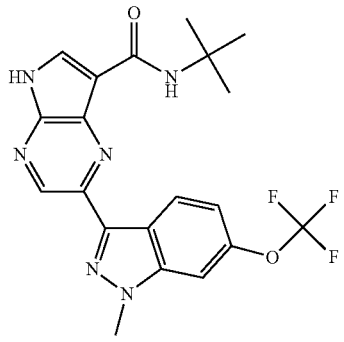 [SMILES: Cn1nc(-c2cnc3[nH]cc(C(=O)NC(C)(C)C)c3n2)c2ccc(OC(F)(F)F)cc21]

Prepared according to the procedure outlined in Example 362, substituting 1-methyl-3-tributylstannanyl-6-trifluoromethoxy-1H-indazole for 6-fluoro-1-methyl-3-tributylstannanyl-1H-indazole in Step 1. MS: (M+H)$^+$=433; $^1$H NMR (DMSO-d$_6$) δ: 9.09 (s, 1H), 8.56 (d, J=8.8 Hz, 1H), 8.40 (s, 1H), 7.92 (s, 2H), 7.25 (d, J=9.0 Hz, 1H), 4.21 (s, 3H), 1.52 (s, 9H).

Example 371

2-(1-Methyl-6-trifluoromethoxy-1H-indazol-3-yl)-5H-pyrrolo[2,3-b]pyrazine-7-carboxylic acid (2-hydroxy-1,1-dimethyl-ethyl)amide

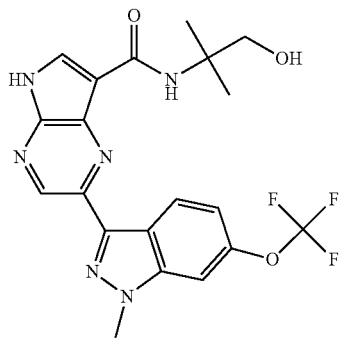 [SMILES: Cn1nc(-c2cnc3[nH]cc(C(=O)NC(C)(C)CO)c3n2)c2ccc(OC(F)(F)F)cc21]

Prepared according to the procedure outlined in Example 364, substituting 1-methyl-3-tributylstannanyl-6-trifluoromethoxy-1H-indazole for 6-chloro-1-methyl-3-tributylstannanyl-1H-indazole in Step 1. MS: (M+H)$^+$=449; $^1$H NMR (DMSO-d$_6$) δ: 9.11 (s, 1H), 8.70 (d, J=9.0 Hz, 1H), 8.38 (d, J=3.0 Hz, 1H), 7.89 (d, J=2.8 Hz, 2H), 7.25 (d, J=8.8 Hz, 1H), 6.52 (s, OH), 5.13 (br. s., 1H), 4.20 (s, 3H), 3.60 (br. s., 2H), 1.44 (s, 6H).

Example 372

2-(7-Methyl-1H-indazol-3-yl)-5H-pyrrolo[2,3-b]pyrazine-7-carboxylic acid (2-hydroxy-1,1-dimethyl-ethyl)-amide

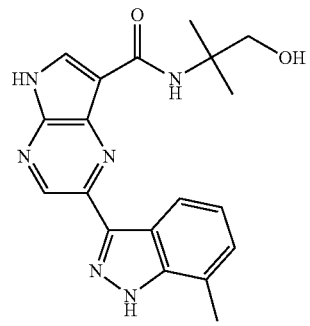 [SMILES: Cc1cccc2c(-c3cnc4[nH]cc(C(=O)NC(C)(C)CO)c4n3)n[nH]c12]

Prepared according to the procedure outlined in Example 364, substituting 7-methyl-3-tributylstannanyl-1H-indazole for 6-chloro-1-methyl-3-tributylstannanyl-1H-indazole in Step 1.

MS: (M+H)$^+$=365; $^1$H NMR (DMSO-d$_6$, 400 MHz): δ (ppm) 13.57 (br. s., 1H), 9.17 (s, 1H), 8.40 (d, J=8.0 Hz, 1H), 8.36 (s, 1H), 7.97 (s, 1H), 7.24 (d, J=7.0 Hz, 1H), 7.12-7.19 (m, 1H), 4.98-5.10 (m, 1H), 3.65 (d, J=5.0 Hz, 2H), 2.59 (s, 3H), 1.45 (s, 6H).

Example 373

N-tert-Butyl-2-(1-methyl-1H-pyrazolo[3,4-b]pyridin-3-yl)-5H-pyrrolo[3,2-b]pyrazine-7-carboxamide

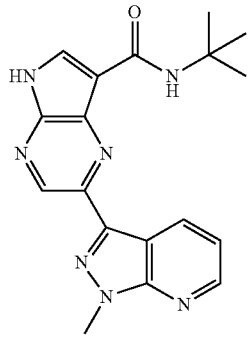 [SMILES: Cn1nc(-c2cnc3[nH]cc(C(=O)NC(C)(C)C)c3n2)c2cccnc21]

Step 1

3-Iodo-1-methyl-1H-pyrazolo[3,4-b]pyridine

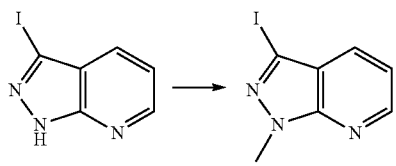

To a stirred solution of 3-iodo-1H-pyrazolo[3,4-b]pyridine (3.5 g, 14.3 mmol) in THF (70 mL) at 0° C. was added potassium tert-butoxide (1.92 g, 17.1 mmol) and the reaction mixture stirred at 0° C. for 1 h. Iodomethane (2.43 g, 1.07 mL, 17.1 mmol) was added drop-wise, then the mixture was warmed to rt. After 6 h the mixture was diluted with water, extracted with dichloromethane, then the combined organic phases were dried (MgSO$_4$), filtered and concentrated in vacuo. Purification by chromatography (silica, 20-60% ethyl acetate in hexanes) gave 3-iodo-1-methyl-1H-pyrazolo[3,4-b]pyridine (1.14 g, 4.4 mmol, 31%) as an off-white solid. MS (M+H)$^+$=260.

Step 2

N-tert-Butyl-2-(1-methyl-1H-pyrazolo[3,4-b]pyridin-3-yl)-5-((2-(trimethylsilyl)ethoxy)methyl)-5H-pyrrolo[3,2-b]pyrazine-7-carboxamide

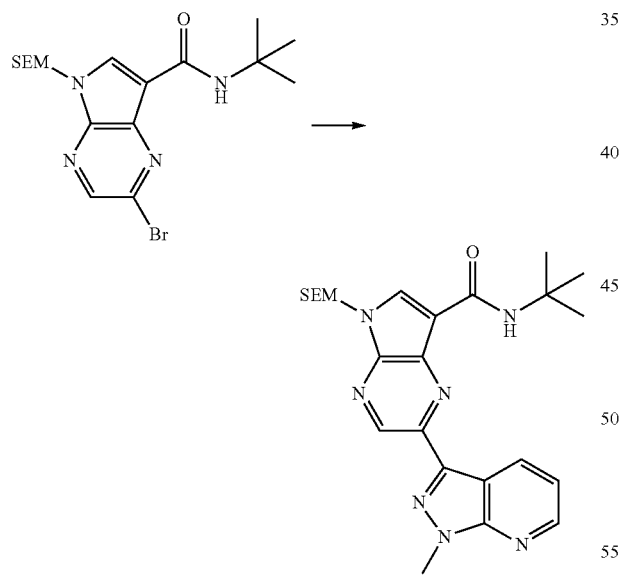

To a solution of 2-bromo-N-tert-butyl-5-((2-(trimethylsilyl)ethoxy)methyl)-5H-pyrrolo[3,2-b]pyrazine-7-carboxamide (400 mg, 936 µmol) and 3-iodo-1-methyl-1H-pyrazolo[3,4-b]pyridine (364 mg, 1.4 mmol) in DMF (8 mL) was added hexabutylditin (814 mg, 709 µL, 1.4 mmol) then the mixture was purged with nitrogen for 10 min. Tetrakis(triphenylphosphine)palladium (0) (54.1 mg, 46.8 µmol) was added and the reaction mixture was heated at 125° C. After 18 h the mixture was filtered through a pad of Celite to remove catalyst, then the filtrates were concentrated in vacuo and purified by chromatography (silica, 10-70% ethyl acetate in hexanes) to obtain N-tert-butyl-2-(1-methyl-1H-pyrazolo[3,4-b]pyridin-3-yl)-5-((2-(trimethylsilyl)ethoxy)methyl)-5H-pyrrolo[3,2-b]pyrazine-7-carboxamide (306 mg, 638 µmol, 68%) as an off-white powder. MS (M+H)$^+$=480.

Step 3

N-tert-Butyl-2-(1-methyl-1H-pyrazolo[3,4-b]pyridin-3-yl)-5H-pyrrolo[3,2-b]pyrazine-7-carboxamide

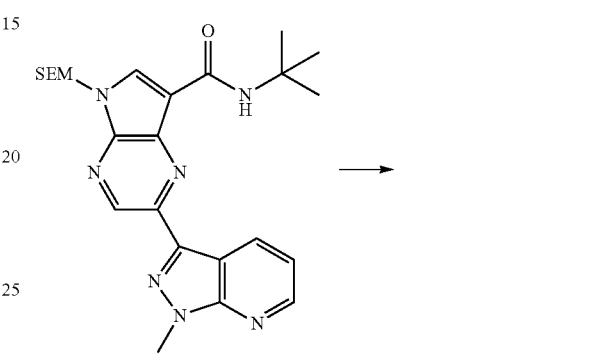

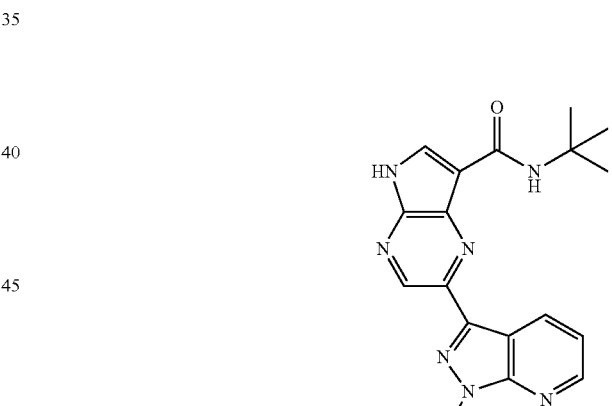

To a stirred solution of N-tert-butyl-2-(1-methyl-1H-pyrazolo[3,4-b]pyridin-3-yl)-5-((2-(trimethylsilyl)ethoxy)methyl)-5H-pyrrolo[3,2-b]pyrazine-7-carboxamide (306 mg, 638 µmol) in DMF (15 mL) was added ethylenediamine (1.92 g, 2.15 mL, 31.9 mmol) followed by TBAF (1.91 mL, 1.91 mmol) and the mixture heated at 60° C. under nitrogen for 15 h. The mixture was cooled, diluted with dichloromethane, washed with water and brine, then dried (MgSO$_4$), filtered and concentrated to obtain an oil. This was triturated with water to remove tetrabutylammonium hydroxide, filtered, and the residue purified by chromatography (silica, 5-10% methanol in dichloromethane) to obtain N-tert-butyl-2-(1-methyl-1H-pyrazolo[3,4-b]pyridin-3-yl)-5H-pyrrolo[3,2-b]pyrazine-7-carboxamide (19.2 mg, 55.0 µmol, 9%) as a light yellow powder. MS (M+H)$^+$=350; $^1$H NMR (DMSO-d$_6$) δ:

9.12 (s, 1H), 8.84 (dd, J=8.2, 1.6 Hz, 1H), 8.70 (dd, J=4.5, 1.5 Hz, 1H), 8.42 (s, 1H), 7.93 (s, 1H), 7.39 (dd, J=8.0, 4.5 Hz, 1H), 4.22 (s, 3H).

Example 374

2-(6-Fluoro-1-methyl-1H-indazol-3-yl)-N-(1-(hydroxymethyl)cyclopropyl)-5H-pyrrolo[3,2-b]pyrazine-7-carboxamide

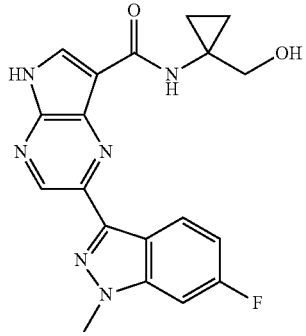 [SMILES: Cn1nc(-c2cnc3[nH]cc(C(=O)NC4(CO)CC4)c3n2)c2ccc(F)cc21]

Step 1

Methyl 2-bromo-5-(pivaloyloxymethyl)-5H-pyrrolo[2,3-b]pyrazine-7-carboxylate

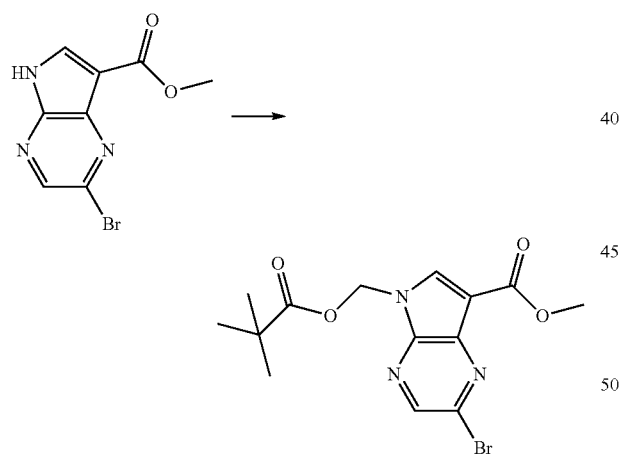

To a stirred mixture of methyl 2-bromo-5H-pyrrolo[2,3-b]pyrazine-7-carboxylate (0.24 g, 0.94 mmol) and K$_2$CO$_3$ (0.156 g, 1.13 mmol) in 10 mL of DMF was added chloromethyl pivalate (0.17 g, 1.13 mmol) drop-wise at room temperature. Then the mixture was stirred at room temperature for 16 hours. The mixture was then poured into 30 mL of water, extracted with ethyl acetate (90 mL). The organic phase was washed with brine (10 mL) and dried over Na$_2$SO$_4$ to give a crude product, which was purified by column chromatography (silica gel, 200-300 mesh, eluting with a mixture of ethyl acetate and petroleum ether (1:1, v/v) to give methyl 2-bromo-5-(pivaloyloxymethyl)-5H-pyrrolo[2,3-b]pyrazine-7-carboxylate (0.276 g, 79.5%) as a pale yellow solid.

LCMS: (M+H)$^+$=370; $^1$H NMR (300 MHz, CDCl$_3$): δ 8.42 (s, 1H), 8.38 (s, 1H), 6.21 (s, 2H), 3.96 (s, 3H), 1.15 (s, 9H).

Step 2

Methyl 2-(6-fluoro-1-methyl-1H-indazol-3-yl)-5-(pivaloyloxymethyl)-5H-pyrrolo[2,3-b]pyrazine-7-carboxylate

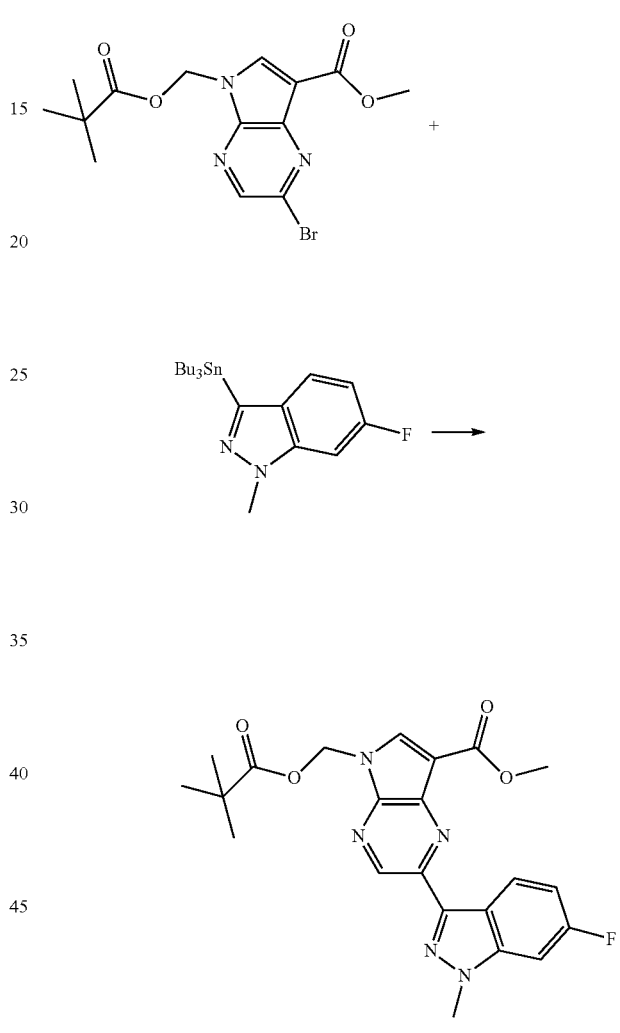

To a stirred solution of 6-fluoro-1-methyl-3-(tributylstannyl)-1H-indazole (0.51 g, 0.616 mmol), methyl 2-bromo-5-(pivaloyloxymethyl)-5H-pyrrolo[2,3-b]pyrazine-7-carboxylate (0.18 g, 0.486 mmol) in 6 mL of DMF were added CuI (0.04 g, 0.21 mmol) and Pd(PPh$_3$)$_4$ (0.057 g, 0.045 mmol) in one portion under nitrogen at room temperature. Then the reaction mixture was degassed by bubbling nitrogen for 10 minutes and stirred at 90° C. under nitrogen for 16 hours. The solvent was evaporated at 70° C. under reduced pressure and the residue was purified by column chromatography (silica gel, 200-300 mesh, eluting with a mixture of ethyl acetate and petroleum ether (1:1, v/v) to give methyl 2-(6-fluoro-1-methyl-1H-indazol-3-yl)-5-(pivaloyloxymethyl)-5H-pyrrolo[2,3-b]pyrazine-7-carboxylate (0.182 g, 85.2%) as a yellow solid. LCMS: (M+H)$^+$=440; $^1$H NMR (300 MHz, DMSO): δ 9.13 (s, 1H), 8.83-8.78 (m, 1H), 8.70 (s, 1H), 7.63 (dd, 1H, $J_1$=9.6 Hz, $J_2$=2.1 Hz), 7.23 (dt, 1H, $J_1$=9.3 Hz, $J_2$=2.1 Hz), 6.30 (s, 2H), 4.13 (s, 3H), 3.92 (s, 3H), 1.08 (s, 9H).

Step 3

2-(6-Fluoro-1-methyl-1H-indazol-3-yl)-5H-pyrrolo[2,3-b]pyrazine-7-carboxylic acid

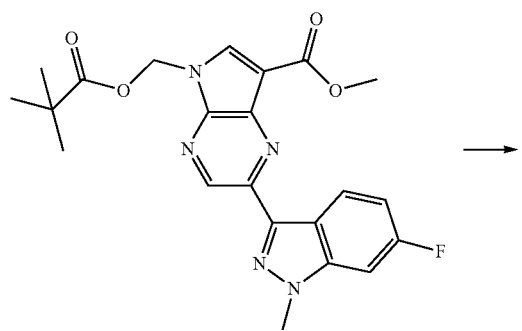

A mixture of methyl 2-(6-fluoro-1-methyl-1H-indazol-3-yl)-5-(pivaloyloxymethyl)-5H-pyrrolo[2,3-b]pyrazine-7-carboxylate (0.24 g, 0.546 mmol), KOH (0.611 g, 10.9 mmol), water (4 mL) and dioxane (10 mL) was stirred at 100° C. for 5 hours. Then the reaction mixture was cooled to room temperature and treated with 1N HCl to pH=2. The solvent was evaporated at 40° C. under reduced pressure and the residue was triturated with water (10 mL), then decanted and dried at 40° C. under reduced pressure to give 2-(6-fluoro-1-methyl-1H-indazol-3-yl)-5-(pivaloyloxymethyl)-5H-pyrrolo[2,3-b]pyrazine-7-carboxylic acid (0.161 g, 94.8%) as a yellow solid. $^1$H NMR (300 MHz, DMSO): δ 12.87 (s, 1H), 12.28 (s, 1H), 9.05 (s, 1H), 8.82 (dd, 1H, $J_1$=9.0 Hz, $J_2$=5.7 Hz), 8.48 (d, 1H, J=2.7 Hz), 7.61 (dd, 1H, $J_1$=10.2 Hz, $J_2$=2.7 Hz), 7.15 (t, 1H, J=12.0 Hz), 4.12 (s, 3H). LCMS: 312.0 [M+H]$^+$, 334.0 [M+Na]$^+$.

Step 4

2-(6-Fluoro-1-methyl-1H-indazol-3-yl)-N-(1-(hydroxymethyl)cyclopropyl)-5H-pyrrolo[3,2-b]pyrazine-7-carboxamide

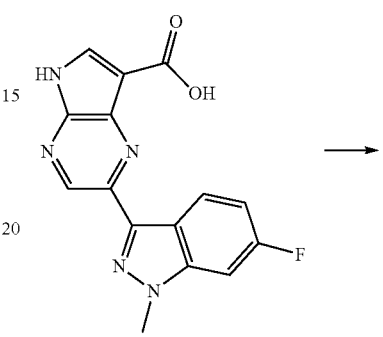

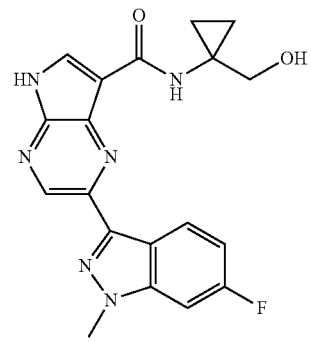

A mixture of 2-(6-fluoro-1-methyl-1H-indazol-3-yl)-5H-pyrrolo[3,2-b]pyrazine-7-carboxylic acid (70 mg, 0.225 mmol), (1-aminocyclopropyl)methanol (30 mg, 0.337 mmol), HATU (171 mg, 0.45 mmol) and DIEA (58 mg, 0.45 mmol) in DMF (3 mL) was stirred at 25° C. for 16 hours. Then the mixture was filtered and the cake was washed with MeOH. The crude product was purified by preparative-HPLC (Gemini 5u C18 150×21.2 mm; inject volume: 3 mL/inj, flow rate: 20 mL/min; wavelength: 214 nm and 254 nm; the gradient conditions were: 55% acetonitrile/45% water (0.1% trifluoroacetic acid, v/v) initially, proceeding to 80% acetonitrile/20% water (0.1% trifluoroacetic acid, v/v) in a linear fashion after 9 min.) to give 2-(6-fluoro-1-methyl-1H-indazol-3-yl)-N-(1-(hydroxymethyl)cyclopropyl)-5H-pyrrolo[3,2-b]pyrazine-7-carboxamide (4 mg, 5%). MS: (M+H)$^+$=381; $^1$H NMR (300 MHz, DMSO): δ 12.88 (s, 1H), 9.12 (s, 1H), 8.71 (s, 1H), 8.60-8.55 (m, 1H), 8.46 (s, 1H), 7.72 (dd, 1H, J=9.6, 2.1 Hz), 7.28-7.21 (m, 1H), 4.17 (s, 3H), 3.60 (s, 2H), 0.96-0.85 (m, 4H).

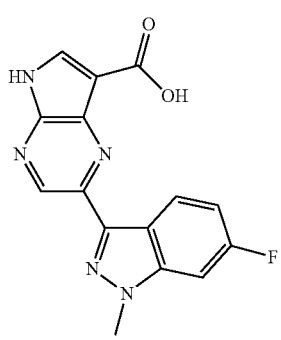

Example 375

2-(6-Fluoro-1-methyl-1H-indazol-3-yl)-N-tert-pentyl-5H-pyrrolo[2,3-b]pyrazine-7-carboxamide

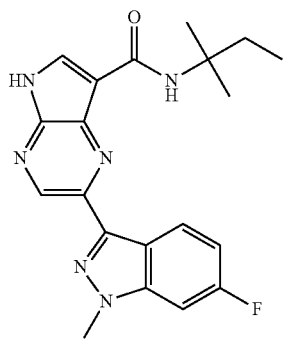 [SMILES: CCC(C)(C)NC(=O)c1c[nH]c2ncc(-c3nn(C)c4cc(F)ccc34)nc12]

To a stirred solution of 2-(6-fluoro-1-methyl-1H-indazol-3-yl)-5H-pyrrolo[2,3-b]pyrazine-7-carboxylic acid (59 mg, 0.19 mmol), HATU (91.20 mmol, 0.24 mmol) and DIPEA (49 mg, 0.38 mmol) in 6 mL of DMF, 2-methylbutan-2-amine (21.60 mg, 0.24 mmol) was added in one portion at room temperature. Then the reaction mixture was stirred for 16 hours. The solvent was evaporated at 70° C. under reduced pressure and the residue was purified by preparative-HPLC (Gemini 5u C18 150×21.2 mm; inject volume: 3 mL/inj, flow rate: 20 mL/min; wavelength: 214 nm and 254 nm; the gradient conditions were: 15% acetonitrile/75% water (0.1% trifluoroacetic acid, v/v) initially, proceeding to 70% acetonitrile/30% water (0.1% trifluoroacetic acid, v/v) in a linear fashion after 9 min.) to give 2-(6-fluoro-1-methyl-1H-indazol-3-yl)-N-tert-pentyl-5H-pyrrolo[2,3-b]pyrazine-7-carboxamide (15 mg, 20.7%) as a white solid. MS: (M+H)$^+$=381; $^1$H NMR (300 MHz, DMSO): δ 12.82 (s, 1H), 9.07 (s, 1H), 8.47-8.37 (m, 2H), 7.81 (s, 1H), 7.70 (dd, 1H, J=9.6, 2.1 Hz), 7.17 (t, 1H, J=2.1 Hz), 4.15 (s, 3H), 1.89 (q, 2H, J=7.6 Hz), 1.46 (s, 6H), 0.87 (t, 3H, J=7.5 Hz).

Example 376

2-(6-Fluoro-1-methyl-1H-indazol-3-yl)-N-(1-methylcyclobutyl)-5H-pyrrolo[2,3-b]pyrazine-7-carboxamide

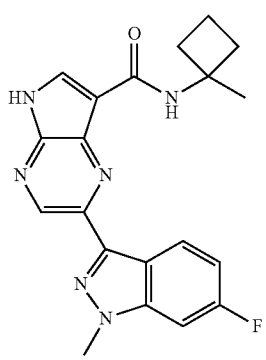 [SMILES: Cn1nc(-c2cnc3[nH]cc(C(=O)NC4(C)CCC4)c3n2)c2ccc(F)cc21]

To a stirred solution of 2-(6-fluoro-1-methyl-1H-indazol-3-yl)-5H-pyrrolo[2,3-b]pyrazine-7-carboxylic acid (59 mg, 0.19 mmol), HATU (91.20 mmol, 0.24 mmol) and DIPEA (49 mg, 0.38 mmol) in 6 mL of DMF, 1-methylcyclobutanamine (21.00 mg, 0.25 mmol) was added in one portion at room temperature and the reaction mixture was stirred for 16 hours. The solvent was evaporated at 80° C. under reduced pressure and the residue was purified by preparative-HPLC (Gemini 5u C18 150×21.2 mm; inject volume: 3 mL/inj; flow rate: 20 mL/min; wavelength: 214 nm and 254 nm; the gradient conditions were: 48% acetonitrile/52% water (0.1% trifluoroacetic acid, v/v) initially, proceeding to 70% acetonitrile/30% water (0.1% trifluoroacetic acid, v/v) in a linear fashion over 9 min.) to give 2-(6-fluoro-1-methyl-1H-indazol-3-yl)-N-(1-methylcyclobutyl)-5H-pyrrolo[2,3-b]pyrazine-7-carboxamide (10 mg, 13.7%) as an off-white solid. MS: (M+H)$^+$=379; $^1$H NMR (300 MHz, DMSO): δ 12.82 (s, 1H), 9.10 (s, 1H), 8.47-8.38 (m, 2H), 8.24 (s, 1H), 7.70 (d, 1H, J=8.7 Hz), 7.17 (t, 1H, J=9.2 Hz), 4.15 (s, 3H), 2.54-2.45 (m, 2H), 2.15-2.13 (m, 2H), 1.96-1.88 (m, 2H), 1.62 (s, 3H).

Example 377

N-(2-Cyanopropan-2-yl)-2-(6-fluoro-1-methyl-1H-indazol-3-yl)-5H-pyrrolo[3,2-b]pyrazine-7-carboxamide

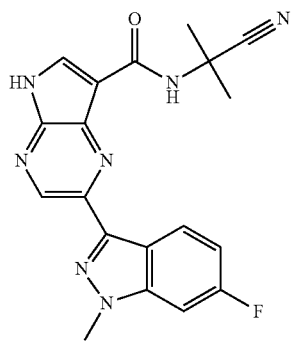 [SMILES: Cn1nc(-c2cnc3[nH]cc(C(=O)NC(C)(C)C#N)c3n2)c2ccc(F)cc21]

A mixture of 2-(6-fluoro-1-methyl-1H-indazol-3-yl)-5H-pyrrolo[3,2-b]pyrazine-7-carboxylic acid (60 mg, 0.193 mmol), 2-amino-2-methylpropanenitrile (25 mg, 0.29 mmol), HATU (217 mg, 0.57 mmol) and DIEA (74 mg, 0.57 mmol) in DMF (3 mL) was stirred at room temperature for 16 hours. Then the mixture was filtered and the cake was washed with DMSO and MeOH to give N-(2-cyanopropan-2-yl)-2-(6-fluoro-1-methyl-1H-indazol-3-yl)-5H-pyrrolo[3,2-b]pyrazine-7-carboxamide (15 mg, 20.5%) as light yellow solid. MS: (M+H)$^+$=400; $^1$H NMR (300 MHz, DMSO): δ

13.03 (s, 1H), 9.13 (s, 1H), 8.58 (s, 1H), 8.54-8.50 (m, 1H), 8.35 (s, 1H), 7.32-7.69 (m, 1H), 7.23-7.22 (m, 1H), 4.17 (s, 3H), 1.88 (s, 6H).

Example 378

2-(6-Fluoro-1-methyl-1H-indazol-3-yl)-N-(1-methylcyclopropyl)-5H-pyrrolo[2,3-b]pyrazine-7-carboxamide

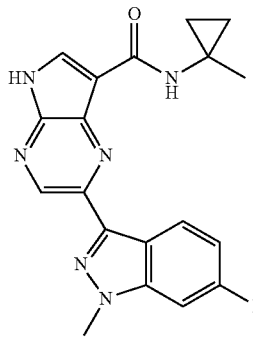

A solution of 2-(6-fluoro-1-methyl-1H-indazol-3-yl)-5H-pyrrolo[2,3-b]pyrazine-7-carboxylic acid (70 mg, 0.23 mmol), 1-methylcyclopropanamine (21 mg, 0.29 mmol), HATU (110 mmol, 0.29 mmol) and DIPEA (46 mg, 0.36 mmol) in 6 mL of DMF was stirred at room temperature for 16 hours. The solvent was evaporated at 70° C. under reduced pressure and the residue was triturated with dichloromethane (10 mL), methanol (10 mL) then decanted and dried to give 2-(6-fluoro-1-methyl-1H-indazol-3-yl)-N-(1-methylcyclopropyl)-5H-pyrrolo[2,3-b]pyrazine-7-carboxamide (45 mg, 54.9%) as a white solid. MS: (M+H)$^+$=365; $^1$H NMR (300 MHz, DMSO): δ 9.09 (s, 1H), 8.54 (s, 1H), 8.48-8.42 (m, 2H), 7.71 (dd, 1H, J=9.9, 2.1 Hz), 7.25-7.24 (m, 1H), 4.16 (s, 3H), 1.49 (s, 3H), 0.81 (brs, 2H), 0.80 (brs, 2H).

Example 379

N-(1-Amino-2-methylpropan-2-yl)-2-(6-fluoro-1-methyl-1H-indazol-3-yl)-5H-pyrrolo[3,2-b]pyrazine-7-carboxamide hydrochloride

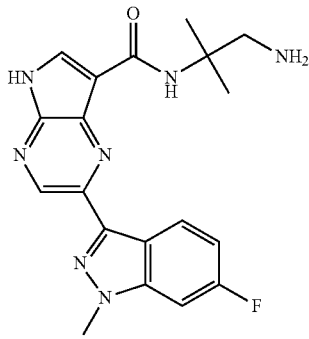

Step 1 tert-Butyl 2-(2-(6-fluoro-1-methyl-1H-indazol-3-yl)-5H-pyrrolo[3,2-b]pyrazine-7-carboxamido)-2-methylpropylcarbamate

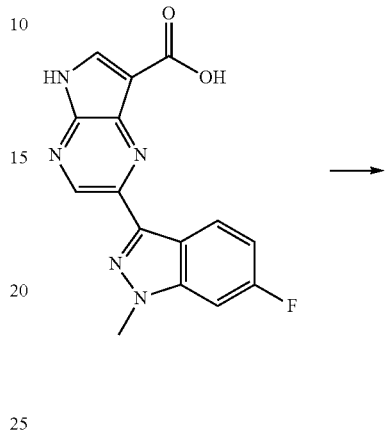

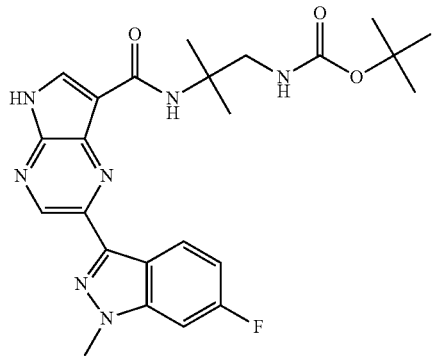

A mixture of 2-(6-fluoro-1-methyl-1H-indazol-3-yl)-5H-pyrrolo[3,2-b]pyrazine-7-carboxylic acid (70 mg, 0.225 mmol), tert-butyl 2-amino-2-methylpropylcarbamate (64 mg, 0.338 mmol), HATU (171 mg, 0.45 mmol) and DIPEA (58 mg, 0.45 mmol) in DMF (3 mL) was stirred at room temperature for 16 hours. The mixture was poured into water (5 mL) and extracted with EtOAc (3×5 mL). The combined organic layers were washed with brine and dried over Na$_2$SO$_4$. After filtration and concentration, the residue was used in the next step without further purification. MS: (M+H)$^+$=482.1.

Step 2

N-(1-Amino-2-methylpropan-2-yl)-2-(6-fluoro-1-methyl-1H-indazol-3-yl)-5H-pyrrolo[3,2-b]pyrazine-7-carboxamide hydrochloride

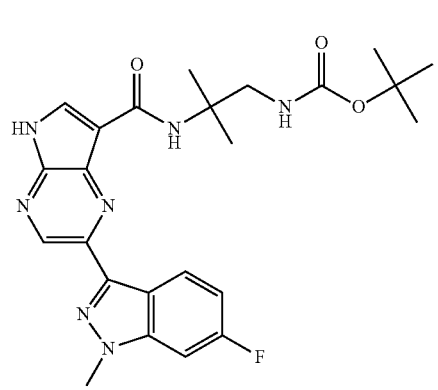

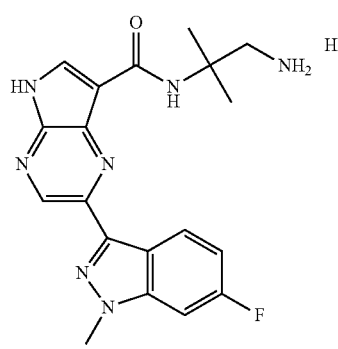

tert-Butyl 2-(2-(6-fluoro-1-methyl-1H-indazol-3-yl)-5H-pyrrolo[3,2-b]pyrazine-7-carboxamido)-2-methylpropylcarbamate (95 mg, 0.198 mmol) was dissolved in a saturated solution of HCl (g) in dioxane (10 mL). The mixture was stirred at room temperature for 16 hours. The solvent was removed under reduced pressure. The residue was triturated with dichloromethane then decanted and dried to give tert-butyl 2-(2-(6-fluoro-1-methyl-1H-indazol-3-yl)-5H-pyrrolo[3,2-b]pyrazine-7-carboxamido)-2-methylpropylcarbamate (35 mg, 46%). MS: (M+H)$^+$=382; $^1$H NMR (300 MHz, DMSO+D$_2$O): δ 9.11 (s, 1H), 8.54-8.49 (m, 1H), 8.47 (s, 1H), 8.05 (s, 1H), 7.69 (d, 1H, J=9.9 Hz), 7.20 (t, 1H, J=5.7 Hz), 4.17 (s, 3H), 3.53-3.52 (m, 2H), 1.55 (s, 6H).

Example 380

2-(6-Fluoro-1-methyl-1H-indazol-3-yl)-N-(2-methylbut-3-yn-2-yl)-5H-pyrrolo[3,2-b]pyrazine-7-carboxamide

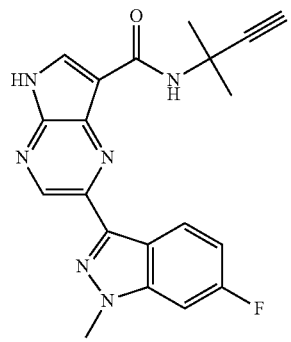 [SMILES: C#CC(C)(C)NC(=O)c1c[nH]c2ncc(-c3nn(C)c4cc(F)ccc34)nc12]

A mixture of 2-(6-fluoro-1-methyl-1H-indazol-3-yl)-5H-pyrrolo[3,2-b]pyrazine-7-carboxylic acid (70 mg, 0.225 mmol), 2-methylbut-3-yn-2-amine (28 mg, 0.338 mmol), HATU (171 mg, 0.45 mmol) and DIEA (58 mg, 0.45 mmol) in DMF (3 mL) was stirred at room temperature for 16 hours. Then the mixture was poured into water and filtered to give the crude product. The crude compound was then washed with MeOH to give 2-(6-fluoro-1-methyl-1H-indazol-3-yl)-N-(2-methylbut-3-yn-2-yl)-5H-pyrrolo[3,2-b]pyrazine-7-carboxamide (20 mg, 23.5%).

MS: (M+H)$^+$=377; $^1$H NMR (300 MHz, DMSO): δ 12.92 (s, 1H), 9.13 (s, 1H), 8.50-8.47 (m, 1H), 8.46 (s, 1H), 8.16 (s, 1H), 7.70 (dd, 1H, J=9.6, 1.5 Hz), 7.19 (t, 1H, J=1.8 Hz), 4.17 (s, 3H), 3.40 (s, 1H), 1.82 (s, 6H).

Example 381 tert-Butyl 2-(2-(6-fluoro-1-methyl-1H-indazol-3-yl)-5H-pyrrolo[2,3-b]pyrazine-7-carboxamido)-2-methylpropanoate

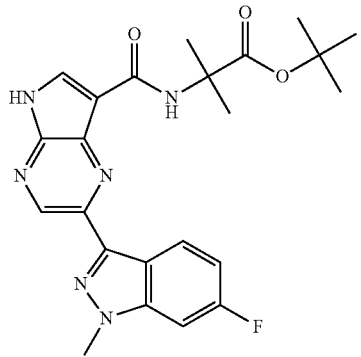 [SMILES: Cn1nc(-c2cnc3[nH]cc(C(=O)NC(C)(C)C(=O)OC(C)(C)C)c3n2)c2ccc(F)cc21]

A solution of 2-(6-fluoro-1-methyl-1H-indazol-3-yl)-5H-pyrrolo[2,3-b]pyrazine-7-carboxylic acid (100 mg, 0.323 mmol), tert-butyl 2-amino-2-methylpropanoate hydrochloride (82 mg, 0.42 mmol), HATU (160 mmol, 0.42 mmol) and DIPEA (66 mg, 0.51 mmol) in 6 mL of DMF was stirred at room temperature for 16 hours. The solvent was evaporated at 70° C. under reduced pressure and the residue was purified by column chromatography (silica gel, 200-300 mesh, eluting with a mixture of petroleum ether and ethyl acetate (1:1, v/v) to give tert-butyl 2-(2-(6-fluoro-1-methyl-1H-indazol-3-yl)-5H-pyrrolo[2,3-b]pyrazine-7-carboxamido)-2-methylpropanoate (75 mg, 51.8%) as a white solid. MS: (M+H)⁺=453; ¹H NMR (300 MHz, DMSO): δ 13.93 (s, 1H), 9.13 (s, 1H), 8.57-8.52 (m, 1H), 8.48 (s, 1H), 8.30 (s, 1H), 7.72 (dd, 1H, J=9.8, 2.1 Hz), 7.21-7.15 (m, 1H), 4.18 (s, 3H), 1.63 (s, 6H), 1.25 (s, 9H).

Example 382

2-(2-(6-Fluoro-1-methyl-1H-indazol-3-yl)-5H-pyrrolo[2,3-b]pyrazine-7-carboxamido)-2-methylpropanoic acid

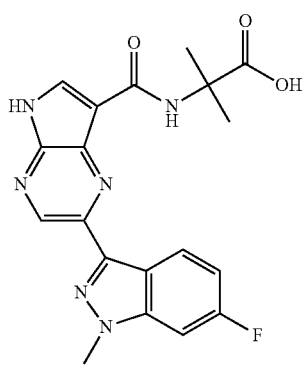 [SMILES: Cn1nc(-c2cnc3[nH]cc(C(=O)NC(C)(C)C(=O)O)c3n2)c2ccc(F)cc21]

To a stirred suspension of tert-butyl 2-(2-(6-fluoro-1-methyl-1H-indazol-3-yl)-5H-pyrrolo[2,3-b]pyrazine-7-carboxamido)-2-methylpropanoate (60 mg, 0.13 mmol) in 10 mL of dichloromethane was added drop-wise trifluoroacetic acid (4 mL) at room temperature. Then the mixture was stirred at room temperature for 16 hours. The solvent was evaporated at 40° C. under reduced pressure and the residue was purified by preparative-HPLC (Gemini 5u C18 150×21.2 mm; inject volume: 3 mL/inj, flow rate: 20 mL/min; wavelength: 214 nm and 254 nm; the gradient conditions were: 40% acetonitrile/60% water (0.1% trifluoroacetic acid, v/v) initially, proceeding to 60% acetonitrile/40% water (0.1% trifluoroacetic acid, v/v) in a linear fashion over 9 min.) to give 2-(2-(6-fluoro-1-methyl-1H-indazol-3-yl)-5H-pyrrolo[2,3-b]pyrazine-7-carboxamido)-2-methylpropanoic acid (21 mg, 40%) as a white solid. MS: (M+H)⁺=397; ¹H NMR (300 MHz, DMSO): δ 12.93 (s, 1H), 12.52 (s, 1H), 9.13 (s, 1H), 8.55-8.54 (m, 1H), 8.45 (s, 1H), 8.34 (s, 1H), 8.71 (dd, 1H, J=9.9, 1.8 Hz), 7.20 (t, 1H, J=2.1 Hz), 4.17 (s, 3H), 1.66 (s, 6H).

Example 383

N-(1,3-Dihydroxy-2-methylpropan-2-yl)-2-(6-fluoro-1-methyl-1H-indazol-3-yl)-5H-pyrrolo[3,2-b]pyrazine-7-carboxamide

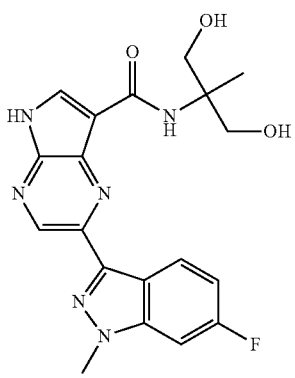 [SMILES: Cn1nc(-c2cnc3[nH]cc(C(=O)NC(C)(CO)CO)c3n2)c2ccc(F)cc21]

Step 1

2,2,3,3,6,9,9,10,10-Nonamethyl-4,8-dioxa-3,9-disilaundecan-6-amine

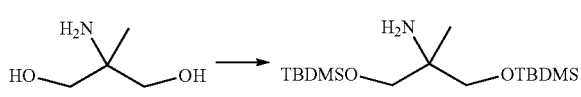

To a stirred solution of 2-amino-2-methylpropane-1,3-diol (1.05 g, 0.01 mol) in dichloromethane (40 mL) was added tert-butyldimethylsilyl chloride (9 g, 0.06 mol) followed by imidazole (6.8 g, 0.1 mol). The mixture was stirred at room temperature for 16 hours. The solvent was removed under reduced pressure. The residue was diluted with water and extracted with EtOAc (3×20 mL). The combined organic layers were washed with aqueous NaHCO₃, and brine, and then dried over sodium sulfate. After filtration and concentration, the residue was purified by column chromatography on silica gel eluting with EtOAc to give 2,2,3,3,6,9,9,10,10-nonamethyl-4,8-dioxa-3,9-disilaundecan-6-amine (2.9 g, 87%) as an oil. MS: (M+H)⁺=334; ¹H NMR (300 MHz, CDCl₃): δ 3.37-3.35 (m, 4H), 0.96 (s, 3H), 0.88 (s, 18H), 0.03 (s, 12H).

Step 2

2-(6-Fluoro-1-methyl-1H-indazol-3-yl)-N-(2,2,3,3,6,9,9,10,10-nonamethyl-4,8-dioxa-3,9-disilaundecan-6-yl)-5H-pyrrolo[3,2-b]pyrazine-7-carboxamide

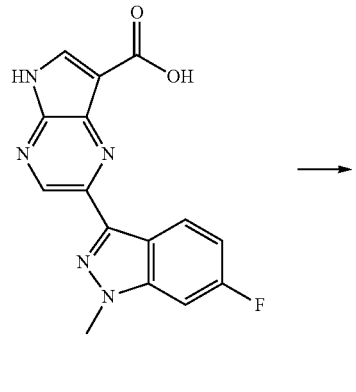

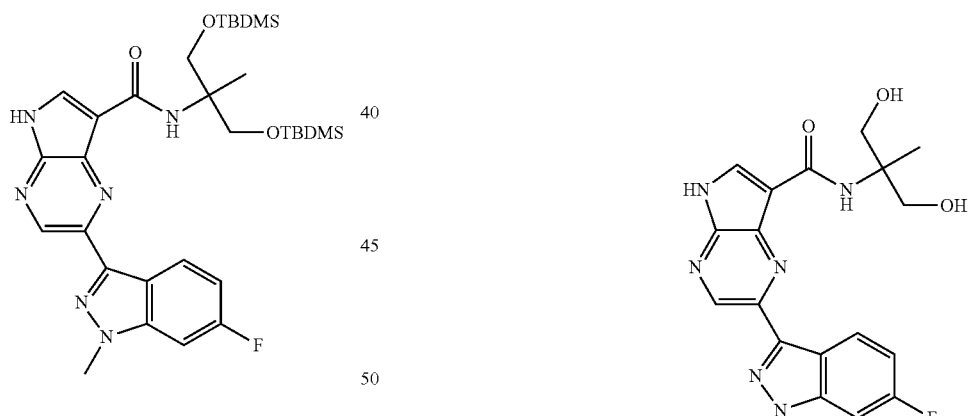

A mixture of 2-(6-fluoro-1-methyl-1H-indazol-3-yl)-5H-pyrrolo[3,2-b]pyrazine-7-carboxylic acid (70 mg, 0.225 mmol), 2,2,3,3,6,9,9,10,10-nonamethyl-4,8-dioxa-3,9-disilaundecan-6-amine (112 mg, 0.338 mmol), HATU (171 mg, 0.45 mmol) and DIPEA (58 mg, 0.45 mmol) in DMF (5 mL) was stirred at room temperature for 16 hours. The mixture was poured into water (5 mL) and extracted with EtOAc (3×10 mL). The combined organic layers were washed with brine and dried over Na₂SO₄. After filtration and concentration, the residue was purified by column chromatography on silica gel eluting with petroleum ether/EtOAc (1:1, v/v) to give 2-(6-fluoro-1-methyl-1H-indazol-3-yl)-N-(2,2,3,3,6,9,9,10,10-nonamethyl-4,8-dioxa-3,9-disilaundecan-6-yl)-5H-pyrrolo[3,2-b]pyrazine-7-carboxamide (65 mg, 46%) as a white solid. ¹H NMR (300 MHz, DMSO): δ 9.00 (s, 1H), 8.44-8.40 (m, 1H), 8.38 (s, 1H), 7.91 (s, 1H), 7.87 (dd, J=10.2, 2.7 Hz, 1H), 7.06-7.05 (m, 1H), 4.13 (s, 3H), 3.92-3.84 (m, 1H), 1.43 (s, 3H), 0.64 (s, 18H), 0.01 (s, 12H).

Step 3

N-(1,3-Dihydroxy-2-methylpropan-2-yl)-2-(6-fluoro-1-methyl-1H-indazol-3-yl)-5H-pyrrolo[3,2-b]pyrazine-7-carboxamide

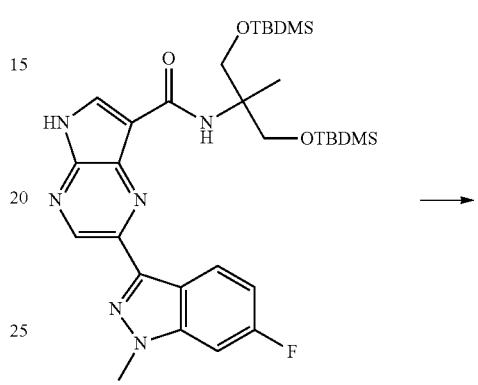

2-(6-Fluoro-1-methyl-1H-indazol-3-yl)-N-(2,2,3,3,6,9,9,10,10-nonamethyl-4,8-dioxa-3,9-disilaundecan-6-yl)-5H-pyrrolo[3,2-b]pyrazine-7-carboxamide (65 mg, 0.104 mmol) was dissolved in a saturated solution of HCl(g) in dioxane (10 mL). The mixture was stirred at room temperature for 16 hours. The solvent was removed under reduced pressure. The residue was triturated with MeOH then decanted and dried to give N-(1,3-dihydroxy-2-methylpropan-2-yl)-2-(6-fluoro-1-methyl-1H-indazol-3-yl)-5H-pyrrolo[3,2-b]pyrazine-7-carboxamide (28 mg, 68%).

MS: (M+H)⁺=399; ¹H NMR (300 MHz, DMSO): δ 12.88 (s, 1H), 9.13 (s, 1H), 8.74-8.72 (m, 1H), 8.41 (s, 1H), 7.97 (s,

1H), 7.68 (d, 1H, J=10.2 Hz), 6.87-6.86 (m, 1H), 5.06 (t, 2H, J=5.4 Hz), 4.17 (s, 3H), 3.82-3.76 (m, 2H), 3.71-3.65 (m, 2H), 1.34 (s, 3H).

Example 384

2-(Fluoro-1-methyl-1H-indazol-3-yl)-N-(1-methyl-cyclopentyl)-5H-pyrrolo[2,3-b]pyrazine-7-carboxamide

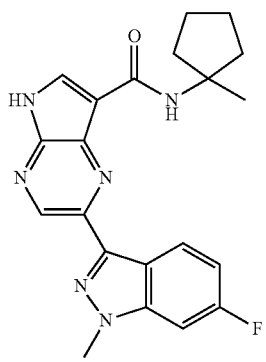 [SMILES: Cn1nc(-c2cnc3[nH]cc(C(=O)NC4(C)CCCC4)c3n2)c2ccc(F)cc21]

Step 1

1-Azido-1-methylcyclopentane

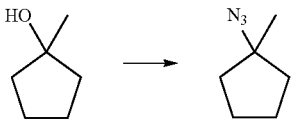

BF$_3$.Et$_2$O (934 mg, 6.23 mmol) was added drop-wise at 20° C. to a stirred solution of 1-methylcyclopentanol (520 mg, 5.19 mmol) and trimethylsilyl azide (716 mg, 6.23 mmol) in 6 mL of toluene. Then the solution was stirred at room temperature for 16 hours. The organic phase was washed with a 10% solution of NaHCO$_3$ (10 mL), water (5 mL) and brine (5 mL), and dried over anhydrous sodium sulfate. The drying agent was removed by filtration and the solvent was evaporated at 35° C. under reduced pressure to give 1-azido-1-methylcyclopentane (720 mg) as a crude product. It was used directly in the next step without further purification.

Step 2

1-Methylcyclopentanamine hydrochloride

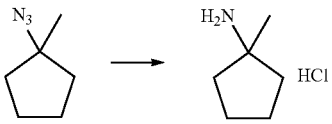

A mixture of 1-azido-1-methylcyclopentane (720 mg, 5.19 mmol) and 10% Pd on carbon in 100 mL of methanol was stirred at room temperature for 16 hours under hydrogen (1 atm). Then concentrated HCl (1 mL) was added and the solvent was evaporated at 40° C. under reduced pressure to give 1-methylcyclopentanamine hydrochloride (700 mg, 99% for two steps) as oil. It was used directly in the next step without further purification. $^1$H NMR (300 MHz, D$_2$O): δ 1.59 (brs, 7H), 1.21 (s, 3H).

Step 3

2-(6-Fluoro-1-methyl-1H-indazol-3-yl)-N-(1-methylcyclopentyl)-5H-pyrrolo[2,3-b]pyrazine-7-carboxamide

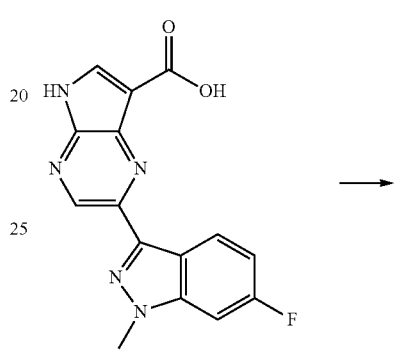

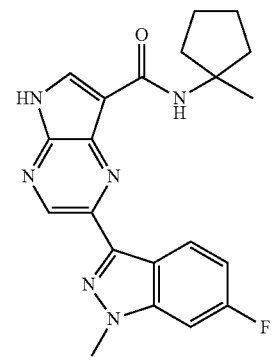

A solution of 2-(6-fluoro-1-methyl-1H-indazol-3-yl)-5H-pyrrolo[2,3-b]pyrazine-7-carboxylic acid (62 mg, 0.20 mmol), 1-methylcyclopentanamine hydrochloride (35 mg, 0.26 mmol), HATU (98 mmol, 0.26 mmol) and DIEA (42 mg, 0.33 mmol) in 6 mL of DMF was stirred at room temperature for 16 hours. The solvent was evaporated at 70° C. under reduced pressure to give a crude product, which was purified by preparative-HPLC (Gemini 5u C18 150×21.2 mm; inject volume: 3 mL/inj, flow rate: 20 mL/min; wavelength: 214 nm and 254 nm; the gradient conditions were: 55% acetonitrile/45% water (0.1% trifluoroacetic acid, v/v) initially, proceeding to 80% acetonitrile/20% water (0.1% trifluoroacetic acid, v/v) in a linear fashion over 9 min.) to give 2-(6-fluoro-1-methyl-1H-indazol-3-yl)-N-(1-methylcyclopentyl)-5H-pyrrolo[2,3-b]pyrazine-7-carboxamide (18 mg, 22.9%) as an off-white solid. MS: (M+H)$^+$=393; $^1$H NMR (300 MHz, DMSO): δ 12.84 (s, 1H), 9.09 (s, 1H), 8.49-8.44 (m, 1H), 8.41

(s, 1H), 8.01 (s, 1H), 7.72 (d, 1H, J=7.8 Hz), 7.17 (t, 1H, J=8.1 Hz), 4.17 (s, 3H), 2.19 (brs, 2H), 1.79-1.76 (m, 6H), 1.57 (s, 3H).

Example 385

2-(6-Fluoro-1-methyl-1H-indazol-3-yl)-N-(4-methylpiperidin-4-yl)-5H-pyrrolo[2,3-b]pyrazine-7-carboxamide hydrochloride

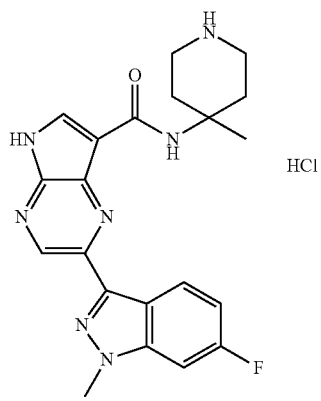

Step 1 tert-Butyl 4-(2-(6-fluoro-1-methyl-1H-indazol-3-yl)-5H-pyrrolo[2,3-b]pyrazine-7-

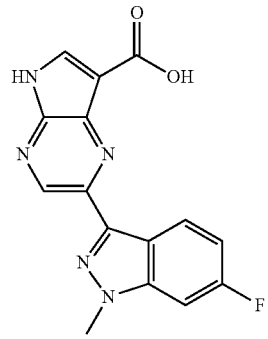

-continued

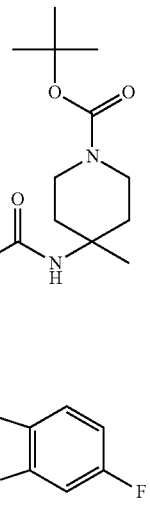

To a stirred solution of 2-(6-fluoro-1-methyl-1H-indazol-3-yl)-5H-pyrrolo[2,3-b]pyrazine-7-carboxylic acid (100 mg, 0.32 mmol) in 10 mL of DMF were added EDCI (122 mg, 0.64 mmol), tert-butyl 4-amino-4-methylpiperidine-1-carboxylate (103 mg, 0.48 mmol) and DMAP (78 mg, 0.64 mmol) in one portion at room temperature. Then the reaction mixture was stirred for 16 hours, then was poured into 50 mL of water and filtered. The filter cake was washed with water (10 mL) and passed through a pad of silica gel (200-300 mesh, eluting with a mixture of petroleum ether and ethyl acetate (1:2, v/v) to give tert-butyl 4-(2-(6-fluoro-1-methyl-1H-indazol-3-yl)-5H-pyrrolo[2,3-b]pyrazine-7-carboxamido)-4-methylpiperidine-1-carboxylate (100 mg, 61.6%) as a white solid which was used for the next step without further purification. MS: (M+H)⁺=508.2.

Step 2

2-(6-Fluoro-1-methyl-1H-indazol-3-yl)-N-(4-methylpiperidin-4-yl)-5H-pyrrolo[2,3-b]pyrazine-7-carboxamide hydrochloride

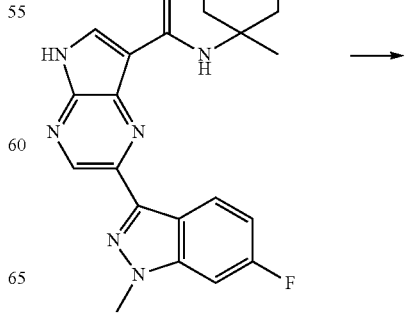

-continued

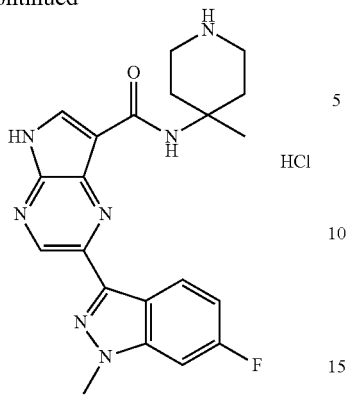

tert-Butyl 4-(2-(6-fluoro-1-methyl-1H-indazol-3-yl)-5H-pyrrolo[2,3-b]pyrazine-7-carboxamido)-4-methylpiperidine-1-carboxylate (100 mg, 0.20 mmol) was dissolved in 30 mL of a saturated solution of HCl (g) in dioxane and the solution was stirred at room temperature for 16 hours. The reaction mixture was filtered, washed with dichloromethane (20 mL), diethyl ether (30 mL) and dried to give 2-(6-fluoro-1-methyl-1H-indazol-3-yl)-N-(4-methylpiperidin-4-yl)-5H-pyrrolo[2,3-b]pyrazine-7-carboxamide hydrochloride (29 mg, 33.2%) as a white solid. MS: (M+H)$^+$=408; $^1$H NMR (300 MHz, DMSO): δ 9.16 (s, 1H), 8.57-8.41 (m, 4H), 7.92 (s, 1H), 7.75 (d, 1H, J=10.5 Hz), 7.32-7.26 (m, 1H), 6.98-6.93 (m, 1H), 5.75 (d, 2H, J=6.9 Hz), 4.19 (s, 3H), 3.16 (brs, 5H), 1.96 (brs, 3H), 1.61 (s, 3H).

Example 386

2-(6-Fluoro-1-methyl-1H-indazol-3-yl)-N-(3-methyloxetan-3-yl)-5H-pyrrolo[2,3-b]pyrazine-7-carboxamide

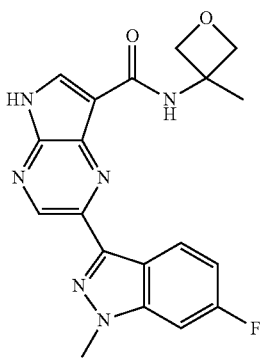 [SMILES: Cn1nc(-c2cnc3[nH]cc(C(=O)NC4(C)COC4)c3n2)c2ccc(F)cc21]

To a stirred solution of 2-(6-fluoro-1-methyl-1H-indazol-3-yl)-5H-pyrrolo[2,3-b]pyrazine-7-carboxylic acid (105 mg, 0.34 mmol) in 6 mL of DMF were added EDCI (128 mmol, 0.67 mmol), DMAP (82 mg, 0.67 mmol) and 3-methyloxetan-3-amine (44 mg, 0.50 mmol) in one portion at room temperature. Then the mixture was stirred for 16 hours. The solvent was evaporated at 70° C. under reduced pressure and the residue was triturated with water (10 mL), dichloromethane (10 mL), methanol (15 mL) then decanted and dried to give 2-(6-fluoro-1-methyl-1H-indazol-3-yl)-N-(3-methyloxetan-3-yl)-5H-pyrrolo[2,3-b]pyrazine-7-carboxamide (50 mg, 38.9%) as a yellow solid. MS: (M+H)$^+$=381; $^1$H NMR (300 MHz, DMSO): δ 12.90 (brs, 1H), 9.13 (s, 1H), 8.53-8.47 (m, 3H), 7.72 (d, 1H, J=7.8 Hz), 7.26-7.21 (m, 1H), 4.91 (d, 2H, J=6.0 Hz), 4.55 (d, 2H, J=6.3 Hz), 4.18 (s, 3H), 1.77 (s, 3H).

Example 387

N-(1-Cyanocyclopropyl)-2-(6-fluoro-1-methyl-1H-indazol-3-yl)-5H-pyrrolo[3,2-b]pyrazine-7-carboxamide

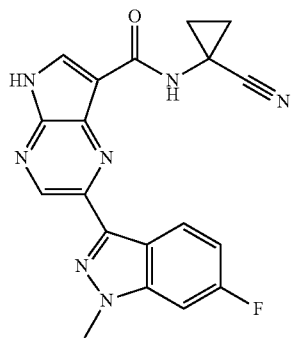 [SMILES: Cn1nc(-c2cnc3[nH]cc(C(=O)NC4(C#N)CC4)c3n2)c2ccc(F)cc21]

A mixture of 2-(6-fluoro-1-methyl-1H-indazol-3-yl)-5H-pyrrolo[3,2-b]pyrazine-7-carboxylic acid (90 mg, 0.29 mmol), 1-aminocyclopropanecarbonitrile hydrochloride (41 mg, 0.348 mmol), EDCI (110 mg, 0.58 mmol) and DMAP (75 mg, 0.58 mmol) in DMF (5 mL) was stirred at room temperature for 16 hours. Then the mixture was poured into water (5 mL) and filtered to give the crude product which was purified by preparative-HPLC (Gemini 5u C18 150×21.2 mm; inject volume: 3 mL/inj, flow rate: 20 mL/min; wavelength: 214 nm and 254 nm; the gradient conditions were: 40% acetonitrile/60% water (0.1% trifluoroacetic acid, v/v) initially, proceeding to 55% acetonitrile/45% water (0.1% trifluoroacetic acid, v/v) in a linear fashion over 9 min.) to give N-(1-cyanocyclopropyl)-2-(6-fluoro-1-methyl-1H-indazol-3-yl)-5H-pyrrolo[3,2-b]pyrazine-7-carboxamide (25 mg, 23%) as a white solid. MS: (M+H)$^+$=376; $^1$H NMR (300 MHz, DMSO): δ 12.95 (s, 1H), 9.10 (s, 1H), 8.87 (s, 1H), 8.56-8.53 (m, 2H), 6.69 (d, 1H, J=8.7 Hz), 7.26 (t, 1H, J=8.7 Hz), 4.15 (s, 3H), 1.70 (brs, 2H), 1.64 (brs, 2H).

Example 388

2-(6-Chloro-1-methyl-1H-indazol-3-yl)-N-(2-phenylpropan-2-yl)-5H-pyrrolo[2,3-b]pyrazine-7-carboxamide

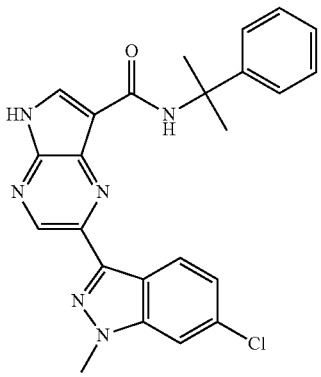 [SMILES: Cn1nc(-c2cnc3[nH]cc(C(=O)NC(C)(C)c4ccccc4)c3n2)c2ccc(Cl)cc21]

A mixture of 2-(6-chloro-1-methyl-1H-indazol-3-yl)-5H-pyrrolo[2,3-b]pyrazine-7-carboxylic acid (0.07 g, 0.3 mmol), 2-phenylpropan-2-amine (0.05 g, 0.37 mmol), EDCI (0.057 g, 0.3 mmol), DMAP (0.037 g, 0.3 mmol), HATU (0.114 g, 0.3 mmol) and DIPEA (0.163 g, 1.26 mmol) in 10 mL of DMF were stirred at room temperature overnight. The solvent was removed under reduced pressure at 70° C. The residue was triturated with 5 mL of water and then purified by preparative-HPLC (Gemini 5u C18 150×21.2 mm; inject volume: 3 mL/inj, flow rate: 20 mL/min; wavelength: 214 nm and 254 nm; the gradient conditions were: 60% acetonitrile/40% water (0.1% trifluoroacetic acid, v/v) initially, proceeding to 80% acetonitrile/20% water (0.1% trifluoroacetic acid, v/v) in a linear fashion over 9 min.) to give 2-(6-chloro-1-methyl-1H-indazol-3-yl)-N-(2-phenylpropan-2-yl)-5H-pyrrolo[2,3-b]pyrazine-7-carboxamide (0.017 g, 18%) as a yellow solid. MS: (M+H)$^+$=445; $^1$H NMR (300 MHz, DMSO): δ 12.89 (s, 1H), 9.13 (s, 1H), 8.46-8.43 (m, 2H), 8.38-8.37 (m, 1H), 8.00 (s, 1H), 7.51-7.49 (m, 2H), 7.34-7.16 (m, 4H), 4.20 (s, 3H), 1.86 (s, 6H).

Example 389

(S)-2-(6-Chloro-1-methyl-1H-indazol-3-yl)-N-(1-phenylethyl)-5H-pyrrolo[2,3-b]pyrazine-7-carboxamide

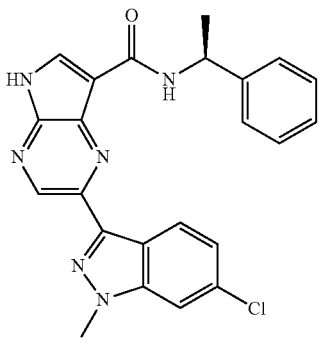 [SMILES: C[C@H](NC(=O)c1c[nH]c2ncc(-c3nn(C)c4cc(Cl)ccc34)nc12)c1ccccc1]

A mixture of 2-(6-chloro-1-methyl-1H-indazol-3-yl)-5H-pyrrolo[2,3-b]pyrazine-7-carboxylic acid (0.07 g, 0.3 mmol), S-1-phenylethanamine (0.05 g, 0.41 mmol), EDCI (0.057 g, 0.3 mmol), DMAP (0.037 g, 0.3 mmol), HATU (0.114 g, 0.3 mmol) and DIPEA (0.163 g, 1.26 mmol) in 10 mL of DMF were stirred at room temperature overnight. The solvent was removed under reduced pressure at 70° C. The residue was triturated with water and then purified by preparative-HPLC (Gemini 5u C18 150×21.2 mm; inject volume: 3 mL/inj, flow rate: 20 mL/min; wavelength: 214 nm and 254 nm; the gradient conditions were: 55% acetonitrile/45% water (0.1% trifluoroacetic acid, v/v) initially, proceeding to 80% acetonitrile/20% water (0.1% trifluoroacetic acid, v/v) in a linear fashion over 9 min.) to give S-2-(6-chloro-1-methyl-1H-indazol-3-yl)-N-(1-phenylethyl)-5H-pyrrolo[2,3-b]pyrazine-7-carboxamide (0.02 g, 22%) as a yellow solid. MS: (M+H)$^+$=431; $^1$H NMR (300 MHz, DMSO): δ 12.93 (s, 1H), 9.13 (s, 1H), 8.52-8.48 (m, 2H), 8.31 (d, 1H, J=8.7 Hz), 8.01 (s, 1H), 7.50-7.48 (m, 2H), 7.38-7.11 (m, 3H), 7.09 (d, 1H, J=2.1 Hz), 5.36 (brs, 1H), 4.19 (s, 3H), 1.67 (d, 3H, J=6.9 Hz).

Example 390

2-(6-Chloro-1-methyl-1H-indazol-3-yl)-N-(1,1,1-trifluoro-2-methylpropan-2-yl)-5H-pyrrolo[2,3-b]pyrazine-7-carboxamide

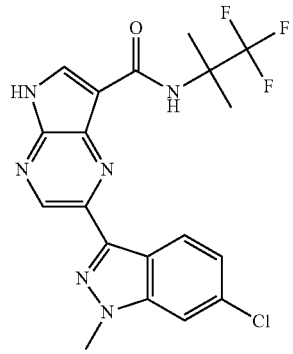 [SMILES: Cn1nc(-c2cnc3[nH]cc(C(=O)NC(C)(C)C(F)(F)F)c3n2)c2ccc(Cl)cc21]

A mixture of 2-(6-chloro-1-methyl-1H-indazol-3-yl)-5H-pyrrolo[2,3-b]pyrazine-7-carboxylic acid (0.07 g, 0.3 mmol), 1,1,1-trifluoro-2-methylpropan-2-amine (0.05 g, 0.39 mmol), EDCI (0.057 g, 0.3 mmol), DMAP (0.037 g, 0.3 mmol), HATU (0.114 g, 0.3 mmol) and DIPEA (0.163 g, 1.26 mmol) in 10 mL of DMF were stirred at room temperature overnight. The solvent was removed under reduced pressure at 70° C. The residue was triturated with water and then purified by preparative-HPLC (Gemini 5u C18 150×21.2 mm; inject volume: 3 mL/inj, flow rate: 20 mL/min; wavelength: 214 nm and 254 nm; the gradient conditions were: 55% acetonitrile/45% water (0.1% trifluoroacetic acid, v/v) initially, proceeding to 80% acetonitrile/20% water (0.1% trifluoroacetic acid, v/v) in a linear fashion over 9 min.) to give 2-(6-chloro-1-methyl-1H-indazol-3-yl)-N-(1,1,1-trifluoro-2-methylpropan-2-yl)-5H-pyrrolo[2,3-b]pyrazine-7-carboxamide (0.015 g, 16%) as a white solid. MS: (M+H)$^+$=437; $^1$H NMR (300 MHz, DMSO): δ 13.03 (s, 1H), 9.10 (s, 1H), 8.53-8.82 (m, 1H), 8.42 (d, 1H, J=8.4 Hz), 8.14 (s, 1H), 8.39 (s, 1H), 7.28 (d, 1H, J=8.7 Hz), 4.20 (s, 3H), 1.77 (s, 6H).

Example 391

2-(6-Chloro-1-methyl-1H-indazol-3-yl)-N-tert-pentyl-5H-pyrrolo[2,3-b]pyrazine-7-carboxamide

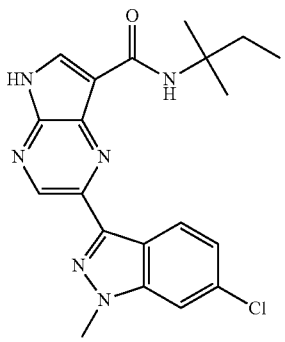 [SMILES: CCC(C)(C)NC(=O)c1c[nH]c2ncc(-c3nn(C)c4cc(Cl)ccc34)nc12]

A mixture of 2-(6-chloro-1-methyl-1H-indazol-3-yl)-5H-pyrrolo[2,3-b]pyrazine-7-carboxylic acid (0.07 g, 0.3 mmol), 2-methylbutan-2-amine (0.05 g, 0.57 mmol), EDCI (0.057 g, 0.3 mmol), DMAP (0.037 g, 0.3 mmol), HATU (0.114 g, 0.3 mmol) and DIPEA (0.163 g, 1.26 mmol) in 10 mL of DMF were stirred at room temperature overnight. The solvent was removed under reduced pressure at 70° C. The residue was triturated with water and then purified by preparative-HPLC (Gemini 5u C18 150×21.2 mm; inject volume: 3 mL/inj, flow rate: 20 mL/min; wavelength: 214 nm and 254 nm; the gradient conditions were: 57% acetonitrile/43% water (0.1% trifluoroacetic acid, v/v) initially, proceeding to 80% acetonitrile/20% water (0.1% trifluoroacetic acid, v/v) in a linear fashion over 9 min.) to give 2-(6-chloro-1-methyl-1H-indazol-3-yl)-N-tert-pentyl-5H-pyrrolo[2,3-b]pyrazine-7-carboxamide (0.019 g, 22%) as a white solid. MS: (M+H)$^+$=397; $^1$H NMR (300 MHz, DMSO): δ12.86 (s, 1H), 9.10 (s, 1H), 8.47-8.40 (m, 2H), 8.03 (s, 1H), 7.83 (s, 1H), 7.32 (d, 1H, J=8.4 Hz), 4.20 (s, 3H), 2.03-1.91 (m, 2H), 1.48 (s, 6H), 0.89 (t, 3H, J=7.4 Hz).

Example 392

2-(6-Fluoro-1-methyl-1H-indazol-3-yl)-N-(1-methylcyclohexyl)-5H-pyrrolo[2,3-b]pyrazine-7-carboxamide

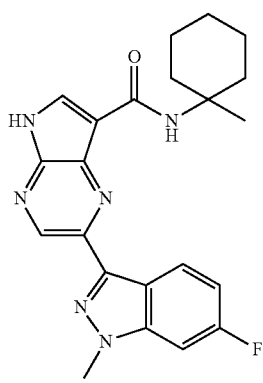 [SMILES: Cn1nc(-c2cnc3[nH]cc(C(=O)NC4(C)CCCCC4)c3n2)c2ccc(F)cc21]

To a stirred solution of 2-(6-fluoro-1-methyl-1H-indazol-3-yl)-5H-pyrrolo[2,3-b]pyrazine-7-carboxylic acid (70 mg, 0.22 mmol) in 6 mL of DMF were added EDCI (64 mg, 0.33 mmol) and DMAP (42 mg, 0.34 mmol), followed by the addition of 1-methylcyclohexanamine hydrochloride (50 mg, 0.33 mmol) in one portion at room temperature and stirred for 16 hours. The reaction mixture was poured into 35 mL of water, and filtered to give a crude product, which was purified by preparative-HPLC (Gemini 5u C18 150×21.2 mm; inject volume: 3 mL/inj, flow rate: 20 mL/min; wavelength: 214 nm and 254 nm; the gradient conditions were: 55% acetonitrile/45% water (0.1% trifluoroacetic acid, v/v) initially, proceeding to 88% acetonitrile/12% water (0.1% trifluoroacetic acid, v/v) in a linear fashion over 9 min.) to give 2-(6-fluoro-1-methyl-1H-indazol-3-yl)-N-(1-methylcyclohexyl)-5H-pyrrolo[2,3-b]pyrazine-7-carboxamide (26 mg, 28.4%) as a pale yellow solid. MS: (M+H)$^+$=407; $^1$H NMR (300 MHz, DMSO): δ 12.68 (s, 1H), 9.10 (s, 1H), 8.45-8.40 (m, 2H), 7.85 (s, 1H), 7.71 (d, 1H, J=9.9 Hz), 7.20-7.14 (m, 1H), 4.17 (s, 3H), 2.33-2.29 (m, 2H), 2.03-2.00 (m, 1H), 1.53-1.46 (m, 10H).

Example 393

N-(3-Amino-2,3-dimethylbutan-2-yl)-2-(6-fluoro-1-methyl-1H-indazol-3-yl)-5H-pyrrolo[2,3-b]pyrazine-7-carboxamide 2,2,2-trifluoroacetate

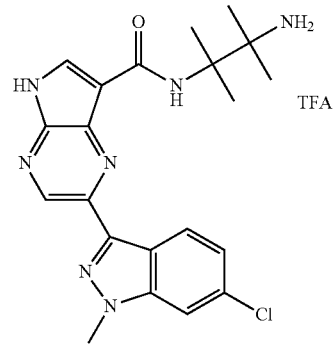 [SMILES: Cn1nc(-c2cnc3[nH]cc(C(=O)NC(C)(C)C(C)(C)N)c3n2)c2ccc(Cl)cc21]

To a stirred solution of 2-(6-fluoro-1-methyl-1H-indazol-3-yl)-5H-pyrrolo[2,3-b]pyrazine-7-carboxylic acid (80 mg, 0.26 mmol) in 6 mL of DMF were added EDCI (102 mg, 0.53 mmol), 2,3-dimethylbutane-2,3-diamine hydrochloride (62 mg, 0.53 mmol) and DMAP (76 mg, 0.62 mmol) at room temperature and stirred for 16 hours. The reaction mixture was poured into 50 mL of water and filtered to give a crude product, which was purified by preparative-HPLC (Gemini 5u C18 150×21.2 mm; inject volume: 3 mL/inj, flow rate: 20 mL/min; wavelength: 214 nm and 254 nm; the gradient conditions were: 20% acetonitrile/80% water (0.1% trifluoroacetic acid, v/v) initially, proceeding to 35% acetonitrile/65% water (0.1% trifluoroacetic acid, v/v) in a linear fashion over 9 min.) to give N-(3-amino-2,3-dimethylbutan-2-yl)-2-(6-fluoro-1-methyl-1H-indazol-3-yl)-5H-pyrrolo[2,3-b]pyrazine-7-carboxamide 2,2,2-trifluoroacetate (15 mg, 11.1%) as a pale yellow solid. MS: (M+H)$^+$=410; $^1$H NMR (300 MHz, DMSO): δ 13.14 (s, 1H), 9.12 (s, 1H), 8.58 (s, 1H), 8.48-8.31

(m, 5H), 7.73 (dd, 1H, J=9.9 Hz, 2.1 Hz), 7.25 (t, 1H, J=9.0 Hz), 4.18 (s, 3H), 1.56 (s, 6 h), 1.38 (s, 6H).

Example 394

N-tert-Butyl 2-(6-cyano-1-methyl-1H-indazol-3-yl)-5H-pyrrolo[3,2-b]pyrazine-7-carboxamide

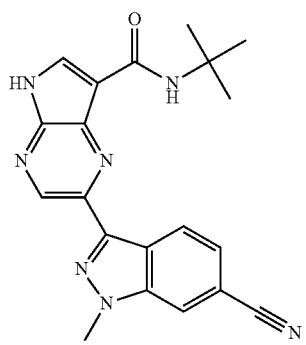 [SMILES: Cn1nc(-c2cnc3[nH]cc(C(=O)NC(C)(C)C)c3n2)c2ccc(C#N)cc21]

Step 1

2-Bromo-N-tert-butyl 5H-pyrrolo[3,2-b]pyrazine-7-carboxamide

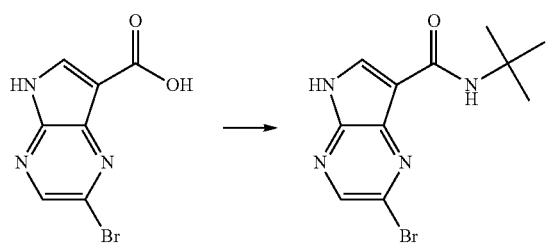 [SMILES: O=C(O)c1c[nH]c2ncc(Br)nc12 ; CC(C)(C)NC(=O)c1c[nH]c2ncc(Br)nc12]

A mixture of 2-bromo-5H-pyrrolo[3,2-b]pyrazine-7-carboxylic acid (242 mg, 1 mmol), 2-methylpropan-2-amine (110 mg, 1.5 mmol), EDCI (382 mg, 2 mmol) and DMAP (244 mg, 2 mmol) in DMF (5 mL) was stirred at room temperature for 3 hours. Then the mixture was poured into water and extracted with EtOAc (3×10 mL). The combined organic layers were washed with brine and dried over Na$_2$SO$_4$. After filtration and concentration, the crude residue was used to the next step without further purification. MS: (M+H)$^+$=297.

Step 2

(2-Bromo-7-(tert-butylcarbamoyl)-5H-pyrrolo[3,2-b]pyrazin-5-yl)methyl pivalate

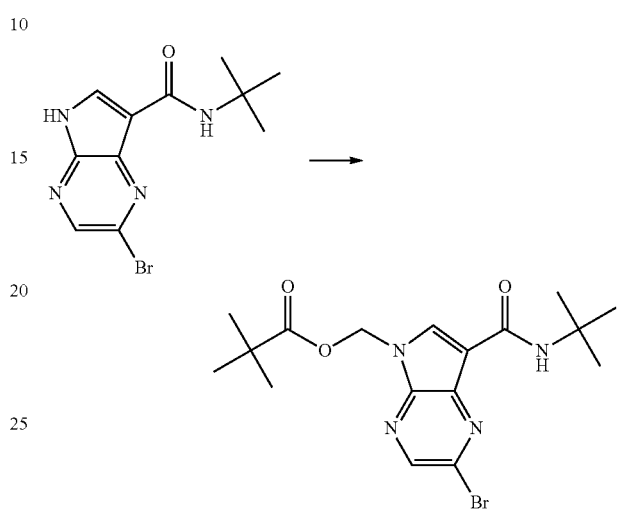

To a stirred mixture of 2-bromo-N-tert-butyl-5H-pyrrolo[3,2-b]pyrazine-7-carboxamide in DMF (5 mL) was added chloromethyl pivalate (225 mg, 1.5 mmol) followed by K$_2$CO$_3$ (276 mg, 2 mmol). The mixture was stirred at room temperature for 16 hours. The mixture was poured into water and extracted with EtOAc (3×10 mL). The combined organic layers were washed with brine and dried over Na$_2$SO$_4$. After filtration and concentration, the residue was purified by column chromatography on silica gel eluting with petroleum ether/EtOAc (5:1, v/v) to give (2-bromo-7-(tert-butylcarbamoyl)-5H-pyrrolo[3,2-b]pyrazin-5-yl)methyl pivalate (140 mg, 34% over two steps) as white solid. MS: (M+H)$^+$=411; $^1$H NMR (300 MHz, CDCl$_3$): δ 8.41 (s, 1H), 8.33 (s, 1H), 7.80 (s, 1H), 6.20 (s, 2H), 1.52 (s, 9H), 1.15 (s, 9H).

Step 3

3-Iodo-1H-indazole-6-carbonitrile

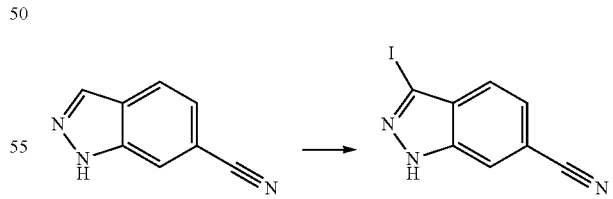

To a suspension of 1H-indazole-6-carbonitrile (4.5 g, 31.4 mmol) and KOH (5.3 g, 94.2 mmol) in DMSO (50 mL), was added iodine (15.9 g, 62.8 mmol) portion-wise over 10 minutes at 0° C. under ice-water bath. The final mixture was stirred for additional 2 hours at room temperature. The mixture was added slowly into saturated sodium sulfite (300 mL), the formed solid was stirred for 10 minutes, filtered, washed with saturated sodium sulfite (2×50 mL), water (2×20 mL) and dried, giving 3-iodo-1H-indazole-6-carbonitrile light as yellow solid (8.1 g, yield 95.6%). MS: (M+H)⁺=411; ¹H NMR (300 MHz, CDCl₃): δ 8.41 (s, 1H), 8.33 (s, 1H), 7.80 (s, 1H), 6.20 (s, 2H), 1.52 (s, 9H), 1.15 (s, 9H).

Step 4

3-Iodo-1-methyl-1H-indazole-6-carbonitrile

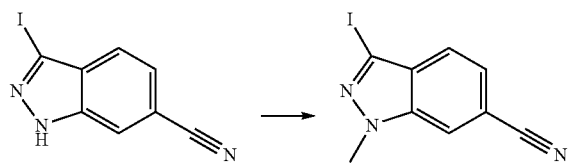

To a suspension of 3-iodo-1H-indazole-6-carbonitrile (2.0 g, 7.43 mmol), t-BuOK (1.2 g, 10.4 mmol) in THF (50 mL), iodomethane (1.2 g, 10.4 mmol) in THF (5 mL) was added dropwise at 0° C. under ice-water bath. The resulting mixture was stirred overnight at room temperature. Two isomers, which are methylated at N-1 and N-2 position respectively, were formed. The excess solvent was removed under reduced pressure, the residue was dissolved in EtOAc (100 mL), washed with brine (2×10 mL), the combined organics were dried over Na₂SO₄. After removal of drying agent and concentration, the crude mixture (1.6 g) was used in the next step without further purification. MS: (M+H)⁺=411;

Step 5

1-Methyl-3-(tributylstannyl)-1H-indazole-6-carbonitrile

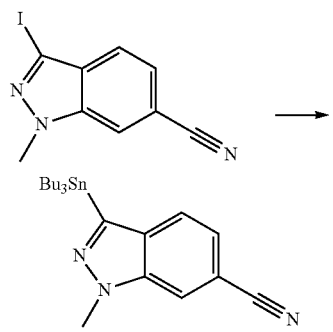

The crude mixture of 3-iodo-1-methyl-1H-indazole-6-carbonitrile and 3-iodo-2-methyl-1H-indazole-6-carbonitrile (97 mg, crude) was dissolved in THF (4 mL). The solution was cooled to −40° C. Isopropylmagnesium chloride (0.21 mL, 0.41 mmol, 2M in THF) was added drop-wise at −40° C. The reaction mixture was stirred at −40° C. for 20 min. Then chlorotributyltin (0.11 mL) was added slowly. The reaction mixture was allowed to warm to room temperature and stirred for 1.5 h. The reaction mixture was quenched with saturated NH₄Cl solution and then extracted with EtOAc (3×5 mL), organics were washed with water (10 mL), brine (2×10 mL) and dried over Na₂SO₄ and concentrated. The residue was used to the next step without further purification.

Step 6

(7-(tert-Butylcarbamoyl)-2-(6-cyano-1-methyl-1H-indazol-3-yl)-5H-pyrrolo[2,3-b]pyrazin-5-yl)methyl pivalate

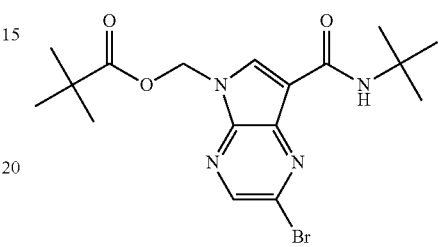

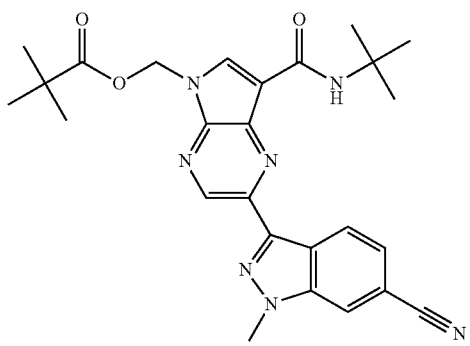

In a round-bottomed flask, (2-bromo-7-(tert-butylcarbamoyl)-5H-pyrrolo[2,3-b]pyrazin-5-yl)methyl pivalate (140 mg, 0.34 mmol) and 1-methyl-3-(tributylstannyl)-1H-indazole-6-carbonitrile (crude, containing some 2-methyl-3-(tributylstannyl)-1H-indazole-6-carbonitrile) was dissolved in DMF (5 mL) under nitrogen. Pd(PPh₃)₄ (20 mg, 0.017 mmol) and CuI (13 mg, 0.068 mmol) were added and mixture sonicated for 5 min while bubbling nitrogen. The reaction mixture was stirred at 80° C. for 16 hours. After solvent removal, the residue was purified by column chromatography on silica gel eluting with petroleum ether/EtOAc (3:1 to 1:1, v/v) to give (7-(tert-butylcarbamoyl)-2-(6-cyano-1-methyl-1H-indazol-3-yl)-5H-pyrrolo[2,3-b]pyrazin-5-yl)methyl pivalate (80 mg, 48.5%). MS: (M+H)⁺=488.3; ¹H NMR (300

MHz, DMSO): δ 9.15 (s, 1H), 8.58-8.53 (m, 3H), 7.83 (s, 1H), 6.31 (s, 2H), 4.25 (s, 3H), 1.52 (s, 9H), 1.10 (s, 9H).

Step 7

N-tert-Butyl-2-(6-cyano-1-methyl-1H-indazol-3-yl)-5H-pyrrolo[2,3-b]pyrazine-7-carboxamide

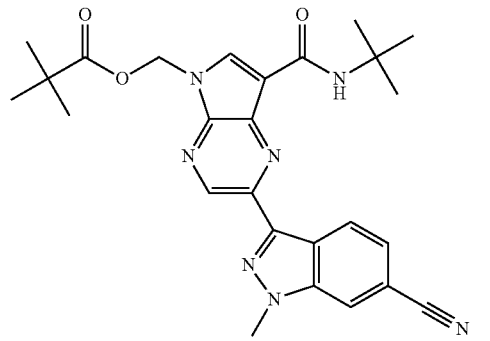

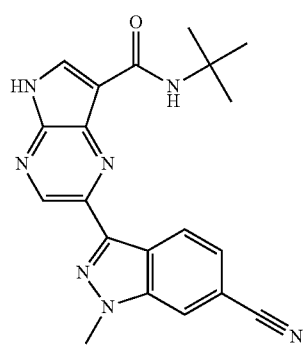

To a stirred solution of (7-(tert-butylcarbamoyl)-2-(6-cyano-1-methyl-1H-indazol-3-yl)-5H-pyrrolo[2,3-b]pyrazin-5-yl)methyl pivalate (80 mg, 0.164 mmol) in THF (5 mL) was added a 15% NaOH aqueous solution (0.5 mL) at room temperature and the reaction mixture stirred for 15 hours. The solvent was evaporated under reduced pressure. The residue was purified by preparative-HPLC (Gemini 5u C18 150×21.2 mm; inject volume: 3 mL/inj, flow rate: 20 mL/min; wavelength: 214 nm and 254 nm; the gradient conditions were: 15% acetonitrile/75% water (0.1% trifluoroacetic acid, v/v) initially, proceeding to 70% acetonitrile/30% water (0.1% trifluoroacetic acid, v/v) in a linear fashion over 9 min.) to give N-tert-butyl-2-(6-cyano-1-methyl-1H-indazol-3-yl)-5H-pyrrolo[2,3-b]pyrazine-7-carboxamide (45 mg, 74%) as white solid.

MS: (M+H)$^+$=541; $^1$H NMR (300 MHz, DMSO): δ 12.35 (s, 1H), 10.56 (s, 1H), 9.35 (s, 1H), 8.95 (s, 1H), 8.90 (s, 1H), 8.55 (s, 1H), 8.36 (s, 1H), 8.05-7.99 (m, 2H), 7.77-7.68 (m, 3H), 7.51 (d, 1H, J=6.9 Hz), 7.38 (d, 1H, J=8.7 Hz), 7.00 (d, 1H, J=8.4 Hz), 3.97 (s, 3H), 3.85 (s, 3H), 3.75 (s, 3H).

Example 395

2-(6-Chloro-1-methyl-1H-indazol-3-yl)-N-(1-methylcyclopropyl)-5H-pyrrolo[2,3-b]pyrazine-7-carboxamide

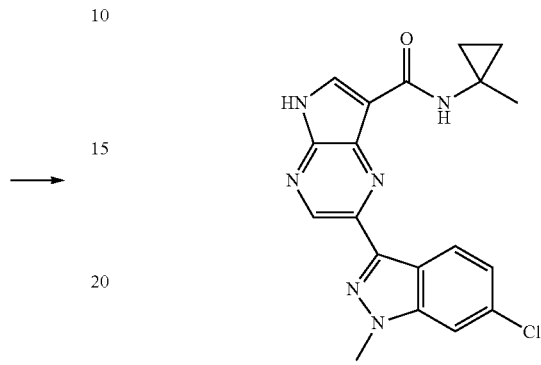

A mixture of 2-(6-chloro-1-methyl-1H-indazol-3-yl)-5H-pyrrolo[2,3-b]pyrazine-7-carboxylic acid (0.07 g, 0.3 mmol), 1-methylcyclopropanamine (0.04 g, 0.56 mmol), EDCI (0.057 g, 0.3 mmol), DMAP (0.037 g, 0.3 mmol), and DIPEA (0.163 g, 1.26 mmol) in 10 mL of DMF was stirred at room temperature for 5 hours, and then HATU (0.114 g, 0.3 mmol) was added. The final reaction mixture was stirred for another 15 hours. The solvent was removed under reduced pressure at 70° C. The residue was triturated with water and then purified by preparative-HPLC (Gemini 5u C18 150×21.2 mm; inject volume: 3 mL/inj, flow rate: 20 mL/min; wavelength: 214 nm and 254 nm; the gradient conditions were: 50% acetonitrile/50% water (0.1% trifluoroacetic acid, v/v) initially, proceeding to 80% acetonitrile/20% water (0.1% trifluoroacetic acid, v/v) in a linear fashion over 9 min.) to give 2-(6-chloro-1-methyl-1H-indazol-3-yl)-N-(1-methylcyclopropyl)-5H-pyrrolo[2,3-b]pyrazine-7-carboxamide (0.035 g, 43%) as a white solid. MS: (M+H)$^+$=381; $^1$H NMR (300 MHz, DMSO): δ 12.87 (s, 1H), 9.11 (s, 1H), 8.55 (s, 1H), 8.46-8.44 (m, 2H), 8.04 (s, 1H), 7.38 (d, 1H, J=8.7 Hz), 4.20 (s, 3H), 1.50 (s, 3H), 0.90-0.82 (m, 4H).

Example 396

2-(6-Chloro-1-methyl-1H-indazol-3-yl)-N-phenyl-5H-pyrrolo[2,3-b]pyrazine-7-carboxamide

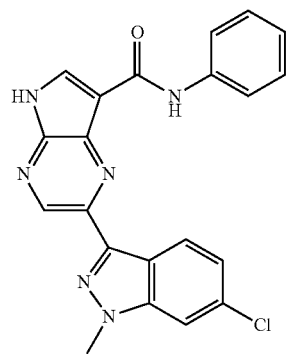 [SMILES: Cn1nc(-c2cnc3[nH]cc(C(=O)Nc4ccccc4)c3n2)c2ccc(Cl)cc21]

A mixture of 2-(6-chloro-1-methyl-1H-indazol-3-yl)-5H-pyrrolo[2,3-b]pyrazine-7-carboxylic acid (0.07 g, 0.3 mmol), aniline (0.05 g, 0.54 mmol), EDCI (0.057 g, 0.3 mmol), DMAP (0.037 g, 0.3 mmol), and DIPEA (0.163 g, 1.26 mmol) in 10 mL of DMF was stirred at room temperature for 5 hours. And then HATU (0.114 g, 0.3 mmol) was added, the final reaction mixture was stirred for 15 hours. The solvent was removed under reduced pressure at 70° C. The residue was triturated with water and then purified by preparative-HPLC (Gemini 5u C18 150×21.2 mm; inject volume: 3 mL/inj, flow rate: 20 mL/min; wavelength: 214 nm and 254 nm; the gradient conditions were: 65% acetonitrile/35% water (0.1% trifluoroacetic acid, v/v) initially, proceeding to 72% acetonitrile/28% water (0.1% trifluoroacetic acid, v/v) in a linear fashion over 9 min.) to give 2-(6-chloro-1-methyl-1H-indazol-3-yl)-N-phenyl-5H-pyrrolo[2,3-b]pyrazine-7-carboxamide (0.025 g, 29%) as a white solid. MS: (M+H)$^+$= 403; $^1$H NMR (300 MHz, DMSO): δ 10.21 (s, 1H), 9.12 (s, 1H), 8.63-8.58 (m, 2H), 8.42 (brs, 2H), 8.04 (s, 1H), 7.83-7.80 (m, 2H), 7.49-7.43 (m, 2H), 7.30 (d, 1H, J=8.7 Hz), 7.17 (d, 1H, J=7.2 Hz), 4.21 (s, 3H).

Example 397

N-(1-Amino-2-methylpropan-2-yl)-2-(6-chloro-1-methyl-1H-indazol-3-yl)-5H-pyrrolo[2,3-b]pyrazine-7-carboxamide

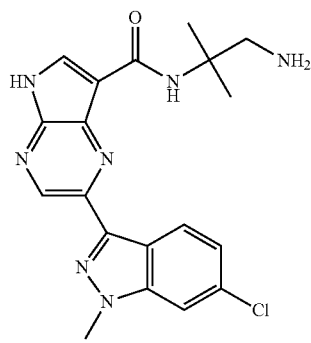 [SMILES: Cn1nc(-c2cnc3[nH]cc(C(=O)NC(C)(C)CN)c3n2)c2ccc(Cl)cc21]

Step 1 tert-Butyl 2-(2-(6-chloro-1-methyl-1H-indazol-3-yl)-5H-pyrrolo[2,3-b]pyrazine-7-carboxamido)-2-methylpropylcarbamate

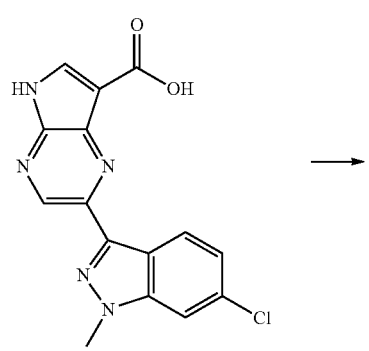

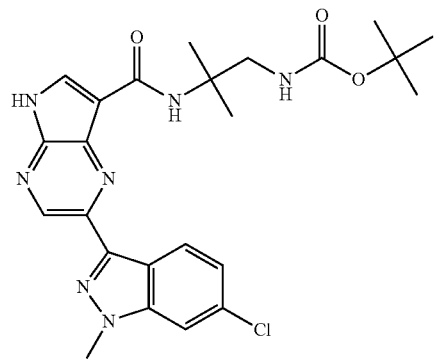

A mixture of 2-(6-fluoro-1-methyl-1H-indazol-3-yl)-5H-pyrrolo[2,3-b]pyrazine-7-carboxylic acid (0.1 g, 0.3 mmol), tert-butyl 2-amino-2-methylpropylcarbamate (0.1 g, 0.53 mmol), EDCI (0.086 g, 0.45 mmol), DMAP (0.055 g, 0.45 mmol), and DIPEA (0.232 g, 1.8 mmol) in 15 mL of DMF was stirred at room temperature for 5 hours. Then HATU (0.17 g, 0.45 mmol) was added, the final reaction mixture was stirred for additional 15 hours. The solvent was removed under reduced pressure. The residue was triturated with water and then passed through a pad of silica gel (200-300 mesh, eluting with a mixture of petroleum ether and ethyl acetate (3:1, v/v) to give tert-butyl 2-(2-(6-chloro-1-methyl-1H-indazol-3-yl)-5H-pyrrolo[2,3-b]pyrazine-7-carboxamido)-2-methylpropylcarbamate (0.1 g, crude) as yellow solid which was used for the next step without further purification. MS: (M+H)$^+$=498.1.

Step 2

N-(1-Amino-2-methylpropan-2-yl)-2-(6-chloro-1-methyl-1H-indazol-3-yl)-5H-pyrrolo[2,3-b]pyrazine-7-carboxamide

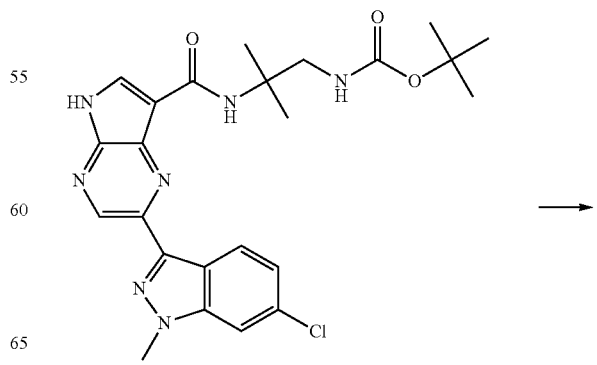

-continued

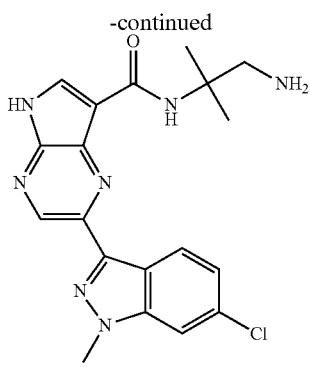

tert-Butyl 2-(2-(6-chloro-1-methyl-1H-indazol-3-yl)-5H-pyrrolo[2,3-b]pyrazine-7-carboxamido)-2-methylpropylcarbamate (0.05 g, 0.1 mmol) in 30 mL of a saturated solution of HCl (g) in dioxane was stirred at room temperature for 2 hours. The solvent was removed and the residue was triturated with ethyl acetate, filtered and filter cake washed with saturated aqueous NaHCO₃ and water successively to give N-(1-amino-2-methylpropan-2-yl)-2-(6-chloro-1-methyl-1H-indazol-3-yl)-5H-pyrrolo[2,3-b]pyrazine-7-carboxamide (22 mg, 55%) as a yellow solid. $^{MS:}$ (M+H)$^+$=398; $^1$H NMR (300 MHz, DMSO): δ 8.97 (s, 1H), 8.60 (d, 1H, J=8.7 Hz), 8.36 (s, 1H), 7.96 (s, 1H), 7.90 (s, 1H), 7.32 (d, 1H, J=8.7 Hz), 4.17 (s, 3H), 2.90 (s, 2H), 1.30 (s, 6H).

Example 398

2-(6-Cyano-1-methyl-1H-indazol-3-yl)-N-(1-hydroxy-2-methylpropan-2-yl)-5H-pyrrolo[3,2-b]pyrazine-7-carboxamide

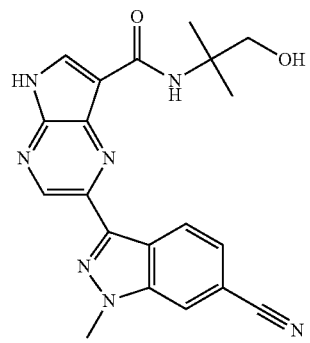 [SMILES: Cn1nc(-c2cnc3[nH]cc(C(=O)NC(C)(C)CO)c3n2)c2ccc(C#N)cc21]

Step 1

1-(tert-Butyldimethylsilyloxy)-2-methylpropan-2-amine

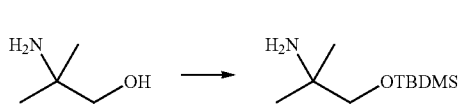

To a stirred solution of 2-amino-2-methylpropan-1-ol (1.78 g, 0.02 mol) in dichloromethane (25 mL) was added tert-butyldimethylsilyl chloride (5.4 g, 0.036 mol) followed by imidazole (3.4 g, 0.05 mol). The mixture was stirred at room temperature for 16 hours. The solvent was removed under reduced pressure. The residue was diluted with water and extracted with EtOAc (3×30 mL). The combined organic layers were washed with NaHCO₃ aqueous, brine and dried over Na₂SO₄. After filtration and concentration, the residue was purified by column chromatography on silica gel eluting with EtOAc to give 1-(tert-butyldimethylsilyloxy)-2-methylpropan-2-amine (3.1 g, 76%) as an oil. $^1$H NMR (300 MHz, CDCl₃): δ 3.26 (s, 2H), 1.02 (s, 6H), 0.88 (s, 9H), 0.03 (s, 6H).

Step 2

2-Bromo-N-(1-(tert-butyldimethylsilyloxy)-2-methylpropan-2-yl)-5H-pyrrolo[3,2-b]pyrazine-7-carboxamide

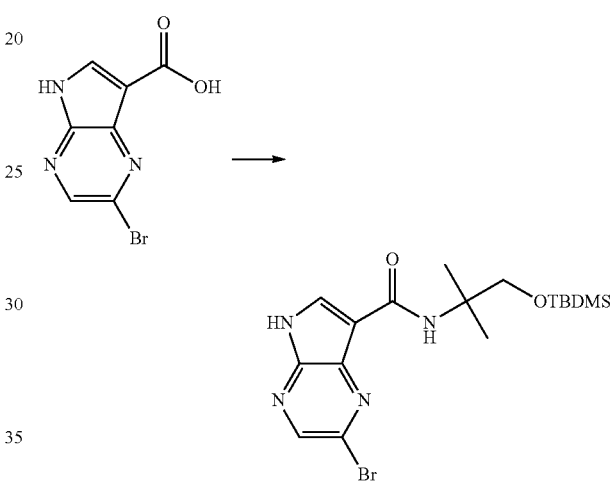

A mixture of 2-bromo-5H-pyrrolo[3,2-b]pyrazine-7-carboxylic acid (310 mg, 1.28 mmol), 1-(tert-butyldimethylsilyloxy)-2-methylpropan-2-amine (390 mg, 1.92 mmol), EDCI (489 mg, 2.56 mmol) and DMAP (312 mg, 2.56 mmol) in 5 mL of DMF was stirred at room temperature for 16 hours. Then the mixture was poured into water and extracted with EtOAc (3×10 mL). The combined organic layers were washed with brine and dried over Na₂SO₄. After filtration and concentration, the residue was used in the next step without further treatment. MS: (M+H)$^+$=427.1.

Step 3

(2-Bromo-7-(1-(tert-butyldimethylsilyloxy)-2-methylpropan-2-ylcarbamoyl)-5H-pyrrolo[3,2-b]pyrazin-5-yl)methyl pivalate

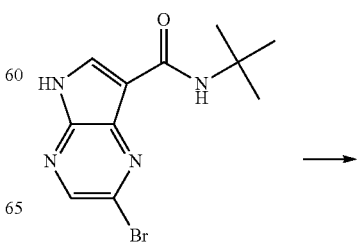

-continued

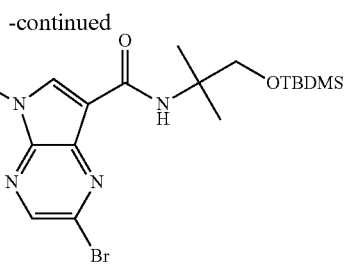

To a stirred mixture of 2-bromo-N-(1-(tert-butyldimethylsilyloxy)-2-methylpropan-2-yl)-5H-pyrrolo[3,2-b]pyrazine-7-carboxamide in DMF (5 mL) was added chloromethyl pivalate (288 mg, 1.92 mmol) followed by $K_2CO_3$ (353 mg, 2.56 mmol). The mixture was stirred at room temperature for 16 hours, then poured into water and extracted with EtOAc (3×10 mL). The combined organic layers were washed with brine and dried over $Na_2SO_4$. After filtration and concentration, the residue was purified by column chromatography on silica gel eluting with petroleum ether/EtOAc (5:1, v/v) to give (2-bromo-7-(1-(tert-butyldimethylsilyloxy)-2-methylpropan-2-ylcarbamoyl)-5H-pyrrolo[3,2-b]pyrazin-5-yl)methyl pivalate (305 mg, 44% over two steps) as a yellow solid. MS: $(M+H)^+$=541; $^1H$ NMR (300 MHz, $CDCl_3$): δ 8.41 (s, 1H), 8.33 (s, 1H), 7.84 (s, 1H), 6.20 (s, 2H), 3.71 (s, 2H), 1.49 (s, 6H), 1.15 (s, 9H), 0.90 (s, 9H), 0.09 (s, 6H).

Step 4

1-Methyl-3-(tributylstannyl)-1H-indazole-6-carbonitrile

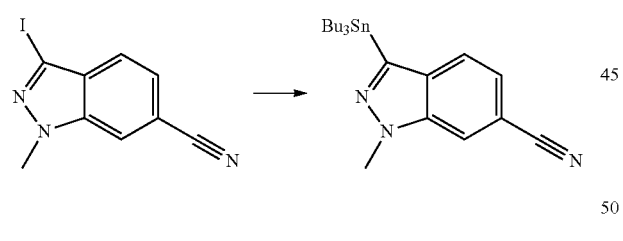

A mixture 3-iodo-1-methyl-1H-indazole-6-carbonitrile and 3-iodo-2-methyl-1H-indazole-6-carbonitrile (160 mg, 0.565 mmol) was dissolved in THF (6 mL). The solution was cooled to −40° C. Isopropylmagnesium chloride 2M in THF (0.34 mL, 0.678 mmol) was added drop-wise at −40° C. The reaction mixture was stirred at −40° C. for 20 min, then chlorotributyltin (0.18 mL, 0.678 mmol) was added slowly. The reaction mixture was allowed to warm to room temperature and stirred for 1.5 h. The reaction mixture was quenched with saturated $NH_4Cl$ solution and then extracted with EtOAc (3×10 mL), combined organics were washed with water (10 mL), brine (10 mL), dried over $Na_2SO_4$ and concentrated. The residue was used in the next step without further treatment.

Step 5

(2-(6-Cyano-1-methyl-1H-indazol-3-yl)-7-(1-hydroxy-2-methylpropan-2-ylcarbamoyl)-5H-pyrrolo[2,3-1)]pyrazin-5-yl)methyl pivalate

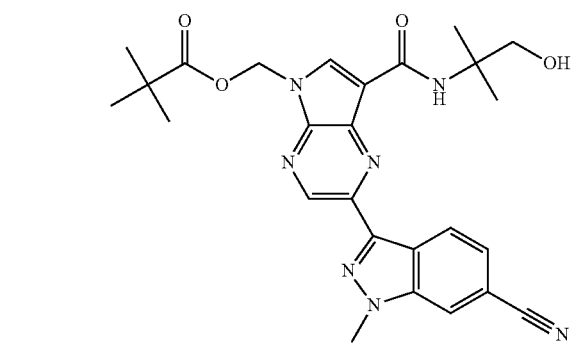

In a round-bottomed flask, (2-bromo-7-(1-(tert-butyldimethylsilyloxy)-2-methylpropan-2-ylcarbamoyl)-5H-pyrrolo[3,2-b]pyrazin-5-yl)methyl pivalate (305 mg, 0.565 mmol) and a crude mixture of 1-methyl-3-(tributylstannyl)-1H-indazole-6-carbonitrile and 1-methyl-3-(tributylstannyl)-1H-indazole-6-carbonitrile were dissolved in DMF (5 mL) under nitrogen. Pd $(PPh_3)_4$ (32 mg, 0.028 mmol) and CuI (21 mg, 0.113 mmol) were added and mixture was sonicated for 5 minutes while bubbling nitrogen. The reaction mixture was stirred at 80° C. for 16 hours. The concentrated mixture was purified by column chromatography on silica gel eluting with petroleum ether/EtOAc (1:1, v/v) to give (2-(6-cyano-1-methyl-1H-indazol-3-yl)-7-(1-hydroxy-2-methylpropan-2-ylcarbamoyl)-5H-pyrrolo[2,3-b]pyrazin-5-yl)methyl pivalate (45 mg, 16%). MS: (M+H)⁺=504.

Step 6

2-(6-Cyano-1-methyl-1H-indazol-3-yl)-N-(1-hydroxy-2-methylpropan-2-yl)-5H-pyrrolo[2,3-b]pyrazine-7-carboxamide

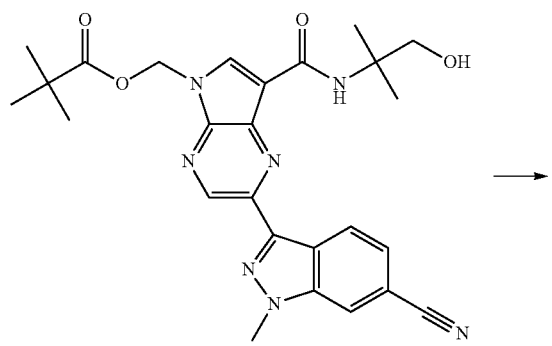

To a stirred solution of (2-(6-cyano-1-methyl-1H-indazol-3-yl)-7-(1-hydroxy-2-methylpropan-2-ylcarbamoyl)-5H-pyrrolo[2,3-b]pyrazin-5-yl)methyl pivalate (45 mg, 0.089 mmol) in 2 mL of THF was added a solution of 10% NaOH (2 mL) at room temperature and the reaction mixture was stirred for 15 hours. The solvent was evaporated under reduced pressure. The residue was diluted with water and adjusted to pH 5-6. The mixture was filtered and the filter cake washed with DMSO (3 mL), MeOH (3 mL) and then dried to give 2-(6-cyano-1-methyl-1H-indazol-3-yl)-N-(1-hydroxy-2-methylpropan-2-yl)-5H-pyrrolo[2,3-b]pyrazine-7-carboxamide (4.5 mg, 12%) as white solid. MS: (M+H)⁺=390; ¹H NMR (300 MHz, DMSO): δ 12.95 (brs, 1H), 9.14 (s, 1H), 8.79 (d, 1H, J=8.1 Hz), 8.54 (s, 1H), 8.42 (s, 1H), 7.91 (s, 1H), 7.62 (d, 1H, J=8.4 Hz), 5.15 (brs, 1H), 4.27 (s, 3H), 3.64 (d, 2H, J=5.4 Hz), 1.47 (s, 6H).

Example 399

N-tert-Butyl-2-(1H-indazol-4-yl)-5H-pyrrolo[3,2-b]pyrazine-7-carboxamide hydrochloride

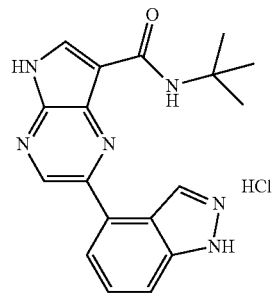 [SMILES: CC(C)(C)NC(=O)c1c[nH]c2ncc(-c3cccc4[nH]ncc34)nc12 ; Cl]

Step 1

(2-Bromo-7-(tert-butylcarbamoyl)-5H-pyrrolo[3,2-b]pyrazin-5-yl)methyl pivalate

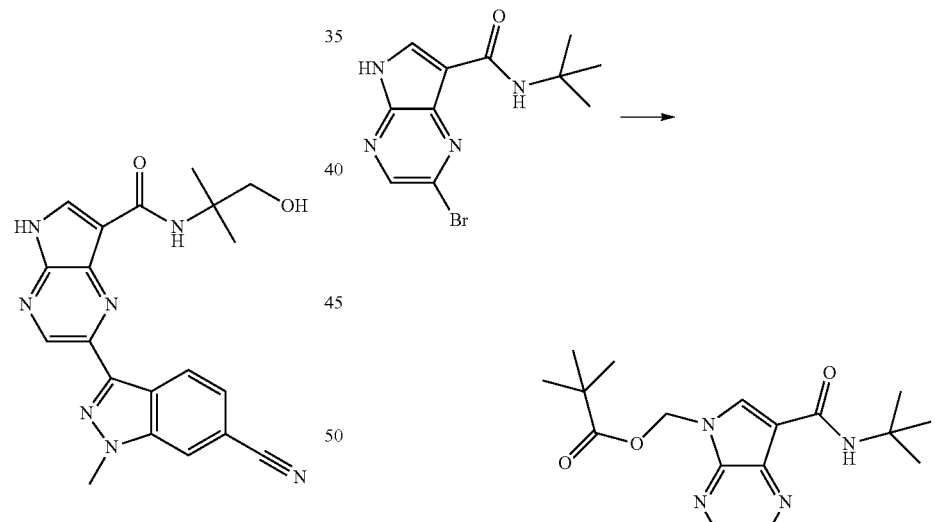

A mixture of methyl 2-bromo-5H-pyrrolo[3,2-b]pyrazine-7-carboxylate (0.345 g, 1.33 mmol), chloromethyl pivalate (406 mg, 2.7 mmol) and K₂CO₃ (373 mg, 2.7 mmol) in dry DMF (8 mL) was heated to 30° C. for 16 hours. Reaction was quenched with water and product extracted with ethyl acetate (100 mL), combined organics were washed with water (3×10 mL) and brine (2×10 mL), then dried over Na₂SO₄, filtered and concentrated. The residue was triturated with ether (5 mL) then decanted and dried to afford (2-bromo-7-(tert-butylcarbamoyl)-5H-pyrrolo[3,2-b]pyrazin-5-yl)methyl pivalate (414 mg, crude) as a yellow solid, which was used into next step without further purification. LCMS: (M+H)⁺=411.

Step 2

1-(Pivaloyloxymethyl)-1H-indazol-4-ylboronic acid

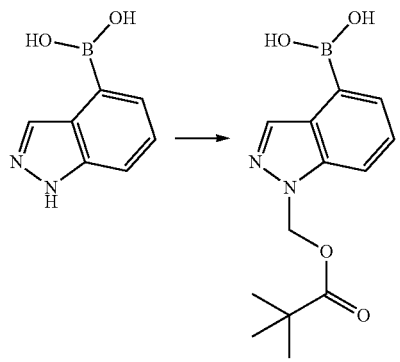 [SMILES: OB(O)c1cccc2[nH]ncc12 ; CC(C)(C)C(=O)OCn1ncc2c(B(O)O)cccc21]

A mixture of 1H-indazol-4-ylboronic acid (0.2 g, 1.227 mmol), chloromethyl pivalate (554 mg, 3.68 mmol) and K₂CO₃ (509 mg, 3.68 mmol) in dry DMF (10 mL) was heated to 30° C. for 16 hours. Reaction was quenched with water and product extracted with ethyl acetate (150 mL), then washed with water (3×20 mL) and brine (2×20 mL), then dried over Na₂SO₄, filtered and concentrated. The product (114 mg, crude) was obtained and used into next step without further purification. LCMS: (M+Na)⁺=299.

Step 3

N-tert-Butyl-2-(1H-indazol-4-yl)-5H-pyrrolo[3,2-b]pyrazine-7-carboxamide hydrochloride

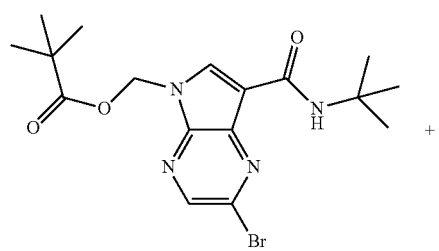

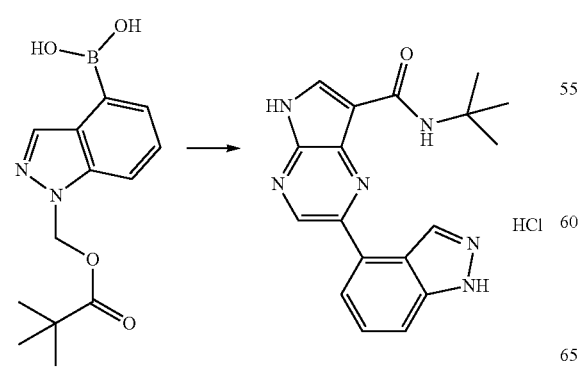

A mixture of (2-bromo-7-(tert-butylcarbamoyl)-5H-pyrrolo[3,2-b]pyrazin-5-yl)methyl pivalate (170 mg, 0.413 mmol), 1-(pivaloyloxymethyl)-1H-indazol-4-ylboronic acid (114 mg, 0.413 mmol), Pd₂(dba)₃ (47 mg, 0.083 mmol), X-Phos (79 mg, 0.166 mmol) and Na₂CO₃ (131 mg, 1.24 mmol) in dioxane (20 mL) and water (5 mL) was heated to 100° C. for 16 hours. Reaction was quenched with water and product extracted with ethyl acetate (90 mL), then washed with water (3×10 mL) and brine (2×10 mL), then dried over Na₂SO₄, filtered and concentrated. The residue was first purified by column chromatography (silica gel, 200-300 mesh, eluting with methanol:dichloromethane=1:30) and then by preparative-HPLC (Gemini 5u C18 150×21.2 mm; inject volume: 3 mL/inj, flow rate: 20 mL/min; wavelength: 214 nm and 254 nm; the gradient conditions are: 62% acetonitrile/38% water (0.1% trifluoroacetic acid, v/v) initially, and then proceed to 64% acetonitrile/36% water (0.1% trifluoroacetic acid, v/v) in a linear fashion after just 9 min.). To the pure product, 1 mL concentrated HCl was added, stirred for 5 min, filtered and dried to afford N-tert-butyl-2-(1H-indazol-4-yl)-5H-pyrrolo[3,2-b]pyrazine-7-carboxamide hydrochloride (33 mg, 22%) as a yellow solid. (M+H)⁺=335; ¹H NMR (300 MHz, CD₃OD): δ 8.94 (s, 1H), 8.86 (s, 1H), 8.33 (s, 1H), 7.81-7.67 (m, 3H), 1.52 (s, 9H).

Example 400

2-(6-Fluoro-1-methyl-1H-indazol-3-yl)-N-(4-hydroxy-2-methylbutan-2-yl)-5H-pyrrolo[2,3-b]pyrazine-7-carboxamide

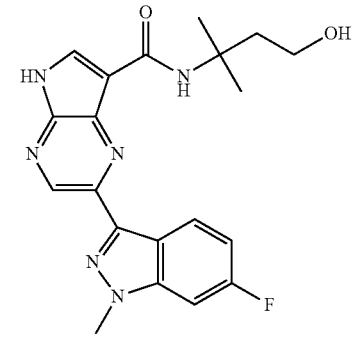 [SMILES: Cn1nc(-c2cnc3[nH]cc(C(=O)NC(C)(C)CCO)c3n2)c2ccc(F)cc21]

Step 1

N-(4-(tert-Butyldimethylsilyloxy)-2-methylbutan-2-yl)-2-(6-fluoro-1-methyl-1H-indazol-3-yl)-5H-pyrrolo[2,3-b]pyrazine-7-carboxamide

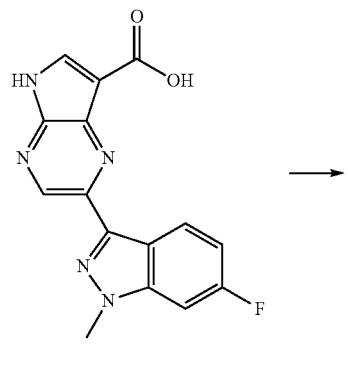

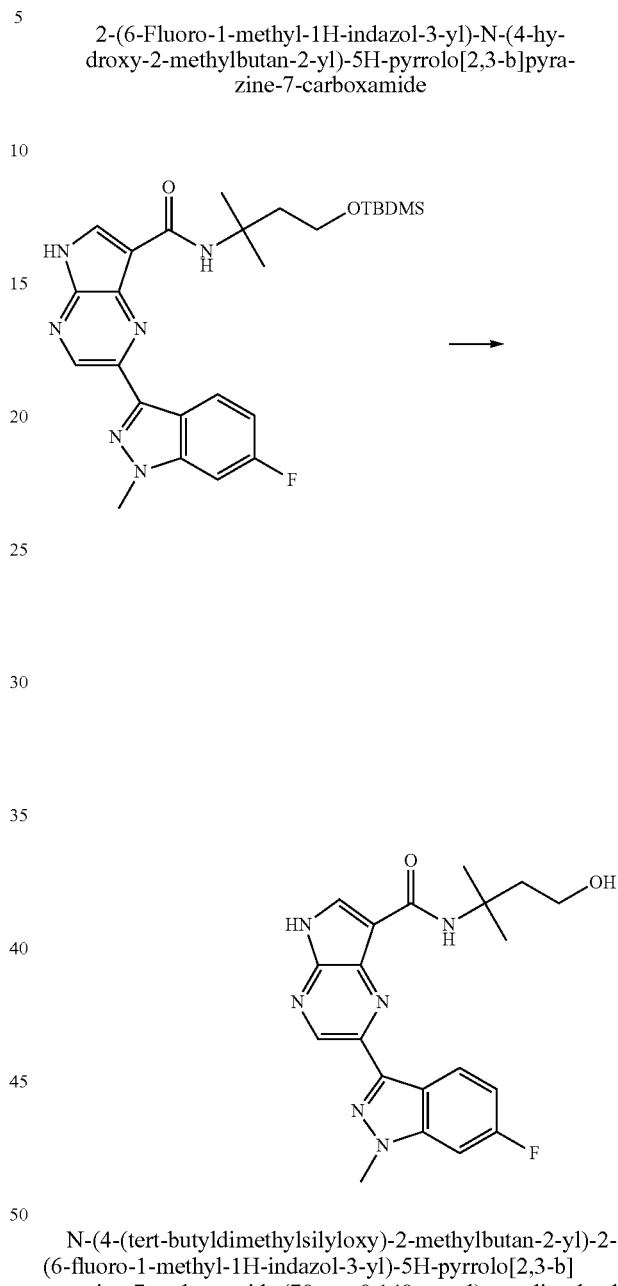

To a stirred solution of 2-(6-fluoro-1-methyl-1H-indazol-3-yl)-5H-pyrrolo[2,3-b]pyrazine-7-carboxylic acid (100 mg, 0.32 mmol) in 6 mL of DMF were added EDCI (123 mg, 0.64 mmol), 4-(tert-butyldimethylsilyloxy)-2-methylbutan-2-amine (139 mg, 0.64 mmol) and DMAP (78 mg, 0.64 mmol) in one portion at room temperature and stirred for 16 hours. The reaction mixture was poured into 35 mL of water filtered and the solid obtained was passed through a pad of silica gel (200-300 mesh, eluting with a mixture of methanol and ethyl acetate (1:20, v/v) to give N-(4-(tert-butyldimethylsilyloxy)-2-methylbutan-2-yl)-2-(6-fluoro-1-methyl-1H-indazol-3-yl)-5H-pyrrolo[2,3-b]pyrazine-7-carboxamide (70 mg, 42.8%) as a pale yellow solid which was used for the next step without further purification. MS: (M+H)$^+$=511.2.

Step 2

2-(6-Fluoro-1-methyl-1H-indazol-3-yl)-N-(4-hydroxy-2-methylbutan-2-yl)-5H-pyrrolo[2,3-b]pyrazine-7-carboxamide N-(4-(tert-butyldimethylsilyloxy)-2-methylbutan-2-yl)-2-(6-fluoro-1-methyl-1H-indazol-3-yl)-5H-pyrrolo[2,3-b]pyrazine-7-carboxamide (70 mg, 0.140 mmol) was dissolved in 30 mL of a saturated solution of HCl (g) in dioxane and the solution was stirred at room temperature for one hour. The solvent was evaporated at 40° C. under reduced pressure and the residue was purified by preparative-HPLC (Gemini 5u C18 150×21.2 mm; inject volume: 3 mL/inj, flow rate: 20 mL/min; wavelength: 214 nm and 254 nm; the gradient conditions were: 38% acetonitrile/62% water (0.1% trifluoroacetic acid, v/v) initially, proceeding to 42% acetonitrile/58% water (0.1% trifluoroacetic acid, v/v) in a linear fashion over 9 min.) to give 2-(6-fluoro-1-methyl-1H-indazol-3-yl)-N-(4-hydroxy-2-methylbutan-2-yl)-5H-pyrrolo[2,3-b]pyrazine-7-carboxamide (15 mg, 27.6%) as a yellow solid. MS: (M+H)$^+$= 397; $^1$H NMR (300 MHz, DMSO): δ 12.84 (s, 1H), 9.10 (s, 1H), 8.55-8.50 (m, 1H), 8.40 (s, 1H), 7.89 (s, 1H), 7.73-7.69

(m, 1H), 7.22-7.16 (m, 1H), 7.42 (t, 2H, J=4.6 Hz), 4.17 (s, 3H), 3.61-3.55 (m, 2H), 2.13-2.09 (m, 2H), 1.25 (s, 6H).

Example 401

2-(6-Chloro-1-methyl-1H-indazol-3-yl)-N-(2-cyclopropylpropan-2-yl)-5H-pyrrolo[2,3-b]pyrazine-7-carboxamide

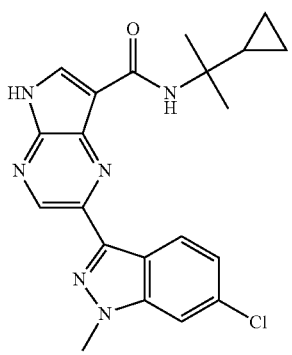 [SMILES: Cn1nc(-c2cnc3[nH]cc(C(=O)NC(C)(C)C4CC4)c3n2)c2ccc(Cl)cc21]

Step 1

(E)-N-(1-Cyclopropylethylidene)-2-methylpropane-2-sulfinamide

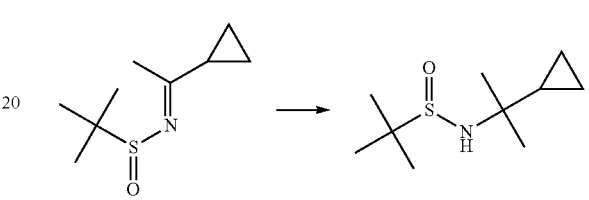

A mixture of 1-cyclopropylethanone (1 g, 12 mmol), 2-methylpropane-2-sulfinamide (1.7 g, 14 mmol), Ti(OEt)$_4$ (5.5 g, 24 mmol) in 10 mL of THF was heated at reflux with stirring overnight. The mixture was cooled to room temperature, solvent was removed under reduced pressure and the crude residue was purified by column chromatography (silica gel, 200-300 mesh, petroleum ether and ethyl acetate (3:1, v/v) to give (E)-N-(1-cyclopropylethylidene)-2-methylpropane-2-sulfinamide (0.6 g, 27%) as clear oil. MS: (M+H)$^+$=188.2; $^1$H NMR (300 MHz, CDCl$_3$): δ 2.36 (s, 3H), 1.69 (m, 1H), 1.18 (s, 9H), 1.07-0.89 (m, 4H).

Step 2

N-(2-Cyclopropylpropan-2-yl)-2-methylpropane-2-sulfinamide

To a stirred solution of (E)-N-(1-cyclopropylethylidene)-2-methylpropane-2-sulfinamide (0.6 g, 3.2 mmol) in 30 mL of toluene at −78° C. was added Me$_3$Al (1.76 mL, 3.5 mmol, 2M in toluene) under nitrogen atmosphere. After stirred 20 minutes at −78° C., MeLi (2.3 mL, 7 mmol, 3M in dimethoxymethane) was added drop-wise and the mixture stirred at −78° C. for 4 hours. The reaction was quenched by adding 2 mL of water. The solvent was removed under reduced pressure and the residue was purified by column chromatography (silica gel, 200-300 mesh, eluting with a mixture of petroleum ether and ethyl acetate (4:1, v/v) to give N-(2-cyclopropylpropan-2-yl)-2-methylpropane-2-sulfinamide (0.18 g, 28%) as a yellow oil. MS: (M+H)$^+$=204.1; $^1$H NMR (300 MHz, CDCl$_3$): δ 3.03 (brs, 1H), 1.17 (s, 3H), 1.16 (s, 9H), 1.12 (s, 3H), 0.98-0.95 (m, 1H), 0.43-0.29 (m, 4H).

Step 3

2-Cyclopropylpropan-2-amine hydrochloride

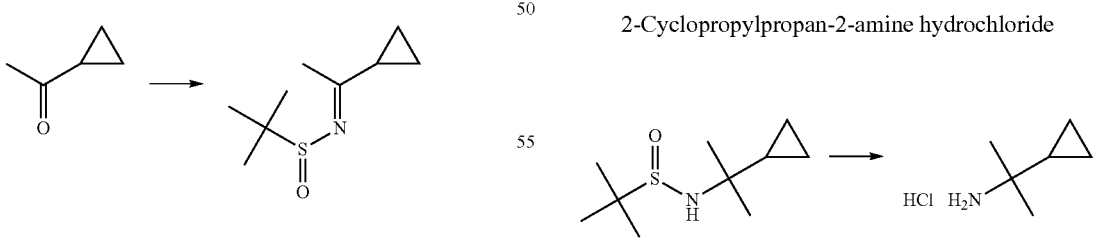

To a stirred solution of N-(2-cyclopropylpropan-2-yl)-2-methylpropane-2-sulfinamide (0.18 g, 0.89 mmol) in 15 mL of MeOH was added a saturated solution of HCl (g) in dioxane (2 mL). The solution was stirred at room temperature for 1 hour. The solvent was removed under reduced pressure the residue was triturated with EtOAc then decanted and dried to give 2-cyclopropylpropan-2-amine hydrochloride (0.12 g, 75%) as a white solid. MS: (M+H)⁺=100.2; ¹H NMR (300 MHz, CD₃OD): δ 1.22 (s, 6H), 1.10-1.07 (m, 1H), 0.61-0.49 (m, 4H).

Step 4

2-(6-Chloro-1-methyl-1H-indazol-3-yl)-N-(2-cyclopropylpropan-2-yl)-5H-pyrrolo[2,3-b]pyrazine-7-carboxamide

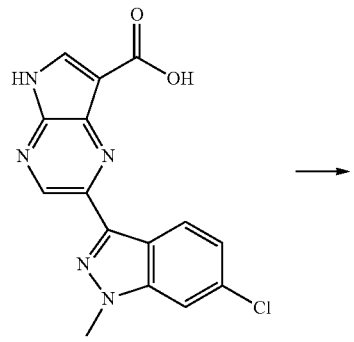

A mixture of 2-(6-chloro-1-methyl-1H-indazol-3-yl)-5H-pyrrolo[2,3-b]pyrazine-7-carboxylic acid (0.07 g, 0.3 mmol), 2-cyclopropylpropan-2-amine hydrochloride (0.05 g, 0.37 mmol), EDCI (0.057 g, 0.3 mmol), DMAP (0.037 g, 0.3 mmol), and DIPEA (0.163 g, 1.26 mmol) in 10 mL of DMF was stirred at room temperature for 5 hours. Then HATU (0.114 g, 0.3 mmol) was added, the final reaction mixture was stirred for additional 15 hour. The mixture was poured into 30 mL of water with stirring. After 30 minutes, the mixture was filtered and the filter cake was purified by preparative-HPLC (Gemini 5u C18 150×21.2 mm; inject volume: 3 mL/inj, flow rate: 20 mL/min; wavelength: 214 nm and 254 nm; the gradient conditions were: 35% acetonitrile/65% water (0.1% trifluoroacetic acid, v/v) initially, proceeding to 65% acetonitrile/35% water (0.1% trifluoroacetic acid, v/v) in a linear fashion over 9 min.) to give 2-(6-chloro-1-methyl-1H-indazol-3-yl)-N-(2-cyclopropylpropan-2-yl)-5H-pyrrolo[2,3-b] pyrazine-7-carboxamide (0.025 g, 28%) as a yellow solid. MS: (M+H)⁺=409; ¹H NMR (300 MHz, DMSO): δ 12.81 (s, 1H), 9.04 (s, 1H), 8.41-8.38 (m, 2H), 7.95-7.87 (m, 2H), 7.21 (d, 1H, J=7.2 Hz), 4.15 (s, 3H), 1.53-1.20 (m, 7H), 0.42 (brs, 4H).

Example 402

N-(cis-4-Aminocyclohexyl)-2-(5-(difluoromethoxy)-1-methyl-1H-indazol-3-yl)-5H-pyrrolo[3,2-b]pyrazine-7-carboxamide hydrochloride

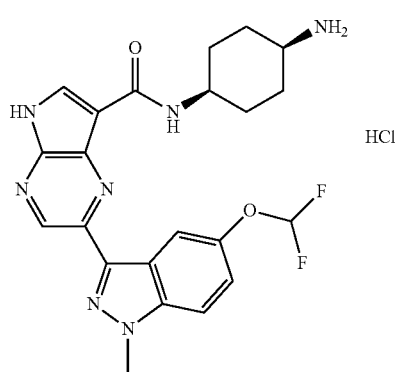 [SMILES: Cn1nc(-c2cnc3[nH]cc(C(=O)N[C@H]4CC[C@@H](N)CC4)c3n2)c2cc(OC(F)F)ccc21 ; Cl]

Step 1

5-(tert-Butyldimethylsilyloxy)-3-iodo-1-methyl-1H-indazole

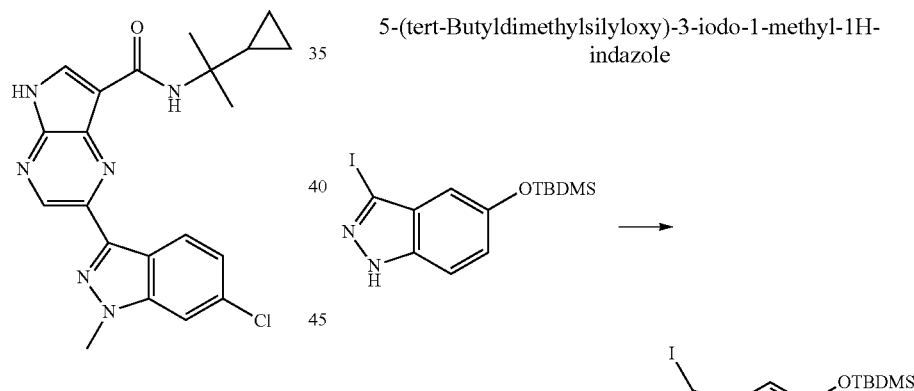

To a solution of 5-(tert-butyldimethylsilyloxy)-3-iodo-1H-indazole (3 g, 8.0 mmol) in THF (25 mL) was added KO-tBu (1.28 g, 11.2 mmol) at 0° C. followed by addition of MeI (1.58 g, 11.2 mmol), after the addition, the reaction mixture was warmed to room temperature and stirred for 4 hours, then H₂O (25 mL) was added to the mixture and product extracted with EtOAc (100 mL). The organic layer was washed with H₂O (100 mL), brine (100 mL), dried over Na₂SO₄ and concentrated under reduced pressure, the residue was purified by column chromatography (silica gel, 200-300 mesh, eluting with petroleum ether/EtOAc=5:1) to give 5-(tert-butyldimethylsilyloxy)-3-iodo-1-methyl-1H-indazole (2.5 g, 80.3%) as a white solid. (M+H)⁺=389; ¹H NMR (300 MHz, CDCl₃), δ 7.22-7.19 (m, 1H), 7.03-7.01 (m, 1H), 6.80 (s, 1H), 4.05 (s, 3H), 1.01 (s, 9H), 0.23 (s, 6H).

Step 2

3-Iodo-1-methyl-1H-indazol-5-ol

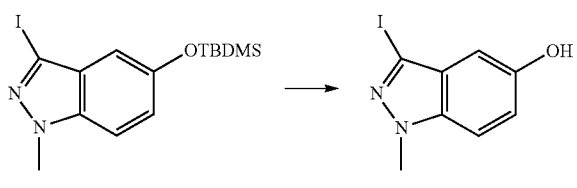 [SMILES: Cn1nc(I)c2cc(O[Si](C)(C)C(C)(C)C)ccc21 ; Cn1nc(I)c2cc(O)ccc21]

To a solution of 5-(tert-butyldimethylsilyloxy)-3-iodo-1-methyl-1H-indazole (1 g, 2.57 mmol) in THF (5 mL) was added TBAF (6.42 mL, 12.85 mmol) at 0° C., after the addition, the reaction mixture was warmed to room temperature and stirred for 0.5 hour, then H2O (25 mL) was added to the mixture and product extracted with EtOAc (100 mL). The organic layer was washed with H$_2$O (100 mL), brine (100 mL), dried over Na$_2$SO$_4$ and concentrated under reduced pressure, the residue was triturated with petroleum ether (5 mL), filtered and dried to give 3-iodo-1-methyl-1H-indazol-5-ol (0.85 g, 93.3%) as a white solid. Crude material used into the next step without further purification. LCMS: (M+H)$^+$= 275.

Step 3

5-(Difluoromethoxy)-3-iodo-1-methyl-1H-indazole

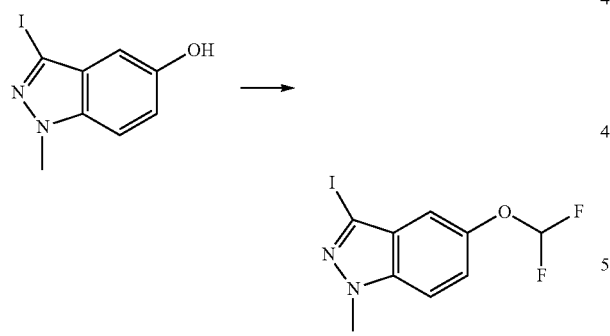

Diethyl bromodifluoromethylphosphonate (9 g, 10.9 mmol) was added in one portion to a cooled (dry ice-acetone bath) solution of 3-iodo-1-methyl-1H-indazol-5-ol (3 g, 37.8 mmol) and KOH (15 g, 267 mmol) in CH$_3$CN (50 mL) and H$_2$O (50 mL) with stirring, the reaction mixture was warmed to room temperature and stirred for 0.5 h, the mixture was diluted with EtOAc (50 mL), The organic layer was washed with H$_2$O (50 mL), brine (100 mL), dried over Na$_2$SO$_4$ and concentrated under reduced pressure, the residue was purified by column chromatography (silica gel, 200-300 mesh, eluting with petroleum ether/EtOAc=3:1) to give 5-(difluoromethoxy)-3-iodo-1-methyl-1H-indazole (1.85 g, 53%) as a white solid. LCMS: (M+H)$^+$=325; $^1$H NMR (300 MHz, CDCl$_3$), δ 7.36-7.33 (m, 1H), 7.28-7.23 (m, 1H), 7.19 (s, 1H), 6.53 (t, 1H, J=73.5 Hz), 4.09 (s, 3H).

Step 4

5-(Difluoromethoxy)-1-methyl-3-(tributylstannyl)-1H-indazole

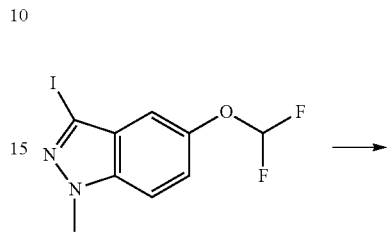

To a solution of 5-(difluoromethoxy)-3-iodo-1-methyl-1H-indazole (400 mg, 1.23 mmol) in dry THF (15 mL) was added isopropylmagnesium chloride (0.75 mL, 1.3 mmol, 2M in THF) drop-wise at −16° C. under nitrogen atmosphere, stirred for 30 minutes, then dibutylchloro(propyl)stannane (0.5 mL, 1.45 mmol) was added drop-wise, the reaction mixture was warmed to room temperature slowly and stirred for 2 hours. The reaction mixture was quenched with a saturated solution of NH$_4$Cl (40 mL) and extracted with EtOAc (3×30 mL). The combined organic layers were dried over Na$_2$SO$_4$, filtered and concentrated under reduced pressure and the residue was used into the next step without purification (500 mg, crude) as oil.

Step 5

Methyl 2-(5-(difluoromethoxy)-1-methyl-1H-indazol-3-yl)-5-(pivaloyloxymethyl)-5H-pyrrolo[2,3-b]pyrazine-7-carboxylate

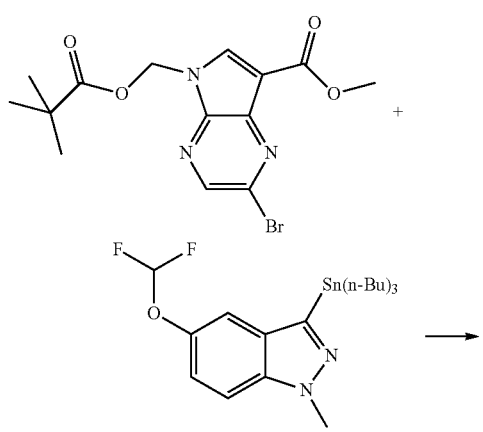

-continued

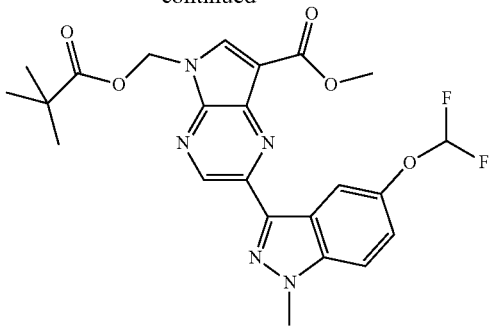

To a solution of methyl 2-bromo-5-(pivaloyloxymethyl)-5H-pyrrolo[3,2-b]pyrazine-7-carboxylate (370 mg, 1.0 mmol) and 5-(difluoromethoxy)-1-methyl-3-(tributylstannyl)-1H-indazole (500 mg, 1 mmol) in DMF (10 mL) were added CuI (30 mg, 0.16 mmol) and Pd(PPh$_3$)$_4$ (47 mg, 0.041 mmol), the reaction mixture was degassed by bubbling nitrogen for 3 minutes and refilled with nitrogen. The mixture was heated to 80° C. for 5 hours under nitrogen, after cooling, water (50 mL) was added and product extracted with EtOAc (3×40 mL), the combined organic layers were dried over Na$_2$SO$_4$ and concentrated under reduced pressure to give methyl 245-(difluoromethoxy)-1-methyl-1H-indazol-3-yl)-5-(pivaloyloxymethyl)-5H-pyrrolo[2,3-b]pyrazine-7-carboxylate (120 mg, crude) as an orange solid, material used in the next step without further purification. LCMS: (M+H)$^+$=88; (M+Na)$^+$=510.

Step 6

2-(5-(Difluoromethoxy)-1-methyl-1H-indazol-3-yl)-5H-pyrrolo[2,3-b]pyrazine-7-carboxylic acid

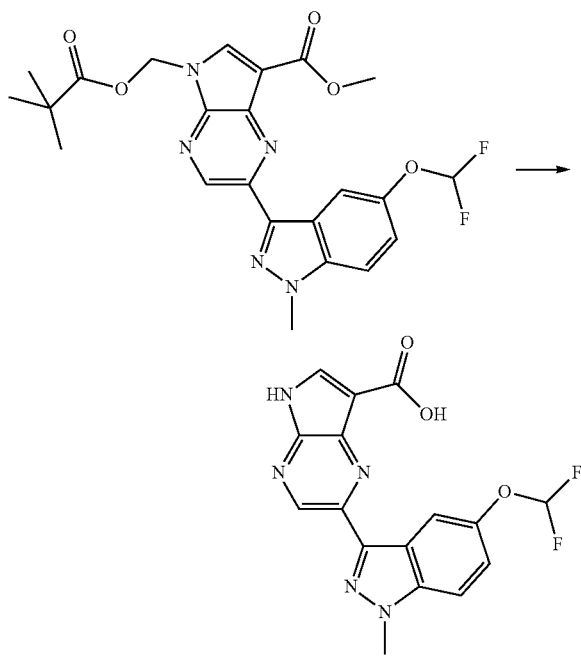

To a suspension of methyl 2-(5-(difluoromethoxy)-1-methyl-1H-indazol-3-yl)-5-(pivaloyloxymethyl)-5H-pyrrolo[2,3-b]pyrazine-7-carboxylate (120 mg, 0.25 mmol) in dioxane/water (10 mL/10 mL) was added NaOH (140 mg, 2.5 mmol), the reaction mixture was heated to 90° C. with stirring for 7 hours, the dioxane was removed under reduced pressure, the aqueous layer was adjusted to pH=4 with conc. HCl, the obtained precipitate was collected by filtration and washed with water (5 mL) and dried to afford 2-(1-methyl-5-(trifluoromethyl)-1H-indazol-3-yl)-5H-pyrrolo[3,2-b]pyrazine-7-carboxylic acid (150 mg, crude as an orange solid, material used in the next step without further purification. LCMS: (M+H)$^+$=360; (M+Na)$^+$=382.

Step 7 tert-Butyl cis-4-(2-(5-(difluoromethoxy)-1-methyl-1H-indazol-3-yl)-5H-pyrrolo[2,3-b]pyrazine-7-carboxamido)cyclohexylcarbamate

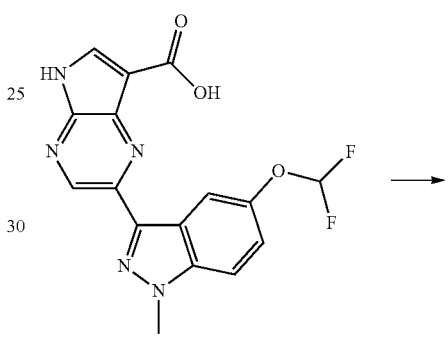

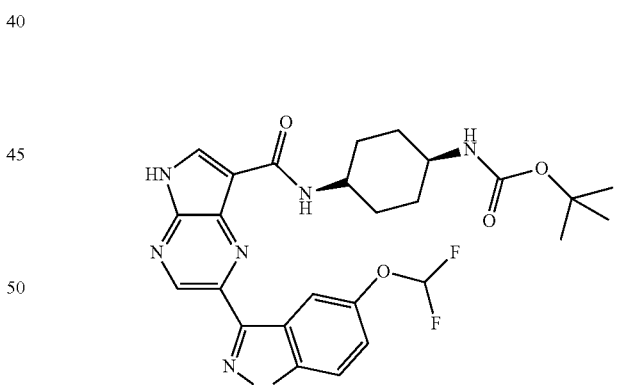

2-(5-(Difluoromethoxy)-1-methyl-1H-indazol-3-yl)-5H-pyrrolo[2,3-b]pyrazine-7-carboxylic acid (150 mg, 0.43 mmol), tert-butyl cis-4-aminocyclohexylcarbamate (102 mg, 0.48 mmol) and HATU (196 mg, 0.51 mmol) in 15 mL of dry THF was stirred for 4 hours. The reaction mixture was evaporated to dryness, the residue was suspended in 50 mL of 0.5N HCl, extracted with ethyl acetate (3×50 mL), dried over sodium sulfate and concentrated to give tert-butyl cis-4-(2-(5-(difluoromethoxy)-1-methyl-1H-indazol-3-yl)-5H-pyrrolo[2,3-b]pyrazine-7-carboxamido)cyclohexylcarbamate (54 mg, crude). LCMS: (M+H)⁺=556; (M+Na)⁺=578. Used in the next step without further purification.

Step 8

N-(cis-4-Aminocyclohexyl)-2-(5-(difluoromethoxy)-1-methyl-1H-indazol-3-yl)-5H-pyrrolo[3,2-b]pyrazine-7-carboxamide hydrochloride

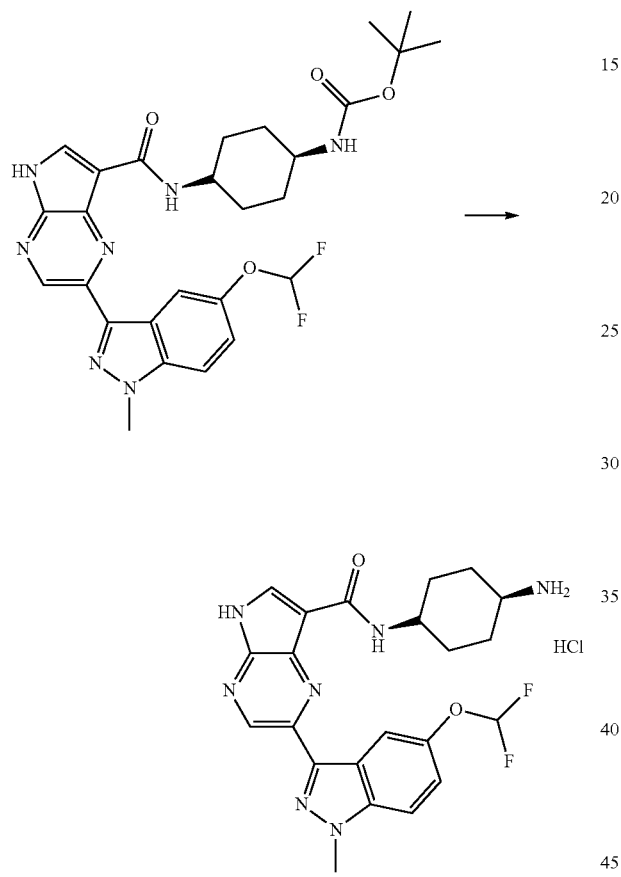

tert-Butyl cis-4-(2-(5-(difluoromethoxy)-1-methyl-1H-indazol-3-yl)-5H-pyrrolo[2,3-b]pyrazine-7-carboxamido)cyclohexylcarbamate (54 mg, 0.1 mmol) in 3 mL of 1,4-dioxane was added 10 mL of concentrated HCl. The reaction mixture was stirred overnight at 25° C. After evaporation under the reduced pressure, the residue was purified by preparative-HPLC (Gemini 5u C18 150×21.2 mm; inject volume: 3 mL/inj, flow rate: 20 mL/min; wavelength: 214 nm and 254 nm; the gradient conditions are: 40% acetonitrile/60% water (0.1% trifluoroacetic acid V/V) initially, and then proceed to 50% acetonitrile/50% water (0.1% trifluoroacetic acid V/V) in a linear fashion after just 9 min). After concentration, the crude solid was treated with 1N HCl (2 mL), the mixture was stirred for 10 min then evaporated and dried to afford N-(cis-4-aminocyclohexyl)-2-(5-(difluoromethoxy)-1-methyl-1H-indazol-3-yl)-5H-pyrrolo[3,2-b]pyrazine-7-carboxamide hydrochloride (13 mg, 29.5%) as yellow solid. LCMS: (M+H)⁺=456; ¹H NMR (300 MHz, CD₃OD): δ 8.96 (s, 1H), 8.22 (s, 1H), 8.01 (d, 1H, J=2.1 Hz), 7.56 (d, 1H, J=9.0 Hz), 7.26 (dd, 1H, J1=9.0 Hz, J2=2.4 Hz), 6.76 (t, 1H, J=74.1 Hz), 4.16-4.14 (m, 1H), 4.11 (s, 3H), 3.17-3.15 (m, 1H), 2.15-2.11 (m, 2H), 1.91-1.78 (m, 4H), 1.60-1.48 (m, 2H).

Example 403

N-(3-Aminocyclohexyl)-2-(6-chloro-1-methyl-1H-indazol-3-yl)-5H-pyrrolo[2,3-b]pyrazine-7-carboxamide 2,2,2-trifluoroacetate A mixture of 2-(6-chloro-1-methyl-1H-indazol-3-yl)-5H-pyrrolo[2,3-b]pyrazine-7-carboxylic acid (0.07 g, 0.3 mmol), cyclohexane-1,3-diamine (0.05 g, 0.44 mmol), EDCI (0.057 g, 0.3 mmol), DMAP (0.037 g, 0.3 mmol), and DIPEA (0.163 g, 1.26 mmol) in 10 mL of DMF were stirred at room temperature for 5 hours. Then HATU (0.114 g, 0.3 mmol) was added, the final reaction mixture was stirred for additional 15 hours. The solvent was removed under reduced pressure at 70° C. The residue was triturated with water and then purified by preparative-HPLC (Gemini 5u C18 150×21.2 mm; inject volume: 3 mL/inj, flow rate: 20 mL/min; wavelength: 214 nm and 254 nm; the gradient conditions were: 23% acetonitrile/77% water (0.1% trifluoroacetic acid, v/v) initially, proceeding to 45% acetonitrile/55% water (0.1% trifluoroacetic acid, v/v) in a linear fashion over 9 min.) to give N-(3-aminocyclohexyl)-2-(6-chloro-1-methyl-1H-indazol-3-yl)-5H-pyrrolo[2,3-b]pyrazine-7-carboxamide 2,2,2-trifluoroacetate (0.013 g, 14%) as a yellow solid. MS: (M+H)⁺=424; ¹H NMR (300 MHz, DMSO): δ 9.02-8.99 (m, 1H), 8.31-8.16 (m, 2H), 7.65 (s, 1H), 7.23-7.18 (m, 1H), 4.10 (s, 3H), 3.42-3.31 (m, 1H), 2.60-2.57 (m, 1H), 2.22-2.06 (m, 3H), 1.93-1.78 (m, 1H), 1.66-1.58 (m, 1H), 1.50-1.38 (m, 3H).

Example 404

2-(6-Chloro-1-methyl-1H-indazol-3-yl)-N-(3-cyanophenyl)-5H-pyrrolo[3,2-b]pyrazine-7-carboxamide

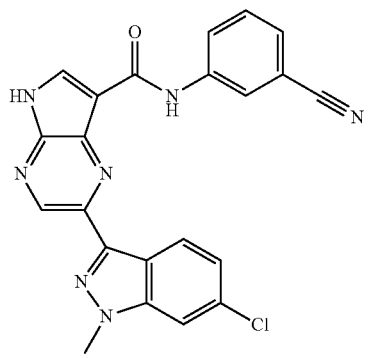 [SMILES: Cn1nc(-c2cnc3[nH]cc(C(=O)Nc4cccc(C#N)c4)c3n2)c2ccc(Cl)cc21]

A mixture of 2-(6-chloro-1-methyl-1H-indazol-3-yl)-5H-pyrrolo[3,2-b]pyrazine-7-carboxylic acid (70 mg, 0.23 mmol), 3-aminobenzonitrile (41 mg, 0.344 mmol), EDCI (88 mg, 0.46 mmol) and DMAP (56 mg, 0.46 mmol) in DMF (5 mL) was stirred at room temperature for 16 hours. Then the mixture was poured into water (5 mL) and filtered to give a crude product. The crude product was triturated with DMSO and MeOH, then decanted and dried to give 2-(6-chloro-1-methyl-1H-indazol-3-yl)-N-(3-cyanophenyl)-5H-pyrrolo[3,2-b]pyrazine-7-carboxamide (20 mg, 20%) as a white solid. MS: (M+H)$^+$=428; $^1$H NMR (300 MHz, DMSO): δ 10.55 (s, 1H), 8.81 (s, 1H), 8.55-8.50 (m, 2H), 8.15 (brs, 1H), 8.03-8.00 (m, 1H), 7.92 (s, 1H), 7.59 (d, 1H, J=8.1 Hz), 7.48 (d, 1H, J=7.8 Hz), 7.26 (d, 1H, J=7.5 Hz), 4.14 (s, 3H).

Example 405

2-(6-Chloro-1-methyl-1H-indazol-3-yl)-N-(pyridin-3-yl)-5H-pyrrolo[2,3-b]pyrazine-7-carboxamide

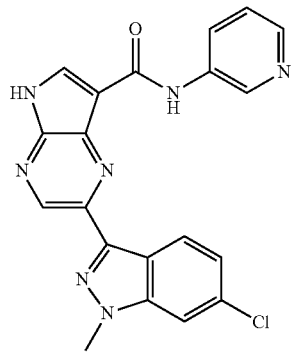 [SMILES: Cn1nc(-c2cnc3[nH]cc(C(=O)Nc4cccnc4)c3n2)c2ccc(Cl)cc21]

A mixture of 2-(6-chloro-1-methyl-1H-indazol-3-yl)-5H-pyrrolo[2,3-b]pyrazine-7-carboxylic acid (0.07 g, 0.3 mmol), pyridin-3-amine (0.05 g, 0.53 mmol), EDCI (0.057 g, 0.3 mmol), DMAP (0.037 g, 0.3 mmol), and DIPEA (0.163 g, 1.26 mmol) in 10 mL of DMF were stirred at room temperature for 5 hours. Then HATU (0.114 g, 0.3 mmol) was added, the final reaction mixture was stirred for additional. The solvent was removed under reduced pressure at 70° C. The residue was triturated with water, EtOAc and DMSO successively then decanted and dried to give 2-(6-chloro-1-methyl-1H-indazol-3-yl)-N-(pyridin-3-yl)-5H-pyrrolo[2,3-b]pyrazine-7-carboxamide (0.022 g, 26%) as a white solid. MS: (M+H)$^+$=404; $^1$H NMR (300 MHz, DMSO): δ 10.20 (s, 1H), 9.09 (s, 1H), 8.90 (s, 1H), 8.63 (s, 1H), 8.54 (d, 1H, J=8.7 Hz), 8.34 (d, 1H, J=4.5 Hz), 8.26 (d, 1H, J=8.7 Hz), 7.98 (s, 1H), 7.47 (dd, 1H, J=8.4, 4.8 Hz), 7.22 (d, 1H, J=8.4 Hz), 4.17 (s, 3H).

Example 406

2-(6-Fluoro-1-methyl-1H-indazol-3-yl)-N-(3-methylpyrrolidin-3-yl)-5H-pyrrolo[2,3-b]pyrazine-7-carboxamide hydrochloride

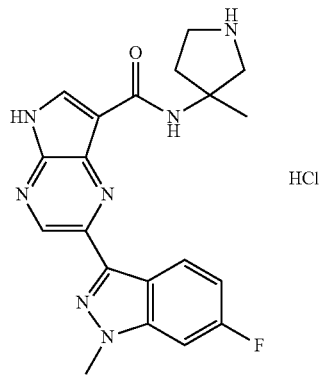 [SMILES: Cn1nc(-c2cnc3[nH]cc(C(=O)NC4(C)CCNC4)c3n2)c2ccc(F)cc21 ; Cl]

Step 1 tert-Butyl 3-(2-(6-fluoro-1-methyl-1H-indazol-3-yl)-5H-pyrrolo[3,2-b]pyrazine-7-carboxamido)-3-methylpyrrolidine-1-carboxylate

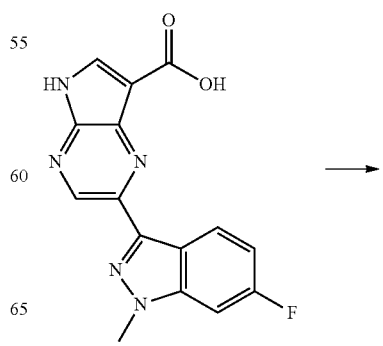

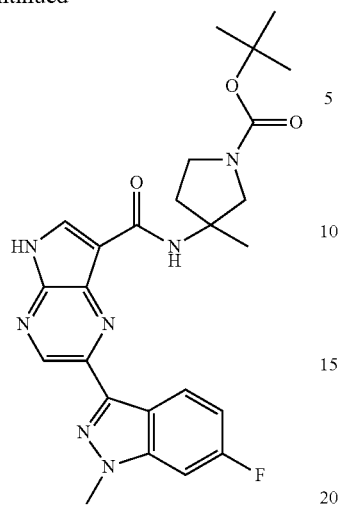

To a stirred solution of 2-(6-fluoro-1-methyl-1H-indazol-3-yl)-5H-pyrrolo[2,3-b]pyrazine-7-carboxylic acid (100 mg, 0.32 mmol) in 6 mL of DMF were added EDCI (123 mmol, 0.64 mmol), DMAP (110 mg, 0.90 mmol) and tert-butyl 3-amino-3-methylpyrrolidine-1-carboxylate (128 mg, 0.64 mmol) in one portion at room temperature and the mixture stirred for 16 hours. The solvent was evaporated at 70° C. under reduced pressure, the residue was triturated with petroleum ether then decanted and dried to give crude tert-butyl 3-(2-(6-fluoro-1-methyl-1H-indazol-3-yl)-5H-pyrrolo[3,2-b]pyrazine-7-carboxamido)-3-methylpyrrolidine-1-carboxylate (103 mg, 65.2%) as a yellow solid which was used for the next step without further purification.

MS: (M+H)$^+$=494.1.

Step 2

2-(6-Fluoro-1-methyl-1H-indazol-3-yl)-N-(3-methylpyrrolidin-3-yl)-5H-pyrrolo[2,3-b]pyrazine-7-carboxamide hydrochloride

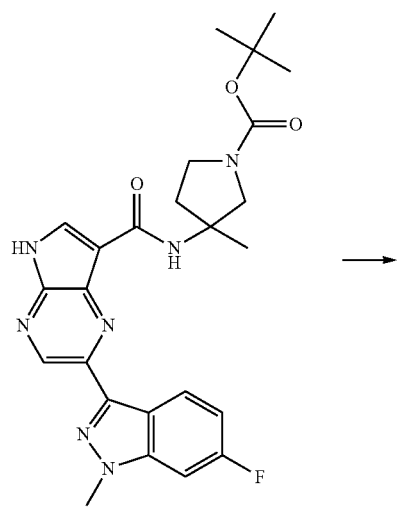

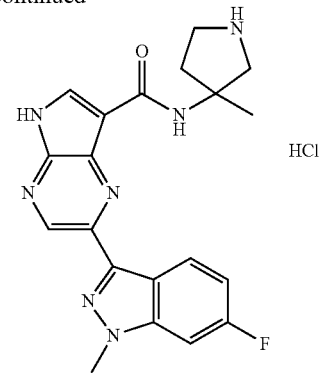

tert-Butyl 4-(2-(6-fluoro-1-methyl-1H-indazol-3-yl)-5H-pyrrolo[2,3-b]pyrazine-7-carboxamido)-4-methylpiperidine-1-carboxylate (103 mg, 0.20 mmol) was dissolved in 20 mL of a saturated solution of HCl (g) in dioxane and the mixture was stirred at room temperature for 2 hours. The solvent was evaporated at 40° C. under reduced pressure and the residue was purified by preparative-HPLC (Gemini 5u C18 150×21.2 mm; inject volume: 3 mL/inj, flow rate: 20 mL/min; wavelength: 214 nm and 254 nm; the gradient conditions were: 20% acetonitrile/80% water (0.1% trifluoroacetic acid, v/v) initially, proceeding to 40% acetonitrile/60% water (0.1% trifluoroacetic acid, v/v) in a linear fashion over 9 min.) to give 2-(6-fluoro-1-methyl-1H-indazol-3-yl)-N-(3-methylpyrrolidin-3-yl)-5H-pyrrolo[2,3-b]pyrazine-7-carboxamide hydrochloride (30 mg, 36.5%) as a pale yellow solid. MS: (M+H)$^+$=408; $^1$H NMR (300 MHz, DMSO): δ 9.16 (s, 1H), 8.57-8.41 (m, 4H), 7.92 (s, 1H), 7.75 (d, 1H, J=10.5 Hz), 7.32-7.26 (m, 1H), 6.98-6.93 (m, 1H), 5.75 (d, 2H, J=6.9 Hz), 4.19 (s, 3H), 3.16 (brs, 5H), 1.96 (brs, 3H), 1.61 (s, 3H).

Example 407

2-(6-Chloro-1-methyl-1H-indazol-3-yl)-N-(2-cyanopropan-2-yl)-5H-pyrrolo[2,3-b]pyrazine-7-carboxamide

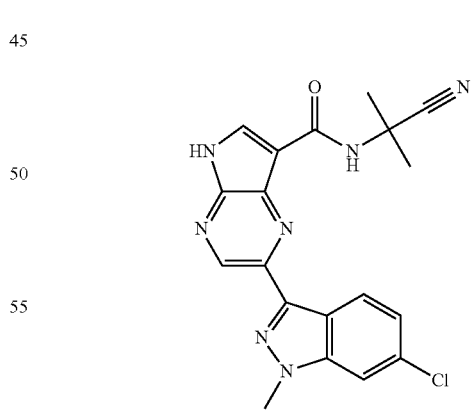

A mixture of 2-(6-chloro-1-methyl-1H-indazol-3-yl)-5H-pyrrolo[2,3-b]pyrazine-7-carboxylic acid (0.07 g, 0.3 mmol), 2-amino-2-methylpropanenitrile hydrochloride (0.05 g, 0.42 mmol), EDCI (0.057 g, 0.3 mmol), DMAP (0.037 g, 0.3 mmol), and DIPEA (0.163 g, 1.26 mmol) in 10 mL of DMF were stirred at room temperature for 5 hours. Then HATU (0.114 g, 0.3 mmol) was added, the final reaction mixture was stirred for additional 15 hours. The solvent was removed under reduced pressure at 70° C., then the residue was triturated with water and ethyl acetate successively then decanted and dried to give 2-(6-chloro-1-methyl-1H-indazol-3-yl)-N-(2-cyanopropan-2-yl)-5H-pyrrolo[2,3-b]pyrazine-7-carboxamide (0.026 g, 31%) as a white solid.

MS: (M+H)⁺=394; ¹H NMR (300 MHz, DMSO): δ 13.04 (s, 1H), 9.13 (s, 1H), 8.57 (s, 1H), 8.50 (d, 1H, J=8.1 Hz), 8.33 (s, 1H), 8.01 (s, 1H), 7.35 (d, 1H, J=8.4 Hz), 4.20 (s, 3H), 1.25 (s, 6H).

Example 408

N-(5-Amino-2-methylpentan-2-yl)-2-(6-fluoro-1-methyl-1H-indazol-3-yl)-5H-pyrrolo[2,3-b]pyrazine-7-carboxamide 2,2,2-trifluoroacetate

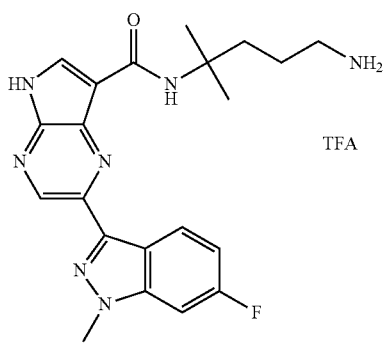 [SMILES: Cn1nc(-c2cnc3[nH]cc(C(=O)NC(C)(C)CCCN)c3n2)c2ccc(F)cc21]

Step 1 tert-Butyl 4-(2-(6-fluoro-1-methyl-1H-indazol-3-yl)-5H-pyrrolo[2,3-b]pyrazine-7-carboxamido)-4-methylpentylcarbamate

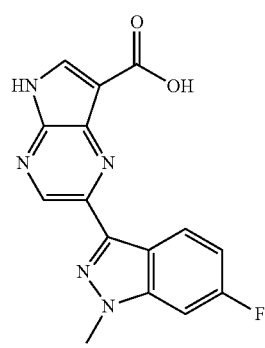

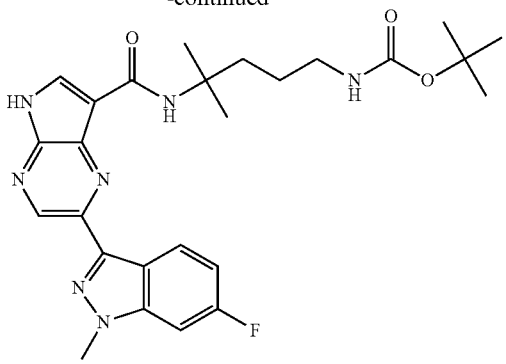

To a stirred solution of 2-(6-fluoro-1-methyl-1H-indazol-3-yl)-5H-pyrrolo[2,3-b]pyrazine-7-carboxylic acid (100 mg, 0.32 mmol) in 6 mL of DMF was added EDCI (123 mmol, 0.64 mmol), DMAP (110 mg, 0.90 mmol) and tert-butyl 4-amino-4-methylpentylcarbamate (139 mg, 0.64 mmol) in one portion at room temperature and the mixture stirred at room temperature for 16 hours. The reaction mixture was poured into 40 mL of water, filtered, the filter cake washed with petroleum ether then dried to give crude tert-butyl 4-(2-(6-fluoro-1-methyl-1H-indazol-3-yl)-5H-pyrrolo[2,3-b]pyrazine-7-carboxamido)-4-methylpentylcarbamate (75 mg, 46%) as a yellow solid. MS: (M+H)⁺=510.2.

Step 2

N-(5-Amino-2-methylpentan-2-yl)-2-(6-fluoro-1-methyl-1H-indazol-3-yl)-5H-pyrrolo[2,3-b]pyrazine-7-carboxamide 2,2,2-trifluoroacetate

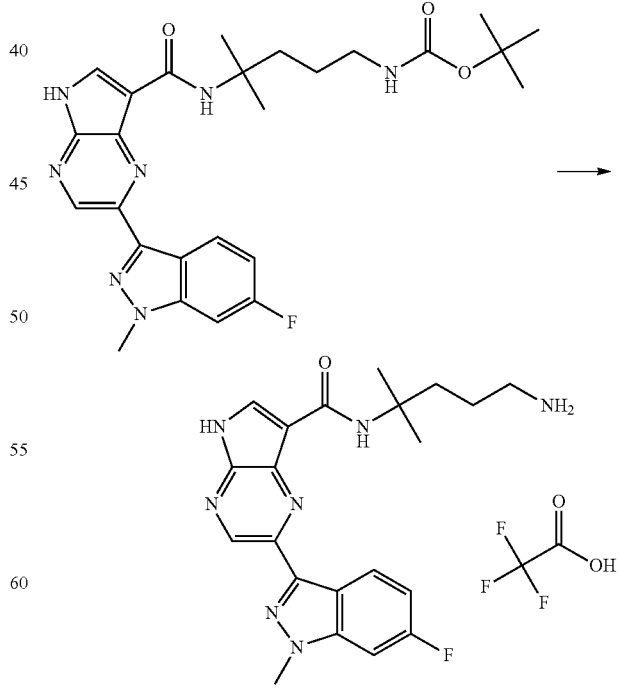

To a stirred solution of tert-butyl 4-(2-(6-fluoro-1-methyl-1H-indazol-3-yl)-5H-pyrrolo[2,3-b]pyrazine-7-carboxamido)-4-methylpentylcarbamate (75 mg, 0.15 mmol) in 6 mL of dichloromethane was added trifluoroacetic acid (3 mL) in one portion at room temperature and the solution stirred for 2 hours. The solvent was evaporated at 40° C. under reduced pressure and the residue was purified by preparative-HPLC (Gemini 5u C18 150×21.2 mm; inject volume: 3 mL/inj, flow rate: 20 mL/min; wavelength: 214 nm and 254 nm; the gradient conditions were: 20% acetonitrile/80% water (0.1% trifluoroacetic acid, v/v) initially, proceeding to 45% acetonitrile/55% water (0.1% trifluoroacetic acid, v/v) in a linear fashion over 9 min.) to give N-(5-amino-2-methylpentan-2-yl)-2-(6-fluoro-1-methyl-1H-indazol-3-yl)-5H-pyrrolo[2,3-b]pyrazine-7-carboxamide 2,2,2-trifluoroacetate (35 mg, 58%) as a pale yellow solid. MS: (M+H)$^+$=410; $^1$H NMR (300 MHz, DMSO): δ 12.98 (s, 1H), 9.11 (s, 1H), 8.49-8.42 (m, 2H), 7.88 (s, 1H), 7.74 (d, 1H, J=9.9 Hz), 7.60 (brs, 3H), 7.20 (t, 1H, J=9.0 Hz), 4.18 (s, 3H), 2.76 (brs, 2H), 2.00-1.94 (m, 2H), 1.61 (brs, 2H), 1.25 (s, 6H).

Example 409

2-(6-Fluoro-1-methyl-1H-indazol-3-yl)-N-(3-methylazetidin-3-yl)-5H-pyrrolo[2,3-b]pyrazine-7-carboxamide 2,2,2-trifluoroacetate

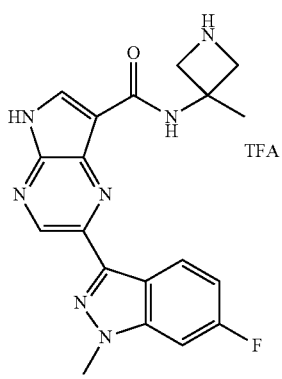 [SMILES: Cn1nc(-c2cnc3[nH]cc(C(=O)NC4(C)CNC4)c3n2)c2ccc(F)cc21]

TFA

Step 1 tert-Butyl 3-(2-(6-fluoro-1-methyl-1H-indazol-3-yl)-5H-pyrrolo[2,3-b]pyrazine-7-carboxamido)-3-methylazetidine-1-carboxylate

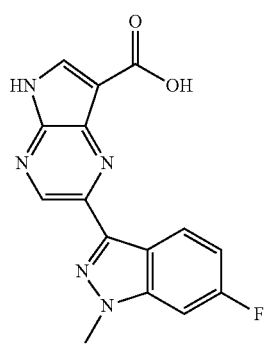

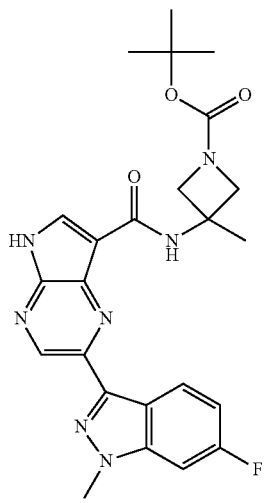

To a stirred solution of 2-(6-fluoro-1-methyl-1H-indazol-3-yl)-5H-pyrrolo[2,3-b]pyrazine-7-carboxylic acid (80 mg, 0.26 mmol) and DIEA (83 mg, 0.64 mmol) in 6 mL of DMF were added EDCI (98 mg, 0.51 mmol) and DMAP (88 mg, 0.72 mmol) at room temperature. 20 minutes later, tert-butyl 3-amino-3-methylazetidine-1-carboxylate (95 mg, 0.51 mmol) was added in one portion and the mixture was stirred at room temperature for 16 hours. The reaction mixture was poured into 40 mL of water, filtered and the filter cake was washed with petroleum ether to give crude tert-butyl 3-(2-(6-fluoro-1-methyl-1H-indazol-3-yl)-5H-pyrrolo[2,3-b]pyrazine-7-carboxamido)-3-methylazetidine-1-carboxylate (75 mg, 76.9%) as a yellow solid. MS: (M+H)$^+$=480.1.

Step 2

2-(6-Fluoro-1-methyl-1H-indazol-3-yl)-N-(3-methylazetidin-3-yl)-5H-pyrrolo[2,3-b]pyrazine-7-carboxamide 2,2,2-trifluoroacetate

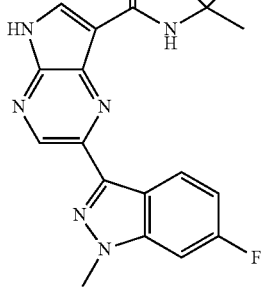

-continued

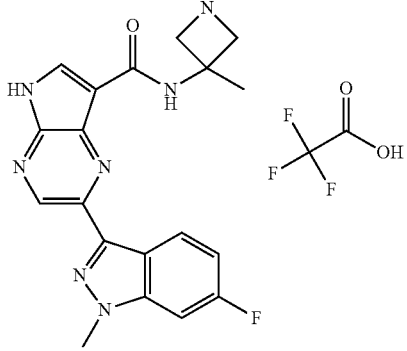
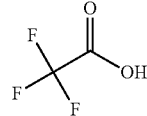

To a stirred solution of tert-butyl 3-(2-(6-fluoro-1-methyl-1H-indazol-3-yl)-5H-pyrrolo[2,3-b]pyrazine-7-carboxamido)-3-methylazetidine-1-carboxylate (75 mg, 0.16 mmol) in 6 mL of dichloromethane was added trifluoroacetic acid (3 mL) in one portion at room temperature. Then the solution was stirred at room temperature for 2 hours. The solvent was evaporated at 40° C. under reduced pressure and the residue was purified by preparative-HPLC (Gemini 5u C18 150×21.2 mm; inject volume: 3 mL/inj, flow rate: 20 mL/min; wavelength: 214 nm and 254 nm; the gradient conditions were: 15% acetonitrile/75% water (0.1% trifluoroacetic acid, v/v) initially, proceeding to 45% acetonitrile/55% water (0.1% trifluoroacetic acid, v/v) in a linear fashion over 9 min.) to give 2-(6-fluoro-1-methyl-1H-indazol-3-yl)-N-(3-methylazetidin-3-yl)-5H-pyrrolo[2,3-b]pyrazine-7-carboxamide 2,2,2-trifluoroacetate (40 mg, 52%) as a pale yellow solid. MS: (M+H)$^+$=380; $^1$H NMR (300 MHz, DMSO): δ 13.04 (brs, 1H), 9.14 (s, 1H), 8.98 (brs, 2H), 8.56-8.51 (m, 2H), 8.38 (s, 1H), 7.72 (dd, 1H, J=9.6, 2.1 Hz), 7.24 (td, J=9.2, 1.8 Hz), 4.57 (d, 1H, J=10.8 Hz), 4.17 (s, 3H), 4.99 (d, 1H, J=10.8 Hz), 1.78 (s, 3H).

Example 410

N-tert-Butyl-2-(1-methyl-1H-indazol-3-yl)-5H-pyrrolo[2,3-b]pyrazine-7-carboxamide

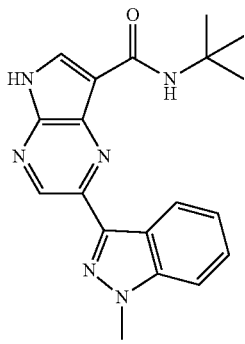 [SMILES: Cn1nc(-c2cnc3[nH]cc(C(=O)NC(C)(C)C)c3n2)c2ccccc21]

Step 1

2-(1-Methyl-1H-indazol-3-yl)-5H-pyrrolo[3,2-b]pyrazine-7-carboxylic acid

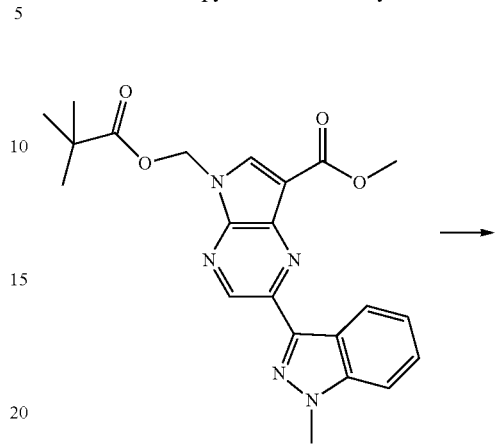

A mixture of methyl 2-(1-methyl-1H-indazol-3-yl)-5-(pivaloyloxymethyl)-5H-pyrrolo[3,2-b]pyrazine-7-carboxylate (150 mg, 0.36 mmol), potassium hydroxide (280 mg, 5 mmol) in 2.5 mL of water and 5 mL of 1,4-dioxane was heated to reflux for 90 mins. The reaction mixture was cooled to room temperature, evaporated, acidified with 1N HCl, then filtered and dried to give 2-(1-methyl-1H-indazol-3-yl)-5H-pyrrolo[3,2-b]pyrazine-7-carboxylic acid (120 mg, crude) as a brown solid. LCMS: (M+H)$^+$=294. Used into the next step without further purification.

Step 2

N-tert-Butyl-2-(1-methyl-1H-indazol-3-yl)-5H-pyrrolo[2,3-b]pyrazine-7-carboxamide 1225
-continued

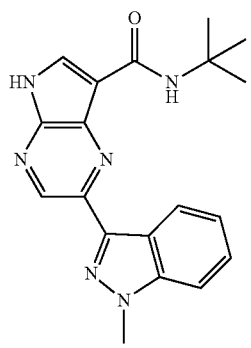

2-(1-Methyl-1H-indazol-3-yl)-5H-pyrrolo[3,2-b]pyrazine-7-carboxylic acid (120 mg, 0.41 mmol), tert-butylamine (0.1 mL, 0.9 mmol) and HATU (233 mg, 0.61 mmol) in 20 mL of dry THF was stirred for 4 hours. The reaction mixture was evaporated to dryness, 20 mL of 0.5N HCl were added to the residue, product extracted with ethyl acetate (3×50 mL), combined organics dried over sodium sulfate and concentrated. The residue was purified by column chromatography (silica gel, 200-300 mesh, eluting with ethyl acetate/petroleum ether=2:1) to give N-tert-butyl-2-(1-methyl-1H-indazol-3-yl)-5H-pyrrolo[2,3-b]pyrazine-7-carboxamide (47 mg, 33.7%). LCMS: (M+H)⁺=349; ¹H NMR (300 MHz, DMSO): δ 12.75 (s, 1H), 9.07 (s, 1H), 8.48 (d, 1H, J=7.8 Hz), 8.35 (s, 1H), 7.96 (s, 1H), 7.5 (d, 1H, J=7.8 Hz), 7.49 (t, 1H, J=7.5 Hz), 7.27-7.22 (m, 1H), 4.17 (s, 3H), 1.52 (s, 9H).

Example 411

N-tert-Butyl-2-(6-fluoro-1H-indazol-3-yl)-5H-pyrrolo[2,3-b]pyrazine-7-carboxamide

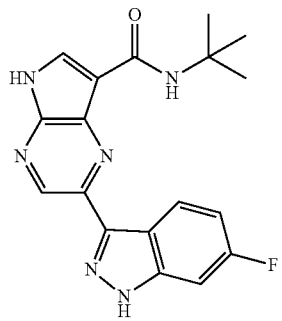 [SMILES: CC(C)(C)NC(=O)c1c[nH]c2ncc(-c3n[nH]c4cc(F)ccc34)nc12]

1226

Step 1

2-Bromo-5H-pyrrolo[2,3-b]pyrazine-7-carboxylic acid

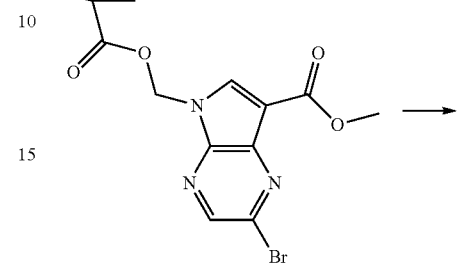

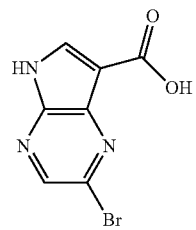

A mixture of methyl 2-bromo-5-(pivaloyloxymethyl)-5H-pyrrolo[2,3-b]pyrazine-7-carboxylate (370 mg, 1 mmol), potassium hydroxide (280 mg, 5 mmol) in 2.5 mL of water and 5 mL of 1,4-dioxane was heated to reflux for 90 mins. The reaction mixture was cooled to room temperature, solvent evaporated, residue acidified with 1N HCl, filtered and dried to give 2-bromo-5H-pyrrolo[2,3-b]pyrazine-7-carboxylic acid as a brown solid (320 mg, crude), material used in the next step without further purification. LCMS: (M+H)⁺=242/244; (M+Na)⁺=264/266.

Step 2

2-Bromo-N-tert-butyl-5H-pyrrolo[2,3-b]pyrazine-7-carboxamide

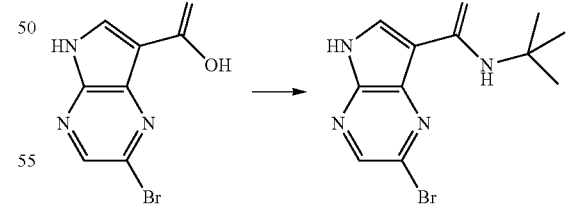

The mixture of 2-bromo-5H-pyrrolo[2,3-b]pyrazine-7-carboxylic acid (320 mg, 0.9 mmol), tert-butylamine (0.5 mL, 4.5 mmol) and HATU (684 mg, 1.8 mmol) in 50 mL of dry THF was stirred for 4 hours at room temperature. The reaction mixture was evaporated to dryness, then the residue was suspended in 50 mL of 0.5 N HCl, product extracted with ethyl acetate (50 mL×3), dried with sodium sulfate, filtered and concentrated to give 2-bromo-N-tert-butyl-5H-pyrrolo[2,3-b]pyrazine-7-carboxamide (258 mg, crude), material used in the next step without further purification. LCMS: (M+H)⁺=297/299; (M+Na)⁺=319/321.

Step 3

6-Fluoro-3-(tributylstannyl)-1H-indazole

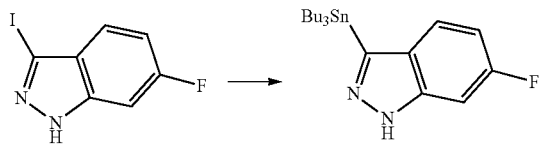

6-Fluoro-3-iodo-1H-indazole (300 mg, 1.1 mmol) in 30 mL of dry THF was cooled to −20° C. under nitrogen atmosphere, then isopropylmagnesium chloride (1.2 mL, 2.42 mmol) was added and mixture stirred for 15 mins at −20° C. Tributylchlorostannane (0.4 mL, 1.32 mmol) was added and the reaction mixture was allowed to warm to room temperature and stirred for 1 h. The reaction was quenched with saturated ammonium chloride, product extracted with ethyl acetate (3×50 mL), dried with sodium sulphate, filtered and concentrated to give 6-fluoro-3-(tributylstannyl)-1H-indazole (500 mg, crude) as a colorless oil which was used directly in the next step without further purification.

Step 4

N-tert-Butyl-2-(6-fluoro-1H-indazol-3-yl)-5H-pyrrolo[2,3-b]pyrazine-7-carboxamide

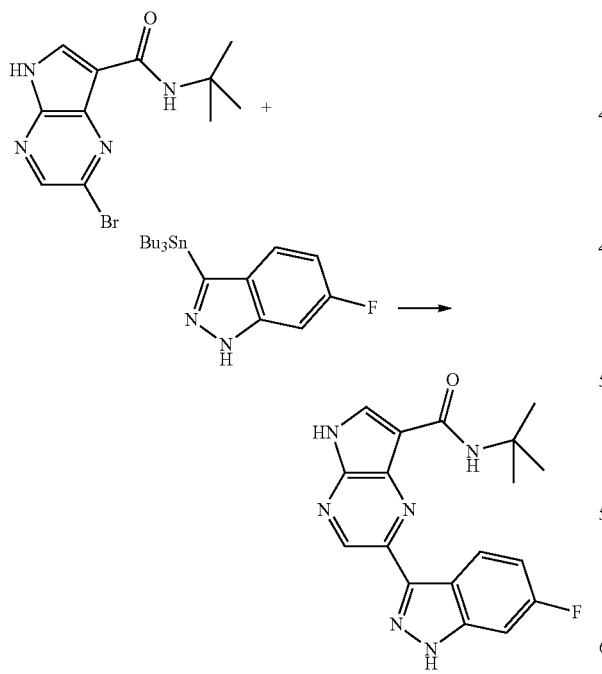

The mixture of 6-fluoro-3-(tributylstannyl)-1H-indazole (500 mg, 1.17 mmol), 2-bromo-N-tert-butyl-5H-pyrrolo[2,3-b]pyrazine-7-carboxamide (258 mg, 0.9 mmol), tetrakis (triphenylphosphine)palladium(0) (20 mg, 0.017 mmol), copper iodide (10 mg 0.052 mmol) in 15 ml of dry DMF was heated to 90° C. for 2.5 hours under nitrogen atmosphere. The reaction mixture was cooled to room temperature, diluted with 50 mL of water and filtered. The solid was washed with dichloromethane and hot methanol, then filtered to give N-tert-butyl-2-(6-fluoro-1H-indazol-3-yl)-5H-pyrrolo[2,3-b]pyrazine-7-carboxamide as a yellow solid (260 mg, 82%). ¹H NMR (300 MHz, DMSO): δ 13.82 (s, 1H), 12.96 (s, 1H), 9.10 (s, 1H), 8.48-8.43 (m, 1H), 8.33 (s, 1H), 7.92 (s, 1H), 7.44-7.41 (m, 1H), 7.12-7.06 (m, 1H), 3.14 (d, 1H, J=5.1 Hz), 1.51 (s, 9H). LCMS: 353.0, [M+H]⁺.

Example 412

N-tert-Butyl-2-(1-methyl-5-(trifluoromethyl)-1H-indazol-3-yl)-5H-pyrrolo[3,2-b]pyrazine-7-carboxamide

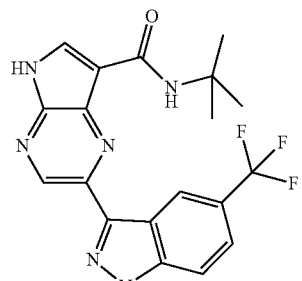

Step 1

3-Iodo-5-(trifluoromethyl)-1H-indazole

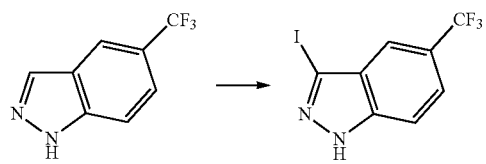 [SMILES: FC(F)(F)c1ccc2[nH]ncc2c1 ; FC(F)(F)c1ccc2[nH]nc(I)c2c1]

To a solution of 6-fluoro-1H-indazole (2.5 g, 13.4 mmol) in DMSO (20 mL) was added KOH (2.3 g, 40.6 mmol) and I₂ (4.3 g, 26.8 mmol) successively at 0° C., then the reaction mixture was stirred at room temperature for 5 hours. Water (60 mL) was added, the precipitate was collected by filtration and washed with water (30 mL), then dried to afford 3-iodo- 5-(trifluoromethyl)-1H-indazole (4.0 g, 95.2%) as an off-white solid. LCMS: (M+H)⁺=313.

Step 2

3-Iodo-1-methyl-5-(trifluoromethyl)-1H-indazole

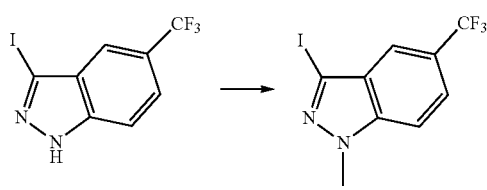

To a solution of 3-iodo-5-(trifluoromethyl)-1H-indazole (4.0 g, 12.8 mmol) in THF (80 mL) was added t-BuOK (2.0 g, 17.9 mmol) slowly at 0° C. and mixture stirred for 30 minutes, iodomethane (1.1 mL, 17.9 mmol) was added at 0° C., then warmed to room temperature and stirred for 1.5 hours, quenched with water (30 mL) and extracted with EtOAc (3×30 mL), the organic layer was dried over Na₂SO₄ and concentrated under reduced pressure. The crude product was washed with ether (5 mL) and filtered to give 3-iodo-1-methyl-5-(trifluoromethyl)-1H-indazole (3.3 g, 79.3%) as a white solid. LCMS: (M+H)⁺=327.

Step 3

1-Methyl-3-(tributylstannyl)-5-(trifluoromethyl)-1H-indazole

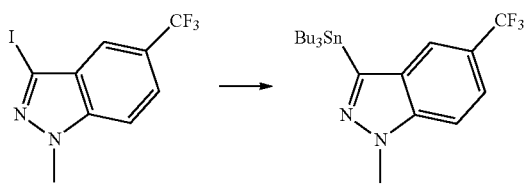

To a solution of 3-iodo-1-methyl-5-(trifluoromethyl)-1H-indazole (400 mg, 1.2 mmol) in dry THF (15 mL) was added isopropylmagnesium chloride (0.7 mL, 1.3 mmol, 2 M in THF) drop-wise at −16° C. under nitrogen atmosphere, stirred for 30 minutes, then tributylchlorostannane (0.4 mL, 1.3 mmol) was added drop-wise at −16° C. under nitrogen, the reaction mixture was warmed to room temperature slowly and stirred for 2 hours, then quenched with a solution of saturated NH₄Cl (40 mL) and product extracted with EtOAc (3×30 mL) then dried over Na₂SO₄, filtered and concentrated, under reduced pressure to give 1-methyl-3-(tributylstannyl)-5-(trifluoromethyl)-1H-indazole (500 mg, crude) as an oil which was used directly to next step without any further purification.

Step 4

Methyl 2-(1-methyl-5-(trifluoromethyl)-1H-indazol-3-yl)-5-(pivaloyloxymethyl)-5H-pyrrolo[3,2-b]pyrazine-7-carboxylate

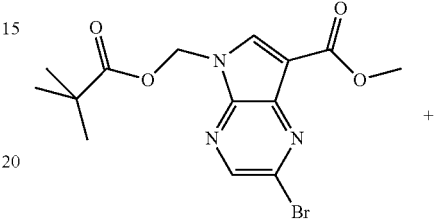

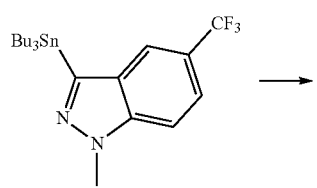

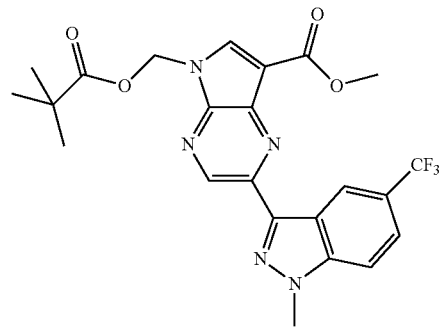

To a solution of methyl 2-bromo-5-(pivaloyloxymethyl)-5H-pyrrolo[3,2-b]pyrazine-7-carboxylate (300 mg, 0.81 mmol) and 1-methyl-3-(tributylstannyl)-5-(trifluoromethyl)-1H-indazole (396 mg, 0.89 mmol) in DMF (10 mL) were added CuI (30 mg, 0.16 mmol) and Pd(PPh₃)₄ (47 mg, 0.041 mmol), the reaction mixture was degassed by bubbling nitrogen for 3 minutes and refilled with nitrogen. The mixture was heated to 80° C. for 5 hours under nitrogen, after cooling, water (50 mL) was added to the mixture and product extracted with EtOAc (3×40 mL), the combined organic layers were dried over Na₂SO₄, concentrated under reduced pressure and the residue was triturated with petroleum ether (2 mL) then decanted and dried to give methyl 2-(1-methyl-5-(trifluoromethyl)-1H-indazol-3-yl)-5-(pivaloyloxymethyl)-5H-pyrrolo[3,2-b]pyrazine-7-carboxylate (280 mg, 70.7%) as an orange solid. LCMS: (M+H)$^+$=490.

Step 5

2-(1-Methyl-5-(trifluoromethyl)-1H-indazol-3-yl)-5H-pyrrolo[3,2-b]pyrazine-7-carboxylic acid

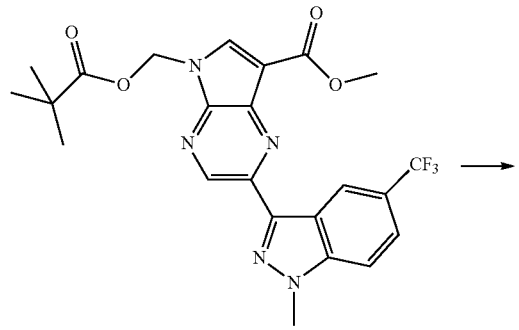

To a suspension of methyl 2-(1-methyl-5-(trifluoromethyl)-1H-indazol-3-yl)-5-(pivaloyloxymethyl)-5H-pyrrolo[3,2-b]pyrazine-7-carboxylate (50 mg, 0.1 mmol) in dioxane/water (4 mL/4 mL) was added NaOH (40 mg, 1.0 mmol), the reaction mixture was heated to 90° C. with stirring for 7 hours, the dioxane was removed under reduced pressure, the aqueous layer was adjusted to pH=3 with 1 N HCl, the precipitate was collected by filtration and washed with water (5 mL) and dried to afford 2-(1-methyl-5-(trifluoromethyl)-1H-indazol-3-yl)-5H-pyrrolo[3,2-b]pyrazine-7-carboxylic acid (40 mg, crude) as an orange solid. LCMS: (M+H)$^+$=362.

Step 6

N-tert-Butyl-2-(1-methyl-5-(trifluoromethyl)-1H-indazol-3-yl)-5H-pyrrolo[3,2-b]pyrazine-7-carboxamide

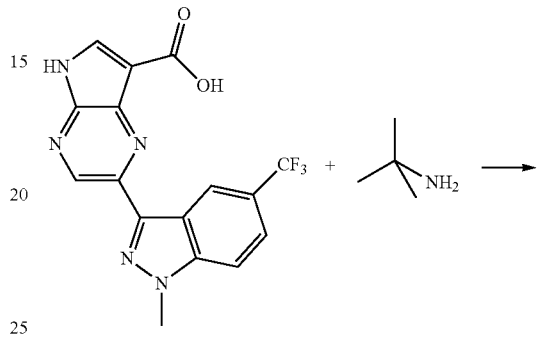

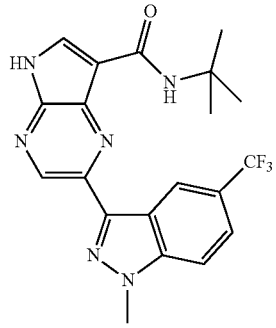

A mixture of 2-(1-methyl-5-(trifluoromethyl)-1H-indazol-3-yl)-5H-pyrrolo[3,2-b]pyrazine-7-carboxylic acid (100 mg, 0.28 mmol), 2-methylpropan-2-amine (20 mg, 0.28 mmol), HOBt (149 mg, 1.12 mmol), EDCI (211 mg, 1.12 mmol) and triethylamine (133 mg, 1.12 mmol) in dichloromethane (15 mL) was stirred at room temperature for 15 hours, then water (30 mL) was added, product extracted with dichloromethane (3×30 mL), the combined organic layers were concentrated and the residue was purified by column chromatography (silica gel, 200-300 mesh, eluting with petroleum ether/ethyl acetate=10:1) to give N-tert-butyl-2-(1-methyl-5-(trifluoromethyl)-1H-indazol-3-yl)-5H-pyrrolo[3,2-b]pyrazine-7-carboxamide (18 mg, 15.6%) as an orange solid. LCMS: (M+H)$^+$=417; $^1$H NMR (300 MHz, DMSO): δ 12.89 (s, 1H), 9.06 (s, 1H), 8.71 (s, 1H), 8.44 (s, 1H), 8.05 (d, 1H, J=9.0 Hz), 7.93 (s, 1H), 7.84 (d, 1H, J=9.0 Hz), 4.28 (s, 3H), 1.47 (s, 9H).

Example 413

2-(6-Chloro-1-methyl-1H-indazol-3-yl)-N-(3-hydroxy-2-methylbutan-2-yl)-5H-pyrrolo[2,3-b]pyrazine-7-carboxamide

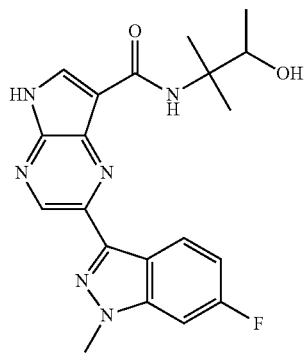 [SMILES: CC(O)C(C)(C)NC(=O)c1c[nH]c2ncc(-c3nn(C)c4cc(F)ccc34)nc12]

Step 1

3-Azido-3-methylbutan-2-one

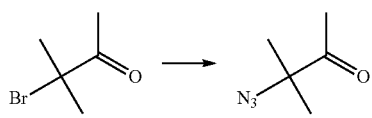

A stirred solution of 3-bromo-3-methylbutan-2-one (1 g, 6.1 mmol) in 50 mL of acetone and 5 mL of water was treated with NaN₃ (0.4 g, 6.1 mmol). The reaction mixture was stirred at reflux for 18 hours and then evaporated to dryness. The residue was partitioned between ethyl acetate and water and the organic layer was washed with brine, evaporated to dryness to give 3-azido-3-methylbutan-2-one (0.5 g, 65%) which was used in the next step without further purification. LCMS: No molecular ion observed for desired mass.

Step 2

3-Amino-3-methylbutan-2-ol

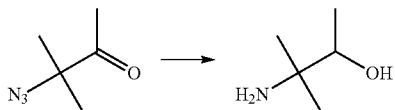

To a suspension of LiAlH₄ (0.4 g, 11 mmol) in 30 mL of dry THF, 3-azido-3-methylbutan-2-one (0.5 g, 3.9 mmol) was added portion-wise at room temperature. After 4 hours, the reaction was quenched by adding 5 mL of water, filtered and the filter cake washed with methanol. The filtrate was concentrated to give 3-amino-3-methylbutan-2-ol (0.32 g, 79.0%) as colorless oil. MS: (M+H)⁺=104.2; ¹H NMR (300 MHz, CD₃OD): δ 3.69 (q, 1H, J=6.6 Hz), 1.29 (s, 3H), 1.25 (s, 3H), 1.20 (d, 3H, J=6.6 Hz).

Step 3

2-(6-Chloro-1-methyl-1H-indazol-3-yl)-N-(3-hydroxy-2-methylbutan-2-yl)-5H-pyrrolo[2,3-b]pyrazine-7-carboxamide

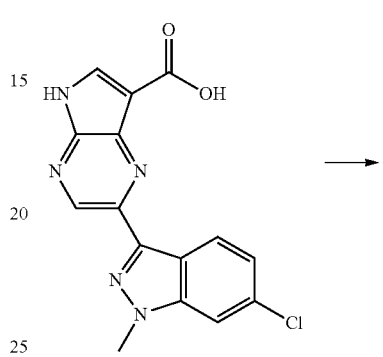

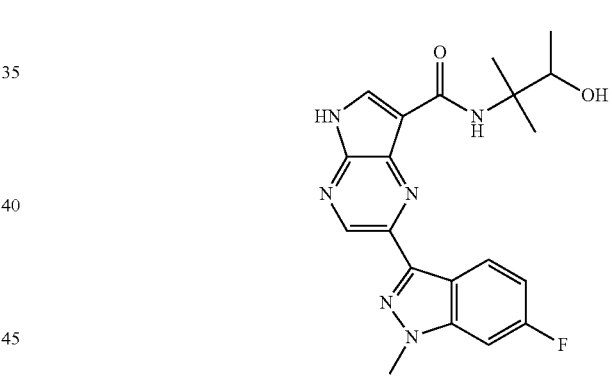

A mixture of 2-(6-chloro-1-methyl-1H-indazol-3-yl)-5H-pyrrolo[2,3-b]pyrazine-7-carboxylic acid (0.07 g, 0.3 mmol), 3-amino-3-methylbutan-2-ol (0.05 g, 0.49 mmol), EDCI (0.057 g, 0.3 mmol), DMAP (0.037 g, 0.3 mmol), HOBT (0.041 g, 0.3 mmol) and DIPEA (0.163 g, 1.26 mmol) in 10 mL of DMF was stirred at room temperature overnight. The solvent was removed under reduced pressure at 70° C., the residue was triturated with water and then purified by preparative-HPLC (Gemini 5u C18 150×21.2 mm; inject volume: 3 mL/inj, flow rate: 20 mL/min; wavelength: 214 nm and 254 nm; the gradient conditions were: 15% acetonitrile/75% water (0.1% trifluoroacetic acid, v/v) initially, proceeding to 70% acetonitrile/30% water (0.1% trifluoroacetic acid, v/v) in a linear fashion over 9 min.) to give 2-(6-chloro-1-methyl-1H-indazol-3-yl)-N-(3-hydroxy-2-methylbutan-2-yl)-5H-pyrrolo[2,3-b]pyrazine-7-carboxamide (0.025 g, 28%) as a yellow solid. MS: (M+H)⁺=413; ¹H NMR (300 MHz, DMSO): δ 12.85 (s, 1H), 9.12 (s, 1H), 8.66 (d, 1H, J=8.7 Hz), 8.41 (s, 1H), 8.00-7.96 (m, 1H), 7.33 (dd, 1H, J=8.7, 1.5 Hz), 5.17 (d, 1H, J=5.7 Hz), 4.20 (s, 1H), 4.04-4.00 (m, 1H), 1.48 (s, 6H), 1.17 (d, 3H, J=6.6 Hz).

Example 414

2-(6-Chloro-1H-indazol-3-yl)-N-(1-hydroxy-2-methylpropan-2-yl)-5H-pyrrolo[3,2-b]pyrazine-7-carboxamide

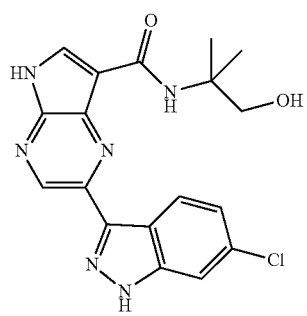 [SMILES: CC(C)(CO)NC(=O)c1c[nH]c2ncc(-c3n[nH]c4cc(Cl)ccc34)nc12]

Step 1

6-Chloro-3-iodo-1H-indazole

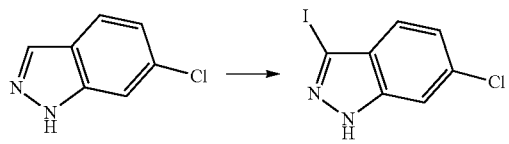 [SMILES: Clc1ccc2cn[nH]c2c1 ; Clc1ccc2c(I)n[nH]c2c1]

A mixture of 6-chloro-1H-indazole (2 g, 13.1 mmol), KOH (2.2 g, 39.3 mmol) and I₂ (6.6 g, 26.2 mmol) in dry DMF (20 mL) was heated to 30° C. for 16 hours. Reaction quenched with water, product was extracted with ethyl acetate (150 mL), organic phase washed with water (3×10 mL), brine (2×10 mL) and dried over Na₂SO₄, then filtered and concentrated to afford 6-chloro-3-iodo-1H-indazole (3.0 g, 83%) as a yellow solid. LCMS: (M+H)⁺=279.

Step 2

6-Chloro-3-(tributylstannyl)-1H-indazole

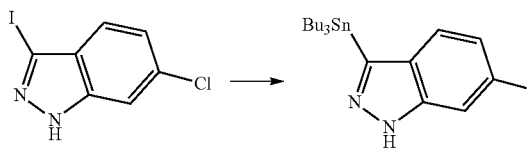

To a solution of 6-chloro-3-iodo-1H-indazole (337 mg, 1.21 mmol) in dry tetrahydrofuran (20 mL) was added drop-wise isopropylmagnesium chloride (1.33 mL, 2M in THF, 2.66 mmol) at −16° C. under N₂ atmosphere. After stirring for 20 minutes, tributylchlorostannane (472 mg, 1.45 mmol) was added drop-wise at −16° C., and then it was warmed to 20° C. for 2 h. Then NH₄Cl solution (2 mL) was added and product extracted with dichloromethane (15 mL), organic phase was washed with water (2×20 mL) and brine (2×20 mL). The organic layer was dried over Na₂SO₄, filtered and concentrated to afford 6-chloro-3-(tributylstannyl)-1H-indazole (413 mg, crude) as yellow oil which was used to next step without further purification.

Step 3

Methyl 2-(6-chloro-1H-indazol-3-yl)-5-(pivaloyloxymethyl)-5H-pyrrolo[3,2-b]pyrazine-7-carboxylate

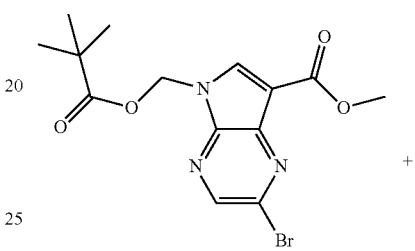

+

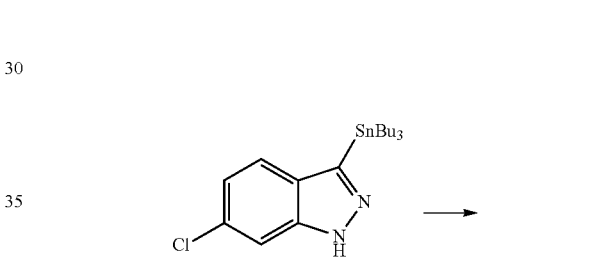

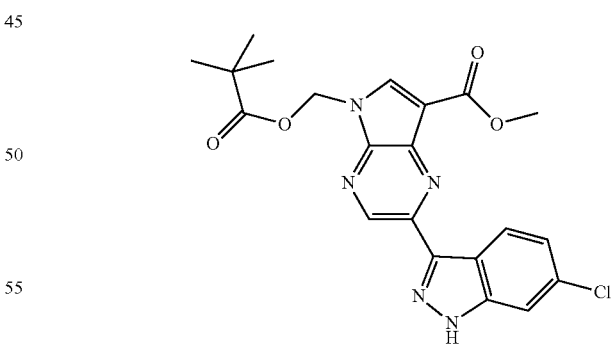

A mixture of methyl 2-bromo-5-(pivaloyloxymethyl)-5H-pyrrolo[3,2-b]pyrazine-7-carboxylate (0.26 g, 0.7 mmol), 6-chloro-3-(tributylstannyl)-1H-indazole (0.31 g, 0.7 mmol), Pd(PPh₃)₄ (81 mg, 0.07 mmol) and CuI (27 mg, 0.14 mmol) in dry DMF (3 mL) was heated to 90° C. for 3 hours. Product was extracted with ethyl acetate (60 mL), and organic phase washed with water (3×10 mL) and brine (2×10 mL), dried over Na₂SO₄, filtered and concentrated to afford methyl 2-(6- chloro-1H-indazol-3-yl)-5-(pivaloyloxymethyl)-5H-pyrrolo[3,2-b]pyrazine-7-carboxylate (265 mg, crude) as a brown oil. LCMS: (M+H)⁺=442.

Step 4

2-(6-Chloro-1H-indazol-3-yl)-5H-pyrrolo[3,2-b]pyrazine-7-carboxylic acid

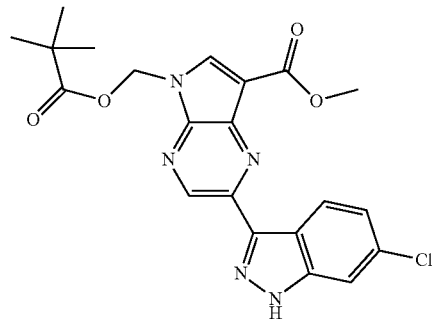

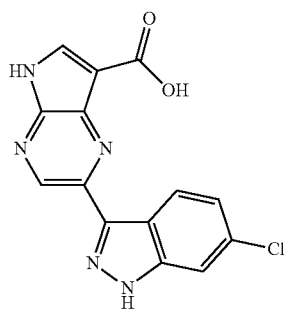

A mixture of methyl 2-(6-chloro-1H-indazol-3-yl)-5-(pivaloyloxymethyl)-5H-pyrrolo[3,2-b]pyrazine-7-carboxylate (202 mg, 0.457 mmol) and KOH (385 mg, 6.86 mmol) in 1,4-dioxane (10 mL) and water (5 mL) was heated to reflux for 3 hours. Reaction mixture was concentrated and the residue was adjusted to pH=5 with 1.0 M HCl aqueous. The precipitate was collected by filtration and dried to afford 2-(6-chloro-1H-indazol-3-yl)-5H-pyrrolo[3,2-b]pyrazine-7-carboxylic acid (178 mg, crude) as a yellow solid. LCMS: (M+H)⁺=314.

Step 5

2-(6-Chloro-1H-indazol-3-yl)-N-(1-hydroxy-2-methylpropan-2-yl)-5H-pyrrolo[3,2-b]pyrazine-7-carboxamide

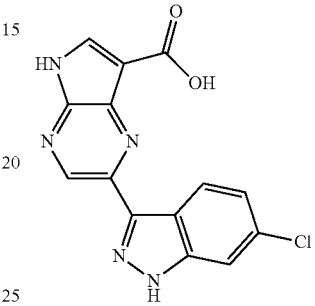

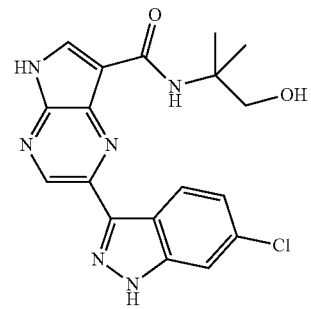

A mixture of 2-(6-chloro-1H-indazol-3-yl)-5H-pyrrolo[3,2-b]pyrazine-7-carboxylic acid (140 mg, 0.446 mmol), 2-amino-2-methylpropan-1-ol (48 mg, 0.536 mmol), EDCI (256 mg, 1.338 mmol), HOBt (181 mg, 1.338 mmol) and DIPEA (173 mg, 1.338 mmol) in dry DMF (5 mL) was stirred for 16 hours at room temperature. Water (5 mL) was added and the formed precipitate was separated by filtration, then was purified by preparative-HPLC (Gemini 5u C18 150×21.2 mm; inject volume: 3 mL/inj, flow rate: 20 mL/min; wavelength: 214 nm and 254 nm; the gradient conditions are: 35% acetonitrile/65% water (0.1% trifluoroacetic acid V/V) initially, and then proceed to 50% acetonitrile/50% water (0.1% trifluoroacetic acid V/V) in a linear fashion after just 9 min) to afford 2-(6-chloro-1H-indazol-3-yl)-N-(1-hydroxy-2-methylpropan-2-yl)-5H-pyrrolo[3,2-b]pyrazine-7-carboxamide (6 mg, 3%) as a white solid. LCMS: (M+H)⁺=385; ¹H NMR (300 MHz, DMSO+D$_2$O): δ 9.09 (s, 1H), 8.52 (d, 1H, J=8.4 Hz), 8.31 (s, 1H), 7.72 (s, 1H), 7.25 (d, 1H, J=9.0 Hz), 3.59 (s, 2H), 1.41 (s, 6H).

Example 415

N-(4-Amino-2-methylbutan-2-yl)-2-(6-fluoro-1-methyl-1H-indazol-3-yl)-5H-pyrrolo[2,3-b]pyrazine-7-carboxamide 2,2,2-trifluoroacetate

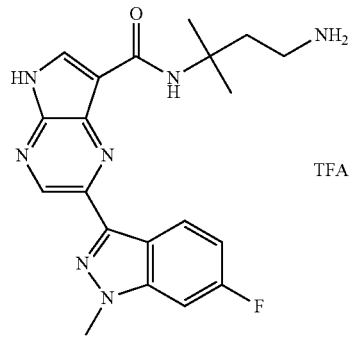 [SMILES: Cn1nc(-c2cnc3[nH]cc(C(=O)NC(C)(C)CCN)c3n2)c2ccc(F)cc21]

Step 1 tert-Butyl 3-(2-(6-fluoro-1-methyl-1H-indazol-3-yl)-5H-pyrrolo[2,3-b]pyrazine-7-carboxamido)-3-methylbutylcarbamate

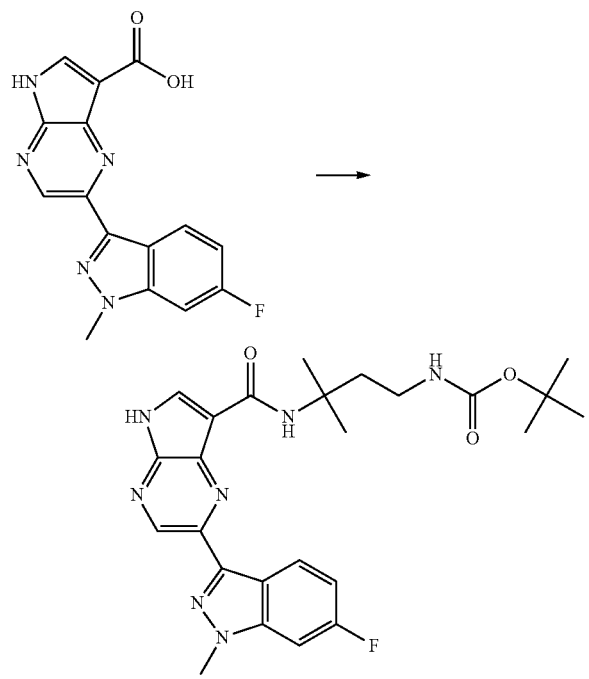

To a stirred solution of 2-(6-fluoro-1-methyl-1H-indazol-3-yl)-5H-pyrrolo[2,3-b]pyrazine-7-carboxylic acid (100 mg, 0.32 mmol) and DIEA (124 mg, 0.96 mmol) in 6 mL of DMF was added EDCI (123 mg, 0.64 mmol) and DMAP (110 mg, 0.90 mmol) at room temperature followed by tert-butyl 3-amino-3-methylbutylcarbamate (260 mg, 1.28 mmol) in one portion and the mixture was stirred at room temperature for 16 hours. The reaction mixture was poured into 40 mL of water, filtered and the filter cake was washed with petroleum ether to give tert-butyl 3-(2-(6-fluoro-1-methyl-1H-indazol-3-yl)-5H-pyrrolo[2,3-b]pyrazine-7-carboxamido)-3-methylbutylcarbamate (110 mg, 69.4%) as a yellow solid which was used for the next step without further purification. MS: (M+H)$^+$=496.2.

Step 2

N-(4-Amino-2-methylbutan-2-yl)-2-(6-fluoro-1-methyl-1H-indazol-3-yl)-5H-pyrrolo[2,3-b]pyrazine-7-carboxamide 2,2,2-trifluoroacetate

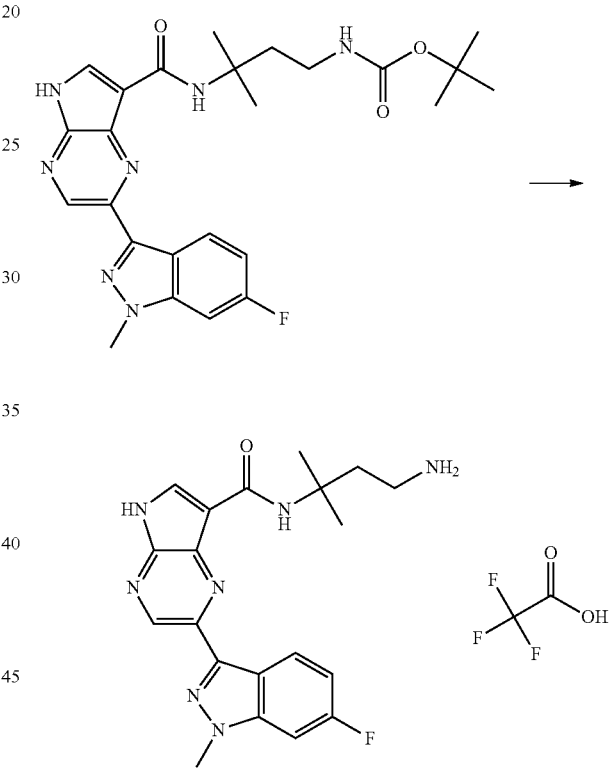

To a stirred solution of tert-butyl 3-(2-(6-fluoro-1-methyl-1H-indazol-3-yl)-5H-pyrrolo[2,3-b]pyrazine-7-carboxamido)-3-methylbutylcarbamate (110 mg, 0.22 mmol) in 6 mL of dichloromethane was added trifluoroacetic acid (3 mL) in one portion at room temperature and the solution stirred for one hour. The solvent was evaporated at 40° C. under reduced pressure and the residue was purified by preparative-HPLC (Gemini 5u C18 150×21.2 mm; inject volume: 3 mL/inj, flow rate: 20 mL/min; wavelength: 214 nm and 254 nm; the gradient conditions were: 20% acetonitrile/80% water (0.1% trifluoroacetic acid, v/v) initially, proceeding to 50% acetonitrile/50% water (0.1% trifluoroacetic acid, v/v) in a linear fashion over 9 min.) to give N-(4-amino-2-methylbutan-2-yl)-2-(6-fluoro-1-methyl-1H-indazol-3-yl)-5H-pyrrolo[2,3-b]pyrazine-7-carboxamide 2,2,2-trifluoroacetate (35 mg, 30.9%) as a yellow solid. MS: (M+H)$^+$=396; $^1$H NMR (300 MHz, DMSO): δ 12.94 (s, 1H), 9.11 (s, 1H), 8.50-8.43 (m, 2H), 7.89 (s, 1H), 7.74-7.70 (m, 3H), 7.70-7.21 (m, 1H), 4.18 (s, 3H), 2.90 (brs, 2H), 2.31-2.26 (m, 2H), 1.53 (s, 6H).

Examples 416 and 417

N-(trans-4-Amino-1-methylcyclohexyl)-2-(6-fluoro-1-methyl-1H-indazol-3-yl)-5H-pyrrolo[2,3-b]pyrazine-7-carboxamide hydrochloride and N-(cis-4-amino-1-methylcyclohexyl)-2-(6-fluoro-1-methyl-1H-indazol-3-yl)-5H-pyrrolo[2,3-b]pyrazine-7-carboxamide hydrochloride

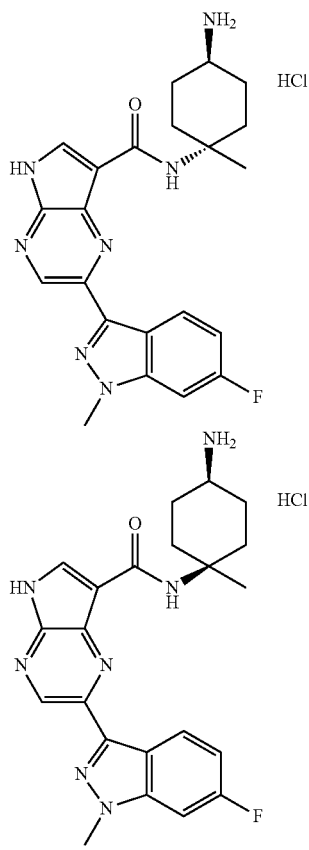

Step 1 tert-Butyl trans-4-hydroxycyclohexylcarbamate

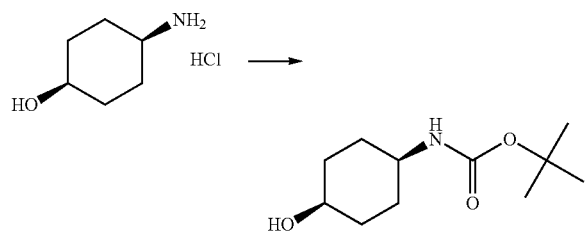

To a solution of trans-4-aminocyclohexanol hydrochloride (15.1 g, 0.1 mol) and Boc$_2$O (23.7 g, 0.11 mol) in THF (100 mL) was added in one portion a solution of NaHCO$_3$ (10.6 g, 0.1 mol) in water (10 mL). The resulting mixture was stirred at room temperature for 15 hours. Excess of solvent was removed under reduced pressure; the residue was extracted by EtOAc (3×100 mL), combined organics washed with brine, dried over Na$_2$SO$_4$ and concentrated to give crude tert-butyl trans-4-hydroxycyclohexylcarbamate (20.1 g, 94%) as white solid which was used for the next step without further purification. MS: (M+Na)$^+$=238.2.

Step 2 tert-Butyl 4-oxocyclohexylcarbamate

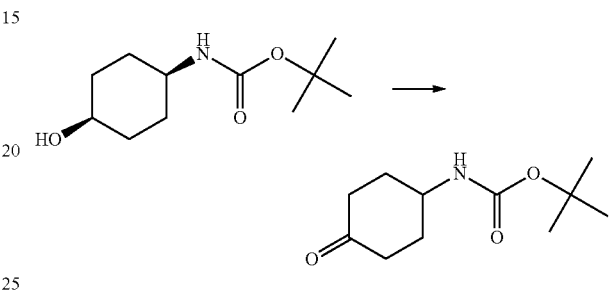

To a stirred solution of tert-butyl trans-4-hydroxycyclohexylcarbamate (2.0 g, 9.3 mmol) in 100 mL of dichloromethane was added PCC (3.0 g, 14 mmol) and celite (5.0 g). The reaction mixture was stirred at room temperature overnight. The reaction mixture was filtered through a celite pad and the residue concentrated under reduced pressure. The crude compound was purified by column chromatography (silica gel, 200-300 mesh, eluting with a mixture of ethyl acetate and petroleum ether (1:1, v/v) to give tert-butyl 4-oxo-cyclohexylcarbamate (1.6 g, 80%) as a white solid. $^1$H NMR (300 MHz, CDCl$_3$): δ 4.52 (brs, 1H), 3.94 (brs, 1H), 2.45-2.40 (m, 4H), 2.20-2.27 (m, 2H), 1.74-1.63 (m, 2H), 1.46 (s, 9H).

Step 3 tert-Butyl 4-(tert-butylsulfinylimino)cyclohexylcarbamate

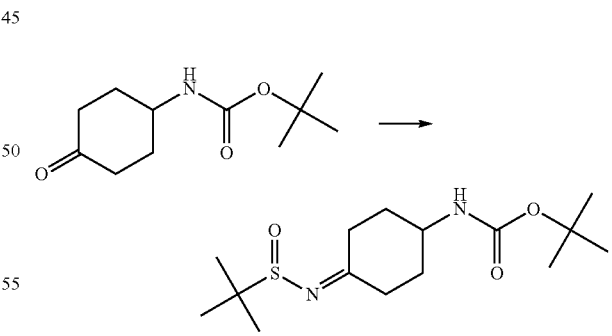

A mixture of tert-butyl 4-oxocyclohexylcarbamate (1.0 g, 4.7 mmol), 2-methylpropane-2-sulfinamide (0.63 g, 5.17 mmol) and Ti(OEt)$_4$ (2.1 g, 9.2 mmol) in 10 mL of THF was stirred at 50-60° C. overnight. The mixture was cooled to room temperature and the residue purified by column chromatography (silica gel, 200-300 mesh, eluting with a mixture of petroleum ether and ethyl acetate (4:1, v/v) to give tert-butyl 4-(tert-butylsulfinylimino)cyclohexylcarbamate (1.0 g, 67%) as an clear oil. MS: (M+H)$^+$=317.3; $^1$H NMR (300

MHz, CDCl₃): δ 4.88-4.86 (m, 1H), 3.83 (brs, 1H), 3.39-3.38 (m, 1H), 2.62-2.15 (m, 5H), 1.68-1.53 (m, 2H), 1.43 (s, 9H), 1.24 (s, 9H).

Step 4 tert-Butyl 4-(1,1-dimethylethylsulfinamido)-4-methylcyclohexylcarbamate

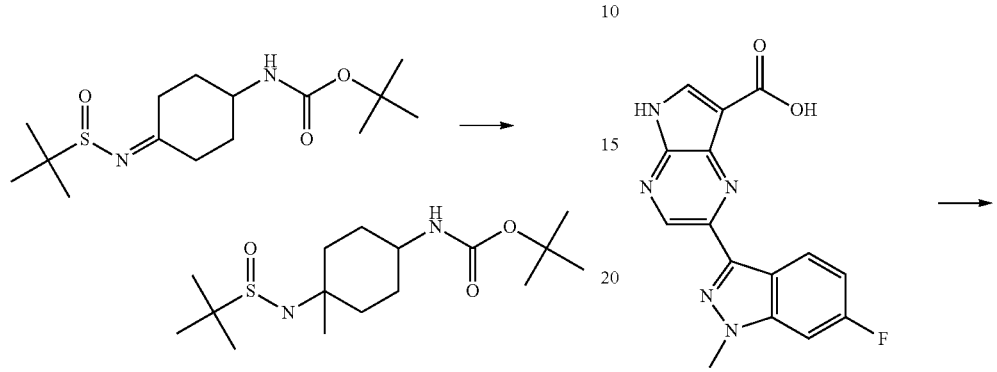

To a stirred solution of tert-butyl 4-(tert-butylsulfinylimino)cyclohexylcarbamate (0.6 g, 1.9 mmol) in 40 mL of toluene at −78° C. was added, under a nitrogen atmosphere, a solution of Me₃Al 2M in toluene (2 mL, 4 mmol). The mixture was stirred for 20 minutes at −78° C., then a solution of MeLi, 3M in dimethoxymethane (2.8 mL, 8.4 mmol), was added slowly and the reaction mixture was stirred at −78° C. for 4 hours. The reaction was quenched by adding 2 mL of water and the solvents evaporated under reduced pressure. The residue was passed through a pad of silica gel (200-300 mesh, eluting with a mixture of petroleum ether and ethyl acetate (4:1, v/v) to give tert-butyl 4-(1,1-dimethylethylsulfinamido)-4-methylcyclohexylcarbamate (0.21 g, 33%) as crude yellow oil which was used for the next step without further purification. MS: (M+H)⁺=333.2.

Step 5 tert-Butyl 4-amino-4-methylcyclohexylcarbamate hydrochloride

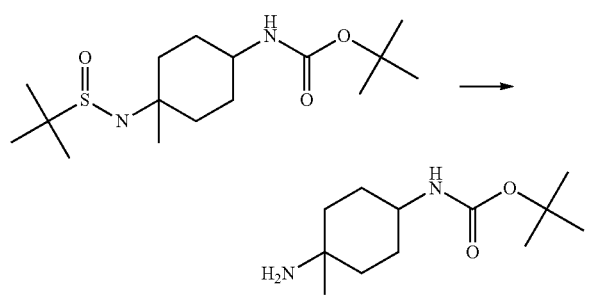

To a stirred solution of tert-butyl 4-(1,1-dimethylethylsulfinamido)-4-methylcyclohexylcarbamate (0.2 g, 0.6 mmol) in 100 mL of MeOH was added a saturated solution of HCl (g) in dioxane (0.72 mL). The solution was stirred at room temperature overnight. The solvent was removed under reduced pressure, the residue was triturated with EtOAc (15 mL), then decanted and dried to give tert-butyl 4-amino-4-methylcyclohexylcarbamate hydrochloride (0.1 g, 63%) as a white solid. MS: (M+H)⁺=229.2. ¹H NMR (300 MHz, CD₃OD): δ 3.36 (m, 1H), 1.91-1.66 (m, 9H), 1.40 (s, 9H), 1.18 (s, 3H).

Step 6 tert-Butyl 4-(2-(6-fluoro-1-methyl-1H-indazol-3-yl)-5H-pyrrolo[2,3-b]pyrazine-7-carboxamido)-4-methylcyclohexylcarbamate

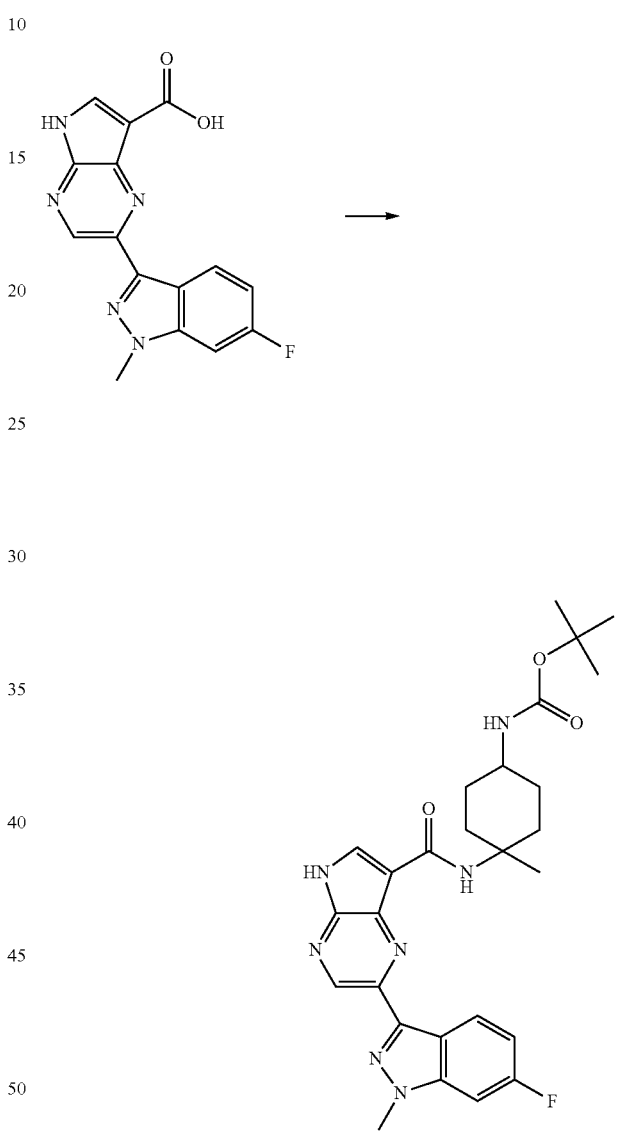

A mixture of 2-(6-fluoro-1-methyl-1H-indazol-3-yl)-5H-pyrrolo[2,3-b]pyrazine-7-carboxylic acid (0.08 g, 0.26 mmol), tert-butyl 4-amino-4-methylcyclohexylcarbamate hydrochloride (0.07 g, 0.26 mmol), EDCI (0.076 g, 0.4 mmol), DMAP (0.05 g, 0.4 mmol), HOBT (0.054 g, 0.4 mmol) and DIPEA (0.206 g, 1.6 mmol) in 20 mL of DMF was stirred at room temperature overnight. The solvent was removed under reduced pressure and the residue was passed through a pad of silica gel (200-300 mesh, eluting with a mixture of petroleum ether and ethyl acetate (4:1, v/v) to give tert-butyl 4-(2-(6-fluoro-1-methyl-1H-indazol-3-yl)-5H-pyrrolo[2,3-b]pyrazine-7-carboxamido)-4-methylcyclohexylcarbamate (0.065 g, 49%) as a white solid which was used for the next step without further purification. MS: (M+H)⁺=522.2.

Step 7

N-(trans-4-amino-1-methylcyclohexyl)-2-(6-fluoro-1-methyl-1H-indazol-3-yl)-5H-pyrrolo[2,3-b]pyrazine-7-carboxamide hydrochloride and N-(cis-4-amino-1-methylcyclohexyl)-2-(6-fluoro-1-methyl-1H-indazol-3-yl)-5H-pyrrolo[2,3-b]pyrazine-7-carboxamide hydrochloride

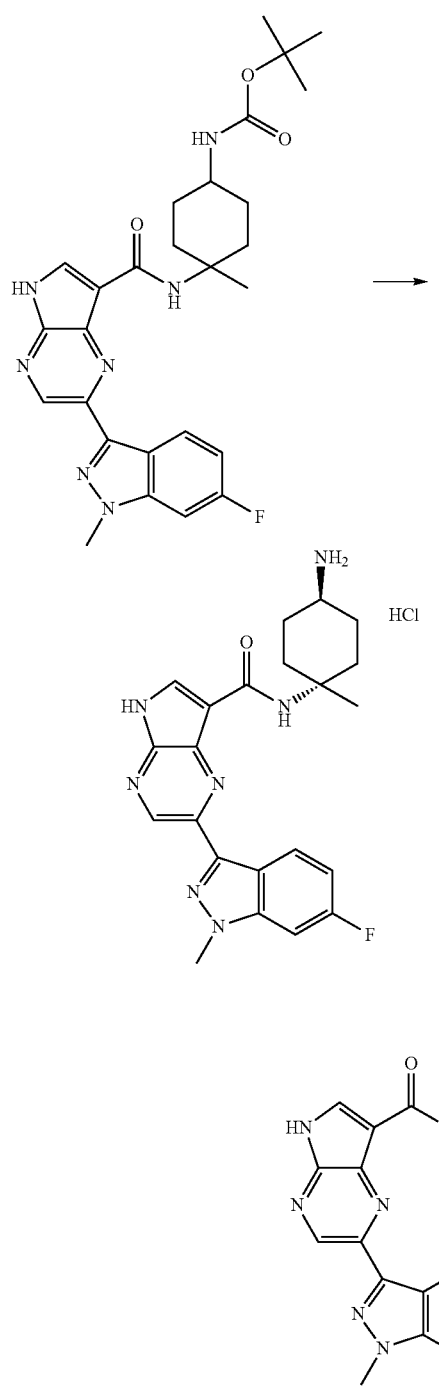

tert-Butyl 4-(2-(6-fluoro-1-methyl-1H-indazol-3-yl)-5H-pyrrolo[2,3-b]pyrazine-7-carboxamido)-4-methylcyclohexylcarbamate (0.08 g, 0.19 mmol) in 30 mL of 4N HCl in dioxane was stirred at room temperature for 4 hours. The solvent was removed under reduced pressure and the residue was purified by preparative-HPLC (Gemini 5u C18 150×21.2 mm; inject volume: 3 mL/inj; flow rate: 20 mL/min; wavelength: 214 nm and 254 nm; the gradient conditions were: 23% acetonitrile/77% water (0.1% trifluoroacetic acid, v/v) initially, proceeding to 32% acetonitrile/68% water (0.1% trifluoroacetic acid, v/v) in a linear fashion over 9 min.) to give N-(trans-4-amino-1-methylcyclohexyl)-2-(6-fluoro-1-methyl-1H-indazol-3-yl)-5H-pyrrolo[2,3-b]pyrazine-7-carboxamide hydrochloride (18 mg, 26%) as a white solid. MS: $(M+H)^+=422$; $^1$H NMR (300 MHz, DMSO): δ 12.91 (s, 1H), 9.10 (s, 1H), 8.50-8.43 (m, 2H), 7.97-7.71 (m, 5H), 7.19 (t, 1H, J=9.2 Hz), 4.18 (s, 3H), 3.20 (brs, 1H), 2.17-1.87 (m, 6H), 1.62-1.58 (m, 5H) and N-(cis-4-amino-1-methylcyclohexyl)-2-(6-fluoro-1-methyl-1H-indazol-3-yl)-5H-pyrrolo[2,3-b]pyrazine-7-carboxamide hydrochloride (12 mg, 17%) as a white solid. MS: $(M+H)^+=541$; $^1$H NMR (300 MHz, DMSO): δ 9.13 (s, 1H), 8.47-8.43 (m, 2H), 7.85 (s, 1H), 7.76-7.72 (m, 3H), 7.26-7.21 (m, 1H), 4.19 (s, 3H), 3.03 (brs, 1H), 2.06-2.01 (m, 2H), 1.72 (brs, 2H), 1.54 (brs, 7H).

Example 418

N-tert-Butyl-2-(6-fluoro-1-(2,2,2-trifluoroethyl)-1H-indazol-3-yl)-5H-pyrrolo[2,3-b]pyrazine-7-carboxamide

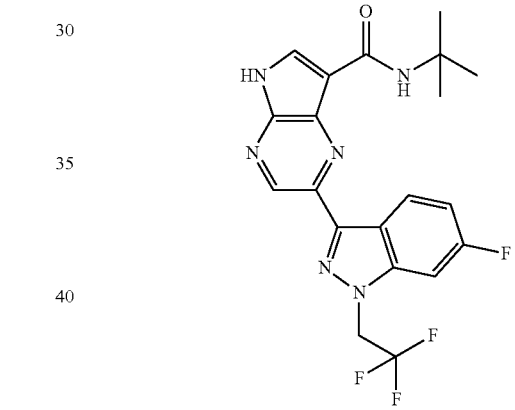

Step 1

N-tert-Butyl-2-(6-fluoro-1-(2,2,2-trifluoroethyl)-1H-indazol-3-yl)-5-((2-(trimethylsilyl)ethoxy)methyl)-5H-pyrrolo[2,3-b]pyrazine-7-carboxamide

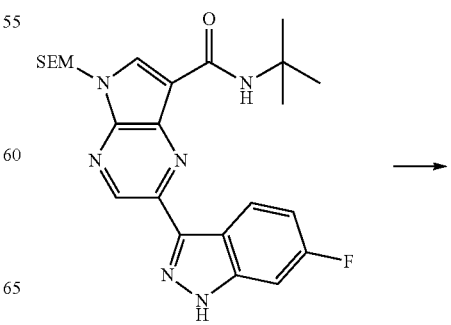

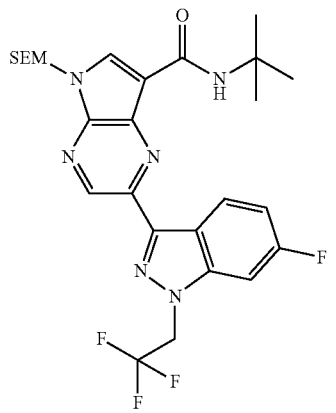

To a mixture of N-tert-Butyl-2-(6-fluoro-1H-indazol-3-yl)-5-((2-(trimethylsilyl)ethoxy)methyl)-5H-pyrrolo[2,3-b]pyrazine-7-carboxamide (60 mg, 0.12 mmol) and potassium carbonate (100 mg, 0.72 mmol) in 10 mL of DMF was added 2-iodo-1,1,1-trifluoroethane (0.5 mL, 5.07 mmol). The reaction mixture was heated to 80° C. for 3 hours. After cooling to room temperature, 50 mL of water were added, and the mixture was extracted with ethyl acetate (2×50 mL), combined organics dried with sodium sulphate, filtered and concentrated to give N-tert-butyl-2-(6-fluoro-1-(2,2,2-trifluoroethyl)-1H-indazol-3-yl)-5-((2-(trimethylsilyl)ethoxy)methyl)-5H-pyrrolo[2,3-b]pyrazine-7-carboxamide (60 mg, crude). LCMS: (M+H)$^+$=565; (M+Na)$^+$=587. Crude material used in the next step without further purification.

Step 2

N-tert-Butyl-2-(6-fluoro-1-(2,2,2-trifluoroethyl)-1H-indazol-3-yl)-5H-pyrrolo[2,3-b]pyrazine-7-carboxamide

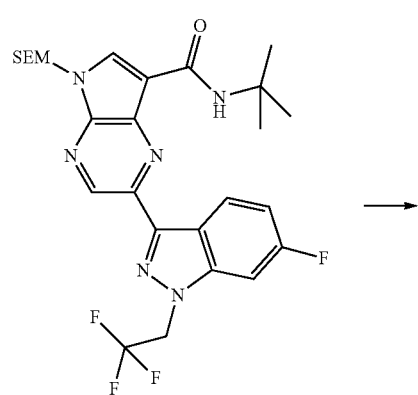

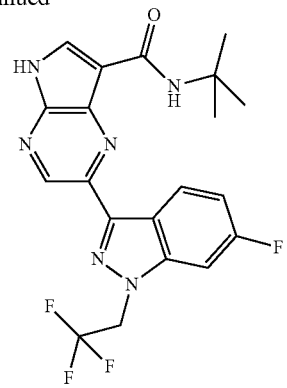

To a mixture of N-tert-Butyl-2-(6-fluoro-1-(2,2,2-trifluoroethyl)-1H-indazol-3-yl)-5-((2-(trimethylsilyl)ethoxy)methyl)-5H-pyrrolo[2,3-b]pyrazine-7-carboxamide (60 mg, 0.12 mmol) in 3 mL of methanol was added concentrated HCl (10 mL). The reaction mixture was heated to 50° C. and stirred overnight. The solvent was evaporated and the residue was triturated with tert-butyl methyl ether, filtered and dried to give N-tert-butyl-2-(6-fluoro-1-(2,2,2-trifluoroethyl)-1H-indazol-3-yl)-5H-pyrrolo[2,3-b]pyrazine-7-carboxamide as a yellow solid (30 mg, 58%). LCMS: (M+H)$^+$=435; $^1$H NMR (300 MHz, DMSO): δ 12.86 (s, 1H), 9.04 (s, 1H), 8.52-8.47 (m, 1H), 8.41 (d, 1H, J=3.0 Hz), 7.89-7.83 (m, 2H), 7.26-7.23 (m, 1H), 5.62-5.53 (m, 2H), 1.51 (s, 9H).

Example 419

(S)-2-(6-Chloro-1H-indazol-3-yl)-N-(1-hydroxypropan-2-yl)-5H-pyrrolo[3,2-b]pyrazine-7-carboxamide

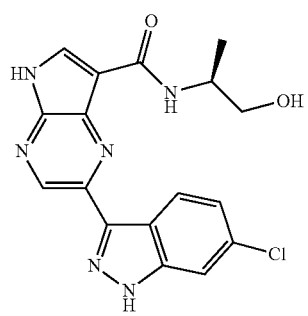 [SMILES: C[C@@H](CO)NC(=O)c1c[nH]c2ncc(-c3n[nH]c4cc(Cl)ccc34)nc12]

A mixture of 2-(6-chloro-1H-indazol-3-yl)-5H-pyrrolo[3,2-b]pyrazine-7-carboxylic acid (200 mg, 0.638 mmol), (S)-2-aminopropan-1-ol (57 mg, 0.765 mmol), EDCI (366 mg, 1.914 mmol), HOBt (258 mg, 1.914 mmol) and DIPEA (247 mg, 1.914 mmol) in dry DMF (10 mL) was stirred for 16 hours at room temperature. Water (10 mL) was added, the formed precipitate was separated by filtration, washed with methanol (1 mL) then was purified by preparative-HPLC (Gemini 5u C18 150×21.2 mm; inject volume: 3 mL/inj, flow rate: 20 mL/min; wavelength: 214 nm and 254 nm; the gradient conditions are: 30% acetonitrile/70% water (0.1% trifluoroacetic acid V/V) initially, and then proceed to 60% acetonitrile/40% water (0.1% trifluoroacetic acid V/V) in a linear fashion after just 9 min.) to afford (S)-2-(6-chloro-1H-indazol-3-yl)-N-(1-hydroxypropan-2-yl)-5H-pyrrolo[3,2-b]pyrazine-7-carboxamide (46 mg, 26% for two steps) as a yellow solid. LCMS: (M+H)⁺=371; ¹H NMR (300 MHz, DMSO+D₂O): δ 9.14 (s, 1H), 8.59 (d, 1H, J=8.7 Hz), 8.36 (s, 1H), 7.72 (s, 1H), 7.27 (dd, 1H, J1=8.4 Hz, J2=1.8 Hz), 4.23-4.18 (m, 1H), 3.55 (d, 1H, J=4.2 Hz), 1.25 (d, 1H, J=6.6 Hz).

Example 420

N-tert-Butyl-2-(1-methyl-6-(trifluoromethyl)-1H-indazol-3-yl)-5H-pyrrolo[3,2-b]pyrazine-7-carboxamide

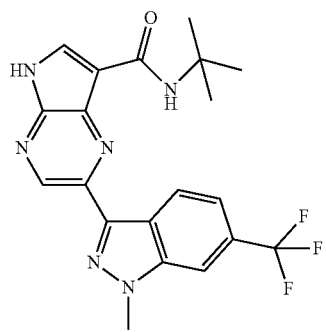 [SMILES: Cn1nc(-c2cnc3[nH]cc(C(=O)NC(C)(C)C)c3n2)c2ccc(C(F)(F)F)cc21]

Step 1

3-Iodo-6-(trifluoromethyl)-1H-indazole

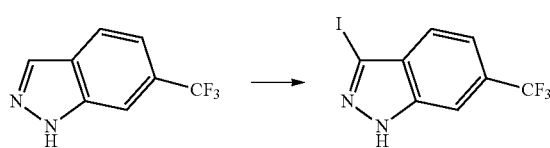 [SMILES: FC(F)(F)c1ccc2cn[nH]c2c1 ; FC(F)(F)c1ccc2c(I)n[nH]c2c1]

A mixture of 6-(trifluoromethyl)-1H-indazole (0.5 g, 2.69 mmol), KOH (0.45 g, 8.1 mmol) and I₂ (1.37 g, 5.38 mmol) in dry DMF (20 mL) was stirred for 16 hours at room temperature. Ethyl acetate (100 mL) was added and the mixture was washed with water (3×10 mL) and brine (2×10 mL). The organic layer was dried over Na₂SO₄, filtered and concentrated. The residue was then washed with ether (2 mL) and filtered to afford 3-iodo-6-(trifluoromethyl)-1H-indazole (688 mg, crude) as a yellow solid. LCMS: (M+H)⁺=313.

Step 2

3-Iodo-1-methyl-6-(trifluoromethyl)-1H-indazole

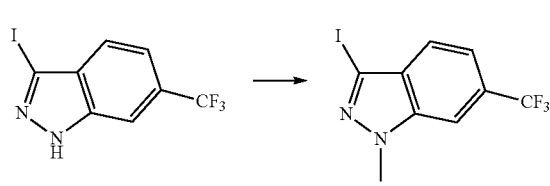

To a solution of 3-iodo-6-(trifluoromethyl)-1H-indazole (650 mg, 2.09 mmol) in dry tetrahydrofuran (20 mL) was added potassium 2-methylpropan-2-olate (0.35 mL, 3.13 mmol) at 0° C. under N₂ atmosphere. After 30 minutes, iodomethane (445 mg, 3.13 mmol) was added dropwise at 0° C., then it was warmed to room temperature for 2 h. Water (2 mL) was added and product extracted with dichloromethane (150 mL), then organic phase washed with water (2×20 mL), brine (2×20 mL) then dried over Na₂SO₄, filtered and concentrated. The residue was washed with petroleum ether (2 mL) and filtered to afford 3-iodo-1-methyl-6-(trifluoromethyl)-1H-indazole (491 mg, 72%) as a white solid. LCMS: (M+H)⁺=327.

Step 3

1-Methyl-3-(tributylstannyl)-6-(trifluoromethyl)-1H-indazole

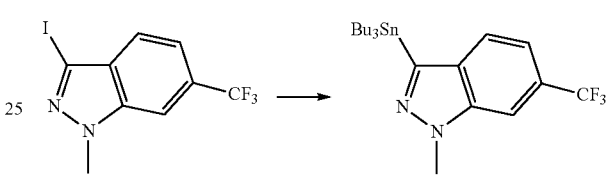

To a solution of 3-iodo-1-methyl-6-(trifluoromethyl)-1H-indazole (491 mg, 1.51 mmol) in dry tetrahydrofuran (20 mL) was added drop-wise isopropylmagnesium chloride (1.66 mL, 2M in THF, 3.31 mmol) at −16° C. under N₂ atmosphere. After stirring for 20 minutes, tributylchlorostannane (0.49 mL, 1.81 mmol) was added drop-wise at −16° C., then it was warmed to room temperature for 2 h. NH₄Cl solution (2 mL) was added and product was extracted with dichloromethane (150 mL), then washed with water (3×20 mL) and brine (2×20 mL). The organic layer was dried over Na₂SO₄, filtered and concentrated to afford 1-methyl-3-(tributylstannyl)-6-(trifluoromethyl)-1H-indazole (0.98 g, crude) as yellow oil which was used to next step without further purification. ¹H NMR (300 MHz, CDCl₃): δ 7.79 (d, 1H, J=11.4 Hz), 7.70 (s, 1H), 7.32 (d, 1H, J=8.4 Hz), 1.48-1.32 (m, 6H), 1.25-1.18 (m, 12H), 0.92-0.79 (m, 9H).

Step 4

Methyl 2-(1-methyl-6-(trifluoromethyl)-1H-indazol-3-yl)-5-(pivaloyloxymethyl)-5H-pyrrolo[3,2-b]pyrazine-7-carboxylate

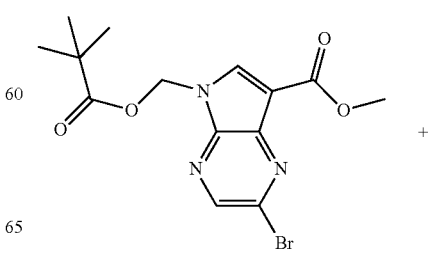

-continued

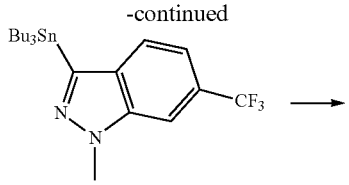

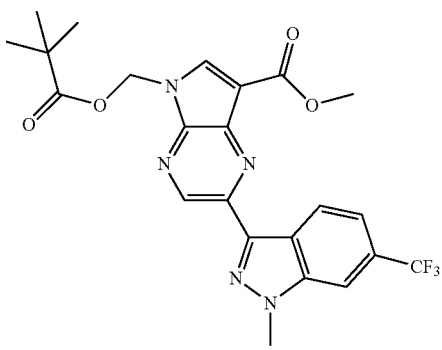

A mixture of methyl 2-bromo-5-(pivaloyloxymethyl)-5H-pyrrolo[3,2-b]pyrazine-7-carboxylate (0.3 g, 0.81 mmol), 1-methyl-3-(tributylstannyl)-6-(trifluoromethyl)-1H-indazole (0.98 g, 1.51 mmol), Pd(PPh₃)₄ (174 mg, 0.151 mmol) and CuI (58 mg, 0.302 mmol) in dry DMF (10 mL) was heated to 90° C. for 3 hours. Water (10 mL) was added. The formed precipitate was separated by filtration, washed with petroleum ether (3 mL) to afford methyl 2-(1-methyl-6-(trifluoromethyl)-1H-indazol-3-yl)-5-(pivaloyloxymethyl)-5H-pyrrolo[3,2-b]pyrazine-7-carboxylate (200 mg, 50%) as a white solid. LCMS: (M+H)⁺=490.

Step 5

2-(1-Methyl-6-(trifluoromethyl)-1H-indazol-3-yl)-5H-pyrrolo[3,2-b]pyrazine-7-carboxylic acid

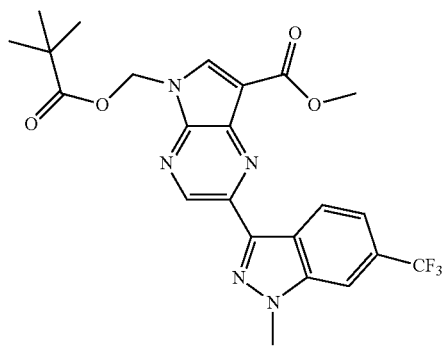

-continued

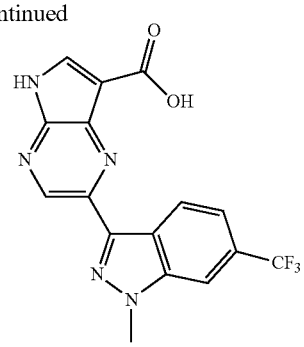

A mixture of methyl 2-(1-methyl-6-(trifluoromethyl)-1H-indazol-3-yl)-5-(pivaloyl oxymethyl)-5H-pyrrolo[3,2-b]pyrazine-7-carboxylate (200 mg, 0.409 mmol) and KOH (229 mg, 4.09 mmol) in 1,4-dioxane (5 mL) and water (2 mL) was heated to reflux for 4 hours. Dioxane was concentrated and the residual aqueous layer was adjusted to pH=4 with 1.0 M HCl. The precipitate was collected by filtration and dried to afford 2-(1-methyl-6-(trifluoromethyl)-1H-indazol-3-yl)-5H-pyrrolo[3,2-b]pyrazine-7-carboxylic acid (230 mg, crude) as a yellow solid. LCMS: (M+H)⁺=362.

Step 6

N-tert-Butyl-2-(1-methyl-6-(trifluoromethyl)-1H-indazol-3-yl)-5H-pyrrolo[3,2-b]pyrazine-7-carboxamide

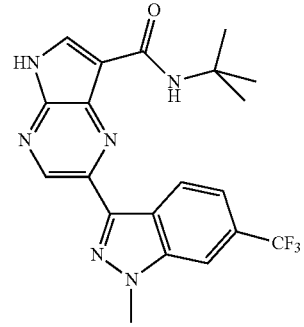

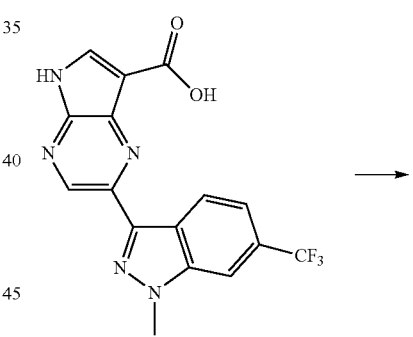

A mixture of 2-(1-methyl-6-(trifluoromethyl)-1H-indazol-3-yl)-5H-pyrrolo[3,2-b]pyrazine-7-carboxylic acid (190 mg, 0.526 mmol), 2-methylpropan-2-amine (58 mg, 0.789 mmol), EDCI (301 mg, 1.578 mmol), HOBt (213 mg, 1.578 mmol) and DIPEA (204 mg, 1.578 mmol) in dry DMF (5 mL) was stirred for 16 hours at room temperature. Water (5 mL) was added, the formed precipitate was separated by filtration then purified by preparative-HPLC (Gemini 5u C18 150× 21.2 mm; inject volume: 3 mL/inj, flow rate: 20 mL/min; wavelength: 214 nm and 254 nm; the gradient conditions are: 50% acetonitrile/50% water (0.1% trifluoroacetic acid V/V) initially, and then proceed to 90% acetonitrile/10% water (0.1% trifluoroacetic acid V/V) in a linear fashion after just 9 min.) to afford N-tert-butyl-2-(1-methyl-6-(trifluoromethyl)-1H-indazol-3-yl)-5H-pyrrolo[3,2-b]pyrazine-7-carboxamide (47 mg, 21%) as a yellow solid. LCMS: (M+H)$^+$=417; $^1$H NMR (300 MHz, DMSO): δ 12.82 (s, 1H), 9.08 (s, 1H), 8.63 (d, 1H, J=8.4 Hz), 8.38 (s, 1H), 8.30 (s, 1H), 7.89 (s, 1H), 7.49 (d, 1H, J=8.7 Hz), 4.28 (s, 3H), 1.22 (s, 9H).

Example 421

N-tert-Butyl-2-(1H-indazol-7-yl)-5H-pyrrolo[3,2-b]pyrazine-7-carboxamide hydrochloride

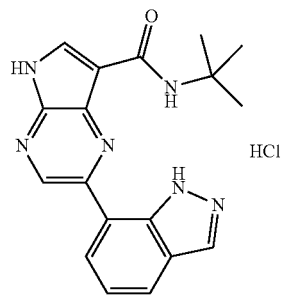 [SMILES: CC(C)(C)NC(=O)c1c[nH]c2ncc(-c3cccc4cn[nH]c34)nc12 ; Cl]

Step 1

7-Bromo-1-((2-(trimethylsilyl)ethoxy)methyl)-1H-indazole

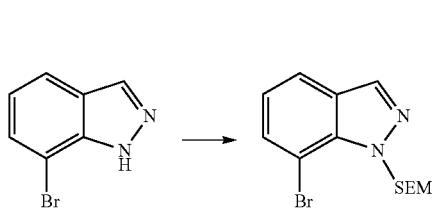 [SMILES: Brc1cccc2cn[nH]c12 ; C[Si](C)(C)CCOCn1ncc2cccc(Br)c21]

To a solution of 7-bromo-1H-indazole (1 g, 5.1 mmol) in dry tetrahydrofuran (20 mL) was added NaH (305 mg, 60%, 7.65 mmol) at –20° C. under N$_2$ atmosphere. After 20 minutes, (2-(chloromethoxy)ethyl)trimethylsilane (1 g, 6.1 mmol) was added and the mixture was warmed to 20° C. and stirred for 1 hour. Water (2 mL) was added and product extracted with dichloromethane (100 mL), organic phase washed with water (2×10 mL) and brine (2×10 mL) then dried over Na$_2$SO$_4$, filtered and concentrated. The residue was purified by column chromatography (silica gel, 200-300 mesh, eluting with ethyl acetate:petroleum ether=1:20) to afford 7-bromo-1-((2-(trimethylsilyl)ethoxy)methyl)-1H-indazole (1.27 g, 77%) as a yellow oil. $^1$H NMR (300 MHz, CDCl$_3$): δ 8.03 (s, 1H), 7.69 (d, 1H, J=8.7 Hz), 7.60 (d, 1H, J=8.1 Hz), 7.06-7.01 (m, 1H), 6.08 (s, 2H), 3.60 (t, 2H, J=7.8 Hz), 0.90 (d, 2H, J=8.1 Hz), 0.01 (s, 9H).

Step 2

7-(4,4,5,5-Tetramethyl-1,3,2-dioxaborolan-2-yl)-1-((2-(trimethylsilyl)ethoxy)methyl)-1H-indazole

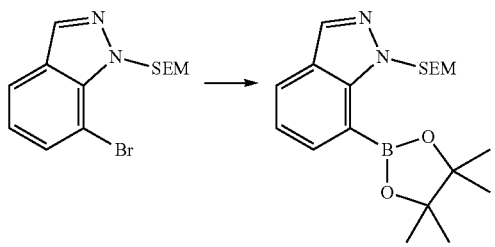 [SMILES: C[Si](C)(C)CCOCn1ncc2cccc(Br)c21 ; CC1(C)OB(c2cccc3cnn(COCC[Si](C)(C)C)c23)OC1(C)C]

A mixture of 7-bromo-1-((2-(trimethylsilyl)ethoxy)methyl)-1H-indazole (0.5 g, 1.53 mmol), 4,4,5,5-tetramethyl-2-(4,4,5,5-tetramethyl-1,3,2-dioxaborolan-2-yl)-1,3,2-dioxaborolane (465 mg, 1.83 mmol), potassium acetate (691 mg, 7.04 mmol) and PdCl$_2$(dppf) CH$_2$Cl$_2$ (125 mg, 153 mmol) in dioxane (20 mL) was heated to 100° C. for 16 hours under N$_2$ atmosphere. Reaction mixture was concentrated and the residue was partitioned between water (10 mL) and ethyl acetate (20 mL). The organic layer was washed with brine (10 mL), dried over Na$_2$SO$_4$ and concentrated to afford 7-(4,4,5,5-tetramethyl-1,3,2-dioxaborolan-2-yl)-1-((2-(trimethylsilyl)ethoxy)methyl)-1H-indazole (516 mg, crude) as a yellow oil. LCMS: (M+H)$^+$=375.

Step 3

N-tert-Butyl-2-(1-((2-(trimethylsilyl)ethoxy)methyl)-1H-indazol-7-yl)-5H-pyrrolo[3,2-b]pyrazine-7-carboxamide

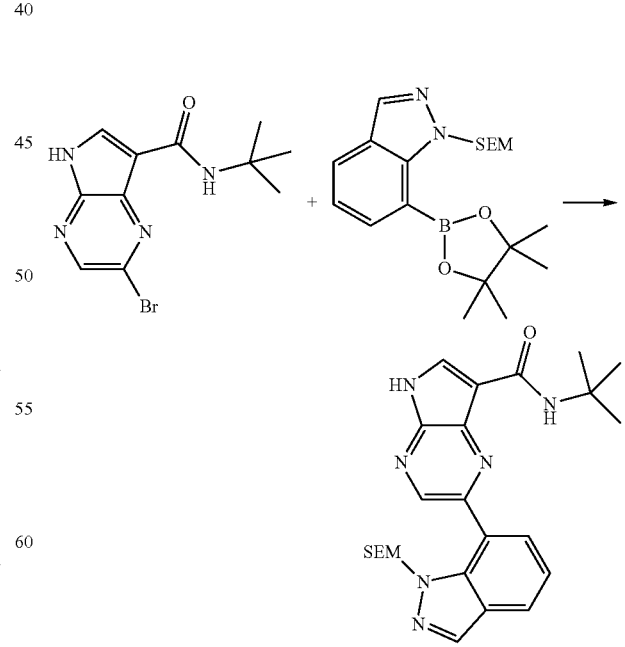

A mixture of 2-bromo-N-tert-butyl-5H-pyrrolo[3,2-b]pyrazine-7-carboxamide (0.1 g, 0.337 mmol), 7-(4,4,5,5-tetramethyl-1,3,2-dioxaborolan-2-yl)-1-((2-(trimethylsilyl) ethoxy)methyl)-1H-indazole (121 mg, 0.37 mmol), Pd$_2$(dba)$_3$ (39 mg, 0.067 mmol), X-Phos (64 mg, 0.135 mmol) and Na$_2$CO$_3$ (107 mg, 1.01 mmol) in dioxane (20 mL) and water (5 mL) was heated to 90° C. for 16 hours under N$_2$ atmosphere. The reaction mixture was concentrated and the residue was partitioned between ethyl acetate (20 mL) and water (10 mL), organic phase was washed with brine (10 mL) then dried over Na$_2$SO$_4$ and concentrated to afford N-tert-butyl-2-(1-((2-(trimethylsilyl)ethoxy)methyl)-1H-indazol-7-yl)-5H-pyrrolo[3,2-b]pyrazine-7-carboxamide (120 mg, crude) as yellow oil. LCMS: (M+H)$^+$=465.

Step 4

N-tert-Butyl-2-(1H-indazol-7-yl)-5H-pyrrolo[3,2-b]pyrazine-7-carboxamide hydrochloride

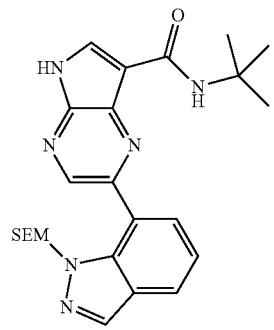

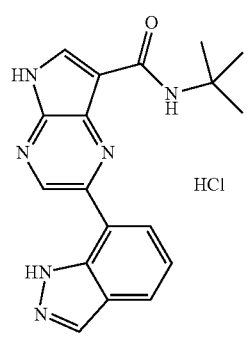

To a stirred solution of N-tert-butyl-2-(1-((2-(trimethylsilyl)ethoxy)methyl)-1H-indazol-7-yl)-5H-pyrrolo[3,2-b]pyrazine-7-carboxamide (120 mg, 0.258 mmol) in dioxane (20 mL) was bubbled HCl gas until saturation and the reaction stirred at room temperature for 16 hours. Reaction mixture was concentrated and the residue purified by preparative-HPLC (Gemini 5u C18 150×21.2 mm; inject volume: 3 mL/inj, flow rate: 20 mL/min; wavelength: 214 nm and 254 nm; the gradient conditions are: 40% acetonitrile/60% water (0.1% trifluoroacetic acid V/V) initially, and then proceed to 50% acetonitrile/50% water (0.1% trifluoroacetic acid V/V) in a linear fashion after just 9 min.). Concentrated HCl was added to the combined fractions containing pure product, then solvents evaporated to afford N-tert-butyl-2-(1H-indazol-7-yl)-5H-pyrrolo[3,2-b]pyrazine-7-carboxamide hydrochloride (20 mg, 21%) as a yellow solid. LCMS: (M+H)$^+$= 335; $^1$H NMR (300 MHz, CD$_3$OD): δ 8.94 (s, 1H), 8.34 (s, 1H), 8.31 (s, 1H), 7.97 (s, 1H), 7.94 (s, 1H), 7.39 (t, 1H, J=6.9 Hz), 1.52 (s, 9H).

Examples 422 and 423

N-(trans-3-Amino-1-methylcyclobutyl)-2-(6-fluoro-1-methyl-1H-indazol-3-yl)-5H-pyrrolo[2,3-b]pyrazine-7-carboxamide 2,2,2-trifluoroacetate; N-(cis-3-Amino-1-methylcyclobutyl)-2-(6-fluoro-1-methyl-1H-indazol-3-yl)-5H-pyrrolo[2,3-b]pyrazine-7-carboxamide 2,2,2-trifluoroacetate

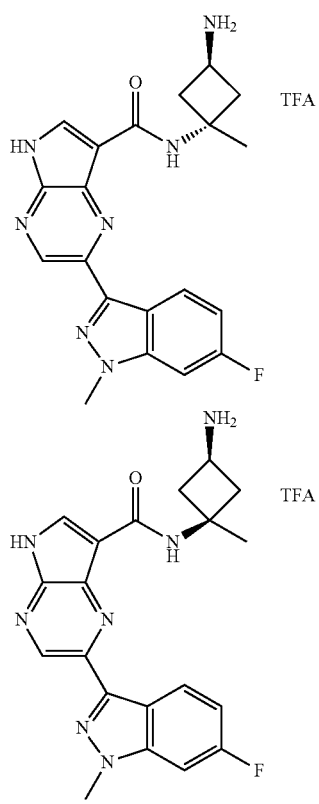

Step 1 tert-Butyl 3-oxocyclobutylcarbamate

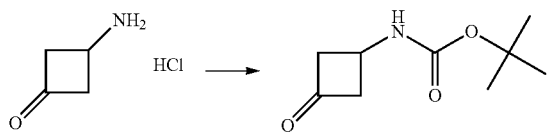

A mixture of 3-aminocyclobutanone hydrochloride (2.0 g, 16.4 mmol), (Boc)$_2$O (3.9 g, 18 mmol) and Na$_2$CO$_3$ (3.5 g, 33 mmol) in water (10 mL) and THF (50 mL) was stirred at room temperature overnight. The solvent was evaporated under reduced pressure and the residue was passed through a pad of silica gel (200-300 mesh), eluting with a mixture of ethyl acetate and petroleum ether (1:3, v/v) to give tert-butyl 3-oxocyclobutylcarbamate (2.2 g, 73%) as a yellow solid which was used for the next step without further purification. MS: (M+H)+=186.1.

Step 2 tert-Butyl 3-(tert-butylsulfinylimino)cyclobutylcarbamate

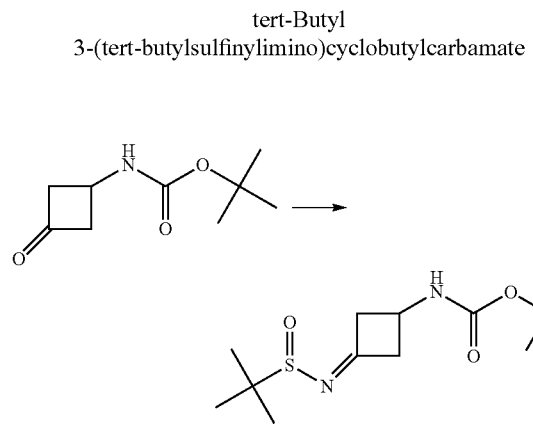

A mixture of tert-butyl 3-oxocyclobutylcarbamate (2.2 g, 11.9 mmol), 2-methylpropane-2-sulfinamide (1.6 g, 13.1 mmol), Ti(OEt)$_4$ (5.5 g, 24 mmol) in 20 mL of THF was stirred at 50-60° C. overnight. The mixture was cooled to room temperature and then quenched with saturated NH$_4$Cl solution. The formed solid was removed by filtration. The filtrate was evaporated to dryness and the crude residue was purified by silica gel chromatography (200-300 mesh, eluting with a mixture of petroleum ether and ethyl acetate (4:1)) to give tert-butyl 3-(tert-butylsulfinylimino)cyclobutylcarbamate as clear oil (2.0 g, 58%). MS: (M+H)+=289.1; $^1$H NMR (300 MHz, CDCl$_3$): δ 5.08 (m, 1H), 4.29 (s, 1H), 3.42-3.00 (m, 4H), 1.43 (s, 9H), 1.22 (s, 9H).

Step 3 tert-Butyl 3-(1,1-dimethylethylsulfinamido)-3-methylcyclobutylcarbamate

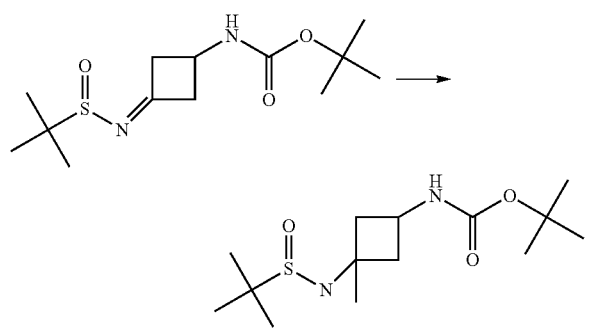

To a stirred solution of tert-butyl 3-(tert-butylsulfinylimino)cyclobutylcarbamate (0.8 g, 2.8 mmol) in 60 mL of toluene at −78° C. was added Me$_3$Al (3.1 mL, 6.2 mmol, 2M in toluene). After stirred 20 minutes at −78° C., MeLi (4.1 mL, 12.3 mmol, 3M in dimethoxymethane) was added slowly. The reaction mixture was stirred at −78° C. for additional 4 hours, and was then quenched by adding 3 mL of water. The solvent was removed under reduced pressure and the residue was passed through a pad of silica gel (200-300 mesh, eluting with a mixture of petroleum ether and ethyl acetate (4:1, v/v) to give tert-butyl 3-(1,1-dimethylethylsulfinamido)-3-methylcyclobutylcarbamate (0.45 g, 53%) as a crude oil which was used for the next step without further purification. MS: (M+H)+=305.2.

Step 4 tert-Butyl 3-amino-3-methylcyclobutylcarbamate hydrochloride

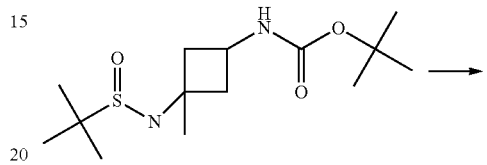

To a stirred solution of tert-butyl 3-(1,1-dimethylethylsulfinamido)-3-methylcyclobutylcarbamate (0.45 g, 1.48 mmol) in 150 mL of MeOH was added 2N HCl in dioxane (1.8 mL). The solution was stirred at room temperature overnight. The solvent was removed under reduced pressure, and the residue was triturated with EtOAc, then decanted and dried to give tert-butyl 3-amino-3-methylcyclobutylcarbamate hydrochloride (0.22 g, 63%) as a white solid. MS: (M+H)+=201.2; $^1$H NMR (300 MHz, DMSO): δ 2.24-2.22 (m, 1H), 1.43-1.383 (m, 13H), 1.10 (s, 3H).

Step 5 tert-Butyl 3-(2-(6-fluoro-1-methyl-1H-indazol-3-yl)-5H-pyrrolo[2,3-b]pyrazine-7-carboxamido)-3-methylcyclobutylcarbamate hydrochloride

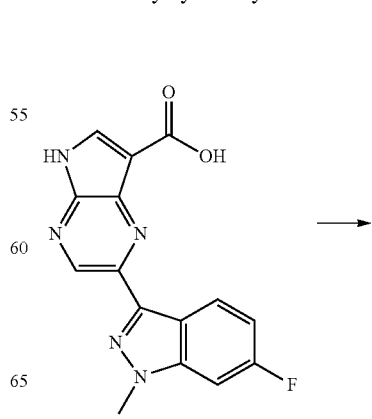

-continued

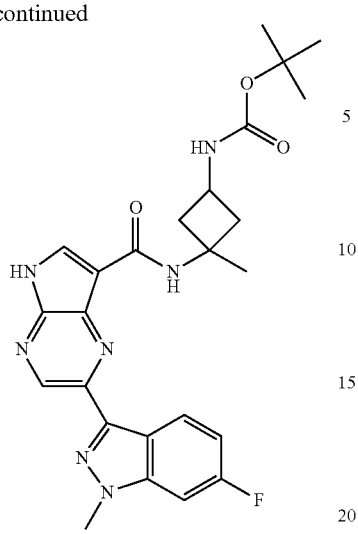

A mixture of 2-(6-fluoro-1-methyl-1H-indazol-3-yl)-5H-pyrrolo[2,3-b]pyrazine-7-carboxylic acid (0.1 g, 0.32 mmol), tert-butyl 3-amino-3-methylcyclobutylcarbamate hydrochloride (0.1 g, 0.42 mmol), EDCI (0.092 g, 0.48 mmol), DMAP (0.059 g, 0.48 mmol), HOBT (0.065 g, 0.48 mmol) and DIPEA (0.248 g, 1.92 mmol) in 25 mL of DMF was stirred at room temperature overnight. The solvent was removed under reduced pressure and the residue was passed through a pad of silica gel (200-300 mesh, eluting with a mixture of petroleum ether and ethyl acetate (4:1, v/v) to give tert-butyl 3-(2-(6-fluoro-1-methyl-1H-indazol-3-yl)-5H-pyrrolo[2,3-b]pyrazine-7-carboxamido)-3-methylcyclobutylcarbamate hydrochloride (0.11 g, 69%) as crude white solid which was used for the next step without further purification. MS: (M+H)$^+$= 494.2.

Step 7

N-(cis-3-Amino-1-methylcyclobutyl)-2-(6-fluoro-1-methyl-1H-indazol-3-yl)-5H-pyrrolo[2,3-b]pyrazine-7-carboxamide 2,2,2-trifluoroacetate; N-(trans-3-Amino-1-methylcyclobutyl)-2-(6-fluoro-1-methyl-1H-indazol-3-yl)-5H-pyrrolo[2,3-b]pyrazine-7-carboxamide 2,2,2-trifluoroacetate

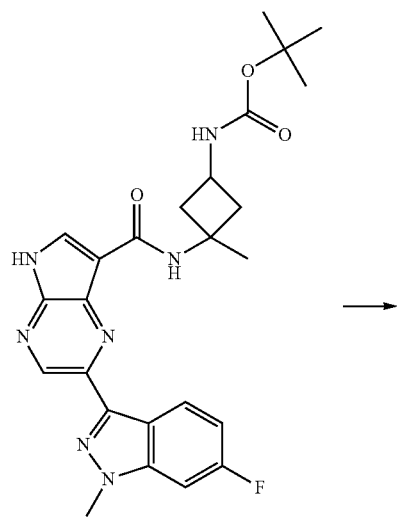

→

-continued

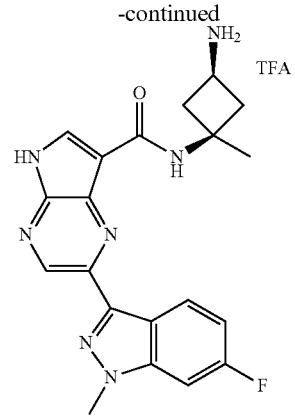

+

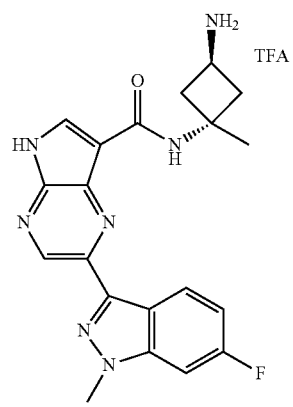

tert-Butyl 3-(2-(6-fluoro-1-methyl-1H-indazol-3-yl)-5H-pyrrolo[2,3-b]pyrazine-7-carboxamido)-3-methylcyclobutylcarbamate hydrochloride (0.11 g, 0.22 mmol) in a mixture of trifluoroacetic acid (10 mL) and dichloromethane (30 mL) was stirred at room temperature overnight. The solvent was removed under reduced pressure and the residue was purified by preparative-HPLC (Gemini 5u C18 150×21.2 mm; inject volume: 3 mL/inj, flow rate: 20 mL/min; wavelength: 214 nm and 254 nm; the gradient conditions were: 23% acetonitrile/77% water (0.1% trifluoroacetic acid, v/v) initially, proceeding to 32% acetonitrile/68% water (0.1% trifluoroacetic acid, v/v) in a linear fashion over 9 min.) to give N-(trans-3-amino-1-methylcyclobutyl)-2-(6-fluoro-1-methyl-1H-indazol-3-yl)-5H-pyrrolo[2,3-b]pyrazine-7-carboxamide 2,2,2-trifluoroacetate (3 mg, 2.7%). MS: (M+H)$^+$=394; $^1$H NMR (300 MHz, DMSO): δ 12.98 (brs, 1H), 9.12 (s, 1H), 8.54-8.47 (m, 2H), 8.26 (s, 1H), 7.75 (d, 1H, J=9.9 Hz), 8.04 (brs, 2H), 7.74 (d, 1H, J=9.6 Hz), 7.31 (t, 1H, J=8.8 Hz), 4.18 (s, 3H), 4.00 (brs, 1H), 2.85-2.78 (brs, 2H), 2.37-2.31 (m, 2H), 1.64 (s, 3H). N-(cis-3-amino-1-methylcyclobutyl)-2-(6-fluoro-1-methyl-1H-indazol-3-yl)-5H-pyrrolo[2,3-b]pyrazine-7-carboxamide 2,2,2-trifluoroacetate (16 mg, 14%). MS: (M+H)$^+$= 394; $^1$H NMR (300 MHz, DMSO): δ 9.14 (s, 1H), 8.54-8.45

(m, 3H), 8.06 (brs, 2H), 7.75 (d, 1H, J=9.9 Hz), 7.25 (t, 1H, J=9.0 Hz), 4.18 (s, 3H), 3.76 (t, 1H, J=7.7 Hz), 2.61 (brs, 4H), 1.63 (s, 3H).

Example 424

N-(1-Cyanocyclopropyl)-2-(1,6-dimethyl-1H-indazol-3-yl)-5H-pyrrolo[3,2-b]pyrazine-7-carboxamide

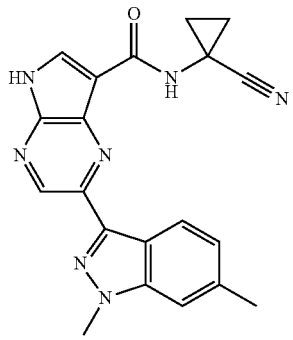 [SMILES: Cc1ccc2c(-c3cnc4[nH]cc(C(=O)NC5(C#N)CC5)c4n3)nn(C)c2c1]

Step 1

Methyl-2-(1,6-dimethyl-1H-indazol-3-yl)-5-(pivaloyloxymethyl)-5H-pyrrolo[3,2-b]pyrazine-7-carboxylate

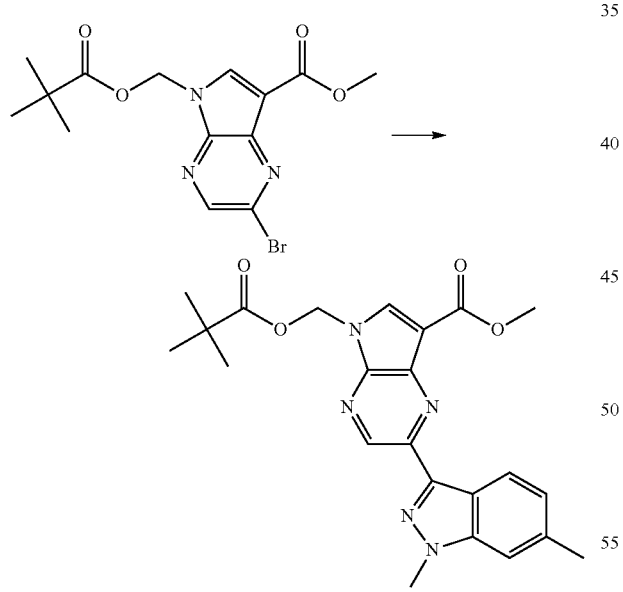

To a solution of methyl 2-bromo-5-(pivaloyloxymethyl)-5H-pyrrolo[3,2-b]pyrazine-7-carboxylate (2.5 g, 6.74 mmol) and 3-iodo-1,6-dimethyl-M-indazole (1.83 g, 6.74 mmol) in DMF (30 mL) was added hexa-n-butylditin (5.86 g, 10.1 mmol) followed by Pd(PPh$_3$)$_4$ (0.78 g, 0.674 mmol). The reaction mixture was degassed by bubbling nitrogen and stirred at 98° C. for 16 hours. The concentrated mixture was purified by column chromatography on silica gel eluting with petroleum ether/EtOAc (5:1 to 2:1, v/v) to give methyl 2-(1, 6-dimethyl-1H-indazol-3-yl)-5-(pivaloyloxymethyl)-5H-pyrrolo[3,2-b]pyrazine-7-carboxylate (1.05 g, 36%) as a yellow solid.

MS: (M+H)$^+$=436.2; $^1$H NMR (300 MHz, DMSO): δ 9.13 (s, 1H), 8.67-8.64 (m, 2H), 7.50 (s, 1H), 7.16 (d, 1H, J=8.1 Hz), 6.30 (s, 2H), 4.10 (s, 3H), 3.92 (s, 3H), 2.48 (s, 3H), 1.07 (s, 9H).

Step 2

2-(1,6-Dimethyl-1H-indazol-3-yl)-5H-pyrrolo[3,2-b]pyrazine-7-carboxylic acid

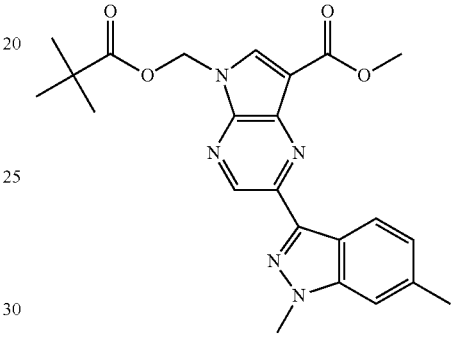

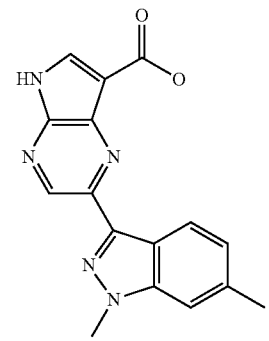

To a stirred solution of methyl 2-(1,6-dimethyl-1H-indazol-3-yl)-5-(pivaloyloxymethyl)-5H-pyrrolo[3,2-b]pyrazine-7-carboxylate (1 g, 2.3 mmol) in dioxane/H$_2$O (40 mL/10 mL) was added a solution of KOH (1.39 g, 34.5 mmol) in water (10 mL) at room temperature. Then the reaction mixture was heated to reflux for 4 hours. After cooling to room temperature, the solvent was evaporated under reduced pressure. The residue was diluted with water and acidified to pH 3-4 with HCl (aqueous, 2 M). The mixture was filtered and the filter cake dried to give 2-(1,6-dimethyl-1H-indazol-3-yl)-5H-pyrrolo[3,2-b]pyrazine-7-carboxylic acid (0.6 g, 84.5%) as a solid, which was used in the next step without further purification. MS: (M+H)+=308.1.

Step 3

N-(1-Cyanocyclopropyl)-2-(1,6-dimethyl-1H-indazol-3-yl)-5H-pyrrolo[3,2-b]pyrazine-7-carboxamide

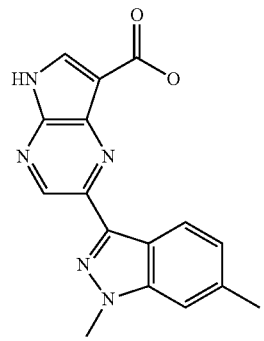

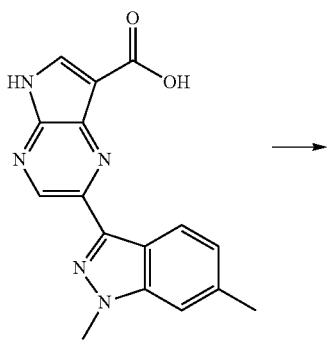

To a stirred mixture of 2-(1,6-dimethyl-1H-indazol-3-yl)-5H-pyrrolo[3,2-b]pyrazine-7-carboxylic acid (80 mg, 0.26 mmol) and 1-aminocyclopropanecarbonitrile hydrochloride (46 mg, 0.39 mmol) in DMF (3 mL) was added EDCI (100 mg, 0.52 mmol) followed by DMAP (63 mg, 0.52 mmol). The mixture was stirred at room temperature for 16 hours. Then the mixture was poured into water (5 mL) and filtered, the solid was washed with DMSO and MeOH then dried to give N-(1-cyanocyclopropyl)-2-(1,6-dimethyl-1H-indazol-3-yl)-5H-pyrrolo[3,2-b]pyrazine-7-carboxamide (22 mg, 23%) as a white solid. MS: (M+H)+=372; $^1$H NMR (300 MHz, DMSO): δ 12.98 (s, 1H), 9.14 (s, 1H), 8.95 (s, 1H), 8.55 (s, 1H), 7.58 (s, 1H), 7.25 (d, 1H, J=8.4 Hz), 4.17 (s, 3H), 2.56 (s, 3H), 1.77 (d, 2H, J=6.0 Hz), 1.48-1.44 (m, 2H).

Example 425

2-(1,6-Dimethyl-1H-indazol-3-yl)-N-(3-methylpyrrolidin-3-yl)-5H-pyrrolo[3,2-b]pyrazine-7-carboxamide

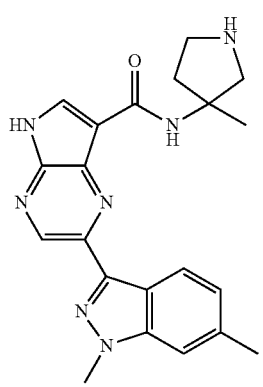

Step 1 tert-Butyl 3-(2-(1,6-dimethyl-1H-indazol-3-yl)-5H-pyrrolo[3,2-b]pyrazine-7-carboxamido)-3-methylpyrrolidine-1-carboxylate -continued

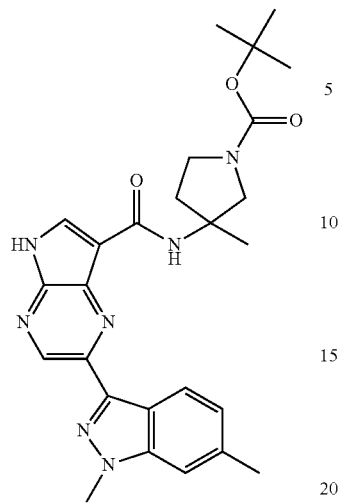

To a stirred mixture of 2-(1,6-dimethyl-1H-indazol-3-yl)-5H-pyrrolo[3,2-b]pyrazine-7-carboxylic acid (100 mg, 0.326 mmol) and 2-cyclopropylpropan-2-amine hydrochloride (100 mg, 0.488 mmol) in DMF (3 mL) was added EDCI (125 mg, 0.652 mmol) followed by DMAP (80 mg, 0.652 mmol). The mixture was stirred at room temperature for 16 hours. Then the mixture was poured into water (5 mL) and filtered to give crude tert butyl-3-(2-(1,6-dimethyl-1H-indazol-3-yl)-5H-pyrrolo[3,2-b]pyrazine-7-carboxamido)-3-methylpyrrolidine-1-carboxylate (130 mg, 81%) which was used in the next step without further purification. MS: (M+H)$^+$=490.2.

Step 2

2-(1,6-Dimethyl-1H-indazol-3-yl)-N-(3-methylpyrrolidin-3-yl)-5H-pyrrolo[3,2-b]pyrazine-7-carboxamide

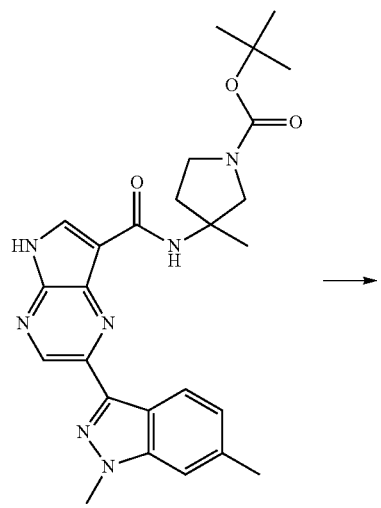

-continued

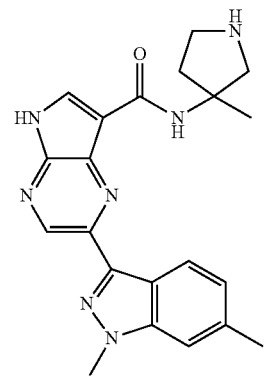 [SMILES: Cc1ccc2c(-c3cnc4[nH]cc(C(=O)NC5(C)CCNC5)c4n3)nn(C)c2c1]

To a stirred mixture of tert-butyl 3-(2-(1,6-dimethyl-1H-indazol-3-yl)-5H-pyrrolo[3,2-b]pyrazine-7-carboxamido)-3-methylpyrrolidine-1-carboxylate (130 mg, 0.266 mmol) in dichloromethane (2.5 mL) was added drop-wise trifluoroacetic acid (2 mL) at room temperature and the reaction mixture stirred for 2 hours. The mixture was diluted with aqueous NaHCO$_3$, filtered, washed with water and dried to give 2-(1,6-dimethyl-1H-indazol-3-yl)-N-(3-methylpyrrolidin-3-yl)-5H-pyrrolo[3,2-b]pyrazine-7-carboxamide (35 mg, 34%) as a pale solid.

MS: (M+H)$^+$=390; $^1$H NMR (300 MHz, DMSO): δ 10.15 (brs, 1H), 9.13 (s, 1H), 8.45 (d, 1H, J=7.5 Hz), 8.38 (d, 1H, J=8.1 Hz), 8.25 (s, 1H), 7.59 (s, 1H), 7.18 (d, 1H, J=8.4 Hz), 4.17 (s, 3H), 3.54-3.33 (m, 4H), 2.55 (s, 3H), 2.44-2.42 (m, 1H), 2.19-2.12 (m, 1H), 1.68 (s, 3H).

Example 426

2-(1-(2-(Dimethylamino)ethyl)-6-methyl-1H-indazol-3-yl)-N-(1-hydroxy-2-methylpropan-2-yl)-5H-pyrrolo[2,3-b]pyrazine-7-carboxamide hydrochloride

Step 1

2-(3-Iodo-6-methyl-1H-indazol-1-yl)-N,N-dimethylethanamine

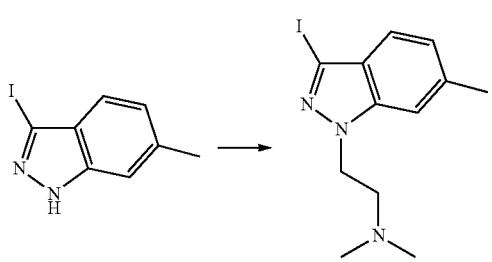

A mixture of 3-iodo-6-methyl-1H-indazole (516 mg, 2 mmol), 2-chloro-N,N-dimethylethanamine hydrochloride (346 mg, 2.4 mmol) and potassium carbonate (828 mg, 6 mmol) in 20 mL of DMF was heated to 80 degree overnight. After cooling to room temperature, water (50 mL) was added, product extracted with dichloromethane (3×50 mL), combined organics were dried with sodium sulfate, and concentrated to give 2-(3-iodo-6-methyl-1H-indazol-1-yl)-N,N-dimethylethanamine (1 g, 100%). $^1$H NMR (300 MHz, CDCl$_3$): δ 7.33 (d, 1H, J=8.1 Hz), 7.15 (s, 1H), 7.03 (d, 1H, J=0.6 Hz), 4.47 (t, 2H, J=7.2 Hz), 2.81 (t, 2H, J=7.2 Hz), 2.51 (s, 3H), 2.34 (m, 6H).

Step 2

N,N-Dimethyl-2-(6-methyl-3-(tributylstannyl)-1H-indazol-1-yl)ethanamine

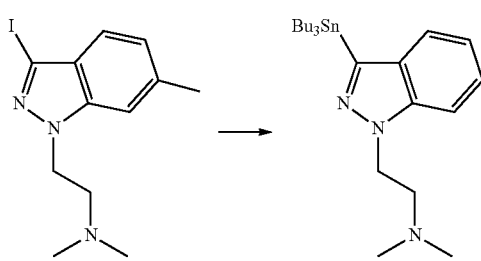

A solution of 2-(3-iodo-6-methyl-1H-indazol-1-yl)-N,N-dimethylethanamine (450 mg, 1.4 mmol) in 20 mL of dry THF was cooled to −20° C. under nitrogen atmosphere, isopropylmagnesium chloride (1.4 mL, 2.8 mmol, 2 M in THF) was added and stirred for 15 min at −20° C. Then tributylchlorostannane (0.8 mL, 2.8 mmol) was added and allowed to warm to room temperature. The reaction was cooled in an ice bath and quenched with saturated ammonium chloride solution, extracted with ethyl acetate (3×30 mL), combined organics dried with sodium sulfate and concentrated to give 1.4 g of crude N,N-dimethyl-2-(6-methyl-3-(tributylstannyl)-1H-indazol-1-yl)ethanamine as an oil which was used in the next step directly without further purification.

Step 3

N-(1-(tert-Butyldimethylsilyloxy)-2-methylpropan-2-yl)-2-(1-(2-(dimethylamino)ethyl)-6-methyl-1H-indazol-3-yl)-5H-pyrrolo[2,3-b]pyrazine-7-carboxamide

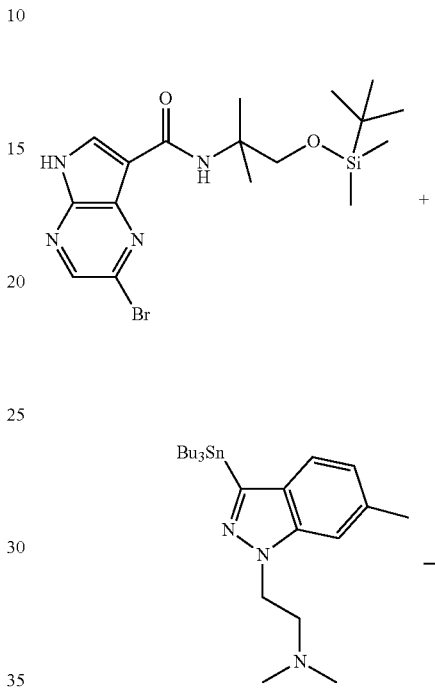

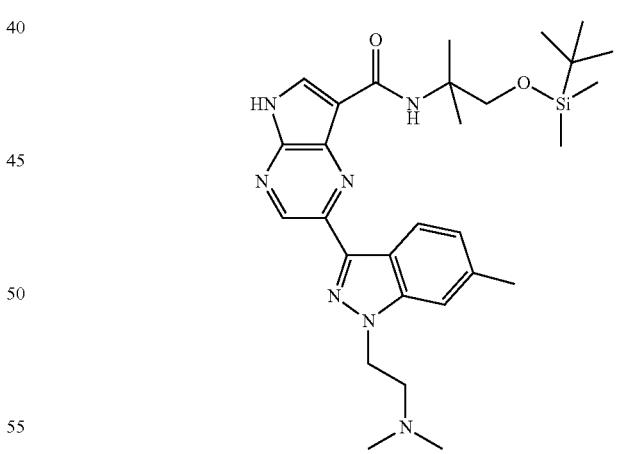

A mixture of 2-bromo-N-(1-(tert-butyldimethylsilyloxy)-2-methylpropan-2-yl)-5H-pyrrolo[2,3-b]pyrazine-7-carboxamide (210 mg, 0.5 mmol) and N,N-dimethyl-2-(6-methyl-3-(tributylstannyl)-1H-indazol-1-yl)ethanamine (1.4 g, 2.85 mmol) with tetrakis(triphenylphosphine)palladium(0) (20 mg, 0.017 mmol), copper iodide (10 mg, 0.52 mmol) in 15 mL of dry DMF was heated to 85° C. overnight under N$_2$. The reaction mixture was cooled to room temperature, diluted with 50 mL of water, extracted with dichloromethane (8×50 mL), combined organics dried with sodium sulfate and concentrated. The crude product was used into the next step without further purification. LCMS: (M+H)+=550.

Step 4

2-(1-(2-(Dimethylamino)ethyl)-6-methyl-1H-indazol-3-yl)-N-(1-hydroxy-2-methylpropan-2-yl)-5H-pyrrolo[2,3-b]pyrazine-7-carboxamide hydrochloride

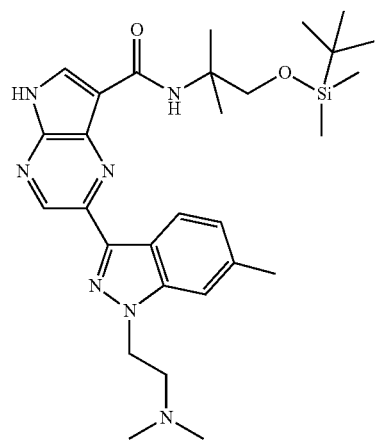

→

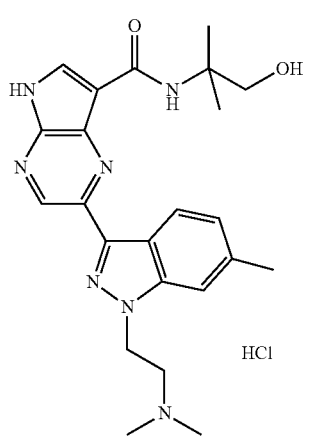 [SMILES: Cc1ccc2c(-c3cnc4[nH]cc(C(=O)NC(C)(C)CO)c4n3)nn(CCN(C)C)c2c1 ; Cl]

To a solution of N-(1-(tert-butyldimethylsilyloxy)-2-methylpropan-2-yl)-2-(1-(2-(dimethylamino)ethyl)-6-methyl-1H-indazol-3-yl)-5H-pyrrolo[2,3-b]pyrazine-7-carboxamide (127 mg, 0.23 mmol) in 5 mL of methanol and 1 mL of THF was added 1 mL of concentrated HCl, then stirred for 3 hours. The precipitate was filtered and filter cake was washed with 2-methoxy-2-methylpropane (5 mL) to give 25 mg of 2-(1-(2-(dimethylamino)ethyl)-6-methyl-1H-indazol-3-yl)-N-(1-hydroxy-2-methylpropan-2-yl)-5H-pyrrolo[2,3-b]pyrazine-7-carboxamide hydrochloride. LCMS: (M+H)+=436; $^1$H NMR (300 MHz, DMSO): δ 12.85 (s, 1H), 10.19 (s, 1H), 9.18 (s, 1H), 8.47 (d, 1H, J=8.1 Hz), 8.37 (s, 1H), 7.92 (s, 1H), 7.68 (s, 1H), 7.17 (d, 1H, J=8.4 Hz), 4.93 (s, 2H), 3.70-3.63 (m, 4H), 2.89 (s, 6H), 2.50 (s, 3H), 1.45 (s, 6H).

Example 427

N-tert-Butyl-2-(1-(3-(dimethylamino)propyl)-6-methyl-1H-indazol-3-yl)-5H-pyrrolo[2,3-b]pyrazine-7-carboxamide hydrochloride

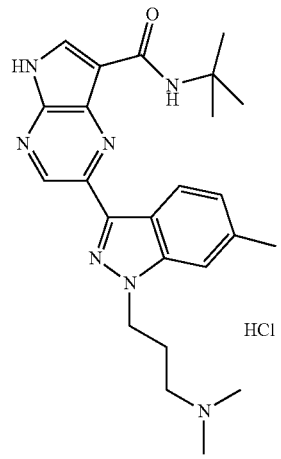 [SMILES: Cc1ccc2c(-c3cnc4[nH]cc(C(=O)NC(C)(C)C)c4n3)nn(CCCN(C)C)c2c1 ; Cl]

Step 1

3-(3-Iodo-6-methyl-1H-indazol-1-yl)-N,N-dimethylpropan-1-amine

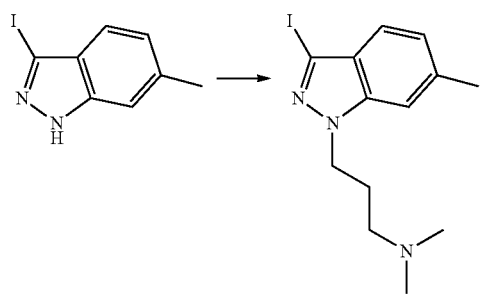 [SMILES: Cc1ccc2c(I)n[nH]c2c1 ; Cc1ccc2c(I)nn(CCCN(C)C)c2c1]

A mixture of 3-iodo-6-methyl-1H-indazole (2.58 g, 10 mmol), 3-chloro-N,N-dimethylpropan-1-amine hydrochloride (2.37 g, 15 mmol) and potassium carbonate (4.14 g, 30 mmol) in 50 ml of DMF was heated to 85° C. for 3 hours. After cooling to room temperature, 100 mL of water was added and the mixture was extracted with ethyl acetate (4×100 mL). Then the combined organic phases were added with 20 mL of 6N HCl, and the solution was extracted with dichloromethane (4×50 mL). The combined organic phases were dried with sodium sulfate, concentrated to give 3-(3-iodo-6-methyl-1H-indazol-1-yl)-N,N-dimethylpropan-1-amine (1.74 g, 50.6%). LCMS: (M+H)+=344; $^1$H NMR (300

MHz, CDCl₃): δ 7.33 (d, 1H, J=8.4 Hz), 7.21 (s, 1H), 7.03 (d, 1H, J=8.4 Hz), 4.43 (t, 2H, J=6.6 Hz), 2.51 (s, 3H), 2.27-2.23 (m, 8H), 2.09-2.07 (m, 2H).

Step 2

N,N-Dimethyl-3-(6-methyl-3-(tributylstannyl)-1H-indazol-1-yl)propan-1-amine

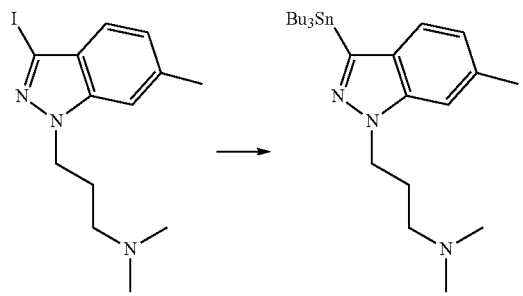

A solution of 3-(3-iodo-6-methyl-1H-indazol1-yl)-N,N-dimethylpropan-1-amine (400 mg, 1.2 mmol) in 20 mL of dry THF was cooled to −20° C. under nitrogen atmosphere, then isopropylmagnesium chloride (1.2 mL, 2.4 mmol, 2M in THF) was added and stirred for 15 min at −20° C. Then tributylchlorostannane (0.7 mL, 2.4 mmol) was added and allowed to warm to room temperature. The reaction was cooled in an ice bath and quenched with saturated ammonium chloride solution, product extracted with ethyl acetate (3×50 mL), combined organics dried with sodium sulfate and concentrated to give N,N-dimethyl-3-(6-methyl-3-(tributylstannyl)-1H-indazol-1-yl)propan-1-amine (1.2 g, crude) as an oil which was used in the next step directly without further purification.

Step 3

N-tert-Butyl-2-(1-(3-(dimethylamino)propyl)-6-methyl-1H-indazol-3-yl)-5H-pyrrolo[2,3-b]pyrazine-7-carboxamide hydrochloride

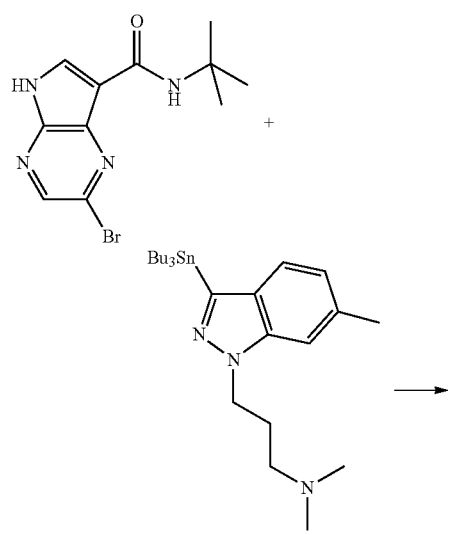

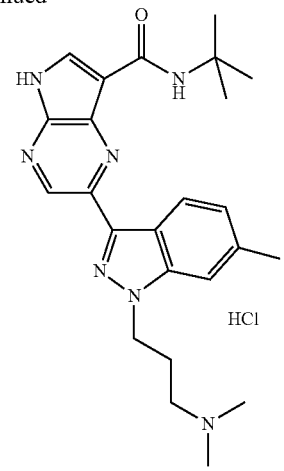

A mixture of 2-bromo-N-tert-butyl-5H-pyrrolo[2,3-b]pyrazine-7-carboxamide (150 mg, 0.5 mmol), N,N-dimethyl-3-(6-methyl-3-(tributylstannyl)-1H-indazol-1-yl)propan-1-amine (1.2 g, crude), tetrakis(triphenylphosphine)palladium (0) (40 mg, 0.035 mmol) and copper iodide (20 mg, 0.1 mmol) in 15 mL of dry DMF was heated to 90° C. for 3 hours under N₂. The reaction mixture was cooled to room temperature, 50 mL of water was added and some precipitate was formed. After filtration, the solid was dissolved in the solution of HCl in 1,4-dioxane (3 mL, 1N) and stirred for 5 mins. The reaction was concentrated and the residue was purified by preparative-HPLC (Gemini 5u C18 150×21.2 mm; inject volume: 3 mL/inj, flow rate: 20 mL/min; wavelength: 214 nm and 254 nm; the gradient conditions are: 40% acetonitrile/60% water (0.1% trifluoroacetic acid V/V) initially, and then proceed to 50% acetonitrile/50% water (0.1% trifluoroacetic acid V/V) in a linear fashion after just 9 min.), to yield 26 mg of N-tert-butyl-2-(1-(3-(dimethylamino)propyl)-6-methyl-1H-indazol-3-yl)-5H-pyrrolo[2,3-b]pyrazine-7-carboxamide hydrochloride. LCMS: (M+H)⁺=434; ¹H NMR (300 MHz, DMSO): δ 12.80 (s, 1H), 9.53 (s, 1H), 9.10 (s, 1H), 8.39-8.36 (m, 2H), 7.96 (s, 1H), 7.60 (s, 1H), 7.13-7.10 (m, 1H), 4.59-4.55 (m, 2H), 3.21-3.16 (m, 2H), 2.73 (s, 6H), 2.51-2.48 (m, 2H), 2.32-2.27 (m, 3H), 1.53 (s, 6H).

Example 428

N-(2-Cyclopropylpropan-2-yl)-2-(1,6-dimethyl-1H-indazol-3-yl)-5H-pyrrolo[3,2-b]pyrazine-7-carboxamide

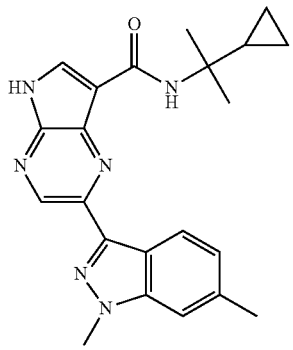

To a stirred mixture of 2-(1,6-dimethyl-1H-indazol-3-yl)-5H-pyrrolo[3,2-b]pyrazine-7-carboxylic acid (80 mg, 0.26 mmol) and 2-cyclopropylpropan-2-amine hydrochloride (53 mg, 0.39 mmol) in DMF (3 mL), was added EDCI (100 mg, 0.52 mmol) followed by DMAP (63 mg, 0.52 mmol). The mixture was stirred at room temperature for 16 hours, and then poured into water (5 mL) and filtered. The crude solid was purified by preparative-HPLC (Gemini 5u C18 150×21.2 mm; inject volume: 3 mL/inj, flow rate: 20 mL/min; wavelength: 214 nm and 254 nm; the gradient conditions were: 58% acetonitrile/42% water (0.1% trifluoroacetic acid, v/v) initially, proceeding to 88% acetonitrile/12% water (0.1% trifluoroacetic acid, v/v) in a linear fashion over 9 min.) to give N-(2-cyclopropylpropan-2-yl)-2-(1,6-dimethyl-1H-indazol-3-yl)-5H-pyrrolo[3,2-b]pyrazine-7-carboxamide (25 mg, 25%) as a white solid. MS: (M+H)$^+$=389; $^1$H NMR (300 MHz, DMSO): δ 9.10 (s, 1H), 8.39-8.36 (m, 2H), 7.97 (s, 1H), 7.55 (s, 1H), 7.08 (d, 1H, J=8.1 Hz), Hz), 4.16 (s, 3H), 2.52 (s, 3H), 1.59-1.53 (m, 1H), 1.25 (s, 6H), 0.47-0.43 (m, 4H).

Example 429

2-(1,6-Dimethyl-1H-indazol-3-yl)-N-(1-(hydroxymethyl)cyclopropyl)-5H-pyrrolo[3,2-b]pyrazine-7-carboxamide

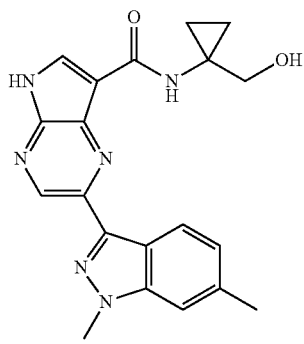 [SMILES: Cc1ccc2c(-c3cnc4[nH]cc(C(=O)NC5(CO)CC5)c4n3)nn(C)c2c1]

To a stirred mixture of 2-(1,6-dimethyl-1H-indazol-3-yl)-5H-pyrrolo[3,2-b]pyrazine-7-carboxylic acid (80 mg, 0.26 mmol) and (1-aminocyclopropyl)methanol (34 mg, 0.39 mmol) in DMF (3 mL), was added EDCI (100 mg, 0.52 mmol) followed by DMAP (63 mg, 0.52 mmol). The mixture was stirred at room temperature for 16 hours. Then the mixture was poured into water (5 mL) and filtered. The crude product was purified by preparative-HPLC (Gemini 5u C18 150×21.2 mm; inject volume: 3 mL/inj, flow rate: 20 mL/min; wavelength: 214 nm and 254 nm; the gradient conditions were: 35% acetonitrile/65% water (0.1% trifluoroacetic acid, v/v) initially, proceeding to 45% acetonitrile/55% water (0.1% trifluoroacetic acid, v/v) in a linear fashion over 9 min.) to give 2-(1,6-dimethyl-1H-indazol-3-yl)-N-(1-(hydroxymethyl)cyclopropyl)-5H-pyrrolo[3,2-b]pyrazine-7-carboxamide (35 mg, 36%) as a white solid. MS: (M+H)$^+$=377; $^1$H NMR (300 MHz, DMSO): δ 13.84 (s, 1H), 9.12 (s, 1H), 8.74 (s, 1H), 8.43-8.40 (m, 2H), 7.56 (s, 1H), 7.21 (d, 1H, J=8.4 Hz), 4.89 (brs, 1H), 4.16 (s, 3H), 3.62 (s, 2H), 2.55 (s, 3H), 0.97-0.86 (m, 4H).

Example 430

2-(1,6-Dimethyl-1H-indazol-3-yl)-N-(1-(dimethylamino)-2-methylpropan-2-yl)-5H-pyrrolo[3,2-b]pyrazine-7-carboxamide 2,2,2-trifluoroacetate

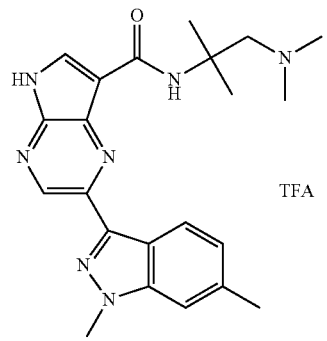 [SMILES: Cc1ccc2c(-c3cnc4[nH]cc(C(=O)NC(C)(C)CN(C)C)c4n3)nn(C)c2c1 ; "TFA"]

TFA

To a stirred mixture of 2-(1,6-dimethyl-1H-indazol-3-yl)-5H-pyrrolo[3,2-b]pyrazine-7-carboxylic acid (80 mg, 0.26 mmol) and N$^1$,N$^1$,2-trimethylpropane-1,2-diamine (45 mg, 0.39 mmol) in DMF (3 mL), was added EDCI (100 mg, 0.52 mmol) followed by DMAP (63 mg, 0.52 mmol). The mixture was stirred at room temperature for 16 hours. Then the mixture was poured into water (5 mL) and extracted with EtOAc (3×10 mL). The combined organic layers were washed with brine and dried over Na$_2$SO$_4$. After filtration and concentration, the residue was purified by preparative-HPLC (Gemini 5u C18 150×21.2 mm; inject volume: 3 mL/inj, flow rate: 20 mL/min; wavelength: 214 nm and 254 nm; the gradient conditions were: 20% acetonitrile/80% water (0.1% trifluoroacetic acid, v/v) initially, proceeding to 55% acetonitrile/45% water (0.1% trifluoroacetic acid, v/v) in a linear fashion over 9 min.) to give 2-(1,6-dimethyl-1H-indazol-3-yl)-N-(1-(dimethylamino)-2-methylpropan-2-yl)-5H-pyrrolo[3,2-b]pyrazine-7-carboxamide 2,2,2-trifluoroacetate (26 mg, 25%) as a yellow solid. MS: (M+H)$^+$=406; $^1$H NMR (300 MHz, CD$_3$OD): δ 9.07-9.05 (m, 1H), 8.51 (s, 1H), 8.34-8.32 (m, 1H), 8.22-8.19 (m, 1H), 7.33 (s, 1H), 7.07 (d, 1H, J=8.1 Hz), 4.08 (t, 1H, J=2.2 Hz), 3.77 (s, 2H), 3.03 (s, 6H), 2.54 (s, 3H), 1.74 (s, 6H).

Example 431

2-(6-Methyl-1H-indazol-3-yl)-N-(3-methylpyrrolidin-3-yl)-5H-pyrrolo[2,3-b]pyrazine-7-carboxamide 2,2,2-trifluoroacetate

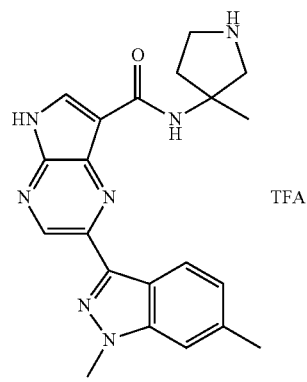 [SMILES: Cc1ccc2c(-c3cnc4[nH]cc(C(=O)NC5(C)CCNC5)c4n3)nn(C)c2c1 ; "TFA"]

TFA

Step 1 tert-Butyl 3-methyl-3-(2-(6-methyl-1H-indazol-3-yl)-5H-pyrrolo[2,3-b]pyrazine-7-carboxamido)pyrrolidine-1-carboxylate

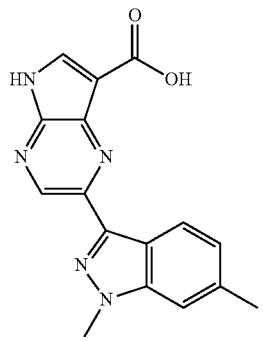

To a stirred solution of 2-(6-methyl-1H-indazol-3-yl)-5H-pyrrolo[2,3-b]pyrazine-7-carboxylic acid (100 mg, 0.34 mmol), EDCI (123 mg, 0.64 mmol), DMAP (110 mg, 0.90 mmol) and DIEA (131 mg, 1.02 mmol) in 6 mL of DMF was added tert-butyl 3-amino-3-methylpyrrolidine-1-carboxylate (100 mg, 0.54 mmol) in one portion at room temperature, then the mixture was stirred for 16 hours. The reaction mixture was poured into 40 mL of water, extracted with ethyl acetate (150 mL). The organic phase was evaporated at 40° C. under reduced pressure and the residue was triturated with petroleum ether then decanted and dried to give crude tert-butyl 3-methyl-3-(2-(6-methyl-1H-indazol-3-yl)-5H-pyrrolo[2,3-b]pyrazine-7-carboxamido)pyrrolidine-1-carboxylate (76 mg, 47.0%) as a yellow solid. MS: (M+H)$^+$=476.2.

Step 2

2-(6-Methyl-1H-indazol-3-yl)-N-(3-methylpyrrolidin-3-yl)-5H-pyrrolo[2,3-b]pyrazine-7-carboxamide 2,2,2-trifluoroacetate

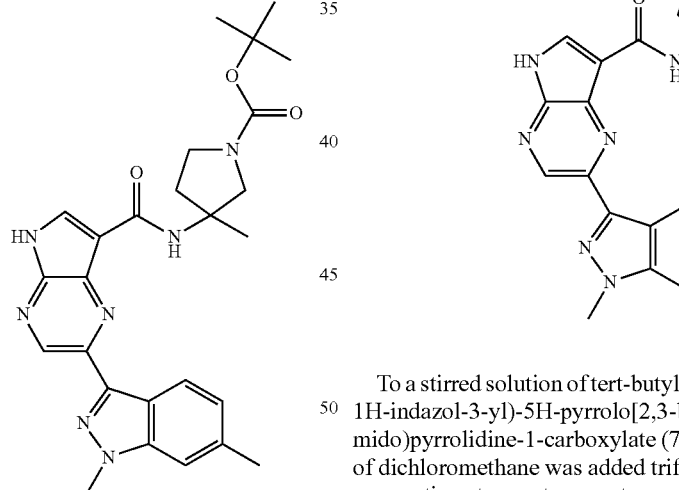

To a stirred solution of tert-butyl 3-methyl-3-(2-(6-methyl-1H-indazol-3-yl)-5H-pyrrolo[2,3-b]pyrazine-7-carboxamido)pyrrolidine-1-carboxylate (76 mg, 0.16 mmol) in 6 mL of dichloromethane was added trifluoroacetic acid (3 mL) in one portion at room temperature and stirred for one hour. The solvent was evaporated at 40° C. under reduced pressure and the residue was purified by preparative-HPLC (Gemini 5u C18 150×21.2 mm; inject volume: 3 mL/inj, flow rate: 20 mL/min; wavelength: 214 nm and 254 nm; the gradient conditions were: 20% acetonitrile/80% water (0.1% trifluoroacetic acid, v/v) initially, proceeding to 45% acetonitrile/65% water (0.1% trifluoroacetic acid, v/v) in a linear fashion over 9 min.) to give 2-(6-methyl-1H-indazol-3-yl)-N-(3-methylpyrrolidin-3-yl)-5H-pyrrolo[2,3-b]pyrazine-7-carboxamide 2,2,2-trifluoroacetate (18 mg, 22.9%) as a white solid. MS: (M+H)$^+$=376; $^1$H NMR (300 MHz, DMSO): δ 13.43 (s, 1H), 9.17 (s, 1H), 8.80 (brs, 1H), 8.49 (s, 1H), 8.38 (d, 1H, J=8.1 Hz), 8.29 (s, 1H), 7.47 (s, 1H), 7.16 (d, 1H, J=8.4 Hz), 3.94 (d, 1H, J=12.0 Hz), 3.51-3.20 (m, 3H), 2.57 (s, 3H), 2.30-2.17 (m, 2H), 1.70 (s, 3H).

Example 432

N-(1-(Hydroxymethyl)cyclopropyl)-2-(6-methyl-1H-indazol-3-yl)-5H-pyrrolo[2,3-b]pyrazine-7-carboxamide

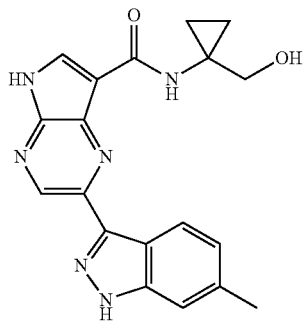 [SMILES: Cc1ccc2c(-c3cnc4[nH]cc(C(=O)NC5(CO)CC5)c4n3)n[nH]c2c1]

To a stirred solution of 2-(6-methyl-1H-indazol-3-yl)-5H-pyrrolo[2,3-b]pyrazine-7-carboxylic acid (100 mg, 0.34 mmol), EDCI (123 mg, 0.64 mmol) and DMAP (110 mg, 0.90 mmol) in 6 mL of DMF was added (1-aminocyclopropyl)methanol (59 mg, 0.68 mmol) in one portion at room temperature, then the mixture was stirred for 16 hours. The reaction mixture was poured into 40 mL of water, filtered and the filter cake was purified by preparative-HPLC (Gemini 5u C18 150×21.2 mm; inject volume: 3 mL/inj, flow rate: 20 mL/min; wavelength: 214 nm and 254 nm; the gradient conditions were: 25% acetonitrile/75% water (0.1% trifluoroacetic acid, v/v) initially, proceeding to 50% acetonitrile/50% water (0.1% trifluoroacetic acid, v/v) in a linear fashion over 9 min.) to give N-(1-(hydroxymethyl)cyclopropyl)-2-(6-methyl-1H-indazol-3-yl)-5H-pyrrolo[2,3-b]pyrazine-7-carboxamide (10 mg, 8.1%) as a yellow solid. MS: (M+H)$^+$=363; $^1$H NMR (300 MHz, DMSO): δ 13.36 (s, 1H), 12.81 (s, 1H), 9.16 (s, 1H), 8.75 (s, 1H), 8.40-8.38 (m, 2H), 7.43 (s, 1H), 7.16 (d, 1H, J=8.7 Hz), 4.89 (brs, 1H), 3.59 (brs, 2H), 2.54 (s, 3H), 0.92-0.83 (m, 4H).

Example 433

N-(2-Cyclopropylpropan-2-yl)-2-(6-methyl-1H-indazol-3-yl)-5H-pyrrolo[2,3-b]pyrazine-7-carboxamide

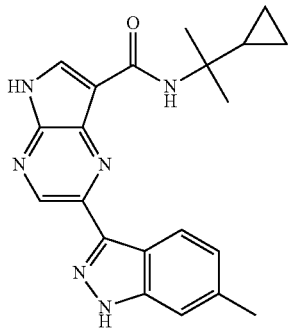 [SMILES: Cc1ccc2c(-c3cnc4[nH]cc(C(=O)NC(C)(C)C5CC5)c4n3)n[nH]c2c1]

To a stirred solution of 2-(6-methyl-1H-indazol-3-yl)-5H-pyrrolo[2,3-b]pyrazine-7-carboxylic acid (100 mg, 0.34 mmol), EDCI (130 mg, 0.68 mmol), DMAP (83 mg, 0.68 mmol) and DIEA (88 mg, 0.68 mmol) in 6 mL of DMF was added 2-cyclopropylpropan-2-amine hydrochloride (92 mg, 0.68 mmol) in one portion at room temperature, then the mixture was stirred for 16 hours. The reaction mixture was poured into 40 mL of water, filtered and the filter cake was purified by preparative-HPLC (Gemini 5u C18 150×21.2 mm; inject volume: 3 mL/inj, flow rate: 20 mL/min; wavelength: 214 nm and 254 nm; the gradient conditions were: 45% acetonitrile/55% water (0.1% trifluoroacetic acid, v/v) initially, proceeding to 75% acetonitrile/25% water (0.1% trifluoroacetic acid, v/v) in a linear fashion over 9 min.) to give N-(2-cyclopropylpropan-2-yl)-2-(6-methyl-1H-indazol-3-yl)-5H-pyrrolo[2,3-b]pyrazine-7-carboxamide (12 mg, 9.4%) as a yellow solid. MS: (M+H)$^+$=375; $^1$H NMR (300 MHz, DMSO): δ 13.38 (s, 1H), 12.80 (s, 1H), 9.16 (s, 1H), 8.41-8.35 (m, 2H), 7.95 (s, 1H), 7.41 (s, 1H), 7.06 (d, 1H, J=8.4 Hz), 2.57 (s, 3H), 1.67-1.54 (m, 1H), 1.59 (s, 6H), 0.48-0.44 (m, 4H).

Example 434

N-(1-Hydroxy-2-methylpropan-2-yl)-2-(6-methyl-1H-indazol-3-yl)-5H-pyrrolo[2,3-b]pyrazine-7-carboxamide

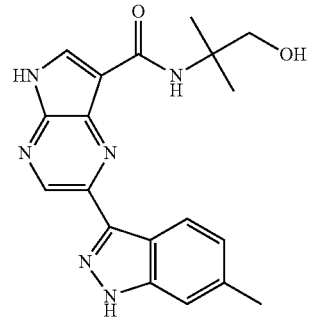 [SMILES: Cc1ccc2c(-c3cnc4[nH]cc(C(=O)NC(C)(C)CO)c4n3)n[nH]c2c1]

Step 1

N-(1-(tert-Butyldimethylsilyloxy)-2-methylpropan-2-yl)-2-(6-methyl-1H-indazol-3-yl)-5H-pyrrolo[2,3-b]pyrazine-7-carboxamide

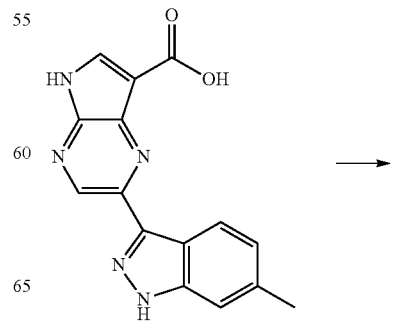

-continued

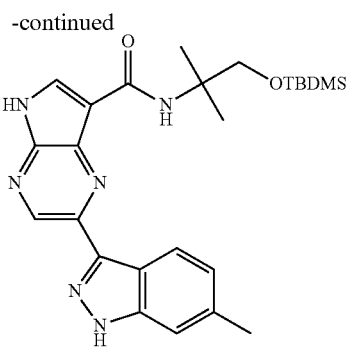

To a stirred solution of 2-(6-methyl-1H-indazol-3-yl)-5H-pyrrolo[2,3-b]pyrazine-7-carboxylic acid (100 mg, 0.34 mmol), EDCI (130 mg, 0.68 mmol), DMAP (83 mg, 0.68 mmol) and DIEA (88 mg, 0.68 mmol) in 6 mL of DMF was added 1-(tert-butyldimethylsilyloxy)-2-methylpropan-2-amine (138 mg, 0.68 mmol) in one portion at room temperature, then the mixture was stirred for 16 hours. The reaction mixture was poured into 40 mL of water, filtered and the filter cake was washed with petroleum ether to give crude N-(1-(tert-butyldimethylsilyloxy)-2-methylpropan-2-yl)-2-(6-methyl-1H-indazol-3-yl)-5H-pyrrolo[2,3-b]pyrazine-7-carboxamide (75 mg, 46.0%) as a pale yellow solid. MS: (M+H)$^+$=479.2.

Step 2

N-(1-Hydroxy-2-methylpropan-2-yl)-2-(6-methyl-1H-indazol-3-yl)-5H-pyrrolo[2,3-b]pyrazine-7-carboxamide

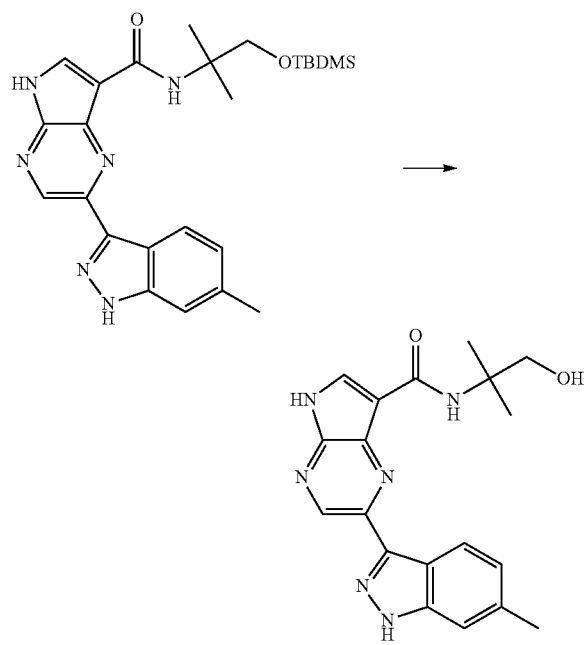

N-(1-(tert-Butyldimethylsilyloxy)-2-methylpropan-2-yl)-2-(6-methyl-1H-indazol-3-yl)-5H-pyrrolo[2,3-b]pyrazine-7-carboxamide (75 mg, 0.16 mmol) was added to a saturated solution of HCl (g) in dioxane (15 mL) at room temperature and stirred for 2 hours. The reaction mixture was filtered, the filter cake washed with 2 mL of methanol, then dried at 40° C. under reduced pressure to give N-(1-hydroxy-2-methylpropan-2-yl)-2-(6-methyl-1H-indazol-3-yl)-5H-pyrrolo[2,3-b]pyrazine-7-carboxamide (15 mg, 26.4%) as a yellow solid. MS: (M+H)$^+$=365; $^1$H NMR (300 MHz, DMSO): δ 13.34 (s, 1H), 12.76 (s, 1H), 9.14 (s, 1H), 8.46 (d, 1H, J=7.8 Hz), 8.35 (s, 1H), 7.95 (s, 1H), 7.41 (s, 1H), 7.09 (d, 1H, J=8.4 Hz), 5.05 (t, 1H, J=5.7 Hz), 3.65 (d, 1H, J=5.7 Hz), 2.50 (s, 3H), 1.46 (s, 6H).

Example 435

N-(1-amino-2-methylpropan-2-yl)-2-(6-methyl-1H-indazol-3-yl)-5H-pyrrolo[2,3-b]pyrazine-7-carboxamide hydrochloride

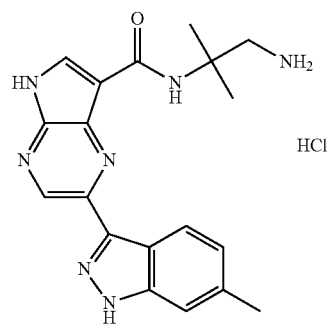 [SMILES: Cc1ccc2c(-c3cnc4[nH]cc(C(=O)NC(C)(C)CN)c4n3)n[nH]c2c1 ; Cl]

Step 1 tert-Butyl 2-methyl-2-(2-(6-methyl-1H-indazol-3-yl)-5H-pyrrolo[2,3-b]pyrazine-7-carboxamido)propylcarbamate

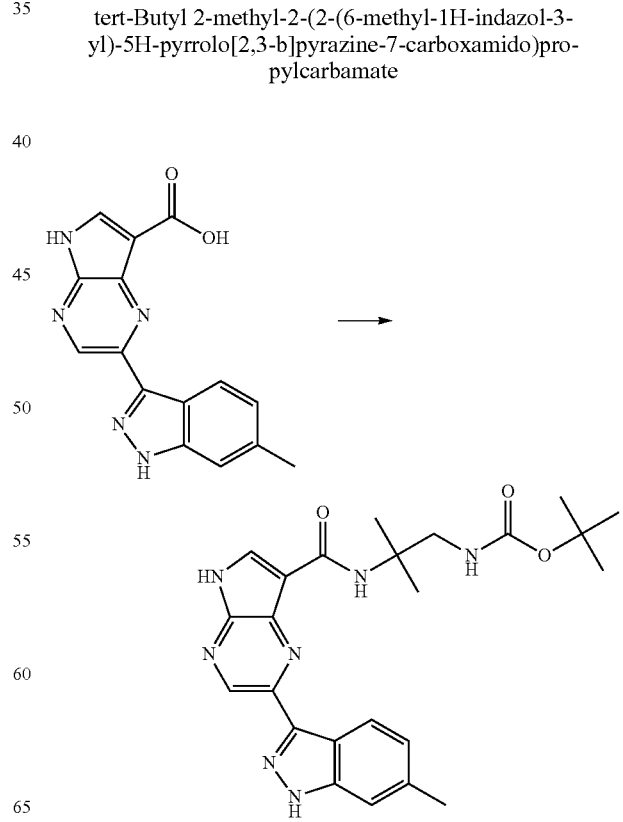

To a stirred solution of 2-(6-methyl-1H-indazol-3-yl)-5H-pyrrolo[2,3-b]pyrazine-7-carboxylic acid (100 mg, 0.34 mmol), EDCI (130 mmol, 0.68 mmol), DMAP (83 mg, 0.68 mmol) and DIEA (88 mg, 0.68 mmol) in 6 mL of DMF was added tert-butyl 2-amino-2-methylpropylcarbamate (128 mg, 0.68 mmol) in one portion at room temperature, then the mixture was stirred for 16 hours. The reaction mixture was poured into 40 mL of water, filtered and the filter cake was washed with petroleum ether to give crude tert-butyl 2-methyl-2-(2-(6-methyl-1H-indazol-3-yl)-5H-pyrrolo[2,3-b]pyrazine-7-carboxamido)propylcarbamate (100 mg, 63.4%) as a pale yellow solid. MS: (M+H)$^+$=463.2.

Step 2

N-(1-Amino-2-methylpropan-2-yl)-2-(6-methyl-1H-indazol-3-yl)-5H-pyrrolo[2,3-b]pyrazine-7-carboxamide hydrochloride

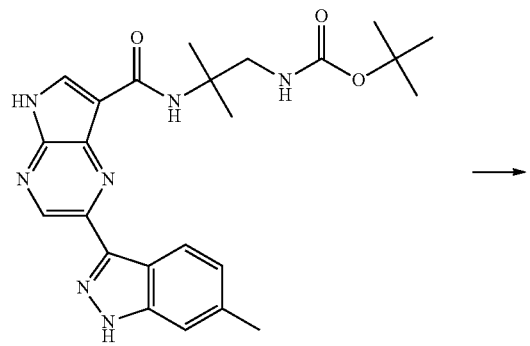

tert-Butyl 2-methyl-2-(2-(6-methyl-1H-indazol-3-yl)-5H-pyrrolo[2,3-b]pyrazine-7-carboxamido)propylcarbamate (100 mg, 0.22 mmol) was added to a saturated solution of HCl gas in ethyl acetate (20 mL) and the mixture was stirred at room temperature for 3 hours. The solid obtained was filtered and washed with 5 mL of ethyl acetate to give N-(1-amino-2-methylpropan-2-yl)-2-(6-methyl-1H-indazol-3-yl)-5H-pyrrolo[2,3-b]pyrazine-7-carboxamide hydrochloride (25 mg, 32%) as a yellow solid. MS: (M+H)$^+$=364; $^1$H NMR (300 MHz, DMSO): δ 13.45 (s, 1H), 12.96 (s, 1H), 9.19 (s, 1H), 8.47-8.40 (m, 2H), 8.12-8.10 (m, 3H), 7.46 (s, 1H), 7.12 (d, 1H, J=8.4 Hz), 3.84 (brs, 5H), 3.42 (d, 2H, J=4.8 Hz), 2.52 (s, 3H), 1.58 (s, 3H).

Example 436

N-(1-(Dimethylamino)-2-methylpropan-2-yl)-2-(6-methyl-1H-indazol-3-yl)-5H-pyrrolo[2,3-b]pyrazine-7-carboxamide

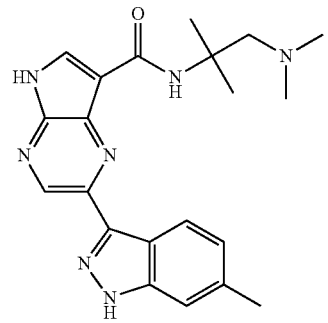 [SMILES: Cc1ccc2c(-c3cnc4[nH]cc(C(=O)NC(C)(C)CN(C)C)c4n3)n[nH]c2c1]

To a stirred solution of 2-(6-methyl-1H-indazol-3-yl)-5H-pyrrolo[2,3-b]pyrazine-7-carboxylic acid (100 mg, 0.34 mmol), DCI (123 mg, 0.64 mmol) and DMAP (110 mg, 0.90 mmol) in 6 mL of DMF was added N$^1$,N$^1$,2-trimethylpropane-1,2-diamine (100 mg, 0.86 mmol) in one portion at room temperature, then the mixture was stirred for 16 hours. The reaction mixture was poured into 40 mL of water, filtered and the filter cake was purified by column chromatography (silica gel, 200-300 mesh, eluting with a mixture of methanol and THF (1:3, v/v) to give N-(1-(dimethylamino)-2-methylpropan-2-yl)-2-(6-methyl-1H-indazol-3-yl)-5H-pyrrolo[2,3-b]pyrazine-7-carboxamide (22 mg, 16.5%) as a yellow solid. MS: (M+H)$^+$=392; $^1$H NMR (300 MHz, DMSO): δ 13.38 (s, 1H), 12.90 (brs, 1H), 9.15 (s, 1H), 8.47 (d, 1H, J=8.4 Hz), 8.37 (s, 1H), 7.97 (s, 1 h), 7.45 (s, 1H), 7.10 (d, 1H, J=8.4 Hz), 2.74 (s, 2H), 2.52 (s, 3H), 2.29 (s, 3H), 2.26 (s, 3H), 2.01 (s, 6H).

Example 437

N-(1-Cyanocyclopropyl)-2-(6-methyl-1H-indazol-3-yl)-5H-pyrrolo[2,3-b]pyrazine-7-carboxamide

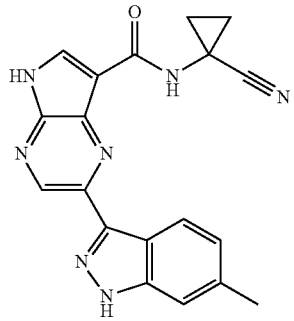 [SMILES: Cc1ccc2c(-c3cnc4[nH]cc(C(=O)NC5(C#N)CC5)c4n3)n[nH]c2c1]

To a stirred solution of 2-(6-methyl-1H-indazol-3-yl)-5H-pyrrolo[2,3-b]pyrazine-7-carboxylic acid (100 mg, 0.34 mmol), DIEA (200 mg, 1.55 mmol), EDCI (123 mg, 0.64 mmol) and DMAP (110 mg, 0.90 mmol) in 6 mL of DMF was added 1-aminocyclopropanecarbonitrile hydrochloride (100 mg, 0.84 mmol) in one portion at room temperature, then the mixture was stirred for 16 hours. The reaction mixture was poured into 40 mL of water, filtered and the filter cake was purified by preparative-HPLC (Gemini 5u C18 150×21.2 mm; inject volume: 3 mL/inj, flow rate: 20 mL/min; wavelength: 214 nm and 254 nm; the gradient conditions were: 35% acetonitrile/65% water (0.1% trifluoroacetic acid, v/v) initially, proceeding to 70% acetonitrile/30% water (0.1% trifluoroacetic acid, v/v) in a linear fashion over 9 min.) to give N-(1-cyanocyclopropyl)-2-(6-methyl-1H-indazol-3-yl)-5H-pyrrolo[2,3-b]pyrazine-7-carboxamide (5 mg, 4.1%) as a yellow solid. MS: (M+H)$^+$=358; $^1$H NMR (300 MHz, DMSO): δ 13.40 (s, 1H), 13.00 (s, 1H), 9.19 (s, 1H), 8.98 (s, 1H), 8.56 (d, 1H, J=3.0 Hz), 8.38 (d, 1H, J=8.1 Hz), 7.46 (s, 1H), 7.21 (d, 1H, J=8.4 Hz), 2.53 (s, 3H), 1.78-1.74 (m, 2H), 1.48-1.44 (m, 2H).

Example 438

N-(1-Hydroxy-2-methylpropan-2-yl)-2-(6-methyl-1-(3-morpholinopropyl)-1H-indazol-3-yl)-5H-pyrrolo[3,2-b]pyrazine-7-carboxamidehydrochloride

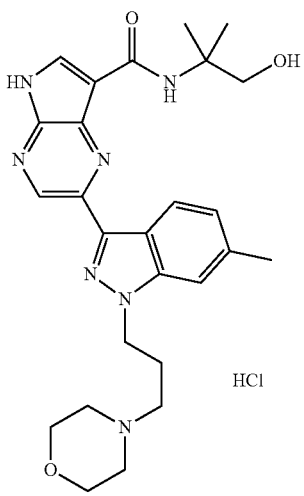 [SMILES: Cc1ccc2c(-c3cnc4[nH]cc(C(=O)NC(C)(C)CO)c4n3)nn(CCCN3CCOCC3)c2c1 ; Cl]

Step 1

2-Bromo-N-(1-(tert-butyldimethylsilyloxy)-2-methylpropan-2-yl)-5H-pyrrolo[3,2-b]pyrazine-7-carboxamide

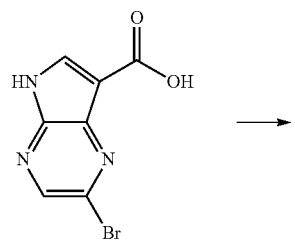

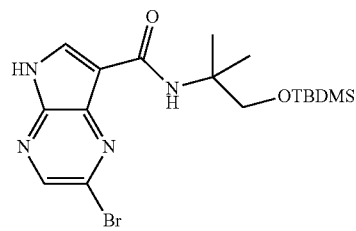

A mixture of 2-bromo-5H-pyrrolo[3,2-b]pyrazine-7-carboxylic acid (2.5 g, 10.33 mmol), 1-(tert-butyldimethylsilyloxy)-2-methylpropan-2-amine (2.52 g, 12.4 mmol), EDCI (1.97 g, 10.33 mmol), HOBt (2.8 g, 20.6 mmol) and DIPEA (2.7 g, 20.66 mmol) in dry DMF (30 mL) was heated to 30° C. for 16 hours. Then water (30 mL) was added, the formed precipitate was separated by filtration and the filter cake was washed with water (10 mL) and dried to afford 1-(2-bromo-5H-pyrrolo[3,2-b]pyrazin-7-yl)-2-(1-(tert-butyldimethylsilyloxy)-2-methylpropan-2-ylamino)ethanone (2.7 g, 61%) as a yellow solid. LCMS: (M+H)$^+$=427.

Step 2

2-Bromo-N-(1-(tert-butyldimethylsilyloxy)-2-methylpropan-2-yl)-5-trityl-5H-pyrrolo[3,2-b]pyrazine-7-carboxamide

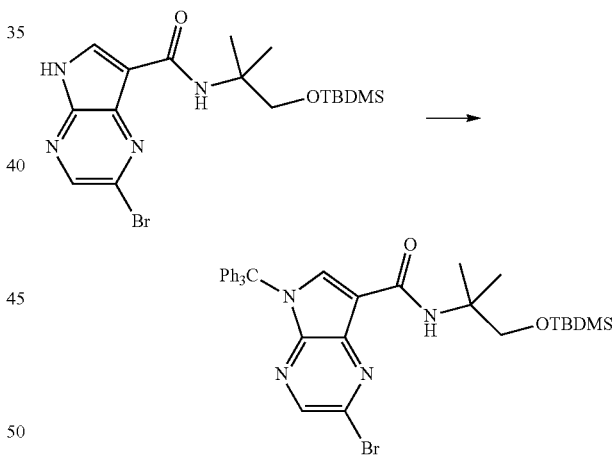

A mixture of 1-(2-bromo-5H-pyrrolo[3,2-b]pyrazin-7-yl)-2-(1-(tert-butyldimethyl silyloxy)-2-methylpropan-2-ylamino)ethanone (1.3 g, 3.04 mmol), chlorotriphenylmethane (1.0 g, 3.65 mmol) and triethylamine (0.46 g, 4.56 mmol) in dry DMF (20 mL) was heated to 90° C. for 5 hours. Product was extracted with ethyl acetate (200 mL), organic phase washed with water (3×20 mL) and brine (2×20 mL). The organic layer was then dried over Na$_2$SO$_4$, filtered and concentrated and the residue was purified by column chromatography (silica gel, 200-300 mesh, eluting with ethyl acetate:petroleum ether=1:10) to afford 2-bromo-N-(1-(tert-butyldimethylsilyloxy)-2-methylpropan-2-yl)-5-trityl-5H-pyrrolo[3,2-b]pyrazine-7-carboxamide (1.73 g, 85%) as a yellow solid. $^1$H NMR (300 MHz, CDCl$_3$): 8.29 (s, 1H), 8.00

(s, 1H), 7.93 (s, 1H), 7.29-7.26 (m, 9H), 7.14-7.11 (m, 6H), 3.71 (s, 2H), 1.48 (s, 6H), 0.90 (s, 9H), 0.11 (s, 6H).

Step 3

N-(1-(tert-Butyldimethylsilyloxy)-2-methylpropan-2-yl)-2-(6-methyl-1H-indazol-3-yl)-5-trityl-5H-pyrrolo[3,2-b]pyrazine-7-carboxamide

Step 4

N-(1-(tert-Butyldimethylsilyloxy)-2-methylpropan-2-yl)-2-(6-methyl-1-(3-morpholinopropyl)-1H-indazol-3-yl)-5-trityl-5H-pyrrolo[3,2-b]pyrazine-7-carboxamide

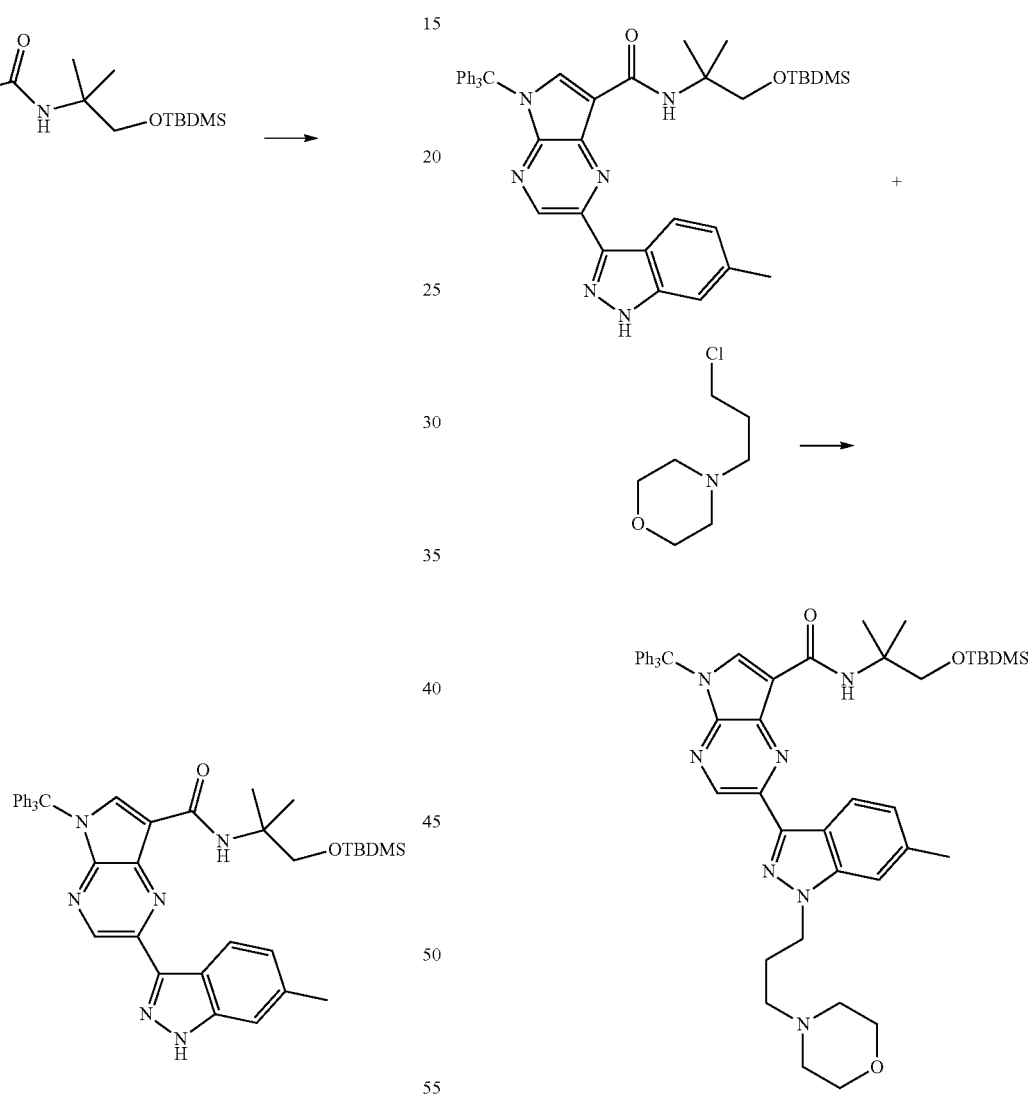

A mixture of 2-bromo-N-(1-(tert-butyldimethylsilyloxy)-2-methylpropan-2-yl)-5-trityl-5H-pyrrolo[3,2-b]pyrazine-7-carboxamide (1.73 g, 2.58 mmol), 6-methyl-3-(tributylstannyl)-1H-indazole (1.2 g, 2.84 mmol), Pd(PPh$_3$)$_4$ (298 mg, 0.258 mmol) and CuI (98 mg, 0.516 mmol) in dry DMF (20 mL) was heated to 90° C. for 4 hours. Product was extracted with ethyl acetate (200 mL), organic phase washed with water (2×50 mL) and brine (2×50 mL), then dried over Na$_2$SO$_4$, filtered and concentrated. The residue was triturated with petroleum ether (10 mL) then decanted and dried to afford N-(1-(tert-butyldimethylsilyloxy)-2-methylpropan-2-yl)-2-(6-methyl-1H-indazol-3-yl)-5-trityl-5H-pyrrolo[3,2-b]pyrazine-7-carboxamide (1.21 g, 65%) as a yellow solid. LCMS: (M+H)$^+$=721.

A mixture of N-(1-(tert-butyldimethylsilyloxy)-2-methylpropan-2-yl)-2-(6-methyl-1H-indazol-3-yl)-5-trityl-5H-pyrrolo[3,2-b]pyrazine-7-carboxamide (100 mg, 0.139 mmol), 4-(3-chloropropyl)morpholine (27 mg, 0.166 mmol) and K$_2$CO$_3$ (58 mg, 0.417 mmol) in dry DMF (20 mL) was heated to 90° C. for 3 hours. Product was extracted with ethyl acetate (100 mL), organic phase washed with water (3×10 mL) and brine (2×10 mL), then dried over Na$_2$SO$_4$, filtered and concentrated to afford N-(1-(tert-butyldimethylsilyloxy)-2-methylpropan-2-yl)-2-(6-methyl-1-(3-morpholinopropyl)-1H- indazol-3-yl)-5-trityl-5H-pyrrolo[3,2-b]pyrazine-7-carboxamide (95 mg, crude) as a yellow oil. LCMS: (M+H)+= 848.

Step 5

N-(1-Hydroxy-2-methylpropan-2-yl)-2-(6-methyl-1-(3-morpholinopropyl)-1H-indazol-3-yl)-5H-pyrrolo[3,2-b]pyrazine-7-carboxamide hydrochloride

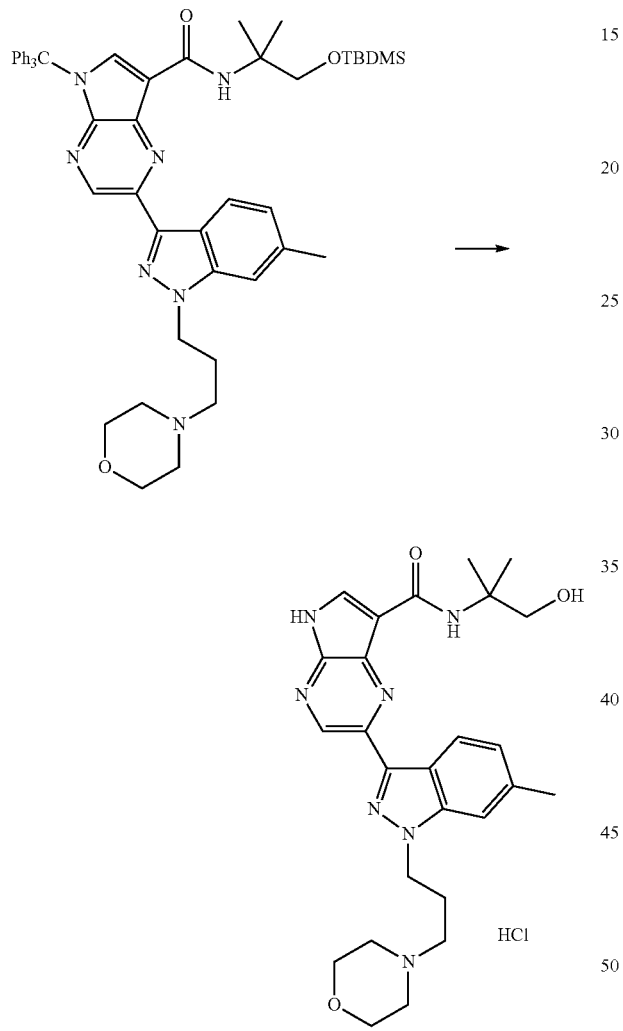

To a stirred solution of N-(1-(tert-butyldimethylsilyloxy)-2-methylpropan-2-yl)-2-(6-methyl-1-(3-morpholinopropyl)-1H-indazol-3-yl)-5-trityl-5H-pyrrolo[3,2-b]pyrazine-7-carboxamide (95 mg, 0.112 mmol) in dioxane (40 mL) was bubbled HCl gas until saturation and then stirred at room temperature for 16 hours. Reaction mixture was concentrated and the residue was triturated with methanol (1 mL) then decanted and dried to afford N-(1-hydroxy-2-methylpropan-2-yl)-2-(6-methyl-1-(3-morpholinopropyl)-1H-indazol-3-yl)-5H-pyrrolo[3,2-b]pyrazine-7-carboxamide hydrochloride (42 mg, 71%) as a yellow solid. LCMS: (M+H)+=492; $^1$H NMR (300 MHz, DMSO+D$_2$O): δ 9.14 (s, 1H), 8.44 (d, 1H, J=8.1 Hz), 8.36 (s, 1H), 7.59 (s, 1H), 7.17 (d, 1H, J=8.4 Hz), 4.59-4.56 (m, 2H), 4.03-3.99 (m, 2H), 3.78-3.75 (m, 4H), 3.43-3.18 (m, 6H), 2.54 (s, 3H), 2.36 (brs, 2H), 1.43 (s, 6H).

Example 439

N-(1-Hydroxy-2-methylpropan-2-yl)-2-(6-methyl-1-(2-morpholino-2-oxoethyl)-1H-indazol-3-yl)-5H-pyrrolo[3,2-b]pyrazine-7-carboxamide hydrochloride Step 1

N-(1-(tert-Butyldimethylsilyloxy)-2-methylpropan-2-yl)-2-(6-methyl-1-(2-morpholino-2-oxoethyl)-1H-indazol-3-yl)-5-trityl-5H-pyrrolo[3,2-b]pyrazine-7-carboxamide

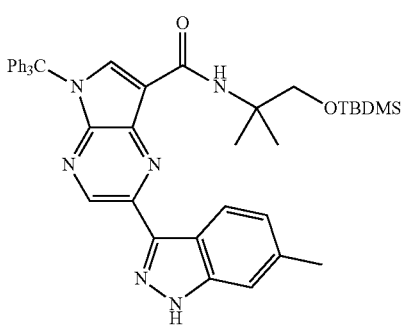

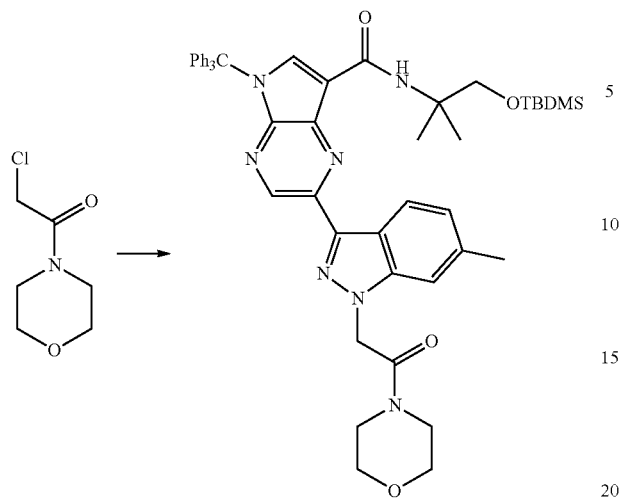
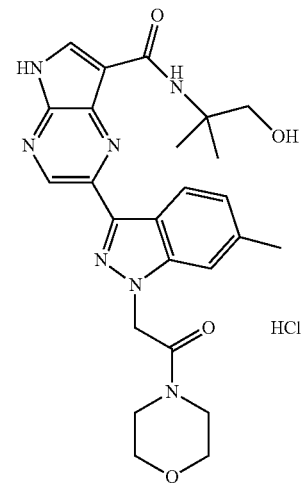

A mixture of N-(1-(tert-butyldimethylsilyloxy)-2-methylpropan-2-yl)-2-(6-methyl-1H-indazol-3-yl)-5-trityl-5H-pyrrolo[3,2-b]pyrazine-7-carboxamide (100 mg, 0.139 mmol), 2-chloro-1-morpholinoethanone (27 mg, 0.166 mmol) and K$_2$CO$_3$ (58 mg, 0.417 mmol) in dry DMF (20 mL) was heated to 90° C. for 3 hours. After cooling to room temperature, ethyl acetate (100 mL) was added, and the solution was washed with water (3×10 mL) and brine (2×10 mL). The combined organic layers were dried over Na$_2$SO$_4$, concentrated to give the residue which was used into the next step without further purification. LCMS: (M+H)$^+$=848.

Step 2

N-(1-Hydroxy-2-methylpropan-2-yl)-2-(6-methyl-1-(2-morpholino-2-oxoethyl)-1H-indazol-3-yl)-5H-pyrrolo[3,2-b]pyrazine-7-carboxamide hydrochloride To a stirred solution of N-(1-(tert-butyldimethylsilyloxy)-2-methylpropan-2-yl)-2-(6-methyl-1-(2-morpholino-2-oxoethyl)-1H-indazol-3-yl)-5-trityl-5H-pyrrolo[3,2-b]pyrazine-7-carboxamide (100 mg, 0.118 mmol) in dioxane (40 mL) was bubbled HCl gas until saturation and then stirred at room temperature for 16 hours. The mixture was concentrated and the residue was triturated with methanol (1 mL), solvent decanted and solid dried to afford N-(1-hydroxy-2-methylpropan-2-yl)-2-(6-methyl-1-(2-morpholino-2-oxoethyl)-1H-indazol-3-yl)-5H-pyrrolo[3,2-b]pyrazine-7-carboxamide hydrochloride (44 mg, 71%) as a yellow solid. LCMS: (M+H)$^+$=492; $^1$H NMR (300 MHz, DMSO+D$_2$O): δ 9.07 (s, 1H), 8.44 (d, 1H, J=8.4 Hz), 8.36 (s, 1H), 7.45 (s, 1H), 7.15 (d, 1H, J=8.4 Hz), 5.55 (s, 2H), 3.72-3.65 (m, 8H), 3.47 (brs, 2H), 2.53 (s, 3H), 2.36 (brs, 2H), 1.46 (s, 6H).

Example 440

2-(1-(3-(Dimethylamino)propyl)-6-methyl-1H-indazol-3-yl)-N-(1-hydroxy-2-methylpropan-2-yl)-5H-pyrrolo[2,3-b]pyrazine-7-carboxamide hydrochloride

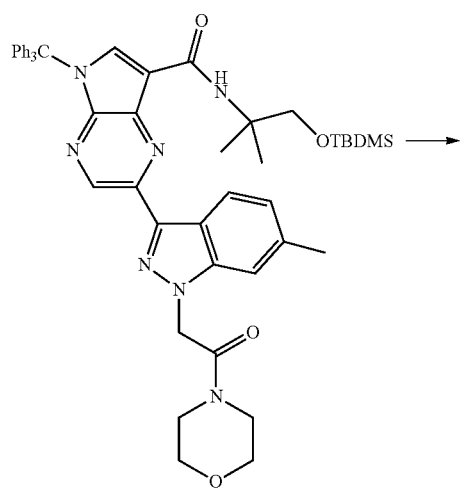
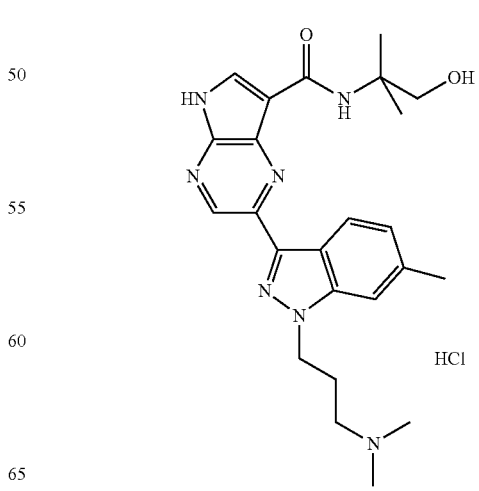

Step 1

N,N-Dimethyl-3-(6-methyl-3-(tributylstannyl)-1H-indazol-1-yl)propan-1-amine

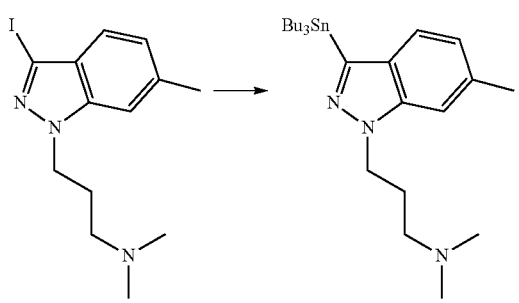

A solution of 3-(3-Iodo-6-methyl-1H-indazol-1-yl)-N,N-dimethylpropan-1-amine (480 mg, 1.4 mmol) in 20 mL of dry THF was cooled to −20° C. under nitrogen atmosphere, isopropylmagnesium chloride (1.4 mL, 2.8 mmol, 2M in THF) was added and stirred for 15 min at −20° C. Then tributylchlorostannane (0.8 mL, 2.8 mmol) was added and allowed to warm to room temperature. The reaction was cooled in an ice bath and quenched with saturated ammonium chloride solution, product extracted with ethyl acetate (3×50 mL), combined organics dried with sodium sulfate and concentrated to give 1.4 g of crude N,N-dimethyl-3-(6-methyl-3-(tributylstannyl)-1H-indazol-1-yl)propan-1-amine as an oil which was used in the next step directly without further purification.

Step 2

N-(1-(tert-Butyldimethylsilyloxy)-2-methylpropan-2-yl)-2-(1-(3-(dimethylamino)propyl)-6-methyl-1H-indazol-3-yl)-5H-pyrrolo[2,3-b]pyrazine-7-carboxamide

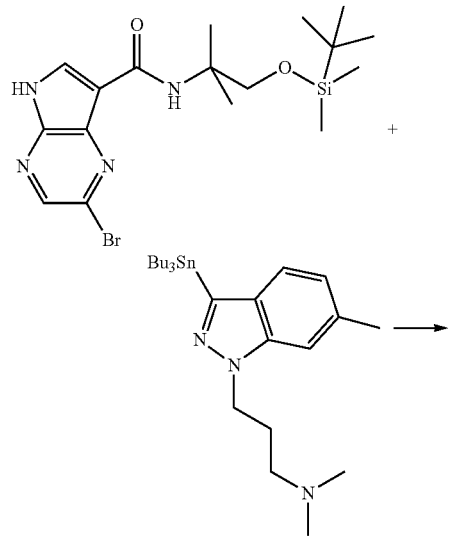

-continued

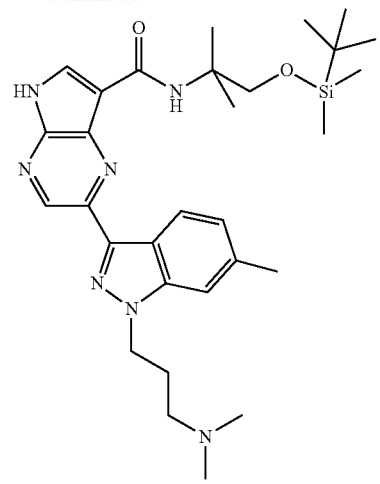

A mixture of 2-bromo-N-(1-(tert-butyldimethylsilyloxy)-2-methylpropan-2-yl)-5H-pyrrolo[2,3-b]pyrazine-7-carboxamide (300 mg, 0.7 mmol) and N,N-dimethyl-3-(6-methyl-3-(tributylstannyl)-1H-indazol-1-yl)propan-1-amine (1.4 g, 2.76 mmol) with tetrakis(triphenylphosphine)palladium(0) (10 mg, 0.087 mmol), copper iodide (10 mg, 0.52 mmol) in 15 mL of dry DMF was heated to 85° C. overnight under N$_2$. The reaction mixture was cooled to room temperature, diluted with 50 mL of water and the formed solid was separated by filtration. The solid was washed with 2-methoxy-2-methylpropane (5 mL) to give N-(1-(tert-butyldimethylsilyloxy)-2-methylpropan-2-yl)-2-(1-(3-(dimethylamino)propyl)-6-methyl-1H-indazol-3-yl)-5H-pyrrolo[2,3-b]pyrazine-7-carboxamide (1 g, crude) which was used in the next step directly without further purification. LCMS: (M+H)$^+$=564.

Step 3

2-(1-(3-(Dimethylamino)propyl)-6-methyl-1H-indazol-3-yl)-N-(1-hydroxy-2-methylpropan-2-yl)-5H-pyrrolo[2,3-b]pyrazine-7-carboxamide hydrochloride

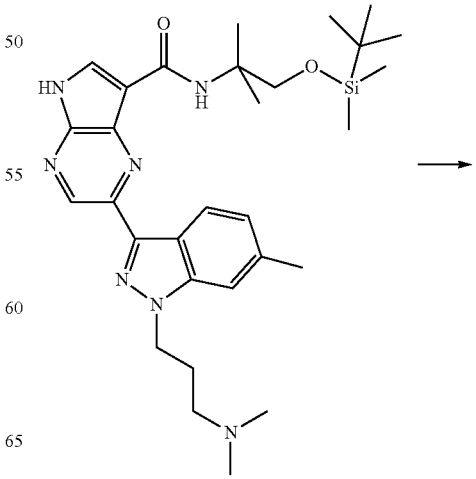

-continued

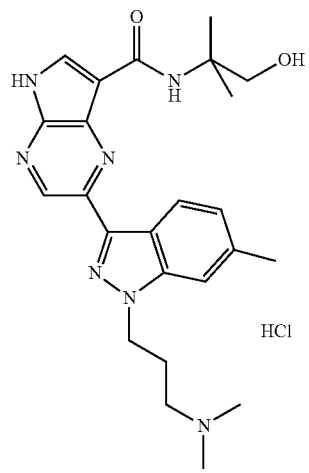 [SMILES: Cc1ccc2c(-c3cnc4[nH]cc(C(=O)NC(C)(C)CO)c4n3)nn(CCCN(C)C)c2c1 ; Cl]

HCl

To the solution of N-(1-(tert-butyldimethylsilyloxy)-2-methylpropan-2-yl)-2-(1-(3-(dimethylamino)propyl)-6-methyl-1H-indazol-3-yl)-5H-pyrrolo[2,3-b]pyrazine-7-carboxamide (1 g, 1.78 mmol) in 10 mL of methanol was added 1 mL of concentrated HCl, stirred for 3 hours, the precipitate was filtered and the filter cake was washed with 2-methoxy-2-methylpropane to give 25 mg of 2-(1-(3-(dimethylamino)propyl)-6-methyl-1H-indazol-3-yl)-N-(1-hydroxy-2-methylpropan-2-yl)-5H-pyrrolo[2,3-b]pyrazine-7-carboxamide hydrochloride. LCMS: (M+H)$^+$=450; $^1$H NMR (300 MHz, DMSO): δ 12.84 (s, 1H), 9.55 (s, 1H), 9.14 (s, 1H), 8.49 (d, 1H, J=8.1 Hz), 8.40 (s, 1H), 7.96 (s, 1H), 7.62 (s, 1H), 7.17 (d, 1H, J=8.4 Hz), 4.61-4.58 (m, 2H), 3.67 (s, 2H), 3.21 (s, 2H), 2.82 (s, 6H), 2.55 (s, 3H), 2.33 (brs, 2H), 1.49 (s, 6H).

Example 441

2-(5-(Difluoromethoxy)-1-(3-(dimethylamino)propyl)-1H-indazol-3-yl)-N-(1-hydroxy-2-methylpropan-2-yl)-5H-pyrrolo[3,2-b]pyrazine-7-carboxamide

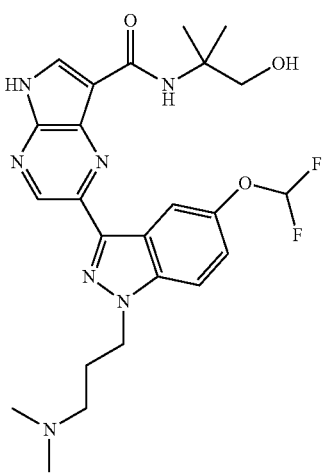 [SMILES: CN(C)CCCn1nc(-c2cnc3[nH]cc(C(=O)NC(C)(C)CO)c3n2)c2cc(OC(F)F)ccc21]

Step 1

3-(5-(Difluoromethoxy)-3-iodo-1H-indazol-1-yl)-N,N-dimethylpropan-1-amine

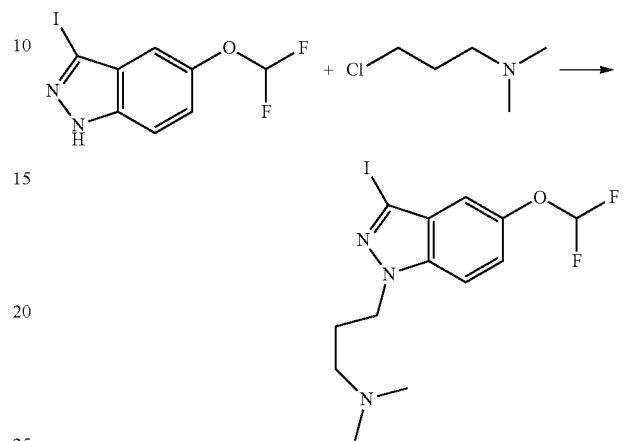

To a solution of 5-(difluoromethoxy)-3-iodo-1H-indazole (1 g, 3.2 mmol) in DMF (25 mL) was added K$_2$CO$_3$ (1.8 g, 12.8 mmol) and 3-chloro-N,N-dimethylpropan-1-amine (1.1 g, 6.4 mmol), after the addition, the reaction mixture was stirred at 80° C. for 4 hour. After cooling to room temperature, H$_2$O (25 mL) was added and product extracted with ethyl acetate (100 mL). The organic layer was washed with H$_2$O (100 mL), brine (100 mL), dried over Na$_2$SO$_4$ and concentrated under reduced pressure, the residue was purified by column chromatography (silica gel, 200-300 mesh, eluting with dichloromethane/CH$_3$OH=10:1) to give 3-(5-(difluoromethoxy)-3-iodo-1H-indazol-1-yl)-N,N-dimethylpropan-1-amine (1.1 g, 78.5%) as yellow oil. $^1$H NMR (300 MHz, CDCl$_3$): δ 7.46-7.42 (m, 1H), 7.27-7.17 (m, 2H), 6.87-6.29 (t, 1H, J=73.8 Hz), 4.47-4.41 (m, 2H), 2.24-2.18 (m, 8H), 2.08-2.03 (m, 2H). LCMS: (M+H)$^+$=396.

Step 2

3-(5-(Difluoromethoxy)-3-(tributylstannyl)-1H-indazol-1-yl)-N,N-dimethylpropan-1-amine

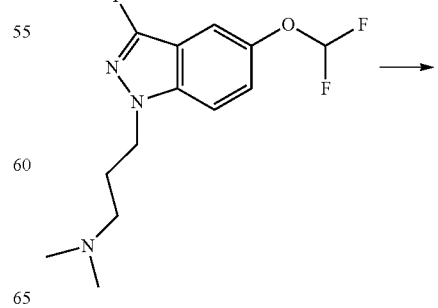

-continued

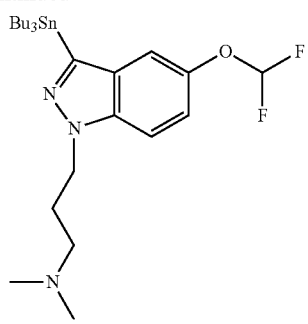

To a solution of 3-(5-(difluoromethoxy)-3-iodo-1H-indazol-1-yl)-N,N-dimethylpropan-1-amine (1.2 g, 2.78 mmol) in dry THF (25 mL) was added isopropylmagnesium chloride (1.5 mL, 2M in THF, 3 mmol) drop-wise at −16° C. under nitrogen atmosphere, stirred for 30 minutes, tributylchlorostannane (3.3 mL, 3.6 mmol) was added drop-wise at −16° C. under nitrogen, then the reaction mixture was warmed to room temperature slowly and stirred for 2 hours. Then the reaction mixture was quenched with a saturated solution of NH$_4$Cl (40 mL) and extracted with EtOAc (3×30 mL), the combined organic layer were dried over Na$_2$SO$_4$, filtered and concentrated under reduced pressure to give 3-(5-(difluoromethoxy)-3-(tributylstannyl)-1H-indazol-1-yl)-N,N-dimethylpropan-1-amine, (1.1 g, 71%) as an oil, used into the next step without purification.

Step 3

N-(1-(tert-Butyldimethylsilyloxy)-2-methylpropan-2-yl)-2-(5-(difluoromethoxy)-1-(3-(dimethylamino)propyl)-1H-indazol-3-yl)-5-trityl-5H-pyrrolo[3,2-b]pyrazine-7-carboxamide

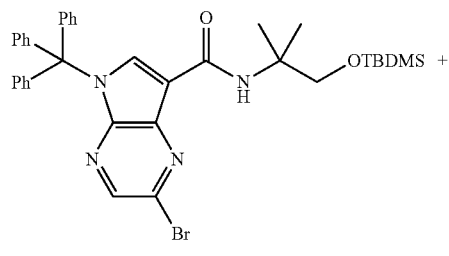

+

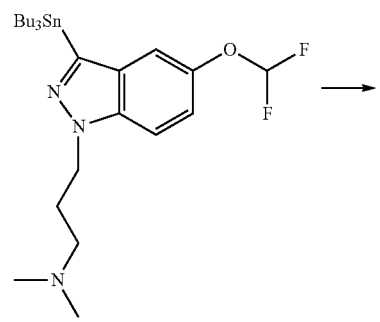

-continued

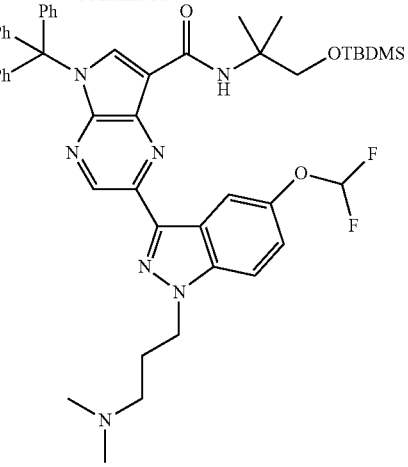

To a solution of 3-(5-(difluoromethoxy)-3-(tributylstannyl)-1H-indazol-1-yl)-N,N-dimethylpropan-1-amine (120 mg, 0.22 mmol) and 2-bromo-N-(1-(tert-butyldimethylsilyloxy)-2-methylpropan-2-yl)-5-trityl-5H-pyrrolo[3,2-b]pyrazine-7-carboxamide (200 mg, 0.26 mmol) in DMF (10 mL) were added CuI (30 mg, 0.16 mmol) and Pd(PPh$_3$)$_4$ (47 mg, 0.041 mmol), Then the reaction mixture was degassed by bubbling nitrogen for 3 minutes and refilled with nitrogen. The mixture was heated to 80° C. for 5 hours under nitrogen. After cooling to room temperature, water (50 mL) was added and product extracted with EtOAc (3×40 mL), the combined organic layers were dried over Na$_2$SO$_4$, filtered and concentrated to give N-(1-(tert-butyldimethylsilyloxy)-2-methylpropan-2-yl)-2-(5-(difluoromethoxy)-1-(3-(dimethylamino)propyl)-1H-indazol-3-yl)-5-trityl-5H-pyrrolo[3,2-b]pyrazine-7-carboxamide (88 mg, crude) as a yellow oil. LCMS: (M+H)$^+$=858.

Step 4

2-(5-(Difluoromethoxy)-1-(3-(dimethylamino)propyl)-1H-indazol-3-yl)-N-(1-hydroxy-2-methylpropan-2-yl)-5H-pyrrolo[3,2-b]pyrazine-7-carboxamide

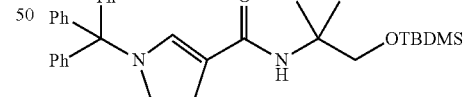

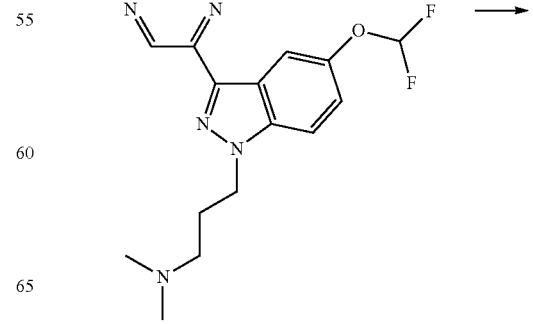

-continued

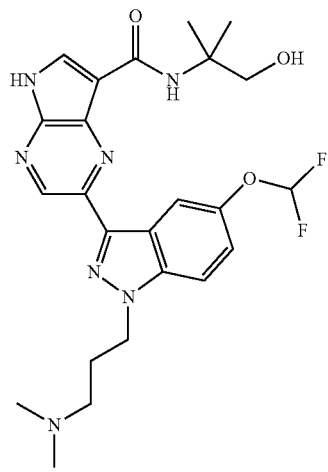

To the solution of N-(1-(tert-butyldimethylsilyloxy)-2-methylpropan-2-yl)-2-(5-(difluoromethoxy)-1-(3-(dimethylamino)propyl)-1H-indazol-3-yl)-5-trityl-5H-pyrrolo[3,2-b]pyrazine-7-carboxamide (88 mg, 0.12 mmol) in 3 mL of dichloromethane was added 3 mL of trifluoroacetic acid. The reaction mixture was stirred overnight at room temperature. After solvent evaporation, the residue was purified by preparative-HPLC (Gemini 5u C18 150×21.2 mm; inject volume: 3 mL/inj, flow rate: 20 mL/min; wavelength: 214 nm and 254 nm; the gradient conditions are: 40% acetonitrile/60% water (0.1% trifluoroacetic acid V/V) initially, and then proceed to 50% acetonitrile/50% water (0.1% trifluoroacetic acid V/V) in a linear fashion after just 9 min) to afford 2-(5-(difluoromethoxy)-1-(3-(dimethylamino)propyl)-1H-indazol-3-yl)-N-(1-hydroxy-2-methylpropan-2-yl)-5H-pyrrolo[3,2-b]pyrazine-7-carboxamide as yellow solid (22 mg, 34.5%). LCMS: $(M+H)^+=502$; $^1H$ NMR (300 MHz, $CD_3OD$): δ 9.04 (s, 1H), 8.17 (s, 1H), 8.11 (s, 1H), 7.66 (d, 1H, J=8.7 Hz), 7.35 (d, 1H, J=8.1 Hz), 6.85 (t, 1H, J=74.1 Hz), 4.59 (s, 2H), 3.84 (s, 2H), 3.34-3.32 (m, 2H), 2.89 (s, 6H), 2.44 (s, 2H), 1.64 (s, 6H).

Example 442 tert-Butyl 3-(2-(6-chloro-1-methyl-1H-indazol-3-yl)-5H-pyrrolo[2,3-b]pyrazine-7-carboxamido)cyclohexylcarbamate

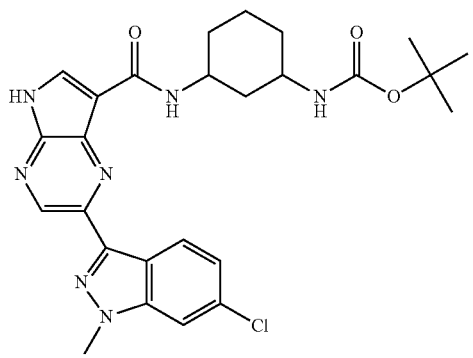 [SMILES: Cn1nc(-c2cnc3[nH]cc(C(=O)NC4CCCC(NC(=O)OC(C)(C)C)C4)c3n2)c2ccc(Cl)cc21]

Step 1

N-(3-Aminocyclohexyl)-2-bromo-5H-pyrrolo[2,3-b]pyrazine-7-carboxamide

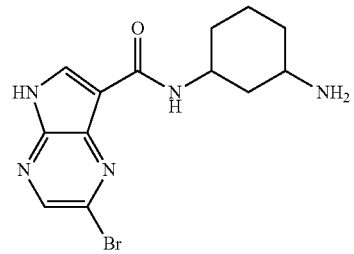

A mixture of 2-bromo-5H-pyrrolo[2,3-b]pyrazine-7-carboxylic acid (0.2 g, 0.83 mmol), cyclohexane-1,3-diamine (0.473 g, 4.15 mmol), HATU (0.475 g, 1.25 mmol), DIPEA (0.322 g, 2.5 mmol) in 15 mL of DMF were stirred at room temperature overnight. The solvent was removed under reduced pressure at 70° C. to give N-(3-aminocyclohexyl)-2-bromo-5H-pyrrolo[2,3-b]pyrazine-7-carboxamide as a crude which was used to the next step without further purification. MS: $(M+H)^+=338.1$.

Step 2 tert-Butyl 3-(2-bromo-5H-pyrrolo[2,3-b]pyrazine-7-carboxamido)cyclohexylcarbamate

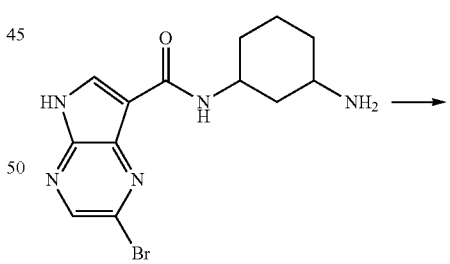

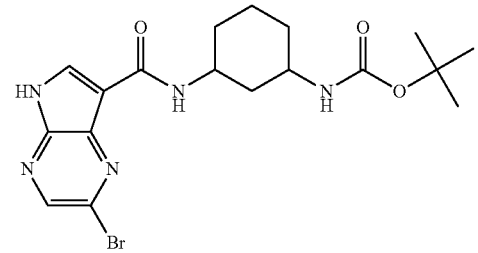

A mixture of N-(3-aminocyclohexyl)-2-bromo-5H-pyrrolo[2,3-b]pyrazine-7-carboxamide, $(Boc)_2O$ (3.0 g, 13.8 mmol) and $Na_2CO_3$ (2.9 g, 27.6 mmol) in a mixture solution of water (50 mL) and THF (150 mL) was stirred at room temperature overnight. The solvent was evaporated under reduced pressure The residue was triturated with petroleum ether then decanted and dried to give tert-butyl 3-(2-bromo-5H-pyrrolo[2,3-b]pyrazine-7-carboxamido)cyclohexylcarbamate (0.5 g, yield 72% over two steps) as a white solid which was used for the next step without further purification. MS: (M+H)$^+$=438.1.

Step 3 tert-Butyl 3-(2-(6-chloro-1-methyl-1H-indazol-3-yl)-5H-pyrrolo[2,3-b]pyrazine-7-carboxamido)cyclohexylcarbamate

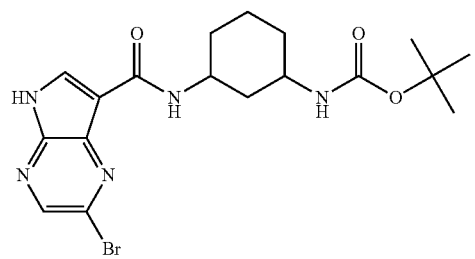

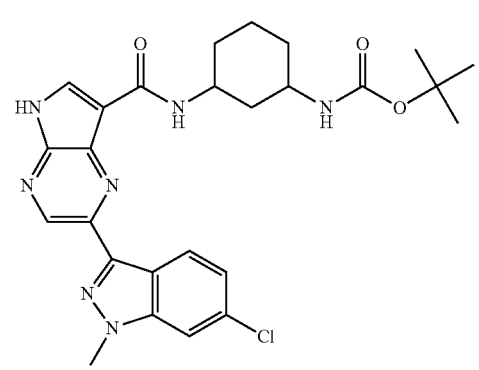

A mixture of 6-chloro-1-methyl-3-(tributylstannyl)-1H-indazole (0.47 g, 1.03 mmol), tert-butyl 3-(2-bromo-5H-pyrrolo[2,3-b]pyrazine-7-carboxamido)cyclohexylcarbamate (0.45 g, 1.03 mmol), CuI (0.07 g, 0.37 mmol) and Pd(PPh$_3$)$_4$ (0.07 g, 0.06 mmol) in 100 mL of DMF was stirred at 80° C. under nitrogen atmosphere overnight. The solvent was removed under reduced pressure and the residue was purified by preparative-HPLC (Gemini 5u C18 150×21.2 mm; inject volume: 3 mL/inj, flow rate: 20 mL/min; wavelength: 214 nm and 254 nm; the gradient conditions were: 50% acetonitrile/50% water (0.1% trifluoroacetic acid, v/v) initially, proceeding to 85% acetonitrile/15% water (0.1% trifluoroacetic acid, v/v) in a linear fashion over 9 min.) to give tert-butyl 3-(2-(6-chloro-1-methyl-1H-indazol-3-yl)-5H-pyrrolo[2,3-b]pyrazine-7-carboxamido)cyclohexylcarbamate (0.3 g, 56%) as a yellow solid. MS: (M+H)$^+$=542.2; $^1$H NMR (300 MHz, DMSO): δ 9.13-9.07 (m, 1H), 8.48-8.39 (m, 2H), 8.13-8.01 (m, 2H), 7.42-7.30 (m, 1H), 5.20 (s, 3H), 3.44-3.35 (m, 1H), 2.30-2.05 (m, 1H), 1.82-1.38 (m, 4H), 1.32-1.17 (m, 13H).

Example 443

N-(1-(Aminomethyl)cyclopropyl)-2-(6-fluoro-1-methyl-1H-indazol-3-yl)-5H-pyrrolo[2,3-b]pyrazine-7-carboxamide hydrochloride

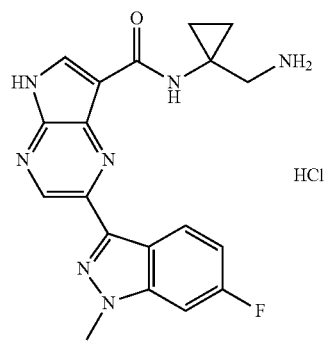 [SMILES: Cn1nc(-c2cnc3[nH]cc(C(=O)NC4(CN)CC4)c3n2)c2ccc(F)cc21 ; Cl]

Step 1

Ethyl 1-aminocyclopropanecarboxylate hydrochloride

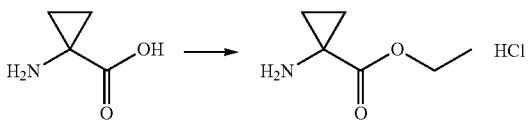

A suspension of 1-aminocyclopropanecarboxylic acid (5.8 g, 57.4 mmol) in 300 mL of ethanol was cooled to 0° C., thionyl chloride (20.5 g, 172.7 mmol) was added drop-wise over 30 minutes. Then the cold bath was removed and the reaction mixture was heated at reflux for 2 hours, then the mixture was stirred at room temperature for 16 hours. The solvent was evaporated at 40° C. under reduced pressure to give ethyl 1-aminocyclopropanecarboxylate hydrochloride (9.53 g, 100%) as a solid. It was used directly in the next step without further purification. MS: (M+H)$^+$=130.2; $^1$H NMR (300 MHz, DMSO): δ 9.04 (brs, 3H), 4.14 (q, 2H, J=6.9 Hz), 1.45 (d, 2H, J=3.3 Hz), 1.37 (d, 2H, J=3.2 Hz), 1.19 (t, 3H, J=6.9 Hz).

Step 2

Ethyl 1-(benzyloxycarbonylamino)cyclopropanecarboxylate

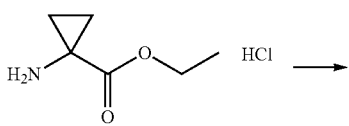

-continued

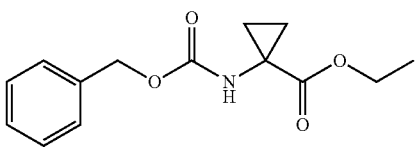

A suspension of ethyl 1-aminocyclopropanecarboxylate hydrochloride (9.5 g, 57.3 mmol) in 450 mL of ethyl acetate was cooled to 0° C., a solution of NaHCO$_3$ (39.5 g, 470.3 mmol) in 325 mL of water was added slowly. Then benzyl chloroformate (13.3 g, 78.2 mmol) was added drop-wise. The cold bath was removed and the mixture was stirred at room temperature for 16 hours. The organic phase was washed with 1N HCl (100 mL), saturated NaHCO$_3$ solution (100 mL), brine (100 mL), and dried over anhydrous sodium sulfate. The drying agent was removed by filtration and the filtrate was concentrated to give a white solid. The solid was purified by column chromatography (silica gel, 200-300 mesh, eluting with a mixture of ethyl acetate and petroleum ether (1:3, v/v) to give ethyl 1-(benzyloxycarbonylamino)cyclopropanecarboxylate (13.7 g, 91%) as a white solid. MS: (M+H)$^+$=286.1; $^1$H NMR (300 MHz, CDCl$_3$): δ 7.37-7.32 (m, 5H), 5.13 (s, 2H), 4.70 (s, 1H), 4.13 (brs, 2H), 1.59-1.53 (m, 2H), 1.23-1.19 (m, 5H).

Step 3

Benzyl 1-(hydroxymethyl)cyclopropylcarbamate

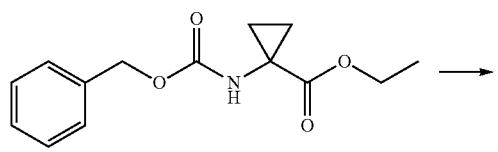

To a stirred solution of ethyl 1-(benzyloxycarbonylamino)cyclopropanecarboxylate (8.7 g, 33.0 mmol) in 50 mL of THF was slowly added at room temperature LiBH4 (2.26 g, 103.76 mmol) and the mixture was stirred at room temperature for 16 hours. The reaction mixture was cooled to 0° C. and quenched by adding a 50% HOAc solution (10 mL). The reaction mixture was partitioned between 70 mL of water and 70 mL of diethyl ether. The organic phase was washed with saturated aqueous NaHCO$_3$ solution (15 mL), brine (10 mL) and dried over anhydrous sodium sulfate. The drying agent was removed by filtration and the filtrate was evaporated at 40° C. under reduced pressure to give a crude product, which was purified by column chromatography (silica gel, 200-300 mesh, eluting with a mixture of petroleum ether and ethyl acetate (1:1, v/v) to give benzyl 1-(hydroxymethyl)cyclopropylcarbamate (6.36 g, 87.1%) as a white solid. MS: (M+H)$^+$= 222.1; $^1$H NMR (300 MHz, CDCl$_3$): δ 7.46-7.35 (m, 5H), 5.38 (brs, 1H), 5.19 (s, 2H), 3.71 (s, 2H), 0.96 (s, 4H).

Step 4

(1-(Benzyloxycarbonylamino)cyclopropyl)methyl methanesulfonate

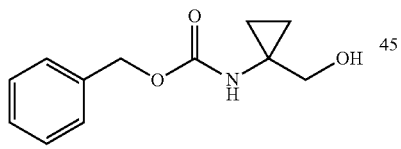

To a stirred solution of benzyl 1-(hydroxymethyl)cyclopropylcarbamate (4 g, 18.1 mmol) in 100 mL of dichloromethane at 0° C. was added DIEA (3 g, 23.5 mmol), followed by slow addition of MS:Cl (2.28 g, 19.9 mmol). The solution was stirred at 0° C. for 30 minutes. The mixture was partitioned between saturated aqueous NaHCO$_3$ solution (20 mL), brine (15 mL), dried over anhydrous sodium sulfate. The drying agent was removed by filtration and the filtrate was evaporated at 40° C. under reduced pressure to give a crude product, which was purified by column chromatography (silica gel, 200-300 mesh, eluting with a mixture of ethyl acetate and petroleum ether (1:1, v/v) to give (1-(benzyloxycarbonylamino)cyclopropyl)methyl methanesulfonate (5 g, 92.4%) as a white solid. MS: (M+H)$^+$=394; MS: (M+H)$^+$= 394; $^1$H NMR (300 MHz, CDCl$_3$): δ 7.45-7.35 (m, 5H), 5.38 (s, 1H), 5.19 (s, 2H), 4.34 (s, 2H), 3.04 (s, 3H), 1.07 (d, 4H, J=4.8 Hz). LCMS: 300.1 [M+H]$^+$, 322.1 [M+Na]$^+$.

Step 5

Benzyl 1-(azidomethyl)cyclopropylcarbamate

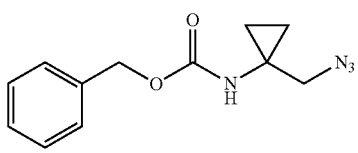

To a stirred solution of (1-(benzyloxycarbonylamino)cyclopropyl)methyl methanesulfonate (5 g, 16.7 mmol) in 100 mL of DMF was added NaN$_3$ (3 g, 46.15 mmol) in one portion at room temperature. Then the reaction mixture was stirred at 70° C. for 16 hours. The mixture was poured into 400 mL of water, extracted with ethyl acetate (600 mL). The organic phase was washed with brine (50 mL) and dried over anhydrous sodium sulfate. The drying agent was removed by filtration and the filtrate was evaporated at 40° C. under reduced pressure to give a crude product as colorless oil, which was used in the next step without further purification MS: $(M+H)^+= 247.2$.

Step 6

[1-(tert-Butoxycarbonylamino-methyl)-cyclopropyl]-carbamic acid benzyl ester

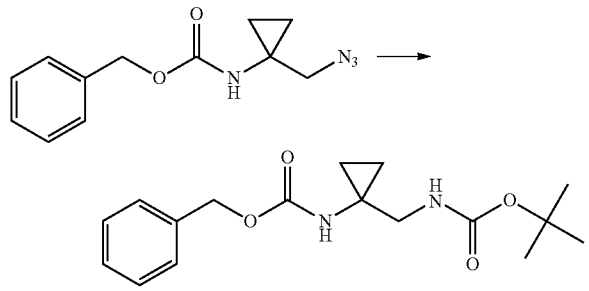

To a stirred solution of benzyl 1-(azidomethyl)cyclopropylcarbamate (2.78 g, 11.3 mmol) in 40 mL of THF and 20 mL of water, was added $PPh_3$ (5.92 g, 22.6 mmol) in one portion at room temperature. Then the mixture was stirred at room temperature for 16 hours. $(Boc)_2O$ (3.75 g, 17.2 mmol) and $Et_3N$ (2.3 g, 23 mmol) were added successively and the final mixture was stirred at room temperature for additional 16 hours. The mixture was diluted with 200 mL of ethyl acetate, washed with brine (20 mL). The solvent was evaporated at 40° C. under reduced pressure and the residue was dissolved in EtOAc (50 mL), washed by brine (20 mL), dried over $Na_2SO_4$. The crude white solid was used for the next step without further purification. MS: $(M+Na)^+=343.2$.

Step 7 tert-Butyl (1-aminocyclopropyl)methylcarbamate

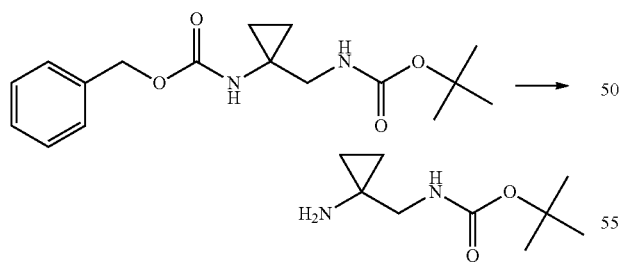

To a stirred solution of [1-(tert-butoxycarbonylamino-methyl)-cyclopropyl]-carbamic acid benzyl ester (0.912 g, 2.85 mmol) in 120 mL of methanol was added 10% Pd on carbon (200 mg) in one portion at room temperature. Then the mixture was degassed by bubbling hydrogen for 5 minutes then stirred under a hydrogen atmosphere at room temperature for 16 hours. The mixture was filtered to remove the catalyst and the filtrate was evaporated at 40° C. under reduced pressure to give tert-butyl (1-aminocyclopropyl)methylcarbamate (0.4 g, 75.4%) as a colorless oil which was used into next step without further purification. MS: $(M+H)^+=187.2$.

Step 8 tert-Butyl (1-(2-(6-fluoro-1-methyl-1H-indazol-3-yl)-5H-pyrrolo[2,3-b]pyrazine-7-carboxamido)cyclopropyl)methylcarbamate

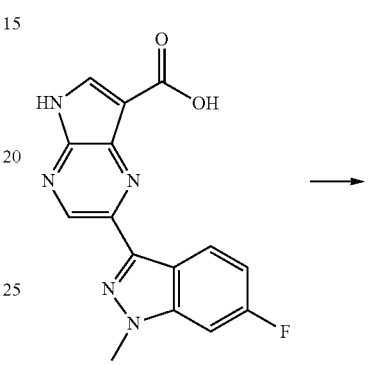

To a stirred solution of 2-(6-fluoro-1-methyl-1H-indazol-3-yl)-5H-pyrrolo[2,3-b]pyrazine-7-carboxylic acid (0.10 g, 0.32 mmol), EDCI (0.123 g, 0.64 mmol), DMAP (0.122 g, 1 mmol) and DIPEA (0.11 g, 0.90 mmol) in 6 mL of DMF was added tert-butyl (1-aminocyclopropyl)methylcarbamate (0.20 g, 1.07 mmol) in one portion at room temperature and stirred for 16 hours. The mixture was poured into 50 mL of water, and filtered. The filter cake was washed with water, dried and used in the next step without further purification. MS: (M+H)⁺=480.2.

Step 9

N-(1-(Aminomethyl)cyclopropyl)-2-(6-fluoro-1-methyl-1H-indazol-3-yl)-5H-pyrrolo[2,3-b]pyrazine-7-carboxamide hydrochloride

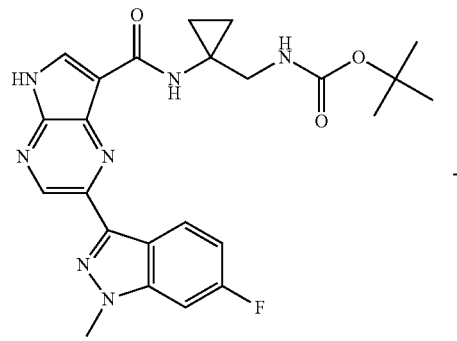

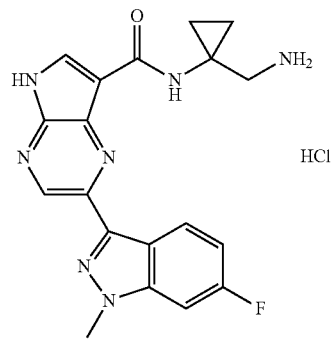

tert-Butyl (1-(2-(6-fluoro-1-methyl-1H-indazol-3-yl)-5H-pyrrolo[2,3-b]pyrazine-7-carboxamido)cyclopropyl)methylcarbamate (95 mg, 0.20 mmol) was dissolved in 20 mL of a saturated solution of HCl (g) in dioxane and the solution was stirred at room temperature for 3 hours. The solvent was evaporated at 40° C. under reduced pressure and the residue was triturated with ethyl acetate (10 mL) then decanted and dried to give N-(1-(aminomethyl)cyclopropyl)-2-(6-fluoro-1-methyl-1H-indazol-3-yl)-5H-pyrrolo[2,3-b]pyrazine-7-carboxamide hydrochloride (13 mg, 15.8%) as a pale yellow solid. MS: (M+H)⁺=380.1; ¹H NMR (300 MHz, CD₃OD): δ 9.18 (s, 1H), 8.43-8.41 (m, 2H), 7.45 (d, 1H, J=9.3 Hz), 7.19 (s, 1H), 4.17 (s, 3H), 3.32 (s, 2H), 1.25 (s, 4H).

Example 444

N-tert-Butyl-2-(isoquinolin-8-yl)-5H-pyrrolo[3,2-b]pyrazine-7-carboxamide

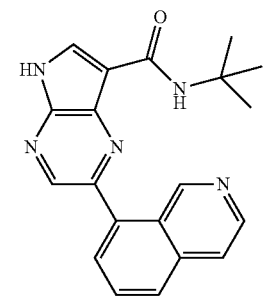 [SMILES: CC(C)(C)NC(=O)c1c[nH]c2ncc(-c3cccc4ccncc34)nc12]

Step 1

2-Bromo-N-tert-butyl-5H-pyrrolo[3,2-b]pyrazine-7-carboxamide

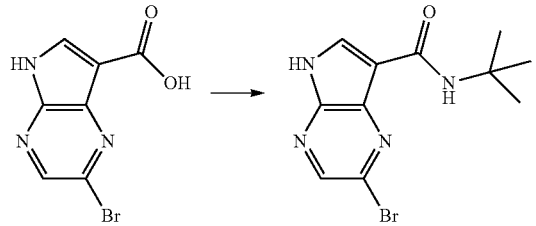 [SMILES: O=C(O)c1c[nH]c2ncc(Br)nc12 ; CC(C)(C)NC(=O)c1c[nH]c2ncc(Br)nc12]

A mixture of 2-bromo-5H-pyrrolo[3,2-b]pyrazine-7-carboxylic acid (0.2 g, 0.83 mmol), 2-methylpropan-2-amine (66 mg, 0.91 mmol), EDCI (476 mg, 2.49 mmol) and HOBt (112 mg, 0.83 mmol) in dry dichloromethane (20 mL) was stirred at room temperature for 16 hours. Reaction mixture was concentrated to about half the volume and the formed precipitate was separated by filtration, the filter cake was washed with dichloromethane and dried to afford 2-bromo- N-tert-butyl-5H-pyrrolo[3,2-b]pyrazine-7-carboxamide (103 mg, 42%) as a yellow solid. LCMS: (M+H)$^+$=297.

Step 2

N-tert-Butyl-2-(isoquinolin-8-yl)-5H-pyrrolo[3,2-b]pyrazine-7-carboxamide

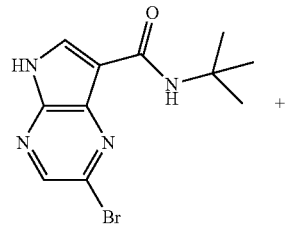

+

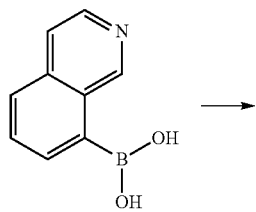

→

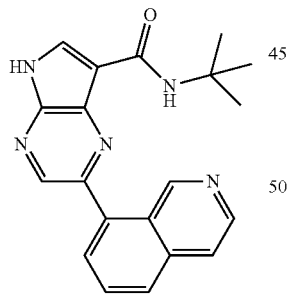

A mixture of 2-bromo-N-tert-butyl-5H-pyrrolo[3,2-b]pyrazine-7-carboxamide (0.1 g, 0.337 mmol), isoquinolin-8-ylboronic acid (64 mg, 0.37 mmol), Pd$_2$ dba$_3$ (77 mg, 0.067 mmol), X-Phos (64 mg, 0.135 mmol) and Na$_2$CO$_3$ (107 mg, 1.01 mmol) in dioxane (20 mL) and water (5 mL) was heated to 90° C. for 16 hours under N$_2$ atmosphere. Reaction mixture was concentrated and the residue was purified by preparative-TLC (methanol:dichloromethane=1:10) to afford N-tert-butyl-2-(isoquinolin-8-yl)-5H-pyrrolo[3,2-b]pyrazine-7-carboxamide (76 mg, 66%) as a white solid. $^1$H NMR (300 MHz, CDCl$_3$): δ 11.77 (s, 1H), 9.95 (s, 1H), 8.89 (s, 1H), 8.69 (d, 1H, J=5.7 Hz), 8.45 (s, 1H), 8.41 (s, 1H), 8.01-7.84 (m, 4H), 1.46 (s, 9H). LCMS: (M+H)$^+$=346.

Example 445

N-(1-Hydroxy-2-methylpropan-2-yl)-2-(6-methyl-1-(2-morpholinoethyl)-1H-indazol-3-yl)-5H-pyrrolo[3,2-b]pyrazine-7-carboxamide hydrochloride

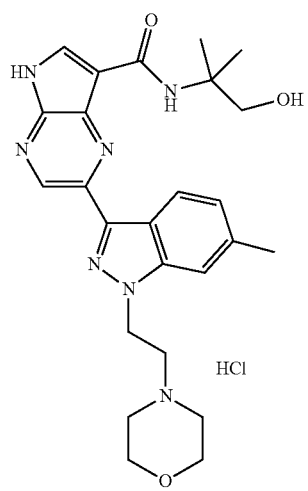 [SMILES: Cc1ccc2c(-c3cnc4[nH]cc(C(=O)NC(C)(C)CO)c4n3)nn(CCN3CCOCC3)c2c1 ; Cl]

Step 1

N-(1-(tert-Butyldimethylsilyloxy)-2-methylpropan-2-yl)-2-(6-methyl-1-(2-morpholinoethyl)-1H-indazol-3-yl)-5-trityl-5H-pyrrolo[3,2-b]pyrazine-7-carboxamide

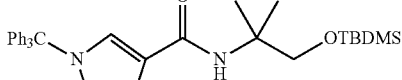

+

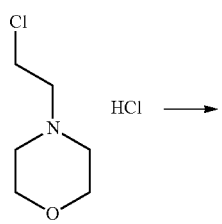

HCl →

1309
-continued

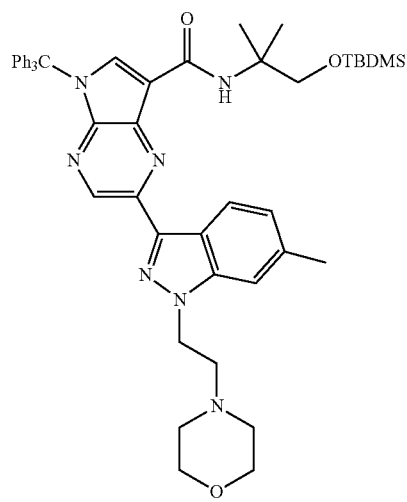

A mixture of N-(1-(tert-butyldimethylsilyloxy)-2-methylpropan-2-yl)-2-(6-methyl-1H-indazol-3-yl)-5-trityl-5H-pyrrolo[3,2-b]pyrazine-7-carboxamide (200 mg, 0.277 mmol), 4-(2-chloroethyl)morpholine hydrochloride (62 mg, 0.333 mmol) and $K_2CO_3$ (191 mg, 1.385 mmol) in dry DMF (20 mL) was heated to 90° C. for 3 hours. Reaction mixture was extracted with ethyl acetate (100 mL), organic phase washed with water (3×10 mL) and brine (2×10 mL). The organic layer was dried over $Na_2SO_4$, filtered and concentrated to afford N-(1-(tert-butyldimethylsilyloxy)-2-methylpropan-2-yl)-2-(6-methyl-1-(2-morpholinoethyl)-1H-indazol-3-yl)-5-trityl-5H-pyrrolo[3,2-b]pyrazine-7-carboxamide (167 mg, crude) as a yellow oil. LCMS: $(M+H)^+=834$.

Step 2

N-(1-Hydroxy-2-methylpropan-2-yl)-2-(6-methyl-1-(2-morpholinoethyl)-1H-indazol-3-yl)-5H-pyrrolo[3,2-b]pyrazine-7-carboxamide hydrochloride

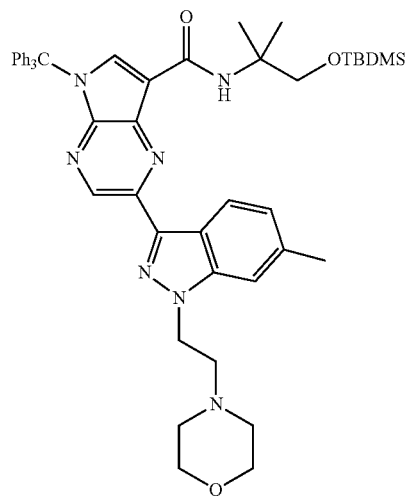

1310
-continued

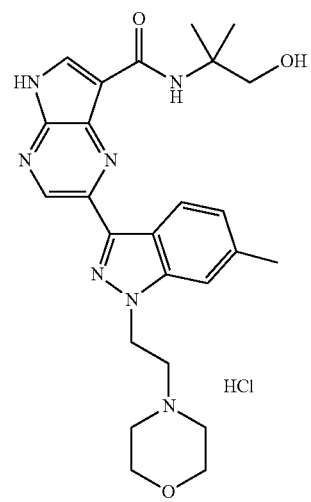

To a stirred solution of N-(1-(tert-butyldimethylsilyloxy)-2-methylpropan-2-yl)-2-(6-methyl-1-(2-morpholinoethyl)-1H-indazol-3-yl)-5-trityl-5H-pyrrolo[3,2-b]pyrazine-7-carboxamide (167 mg, 0.2 mmol) in dioxane (20 mL) was bubbled HCl gas until saturation and then stirred at room temperature for 16 hours. Reaction mixture was concentrated and the residue was triturated with methanol (1 mL) then decanted and dried to afford N-(1-hydroxy-2-methylpropan-2-yl)-2-(6-methyl-1-(2-morpholinoethyl)-1H-indazol-3-yl)-5H-pyrrolo[3,2-b]pyrazine-7-carboxamide hydrochloride (76 mg, 64%) as a white solid. LCMS: $(M+H)^+=478$; $^1H$ NMR (300 MHz, $CD_3OD$): δ 9.15 (s, 1H), 8.49 (d, 1H, J=8.4 Hz), 8.29 (s, 1H), 7.56 (s, 1H), 7.22 (d, 1H, J=8.1 Hz), 5.00-4.96 (m, 2H), 4.08-3.85 (m, 12H), 2.59 (s, 3H), 1.56 (s, 6H).

Example 446

N-tert-Butyl-2-(5-(difluoromethoxy)-1-(3,4-dihydroxybutyl)-1H-indazol-3-yl)-5H-pyrrolo[3,2-b]pyrazine-7-carboxamide

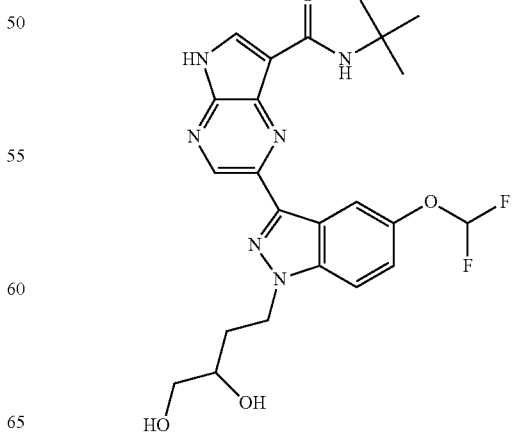

Step 1

5-(tert-Butyldimethylsilyloxy)-1H-indazole

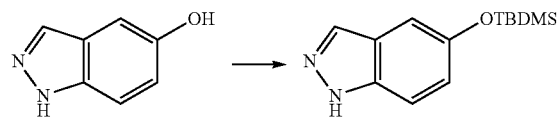 [SMILES: Oc1ccc2[nH]ncc2c1 ; CC(C)(C)[Si](C)(C)Oc1ccc2[nH]ncc2c1]

To a stirred solution of 1H-indazol-5-ol (5.0 g, 37.3 mol) and imidazole (12.7 g, 186.5 mmol) in dichloromethane (200 mL) was added tert-butylchlorodimethylsilane (16.8 g, 112 mol) and the mixture stirred at room temperature overnight. Then the reaction mixture was washed with brine (3×50 mL) and dried over $Na_2SO_4$. The crude mixture was purified by column chromatography (silica gel, 200-300 mesh, EtOAc: petroleum ether=1:10, v/v) to give 5-(tert-Butyldimethylsilyloxy)-1H-indazole (9.5 g, yield 100%) as yellow oil. MS: $(M+H)^+$=249.2; $^1$H NMR (300 MHz, $CDCl_3$): δ 7.95 (d, 1H, J=1.2 Hz), 7.34 (dt, 1H, J=8.7, 0.75 Hz), 7.12 (s, 1H), 6.97 (dd, 1H, J=8.7, 2.1 Hz), 1.01 (s, 9H), 0.23 (s, 6H).

Step 2

5-(tert-Butyldimethylsilyloxy)-3-iodo-1H-indazole

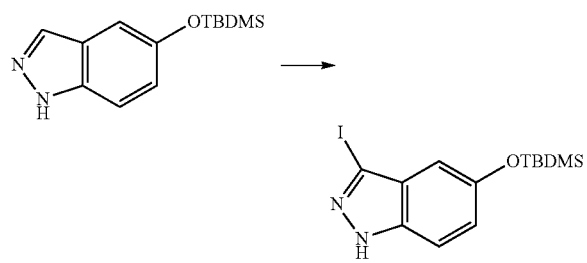

To a stirred solution of 5-(tert-butyldimethylsilyloxy)-1H-indazole (5.3 g, 0.02 mol) in DMSO (50 mL) at 0° C., was added KOH (3.36 g, 0.06 mol) followed by iodine (10.2 g, 0.04 mol) portionwise. The mixture was stirred at room temperature for additional 10 minutes, then the reaction was quenched with 10% $Na_2S_2O_3$ and diluted with water. The mixture was filtered and the filter cake was washed with water and dried to give 5-(tert-butyldimethylsilyloxy)-3-iodo-1H-indazole. The crude solid was used in the next step without purification. MS: $(M+H)^+$=375.

Step 3 tert-Butyl 5-(tert-butyldimethylsilyloxy)-3-iodo-1H-indazole-1-carboxylate

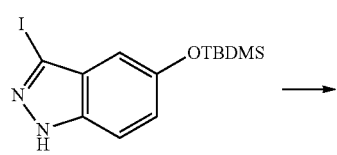

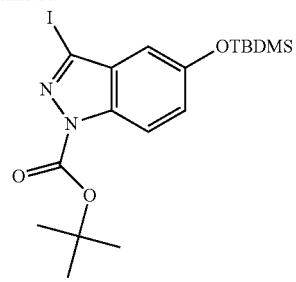

To a stirred solution of 5-(tert-butyldimethylsilyloxy)-3-iodo-1H-indazole (crude, 0.02 mol) in dichloromethane (100 mL) was added $Boc_2O$ (4.75 g, 0.022 mol) followed by DMAP (0.48 g, 0.004 mol) and $Et_3N$ (2.2 g, 0.022 mol). The mixture was stirred at room temperature for 1 hour. The solvent was removed under reduced pressure. The residue was purified by column chromatography on silica gel eluting with petroleum ether/EtOAc (6:1) to give tert-butyl 5-(tert-butyldimethylsilyloxy)-3-iodo-1H-indazole-1-carboxylate (7.8 g, 82% over two steps) as a pale yellow solid. $^1$H NMR (300 MHz, $CDCl_3$): δ 7.96 (d, 1H, J=9.0 Hz), 7.12 (dd, 1H, J=9, 2.4 Hz), 6.84 (d, 1H, J=2.4 Hz), 1.71 (s, 9H), 1.02 (s, 9H), 0.23 (s, 6H).

Step 4 tert-Butyl 5-hydroxy-3-iodo-1H-indazole-1-carboxylate

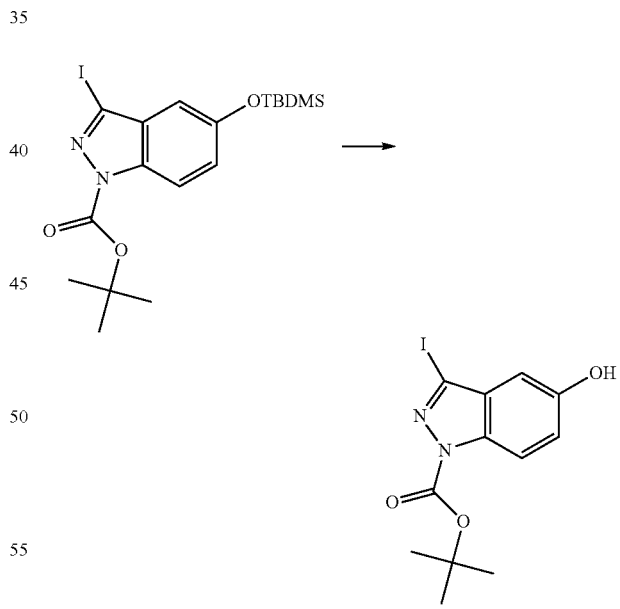

To a stirred solution of tert-butyl 5-(tert-butyldimethylsilyloxy)-3-iodo-1H-indazole-1-carboxylate (1 g, 2.11 mmol) in THF (10 mL), was added TBAF (5.6 g, 21.1 mmol) in THF (5 mL). The mixture was stirred at room temperature for 0.5 hour. The solvent was removed under reduced pressure. The residue was diluted with water and extracted with EtOAc (3×10 mL). The combined organic layers were washed with brine and dried over $Na_2SO_4$. After filtration and concentration, the crude product was used in the next step without purification. LCMS: 361 [M+H]+.

Step 5 tert-Butyl 5-(difluoromethoxy)-3-iodo-1H-indazole-1-carboxylate

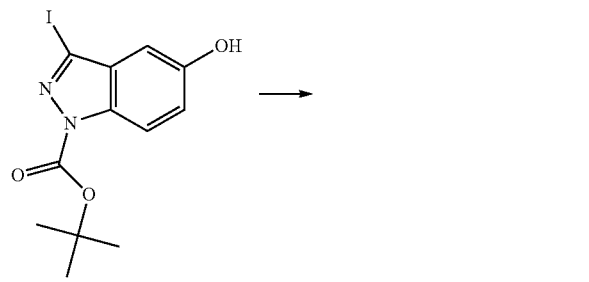

Diethyl bromodifluoromethylphosphonate (1.13 g, 4.22 mmol) was added in one portion to a cooled (−30° C.) solution of tert-butyl 5-hydroxy-3-iodo-1H-indazole-1-carboxylate and KOH (2.36 g, 42.2 mmol) in MeCN/H$_2$O (20 mL/20 mL). The reaction mixture was allowed to warm to room temperature. After 20 min, the reaction mixture was diluted with EtOAc (15 mL), and the organic phase was separated. The water phase was extracted with EtOAc (10 mL). The combined organic layers were dried over Na$_2$SO$_4$. Evaporation of the solvent gave a crude product that was purified by column chromatography on silica gel eluting with petroleum ether/EtOAc (5:1) to give tert-butyl 5-(difluoromethoxy)-3-iodo-1H-indazole-1-carboxylate (0.41 g, 47% over two steps) as a white solid. $^1$H NMR (300 MHz, CDCl$_3$): δ 8.13 (d, 1H, J=9.0 Hz), 7.39 (dd, 1H, J=9, 2.4 Hz), 7.23 (d, 1H, J=2.4 Hz), 6.57 (t, 1H, J=73.2 Hz), 1.73 (s, 9H).

Step 6

5-(difluoromethoxy)-3-iodo-1H-indazole

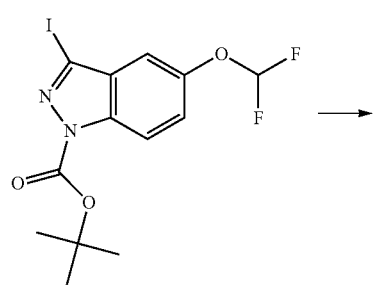

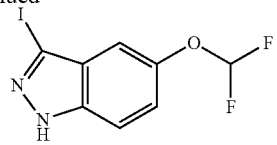

To a stirred solution of tert-butyl 5-(difluoromethoxy)-3-iodo-1H-indazole-1-carboxylate (410 mg, 1 mmol) in dichloromethane (10 mL) was added drop-wise trifluoroacetic acid (5 mL) at room temperature and the reaction mixture was stirred for 1 hour. The mixture was washed with NaHCO$_3$ aqueous, and then organic was dried over Na$_2$SO$_4$. After filtration and concentration, 5-(difluoromethoxy)-3-iodo-1H-indazole (300 mg, 97%) was obtained as a white solid, used in the next step without further purification. MS: (M+H)$^+$=311.

Step 7

Methyl 2-bromo-5-trityl-5H-pyrrolo[3,2-b]pyrazine-7-carboxylate

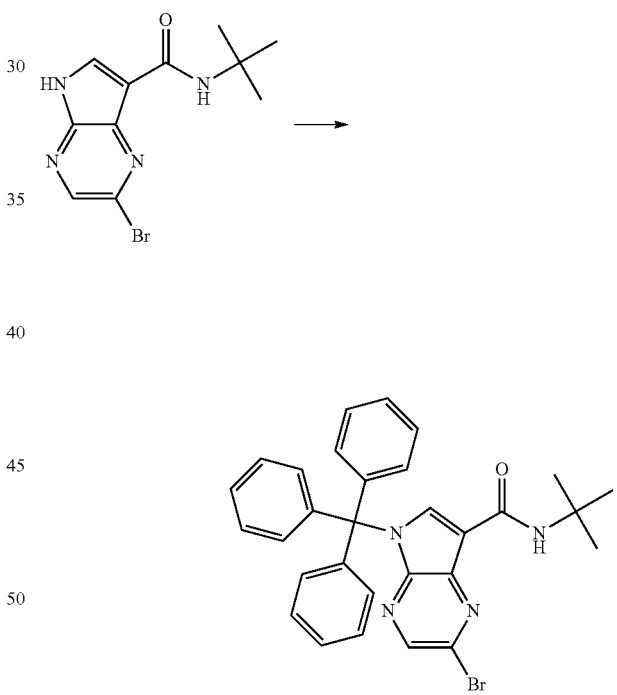

To a stirred solution of 2-bromo-N-tert-butyl-5H-pyrrolo[3,2-b]pyrazine-7-carboxamide and (chloromethanetriyl)tribenzene (1.55 g, 5.56 mmol) in DMF (10 mL) was added triethylamine (0.56 g, 5.56 mmol). The mixture was stirred at room temperature for 16 hours. The mixture was poured into water and extracted with EtOAc (3×15 mL). The combined organic layers were washed with brine and dried over Na$_2$SO$_4$. After filtration and concentration, the residue was purified by column chromatography on silica gel eluting with petroleum ether/EtOAc (10:1) to give 2-bromo-N-tert-butyl-5-trityl-5H-pyrrolo[3,2-b]pyrazine-7-carboxamide (1.1 g, 73%) as a pale yellow solid. $^1$H NMR (300 MHz, DMSO): δ

8.30 (s, 1H), 8.00 (s, 1H), 7.70 (s, 1H), 7.38-7.25 (m, 10H), 7.19-7.15 (m 5H), 1.27 (s, 9H).

Step 8

5-(Difluoromethoxy)-3-(tributylstannyl)-1H-indazole

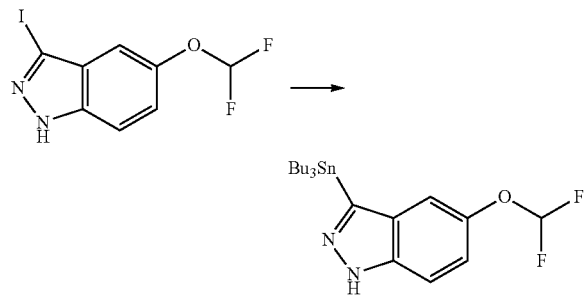

In a flask, 5-(difluoromethoxy)-3-iodo-1H-indazole (1.2 g, 2.93 mmol) was dissolved in THF (30 mL). The solution was cooled to −25° C. Isopropylmagnesium chloride (8.8 mL, 8.8 mmol, 1M in THF) was added drop-wise at −25° C. The reaction mixture was stirred at −25° C. for 20 min. Then chlorotributyltin (1.6 mL, 5.86 mmol) was added slowly. The reaction mixture was allowed to warm to room temperature and stirred for 1.5 h. The reaction mixture was quenched with saturated NH$_4$Cl solution and then extracted with EtOAc (3×20 mL), organics were washed with water (10 mL), brine (2×10 mL) and dried over Na$_2$SO$_4$ and concentrated. The residue was purified by column chromatography on silica gel eluting with petroleum ether/EtOAc (8:1) to give 5-(difluoromethoxy)-3-(tributylstannyl)-1H-indazole (1.1 g, 79%) as an oil. $^1$H NMR (300 MHz, CDCl$_3$): δ 7.52-7.46 (m, 2H), 7.19 (d, 1H, J=7.9 Hz), 6.51 (t, 1H, J=88.6 Hz), 1.68-1.57 (m, 6H), 1.45-1.14 (m, 12H), 0.93-0.84 (m, 9H).

Step 9

N-tert-Butyl-2-(5-(difluoromethoxy)-1H-indazol-3-yl)-5-trityl-5H-pyrrolo[3,2-b]pyrazine-7-carboxamide

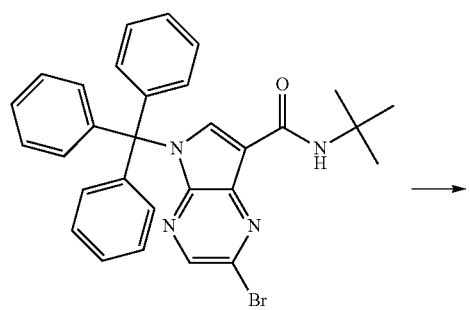

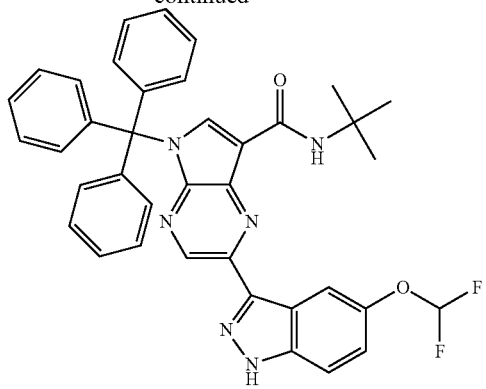

In a round-bottomed flask, 2-bromo-N-tert-butyl-5-trityl-5H-pyrrolo[3,2-b]pyrazine-7-carboxamide (530 mg, 1 mmol) and 5-(difluoromethoxy)-3-(tributylstannyl)-1H-indazole (470 mg, 1 mmol) were dissolved in DMF (10 mL) under nitrogen. Pd(PPh$_3$)$_4$ (58 mg, 0.05 mmol) and CuI (38 mg, 0.2 mmol) were added and mixture sonicated for 5 min while bubbling nitrogen. The reaction mixture was stirred at 80° C. for 4 hours. The concentrated mixture was purified by column chromatography on silica gel eluting with petroleum ether/EtOAc (3:1 to 1:1, v/v) to give N-tert-butyl-2-(5-(difluoromethoxy)-1H-indazol-3-yl)-5-trityl-5H-pyrrolo[3,2-b]pyrazine-7-carboxamide (410 mg, 64%) as a solid. MS: (M+H)$^+$=643.2; $^1$H NMR (300 MHz, CDCl$_3$): δ 8.85 (d, 1H, J=2.4 Hz), 8.35 (s, 1H), 8.26 (s, 1H), 8.13 (s, 1H,), 7.52-7.48 (m, 1H), 6.51 (t, 1H, J=74.0 Hz), 1.60 (s, 9H).

Step 10

2-(2,2-Dimethyl-1,3-dioxolan-4-yl)ethyl methanesulfonate

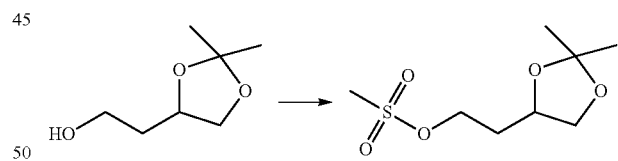

To a stirred solution of 2-(2,2-dimethyl-1,3-dioxolan-4-yl)ethanol (292 mg, 2.00 mmol) in 10 mL of dichloromethane at 0° C. was added DIEA (284 mg, 2.20 mmol), followed by slow addition of MS:Cl (252 mg, 2.20 mmol). Then the reaction mixture was stirred at 0° C. for 30 minutes. The reaction was quenched with saturated sodium bicarbonate solution (3 mL), the organic phase was dried over anhydrous sodium sulfate. The drying agent was removed by filtration and the filtrate was evaporated at 40° C. under reduced pressure to give 2-(2,2-dimethyl-1,3-dioxolan-4-yl)ethyl methanesulfonate (360 mg, 80.20%) as a colorless oil. It was used directly in the next step without further purification. $^1$H NMR (300 MHz, CDCl$_3$): δ 4.40-4.36 (m, 2H), 4.34-4.23 (m, 1H), 4.20-4.19 (m, 1H), 4.12-4.08 (m, 1H), 3.032 (s, 3H), 2.00-1.99 (m, 2H), 1.41 (s, 3H), 1.35 (s, 3H).

Step 11

N-tert-Butyl-2-(5-(difluoromethoxy)-1-(2-(2,2-dimethyl-1,3-dioxolan-4-yl)ethyl)-1H-indazol-3-yl)-5-trityl-5H-pyrrolo[3,2-b]pyrazine-7-carboxamide

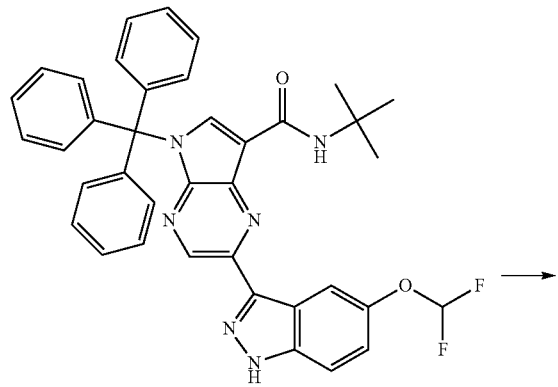

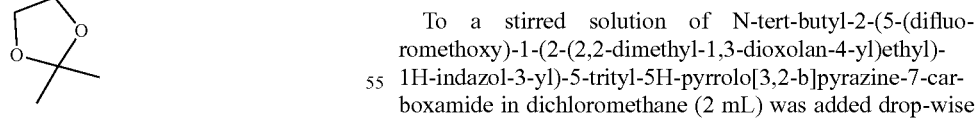

To a solution of N-tert-butyl-2-(5-(difluoromethoxy)-1H-indazol-3-yl)-5-trityl-5H-pyrrolo[3,2-b]pyrazine-7-carboxamide (100 mg, 0.156 mmol) in DMF (5 mL) was added 2-(2,2-dimethyl-1,3-dioxolan-4-yl)ethyl methanesulfonate (42 mg, 0.187 mmol) followed by K$_2$CO$_3$ (65 mg, 0.468 mmol). The mixture was heated at 65° C. for 2 hours. After cooling to room temperature, the mixture was poured into water, filtered, the filter cake washed with water and dried to give N-tert-butyl-2-(5-(difluoromethoxy)-1-(2-(2,2-dimethyl-1,3-dioxolan-4-yl)ethyl)-1H-indazol-3-yl)-5-trityl-5H-pyrrolo[3,2-b]pyrazine-7-carboxamide. The crude product was used in the next step without purification. MS: (M+H)$^+$=771.0.

Step 12

N-tert-Butyl-2-(5-(difluoromethoxy)-1-(3,4-dihydroxybutyl)-1H-indazol-3-yl)-5H-pyrrolo[3,2-b]pyrazine-7-carboxamide

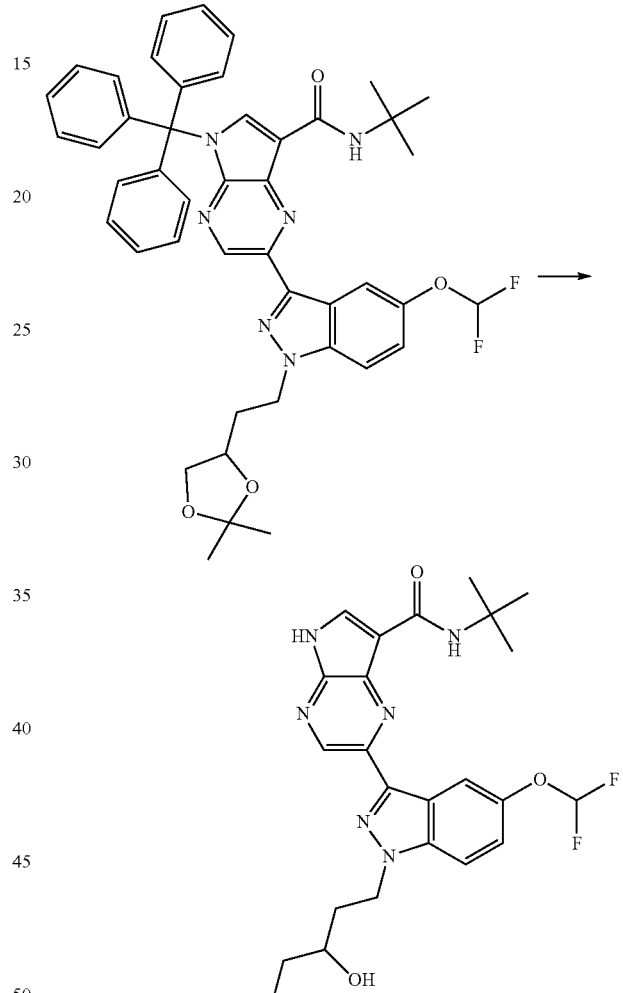

To a stirred solution of N-tert-butyl-2-(5-(difluoromethoxy)-1-(2-(2,2-dimethyl-1,3-dioxolan-4-yl)ethyl)-1H-indazol-3-yl)-5-trityl-5H-pyrrolo[3,2-b]pyrazine-7-carboxamide in dichloromethane (2 mL) was added drop-wise trifluoroacetic acid (1 mL) at room temperature and the reaction mixture was stirred for 2 hours. The solvent was removed under reduced pressure and the residue was purified by preparative-HPLC (Gemini 5u C18 150×21.2 mm; inject volume: 3 mL/inj, flow rate: 20 mL/min; wavelength: 214 nm and 254 nm; the gradient conditions were: 38% acetonitrile/62% water (0.1% trifluoroacetic acid, v/v) initially, proceeding to 46% acetonitrile/54% water (0.1% trifluoroacetic acid, v/v) in a linear fashion over 9 min.) to give N-tert-butyl-2-(5-(difluoromethoxy)-1-(3,4-dihydroxybutyl)-1H-indazol-3-yl)-5H-pyrrolo[3,2-b]pyrazine-7-carboxamide (30 mg, 39% over two steps) as a white solid. MS: (M+H)⁺=489.1; $^1$H NMR (300 MHz, DMSO): δ 12.85 (s, 1H), 9.11 (s, 1H), 8.42 (d, 1H, J=3.0 Hz), 8.24 (d, 1H, J=1.2 Hz), 7.92-7.88 (m, 2H), 7.45 (t, 1H, J=9.2 Hz), 7.23 (t, 1H, J=74.4 Hz), 4.67-4.64 (m, 2H), 3.48-3.26 (m, 4H), 2.16-2.10 (m, 4H), 1.86-1.83 (m, 4H), 1.54 (s, 9H).

Example 447

N-tert-Butyl-2-(5-(difluoromethoxy)-1-(3-hydroxy-butyl)-1H-indazol-3-yl)-5H-pyrrolo[3,2-b]pyrazine-7-carboxamide

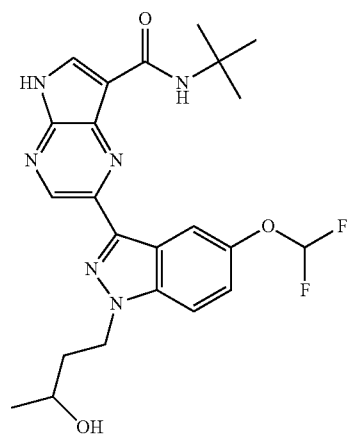

Step 1

4-Chlorobutan-2-one

To a suspension of 4-hydroxybutan-2-one (1.0 g, 11.36 mmol) and NaHCO₃ (2.8 g, 33.3 mmol) in dichloromethane (100 mL), immersed in ice-water bath, was added drop-wise over 10 minutes a solution of SOCl₂ (2.7 g, 22.8 mmol) in dichloromethane (5 mL). The resulting mixture was stirred for additional 5 hours at room temperature. The mixture was transferred to a separatory funnel, washed with brine (2×30 mL), dried over Na₂SO₄ and concentrated, the crude product (1.0 g) was used into next step without further purification as yellow oil. $^1$H NMR (300 MHz, CDCl₃): δ 3.72 (t, 2H, J=6.6 Hz), 2.90 (t, 2H, J=6.5 Hz), 2.19 (s, 3H).

Step 2

N-tert-butyl-2-(5-(difluoromethoxy)-1-(3-oxobutyl)-1H-indazol-3-yl)-5-trityl-5H-pyrrolo[3,2-b]pyrazine-7-carboxamide To a solution of N-tert-butyl-2-(5-(difluoromethoxy)-1H-indazol-3-yl)-5-trityl-5H-pyrrolo[3,2-b]pyrazine-7-carboxamide (100 mg, 0.156 mmol) in DMF (4 mL) was added 4-chlorobutan-2-one (20 mg, 0.187 mmol) followed by K₂CO₃ (65 mg, 0.468 mmol). The mixture was heated at 65° C. for 1.5 hours. After cooling to room temperature, the mixture was poured into water, filtered and dried to give N-tert-butyl-2-(5-(difluoromethoxy)-1-(3-oxobutyl)-1H-indazol-3-yl)-5-trityl-5H-pyrrolo[3,2-b]pyrazine-7-carboxamide. The crude product was used in the next step without purification. MS: (M+H)⁺=713.

Step 3

N-tert-butyl-2-(5-(difluoromethoxy)-1-(3-hydroxy-butyl)-1H-indazol-3-yl)-5-trityl-5H-pyrrolo[3,2-b]pyrazine-7-carboxamide

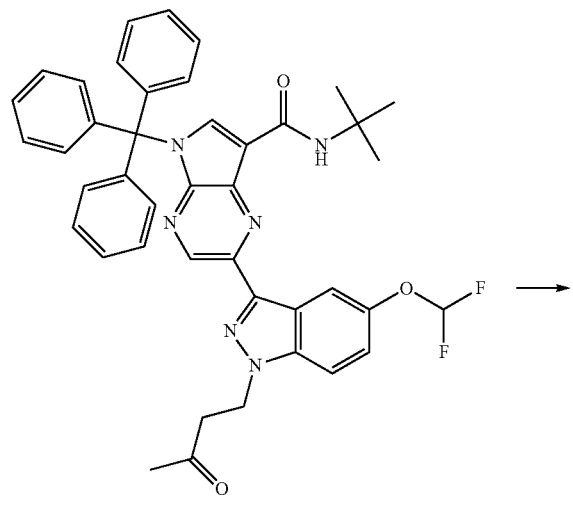

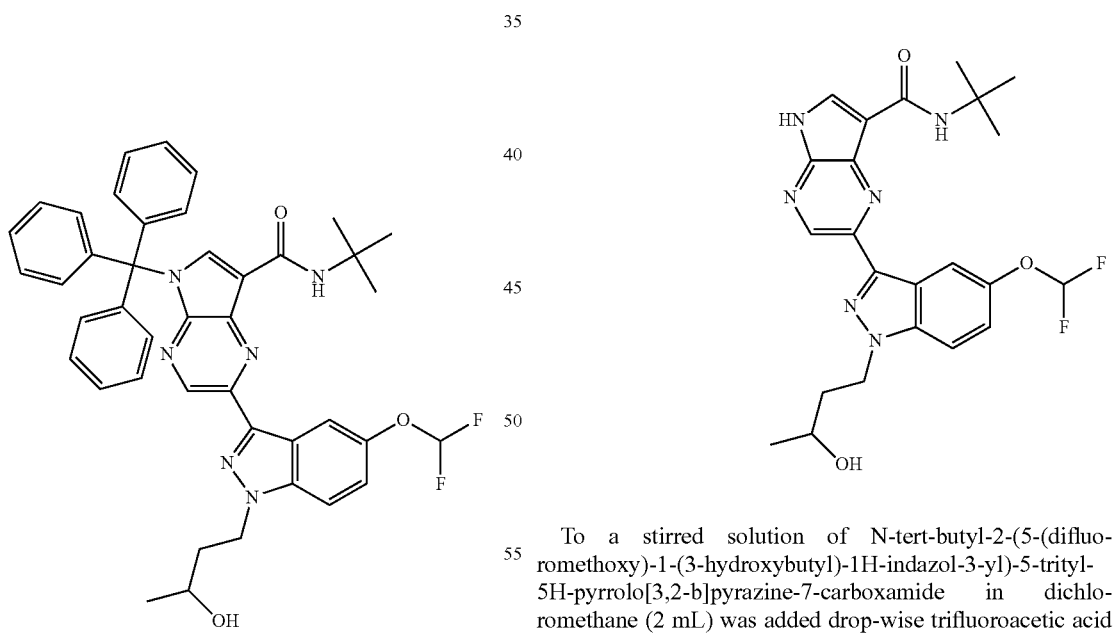

To a solution of N-tert-butyl-2-(5-(difluoromethoxy)-1-(3-oxobutyl)-1H-indazol-3-yl)-5-trityl-5H-pyrrolo[3,2-b]pyrazine-7-carboxamide (0.156 mmol) in MeOH (5 mL) was added NaBH₄ (30 mg, 0.78 mmol) at 0° C. The mixture was warmed at room temperature and stirred for 1 hour. Aqueous NH₄Cl solution was added to the mixture and product extracted with EtOAc (3×10 mL). The combined organic layers were washed with brine and dried over Na₂SO₄. After filtration and concentration, the crude product was used in the next step without purification. MS: (M+H)⁺=715.

Step 4

N-tert-butyl-2-(5-(difluoromethoxy)-1-(3-hydroxy-butyl)-1H-indazol-3-yl)-5H-pyrrolo[3,2-b]pyrazine-7-carboxamide

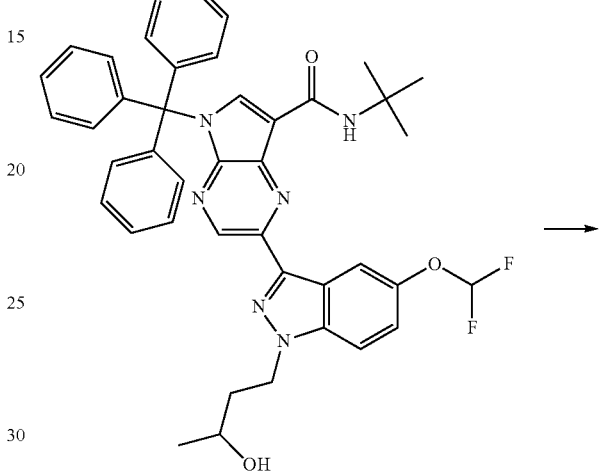

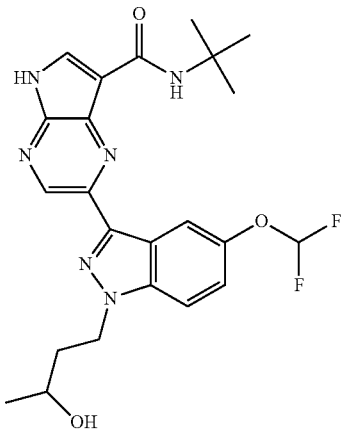 [SMILES: CC(O)CCn1nc(-c2cnc3[nH]cc(C(=O)NC(C)(C)C)c3n2)c2cc(OC(F)F)ccc21]

To a stirred solution of N-tert-butyl-2-(5-(difluoromethoxy)-1-(3-hydroxybutyl)-1H-indazol-3-yl)-5-trityl-5H-pyrrolo[3,2-b]pyrazine-7-carboxamide in dichloromethane (2 mL) was added drop-wise trifluoroacetic acid (1 mL) at room temperature. Then the reaction mixture was stirred for 1.5 hours. The solvent was removed under reduced pressure and the residue was purified by preparative-TLC (silica gel, petroleum ether:EtOAc=1:1) to give N-tert-butyl-2-(5-(difluoromethoxy)-1-(3-hydroxybutyl)-1H-indazol-3-yl)-5H-pyrrolo[3,2-b]pyrazine-7-carboxamide (22 mg, 30% over three steps) as a white solid. MS: (M+H)⁺=473.2; ¹H NMR (300 MHz, DMSO): δ 12.86 (s, 1H), 9.11 (s, 1H), 8.42 (s, 1H), 8.24 (d, 1H, J=1.8 Hz), 7.92-7.89 (m, 2H), 7.47-7.42

(m, 1H), 7.23 (t, 1H, J=74.4 Hz), 4.75-4.61 (m, 3H), 3.65 (brs, 1H), 2.06-1.92 (m, 2H), 1.53 (s, 9H), 1.15 (d, 3H, J=6.3 Hz).

Example 448

N-tert-Butyl-2-(5-(difluoromethoxy)-1-(3-(methylsulfonyl)propyl)-1H-indazol-3-yl)-5H-pyrrolo[3,2-b]pyrazine-7-carboxamide Step 1

N-tert-Butyl-2-(5-(difluoromethoxy)-1-(3-(methylsulfonyl)propyl)-1H-indazol-3-yl)-5-trityl-5H-pyrrolo[3,2-b]pyrazine-7-carboxamide

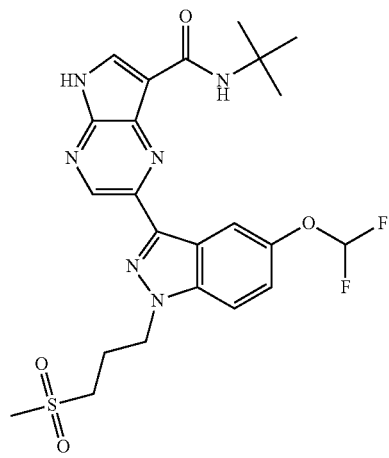 [SMILES: CC(C)(C)NC(=O)c1c[nH]c2ncc(-c3nn(CCCS(C)(=O)=O)c4ccc(OC(F)F)cc34)nc12]

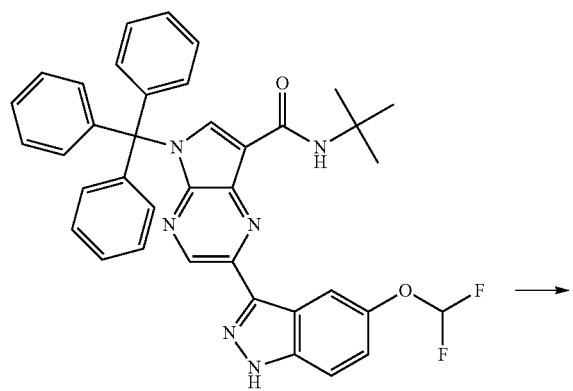

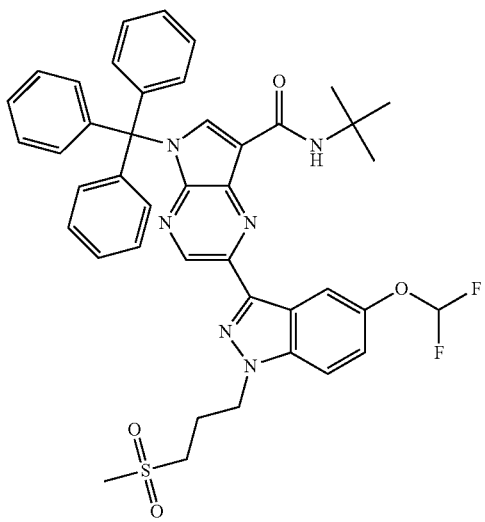

To a solution of N-tert-butyl-2-(5-(difluoromethoxy)-1H-indazol-3-yl)-5-trityl-5H-pyrrolo[3,2-b]pyrazine-7-carboxamide (100 mg, 0.156 mmol) in DMF (5 mL) was added 1-chloro-3-(methylsulfonyl)propane (30 mg, 0.187 mmol) followed by K₂CO₃ (65 mg, 0.468 mmol). The mixture was heated at 65° C. for 3 hours. After cooling to room temperature, the mixture was poured into water, filtered and dried to give N-tert-butyl-2-(5-(difluoromethoxy)-1-(3-(methylsulfonyl)propyl)-1H-indazol-3-yl)-5-trityl-5H-pyrrolo[3,2-b]pyrazine-7-carboxamide (105 mg, 88%). The crude product was used to the next step without purification. MS: (M+H)⁺= 763.

Step 2

N-tert-Butyl-2-(5-(difluoromethoxy)-1-(3-(methylsulfonyl)propyl)-1H-indazol-3-yl)-5H-pyrrolo[3,2-b]pyrazine-7-carboxamide

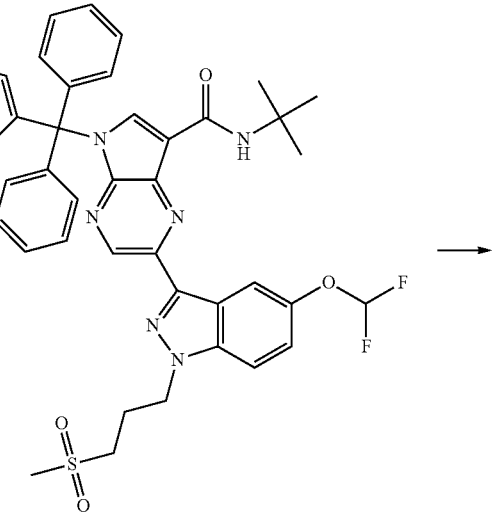

1325

-continued

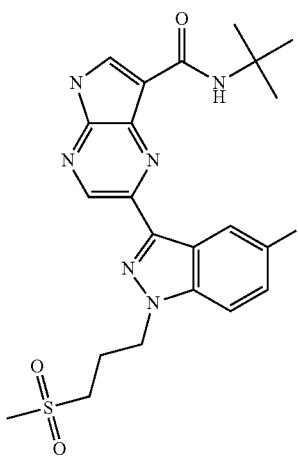

To a stirred solution of N-tert-butyl-2-(5-(difluoromethoxy)-1-(3-(methylsulfonyl)propyl)-1H-indazol-3-yl)-5-trityl-5H-pyrrolo[3,2-b]pyrazine-7-carboxamide (105 mg, 0.138 mmol) in dichloromethane (4 mL) was added drop-wise trifluoroacetic acid (2 mL) at room temperature and the reaction mixture was stirred for 2 hours. The solvent was removed under reduced pressure and the residue was purified by preparative-TLC (silica gel, EtOAc as eluent) to give N-tert-butyl-2-(5-(difluoromethoxy)-1-(3-(methylsulfonyl)propyl)-1H-indazol-3-yl)-5H-pyrrolo[3,2-b]pyrazine-7-carboxamide (50 mg, 72%) as a white solid. MS: (M+H)$^+$= 521.1; $^1$H NMR (300 MHz, DMSO): δ 12.85 (brs, 1H), 9.13 (s, 1H), 8.42 (s, 1H), 8.25 (s, 1H), 7.93 (t, 1H, J=7.8 Hz), 7.47 (d, 1H, J=9.0 Hz), 7.24 (s, 1H), 4.72 (d, 2H, J=6.6 Hz), 3.28-3.18 (m, 2H), 3.02 (s, 3H), 2.40-2.38 (m, 2H), 1.53 (s, 9H).

Example 449

2-(5-(4-Amino-4-methylpentyloxy)-1-methyl-1H-indazol-3-yl)-N-tert-butyl-5H-pyrrolo[3,2-b]pyrazine-7-carboxamide 2,2,2-trifluoroacetate

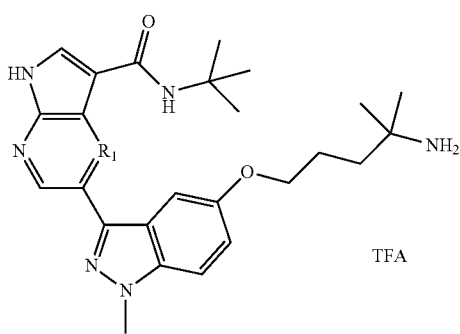

1326

Step 1

5-(tert-Butyldimethylsilyloxy)-1-methyl-3-(tributylstannyl)-1H-indazole

The solution of 5-(tert-butyldimethylsilyloxy)-3-iodo-1-methyl-1H-indazole (3.8 g, 10 mmol) in 30 mL of dry THF was cooled to −20° C. under nitrogen, isopropylmagnesium chloride (6 mL, 12 mmol, 2M in THF) was added and stirred for 15 min at −20° C. Tributylchlorostannane (12 mL, 14 mmol) was added and the reaction mixture was allowed to warm to room temperature and stirred for 1 h. The mixture was quenched with saturated solution of ammonium chloride, extracted with ethyl acetate (3×50 mL), dried over sodium sulfate and concentrated to give 5-(tert-butyldimethylsilyloxy)-1-methyl-3-(tributylstannyl)-1H-indazole (5.2 g, crude) as a colourless oil, which was used directly in the next step without further purification.

Step 2

Methyl 2-(5-(tert-butyldimethylsilyloxy)-1-methyl-1H-indazol-3-yl)-5-trityl-5H-pyrrolo[3,2-b]pyrazine-7-carboxylate

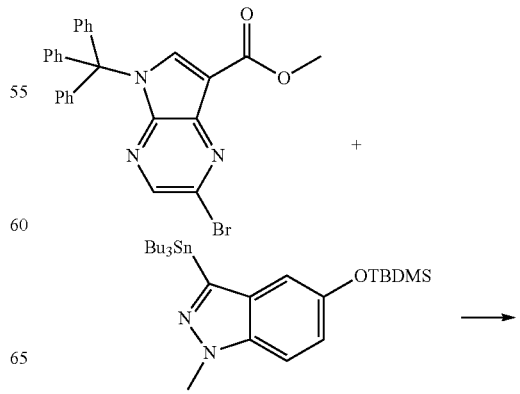

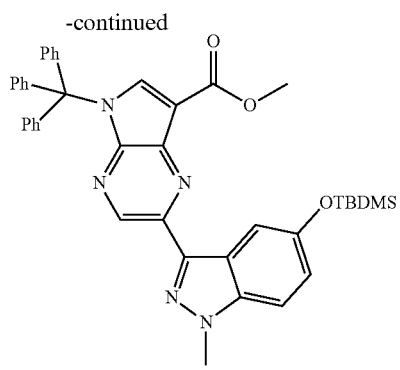

A mixture of 5-(tert-butyldimethylsilyloxy)-1-methyl-3-(tributylstannyl)-1H-indazole (5.2 g, crude from last step), methyl 2-bromo-5-trityl-5H-pyrrolo[3,2-b]pyrazine-7-carboxylate (5.6 g, 11.3 mmol), tetrakis(triphenylphosphine)palladium(0) (300 mg, 0.26 mmol), copper iodide (260 mg, 1.36 mmol) in 40 mL of dry DMF was heated to 90° C. for 3 hours under nitrogen. The reaction mixture was cooled to room temperature, diluted with 50 mL of water, extracted with ethyl acetate (3×50 mL), the organic layer was dried over Na$_2$SO$_4$, filtered and concentrated. The residue was triturated with ether (5 mL) then decanted and dried to give 245-(tert-butyldimethylsilyloxy)-1-methyl-1H-indazol-3-yl)-5-trityl-5H-pyrrolo[3,2-b]pyrazine-7-carboxylate (3.4 g, 52%). LCMS: (M+H)$^+$=680; (M+Na)$^+$=702.

Step 3

Methyl 2-(5-hydroxy-1-methyl-1H-indazol-3-yl)-5-trityl-5H-pyrrolo[3,2-b]pyrazine-7-carboxylate

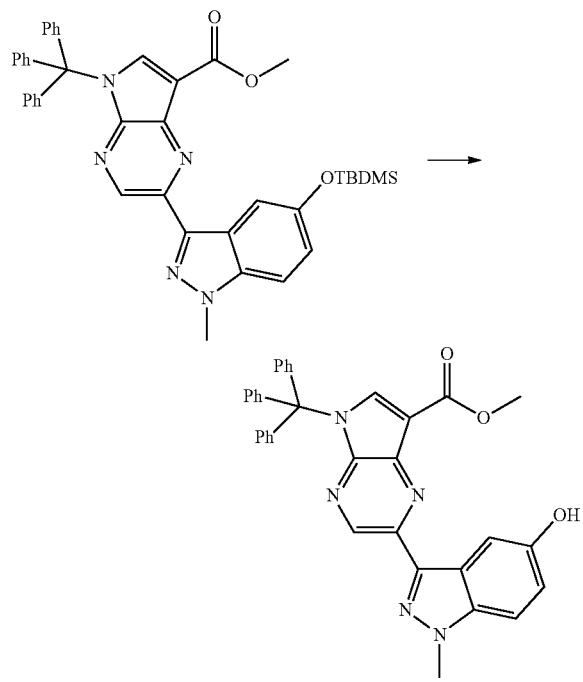

To a solution of 2-(5-(tert-butyldimethylsilyloxy)-1-methyl-1H-indazol-3-yl)-5-trityl-5H-pyrrolo[3,2-b]pyrazine-7-carboxylate (3.4 g, 4.9 mmol) in THF (25 mL) was added TBAF (6.42 mL, 12.85 mmol) at 0° C., after the addition was completed, the reaction mixture was warmed to room temperature and stirred for 0.5 hour, then H$_2$O (25 mL) was added to the mixture extracted with EtOAc (100 mL), the organic layer was washed with H$_2$O (100 mL), brine (100 mL), dried over Na$_2$SO$_4$, filtered and concentrated under reduced pressure to give methyl 2-(5-hydroxy-1-methyl-1H-indazol-3-yl)-5-trityl-5H-pyrrolo[3,2-b]pyrazine-7-carboxylate (3.2 g, >100%) as a yellow solid. LCMS: (M+H)$^+$=566; (M+Na)$^+$=588.

Step 4

Methyl 2-(1-methyl-5-(4-methyl-4-nitropentyloxy)-1H-indazol-3-yl)-5-trityl-5H-pyrrolo[3,2-b]pyrazine-7-carboxylate

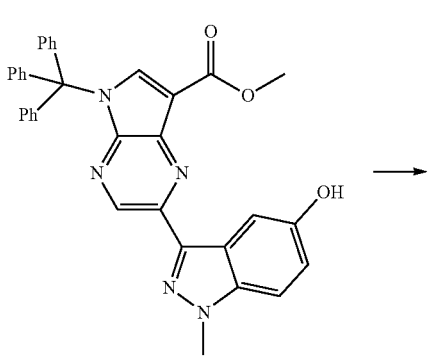

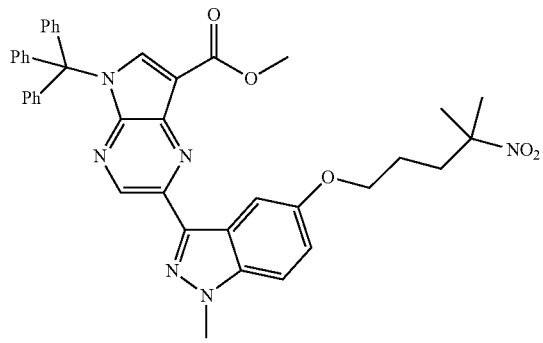

To a solution of methyl 2-(5-hydroxy-1-methyl-1H-indazol-3-yl)-5-trityl-5H-pyrrolo[3,2-b]pyrazine-7-carboxylate (2.2 g, 3.9 mmol) in DMF (25 mL) was added K$_2$CO$_3$ (1.8 g, 12.8 mmol) and 1-chloro-4-methyl-4-nitropentane (1.0 g, 5.9 mmol), after the addition, the reaction mixture was heated to 100° C. with stirring for 4 hours. The reaction mixture was cooled to room temperature, H$_2$O (25 mL) was added and product extracted with EtOAc (100 mL). The organic layer was washed with H$_2$O (100 mL) and brine (100 mL), dried over Na$_2$SO$_4$ and concentrated under reduced pressure to give methyl 2-(1-methyl-5-(4-methyl-4-nitropentyloxy)-1H-indazol-3-yl)-5-trityl-5H-pyrrolo[3,2-b]pyrazine-7-carboxylate (1.8 g, 66.7%) as yellow solid. LCMS: (M+H)⁺=695.

1H-indazol-3-yl)-5-trityl-5H-pyrrolo[3,2-b]pyrazine-7-carboxylate (400 mg, 85%) as yellow solid. LCMS: (M+H)⁺= 665.

Step 5

Methyl 2-(5-(4-amino-4-methylpentyloxy)-1-methyl-1H-indazol-3-yl)-5-trityl-5H-pyrrolo[3,2-b]pyrazine-7-carboxylate Step 6

2-(5-(4-Amino-4-methylpentyloxy)-1-methyl-1H-indazol-3-yl)-5-trityl-5H-pyrrolo[3,2-b]pyrazine-7-carboxylic acid

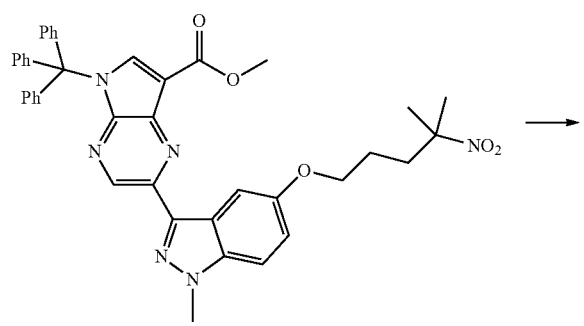

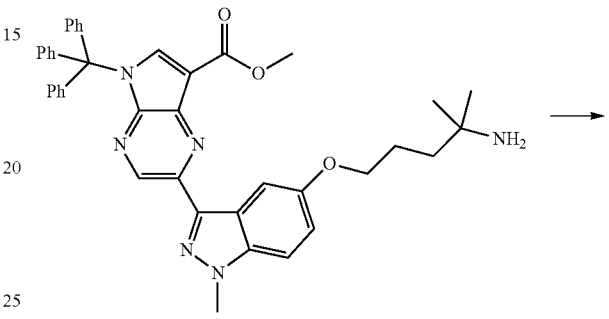

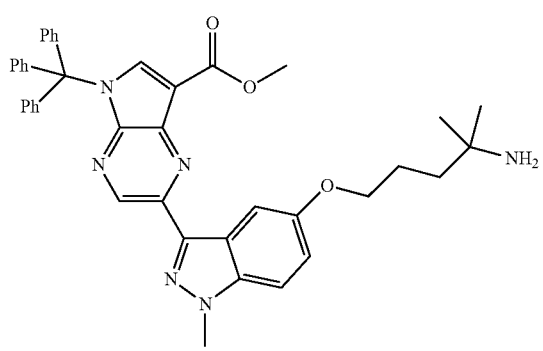

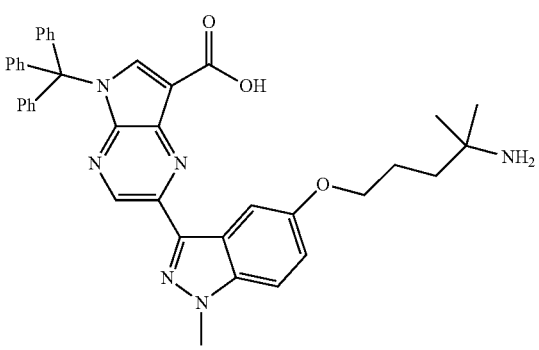

To a solution of methyl 2-(1-methyl-5-(4-methyl-4-nitropentyloxy)-1H-indazol-3-yl)-5-trityl-5H-pyrrolo[3,2-b]pyrazine-7-carboxylate (500 mg, 0.72 mmol) in CH₃OH (15 mL) was added Pd/C (0.1 g, cat.) and HCO₂NH₄ (226 mg, 3.6 mmol), after the addition, the reaction mixture was heated to 80° C. with stirring for 0.5 hour, then the mixture was filtered and filtrate evaporated, the residue was partitioned between H₂O (25 mL) and EtOAc (100 mL). The organic layer was washed with H₂O (100 mL), brine (100 mL) dried over Na₂SO₄, filtered and concentrated under reduced pressure to give methyl 2-(5-(4-amino-4-methylpentyloxy)-1-methyl- A mixture of methyl 2-(5-(4-amino-4-methylpentyloxy)-1-methyl-1H-indazol-3-yl)-5-trityl-5H-pyrrolo[3,2-b]pyrazine-7-carboxylate (100 mg, 0.15 mmol), potassium hydroxide (280 mg, 5 mmol) in 2.5 mL of water and 5 mL of 1,4-dioxane was heated to reflux for 90 min. The reaction mixture was cooled to room temperature, solvent evaporated, the residue diluted with H₂O (25 mL) and the mixture acidified with 1N HCl to pH=7. The residue was extracted with EtOAc (100 mL). The organic layer was washed with H₂O (100 mL), brine (100 mL), dried over Na₂SO₄ and concentrated under reduced pressure to give 2-(5-(4-Amino-4-methylpentyloxy)-1-methyl-1H-indazol-3-yl)-5-trityl-5H-pyrrolo[3,2-b]pyrazine-7-carboxylic acid as yellow solid (100 mg, >100%) which was used to next step without further purification. LCMS: (M+H)⁺=651.

Step 7

2-(5-(4-Amino-4-methylpentyloxy)-1-methyl-1H-indazol-3-yl)-N-tert-butyl-5-trityl-5H-pyrrolo[3,2-b]pyrazine-7-carboxamide

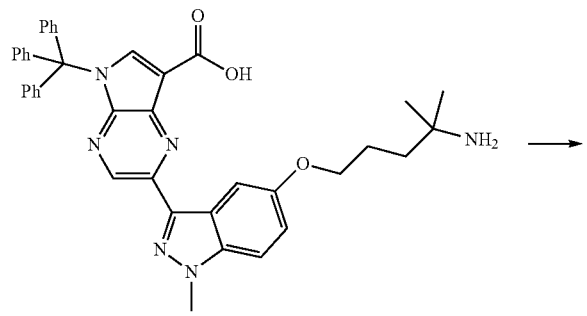

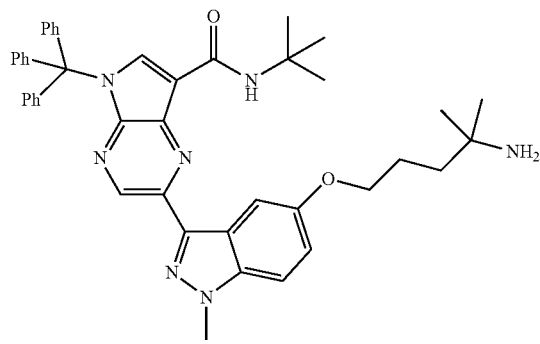

A mixture of 2-(5-(4-Amino-4-methylpentyloxy)-1-methyl-1H-indazol-3-yl)-5-trityl-5H-pyrrolo[3,2-b]pyrazine-7-carboxylic acid (100 mg, 0.15 mmol), tert-butylamine (0.05 mL, 0.45 mmol) and HATU (68.4 mg, 0.18 mmol) in 10 mL of dry THF was stirred for 4 hours at room temperature. The reaction mixture was evaporated to dryness, the residue was suspended in 50 mL of 0.5 N HCl, and product extracted with ethyl acetate (3×50 mL). The combined organic layers were dried over Na₂SO₄, filtered and concentrated to afford 2-(5-(4-amino-4-methylpentyloxy)-1-methyl-1H-indazol-3-yl)-N-tert-butyl-5-trityl-5H-pyrrolo[3,2-b]pyrazine-7-carboxa- mide (88 mg, 62%) as dark oil, material used in the next step without further purification. LCMS: (M+H)⁺=706.

Step 8

2-(5-(4-Amino-4-methylpentyloxy)-1-methyl-1H-indazol-3-yl)-N-tert-butyl-5H-pyrrolo[3,2-b]pyrazine-7-carboxamide 2,2,2-trifluoroacetate

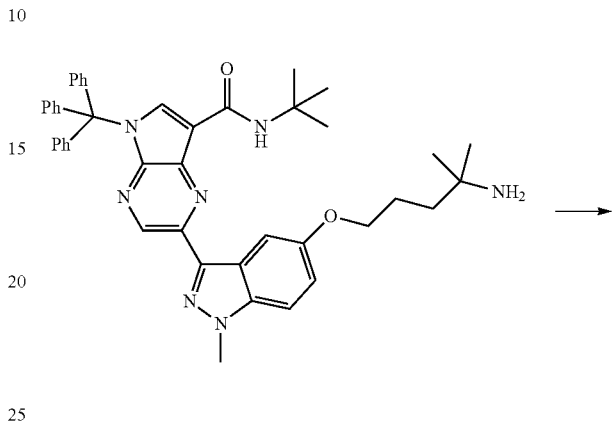

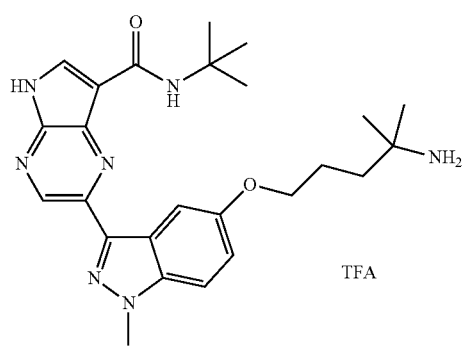

To a solution of 2-(5-(4-amino-4-methylpentyloxy)-1-methyl-1H-indazol-3-yl)-N-tert-butyl-5-trityl-5H-pyrrolo[3,2-b]pyrazine-7-carboxamide (88 mg, 0.12 mmol) in 3 mL of dichloromethane was added trifluoroacetic acid (3 mL). The reaction mixture was stirred overnight at 25° C. After solvent evaporation, the residue was purified by preparative-HPLC (Gemini 5u C18 150×21.2 mm; inject volume: 3 mL/inj, flow rate: 20 mL/min; wavelength: 214 nm and 254 nm; the gradient conditions are: 40% acetonitrile/60% water (0.1% trifluoroacetic acid V/V) initially, and then proceed to 50% acetonitrile/50% water (0.1% trifluoroacetic acid V/V) in a linear fashion after just 9 min) to afford 2-(5-(4-amino-4-methylpentyloxy)-1-methyl-1H-indazol-3-yl)-N-tert-butyl-5H-pyrrolo[3,2-b]pyrazine-7-carboxamide 2,2,2-trifluoroacetate as yellow solid (9 mg, 13%). LCMS: (M+H)⁺=464; ¹H NMR (300 MHz, CD₃OD): δ 9.01 (s, 1H), 8.26 (s, 1H), 7.85 (s, 1H), 7.56 (d, 1H, J=9.0 Hz), 7.24 (dd, 1H, J1=9.0 Hz, J2=2.4 Hz), 4.15-4.12 (m, 5H), 1.87-1.84 (m, 4H), 1.59 (s, 9H), 1.27 (s, 6H).

Example 450

2-(5-(Difluoromethoxy)-1-methyl-1H-indazol-3-yl)-N-isopropyl-5H-pyrrolo[3,2-b]pyrazine-7-carboxamide

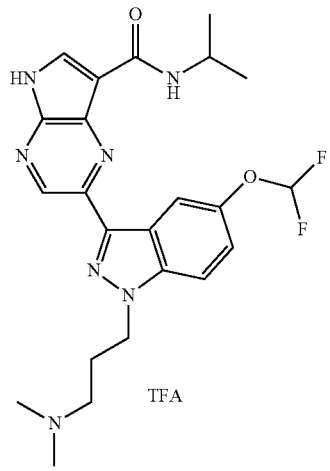 [SMILES: CC(C)NC(=O)c1c[nH]c2ncc(-c3nn(CCCN(C)C)c4ccc(OC(F)F)cc34)nc12]

Step 1

2-Bromo-N-isopropyl-5H-pyrrolo[3,2-b]pyrazine-7-carboxamide

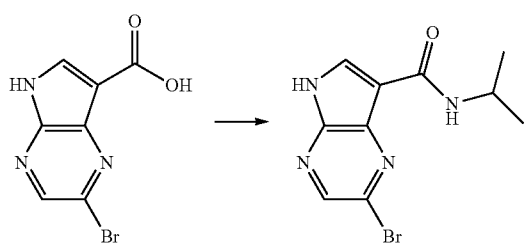 [SMILES: O=C(O)c1c[nH]c2ncc(Br)nc12 ; CC(C)NC(=O)c1c[nH]c2ncc(Br)nc12]

A mixture of 2-bromo-5H-pyrrolo[3,2-b]pyrazine-7-carboxylic acid (250 mg, 1.03 mmol), propan-2-amine (0.15 mL, 1.5 mmol) and HATU (456 mg, 1.2 mmol) in 20 mL of dry THF was stirred for 4 hours. The reaction mixture was evaporated to dryness, the residue was suspended in 20 mL of 0.5 N HCl, product extracted with ethyl acetate (3×50 mL), organics combined were dried with sodium sulfate and concentrated. The residue was purified by column chromatography (silica gel. 200-300 mesh, eluting with ethyl acetate/petroleum ether=2:1) to give 2-bromo-N-isopropyl-5H-pyrrolo[3,2-b]pyrazine-7-carboxamide (180 mg, 62%). $^1$H NMR (300 MHz, DMSO): δ 12.95 (s, 1H), 8.49 (s, 1H), 8.43 (s, 1H), 7.59-7.56 (m, 1H), 4.13-4.06 (m, 1H), 1.24-1.20 (m, 6H). LCMS: (M+H)$^+$=283/285.

Step 2

2-(5-(Difluoromethoxy)-1-methyl-1H-indazol-3-yl)-N-isopropyl-5H-pyrrolo[3,2-b]pyrazine-7-carboxamide

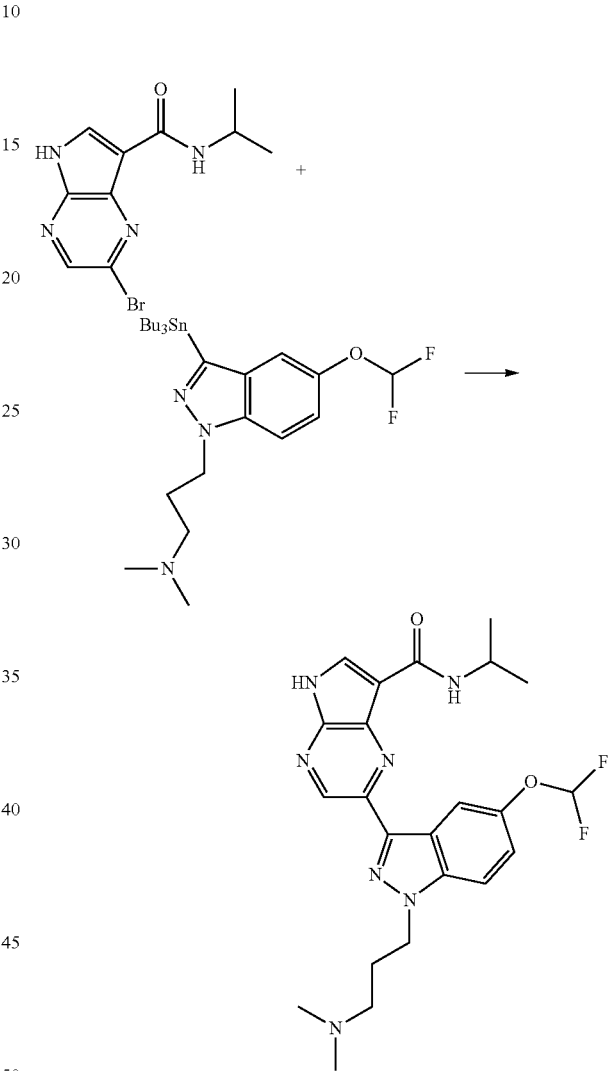

To a solution of 3-(5-(difluoromethoxy)-3-(tributylstannyl)-1H-indazol-1-yl)-N,N-dimethylpropan-1-amine (200 mg, 0.36 mmol) and 2-bromo-N-isopropyl-5H-pyrrolo[3,2-b]pyrazine-7-carboxamide (180 mg, 0.43 mmol) in DMF (10 mL) were added CuI (18 mg, 0.08 mmol) and Pd(PPh$_3$)$_4$ (14 mg, 0.014 mmol), Then the reaction mixture was degassed by bubbling nitrogen for 3 minutes and refilled with nitrogen. The mixture was heated to 80° C. for 5 hours under nitrogen, after cooling to room temperature, water (50 mL) was added and product extracted with EtOAc (3×40 mL), the combined organic layers were dried over Na$_2$SO$_4$, concentrated under reduced pressure and the residue was purified by preparative-HPLC (Gemini 5u C18 150×21.2 mm; inject volume: 3 mL/inj, flow rate: 20 mL/min; wavelength: 214 nm and 254 nm; the gradient conditions are: 40% acetonitrile/60% water (0.1% trifluoroacetic acid V/V) initially, and then proceed to 50% acetonitrile/50% water (0.1% trifluoroacetic acid V/V) in a linear fashion after just 9 min) to afford 2-(5-(difluoromethoxy)-1-methyl-1H-indazol-3-yl)-N-isopropyl-5H-pyrrolo[3,2-b]pyrazine-7-carboxamide as yellow solid (13 mg, 9%). LCMS: (M+H)$^+$=472; $^1$H NMR (300 MHz, CD$_3$OD): δ 9.11 (s, 1H), 8.24 (s, 1H), 8.11 (s, 1H), 7.69 (d, 1H, J=9.0 Hz), 7.38 (d, 1H, J=8.7 Hz), 6.85 (t, 1H, J=74.1 Hz), 4.85-4.78 (m, 2H), 4.65-4.60 (m, 1H), 3.34-3.32 (m, 2H), 2.89 (s, 6H), 2.50-2.40 (m, 2H), 1.43 (s, 3H), 1.40 (s, 3H).

Example 451

N-tert-Butyl-2-(1-methyl-1H-indazol-4-yl)-5H-pyrrolo[3,2-b]pyrazine-7-carboxamide hydrochloride

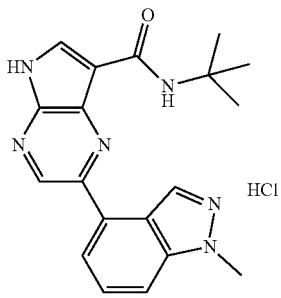 [SMILES: Cn1ncc2c(-c3cnc4[nH]cc(C(=O)NC(C)(C)C)c4n3)cccc21 ; Cl]

Step 1

2-Bromo-N-tert-butyl-5-trityl-5H-pyrrolo[3,2-b]pyrazine-7-carboxamide

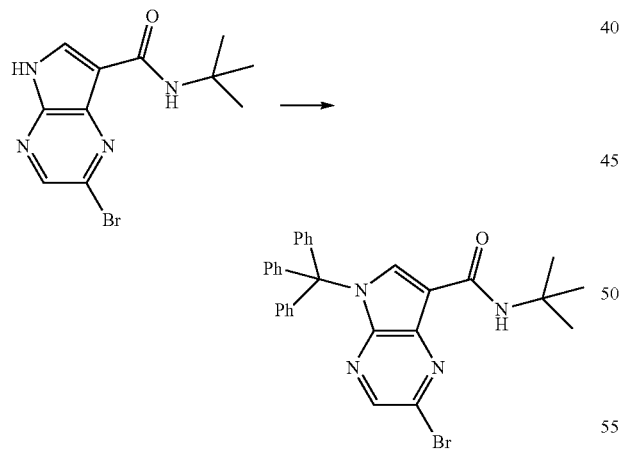

A mixture of 2-bromo-N-tert-butyl-5H-pyrrolo[3,2-b]pyrazine-7-carboxamide (378 mg, 1.272 mmol), (chloromethanetriyl)tribenzene (426 mg, 1.53 mmol) and triethylamine (193 mg, 1.91 mmol) in dry DMF (20 mL) was heated to 90° C. for 16 hours. Reaction mixture was extracted with ethyl acetate (100 mL), organic phase washed with water (3×10 mL) and brine (2×10 mL), then dried over Na$_2$SO$_4$, filtered and concentrated. The residue was purified by column chromatography (silica gel, 200-300 mesh, eluting with EtOAc: petroleum ether=1:15) to afford 2-bromo-N-tert-butyl-5-trityl-5H-pyrrolo[3,2-b]pyrazine-7-carboxamide (515 mg, 75%) as a white solid. $^1$H NMR (300 MHz, CDCl$_3$): δ 8.29 (s, 1H), 8.01 (s, 1H), 7.29-7.26 (m, 10H), 7.13-7.11 (m, 5H), 1.51 (s, 9H). LCMS: (M+H)$^+$=539.

Step 2

N-tert-Butyl-2-(1H-indazol-4-yl)-5-trityl-5H-pyrrolo[3,2-b]pyrazine-7-carboxamide

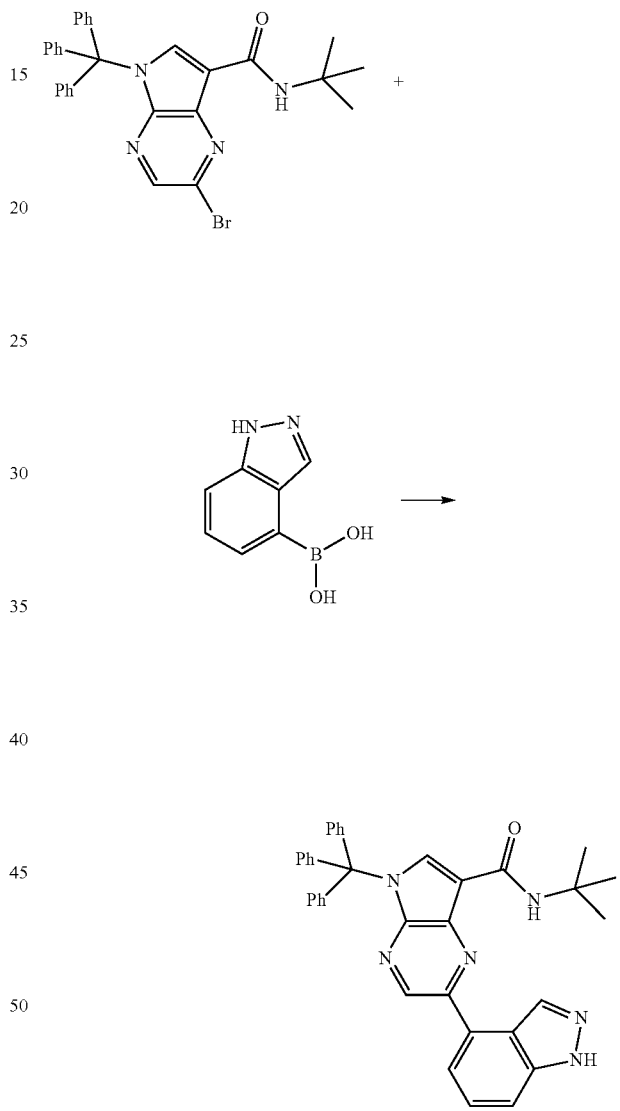

A mixture of 2-bromo-N-tert-butyl-5-trityl-5H-pyrrolo[3,2-b]pyrazine-7-carboxamide (0.5 g, 0.928 mmol), 1H-indazol-4-ylboronic acid (165 mg, 1.02 mmol), Pd(PPh$_3$)$_4$ (214 mg, 0.186 mmol), X-Phos (177 mg, 0.371 mmol) and Na$_2$CO$_3$ (295 mg, 2.78 mmol) in dioxane (20 mL) and water (5 mL) was heated to 100° C. for 16 hours under N$_2$ atmosphere. Reaction mixture was concentrated and the residue was purified by preparative-TLC (eluting with methanol:dichloromethane=1:100) to afford N-tert-butyl-2-(isoquinolin-8-yl)-5H-pyrrolo[3,2-b]pyrazine-7-carboxamide (375 mg, 70%) as a yellow solid. $^1$H NMR (300 MHz, CDCl$_3$): δ 10.37 (s, 1H), 8.61 (s, 1H), 8.60 (s, 1H), 8.54 (s, 1H), 8.36 (s, 1H), 7.55-7.49 (m, 3H), 7.30-7.26 (m, 9H), 7.22-7.18 (m, 6H), 1.53 (s, 9H). LCMS: (M+H)+=577.

Step 3

N-tert-Butyl-2-(1-methyl-1H-indazol-4-yl)-5-trityl-5H-pyrrolo[3,2-b]pyrazine-7-carboxamide

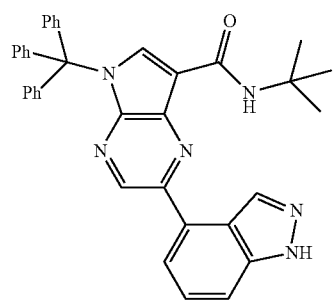

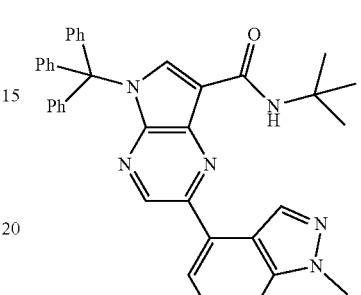

To a solution of N-tert-butyl-2-(1H-indazol-4-yl)-5-trityl-5H-pyrrolo[3,2-b]pyrazine-7-carboxamide (375 mg, 0.65 mmol) in dry THF (20 mL) was added potassium 2-methyl-propan-2-olate (109 mg, 0.975 mmol) at 0° C. After stirring for 30 minutes, iodomethane (138 mg, 0.975 mmol) was added at 0° C. Then it was warmed to room temperature and stirred for 1 hour. Reaction mixture was quenched by the addition of water (2 mL), extracted with ethyl acetate (100 mL), then organic phase washed with water (3×10 mL) and brine (2×10 mL). The organic layer was dried over Na₂SO₄, filtered and concentrated. The residue was purified by column chromatography (silica gel, 200-300 mesh, eluting with EtOAc: petroleum ether=1:3) to afford N-tert-butyl-2-(1-methyl-1H-indazol-4-yl)-5-trityl-5H-pyrrolo[3,2-b]pyrazine-7-carboxamide (154 mg, 40%) as a white solid. LCMS: (M+H)+= 591; ¹H NMR (300 MHz, CDCl₃): δ 8.54 (s, 1H), 8.50 (s, 1H), 8.40 (s, 1H), 8.35 (s, 1H), 7.53-7.47 (m, 3H), 7.32-7.27 (m, 9H), 7.24-7.19 (m, 6H), 4.14 (s, 3H), 1.52 (s, 9H).

Step 4

N-tert-Butyl-2-(1-methyl-1H-indazol-4-yl)-5H-pyrrolo[3,2-b]pyrazine-7-carboxamide hydrochloride

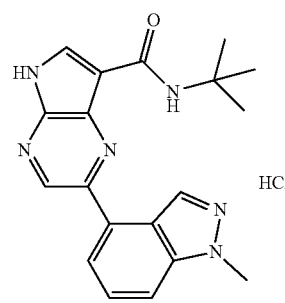

To a stirred solution of N-tert-butyl-2-(1-methyl-1H-indazol-4-yl)-5-trityl-5H-pyrrolo[3,2-b]pyrazine-7-carboxamide (154 mg, 0.261 mmol) in dioxane (20 mL) was bubbled HCl gas until saturation and then stirred at room temperature for 4 hours. Reaction mixture was concentrated and the residue was triturated with methanol (1 mL) then decanted and dried to afford N-tert-butyl-2-(1-methyl-1H-indazol-4-yl)-5H-pyrrolo[3,2-b]pyrazine-7-carboxamide hydrochloride (38 mg, 38%) as a white solid. LCMS: (M+H)+=349; ¹H NMR (300

MHz, CDCl₃): δ 9.77 (s, 1H), 8.89 (s, 1H), 8.54 (s, 1H), 8.39 (s, 2H), 7.66-7.52 (m, 3H), 4.20 (s, 3H), 1.58 (s, 9H).

Example 452

2-(5-(Difluoromethoxy)-1-(3-(dimethylamino)propyl)-1H-indazol-3-yl)-N-(1-methylcyclopropyl)-5H-pyrrolo[3,2-b]pyrazine-7-carboxamide trifluoroacetate

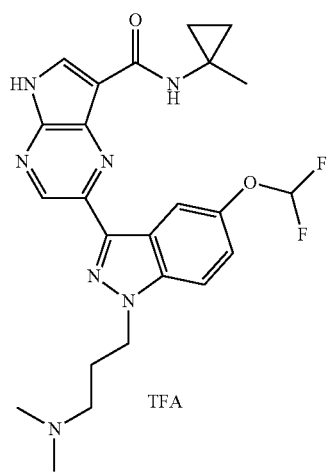 [SMILES: CN(C)CCCn1nc(-c2cnc3[nH]cc(C(=O)NC4(C)CC4)c3n2)c2cc(OC(F)F)ccc21]

Step 1

2-Bromo-N-(1-methylcyclopropyl)-5H-pyrrolo[3,2-b]pyrazine-7-carboxamide

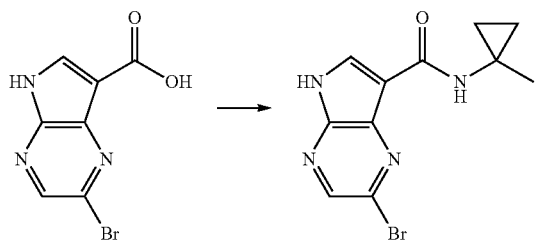 [SMILES: O=C(O)c1c[nH]c2ncc(Br)nc12 ; CC1(NC(=O)c2c[nH]c3ncc(Br)nc23)CC1]

A mixture of 2-bromo-5H-pyrrolo[3,2-b]pyrazine-7-carboxylic acid (250 mg, 1.03 mmol), 1-methylcyclopropanamine (150 mg, 2.2 mmol) and HATU (456 mg, 1.2 mmol) in 20 mL of dry THF was stirred for 4 hours. The reaction mixture was evaporated to dryness, the residue suspended in 20 mL of 0.5 N HCl, product extracted with ethyl acetate (3×50 mL), organics combined dried with sodium sulfate, filtered and concentrated. The residue was triturated with petroleum ether (2 mL) then decanted and dried to give 2-bromo-N-isopropyl-5H-pyrrolo[3,2-b]pyrazine-7-carboxamide (125 mg, crude). LCMS: (M+H)⁺=285/287.

Step 2

2-Bromo-N-(1-methylcyclopropyl)-5-trityl-5H-pyrrolo[3,2-b]pyrazine-7-carboxamide

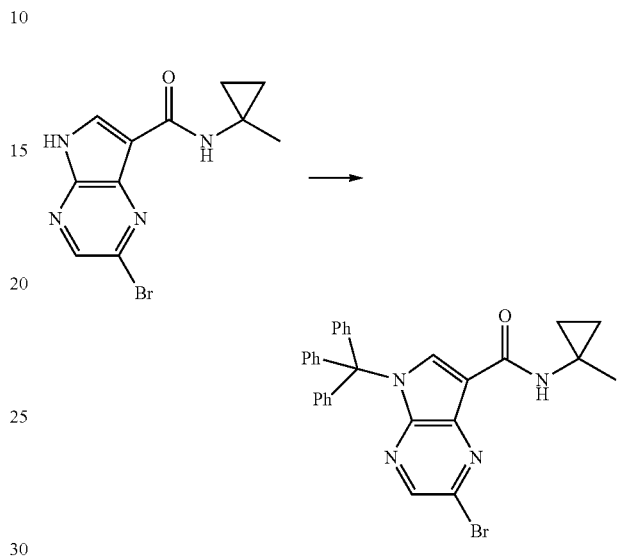

To a solution of 2-bromo-N-(1-methylcyclopropyl)-5H-pyrrolo[3,2-b]pyrazine-7-carboxamide (600 mg, 2.1 mmol) in 20 mL of dry THF was added Et₃N (0.42 mL, 4.2 mmol) and reaction mixture stirred for 5 mins, then (chloromethanetriyl)tribenzene (540 mg, 2.53 mmol) was added and reaction mixture stirred for 10 mins. Then, the reaction was heated to 60° C. and stirring continued for 3 hrs. The reaction was quenched with brine (10 mL), product extracted with ethyl acetate (3×20 mL), organics combined dried with sodium sulfate, filtered and concentrated to give 2-bromo-N-(1-methylcyclopropyl)-5-trityl-5H-pyrrolo[3,2-b]pyrazine-7-carboxamide (400 mg, 37%) as yellow solid. ¹H NMR (300 MHz, CDCl₃): δ 8.32 (s, 1H), 8.01 (s, 1H), 7.31-7.26 (m, 15H), 1.51 (s, 3H), 1.25 (s, 2H), 0.90-0.74 (m, 2H). LCMS: (M+H)⁺=537/539.

Step 3

2-(5-(Difluoromethoxy)-1-(3-(dimethylamino)propyl)-1H-indazol-3-yl)-N-(1-methylcyclopropyl)-5-trityl-5H-pyrrolo[3,2-b]pyrazine-7-carboxamide

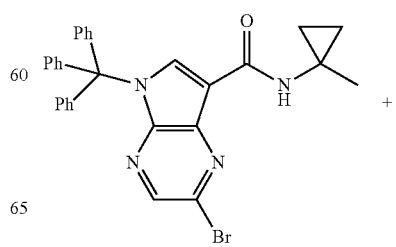 +

-continued

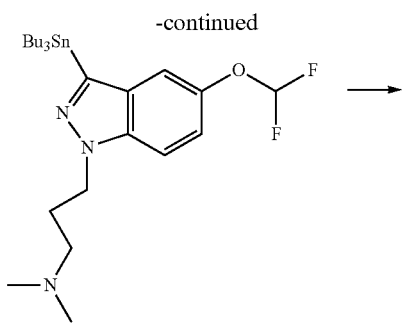

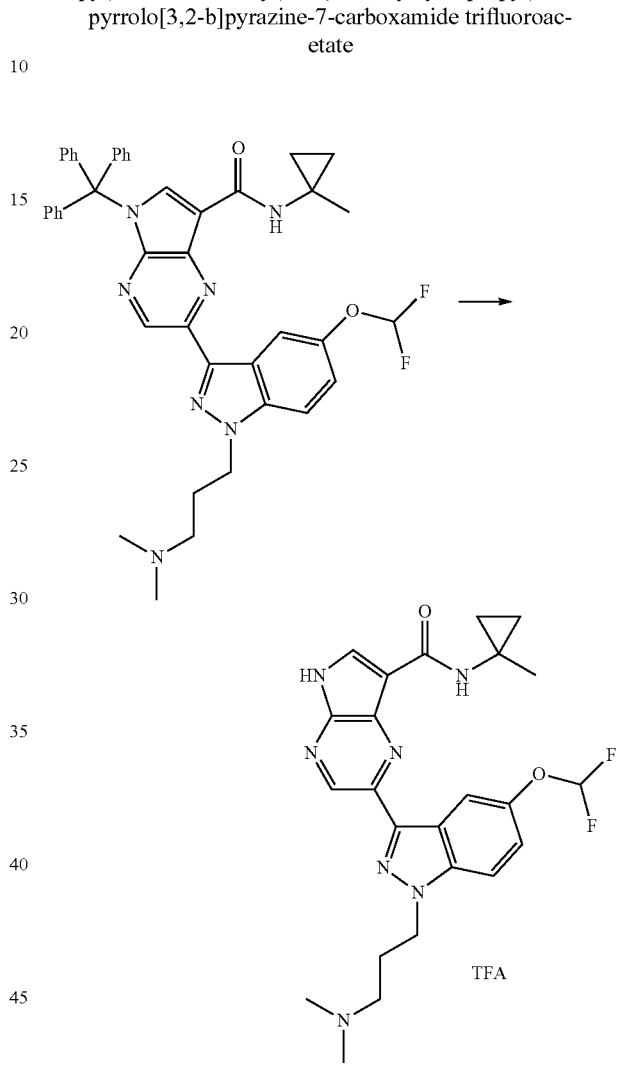

To a solution of 3-(5-(difluoromethoxy)-3-(tributylstannyl)-1H-indazol-1-yl)-N,N-dimethylpropan-1-amine (200 mg, 0.36 mmol) and 2-bromo-N-(1-methylcyclopropyl)-5-trityl-5H-pyrrolo[3,2-b]pyrazine-7-carboxamide (250 mg, 0.43 mmol) in DMF (10 mL) were added CuI (18 mg, 0.08 mmol) and Pd(PPh₃)₄ (14 mg, 0.014 mmol), Then the reaction mixture was degassed by bubbling nitrogen for 3 minutes and refilled with nitrogen. The mixture was heated to 80° C. for 5 hours under nitrogen, after cooling to room temperature, water (50 mL) was added and product extracted with EtOAc (3×40 mL), the combined organic layers were dried over Na₂SO₄ concentrated under reduced pressure to afford 2-(5-(difluoromethoxy)-1-(3-(dimethylamino)propyl)-1H-indazol-3-yl)-N-(1-methylcyclopropyl)-5-trityl-5H-pyrrolo[3,2-b]pyrazine-7-carboxamide as yellow solid (200 mg, 47%), material used in the next step without further purification. LCMS: (M+H)⁺=726; (M+Na)⁺=748.

Step 4

2-(5-(Difluoromethoxy)-1-(3-(dimethylamino)propyl)-1H-indazol-3-yl)-N-(1-methylcyclopropyl)-5H-pyrrolo[3,2-b]pyrazine-7-carboxamide trifluoroacetate To a solution of 2-(5-(difluoromethoxy)-1-(3-(dimethylamino)propyl)-1H-indazol-3-yl)-N-(1-methylcyclopropyl)-5-trityl-5H-pyrrolo[3,2-b]pyrazine-7-carboxamide (200 mg, 0.3 mmol) in 3 mL of dichloromethane was added trifluoroacetic acid (3 mL). The reaction mixture was stirred at room temperature overnight. After solvent evaporation, the residue was purified by preparative-HPLC (Gemini 5u C18 150×21.2 mm; inject volume: 3 mL/inj, flow rate: 20 mL/min; wavelength: 214 nm and 254 nm; the gradient conditions are: 40% acetonitrile/60% water (0.1% trifluoroacetic acid V/V) initially, and then proceed to 50% acetonitrile/50% water (0.1% trifluoroacetic acid V/V) in a linear fashion after just 9 min) to afford 245-(difluoromethoxy)-1-(3-(dimethylamino)propyl)-1H-indazol-3-yl)-N-(1-methylcyclopropyl)-5H-pyrrolo[3,2-b]pyrazine-7-carboxamide trifluoroacetate (20 mg, 7%) as a yellow solid. LCMS: (M+H)⁺=484; ¹H NMR (300 MHz, CD₃OD): δ 9.04 (s, 1H), 8.13 (s, 1H), 8.02 (s, 1H), 7.61 (d, 1H, J=9.0 Hz), 7.29 (dd, 1H, J1=9.0 Hz, J2=2.1 Hz), 6.78 (t, 1H, J=73.8 Hz), 4.56-4.52 (m, 2H), 3.19-3.12 (m, 2H), 2.79 (s, 6H), 2.39-2.33 (m, 2H), 1.47 (s, 3H), 0.93-0.89 (m, 2H), 0.76-0.72 (m, 2H).

Example 453

2-(5-(Difluoromethoxy)-1-(3-(dimethylamino)propyl)-1H-indazol-3-yl)-N-ethyl-5H-pyrrolo[3,2-b]pyrazine-7-carboxamide trifluoroacetate

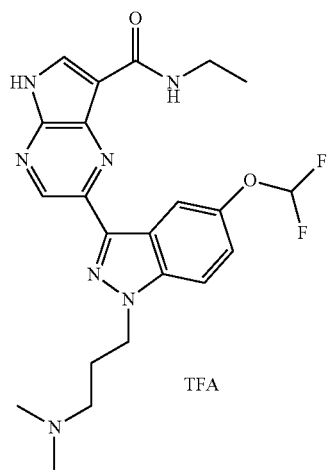 [SMILES: CCNC(=O)c1c[nH]c2ncc(-c3nn(CCCN(C)C)c4ccc(OC(F)F)cc34)nc12]

Step 1

2-Bromo-N-ethyl-5H-pyrrolo[3,2-b]pyrazine-7-carboxamide

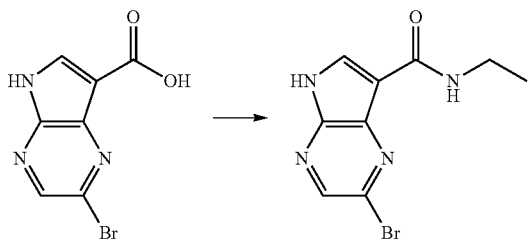

A mixture of 2-bromo-5H-pyrrolo[3,2-b]pyrazine-7-carboxylic acid (250 mg, 1.03 mmol), ethanamine (0.2 mL 2.2 mmol) and HATU (456 mg, 1.2 mmol) in 20 mL of dry THF was stirred for 4 hours at room temperature. The reaction mixture was evaporated to dryness, the residue was suspended in 20 mL of 0.5 N HCl, product extracted with ethyl acetate (3×50 mL), organics combined dried with sodium sulfate, filtered and concentrated. Residue purified by column chromatography (silica gel, 200-300 mesh, eluting with ethyl acetate/petroleum ether 2:1) to give 2-bromo-N-isopropyl-5H-pyrrolo[3,2-b]pyrazine-7-carboxamide (180 mg, 43%). LCMS: (M+H)+=269/271; $^1$H NMR (300 MHz, CD$_3$OD): δ 12.95 (s, 1H), 8.50 (s, 1H), 8.43 (s, 1H), 7.77-7.72 (m, 1H), 3.42-3.36 (m, 2H), 1.25-1.12 (m, 3H).

Step 2

2-(5-(Difluoromethoxy)-1-(3-(dimethylamino)propyl)-1H-indazol-3-yl)-N-ethyl-5H-pyrrolo[3,2-b]pyrazine-7-carboxamide trifluoroacetate

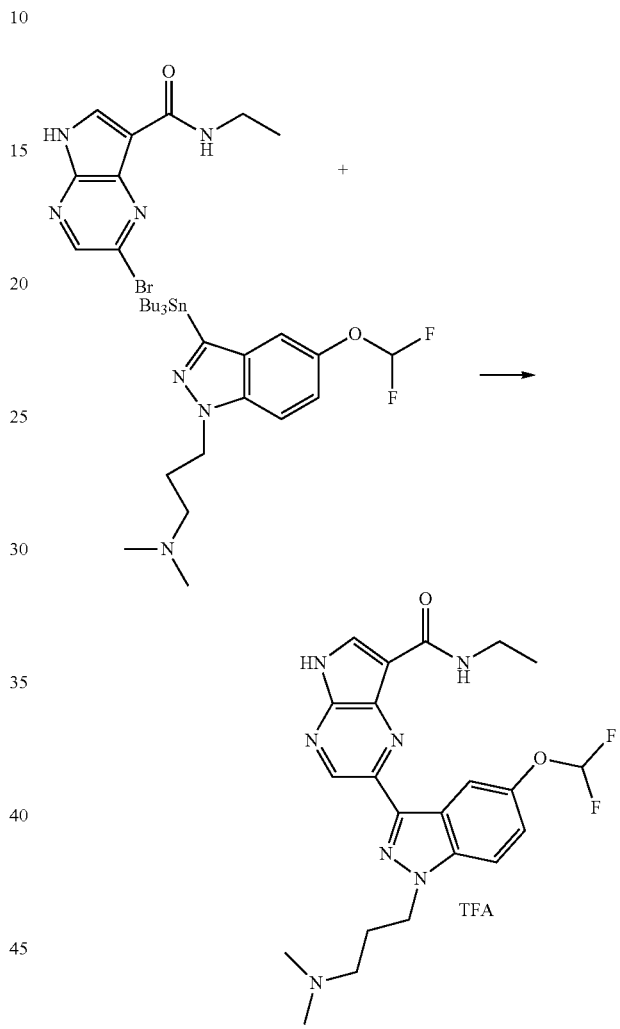

To a solution of 3-(5-(difluoromethoxy)-3-(tributylstannyl)-1H-indazol-1-yl)-N,N-dimethylpropan-1-amine (200 mg, 0.36 mmol) and 2-bromo-N-ethyl-5H-pyrrolo[3,2-b]pyrazine-7-carboxamide (180 mg, 0.38 mmol) in DMF (10 mL) were added CuI (18 mg, 0.08 mmol) and Pd(PPh$_3$)$_4$ (14 mg, 0.014 mmol), Then the reaction mixture was degassed by bubbling nitrogen for 3 minutes and refilled with nitrogen. The mixture was heated to 80° C. for 5 hours under nitrogen. After cooling to room temperature, water (50 mL) was added to the mixture and product extracted with EtOAc (3×40 mL), the combined organic layers were dried over Na$_2$SO$_4$, filtered and concentrated under reduced pressure. The residue was purified by preparative-HPLC (Gemini 5u C18 150×21.2 mm; inject volume: 3 mL/inj, flow rate: 20 mL/min; wavelength: 214 nm and 254 nm; the gradient conditions are: 40% acetonitrile/60% water (0.1% trifluoroacetic acid V/V) initially, and then proceed to 50% acetonitrile/50% water (0.1% trifluoroacetic acid V/V) in a linear fashion after just 9 min to afford 2-(5-(difluoromethoxy)-1-(3-(dimethylamino)propyl)-1H-indazol-3-yl)-N-ethyl-5H-pyrrolo[3,2-b]pyrazine-7-carboxamide trifluoroacetate (20 mg, 7%) as yellow solid. LCMS: (M+H)⁺=458; ¹H NMR (300 MHz, CD₃OD): δ 8.97 (s, 1H), 8.09 (s, 1H), 7.90 (d, 1H, J=1.8 Hz), 7.57 (d, 1H, J=9.3 Hz), 7.24 (d, 1H, J=9.0 Hz), 6.75 (t, 1H, J=73.8 Hz), 4.53-4.48 (m, 2H), 3.44 (q, 2H, J=7.2 Hz), 3.19-3.12 (m, 2H), 2.79 (s, 6H), 2.37-2.34 (m, 2H), 1.26 (t, 3H, J=7.2 Hz).

Example 454

2-(1-(4-Amino-4-methylpentyl)-5-(difluoromethoxy)-1H-indazol-3-yl)-N-tert-butyl-5H-pyrrolo[3,2-b]pyrazine-7-carboxamide trifluoroacetate

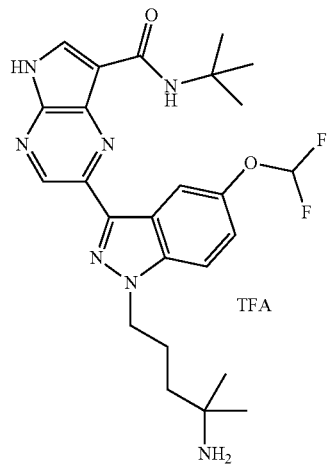 [SMILES: CC(C)(N)CCCn1nc(-c2cnc3[nH]cc(C(=O)NC(C)(C)C)c3n2)c2cc(OC(F)F)ccc21]

Step 1

5-(Difluoromethoxy)-3-(tributylstannyl)-1H-indazole

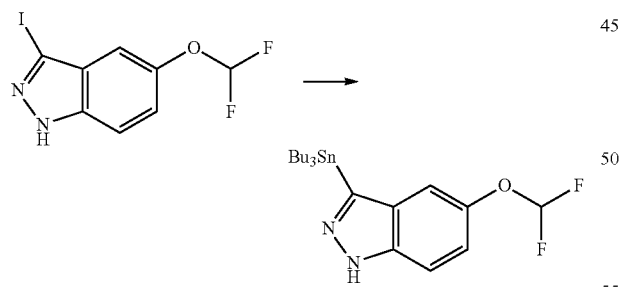

To a solution of 3-(5-(difluoromethoxy)-3-iodo-1H-indazol-1-yl)-N,N-dimethylpropan-1-amine (1.2 g, 2.78 mmol) in dry THF (25 mL) was added isopropylmagnesium chloride (1.5 mL, 2M in THF, 3 mmol) drop-wise at −16° C. under nitrogen atmosphere. The reaction was stirred for 30 minutes, then dibutylchloro(propyl)stannane (3.3 mL, 3.6 mmol) was added dropwise at −16° C. under nitrogen, then the reaction mixture was slowly warmed to room temperature and stirred for 2 hours. The reaction mixture was quenched with a solution of saturated NH₄Cl (40 mL) and product extracted with EtOAc (3×30 mL), organics combined dried with sodium sulfate, filtered and concentrated. Crude oil used into the next step without further purification (1.1 g, crude).

Step 2

N-tert-Butyl-2-(5-(difluoromethoxy)-1H-indazol-3-yl)-5-trityl-5H-pyrrolo[3,2-b]pyrazine-7-carboxamide

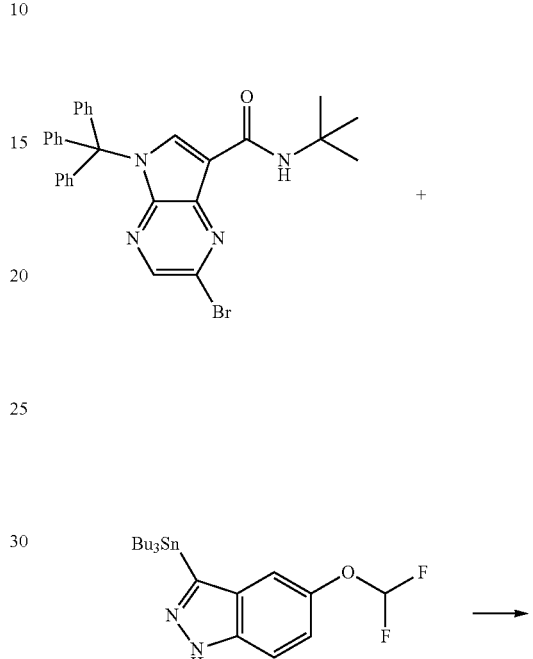

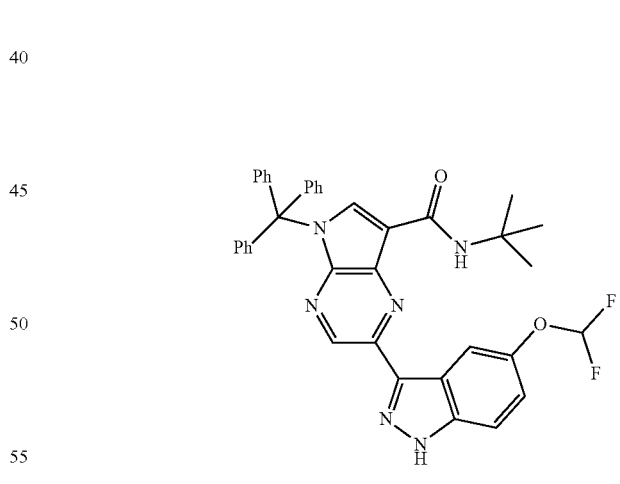

A mixture of 5-(difluoromethoxy)-3-(tributylstannyl)-1H-indazole (250 mg, 0.57 mmol), 2-bromo-N-tert-butyl-5-trityl-5H-pyrrolo[3,2-b]pyrazine-7-carboxamide (280 mg, 0.58 mmol), tetrakis(triphenylphosphine)palladium(0) (23 mg, 0.02 mmol), copper iodide (26 mg, 1.36 mmol) in 10 mL of dry DMF was heated to 90° C. for 3 hours under N₂. The reaction mixture was cooled to room temperature, diluted with 50 mL of water, product extracted with ethyl acetate (3×20 mL), organics combined dried with sodium sulfate, filtered and concentrated to give N-tert-butyl-2-(5-(difluoromethoxy)-1H-indazol-3-yl)-5-trityl-5H-pyrrolo[3,2-b]pyrazine-7-carboxamide (208 mg, crude). LCMS: (M+H)⁺= 643.

Step 3

N-tert-Butyl-2-(5-(difluoromethoxy)-1-(4-methyl-4-nitropentyl)-1H-indazol-3-yl)-5-trityl-5H-pyrrolo[3,2-b]pyrazine-7-carboxamide

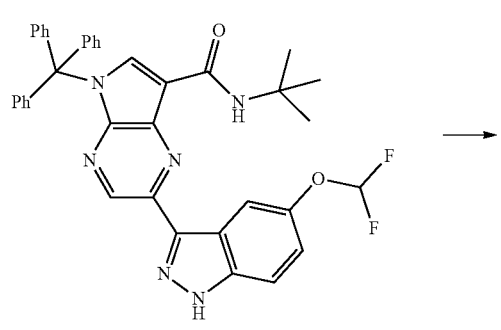

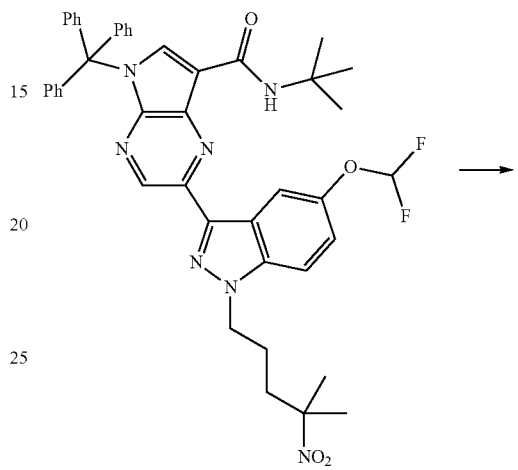

(200 mg, 69%) as yellow solid, material used in the next step without further purification. LCMS: (M+H)⁺=772; (M+Na)⁺= 794.0.

Step 4

2-(1-(4-Amino-4-methylpentyl)-5-(difluoromethoxy)-1H-indazol-3-yl)-N-tert-butyl-5-trityl-5H-pyrrolo[3,2-b]pyrazine-7-carboxamide

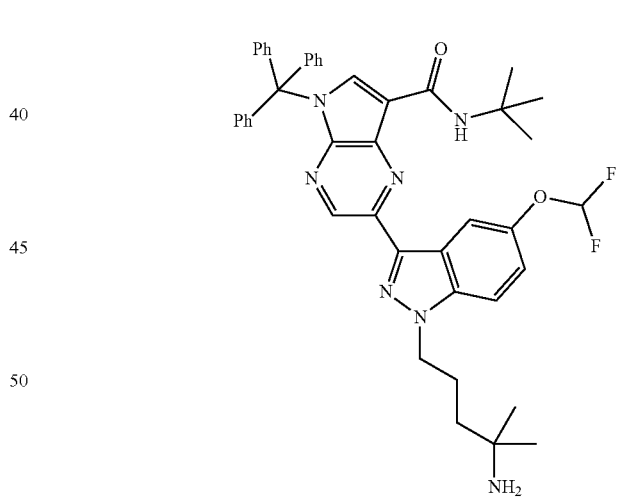

To a solution of N-tert-butyl-2-(5-(difluoromethoxy)-1H-indazol-3-yl)-5-trityl-5H-pyrrolo[3,2-b]pyrazine-7-carboxamide (208 mg, 0.35 mmol) in DMF (15 mL) was added K₂CO₃ (193 mg, 1.4 mmol) and 1-chloro-4-methyl-4-nitropentane (100 mg, 0.59 mmol), after the addition, the reaction mixture was heated to 100° C. with stirring for 4 hours. Then, the mixture was quenched with H₂O (25 mL) and product extracted with EtOAc (50 mL). The organic layer was washed with H₂O (100 mL), brine (100 mL), dried over Na₂SO₄ and concentrated under reduced pressure to give N-tert-butyl-2-(5-(difluoromethoxy)-1-(4-methyl-4-nitropentyl)-1H-indazol-3-yl)-5-trityl-5H-pyrrolo[3,2-b]pyrazine-7-carboxamide To a solution of 2-(1-(4-amino-4-methylpentyl)-5-(difluoromethoxy)-1H-indazol-3-yl)-N-tert-butyl-5-trityl-5H-pyrrolo[3,2-b]pyrazine-7-carboxamide (200 mg, 0.3 mmol) in CH₃OH (10 mL) was added 10% Pd/C (0.1 g) and HCO₂NH₄ (113 mg, 1.8 mmol), after the addition, the reaction mixture was heated to 80° C. with stirring for 0.5 hour, then the mixture was filtered and evaporated. The residue was partitioned between H₂O (25 mL) and EtOAc (50 mL). The organic layer was washed with H₂O (100 mL), brine (100 mL), dried over Na₂SO₄ and concentrated under reduced pressure to give 2-(1-(4-amino-4-methylpentyl)-5-(difluoromethoxy)-1H-indazol-3-yl)-N-tert-butyl-5-trityl-5H-pyrrolo[3,2-b]pyrazine-7-carboxamide (54 mg, 39%) as white solid, material used in the next step without further purification. LCMS: (M+H)$^+$=742.

Step 5

2-(1-(4-Amino-4-methylpentyl)-5-(difluoromethoxy)-1H-indazol-3-yl)-N-tert-butyl-5H-pyrrolo[3,2-b]pyrazine-7-carboxamide trifluoroacetate

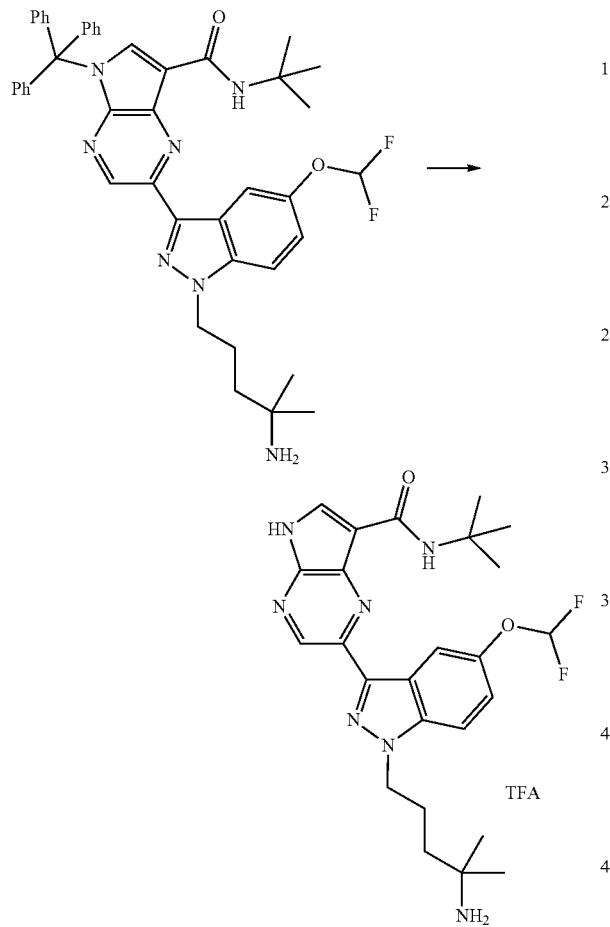

To a solution of 2-(1-(4-amino-4-methylpentyl)-5-(difluoromethoxy)-1H-indazol-3-yl)-N-tert-butyl-5-trityl-5H-pyrrolo[3,2-b]pyrazine-7-carboxamide (54 mg, 0.08 mmol) in 3 mL of dichloromethane was added 3 mL of trifluoroacetic acid. The reaction mixture was stirred overnight at room temperature. After solvent evaporation, the residue was purified by preparative-HPLC (Gemini 5u C18 150×21.2 mm; inject volume: 3 mL/inj, flow rate: 20 mL/min; wavelength: 214 nm and 254 nm; the gradient conditions are: 40% acetonitrile/60% water (0.1% trifluoroacetic acid V/V) initially, and then proceed to 50% acetonitrile/50% water (0.1% trifluoroacetic acid V/V) in a linear fashion after just 9 min) to afford 2-(1-(4-amino-4-methylpentyl)-5-(difluoromethoxy)-1H-indazol-3-yl)-N-tert-butyl-5H-pyrrolo[3,2-b]pyrazine-7-carboxamide 2,2,2-trifluoroacetate (13 mg, 34%) as yellow solid. LCMS: (M+H)$^+$=500; $^1$H NMR (300 MHz, CD$_3$OD): δ 8.98 (s, 1H), 8.13 (s, 1H), 8.07 (d, 1H, J=2.1 Hz), 7.60 (d, 1H, J=9.3 Hz), 7.29 (dd, 1H, J1=8.7 Hz, J2=2.1 Hz), 6.72 (t, 1H, J=74.1 Hz), 4.49-4.47 (m, 2H), 2.03-1.98 (m, 2H), 1.58-1.53 (m, 2H), 1.49 (s, 9H), 1.19 (s, 6H).

Example 455

N-tert-Butyl-2-(1-(3,4-dihydroxybutyl)-6-fluoro-1H-indazol-3-yl)-5H-pyrrolo[3,2-b]pyrazine-7-carboxamide

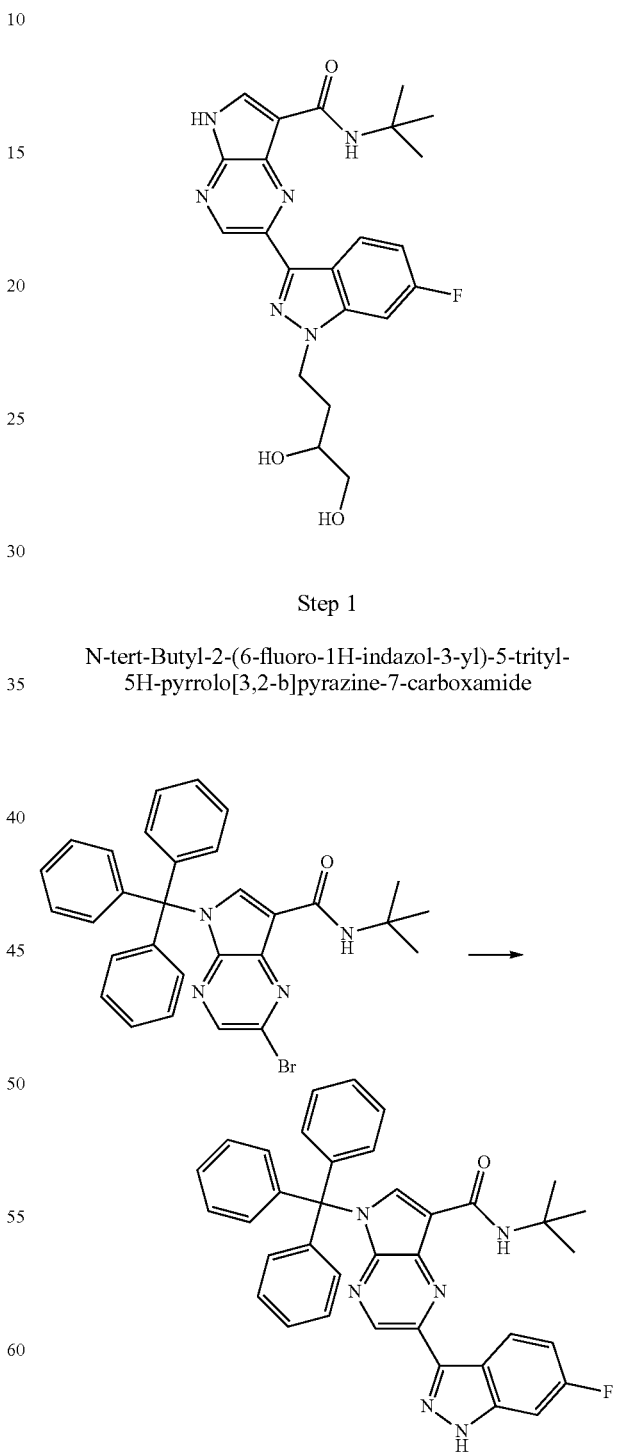

Step 1

N-tert-Butyl-2-(6-fluoro-1H-indazol-3-yl)-5-trityl-5H-pyrrolo[3,2-b]pyrazine-7-carboxamide In a round-bottomed flask, 2-bromo-N-tert-butyl-5-trityl-5H-pyrrolo[3,2-b]pyrazine-7-carboxamide (600 mg, 1.12 mmol) and 6-fluoro-3-(tributylstannyl)-1H-indazole (475 mg, 1.12 mmol) were dissolved in DMF (10 mL) under nitrogen. Pd(PPh$_3$)$_4$ (65 mg, 0.056 mmol) and CuI (43 mg, 0.224 mmol) were added and the mixture sonicated for 5 min while bubbling nitrogen. The reaction mixture was stirred at 85° C. for 16 hours. After solvent removal, the concentrated mixture was purified by column chromatography on silica gel eluting with petroleum ether/EtOAc (3:1 v/v) to give N-tert-butyl-2-(6-fluoro-1H-indazol-3-yl)-5-trityl-5H-pyrrolo[3,2-b]pyrazine-7-carboxamide (180 mg, 27%) as a white solid. LCMS: (M+H)$^+$=595; $^1$H NMR (300 MHz, DMSO): δ 13.60 (s, 1H), 8.78 (s, 1H), 8.45-8.40 (m, 1H), 8.01 (s, 1H), 7.95 (s, 1H), 7.45-7.33 (m, 10H), 7.21-7.09 (m, 7H), 1.50 (s, 9H).

Step 2

N-tert-Butyl-2-(1-(2-(2,2-dimethyl-1,3-dioxolan-4-yl)ethyl)-6-fluoro-1H-indazol-3-yl)-5-trityl-5H-pyrrolo[3,2-b]pyrazine-7-carboxamide

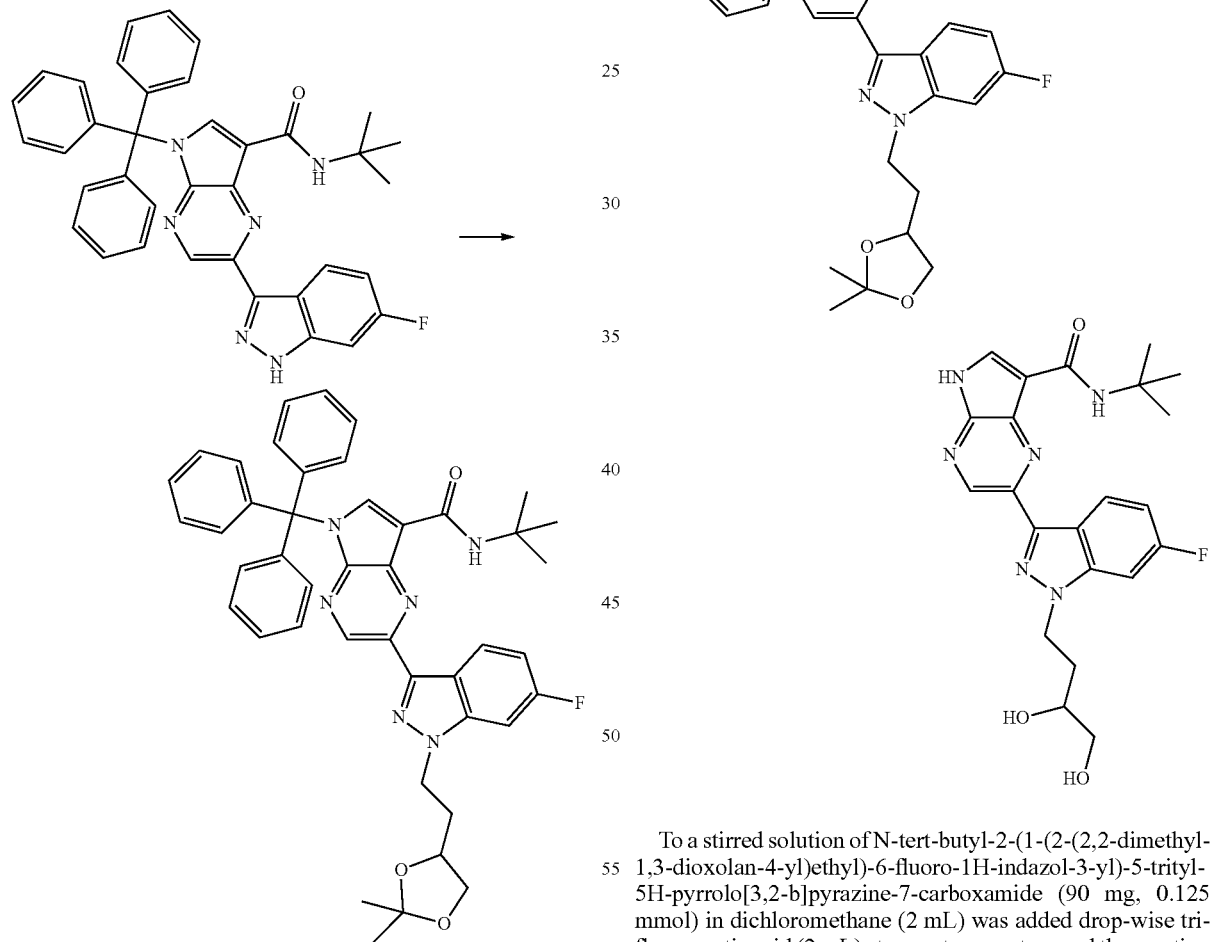

To a solution of N-tert-butyl-2-(6-fluoro-1H-indazol-3-yl)-5-trityl-5H-pyrrolo[3,2-b]pyrazine-7-carboxamide (80 mg, 0.135 mmol) in DMF (5 mL) was added 2-(2,2-dimethyl-1,3-dioxolan-4-yl)ethyl methanesulfonate (36 mg, 0.162 mmol) followed by K$_2$CO$_3$ (56 mg, 0.405 mmol). The mixture was heated at 65° C. for 4 hours. After cooling to room temperature, the mixture was poured into water, filtered and dried to give N-tert-butyl-2-(1-(2-(2,2-dimethyl-1,3-dioxolan-4-yl)ethyl)-6-fluoro-1H-indazol-3-yl)-5-trityl-5H-pyrrolo[3,2-b]pyrazine-7-carboxamide (90 mg, 92%) The crude was used to the next step without purification. LCMS: (M+H)$^+$=723.

Step 3

N-tert-Butyl-2-(1-(3,4-dihydroxybutyl)-6-fluoro-1H-indazol-3-yl)-5H-pyrrolo[3,2-b]pyrazine-7-carboxamide

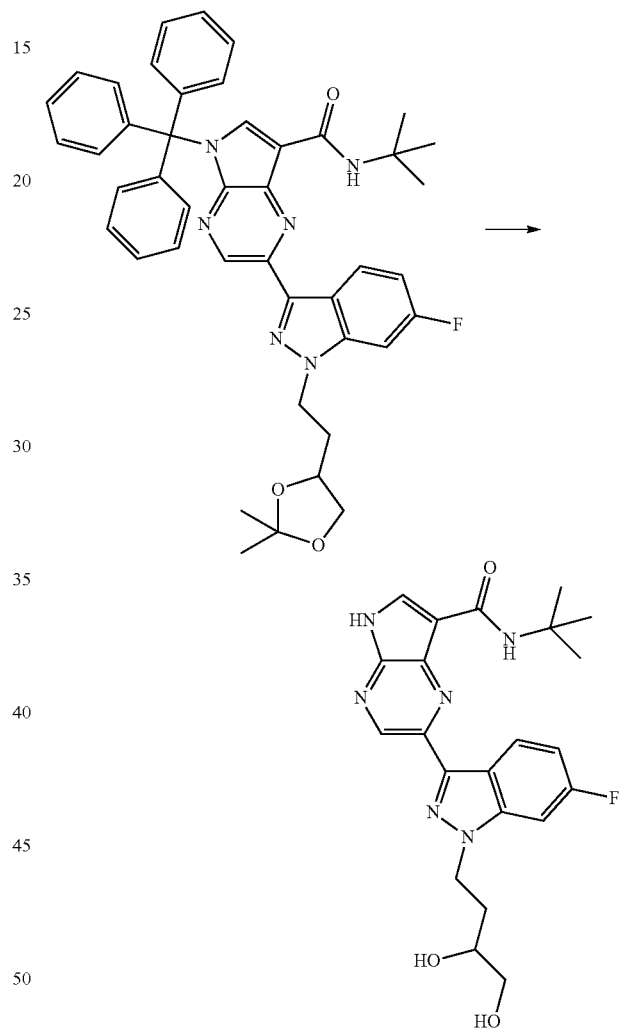

To a stirred solution of N-tert-butyl-2-(1-(2-(2,2-dimethyl-1,3-dioxolan-4-yl)ethyl)-6-fluoro-1H-indazol-3-yl)-5-trityl-5H-pyrrolo[3,2-b]pyrazine-7-carboxamide (90 mg, 0.125 mmol) in dichloromethane (2 mL) was added drop-wise trifluoroacetic acid (2 mL) at room temperature and the reaction mixture was stirred for 2 hours. The solvent was removed under reduced pressure. The residue was purified by preparative-HPLC (Gemini 5u C18 150×21.2 mm; inject volume: 3 mL/inj, flow rate: 20 mL/min; wavelength: 214 nm and 254 nm; the gradient conditions are: 30% acetonitrile/70% water (0.1% trifluoroacetic acid, v/v) initially, and then proceed to 70% acetonitrile/30% water (0.1% trifluoroacetic acid, v/v) in a linear fashion after just 9 min.) to give N-tert-butyl-2-(1-(3,4-dihydroxybutyl)-6-fluoro-1H-indazol-3-yl)-5H-pyrrolo

[3,2-b]pyrazine-7-carboxamide (30 mg, 54.5%) as a white solid. LCMS: (M+H)⁺=441, (M+Na)⁺=463; ¹H NMR (300 MHz, DMSO): δ12.81 (s, 1H), 9.06 (s, 1H), 8.47-8.42 (m, 1H), 8.37 (s, 1H), 7.91 (s, 1H), 7.64 (d, 1H, J=9.9 Hz), 7.14 (dd, 1H, J1=9.0 Hz, J2=1.8 Hz), 4.57 (t, 2H, J=6.5 Hz), 3.46-3.24 (m, 5H), 2.10-2.08 (m, 1H), 2.06-1.77 (m, 1H), 1.51 (s, 9H).

Example 456

N-tert-Butyl-2-(6-fluoro-1-(3-(methylsulfonyl)propyl)-1H-indazol-3-yl)-5H-pyrrolo[3,2-b]pyrazine-7-carboxamide

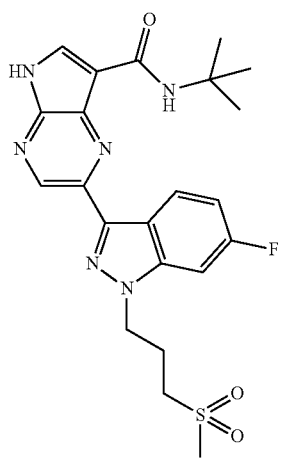

Step 1

N-tert-Butyl-2-(6-fluoro-1-(3-(methylsulfonyl)propyl)-1H-indazol-3-yl)-5-trityl-5H-pyrrolo[3,2-b]pyrazine-7-carboxamide

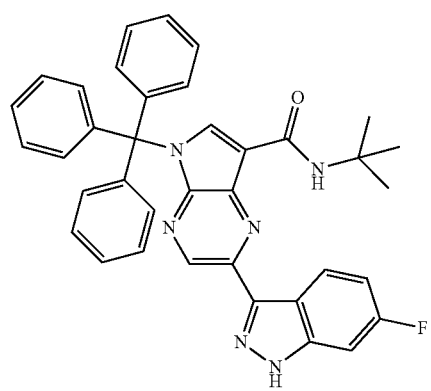

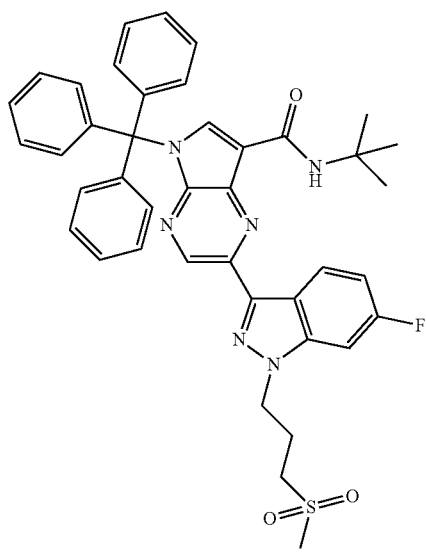

To a solution of N-tert-butyl-2-(6-fluoro-1H-indazol-3-yl)-5-trityl-5H-pyrrolo[3,2-b]pyrazine-7-carboxamide (60 mg, 0.1 mmol) in DMF (5 mL) was added 1-chloro-3-(methylsulfonyl)propane (19 mg, 0.12 mmol) followed by K₂CO₃ (42 mg, 0.3 mmol). The mixture was heated at 65° C. for 4 hours. After cooling to room temperature, the mixture was poured into water, filtered and dried to give N-tert-butyl-2-(6-fluoro-1-(3-(methylsulfonyl)propyl)-1H-indazol-3-yl)-5-trityl-5H-pyrrolo[3,2-b]pyrazine-7-carboxamide (55 mg, 77%). The crude was used to the next step without further purification. LCMS: (M+H)⁺=715.

Step 2

N-tert-Butyl-2-(6-fluoro-1-(3-(methylsulfonyl)propyl)-1H-indazol-3-yl)-5H-pyrrolo[3,2-b]pyrazine-7-carboxamide

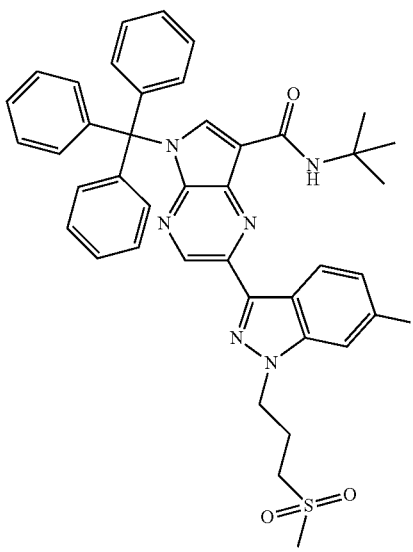

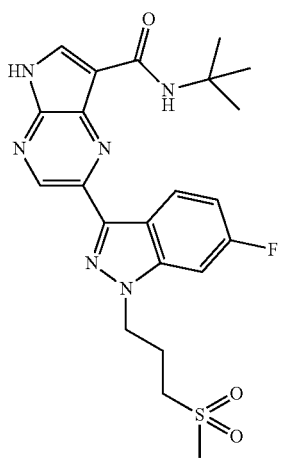 [SMILES: CC(C)(C)NC(=O)c1c[nH]c2ncc(-c3nn(CCCS(C)(=O)=O)c4cc(F)ccc34)nc12]

To a stirred solution of N-tert-butyl-2-(6-fluoro-1-(3-(methylsulfonyl)propyl)-1H-indazol-3-yl)-5-trityl-5H-pyrrolo[3,2-b]pyrazine-7-carboxamide (55 mg, 0.077 mmol) in dichloromethane (2 mL) was added drop-wise trifluoroacetic acid (2 mL) at room temperature and the reaction mixture was stirred for 2 hours. The solvent was removed under reduced pressure. The residue was triturated with MeOH then decanted and dried and dried to give N-tert-butyl-2-(6-fluoro-1-(3-(methylsulfonyl)propyl)-1H-indazol-3-yl)-5H-pyrrolo[3,2-b]pyrazine-7-carboxamide (26 mg, 72%) as a white solid. LCMS: (M+H)$^+$=473; (M+Na)$^+$=495; $^1$H NMR (300 MHz, DMSO): δ 12.84 (s, 1H), 9.09 (s, 1H), 8.51-8.46 (m, 1H), 8.38 (s, 1H), 7.93 (s, 1H), 7.74 (d, 1H, J=9.9 Hz), 7.18 (t, 1H, J=9.0 Hz), 4.63 (t, 2H, J=6.6 Hz), 3.22 (t, 2H, J=7.8 Hz), 2.99 (s, 3H), 2.33 (t, 2H, J=7.4 Hz), 1.52 (s, 9H).

Example 457

N-(5-Amino-tetrahydro-2H-pyran-3-yl)-2-(6-fluoro-1-methyl-1H-indazol-3-yl)-5H-pyrrolo[2,3-b]pyrazine-7-carboxamide hydrochloride

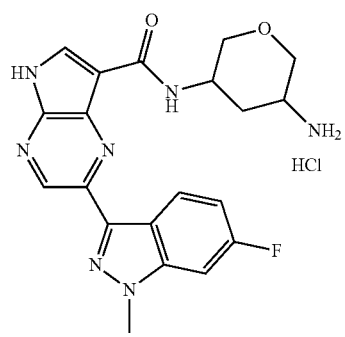 [SMILES: Cn1nc(-c2cnc3[nH]cc(C(=O)NC4COCC(N)C4)c3n2)c2ccc(F)cc21 ; Cl]

Step 1

5-Ethoxy-2H-pyran-3(6H)-one

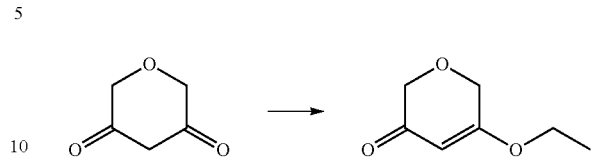

To a solution of 2H-pyran-3,5(4H,6H)-dione, sodium salt (1.36 g, 10 mmol) in 50 mL of ethanol were added 1.5 mL of concentrated sulphuric acid and the reaction mixture was stirred at room temperature overnight. Most of the solution was evaporated under vacuum, the residue was neutralized with saturated sodium bicarbonate, product extracted with ethyl acetate (4×50 mL), organics combined dried with sodium sulfate, filtered and concentrated. Residue purified by column chromatography (silica gel. 200-300 mesh, eluting with ethyl acetate/petroleum ether=1/1) to afford 5-ethoxy-2H-pyran-3(6H)-one (641 mg, 45%) as yellow solid. LCMS: (M+H)$^+$=143; $^1$H NMR (300 MHz, CDCl$_3$): δ 5.44 (s, 1H), 4.25 (s, 2H), 4.06 (s, 2H), 3.98 (q, 2H, J=6.9 Hz), 1.38 (t, 3H, J=6.9 Hz).

Step 2

5-Amino-2H-pyran-3(6H)-one

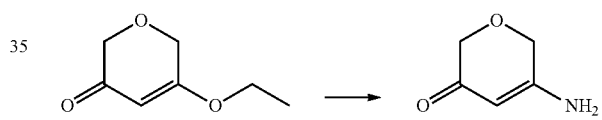

A solution of 5-ethoxy-2H-pyran-3(6H)-one (641 mg, 4.5 mmol) in 50 mL of ethanol was cooled in a dry ice bath, and ammonia gas was bubbled for 10 min. The reaction mixture was stirred overnight, concentrated to dryness and purified by column chromatography (silica gel. 200-300 mesh, eluting with methanol/dichloromethane=1/10) to afford 5-amino-2H-pyran-3(6H)-one (290 mg, 57%) as pale yellow solid. LCMS: (M+H)$^+$=114; $^1$H NMR (300 MHz, DMSO): δ 4.99 (s, 1H), 4.17 (s, 2H), 3.79 (s, 2H).

Step 3

5-Amino-tetrahydro-2H-pyran-3-ol

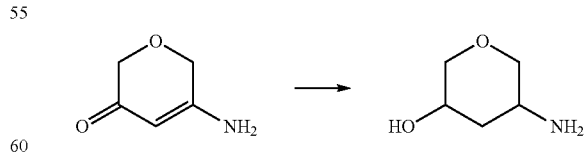

A mixture of 5-amino-2H-pyran-3(6H)-one (290 mg, 2.6 mmol) and 500 mg of wet Raney nickel in 20 mL of ethanol was stirred for 6 hours under 4 atm hydrogen gas at 60° C. in a hydrogen apparatus. The reaction mixture was cooled to room temperature, filtered over celite, the filtrate was concentrated to dryness to afford 5-amino-tetrahydro-2H-pyran-3-ol (389 mg, crude) as pale yellow solid, material used in the next step without further purification. LCMS: (M+H)$^+$=118.

Step 4 tert-Butyl 5-hydroxy-tetrahydro-2H-pyran-3-ylcarbamate

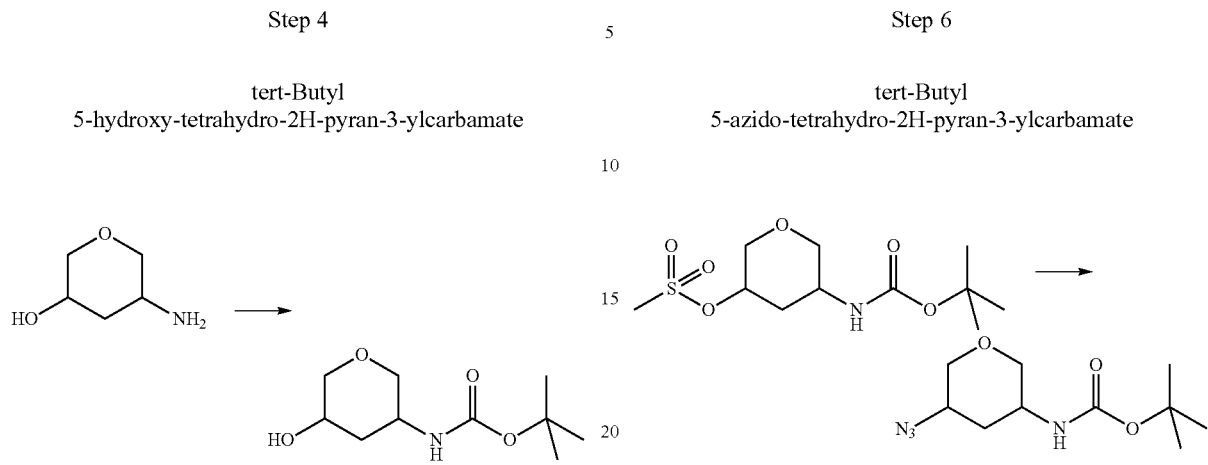

A mixture of 5-amino-tetrahydro-2H-pyran-3-ol (389 mg, crude, about 3.3 mmol), di-tert-butyl dicarbonate (700 mg, 3.3 mmol) and TEA (0.5 mL, 3.3 mmol) in 40 mL of THF was stirred for 4 h at room temperature, then concentrated to dryness and the residue purified by column chromatography (silica gel. 200-300 mesh, eluting with ethyl acetate/petroleum ether=1/1) to afford tert-butyl 5-hydroxy-tetrahydro-2H-pyran-3-ylcarbamate (400 mg, 56%) as pale yellow solid. LCMS: (M+H)$^+$=240; $^1$H NMR (300 MHz, CDCl$_3$): δ 4.78-4.72 (m, 1H), 3.94-3.85 (m, 2H), 3.77-3.59 (m, 3H), 3.47-3.33 (m, 2H), 1.92-1.85 (m, 2H), 1.42 (s, 9H).

Step 5

5-(tert-Butoxycarbonylamino)-tetrahydro-2H-pyran-3-yl methanesulfonate

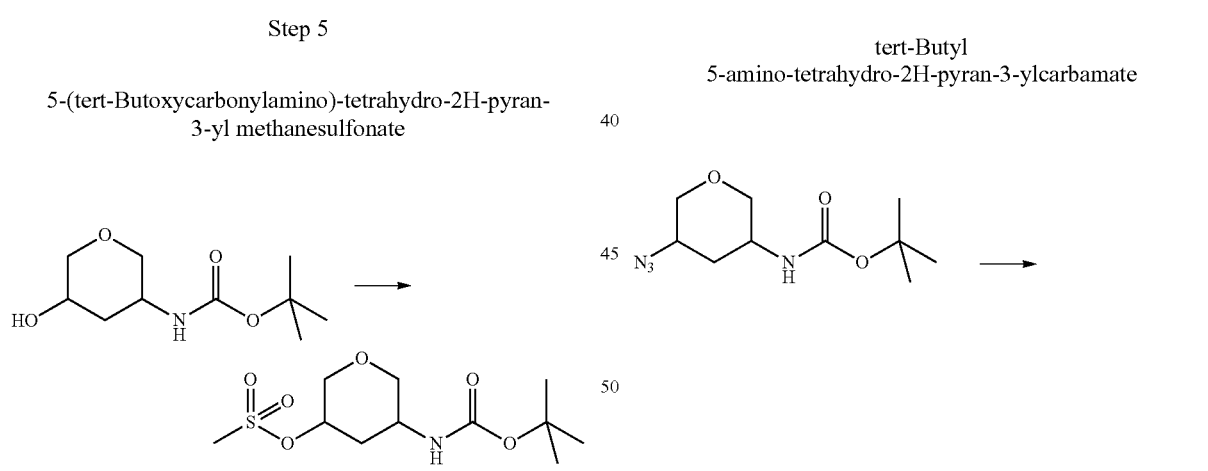

A solution of tert-butyl 5-hydroxy-tetrahydro-2H-pyran-3-ylcarbamate (109 mg, 0.5 mmol) and N,N-dimethylpyridin-4-amine (80 mg, 0.65 mmol) in 10 mL of dichloromethane was cooled in an ice bath, methanesulfonyl chloride (0.05 mL, 0.6 mmol) was added drop-wise. The reaction mixture was stirred overnight at room temperature, then was washed with 50 mL of water, organic phase dried with sodium sulfate filtered and concentrated. The residue was purified by column chromatography (silica gel. 200-300 mesh, eluting with ethyl acetate/petroleum ether=1/1) to afford 5-(tert-butoxycarbonylamino)-tetrahydro-2H-pyran-3-yl methanesulfonate (100 mg, 67%) as white solid. LCMS: (M+H)$^+$=318; $^1$H NMR (300 MHz, CDCl$_3$): δ 4.89-4.83 (m, 1H), 3.99-3.62 (m, 5H), 3.06 (s, 3H), 2.26-2.20 (m, 2H), 1.45 (s, 9H).

Step 6 tert-Butyl 5-azido-tetrahydro-2H-pyran-3-ylcarbamate

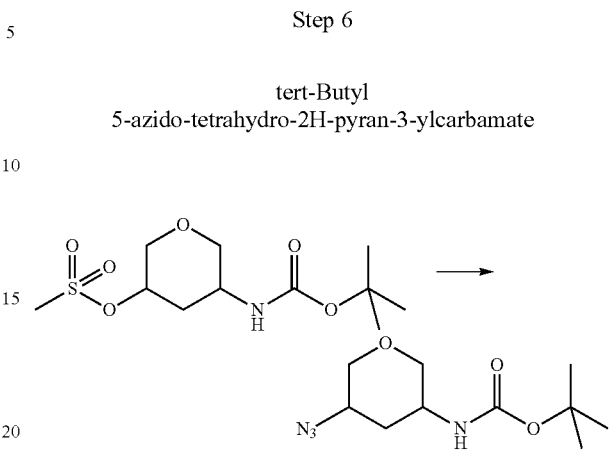

A solution of 5-(tert-butoxycarbonylamino)-tetrahydro-2H-pyran-3-yl methanesulfonate (90 mg, 0.3 mmol) and sodium azide (30 mg, 0.5 mmol) in 10 mL of dry N,N-dimethylformamide was heated to 100° C. for 3 h. The reaction mixture was cooled to room temperature, 40 mL of water were added, product extracted with ethyl acetate (2×50 mL), organics combined dried with sodium sulfate, filtered and concentrated to give tert-butyl 5-azido-tetrahydro-2H-pyran-3-ylcarbamate (100 mg, crude) which was used directly in the next step without further purification.

Step 7 tert-Butyl 5-amino-tetrahydro-2H-pyran-3-ylcarbamate

To a solution of tert-butyl 5-azido-tetrahydro-2H-pyran-3-ylcarbamate (1 g, 4.13 mmol) in 30 mL of ethyl acetate was added Pd/C (10%, 1 g), the reaction mixture was stirred overnight at room temperature under a hydrogen filled balloon. The reaction mixture was filtered over celite, the filtrate was concentrated to give tert-butyl 5-amino-tetrahydro-2H-pyran-3-ylcarbamate (188 mg, 21%) as white solid. LCMS:

(M+H)⁺=217; ¹H NMR (300 MHz, CDCl₃): δ 3.84-3.57 (m, 4H), 3.19-3.05 (m, 2H), 2.21-1.65 (m, 2H), 1.44 (s, 9H).

Step 8 tert-Butyl 5-(2-(6-fluoro-1-methyl-1H-indazol-3-yl)-5H-pyrrolo[2,3-b]pyrazine-7-carboxamido)-tetrahydro-2H-pyran-3-ylcarbamate

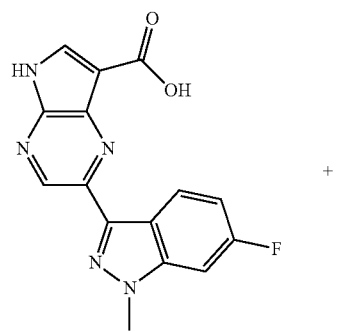

+

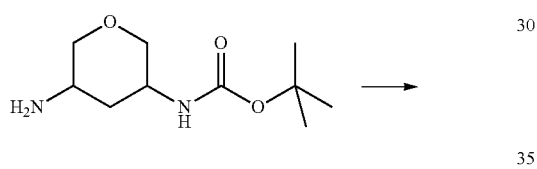

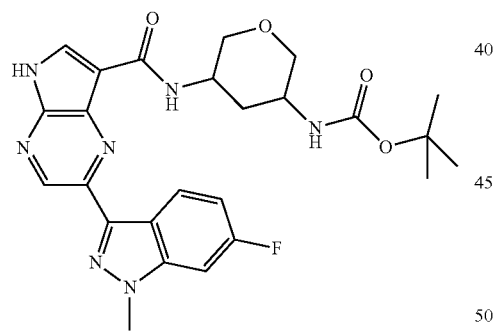

A mixture of tert-butyl 5-amino-tetrahydro-2H-pyran-3-ylcarbamate (100 mg, 0.46 mmol), 2-(6-fluoro-1-methyl-1H-indazol-3-yl)-5H-pyrrolo[3,2-b]pyrazine-7-carboxylic acid (200 mg, 0.7 mmol), EDCI (134 mg, 0.7 mmol), N,N-dimethylpyridin-4-amine (85 mg, 0.7 mmol), HOBt (95 mg, 0.7 mmol) and TEA (0.4 mL, 2.3 mmol) in 10 mL of dry DMF was stirred for 6 h at room temperature. The reaction mixture was concentrated to dryness and residue purified by column chromatography (silica gel, 200-300 mesh, eluting with ethyl acetate) to afford 5-(2-(6-fluoro-1-methyl-1H-indazol-3-yl)-5H-pyrrolo[2,3-b]pyrazine-7-carboxamido)tetrahydro-2H-pyran-3-ylcarbamate (120 mg, 51%) as yellow solid. LCMS: (M+H)⁺=510; (M+Na)⁺=532; ¹H NMR (300 MHz, DMSO): δ 12.87 (s, 1H), 9.08 (d, 1H, J=9.3 Hz), 8.45-8.34 (m, 2H), 7.96-7.94 (m, 1H), 7.68-7.65 (m, 1H), 7.23-7.14 (m, 1H), 7.04-7.01 (m, 1H), 4.13-4.04 (m, 5H), 3.82-3.78 (m, 4H), 3.07-3.01 (m, 2H), 1.46 (s, 9H).

Step 9

N-(5-Amino-tetrahydro-2H-pyran-3-yl)-2-(6-fluoro-1-methyl-1H-indazol-3-yl)-5H-pyrrolo[2,3-b]pyrazine-7-carboxamide hydrochloride

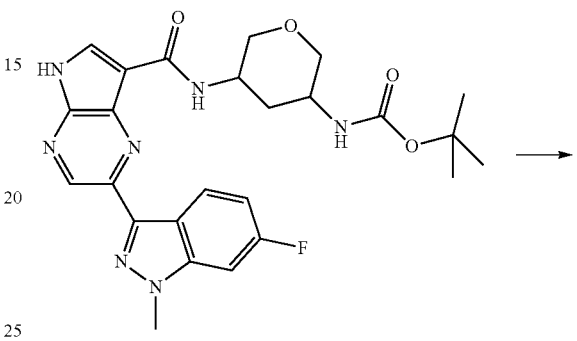

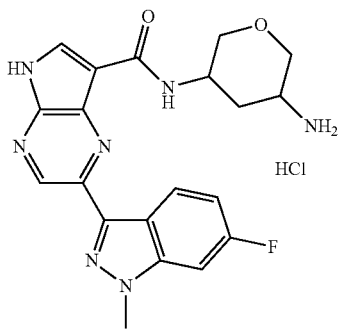

To a solution of 5-(2-(6-fluoro-1-methyl-1H-indazol-3-yl)-5H-pyrrolo[2,3-b]pyrazine-7-carboxamido)-tetrahydro-2H-pyran-3-ylcarbamate (120 mg, 0.24 mmol) in 10 mL of dioxane was bubbled HCl gas for 3 h. The reaction mixture was stirred overnight at room temperature. The formed precipitate was separated by filtration and the filter cake was washed with 10 mL of ether to give 30 mg of N-(5-amino-tetrahydro-2H-pyran-3-yl)-2-(6-fluoro-1-methyl-1H-indazol-3-yl)-5H-pyrrolo[2,3-b]pyrazine-7-carboxamide hydrochloride. LCMS: (M+H)+=410.

Example 458

N-tert-Butyl-2-(5-isopropyl-1-methyl-1H-indazol-3-yl)-5H-pyrrolo[2,3-b]pyrazine-7-carboxamide

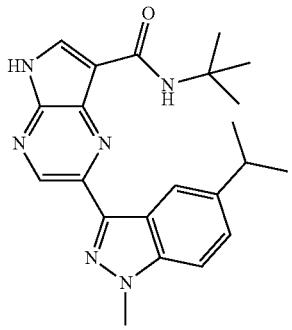 [SMILES: CC(C)c1ccc2c(c1)c(-c1cnc3[nH]cc(C(=O)NC(C)(C)C)c3n1)nn2C]

Step 1

Prop-1-en-2-ylboronic acid

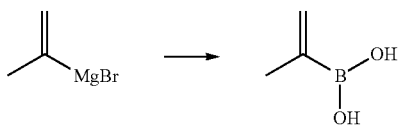

To a stirred solution of prop-1-en-2-ylmagnesium bromide (0.5 N in THF 10 mL, 5 mmol) in 10 mL of dry THF at room temperature was added trimethyl borate (1.67 mL, 15 mL). The reaction was stirred at room temperature for 2.5 hours and then cooled to 0° C. 1 N HCl in water (6 mL, 6 mmol) was added and stirring continued for 10 min. The resulting mixture was extracted with ethyl acetate (2×20 mL). The combined organic layers were dried over $Na_2SO_4$ and concentrated under reduced pressure to yield crude prop-1-en-2-ylboronic acid (0.6 g, crude) as a white solid. $^1$H NMR (300 MHz, DMSO): δ 4.09 (q, 2H, J=7.0 Hz), 1.99 (s, 3H).

Step 2

5-(Prop-1-en-2-yl)-1H-indazole

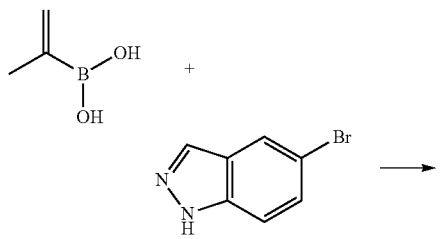

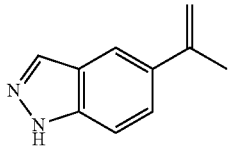

A mixture of prop-1-en-2-ylboronic acid (1.2 g), 5-bromo-1H-indazole (1.0 g, 5.1 mmol), Pd(dba)$_2$ (0.04 g, 0.07 mmol), X-phos (0.04 g, 0.08 mmol) and Cs$_2$CO$_3$ (3.0 g, 9.2 mmol) in a mixture of 30 mL of DMF and 5 mL of water was stirred at 130° C. under nitrogen for 8 hours. The solvent was removed under reduced pressure and the residue was purified by silica gel chromatography (200-300 mesh, eluting with a mixture of ethyl acetate and petroleum ether (1:5, v/v) to give a 2:3 mixture 5-(prop-1-en-2-yl)-1H-indazole and 1H-indazole (0.9 g). The crude mixture was used into the next step without further purification. LCMS: (M+H)+=159; $^1$H NMR (300 MHz, DMSO): δ 8.08 (s, 1H), 7.81-7.80 (m, 1H), 7.62 (dd, 1H, J$_1$=8.7 Hz, J$_2$=1.5 Hz), 7.53-7.46 (m, 1H), 5.40-5.39 (m, 1H), 5.12-5.11 (m, 1H), 2.24 (s, 3H).

Step 3

5-Isopropyl-1H-indazole

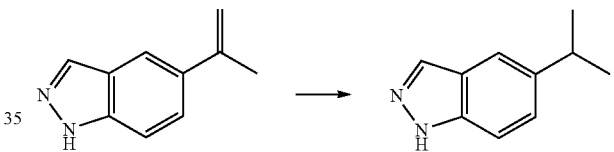

A 2:3 mixture of 5-(prop-1-en-2-yl)-1H-indazole and 1H-indazole (0.9 g), 10% Pd/C (0.2 g) in 150 mL of methanol was stirred at room temperature under H$_2$ balloon for 3 hours. Pd/C was filtered off and the filtrate was concentrated under reduced pressure to give crude 5-isopropyl-1H-indazole (0.85 g) as an oil. LCMS: (M+H)+=161.

Step 4

3-Iodo-5-isopropyl-1H-indazole

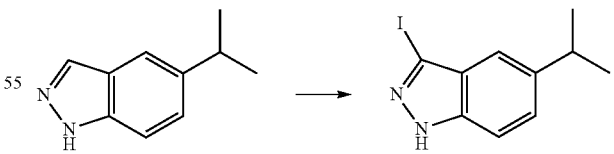

To a stirred solution containing mainly 5-isopropyl-1H-indazole (0.85 g, crude) in 70 mL of DMSO was added KOH (0.52 g, 8 mmol) at room temperature. Then I$_2$ (1.35 g, 5.3 mmol) was added slowly, after the addition, the mixture was stirred at room temperature for 2 hours. The mixture was poured into 200 mL of saturated Na$_2$SO$_3$ solution, then extracted with ethyl acetate (2×100 mL). The combined organic layers was washed with water (100 mL) and brine (100 mL) dried over Na$_2$SO$_4$ and concentrated under reduced pressure to give crude 3-iodo-5-isopropyl-1H-indazole (0.78 g). LCMS: (M+H)$^+$=287.

Step 5

3-Iodo-5-isopropyl-1-methyl-1H-indazole

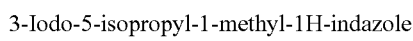

To a stirred solution of 3-iodo-5-isopropyl-1H-indazole (0.75 g, crude) in 50 mL of THF at 0° C. was added t-BuOK (0.59 g, 5.2 mmol) in one portion. The mixture was stirred at 0° C. for 30 minutes. CH$_3$I (1.1 g, 7.7 mmol) was added and the solution was stirred at room temperature overnight. The reaction was quenched with 30 mL of water and extracted with ethyl acetate (2×100 mL). The combined organic layers were washed with water (100 mL), brine (100 mL) and dried over anhydrous Na$_2$SO$_4$. The drying agent was removed by filtration and the filtrate was evaporated under reduced pressure to give crude 3-iodo-5-isopropyl-1-methyl-1H-indazole which contained some N-2 alkylation isomer (0.7 g) as oil. LCMS: (M+H)$^+$=301.

Step 6

5-Isopropyl-1-methyl-3-(tributylstannyl)-1H-indazole

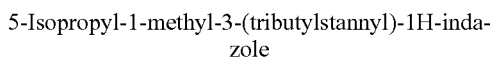

To a stirred solution of 3-iodo-5-isopropyl-1-methyl-1H-indazole (0.3 g, crude) in 100 mL of dry THF at −16° C. under nitrogen was added i-PrMgCl (0.69 mL, 1.38 mmol, 2M in THF) drop-wise. Then the mixture was stirred at −16° C. for 20 minutes. Tributylchlorostannane (0.39 g, 1.2 mmol) was added slowly and the mixture was stirred at room temperature for 2.5 hours. The solution was quenched by 40 mL of water, extracted with ethyl acetate (2×100 mL), washed with water (2×50 mL), brine (50 mL) and dried over anhydrous sodium sulfate. The drying agent was removed by filtration and the filtrate was evaporated under reduced pressure to give crude 5-isopropyl-1-methyl-3-(tributylstannyl)-1H-indazole as an oil, which was used into next step without further purification.

Step 7

(7-(tert-Butylcarbamoyl)-2-(5-isopropyl-1-methyl-1H-indazol-3-yl)-5H-pyrrolo[2,3-b]pyrazin-5-yl)methyl pivalate

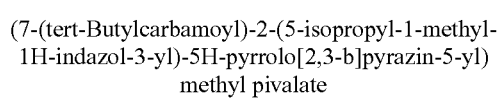

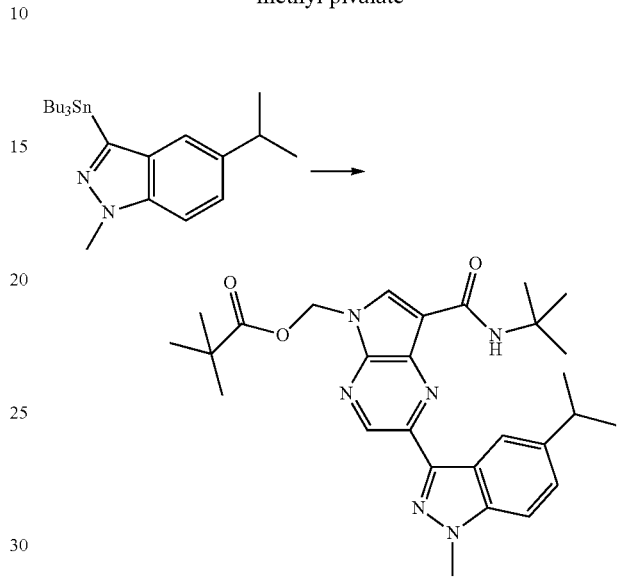

A mixture 5-isopropyl-1-methyl-3-(tributylstannyl)-1H-indazole, (2-bromo-7-(tert-butylcarbamoyl)-5H-pyrrolo[2,3-b]pyrazin-5-yl)methyl pivalate (0.408 g, 1 mmol), CuI (0.06 g, 0.32 mmol) and Pd(PPh$_3$)$_4$ (0.06 g, 0.052 mmol) in 40 mL of DMF was stirred at 80° C. under nitrogen for 4 hours. The solvent was removed under reduced pressure and the residue was triturated with water (15 mL) and petroleum ether (30 mL) then decanted and dried to give crude (7-(tert-butylcarbamoyl)-2-(5-isopropyl-1-methyl-1H-indazol-3-yl)-5H-pyrrolo[2,3-b]pyrazin-5-yl)methyl pivalate (0.15 g) as a yellow solid, which was used into next step without further purification. LCMS: (M+H)$^+$=505.

Step 8

N-tert-Butyl-2-(5-isopropyl-1-methyl-1H-indazol-3-yl)-5H-pyrrolo[2,3-b]pyrazine-7-carboxamide

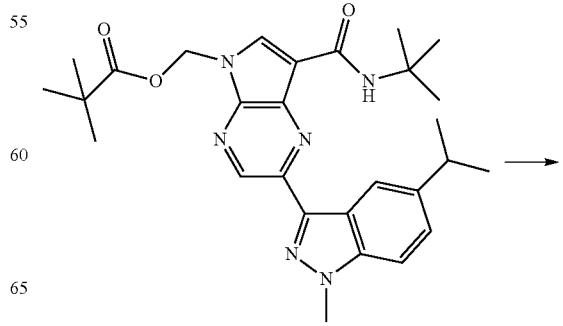

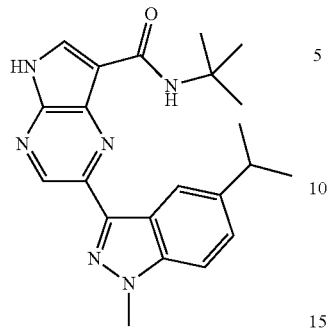

To a stirred solution of (7-(tert-butylcarbamoyl)-2-(5-isopropyl-1-methyl-1H-indazol-3-yl)-5H-pyrrolo[2,3-b]pyrazin-5-yl)methyl pivalate (0.2 g, crude) in dioxane/water (5 mL/10 mL) was added KOH (0.23 g, 4.1 mmol). The mixture was stirred at room temperature for 3 hours. Then the reaction mixture treated with 1N HCl to pH=3-4. The solvent was removed under reduced pressure and the residue triturated with water (15 mL) and dried to give a crude product which was purified by preparative-HPLC (Gemini 5u C18 150×21.2 mm; inject volume: 3 mL/inj, flow rate: 20 mL/min; wavelength: 214 nm and 254 nm; the gradient conditions are: 62% acetonitrile/38% water (0.1% trifluoroacetic acid, v/v) initially, and then proceed to 64% acetonitrile/36% water (0.1% trifluoroacetic acid, v/v) in a linear fashion after just 9 min.) to give N-tert-butyl-2-(5-isopropyl-1-methyl-1H-indazol-3-yl)-5H-pyrrolo[2,3-b]pyrazine-7-carboxamide (0.05 g) as a yellow solid. LCMS: (M+H)$^+$=391; $^1$H NMR (300 MHz, CD$_3$OD): δ 9.05 (s, 1H), 8.29 (s, 1H), 8.16 (s, 1H), 7.61 (d, 1H, J=8.7 Hz), 7.48 (dd, 1H, J$_1$=8.7 Hz, J$_2$=1.5 Hz), 4.18 (s, 3H), 3.19-3.02 (m, 1H), 1.58 (s, 9H), 1.35 (d, 6H, J=6.6 Hz).

Examples 459 and 460

N-(5-Amino-tetrahydro-2H-pyran-3-yl)-2-(6-fluoro-1-methyl-1H-indazol-3-yl)-5H-pyrrolo[2,3-b]pyrazine-7-carboxamide hydrochloride (diastereomers A and B)

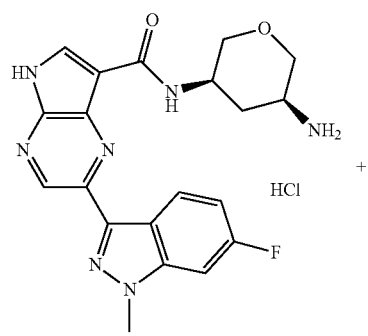

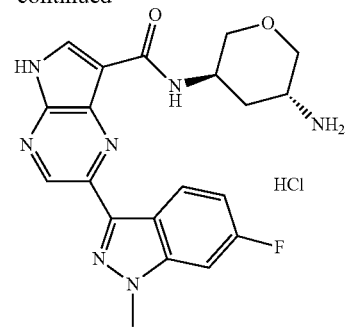

The filtrate from Example 457 was concentrated to dryness and purified by preparative HPLC (Gemini 5u C18 150×21.2 mm; inject volume: 3 mL/inj, flow rate: 20 mL/min; wavelength: 214 nm and 254 nm; the gradient conditions are: 40% acetonitrile/60% water (0.1% trifluoroacetic acid V/V) initially, and then proceed to 10% acetonitrile/90% water (0.1% trifluoroacetic acid V/V) in a linear fashion after just 9 min.) to give two diastereoisomers (10 mg each) the relative stereochemistry of which was arbitrarily assigned. The more polar diastereoisomer A: LCMS: (M+H)$^+$=410; $^1$H NMR (300 MHz, DMSO+D$_2$O): δ 9.02 (s, 1H), 8.34-8.28 (m, 2H), 7.51 (d, 1H, J=9.6 Hz), 7.24 (t, 1H, J=9.3 Hz), 4.14-4.04 (m, 8H), 3.37-3.12 (m, 3H). The less polar diastereoisomer B: LCMS: (M+H)$^+$=410; $^1$H NMR (300 MHz, DMSO+D$_2$O): δ 9.03 (s, 1H), 8.41-8.37 (m, 2H), 8.20 (d, 1H, J=7.8 Hz), 7.49 (d, 1H, J=9.3 Hz), 7.09 (t, 1H, J=8.7 Hz), 4.38 (brs, 1H), 4.04 (s, 3H), 3.89-3.86 (m, 2H), 3.67-3.42 (m, 3H), 2.23-2.01 (m, 2H).

Example 461

N-tert-Butyl-2-(1-methyl-5-(methylsulfonyl)-1H-indazol-3-yl)-5H-pyrrolo[3,2-b]pyrazine-7-carboxamide

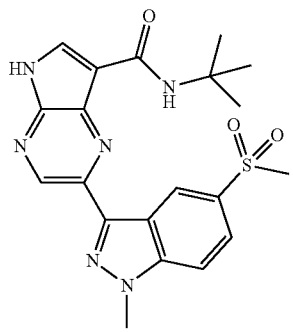 [SMILES: Cn1nc(-c2cnc3[nH]cc(C(=O)NC(C)(C)C)c3n2)c2cc(S(C)(=O)=O)ccc21]

Step 1

3-Iodo-5-(methylsulfonyl)-1H-indazole

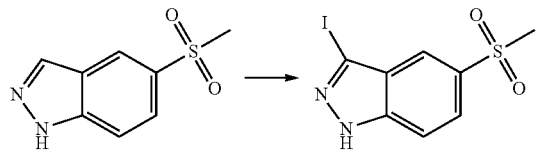

To a solution of 5-(methylsulfonyl)-1H-indazole (430 mg, 2.19 mmol) in DMSO (10 mL) at 0° C., were added KOH (0.4 g, 6.57 mmol) and I₂ (1.2 g, 4.38 mmol) successively, then the reaction mixture was stirred at room temperature for 3 hours. Water (40 mL) was added, product extracted with EtOAc (3×30 mL), organics combined dried with sodium sulfate, filtered and concentrated under reduced pressure. The residue was purified by column chromatography (silica gel, 200-300 mesh, eluting with petroleum ether/EtOAc=20:1) to give 3-iodo-5-(methylsulfonyl)-1H-indazole (410 mg, 59.9%) as an off-white solid. LCMS: (M+H)⁺=323; ¹H NMR (300 MHz, DMSO): δ 7.98-7.95 (m, 4H), 3.27 (s, 3H).

Step 2

3-Iodo-1-methyl-5-(methylsulfonyl)-1H-indazole

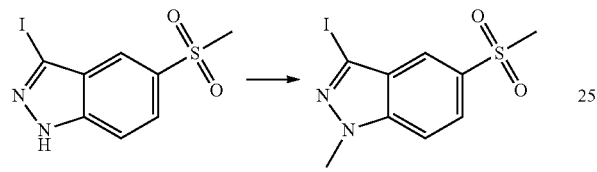

To a solution of 3-iodo-5-(methylsulfonyl)-1H-indazole (400 mg, 1.24 mmol) in THF (15 mL) was added t-BuOK (208 mg, 1.86 mmol) slowly at 0° C., mixture stirred for 30 minutes, then iodomethane (262 mg, 1.86 mmol) was added at 0° C., then warmed to room temperature and stirred for 2 hours. Reaction quenched with water (40 mL) and product extracted with EtOAc (3×30 mL), organics combined dried with sodium sulfate, filtered and concentrated under reduced pressure to afford a solid which was purified by column chromatography (silica gel, 200-300 mesh, eluting with dichloromethane/methanol=10:1) to give 3-iodo-1-methyl-5-(methylsulfonyl)-1H-indazole (210 mg, 50.6%) as a white solid. LCMS: (M+H)⁺=337; ¹H NMR (300 MHz, DMSO): δ 7.97-7.94 (m, 3H), 4.13 (s, 3H), 3.26 (s, 3H).

Step 3

Methyl 2-(1-methyl-5-(methylsulfonyl)-1H-indazol-3-yl)-5-(pivaloyloxymethyl)-5H-pyrrolo[3,2-b]pyrazine-7-carboxylate

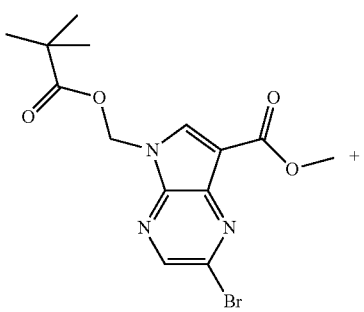

+

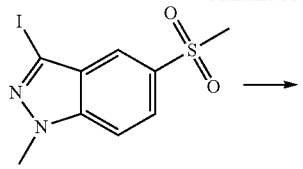

-continued

To a solution of 3-iodo-1-methyl-5-(methylsulfonyl)-1H-indazole (127 mg, 0.37 mmol), methyl 2-bromo-5-(pivaloyloxymethyl)-5H-pyrrolo[3,2-b]pyrazine-7-carboxylate (128 mg, 0.34 mmol) and Pd(PPh₃)₄ (20 mg, 0.017 mmol) in DMF (8 mL) was added hexa-N-butylditin (299 mg, 0.51 mmol). The reaction mixture was degassed by bubbling nitrogen for 3 minutes and refilled with nitrogen. The mixture was heated to 100° C. for 15 hours under nitrogen. After cooling to room temperature, water (40 mL) was added and product extracted with EtOAc (3×30 mL), organics combined dried with sodium sulfate, filtered and concentrated under reduced pressure. The residue was purified by column chromatography (silica gel, 200-300 mesh, eluting with EtOAc/petroleum ether=2:1) to give methyl2-(1-methyl-5-(methylsulfonyl)-1H-indazol-3-yl)-5-(pivaloyloxymethyl)-5H-pyrrolo[3,2-b]pyrazine-7-carboxylate (120 mg, 69.7%) as an off-white solid. LCMS: (M+H)⁺=500; ¹H NMR (300 MHz, DMSO): δ 9.43 (d, 1H, J=1.2 Hz), 9.21 (s, 1H), 8.95 (d, 1H, J=1.2 Hz), 8.77 (s, 1H), 8.01 (s, 1H), 6.33 (s, 2H), 4.24 (s, 3H), 4.04 (s, 3H), 3.28 (s, 3H), 1.09 (s, 9H).

Step 4

2-(5-Methanesulfonyl-1-methyl-1H-indazol-3-yl)-5H-pyrrolo[2,3-b]pyrazine-7-carboxylic acid

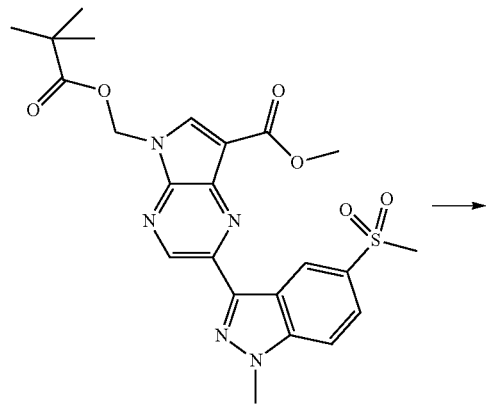

To a suspension of methyl2-(1-methyl-5-(methylsulfonyl)-1H-indazol-3-yl)-5-(pivaloyloxymethyl)-5H-pyrrolo[3,2-b]pyrazine-7-carboxylate (80 mg, 0.16 mmol) in dioxane/water (6 mL/4 mL) was added NaOH (100 mg, 2.5 mmol), the reaction mixture was heated to 85° C. with stirring for 4 hours, the dioxane was removed under reduced pressure, the aqueous layer was adjusted to pH=4 with 2 N HCl. The formed precipitate was collected by filtration, washed with water (3 mL) and dried to afford 2-(5-methanesulfonyl-1-methyl-1H-indazol-3-yl)-5H-pyrrolo[2,3-b]pyrazine-7-carboxylic acid (40 mg, 67.7%) as an orange solid. LCMS: $(M+H)^+=372$; $^1$H NMR (300 MHz, DMSO): δ 12.89 (d, 1H, J=2.7 Hz), 12.49 (brs, 1H), 9.47 (s, 1H), 9.08 (s, 1H), 8.50 (d, 2H, J=3.3 Hz), 8.01-7.95 (m, 1H), 4.23 (s, 3H), 3.27 (s, 3H).

Step 5

N-tert-Butyl-2-(1-methyl-5-(methylsulfonyl)-1H-indazol-3-yl)-5H-pyrrolo[3,2-b]pyrazine-7-carboxamide

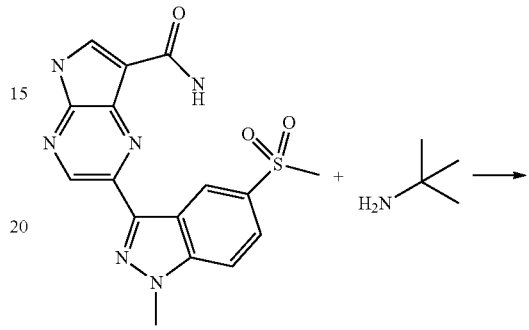

A mixture of 2-(5-methanesulfonyl-1-methyl-1H-indazol-3-yl)-5H-pyrrolo[2,3-b]pyrazine-7-carboxylic acid (75 mg, 0.20 mmol), 2-methylpropan-2-amine (15 mg, 0.20 mmol), HOBt (108 mg, 0.80 mmol), EDCI (153 mg, 0.80 mmol) and DIPEA (103 mg, 0.80 mmol) in DMF (6 mL) was stirred at room temperature for 15 hours, then water (30 mL) was added, product extracted with EtOAc (3×30 mL), organics combined dried with sodium sulfate, filtered and concentrated under reduced pressure and residue purified by preparative-HPLC (Gemini 5u C18 150×21.2 mm; inject volume: 3 mL/inj, flow rate: 20 mL/min; wavelength: 214 nm and 254 nm; the gradient conditions are: 30% methanol/70% water (0.1% trifluoroacetic acid, v/v) initially, and then proceed to 50% methanol/50% water (0.1% trifluoroacetic acid, v/v) in a linear fashion after just 9 min.) to give N-tert-butyl-2-(1-methyl-5-(methylsulfonyl)-1H-indazol-3-yl)-5H-pyrrolo[3,2-b]pyrazine-7-carboxamide (7 mg, 8.1%) as a white solid. LCMS: $(M+H)^+=427$; $^1$H NMR (300 MHz, CD$_3$OD): δ

9.08 (s, 1H), 8.99 (s, 1H), 8.33 (s, 1H), 8.01 (d, 1H, J=8.7 Hz), 7.90 (d, 1H, J=8.7 Hz), 4.28 (s, 3H), 3.17 (s, 3H), 1.57 (s, 9H).

Example 462

2-(6-Fluoro-1-(3-hydroxybutyl)-1H-indazol-3-yl)-N-(1-hydroxy-2-methylpropan-2-yl)-5H-pyrrolo[3,2-b]pyrazine-7-carboxamide

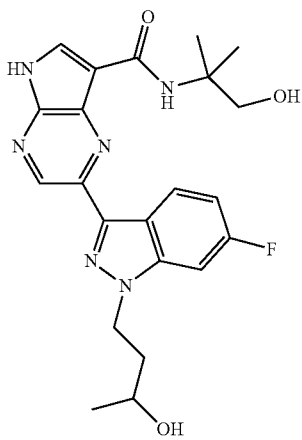 [SMILES: CC(O)CCn1nc(-c2cnc3[nH]cc(C(=O)NC(C)(C)CO)c3n2)c2ccc(F)cc21]

Step 1

N-(1-(tert-Butyldimethylsilyloxy)-2-methylpropan-2-yl)-2-(6-fluoro-1-(3-oxobutyl)-1H-indazol-3-yl)-5-trityl-5H-pyrrolo[3,2-b]pyrazine-7-carboxamide

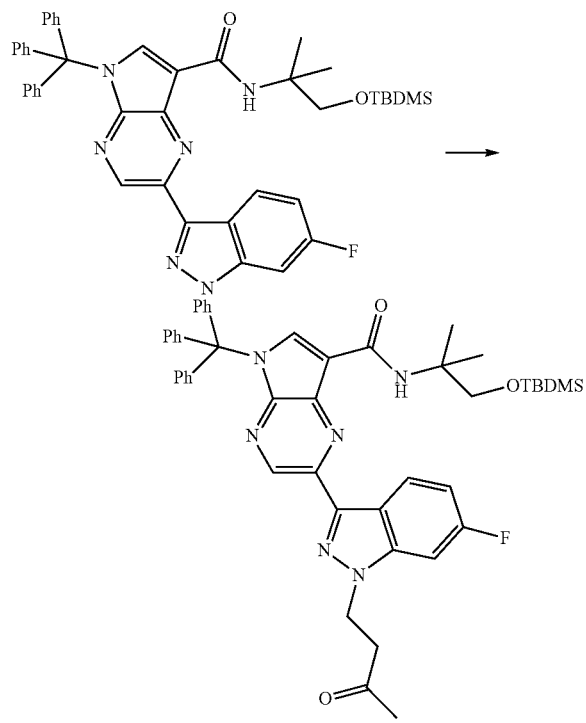

To a solution of N-(1-(tert-butyldimethylsilyloxy)-2-methylpropan-2-yl)-2-(6-fluoro-1H-indazol-3-yl)-5-trityl-5H-pyrrolo[3,2-b]pyrazine-7-carboxamide (60 mg, 0.083 mmol) in DMF (4 mL) was added 4-chlorobutan-2-one (11 mg, 0.1 mmol) followed by K$_2$CO$_3$ (34 mg, 0.25 mmol). The mixture was heated at 65° C. for 1.5 hours. After cooling to room temperature, the mixture was poured into water and filtered to give N-(1-(tert-butyldimethylsilyloxy)-2-methylpropan-2-yl)-2-(6-fluoro-1-(3-oxobutyl)-1H-indazol-3-yl)-5-trityl-5H-pyrrolo[3,2-b]pyrazine-7-carboxamide (40 mg, 61%). After drying, the crude was used into the next step without further purification. LCMS: (M+H)$^+$=795.

Step 2

N-(1-(tert-Butyldimethylsilyloxy)-2-methylpropan-2-yl)-2-(6-fluoro-1-(3-hydroxybutyl)-1H-indazol-3-yl)-5-trityl-5H-pyrrolo[3,2-b]pyrazine-7-carboxamide

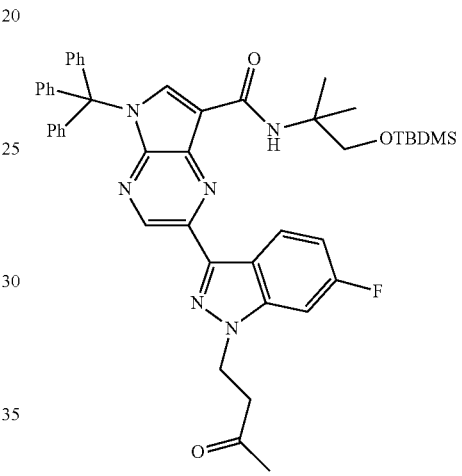

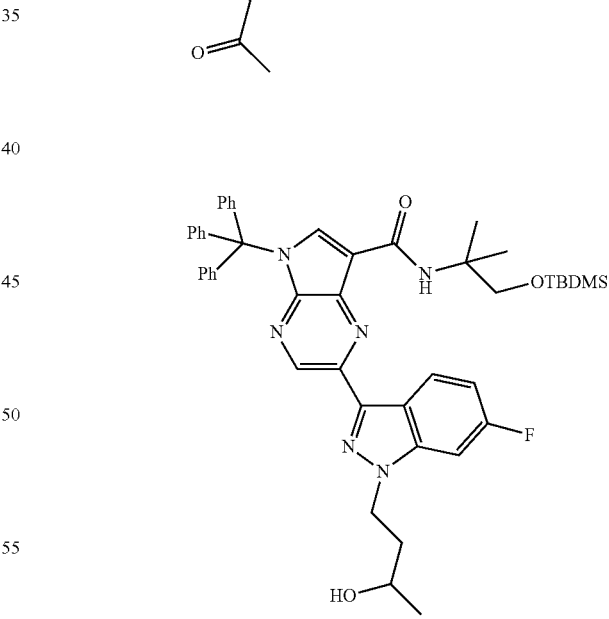

To a solution of N-(1-(tert-butyldimethylsilyloxy)-2-methylpropan-2-yl)-2-(6-fluoro-1-(3-oxobutyl)-1H-indazol-3-yl)-5-trityl-5H-pyrrolo[3,2-b]pyrazine-7-carboxamide (40 mg, 0.05 mmol) in MeOH (5 mL) was added NaBH$_4$ (10 mg, 0.25 mmol) at 0° C. The mixture was stirred at room temperature for 1 hour. NH$_4$Cl (aqueous) was added to the mixture to quench the reaction. The mixture was extracted with EtOAc (3×5 mL). The combined organic layers were washed with brine and dried over Na$_2$SO$_4$. After filtration and concentration, the crude was used into the next step without purification. LCMS: (M+H)$^+$=797.

Step 3

2-(6-Fluoro-1-(3-hydroxybutyl)-1H-indazol-3-yl)-N-(1-hydroxy-2-methylpropan-2-yl)-5H-pyrrolo[3,2-b]pyrazine-7-carboxamide

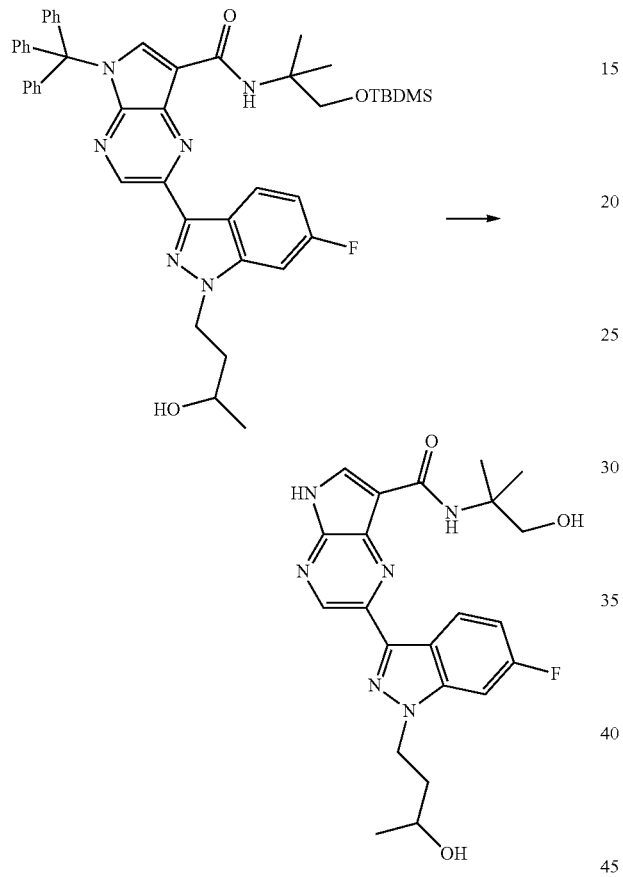

To a stirred solution of N-(1-(tert-butyldimethylsilyloxy)-2-methylpropan-2-yl)-2-(6-fluoro-1-(3-hydroxybutyl)-1H-indazol-3-yl)-5-trityl-5H-pyrrolo[3,2-b]pyrazine-7-carboxamide in dichloromethane (2 mL) was added drop-wise trifluoroacetic acid (1 mL) at room temperature and the reaction mixture was stirred for 1 hour. The solvent was removed under reduced pressure. The residue was dissolved in dichloromethane and washed with NaHCO$_3$ (aqueous), The organic layer was concentrated, and the residue was purified by preparative-HPLC (Gemini 5u C18 150×21.2 mm; inject volume: 3 mL/inj, flow rate: 20 mL/min; wavelength: 214 nm and 254 nm; the gradient conditions are: 36% acetonitrile/64% water (0.1% trifluoroacetic acid, v/v) initially, and then proceed to 42% acetonitrile/58% water (0.1% trifluoroacetic acid, v/v) in a linear fashion after just 9 min.) to give 2-(6-fluoro-1-(3-hydroxybutyl)-1H-indazol-3-yl)-N-(1-hydroxy-2-methylpropan-2-yl)-5H-pyrrolo[3,2-b]pyrazine-7-carboxamide (10 mg, 45% over three steps) as a white solid. LCMS: (M+H)$^+$=441; $^1$H NMR (300 MHz, CD$_3$OD): δ 9.15 (s, 1H), 8.58 (dd, 1H, J$_1$=9. Hz, J$_2$=5.4 Hz), 8.29 (s, 1H), 7.42 (d, 1H, J=7.8 Hz), 7.10 (d, 1H, J=7.2 Hz), 4.62-4.56 (m, 2H), 3.82 (s, 2H), 3.76 (brs, 1H), 2.19-2.13 (m, 2H), 2.04-1.99 (m, 2H), 1.55 (s, 6H), 1.22 (d, 3H, J=6.3 Hz).

Example 463

2-(6-Fluoro-1-methyl-1H-indazol-3-yl)-N-((3-hydroxyazetidin-3-yl)methyl)-5H-pyrrolo[3,2-b]pyrazine-7-carboxamide trifluoroacetate

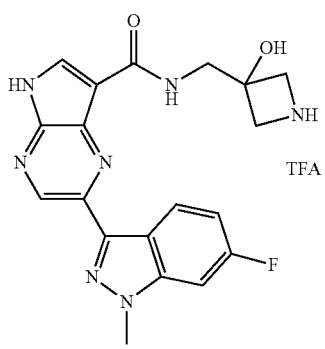 [SMILES: Cn1nc(-c2cnc3[nH]cc(C(=O)NCC4(O)CNC4)c3n2)c2ccc(F)cc21]

Step 1 tert-Butyl 3-oxoazetidine-1-carboxylate

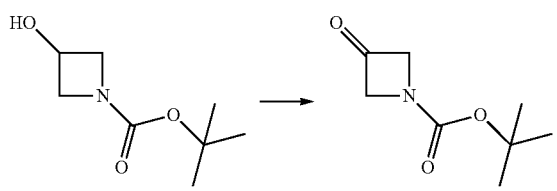

Triethylamine (2.47 mL) was added to a solution of tert-butyl 3-hydroxyazetidine-1-carboxylate (0.5 g, 2.9 mmol) in DMSO (5 mL). To this mixture, a solution of pyridine sulphur trioxide (1.8 g, 11.3 mmol) in DMSO (6.5 mL) was added drop-wise and the mixture was stirred at room temperature for 1.5 hrs. The mixture was poured onto ice-water and extracted with ethyl acetate (3×50 mL), organics combined dried with sodium sulfate, filtered and concentrated to afford tert-butyl 3-oxoazetidine-1-carboxylate as white solid (500 mg, 100%). $^1$H NMR (300 MHz, CDCl$_3$): δ 4.68 (s, 4H), 1.48 (s, 9H).

Step 2 tert-Butyl 3-cyano-3-(trimethylsilyloxy)azetidine-1-carboxylate

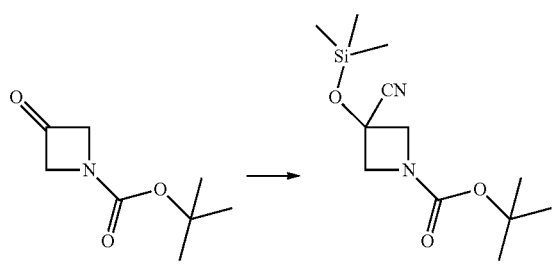 [SMILES: CC(C)(C)OC(=O)N1CC(=O)C1 ; CC(C)(C)OC(=O)N1CC(C#N)(O[Si](C)(C)C)C1]

Tetrabuylammonium cyanide (28 mg) in dichloromethane (5 mL) was added drop-wise to a stirred solution of tert-butyl 3-oxoazetidine-1-carboxylate (250 mg) and trimethylsilyl cyanide (0.28 mL) in dichloromethane (5 mL) at room temperature under nitrogen. The mixture was stirred for 1 h. The mixture was diluted with 50 mL of water, extracted with dichloromethane (3×15 mL), dried over sodium sulfate and concentrated to afford tert-butyl 3-cyano-3-(trimethylsilyloxy)azetidine-1-carboxylate (300 mg, crude) which was used directly to next step without further purification. $^1$H NMR (300 MHz, CDCl$_3$): δ 4.35-4.32 (m, 2H), 4.04-4.01 (m, 2H), 1.45 (s, 9H), 0.27 (s, 9H).

Step 3 tert-Butyl 3-(aminomethyl)-3-hydroxyazetidine-1-carboxylate

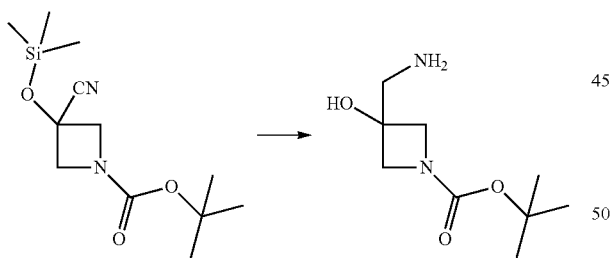

A solution of tert-butyl 3-cyano-3-(trimethylsilyloxy)azetidine-1-carboxylate (300 mg, 1.11 mmol) in THF (5 mL) was treated with borane methylsulfide complex (2M in THF, 2 mL) and the mixture was heated at 70° C. for 1 h under nitrogen. Then the mixture was cooled to room temperature and quenched with methanol (5 mL) followed by treatment with ethylenediamine (0.28 mL), this mixture was stirred at 25° C. for 1 h, and then warmed to 55° C. for 1 h. After cooling to room temperature, the reaction mixture was treated with tetrabutylammonium fluoride (1 M in THF, 2 mL, 2 mmol), then stirred at 25° C. for 1 h. The mixture was diluted with 50 mL of water, product extracted with ethyl acetate (3×25 mL), organics combined dried with sodium sulfate, filtered and concentrated to afford tert-butyl 3-(aminomethyl)-3-hydroxyazetidine-1-carboxylate (200 mg, crude) as white solid which was used to next step without further purification.

Step 4 tert-Butyl 3-((2-(6-fluoro-1-methyl-1H-indazol-3-yl)-5H-pyrrolo[3,2-b]pyrazine-7-carboxamido)methyl)-3-hydroxyazetidine-1-carboxylate

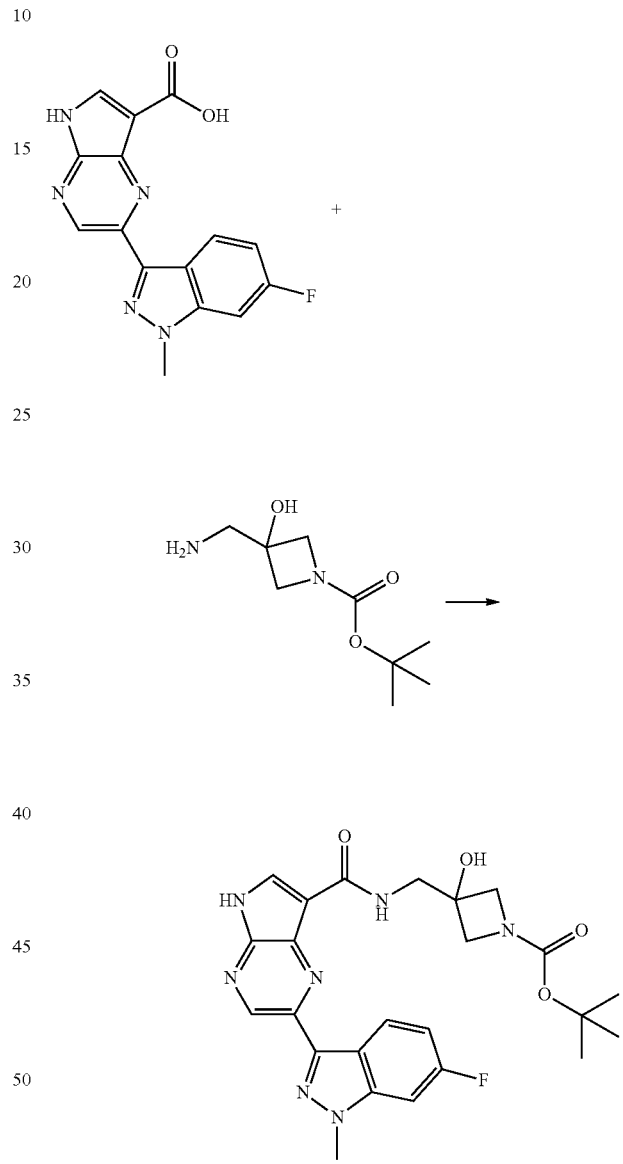

A mixture of 2-(6-fluoro-1-methyl-1H-indazol-3-yl)-5H-pyrrolo[3,2-b]pyrazine-7-carboxylic acid (100 mg, 0.32 mmol), tert-butyl 3-(aminomethyl)-3-hydroxyazetidine-1-carboxylate (196 mg, 0.64 mmol), HATU (145 mg, 0.38 mmol) and DIPEA (0.2 mL, 1.15 mmol) in 10 ml, of dry THF was stirred for 4 hours at room temperature. The reaction mixture was evaporated to dryness, the residue was suspended in 20 mL of 0.5 N HCl, product extracted with ethyl acetate (3×20 mL), organics combined dried with sodium sulfate, filtered and concentrated. The residue was triturated with petroleum ether (1 mL) then decanted and dried to give tert-butyl 342-(6-fluoro-1-methyl-1H-indazol-3-yl)-5H-pyrrolo[3,2-b]pyrazine-7-carboxamido) methyl)-3-hydroxyazetidine-1-carboxylate (86 mg, 54%) as yellow solid, material used in the next step without further purification. LCMS: (M+H)⁺=496.

Step 5

2-(6-Fluoro-1-methyl-1H-indazol-3-yl)-N-((3-hydroxyazetidin-3-yl)methyl)-5H-pyrrolo[3,2-b]pyrazine-7-carboxamide trifluoroacetate

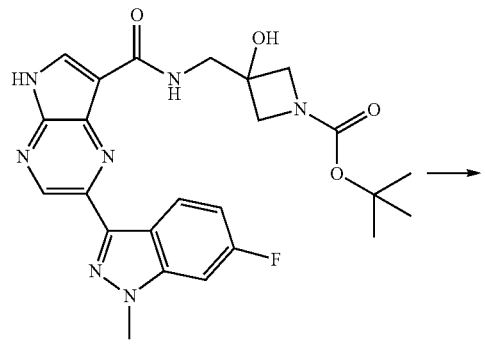

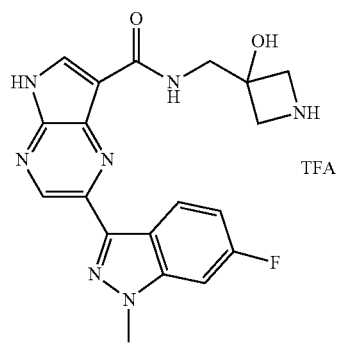

To a solution of tert-butyl 3-((2-(6-fluoro-1-methyl-1H-indazol-3-yl)-5H-pyrrolo[3,2-b]pyrazine-7-carboxamido)methyl)-3-hydroxyazetidine-1-carboxylate (86 mg, 0.16 mmol) in 3 mL of dichloromethane was added 3 mL of trifluoroacetic acid. The reaction mixture was stirred overnight at room temperature. After solvent evaporation, the residue was purified by preparative-HPLC (Gemini 5u C18 150×21.2 mm; inject volume: 3 mL/inj, flow rate: 20 mL/min; wavelength: 214 nm and 254 nm; the gradient conditions are: 40% acetonitrile/60% water (0.1% trifluoroacetic acid V/V) initially, and then proceed to 50% acetonitrile/50% water (0.1% trifluoroacetic acid V/V) in a linear fashion after just 9 min) to afford 2-(6-fluoro-1-methyl-1H-indazol-3-yl)-N-((3-hydroxyazetidin-3-yl)methyl)-5H-pyrrolo[3,2-b]pyrazine-7-carboxamide trifluoroacetate (6 mg, 9%) as yellow solid. LCMS: (M+H)⁺=396; ¹H NMR (300 MHz, CD₃OD): δ 9.05 (s, 1H), 8.48-8.42 (m, 1H), 8.23 (s, 1H), 7.20 (d, 1H, J=9.0 Hz), 6.99 (t, 1H, J=9.3 Hz), 4.10-3.89 (m, 6H).

Example 464

2-(6-Fluoro-1-(3-(methylsulfonyl)propyl)-1H-indazol-3-yl)-N-(1-hydroxy-2-methylpropan-2-yl)-5H-pyrrolo[3,2-b]pyrazine-7-carboxamide Step 1

N-(1-(tert-Butyldimethylsilyloxy)-2-methylpropan-2-yl)-2-(6-fluoro-1H-indazol-3-yl)-5-trityl-5H-pyrrolo[3,2-b]pyrazine-7-carboxamide

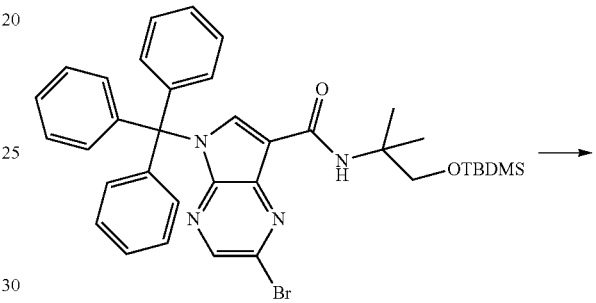

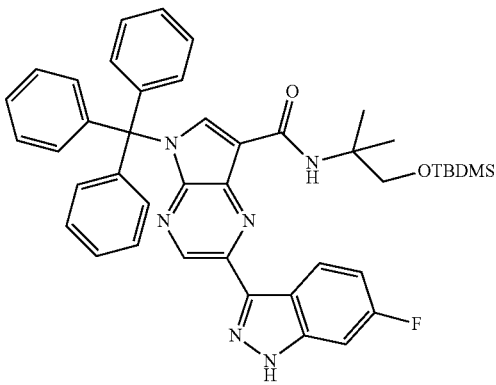

2-Bromo-N-(1-(tert-butyldimethylsilyloxy)-2-methylpropan-2-yl)-5-trityl-5H-pyrrolo[3,2-b]pyrazine-7-carboxamide (287 mg, 0.674 mmol) and 6-fluoro-3-(tributylstannyl)-1H-indazole (450 mg, 0.674 mmol) were dissolved in DMF (8 mL) under nitrogen. Pd(PPh₃)₄ (39 mg, 0.034 mmol) and CuI (26 mg, 0.136 mmol) were added and the mixture was sonicated for 5 min while bubbling nitrogen through it. The reaction mixture was then stirred at 85° C. for 4 h. The mixture was cooled, concentrated in vacuo and then purified by chromatography (silica, petroleum ether:EtOAC 5:1 v/v) to give N-(1-(tert-butyldimethylsilyloxy)-2-methylpropan-2-yl)-2-(6-fluoro-1H-indazol-3-yl)-5-trityl-5H-pyrrolo[3,2-b]pyrazine-7-carboxamide (100 mg, 20%) as a white solid. ¹H NMR (300 MHz, CD₃Cl): δ 8.55 (s, 1H), 8.35 (s, 1H), 8.13

(s, 1H), 8.32 (s, 1H), 7.49-7.47 (m, 3H), 7.29-7.01 (m, 15H), 3.87 (s, 2H), 1.55 (s, 6H), 0.78 (s, 9H), 0.02 (s, 6H). LC-MS: 725.3 [M+H]+.

Step 2

N-(1-(tert-Butyldimethylsilyloxy)-2-methylpropan-2-yl)-2-(6-fluoro-1-(3-(methylsulfonyl)propyl)-1H-indazol-3-yl)-5-trityl-5H-pyrrolo[3,2-b]pyrazine-7-carboxamide

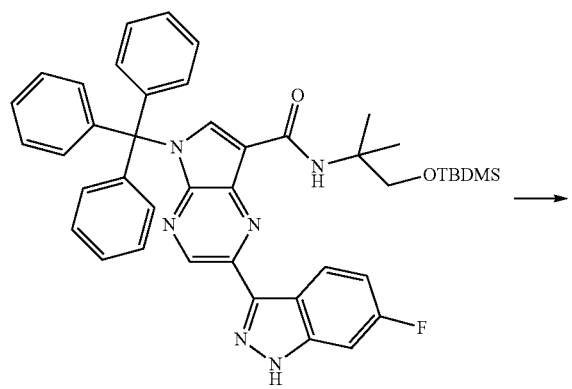

To a mixture of N-(1-(tert-butyldimethylsilyloxy)-2-methylpropan-2-yl)-2-(6-fluoro-1H-indazol-3-yl)-5-trityl-5H-pyrrolo[3,2-b]pyrazine-7-carboxamide (40 mg, 0.055 mmol) in DMF (3 mL) was added 1-chloro-3-(methylsulfonyl)propane (13 mg, 0.083 mmol) followed by K$_2$CO$_3$ (23 mg, 0.165 mmol). The mixture was heated at 40° C. for 16 h, then cooled, poured into water and filtered to give N-(1-(tert-butyldimethylsilyloxy)-2-methylpropan-2-yl)-2-(6-fluoro-1-(3-(methylsulfonyl)propyl)-1H-indazol-3-yl)-5-trityl-5H-pyrrolo[3,2-b]pyrazine-7-carboxamide (35 mg, 76%). The crude material was used directly in the next step without purification. LCMS: 845.2 [M+H]+.

Step 3

N-tert-2-(6-Fluoro-1-(3-(methylsulfonyl)propyl)-1H-indazol-3-yl)-N-(1-hydroxy-2-methylpropan-2-yl)-5H-pyrrolo[3,2-b]pyrazine-7-carboxamide

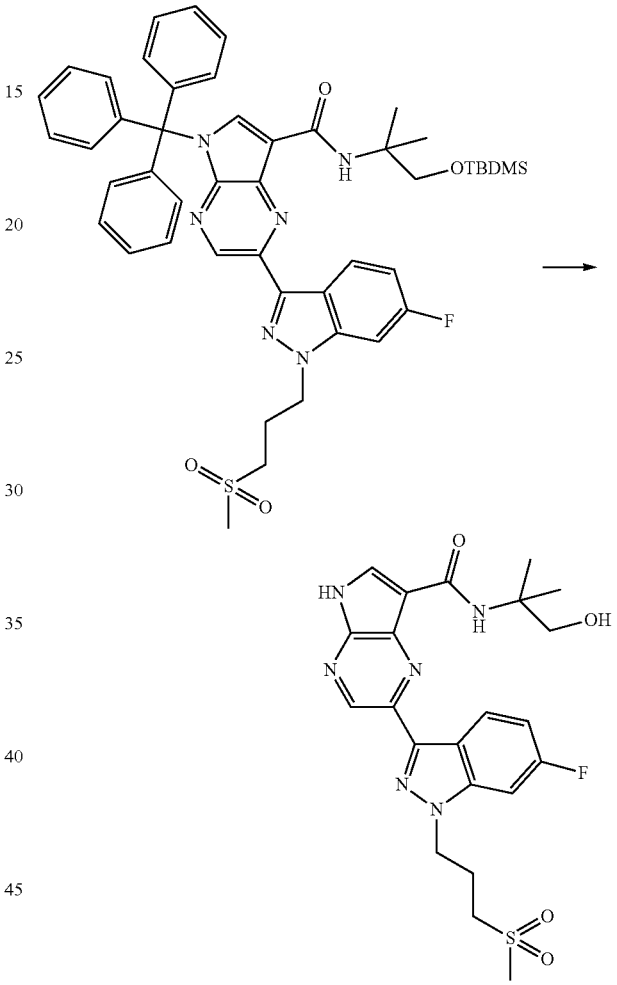

To a stirred solution of N-(1-(tert-butyldimethylsilyloxy)-2-methylpropan-2-yl)-2-(6-fluoro-1-(3-(methylsulfonyl)propyl)-1H-indazol-3-yl)-5-trityl-5H-pyrrolo[3,2-b]pyrazine-7-carboxamide (35 mg, 0.042 mmol) in DCM (2 mL) was added trifluoroacetic acid (1 mL) dropwise at room temperature. The reaction mixture was stirred at room temperature for 1 h, then concentrated in vacuo. The residue obtained was dissolved in DCM, washed with NaHCO$_3$ (aq.), and then the organic layer was concentrated and purified by prep-HPLC (Gemini 5u C18 150×21.2 mm; inject volume: 3 mL/inj, flow rate: 20 mL/min; wavelength: 214 nm and 254 nm; 25% acetonitrile/75% water (doped with 0.1% TFA, v/v) to 42% acetonitrile/58% water (doped with 0.1% TFA, v/v) over 9 min) to give 2-(6-fluoro-1-(3-(methylsulfonyl)propyl)-1H-indazol-3-yl)-N-(1-hydroxy-2-methylpropan-2-yl)-5H-pyrrolo[3,2-b]pyrazine-7-carboxamide (10 mg, 50%) as a white solid. $^1$H NMR (300 MHz, DMSO): δ 12.81 (s, 1H), 9.10 (s, 1H), 8.63-8.58 (m, 1H), 8.37 (s, 1H), 7.90 (s, 1H), 7.71 (d, 1H, J=8.1 Hz), 7.16 (t, 1H, J=9.2 Hz), 5.08 (t, 1H, J=5.5 Hz), 4.62 (t, 2H, J=6.6 Hz), 3.60 (d, 2H, J=5.4 Hz), 3.18 (t, 2H, J=6.4 Hz), 2.96 (s, 3H), 2.32 (t, 2H, J=7.6 Hz), 1.43 (s, 6H). LC/MS: 489.2 [M+H]$^+$, 487.0 [M–H]$^-$.

Example I-465

2-(6-Fluoro-1-methyl-1H-indazol-3-yl)-5H-pyrrolo[2,3-b]pyrazine-7-carboxylic acid (cis-3-hydroxy-cyclobutyl)-amide

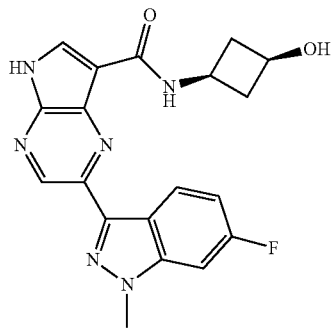 [SMILES: Cn1nc(-c2cnc3[nH]cc(C(=O)N[C@H]4C[C@@H](O)C4)c3n2)c2ccc(F)cc21]

Step 1

A flask was charged with 2-(6-fluoro-1-methyl-1H-indazol-3-yl)-5-(2-trimethylsilanylethoxymethyl)-5H-pyrrolo[2,3-b]pyrazine-7-carboxylic acid (250 mg, 0.57 mmol), 3-aminocyclobutanol hydrochloride (98 mg, 0.79 mmol) and DMF (2.8 mL). N,N-diisopropylethylamine (266 mg, 0.36 mL, 2.06 mmol) was added followed by HATU (237 mg, 0.62 mmol). The yellow solution was stirred at room temperature overnight (a precipitate was formed). The reaction mixture was diluted with water and petroleum ether. The suspension was filtered. The solid was washed with water and a little petroleum ether. The resulting off-white powder was dried under high vacuum. The mixture of cis- and trans-product (265 mg off-white powder) was submitted for further separation by SFC chromatography (KROMASIL OD 3×25 cm, 25% MeOH/CO$_2$+0.1% Triethylamine) to afford 139 mg (48%) 2-(6-fluoro-1-methyl-1H-indazol-3-yl)-5-(2-trimethylsilanyl-ethoxymethyl)-5H-pyrrolo[2,3-b]pyrazine-7-carboxylic acid (cis-3-hydroxy-cyclobutyl)-amide as an off-white solid and 102 mg (35%) 2-(6-fluoro-1-methyl-1H-indazol-3-yl)-5-(2-trimethylsilanyl-ethoxymethyl)-5H-pyrrolo[2,3-b]pyrazine-7-carboxylic acid (trans-3-hydroxy-cyclobutyl)-amide as an off-white solid.

Step 2

In a flask, 2-(6-fluoro-1-methyl-1H-indazol-3-yl)-5-(2-trimethylsilanyl-ethoxymethyl)-5H-pyrrolo[2,3-b]pyrazine-7-carboxylic acid (cis-3-hydroxy-cyclobutyl)-amide (138 mg, 0.27 mmol) was dissolved in dichloromethane (1.3 mL). Trifluoroacetic acid (0.84 mL, 10.9 mmol) was added and the orange solution was stirred at room temperature for 2 h. The reaction mixture was concentrated. The residue (light orange foam) was suspended in dichloromethane (1.3 mL) and ethylenediamine (1.1 mL, 16.3 mmol) was added. The light yellow suspension was stirred at room temperature for 1 h. The reaction mixture was diluted with water and ethyl acetate. The suspension was filtered and washed with water (hot) and ethyl acetate. The resulting off-white powder was dried under high vacuum to afford 81 mg (79%) 2-(6-fluoro-1-methyl-1H-indazol-3-yl)-5H-pyrrolo[2,3-b]pyrazine-7-carboxylic acid (cis-3-hydroxy-cyclobutyl)-amide. LC/MS: [M–H]$^-$=379.

$^1$H NMR (DMSO-d$_6$, 400 MHz): δ (ppm) 12.40-12.97 (br. s., 1H), 9.12 (s, 1H), 8.58 (dd, J=9.0, 5.4 Hz, 1H), 8.43 (s, 1H), 8.37 (d, J=8.3 Hz, 1H), 7.73 (dd, J=9.9, 2.3 Hz, 1H), 7.30 (td, J=9.2, 2.1 Hz, 1H), 5.31 (d, J=4.5 Hz, 1H), 4.17 (s, 3H), 4.08-4.16 (m, 1H), 3.94-4.03 (m, 1H), 2.73-2.84 (m, 2H), 1.91 (qd, J=8.6, 2.8 Hz, 2H).

Example I-466

2-(6-Fluoro-1-methyl-1H-indazol-3-yl)-5H-pyrrolo[2,3-b]pyrazine-7-carboxylic acid (trans-3-hydroxy-cyclobutyl)-amide

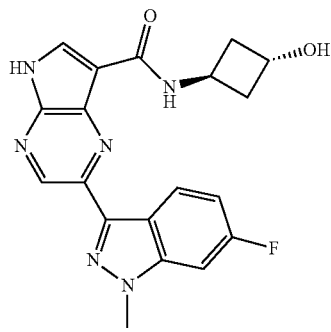 [SMILES: Cn1nc(-c2cnc3[nH]cc(C(=O)N[C@H]4C[C@H](O)C4)c3n2)c2ccc(F)cc21]

In a flask, 2-(6-fluoro-1-methyl-1H-indazol-3-yl)-5-(2-trimethylsilanyl-ethoxymethyl)-5H-pyrrolo[2,3-b]pyrazine-7-carboxylic acid (trans-3-hydroxy-cyclobutyl)-amide (100 mg, 0.20 mmol) was dissolved in dichloromethane (1.0 mL). Trifluoroacetic acid (0.61 mL, 7.92 mmol) was added and the orange solution was stirred at room temperature for 2 h. The reaction mixture was concentrated. The residue (light orange foam) was suspended in dichloromethane (1.0 mL) and ethylenediamine (0.80 ml, 11.8 mmol) was added. The light yellow suspension was stirred at room temperature for 1 h. The reaction mixture was diluted with water and ethyl acetate. The suspension was filtered and washed with water (hot) and ethyl acetate. The resulting off-white powder was dried under high vacuum to provide 55 mg (66%; purity=90%) 2-(6-fluoro-1-methyl-1H-indazol-3-yl)-5H-pyrrolo[2,3-b]pyrazine-7-carboxylic acid (trans-3-hydroxy-cyclobutyl)-amide. LC/MS: [M–H]$^-$=379. $^1$H NMR (DMSO-d$_6$, 400 MHz): δ (ppm) 12.31-12.64 (br. s., 1H), 9.10 (s, 1H), 8.52 (dd, J=9.0, 5.2 Hz, 1H), 8.43 (s, 1H), 8.36 (d, J=7.1 Hz, 1H), 7.72 (dd, J=9.7, 2.1 Hz, 1H), 7.20 (td, J=9.1, 2.3 Hz, 1H), 5.19-5.26 (m, 1H), 4.52-4.61 (m, 1H), 4.44-4.61 (m, 1H), 4.16 (s, 3H), 2.25-2.40 (m, 4H).

BIOLOGICAL EXAMPLES

JAK Assay Information

Determination of IC$_{50}$ of Janus Kinase (JAK) Inhibition:
Enzymes and peptide substrate used are described below:
JAK1: Recombinant human kinase domain from Invitrogen (Cat #PV4774)

JAK3: Recombinant human kinase domain from Millipore (Cat #14-629) or prepared.

JAK2: Recombinant human kinase domain from Millipore (Cat #14-640)

Substrate: N-terminally biotinylated 14-mer peptide derived from activation loop of JAK1 with sequence of the peptide substrate: Biotin-KAIETDKEYYTVKD Assay conditions used are described below:

Assay Buffer: JAK Kinase Buffer: 50 mM Hepes [pH 7.2], 10 mM MgCl$_2$, 1 mM DTT, 1 mg/ml BSA. The assay was carried out in this buffer.

Assay Format The kinase activity of all three JAK kinases was measured using a radioactive, end-point assay and with trace amounts of $^{33}$P-ATP. The assays were carried out in 96-well polypropylene plates.

Experimental Method:

All concentrations were final in the reaction mixture and all incubations were carried at room temperature. Assay steps are described below:

1) Compounds were serially diluted in 100% DMSO typically at a 10× starting concentration of 1 mM. Final concentration of DMSO in the reaction was 10%.
2) Compounds were preincubated with enzyme (0.5 nM JAK3 (commercially available), 0.2 nM JAK3 (prepared), 1 nM JAK2, 5 nM JAK1) for 10 minutes.
3) Reactions were initiated by the addition of a cocktail of the two substrates (ATP and peptide premixed in the JAK Kinase Buffer). In the JAK2/JAK3 assays, ATP and the peptide were used at concentrations of 1.5 uM and 50 uM, respectively. JAK1 assay was carried out at an ATP concentration of 10 uM and a peptide concentration of 50 uM.
4) The duration of the assay for JAK2 and JAK3 is 20 minutes. JAK1 assay was carried out for 40 minutes. With all three enzymes, reactions were terminated by the addition of 0.5M EDTA to a final concentration of 100 mM.
5) 25 ul of terminated reactions were transferred to 150 ul of a 7.5% (v/v) slurry of streptavidin-coated sepharose beads in MgCl$_2$- and CaCl$_2$-free 1× Phosphate Buffered Saline containing 50 mM of EDTA in 96-well, 1.2 um MultiScreen-BV filter plates.
6) After a 30-minute incubation, the beads were washed under vacuum with the following buffers:
    a. 3 to 4 washes with 200 ul of 2M NaCl.
    b. 3 to 4 washes with 200 ul of 2M NaCl plus 1% (v/v) phosphoric acid.
    c. 1 wash with water.
7) Washed plates were dried in a 60° C. oven for between 1 to 2 hours.
8) 70 ul of Microscint 20 scintillation fluid was added to each well of filter plates and after at least 30 minutes of incubation, radioactive counts were measured in a Perkinelmer microplate scintillation counter.

SYK Assay Information

Determination of IC$_{50}$ of Spleen Tyrosine Kinase (SYK) Inhibition:

SYK kinase assay is a standard kinase assay adapted to a 96 well plate format. This assay is performed in 96-well format for IC$_{50}$ determination with 8 samples which represented 10 half log dilutions and a 40 µL reaction volume. The assay measures the incorporation of radiolabeled $^{33}$P γATP into an N-terminally biotinylated peptide substrate, derived from naturally occurring phosphoacceptor consensus sequence (Biotin-11aa DY*E). Phosphorylated products were detected upon termination of reactions with EDTA and the addition of Streptavidin coated beads.

Assay plates: 96-well MultiScreen 0.65 um filter plates (Millipore Cat. No.: MADVNOB10)

Streptavidin coated beads: Streptavidin Sepharose™, suspension 5.0 mL, in 50 mM EDTA/PBS diluted (1:100), (Amersham, Cat. No.: 17-5113-01)

Compounds: 10 mM in 100% dimethylsulfoxide (DMSO), final conc.: compound 0.003-100 uM in 10% DMSO Enzyme: SYK RPA purified, truncated construct of Spleen Tyrosine Kinase aa 360-635, stock solution 1 mg/mL, MW: 31.2 KDa, final conc.: 0.0005 µM.

Peptide 1: biotinylated peptide is derived from a naturally occurring phosphoracceptor consensus sequence (Biotin-EPEGDYEEVLE), special order from QCB, stock solution 20 mM, final conc.: 5.0 µM.

ATP: Adenosine-5'-triphosphate 20 mM, (ROCHE Cat. No.: 93202720), final concentration: 20 µM Buffer: HEPES: 2-Hydroxyethyl piperazine-2-ethane-sulfonic acid (Sigma™, Cat. No.: H-3375) final concentration: 50 mM HEPES pH7.5

BSA: Bovine Serum Albumin Fraction V, fatty acid free (Roche Diagnostics GmbH, Cat. No. 9100221) diluted to a final concentration of 0.1%

EDTA: EDTA stock solution 500 mM, (GIBCO, Cat. No.: 15575-038) final concentration: 0.1 mM DTT: 1,4-Dithiothreitol (Roche Diagnostics GmbH, Cat. No.: 197777), final conc.: 1 mM MgCl$_2$×6H$_2$O: MERCK, Cat. No.: 105833.1000, final concentration: 10 mM Assay Dilution Buffer (ADB): 50 mM HEPES, 0.1 mM EGTA, 0.1 mM Na Vanadate, 0.1 mM β-glycerophosphate, 10 mM MgCl$_2$, 1 mM DTT, 0.1% BSA, pH 7.5

Bead wash buffer: 10 g/L PBS (Phosphate buffered saline) with 2M NaCl+ 1% phosphoric acid.

Experimental Method:

In 40 µL volume, 26 µL of ADB diluted, purified recombinant human SYK360-635 [0.5 nM] was mixed with 4 µL of 10× concentrations of the test compounds, [usually 100 µM-0.003 µM] in [10%] DMSO and the mixture was incubated for 10 min at RT.

The kinase reaction was initiated by the addition of 10 µL 4× substrate cocktail containing the DYE peptide substrate [0 or 5 µM], ATP [20 µM] and $^{33}$PγATP [2 µCi/rxn]. After incubation at 30° C. for 15 min, the reaction was terminated by the transfer of 25 µL pf the reaction sample to a 96 well 0.65 µm Millipore MADVNOB membrane/plate containing 200 µL 5 mM EDTA and 20% Streptavidine coated beads in PBS.

The unbound radionucleotides were washed under vacuum with 3×250 µL 2M NaCl; 2×250 µL 2M NaCl+1% phosphoric acid; 1×250 µL H$_2$O. After the last wash membrane/plates were transferred to an adaptor plate, heat dried for 15 min at 60° C., and 50 µL scintillation cocktail was added to each well and 4 h later the amount of radioactivity was counted in a top counter.

The percent inhibition was calculated based on the uninhibited enzyme rate:

$$\% \text{ Inhibition} = 100/(1+(IC_{50}/\text{Inhibitor conc})^n)$$

The IC$_{50}$ was calculated using a non-linear curve fit with XLfit software (ID Business Solution Ltd., Guilford, Surrey, UK).

Representative IC$_{50}$ for the JAK3 and SYK assays are in Table II below:

TABLE II

| COMPOUND | JAK3-INHIB-DR/v1~NO ADDITIVE~Enzyme_Conc = 100 | SYK_ENZYME_FILTRATION/ v1, BSA |
|---|---|---|
| I-1 | 0.00172 | |
| I-2 | 0.000575 | |
| I-3 | 0.001065 | |
| I-4 | 0.0010525 | |
| I-5 | 0.003005 | |
| I-6 | 0.00123 | |
| I-7 | 0.00112 | |
| I-8 | 0.00283 | |
| I-9 | 0.00401 | |
| I-10 | 0.00151 | |
| I-11 | 0.00177 | |
| I-12 | 0.019195 | |
| I-13 | 0.03108 | |
| I-14 | 0.02752 | |
| I-15 | 0.013565 | |
| I-16 | 0.004815 | |
| I-17 | 0.00286 | |
| I-18 | 0.00115 | |
| I-19 | 0.002115 | |
| I-20 | 0.0004 | |
| I-21 | 0.000285 | |
| I-22 | 0.000725 | 0.04565 |
| I-23 | 0.00059 | |
| I-24 | 0.002345 | |
| I-25 | 0.01923 | 0.05425 |
| I-26 | 0.005695 | |
| I-27 | 0.020465 | |
| I-28 | 0.084595 | |
| I-29 | 0.00081 | 0.0041 |
| I-30 | 0.001445 | |
| I-31 | 0.000335 | 0.053075 |
| I-32 | 0.00026 | |
| I-33 | 0.000975 | |
| I-34 | 0.00127 | |
| I-35 | 0.00033 | |
| I-36 | 0.019045 | 0.0272 |
| I-37 | 0.039175 | 0.0064 |
| I-38 | 0.009005 | 0.0159 |
| I-39 | 0.005805 | 0.24255 |
| I-40 | 0.010185 | 0.9937 |
| I-41 | 0.000375 | |
| I-42 | 0.001245 | |
| I-43 | 0.00063 | |
| I-44 | 0.013945 | 0.015975 |
| I-45 | 0.000535 | 0.01104 |
| I-46 | 0.002855 | 0.01025 |
| I-47 | 0.00531 | 0.0219 |
| I-48 | 0.004915 | 0.02205 |
| I-49 | 0.00566 | |
| I-50 | 0.00263 | |
| I-51 | 0.009105 | |
| I-52 | 0.008865 | 0.01945 |
| I-53 | 0.00707 | |
| I-54 | 0.013955 | 0.07765 |
| I-55 | 0.01688 | 0.0564 |
| I-56 | 0.01168 | 0.007225 |
| I-57 | 0.01057 | 0.04445 |
| I-58 | 0.00231 | |
| I-59 | 0.00319 | |
| I-60 | 0.02735 | 0.03195 |
| I-61 | 0.01678 | |
| I-62 | 0.01514 | |
| I-63 | 0.006665 | |
| I-64 | 0.01327 | |
| I-65 | | 0.0058 |
| I-66 | 0.00217 | |
| I-67 | 0.00048 | |
| I-68 | 0.005755 | |
| I-69 | 0.00461 | |
| I-70 | 0.029845 | |
| I-71 | 0.007955 | |
| I-72 | 0.28472 | |
| I-73 | 0.019655 | 0.00995 |
| I-74 | 0.009345 | |
| I-75 | 0.02062 | 0.0092 |
| I-76 | 0.012695 | |
| I-77 | 0.053795 | >10 |
| I-78 | 0.0142 | 0.03015 |
| I-79 | 0.01513 | |
| I-80 | 0.0126 | 0.0291 |
| I-81 | 0.01002 | |
| I-82 | 0.00136 | |
| I-83 | 0.000635 | |
| I-84 | 0.000735 | |
| I-85 | 0.0009 | 0.033433 |
| I-86 | 0.000745 | 0.10905 |
| I-87 | 0.0017825 | 0.1584 |
| I-88 | 0.001575 | |
| I-89 | 0.001095 | |
| I-90 | 0.00383 | |
| I-91 | 0.00313 | |
| I-92 | 0.002085 | |
| I-93 | 0.000775 | |
| I-94 | 0.01258 | |
| I-95 | 0.004825 | |
| I-96 | 0.005395 | |
| I-97 | 0.05708 | |
| I-98 | 0.00678 | |
| I-99 | 0.00085 | |
| I-100 | 0.15625 | |
| I-101 | 0.01083 | 0.01384 |
| I-102 | 0.00163 | 0.01875 |
| I-103 | 0.00026 | 0.043825 |
| I-104 | 0.005675 | 0.04095 |
| I-105 | 0.05438 | |
| I-106 | 0.00526 | |
| I-107 | 0.01148 | 0.0208 |
| I-108 | 0.007055 | 0.03555 |
| I-109 | 0.044345 | |
| I-110 | 0.0073 | 0.24865 |
| I-111 | 0.00397 | 0.02165 |
| I-112 | 0.014605 | 0.0333 |
| I-113 | 0.256345 | 0.1977 |
| I-114 | 0.01275 | 0.0121 |
| I-115 | 0.008235 | 0.01925 |
| I-116 | 0.00944 | 0.01765 |
| I-117 | 0.008485 | |
| I-118 | 0.002015 | |
| I-119 | 0.003635 | |
| I-120 | 0.002725 | |
| I-121 | 0.12363 | 0.37225 |
| I-122 | 0.082395 | 0.28402 |
| I-123 | 0.068605 | 0.1439 |
| I-124 | 0.001125 | |
| I-125 | 0.029325 | 0.0835 |
| I-126 | 0.018295 | |
| I-127 | 0.01103 | 0.02255 |
| I-128 | 0.01329 | 0.18575 |
| I-129 | 0.004405 | 0.04945 |
| I-130 | 0.01434 | |
| I-131 | 0.007065 | 0.0398 |
| I-132 | 0.00472 | 0.02335 |
| I-133 | 0.056685 | |
| I-134 | 0.067285 | 0.48195 |
| I-135 | 0.006905 | |
| I-136 | 0.1764 | |
| I-137 | 0.132075 | |
| I-138 | 0.03139 | 0.0219 |
| I-139 | 0.00459 | 0.0085 |
| I-140 | 0.00111 | 0.00915 |
| I-141 | 0.00377 | |
| I-142 | 0.00804 | 0.0205 |
| I-143 | >1, 0.53621 | 0.05485 |
| I-144 | 0.013145 | 0.037067 |
| I-145 | 0.01737 | 0.0019 |
| I-146 | 0.01832 | 0.00865 |
| I-147 | 0.038355 | |
| I-148 | 0.05546 | 0.019333 |
| I-149 | 0.010325 | 0.052 |
| I-150 | 0.022485 | 1.5425 |

TABLE II-continued

| COMPOUND | JAK3-INHIB-DR/v1~NO ADDITIVE~Enzyme_Conc = 100 | SYK_ENZYME_FILTRATION/v1, BSA |
|---|---|---|
| I-151 | 0.00347 | 0.02305 |
| I-152 | 0.00115 | |
| I-153 | 0.00402 | |
| I-154 | 0.00495 | 0.0473 |
| I-155 | 0.078295 | |
| I-156 | 0.00547 | 0.0851 |
| I-157 | 0.07158 | 0.41335 |
| I-158 | 0.002025 | 0.0097 |
| I-159 | 0.005825 | 0.066467 |
| I-160 | 0.019375 | 0.0373 |
| I-161 | 0.01632 | 0.0173 |
| I-162 | 0.011275 | |
| I-163 | 0.080685 | 0.356 |
| I-164 | 0.01697 | 0.013475 |
| I-165 | 0.00114 | 0.017 |
| I-166 | 0.0126, >1, >1, 0.012 | 0.1058 |
| I-167 | 0.19713 | 0.07505 |
| I-168 | 0.11803 | 3.7149 |
| I-169 | 0.391485 | 0.012 |
| I-170 | 0.007125 | |
| I-171 | 0.005775 | |
| I-172 | 0.004645 | 0.0135 |
| I-173 | 0.003565 | |
| I-174 | 0.00109 | |
| I-175 | 0.00054 | |
| I-176 | 0.16513 | |
| I-177 | 0.08089 | 0.70355 |
| I-178 | 0.001895 | 0.0046 |
| I-179 | 0.005905 | 0.1489 |
| I-180 | 0.00389 | |
| I-181 | | |
| I-182 | 0.00107 | |
| I-183 | 0.080015 | 0.16135 |
| I-184 | 0.004965 | 0.03715 |
| I-185 | 0.005025 | |
| I-186 | | 0.12935 |
| I-187 | 0.020355 | |
| I-188 | 0.03165 | 0.16825 |
| I-189 | 0.01854 | 0.24785 |
| I-190 | 0.140655 | 0.1266 |
| I-191 | | |
| I-192 | 0.00188 | 0.13545 |
| I-193 | 0.000795 | 0.1397 |
| I-194 | | 0.01185 |
| I-195 | | 0.012017 |
| I-196 | | 0.008 |
| I-197 | | 0.004788 |
| I-198 | 0.001615 | 0.12025 |
| I-199 | 0.177605 | 0.0644 |
| I-200 | 0.054455 | |
| I-201 | 0.010505 | 0.007567 |
| I-202 | 0.13616 | |
| I-203 | 0.26335 | 0.1973 |
| I-204 | 0.216955 | 0.2046 |
| I-205 | 0.0184 | |
| I-206 | 0.017565 | |
| I-207 | 0.00545 | |
| I-208 | 0.077695 | 4.0213, >10 |
| I-209 | >1, 0.82989 | |
| I-210 | 0.10208 | |
| I-211 | >1 | |
| I-212 | 0.002125 | |
| I-213 | 0.076065 | |
| I-214 | 0.027305 | |
| I-215 | 0.02727 | |
| I-216 | 0.012965 | |
| I-217 | 0.0232 | |
| I-218 | 0.01471 | |
| I-219 | 0.003045 | |
| I-220 | 0.002175 | |
| I-221 | 0.00248 | |
| I-222 | 0.009905 | |
| I-223 | 0.189045 | 0.41595 |
| I-224 | 0.3465 | 0.35735 |
| I-225 | 0.14393 | |
| I-226 | 0.008095 | |
| I-227 | 0.00417 | |
| I-228 | 0.00211 | |
| I-229 | 0.00334 | |
| I-230 | 0.012285 | |
| I-231 | 0.002075 | |
| I-232 | 0.00356 | |
| I-233 | 0.00129 | |
| I-234 | 0.002885 | 0.0951 |
| I-235 | 0.00049 | |
| I-236 | 0.000805 | |
| I-237 | 0.000725 | 0.02275 |
| I-238 | 0.000815 | |
| I-239 | 0.001835 | |
| I-240 | 0.000615 | |
| I-241 | 0.00041 | 0.0203 |
| I-242 | 0.002105 | 0.2095 |
| I-243 | 0.001475 | 0.07055 |
| I-244 | 0.00546 | 0.3237 |
| I-245 | 0.047155 | 0.1312 |
| I-246 | 0.04153 | 0.3544 |
| I-247 | 0.06665 | 0.0692 |
| I-248 | 0.053465 | 0.514 |
| I-249 | 0.17046 | 1.98825 |
| I-250 | >1 | 8.9297 |
| I-251 | | 0.0143 |
| I-252 | 0.019435 | 0.06715 |
| I-253 | >1 | 6.37135 |
| I-254 | 0.018575 | 3.2325 |
| I-255 | | 0.6069 |
| I-256 | | 0.02355 |
| I-257 | | 0.004375 |
| I-258 | | 0.02465 |
| I-259 | | 0.04285 |
| I-260 | | 0.00685 |
| I-261 | | 0.001833 |
| I-262 | | 0.00275 |
| I-263 | | 0.0144 |
| I-264 | | 0.00467 |
| I-265 | | 0.008625 |
| I-266 | | 0.00345 |
| I-267 | | 0.03025 |
| I-268 | | 0.0103 |
| I-269 | | 0.0221 |
| I-270 | | 0.0164 |
| I-271 | | 0.0303 |
| I-272 | | 0.07525 |
| I-273 | | 0.005 |
| I-274 | | 0.0025 |
| I-275 | | 0.03305 |
| I-276 | | 0.01635 |
| I-277 | | 0.04 |
| I-278 | | 0.13245 |
| I-279 | | 0.276633 |
| I-280 | 0.239895 | 0.3772 |
| I-281 | 0.06091 | 0.01255 |
| I-282 | 0.012715 | 0.03185 |
| I-283 | 0.01429 | 0.0045 |
| I-284 | 0.071185 | 0.00685 |
| I-285 | 0.08246 | 0.004583 |
| I-286 | 0.74762 | 0.08365 |
| I-287 | | 0.003225 |
| I-288 | | 0.00795 |
| I-289 | | 0.002325 |
| I-290 | | 2.13435 |
| I-291 | | 1.0027 |
| I-292 | | 0.0057 |
| I-293 | | 2.71405 |
| I-294 | | 4.18995 |
| I-295 | | 0.0126 |
| I-296 | 0.078745 | 0.01385 |
| I-297 | | 0.02815 |
| I-298 | | 0.003775 |
| I-299 | | 0.003 |

TABLE II-continued

| COMPOUND | JAK3-INHIB-DR/v1~NO ADDITIVE~Enzyme_Conc = 100 | SYK_ENZYME_FILTRATION/v1, BSA |
|---|---|---|
| I-300 |  | 0.0031 |
| I-301 |  | 0.003925 |
| I-302 |  | 0.0085 |
| I-303 |  | 0.06405 |
| I-304 |  | 0.00735 |
| I-305 | 0.443615 | 0.01305 |
| I-306 |  | 0.007247 |
| I-307 |  | 0.032575 |
| I-308 |  | 0.859833 |
| I-309 | 0.028555 |  |
| I-310 | 0.03139 | 0.0353 |
| I-311 | 0.00446 | 0.010886 |
| I-312 | 0.008245 | 0.07355 |
| I-313 | 0.15686 | 0.046 |
| I-314 |  | 0.1554 |
| I-315 |  | 0.0046 |
| I-316 |  | 0.0146 |
| I-317 |  | 0.011325 |
| I-318 |  | 0.05685 |
| I-319 |  | 0.0346 |
| I-320 |  | 0.05665 |
| I-321 |  | 0.1501 |
| I-322 |  | 0.02425 |
| I-323 |  | 0.02565 |
| I-324 |  | 0.10785 |
| I-325 |  | 0.03755 |
| I-326 |  | 0.0434 |
| I-327 |  | 0.2206 |
| I-328 |  | 0.9704 |
| I-329 |  | 0.0822 |
| I-330 |  | 0.9885 |
| I-331 |  | 0.06945 |
| I-332 |  | 0.1068 |
| I-333 |  | 0.06395 |
| I-334 |  | 1.83575 |
| I-335 |  | 0.06165 |
| I-336 |  | 0.12505 |
| I-337 |  | 0.59485 |
| I-338 |  | 0.03285 |
| I-339 |  | 0.01795 |
| I-340 |  | 0.29515 |
| I-341 |  | 0.0165 |
| I-342 |  | 0.01725 |
| I-343 |  | 0.036975 |
| I-344 |  | 0.008883 |
| I-345 |  | 0.00512 |
| I-346 |  | 0.00555 |
| I-347 |  | 0.014325 |
| I-348 |  | 0.019275 |
| I-349 |  |  |
| I-350 |  | 0.005975 |
| I-351 |  | 0.01845 |
| I-352 |  | 0.01585 |
| I-353 |  | 0.05635 |
| I-354 |  | 0.01445 |
| I-355 |  | 0.003188 |
| I-356 |  | 0.008925 |
| I-357 | 0.005305 | 0.0148 |
| I-358 |  | 0.10675 |
| I-359 |  | 0.1116 |
| I-360 |  | 1.5489 |
| I-361 |  | 0.213875 |
| I-362 |  | 0.00365 |
| I-363 | >1 |  |
| I-364 |  | 0.00484 |
| I-365 | 0.058325 | 0.003325 |
| I-366 | 0.06372 | <0.001, <0.001, <0.001, 0.0016 |
| I-367 |  | 0.004775 |
| I-368 |  | 0.00895 |
| I-369 |  | 0.008 |
| I-370 |  | 0.040975 |
| I-371 |  | 0.02305 |
| I-372 |  | 0.005125 |
| I-373 |  | 0.019 |
| I-374 |  | 0.00765 |
| I-375 | 0.02291 | 0.003375 |
| I-376 |  | 0.002817 |
| I-377 | 0.0054 | 0.00455 |
| I-378 | 0.01277 | 0.003075 |
| I-379 |  | 0.1448 |
| I-380 |  | 0.00995 |
| I-381 |  | 0.7157 |
| I-382 |  | 0.9453 |
| I-383 |  | 0.00805 |
| I-384 |  | 0.00375 |
| I-385 |  | 0.06365 |
| I-386 |  | 0.1039 |
| I-387 |  | 0.0317 |
| I-388 |  | 0.0638 |
| I-389 |  | 0.1829 |
| I-390 |  | 0.0424 |
| I-391 |  | 0.008683 |
| I-392 |  | 0.0102 |
| I-393 |  | 0.4918 |
| I-394 |  | 0.004375 |
| I-395 |  | 0.002275 |
| I-396 |  | >10 |
| I-397 |  | 0.21915 |
| I-398 |  | 0.0122 |
| I-399 | 0.01814 | 0.004725 |
| I-400 |  | 0.008575 |
| I-401 |  | 0.01855 |
| I-402 |  | 0.1013 |
| I-403 |  | 0.01365 |
| I-404 |  | >10 |
| I-405 |  | 0.18625 |
| I-406 |  | 0.08735 |
| I-407 |  | 0.0058 |
| I-408 |  | 0.05265 |
| I-409 |  | 0.3165 |
| I-410 |  | 0.0047 |
| I-411 |  | 0.0954 |
| I-412 |  | 0.07365 |
| I-413 |  | 0.0346 |
| I-414 |  | 0.00525 |
| I-415 |  | 0.322 |
| I-416 |  | 0.00195 |
| I-417 |  | 0.78735 |
| I-418 |  | 0.01995 |
| I-419 |  | 0.0069 |
| I-420 |  | 0.03345 |
| I-421 |  | 0.1635 |
| I-422 |  | 0.00805 |
| I-423 |  | 0.00355 |
| I-424 |  | 0.0077 |
| I-425 |  | 0.025 |
| I-426 |  | 0.0574 |
| I-427 |  | 0.0133 |
| I-428 |  | 0.01185 |
| I-429 |  | 0.0125 |
| I-430 |  | 1.3628 |
| I-431 |  | 0.020675 |
| I-432 |  | 0.0056 |
| I-433 |  | 0.00855 |
| I-434 |  | 0.0046 |
| I-435 |  | 0.01675 |
| I-436 |  | 0.04795 |
| I-437 |  | 0.00395 |
| I-438 |  | 0.027417 |
| I-439 |  | 0.0097 |
| I-440 |  | 0.068 |
| I-441 |  | 0.03025 |
| I-442 |  | 0.87885 |
| I-443 |  | 0.65575 |
| I-444 |  | 1.03685 |
| I-445 |  | 0.0247 |
| I-446 |  | 0.0011 |
| I-447 |  | 0.0027 |
| I-448 |  | 0.0031 |

TABLE II-continued

| COMPOUND | JAK3-INHIB-DR/v1~NO ADDITIVE~Enzyme_Conc = 100 | SYK_ENZYME_FILTRATION/ v1, BSA |
|---|---|---|
| I-449 | | 0.04695 |
| I-450 | | 0.013317 |
| I-451 | | 0.0048 |
| I-452 | | 0.013867 |
| I-453 | | 0.0857 |
| I-454 | | 0.0076 |
| I-455 | | 0.004488 |
| I-456 | | 0.004513 |
| I-457 | | 0.06055 |
| I-458 | | 0.0151 |
| I-459 | | 0.06795 |
| I-460 | | 0.134825 |
| I-461 | | 0.1444 |
| I-462 | | 0.017625 |
| I-463 | | 0.005425 |
| I-464 | | 0.01597 |
| I-465 | | 0.0366 |
| I-466 | | 0.0469 |

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:

1. A compound of Formula I wherein:
R is H;
R' is lower alkoxy or or R and R' together form heterocycloalkyl, optionally substituted with —CN;

$R^1$ is H or $R^{1a}$;
  $R^{1a}$ is lower alkyl, cycloalkyl, lower alkoxy, hydroxy lower alkyl, or lower haloalkyl;
$R^{1'}$ is H or lower alkyl;
  or $R^{1a}$ and $R^{1'}$ together form heterocycloalkyl, cycloalkyl, indan-1-yl, phenyl, or heteroaryl, optionally substituted with one or more $R^{1''}$;
    each $R^{1''}$ is independently hydroxy, amino, oxo, lower alkyl, —C(=O)NH$_2$, —CN, lower haloalkyl, benzyl, cyano lower alkyl, or —NHC(=O)OC(CH$_3$)$_3$;
$R^2$ is H, hydroxy, —CN, —C(=O)NH$_2$, —C(=O)OH, —C(=O)OC(CH$_3$)$_3$, $R^{2a}$, or $R^{2b}$;
  $R^{2a}$ is lower alkyl, phenyl, phenyl lower alkyl, cycloalkyl, heteroaryl, heterocycloalkyl, heterocycloalkyl lower alkyl, heteroaryl lower alkyl, phenyl lower alkoxy, lower alkoxy, optionally substituted with one or more $R^{2a'}$;
    each $R^{2a'}$ is independently hydroxy, —CN, amino, lower alkyl sulfonylamino, lower alkoxy, halo, lower alkyl, cyano lower alkyl, lower haloalkyl, lower alkyl sulfonyl, oxo, halo lower alkoxy, cycloalkyl, —C(=O)OCH$_3$;
  $R^{2b}$ is —C(=O)R$^3$ or —CH$_2$C(=O)R$^3$;
    $R^3$ is heterocycloalkyl, optionally substituted with one or more $R^{3'}$;
      each $R^{3'}$ is independently —CN, halo, lower alkyl, or lower alkyl sulfonyl;
Q is a 1H-indazol-3-yl, 4,5,6,7-tetrahydro-1H-indazol-3-yl, 1H-indol-3-yl, 5,6,7,8-Tetrahydro-imidazo[1,5-a]pyridin-1-yl, imidazo[1,5-a]pyridin-1-yl, indazol-1-yl, 1H-pyrazolo[3,4-b]pyridin-3-yl, 1H-pyrazolo[4,3-b]pyridin-3-yl, imidazo[1,2-a]pyridin-3-yl, 2-oxy-4,5,6,7-tetrahydro-1H-indazol-3-yl, benzoimidazol-1-yl, isoquinolin-1-yl, isoquinolin-8-yl, 1H-thieno[3,2-c]pyrazol-3-yl, 1,4,5,6-tetrahydro-cyclopentapyrazol-3-yl, 5,6-dihydro-4H-cyclopentapyrazol-1-yl, 1,4,5,6,7,8-hexahydro-cycloheptapyrazol-3-yl, 1H-indol-7-yl, 1H-pyrrolo[2,3-c]pyridin-7-yl, 1H-indazol-4-yl or 1H-indazol-7-yl, optionally substituted with one or more $Q^a$ or $Q^b$;
  each $Q^a$ is independently halo, —CN, hydroxy, or —(CH$_2$)$_n$C(=O)Q$^{a'}$;
    each $Q^{a'}$ is independently hydroxy, amino, or heterocycloalkyl, wherein heterocycloalkyl is optionally substituted by one or more $Q^{a''}$;
      each $Q^{a''}$ is independently lower alkyl or lower haloalkyl;
    n is 1, 2, or 3;
  each $Q^b$ is independently lower alkyl, cycloalkyl, lower alkoxy, phenoxy, lower alkyl sulfonyl, heterocycloalkyl, heterocycloalkyl lower alkyl, or heteroaryl lower alkyl, optionally substituted with one or more $Q^{b'}$; and
    each $Q^{b'}$ is independently hydroxy, halo, —CN, amino, heterocycloalkyl, lower alkyl, benzyl, or lower alkyl sulfonyl;
or a pharmaceutically acceptable salt thereof.

2. The compound of claim 1, wherein R is H and R' is

3. The compound of claim 2, wherein $R^{1'}$ is H or lower alkyl.

4. The compound of claim 3, wherein $R^1$ is lower alkyl.

5. The compound of claim 3, wherein both $R^1$ and $R^{1'}$ are H.

6. The compound of claim 4, wherein $R^2$ is —C(=O)$R^3$.

7. The compound of claim 4, wherein $R^2$ is lower alkyl, optionally substituted with one or more $R^{2a'}$.

8. The compound of claim 7, wherein Q is a 1H-indazol-3-yl, 4,5,6,7-tetrahydro-1H-indazol-3-yl, 1H-indol-3-yl, 5,6,7,8-Tetrahydro-imidazo[1,5-a]pyridin-1-yl, imidazo[1,5-a]pyridin-1-yl, indazol-1-yl, 1H-pyrazolo[3,4-b]pyridin-3-yl, 1H-pyrazolo[4,3-b]pyridin-3-yl, imidazo[1,2-a]pyridin-3-yl, 2-oxy-4,5,6,7-tetrahydro-1H-indazol-3-yl or benzoimidazol-1-yl, optionally substituted with one or more $Q^a$ or $Q^b$.

9. The compound of claim 1, wherein Q is indazol-3-yl, optionally substituted with one or more $Q^a$ or $Q^b$.

10. The compound of claim 9, wherein $Q^a$ is halo.

11. The compound of claim 10, wherein $Q^b$ is lower alkyl.

12. The compound of claim 11, wherein $R^{1a}$ and $R^{1'}$ together form heterocycloalkyl or cycloalkyl, optionally substituted with one or more $R^{1''}$.

13. The compound of claim 12, wherein $R^{1''}$ is amino or —CN.

14. The compound of claim 13, wherein $R^2$ is lower alkyl.

15. A pharmaceutical composition comprising the compound of claim 1, admixed with at least one pharmaceutically acceptable carrier, excipient or diluent.

16. A compound selected from the group consisting of
2-(1-Methyl-1H-indazol-3-yl)-5H-pyrrolo[2,3-b]pyrazine-7-carboxylic acid [(R)-2-(4-cyano-piperidin-1-yl)-1-cyclopropyl-2-oxo-ethyl]-amide;
2-(6-Chloro-1-methyl-1H-indazol-3-yl)-5H-pyrrolo[2,3-b]pyrazine-7-carboxylic acid [(R)-2-(4-cyano-piperidin-1-yl)-1-cyclopropyl-2-oxo-ethyl]-amide;
2-(5-Chloro-1-methyl-1H-indazol-3-yl)-5H-pyrrolo[2,3-b]pyrazine-7-carboxylic acid [(R)-2-(4-cyano-piperidin-1-yl)-1-cyclopropyl-2-oxo-ethyl]-amide;
2-(6-Chloro-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide;
2-(5-Chloro-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide;
2-(5,6-Dichloro-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide;
2-(1-Methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide;
2-(5-Chloro-1-methyl-1H-indazol-3-yl)-5H-pyrrolo[2,3-b]pyrazine-7-carboxylic acid [(R)-1-(4-cyano-piperidine-1-carbonyl)-2,2-dimethyl-propyl]-amide;
2-(6-Cyclopropyl-1-methyl-1H-indazol-3-yl)-5H-pyrrolo[2,3-b]pyrazine-7-carboxylic acid [(R)-2-(4-cyano-piperidin-1-yl)-1-cyclopropyl-2-oxo-ethyl]-amide;
2-(1-Methyl-4,5,6,7-tetrahydro-1H-indazol-3-yl)-5H-pyrrolo[2,3-b]pyrazine-7-carboxylic acid [(R)-2-(4-cyano-piperidin-1-yl)-1-cyclopropyl-2-oxo-ethyl]-amide;
2-(5-Chloro-1-methyl-1H-indazol-3-yl)-5H-pyrrolo[2,3-b]pyrazine-7-carboxylic acid ((S)-1,2,2-trimethyl-propyl)-amide;
2-(6-Chloro-1-methyl-1H-indazol-3-yl)-5H-pyrrolo[2,3-b]pyrazine-7-carboxylic acid ((R)-2-hydroxy-1,2-dimethyl-propyl)-amide;
2-(1,5,5-Trimethyl-4,5,6,7-tetrahydro-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide;
2-(6-Chloro-1-methyl-1H-indazol-3-yl)-5H-pyrrolo[2,3-b]pyrazine-7-carboxylic acid [(R)-2-(3,3-difluoro-azetidin-1-yl)-1-methyl-2-oxo-ethyl]-amide;
2-(6-Chloro-1-methyl-1H-indazol-3-yl)-5H-pyrrolo[2,3-b]pyrazine-7-carboxylic acid ((R)-1-methanesulfonyl-piperidin-3-yl)-amide;
2-(6-Chloro-1-methyl-1H-indazol-3-yl)-5H-pyrrolo[2,3-b]pyrazine-7-carboxylic acid ((R)-1-cyclopropyl-ethyl)-amide;
2-(6-Cyclopropyl-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide;
2-(1-Methyl-6-trifluoromethyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide;
2-(6-Chloro-1-methyl-1H-indazol-3-yl)-5H-pyrrolo[2,3-b]pyrazine-7-carboxylic acid [(R)-1-(4-cyano-piperidine-1-carbonyl)-2,2-dimethyl-propyl]-amide;
2-(6-Chloro-1-methyl-1H-indazol-3-yl)-5H-pyrrolo[2,3-b]pyrazine-7-carboxylic acid [(R)-1-(3-cyano-azetidine-1-carbonyl)-propyl]-amide;
2-(6-Chloro-1-methyl-1H-indazol-3-yl)-5H-pyrrolo[2,3-b]pyrazine-7-carboxylic acid [(R)-2-(3-cyano-azetidin-1-yl)-1-cyclopropyl-2-oxo-ethyl]-amide;
2-(6-Cyano-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide;
2-(6-Chloro-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide;
2-[6-Chloro-1-(2-methoxy-ethyl)-1H-indazol-3-yl]-5H-pyrrolo[2,3-b]pyrazine-7-carboxylic acid [(R)-2-(3-cyano-azetidin-1-yl)-1-methyl-2-oxo-ethyl]-amide;
2-(6-Chloro-1-methyl-1H-indazol-3-yl)-5H-pyrrolo[2,3-b]pyrazine-7-carboxylic acid ((R)-1-phenyl-ethyl)-amide;
2-(1-Methyl-4,5,6,7-tetrahydro-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide;
2-(6-Chloro-1-methyl-1H-indazol-3-yl)-5H-pyrrolo[2,3-b]pyrazine-7-carboxylic acid [(R)-1-methyl-2-(2-oxa-6-aza-spiro[3.3]hept-6-yl)-2-oxo-ethyl]-amide;
2-(6-Chloro-1-methyl-1H-indazol-3-yl)-5H-pyrrolo[2,3-b]pyrazine-7-carboxylic acid ((R)-1-methyl-2-morpholin-4-yl-2-oxo-ethyl)-amide;
2-(6-Chloro-1-methyl-1H-indol-3-yl)-5H-pyrrolo[2,3-b]pyrazine-7-carboxylic acid [(R)-2-(3-cyano-azetidin-1-yl)-1-methyl-2-oxo-ethyl]-amide;
2-(6-Chloro-5-fluoro-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide;
2-(6-Methyl-imidazo[1,5-a]pyridin-1-yl)-5H-pyrrolo[2,3-b]pyrazine-7-carboxylic acid [(R)-2-(3-cyano-azetidin-1-yl)-1-methyl-2-oxo-ethyl]-amide;
2-(6-Fluoro-imidazo[1,5-a]pyridin-1-yl)-5H-pyrrolo[2,3-b]pyrazine-7-carboxylic acid [(R)-2-(3-cyano-azetidin-1-yl)-1-methyl-2-oxo-ethyl]-amide;
2-(6,8-Difluoro-imidazo[1,5-a]pyridin-1-yl)-5H-pyrrolo[2,3-b]pyrazine-7-carboxylic acid [(R)-2-(3-cyano-azetidin-1-yl)-1-methyl-2-oxo-ethyl]-amide;
2-(6-Fluoro-3-methyl-imidazo[1,5-a]pyridin-1-yl)-5H-pyrrolo[2,3-b]pyrazine-7-carboxylic acid [(R)-2-(3-cyano-azetidin-1-yl)-1-methyl-2-oxo-ethyl]-amide;
2-(6-Fluoro-3-hydroxymethyl-imidazo[1,5-a]pyridin-1-yl)-5H-pyrrolo[2,3-b]pyrazine-7-carboxylic acid [(R)-2-(3-cyano-azetidin-1-yl)-1-methyl-2-oxo-ethyl]-amide;

2-(6-Chloro-1-methyl-1H-indazol-3-yl)-5H-pyrrolo[2,3-b]pyrazine-7-carboxylic acid ((1R,3R)-3-cyano-cyclopentyl)-amide;
2-(6-Chloro-1-methyl-1H-indazol-3-yl)-5H-pyrrolo[2,3-b]pyrazine-7-carboxylic acid (3-amino-cyclopentyl)-amide;
2-(6-Chloro-1-methyl-1H-indazol-3-yl)-5H-pyrrolo[2,3-b]pyrazine-7-carboxylic acid (3-methanesulfonylamino-cyclopentyl)-amide;
2-(3-Chloro-6-fluoro-imidazo[1,5-a]pyridin-1-yl)-5H-pyrrolo[2,3-b]pyrazine-7-carboxylic acid ((S)-2-methoxy-1-methyl-ethyl)-amide;
2-(6,8-Difluoro-imidazo[1,5-a]pyridin-1-yl)-5H-pyrrolo[2,3-b]pyrazine-7-carboxylic acid ((S)-2-methoxy-1-methyl-ethyl)-amide;
2-(6-Fluoro-imidazo[1,5-a]pyridin-1-yl)-5H-pyrrolo[2,3-b]pyrazine-7-carboxylic acid ((S)-2-methoxy-1-methyl-ethyl)-amide;
2-(6-Fluoro-3-methanesulfonyl-imidazo[1,5-a]pyridin-1-yl)-5H-pyrrolo[2,3-b]pyrazine-7-carboxylic acid [(R)-2-(3-cyano-azetidin-1-yl)-1-methyl-2-oxo-ethyl]-amide;
2-(6-Chloro-1-methyl-1H-indazol-3-yl)-5H-pyrrolo[2,3-b]pyrazine-7-carboxylic acid [(R)-1-(3-cyano-azetidine-1-carbonyl)-2,2-dimethyl-propyl]-amide;
2-(6-Fluoro-1-methyl-1H-indazol-3-yl)-5H-pyrrolo[2,3-b]pyrazine-7-carboxylic acid ((R)-2-fluoro-1,2-dimethyl-propyl)-amide;
2-(6-Fluoro-1-methyl-1H-indazol-3-yl)-5H-pyrrolo[2,3-b]pyrazine-7-carboxylic acid ((S)-1,2,2-trimethyl-propyl)-amide;
2-(6-Fluoro-1-methyl-1H-indazol-3-yl)-5H-pyrrolo[2,3-b]pyrazine-7-carboxylic acid (cis-3-hydroxy-cyclopentyl)-amide;
2-(6-Fluoro-1-methyl-1H-indazol-3-yl)-5H-pyrrolo[2,3-b]pyrazine-7-carboxylic acid (trans-3-hydroxy-cyclopentyl)-amide;
2-(6-Chloro-1-methyl-1H-indazol-3-yl)-5H-pyrrolo[2,3-b]pyrazine-7-carboxylic acid (1-oxazol-2-yl-ethyl)-amide;
2-(6-Fluoro-1-methyl-1H-indazol-3-yl)-5H-pyrrolo[2,3-b]pyrazine-7-carboxylic acid (1-oxazol-2-yl-ethyl)-amide;
2-(6-Fluoro-1-methyl-1H-indazol-3-yl)-5H-pyrrolo[2,3-b]pyrazine-7-carboxylic acid ((R)-1-oxazol-2-yl-ethyl)-amide;
2-(6-Fluoro-1-methyl-1H-indazol-3-yl)-5H-pyrrolo[2,3-b]pyrazine-7-carboxylic acid ((S)-1-oxazol-2-yl-ethyl)-amide;
2-(6-Fluoro-1-methyl-1H-indazol-3-yl)-5H-pyrrolo[2,3-b]pyrazine-7-carboxylic acid (1-oxazol-4-yl-ethyl)-amide;
2-(6-Fluoro-1-methyl-1H-indazol-3-yl)-5H-pyrrolo[2,3-b]pyrazine-7-carboxylic acid (1-isoxazol-3-yl-ethyl)-amide;
2-(6-Fluoro-1-methyl-1H-indazol-3-yl)-5H-pyrrolo[2,3-b]pyrazine-7-carboxylic acid [1-(5-methyl-isoxazol-3-yl)-ethyl]-amide;
2-(6-Fluoro-1-methyl-1H-indazol-3-yl)-5H-pyrrolo[2,3-b]pyrazine-7-carboxylic acid (1-isoxazol-3-yl-ethyl)-amide;
2-(6-Fluoro-1-methyl-1H-indazol-3-yl)-5H-pyrrolo[2,3-b]pyrazine-7-carboxylic acid ((R)-2,2-difluoro-1-methyl-propyl)-amide;
2-(6-Fluoro-1-methyl-1H-indazol-3-yl)-5H-pyrrolo[2,3-b]pyrazine-7-carboxylic acid (cis-3-cyanomethyl-cyclopentyl)-amide;
2-(6-Fluoro-imidazo[1,5-a]pyridin-1-yl)-5H-pyrrolo[2,3-b]pyrazine-7-carboxylic acid ((R)-1-oxazol-2-yl-ethyl)-amide;
2-(6-Fluoro-1-methyl-1H-indazol-3-yl)-5H-pyrrolo[2,3-b]pyrazine-7-carboxylic acid [(R)-1-(3-fluoro-azetidine-1-carbonyl)-butyl]-amide;
2-(6-Fluoro-1-methyl-1H-indazol-3-yl)-5H-pyrrolo[2,3-b]pyrazine-7-carboxylic acid [(R)-1-(4,5-dihydro-oxazol-2-yl)-ethyl]-amide;
2-(6-Fluoro-1-methyl-1H-indazol-3-yl)-5H-pyrrolo[2,3-b]pyrazine-7-carboxylic acid ((R)-2,2-difluoro-1-methyl-3-phenyl-propyl)-amide;
2-(6-Fluoro-1-methyl-1H-indazol-3-yl)-5H-pyrrolo[2,3-b]pyrazine-7-carboxylic acid [(R)-1-(4-cyanomethyl-oxazol-2-yl)-ethyl]-amide;
2-(6-Fluoro-1-methyl-1H-indazol-3-yl)-5H-pyrrolo[2,3-b]pyrazine-7-carboxylic acid [(R)—(S)-1-(tetrahydro-furan-2-yl)-ethyl]-amide;
2-(6-Fluoro-1-methyl-1H-indazol-3-yl)-5H-pyrrolo[2,3-b]pyrazine-7-carboxylic acid [(R)—(R)-1-(tetrahydro-furan-2-yl)-ethyl]-amide;
2-(5-Hydroxy-1-methyl-1H-indazol-3-yl)-5H-pyrrolo[2,3-b]pyrazine-7-carboxylic acid isopropylamide;
2-(5-Chloro-indazol-1-yl)-5H-pyrrolo[2,3-b]pyrazine-7-carboxylic acid [(R)-2-(4-cyano-piperidin-1-yl)-1-cyclopropyl-2-oxo-ethyl]-amide;
2-(5,6-Dichloro-1-methyl-1H-indazol-3-yl)-5H-pyrrolo[2,3-b]pyrazine-7-carboxylic acid [(R)-2-(4-cyano-piperidin-1-yl)-1-cyclopropyl-2-oxo-ethyl]-amide;
2-(5,6-Dichloro-indazol-1-yl)-5H-pyrrolo[2,3-b]pyrazine-7-carboxylic acid [(R)-2-(4-cyano-piperidin-1-yl)-1-cyclopropyl-2-oxo-ethyl]-amide;
2-(5-Chloro-indazol-1-yl)-5H-pyrrolo[2,3-b]pyrazine-7-carboxylic acid [(R)-2-(3-cyano-azetidin-1-yl)-1-methyl-2-oxo-ethyl]-amide;
2-(1,6,6-Trimethyl-4,5 6,7-tetrahydro-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide;
2-(6-Chloro-1-methyl-1H-indazol-3-yl)-5H-pyrrolo[2,3-b]pyrazine-7-carboxylic acid [1-(1-methanesulfonyl-azetidin-3-yl)-ethyl]-amide;
2-(6-Chloro-1-methyl-1H-indazol-3-yl)-5H-pyrrolo[2,3-b]pyrazine-7-carboxylic acid ((R)-1-methyl-3-oxo-3-pyrrolidin-1-yl-propyl)-amide;
2-(6-Fluoro-1-methyl-1H-indazol-3-yl)-5H-pyrrolo[2,3-b]pyrazine-7-carboxylic acid [1-(cis-3-hydroxy-cyclobutyl)-ethyl]-amide;
2-(6-Fluoro-1-methyl-1H-indazol-3-yl)-5H-pyrrolo[2,3-b]pyrazine-7-carboxylic acid [1-(trans-3-cyano-cyclobutyl)-ethyl]-amide;
2-(6-Fluoro-1-methyl-1H-indazol-3-yl)-5H-pyrrolo[2,3-b]pyrazine-7-carboxylic acid [1-(trans-3-hydroxy-cyclobutyl)-ethyl]-amide;
2-(6-Fluoro-1-methyl-1H-indazol-3-yl)-5H-pyrrolo[2,3-b]pyrazine-7-carboxylic acid [1-(cis-3-cyano-cyclobutyl)-ethyl]-amide;
2-Isoquinolin-1-yl-5H-pyrrolo[2,3-b]pyrazine-7-carboxylic acid [(R)-2-(3-cyano-azetidin-1-yl)-1-methyl-2-oxo-ethyl]-amide;
2-(6-Fluoro-1-methyl-1H-indazol-3-yl)-5H-pyrrolo[2,3-b]pyrazine-7-carboxylic acid ((R)-1-pyridin-2-yl-ethyl)-amide;
2-(6-Fluoro-1-methyl-1H-indazol-3-yl)-5H-pyrrolo[2,3-b]pyrazine-7-carboxylic acid [(R)-1-(4-trifluoromethyl-pyridin-2-yl)-ethyl]-amide;

2-(6-Chloro-1-methyl-1H-indazol-3-yl)-5H-pyrrolo[2,3-b]pyrazine-7-carboxylic acid ((S)-2-cyano-1,2,2-trimethyl-ethyl)-amide;

2-(6-tert-Butyl-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide;

2-(1,6-Dimethyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide;

2-(6-Fluoro-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide;

2-(6-Methoxy-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide;

2-(6-Chloro-1-ethyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide;

2-(6,7-Difluoro-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide;

2-(6-Ethyl-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide;

2-(4,6-Difluoro-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide;

2-(1,6-Dimethyl-1H-pyrazolo[3,4-b]pyridin-3-yl)-5H-pyrrolo[2,3-b]pyrazine-7-carboxylic acid [(R)-2-(3-cyano-azetidin-1-yl)-1-methyl-2-oxo-ethyl]-amide;

2-[6-Chloro-1-(2-hydroxy-ethyl)-1H-indazol-3-yl]-5H-pyrrolo[2,3-b]pyrazine-7-carboxylic acid [(R)-2-(3-cyano-azetidin-1-yl)-1-methyl-2-oxo-ethyl]-amide;

2-(6-Chloro-1-isopropyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide;

2-(6-Chloro-1-propyl-1H-indazol-3-yl)-5H-pyrrolo[2,3-b]pyrazine-7-carboxylic acid acid [(R)-2-(3-cyano-azetidin-1-yl)-1-methyl-2-oxo-ethyl]-amide;

2-[6-Chloro-1-(2,3-dihydroxy-propyl-1H-indazol-3-yl]-5H-pyrrolo[2,3-b]pyrazine-7-carboxylic acid [(R)-2-(3-cyano-azetidin-1-yl)-1-methyl-2-oxo-ethyl]-amide;

2-[6-Chloro-1-(2-hydroxy-propyl)-1H-indazol-3-yl]-5H-pyrrolo[2,3-b]pyrazine-7-carboxylic acid [(R)-2-(3-cyano-azetidin-1-yl)-1-methyl-2-oxo-ethyl]-amide;

2-[6-Chloro-1-(3-hydroxy-propyl)-1H-indazol-3-yl]-5H-pyrrolo[2,3-b]pyrazine-7-carboxylic acid [(R)-2-(3-cyano-azetidin-1-yl)-1-methyl-2-oxo-ethyl]-amide;

2-(4,6-Dichloro-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide;

2-(1-Methyl-1H-pyrazolo[4,3-b]pyridin-3-yl)-5H-pyrrolo[2,3-b]pyrazine-7-carboxylic acid [(R)-2-(3-cyano-azetidin-1-yl)-1-methyl-2-oxo-ethyl]-amide;

2-(1-Methyl-1H-thieno[3,2-c]pyridin-3-yl)-5H-pyrrolo[2,3-b]pyrazine-7-carboxylic acid [(R)-2-(3-cyano-azetidin-1-yl)-1-methyl-2-oxo-ethyl]-amide;

2-(6-Fluoro-1-methyl-1H-indazol-3-yl)-5H-pyrrolo[2,3-b]pyrazine-7-carboxylic acid [(R)-1-(1-cyano-cyclopentyl)-ethyl]-amide;

2-(4,6-Difluoro-1-methyl-1H-indazol-3-yl)-5H-pyrrolo[2,3-b]pyrazine-7-carboxylic acid isopropylamide;

2-(6-Fluoro-1-oxetan-3-yl-1H-indazol-3-yl)-5H-pyrrolo[2,3-b]pyrazine-7-carboxyli acid isopropylamide, 2-(6-Fluoro-1-oxetan-3-yl-1H-indazol-3-yl)-5H-pyrrolo[2,3-b]pyrazine-7-carboxylic acid ((S)-2-methoxy-1-methyl-ethyl)-amide;

2-(1-Azetidin-3-yl-6-fluoro-1H-indazol-3-yl)-5H-pyrrolo[2,3-b]pyrazine-7-carboxylic acid isopropylamide, 2-(6-Chloro-1-methyl-1H-indazol-3-yl)-5H-pyrrolo[2,3-b]pyrazine-7-carboxylic acid ((R)-2-methanesulfonyl-1-methyl-ethyl)-amide;

2-(6-Chloro-1-methyl-1H-indazol-3-yl)-5H-pyrrolo[2,3-b]pyrazine-7-carboxylic acid cycyclopentylamide;

2-(6-Chloro-1-methyl-1H-indazol-3-yl)-5H-pyrrolo[2,3-b]pyrazine-7-carboxylic acid (tetrahydro-furan-3-yl)-amide;

2-(6-Chloro-1-methyl-1H-indazol-3-yl)-5H-pyrrolo[2,3-b]pyrazine-7-carboxylic acid isopropylamide;

2-(6-Chloro-1-methyl-1H-indazol-3-yl)-5H-pyrrolo[2,3-b]pyrazine-7-carboxylic acid ethylamide;

2-(6-Chloro-1-methyl-1H-indazol-3-yl)-5H-pyrrolo[2,3-b]pyrazine-7-carboxylic acid cyclohexylamide;

2-(6-Chloro-1-methyl-1H-indazol-3-yl)-5H-pyrrolo[2,3-b]pyrazine-7-carboxylic acid (tetrahydro-pyran-3-yl)-amide;

2-(6-Chloro-1-methyl-1H-indazol-3-yl)-5H-pyrrolo[2,3-b]pyrazine-7-carboxylic acid (tetrahydro-pyran-4-yl)-amide;

2-(6-Chloro-1-methyl-1H-indazol-3-yl)-5H-pyrrolo[2,3-b]pyrazine-7-carboxylic acid (1,1-dioxo-tetrahydro-1$\lambda$6-thiophen-3-yl)-amide;

2-(6-Fluoro-1-methyl-1H-indazol-3-yl)-5H-pyrrolo[2,3-b]pyrazine-7-carboxylic acid (3-hydroxy-2,2-dimethyl-propyl)-amide;

2-(6-Fluoro-1-methyl-1H-indazol-3-yl)-5H-pyrrolo[2,3-b]pyrazine-7-carboxylic acid (2,2-dimethyl-propyl)-amide;

2-(6-Fluoro-1-methyl-1H-indazol-3-yl)-5H-pyrrolo[2,3-b]pyrazine-7-carboxylic acid isobutyl-amide;

2-(6-Fluoro-1-methyl-1H-indazol-3-yl)-5H-pyrrolo[2,3-b]pyrazine-7-carboxylic acid cyclopropylmethyl-amide;

2-(6-Chloro-1-methyl-1H-indazol-3-yl)-5H-pyrrolo[2,3-b]pyrazine-7-carboxylic acid [(R)-2-((S)-3-fluoro-pyrrolidin-1-yl)-1-methyl-2-oxo-ethyl]-amide;

2-(6-Chloro-1-methyl-1H-indazol-3-yl)-5H-pyrrolo[2,3-b]pyrazine-7-carboxylic acid [(R)-2-((R)-3-fluoro-pyrrolidin-1-yl)-1-methyl-2-oxo-ethyl]-amide;

2-(6-Chloro-1-methyl-1H-indazol-3-yl)-5H-pyrrolo[2,3-b]pyrazine-7-carboxylic acid [(R)-2-(3-fluoro-azetidin-1-yl)-1-methyl-2-oxo-ethyl]-amide;

2-(6-Chloro-1-methyl-1H-indazol-3-yl)-5H-pyrrolo[2,3-b]pyrazine-7-carboxylic acid [(R)-2-((R)-3-fluoro-pyrrolidin-1-yl)-1-methyl-ethyl]-amide;

2-(6-Chloro-1-methyl-1H-indazol-3-yl)-5H-pyrrolo[2,3-b]pyrazine-7-carboxylic acid [(R)-2-((S)-3-fluoro-pyrrolidin-1-yl)-1-methyl-ethyl]-amide;

2-(6-Chloro-1-methyl-1H-indazol-3-yl)-5H-pyrrolo[2,3-b]pyrazine-7-carboxylic acid [(R)-2-(3-fluoro-azetidin-1-yl)-1-methyl-ethyl]-amide;

2-(6-Chloro-4-fluoro-1-methyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide;

2-(6-Chloro-1-methyl-1H-indazol-3-yl)-5H-pyrrolo[2,3-b]pyrazine-7-carboxylic acid [2-(3-cyano-pyrrolidin-1-yl)-1-methyl-ethyl]-amide;

2-(6-Chloro-1-methyl-1H-indazol-3-yl)-5H-pyrrolo[2,3-b]pyrazine-7-carboxylic acid [(R)-2-(3-cyano-azetidin-1-yl)-1-methyl-ethyl]-amide;

2-(6-Chloro-4-fluoro-1-methyl-1H-indazol-3-yl)-5H-pyrrolo[2,3-b]pyrazine-7-carboxylic acid isopropylamide;

2-[6-Chloro-1-(2-dimethylamino-ethyl)-4-fluoro-1H-indazol-3-yl]-5H-pyrrolo[2,3-b]pyrazine-7-carboxylic acid isopropylamide;
2-[6-Chloro-4-fluoro-1-(2-morpholin-4-yl-ethyl)-1H-indazol-3-]-5H-pyrrolo[2,3-b]pyrazine-7-carboxylic acid isopropylamide;
2-[6-Chloro-1-(3-dimethylamino-propyl)-4-fluoro-1H-indazol-3-yl]-5H-pyrrolo[2,3-b]pyrazine-7-carboxylic acid isopropylamide;
2-[6-Chloro-1-(3-dimethylamino-propyl-4-fluoro-1H-indazol-3-yl]-5H-pyrrolo[2,3-b]pyrazine-7-carboxylic acid isopropylamide;
2-[6-Chloro-4-fluoro-1-(3-morpholin-4-yl-propyl-1H-indazol-3-yl]-5H-pyrrolo[2,3-b]pyrazine-7-carboxylic acid isopropylamide;
2-(6-Fluoro-1-methyl-1H-indazol-3-yl)-5H-pyrrolo[2,3-b]pyrazine-7-carboxylic acid ((R)-1-methyl-2-pyrazol-1-yl-ethyl)-amide;
2-(6-Chloro-1-methyl-1H-indazol-3-yl)-5H-pyrrolo[2,3-b]pyrazine-7-carboxylic acid ((R)-2-imidazol-1-yl-1-methyl-ethyl)-amide;
2-(6-Fluoro-1-methyl-1H-indazol-3-yl)-5H-pyrrolo[2,3-b]pyrazine-7-carboxylic acid ((S)-2-methoxy-propyl)-amide;
2-(6-Fluoro-1-methyl-1H-indazol-3-yl)-5H-pyrrolo[2,3-b]pyrazine-7-carboxylic acid ((R)-2-cyano-2-methyl-ethyl)-amide;
2-(6-Fluoro-1-methyl-1H-indazol-3-yl)-5H-pyrrolo[2,3-b]pyrazine-7-carboxylic acid ((R)-2-carbamoyl-propyl)-amide;
2-(6-Chloro-1-methyl-1H-indazol-3-yl)-5H-pyrrolo[2,3-b]pyrazine-7-carboxylic acid (S)-tetrahydro-pyran-3-ylamide;
2-(6-Chloro-1-methyl-1H-indazol-3-yl)-5H-pyrrolo[2,3-b]pyrazine-7-carboxylic acid (R)-tetrahydro-pyran-3-ylamide;
2-(6-Chloro-1-methyl-1H-indazol-3-yl)-5H-pyrrolo[2,3-b]pyrazine-7-carboxylic acid ((S)-1-cyclopropyl-ethyl)-amide;
2-(6-Chloro-4-fluoro-1-methyl-1H-indazol-3-yl)-5H-pyrrolo[2,3-b]pyrazine-7-carboxylic acid ((S)-1-cyclopropyl-ethyl)-amide;
2-(6-Chloro-1-methyl-1H-indazol-3-yl)-5H-pyrrolo[2,3-b]pyrazine-7-carboxylic acid ((S)-2-cyano-1-methyl-ethyl)-amide;
2-(6-Chloro-1-methyl-1H-indazol-3-yl)-5H-pyrrolo[2,3-b]pyrazine-7-carboxylic acid (2-amino-ethyl)-amide;
2-(6-Chloro-1-methyl-1H-indazol-3-yl)-5H-pyrrolo[2,3-b]pyrazine-7-carboxylic acid (trans-4-hydroxy-cyclohexyl)-amide;
2-(6-Chloro-1-methyl-1H-indazol-3-yl)-5H-pyrrolo[2,3-b]pyrazine-7-carboxylic acid (cis-4-amino-cyclohexyl)-amide;
2-(6-Chloro-1-methyl-1H-indazol-3-yl)-5H-pyrrolo[2,3-b]pyrazine-7-carboxylic acid (trans-4-amino-cyclohexyl)-amide;
2-(6-Chloro-1-methyl-1H-indazol-3-yl)-5H-pyrrolo[2,3-b]pyrazine-7-carboxylic acid (3-oxo-cyclohexyl)-amide;
2-(6-Chloro-1-methyl-1H-indazol-3-yl)-5H-pyrrolo[2,3-b]pyrazine-7-carboxylic acid (trans-3-hydroxy-cyclohexyl)-amide;
2-(6-Chloro-1-methyl-1H-indazol-3-yl)-5H-pyrrolo[2,3-b]pyrazine-7-carboxylic acid (cis-3-hydroxy-cyclohexyl)-amide;
2-(6-Chloro-1-methyl-1H-indazol-3-yl)-5H-pyrrolo[2,3-b]pyrazine-7-carboxylic acid (1-methyl-2-phenyl-ethyl)-amide;
2-(6-Chloro-1-methyl-1H-indazol-3-yl)-5H-pyrrolo[2,3-b]pyrazine-7-carboxylic acid ((1R,3S)-3-hydroxy-cyclopentyl)-amide;
2-(6-Chloro-1-methyl-1H-indazol-3-yl)-5H-pyrrolo[2,3-b]pyrazine-7-carboxylic acid (2-methoxy-1-methyl-ethyl)-amide;
2-(6-Chloro-1-methyl-1H-indazol-3-yl)-5H-pyrrolo[2,3-b]pyrazine-7-carboxylic acid (2-methyl-cyclohexyl)-amide;
2-(6-Chloro-1-methyl-1H-indazol-3-yl)-5H-pyrrolo[2,3-b]pyrazine-7-carboxylic acid [1-(tetrahydro-furan-2-yl)-ethyl]-amide;
2-(6-Chloro-1-methyl-1H-indazol-3-yl)-5H-pyrrolo[2,3-b]pyrazine-7-carboxylic acid (trans-3-carbamoyl-cyclohexyl)-amide;
2-(6-Chloro-1-methyl-1H-indazol-3-yl)-5H-pyrrolo[2,3-b]pyrazine-7-carboxylic acid (trans-3-cyano-cyclohexyl)-amide;
2-(6-Chloro-1-methyl-1H-indazol-3-yl)-5H-pyrrolo[2,3-b]pyrazine-7-carboxylic acid (R)-indan-1-ylamide;
2-(6-Chloro-1-methyl-1H-indazol-3-yl)-5H-pyrrolo[2,3-b]pyrazine-7-carboxylic acid (cis-4-hydroxy-cyclohexyl)-amide;
2-(6-Chloro-1-methyl-1H-indazol-3-yl)-5H-pyrrolo[2,3-b]pyrazine-7-carboxylic acid ((R)-2-methoxy-1-methyl-ethyl)-amide;
2-(6-Chloro-1-methyl-1H-indazol-3-yl)-5H-pyrrolo[2,3-b]pyrazine-7-carboxylic acid (2,2,2-trifluoro-1-methyl-ethyl)-amide;
2-(6-Chloro-1-methyl-1H-indazol-3-yl)-5H-pyrrolo[2,3-b]pyrazine-7-carboxylic acid ((R)-1-hydroxymethyl-propyl)-amide;
2-(6-Chloro-1-methyl-1H-indazol-3-yl)-5H-pyrrolo[2,3-b]pyrazine-7-carboxylic acid ((R)-1-methoxymethyl-propyl)-amide;
2-(6-Chloro-1-methyl-1H-indazol-3-yl)-5H-pyrrolo[2,3-b]pyrazine-7-carboxylic acid (5-hydroxy-1,5-dimethyl-hexyl)-amide;
2-(6-Chloro-1-methyl-1H-indazol-3-yl)-5H-pyrrolo[2,3-b]pyrazine-7-carboxylic acid ((S)-2-hydroxy-1-methyl-ethyl)-amide;
2-(6-Chloro-1-methyl-1H-indazol-3-yl)-5H-pyrrolo[2,3-b]pyrazine-7-carboxylic acid ((S)-2-methoxy-1-methyl-ethyl)-amide;
2-(6-Chloro-1-methyl-1H-indazol-3-yl)-5H-pyrrolo[2,3-b]pyrazine-7-carboxylic acid (2-methoxy-1-methoxymethyl-ethyl)-amide;
2-(6-Chloro-1-methyl-1H-indazol-3-yl)-5H-pyrrolo[2,3-b]pyrazine-7-carboxylic acid (cis-3-cyano-cyclohexyl)-amide;
2-(6-Chloro-1-methyl-1H-indazol-3-yl)-5H-pyrrolo[2,3-b]pyrazine-7-carboxylic acid [(R)-1-(2,2,2-trifluoro-ethyl)-piperidin-3-yl]-amide;
2-(6-Chloro-1-methyl-1H-indazol-3-yl)-5H-pyrrolo[2,3-b]pyrazine-7-carboxylic acid (3-amino-cyclohexyl)-amide;
2-(6-Chloro-4-fluoro-1-methyl-1H-indazol-3-yl)-5H-pyrrolo[2,3-b]pyrazine-7-carboxylic acid ((S)-2-methoxy-1-methyl-ethyl)-amide;
2-(6-Chloro-1-methyl-1H-indazol-3-yl)-5H-pyrrolo[2,3-b]pyrazine-7-carboxylic acid ((S)-2-ethoxy-1-methyl-ethyl)-amide;

2-(6-Chloro-1-methyl-1H-indazol-3-yl)-5H-pyrrolo[2,3-b]pyrazine-7-carboxylic acid (2-hydroxy-1-methyl-propyl)-amide;
2-(6-Chloro-1-methyl-1H-indazol-3-yl)-5H-pyrrolo[2,3-b]pyrazine-7-carboxylic acid ((S)-1-methoxymethyl-propy)-amide;
2-(6-Chloro-1-methyl-1H-indazol-3-yl)-5H-pyrrolo[2,3-b]pyrazine-7-carboxylic acid [(R)-2-(3-fluoro-azetidin-1-yl)-1-methoxymethyl-2-oxo-ethyl]-amide;
2-(6-Chloro-1-methyl-1H-indazol-3-yl)-5H-pyrrolo[2,3-b]pyrazine-7-carboxylic acid [(R)-2-(3-cyano-azetidin-1-yl)-1-methoxymethyl-2-oxo-ethyl]-amide;
2-(6-Fluoro-1-methyl-1H-indazol-3-yl)-5H-pyrrolo[2,3-b]pyrazine-7-carboxylic acid ((1R,2R)-2-hydroxy-1-hydroxymethyl-propyl)-amide;
2-(6-Fluoro-1-methyl-1H-indazol-3-yl)-5H-pyrrolo[2,3-b]pyrazine-7-carboxylic acid ((1R,2R)-2-hydroxy-1-methoxymethyl-propyl)-amide;
2-(6-Fluoro-1-methyl-1H-indazol-3-yl)-5H-pyrrolo[2,3-b]pyrazine-7-carboxylic acid ((S)-sec-butyl)-amide;
2-(6-Fluoro-1-methyl-1H-indazol-3-yl)-5H-pyrrolo[2,3-b]pyrazine-7-carboxylic acid ((S)-1-methoxymethyl)-3-methyl-butyl)-amide;
2-(6-Fluoro-1-methyl-1H-indazol-3-yl)-5H-pyrrolo[2,3-b]pyrazine-7-carboxylic acid ((R)-sec-butyl)-amide;
2-(6-Fluoro-1-methyl-1H-indazol-3-yl)-5H-pyrrolo[2,3-b]pyrazine-7-carboxylic acid ((S)-2-methoxy-1-methyl-ethyl)-amide;
2-(6-Fluoro-1-methyl-1H-indazol-3-yl)-5H-pyrrolo[2,3-b]pyrazine-7-carboxylic acid ((S)-1-methyl-2-trideuteromethoxy-ethyl)-amide;
2-(6-Fluoro-1-methyl-1H-indazol-3-yl)-5H-pyrrolo[2,3-b]pyrazine-7-carboxylic acid (3-hydroxy-1,3-dimethyl-butyl)-amide;
2-(6-Fluoro-1-methyl-1H-indazol-3-yl)-5H-pyrrolo[2,3-b]pyrazine-7-carboxylic acid (1-methyl-butyl)-amide;
2-(6-Fluoro-1-methyl-1H-indazol-3-yl)-5H-pyrrolo[2,3-b]pyrazine-7-carboxylic acid (3,3,3-trifluoro-1-methyl-propyl)-amide;
2-(6-Fluoro-1-methyl-1H-indazol-3-yl)-5H-pyrrolo[2,3-b]pyrazine-7-carboxylic acid (2-cyclopropyl-1-methyl-ethyl)-amide;
2-(6-Fluoro-1-methyl-1H-indazol-3-yl)-5H-pyrrolo[2,3-b]pyrazine-7-carboxylic acid (1,3-dimethyl-butyl)-amide;
2-(6-Fluoro-1-methyl-1H-indazol-3-yl)-5H-pyrrolo[2,3-b]pyrazine-7-carboxylic acid ((1R,2S)-2-hydroxy-1-methoxymethyl-propyl)-amide;
2-(6-Fluoro-1-methyl-1H-indazol-3-yl)-5H-pyrrolo[2,3-b]pyrazine-7-carboxylic acid ((1R,2S)-2-methoxy-1-methoxymethyl-propyl)-amide;
2-(6-Fluoro-1-methyl-1H-indazol-3-yl)-5H-pyrrolo[2,3-b]pyrazine-7-carboxylic acid [2-hydroxy-1-(tetrahydro-furan-2-yl)-ethyl]-amide;
2-(6-Fluoro-1-methyl-1H-indazol-3-yl)-5H-pyrrolo[2,3-b]pyrazine-7-carboxylic acid [2-methoxy-1-(tetrahydro-furan-2-yl)-ethyl]-amide;
2-(6-Fluoro-1-methyl-1H-indazol-3-yl)-5H-pyrrolo[2,3-b]pyrazine-7-carboxylic acid ((S)-3-methanesulfonyl-1-methoxymethyl-propyl)-amide;
2-(6-Fluoro-1-methyl-1H-indazol-3-yl)-5H-pyrrolo[2,3-b]pyrazine-7-carboxylic acid ((S)-2-difluoromethoxy-1-methyl-ethyl)-amide;
2-(5-Cyclopropyl-1-methyl-1H-indazol-3-yl)-5H-pyrrolo[2,3-b]pyrazine-7-carboxylic acid ((S)-2-methoxy-1-methyl-ethyl)-amide;
2-(5-Cyclopropyl-1-methyl-1H-indazol-3-yl)-5H-pyrrolo[2,3-b]pyrazine-7-carboxylic acid isopropylamide;
2-(5-Cyclopropyl-1-methyl-1H-indazol-3-yl)-5H-pyrrolo[2,3-b]pyrazine-7-carboxylic acid (2-hydroxy-1,1-dimethyl-ethyl)-amide;
2-(5-Cyclopropyl-1-methyl-1H-indazol-3-yl)-5H-pyrrolo[2,3-b]pyrazine-7-carboxylic acid tert-butylamide;
2-(6-Fluoro-1-methyl-1H-indazol-3-yl)-5H-pyrrolo[2,3-b]pyrazine-7-carboxylic acid [(1R,2R)-1-(3-fluoro-azetidine-1-carbonyl)-2-hydroxy-propyl]-amide;
2-(6-Chloro-1-methyl-1H-indazol-3-yl)-5H-pyrrolo[2,3-b]pyrazine-7-carboxylic acid [1-(1-methyl-1H-imidazol-2-yl)-ethyl]-amide;
2-(6-Chloro-1-methyl-1H-indazol-3-yl)-5H-pyrrolo[2,3-b]pyrazine-7-carboxylic acid ((R)-2-hydroxy-1-methyl-ethyl)-amide;
2-(6-Chloro-1-methyl-1H-indazol-3-yl)-5H-pyrrolo[2,3-b]pyrazine-7-carboxylic acid (trans-2-hydroxy-1-methyl-propyl)-amide;
2-(6-Fluoro-1-methyl-1H-indazol-3-yl)-5H-pyrrolo[2,3-b]pyrazine-7-carboxylic acid (1-methyl-2-phenoxy-ethyl)-amide;
2-(6-Fluoro-1-methyl-1H-indazol-3-yl)-5H-pyrrolo[2,3-b]pyrazine-7-carboxylic acid [cis-2-hydroxy-1-methyl-2-(tetrahydro-pyran-4-yl)-ethyl]-amide;
2-(6-Fluoro-1-methyl-1H-indazol-3-yl)-5H-pyrrolo[2,3-b]pyrazine-7-carboxylic acid [trans-2-hydroxy-1-methyl-2-(tetrahydro-pyran-4-Yl)-ethyl]-amide;
2-(6-Chloro-1-methyl-1H-indazol-3-yl)-5H-pyrrolo[2,3-b]pyrazine-7-carboxylic acid ((R)-3-cyano-1-methyl-propyl)-amide;
2-(6-Chloro-1-methyl-1H-indazol-3-yl)-5H-pyrrolo[2,3-b]pyrazine-7-carboxylic acid [(R)-1-((1R,2S)-2-cyano-cyclopropyl)-ethyl]-amide;
2-(6-Chloro-1-methyl-1H-indazol-3-yl)-5H-pyrrolo[2,3-b]pyrazine-7-carboxylic acid [(R)-1-((1S,2R)-2-cyano-cyclopropyl)-ethyl]-amide;
2-(6-Fluoro-1-methyl-1H-indazol-3-yl)-5H-pyrrolo[2,3-b]pyrazine-7-carboxylic acid [1-(4-bromo-phenyl)-cyclopropyl]-amide;
2-(6-Fluoro-1-methyl-1H-indazol-3-yl)-5H-pyrrolo[2,3-b]pyrazine-7-carboxylic acid [1-(3-bromo-phenyl)-cyclobutyl]-amide;
2-(6-Fluoro-1-methyl-1H-indazol-3-yl)-5H-pyrrolo[2,3-b]pyrazine-7-carboxylic acid [1-(4-bromo-phenyl)-cyclobutyl]-amide;
2-(6-Fluoro-1-methyl-1H-indazol-3-yl)-5H-pyrrolo[2,3-b]pyrazine-7-carboxylic acid [(R)-1-(4-bromo-phenyl)-2,2,2-trifluoro-ethyl]-amide;
2-(5,6-Difluoro-1-methyl-1H-indazol-3-yl)-5H-pyrrolo[2,3-b]pyrazine-7-carboxylic acid ((S)-2-methoxy-1-methyl-ethyl)-amide;
2-(6-Fluoro-1-methyl-1H-indazol-3-yl)-5H-pyrrolo[2,3-b]pyrazine-7-carboxylic acid ((R)-1-benzyl-pyrrolidin-3-yl)-amide;
2-(6-Fluoro-1-methyl-1H-indazol-3-yl)-5H-pyrrolo[2,3-b]pyrazine-7-carboxylic acid ((R)-1-cyanomethyl-pyrrolidin-3-yl)-amide;
2-(6-Fluoro-1-methyl-1H-indazol-3-yl)-5H-pyrrolo[2,3-b]pyrazine-7-carboxylic acid [(R)-1-(3-bromo-phenyl)-ethyl]-amide;
2-(6-Fluoro-1-methyl-1H-indazol-3-yl)-5H-pyrrolo[2,3-b]pyrazine-7-carboxylic acid [(R)-1-(4-bromo-phenyl)-ethyl]-amide;
2-(6-Fluoro-1-methyl-1H-indazol-3-yl)-5H-pyrrolo[2,3-b]pyrazine-7-carboxylic acid [(R)-1-(3-cyano-phenyl)-ethyl]-amide;

2-(6-Fluoro-1-methyl-1H-indazol-3-yl)-5H-pyrrolo[2,3-b]pyrazine-7-carboxylic acid [(R)-1-(4-cyano-phenyl)-ethyl]-amide;

2-(6-Fluoro-1-methyl-1H-indazol-3-yl)-5H-pyrrolo[2,3-b]pyrazine-7-carboxylic acid ((S)-2-cyanomethoxy-1-methyl-ethyl)-amide;

2-Imidazo[1,2-a]pyridin-3-yl-5H-pyrrolo[2,3-b]pyrazine-7-carboxylic acid [(R)-2-(3-cyano-azetidin-1-yl)-1-methyl-2-oxo-ethyl]-amide;

2-(7-Chloro-imidazo[1,2-a]pyridin-3-yl)-5H-pyrrolo[2,3-b]pyrazine-7-carboxylic acid [(R)-2-(3-cyano-azetidin-1-yl)-1-methyl-2-oxo-ethyl]-amide;

2-(7-Cyano-imidazo[1,2-a]pyridin-3-yl)-5H-pyrrolo[2,3-b]pyrazine-7-carboxylic acid ((S)-2-methoxy-1-methyl-ethyl)-amide;

2-(5-Chloro-benzoimidazol-1-yl)-5H-pyrrolo[2,3-b]pyrazine-7-carboxylic acid ((S)-2-methoxy-1-methyl-ethyl)-amide;

2-(6-Chloro-benzoimidazol-1-yl)-5H-pyrrolo[2,3-b]pyrazine-7-carboxylic acid ((S)-2-methoxy-1-methyl-ethyl)-amide;

2-(5-Chloro-benzoimidazol-1-yl)-5H-pyrrolo[2,3-b]pyrazine-7-carboxylic acid [(R)-2-(3-cyano-azetidin-1-yl)-1-methyl-2-oxo-ethyl]-amide;

(6-Chloro-3-{7-[(R)-2-(3-cyano-azetidin-1-yl)-methyl-2-oxo-ethylcarbamoyl]5H-pyrrolo[2,3-b]pyrazin-2-yl}-indazol-1-yl)-acetic acid;

2-(6-Chloro-1-dimethylcarbamoylmethyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide;

2-[6-Chloro-1-(2-morpholin-4-yl-2-oxo-ethyl-1H-indazol-3-yl]5H-pyrrolo[2,3-b]pyrazine-7-carboxylic acid [(R)-2-(3-cyano-azetidin-1-yl)-1-methyl-2-oxo-ethyl]-amide;

2-[6-Chloro-1-(2-dimethylamino-ethyl)-1H-indazol-3-yl]-5H-pyrrolo[2,3-b]pyrazine-7-carboxylic acid [(R)-2-(3-cyano-azetidin-1-yl)-1-methyl-2-oxo-ethyl]-amide;

2-[6-Chloro-1-(2-dimethylamino-ethyl)-1H-indazol-3-yl]-5H-pyrrolo[2,3-b]pyrazine-7-carboxylic acid [(R)-2-(3-cyano-azetidin-1-yl)-1-methyl-2-oxo-ethyl]-amide;

2-[6-Chloro-1-(2-morpholin-4-yl-ethyl)-1H-indazol-3-yl]-5H-pyrrolo[2,3-b]pyrazine-7-carboxylic acid [(R)-2-(3-cyano-azetidin-1-yl)-1-methyl-2-oxo-ethyl]-amide;

2-[6-Chloro-1-(2-pyridin-2-yl-ethyl)-1H-indazol-3-yl]-5H-pyrrolo[2,3-b]pyrazine-7-carboxylic acid [(R)-2-(3-cyano-azetidin-1-yl)-1-methyl-2-oxo-ethyl]-amide;

2-(6-Chloro-1-pyridin-2-ylmethyl-1H-indazol-3-yl)-5H-pyrrolo[2,3-b]pyrazine-7-carboxylic acid [(R)-2-(3-cyano-azetidin-1-yl)-1-methyl-2-oxo-ethyl]-amide;

2-[6-Chloro-1-(2-dimethylamino-ethyl)-1H-indazol-3-yl]-5H-pyrrolo[2,3-b]pyrazine-7-carboxylic acid ((S)-2-methoxy-1-methyl-ethyl)-amide;

2-(6-Chloro-1-pyridin-3-ylmethyl-1H-indazol-3-yl)-5H-pyrrolo[2,3-b]pyrazine-7-carboxylic acid ((S)-2-methoxy-1-methyl-ethyl)-amide;

2-[6-Chloro-1-(2-morpholin-4-yl-ethyl)-1H-indazol-3-yl]-5H-pyrrolo[2,3-b]pyrazine-7-carboxylic acid ((S)-2-methoxy-1-methyl-ethyl)-amide;

2-[6-Fluoro-1-(6-morpholin-4-yl-pyridin-3-ylmethyl)-1H-indazol-3-yl]-5H-pyrrolo[2,3-b]pyrazine-7-carboxylic acid ((S)-2-methoxy-1-methyl-ethyl)-amide;

2-[6-Fluoro-1-(2-morpholin-4-yl-ethyl)-1H-indazol-3-yl]-5H-pyrrolo[2,3-b]pyrazine-7-carboxylic acid ((S)-2-methoxy-1-methyl-ethyl)-amide;

2-[1-(2-Dimethylamino-ethyl)-6-fluoro-1H-indazol-3-yl]-5H-pyrrolo[2,3-b]pyrazine-7-carboxylic acid ((S)-2-methoxy-1-methyl-ethyl)-amide;

2-(6-Fluoro-1-pyridin-2-ylmethyl-1H-indazol-3-yl)-5H-pyrrolo[2,3-b]pyrazine-7-carboxylic acid ((S)-2-methoxy-1-methyl-ethyl)-amide;

2-(6-Fluoro-1-pyridin-3-ylmethyl-1H-indazol-3-yl)-5H-pyrrolo[2,3-b]pyrazine-7-carboxylic acid ((S)-2-methoxy-1-methyl-ethyl)-amide;

2-[6-Fluoro-1-(2-pyrrolidin-1-yl-ethyl)-1H-indazol-3-yl]-5H-pyrrolo[2,3-b]pyrazine-7-carboxylic acid ((S)-2-methoxy-1-methyl-ethyl)-amide;

2-{6-Fluoro-1-[2-((S)-3-fluoro-pyrrolidin-1-yl)-ethyl]-1H-indazol-3-yl}-5H-pyrrolo[2,3-b]pyrazine-7-carboxylic acid ((S)-2-methoxy-1-methyl-ethyl)-amide;

2-[6-Fluoro-1-(2-pyrazol-1-yl-ethyl)-1H-indazol-3-yl]-5H-pyrrolo[2,3-b]pyrazine-7-carboxylic acid ((S)-2-methoxy-1-methyl-ethyl)-amide;

2-[6-Chloro-1-(2-morpholin-4-yl-ethyl)-1H-indazol-3-yl]-5H-pyrrolo[2,3-b]pyrazine-7-carboxylic acid (1-pyridin-3-yl-ethyl)-amide;

2-[6-Chloro-1-(2-dimethylamino-ethyl)-1H-indazol-3-yl]-5H-pyrrolo[2,3-b]pyrazine-7-carboxylic acid (1-pyridin-3-yl-ethyl)-amide;

2-(6-Chloro-1-methyl-1H-indazol-3-yl)-5H-pyrrolo[2,3-b]pyrazine-7-carboxylic acid (1-pyridin-3-yl-ethyl)-amide;

2-[6-Fluoro-1-(2-morpholin-4-yl-ethyl)-1H-indazol-3-yl]-5H-pyrrolo[2,3-b]pyrazine-7-carboxylic acid (1-pyridin-4-yl-ethyl)-amide;

2-[1-(2-Dimethylamino-ethyl)-6-fluoro-1H-indazol-3-yl]-5H-pyrrolo[2,3-b]pyrazine-7-carboxylic acid (1-pyridin-4-yl-ethyl)-amide;

2-[6-Fluoro-1-(2-pyrrolidin-1-yl-ethyl)-1H-indazol-3-yl]-5H-pyrrolo[2,3-b]pyrazine-7-carboxylic acid (1-methyl-2-pyridin-2-yl-ethyl)-amide;

2-[6-Fluoro-1-(2-morpholin-4-yl-2-oxo-ethyl)-1H-indazol-3-yl]-5H-pyrrolo[2,3-b]pyrazine-7-carboxylic acid tert-butylamide;

2-(6-Fluoro-1-methyl-1H-indazol-3-yl)-5H-pyrrolo[2,3-b]pyrazine-7-carboxylic acid ((R)-1-oxetan-3-yl-ethyl)-amide;

2-(6-Fluoro-1-methyl-1H-indazol-3-yl)-5H-pyrrolo[2,3-b]pyrazine-7-carboxylic acid [(S)-1-(3-trifluoromethoxy-phenyl)-ethyl]-amide;

2-(6-Fluoro-1-methyl-1H-indazol-3-yl)-5H-pyrrolo[2,3-b]pyrazine-7-carboxylic acid [(R)-1-(3-trifluoromethoxy-phenyl)-ethyl]-amide;

2-(6-Fluoro-1-methyl-1H-indazol-3-yl)-5H-pyrrolo[2,3-b]pyrazine-7-carboxylic acid [1-(1-hydroxy-1-methyl-ethyl)-cyclobutyl]-amide;

2-(6-Fluoro-1-methyl-1H-indazol-3-yl)-5H-pyrrolo[2,3-b]pyrazine-7-carboxylic acid (1-hydroxymethyl-cyclobutyl)-amide;

2-(6-Fluoro-1-piperidin-4-yl-1H-indazol-3-yl)-5H-pyrrolo[2,3-b]pyrazine-7-carboxylic acid tert-butylamide;

2-(6-Fluoro-1-pyrrolidin-3-yl-1H-indazol-3-yl)-5H-pyrrolo[2,3-b]pyrazine-7-carboxylic acid tert-butylamide;

2-(1-Methyl-1H-pyrazolo[4,3-b]pyridin-3-yl)-5H-pyrrolo[2,3-b]pyrazine-7-carboxylic acid tert-butylamide;

2-(5-Cyano-1-methyl-1H-indazol-3-yl)-5H-pyrrolo[2,3-b]pyrazine-7-carboxylic acid tert-butylamide;

2-(5-Difluoromethoxy-1-piperidin-4-yl-1H-indazol-3-yl)-5H-pyrrolo[2,3-b]pyrazine-7-carboxylic acid tert-butylamide;

4-[3-(7-tert-Butylcarbamoyl-5H-pyrrolo[2,3-b]pyrazin-2-yl)-5-difluoromethoxy-indazol-1-yl]-butyric acid;

2-[5-Difluoromethoxy-1-(1-methyl-piperidin-4-yl)-1H-indazol-3-yl]-5H-pyrrolo[2,3-b]pyrazine-7-carboxylic acid tert-butylamide;

2-(5-Difluoromethoxy-1-pyridin-3-ylmethyl-1H-indazol-3-yl)-5H-pyrrolo[2,3-b]pyrazine-7-carboxylic acid tert-butylamide;

2-(5-Difluoromethoxy-1-pyrrolidin-3-ylmethyl-1H-indazol-3-yl)-5H-pyrrolo[2,3-b]pyrazine-7-carboxylic acid tert-butylamide;

2-(7-Hydroxymethyl-1H-indazol-3-yl)-5H-pyrrolo[2,3-b]pyrazine-7-carboxylic acid tert-butylamide;

2-(6-Fluoro-1-piperidin-4-yl-1H-indazol-3-yl)-5H-pyrrolo[2,3-b]pyrazine-7-carboxylic acid (3-amino-cyclopentyl)-amide;

2-[7-(1-Hydroxy-1-methyl-ethyl)-1H-indazol-3-yl]-5H-pyrrolo[2,3-b]pyrazine-7-carboxylic acid tert-butylamide;

2-[5-(1-Hydroxy-ethyl)-1-methyl-1H-indazol-3-yl]-5H-pyrrolo[2,3-b]pyrazine-7-carboxylic acid isopropylamide;

2-(6-Methanesulfonyl-1-methyl-1H-indazol-3-yl)-5H-pyrrolo[2,3-b]pyrazine-7-carboxylic acid tert-butylamide;

2-(6-Fluoro-1-methyl-1H-indazol-3-yl)-5H-pyrrolo[2,3-b]pyrazine-7-carboxylic acid (cis-3-amino-cyclobutyl)-amide;

2-(1-Methyl-1,4,5,6,7,8-hexahydro-cycloheptapyrazol-3-yl)-5H-pyrrolo[2,3-b]pyrazine-7-carboxylic acid tert-butylamide;

2-(5-Hydroxymethyl-1-methyl-1H-indazol-3-yl)-5H-pyrrolo[2,3-b]pyrazine-7-carboxylic acid tert-butylamide;

2-[5-Difluoromethoxy-1-(1-methyl-1H-pyrazol-4-ylmethyl)-1H-indazol-3-yl]-5H-pyrrolo[2,3-b]pyrazine-7-carboxylic acid tert-butylamide;

2-(5,6,7,8-Tetrahydro-imidazo[1,5-a]pyridin-1-yl)-5H-pyrrolo[2,3-b]pyrazine-7-carboxylic acid tert-butylamide;

2-(6-Chloro-1-methyl-1H-indazol-3-yl)-5H-pyrrolo[2,3-b]pyrazine-7-carboxylic acid (trans-3-amino-cyclohexyl)-amide;

2-(6-Chloro-1-methyl-1H-indazol-3-yl)-5H-pyrrolo[2,3-b]pyrazine-7-carboxylic acid (cis-3-amino-cyclohexyl)-amide;

2-(1,5,5-Trimethyl-4,5,6,7-tetrahydro-1H-indazol-3-yl)-5H-pyrrolo[2,3-b]pyrazine-7-carboxylic acid isopropylamide;

2-(1,6,6-Trimethyl-4,5,6,7-tetrahydro-1H-indazol-3-yl)-5H-pyrrolo[2,3-b]pyrazine-7-carboxylic acid isopropylamide;

2-[5-(3-Chloro-phenoxy)-1-methyl-1H-indazol-3-yl]-5H-pyrrolo[2,3-b]pyrazine-7-carboxylic acid isopropylamide;

2-(1-Methyl-5-trifluoromethoxy-1H-indazol-3-yl)-5H-pyrrolo[2,3-b]pyrazine-7-carboxylic acid isopropylamide;

2-(1-Methyl 1,4,5,6-tetrahydro-cyclopentapyrazol-3-yl)-5H-pyrrolo[2,3-b]pyrazine-7-carboxylic acid isopropylamide;

2-(5-Difluoromethoxy-1-methyl-1H-indazol-3-yl)-5H-pyrrolo[2,3-b]pyrazine-7-carboxylic acid isopropylamide;

2-(5-Difluoromethoxy-1-methyl-1H-indazol-3-yl)-5H-pyrrolo[2,3-b]pyrazine-7-carboxylic acid tert-butylamide;

2-(5-Difluoromethoxy-1-methyl-1H-indazol-3-yl)-5H-pyrrolo[2,3-b]pyrazine-7-carboxylic acid (2-hydroxy-1,1-dimethyl-ethyl)-amide;

2-(5-Difluoromethoxy-1-methyl-1H-indazol-3-yl)-5H-pyrrolo[2,3-b]pyrazine-7-carboxylic acid (4-hydroxymethyl-tetrahydro-pyran-4-yl)-amide;

2-(5-Methoxy-1-methyl-1H-indazol-3-yl)-5H-pyrrolo[2,3-b]pyrazine-7-carboxylic acid tert-butylamide;

2-(5-Methoxy-1-methyl-1H-indazol-3-yl)-5H-pyrrolo[2,3-b]pyrazine-7-carboxylic acid (2-hydroxy-1,1-dimethyl-ethyl)-amide;

2-(5-Difluoromethoxy-1H-indazol-3-yl)-5H-pyrrolo[2,3-b]pyrazine-7-carboxylic acid tert-butylamide;

2-(5-Methoxy-1-methyl-1H-indazol-3-yl)-5H-pyrrolo[2,3-b]pyrazine-7-carboxylic acid ((3R,4R)-3-amino-tetrahydro-pyran-4-yl)-amide;

2-(5-Methoxy-1-methyl-1H-indazol-3-yl)-5H-pyrrolo[2,3-b]pyrazine-7-carboxylic acid ((1R,2S)-2-amino-cyclohexyl)-amide;

2-[5-Difluoromethoxy-1-(3-dimethylamino-propyl-1H-indazol-3-yl]-5H-pyrrolo[2,3-b]pyrazine-7-carboxylic acid tert-butylamide;

2-(1-Methyl-2-oxy-4,5,6,7-tetrahydro-1H-indazol-3-yl)-5H-pyrrolo[2,3-b]pyrazine-7-carboxylic acid isopropylamide;

2-(1-Methyl-2-oxy-4,5,6,7-tetrahydro-1H-indazol-3-yl)-5H-pyrrolo[2,3-b]pyrazine-7-carboxylic acid tert-butylamide;

2-(1-Methyl-4,5,6,7-tetrahydro-1H-indazol-3-yl)-5H-pyrrolo[2,3-b]pyrazine-7-carboxylic acid tert-butylamide;

2-{1-[3-(3,3-Difluoro-azetidin-1-yl)-propyl]-5-difluoromethoxy-1H-indazol-3-yl}-5H-pyrrolo[2,3-b]pyrazine-7-carboxylic acid tert-butylamide;

2-[5-Difluoromethoxy-1-(2-[1,3]dioxan-2-yl-ethyl)-1H-indazol-3-yl]-5H-pyrrolo[2,3-b]pyrazine-7-carboxylic acid tert-butylamide;

2-[5-Difluoromethoxy-1-(3-hydroxy-propyl)-1H-indazol-3-yl]-5H-pyrrolo[2-b]pyrazine-7-carboxylic acid tert-butylamide;

2-[5-Difluoromethoxy-1-(3-morpholin-4-yl-propyl)-1H-indazol-3-yl]-5H-pyrrolo[2,3-b]pyrazine-7-carboxylic acid tert-butylamide;

2-{5-Difluoromethoxy-1-[3-(3-hydroxy-azetidin-1-yl)-propyl]-1H-indazol-3-yl}-5H-pyrrolo[2,3-b]pyrazine-7-carboxylic acid tert-butylamide;

2-{1-[3-(3-Cyano-azetidin-1-yl)-propyl]-5-difluoromethoxy-1H-indazol-3-yl}-5H-pyrrolo[2,3-b]pyrazine-7-carboxylic acid tert-butylamide;

2-[1-(2-Azetidin-3-yl-ethyl)-6-fluoro-1H-indazol-3-yl]-5H-pyrrolo[2,3-b]pyrazine-7-carboxylic acid tert-butylamide;

2-(2-Methyl-1H-indol-7-yl)-5H-pyrrolo[2,3-b]pyrazine-7-carboxylic acid tert-butylamide;

2-(1H-Indol-7-yl)-5H-pyrrolo[2,3-b]pyrazine-7-carboxylic acid tert-butylamide;

2-(6-Chloro-1-methyl-1H-indazol-3-yl)-5H-pyrrolo[2,3-b]pyrazine-7-carboxylic acid tert-butylamide;

2-(6-Chloro-1H-indazol-3-yl)-5H-pyrrolo[2,3-b]pyrazine-7-carboxylic acid isopropylamide;

2-(6-Chloro-1-ethyl-1H-indazol-3-yl)-5H-pyrrolo[2,3-b]pyrazine-7-carboxylic acid isopropylamide;

2-(1-Benzyl-6-chloro-1H-indazol-3-yl)-5H-pyrrolo[2,3-b]pyrazine-7-carboxylic acid isopropylamide;

2-(6-Chloro-1-cyclopropylmethyl-1H-indazol-3-yl)-5H-pyrrolo[2,3-b]pyrazine-7-carboxylic acid isopropylamide;

2-(6-Chloro-1-isoxazol-ylmethyl-1H-indazol-3-yl)-5H-pyrrolo[2,3-b]pyrazine-7-carboxylic acid isopropylamide;

2-[6-Chloro-1-(1-methyl-1H-imidazol-2-ylmethyl)-1H-indazol-3-yl]-5H-pyrrolo[2,3-b]pyrazine-7-carboxylic acid isopropylamide;

2-[6-Chloro-1-(5-methyl-isoxazol-3-ylmethyl)-1H-indazol-3-yl-]-5H-pyrrolo[2,3-b]pyrazine-7-carboxylic acid isopropylamide;

2-[1-(2-Dimethylamino-ethyl)-6-fluoro-1H-indazol-3-yl]-5H-pyrrolo[2,3-b]pyrazine-7-carboxylic acid tert-butylamide;

2-[6-Fluoro-1-(2-morpholin-4-yl-2-oxo-ethyl)-1H-indazol-3-yl]-5H-pyrrolo[2,3-b]pyrazine-7-carboxylic acid amide;

2-(6-Fluoro-1-methyl-1H-indazol-3-yl)-5H-pyrrolo[2,3-b]pyrazine-7-carboxylic acid-d9-tert-butylamide;

2-(6-Chloro-1-methyl-1H-indazol-3-yl)-5H-pyrrolo[2,3-b]pyrazine-7-carboxylic acid (2-hydroxy-1-hydroxymethyl-ethyl)-amide;

2-(6-Chloro-1-methyl-1H-indazol-3-yl)-5H-pyrrolo[2,3-b]pyrazine-7-carboxylic acid cyclopropylmethyl-amide;

2-(5-Chloro-indazol-1-yl)-5H-pyrrolo[2,3-b]pyrazine-7-carboxylic acid (2-hydroxy-1,1-dimethyl-ethyl)-amide;

2-(5-Chloro-3-methyl-indazol-1-yl)-5H-pyrrolo[2,3-b]pyrazine-7-carboxylic acid (2-hydroxy-1,1-dimethyl-ethyl)-amide;

2-(5-Fluoro-indazol-3-yl)-5H-pyrrolo[2,3-b]pyrazine-7-carboxylic acid (2-hydroxy-1,1-dimethyl-ethyl)-amide;

2-Indazol-1-yl-5H-pyrrolo[2,3-b]pyrazine-7-carboxylic acid (2-hydroxy-1,1-dimethyl-ethyl)-amide;

2-(6-Chloro-indazol-1-yl)-5H-pyrrolo[2,3-b]pyrazine-7-carboxylic acid (2-hydroxy-1,1-dimethyl-ethyl)-amide;

2-(5-Methoxy-indazol-1-yl)-5H-pyrrolo[2,3-b]pyrazine-7-carboxylic acid tert-butylamide;

2-(5-Chloro-indazol-1-yl)-5H-pyrrolo[2,3-b]pyrazine-7-carboxylic acid tert-butylamide;

2-(5-Difluoromethoxy-indazol-1-yl)-5H-pyrrolo[2,3-b]pyrazine-7-carboxylic acid tert-butylamide;

2-(5-Fluoro-indazol-1-yl)-5H-pyrrolo[2,3-b]pyrazine-7-carboxylic acid tert-butylamide;

2-(5,6-Difluoro-indazol-1-yl)-5H-pyrrolo[2,3-b]pyrazine-7-carboxylic acid tert-butylamide;

2-(1H-pyrrolo[2,3-c]pyridin-7-yl)-5H-pyrrolo[2,3-b]pyrazine-7-carboxylic acid tert-butylamide;

2-(6-Chloro-indazol-1-yl)-5H-pyrrolo[2,3-b]pyrazine-7-carboxylic acid tert-butylamide;

2-(6-Trifluoromethyl-indazol-1-yl)-5H-pyrrolo[2,3-b]pyrazine-7-carboxylic acid tert-butylamide;

2-(6-Methyl-indazol-1-yl)-5H-pyrrolo[2,3-b]pyrazine-7-carboxylic acid tert-butylamide;

2-(6-Fluoro-indazol-1-yl)-5H-pyrrolo[2,3-b]pyrazine-7-carboxylic acid tert-butylamide;

2-(5-Methyl-indazol-1-yl)-5H-pyrrolo[2,3-b]pyrazine-7-carboxylic acid tert-butylamide;

2-(3-Trifluoromethyl-5,6-dihydro-4H-cyclopentapyrazol-1-yl)-5H-pyrrolo[2,3-b]pyrazine-7-carboxylic acid tert-butylamide;

2-(3-Chloro-indazol-1-yl)-5H-pyrrolo[2,3-b]pyrazine-7-carboxylic acid tert-butylamide;

2-(5-Methyl-pyrazolo[3,4-b]pyridin-1-yl)-5H-pyrrolo[2,3-b]pyrazine-7-carboxylic acid tert-butylamide;

2-(5-Trifluoromethyl-indazol-1-yl)-5H-pyrrolo[2,3-b]pyrazine-7-carboxylic acid tert-butylamide;

2-(6-Methoxy-indazol-1-yl)-5H-pyrrolo[2,3-b]pyrazine-7-carboxylic acid tert-butylamide;

2-[5-Difluoromethoxy-1-(2-dimethylcarbamoyl-ethyl)-1H-indazol-3-yl]-5H-pyrrolo[2,3-b]pyrazine-7-carboxylic acid tert-butylamide;

2-[1-(4-Benzyl-morpholin-2-ylmethyl)-5-difluoromethoxy-1H-indazol-3-yl]-5H-pyrrolo[2,3-b]pyrazine-7-carboxylic acid tert-butylamide;

2-[5-Difluoromethoxy-1-(1-methyl-azetidin-3-ylmethyl)-1H-indazol-3-yl]-5H-pyrrolo[2,3-b]pyrazine-7-carboxylic acid tert-butylamide;

2-[5-Difluoromethoxy-1-(4-methyl-morpholin-2-ylmethyl)-1H-indazol-3-yl]-5H-pyrrolo[2,3-b]pyrazine-7-carboxylic acid tert-butylamide;

2-{5-Difluoromethoxy-1-[3-(3,3-difluoro-pyrrolidin-1-yl)-propyl]-1H-indazol-3-yl}-5H-pyrrolo[2,3-b]pyrazine-7-carboxylic acid tert-butylamide;

2-(3-Methoxy-indazol-1-yl)-5H-pyrrolo[2,3-b]pyrazine-7-carboxylic acid (2-hydroxy-1,1-dimethyl-ethyl)-amide;

2-[5-Difluoromethoxy-1-(3-methylamino-propyl)-1H-indazol-3-yl]-5H-pyrrolo[2,3-b]pyrazine-7-carboxylic acid tert-butylamide;

2-{1-[3-(Acetyl-methyl-amino)-propyl]-5-difluoromethoxy-1H-indazol-3-yl}-5H-pyrrolo[2,3-b]pyrazine-7-carboxylic acid tert-butylamide;

2-(3-Piperidin-4-yl-indazol-3-yl)-5H-pyrrolo[2,3-b]pyrazine-7-carboxylic acid (2-hydroxy-1,1-dimethyl-ethyl)-amide;

2-[3-(1-Methyl-piperidin-4-yl)-indazol-1-yl]-5H-pyrrolo[2,3-b]pyrazine-7-carboxylic acid (2-hydroxy-1,1-dimethyl-ethyl)-amide;

2-(1-Azetidin-3-ylmethyl-6-fluoro-1H-indazol-3-yl)-5H-pyrrolo[2,3-b]pyrazine-7-carboxylic acid tert-butylamide;

2-(1-Azetidin-3-ylmethyl-5-difluoromethoxy-1H-indazol-3-yl)-5H-pyrrolo[2,3-b]pyrazine-7-carboxylic acid tert-butylamide;

2-(1-Cyclopropylmethyl-5-difluoromethoxy-1H-indazol-3-yl)-5H-pyrrolo[2,3-b]pyrazine-7-carboxylic acid tert-butylamide;

2-(5-Difluoromethoxy-1-{2-oxo-2-[4-(2,2,2-trifluoro-ethyl)-piperazin-1-yl]-ethyl}-1H-indazol-3-yl)-5H-pyrrolo[2,3-b]pyrazine-7-carboxylic acid tert-butylamide;

2-{5-Difluoromethoxy-1-[2-(4-methyl-piperazin-1-yl)-2-oxo-ethyl]-1H-indazol-3-yl}-5H-pyrrolo[2,3-b]pyrazine-7-carboxylic acid tert-butylamide;

2-(5-Difluoromethoxy-1-methylcarbamoylmethyl-1H-indazol-3-yl)-5H-pyrrolo[2,3-b]pyrazine-7-carboxylic acid tert-butylamide;

2-(7-Ethyl-1H-indazol-3-yl)-5H-pyrrolo[2,3-b]pyrazine-7-carboxylic acid tert-butylamide;

2-(6-Chloro-imidazo[1,5-a]pyridin-1-yl)-5H-pyrrolo[2,3-b]pyrazine-7-carboxylic acid tert-butylamide;

2-(6-Fluoro-imidazo[1,5-a]pyridin-1-yl)-5H-pyrrolo[2,3-b]pyrazine-7-carboxylic acid tert-butylamide;

2-(6-Fluoro-1-methyl-1H-indazol-3-yl)-5H-pyrrolo[2,3-b]pyrazine-7-carboxylic acid [(S)-1-(5-trifluoromethyl-1H-imidazol-2-yl)-ethyl]-amide;

2-((S)-1-{[2-(6-Fluoro-1-methyl-1H-indazol-3-yl)-5H-pyrrolo[2,3-b]pyrazine-7-carbonyl]-amino}-ethyl)-3H-imidazole-4-carboxylic acid methyl ester;

(3-Ethynyl-azetidin-1-yl)-[2-(6-fluoro-1-methyl-1H-indazol-3-yl)-5H-pyrrolo-[2,3-b]pyrazin-7-yl]-methanone;

2-(6-Fluoro-1-methyl-1H-indazol-3-yl)-5H-pyrrolo[2,3-b]pyrazine-7-carboxylic acid methoxy-amide;

2-(6-Fluoro-1-methyl-1H-indazol-3-yl)-5H-pyrrolo[2,3-b]pyrazine-7-carboxylic acid tert-butylamide;

2-(6-Fluoro-1-methyl-1H-indazol-3-yl)-5H-pyrrolo[2,3-b]pyrazine-7-carboxylic acid (2-hydroxy-1,1-dimethyl-ethyl)-amide;

2-(6-Chloro-1-methyl-1H-indazol-3-yl)-5H-pyrrolo[2,3-b]pyrazine-7-carboxylic acid (2-hydroxy-1,1-dimethyl-ethyl)-amide;

2-(6-Methoxy-1-methyl-1H-indazol-3-yl)-5H-pyrrolo[2,3-b]pyrazine-7-carboxylic acid (2-hydroxy-1,1-dimethyl-ethyl)-amide;

2-(6-Methoxy-1-methyl-1H-indazol-3-yl)-5H-pyrrolo[2,3-b]pyrazine-7-carboxylic acid tert-butylamide;

2-(6-Ethyl-1-methyl-1H-indazol-3-yl)-5H-pyrrolo[2,3-b]pyrazine-7-carboxylic acid tert-butylamide;

2-(1,6-Dimethyl-1H-indazol-3-yl)-5H-pyrrolo[2,3-b]pyrazine-7-carboxylic acid (2-hydroxy-1,1-dimethyl-ethyl)-amide;

2-(7-Methyl-1H-indazol-3-yl)-5H-pyrrolo[2,3-b]pyrazine-7-carboxylic acid tert-butylamide;

2-(1-Methyl-6-trifluoromethoxy-1H-indazol-3-yl)-5H-pyrrolo[2,3-b]pyrazine-7-carboxylic acid tert-butylamide;

2-(1-Methyl-6-trifluoromethoxy-1H-indazol-3-yl)-5H-pyrrolo[2,3-b]pyrazine-7-carboxylic acid (2-hydroxy-1,1-dimethyl-ethyl)-amide;

2-(7-Methyl-1H-indazol-3-yl)-5H-pyrrolo[2,3-b]pyrazine-7-carboxylic acid (2-hydroxy-1,1-dimethyl-ethyl)-amide;

2-(1-Methyl-1H-pyrazolo[3,4-b]pyridin-3-yl)-5H-pyrrolo[2,3-b]pyrazine-7-carboxylic acid tert-butylamide;

2-(6-Fluoro-1-methyl-1H-indazol-3-yl)-5H-pyrrolo[2,3-b]pyrazine-7-carboxylic acid (1-hydroxymethyl-cyclopropyl)-amide;

2-(6-Fluoro-1-methyl-1H-indazol-3-yl)-5H-pyrrolo[2,3-b]pyrazine-7-carboxylic acid (1,1-dimethyl-propy)-amide;

2-(6-Fluoro-1-methyl-1H-indazol-3-yl)-5H-pyrrolo[2,3-b]pyrazine-7-carboxylic acid (1-methyl-cyclobutyl)-amide;

2-(6-Fluoro-1-methyl-1H-indazol-3-yl)-5H-pyrrolo[2,3-b]pyrazine-7-carboxylic acid (cyano-dimethyl-methyl)-amide;

2-(6-Fluoro-1-methyl-1H-indazol-3-yl)-5H-pyrrolo[2,3-b]pyrazine-7-carboxylic acid (1-methyl-cyclopropyl)-amide;

2-(6-Fluoro-1-methyl-1H-indazol-3-yl)-5H-pyrrolo[2,3-b]pyrazine-7-carboxylic acid (2-amino-1,1-dimethyl-ethyl)-amide;

2-(6-Fluoro-1-methyl-1H-indazol-3-yl)-5H-pyrrolo[2,3-b]pyrazine-7-carboxylic acid (1,1-dimethyl-prop-2-ynyl)-amide;

2-{[2-(6-Fluoro-1-methyl-1H-indazol-3-yl)-5H-pyrrolo[2,3-b]pyrazine-7-carbonl]-amino}-2-methylpropionic acid tert-butyl ester;

2-{[2-(6-Fluoro-1-methyl-1H-indazol-3-yl)-5H-pyrrolo[2,3-b]pyrazine-7-carbonyl]-amino}-2-methyl-propionic acid;

2-(6-Fluoro-1-methyl-1H-indazol-3-yl)-5H-pyrrolo[2,3-b]pyrazine-7-carboxylic acid (2-hydroxy-1-hydroxymethyl-1-methyl-ethyl)-amide;

2-(6-Fluoro-1-methyl-1H-indazol-3-yl)-5H-pyrrolo[2,3-b]pyrazine-7-carboxylic acid (1-methyl-cyclopentyl)-amide;

2-(6-Fluoro-1-methyl-1H-indazol-3-yl)-5H-pyrrolo[2,3-b]pyrazine-7-carboxylic acid (4-methyl-piperidin-4-yl)-amide;

2-(6-Fluoro-1-methyl-1H-indazol-3-yl)-5H-pyrrolo[2,3-b]pyrazine-7-carboxylic acid (3-methyl-oxetan-3-yl)-amide;

2-(6-Fluoro-1-methyl-1H-indazol-3-yl)-5H-pyrrolo[2,3-b]pyrazine-7-carboxylic acid (1-cyano-cyclopropyl)-amide;

2-(6-Chloro-1-methyl-1H-indazol-3-yl)-5H-pyrrolo[2,3-b]pyrazine-7-carboxylic acid (1-methyl-1-phenyl-ethyl)-amide;

2-(6-Chloro-1-methyl-1H-indazol-3-yl)-5H-pyrrolo[2,3-b]pyrazine-7-carboxylic acid ((S)-1-phenyl-ethyl)-amide;

2-(6-Chloro-1-methyl-1H-indazol-3-yl)-5H-pyrrolo[2,3-b]pyrazine-7-carboxylic acid (2,2,2-trifluoro-1,1-dimethyl-ethyl)-amide;

2-(6-Chloro-1-methyl-1H-indazol-3-yl)-5H-pyrrolo[2,3-b]pyrazine-7-carboxylic acid (1,1-dimethyl-propy)-amide;

2-(6-Fluoro-1-methyl-1H-indazol-3-yl)-5H-pyrrolo[2,3-b]pyrazine-7-carboxylic acid (1-methyl-cyclohexyl)-amide;

2-(6-Fluoro-1-methyl-1H-indazol-3-yl)-5H-pyrrolo[2,3-b]pyrazine-7-carboxylic acid (2-amino-1,1,2-trimethyl-propyl)-amide;

2-(6-Cyano-1-methyl-1H-indazol-3-yl)-5H-pyrrolo[2,3-b]pyrazine-7-carboxylic acid tert-butylamide;

2-(6-Chloro-1-methyl-1H-indazol-3-yl)-5H-pyrrolo[2,3-b]pyrazine-7-carboxylic acid (1-methyl-cyclopropyl)-amide;

2-(6-Chloro-1-methyl-1H-indazol-3-yl)-5H-pyrrolo[2,3-b]pyrazine-7-carboxylic acid phenylamide;

2-(6-Chloro-1-methyl-1H-indazol-3-yl)-5H-pyrrolo[2,3-b]pyrazine-7-carboxylic acid (2-amino-1,1-dimethyl-ethyl)-amide;

2-(6-Cyano-1-methyl-1H-indazol-3-yl)-5H-pyrrolo[2,3-b]pyrazine-7-carboxylic acid (2-hydroxy-1,1-dimethyl-ethyl)-amide;

2-(1H-Indazol-4-yl)-5H-pyrrolo[2,3-b]pyrazine-7-carboxylic acid tert-butylamide;

2-(6-Fluoro-1-methyl-1H-indazol-3-yl)-5H-pyrrolo[2,3-b]pyrazine-7-carboxylic acid (3-hydroxy-1,1-dimethyl-propyl)-amide;

2-(6-Chloro-1-methyl-1H-indazol-3-yl)-5H-pyrrolo[2,3-b]pyrazine-7-carboxylic acid (1-cyclopropyl-1-methyl-ethyl)-amide;

2-(5-Difluoromethoxy-1-methyl-1H-indazol-3-yl)-5H-pyrrolo[2,3-b]pyrazine-7-carboxylic acid (cis-4-amino-cyclohexyl)-amide;

2-(6-Chloro-1-methyl-1H-indazol-3-yl)-5H-pyrrolo[2,3-b]pyrazine-7-carboxylic acid (3-amino-cyclohexyl)-amide;

2-(6-Chloro-1-methyl-1H-indazol-3-yl)-5H-pyrrolo[2,3-b]pyrazine-7-carboxylic acid (3-cyano-phenyl)-amide;

2-(6-Chloro-1-methyl-1H-indazol-3-yl)-5H-pyrrolo[2,3-b]pyrazine-7-carboxylic acid pyridin-3-ylamide;

2-(6-Fluoro-1-methyl-1H-indazol-3-yl)-5H-pyrrolo[2,3-b]pyrazine-7-carboxylic acid (3-methyl-pyrrolidin-3-yl)-amide;

2-(6-Chloro-1-methyl-1H-indazol-3-yl)-5H-pyrrolo[2,3-b]pyrazine-7-carboxylic acid (cyano-dimethyl-methyl)-amide;

2-(6-Fluoro-1-methyl-1H-indazol-3-yl)-5H-pyrrolo[2,3-b]pyrazine-7-carboxylic acid (4-amino-1,1-dimethyl-butyl)-amide;

2-(6-Fluoro-1-methyl-1H-indazol-3-yl)-5H-pyrrolo[2,3-b]pyrazine-7-carboxylic acid (3-methyl-azetidin-3-yl)-amide;

2-(1-Methyl-1H-indazol-3-yl)-5H-pyrrolo[2,3-b]pyrazine-7-carboxylic acid tert-butylamide;

2-(6-Fluoro-1H-indazol-3-yl)-5H-pyrrolo[2,3-b]pyrazine-7-carboxylic acid tert-butylamide;

2-(1-Methyl-5-trifluoromethyl-1H-indazol-3-yl)-5H-pyrrolo[2,3-b]pyrazine-7-carboxylic acid tert-butylamide;

2-(6-Chloro-1-methyl-1H-indazol-3-yl)-5H-pyrrolo[2,3-b]pyrazine-7-carboxylic acid (2-hydroxy-1,1-dimethyl-propyl)-amide;

2-(6-Chloro-1H-indazol-3-yl)-5H-pyrrolo[2,3-b]pyrazine-7-carboxylic acid (2-hydroxy-1,1-dimethyl-ethyl)-amide;

2-(6-Fluoro-1-methyl-1H-indazol-3-yl)-5H-pyrrolo[2,3-b]pyrazine-7-carboxylic acid (3-amino-1,1-dimethyl-propyl)-amide;

2-(6-Fluoro-1-methyl-1H-indazol-3-yl)-5H-pyrrolo[2,3-b]pyrazine-7-carboxylic acid (trans-4-amino-1-methyl-cyclohexyl)-amide;

2-(6-Fluoro-1-methyl-1H-indazol-3-yl)-5H-pyrrolo[2,3-b]pyrazine-7-carboxylic acid (cis-4-amino-1-methyl-cyclohexyl)-amide;

2-[6-Fluoro-1-(2,2,2-trifluoro-ethyl)-1H-indazol-3-yl]-5H-pyrrolo[2,3-b]pyrazine-7-carboxylic acid tert-butylamide;

2-(6-Chloro-1H-indazol-3-yl)-5H-pyrrolo[2,3-b]pyrazine-7-carboxylic acid ((S)-2-hydroxy-1-methyl-ethyl)-amide;

2-(1-Methyl-6-trifluoromethyl-1H-indazol-3-yl)-5H-pyrrolo[2,3-b]pyrazine-7-carboxylic acid tert-butylamide;

2-(1H-Indazol-7-yl)-5H-pyrrolo[2,3-b]pyrazine-7-carboxylic acid tert-butylamide;

2-(6-Fluoro-1-methyl-1H-indazol-3-yl)-5H-pyrrolo[2,3-b]pyrazine-7-carboxylic acid (trans-3-amino-1-methyl-cyclobutyl)-amide;

2-(6-Fluoro-1-methyl-1H-indazol-3-yl)-5H-pyrrolo[2,3-b]pyrazine-7-carboxylic acid (cis-3-amino-1-methyl-cyclobutyl)-amide;

2-(1,6-Dimethyl-1H-indazol-3-yl)-5H-pyrrolo[2,3-b]pyrazine-7-carboxylic acid (1-cyano-cyclopropyl)-amide;

2-(1,6-Dimethyl-1H-indazol-3-yl)-5H-pyrrolo[2,3-b]pyrazine-7-carboxylic acid (3-methyl-pyrrolidin-3-yl)-amide;

2-[1-(2-Dimethylamino-ethyl)-6-methyl-1H-indazol-3-yl]5H-pyrrolo[2,3-b]pyrazine-7-carboxylic acid (2-hydroxy-1,1-dimethyl-ethyl)-amide;

2-[1-(3-Dimethylamino-propyl)-6-methy-1H-indazol-3-yl]-5H-pyrrolo[2,3-b]pyrazine-7-carboxylic acid tert-butylamide;

2-(1,6-Dimethyl-1H-indazol-3-yl)-5H-pyrrolo[2,3-b]pyrazine-7-carboxylic acid (1-cyclopropyl-1-methyl-ethyl)-amide;

2-(1,6-Dimethyl-1H-indazol-3-yl)-5H-pyrrolo[2,3-b]pyrazine-7-carboxylic acid (1-hydroxymethyl-cyclopropyl)-amide;

2-(1,6-Dimethyl-1H-indazol-3-yl)-5H-pyrrolo[2,3-b]pyrazine-7-carboxylic acid (2-dimethylamino-1,1-dimethyl-ethyl)-amide;

2-(6-Methyl-1H-indazol-3-yl)-5H-pyrrolo[2,3-b]pyrazine-7-carboxylic acid (3-methyl-pyrrolidin-3-yl)-amide;

2-(6-Methyl-1H-indazol-3-yl)-5H-pyrrolo[2,3-b]pyrazine-7-carboxylic acid (1-hydroxymethyl-cyclopropyl)-amide;

2-(6-Methyl-1H-indazol-3-yl)-5H-pyrrolo[2,3-b]pyrazine-7-carboxylic acid (1-cyclopropyl-1-methyl-ethyl)-amide;

2-(6-Methyl-1H-indazol-3-yl)-5H-pyrrolo[2,3-b]pyrazine-7-carboxylic acid (2-hydroxy-1,1-dimethyl-ethyl)-amide;

2-(6-Methyl-1H-indazol-3-yl)-5H-pyrrolo[2,3-b]pyrazine-7-carboxylic acid (2-amino-1,1-dimethyl-ethyl)-amide;

2-(6-Methyl-1H-indazol-3-yl)-5H-pyrrolo[2,3-b]pyrazine-7-carboxylic acid (2-dimethylamino-1,1-dimethyl-ethyl)-amide;

2-(6-Methyl-1H-indazol-3-yl)-5H-pyrrolo[2,3-b]pyrazine-7-carboxylic acid (1-cyano-cyclopropyl)-amide;

2-[6-Methyl-1-(3-morpholin-4-yl-propyl)-1H-indazol-3-yl]-5H-pyrrolo[2,3-b]pyrazine-7-carboxylic acid (2-hydroxy-1,1-dimethyl-ethyl)-amide;

2-[6-Methyl-1-(2-morpholin-4-yl-2-oxo-ethyl)-1H-indazol-3-yl]-5H-pyrrolo[2,3-b]pyrazine-7-carboxylic acid (2-hydroxy-1,1-dimethyl-ethyl)-amide;

2-[1-(3-Dimethylamino-propyl)-6-methyl-1H-indazol-3-yl]-5H-pyrrolo[2,3-b]pyrazine-7-carboxylic acid (2-hydroxy-1,1-dimethyl-ethyl)-amide;

2-[5-Difluoromethoxy-1-(3-dimethylamino-propyl)-1H-indazol-3-yl]-5H-pyrrolo[2,3-b]pyrazine-7-carboxylic acid (2-hydroxy-1,1-dimethyl-ethyl)-amide;

(3-{[2-(6-Chloro-1-methyl-1H-indazol-3-yl)-5H-pyrrolo[2,3-b]pyrazine-7-carbonyl]-amino}-cyclohexyl)-carbamic acid tert-butyl ester;

2-(6-Fluoro-1-methyl-1H-indazol-3-yl)-5H-pyrrolo[2,3-b]pyrazine-7-carboxylic acid (1-aminomethyl-cyclopropyl)-amide;

2-Isoquinolin-8-yl-5H-pyrrolo[2,3-b]pyrazine-7-carboxylic acid tert-butylamide;

2-[6-Methyl-1-(2-morpholin-4-yl-ethyl)-1H-indazol-3-yl]-5H-pyrrolo[2,3-b]pyrazine-7-carboxylic acid (2-hydroxy-1,1-dimethyl-ethyl)-amide;

2-[5-Difluoromethoxy-1-(3,4-dihydroxy-butyl)-1H-indazol-3-yl]-5H-pyrrolo[2,3-b]pyrazine-7-carboxylic acid tert-butylamide;

2-[5-Difluoromethoxy-1-(3-hydroxy-butyl)-1H-indazol-3-yl]-5H-pyrrolo[2,3-b]pyrazine-7-carboxylic acid tert-butylamide;

2-[5-Difluoromethoxy-1-(3-methanesulfonyl-propyl)-1H-indazol-3-yl]-5H-pyrrolo[2,3-b]pyrazine-7-carboxylic acid tert-butylamide;

2-[5-(4-Amino-4-methyl-pentyloxy)-1-methyl-1H-indazol-3-yl]-5H-pyrrolo[2,3-b]pyrazine-7-carboxylic acid tert-butylamide;

2-[5-Difluoromethoxy-1-(3-dimethylamino-propyl)-1H-indazol-3-yl]-5H-pyrrolo[2,3-b]pyrazine-7-carboxylic acid isopropylamide;

2-(1-Methyl-1H-indazol-4-yl)-5H-pyrrolo[2,3-b]pyrazine-7-carboxylic acid tert-butylamide;

2-[5-Difluoromethoxy-1-(3-dimethylamino-propyl)-1H-indazol-3-yl]-5H-pyrrolo[2,3-b]pyrazine-7-carboxylic acid (1-methyl-cyclopropyl)-amide;

2-[5-Difluoromethoxy-1-(3-dimethylamino-propyl)-1H-indazol-3-yl]-5H-pyrrolo[2,3-b]pyrazine-7-carboxylic acid ethylamide;

2-[1-(4-Amino-4-methyl-pentyl)-5-difluoromethoxy-1H-indazol-3-yl]-5H-pyrrolo[2,3-b]pyrazine-7-carboxylic acid tert-butylamide;

2-[1-(3,4-Dihydroxy-butyl)-6-fluoro-1H-indazol-3-yl]-5H-pyrrolo[2,3-b]pyrazine-7-carboxylic acid tert-butylamide;

2-[6-Fluoro-1-(3-methanesulfonyl-propyl)-1H-indazol-3-yl]-5H-pyrrolo[2,3-b]pyrazine-7-carboxylic acid tert-butylamide;

2-(6-Fluoro-1-methyl-1H-indazol-3-yl)-5H-pyrrolo[2,3-b]pyrazine-7-carboxylic acid (5-amino-tetrahydro-pyran-3-yl)-amide;

2-(5-Isopropyl-1-methyl-1H-indazol-3-yl)-5H-pyrrolo[2,3-b]pyrazine-7-carboxylic acid tert-butylamide;

2-(6-Fluoro-1-methyl-1H-indazol-3-yl)-5H-pyrrolo[2,3-b]pyrazine-7-carboxylic acid ((cis)-5-amino-tetrahydro-pyran-3-yl)-amide;

2-(6-Fluoro-1-methyl-1H-indazol-3-yl)-5H-pyrrolo[2,3-b]pyrazine-7-carboxylic acid ((trans)-5-amino-tetrahydro-pyran-3-yl)-amide;

2-(5-Methanesulfonyl-1-methyl-1H-indazol-3-yl)-5H-pyrrolo[2,3-b]pyrazine-7-carboxylic acid tert-butylamide;

2-[6-Fluoro-1-(3-hydroxy-butyl)-1H-indazol-3-yl]-5H-pyrrolo[2,3-b]pyrazine-7-carboxylic acid (2-hydroxy-1,1-dimethyl-ethyl)-amide;

2-(6-Fluoro-1-methyl-1H-indazol-3-yl)-5H-pyrrolo[2,3-b]pyrazine-7-carboxylic acid (3-hydroxy-azetidin-3-yl-methyl)-amide;

or a pharmaceutically acceptable salt thereof.

17. The compound of claim 16 wherein said compound is 2-(6-Fluoro-1-methyl-1H-indazol-3-yl)-5H-pyrrolo[2,3-b]pyrazine-7-carboxylic acid ((S)-1,2,2-trimethyl-propyl)-amide or a pharmaceutically acceptable salt thereof.

\* \* \* \* \*